US007553653B2

(12) United States Patent
Kakkis et al.

(10) Patent No.: US 7,553,653 B2
(45) Date of Patent: Jun. 30, 2009

(54) VARIANTS AND CHEMICALLY-MODIFIED VARIANTS OF PHENYLALANINE AMMONIA-LYASE

(75) Inventors: Emilio Kakkis, Novato, CA (US); Daniel Oppenheimer, Castro Valley, CA (US); Paul Fitzpatrick, Albany, CA (US); Robert Heft, D.D.O. (CA); Alejandra Gamez, San Diego, CA (US); Lin Wang, San Diego, CA (US); Woomi Kim, Busan (KR); Mary Straub, Malibu, CA (US); Marianne Patch, San Diego, CA (US); Raymond C. Stevens, La Jolla, CA (US)

(73) Assignees: BioMarin Pharmaceutical Inc., Novato, CA (US); The Scripps Research Institute, La Jolla, CA (US)

( * ) Notice: Subject to any disclaimer, the term of this patent is extended or adjusted under 35 U.S.C. 154(b) by 424 days.

(21) Appl. No.: 11/230,374

(22) Filed: Sep. 19, 2005

(65) Prior Publication Data

US 2007/0048855 A1 Mar. 1, 2007

Related U.S. Application Data

(60) Provisional application No. 60/651,950, filed on Feb. 9, 2005, provisional application No. 60/610,770, filed on Sep. 17, 2004.

(51) Int. Cl.
*C12N 9/88* (2006.01)
(52) U.S. Cl. .................................... 435/232
(58) Field of Classification Search .................. 435/232
See application file for complete search history.

(56) References Cited

U.S. PATENT DOCUMENTS

| 4,562,151 | A | 12/1985 | Kishore |
| 5,166,322 | A | 11/1992 | Shaw et al. |
| 5,206,344 | A | 4/1993 | Katre et al. |
| 5,753,487 | A | 5/1998 | Eigtved et al. |
| 5,766,897 | A | 6/1998 | Braxton |
| 5,981,239 | A | 11/1999 | Liu |
| 6,451,986 | B1 | 9/2002 | Pettit |
| 6,461,849 | B1 | 10/2002 | Olsen et al. |
| 6,586,398 | B1 | 7/2003 | Kinstler et al. |
| 6,686,164 | B1 | 2/2004 | Olsen et al. |
| 2002/0052038 | A1 | 5/2002 | Roberts et al. |
| 2002/0102712 | A1 | 8/2002 | Yoshida et al. |
| 2003/0082238 | A1 | 5/2003 | Babich et al. |

FOREIGN PATENT DOCUMENTS

WO WO 90/12874 A2 11/1990
WO WO 03/072743 A2 9/2003
WO WO 2004/044169 A 5/2004

OTHER PUBLICATIONS

Langer et al. Identification of Essential Amino Acids in Phenylalanine Ammonia-Lyase by Site-Directed Mutagenesis. Biochemistry, 1997. vol. 36, pp. 10867-10871.*
Christiansen et al. The Role of the MoFe protein alpha-125-Phe and beta-125-Phe Residues in Azotobacter vinelandii MoFe-Fe protein Interaction. Journal of Inorganic Biochemistry. 2000, vol. 80, pp. 195-204.*
Sorlie et al. Mechanistic Features and Structure of the Nitrogenase alpha-Gin-195 MoFe protein. Biochemistry. 2001, vol. 40, pp. 1540-1549.*
Abell et al., "An In Vivo Evaluation of the Chemotherapeutic Potency of Phenylalanine Ammonia-Lyase," Cancer Research, Oct. 1973, pp. 2529-2532, vol. 33.
Abell et al., "Phenylalanine Ammonia-Lyase from the Yeast Rhodotorula Glutinis," Methods in Enzymology, 1987, pp. 242-253, vol. 142.
Abrams et al., "Rational Antigen Modification as a Strategy to Upregulate or Downregulate Antigen Recognition," Current Opinion Immunology, 2000, pp. 85-91, vol. 12.
Alunni et al., "Mechanisms of Inhibition of Phenlalanine Ammonia-Lyase by Phenol Inhibitors and Phenol/Glycine Synergistic Inhibitors," Archives of Biochemistry and Biophysics, 2003, pp. 170-175, vol. 412.
Ambrus et al., "Depletion of Phenylalanine in the Blood of Phenylketonuric Patients Using a PAL-Enzyme Reactor, an In Vitro Study," Research Communications in Chemical Pathology and Phamacology, Jun. 1982, pp. 105-111, vol. 37, No. 1.
Ambrus et al., "Extracorporeal Enzyme Reactors for Depletion of Phenylalanine in Phenylketonuria," Annals of Internal Medicine, 1987, pp. 531-537, vol. 106.
Ambrus et al., "In Vivo Safety of Hollow Fiber Enzyme-Reactors with Immobilized Phenylalanine Ammonia-Lyase in a Large Animal Model for Phenylketonuria," The Journal of Pharmacology and Experimental Therapeutics, 1983, pp. 598-602, vol. 224, No. 3.
Ambrus et al., "Phenylalanine Depletion for the Management of Phenylketonuria: Use of Enzyme Reactors with Immobilized Enzymes," Science, Sep. 1978, pp. 837-839, vol. 201.

(Continued)

*Primary Examiner*—Karen Cochrane Carlson
*Assistant Examiner*—Suzanne M. Noakes
(74) *Attorney, Agent, or Firm*—Fenwick & West LLP

(57) ABSTRACT

The present invention pertains to the use of the protein phenylalanine ammonia-lyase, as well as the biologically-active derivatives of the said protein for preventing or treating diseases associated with a phenylalanine imbalance in a human or animal body. More particularly, the present invention relates to the therapeutic use of the above-cited molecules for preventing or treating a phenylalanine imbalance in vivo. This invention also deals with therapeutic compositions comprising a pharmaceutically active amount of the above-described therapeutic molecules as well as with therapeutic methods using the said therapeutic compositions. Finally, the present invention relates to processes for selecting more therapeutically-effective variants of said protein as well as to the selected variants themselves.

7 Claims, 24 Drawing Sheets

OTHER PUBLICATIONS

Bourget et al., "Artificial Cell-Microencapsulated Phenylalanine Ammonia-Lyase," Applied Biochemistry and Biotechnology, 1984, pp. 57-59, vol. 10.

Bourget et al., "Phenylalanine Ammonia-Lyase Immobilized in Semipermeable Microcapsules for Enzyme Replacement in Phenylketonuria," Federation of European Biochemical Societies Letters, Jan. 1985, pp. 5-8, vol. 180, No. 1.

Bourget et al., "Phenylalanine Ammonica-Lyase Immobilized in Microcapsules for the Depletion of Phenylalanine in Plasma in Phenylketonuric Rat Model," Biochimica et Biophysica Acta, 1986, pp. 432-438, vol. 883.

Brannigan et al., "Protein Engineering 20 Years On," Nature Reviews, Molecular Cell Biology, Dec. 2002, pp. 964-970, vol. 3.

Chang et al., "A New Theory of Enterorecirculation of Amino Acids and Its Use for Depleting Unwanted Amino Acids Using Oral Enzyme-Artificial Cells, as in Removing Phenylalanine in Phenylketonuria," Art. Cells Blood Subs. and Immob. Biotech., 1995, pp. 1-21, vol. 23, No. 1.

Chang et al., "Procedures for Microencapsulation of Enzymes, Cells and Genetically Engineered Microorganisms," Molecular Biotechnology, 2001, pp. 249-260, vol. 17.

Chen et al., "Tuning the Activity of an Enzyme for Unusual Environments: Sequential Random Mutagenesis of Subtilism E for Catalysis in Dimethylformamide," Proc. Natl. Acad. Sci. U.S.A., Jun. 1993, pp. 5816-5622, vol. 90.

Chirino et al., "Minimizing the Immunogenicity of Protein Therapeutics," Drug Discovery Today, Jan. 2004, pp. 82-90, vol. 9, No. 2.

Delgado et al., "The Uses and Properties of PEG-Linked Proteins," Critical Reviews in Therapeutic Drug Carrier Systems, 1992, pp. 249-304, vol. 9, No. 3-4.

Egrie et al., "Development and Characterization of Novel Erythropoiesis Stimulating Protein (NESP)," British Journal of Cancer, 2001, pp. 3-10, vol. 84, (Supplement 1).

Fritz et al., "Phenylalanine Ammonia-Lyase," The Journal of Biological Chemistry, Aug. 10, 1976, pp. 4646-4650, vol. 251, No. 15.

Gilbert et al., "The Effect of Proteinases on Phenylalanine Ammonia-Lyase from the Yeast Rhodotorula Glutinis," Biochem. J., 1981, pp. 715-723, vol. 199.

Gilbert et al., "Protection of Phenylalanine Ammonia-Lyase from Proteolytic Attack," Biochemical and Biophysical Research Communications, Sep. 16, 1985, pp. 557-563, vol. 131, No. 2.

Goodson et al., "Site-Directed Pegylation of Recombinant Interleukin-2 at Its Glycosylation Site," Biotechnology, Apr. 1990, pp. 343-346, vol. 8.

Graham, "Pegaspargase: A Review of Clinical Studies," Advanced Drug Delivery Reviews, 2003, pp. 1293-1302, vol. 55.

Greenwald et al., "Effective Drug Delivery by PEGylated Drug Conjugates," Advanced Drug Delivery Reviews, 2003, pp. 217-250, vol. 55.

Harris et al., "Effect of Pegylation on Pharmaceuticals," Nature Reviews, Drug Discovery, Mar. 2003, pp. 214-221, vol. 2.

Hedstrom et al., "Converting Trypsin to Chymotrypsin: The Role of Surface Loops," Science, Mar. 6, 1992, pp. 1249-1253, vol. 255, No. 5049.

Hemeling et al., "Structure-Immunogenicity Relationships of Therapeutic Proteins," Pharmaceutical Research, Jun. 2004, pp. 897-903, vol. 21, No. 6.

Hershfield, Enzyme Replacement Therapy of Adenosine Deaminase Deficiency with Polyethylene Glycol-Modified Adenosine Deaminase (PEG-ADA), Immunodeficiency, 1993, pp. 93-97, vol. 4.

Hershfield et al., "Use of Site-Directed Mutagenesis to Enhance the Epitope-Shielding Effect of Covalent Modification of Proteins with Polyethylene Glycol," Proc. Natl. Acad. Sci. USA, Aug. 1991, pp. 7185-7189, vol. 88.

Hopfner et al., "New Enzyme Lineages by Subdomain Shuffling," Proc. Natl. Acad. Sci., USA, Aug. 1998, pp. 9813-9818, vol. 95.

Hoskins et al., "Enzymatic Control of Phenylalanine Intake in Phenylketonuria," The Lancet, Feb. 23, 1980, pp. 392-394.

Hoskins et al., "The Metabolism of Cinnamic Acid by Healthy and Phenylketonuric Adults: a Kinetic Study," Biomedical Mass Spectrometry, 1984, pp. 296-300, vol. 11, No. 6.

Hoskins et al., "Phenylalanine Ammonia Lyase in the Management of Phenylketonuria: The Relationship Between Ingested Cinnamate and Urinary Hippurate in Humans," Research Communications in Chemical Pathology and Pharmacology, Feb. 1982, pp. 275-282, vol. 35, No. 5.

Kalghatgi et al., "Multitubular Reactors with Immobilized L-Phenylalanine Ammonia-Lyase for Use in Extracorporeal Shunts," Research Communications in Chemical Pathology and Pharmacology, Mar. 1980, pp. 551-561, vol. 27, No. 3.

Kim et al., "Trends in Enzyme Therapy for Phenylketonuria," Molecular Therapy, Aug. 2004, pp. 220-224, vol. 10, No. 2.

Kinstler et al., "Characterization and Stability of N-Terminally PEGylated rhG-CSF," Pharmaceutical Research, 1996, pp. 996-1002, vol. 13, No. 7.

Koukol et al., "The Metabolism of Aromatic Compounds in Higher Plants," The Journal of Biological Chemistry, Oct. 1961, pp. 2692-2698, vol. 236, No. 10.

Larue et al., "An Extracorporeal Hollow-Fiber Reactor for Pheylketonuria Using Immobilized Phenylalanine Ammonia Lyase," Dev. Pharmacol. Ther., 1986, pp. 73-81, vol. 9.

Lazar et al., "Designing Proteins for Therapeutic Applications," Current Opinion in Structural Biology, 2003, pp. 513-518, vol. 13.

Lee et al., "N-Terminal Site-Specific Mono-PEGylation of Epidermal Growth Factor," Pharmaceutical Research, May 2003, pp. 818-825, vol. 20, No. 5.

Levy, "Phenylketonuria: Old Disease, New Approach to Treatment," Proc. Natl. Acad. Sci. USA, Mar. 1999, pp. 1811-1813, vol. 96.

Liu et al., "Study on the Novel Strategy to Treatment of Phenylketonuria," Art. Cells Blood Subs. Immob. Biotech., 2002, pp. 243-257, vol. 30, No. 4.

Marconi et al., "Phenylalanine Ammonia-Lyase Entrapped in Fibers," Biochimie, 1980, pp. 575-580, vol. 62.

Marshall et al., "Rational Design and Engineering of Therapeutic Proteins," Drug Discovery Today, Mar. 2003, pp. 212-221, vol. 8, No. 5.

Matalon et al., "Biopterin Responsive Phenylalanine Hydroxylase Deficiency," Genetics in Medicine, Jan./Feb. 2004, pp. 27-32, vol. 6, No.1.

Mehvar, "Modulation of the Pharmacokinetics and Pharmacodynamics of Proteins by Polyethylene Glycol Conjugation," J. Pharm. Pharmaceut. Sci., 2000, pp. 125-136, vol. 3, No. 1.

Meyer et al., "Reduced Antibody Response to Streptavidin Through Site-Directed Mutagenesis," Protein Science, 2001, pp. 491-503, vol. 10.

Parkinson et al., "Pegvisomant in the Treatment of Acromegaly," Advanced Drug Delivery Reviews, 2003, pp. 1303-1314, vol. 55.

Pedersen et al., "Preparation of Immobilized L-Phenylalanine Ammonia-Lyase in Tubular Form for Depletion of L-Phenylalanine," Research Communications in Chemical Pathology and Pharmacology, Jun. 1978, pp. 559-569, vol. 20, No. 3.

Pettit et al., "Structure-Function Studies of Interleukin 15 Using Site-Specific Multigenesis, Polyethylene Glycol Conjugation, and Homology Modeling," The Journal of Biological Chemistry, Jan. 24, 1997, pp. 2312-2318, vol. 272, No. 4.

Poppe et al., "Properties and Synthetic Applications of Ammonia-Lyases," Current Organic Chemistry 2003, pp. 1297-1315, vol. 7.

Rao et al., "Degradation of Aromatic Amino Acids by Fungi," Canadian Journal of Biochemistry, 1967, pp. 1863-1872, vol. 45.

Reddy et al., "Use of Peginterferon alfa-2a (40 KD) (Pegasys®) for the Treatment of Hepatitis C," Advanced Drug Delivery Reviews, 2002, pp. 571-586, vol. 54.

Roberts et al., "In Vivo Effects of Phenylalanine Ammmonia-Lyase," Cancer Treatment Reports, Mar. 1976, pp. 261-263, vol. 60, No. 3.

Russell et al., "Recombinant Proteins for Genetic Disease," Clin. Genet., 1999, pp. 389-394, vol. 55.

Sarkissian et al., "A Heteroallelic Mutant Mouse Model: A New Orthologue for Human Hyperphenylalaninemia," Molecular Genetics and Metabolism, 2000, pp. 188-194, vol. 69.

Schwede et al., "Crystal Structure of Histidine Ammonia-Lyase Revealing a Novel Polypeptide Modification as the Catalytic Electrophile," Biochemistry, 1999, pp. 5355-5361, vol. 38.

Shen et al., "Biochemical Properties and Immunogenicity of L-Phenylalanine Ammonia-Lyase: Effects on Tumor-Bearing Mice," Cancer Treatment Reports, Jun. 1979, pp. 1063-1068, vol. 63, No. 6.

Shen et al., "Clearance of Phenylalanine Ammonia-Lyase from Normal and Tumor-Bearing Mice," Cancer Research, Apr. 1977, pp. 1051-1056, vol. 37.

Suchi et al., "Molecular Cloning of a cDNA Encoding Human Histidase," Biochimica et Biophysica Acta, 1993 pp. 293-295, vol. 1216.

Tangri et al., "Rationally Engineered Proteins or Antibodies with Absent or Reduced Immunogenicity," Current Medical Chemistry, 2002, pp. 2191-2199, vol. 9.

Taylor et al., "Cloning and Expression of Rat Histidase," The Journal of Biological Chemistry, Oct. 25, 1990, pp. 18192-18199, vol. 265, No. 30.

Veronese et al., "Introduction and Overview of Peptide and Protein Pegylation," Advanced Drug Delivery Reviews, 2002, pp. 453-456, vol. 54(4).

Wang et al., "New Preparation for Oral Adminstration of Digestive Enzyme. Lactase Complex Microcapsules," Biomat. Art. Cells Immob. Biotech., 1993, pp. 637-646, vol. 21, No. 5.

Wang et al., "Structural and Biological Characterization of Pegylated Recombinant Interferon alpha-2b and Its Therapeutic Implications," Advanced Drug Delivery Reviews, 2002, pp. 547-570, vol. 54.

Wieder et al., "Some Properties of Polyethylene Glycol: Phenylalanine Ammonia-Lyase Adducts," The Journal of Biological Chemistry, Dec. 25, 1979, pp. 12579-12587, vol. 254, No. 24.

Wilks et al., "Design of a Specific Phenyllactate Dehydrogenase by Peptide Loop Exchange on the Bacillus Stearothermophilus Lactate Dehydrogenase Framework," Biochemistry, 1992, pp. 7802-7806, vol. 31.

Woolf et al., "The Dietary Treatment of Phenylketonuria," Archives of Disease in Childhood, 1958, pp. 31-45, vol. 33.

Yoshioka et al., "Optimal Site-Specific PEGylation of Mutant TNF-$\alpha$ Improves Its Antitumor Potency," Biochemical and Biophysical Research Communications, 2004, pp. 808-814, vol. 315.

Calabrese, J. C., et al., "Crystal Structure of Phenylalanine Ammonia Lyase: Multiple Helix Dipoles Implicated in Catalysis," Biochemistry, Sep. 14, 2004, pp. 11403-11416, vol. 43, No. 36, American Chemical Society.

Gamez, A., et al., Development of Pegylated Forms of Recombinant Rhodosporidium Toruloides Phenylalanine Ammonia-Lyase for the Treatment of Classical Phenylketonuria, Molecular Theory, Jun. 2005, pp. 986-989, vol. 11, No. 6, The American Society of Gene Therapy.

Ikeda, K., et al., "Phenylalanine Ammonia-Lyase Modified with Polyethylene Glycol: Potential Therapeutic Agent for Phenylketonuria," Amino Acids, Nov. 2005, vol. 29, No. 3, Springer-Verlag, Vienna, Austria.

International Search Report and Written Opinion, PCT/US2005/033895, Sep. 5, 2006.

Moola, Z. B., et al., "Erwinia Chrysantheml L-Asparaginase: Epitope Mapping and Production of Antigenically Modified Enzymes," Biochemical Journal, 1994, pp. 921-927, vol. 302, no. Part 3, Portland Press, London, Great Britian.

Spencer, D. I. R., et al., "A Strategy for Mapping and Neutralizing Conformational Immunogenic Sites on Protein Therapeutics," Proteomics, Mar. 2002, pp. 271-279, vol. 2, No. 3, Wiley-VCH Verlag, Weinheim.

Wang, L., et al., "Structure-Based Chemical Modification Strategy for Enzyme Replacement Treatment of Phenylketonuria," Molecular Genetics and Metabolism, Sep. 2005, pp. 134-140, vol. 86, Nol. 1-2, Academic Press, San Diego, CA.

Whittle, P. J., et al., "Protein Structure-Based Drug Design," Annual Review of Biophysics and Biomolecular Structure, 1994, pp. 349-375, vol. 23, Annual Reviews Inc., Palo Alto, CA.

* cited by examiner

1 MAPSLDSISH SFANGVASAK QAVNGASTNL AVAGSHLPTT QVTQVDIVEK MLAAPTDSTL
  cccccccccc cccccccccc cccccccccc hhhccccccc ccchhhhhhh hhccccccce
61 ELDGYSLNLG DVVSAARKGR PVRVKDSDEI RSKIDKSVEF LRSQLSMSVY GVTTGFGGSA
  eeccccccch hhhhhhhhcc eeeeecchhh hhhhhhhhhh cccccccccc cccccccccc
121 DTRTEDAISL QKALLEHQLC GVLPSSFDSF RLGRGLENSL PLEVVRGAMT IRVNSLTRGH
  cccchhhhhh hhhhhhhhcc cccccccccc cceeecceee ehhhhhhhhh hhhhhhhccc
181 SAVRLVVLEA LTNFLNHGIT PIVPLRGTIS ASGDLSPLSY IAAAISGHPD SKVHVVHEGK
  cccchhhhhh hhhhhhhcce eeeeecccccc cccchhhhhh hhhhhhcccc eeeeeeecce
241 EKILYAREAM ALFNLEPVVL GPKEGLGLVN GTAVSASMAT LALHDAHMLS LLSQSLTAMT
  eeeeeehhhh hccccccccc ccchhhhhhc cchhhhhhhh hhhhhhhhhh hhhhhhhhhh
301 VEAMVGHAGS FHPFLHDVTR PHPTQIEVAG NIRKLLEGSR FAVHHEEEVK VKDDEGILRQ
  hhhhccchh cccccccccc cchhhhhhhh hhhhhhcccc cccccccccc cccccccccc
361 DRYPLRTSPQ WLGPLVSDLI HAHAVLTIEA GQSTTDNPLI DVENKTSHHG GNFQAAAVAN
  cchhhcccc hhhhhhhhhh hhhhhhhhhh hccccccccee eeccccccc ccccchhhh
421 TMEKTRLGLA QIGKLNFTQL TEMLNAGMNR GLPSCLAAED PSLSYHCKGL DIAAAAYTSE
  hhhhhhhhhh hhhhhhhhhh hhhhcccccc cccccccccc ccccccchh hhhhhhhhhh
481 LGHLANPVTT HVQPAEMANQ AVNSLALISA RRTTESNDVL SLLLATHLYC VLQAIDLRAI
  hhhhccccc cccccccccc ccccchhhhh hhhhhhhhhh hhhhhhhhhh hhhhhhhhhh
541 EFEFKKQFGP AIVSLIDQHF GSAMTGSNLR DELVEKVNKT LAKRLEQTNS YDLVPRWHDA
  hhhhhhhhhh hhhhhhhcc chhhcccch hhhhhcccc cccccccccc ccbhhhhhhh
601 FSFAAGTVVE VLSSTSLSLA AVNAWKVAAA ESAISLTRQV RETFWSAAST SSPALSYLSP
  hhhhhhhhhh hccccccchh hhhhhhhhhh hhhhhhhhhh hhhhccccc ccchhcccch
661 RTQILYAFVR EELGVKARRG DVFLGKQEVT IGSNVSKIYE AIKSGRINNV LLKMLA
  hhhhhhhhhh hhccccccc cccccccccc hhhhhhhhhh hhhccchhhh hhhhcc Plasma Phe Levels in ENU-2 Mice Following SC Injection of 20 kDa Linear rPAL-PEG Conjugate Anti-rPAL Serum Antibody Titers in ENU2 Mice
Following SC Injection of 20 kDa Linear rPAL-PEG Conjugate Plasma Phe Levels in ENU-2 Mice Following SC Injection of Escalating Doses of 1:8 20 kDa Linear rPAL-PEG Conjugate Anti-rPAL Serum Antibody Titers in ENU2 Mice Following SC Injection of Escalating Doses of 1:8 20 kDa Linear rPAL-PEG Conjugate

SEQUENCE LISTING

<160> NUMBER OF SEQ ID NOS: 100

<210> SEQ ID NO 1
<211> LENGTH: 716
<212> TYPE: PRT
<213> ORGANISM: Rhodosporidium toruloides

<400> SEQUENCE: 1

```
Met Ala Pro Ser Leu Asp Ser Ile Ser His Ser Phe Ala Asn Gly Val
  1               5                  10                  15

Ala Ser Ala Lys Gln Ala Val Asn Gly Ala Ser Thr Asn Leu Ala Val
             20                  25                  30

Ala Gly Ser His Leu Pro Thr Thr Gln Val Thr Gln Val Asp Ile Val
         35                  40                  45

Glu Lys Met Leu Ala Ala Pro Thr Asp Ser Thr Leu Glu Leu Asp Gly
     50                  55                  60

Tyr Ser Leu Asn Leu Gly Asp Val Val Ser Ala Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
            115                 120                 125

Ser Leu Gln Lys Ala Leu Leu Glu His Gln Leu Cys Gly Val Leu Pro
        130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
```

```
                355                 360                 365
Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Asn Phe Gln Ala Ala
                405                 410                 415

Ala Val Ala Asn Thr Met Glu Lys Thr Arg Leu Gly Leu Ala Gln Ile
                420                 425                 430

Gly Lys Leu Asn Phe Thr Gln Leu Thr Glu Met Leu Asn Ala Gly Met
                435                 440                 445

Asn Arg Gly Leu Pro Ser Cys Leu Ala Ala Glu Asp Pro Ser Leu Ser
            450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
        515                 520                 525

Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
                580                 585                 590

Leu Val Pro Arg Trp His Asp Ala Phe Ser Phe Ala Ala Gly Thr Val
            595                 600                 605

Val Glu Val Leu Ser Ser Thr Ser Leu Ser Leu Ala Ala Val Asn Ala
        610                 615                 620

Trp Lys Val Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
            675                 680                 685

Val Thr Ile Gly Ser Asn Val Ser Lys Ile Tyr Glu Ala Ile Lys Ser
        690                 695                 700

Gly Arg Ile Asn Asn Val Leu Leu Lys Met Leu Ala
705                 710                 715

<210> SEQ ID NO 2
<211> LENGTH: 507
<212> TYPE: PRT
<213> ORGANISM: Pseudomonas putida

<400> SEQUENCE: 2

Thr Glu Leu Thr Leu Lys Pro Gly Thr Leu Thr Leu Ala Gln Leu Arg
  1               5                  10                  15
```

```
Ala Ile His Ala Ala Pro Val Arg Leu Gln Leu Asp Ala Ser Ala Ala
            20                  25                  30

Pro Ala Ile Asp Ala Ser Val Ala Cys Val Glu Gln Ile Ile Ala Glu
        35                  40                  45

Asp Arg Thr Ala Tyr Gly Ile Asn Thr Gly Phe Gly Leu Leu Ala Ser
    50                  55                  60

Thr Arg Ile Ala Ser His Asp Leu Glu Asn Leu Gln Arg Ser Leu Val
65                  70                  75                  80

Leu Ser His Ala Ala Gly Ile Gly Ala Pro Leu Asp Asp Asp Leu Val
                85                  90                  95

Arg Leu Ile Met Val Leu Lys Ile Asn Ser Leu Ser Arg Gly Phe Ser
            100                 105                 110

Gly Ile Arg Arg Lys Val Ile Asp Ala Leu Ile Ala Leu Val Asn Ala
        115                 120                 125

Glu Val Tyr Pro His Ile Pro Leu Lys Gly Ser Val Gly Ala Ser Gly
    130                 135                 140

Asp Leu Ala Pro Leu Ala His Met Ser Leu Val Leu Leu Gly Glu Gly
145                 150                 155                 160

Lys Ala Arg Tyr Lys Gly Gln Trp Leu Ser Ala Thr Glu Ala Leu Ala
                165                 170                 175

Val Ala Gly Leu Glu Pro Leu Thr Leu Ala Ala Lys Glu Gly Leu Ala
            180                 185                 190

Leu Leu Asn Gly Thr Gln Ala Ser Thr Ala Tyr Ala Leu Arg Gly Leu
        195                 200                 205

Phe Tyr Ala Glu Asp Leu Tyr Ala Ala Ala Ile Ala Cys Gly Gly Leu
    210                 215                 220

Ser Val Glu Ala Val Leu Gly Ser Arg Ser Pro Phe Asp Ala Arg Ile
225                 230                 235                 240

His Glu Ala Arg Gly Gln Arg Gly Gln Ile Asp Thr Ala Ala Cys Phe
                245                 250                 255

Arg Asp Leu Leu Gly Asp Ser Ser Glu Val Ser Leu Ser His Lys Asn
            260                 265                 270

Ala Asp Lys Val Gln Asp Pro Tyr Ser Leu Arg Cys Gln Pro Gln Val
        275                 280                 285

Met Gly Ala Cys Leu Thr Gln Leu Arg Gln Ala Ala Glu Val Leu Gly
    290                 295                 300

Ile Glu Ala Asn Ala Val Ser Asp Asn Pro Leu Val Phe Ala Ala Glu
305                 310                 315                 320

Gly Asp Val Ile Ser Gly Gly Asn Phe His Ala Glu Pro Val Ala Met
                325                 330                 335

Ala Ala Asp Asn Leu Ala Leu Ala Ile Ala Glu Ile Gly Ser Leu Ser
            340                 345                 350

Glu Arg Arg Ile Ser Leu Met Met Asp Lys His Met Ser Gln Leu Pro
        355                 360                 365

Pro Phe Leu Val Glu Asn Gly Gly Val Asn Ser Gly Phe Met Ile Ala
    370                 375                 380

Gln Val Thr Ala Ala Ala Leu Ala Ser Glu Asn Lys Ala Leu Ser His
385                 390                 395                 400

Pro His Ser Val Asp Ser Leu Pro Ile Ser Ala Asn Gln Glu Asp His
                405                 410                 415

Val Ser Met Ala Pro Ala Ala Gly Lys Arg Leu Trp Glu Met Ala Glu
            420                 425                 430

Asn Thr Arg Gly Val Leu Ala Ile Glu Trp Leu Gly Ala Cys Gln Gly
```

```
                435                 440                 445
Leu Asp Leu Arg Lys Gly Leu Lys Thr Ser Ala Lys Leu Glu Lys Ala
    450                 455                 460

Arg Gln Ala Leu Arg Ser Glu Val Ala His Tyr Asp Arg Asp Arg Phe
465                 470                 475                 480

Phe Ala Pro Asp Ile Glu Lys Ala Val Glu Leu Leu Ala Lys Gly Ser
                485                 490                 495

Leu Thr Gly Leu Leu Pro Ala Gly Val Leu Pro
            500                 505

<210> SEQ ID NO 3
<211> LENGTH: 636
<212> TYPE: PRT
<213> ORGANISM: Homo sapiens

<400> SEQUENCE: 3

Met Pro Arg Tyr Thr Val His Val Arg Gly Glu Trp Leu Ala Val Pro
  1               5                  10                  15

Cys Gln Asp Ala Gln Leu Thr Val Gly Trp Leu Gly Arg Glu Ala Val
                 20                  25                  30

Arg Arg Tyr Ile Lys Asn Lys Pro Asp Asn Gly Gly Phe Thr Ser Val
             35                  40                  45

Asp Asp Ala His Phe Leu Val Arg Arg Cys Lys Gly Leu Gly Leu Leu
         50                  55                  60

Asp Asn Glu Asp Arg Leu Glu Val Ala Leu Glu Asn Asn Glu Phe Val
 65                  70                  75                  80

Glu Val Val Ile Glu Gly Asp Ala Met Ser Pro Asp Phe Ile Pro Ser
                 85                  90                  95

Gln Pro Glu Gly Val Tyr Leu Tyr Ser Lys Tyr Arg Glu Pro Glu Lys
                100                 105                 110

Tyr Ile Glu Leu Asp Gly Asp Arg Leu Thr Thr Glu Asp Leu Val Asn
            115                 120                 125

Leu Gly Lys Gly Arg Tyr Lys Ile Lys Leu Thr Pro Thr Ala Glu Lys
        130                 135                 140

Arg Val Gln Lys Ser Arg Glu Val Ile Asp Ser Ile Lys Glu Lys
145                 150                 155                 160

Thr Val Val Tyr Gly Ile Thr Thr Gly Phe Gly Lys Phe Ala Arg Thr
                165                 170                 175

Val Ile Pro Ile Asn Lys Leu Gln Glu Leu Gln Val Asn Leu Val Arg
            180                 185                 190

Ser His Ser Ser Gly Val Gly Lys Pro Leu Ser Pro Glu Arg Cys Arg
        195                 200                 205

Met Leu Leu Ala Leu Arg Ile Asn Val Leu Ala Lys Gly Tyr Ser Gly
    210                 215                 220

Ile Ser Leu Glu Thr Leu Lys Gln Val Ile Glu Met Phe Asn Ala Ser
225                 230                 235                 240

Cys Leu Pro Tyr Val Pro Glu Lys Gly Thr Val Gly Ala Ser Gly Asp
                245                 250                 255

Leu Ala Pro Leu Ser His Leu Ala Leu Gly Leu Val Gly Glu Gly Lys
            260                 265                 270

Met Trp Ser Pro Lys Ser Gly Trp Ala Asp Ala Lys Tyr Val Leu Glu
        275                 280                 285

Ala His Gly Leu Lys Pro Val Ile Leu Lys Pro Lys Glu Gly Leu Ala
    290                 295                 300
```

-continued

Leu Ile Asn Gly Thr Gln Met Ile Thr Ser Leu Gly Cys Glu Ala Val
305                 310                 315                 320

Glu Arg Ala Ser Ala Ile Ala Arg Gln Ala Asp Ile Val Ala Ala Leu
            325                 330                 335

Thr Leu Glu Val Leu Lys Gly Thr Lys Ala Phe Asp Thr Asp Ile
        340                 345                 350

His Ala Leu Arg Pro His Arg Gly Gln Ile Glu Val Ala Phe Arg Phe
            355                 360                 365

Arg Ser Leu Leu Asp Ser Asp His His Pro Ser Glu Ile Ala Glu Ser
370                 375                 380

His Arg Phe Cys Asp Arg Val Gln Asp Ala Tyr Thr Leu Arg Cys Cys
385                 390                 395                 400

Pro Gln Val His Gly Val Val Asn Asp Thr Ile Ala Phe Val Lys Asn
                405                 410                 415

Ile Ile Thr Thr Glu Leu Asn Ser Ala Thr Asp Asn Pro Met Val Phe
            420                 425                 430

Ala Asn Arg Gly Glu Thr Val Ser Gly Gly Asn Phe His Gly Glu Tyr
            435                 440                 445

Pro Ala Lys Ala Leu Asp Tyr Leu Ala Ile Gly Ile His Glu Leu Ala
    450                 455                 460

Ala Ile Ser Glu Arg Arg Ile Glu Arg Leu Cys Asn Pro Ser Leu Ser
465                 470                 475                 480

Glu Leu Pro Ala Phe Leu Val Ala Glu Gly Gly Leu Asn Ser Gly Phe
                485                 490                 495

Met Ile Ala His Cys Thr Ala Ala Leu Val Ser Glu Asn Lys Ala
            500                 505                 510

Leu Cys His Pro Ser Ser Val Asp Ser Leu Ser Thr Ser Ala Ala Thr
    515                 520                 525

Glu Asp His Val Ser Met Gly Gly Trp Ala Ala Arg Lys Ala Leu Arg
530                 535                 540

Val Ile Glu His Val Glu Gln Val Leu Ala Ile Glu Leu Leu Ala Ala
545                 550                 555                 560

Cys Gln Gly Ile Glu Phe Leu Arg Pro Leu Lys Thr Thr Pro Leu
                565                 570                 575

Glu Lys Val Tyr Asp Leu Val Arg Ser Val Val Arg Pro Trp Ile Lys
        580                 585                 590

Asp Arg Phe Met Ala Pro Asp Ile Glu Ala Ala His Arg Leu Leu Leu
            595                 600                 605

Glu Gln Lys Val Trp Glu Val Ala Ala Pro Tyr Ile Glu Lys Tyr Arg
    610                 615                 620

Met Glu His Ile Pro Glu Ser Arg Pro Leu Ser Pro
625                 630                 635

<210> SEQ ID NO 4
<211> LENGTH: 633
<212> TYPE: PRT
<213> ORGANISM: Rhodosporidium toruloides

<400> SEQUENCE: 4

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

-continued

```
Glu Lys Met Leu Ala Ala Pro Thr Asp Ser Thr Leu Glu Leu Asp Gly
     50                  55                  60

Tyr Ser Leu Asn Leu Gly Asp Val Val Ser Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
             115                 120                 125

Ser Leu Gln Lys Ala Leu Leu Glu His Gln Leu Cys Gly Val Leu Pro
130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
                260                 265                 270

Ala Val Ser Ala Ser Met Ala Thr Leu Ala Leu His Asp Ala His Met
            275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
            355                 360                 365

Pro Gln Trp Leu Gly Pro Leu Val Ser Asp Leu Ile His Ala His Ala
370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
450                 455                 460
```

-continued

Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
        515                 520                 525

Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala
625                 630

<210> SEQ ID NO 5
<211> LENGTH: 626
<212> TYPE: PRT
<213> ORGANISM: Petroselinum crispum

<400> SEQUENCE: 5

Met Glu Asn Gly Asn Gly Ala Thr Thr Asn Gly His Val Asn Gly Asn
1               5                   10                  15

Gly Met Asp Phe Cys Met Lys Thr Glu Asp Pro Leu Tyr Trp Gly Ile
            20                  25                  30

Ala Ala Glu Ala Met Thr Gly Ser His Leu Asp Glu Val Lys Lys Met
        35                  40                  45

Val Ala Glu Tyr Arg Lys Pro Val Val Lys Leu Gly Gly Glu Thr Leu
    50                  55                  60

Thr Ile Ser Gln Val Ala Ala Ile Ser Ala Arg Asp Gly Ser Gly Val
65                  70                  75                  80

Thr Val Glu Leu Ser Glu Ala Ala Arg Ala Gly Val Lys Ala Ser Ser
                85                  90                  95

Asp Trp Val Met Asp Ser Met Asn Lys Gly Thr Asp Ser Tyr Gly Val
            100                 105                 110

Thr Thr Gly Phe Gly Ala Thr Ser His Arg Arg Thr Lys Gln Gly Gly
        115                 120                 125

Ala Leu Gln Lys Glu Leu Ile Arg Phe Leu Asn Ala Gly Ile Phe Gly
    130                 135                 140

Asn Gly Ser Asp Asn Thr Leu Pro His Ser Ala Thr Arg Ala Ala Met
145                 150                 155                 160

Leu Val Arg Ile Asn Thr Leu Leu Gln Gly Tyr Ser Gly Ile Arg Phe
                165                 170                 175

Glu Ile Leu Glu Ala Ile Thr Lys Phe Leu Asn Gln Asn Ile Thr Pro
            180                 185                 190

Cys Leu Pro Leu Arg Gly Thr Ile Thr Ala Ser Gly Asp Leu Val Pro
        195                 200                 205

```
Leu Ser Tyr Ile Ala Gly Leu Leu Thr Gly Arg Pro Asn Ser Lys Ala
    210                 215                 220

Val Gly Pro Thr Gly Val Ile Leu Ser Pro Glu Glu Ala Phe Lys Leu
225                 230                 235                 240

Ala Gly Val Glu Gly Gly Phe Phe Glu Leu Gln Pro Lys Glu Gly Leu
                245                 250                 255

Ala Leu Val Asn Gly Thr Ala Val Gly Ser Gly Met Ala Ser Met Val
            260                 265                 270

Leu Phe Glu Ala Asn Ile Leu Ala Val Leu Ala Glu Val Met Ser Ala
        275                 280                 285

Ile Phe Ala Glu Val Met Gln Gly Lys Pro Glu Phe Thr Asp His Leu
    290                 295                 300

Thr His Lys Leu Lys His His Pro Gly Gln Ile Glu Ala Ala Ala Ile
305                 310                 315                 320

Met Glu His Ile Leu Asp Gly Ser Ala Tyr Val Lys Ala Ala Gln Lys
                325                 330                 335

Leu His Glu Met Asp Pro Leu Gln Lys Pro Lys Gln Asp Arg Tyr Ala
            340                 345                 350

Leu Arg Thr Ser Pro Gln Trp Leu Gly Pro Gln Ile Glu Val Ile Arg
        355                 360                 365

Ser Ser Thr Lys Met Ile Glu Arg Glu Ile Asn Ser Val Asn Asp Asn
    370                 375                 380

Pro Leu Ile Asp Val Ser Arg Asn Lys Ala Ile His Gly Gly Asn Phe
385                 390                 395                 400

Gln Gly Thr Pro Ile Gly Val Ser Met Asp Asn Thr Arg Leu Ala Ile
                405                 410                 415

Ala Ala Ile Gly Lys Leu Met Phe Ala Gln Phe Ser Glu Leu Val Asn
            420                 425                 430

Asp Phe Tyr Asn Asn Gly Leu Pro Ser Asn Leu Ser Gly Gly Arg Asn
        435                 440                 445

Pro Ser Leu Asp Tyr Gly Phe Lys Gly Ala Glu Ile Ala Met Ala Ser
    450                 455                 460

Tyr Cys Ser Glu Leu Gln Phe Leu Ala Asn Pro Val Thr Asn His Val
465                 470                 475                 480

Gln Ser Ala Glu Gln His Asn Gln Asp Val Asn Ser Leu Gly Leu Ile
                485                 490                 495

Ser Ser Arg Lys Thr Ser Glu Ala Val Glu Ile Leu Lys Leu Met Ser
            500                 505                 510

Thr Thr Phe Leu Val Gly Leu Cys Gln Ala Ile Asp Leu Arg His Leu
        515                 520                 525

Glu Glu Asn Leu Lys Ser Thr Val Lys Asn Thr Val Ser Ser Val Ala
    530                 535                 540

Lys Arg Val Leu Thr Met Gly Val Asn Gly Glu Leu His Pro Ser Arg
545                 550                 555                 560

Phe Cys Glu Lys Asp Leu Leu Arg Val Val Asp Arg Glu Tyr Ile Phe
                565                 570                 575

Ala Tyr Ile Asp Asp Pro Cys Ser Ala Thr Tyr Pro Leu Met Gln Lys
            580                 585                 590

Leu Arg Gln Thr Leu Val Glu His Ala Leu Lys Asn Gly Asp Asn Glu
        595                 600                 605

Arg Asn Leu Ser Thr Ser Ile Phe Gln Lys Ile Ala Thr Phe Glu Asp
    610                 615                 620
```

Glu Leu
625

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggacagcgac gagatcaagt caaagattga caaatcgg                              38

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccgatttgtc aatctttgac ttgatctcgt cgctgtcc                              38

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggtcgagtt cttgaagtcg caactctcca tgag                                  34

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcatggaga gttgcgactt caagaactcg accg                                  34

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgagttcttg cgctcgaaac tctccatgag cgtc                                  34

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
gacgctcatg gagagtttcg agcgcaagaa ctcg                                    34
```

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
gcgctcgcaa ctctccatga aagtctacgg cgtcacgac                               39
```

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
gtcgtgacgc cgtagacttt catggagagt tgcgagcgc                               39
```

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
gcaactctcc atgagcaagt acggcgtcac gactggattt ggcgg                        45
```

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
gcaactctcc atgagcgtcc acggcgtcac gactggattt ggcgg                        45
```

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
ccgccaaatc cagtcgtgac gccgtggacg ctcatggaga gttgc                        45
```

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
gcaactctcc atgagcgtcg ccggcgtcac gactggattt ggcgg                        45
```

```
<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccgccaaatc cagtcgtgac gccggcgacg ctcatggaga gttgc              45

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcaactctcc atgagcgtcc tcggcgtcac gactggattt ggcgg              45

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccgccaaatc cagtcgtgac gccgaggacg ctcatggaga gttgc              45

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcaactctcc atgagcgtca agggcgtcac gactggattt ggcgg              45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcaactctcc atgagcgtca ccggcgtcac gactggattt ggcgg              45

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcaactctcc atgagcgtcc agggcgtcac gactggattt ggcgg              45
```

```
<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcaactctcc atgagcgtca acggcgtcac gactggattt ggcgg            45

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcaactctcc atgagcgtca tgggcgtcac gactggattt ggcgg            45

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gagcgtctac ggcgtcacga aaggatttgg cggatccgc                   39

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcggatccgc caaatccttt cgtgacgccg tagacgctc                   39

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgcagacac ccacaccgag gacgccatct cg                          32

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgagatggcg tcctcggtgt gggtgtctgc gg                          32
```

```
<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccgcagacac cgccaccgag gacgccatct cg                                32

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgagatggcg tcctcggtgg cggtgtctgc gg                                32

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgcagacac ccagaccgag gacgccatct cg                                32

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgagatggcg tcctcggtct gggtgtctgc gg                                32

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccgcagacac caagaccgag gacgccatct cg                                32

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccgcagacac cgtcaccgag gacgccatct cg                                32

<210> SEQ ID NO 36
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccgcagacac caacaccgag gacgccatct cg                                    32

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccgcagacac caccaccgag gacgccatct cg                                    32

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cggatccgca gacacccgcc cagaggacgc catctcgctc                            40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gagcgagatg gcgtcctctg ggcgggtgtc tgcggatccg                            40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cggatccgca gacacccgca aagaggacgc catctcgctc                            40

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gagcgagatg gcgtcctctt tgcgggtgtc tgcggatccg                            40

<210> SEQ ID NO 42
<211> LENGTH: 36
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccgaggacgc catctcgctc aagaaggctc tcctcg                              36

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgaggagagc cttcttgagc gagatggcgt cctcgg                              36

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cagaaggctc tcctcgagaa acagctctgc ggtgttc                             37

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gaacaccgca gagctgtttc tcgaggagag ccttctg                             37

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcaaggtgca cgtcgtcagc gagggcaagg agaag                               35

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cttctccttg ccctcgctga cgacgtgcac cttgc                               35

<210> SEQ ID NO 48
<211> LENGTH: 39
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 48
gcaaggtgca cgtcgtccaa gagggcaagg agaagatcc                               39

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggatcttctc cttgccctct tggacgacgt gcaccttgc                               39

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcaaggtgca cgtcgtcggc gagggcaagg agaag                                   35

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cttctccttg ccctcgccga cgacgtgcac cttgc                                   35

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agcaaggtgc acgtcgtcca ccagggcaag gagaag                                  36

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cttctccttg ccctggtgga cgacgtgcac cttgct                                  36

<210> SEQ ID NO 54
<211> LENGTH: 42
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 54
ccctctcatc gacgtccaga acaagacttc gcaccacggc gg                           42

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccgccgtggt gcgaagtctt gttctggacg tcgatgagag gg                           42

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gctcctcgag ggaagcaagt ttgctgtcca ccatgaggag g                            41

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cctcctcatg gtggacagca aacttgcttc cctcgaggag c                            41

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggaggtcaag gtcagggacg acgagggc                                           28

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gccctcgtcg tccctgacct tgacctcc                                           28

<210> SEQ ID NO 60
<211> LENGTH: 33
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 60
catccgcaag ctcctccagg gaagccgctt tgc                                    33

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcaaagcggc ttccctggag gagcttgcgg atg                                    33

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gctgtccacc atcaggagga ggtcaaggtc                                        30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gaccttgacc tcctcctgat ggtggacagc                                        30

<210> SEQ ID NO 64
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gctgtccacc atgagcagga ggtcaaggtc aagg                                   34

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccttgacctt gacctcctgc tcatggtgga cagc                                   34

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 66
ccggctcgaa cctgaaggac gagctcgtcg agaagg                                    36

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccttctcgac gagctcgtcc ttcaggttcg agccgg                                    36

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcgcgacgag ctcgtccaga aggtgaacaa gacgc                                     35

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gcgtcttgtt caccttctgg acgagctcgt cgcgc                                     35

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cgccaagcgc ctccagcaga ccaactcg                                             28

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgagttggtc tgctggaggc gcttggcg                                             28

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 72
ggctcgaacc tgcgctccga gctcgtcgag aaggtg                                36

<210> SEQ ID NO 73
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
caccttctcg acgagctcgg agcgcaggtt cgagcc                                36

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cgccgccgcc cagtcggcca tctcgc                                           26

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcgagatggc cgactgggcg gcggcg                                           26

<210> SEQ ID NO 76
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gttctccaag ccatcgactt gcgcgcgatc tcgtacctct cgccgcgcac tcag            54

<210> SEQ ID NO 77
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctgagtgcgc ggcgagaggt acgagatcgc gcgcaagtcg atggcttgga gaac            54

<210> SEQ ID NO 78
<211> LENGTH: 45
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 78
gacagcaagg tgcacgtcgt cggcaaggag aagatcctgt acgcc            45

<210> SEQ ID NO 79
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggcgtacagg atcttctcct tgccgacgac gtgcaccttg ctgtc            45

<210> SEQ ID NO 80
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gccgctttgc tgtccaccat gaggagattc tccgccagga ccgctacccc       50

<210> SEQ ID NO 81
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggggtagcgg tcctggcgga gaatctcctc atggtggaca gcaaagcggc       50

<210> SEQ ID NO 82
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ccgcgccgac cgactcgacg ctcaaggaca gcgacgagat ccgctc           46

<210> SEQ ID NO 83
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gagcggatct cgtcgctgtc cttgagcgtc gagtcggtcg gcgcgg           46

<210> SEQ ID NO 84
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
```

-continued catcgaggcc ggccagtcga cgaccggcaa tttccaggct gccgctgtgg c        51

<210> SEQ ID NO 85
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gccacagcgg cagcctggaa attgccggtc gtcgactggc cggcctcgat g        51

<210> SEQ ID NO 86
<211> LENGTH: 13
<212> TYPE: PRT
<213> ORGANISM: Rhodosporidium toruloides

<400> SEQUENCE: 86

Ser Ser Phe Asp Ser Phe Arg Leu Gly Arg Gly Leu Glu
 1               5                  10

<210> SEQ ID NO 87
<211> LENGTH: 13
<212> TYPE: PRT
<213> ORGANISM: Rhodosporidium toruloides

<400> SEQUENCE: 87

Phe Asp Ser Phe Arg Leu Gly Arg Gly Leu Glu Asn Ser
 1               5                  10

<210> SEQ ID NO 88
<211> LENGTH: 13
<212> TYPE: PRT
<213> ORGANISM: Rhodosporidium toruloides

<400> SEQUENCE: 88

Val Gly His Ala Gly Ser Phe His Pro Phe Leu His Asp
 1               5                  10

<210> SEQ ID NO 89
<211> LENGTH: 13
<212> TYPE: PRT
<213> ORGANISM: Rhodosporidium toruloides

<400> SEQUENCE: 89

His Ala Gly Ser Phe His Pro Phe Leu His Asp Val Thr
 1               5                  10

<210> SEQ ID NO 90
<211> LENGTH: 13
<212> TYPE: PRT
<213> ORGANISM: Rhodosporidium toruloides

<400> SEQUENCE: 90

Asn Ser Tyr Asp Leu Val Pro Arg Trp His Asp Ala Phe
 1               5                  10

<210> SEQ ID NO 91
<211> LENGTH: 13
<212> TYPE: PRT
<213> ORGANISM: Rhodosporidium toruloides

<400> SEQUENCE: 91

```
Tyr Asp Leu Val Pro Arg Trp His Asp Ala Phe Ser Phe
 1               5                  10
```

<210> SEQ ID NO 92
<211> LENGTH: 13
<212> TYPE: PRT
<213> ORGANISM: Rhodosporidium toruloides

<400> SEQUENCE: 92

```
Leu Val Pro Arg Trp His Asp Ala Phe Ser Phe Ala Ala
 1               5                  10
```

<210> SEQ ID NO 93
<211> LENGTH: 13
<212> TYPE: PRT
<213> ORGANISM: Rhodosporidium toruloides

<400> SEQUENCE: 93

```
Pro Arg Trp His Asp Ala Phe Ser Phe Ala Ala Gly Thr
 1               5                  10
```

<210> SEQ ID NO 94
<211> LENGTH: 13
<212> TYPE: PRT
<213> ORGANISM: Rhodosporidium toruloides

<400> SEQUENCE: 94

```
Trp His Asp Ala Phe Ser Phe Ala Ala Gly Thr Val Val
 1               5                  10
```

<210> SEQ ID NO 95
<211> LENGTH: 9
<212> TYPE: PRT
<213> ORGANISM: Rhodosporidium toruloides

<400> SEQUENCE: 95

```
Val Tyr Gly Ile Thr Thr Gly Phe Gly
 1               5
```

<210> SEQ ID NO 96
<211> LENGTH: 9
<212> TYPE: PRT
<213> ORGANISM: Homo sapiens

<400> SEQUENCE: 96

```
Val Tyr Gly Val Thr Thr Gly Phe Gly
 1               5
```

<210> SEQ ID NO 97
<211> LENGTH: 9
<212> TYPE: PRT
<213> ORGANISM: Rhodosporidium toruloides

<400> SEQUENCE: 97

```
Val Leu Ser Ser Thr Ser Leu Ser Leu
 1               5
```

<210> SEQ ID NO 98
<211> LENGTH: 9
<212> TYPE: PRT
<213> ORGANISM: Homo sapiens

<400> SEQUENCE: 98

```
Val Leu Ser Ser Thr Ser Leu Arg Leu
 1               5
```

```
<210> SEQ ID NO 99
<211> LENGTH: 9
<212> TYPE: PRT
<213> ORGANISM: Rhodosporidium toruloides

<400> SEQUENCE: 99

Ala Leu Ser Tyr Leu Ser Pro Arg Thr
 1               5

<210> SEQ ID NO 100
<211> LENGTH: 9
<212> TYPE: PRT
<213> ORGANISM: Homo sapiens

<400> SEQUENCE: 100

Ala Leu Ser Tyr Leu Lys Pro Arg Thr
 1               5
```

VARIANTS AND CHEMICALLY-MODIFIED VARIANTS OF PHENYLALANINE AMMONIA-LYASE

CROSS-REFERENCE TO RELATED APPLICATIONS

This application claims the benefit of U.S. Provisional Patent Application Nos. 60/610,770 filed on Sep. 17, 2004 and 60/651,950 filed on Feb. 9, 2005, all of which are herein incorporated by reference in their entirety.

TECHNICAL FIELD OF INVENTION

This invention relates to X-ray crystal data for phenylalanine ammonia-lyase (PAL), PAL analogs, compositions thereof, and optimization of such compositions to enhance PAL stability and to reduce immunogenicity and/or proteolytic sensitivity of PAL. The invention further relates to the use of such optimal compositions of PAL for therapeutic and industrial purposes. This invention also relates to histidine ammonia-lyase (HAL) analogs, compositions containing such analogs, and related compositions.

BACKGROUND OF THE INVENTION

PAL is a non-mammalian enzyme widely distributed in plants (Koukol, et al., J. Biol. Chem., 236, pp. 2692-2698 (1961); Hanson, et al., The Enzymes (Boyer, P. D., Ed.), Academic Press, New York, Vol. 7, pp. 75-166 (1972); Poppe, et al., (2003) ibid.) some fungi (Rao, et al., Can. J. Biochem., 4512), pp. 1863-1872 (1967)) and yeast (Abell, et al., Methods Enzymol. 142, pp. 242-253 (1987)) and can also be recombinantly produced in *Escherichia coli*.

A representative list of PALs includes: Q9ATN7 *Agastache rugosa*; O93967 *Amanita muscaria* (Fly agaric); P35510, P45724, P45725, Q9SS45, Q8RWP4 *Arabidopsis thaliana* (Mouse-ear cress); Q6ST23 *Bambusa oldhamii* (Giant timber bamboo); Q42609 *Bromheadia finlaysoniana* (Orchid); P45726 *Camellia sinensis* (Tea); Q9MAX1 *Catharanthus roseus* (Rosy periwinkle) (Madagascar periwinkle); Q9SMK9 *Cicer arietinum* (Chickpea); Q9XFX5, Q9XFX6 *Citrus clementina* x *Citrus reticulate*; Q42667 *Citrus limon* (Lemon); Q8H6V9, Q8H6W0 *Coffea canephora* (Robusta coffee); Q852S1 *Daucus carota* (Carrot); O23924) *Digitalis lanata* (Foxglove); O23865) *Daucus carota* (Carrot); P27991) *Glycine max* (Soybean); O04058) *Helianthus annuus* (Common sunflower); P14166, (Q42858) *Ipomoea batatas* (Sweet potato); Q8GZR8, Q8W2E4 *Lactuca sativa* (Garden lettuce); O49835, O49836 *Lithospermum erythrorhizon*; P35511, P26600 *Lycopersicon esculentum* (Tomato); P35512 *Malus domestica* (Apple) (*Malus sylvestris*); Q94C45, Q94F89 *Manihot esculenta* (Cassaya) (Manioc); P27990 *Medicago sativa* (Alfalfa); P25872, P35513, P45733 *Nicotiana tabacum* (Common tobacco); Q6T1C9 *Quercus suber* (Cork oak); P14717, P53443, Q7M1Q5, Q84VE0, Q84VE0 *Oryza sativa* (Rice); P45727 *Persea americana* (Avocado); Q9AXI5 *Pharbitis nil* (Violet) (Japanese morning glory); P52777 *Pinus taeda* (Loblolly pine); Q01861, Q04593 *Pisum sativum* (Garden pea); P24481, P45728, P45729 *Petroselinum crispum* (Parsley) (*Petroselinum hortense*); Q84LI2 *Phalaenopsis* x *Doritaenopsis* hybrid cultivar; P07218, P19142, P19143 *Phaseolus vulgaris* (Kidney bean) (French bean); Q7XJC3, Q7XJC4 *Pinus pinaster* (Maritime pine); Q6UD65 *Populus balsamifera* subsp. *trichocarpa* x *Populus deltoides*; P45731, Q43052, O24266 *Populus kitakamiensis* (Aspen); Q8H6V5, Q8H6V6 *Populus tremuloides* (Quaking aspen); P45730 *Populus trichocarpa* (Western balsam poplar); O64963 *Prunus avium* (Cherry); Q94ENO *Rehmannia glutinosa*; P11544 *Rhodosporidium toruloides* (Yeast) (*Rhodotorula gracilis*); P10248 *Rhodotorula rubra* (Yeast) (*Rhodotorula mucilaginosa*); Q9M568, Q9M567 *Rubus idaeus* (Raspberry); P31425, P31426 *Solanum tuberosum* (Potato); Q6SPE8 *Stellaria longipes* (Longstalk starwort); P45732 *Stylosanthes humilis* (Townsville stylo); P45734 *Trifolium subterraneum* (Subterranean clover); Q43210, Q43664 *Triticum aestivum* (Wheat); Q96V77 *Ustilago maydis* (Smut fungus); P45735 *Vitis vinifera* (Grape); and Q8VXG7 *Zea mays* (Maize).

Histidine ammonia-lyase (HAL, E.C. 4.3.1.3) is found in mammalian as well as bacterial sources (Taylor, et al., J. Biol. Chem., 265(30), pp. 18192-18199 (1990); Suchi, et al., Biochim. Biophys. Acta, 1216(2), pp. 293-295 (1993)) and the crystal structure of histidase from *Pseudomonas putida* is known (Schwede, et al., Biochemistry, 38(17), pp. 5355-5361 (1999)). HAL from *Corynebacteriaceae* has been proposed to be used for combination therapy with L-histidinol to treat histidine- and/or histamine-dependent pathologies such as human respiratory syncytial virus (HSV), herpes simplex virus (HSV), human immunodeficiency virus (HIV), and cancer (U.S. Patent Application No. 20020052038).

A representative list of HALs includes: Q9 KWE4 (*Agrobacterium rhizogenes*), Q8U8Z7 (*Agrobacterium tumefaciens*), Q6 KPK9, Q81Y45 (*Bacillus anthracis*), Q733H8, Q81AC6 (*Bacillus cereus*), Q9 KBE6 (*Bacillus halodurans*), P10944 *Bacillus subtilis*), Q8A4B3 (*Bacteroides thetaiotaomicron*), Q8G4X5 (*Bifidobacterium longum*), Q89GV3 (*Bradyrhizobium japonicum*), Q8YD10 (*Brucella melitensis*), Q8FVB4 (*Brucella suis*), Q20502 (*Caenorhabditis elegans*), P58082 (*Caulobacter crescentus*), Q7P188 (*Chromobacterium violaceum*), Q891Q1 (*Clostridium tetani*), Q9RZ06 (*Deinococcus radiodurans*), Q8RFC2, Q8RDU4, Q7P5N4 (*Fusobacterium nucleatum*), Q7NCB3 (*Gloeobacter violaceus*), Q9HQD5 (*Halobacterium* sp.), P42357 (*Homo sapiens* (Human)), P35492 (*Mus musculus* (Mouse)), Q7N296 (*Photorhabdus luminescens*), Q6L2V9 (*Picrophilus torridus*), Q7MX86 (*Porphyromonas gingivalis*), Q9HU85 (*Pseudomonas aeruginosa*), Q9HU90 (histidine/phenylalanine ammonia-lyase, *Pseudomonas aeruginosa*), Q8VMR3 (*Pseudomonas fluorescens*), Q88CZ7, P21310 (*Pseudomonas putida*), Q87UM1, Q87UM2, Q87V42 (*Pseudomonas syringae*), Q8XW29 (*Ralstonia solanacearum, Pseudomonas solanacearum*), P21213 (*Rattus norvegicus* (Rat), Q98310, Q987B4, Q98JY1, Q98NG3 (*Rhizobium loti, Mesorhizobium loti*), 031197 *Rhizobium meliloti* (*Sinorhizobium meliloti*), Q8Z896 (*Salmonella typhi*), Q8ZQQ9 (*Salmonella typhimurium*), Q8E9B0, Q8EKJ4 (*Shewanella oneidensis*), Q99XG3, Q8NYY3 (*Staphylococcus aureus*), Q93TX3 (*Stigmatella aurantiaca*), Q9EWW1 (*Streptomyces coelicolor*), P24221 (*Streptomyces griseus*), Q8K5L, Q8NZ46, P58083 (*Streptococcus pyrogenes*), Q9HLI6 (*Thermplasma acidophilum*), Q8RBH4 (*Thermoanaerobacter tengcongensis*), Q978N8 (*Thermoplasma volcanium*), Q73Q56 (*Treponema denticola*), Q9KSQ4 (*Vibrio cholerae*), Q87Q77 (*Vibrio parahaemolyticus*), Q8DA21, Q7MK58, Q7MMJ6, Q8DFZ8 (*Vibrio vulnificus*), Q8PLZ8 (*Xanthomonas axonopodis*), Q8PAA7 (*Xanthomonas campestris*), Q8ZA10 (*Yersinia pestis*).

Enzyme Substitution Therapy for PKU Treatment

Numerous studies have focused on the application of the enzyme phenylalanine ammonia-lyase (PAL, EC 4.3.1.5) for enzyme substitution treatment of PKU (Hoskins, Lancet, i(8165), pp. 392-394 (1980); Gilbert, et al., Biochem. J., 199(3):715-723 (1981); Hoskins, et al., (1982) ibid.; Sarkissian, et al., (1999) ibid.; Liu, et al., Artif. Cells Blood Substit. Immobil. Biotechnol., 30(4):243-257 (2002); Wieder, J Biol Chem., 254(24):12579-12587 (1979); Gamez, In press; Ambrus, et al., J. Pharmacol. Exp. Ther., 224(3):598-602 (1983); Ambrus, et al., Science, 201(4358):837-839 (1978); Kalghatgi, Res. Commun. Chem. Pathol. Pharmacol., 27(3): 551-561 (1980); Ambrus, Res. Commun. Chem. Pathol. Pharmacol., 37(1):105-111 (1982); Gilbert, et al., Biochem. Biophys. Res. Commun., 131(2):557-563 (1985); Pedersen, Res. Commun. Chem. Pathol. Pharmacol., 20(3):559-569 (1978); Marconi, et al., Biochimie, 62(8-9):575-580 (1980); Larue, et al., Dev. Pharmacol. Ther., 9(2):73-81 (1986); Ambrus, C. M., et al., (1987) ibid.; Bourget, et al., Appl. Biochem. Biotechnol., 10:57-59 (1984); Bourget, et al., FEBS Lett., 180(1):5-8 (1985); Bourget, et al., Biochim. Biophys. Acta, 883(3):432-438 (1986); Chang, et al., Artif. Cells Blood Substit. Immobil. Biotechnol., 23(1):1-21 (1995); Chang, et al., Mol Biotechnol., 17(3):249-260 (2001); U.S. Pat. No. 5,753,487).

Phenylketonuria (PKU) is an inborn error of amino acid metabolism that results from impaired activity of hepatic phenylalanine hydroxylase (PAH), the enzyme responsible for the metabolism of phenylalanine. Patients with PAH mutations that lead to PKU and hyperphenylalaninemia (HPA) display impaired neurophysiological functioning and reduced cognitive development. For patients that have severe PKU, there is the potential for irreversible mental retardation unless phenylalanine is controlled at low levels using dietary restrictions. PAL converts phenylalanine to ammonia and trans-cinnamic acid, a harmless metabolite, which is further metabolized and excreted in the urine as hippurate ((Hoskins, et al., (1980) ibid; Hoskins, J. A., et al., "The metabolism of cinnamic acid by healthy and phenylketonuric adults: a kinetic study", Biomed Mass Spectrom, 11(6), pp. 296-300 (1984)).

Current treatment for PKU involves the adherence to a restricted diet for life that is low in proteins and the amino acid phenylalanine (Levy, Proc. Natl. Acad. Sci. U.S.A., 96(5), pp. 1811-1813 (1999)). This dietary therapy is difficult to maintain (Matalon, et al., Genet. Med., 6(1), pp. 27-32 (2004); Woolf, et al., Arch. Dis. Child., 33(167), pp. 31-45 (1958); Kim, Mol Ther., 10(2), pp. 220-224 (2004)) and does not always eliminate the damaging neurological effects that can be caused by elevated phenylalanine levels (Sarkissian, et al., Mol. Genet. Metab., 69, pp. 188-194 (2000)); less than ideal dietary control during pregnancy can lead to birth defects (Levy, H. L., (1999) ibid.). In addition, it is very difficult for PKU/HPA patients to live a normal life while following the restrictive diet, and the dietary therapy can be associated with deficiencies of several nutrients, some of which are detrimental for brain development (Levy, H. L., (1999) ibid.). Most low phenylalanine diet products have organoleptic properties sufficiently unsatisfactory that compliance with this treatment is compromised (Levy, H. L., (1999) ibid.). Therefore, development of a therapeutic treatment would assist the current dietary treatment and prevent the neurological damages inflicted on those individuals with PKU, particularly for those patients with the most severe forms of the disease.

In 1999, Scriver and colleagues reported their initial studies on the use of the enzyme PAL from *Rhodosporidium toruloides* (Sarkissian, C. N., et al., 1999 ibid.) for PKU enzyme substitution applications. Mouse PKU and HPA model studies demonstrated that PAL administration (either by i.p. injection or orally using either PAL in combination with aprotinin protease inhibitor or PAL recombinantly expressed and present inside *E. coli* cells) was able to successfully lower blood plasma phenylalanine levels. In addition, preliminary studies describing the use of PAL with PKU patients have shown reduction in phenylalanine levels using PAL administered in enteric-coated gelatin capsules (Hoskins, J. A., et al., (1980) ibid.) or using an extracorporeal enzyme factory (Ambrus, et al., Ann. Intern. Med., 106(4), pp. 531-537 (1987)). However, the sensitivity of PAL to protease inactivation (low activity in gastric conditions due to protease degradation) and the reduced half-life found after repeated in vivo injection (due to elicitation of an immune response) limits further development of the native PAL protein as a clinical therapeutic.

Other Therapeutic Uses

The use of PAL for cancer treatment has also been suggested based on its ability to limit the nutrient supply of phenylalanine to cancer cells and thereby inhibit neoplastic growth (Fritz, et al., J Biol Chem. 251(15):726 (1976); Roberts, et al., Cancer Treat Rep., 60(3):261-263 (1976); Shen, et al., Cancer Res. 37(4):1051-1056 (1977); Shen, et al., Cancer Treat Rep. 63(6):1063-1068 (1979); Wieder, et al, J Biol Chem., 254(24):12579-12587 (1979)). However, intravenously injected pegylated PAL was cleared rapidly from circulating blood after the 13th injection. In addition, PAL-mediated reduction in phenylalanine prevented the proliferation of murine leukemia and metastatic melanoma (Abell, et al., Cancer Res. 33:2529-2532 (1973)), Roberts, et al., ((1976) ibid) Shen, et al., ((1977) ibid)).

PAL has also been used for tyrosinemia (Marconi, W., et al., (1980) ibid.). Histidine ammonia-lyase (HAL) has been used in enzyme substitution therapy for histidinemia treatment. Histidinemia is an autosomal recessive disorder of histidine metabolism due to defective HAL, and is traditionally a benign condition (Taylor, R. G., et al., (1990) ibid.).

Additional Uses of PAL

PAL has an important industrial use for the synthesis of L-phenylalanine methyl ester (for Aspartame production (D'Cunha, et al., Enzyme and Microbial Technology, 19(6), pp. 421-427 (1996); Hamilton, et al., Trends in Biotechnol., 3(3), pp. 64-68 (1985)) and other substituted L-phenylalanine derivatives that are used as pharmaceutical precursors (U.S. Patent App. 20020102712).

PAL also has agricultural importance, being the initial enzymatic process leading to the phenylpropaniods that produce lignins, coumarins, and flavaniods in plants, fungi, and bacteria. All phenylalanine ammonia-lyase (PAL, EC 4.3.1.5) produce cinnamic acid, which is a precursor for lignins, flavonoids, and coumarins in plants (Alunni, et al., Arch Biochem Biophys., 412(2), pp. 170-175 (2003)). Hence, modulation of PAL activity can influence a number of agricultural phenomena such as the browning of fruit. In addition, structure-based drug design of active site PAL inhibitors could lead to effective herbicides (Poppe, L., et al., ibid.).

Although PAL potentially has various industrial and therapeutic applications, the use of PAL may be limited by reduced specific activity and proteolytic instability. Similar to other therapeutic proteins, use of PAL as an enzyme therapy is accompanied by several disadvantages such as immunogenicity and proteolytic sensitivity. Further, a delicate balance is required between substrate affinity and enzyme activity to achieve and maintain control of plasma phenylalanine levels within a normal somewhat narrow range in disorders characterized by hyperphenylalanemia. As yet, a concerted effort toward improving these parameters has not been made due to a paucity of structural and biochemical knowledge regarding this protein.

Protein Therapeutics and Effective Redesign for Therapeutic Advantage

Numerous proteins are used therapeutically to alleviate metabolic deficiencies caused by genetic disorders. Among the most notable examples are parenterally administered insulin for the treatment of diabetes, alpha-glucosidase for enzyme replacement therapy in Pompe's disease (and other enzymes that are used for other lysosomal storage diseases ("Enzyme Therapy In Genetic Diseases", Birth Defects Original Article Series, Volume 9, E. D. Bergsma, Ed. Baltimore: Williams and Wilkins Company (1973))), interferon-alpha for hepatitis C or cancer treatment, and adenosine deaminase for severe combined immunodeficiency (SCID) therapy (Russell, et al., Clin. Genet., 55(6): pp. 389-394 (1999)). Unfortunately, the lifetimes of these injected foreign proteins are usually diminished due to acute allergic reactions and rapid clearance from the bloodstream.

The efficacy of protein therapeutics can be improved with protein engineering methods, including rational design, directed evolution, chemical modification, and combinatorial optimization strategies. Rational design requires the availability of three-dimensional structural information and consideration of side-chain orientations and mobilities in the context of the structure, combined with generic properties such as side-chain hydrophobicity, polarity, charge, electronic contributions, and propensities to form specific secondary structures. Among rational protein modification methods, a most promising solution involves producing variants using structure-based protein engineering.

Numerous examples of structure-based protein engineering exist, wherein improved properties have been designed into proteins using structure-based design techniques (Lazar, et al., Curr. Opin. Struct. Biol., 13(4), pp. 513-518 (2003); Marshall, et al., Drug Discov. Today, 8(5), pp. 212-221 (2003)). Site-directed mutagenesis of proteins can be used to generate protein variants containing truncations, insertions, and/or point mutations, leading to improved stability, activity, and/or altered activity (Brannigan, et al., Nat Rev Mol Cell Biol., 3(12), pp. 964-970 (2002)). Chimeras, or combinations of two proteins, have been successfully exploited for a number of therapeutic antibody and protein examples. Additional effective protein engineering approaches have used specific protein loop re-engineering (Chen, et al., Proc. Natl. Acad. Sci. U.S.A., 90(12), pp. 5618-5622 (1993)), loop swapping (Wilks, et al., Biochemistry, 31(34), pp. 7802-7806 (1992); 36 Hedstrom, et al., Science, 255(5049), pp. 1249-1253 (1992)), and subdomain shuffling (Hopfner, et al., Proc. Natl. Acad. Sci., U.S.A., 95(17), pp. 9813-9818 (1998)) approaches.

Immunologic Response Reduction for Protein Therapeutics

Numerous strategies have been devised for minimizing immune responses of therapeutically-administered proteins (Chirino, et al., Drug Discov. Today, 9(2), pp. 82-90 (2004); U.S. Pat. Nos. 6,686,164 and 6,461,849). For some protein classes such as antibodies, increasing human sequence content (chimeras and/or 'humanization') has reduced immunoreactivity, whereas another effective strategy wherein protein solution properties have been improved (e.g. to reduce aggregation propensity) has also led to reduced immune response. Numerous proteins have had antibody epitopes and agretopes removed using iterative site-directed mutagenesis including replacement of hydrophobic and charged residues with polar neutral residues, alanines, or computationally-selected residues to produce less immunoreactive protein variants. In one example, site-directed mutagenesis of streptavidin was used to reduce immunogenicity (Meyer, et al., Protein Sci., 10(3), pp. 491-503 (2001)). In this case, surface "veneering" was used to mutate surface residues capable of forming high energy ionic or hydrophobic interactions to remove such potential interacting sites. Mutants producing high yields of active tetrameric protein were then tested for reduced antibody recognition in mice and humans, and minimized antibody response upon mutant injection in rabbits. In general, substitution of smaller neutral residues for charged, aromatic, or large hydrophobic surface residues reduced the ability to elicit an immune response in rabbits.

Site-directed mutagenesis has been successfully used for point mutagenesis to alleviate immunoreactivity. For example, site-directed rational modification of antigenic determinants was used to downregulate the CD8(+) and CD4 (+) T lymphocyte responses (Abrams, et al. Curr. Opin. Immunol., 12(1), pp. 85-91 (2000)). Alternate immunoreactivity reduction routes include the removal of agretopes, the generation of variants less susceptible to antigen-processing cell recognition or binding, or the reduction or removal of MHC binding ability. Different approaches have relied upon humanization (making protein variants with more human sequence content), surface veneering (making protein variants with less immunoreactive surface features), and other similar methods wherein specific mutations are made and then screened for lessened immunoreactivity. For example, the "Immunostealth" method uses a combination of in silico sequence analysis methods and high-throughput in vitro biochemical screening assays to identify HTL epitopes, followed by rational modification to alter their HTL binding capacity, resulting in protein variants non-recognizable by the immune system (Tangri, et al., Curr. Med. Chem., 9(24), pp. 2191-2199 (2002)). In addition, the methods of structure-based protein engineering can be combined with more 'random' protein modification methods, such as directed evolution, that can use screening and/or selection to develop more favorable protein variants.

In another approach, the chemical conjugation of a water-soluble polymer, such as polyethylene glycol (PEG), to the protein of interest is a common approach often used to extend the half-lives of proteins in vivo. Generally, polyethylene glycol molecules are connected to the protein via a reactive group found on the protein. Amino groups, such as those on lysine residues or at the N-terminus, are convenient for such attachment. The covalent coupling of activated PEG molecules to the protein of interest (pegylation) has been shown to increase circulation half-times, reduce immunogenicity and antigenicity, and allow retention of bioactivity (Harris, et al., Nat. Rev. Drug Discov., 2(3), pp. 214-221 (2003); Greenwald, et al., Adv Drug Deliv Rev., 55(2), pp. 217-250 (2003); Veronese, et al., Adv Drug Deliv Rev., 54(4), pp. 453-456 (2002); Mehvar, J. Pharm. Pharmaceut. Sci., 3(1), p. 125-136 (2000); Delgado, et al., Critical Reviews in Therapeutic Drug Carrier Systems, 9(3-4), pp. 249-304 (1992)).

Currently, a number of pegylated protein therapeutics have received FDA approval and are being used parenterally to treat a number of diseases such as: hepatitis C and metastatic renal cell carcinoma using PEG-INTRON™ (pegylated interferon-alpha2b [Wang, et al., Adv Drug Deliv Rev., 54(4), pp. 547-570 (2002)]) or PEGASYS™ (pegylated interferon-alpha2a [Rajender Reddy, et al., Adv Drug Deliv Rev., 54(4), pp. 571-586 (2002)]); acute lymphoblastic leukemia using ONCASPAR™ (PEGASPARGASE™ or pegylated L-asparaginase [Graham, Adv Drug Deliv Rev., 55(10), pp. 1293-1302 (2003)]); severe combined immunodeficiency (SCID) using ADAGEN™ (bovine PEGADEMASE™ or pegylated adenosine deaminase [Hershfield, Immunodeficiency, 4(1-4), pp. 93-97 (1993)]); and acromegaly using SOMAVERT™

(PEGVISOMANT™ or pegylated human growth hormone antagonist [Parkinson, et al., Adv Drug Deliv Rev., 55(10), pp. 1303-1314 (2003)]).

Pegylated Proteins

In addition to the pegylation of native protein, site-specific pegylation of proteins has also been performed. Examples of site-specific pegylation include Cys-pegylated IL-3 (U.S. Pat. No. 5,166,322 and WO 90/12874) and Cys-pegylated IL-2 (U.S. Pat. No. 5,206,344) as well as Lys-pegylated purine nucleoside phosphorylase (Hershfield, et al., Proc. Natl. Acad. Sci. USA, 88, pp. 7185-7189 (1991)), an N-terminal selectively pegylated lysine-deficient mutant TNF-α (Yoshioka, et al., Biochem Biophys Res Commun., 315(4), pp. 808-814 (2004)), an N-terminally site-specific pegylated G-CSF (Kinstler, et al., Pharm. Res., 13(7), pp. 996-1002 (1996)), and gylcosylation site-specific pegylated IL-2 (Goodson, et al., Biotechnology, 8(4), pp. 343-346 (1990)). U.S. Pat. No. 6,451,986 discloses site-specific mutation and pegylation of p75 tumor necrosis factor receptor, and U.S. Pat. No. 5,766,897 discloses site-specific pegylation via an exisiting cysteine residue or introduction of a site-specific cysteine residue (at an N-linked glycosylation site or the position of a residue that is normally solvent-accessible in the naturally-occurring protein). Hermeling, S., et al. discuss the use of site-specific PEG attachment around possible antigenic epitope regions to reduce immunogenicity (Hermeling et al. Pharm Res., 21(6), pp. 897-903 (2004)). Similar approaches to improve protein in vivo lifetimes have been adopted for a Cys-pegylated humanized anti-interleukin-8 antibody (Leong, et al., (2001) ibid.) and an N-terminal aldehyde activated alpha-amine group derivatized on epidermal growth factor (Lee, et al., Pharm. Res., 20(5), pp. 818-825 (2003)). In a related approach, a hyper-glycosylated form of human erythropoietin displayed an improved serum half-life and greater in vivo potency, thereby allowing for less frequent administration to obtain the same biological response (Egrie, et al., Br J Cancer, 84(Suppl 1), pp. 3-10 (2001)); chemical modification of this form of erythropoietin improved in vivo efficacy even more (U.S. Pat. No. 6,586,398). In one example, pegylation plus additional site-directed mutagenesis was necessary in order to engineer an active IL-15 variant (Pettit, et al., J. Biol. Chem., 272(4), pp. 2312-2318 (1997)).

Native *Rhodotorula glutinis* PAL stabilized with pegylation has been investigated as a therapeutic agent in cancer therapy. However, these agents exhibited residual immunogenicity and protease sensitivity, thereby precluding them from use in human, such as in clinical testing (Wieder, J Biol Chem., 254(24), pp. 12579-12587 (1979)).

The pegylation of PAL to improve L-phenylalanine synthetic capability for industrial applications, and to reduce the immunogenicity of PAL for therapeutic applications has been reported. U.S. Pat. Nos. 4,562,151 and 5,981,239 disclose the use of polyethylene glycol as an agent to improve the activity of PAL for the production of L-phenylalanine and L-phenylalanine analogs, respectively. U.S. patent application Nos. 20020102712 and 20030082238 describe the use of PEG to stabilize, solubilize, and/or reduce the immunogenicity of PAL for phenylketonuria treatment. U.S. Pat. No. 5,766,897 discloses the use of site-specific introduction of cysteine residues in proteins such as PAL for covalent PEG attachment to improve half-life, decrease immunogenicity and antigenicity, and retain substantially the same level of biological activity.

Oral Therapeutics

Parenterally administered protein therapeutics have demonstrated their clinical effectiveness, but alternative routes of administration are also used. For example, there are two "over-the-counter" oral enzyme replacement therapies that are used for dietary digestion remediation. BEANO™, alpha-galactosidase from *Aspergillis niger* (a food grade mold), is used to correct digestive deficiencies associated with deficient carbohydrate processing (and intestinal gas formation) from legume consumption. Additionally, LACTAID™, an orally active form of the lactase enzyme, is used to alleviate problems associated with lactose (milk sugar) intolerance. Both these products demonstrate that orally administered enzymes can function in the gastrointestinal tract and can successfully correct dietary metabolic deficiencies.

Native *R. toruloides* PAL is very susceptible to protease inactivation (Sarkissian, C. N., et al., (1999) ibid.), requiring either site-directed mutagenesis and/or the introduction of protein surface protective features such as pegylation to produce an orally-effective PAL variant. Additional protease protection can be provided for by using microcapsules (Wang, et al., "Biomater. Artif. Cells Immobilization Biotechnol., 21(5), pp. 637-646 (1993)). Complex microcapsules could be used as an additional measure to protect a therapeutic enzyme from inactivation in both the stomach and the intestine. Semipermeable microcapsules can be further encapsulated by enteric-soluble materials to protect the microcapsules from gastric juice. When the encapsulated enzyme passes into the intestine, the small molecule L-phenylalanine can rapidly diffuse and equilibrate across the semipermeable membrane, allowing conversion to non-toxic products via the encapsulated enzyme.

U.S. Pat. No. 5,753,487 discloses mutants of *R. toruloides* PAL wherein one or more amino acids susceptible to proteolytic cleavage are replaced by other amino acids less susceptible to proteolytic cleavage.

Thus, there remains a need for PAL and HAL molecules with optimal kinetic characteristics including potent catalytic activity and greater biological half-life, greater biochemical stability and attenuated immunogenicity.

SUMMARY OF THE INVENTION

The present invention is based on the identification and characterization of three-dimensional structure of the crystallized *R. toruloides* phenylalanine ammonia lyase (PAL). The present invention provides crystallized *R. toruloides* phenylalanine ammonia-lyase (PAL) and the three-dimensional structure of the crystallized *R. toruloides* PAL determined to a resolution of 1.6 Å or better. The invention contemplates the preparation of variants, including mutants and analogs, with enhanced properties, such as more potent catalytic activity, greater biochemical stability and, for therapeutic applications, attenuated immunogenicity and greater biological half-life. The present invention thus provides optimal compositions of PAL and biologically active fragments, mutants, variants and analogs thereof, their production and purification, and methods of using such compositions for therapeutic and industrial purposes.

In a first aspect, the present invention provides crystallized *R. toruloides* phenylalanine ammonia-lyase (PAL) and the three-dimensional structure of the crystallized *R. toruloides* PAL determined to a resolution of 1.6 Å or better. In a further embodiment, the present invention provides methods for determining the surface-exposed residues of PAL by evaluating the three-dimensional structure of PAL, and the use of the information to design variants and mutants of PAL. The variants and mutants of PAL thus obtained find use as therapeutic agents or in industrial applications.

In a second aspect, the present invention provides compositions of optimized PAL obtained by structure-based molecular engineering approaches and/or chemically-modified (e.g. pegylated) forms of PAL. Specific embodiments contemplate optimal compositions of PAL with enhanced stability, reduced immunogenicity and/or proteolytic sensitivity.

In a third aspect, the invention features novel methods of using PAL compositions for therapeutic and industrial purposes. In one embodiment, the invention contemplates methods of treating disorders caused all or in part by a deficiency in PAH activity by administering a therapeutically effective amount of a pharmaceutical composition comprising PAL to a subject in need of such treatment. The deficiency in PAH activity can be observed, e.g., as activity levels of 50% or less, 25% or less, or 10% or less or 1% or less, compared to normal levels of PAH activity and can manifest as elevated phenylalanine levels, for example, as in hyperphenylalanemia, mild phenylketonuria or classic severe phenylketonuria. In preferred embodiments, the disease is phenylketonuria (PKU).

In specific embodiments, the subject is one who has been diagnosed as having a mutant phenylalanine hydroxylase (PAH). The mutant PAH may comprise a mutation in the catalytic domain of PAH. Exemplary such mutations include but are not limited to mutations F39L, L48S, 165T, R68S, A104D, S110C, D129G, E178G, V190A, P211T, R241C, R261Q, A300S, L308F, A313T, K320N, A373T, V388M E390G, A395P, P407S, and Y414C.

Also contemplated is a method of treating a subject having above normal concentration of plasma phenylalanine (e.g., greater than 180 µM and more preferably, greater than 360 µM) comprising administering to the subject a PAL composition in an amount effective to produce a decrease in the plasma phenylalanine concentration of the subject. The subject will likely have a plasma phenylalanine concentration greater than 180 µM prior to administration of the PAL. More particularly, the subject has a plasma phenylalanine concentration of between 120 µM and 200 µM. In other embodiments, the subject has a plasma phenylalanine concentration of between 200 µM and 600 µM. In still other embodiments, the subject has a plasma phenylalanine concentration of between 600 µM and 1200 µM. Yet another class of subjects to be treated is those that have an unrestricted plasma phenylalanine concentration greater than 1200 µM.

In specific embodiments, the subject is an infant, more particularly, an infant having a plasma phenylalanine concentration greater than 1200 µM. The invention contemplates methods of treating an infant having phenylketonuria, comprising administering a PAL composition to the subject in an amount effective to produce a decrease in the plasma phenylalanine concentration of the infant wherein the infant is between 0 and 3 years of age and the infant has a plasma phenylalanine concentration of between about 360 µM to about 4800 µM. Prior to the administering of PAL, the infant has a phenylalanine concentration of about 1200 µM and the administering of PAL decreases the plasma phenylalanine concentration to about 1000 µM. In other embodiments, prior to the administering of PAL the infant has a phenylalanine concentration of about 800 µM and the administering of PAL decreases the plasma phenylalanine concentration to about 600 µM. In still further embodiments, prior to the administering of PAL the infant has a phenylalanine concentration of about 400 µM and the administering of PAL decreases the plasma phenylalanine concentration to about 300 µM. The therapeutic methods contemplated herein should preferably reduce the plasma phenylalanine concentration of the infant to a range of between about 120 µM to about 360 µM and most preferably to a range of between about 120 µM to about 240 µM.

Also contemplated herein is a method for the treating a pregnant female having hyperphenylalaninemia (HPA) comprising administering to the subject PAL alone or in combination with a protein-restricted diet, wherein administration of PAL alone or in combination with the protein-restricted diet is effective to lower the phenylalanine concentration in the plasma of the subject as compared to the concentration in the absence of the combined administration. In certain embodiments, the subject has an unrestricted plasma phenylalanine concentration of greater than 180 µM but less than 600 µM. In other embodiments, the subject has an unrestricted plasma phenylalanine concentration of greater than 500 µM but less than 1200 µM. In still other embodiments, the subject has an unrestricted plasma phenylalanine concentration of greater than 1200 µM. Pregnant subjects with a plasma phenylalanine concentration greater than 1200 µM are particularly attractive candidates for this type of therapy, as are subject who are females of child-bearing age that are contemplating pregnancy. In those embodiments, in which the subject has a plasma phenylalanine concentration greater than 1200 µM, and the method further comprises administering a protein-restricted diet to the subject.

The invention describes methods of treating classic severe phenylketonuria (PKU) in a subject comprising administering to the subject a PAL or a biologically active fragment, mutant, variant or analog thereof wherein the administration of PAL is effective to lower the phenylalanine concentration in the plasma of the subject as compared to the concentration in the absence of PAL administration. A subject selected for treatment according to the methods of the invention will have an elevated plasma Phe concentration, such a concentration may be greater than 1800 µM in the absence of the therapeutic. Other embodiments contemplate a subject that has a plasma phenylalanine concentration of greater than 1000 µM in the absence of a therapeutic regimen. In preferred embodiments, the combined administration methods of the invention decrease the plasma phenylalanine concentration of the subject to less than 600 µM. More preferably, it is decreased to less than 500 µM. Even more preferably, the combined administration decreases the plasma phenylalanine concentration of the subject in the range from about 120 µM to about 360 µM. Most preferably, the plasma phenylalanine concentration of the subject is reduced in the range from about 120 µM to about 240 µM.

Preferred embodiments include optimizing the dosage to the needs of the organism to be treated, preferably mammals or humans, to effectively ameliorate the disease symptoms. PAL may be administered in a single daily dose, multiple doses on a daily basis, in a single weekly dose or multiple doses on a weekly basis. In some embodiments, the PAL therapy is not continuous, but rather PAL is administered on a daily basis until the plasma phenylalanine concentration of the subject is decreased to less than 360 µM. Preferably, wherein the plasma phenylalanine concentration of the subject is monitored on a daily basis and the PAL is administered when a 10% increase in plasma phenylalanine concentration is observed. In yet other preferred embodiments, doses are delivered once weekly. The invention contemplates doses of at least 0.001 mg/kg, 0.005 mg/kg, 0.01 mg/kg, 0.05 mg/kg, and may range up to 0.1 mg/kg, 0.5 mg/kg, 1.0 mg/kg or higher per week. The preferred dose is 0.001 mg/kg/week.

A variety of parenteral or nonparenteral routes of administration, including oral, transdermal, transmucosal, intrapulmonary (including aerosolized), intramuscular, subcutaneous, or intravenous that deliver equivalent dosages are contemplated. Administration by bolus injection or infusion directly into the joints or CSF is also specifically contemplated, such as intrathecal, intracerebral, intraventricular, via lumbar puncture, or via the cisterna magna. Preferably the doses are delivered subcutaneously or orally.

Other means of increasing PAL activity in the human subjects are also contemplated, including gene therapy. Transfer of a PAL gene is possible through a variety of means known in the art, including viral vectors, homologous recombination, or direct DNA injection. Within the scope of this aspect are embodiments featuring nucleic acid sequences encoding all or a part of PAL or a biologically active mutant or analogs thereof, which may be administered in vivo into cells affected with PAH deficiency.

In another embodiment, PAL may also be administered in combination with a protein restricted diet. The protein-restricted diet administered in the methods herein is one that is a phenylalanine-restricted diet wherein the total phenylalanine intake of the subject is restricted to less than 600 mg per day. In other embodiments, the protein-restricted diet is a phenylalanine-restricted diet wherein the total phenylalanine is restricted to less than 300 mg per day. In still other embodiments, the protein-restricted diet is one, which is supplemented with amino acids, such as tyrosine, valine, isoleucine and leucine. Also contemplated is a composition comprising PAL and a pharmaceutically acceptable carrier, diluent or excipient. The composition may further comprise a medical protein supplement. In other embodiments, the PAL composition is part of an infant formula. In still other embodiments, the protein supplement is phenylalanine free. The protein supplement preferably is fortified with L-tyrosine, L-glutamine, L-carnitine at a concentration of 20 mg/100 g supplement, L-taurine at a concentration of 40 mg/100 g supplement and selenium. It may further comprise the recommended daily doses of minerals, e.g., calcium, phosphorus and magnesium. The supplement further may comprise the recommended daily dose of one or more amino acids selected from the group consisting of L-leucine, L-pro line, L-lysine acetate, L-valine, L-isoleucine, L-arginine, -alanine, glycine, L-asparagine monohydrate, L-tryptophan, L-serine, L-threonine, L-histidine, L-methionine, L-glutamic acid, and L-aspartic acid. In addition, the supplement may be fortified with the recommended daily dosage of vitamins A, D and E. The supplement preferably comprises a fat content that provides at least 40% of the energy of the supplement. Such a supplement may be provided in the form of a powder supplement or in the form of a protein bar.

The invention contemplates methods of treating various forms of neoplastic growth and cancer, including but not limited to lymphoblastic leukemia, mammary tumors, and melanomas.

The invention contemplates methods of using PAL for the commercial production of phenylalanine from ammonia and t-cinnamate. Phenylalanine is used in aspartame, a sweetener and other food products, including beverages, cereals, cakes, desserts, egg and cheese dishes, fats, oils, fish and other seafoods, meat and meat products, milk and milk products, nuts, sauces and condiments, soups, sugars, jams and spreads, and vegetables.

It is further contemplated that PAL may be used for the production of herbicides and antimicrobial agents including enterocin and erythromycin.

In a fourth aspect, the present invention features a method to produce PAL or a biologically active fragment, mutant, variant or analog thereof in amounts which enable using the enzyme therapeutically. In a broad embodiment, the method comprises the step of transforming a cDNA or DNA encoding for all or a part of a PAL or a biologically active fragment, mutant, variant or analog thereof into a cell suitable for the expression thereof. In preferred embodiments, an expression vector is used to transfer the DNA into a suitable cell or cell line for expression thereof. In one particularly preferred embodiment, the cDNA is transformed into *E. coli* and recombinant PAL is overexpressed as fusion protein. In a further embodiment, the method of producing PAL comprises the steps of: (a) growing cells transformed with a cDNA encoding all or a biologically active variant, fragment or mutant of PAL in a suitable growth medium to an appropriate density to produce a seed culture, (b) introducing the transformed cells into a bioreactor, (c) supplying a suitable growth medium to the bioreactor, and (d) separating the transfected cells from the media containing the enzyme.

In another embodiment, recombinant PAL or variants thereof are over-expressed as an N-terminal octahistidyl-tagged fusion protein in a vector preferably *E coli* BL21 (DE3)/pLyseS (Invitrogen) with an inducible promoter such as with IPTG (isopropyl-beta-D-thiogalactopyranoside). In a further embodiment, the method of producing PAL comprises the steps of: (1) growing a seed culture for a bioreactor/fermenter from a glycerol stock in shake flasks, (2) introducing such seed culture into a controlled bioreactor in fed-batch mode; (3) growing said culture in glucose-supplemented media, pH (7.8), >20% dissolved oxygen, agitation up to 1200 rpm, 300 C until reaching a cell density of OD600 of 70-100 (~22-25 hrs); (4) inducing said culture with 0.4 mM IPTG; (5) growing said culture at a reduced temperature of 22 to 260 C until activity change is <0.1 IU/ml (approximately 40-48 hrs and an OD600 typically of 200); and (5) harvesting bacteria by continuous centrifugation. In another embodiment, the cell culture media is typically defined and composed of yeast extract protein, peptone-tryptone, glucose, glycerol, casamino acids, trace salts and phosphate buffering salts.

In a fifth aspect, the present invention features a method to purify PAL or a biologically active fragment, mutant or analog thereof. According to one embodiment, a transformed cell mass is grown and ruptured leaving crude recombinant enzyme. Exogenous materials are normally separated from the crude bulk to prevent fouling of the columns. Chromatographic purification can be conducted using one or several chromatographic resins. Subsequently, the purified protein can be formulated into a buffer designed to provide stable activity over an extended period of time. In another embodiment, the method to purify the PAL comprises the steps of: (a) Lysis of the bacteria containing recombinant PAL; (b) treatment of lysate with heat to inactivate viruses; (c) clarification of this lysate using a second continuous centrifugation step and/or depth filtration (d) passage of clarified lysate through a charcoal filtration step; (e) passage of filtrate in (d) through a final filtration step (as with a Sartorious Sartopore 0.2 µm filter); (f) passage of final filtrate over a hydrophobic interaction chromatography resin, such as a butyl hydrophobic interaction chromatography; (g) passage of eluate in (f) over an anionic chromatography resin, such as a Q ion exchange column; (h) recovery of final product by buffer exchange with tangential flow filtration; and (i) sterilization of the final product. Those skilled in the art readily appreciate that one or more of the chromatography steps may be omitted or substituted, or that the order of the chromatography steps may be changed within the scope of the present invention. Optionally, appropriate sterilizing steps may be performed as desired.

In a sixth aspect, the invention provides methods of using PAL compositions for the diagnosis of diseases, including but not limited to disorders caused all or in part by a deficiency in PAH activity. In one embodiment, PAL is used to measure levels of phenylalanine in blood samples. In a further embodiment, the invention contemplates a diagnostic kit comprising PAL for use in monitoring blood samples of subjects with elevated levels of phenylalanine.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE FIGURES

FIG. 2 is the sequence alignment for *R. toruloides* PAL (SEQ ID NO: 4), P. p HAL, (SEQ ID NO: 2)P. c HAL (SEQ ID NO: 5) and human HAL (SEQ ID NO: 3).

FIG. 5 shows the deduced amino acid sequence of wild-type *Rhodosporidium toruloides* PAL (SEQ ID NO: 1) including their assignment to secondary structural elements found in the three-dimensional structure of PAL determined by X-ray crystallography.

FIG. 9B samples are: Group 1 Branched 1:8 10 kDa; Group 2 Branched 1:24 10 kDa; Group 3 Branched 1:32 10 kDa; Group 4 Linear 1:32 5 kDa; Group 5 wt PAL; Group 6 buffer control. FIG. 9C samples are: Group 1 Branched 1:16 10 kDa; Group 2 Branched 1:24 10 kDa; Group 3 Branched 1:32 10 kDa; Group 4 Linear 1:8 20 kDa; Group 5 wt PAL; Group 6 buffer control.

DETAILED DESCRIPTION OF THE INVENTION

Figure 1:
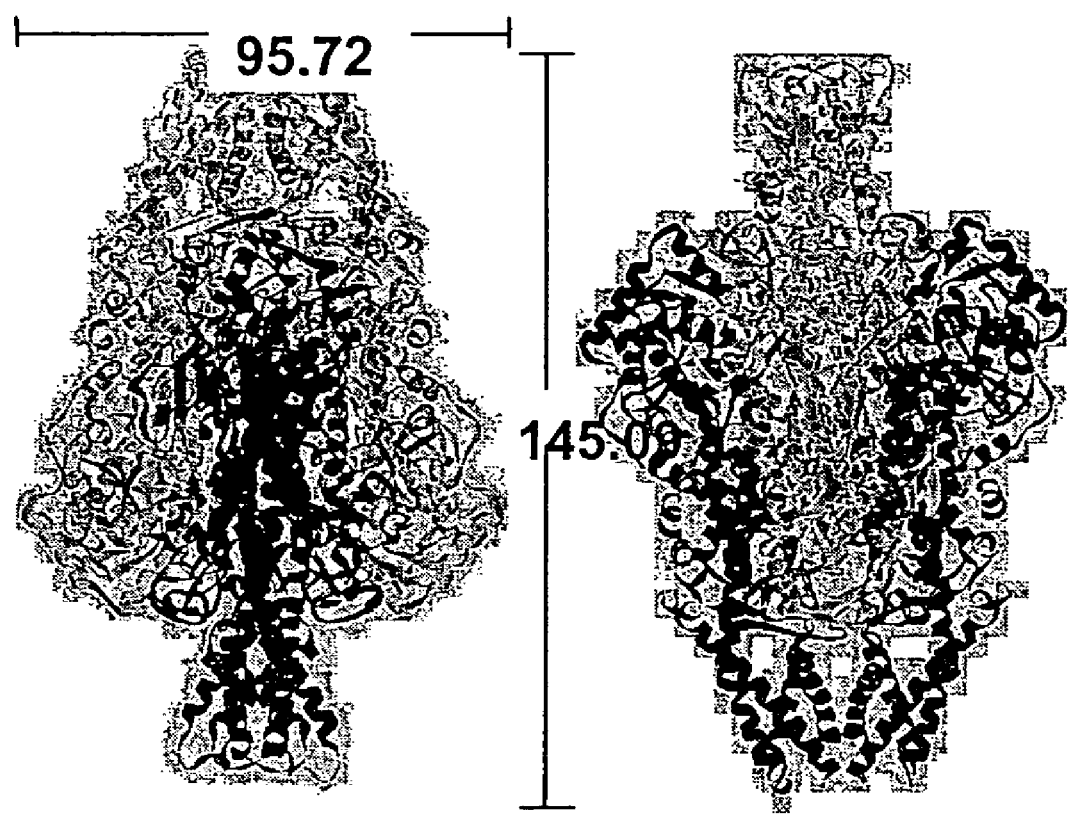
FIG. 1 is a schematic drawing of the 1.6 Å X-ray crystallographically-determined structure of the PAL tetramer.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology, within the skill of the art. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990).

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |

| | |
|---|---|
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations arising with hosts that produce the proteins or errors due to PCR amplification.

As used herein, an "analogue" or "derivative" is a compound, e.g., a peptide, having more than about 70% sequence but less than 100% sequence similarity with a given compound, e.g., a peptide. Such analogues or derivatives may be comprised of non-naturally occurring amino acid residues, including by way of example and not limitation, homoarginine, ornithine, penicillamine, and norvaline, as well as naturally occurring amino acid residues. Such analogues or derivatives may also be composed of one or a plurality of D-amino acid residues, and may contain non-peptide interlinkages between two or more amino acid residues.

The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. For example, an "effective amount" for therapeutic uses is the amount of the composition comprising an oligonucleotide disclosed herein required to provide a clinically significant decrease in the symptoms of a cardiovascular disease, such as those resulting from a heart attack, for example. An appropriate "effective" amount in any individual case may be determined by one of ordinary skill in the art using routine experimentation.

"Treatment" refers to prophylactic treatment or therapeutic treatment or diagnostic treatment.

A "prophylactic" treatment is a treatment administered to a subject who does not exhibit signs of a disease or exhibits only early signs for the purpose of decreasing the risk of developing pathology. The conjugate compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective. The conjugate compounds of the invention may be given as a therapeutic treatment or for diagnosis.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a pharmacologically effective amount of a PAL polypeptide and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a conjugate compound of the present invention and a pharmaceutically acceptable carrier.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular conjugate employed and the effect to be achieved, and the pharmacodynamics associated with each compound in the host.

By "physiological pH" or a "pH in the physiological range" is meant a pH in the range of approximately 7.2 to 8.0 inclusive, more typically in the range of approximately 7.2 to 7.6 inclusive.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

A. Structure-Based Protein Engineering

Numerous methods are known for protein engineering using rational optimization based primarily on protein structural information (Brannigan, J. A., et al., (2002) ibid.; 735 Marshall, S. A., et al., "Rational design and engineering of therapeutic proteins", Drug Discov. Today, 8(5), pp. 212-221 (2003)). Systematic replacement of structural features can lead to improved protein properties and/or a redesign of substrate specificity. Recruitment of function from one member of a gene family into another homologous member can be accomplished by the introduction of a limited number of amino acid substitutions in the immediate substrate binding vicinity. Such improvements in protein function by generating improved protein variants can lead to useful proteins for industrial, agricultural, and therapeutic applications (Bocanegra, et al, Biochemistry, 32(11):2737-2740 (1993); Failla, et al., Fold Des., 1(1):35-42 (1996); Hayes, Proc Natl Acad Sci USA., 99(25):15926-15931 (2002); Voigt, et al., Nat. Struct. Biol., 9(7):553-558 (2002); Malashkevich, et al., Nat Struct Biol., 2(7):548-553 (1995); Wells et al, Proc Natl Acad Sci USA., 84(15):5167-5171 (1987); Wilks et al., Science, 242(4885):1541-1544 (1988)).

B. The Structure of PAL

The three dimensional structure of wild-type unliganded *Rhodosporidium toruloides* PAL (FIG. 1) was determined using x-ray crystallography at 1.6 Å resolution. The resolution can be at least 3.0 Angstrom, preferably at least 2.5 Angstrom, or more preferably at least 2.0 Angstrom.

The PAL protein is a homotetramer, with each monomer consisting of mainly alpha-helices and subdividible into four domains—a central catalytic domain, an N-terminal domain, and a small C-terminal domain with similarity to the *Pseudomonas putida* histidine ammonia-lyase structure (HAL, Schwede, et al., Biochemistry, 38(17), pp. 5355-5361 (1999)) plus an additional domain inserted in the C-terminal region that protrudes from the ends of the intact tetramer molecule. The N-terminal first 25 residues are not visible in the structure for all four monomers in the tetramer, and this region is probably disordered. The loop regions between residues 109-123 and 350-353 are disordered for monomer B, with regions 103-123 and 350-353 disordered for monomers A, C, and D in the PAL tetramer. Two other X-ray structures of *Rhodosporidium toruloides* PAL have been determined using trans-cinnamate and $NH_4$ ion addition during the crystallization process, with resolutions of 2.1 Å ($P3_221$ space group) and 2.7 Å ($P2_1$ space group; Calabrese, et al., Biochemistry, 43(36), pp. 11403-11416 (2004)). The lower pH used for crystallization and the lower resolution of these structures led to more inherent disorder in the structures (especially in the N-terminal regions) and the inability to unambiguously assign additional electron density present on the MIO cofactor to an $NH_2$ adduct.

There are a number of related structures (using DALI, Holm, et al., J. Mol. Biol., 233, 123-138 (1993)) in this family of tetrameric enzymes that catalyze the elimination of various groups from carboxylic acids, including the ammonia-lyases (PAL, HAL, and aspartate ammonia-lyase (AAL)), fumarase, and arginosuccinate lyase (Schwede, et al. Biochemistry, 38(17), pp. 5355-5361 (1999)). In addition, the δ-crystallin avian eye lens protein has a similar fold but is a non-enzymatic form of this structural family (Schwede, et al., (1999), ibid.).

The high-resolution three-dimensional protein crystal structure of PAL provided herein can be used in methods using protein engineering to improve the biochemical and biophysical properties of PAL, and to increase the in vivo therapeutic effectiveness of PAL. In addition, the structure provides information regarding which regions of the structure are the most flexible (to remove and generate a more compact and stable form of PAL), which residues are located near the active site (to mutate in order to enhance activity and/or minimize the size of the protein as well as to provide information for structure-based inhibitor design), and which surface locations are close to immunogenic (e.g. linear epitopes identified in mapping studies) and/or proteolytic sensitive sites (from protease mapping studies), allowing for the introduction of site-specific mutants for direct disruption of problem sites or, alternatively, for surface pegylation or other chemical derivatization to protect sensitive sites present in native PAL.

C. Uses of the Structure Coordinates of PAL

The high-resolution three-dimensional crystal structure of PAL provided herein can be used in computerized methods for selecting regions of the protein for mutation, modification, or combined mutation and modification. For example, the commercially available program GETAREA calculates surface-exposure for amino acid residues based upon X-ray crystallographic coordinates.

The high-resolution three-dimensional crystal structure provided herein can further be used in in-silico methods to design ligands for the active site of the enzyme. For example, commercially available software programs for docking and designing structure-based small-molecules can be used to design PAL inhibitors (Billett, et al., Biochim Biophys Acta, 524(1), pp. 219-230 (1978); Janas, et al., Acta Biochim Pol., 32(2), pp. 131-143 (1985); Zon, et al., Phytochemistry, 59(1), pp. 9-21 (2002); Alunni, et al., Arch Biochem Biophys., 412 (2), pp. 170-175 (2003))

Structure-Based PAL Engineering

Once a reliable three-dimensional structure or structural model is available for a specific macromolecule, rational design has become a productive method for optimization of specific structure and/or function of said macromolecule (Penning, et al., Chem Rev., 101(10), pp. 3027-3046 (2001)). For example, coenzyme specificity has been re-engineered (Bocanegra, et al., Biochemistry, 32(11), pp. 2737-2740 (1993)), protein stabilities have been improved (Malakauskas, et al., Nat Struct Biol., 5(6), pp. 470-475 (1998); Jiang, et al., Protein Sci., 10(7), pp. 1454-1465 (2001); Luo, et al., Protein Sci., 11(5), pp. 1218-1226 (2002); Filikov, et al., Protein Sci., 11(6), pp. 1452-1461 (2002); O'Fagain, Enz Microb Technol., 33, pp. 137-149 (2003); Cammett, et al., J Mol Biol., 327(1, pp. 285-297 (2003)), substrate specificities have been redesigned (Hedstrom, et al., Science, 255(5049), pp. 1249-1253 (1992); Failla, et al., Fold Des., 1(1), pp. 35-42 (1996); Malashkevich, et al., Nat Struct Biol., 2(7), pp. 548-553 (1995); Wilks, et al., Biochemistry, 31(34), pp. 7802-7806 (1992); Feil, et al., Protein Eng., 10(3), pp. 255-262 (1997); Whittle, et al., J Biol Chem., 276(24), pp. 21500-21505 (2001)), ligand or receptor binding specificities have been altered (Cunningham, et al., Proc Natl Acad Sci USA, 88(8), pp. 3407-3411 (1991); Reddy, et al., Nat Biotechnol., 14(13), pp. 1696-1699 (1996); Doyle, et al., Curr Opin Chem Biol., 4(1), pp. 60-63 (2000)), and biological activities have been re-engineered (Chen, et al., Proc. Natl. Acad. Sci. U.S.A., 90(12), pp. 5618-5622 (1993); Sarkar, et al., Nat Biotechnol., 20, pp. 908-913 (2002); Blatt, et al., J Interferon Cytokine Res., 16(7), pp. 489-499 (1996)).

Structure-based engineering can be used to generate PAL variants including rational mutants such as truncations, deletions, insertions, splice variants, point mutations, substitutions, chimeras, loop re-engineered mutants, loop swapping mutants, surface veneering mutants, as well as stochastically-derived mutants (including directed evolution-derived mutants, alone or in combination with rationally developed mutants). In addition, PAL variants can be made comprising PAL mutants wherein mutations have been introduced for site-specific pegylation and/or other chemical derivatizations. The PAL mutants for use in such methods includes any PAL variant having substantially the same functional activity as wild-type *R. toruloides* PAL, including variants, fragments, and chemical derivatives of the parent PAL protein.

Directed Evolution Protein Optimization

Directed evolution methods randomly mutate gene(s) of interest to explore more completely larger regions of protein mutational space. Numerous directed evolution methods exist, including error-prone PCR and random insertion and deletion (RID) mutagenesis to introduce diversity throughout a DNA sequence, and more focused or "directed" diversity-generating methods such as site-saturation mutagenesis and other oligonucleotide-based mutagenesis methods (Brannigan, J. A., et al., (2002) ibid.). In addition, DNA sequence recombinational methods have been used to combine advantageous sites of mutation and simultaneously remove deleterious mutations, producing novel DNA sequences (e.g. methods of DNA shuffling, StEP, RACHITT, ITCHY). Finally, structure-based directed evolution techniques have been used to redesign proteins for therapeutic advantage (structure-based combinatortial engineering, SCOPE, and protein design automation, PDA, methods). The SCOPE method is based on a semi-rational protein engineering approach that uses protein structure information coupled with DNA manipulation techniques to design and create multiple cross-over protein variant libraries from non-homologous genes (O'Maille, et al., J Mol Biol., 321(4), pp. 677-691 (2002)). In PDA, a computational pre-screening of mutational space allows the inclusion of only mutations compatible with a specific protein fold, thus reducing the number of sequence variants to a size amenable to experimental screening (U.S. Pat. No. 6,403,312; Dahiyat, et al., Proc Natl Acad Sci, USA., 94(19), pp. 10172-10177 (1997); Dahiyat, et al., Protein Sci., 6(6), pp. 1333-1337 (1997); Hayes, et al., Proc Natl Acad Sci USA., 99(25), pp. 15926-15931 (2002)).

A large number of examples exist where the use of directed evolution (with coupling to an effective selection or screening protocol) has led to improved catalytic function and biophysical properties (e.g. reduced immunogenicity, increased stability), starting from an initial enzyme species and mutating that species for altered and/or improved function (Vasserot, et al., Drug Discovery Today, 8(3), pp. 118-126 (2003)). For example, successful mutants have been obtained using directed evolution and other "random" mutagenesis methods on a number of different proteins (Triose-phosphate isomerase, Hermes, et al., Proc Natl Acad Sci USA, 87(2): 696-700 (1990); Beta-lactamase, Stemmer, Nature, 370(6488):389-391 (1994), Orencia, et al., Nature Struct Biol, 8:238-242 (2001), Voigt, et al., (2002) ibid; para-nitrobenzyl esterase,) Moore, et al., Nature Biotechnol., 14:458-467 (1996); Galactosidase to fucosidase, Zhang, et al., Proc Natl Acad Sci USA, 94(9):4504-4509 (1997); Aspartate aminotransferase, Yano, et al., Proc Natl Acad Sci USA, 95(10):5511-5515 (1998); Green fluorescent protein, Crameri, et al., Nat Biotechnol, 14(3):315-319 (1996); Horseradish peroxidase, Lin, et al., Biotechnol Prog, 15: 467-471 (1999); Cytochrome P450, Joo, et al., Nature, 399(6737): 670-673 (1999); Biphenyl dioxygenase, Kumamaru, et al., Nat Biotechnol, 16(7):663-666 (1998); Arsenate detoxification pathway, Crameri, et al., Nat Biotechnol, 15(5):436-438 (1997); Cephalosporinase, Crameri, et al., Nature, 391(6664):288-291 (1998); various proteins, Shao, et al., Curr Opin Struct Biol, 6(4):513-518 (1996), various proteins, Skandalis, et al., Chem Biol, 4, pp. 889-898 (1997); Subtilisin, Cunningham, et al., Protein Eng., 1(4):319-325 (1987); Nitrilase, DeSantis, et al., J Am Chem Soc., 125(38): 11476-11477 (2003); Alpha-aspartyl dipeptidase, Kong, et al., Biochem Biophys Res Commun., 289(1):137-142 (2001); Aspartate aminotransferase, Rothman, et al., Protein Science, 13(3):763-772 (2004); L-aspartase, Wang, et al., Biochem Biophys Res Commun., 276(1):346-349 (2000); and lactate dehydrogenase, Wilks, et al., Biochemistry 31(34):7802-7806 (1992).

These studies have repeatedly demonstrated the utility of applying "random" mutagenesis techniques to the development of improved enzyme variants with increased stability, activity, and resistance to degradative pathways. Structural analysis of evolved protein clones leads to insight on the molecular changes that are involved with the improved physical and chemical properties that are obtained (Orencia, et al., in Advances in protein chemistry: Evolutionary protein design, F. H. Arnold, Editor, Academic Press: San Diego, pp. 227-259 (2001)). The rewards to be gained with directed evolution techniques are especially evident in light of the repeated occurrence of beneficial mutations that involve non-active site residues, with some sites of mutation located over 15-20 Å from enzyme active site regions having beneficial effects (Oue, et al., J. Biol. Chem., 274(4), pp. 2344-2349 (1999)). Directed evolution and other random mutagenesis techniques, coupled to selection and screening procedures, can be used to develop more proteolytically stable and chemically robust forms of PAL to be used in industrial applications or, alternatively, for enzyme substitution therapy, e.g. for PKU.

D. Mutants of PAL

Previous experiments have described mutants of PAL (Schuster, et al., FEBS Lett., 349(2), pp. 252-254 (1994); Schuster, et al., Proc Natl Acad Sci USA., 92(18), pp. 8433-8437 (1995); Langer, et al., Biochemistry, 36, pp. 10867-10871 (1997); El-Batal, et al., Acta Microbiol Pol., 49(1), pp. 51-61 (2000); Röther, et al., Eur. J. Biochem., 269, pp. 3065-3075 (2002)) and HAL mutants (Taylor, et al., J. Biol. Chem., 269(44), pp. 27473-27477 (1994); Baedeker, et al., J. Biochem., 269(6), pp. 1790-1797 (2002)).

Optimization of PAL Kinetics—Mutants with Enhanced Catalytic Activity

The biologically active sites of wild-type PAL according to the invention may be modified as desired to optimize PAL kinetic characteristics. Km, the concentration of substrate that gives half-maximal activity, is intimately associated with the therapeutic efficacy of PAL in maintaining phe levels within an acceptable range, i.e. 120 uM to 240 uM. Km is the affinity of the enzyme for the substrate. By controlling affinity, one can limit or control the efficacy of any enzyme against substrate at different concentrations. For example, if Km is 1000 uM (*Rhodosporidium toruloides*), the activity of the enzyme will be reduced to about 12.5% at blood phe levels of 240 uM and to about 3% at blood phe levels of 60 uM. If Km is 240 uM, the activity of the enzyme will be reduced to about 50% at blood phe levels of 240 uM and to about 12% at blood phe levels of 60 uM. If Km is 120 uM, the activity of the enzyme will be reduced to about 70% at blood phe levels of 240 uM and to about 35% at blood phe levels of 60 uM.

Optimally, a preferred therapeutic objective would be to have an enzyme with sufficient activity to reduce but also maintain phe within the optimal range of about 120 uM to about 240 uM. An enzyme with a high Km (i.e. 1000 uM) will lose activity rapidly as phe levels drop to within normal range and will also require the impractical administration of highly concentrated or large volumes of doses. On the other hand, an enzyme with a very low Km may rapidly deplete phe levels, which may be fatal for hyperphenylanemias but may be useful in the management of cancer.

In most preferred embodiments, the biologically active modified mutant PAL has a kcat of at least about 4.0 s-1 and preferably greater than 20 s-1. In other preferred embodiments, the biologically active modified PAL has a Km of between about 100 μM to about 1000 μM. In most preferred embodiments, the biologically active modified PAL exhibits enzymatic activity that is from about two-fold to about 1000-fold times greater that that of the wild-type. Such biological active mutants may be formed using methods well known in the art, such as by site-directed mutagenesis.

Specific Protein Variants: Variants Having Reduced Immunogenicity

A number of strategies are currently used to reduce protein imunogenicity. Preferably, modifications that are introduced to minimize the immune response do not destroy the structure, function, or stability of the macromolecule. Effective strategies used include increasing human sequence content (chimeras and/or other 'humanization' approaches), improving solution properties, removing antibody epitopes, introducing chemical derivatization (such as pegylation), and/or indetifying and removing MHC agretopes. For an injected therapeutic, in vivo immunoreactivity can be addressed by performing epitope mapping followed by rational mutagenesis to modify and/or otherwise mutate these sites of immunogenicity, alone or in combination with site-specific pegylation (Hershfield, et al., (1991) ibid.; Leong, et al., (2001) ibid.; Lee, et al., Pharm. Res., 20(5), pp. 818-825 (2003)) or other chemical derivatization methods to reduce protein immunoreactivity to an acceptable level.

Modification of antigenic surface protein regions reduces immunogenicity (Chirino, et al., (2004) ibid.). One method of improvement involves the construction of smaller sized proteins that retain catalytic activity (e.g. an absorbance assay is used for activity measurement). A second method of improvement, protein engineering coupled to ELISA screening, can also be used to identify mutants with reduced immunoreactivity. Another method introduces point mutations for additional surface Lys sites for pegylation derivatization, a method shown to reduce immunogencity with the test enzyme purine nucleoside phosphorylase (Hershfield, et al., (1991) ibid.). An alternative pathway uses mutation of residues located in protein epitope regions to remove immunogenic sites (Yeung, et al., Immunol., 172(11), pp. 6658-6665 (2004)). In an approach that is analogous to antibody humanization, homologous loop regions and/or residues from human antibodies are substituted into the corresponding loop regions of a homologous protein.

Removal of protein therapeutic proteolytic processing sites can also provide a reduction in immunogenicity by preventing proteasomal processing, thereby preventing clipping and processing into peptide fragments for antigen presenting cell binding. A similar phenomenon has been observed in the alteration of flanking regions for class II MHC determinants, preventing display to autoreactive T cells (Maverakis, et al., Proc Natl Acad Sci, USA., 100(9), pp. 5342-5347 (2003)).

Epitope Mapping

Protein therapeutic epitopes can be calculated using a number of algorithms or experimentally determined with in vitro or in vivo approaches. Computer programs such as "Peptide Companion" ( www.5z.com./csps/comer/pcom/manual.html) and "Protean" in the Lasergene program suite from DNAStar (www.dnastar.com) are commonly used to estimate surface epitope regions of a protein based on the chemical composition and conformation of a protein. Immunogenic regions in a protein sequence are those regions of highest calculated hydrophilicity, based on a hydrophilicity index, and antigenicity, based on the amphipathicity and other conformational parameters of calculated surface protein regions. Alternatively, agretopes in a protein sequence can be located based on computer-modeled predictions of potential HLA binding (Robinson, et al., Nucleic Acids Res., 31(1), pp. 311-314 (2003); De Groot, et al., Novartis Found. Symp., 254, pp. 57-72 (2003)). In addition, epitopes can be identified using in vitro biochemical (Tangri, et al., (2002) ibid.) and in vitro cell-based methods (Stickler, et al., J Immunother., 23(6), pp. 654-660 (2000); Stickler, et al., J Immunol Methods, 281(1-2), pp. 95-108 (2003)). For protein engineering, the relative reduction in immunogenicity can be monitored using assays similar to the in vitro cell-based assay of Stickler, et al. (Stickler, et al., Toxicol Sci., 77(2), pp. 280-289 (2004)).

Figure 3A:
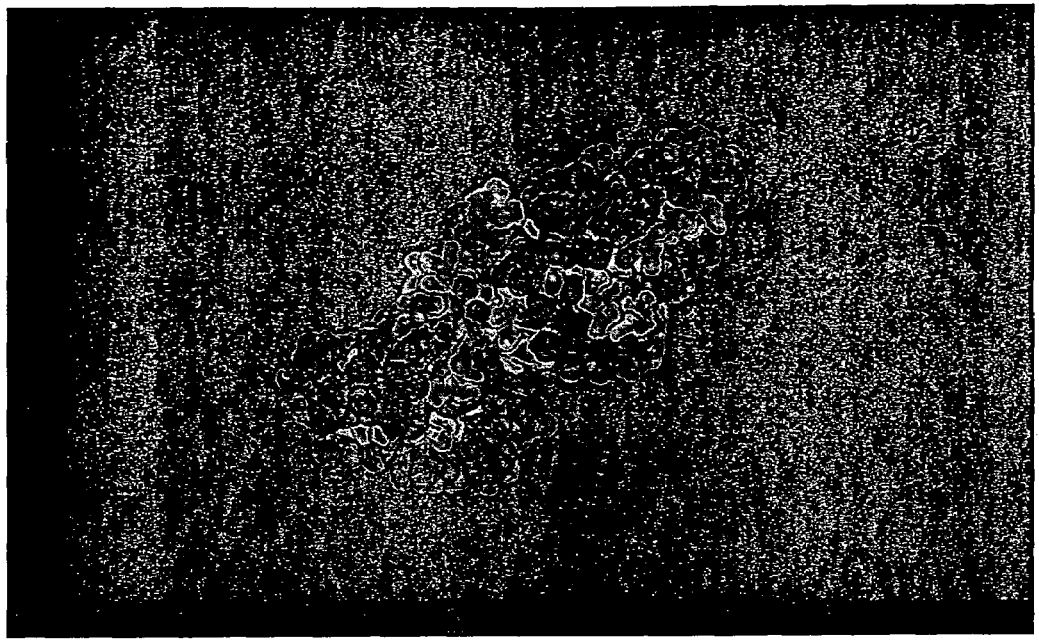
FIG. 3 provides schematic drawings of the structure of a PAL monomer indicating the location of surface regions with calculated immunogenicity (green) using the Protean protein structure annotation module in the Lasergene DNAStar program (Strategic BioSolutions, FIG. 3A) or the Peptide Companion program (BioNexus, FIG. 3B).
Figure 3B:
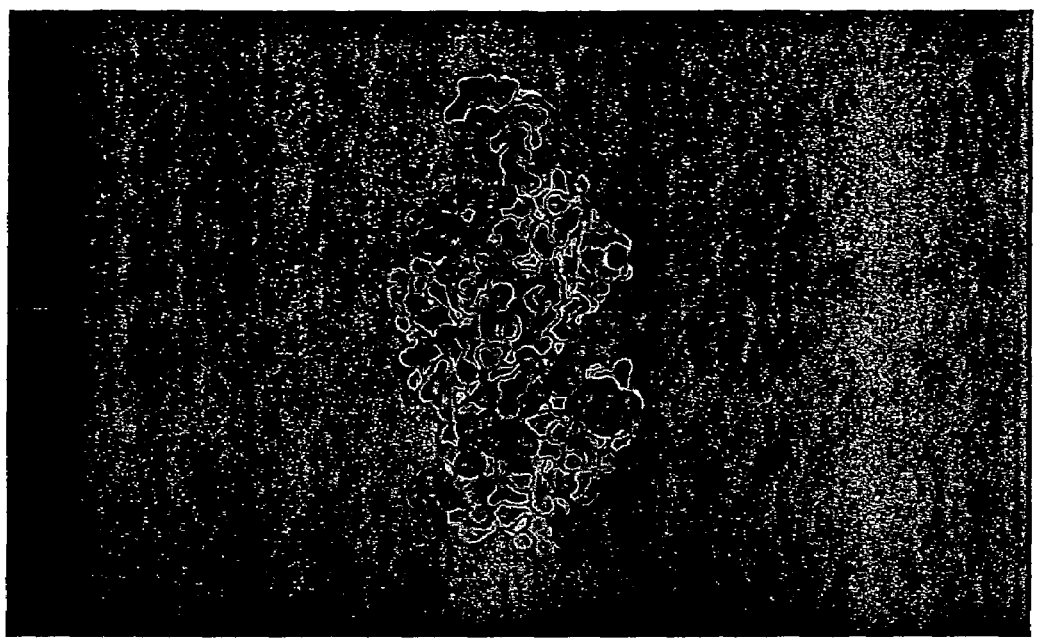

Theoretical epitope mapping, using algorithms, has indicated six regions of immunogenicity on the wild-type R. toruloides PAL protein surface (residues 70-88, 226-243, 337-356, 396-413, 569-589, and 619-636) or alternatively seven regions (71-170, 231-270, 331-370, 391-430, 511-550, 571-650, and 671-710) (FIG. 3). Alternatively, pepscan analysis (epitope mapping), using a library of overlapping peptides covering surface regions of the PAL sequence and probing with rabbit polyclonal antibodies raised against overlapping peptides covering the entire PAL protein sequence, indicates linear epitopes present in PAL. Based on the three-dimensional structure of PAL, these experimentally-identified sites of antigenicity are mutated by either randomly mutating epitope region residues to remove the epitope recognition sites or using site-specific mutation to introduce Lys or Cys residues on the surface near these epitope sites to provide locations for pegylation to cover and protect these sites from immunogenic recognition. ELISA screening of these potentially non-immunogenic PAL mutants (or pegylated forms of these PAL mutants) provides in vitro identification of subsets of PAL mutants that display decreased immunoreactivity.

Surface Residue Identification and Mutation

The surface-exposed residues in or near the immunogenic regions of PAL can be identified. These locations will be a subset of the total number of solvent-accessible surface locations present in the protein, dependent upon proximity to the surface as well as proximity to regions of immunogenicity/antigenicity. The three-dimensional structure of the protein, determined using X-ray crystallography, NMR, or homology modeling, can be used in commercially available software programs to calculate macromolecule solvent-accessible surface area. The output provided using the program GETAREA 1.1 (Fraczkiewicz, et al., J. Comp. Chem., 19, pp. 319-333 (1998)) gives a reliable estimate of surface accessibility for R. toruloides PAL (Table 7). GETAREA and PARAREA and similar programs calculate solvent-accessible surface area using continuum methods with a parametric approach based on the Gauss-Bonnet theorem. PARAREA finds potential intersection points in the Gauss-Bonnet path using all atom pairs in the neighbor list of each atom, whereas GETAREA more efficiently calculates the solvent-exposed vertices using intersection half-spaces defined by planes of two-sphere intersections.

In native PAL, GETAREA identified twelve surface-exposed Lys residues, distributed throughout the tetrameric PAL protein surface, as well as one partially-exposed surface Cys residue (Cys140). These positions are directly available for pegylation derivatization. Further, the three-dimensional structure of PAL can be used to identify additional surface residues available for site-directed mutagenesis. These additional sites can be mutated using standard protein engineering techniques to generate more favorable PAL mutants with reduced immunogenicity, improved proteolytic resistance, and/or improved stability/activity.

Strategies for mutation of the protein to provide protein mutants with improved properties, such as reduced immunogenicity are known in the art. One popular route mutates every non-alanine residue in an epitope to Ala, and mutate every alanine residue in an epitope to Gly. Other methods remove charged and hydrophobic residues from epitope regions, either by mutation or deletion. Additional mutation strategies introduce site-specific mutations followed by site-specific chemical derivatization.

Truncations can also be used for the production of protein improvements. Bioinformatics analysis of PAL relative to histidine ammonia-lyase (HAL) has suggested truncation mutants (residues 23-716 and 1-564). In addition, analysis of the PAL 3-D structure provides an alternative region for truncation, based on the absence of a C-terminal domain region in the structure of the highly homologous HAL protein. C-terminal domain deletion mutants, including mutants where the corresponding loop region from HAL is fused into the PAL sequence to substitute for the C-terminal domain protruding region of the PAL structure (calculated to have major epitope regions), form smaller, more robust, and predicted less immunogenic variants of PAL.

In another method, protein engineering using rational mutagenesis in combination with directed evolution can be used to obtain mutant forms of PAL. For example, implementation of rational design along with experimental and combinatorial design has improved the activity of compstatin (Morikis, et al., Biochem. Soc. Trans., 32(Pt 1), pp. 28-32 (2004)). The combination of rational mutagenesis and directed evolution has also shown promise (Bornscheuer, et al., Curr. Opin. Chem. Biol., 5(2), pp. 137-143 (2001); Dwyer, et al., Science, 304(5679), pp. 1967-1971 (2004)).

Mutant forms of PAL that display less than optimal enzymatic activity can be evolved for activity using the protein engineering method of directed molecular evolution, wherein a random mutagenesis step is followed by a selection procedure for mutants that are active, producing a new protein mutant pool of only those clones that have activity. For example, if a specific mutant PAL (that we have designed to introduce a surface lysine residue near an epitope-containing region of the structure) is inactive, performing directed evolution on this mutant (mutating the inactive mutant and selecting for transformants with activity) generates a new mutant pool containing this beneficial mutation (the surface lysine site) plus a subset of additional random mutations located throughout the structure that restore activity to each active clone. In addition, the directed evolution technique of molecular breeding that can cross different species of the same protein or similar sequences of different proteins (Crameri, et al., Nature, 391, pp. 288-291 (1998); Minshull, et al., Curr. Opin. Chem. Biol., 3(3), pp. 284-290 (1999)) can substitute the sequence of human histidine ammonia-lyase to replace some of the most immunogenic regions of PAL with a human sequence that won't be recognized by the immune system.

Mutant forms of PAL can be obtained by making hybrid protein variants based on semi-rational approaches thereby allowing for a more directed level of protein design relative to pure directed evolution-based methods, as well as providing for a more random level of mutational manipulation for those regions of a protein structure identified using such biased protein engineering approaches. For example, the PDA method generates computationally pre-screened libraries of protein variants, allowing for more rapid optimization of protein properties over pure random, or non-biased protein engineering methods (U.S. Pat. No. 6,403,312; Dahiyat, Curr Opin Biotechnol., 10(4), pp. 387-390 (1999); Filikov, et al., ibid. (2002); Hayes, et al., (2002) ibid.; Luo, et al., (2002) ibid.). Similarly, the SCOPE method constructs hybrid enzyme variants based on "equivalent" subdomains of structure, allowing the creation of multiple crossover protein variant libraries starting from non-homologous genes (O'Maille, et al., (2002) ibid.). In a similar fashion, the method developed by Voigt, et al., constructs hybrids based upon the application of a computational algorithm that identifies fragments of proteins, or 'schemas,' that can be recombined without disrupting the integrity of a protein's three-dimensional structure (Voigt, et al., (2002) ibid.). Computational analysis can also identify conserved core regions of structurally and functionally important positions in a protein fold, based on secondary structural element assignments (Mizuguchi, et al., Bioinformatics, 16(12), pp. 1111-1119 (2000)). Mutant forms of PAL can be obtained following the procedures of any of the art methods.

Hal as an Alternative Enzyme Substitute

The structure of human HAL has been homology modeled based on the structure of *P. putida* HAL (FIG. 6). Although smaller than PAL, the structure of human HAL is very similar, making human HAL a less immunogenic form of an ammonia-lyase to use for PAL protein engineering. An alternative method for obtaining non-immunogenic PAL variants involves directed evolution mutation of human histidine ammonia-lyase (HAL, Suchi, et al., (1993) ibid.), using mutation followed by selection for HAL mutants with PAL activity, to obtain a "humanized" PAL protein that can be further pegylated following the steps of mutation and selection for activity.

Specific Protein Variants: Variants Having Reduced Protease Sensitivity

A number of strategies are currently used to reduce protein protease susceptibility. The modifications introduced to minimize protolytic sensitivity preferably do not destroy the structure, function, or stability of the macromolecule. Effective strategies include providing an enzyme with an active-site stabilizing species such as a competitive inhibitor (Gilbert, et al. (1981) ibid.; U.S. Pat. Nos. 6,584,644; 6,451,986; 6,433,158; 6,461,849), chemically modifying the amino groups in susceptible Lys and/or Arg sites to block trypsin binding sites, mutating chymotrypsin-sensitive Tyr, Phe, and/or Trp residues to smaller neutral amino acids to abolish cleavage susceptibility, ligate or couple PAL to other protective macromolecules (such as Fc antibody domains or the botulinum neurotoxin nontoxic components), and/or introducing Lys or Cys sites near protease susceptible sites for subsequent chemical derivatization with PEG or other chemically protective and stabilizing groups.

Protein engineering was performed on wild-type PAL to construct site-directed mutants to remove the two primary sites of protease sensitivity. Using two different partial proteolytic digests of His-tagged PAL, followed by separation of the two major protein fragments by passage of the protein digest over a nickel chelate column, the primary sites of trypsin and chymotrypsin sensitivity in native PAL were identified based on the N-terminal protein sequences determined for the largest PAL fragments. The primary trypsin site was identified as Arg123, whereas the primary chymotrypsin sensitive site was identified as Tyr110. Six mutants of these protease recognition sites were made (R123H, R123A, R123Q, and Y110H, Y110A, Y110L). All six mutants expressed in levels similar to the wild-type protein and did not show signs of aggregation, but all displayed low specific activity (all units μmol×min$^{-1}$ mg$^{-1}$) Y110H 0.084, Y110A 0, Y110L 0, R123A 0.11, R123H 0.074, R123Q 0.033 (versus wild-type 1.32). Testing of protease susceptibility indicated that point mutation provided protection for the three R123 PAL mutants (both the activity and the intact protein size were retained with trypsin exposure) and the three Y110 mutants (low activity negated any observations about residual activity, but SDS-PAGE gel analysis indicated retention of intact protein size upon chymotrypsin incubation). These PAL mutants were then subjected to directed evolution and proteins exhibiting improved activity for these inactive site-directed mutants were selected.

Figure 4:
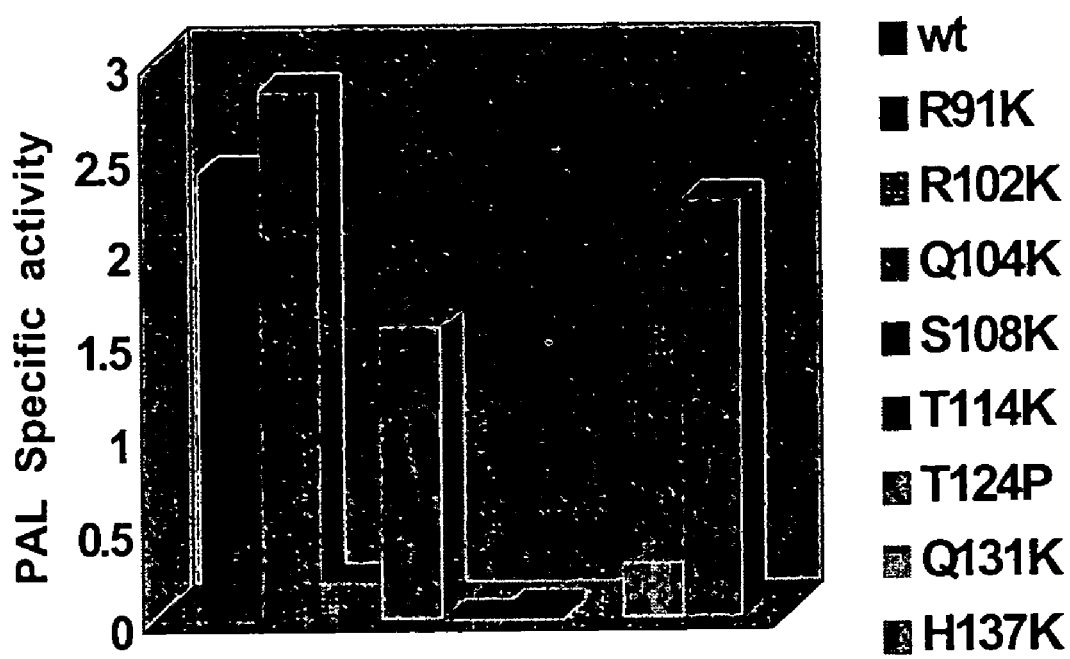
FIG. 4 is a graph that shows the activity of PAL mutants relative to wild-type PAL (activities are in μmol/min×mg).

Alternatively, in order to chemically protect the enzyme (e.g. pegylation), a number of surface sites in the proximity of the Tyr110 and Arg123 protease susceptible sites were mutated to lysine to generate additional sites for surface pegylation. Eight lysine mutants of wild-type PAL were constructed and the specific activities of the modified enzymes are shown in FIG. 4 (T124K mutant with zero activity not shown). The Lys mutants R91K and H137K exhibited favorable characteristics.

Specific Protein Variants: Variants Having Improved Activity

The mutants R91K, H137K, H598Q and K132R PAL have shown improved activity relative to wild-type *R. toruloides* PAL. R91K is located in the helix spanning Asp86 to Leu 01, near the surface of the protein (non-"i" scores, see Table 7 output). H137K is located in the helix spanning Asp126 to Leu139, with wild-type His137 forming hydrogen bonds to the amide carbonyls of Ala133 and Leu134 (for ND1) and the NE2 of Gln138 (for NE2); using the program that mutates position 137 to Lys, the side chain moves relative to the position in H137, but hydrogen bonding interactions are still present.

E. Chemically Modified PAL Variants

Macromolecule chemical modification can be performed in a non-specific fashion (leading to mixtures of derivatized species) or in a site-specific fashion (based on wild-type macromolecule reactivity-directed derivatization and/or site-selective modification using a combination of site-directed mutagenesis and chemical modification) or, alternatively, using expressed protein ligation methods (Hofmann, et al., Curr Opin Biotechnol., 13(4), pp. 297-303 (2002)). Preferably, chemical modification is used to reduce immunogenicity. Pegylation is a demonstrated method to reduce immunogenicity of proteins (Bhadra, et al., Pharmazie, 57(1), pp. 5-29 (2002)) but glycosylation and other chemical derivatization procedures, using modification with phosphorylation, amidation, carboxylation, acetylation, methylation, creation of acid-addition salts, amides, esters, and N-acyl derivatives are also possible (Davis, Science, 303, pp. 480-482 (2004)).

Pegylated Proteins

A series of different pegylation reactions on PAL, using a range of PEG chemical reagent to PAL protein ratios, provided PEG-PAL derivatives for each modification method. The optimal degree of pegylation can be determined based upon the residual activity obtained for each derivatized PAL species using the absorbance assay in combination with PAGE and Native gel analysis to determine the extent of PEG derivatization. After initial ranges of optimal modification are determined, comparative kinetic analysis (including $V_{max}$ and $K_m$ determinations, binding constants of substrates, proteolytic stability, pH dependence of activity, temperature-dependence of activity) and immunoreactivity of optimal PEG-PAL species can be determined by ELISA, immunoprecipitation, and Western blot. Protein engineering can also be used to generate the most favorable PAL mutant for pegylation using the optimal derviatization conditions; by minimizing the size of the PAL protein and only modifying the most antigenic regions of the PAL surface, cost of PEG modification will be reduced while at the same time retaining the maximum amount of enzymatic activity and minimum amount of immunogenicity. Similarly, site-specific pegylation can be used to provide enzyme derivatives.

Other chemical modifications such as phosphorylation or other chemical modification of lys, arg, cys residues can be used to mask immunogenic regions and/or proteolytic sensitive regions. Such chemical modifications include the polymer addition method of Bednarsaki and the Altus Corporation cross-linking method for improving PAL stability, reducing immunogenicity, and improving protease resistance are representative examples. Bednarsaki demonstrated that polymer addition improves protein temperature stability (Wang, et al., J. Am. Chem. Soc., 114(1), pp. 378-380 (1992)), and Altus Corporation has found that glutaraldehyde cross-linking improves enzyme stability.

To discover if the in vivo therapeutic half-life of a protein such as PAL would benefit from pegylation, a variety of different PEG:PAL conjugates were synthesized, characterized in vitro and tested in vivo for L-Phe reduction. In order to both optimize the potential effects of pegylation and to identify the preferred sites of PEG attachment, a design strategy was employed wherein polymer length, conformation, and the degree of PEG attachment were varied.

Methods for preparing the pegylated PAL of the present invention generally comprise the steps of (a) reacting PAL with polyethylene glycol under conditions whereby PAL becomes attached to one or more PEG groups, and (b) obtaining the reaction product(s). Because the specific sites of PAL modification might significantly alter the intrinsic activity of the conjugate, different types and amounts of PEG were explored. The chemistry used for pegylation of PAL was the acylation of the primary amines of PAL using the NHS-ester of methoxy-PEG (O-[(N-Succinimidyloxycarbonyl)-methyl]-O'-methylpolyethylene glycol). Acylation with methoxy-PEG-NHS or methoxy-PEG-SPA results in an amide linkage that eliminates the charge from the original primary amine.

The present methods provide for a substantially homogenous mixture of polymer:protein conjugate. "Substantially homogenous" as used herein means that only polymer:protein conjugate molecules are observed. The polymer:protein conjugate has biological activity and the present "substantially homogenous" pegylated PAL preparations provided herein are those which are homogenous enough to display the advantages of a homogenous preparation, e.g., ease in clinical application in predictability of lot to lot pharmacokinetics.

The polymer molecules contemplated for use in the pegylation approaches described herein may be selected from among water-soluble polymers or a mixture thereof. The water-soluble polymer may be selected from the group consisting of, for example, polyethylene glycol, monomethoxy-polyethylene glycol, dextran, poly-(N-vinyl pyrrolidone), propylene glycol homopolymers, a polypropylene oxide/ethylene oxide co-polymer, polyoxyethylated polyols (e.g., glycerol), dextran, HPMA, FLEXIMER™, and polyvinyl alcohol. The polymer selected should be water-soluble so that the protein to which it is attached does not precipitate in an aqueous environment, such as a physiological environment. The polymer may be branched or unbranched. Preferably, for therapeutic use of the end-product preparation, the polymer will be pharmaceutically acceptable.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol.

The proportion of polyethylene glycol molecules to protein molecules will vary, as will their concentrations in the reaction mixture. In general, the optimum ratio (in terms of efficiency of reaction in that there is no excess unreacted protein or polymer) will be determined by the molecular weight of the polyethylene glycol selected and on the number of available reactive groups (typically ε amino groups) present. As relates to molecular weight, in general, the higher the molecular weight of the polymer used, the fewer number of polymer molecules which may be attached to the protein. Similarly, branching of the polymer should be taken into account when optimizing these parameters. Generally, the higher the molecular weight (or the more branches) the higher the polymer:protein ratio. In the present invention, several different linear PEG polymer lengths were evaluated (5 kDa and 20 kDa). Similarly, conjugates of two-armed branched PEG polymers (10 kDa and 40 kDa) were also tested. In general, for the PEGylation reactions contemplated herein, the preferred average molecular weight is about 2 kDa to about 100 kDa (the term "about" indicating +/−1 kDa). More preferably, the average molecular weight is about 5 kDa to about 40 kDa. The ratio of water-soluble polymer to PAL will generally range from 1:1 for monoPEG-, 2:1 for diPEG etc.

The PAL of the present invention may also include conservative amino acid changes at one or more residues in SEQ ID NO: 1. These changes will have little effect on the biological activity of the analog.

```
MAPSLDSISHSFANGVASAKQAVNGASTNLAVAGSHL    SEQ ID NO: 1
PTTQVTQVDIVEKMLAAPTDSTLELDGYSLNLGDVVS
AARKGRPVRVKDSDEIRSKIDKSVEFLRSQLSMSVYG
VTTGFGGSADTRTEDAISLQKALLEHQLCGVLPSSF
DSFRLGRGLENSLPLEVVRGAMTIRVNSLTRGHSAVR
LVVLEALTNFLNHGITPIVPLRGTISASGDLSPLSYI
AAAISGHPDSKVHVVHEGKEKILYAREAMALFNLEPV
VLGPKEGLGLVNGTAVSASMATLALHDAHMLSLLSQS
LTAMTVEAMVGHAGSFHPFLHDVTRPHPTQIEVAGNI
RKLLEGSRFAVHHEEEVKVKDDEGILRQDRYPLRTSP
QWLGPLVSDLIHAHAVLTIEAGQSTTDNPLIDVENKT
SHHGGNFQAAAVANTMEKTRLGLAQIGKLNFTQLTEM
LNAGMNRGLPSCLAAEDPSLSYHCKGLDIAAAAYTSE
LGHLANPVTTHVQPAEMANQAVNSLALISARRTTESN
DVLSLLLATHLYCVLQAIDLRAIEFEFKKQFGPAIVS
LIDQHFGSAMTGSNLRDELVEKVNKTLAKRLEQTNSY
DLVPRWHDAFSFAAGTVVEVLSSTSLSLAAVNAWKVA
AAESAISLTRQVRETFWSAASTSSPALSYLSPRTQIL
YAFVREELGVKARRGDVFLGKQEVTIGSNVSKIYEAI
KSGRINNVLLKMLA
```

F. PAL and HAL Fusion Proteins

The invention contemplates the preparation and use of fusion proteins comprising a combination of different species of HAL and PAL, including but not limited to bacterial and human HAL, PAL produced by bacterial such as encPAL, yeast (Pichia), and human. A fusion protein refers to a compound comprising PAL or HAL protein or a HAL or PAL polypeptide, or a fragment thereof, attached to another PAL or HAL protein or a HAL or PAL polypeptide, or a fragment thereof. Such fusion proteins may be produced by recombinant genetic engineering methods known to one of ordinary skill in the art. Fusion proteins may be prepared using standard techniques known in the art. Typically, a DNA molecule encoding HAL or PAL or a portion thereof is linked to a DNA molecule encoding the other HAL or PAL proteins or portion thereof. The chimeric DNA construct, along with suitable regulatory elements can be cloned into an expression vector and expressed in a suitable host. The resultant fusion proteins contain HAL or PAL or a portion thereof linked to the other HAL or PAL protein or portion thereof. The fusion protein of the present invention can be produced using host cells expressing a single nucleic acid encoding the entire chimeric protein or more than one nucleic acid sequence, each encoding a domain of the fusion protein and, optionally, an amino acid or amino acids which will serve to link the domains.

G. Selection and Screening Assays

For production and screening of active PAL or HAL variants, initial mutant clone expression can utilize any of the known vector expression systems, such as the His-tag vector expression system, facilitating a high-throughput metal chelate purification step for protein variant isolation. A three-tier screening system can be used to identify favorable protein variants. Initial positive clone identification can use transformation and selection for growth in a phenylalanine auxotrophic $E.$ $coli$ strain. A second round of screening can utilize the $OD_{290}$ absorbance measurement (Hodgins, D. S., (1968) ibid.) amenable to high-throughput processing. Finally, screening for proteolysis resistance (using incubation in the presence of protease cocktail) or, alternatively, immunogenicity reduction (using competitive ELISA measurements), can be used to identify favorable protein variants.

H. Therapeutic Uses and Administration of Optimized PAL Proteins

Various Forms of Hyperphenylalanemia (HPA)

The present invention is directed to the treatment of a variety of HPA patient populations with methods that comprise the use of PAL compositions, either alone or in combination with other therapeutic regimens, for managing HPA and/or PKU. In particular, it is contemplated that PAL compositions may be used to treat that patient population with phenylalanine concentrations that are low enough that dietary intervention is not normally used (i.e., patients with mild HPA), patients with moderate PKU, patients with classic or severe PKU, and any subpopulations thereof. Such patients that are amenable to treatment with PAL compositions to ameliorate the effects of mild HPA, include pregnant women and infants with serum concentrations of less than 200 µM. The various patient populations, and their different therapeutic needs, are discussed in further detail in the present section.

Certain embodiments of the present invention are directed to treating classic severe PKU by administering to the subject a protein-restricted diet in combination with a composition comprising PAL or biologically active variants, mutants, and fragments thereof, wherein the combined administration of the protein-restricted diet and PAL is effective to lower the phenylalanine concentration in the plasma of said subject as compared to said concentration in the absence of said combined administration. In addition, the invention also contemplates treating a pregnant female that has HPA by administering to the female a protein-restricted diet in combination with PAL or a biologically active derivative thereof, such that the combined administration of the protein-restricted diet and PAL is effective to lower the phenylalanine concentration in the plasma of the pregnant woman as compared to such a concentration in the absence of said combined administration. In specific embodiments, therapy is contemplated for patient who manifest Phe levels greater than 420 µM Other embodiments of the invention entail administering a PAL composition to any individual that has HPA, characterized by a plasma Phe concentration greater than 180 µM prior to the administration of PAL, in an amount effective to produce a decrease in such a plasma Phe concentration of the patient. The methods of the invention will be useful in treating an infant having PKU characterized by an elevated Phe concentrations of between greater than 300 µM with PAL compositions described herein. By "infant" the present application refers to a patient that is between the ages of 0 to about 36 months.

Characteristics of Severe Classical PKU and Methods of Treatment Thereof according to the Present Invention.

Severe PKU manifests in a plasma Phe concentration greater than 1200 µM and may be found to be as high as 4800 µM. Patients that have this disorder must be treated with a Phe-free diet in order to bring their plasma Phe concentrations down to a level that is clinically acceptable (typically, less than 600 µM and preferably less than 300 µM). These patients are only able to tolerate a maximum of between 250-350 mg dietary Phe per day (Spaapen et al., Mol. Genet and Metab. 78: 93-99 (2003)). As such, these patients are started on a Phe-restricted formula diet between 7-10 days after birth and are burdened with this dietary restriction for the remainder their lifespan. Any alleviation of the strict dietary restrictions that these individuals are encumbered with would be beneficial.

The tests used for the diagnosis of individuals with classical Phe are described in further detail below. These tests have revealed that patients with classical severe PKU require a low phenylalanine diet (Lucke et al., Pediatr. Neurol. 28: 228-230 (2003)). Thus, it is contemplated that the methods of the invention will entail determining that the patient is suffering from classical PKU by monitoring the plasma Phe concentration of the individual. The patient is then treated by administering PAL compositions alone or a combined regimen of a low protein diet and PAL such that there is produced at least a 25% decrease in the plasma Phe concentrations of the patient. Preferably, the method will produce a 30% decrease in the plasma Phe concentration. Even more preferably, the method will produce a 40%, 50%, 60%, 70%, 80%, 90% or greater decrease in the plasma Phe concentration of the individual (for example, where a patient with severe classical PKU has a Phe concentration of 4800 µM a 90% decrease in the Phe concentration will produce a plasma Phe concentration of 480 µM, a concentration that is sufficiently low to require little dietary restriction). Of course, it should be understood that the treatment methods of the present invention (whether for treating severe classical PKU or any other HPA described herein), should attempt to lower the plasma Phe concentrations of the patient to levels as close to a range of about 120 µM to about 360 µM±15 µM as possible, and most preferably to an optimal range of about 120 µM to about 240 µM.

In preferred embodiments the plasma Phe concentrations of the classical PKU patient being treated is reduced from any amount of unrestricted plasma Phe concentration that is greater than 1000 µM to any plasma Phe level that is less than 600 µM. Of course, even if the combined treatment with PAL and the protein-restricted diet produces a lesser decrease in plasma Phe concentration, e.g., to a level of between 800 µM to about 1200 µM, this will be viewed as a clinically useful outcome of the therapy because patients that have a plasma Phe concentration in this range can manage the disease by simply restricting the amount of protein in the diet as opposed to eating a Phe-restricted formula, thereby resulting in a marked improvement in the quality of life of the individual, as well as leading to greater patient compliance with the dietary restriction.

Any increase in the amount of dietary Phe levels that can be tolerated by the patient as a result of the treatment will be considered to be a therapeutically effective outcome. For example, it is contemplated that as a result of administering the PAL therapy, the patient will be able to increase his/her intake of dietary Phe from 250-350 mg/day to 350-400 mg/day (i.e., the Phe tolerance phenotype of the patient is altered from that of a classic PKU patient to a moderate PKU patient). Of course, it would be preferable that the therapeutic intervention taught herein would allow the patient to increase his/her intake of dietary Phe from 250-350 mg/day to 400-600 mg/day (i.e., the Phe tolerance phenotype of the patient is altered from that of a classic PKU patient to a mild PKU patient), or even more preferably, to allow the patient to have an intake of greater than 600 mg Phe/day (i.e., normal dietary intake).

Characteristics of BH4-Non Responsive PKU Patients and Methods of Treatment Thereof According to the Present Invention.

A second group of patients that can be treated with the methods of the present invention are those individuals that have been determined to have an elevated plasma Phe concentrations i.e., any concentration that is greater than 200 µM, but have been diagnosed to be non-responsive to BH4 therapy (as determined by the BH4 loading test described below). Such patients may include those individuals that have mild PKU (i.e., plasma Phe concentrations of up to 600 µM), individuals that have moderate PKU (i.e., plasma Phe concentrations of between 600 µM to about 1200 µM), as well as patients that have classic severe PKU (i.e., plasma Phe concentrations that are greater than 1200 µM).

The patients that are non-responsive to BH4 therapy are given PAL in combination with a reduced amount of protein in their diet in order to decrease the plasma Phe concentrations of the patient. The methods of the present invention are such that the administration of PAL produces a greater decrease in the plasma Phe concentrations of the patient as compared to the decrease that is produced with the same dietary protocol administered in the absence of PAL therapy. The dietary restrictions may be a diet that restricts the Phe intake by providing a synthetic medical protein formula that has a diminished amount of Phe or alternatively, the dietary restriction may be one which simply requires that the patient limit his/her overall protein intake but nevertheless allows the patient to eat normal foodstuffs in limited quantities.

The preferred therapeutic outcomes discussed for classical PKU patients are incorporated into the present section by reference. Preferred therapeutic outcomes for patients with moderate PKU (i.e., patients that has an unrestricted plasma Phe concentration of 600 µM/L to 1200M) include at least a 25% decrease in the plasma Phe concentrations of the patient. Preferably, the method will produce a 30% decrease in the plasma Phe concentration. Even more preferably, the method will produce a 40%, 50%, 60%, 70%, 80%, 90% or greater decrease in the plasma Phe concentration of the individual (for example, where a patient with moderate classical PKU has a Phe concentration of 1000 µM, a 90% decrease in the Phe concentration will produce a plasma Phe concentration of 100 µM, a concentration that is sufficiently low to require little or no dietary restriction).

In preferred embodiments, the plasma Phe concentrations of the moderate PKU patient being treated is reduced from any amount of unrestricted plasma Phe concentration that is between 600 µM to 1200 µM to any plasma Phe level that is less than 300 µM. A particularly preferred treatment with PAL (either alone or in combination with a dietary restriction) produces a decrease in plasma Phe concentration, e.g., to a level of between 200 µM to about 400 µM, which will be viewed as a clinically useful outcome of the therapy because patients that have a plasma Phe concentration in this range can manage the disease by simply restricting the amount of protein in the diet as opposed to eating a Phe-restricted formula. Indeed, in many studies, it is taught that such patients may even eat a normal diet.

Any increase in the amount of dietary Phe levels that can be tolerated by the patient as a result of the treatment will be considered to be a therapeutically effective outcome. For example, it is contemplated that as a result of administering the PAL therapy (either alone or in combination with other therapeutic intervention), the patient will be able to increase his/her intake of dietary Phe from 350-400 mg/day to 400-600 mg/day (i.e., the Phe tolerance phenotype of the patient is altered from that of a moderate PKU patient to a mild PKU patient). Of course, it would be preferable that the therapeutic intervention taught herein would allow the patient to increase his/her intake of dietary Phe from 350-400 mg/day to 400 to allow the patient to have an intake of greater than 600 mg Phe/day (i.e., normal dietary intake).

Even if the patient being treated is one who manifests only mild PKU, i.e., has a dietary allowance of 400-600 mg Phe intake/day) will benefit from the PAL-based therapies of the present invention because it is desirable to produce a normalized plasma Phe concentration that is as close to 360 µM± 15 µM as possible. For such patients, a preferred therapeutic outcome will include at least a 25% decrease in the plasma Phe concentrations of the patient. Preferably, the method will produce a 30% decrease in the plasma Phe concentration. Even more preferably, the method will produce a 40%, 50%, 60%, or greater decrease in the plasma Phe concentration of the individual (for example, where a patient with mild PKU has a Phe concentration of 600 µM, a 60% decrease in the Phe concentration will produce a plasma Phe concentration of 360 µM, i.e., an acceptable, normal concentration of plasma Phe).

In preferred embodiments, the plasma Phe concentrations of the mild PKU patient being treated is reduced from any amount of non-restricted plasma Phe concentration that is between 400 µM to 600 µM to any plasma Phe level that is less than 100 µM. Of course, even if the treatment with PAL (either alone or in combination with a dietary restriction) produces a lesser decrease in plasma Phe concentration, e.g., to a level of between 200 µM to about 400 µM, this will be viewed as a clinically useful outcome of the therapy.

Any increase the amount of dietary Phe levels that can be tolerated by the patient as a result of the treatment will be considered to be a therapeutically effective outcome. For example, it is contemplated that as a result of administering PAL therapy (either alone or in combination with other therapeutic intervention), the patient will be able to increase his/her intake of dietary Phe from 400-600 mg/day (i.e., the Phe tolerance phenotype of the patient is altered from that of a mild PKU patient to a mild HPA patient) to allow the patient to have an intake of greater than 600 mg Phe/day (i.e., normal dietary intake).

Furthermore, even if the patient is one who only manifests the symptoms of non PKU HPA, i.e., has an elevated plasma Phe concentration of up to 600 µM, but is otherwise allowed to eat a normal protein diet will benefit from PAL therapy of the invention because it has been shown that elevated Phe concentrations have significant effects on the IQ of such individuals. Moreover, as discussed below, PAL therapeutic intervention of subjects with special needs, e.g., pregnant women and infants, is particularly important even if that patient's plasma Phe levels are within the perceived "safe" level of less than 200 µM.

Maternal PKU and Methods of Treatment Thereof According to the Present Invention.

Metabolic control of plasma Phe levels in PKU women planning conception and those who are pregnant is important because of the serious consequences to the fetus exposed to even moderately elevated Phe levels in utero, regardless of the PAH status of the fetus. Therapeutic control of plasma Phe concentration is especially important in the first trimester of pregnancy, as failure to achieve adequate control will result in disorders including microcephaly, mental deficiency and congenital heart disease.

For example, the NIH Consensus Statement (vol 17 #3, October 2000) on Phenylketonuria reported that exposure of a fetus to maternal Phe levels of 3-10 mg/dL produced a 24% incidence of microcephaly, whilst those exposed to greater than 20 mg/dL (i.e., greater than 1200 µM) had a 73% incidence of microcephaly. Likewise congenital heart disease was found in over 10% of children exposed to maternal Phe levels that were greater than 20 mg/dL. Importantly, it has been noted that levels of Phe greater than 6 mg/dL significantly decrease the IQ of the child. Thus, it is imperative to ensure that the plasma Phe concentration of women with all forms of phenylketonuria, even those manifesting the mildest HPA, must be tightly controlled in order to avoid the risk of maternal PKU syndrome. However, the acceptable target levels for the plasma Phe concentrations of PKU women that have been used in U.S. clinics have ranged between 10 mg/dL and 15 mg/dL, which are much higher than the 2-6 mg/dL levels recommended for pregnant women or the 1-4 mg/dL that are used in British and German clinics to diminish the risks of developing maternal PKU syndrome.

Another important consideration for pregnant women is their overall protein intake. During pregnancy, it is important that women eat sufficient protein because it has been suggested that a low protein diet during pregnancy will result in retarded renal development and subsequent reduction in the number of nephrons and potentially leads to hypertension in adulthood. (D'Agostino, *N. Engl. J. Med.* 348(17): 1723-1724 (2003)). The following table provides exemplary guidelines for the recommended total dietary protein intake for various individuals.

TABLE 1

United States Guidelines for dietary protein requirements

|  | Age | Recommended Total Protein Intake (g) |
|---|---|---|
| Infant | 6 months or less | 13 |
|  | 6 months-1 year | 14 |
|  | 1-3 years | 16 |

TABLE 1-continued

United States Guidelines for dietary protein requirements

| | Age | Recommended Total Protein Intake (g) |
|---|---|---|
| Children | 4-6 years | 24 |
| | 7-10 years | 28 |
| Males | 11-14 years | 45 |
| | 15-18 years | 59 |
| | 19-24 | 58 |
| | 25-50 | 63 |
| | 51+ | 63 |
| Females | 11-14 years | 46 |
| | 15-18 years | 44 |
| | 19-24 | 46 |
| | 25-50 | 50 |
| | 51+ | 50 |
| Pregnant | | 60 |
| Lactating | | 65 |

As can be seen from the above exemplary guidelines, in the United States, the recommended protein intake for women of child-bearing age (e.g., less than 51) is from about 44 to 50 g/day, whereas pregnant women require are recommended an intake of about 60 g/day. In Canada and the United Kingdom, the recommended protein intake for pregnant women is in the order of about 70 g/day and 52 g/day. Thus, the need to ensure that the plasma Phe concentration levels of pregnant women are tightly controlled is further complicated by the fact that this group of PKU patient requires more protein than non-pregnant PKU females of comparable age.

In view of the above, it is contemplated that PAL therapies of the present invention will be particularly useful in pregnant women. It is contemplated that a woman suffering from any form of HPA who is pregnant or is contemplating pregnancy will be placed on a course of PAL therapy to ensure that her plasma Phe concentration levels are maintained as close to 180 μM to about 360 μM as possible. Such a course of therapy will preferably allow that woman to increase her level of normal protein intake.

The discussion of levels of plasma Phe concentrations and the degrees to which such Phe concentrations should be decreased discussed herein above in Sections 1A and 1B are incorporated into the present section for pregnant women.

Managing PKU in Infants and Methods of Treatment Thereof According to the Present Invention.

As discussed herein throughout, it has been determined that an elevation in the plasma Phe concentration in infants (ages zero to 3 years old) results in significant drop in IQ of the child. However, as has been discussed elsewhere in the specification, patients that have an elevated plasma Phe concentration of anywhere up to 400 μM do not normally receive any dietary intervention. Thus, infants at the age of zero to 3 years in age suffer from significant deleterious effects from the present therapies. The instant application contemplates treating any infant having an unrestricted plasma Phe concentration that is greater than 360 μM±15 μM with a therapeutic composition that comprises PAL in order to produce a beneficial decrease the plasma Phe concentration of that subject.

In preferred embodiments, the infant is aged between zero and 3 years of age and has an unrestricted plasma Phe concentration of about 1200 μM prior to the administration of PAL and said administration decreases the plasma Phe concentration. Preferably, the plasma Phe concentration is decreased to from greater than 1800 to about 1500 μM, about 1200 μM, about 1100 μM, about 1000 μM, about 900 μM, about 800 μM, about 700 μM, about 600 μM, about 550 μM, about 500 μM, about 450 μM, 400 μM, about 350 μM, about 300 μM, about 275 μM, about 250 μM upon administration. In other embodiments, the infant is aged between zero and 3 years of age and has an unrestricted plasma Phe concentration of greater than 1200 μM and preferably, this plasma Phe concentration is decreased to about 800 μM, or more preferably to about 500 μM or even more preferably to about 360 μM upon administration of PAL, either alone or in combination with diet. Those of skill in the art would understand that the invention contemplates treating infants with unrestricted plasma Phe concentrations of greater than 360 μM with PAL to produce decreases in such plasma Phe concentrations. The discussion of therapeutic reductions of plasma Phe concentrations above are incorporated herein by reference. Further, any decrease over 10% of the initial unrestricted plasma Phe concentration will be considered a therapeutic outcome for the therapeutic regimens for the infants. It should be understood that the PAL therapies may be combined with dietary restrictions to effect the therapeutic decrease in plasma Phe concentrations in such infants.

Table 2 lists a number of disease conditions wherein administration of therapeutically effective amounts of PAL would be beneficial. Parenteral, oral, or other standard routes of administration and dosage can be determined using standard methods.

TABLE 2

Exemplary disease conditions amenable to PAL protein therapy

Phenylketonuria
Hyperphenylalanemia
Tyrosinemia
Cancer

2. Compositions for Use in the Treatment

The present invention contemplates therapeutic intervention of PKU/HPA. Such intervention is based initially on the use of PAL, which may be used alone or in combination with dietary restrictions. Further PAL and/or dietary restrictions may further be combined with other therapeutic compositions that are designed, for example to combat other manifestations of PKU, such as for example, large neutral amino acids to prevent Phe accumulation in the brain (see Koch et al., Mol. Genet. Metabol. 79: 110-113 (2003)) or tyrosine supplementation. The present section provides a discussion of the compositions that may be used in the treatments contemplated herein.

PAL Compositions

In general, the present invention contemplates pharmaceutical compositions comprising effective amounts of protein or derivative products of the invention together with pharmaceutically acceptable diluents, stabilizers, preservatives, solubilizers, emulsifiers, adjuvants and/or carriers. Such compositions include diluents of various buffer content (e.g., Tris-HCl, phosphate), pH and ionic strength; additives such as detergents and solubilizing agents (e.g., Polysorbate 20, Polysorbate 80), anti-oxidants (e.g., ascorbic acid, sodium metabisulfite), preservatives (e.g., Thimerosol, benzyl alcohol) and bulking substances (e.g., lactose, mannitol); see, e.g., Remington's Pharmaceutical Sciences, $18^{th}$ Ed. (1990, Mack Publishing Co., Easton, Pa. 18042) pages 1435-1712. An effective amount of active ingredient is a therapeutically, prophylactically, or diagnostically effective amount, which can be readily determined by a person skilled in the art by taking into consideration such factors as body weight, age, and therapeutic goal.

The PEG:PAL compositions of the present invention may also include a buffering agent to maintain the pH of the solution within a desired range. Preferred agents include sodium acetate, sodium phosphate, and sodium citrate. Mixtures of these buffering agents may also be used. The amount of buffering agent useful in the composition depends largely on the particular buffer used and the pH of the solution. For example, acetate is a more efficient buffer at pH 5 than pH 6 so less acetate may be used in a solution at pH 5 than at pH 6. The preferred pH range for the compositions of the present invention is pH 3.0-7.5.

The compositions of the present invention may further include an isotonicity adjusting agent to render the solution isotonic and more compatible for injection. The most preferred agent is sodium chloride within a concentration range of 0-150 mM.

As used herein, and when contemplating PEG:PAL conjugates, the term "therapeutically effective amount" refers to an amount, which gives a decrease in serum L-phenylalanine that provides benefit to a patient. The amount will vary from one individual to another and will depend upon a number of factors, including the overall physical condition of the patient. The amount of PAL used for therapy gives an acceptable rate of serum L-phenylalanine decrease and maintains this value at a beneficial level (usually at least about 30% and typically in a range of 10% to 50%). A therapeutically effective amount of the present compositions can be readily ascertained by one skilled in the art using publicly available materials and procedures.

The invention provides for administering PEG:PAL conjugates less frequently than native PAL. The dosing frequency will vary depending upon the condition being treated, but in general will be about one time per week. It is understood that the dosing frequencies actually used may vary somewhat from the frequencies disclosed herein due to variations in responses by different individuals to the PEG:PAL conjugates; the term "about" is intended to reflect such variations.

The present invention may thus be used to reduce serum L-phenylalanine levels. Most commonly, serum L-phenylalanine levels are increased due to hyperphenylalaninemia. Among the conditions treatable by the present invention include hyperphenylalaninemia associated with phenylketonuria. Also treatable are conditions that may lead to increased serum L-tyrosine levels such as found in tyrosinemia. In addition, numerous cancer-related conditions, where depletion of serum L-phenylalanine and/or serum L-tyrosine levels would be beneficial, may also be treated with the PEG:PAL conjugates of the invention.

PEG:PAL conjugates prepared in accordance with the present invention are preferably administered by injection intraperitoneally, subcutaneously, or intramuscularly. However, it would be clear to one skilled in the art that other routes of delivery could also be effectively utilized using the compositions of the present invention.

The methods described herein use pharmaceutical compositions comprising the molecules described above, together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, cyclodextrins, modified cyclodextrins (i.e., sulfobutyl ether cyclodextrins) etc. Suitable excipients for non-liquid formulations are also known to those of skill in the art.

Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences,* 18th Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is intravenous using a convenient daily dosage regimen, which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, a softgel capsule or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a non-toxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. In addition, parenteral administration may involve the use of a slow release or sustained release system such that a constant level of dosage is maintained.

The PEG:PAL compounds identified described above can be administered to a patient at therapeutically effective doses to treat or ameliorate cardiovascular disease. The toxicity and therapeutic efficacy of such compounds can be determined by standard pharmaceutical procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are normally preferred.

The data obtained from the cell culture assays and animal studies can be used in formulating a range of dosage for use in humans. The dosage preferably lies within a range of circulating concentrations that include the $ED_{50}$ with little or minimal toxicity. The dosage can vary within this range depending upon the dosage form employed and the route of administration utilized. The therapeutically effective dose can be determined from cell culture assays, and from animal models.

Dietary Protein

In addition to administering PAL and related analogs to HPA/PKU patients, it is contemplated that the dietary protein of the patients also may be restricted or modified. Those of skill in the art are aware of various commercially available protein formulas for use in the treatment of PKU. Such formulas include MAXIMAID, PHENEX 1, PHENEX 2 (Ross Laboratories, Liverpool, UK), LOFENALAC, PHENYL-FREE (Mead-Johnson), and the like.

Those of skill in the art may use the referenced protein formulas, which are generally free of Phe concentrations. The protein formulas often are supplemented with amino acids that are deficient in PKU patients. Such amino acids include, for example, L-tyrosine, and L-glutamine. It has been suggested that it may be desirable to supplement the diet of PKU patients with valine, isoleucine and leucine (see U.S. Pat. No. 4,252,822). In certain clinical manifestations, the toxic effects of PKU are caused by Phe blocking the brain uptake of other amino acids such as tyrosine and tryptophan. It has been found that supplementing the diet of a PKU patient with excess of such large neutral amino acids blocks Phe uptake into the brain and lowers brain Phe levels. Thus, it is contemplated that for the methods of the present invention, the dietary regimen may further be supplemented with compositions that comprise one or more of these amino acids (Koch et al., Mol. Genet. Metabol. 79: 110-113 (2003)).

Further, as it is known that L-carnitine and taurine, which are normally found in human milk and other foodstuffs of animal origin, also should be supplied in addition to the protein restriction. In certain embodiments, the L-carnitine may be supplied as 20 mg/100 g of protein supplement, and the taurine may be supplied as 40 mg/100 g protein supplement in order to help supply amounts of these factors normally found in human milk and foods of animal origin.

In addition, those of skill in the art are referred to the 2000 National Academy of Sciences-National Research Council Dietary Reference Intakes for a further listing of other components, such as essential vitamins and minerals that should be supplied to the patient to ensure that other supplements are being provided despite the dietary protein restriction.

Referring to the discussion above regarding total protein amounts and desirable plasma Phe concentrations, one of skill in the art will be able to determine the amount of dietary protein restriction that is required and thus adjust the diet of the patient accordingly. Taking for example, a male of about 11-14 years of age, that individual should preferably receive 45 g protein/day. In the event that the individual is one that has severe classic PKU, his unrestricted plasma Phe concentration will likely be greater than 1200 μM, and most, if not all of the dietary protein source for that individual is likely to be from a powdered protein supplement, which preferably lowers his plasma Phe concentrations to less than 600 μM. By administering PAL to that subject, a therapeutic outcome would be one which produces greater decrease in the plasma Phe concentrations of patient or alternatively, the therapeutic outcome is one in which the individual's plasma Phe concentrations is lowered to a similar degree, but that individual is able to tolerate protein from a normal diet rather than from a dietary formula.

Similarly, a male of about 11-14 years of age, is one who has moderate PKU, it may be possible using the methods of the present invention to give him the allotted 45 g protein/day through a normal protein intake rather than a restricted formula. Determining whether the methods of the invention are effective will entail determining the plasma Phe concentrations of the patient on a regular basis to ensure that the plasma Phe concentrations remain below at least 400 μM. Tests for determining such concentrations are described below. Preferably, concentrations of less than or about 360 μM are achieved.

3. Identifying and Monitoring Patient Populations

As discussed herein throughout, it will be necessary in various embodiments of the present invention to determine whether a given patient is responsive to PAL therapy, and to determine the phenylalanine concentrations of the patient both initially to identify the class of PKU patient being treated and during an ongoing therapeutic regimen to monitor the efficacy of the regimen. Exemplary such methods are described herein below.

BH4 Loading Test

The BH4 loading test allows discrimination between patients that have HPA due to a deficit in BH4 or through a deficiency in PAH.

The simplest BH4 loading test is one in which exogenous BH4 is administered and the effects of the administration on lowering of plasma Phe concentrations is determined. Intravenous loading of 2 mg/kg BH4 was initially proposed by Danks et al., (Lancet 1:1236, 1976), as BH4 of greater purity has become available it has become possible to perform the test using an oral administration of BH4 in amounts of about 2.5 mg/kg body weight. Ultimately, a standardized approach was proposed by Niederwieser et al. in which a 7.5 mg/kg single oral dose of BH4 is administered (Eur. J. Pediatr. 138: 441 (1982)), although some laboratories do still use upwards of 20 mg BH4/kg body weight.

In order for the simple BH4 loading test to produce reliable results, the blood Phe levels of the patient need to be higher than 400 μM. Therefore, it is often customary for the patient to be removed from the PKU diet for 2 days prior to performing the loading test. A BH4 test kit is available and distributed by Dr. Schircks Laboratories (Jona, Switzerland). This kit recommends a dosage of 20 mg BH4/kg body weight about 30 minutes after intake of a normal meal.

Determination of Phe Concentrations

There are numerous methods for determining the presence of Phe in blood (Shaw et al., Analytical Methods in Phenylketonuria-Clinical Biochemistry, In Bickett et al. Eds. Phenylketonuria and Some Other Inborn Errors of Amino Acid Metabolism, Stuttgart, Georg Thiem Verlag, 47-56 (1971)). Typically, phenylalanine and tyrosine concentrations are determined from the serum of a patient using a fluorometric assay. This assay relies on the formation of fluorescent substance when phenylalanine is heated with ninhydrin in the presence of leucylalanine (McCaman et al., J. Lab. Clin. Med. 59: 885-890 (1962)).

The most popular method for determining Phe concentrations is the Guthrie test in which discs are punctured from filter paper that has been saturated with a blood sample from the patient. The uniform discs are incubated in a tray of agar that has been seeded with *Bacillus subtilis* and contains a specific inhibitor of *Bacillus subtilis* growth. As the phenylalanine transfers from the uniform discs onto the agar, the Phe reverse the inhibition of growth thereby yielding an area of growth that can be correlated to phenylalanine concentration by comparison to similar assays performed using discs containing known amounts of Phe.

Other methods of quantifying Phe concentration include HPLC, mass spectrometry, thin layer chromatography and the like. Such methods can be used to determine the plasma Phe concentration of a patient before the therapy and to monitor the Phe concentration during the therapeutic regimen to determine the efficacy thereof.

It is contemplated that the plasma Phe levels of the patients will be monitored at convenient intervals (e.g., daily, every other day or weekly) throughout the time course of the therapeutic regimen. By monitoring the plasma Phe levels with such regularity, the clinician will be able to assess the efficacy of the treatment and adjust the PAL and/or dietary protein requirements accordingly.

Combination Therapy

Certain methods of the invention involve the combined use of PAL and dietary protein restriction to effect a therapeutic outcome in patients with various forms of HPA. To achieve the appropriate therapeutic outcome in the combination therapies contemplated herein, one would generally administer to the subject the PAL composition and the dietary restriction in a combined amount effective to produce the desired therapeutic outcome (i.e., a lowering of plasma Phe concentration and/or the ability to tolerate greater amounts of Phe/protein intake without producing a concomitant increase in plasma Phe concentrations). This process may involve administering the PAL composition and the dietary protein therapeutic composition at the same time. This may be achieved by administering a single composition or pharmacological protein formulation that includes all of the dietary protein requirements and also includes the PAL within said protein formulation. Alternatively, the dietary protein (supplement or normal protein meal) is taken at about the same time as a pharmacological formulation (tablet, injection or drink) of PAL. PAL also may be formulated into a protein bar or other foodstuff such as brownies, pancakes, cake, suitable for ingestion.

In other alternatives, PAL treatment may precede or follow the dietary protein therapy by intervals ranging from minutes to hours. In embodiments where the protein and the PAL compositions are administered separately, one would generally ensure that a significant period of time did not expire between the time of each delivery, such that PAL will still be able to exert an advantageously effect on the patient. In such instances, it is contemplated that one would administer the PAL within about 2-6 hours (before or after) of the dietary protein intake, with a delay time of only about 1 hour being most preferred. In certain embodiments, it is contemplated that PAL therapy will be a continuous therapy where a daily dose of PAL is administered to the patient indefinitely. In other situations, e.g., in pregnant women having only the milder forms of PKU and HPA, it may be that PAL therapy is only continued for as long as the woman is pregnant and/or breast feeding.

Further, in addition to therapies based solely on the delivery of PAL and dietary protein regulation, the methods of the present invention also contemplate combination therapy with a third composition that specifically targets one or more of the symptoms of HPA. For example, it is known that the deficit in tyrosine caused by HPA results in a deficiency in neurotransmitters dopamine and serotonin. Thus, in the context of the present invention, it is contemplated that PAL and dietary protein based methods could be further combined with administration of L-dopa, carbidopa and 5-hydroxytryptophan neurotransmitters to correct the defects that result from decreased amounts of tyrosine in the diet.

As the administration of phenylase would not generate tyrosine (unlike administration of PAH), such treatment will still result in tyrosine being an essential amino acid for such patients. Therefore dietary supplementation with tyrosine may be desirable for patients receiving phenylase in combination with the BH4 therapy.

I. Production of PAL

Another aspect of the invention is a method of producing PAL. In a preferred embodiment, recombinant PAL is overexpressed as an N-terminal octahistidyl-tagged fusion protein in a vector preferably *E coli* BL21(DE3)/pLysS (Invitrogen) with an inducible promoter such as with IPTG (isopropyl-beta-D-thiogalactopyranoside). Seed culture for a bioreactor/fermenter can be grown from a glycerol stock in shake flasks. Such seed culture can then be used to spike into a controlled bioreactor in fed-batch mode. Glucose can be supplemented and pH is controlled with base ($NH_4OH$) and agitation is up to 1200 rpm. $O_2$ feed keeps dissolved oxygen to greater than 20%. The cells can be grown at a temperature of 30° C. until reaching and $OD_{600}$ of 70-100 (~22-25 hrs) and then induced with 0.4 mM IPTG. The temperature can be reduced to 22 to 26° C. and grown until activity change is <0.1 IU/ml (approximately 40-48 hrs and an $OD_{600}$ typically of 200). Cell culture media is typically defined and composed of yeast extract protein, peptone-tryptone, glucose, glycerol, casamino acids, trace salts and phosphate buffering salts. The recombinant PAL product is produced intra-cellularly and not secreted. The bacteria can be harvested by continuous centrifugation (Alfa-Laval, Carr, Ceba, or equivalent).

J. Purification of PAL

A further aspect of the present invention features a method to purify PAL or a biologically active fragment, mutant or analog thereof. According to a first embodiment, a transformed cell mass can be grown and ruptured leaving crude recombinant enzyme. Exogenous materials can optionally be separated from the crude bulk to prevent fouling of the columns. Chromatographic purification can be conducted using one or several chromatographic resins. Subsequently, the purified protein can be formulated into a buffer designed to provide stable activity over an extended period of time. In another preferred embodiment, the method to purify the PAL comprises: (a) Lysis of the bacteria containing recombinant PAL using a pressure homogenizer (but potentially by other physical means such as glass bead lysis); (b) Heat treatment (c) Clarification of this lysate using a second continuous centrifugation step and/or depth filtration (as with Cuono Zeta Plus or Maximizer, Pall Filtron, or Millipore Millistak or Opticao filters) (d) passage through a charcoal filtration step (as with Millipore Millistak 40AC); (e) passage through a final filtration step (as with a Sartorious Sartopore 0.2 µm filter); (f) Passage over a butyl hydrophobic interaction chromatography (as in Toyopearl Butyl 650M from Tosoh Biosciences); (g) passage over a Q ion exchange column (as in a Macroprep High Q from BioRad); (h) recovery of final product by buffer exchange with tangential flow filtration (as with a Sartorious Hydrosart or PES 100 kDa membrane). Those skilled in the art readily appreciate that one or more of the chromatography steps may be omitted or substituted, or that the order of the chromatography steps may be changed within the scope of the present invention. Finally, appropriate sterilizing steps may be performed as desired.

EXAMPLES

Having now generally described the invention, the same may be more readily understood through the following reference to the following examples. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Crystal Structure of PAL

PAL Protein Expression and Purification

Both a full-length *R. toruloides* PAL DNA clone (pIBX-PAL (Sarkissian, et al., 1999 ibid.), wt-PAL amino acid sequence (shown in FIG. 5) and a recloned construct in the His-tag-containing pET-28a(+) expression vector (Novagen) between NdeI and NotI restriction sites (pET-PAL) have been used. With the pET vector construct, the PAL protein was expressed with a thrombin-cleavable His tag on the N-terminus. The wild-type pET-PAL construct produces 3.5 mg/L levels of active PAL (versus 1 mg/L for the pIBX-PAL PAL construct) and provides for one-step immobilized metal affinity chromatography purification of PAL. Both forms of the PAL protein was used for crystallization trials.

His-tagged PAL was expressed in BL21(DE3) *E. coli* cells (Novagen) grown in LB medium with 30 µg/ml kanamycin at 37° C. with induction using 1 mM IPTG at an $OD_{600}$ of 0.8. The temperature was reduced to 23° C. and expression proceeds for 3 hours. Cells were spun down and frozen at −80° C. Cell pellets were resuspended in 100 mM Tris, 90 mM NaCl pH 7.8 with inclusion of an EDTA-free protease inhibitor tablet (Roche Diagnostics GmbH). Solutions were then sonicated for 3 minutes, followed by a centrifugation step at 45,000 rpm for 25 minutes. Lysates were then filtered through a 0.22 µm membrane. Clarified lysate was loaded onto a 7 mL POROS MC 20 column charged with $Ni^{+2}$. Equilibration/wash buffer contained 25 mM Tris, 100 mM NaCl, 20 mM imidazole, pH 7.8. Elution buffer was the same equilibration/wash buffer but with 500 mM imidazole added. A linear gradient from 0 to 500 mM imidazole was run over the column (20 column volume gradient) and the His-PAL protein begins to elute at approx. 70 mM imidazole. Fractions containing PAL were pooled and ammonium sulfate was added to a concentration of 0.6 M, with stirring at 4° C. for 30 minutes until dissolved, followed by a centrifugation step at 45,000 rpm for 30 minutes and filtering through a 0.22 µm membrane. The protein solution was then run over a 7 mL POROS HP column equilibrated with 25 mM Tris, 0.6 M ammonium sulfate, pH 7.8. PAL does not bind to the column and was collected in the flow through. The PAL fraction was collected and concentrated to 7.5 mg/ml using an Orbital Biosciences Apollo 20-30 kDa molecular weight cut off spin concentrator, with a buffer exchange step to 25 mM Tris, pH 7.8, 90 mM NaCl. Crystallization follows the selenomethionine PAL procedure outlined below. Enzyme purity was determined by SDS-PAGE and enzyme activity was determined using $OD_{290}$ measurements. Purified PAL samples were tested for in vitro stability and activity.

Alternatively, selenomethionine-expressed PAL was used, since direct MAD (Hendrickson, et al., EMBO J, 9(5), pp. 1665-1672 (1990)) and/or SAD (Brodersen, et al., Acta Crystallogr. D Biol Crystallogr., 56(Pt 4), pp. 431-441 (2000)) crystallographic solutions are possible. For selenomethionine expression, the pIBX-PAL construct was transformed into the *E coli* methionine-auxotroph B834(DE3) (Novagen), and the cells were grown at 37° C. in minimal medium containing 30 µg/ml kanamycin and 0.76 mM selenomethionine. Cultures were induced at 24° C. for 3 hours by adding 1 mM IPTG when the $OD_{600}$ reaches 0.6-0.8. Cells were harvested by centrifugation and the cell pellets were frozen at −80° C.

Purification for protein crystallization trials was carried out at 4° C. under helium. Cells from a 9 L culture were lysed in 100 mM Tris, pH 7.8, 10 mM NaCl, 1 mM $MgCl_2$, 0.01% β-mercaptoethanol, EDTA-free protease inhibitor cocktail (Roche Diagnostics GmbH) under vacuum. Solutions were then sonicated for 3 minutes, followed by a centrifugation step at 45,000 rpm for 30 minutes. Lysates were then filtered through a 0.22 µm membrane. The protein solution was then run over a 7 mL POROS HQ column equilibrated with 25 mM Tris, 0.01% β-mercaptoethanol, pH 7.8. PAL was eluted using 25 mM Tris, 1 M NaCl, 0.01% β-mercaptoethanol, pH 7.8 with a linear gradient. The PAL fraction was identified using the activity assay on the elution fractions, and the active samples were collected and ammonium sulfate is added to a concentration of 1.7 M, with stirring at 4° C. for 30 minutes under vacuum, followed by a centrifugation step at 45,000 rpm for 30 minutes and filtering through a 0.22 µm membrane. The protein solution was then run over a 7 mL POROS HP column equilibrated with 25 mM Tris, 1.7 M ammonium sulfate, pH 7.8. Elution used 25 mM Tris, pH 7.8 buffer, with a 20 column volume gradient. The fraction that was active was collected, which is at around 0.8 M ammonium sulfate. The active PAL fraction was then concentrated along with a buffer exchange step to 25 mM Tris, pH 7.8. A DEAE column was then run, using 25 mM Tris, pH 7.8 running buffer and 25 mM Tris, 500 mM NaCl elution buffer using a 20 column volume gradient; the active fraction was collected (the first peak), concentrated, and buffer was exchanged to run a final HQ column (25 mM Tris, pH 7.8 load buffer, 25 mM Tris, 500 mM NaCl, pH 7.8 elution buffer using a 20 column volume gradient) with fractions containing active PAL collected.

Active PAL was then concentrated using an Orbital Biosciences Apollo 20-30 kDa molecular weight cut off spin concentrator to 7.5 mg/ml, with buffer exchange to 25 mM Tris pH 7.8, 90 mM NaCl.

Protein Structure Determination of PAL

Active PAL expressed without the His-tag (pIBX-PAL) was produced at 1 mg/L culture yield. Selenomethionine-expressed PAL at a concentration of 5-10 mg/mL, preferably 7.5 mg/mL, in 25 mM Tris pH 7.8, 90 mM NaCl was used in sitting drop crystallization trials at 4° C. Wild type crystals of PAL diffract to 1.6 Å and were obtained using 11-16% MPEG 5K, 80-100 mM MES, pH 6.5. Flash freezing uses a 15% MPD cryoprotectant soak.

For initial evaluation of crystals and cryopreservation strategies, data was collected on an in-house rotating anode FR-D (Rigaku) with R-axis 4 detector and cryo-freezing equipment. Crystals found to exhibit a combination of low mosaicity, reasonable lifetimes, and good diffraction will be transported to a synchrotron radiation source for final data collection. The native PAL processed data was solved by SAD using SHELXD (Sheldrick, et al., Meth Enzymol, 277, pp. 319-343 (1997)) to locate the positions of 52 of the 60 the selenium atoms. The phase was calculated using SHELX and was improved with solvent flattening using DM (Cowtan, Joint CCP4 and ESF-EACBM Newsletter on Protein Crystallography, 31, pp. 34-38 (1994)). The main chain was traced by ARP/wARP (Perrakis, et al., Acta Crystallogr. D Biol. Crystallogr., 57(Pt 10), pp. 1445-1450 (2001)) and the side chains traced using guiSIDE. Model building was carried out with the program O (Jones, et al., Acta Crystallogr., A47, pp. 110-119 (1991)). Refinement used the program REFMAC (Murshudov, et al., Acta Cryst., D53, pp. 240-255 (1997)).

The output of crystal structure coordinates, shown in Appendix A, includes residues (e.g. 103-123 and 350-353) that contain high B-values and are very dynamic.

Structural Features of PAL

Using X-ray crystallography, the structure of *Rhodosporidium toruloides* PAL has been determined (FIG. 1). The full-length wild-type PAL was crystallized in space group P212121 (a=104.759, b=151.612, c=179.922) with four molecules per asymmetric unit. The crystal structure reveals a tetrameric enzyme (Mr=307,518) (FIG. 1), which is consistent with previous biochemical studies that indicated the enzyme is a tetramer in solution (Havir, et al., Biochemistry, 14(8), 1620-1626 (1975)). There are four 2-fold axes within the unit cell. In the PAL tetramer, side-chains and portions of backbone residues for 50 residues (positions 1-25, 103-123 and 350-353) have weak density and are present in surface loops in all four monomers and are not visible in the structure. These regions of the structure are probably disordered and are located within surface-exposed flexible loops. The chain fold topology of the PAL tetramer consists mainly of alpha-helices, a structure which is similar to *P. putida* histidine ammonia-lyase (HAL, Schwede, et al., (1999) ibid.) and some other tetrameric enzymes, such as aspartate ammonia-lyase (Shi, et al., Biochemistry, 36(30), pp. 9136-9144 (1997)), fumarase (Weaver, et al., Nat. Struct. Biol., 2(8), pp. 654-662 (1995)), and argininosuccinate lase (Turner, et al., Proc Natl Acad Sci USA., 94(17), pp. 9063-9068 (1997)).

Each monomer of PAL consists mainly of alpha-helices and is subdividable into four domains—a central catalytic domain, N-terminal domain, and small C-terminal domain with similarity to the histidine ammonia-lyase structure (Schwede, et al., (1999) ibid.) plus an additional domain inserted in the C-terminal region that protrudes from the ends of the intact tetramer molecule, forming an elongated structure with approximate dimensions of 111 Å ×47 Å ×44 Å (FIG. 1). Domains 1, 2, and 4 together overlap with the core of the HAL structure with an r.m.s.d. of 0.892 Å.

Figure 2:
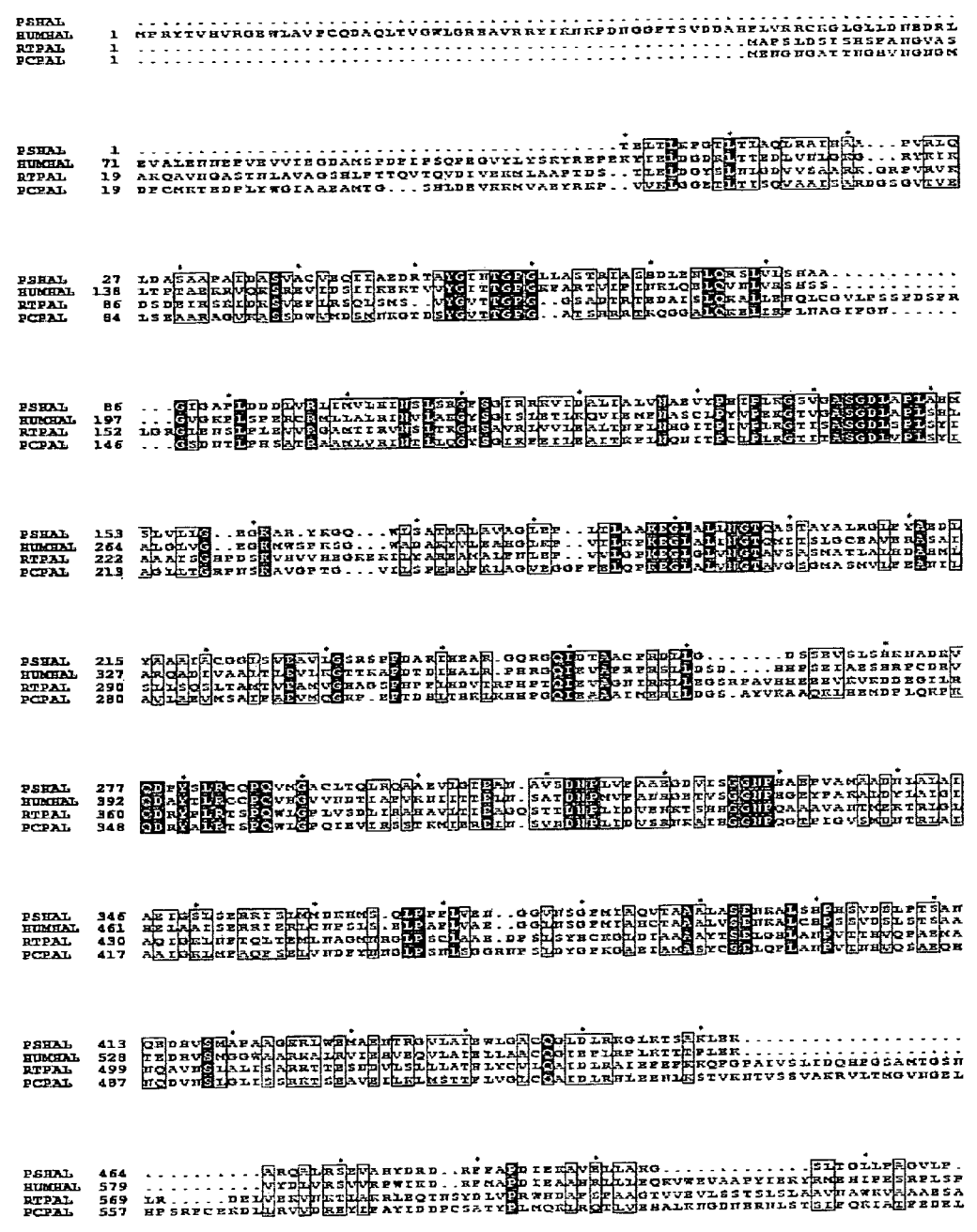

Domain 1 (D1) includes residues 1-273, which consists of 11 α-helices of various lengths and 7 short β-strands. D1 overlaps well with the N-terminal region of HAL and is the most conserved sequence with HAL (FIG. 2). The MIO prosthetic catalytic active center (residues 211-213) of PAL is located in this domain. The flexible surface loop located in the region of residues 102-124 that may be involved in substrate binding is also located in this domain. Residues 1-25, 103-123, and 350-353 are located in surface regions of the structure and have high B-values. Our biochemical, site-directed mutagenesis and truncation experiments show that this domain is important for activity. The truncation mutant 10-716 did not exhibit activity, indicating that the very end of the N-terminus is necessary for PAL function.

Domain 2 (D2) is the central domain of both the monomer and tetramer of PAL, contains residues 274-540 and is comprised of almost all α-helical segments. The core of D2 is made up of six nearly parallel α-helices, whose length range varies from 15-38 residues. In the PAL tetramer, the six-helix bundles assemble to form a central core of 24 nearly parallel α-helices. The six α-helical bundles of D2 are connected to each other by loops that range from 10-30 residues in length, which may make this region of the structure very flexible.

Domain 3 (D3) is the major structurally distinct domain between PAL and HAL and is an extra domain in the PAL structure relative to HAL. D3 includes residues 541-655 and consists of a four α-helix bundle. The four α-helices are nearly parallel to each other with only about a 30 degree deviation from co-planarity. One of the α-helices in D3 (residues 541-549) and one α-helix in D2 (residues 505-540) together form a 44 residue long α-helix. D3 has no similar structural architectures when doing a rigid search using DALI (947 Holm, et al., J. Mol. Biol., 233, pp. 123-138 (1993)), however, D3 can be aligned well (with an r.m.s.d. of 1.99 Å) with the end of the C-terminal region of HAL (residues 453-509) with one twist when doing flexible alignment using the program FATCAT (944 Ye, Y., Bioinformatics, 19(Suppl 2), pp. ii246-ii255 (2003)). D3 is not located in the central interface among the four PAL monomers, but instead is sticking out from the main region of the tetramer with a head-to-head packing arrangement with its D3 tetramer-related counterpart (monomers A-D or monomers B-C).

Domain 4 (D4) is the smallest domain in PAL (residues 656-716), containing a three α-helix bundle and a 20 residue long loop. D4 has a similar arrangement with the end of the C-terminal structure of HAL (residues 453-509). Domain D4 in PAL is located at the periphery of the bundle of 24 α-helices, but is still situated in the main region of the tetramer. Our truncation experiments showed that D4 is important for activity.

The following table summarizes the X-ray crystallography data set of PAL that was used to determine the structure of PAL according to this invention (Table 3).

TABLE 3

Crystallographic data collection and refinement statistics

Data collection

| | |
|---|---|
| Wavelength (Å) | 0.9794 |
| Resolution range (Å) | 50.0-1.47 |
| No. of observations | 2,866,525 |
| No. of unique observations | 844,536 |
| Completeness (%) | 89.2 |

TABLE 3-continued

Crystallographic data collection and refinement statistics

| | |
|---|---|
| $R_{unmerge}$ (%) | 11 |
| I/σ(I) | 4.9 |
| Space group | P212121 |
| Cell dimensions (a, b, c, α, β, γ) | 104.759, 151.612, 179.922, 90, 90, 90 |
| Refinement | |
| Resolution range (Å) | 41.88-1.6 |
| Reflections (test set) | 353.019 (18674) |
| $R_{work}$ (%) | 16.24 |
| $R_{free}$ (%) | 18.86 |
| r.m.s. deviations | |
| Bond length (Å) | 0.017 |
| Bond angles (°) | 1.584 |
| Average B of overall | 15.022 |
| Completeness (%) | 99.1 |

Example 2

Structure of Human Histidine Ammonia-Lyase (HAL)

Figure 6:
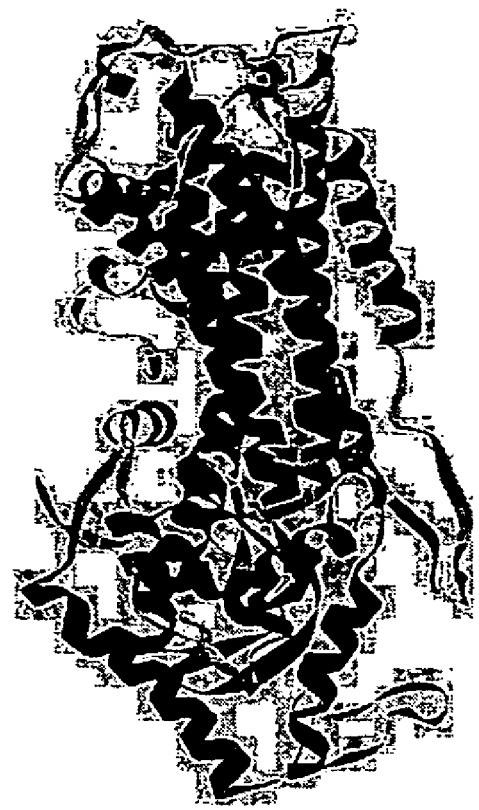
FIG. 6 is a modeled structure of the human HAL monomer.

The three-dimensional structure of residues 114-607 of human HAL (FIG. 6) was modeleled using the JIGSAW server available over the internet (www.w3.org/Jigsaw/) based upon the 3-D structure of *P. putida* HAL (427 Schwede, et al., (1999) ibid.). Human HAL has 657 amino acids in total with a core that is homologous to *P. putida* HAL, but N- and C-termini display differences.

Example 3

Confirmation of the Active Site of PAL

The active site of PAL was identified based on the combined information from the comparison to the HAL structure, sequence alignments, mechanistic studies and site-directed mutagenesis. PAL has the same active site MIO prosthetic group as HAL that is formed by residues Ala211, Ser212, and Gly213. We define residues in the *R. toruloides* PAL active site that are within 5 Å of the MIO. The PAL active site consists of residues from three different monomers in a PAL tetramer, including residues from monomer A (A138, A208-A218, A266, A270-A272, A274-A275, A395-A396, A411-A415, A496, A499-A500, and A502-A505), residues from monomer B (B360, B363, B366-B367, and B370-B371), and residues from monomer C(C472). All residues in the *R. toruloides* PAL active site are from domains D1 and D2. The flexible loop region A106-A124 acts as a cover to the entrance of the active site. Most residues that have been proposed and characterized structurally and biochemically in the HAL active site are found in the PAL active site: Ala211 vs. Ala142, Ser212 vs. Ser143, Gly213 vs. Gly144, Asp214 vs. Asp145, Tyr363 vs. Tyr280, Phe413 vs. Phe329, Arg366 vs. Arg283, Asn270 vs. Asn195, Gly271 vs. Gly196, Leu214 vs. Leu146, Phe116 vs. Phe59, 360 vs. Gln277, the only two different residues between PAL and HAL active site are Gln499 vs. Glu414 and Gln138 vs. His83.

Consistent with the assignment of the active site region, numerous mutations made in these regions are not tolerated (R102K, Q104K, S108K, Y110H, Y110A, Y110L, T114K, R123H, R123A, R123Q, T124P, T124K, and Q131K), however, other mutations of the residues present in active site regions produce similar activity, if not improved activity, variants of PAL (R91K, H137K, R91K+H137K). Pegylation or other chemical derivatization of such variants would lead to PAL conjugates with improved qualities, such as improved immunoprotection and/or improved proteolytic resistance.

Surrounding the PAL active site are five flexible loops: loop 197-218, loop 101-124, loop 392-415 and loop 486-505 from monomer A, as well as loop 360-363 from monomer B. Mutagenesis studies have shown that a number of mutants of Y110 abolish activity, indicating that residue Tyr110 in this loop is important for PAL activity. Our proteolysis study combined with protein sequencing of the cleavage products showed that the most accessible cleavage sites in PAL for trypsin and chymotrypsin are Tyr110 and Arg123 respectively, both are in the 101-124 loop, thus provides further evidence for the flexibility and importance of this loop. Similar to PAL from other species, *R. toruloides* PAL can be protected from protease inactivation by incubating it with a competitive inhibitor such as tyrosine. Mutants of PAL designed to 'lock down' this flexible portion of the active site can lead to variants with less protease susceptibility, especially in light of the observation that flexible loop regions are common sites of protease cleavage (U.S. Pat. No. 6,261,550). In addition, mutation of sites in the proximity of Tyr110 and Arg123 (e.g. Asp95, Lys96, Glu99, Arg102, Thr124, Glu125, Asp126, Glu403, Asn404, Lys405, Val259, Pro262, Val186, Arg359, Val349, Lys350, Val351, Lys352, Gly685, Lys686) to Lys, Cys, or other residues capable of being chemically derivatized can also generate PAL variants with protease resistance.

Example 4

Confirmation of Surface Residues of PAL

The program GETAREA 1.1, available on the internet (www.scsb.utmb.edu/getarea/area_form.html), was used to determine solvent accessible residues (In/Out ratio designation "o"), residues inside the structure (In/Out ratio designation "i"), and residues partially surface-exposed (In/Out ratio designation missing) based on the PAL crystal structure atomic coordinates (Table 4). With information of this type, residues can be selected for mutation based on their surface accessibility.

TABLE 4

GETAREA 1.1 output for residues in monomer A of the R. toruloides PAL tetramer (Probe radius of 1.400 used for calculation). (residues 26-102, 124-349,and 354-715 of SEQ ID NO: 1). Similar values are obtained for the B, C, and D monomers of PAL.

| Residue | | Total | Apolar | Backbone | Sidechain | Ratio (%) | In/Out |
|---|---|---|---|---|---|---|---|
| ALA | 26 | 71.07 | 31.60 | 43.72 | 27.34 | 42.1 | |
| SER | 27 | 52.92 | 36.54 | 24.22 | 28.70 | 37.1 | |
| THR | 28 | 131.29 | 87.63 | 21.51 | 109.78 | 100.0 | o |
| ASN | 29 | 86.67 | 34.32 | 11.82 | 74.85 | 65.5 | o |
| LEU | 30 | 50.91 | 49.38 | 1.53 | 49.38 | 33.8 | |
| ALA | 31 | 17.92 | 17.33 | 0.59 | 17.33 | 26.7 | |
| VAL | 32 | 8.16 | 7.47 | 1.87 | 6.29 | 5.1 | i |
| ALA | 33 | 25.47 | 24.49 | 1.01 | 24.46 | 37.7 | |
| GLY | 34 | 1.76 | 0.00 | 1.76 | 0.00 | 2.0 | i |
| SER | 35 | 14.18 | 4.12 | 5.17 | 9.01 | 11.6 | i |
| HIS | 36 | 29.02 | 26.01 | 2.93 | 26.09 | 16.9 | i |
| LEU | 37 | 31.13 | 30.97 | 0.17 | 30.97 | 21.2 | |
| PRO | 38 | 24.29 | 10.80 | 16.08 | 8.21 | 7.8 | i |
| THR | 39 | 36.58 | 28.64 | 9.42 | 27.17 | 25.6 | |
| THR | 40 | 93.02 | 47.34 | 23.53 | 69.50 | 65.4 | o |
| GLN | 41 | 140.60 | 45.99 | 32.08 | 108.52 | 75.5 | o |
| VAL | 42 | 3.91 | 2.51 | 2.04 | 1.86 | 1.5 | i |
| THR | 43 | 36.82 | 34.94 | 0.00 | 36.82 | 34.7 | |

TABLE 4-continued

GETAREA 1.1 output for residues in monomer A of the R. toruloides PAL tetramer (Probe radius of 1.400 used for calculation). (residues 26-102, 124-349, and 354-715 of SEQ ID NO: 1). Similar values are obtained for the B, C, and D monomers of PAL.

| Residue | | Total | Apolar | Backbone | Sidechain | Ratio (%) | In/Out |
|---|---|---|---|---|---|---|---|
| GLN | 44 | 0.03 | 0.03 | 0.00 | 0.03 | 0.0 | i |
| VAL | 45 | 22.34 | 22.34 | 0.00 | 22.34 | 18.3 | i |
| ASP | 46 | 48.82 | 5.65 | 1.14 | 47.67 | 42.2 | |
| ILE | 47 | 0.04 | 0.03 | 0.01 | 0.03 | 0.0 | i |
| VAL | 48 | 0.00 | 0.00 | 0.00 | 0.00 | 0.0 | i |
| GLU | 49 | 88.05 | 17.28 | 0.52 | 87.54 | 62.0 | o |
| LYS | 50 | 61.03 | 30.38 | 7.70 | 53.33 | 32.4 | |
| MET | 51 | 7.52 | 2.39 | 5.13 | 2.38 | 1.5 | i |
| LEU | 52 | 50.21 | 25.78 | 29.64 | 20.57 | 14.1 | i |
| ALA | 53 | 76.76 | 59.88 | 29.25 | 47.51 | 73.2 | o |
| ALA | 54 | 18.64 | 10.76 | 13.69 | 4.95 | 7.6 | i |
| PRO | 55 | 68.48 | 68.48 | 14.02 | 54.46 | 51.8 | o |
| THR | 56 | 57.20 | 30.87 | 5.36 | 51.84 | 48.8 | |
| ASP | 57 | 125.51 | 42.99 | 14.28 | 111.22 | 98.4 | o |
| SER | 58 | 69.60 | 63.44 | 12.17 | 57.42 | 74.2 | o |
| THR | 59 | 63.03 | 26.40 | 13.75 | 49.29 | 46.4 | |
| LEU | 60 | 10.29 | 10.29 | 0.88 | 9.41 | 6.4 | i |
| GLU | 61 | 75.97 | 22.68 | 10.28 | 65.69 | 46.5 | |
| LEU | 62 | 1.05 | 1.05 | 0.96 | 0.08 | 0.1 | i |
| ASP | 63 | 26.44 | 9.30 | 2.27 | 24.16 | 21.4 | |
| GLY | 64 | 0.00 | 0.00 | 0.00 | 0.00 | 0.0 | i |
| TYR | 65 | 86.03 | 69.91 | 1.13 | 84.90 | 44.0 | |
| SER | 66 | 61.93 | 34.90 | 13.13 | 48.80 | 63.0 | o |
| LEU | 67 | 4.32 | 2.11 | 4.22 | 0.11 | 0.1 | i |
| ASN | 68 | 21.42 | 3.68 | 0.00 | 21.42 | 18.7 | i |
| LEU | 69 | 1.12 | 0.73 | 0.39 | 0.72 | 0.5 | i |
| GLY | 70 | 3.09 | 1.35 | 3.09 | 0.00 | 3.5 | i |
| ASP | 71 | 14.51 | 0.00 | 0.00 | 14.51 | 12.8 | i |
| VAL | 72 | 0.00 | 0.00 | 0.00 | 0.00 | 0.0 | i |
| VAL | 73 | 9.80 | 9.80 | 0.00 | 9.80 | 8.0 | i |
| SER | 74 | 3.73 | 3.73 | 1.26 | 2.48 | 3.2 | i |
| ALA | 75 | 0.00 | 0.00 | 0.00 | 0.00 | 0.0 | i |
| ALA | 76 | 3.48 | 0.00 | 3.48 | 0.00 | 0.0 | i |
| ARG | 77 | 70.61 | 31.66 | 31.77 | 38.85 | 19.9 | i |
| LYS | 78 | 118.75 | 64.94 | 24.33 | 94.42 | 57.4 | o |
| GLY | 79 | 50.54 | 30.27 | 50.54 | 0.00 | 58.0 | o |
| ARG | 80 | 12.47 | 0.00 | 0.37 | 12.09 | 6.2 | i |
| PRO | 81 | 50.07 | 50.07 | 1.56 | 48.51 | 46.1 | |
| VAL | 82 | 0.00 | 0.00 | 0.00 | 0.00 | 0.0 | i |
| ARG | 83 | 86.04 | 44.04 | 0.00 | 86.04 | 44.0 | |
| VAL | 84 | 9.27 | 5.04 | 4.23 | 5.04 | 4.1 | i |
| LYS | 85 | 75.96 | 40.70 | 1.25 | 74.70 | 45.4 | |
| ASP | 86 | 109.57 | 33.72 | 20.81 | 88.77 | 78.6 | o |
| SER | 87 | 23.61 | 21.72 | 10.58 | 13.03 | 16.8 | i |
| ASP | 88 | 115.80 | 43.87 | 5.12 | 110.69 | 98.0 | o |
| GLU | 89 | 134.52 | 51.30 | 8.90 | 125.63 | 89.0 | o |
| ILE | 90 | 10.01 | 10.01 | 0.00 | 10.01 | 6.8 | i |
| ARG | 91 | 70.59 | 48.02 | 0.00 | 70.59 | 36.1 | |
| SER | 92 | 36.79 | 33.03 | 6.40 | 30.39 | 39.3 | |
| LYS | 93 | 59.96 | 44.56 | 6.94 | 53.01 | 32.2 | |
| ILE | 94 | 1.25 | 1.25 | 0.30 | 0.95 | 0.6 | i |
| ASP | 95 | 71.89 | 31.44 | 3.30 | 68.58 | 60.7 | o |
| LYS | 96 | 118.86 | 85.97 | 2.45 | 116.40 | 70.8 | o |
| SER | 97 | 0.80 | 0.00 | 0.00 | 0.80 | 1.0 | i |
| VAL | 98 | 34.27 | 34.01 | 0.27 | 34.01 | 27.8 | |
| GLU | 99 | 123.42 | 58.45 | 4.39 | 119.03 | 84.3 | o |
| PHE | 100 | 35.91 | 35.91 | 9.88 | 26.03 | 14.5 | i |
| LEU | 101 | 44.37 | 33.09 | 14.86 | 29.51 | 20.2 | |
| ARG | 102 | 182.68 | 118.43 | 35.02 | 147.65 | 75.5 | o |
| THR | 124 | 140.49 | 90.64 | 31.67 | 108.81 | 100.0 | o |
| GLU | 125 | 145.75 | 60.45 | 4.95 | 140.80 | 99.7 | o |
| ASP | 126 | 109.73 | 35.14 | 2.93 | 106.80 | 94.5 | o |
| ALA | 127 | 21.51 | 21.51 | 2.88 | 18.63 | 28.7 | |
| ILE | 128 | 58.42 | 58.29 | 0.13 | 58.29 | 39.6 | |
| SER | 129 | 25.87 | 2.57 | 0.55 | 25.32 | 32.7 | |
| LEU | 130 | 70.82 | 70.82 | 0.00 | 70.82 | 48.4 | |
| GLN | 131 | 2.62 | 0.95 | 0.00 | 2.62 | 1.8 | i |
| LYS | 132 | 75.10 | 37.08 | 0.14 | 74.97 | 45.6 | |
| ALA | 133 | 0.01 | 0.00 | 0.01 | 0.00 | 0.0 | i |
| LEU | 134 | 23.71 | 23.68 | 0.03 | 23.68 | 16.2 | i |
| LEU | 135 | 3.15 | 3.15 | 0.00 | 3.15 | 2.2 | i |
| GLU | 136 | 3.28 | 2.56 | 2.61 | 0.67 | 0.5 | i |
| HIS | 137 | 9.58 | 6.23 | 0.03 | 9.55 | 6.2 | i |
| GLN | 138 | 3.33 | 1.36 | 0.00 | 3.33 | 2.3 | i |
| LEU | 139 | 2.01 | 2.01 | 0.00 | 2.01 | 1.4 | i |
| CYS | 140 | 0.40 | 0.01 | 0.10 | 0.30 | 0.3 | i |
| GLY | 141 | 1.65 | 0.04 | 1.65 | 0.00 | 1.9 | i |
| VAL | 142 | 5.99 | 4.01 | 2.04 | 3.95 | 3.2 | i |
| LEU | 143 | 20.49 | 19.28 | 1.27 | 19.22 | 13.1 | i |
| PRO | 144 | 15.63 | 14.04 | 6.77 | 8.87 | 8.4 | i |
| SER | 145 | 52.60 | 17.09 | 33.09 | 19.51 | 25.2 | |
| SER | 146 | 48.47 | 40.77 | 10.46 | 38.02 | 49.1 | |
| PHE | 147 | 109.36 | 101.78 | 7.69 | 101.67 | 56.5 | o |
| ASP | 148 | 122.14 | 41.51 | 19.84 | 102.30 | 90.5 | o |
| SER | 149 | 59.16 | 46.82 | 20.52 | 38.63 | 49.9 | |
| PHE | 150 | 31.20 | 19.82 | 11.38 | 19.82 | 11.0 | i |
| ARG | 151 | 131.45 | 64.95 | 11.33 | 120.12 | 61.4 | o |
| LEU | 152 | 49.98 | 47.07 | 12.93 | 37.04 | 25.3 | |
| GLY | 153 | 4.35 | 1.17 | 4.35 | 0.00 | 5.0 | i |
| ARG | 154 | 54.53 | 32.43 | 0.89 | 53.64 | 27.4 | |
| GLY | 155 | 12.53 | 7.07 | 12.53 | 0.00 | 14.4 | i |
| LEU | 156 | 2.23 | 2.23 | 0.00 | 2.23 | 1.5 | i |
| GLU | 157 | 86.08 | 63.88 | 16.59 | 69.49 | 49.2 | |
| ASN | 158 | 31.29 | 3.99 | 0.81 | 30.49 | 26.7 | |
| SER | 159 | 2.68 | 0.02 | 2.36 | 0.32 | 0.4 | i |
| LEU | 160 | 0.79 | 0.07 | 0.71 | 0.07 | 0.1 | i |
| PRO | 161 | 47.03 | 47.03 | 0.42 | 46.61 | 44.3 | |
| LEU | 162 | 41.50 | 39.65 | 1.85 | 39.65 | 27.1 | |
| GLU | 163 | 52.00 | 19.33 | 2.75 | 49.24 | 34.9 | |
| VAL | 164 | 2.37 | 2.37 | 0.00 | 2.37 | 1.9 | i |
| VAL | 165 | 0.20 | 0.20 | 0.06 | 0.14 | 0.1 | i |
| ARG | 166 | 25.35 | 23.08 | 0.00 | 25.35 | 13.0 | i |
| GLY | 167 | 0.00 | 0.00 | 0.00 | 0.00 | 0.0 | i |
| ALA | 168 | 0.00 | 0.00 | 0.00 | 0.00 | 0.0 | i |
| MET | 169 | 0.07 | 0.07 | 0.00 | 0.07 | 0.0 | i |
| THR | 170 | 0.00 | 0.00 | 0.00 | 0.00 | 0.0 | i |
| ILE | 171 | 3.37 | 3.37 | 0.00 | 3.37 | 2.3 | i |
| ARG | 172 | 0.78 | 0.63 | 0.00 | 0.78 | 0.4 | i |
| VAL | 173 | 0.00 | 0.00 | 0.00 | 0.00 | 0.0 | i |
| ASN | 174 | 1.02 | 0.00 | 0.00 | 1.02 | 0.9 | i |
| SER | 175 | 2.90 | 2.86 | 0.68 | 2.22 | 2.9 | i |
| LEU | 176 | 2.10 | 0.06 | 2.10 | 0.00 | 0.0 | i |
| THR | 177 | 0.00 | 0.00 | 0.00 | 0.00 | 0.0 | i |
| ARG | 178 | 1.43 | 0.09 | 0.41 | 1.01 | 0.5 | i |
| GLY | 179 | 9.07 | 3.25 | 9.07 | 0.00 | 10.4 | i |
| HIS | 180 | 19.28 | 16.62 | 0.06 | 19.22 | 12.4 | i |
| SER | 181 | 0.79 | 0.72 | 0.03 | 0.76 | 1.0 | i |
| ALA | 182 | 2.43 | 0.19 | 2.43 | 0.00 | 0.0 | i |
| VAL | 183 | 1.81 | 0.05 | 1.75 | 0.05 | 0.0 | i |
| ARG | 184 | 78.71 | 47.67 | 0.97 | 77.74 | 39.8 | |
| LEU | 185 | 30.23 | 29.78 | 0.45 | 29.78 | 20.4 | |
| VAL | 186 | 77.44 | 76.05 | 1.98 | 75.46 | 61.7 | o |
| VAL | 187 | 0.00 | 0.00 | 0.00 | 0.00 | 0.0 | i |
| LEU | 188 | 0.00 | 0.00 | 0.00 | 0.00 | 0.0 | i |
| GLU | 189 | 56.00 | 8.08 | 0.00 | 56.00 | 39.7 | |
| ALA | 190 | 11.40 | 11.40 | 7.44 | 3.97 | 6.1 | i |
| LEU | 191 | 0.00 | 0.00 | 0.00 | 0.00 | 0.0 | i |
| THR | 192 | 0.00 | 0.00 | 0.00 | 0.00 | 0.0 | i |
| ASN | 193 | 31.41 | 0.25 | 0.00 | 31.41 | 27.5 | |
| PHE | 194 | 1.12 | 1.11 | 0.01 | 1.11 | 0.6 | i |
| LEU | 195 | 3.94 | 0.03 | 3.93 | 0.01 | 0.0 | i |
| ASN | 196 | 59.53 | 24.57 | 32.67 | 26.86 | 23.5 | |
| HIS | 197 | 75.62 | 51.55 | 16.35 | 59.27 | 38.3 | |
| GLY | 198 | 34.36 | 28.45 | 34.36 | 0.00 | 39.4 | |
| ILE | 199 | 0.18 | 0.00 | 0.18 | 0.00 | 0.0 | i |
| THR | 200 | 4.41 | 0.00 | 0.00 | 4.41 | 4.1 | i |
| PRO | 201 | 0.85 | 0.78 | 0.07 | 0.78 | 0.7 | i |
| ILE | 202 | 3.73 | 1.17 | 3.17 | 0.55 | 0.4 | i |
| VAL | 203 | 0.02 | 0.00 | 0.02 | 0.00 | 0.0 | i |
| PRO | 204 | 4.35 | 2.14 | 2.21 | 2.14 | 2.0 | i |
| LEU | 205 | 25.59 | 24.56 | 1.03 | 24.56 | 16.8 | i |
| ARG | 206 | 26.61 | 10.12 | 7.15 | 19.46 | 10.0 | i |

TABLE 4-continued

GETAREA 1.1 output for residues in monomer A of the R. toruloides PAL tetramer (Probe radius of 1.400 used for calculation). (residues 26-102, 124-349, and 354-715 of SEQ ID NO: 1). Similar values are obtained for the B, C, and D monomers of PAL.

| Residue | | Total | Apolar | Backbone | Sidechain | Ratio (%) | In/Out |
|---|---|---|---|---|---|---|---|
| GLY | 207 | 1.41 | 0.34 | 1.41 | 0.00 | 1.6 | i |
| THR | 208 | 3.01 | 2.04 | 0.82 | 2.19 | 2.1 | i |
| ILE | 209 | 0.25 | 0.25 | 0.00 | 0.25 | 0.2 | i |
| SER | 210 | 0.06 | 0.00 | 0.00 | 0.06 | 0.1 | i |
| ALA | 211 | 0.01 | 0.01 | 0.01 | 0.00 | 0.0 | i |
| SER | 212 | 10.49 | 10.49 | 0.00 | 10.49 | 13.6 | i |
| GLY | 213 | 0.49 | 0.00 | 0.49 | 0.00 | 0.6 | i |
| ASP | 214 | 0.00 | 0.00 | 0.00 | 0.00 | 0.0 | i |
| LEU | 215 | 13.20 | 13.20 | 0.00 | 13.20 | 9.0 | i |
| SER | 216 | 2.38 | 2.34 | 0.03 | 2.35 | 3.0 | i |
| PRO | 217 | 3.85 | 3.85 | 0.00 | 3.85 | 3.7 | i |
| LEU | 218 | 0.84 | 0.30 | 0.54 | 0.30 | 0.2 | i |
| SER | 219 | 0.00 | 0.00 | 0.00 | 0.00 | 0.0 | i |
| TYR | 220 | 15.88 | 13.97 | 0.87 | 15.01 | 7.8 | i |
| ILE | 221 | 1.83 | 1.83 | 0.00 | 1.83 | 1.2 | i |
| ALA | 222 | 0.12 | 0.12 | 0.00 | 0.12 | 0.2 | i |
| ALA | 223 | 0.08 | 0.08 | 0.00 | 0.08 | 0.1 | i |
| ALA | 224 | 0.02 | 0.02 | 0.00 | 0.02 | 0.0 | i |
| ILE | 225 | 0.06 | 0.00 | 0.06 | 0.00 | 0.0 | i |
| SER | 226 | 21.48 | 8.85 | 9.95 | 11.53 | 14.9 | i |
| GLY | 227 | 1.95 | 0.00 | 1.95 | 0.00 | 2.2 | i |
| HIS | 228 | 2.89 | 1.59 | 1.46 | 1.42 | 0.9 | i |
| PRO | 229 | 79.31 | 69.49 | 15.98 | 63.34 | 60.2 | o |
| ASP | 230 | 24.42 | 1.32 | 10.26 | 14.17 | 12.5 | i |
| SER | 231 | 7.92 | 6.23 | 5.59 | 2.33 | 3.0 | i |
| LYS | 232 | 53.72 | 36.99 | 3.48 | 50.24 | 30.5 | |
| VAL | 233 | 0.00 | 0.00 | 0.00 | 0.00 | 0.0 | i |
| HIS | 234 | 11.57 | 10.76 | 0.00 | 11.57 | 7.5 | i |
| VAL | 235 | 0.31 | 0.31 | 0.00 | 0.31 | 0.3 | i |
| VAL | 236 | 93.91 | 77.69 | 16.22 | 77.69 | 63.5 | o |
| HIS | 237 | 46.52 | 41.49 | 6.57 | 39.95 | 25.8 | |
| GLU | 238 | 146.51 | 57.98 | 40.05 | 106.46 | 75.4 | o |
| GLY | 239 | 77.79 | 42.36 | 77.79 | 0.00 | 89.2 | o |
| LYS | 240 | 130.49 | 84.87 | 8.19 | 122.30 | 74.3 | o |
| GLU | 241 | 38.53 | 19.05 | 10.04 | 28.49 | 20.2 | |
| LYS | 242 | 41.12 | 41.12 | 2.90 | 38.23 | 23.2 | |
| ILE | 243 | 14.90 | 3.21 | 11.68 | 3.21 | 2.2 | i |
| LEU | 244 | 37.06 | 37.06 | 4.87 | 32.20 | 22.0 | |
| TYR | 245 | 106.10 | 67.30 | 0.26 | 105.85 | 54.8 | o |
| ALA | 246 | 0.02 | 0.00 | 0.02 | 0.00 | 0.0 | i |
| ARG | 247 | 118.85 | 58.85 | 4.60 | 114.25 | 58.4 | o |
| GLU | 248 | 86.33 | 40.74 | 8.20 | 78.13 | 55.3 | o |
| ALA | 249 | 0.00 | 0.00 | 0.00 | 0.00 | 0.0 | i |
| MET | 250 | 4.00 | 4.00 | 0.00 | 4.00 | 2.5 | i |
| ALA | 251 | 81.18 | 61.58 | 29.76 | 51.42 | 79.2 | o |
| LEU | 252 | 75.98 | 50.38 | 30.18 | 45.80 | 31.3 | |
| PHE | 253 | 53.95 | 45.87 | 15.25 | 38.69 | 21.5 | |
| ASN | 254 | 131.44 | 44.71 | 15.79 | 115.66 | 100.0 | o |
| LEU | 255 | 30.91 | 23.24 | 10.68 | 20.23 | 13.8 | i |
| GLU | 256 | 142.22 | 60.49 | 12.67 | 129.55 | 91.8 | o |
| PRO | 257 | 37.01 | 25.05 | 11.95 | 25.05 | 23.8 | |
| VAL | 258 | 12.15 | 11.99 | 6.50 | 5.64 | 4.6 | i |
| VAL | 259 | 88.44 | 81.81 | 9.10 | 79.35 | 64.9 | o |
| LEU | 260 | 7.45 | 5.20 | 2.33 | 5.12 | 3.5 | i |
| GLY | 261 | 11.36 | 11.36 | 11.36 | 0.00 | 13.0 | i |
| PRO | 262 | 66.18 | 64.26 | 3.87 | 62.31 | 59.2 | o |
| LYS | 263 | 18.79 | 15.28 | 10.95 | 7.85 | 4.8 | i |
| GLU | 264 | 3.05 | 2.17 | 0.00 | 3.05 | 2.2 | i |
| GLY | 265 | 0.00 | 0.00 | 0.00 | 0.00 | 0.0 | i |
| LEU | 266 | 59.90 | 59.90 | 0.00 | 59.90 | 41.0 | |
| GLY | 267 | 0.00 | 0.00 | 0.00 | 0.00 | 0.0 | i |
| LEU | 268 | 1.88 | 1.22 | 0.66 | 1.22 | 0.8 | i |
| VAL | 269 | 1.93 | 1.93 | 0.00 | 1.93 | 1.6 | i |
| ASN | 270 | 5.52 | 0.19 | 0.00 | 5.52 | 4.8 | i |
| GLY | 271 | 0.00 | 0.00 | 0.00 | 0.00 | 0.0 | i |
| THR | 272 | 0.62 | 0.00 | 0.00 | 0.62 | 0.6 | i |
| ALA | 273 | 1.27 | 1.27 | 0.31 | 0.96 | 1.5 | i |
| VAL | 274 | 0.05 | 0.05 | 0.00 | 0.05 | 0.0 | i |
| SER | 275 | 0.00 | 0.00 | 0.00 | 0.00 | 0.0 | i |
| ALA | 276 | 0.00 | 0.00 | 0.00 | 0.00 | 0.0 | i |
| SER | 277 | 0.00 | 0.00 | 0.00 | 0.00 | 0.0 | i |
| MET | 278 | 4.94 | 4.85 | 0.08 | 4.85 | 3.1 | i |
| ALA | 279 | 0.00 | 0.00 | 0.00 | 0.00 | 0.0 | i |
| THR | 280 | 0.00 | 0.00 | 0.00 | 0.00 | 0.0 | i |
| LEU | 281 | 4.54 | 4.54 | 0.00 | 4.54 | 3.1 | i |
| ALA | 282 | 1.20 | 1.20 | 1.19 | 0.00 | 0.0 | i |
| LEU | 283 | 0.00 | 0.00 | 0.00 | 0.00 | 0.0 | i |
| HIS | 284 | 12.56 | 9.38 | 0.00 | 12.56 | 8.1 | i |
| ASP | 285 | 34.78 | 10.76 | 1.51 | 33.27 | 29.4 | |
| ALA | 286 | 0.00 | 0.00 | 0.00 | 0.00 | 0.0 | i |
| HIS | 287 | 0.00 | 0.00 | 0.00 | 0.00 | 0.0 | i |
| MET | 288 | 5.83 | 5.79 | 0.04 | 5.79 | 3.7 | i |
| LEU | 289 | 2.53 | 2.53 | 0.04 | 2.49 | 1.7 | i |
| SER | 290 | 0.27 | 0.01 | 0.05 | 0.22 | 0.3 | i |
| LEU | 291 | 0.04 | 0.04 | 0.00 | 0.04 | 0.0 | i |
| LEU | 292 | 0.48 | 0.48 | 0.00 | 0.48 | 0.3 | i |
| SER | 293 | 0.00 | 0.00 | 0.00 | 0.00 | 0.0 | i |
| GLN | 294 | 0.14 | 0.00 | 0.00 | 0.14 | 0.1 | i |
| SER | 295 | 0.04 | 0.04 | 0.00 | 0.04 | 0.1 | i |
| LEU | 296 | 0.00 | 0.00 | 0.00 | 0.00 | 0.0 | i |
| THR | 297 | 0.00 | 0.00 | 0.00 | 0.00 | 0.0 | i |
| ALA | 298 | 0.00 | 0.00 | 0.00 | 0.00 | 0.0 | i |
| MET | 299 | 0.05 | 0.05 | 0.00 | 0.05 | 0.0 | i |
| THR | 300 | 0.56 | 0.56 | 0.00 | 0.56 | 0.5 | i |
| VAL | 301 | 0.07 | 0.07 | 0.00 | 0.07 | 0.1 | i |
| GLU | 302 | 0.00 | 0.00 | 0.00 | 0.00 | 0.0 | i |
| ALA | 303 | 0.00 | 0.00 | 0.00 | 0.00 | 0.0 | i |
| MET | 304 | 2.16 | 2.16 | 0.00 | 2.16 | 1.4 | i |
| VAL | 305 | 28.14 | 25.19 | 2.95 | 25.19 | 20.6 | |
| GLY | 306 | 0.00 | 0.00 | 0.00 | 0.00 | 0.0 | i |
| HIS | 307 | 25.29 | 14.87 | 0.12 | 25.17 | 16.3 | i |
| ALA | 308 | 14.34 | 10.26 | 4.09 | 10.26 | 15.8 | i |
| GLY | 309 | 10.62 | 9.89 | 10.62 | 0.00 | 12.2 | i |
| SER | 310 | 0.90 | 0.29 | 0.55 | 0.35 | 0.4 | i |
| PHE | 311 | 0.17 | 0.17 | 0.00 | 0.17 | 0.1 | i |
| HIS | 312 | 51.25 | 36.77 | 2.44 | 48.81 | 31.6 | |
| PRO | 313 | 46.58 | 46.58 | 0.00 | 46.58 | 44.3 | |
| PHE | 314 | 11.94 | 11.94 | 0.71 | 11.23 | 6.2 | i |
| LEU | 315 | 0.35 | 0.35 | 0.00 | 0.35 | 0.2 | i |
| HIS | 316 | 0.01 | 0.00 | 0.00 | 0.01 | 0.0 | i |
| ASP | 317 | 54.00 | 18.41 | 12.26 | 41.74 | 36.9 | |
| VAL | 318 | 74.35 | 68.57 | 12.12 | 62.23 | 50.9 | o |
| THR | 319 | 0.00 | 0.00 | 0.00 | 0.00 | 0.0 | i |
| ARG | 320 | 0.84 | 0.33 | 0.00 | 0.84 | 0.4 | i |
| PRO | 321 | 35.32 | 31.81 | 3.51 | 31.81 | 30.2 | |
| HIS | 322 | 12.19 | 9.94 | 0.00 | 12.19 | 7.9 | i |
| PRO | 323 | 15.48 | 13.35 | 2.13 | 13.35 | 12.7 | i |
| THR | 324 | 4.50 | 1.62 | 0.00 | 4.50 | 4.2 | i |
| GLN | 325 | 2.29 | 0.80 | 0.00 | 2.29 | 1.6 | i |
| ILE | 326 | 33.97 | 33.65 | 0.33 | 33.65 | 22.8 | |
| GLU | 327 | 15.11 | 13.18 | 9.66 | 5.45 | 3.9 | i |
| VAL | 328 | 0.00 | 0.00 | 0.00 | 0.00 | 0.0 | i |
| ALA | 329 | 0.00 | 0.00 | 0.00 | 0.00 | 0.0 | i |
| GLY | 330 | 18.64 | 13.97 | 18.64 | 0.00 | 21.4 | |
| ASN | 331 | 12.97 | 0.68 | 0.88 | 12.09 | 10.6 | i |
| ILE | 332 | 0.00 | 0.00 | 0.00 | 0.00 | 0.0 | i |
| ARG | 333 | 69.83 | 32.79 | 1.63 | 68.20 | 34.9 | |
| LYS | 334 | 63.20 | 35.11 | 0.74 | 62.46 | 38.0 | |
| LEU | 335 | 0.00 | 0.00 | 0.00 | 0.00 | 0.0 | i |
| LEU | 336 | 1.33 | 1.33 | 0.00 | 1.33 | 0.9 | i |
| GLU | 337 | 101.35 | 40.33 | 5.12 | 96.23 | 68.1 | o |
| GLY | 338 | 54.50 | 40.68 | 54.50 | 0.00 | 62.5 | o |
| SER | 339 | 2.90 | 0.00 | 2.90 | 0.00 | 0.0 | i |
| ARG | 340 | 150.18 | 69.97 | 19.67 | 130.52 | 66.8 | o |
| PHE | 341 | 3.55 | 0.00 | 3.55 | 0.00 | 0.0 | i |
| ALA | 342 | 4.31 | 0.00 | 4.31 | 0.00 | 0.0 | i |
| VAL | 343 | 60.01 | 60.01 | 4.92 | 55.09 | 45.0 | |
| HIS | 344 | 17.46 | 13.08 | 0.08 | 17.39 | 11.2 | i |
| HIS | 345 | 24.14 | 13.23 | 0.23 | 23.91 | 15.5 | i |
| GLU | 346 | 129.45 | 70.99 | 26.69 | 102.76 | 72.8 | o |
| GLU | 347 | 127.97 | 44.84 | 29.76 | 98.21 | 69.6 | o |
| GLU | 348 | 84.19 | 31.47 | 41.25 | 42.93 | 30.4 | |

TABLE 4-continued

GETAREA 1.1 output for residues in monomer A of the R. toruloides PAL tetramer (Probe radius of 1.400 used for calculation). (residues 26-102, 124-349, and 354-715 of SEQ ID NO: 1). Similar values are obtained for the B, C, and D monomers of PAL.

| Residue | | Total | Apolar | Backbone | Sidechain | Ratio (%) | In/Out |
|---|---|---|---|---|---|---|---|
| VAL | 349 | 125.59 | 88.78 | 65.27 | 60.32 | 49.3 | |
| ASP | 354 | 98.03 | 24.67 | 38.18 | 59.84 | 53.0 | o |
| GLU | 355 | 52.39 | 5.40 | 6.57 | 45.81 | 32.4 | |
| GLY | 356 | 58.63 | 35.30 | 58.63 | 0.00 | 67.2 | o |
| ILE | 357 | 130.62 | 112.31 | 25.86 | 104.76 | 71.1 | o |
| LEU | 358 | 76.87 | 65.17 | 20.95 | 55.92 | 38.2 | |
| ARG | 359 | 202.43 | 95.66 | 16.34 | 186.09 | 95.2 | o |
| GLN | 360 | 32.27 | 20.01 | 1.18 | 31.09 | 21.6 | |
| ASP | 361 | 3.67 | 3.38 | 3.29 | 0.38 | 0.3 | i |
| ARG | 362 | 31.68 | 1.16 | 0.15 | 31.53 | 16.1 | i |
| TYR | 363 | 4.95 | 1.48 | 0.00 | 4.95 | 2.6 | i |
| PRO | 364 | 0.08 | 0.08 | 0.00 | 0.08 | 0.1 | i |
| LEU | 365 | 2.59 | 2.59 | 0.00 | 2.59 | 1.8 | i |
| ARG | 366 | 19.46 | 1.70 | 0.09 | 19.37 | 9.9 | i |
| THR | 367 | 0.00 | 0.00 | 0.00 | 0.00 | 0.0 | i |
| SER | 368 | 0.00 | 0.00 | 0.00 | 0.00 | 0.0 | i |
| PRO | 369 | 0.01 | 0.01 | 0.00 | 0.01 | 0.0 | i |
| GLN | 370 | 1.49 | 0.75 | 1.26 | 0.23 | 0.2 | i |
| TRP | 371 | 4.99 | 2.27 | 2.72 | 2.27 | 1.0 | i |
| LEU | 372 | 0.29 | 0.29 | 0.00 | 0.29 | 0.2 | i |
| GLY | 373 | 0.44 | 0.44 | 0.44 | 0.00 | 0.5 | i |
| PRO | 374 | 14.28 | 14.28 | 5.23 | 9.05 | 8.6 | i |
| LEU | 375 | 7.02 | 6.93 | 0.09 | 6.93 | 4.7 | i |
| VAL | 376 | 0.03 | 0.03 | 0.00 | 0.03 | 0.0 | i |
| SER | 377 | 3.08 | 2.00 | 1.02 | 2.06 | 2.7 | i |
| ASP | 378 | 6.68 | 1.17 | 0.10 | 6.59 | 5.8 | i |
| LEU | 379 | 1.55 | 1.55 | 0.16 | 1.38 | 0.9 | i |
| ILE | 380 | 4.12 | 4.12 | 0.00 | 4.12 | 2.8 | i |
| HIS | 381 | 0.49 | 0.49 | 0.00 | 0.49 | 0.3 | i |
| ALA | 382 | 0.23 | 0.23 | 0.00 | 0.23 | 0.3 | i |
| HIS | 383 | 2.84 | 0.00 | 0.00 | 2.84 | 1.8 | i |
| ALA | 384 | 2.94 | 2.43 | 0.71 | 2.23 | 3.4 | i |
| VAL | 385 | 6.85 | 6.85 | 0.00 | 6.85 | 5.6 | i |
| LEU | 386 | 0.00 | 0.00 | 0.00 | 0.00 | 0.0 | i |
| THR | 387 | 5.56 | 5.53 | 0.00 | 5.56 | 5.2 | i |
| ILE | 388 | 21.95 | 21.95 | 0.00 | 21.95 | 14.9 | i |
| GLU | 389 | 1.07 | 0.00 | 1.07 | 0.00 | 0.0 | i |
| ALA | 390 | 2.12 | 0.00 | 2.11 | 0.00 | 0.0 | i |
| GLY | 391 | 0.10 | 0.10 | 0.10 | 0.00 | 0.1 | i |
| GLN | 392 | 25.99 | 1.42 | 0.01 | 25.98 | 18.1 | i |
| SER | 393 | 2.40 | 0.00 | 2.40 | 0.00 | 0.0 | i |
| THR | 394 | 0.00 | 0.00 | 0.00 | 0.00 | 0.0 | i |
| THR | 395 | 3.69 | 1.89 | 0.00 | 3.69 | 3.5 | i |
| ASP | 396 | 0.04 | 0.00 | 0.04 | 0.00 | 0.0 | i |
| ASN | 397 | 10.27 | 3.09 | 0.25 | 10.02 | 8.8 | i |
| PRO | 398 | 28.00 | 28.00 | 0.00 | 28.00 | 26.6 | |
| LEU | 399 | 0.31 | 0.31 | 0.00 | 0.31 | 0.2 | i |
| ILE | 400 | 4.84 | 3.53 | 1.30 | 3.53 | 2.4 | i |
| ASP | 401 | 8.18 | 0.74 | 0.74 | 7.44 | 6.6 | i |
| VAL | 402 | 36.65 | 33.23 | 3.42 | 33.23 | 27.2 | |
| GLU | 403 | 146.50 | 71.50 | 31.65 | 114.85 | 81.3 | o |
| ASN | 404 | 104.42 | 27.17 | 21.03 | 83.39 | 73.0 | o |
| LYS | 405 | 148.53 | 111.15 | 17.69 | 130.84 | 79.5 | o |
| THR | 406 | 18.92 | 16.20 | 6.28 | 12.64 | 11.9 | i |
| SER | 407 | 42.87 | 10.58 | 6.90 | 35.97 | 46.5 | |
| HIS | 408 | 4.69 | 4.69 | 3.40 | 1.30 | 0.8 | i |
| HIS | 409 | 80.68 | 60.75 | 4.05 | 76.63 | 49.6 | |
| GLY | 410 | 0.27 | 0.27 | 0.27 | 0.00 | 0.3 | i |
| GLY | 411 | 0.06 | 0.00 | 0.06 | 0.00 | 0.1 | i |
| ASN | 412 | 0.61 | 0.42 | 0.18 | 0.42 | 0.4 | i |
| PHE | 413 | 4.79 | 4.79 | 0.00 | 4.79 | 2.7 | i |
| GLN | 414 | 0.00 | 0.00 | 0.00 | 0.00 | 0.0 | i |
| ALA | 415 | 0.00 | 0.00 | 0.00 | 0.00 | 0.0 | i |
| ALA | 416 | 10.99 | 10.12 | 0.89 | 10.10 | 15.6 | i |
| ALA | 417 | 2.69 | 2.69 | 0.00 | 2.69 | 4.1 | i |
| VAL | 418 | 0.00 | 0.00 | 0.00 | 0.00 | 0.0 | i |
| ALA | 419 | 2.29 | 2.29 | 0.00 | 2.29 | 3.5 | i |
| ASN | 420 | 19.04 | 9.97 | 7.24 | 11.80 | 10.3 | i |
| THR | 421 | 0.00 | 0.00 | 0.00 | 0.00 | 0.0 | i |
| MET | 422 | 0.00 | 0.00 | 0.00 | 0.00 | 0.0 | i |
| GLU | 423 | 7.15 | 3.64 | 3.82 | 3.33 | 2.4 | i |
| LYS | 424 | 10.80 | 9.51 | 5.28 | 5.52 | 3.4 | i |
| THR | 425 | 0.90 | 0.63 | 0.65 | 0.25 | 0.2 | i |
| ARG | 426 | 0.28 | 0.06 | 0.09 | 0.19 | 0.1 | i |
| LEU | 427 | 27.58 | 27.58 | 0.00 | 27.58 | 18.9 | i |
| GLY | 428 | 4.70 | 4.70 | 4.70 | 0.00 | 5.4 | i |
| LEU | 429 | 0.48 | 0.46 | 0.02 | 0.46 | 0.3 | i |
| ALA | 430 | 4.53 | 2.52 | 2.03 | 2.50 | 3.9 | i |
| GLN | 431 | 19.87 | 13.05 | 0.00 | 19.87 | 13.8 | i |
| ILE | 432 | 0.29 | 0.29 | 0.00 | 0.29 | 0.2 | i |
| GLY | 433 | 0.00 | 0.00 | 0.00 | 0.00 | 0.0 | i |
| LYS | 434 | 11.66 | 11.07 | 0.00 | 11.66 | 7.1 | i |
| LEU | 435 | 0.00 | 0.00 | 0.00 | 0.00 | 0.0 | i |
| ASN | 436 | 0.00 | 0.00 | 0.00 | 0.00 | 0.0 | i |
| PHE | 437 | 0.03 | 0.03 | 0.00 | 0.03 | 0.0 | i |
| THR | 438 | 2.55 | 2.12 | 0.43 | 2.12 | 2.0 | i |
| GLN | 439 | 0.85 | 0.49 | 0.85 | 0.00 | 0.0 | i |
| LEU | 440 | 0.00 | 0.00 | 0.00 | 0.00 | 0.0 | i |
| THR | 441 | 13.67 | 12.45 | 0.32 | 13.36 | 12.6 | i |
| GLU | 442 | 7.15 | 4.11 | 0.00 | 7.15 | 5.1 | i |
| MET | 443 | 0.00 | 0.00 | 0.00 | 0.00 | 0.0 | i |
| LEU | 444 | 4.97 | 1.69 | 3.60 | 1.37 | 0.9 | i |
| ASN | 445 | 13.80 | 0.11 | 0.00 | 13.80 | 12.1 | i |
| ALA | 446 | 11.44 | 9.33 | 2.13 | 9.31 | 14.3 | i |
| GLY | 447 | 70.07 | 39.73 | 70.07 | 0.00 | 80.4 | o |
| MET | 448 | 35.51 | 32.87 | 6.28 | 29.23 | 18.5 | i |
| ASN | 449 | 0.66 | 0.00 | 0.07 | 0.59 | 0.5 | i |
| ARG | 450 | 56.64 | 32.99 | 10.58 | 46.07 | 23.6 | |
| GLY | 451 | 8.66 | 5.94 | 8.66 | 0.00 | 9.9 | i |
| LEU | 452 | 0.46 | 0.46 | 0.02 | 0.44 | 0.3 | i |
| PRO | 453 | 27.57 | 27.48 | 0.59 | 26.97 | 25.6 | |
| SER | 454 | 10.20 | 9.89 | 0.42 | 9.78 | 12.6 | i |
| CYS | 455 | 12.38 | 0.84 | 2.14 | 10.24 | 10.0 | i |
| LEU | 456 | 0.15 | 0.15 | 0.00 | 0.15 | 0.1 | i |
| ALA | 457 | 1.40 | 0.56 | 1.40 | 0.00 | 0.0 | i |
| ALA | 458 | 5.27 | 0.46 | 5.03 | 0.25 | 0.4 | i |
| GLU | 459 | 15.26 | 4.79 | 2.45 | 12.81 | 9.1 | i |
| ASP | 460 | 50.55 | 18.89 | 2.57 | 47.98 | 42.5 | |
| PRO | 461 | 16.71 | 14.28 | 2.42 | 14.28 | 13.6 | i |
| SER | 462 | 46.54 | 33.70 | 14.59 | 31.95 | 41.3 | |
| LEU | 463 | 49.90 | 49.64 | 0.27 | 49.64 | 34.0 | |
| SER | 464 | 4.52 | 3.65 | 0.15 | 4.37 | 5.6 | i |
| TYR | 465 | 36.57 | 30.83 | 0.05 | 36.52 | 18.9 | i |
| HIS | 466 | 2.95 | 2.84 | 0.01 | 2.94 | 1.9 | i |
| CYS | 467 | 0.03 | 0.03 | 0.00 | 0.03 | 0.0 | i |
| LYS | 468 | 45.94 | 39.20 | 2.53 | 43.41 | 26.4 | |
| GLY | 469 | 1.01 | 0.19 | 1.01 | 0.00 | 1.2 | i |
| LEU | 470 | 0.05 | 0.05 | 0.00 | 0.05 | 0.0 | i |
| ASP | 471 | 2.42 | 1.02 | 0.00 | 2.42 | 2.1 | i |
| ILE | 472 | 3.29 | 3.29 | 0.00 | 3.29 | 2.2 | i |
| ALA | 473 | 0.02 | 0.02 | 0.00 | 0.02 | 0.0 | i |
| ALA | 474 | 0.00 | 0.00 | 0.00 | 0.00 | 0.0 | i |
| ALA | 475 | 0.12 | 0.12 | 0.00 | 0.12 | 0.2 | i |
| ALA | 476 | 1.49 | 1.32 | 0.17 | 1.32 | 2.0 | i |
| TYR | 477 | 0.99 | 0.35 | 0.14 | 0.85 | 0.4 | i |
| THR | 478 | 5.42 | 4.02 | 1.40 | 4.02 | 3.8 | i |
| SER | 479 | 0.23 | 0.11 | 0.11 | 0.12 | 0.2 | i |
| GLU | 480 | 0.95 | 0.00 | 0.00 | 0.95 | 0.7 | i |
| LEU | 481 | 0.52 | 0.45 | 0.07 | 0.45 | 0.3 | i |
| GLY | 482 | 5.74 | 5.74 | 5.74 | 0.00 | 6.6 | i |
| HIS | 483 | 0.72 | 0.70 | 0.01 | 0.70 | 0.5 | i |
| LEU | 484 | 1.68 | 1.68 | 0.00 | 1.68 | 1.1 | i |
| ALA | 485 | 3.22 | 0.00 | 3.22 | 0.00 | 0.0 | i |
| ASN | 486 | 0.60 | 0.00 | 0.00 | 0.60 | 0.5 | i |
| PRO | 487 | 5.14 | 5.13 | 1.34 | 3.80 | 3.6 | i |
| VAL | 488 | 0.00 | 0.00 | 0.00 | 0.00 | 0.0 | i |
| THR | 489 | 7.73 | 6.71 | 0.52 | 7.21 | 6.8 | i |
| THR | 490 | 14.65 | 6.72 | 14.49 | 0.15 | 0.1 | i |
| HIS | 491 | 3.75 | 3.21 | 2.58 | 1.17 | 0.8 | i |
| VAL | 492 | 5.74 | 0.74 | 5.00 | 0.74 | 0.6 | i |
| GLN | 493 | 8.24 | 0.29 | 0.23 | 8.01 | 5.6 | i |
| PRO | 494 | 14.74 | 12.68 | 2.24 | 12.49 | 11.9 | i |

TABLE 4-continued

GETAREA 1.1 output for residues in monomer A of the R. toruloides PAL tetramer (Probe radius of 1.400 used for calculation). (residues 26-102, 124-349, and 354-715 of SEQ ID NO: 1). Similar values are obtained for the B, C, and D monomers of PAL.

| Residue | | Total | Apolar | Backbone | Sidechain | Ratio (%) | In/Out |
|---|---|---|---|---|---|---|---|
| ALA | 495 | 0.00 | 0.00 | 0.00 | 0.00 | 0.0 | i |
| GLU | 496 | 15.22 | 0.45 | 0.00 | 15.22 | 10.8 | i |
| MET | 497 | 69.56 | 64.85 | 9.05 | 60.51 | 38.2 | |
| ALA | 498 | 23.31 | 22.76 | 0.54 | 22.76 | 35.1 | |
| ASN | 499 | 29.56 | 9.88 | 0.00 | 29.56 | 25.9 | |
| GLN | 500 | 2.66 | 0.00 | 0.00 | 2.66 | 1.9 | i |
| ALA | 501 | 5.13 | 5.11 | 0.01 | 5.11 | 7.9 | i |
| VAL | 502 | 0.00 | 0.00 | 0.00 | 0.00 | 0.0 | i |
| ASN | 503 | 0.17 | 0.00 | 0.00 | 0.17 | 0.1 | i |
| SER | 504 | 1.13 | 1.13 | 1.13 | 0.00 | 0.0 | i |
| LEU | 505 | 0.03 | 0.03 | 0.03 | 0.00 | 0.0 | i |
| ALA | 506 | 0.00 | 0.00 | 0.00 | 0.00 | 0.0 | i |
| LEU | 507 | 1.81 | 1.81 | 0.00 | 1.81 | 1.2 | i |
| ILE | 508 | 4.66 | 4.66 | 0.00 | 4.66 | 3.2 | i |
| SER | 509 | 0.00 | 0.00 | 0.00 | 0.00 | 0.0 | i |
| ALA | 510 | 0.00 | 0.00 | 0.00 | 0.00 | 0.0 | i |
| ARG | 511 | 21.63 | 12.67 | 5.62 | 16.01 | 8.2 | i |
| ARG | 512 | 7.45 | 2.06 | 0.00 | 7.45 | 3.8 | i |
| THR | 513 | 0.00 | 0.00 | 0.00 | 0.00 | 0.0 | i |
| THR | 514 | 51.15 | 50.40 | 0.51 | 50.65 | 47.7 | |
| GLU | 515 | 36.21 | 18.73 | 5.92 | 30.29 | 21.5 | |
| SER | 516 | 0.04 | 0.01 | 0.00 | 0.04 | 0.1 | |
| ASN | 517 | 6.83 | 6.67 | 0.00 | 6.83 | 6.0 | i |
| ASP | 518 | 23.01 | 6.68 | 0.12 | 22.89 | 20.3 | |
| VAL | 519 | 0.00 | 0.00 | 0.00 | 0.00 | 0.0 | i |
| LEU | 520 | 0.00 | 0.00 | 0.00 | 0.00 | 0.0 | i |
| SER | 521 | 2.32 | 0.00 | 0.00 | 2.32 | 3.0 | i |
| LEU | 522 | 2.72 | 2.72 | 0.00 | 2.72 | 1.9 | i |
| LEU | 523 | 0.00 | 0.00 | 0.00 | 0.00 | 0.0 | i |
| LEU | 524 | 0.00 | 0.00 | 0.00 | 0.00 | 0.0 | i |
| ALA | 525 | 0.00 | 0.00 | 0.00 | 0.00 | 0.0 | i |
| THR | 526 | 0.04 | 0.00 | 0.00 | 0.04 | 0.0 | i |
| HIS | 527 | 0.00 | 0.00 | 0.00 | 0.00 | 0.0 | i |
| LEU | 528 | 0.02 | 0.02 | 0.00 | 0.02 | 0.0 | i |
| TYR | 529 | 6.54 | 4.49 | 1.82 | 4.72 | 2.4 | i |
| CYS | 530 | 0.00 | 0.00 | 0.00 | 0.00 | 0.0 | i |
| VAL | 531 | 0.00 | 0.00 | 0.00 | 0.00 | 0.0 | i |
| LEU | 532 | 1.26 | 1.26 | 0.00 | 1.26 | 0.9 | i |
| GLN | 533 | 1.71 | 1.26 | 0.00 | 1.71 | 1.2 | i |
| ALA | 534 | 0.00 | 0.00 | 0.00 | 0.00 | 0.0 | i |
| ILE | 535 | 0.00 | 0.00 | 0.00 | 0.00 | 0.0 | i |
| ASP | 536 | 0.60 | 0.59 | 0.00 | 0.60 | 0.5 | i |
| LEU | 537 | 8.12 | 5.77 | 2.35 | 5.77 | 3.9 | i |
| ARG | 538 | 8.16 | 1.40 | 0.10 | 8.06 | 4.1 | i |
| ALA | 539 | 0.00 | 0.00 | 0.00 | 0.00 | 0.0 | i |
| ILE | 540 | 15.44 | 15.44 | 0.01 | 15.43 | 10.5 | i |
| GLU | 541 | 40.95 | 9.17 | 3.19 | 37.76 | 26.7 | |
| PHE | 542 | 43.55 | 42.72 | 1.90 | 41.66 | 23.1 | |
| GLU | 543 | 35.05 | 8.42 | 0.05 | 35.00 | 24.8 | |
| PHE | 544 | 13.40 | 13.40 | 0.00 | 13.40 | 7.4 | i |
| LYS | 545 | 116.34 | 72.41 | 9.00 | 107.34 | 65.3 | o |
| LYS | 546 | 129.06 | 94.61 | 21.23 | 107.83 | 65.6 | o |
| GLN | 547 | 83.58 | 40.27 | 9.33 | 74.25 | 51.7 | o |
| PHE | 548 | 5.68 | 5.68 | 0.00 | 5.68 | 3.2 | i |
| GLY | 549 | 30.53 | 28.93 | 30.53 | 0.00 | 35.0 | |
| PRO | 550 | 90.58 | 88.10 | 10.03 | 80.55 | 76.6 | o |
| ALA | 551 | 24.84 | 24.84 | 6.40 | 18.45 | 28.4 | |
| ILE | 552 | 11.86 | 11.85 | 0.87 | 11.00 | 7.5 | i |
| VAL | 553 | 44.87 | 44.87 | 0.00 | 44.87 | 36.7 | |
| SER | 554 | 63.33 | 31.18 | 8.99 | 54.34 | 70.2 | o |
| LEU | 555 | 27.10 | 27.10 | 0.00 | 27.10 | 18.5 | i |
| ILE | 556 | 0.00 | 0.00 | 0.00 | 0.00 | 0.0 | i |
| ASP | 557 | 49.58 | 26.09 | 6.39 | 43.19 | 38.2 | |
| GLN | 558 | 133.55 | 47.42 | 35.73 | 97.82 | 68.1 | o |
| HIS | 559 | 50.06 | 26.64 | 20.29 | 29.77 | 19.3 | i |
| PHE | 560 | 0.14 | 0.14 | 0.14 | 0.00 | 0.0 | i |
| GLY | 561 | 25.59 | 20.43 | 25.59 | 0.00 | 29.3 | |
| SER | 562 | 95.77 | 52.85 | 11.41 | 84.36 | 100.0 | o |
| ALA | 563 | 25.78 | 13.41 | 21.35 | 4.43 | 6.8 | i |
| MET | 564 | 9.49 | 5.75 | 3.76 | 5.74 | 3.6 | i |
| THR | 565 | 107.91 | 70.57 | 27.75 | 80.15 | 75.5 | o |
| GLY | 566 | 94.82 | 54.29 | 94.82 | 0.00 | 100.0 | o |
| SER | 567 | 55.57 | 31.80 | 35.91 | 19.66 | 25.4 | |
| ASN | 568 | 129.49 | 56.34 | 19.06 | 110.43 | 96.6 | o |
| LEU | 569 | 29.23 | 29.21 | 0.05 | 29.18 | 20.0 | i |
| ARG | 570 | 104.82 | 51.97 | 0.03 | 104.79 | 53.6 | o |
| ASP | 571 | 112.62 | 36.90 | 4.41 | 108.21 | 95.8 | o |
| GLU | 572 | 63.76 | 30.07 | 4.25 | 59.51 | 42.1 | |
| LEU | 573 | 0.00 | 0.00 | 0.00 | 0.00 | 0.0 | i |
| VAL | 574 | 27.42 | 27.42 | 0.00 | 27.42 | 22.4 | |
| GLU | 575 | 88.06 | 28.39 | 6.61 | 81.44 | 57.7 | o |
| LYS | 576 | 71.21 | 35.89 | 0.54 | 70.67 | 43.0 | |
| VAL | 577 | 0.00 | 0.00 | 0.00 | 0.00 | 0.0 | i |
| ASN | 578 | 49.30 | 26.88 | 2.11 | 47.19 | 41.3 | |
| LYS | 579 | 129.15 | 85.44 | 5.69 | 123.46 | 75.1 | o |
| THR | 580 | 7.67 | 0.32 | 0.19 | 7.48 | 7.0 | i |
| LEU | 581 | 5.48 | 5.48 | 0.00 | 5.48 | 3.8 | i |
| ALA | 582 | 62.20 | 54.95 | 12.87 | 49.33 | 76.0 | o |
| LYS | 583 | 83.37 | 51.76 | 12.46 | 70.91 | 43.1 | |
| ARG | 584 | 4.99 | 0.57 | 0.00 | 4.99 | 2.6 | i |
| LEU | 585 | 26.89 | 26.84 | 0.05 | 26.84 | 18.4 | i |
| GLU | 586 | 84.40 | 22.33 | 4.44 | 79.96 | 56.6 | o |
| GLN | 587 | 74.87 | 35.66 | 26.51 | 48.36 | 33.7 | |
| THR | 588 | 0.42 | 0.42 | 0.02 | 0.40 | 0.4 | i |
| ASN | 589 | 5.53 | 0.11 | 2.24 | 3.28 | 2.9 | i |
| SER | 590 | 26.68 | 13.94 | 1.11 | 25.56 | 33.0 | |
| TYR | 591 | 17.82 | 8.73 | 3.99 | 13.82 | 7.2 | i |
| ASP | 592 | 16.05 | 4.03 | 0.00 | 16.05 | 14.2 | i |
| LEU | 593 | 15.41 | 15.27 | 2.91 | 12.50 | 8.6 | i |
| VAL | 594 | 69.95 | 69.89 | 0.06 | 69.89 | 57.1 | o |
| PRO | 595 | 33.58 | 32.21 | 6.75 | 26.83 | 25.5 | |
| ARG | 596 | 33.04 | 4.28 | 0.00 | 33.04 | 16.9 | i |
| TRP | 597 | 12.26 | 10.73 | 0.00 | 12.26 | 5.5 | i |
| HIS | 598 | 48.99 | 41.84 | 0.27 | 48.72 | 31.5 | |
| ASP | 599 | 21.09 | 14.83 | 6.70 | 14.39 | 12.7 | i |
| ALA | 600 | 0.00 | 0.00 | 0.00 | 0.00 | 0.0 | i |
| PHE | 601 | 0.24 | 0.24 | 0.00 | 0.24 | 0.1 | i |
| SER | 602 | 13.25 | 9.86 | 0.38 | 12.87 | 16.6 | i |
| PHE | 603 | 2.19 | 2.19 | 0.00 | 2.19 | 1.2 | i |
| ALA | 604 | 0.00 | 0.00 | 0.00 | 0.00 | 0.0 | i |
| ALA | 605 | 0.36 | 0.36 | 0.00 | 0.36 | 0.6 | i |
| GLY | 606 | 1.29 | 0.00 | 1.29 | 0.00 | 1.5 | i |
| THR | 607 | 9.62 | 4.75 | 0.55 | 9.07 | 8.5 | i |
| VAL | 608 | 0.00 | 0.00 | 0.00 | 0.00 | 0.0 | i |
| VAL | 609 | 0.61 | 0.61 | 0.00 | 0.61 | 0.5 | i |
| GLU | 610 | 77.36 | 17.93 | 6.16 | 71.21 | 50.4 | o |
| VAL | 611 | 11.36 | 4.69 | 11.14 | 0.22 | 0.2 | i |
| LEU | 612 | 0.00 | 0.00 | 0.00 | 0.00 | 0.0 | i |
| SER | 613 | 27.52 | 2.79 | 0.54 | 26.98 | 34.9 | |
| SER | 614 | 99.75 | 62.14 | 38.17 | 61.57 | 79.6 | o |
| THR | 615 | 20.20 | 13.13 | 16.25 | 3.96 | 3.7 | i |
| SER | 616 | 107.98 | 69.69 | 36.15 | 71.83 | 92.8 | o |
| LEU | 617 | 18.39 | 16.31 | 6.35 | 12.04 | 8.2 | i |
| SER | 618 | 51.34 | 45.94 | 6.92 | 44.42 | 57.4 | o |
| LEU | 619 | 0.00 | 0.00 | 0.00 | 0.00 | 0.0 | i |
| ALA | 620 | 51.91 | 49.73 | 3.10 | 48.81 | 75.2 | o |
| ALA | 621 | 30.63 | 30.63 | 8.91 | 21.72 | 33.5 | |
| VAL | 622 | 0.00 | 0.00 | 0.00 | 0.00 | 0.0 | i |
| ASN | 623 | 22.50 | 0.61 | 0.00 | 22.50 | 19.7 | i |
| ALA | 624 | 51.80 | 50.10 | 7.93 | 43.87 | 67.6 | o |
| TRP | 625 | 0.64 | 0.64 | 0.00 | 0.64 | 0.3 | i |
| LYS | 626 | 12.24 | 2.50 | 0.00 | 12.24 | 7.4 | i |
| VAL | 627 | 55.14 | 55.14 | 0.00 | 55.14 | 45.1 | |
| ALA | 628 | 32.00 | 29.99 | 3.72 | 28.28 | 43.6 | |
| ALA | 629 | 0.37 | 0.37 | 0.00 | 0.37 | 0.6 | i |
| ALA | 630 | 0.00 | 0.00 | 0.00 | 0.00 | 0.0 | i |
| GLU | 631 | 96.36 | 33.38 | 3.25 | 93.11 | 65.9 | o |
| SER | 632 | 30.47 | 20.83 | 9.41 | 21.06 | 27.2 | |
| ALA | 633 | 0.00 | 0.00 | 0.00 | 0.00 | 0.0 | i |
| ILE | 634 | 11.88 | 11.88 | 0.00 | 11.88 | 8.1 | i |
| SER | 635 | 66.80 | 47.52 | 3.36 | 63.44 | 82.0 | o |
| LEU | 636 | 19.70 | 19.70 | 2.22 | 17.48 | 12.0 | i |

TABLE 4-continued

GETAREA 1.1 output for residues in monomer A of the R.
toruloides PAL tetramer (Probe radius of 1.400 used for calculation).
(residues 26-102, 124-349,and 354-715 of SEQ ID NO: 1).
Similar values are obtained for the B, C, and D monomers of PAL.

| Residue | | Total | Apolar | Backbone | Sidechain | Ratio (%) | In/Out |
|---|---|---|---|---|---|---|---|
| THR | 637 | 14.89 | 13.81 | 0.05 | 14.84 | 14.0 | i |
| ARG | 638 | 117.95 | 61.95 | 1.28 | 116.66 | 59.7 | o |
| GLN | 639 | 108.05 | 34.74 | 6.40 | 101.64 | 70.7 | o |
| VAL | 640 | 6.41 | 5.67 | 1.45 | 4.95 | 4.1 | i |
| ARG | 641 | 32.25 | 2.42 | 0.00 | 32.25 | 16.5 | i |
| GLU | 642 | 80.54 | 44.47 | 0.00 | 80.54 | 57.0 | o |
| THR | 643 | 93.79 | 76.75 | 7.56 | 86.23 | 81.2 | o |
| PHE | 644 | 22.26 | 16.30 | 9.40 | 12.86 | 7.1 | i |
| TRP | 645 | 59.61 | 35.04 | 25.88 | 33.74 | 15.0 | i |
| SER | 646 | 92.61 | 44.10 | 43.18 | 49.43 | 63.9 | o |
| ALA | 647 | 56.09 | 43.11 | 22.93 | 33.16 | 51.1 | o |
| ALA | 648 | 70.74 | 67.32 | 17.68 | 53.06 | 81.8 | o |
| SER | 649 | 20.92 | 16.76 | 7.61 | 13.30 | 17.2 | i |
| THR | 650 | 88.64 | 60.30 | 18.77 | 69.87 | 65.8 | o |
| SER | 651 | 79.05 | 31.30 | 23.79 | 55.26 | 71.4 | o |
| SER | 652 | 6.54 | 4.13 | 5.60 | 0.94 | 1.2 | i |
| PRO | 653 | 23.93 | 23.93 | 5.52 | 18.41 | 17.5 | i |
| ALA | 654 | 0.00 | 0.00 | 0.00 | 0.00 | 0.0 | i |
| LEU | 655 | 54.76 | 43.36 | 11.40 | 43.36 | 29.7 | |
| SER | 656 | 59.86 | 27.54 | 21.67 | 38.19 | 49.3 | |
| TYR | 657 | 9.52 | 9.42 | 0.41 | 9.11 | 4.7 | i |
| LEU | 658 | 5.06 | 0.00 | 5.06 | 0.00 | 0.0 | i |
| SER | 659 | 0.00 | 0.00 | 0.00 | 0.00 | 0.0 | i |
| PRO | 660 | 85.90 | 80.38 | 6.91 | 78.98 | 75.1 | o |
| ARG | 661 | 73.35 | 16.78 | 0.09 | 73.26 | 37.5 | |
| THR | 662 | 0.06 | 0.06 | 0.00 | 0.06 | 0.1 | i |
| GLN | 663 | 45.92 | 7.59 | 0.16 | 45.75 | 31.8 | |
| ILE | 664 | 40.57 | 39.01 | 6.26 | 34.31 | 23.3 | |
| LEU | 665 | 0.00 | 0.00 | 0.00 | 0.00 | 0.0 | i |
| TYR | 666 | 1.70 | 1.15 | 0.00 | 1.70 | 0.9 | i |
| ALA | 667 | 39.28 | 39.22 | 0.55 | 38.73 | 59.7 | o |
| PHE | 668 | 4.74 | 4.74 | 1.72 | 3.02 | 1.7 | i |
| VAL | 669 | 0.00 | 0.00 | 0.00 | 0.00 | 0.0 | i |
| ARG | 670 | 5.79 | 0.43 | 0.00 | 5.79 | 3.0 | i |
| GLU | 671 | 60.54 | 30.37 | 18.82 | 41.71 | 29.5 | |
| GLU | 672 | 105.18 | 38.07 | 27.70 | 77.47 | 54.9 | o |
| LEU | 673 | 19.32 | 12.90 | 10.94 | 8.38 | 5.7 | i |
| GLY | 674 | 38.67 | 22.01 | 38.67 | 0.00 | 44.4 | |
| VAL | 675 | 2.99 | 2.99 | 0.45 | 2.55 | 2.1 | i |
| LYS | 676 | 97.68 | 80.01 | 7.95 | 89.73 | 54.5 | o |
| ALA | 677 | 11.31 | 4.27 | 8.19 | 3.12 | 4.8 | i |
| ARG | 678 | 13.16 | 8.02 | 3.91 | 9.25 | 4.7 | i |
| ARG | 679 | 19.53 | 5.30 | 0.97 | 18.56 | 9.5 | i |
| GLY | 680 | 3.16 | 3.16 | 3.16 | 0.00 | 3.6 | i |
| ASP | 681 | 3.17 | 0.43 | 2.11 | 1.06 | 0.9 | i |
| VAL | 682 | 31.89 | 22.10 | 14.15 | 17.74 | 14.5 | i |
| PHE | 683 | 102.66 | 82.71 | 29.57 | 73.10 | 40.6 | |
| LEU | 684 | 69.80 | 46.40 | 27.27 | 42.54 | 29.1 | |
| GLY | 685 | 69.88 | 40.40 | 69.88 | 0.00 | 80.1 | o |
| LYS | 686 | 119.15 | 75.29 | 9.61 | 109.54 | 66.6 | o |
| GLN | 687 | 28.50 | 4.81 | 3.29 | 25.20 | 17.5 | i |
| GLU | 688 | 53.59 | 12.72 | 3.72 | 49.87 | 35.3 | |
| VAL | 689 | 87.78 | 85.56 | 2.50 | 85.28 | 69.7 | o |
| THR | 690 | 7.42 | 4.34 | 1.07 | 6.35 | 6.0 | i |
| ILE | 691 | 0.02 | 0.02 | 0.00 | 0.02 | 0.0 | i |
| GLY | 692 | 0.80 | 0.80 | 0.80 | 0.00 | 0.9 | i |
| SER | 693 | 24.12 | 18.32 | 7.17 | 16.95 | 21.9 | |
| ASN | 694 | 24.85 | 0.04 | 0.00 | 24.85 | 21.7 | |
| VAL | 695 | 0.15 | 0.15 | 0.00 | 0.15 | 0.1 | i |
| SER | 696 | 0.85 | 0.55 | 0.00 | 0.85 | 1.1 | i |
| LYS | 697 | 79.06 | 58.45 | 3.25 | 75.82 | 46.1 | |
| ILE | 698 | 0.01 | 0.01 | 0.00 | 0.01 | 0.0 | i |
| TYR | 699 | 13.96 | 10.43 | 0.00 | 13.96 | 7.2 | i |
| GLU | 700 | 48.25 | 34.54 | 1.74 | 46.52 | 32.9 | |
| ALA | 701 | 4.35 | 4.35 | 3.89 | 0.46 | 0.7 | i |
| ILE | 702 | 12.62 | 5.37 | 7.25 | 5.37 | 3.6 | i |
| LYS | 703 | 97.78 | 47.11 | 24.75 | 73.03 | 44.4 | |
| SER | 704 | 77.91 | 58.57 | 33.27 | 44.64 | 57.7 | o |
| GLY | 705 | 23.17 | 14.11 | 23.17 | 0.00 | 26.6 | |
| ARG | 706 | 119.15 | 64.63 | 18.02 | 101.13 | 51.7 | o |
| ILE | 707 | 0.38 | 0.38 | 0.00 | 0.38 | 0.3 | i |
| ASN | 708 | 7.22 | 2.32 | 0.00 | 7.22 | 6.3 | i |
| ASN | 709 | 94.42 | 32.56 | 3.44 | 90.98 | 79.6 | o |
| VAL | 710 | 17.16 | 17.16 | 1.71 | 15.45 | 12.6 | i |
| LEU | 711 | 0.22 | 0.22 | 0.00 | 0.22 | 0.2 | i |
| LEU | 712 | 45.20 | 40.06 | 5.14 | 40.06 | 27.4 | |
| LYS | 713 | 143.75 | 91.18 | 24.27 | 119.48 | 72.6 | o |
| MET | 714 | 0.06 | 0.06 | 0.00 | 0.06 | 0.0 | i |
| LEU | 715 | 13.96 | 6.88 | 13.96 | 0.00 | 0.0 | I |

Example 5

The Use of Molecular Replacement and Other Methods to Solve an Unknown Pal Crystal Structure In the event that significant changes occur to the 3-dimensional structure (e.g. large truncations) and molecular replacement cannot be used, direct MAD (Hendrickson, W. A., et al., (1990) ibid.) and/or SAD (Brodersen, D. E., et al., (2000) ibid.) phasing using selenomethionine-containing PAL was used. For structures that do not change significantly, such as substrate and/or inhibitor-complexed wild-type PAL as well as PAL mutants, these structures were determined using molecular replacement.

Example 6

Protein Engineering of PAL

With the high-resolution three-dimensional PAL protein crystal structure, molecular engineering methods were applied to improve the catalytic efficiency, stability, immunoresistance, and protease resistance to increase the in vivo effectiveness of PAL. With the 1.6 Å resolution structure disclosed above, one of skill in the art can determine the regions of the structure that are the most flexible (to remove and generate a more compact and stable form of PAL), the residues located near the active site (to mutate in order to enhance activity and/or minimize the size of the protein), and the surface locations close to immunogenic (e.g. linear or conformational epitopes identified in mapping studies) and/or proteolytic sensitive sites (from protease mapping studies), thereby allowing for the introduction of site-specific mutants for direct disruption of problem sites or, alternatively, for surface pegylation or other chemical derivatization to protect sensitive sites present in PAL from immunoreaction and/or proteolysis.

Mutagenesis of PAL

The general rationale for mutant generation is based upon four general methods of design. Firstly, truncations, insertions, and point mutations including surface veneering to obstruct or otherwise remove protease and/or immunogenicity sites is used. Secondly, chimeras, including loop re-engineering, loop swapping to graft HAL sequences into the PAL sequence can be used to produce improved PAL variants. Thirdly, point mutants are made to introduce sites for site-specific derivatization. Finally, directed evolution can be used to improve the activity of any mutants made using methods 1-3.

Truncation and Other Mutant Production

Site-directed mutagenesis was performed using the QuikChange kit (Stratagene, U.S. Pat. Nos. 5,789,166 and 6,391,548) and truncations were made with PCR using the appropriate primers designed to generate truncated PAL sequences. Loop spliced mutants were constructed in a two-step PCR process to splice in the appropriate (truncated) loop sequence into the wild-type PAL sequence. All mutations were confirmed with DNA sequencing.

Loop-directed engineering were used for PAL molecular architecture improvement, with surface loops in the PAL structure selected for incorporation of point mutagenesis or alternatively, incorporation of saturation site mutagenesis, along with the possible inclusion of directed evolution methods to fully improve the PAL molecular framework for therapeutic advantage.

Based on the overall 3-D structure of PAL and the mapping results of protease-sensitive sites and major epitope immunogenic sites in PAL, specific point mutants of His-tagged PAL were constructed to remove these sites of protease/immunogenic sensitivity followed by selection for activity, or, alternatively, point mutants were made to introduce specific amino acid residues in these PAL loop regions for site-specific pegylation derivatization (Hershfield, et al., (1991) ibid.; Bhadra, et al., (2002) ibid., Vasserot, et al., (2003) ibid., Sato, Adv. Drug Deliv. Rev., 54(4), pp. 487-504 (2002)).

Single point mutations in the trypsin (Arg123) and chymotrypsin (Tyr110) primary recognition sites that were identified by protein sequence were made: mutations in the trypsin site were Arg123His, Arg123Ala and Arg123Gln, and in the chymotrypsin site Tyr110His, Tyr110Ala and Tyr110Leu. The mutant T124P was made to test if the trypsin target site, Arg123, was protected from proteolysis when the recognition sequence for this protease was modified. All mutants had decreased activity relative to wt-PAL, however, reduced proteolytic susceptibility was evident in numerous samples (reduced proteolysis as determined by SDS-PAGE analysis of PAL variant protease digestions).

Figures 7A, 7B:
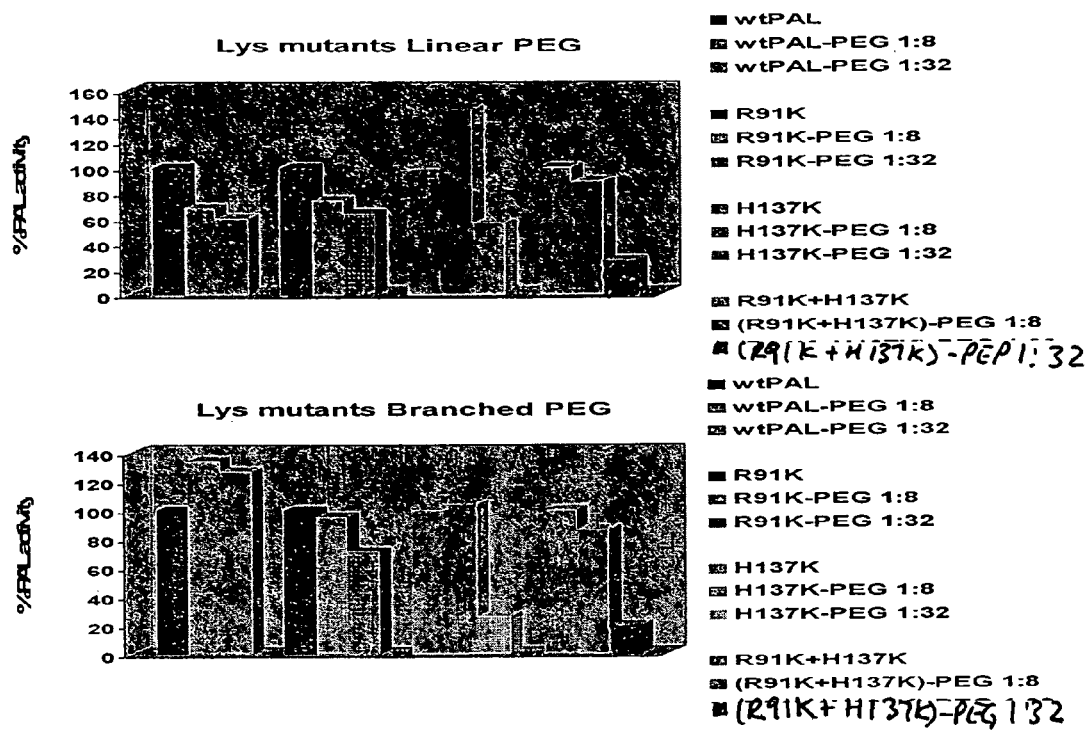
FIGS. 7A and 7B are graphs that show the activity of pegylated PAL mutants relative to wild-type PAL (activities are in μmol/min×mg).

Single point mutations in several residues were made to introduce additional lysine sites in the protein that can be pegylated: R91K, R102K, Q104K, S108K, T114K, T124K, Q131K, and H137K (FIG. 4). Among these mutations, the R91K and H137K showed an increase or similar catalytically activity compared to wt-PAL, respectively, and these mutations were then introduced in the pIBXPAL vector for further expression and pegylation analysis. The double mutant R91K+H137K was also made and the pegylation of these new constructs looks promising in terms of activity (FIG. 7) and immune protection. Residue R91K is partially surface-exposed and located in alpha-helix Asp86-Leu101, whereas residue H137K is internal to the PAL structure and located in alpha-helix Asp126-Leu139 (the ND1 of H137 forms hydrogen bonds with the amide carbonyls of Ala133 and Leu134 while the NE2 of H137 hydrogen bonds to Gln138). Table 5 shows the catalytic activity of several mutants generated by single point mutation in comparison with the activity of wild-type PAL and the double mutant R91K+E403Q before and after pegylation. The H598Q mutant was generated to attempt to attenuate the immunogenicity of the epitope predicted by the B-Cell epitope mapping data wherein a region defined by residues 597-601 was defined as immunodominant. H598 is the only one partially exposed residue in this region and was mutated into a smaller and neutral amino acid Gln. K132 is located at the helix 125-138, which connects with loop 101-124 and loop 139-152. This helix is the only one that shows positive polarity around MIO. K132 is partially exposed on surface and was mutated into Arg to reduce the lysine number and enhance polarity of this helix. The triple mutants, R91K+E403Q+H598Q and R91K+E403Q+K132R, showed an increase in activity in comparison with that of the double mutant R91K+E403Q after pegylation.

TABLE 5

| MUTATION | ACTIVITY (IU/mg) (−PEG) | ACTIVITY (% WT) | ACTIVITY (IU/mg) (+PEG) | ACTIVITY (% WT) |
| --- | --- | --- | --- | --- |
| Control: wild-type (WT) | 2.13 | 100 | 2.08 | 100 |
| Control: R91K + E403Q | 2.47 | 116 | 2.37 | 114 |
| H598Q | 3.43 | 161 | 2.45 | 118 |
| K132R | 3.16 | 148 | 3.7 | 178 |
| H312N | 2.9 | 136 | 2.28 | 110 |
| K78R | 2.76 | 130 | 2.04 | 98 |
| K240R | 2.61 | 123 | 2.33 | 112 |

Additional site-directed mutants of PAL can be constructed to introduce Lys residues in the vicinity of proteolytic and/or immunogenic regions to provide regions for PEG derivatization that will prevent PAL proteolytic and/or immunogenic sensitivity.

The following primers are used for PAL mutagenesis.

```
PAL_R91K      5'-GGA CAG CGA CGA GAT CAA GTC AAA
              GAT TGA CAA ATC GG-3'
COMPLEMENT:   5'-CCG ATT TGT CAA TCT TTG ACT TGA
              TCT CGT CGC TGT CC-3'
              (SEQ ID NOS 6 and 7)

PAL_R102K     5'-CGG TCG AGT TCT TGA AGT CGC AAC
              TCT CCA TGA G-3'
COMPLEMENT:   5'-CTC ATG GAG AGT TGC GAC TTC AAG
              AAC TCG ACC G-3'
              (SEQ ID NOS 8 and 9)

PAL_Q104K     5'-CGA GTT CTT GCG CTC GAA ACT CTC
              CAT GAG CGT C-3'
              (SEQ ID NOS 14)
COMPLEMENT:   5'-GAC GCT CAT GGA GAG TTT CGA GCG
              CAA GAA CTC G-3'
              (SEQ ID NOS 10 and 11)

PAL_S108K     5'-GCG CTC GCA ACT CTC CAT GAA AGT
              CTA CGG CGT CAC GAC-3'
COMPLEMENT:   5'-GTC GTG ACG CCG TAG ACT TTC ATG
              GAG AGT TGC GAG CGC-3'
              (SEQ ID NOS 12 and 13)

PAL_V109K     5'-GCA ACT CTC CAT GAG CAA GTA CGG
              CGT CAC GAC TGG ATT TGG CGG-3'
              (SEQ ID NO: 14)

PAL_Tyr110His 5'-GCA ACT CTC CAT GAG CGT CCA CGG
              CGT CAC GAC TGG ATT TGG CGG-3'
COMPLEMENT:   5'-CCG CCA AAT CCA GTC GTG ACG CCG
              TGG ACG CTC ATG GAG AGT TGC-3'
              (SEQ ID NOS 15 and 16)

PAL_Tyr110Ala 5'-GCA ACT CTC CAT GAG CGT CGC CGG
              CGT CAC GAC TGG ATT TGG CGG-3'
COMPLEMENT:   5'-CCG CCA AAT CCA GTC GTG ACG CCG
              GCG ACG CTC ATG GAG AGT TGC-3'
              (SEQ ID NOS 17 and 18)

PAL_Tyr110Leu 5'-GCA ACT CTC CAT GAG CGT CCT CGG
              CGT CAC GAC TGG ATT TGG CGG-3'
COMPLEMENT:   5'-CCG CCA AAT CCA GTC GTG ACG CCG
              AGG ACG CTC ATG GAG AGT TGC-3'
              (SEQ ID NOS 19 and 20)
```

```
PAL_Y110K    5'-GCA ACT CTC CAT GAG CGT CAA GGG
             CGT CAC GAC TGG ATT TGG CGG-3'
             (SEQ ID NO: 21)

PAL_Y110T    5'-GCA ACT CTC CAT GAG CGT CAC CGG
             CGT CAC GAC TGG ATT TGG CGG-3'
             (SEQ ID NO: 22)

PAL_Y110Q    5'-GCA ACT CTC CAT GAG CGT CCA GGG
             CGT CAC GAC TGG ATT TGG CGG-3'
             (SEQ ID NO: 23)

PAL_Y110N    5'-GCA ACT CTC CAT GAG CGT CAA CGG
             CGT CAC GAC TGG ATT TGG CGG-3'
             (SEQ ID NO: 24)

PAL_Y110M    5'-GCA ACT CTC CAT GAG CGT CAT GGG
             CGT CAC GAC TGG ATT TGG CGG-3'
             (SEQ ID NO: 25)

PAL_T114K    5'-GAG CGT CTA CGG CGT CAC GAA AGG
             ATT TGG CGG ATC CGC-3'
COMPLEMENT:  5'-GCG GAT CCG CCA AAT CCT TTC GTG
             ACG CCG TAG ACG CTC-3'
             (SEQ ID NOS 26 and 27)

PAL_Arg123His 5'-CCG CAG ACA CCC ACA CCG AGG ACG
             CCA TCT CG-3'
COMPLEMENT:  5'-CGA GAT GGC GTC CTC GGT GTG GGT
             GTC TGC GG-3'
             (SEQ ID NOS 28 and 29)

PAL_Arg123Ala 5'-CCG CAG ACA CCG CCA CCG AGG ACG
             CCA TCT CG-3'
COMPLEMENT:  5'-CGA GAT GGC GTC CTC GGT GGC GGT
             GTC TGC GG-3'
             (SEQ ID NOS 30 and 31)

PAL_Arg123Gln 5'-CCG CAG ACA CCC AGA CCG AGG ACG
             CCA TCT CG-3'
COMPLIMENT:  5'-CGA GAT GGC GTC CTC GGT CTG GGT
             GTC TGC GG-3'
             (SEQ ID NOS 32 and 33)

PAL_R123K    5'-CCG CAG ACA CCA AGA CCG AGG ACG
             CCA TCT CG-3'
             (SEQ ID NO: 34)

PAL_R123V    5'-CCG CAG ACA CCG TCA CCG AGG ACG
             CCA TCT CG-3'
             (SEQ ID NO: 35)

PAL_R123N    5'-CCG CAG ACA CCA ACA CCG AGG ACG
             CCA TCT CG-3'
             (SEQ ID NO: 36)

PAL_R123T    5'-CCG CAG ACA CCA CCA CCG AGG ACG
             CCA TCT CG-3'
             (SEQ ID NO: 37)

PAL_T124P    5'-CGG ATC CGC AGA CAC CCG CCC AGA
             GGA CGC CAT CTC GCT C-3'
COMPLEMENT:  5'-GAG CGA GAT GGC GTC CTC TGG GCG
             GGT GTC TGC GGA TCC G-3'
             (SEQ ID NOS 38 and 39)

PAL_T124K    5'-CGG ATC CGC AGA CAC CCG CAA AGA
             GGA CGC CAT CTC GCT C-3'
COMPLEMENT:  5'-GAG CGA GAT GGC GTC CTC TTT GCG
             GGT GTC TGC GGA TCC G-3'
             (SEQ ID NOS 40 and 41)

PAL_Q131K    5'-CCG AGG ACG CCA TCT CGC TCA AGA
             AGG CTC TCC TCG-3
COMPLEMENT:  5'-CGA GGA GAG CCT TCT TGA GCG AGA
             TGG CGT CCT CGG-3'
             (SEQ ID NOS 42 and 43)

PAL_H137K    5'-CAG AAG GCT CTC CTC GAG AAA CAG
             CTC TGC GGT GTT C-3'
COMPLEMENT:  5'-GAA CAC CGC AGA GCT GTT TCT CGA
             GGA GAG CCT TCT G-3'
             (SEQ ID NOS 44 and 45)
```

Additional mutations based on the computational predicted PAL epitopes using the program Peptide Companion (predictions determined by Bionexus) were made in the R91K mutant form of the protein. The positive mutations (catalytically active and improved immune resistance) were introduced into wt-PAL and R91K-PAL constructs for further expression, activity, pegylation, immunogenicity, protease susceptibility and in vivo studies.

Single point mutations made included:
In the epitope 226-243: H237S, H237Q, H237G, E238Q
In the epitope 337-356: R340K, K352R, E337Q, E346Q, E347Q
In the epitope 396-413: E403Q
In the epitope 569-589: R570K, E575Q, E586Q, D571S
In the epitope 619-630: E631Q In addition, deletion of residues in PAL epitopes included:
del__61-84, del__237-238, del__348-356, del__396-410, and del__541-655

The following primers are used for R91K-PAL variant mutagenesis.

Mutagenesis Epitopes PAL

```
H237S_Fwd   5'-GCA AGG TGC ACG TCG TCA GCG AGG GCA
            AGG AGA AG-3'
            (SEQ ID NO: 46)

H237S_Rev   5'-CTT CTC CTT GCC CTC GCT GAC GAC GTG
            CAC CTT GC-3'
            (SEQ ID NO: 47)

H237Q_Fwd   5'-GCA AGG TGC ACG TCG TCC AAG AGG GCA
            AGG AGA AGA TCC-3'
            (SEQ ID NO: 48)

H237Q_Rev   5'-GGA TCT TCT CCT TGC CCT CTT GGA CGA
            CGT GCA CCT TGC-3'
            (SEQ ID NO: 49)

H237G_Fwd   5'-GCA AGG TGC ACG TCG TCG GCG AGG GCA
            AGG AGA AG-3'
            (SEQ ID NO: 50)

H237G_Rev   5'-CTT CTC CTT GCC CTC GCC GAC GAC GTG
            CAC CTT GC-3'
            (SEQ ID NO: 51)

E238Q_Fwd   5'-AGC AAG GTG CAC GTC GTC CAC CAG GGC
            AAG GAG AAG-3'
            (SEQ ID NO: 52)

E238Q_Rev   5'-CTT CTC CTT GCC CTG GTG GAC GAC GTG
            CAC CTT GCT-3'
            (SEQ ID NO: 53)

E403Q_Fwd   5'-CCC TCT CAT CGA CGT CCA GAA CAA GAC
            TTC GCA CCA CGG CGG-3'
            (SEQ ID NO: 54)

E403Q_Rev   5'-CCG CCG TGG TGC GAA GTC TTG TTC TGG
            AGC TCG ATG AGA GGG-3'
            (SEQ ID NO: 55)

R340K_Fwd   5'-GCT CCT CGA GGG AAG CAA GTT GCT GT
            CCA CCA TGA GGA GG-3'
            (SEQ ID NO: 56)
```

```
R340K_Rev  5'-CCT CCT CAT GGT GGA CAG CAA ACT TGC
           TTC CCT CGA GGA GC-3'
           (SEQ ID NO: 57)

K352R_Fwd  5'-GGA GGT CAA GGT CAG GGA CGA CGA GGG
           C-3'
           (SEQ ID NO: 58)

K352R_Rev  5'-GCC CTC GTC GTC CCT GAC CTT GAC CTC
           C-3'
           (SEQ ID NO: 59)

E337Q_Fwd  5'-CAT CCG AAG CTT CCT CCA GGG AAG CCG
           CTT TGC-3'
           (SEQ ID NO: 60)

E337Q_Rev  5'-GCA AAG CGG CTT CCC TGG AGG AGC TTG
           CGG ATG-3'
           (SEQ ID NO: 61)

E346Q_Fwd  5'-GCT GTC CAC CAT CAG GAG GAG GTC AAG
           GTC-3'
           (SEQ ID NO: 62)

E346Q_Rev  5'-GAC CTT GAC CTC CTC CTG ATG GTG GAC
           AGC-3'
           (SEQ ID NO: 63)

E347Q_Fwd  5'-GCT GTC CAC CAT GAG CAG GAG GTC AAG
           GTC AAG G-3'
           (SEQ ID NO: 64)

E347Q_Rev  5'-CCT TGA CCT TGA CCT CCT GCT CAT GGT
           GGA CAG C-3'
           (SEQ ID NO: 65)

R570K_Fwd  5'-CCG GCT CGA ACC TGA AGG ACG AGC TCG
           TCG AGA AGG-3
           (SEQ ID NO: 66)

R570K_Rev  5'-CCT TCT CGA CGA GCT CGT CCT TCA GGT
           TCG AGC CGG-3'
           (SEQ ID NO: 67)

E575Q_Fwd  5'-GCG CGA CGA GCT CGT CCA GAA GGT GAA
           CAA GAC GC-3'
           (SEQ ID NO: 68)

E575Q_Rev  5'-GCG TCT TGT TCA CCT TCT GGA CGA GCT
           CGT CGC GC-3'
           (SEQ ID NO: 69)

E586Q_Fwd  5'-CGC CAA GCG CCT CCA GCA GAC CAA CTC
           G-3'
           (SEQ ID NO: 70)

E586Q_Rev  5'-CGA GTT GGT CTG CTG GAG GCG CTT GGC
           G-3'
           (SEQ ID NO: 71)

D571S_Fwd  5'-GGC TCG AAC CTG CGC TCC GAG CTC GTC
           GAG AAG GTG-3'
           (SEQ ID NO: 72)

D571S_Rev  5'-CAC CTT CTC GAC GAG CTC GGA GCG CAG
           GTT CGA GCC-3'
           (SEQ ID NO: 73)

E631Q_Fwd  5'-CGC CGC CGC CCA GTC GGC CAT CTC GC-
           3'
           (SEQ ID NO: 74)

E631Q_Rev  5'-GCG AGA TGG CCG ACT GGG CGG CGG CG-
           3'
           (SEQ ID NO: 75)
```

Deletions PAL Epitopes

```
                          (SEQ ID NO: 76)
del_541-655 Fwd  5'-GTT CTC AAC GCC ATC GAC TTG CGC
                 GCG ATC TCG TAC CTC TCG CCG CGC
                 ACT CAG-3'

(SEQ ID NO: 77)
del_541-655 Rev  5'-CTG AGT GCG CGG CGA GAG GTA CGA
                 GAT CGC GCG CAA GTC GAT GGC TTG
                 GAG AAC-3'

(SEQ ID NO: 78)
del_237-238 Fwd  5'-GAC AGC AAG GTG CAC GTC GTC GGC
                 AAG GAG AAG ATC CTG TAC GCC-3'

(SEQ ID NO: 79)
del_237-238 Rev  5'-GGC GTA CAG GAT CTT CTC CTT GCC
                 GAC GAC GTG CAC CTT GCT GTC-3'

(SEQ ID NO: 80)
del_348-356 Fwd  5'-GCC GCT TTG CTG TCC ACC ATG AGG
                 AGA TTC TCC GCC AGG ACC GCT ACC
                 CC-3'

(SEQ ID NO: 81)
del_348-356 Rev  5'-GGG GTA GCG GTC CTG GCG GAG AAT
                 CTC CTC ATG GTG GAC AGC AAA GCG
                 GC-3'

(SEQ ID NO: 82)
del_61-84 Fwd    5'-CCG CGC CGA CCG ACT CGA CGC TCA
                 AGG ACA GCG ACG AGA TCC GCT C-3'

(SEQ ID NO: 83)
del_61-84 Rev    5'-GAG CGG ATC TCG TCG CTG TCC TTG
                 AGC GTC GAG TCG GTC GGC GCG G-3'

(SEQ ID NO: 84)
del_396-410 Fwd  5'-CAT CGA GGC CGG CCA GTC GAC GAC
                 CGG CAA TTT CCA GGC TGC GGC TGT
                 GGC-3'

(SEQ ID NO: 85)
del_396-410 Rev  5'-GCC ACA GCG GCA GCC TGG AAA TTG
                 CCG GTC GTC GAC TGG CCG GCC TCG
                 ATG-3'
```

In another method, site saturation mutagenesis is applied to specific loop sequences to mutate these regions of the PAL sequence to remove any unfavorable features found on the PAL surface (Miyazaki, et al., J. Mol. Evol., 49(6), pp. 716-720 (1999); Palzkill, et al., Proteins, 14(1), pp. 29-44 (1992)). Finally, if rational engineering proves difficult to generate an improved PAL mutant, the directed evolution methods of DNA shuffling (Crameri, et al., (1998) ibid.) and molecular breeding (Minshull, et al., (1999) ibid.) can be used on PAL in combination with HAL and/or mutants of PAL to optimize the PAL protein architecture. Directed evolution techniques have been used to improve kinetic and other biophysical features of enzymes, and can be used to alter the pH activity profile for PAL, using alternative pH values for the mutant selection process. In addition, for rationally-designed PAL clones that produce enzymatically poor PAL mutants (such as the R123H, R123A, and R123Q PAL mutants with protease resistance but minimal activity), these mutants can be used as starting points for directed evolution enzymatic activity improvement (as exemplified in (Vasserot, et al., (2003) ibid.)).

Protease mapping studies on native PAL have indicated primary sites of proteolytic sensitivity. These sites cab be removed for the development of an effective oral PKU enzyme substitute. In the first cycle of improvement of the PAL architecture, smaller sized PAL proteins were constructed and screened for retention of activity (using a simple absorbance assay for activity measurement), and in the second cycle of improvement, protein engineering was used to screen for mutants with reduced proteolytic sensitivity. Once the size of the PAL protein is minimized, protease susceptible sites were removed from the PAL framework using a combination of rational and directed evolution methods. The first avenue of modification used site-specific pegylation to mask and remove proteolytically sensitive sites from the surface of PAL. Mutations were made in PAL surface residues at or near the protease sensitive sites (primary sites Tyr110 and Arg123) to add Lys or Cys sites, or to mutate to other residues to abolish such sites. For rationally designed PAL mutants that are inactive, protein engineering using directed evolution with selection in phenylalanine auxotrophic E. coli strains for active mutant proteins was used to produce active mutant forms of PAL, e.g. for further pegylation derivatization.

All directed evolution mutagenesis methods used initial growth and selection in defined minimal media with transformation into an E. coli mutant deficient in PAL activity to identify enzymatically-active mutants. Mutation used mutant PAL clones that display minimal activity (e.g. Y110A, Y101L, or S108K) such that positive selection for new mutants with activity will be the first clone identification step. Either strain JP2250, an E. coli strain that requires tyrosine for growth (Baldwin, et al., Biochem. Biophys., 211(1), pp. 66-75 (1981)), or strain AT2471 (tyrA) which is a mutant auxotrophic for tyrosine (Zhao, et al., Proc. Natl. Acad. Sci. U.S.A., 91(4), pp. 1366-1370 (1994)), were used for positive selection of functional His-tagged PAL clones by inducing and plating transformed cells on M9 minimal media lacking tyrosine and phenylalanine.

Alternatively, the phenylalanine auxotroph studied by Simmonds, et al., were utilized (Simmonds, et al., J. Bacteriol., 83, pp. 256-263 (1962)). Since R. toruloides PAL reacts in a reversible fashion with both L-Phe and tyrosine as substrates, active PAL mutants are selected by growing the transformed and IPTG induced E. coli cells in the presence of the products of the PAL reaction (trans-cinnamic acid, trans-coumaric acid, and ammonium chloride) to select for mutant PALs displaying reverse PAL reaction reactivity. Alternatively, the phenylalanine auxotroph [cited in Gu, et al., Microb Comp Genomics 2(2): 141-158 (1997)] is used for selection.

Analysis of promising clones made with PAL mutagenesis experimentation involved the characterization of purified clones (including $V_{max}$ and $K_m$ determinations, binding constants of substrates, proteolytic stability, in vitro immunogenicity, pH dependence of activity, temperature-dependence of activity), using the optical absorbance kinetic measurement method for PAL, as well as sequencing to determine the sites of mutation that are present in mutant candidates. Promising PAL clones that pass the activity, immunogenicity, and protease susceptibility requirements are subjected to testing in the murine PKU model system, possibly after pegylation derivatization, dependent on the engineering scheme under consideration. Additionally, mapping of these favorable sites of mutation onto the PAL 3-D structure allows the mechanisms involved with the improved stability to be determined. After initial rounds of directed evolution, the results indicate whether 'hotspots' and/or other structure-based functional correlations exist. Further rounds of directed evolution can incorporate site-saturation mutagenesis of functionally important 'hotspots' to improve in vivo enzymatic efficiency further.

Mutants obtained by directed evolution are studied using pegylation. If pegylation of mutant PAL proteins does not occur under normal pegylation conditions (varied pH, pegylation reaction time, molar ratio PEG:protein, varying the molecular weights of the PEGs (Hershfield, et al., 1991 ibid.)), further site-directed mutagenesis of surface residues into lysine or cysteine residues is employed to introduce further pegylation sites into the positive clones from the directed evolution experiments.

Activity Assay for PAL variants

Initial selection for active PAL variants uses the optical density activity measurement, the same as native or pegylated PAL samples.

Example 7

The vector pIBEX-PAL was used to express PAL in E. coli with no tags, and protein was purified using literature method (Sarkissian et al. Proc. Natl. Acad. Sci. USA (1999)) with the following modifications. After homogenization, the PAL lysate was heated at 55° C. for two hours followed by centrifugation. Activated charcoal was added to the filtrated liquid fraction and rocked overnight. The clarified lysate was loaded onto a hydrophobic interaction chromatography resin (Toyopearl Butyl 650M; Tosoh Biosciences, San Diego, Calif.) once the solution was adjusted by adding 1 M Tris, pH 7.8 and ammonium sulfate salt. The product was eluted using a buffer having 25 mM Tris, 120 mM ammonium sulfate, pH 7.8. The PAL eluate solution was diluted with 25 mM Tris, pH 7.8, to a conductivity of 5 mS and loaded onto a Macro Prep High Q column (BioRad, Hercules, Calif.); the product was eluted with a step gradient of 90 mM NaCl. PAL activity measurements were performed using standard reaction conditions with a Cary 50 UV spectrophotometer in the kinetics mode.

Example 8

PEG:PAL conjugates were produced by coupling either linear 5 kDa or 20 kDa methoxy-PEG-SPA (Nektar Therapeutics) or 10 kDa or 40 kDa branched methoxy-(PEG)2-NHS (Nektar Therapeutics) to PAL. A number of pegylation conditions were initially tested for each PEG reactant, using an established reaction protocol (Hershfield, et al., Proc. Natl. Acad. Sci., USA, 88 (1991), pp. 7185-7189). Reaction conditions were optimized for PAL protein with regards to different buffers, different temperatures for a given reaction, various molar ratios of PAL to PEG, different pH values, and reaction times.

The concentration of PAL in the reaction mixture was 1 mg/ml in 50 mM potassium phosphate buffer, pH 8.5. The amount of PEG to add was calculated based on the number of lysines present in PAL (29), the number of subunits in PAL (4), and the molar ratio excess of PEG chosen (n), as described by:

grams mPEG-SPA or m(PEG)2-NHS=(moles PAL)(# PAL subunits)(# lysines/subunit)(MW mPEG-SPA)(n-fold increase of mPEG-SPA or m(PEG)2-NHS to PAL)

The molar excess of PEG used was 1-32 fold (Table 6).

TABLE 6

PEG:PAL ratios studied for the different PEGs used (linear mPEG-SPA succinimidyl active ester and branched m(PEG)2-NHS ester)

| PEGs | Molar ratios |
|---|---|
| Linear 5 kDa | 1:2, 1:4, 1:8, 1:16, 1:32 |
| Linear 20 kDa | 1:1, 1:2, 1:4, 1:8, 1:12, 1:16 |

TABLE 6-continued

PEG:PAL ratios studied for the different PEGs used
(linear mPEG-SPA succinimidyl active ester and
branched m(PEG)2-NHS ester)

| PEGs | Molar ratios |
|---|---|
| Linear (5 + 20) kDa | (1:4 + 1:16), (1:4 + 1:2) |
| Branched 10 kDa | 1:2, 1:4, 1:8, 1:16, 1:24, 1:32 |
| Branched 40 kDa | 1:1, 1:2, 1:5 |

After the appropriate amounts of PEG and PAL were mixed together, pegylation reactions were incubated, while rocking, at 25° C. for 5 hours up to overnight and then stopped by placing the reactions at 4° C. or −20° C. The degree of modification was controlled by varying the PEG concentration, temperature and time of reaction. Prior to sample characterization, and in order to remove the unreacted excess of PEG, all samples were extensively dialyzed. After the protein modification reaction was completed and in order to remove excess of unreacted PEG, the samples were dialyzed against 1×DPBS, pH 7.4 buffer overnight at 4° C. with stirring using Tube-O-Dialyzer (GenoTechnology). Once protein concentration was determined using the NI protein assay kit (Geno Technology), PAL activity measurements were performed on underivatized and PEG derivatized PAL samples using standard reaction conditions measuring the trans-cinnamic acid production at Abs 290 nm at RT.

Example 9

Figure 8:
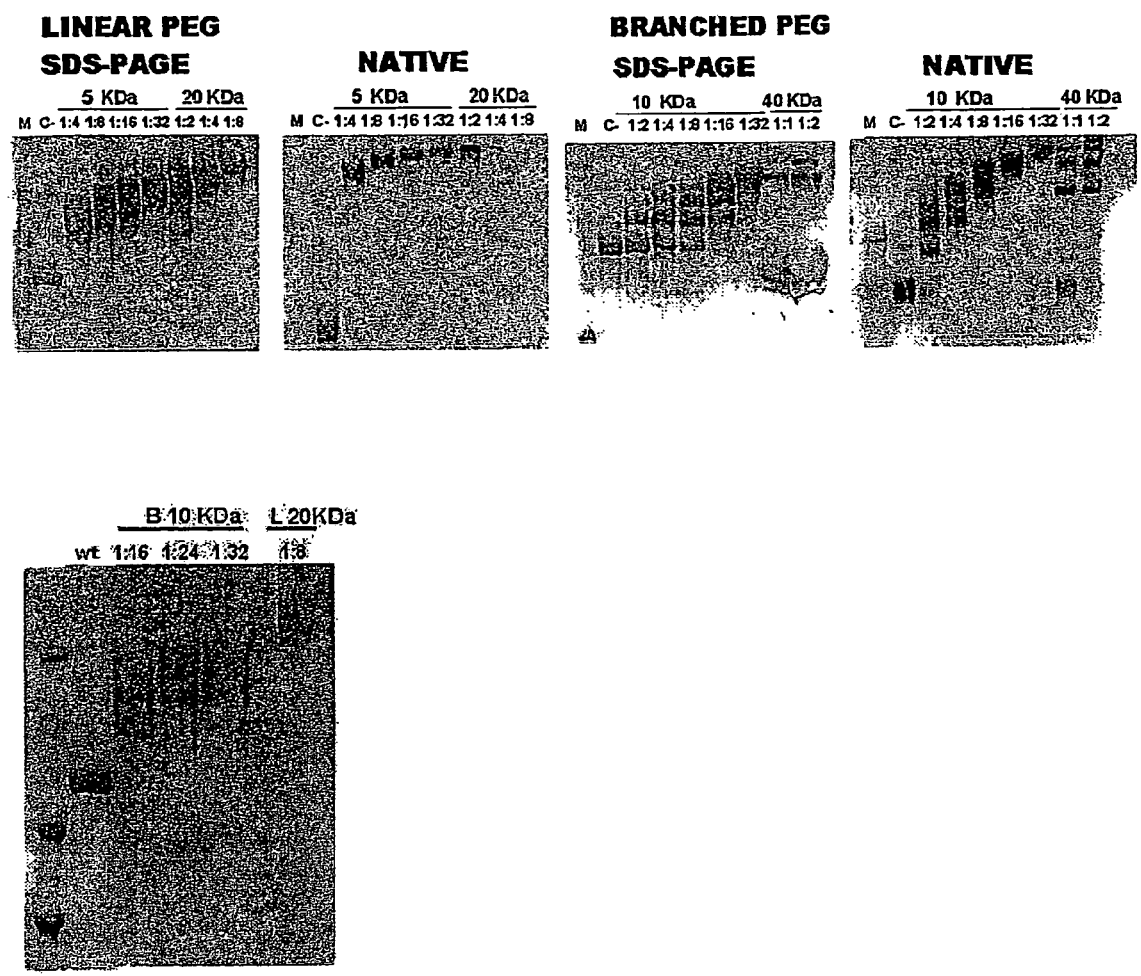
FIG. 8 depicts the SDS-PAGE and Native gel analysis of the 5 kDa and 20 kDa linear and 10 kDa and 40 kDa branched PEG:PAL conjugates.

This example demonstrates the effects on activity of the degree of substitution and variations of the polymer size and conformation for PEG:PAL conjugates. Using both methoxy-PEG-SPA and methoxy-(PEG)-NHS, a variety of PEG:PAL conjugates were synthesized from 5 kDa or 20 kDa or a combination of 5 kDa +20 kDa linear polymers as well as 10 kDa or 40 kDa branched polymers. Samples of PEG:PAL were characterized with SDS-PAGE and MALDI-TOF-MS analysis for analysis of the extent of derivatization. The resultant preparations ranged in size from about 80 kDa to about 200 kDa, as estimated by SDS-PAGE (FIG. 8). In addition, degree of retention of activity was measured with the optical absorbance assay (Table 8).

Pegylated PAL samples were analyzed by sodium dodecylsulfate-polyacrylamide gel electrophoresis (SDS-PAGE) using 4-10% Bis-Tris gels and 4% and 4-12% Tris-Glycine native gels (NuPage gels from Invitrogen) (FIG. 8). Native gel analysis on pegylated forms of PAL have shown no evidence for tetramer dissociation, even at high PAL:PEG ratios, confirming the oligomeric states of the pegylated PAL species formed.

The number of PEG molecules attached to each pegylated PAL conjugate was quantitatively determined using matrix-assisted laser desorption ionization time-of-flight mass spectrometry (MALDI-TOF MS) using 0.5 M urea or 0.025 M guanidine-HCl to improve subunit dissociation. As shown in Table 8, a number of different pegylated species are formed with PAL. All the lysine residues present in PAL (29 total) are surface exposed and presumably available for derivatization. As published previously, MALDI-TOF MS provides an accurate technique to characterize the number of PEGs that are attached to protein-derivatized species (Lee, et al., Pharm. Res., 1999, 16(6), pp. 813-818; Lee, et al., Pharm. Res., 2003, 20(5), pp. 818-825; Diwan, et al., Int. J. Pharm., 2003, 252 (1-2), pp. 111-122; Na, et al., Rapid Commun. Mass Spectrom. 2003, 17, pp. 2241-2244). The relative number of PEG units present in each PAL derivative species can be directly determined from the MALDI-TOF MS spectra; MALDI ionization disrupts the PAL oligomeric associations along with the use of agents such as urea or guanidine-HCl, which help to release the respective PAL subunits from their oligomeric conformation.

In the case of the linear 20 KDa PALPEG molecules, due to the high MW of them, it was not possible to determine the state of the modified protein by either native gel or MALDI-TOF analysis due to the limitation of resolution for high MW molecules with this particular technique. The MALDI-TOF results of the branched 10 KDa series showed that 1 and 2 PEG molecules were attached per PAL monomer for the ratio 1:16 and 1, 2 and 3 for the 1:24 specie.

Western blot analysis was used to characterize in vitro the degree of PAL sample's immunological reactivity for the branched PEG samples using Native gels. The results showed a slight immune protection by the branched PEG compared to the native protein which also correlates with the in vivo results described below. The linear PEG 20 KDa was unable to be tested by this technique due to the high MW of the sample but in other samples using the same type of PEG, the ratio 1:8 of the linear 20 KDa PEG conferred a complete immune protection when it was tested by Immunoprecipitation.

One of the aims in developing an enzyme substitute to use for PKU or tyrosinemia therapy is to have the PEG derivatized form(s) of the enzyme retain catalytic activity. As listed in Table 8, activity measurements on pegylated PAL samples indicated that this was indeed the case, with only very highly pegylated samples losing a small degree of catalytic activity. In most cases of enzyme pegylation, decreases in catalytic activity are realized (Harris, et al., Nat. Rev. Drug Discov. 2(3): 214-221 (2003)), however, a similar improvement in activity has been observed upon pegylation of the enzyme phenylalanine hydroxylase (Gamez, et al., Mol. Ther., 9(1): 124-129 (2004)). Surprisingly, all of these pegylated forms of PAL retained, and in some instances possessed increased catalytic activity versus their non-pegylated forms (Table 7).

TABLE 7

Activity measurements for different PEG:PAL conjugates (based on spectrophotometric analysis of trans-cinnamic acid production at 290 nm) and MALDI-TOF MS characterization of extent of PEG derivatization.

| | PAL specific activity (μmol/min · mg) | # PEG/PAL monomer[a] | Immunoassays | | |
|---|---|---|---|---|---|
| | | | Western[c] | ELISA[d] | Immunoprecipitation[e] |
| Wild-type PAL Linear PEG 5 kDa | 2.43 | 0 | + | + | + |
| PAL:PEG 1:2 | 2.24 | nt | nt | nt | nt |
| PAL:PEG 1:4 | 2.71 | 2, 3, 4, 5, 6, 7 | nt | nt | nt |
| PAL:PEG 1:8 | 3.07 | 7, 8, 9 | + | − | + |

TABLE 7-continued

Activity measurements for different PEG:PAL conjugates (based on spectrophotometric analysis of trans-cinnamic acid production at 290 nm) and MALDI-TOF MS characterization of extent of PEG derivatization.

| | PAL specific activity (μmol/min · mg) | # PEG/PAL monomer[a] | Western[c] | Immunoassays ELISA[d] | Immunoprecipitation[e] |
|---|---|---|---|---|---|
| PAL:PEG 1:16 | 2.23 | 11 | +/− | − | − |
| PAL:PEG 1:32 | 2.12 | 12 | − | − | − |
| Linear PEG 20 kDa | | | | | |
| PAL:PEG 1:2 | 2.57 | 1, 2, 3, 4 | + | + | +/− |
| PAL:PEG 1:4 | 2.4 | 1, 2, 3, 4, 5 | n/a | +/− | − |
| PAL:PEG 1:8 | 2.34 | 6[b] | n/a | − | − |
| PAL:PEG 1:16 | 2.35 | 7[b] | n/a | nt | − |
| PAL:PEG 1:32 | 1.59 | 8[b] | n/a | nt | − |
| LinearPEG (5 + 20 kDa) | 1.71 | nt | nt | nt | nt |
| Branched PEG 10 kDa | | | | | |
| PAL:PEG 1:2 | 3.12 | 1, 2 | nt | nt | nt |
| PAL:PEG 1:4 | 2.61 | 1, 2 | nt | nt | nt |
| PAL:PEG 1:8 | 2.8 | 1, 2, 3 | + | + | + |
| PAL:PEG 1:16 | 2.39 | 1, 2, 3 | + | + | +/− |
| PAL:PEG 1:18 | 2.37 | 1, 2, 3, 4, 5 | + | + | +/− |
| PAL:PEG 1:24 | 2.19 | 1, 2, 3 | +/− | +/− | − |
| PAL:PEG 1:28 | 2.85 | 1, 2, 3, 4 | − | − | − |
| PAL:PEG 1:32 | 1.97 | 3, 4, 5 | − | − | − |
| PAT:PEG 1:32 4C | 1.88 | nt | nt | nt | nt |
| PAT:PEG 1:32 RT | 2.99 | 1, 2, 3, 4, 5 or 3, 4, 5 | nt | nt | nt |
| Branched PEG 40 kDa | | | | | |
| PAL:PEG 1:1 | 2.84 | 1, 2[b] | + | + | nt |
| PAL:PEG 1:2 | 2.99 | 1, 2[b] | + | + | nt |
| PAL:PEG 1:5 | 1.86 | 2, 3[b] | n/a | nt | nt |

Abbreviations:

nt, not tested;

n/a, not applicable (samples unable to run on Native gel)

+: binding;

−: non binding;

+/−: partial binding

[a]Number of PEG molecules attached to each PAL monomer using matrix-assisted laser desorption ionization time-of-flight mass spectrometry (MALDI-TOF MS) using 0.5M urea or 0.4M guanidine-HCl to improve subunit dissociation and detection reproducibility.

[b]To estimate the number of PEGs attached per monomer of PAL of high molecular weight pegylated species, we used reducing and native 4-12% Bis-Tris gels which were run in MES (2-(N morpholino) ethane sulfonic acid) buffer using MultiMark and HWM native marker in reducing conditions (Amersham Bioscience, Piscataway, NJ).

[c]Western blot samples were run on native gels and transferred to nitrocellulose membranes. Anti-serum from PAL treated mice was the positive control, antibody and serum from buffer-treated mice was the negative control. Alkaline phosphatase-conjugated goat anti-mouse IgG (Promega, Madison, WI) was the secondary antibody and color was developed using Western Blue (Promega). These results were scored as follows: (+) for antibody binding, (+/−) for partial binding, and (−) for no antibody binding.

[d]ELISA assays of samples, 2-8 μg/mL in pH 8.5 Tris-HCl buffer, were done under standard conditions and scored: positive (+), when the positive control incubation with anti-PAL antibody gave a higher value than the incubation with the negative control serum; negative (−), when there were equivalent absorbance values with either serum-sample; and (+/−) when the positive control scored slightly higher.

[e]Immunoprecipitation was performed in TTBS buffer (0.1% Tween in Tris buffered saline); PAL activity was measured before adding the antibody sample. Each sample was incubated with an 8-fold excess of anti-PAL serum and a duplicate negative control reaction using non-immune mouse serum. After incubation, protein G Sepharose 4 (50%, v/v) was added in excess and the samples were incubated at 4° C. overnight with rotation. Beads were removed by centrifugation and the PAL activity of each supernatant was assayed. The bead pellets were analyzed by Western blot to confirm that antibody-bead binding occurred. PAL variants with poor antibody binding had correspondingly little-PAL in the bead fractions as detected by Western blot and had higher activities remaining in the supernatant. Immunoprecipitation results were scored in a similar fashion to the ELISA results, with samples showing anti-PAL antibody binding being scored a (+) or (+/−), dependent upon the magnitude of the value, whereas samples yielding low values of anti-PAL antibody binding scored a negative.

Pegylated PAL samples were analyzed by sodium dodecylsulfate-polyacrylamide gel electrophoresis (SDS-PAGE) using 10% Bis-Tris gels in MOPS (3-(N-morpholino) propane sulfonic acid) buffer. To detect unreacted and potentially immunogenic PAL protein after pegylation, size exclusion chromatography was run using an HPLC (Vision, Applied Biosystems, Foster City, Calif.) on a Superdex 200HR 10/30 column (Amersham Biosciences) equilibrated with 1× Dulbecco's PBS, pH 7.4 (Cellgro) at a flow rate of 0.4 mL/min. In vitro characterization of the linear 20 kDa PEG-PAL series formulations tested in vivo is provided in Table 8.

TABLE 8

|  | Ratio PAL:PEG | Prot. Conc. (mg/mL)[a] | PAL Activity IU/mg[b] | # PEG/ monomer SDS-PAGE |
|---|---|---|---|---|
| Wild-type PAL |  | 1.92 | 2.1 |  |
| Linear 20 kDa PEG-PAL | 1:4 | 1.15 | 2.44 | 6 |
| Linear 20 kDa PEG-PAL | 1:8 | 0.87 | 2.54 | 7 |
| Linear 20 kDa PEG-PAL | 1:16 | 0.54 | 2.13 | 8 |

[a]Protein concentration was determined using the PAL extinction coefficient (0.5 mg mL$^{-1}$cm$^{-1}$) at 280 nm for non-modified protein samples. For polyethylene glycol (PEG) modified (pegylated) PAL, the concentration was calculated using a BSA standard curve and the NI Protein Assay (GenoTechnology, St. Louis, MO).
[b]One unit of PAL is defined as that amount of enzyme that produces 1 μmol of trans-cinnamic acid per minute at room temperature.

Example 10

Figure 9A:
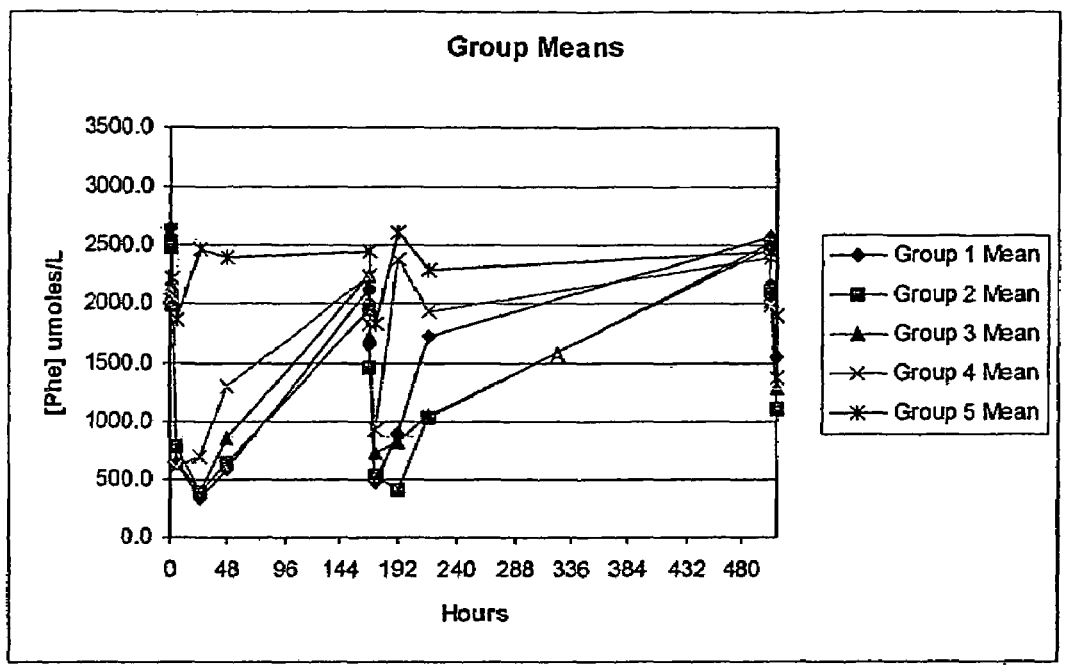
FIG. 9A samples are: Group 1 Linear 1:8 5 kDa; Group 2 Linear 1:24 5 kDa; Group 3 Linear 1:32 5 kDa; Group 4 wt PAL; Group 5 buffer control.
Figure 9:
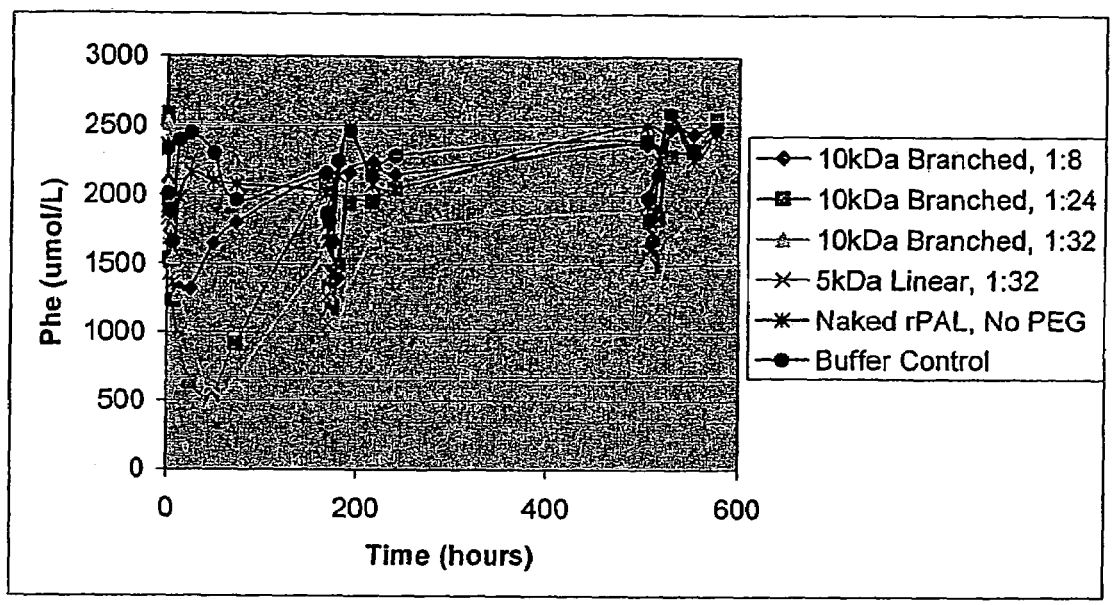
FIG. 9 is a graph depicting in vivo activity data of various pegylated PAL conjugates vs. unmodified PAL. PEG:PAL conjugates were studied with 5 kDa linear, 10 kDa branched, or 20 kDa linear PEG attached, with progressively higher degrees of substitution. Plasma L-Phe concentrations are plotted vs. time after administration.
Figure 9:
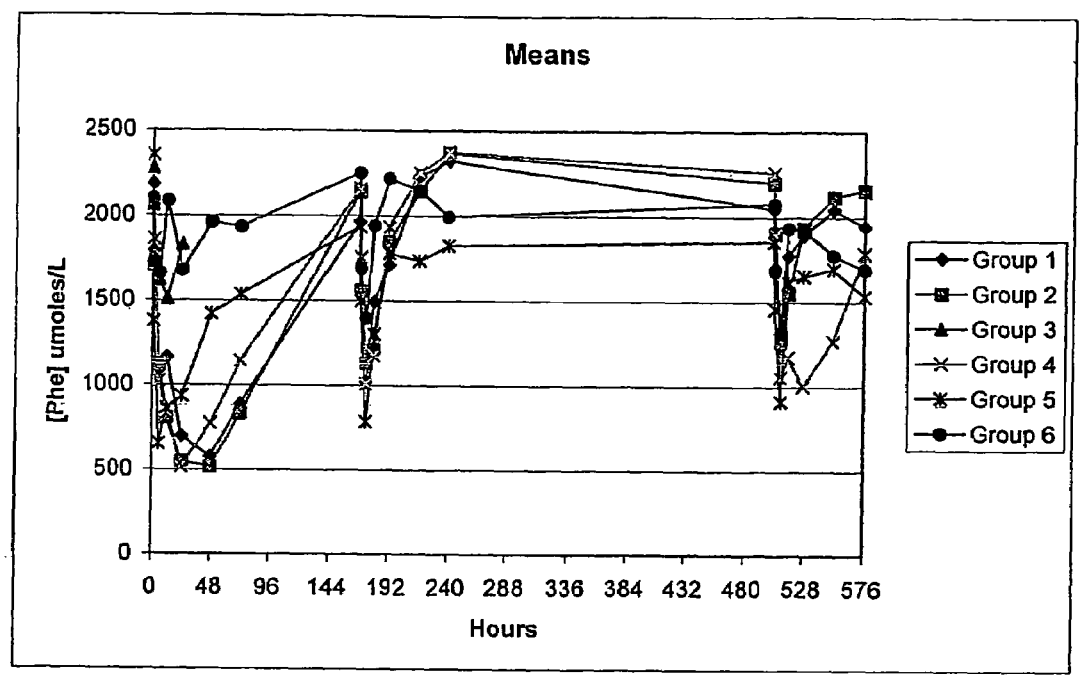

In this example, different PEG:PAL conjugates with varying degrees of pegylation were evaluated in Enu2/Enu2 mice (PKU model genotype (Sarkissian, et al., Proc Natl Acad Sci USA, 96(5), pp. 2339-2344 (1999); McDonald, et al., Mol. Genet. Metab., 76(4), pp. 256-261 (2002); Sarkissian, et al., Mol. Genet. Metab., 69, pp. 188-194 (2000)) to compare and contrast their L-phenylalanine reduction potential and duration as well as antibody titers (immunogenicity measurement). The three series of compounds tested were: linear 5 kDa PEG:PAL, branched 10 kDa PEG:PAL, and linear 20 kDa PEG:PAL conjugate. Each PEG:PAL conjugate was tested as a single bolus, subcutaneous dose at a dosage of 1 unit. Unmodified PAL was used at a dosage of 1 unit in a single, bolus injection. Injections were performed at days 1, 8, and 22. The in vivo assay results are depicted in FIG. 9, and demonstrate that the PEG:PAL conjugates prepared by coupling M-PEG-SPA or m(PEG)2-NHS to PAL perform better or at least comparably to PAL alone in the Enu2/Enu2 mouse assay. Moreover, these PEG:PAL conjugates demonstrate a prolonged efficacy relative to the unmodified PAL. For Enu2/Enu2 mice, a darkening of their coat color with enzyme administration is indicative of attainment of euphenylalaninemia, and a number of PEG:PAL treated mice displayed this change in phenotype.

Figure 10:
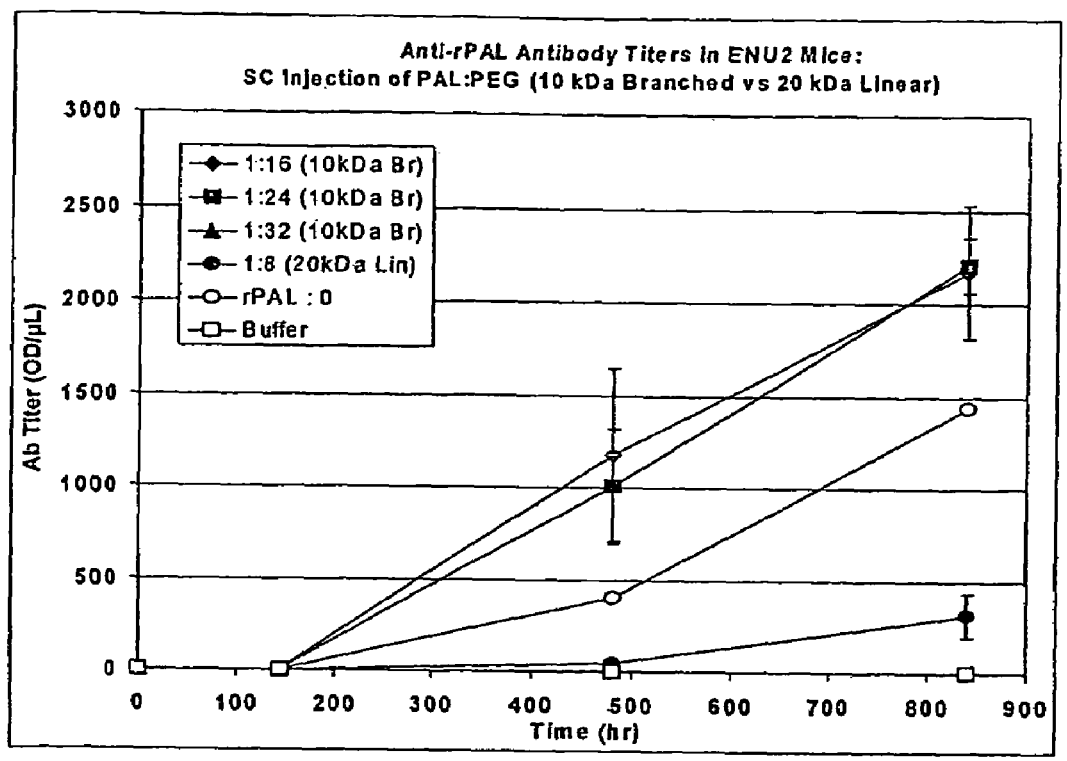
FIG. 10 is a graph depicting antibody response of mice after single subcutaneous bolus injections of 1 unit PEG:PAL conjugate up to 840 hours: (♦), 1:16 branched 10 kDa PEG:PAL conjugate; (■), 1:24 branched 10 kDa PEG:PAL conjugate; (▲), 1:32 branched 10 kDa PEG:PAL conjugate; and (●), 1:8 linear 20 kDa PEG:PAL conjugate vs. unmodified PAL (○). Antibody titer (in optical density per microliter) is plotted vs. hours post-treatment.

Each PEG:PAL conjugate from the linear and branched polymer series showed significant and comparable prolongation of the L-phenylalanine reduction effect (see FIG. 9). Antibody titers for these series of conjugates differed appreciably (FIG. 10). The linear 5 kDa- and branched 10 kDa-substituted PEG:PAL conjugates were more immunogenic, but unexpectedly, the linear 20 kDa substituted PEG:PAL conjugate demonstrated an improved activity and reduced immunoreactivity relative to native PAL. All of the PEG substituted PAL conjugates demonstrated prolonged activity comparable to the linear 20 kDa substituted PEG:PAL conjugates. These examples thus demonstrate the enhanced duration of L-phenylalanine reduction by a variety of PEG:PAL conjugates using single-dose, bolus injections in the PKU mouse model.

These data demonstrate the unexpected advantage of an increase in L-phenylalanine reduction activity half-life for the PEG:PAL conjugates relative to PAL alone, in that the results demonstrate a clear increase in the magnitude and duration of the response to the PEG:PAL conjugates. In some cases, the linear 5 kDa PEG:PAL conjugate appears to modestly outperform the branched 10 kDa PEG:PAL conjugate, which modestly outperforms the linear 20 kDa PEG:PAL conjugate. Based on an immunogenicity criterion, the 20 kDa PEG:PAL conjugate might be a preferred configuration.

Example 11

Generation of Pegylated PAL Variants

Protein Pegylation

The pegylation of the PAL variants was performed using modifications of literature methods (Hershfield, et al., (1991) ibid.; 304 U.S. Pat. No. 6,057,292; 558 Lu, et al., Biochemistry, 40(44), pp. 13288-13301 (2001); Nektar Therapeutics, 2003 catalog). Activated PEGs included both the linear PEG succinimidyl succinates (mPEG-SPA, MW 5 kDa or MW 20 kDa) and the branched PEG hydrosuccinimides (mPEG$_2$-NHS ester, MW 10 kDa or MW 40 kDa), which are both capped on one end with a methoxy group and available from Nektar Therapeutics; experimental determination of optimal pegylated proteins is normally required (Veronese, et al., Journal of Bioactive and Compatible Polymers, 12: 196-207 (1997)). Optimal pegylation conditions were determined using different ratios of PAL:PEG (taking into account the molar ratio of protein along with the number of lysines per protein monomer), different pHs, different buffers, various temperatures and incubation times. High PAL protein:PEG derivatization ratios are necessary since native PAL has a large number of lysines (29 per monomer) and because unmodified PAL displays immunoreactivity upon repeated injection in mice and since naked (wild-type) PAL is quickly inactivated upon exposure to proteases. Pegylation reactions were stopped by freezing at −20° C., and the samples were analyzed by SDS-PAGE, MALDI-TOF mass spectroscopy, activity assessment, proteolytic sensitivity, and immunoreactivity.

Prior to activity, proteolysis, and immune assessment, and in order to remove excess unreacted PEG, reactions were dialyzed against pH 8.5, 0.05 M potassium phosphate buffer overnight at 4° C. with stirring using Tube-O-Dialyzers (GenoTechnology). After protein concentration was determined using the NI protein assay kit (Geno Technology), PAL activity measurements were performed on underivatized and PEG derivatized PAL samples using standard reaction conditions, as previously described. Following in vitro characterization, in vivo trials were conducted with the most promising pegylated therapeutic candidates using the PKU mouse model.

Characterization

Protein concentration was determined using the PAL extinction coefficient (0.5 mg mL$^{-1}$ cm$^{-1}$) at 280 nm for non-modified protein samples and for pegylated protein samples the concentration is calculated using the NI Protein Assay (GenoTechnology) that includes sample processing to remove non-protein contaminants that might interfere with accurate protein concentration determination.

PEG-PAL products were characterized with MALDI-TOF MS to determine the number of PEG molecules attached to each PAL monomer, as well as characterized using activity assessment and SDS-PAGE and native gel analysis, to assure retention of activity, complete derivatization, and no loss of tetrameric PAL formation, respectively. For PAL and PEG-PAL samples, MALDI-TOF mass spectroscopic analysis requires the use of 0.5 M urea or 0.025 M guanidine-HCl to improve subunit dissociation and the reproducibility of species detection.

Activity

PAL activity assay were conducted using a Cary UV spectrophotometer (Cary 50) in the kinetics mode. The activity of PAL with L-phenylalanine substrate was assayed at room temperature (25° C.) by measuring the production of trans-cinnamate monitored by the absorbance increase at 290 nm (Hodgins, D. S., 'The presence of a carbonyl group at the active site of L-phenylalanine ammonia-lyase", Biochem. Biophys. Res. Commun., 32, pp. 246-253 (1968)). The molar extinction coefficient of trans-cinnamic acid at 290 nm is 10.2381 liter $M^{-1}$ $cm^{-1}$. Reaction mixtures contained 22.5 mM phenylalanine in 100 mM Tris-HCl buffer, pH 8.5. For standard measurements, the final enzyme concentration was 0.0035 mg/mL, but for kinetic studies the enzyme concentration in the assay was adjusted so that the slope at 290 nm per min is in the range of 0.005 to 0.02. Activity data is expressed as specific activity ($\mu mol \times min^{-1}$ $mg^{-1}$). One unit of PAL is defined as that amount of enzyme that produces 1 $\mu mol$ of trans-cinnamic acid per minute at room temperature.

TABLE 9

Activity measurements for different PEG:PAL conjugates

| Sample | Enzyme Activity (%) |
|---|---|
| native wt-PAL | 100 |
| pegylated PAL, 1:4 (linear PEG, 5 kD) | 128 |
| pegylated PAL, 1:1 (branched PEG, 40 kD) | 161 |

Test of In Vivo Half-Life and Immunogenicity

After biochemical characterization, the most promising PEG-PAL candidates were screened for immunoreactivity against antibodies raised by PKU mice injected with native PAL (non-pegylated) using three different and complimentary techniques (Western blot, ELISA, and immunoprecipitation (IP)).

For Western blot analysis, PAL anti-serum (from mice injected with native PAL) was used in a dilution 1:10,000. As a negative control the serum from buffer treated-mice was also used in the same dilution. The secondary antibody, alkaline phosphatase-conjugated goat anti-mouse IgG (Promega), was diluted to 1:5,000 and color was developed using the AP substrate Western Blue (Promega). The ELISA test was performed using Nunc/Immuno Maxisorp plates (Nalge Nunc International) following standard procedures using 1 mg/mL of PAL in PBS and blocking with PBS, 0.05% Tween-20, 2% BSA. The mouse antisera (from native PAL exposed mice) was diluted 1:10,000 in EB block solution (PBS, 0.05% Tween-20, 2% BSA), and a HRP-goat anti-mouse IgG was used as secondary antibody with TMB used for detection at 450 nm.

Immunoprecipitation was used to test for PAL antibody binding. Protein samples (PAL or pegylated PAL) were incubated in TTBS buffer (Tris buffered saline with 0.1% Tween) and PAL activity was measured before adding the antibody sample. Each sample was incubated with 8-fold excess of positive control anti-PAL serum and a duplicate negative control reaction using non-immune mouse serum. After incubation, protein G Sepharose 4 (50%, v/v) was added in excess, taking into account the mouse IgG binding capacity of the beads, and the samples were incubated again at 4° C. overnight with rotation.

Supernatants were recovered by centrifugation and the PAL activity of each sample was assayed on the supernatants. The bead pellets were not discarded, so that further analysis by Western blot can be performed. To confirm that antibody-bead binding had occurred, Western blot was used to detect the PAL antigen on the beads. Beads that have been recovered by centrifugation after the PAL binding step were washed several times with TTBS and TBS buffers. Following these rinses, SDS-PAGE loading buffer was added to the beads and the samples were heated at 95° C. for 5 minutes. Samples were then analyzed by Western blot using PAL anti-serum. Enzyme variants showing poor antibody binding have corresponding little PAL in the pelleted bead fractions as detected by Western blot and show higher activities remaining in the supernatant as compared to native unmodified PAL which displays high antibody binding.

Promising PAL variants based upon in vitro experimentation include pegylated samples using 1:32 linear 5 kDa PEG, 1:32 branched 10 kDa PEG, 1:8 linear 20 kDa PEG, and 1:16 linear 20 kDa PEG.

Test of Protease Sensitivity

Improved PAL (and PEG-PAL) mutants obtained via protein engineering methods described above that retain activity, screening for protease resistance using incubation with a trypsin/chymotrypsin protease cocktail, followed by monitoring for retention of activity (via $OD_{290}$ measurement) and reduced protein cleavage (via PAGE gel analysis) allowed for the identification of mutants with appropriate in vitro properties for use in in vivo testing.

Proteolytic stability was assessed using incubation with a protease cocktail that approximates the intestinal environment and contains 2.3 mM trypsin, 3.5 mM chymotrypsin, 3.05 mM carboxypeptidase A, and 3.65 mM carboxypeptidase B. Proteolysis testing involved enzymatic incubations, adding proteases to the PAL solutions to determine the degree of protease sensitivity for the different protein variants being examined (native or mutant protein with or without pegylation or other chemical modification), including time courses of activity retention and stability retention after protease exposure. SDS-PAGE and MALDI-TOF mass spectrometric mapping experiments were used to determine the location of any protease sensitive sites (Kriwacki, et al., abrf.org/JBT/1998/September98/sep98m_r.html) (1998). These mapping results are important to determine primary sites of protease susceptibility (such as the two primary sites already identified), so that all major sensitivity sites can be removed using pegylation protection and/or mutation to remove and/or protect susceptible regions from the PAL architecture.

Example 12

The various formulations of branched and linear PEG-rPAL and naked rPAL, in 10 mM Na-phosphate, 150 mM NaCl, pH 7.4 and the control buffer, 10 mM Na-phosphate, 150 mM NaCl, pH 7.4, were formulated for injection as shown in Table 10.

TABLE 10

| Group | Number of Animals | PAL:PEG ratio | Dose Level (IU/animal) | Dose Concentration (IU/ml) | Dose Volume (ml) |
|---|---|---|---|---|---|
| 1 | 5 | 10 KDa Branched, 1:16 | 1.0 | 1.9 | 0.52 |
| 2 | 5 | 10 KDa Branched, 1:24 | 1.0 | 1.4 | 0.71 |
| 3 | 5 | 10 KDa Branched, 1:32 | 1.0 | 0.66 | 1.52 |
| 4 | 5 | 20 KDa Linear, 1:8 | 1.0 | 3.2 | 0.31 |
| 5 | 2 | Naked rPAL, No Peg | 1.0 | 3.1 | 0.32 |
| 6 | 2 | 0.0 | 0.00 | 0.0 | 1.52 |

Plasma Phe Determination

Figure 11:
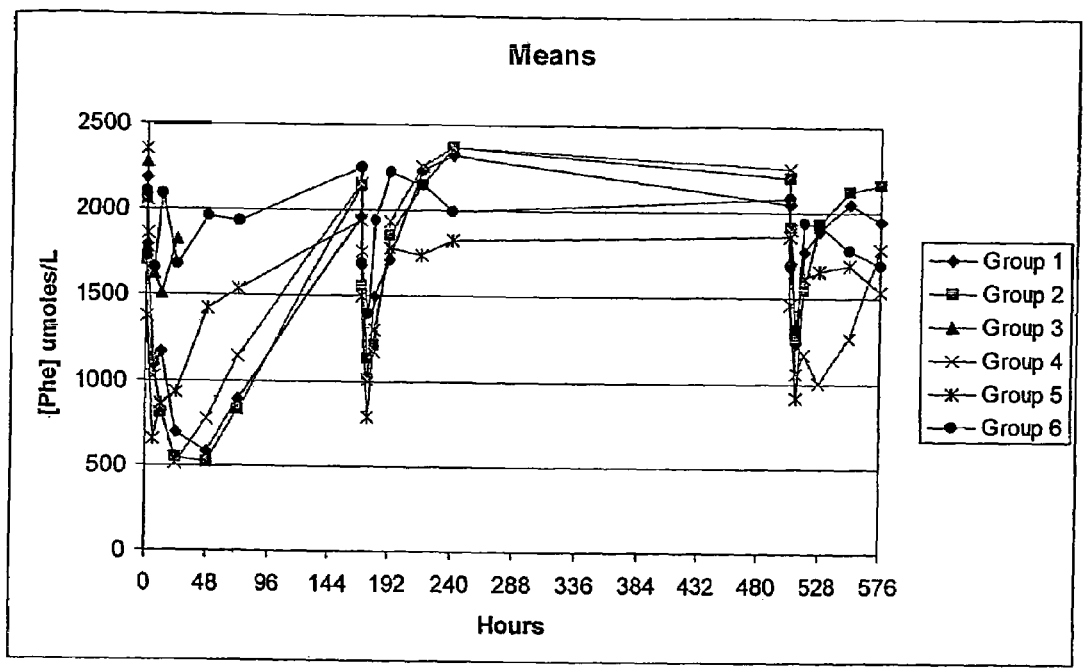
FIG. 11 illustrates the Phe levels of PALPEG molecules tested in Pku mice models.

Animals were bled via the tail vein (approximately 100 μL blood) to collect plasma for Phe determination at 0 hr, 60, 360 and 720 minutes, 24, 48 and 72 hours post dose on days 1, 8 and 22. Plasma was isolated from the blood sample, frozen and transferred on dry ice till analysis (determination of Phe concentration). The data is shown in FIG. 11 where Group 1 corresponds to the branched 10 KDa 1:16 sample, group 2 to the branched 10 KDa 1:24, group 3 to the branched 10 KDa 1:32 one, group 4 to the linear 20 KDa 1:8, group 5 to the wtPAL protein non-modified and group 6 to the control buffer. As it can be seen in this figure the group of linear 20 KDa 1:8 produces the most pronounced and longer maintained drop off of the blood Phe levels of all of the formulations tested.

Anti-PEG-rPAL/rPAL Antibodies Analysis

Animals were bled via the tail vein (approximately 100 μL blood) to collect serum for PEG-rPAL/rPAL antibody determination at −1 day pre-dose on study days 7, 21 and 36. Collection took place prior to dose administration on applicable days.

Figure 12:
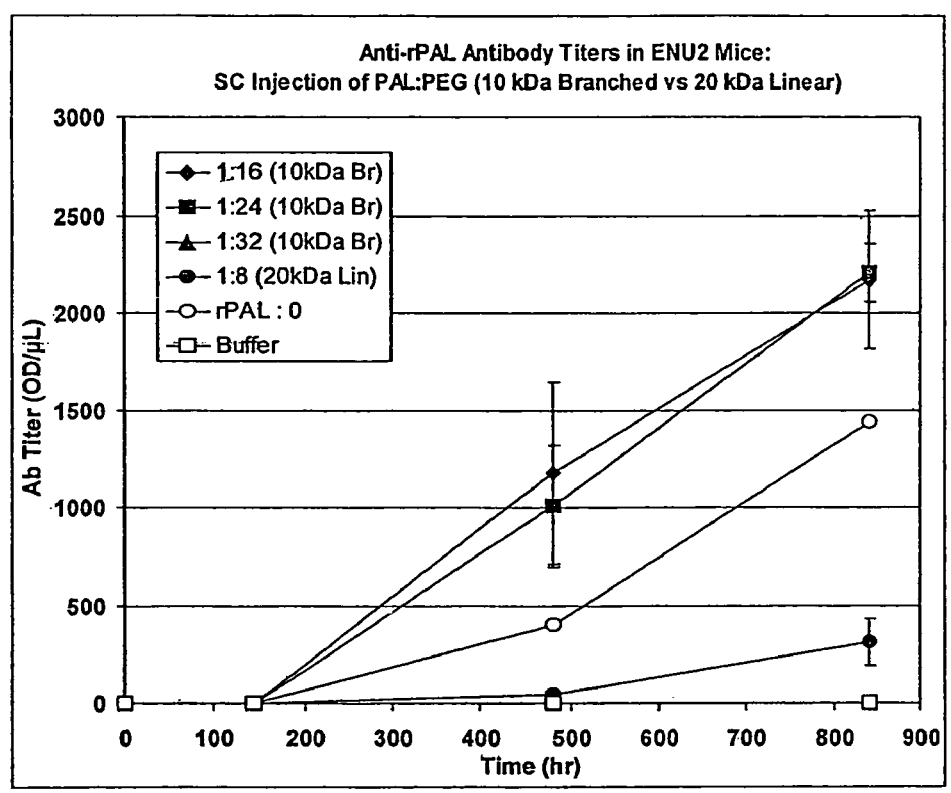
FIG. 12 illustrates the anti-rPAL antibody titers in ENU2 mice that were SC injected with PAL:PEG (10 kDa branched vs 20 kDa linear).

The immune in vivo effect of these preparations is shown in FIG. 12. The results demonstrate that the linear 20 KDa 1:8 PALPEG molecule confers protection compared to the wtPAL.

The combined effect of reduced Phe levels along with the lower anti-PAL antibody production that this preparation of PALPEG produces makes the linear PEG 20 KDa the most promising formulation to be used for PKU enzyme replacement therapy using the ratio 1:8 PAL:PEG.

Example 13

A series of PEG-rPAL derivatives were constructed to determine the effect of varying the proportion of PEG to rPAL on reducing plasma Phe and attenuating the immune response against rPAL. Conjugates consisting of linear 20 kDa PEG and rPAL, at ratios (rPAL:PEG) of: 1:4, 1:8 and 1:16 were formulated in 10 mM Na-phosphate, 150 mM NaCl buffer (pH 7.4). The formulations were injected subcutaneously into ENU-2 mice. Unconjugated rPAL and buffer alone were used as controls (see Table 11).

TABLE 11

| Group | Number of Animals | rPAL:PEG ratio | Dose Level (IU/animal) | Dose Concentration (IU/ml) | Dose Volume (ml) |
|---|---|---|---|---|---|
| 1 | 4 | 20 kDa Linear, 1:4 | 1.0 | 4.7 | 0.21 |
| 2 | 4 | 20 kDa Linear, 1:8 | 1.0 | 4.8 | 0.21 |
| 3 | 4 | 20 kDa Linear, 1:16 | 1.0 | 2.4 | 0.42 |

TABLE 11-continued

| Group | Number of Animals | rPAL:PEG ratio | Dose Level (IU/animal) | Dose Concentration (IU/ml) | Dose Volume (ml) |
|---|---|---|---|---|---|
| 4 | 4 | Native rPAL | 1.0 | 4.3 | 0.23 |
| 5 | 4 | Buffer | 0.0 | 0.0 | 0.42 |

Plasma Phe Determination

Figure 13:
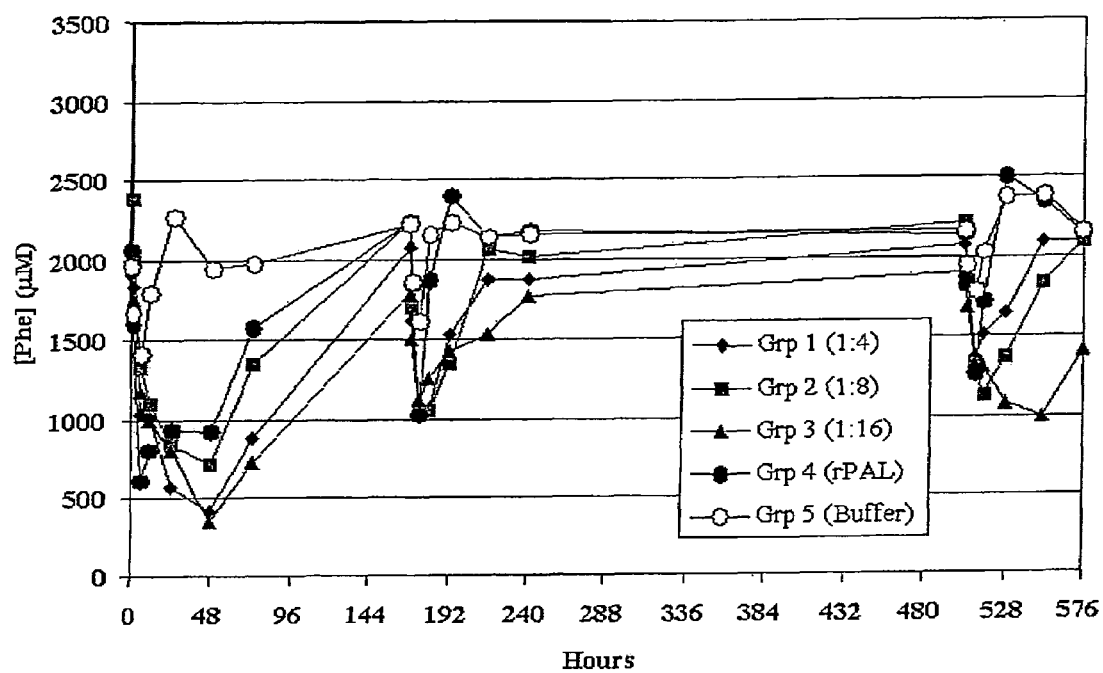
FIG. 13 shows the effects of conjugates of linear 20 kDA PEG and rPAL in ratios (rPAL:PEG) of: 1:4, 1:8 and 1:16 on plasma phe levels in ENU-2 mice following subcutaneous injection.

Animals were bled via the tail vein (approximately 100 μL blood) to collect plasma for Phe determination at 0 hr, 60, 360 and 720 minutes, 24, 48 and 72 hours post dose on days 1, 8 and 22. Plasma was isolated from the blood sample, frozen and transferred on dry ice until analysis (determination of Phe concentration). These data, as depicted in FIG. 13 show that at each time-point, the 1:16 rPAL:PEG ratio (group 3), tended to yield a greater reduction in plasma Phe over time than other derivatives.

Anti-PEG-rPAL/rPAL Antibodies Analysis

Figure 14:
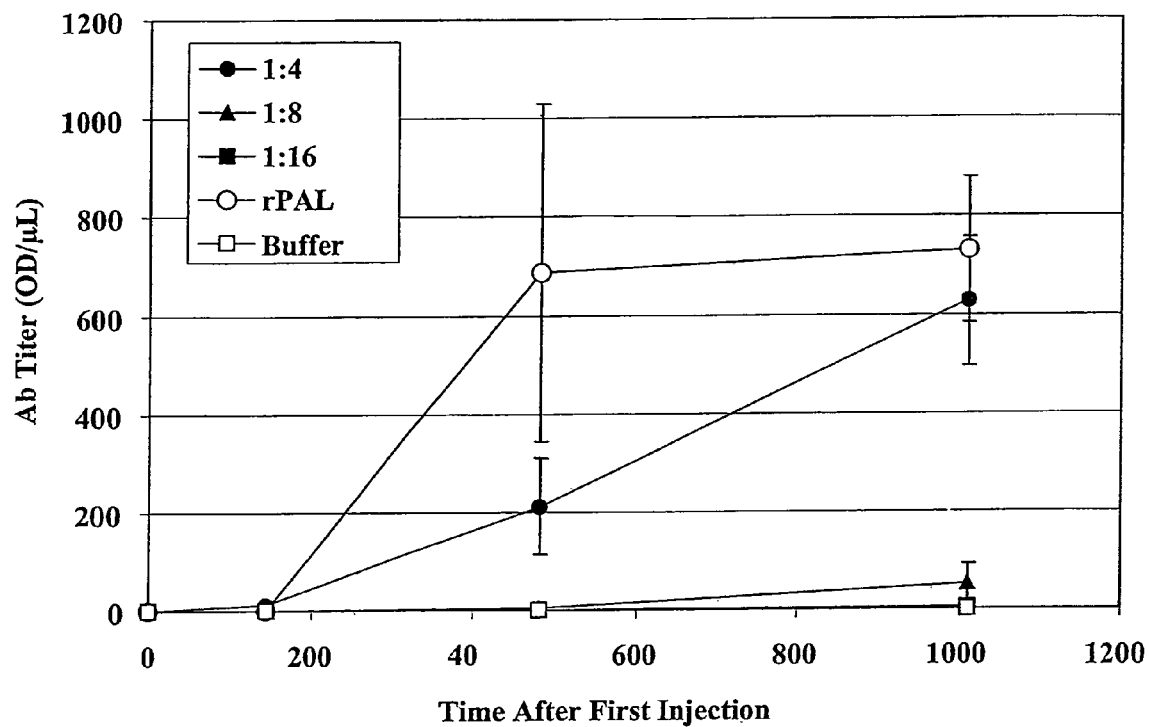
FIG. 14 shows the effects of conjugates of linear 20 kDA PEG and rPAL in ratios (rPAL:PEG) of: 1:4, 1:8 and 1:16 on anti-rPAL serum antibody titers in ENU2 Mice following subcutaneous injection.

Animals were bled via the tail vein (approximately 100 μL blood) to collect serum for anti-rPAL antibody determination at −1 day pre-dose on study days 7, 21 and 43. Serum collection took place prior to dose administration on applicable days. Conjugation of PEG to rPAL at all ratios tested reduced the anti-rPAL serum antibody titres. The capacity of these derivatives to reduce the immune response against rPAL tended to increase with greater amounts of conjugated PEG (FIG. 14). At the 1:16 rPAL:PEG ratio, Ab titres were decreased 100-fold versus native rPAL.

Example 14

To determine the effect of increasing the dose of the 1:8 rPAL:PEG conjugate on reducing plasma Phe and attenuating the immune response against rPAL, 1:8 PEG-rPAL was delivered subcutaneously to ENU-2 mice at 3 different doses-0.2, 0.6, 1.25 IU. Each dose, in addition to a native rPAL treatment, was formulated in 10 mM Na-phosphate, 150 mM NaCl buffer (pH 7.4). Buffer alone was also injected as a negative control (see Table 12).

TABLE 12

| Group | Number of Animals | rPAL:PEG ratio | Dose Level (IU/animal) | Dose Concentration (IU/ml) | Dose Volume (ml) |
|---|---|---|---|---|---|
| 1 | 4 | 20 KDa linear, 1:8 | 0.2 | 0.48 | 0.42 |
| 2 | 4 | 20 KDa linear, 1:8 | 0.6 | 1.45 | 0.41 |
| 3 | 4 | 20 KDa linear, 1:8 | 1.25 | 2.90 | 0.43 |
| 4 | 4 | Naked rPAL, No Peg | 1.25 | 2.40 | 0.52 |
| 5 | 1 | Buffer | 0.0 | 0.0 | 0.52 |

Plasma Phe Determination

Figure 15:
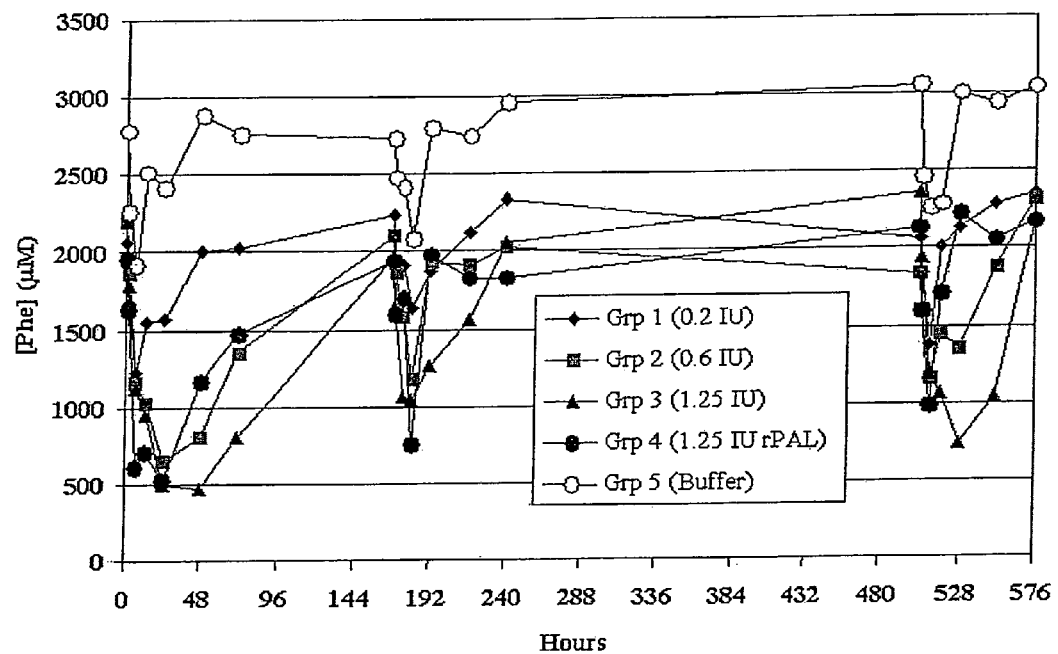
FIG. 15 shows the effects of increasing doses of 1:8 20 kDA linear rPAL-PEG conjugate on plasma phe levels in ENU-2 mice following subcutaneous injection.

Animals were bled via the tail vein (approximately 100 μL blood) to collect plasma for Phe determination at 0 hr, 60, 360 and 720 minutes, 24, 48 and 72 hours post-dose on days 1, 8 and 22. Plasma was isolated, frozen and transferred to dry ice until analysis (determination of Phe concentration). These data, as depicted in FIG. 15, show that at each time-point, the highest dose of rPAL tended to yield the greatest reductions in plasma Phe. Conjugated molecule at the highest dose produced a more prolonged reduction in plasma Phe when compared to unconjugated molecule at the same dose.

Anti-PEG-rPAL/rPAL Antibodies Analysis

Figure 16:
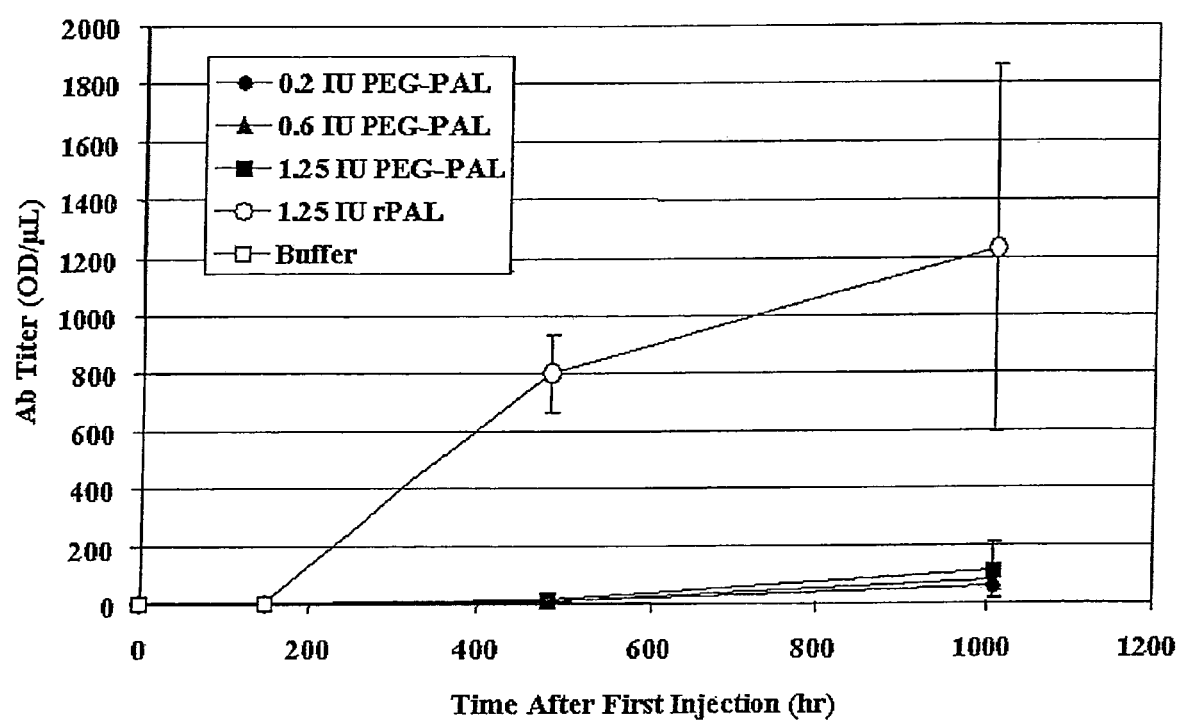
FIG. 16 shows the effects of increasing doses of 1:8 20 kDA linear rPAL-PEG conjugate on anti-rPAL serum antibody titers levels in ENU-2 mice following subcutaneous injection.

Animals were bled via the tail vein (approximately 100 μL blood) to collect serum for anti-rPAL antibody determination at −1 day pre-dose on study days 7, 21 and 43. Collection took place prior to dose administration on applicable days. Conjugation of PEG to rPAL at all doses tested reduced the anti-rPAL serum antibody titres approximately 10-fold relative to those of native rPAL. There was no significant difference in antibody titre between the 3 doses of conjugated rPAL (FIG. 16).

Example 15

Antibody Epitope Mapping

The major binding sites recognized by antibody anti-PAL was determined by scanning an antigen peptide library (peptide scan format 13/11) of PAL (SwissProt-ID:PALY_RHOTO; 716 amino acid residues, resulting in 353 peptides). All of the cysteine residues contained in the synthesized antigen peptides were substituted by serine and all N-termini were acetylated.

Materials and Methods

The materials consisted of primary antibody anti-PAL (format mouse IgG1, 10 μg/mL) and secondary antibody anti-mouse IgG (Sigma A5906, 1.0 μg/mL) labeled with horseradish peroxidase.

Antigen peptides were synthesized on a cellulose membrane in a stepwise manner resulting in a defined arrangement (peptide array) and are covalently bound to the cellulose membrane. Binding assays were performed directly on the peptide array. The peptide array was incubated with a primary (antigen peptide binding) antibody in blocking buffer and then incubated with horseradish peroxidase (HRP)-labeled secondary antibody, which selectively binds the primary antibody. The antigen peptide array was incubated with a blocking buffer for several hours to reduce non-specific binding of the antibody. Alternatively, an HRP-labeled primary antibody in blocking buffer can be used. A short T(Tween-TBS-buffer washing directly after incubation of the antigen peptide array with the secondary antibody or the HRP-labeled primary antibody followed by the first chemiluminescence experiment was made to obtain an initial overview of which antigen peptides do bind the primary antibody. Several buffer washing steps follow (T-TBS- and TBS-buffer) to reduce false-positive binding (unspecific antibody binding to the cellulose membrane itself). After these washing steps the final chemiluminescence analysis is performed. The data were analyzed with an imaging system showing the signal intensity (Boehringer Light units, BLU) as single measurement for each peptide. In order to evaluate non-specific binding of secondary antibodies, incubations have to be performed in the absence of the primary antibody as control incubation. In this case, the secondary antibody showed no binding in the control experiment.

Results

Figure 17:
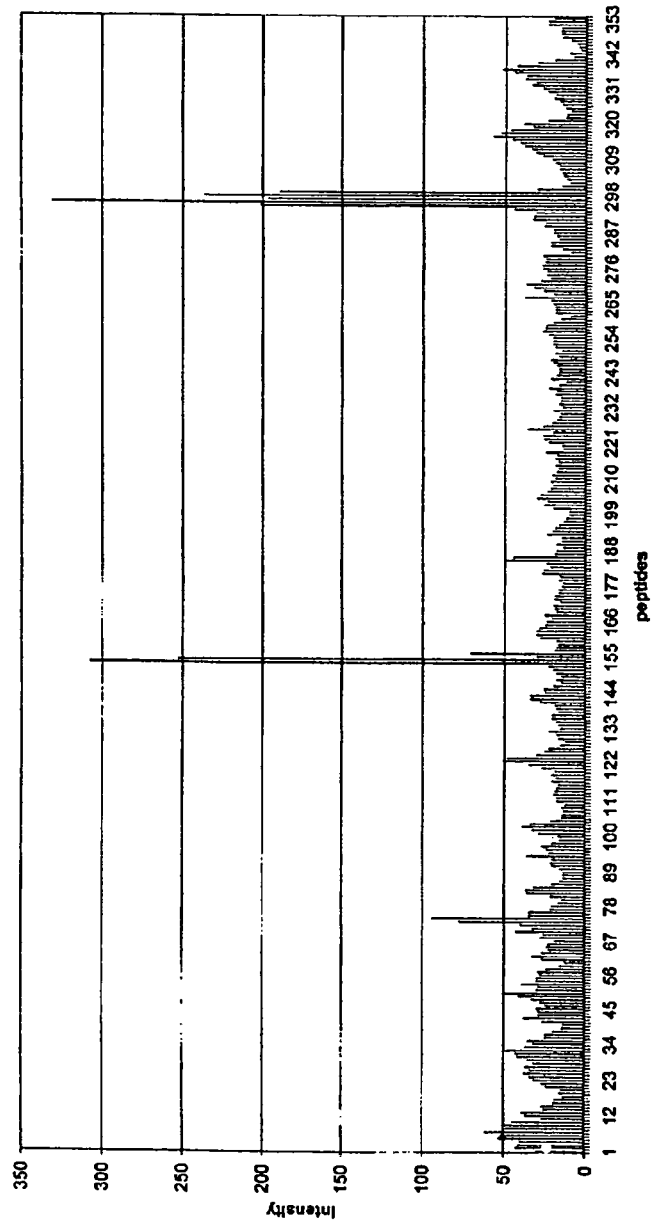
FIG. 17 shows the results of the chemiluminescence experiments of PAL antigen peptide array with antibody anti-PAL and IgG anti-mouse-HRP, with peaks at peptide nos. 73-74 (aa residues 147-157), peptide nos. 153-154 (aa residues 307-317) and peptide nos. 295-299 (aa residues 597-601).
Figure 18:
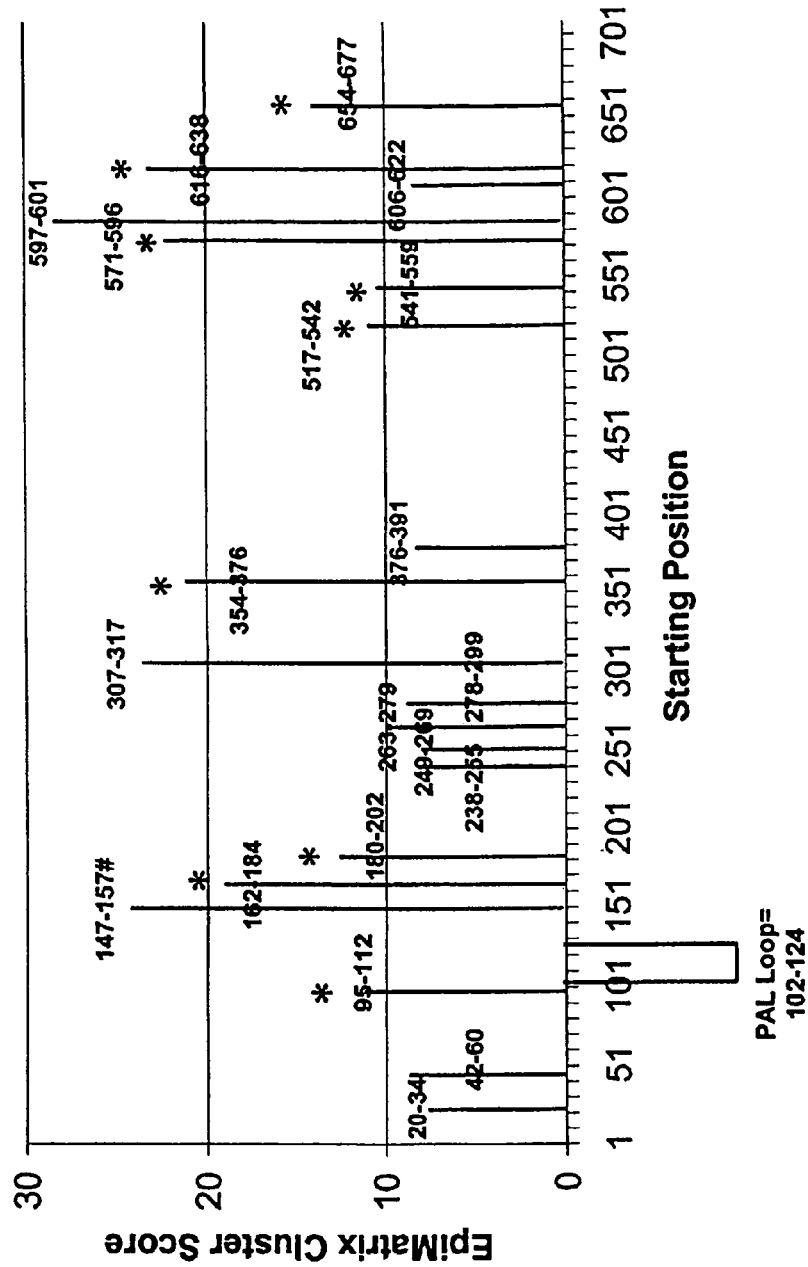
FIG. 18 shows the EpiMatrix Cluster Analysis for PAL-P11455.
Figure 19:
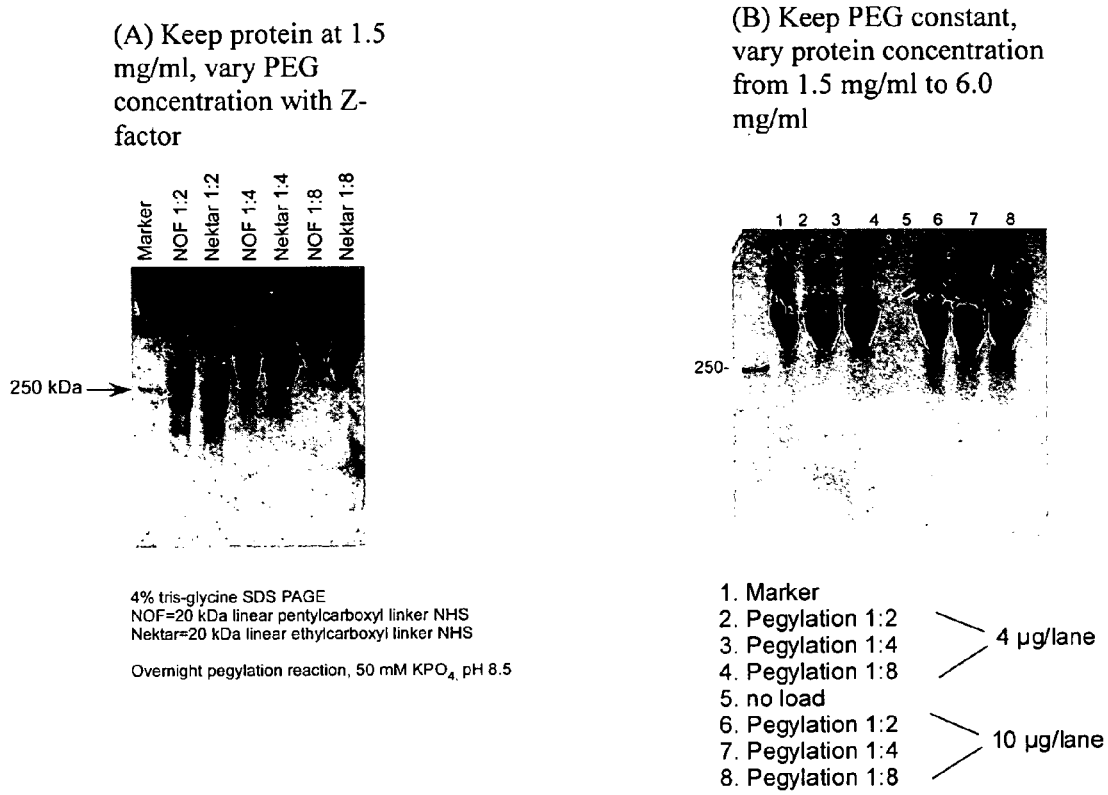
FIG. 19 shows PEGylation performed using various Z-factors with two different PEG sources (20 kDa linear SPA (PEG-propanoic acid-NHS) and 20 kDa linear MER-200HS (PEG-hexanoic acid NHS).

The antibody anti-PAL recognized three major binding sites: peptides nos. 73-74 corresponding to amino acid residues 147-157, peptide nos. 153-154 corresponding to amino acid residues 307-317, and peptide nos. 295-299 corresponding to amino acid residues 597-601 (See FIG. 17). The most intense signals and the corresponding peptides sequences are listed below. Overlapping amino acid residues are marked in bold with the corresponding amino acid residues listed below each group of peptides:

```
   73:     SSFDSFRLGRGLE
           (SEQ ID NO: 86)

74:       FDSFRLGRGLENS
           (SEQ ID NO: 87)

amino acid residues 147 to 157
  153:     VGHAGSFHPFLHD
           (SEQ ID NO: 88)

154:       HAGSFHPFLHDVT
           (SEQ ID NO: 89)

amino acid residues 307 to 317
  295:     NSYDLVPRWHDAF
           (SEQ ID NO: 90)

296:        YDLVPRWHDAFSF
           (SEQ ID NO: 91)

297:          LVPRWHDAFSFAA
           (SEQ ID NO: 92)

298:            PRWHDAFSFAAGT
           (SEQ ID NO: 93)

299:              WHDAFSFAAGTVV
           (SEQ ID NO: 94)

amino acid residues 597 to 601
```

In summary, the antibody recognized three immunodominant regions with major peptide nos. 74, 307 and 296.

Example 16

In Silico Immunogenic Region Identification

The overall immunogenic potential of PAL was assessed and regions (15 to 25 amino acids in length) containing the sequence of PAL with significant potential immunogenicity were identified.

Materials and Methods

Materials included the complete amino acid sequence of PAL (P11544, BIOMARIN™) and EPIMATRIX™ System (EpiVax).

The complete amino acid sequence of PAL was parsed into 9-mer analysis frames where each frame overlapped the last 8 amino acids. Each 9-mer frame was evaluated for potential immunogenicity relative to a panel of eight, DRB1*0401 common class II HLA including DRB1*0101, DRB1*0301, DRB1*0401, DRB1*0801, DRB*1*101, DRB1*1301, and DRB1*1501. Each of the analysis frames were blasted against the protein database at Genbank and a report listing of all significant homologies were produced. Each of the analysis frames were blasted against the EpiVax proprietary database of known epitopes and MHC ligands and a report listing of all significant homologies identified was produced. Based on the results of the analysis, the overall immunogenic potential of PAL and regions (15 to 20 amino acids in length) contained within the sequence of PAL with a significant potential for immunogenicity were evaluated.

Results:

The PAL protein is not inherently immunogenic but contains some regions of higher immunogenic potential that could be modified so as to reduce large potential immunogenicity of the protein to the same level as other, safe, non-immunogenic proteins such as albumin, or the constant domain of immunoglobulin.

Overall Immunogenicity Evaluation Upon analysis of the 708 9-mer frames within the 716 amino acid long sequence against a panel of 8 common Class II alleles, there were 303 potential epitopes identified representing about 5% of the sample. When taking into account the number of potential epitopes and length of the PAL p[protein, the overall immunogenicity score was average. However, when assessing the risk of immunogenicity, it is important to consider not only the overall potential but also regional potential. Potential T cell epitopes are not randomly distributed throughout protein sequences but instead tend to clump together and are referred to as "T cell epitope clusters" or just "cluster". Clusters range from 9 to 25 amino acids in length and considering their affinity to multiple alleles and across multiple frames, can contain from 4 to 40 binding motifs. Thus a protein with an overall average immunogenicity potential may have enhanced immunogenicity due to one or more clustered regions.

When the PAL protein was scanned for clusters of potential T cell epitopes, nine clusters with significant potential for immunogenicity containing 118 or 39% of the 303 potential epitopes. Another eight clusters less significant potential for immunogenicity contained 51 potential epitopes or 17 percent of the total. The 17 clusters would be considered targets for deimmunizing PAL. Within the 17 target regions, a detailed analysis was conducted highlighting the individual amino acids making the highest aggregate contribution to binding affinity when considering multiple alleles and multiple frames. Such sensitive amino acids would be considered the target of modification when deimmunizing the protein.

FIG. 18 shows the EpiMatrix cluster analysis of the PAL-P1145 protein. Notably, cluster scores are high within the range of amino acid residues, 147-157, 307-317 and 597-601 identified by antibody epitope mapping described in Example 15.

When the 9-mer frames contained in the PAL protein were screened against a database of known MHC legends and T cell epitopes, no significant homologies were found. Peptide sequences that are homologous to human sequences may run an increased risk of breaking immune tolerance resulting in unwanted autoimmune reactions. Thus, the 9-mer frames contained in the clustered regions identified in the PAL sequence were blasted against the human sequence protein database in Genbank. There were only a few significant homologies identified.

There were three examples where a 9-mer frame of the PAL protein was an eight of nine match to the human peptide and also was a potential epitope. Frame 109 with peptide VYGITTGFG SEQ ID NO: 95 matched eight of nine to human peptide VYGVTTGFG SEQ ID NO: 96 and was a "hit" on alleles DRB1101 and DRB1*1501. Frame 611 with peptide VLSSTSLSL SEQ ID NO: 97 was an eight of nine match to human peptide VLSSTSLRL SEQ ID NO: 98 and was a "hit" on alleles DRB1*0701 and DRB1*1501. Frame 654 with peptide ALSYLSPRT SEQ ID NO: 99 was an eight of nine match to human peptide ALSYLKPRT SEQ ID NO: 100 and was a "hit" on allele DRB1*1501. No perfect matches were identified. The limited homology found between the sequence of the PAL protein and the human genome does not represent a significant deterrent to the further development of the PAL protein as a human therapeutic agent.

Based on the average amount of predicted immunogenicity for the PAL protein of its size but significant number of high scoring clusters, the protein will be tested in mice before advancing to the clinic If PAL elicits T-cell activity and antibody formation in transgenic mice, the protein will be deimmunized prior to entry into the clinic.

Example 17

New PEGylation Technique for Production of Phenylase (PEG-PAL)

The current PEGylation process for the production of PEG-PAL involves a reaction between 20 kDa linear PEG SPA (PEG-propanoic acid-NHS) at 1.5 mg/ml enzyme concentration and an amount of PEG equal to the molar lysine concentration times a ratio (called the Z-factor). For a Z-factor of 1:8, the final PEG concentration would be 93.5 mg/ml while the enzyme concentration is 1.5 mg/ml. For a Z-factor of 1:16, the final concentration of PEG would be 187 mg/ml while the enzyme concentration remains 1.5 mg/ml enzyme.

The relatively high Z-factors of 1:8 and 1:16 have not been considered economically viable. In addition, the Z-factor of 1:8 using 20 kDa linear PEG SPA (PEG-propanoic acid-NHS) has not conferred sufficient protection to the PEG-PAL molecule against the immune response observed in mice. In fact, by the third injection of PEG-PAL, antibody specific to PEG-PAL titers are greater than $10^4$ compared to controls. An improved PEGylation protocol was considered essential both to improve the economic viability of the final drug substance and to improve its efficacy.

The reasoning for the PEGylation process improvement is as follows. The half-life of 20 kDa linear PEG SPA (PEG-propanoic acid-NHS) in aqueous solution is relatively short, approximately 20 minutes. This loss of activity is essentially an unproductive, competing hydrolysis reaction. Both the hydrolysis and the useful PEGylation reaction are likely proportional to reagent concentrations as typical bimolecular reactions:

(1) PEG-NHS+$H_2O$→PEG (un-reactive, "wasted"), reaction rate=$k_1$[PEG-NHS][$H_2O$]

(2) PEG-NHS+PAL lysines→PEG-PAL, reaction rate=$k_2$ [PEG-NHS][lysine]

To reduce the proportion of reaction material wasted in reaction (1) an increase in the concentration of the components in reaction (2), in particular the protein (lysines) is desired. Therefore, the Z-factor should be altered by increasing the protein concentration while keeping the PEG-NHS at a constant (high) level.

FIG. 19A shows an experiment where PEGylation was performed using various Z-factors with two different PEG sources (20 kDa linear PEG SPA (PEG-propanoic acid-NHS) and 20 kDa linear ME-200HS (PEG-hexanoic acid-NHS)) using the original reaction conditions. The molecular weight observed by SDS PAGE was greatly dependent on the Z-factor. In FIG. 19B, the Z-factor was altered by increasing the protein concentration from 1.5 to 6.0 mg/ml. In this case, the apparent molecular weight was less dependent on the Z-factor and was generally high in all cases.

Procedure

The final PEG concentration was set at 8 mM (160 mg/ml) because higher concentrations were excessively viscous and difficult to handle and dissolve. Therefore, for a 1:3 Z-factor, the final lysine concentration was 2.67 mM, which gave a protein concentration of 6.85 mg/ml for a PAL molecule with 30 lysines/monomer. The PEGylation procedure was as follows:

1) The protein (PAL) was concentrated to 50-70 mg/ml and buffer-exchanged to 50 mM potassium phosphate, pH 8.5.
2) The amount of dry PEG needed was dissolved in 50 mM potassium phosphate, pH 8.5 and vortexed to dissolve. This step was done rapidly.

3) The protein solution was mixed immediately with the PEG solution to make the final concentrations of PEG and PAL and gently inverted several times.
4) The material was left with very gentle rocking at room temperature for 3 hours.
5) The PEG-PAL was ready to be formulated.

Results

The new PEGylation procedure was used to make PEG-PAL with a Z-factor of 1:3 and was tested in an in vivo mouse model for immunogenicity. The PAL used was the un-mutated wild-type form. Table 13 shows PEGylation results:

| PEGylation Method | Z-factor | PEG Source | Activity recovery (%) | Specific Activity | Remaining free amines/monomer |
|---|---|---|---|---|---|
| None | N/A | N/A | N/A | 3.6 | 30 |
| New | 1:3 | PEG-propanoic acid-NHS | 66 | 2.4 | 20.1 |
| Original | 1:8 | PEG-propanoic acid-NHS | 66 | 2.4 | 26.2 |

Figure 20:
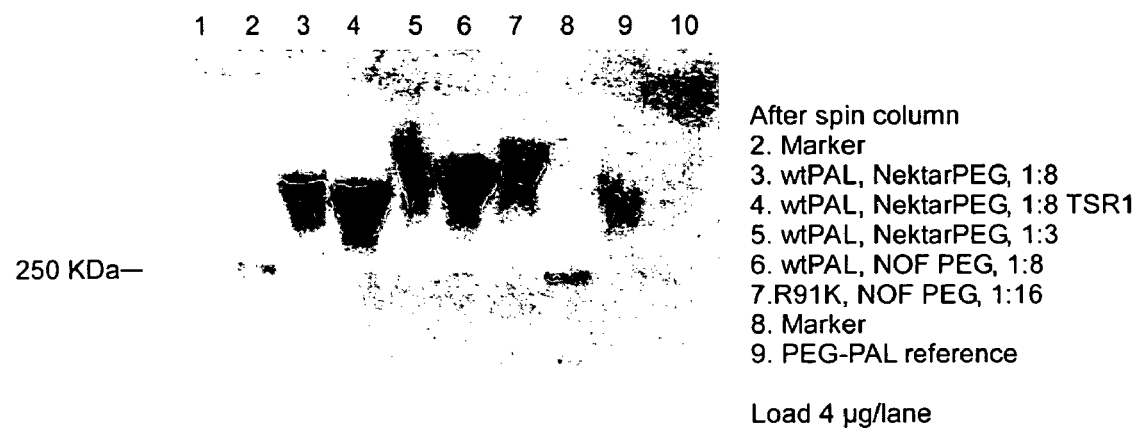
FIG. 20 shows SDS PAGE migration with Lanes 3 and 5 containing the relevant PEG-PAL forms.

FIG. 20 shows the SDS PAGE migration of these materials (as well as others). Lanes 3 and 5 show the relevant PEG-PAL forms.

The mouse study indicated that the new PEGylation method resulted in a PEG-PAL that was much less immunogenic than that of the original PEGylation method.

A follow-up study was performed using the new PEGylation procedure at lower Z-factors and using the alternate PEG supplier (20 kDa linear ME-200HS (PEG-hexanoic acid-NHS). The characterization results are shown in Table 14. Note that the new PEGylation protocol is referred to as "HC" (High Concentration). The form of PAL used was the R91K mutant.

TABLE 14

| | Primary amines per monomer | Pegylation % | Specific activity (U/mg) |
|---|---|---|---|
| Nektar 1:8 | 22.63 | 30.19 | 3.12 |
| NOF 1:4 | 21.56 | 33.49 | 2.39 |
| NOF 1:8 | 18.56 | 42.73 | 1.55 |
| NOF 1:1 HC | 15.89 | 50.98 | 1.93 |
| NOF 1:2 HC | 17.30 | 46.64 | 1.79 |
| NOF 1:3 HC | 16.08 | 50.38 | 1.44 |
| R91K | 32.41 | | |
| PEG-R91K | 21.94 | 32.31 | |

For the 1:1 "HC" material the PEG concentration was 8 mM (160 mg/ml) and the molar lysine concentration was 8 mM (20.5 mg/ml PAL). For the 1:2 "HC" material the PEG concentration was 8 mM and the molar lysine concentration was 4 mM (10.3 mg/ml PAL). The 1:3 material was made as described in the prior experiment.

Figure 21:
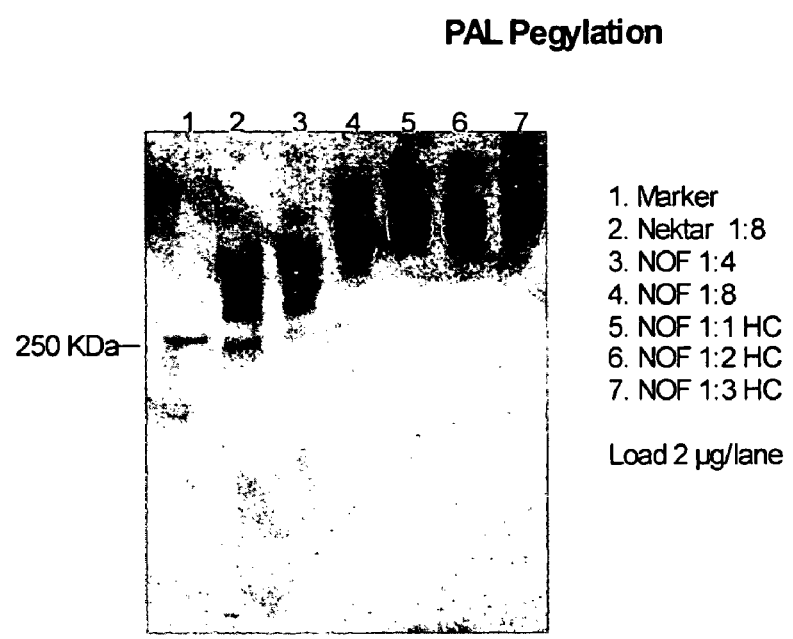
FIG. 21 shows SDS PAGE results for PEG-propanoic acid-NHS (1:8), and PEG-hexanoic acid-NHS (1:4, 1:8, 1:1 HC, 1:2 HC, and 1:3 HC).

SDS PAGE results of the above materials are shown in FIG. 21. The new PEGylation protocol gave higher molecular weights at all Z-factors tested, suggesting a greater extent of PEGylation in all new ("HC") samples tested.

Table 15 shows the recoveries from the PEGylation procedures.

| | Starting Vol Samp | Starting IU | Ending IU | Yield |
|---|---|---|---|---|
| R91K NOF PEG 1:4 | 2.13 | 94.7 | 58.8 | 62.1 |
| R91K NOF PEG 1:8 | 4.26 | 189.5 | 76.5 | 40.4 |
| R91K NOF PEG 1:1 HC | 0.33 | 83.5 | 38.7 | 46.3 |
| R91K NOF PEG 1:2 HC | 0.46 | 116.9 | 47.5 | 40.6 |
| R91K NOF PEG 1:3 HC | 0.77 | 194.8 | 71.3 | 36.6 |
| R91K Nektar PEG 1:8 | 1.83 | 81.2 | 56.1 | 69.1 |

Example 18

Clinical Evaluation with PAL Compositions

The following example provides guidance on the parameters to be used for the clinical evaluation of compositions comprising PAL or biologically active variants, mutants, and fragments thereof ("PAL") in the therapeutic methods of the present invention. As discussed herein throughout, PAL will be used in the treatment of HPA including HPA, mild phenylketonuria (PKU) and classic PKU. Clinical trials will be conducted which will provide an assessment of oral or subcutaneous doses of PAL for safety, pharmacokinetics, and initial response of both surrogate and defined clinical endpoints. The trial will be conducted for a minimum, but not necessarily limited to, 24 weeks to collect sufficient safety information for 100 evaluable patients. The initial dose for the trials will vary from about 0.001 to about 1.0 mg/kg/week. In the event that this dose does not produce a reduction in excess plasma phenylalanine (Phe) levels in a patient, or produce a significant direct clinical benefit measured as an ability to increase daily oral Phe intake without increases in plasma Phe levels, the dose should be increased as necessary, and maintained for an additional minimal period of, but necessarily limited to, 24 weeks to establish safety and to evaluate further efficacy.

Measurements of safety will include adverse events, allergic reactions, complete clinical chemistry panel (kidney and liver function), urinalysis, and CBC with differential. In addition, other parameters including the reduction in levels of blood Phe levels, neuropsychological and cognitive testing, and global assessments also will be monitored. The present example also contemplates the determination of pharmacokinetic parameters of the drug in the circulation, and general distribution and half-life of PAL in blood. It is anticipated that these measures will help relate dose to clinical response.

Methods

Patients who have elevated levels of plasma Phe will undergo a baseline a medical history and physical exam, neuropsychological and cognitive testing, a standard set of clinical laboratory tests (CBC, Panel 20, CH50, UA), levels of urinary pterins, dihydropteridine reductase (DHPR) levels, and a fasting blood (plasma) panel of serum amino acids. The patient will be followed closely with weekly visits to the clinic. Patients will return to the clinic for a complete evaluation one week after completing the treatment period. Should dose escalation be required, the patients will follow the same schedule outlined above. Safety will be monitored throughout the trial.

Diagnosis and Inclusion/Exclusion Criteria

The patient can be male or female, with a documented diagnosis of HPA or mild PKU confirmed by genetic testing and evidence of elevated Phe levels in blood. The study will include HPA or PKU patients who do not accurately follow dietary control. Female patients of childbearing potential must have a negative pregnancy test (urine β-hCG) just prior to each dosing and must be advised to use a medically accepted method of contraception throughout the study. A patient will be excluded from this study if the patient is pregnant or lactating; has received an investigational drug within 30 days prior to study enrollment; or has a medical condition, serious intercurrent illness, or other extenuating circumstance that may significantly decrease study compliance.

Dietary Intervention

Following the initial randomization and two-week treatment period, all study participants will undergo dietary counseling and will follow a standard Phe-restricted diet complemented with Phe-specific medical foods for a total of four to six weeks. Diets will be managed at home and dietary intake will be recorded in daily logs. Analyses of the intakes of nutrients and medical foods and the percent of Recommended Dietary Intakes (RDI) will be compared among the treatment groups.

PAL Safety

PAL therapy will be determined to be safe if no significant acute or chronic drug reactions occur during the course of the study. The longer-term administration of the drug will be determined to be safe if no significant abnormalities are observed in the clinical examinations, clinical labs, or other appropriate studies.

All printed patents and publications referred to in this application are hereby incorporated herein in their entirety by this reference.

While the preferred embodiment of the invention has been illustrated and described, it will be appreciated that various changes can be made therein without departing from the spirit and scope of the invention.

APPENDIX A

Docket No. 24501-10799

Table 16 - Gamez et al.  TSRI  Seq ID No: 4

```
HEADER    ----                                            XX-XXX-XX    xxxx
COMPND    ---
REMARK  3
REMARK  3 REFINEMENT.
REMARK  3   PROGRAM     : REFMAC 5.2.0005
REMARK  3   AUTHORS     : MURSHUDOV,VAGIN,DODSON
REMARK  3
REMARK  3   REFINEMENT TARGET : MAXIMUM LIKELIHOOD
REMARK  3
REMARK  3  DATA USED IN REFINEMENT.
REMARK  3   RESOLUTION RANGE HIGH (ANGSTROMS) :   1.60
REMARK  3   RESOLUTION RANGE LOW  (ANGSTROMS) :  41.89
REMARK  3   DATA CUTOFF            (SIGMA(F)) :   NONE
REMARK  3   COMPLETENESS FOR RANGE        (%) :  99.19
REMARK  3   NUMBER OF REFLECTIONS             : 353019
REMARK  3
REMARK  3  FIT TO DATA USED IN REFINEMENT.
REMARK  3   CROSS-VALIDATION METHOD           : THROUGHOUT
REMARK  3   FREE R VALUE TEST SET SELECTION   : RANDOM
REMARK  3   R VALUE     (WORKING + TEST SET)  : 0.16373
REMARK  3   R VALUE            (WORKING SET)  : 0.16241
REMARK  3   FREE R VALUE                      : 0.18860
REMARK  3   FREE R VALUE TEST SET SIZE   (%)  : 5.0
REMARK  3   FREE R VALUE TEST SET COUNT       : 18674
REMARK  3
REMARK  3  FIT IN THE HIGHEST RESOLUTION BIN.
REMARK  3   TOTAL NUMBER OF BINS USED             :    20
REMARK  3   BIN RESOLUTION RANGE HIGH             : 1.600
REMARK  3   BIN RESOLUTION RANGE LOW              : 1.642
REMARK  3   REFLECTION IN BIN     (WORKING SET)   : 24714
REMARK  3   BIN COMPLETENESS (WORKING+TEST) (%)   : 94.59
REMARK  3   BIN R VALUE           (WORKING SET)   : 0.248
REMARK  3   BIN FREE R VALUE SET COUNT            :  1306
REMARK  3   BIN FREE R VALUE                      : 0.291
REMARK  3
REMARK  3  NUMBER OF NON-HYDROGEN ATOMS USED IN REFINEMENT.
REMARK  3   ALL ATOMS            :   22122
REMARK  3
REMARK  3  B VALUES.
REMARK  3   FROM WILSON PLOT            (A**2) : NULL
REMARK  3   MEAN B VALUE     (OVERALL,  A**2) : 15.022
REMARK  3   OVERALL ANISOTROPIC B VALUE.
REMARK  3    B11 (A**2) :   0.03
REMARK  3    B22 (A**2) :   0.02
REMARK  3    B33 (A**2) :  -0.05
REMARK  3    B12 (A**2) :   0.00
REMARK  3    B13 (A**2) :   0.00
REMARK  3    B23 (A**2) :   0.00
REMARK  3
REMARK  3  ESTIMATED OVERALL COORDINATE ERROR.
REMARK  3   ESU BASED ON R VALUE                      (A):  0.077
REMARK  3   ESU BASED ON FREE R VALUE                 (A):  0.077
REMARK  3   ESU BASED ON MAXIMUM LIKELIHOOD           (A):  0.053
REMARK  3   ESU FOR B VALUES BASED ON MAXIMUM LIKELIHOOD (A**2):  2.943
REMARK  3
```

```
REMARK   3 CORRELATION COEFFICIENTS.
REMARK   3    CORRELATION COEFFICIENT FO-FC      :  0.964
REMARK   3    CORRELATION COEFFICIENT FO-FC FREE :  0.954
REMARK   3
REMARK   3  RMS DEVIATIONS FROM IDEAL VALUES         COUNT     RMS      WEIGHT
REMARK   3   BOND LENGTHS REFINED ATOMS       (A): 20550 ; 0.017 ; 0.022
REMARK   3   BOND LENGTHS OTHERS              (A): 19204 ; 0.001 ; 0.020
REMARK   3   BOND ANGLES REFINED ATOMS  (DEGREES): 27898 ; 1.584 ; 1.964
REMARK   3   BOND ANGLES OTHERS         (DEGREES): 44547 ; 0.884 ; 3.000
REMARK   3   TORSION ANGLES, PERIOD 1   (DEGREES):  2651 ; 6.427 ; 5.000
REMARK   3   TORSION ANGLES, PERIOD 2   (DEGREES):   837 ;35.462 ;24.002
REMARK   3   TORSION ANGLES, PERIOD 3   (DEGREES):  3503 ;12.831 ;15.000
REMARK   3   TORSION ANGLES, PERIOD 4   (DEGREES):   134 ;17.821 ;15.000
REMARK   3   CHIRAL-CENTER RESTRAINTS      (A**3):  3345 ; 0.097 ; 0.200
REMARK   3   GENERAL PLANES REFINED ATOMS     (A): 22831 ; 0.007 ; 0.020
REMARK   3   GENERAL PLANES OTHERS            (A):  3921 ; 0.001 ; 0.020
REMARK   3   NON-BONDED CONTACTS REFINED ATOMS(A):  5028 ; 0.233 ; 0.200
REMARK   3   NON-BONDED CONTACTS OTHERS       (A): 20008 ; 0.187 ; 0.200
REMARK   3   NON-BONDED TORSION REFINED ATOMS (A): 10621 ; 0.179 ; 0.200
REMARK   3   NON-BONDED TORSION OTHERS        (A): 11775 ; 0.084 ; 0.200
REMARK   3   H-BOND (X...Y) REFINED ATOMS     (A):  1474 ; 0.115 ; 0.200
REMARK   3   H-BOND (X...Y) OTHERS            (A):     1 ; 0.040 ; 0.200
REMARK   3   SYMMETRY VDW REFINED ATOMS       (A):     9 ; 0.165 ; 0.200
REMARK   3   SYMMETRY VDW OTHERS              (A):    52 ; 0.230 ; 0.200
REMARK   3   SYMMETRY H-BOND REFINED ATOMS    (A):    23 ; 0.162 ; 0.200
REMARK   3
REMARK   3  ISOTROPIC THERMAL FACTOR RESTRAINTS.    COUNT    RMS     WEIGHT
REMARK   3   MAIN-CHAIN BOND REFINED ATOMS  (A**2): 14211 ; 1.248 ; 1.500
REMARK   3   MAIN-CHAIN BOND OTHER ATOMS    (A**2):  5401 ; 0.310 ; 1.500
REMARK   3   MAIN-CHAIN ANGLE REFINED ATOMS (A**2): 21289 ; 1.501 ; 2.000
REMARK   3   SIDE-CHAIN BOND REFINED ATOMS  (A**2):  7754 ; 2.670 ; 3.000
REMARK   3   SIDE-CHAIN ANGLE REFINED ATOMS (A**2):  6609 ; 3.733 ; 4.500
REMARK   3
REMARK   3  NCS RESTRAINTS STATISTICS
REMARK   3   NUMBER OF NCS GROUPS : NULL
REMARK   3
REMARK   3
REMARK   3  TLS DETAILS
REMARK   3   NUMBER OF TLS GROUPS  :    4
REMARK   3   ATOM RECORD CONTAINS RESIDUAL B FACTORS ONLY
REMARK   3
REMARK   3   TLS GROUP :     1
REMARK   3    NUMBER OF COMPONENTS GROUP :    1
REMARK   3    COMPONENTS        C SSSEQI   TO   C SSSEQI
REMARK   3    RESIDUE RANGE :   A    26        A    716
REMARK   3    ORIGIN FOR THE GROUP (A):  35.2414   61.3812    2.0992
REMARK   3    T TENSOR
REMARK   3      T11:  -0.0046 T22:  -0.0514
REMARK   3      T33:  -0.0138 T12:   0.0177
REMARK   3      T13:  -0.0139 T23:  -0.0380
REMARK   3    L TENSOR
REMARK   3      L11:   0.5401 L22:   0.0733
REMARK   3      L33:   0.2912 L12:   0.0274
REMARK   3      L13:   0.2140 L23:   0.0133
REMARK   3    S TENSOR
REMARK   3      S11:   0.0576 S12:   0.1179 S13:  -0.1220
REMARK   3      S21:  -0.0242 S22:  -0.0097 S23:  -0.0155
```

```
REMARK   3        S31:   0.0864 S32:    0.0384 S33:  -0.0479
REMARK   3
REMARK   3    TLS GROUP :     2
REMARK   3     NUMBER OF COMPONENTS GROUP :    1
REMARK   3     COMPONENTS        C SSSEQI    TO   C SSSEQI
REMARK   3     RESIDUE RANGE :    B    26         B    716
REMARK   3     ORIGIN FOR THE GROUP (A):  54.3329  93.9613   9.1029
REMARK   3     T TENSOR
REMARK   3       T11:  -0.0510 T22:   -0.0537
REMARK   3       T33:  -0.0622 T12:    0.0011
REMARK   3       T13:   0.0193 T23:    0.0160
REMARK   3     L TENSOR
REMARK   3       L11:   0.4371 L22:    0.1840
REMARK   3       L33:   0.3807 L12:   -0.0001
REMARK   3       L13:   0.1501 L23:   -0.0249
REMARK   3     S TENSOR
REMARK   3       S11:   0.0044 S12:    0.1146 S13:    0.0103
REMARK   3       S21:  -0.0395 S22:   -0.0221 S23:   -0.0269
REMARK   3       S31:  -0.0150 S32:    0.1002 S33:    0.0177
REMARK   3
REMARK   3    TLS GROUP :     3
REMARK   3     NUMBER OF COMPONENTS GROUP :    1
REMARK   3     COMPONENTS        C SSSEQI    TO   C SSSEQI
REMARK   3     RESIDUE RANGE :    C    26         C    716
REMARK   3     ORIGIN FOR THE GROUP (A):  39.4919  66.4837  38.2387
REMARK   3     T TENSOR
REMARK   3       T11:  -0.0302 T22:   -0.0713
REMARK   3       T33:  -0.0391 T12:   -0.0121
REMARK   3       T13:  -0.0071 T23:    0.0282
REMARK   3     L TENSOR
REMARK   3       L11:   0.4726 L22:    0.1164
REMARK   3       L33:   0.3460 L12:   -0.0294
REMARK   3       L13:   0.1836 L23:   -0.0183
REMARK   3     S TENSOR
REMARK   3       S11:   0.0462 S12:   -0.0915 S13:   -0.0862
REMARK   3       S21:   0.0189 S22:   -0.0111 S23:    0.0110
REMARK   3       S31:   0.0641 S32:   -0.0559 S33:   -0.0350
REMARK   3
REMARK   3    TLS GROUP :     4
REMARK   3     NUMBER OF COMPONENTS GROUP :    1
REMARK   3     COMPONENTS        C SSSEQI    TO   C SSSEQI
REMARK   3     RESIDUE RANGE :    D    26         D    716
REMARK   3     ORIGIN FOR THE GROUP (A):  20.0100  95.7143  22.1331
REMARK   3     T TENSOR
REMARK   3       T11:  -0.0547 T22:   -0.0582
REMARK   3       T33:  -0.0613 T12:    0.0184
REMARK   3       T13:   0.0069 T23:   -0.0012
REMARK   3     L TENSOR
REMARK   3       L11:   0.4123 L22:    0.1456
REMARK   3       L33:   0.4070 L12:    0.0398
REMARK   3       L13:   0.1953 L23:    0.0840
REMARK   3     S TENSOR
REMARK   3       S11:  -0.0076 S12:   -0.0713 S13:    0.0313
REMARK   3       S21:   0.0108 S22:   -0.0284 S23:    0.0321
REMARK   3       S31:  -0.0332 S32:   -0.1113 S33:    0.0361
REMARK   3
REMARK   3
```

```
REMARK   3  BULK SOLVENT MODELLING.
REMARK   3   METHOD USED : MASK
REMARK   3   PARAMETERS FOR MASK CALCULATION
REMARK   3   VDW PROBE RADIUS    :  1.20
REMARK   3   ION PROBE RADIUS    :  0.80
REMARK   3   SHRINKAGE RADIUS    :  0.80
REMARK   3
REMARK   3  OTHER REFINEMENT REMARKS:
REMARK   3  HYDROGENS HAVE BEEN ADDED IN THE RIDING POSITIONS
REMARK   3
LINK            ARG A 102                 THR A 124                gap
CISPEP   1 VAL A 173    ASN A 174                  0.00
LINK            VAL A 349                 ASP A 354                gap
LINK            ASN A 397                 PRO A 398                NMCIS
LINK            GLY B  34                 THR B  39                gap
LINK            SER B 108                 THR B 124                gap
LINK            LYS B 350                 ASP B 354                gap
LINK            ASN B 397                 PRO B 398                NMCIS
LINK            SER C 103                 GLU C 125                gap
LINK            GLU C 347                 ASP C 354                gap
LINK            ASN C 397                 PRO C 398                NMCIS
LINK            VAL D  32                 THR D  39                gap
LINK            SER D 103                 THR D 124                gap
LINK            VAL D 349                 ASP D 354                gap
LINK            ASN D 397                 PRO D 398                NMCIS
LINK            VAL B 349                 ASP B 354                gap
LINK            ARG B 102                 THR B 124                gap
LINK            ILE B 209                 GLY B 213                gap
LINK            ARG C 102                 GLU C 125                gap
LINK            LEU C 101                 GLU C 125                gap
LINK            ILE C 209                 GLY C 213                gap
LINK            ARG D 102                 THR D 124                gap
LINK            ILE D 209                 GLY D 213                gap
CRYST1  104.759  151.612  179.922  90.00  90.00  90.00 P 21 21 21
SCALE1     0.009546  0.000000  0.000000       0.00000
SCALE2     0.000000  0.006596  0.000000       0.00000
SCALE3     0.000000  0.000000  0.005558       0.00000
ATOM     1  N    ALA A  26      63.728  62.054  -5.647  1.00 32.19           N
ATOM     2  CA   ALA A  26      62.304  62.497  -5.487  1.00 31.73           C
ATOM     4  CB   ALA A  26      62.248  63.809  -4.750  1.00 32.17           C
ATOM     8  C    ALA A  26      61.626  62.624  -6.866  1.00 31.82           C
ATOM     9  O    ALA A  26      62.274  62.996  -7.854  1.00 31.26           O
ATOM    13  N    SER A  27      60.333  62.305  -6.935  1.00 31.19           N
ATOM    14  CA   SER A  27      59.613  62.369  -8.205  1.00 31.13           C
ATOM    16  CB   SER A  27      58.313  61.563  -8.146  1.00 31.39           C
ATOM    19  OG   SER A  27      57.521  61.775  -9.307  1.00 31.31           O
ATOM    21  C    SER A  27      59.334  63.819  -8.575  1.00 31.00           C
ATOM    22  O    SER A  27      58.974  64.623  -7.724  1.00 30.04           O
ATOM    24  N    THR A  28      59.527  64.147  -9.853  1.00 30.53           N
ATOM    25  CA   THR A  28      59.162  65.461 -10.371  1.00 31.07           C
ATOM    27  CB   THR A  28      60.139  65.954 -11.463  1.00 31.34           C
ATOM    29  OG1  THR A  28      60.177  65.008 -12.542  1.00 32.59           O
ATOM    31  CG2  THR A  28      61.528  66.117 -10.885  1.00 32.91           C
ATOM    35  C    THR A  28      57.786  65.399 -10.980  1.00 30.70           C
ATOM    36  O    THR A  28      57.316  66.407 -11.504  1.00 30.88           O
ATOM    38  N    ASN A  29      57.155  64.219 -10.943  1.00 29.91           N
ATOM    39  CA   ASN A  29      55.782  64.059 -11.399  1.00 29.44           C
```

| ATOM | 41 | CB | ASN | A | 29 | 55.441 | 62.571 | -11.555 | 1.00 | 29.48 | C |
|---|---|---|---|---|---|---|---|---|---|---|---|
| ATOM | 44 | CG | ASN | A | 29 | 54.050 | 62.337 | -12.113 | 1.00 | 31.33 | C |
| ATOM | 45 | OD1 | ASN | A | 29 | 53.255 | 63.258 | -12.250 | 1.00 | 31.52 | O |
| ATOM | 46 | ND2 | ASN | A | 29 | 53.760 | 61.086 | -12.455 | 1.00 | 34.57 | N |
| ATOM | 49 | C | ASN | A | 29 | 54.836 | 64.722 | -10.395 | 1.00 | 28.65 | C |
| ATOM | 50 | O | ASN | A | 29 | 54.760 | 64.286 | -9.233 | 1.00 | 26.78 | O |
| ATOM | 52 | N | LEU | A | 30 | 54.128 | 65.770 | -10.833 | 1.00 | 27.50 | N |
| ATOM | 53 | CA | LEU | A | 30 | 53.246 | 66.515 | -9.909 | 1.00 | 27.51 | C |
| ATOM | 55 | CB | LEU | A | 30 | 52.619 | 67.764 | -10.565 | 1.00 | 27.95 | C |
| ATOM | 58 | CG | LEU | A | 30 | 53.538 | 68.912 | -10.999 | 1.00 | 29.22 | C |
| ATOM | 60 | CD1 | LEU | A | 30 | 52.685 | 70.100 | -11.391 | 1.00 | 31.14 | C |
| ATOM | 64 | CD2 | LEU | A | 30 | 54.482 | 69.329 | -9.902 | 1.00 | 30.38 | C |
| ATOM | 68 | C | LEU | A | 30 | 52.132 | 65.658 | -9.325 | 1.00 | 26.92 | C |
| ATOM | 69 | O | LEU | A | 30 | 51.636 | 65.952 | -8.213 | 1.00 | 26.23 | O |
| ATOM | 71 | N | ALA | A | 31 | 51.702 | 64.632 | -10.067 | 1.00 | 26.29 | N |
| ATOM | 72 | CA | ALA | A | 31 | 50.721 | 63.661 | -9.531 | 1.00 | 26.11 | C |
| ATOM | 74 | CB | ALA | A | 31 | 50.335 | 62.632 | -10.574 | 1.00 | 25.94 | C |
| ATOM | 78 | C | ALA | A | 31 | 51.246 | 62.947 | -8.280 | 1.00 | 26.15 | C |
| ATOM | 79 | O | ALA | A | 31 | 50.461 | 62.526 | -7.420 | 1.00 | 26.13 | O |
| ATOM | 81 | N | VAL | A | 32 | 52.575 | 62.800 | -8.189 | 1.00 | 24.75 | N |
| ATOM | 82 | CA | VAL | A | 32 | 53.221 | 62.316 | -6.961 | 1.00 | 25.35 | C |
| ATOM | 84 | CB | VAL | A | 32 | 54.601 | 61.616 | -7.269 | 1.00 | 24.98 | C |
| ATOM | 86 | CG1 | VAL | A | 32 | 55.266 | 61.130 | -5.977 | 1.00 | 26.10 | C |
| ATOM | 90 | CG2 | VAL | A | 32 | 54.410 | 60.474 | -8.224 | 1.00 | 24.44 | C |
| ATOM | 94 | C | VAL | A | 32 | 53.477 | 63.461 | -5.970 | 1.00 | 25.19 | C |
| ATOM | 95 | O | VAL | A | 32 | 53.221 | 63.333 | -4.762 | 1.00 | 25.34 | O |
| ATOM | 97 | N | ALA | A | 33 | 54.029 | 64.558 | -6.496 | 1.00 | 25.29 | N |
| ATOM | 98 | CA | ALA | A | 33 | 54.586 | 65.612 | -5.673 | 1.00 | 25.02 | C |
| ATOM | 100 | CB | ALA | A | 33 | 55.629 | 66.369 | -6.439 | 1.00 | 25.54 | C |
| ATOM | 104 | C | ALA | A | 33 | 53.551 | 66.589 | -5.159 | 1.00 | 25.26 | C |
| ATOM | 105 | O | ALA | A | 33 | 53.843 | 67.277 | -4.215 | 1.00 | 25.16 | O |
| ATOM | 107 | N | GLY | A | 34 | 52.364 | 66.666 | -5.770 | 1.00 | 24.57 | N |
| ATOM | 108 | CA | GLY | A | 34 | 51.415 | 67.784 | -5.474 | 1.00 | 24.23 | C |
| ATOM | 111 | C | GLY | A | 34 | 52.020 | 69.105 | -5.967 | 1.00 | 24.00 | C |
| ATOM | 112 | O | GLY | A | 34 | 53.067 | 69.121 | -6.660 | 1.00 | 22.90 | O |
| ATOM | 114 | N | SER | A | 35 | 51.422 | 70.225 | -5.562 | 1.00 | 22.22 | N |
| ATOM | 115 | CA | SER | A | 35 | 51.962 | 71.522 | -5.977 | 1.00 | 22.18 | C |
| ATOM | 117 | CB | SER | A | 35 | 51.304 | 71.968 | -7.258 | 1.00 | 21.83 | C |
| ATOM | 120 | OG | SER | A | 35 | 51.827 | 73.196 | -7.662 | 1.00 | 20.55 | O |
| ATOM | 122 | C | SER | A | 35 | 51.734 | 72.601 | -4.938 | 1.00 | 21.94 | C |
| ATOM | 123 | O | SER | A | 35 | 50.639 | 72.667 | -4.368 | 1.00 | 21.86 | O |
| ATOM | 125 | N | HIS | A | 36 | 52.762 | 73.428 | -4.707 | 1.00 | 22.69 | N |
| ATOM | 126 | CA | HIS | A | 36 | 52.642 | 74.556 | -3.748 | 1.00 | 22.63 | C |
| ATOM | 128 | CB | HIS | A | 36 | 54.041 | 75.001 | -3.266 | 1.00 | 20.79 | C |
| ATOM | 131 | CG | HIS | A | 36 | 54.712 | 74.013 | -2.369 | 1.00 | 23.06 | C |
| ATOM | 132 | ND1 | HIS | A | 36 | 55.742 | 73.206 | -2.803 | 1.00 | 23.12 | N |
| ATOM | 134 | CE1 | HIS | A | 36 | 56.157 | 72.447 | -1.796 | 1.00 | 23.64 | C |
| ATOM | 136 | NE2 | HIS | A | 36 | 55.449 | 72.757 | -0.728 | 1.00 | 23.53 | N |
| ATOM | 138 | CD2 | HIS | A | 36 | 54.559 | 73.749 | -1.053 | 1.00 | 20.85 | C |
| ATOM | 140 | C | HIS | A | 36 | 51.885 | 75.768 | -4.296 | 1.00 | 23.80 | C |
| ATOM | 141 | O | HIS | A | 36 | 51.455 | 76.654 | -3.523 | 1.00 | 24.02 | O |
| ATOM | 143 | N | LEU | A | 37 | 51.719 | 75.839 | -5.603 | 1.00 | 22.27 | N |
| ATOM | 144 | CA | LEU | A | 37 | 50.817 | 76.818 | -6.191 | 1.00 | 23.23 | C |
| ATOM | 146 | CB | LEU | A | 37 | 51.635 | 77.745 | -7.106 | 1.00 | 23.16 | C |
| ATOM | 149 | CG | LEU | A | 37 | 52.640 | 78.504 | -6.225 | 1.00 | 24.52 | C |
| ATOM | 151 | CD1 | LEU | A | 37 | 53.914 | 78.875 | -7.001 | 1.00 | 20.83 | C |
| ATOM | 155 | CD2 | LEU | A | 37 | 51.902 | 79.675 | -5.473 | 1.00 | 21.36 | C |

| ATOM | 159 | C | LEU | A | 37 | 49.694 | 76.220 | -7.051 | 1.00 | 23.21 | C |
| ATOM | 160 | O | LEU | A | 37 | 49.825 | 75.115 | -7.623 | 1.00 | 23.62 | O |
| ATOM | 162 | N | PRO | A | 38 | 48.610 | 76.987 | -7.214 | 1.00 | 22.42 | N |
| ATOM | 163 | CA | PRO | A | 38 | 47.614 | 76.539 | -8.216 | 1.00 | 22.72 | C |
| ATOM | 165 | CB | PRO | A | 38 | 46.597 | 77.690 | -8.225 | 1.00 | 23.28 | C |
| ATOM | 168 | CG | PRO | A | 38 | 46.823 | 78.483 | -6.871 | 1.00 | 21.40 | C |
| ATOM | 171 | CD | PRO | A | 38 | 48.275 | 78.284 | -6.596 | 1.00 | 21.98 | C |
| ATOM | 174 | C | PRO | A | 38 | 48.187 | 76.322 | -9.645 | 1.00 | 23.03 | C |
| ATOM | 175 | O | PRO | A | 38 | 48.914 | 77.164 | -10.160 | 1.00 | 22.48 | O |
| ATOM | 176 | N | THR | A | 39 | 47.835 | 75.213 | -10.295 | 1.00 | 23.29 | N |
| ATOM | 177 | CA | THR | A | 39 | 48.314 | 74.929 | -11.617 | 1.00 | 24.06 | C |
| ATOM | 179 | CB | THR | A | 39 | 49.762 | 74.341 | -11.607 | 1.00 | 24.22 | C |
| ATOM | 181 | OG1 | THR | A | 39 | 50.114 | 73.882 | -12.920 | 1.00 | 23.98 | O |
| ATOM | 183 | CG2 | THR | A | 39 | 49.891 | 73.173 | -10.663 | 1.00 | 24.63 | C |
| ATOM | 187 | C | THR | A | 39 | 47.406 | 73.941 | -12.311 | 1.00 | 24.53 | C |
| ATOM | 188 | O | THR | A | 39 | 46.935 | 72.983 | -11.699 | 1.00 | 25.31 | O |
| ATOM | 190 | N | THR | A | 40 | 47.173 | 74.169 | -13.592 | 1.00 | 24.90 | N |
| ATOM | 191 | CA | THR | A | 40 | 46.385 | 73.239 | -14.383 | 1.00 | 26.03 | C |
| ATOM | 193 | CB | THR | A | 40 | 45.870 | 73.926 | -15.690 | 1.00 | 26.44 | C |
| ATOM | 195 | OG1 | THR | A | 40 | 46.998 | 74.385 | -16.454 | 1.00 | 25.97 | O |
| ATOM | 197 | CG2 | THR | A | 40 | 44.940 | 75.129 | -15.341 | 1.00 | 27.53 | C |
| ATOM | 201 | C | THR | A | 40 | 47.205 | 71.992 | -14.758 | 1.00 | 26.23 | C |
| ATOM | 202 | O | THR | A | 40 | 46.650 | 71.046 | -15.350 | 1.00 | 26.70 | O |
| ATOM | 204 | N | GLN | A | 41 | 48.502 | 71.988 | -14.435 | 1.00 | 25.88 | N |
| ATOM | 205 | CA | GLN | A | 41 | 49.373 | 70.845 | -14.735 | 1.00 | 26.92 | C |
| ATOM | 207 | CB | GLN | A | 41 | 50.866 | 71.202 | -14.623 | 1.00 | 26.41 | C |
| ATOM | 210 | CG | GLN | A | 41 | 51.442 | 72.178 | -15.650 | 1.00 | 29.69 | C |
| ATOM | 213 | CD | GLN | A | 41 | 52.983 | 72.064 | -15.706 | 1.00 | 31.92 | C |
| ATOM | 214 | OE1 | GLN | A | 41 | 53.615 | 71.492 | -14.790 | 1.00 | 38.11 | O |
| ATOM | 215 | NE2 | GLN | A | 41 | 53.587 | 72.588 | -16.782 | 1.00 | 38.01 | N |
| ATOM | 218 | C | GLN | A | 41 | 49.120 | 69.650 | -13.798 | 1.00 | 25.99 | C |
| ATOM | 219 | O | GLN | A | 41 | 49.684 | 68.591 | -14.028 | 1.00 | 27.10 | O |
| ATOM | 221 | N | VAL | A | 42 | 48.370 | 69.804 | -12.710 | 1.00 | 23.12 | N |
| ATOM | 222 | CA | VAL | A | 42 | 48.050 | 68.631 | -11.900 | 1.00 | 22.78 | C |
| ATOM | 224 | CB | VAL | A | 42 | 49.098 | 68.312 | -10.823 | 1.00 | 22.11 | C |
| ATOM | 226 | CG1 | VAL | A | 42 | 49.012 | 69.290 | -9.635 | 1.00 | 25.52 | C |
| ATOM | 230 | CG2 | VAL | A | 42 | 48.968 | 66.865 | -10.324 | 1.00 | 22.68 | C |
| ATOM | 234 | C | VAL | A | 42 | 46.681 | 68.780 | -11.260 | 1.00 | 21.45 | C |
| ATOM | 235 | O | VAL | A | 42 | 46.181 | 69.894 | -11.071 | 1.00 | 23.55 | O |
| ATOM | 237 | N | THR | A | 43 | 46.046 | 67.643 | -11.006 | 1.00 | 19.33 | N |
| ATOM | 238 | CA | THR | A | 43 | 44.742 | 67.635 | -10.389 | 1.00 | 17.55 | C |
| ATOM | 240 | CB | THR | A | 43 | 43.655 | 67.204 | -11.394 | 1.00 | 18.29 | C |
| ATOM | 242 | OG1 | THR | A | 43 | 43.868 | 65.852 | -11.770 | 1.00 | 18.96 | O |
| ATOM | 244 | CG2 | THR | A | 43 | 43.628 | 68.116 | -12.640 | 1.00 | 17.35 | C |
| ATOM | 248 | C | THR | A | 43 | 44.663 | 66.666 | -9.204 | 1.00 | 16.12 | C |
| ATOM | 249 | O | THR | A | 43 | 45.476 | 65.765 | -9.073 | 1.00 | 14.93 | O |
| ATOM | 251 | N | GLN | A | 44 | 43.631 | 66.841 | -8.368 | 1.00 | 15.81 | N |
| ATOM | 252 | CA | GLN | A | 44 | 43.405 | 65.937 | -7.265 | 1.00 | 15.03 | C |
| ATOM | 254 | CB | GLN | A | 44 | 42.240 | 66.412 | -6.405 | 1.00 | 15.53 | C |
| ATOM | 257 | CG | GLN | A | 44 | 42.002 | 65.642 | -5.142 | 1.00 | 14.85 | C |
| ATOM | 260 | CD | GLN | A | 44 | 41.086 | 66.441 | -4.246 | 1.00 | 15.48 | C |
| ATOM | 261 | OE1 | GLN | A | 44 | 39.987 | 66.831 | -4.680 | 1.00 | 13.51 | O |
| ATOM | 262 | NE2 | GLN | A | 44 | 41.484 | 66.660 | -3.000 | 1.00 | 14.96 | N |
| ATOM | 265 | C | GLN | A | 44 | 43.168 | 64.528 | -7.755 | 1.00 | 14.97 | C |
| ATOM | 266 | O | GLN | A | 44 | 43.690 | 63.585 | -7.168 | 1.00 | 15.32 | O |
| ATOM | 268 | N | VAL | A | 45 | 42.354 | 64.354 | -8.803 | 1.00 | 14.71 | N |
| ATOM | 269 | CA | VAL | A | 45 | 42.198 | 63.016 | -9.421 | 1.00 | 15.73 | C |

| | | | | | | | | | |
|---|---|---|---|---|---|---|---|---|---|
| ATOM | 271 | CB | VAL A | 45 | 41.210 | 63.026 | -10.640 | 1.00 15.74 | C |
| ATOM | 273 | CG1 | VAL A | 45 | 41.251 | 61.690 | -11.384 | 1.00 18.68 | C |
| ATOM | 277 | CG2 | VAL A | 45 | 39.806 | 63.311 | -10.184 | 1.00 17.06 | C |
| ATOM | 281 | C | VAL A | 45 | 43.553 | 62.374 | -9.779 | 1.00 14.32 | C |
| ATOM | 282 | O | VAL A | 45 | 43.792 | 61.187 | -9.472 | 1.00 15.33 | O |
| ATOM | 284 | N | ASP A | 46 | 44.441 | 63.144 | -10.421 | 1.00 14.87 | N |
| ATOM | 285 | CA | ASP A | 46 | 45.804 | 62.649 | -10.782 | 1.00 15.49 | C |
| ATOM | 287 | CB | ASP A | 46 | 46.684 | 63.762 | -11.385 | 1.00 16.60 | C |
| ATOM | 290 | CG | ASP A | 46 | 46.249 | 64.248 | -12.732 | 1.00 19.32 | C |
| ATOM | 291 | OD1 | ASP A | 46 | 45.558 | 63.499 | -13.459 | 1.00 20.46 | O |
| ATOM | 292 | OD2 | ASP A | 46 | 46.641 | 65.410 | -13.074 | 1.00 19.12 | O |
| ATOM | 293 | C | ASP A | 46 | 46.542 | 62.158 | -9.513 | 1.00 14.58 | C |
| ATOM | 294 | O | ASP A | 46 | 47.141 | 61.080 | -9.475 | 1.00 13.51 | O |
| ATOM | 296 | N | ILE A | 47 | 46.464 | 62.960 | -8.443 | 1.00 14.23 | N |
| ATOM | 297 | CA | ILE A | 47 | 47.109 | 62.621 | -7.167 | 1.00 14.98 | C |
| ATOM | 299 | CB | ILE A | 47 | 47.026 | 63.869 | -6.210 | 1.00 14.12 | C |
| ATOM | 301 | CG1 | ILE A | 47 | 47.913 | 65.007 | -6.745 | 1.00 15.96 | C |
| ATOM | 304 | CD1 | ILE A | 47 | 47.710 | 66.317 | -5.974 | 1.00 17.79 | C |
| ATOM | 308 | CG2 | ILE A | 47 | 47.373 | 63.510 | -4.777 | 1.00 15.22 | C |
| ATOM | 312 | C | ILE A | 47 | 46.505 | 61.375 | -6.508 | 1.00 14.20 | C |
| ATOM | 313 | O | ILE A | 47 | 47.224 | 60.477 | -6.038 | 1.00 14.27 | O |
| ATOM | 315 | N | VAL A | 48 | 45.178 | 61.319 | -6.486 | 1.00 13.64 | N |
| ATOM | 316 | CA | VAL A | 48 | 44.475 | 60.128 | -6.006 | 1.00 13.77 | C |
| ATOM | 318 | CB | VAL A | 48 | 42.967 | 60.366 | -5.950 | 1.00 13.78 | C |
| ATOM | 320 | CG1 | VAL A | 48 | 42.235 | 59.032 | -5.693 | 1.00 15.72 | C |
| ATOM | 324 | CG2 | VAL A | 48 | 42.674 | 61.468 | -4.843 | 1.00 13.62 | C |
| ATOM | 328 | C | VAL A | 48 | 44.817 | 58.859 | -6.769 | 1.00 14.18 | C |
| ATOM | 329 | O | VAL A | 48 | 45.100 | 57.813 | -6.163 | 1.00 13.80 | O |
| ATOM | 331 | N | GLU A | 49 | 44.802 | 58.952 | -8.095 | 1.00 14.10 | N |
| ATOM | 332 | CA | GLU A | 49 | 45.120 | 57.819 | -8.940 | 1.00 15.90 | C |
| ATOM | 334 | CB | GLU A | 49 | 45.118 | 58.253 | -10.391 | 1.00 14.98 | C |
| ATOM | 337 | CG | GLU A | 49 | 45.307 | 57.120 | -11.351 | 1.00 20.31 | C |
| ATOM | 340 | CD | GLU A | 49 | 45.282 | 57.601 | -12.794 | 1.00 22.35 | C |
| ATOM | 341 | OE1 | GLU A | 49 | 45.887 | 58.688 | -13.088 | 1.00 29.58 | O |
| ATOM | 342 | OE2 | GLU A | 49 | 44.686 | 56.871 | -13.639 | 1.00 30.53 | O |
| ATOM | 343 | C | GLU A | 49 | 46.494 | 57.252 | -8.567 | 1.00 14.80 | C |
| ATOM | 344 | O | GLU A | 49 | 46.643 | 56.049 | -8.427 | 1.00 14.84 | O |
| ATOM | 346 | N | LYS A | 50 | 47.485 | 58.128 | -8.414 | 1.00 15.99 | N |
| ATOM | 347 | CA | LYS A | 50 | 48.842 | 57.694 | -8.069 | 1.00 16.93 | C |
| ATOM | 349 | CB | LYS A | 50 | 49.820 | 58.859 | -8.207 | 1.00 17.59 | C |
| ATOM | 352 | CG | LYS A | 50 | 51.253 | 58.571 | -7.798 | 1.00 20.50 | C |
| ATOM | 355 | CD | LYS A | 50 | 51.989 | 57.707 | -8.810 | 1.00 25.52 | C |
| ATOM | 358 | CE | LYS A | 50 | 53.250 | 56.984 | -8.174 | 1.00 25.77 | C |
| ATOM | 361 | NZ | LYS A | 50 | 53.712 | 55.797 | -9.001 | 1.00 28.26 | N |
| ATOM | 365 | C | LYS A | 50 | 48.882 | 57.040 | -6.684 | 1.00 16.55 | C |
| ATOM | 366 | O | LYS A | 50 | 49.505 | 55.993 | -6.517 | 1.00 15.88 | O |
| ATOM | 368 | N | MSE A | 51 | 48.188 | 57.613 | -5.706 | 1.00 17.37 | N |
| ATOM | 369 | CA | MSE A | 51 | 48.148 | 57.039 | -4.350 | 1.00 19.03 | C |
| ATOM | 371 | CB | MSE A | 51 | 47.369 | 57.934 | -3.351 | 1.00 19.27 | C |
| ATOM | 374 | CG | MSE A | 51 | 48.124 | 59.134 | -2.887 | 1.00 19.27 | C |
| ATOM | 377 | SE | MSE A | 51 | 47.141 | 59.910 | -1.344 | 1.00 30.03 | SE |
| ATOM | 378 | CE | MSE A | 51 | 48.330 | 59.342 | 0.198 | 1.00 31.07 | C |
| ATOM | 382 | C | MSE A | 51 | 47.535 | 55.658 | -4.338 | 1.00 18.62 | C |
| ATOM | 383 | O | MSE A | 51 | 48.063 | 54.749 | -3.698 | 1.00 19.37 | O |
| ATOM | 385 | N | LEU A | 52 | 46.448 | 55.482 | -5.074 | 1.00 18.56 | N |
| ATOM | 386 | CA | LEU A | 52 | 45.717 | 54.225 | -5.079 | 1.00 19.25 | C |
| ATOM | 388 | CB | LEU A | 52 | 44.295 | 54.402 | -5.609 | 1.00 19.76 | C |

| ATOM | 391 | CG | LEU A | 52 | 43.382 | 55.322 | -4.761 | 1.00 | 20.17 | C |
| ATOM | 393 | CD1 | LEU A | 52 | 41.980 | 55.389 | -5.329 | 1.00 | 22.98 | C |
| ATOM | 397 | CD2 | LEU A | 52 | 43.348 | 54.895 | -3.353 | 1.00 | 21.26 | C |
| ATOM | 401 | C | LEU A | 52 | 46.460 | 53.191 | -5.895 | 1.00 | 18.77 | C |
| ATOM | 402 | O | LEU A | 52 | 46.146 | 52.012 | -5.848 | 1.00 | 20.94 | O |
| ATOM | 404 | N | ALA A | 53 | 47.439 | 53.622 | -6.663 | 1.00 | 18.28 | N |
| ATOM | 405 | CA | ALA A | 53 | 48.247 | 52.697 | -7.428 | 1.00 | 18.26 | C |
| ATOM | 407 | CB | ALA A | 53 | 48.636 | 53.328 | -8.755 | 1.00 | 17.89 | C |
| ATOM | 411 | C | ALA A | 53 | 49.499 | 52.207 | -6.653 | 1.00 | 18.32 | C |
| ATOM | 412 | O | ALA A | 53 | 50.220 | 51.372 | -7.157 | 1.00 | 18.19 | O |
| ATOM | 414 | N | ALA A | 54 | 49.746 | 52.720 | -5.446 | 1.00 | 18.04 | N |
| ATOM | 415 | CA | ALA A | 54 | 50.858 | 52.230 | -4.610 | 1.00 | 18.57 | C |
| ATOM | 417 | CB | ALA A | 54 | 50.851 | 52.920 | -3.238 | 1.00 | 18.12 | C |
| ATOM | 421 | C | ALA A | 54 | 50.743 | 50.710 | -4.452 | 1.00 | 18.35 | C |
| ATOM | 422 | O | ALA A | 54 | 49.683 | 50.206 | -4.083 | 1.00 | 19.10 | O |
| ATOM | 424 | N | PRO A | 55 | 51.835 | 49.968 | -4.719 | 1.00 | 19.18 | N |
| ATOM | 425 | CA | PRO A | 55 | 51.808 | 48.521 | -4.508 | 1.00 | 20.25 | C |
| ATOM | 427 | CB | PRO A | 55 | 53.215 | 48.060 | -4.930 | 1.00 | 20.41 | C |
| ATOM | 430 | CG | PRO A | 55 | 53.805 | 49.185 | -5.695 | 1.00 | 20.12 | C |
| ATOM | 433 | CD | PRO A | 55 | 53.137 | 50.435 | -5.226 | 1.00 | 19.31 | C |
| ATOM | 436 | C | PRO A | 55 | 51.550 | 48.178 | -3.056 | 1.00 | 21.16 | C |
| ATOM | 437 | O | PRO A | 55 | 51.927 | 48.940 | -2.179 | 1.00 | 19.44 | O |
| ATOM | 438 | N | THR A | 56 | 50.868 | 47.065 | -2.812 | 1.00 | 22.14 | N |
| ATOM | 439 | CA | THR A | 56 | 50.657 | 46.589 | -1.457 | 1.00 | 24.49 | C |
| ATOM | 441 | CB | THR A | 56 | 49.168 | 46.342 | -1.148 | 1.00 | 25.26 | C |
| ATOM | 443 | OG1 | THR A | 56 | 48.627 | 45.391 | -2.064 | 1.00 | 26.62 | O |
| ATOM | 445 | CG2 | THR A | 56 | 48.374 | 47.639 | -1.228 | 1.00 | 26.84 | C |
| ATOM | 449 | C | THR A | 56 | 51.416 | 45.312 | -1.143 | 1.00 | 24.53 | C |
| ATOM | 450 | O | THR A | 56 | 51.498 | 44.941 | 0.034 | 1.00 | 25.60 | O |
| ATOM | 452 | N | ASP A | 57 | 51.969 | 44.668 | -2.170 | 1.00 | 24.88 | N |
| ATOM | 453 | CA | ASP A | 57 | 52.612 | 43.379 | -2.009 | 1.00 | 25.41 | C |
| ATOM | 455 | CB | ASP A | 57 | 52.062 | 42.372 | -3.044 | 1.00 | 26.33 | C |
| ATOM | 458 | CG | ASP A | 57 | 50.768 | 41.683 | -2.573 | 1.00 | 30.26 | C |
| ATOM | 459 | OD1 | ASP A | 57 | 50.296 | 41.944 | -1.435 | 1.00 | 34.74 | O |
| ATOM | 460 | OD2 | ASP A | 57 | 50.218 | 40.871 | -3.352 | 1.00 | 36.19 | O |
| ATOM | 461 | C | ASP A | 57 | 54.129 | 43.449 | -2.141 | 1.00 | 24.00 | C |
| ATOM | 462 | O | ASP A | 57 | 54.847 | 42.850 | -1.345 | 1.00 | 24.52 | O |
| ATOM | 464 | N | SER A | 58 | 54.612 | 44.131 | -3.174 | 1.00 | 21.93 | N |
| ATOM | 465 | CA | SER A | 58 | 56.038 | 44.282 | -3.379 | 1.00 | 20.17 | C |
| ATOM | 467 | CB | SER A | 58 | 56.305 | 44.904 | -4.750 | 1.00 | 20.52 | C |
| ATOM | 470 | OG | SER A | 58 | 55.791 | 46.204 | -4.867 | 1.00 | 23.15 | O |
| ATOM | 472 | C | SER A | 58 | 56.632 | 45.156 | -2.264 | 1.00 | 18.55 | C |
| ATOM | 473 | O | SER A | 58 | 55.968 | 46.064 | -1.727 | 1.00 | 17.41 | O |
| ATOM | 475 | N | THR A | 59 | 57.884 | 44.881 | -1.917 | 1.00 | 16.56 | N |
| ATOM | 476 | CA | THR A | 59 | 58.524 | 45.550 | -0.804 | 1.00 | 16.36 | C |
| ATOM | 478 | CB | THR A | 59 | 59.867 | 44.882 | -0.460 | 1.00 | 16.64 | C |
| ATOM | 480 | OG1 | THR A | 59 | 59.675 | 43.476 | -0.201 | 1.00 | 18.10 | O |
| ATOM | 482 | CG2 | THR A | 59 | 60.557 | 45.577 | 0.727 | 1.00 | 16.82 | C |
| ATOM | 486 | C | THR A | 59 | 58.790 | 47.019 | -1.103 | 1.00 | 15.32 | C |
| ATOM | 487 | O | THR A | 59 | 59.314 | 47.385 | -2.166 | 1.00 | 15.12 | O |
| ATOM | 489 | N | LEU A | 60 | 58.425 | 47.861 | -0.149 | 1.00 | 14.31 | N |
| ATOM | 490 | CA | LEU A | 60 | 58.771 | 49.263 | -0.213 | 1.00 | 14.03 | C |
| ATOM | 492 | CB | LEU A | 60 | 57.809 | 50.016 | 0.717 | 1.00 | 14.05 | C |
| ATOM | 495 | CG | LEU A | 60 | 58.063 | 51.497 | 0.909 | 1.00 | 12.83 | C |
| ATOM | 497 | CD1 | LEU A | 60 | 58.077 | 52.183 | -0.407 | 1.00 | 14.42 | C |
| ATOM | 501 | CD2 | LEU A | 60 | 56.997 | 52.091 | 1.831 | 1.00 | 12.93 | C |
| ATOM | 505 | C | LEU A | 60 | 60.221 | 49.463 | 0.191 | 1.00 | 14.73 | C |

| | | | | | | | | | | |
|---|---|---|---|---|---|---|---|---|---|---|
| ATOM | 506 | O | LEU | A | 60 | 60.588 | 49.206 | 1.326 | 1.00 14.05 | O |
| ATOM | 508 | N | GLU | A | 61 | 61.071 | 49.851 | -0.756 | 1.00 14.70 | N |
| ATOM | 509 | CA | GLU | A | 61 | 62.469 | 50.094 | -0.456 | 1.00 16.22 | C |
| ATOM | 511 | CB | GLU | A | 61 | 63.350 | 49.707 | -1.635 | 1.00 16.08 | C |
| ATOM | 514 | CG | GLU | A | 61 | 63.540 | 48.186 | -1.727 | 1.00 20.15 | C |
| ATOM | 517 | CD | GLU | A | 61 | 64.702 | 47.807 | -2.652 | 1.00 20.47 | C |
| ATOM | 518 | OE1 | GLU | A | 61 | 64.513 | 48.058 | -3.866 | 1.00 26.76 | O |
| ATOM | 519 | OE2 | GLU | A | 61 | 65.758 | 47.264 | -2.185 | 1.00 27.67 | O |
| ATOM | 520 | C | GLU | A | 61 | 62.699 | 51.541 | -0.120 | 1.00 14.75 | C |
| ATOM | 521 | O | GLU | A | 61 | 62.441 | 52.415 | -0.939 | 1.00 16.44 | O |
| ATOM | 523 | N | LEU | A | 62 | 63.184 | 51.799 | 1.075 | 1.00 13.05 | N |
| ATOM | 524 | CA | LEU | A | 62 | 63.395 | 53.173 | 1.529 | 1.00 12.65 | C |
| ATOM | 526 | CB | LEU | A | 62 | 63.137 | 53.267 | 3.042 | 1.00 12.82 | C |
| ATOM | 529 | CG | LEU | A | 62 | 61.752 | 52.815 | 3.500 | 1.00 14.25 | C |
| ATOM | 531 | CD1 | LEU | A | 62 | 61.645 | 52.735 | 5.029 | 1.00 13.82 | C |
| ATOM | 535 | CD2 | LEU | A | 62 | 60.700 | 53.694 | 2.894 | 1.00 15.11 | C |
| ATOM | 539 | C | LEU | A | 62 | 64.821 | 53.621 | 1.209 | 1.00 12.91 | C |
| ATOM | 540 | O | LEU | A | 62 | 65.777 | 52.947 | 1.574 | 1.00 13.03 | O |
| ATOM | 542 | N | ASP | A | 63 | 64.944 | 54.739 | 0.488 | 1.00 13.36 | N |
| ATOM | 543 | CA | ASP | A | 63 | 66.241 | 55.290 | 0.083 | 1.00 12.72 | C |
| ATOM | 545 | CB | ASP | A | 63 | 66.429 | 55.218 | -1.439 | 1.00 12.28 | C |
| ATOM | 548 | CG | ASP | A | 63 | 65.398 | 56.018 | -2.217 | 1.00 14.09 | C |
| ATOM | 549 | OD1 | ASP | A | 63 | 64.947 | 57.049 | -1.754 | 1.00 13.13 | O |
| ATOM | 550 | OD2 | ASP | A | 63 | 65.003 | 55.582 | -3.330 | 1.00 16.19 | O |
| ATOM | 551 | C | ASP | A | 63 | 66.461 | 56.746 | 0.559 | 1.00 12.04 | C |
| ATOM | 552 | O | ASP | A | 63 | 67.486 | 57.331 | 0.231 | 1.00 13.31 | O |
| ATOM | 554 | N | GLY | A | 64 | 65.513 | 57.292 | 1.319 | 1.00 11.98 | N |
| ATOM | 555 | CA | GLY | A | 64 | 65.650 | 58.652 | 1.914 | 1.00 11.87 | C |
| ATOM | 558 | C | GLY | A | 64 | 65.061 | 59.770 | 1.052 | 1.00 12.37 | C |
| ATOM | 559 | O | GLY | A | 64 | 64.971 | 60.908 | 1.489 | 1.00 11.85 | O |
| ATOM | 561 | N | TYR | A | 65 | 64.640 | 59.448 | -0.180 | 1.00 12.17 | N |
| ATOM | 562 | CA | TYR | A | 65 | 64.217 | 60.457 | -1.145 | 1.00 11.75 | C |
| ATOM | 564 | CB | TYR | A | 65 | 65.352 | 60.717 | -2.118 | 1.00 12.34 | C |
| ATOM | 567 | CG | TYR | A | 65 | 66.542 | 61.361 | -1.448 | 1.00 12.82 | C |
| ATOM | 568 | CD1 | TYR | A | 65 | 66.712 | 62.743 | -1.470 | 1.00 14.70 | C |
| ATOM | 570 | CE1 | TYR | A | 65 | 67.813 | 63.346 | -0.837 | 1.00 15.90 | C |
| ATOM | 572 | CZ | TYR | A | 65 | 68.718 | 62.551 | -0.153 | 1.00 15.42 | C |
| ATOM | 573 | OH | TYR | A | 65 | 69.816 | 63.105 | 0.481 | 1.00 17.82 | O |
| ATOM | 575 | CE2 | TYR | A | 65 | 68.578 | 61.173 | -0.137 | 1.00 15.57 | C |
| ATOM | 577 | CD2 | TYR | A | 65 | 67.482 | 60.589 | -0.761 | 1.00 15.49 | C |
| ATOM | 579 | C | TYR | A | 65 | 62.964 | 60.125 | -1.936 | 1.00 12.41 | C |
| ATOM | 580 | O | TYR | A | 65 | 62.200 | 61.024 | -2.287 | 1.00 12.59 | O |
| ATOM | 582 | N | SER | A | 66 | 62.729 | 58.831 | -2.211 | 1.00 12.32 | N |
| ATOM | 583 | CA | SER | A | 66 | 61.668 | 58.413 | -3.154 | 1.00 13.57 | C |
| ATOM | 585 | CB | SER | A | 66 | 62.059 | 57.070 | -3.790 | 1.00 13.01 | C |
| ATOM | 588 | OG | SER | A | 66 | 63.281 | 57.154 | -4.454 | 1.00 19.13 | O |
| ATOM | 590 | C | SER | A | 66 | 60.316 | 58.199 | -2.514 | 1.00 12.78 | C |
| ATOM | 591 | O | SER | A | 66 | 59.287 | 58.024 | -3.224 | 1.00 13.18 | O |
| ATOM | 593 | N | LEU | A | 67 | 60.300 | 58.131 | -1.191 | 1.00 12.03 | N |
| ATOM | 594 | CA | LEU | A | 67 | 59.073 | 57.722 | -0.489 | 1.00 12.65 | C |
| ATOM | 596 | CB | LEU | A | 67 | 59.336 | 57.596 | 1.008 | 1.00 12.96 | C |
| ATOM | 599 | CG | LEU | A | 67 | 58.179 | 57.284 | 1.924 | 1.00 12.98 | C |
| ATOM | 601 | CD1 | LEU | A | 67 | 57.622 | 55.927 | 1.638 | 1.00 13.60 | C |
| ATOM | 605 | CD2 | LEU | A | 67 | 58.572 | 57.363 | 3.381 | 1.00 12.39 | C |
| ATOM | 609 | C | LEU | A | 67 | 57.961 | 58.730 | -0.737 | 1.00 12.61 | C |
| ATOM | 610 | O | LEU | A | 67 | 58.142 | 59.918 | -0.504 | 1.00 14.12 | O |
| ATOM | 612 | N | ASN | A | 68 | 56.801 | 58.249 | -1.178 | 1.00 13.03 | N |

| ATOM | 613 | CA | ASN A | 68 | 55.676 | 59.133 | -1.424 | 1.00 | 13.40 | C |
|------|-----|----|----|----|--------|--------|--------|------|-------|---|
| ATOM | 615 | CB | ASN A | 68 | 55.255 | 59.116 | -2.893 | 1.00 | 13.38 | C |
| ATOM | 618 | CG | ASN A | 68 | 54.786 | 57.733 | -3.359 | 1.00 | 15.31 | C |
| ATOM | 619 | OD1 | ASN A | 68 | 54.013 | 57.064 | -2.677 | 1.00 | 13.99 | O |
| ATOM | 620 | ND2 | ASN A | 68 | 55.258 | 57.311 | -4.519 | 1.00 | 16.55 | N |
| ATOM | 623 | C | ASN A | 68 | 54.509 | 58.838 | -0.494 | 1.00 | 12.92 | C |
| ATOM | 624 | O | ASN A | 68 | 54.561 | 57.904 | 0.321 | 1.00 | 13.34 | O |
| ATOM | 626 | N | LEU A | 69 | 53.480 | 59.672 | -0.556 | 1.00 | 13.07 | N |
| ATOM | 627 | CA | LEU A | 69 | 52.402 | 59.519 | 0.403 | 1.00 | 12.53 | C |
| ATOM | 629 | CB | LEU A | 69 | 51.492 | 60.746 | 0.412 | 1.00 | 12.73 | C |
| ATOM | 632 | CG | LEU A | 69 | 52.132 | 62.081 | 0.756 | 1.00 | 13.15 | C |
| ATOM | 634 | CD1 | LEU A | 69 | 51.023 | 63.078 | 1.023 | 1.00 | 14.48 | C |
| ATOM | 638 | CD2 | LEU A | 69 | 53.043 | 61.916 | 1.936 | 1.00 | 12.86 | C |
| ATOM | 642 | C | LEU A | 69 | 51.583 | 58.236 | 0.193 | 1.00 | 12.72 | C |
| ATOM | 643 | O | LEU A | 69 | 51.164 | 57.575 | 1.158 | 1.00 | 12.88 | O |
| ATOM | 645 | N | GLY A | 70 | 51.373 | 57.859 | -1.057 | 1.00 | 13.56 | N |
| ATOM | 646 | CA | GLY A | 70 | 50.742 | 56.574 | -1.315 | 1.00 | 12.96 | C |
| ATOM | 649 | C | GLY A | 70 | 51.501 | 55.388 | -0.689 | 1.00 | 13.27 | C |
| ATOM | 650 | O | GLY A | 70 | 50.915 | 54.448 | -0.134 | 1.00 | 13.91 | O |
| ATOM | 652 | N | ASP A | 71 | 52.826 | 55.427 | -0.779 | 1.00 | 12.45 | N |
| ATOM | 653 | CA | ASP A | 71 | 53.662 | 54.391 | -0.192 | 1.00 | 13.43 | C |
| ATOM | 655 | CB | ASP A | 71 | 55.133 | 54.719 | -0.389 | 1.00 | 12.66 | C |
| ATOM | 658 | CG | ASP A | 71 | 55.647 | 54.520 | -1.816 | 1.00 | 14.35 | C |
| ATOM | 659 | OD1 | ASP A | 71 | 55.140 | 53.653 | -2.562 | 1.00 | 14.59 | O |
| ATOM | 660 | OD2 | ASP A | 71 | 56.643 | 55.239 | -2.156 | 1.00 | 14.51 | O |
| ATOM | 661 | C | ASP A | 71 | 53.420 | 54.330 | 1.341 | 1.00 | 13.45 | C |
| ATOM | 662 | O | ASP A | 71 | 53.328 | 53.259 | 1.916 | 1.00 | 14.18 | O |
| ATOM | 664 | N | VAL A | 72 | 53.462 | 55.483 | 1.989 | 1.00 | 13.09 | N |
| ATOM | 665 | CA | VAL A | 72 | 53.262 | 55.536 | 3.442 | 1.00 | 12.78 | C |
| ATOM | 667 | CB | VAL A | 72 | 53.288 | 56.990 | 3.977 | 1.00 | 13.07 | C |
| ATOM | 669 | CG1 | VAL A | 72 | 52.870 | 57.015 | 5.423 | 1.00 | 14.45 | C |
| ATOM | 673 | CG2 | VAL A | 72 | 54.687 | 57.592 | 3.797 | 1.00 | 13.57 | C |
| ATOM | 677 | C | VAL A | 72 | 51.940 | 54.864 | 3.831 | 1.00 | 12.63 | C |
| ATOM | 678 | O | VAL A | 72 | 51.894 | 54.017 | 4.732 | 1.00 | 13.97 | O |
| ATOM | 680 | N | VAL A | 73 | 50.852 | 55.203 | 3.138 | 1.00 | 12.28 | N |
| ATOM | 681 | CA | VAL A | 73 | 49.532 | 54.597 | 3.465 | 1.00 | 12.63 | C |
| ATOM | 683 | CB | VAL A | 73 | 48.438 | 55.226 | 2.621 | 1.00 | 13.56 | C |
| ATOM | 685 | CG1 | VAL A | 73 | 47.111 | 54.569 | 2.882 | 1.00 | 13.57 | C |
| ATOM | 689 | CG2 | VAL A | 73 | 48.345 | 56.709 | 2.969 | 1.00 | 11.99 | C |
| ATOM | 693 | C | VAL A | 73 | 49.590 | 53.058 | 3.220 | 1.00 | 12.85 | C |
| ATOM | 694 | O | VAL A | 73 | 49.036 | 52.292 | 3.997 | 1.00 | 13.89 | O |
| ATOM | 696 | N | SER A | 74 | 50.231 | 52.628 | 2.136 | 1.00 | 12.38 | N |
| ATOM | 697 | CA | SER A | 74 | 50.337 | 51.186 | 1.842 | 1.00 | 12.96 | C |
| ATOM | 699 | CB | SER A | 74 | 51.054 | 50.935 | 0.473 | 1.00 | 13.57 | C |
| ATOM | 702 | OG | SER A | 74 | 52.430 | 51.270 | 0.509 | 1.00 | 14.38 | O |
| ATOM | 704 | C | SER A | 74 | 51.038 | 50.410 | 2.974 | 1.00 | 13.30 | C |
| ATOM | 705 | O | SER A | 74 | 50.637 | 49.291 | 3.322 | 1.00 | 15.55 | O |
| ATOM | 707 | N | ALA A | 75 | 52.087 | 51.008 | 3.534 | 1.00 | 14.46 | N |
| ATOM | 708 | CA | ALA A | 75 | 52.807 | 50.441 | 4.684 | 1.00 | 13.93 | C |
| ATOM | 710 | CB | ALA A | 75 | 54.166 | 51.111 | 4.865 | 1.00 | 14.80 | C |
| ATOM | 714 | C | ALA A | 75 | 52.030 | 50.533 | 5.976 | 1.00 | 14.75 | C |
| ATOM | 715 | O | ALA A | 75 | 52.047 | 49.610 | 6.787 | 1.00 | 14.96 | O |
| ATOM | 717 | N | ALA A | 76 | 51.393 | 51.672 | 6.217 | 1.00 | 13.39 | N |
| ATOM | 718 | CA | ALA A | 76 | 50.682 | 51.890 | 7.458 | 1.00 | 14.49 | C |
| ATOM | 720 | CB | ALA A | 76 | 50.278 | 53.359 | 7.562 | 1.00 | 14.42 | C |
| ATOM | 724 | C | ALA A | 76 | 49.451 | 50.992 | 7.563 | 1.00 | 14.95 | C |
| ATOM | 725 | O | ALA A | 76 | 49.215 | 50.362 | 8.589 | 1.00 | 14.28 | O |

| ATOM | 727 | N   | ARG A | 77 | 48.662 | 50.967 | 6.492  | 1.00 16.34 | N |
| ATOM | 728 | CA  | ARG A | 77 | 47.338 | 50.342 | 6.479  | 1.00 16.75 | C |
| ATOM | 730 | CB  | ARG A | 77 | 46.323 | 51.256 | 5.787  | 1.00 17.39 | C |
| ATOM | 733 | CG  | ARG A | 77 | 45.962 | 52.426 | 6.542  | 1.00 17.97 | C |
| ATOM | 736 | CD  | ARG A | 77 | 44.710 | 53.110 | 5.935  | 1.00 17.65 | C |
| ATOM | 739 | NE  | ARG A | 77 | 44.322 | 54.200 | 6.806  | 1.00 18.47 | N |
| ATOM | 741 | CZ  | ARG A | 77 | 43.642 | 55.273 | 6.405  | 1.00 15.87 | C |
| ATOM | 742 | NH1 | ARG A | 77 | 43.330 | 55.388 | 5.115  | 1.00 15.23 | N |
| ATOM | 745 | NH2 | ARG A | 77 | 43.330 | 56.246 | 7.249  | 1.00 17.50 | N |
| ATOM | 748 | C   | ARG A | 77 | 47.230 | 49.019 | 5.779  | 1.00 17.41 | C |
| ATOM | 749 | O   | ARG A | 77 | 46.296 | 48.277 | 6.076  | 1.00 18.70 | O |
| ATOM | 751 | N   | LYS A | 78 | 48.086 | 48.725 | 4.799  | 1.00 16.63 | N |
| ATOM | 752 | CA  | LYS A | 78 | 47.887 | 47.528 | 3.974  | 1.00 17.39 | C |
| ATOM | 754 | CB  | LYS A | 78 | 47.773 | 47.882 | 2.486  | 1.00 19.50 | C |
| ATOM | 757 | CG  | LYS A | 78 | 46.920 | 49.098 | 2.171  | 1.00 20.75 | C |
| ATOM | 760 | CD  | LYS A | 78 | 45.501 | 48.880 | 2.617  | 1.00 25.95 | C |
| ATOM | 763 | CE  | LYS A | 78 | 44.530 | 49.984 | 2.130  | 1.00 27.92 | C |
| ATOM | 766 | NZ  | LYS A | 78 | 43.567 | 49.448 | 1.121  | 1.00 29.38 | N |
| ATOM | 770 | C   | LYS A | 78 | 48.970 | 46.503 | 4.153  | 1.00 17.22 | C |
| ATOM | 771 | O   | LYS A | 78 | 49.024 | 45.520 | 3.394  | 1.00 16.58 | O |
| ATOM | 773 | N   | GLY A | 79 | 49.821 | 46.678 | 5.167  | 1.00 16.17 | N |
| ATOM | 774 | CA  | GLY A | 79 | 50.779 | 45.618 | 5.513  | 1.00 16.20 | C |
| ATOM | 777 | C   | GLY A | 79 | 51.875 | 45.421 | 4.504  | 1.00 15.95 | C |
| ATOM | 778 | O   | GLY A | 79 | 52.512 | 44.349 | 4.447  | 1.00 17.17 | O |
| ATOM | 780 | N   | ARG A | 80 | 52.124 | 46.439 | 3.679  | 1.00 14.97 | N |
| ATOM | 781 | CA  | ARG A | 80 | 53.184 | 46.273 | 2.705  | 1.00 14.95 | C |
| ATOM | 783 | CB  | ARG A | 80 | 53.299 | 47.480 | 1.822  | 1.00 15.14 | C |
| ATOM | 786 | CG  | ARG A | 80 | 54.262 | 47.289 | 0.657  | 1.00 13.53 | C |
| ATOM | 789 | CD  | ARG A | 80 | 54.192 | 48.531 | -0.108 | 1.00 15.92 | C |
| ATOM | 792 | NE  | ARG A | 80 | 55.063 | 48.608 | -1.244 | 1.00 12.67 | N |
| ATOM | 794 | CZ  | ARG A | 80 | 55.209 | 49.738 | -1.935 | 1.00 13.97 | C |
| ATOM | 795 | NH1 | ARG A | 80 | 54.560 | 50.834 | -1.577 | 1.00 15.82 | N |
| ATOM | 798 | NH2 | ARG A | 80 | 56.059 | 49.768 | -2.958 | 1.00 15.06 | N |
| ATOM | 801 | C   | ARG A | 80 | 54.509 | 46.068 | 3.428  | 1.00 14.53 | C |
| ATOM | 802 | O   | ARG A | 80 | 54.794 | 46.824 | 4.364  | 1.00 14.04 | O |
| ATOM | 804 | N   | PRO A | 81 | 55.323 | 45.067 | 2.992  | 1.00 13.45 | N |
| ATOM | 805 | CA  | PRO A | 81 | 56.686 | 44.915 | 3.534  | 1.00 13.72 | C |
| ATOM | 807 | CB  | PRO A | 81 | 57.257 | 43.703 | 2.765  | 1.00 13.77 | C |
| ATOM | 810 | CG  | PRO A | 81 | 56.071 | 43.014 | 2.258  | 1.00 13.74 | C |
| ATOM | 813 | CD  | PRO A | 81 | 55.048 | 44.032 | 1.971  | 1.00 13.64 | C |
| ATOM | 816 | C   | PRO A | 81 | 57.546 | 46.171 | 3.291  | 1.00 13.60 | C |
| ATOM | 817 | O   | PRO A | 81 | 57.382 | 46.859 | 2.268  | 1.00 12.86 | O |
| ATOM | 818 | N   | VAL A | 82 | 58.441 | 46.442 | 4.226  | 1.00 12.63 | N |
| ATOM | 819 | CA  | VAL A | 82 | 59.325 | 47.612 | 4.158  | 1.00 12.57 | C |
| ATOM | 821 | CB  | VAL A | 82 | 58.859 | 48.693 | 5.191  | 1.00 12.34 | C |
| ATOM | 823 | CG1 | VAL A | 82 | 59.796 | 49.890 | 5.196  | 1.00 12.56 | C |
| ATOM | 827 | CG2 | VAL A | 82 | 57.443 | 49.133 | 4.902  | 1.00 13.12 | C |
| ATOM | 831 | C   | VAL A | 82 | 60.776 | 47.255 | 4.443  | 1.00 13.36 | C |
| ATOM | 832 | O   | VAL A | 82 | 61.069 | 46.500 | 5.356  | 1.00 14.12 | O |
| ATOM | 834 | N   | ARG A | 83 | 61.692 | 47.784 | 3.642  | 1.00 14.45 | N |
| ATOM | 835 | CA  | ARG A | 83 | 63.113 | 47.578 | 3.885  | 1.00 15.28 | C |
| ATOM | 837 | CB  | ARG A | 83 | 63.585 | 46.383 | 3.016  | 1.00 15.46 | C |
| ATOM | 840 | CG  | ARG A | 83 | 64.354 | 45.345 | 3.732  | 1.00 24.96 | C |
| ATOM | 843 | CD  | ARG A | 83 | 63.704 | 44.811 | 5.022  | 1.00 31.02 | C |
| ATOM | 846 | NE  | ARG A | 83 | 64.749 | 44.116 | 5.798  | 1.00 34.99 | N |
| ATOM | 848 | CZ  | ARG A | 83 | 64.725 | 43.898 | 7.117  | 1.00 33.99 | C |
| ATOM | 849 | NH1 | ARG A | 83 | 63.676 | 44.266 | 7.863  | 1.00 24.49 | N |

| | | | | | | | | | |
|---|---|---|---|---|---|---|---|---|---|
| ATOM | 852 | NH2 | ARG A | 83 | 65.771 | 43.274 | 7.679 | 1.00 34.55 | N |
| ATOM | 855 | C | ARG A | 83 | 63.920 | 48.813 | 3.533 | 1.00 14.14 | C |
| ATOM | 856 | O | ARG A | 83 | 63.542 | 49.564 | 2.632 | 1.00 13.37 | O |
| ATOM | 858 | N | VAL A | 84 | 65.045 | 49.024 | 4.217 | 1.00 13.13 | N |
| ATOM | 859 | CA | VAL A | 84 | 66.037 | 49.964 | 3.712 | 1.00 14.77 | C |
| ATOM | 861 | CB | VAL A | 84 | 67.242 | 50.101 | 4.666 | 1.00 14.92 | C |
| ATOM | 863 | CG1 | VAL A | 84 | 68.374 | 50.970 | 4.038 | 1.00 15.24 | C |
| ATOM | 867 | CG2 | VAL A | 84 | 66.779 | 50.691 | 5.992 | 1.00 16.75 | C |
| ATOM | 871 | C | VAL A | 84 | 66.516 | 49.421 | 2.371 | 1.00 15.21 | C |
| ATOM | 872 | O | VAL A | 84 | 66.803 | 48.232 | 2.261 | 1.00 16.52 | O |
| ATOM | 874 | N | LYS A | 85 | 66.564 | 50.265 | 1.345 | 1.00 16.43 | N |
| ATOM | 875 | CA | LYS A | 85 | 67.048 | 49.843 | 0.028 | 1.00 18.27 | C |
| ATOM | 877 | CB | LYS A | 85 | 67.194 | 51.046 | -0.905 | 1.00 18.71 | C |
| ATOM | 880 | CG | LYS A | 85 | 67.512 | 50.694 | -2.352 | 1.00 19.45 | C |
| ATOM | 883 | CD | LYS A | 85 | 67.678 | 51.946 | -3.192 | 1.00 20.80 | C |
| ATOM | 886 | CE | LYS A | 85 | 68.195 | 51.645 | -4.581 | 1.00 22.33 | C |
| ATOM | 889 | NZ | LYS A | 85 | 67.263 | 50.753 | -5.322 | 1.00 26.93 | N |
| ATOM | 893 | C | LYS A | 85 | 68.378 | 49.118 | 0.111 | 1.00 19.62 | C |
| ATOM | 894 | O | LYS A | 85 | 69.296 | 49.533 | 0.832 | 1.00 18.69 | O |
| ATOM | 896 | N | ASP A | 86 | 68.454 | 48.032 | -0.659 | 1.00 20.69 | N |
| ATOM | 897 | CA | ASP A | 86 | 69.635 | 47.176 | -0.750 | 1.00 23.03 | C |
| ATOM | 899 | CB | ASP A | 86 | 69.178 | 45.777 | -1.209 | 1.00 23.47 | C |
| ATOM | 902 | CG | ASP A | 86 | 70.235 | 44.702 | -1.015 | 1.00 25.54 | C |
| ATOM | 903 | OD1 | ASP A | 86 | 70.065 | 43.624 | -1.631 | 1.00 29.93 | O |
| ATOM | 904 | OD2 | ASP A | 86 | 71.215 | 44.904 | -0.267 | 1.00 29.11 | O |
| ATOM | 905 | C | ASP A | 86 | 70.640 | 47.801 | -1.734 | 1.00 24.08 | C |
| ATOM | 906 | O | ASP A | 86 | 70.576 | 47.547 | -2.963 | 1.00 25.06 | O |
| ATOM | 908 | N | SER A | 87 | 71.546 | 48.620 | -1.197 | 1.00 23.75 | N |
| ATOM | 909 | CA | SER A | 87 | 72.538 | 49.332 | -1.996 | 1.00 24.31 | C |
| ATOM | 911 | CB | SER A | 87 | 71.950 | 50.606 | -2.627 | 1.00 24.38 | C |
| ATOM | 914 | OG | SER A | 87 | 72.261 | 51.803 | -1.925 | 1.00 24.98 | O |
| ATOM | 916 | C | SER A | 87 | 73.762 | 49.668 | -1.149 | 1.00 24.59 | C |
| ATOM | 917 | O | SER A | 87 | 73.638 | 50.075 | -0.003 | 1.00 23.52 | O |
| ATOM | 919 | N | ASP A | 88 | 74.949 | 49.474 | -1.714 | 1.00 25.29 | N |
| ATOM | 920 | CA | ASP A | 88 | 76.184 | 49.750 | -1.008 | 1.00 26.63 | C |
| ATOM | 922 | CB | ASP A | 88 | 77.410 | 49.347 | -1.858 | 1.00 27.16 | C |
| ATOM | 925 | CG | ASP A | 88 | 77.593 | 47.819 | -1.981 | 1.00 30.65 | C |
| ATOM | 926 | OD1 | ASP A | 88 | 77.131 | 47.057 | -1.098 | 1.00 33.42 | O |
| ATOM | 927 | OD2 | ASP A | 88 | 78.242 | 47.380 | -2.958 | 1.00 34.48 | O |
| ATOM | 928 | C | ASP A | 88 | 76.270 | 51.223 | -0.710 | 1.00 26.70 | C |
| ATOM | 929 | O | ASP A | 88 | 76.750 | 51.627 | 0.331 | 1.00 27.23 | O |
| ATOM | 931 | N | GLU A | 89 | 75.792 | 52.032 | -1.641 | 1.00 27.03 | N |
| ATOM | 932 | CA | GLU A | 89 | 75.860 | 53.466 | -1.489 | 1.00 27.76 | C |
| ATOM | 934 | CB | GLU A | 89 | 75.320 | 54.099 | -2.757 | 1.00 28.03 | C |
| ATOM | 937 | CG | GLU A | 89 | 75.259 | 55.604 | -2.746 | 1.00 31.04 | C |
| ATOM | 940 | CD | GLU A | 89 | 74.426 | 56.115 | -3.893 | 1.00 31.75 | C |
| ATOM | 941 | OE1 | GLU A | 89 | 74.826 | 55.876 | -5.068 | 1.00 36.46 | O |
| ATOM | 942 | OE2 | GLU A | 89 | 73.376 | 56.746 | -3.617 | 1.00 38.08 | O |
| ATOM | 943 | C | GLU A | 89 | 75.074 | 53.957 | -0.247 | 1.00 26.56 | C |
| ATOM | 944 | O | GLU A | 89 | 75.581 | 54.770 | 0.541 | 1.00 26.49 | O |
| ATOM | 946 | N | ILE A | 90 | 73.859 | 53.450 | -0.072 | 1.00 25.20 | N |
| ATOM | 947 | CA | ILE A | 90 | 73.052 | 53.814 | 1.105 | 1.00 24.72 | C |
| ATOM | 949 | CB | ILE A | 90 | 71.618 | 53.323 | 0.979 | 1.00 25.30 | C |
| ATOM | 951 | CG1 | ILE A | 90 | 70.916 | 54.097 | -0.133 | 1.00 26.10 | C |
| ATOM | 954 | CD1 | ILE A | 90 | 69.601 | 53.543 | -0.488 | 1.00 29.76 | C |
| ATOM | 958 | CG2 | ILE A | 90 | 70.865 | 53.513 | 2.324 | 1.00 24.91 | C |
| ATOM | 962 | C | ILE A | 90 | 73.670 | 53.270 | 2.396 | 1.00 23.96 | C |

| ATOM | 963 | O | ILE A | 90 | 73.823 | 53.950 | 3.389 | 1.00 | 22.76 | O |
|------|-----|-----|-------|-----|--------|--------|-------|------|-------|---|
| ATOM | 965 | N | ARG A | 91 | 74.069 | 52.017 | 2.348 | 1.00 | 23.74 | N |
| ATOM | 966 | CA | ARG A | 91 | 74.737 | 51.383 | 3.455 | 1.00 | 24.92 | C |
| ATOM | 968 | CB | ARG A | 91 | 75.081 | 49.989 | 2.971 | 1.00 | 25.13 | C |
| ATOM | 971 | CG | ARG A | 91 | 75.262 | 48.917 | 3.972 | 1.00 | 28.03 | C |
| ATOM | 974 | CD | ARG A | 91 | 75.456 | 47.583 | 3.180 | 1.00 | 28.31 | C |
| ATOM | 977 | NE | ARG A | 91 | 74.181 | 47.202 | 2.561 | 1.00 | 30.65 | N |
| ATOM | 979 | CZ | ARG A | 91 | 73.951 | 46.939 | 1.275 | 1.00 | 30.34 | C |
| ATOM | 980 | NH1 | ARG A | 91 | 74.912 | 46.939 | 0.360 | 1.00 | 32.11 | N |
| ATOM | 983 | NH2 | ARG A | 91 | 72.716 | 46.628 | 0.912 | 1.00 | 31.64 | N |
| ATOM | 986 | C | ARG A | 91 | 76.003 | 52.158 | 3.850 | 1.00 | 24.87 | C |
| ATOM | 987 | O | ARG A | 91 | 76.251 | 52.420 | 5.031 | 1.00 | 24.14 | O |
| ATOM | 989 | N | SER A | 92 | 76.833 | 52.501 | 2.867 | 1.00 | 24.97 | N |
| ATOM | 990 | CA | SER A | 92 | 78.073 | 53.211 | 3.156 | 1.00 | 25.76 | C |
| ATOM | 992 | CB | SER A | 92 | 78.932 | 53.319 | 1.899 | 1.00 | 25.80 | C |
| ATOM | 995 | OG | SER A | 92 | 80.035 | 54.151 | 2.168 | 1.00 | 28.50 | O |
| ATOM | 997 | C | SER A | 92 | 77.814 | 54.602 | 3.737 | 1.00 | 25.77 | C |
| ATOM | 998 | O | SER A | 92 | 78.477 | 55.037 | 4.679 | 1.00 | 26.34 | O |
| ATOM | 1000 | N | LYS A | 93 | 76.831 | 55.286 | 3.165 | 1.00 | 25.46 | N |
| ATOM | 1001 | CA | LYS A | 93 | 76.425 | 56.601 | 3.611 | 1.00 | 24.67 | C |
| ATOM | 1003 | CB | LYS A | 93 | 75.274 | 57.045 | 2.714 | 1.00 | 25.44 | C |
| ATOM | 1006 | CG | LYS A | 93 | 74.609 | 58.294 | 3.084 | 1.00 | 26.18 | C |
| ATOM | 1009 | CD | LYS A | 93 | 73.210 | 58.381 | 2.428 | 1.00 | 26.08 | C |
| ATOM | 1012 | CE | LYS A | 93 | 73.281 | 58.477 | 0.927 | 1.00 | 26.93 | C |
| ATOM | 1015 | NZ | LYS A | 93 | 72.093 | 59.116 | 0.353 | 1.00 | 25.34 | N |
| ATOM | 1019 | C | LYS A | 93 | 76.011 | 56.609 | 5.112 | 1.00 | 23.70 | C |
| ATOM | 1020 | O | LYS A | 93 | 76.460 | 57.458 | 5.886 | 1.00 | 23.15 | O |
| ATOM | 1022 | N | ILE A | 94 | 75.156 | 55.663 | 5.483 | 1.00 | 22.56 | N |
| ATOM | 1023 | CA | ILE A | 94 | 74.703 | 55.496 | 6.863 | 1.00 | 22.80 | C |
| ATOM | 1025 | CB | ILE A | 94 | 73.639 | 54.369 | 6.942 | 1.00 | 22.25 | C |
| ATOM | 1027 | CG1 | ILE A | 94 | 72.314 | 54.805 | 6.319 | 1.00 | 22.73 | C |
| ATOM | 1030 | CD1 | ILE A | 94 | 71.401 | 53.634 | 6.061 | 1.00 | 23.08 | C |
| ATOM | 1034 | CG2 | ILE A | 94 | 73.417 | 53.864 | 8.394 | 1.00 | 22.82 | C |
| ATOM | 1038 | C | ILE A | 94 | 75.910 | 55.168 | 7.761 | 1.00 | 22.51 | C |
| ATOM | 1039 | O | ILE A | 94 | 76.174 | 55.843 | 8.773 | 1.00 | 21.94 | O |
| ATOM | 1041 | N | ASP A | 95 | 76.682 | 54.168 | 7.327 | 1.00 | 22.05 | N |
| ATOM | 1042 | CA | ASP A | 95 | 77.851 | 53.695 | 8.060 | 1.00 | 22.84 | C |
| ATOM | 1044 | CB | ASP A | 95 | 78.480 | 52.482 | 7.333 | 1.00 | 23.10 | C |
| ATOM | 1047 | CG | ASP A | 95 | 77.524 | 51.238 | 7.240 | 1.00 | 26.57 | C |
| ATOM | 1048 | OD1 | ASP A | 95 | 76.318 | 51.283 | 7.652 | 1.00 | 30.90 | O |
| ATOM | 1049 | OD2 | ASP A | 95 | 77.994 | 50.186 | 6.711 | 1.00 | 30.07 | O |
| ATOM | 1050 | C | ASP A | 95 | 78.876 | 54.824 | 8.256 | 1.00 | 22.61 | C |
| ATOM | 1051 | O | ASP A | 95 | 79.416 | 54.999 | 9.355 | 1.00 | 22.46 | O |
| ATOM | 1053 | N | LYS A | 96 | 79.100 | 55.632 | 7.217 | 1.00 | 22.90 | N |
| ATOM | 1054 | CA | LYS A | 96 | 80.063 | 56.734 | 7.308 | 1.00 | 23.86 | C |
| ATOM | 1056 | CB | LYS A | 96 | 80.377 | 57.323 | 5.922 | 1.00 | 24.31 | C |
| ATOM | 1059 | CG | LYS A | 96 | 81.323 | 56.453 | 5.119 | 1.00 | 27.19 | C |
| ATOM | 1062 | CD | LYS A | 96 | 81.310 | 56.803 | 3.624 | 1.00 | 26.76 | C |
| ATOM | 1065 | CE | LYS A | 96 | 82.374 | 56.047 | 2.832 | 1.00 | 29.16 | C |
| ATOM | 1068 | NZ | LYS A | 96 | 82.048 | 56.042 | 1.357 | 1.00 | 31.81 | N |
| ATOM | 1072 | C | LYS A | 96 | 79.652 | 57.840 | 8.286 | 1.00 | 23.29 | C |
| ATOM | 1073 | O | LYS A | 96 | 80.524 | 58.444 | 8.933 | 1.00 | 22.51 | O |
| ATOM | 1075 | N | SER A | 97 | 78.349 | 58.118 | 8.425 | 1.00 | 23.53 | N |
| ATOM | 1076 | CA | SER A | 97 | 77.922 | 59.115 | 9.436 | 1.00 | 22.71 | C |
| ATOM | 1078 | CB | SER A | 97 | 76.448 | 59.529 | 9.241 | 1.00 | 23.35 | C |
| ATOM | 1081 | OG | SER A | 97 | 75.633 | 58.407 | 9.385 | 1.00 | 23.08 | O |
| ATOM | 1083 | C | SER A | 97 | 78.146 | 58.628 | 10.872 | 1.00 | 22.17 | C |

| ATOM | 1084 | O | SER | A | 97 | 78.453 | 59.419 | 11.781 | 1.00 | 21.49 | O |
|---|---|---|---|---|---|---|---|---|---|---|---|
| ATOM | 1086 | N | VAL | A | 98 | 77.975 | 57.327 | 11.078 | 1.00 | 21.10 | N |
| ATOM | 1087 | CA | VAL | A | 98 | 78.191 | 56.738 | 12.403 | 1.00 | 21.10 | C |
| ATOM | 1089 | CB | VAL | A | 98 | 77.680 | 55.277 | 12.428 | 1.00 | 20.94 | C |
| ATOM | 1091 | CG1 | VAL | A | 98 | 78.181 | 54.516 | 13.651 | 1.00 | 19.77 | C |
| ATOM | 1095 | CG2 | VAL | A | 98 | 76.157 | 55.256 | 12.401 | 1.00 | 21.06 | C |
| ATOM | 1099 | C | VAL | A | 98 | 79.682 | 56.841 | 12.752 | 1.00 | 21.45 | C |
| ATOM | 1100 | O | VAL | A | 98 | 80.074 | 57.258 | 13.850 | 1.00 | 18.27 | O |
| ATOM | 1102 | N | GLU | A | 99 | 80.500 | 56.499 | 11.775 | 1.00 | 22.76 | N |
| ATOM | 1103 | CA | GLU | A | 99 | 81.937 | 56.485 | 11.977 | 1.00 | 24.82 | C |
| ATOM | 1105 | CB | GLU | A | 99 | 82.632 | 55.829 | 10.773 | 1.00 | 25.58 | C |
| ATOM | 1108 | CG | GLU | A | 99 | 83.589 | 54.714 | 11.154 | 1.00 | 30.55 | C |
| ATOM | 1111 | CD | GLU | A | 99 | 83.066 | 53.860 | 12.330 | 1.00 | 36.14 | C |
| ATOM | 1112 | OE1 | GLU | A | 99 | 81.918 | 53.334 | 12.248 | 1.00 | 40.04 | O |
| ATOM | 1113 | OE2 | GLU | A | 99 | 83.795 | 53.760 | 13.350 | 1.00 | 38.85 | O |
| ATOM | 1114 | C | GLU | A | 99 | 82.439 | 57.898 | 12.225 | 1.00 | 25.47 | C |
| ATOM | 1115 | O | GLU | A | 99 | 83.261 | 58.129 | 13.126 | 1.00 | 24.18 | O |
| ATOM | 1117 | N | PHE | A | 100 | 81.915 | 58.863 | 11.466 | 1.00 | 27.17 | N |
| ATOM | 1118 | CA | PHE | A | 100 | 82.317 | 60.247 | 11.665 | 1.00 | 28.71 | C |
| ATOM | 1120 | CB | PHE | A | 100 | 81.670 | 61.219 | 10.662 | 1.00 | 28.98 | C |
| ATOM | 1123 | CG | PHE | A | 100 | 81.899 | 62.660 | 11.034 | 1.00 | 28.77 | C |
| ATOM | 1124 | CD1 | PHE | A | 100 | 83.154 | 63.237 | 10.865 | 1.00 | 30.34 | C |
| ATOM | 1126 | CE1 | PHE | A | 100 | 83.385 | 64.545 | 11.259 | 1.00 | 29.48 | C |
| ATOM | 1128 | CZ | PHE | A | 100 | 82.390 | 65.268 | 11.858 | 1.00 | 30.28 | C |
| ATOM | 1130 | CE2 | PHE | A | 100 | 81.155 | 64.701 | 12.054 | 1.00 | 30.75 | C |
| ATOM | 1132 | CD2 | PHE | A | 100 | 80.926 | 63.397 | 11.659 | 1.00 | 29.96 | C |
| ATOM | 1134 | C | PHE | A | 100 | 82.034 | 60.736 | 13.093 | 1.00 | 29.66 | C |
| ATOM | 1135 | O | PHE | A | 100 | 82.880 | 61.394 | 13.714 | 1.00 | 29.95 | O |
| ATOM | 1137 | N | LEU | A | 101 | 80.839 | 60.436 | 13.596 | 1.00 | 30.64 | N |
| ATOM | 1138 | CA | LEU | A | 101 | 80.428 | 60.859 | 14.923 | 1.00 | 32.49 | C |
| ATOM | 1140 | CB | LEU | A | 101 | 78.958 | 60.513 | 15.156 | 1.00 | 31.94 | C |
| ATOM | 1143 | CG | LEU | A | 101 | 78.270 | 61.036 | 16.418 | 1.00 | 31.38 | C |
| ATOM | 1145 | CD1 | LEU | A | 101 | 77.188 | 61.979 | 16.048 | 1.00 | 31.23 | C |
| ATOM | 1149 | CD2 | LEU | A | 101 | 77.657 | 59.924 | 17.268 | 1.00 | 31.74 | C |
| ATOM | 1153 | C | LEU | A | 101 | 81.300 | 60.183 | 15.972 | 1.00 | 33.46 | C |
| ATOM | 1154 | O | LEU | A | 101 | 81.737 | 60.834 | 16.908 | 1.00 | 34.18 | O |
| ATOM | 1156 | N | ARG | A | 102 | 81.556 | 58.885 | 15.788 | 1.00 | 34.94 | N |
| ATOM | 1157 | CA | ARG | A | 102 | 82.322 | 58.035 | 16.740 | 1.00 | 36.08 | C |
| ATOM | 1159 | CB | ARG | A | 102 | 83.726 | 58.593 | 17.010 | 1.00 | 36.39 | C |
| ATOM | 1162 | CG | ARG | A | 102 | 84.566 | 58.684 | 15.777 | 1.00 | 37.36 | C |
| ATOM | 1165 | CD | ARG | A | 102 | 85.762 | 59.583 | 15.940 | 1.00 | 39.08 | C |
| ATOM | 1168 | NE | ARG | A | 102 | 85.472 | 60.885 | 15.363 | 1.00 | 42.16 | N |
| ATOM | 1170 | CZ | ARG | A | 102 | 84.932 | 61.921 | 16.012 | 1.00 | 44.27 | C |
| ATOM | 1171 | NH1 | ARG | A | 102 | 84.627 | 61.860 | 17.308 | 1.00 | 45.81 | N |
| ATOM | 1174 | NH2 | ARG | A | 102 | 84.687 | 63.052 | 15.346 | 1.00 | 44.68 | N |
| ATOM | 1177 | C | ARG | A | 102 | 81.607 | 57.771 | 18.069 | 1.00 | 36.90 | C |
| ATOM | 1178 | O | ARG | A | 102 | 80.510 | 58.302 | 18.345 | 1.00 | 38.38 | O |
| ATOM | 1180 | N | THR | A | 124 | 81.809 | 54.460 | 26.899 | 1.00 | 38.11 | N |
| ATOM | 1181 | CA | THR | A | 124 | 80.770 | 53.841 | 26.074 | 1.00 | 38.06 | C |
| ATOM | 1183 | CB | THR | A | 124 | 81.337 | 52.650 | 25.250 | 1.00 | 38.70 | C |
| ATOM | 1185 | OG1 | THR | A | 124 | 81.201 | 51.429 | 25.985 | 1.00 | 38.77 | O |
| ATOM | 1187 | CG2 | THR | A | 124 | 82.812 | 52.872 | 24.891 | 1.00 | 38.14 | C |
| ATOM | 1191 | C | THR | A | 124 | 79.578 | 53.390 | 26.947 | 1.00 | 37.60 | C |
| ATOM | 1192 | O | THR | A | 124 | 78.416 | 53.447 | 26.526 | 1.00 | 36.85 | O |
| ATOM | 1194 | N | GLU | A | 125 | 79.893 | 52.931 | 28.158 | 1.00 | 37.06 | N |
| ATOM | 1195 | CA | GLU | A | 125 | 78.901 | 52.720 | 29.212 | 1.00 | 36.87 | C |
| ATOM | 1197 | CB | GLU | A | 125 | 79.608 | 52.144 | 30.460 | 1.00 | 37.35 | C |

| | | | | | | | | | |
|---|---|---|---|---|---|---|---|---|---|
| ATOM | 1200 | CG | GLU | A | 125 | 79.021 | 52.521 | 31.853 | 1.00 39.83 | C |
| ATOM | 1203 | CD | GLU | A | 125 | 79.742 | 51.791 | 33.027 | 1.00 40.81 | C |
| ATOM | 1204 | OE1 | GLU | A | 125 | 80.954 | 51.450 | 32.883 | 1.00 44.81 | O |
| ATOM | 1205 | OE2 | GLU | A | 125 | 79.088 | 51.560 | 34.085 | 1.00 45.16 | O |
| ATOM | 1206 | C | GLU | A | 125 | 78.172 | 54.049 | 29.501 | 1.00 35.61 | C |
| ATOM | 1207 | O | GLU | A | 125 | 76.953 | 54.072 | 29.724 | 1.00 34.94 | O |
| ATOM | 1209 | N | ASP | A | 126 | 78.939 | 55.140 | 29.482 | 1.00 34.22 | N |
| ATOM | 1210 | CA | ASP | A | 126 | 78.418 | 56.513 | 29.568 | 1.00 33.74 | C |
| ATOM | 1212 | CB | ASP | A | 126 | 79.593 | 57.524 | 29.460 | 1.00 34.55 | C |
| ATOM | 1215 | CG | ASP | A | 126 | 80.190 | 57.626 | 28.021 | 1.00 39.04 | C |
| ATOM | 1216 | OD1 | ASP | A | 126 | 80.783 | 56.622 | 27.498 | 1.00 42.59 | O |
| ATOM | 1217 | OD2 | ASP | A | 126 | 80.040 | 58.725 | 27.407 | 1.00 43.62 | O |
| ATOM | 1218 | C | ASP | A | 126 | 77.357 | 56.854 | 28.489 | 1.00 30.42 | C |
| ATOM | 1219 | O | ASP | A | 126 | 76.280 | 57.410 | 28.795 | 1.00 29.08 | O |
| ATOM | 1221 | N | ALA | A | 127 | 77.655 | 56.538 | 27.227 | 1.00 27.14 | N |
| ATOM | 1222 | CA | ALA | A | 127 | 76.746 | 56.927 | 26.157 | 1.00 25.05 | C |
| ATOM | 1224 | CB | ALA | A | 127 | 77.391 | 56.839 | 24.782 | 1.00 25.56 | C |
| ATOM | 1228 | C | ALA | A | 127 | 75.519 | 56.061 | 26.223 | 1.00 22.96 | C |
| ATOM | 1229 | O | ALA | A | 127 | 74.425 | 56.540 | 25.959 | 1.00 21.31 | O |
| ATOM | 1231 | N | ILE | A | 128 | 75.696 | 54.795 | 26.596 | 1.00 20.82 | N |
| ATOM | 1232 | CA | ILE | A | 128 | 74.556 | 53.892 | 26.757 | 1.00 21.28 | C |
| ATOM | 1234 | CB | ILE | A | 128 | 75.002 | 52.452 | 27.118 | 1.00 20.76 | C |
| ATOM | 1236 | CG1 | ILE | A | 128 | 75.619 | 51.785 | 25.879 | 1.00 21.39 | C |
| ATOM | 1239 | CD1 | ILE | A | 128 | 76.314 | 50.407 | 26.147 | 1.00 22.32 | C |
| ATOM | 1243 | CG2 | ILE | A | 128 | 73.824 | 51.609 | 27.609 | 1.00 22.32 | C |
| ATOM | 1247 | C | ILE | A | 128 | 73.626 | 54.458 | 27.817 | 1.00 20.06 | C |
| ATOM | 1248 | O | ILE | A | 128 | 72.408 | 54.485 | 27.626 | 1.00 19.77 | O |
| ATOM | 1250 | N | SER | A | 129 | 74.197 | 54.911 | 28.937 | 1.00 19.69 | N |
| ATOM | 1251 | CA | SER | A | 129 | 73.395 | 55.490 | 30.025 | 1.00 19.33 | C |
| ATOM | 1253 | CB | SER | A | 129 | 74.274 | 55.806 | 31.258 | 1.00 19.77 | C |
| ATOM | 1256 | OG | SER | A | 129 | 74.537 | 54.609 | 31.975 | 1.00 22.88 | O |
| ATOM | 1258 | C | SER | A | 129 | 72.642 | 56.747 | 29.574 | 1.00 18.57 | C |
| ATOM | 1259 | O | SER | A | 129 | 71.488 | 56.966 | 29.958 | 1.00 17.74 | O |
| ATOM | 1261 | N | LEU | A | 130 | 73.318 | 57.607 | 28.818 | 1.00 18.72 | N |
| ATOM | 1262 | CA | LEU | A | 130 | 72.698 | 58.826 | 28.342 | 1.00 19.36 | C |
| ATOM | 1264 | CB | LEU | A | 130 | 73.662 | 59.611 | 27.483 | 1.00 19.90 | C |
| ATOM | 1267 | CG | LEU | A | 130 | 73.085 | 60.893 | 26.894 | 1.00 22.35 | C |
| ATOM | 1269 | CD1 | LEU | A | 130 | 72.491 | 61.811 | 27.959 | 1.00 25.97 | C |
| ATOM | 1273 | CD2 | LEU | A | 130 | 74.194 | 61.581 | 26.102 | 1.00 22.37 | C |
| ATOM | 1277 | C | LEU | A | 130 | 71.456 | 58.541 | 27.522 | 1.00 17.94 | C |
| ATOM | 1278 | O | LEU | A | 130 | 70.430 | 59.200 | 27.690 | 1.00 17.18 | O |
| ATOM | 1280 | N | GLN | A | 131 | 71.527 | 57.534 | 26.652 | 1.00 17.02 | N |
| ATOM | 1281 | CA | GLN | A | 131 | 70.370 | 57.207 | 25.831 | 1.00 16.06 | C |
| ATOM | 1283 | CB | GLN | A | 131 | 70.673 | 56.176 | 24.733 | 1.00 15.83 | C |
| ATOM | 1286 | CG | GLN | A | 131 | 71.975 | 56.371 | 23.998 | 1.00 14.18 | C |
| ATOM | 1289 | CD | GLN | A | 131 | 72.231 | 57.771 | 23.541 | 1.00 15.81 | C |
| ATOM | 1290 | OE1 | GLN | A | 131 | 71.405 | 58.418 | 22.864 | 1.00 14.08 | O |
| ATOM | 1291 | NE2 | GLN | A | 131 | 73.401 | 58.259 | 23.885 | 1.00 16.23 | N |
| ATOM | 1294 | C | GLN | A | 131 | 69.236 | 56.719 | 26.716 | 1.00 14.84 | C |
| ATOM | 1295 | O | GLN | A | 131 | 68.086 | 57.044 | 26.474 | 1.00 14.58 | O |
| ATOM | 1297 | N | LYS | A | 132 | 69.559 | 55.943 | 27.750 | 1.00 14.81 | N |
| ATOM | 1298 | CA | LYS | A | 132 | 68.519 | 55.473 | 28.681 | 1.00 14.40 | C |
| ATOM | 1300 | CB | LYS | A | 132 | 69.117 | 54.423 | 29.624 | 1.00 14.89 | C |
| ATOM | 1303 | CG | LYS | A | 132 | 69.456 | 53.120 | 28.903 | 1.00 15.43 | C |
| ATOM | 1306 | CD | LYS | A | 132 | 70.132 | 52.151 | 29.846 | 1.00 15.82 | C |
| ATOM | 1309 | CE | LYS | A | 132 | 70.387 | 50.808 | 29.159 | 1.00 17.83 | C |
| ATOM | 1312 | NZ | LYS | A | 132 | 71.181 | 49.843 | 30.002 | 1.00 18.30 | N |

| ATOM | 1316 | C | LYS | A | 132 | 67.861 | 56.634 | 29.469 | 1.00 | 14.05 | C |
|------|------|------|-----|---|-----|--------|--------|--------|------|-------|---|
| ATOM | 1317 | O | LYS | A | 132 | 66.647 | 56.647 | 29.681 | 1.00 | 14.52 | O |
| ATOM | 1319 | N | ALA | A | 133 | 68.663 | 57.624 | 29.861 | 1.00 | 13.85 | N |
| ATOM | 1320 | CA | ALA | A | 133 | 68.119 | 58.855 | 30.463 | 1.00 | 13.84 | C |
| ATOM | 1322 | CB | ALA | A | 133 | 69.249 | 59.778 | 30.912 | 1.00 | 14.02 | C |
| ATOM | 1326 | C | ALA | A | 133 | 67.175 | 59.585 | 29.533 | 1.00 | 14.98 | C |
| ATOM | 1327 | O | ALA | A | 133 | 66.177 | 60.144 | 29.979 | 1.00 | 14.39 | O |
| ATOM | 1329 | N | LEU | A | 134 | 67.498 | 59.603 | 28.246 | 1.00 | 15.04 | N |
| ATOM | 1330 | CA | LEU | A | 134 | 66.651 | 60.290 | 27.290 | 1.00 | 15.50 | C |
| ATOM | 1332 | CB | LEU | A | 134 | 67.312 | 60.347 | 25.911 | 1.00 | 15.83 | C |
| ATOM | 1335 | CG | LEU | A | 134 | 68.552 | 61.248 | 25.819 | 1.00 | 21.15 | C |
| ATOM | 1337 | CD1 | LEU | A | 134 | 69.173 | 61.203 | 24.404 | 1.00 | 22.53 | C |
| ATOM | 1341 | CD2 | LEU | A | 134 | 68.204 | 62.675 | 26.194 | 1.00 | 25.25 | C |
| ATOM | 1345 | C | LEU | A | 134 | 65.295 | 59.568 | 27.233 | 1.00 | 14.36 | C |
| ATOM | 1346 | O | LEU | A | 134 | 64.251 | 60.231 | 27.350 | 1.00 | 15.10 | O |
| ATOM | 1348 | N | LEU | A | 135 | 65.281 | 58.234 | 27.073 | 1.00 | 14.36 | N |
| ATOM | 1349 | CA | LEU | A | 135 | 64.007 | 57.487 | 27.035 | 1.00 | 13.83 | C |
| ATOM | 1351 | CB | LEU | A | 135 | 64.163 | 55.994 | 26.659 | 1.00 | 14.88 | C |
| ATOM | 1354 | CG | LEU | A | 135 | 64.910 | 55.754 | 25.342 | 1.00 | 17.69 | C |
| ATOM | 1356 | CD1 | LEU | A | 135 | 64.847 | 54.325 | 24.966 | 1.00 | 17.91 | C |
| ATOM | 1360 | CD2 | LEU | A | 135 | 64.408 | 56.559 | 24.223 | 1.00 | 19.07 | C |
| ATOM | 1364 | C | LEU | A | 135 | 63.247 | 57.603 | 28.343 | 1.00 | 12.88 | C |
| ATOM | 1365 | O | LEU | A | 135 | 62.061 | 57.869 | 28.339 | 1.00 | 14.15 | O |
| ATOM | 1367 | N | GLU | A | 136 | 63.951 | 57.449 | 29.477 | 1.00 | 11.84 | N |
| ATOM | 1368 | CA | GLU | A | 136 | 63.310 | 57.443 | 30.782 | 1.00 | 12.21 | C |
| ATOM | 1370 | CB | GLU | A | 136 | 64.341 | 57.684 | 31.884 | 1.00 | 11.94 | C |
| ATOM | 1373 | CG | GLU | A | 136 | 63.749 | 57.684 | 33.299 | 1.00 | 10.93 | C |
| ATOM | 1376 | CD | GLU | A | 136 | 64.777 | 58.033 | 34.393 | 1.00 | 13.93 | C |
| ATOM | 1377 | OE1 | GLU | A | 136 | 65.789 | 58.707 | 34.088 | 1.00 | 13.56 | O |
| ATOM | 1378 | OE2 | GLU | A | 136 | 64.548 | 57.623 | 35.567 | 1.00 | 13.83 | O |
| ATOM | 1379 | C | GLU | A | 136 | 62.300 | 58.571 | 30.897 | 1.00 | 12.40 | C |
| ATOM | 1380 | O | GLU | A | 136 | 61.160 | 58.329 | 31.240 | 1.00 | 12.18 | O |
| ATOM | 1382 | N | HIS | A | 137 | 62.733 | 59.812 | 30.649 | 1.00 | 11.67 | N |
| ATOM | 1383 | CA | HIS | A | 137 | 61.890 | 60.971 | 30.955 | 1.00 | 11.65 | C |
| ATOM | 1385 | CB | HIS | A | 137 | 62.715 | 62.239 | 31.160 | 1.00 | 12.09 | C |
| ATOM | 1388 | CG | HIS | A | 137 | 63.189 | 62.897 | 29.892 | 1.00 | 13.57 | C |
| ATOM | 1389 | ND1 | HIS | A | 137 | 64.340 | 62.505 | 29.241 | 1.00 | 14.96 | N |
| ATOM | 1391 | CE1 | HIS | A | 137 | 64.530 | 63.276 | 28.184 | 1.00 | 15.23 | C |
| ATOM | 1393 | NE2 | HIS | A | 137 | 63.526 | 64.116 | 28.094 | 1.00 | 14.34 | N |
| ATOM | 1395 | CD2 | HIS | A | 137 | 62.674 | 63.910 | 29.155 | 1.00 | 13.87 | C |
| ATOM | 1397 | C | HIS | A | 137 | 60.786 | 61.114 | 29.927 | 1.00 | 11.36 | C |
| ATOM | 1398 | O | HIS | A | 137 | 59.760 | 61.773 | 30.196 | 1.00 | 12.71 | O |
| ATOM | 1400 | N | GLN | A | 138 | 60.976 | 60.518 | 28.746 | 1.00 | 11.31 | N |
| ATOM | 1401 | CA | GLN | A | 138 | 59.969 | 60.672 | 27.661 | 1.00 | 12.47 | C |
| ATOM | 1403 | CB | GLN | A | 138 | 60.657 | 60.694 | 26.308 | 1.00 | 13.09 | C |
| ATOM | 1406 | CG | GLN | A | 138 | 61.413 | 62.016 | 26.011 | 1.00 | 13.08 | C |
| ATOM | 1409 | CD | GLN | A | 138 | 60.516 | 63.224 | 25.917 | 1.00 | 14.22 | C |
| ATOM | 1410 | OE1 | GLN | A | 138 | 59.356 | 63.108 | 25.584 | 1.00 | 16.46 | O |
| ATOM | 1411 | NE2 | GLN | A | 138 | 61.079 | 64.399 | 26.135 | 1.00 | 19.64 | N |
| ATOM | 1414 | C | GLN | A | 138 | 58.904 | 59.596 | 27.683 | 1.00 | 12.03 | C |
| ATOM | 1415 | O | GLN | A | 138 | 57.867 | 59.741 | 26.974 | 1.00 | 12.20 | O |
| ATOM | 1417 | N | LEU | A | 139 | 59.116 | 58.534 | 28.477 | 1.00 | 10.99 | N |
| ATOM | 1418 | CA | LEU | A | 139 | 58.115 | 57.483 | 28.625 | 1.00 | 11.02 | C |
| ATOM | 1420 | CB | LEU | A | 139 | 58.813 | 56.125 | 28.880 | 1.00 | 11.35 | C |
| ATOM | 1423 | CG | LEU | A | 139 | 59.790 | 55.638 | 27.790 | 1.00 | 12.75 | C |
| ATOM | 1425 | CD1 | LEU | A | 139 | 60.665 | 54.500 | 28.284 | 1.00 | 13.46 | C |
| ATOM | 1429 | CD2 | LEU | A | 139 | 59.008 | 55.160 | 26.523 | 1.00 | 15.65 | C |

| | | | | | | | | | |
|---|---|---|---|---|---|---|---|---|---|
| ATOM | 1433 | C | LEU | A | 139 | 57.162 | 57.879 | 29.736 | 1.00 11.94 | C |
| ATOM | 1434 | O | LEU | A | 139 | 57.063 | 57.229 | 30.787 | 1.00 12.76 | O |
| ATOM | 1436 | N | CYS | A | 140 | 56.421 | 58.968 | 29.452 | 1.00 12.13 | N |
| ATOM | 1437 | CA | CYS | A | 140 | 55.692 | 59.647 | 30.497 | 1.00 13.04 | C |
| ATOM | 1439 | CB | CYS | A | 140 | 56.335 | 61.030 | 30.733 | 1.00 13.80 | C |
| ATOM | 1442 | SG | CYS | A | 140 | 56.284 | 62.125 | 29.275 | 1.00 16.73 | S |
| ATOM | 1444 | C | CYS | A | 140 | 54.207 | 59.824 | 30.173 | 1.00 13.25 | C |
| ATOM | 1445 | O | CYS | A | 140 | 53.567 | 60.645 | 30.808 | 1.00 12.60 | O |
| ATOM | 1447 | N | GLY | A | 141 | 53.683 | 59.108 | 29.170 | 1.00 11.22 | N |
| ATOM | 1448 | CA | GLY | A | 141 | 52.311 | 59.250 | 28.810 | 1.00 11.80 | C |
| ATOM | 1451 | C | GLY | A | 141 | 51.414 | 58.208 | 29.477 | 1.00 11.10 | C |
| ATOM | 1452 | O | GLY | A | 141 | 51.875 | 57.207 | 30.093 | 1.00 12.33 | O |
| ATOM | 1454 | N | VAL | A | 142 | 50.119 | 58.393 | 29.248 | 1.00 10.75 | N |
| ATOM | 1455 | CA | VAL | A | 142 | 49.074 | 57.619 | 29.926 | 1.00 10.87 | C |
| ATOM | 1457 | CB | VAL | A | 142 | 47.981 | 58.507 | 30.491 | 1.00 10.54 | C |
| ATOM | 1459 | CG1 | VAL | A | 142 | 46.789 | 57.711 | 30.938 | 1.00 13.08 | C |
| ATOM | 1463 | CG2 | VAL | A | 142 | 48.515 | 59.372 | 31.647 | 1.00 11.52 | C |
| ATOM | 1467 | C | VAL | A | 142 | 48.523 | 56.521 | 28.996 | 1.00 10.67 | C |
| ATOM | 1468 | O | VAL | A | 142 | 48.165 | 56.768 | 27.842 | 1.00 10.99 | O |
| ATOM | 1470 | N | LEU | A | 143 | 48.512 | 55.298 | 29.521 | 1.00 11.04 | N |
| ATOM | 1471 | CA | LEU | A | 143 | 47.986 | 54.084 | 28.849 | 1.00 10.64 | C |
| ATOM | 1473 | CB | LEU | A | 143 | 49.113 | 53.249 | 28.252 | 1.00 11.37 | C |
| ATOM | 1476 | CG | LEU | A | 143 | 49.865 | 53.739 | 27.012 | 1.00 11.50 | C |
| ATOM | 1478 | CD1 | LEU | A | 143 | 51.209 | 53.025 | 26.747 | 1.00 12.54 | C |
| ATOM | 1482 | CD2 | LEU | A | 143 | 48.911 | 53.645 | 25.847 | 1.00 13.47 | C |
| ATOM | 1486 | C | LEU | A | 143 | 47.296 | 53.303 | 29.974 | 1.00 12.36 | C |
| ATOM | 1487 | O | LEU | A | 143 | 47.631 | 53.482 | 31.155 | 1.00 10.97 | O |
| ATOM | 1489 | N | PRO | A | 144 | 46.348 | 52.418 | 29.610 | 1.00 13.21 | N |
| ATOM | 1490 | CA | PRO | A | 144 | 45.685 | 51.568 | 30.605 | 1.00 12.93 | C |
| ATOM | 1492 | CB | PRO | A | 144 | 44.709 | 50.722 | 29.792 | 1.00 12.97 | C |
| ATOM | 1495 | CG | PRO | A | 144 | 45.057 | 51.018 | 28.327 | 1.00 13.57 | C |
| ATOM | 1498 | CD | PRO | A | 144 | 45.839 | 52.223 | 28.245 | 1.00 12.64 | C |
| ATOM | 1501 | C | PRO | A | 144 | 46.696 | 50.694 | 31.350 | 1.00 14.27 | C |
| ATOM | 1502 | O | PRO | A | 144 | 47.644 | 50.176 | 30.738 | 1.00 13.67 | O |
| ATOM | 1503 | N | SER | A | 145 | 46.538 | 50.585 | 32.662 | 1.00 14.92 | N |
| ATOM | 1504 | CA | SER | A | 145 | 47.493 | 49.864 | 33.478 | 1.00 16.95 | C |
| ATOM | 1506 | CB | SER | A | 145 | 47.334 | 50.259 | 34.957 | 1.00 17.68 | C |
| ATOM | 1509 | OG | SER | A | 145 | 46.074 | 49.830 | 35.461 | 1.00 20.32 | O |
| ATOM | 1511 | C | SER | A | 145 | 47.362 | 48.360 | 33.310 | 1.00 17.69 | C |
| ATOM | 1512 | O | SER | A | 145 | 48.332 | 47.628 | 33.547 | 1.00 19.49 | O |
| ATOM | 1514 | N | SER | A | 146 | 46.170 | 47.910 | 32.935 | 1.00 18.05 | N |
| ATOM | 1515 | CA | SER | A | 146 | 45.834 | 46.488 | 32.947 | 1.00 20.84 | C |
| ATOM | 1517 | CB | SER | A | 146 | 45.238 | 46.146 | 34.323 | 1.00 20.73 | C |
| ATOM | 1520 | OG | SER | A | 146 | 44.670 | 44.863 | 34.375 | 1.00 24.83 | O |
| ATOM | 1522 | C | SER | A | 146 | 44.787 | 46.222 | 31.922 | 1.00 21.13 | C |
| ATOM | 1523 | O | SER | A | 146 | 44.079 | 47.115 | 31.506 | 1.00 20.60 | O |
| ATOM | 1525 | N | PHE | A | 147 | 44.639 | 44.957 | 31.548 | 1.00 22.33 | N |
| ATOM | 1526 | CA | PHE | A | 147 | 43.473 | 44.547 | 30.778 | 1.00 22.90 | C |
| ATOM | 1528 | CB | PHE | A | 147 | 43.643 | 43.125 | 30.230 | 1.00 23.89 | C |
| ATOM | 1531 | CG | PHE | A | 147 | 44.551 | 43.048 | 29.061 | 1.00 25.99 | C |
| ATOM | 1532 | CD1 | PHE | A | 147 | 44.219 | 43.684 | 27.880 | 1.00 27.35 | C |
| ATOM | 1534 | CE1 | PHE | A | 147 | 45.049 | 43.623 | 26.778 | 1.00 28.31 | C |
| ATOM | 1536 | CZ | PHE | A | 147 | 46.230 | 42.914 | 26.847 | 1.00 28.45 | C |
| ATOM | 1538 | CE2 | PHE | A | 147 | 46.578 | 42.268 | 28.020 | 1.00 28.98 | C |
| ATOM | 1540 | CD2 | PHE | A | 147 | 45.733 | 42.342 | 29.133 | 1.00 28.10 | C |
| ATOM | 1542 | C | PHE | A | 147 | 42.180 | 44.586 | 31.597 | 1.00 23.13 | C |
| ATOM | 1543 | O | PHE | A | 147 | 41.087 | 44.468 | 31.035 | 1.00 23.00 | O |

| ATOM | 1545 | N   | ASP A 148 | 42.286 | 44.701 | 32.916 | 1.00 | 22.90 | N |
|------|------|-----|-----------|--------|--------|--------|------|-------|---|
| ATOM | 1546 | CA  | ASP A 148 | 41.089 | 44.733 | 33.742 | 1.00 | 23.65 | C |
| ATOM | 1548 | CB  | ASP A 148 | 41.432 | 44.850 | 35.223 | 1.00 | 24.60 | C |
| ATOM | 1551 | CG  | ASP A 148 | 42.131 | 43.623 | 35.765 | 1.00 | 28.57 | C |
| ATOM | 1552 | OD1 | ASP A 148 | 42.370 | 42.649 | 35.006 | 1.00 | 33.35 | O |
| ATOM | 1553 | OD2 | ASP A 148 | 42.444 | 43.658 | 36.973 | 1.00 | 35.03 | O |
| ATOM | 1554 | C   | ASP A 148 | 40.184 | 45.890 | 33.397 | 1.00 | 22.25 | C |
| ATOM | 1555 | O   | ASP A 148 | 39.006 | 45.821 | 33.684 | 1.00 | 22.27 | O |
| ATOM | 1557 | N   | SER A 149 | 40.717 | 46.960 | 32.815 | 1.00 | 21.04 | N |
| ATOM | 1558 | CA  | SER A 149 | 39.874 | 48.119 | 32.454 | 1.00 | 20.65 | C |
| ATOM | 1560 | CB  | SER A 149 | 40.698 | 49.398 | 32.425 | 1.00 | 20.49 | C |
| ATOM | 1563 | OG  | SER A 149 | 41.828 | 49.220 | 31.594 | 1.00 | 19.93 | O |
| ATOM | 1565 | C   | SER A 149 | 39.146 | 47.960 | 31.115 | 1.00 | 20.14 | C |
| ATOM | 1566 | O   | SER A 149 | 38.188 | 48.694 | 30.849 | 1.00 | 20.19 | O |
| ATOM | 1568 | N   | PHE A 150 | 39.571 | 46.992 | 30.289 | 1.00 | 19.92 | N |
| ATOM | 1569 | CA  | PHE A 150 | 38.982 | 46.833 | 28.951 | 1.00 | 18.72 | C |
| ATOM | 1571 | CB  | PHE A 150 | 39.777 | 45.867 | 28.040 | 1.00 | 18.41 | C |
| ATOM | 1574 | CG  | PHE A 150 | 41.109 | 46.419 | 27.536 | 1.00 | 17.31 | C |
| ATOM | 1575 | CD1 | PHE A 150 | 41.944 | 47.167 | 28.355 | 1.00 | 17.26 | C |
| ATOM | 1577 | CE1 | PHE A 150 | 43.163 | 47.652 | 27.881 | 1.00 | 16.86 | C |
| ATOM | 1579 | CZ  | PHE A 150 | 43.558 | 47.360 | 26.585 | 1.00 | 17.81 | C |
| ATOM | 1581 | CE2 | PHE A 150 | 42.741 | 46.621 | 25.779 | 1.00 | 17.81 | C |
| ATOM | 1583 | CD2 | PHE A 150 | 41.526 | 46.155 | 26.251 | 1.00 | 17.51 | C |
| ATOM | 1585 | C   | PHE A 150 | 37.569 | 46.312 | 29.057 | 1.00 | 19.18 | C |
| ATOM | 1586 | O   | PHE A 150 | 37.238 | 45.517 | 29.942 | 1.00 | 19.94 | O |
| ATOM | 1588 | N   | ARG A 151 | 36.747 | 46.752 | 28.126 | 1.00 | 18.14 | N |
| ATOM | 1589 | CA  | ARG A 151 | 35.369 | 46.329 | 28.020 | 1.00 | 16.97 | C |
| ATOM | 1591 | CB  | ARG A 151 | 34.427 | 47.395 | 28.541 | 1.00 | 18.69 | C |
| ATOM | 1594 | CG  | ARG A 151 | 34.583 | 47.693 | 30.008 | 1.00 | 20.86 | C |
| ATOM | 1597 | CD  | ARG A 151 | 34.141 | 46.519 | 30.875 | 1.00 | 22.17 | C |
| ATOM | 1600 | NE  | ARG A 151 | 34.224 | 46.934 | 32.284 | 1.00 | 25.12 | N |
| ATOM | 1602 | CZ  | ARG A 151 | 35.295 | 46.817 | 33.075 | 1.00 | 25.13 | C |
| ATOM | 1603 | NH1 | ARG A 151 | 36.423 | 46.273 | 32.638 | 1.00 | 24.93 | N |
| ATOM | 1606 | NH2 | ARG A 151 | 35.238 | 47.261 | 34.331 | 1.00 | 23.94 | N |
| ATOM | 1609 | C   | ARG A 151 | 35.118 | 46.065 | 26.552 | 1.00 | 17.32 | C |
| ATOM | 1610 | O   | ARG A 151 | 35.919 | 46.444 | 25.681 | 1.00 | 17.67 | O |
| ATOM | 1612 | N   | LEU A 152 | 34.048 | 45.348 | 26.277 | 1.00 | 16.31 | N |
| ATOM | 1613 | CA  | LEU A 152 | 33.603 | 45.137 | 24.912 | 1.00 | 16.54 | C |
| ATOM | 1615 | CB  | LEU A 152 | 32.216 | 44.460 | 24.916 | 1.00 | 16.31 | C |
| ATOM | 1618 | CG  | LEU A 152 | 31.613 | 44.117 | 23.571 | 1.00 | 17.66 | C |
| ATOM | 1620 | CD1 | LEU A 152 | 32.573 | 43.246 | 22.782 | 1.00 | 19.33 | C |
| ATOM | 1624 | CD2 | LEU A 152 | 30.289 | 43.377 | 23.763 | 1.00 | 18.79 | C |
| ATOM | 1628 | C   | LEU A 152 | 33.603 | 46.452 | 24.102 | 1.00 | 14.90 | C |
| ATOM | 1629 | O   | LEU A 152 | 32.983 | 47.450 | 24.500 | 1.00 | 14.72 | O |
| ATOM | 1631 | N   | GLY A 153 | 34.354 | 46.453 | 22.995 | 1.00 | 14.42 | N |
| ATOM | 1632 | CA  | GLY A 153 | 34.426 | 47.578 | 22.102 | 1.00 | 14.94 | C |
| ATOM | 1635 | C   | GLY A 153 | 35.206 | 48.784 | 22.635 | 1.00 | 14.11 | C |
| ATOM | 1636 | O   | GLY A 153 | 35.189 | 49.846 | 22.004 | 1.00 | 12.86 | O |
| ATOM | 1638 | N   | ARG A 154 | 35.918 | 48.620 | 23.766 | 1.00 | 13.55 | N |
| ATOM | 1639 | CA  | ARG A 154 | 36.580 | 49.741 | 24.411 | 1.00 | 13.01 | C |
| ATOM | 1641 | CB  | ARG A 154 | 35.727 | 50.328 | 25.561 | 1.00 | 13.38 | C |
| ATOM | 1644 | CG  | ARG A 154 | 34.268 | 50.615 | 25.279 | 1.00 | 14.39 | C |
| ATOM | 1647 | CD  | ARG A 154 | 34.031 | 51.864 | 24.559 | 1.00 | 15.60 | C |
| ATOM | 1650 | NE  | ARG A 154 | 32.629 | 52.220 | 24.511 | 1.00 | 15.13 | N |
| ATOM | 1652 | CZ  | ARG A 154 | 32.173 | 53.354 | 23.989 | 1.00 | 17.30 | C |
| ATOM | 1653 | NH1 | ARG A 154 | 33.011 | 54.230 | 23.469 | 1.00 | 16.77 | N |
| ATOM | 1656 | NH2 | ARG A 154 | 30.864 | 53.605 | 23.955 | 1.00 | 16.80 | N |

| ATOM | 1659 | C | ARG | A | 154 | 37.901 | 49.302 | 25.015 | 1.00 | 14.28 | C |
| ATOM | 1660 | O | ARG | A | 154 | 38.146 | 48.112 | 25.169 | 1.00 | 15.20 | O |
| ATOM | 1662 | N | GLY | A | 155 | 38.744 | 50.279 | 25.357 | 1.00 | 12.78 | N |
| ATOM | 1663 | CA | GLY | A | 155 | 39.919 | 50.020 | 26.183 | 1.00 | 14.02 | C |
| ATOM | 1666 | C | GLY | A | 155 | 41.204 | 50.689 | 25.756 | 1.00 | 13.42 | C |
| ATOM | 1667 | O | GLY | A | 155 | 42.057 | 50.940 | 26.621 | 1.00 | 14.23 | O |
| ATOM | 1669 | N | LEU | A | 156 | 41.384 | 50.933 | 24.452 | 1.00 | 13.43 | N |
| ATOM | 1670 | CA | LEU | A | 156 | 42.661 | 51.441 | 23.922 | 1.00 | 13.60 | C |
| ATOM | 1672 | CB | LEU | A | 156 | 43.250 | 50.476 | 22.851 | 1.00 | 13.55 | C |
| ATOM | 1675 | CG | LEU | A | 156 | 44.089 | 49.361 | 23.434 | 1.00 | 12.17 | C |
| ATOM | 1677 | CD1 | LEU | A | 156 | 44.435 | 48.311 | 22.307 | 1.00 | 10.98 | C |
| ATOM | 1681 | CD2 | LEU | A | 156 | 45.330 | 49.793 | 24.131 | 1.00 | 13.73 | C |
| ATOM | 1685 | C | LEU | A | 156 | 42.532 | 52.903 | 23.430 | 1.00 | 13.78 | C |
| ATOM | 1686 | O | LEU | A | 156 | 43.390 | 53.406 | 22.710 | 1.00 | 12.70 | O |
| ATOM | 1688 | N | GLU | A | 157 | 41.486 | 53.584 | 23.899 | 1.00 | 14.85 | N |
| ATOM | 1689 | CA | GLU | A | 157 | 41.213 | 54.968 | 23.559 | 1.00 | 14.46 | C |
| ATOM | 1691 | CB | GLU | A | 157 | 39.989 | 55.518 | 24.302 | 1.00 | 15.65 | C |
| ATOM | 1694 | CG | GLU | A | 157 | 38.668 | 54.868 | 23.988 | 1.00 | 20.07 | C |
| ATOM | 1697 | CD | GLU | A | 157 | 38.355 | 53.684 | 24.926 | 1.00 | 23.04 | C |
| ATOM | 1698 | OE1 | GLU | A | 157 | 39.276 | 53.203 | 25.593 | 1.00 | 19.09 | O |
| ATOM | 1699 | OE2 | GLU | A | 157 | 37.178 | 53.230 | 24.969 | 1.00 | 26.11 | O |
| ATOM | 1700 | C | GLU | A | 157 | 42.398 | 55.884 | 23.858 | 1.00 | 13.91 | C |
| ATOM | 1701 | O | GLU | A | 157 | 42.588 | 56.881 | 23.156 | 1.00 | 15.65 | O |
| ATOM | 1703 | N | ASN | A | 158 | 43.183 | 55.567 | 24.897 | 1.00 | 13.01 | N |
| ATOM | 1704 | CA | ASN | A | 158 | 44.360 | 56.438 | 25.216 | 1.00 | 12.36 | C |
| ATOM | 1706 | CB | ASN | A | 158 | 44.594 | 56.510 | 26.725 | 1.00 | 12.74 | C |
| ATOM | 1709 | CG | ASN | A | 158 | 43.576 | 57.361 | 27.439 | 1.00 | 13.45 | C |
| ATOM | 1710 | OD1 | ASN | A | 158 | 43.117 | 58.369 | 26.903 | 1.00 | 16.49 | O |
| ATOM | 1711 | ND2 | ASN | A | 158 | 43.233 | 56.970 | 28.655 | 1.00 | 14.02 | N |
| ATOM | 1714 | C | ASN | A | 158 | 45.672 | 56.039 | 24.496 | 1.00 | 13.40 | C |
| ATOM | 1715 | O | ASN | A | 158 | 46.740 | 56.541 | 24.869 | 1.00 | 13.59 | O |
| ATOM | 1717 | N | SER | A | 159 | 45.540 | 55.207 | 23.461 | 1.00 | 13.46 | N |
| ATOM | 1718 | CA | SER | A | 159 | 46.691 | 54.824 | 22.627 | 1.00 | 13.30 | C |
| ATOM | 1720 | CB | SER | A | 159 | 46.988 | 53.324 | 22.659 | 1.00 | 14.22 | C |
| ATOM | 1723 | OG | SER | A | 159 | 45.993 | 52.602 | 21.941 | 1.00 | 13.27 | O |
| ATOM | 1725 | C | SER | A | 159 | 46.551 | 55.296 | 21.187 | 1.00 | 13.49 | C |
| ATOM | 1726 | O | SER | A | 159 | 45.437 | 55.480 | 20.640 | 1.00 | 12.89 | O |
| ATOM | 1728 | N | LEU | A | 160 | 47.705 | 55.534 | 20.564 | 1.00 | 13.24 | N |
| ATOM | 1729 | CA | LEU | A | 160 | 47.679 | 55.879 | 19.143 | 1.00 | 13.21 | C |
| ATOM | 1731 | CB | LEU | A | 160 | 49.067 | 56.239 | 18.648 | 1.00 | 13.65 | C |
| ATOM | 1734 | CG | LEU | A | 160 | 49.597 | 57.622 | 18.876 | 1.00 | 16.62 | C |
| ATOM | 1736 | CD1 | LEU | A | 160 | 51.063 | 57.602 | 18.364 | 1.00 | 17.04 | C |
| ATOM | 1740 | CD2 | LEU | A | 160 | 48.784 | 58.729 | 18.221 | 1.00 | 17.49 | C |
| ATOM | 1744 | C | LEU | A | 160 | 47.185 | 54.740 | 18.286 | 1.00 | 13.25 | C |
| ATOM | 1745 | O | LEU | A | 160 | 47.487 | 53.569 | 18.564 | 1.00 | 12.97 | O |
| ATOM | 1747 | N | PRO | A | 161 | 46.395 | 55.068 | 17.232 | 1.00 | 13.39 | N |
| ATOM | 1748 | CA | PRO | A | 161 | 46.003 | 53.985 | 16.343 | 1.00 | 13.85 | C |
| ATOM | 1750 | CB | PRO | A | 161 | 45.244 | 54.720 | 15.237 | 1.00 | 15.18 | C |
| ATOM | 1753 | CG | PRO | A | 161 | 44.659 | 55.899 | 15.930 | 1.00 | 14.33 | C |
| ATOM | 1756 | CD | PRO | A | 161 | 45.806 | 56.365 | 16.811 | 1.00 | 13.09 | C |
| ATOM | 1759 | C | PRO | A | 161 | 47.220 | 53.210 | 15.789 | 1.00 | 13.64 | C |
| ATOM | 1760 | O | PRO | A | 161 | 48.254 | 53.794 | 15.509 | 1.00 | 13.72 | O |
| ATOM | 1761 | N | LEU | A | 162 | 47.063 | 51.932 | 15.566 | 1.00 | 14.10 | N |
| ATOM | 1762 | CA | LEU | A | 162 | 48.215 | 51.110 | 15.166 | 1.00 | 13.60 | C |
| ATOM | 1764 | CB | LEU | A | 162 | 47.829 | 49.625 | 15.144 | 1.00 | 14.12 | C |
| ATOM | 1767 | CG | LEU | A | 162 | 47.301 | 49.009 | 16.472 | 1.00 | 16.52 | C |
| ATOM | 1769 | CD1 | LEU | A | 162 | 46.811 | 47.546 | 16.354 | 1.00 | 18.68 | C |

| ATOM | 1773 | CD2 | LEU A 162 | 48.382 | 49.129 | 17.525 | 1.00 | 17.11 | C |
| --- | --- | --- | --- | --- | --- | --- | --- | --- | --- |
| ATOM | 1777 | C | LEU A 162 | 48.729 | 51.566 | 13.799 | 1.00 | 13.70 | C |
| ATOM | 1778 | O | LEU A 162 | 49.939 | 51.586 | 13.564 | 1.00 | 11.83 | O |
| ATOM | 1780 | N | GLU A 163 | 47.812 | 51.961 | 12.906 | 1.00 | 13.57 | N |
| ATOM | 1781 | CA | GLU A 163 | 48.204 | 52.428 | 11.585 | 1.00 | 13.39 | C |
| ATOM | 1783 | CB | GLU A 163 | 46.977 | 52.680 | 10.660 | 1.00 | 13.93 | C |
| ATOM | 1786 | CG | GLU A 163 | 46.061 | 53.816 | 11.042 | 1.00 | 15.69 | C |
| ATOM | 1789 | CD | GLU A 163 | 44.971 | 54.146 | 10.009 | 1.00 | 18.67 | C |
| ATOM | 1790 | OE1 | GLU A 163 | 44.425 | 53.226 | 9.374 | 1.00 | 25.82 | O |
| ATOM | 1791 | OE2 | GLU A 163 | 44.610 | 55.346 | 9.906 | 1.00 | 19.14 | O |
| ATOM | 1792 | C | GLU A 163 | 49.106 | 53.660 | 11.665 | 1.00 | 12.62 | C |
| ATOM | 1793 | O | GLU A 163 | 50.048 | 53.776 | 10.887 | 1.00 | 13.40 | O |
| ATOM | 1795 | N | VAL A 164 | 48.857 | 54.543 | 12.633 | 1.00 | 11.30 | N |
| ATOM | 1796 | CA | VAL A 164 | 49.683 | 55.739 | 12.795 | 1.00 | 11.88 | C |
| ATOM | 1798 | CB | VAL A 164 | 49.062 | 56.733 | 13.793 | 1.00 | 10.52 | C |
| ATOM | 1800 | CG1 | VAL A 164 | 50.025 | 57.880 | 14.077 | 1.00 | 12.00 | C |
| ATOM | 1804 | CG2 | VAL A 164 | 47.739 | 57.277 | 13.167 | 1.00 | 11.87 | C |
| ATOM | 1808 | C | VAL A 164 | 51.106 | 55.359 | 13.209 | 1.00 | 12.09 | C |
| ATOM | 1809 | O | VAL A 164 | 52.109 | 55.960 | 12.755 | 1.00 | 11.84 | O |
| ATOM | 1811 | N | VAL A 165 | 51.211 | 54.398 | 14.112 | 1.00 | 12.80 | N |
| ATOM | 1812 | CA | VAL A 165 | 52.522 | 53.968 | 14.602 | 1.00 | 12.52 | C |
| ATOM | 1814 | CB | VAL A 165 | 52.362 | 53.034 | 15.848 | 1.00 | 12.91 | C |
| ATOM | 1816 | CG1 | VAL A 165 | 53.704 | 52.515 | 16.353 | 1.00 | 12.96 | C |
| ATOM | 1820 | CG2 | VAL A 165 | 51.581 | 53.765 | 16.992 | 1.00 | 14.96 | C |
| ATOM | 1824 | C | VAL A 165 | 53.301 | 53.266 | 13.467 | 1.00 | 12.66 | C |
| ATOM | 1825 | O | VAL A 165 | 54.493 | 53.452 | 13.309 | 1.00 | 12.41 | O |
| ATOM | 1827 | N | ARG A 166 | 52.616 | 52.442 | 12.664 | 1.00 | 11.60 | N |
| ATOM | 1828 | CA | ARG A 166 | 53.303 | 51.798 | 11.515 | 1.00 | 11.94 | C |
| ATOM | 1830 | CB | ARG A 166 | 52.360 | 50.863 | 10.802 | 1.00 | 12.05 | C |
| ATOM | 1833 | CG | ARG A 166 | 52.228 | 49.551 | 11.515 | 1.00 | 10.81 | C |
| ATOM | 1836 | CD | ARG A 166 | 51.368 | 48.514 | 10.776 | 1.00 | 13.39 | C |
| ATOM | 1839 | NE | ARG A 166 | 51.862 | 48.266 | 9.435 | 1.00 | 13.53 | N |
| ATOM | 1841 | CZ | ARG A 166 | 52.820 | 47.408 | 9.141 | 1.00 | 14.36 | C |
| ATOM | 1842 | NH1 | ARG A 166 | 53.396 | 46.713 | 10.093 | 1.00 | 13.45 | N |
| ATOM | 1845 | NH2 | ARG A 166 | 53.208 | 47.245 | 7.894 | 1.00 | 14.63 | N |
| ATOM | 1848 | C | ARG A 166 | 53.795 | 52.848 | 10.497 | 1.00 | 12.15 | C |
| ATOM | 1849 | O | ARG A 166 | 54.917 | 52.819 | 10.012 | 1.00 | 10.96 | O |
| ATOM | 1851 | N | GLY A 167 | 52.964 | 53.832 | 10.191 | 1.00 | 11.48 | N |
| ATOM | 1852 | CA | GLY A 167 | 53.394 | 54.896 | 9.284 | 1.00 | 12.62 | C |
| ATOM | 1855 | C | GLY A 167 | 54.561 | 55.668 | 9.870 | 1.00 | 12.35 | C |
| ATOM | 1856 | O | GLY A 167 | 55.477 | 56.063 | 9.164 | 1.00 | 12.90 | O |
| ATOM | 1858 | N | ALA A 168 | 54.553 | 55.854 | 11.183 | 1.00 | 12.54 | N |
| ATOM | 1859 | CA | ALA A 168 | 55.602 | 56.593 | 11.837 | 1.00 | 12.57 | C |
| ATOM | 1861 | CB | ALA A 168 | 55.250 | 56.823 | 13.309 | 1.00 | 12.72 | C |
| ATOM | 1865 | C | ALA A 168 | 56.927 | 55.856 | 11.718 | 1.00 | 12.31 | C |
| ATOM | 1866 | O | ALA A 168 | 57.999 | 56.444 | 11.414 | 1.00 | 12.45 | O |
| ATOM | 1868 | N | MSE A 169 | 56.883 | 54.559 | 11.978 | 1.00 | 13.10 | N |
| ATOM | 1869 | CA | MSE A 169 | 58.105 | 53.754 | 11.912 | 1.00 | 13.56 | C |
| ATOM | 1871 | CB | MSE A 169 | 57.843 | 52.330 | 12.384 | 1.00 | 13.31 | C |
| ATOM | 1874 | CG | MSE A 169 | 57.471 | 52.263 | 13.825 | 1.00 | 15.03 | C |
| ATOM | 1877 | SE | MSE A 169 | 57.628 | 50.399 | 14.551 | 1.00 | 22.37 | SE |
| ATOM | 1878 | CE | MSE A 169 | 55.963 | 49.627 | 13.743 | 1.00 | 17.26 | C |
| ATOM | 1882 | C | MSE A 169 | 58.670 | 53.830 | 10.494 | 1.00 | 12.31 | C |
| ATOM | 1883 | O | MSE A 169 | 59.876 | 53.897 | 10.321 | 1.00 | 11.23 | O |
| ATOM | 1885 | N | THR A 170 | 57.790 | 53.849 | 9.491 | 1.00 | 11.44 | N |
| ATOM | 1886 | CA | THR A 170 | 58.193 | 53.835 | 8.095 | 1.00 | 11.80 | C |
| ATOM | 1888 | CB | THR A 170 | 56.960 | 53.626 | 7.172 | 1.00 | 11.87 | C |

| | | | | | | | | | |
|---|---|---|---|---|---|---|---|---|---|
|ATOM|1890|OG1|THR|A|170|56.364|52.348|7.438|1.00 11.77|O|
|ATOM|1892|CG2|THR|A|170|57.340|53.699|5.694|1.00 13.60|C|
|ATOM|1896|C|THR|A|170|58.900|55.160|7.755|1.00 11.22|C|
|ATOM|1897|O|THR|A|170|60.025|55.164|7.228|1.00 11.98|O|
|ATOM|1899|N|ILE|A|171|58.276|56.274|8.077|1.00 11.88|N|
|ATOM|1900|CA|ILE|A|171|58.884|57.569|7.878|1.00 12.43|C|
|ATOM|1902|CB|ILE|A|171|57.860|58.651|8.216|1.00 12.28|C|
|ATOM|1904|CG1|ILE|A|171|56.678|58.550|7.214|1.00 12.07|C|
|ATOM|1907|CD1|ILE|A|171|55.464|59.491|7.551|1.00 13.91|C|
|ATOM|1911|CG2|ILE|A|171|58.466|60.048|8.183|1.00 13.30|C|
|ATOM|1915|C|ILE|A|171|60.168|57.735|8.672|1.00 12.66|C|
|ATOM|1916|O|ILE|A|171|61.131|58.291|8.162|1.00 12.96|O|
|ATOM|1918|N|ARG|A|172|60.172|57.283|9.929|1.00 12.36|N|
|ATOM|1919|CA|ARG|A|172|61.390|57.392|10.793|1.00 12.04|C|
|ATOM|1921|CB|ARG|A|172|61.140|56.743|12.151|1.00 12.60|C|
|ATOM|1924|CG|ARG|A|172|62.353|56.635|13.079|1.00 12.41|C|
|ATOM|1927|CD|ARG|A|172|62.644|57.845|13.841|1.00 14.54|C|
|ATOM|1930|NE|ARG|A|172|63.218|58.888|13.003|1.00 15.11|N|
|ATOM|1932|CZ|ARG|A|172|63.440|60.118|13.451|1.00 16.80|C|
|ATOM|1933|NH1|ARG|A|172|63.170|60.425|14.710|1.00 14.72|N|
|ATOM|1936|NH2|ARG|A|172|63.984|61.025|12.641|1.00 18.19|N|
|ATOM|1939|C|ARG|A|172|62.568|56.737|10.085|1.00 12.66|C|
|ATOM|1940|O|ARG|A|172|63.661|57.303|10.024|1.00 13.59|O|
|ATOM|1942|N|VAL|A|173|62.348|55.552|9.573|1.00 13.12|N|
|ATOM|1943|CA|VAL|A|173|63.419|54.859|8.920|1.00 12.95|C|
|ATOM|1945|CB|VAL|A|173|62.999|53.377|8.531|1.00 12.65|C|
|ATOM|1947|CG1|VAL|A|173|64.065|52.726|7.619|1.00 13.50|C|
|ATOM|1951|CG2|VAL|A|173|62.790|52.490|9.781|1.00 13.50|C|
|ATOM|1955|C|VAL|A|173|63.899|55.450|7.626|1.00 13.47|C|
|ATOM|1956|O|VAL|A|173|65.077|55.698|7.468|1.00 13.17|O|
|ATOM|1958|N|ASN|A|174|62.983|55.840|6.740|1.00 13.24|N|
|ATOM|1959|CA|ASN|A|174|63.279|56.820|5.699|1.00 13.51|C|
|ATOM|1961|CB|ASN|A|174|62.040|57.215|4.893|1.00 13.64|C|
|ATOM|1964|CG|ASN|A|174|62.404|57.686|3.475|1.00 13.12|C|
|ATOM|1965|OD1|ASN|A|174|62.828|56.902|2.644|1.00 11.74|O|
|ATOM|1966|ND2|ASN|A|174|62.308|59.008|3.248|1.00 14.34|N|
|ATOM|1969|C|ASN|A|174|64.133|57.988|6.009|1.00 13.38|C|
|ATOM|1970|O|ASN|A|174|65.120|58.185|5.349|1.00 13.49|O|
|ATOM|1972|N|SER|A|175|63.733|58.747|7.009|1.00 14.03|N|
|ATOM|1973|CA|SER|A|175|64.423|59.960|7.382|1.00 15.01|C|
|ATOM|1975|CB|SER|A|175|63.630|60.721|8.460|1.00 14.41|C|
|ATOM|1978|OG|SER|A|175|63.560|60.024|9.707|1.00 18.38|O|
|ATOM|1980|C|SER|A|175|65.849|59.722|7.877|1.00 15.49|C|
|ATOM|1981|O|SER|A|175|66.635|60.656|7.915|1.00 18.66|O|
|ATOM|1983|N|LEU|A|176|66.131|58.523|8.372|1.00 13.41|N|
|ATOM|1984|CA|LEU|A|176|67.452|58.187|8.897|1.00 13.77|C|
|ATOM|1986|CB|LEU|A|176|67.308|57.324|10.156|1.00 12.96|C|
|ATOM|1989|CG|LEU|A|176|66.610|57.920|11.348|1.00 15.13|C|
|ATOM|1991|CD1|LEU|A|176|66.267|56.801|12.343|1.00 17.67|C|
|ATOM|1995|CD2|LEU|A|176|67.462|58.972|11.964|1.00 15.79|C|
|ATOM|1999|C|LEU|A|176|68.352|57.491|7.878|1.00 12.61|C|
|ATOM|2000|O|LEU|A|176|69.553|57.365|8.093|1.00 12.21|O|
|ATOM|2002|N|THR|A|177|67.788|57.031|6.763|1.00 13.69|N|
|ATOM|2003|CA|THR|A|177|68.591|56.470|5.666|1.00 13.57|C|
|ATOM|2005|CB|THR|A|177|67.731|55.690|4.637|1.00 15.00|C|
|ATOM|2007|OG1|THR|A|177|66.918|56.628|3.891|1.00 17.86|O|
|ATOM|2009|CG2|THR|A|177|66.872|54.647|5.322|1.00 13.89|C|

| | | | | | | | | | |
|---|---|---|---|---|---|---|---|---|---|
| ATOM | 2013 | C | THR | A | 177 | 69.377 | 57.540 | 4.870 | 1.00 14.07 | C |
| ATOM | 2014 | O | THR | A | 177 | 70.245 | 57.219 | 4.052 | 1.00 14.53 | O |
| ATOM | 2016 | N | ARG | A | 178 | 69.107 | 58.811 | 5.146 | 1.00 14.82 | N |
| ATOM | 2017 | CA | ARG | A | 178 | 69.670 | 59.911 | 4.368 | 1.00 14.68 | C |
| ATOM | 2019 | CB | ARG | A | 178 | 68.791 | 61.162 | 4.507 | 1.00 14.77 | C |
| ATOM | 2022 | CG | ARG | A | 178 | 67.388 | 60.977 | 3.873 | 1.00 15.03 | C |
| ATOM | 2025 | CD | ARG | A | 178 | 66.332 | 61.946 | 4.414 | 1.00 14.46 | C |
| ATOM | 2028 | NE | ARG | A | 178 | 66.714 | 63.361 | 4.266 | 1.00 15.44 | N |
| ATOM | 2030 | CZ | ARG | A | 178 | 66.696 | 64.034 | 3.118 | 1.00 16.07 | C |
| ATOM | 2031 | NH1 | ARG | A | 178 | 66.262 | 63.454 | 2.006 | 1.00 14.67 | N |
| ATOM | 2034 | NH2 | ARG | A | 178 | 67.088 | 65.312 | 3.085 | 1.00 15.84 | N |
| ATOM | 2037 | C | ARG | A | 178 | 71.098 | 60.218 | 4.764 | 1.00 14.05 | C |
| ATOM | 2038 | O | ARG | A | 178 | 71.747 | 61.001 | 4.097 | 1.00 15.97 | O |
| ATOM | 2040 | N | GLY | A | 179 | 71.595 | 59.626 | 5.848 | 1.00 15.04 | N |
| ATOM | 2041 | CA | GLY | A | 179 | 73.015 | 59.702 | 6.159 | 1.00 14.83 | C |
| ATOM | 2044 | C | GLY | A | 179 | 73.440 | 60.944 | 6.939 | 1.00 14.59 | C |
| ATOM | 2045 | O | GLY | A | 179 | 74.623 | 61.225 | 7.063 | 1.00 14.29 | O |
| ATOM | 2047 | N | HIS | A | 180 | 72.473 | 61.685 | 7.475 | 1.00 14.06 | N |
| ATOM | 2048 | CA | HIS | A | 180 | 72.732 | 62.911 | 8.241 | 1.00 13.46 | C |
| ATOM | 2050 | CB | HIS | A | 180 | 71.690 | 63.982 | 7.853 | 1.00 12.46 | C |
| ATOM | 2053 | CG | HIS | A | 180 | 71.568 | 64.204 | 6.383 | 1.00 12.47 | C |
| ATOM | 2054 | ND1 | HIS | A | 180 | 70.344 | 64.315 | 5.759 | 1.00 12.49 | N |
| ATOM | 2056 | CE1 | HIS | A | 180 | 70.537 | 64.497 | 4.464 | 1.00 12.41 | C |
| ATOM | 2058 | NE2 | HIS | A | 180 | 71.839 | 64.482 | 4.227 | 1.00 12.66 | N |
| ATOM | 2060 | CD2 | HIS | A | 180 | 72.499 | 64.292 | 5.409 | 1.00 12.16 | C |
| ATOM | 2062 | C | HIS | A | 180 | 72.638 | 62.714 | 9.764 | 1.00 14.14 | C |
| ATOM | 2063 | O | HIS | A | 180 | 72.800 | 63.683 | 10.518 | 1.00 14.96 | O |
| ATOM | 2065 | N | SER | A | 181 | 72.353 | 61.487 | 10.212 | 1.00 12.65 | N |
| ATOM | 2066 | CA | SER | A | 181 | 71.882 | 61.250 | 11.588 | 1.00 12.39 | C |
| ATOM | 2068 | CB | SER | A | 181 | 70.455 | 60.689 | 11.569 | 1.00 12.33 | C |
| ATOM | 2071 | OG | SER | A | 181 | 69.577 | 61.543 | 10.828 | 1.00 10.96 | O |
| ATOM | 2073 | C | SER | A | 181 | 72.763 | 60.399 | 12.516 | 1.00 13.65 | C |
| ATOM | 2074 | O | SER | A | 181 | 72.618 | 60.476 | 13.742 | 1.00 14.36 | O |
| ATOM | 2076 | N | ALA | A | 182 | 73.650 | 59.589 | 11.937 | 1.00 13.02 | N |
| ATOM | 2077 | CA | ALA | A | 182 | 74.513 | 58.694 | 12.717 | 1.00 13.41 | C |
| ATOM | 2079 | CB | ALA | A | 182 | 75.430 | 59.498 | 13.613 | 1.00 12.41 | C |
| ATOM | 2083 | C | ALA | A | 182 | 73.755 | 57.658 | 13.534 | 1.00 13.88 | C |
| ATOM | 2084 | O | ALA | A | 182 | 74.222 | 57.238 | 14.616 | 1.00 15.46 | O |
| ATOM | 2086 | N | VAL | A | 183 | 72.642 | 57.168 | 12.981 | 1.00 13.89 | N |
| ATOM | 2087 | CA | VAL | A | 183 | 71.925 | 56.034 | 13.552 | 1.00 14.45 | C |
| ATOM | 2089 | CB | VAL | A | 183 | 70.430 | 56.248 | 13.531 | 1.00 14.04 | C |
| ATOM | 2091 | CG1 | VAL | A | 183 | 69.684 | 54.958 | 14.012 | 1.00 14.17 | C |
| ATOM | 2095 | CG2 | VAL | A | 183 | 70.047 | 57.454 | 14.387 | 1.00 13.83 | C |
| ATOM | 2099 | C | VAL | A | 183 | 72.320 | 54.795 | 12.721 | 1.00 15.11 | C |
| ATOM | 2100 | O | VAL | A | 183 | 72.277 | 54.834 | 11.504 | 1.00 15.61 | O |
| ATOM | 2102 | N | ARG | A | 184 | 72.776 | 53.722 | 13.380 | 1.00 14.85 | N |
| ATOM | 2103 | CA | ARG | A | 184 | 73.248 | 52.506 | 12.679 | 1.00 14.69 | C |
| ATOM | 2105 | CB | ARG | A | 184 | 73.774 | 51.479 | 13.666 | 1.00 15.48 | C |
| ATOM | 2108 | CG | ARG | A | 184 | 75.043 | 51.904 | 14.362 | 1.00 16.30 | C |
| ATOM | 2111 | CD | ARG | A | 184 | 75.363 | 50.958 | 15.486 | 1.00 17.10 | C |
| ATOM | 2114 | NE | ARG | A | 184 | 74.289 | 51.028 | 16.466 | 1.00 16.88 | N |
| ATOM | 2116 | CZ | ARG | A | 184 | 73.956 | 50.085 | 17.350 | 1.00 18.87 | C |
| ATOM | 2117 | NH1 | ARG | A | 184 | 74.617 | 48.940 | 17.409 | 1.00 18.69 | N |
| ATOM | 2120 | NH2 | ARG | A | 184 | 72.930 | 50.296 | 18.186 | 1.00 18.38 | N |
| ATOM | 2123 | C | ARG | A | 184 | 72.172 | 51.837 | 11.866 | 1.00 14.59 | C |
| ATOM | 2124 | O | ARG | A | 184 | 70.992 | 51.872 | 12.219 | 1.00 13.62 | O |
| ATOM | 2126 | N | LEU | A | 185 | 72.584 | 51.211 | 10.774 | 1.00 15.21 | N |

| ATOM | 2127 | CA | LEU A 185 | 71.661 | 50.418 | 9.962 | 1.00 | 14.94 | C |
| --- | --- | --- | --- | --- | --- | --- | --- | --- | --- |
| ATOM | 2129 | CB | LEU A 185 | 72.386 | 49.749 | 8.788 | 1.00 | 15.14 | C |
| ATOM | 2132 | CG | LEU A 185 | 71.481 | 49.011 | 7.798 | 1.00 | 16.05 | C |
| ATOM | 2134 | CD1 | LEU A 185 | 70.575 | 49.916 | 7.048 | 1.00 | 17.16 | C |
| ATOM | 2138 | CD2 | LEU A 185 | 72.357 | 48.216 | 6.846 | 1.00 | 16.91 | C |
| ATOM | 2142 | C | LEU A 185 | 70.934 | 49.354 | 10.785 | 1.00 | 13.69 | C |
| ATOM | 2143 | O | LEU A 185 | 69.759 | 49.115 | 10.555 | 1.00 | 13.39 | O |
| ATOM | 2145 | N | VAL A 186 | 71.619 | 48.727 | 11.737 | 1.00 | 14.30 | N |
| ATOM | 2146 | CA | VAL A 186 | 71.001 | 47.652 | 12.539 | 1.00 | 13.92 | C |
| ATOM | 2148 | CB | VAL A 186 | 72.037 | 46.951 | 13.459 | 1.00 | 14.97 | C |
| ATOM | 2150 | CG1 | VAL A 186 | 72.556 | 47.855 | 14.551 | 1.00 | 15.19 | C |
| ATOM | 2154 | CG2 | VAL A 186 | 71.426 | 45.706 | 14.074 | 1.00 | 17.02 | C |
| ATOM | 2158 | C | VAL A 186 | 69.816 | 48.177 | 13.351 | 1.00 | 14.22 | C |
| ATOM | 2159 | O | VAL A 186 | 68.823 | 47.474 | 13.609 | 1.00 | 14.49 | O |
| ATOM | 2161 | N | VAL A 187 | 69.877 | 49.458 | 13.698 | 1.00 | 13.00 | N |
| ATOM | 2162 | CA | VAL A 187 | 68.777 | 50.098 | 14.432 | 1.00 | 13.76 | C |
| ATOM | 2164 | CB | VAL A 187 | 69.219 | 51.403 | 15.110 | 1.00 | 13.79 | C |
| ATOM | 2166 | CG1 | VAL A 187 | 68.026 | 52.147 | 15.758 | 1.00 | 14.67 | C |
| ATOM | 2170 | CG2 | VAL A 187 | 70.282 | 51.125 | 16.173 | 1.00 | 13.96 | C |
| ATOM | 2174 | C | VAL A 187 | 67.606 | 50.315 | 13.455 | 1.00 | 12.76 | C |
| ATOM | 2175 | O | VAL A 187 | 66.449 | 50.065 | 13.792 | 1.00 | 13.31 | O |
| ATOM | 2177 | N | LEU A 188 | 67.896 | 50.809 | 12.250 | 1.00 | 12.65 | N |
| ATOM | 2178 | CA | LEU A 188 | 66.858 | 50.940 | 11.219 | 1.00 | 12.50 | C |
| ATOM | 2180 | CB | LEU A 188 | 67.417 | 51.560 | 9.934 | 1.00 | 13.20 | C |
| ATOM | 2183 | CG | LEU A 188 | 68.131 | 52.912 | 10.129 | 1.00 | 15.22 | C |
| ATOM | 2185 | CD1 | LEU A 188 | 68.357 | 53.557 | 8.759 | 1.00 | 17.31 | C |
| ATOM | 2189 | CD2 | LEU A 188 | 67.399 | 53.820 | 11.095 | 1.00 | 19.99 | C |
| ATOM | 2193 | C | LEU A 188 | 66.211 | 49.611 | 10.883 | 1.00 | 12.83 | C |
| ATOM | 2194 | O | LEU A 188 | 65.002 | 49.534 | 10.745 | 1.00 | 13.14 | O |
| ATOM | 2196 | N | GLU A 189 | 67.017 | 48.548 | 10.806 | 1.00 | 12.72 | N |
| ATOM | 2197 | CA | GLU A 189 | 66.508 | 47.192 | 10.546 | 1.00 | 13.59 | C |
| ATOM | 2199 | CB | GLU A 189 | 67.689 | 46.246 | 10.318 | 1.00 | 13.69 | C |
| ATOM | 2202 | CG | GLU A 189 | 68.402 | 46.585 | 9.021 | 1.00 | 15.32 | C |
| ATOM | 2205 | CD | GLU A 189 | 69.588 | 45.702 | 8.751 | 1.00 | 16.95 | C |
| ATOM | 2206 | OE1 | GLU A 189 | 70.257 | 45.275 | 9.719 | 1.00 | 19.19 | O |
| ATOM | 2207 | OE2 | GLU A 189 | 69.850 | 45.446 | 7.550 | 1.00 | 19.23 | O |
| ATOM | 2208 | C | GLU A 189 | 65.619 | 46.670 | 11.684 | 1.00 | 12.70 | C |
| ATOM | 2209 | O | GLU A 189 | 64.686 | 45.882 | 11.454 | 1.00 | 12.49 | O |
| ATOM | 2211 | N | ALA A 190 | 65.886 | 47.127 | 12.910 | 1.00 | 13.43 | N |
| ATOM | 2212 | CA | ALA A 190 | 65.033 | 46.791 | 14.049 | 1.00 | 12.88 | C |
| ATOM | 2214 | CB | ALA A 190 | 65.628 | 47.337 | 15.353 | 1.00 | 12.95 | C |
| ATOM | 2218 | C | ALA A 190 | 63.613 | 47.280 | 13.840 | 1.00 | 12.47 | C |
| ATOM | 2219 | O | ALA A 190 | 62.652 | 46.573 | 14.092 | 1.00 | 11.25 | O |
| ATOM | 2221 | N | LEU A 191 | 63.491 | 48.494 | 13.335 | 1.00 | 13.02 | N |
| ATOM | 2222 | CA | LEU A 191 | 62.193 | 49.053 | 12.985 | 1.00 | 13.17 | C |
| ATOM | 2224 | CB | LEU A 191 | 62.334 | 50.528 | 12.665 | 1.00 | 13.72 | C |
| ATOM | 2227 | CG | LEU A 191 | 62.757 | 51.392 | 13.868 | 1.00 | 11.60 | C |
| ATOM | 2229 | CD1 | LEU A 191 | 63.220 | 52.749 | 13.391 | 1.00 | 14.01 | C |
| ATOM | 2233 | CD2 | LEU A 191 | 61.655 | 51.461 | 14.946 | 1.00 | 12.90 | C |
| ATOM | 2237 | C | LEU A 191 | 61.535 | 48.349 | 11.785 | 1.00 | 12.64 | C |
| ATOM | 2238 | O | LEU A 191 | 60.325 | 48.114 | 11.793 | 1.00 | 13.38 | O |
| ATOM | 2240 | N | THR A 192 | 62.309 | 48.069 | 10.728 | 1.00 | 12.57 | N |
| ATOM | 2241 | CA | THR A 192 | 61.757 | 47.352 | 9.585 | 1.00 | 12.34 | C |
| ATOM | 2243 | CB | THR A 192 | 62.627 | 47.395 | 8.306 | 1.00 | 12.15 | C |
| ATOM | 2245 | OG1 | THR A 192 | 63.882 | 46.761 | 8.513 | 1.00 | 12.27 | O |
| ATOM | 2247 | CG2 | THR A 192 | 62.814 | 48.824 | 7.818 | 1.00 | 12.53 | C |
| ATOM | 2251 | C | THR A 192 | 61.330 | 45.946 | 9.970 | 1.00 | 11.86 | C |

| ATOM | 2252 | O | THR | A | 192 | 60.290 | 45.469 | 9.499 | 1.00 | 13.57 | O |
| ATOM | 2254 | N | ASN | A | 193 | 62.081 | 45.302 | 10.864 | 1.00 | 11.47 | N |
| ATOM | 2255 | CA | ASN | A | 193 | 61.668 | 43.996 | 11.379 | 1.00 | 11.19 | C |
| ATOM | 2257 | CB | ASN | A | 193 | 62.790 | 43.339 | 12.171 | 1.00 | 11.55 | C |
| ATOM | 2260 | CG | ASN | A | 193 | 63.878 | 42.800 | 11.258 | 1.00 | 12.36 | C |
| ATOM | 2261 | OD1 | ASN | A | 193 | 63.627 | 42.552 | 10.072 | 1.00 | 17.45 | O |
| ATOM | 2262 | ND2 | ASN | A | 193 | 65.082 | 42.642 | 11.775 | 1.00 | 13.31 | N |
| ATOM | 2265 | C | ASN | A | 193 | 60.361 | 44.044 | 12.158 | 1.00 | 11.85 | C |
| ATOM | 2266 | O | ASN | A | 193 | 59.508 | 43.212 | 11.959 | 1.00 | 10.78 | O |
| ATOM | 2268 | N | PHE | A | 194 | 60.173 | 45.069 | 12.987 | 1.00 | 11.18 | N |
| ATOM | 2269 | CA | PHE | A | 194 | 58.894 | 45.302 | 13.665 | 1.00 | 11.31 | C |
| ATOM | 2271 | CB | PHE | A | 194 | 58.964 | 46.560 | 14.547 | 1.00 | 11.76 | C |
| ATOM | 2274 | CG | PHE | A | 194 | 59.425 | 46.300 | 15.977 | 1.00 | 12.49 | C |
| ATOM | 2275 | CD1 | PHE | A | 194 | 60.352 | 45.301 | 16.300 | 1.00 | 13.10 | C |
| ATOM | 2277 | CE1 | PHE | A | 194 | 60.739 | 45.094 | 17.640 | 1.00 | 13.66 | C |
| ATOM | 2279 | CZ | PHE | A | 194 | 60.181 | 45.848 | 18.652 | 1.00 | 14.44 | C |
| ATOM | 2281 | CE2 | PHE | A | 194 | 59.256 | 46.824 | 18.340 | 1.00 | 14.38 | C |
| ATOM | 2283 | CD2 | PHE | A | 194 | 58.890 | 47.045 | 17.033 | 1.00 | 12.99 | C |
| ATOM | 2285 | C | PHE | A | 194 | 57.754 | 45.457 | 12.647 | 1.00 | 11.77 | C |
| ATOM | 2286 | O | PHE | A | 194 | 56.684 | 44.830 | 12.755 | 1.00 | 11.82 | O |
| ATOM | 2288 | N | LEU | A | 195 | 57.998 | 46.288 | 11.635 | 1.00 | 12.15 | N |
| ATOM | 2289 | CA | LEU | A | 195 | 56.999 | 46.482 | 10.605 | 1.00 | 12.51 | C |
| ATOM | 2291 | CB | LEU | A | 195 | 57.498 | 47.488 | 9.579 | 1.00 | 12.85 | C |
| ATOM | 2294 | CG | LEU | A | 195 | 57.407 | 48.959 | 9.990 | 1.00 | 13.46 | C |
| ATOM | 2296 | CD1 | LEU | A | 195 | 58.307 | 49.758 | 9.057 | 1.00 | 13.45 | C |
| ATOM | 2300 | CD2 | LEU | A | 195 | 55.943 | 49.469 | 9.971 | 1.00 | 15.00 | C |
| ATOM | 2304 | C | LEU | A | 195 | 56.688 | 45.166 | 9.894 | 1.00 | 12.13 | C |
| ATOM | 2305 | O | LEU | A | 195 | 55.509 | 44.810 | 9.707 | 1.00 | 12.24 | O |
| ATOM | 2307 | N | ASN | A | 196 | 57.723 | 44.470 | 9.449 | 1.00 | 13.12 | N |
| ATOM | 2308 | CA | ASN | A | 196 | 57.508 | 43.250 | 8.632 | 1.00 | 13.25 | C |
| ATOM | 2310 | CB | ASN | A | 196 | 58.768 | 42.916 | 7.886 | 1.00 | 13.21 | C |
| ATOM | 2313 | CG | ASN | A | 196 | 59.150 | 44.001 | 6.922 | 1.00 | 10.04 | C |
| ATOM | 2314 | OD1 | ASN | A | 196 | 58.293 | 44.761 | 6.434 | 1.00 | 12.47 | O |
| ATOM | 2315 | ND2 | ASN | A | 196 | 60.435 | 44.090 | 6.629 | 1.00 | 13.45 | N |
| ATOM | 2318 | C | ASN | A | 196 | 56.942 | 42.056 | 9.385 | 1.00 | 13.85 | C |
| ATOM | 2319 | O | ASN | A | 196 | 56.370 | 41.164 | 8.772 | 1.00 | 14.90 | O |
| ATOM | 2321 | N | HIS | A | 197 | 57.101 | 42.047 | 10.711 | 1.00 | 14.61 | N |
| ATOM | 2322 | CA | HIS | A | 197 | 56.513 | 41.007 | 11.562 | 1.00 | 14.64 | C |
| ATOM | 2324 | CB | HIS | A | 197 | 57.552 | 40.520 | 12.586 | 1.00 | 13.67 | C |
| ATOM | 2327 | CG | HIS | A | 197 | 58.673 | 39.730 | 11.987 | 1.00 | 16.78 | C |
| ATOM | 2328 | ND1 | HIS | A | 197 | 58.464 | 38.515 | 11.363 | 1.00 | 16.12 | N |
| ATOM | 2330 | CE1 | HIS | A | 197 | 59.626 | 38.036 | 10.948 | 1.00 | 18.33 | C |
| ATOM | 2332 | NE2 | HIS | A | 197 | 60.579 | 38.891 | 11.283 | 1.00 | 19.57 | N |
| ATOM | 2334 | CD2 | HIS | A | 197 | 60.009 | 39.959 | 11.931 | 1.00 | 17.15 | C |
| ATOM | 2336 | C | HIS | A | 197 | 55.238 | 41.518 | 12.252 | 1.00 | 14.62 | C |
| ATOM | 2337 | O | HIS | A | 197 | 54.680 | 40.852 | 13.119 | 1.00 | 14.16 | O |
| ATOM | 2339 | N | GLY | A | 198 | 54.777 | 42.714 | 11.896 | 1.00 | 14.20 | N |
| ATOM | 2340 | CA | GLY | A | 198 | 53.517 | 43.195 | 12.444 | 1.00 | 14.67 | C |
| ATOM | 2343 | C | GLY | A | 198 | 53.568 | 43.382 | 13.953 | 1.00 | 14.92 | C |
| ATOM | 2344 | O | GLY | A | 198 | 52.564 | 43.202 | 14.647 | 1.00 | 16.82 | O |
| ATOM | 2346 | N | ILE | A | 199 | 54.720 | 43.815 | 14.443 | 1.00 | 13.23 | N |
| ATOM | 2347 | CA | ILE | A | 199 | 54.888 | 44.202 | 15.843 | 1.00 | 12.90 | C |
| ATOM | 2349 | CB | ILE | A | 199 | 56.293 | 43.826 | 16.363 | 1.00 | 12.65 | C |
| ATOM | 2351 | CG1 | ILE | A | 199 | 56.517 | 42.298 | 16.328 | 1.00 | 13.60 | C |
| ATOM | 2354 | CD1 | ILE | A | 199 | 57.952 | 41.838 | 16.596 | 1.00 | 13.84 | C |
| ATOM | 2358 | CG2 | ILE | A | 199 | 56.516 | 44.395 | 17.762 | 1.00 | 13.28 | C |
| ATOM | 2362 | C | ILE | A | 199 | 54.731 | 45.740 | 15.947 | 1.00 | 13.04 | C |

| ATOM | 2363 | O | ILE | A | 199 | 55.582 | 46.484 | 15.449 | 1.00 | 13.26 | O |
|------|------|------|------|---|-----|--------|--------|--------|------|-------|---|
| ATOM | 2365 | N | THR | A | 200 | 53.677 | 46.192 | 16.619 | 1.00 | 13.27 | N |
| ATOM | 2366 | CA | THR | A | 200 | 53.331 | 47.619 | 16.659 | 1.00 | 12.21 | C |
| ATOM | 2368 | CB | THR | A | 200 | 51.942 | 47.946 | 15.981 | 1.00 | 13.57 | C |
| ATOM | 2370 | OG1 | THR | A | 200 | 51.859 | 47.350 | 14.674 | 1.00 | 13.88 | O |
| ATOM | 2372 | CG2 | THR | A | 200 | 51.777 | 49.451 | 15.872 | 1.00 | 12.29 | C |
| ATOM | 2376 | C | THR | A | 200 | 53.348 | 48.154 | 18.107 | 1.00 | 11.84 | C |
| ATOM | 2377 | O | THR | A | 200 | 52.551 | 47.693 | 18.912 | 1.00 | 12.07 | O |
| ATOM | 2379 | N | PRO | A | 201 | 54.326 | 49.007 | 18.456 | 1.00 | 12.70 | N |
| ATOM | 2380 | CA | PRO | A | 201 | 54.358 | 49.582 | 19.817 | 1.00 | 11.72 | C |
| ATOM | 2382 | CB | PRO | A | 201 | 55.510 | 50.594 | 19.756 | 1.00 | 13.28 | C |
| ATOM | 2385 | CG | PRO | A | 201 | 56.427 | 50.010 | 18.724 | 1.00 | 12.87 | C |
| ATOM | 2388 | CD | PRO | A | 201 | 55.488 | 49.452 | 17.671 | 1.00 | 12.16 | C |
| ATOM | 2391 | C | PRO | A | 201 | 53.052 | 50.218 | 20.240 | 1.00 | 12.02 | C |
| ATOM | 2392 | O | PRO | A | 201 | 52.343 | 50.860 | 19.436 | 1.00 | 11.95 | O |
| ATOM | 2393 | N | ILE | A | 202 | 52.697 | 49.982 | 21.504 | 1.00 | 12.22 | N |
| ATOM | 2394 | CA | ILE | A | 202 | 51.542 | 50.630 | 22.107 | 1.00 | 12.98 | C |
| ATOM | 2396 | CB | ILE | A | 202 | 51.001 | 49.820 | 23.248 | 1.00 | 13.55 | C |
| ATOM | 2398 | CG1 | ILE | A | 202 | 50.506 | 48.469 | 22.737 | 1.00 | 15.01 | C |
| ATOM | 2401 | CD1 | ILE | A | 202 | 49.368 | 48.529 | 21.795 | 1.00 | 18.12 | C |
| ATOM | 2405 | CG2 | ILE | A | 202 | 49.925 | 50.573 | 23.985 | 1.00 | 13.67 | C |
| ATOM | 2409 | C | ILE | A | 202 | 52.075 | 51.970 | 22.634 | 1.00 | 12.41 | C |
| ATOM | 2410 | O | ILE | A | 202 | 52.982 | 51.998 | 23.455 | 1.00 | 13.23 | O |
| ATOM | 2412 | N | VAL | A | 203 | 51.516 | 53.056 | 22.134 | 1.00 | 12.54 | N |
| ATOM | 2413 | CA | VAL | A | 203 | 52.052 | 54.392 | 22.326 | 1.00 | 11.59 | C |
| ATOM | 2415 | CB | VAL | A | 203 | 52.562 | 54.964 | 20.975 | 1.00 | 12.28 | C |
| ATOM | 2417 | CG1 | VAL | A | 203 | 53.120 | 56.392 | 21.138 | 1.00 | 15.51 | C |
| ATOM | 2421 | CG2 | VAL | A | 203 | 53.625 | 54.044 | 20.388 | 1.00 | 13.05 | C |
| ATOM | 2425 | C | VAL | A | 203 | 50.913 | 55.262 | 22.877 | 1.00 | 11.29 | C |
| ATOM | 2426 | O | VAL | A | 203 | 49.824 | 55.182 | 22.373 | 1.00 | 11.53 | O |
| ATOM | 2428 | N | PRO | A | 204 | 51.174 | 56.063 | 23.915 | 1.00 | 10.92 | N |
| ATOM | 2429 | CA | PRO | A | 204 | 50.111 | 56.975 | 24.392 | 1.00 | 11.29 | C |
| ATOM | 2431 | CB | PRO | A | 204 | 50.831 | 57.747 | 25.520 | 1.00 | 11.82 | C |
| ATOM | 2434 | CG | PRO | A | 204 | 51.940 | 56.854 | 25.961 | 1.00 | 11.59 | C |
| ATOM | 2437 | CD | PRO | A | 204 | 52.421 | 56.286 | 24.672 | 1.00 | 12.06 | C |
| ATOM | 2440 | C | PRO | A | 204 | 49.602 | 57.926 | 23.264 | 1.00 | 11.35 | C |
| ATOM | 2441 | O | PRO | A | 204 | 50.366 | 58.378 | 22.377 | 1.00 | 12.32 | O |
| ATOM | 2442 | N | LEU | A | 205 | 48.304 | 58.215 | 23.279 | 1.00 | 11.44 | N |
| ATOM | 2443 | CA | LEU | A | 205 | 47.700 | 59.100 | 22.287 | 1.00 | 11.86 | C |
| ATOM | 2445 | CB | LEU | A | 205 | 46.214 | 59.046 | 22.517 | 1.00 | 12.43 | C |
| ATOM | 2448 | CG | LEU | A | 205 | 45.340 | 59.927 | 21.622 | 1.00 | 12.36 | C |
| ATOM | 2450 | CD1 | LEU | A | 205 | 45.440 | 59.425 | 20.194 | 1.00 | 12.37 | C |
| ATOM | 2454 | CD2 | LEU | A | 205 | 43.919 | 59.931 | 22.110 | 1.00 | 11.90 | C |
| ATOM | 2458 | C | LEU | A | 205 | 48.192 | 60.559 | 22.465 | 1.00 | 11.67 | C |
| ATOM | 2459 | O | LEU | A | 205 | 48.403 | 61.323 | 21.498 | 1.00 | 12.80 | O |
| ATOM | 2461 | N | ARG | A | 206 | 48.334 | 60.960 | 23.735 | 1.00 | 11.93 | N |
| ATOM | 2462 | CA | ARG | A | 206 | 48.612 | 62.341 | 24.111 | 1.00 | 12.14 | C |
| ATOM | 2464 | CB | ARG | A | 206 | 47.479 | 62.886 | 25.000 | 1.00 | 11.95 | C |
| ATOM | 2467 | CG | ARG | A | 206 | 46.111 | 62.930 | 24.362 | 1.00 | 11.10 | C |
| ATOM | 2470 | CD | ARG | A | 206 | 45.092 | 63.544 | 25.250 | 1.00 | 13.92 | C |
| ATOM | 2473 | NE | ARG | A | 206 | 43.791 | 63.821 | 24.620 | 1.00 | 14.06 | N |
| ATOM | 2475 | CZ | ARG | A | 206 | 42.707 | 63.081 | 24.835 | 1.00 | 14.83 | C |
| ATOM | 2476 | NH1 | ARG | A | 206 | 42.784 | 61.977 | 25.593 | 1.00 | 18.59 | N |
| ATOM | 2479 | NH2 | ARG | A | 206 | 41.526 | 63.420 | 24.306 | 1.00 | 14.64 | N |
| ATOM | 2482 | C | ARG | A | 206 | 49.922 | 62.508 | 24.859 | 1.00 | 11.83 | C |
| ATOM | 2483 | O | ARG | A | 206 | 50.470 | 61.569 | 25.464 | 1.00 | 11.29 | O |
| ATOM | 2485 | N | GLY | A | 207 | 50.446 | 63.716 | 24.788 | 1.00 | 11.82 | N |

| ATOM | 2486 | CA | GLY | A | 207 | 51.626 | 64.098 | 25.570 | 1.00 | 12.70 | C |
|------|------|-----|-----|---|-----|--------|--------|--------|------|-------|---|
| ATOM | 2489 | C | GLY | A | 207 | 52.655 | 64.843 | 24.750 | 1.00 | 13.41 | C |
| ATOM | 2490 | O | GLY | A | 207 | 53.509 | 65.505 | 25.325 | 1.00 | 15.03 | O |
| ATOM | 2492 | N | THR | A | 208 | 52.595 | 64.746 | 23.424 | 1.00 | 13.28 | N |
| ATOM | 2493 | CA | THR | A | 208 | 53.579 | 65.477 | 22.600 | 1.00 | 13.37 | C |
| ATOM | 2495 | CB | THR | A | 208 | 54.098 | 64.670 | 21.370 | 1.00 | 14.10 | C |
| ATOM | 2497 | OG1 | THR | A | 208 | 55.115 | 65.441 | 20.699 | 1.00 | 14.00 | O |
| ATOM | 2499 | CG2 | THR | A | 208 | 52.980 | 64.315 | 20.410 | 1.00 | 13.95 | C |
| ATOM | 2503 | C | THR | A | 208 | 53.047 | 66.820 | 22.122 | 1.00 | 11.57 | C |
| ATOM | 2504 | O | THR | A | 208 | 51.860 | 66.980 | 21.839 | 1.00 | 11.39 | O |
| ATOM | 2506 | N | ILE | A | 209 | 53.953 | 67.797 | 22.061 | 1.00 | 12.04 | N |
| ATOM | 2507 | CA | ILE | A | 209 | 53.716 | 69.115 | 21.438 | 1.00 | 11.41 | C |
| ATOM | 2509 | CB | ILE | A | 209 | 54.249 | 70.282 | 22.316 | 1.00 | 12.05 | C |
| ATOM | 2511 | CG1 | ILE | A | 209 | 55.747 | 70.144 | 22.512 | 1.00 | 11.99 | C |
| ATOM | 2514 | CD1 | ILE | A | 209 | 56.208 | 71.253 | 23.418 | 1.00 | 10.37 | C |
| ATOM | 2518 | CG2 | ILE | A | 209 | 53.418 | 70.401 | 23.662 | 1.00 | 11.88 | C |
| ATOM | 2522 | C | ILE | A | 209 | 54.318 | 69.200 | 20.031 | 1.00 | 10.59 | C |
| ATOM | 2523 | O | ILE | A | 209 | 54.284 | 70.235 | 19.399 | 1.00 | 11.04 | O |
| ATOM | 2525 | N | SER | A | 210 | 54.882 | 68.078 | 19.550 | 1.00 | 11.50 | N |
| ATOM | 2526 | CA | SER | A | 210 | 55.377 | 67.998 | 18.201 | 1.00 | 11.86 | C |
| ATOM | 2528 | CB | SER | A | 210 | 54.213 | 67.985 | 17.194 | 1.00 | 12.92 | C |
| ATOM | 2531 | OG | SER | A | 210 | 53.293 | 66.951 | 17.490 | 1.00 | 12.70 | O |
| ATOM | 2533 | C | SER | A | 210 | 56.441 | 69.065 | 17.878 | 1.00 | 12.34 | C |
| ATOM | 2534 | O | SER | A | 210 | 56.466 | 69.669 | 16.770 | 1.00 | 12.65 | O |
| ATOM | 2536 | N | ALA | A | 211 | 57.378 | 69.260 | 18.816 | 1.00 | 11.36 | N |
| ATOM | 2537 | CA | ALA | A | 211 | 58.619 | 70.027 | 18.537 | 1.00 | 12.07 | C |
| ATOM | 2539 | CB | ALA | A | 211 | 58.659 | 71.309 | 19.226 | 1.00 | 11.89 | C |
| ATOM | 2543 | C | ALA | A | 211 | 59.792 | 69.143 | 18.911 | 1.00 | 12.60 | C |
| ATOM | 2546 | N | SER | A | 212 | 60.857 | 69.399 | 19.659 | 1.00 | 12.88 | N |
| ATOM | 2547 | CA | SER | A | 212 | 61.933 | 68.448 | 19.401 | 1.00 | 14.65 | C |
| ATOM | 2549 | CB | SER | A | 212 | 62.974 | 68.167 | 20.456 | 1.00 | 15.64 | C |
| ATOM | 2553 | C | SER | A | 212 | 61.202 | 67.318 | 18.715 | 1.00 | 13.21 | C |
| ATOM | 2554 | O | SER | A | 212 | 61.684 | 66.237 | 18.405 | 1.00 | 13.29 | O |
| ATOM | 2556 | N | GLY | A | 213 | 60.000 | 67.730 | 18.311 | 1.00 | 13.08 | N |
| ATOM | 2557 | CA | GLY | A | 213 | 59.135 | 67.009 | 17.463 | 1.00 | 12.35 | C |
| ATOM | 2560 | C | GLY | A | 213 | 58.308 | 66.145 | 18.387 | 1.00 | 12.46 | C |
| ATOM | 2561 | O | GLY | A | 213 | 58.004 | 66.492 | 19.525 | 1.00 | 13.43 | O |
| ATOM | 2563 | N | ASP | A | 214 | 57.966 | 64.968 | 17.861 | 1.00 | 13.57 | N |
| ATOM | 2564 | CA | ASP | A | 214 | 57.071 | 64.005 | 18.506 | 1.00 | 12.43 | C |
| ATOM | 2566 | CB | ASP | A | 214 | 56.435 | 63.160 | 17.408 | 1.00 | 13.13 | C |
| ATOM | 2569 | CG | ASP | A | 214 | 55.637 | 63.988 | 16.405 | 1.00 | 15.06 | C |
| ATOM | 2570 | OD1 | ASP | A | 214 | 54.860 | 64.850 | 16.833 | 1.00 | 16.34 | O |
| ATOM | 2571 | OD2 | ASP | A | 214 | 55.713 | 63.686 | 15.193 | 1.00 | 17.52 | O |
| ATOM | 2572 | C | ASP | A | 214 | 57.843 | 63.136 | 19.507 | 1.00 | 12.74 | C |
| ATOM | 2573 | O | ASP | A | 214 | 57.858 | 61.887 | 19.401 | 1.00 | 11.87 | O |
| ATOM | 2575 | N | LEU | A | 215 | 58.454 | 63.797 | 20.504 | 1.00 | 11.80 | N |
| ATOM | 2576 | CA | LEU | A | 215 | 59.408 | 63.173 | 21.407 | 1.00 | 11.67 | C |
| ATOM | 2578 | CB | LEU | A | 215 | 59.947 | 64.239 | 22.395 | 1.00 | 12.20 | C |
| ATOM | 2581 | CG | LEU | A | 215 | 60.805 | 65.348 | 21.843 | 1.00 | 12.88 | C |
| ATOM | 2583 | CD1 | LEU | A | 215 | 60.955 | 66.365 | 22.915 | 1.00 | 16.64 | C |
| ATOM | 2587 | CD2 | LEU | A | 215 | 62.196 | 64.783 | 21.448 | 1.00 | 15.35 | C |
| ATOM | 2591 | C | LEU | A | 215 | 58.850 | 61.967 | 22.171 | 1.00 | 11.13 | C |
| ATOM | 2592 | O | LEU | A | 215 | 59.443 | 60.889 | 22.122 | 1.00 | 12.36 | O |
| ATOM | 2594 | N | SER | A | 216 | 57.724 | 62.155 | 22.871 | 1.00 | 11.77 | N |
| ATOM | 2595 | CA | SER | A | 216 | 57.237 | 61.085 | 23.724 | 1.00 | 13.24 | C |
| ATOM | 2597 | CB | SER | A | 216 | 56.086 | 61.534 | 24.614 | 1.00 | 14.95 | C |
| ATOM | 2600 | OG | SER | A | 216 | 55.762 | 60.523 | 25.530 | 1.00 | 15.31 | O |

| ATOM | 2602 | C | SER | A | 216 | 56.878 | 59.862 | 22.870 | 1.00 | 12.36 | C |
| --- | --- | --- | --- | --- | --- | --- | --- | --- | --- | --- | --- |
| ATOM | 2603 | O | SER | A | 216 | 57.374 | 58.761 | 23.141 | 1.00 | 13.35 | O |
| ATOM | 2605 | N | PRO | A | 217 | 56.004 | 60.020 | 21.844 | 1.00 | 12.31 | N |
| ATOM | 2606 | CA | PRO | A | 217 | 55.644 | 58.788 | 21.118 | 1.00 | 12.02 | C |
| ATOM | 2608 | CB | PRO | A | 217 | 54.558 | 59.277 | 20.108 | 1.00 | 12.22 | C |
| ATOM | 2611 | CG | PRO | A | 217 | 54.769 | 60.747 | 20.031 | 1.00 | 12.34 | C |
| ATOM | 2614 | CD | PRO | A | 217 | 55.247 | 61.177 | 21.367 | 1.00 | 13.13 | C |
| ATOM | 2617 | C | PRO | A | 217 | 56.816 | 58.117 | 20.399 | 1.00 | 11.70 | C |
| ATOM | 2618 | O | PRO | A | 217 | 56.893 | 56.884 | 20.369 | 1.00 | 12.51 | O |
| ATOM | 2619 | N | LEU | A | 218 | 57.735 | 58.917 | 19.832 | 1.00 | 13.10 | N |
| ATOM | 2620 | CA | LEU | A | 218 | 58.905 | 58.359 | 19.223 | 1.00 | 12.30 | C |
| ATOM | 2622 | CB | LEU | A | 218 | 59.729 | 59.410 | 18.463 | 1.00 | 12.47 | C |
| ATOM | 2625 | CG | LEU | A | 218 | 59.133 | 59.896 | 17.134 | 1.00 | 14.02 | C |
| ATOM | 2627 | CD1 | LEU | A | 218 | 59.856 | 61.113 | 16.633 | 1.00 | 15.90 | C |
| ATOM | 2631 | CD2 | LEU | A | 218 | 59.088 | 58.822 | 16.100 | 1.00 | 14.55 | C |
| ATOM | 2635 | C | LEU | A | 218 | 59.770 | 57.634 | 20.275 | 1.00 | 12.09 | C |
| ATOM | 2636 | O | LEU | A | 218 | 60.400 | 56.670 | 19.962 | 1.00 | 12.91 | O |
| ATOM | 2638 | N | SER | A | 219 | 59.766 | 58.107 | 21.524 | 1.00 | 12.21 | N |
| ATOM | 2639 | CA | SER | A | 219 | 60.523 | 57.412 | 22.591 | 1.00 | 12.77 | C |
| ATOM | 2641 | CB | SER | A | 219 | 60.640 | 58.301 | 23.843 | 1.00 | 13.86 | C |
| ATOM | 2644 | OG | SER | A | 219 | 61.388 | 59.472 | 23.536 | 1.00 | 19.30 | O |
| ATOM | 2646 | C | SER | A | 219 | 59.898 | 56.052 | 22.924 | 1.00 | 11.84 | C |
| ATOM | 2647 | O | SER | A | 219 | 60.602 | 55.092 | 23.253 | 1.00 | 11.77 | O |
| ATOM | 2649 | N | TYR | A | 220 | 58.567 | 55.957 | 22.870 | 1.00 | 11.91 | N |
| ATOM | 2650 | CA | TYR | A | 220 | 57.917 | 54.657 | 23.024 | 1.00 | 12.90 | C |
| ATOM | 2652 | CB | TYR | A | 220 | 56.393 | 54.764 | 23.030 | 1.00 | 12.72 | C |
| ATOM | 2655 | CG | TYR | A | 220 | 55.896 | 55.219 | 24.373 | 1.00 | 12.75 | C |
| ATOM | 2656 | CD1 | TYR | A | 220 | 55.895 | 56.575 | 24.722 | 1.00 | 11.61 | C |
| ATOM | 2658 | CE1 | TYR | A | 220 | 55.469 | 56.993 | 25.989 | 1.00 | 10.77 | C |
| ATOM | 2660 | CZ | TYR | A | 220 | 55.063 | 56.046 | 26.909 | 1.00 | 12.49 | C |
| ATOM | 2661 | OH | TYR | A | 220 | 54.685 | 56.366 | 28.204 | 1.00 | 14.40 | O |
| ATOM | 2663 | CE2 | TYR | A | 220 | 55.129 | 54.696 | 26.601 | 1.00 | 12.69 | C |
| ATOM | 2665 | CD2 | TYR | A | 220 | 55.503 | 54.297 | 25.318 | 1.00 | 11.96 | C |
| ATOM | 2667 | C | TYR | A | 220 | 58.377 | 53.650 | 21.937 | 1.00 | 13.00 | C |
| ATOM | 2668 | O | TYR | A | 220 | 58.627 | 52.492 | 22.198 | 1.00 | 13.33 | O |
| ATOM | 2670 | N | ILE | A | 221 | 58.490 | 54.124 | 20.706 | 1.00 | 12.25 | N |
| ATOM | 2671 | CA | ILE | A | 221 | 58.953 | 53.262 | 19.620 | 1.00 | 11.89 | C |
| ATOM | 2673 | CB | ILE | A | 221 | 58.777 | 53.936 | 18.262 | 1.00 | 12.46 | C |
| ATOM | 2675 | CG1 | ILE | A | 221 | 57.288 | 54.036 | 17.932 | 1.00 | 12.84 | C |
| ATOM | 2678 | CD1 | ILE | A | 221 | 56.938 | 55.043 | 16.856 | 1.00 | 12.37 | C |
| ATOM | 2682 | CG2 | ILE | A | 221 | 59.569 | 53.216 | 17.158 | 1.00 | 13.66 | C |
| ATOM | 2686 | C | ILE | A | 221 | 60.438 | 52.843 | 19.868 | 1.00 | 11.66 | C |
| ATOM | 2687 | O | ILE | A | 221 | 60.777 | 51.656 | 19.792 | 1.00 | 11.63 | O |
| ATOM | 2689 | N | ALA | A | 222 | 61.272 | 53.805 | 20.239 | 1.00 | 10.69 | N |
| ATOM | 2690 | CA | ALA | A | 222 | 62.678 | 53.504 | 20.585 | 1.00 | 11.93 | C |
| ATOM | 2692 | CB | ALA | A | 222 | 63.502 | 54.760 | 20.849 | 1.00 | 12.18 | C |
| ATOM | 2696 | C | ALA | A | 222 | 62.858 | 52.526 | 21.746 | 1.00 | 11.64 | C |
| ATOM | 2697 | O | ALA | A | 222 | 63.700 | 51.616 | 21.701 | 1.00 | 12.74 | O |
| ATOM | 2699 | N | ALA | A | 223 | 62.069 | 52.710 | 22.788 | 1.00 | 12.49 | N |
| ATOM | 2700 | CA | ALA | A | 223 | 62.098 | 51.826 | 23.928 | 1.00 | 12.58 | C |
| ATOM | 2702 | CB | ALA | A | 223 | 61.222 | 52.370 | 25.048 | 1.00 | 12.91 | C |
| ATOM | 2706 | C | ALA | A | 223 | 61.664 | 50.407 | 23.544 | 1.00 | 12.66 | C |
| ATOM | 2707 | O | ALA | A | 223 | 62.167 | 49.418 | 24.088 | 1.00 | 13.92 | O |
| ATOM | 2709 | N | ALA | A | 224 | 60.730 | 50.287 | 22.602 | 1.00 | 12.14 | N |
| ATOM | 2710 | CA | ALA | A | 224 | 60.268 | 48.952 | 22.204 | 1.00 | 11.54 | C |
| ATOM | 2712 | CB | ALA | A | 224 | 59.002 | 49.037 | 21.424 | 1.00 | 12.00 | C |
| ATOM | 2716 | C | ALA | A | 224 | 61.366 | 48.184 | 21.436 | 1.00 | 11.40 | C |

| ATOM | 2717 | O | ALA A 224 | 61.659 | 47.053 | 21.748 | 1.00 | 12.25 | O |
| --- | --- | --- | --- | --- | --- | --- | --- | --- | --- |
| ATOM | 2719 | N | ILE A 225 | 62.003 | 48.822 | 20.459 | 1.00 | 11.78 | N |
| ATOM | 2720 | CA | ILE A 225 | 63.043 | 48.091 | 19.717 | 1.00 | 12.33 | C |
| ATOM | 2722 | CB | ILE A 225 | 63.441 | 48.760 | 18.383 | 1.00 | 12.35 | C |
| ATOM | 2724 | CG1 | ILE A 225 | 64.109 | 50.085 | 18.658 | 1.00 | 11.48 | C |
| ATOM | 2727 | CD1 | ILE A 225 | 64.688 | 50.840 | 17.465 | 1.00 | 13.17 | C |
| ATOM | 2731 | CG2 | ILE A 225 | 62.243 | 48.849 | 17.452 | 1.00 | 13.73 | C |
| ATOM | 2735 | C | ILE A 225 | 64.302 | 47.820 | 20.573 | 1.00 | 12.57 | C |
| ATOM | 2736 | O | ILE A 225 | 65.113 | 46.953 | 20.219 | 1.00 | 11.98 | O |
| ATOM | 2738 | N | SER A 226 | 64.455 | 48.582 | 21.672 | 1.00 | 12.56 | N |
| ATOM | 2739 | CA | SER A 226 | 65.559 | 48.336 | 22.592 | 1.00 | 13.87 | C |
| ATOM | 2741 | CB | SER A 226 | 66.272 | 49.634 | 22.975 | 1.00 | 14.00 | C |
| ATOM | 2744 | OG | SER A 226 | 65.452 | 50.511 | 23.628 | 1.00 | 19.53 | O |
| ATOM | 2746 | C | SER A 226 | 65.164 | 47.456 | 23.794 | 1.00 | 13.60 | C |
| ATOM | 2747 | O | SER A 226 | 65.994 | 47.199 | 24.665 | 1.00 | 13.60 | O |
| ATOM | 2749 | N | GLY A 227 | 63.932 | 46.922 | 23.792 | 1.00 | 13.51 | N |
| ATOM | 2750 | CA | GLY A 227 | 63.517 | 45.961 | 24.795 | 1.00 | 13.54 | C |
| ATOM | 2753 | C | GLY A 227 | 63.436 | 46.521 | 26.221 | 1.00 | 12.63 | C |
| ATOM | 2754 | O | GLY A 227 | 63.739 | 45.843 | 27.221 | 1.00 | 11.73 | O |
| ATOM | 2756 | N | HIS A 228 | 62.958 | 47.747 | 26.318 | 1.00 | 12.93 | N |
| ATOM | 2757 | CA | HIS A 228 | 62.714 | 48.345 | 27.624 | 1.00 | 13.34 | C |
| ATOM | 2759 | CB | HIS A 228 | 62.081 | 49.726 | 27.472 | 1.00 | 13.13 | C |
| ATOM | 2762 | CG | HIS A 228 | 61.984 | 50.515 | 28.746 | 1.00 | 14.01 | C |
| ATOM | 2763 | ND1 | HIS A 228 | 61.186 | 50.131 | 29.802 | 1.00 | 14.61 | N |
| ATOM | 2765 | CE1 | HIS A 228 | 61.318 | 51.009 | 30.785 | 1.00 | 14.12 | C |
| ATOM | 2767 | NE2 | HIS A 228 | 62.159 | 51.952 | 30.397 | 1.00 | 14.32 | N |
| ATOM | 2769 | CD2 | HIS A 228 | 62.588 | 51.668 | 29.125 | 1.00 | 14.88 | C |
| ATOM | 2771 | C | HIS A 228 | 61.785 | 47.381 | 28.380 | 1.00 | 12.25 | C |
| ATOM | 2772 | O | HIS A 228 | 60.798 | 46.872 | 27.800 | 1.00 | 12.25 | O |
| ATOM | 2774 | N | PRO A 229 | 62.078 | 47.139 | 29.666 | 1.00 | 13.76 | N |
| ATOM | 2775 | CA | PRO A 229 | 61.280 | 46.173 | 30.447 | 1.00 | 14.28 | C |
| ATOM | 2777 | CB | PRO A 229 | 61.942 | 46.231 | 31.840 | 1.00 | 15.20 | C |
| ATOM | 2780 | CG | PRO A 229 | 63.258 | 46.840 | 31.648 | 1.00 | 15.75 | C |
| ATOM | 2783 | CD | PRO A 229 | 63.197 | 47.687 | 30.451 | 1.00 | 13.07 | C |
| ATOM | 2786 | C | PRO A 229 | 59.789 | 46.490 | 30.606 | 1.00 | 14.94 | C |
| ATOM | 2787 | O | PRO A 229 | 58.980 | 45.588 | 30.944 | 1.00 | 15.30 | O |
| ATOM | 2788 | N | ASP A 230 | 59.436 | 47.759 | 30.416 | 1.00 | 15.07 | N |
| ATOM | 2789 | CA | ASP A 230 | 58.062 | 48.247 | 30.610 | 1.00 | 15.44 | C |
| ATOM | 2791 | CB | ASP A 230 | 58.026 | 49.433 | 31.622 | 1.00 | 16.12 | C |
| ATOM | 2794 | CG | ASP A 230 | 56.591 | 49.738 | 32.157 | 1.00 | 16.44 | C |
| ATOM | 2795 | OD1 | ASP A 230 | 55.775 | 48.815 | 32.211 | 1.00 | 21.90 | O |
| ATOM | 2796 | OD2 | ASP A 230 | 56.244 | 50.891 | 32.512 | 1.00 | 14.30 | O |
| ATOM | 2797 | C | ASP A 230 | 57.397 | 48.605 | 29.274 | 1.00 | 16.01 | C |
| ATOM | 2798 | O | ASP A 230 | 56.303 | 49.205 | 29.255 | 1.00 | 17.72 | O |
| ATOM | 2800 | N | SER A 231 | 58.029 | 48.220 | 28.162 | 1.00 | 14.49 | N |
| ATOM | 2801 | CA | SER A 231 | 57.504 | 48.536 | 26.844 | 1.00 | 14.24 | C |
| ATOM | 2803 | CB | SER A 231 | 58.634 | 48.669 | 25.822 | 1.00 | 14.73 | C |
| ATOM | 2806 | OG | SER A 231 | 58.125 | 48.660 | 24.514 | 1.00 | 17.70 | O |
| ATOM | 2808 | C | SER A 231 | 56.512 | 47.460 | 26.394 | 1.00 | 13.34 | C |
| ATOM | 2809 | O | SER A 231 | 56.824 | 46.268 | 26.454 | 1.00 | 14.21 | O |
| ATOM | 2811 | N | LYS A 232 | 55.332 | 47.895 | 25.954 | 1.00 | 14.03 | N |
| ATOM | 2812 | CA | LYS A 232 | 54.327 | 47.013 | 25.396 | 1.00 | 15.39 | C |
| ATOM | 2814 | CB | LYS A 232 | 52.978 | 47.190 | 26.104 | 1.00 | 15.02 | C |
| ATOM | 2817 | CG | LYS A 232 | 53.007 | 46.589 | 27.540 | 1.00 | 21.29 | C |
| ATOM | 2820 | CD | LYS A 232 | 51.701 | 45.838 | 27.963 | 1.00 | 22.79 | C |
| ATOM | 2823 | CE | LYS A 232 | 50.600 | 46.738 | 28.717 | 1.00 | 29.33 | C |
| ATOM | 2826 | NZ | LYS A 232 | 49.094 | 46.284 | 28.599 | 1.00 | 29.04 | N |

| ATOM | 2830 | C | LYS | A | 232 | 54.169 | 47.181 | 23.888 | 1.00 | 13.62 | C |
|------|------|------|-----|---|-----|--------|--------|--------|------|-------|---|
| ATOM | 2831 | O | LYS | A | 232 | 54.311 | 48.298 | 23.344 | 1.00 | 13.25 | O |
| ATOM | 2833 | N | VAL | A | 233 | 53.880 | 46.044 | 23.236 | 1.00 | 13.04 | N |
| ATOM | 2834 | CA | VAL | A | 233 | 53.648 | 46.021 | 21.820 | 1.00 | 12.32 | C |
| ATOM | 2836 | CB | VAL | A | 233 | 54.881 | 45.583 | 21.026 | 1.00 | 13.10 | C |
| ATOM | 2838 | CG1 | VAL | A | 233 | 56.139 | 46.340 | 21.424 | 1.00 | 12.75 | C |
| ATOM | 2842 | CG2 | VAL | A | 233 | 55.133 | 44.087 | 21.210 | 1.00 | 12.06 | C |
| ATOM | 2846 | C | VAL | A | 233 | 52.430 | 45.152 | 21.464 | 1.00 | 12.28 | C |
| ATOM | 2847 | O | VAL | A | 233 | 52.083 | 44.197 | 22.176 | 1.00 | 13.09 | O |
| ATOM | 2849 | N | HIS | A | 234 | 51.847 | 45.456 | 20.314 | 1.00 | 13.16 | N |
| ATOM | 2850 | CA | HIS | A | 234 | 50.707 | 44.743 | 19.740 | 1.00 | 14.00 | C |
| ATOM | 2852 | CB | HIS | A | 234 | 49.746 | 45.757 | 19.128 | 1.00 | 14.69 | C |
| ATOM | 2855 | CG | HIS | A | 234 | 48.592 | 45.134 | 18.409 | 1.00 | 14.95 | C |
| ATOM | 2856 | ND1 | HIS | A | 234 | 48.686 | 44.680 | 17.110 | 1.00 | 15.13 | N |
| ATOM | 2858 | CE1 | HIS | A | 234 | 47.527 | 44.160 | 16.744 | 1.00 | 16.24 | C |
| ATOM | 2860 | NE2 | HIS | A | 234 | 46.668 | 44.307 | 17.737 | 1.00 | 15.47 | N |
| ATOM | 2862 | CD2 | HIS | A | 234 | 47.305 | 44.922 | 18.789 | 1.00 | 16.89 | C |
| ATOM | 2864 | C | HIS | A | 234 | 51.223 | 43.794 | 18.653 | 1.00 | 14.54 | C |
| ATOM | 2865 | O | HIS | A | 234 | 52.064 | 44.153 | 17.834 | 1.00 | 14.99 | O |
| ATOM | 2867 | N | VAL | A | 235 | 50.735 | 42.568 | 18.673 | 1.00 | 15.16 | N |
| ATOM | 2868 | CA | VAL | A | 235 | 51.072 | 41.619 | 17.611 | 1.00 | 16.19 | C |
| ATOM | 2870 | CB | VAL | A | 235 | 52.268 | 40.707 | 17.969 | 1.00 | 17.46 | C |
| ATOM | 2872 | CG1 | VAL | A | 235 | 53.504 | 41.489 | 18.278 | 1.00 | 19.44 | C |
| ATOM | 2876 | CG2 | VAL | A | 235 | 51.967 | 39.804 | 19.166 | 1.00 | 16.11 | C |
| ATOM | 2880 | C | VAL | A | 235 | 49.840 | 40.749 | 17.408 | 1.00 | 16.91 | C |
| ATOM | 2881 | O | VAL | A | 235 | 49.030 | 40.598 | 18.314 | 1.00 | 16.40 | O |
| ATOM | 2883 | N | VAL | A | 236 | 49.712 | 40.174 | 16.221 | 1.00 | 17.37 | N |
| ATOM | 2884 | CA | VAL | A | 236 | 48.699 | 39.154 | 15.961 | 1.00 | 18.62 | C |
| ATOM | 2886 | CB | VAL | A | 236 | 48.039 | 39.354 | 14.597 | 1.00 | 18.65 | C |
| ATOM | 2888 | CG1 | VAL | A | 236 | 47.162 | 38.136 | 14.269 | 1.00 | 19.87 | C |
| ATOM | 2892 | CG2 | VAL | A | 236 | 47.218 | 40.636 | 14.580 | 1.00 | 18.81 | C |
| ATOM | 2896 | C | VAL | A | 236 | 49.464 | 37.865 | 15.964 | 1.00 | 19.91 | C |
| ATOM | 2897 | O | VAL | A | 236 | 50.449 | 37.762 | 15.259 | 1.00 | 20.22 | O |
| ATOM | 2899 | N | HIS | A | 237 | 49.040 | 36.904 | 16.775 | 1.00 | 20.42 | N |
| ATOM | 2900 | CA | HIS | A | 237 | 49.791 | 35.690 | 16.961 | 1.00 | 22.07 | C |
| ATOM | 2902 | CB | HIS | A | 237 | 50.881 | 35.928 | 18.011 | 1.00 | 22.70 | C |
| ATOM | 2905 | CG | HIS | A | 237 | 51.652 | 34.700 | 18.391 | 1.00 | 24.17 | C |
| ATOM | 2906 | ND1 | HIS | A | 237 | 51.431 | 34.015 | 19.570 | 1.00 | 25.03 | N |
| ATOM | 2908 | CE1 | HIS | A | 237 | 52.276 | 33.001 | 19.648 | 1.00 | 26.76 | C |
| ATOM | 2910 | NE2 | HIS | A | 237 | 53.043 | 33.015 | 18.570 | 1.00 | 27.05 | N |
| ATOM | 2912 | CD2 | HIS | A | 237 | 52.681 | 34.075 | 17.776 | 1.00 | 25.91 | C |
| ATOM | 2914 | C | HIS | A | 237 | 48.806 | 34.591 | 17.357 | 1.00 | 23.24 | C |
| ATOM | 2915 | O | HIS | A | 237 | 47.934 | 34.797 | 18.226 | 1.00 | 21.90 | O |
| ATOM | 2917 | N | GLU | A | 238 | 48.940 | 33.432 | 16.693 | 1.00 | 24.23 | N |
| ATOM | 2918 | CA | GLU | A | 238 | 48.035 | 32.304 | 16.886 | 1.00 | 25.99 | C |
| ATOM | 2920 | CB | GLU | A | 238 | 48.269 | 31.676 | 18.267 | 1.00 | 26.33 | C |
| ATOM | 2923 | CG | GLU | A | 238 | 49.641 | 31.001 | 18.364 | 1.00 | 28.65 | C |
| ATOM | 2926 | CD | GLU | A | 238 | 50.059 | 30.609 | 19.791 | 1.00 | 29.94 | C |
| ATOM | 2927 | OE1 | GLU | A | 238 | 49.806 | 31.395 | 20.743 | 1.00 | 37.75 | O |
| ATOM | 2928 | OE2 | GLU | A | 238 | 50.679 | 29.524 | 19.957 | 1.00 | 34.20 | O |
| ATOM | 2929 | C | GLU | A | 238 | 46.598 | 32.763 | 16.675 | 1.00 | 25.49 | C |
| ATOM | 2930 | O | GLU | A | 238 | 45.698 | 32.417 | 17.433 | 1.00 | 26.71 | O |
| ATOM | 2932 | N | GLY | A | 239 | 46.408 | 33.580 | 15.643 | 1.00 | 24.86 | N |
| ATOM | 2933 | CA | GLY | A | 239 | 45.091 | 34.044 | 15.253 | 1.00 | 25.00 | C |
| ATOM | 2936 | C | GLY | A | 239 | 44.385 | 35.004 | 16.201 | 1.00 | 24.94 | C |
| ATOM | 2937 | O | GLY | A | 239 | 43.188 | 35.232 | 16.038 | 1.00 | 24.98 | O |
| ATOM | 2939 | N | LYS | A | 240 | 45.091 | 35.575 | 17.185 | 1.00 | 24.23 | N |

| | | | | | | | | | |
|---|---|---|---|---|---|---|---|---|---|
| ATOM | 2940 | CA | LYS | A | 240 | 44.470 | 36.600 | 18.033 | 1.00 23.57 | C |
| ATOM | 2942 | CB | LYS | A | 240 | 44.101 | 36.090 | 19.443 | 1.00 23.56 | C |
| ATOM | 2945 | CG | LYS | A | 240 | 45.276 | 35.628 | 20.293 | 1.00 25.73 | C |
| ATOM | 2948 | CD | LYS | A | 240 | 44.923 | 35.303 | 21.773 | 1.00 27.40 | C |
| ATOM | 2951 | CE | LYS | A | 240 | 44.077 | 34.049 | 21.911 | 1.00 30.27 | C |
| ATOM | 2954 | NZ | LYS | A | 240 | 44.638 | 33.081 | 22.949 | 1.00 33.96 | N |
| ATOM | 2958 | C | LYS | A | 240 | 45.403 | 37.779 | 18.173 | 1.00 21.23 | C |
| ATOM | 2959 | O | LYS | A | 240 | 46.627 | 37.644 | 18.055 | 1.00 20.75 | O |
| ATOM | 2961 | N | GLU | A | 241 | 44.791 | 38.920 | 18.435 | 1.00 19.10 | N |
| ATOM | 2962 | CA | GLU | A | 241 | 45.523 | 40.119 | 18.850 | 1.00 18.44 | C |
| ATOM | 2964 | CB | GLU | A | 241 | 44.605 | 41.339 | 18.817 | 1.00 17.38 | C |
| ATOM | 2967 | CG | GLU | A | 241 | 44.144 | 41.696 | 17.471 | 1.00 16.70 | C |
| ATOM | 2970 | CD | GLU | A | 241 | 43.316 | 42.977 | 17.498 | 1.00 18.99 | C |
| ATOM | 2971 | OE1 | GLU | A | 241 | 43.923 | 44.077 | 17.589 | 1.00 18.50 | O |
| ATOM | 2972 | OE2 | GLU | A | 241 | 42.065 | 42.876 | 17.445 | 1.00 20.07 | O |
| ATOM | 2973 | C | GLU | A | 241 | 46.047 | 39.934 | 20.273 | 1.00 18.83 | C |
| ATOM | 2974 | O | GLU | A | 241 | 45.330 | 39.460 | 21.170 | 1.00 19.02 | O |
| ATOM | 2976 | N | LYS | A | 242 | 47.302 | 40.308 | 20.461 | 1.00 17.61 | N |
| ATOM | 2977 | CA | LYS | A | 242 | 47.940 | 40.242 | 21.762 | 1.00 17.61 | C |
| ATOM | 2979 | CB | LYS | A | 242 | 48.899 | 39.058 | 21.824 | 1.00 17.82 | C |
| ATOM | 2982 | CG | LYS | A | 242 | 48.193 | 37.725 | 21.913 | 1.00 21.67 | C |
| ATOM | 2985 | CD | LYS | A | 242 | 49.146 | 36.627 | 22.223 | 1.00 25.20 | C |
| ATOM | 2988 | CE | LYS | A | 242 | 49.307 | 35.721 | 21.060 | 1.00 29.95 | C |
| ATOM | 2991 | NZ | LYS | A | 242 | 48.182 | 34.744 | 20.915 | 1.00 33.27 | N |
| ATOM | 2995 | C | LYS | A | 242 | 48.700 | 41.528 | 22.023 | 1.00 16.01 | C |
| ATOM | 2996 | O | LYS | A | 242 | 49.227 | 42.145 | 21.094 | 1.00 14.82 | O |
| ATOM | 2998 | N | ILE | A | 243 | 48.721 | 41.922 | 23.288 | 1.00 15.46 | N |
| ATOM | 2999 | CA | ILE | A | 243 | 49.659 | 42.909 | 23.764 | 1.00 16.01 | C |
| ATOM | 3001 | CB | ILE | A | 243 | 48.931 | 44.090 | 24.435 | 1.00 15.67 | C |
| ATOM | 3003 | CG1 | ILE | A | 243 | 48.082 | 44.815 | 23.383 | 1.00 18.50 | C |
| ATOM | 3006 | CD1 | ILE | A | 243 | 47.049 | 45.698 | 23.947 | 1.00 20.86 | C |
| ATOM | 3010 | CG2 | ILE | A | 243 | 49.923 | 45.071 | 24.991 | 1.00 13.69 | C |
| ATOM | 3014 | C | ILE | A | 243 | 50.632 | 42.209 | 24.690 | 1.00 16.16 | C |
| ATOM | 3015 | O | ILE | A | 243 | 50.226 | 41.557 | 25.663 | 1.00 16.36 | O |
| ATOM | 3017 | N | LEU | A | 244 | 51.913 | 42.282 | 24.323 | 1.00 14.61 | N |
| ATOM | 3018 | CA | LEU | A | 244 | 52.995 | 41.652 | 25.031 | 1.00 14.43 | C |
| ATOM | 3020 | CB | LEU | A | 244 | 53.632 | 40.617 | 24.097 | 1.00 15.06 | C |
| ATOM | 3023 | CG | LEU | A | 244 | 52.687 | 39.603 | 23.481 | 1.00 16.50 | C |
| ATOM | 3025 | CD1 | LEU | A | 244 | 53.495 | 38.825 | 22.450 | 1.00 15.73 | C |
| ATOM | 3029 | CD2 | LEU | A | 244 | 52.084 | 38.688 | 24.548 | 1.00 17.09 | C |
| ATOM | 3033 | C | LEU | A | 244 | 54.051 | 42.657 | 25.414 | 1.00 14.11 | C |
| ATOM | 3034 | O | LEU | A | 244 | 54.065 | 43.746 | 24.854 | 1.00 12.74 | O |
| ATOM | 3036 | N | TYR | A | 245 | 54.955 | 42.281 | 26.325 | 1.00 13.22 | N |
| ATOM | 3037 | CA | TYR | A | 245 | 56.176 | 43.039 | 26.515 | 1.00 14.13 | C |
| ATOM | 3039 | CB | TYR | A | 245 | 56.955 | 42.546 | 27.740 | 1.00 15.63 | C |
| ATOM | 3042 | CG | TYR | A | 245 | 56.277 | 42.963 | 29.016 | 1.00 18.39 | C |
| ATOM | 3043 | CD1 | TYR | A | 245 | 56.325 | 44.292 | 29.453 | 1.00 20.77 | C |
| ATOM | 3045 | CE1 | TYR | A | 245 | 55.701 | 44.689 | 30.631 | 1.00 20.53 | C |
| ATOM | 3047 | CZ | TYR | A | 245 | 55.004 | 43.767 | 31.368 | 1.00 22.68 | C |
| ATOM | 3048 | OH | TYR | A | 245 | 54.368 | 44.165 | 32.521 | 1.00 23.09 | O |
| ATOM | 3050 | CE2 | TYR | A | 245 | 54.905 | 42.451 | 30.944 | 1.00 22.44 | C |
| ATOM | 3052 | CD2 | TYR | A | 245 | 55.550 | 42.054 | 29.772 | 1.00 21.89 | C |
| ATOM | 3054 | C | TYR | A | 245 | 57.038 | 42.978 | 25.257 | 1.00 13.82 | C |
| ATOM | 3055 | O | TYR | A | 245 | 57.018 | 41.941 | 24.536 | 1.00 13.39 | O |
| ATOM | 3057 | N | ALA | A | 246 | 57.799 | 44.047 | 25.002 | 1.00 13.05 | N |
| ATOM | 3058 | CA | ALA | A | 246 | 58.599 | 44.126 | 23.793 | 1.00 14.05 | C |
| ATOM | 3060 | CB | ALA | A | 246 | 59.374 | 45.449 | 23.722 | 1.00 13.93 | C |

| ATOM | 3064 | C | ALA A 246 | 59.547 | 42.922 | 23.634 | 1.00 | 14.25 | C |
|------|------|------|------|--------|--------|--------|------|-------|----|
| ATOM | 3065 | O | ALA A 246 | 59.612 | 42.345 | 22.555 | 1.00 | 13.43 | O |
| ATOM | 3067 | N | ARG A 247 | 60.238 | 42.529 | 24.708 | 1.00 | 14.41 | N |
| ATOM | 3068 | CA | ARG A 247 | 61.132 | 41.360 | 24.640 | 1.00 | 15.58 | C |
| ATOM | 3070 | CB | ARG A 247 | 61.936 | 41.249 | 25.909 | 1.00 | 15.64 | C |
| ATOM | 3073 | CG | ARG A 247 | 63.035 | 42.262 | 25.898 | 1.00 | 18.11 | C |
| ATOM | 3076 | CD | ARG A 247 | 63.733 | 42.327 | 27.218 | 1.00 | 21.33 | C |
| ATOM | 3079 | NE | ARG A 247 | 64.828 | 43.297 | 27.162 | 1.00 | 23.39 | N |
| ATOM | 3081 | CZ | ARG A 247 | 66.071 | 42.986 | 26.794 | 1.00 | 24.23 | C |
| ATOM | 3082 | NH1 | ARG A 247 | 66.406 | 41.735 | 26.499 | 1.00 | 19.92 | N |
| ATOM | 3085 | NH2 | ARG A 247 | 67.003 | 43.923 | 26.771 | 1.00 | 22.64 | N |
| ATOM | 3088 | C | ARG A 247 | 60.425 | 40.049 | 24.340 | 1.00 | 16.80 | C |
| ATOM | 3089 | O | ARG A 247 | 60.994 | 39.251 | 23.593 | 1.00 | 15.68 | O |
| ATOM | 3091 | N | GLU A 248 | 59.223 | 39.855 | 24.896 | 1.00 | 17.46 | N |
| ATOM | 3092 | CA | GLU A 248 | 58.371 | 38.696 | 24.586 | 1.00 | 18.97 | C |
| ATOM | 3094 | CB | GLU A 248 | 57.024 | 38.759 | 25.318 | 1.00 | 19.25 | C |
| ATOM | 3097 | CG | GLU A 248 | 57.134 | 38.709 | 26.800 | 1.00 | 21.66 | C |
| ATOM | 3100 | CD | GLU A 248 | 55.797 | 38.676 | 27.514 | 1.00 | 22.71 | C |
| ATOM | 3101 | OE1 | GLU A 248 | 54.888 | 39.501 | 27.211 | 1.00 | 23.83 | O |
| ATOM | 3102 | OE2 | GLU A 248 | 55.691 | 37.820 | 28.427 | 1.00 | 31.05 | O |
| ATOM | 3103 | C | GLU A 248 | 58.080 | 38.595 | 23.117 | 1.00 | 17.66 | C |
| ATOM | 3104 | O | GLU A 248 | 58.222 | 37.522 | 22.510 | 1.00 | 17.45 | O |
| ATOM | 3106 | N | ALA A 249 | 57.627 | 39.712 | 22.556 | 1.00 | 17.13 | N |
| ATOM | 3107 | CA | ALA A 249 | 57.262 | 39.759 | 21.162 | 1.00 | 18.07 | C |
| ATOM | 3109 | CB | ALA A 249 | 56.672 | 41.152 | 20.784 | 1.00 | 18.33 | C |
| ATOM | 3113 | C | ALA A 249 | 58.474 | 39.441 | 20.318 | 1.00 | 19.36 | C |
| ATOM | 3114 | O | ALA A 249 | 58.380 | 38.692 | 19.368 | 1.00 | 19.64 | O |
| ATOM | 3116 | N | MSE A 250 | 59.626 | 39.986 | 20.691 | 1.00 | 21.08 | N |
| ATOM | 3117 | CA | MSE A 250 | 60.820 | 39.820 | 19.877 | 1.00 | 23.99 | C |
| ATOM | 3119 | CB | MSE A 250 | 61.920 | 40.781 | 20.342 | 1.00 | 24.20 | C |
| ATOM | 3122 | CG | MSE A 250 | 61.661 | 42.230 | 19.896 | 1.00 | 25.63 | C |
| ATOM | 3125 | SE | MSE A 250 | 63.161 | 43.497 | 20.281 | 1.00 | 35.35 | SE |
| ATOM | 3126 | CE | MSE A 250 | 63.743 | 42.573 | 21.693 | 1.00 | 19.08 | C |
| ATOM | 3130 | C | MSE A 250 | 61.292 | 38.364 | 19.880 | 1.00 | 22.74 | C |
| ATOM | 3131 | O | MSE A 250 | 61.755 | 37.855 | 18.865 | 1.00 | 22.94 | O |
| ATOM | 3133 | N | ALA A 251 | 61.140 | 37.696 | 21.019 | 1.00 | 21.82 | N |
| ATOM | 3134 | CA | ALA A 251 | 61.476 | 36.269 | 21.128 | 1.00 | 21.62 | C |
| ATOM | 3136 | CB | ALA A 251 | 61.415 | 35.820 | 22.585 | 1.00 | 21.15 | C |
| ATOM | 3140 | C | ALA A 251 | 60.568 | 35.411 | 20.244 | 1.00 | 21.54 | C |
| ATOM | 3141 | O | ALA A 251 | 60.995 | 34.342 | 19.784 | 1.00 | 22.30 | O |
| ATOM | 3143 | N | LEU A 252 | 59.327 | 35.838 | 19.992 | 1.00 | 21.01 | N |
| ATOM | 3144 | CA | LEU A 252 | 58.451 | 35.109 | 19.073 | 1.00 | 21.87 | C |
| ATOM | 3146 | CB | LEU A 252 | 57.035 | 35.693 | 19.019 | 1.00 | 22.13 | C |
| ATOM | 3149 | CG | LEU A 252 | 56.134 | 35.462 | 20.227 | 1.00 | 23.36 | C |
| ATOM | 3151 | CD1 | LEU A 252 | 54.851 | 36.317 | 20.059 | 1.00 | 25.06 | C |
| ATOM | 3155 | CD2 | LEU A 252 | 55.801 | 33.989 | 20.384 | 1.00 | 25.77 | C |
| ATOM | 3159 | C | LEU A 252 | 59.034 | 35.095 | 17.679 | 1.00 | 22.33 | C |
| ATOM | 3160 | O | LEU A 252 | 58.891 | 34.122 | 16.957 | 1.00 | 22.17 | O |
| ATOM | 3162 | N | PHE A 253 | 59.692 | 36.180 | 17.291 | 1.00 | 23.15 | N |
| ATOM | 3163 | CA | PHE A 253 | 60.209 | 36.317 | 15.926 | 1.00 | 23.32 | C |
| ATOM | 3165 | CB | PHE A 253 | 59.659 | 37.618 | 15.335 | 1.00 | 24.66 | C |
| ATOM | 3168 | CG | PHE A 253 | 58.165 | 37.664 | 15.339 | 1.00 | 24.86 | C |
| ATOM | 3169 | CD1 | PHE A 253 | 57.429 | 37.012 | 14.354 | 1.00 | 26.54 | C |
| ATOM | 3171 | CE1 | PHE A 253 | 56.057 | 37.015 | 14.378 | 1.00 | 24.01 | C |
| ATOM | 3173 | CZ | PHE A 253 | 55.380 | 37.641 | 15.398 | 1.00 | 25.25 | C |
| ATOM | 3175 | CE2 | PHE A 253 | 56.097 | 38.265 | 16.403 | 1.00 | 25.22 | C |
| ATOM | 3177 | CD2 | PHE A 253 | 57.486 | 38.249 | 16.375 | 1.00 | 25.66 | C |

| | | | | | | | | | |
|---|---|---|---|---|---|---|---|---|---|
| ATOM | 3179 | C | PHE | A | 253 | 61.730 | 36.207 | 15.843 | 1.00 22.84 | C |
| ATOM | 3180 | O | PHE | A | 253 | 62.321 | 36.493 | 14.808 | 1.00 23.98 | O |
| ATOM | 3182 | N | ASN | A | 254 | 62.375 | 35.762 | 16.916 | 1.00 21.91 | N |
| ATOM | 3183 | CA | ASN | A | 254 | 63.826 | 35.605 | 16.906 | 1.00 21.81 | C |
| ATOM | 3185 | CB | ASN | A | 254 | 64.205 | 34.540 | 15.864 | 1.00 23.52 | C |
| ATOM | 3188 | CG | ASN | A | 254 | 65.510 | 33.865 | 16.150 | 1.00 27.04 | C |
| ATOM | 3189 | OD1 | ASN | A | 254 | 66.287 | 34.292 | 17.019 | 1.00 35.37 | O |
| ATOM | 3190 | ND2 | ASN | A | 254 | 65.785 | 32.790 | 15.400 | 1.00 31.70 | N |
| ATOM | 3193 | C | ASN | A | 254 | 64.572 | 36.939 | 16.663 | 1.00 20.67 | C |
| ATOM | 3194 | O | ASN | A | 254 | 65.667 | 36.995 | 16.085 | 1.00 19.50 | O |
| ATOM | 3196 | N | LEU | A | 255 | 63.969 | 38.024 | 17.146 | 1.00 18.18 | N |
| ATOM | 3197 | CA | LEU | A | 255 | 64.546 | 39.365 | 17.013 | 1.00 17.98 | C |
| ATOM | 3199 | CB | LEU | A | 255 | 63.429 | 40.389 | 16.842 | 1.00 16.95 | C |
| ATOM | 3202 | CG | LEU | A | 255 | 62.562 | 40.190 | 15.607 | 1.00 17.74 | C |
| ATOM | 3204 | CD1 | LEU | A | 255 | 61.539 | 41.315 | 15.569 | 1.00 16.83 | C |
| ATOM | 3208 | CD2 | LEU | A | 255 | 63.384 | 40.154 | 14.329 | 1.00 15.93 | C |
| ATOM | 3212 | C | LEU | A | 255 | 65.347 | 39.687 | 18.261 | 1.00 17.85 | C |
| ATOM | 3213 | O | LEU | A | 255 | 64.973 | 39.254 | 19.350 | 1.00 17.97 | O |
| ATOM | 3215 | N | GLU | A | 256 | 66.462 | 40.396 | 18.082 | 1.00 17.80 | N |
| ATOM | 3216 | CA | GLU | A | 256 | 67.318 | 40.828 | 19.191 | 1.00 18.12 | C |
| ATOM | 3218 | CB | GLU | A | 256 | 68.781 | 40.583 | 18.868 | 1.00 19.19 | C |
| ATOM | 3221 | CG | GLU | A | 256 | 69.204 | 39.115 | 18.789 | 1.00 24.54 | C |
| ATOM | 3224 | CD | GLU | A | 256 | 69.073 | 38.352 | 20.132 | 1.00 29.38 | C |
| ATOM | 3225 | OE1 | GLU | A | 256 | 69.036 | 38.984 | 21.222 | 1.00 32.09 | O |
| ATOM | 3226 | OE2 | GLU | A | 256 | 69.007 | 37.102 | 20.087 | 1.00 35.05 | O |
| ATOM | 3227 | C | GLU | A | 256 | 67.115 | 42.339 | 19.449 | 1.00 17.30 | C |
| ATOM | 3228 | O | GLU | A | 256 | 67.045 | 43.135 | 18.511 | 1.00 15.87 | O |
| ATOM | 3230 | N | PRO | A | 257 | 67.036 | 42.727 | 20.719 | 1.00 17.07 | N |
| ATOM | 3231 | CA | PRO | A | 257 | 66.940 | 44.154 | 21.034 | 1.00 17.23 | C |
| ATOM | 3233 | CB | PRO | A | 257 | 66.825 | 44.188 | 22.553 | 1.00 17.39 | C |
| ATOM | 3236 | CG | PRO | A | 257 | 67.226 | 42.869 | 23.011 | 1.00 19.10 | C |
| ATOM | 3239 | CD | PRO | A | 257 | 67.034 | 41.880 | 21.918 | 1.00 17.13 | C |
| ATOM | 3242 | C | PRO | A | 257 | 68.207 | 44.863 | 20.616 | 1.00 16.32 | C |
| ATOM | 3243 | O | PRO | A | 257 | 69.270 | 44.235 | 20.645 | 1.00 17.47 | O |
| ATOM | 3244 | N | VAL | A | 258 | 68.100 | 46.141 | 20.241 | 1.00 16.90 | N |
| ATOM | 3245 | CA | VAL | A | 258 | 69.280 | 46.972 | 19.995 | 1.00 16.53 | C |
| ATOM | 3247 | CB | VAL | A | 258 | 69.045 | 48.001 | 18.863 | 1.00 18.03 | C |
| ATOM | 3249 | CG1 | VAL | A | 258 | 68.765 | 47.289 | 17.552 | 1.00 18.76 | C |
| ATOM | 3253 | CG2 | VAL | A | 258 | 67.914 | 48.963 | 19.214 | 1.00 16.96 | C |
| ATOM | 3257 | C | VAL | A | 258 | 69.638 | 47.673 | 21.278 | 1.00 16.43 | C |
| ATOM | 3258 | O | VAL | A | 258 | 68.784 | 47.880 | 22.124 | 1.00 16.10 | O |
| ATOM | 3260 | N | VAL | A | 259 | 70.901 | 48.025 | 21.418 | 1.00 15.73 | N |
| ATOM | 3261 | CA | VAL | A | 259 | 71.359 | 48.803 | 22.555 | 1.00 15.30 | C |
| ATOM | 3263 | CB | VAL | A | 259 | 72.567 | 48.197 | 23.304 | 1.00 15.53 | C |
| ATOM | 3265 | CG1 | VAL | A | 259 | 73.012 | 49.149 | 24.436 | 1.00 17.26 | C |
| ATOM | 3269 | CG2 | VAL | A | 259 | 72.186 | 46.892 | 23.882 | 1.00 15.19 | C |
| ATOM | 3273 | C | VAL | A | 259 | 71.733 | 50.133 | 21.938 | 1.00 16.07 | C |
| ATOM | 3274 | O | VAL | A | 259 | 72.608 | 50.220 | 21.033 | 1.00 16.36 | O |
| ATOM | 3276 | N | LEU | A | 260 | 71.069 | 51.165 | 22.405 | 1.00 15.52 | N |
| ATOM | 3277 | CA | LEU | A | 260 | 71.282 | 52.489 | 21.804 | 1.00 16.18 | C |
| ATOM | 3279 | CB | LEU | A | 260 | 70.134 | 53.464 | 22.123 | 1.00 15.68 | C |
| ATOM | 3282 | CG | LEU | A | 260 | 68.707 | 53.067 | 21.745 | 1.00 16.02 | C |
| ATOM | 3284 | CD1 | LEU | A | 260 | 67.763 | 54.205 | 22.013 | 1.00 17.23 | C |
| ATOM | 3288 | CD2 | LEU | A | 260 | 68.576 | 52.608 | 20.310 | 1.00 17.38 | C |
| ATOM | 3292 | C | LEU | A | 260 | 72.647 | 53.100 | 22.157 | 1.00 16.51 | C |
| ATOM | 3293 | O | LEU | A | 260 | 73.073 | 53.146 | 23.327 | 1.00 16.97 | O |
| ATOM | 3295 | N | GLY | A | 261 | 73.347 | 53.548 | 21.110 | 1.00 16.88 | N |

| | | | | | | | | | |
|---|---|---|---|---|---|---|---|---|---|
| ATOM | 3296 | CA | GLY | A | 261 | 74.621 | 54.216 | 21.281 | 1.00 16.43 | C |
| ATOM | 3299 | C | GLY | A | 261 | 74.592 | 55.726 | 21.141 | 1.00 16.33 | C |
| ATOM | 3300 | O | GLY | A | 261 | 73.537 | 56.366 | 21.151 | 1.00 16.26 | O |
| ATOM | 3302 | N | PRO | A | 262 | 75.771 | 56.316 | 20.984 | 1.00 16.53 | N |
| ATOM | 3303 | CA | PRO | A | 262 | 75.907 | 57.774 | 20.878 | 1.00 16.45 | C |
| ATOM | 3305 | CB | PRO | A | 262 | 77.392 | 57.979 | 20.560 | 1.00 17.29 | C |
| ATOM | 3308 | CG | PRO | A | 262 | 78.028 | 56.748 | 21.027 | 1.00 17.77 | C |
| ATOM | 3311 | CD | PRO | A | 262 | 77.063 | 55.635 | 20.856 | 1.00 16.43 | C |
| ATOM | 3314 | C | PRO | A | 262 | 75.047 | 58.334 | 19.758 | 1.00 15.50 | C |
| ATOM | 3315 | O | PRO | A | 262 | 75.030 | 57.805 | 18.666 | 1.00 15.12 | O |
| ATOM | 3316 | N | LYS | A | 263 | 74.278 | 59.360 | 20.089 | 1.00 16.11 | N |
| ATOM | 3317 | CA | LYS | A | 263 | 73.386 | 60.045 | 19.156 | 1.00 16.14 | C |
| ATOM | 3319 | CB | LYS | A | 263 | 74.169 | 60.490 | 17.915 | 1.00 15.24 | C |
| ATOM | 3322 | CG | LYS | A | 263 | 73.343 | 61.170 | 16.825 | 1.00 17.02 | C |
| ATOM | 3325 | CD | LYS | A | 263 | 72.659 | 62.431 | 17.252 | 1.00 16.12 | C |
| ATOM | 3328 | CE | LYS | A | 263 | 71.383 | 62.622 | 16.388 | 1.00 16.28 | C |
| ATOM | 3331 | NZ | LYS | A | 263 | 71.606 | 62.866 | 14.928 | 1.00 15.58 | N |
| ATOM | 3335 | C | LYS | A | 263 | 72.115 | 59.249 | 18.791 | 1.00 15.45 | C |
| ATOM | 3336 | O | LYS | A | 263 | 71.169 | 59.815 | 18.246 | 1.00 15.37 | O |
| ATOM | 3338 | N | GLU | A | 264 | 72.060 | 57.952 | 19.108 | 1.00 14.26 | N |
| ATOM | 3339 | CA | GLU | A | 264 | 70.938 | 57.144 | 18.617 | 1.00 14.84 | C |
| ATOM | 3341 | CB | GLU | A | 264 | 71.313 | 55.693 | 18.649 | 1.00 14.77 | C |
| ATOM | 3344 | CG | GLU | A | 264 | 72.450 | 55.412 | 17.638 | 1.00 15.45 | C |
| ATOM | 3347 | CD | GLU | A | 264 | 72.708 | 53.953 | 17.434 | 1.00 16.84 | C |
| ATOM | 3348 | OE1 | GLU | A | 264 | 72.495 | 53.161 | 18.385 | 1.00 16.77 | O |
| ATOM | 3349 | OE2 | GLU | A | 264 | 73.091 | 53.574 | 16.315 | 1.00 15.92 | O |
| ATOM | 3350 | C | GLU | A | 264 | 69.625 | 57.440 | 19.339 | 1.00 14.71 | C |
| ATOM | 3351 | O | GLU | A | 264 | 68.544 | 57.325 | 18.753 | 1.00 14.55 | O |
| ATOM | 3353 | N | GLY | A | 265 | 69.695 | 57.848 | 20.608 | 1.00 15.70 | N |
| ATOM | 3354 | CA | GLY | A | 265 | 68.526 | 58.295 | 21.326 | 1.00 16.03 | C |
| ATOM | 3357 | C | GLY | A | 265 | 67.888 | 59.496 | 20.651 | 1.00 15.43 | C |
| ATOM | 3358 | O | GLY | A | 265 | 66.722 | 59.455 | 20.282 | 1.00 15.75 | O |
| ATOM | 3360 | N | LEU | A | 266 | 68.652 | 60.564 | 20.468 | 1.00 15.10 | N |
| ATOM | 3361 | CA | LEU | A | 266 | 68.134 | 61.742 | 19.738 | 1.00 14.83 | C |
| ATOM | 3363 | CB | LEU | A | 266 | 69.141 | 62.860 | 19.737 | 1.00 15.64 | C |
| ATOM | 3366 | CG | LEU | A | 266 | 69.313 | 63.497 | 21.116 | 1.00 17.00 | C |
| ATOM | 3368 | CD1 | LEU | A | 266 | 70.409 | 64.529 | 20.980 | 1.00 19.33 | C |
| ATOM | 3372 | CD2 | LEU | A | 266 | 68.009 | 64.096 | 21.636 | 1.00 19.17 | C |
| ATOM | 3376 | C | LEU | A | 266 | 67.788 | 61.435 | 18.292 | 1.00 14.16 | C |
| ATOM | 3377 | O | LEU | A | 266 | 66.795 | 61.943 | 17.747 | 1.00 15.21 | O |
| ATOM | 3379 | N | GLY | A | 267 | 68.601 | 60.596 | 17.660 | 1.00 13.92 | N |
| ATOM | 3380 | CA | GLY | A | 267 | 68.369 | 60.156 | 16.286 | 1.00 14.31 | C |
| ATOM | 3383 | C | GLY | A | 267 | 67.003 | 59.515 | 16.099 | 1.00 14.72 | C |
| ATOM | 3384 | O | GLY | A | 267 | 66.303 | 59.737 | 15.093 | 1.00 15.22 | O |
| ATOM | 3386 | N | LEU | A | 268 | 66.601 | 58.732 | 17.081 | 1.00 12.97 | N |
| ATOM | 3387 | CA | LEU | A | 268 | 65.276 | 58.113 | 17.055 | 1.00 13.30 | C |
| ATOM | 3389 | CB | LEU | A | 268 | 65.287 | 56.828 | 17.863 | 1.00 12.30 | C |
| ATOM | 3392 | CG | LEU | A | 268 | 66.102 | 55.664 | 17.295 | 1.00 14.13 | C |
| ATOM | 3394 | CD1 | LEU | A | 268 | 66.241 | 54.548 | 18.338 | 1.00 15.31 | C |
| ATOM | 3398 | CD2 | LEU | A | 268 | 65.443 | 55.144 | 16.029 | 1.00 13.30 | C |
| ATOM | 3402 | C | LEU | A | 268 | 64.138 | 58.942 | 17.571 | 1.00 13.59 | C |
| ATOM | 3403 | O | LEU | A | 268 | 63.035 | 58.842 | 17.070 | 1.00 15.24 | O |
| ATOM | 3405 | N | VAL | A | 269 | 64.364 | 59.713 | 18.618 | 1.00 13.18 | N |
| ATOM | 3406 | CA | VAL | A | 269 | 63.262 | 60.406 | 19.288 | 1.00 13.72 | C |
| ATOM | 3408 | CB | VAL | A | 269 | 63.358 | 60.403 | 20.833 | 1.00 13.41 | C |
| ATOM | 3410 | CG1 | VAL | A | 269 | 63.600 | 59.000 | 21.356 | 1.00 15.00 | C |
| ATOM | 3414 | CG2 | VAL | A | 269 | 64.374 | 61.369 | 21.310 | 1.00 16.66 | C |

| | | | | | | | | | | |
|---|---|---|---|---|---|---|---|---|---|---|
| ATOM | 3418 | C | VAL | A | 269 | 62.989 | 61.846 | 18.803 | 1.00 12.55 | C |
| ATOM | 3419 | O | VAL | A | 269 | 61.872 | 62.347 | 18.973 | 1.00 14.55 | O |
| ATOM | 3421 | N | ASN | A | 270 | 63.989 | 62.499 | 18.206 | 1.00 13.65 | N |
| ATOM | 3422 | CA | ASN | A | 270 | 63.827 | 63.872 | 17.698 | 1.00 13.05 | C |
| ATOM | 3424 | CB | ASN | A | 270 | 65.153 | 64.633 | 17.578 | 1.00 13.55 | C |
| ATOM | 3427 | CG | ASN | A | 270 | 65.563 | 65.364 | 18.805 | 1.00 17.29 | C |
| ATOM | 3428 | OD1 | ASN | A | 270 | 64.862 | 65.412 | 19.841 | 1.00 22.44 | O |
| ATOM | 3429 | ND2 | ASN | A | 270 | 66.779 | 65.924 | 18.729 | 1.00 19.20 | N |
| ATOM | 3432 | C | ASN | A | 270 | 63.288 | 63.751 | 16.282 | 1.00 12.95 | C |
| ATOM | 3433 | O | ASN | A | 270 | 63.859 | 63.049 | 15.424 | 1.00 12.52 | O |
| ATOM | 3435 | N | GLY | A | 271 | 62.196 | 64.426 | 15.980 | 1.00 12.79 | N |
| ATOM | 3436 | CA | GLY | A | 271 | 61.651 | 64.301 | 14.643 | 1.00 13.23 | C |
| ATOM | 3439 | C | GLY | A | 271 | 60.162 | 64.384 | 14.535 | 1.00 12.83 | C |
| ATOM | 3440 | O | GLY | A | 271 | 59.490 | 64.523 | 15.522 | 1.00 12.74 | O |
| ATOM | 3442 | N | THR | A | 272 | 59.670 | 64.317 | 13.314 | 1.00 12.40 | N |
| ATOM | 3443 | CA | THR | A | 272 | 58.240 | 64.622 | 13.026 | 1.00 12.99 | C |
| ATOM | 3445 | CB | THR | A | 272 | 58.114 | 65.772 | 11.999 | 1.00 13.29 | C |
| ATOM | 3447 | OG1 | THR | A | 272 | 58.565 | 65.341 | 10.704 | 1.00 14.35 | O |
| ATOM | 3449 | CG2 | THR | A | 272 | 58.892 | 66.956 | 12.451 | 1.00 13.78 | C |
| ATOM | 3453 | C | THR | A | 272 | 57.424 | 63.409 | 12.501 | 1.00 12.01 | C |
| ATOM | 3454 | O | THR | A | 272 | 56.313 | 63.575 | 12.002 | 1.00 12.03 | O |
| ATOM | 3456 | N | ALA | A | 273 | 57.992 | 62.206 | 12.602 | 1.00 13.85 | N |
| ATOM | 3457 | CA | ALA | A | 273 | 57.416 | 61.051 | 11.906 | 1.00 12.33 | C |
| ATOM | 3459 | CB | ALA | A | 273 | 58.352 | 59.816 | 11.991 | 1.00 13.80 | C |
| ATOM | 3463 | C | ALA | A | 273 | 55.996 | 60.677 | 12.372 | 1.00 12.36 | C |
| ATOM | 3464 | O | ALA | A | 273 | 55.196 | 60.100 | 11.602 | 1.00 10.94 | O |
| ATOM | 3466 | N | VAL | A | 274 | 55.674 | 60.968 | 13.634 | 1.00 12.24 | N |
| ATOM | 3467 | CA | VAL | A | 274 | 54.385 | 60.571 | 14.151 | 1.00 12.90 | C |
| ATOM | 3469 | CB | VAL | A | 274 | 54.374 | 60.495 | 15.689 | 1.00 12.22 | C |
| ATOM | 3471 | CG1 | VAL | A | 274 | 52.989 | 60.063 | 16.191 | 1.00 13.40 | C |
| ATOM | 3475 | CG2 | VAL | A | 274 | 55.427 | 59.481 | 16.172 | 1.00 12.41 | C |
| ATOM | 3479 | C | VAL | A | 274 | 53.288 | 61.485 | 13.628 | 1.00 12.22 | C |
| ATOM | 3480 | O | VAL | A | 274 | 52.273 | 61.052 | 13.063 | 1.00 13.51 | O |
| ATOM | 3482 | N | SER | A | 275 | 53.537 | 62.775 | 13.781 | 1.00 12.85 | N |
| ATOM | 3483 | CA | SER | A | 275 | 52.653 | 63.766 | 13.192 | 1.00 13.28 | C |
| ATOM | 3485 | CB | SER | A | 275 | 53.272 | 65.132 | 13.489 | 1.00 14.95 | C |
| ATOM | 3488 | OG | SER | A | 275 | 53.151 | 65.334 | 14.861 | 1.00 21.79 | O |
| ATOM | 3490 | C | SER | A | 275 | 52.543 | 63.555 | 11.689 | 1.00 12.65 | C |
| ATOM | 3491 | O | SER | A | 275 | 51.439 | 63.603 | 11.096 | 1.00 12.73 | O |
| ATOM | 3493 | N | ALA | A | 276 | 53.680 | 63.304 | 11.035 | 1.00 12.93 | N |
| ATOM | 3494 | CA | ALA | A | 276 | 53.649 | 63.227 | 9.574 | 1.00 12.46 | C |
| ATOM | 3496 | CB | ALA | A | 276 | 55.077 | 63.184 | 8.984 | 1.00 13.42 | C |
| ATOM | 3500 | C | ALA | A | 276 | 52.872 | 62.001 | 9.124 | 1.00 13.17 | C |
| ATOM | 3501 | O | ALA | A | 276 | 52.164 | 62.014 | 8.103 | 1.00 12.73 | O |
| ATOM | 3503 | N | SER | A | 277 | 53.015 | 60.931 | 9.891 | 1.00 12.68 | N |
| ATOM | 3504 | CA | SER | A | 277 | 52.258 | 59.700 | 9.627 | 1.00 12.42 | C |
| ATOM | 3506 | CB | SER | A | 277 | 52.610 | 58.639 | 10.641 | 1.00 14.41 | C |
| ATOM | 3509 | OG | SER | A | 277 | 51.835 | 57.485 | 10.404 | 1.00 12.00 | O |
| ATOM | 3511 | C | SER | A | 277 | 50.748 | 59.958 | 9.713 | 1.00 13.34 | C |
| ATOM | 3512 | O | SER | A | 277 | 49.970 | 59.673 | 8.785 | 1.00 11.47 | O |
| ATOM | 3514 | N | MSE | A | 278 | 50.328 | 60.517 | 10.847 | 1.00 12.69 | N |
| ATOM | 3515 | CA | MSE | A | 278 | 48.867 | 60.685 | 11.045 | 1.00 14.56 | C |
| ATOM | 3517 | CB | MSE | A | 278 | 48.505 | 61.157 | 12.443 | 1.00 14.62 | C |
| ATOM | 3520 | CG | MSE | A | 278 | 47.073 | 60.925 | 12.659 | 1.00 16.09 | C |
| ATOM | 3523 | SE | MSE | A | 278 | 46.643 | 61.058 | 14.607 | 1.00 23.84 | SE |
| ATOM | 3524 | CE | MSE | A | 278 | 44.851 | 60.134 | 14.559 | 1.00 15.38 | C |
| ATOM | 3528 | C | MSE | A | 278 | 48.307 | 61.680 | 10.013 | 1.00 13.29 | C |

| ATOM | 3529 | O | MSE A 278 | 47.191 | 61.503 | 9.467 | 1.00 | 13.15 | O |
|------|------|-----|-----------|--------|--------|-------|------|-------|---|
| ATOM | 3531 | N | ALA A 279 | 49.107 | 62.696 | 9.698 | 1.00 | 13.71 | N |
| ATOM | 3532 | CA | ALA A 279 | 48.736 | 63.742 | 8.723 | 1.00 | 12.83 | C |
| ATOM | 3534 | CB | ALA A 279 | 49.759 | 64.833 | 8.720 | 1.00 | 12.73 | C |
| ATOM | 3538 | C | ALA A 279 | 48.590 | 63.175 | 7.297 | 1.00 | 11.24 | C |
| ATOM | 3539 | O | ALA A 279 | 47.691 | 63.563 | 6.508 | 1.00 | 12.05 | O |
| ATOM | 3541 | N | THR A 280 | 49.513 | 62.265 | 6.974 | 1.00 | 12.43 | N |
| ATOM | 3542 | CA | THR A 280 | 49.496 | 61.626 | 5.684 | 1.00 | 12.47 | C |
| ATOM | 3544 | CB | THR A 280 | 50.719 | 60.709 | 5.467 | 1.00 | 13.00 | C |
| ATOM | 3546 | OG1 | THR A 280 | 51.907 | 61.518 | 5.437 | 1.00 | 12.04 | O |
| ATOM | 3548 | CG2 | THR A 280 | 50.592 | 60.005 | 4.142 | 1.00 | 12.21 | C |
| ATOM | 3552 | C | THR A 280 | 48.205 | 60.815 | 5.511 | 1.00 | 11.73 | C |
| ATOM | 3553 | O | THR A 280 | 47.550 | 60.878 | 4.466 | 1.00 | 12.95 | O |
| ATOM | 3555 | N | LEU A 281 | 47.874 | 60.029 | 6.525 | 1.00 | 11.65 | N |
| ATOM | 3556 | CA | LEU A 281 | 46.651 | 59.235 | 6.516 | 1.00 | 12.65 | C |
| ATOM | 3558 | CB | LEU A 281 | 46.591 | 58.363 | 7.764 | 1.00 | 12.97 | C |
| ATOM | 3561 | CG | LEU A 281 | 47.670 | 57.240 | 7.828 | 1.00 | 14.52 | C |
| ATOM | 3563 | CD1 | LEU A 281 | 47.863 | 56.730 | 9.202 | 1.00 | 17.88 | C |
| ATOM | 3567 | CD2 | LEU A 281 | 47.390 | 56.118 | 6.855 | 1.00 | 19.98 | C |
| ATOM | 3571 | C | LEU A 281 | 45.431 | 60.131 | 6.408 | 1.00 | 13.21 | C |
| ATOM | 3572 | O | LEU A 281 | 44.484 | 59.864 | 5.668 | 1.00 | 11.94 | O |
| ATOM | 3574 | N | ALA A 282 | 45.394 | 61.205 | 7.183 | 1.00 | 11.80 | N |
| ATOM | 3575 | CA | ALA A 282 | 44.258 | 62.163 | 7.177 | 1.00 | 12.89 | C |
| ATOM | 3577 | CB | ALA A 282 | 44.444 | 63.235 | 8.249 | 1.00 | 11.96 | C |
| ATOM | 3581 | C | ALA A 282 | 44.161 | 62.861 | 5.820 | 1.00 | 13.23 | C |
| ATOM | 3582 | O | ALA A 282 | 43.053 | 63.052 | 5.307 | 1.00 | 12.11 | O |
| ATOM | 3584 | N | LEU A 283 | 45.304 | 63.242 | 5.232 | 1.00 | 11.18 | N |
| ATOM | 3585 | CA | LEU A 283 | 45.233 | 63.898 | 3.925 | 1.00 | 13.02 | C |
| ATOM | 3587 | CB | LEU A 283 | 46.556 | 64.491 | 3.511 | 1.00 | 11.93 | C |
| ATOM | 3590 | CG | LEU A 283 | 46.534 | 65.188 | 2.135 | 1.00 | 11.72 | C |
| ATOM | 3592 | CD1 | LEU A 283 | 45.602 | 66.386 | 2.142 | 1.00 | 14.54 | C |
| ATOM | 3596 | CD2 | LEU A 283 | 47.943 | 65.606 | 1.782 | 1.00 | 14.15 | C |
| ATOM | 3600 | C | LEU A 283 | 44.709 | 62.932 | 2.854 | 1.00 | 12.20 | C |
| ATOM | 3601 | O | LEU A 283 | 43.881 | 63.316 | 2.005 | 1.00 | 13.00 | O |
| ATOM | 3603 | N | HIS A 284 | 45.221 | 61.706 | 2.837 | 1.00 | 11.56 | N |
| ATOM | 3604 | CA | HIS A 284 | 44.709 | 60.641 | 1.951 | 1.00 | 12.69 | C |
| ATOM | 3606 | CB | HIS A 284 | 45.406 | 59.327 | 2.321 | 1.00 | 11.79 | C |
| ATOM | 3609 | CG | HIS A 284 | 44.847 | 58.103 | 1.655 | 1.00 | 13.40 | C |
| ATOM | 3610 | ND1 | HIS A 284 | 43.656 | 57.527 | 2.047 | 1.00 | 15.12 | N |
| ATOM | 3612 | CE1 | HIS A 284 | 43.436 | 56.450 | 1.316 | 1.00 | 15.77 | C |
| ATOM | 3614 | NE2 | HIS A 284 | 44.449 | 56.288 | 0.482 | 1.00 | 14.88 | N |
| ATOM | 3616 | CD2 | HIS A 284 | 45.352 | 57.304 | 0.690 | 1.00 | 15.09 | C |
| ATOM | 3618 | C | HIS A 284 | 43.198 | 60.551 | 2.048 | 1.00 | 11.80 | C |
| ATOM | 3619 | O | HIS A 284 | 42.504 | 60.661 | 1.015 | 1.00 | 12.00 | O |
| ATOM | 3621 | N | ASP A 285 | 42.672 | 60.439 | 3.271 | 1.00 | 12.48 | N |
| ATOM | 3622 | CA | ASP A 285 | 41.221 | 60.316 | 3.461 | 1.00 | 12.22 | C |
| ATOM | 3624 | CB | ASP A 285 | 40.907 | 59.950 | 4.885 | 1.00 | 11.99 | C |
| ATOM | 3627 | CG | ASP A 285 | 41.440 | 58.556 | 5.269 | 1.00 | 15.72 | C |
| ATOM | 3628 | OD1 | ASP A 285 | 41.827 | 57.787 | 4.376 | 1.00 | 15.17 | O |
| ATOM | 3629 | OD2 | ASP A 285 | 41.402 | 58.223 | 6.456 | 1.00 | 15.94 | O |
| ATOM | 3630 | C | ASP A 285 | 40.482 | 61.589 | 3.030 | 1.00 | 12.72 | C |
| ATOM | 3631 | O | ASP A 285 | 39.402 | 61.508 | 2.427 | 1.00 | 14.52 | O |
| ATOM | 3633 | N | ALA A 286 | 41.035 | 62.756 | 3.338 | 1.00 | 12.56 | N |
| ATOM | 3634 | CA | ALA A 286 | 40.436 | 64.007 | 2.862 | 1.00 | 12.70 | C |
| ATOM | 3636 | CB | ALA A 286 | 41.177 | 65.222 | 3.427 | 1.00 | 13.21 | C |
| ATOM | 3640 | C | ALA A 286 | 40.317 | 64.116 | 1.333 | 1.00 | 13.04 | C |
| ATOM | 3641 | O | ALA A 286 | 39.329 | 64.607 | 0.837 | 1.00 | 13.27 | O |

| ATOM | 3643 | N | HIS A 287 | 41.364 | 63.737 | 0.617 | 1.00 | 11.62 | N |
| --- | --- | --- | --- | --- | --- | --- | --- | --- | --- |
| ATOM | 3644 | CA | HIS A 287 | 41.319 | 63.728 | -0.863 | 1.00 | 12.23 | C |
| ATOM | 3646 | CB | HIS A 287 | 42.567 | 63.090 | -1.489 | 1.00 | 12.65 | C |
| ATOM | 3649 | CG | HIS A 287 | 43.801 | 63.958 | -1.475 | 1.00 | 12.99 | C |
| ATOM | 3650 | ND1 | HIS A 287 | 43.815 | 65.255 | -1.939 | 1.00 | 13.71 | N |
| ATOM | 3652 | CE1 | HIS A 287 | 45.053 | 65.719 | -1.884 | 1.00 | 13.28 | C |
| ATOM | 3654 | NE2 | HIS A 287 | 45.850 | 64.758 | -1.448 | 1.00 | 13.44 | N |
| ATOM | 3656 | CD2 | HIS A 287 | 45.085 | 63.653 | -1.156 | 1.00 | 11.58 | C |
| ATOM | 3658 | C | HIS A 287 | 40.088 | 62.917 | -1.317 | 1.00 | 12.41 | C |
| ATOM | 3659 | O | HIS A 287 | 39.374 | 63.303 | -2.231 | 1.00 | 14.08 | O |
| ATOM | 3661 | N | MSE A 288 | 39.845 | 61.774 | -0.692 | 1.00 | 12.66 | N |
| ATOM | 3662 | CA | MSE A 288 | 38.722 | 60.918 | -1.139 | 1.00 | 13.61 | C |
| ATOM | 3664 | CB | MSE A 288 | 38.766 | 59.590 | -0.411 | 1.00 | 14.70 | C |
| ATOM | 3667 | CG | MSE A 288 | 40.099 | 58.834 | -0.557 | 1.00 | 14.95 | C |
| ATOM | 3670 | SE | MSE A 288 | 40.702 | 58.646 | -2.407 | 1.00 | 24.12 | SE |
| ATOM | 3671 | CE | MSE A 288 | 42.788 | 58.647 | -1.974 | 1.00 | 24.66 | C |
| ATOM | 3675 | C | MSE A 288 | 37.382 | 61.595 | -0.854 | 1.00 | 12.58 | C |
| ATOM | 3676 | O | MSE A 288 | 36.453 | 61.588 | -1.644 | 1.00 | 12.36 | O |
| ATOM | 3678 | N | LEU A 289 | 37.314 | 62.267 | 0.274 | 1.00 | 11.54 | N |
| ATOM | 3679 | CA | LEU A 289 | 36.068 | 62.940 | 0.666 | 1.00 | 12.26 | C |
| ATOM | 3681 | CB | LEU A 289 | 36.102 | 63.314 | 2.136 | 1.00 | 12.68 | C |
| ATOM | 3684 | CG | LEU A 289 | 36.099 | 62.144 | 3.134 | 1.00 | 13.20 | C |
| ATOM | 3686 | CD1 | LEU A 289 | 36.444 | 62.565 | 4.545 | 1.00 | 15.95 | C |
| ATOM | 3690 | CD2 | LEU A 289 | 34.801 | 61.417 | 3.134 | 1.00 | 14.70 | C |
| ATOM | 3694 | C | LEU A 289 | 35.805 | 64.145 | -0.247 | 1.00 | 12.29 | C |
| ATOM | 3695 | O | LEU A 289 | 34.686 | 64.452 | -0.591 | 1.00 | 13.33 | O |
| ATOM | 3697 | N | SER A 290 | 36.878 | 64.839 | -0.619 | 1.00 | 13.28 | N |
| ATOM | 3698 | CA | SER A 290 | 36.790 | 65.931 | -1.585 | 1.00 | 13.50 | C |
| ATOM | 3700 | CB | SER A 290 | 38.178 | 66.496 | -1.845 | 1.00 | 13.87 | C |
| ATOM | 3703 | OG | SER A 290 | 38.138 | 67.477 | -2.862 | 1.00 | 15.89 | O |
| ATOM | 3705 | C | SER A 290 | 36.159 | 65.400 | -2.920 | 1.00 | 13.25 | C |
| ATOM | 3706 | O | SER A 290 | 35.214 | 65.963 | -3.475 | 1.00 | 14.14 | O |
| ATOM | 3708 | N | LEU A 291 | 36.673 | 64.292 | -3.417 | 1.00 | 12.30 | N |
| ATOM | 3709 | CA | LEU A 291 | 36.126 | 63.707 | -4.680 | 1.00 | 12.74 | C |
| ATOM | 3711 | CB | LEU A 291 | 37.005 | 62.565 | -5.237 | 1.00 | 13.61 | C |
| ATOM | 3714 | CG | LEU A 291 | 38.413 | 62.988 | -5.623 | 1.00 | 14.74 | C |
| ATOM | 3716 | CD1 | LEU A 291 | 39.146 | 61.818 | -6.207 | 1.00 | 15.75 | C |
| ATOM | 3720 | CD2 | LEU A 291 | 38.381 | 64.170 | -6.599 | 1.00 | 14.94 | C |
| ATOM | 3724 | C | LEU A 291 | 34.674 | 63.245 | -4.502 | 1.00 | 11.70 | C |
| ATOM | 3725 | O | LEU A 291 | 33.801 | 63.471 | -5.392 | 1.00 | 13.10 | O |
| ATOM | 3727 | N | LEU A 292 | 34.390 | 62.640 | -3.343 | 1.00 | 12.09 | N |
| ATOM | 3728 | CA | LEU A 292 | 33.024 | 62.205 | -3.021 | 1.00 | 12.69 | C |
| ATOM | 3730 | CB | LEU A 292 | 32.960 | 61.402 | -1.711 | 1.00 | 13.79 | C |
| ATOM | 3733 | CG | LEU A 292 | 31.596 | 60.853 | -1.305 | 1.00 | 11.81 | C |
| ATOM | 3735 | CD1 | LEU A 292 | 30.911 | 59.936 | -2.384 | 1.00 | 15.07 | C |
| ATOM | 3739 | CD2 | LEU A 292 | 31.685 | 60.112 | 0.041 | 1.00 | 11.62 | C |
| ATOM | 3743 | C | LEU A 292 | 32.057 | 63.397 | -2.993 | 1.00 | 13.54 | C |
| ATOM | 3744 | O | LEU A 292 | 30.904 | 63.299 | -3.463 | 1.00 | 14.34 | O |
| ATOM | 3746 | N | SER A 293 | 32.504 | 64.522 | -2.417 | 1.00 | 13.44 | N |
| ATOM | 3747 | CA | SER A 293 | 31.713 | 65.743 | -2.389 | 1.00 | 13.68 | C |
| ATOM | 3749 | CB | SER A 293 | 32.470 | 66.930 | -1.706 | 1.00 | 13.99 | C |
| ATOM | 3752 | OG | SER A 293 | 31.650 | 68.069 | -1.716 | 1.00 | 12.77 | O |
| ATOM | 3754 | C | SER A 293 | 31.273 | 66.143 | -3.790 | 1.00 | 13.25 | C |
| ATOM | 3755 | O | SER A 293 | 30.144 | 66.602 | -4.004 | 1.00 | 14.03 | O |
| ATOM | 3757 | N | GLN A 294 | 32.187 | 66.049 | -4.737 | 1.00 | 12.60 | N |
| ATOM | 3758 | CA | GLN A 294 | 31.929 | 66.440 | -6.132 | 1.00 | 12.76 | C |
| ATOM | 3760 | CB | GLN A 294 | 33.219 | 66.556 | -6.926 | 1.00 | 13.31 | C |

| ATOM | 3763 | CG | GLN | A | 294 | 34.084 | 67.700 | -6.419 | 1.00 | 13.74 | C |
|---|---|---|---|---|---|---|---|---|---|---|---|
| ATOM | 3766 | CD | GLN | A | 294 | 35.428 | 67.786 | -7.086 | 1.00 | 14.66 | C |
| ATOM | 3767 | OE1 | GLN | A | 294 | 35.532 | 67.688 | -8.322 | 1.00 | 13.68 | O |
| ATOM | 3768 | NE2 | GLN | A | 294 | 36.484 | 67.919 | -6.269 | 1.00 | 16.04 | N |
| ATOM | 3771 | C | GLN | A | 294 | 30.974 | 65.456 | -6.794 | 1.00 | 13.21 | C |
| ATOM | 3772 | O | GLN | A | 294 | 30.097 | 65.860 | -7.534 | 1.00 | 12.79 | O |
| ATOM | 3774 | N | SER | A | 295 | 31.152 | 64.173 | -6.500 | 1.00 | 12.96 | N |
| ATOM | 3775 | CA | SER | A | 295 | 30.231 | 63.152 | -7.033 | 1.00 | 13.43 | C |
| ATOM | 3777 | CB | SER | A | 295 | 30.723 | 61.756 | -6.679 | 1.00 | 14.04 | C |
| ATOM | 3780 | OG | SER | A | 295 | 31.945 | 61.477 | -7.317 | 1.00 | 14.90 | O |
| ATOM | 3782 | C | SER | A | 295 | 28.811 | 63.367 | -6.480 | 1.00 | 13.54 | C |
| ATOM | 3783 | O | SER | A | 295 | 27.779 | 63.295 | -7.213 | 1.00 | 13.78 | O |
| ATOM | 3785 | N | LEU | A | 296 | 28.739 | 63.711 | -5.203 | 1.00 | 11.23 | N |
| ATOM | 3786 | CA | LEU | A | 296 | 27.464 | 64.014 | -4.593 | 1.00 | 13.06 | C |
| ATOM | 3788 | CB | LEU | A | 296 | 27.606 | 64.068 | -3.095 | 1.00 | 14.06 | C |
| ATOM | 3791 | CG | LEU | A | 296 | 27.846 | 62.732 | -2.416 | 1.00 | 12.25 | C |
| ATOM | 3793 | CD1 | LEU | A | 296 | 28.255 | 63.011 | -1.008 | 1.00 | 14.91 | C |
| ATOM | 3797 | CD2 | LEU | A | 296 | 26.590 | 61.850 | -2.420 | 1.00 | 16.03 | C |
| ATOM | 3801 | C | LEU | A | 296 | 26.823 | 65.267 | -5.175 | 1.00 | 12.87 | C |
| ATOM | 3802 | O | LEU | A | 296 | 25.580 | 65.323 | -5.350 | 1.00 | 13.12 | O |
| ATOM | 3804 | N | THR | A | 297 | 27.650 | 66.254 | -5.518 | 1.00 | 13.42 | N |
| ATOM | 3805 | CA | THR | A | 297 | 27.143 | 67.447 | -6.168 | 1.00 | 13.43 | C |
| ATOM | 3807 | CB | THR | A | 297 | 28.240 | 68.453 | -6.421 | 1.00 | 14.17 | C |
| ATOM | 3809 | OG1 | THR | A | 297 | 28.773 | 68.860 | -5.136 | 1.00 | 12.33 | O |
| ATOM | 3811 | CG2 | THR | A | 297 | 27.674 | 69.680 | -7.128 | 1.00 | 15.16 | C |
| ATOM | 3815 | C | THR | A | 297 | 26.459 | 67.086 | -7.472 | 1.00 | 14.07 | C |
| ATOM | 3816 | O | THR | A | 297 | 25.288 | 67.439 | -7.690 | 1.00 | 14.51 | O |
| ATOM | 3818 | N | ALA | A | 298 | 27.165 | 66.353 | -8.333 | 1.00 | 14.38 | N |
| ATOM | 3819 | CA | ALA | A | 298 | 26.602 | 65.879 | -9.610 | 1.00 | 14.18 | C |
| ATOM | 3821 | CB | ALA | A | 298 | 27.576 | 64.994 | -10.334 | 1.00 | 14.79 | C |
| ATOM | 3825 | C | ALA | A | 298 | 25.286 | 65.139 | -9.410 | 1.00 | 13.59 | C |
| ATOM | 3826 | O | ALA | A | 298 | 24.302 | 65.401 | -10.100 | 1.00 | 14.19 | O |
| ATOM | 3828 | N | MSE | A | 299 | 25.254 | 64.239 | -8.439 | 1.00 | 13.20 | N |
| ATOM | 3829 | CA | MSE | A | 299 | 24.086 | 63.372 | -8.261 | 1.00 | 16.14 | C |
| ATOM | 3831 | CB | MSE | A | 299 | 24.434 | 62.181 | -7.379 | 1.00 | 16.23 | C |
| ATOM | 3834 | CG | MSE | A | 299 | 25.305 | 61.217 | -8.158 | 1.00 | 19.11 | C |
| ATOM | 3837 | SE | MSE | A | 299 | 25.754 | 59.608 | -7.144 | 1.00 | 34.56 | SE |
| ATOM | 3838 | CE | MSE | A | 299 | 24.241 | 58.513 | -7.848 | 1.00 | 33.25 | C |
| ATOM | 3842 | C | MSE | A | 299 | 22.920 | 64.139 | -7.688 | 1.00 | 14.02 | C |
| ATOM | 3843 | O | MSE | A | 299 | 21.772 | 63.848 | -7.994 | 1.00 | 12.48 | O |
| ATOM | 3845 | N | THR | A | 300 | 23.206 | 65.171 | -6.904 | 1.00 | 13.13 | N |
| ATOM | 3846 | CA | THR | A | 300 | 22.149 | 66.055 | -6.394 | 1.00 | 13.08 | C |
| ATOM | 3848 | CB | THR | A | 300 | 22.685 | 66.908 | -5.252 | 1.00 | 12.30 | C |
| ATOM | 3850 | OG1 | THR | A | 300 | 23.172 | 66.019 | -4.220 | 1.00 | 14.56 | O |
| ATOM | 3852 | CG2 | THR | A | 300 | 21.654 | 67.836 | -4.681 | 1.00 | 12.00 | C |
| ATOM | 3856 | C | THR | A | 300 | 21.611 | 66.914 | -7.532 | 1.00 | 13.30 | C |
| ATOM | 3857 | O | THR | A | 300 | 20.409 | 67.108 | -7.614 | 1.00 | 12.60 | O |
| ATOM | 3859 | N | VAL | A | 301 | 22.482 | 67.421 | -8.416 | 1.00 | 12.84 | N |
| ATOM | 3860 | CA | VAL | A | 301 | 21.977 | 68.091 | -9.620 | 1.00 | 12.26 | C |
| ATOM | 3862 | CB | VAL | A | 301 | 23.091 | 68.505 | -10.600 | 1.00 | 12.40 | C |
| ATOM | 3864 | CG1 | VAL | A | 301 | 22.471 | 68.978 | -11.893 | 1.00 | 13.85 | C |
| ATOM | 3868 | CG2 | VAL | A | 301 | 24.003 | 69.602 | -10.015 | 1.00 | 12.98 | C |
| ATOM | 3872 | C | VAL | A | 301 | 20.969 | 67.152 | -10.350 | 1.00 | 11.69 | C |
| ATOM | 3873 | O | VAL | A | 301 | 19.856 | 67.581 | -10.781 | 1.00 | 13.11 | O |
| ATOM | 3875 | N | GLU | A | 302 | 21.337 | 65.879 | -10.506 | 1.00 | 12.55 | N |
| ATOM | 3876 | CA | GLU | A | 302 | 20.417 | 64.937 | -11.177 | 1.00 | 12.56 | C |
| ATOM | 3878 | CB | GLU | A | 302 | 21.079 | 63.587 | -11.360 | 1.00 | 12.91 | C |

| ATOM | 3881 | CG | GLU | A | 302 | 22.243 | 63.646 | -12.283 | 1.00 | 12.54 | C |
| --- | --- | --- | --- | --- | --- | --- | --- | --- | --- | --- | --- |
| ATOM | 3884 | CD | GLU | A | 302 | 22.782 | 62.271 | -12.632 | 1.00 | 13.99 | C |
| ATOM | 3885 | OE1 | GLU | A | 302 | 23.438 | 61.632 | -11.752 | 1.00 | 16.18 | O |
| ATOM | 3886 | OE2 | GLU | A | 302 | 22.528 | 61.790 | -13.798 | 1.00 | 15.32 | O |
| ATOM | 3887 | C | GLU | A | 302 | 19.092 | 64.760 | -10.412 | 1.00 | 13.64 | C |
| ATOM | 3888 | O | GLU | A | 302 | 17.985 | 64.892 | -10.970 | 1.00 | 12.62 | O |
| ATOM | 3890 | N | ALA | A | 303 | 19.184 | 64.510 | -9.116 | 1.00 | 13.65 | N |
| ATOM | 3891 | CA | ALA | A | 303 | 17.978 | 64.322 | -8.304 | 1.00 | 14.35 | C |
| ATOM | 3893 | CB | ALA | A | 303 | 18.381 | 63.954 | -6.879 | 1.00 | 14.92 | C |
| ATOM | 3897 | C | ALA | A | 303 | 17.094 | 65.586 | -8.301 | 1.00 | 13.21 | C |
| ATOM | 3898 | O | ALA | A | 303 | 15.867 | 65.496 | -8.223 | 1.00 | 13.44 | O |
| ATOM | 3900 | N | MSE | A | 304 | 17.718 | 66.762 | -8.378 | 1.00 | 13.35 | N |
| ATOM | 3901 | CA | MSE | A | 304 | 17.004 | 68.050 | -8.373 | 1.00 | 14.00 | C |
| ATOM | 3903 | CB | MSE | A | 304 | 17.909 | 69.114 | -7.779 | 1.00 | 14.30 | C |
| ATOM | 3906 | CG | MSE | A | 304 | 18.168 | 68.875 | -6.321 | 1.00 | 14.17 | C |
| ATOM | 3909 | SE | MSE | A | 304 | 16.596 | 69.426 | -5.192 | 1.00 | 26.74 | SE |
| ATOM | 3910 | CE | MSE | A | 304 | 16.571 | 71.408 | -5.586 | 1.00 | 22.33 | C |
| ATOM | 3914 | C | MSE | A | 304 | 16.540 | 68.515 | -9.730 | 1.00 | 14.85 | C |
| ATOM | 3915 | O | MSE | A | 304 | 15.885 | 69.560 | -9.833 | 1.00 | 14.40 | O |
| ATOM | 3917 | N | VAL | A | 305 | 16.780 | 67.698 | -10.751 | 1.00 | 15.33 | N |
| ATOM | 3918 | CA | VAL | A | 305 | 16.572 | 68.080 | -12.150 | 1.00 | 16.37 | C |
| ATOM | 3920 | CB | VAL | A | 305 | 15.123 | 67.738 | -12.602 | 1.00 | 17.37 | C |
| ATOM | 3922 | CG1 | VAL | A | 305 | 14.958 | 66.198 | -12.580 | 1.00 | 18.55 | C |
| ATOM | 3926 | CG2 | VAL | A | 305 | 14.108 | 68.336 | -11.766 | 1.00 | 18.48 | C |
| ATOM | 3930 | C | VAL | A | 305 | 17.064 | 69.545 | -12.361 | 1.00 | 15.83 | C |
| ATOM | 3931 | O | VAL | A | 305 | 16.411 | 70.427 | -12.975 | 1.00 | 17.26 | O |
| ATOM | 3933 | N | GLY | A | 306 | 18.265 | 69.760 | -11.845 | 1.00 | 15.90 | N |
| ATOM | 3934 | CA | GLY | A | 306 | 18.974 | 71.018 | -11.911 | 1.00 | 15.53 | C |
| ATOM | 3937 | C | GLY | A | 306 | 19.775 | 71.132 | -13.193 | 1.00 | 15.37 | C |
| ATOM | 3938 | O | GLY | A | 306 | 19.702 | 70.321 | -14.103 | 1.00 | 14.65 | O |
| ATOM | 3940 | N | HIS | A | 307 | 20.597 | 72.159 | -13.228 | 1.00 | 15.20 | N |
| ATOM | 3941 | CA | HIS | A | 307 | 21.200 | 72.628 | -14.457 | 1.00 | 15.28 | C |
| ATOM | 3943 | CB | HIS | A | 307 | 21.104 | 74.134 | -14.522 | 1.00 | 16.31 | C |
| ATOM | 3946 | CG | HIS | A | 307 | 19.710 | 74.614 | -14.726 | 1.00 | 19.72 | C |
| ATOM | 3947 | ND1 | HIS | A | 307 | 18.826 | 74.788 | -13.682 | 1.00 | 22.67 | N |
| ATOM | 3949 | CE1 | HIS | A | 307 | 17.660 | 75.183 | -14.167 | 1.00 | 25.88 | C |
| ATOM | 3951 | NE2 | HIS | A | 307 | 17.760 | 75.255 | -15.485 | 1.00 | 24.11 | N |
| ATOM | 3953 | CD2 | HIS | A | 307 | 19.024 | 74.880 | -15.861 | 1.00 | 23.69 | C |
| ATOM | 3955 | C | HIS | A | 307 | 22.656 | 72.253 | -14.584 | 1.00 | 14.39 | C |
| ATOM | 3956 | O | HIS | A | 307 | 23.505 | 72.691 | -13.796 | 1.00 | 14.40 | O |
| ATOM | 3958 | N | ALA | A | 308 | 22.945 | 71.474 | -15.620 | 1.00 | 13.44 | N |
| ATOM | 3959 | CA | ALA | A | 308 | 24.327 | 71.135 | -15.951 | 1.00 | 13.83 | C |
| ATOM | 3961 | CB | ALA | A | 308 | 24.363 | 70.091 | -17.082 | 1.00 | 14.78 | C |
| ATOM | 3965 | C | ALA | A | 308 | 25.113 | 72.392 | -16.369 | 1.00 | 13.27 | C |
| ATOM | 3966 | O | ALA | A | 308 | 26.349 | 72.374 | -16.348 | 1.00 | 14.02 | O |
| ATOM | 3968 | N | GLY | A | 309 | 24.383 | 73.462 | -16.760 | 1.00 | 13.90 | N |
| ATOM | 3969 | CA | GLY | A | 309 | 24.985 | 74.667 | -17.297 | 1.00 | 12.76 | C |
| ATOM | 3972 | C | GLY | A | 309 | 25.907 | 75.402 | -16.341 | 1.00 | 12.41 | C |
| ATOM | 3973 | O | GLY | A | 309 | 26.798 | 76.187 | -16.764 | 1.00 | 12.11 | O |
| ATOM | 3975 | N | SER | A | 310 | 25.737 | 75.154 | -15.055 | 1.00 | 11.51 | N |
| ATOM | 3976 | CA | SER | A | 310 | 26.591 | 75.836 | -14.027 | 1.00 | 11.44 | C |
| ATOM | 3978 | CB | SER | A | 310 | 26.176 | 75.493 | -12.590 | 1.00 | 11.60 | C |
| ATOM | 3981 | OG | SER | A | 310 | 24.786 | 75.683 | -12.341 | 1.00 | 13.85 | O |
| ATOM | 3983 | C | SER | A | 310 | 28.055 | 75.429 | -14.195 | 1.00 | 11.31 | C |
| ATOM | 3984 | O | SER | A | 310 | 28.953 | 76.129 | -13.695 | 1.00 | 11.85 | O |
| ATOM | 3986 | N | PHE | A | 311 | 28.302 | 74.296 | -14.901 | 1.00 | 11.00 | N |
| ATOM | 3987 | CA | PHE | A | 311 | 29.647 | 73.711 | -15.013 | 1.00 | 11.34 | C |

| | | | | | | | | | |
|---|---|---|---|---|---|---|---|---|---|
| ATOM | 3989 | CB | PHE | A | 311 | 29.606 | 72.241 | -14.559 | 1.00 11.05 | C |
| ATOM | 3992 | CG | PHE | A | 311 | 28.842 | 72.058 | -13.268 | 1.00 11.24 | C |
| ATOM | 3993 | CD1 | PHE | A | 311 | 29.388 | 72.440 | -12.045 | 1.00 10.68 | C |
| ATOM | 3995 | CE1 | PHE | A | 311 | 28.634 | 72.367 | -10.867 | 1.00 12.19 | C |
| ATOM | 3997 | CZ | PHE | A | 311 | 27.347 | 72.002 | -10.892 | 1.00 11.52 | C |
| ATOM | 3999 | CE2 | PHE | A | 311 | 26.755 | 71.660 | -12.091 | 1.00 14.12 | C |
| ATOM | 4001 | CD2 | PHE | A | 311 | 27.501 | 71.697 | -13.279 | 1.00 14.71 | C |
| ATOM | 4003 | C | PHE | A | 311 | 30.258 | 73.891 | -16.375 | 1.00 11.66 | C |
| ATOM | 4004 | O | PHE | A | 311 | 31.330 | 73.374 | -16.648 | 1.00 12.42 | O |
| ATOM | 4006 | N | HIS | A | 312 | 29.608 | 74.677 | -17.231 | 1.00 11.54 | N |
| ATOM | 4007 | CA | HIS | A | 312 | 30.147 | 74.964 | -18.551 | 1.00 11.67 | C |
| ATOM | 4009 | CB | HIS | A | 312 | 29.145 | 75.806 | -19.311 | 1.00 11.92 | C |
| ATOM | 4012 | CG | HIS | A | 312 | 29.446 | 75.955 | -20.753 | 1.00 13.27 | C |
| ATOM | 4013 | ND1 | HIS | A | 312 | 30.484 | 76.735 | -21.210 | 1.00 12.34 | N |
| ATOM | 4015 | CE1 | HIS | A | 312 | 30.517 | 76.688 | -22.531 | 1.00 15.95 | C |
| ATOM | 4017 | NE2 | HIS | A | 312 | 29.517 | 75.932 | -22.943 | 1.00 15.46 | N |
| ATOM | 4019 | CD2 | HIS | A | 312 | 28.832 | 75.455 | -21.854 | 1.00 13.76 | C |
| ATOM | 4021 | C | HIS | A | 312 | 31.475 | 75.684 | -18.488 | 1.00 11.68 | C |
| ATOM | 4022 | O | HIS | A | 312 | 31.646 | 76.582 | -17.660 | 1.00 12.31 | O |
| ATOM | 4024 | N | PRO | A | 313 | 32.449 | 75.269 | -19.328 | 1.00 12.51 | N |
| ATOM | 4025 | CA | PRO | A | 313 | 33.755 | 75.896 | -19.204 | 1.00 11.27 | C |
| ATOM | 4027 | CB | PRO | A | 313 | 34.614 | 75.178 | -20.272 | 1.00 12.71 | C |
| ATOM | 4030 | CG | PRO | A | 313 | 33.687 | 74.528 | -21.162 | 1.00 13.11 | C |
| ATOM | 4033 | CD | PRO | A | 313 | 32.443 | 74.245 | -20.398 | 1.00 12.25 | C |
| ATOM | 4036 | C | PRO | A | 313 | 33.823 | 77.422 | -19.389 | 1.00 11.42 | C |
| ATOM | 4037 | O | PRO | A | 313 | 34.778 | 78.025 | -18.899 | 1.00 11.36 | O |
| ATOM | 4038 | N | PHE | A | 314 | 32.845 | 78.030 | -20.063 | 1.00 12.08 | N |
| ATOM | 4039 | CA | PHE | A | 314 | 32.838 | 79.498 | -20.197 | 1.00 11.55 | C |
| ATOM | 4041 | CB | PHE | A | 314 | 31.663 | 80.019 | -21.013 | 1.00 13.03 | C |
| ATOM | 4044 | CG | PHE | A | 314 | 31.683 | 81.502 | -21.170 | 1.00 13.45 | C |
| ATOM | 4045 | CD1 | PHE | A | 314 | 32.545 | 82.105 | -22.068 | 1.00 16.07 | C |
| ATOM | 4047 | CE1 | PHE | A | 314 | 32.548 | 83.504 | -22.212 | 1.00 16.60 | C |
| ATOM | 4049 | CZ | PHE | A | 314 | 31.695 | 84.249 | -21.399 | 1.00 14.22 | C |
| ATOM | 4051 | CE2 | PHE | A | 314 | 30.876 | 83.643 | -20.543 | 1.00 14.74 | C |
| ATOM | 4053 | CD2 | PHE | A | 314 | 30.866 | 82.299 | -20.403 | 1.00 15.83 | C |
| ATOM | 4055 | C | PHE | A | 314 | 32.827 | 80.127 | -18.788 | 1.00 11.90 | C |
| ATOM | 4056 | O | PHE | A | 314 | 33.453 | 81.155 | -18.571 | 1.00 11.20 | O |
| ATOM | 4058 | N | LEU | A | 315 | 32.149 | 79.458 | -17.862 | 1.00 11.06 | N |
| ATOM | 4059 | CA | LEU | A | 315 | 31.917 | 79.989 | -16.518 | 1.00 11.14 | C |
| ATOM | 4061 | CB | LEU | A | 315 | 30.670 | 79.318 | -15.941 | 1.00 11.87 | C |
| ATOM | 4064 | CG | LEU | A | 315 | 29.359 | 79.874 | -16.528 | 1.00 11.90 | C |
| ATOM | 4066 | CD1 | LEU | A | 315 | 28.238 | 79.080 | -15.917 | 1.00 13.41 | C |
| ATOM | 4070 | CD2 | LEU | A | 315 | 29.142 | 81.408 | -16.319 | 1.00 13.76 | C |
| ATOM | 4074 | C | LEU | A | 315 | 33.116 | 79.771 | -15.604 | 1.00 12.38 | C |
| ATOM | 4075 | O | LEU | A | 315 | 33.082 | 80.144 | -14.431 | 1.00 10.90 | O |
| ATOM | 4077 | N | HIS | A | 316 | 34.178 | 79.164 | -16.110 | 1.00 11.89 | N |
| ATOM | 4078 | CA | HIS | A | 316 | 35.311 | 78.828 | -15.279 | 1.00 12.24 | C |
| ATOM | 4080 | CB | HIS | A | 316 | 35.219 | 77.365 | -14.770 | 1.00 12.08 | C |
| ATOM | 4083 | CG | HIS | A | 316 | 33.903 | 77.064 | -14.129 | 1.00 12.85 | C |
| ATOM | 4084 | ND1 | HIS | A | 316 | 33.637 | 77.355 | -12.811 | 1.00 12.47 | N |
| ATOM | 4086 | CE1 | HIS | A | 316 | 32.385 | 77.063 | -12.535 | 1.00 10.76 | C |
| ATOM | 4088 | NE2 | HIS | A | 316 | 31.797 | 76.640 | -13.648 | 1.00 11.47 | N |
| ATOM | 4090 | CD2 | HIS | A | 316 | 32.738 | 76.608 | -14.655 | 1.00 11.21 | C |
| ATOM | 4092 | C | HIS | A | 316 | 36.578 | 79.107 | -16.047 | 1.00 12.16 | C |
| ATOM | 4093 | O | HIS | A | 316 | 37.278 | 80.128 | -15.824 | 1.00 13.10 | O |
| ATOM | 4095 | N | ASP | A | 317 | 36.889 | 78.215 | -16.982 | 1.00 12.03 | N |
| ATOM | 4096 | CA | ASP | A | 317 | 38.107 | 78.341 | -17.772 | 1.00 12.60 | C |

| ATOM | 4098 | CB | ASP A 317 | 38.082 | 77.309 | -18.917 | 1.00 | 13.31 | C |
| ATOM | 4101 | CG | ASP A 317 | 37.906 | 75.904 | -18.434 | 1.00 | 15.39 | C |
| ATOM | 4102 | OD1 | ASP A 317 | 36.966 | 75.622 | -17.645 | 1.00 | 13.10 | O |
| ATOM | 4103 | OD2 | ASP A 317 | 38.698 | 75.066 | -18.914 | 1.00 | 18.26 | O |
| ATOM | 4104 | C | ASP A 317 | 38.265 | 79.708 | -18.432 | 1.00 | 12.46 | C |
| ATOM | 4105 | O | ASP A 317 | 39.345 | 80.261 | -18.474 | 1.00 | 13.90 | O |
| ATOM | 4107 | N | VAL A 318 | 37.176 | 80.247 | -18.965 | 1.00 | 11.80 | N |
| ATOM | 4108 | CA | VAL A 318 | 37.256 | 81.474 | -19.718 | 1.00 | 12.10 | C |
| ATOM | 4110 | CB | VAL A 318 | 36.157 | 81.554 | -20.803 | 1.00 | 13.19 | C |
| ATOM | 4112 | CG1 | VAL A 318 | 36.198 | 82.848 | -21.521 | 1.00 | 11.80 | C |
| ATOM | 4116 | CG2 | VAL A 318 | 36.289 | 80.404 | -21.809 | 1.00 | 11.98 | C |
| ATOM | 4120 | C | VAL A 318 | 37.148 | 82.670 | -18.768 | 1.00 | 13.35 | C |
| ATOM | 4121 | O | VAL A 318 | 37.946 | 83.588 | -18.832 | 1.00 | 14.61 | O |
| ATOM | 4123 | N | THR A 319 | 36.184 | 82.640 | -17.864 | 1.00 | 11.69 | N |
| ATOM | 4124 | CA | THR A 319 | 35.854 | 83.879 | -17.128 | 1.00 | 11.59 | C |
| ATOM | 4126 | CB | THR A 319 | 34.340 | 84.017 | -16.972 | 1.00 | 11.55 | C |
| ATOM | 4128 | OG1 | THR A 319 | 33.807 | 82.830 | -16.380 | 1.00 | 10.93 | O |
| ATOM | 4130 | CG2 | THR A 319 | 33.617 | 84.285 | -18.315 | 1.00 | 10.99 | C |
| ATOM | 4134 | C | THR A 319 | 36.517 | 84.085 | -15.748 | 1.00 | 12.41 | C |
| ATOM | 4135 | O | THR A 319 | 36.757 | 85.224 | -15.369 | 1.00 | 13.13 | O |
| ATOM | 4137 | N | ARG A 320 | 36.810 | 83.001 | -15.043 | 1.00 | 10.39 | N |
| ATOM | 4138 | CA | ARG A 320 | 37.417 | 83.023 | -13.721 | 1.00 | 11.08 | C |
| ATOM | 4140 | CB | ARG A 320 | 36.335 | 83.090 | -12.669 | 1.00 | 10.95 | C |
| ATOM | 4143 | CG | ARG A 320 | 36.897 | 83.219 | -11.249 | 1.00 | 12.03 | C |
| ATOM | 4146 | CD | ARG A 320 | 35.815 | 83.546 | -10.319 | 1.00 | 13.68 | C |
| ATOM | 4149 | NE | ARG A 320 | 36.158 | 83.919 | -8.957 | 1.00 | 12.98 | N |
| ATOM | 4151 | CZ | ARG A 320 | 35.629 | 83.328 | -7.890 | 1.00 | 15.15 | C |
| ATOM | 4152 | NH1 | ARG A 320 | 34.922 | 82.210 | -8.010 | 1.00 | 14.29 | N |
| ATOM | 4155 | NH2 | ARG A 320 | 35.844 | 83.834 | -6.675 | 1.00 | 15.73 | N |
| ATOM | 4158 | C | ARG A 320 | 38.385 | 81.845 | -13.513 | 1.00 | 11.00 | C |
| ATOM | 4159 | O | ARG A 320 | 38.071 | 80.867 | -12.843 | 1.00 | 11.03 | O |
| ATOM | 4161 | N | PRO A 321 | 39.540 | 81.912 | -14.181 | 1.00 | 10.90 | N |
| ATOM | 4162 | CA | PRO A 321 | 40.391 | 80.721 | -14.360 | 1.00 | 11.20 | C |
| ATOM | 4164 | CB | PRO A 321 | 41.232 | 81.092 | -15.571 | 1.00 | 10.79 | C |
| ATOM | 4167 | CG | PRO A 321 | 41.428 | 82.571 | -15.468 | 1.00 | 13.11 | C |
| ATOM | 4170 | CD | PRO A 321 | 40.086 | 83.089 | -14.903 | 1.00 | 10.93 | C |
| ATOM | 4173 | C | PRO A 321 | 41.276 | 80.343 | -13.192 | 1.00 | 11.05 | C |
| ATOM | 4174 | O | PRO A 321 | 42.496 | 80.064 | -13.350 | 1.00 | 11.63 | O |
| ATOM | 4175 | N | HIS A 322 | 40.690 | 80.311 | -12.003 | 1.00 | 11.00 | N |
| ATOM | 4176 | CA | HIS A 322 | 41.380 | 79.640 | -10.871 | 1.00 | 10.91 | C |
| ATOM | 4178 | CB | HIS A 322 | 40.563 | 79.745 | -9.605 | 1.00 | 11.28 | C |
| ATOM | 4181 | CG | HIS A 322 | 40.517 | 81.132 | -9.051 | 1.00 | 11.95 | C |
| ATOM | 4182 | ND1 | HIS A 322 | 41.618 | 81.750 | -8.502 | 1.00 | 12.34 | N |
| ATOM | 4184 | CE1 | HIS A 322 | 41.268 | 82.951 | -8.082 | 1.00 | 10.90 | C |
| ATOM | 4186 | NE2 | HIS A 322 | 39.973 | 83.124 | -8.307 | 1.00 | 11.29 | N |
| ATOM | 4188 | CD2 | HIS A 322 | 39.488 | 82.000 | -8.928 | 1.00 | 10.24 | C |
| ATOM | 4190 | C | HIS A 322 | 41.566 | 78.165 | -11.258 | 1.00 | 12.28 | C |
| ATOM | 4191 | O | HIS A 322 | 40.562 | 77.506 | -11.537 | 1.00 | 11.58 | O |
| ATOM | 4193 | N | PRO A 323 | 42.824 | 77.660 | -11.311 | 1.00 | 12.37 | N |
| ATOM | 4194 | CA | PRO A 323 | 43.033 | 76.288 | -11.816 | 1.00 | 13.27 | C |
| ATOM | 4196 | CB | PRO A 323 | 44.505 | 76.031 | -11.541 | 1.00 | 14.03 | C |
| ATOM | 4199 | CG | PRO A 323 | 45.134 | 77.418 | -11.701 | 1.00 | 14.60 | C |
| ATOM | 4202 | CD | PRO A 323 | 44.124 | 78.331 | -11.060 | 1.00 | 12.65 | C |
| ATOM | 4205 | C | PRO A 323 | 42.168 | 75.247 | -11.145 | 1.00 | 11.88 | C |
| ATOM | 4206 | O | PRO A 323 | 41.643 | 74.351 | -11.848 | 1.00 | 13.67 | O |
| ATOM | 4207 | N | THR A 324 | 41.940 | 75.364 | -9.827 | 1.00 | 11.45 | N |
| ATOM | 4208 | CA | THR A 324 | 41.130 | 74.305 | -9.161 | 1.00 | 11.15 | C |

| ATOM | 4210 | CB | THR A 324 | 41.505 | 74.111 | -7.703 | 1.00 | 12.73 | C |
| --- | --- | --- | --- | --- | --- | --- | --- | --- | --- |
| ATOM | 4212 | OG1 | THR A 324 | 41.411 | 75.392 | -7.039 | 1.00 | 12.54 | O |
| ATOM | 4214 | CG2 | THR A 324 | 42.886 | 73.529 | -7.591 | 1.00 | 12.82 | C |
| ATOM | 4218 | C | THR A 324 | 39.628 | 74.493 | -9.281 | 1.00 | 12.07 | C |
| ATOM | 4219 | O | THR A 324 | 38.851 | 73.555 | -9.119 | 1.00 | 11.73 | O |
| ATOM | 4221 | N | GLN A 325 | 39.206 | 75.716 | -9.547 | 1.00 | 11.37 | N |
| ATOM | 4222 | CA | GLN A 325 | 37.797 | 75.922 | -9.934 | 1.00 | 11.74 | C |
| ATOM | 4224 | CB | GLN A 325 | 37.500 | 77.392 | -10.094 | 1.00 | 11.11 | C |
| ATOM | 4227 | CG | GLN A 325 | 35.980 | 77.684 | -10.201 | 1.00 | 12.55 | C |
| ATOM | 4230 | CD | GLN A 325 | 35.695 | 79.185 | -10.314 | 1.00 | 10.65 | C |
| ATOM | 4231 | OE1 | GLN A 325 | 36.233 | 80.008 | -9.515 | 1.00 | 12.59 | O |
| ATOM | 4232 | NE2 | GLN A 325 | 34.868 | 79.562 | -11.298 | 1.00 | 10.40 | N |
| ATOM | 4235 | C | GLN A 325 | 37.531 | 75.243 | -11.282 | 1.00 | 11.54 | C |
| ATOM | 4236 | O | GLN A 325 | 36.529 | 74.565 | -11.469 | 1.00 | 12.22 | O |
| ATOM | 4238 | N | ILE A 326 | 38.434 | 75.478 | -12.221 | 1.00 | 12.13 | N |
| ATOM | 4239 | CA | ILE A 326 | 38.391 | 74.793 | -13.531 | 1.00 | 11.44 | C |
| ATOM | 4241 | CB | ILE A 326 | 39.640 | 75.182 | -14.373 | 1.00 | 11.08 | C |
| ATOM | 4243 | CG1 | ILE A 326 | 39.571 | 76.687 | -14.767 | 1.00 | 11.57 | C |
| ATOM | 4246 | CD1 | ILE A 326 | 40.788 | 77.177 | -15.479 | 1.00 | 12.02 | C |
| ATOM | 4250 | CG2 | ILE A 326 | 39.815 | 74.231 | -15.596 | 1.00 | 13.84 | C |
| ATOM | 4254 | C | ILE A 326 | 38.305 | 73.257 | -13.338 | 1.00 | 11.57 | C |
| ATOM | 4255 | O | ILE A 326 | 37.509 | 72.572 | -13.983 | 1.00 | 12.39 | O |
| ATOM | 4257 | N | GLU A 327 | 39.138 | 72.741 | -12.457 | 1.00 | 11.98 | N |
| ATOM | 4258 | CA | GLU A 327 | 39.203 | 71.315 | -12.148 | 1.00 | 13.75 | C |
| ATOM | 4260 | CB | GLU A 327 | 40.331 | 71.071 | -11.138 | 1.00 | 13.91 | C |
| ATOM | 4263 | CG | GLU A 327 | 40.386 | 69.697 | -10.599 | 1.00 | 15.94 | C |
| ATOM | 4266 | CD | GLU A 327 | 41.494 | 69.497 | -9.543 | 1.00 | 16.17 | C |
| ATOM | 4267 | OE1 | GLU A 327 | 41.383 | 68.487 | -8.821 | 1.00 | 19.95 | O |
| ATOM | 4268 | OE2 | GLU A 327 | 42.433 | 70.342 | -9.468 | 1.00 | 17.28 | O |
| ATOM | 4269 | C | GLU A 327 | 37.899 | 70.774 | -11.614 | 1.00 | 12.29 | C |
| ATOM | 4270 | O | GLU A 327 | 37.351 | 69.794 | -12.117 | 1.00 | 12.43 | O |
| ATOM | 4272 | N | VAL A 328 | 37.357 | 71.449 | -10.611 | 1.00 | 12.66 | N |
| ATOM | 4273 | CA | VAL A 328 | 36.129 | 70.979 | -9.991 | 1.00 | 12.52 | C |
| ATOM | 4275 | CB | VAL A 328 | 35.785 | 71.792 | -8.732 | 1.00 | 12.52 | C |
| ATOM | 4277 | CG1 | VAL A 328 | 34.433 | 71.389 | -8.232 | 1.00 | 12.72 | C |
| ATOM | 4281 | CG2 | VAL A 328 | 36.881 | 71.553 | -7.703 | 1.00 | 11.72 | C |
| ATOM | 4285 | C | VAL A 328 | 34.978 | 71.070 | -10.986 | 1.00 | 12.23 | C |
| ATOM | 4286 | O | VAL A 328 | 34.197 | 70.139 | -11.132 | 1.00 | 12.46 | O |
| ATOM | 4288 | N | ALA A 329 | 34.876 | 72.194 | -11.692 | 1.00 | 12.46 | N |
| ATOM | 4289 | CA | ALA A 329 | 33.810 | 72.296 | -12.695 | 1.00 | 12.49 | C |
| ATOM | 4291 | CB | ALA A 329 | 33.813 | 73.634 | -13.366 | 1.00 | 12.60 | C |
| ATOM | 4295 | C | ALA A 329 | 33.950 | 71.203 | -13.749 | 1.00 | 11.99 | C |
| ATOM | 4296 | O | ALA A 329 | 32.949 | 70.648 | -14.190 | 1.00 | 12.58 | O |
| ATOM | 4298 | N | GLY A 330 | 35.182 | 70.917 | -14.162 | 1.00 | 11.27 | N |
| ATOM | 4299 | CA | GLY A 330 | 35.428 | 69.880 | -15.164 | 1.00 | 12.38 | C |
| ATOM | 4302 | C | GLY A 330 | 35.006 | 68.492 | -14.658 | 1.00 | 12.22 | C |
| ATOM | 4303 | O | GLY A 330 | 34.451 | 67.688 | -15.440 | 1.00 | 13.04 | O |
| ATOM | 4305 | N | ASN A 331 | 35.276 | 68.181 | -13.385 | 1.00 | 12.24 | N |
| ATOM | 4306 | CA | ASN A 331 | 34.910 | 66.883 | -12.795 | 1.00 | 12.60 | C |
| ATOM | 4308 | CB | ASN A 331 | 35.451 | 66.708 | -11.355 | 1.00 | 11.76 | C |
| ATOM | 4311 | CG | ASN A 331 | 36.946 | 66.498 | -11.279 | 1.00 | 13.84 | C |
| ATOM | 4312 | OD1 | ASN A 331 | 37.587 | 66.112 | -12.282 | 1.00 | 15.29 | O |
| ATOM | 4313 | ND2 | ASN A 331 | 37.530 | 66.729 | -10.071 | 1.00 | 12.08 | N |
| ATOM | 4316 | C | ASN A 331 | 33.382 | 66.757 | -12.810 | 1.00 | 12.36 | C |
| ATOM | 4317 | O | ASN A 331 | 32.837 | 65.758 | -13.294 | 1.00 | 12.16 | O |
| ATOM | 4319 | N | ILE A 332 | 32.690 | 67.781 | -12.351 | 1.00 | 12.06 | N |
| ATOM | 4320 | CA | ILE A 332 | 31.220 | 67.705 | -12.266 | 1.00 | 11.96 | C |

| | | | | | | | | | |
|---|---|---|---|---|---|---|---|---|---|
| ATOM | 4322 | CB | ILE A 332 | 30.659 | 68.827 | -11.379 | 1.00 | 11.95 | C |
| ATOM | 4324 | CG1 | ILE A 332 | 31.260 | 68.709 | -9.954 | 1.00 | 11.79 | C |
| ATOM | 4327 | CD1 | ILE A 332 | 31.002 | 69.866 | -9.046 | 1.00 | 12.47 | C |
| ATOM | 4331 | CG2 | ILE A 332 | 29.133 | 68.802 | -11.424 | 1.00 | 11.78 | C |
| ATOM | 4335 | C | ILE A 332 | 30.607 | 67.681 | -13.685 | 1.00 | 12.66 | C |
| ATOM | 4336 | O | ILE A 332 | 29.657 | 66.942 | -13.965 | 1.00 | 13.68 | O |
| ATOM | 4338 | N | ARG A 333 | 31.164 | 68.494 | -14.589 | 1.00 | 12.72 | N |
| ATOM | 4339 | CA | ARG A 333 | 30.727 | 68.488 | -15.973 | 1.00 | 12.51 | C |
| ATOM | 4341 | CB | ARG A 333 | 31.534 | 69.524 | -16.759 | 1.00 | 13.68 | C |
| ATOM | 4344 | CG | ARG A 333 | 31.178 | 69.540 | -18.235 | 1.00 | 13.19 | C |
| ATOM | 4347 | CD | ARG A 333 | 31.781 | 70.703 | -18.956 | 1.00 | 14.16 | C |
| ATOM | 4350 | NE | ARG A 333 | 33.241 | 70.612 | -19.043 | 1.00 | 14.69 | N |
| ATOM | 4352 | CZ | ARG A 333 | 34.131 | 71.324 | -18.349 | 1.00 | 15.57 | C |
| ATOM | 4353 | NH1 | ARG A 333 | 33.760 | 72.217 | -17.427 | 1.00 | 13.60 | N |
| ATOM | 4356 | NH2 | ARG A 333 | 35.431 | 71.101 | -18.553 | 1.00 | 16.79 | N |
| ATOM | 4359 | C | ARG A 333 | 30.840 | 67.081 | -16.569 | 1.00 | 14.15 | C |
| ATOM | 4360 | O | ARG A 333 | 29.894 | 66.585 | -17.193 | 1.00 | 13.21 | O |
| ATOM | 4362 | N | LYS A 334 | 31.976 | 66.438 | -16.351 | 1.00 | 12.74 | N |
| ATOM | 4363 | CA | LYS A 334 | 32.209 | 65.078 | -16.838 | 1.00 | 15.39 | C |
| ATOM | 4365 | CB | LYS A 334 | 33.616 | 64.682 | -16.483 | 1.00 | 15.62 | C |
| ATOM | 4368 | CG | LYS A 334 | 34.032 | 63.390 | -17.059 | 1.00 | 21.56 | C |
| ATOM | 4371 | CD | LYS A 334 | 35.568 | 63.327 | -17.252 | 1.00 | 27.67 | C |
| ATOM | 4374 | CE | LYS A 334 | 36.168 | 62.310 | -16.393 | 1.00 | 31.13 | C |
| ATOM | 4377 | NZ | LYS A 334 | 37.569 | 62.040 | -16.898 | 1.00 | 35.15 | N |
| ATOM | 4381 | C | LYS A 334 | 31.200 | 64.088 | -16.242 | 1.00 | 13.91 | C |
| ATOM | 4382 | O | LYS A 334 | 30.598 | 63.276 | -16.966 | 1.00 | 14.26 | O |
| ATOM | 4384 | N | LEU A 335 | 30.967 | 64.177 | -14.939 | 1.00 | 14.35 | N |
| ATOM | 4385 | CA | LEU A 335 | 29.975 | 63.320 | -14.287 | 1.00 | 14.48 | C |
| ATOM | 4387 | CB | LEU A 335 | 29.956 | 63.588 | -12.767 | 1.00 | 14.82 | C |
| ATOM | 4390 | CG | LEU A 335 | 31.231 | 63.160 | -12.016 | 1.00 | 16.58 | C |
| ATOM | 4392 | CD1 | LEU A 335 | 31.067 | 63.559 | -10.528 | 1.00 | 14.99 | C |
| ATOM | 4396 | CD2 | LEU A 335 | 31.464 | 61.667 | -12.168 | 1.00 | 16.63 | C |
| ATOM | 4400 | C | LEU A 335 | 28.535 | 63.494 | -14.821 | 1.00 | 14.62 | C |
| ATOM | 4401 | O | LEU A 335 | 27.738 | 62.534 | -14.856 | 1.00 | 14.76 | O |
| ATOM | 4403 | N | LEU A 336 | 28.175 | 64.720 | -15.182 | 1.00 | 14.02 | N |
| ATOM | 4404 | CA | LEU A 336 | 26.819 | 65.004 | -15.690 | 1.00 | 14.27 | C |
| ATOM | 4406 | CB | LEU A 336 | 26.442 | 66.470 | -15.422 | 1.00 | 13.92 | C |
| ATOM | 4409 | CG | LEU A 336 | 26.274 | 66.763 | -13.925 | 1.00 | 12.17 | C |
| ATOM | 4411 | CD1 | LEU A 336 | 26.048 | 68.248 | -13.654 | 1.00 | 14.77 | C |
| ATOM | 4415 | CD2 | LEU A 336 | 25.116 | 65.914 | -13.311 | 1.00 | 15.20 | C |
| ATOM | 4419 | C | LEU A 336 | 26.624 | 64.688 | -17.180 | 1.00 | 15.16 | C |
| ATOM | 4420 | O | LEU A 336 | 25.464 | 64.726 | -17.670 | 1.00 | 14.60 | O |
| ATOM | 4422 | N | GLU A 337 | 27.712 | 64.432 | -17.912 | 1.00 | 14.63 | N |
| ATOM | 4423 | CA | GLU A 337 | 27.595 | 64.165 | -19.346 | 1.00 | 16.04 | C |
| ATOM | 4425 | CB | GLU A 337 | 28.936 | 63.822 | -19.979 | 1.00 | 16.74 | C |
| ATOM | 4428 | CG | GLU A 337 | 29.789 | 65.028 | -20.161 | 1.00 | 20.92 | C |
| ATOM | 4431 | CD | GLU A 337 | 31.210 | 64.732 | -20.596 | 1.00 | 23.39 | C |
| ATOM | 4432 | OE1 | GLU A 337 | 31.625 | 63.527 | -20.620 | 1.00 | 30.55 | O |
| ATOM | 4433 | OE2 | GLU A 337 | 31.898 | 65.735 | -20.934 | 1.00 | 33.30 | O |
| ATOM | 4434 | C | GLU A 337 | 26.668 | 62.970 | -19.520 | 1.00 | 15.17 | C |
| ATOM | 4435 | O | GLU A 337 | 26.823 | 61.940 | -18.864 | 1.00 | 14.77 | O |
| ATOM | 4437 | N | GLY A 338 | 25.697 | 63.121 | -20.405 | 1.00 | 15.03 | N |
| ATOM | 4438 | CA | GLY A 338 | 24.777 | 62.016 | -20.703 | 1.00 | 15.13 | C |
| ATOM | 4441 | C | GLY A 338 | 23.662 | 61.788 | -19.702 | 1.00 | 15.39 | C |
| ATOM | 4442 | O | GLY A 338 | 22.819 | 60.908 | -19.890 | 1.00 | 15.61 | O |
| ATOM | 4444 | N | SER A 339 | 23.588 | 62.605 | -18.659 | 1.00 | 15.20 | N |
| ATOM | 4445 | CA | SER A 339 | 22.470 | 62.486 | -17.721 | 1.00 | 15.32 | C |

| ATOM | 4447 | CB | SER A 339 | 22.645 | 63.432 | -16.532 | 1.00 | 14.76 | C |
|------|------|-----|-----------|--------|--------|---------|------|-------|---|
| ATOM | 4450 | OG | SER A 339 | 21.588 | 63.224 | -15.607 | 1.00 | 15.50 | O |
| ATOM | 4452 | C | SER A 339 | 21.181 | 62.873 | -18.416 | 1.00 | 15.67 | C |
| ATOM | 4453 | O | SER A 339 | 21.181 | 63.810 | -19.183 | 1.00 | 15.85 | O |
| ATOM | 4455 | N | ARG A 340 | 20.101 | 62.146 | -18.156 | 1.00 | 15.51 | N |
| ATOM | 4456 | CA | ARG A 340 | 18.769 | 62.562 | -18.599 | 1.00 | 17.22 | C |
| ATOM | 4458 | CB | ARG A 340 | 18.051 | 61.400 | -19.307 | 1.00 | 17.38 | C |
| ATOM | 4461 | CG | ARG A 340 | 18.811 | 60.904 | -20.507 | 1.00 | 20.67 | C |
| ATOM | 4464 | CD | ARG A 340 | 18.182 | 59.645 | -21.080 | 1.00 | 23.42 | C |
| ATOM | 4467 | NE | ARG A 340 | 16.778 | 59.859 | -21.412 | 1.00 | 29.63 | N |
| ATOM | 4469 | CZ | ARG A 340 | 15.818 | 58.919 | -21.435 | 1.00 | 31.70 | C |
| ATOM | 4470 | NH1 | ARG A 340 | 16.053 | 57.645 | -21.103 | 1.00 | 28.98 | N |
| ATOM | 4473 | NH2 | ARG A 340 | 14.578 | 59.285 | -21.760 | 1.00 | 32.48 | N |
| ATOM | 4476 | C | ARG A 340 | 17.942 | 63.115 | -17.439 | 1.00 | 16.29 | C |
| ATOM | 4477 | O | ARG A 340 | 16.790 | 63.493 | -17.600 | 1.00 | 17.44 | O |
| ATOM | 4479 | N | PHE A 341 | 18.560 | 63.254 | -16.265 | 1.00 | 16.08 | N |
| ATOM | 4480 | CA | PHE A 341 | 17.936 | 63.931 | -15.158 | 1.00 | 15.79 | C |
| ATOM | 4482 | CB | PHE A 341 | 18.426 | 63.363 | -13.840 | 1.00 | 15.16 | C |
| ATOM | 4485 | CG | PHE A 341 | 17.785 | 62.075 | -13.424 | 1.00 | 15.40 | C |
| ATOM | 4486 | CD1 | PHE A 341 | 16.407 | 61.994 | -13.232 | 1.00 | 16.13 | C |
| ATOM | 4488 | CE1 | PHE A 341 | 15.822 | 60.803 | -12.737 | 1.00 | 16.85 | C |
| ATOM | 4490 | CZ | PHE A 341 | 16.625 | 59.718 | -12.436 | 1.00 | 15.57 | C |
| ATOM | 4492 | CE2 | PHE A 341 | 17.991 | 59.792 | -12.635 | 1.00 | 17.73 | C |
| ATOM | 4494 | CD2 | PHE A 341 | 18.570 | 60.973 | -13.111 | 1.00 | 15.27 | C |
| ATOM | 4496 | C | PHE A 341 | 18.322 | 65.429 | -15.177 | 1.00 | 15.71 | C |
| ATOM | 4497 | O | PHE A 341 | 17.477 | 66.302 | -15.037 | 1.00 | 16.37 | O |
| ATOM | 4499 | N | ALA A 342 | 19.630 | 65.703 | -15.275 | 1.00 | 16.85 | N |
| ATOM | 4500 | CA | ALA A 342 | 20.131 | 67.081 | -15.310 | 1.00 | 17.25 | C |
| ATOM | 4502 | CB | ALA A 342 | 21.659 | 67.101 | -15.201 | 1.00 | 18.04 | C |
| ATOM | 4506 | C | ALA A 342 | 19.685 | 67.721 | -16.626 | 1.00 | 18.69 | C |
| ATOM | 4507 | O | ALA A 342 | 19.567 | 67.032 | -17.660 | 1.00 | 18.95 | O |
| ATOM | 4509 | N | VAL A 343 | 19.395 | 69.010 | -16.569 | 1.00 | 18.65 | N |
| ATOM | 4510 | CA | VAL A 343 | 18.968 | 69.792 | -17.727 | 1.00 | 20.38 | C |
| ATOM | 4512 | CB | VAL A 343 | 18.087 | 70.985 | -17.278 | 1.00 | 21.08 | C |
| ATOM | 4514 | CG1 | VAL A 343 | 17.898 | 71.970 | -18.415 | 1.00 | 21.91 | C |
| ATOM | 4518 | CG2 | VAL A 343 | 16.746 | 70.493 | -16.770 | 1.00 | 23.66 | C |
| ATOM | 4522 | C | VAL A 343 | 20.220 | 70.295 | -18.425 | 1.00 | 22.38 | C |
| ATOM | 4523 | O | VAL A 343 | 21.096 | 70.892 | -17.793 | 1.00 | 19.68 | O |
| ATOM | 4525 | N | HIS A 344 | 20.306 | 70.061 | -19.736 | 1.00 | 25.52 | N |
| ATOM | 4526 | CA | HIS A 344 | 21.487 | 70.436 | -20.504 | 1.00 | 29.63 | C |
| ATOM | 4528 | CB | HIS A 344 | 21.943 | 69.275 | -21.358 | 1.00 | 28.90 | C |
| ATOM | 4531 | CG | HIS A 344 | 22.464 | 68.138 | -20.544 | 1.00 | 29.05 | C |
| ATOM | 4532 | ND1 | HIS A 344 | 23.767 | 68.083 | -20.091 | 1.00 | 26.67 | N |
| ATOM | 4534 | CE1 | HIS A 344 | 23.935 | 66.979 | -19.383 | 1.00 | 26.70 | C |
| ATOM | 4536 | NE2 | HIS A 344 | 22.780 | 66.333 | -19.339 | 1.00 | 29.46 | N |
| ATOM | 4538 | CD2 | HIS A 344 | 21.844 | 67.036 | -20.056 | 1.00 | 28.87 | C |
| ATOM | 4540 | C | HIS A 344 | 21.331 | 71.717 | -21.314 | 1.00 | 34.65 | C |
| ATOM | 4541 | O | HIS A 344 | 20.225 | 72.138 | -21.606 | 1.00 | 34.88 | O |
| ATOM | 4543 | N | HIS A 345 | 22.478 | 72.321 | -21.619 | 1.00 | 41.49 | N |
| ATOM | 4544 | CA | HIS A 345 | 22.604 | 73.692 | -22.164 | 1.00 | 47.01 | C |
| ATOM | 4546 | CB | HIS A 345 | 23.888 | 74.400 | -21.624 | 1.00 | 48.30 | C |
| ATOM | 4549 | CG | HIS A 345 | 24.574 | 75.299 | -22.630 | 1.00 | 51.74 | C |
| ATOM | 4550 | ND1 | HIS A 345 | 25.642 | 74.881 | -23.404 | 1.00 | 53.99 | N |
| ATOM | 4552 | CE1 | HIS A 345 | 26.041 | 75.875 | -24.182 | 1.00 | 54.07 | C |
| ATOM | 4554 | NE2 | HIS A 345 | 25.272 | 76.923 | -23.945 | 1.00 | 54.24 | N |
| ATOM | 4556 | CD2 | HIS A 345 | 24.344 | 76.591 | -22.982 | 1.00 | 54.11 | C |
| ATOM | 4558 | C | HIS A 345 | 22.612 | 73.660 | -23.682 | 1.00 | 50.29 | C |

| | | | | | | | | | |
|---|---|---|---|---|---|---|---|---|---|
| ATOM | 4559 | O | HIS | A | 345 | 21.949 | 74.485 | -24.327 | 1.00 51.07 | O |
| ATOM | 4561 | N | GLU | A | 346 | 23.358 | 72.705 | -24.246 | 1.00 54.44 | N |
| ATOM | 4562 | CA | GLU | A | 346 | 23.208 | 72.366 | -25.670 | 1.00 57.71 | C |
| ATOM | 4564 | CB | GLU | A | 346 | 24.404 | 71.535 | -26.203 | 1.00 58.05 | C |
| ATOM | 4567 | CG | GLU | A | 346 | 24.335 | 70.007 | -26.040 | 1.00 59.37 | C |
| ATOM | 4570 | CD | GLU | A | 346 | 23.976 | 69.558 | -24.632 | 1.00 61.08 | C |
| ATOM | 4571 | OE1 | GLU | A | 346 | 24.602 | 70.068 | -23.663 | 1.00 61.59 | O |
| ATOM | 4572 | OE2 | GLU | A | 346 | 23.078 | 68.684 | -24.509 | 1.00 61.20 | O |
| ATOM | 4573 | C | GLU | A | 346 | 21.818 | 71.718 | -25.915 | 1.00 60.10 | C |
| ATOM | 4574 | O | GLU | A | 346 | 21.590 | 71.047 | -26.935 | 1.00 60.53 | O |
| ATOM | 4576 | N | GLU | A | 347 | 20.916 | 71.915 | -24.940 | 1.00 62.69 | N |
| ATOM | 4577 | CA | GLU | A | 347 | 19.463 | 71.889 | -25.136 | 1.00 64.89 | C |
| ATOM | 4579 | CB | GLU | A | 347 | 18.851 | 70.673 | -24.447 | 1.00 64.88 | C |
| ATOM | 4582 | CG | GLU | A | 347 | 19.426 | 69.334 | -24.896 | 1.00 65.69 | C |
| ATOM | 4585 | CD | GLU | A | 347 | 19.424 | 68.290 | -23.785 | 1.00 65.75 | C |
| ATOM | 4586 | OE1 | GLU | A | 347 | 18.544 | 68.347 | -22.885 | 1.00 66.38 | O |
| ATOM | 4587 | OE2 | GLU | A | 347 | 20.319 | 67.413 | -23.816 | 1.00 67.37 | O |
| ATOM | 4588 | C | GLU | A | 347 | 18.813 | 73.167 | -24.571 | 1.00 65.61 | C |
| ATOM | 4589 | O | GLU | A | 347 | 18.207 | 73.935 | -25.329 | 1.00 65.82 | O |
| ATOM | 4591 | N | GLU | A | 348 | 18.959 | 73.388 | -23.254 | 1.00 66.86 | N |
| ATOM | 4592 | CA | GLU | A | 348 | 18.288 | 74.486 | -22.497 | 1.00 67.50 | C |
| ATOM | 4594 | CB | GLU | A | 348 | 19.001 | 74.722 | -21.156 | 1.00 67.51 | C |
| ATOM | 4597 | CG | GLU | A | 348 | 18.407 | 75.840 | -20.263 | 1.00 67.71 | C |
| ATOM | 4600 | CD | GLU | A | 348 | 19.322 | 76.241 | -19.069 | 1.00 68.27 | C |
| ATOM | 4601 | OE1 | GLU | A | 348 | 18.872 | 77.035 | -18.208 | 1.00 68.61 | O |
| ATOM | 4602 | OE2 | GLU | A | 348 | 20.484 | 75.772 | -18.984 | 1.00 68.51 | O |
| ATOM | 4603 | C | GLU | A | 348 | 18.168 | 75.833 | -23.248 | 1.00 68.31 | C |
| ATOM | 4604 | O | GLU | A | 348 | 17.168 | 76.557 | -23.067 | 1.00 68.19 | O |
| ATOM | 4606 | N | VAL | A | 349 | 19.193 | 76.167 | -24.050 | 1.00 68.83 | N |
| ATOM | 4607 | CA | VAL | A | 349 | 19.184 | 77.356 | -24.923 | 1.00 68.92 | C |
| ATOM | 4609 | CB | VAL | A | 349 | 20.607 | 78.043 | -25.037 | 1.00 69.28 | C |
| ATOM | 4611 | CG1 | VAL | A | 349 | 21.073 | 78.568 | -23.671 | 1.00 69.39 | C |
| ATOM | 4615 | CG2 | VAL | A | 349 | 21.673 | 77.106 | -25.665 | 1.00 69.29 | C |
| ATOM | 4619 | C | VAL | A | 349 | 18.642 | 76.998 | -26.316 | 1.00 69.23 | C |
| ATOM | 4620 | O | VAL | A | 349 | 19.187 | 77.408 | -27.348 | 1.00 69.41 | O |
| ATOM | 4622 | N | ASP | A | 354 | 6.378 | 87.419 | -13.406 | 1.00 30.71 | N |
| ATOM | 4623 | CA | ASP | A | 354 | 5.442 | 88.069 | -12.474 | 1.00 30.41 | C |
| ATOM | 4625 | CB | ASP | A | 354 | 4.406 | 88.935 | -13.249 | 1.00 30.22 | C |
| ATOM | 4628 | CG | ASP | A | 354 | 3.383 | 88.122 | -14.016 | 1.00 31.32 | C |
| ATOM | 4629 | OD1 | ASP | A | 354 | 3.468 | 86.859 | -14.065 | 1.00 29.81 | O |
| ATOM | 4630 | OD2 | ASP | A | 354 | 2.470 | 88.782 | -14.599 | 1.00 34.94 | O |
| ATOM | 4631 | C | ASP | A | 354 | 4.755 | 87.090 | -11.493 | 1.00 30.40 | C |
| ATOM | 4632 | O | ASP | A | 354 | 3.641 | 87.343 | -11.002 | 1.00 28.62 | O |
| ATOM | 4634 | N | GLU | A | 355 | 5.428 | 85.966 | -11.232 | 1.00 30.67 | N |
| ATOM | 4635 | CA | GLU | A | 355 | 4.993 | 85.000 | -10.224 | 1.00 31.71 | C |
| ATOM | 4637 | CB | GLU | A | 355 | 4.390 | 83.777 | -10.910 | 1.00 31.59 | C |
| ATOM | 4640 | CG | GLU | A | 355 | 3.172 | 84.121 | -11.719 | 1.00 32.57 | C |
| ATOM | 4643 | CD | GLU | A | 355 | 2.620 | 82.936 | -12.473 | 1.00 33.79 | C |
| ATOM | 4644 | OE1 | GLU | A | 355 | 3.134 | 81.805 | -12.282 | 1.00 38.03 | O |
| ATOM | 4645 | OE2 | GLU | A | 355 | 1.660 | 83.158 | -13.244 | 1.00 36.56 | O |
| ATOM | 4646 | C | GLU | A | 355 | 6.107 | 84.574 | -9.278 | 1.00 32.21 | C |
| ATOM | 4647 | O | GLU | A | 355 | 5.939 | 83.653 | -8.492 | 1.00 31.99 | O |
| ATOM | 4649 | N | GLY | A | 356 | 7.246 | 85.261 | -9.349 | 1.00 33.48 | N |
| ATOM | 4650 | CA | GLY | A | 356 | 8.354 | 84.987 | -8.468 | 1.00 34.33 | C |
| ATOM | 4653 | C | GLY | A | 356 | 8.925 | 83.595 | -8.626 | 1.00 34.74 | C |
| ATOM | 4654 | O | GLY | A | 356 | 9.404 | 83.018 | -7.654 | 1.00 35.76 | O |
| ATOM | 4656 | N | ILE | A | 357 | 8.893 | 83.061 | -9.848 | 1.00 35.32 | N |

| | | | | | | | | | |
|---|---|---|---|---|---|---|---|---|---|
| ATOM | 4657 | CA | ILE A 357 | 9.427 | 81.721 | -10.108 | 1.00 | 35.88 | C |
| ATOM | 4659 | CB | ILE A 357 | 8.898 | 81.133 | -11.432 | 1.00 | 36.14 | C |
| ATOM | 4661 | CG1 | ILE A 357 | 7.441 | 80.701 | -11.247 | 1.00 | 36.37 | C |
| ATOM | 4664 | CD1 | ILE A 357 | 6.725 | 80.382 | -12.560 | 1.00 | 36.83 | C |
| ATOM | 4668 | CG2 | ILE A 357 | 9.744 | 79.925 | -11.887 | 1.00 | 37.53 | C |
| ATOM | 4672 | C | ILE A 357 | 10.959 | 81.762 | -10.115 | 1.00 | 35.81 | C |
| ATOM | 4673 | O | ILE A 357 | 11.567 | 82.635 | -10.740 | 1.00 | 35.44 | O |
| ATOM | 4675 | N | LEU A 358 | 11.560 | 80.806 | -9.404 | 1.00 | 36.02 | N |
| ATOM | 4676 | CA | LEU A 358 | 13.008 | 80.656 | -9.338 | 1.00 | 35.57 | C |
| ATOM | 4678 | CB | LEU A 358 | 13.377 | 79.878 | -8.066 | 1.00 | 36.37 | C |
| ATOM | 4681 | CG | LEU A 358 | 14.838 | 79.478 | -7.830 | 1.00 | 38.06 | C |
| ATOM | 4683 | CD1 | LEU A 358 | 15.287 | 79.818 | -6.415 | 1.00 | 39.18 | C |
| ATOM | 4687 | CD2 | LEU A 358 | 15.047 | 77.969 | -8.115 | 1.00 | 40.92 | C |
| ATOM | 4691 | C | LEU A 358 | 13.477 | 79.918 | -10.586 | 1.00 | 34.21 | C |
| ATOM | 4692 | O | LEU A 358 | 13.142 | 78.747 | -10.802 | 1.00 | 34.74 | O |
| ATOM | 4694 | N | ARG A 359 | 14.220 | 80.597 | -11.442 | 1.00 | 31.86 | N |
| ATOM | 4695 | CA | ARG A 359 | 14.602 | 79.980 | -12.725 | 1.00 | 30.29 | C |
| ATOM | 4697 | CB | ARG A 359 | 14.405 | 80.968 | -13.862 | 1.00 | 31.23 | C |
| ATOM | 4700 | CG | ARG A 359 | 13.021 | 81.547 | -13.782 | 1.00 | 35.43 | C |
| ATOM | 4703 | CD | ARG A 359 | 12.669 | 82.413 | -14.925 | 1.00 | 40.34 | C |
| ATOM | 4706 | NE | ARG A 359 | 11.214 | 82.512 | -14.978 | 1.00 | 42.52 | N |
| ATOM | 4708 | CZ | ARG A 359 | 10.541 | 83.232 | -15.864 | 1.00 | 46.47 | C |
| ATOM | 4709 | NH1 | ARG A 359 | 11.186 | 83.946 | -16.791 | 1.00 | 49.64 | N |
| ATOM | 4712 | NH2 | ARG A 359 | 9.213 | 83.239 | -15.823 | 1.00 | 46.33 | N |
| ATOM | 4715 | C | ARG A 359 | 16.031 | 79.431 | -12.759 | 1.00 | 27.14 | C |
| ATOM | 4716 | O | ARG A 359 | 16.392 | 78.720 | -13.706 | 1.00 | 26.65 | O |
| ATOM | 4718 | N | AGLN A 360 | 16.829 | 79.752 | -11.743 | 0.50 | 24.66 | N |
| ATOM | 4719 | N | BGLN A 360 | 16.843 | 79.763 | -11.757 | 0.50 | 24.77 | N |
| ATOM | 4720 | CA | AGLN A 360 | 18.173 | 79.230 | -11.698 | 0.50 | 22.69 | C |
| ATOM | 4721 | CA | BGLN A 360 | 18.197 | 79.243 | -11.711 | 0.50 | 22.84 | C |
| ATOM | 4724 | CB | AGLN A 360 | 19.186 | 80.353 | -11.922 | 0.50 | 22.75 | C |
| ATOM | 4725 | CB | BGLN A 360 | 19.209 | 80.373 | -11.881 | 0.50 | 23.15 | C |
| ATOM | 4730 | CG | AGLN A 360 | 20.430 | 79.931 | -12.703 | 0.50 | 23.00 | C |
| ATOM | 4731 | CG | BGLN A 360 | 18.981 | 81.257 | -13.125 | 0.50 | 23.16 | C |
| ATOM | 4736 | CD | AGLN A 360 | 20.260 | 78.577 | -13.388 | 0.50 | 18.97 | C |
| ATOM | 4737 | CD | BGLN A 360 | 18.936 | 80.475 | -14.427 | 0.50 | 24.53 | C |
| ATOM | 4738 | OE1 | AGLN A 360 | 20.790 | 77.563 | -12.917 | 0.50 | 10.46 | O |
| ATOM | 4739 | OE1 | BGLN A 360 | 19.504 | 79.389 | -14.546 | 0.50 | 25.12 | O |
| ATOM | 4740 | NE2 | AGLN A 360 | 19.460 | 78.556 | -14.486 | 0.50 | 20.28 | N |
| ATOM | 4741 | NE2 | BGLN A 360 | 18.262 | 81.037 | -15.424 | 0.50 | 24.79 | N |
| ATOM | 4746 | C | AGLN A 360 | 18.441 | 78.475 | -10.401 | 0.50 | 21.10 | C |
| ATOM | 4747 | C | BGLN A 360 | 18.437 | 78.471 | -10.414 | 0.50 | 21.21 | C |
| ATOM | 4748 | O | AGLN A 360 | 17.811 | 78.729 | -9.376 | 0.50 | 20.37 | O |
| ATOM | 4749 | O | BGLN A 360 | 17.785 | 78.713 | -9.401 | 0.50 | 20.45 | O |
| ATOM | 4752 | N | ASP A 361 | 19.367 | 77.522 | -10.471 | 1.00 | 18.98 | N |
| ATOM | 4753 | CA | ASP A 361 | 19.728 | 76.695 | -9.289 | 1.00 | 17.57 | C |
| ATOM | 4755 | CB | ASP A 361 | 20.816 | 75.676 | -9.649 | 1.00 | 17.32 | C |
| ATOM | 4758 | CG | ASP A 361 | 20.279 | 74.503 | -10.462 | 1.00 | 18.34 | C |
| ATOM | 4759 | OD1 | ASP A 361 | 19.048 | 74.428 | -10.687 | 1.00 | 20.35 | O |
| ATOM | 4760 | OD2 | ASP A 361 | 21.075 | 73.666 | -10.899 | 1.00 | 16.39 | O |
| ATOM | 4761 | C | ASP A 361 | 20.209 | 77.602 | -8.129 | 1.00 | 15.04 | C |
| ATOM | 4762 | O | ASP A 361 | 20.798 | 78.644 | -8.335 | 1.00 | 14.49 | O |
| ATOM | 4764 | N | ARG A 362 | 19.963 | 77.156 | -6.906 | 1.00 | 13.80 | N |
| ATOM | 4765 | CA | ARG A 362 | 20.439 | 77.872 | -5.726 | 1.00 | 13.36 | C |
| ATOM | 4767 | CB | ARG A 362 | 19.657 | 77.406 | -4.495 | 1.00 | 12.93 | C |
| ATOM | 4770 | CG | ARG A 362 | 18.223 | 77.596 | -4.609 | 1.00 | 13.96 | C |
| ATOM | 4773 | CD | ARG A 362 | 17.475 | 77.304 | -3.330 | 1.00 | 13.69 | C |

| | | | | | | | | | |
|---|---|---|---|---|---|---|---|---|---|
| ATOM | 4776 | NE | ARG | A | 362 | 16.044 | 77.552 | -3.453 | 1.00 16.43 | N |
| ATOM | 4778 | CZ | ARG | A | 362 | 15.176 | 76.657 | -3.949 | 1.00 15.40 | C |
| ATOM | 4779 | NH1 | ARG | A | 362 | 15.549 | 75.478 | -4.471 | 1.00 18.97 | N |
| ATOM | 4782 | NH2 | ARG | A | 362 | 13.894 | 77.003 | -4.013 | 1.00 19.52 | N |
| ATOM | 4785 | C | ARG | A | 362 | 21.946 | 77.644 | -5.563 | 1.00 13.26 | C |
| ATOM | 4786 | O | ARG | A | 362 | 22.564 | 76.862 | -6.304 | 1.00 13.43 | O |
| ATOM | 4788 | N | TYR | A | 363 | 22.556 | 78.391 | -4.650 | 1.00 13.04 | N |
| ATOM | 4789 | CA | TYR | A | 363 | 24.017 | 78.397 | -4.610 | 1.00 13.05 | C |
| ATOM | 4791 | CB | TYR | A | 363 | 24.464 | 79.454 | -3.597 | 1.00 13.56 | C |
| ATOM | 4794 | CG | TYR | A | 363 | 24.286 | 80.859 | -4.029 | 1.00 13.64 | C |
| ATOM | 4795 | CD1 | TYR | A | 363 | 23.513 | 81.230 | -5.141 | 1.00 14.01 | C |
| ATOM | 4797 | CE1 | TYR | A | 363 | 23.395 | 82.568 | -5.476 | 1.00 16.27 | C |
| ATOM | 4799 | CZ | TYR | A | 363 | 23.985 | 83.522 | -4.649 | 1.00 15.60 | C |
| ATOM | 4800 | OH | TYR | A | 363 | 23.886 | 84.852 | -4.925 | 1.00 19.42 | O |
| ATOM | 4802 | CE2 | TYR | A | 363 | 24.734 | 83.168 | -3.592 | 1.00 16.35 | C |
| ATOM | 4804 | CD2 | TYR | A | 363 | 24.854 | 81.854 | -3.261 | 1.00 14.86 | C |
| ATOM | 4806 | C | TYR | A | 363 | 24.706 | 77.078 | -4.296 | 1.00 13.94 | C |
| ATOM | 4807 | O | TYR | A | 363 | 25.835 | 76.834 | -4.768 | 1.00 13.49 | O |
| ATOM | 4809 | N | PRO | A | 364 | 24.086 | 76.210 | -3.464 | 1.00 12.94 | N |
| ATOM | 4810 | CA | PRO | A | 364 | 24.783 | 74.901 | -3.182 | 1.00 12.70 | C |
| ATOM | 4812 | CB | PRO | A | 364 | 23.813 | 74.168 | -2.277 | 1.00 13.45 | C |
| ATOM | 4815 | CG | PRO | A | 364 | 23.067 | 75.257 | -1.587 | 1.00 15.73 | C |
| ATOM | 4818 | CD | PRO | A | 364 | 22.886 | 76.353 | -2.619 | 1.00 14.77 | C |
| ATOM | 4821 | C | PRO | A | 364 | 25.190 | 74.091 | -4.411 | 1.00 12.44 | C |
| ATOM | 4822 | O | PRO | A | 364 | 26.226 | 73.378 | -4.383 | 1.00 12.86 | O |
| ATOM | 4823 | N | LEU | A | 365 | 24.382 | 74.192 | -5.466 | 1.00 12.72 | N |
| ATOM | 4824 | CA | LEU | A | 365 | 24.730 | 73.557 | -6.742 | 1.00 12.62 | C |
| ATOM | 4826 | CB | LEU | A | 365 | 23.472 | 72.942 | -7.401 | 1.00 13.31 | C |
| ATOM | 4829 | CG | LEU | A | 365 | 22.706 | 71.897 | -6.561 | 1.00 15.19 | C |
| ATOM | 4831 | CD1 | LEU | A | 365 | 21.449 | 71.484 | -7.298 | 1.00 15.78 | C |
| ATOM | 4835 | CD2 | LEU | A | 365 | 23.588 | 70.708 | -6.271 | 1.00 15.77 | C |
| ATOM | 4839 | C | LEU | A | 365 | 25.440 | 74.535 | -7.673 | 1.00 12.83 | C |
| ATOM | 4840 | O | LEU | A | 365 | 26.545 | 74.247 | -8.170 | 1.00 14.41 | O |
| ATOM | 4842 | N | ARG | A | 366 | 24.880 | 75.735 | -7.840 | 1.00 12.30 | N |
| ATOM | 4843 | CA | ARG | A | 366 | 25.384 | 76.650 | -8.853 | 1.00 12.60 | C |
| ATOM | 4845 | CB | ARG | A | 366 | 24.369 | 77.753 | -9.161 | 1.00 13.31 | C |
| ATOM | 4848 | CG | ARG | A | 366 | 24.821 | 78.738 | -10.155 | 1.00 11.54 | C |
| ATOM | 4851 | CD | ARG | A | 366 | 23.660 | 79.474 | -10.788 | 1.00 13.93 | C |
| ATOM | 4854 | NE | ARG | A | 366 | 22.707 | 80.023 | -9.840 | 1.00 14.26 | N |
| ATOM | 4856 | CZ | ARG | A | 366 | 22.646 | 81.303 | -9.493 | 1.00 14.99 | C |
| ATOM | 4857 | NH1 | ARG | A | 366 | 23.462 | 82.208 | -10.030 | 1.00 14.65 | N |
| ATOM | 4860 | NH2 | ARG | A | 366 | 21.687 | 81.709 | -8.670 | 1.00 18.43 | N |
| ATOM | 4863 | C | ARG | A | 366 | 26.795 | 77.230 | -8.516 | 1.00 11.80 | C |
| ATOM | 4864 | O | ARG | A | 366 | 27.538 | 77.575 | -9.435 | 1.00 12.68 | O |
| ATOM | 4866 | N | THR | A | 367 | 27.125 | 77.336 | -7.232 | 1.00 11.63 | N |
| ATOM | 4867 | CA | THR | A | 367 | 28.423 | 77.902 | -6.821 | 1.00 12.25 | C |
| ATOM | 4869 | CB | THR | A | 367 | 28.290 | 79.085 | -5.800 | 1.00 12.77 | C |
| ATOM | 4871 | OG1 | THR | A | 367 | 28.004 | 78.597 | -4.483 | 1.00 12.02 | O |
| ATOM | 4873 | CG2 | THR | A | 367 | 27.256 | 80.123 | -6.251 | 1.00 13.52 | C |
| ATOM | 4877 | C | THR | A | 367 | 29.403 | 76.860 | -6.330 | 1.00 12.28 | C |
| ATOM | 4878 | O | THR | A | 367 | 30.462 | 77.221 | -5.770 | 1.00 11.46 | O |
| ATOM | 4880 | N | SER | A | 368 | 29.084 | 75.593 | -6.590 | 1.00 12.33 | N |
| ATOM | 4881 | CA | SER | A | 368 | 29.841 | 74.473 | -6.061 | 1.00 11.50 | C |
| ATOM | 4883 | CB | SER | A | 368 | 29.095 | 73.154 | -6.245 | 1.00 13.30 | C |
| ATOM | 4886 | OG | SER | A | 368 | 28.815 | 72.828 | -7.609 | 1.00 11.97 | O |
| ATOM | 4888 | C | SER | A | 368 | 31.317 | 74.463 | -6.513 | 1.00 11.76 | C |
| ATOM | 4889 | O | SER | A | 368 | 32.199 | 74.273 | -5.665 | 1.00 12.27 | O |

| | | | | | | | | | |
|---|---|---|---|---|---|---|---|---|---|
| ATOM | 4891 | N | PRO | A | 369 | 31.604 | 74.764 | -7.795 | 1.00 11.87 | N |
| ATOM | 4892 | CA | PRO | A | 369 | 33.044 | 74.821 | -8.156 | 1.00 10.46 | C |
| ATOM | 4894 | CB | PRO | A | 369 | 33.019 | 75.019 | -9.683 | 1.00 12.04 | C |
| ATOM | 4897 | CG | PRO | A | 369 | 31.656 | 74.501 | -10.094 | 1.00 11.14 | C |
| ATOM | 4900 | CD | PRO | A | 369 | 30.761 | 74.995 | -8.990 | 1.00 12.03 | C |
| ATOM | 4903 | C | PRO | A | 369 | 33.806 | 75.995 | -7.452 | 1.00 11.12 | C |
| ATOM | 4904 | O | PRO | A | 369 | 34.982 | 75.861 | -7.145 | 1.00 10.58 | O |
| ATOM | 4905 | N | GLN | A | 370 | 33.139 | 77.124 | -7.292 | 1.00 10.93 | N |
| ATOM | 4906 | CA | GLN | A | 370 | 33.723 | 78.313 | -6.664 | 1.00 11.73 | C |
| ATOM | 4908 | CB | GLN | A | 370 | 32.820 | 79.503 | -6.891 | 1.00 11.35 | C |
| ATOM | 4911 | CG | GLN | A | 370 | 32.695 | 79.986 | -8.367 | 1.00 13.14 | C |
| ATOM | 4914 | CD | GLN | A | 370 | 31.626 | 79.236 | -9.178 | 1.00 12.89 | C |
| ATOM | 4915 | OE1 | GLN | A | 370 | 30.992 | 78.324 | -8.673 | 1.00 10.53 | O |
| ATOM | 4916 | NE2 | GLN | A | 370 | 31.406 | 79.657 | -10.420 | 1.00 12.14 | N |
| ATOM | 4919 | C | GLN | A | 370 | 33.893 | 78.079 | -5.162 | 1.00 12.51 | C |
| ATOM | 4920 | O | GLN | A | 370 | 34.739 | 78.687 | -4.512 | 1.00 12.95 | O |
| ATOM | 4922 | N | TRP | A | 371 | 33.050 | 77.216 | -4.612 | 1.00 11.96 | N |
| ATOM | 4923 | CA | TRP | A | 371 | 33.157 | 76.844 | -3.193 | 1.00 12.00 | C |
| ATOM | 4925 | CB | TRP | A | 371 | 31.825 | 76.312 | -2.735 | 1.00 12.23 | C |
| ATOM | 4928 | CG | TRP | A | 371 | 31.720 | 76.207 | -1.257 | 1.00 12.50 | C |
| ATOM | 4929 | CD1 | TRP | A | 371 | 31.917 | 75.086 | -0.478 | 1.00 11.33 | C |
| ATOM | 4931 | NE1 | TRP | A | 371 | 31.702 | 75.390 | 0.855 | 1.00 13.17 | N |
| ATOM | 4933 | CE2 | TRP | A | 371 | 31.380 | 76.715 | 0.968 | 1.00 12.45 | C |
| ATOM | 4934 | CD2 | TRP | A | 371 | 31.363 | 77.267 | -0.341 | 1.00 10.50 | C |
| ATOM | 4935 | CE3 | TRP | A | 371 | 31.107 | 78.647 | -0.474 | 1.00 12.29 | C |
| ATOM | 4937 | CZ3 | TRP | A | 371 | 30.811 | 79.388 | 0.667 | 1.00 12.69 | C |
| ATOM | 4939 | CH2 | TRP | A | 371 | 30.793 | 78.786 | 1.945 | 1.00 11.30 | C |
| ATOM | 4941 | CZ2 | TRP | A | 371 | 31.078 | 77.463 | 2.104 | 1.00 14.33 | C |
| ATOM | 4943 | C | TRP | A | 371 | 34.233 | 75.821 | -2.929 | 1.00 12.38 | C |
| ATOM | 4944 | O | TRP | A | 371 | 35.028 | 75.977 | -1.997 | 1.00 14.55 | O |
| ATOM | 4946 | N | LEU | A | 372 | 34.231 | 74.747 | -3.711 | 1.00 12.85 | N |
| ATOM | 4947 | CA | LEU | A | 372 | 35.191 | 73.681 | -3.502 | 1.00 12.56 | C |
| ATOM | 4949 | CB | LEU | A | 372 | 34.639 | 72.415 | -4.143 | 1.00 12.77 | C |
| ATOM | 4952 | CG | LEU | A | 372 | 33.395 | 71.827 | -3.514 | 1.00 13.44 | C |
| ATOM | 4954 | CD1 | LEU | A | 372 | 32.992 | 70.623 | -4.355 | 1.00 14.32 | C |
| ATOM | 4958 | CD2 | LEU | A | 372 | 33.621 | 71.412 | -2.088 | 1.00 17.11 | C |
| ATOM | 4962 | C | LEU | A | 372 | 36.596 | 74.006 | -4.073 | 1.00 12.75 | C |
| ATOM | 4963 | O | LEU | A | 372 | 37.634 | 73.514 | -3.560 | 1.00 11.99 | O |
| ATOM | 4965 | N | GLY | A | 373 | 36.678 | 74.767 | -5.157 | 1.00 11.17 | N |
| ATOM | 4966 | CA | GLY | A | 373 | 37.972 | 75.086 | -5.764 | 1.00 12.12 | C |
| ATOM | 4969 | C | GLY | A | 373 | 39.040 | 75.495 | -4.775 | 1.00 12.21 | C |
| ATOM | 4970 | O | GLY | A | 373 | 40.140 | 74.938 | -4.761 | 1.00 12.31 | O |
| ATOM | 4972 | N | PRO | A | 374 | 38.750 | 76.513 | -3.949 | 1.00 11.59 | N |
| ATOM | 4973 | CA | PRO | A | 374 | 39.808 | 76.972 | -3.034 | 1.00 13.10 | C |
| ATOM | 4975 | CB | PRO | A | 374 | 39.161 | 78.183 | -2.333 | 1.00 13.29 | C |
| ATOM | 4978 | CG | PRO | A | 374 | 38.129 | 78.681 | -3.327 | 1.00 14.60 | C |
| ATOM | 4981 | CD | PRO | A | 374 | 37.584 | 77.432 | -3.954 | 1.00 12.65 | C |
| ATOM | 4984 | C | PRO | A | 374 | 40.338 | 75.927 | -2.071 | 1.00 13.02 | C |
| ATOM | 4985 | O | PRO | A | 374 | 41.565 | 75.816 | -1.872 | 1.00 13.80 | O |
| ATOM | 4986 | N | LEU | A | 375 | 39.433 | 75.131 | -1.501 | 1.00 12.07 | N |
| ATOM | 4987 | CA | LEU | A | 375 | 39.850 | 74.125 | -0.542 | 1.00 12.62 | C |
| ATOM | 4989 | CB | LEU | A | 375 | 38.711 | 73.677 | 0.337 | 1.00 14.33 | C |
| ATOM | 4992 | CG | LEU | A | 375 | 37.653 | 72.854 | -0.311 | 1.00 12.67 | C |
| ATOM | 4994 | CD1 | LEU | A | 375 | 37.960 | 71.359 | -0.356 | 1.00 15.87 | C |
| ATOM | 4998 | CD2 | LEU | A | 375 | 36.289 | 73.053 | 0.424 | 1.00 14.42 | C |
| ATOM | 5002 | C | LEU | A | 375 | 40.585 | 72.952 | -1.231 | 1.00 12.20 | C |
| ATOM | 5003 | O | LEU | A | 375 | 41.493 | 72.360 | -0.636 | 1.00 14.13 | O |

| ATOM | 5005 | N | VAL | A | 376 | 40.254 | 72.662 | -2.508 | 1.00 | 12.33 | N |
|------|------|-----|-----|---|-----|--------|--------|--------|------|-------|---|
| ATOM | 5006 | CA | VAL | A | 376 | 41.002 | 71.680 | -3.277 | 1.00 | 12.61 | C |
| ATOM | 5008 | CB | VAL | A | 376 | 40.318 | 71.295 | -4.586 | 1.00 | 12.29 | C |
| ATOM | 5010 | CG1 | VAL | A | 376 | 41.217 | 70.472 | -5.487 | 1.00 | 12.79 | C |
| ATOM | 5014 | CG2 | VAL | A | 376 | 39.040 | 70.556 | -4.279 | 1.00 | 13.76 | C |
| ATOM | 5018 | C | VAL | A | 376 | 42.438 | 72.128 | -3.518 | 1.00 | 12.67 | C |
| ATOM | 5019 | O | VAL | A | 376 | 43.368 | 71.316 | -3.387 | 1.00 | 13.37 | O |
| ATOM | 5021 | N | SER | A | 377 | 42.626 | 73.415 | -3.810 | 1.00 | 12.95 | N |
| ATOM | 5022 | CA | SER | A | 377 | 43.982 | 73.944 | -3.989 | 1.00 | 12.73 | C |
| ATOM | 5024 | CB | SER | A | 377 | 43.982 | 75.383 | -4.410 | 1.00 | 14.03 | C |
| ATOM | 5027 | OG | SER | A | 377 | 45.298 | 75.785 | -4.799 | 1.00 | 14.66 | O |
| ATOM | 5029 | C | SER | A | 377 | 44.797 | 73.774 | -2.686 | 1.00 | 12.06 | C |
| ATOM | 5030 | O | SER | A | 377 | 45.993 | 73.444 | -2.736 | 1.00 | 11.24 | O |
| ATOM | 5032 | N | ASP | A | 378 | 44.141 | 73.984 | -1.532 | 1.00 | 12.79 | N |
| ATOM | 5033 | CA | ASP | A | 378 | 44.783 | 73.750 | -0.248 | 1.00 | 12.85 | C |
| ATOM | 5035 | CB | ASP | A | 378 | 43.882 | 74.167 | 0.904 | 1.00 | 13.15 | C |
| ATOM | 5038 | CG | ASP | A | 378 | 43.797 | 75.644 | 1.065 | 1.00 | 15.61 | C |
| ATOM | 5039 | OD1 | ASP | A | 378 | 44.565 | 76.373 | 0.397 | 1.00 | 17.65 | O |
| ATOM | 5040 | OD2 | ASP | A | 378 | 42.952 | 76.114 | 1.875 | 1.00 | 18.91 | O |
| ATOM | 5041 | C | ASP | A | 378 | 45.204 | 72.295 | -0.044 | 1.00 | 12.78 | C |
| ATOM | 5042 | O | ASP | A | 378 | 46.270 | 72.018 | 0.474 | 1.00 | 13.35 | O |
| ATOM | 5044 | N | LEU | A | 379 | 44.337 | 71.364 | -0.438 | 1.00 | 12.91 | N |
| ATOM | 5045 | CA | LEU | A | 379 | 44.629 | 69.910 | -0.325 | 1.00 | 13.19 | C |
| ATOM | 5047 | CB | LEU | A | 379 | 43.416 | 69.047 | -0.655 | 1.00 | 13.81 | C |
| ATOM | 5050 | CG | LEU | A | 379 | 42.246 | 69.182 | 0.346 | 1.00 | 13.90 | C |
| ATOM | 5052 | CD1 | LEU | A | 379 | 41.011 | 68.484 | -0.175 | 1.00 | 12.94 | C |
| ATOM | 5056 | CD2 | LEU | A | 379 | 42.659 | 68.653 | 1.682 | 1.00 | 19.03 | C |
| ATOM | 5060 | C | LEU | A | 379 | 45.806 | 69.513 | -1.218 | 1.00 | 12.52 | C |
| ATOM | 5061 | O | LEU | A | 379 | 46.697 | 68.752 | -0.841 | 1.00 | 12.64 | O |
| ATOM | 5063 | N | ILE | A | 380 | 45.857 | 70.107 | -2.404 | 1.00 | 12.32 | N |
| ATOM | 5064 | CA | ILE | A | 380 | 46.996 | 69.894 | -3.307 | 1.00 | 12.19 | C |
| ATOM | 5066 | CB | ILE | A | 380 | 46.706 | 70.427 | -4.709 | 1.00 | 13.08 | C |
| ATOM | 5068 | CG1 | ILE | A | 380 | 45.536 | 69.624 | -5.285 | 1.00 | 12.84 | C |
| ATOM | 5071 | CD1 | ILE | A | 380 | 45.004 | 70.142 | -6.609 | 1.00 | 13.76 | C |
| ATOM | 5075 | CG2 | ILE | A | 380 | 47.932 | 70.352 | -5.599 | 1.00 | 12.43 | C |
| ATOM | 5079 | C | ILE | A | 380 | 48.281 | 70.475 | -2.722 | 1.00 | 12.21 | C |
| ATOM | 5080 | O | ILE | A | 380 | 49.349 | 69.863 | -2.873 | 1.00 | 12.22 | O |
| ATOM | 5082 | N | HIS | A | 381 | 48.192 | 71.658 | -2.134 | 1.00 | 11.73 | N |
| ATOM | 5083 | CA | HIS | A | 381 | 49.324 | 72.282 | -1.466 | 1.00 | 11.83 | C |
| ATOM | 5085 | CB | HIS | A | 381 | 48.909 | 73.684 | -0.960 | 1.00 | 12.14 | C |
| ATOM | 5088 | CG | HIS | A | 381 | 50.036 | 74.454 | -0.339 | 1.00 | 12.62 | C |
| ATOM | 5089 | ND1 | HIS | A | 381 | 50.400 | 74.292 | 0.976 | 1.00 | 14.64 | N |
| ATOM | 5091 | CE1 | HIS | A | 381 | 51.446 | 75.067 | 1.229 | 1.00 | 14.47 | C |
| ATOM | 5093 | NE2 | HIS | A | 381 | 51.741 | 75.746 | 0.139 | 1.00 | 16.14 | N |
| ATOM | 5095 | CD2 | HIS | A | 381 | 50.873 | 75.382 | -0.854 | 1.00 | 14.94 | C |
| ATOM | 5097 | C | HIS | A | 381 | 49.810 | 71.427 | -0.294 | 1.00 | 10.94 | C |
| ATOM | 5098 | O | HIS | A | 381 | 51.001 | 71.200 | -0.145 | 1.00 | 12.23 | O |
| ATOM | 5100 | N | ALA | A | 382 | 48.880 | 70.968 | 0.536 | 1.00 | 11.37 | N |
| ATOM | 5101 | CA | ALA | A | 382 | 49.189 | 70.084 | 1.656 | 1.00 | 11.63 | C |
| ATOM | 5103 | CB | ALA | A | 382 | 47.939 | 69.683 | 2.369 | 1.00 | 11.98 | C |
| ATOM | 5107 | C | ALA | A | 382 | 49.918 | 68.835 | 1.167 | 1.00 | 10.72 | C |
| ATOM | 5108 | O | ALA | A | 382 | 50.868 | 68.386 | 1.811 | 1.00 | 11.96 | O |
| ATOM | 5110 | N | HIS | A | 383 | 49.520 | 68.341 | -0.002 | 1.00 | 9.85 | N |
| ATOM | 5111 | CA | HIS | A | 383 | 50.111 | 67.154 | -0.570 | 1.00 | 11.97 | C |
| ATOM | 5113 | CB | HIS | A | 383 | 49.325 | 66.717 | -1.815 | 1.00 | 11.57 | C |
| ATOM | 5116 | CG | HIS | A | 383 | 49.537 | 65.291 | -2.163 | 1.00 | 11.55 | C |
| ATOM | 5117 | ND1 | HIS | A | 383 | 48.712 | 64.272 | -1.706 | 1.00 | 13.67 | N |

| | | | | | | | | | |
|---|---|---|---|---|---|---|---|---|---|
| ATOM | 5119 | CE1 | HIS | A | 383 | 49.195 | 63.120 | -2.109 | 1.00 15.34 | C |
| ATOM | 5121 | NE2 | HIS | A | 383 | 50.313 | 63.339 | -2.788 | 1.00 15.16 | N |
| ATOM | 5123 | CD2 | HIS | A | 383 | 50.568 | 64.682 | -2.796 | 1.00 15.09 | C |
| ATOM | 5125 | C | HIS | A | 383 | 51.577 | 67.391 | -0.871 | 1.00 11.69 | C |
| ATOM | 5126 | O | HIS | A | 383 | 52.420 | 66.559 | -0.565 | 1.00 12.73 | O |
| ATOM | 5128 | N | ALA | A | 384 | 51.909 | 68.531 | -1.468 | 1.00 11.30 | N |
| ATOM | 5129 | CA | ALA | A | 384 | 53.312 | 68.844 | -1.743 | 1.00 12.82 | C |
| ATOM | 5131 | CB | ALA | A | 384 | 53.412 | 70.068 | -2.543 | 1.00 13.08 | C |
| ATOM | 5135 | C | ALA | A | 384 | 54.127 | 69.000 | -0.459 | 1.00 12.43 | C |
| ATOM | 5136 | O | ALA | A | 384 | 55.263 | 68.529 | -0.375 | 1.00 12.29 | O |
| ATOM | 5138 | N | VAL | A | 385 | 53.535 | 69.623 | 0.546 | 1.00 11.95 | N |
| ATOM | 5139 | CA | VAL | A | 385 | 54.229 | 69.858 | 1.799 | 1.00 11.84 | C |
| ATOM | 5141 | CB | VAL | A | 385 | 53.422 | 70.736 | 2.726 | 1.00 10.92 | C |
| ATOM | 5143 | CG1 | VAL | A | 385 | 54.085 | 70.765 | 4.117 | 1.00 14.32 | C |
| ATOM | 5147 | CG2 | VAL | A | 385 | 53.270 | 72.133 | 2.107 | 1.00 11.95 | C |
| ATOM | 5151 | C | VAL | A | 385 | 54.519 | 68.505 | 2.464 | 1.00 10.54 | C |
| ATOM | 5152 | O | VAL | A | 385 | 55.651 | 68.214 | 2.874 | 1.00 11.05 | O |
| ATOM | 5154 | N | LEU | A | 386 | 53.495 | 67.677 | 2.626 | 1.00 11.65 | N |
| ATOM | 5155 | CA | LEU | A | 386 | 53.673 | 66.384 | 3.296 | 1.00 12.51 | C |
| ATOM | 5157 | CB | LEU | A | 386 | 52.351 | 65.702 | 3.585 | 1.00 12.71 | C |
| ATOM | 5160 | CG | LEU | A | 386 | 51.502 | 66.307 | 4.671 | 1.00 16.14 | C |
| ATOM | 5162 | CD1 | LEU | A | 386 | 50.242 | 65.492 | 4.913 | 1.00 14.16 | C |
| ATOM | 5166 | CD2 | LEU | A | 386 | 52.258 | 66.399 | 6.018 | 1.00 16.42 | C |
| ATOM | 5170 | C | LEU | A | 386 | 54.574 | 65.421 | 2.515 | 1.00 12.17 | C |
| ATOM | 5171 | O | LEU | A | 386 | 55.289 | 64.585 | 3.108 | 1.00 12.15 | O |
| ATOM | 5173 | N | THR | A | 387 | 54.580 | 65.540 | 1.181 | 1.00 12.22 | N |
| ATOM | 5174 | CA | THR | A | 387 | 55.486 | 64.723 | 0.390 | 1.00 12.24 | C |
| ATOM | 5176 | CB | THR | A | 387 | 55.257 | 64.858 | -1.103 | 1.00 12.38 | C |
| ATOM | 5178 | OG1 | THR | A | 387 | 53.935 | 64.387 | -1.382 | 1.00 12.81 | O |
| ATOM | 5180 | CG2 | THR | A | 387 | 56.256 | 64.017 | -1.879 | 1.00 13.63 | C |
| ATOM | 5184 | C | THR | A | 387 | 56.948 | 64.990 | 0.750 | 1.00 11.91 | C |
| ATOM | 5185 | O | THR | A | 387 | 57.711 | 64.056 | 0.975 | 1.00 12.25 | O |
| ATOM | 5187 | N | ILE | A | 388 | 57.317 | 66.252 | 0.908 | 1.00 13.02 | N |
| ATOM | 5188 | CA | ILE | A | 388 | 58.674 | 66.568 | 1.321 | 1.00 12.96 | C |
| ATOM | 5190 | CB | ILE | A | 388 | 58.969 | 68.070 | 1.137 | 1.00 12.79 | C |
| ATOM | 5192 | CG1 | ILE | A | 388 | 58.979 | 68.374 | -0.368 | 1.00 13.63 | C |
| ATOM | 5195 | CD1 | ILE | A | 388 | 59.053 | 69.821 | -0.705 | 1.00 15.64 | C |
| ATOM | 5199 | CG2 | ILE | A | 388 | 60.280 | 68.457 | 1.854 | 1.00 14.15 | C |
| ATOM | 5203 | C | ILE | A | 388 | 58.927 | 66.126 | 2.760 | 1.00 13.04 | C |
| ATOM | 5204 | O | ILE | A | 388 | 59.945 | 65.517 | 3.071 | 1.00 13.41 | O |
| ATOM | 5206 | N | GLU | A | 389 | 57.982 | 66.405 | 3.642 | 1.00 12.90 | N |
| ATOM | 5207 | CA | GLU | A | 389 | 58.190 | 66.130 | 5.052 | 1.00 12.87 | C |
| ATOM | 5209 | CB | GLU | A | 389 | 57.012 | 66.703 | 5.835 | 1.00 13.86 | C |
| ATOM | 5212 | CG | GLU | A | 389 | 57.152 | 66.551 | 7.357 | 1.00 15.62 | C |
| ATOM | 5215 | CD | GLU | A | 389 | 58.200 | 67.444 | 7.949 | 1.00 16.50 | C |
| ATOM | 5216 | OE1 | GLU | A | 389 | 58.875 | 68.198 | 7.171 | 1.00 14.44 | O |
| ATOM | 5217 | OE2 | GLU | A | 389 | 58.301 | 67.442 | 9.208 | 1.00 14.91 | O |
| ATOM | 5218 | C | GLU | A | 389 | 58.320 | 64.610 | 5.342 | 1.00 13.49 | C |
| ATOM | 5219 | O | GLU | A | 389 | 59.161 | 64.159 | 6.146 | 1.00 13.71 | O |
| ATOM | 5221 | N | ALA | A | 390 | 57.414 | 63.845 | 4.747 | 1.00 12.73 | N |
| ATOM | 5222 | CA | ALA | A | 390 | 57.361 | 62.406 | 4.965 | 1.00 14.50 | C |
| ATOM | 5224 | CB | ALA | A | 390 | 55.992 | 61.871 | 4.652 | 1.00 15.20 | C |
| ATOM | 5228 | C | ALA | A | 390 | 58.438 | 61.653 | 4.196 | 1.00 14.14 | C |
| ATOM | 5229 | O | ALA | A | 390 | 58.975 | 60.658 | 4.696 | 1.00 17.01 | O |
| ATOM | 5231 | N | GLY | A | 391 | 58.769 | 62.133 | 3.001 | 1.00 13.39 | N |
| ATOM | 5232 | CA | GLY | A | 391 | 59.586 | 61.382 | 2.037 | 1.00 13.45 | C |
| ATOM | 5235 | C | GLY | A | 391 | 61.000 | 61.875 | 1.783 | 1.00 14.05 | C |

| | | | | | | | | |
|---|---|---|---|---|---|---|---|---|
| ATOM | 5236 | O | GLY A 391 | 61.802 | 61.138 | 1.211 | 1.00 14.00 | O |
| ATOM | 5238 | N | GLN A 392 | 61.307 | 63.138 | 2.129 | 1.00 13.93 | N |
| ATOM | 5239 | CA | GLN A 392 | 62.556 | 63.751 | 1.699 | 1.00 14.71 | C |
| ATOM | 5241 | CB | GLN A 392 | 62.309 | 64.622 | 0.455 | 1.00 15.30 | C |
| ATOM | 5244 | CG | GLN A 392 | 61.610 | 63.923 | -0.678 | 1.00 16.60 | C |
| ATOM | 5247 | CD | GLN A 392 | 61.047 | 64.911 | -1.700 | 1.00 17.20 | C |
| ATOM | 5248 | OE1 | GLN A 392 | 59.933 | 64.695 | -2.212 | 1.00 21.45 | O |
| ATOM | 5249 | NE2 | GLN A 392 | 61.790 | 66.010 | -1.975 | 1.00 16.02 | N |
| ATOM | 5252 | C | GLN A 392 | 63.232 | 64.612 | 2.770 | 1.00 14.02 | C |
| ATOM | 5253 | O | GLN A 392 | 64.038 | 65.508 | 2.441 | 1.00 14.30 | O |
| ATOM | 5255 | N | SER A 393 | 62.902 | 64.348 | 4.027 | 1.00 13.20 | N |
| ATOM | 5256 | CA | SER A 393 | 63.353 | 65.183 | 5.153 | 1.00 12.89 | C |
| ATOM | 5258 | CB | SER A 393 | 62.185 | 65.985 | 5.721 | 1.00 13.51 | C |
| ATOM | 5261 | OG | SER A 393 | 61.710 | 66.872 | 4.719 | 1.00 14.72 | O |
| ATOM | 5263 | C | SER A 393 | 64.030 | 64.397 | 6.273 | 1.00 14.42 | C |
| ATOM | 5264 | O | SER A 393 | 63.593 | 63.283 | 6.660 | 1.00 14.34 | O |
| ATOM | 5266 | N | THR A 394 | 65.140 | 64.976 | 6.736 | 1.00 12.66 | N |
| ATOM | 5267 | CA | THR A 394 | 65.801 | 64.545 | 7.955 | 1.00 12.30 | C |
| ATOM | 5269 | CB | THR A 394 | 67.311 | 64.715 | 7.801 | 1.00 11.88 | C |
| ATOM | 5271 | OG1 | THR A 394 | 67.781 | 63.934 | 6.675 | 1.00 11.48 | O |
| ATOM | 5273 | CG2 | THR A 394 | 68.003 | 64.332 | 9.065 | 1.00 13.94 | C |
| ATOM | 5277 | C | THR A 394 | 65.289 | 65.487 | 9.058 | 1.00 14.25 | C |
| ATOM | 5278 | O | THR A 394 | 65.414 | 66.736 | 8.961 | 1.00 12.02 | O |
| ATOM | 5280 | N | THR A 395 | 64.684 | 64.915 | 10.090 | 1.00 13.56 | N |
| ATOM | 5281 | CA | THR A 395 | 64.008 | 65.731 | 11.083 | 1.00 14.08 | C |
| ATOM | 5283 | CB | THR A 395 | 62.492 | 65.501 | 11.053 | 1.00 13.79 | C |
| ATOM | 5285 | OG1 | THR A 395 | 62.163 | 64.161 | 11.441 | 1.00 13.94 | O |
| ATOM | 5287 | CG2 | THR A 395 | 61.953 | 65.841 | 9.660 | 1.00 14.21 | C |
| ATOM | 5291 | C | THR A 395 | 64.538 | 65.561 | 12.509 | 1.00 14.50 | C |
| ATOM | 5292 | O | THR A 395 | 64.007 | 66.144 | 13.450 | 1.00 14.91 | O |
| ATOM | 5294 | N | ASP A 396 | 65.632 | 64.828 | 12.668 | 1.00 14.50 | N |
| ATOM | 5295 | CA | ASP A 396 | 66.276 | 64.769 | 13.958 | 1.00 14.17 | C |
| ATOM | 5297 | CB | ASP A 396 | 66.866 | 63.361 | 14.212 | 1.00 14.23 | C |
| ATOM | 5300 | CG | ASP A 396 | 68.021 | 63.032 | 13.284 | 1.00 13.94 | C |
| ATOM | 5301 | OD1 | ASP A 396 | 67.799 | 62.939 | 12.047 | 1.00 15.04 | O |
| ATOM | 5302 | OD2 | ASP A 396 | 69.125 | 62.734 | 13.804 | 1.00 16.86 | O |
| ATOM | 5303 | C | ASP A 396 | 67.293 | 65.902 | 14.071 | 1.00 14.15 | C |
| ATOM | 5304 | O | ASP A 396 | 67.277 | 66.814 | 13.287 | 1.00 14.10 | O |
| ATOM | 5306 | N | ASN A 397 | 68.130 | 65.856 | 15.101 | 1.00 14.71 | N |
| ATOM | 5307 | CA | ASN A 397 | 69.041 | 66.937 | 15.443 | 1.00 13.14 | C |
| ATOM | 5309 | CB | ASN A 397 | 68.263 | 68.171 | 15.978 | 1.00 13.71 | C |
| ATOM | 5312 | CG | ASN A 397 | 69.140 | 69.394 | 16.137 | 1.00 13.94 | C |
| ATOM | 5313 | OD1 | ASN A 397 | 69.582 | 69.968 | 15.145 | 1.00 16.49 | O |
| ATOM | 5314 | ND2 | ASN A 397 | 69.407 | 69.788 | 17.383 | 1.00 14.95 | N |
| ATOM | 5317 | C | ASN A 397 | 69.971 | 66.369 | 16.534 | 1.00 13.50 | C |
| ATOM | 5318 | O | ASN A 397 | 69.501 | 65.555 | 17.367 | 1.00 13.56 | O |
| ATOM | 5320 | N | PRO A 398 | 71.198 | 66.879 | 16.662 | 1.00 13.79 | N |
| ATOM | 5321 | CA | PRO A 398 | 71.950 | 67.604 | 15.631 | 1.00 14.02 | C |
| ATOM | 5323 | CB | PRO A 398 | 73.294 | 67.971 | 16.327 | 1.00 14.37 | C |
| ATOM | 5326 | CG | PRO A 398 | 73.195 | 67.378 | 17.702 | 1.00 16.65 | C |
| ATOM | 5329 | CD | PRO A 398 | 71.984 | 66.576 | 17.866 | 1.00 14.34 | C |
| ATOM | 5332 | C | PRO A 398 | 72.214 | 66.738 | 14.421 | 1.00 13.23 | C |
| ATOM | 5333 | O | PRO A 398 | 72.132 | 65.507 | 14.496 | 1.00 14.09 | O |
| ATOM | 5334 | N | LEU A 399 | 72.568 | 67.381 | 13.337 | 1.00 13.25 | N |
| ATOM | 5335 | CA | LEU A 399 | 72.718 | 66.706 | 12.041 | 1.00 13.94 | C |
| ATOM | 5337 | CB | LEU A 399 | 71.768 | 67.322 | 11.009 | 1.00 14.39 | C |
| ATOM | 5340 | CG | LEU A 399 | 70.304 | 67.126 | 11.362 | 1.00 14.65 | C |

| ATOM | 5342 | CD1 | LEU A 399 | 69.443 | 67.633 | 10.233 | 1.00 | 16.53 | C |
| --- | --- | --- | --- | --- | --- | --- | --- | --- | --- |
| ATOM | 5346 | CD2 | LEU A 399 | 69.971 | 65.694 | 11.674 | 1.00 | 15.09 | C |
| ATOM | 5350 | C | LEU A 399 | 74.165 | 66.776 | 11.605 | 1.00 | 14.90 | C |
| ATOM | 5351 | O | LEU A 399 | 74.863 | 67.760 | 11.869 | 1.00 | 15.18 | O |
| ATOM | 5353 | N | ILE A 400 | 74.596 | 65.713 | 10.927 | 1.00 | 15.17 | N |
| ATOM | 5354 | CA | ILE A 400 | 76.008 | 65.475 | 10.666 | 1.00 | 16.05 | C |
| ATOM | 5356 | CB | ILE A 400 | 76.335 | 64.006 | 11.029 | 1.00 | 16.89 | C |
| ATOM | 5358 | CG1 | ILE A 400 | 75.991 | 63.697 | 12.496 | 1.00 | 19.64 | C |
| ATOM | 5361 | CD1 | ILE A 400 | 76.640 | 64.596 | 13.493 | 1.00 | 23.53 | C |
| ATOM | 5365 | CG2 | ILE A 400 | 77.745 | 63.686 | 10.726 | 1.00 | 18.30 | C |
| ATOM | 5369 | C | ILE A 400 | 76.302 | 65.686 | 9.182 | 1.00 | 15.89 | C |
| ATOM | 5370 | O | ILE A 400 | 75.642 | 65.064 | 8.354 | 1.00 | 14.20 | O |
| ATOM | 5372 | N | ASP A 401 | 77.248 | 66.581 | 8.862 | 1.00 | 16.38 | N |
| ATOM | 5373 | CA | ASP A 401 | 77.672 | 66.770 | 7.491 | 1.00 | 17.67 | C |
| ATOM | 5375 | CB | ASP A 401 | 77.785 | 68.237 | 7.092 | 1.00 | 17.59 | C |
| ATOM | 5378 | CG | ASP A 401 | 78.249 | 68.403 | 5.630 | 1.00 | 18.52 | C |
| ATOM | 5379 | OD1 | ASP A 401 | 78.470 | 67.382 | 4.895 | 1.00 | 24.86 | O |
| ATOM | 5380 | OD2 | ASP A 401 | 78.366 | 69.548 | 5.193 | 1.00 | 24.65 | O |
| ATOM | 5381 | C | ASP A 401 | 79.023 | 66.099 | 7.331 | 1.00 | 18.91 | C |
| ATOM | 5382 | O | ASP A 401 | 80.042 | 66.652 | 7.683 | 1.00 | 18.42 | O |
| ATOM | 5384 | N | VAL A 402 | 78.993 | 64.904 | 6.786 | 1.00 | 20.75 | N |
| ATOM | 5385 | CA | VAL A 402 | 80.190 | 64.062 | 6.719 | 1.00 | 22.70 | C |
| ATOM | 5387 | CB | VAL A 402 | 79.778 | 62.593 | 6.374 | 1.00 | 22.26 | C |
| ATOM | 5389 | CG1 | VAL A 402 | 80.974 | 61.726 | 6.089 | 1.00 | 24.64 | C |
| ATOM | 5393 | CG2 | VAL A 402 | 78.987 | 61.980 | 7.519 | 1.00 | 20.88 | C |
| ATOM | 5397 | C | VAL A 402 | 81.178 | 64.626 | 5.705 | 1.00 | 24.48 | C |
| ATOM | 5398 | O | VAL A 402 | 82.395 | 64.599 | 5.921 | 1.00 | 25.03 | O |
| ATOM | 5400 | N | GLU A 403 | 80.656 | 65.154 | 4.608 | 1.00 | 26.96 | N |
| ATOM | 5401 | CA | GLU A 403 | 81.498 | 65.657 | 3.517 | 1.00 | 29.11 | C |
| ATOM | 5403 | CB | GLU A 403 | 80.625 | 66.048 | 2.317 | 1.00 | 29.65 | C |
| ATOM | 5406 | CG | GLU A 403 | 79.821 | 64.859 | 1.698 | 1.00 | 32.64 | C |
| ATOM | 5409 | CD | GLU A 403 | 78.715 | 65.317 | 0.700 | 1.00 | 33.94 | C |
| ATOM | 5410 | OE1 | GLU A 403 | 79.051 | 65.998 | -0.311 | 1.00 | 40.16 | O |
| ATOM | 5411 | OE2 | GLU A 403 | 77.507 | 64.984 | 0.918 | 1.00 | 40.89 | O |
| ATOM | 5412 | C | GLU A 403 | 82.347 | 66.839 | 3.990 | 1.00 | 27.99 | C |
| ATOM | 5413 | O | GLU A 403 | 83.502 | 66.989 | 3.580 | 1.00 | 28.10 | O |
| ATOM | 5415 | N | ASN A 404 | 81.792 | 67.654 | 4.882 | 1.00 | 26.80 | N |
| ATOM | 5416 | CA | ASN A 404 | 82.511 | 68.778 | 5.445 | 1.00 | 25.93 | C |
| ATOM | 5418 | CB | ASN A 404 | 81.666 | 70.027 | 5.259 | 1.00 | 26.75 | C |
| ATOM | 5421 | CG | ASN A 404 | 81.379 | 70.285 | 3.791 | 1.00 | 28.41 | C |
| ATOM | 5422 | OD1 | ASN A 404 | 82.314 | 70.485 | 3.001 | 1.00 | 33.57 | O |
| ATOM | 5423 | ND2 | ASN A 404 | 80.112 | 70.222 | 3.403 | 1.00 | 27.78 | N |
| ATOM | 5426 | C | ASN A 404 | 82.951 | 68.578 | 6.885 | 1.00 | 25.01 | C |
| ATOM | 5427 | O | ASN A 404 | 83.399 | 69.513 | 7.545 | 1.00 | 24.20 | O |
| ATOM | 5429 | N | LYS A 405 | 82.835 | 67.341 | 7.362 | 1.00 | 24.35 | N |
| ATOM | 5430 | CA | LYS A 405 | 83.367 | 66.939 | 8.656 | 1.00 | 24.12 | C |
| ATOM | 5432 | CB | LYS A 405 | 84.904 | 66.841 | 8.603 | 1.00 | 24.55 | C |
| ATOM | 5435 | CG | LYS A 405 | 85.395 | 65.740 | 7.675 | 1.00 | 27.24 | C |
| ATOM | 5438 | CD | LYS A 405 | 86.894 | 65.525 | 7.881 | 1.00 | 27.80 | C |
| ATOM | 5441 | CE | LYS A 405 | 87.591 | 65.137 | 6.575 | 1.00 | 32.15 | C |
| ATOM | 5444 | NZ | LYS A 405 | 89.100 | 65.063 | 6.755 | 1.00 | 33.67 | N |
| ATOM | 5448 | C | LYS A 405 | 82.901 | 67.843 | 9.774 | 1.00 | 22.82 | C |
| ATOM | 5449 | O | LYS A 405 | 83.679 | 68.293 | 10.623 | 1.00 | 21.31 | O |
| ATOM | 5451 | N | THR A 406 | 81.588 | 68.077 | 9.800 | 1.00 | 21.71 | N |
| ATOM | 5452 | CA | THR A 406 | 81.036 | 68.991 | 10.795 | 1.00 | 22.18 | C |
| ATOM | 5454 | CB | THR A 406 | 81.056 | 70.451 | 10.254 | 1.00 | 22.61 | C |
| ATOM | 5456 | OG1 | THR A 406 | 80.763 | 71.361 | 11.319 | 1.00 | 26.05 | O |

| ATOM | 5458 | CG2 | THR A 406 | 80.086 | 70.632 | 9.093 | 1.00 | 23.29 | C |
| --- | --- | --- | --- | --- | --- | --- | --- | --- | --- |
| ATOM | 5462 | C | THR A 406 | 79.624 | 68.584 | 11.180 | 1.00 | 20.54 | C |
| ATOM | 5463 | O | THR A 406 | 78.965 | 67.836 | 10.485 | 1.00 | 21.73 | O |
| ATOM | 5465 | N | SER A 407 | 79.182 | 69.078 | 12.314 | 1.00 | 19.18 | N |
| ATOM | 5466 | CA | SER A 407 | 77.808 | 68.881 | 12.710 | 1.00 | 18.71 | C |
| ATOM | 5468 | CB | SER A 407 | 77.717 | 68.061 | 13.971 | 1.00 | 19.31 | C |
| ATOM | 5471 | OG | SER A 407 | 78.396 | 68.756 | 14.984 | 1.00 | 25.19 | O |
| ATOM | 5473 | C | SER A 407 | 77.144 | 70.232 | 12.890 | 1.00 | 17.17 | C |
| ATOM | 5474 | O | SER A 407 | 77.815 | 71.243 | 13.057 | 1.00 | 16.50 | O |
| ATOM | 5476 | N | HIS A 408 | 75.822 | 70.217 | 12.815 | 1.00 | 14.23 | N |
| ATOM | 5477 | CA | HIS A 408 | 75.006 | 71.432 | 12.795 | 1.00 | 13.81 | C |
| ATOM | 5479 | CB | HIS A 408 | 74.448 | 71.692 | 11.410 | 1.00 | 13.06 | C |
| ATOM | 5482 | CG | HIS A 408 | 75.493 | 71.952 | 10.374 | 1.00 | 12.92 | C |
| ATOM | 5483 | ND1 | HIS A 408 | 75.941 | 73.222 | 10.071 | 1.00 | 14.75 | N |
| ATOM | 5485 | CE1 | HIS A 408 | 76.846 | 73.144 | 9.104 | 1.00 | 16.14 | C |
| ATOM | 5487 | NE2 | HIS A 408 | 76.983 | 71.874 | 8.749 | 1.00 | 13.58 | N |
| ATOM | 5489 | CD2 | HIS A 408 | 76.140 | 71.111 | 9.530 | 1.00 | 15.02 | C |
| ATOM | 5491 | C | HIS A 408 | 73.833 | 71.279 | 13.772 | 1.00 | 13.05 | C |
| ATOM | 5492 | O | HIS A 408 | 73.226 | 70.220 | 13.893 | 1.00 | 12.84 | O |
| ATOM | 5494 | N | HIS A 409 | 73.536 | 72.364 | 14.483 | 1.00 | 13.44 | N |
| ATOM | 5495 | CA | HIS A 409 | 72.490 | 72.401 | 15.491 | 1.00 | 13.59 | C |
| ATOM | 5497 | CB | HIS A 409 | 73.065 | 73.014 | 16.760 | 1.00 | 15.90 | C |
| ATOM | 5500 | CG | HIS A 409 | 74.113 | 72.156 | 17.369 | 1.00 | 18.61 | C |
| ATOM | 5501 | ND1 | HIS A 409 | 73.817 | 71.045 | 18.144 | 1.00 | 21.33 | N |
| ATOM | 5503 | CE1 | HIS A 409 | 74.948 | 70.462 | 18.511 | 1.00 | 21.66 | C |
| ATOM | 5505 | NE2 | HIS A 409 | 75.957 | 71.133 | 17.979 | 1.00 | 22.90 | N |
| ATOM | 5507 | CD2 | HIS A 409 | 75.459 | 72.200 | 17.262 | 1.00 | 21.64 | C |
| ATOM | 5509 | C | HIS A 409 | 71.333 | 73.223 | 14.983 | 1.00 | 13.16 | C |
| ATOM | 5510 | O | HIS A 409 | 71.429 | 74.438 | 14.815 | 1.00 | 12.86 | O |
| ATOM | 5512 | N | GLY A 410 | 70.258 | 72.529 | 14.668 | 1.00 | 12.80 | N |
| ATOM | 5513 | CA | GLY A 410 | 69.139 | 73.176 | 13.984 | 1.00 | 12.21 | C |
| ATOM | 5516 | C | GLY A 410 | 67.811 | 72.838 | 14.594 | 1.00 | 12.52 | C |
| ATOM | 5517 | O | GLY A 410 | 67.720 | 72.563 | 15.788 | 1.00 | 12.97 | O |
| ATOM | 5519 | N | GLY A 411 | 66.760 | 72.888 | 13.765 | 1.00 | 13.05 | N |
| ATOM | 5520 | CA | GLY A 411 | 65.377 | 72.773 | 14.250 | 1.00 | 12.42 | C |
| ATOM | 5523 | C | GLY A 411 | 64.412 | 72.027 | 13.381 | 1.00 | 10.78 | C |
| ATOM | 5524 | O | GLY A 411 | 63.206 | 72.355 | 13.353 | 1.00 | 12.02 | O |
| ATOM | 5526 | N | ASN A 412 | 64.933 | 71.027 | 12.661 | 1.00 | 11.35 | N |
| ATOM | 5527 | CA | ASN A 412 | 64.104 | 70.271 | 11.705 | 1.00 | 11.74 | C |
| ATOM | 5529 | CB | ASN A 412 | 64.982 | 69.513 | 10.690 | 1.00 | 12.04 | C |
| ATOM | 5532 | CG | ASN A 412 | 65.608 | 70.438 | 9.651 | 1.00 | 13.99 | C |
| ATOM | 5533 | OD1 | ASN A 412 | 65.089 | 71.543 | 9.415 | 1.00 | 11.84 | O |
| ATOM | 5534 | ND2 | ASN A 412 | 66.726 | 70.022 | 9.047 | 1.00 | 14.89 | N |
| ATOM | 5537 | C | ASN A 412 | 63.057 | 69.368 | 12.322 | 1.00 | 11.74 | C |
| ATOM | 5538 | O | ASN A 412 | 62.239 | 68.809 | 11.607 | 1.00 | 12.72 | O |
| ATOM | 5540 | N | PHE A 413 | 63.065 | 69.239 | 13.645 | 1.00 | 12.11 | N |
| ATOM | 5541 | CA | PHE A 413 | 62.016 | 68.530 | 14.378 | 1.00 | 11.35 | C |
| ATOM | 5543 | CB | PHE A 413 | 62.611 | 68.082 | 15.693 | 1.00 | 11.23 | C |
| ATOM | 5546 | CG | PHE A 413 | 63.338 | 69.169 | 16.400 | 1.00 | 10.96 | C |
| ATOM | 5547 | CD1 | PHE A 413 | 62.629 | 70.237 | 16.933 | 1.00 | 13.44 | C |
| ATOM | 5549 | CE1 | PHE A 413 | 63.283 | 71.262 | 17.578 | 1.00 | 11.15 | C |
| ATOM | 5551 | CZ | PHE A 413 | 64.663 | 71.240 | 17.675 | 1.00 | 13.97 | C |
| ATOM | 5553 | CE2 | PHE A 413 | 65.372 | 70.165 | 17.168 | 1.00 | 13.37 | C |
| ATOM | 5555 | CD2 | PHE A 413 | 64.723 | 69.152 | 16.518 | 1.00 | 12.34 | C |
| ATOM | 5557 | C | PHE A 413 | 60.758 | 69.419 | 14.656 | 1.00 | 11.83 | C |
| ATOM | 5558 | O | PHE A 413 | 59.776 | 68.938 | 15.217 | 1.00 | 11.31 | O |
| ATOM | 5560 | N | GLN A 414 | 60.839 | 70.710 | 14.338 | 1.00 | 11.01 | N |

| | | | | | | | | | |
|---|---|---|---|---|---|---|---|---|---|
| ATOM | 5561 | CA | GLN | A | 414 | 59.708 | 71.633 | 14.566 | 1.00 11.47 | C |
| ATOM | 5563 | CB | GLN | A | 414 | 60.199 | 73.076 | 14.517 | 1.00 11.22 | C |
| ATOM | 5566 | CG | GLN | A | 414 | 59.111 | 74.104 | 14.729 | 1.00 10.52 | C |
| ATOM | 5569 | CD | GLN | A | 414 | 58.574 | 74.045 | 16.151 | 1.00 11.95 | C |
| ATOM | 5570 | OE1 | GLN | A | 414 | 57.684 | 73.247 | 16.433 | 1.00 13.74 | O |
| ATOM | 5571 | NE2 | GLN | A | 414 | 59.177 | 74.840 | 17.072 | 1.00 13.00 | N |
| ATOM | 5574 | C | GLN | A | 414 | 58.664 | 71.349 | 13.475 | 1.00 11.40 | C |
| ATOM | 5575 | O | GLN | A | 414 | 58.821 | 71.782 | 12.359 | 1.00 11.65 | O |
| ATOM | 5577 | N | ALA | A | 415 | 57.604 | 70.617 | 13.809 | 1.00 11.66 | N |
| ATOM | 5578 | CA | ALA | A | 415 | 56.693 | 70.096 | 12.813 | 1.00 12.38 | C |
| ATOM | 5580 | CB | ALA | A | 415 | 56.012 | 68.841 | 13.364 | 1.00 11.65 | C |
| ATOM | 5584 | C | ALA | A | 415 | 55.641 | 71.101 | 12.322 | 1.00 11.36 | C |
| ATOM | 5585 | O | ALA | A | 415 | 54.480 | 70.742 | 12.040 | 1.00 12.03 | O |
| ATOM | 5587 | N | ALA | A | 416 | 56.027 | 72.358 | 12.175 | 1.00 12.01 | N |
| ATOM | 5588 | CA | ALA | A | 416 | 55.030 | 73.355 | 11.781 | 1.00 13.22 | C |
| ATOM | 5590 | CB | ALA | A | 416 | 55.593 | 74.729 | 11.888 | 1.00 13.23 | C |
| ATOM | 5594 | C | ALA | A | 416 | 54.491 | 73.069 | 10.363 | 1.00 12.38 | C |
| ATOM | 5595 | O | ALA | A | 416 | 53.328 | 73.350 | 10.071 | 1.00 13.15 | O |
| ATOM | 5597 | N | ALA | A | 417 | 55.345 | 72.558 | 9.489 | 1.00 12.16 | N |
| ATOM | 5598 | CA | ALA | A | 417 | 54.916 | 72.195 | 8.122 | 1.00 12.44 | C |
| ATOM | 5600 | CB | ALA | A | 417 | 56.071 | 71.668 | 7.268 | 1.00 12.87 | C |
| ATOM | 5604 | C | ALA | A | 417 | 53.747 | 71.202 | 8.179 | 1.00 11.85 | C |
| ATOM | 5605 | O | ALA | A | 417 | 52.774 | 71.334 | 7.448 | 1.00 12.62 | O |
| ATOM | 5607 | N | VAL | A | 418 | 53.841 | 70.211 | 9.066 | 1.00 12.87 | N |
| ATOM | 5608 | CA | VAL | A | 418 | 52.789 | 69.216 | 9.209 | 1.00 12.13 | C |
| ATOM | 5610 | CB | VAL | A | 418 | 53.197 | 68.065 | 10.119 | 1.00 12.72 | C |
| ATOM | 5612 | CG1 | VAL | A | 418 | 52.077 | 67.050 | 10.299 | 1.00 14.34 | C |
| ATOM | 5616 | CG2 | VAL | A | 418 | 54.435 | 67.362 | 9.582 | 1.00 14.80 | C |
| ATOM | 5620 | C | VAL | A | 418 | 51.569 | 69.901 | 9.829 | 1.00 11.56 | C |
| ATOM | 5621 | O | VAL | A | 418 | 50.458 | 69.742 | 9.373 | 1.00 12.22 | O |
| ATOM | 5623 | N | ALA | A | 419 | 51.751 | 70.630 | 10.915 | 1.00 12.61 | N |
| ATOM | 5624 | CA | ALA | A | 419 | 50.593 | 71.314 | 11.524 | 1.00 12.54 | C |
| ATOM | 5626 | CB | ALA | A | 419 | 50.994 | 72.085 | 12.757 | 1.00 13.30 | C |
| ATOM | 5630 | C | ALA | A | 419 | 49.854 | 72.210 | 10.553 | 1.00 12.60 | C |
| ATOM | 5631 | O | ALA | A | 419 | 48.616 | 72.216 | 10.531 | 1.00 11.38 | O |
| ATOM | 5633 | N | ASN | A | 420 | 50.602 | 72.961 | 9.759 | 1.00 13.16 | N |
| ATOM | 5634 | CA | ASN | A | 420 | 50.062 | 73.822 | 8.707 | 1.00 13.69 | C |
| ATOM | 5636 | CB | ASN | A | 420 | 51.218 | 74.398 | 7.878 | 1.00 14.08 | C |
| ATOM | 5639 | CG | ASN | A | 420 | 50.736 | 75.244 | 6.684 | 1.00 16.55 | C |
| ATOM | 5640 | OD1 | ASN | A | 420 | 50.614 | 74.740 | 5.534 | 1.00 19.09 | O |
| ATOM | 5641 | ND2 | ASN | A | 420 | 50.512 | 76.535 | 6.942 | 1.00 21.66 | N |
| ATOM | 5644 | C | ASN | A | 420 | 49.073 | 73.060 | 7.819 | 1.00 13.40 | C |
| ATOM | 5645 | O | ASN | A | 420 | 47.959 | 73.512 | 7.584 | 1.00 14.44 | O |
| ATOM | 5647 | N | THR | A | 421 | 49.473 | 71.890 | 7.338 | 1.00 11.86 | N |
| ATOM | 5648 | CA | THR | A | 421 | 48.594 | 71.095 | 6.476 | 1.00 11.49 | C |
| ATOM | 5650 | CB | THR | A | 421 | 49.298 | 69.819 | 5.920 | 1.00 11.21 | C |
| ATOM | 5652 | OG1 | THR | A | 421 | 49.527 | 68.821 | 6.942 | 1.00 12.18 | O |
| ATOM | 5654 | CG2 | THR | A | 421 | 50.608 | 70.201 | 5.242 | 1.00 11.63 | C |
| ATOM | 5658 | C | THR | A | 421 | 47.347 | 70.696 | 7.185 | 1.00 11.52 | C |
| ATOM | 5659 | O | THR | A | 421 | 46.254 | 70.680 | 6.580 | 1.00 12.50 | O |
| ATOM | 5661 | N | MSE | A | 422 | 47.469 | 70.368 | 8.474 | 1.00 10.84 | N |
| ATOM | 5662 | CA | MSE | A | 422 | 46.316 | 69.818 | 9.199 | 1.00 11.36 | C |
| ATOM | 5664 | CB | MSE | A | 422 | 46.761 | 69.042 | 10.436 | 1.00 12.28 | C |
| ATOM | 5667 | CG | MSE | A | 422 | 47.503 | 67.766 | 10.105 | 1.00 11.50 | C |
| ATOM | 5670 | SE | MSE | A | 422 | 46.300 | 66.484 | 9.243 | 1.00 21.41 | SE |
| ATOM | 5671 | CE | MSE | A | 422 | 46.730 | 66.876 | 7.250 | 1.00 16.63 | C |
| ATOM | 5675 | C | MSE | A | 422 | 45.302 | 70.903 | 9.560 | 1.00 12.20 | C |

| ATOM | 5676 | O | MSE A 422 | 44.099 | 70.683 | 9.510 | 1.00 | 12.65 | O |
|------|------|-----|-----------|--------|--------|-------|------|-------|---|
| ATOM | 5678 | N | GLU A 423 | 45.797 | 72.114 | 9.815 | 1.00 | 12.62 | N |
| ATOM | 5679 | CA | GLU A 423 | 44.905 | 73.218 | 10.151 | 1.00 | 13.60 | C |
| ATOM | 5681 | CB | GLU A 423 | 45.683 | 74.458 | 10.627 | 1.00 | 14.51 | C |
| ATOM | 5684 | CG | GLU A 423 | 46.552 | 74.260 | 11.856 | 1.00 | 14.15 | C |
| ATOM | 5687 | CD | GLU A 423 | 45.820 | 74.290 | 13.185 | 1.00 | 15.74 | C |
| ATOM | 5688 | OE1 | GLU A 423 | 45.831 | 75.385 | 13.786 | 1.00 | 18.66 | O |
| ATOM | 5689 | OE2 | GLU A 423 | 45.284 | 73.212 | 13.614 | 1.00 | 15.96 | O |
| ATOM | 5690 | C | GLU A 423 | 44.063 | 73.581 | 8.917 | 1.00 | 14.97 | C |
| ATOM | 5691 | O | GLU A 423 | 42.845 | 73.758 | 9.023 | 1.00 | 14.17 | O |
| ATOM | 5693 | N | LYS A 424 | 44.722 | 73.680 | 7.764 | 1.00 | 15.10 | N |
| ATOM | 5694 | CA | LYS A 424 | 44.000 | 74.052 | 6.534 | 1.00 | 17.47 | C |
| ATOM | 5696 | CB | LYS A 424 | 44.937 | 74.406 | 5.374 | 1.00 | 18.54 | C |
| ATOM | 5699 | CG | LYS A 424 | 45.888 | 75.567 | 5.649 | 1.00 | 23.96 | C |
| ATOM | 5702 | CD | LYS A 424 | 46.605 | 76.032 | 4.343 | 1.00 | 23.50 | C |
| ATOM | 5705 | CE | LYS A 424 | 47.207 | 74.909 | 3.554 | 1.00 | 27.09 | C |
| ATOM | 5708 | NZ | LYS A 424 | 48.346 | 75.498 | 2.786 | 1.00 | 28.28 | N |
| ATOM | 5712 | C | LYS A 424 | 43.041 | 72.947 | 6.118 | 1.00 | 15.58 | C |
| ATOM | 5713 | O | LYS A 424 | 41.932 | 73.219 | 5.663 | 1.00 | 14.64 | O |
| ATOM | 5715 | N | THR A 425 | 43.498 | 71.710 | 6.232 | 1.00 | 13.86 | N |
| ATOM | 5716 | CA | THR A 425 | 42.676 | 70.569 | 5.846 | 1.00 | 13.06 | C |
| ATOM | 5718 | CB | THR A 425 | 43.446 | 69.263 | 5.906 | 1.00 | 14.18 | C |
| ATOM | 5720 | OG1 | THR A 425 | 44.505 | 69.311 | 4.950 | 1.00 | 11.52 | O |
| ATOM | 5722 | CG2 | THR A 425 | 42.550 | 68.069 | 5.592 | 1.00 | 13.90 | C |
| ATOM | 5726 | C | THR A 425 | 41.389 | 70.526 | 6.696 | 1.00 | 13.13 | C |
| ATOM | 5727 | O | THR A 425 | 40.306 | 70.292 | 6.191 | 1.00 | 14.14 | O |
| ATOM | 5729 | N | ARG A 426 | 41.513 | 70.753 | 8.000 | 1.00 | 11.78 | N |
| ATOM | 5730 | CA | ARG A 426 | 40.355 | 70.660 | 8.868 | 1.00 | 11.92 | C |
| ATOM | 5732 | CB | ARG A 426 | 40.803 | 70.731 | 10.323 | 1.00 | 12.38 | C |
| ATOM | 5735 | CG | ARG A 426 | 39.754 | 70.288 | 11.266 | 1.00 | 12.51 | C |
| ATOM | 5738 | CD | ARG A 426 | 40.291 | 69.995 | 12.694 | 1.00 | 12.66 | C |
| ATOM | 5741 | NE | ARG A 426 | 40.876 | 71.152 | 13.315 | 1.00 | 13.64 | N |
| ATOM | 5743 | CZ | ARG A 426 | 42.174 | 71.379 | 13.388 | 1.00 | 14.71 | C |
| ATOM | 5744 | NH1 | ARG A 426 | 43.077 | 70.523 | 12.874 | 1.00 | 13.14 | N |
| ATOM | 5747 | NH2 | ARG A 426 | 42.603 | 72.469 | 13.960 | 1.00 | 12.99 | N |
| ATOM | 5750 | C | ARG A 426 | 39.351 | 71.764 | 8.552 | 1.00 | 11.90 | C |
| ATOM | 5751 | O | ARG A 426 | 38.120 | 71.531 | 8.607 | 1.00 | 13.51 | O |
| ATOM | 5753 | N | LEU A 427 | 39.822 | 72.963 | 8.225 | 1.00 | 13.58 | N |
| ATOM | 5754 | CA | LEU A 427 | 38.892 | 74.022 | 7.809 | 1.00 | 13.66 | C |
| ATOM | 5756 | CB | LEU A 427 | 39.597 | 75.363 | 7.665 | 1.00 | 14.59 | C |
| ATOM | 5759 | CG | LEU A 427 | 38.707 | 76.551 | 7.297 | 1.00 | 14.62 | C |
| ATOM | 5761 | CD1 | LEU A 427 | 37.519 | 76.738 | 8.270 | 1.00 | 17.08 | C |
| ATOM | 5765 | CD2 | LEU A 427 | 39.549 | 77.810 | 7.243 | 1.00 | 16.11 | C |
| ATOM | 5769 | C | LEU A 427 | 38.239 | 73.643 | 6.464 | 1.00 | 13.12 | C |
| ATOM | 5770 | O | LEU A 427 | 37.058 | 73.780 | 6.285 | 1.00 | 13.68 | O |
| ATOM | 5772 | N | GLY A 428 | 39.016 | 73.105 | 5.549 | 1.00 | 13.21 | N |
| ATOM | 5773 | CA | GLY A 428 | 38.464 | 72.612 | 4.279 | 1.00 | 12.48 | C |
| ATOM | 5776 | C | GLY A 428 | 37.364 | 71.553 | 4.452 | 1.00 | 12.27 | C |
| ATOM | 5777 | O | GLY A 428 | 36.335 | 71.576 | 3.769 | 1.00 | 12.54 | O |
| ATOM | 5779 | N | LEU A 429 | 37.571 | 70.628 | 5.384 | 1.00 | 12.41 | N |
| ATOM | 5780 | CA | LEU A 429 | 36.559 | 69.577 | 5.677 | 1.00 | 11.80 | C |
| ATOM | 5782 | CB | LEU A 429 | 37.083 | 68.560 | 6.675 | 1.00 | 12.62 | C |
| ATOM | 5785 | CG | LEU A 429 | 38.240 | 67.735 | 6.113 | 1.00 | 11.23 | C |
| ATOM | 5787 | CD1 | LEU A 429 | 38.921 | 67.047 | 7.283 | 1.00 | 12.49 | C |
| ATOM | 5791 | CD2 | LEU A 429 | 37.782 | 66.697 | 5.071 | 1.00 | 12.89 | C |
| ATOM | 5795 | C | LEU A 429 | 35.268 | 70.177 | 6.157 | 1.00 | 12.87 | C |
| ATOM | 5796 | O | LEU A 429 | 34.194 | 69.733 | 5.770 | 1.00 | 13.13 | O |

| | | | | | | | | | |
|---|---|---|---|---|---|---|---|---|---|
| ATOM | 5798 | N | ALA | A | 430 | 35.356 | 71.229 | 6.957 | 1.00 12.13 | N |
| ATOM | 5799 | CA | ALA | A | 430 | 34.166 | 71.917 | 7.418 | 1.00 12.63 | C |
| ATOM | 5801 | CB | ALA | A | 430 | 34.527 | 72.951 | 8.461 | 1.00 12.67 | C |
| ATOM | 5805 | C | ALA | A | 430 | 33.444 | 72.576 | 6.226 | 1.00 12.71 | C |
| ATOM | 5806 | O | ALA | A | 430 | 32.205 | 72.669 | 6.201 | 1.00 13.50 | O |
| ATOM | 5808 | N | GLN | A | 431 | 34.240 | 73.113 | 5.302 | 1.00 13.10 | N |
| ATOM | 5809 | CA | GLN | A | 431 | 33.675 | 73.824 | 4.142 | 1.00 13.24 | C |
| ATOM | 5811 | CB | GLN | A | 431 | 34.760 | 74.614 | 3.428 | 1.00 14.03 | C |
| ATOM | 5814 | CG | GLN | A | 431 | 35.303 | 75.731 | 4.296 | 1.00 18.27 | C |
| ATOM | 5817 | CD | GLN | A | 431 | 34.289 | 76.655 | 4.902 | 1.00 25.29 | C |
| ATOM | 5818 | OE1 | GLN | A | 431 | 33.992 | 76.541 | 6.108 | 1.00 29.67 | O |
| ATOM | 5819 | NE2 | GLN | A | 431 | 33.767 | 77.603 | 4.108 | 1.00 23.31 | N |
| ATOM | 5822 | C | GLN | A | 431 | 32.984 | 72.846 | 3.183 | 1.00 12.05 | C |
| ATOM | 5823 | O | GLN | A | 431 | 31.874 | 73.111 | 2.635 | 1.00 11.18 | O |
| ATOM | 5825 | N | ILE | A | 432 | 33.607 | 71.716 | 2.966 | 1.00 12.83 | N |
| ATOM | 5826 | CA | ILE | A | 432 | 32.971 | 70.636 | 2.170 | 1.00 12.47 | C |
| ATOM | 5828 | CB | ILE | A | 432 | 33.872 | 69.410 | 2.052 | 1.00 12.02 | C |
| ATOM | 5830 | CG1 | ILE | A | 432 | 35.123 | 69.701 | 1.238 | 1.00 11.68 | C |
| ATOM | 5833 | CD1 | ILE | A | 432 | 36.197 | 68.590 | 1.370 | 1.00 13.35 | C |
| ATOM | 5837 | CG2 | ILE | A | 432 | 33.113 | 68.226 | 1.450 | 1.00 12.90 | C |
| ATOM | 5841 | C | ILE | A | 432 | 31.659 | 70.237 | 2.892 | 1.00 13.47 | C |
| ATOM | 5842 | O | ILE | A | 432 | 30.585 | 70.166 | 2.281 | 1.00 13.23 | O |
| ATOM | 5844 | N | GLY | A | 433 | 31.747 | 70.002 | 4.207 | 1.00 12.22 | N |
| ATOM | 5845 | CA | GLY | A | 433 | 30.546 | 69.607 | 4.981 | 1.00 13.15 | C |
| ATOM | 5848 | C | GLY | A | 433 | 29.403 | 70.608 | 4.820 | 1.00 13.47 | C |
| ATOM | 5849 | O | GLY | A | 433 | 28.225 | 70.215 | 4.586 | 1.00 13.10 | O |
| ATOM | 5851 | N | LYS | A | 434 | 29.718 | 71.904 | 4.996 | 1.00 12.83 | N |
| ATOM | 5852 | CA | LYS | A | 434 | 28.689 | 72.931 | 4.862 | 1.00 13.34 | C |
| ATOM | 5854 | CB | LYS | A | 434 | 29.262 | 74.304 | 5.096 | 1.00 14.11 | C |
| ATOM | 5857 | CG | LYS | A | 434 | 28.242 | 75.423 | 5.007 | 1.00 13.72 | C |
| ATOM | 5860 | CD | LYS | A | 434 | 27.145 | 75.373 | 6.059 | 1.00 16.34 | C |
| ATOM | 5863 | CE | LYS | A | 434 | 26.272 | 76.628 | 5.984 | 1.00 17.65 | C |
| ATOM | 5866 | NZ | LYS | A | 434 | 25.177 | 76.826 | 7.045 | 1.00 16.85 | N |
| ATOM | 5870 | C | LYS | A | 434 | 28.047 | 72.848 | 3.473 | 1.00 12.41 | C |
| ATOM | 5871 | O | LYS | A | 434 | 26.804 | 72.889 | 3.308 | 1.00 12.91 | O |
| ATOM | 5873 | N | LEU | A | 435 | 28.872 | 72.685 | 2.441 | 1.00 12.48 | N |
| ATOM | 5874 | CA | LEU | A | 435 | 28.307 | 72.617 | 1.095 | 1.00 12.19 | C |
| ATOM | 5876 | CB | LEU | A | 435 | 29.404 | 72.449 | 0.055 | 1.00 12.04 | C |
| ATOM | 5879 | CG | LEU | A | 435 | 28.864 | 72.498 | -1.392 | 1.00 13.12 | C |
| ATOM | 5881 | CD1 | LEU | A | 435 | 28.362 | 73.877 | -1.740 | 1.00 15.25 | C |
| ATOM | 5885 | CD2 | LEU | A | 435 | 29.979 | 72.115 | -2.362 | 1.00 13.53 | C |
| ATOM | 5889 | C | LEU | A | 435 | 27.355 | 71.425 | 0.903 | 1.00 12.69 | C |
| ATOM | 5890 | O | LEU | A | 435 | 26.198 | 71.584 | 0.486 | 1.00 13.18 | O |
| ATOM | 5892 | N | ASN | A | 436 | 27.831 | 70.238 | 1.202 | 1.00 13.40 | N |
| ATOM | 5893 | CA | ASN | A | 436 | 26.994 | 69.058 | 1.031 | 1.00 13.62 | C |
| ATOM | 5895 | CB | ASN | A | 436 | 27.815 | 67.772 | 1.130 | 1.00 13.99 | C |
| ATOM | 5898 | CG | ASN | A | 436 | 28.851 | 67.678 | 0.006 | 1.00 15.63 | C |
| ATOM | 5899 | OD1 | ASN | A | 436 | 30.032 | 67.674 | 0.248 | 1.00 16.29 | O |
| ATOM | 5900 | ND2 | ASN | A | 436 | 28.391 | 67.630 | -1.246 | 1.00 18.60 | N |
| ATOM | 5903 | C | ASN | A | 436 | 25.770 | 69.090 | 1.952 | 1.00 14.09 | C |
| ATOM | 5904 | O | ASN | A | 436 | 24.686 | 68.653 | 1.567 | 1.00 14.39 | O |
| ATOM | 5906 | N | PHE | A | 437 | 25.917 | 69.656 | 3.150 | 1.00 12.21 | N |
| ATOM | 5907 | CA | PHE | A | 437 | 24.769 | 69.800 | 4.035 | 1.00 12.34 | C |
| ATOM | 5909 | CB | PHE | A | 437 | 25.150 | 70.423 | 5.385 | 1.00 12.98 | C |
| ATOM | 5912 | CG | PHE | A | 437 | 23.957 | 70.862 | 6.174 | 1.00 13.52 | C |
| ATOM | 5913 | CD1 | PHE | A | 437 | 23.133 | 69.971 | 6.732 | 1.00 16.15 | C |
| ATOM | 5915 | CE1 | PHE | A | 437 | 22.006 | 70.348 | 7.413 | 1.00 17.27 | C |

| ATOM | 5917 | CZ | PHE A 437 | 21.698 | 71.676 | 7.553 | 1.00 | 14.58 | C |
| ATOM | 5919 | CE2 | PHE A 437 | 22.483 | 72.614 | 6.977 | 1.00 | 16.59 | C |
| ATOM | 5921 | CD2 | PHE A 437 | 23.629 | 72.204 | 6.268 | 1.00 | 13.25 | C |
| ATOM | 5923 | C | PHE A 437 | 23.701 | 70.668 | 3.340 | 1.00 | 11.61 | C |
| ATOM | 5924 | O | PHE A 437 | 22.513 | 70.336 | 3.332 | 1.00 | 13.02 | O |
| ATOM | 5926 | N | THR A 438 | 24.137 | 71.802 | 2.799 | 1.00 | 10.58 | N |
| ATOM | 5927 | CA | THR A 438 | 23.156 | 72.750 | 2.197 | 1.00 | 12.55 | C |
| ATOM | 5929 | CB | THR A 438 | 23.767 | 74.132 | 1.874 | 1.00 | 14.60 | C |
| ATOM | 5931 | OG1 | THR A 438 | 24.773 | 73.995 | 0.859 | 1.00 | 13.90 | O |
| ATOM | 5933 | CG2 | THR A 438 | 24.326 | 74.783 | 3.123 | 1.00 | 13.42 | C |
| ATOM | 5937 | C | THR A 438 | 22.504 | 72.123 | 0.985 | 1.00 | 12.72 | C |
| ATOM | 5938 | O | THR A 438 | 21.283 | 72.296 | 0.757 | 1.00 | 12.14 | O |
| ATOM | 5940 | N | GLN A 439 | 23.272 | 71.314 | 0.236 | 1.00 | 11.97 | N |
| ATOM | 5941 | CA | GLN A 439 | 22.668 | 70.576 | -0.913 | 1.00 | 12.17 | C |
| ATOM | 5943 | CB | GLN A 439 | 23.762 | 69.822 | -1.683 | 1.00 | 12.16 | C |
| ATOM | 5946 | CG | GLN A 439 | 24.810 | 70.690 | -2.360 | 1.00 | 13.91 | C |
| ATOM | 5949 | CD | GLN A 439 | 25.955 | 69.875 | -2.986 | 1.00 | 12.20 | C |
| ATOM | 5950 | OE1 | GLN A 439 | 26.084 | 68.689 | -2.712 | 1.00 | 16.22 | O |
| ATOM | 5951 | NE2 | GLN A 439 | 26.826 | 70.544 | -3.801 | 1.00 | 12.79 | N |
| ATOM | 5954 | C | GLN A 439 | 21.604 | 69.589 | -0.467 | 1.00 | 13.12 | C |
| ATOM | 5955 | O | GLN A 439 | 20.495 | 69.538 | -1.025 | 1.00 | 15.15 | O |
| ATOM | 5957 | N | LEU A 440 | 21.986 | 68.759 | 0.489 | 1.00 | 12.66 | N |
| ATOM | 5958 | CA | LEU A 440 | 21.110 | 67.779 | 1.099 | 1.00 | 13.09 | C |
| ATOM | 5960 | CB | LEU A 440 | 21.892 | 66.966 | 2.162 | 1.00 | 14.32 | C |
| ATOM | 5963 | CG | LEU A 440 | 21.077 | 65.886 | 2.854 | 1.00 | 15.72 | C |
| ATOM | 5965 | CD1 | LEU A 440 | 20.433 | 64.941 | 1.859 | 1.00 | 16.62 | C |
| ATOM | 5969 | CD2 | LEU A 440 | 21.995 | 65.144 | 3.838 | 1.00 | 14.92 | C |
| ATOM | 5973 | C | LEU A 440 | 19.853 | 68.353 | 1.703 | 1.00 | 14.36 | C |
| ATOM | 5974 | O | LEU A 440 | 18.765 | 67.852 | 1.453 | 1.00 | 14.07 | O |
| ATOM | 5976 | N | THR A 441 | 19.997 | 69.354 | 2.554 | 1.00 | 13.92 | N |
| ATOM | 5977 | CA | THR A 441 | 18.839 | 69.900 | 3.225 | 1.00 | 14.87 | C |
| ATOM | 5979 | CB | THR A 441 | 19.236 | 70.741 | 4.462 | 1.00 | 15.40 | C |
| ATOM | 5981 | OG1 | THR A 441 | 18.125 | 70.829 | 5.389 | 1.00 | 15.92 | O |
| ATOM | 5983 | CG2 | THR A 441 | 19.683 | 72.044 | 4.065 | 1.00 | 15.19 | C |
| ATOM | 5987 | C | THR A 441 | 17.895 | 70.635 | 2.256 | 1.00 | 14.78 | C |
| ATOM | 5988 | O | THR A 441 | 16.689 | 70.653 | 2.494 | 1.00 | 15.36 | O |
| ATOM | 5990 | N | GLU A 442 | 18.392 | 71.179 | 1.150 | 1.00 | 14.95 | N |
| ATOM | 5991 | CA | GLU A 442 | 17.500 | 71.744 | 0.128 | 1.00 | 16.10 | C |
| ATOM | 5993 | CB | GLU A 442 | 18.332 | 72.388 | -0.948 | 1.00 | 15.53 | C |
| ATOM | 5996 | CG | GLU A 442 | 17.538 | 73.026 | -2.115 | 1.00 | 16.17 | C |
| ATOM | 5999 | CD | GLU A 442 | 18.456 | 73.754 | -3.136 | 1.00 | 21.31 | C |
| ATOM | 6000 | OE1 | GLU A 442 | 19.621 | 74.122 | -2.772 | 1.00 | 22.23 | O |
| ATOM | 6001 | OE2 | GLU A 442 | 17.997 | 74.012 | -4.269 | 1.00 | 23.44 | O |
| ATOM | 6002 | C | GLU A 442 | 16.684 | 70.609 | -0.517 | 1.00 | 16.28 | C |
| ATOM | 6003 | O | GLU A 442 | 15.470 | 70.679 | -0.721 | 1.00 | 16.33 | O |
| ATOM | 6005 | N | MSE A 443 | 17.384 | 69.549 | -0.853 | 1.00 | 17.51 | N |
| ATOM | 6006 | CA | MSE A 443 | 16.755 | 68.382 | -1.449 | 1.00 | 17.62 | C |
| ATOM | 6008 | CB | MSE A 443 | 17.821 | 67.362 | -1.874 | 1.00 | 18.33 | C |
| ATOM | 6011 | CG | MSE A 443 | 17.271 | 66.142 | -2.531 | 1.00 | 19.10 | C |
| ATOM | 6014 | SE | MSE A 443 | 18.708 | 64.976 | -3.271 | 1.00 | 25.30 | SE |
| ATOM | 6015 | CE | MSE A 443 | 19.366 | 64.299 | -1.518 | 1.00 | 22.84 | C |
| ATOM | 6019 | C | MSE A 443 | 15.698 | 67.712 | -0.549 | 1.00 | 16.69 | C |
| ATOM | 6020 | O | MSE A 443 | 14.737 | 67.115 | -1.045 | 1.00 | 15.93 | O |
| ATOM | 6022 | N | LEU A 444 | 15.876 | 67.800 | 0.762 | 1.00 | 15.51 | N |
| ATOM | 6023 | CA | LEU A 444 | 14.950 | 67.208 | 1.737 | 1.00 | 15.36 | C |
| ATOM | 6025 | CB | LEU A 444 | 15.703 | 66.728 | 2.993 | 1.00 | 16.80 | C |
| ATOM | 6028 | CG | LEU A 444 | 16.719 | 65.603 | 2.721 | 1.00 | 14.38 | C |

```
ATOM   6030  CD1 LEU A 444      17.379  65.212   4.037  1.00 17.11           C
ATOM   6034  CD2 LEU A 444      16.134  64.376   2.029  1.00 14.73           C
ATOM   6038  C   LEU A 444      13.840  68.175   2.175  1.00 16.39           C
ATOM   6039  O   LEU A 444      13.043  67.823   3.060  1.00 17.88           O
ATOM   6041  N   ASN A 445      13.813  69.355   1.563  1.00 16.09           N
ATOM   6042  CA  ASN A 445      12.828  70.393   1.836  1.00 15.76           C
ATOM   6044  CB  ASN A 445      13.493  71.769   1.924  1.00 15.65           C
ATOM   6047  CG  ASN A 445      12.555  72.874   2.346  1.00 18.34           C
ATOM   6048  OD1 ASN A 445      11.414  72.936   1.881  1.00 19.52           O
ATOM   6049  ND2 ASN A 445      13.040  73.774   3.209  1.00 15.58           N
ATOM   6052  C   ASN A 445      11.792  70.381   0.736  1.00 14.82           C
ATOM   6053  O   ASN A 445      12.093  70.673  -0.395  1.00 14.88           O
ATOM   6055  N   ALA A 446      10.564  70.023   1.094  1.00 16.36           N
ATOM   6056  CA  ALA A 446       9.494  69.821   0.102  1.00 16.73           C
ATOM   6058  CB  ALA A 446       8.272  69.308   0.807  1.00 16.09           C
ATOM   6062  C   ALA A 446       9.162  71.118  -0.657  1.00 15.52           C
ATOM   6063  O   ALA A 446       8.663  71.089  -1.780  1.00 15.74           O
ATOM   6065  N   GLY A 447       9.427  72.254  -0.022  1.00 17.05           N
ATOM   6066  CA  GLY A 447       9.139  73.553  -0.622  1.00 17.03           C
ATOM   6069  C   GLY A 447      10.175  73.962  -1.657  1.00 19.34           C
ATOM   6070  O   GLY A 447       9.930  74.852  -2.480  1.00 20.62           O
ATOM   6072  N   MSE A 448      11.332  73.304  -1.630  1.00 18.63           N
ATOM   6073  CA  MSE A 448      12.474  73.668  -2.476  1.00 19.59           C
ATOM   6075  CB  MSE A 448      13.671  74.048  -1.578  1.00 19.41           C
ATOM   6078  CG  MSE A 448      13.287  74.923  -0.438  1.00 19.17           C
ATOM   6081  SE  MSE A 448      14.920  75.248   0.691  1.00 29.82          SE
ATOM   6082  CE  MSE A 448      15.938  76.290  -0.552  1.00 22.05           C
ATOM   6086  C   MSE A 448      12.958  72.603  -3.469  1.00 18.41           C
ATOM   6087  O   MSE A 448      13.798  72.925  -4.298  1.00 17.75           O
ATOM   6089  N   ASN A 449      12.452  71.359  -3.416  1.00 17.13           N
ATOM   6090  CA  ASN A 449      13.071  70.242  -4.132  1.00 17.39           C
ATOM   6092  CB  ASN A 449      13.220  69.054  -3.167  1.00 16.25           C
ATOM   6095  CG  ASN A 449      11.897  68.539  -2.669  1.00 17.40           C
ATOM   6096  OD1 ASN A 449      10.810  68.942  -3.174  1.00 16.41           O
ATOM   6097  ND2 ASN A 449      11.972  67.547  -1.735  1.00 15.10           N
ATOM   6100  C   ASN A 449      12.364  69.826  -5.418  1.00 17.24           C
ATOM   6101  O   ASN A 449      12.473  68.695  -5.867  1.00 18.02           O
ATOM   6103  N   ARG A 450      11.656  70.762  -6.031  1.00 17.21           N
ATOM   6104  CA  ARG A 450      11.058  70.555  -7.318  1.00 19.30           C
ATOM   6106  CB  ARG A 450      12.125  70.428  -8.397  1.00 19.27           C
ATOM   6109  CG  ARG A 450      12.901  71.724  -8.622  1.00 23.37           C
ATOM   6112  CD  ARG A 450      13.564  71.702 -10.012  1.00 27.49           C
ATOM   6115  NE  ARG A 450      14.415  72.879 -10.236  1.00 35.96           N
ATOM   6117  CZ  ARG A 450      15.631  73.054  -9.721  1.00 37.88           C
ATOM   6118  NH1 ARG A 450      16.182  72.116  -8.968  1.00 37.71           N
ATOM   6121  NH2 ARG A 450      16.306  74.192  -9.973  1.00 39.69           N
ATOM   6124  C   ARG A 450      10.148  69.327  -7.315  1.00 17.45           C
ATOM   6125  O   ARG A 450      10.161  68.521  -8.265  1.00 18.85           O
ATOM   6127  N   GLY A 451       9.364  69.187  -6.263  1.00 16.91           N
ATOM   6128  CA  GLY A 451       8.326  68.157  -6.244  1.00 16.96           C
ATOM   6131  C   GLY A 451       8.748  66.760  -5.839  1.00 16.30           C
ATOM   6132  O   GLY A 451       7.972  65.823  -6.043  1.00 17.81           O
ATOM   6134  N   LEU A 452       9.956  66.589  -5.276  1.00 16.89           N
ATOM   6135  CA  LEU A 452      10.244  65.290  -4.678  1.00 16.24           C
ATOM   6137  CB  LEU A 452      11.697  65.138  -4.232  1.00 16.62           C
ATOM   6140  CG  LEU A 452      12.701  64.948  -5.374  1.00 18.03           C
ATOM   6142  CD1 LEU A 452      14.106  65.288  -4.901  1.00 20.41           C
```

| | | | | | | | | | |
|---|---|---|---|---|---|---|---|---|---|
| ATOM | 6146 | CD2 | LEU A 452 | 12.681 | 63.561 | -5.978 | 1.00 | 20.95 | C |
| ATOM | 6150 | C | LEU A 452 | 9.337 | 65.038 | -3.492 | 1.00 | 16.36 | C |
| ATOM | 6151 | O | LEU A 452 | 8.971 | 65.964 | -2.771 | 1.00 | 15.74 | O |
| ATOM | 6153 | N | PRO A 453 | 8.960 | 63.780 | -3.279 | 1.00 | 16.50 | N |
| ATOM | 6154 | CA | PRO A 453 | 8.094 | 63.501 | -2.111 | 1.00 | 16.27 | C |
| ATOM | 6156 | CB | PRO A 453 | 8.000 | 61.969 | -2.094 | 1.00 | 16.76 | C |
| ATOM | 6159 | CG | PRO A 453 | 8.263 | 61.582 | -3.512 | 1.00 | 17.31 | C |
| ATOM | 6162 | CD | PRO A 453 | 9.259 | 62.563 | -4.054 | 1.00 | 17.09 | C |
| ATOM | 6165 | C | PRO A 453 | 8.657 | 64.049 | -0.800 | 1.00 | 16.29 | C |
| ATOM | 6166 | O | PRO A 453 | 9.863 | 64.019 | -0.607 | 1.00 | 16.33 | O |
| ATOM | 6167 | N | SER A 454 | 7.779 | 64.519 | 0.075 | 1.00 | 17.12 | N |
| ATOM | 6168 | CA | SER A 454 | 8.178 | 65.006 | 1.379 | 1.00 | 18.66 | C |
| ATOM | 6170 | CB | SER A 454 | 6.971 | 65.382 | 2.240 | 1.00 | 19.16 | C |
| ATOM | 6173 | OG | SER A 454 | 6.167 | 64.254 | 2.413 | 1.00 | 28.34 | O |
| ATOM | 6175 | C | SER A 454 | 9.000 | 63.930 | 2.089 | 1.00 | 17.02 | C |
| ATOM | 6176 | O | SER A 454 | 8.634 | 62.736 | 2.110 | 1.00 | 15.34 | O |
| ATOM | 6178 | N | CYS A 455 | 10.107 | 64.368 | 2.670 | 1.00 | 16.61 | N |
| ATOM | 6179 | CA | CYS A 455 | 11.045 | 63.458 | 3.405 | 1.00 | 16.54 | C |
| ATOM | 6181 | CB | CYS A 455 | 10.392 | 62.917 | 4.675 | 1.00 | 16.85 | C |
| ATOM | 6184 | SG | CYS A 455 | 9.802 | 64.238 | 5.738 | 1.00 | 21.30 | S |
| ATOM | 6186 | C | CYS A 455 | 11.598 | 62.300 | 2.571 | 1.00 | 14.90 | C |
| ATOM | 6187 | O | CYS A 455 | 12.130 | 61.323 | 3.110 | 1.00 | 13.34 | O |
| ATOM | 6189 | N | LEU A 456 | 11.493 | 62.411 | 1.245 | 1.00 | 13.98 | N |
| ATOM | 6190 | CA | LEU A 456 | 11.767 | 61.274 | 0.353 | 1.00 | 14.14 | C |
| ATOM | 6192 | CB | LEU A 456 | 13.275 | 61.010 | 0.192 | 1.00 | 13.02 | C |
| ATOM | 6195 | CG | LEU A 456 | 14.068 | 62.273 | -0.197 | 1.00 | 13.27 | C |
| ATOM | 6197 | CD1 | LEU A 456 | 15.574 | 61.968 | -0.311 | 1.00 | 13.18 | C |
| ATOM | 6201 | CD2 | LEU A 456 | 13.574 | 62.881 | -1.415 | 1.00 | 15.68 | C |
| ATOM | 6205 | C | LEU A 456 | 11.035 | 59.995 | 0.751 | 1.00 | 13.63 | C |
| ATOM | 6206 | O | LEU A 456 | 11.529 | 58.883 | 0.551 | 1.00 | 14.72 | O |
| ATOM | 6208 | N | ALA A 457 | 9.824 | 60.182 | 1.264 | 1.00 | 14.85 | N |
| ATOM | 6209 | CA | ALA A 457 | 8.925 | 59.065 | 1.517 | 1.00 | 13.98 | C |
| ATOM | 6211 | CB | ALA A 457 | 7.717 | 59.571 | 2.345 | 1.00 | 15.21 | C |
| ATOM | 6215 | C | ALA A 457 | 8.472 | 58.484 | 0.189 | 1.00 | 13.93 | C |
| ATOM | 6216 | O | ALA A 457 | 8.091 | 59.203 | -0.726 | 1.00 | 13.95 | O |
| ATOM | 6218 | N | ALA A 458 | 8.511 | 57.151 | 0.081 | 1.00 | 13.11 | N |
| ATOM | 6219 | CA | ALA A 458 | 8.085 | 56.473 | -1.139 | 1.00 | 13.46 | C |
| ATOM | 6221 | CB | ALA A 458 | 8.772 | 55.164 | -1.236 | 1.00 | 14.10 | C |
| ATOM | 6225 | C | ALA A 458 | 6.556 | 56.289 | -1.228 | 1.00 | 13.94 | C |
| ATOM | 6226 | O | ALA A 458 | 6.028 | 56.143 | -2.330 | 1.00 | 15.21 | O |
| ATOM | 6228 | N | GLU A 459 | 5.878 | 56.340 | -0.085 | 1.00 | 13.96 | N |
| ATOM | 6229 | CA | GLU A 459 | 4.421 | 56.116 | -0.006 | 1.00 | 14.98 | C |
| ATOM | 6231 | CB | GLU A 459 | 4.144 | 54.728 | 0.596 | 1.00 | 14.93 | C |
| ATOM | 6234 | CG | GLU A 459 | 4.727 | 53.596 | -0.207 | 1.00 | 16.27 | C |
| ATOM | 6237 | CD | GLU A 459 | 3.885 | 53.227 | -1.398 | 1.00 | 15.65 | C |
| ATOM | 6238 | OE1 | GLU A 459 | 2.669 | 53.586 | -1.410 | 1.00 | 16.86 | O |
| ATOM | 6239 | OE2 | GLU A 459 | 4.417 | 52.539 | -2.300 | 1.00 | 15.35 | O |
| ATOM | 6240 | C | GLU A 459 | 3.817 | 57.287 | 0.756 | 1.00 | 14.99 | C |
| ATOM | 6241 | O | GLU A 459 | 4.468 | 58.341 | 0.867 | 1.00 | 15.75 | O |
| ATOM | 6243 | N | ASP A 460 | 2.589 | 57.173 | 1.262 | 1.00 | 14.46 | N |
| ATOM | 6244 | CA | ASP A 460 | 1.910 | 58.367 | 1.795 | 1.00 | 14.37 | C |
| ATOM | 6246 | CB | ASP A 460 | 0.511 | 58.021 | 2.301 | 1.00 | 15.06 | C |
| ATOM | 6249 | CG | ASP A 460 | -0.532 | 58.055 | 1.194 | 1.00 | 16.89 | C |
| ATOM | 6250 | OD1 | ASP A 460 | -0.186 | 58.426 | 0.036 | 1.00 | 15.42 | O |
| ATOM | 6251 | OD2 | ASP A 460 | -1.707 | 57.729 | 1.495 | 1.00 | 16.13 | O |
| ATOM | 6252 | C | ASP A 460 | 2.715 | 59.029 | 2.901 | 1.00 | 15.27 | C |
| ATOM | 6253 | O | ASP A 460 | 3.024 | 58.382 | 3.913 | 1.00 | 15.06 | O |

| ATOM | 6255 | N | PRO A 461 | 3.013 | 60.329 | 2.725 | 1.00 | 15.81 | N |
|------|------|------|----------|--------|--------|--------|------|-------|---|
| ATOM | 6256 | CA | PRO A 461 | 3.807 | 61.056 | 3.717 | 1.00 | 16.50 | C |
| ATOM | 6258 | CB | PRO A 461 | 3.993 | 62.435 | 3.071 | 1.00 | 17.79 | C |
| ATOM | 6261 | CG | PRO A 461 | 3.571 | 62.331 | 1.700 | 1.00 | 18.98 | C |
| ATOM | 6264 | CD | PRO A 461 | 2.638 | 61.199 | 1.592 | 1.00 | 16.84 | C |
| ATOM | 6267 | C | PRO A 461 | 3.177 | 61.202 | 5.114 | 1.00 | 16.34 | C |
| ATOM | 6268 | O | PRO A 461 | 3.905 | 61.436 | 6.078 | 1.00 | 16.67 | O |
| ATOM | 6269 | N | SER A 462 | 1.864 | 60.998 | 5.256 | 1.00 | 17.17 | N |
| ATOM | 6270 | CA | SER A 462 | 1.243 | 61.143 | 6.559 | 1.00 | 16.91 | C |
| ATOM | 6272 | CB | SER A 462 | -0.287 | 61.107 | 6.441 | 1.00 | 17.48 | C |
| ATOM | 6275 | OG | SER A 462 | -0.757 | 59.830 | 6.030 | 1.00 | 15.84 | O |
| ATOM | 6277 | C | SER A 462 | 1.759 | 60.081 | 7.545 | 1.00 | 17.19 | C |
| ATOM | 6278 | O | SER A 462 | 1.717 | 60.300 | 8.766 | 1.00 | 18.03 | O |
| ATOM | 6280 | N | LEU A 463 | 2.245 | 58.952 | 7.034 | 1.00 | 15.82 | N |
| ATOM | 6281 | CA | LEU A 463 | 2.750 | 57.873 | 7.877 | 1.00 | 17.05 | C |
| ATOM | 6283 | CB | LEU A 463 | 1.784 | 56.681 | 7.899 | 1.00 | 18.93 | C |
| ATOM | 6286 | CG | LEU A 463 | 0.511 | 56.975 | 8.719 | 1.00 | 20.02 | C |
| ATOM | 6288 | CD1 | LEU A 463 | -0.541 | 55.920 | 8.477 | 1.00 | 22.93 | C |
| ATOM | 6292 | CD2 | LEU A 463 | 0.791 | 57.107 | 10.219 | 1.00 | 21.33 | C |
| ATOM | 6296 | C | LEU A 463 | 4.169 | 57.448 | 7.494 | 1.00 | 14.94 | C |
| ATOM | 6297 | O | LEU A 463 | 4.618 | 56.317 | 7.785 | 1.00 | 15.93 | O |
| ATOM | 6299 | N | SER A 464 | 4.899 | 58.373 | 6.869 | 1.00 | 14.28 | N |
| ATOM | 6300 | CA | SER A 464 | 6.289 | 58.070 | 6.489 | 1.00 | 15.52 | C |
| ATOM | 6302 | CB | SER A 464 | 6.347 | 57.347 | 5.137 | 1.00 | 15.66 | C |
| ATOM | 6305 | OG | SER A 464 | 7.678 | 57.018 | 4.739 | 1.00 | 15.91 | O |
| ATOM | 6307 | C | SER A 464 | 7.089 | 59.377 | 6.419 | 1.00 | 15.12 | C |
| ATOM | 6308 | O | SER A 464 | 6.761 | 60.256 | 5.631 | 1.00 | 14.29 | O |
| ATOM | 6310 | N | TYR A 465 | 8.136 | 59.476 | 7.252 | 1.00 | 15.59 | N |
| ATOM | 6311 | CA | TYR A 465 | 8.973 | 60.684 | 7.353 | 1.00 | 16.53 | C |
| ATOM | 6313 | CB | TYR A 465 | 8.854 | 61.342 | 8.771 | 1.00 | 18.62 | C |
| ATOM | 6316 | CG | TYR A 465 | 7.459 | 61.225 | 9.331 | 1.00 | 21.17 | C |
| ATOM | 6317 | CD1 | TYR A 465 | 6.389 | 61.813 | 8.695 | 1.00 | 25.63 | C |
| ATOM | 6319 | CE1 | TYR A 465 | 5.050 | 61.634 | 9.175 | 1.00 | 25.37 | C |
| ATOM | 6321 | CZ | TYR A 465 | 4.831 | 60.850 | 10.281 | 1.00 | 24.45 | C |
| ATOM | 6322 | OH | TYR A 465 | 3.538 | 60.638 | 10.789 | 1.00 | 28.69 | O |
| ATOM | 6324 | CE2 | TYR A 465 | 5.906 | 60.258 | 10.940 | 1.00 | 26.68 | C |
| ATOM | 6326 | CD2 | TYR A 465 | 7.206 | 60.437 | 10.449 | 1.00 | 25.17 | C |
| ATOM | 6328 | C | TYR A 465 | 10.414 | 60.323 | 7.009 | 1.00 | 15.29 | C |
| ATOM | 6329 | O | TYR A 465 | 11.348 | 60.973 | 7.479 | 1.00 | 15.04 | O |
| ATOM | 6331 | N | HIS A 466 | 10.538 | 59.346 | 6.108 | 1.00 | 13.17 | N |
| ATOM | 6332 | CA | HIS A 466 | 11.763 | 58.614 | 5.747 | 1.00 | 13.57 | C |
| ATOM | 6334 | CB | HIS A 466 | 11.734 | 58.276 | 4.249 | 1.00 | 13.49 | C |
| ATOM | 6337 | CG | HIS A 466 | 12.893 | 57.440 | 3.790 | 1.00 | 12.96 | C |
| ATOM | 6338 | ND1 | HIS A 466 | 13.168 | 57.199 | 2.455 | 1.00 | 15.16 | N |
| ATOM | 6340 | CE1 | HIS A 466 | 14.253 | 56.449 | 2.359 | 1.00 | 16.70 | C |
| ATOM | 6342 | NE2 | HIS A 466 | 14.710 | 56.224 | 3.572 | 1.00 | 14.35 | N |
| ATOM | 6344 | CD2 | HIS A 466 | 13.872 | 56.826 | 4.488 | 1.00 | 13.94 | C |
| ATOM | 6346 | C | HIS A 466 | 13.029 | 59.344 | 6.162 | 1.00 | 13.90 | C |
| ATOM | 6347 | O | HIS A 466 | 13.655 | 58.943 | 7.129 | 1.00 | 14.32 | O |
| ATOM | 6349 | N | CYS A 467 | 13.386 | 60.382 | 5.420 | 1.00 | 12.83 | N |
| ATOM | 6350 | CA | CYS A 467 | 14.710 | 60.998 | 5.604 | 1.00 | 13.17 | C |
| ATOM | 6352 | CB | CYS A 467 | 15.267 | 61.379 | 4.266 | 1.00 | 13.17 | C |
| ATOM | 6355 | SG | CYS A 467 | 15.821 | 59.947 | 3.272 | 1.00 | 14.91 | S |
| ATOM | 6357 | C | CYS A 467 | 14.764 | 62.197 | 6.554 | 1.00 | 14.17 | C |
| ATOM | 6358 | O | CYS A 467 | 15.799 | 62.879 | 6.604 | 1.00 | 15.04 | O |
| ATOM | 6360 | N | LYS A 468 | 13.697 | 62.453 | 7.319 | 1.00 | 14.99 | N |
| ATOM | 6361 | CA | LYS A 468 | 13.682 | 63.629 | 8.208 | 1.00 | 14.14 | C |

| | | | | | | | | |
|---|---|---|---|---|---|---|---|---|
| ATOM | 6363 | CB | LYS A 468 | 12.295 | 63.826 | 8.815 | 1.00 15.53 | C |
| ATOM | 6366 | CG | LYS A 468 | 12.108 | 65.052 | 9.701 | 1.00 15.77 | C |
| ATOM | 6369 | CD | LYS A 468 | 10.733 | 65.097 | 10.338 | 1.00 19.22 | C |
| ATOM | 6372 | CE | LYS A 468 | 9.658 | 65.571 | 9.356 | 1.00 21.78 | C |
| ATOM | 6375 | NZ | LYS A 468 | 10.165 | 66.749 | 8.561 | 1.00 29.54 | N |
| ATOM | 6379 | C | LYS A 468 | 14.770 | 63.533 | 9.303 | 1.00 14.16 | C |
| ATOM | 6380 | O | LYS A 468 | 15.430 | 64.547 | 9.659 | 1.00 15.44 | O |
| ATOM | 6382 | N | GLY A 469 | 14.969 | 62.322 | 9.833 | 1.00 14.37 | N |
| ATOM | 6383 | CA | GLY A 469 | 15.952 | 62.094 | 10.886 | 1.00 13.66 | C |
| ATOM | 6386 | C | GLY A 469 | 17.344 | 62.400 | 10.333 | 1.00 13.82 | C |
| ATOM | 6387 | O | GLY A 469 | 18.220 | 63.023 | 10.987 | 1.00 15.09 | O |
| ATOM | 6389 | N | LEU A 470 | 17.555 | 61.972 | 9.092 | 1.00 13.29 | N |
| ATOM | 6390 | CA | LEU A 470 | 18.835 | 62.196 | 8.399 | 1.00 12.95 | C |
| ATOM | 6392 | CB | LEU A 470 | 18.916 | 61.347 | 7.145 | 1.00 12.07 | C |
| ATOM | 6395 | CG | LEU A 470 | 19.090 | 59.844 | 7.322 | 1.00 12.44 | C |
| ATOM | 6397 | CD1 | LEU A 470 | 19.111 | 59.100 | 5.990 | 1.00 15.80 | C |
| ATOM | 6401 | CD2 | LEU A 470 | 20.376 | 59.487 | 8.132 | 1.00 14.95 | C |
| ATOM | 6405 | C | LEU A 470 | 19.096 | 63.671 | 8.102 | 1.00 14.44 | C |
| ATOM | 6406 | O | LEU A 470 | 20.245 | 64.125 | 8.143 | 1.00 14.89 | O |
| ATOM | 6408 | N | ASP A 471 | 18.040 | 64.404 | 7.795 | 1.00 14.74 | N |
| ATOM | 6409 | CA | ASP A 471 | 18.148 | 65.865 | 7.662 | 1.00 15.06 | C |
| ATOM | 6411 | CB | ASP A 471 | 16.779 | 66.437 | 7.334 | 1.00 16.84 | C |
| ATOM | 6414 | CG | ASP A 471 | 16.847 | 67.839 | 6.700 | 1.00 19.54 | C |
| ATOM | 6415 | OD1 | ASP A 471 | 17.916 | 68.261 | 6.137 | 1.00 21.37 | O |
| ATOM | 6416 | OD2 | ASP A 471 | 15.784 | 68.546 | 6.738 | 1.00 21.47 | O |
| ATOM | 6417 | C | ASP A 471 | 18.716 | 66.486 | 8.941 | 1.00 15.03 | C |
| ATOM | 6418 | O | ASP A 471 | 19.648 | 67.304 | 8.914 | 1.00 15.57 | O |
| ATOM | 6420 | N | ILE A 472 | 18.192 | 66.048 | 10.075 | 1.00 13.86 | N |
| ATOM | 6421 | CA | ILE A 472 | 18.634 | 66.534 | 11.384 | 1.00 13.64 | C |
| ATOM | 6423 | CB | ILE A 472 | 17.663 | 66.018 | 12.472 | 1.00 13.79 | C |
| ATOM | 6425 | CG1 | ILE A 472 | 16.321 | 66.720 | 12.343 | 1.00 14.17 | C |
| ATOM | 6428 | CD1 | ILE A 472 | 15.161 | 65.982 | 12.968 | 1.00 15.86 | C |
| ATOM | 6432 | CG2 | ILE A 472 | 18.200 | 66.215 | 13.867 | 1.00 14.83 | C |
| ATOM | 6436 | C | ILE A 472 | 20.062 | 66.062 | 11.692 | 1.00 14.91 | C |
| ATOM | 6437 | O | ILE A 472 | 20.894 | 66.845 | 12.191 | 1.00 13.40 | O |
| ATOM | 6439 | N | ALA A 473 | 20.327 | 64.802 | 11.422 | 1.00 14.02 | N |
| ATOM | 6440 | CA | ALA A 473 | 21.683 | 64.241 | 11.627 | 1.00 14.27 | C |
| ATOM | 6442 | CB | ALA A 473 | 21.744 | 62.774 | 11.319 | 1.00 14.99 | C |
| ATOM | 6446 | C | ALA A 473 | 22.714 | 65.005 | 10.789 | 1.00 13.74 | C |
| ATOM | 6447 | O | ALA A 473 | 23.822 | 65.371 | 11.271 | 1.00 14.58 | O |
| ATOM | 6449 | N | ALA A 474 | 22.377 | 65.266 | 9.533 | 1.00 14.19 | N |
| ATOM | 6450 | CA | ALA A 474 | 23.297 | 66.067 | 8.690 | 1.00 14.17 | C |
| ATOM | 6452 | CB | ALA A 474 | 22.774 | 66.241 | 7.286 | 1.00 15.41 | C |
| ATOM | 6456 | C | ALA A 474 | 23.603 | 67.429 | 9.330 | 1.00 13.65 | C |
| ATOM | 6457 | O | ALA A 474 | 24.751 | 67.857 | 9.307 | 1.00 12.94 | O |
| ATOM | 6459 | N | ALA A 475 | 22.595 | 68.094 | 9.912 | 1.00 13.49 | N |
| ATOM | 6460 | CA | ALA A 475 | 22.856 | 69.348 | 10.643 | 1.00 13.29 | C |
| ATOM | 6462 | CB | ALA A 475 | 21.578 | 69.957 | 11.135 | 1.00 14.16 | C |
| ATOM | 6466 | C | ALA A 475 | 23.835 | 69.130 | 11.788 | 1.00 13.43 | C |
| ATOM | 6467 | O | ALA A 475 | 24.796 | 69.890 | 11.955 | 1.00 13.86 | O |
| ATOM | 6469 | N | ALA A 476 | 23.580 | 68.082 | 12.563 | 1.00 13.02 | N |
| ATOM | 6470 | CA | ALA A 476 | 24.443 | 67.766 | 13.708 | 1.00 12.91 | C |
| ATOM | 6472 | CB | ALA A 476 | 23.992 | 66.583 | 14.427 | 1.00 13.91 | C |
| ATOM | 6476 | C | ALA A 476 | 25.869 | 67.545 | 13.264 | 1.00 11.92 | C |
| ATOM | 6477 | O | ALA A 476 | 26.817 | 68.041 | 13.923 | 1.00 12.18 | O |
| ATOM | 6479 | N | TYR A 477 | 26.068 | 66.737 | 12.216 | 1.00 10.66 | N |
| ATOM | 6480 | CA | TYR A 477 | 27.436 | 66.490 | 11.749 | 1.00 12.09 | C |

| | | | | | | | | |
|---|---|---|---|---|---|---|---|---|
| ATOM | 6482 | CB | TYR A 477 | 27.461 | 65.514 | 10.565 | 1.00 11.57 | C |
| ATOM | 6485 | CG | TYR A 477 | 26.772 | 64.185 | 10.846 | 1.00 12.15 | C |
| ATOM | 6486 | CD1 | TYR A 477 | 26.841 | 63.594 | 12.083 | 1.00 13.21 | C |
| ATOM | 6488 | CE1 | TYR A 477 | 26.211 | 62.381 | 12.333 | 1.00 13.32 | C |
| ATOM | 6490 | CZ | TYR A 477 | 25.489 | 61.750 | 11.323 | 1.00 13.21 | C |
| ATOM | 6491 | OH | TYR A 477 | 24.889 | 60.538 | 11.600 | 1.00 13.31 | O |
| ATOM | 6493 | CE2 | TYR A 477 | 25.447 | 62.331 | 10.081 | 1.00 11.38 | C |
| ATOM | 6495 | CD2 | TYR A 477 | 26.076 | 63.520 | 9.850 | 1.00 13.72 | C |
| ATOM | 6497 | C | TYR A 477 | 28.136 | 67.788 | 11.321 | 1.00 11.51 | C |
| ATOM | 6498 | O | TYR A 477 | 29.301 | 68.039 | 11.618 | 1.00 12.50 | O |
| ATOM | 6500 | N | THR A 478 | 27.387 | 68.639 | 10.608 | 1.00 11.65 | N |
| ATOM | 6501 | CA | THR A 478 | 27.899 | 69.930 | 10.134 | 1.00 11.96 | C |
| ATOM | 6503 | CB | THR A 478 | 26.843 | 70.573 | 9.207 | 1.00 11.85 | C |
| ATOM | 6505 | OG1 | THR A 478 | 26.587 | 69.612 | 8.154 | 1.00 13.18 | O |
| ATOM | 6507 | CG2 | THR A 478 | 27.399 | 71.836 | 8.578 | 1.00 12.87 | C |
| ATOM | 6511 | C | THR A 478 | 28.314 | 70.855 | 11.287 | 1.00 11.64 | C |
| ATOM | 6512 | O | THR A 478 | 29.364 | 71.523 | 11.251 | 1.00 13.17 | O |
| ATOM | 6514 | N | SER A 479 | 27.453 | 70.970 | 12.288 | 1.00 11.63 | N |
| ATOM | 6515 | CA | SER A 479 | 27.750 | 71.747 | 13.446 | 1.00 12.24 | C |
| ATOM | 6517 | CB | SER A 479 | 26.584 | 71.584 | 14.409 | 1.00 13.53 | C |
| ATOM | 6520 | OG | SER A 479 | 25.433 | 72.252 | 13.947 | 1.00 12.59 | O |
| ATOM | 6522 | C | SER A 479 | 29.068 | 71.279 | 14.125 | 1.00 12.78 | C |
| ATOM | 6523 | O | SER A 479 | 29.926 | 72.065 | 14.506 | 1.00 12.48 | O |
| ATOM | 6525 | N | GLU A 480 | 29.196 | 69.968 | 14.301 | 1.00 12.73 | N |
| ATOM | 6526 | CA | GLU A 480 | 30.407 | 69.383 | 14.912 | 1.00 12.43 | C |
| ATOM | 6528 | CB | GLU A 480 | 30.209 | 67.889 | 15.094 | 1.00 13.08 | C |
| ATOM | 6531 | CG | GLU A 480 | 31.366 | 67.316 | 15.842 | 1.00 12.51 | C |
| ATOM | 6534 | CD | GLU A 480 | 31.095 | 65.875 | 16.366 | 1.00 12.07 | C |
| ATOM | 6535 | OE1 | GLU A 480 | 29.889 | 65.437 | 16.439 | 1.00 13.53 | O |
| ATOM | 6536 | OE2 | GLU A 480 | 32.058 | 65.163 | 16.741 | 1.00 15.15 | O |
| ATOM | 6537 | C | GLU A 480 | 31.655 | 69.678 | 14.099 | 1.00 12.14 | C |
| ATOM | 6538 | O | GLU A 480 | 32.705 | 70.080 | 14.647 | 1.00 12.90 | O |
| ATOM | 6540 | N | LEU A 481 | 31.543 | 69.599 | 12.767 | 1.00 12.52 | N |
| ATOM | 6541 | CA | LEU A 481 | 32.672 | 69.974 | 11.894 | 1.00 12.41 | C |
| ATOM | 6543 | CB | LEU A 481 | 32.267 | 69.812 | 10.405 | 1.00 12.58 | C |
| ATOM | 6546 | CG | LEU A 481 | 32.271 | 68.361 | 9.964 | 1.00 12.40 | C |
| ATOM | 6548 | CD1 | LEU A 481 | 31.589 | 68.172 | 8.595 | 1.00 15.83 | C |
| ATOM | 6552 | CD2 | LEU A 481 | 33.687 | 67.785 | 9.928 | 1.00 13.92 | C |
| ATOM | 6556 | C | LEU A 481 | 33.107 | 71.442 | 12.077 | 1.00 11.57 | C |
| ATOM | 6557 | O | LEU A 481 | 34.278 | 71.783 | 11.981 | 1.00 10.70 | O |
| ATOM | 6559 | N | GLY A 482 | 32.129 | 72.326 | 12.312 | 1.00 11.70 | N |
| ATOM | 6560 | CA | GLY A 482 | 32.409 | 73.740 | 12.467 | 1.00 12.75 | C |
| ATOM | 6563 | C | GLY A 482 | 33.278 | 73.995 | 13.683 | 1.00 12.36 | C |
| ATOM | 6564 | O | GLY A 482 | 34.297 | 74.706 | 13.641 | 1.00 14.02 | O |
| ATOM | 6566 | N | HIS A 483 | 32.901 | 73.379 | 14.792 | 1.00 12.53 | N |
| ATOM | 6567 | CA | HIS A 483 | 33.652 | 73.543 | 16.036 | 1.00 12.49 | C |
| ATOM | 6569 | CB | HIS A 483 | 32.897 | 72.916 | 17.215 | 1.00 12.21 | C |
| ATOM | 6572 | CG | HIS A 483 | 33.710 | 72.831 | 18.476 | 1.00 14.89 | C |
| ATOM | 6573 | ND1 | HIS A 483 | 34.458 | 71.718 | 18.785 | 1.00 16.54 | N |
| ATOM | 6575 | CE1 | HIS A 483 | 35.054 | 71.914 | 19.955 | 1.00 16.99 | C |
| ATOM | 6577 | NE2 | HIS A 483 | 34.724 | 73.116 | 20.402 | 1.00 13.42 | N |
| ATOM | 6579 | CD2 | HIS A 483 | 33.861 | 73.699 | 19.509 | 1.00 14.89 | C |
| ATOM | 6581 | C | HIS A 483 | 35.033 | 72.913 | 15.892 | 1.00 12.28 | C |
| ATOM | 6582 | O | HIS A 483 | 36.017 | 73.464 | 16.337 | 1.00 13.04 | O |
| ATOM | 6584 | N | LEU A 484 | 35.114 | 71.769 | 15.225 | 1.00 10.74 | N |
| ATOM | 6585 | CA | LEU A 484 | 36.441 | 71.095 | 15.037 | 1.00 11.65 | C |
| ATOM | 6587 | CB | LEU A 484 | 36.239 | 69.802 | 14.259 | 1.00 12.37 | C |

| ATOM | 6590 | CG | LEU A 484 | 35.871 | 68.645 | 15.176 | 1.00 | 13.03 | C |
|------|------|------|-----------|--------|--------|--------|------|-------|---|
| ATOM | 6592 | CD1 | LEU A 484 | 35.228 | 67.444 | 14.471 | 1.00 | 12.54 | C |
| ATOM | 6596 | CD2 | LEU A 484 | 37.111 | 68.175 | 15.929 | 1.00 | 15.53 | C |
| ATOM | 6600 | C | LEU A 484 | 37.412 | 71.995 | 14.284 | 1.00 | 12.57 | C |
| ATOM | 6601 | O | LEU A 484 | 38.621 | 71.974 | 14.524 | 1.00 | 11.98 | O |
| ATOM | 6603 | N | ALA A 485 | 36.876 | 72.766 | 13.354 | 1.00 | 12.81 | N |
| ATOM | 6604 | CA | ALA A 485 | 37.711 | 73.574 | 12.437 | 1.00 | 11.66 | C |
| ATOM | 6606 | CB | ALA A 485 | 36.905 | 74.043 | 11.246 | 1.00 | 13.75 | C |
| ATOM | 6610 | C | ALA A 485 | 38.478 | 74.747 | 13.025 | 1.00 | 11.91 | C |
| ATOM | 6611 | O | ALA A 485 | 39.307 | 75.330 | 12.333 | 1.00 | 13.01 | O |
| ATOM | 6613 | N | ASN A 486 | 38.187 | 75.149 | 14.266 | 1.00 | 11.85 | N |
| ATOM | 6614 | CA | ASN A 486 | 39.020 | 76.189 | 14.905 | 1.00 | 11.95 | C |
| ATOM | 6616 | CB | ASN A 486 | 38.505 | 76.516 | 16.280 | 1.00 | 12.13 | C |
| ATOM | 6619 | CG | ASN A 486 | 37.135 | 77.109 | 16.233 | 1.00 | 14.76 | C |
| ATOM | 6620 | OD1 | ASN A 486 | 36.908 | 78.085 | 15.468 | 1.00 | 12.88 | O |
| ATOM | 6621 | ND2 | ASN A 486 | 36.213 | 76.567 | 17.026 | 1.00 | 14.90 | N |
| ATOM | 6624 | C | ASN A 486 | 40.473 | 75.648 | 14.988 | 1.00 | 11.95 | C |
| ATOM | 6625 | O | ASN A 486 | 40.697 | 74.438 | 15.070 | 1.00 | 12.72 | O |
| ATOM | 6627 | N | PRO A 487 | 41.446 | 76.571 | 14.906 | 1.00 | 14.22 | N |
| ATOM | 6628 | CA | PRO A 487 | 42.846 | 76.145 | 14.899 | 1.00 | 13.35 | C |
| ATOM | 6630 | CB | PRO A 487 | 43.607 | 77.424 | 14.616 | 1.00 | 13.48 | C |
| ATOM | 6633 | CG | PRO A 487 | 42.651 | 78.571 | 14.983 | 1.00 | 14.32 | C |
| ATOM | 6636 | CD | PRO A 487 | 41.282 | 78.014 | 14.712 | 1.00 | 14.57 | C |
| ATOM | 6639 | C | PRO A 487 | 43.281 | 75.618 | 16.256 | 1.00 | 13.57 | C |
| ATOM | 6640 | O | PRO A 487 | 42.820 | 76.132 | 17.309 | 1.00 | 13.42 | O |
| ATOM | 6641 | N | VAL A 488 | 44.166 | 74.626 | 16.199 | 1.00 | 12.22 | N |
| ATOM | 6642 | CA | VAL A 488 | 44.869 | 74.165 | 17.396 | 1.00 | 12.36 | C |
| ATOM | 6644 | CB | VAL A 488 | 45.228 | 72.657 | 17.247 | 1.00 | 13.04 | C |
| ATOM | 6646 | CG1 | VAL A 488 | 46.265 | 72.235 | 18.267 | 1.00 | 14.01 | C |
| ATOM | 6650 | CG2 | VAL A 488 | 43.958 | 71.842 | 17.311 | 1.00 | 13.53 | C |
| ATOM | 6654 | C | VAL A 488 | 46.116 | 75.013 | 17.620 | 1.00 | 12.41 | C |
| ATOM | 6655 | O | VAL A 488 | 46.554 | 75.219 | 18.759 | 1.00 | 12.73 | O |
| ATOM | 6657 | N | THR A 489 | 46.711 | 75.502 | 16.531 | 1.00 | 12.32 | N |
| ATOM | 6658 | CA | THR A 489 | 48.054 | 76.134 | 16.586 | 1.00 | 13.07 | C |
| ATOM | 6660 | CB | THR A 489 | 48.707 | 76.201 | 15.224 | 1.00 | 12.41 | C |
| ATOM | 6662 | OG1 | THR A 489 | 47.882 | 76.940 | 14.324 | 1.00 | 14.20 | O |
| ATOM | 6664 | CG2 | THR A 489 | 48.890 | 74.765 | 14.722 | 1.00 | 15.57 | C |
| ATOM | 6668 | C | THR A 489 | 48.133 | 77.487 | 17.272 | 1.00 | 12.48 | C |
| ATOM | 6669 | O | THR A 489 | 49.232 | 77.993 | 17.506 | 1.00 | 15.94 | O |
| ATOM | 6671 | N | THR A 490 | 46.983 | 78.070 | 17.603 | 1.00 | 12.30 | N |
| ATOM | 6672 | CA | THR A 490 | 46.949 | 79.265 | 18.410 | 1.00 | 13.30 | C |
| ATOM | 6674 | CB | THR A 490 | 45.704 | 80.028 | 18.100 | 1.00 | 13.68 | C |
| ATOM | 6676 | OG1 | THR A 490 | 44.536 | 79.193 | 18.254 | 1.00 | 13.47 | O |
| ATOM | 6678 | CG2 | THR A 490 | 45.795 | 80.587 | 16.658 | 1.00 | 15.29 | C |
| ATOM | 6682 | C | THR A 490 | 47.025 | 79.018 | 19.925 | 1.00 | 13.24 | C |
| ATOM | 6683 | O | THR A 490 | 46.921 | 79.975 | 20.706 | 1.00 | 16.40 | O |
| ATOM | 6685 | N | HIS A 491 | 47.144 | 77.731 | 20.313 | 1.00 | 13.17 | N |
| ATOM | 6686 | CA | HIS A 491 | 47.124 | 77.337 | 21.738 | 1.00 | 12.28 | C |
| ATOM | 6688 | CB | HIS A 491 | 46.025 | 76.306 | 21.935 | 1.00 | 13.01 | C |
| ATOM | 6691 | CG | HIS A 491 | 44.678 | 76.896 | 21.698 | 1.00 | 12.07 | C |
| ATOM | 6692 | ND1 | HIS A 491 | 44.090 | 77.744 | 22.603 | 1.00 | 13.03 | N |
| ATOM | 6694 | CE1 | HIS A 491 | 42.962 | 78.217 | 22.081 | 1.00 | 13.18 | C |
| ATOM | 6696 | NE2 | HIS A 491 | 42.810 | 77.696 | 20.865 | 1.00 | 13.97 | N |
| ATOM | 6698 | CD2 | HIS A 491 | 43.891 | 76.902 | 20.589 | 1.00 | 14.10 | C |
| ATOM | 6700 | C | HIS A 491 | 48.496 | 76.897 | 22.266 | 1.00 | 12.94 | C |
| ATOM | 6701 | O | HIS A 491 | 48.594 | 76.228 | 23.274 | 1.00 | 11.76 | O |
| ATOM | 6703 | N | VAL A 492 | 49.545 | 77.414 | 21.642 | 1.00 | 13.52 | N |

| | | | | | | | | | |
|---|---|---|---|---|---|---|---|---|---|
| ATOM | 6704 | CA | VAL A 492 | 50.942 | 77.063 | 22.010 | 1.00 | 13.29 | C |
| ATOM | 6706 | CB | VAL A 492 | 51.914 | 77.664 | 20.984 | 1.00 | 14.39 | C |
| ATOM | 6708 | CG1 | VAL A 492 | 53.392 | 77.495 | 21.455 | 1.00 | 14.89 | C |
| ATOM | 6712 | CG2 | VAL A 492 | 51.643 | 77.026 | 19.621 | 1.00 | 14.67 | C |
| ATOM | 6716 | C | VAL A 492 | 51.261 | 77.571 | 23.398 | 1.00 | 12.67 | C |
| ATOM | 6717 | O | VAL A 492 | 51.033 | 78.787 | 23.697 | 1.00 | 13.35 | O |
| ATOM | 6719 | N | GLN A 493 | 51.759 | 76.669 | 24.252 | 1.00 | 13.07 | N |
| ATOM | 6720 | CA | GLN A 493 | 52.252 | 76.983 | 25.599 | 1.00 | 12.68 | C |
| ATOM | 6722 | CB | GLN A 493 | 51.755 | 75.922 | 26.601 | 1.00 | 12.74 | C |
| ATOM | 6725 | CG | GLN A 493 | 50.201 | 75.692 | 26.567 | 1.00 | 13.61 | C |
| ATOM | 6728 | CD | GLN A 493 | 49.485 | 77.001 | 27.006 | 1.00 | 13.19 | C |
| ATOM | 6729 | OE1 | GLN A 493 | 49.906 | 77.637 | 27.996 | 1.00 | 15.50 | O |
| ATOM | 6730 | NE2 | GLN A 493 | 48.474 | 77.454 | 26.236 | 1.00 | 13.26 | N |
| ATOM | 6733 | C | GLN A 493 | 53.770 | 77.074 | 25.651 | 1.00 | 13.33 | C |
| ATOM | 6734 | O | GLN A 493 | 54.452 | 76.463 | 24.830 | 1.00 | 13.95 | O |
| ATOM | 6736 | N | PRO A 494 | 54.315 | 77.821 | 26.627 | 1.00 | 15.23 | N |
| ATOM | 6737 | CA | PRO A 494 | 55.763 | 77.974 | 26.821 | 1.00 | 15.75 | C |
| ATOM | 6739 | CB | PRO A 494 | 55.854 | 79.127 | 27.831 | 1.00 | 15.86 | C |
| ATOM | 6742 | CG | PRO A 494 | 54.602 | 78.979 | 28.645 | 1.00 | 17.33 | C |
| ATOM | 6745 | CD | PRO A 494 | 53.544 | 78.605 | 27.611 | 1.00 | 15.77 | C |
| ATOM | 6748 | C | PRO A 494 | 56.426 | 76.745 | 27.399 | 1.00 | 17.77 | C |
| ATOM | 6749 | O | PRO A 494 | 56.960 | 76.782 | 28.528 | 1.00 | 20.31 | O |
| ATOM | 6750 | N | ALA A 495 | 56.510 | 75.694 | 26.617 | 1.00 | 17.60 | N |
| ATOM | 6751 | CA | ALA A 495 | 56.920 | 74.405 | 27.097 | 1.00 | 16.64 | C |
| ATOM | 6753 | CB | ALA A 495 | 56.577 | 73.326 | 26.018 | 1.00 | 17.05 | C |
| ATOM | 6757 | C | ALA A 495 | 58.403 | 74.297 | 27.453 | 1.00 | 17.23 | C |
| ATOM | 6758 | O | ALA A 495 | 59.288 | 74.933 | 26.821 | 1.00 | 15.68 | O |
| ATOM | 6760 | N | GLU A 496 | 58.647 | 73.459 | 28.470 | 1.00 | 17.14 | N |
| ATOM | 6761 | CA | GLU A 496 | 60.003 | 73.005 | 28.829 | 1.00 | 16.75 | C |
| ATOM | 6763 | CB | GLU A 496 | 60.630 | 72.146 | 27.708 | 1.00 | 16.87 | C |
| ATOM | 6766 | CG | GLU A 496 | 61.768 | 71.255 | 28.181 | 1.00 | 20.18 | C |
| ATOM | 6769 | CD | GLU A 496 | 63.056 | 71.444 | 27.379 | 1.00 | 24.66 | C |
| ATOM | 6770 | OE1 | GLU A 496 | 63.093 | 71.348 | 26.105 | 1.00 | 24.97 | O |
| ATOM | 6771 | OE2 | GLU A 496 | 64.055 | 71.662 | 28.064 | 1.00 | 28.33 | O |
| ATOM | 6772 | C | GLU A 496 | 60.936 | 74.169 | 29.188 | 1.00 | 17.69 | C |
| ATOM | 6773 | O | GLU A 496 | 61.915 | 74.422 | 28.504 | 1.00 | 18.38 | O |
| ATOM | 6775 | N | MSE A 497 | 60.619 | 74.860 | 30.278 | 1.00 | 18.07 | N |
| ATOM | 6776 | CA | MSE A 497 | 61.386 | 76.044 | 30.681 | 1.00 | 19.68 | C |
| ATOM | 6778 | CB | MSE A 497 | 62.763 | 75.635 | 31.164 | 1.00 | 19.66 | C |
| ATOM | 6781 | CG | MSE A 497 | 62.657 | 74.764 | 32.357 | 1.00 | 20.36 | C |
| ATOM | 6784 | SE | MSE A 497 | 64.470 | 74.302 | 33.067 | 1.00 | 34.40 | SE |
| ATOM | 6785 | CE | MSE A 497 | 65.237 | 76.049 | 33.412 | 1.00 | 29.46 | C |
| ATOM | 6789 | C | MSE A 497 | 61.516 | 77.104 | 29.579 | 1.00 | 17.67 | C |
| ATOM | 6790 | O | MSE A 497 | 62.496 | 77.841 | 29.552 | 1.00 | 18.25 | O |
| ATOM | 6792 | N | ALA A 498 | 60.494 | 77.178 | 28.726 | 1.00 | 16.79 | N |
| ATOM | 6793 | CA | ALA A 498 | 60.471 | 78.026 | 27.543 | 1.00 | 16.81 | C |
| ATOM | 6795 | CB | ALA A 498 | 60.428 | 79.512 | 27.898 | 1.00 | 17.70 | C |
| ATOM | 6799 | C | ALA A 498 | 61.582 | 77.734 | 26.543 | 1.00 | 15.54 | C |
| ATOM | 6800 | O | ALA A 498 | 61.748 | 78.485 | 25.557 | 1.00 | 14.10 | O |
| ATOM | 6802 | N | ASN A 499 | 62.294 | 76.598 | 26.674 | 1.00 | 14.43 | N |
| ATOM | 6803 | CA | ASN A 499 | 63.198 | 76.192 | 25.605 | 1.00 | 15.56 | C |
| ATOM | 6805 | CB | ASN A 499 | 64.006 | 74.964 | 25.978 | 1.00 | 15.32 | C |
| ATOM | 6808 | CG | ASN A 499 | 64.917 | 74.487 | 24.835 | 1.00 | 22.82 | C |
| ATOM | 6809 | OD1 | ASN A 499 | 65.576 | 75.298 | 24.157 | 1.00 | 24.26 | O |
| ATOM | 6810 | ND2 | ASN A 499 | 64.934 | 73.152 | 24.589 | 1.00 | 25.61 | N |
| ATOM | 6813 | C | ASN A 499 | 62.363 | 75.896 | 24.363 | 1.00 | 13.69 | C |
| ATOM | 6814 | O | ASN A 499 | 62.724 | 76.280 | 23.252 | 1.00 | 15.29 | O |

| ATOM | 6816 | N | GLN | A | 500 | 61.200 | 75.282 | 24.583 | 1.00 | 12.50 | N |
|------|------|-----|-----|---|-----|--------|--------|--------|------|-------|---|
| ATOM | 6817 | CA | GLN | A | 500 | 60.265 | 74.943 | 23.500 | 1.00 | 13.46 | C |
| ATOM | 6819 | CB | GLN | A | 500 | 59.727 | 73.489 | 23.629 | 1.00 | 13.74 | C |
| ATOM | 6822 | CG | GLN | A | 500 | 60.897 | 72.478 | 23.783 | 1.00 | 14.52 | C |
| ATOM | 6825 | CD | GLN | A | 500 | 60.530 | 71.055 | 23.512 | 1.00 | 14.47 | C |
| ATOM | 6826 | OE1 | GLN | A | 500 | 59.607 | 70.771 | 22.733 | 1.00 | 16.45 | O |
| ATOM | 6827 | NE2 | GLN | A | 500 | 61.241 | 70.151 | 24.175 | 1.00 | 14.05 | N |
| ATOM | 6830 | C | GLN | A | 500 | 59.111 | 75.960 | 23.440 | 1.00 | 13.36 | C |
| ATOM | 6831 | O | GLN | A | 500 | 57.968 | 75.566 | 23.270 | 1.00 | 14.87 | O |
| ATOM | 6833 | N | ALA | A | 501 | 59.453 | 77.255 | 23.525 | 1.00 | 13.51 | N |
| ATOM | 6834 | CA | ALA | A | 501 | 58.420 | 78.310 | 23.657 | 1.00 | 12.42 | C |
| ATOM | 6836 | CB | ALA | A | 501 | 59.026 | 79.629 | 23.945 | 1.00 | 13.54 | C |
| ATOM | 6840 | C | ALA | A | 501 | 57.500 | 78.417 | 22.453 | 1.00 | 12.29 | C |
| ATOM | 6841 | O | ALA | A | 501 | 56.386 | 78.962 | 22.557 | 1.00 | 13.49 | O |
| ATOM | 6843 | N | VAL | A | 502 | 57.998 | 77.937 | 21.305 | 1.00 | 11.48 | N |
| ATOM | 6844 | CA | VAL | A | 502 | 57.181 | 77.717 | 20.102 | 1.00 | 11.81 | C |
| ATOM | 6846 | CB | VAL | A | 502 | 57.590 | 78.493 | 18.837 | 1.00 | 13.02 | C |
| ATOM | 6848 | CG1 | VAL | A | 502 | 57.122 | 79.948 | 18.934 | 1.00 | 10.53 | C |
| ATOM | 6852 | CG2 | VAL | A | 502 | 59.029 | 78.358 | 18.482 | 1.00 | 12.99 | C |
| ATOM | 6856 | C | VAL | A | 502 | 57.214 | 76.235 | 19.838 | 1.00 | 12.38 | C |
| ATOM | 6857 | O | VAL | A | 502 | 58.286 | 75.603 | 19.821 | 1.00 | 12.70 | O |
| ATOM | 6859 | N | ASN | A | 503 | 56.040 | 75.655 | 19.637 | 1.00 | 10.70 | N |
| ATOM | 6860 | CA | ASN | A | 503 | 55.928 | 74.197 | 19.380 | 1.00 | 9.52 | C |
| ATOM | 6862 | CB | ASN | A | 503 | 55.822 | 73.355 | 20.649 | 1.00 | 11.32 | C |
| ATOM | 6865 | CG | ASN | A | 503 | 54.816 | 73.911 | 21.626 | 1.00 | 11.85 | C |
| ATOM | 6866 | OD1 | ASN | A | 503 | 53.602 | 73.590 | 21.515 | 1.00 | 12.58 | O |
| ATOM | 6867 | ND2 | ASN | A | 503 | 55.300 | 74.745 | 22.603 | 1.00 | 10.81 | N |
| ATOM | 6870 | C | ASN | A | 503 | 54.719 | 73.998 | 18.446 | 1.00 | 10.70 | C |
| ATOM | 6871 | O | ASN | A | 503 | 53.741 | 74.740 | 18.517 | 1.00 | 9.54 | O |
| ATOM | 6873 | N | SER | A | 504 | 54.850 | 73.090 | 17.479 | 1.00 | 10.81 | N |
| ATOM | 6874 | CA | SER | A | 504 | 53.906 | 73.064 | 16.337 | 1.00 | 11.58 | C |
| ATOM | 6876 | CB | SER | A | 504 | 54.481 | 72.222 | 15.206 | 1.00 | 12.66 | C |
| ATOM | 6879 | OG | SER | A | 504 | 54.350 | 70.805 | 15.455 | 1.00 | 13.42 | O |
| ATOM | 6881 | C | SER | A | 504 | 52.521 | 72.523 | 16.623 | 1.00 | 11.76 | C |
| ATOM | 6882 | O | SER | A | 504 | 51.591 | 72.857 | 15.915 | 1.00 | 11.93 | O |
| ATOM | 6884 | N | LEU | A | 505 | 52.408 | 71.660 | 17.627 | 1.00 | 10.54 | N |
| ATOM | 6885 | CA | LEU | A | 505 | 51.164 | 70.995 | 17.979 | 1.00 | 9.96 | C |
| ATOM | 6887 | CB | LEU | A | 505 | 50.115 | 72.001 | 18.511 | 1.00 | 9.37 | C |
| ATOM | 6890 | CG | LEU | A | 505 | 50.498 | 72.798 | 19.759 | 1.00 | 11.06 | C |
| ATOM | 6892 | CD1 | LEU | A | 505 | 49.399 | 73.885 | 20.048 | 1.00 | 13.05 | C |
| ATOM | 6896 | CD2 | LEU | A | 505 | 50.830 | 71.918 | 20.952 | 1.00 | 13.82 | C |
| ATOM | 6900 | C | LEU | A | 505 | 50.594 | 70.160 | 16.808 | 1.00 | 10.72 | C |
| ATOM | 6901 | O | LEU | A | 505 | 49.372 | 69.847 | 16.765 | 1.00 | 11.53 | O |
| ATOM | 6903 | N | ALA | A | 506 | 51.508 | 69.640 | 15.951 | 1.00 | 10.65 | N |
| ATOM | 6904 | CA | ALA | A | 506 | 51.069 | 68.936 | 14.726 | 1.00 | 11.96 | C |
| ATOM | 6906 | CB | ALA | A | 506 | 52.287 | 68.453 | 13.943 | 1.00 | 11.36 | C |
| ATOM | 6910 | C | ALA | A | 506 | 50.224 | 67.740 | 15.059 | 1.00 | 12.12 | C |
| ATOM | 6911 | O | ALA | A | 506 | 49.243 | 67.489 | 14.389 | 1.00 | 12.19 | O |
| ATOM | 6913 | N | LEU | A | 507 | 50.626 | 66.933 | 16.052 | 1.00 | 12.01 | N |
| ATOM | 6914 | CA | LEU | A | 507 | 49.910 | 65.653 | 16.261 | 1.00 | 12.24 | C |
| ATOM | 6916 | CB | LEU | A | 507 | 50.645 | 64.754 | 17.255 | 1.00 | 13.01 | C |
| ATOM | 6919 | CG | LEU | A | 507 | 49.953 | 63.375 | 17.330 | 1.00 | 13.45 | C |
| ATOM | 6921 | CD1 | LEU | A | 507 | 49.898 | 62.628 | 15.977 | 1.00 | 15.49 | C |
| ATOM | 6925 | CD2 | LEU | A | 507 | 50.631 | 62.531 | 18.386 | 1.00 | 15.19 | C |
| ATOM | 6929 | C | LEU | A | 507 | 48.488 | 65.934 | 16.761 | 1.00 | 11.96 | C |
| ATOM | 6930 | O | LEU | A | 507 | 47.530 | 65.279 | 16.370 | 1.00 | 12.95 | O |
| ATOM | 6932 | N | ILE | A | 508 | 48.381 | 66.899 | 17.670 | 1.00 | 11.47 | N |

| ATOM | 6933 | CA | ILE A 508 | 47.048 | 67.278 | 18.180 | 1.00 | 12.04 | C |
| --- | --- | --- | --- | --- | --- | --- | --- | --- | --- |
| ATOM | 6935 | CB | ILE A 508 | 47.133 | 68.349 | 19.284 | 1.00 | 11.56 | C |
| ATOM | 6937 | CG1 | ILE A 508 | 47.844 | 67.785 | 20.516 | 1.00 | 11.41 | C |
| ATOM | 6940 | CD1 | ILE A 508 | 48.354 | 68.845 | 21.500 | 1.00 | 12.63 | C |
| ATOM | 6944 | CG2 | ILE A 508 | 45.702 | 68.859 | 19.643 | 1.00 | 12.52 | C |
| ATOM | 6948 | C | ILE A 508 | 46.164 | 67.738 | 16.987 | 1.00 | 11.23 | C |
| ATOM | 6949 | O | ILE A 508 | 45.015 | 67.312 | 16.812 | 1.00 | 12.16 | O |
| ATOM | 6951 | N | SER A 509 | 46.733 | 68.589 | 16.147 | 1.00 | 11.89 | N |
| ATOM | 6952 | CA | SER A 509 | 46.009 | 69.078 | 14.963 | 1.00 | 11.81 | C |
| ATOM | 6954 | CB | SER A 509 | 46.865 | 70.098 | 14.223 | 1.00 | 11.85 | C |
| ATOM | 6957 | OG | SER A 509 | 46.051 | 70.781 | 13.226 | 1.00 | 13.97 | O |
| ATOM | 6959 | C | SER A 509 | 45.605 | 67.910 | 14.077 | 1.00 | 12.17 | C |
| ATOM | 6960 | O | SER A 509 | 44.478 | 67.773 | 13.635 | 1.00 | 11.41 | O |
| ATOM | 6962 | N | ALA A 510 | 46.553 | 67.037 | 13.801 | 1.00 | 11.10 | N |
| ATOM | 6963 | CA | ALA A 510 | 46.267 | 65.838 | 13.000 | 1.00 | 12.20 | C |
| ATOM | 6965 | CB | ALA A 510 | 47.546 | 65.050 | 12.779 | 1.00 | 12.09 | C |
| ATOM | 6969 | C | ALA A 510 | 45.177 | 64.978 | 13.590 | 1.00 | 12.17 | C |
| ATOM | 6970 | O | ALA A 510 | 44.358 | 64.375 | 12.857 | 1.00 | 13.02 | O |
| ATOM | 6972 | N | ARG A 511 | 45.151 | 64.878 | 14.929 | 1.00 | 11.03 | N |
| ATOM | 6973 | CA | ARG A 511 | 44.087 | 64.118 | 15.577 | 1.00 | 11.76 | C |
| ATOM | 6975 | CB | ARG A 511 | 44.374 | 64.016 | 17.049 | 1.00 | 11.71 | C |
| ATOM | 6978 | CG | ARG A 511 | 45.407 | 62.938 | 17.401 | 1.00 | 12.80 | C |
| ATOM | 6981 | CD | ARG A 511 | 45.760 | 62.884 | 18.899 | 1.00 | 11.18 | C |
| ATOM | 6984 | NE | ARG A 511 | 44.524 | 63.013 | 19.689 | 1.00 | 12.79 | N |
| ATOM | 6986 | CZ | ARG A 511 | 44.322 | 63.916 | 20.645 | 1.00 | 11.43 | C |
| ATOM | 6987 | NH1 | ARG A 511 | 45.326 | 64.637 | 21.110 | 1.00 | 12.79 | N |
| ATOM | 6990 | NH2 | ARG A 511 | 43.145 | 63.979 | 21.241 | 1.00 | 12.26 | N |
| ATOM | 6993 | C | ARG A 511 | 42.738 | 64.749 | 15.341 | 1.00 | 11.27 | C |
| ATOM | 6994 | O | ARG A 511 | 41.749 | 64.063 | 15.019 | 1.00 | 12.37 | O |
| ATOM | 6996 | N | ARG A 512 | 42.688 | 66.064 | 15.427 | 1.00 | 10.50 | N |
| ATOM | 6997 | CA | ARG A 512 | 41.421 | 66.755 | 15.190 | 1.00 | 10.76 | C |
| ATOM | 6999 | CB | ARG A 512 | 41.491 | 68.201 | 15.648 | 1.00 | 11.62 | C |
| ATOM | 7002 | CG | ARG A 512 | 41.738 | 68.411 | 17.114 | 1.00 | 11.39 | C |
| ATOM | 7005 | CD | ARG A 512 | 40.700 | 67.619 | 17.920 | 1.00 | 14.13 | C |
| ATOM | 7008 | NE | ARG A 512 | 40.821 | 67.920 | 19.359 | 1.00 | 13.36 | N |
| ATOM | 7010 | CZ | ARG A 512 | 40.648 | 67.065 | 20.353 | 1.00 | 14.09 | C |
| ATOM | 7011 | NH1 | ARG A 512 | 40.418 | 65.799 | 20.126 | 1.00 | 16.47 | N |
| ATOM | 7014 | NH2 | ARG A 512 | 40.734 | 67.503 | 21.602 | 1.00 | 14.80 | N |
| ATOM | 7017 | C | ARG A 512 | 41.000 | 66.654 | 13.712 | 1.00 | 10.57 | C |
| ATOM | 7018 | O | ARG A 512 | 39.791 | 66.475 | 13.421 | 1.00 | 11.69 | O |
| ATOM | 7020 | N | THR A 513 | 41.943 | 66.740 | 12.793 | 1.00 | 10.72 | N |
| ATOM | 7021 | CA | THR A 513 | 41.589 | 66.622 | 11.359 | 1.00 | 11.70 | C |
| ATOM | 7023 | CB | THR A 513 | 42.742 | 67.008 | 10.498 | 1.00 | 12.24 | C |
| ATOM | 7025 | OG1 | THR A 513 | 43.113 | 68.329 | 10.844 | 1.00 | 10.72 | O |
| ATOM | 7027 | CG2 | THR A 513 | 42.397 | 66.933 | 9.022 | 1.00 | 13.57 | C |
| ATOM | 7031 | C | THR A 513 | 41.080 | 65.206 | 11.057 | 1.00 | 11.94 | C |
| ATOM | 7032 | O | THR A 513 | 40.139 | 64.999 | 10.288 | 1.00 | 13.44 | O |
| ATOM | 7034 | N | THR A 514 | 41.677 | 64.190 | 11.694 | 1.00 | 11.93 | N |
| ATOM | 7035 | CA | THR A 514 | 41.214 | 62.793 | 11.590 | 1.00 | 11.89 | C |
| ATOM | 7037 | CB | THR A 514 | 42.154 | 61.866 | 12.354 | 1.00 | 12.40 | C |
| ATOM | 7039 | OG1 | THR A 514 | 43.468 | 62.018 | 11.794 | 1.00 | 12.67 | O |
| ATOM | 7041 | CG2 | THR A 514 | 41.737 | 60.431 | 12.254 | 1.00 | 14.34 | C |
| ATOM | 7045 | C | THR A 514 | 39.770 | 62.647 | 12.051 | 1.00 | 12.21 | C |
| ATOM | 7046 | O | THR A 514 | 38.959 | 61.967 | 11.409 | 1.00 | 10.96 | O |
| ATOM | 7048 | N | GLU A 515 | 39.446 | 63.319 | 13.141 | 1.00 | 12.25 | N |
| ATOM | 7049 | CA | GLU A 515 | 38.040 | 63.313 | 13.653 | 1.00 | 12.17 | C |
| ATOM | 7051 | CB | GLU A 515 | 37.937 | 64.005 | 15.028 | 1.00 | 12.40 | C |

| ATOM | 7054 | CG | GLU A 515 | 36.527 | 63.882 | 15.597 | 1.00 | 14.45 | C |
|---|---|---|---|---|---|---|---|---|---|
| ATOM | 7057 | CD | GLU A 515 | 36.374 | 64.137 | 17.067 | 1.00 | 16.29 | C |
| ATOM | 7058 | OE1 | GLU A 515 | 37.371 | 64.445 | 17.776 | 1.00 | 18.11 | O |
| ATOM | 7059 | OE2 | GLU A 515 | 35.187 | 63.997 | 17.535 | 1.00 | 18.72 | O |
| ATOM | 7060 | C | GLU A 515 | 37.100 | 64.004 | 12.642 | 1.00 | 12.06 | C |
| ATOM | 7061 | O | GLU A 515 | 36.014 | 63.501 | 12.323 | 1.00 | 11.17 | O |
| ATOM | 7063 | N | SER A 516 | 37.534 | 65.136 | 12.106 | 1.00 | 11.42 | N |
| ATOM | 7064 | CA | SER A 516 | 36.778 | 65.782 | 11.043 | 1.00 | 11.25 | C |
| ATOM | 7066 | CB | SER A 516 | 37.491 | 67.090 | 10.645 | 1.00 | 11.22 | C |
| ATOM | 7069 | OG | SER A 516 | 37.306 | 68.050 | 11.715 | 1.00 | 11.49 | O |
| ATOM | 7071 | C | SER A 516 | 36.543 | 64.889 | 9.827 | 1.00 | 12.19 | C |
| ATOM | 7072 | O | SER A 516 | 35.457 | 64.896 | 9.248 | 1.00 | 11.78 | O |
| ATOM | 7074 | N | ASN A 517 | 37.559 | 64.133 | 9.398 | 1.00 | 11.17 | N |
| ATOM | 7075 | CA | ASN A 517 | 37.347 | 63.149 | 8.308 | 1.00 | 12.54 | C |
| ATOM | 7077 | CB | ASN A 517 | 38.614 | 62.364 | 7.981 | 1.00 | 13.33 | C |
| ATOM | 7080 | CG | ASN A 517 | 39.599 | 63.102 | 7.103 | 1.00 | 13.76 | C |
| ATOM | 7081 | OD1 | ASN A 517 | 39.233 | 64.002 | 6.324 | 1.00 | 14.02 | O |
| ATOM | 7082 | ND2 | ASN A 517 | 40.905 | 62.731 | 7.253 | 1.00 | 15.57 | N |
| ATOM | 7085 | C | ASN A 517 | 36.244 | 62.147 | 8.678 | 1.00 | 11.83 | C |
| ATOM | 7086 | O | ASN A 517 | 35.397 | 61.779 | 7.865 | 1.00 | 12.36 | O |
| ATOM | 7088 | N | ASP A 518 | 36.196 | 61.758 | 9.940 | 1.00 | 11.92 | N |
| ATOM | 7089 | CA | ASP A 518 | 35.222 | 60.774 | 10.393 | 1.00 | 13.35 | C |
| ATOM | 7091 | CB | ASP A 518 | 35.596 | 60.330 | 11.813 | 1.00 | 12.81 | C |
| ATOM | 7094 | CG | ASP A 518 | 34.818 | 59.120 | 12.286 | 1.00 | 16.31 | C |
| ATOM | 7095 | OD1 | ASP A 518 | 34.490 | 58.260 | 11.427 | 1.00 | 17.76 | O |
| ATOM | 7096 | OD2 | ASP A 518 | 34.534 | 59.007 | 13.514 | 1.00 | 19.26 | O |
| ATOM | 7097 | C | ASP A 518 | 33.829 | 61.347 | 10.348 | 1.00 | 13.18 | C |
| ATOM | 7098 | O | ASP A 518 | 32.906 | 60.727 | 9.835 | 1.00 | 13.34 | O |
| ATOM | 7100 | N | VAL A 519 | 33.690 | 62.553 | 10.887 | 1.00 | 13.10 | N |
| ATOM | 7101 | CA | VAL A 519 | 32.402 | 63.229 | 10.909 | 1.00 | 12.63 | C |
| ATOM | 7103 | CB | VAL A 519 | 32.442 | 64.480 | 11.822 | 1.00 | 13.29 | C |
| ATOM | 7105 | CG1 | VAL A 519 | 31.114 | 65.228 | 11.814 | 1.00 | 12.56 | C |
| ATOM | 7109 | CG2 | VAL A 519 | 32.810 | 64.099 | 13.260 | 1.00 | 14.09 | C |
| ATOM | 7113 | C | VAL A 519 | 31.925 | 63.579 | 9.495 | 1.00 | 12.17 | C |
| ATOM | 7114 | O | VAL A 519 | 30.730 | 63.417 | 9.183 | 1.00 | 12.94 | O |
| ATOM | 7116 | N | LEU A 520 | 32.845 | 64.014 | 8.634 | 1.00 | 11.56 | N |
| ATOM | 7117 | CA | LEU A 520 | 32.445 | 64.296 | 7.252 | 1.00 | 11.87 | C |
| ATOM | 7119 | CB | LEU A 520 | 33.605 | 64.980 | 6.500 | 1.00 | 12.51 | C |
| ATOM | 7122 | CG | LEU A 520 | 33.254 | 65.367 | 5.047 | 1.00 | 11.19 | C |
| ATOM | 7124 | CD1 | LEU A 520 | 32.052 | 66.297 | 4.963 | 1.00 | 12.71 | C |
| ATOM | 7128 | CD2 | LEU A 520 | 34.402 | 66.082 | 4.339 | 1.00 | 13.02 | C |
| ATOM | 7132 | C | LEU A 520 | 32.050 | 62.994 | 6.559 | 1.00 | 11.45 | C |
| ATOM | 7133 | O | LEU A 520 | 31.174 | 62.974 | 5.699 | 1.00 | 11.94 | O |
| ATOM | 7135 | N | SER A 521 | 32.684 | 61.878 | 6.921 | 1.00 | 11.72 | N |
| ATOM | 7136 | CA | SER A 521 | 32.267 | 60.577 | 6.349 | 1.00 | 12.44 | C |
| ATOM | 7138 | CB | SER A 521 | 33.223 | 59.481 | 6.791 | 1.00 | 12.57 | C |
| ATOM | 7141 | OG | SER A 521 | 34.556 | 59.757 | 6.360 | 1.00 | 13.01 | O |
| ATOM | 7143 | C | SER A 521 | 30.841 | 60.195 | 6.734 | 1.00 | 12.62 | C |
| ATOM | 7144 | O | SER A 521 | 30.090 | 59.637 | 5.930 | 1.00 | 12.22 | O |
| ATOM | 7146 | N | LEU A 522 | 30.475 | 60.497 | 7.976 | 1.00 | 12.48 | N |
| ATOM | 7147 | CA | LEU A 522 | 29.101 | 60.286 | 8.432 | 1.00 | 13.10 | C |
| ATOM | 7149 | CB | LEU A 522 | 28.953 | 60.655 | 9.894 | 1.00 | 13.90 | C |
| ATOM | 7152 | CG | LEU A 522 | 29.634 | 59.742 | 10.909 | 1.00 | 15.18 | C |
| ATOM | 7154 | CD1 | LEU A 522 | 29.587 | 60.366 | 12.295 | 1.00 | 14.50 | C |
| ATOM | 7158 | CD2 | LEU A 522 | 29.041 | 58.441 | 10.992 | 1.00 | 15.85 | C |
| ATOM | 7162 | C | LEU A 522 | 28.142 | 61.151 | 7.575 | 1.00 | 13.01 | C |
| ATOM | 7163 | O | LEU A 522 | 27.101 | 60.689 | 7.074 | 1.00 | 12.59 | O |

| ATOM | 7165 | N   | LEU A 523 | 28.514 | 62.410 | 7.372  | 1.00 | 12.45 | N |
|------|------|-----|-----------|--------|--------|--------|------|-------|---|
| ATOM | 7166 | CA  | LEU A 523 | 27.661 | 63.309 | 6.607  | 1.00 | 13.33 | C |
| ATOM | 7168 | CB  | LEU A 523 | 28.227 | 64.707 | 6.683  | 1.00 | 12.93 | C |
| ATOM | 7171 | CG  | LEU A 523 | 27.500 | 65.824 | 5.940  | 1.00 | 15.59 | C |
| ATOM | 7173 | CD1 | LEU A 523 | 26.016 | 65.955 | 6.283  | 1.00 | 16.48 | C |
| ATOM | 7177 | CD2 | LEU A 523 | 28.265 | 67.111 | 6.251  | 1.00 | 15.93 | C |
| ATOM | 7181 | C   | LEU A 523 | 27.538 | 62.922 | 5.156  | 1.00 | 13.52 | C |
| ATOM | 7182 | O   | LEU A 523 | 26.434 | 62.970 | 4.572  | 1.00 | 13.33 | O |
| ATOM | 7184 | N   | LEU A 524 | 28.664 | 62.569 | 4.544  | 1.00 | 12.23 | N |
| ATOM | 7185 | CA  | LEU A 524 | 28.612 | 62.202 | 3.120  | 1.00 | 12.85 | C |
| ATOM | 7187 | CB  | LEU A 524 | 29.979 | 62.345 | 2.440  | 1.00 | 11.37 | C |
| ATOM | 7190 | CG  | LEU A 524 | 30.595 | 63.737 | 2.526  | 1.00 | 12.85 | C |
| ATOM | 7192 | CD1 | LEU A 524 | 31.810 | 63.789 | 1.653  | 1.00 | 15.34 | C |
| ATOM | 7196 | CD2 | LEU A 524 | 29.621 | 64.814 | 2.083  | 1.00 | 12.43 | C |
| ATOM | 7200 | C   | LEU A 524 | 27.953 | 60.843 | 2.889  | 1.00 | 13.00 | C |
| ATOM | 7201 | O   | LEU A 524 | 27.293 | 60.641 | 1.868  | 1.00 | 14.25 | O |
| ATOM | 7203 | N   | ALA A 525 | 28.104 | 59.897 | 3.841  | 1.00 | 12.15 | N |
| ATOM | 7204 | CA  | ALA A 525 | 27.371 | 58.621 | 3.797  | 1.00 | 13.01 | C |
| ATOM | 7206 | CB  | ALA A 525 | 27.749 | 57.776 | 4.976  | 1.00 | 13.68 | C |
| ATOM | 7210 | C   | ALA A 525 | 25.866 | 58.928 | 3.811  | 1.00 | 12.71 | C |
| ATOM | 7211 | O   | ALA A 525 | 25.077 | 58.318 | 3.081  | 1.00 | 13.05 | O |
| ATOM | 7213 | N   | THR A 526 | 25.487 | 59.888 | 4.655  | 1.00 | 12.16 | N |
| ATOM | 7214 | CA  | THR A 526 | 24.090 | 60.281 | 4.838  | 1.00 | 12.10 | C |
| ATOM | 7216 | CB  | THR A 526 | 23.944 | 61.253 | 6.031  | 1.00 | 12.34 | C |
| ATOM | 7218 | OG1 | THR A 526 | 24.258 | 60.548 | 7.234  | 1.00 | 12.73 | O |
| ATOM | 7220 | CG2 | THR A 526 | 22.557 | 61.789 | 6.091  | 1.00 | 12.01 | C |
| ATOM | 7224 | C   | THR A 526 | 23.549 | 60.923 | 3.556  | 1.00 | 11.78 | C |
| ATOM | 7225 | O   | THR A 526 | 22.479 | 60.530 | 3.052  | 1.00 | 12.70 | O |
| ATOM | 7227 | N   | HIS A 527 | 24.312 | 61.859 | 2.993  | 1.00 | 12.17 | N |
| ATOM | 7228 | CA  | HIS A 527 | 23.932 | 62.525 | 1.727  | 1.00 | 12.24 | C |
| ATOM | 7230 | CB  | HIS A 527 | 25.004 | 63.537 | 1.348  | 1.00 | 13.61 | C |
| ATOM | 7233 | CG  | HIS A 527 | 24.611 | 64.484 | 0.244  | 1.00 | 13.75 | C |
| ATOM | 7234 | ND1 | HIS A 527 | 25.388 | 65.567 | -0.111 | 1.00 | 13.93 | N |
| ATOM | 7236 | CE1 | HIS A 527 | 24.817 | 66.189 | -1.142 | 1.00 | 15.86 | C |
| ATOM | 7238 | NE2 | HIS A 527 | 23.721 | 65.535 | -1.486 | 1.00 | 13.26 | N |
| ATOM | 7240 | CD2 | HIS A 527 | 23.564 | 64.469 | -0.631 | 1.00 | 14.97 | C |
| ATOM | 7242 | C   | HIS A 527 | 23.769 | 61.434 | 0.630  | 1.00 | 12.00 | C |
| ATOM | 7243 | O   | HIS A 527 | 22.794 | 61.396 | -0.106 | 1.00 | 12.09 | O |
| ATOM | 7245 | N   | LEU A 528 | 24.716 | 60.501 | 0.549  | 1.00 | 11.77 | N |
| ATOM | 7246 | CA  | LEU A 528 | 24.702 | 59.489 | -0.504 | 1.00 | 11.99 | C |
| ATOM | 7248 | CB  | LEU A 528 | 25.943 | 58.610 | -0.427 | 1.00 | 12.71 | C |
| ATOM | 7251 | CG  | LEU A 528 | 26.131 | 57.559 | -1.499 | 1.00 | 12.25 | C |
| ATOM | 7253 | CD1 | LEU A 528 | 25.889 | 58.018 | -2.946 | 1.00 | 14.51 | C |
| ATOM | 7257 | CD2 | LEU A 528 | 27.549 | 56.978 | -1.409 | 1.00 | 13.69 | C |
| ATOM | 7261 | C   | LEU A 528 | 23.451 | 58.618 | -0.410 | 1.00 | 12.30 | C |
| ATOM | 7262 | O   | LEU A 528 | 22.758 | 58.375 | -1.384 | 1.00 | 11.52 | O |
| ATOM | 7264 | N   | TYR A 529 | 23.142 | 58.195 | 0.801  | 1.00 | 12.21 | N |
| ATOM | 7265 | CA  | TYR A 529 | 21.932 | 57.424 | 1.091  | 1.00 | 12.17 | C |
| ATOM | 7267 | CB  | TYR A 529 | 21.814 | 57.167 | 2.619  | 1.00 | 12.77 | C |
| ATOM | 7270 | CG  | TYR A 529 | 20.514 | 56.492 | 2.986  | 1.00 | 13.33 | C |
| ATOM | 7271 | CD1 | TYR A 529 | 20.398 | 55.091 | 3.029  | 1.00 | 14.65 | C |
| ATOM | 7273 | CE1 | TYR A 529 | 19.168 | 54.469 | 3.309  | 1.00 | 13.39 | C |
| ATOM | 7275 | CZ  | TYR A 529 | 18.035 | 55.267 | 3.523  | 1.00 | 14.52 | C |
| ATOM | 7276 | OH  | TYR A 529 | 16.816 | 54.644 | 3.790  | 1.00 | 14.98 | O |
| ATOM | 7278 | CE2 | TYR A 529 | 18.169 | 56.661 | 3.490  | 1.00 | 12.41 | C |
| ATOM | 7280 | CD2 | TYR A 529 | 19.367 | 57.244 | 3.221  | 1.00 | 13.46 | C |
| ATOM | 7282 | C   | TYR A 529 | 20.680 | 58.203 | 0.559  | 1.00 | 10.92 | C |

| ATOM | 7283 | O | TYR A 529 | 19.854 | 57.682 | -0.206 | 1.00 | 12.15 | O |
|------|------|-----|-----------|--------|--------|--------|------|-------|---|
| ATOM | 7285 | N | CYS A 530 | 20.597 | 59.468 | 0.945 | 1.00 | 12.07 | N |
| ATOM | 7286 | CA | CYS A 530 | 19.447 | 60.295 | 0.597 | 1.00 | 11.68 | C |
| ATOM | 7288 | CB | CYS A 530 | 19.479 | 61.621 | 1.364 | 1.00 | 13.01 | C |
| ATOM | 7291 | SG | CYS A 530 | 19.134 | 61.410 | 3.082 | 1.00 | 14.32 | S |
| ATOM | 7293 | C | CYS A 530 | 19.379 | 60.534 | -0.922 | 1.00 | 12.32 | C |
| ATOM | 7294 | O | CYS A 530 | 18.281 | 60.486 | -1.530 | 1.00 | 12.64 | O |
| ATOM | 7296 | N | VAL A 531 | 20.508 | 60.789 | -1.572 | 1.00 | 12.07 | N |
| ATOM | 7297 | CA | VAL A 531 | 20.423 | 61.189 | -2.970 | 1.00 | 12.77 | C |
| ATOM | 7299 | CB | VAL A 531 | 21.742 | 61.885 | -3.546 | 1.00 | 13.29 | C |
| ATOM | 7301 | CG1 | VAL A 531 | 22.864 | 60.853 | -3.769 | 1.00 | 14.18 | C |
| ATOM | 7305 | CG2 | VAL A 531 | 21.424 | 62.656 | -4.800 | 1.00 | 13.28 | C |
| ATOM | 7309 | C | VAL A 531 | 19.974 | 59.989 | -3.800 | 1.00 | 13.21 | C |
| ATOM | 7310 | O | VAL A 531 | 19.316 | 60.140 | -4.815 | 1.00 | 13.25 | O |
| ATOM | 7312 | N | LEU A 532 | 20.325 | 58.787 | -3.360 | 1.00 | 12.96 | N |
| ATOM | 7313 | CA | LEU A 532 | 19.952 | 57.572 | -4.120 | 1.00 | 13.95 | C |
| ATOM | 7315 | CB | LEU A 532 | 20.726 | 56.348 | -3.668 | 1.00 | 15.69 | C |
| ATOM | 7318 | CG | LEU A 532 | 22.225 | 56.439 | -3.905 | 1.00 | 15.57 | C |
| ATOM | 7320 | CD1 | LEU A 532 | 22.901 | 55.278 | -3.162 | 1.00 | 19.35 | C |
| ATOM | 7324 | CD2 | LEU A 532 | 22.577 | 56.455 | -5.383 | 1.00 | 16.73 | C |
| ATOM | 7328 | C | LEU A 532 | 18.456 | 57.345 | -4.036 | 1.00 | 13.05 | C |
| ATOM | 7329 | O | LEU A 532 | 17.841 | 57.019 | -5.020 | 1.00 | 12.36 | O |
| ATOM | 7331 | N | GLN A 533 | 17.878 | 57.557 | -2.856 | 1.00 | 13.13 | N |
| ATOM | 7332 | CA | GLN A 533 | 16.419 | 57.528 | -2.706 | 1.00 | 13.26 | C |
| ATOM | 7334 | CB | GLN A 533 | 16.023 | 57.690 | -1.233 | 1.00 | 14.00 | C |
| ATOM | 7337 | CG | GLN A 533 | 14.529 | 57.659 | -0.927 | 1.00 | 13.77 | C |
| ATOM | 7340 | CD | GLN A 533 | 13.894 | 56.300 | -0.846 | 1.00 | 14.57 | C |
| ATOM | 7341 | OE1 | GLN A 533 | 14.556 | 55.253 | -0.982 | 1.00 | 15.11 | O |
| ATOM | 7342 | NE2 | GLN A 533 | 12.578 | 56.298 | -0.589 | 1.00 | 13.33 | N |
| ATOM | 7345 | C | GLN A 533 | 15.744 | 58.569 | -3.576 | 1.00 | 13.54 | C |
| ATOM | 7346 | O | GLN A 533 | 14.770 | 58.264 | -4.283 | 1.00 | 12.79 | O |
| ATOM | 7348 | N | ALA A 534 | 16.267 | 59.778 | -3.545 | 1.00 | 13.71 | N |
| ATOM | 7349 | CA | ALA A 534 | 15.711 | 60.877 | -4.383 | 1.00 | 14.34 | C |
| ATOM | 7351 | CB | ALA A 534 | 16.463 | 62.147 | -4.147 | 1.00 | 14.87 | C |
| ATOM | 7355 | C | ALA A 534 | 15.738 | 60.507 | -5.872 | 1.00 | 13.88 | C |
| ATOM | 7356 | O | ALA A 534 | 14.752 | 60.666 | -6.612 | 1.00 | 14.44 | O |
| ATOM | 7358 | N | ILE A 535 | 16.854 | 59.973 | -6.306 | 1.00 | 13.37 | N |
| ATOM | 7359 | CA | ILE A 535 | 17.014 | 59.520 | -7.684 | 1.00 | 14.16 | C |
| ATOM | 7361 | CB | ILE A 535 | 18.466 | 58.987 | -7.911 | 1.00 | 15.36 | C |
| ATOM | 7363 | CG1 | ILE A 535 | 19.443 | 60.185 | -7.996 | 1.00 | 15.18 | C |
| ATOM | 7366 | CD1 | ILE A 535 | 20.921 | 59.846 | -7.892 | 1.00 | 17.62 | C |
| ATOM | 7370 | CG2 | ILE A 535 | 18.535 | 58.052 | -9.134 | 1.00 | 15.95 | C |
| ATOM | 7374 | C | ILE A 535 | 15.982 | 58.433 | -8.081 | 1.00 | 13.93 | C |
| ATOM | 7375 | O | ILE A 535 | 15.355 | 58.529 | -9.136 | 1.00 | 14.41 | O |
| ATOM | 7377 | N | ASP A 536 | 15.773 | 57.447 | -7.228 | 1.00 | 13.58 | N |
| ATOM | 7378 | CA | ASP A 536 | 14.730 | 56.432 | -7.494 | 1.00 | 13.01 | C |
| ATOM | 7380 | CB | ASP A 536 | 14.797 | 55.298 | -6.494 | 1.00 | 12.29 | C |
| ATOM | 7383 | CG | ASP A 536 | 15.975 | 54.389 | -6.721 | 1.00 | 12.44 | C |
| ATOM | 7384 | OD1 | ASP A 536 | 16.344 | 54.176 | -7.917 | 1.00 | 14.79 | O |
| ATOM | 7385 | OD2 | ASP A 536 | 16.497 | 53.830 | -5.716 | 1.00 | 14.28 | O |
| ATOM | 7386 | C | ASP A 536 | 13.326 | 57.056 | -7.513 | 1.00 | 12.36 | C |
| ATOM | 7387 | O | ASP A 536 | 12.502 | 56.720 | -8.406 | 1.00 | 12.80 | O |
| ATOM | 7389 | N | LEU A 537 | 13.074 | 58.003 | -6.615 | 1.00 | 12.13 | N |
| ATOM | 7390 | CA | LEU A 537 | 11.767 | 58.669 | -6.595 | 1.00 | 11.91 | C |
| ATOM | 7392 | CB | LEU A 537 | 11.589 | 59.482 | -5.333 | 1.00 | 12.65 | C |
| ATOM | 7395 | CG | LEU A 537 | 11.519 | 58.667 | -4.050 | 1.00 | 13.70 | C |
| ATOM | 7397 | CD1 | LEU A 537 | 11.480 | 59.623 | -2.852 | 1.00 | 16.30 | C |

| ATOM | 7401 | CD2 | LEU A 537 | 10.328 | 57.769 | -4.052 | 1.00 | 15.91 | C |
|---|---|---|---|---|---|---|---|---|---|
| ATOM | 7405 | C | LEU A 537 | 11.561 | 59.539 | -7.842 | 1.00 | 12.70 | C |
| ATOM | 7406 | O | LEU A 537 | 10.439 | 59.621 | -8.430 | 1.00 | 13.12 | O |
| ATOM | 7408 | N | ARG A 538 | 12.639 | 60.128 | -8.319 | 1.00 | 11.81 | N |
| ATOM | 7409 | CA | ARG A 538 | 12.538 | 60.977 | -9.513 | 1.00 | 13.02 | C |
| ATOM | 7411 | CB | ARG A 538 | 13.791 | 61.840 | -9.663 | 1.00 | 13.49 | C |
| ATOM | 7414 | CG | ARG A 538 | 13.701 | 62.850 | -10.803 | 1.00 | 10.67 | C |
| ATOM | 7417 | CD | ARG A 538 | 12.706 | 64.008 | -10.447 | 1.00 | 13.92 | C |
| ATOM | 7420 | NE | ARG A 538 | 13.267 | 64.954 | -9.498 | 1.00 | 12.07 | N |
| ATOM | 7422 | CZ | ARG A 538 | 12.629 | 65.995 | -8.927 | 1.00 | 13.81 | C |
| ATOM | 7423 | NH1 | ARG A 538 | 11.344 | 66.191 | -9.139 | 1.00 | 14.85 | N |
| ATOM | 7426 | NH2 | ARG A 538 | 13.264 | 66.850 | -8.149 | 1.00 | 14.29 | N |
| ATOM | 7429 | C | ARG A 538 | 12.332 | 60.086 | -10.756 | 1.00 | 13.38 | C |
| ATOM | 7430 | O | ARG A 538 | 11.579 | 60.419 | -11.696 | 1.00 | 14.97 | O |
| ATOM | 7432 | N | ALA A 539 | 12.972 | 58.918 | -10.746 | 1.00 | 12.61 | N |
| ATOM | 7433 | CA | ALA A 539 | 12.763 | 57.934 | -11.831 | 1.00 | 13.20 | C |
| ATOM | 7435 | CB | ALA A 539 | 13.680 | 56.770 | -11.664 | 1.00 | 13.94 | C |
| ATOM | 7439 | C | ALA A 539 | 11.308 | 57.483 | -11.870 | 1.00 | 13.41 | C |
| ATOM | 7440 | O | ALA A 539 | 10.687 | 57.423 | -12.939 | 1.00 | 14.64 | O |
| ATOM | 7442 | N | ILE A 540 | 10.745 | 57.212 | -10.705 | 1.00 | 13.62 | N |
| ATOM | 7443 | CA | ILE A 540 | 9.321 | 56.845 | -10.612 | 1.00 | 14.11 | C |
| ATOM | 7445 | CB | ILE A 540 | 8.948 | 56.494 | -9.165 | 1.00 | 13.74 | C |
| ATOM | 7447 | CG1 | ILE A 540 | 9.532 | 55.127 | -8.798 | 1.00 | 14.80 | C |
| ATOM | 7450 | CD1 | ILE A 540 | 9.540 | 54.850 | -7.300 | 1.00 | 16.52 | C |
| ATOM | 7454 | CG2 | ILE A 540 | 7.443 | 56.514 | -8.994 | 1.00 | 15.70 | C |
| ATOM | 7458 | C | ILE A 540 | 8.423 | 57.977 | -11.173 | 1.00 | 14.36 | C |
| ATOM | 7459 | O | ILE A 540 | 7.475 | 57.743 | -11.948 | 1.00 | 13.94 | O |
| ATOM | 7461 | N | GLU A 541 | 8.750 | 59.211 | -10.856 | 1.00 | 13.76 | N |
| ATOM | 7462 | CA | GLU A 541 | 7.994 | 60.356 | -11.407 | 1.00 | 14.41 | C |
| ATOM | 7464 | CB | GLU A 541 | 8.594 | 61.652 | -10.869 | 1.00 | 14.84 | C |
| ATOM | 7467 | CG | GLU A 541 | 8.077 | 62.903 | -11.502 | 1.00 | 15.49 | C |
| ATOM | 7470 | CD | GLU A 541 | 8.863 | 64.145 | -11.048 | 1.00 | 18.80 | C |
| ATOM | 7471 | OE1 | GLU A 541 | 8.967 | 65.106 | -11.843 | 1.00 | 27.24 | O |
| ATOM | 7472 | OE2 | GLU A 541 | 9.380 | 64.147 | -9.915 | 1.00 | 19.48 | O |
| ATOM | 7473 | C | GLU A 541 | 8.075 | 60.380 | -12.918 | 1.00 | 13.71 | C |
| ATOM | 7474 | O | GLU A 541 | 7.061 | 60.562 | -13.637 | 1.00 | 14.05 | O |
| ATOM | 7476 | N | PHE A 542 | 9.286 | 60.158 | -13.436 | 1.00 | 13.72 | N |
| ATOM | 7477 | CA | PHE A 542 | 9.470 | 60.184 | -14.895 | 1.00 | 14.29 | C |
| ATOM | 7479 | CB | PHE A 542 | 10.951 | 60.073 | -15.274 | 1.00 | 15.60 | C |
| ATOM | 7482 | CG | PHE A 542 | 11.728 | 61.367 | -15.148 | 1.00 | 14.53 | C |
| ATOM | 7483 | CD1 | PHE A 542 | 11.253 | 62.465 | -14.427 | 1.00 | 15.26 | C |
| ATOM | 7485 | CE1 | PHE A 542 | 12.017 | 63.648 | -14.355 | 1.00 | 17.66 | C |
| ATOM | 7487 | CZ | PHE A 542 | 13.262 | 63.711 | -14.938 | 1.00 | 16.71 | C |
| ATOM | 7489 | CE2 | PHE A 542 | 13.765 | 62.622 | -15.617 | 1.00 | 19.21 | C |
| ATOM | 7491 | CD2 | PHE A 542 | 12.997 | 61.451 | -15.717 | 1.00 | 18.65 | C |
| ATOM | 7493 | C | PHE A 542 | 8.670 | 59.080 | -15.599 | 1.00 | 14.98 | C |
| ATOM | 7494 | O | PHE A 542 | 8.064 | 59.308 | -16.666 | 1.00 | 14.80 | O |
| ATOM | 7496 | N | GLU A 543 | 8.681 | 57.882 | -15.013 | 1.00 | 14.74 | N |
| ATOM | 7497 | CA | GLU A 543 | 7.929 | 56.752 | -15.590 | 1.00 | 15.20 | C |
| ATOM | 7499 | CB | GLU A 543 | 8.213 | 55.455 | -14.835 | 1.00 | 16.07 | C |
| ATOM | 7502 | CG | GLU A 543 | 9.677 | 54.991 | -14.940 | 1.00 | 16.29 | C |
| ATOM | 7505 | CD | GLU A 543 | 10.118 | 54.608 | -16.360 | 1.00 | 20.09 | C |
| ATOM | 7506 | OE1 | GLU A 543 | 9.363 | 53.893 | -17.055 | 1.00 | 23.60 | O |
| ATOM | 7507 | OE2 | GLU A 543 | 11.240 | 55.008 | -16.766 | 1.00 | 24.33 | O |
| ATOM | 7508 | C | GLU A 543 | 6.432 | 57.071 | -15.571 | 1.00 | 14.32 | C |
| ATOM | 7509 | O | GLU A 543 | 5.711 | 56.762 | -16.521 | 1.00 | 13.65 | O |
| ATOM | 7511 | N | PHE A 544 | 5.982 | 57.658 | -14.466 | 1.00 | 13.85 | N |

| ATOM | 7512 | CA | PHE A 544 | 4.594 | 58.072 | -14.319 | 1.00 | 13.54 | C |
|---|---|---|---|---|---|---|---|---|---|
| ATOM | 7514 | CB | PHE A 544 | 4.342 | 58.712 | -12.950 | 1.00 | 14.01 | C |
| ATOM | 7517 | CG | PHE A 544 | 2.967 | 59.271 | -12.820 | 1.00 | 13.81 | C |
| ATOM | 7518 | CD1 | PHE A 544 | 1.917 | 58.467 | -12.421 | 1.00 | 14.11 | C |
| ATOM | 7520 | CE1 | PHE A 544 | 0.650 | 58.982 | -12.298 | 1.00 | 15.97 | C |
| ATOM | 7522 | CZ | PHE A 544 | 0.424 | 60.330 | -12.603 | 1.00 | 12.14 | C |
| ATOM | 7524 | CE2 | PHE A 544 | 1.456 | 61.118 | -13.013 | 1.00 | 16.80 | C |
| ATOM | 7526 | CD2 | PHE A 544 | 2.726 | 60.594 | -13.104 | 1.00 | 15.38 | C |
| ATOM | 7528 | C | PHE A 544 | 4.213 | 59.059 | -15.399 | 1.00 | 14.73 | C |
| ATOM | 7529 | O | PHE A 544 | 3.195 | 58.889 | -16.064 | 1.00 | 13.62 | O |
| ATOM | 7531 | N | LYS A 545 | 5.031 | 60.103 | -15.557 | 1.00 | 14.65 | N |
| ATOM | 7532 | CA | LYS A 545 | 4.744 | 61.140 | -16.548 | 1.00 | 16.58 | C |
| ATOM | 7534 | CB | LYS A 545 | 5.805 | 62.230 | -16.459 | 1.00 | 16.53 | C |
| ATOM | 7537 | CG | LYS A 545 | 5.718 | 63.051 | -15.187 | 1.00 | 18.97 | C |
| ATOM | 7540 | CD | LYS A 545 | 6.754 | 64.167 | -15.172 | 1.00 | 21.42 | C |
| ATOM | 7543 | CE | LYS A 545 | 6.466 | 65.136 | -14.058 | 1.00 | 26.94 | C |
| ATOM | 7546 | NZ | LYS A 545 | 7.517 | 66.201 | -14.025 | 1.00 | 29.07 | N |
| ATOM | 7550 | C | LYS A 545 | 4.659 | 60.569 | -17.989 | 1.00 | 16.83 | C |
| ATOM | 7551 | O | LYS A 545 | 3.840 | 61.002 | -18.790 | 1.00 | 15.61 | O |
| ATOM | 7553 | N | LYS A 546 | 5.514 | 59.609 | -18.310 | 1.00 | 16.59 | N |
| ATOM | 7554 | CA | LYS A 546 | 5.494 | 58.975 | -19.642 | 1.00 | 18.57 | C |
| ATOM | 7556 | CB | LYS A 546 | 6.565 | 57.858 | -19.756 | 1.00 | 18.79 | C |
| ATOM | 7559 | CG | LYS A 546 | 7.971 | 58.359 | -20.121 | 1.00 | 24.43 | C |
| ATOM | 7562 | CD | LYS A 546 | 9.133 | 57.332 | -19.770 | 1.00 | 25.01 | C |
| ATOM | 7565 | CE | LYS A 546 | 9.079 | 56.008 | -20.537 | 1.00 | 30.12 | C |
| ATOM | 7568 | NZ | LYS A 546 | 10.093 | 54.981 | -19.972 | 1.00 | 29.76 | N |
| ATOM | 7572 | C | LYS A 546 | 4.104 | 58.389 | -19.932 | 1.00 | 17.51 | C |
| ATOM | 7573 | O | LYS A 546 | 3.561 | 58.460 | -21.048 | 1.00 | 16.67 | O |
| ATOM | 7575 | N | GLN A 547 | 3.542 | 57.766 | -18.913 | 1.00 | 16.14 | N |
| ATOM | 7576 | CA | GLN A 547 | 2.273 | 57.095 | -19.053 | 1.00 | 16.36 | C |
| ATOM | 7578 | CB | GLN A 547 | 2.223 | 55.937 | -18.089 | 1.00 | 17.04 | C |
| ATOM | 7581 | CG | GLN A 547 | 3.161 | 54.791 | -18.515 | 1.00 | 18.73 | C |
| ATOM | 7584 | CD | GLN A 547 | 3.296 | 53.720 | -17.449 | 1.00 | 18.98 | C |
| ATOM | 7585 | OE1 | GLN A 547 | 2.308 | 53.062 | -17.110 | 1.00 | 21.68 | O |
| ATOM | 7586 | NE2 | GLN A 547 | 4.538 | 53.519 | -16.934 | 1.00 | 22.98 | N |
| ATOM | 7589 | C | GLN A 547 | 1.099 | 57.999 | -18.821 | 1.00 | 15.85 | C |
| ATOM | 7590 | O | GLN A 547 | 0.041 | 57.775 | -19.423 | 1.00 | 14.02 | O |
| ATOM | 7592 | N | PHE A 548 | 1.258 | 59.025 | -17.981 | 1.00 | 14.97 | N |
| ATOM | 7593 | CA | PHE A 548 | 0.099 | 59.851 | -17.642 | 1.00 | 15.74 | C |
| ATOM | 7595 | CB | PHE A 548 | 0.193 | 60.467 | -16.257 | 1.00 | 17.25 | C |
| ATOM | 7598 | CG | PHE A 548 | -1.164 | 60.869 | -15.715 | 1.00 | 19.42 | C |
| ATOM | 7599 | CD1 | PHE A 548 | -2.232 | 59.942 | -15.698 | 1.00 | 19.08 | C |
| ATOM | 7601 | CE1 | PHE A 548 | -3.486 | 60.313 | -15.220 | 1.00 | 20.50 | C |
| ATOM | 7603 | CZ | PHE A 548 | -3.664 | 61.620 | -14.767 | 1.00 | 18.95 | C |
| ATOM | 7605 | CE2 | PHE A 548 | -2.617 | 62.534 | -14.793 | 1.00 | 19.37 | C |
| ATOM | 7607 | CD2 | PHE A 548 | -1.383 | 62.153 | -15.272 | 1.00 | 19.62 | C |
| ATOM | 7609 | C | PHE A 548 | -0.221 | 60.884 | -18.725 | 1.00 | 15.98 | C |
| ATOM | 7610 | O | PHE A 548 | -1.384 | 61.188 | -18.955 | 1.00 | 16.18 | O |
| ATOM | 7612 | N | GLY A 549 | 0.784 | 61.350 | -19.466 | 1.00 | 15.46 | N |
| ATOM | 7613 | CA | GLY A 549 | 0.530 | 62.324 | -20.521 | 1.00 | 15.88 | C |
| ATOM | 7616 | C | GLY A 549 | -0.529 | 61.865 | -21.507 | 1.00 | 15.68 | C |
| ATOM | 7617 | O | GLY A 549 | -1.514 | 62.555 | -21.762 | 1.00 | 16.68 | O |
| ATOM | 7619 | N | PRO A 550 | -0.348 | 60.684 | -22.108 | 1.00 | 14.80 | N |
| ATOM | 7620 | CA | PRO A 550 | -1.428 | 60.140 | -22.945 | 1.00 | 14.57 | C |
| ATOM | 7622 | CB | PRO A 550 | -0.870 | 58.779 | -23.406 | 1.00 | 15.56 | C |
| ATOM | 7625 | CG | PRO A 550 | 0.596 | 58.967 | -23.302 | 1.00 | 16.15 | C |
| ATOM | 7628 | CD | PRO A 550 | 0.861 | 59.837 | -22.127 | 1.00 | 15.68 | C |

| ATOM | 7631 | C | PRO | A | 550 | -2.770 | 59.928 | -22.231 | 1.00 | 14.52 | C |
| --- | --- | --- | --- | --- | --- | --- | --- | --- | --- | --- | --- |
| ATOM | 7632 | O | PRO | A | 550 | -3.819 | 59.987 | -22.875 | 1.00 | 14.12 | O |
| ATOM | 7633 | N | ALA | A | 551 | -2.718 | 59.615 | -20.937 | 1.00 | 14.55 | N |
| ATOM | 7634 | CA | ALA | A | 551 | -3.949 | 59.321 | -20.203 | 1.00 | 15.35 | C |
| ATOM | 7636 | CB | ALA | A | 551 | -3.678 | 58.728 | -18.855 | 1.00 | 14.18 | C |
| ATOM | 7640 | C | ALA | A | 551 | -4.755 | 60.598 | -20.091 | 1.00 | 15.49 | C |
| ATOM | 7641 | O | ALA | A | 551 | -5.962 | 60.566 | -20.273 | 1.00 | 15.80 | O |
| ATOM | 7643 | N | ILE | A | 552 | -4.077 | 61.707 | -19.877 | 1.00 | 14.73 | N |
| ATOM | 7644 | CA | ILE | A | 552 | -4.734 | 62.996 | -19.791 | 1.00 | 15.82 | C |
| ATOM | 7646 | CB | ILE | A | 552 | -3.712 | 64.132 | -19.459 | 1.00 | 16.14 | C |
| ATOM | 7648 | CG1 | ILE | A | 552 | -3.268 | 63.994 | -18.013 | 1.00 | 17.83 | C |
| ATOM | 7651 | CD1 | ILE | A | 552 | -2.031 | 64.800 | -17.699 | 1.00 | 17.90 | C |
| ATOM | 7655 | CG2 | ILE | A | 552 | -4.326 | 65.516 | -19.714 | 1.00 | 18.32 | C |
| ATOM | 7659 | C | ILE | A | 552 | -5.485 | 63.309 | -21.078 | 1.00 | 15.00 | C |
| ATOM | 7660 | O | ILE | A | 552 | -6.646 | 63.711 | -21.052 | 1.00 | 14.73 | O |
| ATOM | 7662 | N | VAL | A | 553 | -4.821 | 63.136 | -22.222 | 1.00 | 14.15 | N |
| ATOM | 7663 | CA | VAL | A | 553 | -5.451 | 63.416 | -23.516 | 1.00 | 13.71 | C |
| ATOM | 7665 | CB | VAL | A | 553 | -4.448 | 63.247 | -24.685 | 1.00 | 14.17 | C |
| ATOM | 7667 | CG1 | VAL | A | 553 | -5.104 | 63.437 | -26.022 | 1.00 | 15.47 | C |
| ATOM | 7671 | CG2 | VAL | A | 553 | -3.310 | 64.202 | -24.477 | 1.00 | 14.29 | C |
| ATOM | 7675 | C | VAL | A | 553 | -6.626 | 62.490 | -23.725 | 1.00 | 12.37 | C |
| ATOM | 7676 | O | VAL | A | 553 | -7.697 | 62.893 | -24.187 | 1.00 | 13.32 | O |
| ATOM | 7678 | N | SER | A | 554 | -6.438 | 61.235 | -23.378 | 1.00 | 12.25 | N |
| ATOM | 7679 | CA | SER | A | 554 | -7.511 | 60.251 | -23.530 | 1.00 | 13.71 | C |
| ATOM | 7681 | CB | SER | A | 554 | -6.996 | 58.869 | -23.117 | 1.00 | 14.19 | C |
| ATOM | 7684 | OG | SER | A | 554 | -8.005 | 57.907 | -23.319 | 1.00 | 21.12 | O |
| ATOM | 7686 | C | SER | A | 554 | -8.763 | 60.611 | -22.711 | 1.00 | 12.62 | C |
| ATOM | 7687 | O | SER | A | 554 | -9.909 | 60.504 | -23.223 | 1.00 | 13.03 | O |
| ATOM | 7689 | N | LEU | A | 555 | -8.553 | 60.999 | -21.456 | 1.00 | 11.60 | N |
| ATOM | 7690 | CA | LEU | A | 555 | -9.671 | 61.388 | -20.601 | 1.00 | 12.32 | C |
| ATOM | 7692 | CB | LEU | A | 555 | -9.267 | 61.423 | -19.138 | 1.00 | 13.27 | C |
| ATOM | 7695 | CG | LEU | A | 555 | -9.280 | 60.056 | -18.404 | 1.00 | 17.54 | C |
| ATOM | 7697 | CD1 | LEU | A | 555 | -9.594 | 60.320 | -17.017 | 1.00 | 21.94 | C |
| ATOM | 7701 | CD2 | LEU | A | 555 | -10.272 | 59.026 | -18.898 | 1.00 | 23.75 | C |
| ATOM | 7705 | C | LEU | A | 555 | -10.334 | 62.680 | -21.085 | 1.00 | 12.12 | C |
| ATOM | 7706 | O | LEU | A | 555 | -11.578 | 62.794 | -21.067 | 1.00 | 12.04 | O |
| ATOM | 7708 | N | ILE | A | 556 | -9.538 | 63.633 | -21.555 | 1.00 | 11.76 | N |
| ATOM | 7709 | CA | ILE | A | 556 | -10.112 | 64.857 | -22.175 | 1.00 | 11.53 | C |
| ATOM | 7711 | CB | ILE | A | 556 | -8.985 | 65.847 | -22.558 | 1.00 | 10.43 | C |
| ATOM | 7713 | CG1 | ILE | A | 556 | -8.489 | 66.570 | -21.274 | 1.00 | 11.89 | C |
| ATOM | 7716 | CD1 | ILE | A | 556 | -7.224 | 67.398 | -21.431 | 1.00 | 11.84 | C |
| ATOM | 7720 | CG2 | ILE | A | 556 | -9.438 | 66.797 | -23.647 | 1.00 | 12.17 | C |
| ATOM | 7724 | C | ILE | A | 556 | -10.980 | 64.519 | -23.385 | 1.00 | 11.26 | C |
| ATOM | 7725 | O | ILE | A | 556 | -12.109 | 65.008 | -23.553 | 1.00 | 10.55 | O |
| ATOM | 7727 | N | ASP | A | 557 | -10.473 | 63.659 | -24.248 | 1.00 | 10.49 | N |
| ATOM | 7728 | CA | ASP | A | 557 | -11.257 | 63.235 | -25.403 | 1.00 | 11.77 | C |
| ATOM | 7730 | CB | ASP | A | 557 | -10.433 | 62.348 | -26.293 | 1.00 | 12.01 | C |
| ATOM | 7733 | CG | ASP | A | 557 | -9.405 | 63.132 | -27.071 | 1.00 | 15.59 | C |
| ATOM | 7734 | OD1 | ASP | A | 557 | -9.538 | 64.380 | -27.162 | 1.00 | 16.48 | O |
| ATOM | 7735 | OD2 | ASP | A | 557 | -8.472 | 62.495 | -27.597 | 1.00 | 19.32 | O |
| ATOM | 7736 | C | ASP | A | 557 | -12.545 | 62.527 | -25.026 | 1.00 | 11.55 | C |
| ATOM | 7737 | O | ASP | A | 557 | -13.612 | 62.850 | -25.535 | 1.00 | 12.84 | O |
| ATOM | 7739 | N | GLN | A | 558 | -12.437 | 61.605 | -24.073 | 1.00 | 11.63 | N |
| ATOM | 7740 | CA | GLN | A | 558 | -13.580 | 60.841 | -23.626 | 1.00 | 12.46 | C |
| ATOM | 7742 | CB | GLN | A | 558 | -13.184 | 59.841 | -22.543 | 1.00 | 13.26 | C |
| ATOM | 7745 | CG | GLN | A | 558 | -14.336 | 58.951 | -22.123 | 1.00 | 15.65 | C |
| ATOM | 7748 | CD | GLN | A | 558 | -13.970 | 57.897 | -21.089 | 1.00 | 17.04 | C |

| | | | | | | | | |
|---|---|---|---|---|---|---|---|---|
| ATOM | 7749 | OE1 | GLN A 558 | -13.025 | 58.041 | -20.308 | 1.00 | 20.02 | O |
| ATOM | 7750 | NE2 | GLN A 558 | -14.734 | 56.811 | -21.101 | 1.00 | 21.33 | N |
| ATOM | 7753 | C | GLN A 558 | -14.679 | 61.735 | -23.093 | 1.00 | 11.85 | C |
| ATOM | 7754 | O | GLN A 558 | -15.847 | 61.552 | -23.460 | 1.00 | 13.45 | O |
| ATOM | 7756 | N | HIS A 559 | -14.310 | 62.661 | -22.207 | 1.00 | 11.00 | N |
| ATOM | 7757 | CA | HIS A 559 | -15.299 | 63.476 | -21.507 | 1.00 | 11.32 | C |
| ATOM | 7759 | CB | HIS A 559 | -14.809 | 63.843 | -20.118 | 1.00 | 12.41 | C |
| ATOM | 7762 | CG | HIS A 559 | -14.743 | 62.680 | -19.180 | 1.00 | 12.24 | C |
| ATOM | 7763 | ND1 | HIS A 559 | -15.739 | 62.404 | -18.271 | 1.00 | 14.20 | N |
| ATOM | 7765 | CE1 | HIS A 559 | -15.407 | 61.337 | -17.564 | 1.00 | 15.30 | C |
| ATOM | 7767 | NE2 | HIS A 559 | -14.243 | 60.888 | -18.001 | 1.00 | 13.28 | N |
| ATOM | 7769 | CD2 | HIS A 559 | -13.819 | 61.697 | -19.034 | 1.00 | 14.70 | C |
| ATOM | 7771 | C | HIS A 559 | -15.714 | 64.749 | -22.261 | 1.00 | 11.42 | C |
| ATOM | 7772 | O | HIS A 559 | -16.866 | 65.200 | -22.166 | 1.00 | 11.17 | O |
| ATOM | 7774 | N | PHE A 560 | -14.770 | 65.321 | -23.001 | 1.00 | 10.24 | N |
| ATOM | 7775 | CA | PHE A 560 | -14.972 | 66.632 | -23.627 | 1.00 | 9.90 | C |
| ATOM | 7777 | CB | PHE A 560 | -13.929 | 67.640 | -23.102 | 1.00 | 9.19 | C |
| ATOM | 7780 | CG | PHE A 560 | -13.863 | 67.765 | -21.585 | 1.00 | 8.78 | C |
| ATOM | 7781 | CD1 | PHE A 560 | -15.011 | 67.741 | -20.799 | 1.00 | 8.17 | C |
| ATOM | 7783 | CE1 | PHE A 560 | -14.923 | 67.884 | -19.411 | 1.00 | 9.51 | C |
| ATOM | 7785 | CZ | PHE A 560 | -13.753 | 68.080 | -18.821 | 1.00 | 8.48 | C |
| ATOM | 7787 | CE2 | PHE A 560 | -12.582 | 68.142 | -19.594 | 1.00 | 9.12 | C |
| ATOM | 7789 | CD2 | PHE A 560 | -12.657 | 67.968 | -20.960 | 1.00 | 9.60 | C |
| ATOM | 7791 | C | PHE A 560 | -14.937 | 66.647 | -25.147 | 1.00 | 11.25 | C |
| ATOM | 7792 | O | PHE A 560 | -15.273 | 67.676 | -25.753 | 1.00 | 11.67 | O |
| ATOM | 7794 | N | GLY A 561 | -14.646 | 65.495 | -25.764 | 1.00 | 11.79 | N |
| ATOM | 7795 | CA | GLY A 561 | -14.478 | 65.436 | -27.211 | 1.00 | 12.67 | C |
| ATOM | 7798 | C | GLY A 561 | -15.683 | 65.967 | -27.943 | 1.00 | 14.15 | C |
| ATOM | 7799 | O | GLY A 561 | -15.560 | 66.815 | -28.819 | 1.00 | 14.19 | O |
| ATOM | 7801 | N | SER A 562 | -16.858 | 65.460 | -27.578 | 1.00 | 14.08 | N |
| ATOM | 7802 | CA | SER A 562 | -18.110 | 65.866 | -28.209 | 1.00 | 15.43 | C |
| ATOM | 7804 | CB | SER A 562 | -19.267 | 65.140 | -27.546 | 1.00 | 16.88 | C |
| ATOM | 7807 | OG | SER A 562 | -19.232 | 63.772 | -27.910 | 1.00 | 21.17 | O |
| ATOM | 7809 | C | SER A 562 | -18.320 | 67.366 | -28.075 | 1.00 | 15.25 | C |
| ATOM | 7810 | O | SER A 562 | -18.662 | 68.048 | -29.042 | 1.00 | 14.81 | O |
| ATOM | 7812 | N | ALA A 563 | -18.122 | 67.879 | -26.860 | 1.00 | 13.17 | N |
| ATOM | 7813 | CA | ALA A 563 | -18.328 | 69.318 | -26.609 | 1.00 | 13.97 | C |
| ATOM | 7815 | CB | ALA A 563 | -18.232 | 69.604 | -25.123 | 1.00 | 13.73 | C |
| ATOM | 7819 | C | ALA A 563 | -17.374 | 70.222 | -27.407 | 1.00 | 14.18 | C |
| ATOM | 7820 | O | ALA A 563 | -17.732 | 71.360 | -27.731 | 1.00 | 15.18 | O |
| ATOM | 7822 | N | MSE A 564 | -16.201 | 69.713 | -27.759 | 1.00 | 13.85 | N |
| ATOM | 7823 | CA | MSE A 564 | -15.184 | 70.487 | -28.491 | 1.00 | 15.42 | C |
| ATOM | 7825 | CB | MSE A 564 | -13.779 | 70.068 | -28.043 | 1.00 | 15.47 | C |
| ATOM | 7828 | CG | MSE A 564 | -13.543 | 70.394 | -26.601 | 1.00 | 13.59 | C |
| ATOM | 7831 | SE | MSE A 564 | -11.731 | 70.022 | -26.037 | 1.00 | 23.04 | SE |
| ATOM | 7832 | CE | MSE A 564 | -11.631 | 67.971 | -26.430 | 1.00 | 16.91 | C |
| ATOM | 7836 | C | MSE A 564 | -15.291 | 70.309 | -29.989 | 1.00 | 17.04 | C |
| ATOM | 7837 | O | MSE A 564 | -14.515 | 70.921 | -30.736 | 1.00 | 17.27 | O |
| ATOM | 7839 | N | THR A 565 | -16.254 | 69.510 | -30.423 | 1.00 | 18.18 | N |
| ATOM | 7840 | CA | THR A 565 | -16.347 | 69.196 | -31.854 | 1.00 | 20.43 | C |
| ATOM | 7842 | CB | THR A 565 | -17.344 | 68.052 | -32.179 | 1.00 | 21.24 | C |
| ATOM | 7844 | OG1 | THR A 565 | -18.603 | 68.247 | -31.519 | 1.00 | 23.05 | O |
| ATOM | 7846 | CG2 | THR A 565 | -16.740 | 66.677 | -31.760 | 1.00 | 23.52 | C |
| ATOM | 7850 | C | THR A 565 | -16.632 | 70.472 | -32.640 | 1.00 | 20.00 | C |
| ATOM | 7851 | O | THR A 565 | -17.491 | 71.272 | -32.267 | 1.00 | 20.97 | O |
| ATOM | 7853 | N | GLY A 566 | -15.848 | 70.664 | -33.699 | 1.00 | 20.68 | N |
| ATOM | 7854 | CA | GLY A 566 | -16.000 | 71.818 | -34.577 | 1.00 | 19.86 | C |

| | | | | | | | | | |
|---|---|---|---|---|---|---|---|---|---|
| ATOM | 7857 | C | GLY | A | 566 | -15.157 | 73.005 | -34.113 | 1.00 20.38 | C |
| ATOM | 7858 | O | GLY | A | 566 | -15.179 | 74.034 | -34.781 | 1.00 20.51 | O |
| ATOM | 7860 | N | SER | A | 567 | -14.415 | 72.850 | -32.998 | 1.00 20.46 | N |
| ATOM | 7861 | CA | SER | A | 567 | -13.649 | 73.928 | -32.353 | 1.00 19.54 | C |
| ATOM | 7863 | CB | SER | A | 567 | -13.990 | 74.022 | -30.862 | 1.00 19.55 | C |
| ATOM | 7866 | OG | SER | A | 567 | -13.215 | 73.102 | -30.090 | 1.00 17.91 | O |
| ATOM | 7868 | C | SER | A | 567 | -12.167 | 73.687 | -32.473 | 1.00 19.84 | C |
| ATOM | 7869 | O | SER | A | 567 | -11.734 | 72.574 | -32.786 | 1.00 21.64 | O |
| ATOM | 7871 | N | ASN | A | 568 | -11.371 | 74.714 | -32.184 | 1.00 19.12 | N |
| ATOM | 7872 | CA | ASN | A | 568 | -9.928 | 74.573 | -32.103 | 1.00 18.61 | C |
| ATOM | 7874 | CB | ASN | A | 568 | -9.231 | 75.798 | -32.743 | 1.00 19.04 | C |
| ATOM | 7877 | CG | ASN | A | 568 | -9.261 | 77.036 | -31.842 | 1.00 22.39 | C |
| ATOM | 7878 | OD1 | ASN | A | 568 | -10.266 | 77.272 | -31.141 | 1.00 24.17 | O |
| ATOM | 7879 | ND2 | ASN | A | 568 | -8.141 | 77.811 | -31.812 | 1.00 21.53 | N |
| ATOM | 7882 | C | ASN | A | 568 | -9.438 | 74.391 | -30.655 | 1.00 17.67 | C |
| ATOM | 7883 | O | ASN | A | 568 | -8.256 | 74.615 | -30.380 | 1.00 20.10 | O |
| ATOM | 7885 | N | LEU | A | 569 | -10.309 | 73.992 | -29.711 | 1.00 14.90 | N |
| ATOM | 7886 | CA | LEU | A | 569 | -10.007 | 74.131 | -28.269 | 1.00 14.35 | C |
| ATOM | 7888 | CB | LEU | A | 569 | -11.321 | 74.213 | -27.465 | 1.00 13.94 | C |
| ATOM | 7891 | CG | LEU | A | 569 | -12.163 | 75.450 | -27.829 | 1.00 14.56 | C |
| ATOM | 7893 | CD1 | LEU | A | 569 | -13.515 | 75.338 | -27.185 | 1.00 16.87 | C |
| ATOM | 7897 | CD2 | LEU | A | 569 | -11.507 | 76.726 | -27.416 | 1.00 16.94 | C |
| ATOM | 7901 | C | LEU | A | 569 | -9.129 | 73.041 | -27.663 | 1.00 12.95 | C |
| ATOM | 7902 | O | LEU | A | 569 | -8.537 | 73.201 | -26.609 | 1.00 10.94 | O |
| ATOM | 7904 | N | ARG | A | 570 | -9.056 | 71.927 | -28.358 | 1.00 13.19 | N |
| ATOM | 7905 | CA | ARG | A | 570 | -8.430 | 70.759 | -27.781 | 1.00 12.81 | C |
| ATOM | 7907 | CB | ARG | A | 570 | -8.616 | 69.569 | -28.737 | 1.00 12.77 | C |
| ATOM | 7910 | CG | ARG | A | 570 | -8.095 | 68.272 | -28.216 | 1.00 13.79 | C |
| ATOM | 7913 | CD | ARG | A | 570 | -8.546 | 67.140 | -29.156 | 1.00 15.93 | C |
| ATOM | 7916 | NE | ARG | A | 570 | -7.950 | 65.848 | -28.779 | 1.00 19.34 | N |
| ATOM | 7918 | CZ | ARG | A | 570 | -6.950 | 65.242 | -29.425 | 1.00 23.30 | C |
| ATOM | 7919 | NH1 | ARG | A | 570 | -6.321 | 65.817 | -30.449 | 1.00 24.77 | N |
| ATOM | 7922 | NH2 | ARG | A | 570 | -6.517 | 64.071 | -28.982 | 1.00 21.25 | N |
| ATOM | 7925 | C | ARG | A | 570 | -6.965 | 70.943 | -27.425 | 1.00 11.85 | C |
| ATOM | 7926 | O | ARG | A | 570 | -6.526 | 70.555 | -26.358 | 1.00 12.59 | O |
| ATOM | 7928 | N | ASP | A | 571 | -6.182 | 71.473 | -28.352 | 1.00 12.71 | N |
| ATOM | 7929 | CA | ASP | A | 571 | -4.770 | 71.640 | -28.084 | 1.00 12.94 | C |
| ATOM | 7931 | CB | ASP | A | 571 | -4.055 | 72.247 | -29.288 | 1.00 12.68 | C |
| ATOM | 7934 | CG | ASP | A | 571 | -3.780 | 71.259 | -30.394 | 1.00 16.32 | C |
| ATOM | 7935 | OD1 | ASP | A | 571 | -3.755 | 70.040 | -30.156 | 1.00 14.30 | O |
| ATOM | 7936 | OD2 | ASP | A | 571 | -3.593 | 71.752 | -31.534 | 1.00 15.08 | O |
| ATOM | 7937 | C | ASP | A | 571 | -4.513 | 72.597 | -26.893 | 1.00 12.03 | C |
| ATOM | 7938 | O | ASP | A | 571 | -3.645 | 72.361 | -26.033 | 1.00 12.28 | O |
| ATOM | 7940 | N | GLU | A | 572 | -5.259 | 73.704 | -26.894 | 1.00 12.82 | N |
| ATOM | 7941 | CA | GLU | A | 572 | -5.165 | 74.694 | -25.803 | 1.00 13.93 | C |
| ATOM | 7943 | CB | GLU | A | 572 | -6.104 | 75.884 | -26.065 | 1.00 14.67 | C |
| ATOM | 7946 | CG | GLU | A | 572 | -5.848 | 77.032 | -25.086 | 1.00 19.02 | C |
| ATOM | 7949 | CD | GLU | A | 572 | -6.945 | 78.088 | -25.064 | 1.00 20.04 | C |
| ATOM | 7950 | OE1 | GLU | A | 572 | -7.870 | 78.020 | -25.905 | 1.00 25.40 | O |
| ATOM | 7951 | OE2 | GLU | A | 572 | -6.875 | 78.979 | -24.151 | 1.00 27.51 | O |
| ATOM | 7952 | C | GLU | A | 572 | -5.553 | 74.021 | -24.476 | 1.00 11.42 | C |
| ATOM | 7953 | O | GLU | A | 572 | -4.861 | 74.217 | -23.461 | 1.00 10.83 | O |
| ATOM | 7955 | N | LEU | A | 573 | -6.629 | 73.242 | -24.485 | 1.00 10.02 | N |
| ATOM | 7956 | CA | LEU | A | 573 | -7.019 | 72.578 | -23.226 | 1.00 10.97 | C |
| ATOM | 7958 | CB | LEU | A | 573 | -8.341 | 71.835 | -23.391 | 1.00 10.35 | C |
| ATOM | 7961 | CG | LEU | A | 573 | -8.846 | 71.259 | -22.067 | 1.00 10.24 | C |
| ATOM | 7963 | CD1 | LEU | A | 573 | -9.114 | 72.400 | -21.065 | 1.00 9.45 | C |

| | | | | | | | | |
|---|---|---|---|---|---|---|---|---|
| ATOM | 7967 | CD2 | LEU A 573 | -10.055 | 70.396 | -22.323 | 1.00 13.76 | C |
| ATOM | 7971 | C | LEU A 573 | -5.921 | 71.648 | -22.684 | 1.00 10.61 | C |
| ATOM | 7972 | O | LEU A 573 | -5.580 | 71.659 | -21.521 | 1.00 10.32 | O |
| ATOM | 7974 | N | VAL A 574 | -5.387 | 70.802 | -23.551 | 1.00 10.63 | N |
| ATOM | 7975 | CA | VAL A 574 | -4.363 | 69.879 | -23.133 | 1.00 12.05 | C |
| ATOM | 7977 | CB | VAL A 574 | -3.963 | 68.947 | -24.326 | 1.00 11.77 | C |
| ATOM | 7979 | CG1 | VAL A 574 | -2.721 | 68.165 | -23.981 | 1.00 13.68 | C |
| ATOM | 7983 | CG2 | VAL A 574 | -5.125 | 68.017 | -24.735 | 1.00 13.34 | C |
| ATOM | 7987 | C | VAL A 574 | -3.175 | 70.635 | -22.602 | 1.00 11.48 | C |
| ATOM | 7988 | O | VAL A 574 | -2.656 | 70.323 | -21.546 | 1.00 11.56 | O |
| ATOM | 7990 | N | GLU A 575 | -2.726 | 71.652 | -23.335 | 1.00 11.68 | N |
| ATOM | 7991 | CA | GLU A 575 | -1.576 | 72.414 | -22.895 | 1.00 13.83 | C |
| ATOM | 7993 | CB | GLU A 575 | -1.273 | 73.521 | -23.906 | 1.00 13.29 | C |
| ATOM | 7996 | CG | GLU A 575 | -0.254 | 74.525 | -23.399 | 1.00 17.56 | C |
| ATOM | 7999 | CD | GLU A 575 | -0.109 | 75.729 | -24.304 | 1.00 21.93 | C |
| ATOM | 8000 | OE1 | GLU A 575 | -0.780 | 76.776 | -24.027 | 1.00 30.95 | O |
| ATOM | 8001 | OE2 | GLU A 575 | 0.664 | 75.620 | -25.289 | 1.00 32.87 | O |
| ATOM | 8002 | C | GLU A 575 | -1.793 | 73.047 | -21.515 | 1.00 13.12 | C |
| ATOM | 8003 | O | GLU A 575 | -0.969 | 72.938 | -20.626 | 1.00 14.52 | O |
| ATOM | 8005 | N | LYS A 576 | -2.917 | 73.735 | -21.371 | 1.00 12.55 | N |
| ATOM | 8006 | CA | LYS A 576 | -3.173 | 74.466 | -20.129 | 1.00 13.12 | C |
| ATOM | 8008 | CB | LYS A 576 | -4.252 | 75.519 | -20.373 | 1.00 13.50 | C |
| ATOM | 8011 | CG | LYS A 576 | -3.844 | 76.648 | -21.344 | 1.00 17.98 | C |
| ATOM | 8014 | CD | LYS A 576 | -4.761 | 77.811 | -21.117 | 1.00 24.83 | C |
| ATOM | 8017 | CE | LYS A 576 | -4.791 | 78.827 | -22.242 | 1.00 29.94 | C |
| ATOM | 8020 | NZ | LYS A 576 | -3.599 | 79.594 | -22.297 | 1.00 32.04 | N |
| ATOM | 8024 | C | LYS A 576 | -3.528 | 73.569 | -18.952 | 1.00 12.46 | C |
| ATOM | 8025 | O | LYS A 576 | -3.125 | 73.834 | -17.795 | 1.00 12.39 | O |
| ATOM | 8027 | N | VAL A 577 | -4.224 | 72.469 | -19.202 | 1.00 11.36 | N |
| ATOM | 8028 | CA | VAL A 577 | -4.422 | 71.457 | -18.140 | 1.00 11.64 | C |
| ATOM | 8030 | CB | VAL A 577 | -5.403 | 70.357 | -18.587 | 1.00 11.95 | C |
| ATOM | 8032 | CG1 | VAL A 577 | -5.367 | 69.158 | -17.642 | 1.00 11.93 | C |
| ATOM | 8036 | CG2 | VAL A 577 | -6.819 | 70.892 | -18.716 | 1.00 11.76 | C |
| ATOM | 8040 | C | VAL A 577 | -3.072 | 70.889 | -17.643 | 1.00 12.14 | C |
| ATOM | 8041 | O | VAL A 577 | -2.809 | 70.824 | -16.431 | 1.00 12.72 | O |
| ATOM | 8043 | N | ASN A 578 | -2.209 | 70.503 | -18.590 | 1.00 13.84 | N |
| ATOM | 8044 | CA | ASN A 578 | -0.878 | 70.028 | -18.239 | 1.00 15.70 | C |
| ATOM | 8046 | CB | ASN A 578 | -0.080 | 69.622 | -19.482 | 1.00 16.35 | C |
| ATOM | 8049 | CG | ASN A 578 | -0.549 | 68.310 | -20.077 | 1.00 19.39 | C |
| ATOM | 8050 | OD1 | ASN A 578 | -1.043 | 67.440 | -19.354 | 1.00 29.72 | O |
| ATOM | 8051 | ND2 | ASN A 578 | -0.387 | 68.154 | -21.375 | 1.00 26.04 | N |
| ATOM | 8054 | C | ASN A 578 | -0.120 | 71.065 | -17.404 | 1.00 16.09 | C |
| ATOM | 8055 | O | ASN A 578 | 0.485 | 70.713 | -16.403 | 1.00 17.80 | O |
| ATOM | 8057 | N | LYS A 579 | -0.119 | 72.332 | -17.826 | 1.00 16.22 | N |
| ATOM | 8058 | CA | LYS A 579 | 0.591 | 73.383 | -17.091 | 1.00 18.08 | C |
| ATOM | 8060 | CB | LYS A 579 | 0.528 | 74.738 | -17.805 | 1.00 18.53 | C |
| ATOM | 8063 | CG | LYS A 579 | 1.361 | 74.813 | -19.047 | 1.00 22.92 | C |
| ATOM | 8066 | CD | LYS A 579 | 1.263 | 76.186 | -19.717 | 1.00 23.91 | C |
| ATOM | 8069 | CE | LYS A 579 | 1.956 | 76.165 | -21.115 | 1.00 29.29 | C |
| ATOM | 8072 | NZ | LYS A 579 | 3.389 | 75.805 | -20.988 | 1.00 35.13 | N |
| ATOM | 8076 | C | LYS A 579 | 0.017 | 73.551 | -15.696 | 1.00 16.08 | C |
| ATOM | 8077 | O | LYS A 579 | 0.756 | 73.655 | -14.734 | 1.00 16.20 | O |
| ATOM | 8079 | N | THR A 580 | -1.308 | 73.561 | -15.591 | 1.00 15.26 | N |
| ATOM | 8080 | CA | THR A 580 | -1.927 | 73.659 | -14.285 | 1.00 15.12 | C |
| ATOM | 8082 | CB | THR A 580 | -3.462 | 73.822 | -14.395 | 1.00 14.97 | C |
| ATOM | 8084 | OG1 | THR A 580 | -3.766 | 75.052 | -15.068 | 1.00 16.67 | O |
| ATOM | 8086 | CG2 | THR A 580 | -4.126 | 73.841 | -13.003 | 1.00 14.70 | C |

| | | | | | | | | | |
|---|---|---|---|---|---|---|---|---|---|
| ATOM | 8090 | C | THR | A | 580 | -1.545 | 72.511 | -13.358 | 1.00 15.08 | C |
| ATOM | 8091 | O | THR | A | 580 | -1.208 | 72.746 | -12.180 | 1.00 16.55 | O |
| ATOM | 8093 | N | LEU | A | 581 | -1.665 | 71.286 | -13.862 | 1.00 15.06 | N |
| ATOM | 8094 | CA | LEU | A | 581 | -1.310 | 70.096 | -13.072 | 1.00 16.69 | C |
| ATOM | 8096 | CB | LEU | A | 581 | -1.545 | 68.826 | -13.871 | 1.00 15.96 | C |
| ATOM | 8099 | CG | LEU | A | 581 | -3.004 | 68.487 | -14.156 | 1.00 14.15 | C |
| ATOM | 8101 | CD1 | LEU | A | 581 | -3.055 | 67.374 | -15.168 | 1.00 14.14 | C |
| ATOM | 8105 | CD2 | LEU | A | 581 | -3.741 | 68.093 | -12.860 | 1.00 14.70 | C |
| ATOM | 8109 | C | LEU | A | 581 | 0.144 | 70.189 | -12.606 | 1.00 18.77 | C |
| ATOM | 8110 | O | LEU | A | 581 | 0.436 | 70.075 | -11.395 | 1.00 18.76 | O |
| ATOM | 8112 | N | ALA | A | 582 | 1.039 | 70.450 | -13.562 | 1.00 21.19 | N |
| ATOM | 8113 | CA | ALA | A | 582 | 2.476 | 70.522 | -13.246 | 1.00 23.00 | C |
| ATOM | 8115 | CB | ALA | A | 582 | 3.292 | 70.793 | -14.503 | 1.00 23.71 | C |
| ATOM | 8119 | C | ALA | A | 582 | 2.801 | 71.545 | -12.181 | 1.00 24.34 | C |
| ATOM | 8120 | O | ALA | A | 582 | 3.578 | 71.257 | -11.255 | 1.00 26.53 | O |
| ATOM | 8122 | N | LYS | A | 583 | 2.239 | 72.739 | -12.266 | 1.00 24.73 | N |
| ATOM | 8123 | CA | LYS | A | 583 | 2.567 | 73.754 | -11.308 | 1.00 26.39 | C |
| ATOM | 8125 | CB | LYS | A | 583 | 2.077 | 75.155 | -11.732 | 1.00 27.09 | C |
| ATOM | 8128 | CG | LYS | A | 583 | 0.547 | 75.412 | -11.724 | 1.00 30.69 | C |
| ATOM | 8131 | CD | LYS | A | 583 | 0.200 | 76.916 | -11.887 | 1.00 31.17 | C |
| ATOM | 8134 | CE | LYS | A | 583 | -1.233 | 77.139 | -12.499 | 1.00 31.64 | C |
| ATOM | 8137 | NZ | LYS | A | 583 | -1.805 | 78.476 | -12.153 | 1.00 35.37 | N |
| ATOM | 8141 | C | LYS | A | 583 | 2.023 | 73.390 | -9.933 | 1.00 24.67 | C |
| ATOM | 8142 | O | LYS | A | 583 | 2.678 | 73.674 | -8.908 | 1.00 25.12 | O |
| ATOM | 8144 | N | ARG | A | 584 | 0.828 | 72.776 | -9.898 | 1.00 21.25 | N |
| ATOM | 8145 | CA | ARG | A | 584 | 0.187 | 72.504 | -8.627 | 1.00 20.06 | C |
| ATOM | 8147 | CB | ARG | A | 584 | -1.317 | 72.182 | -8.801 | 1.00 19.76 | C |
| ATOM | 8150 | CG | ARG | A | 584 | -2.047 | 71.893 | -7.505 | 1.00 19.79 | C |
| ATOM | 8153 | CD | ARG | A | 584 | -1.857 | 72.974 | -6.437 | 1.00 19.04 | C |
| ATOM | 8156 | NE | ARG | A | 584 | -2.651 | 72.716 | -5.249 | 1.00 17.87 | N |
| ATOM | 8158 | CZ | ARG | A | 584 | -2.533 | 73.384 | -4.109 | 1.00 19.95 | C |
| ATOM | 8159 | NH1 | ARG | A | 584 | -1.662 | 74.390 | -3.988 | 1.00 23.11 | N |
| ATOM | 8162 | NH2 | ARG | A | 584 | -3.297 | 73.082 | -3.080 | 1.00 19.41 | N |
| ATOM | 8165 | C | ARG | A | 584 | 0.886 | 71.342 | -7.939 | 1.00 19.27 | C |
| ATOM | 8166 | O | ARG | A | 584 | 1.090 | 71.378 | -6.720 | 1.00 17.79 | O |
| ATOM | 8168 | N | LEU | A | 585 | 1.268 | 70.345 | -8.717 | 1.00 19.52 | N |
| ATOM | 8169 | CA | LEU | A | 585 | 1.797 | 69.126 | -8.152 | 1.00 20.06 | C |
| ATOM | 8171 | CB | LEU | A | 585 | 1.905 | 68.033 | -9.181 | 1.00 20.03 | C |
| ATOM | 8174 | CG | LEU | A | 585 | 0.544 | 67.446 | -9.578 | 1.00 20.53 | C |
| ATOM | 8176 | CD1 | LEU | A | 585 | 0.660 | 66.683 | -10.865 | 1.00 19.62 | C |
| ATOM | 8180 | CD2 | LEU | A | 585 | -0.061 | 66.532 | -8.503 | 1.00 20.65 | C |
| ATOM | 8184 | C | LEU | A | 585 | 3.136 | 69.376 | -7.495 | 1.00 21.34 | C |
| ATOM | 8185 | O | LEU | A | 585 | 3.457 | 68.707 | -6.519 | 1.00 20.97 | O |
| ATOM | 8187 | N | GLU | A | 586 | 3.855 | 70.390 | -7.958 | 1.00 22.43 | N |
| ATOM | 8188 | CA | GLU | A | 586 | 5.160 | 70.711 | -7.355 | 1.00 23.36 | C |
| ATOM | 8190 | CB | GLU | A | 586 | 5.878 | 71.803 | -8.167 | 1.00 23.58 | C |
| ATOM | 8193 | CG | GLU | A | 586 | 7.198 | 72.276 | -7.531 | 1.00 25.77 | C |
| ATOM | 8196 | CD | GLU | A | 586 | 8.293 | 72.668 | -8.526 | 1.00 28.54 | C |
| ATOM | 8197 | OE1 | GLU | A | 586 | 8.380 | 71.999 | -9.619 | 1.00 31.13 | O |
| ATOM | 8198 | OE2 | GLU | A | 586 | 9.090 | 73.605 | -8.146 | 1.00 29.12 | O |
| ATOM | 8199 | C | GLU | A | 586 | 5.033 | 71.142 | -5.902 | 1.00 22.51 | C |
| ATOM | 8200 | O | GLU | A | 586 | 5.980 | 70.986 | -5.128 | 1.00 22.64 | O |
| ATOM | 8202 | N | GLN | A | 587 | 3.874 | 71.680 | -5.529 | 1.00 20.61 | N |
| ATOM | 8203 | CA | GLN | A | 587 | 3.615 | 72.221 | -4.235 | 1.00 21.46 | C |
| ATOM | 8205 | CB | GLN | A | 587 | 2.737 | 73.467 | -4.386 | 1.00 22.61 | C |
| ATOM | 8208 | CG | GLN | A | 587 | 3.042 | 74.374 | -5.561 | 1.00 26.37 | C |
| ATOM | 8211 | CD | GLN | A | 587 | 1.958 | 75.433 | -5.733 | 1.00 27.22 | C |

| | | | | | | | | |
|---|---|---|---|---|---|---|---|---|
| ATOM | 8212 | OE1 | GLN A 587 | 0.753 | 75.111 | -5.783 | 1.00 30.23 | O |
| ATOM | 8213 | NE2 | GLN A 587 | 2.369 | 76.692 | -5.761 | 1.00 33.40 | N |
| ATOM | 8216 | C | GLN A 587 | 2.820 | 71.304 | -3.333 | 1.00 19.34 | C |
| ATOM | 8217 | O | GLN A 587 | 2.505 | 71.727 | -2.233 | 1.00 20.34 | O |
| ATOM | 8219 | N | THR A 588 | 2.382 | 70.143 | -3.822 | 1.00 17.56 | N |
| ATOM | 8220 | CA | THR A 588 | 1.506 | 69.282 | -3.039 | 1.00 16.44 | C |
| ATOM | 8222 | CB | THR A 588 | 0.132 | 69.062 | -3.724 | 1.00 16.49 | C |
| ATOM | 8224 | OG1 | THR A 588 | 0.321 | 68.439 | -4.996 | 1.00 16.04 | O |
| ATOM | 8226 | CG2 | THR A 588 | -0.623 | 70.405 | -3.857 | 1.00 16.10 | C |
| ATOM | 8230 | C | THR A 588 | 2.196 | 67.941 | -2.751 | 1.00 16.24 | C |
| ATOM | 8231 | O | THR A 588 | 1.559 | 66.947 | -2.448 | 1.00 16.77 | O |
| ATOM | 8233 | N | ASN A 589 | 3.520 | 67.980 | -2.746 | 1.00 16.48 | N |
| ATOM | 8234 | CA | ASN A 589 | 4.334 | 66.820 | -2.506 | 1.00 16.42 | C |
| ATOM | 8236 | CB | ASN A 589 | 5.790 | 67.046 | -3.008 | 1.00 17.13 | C |
| ATOM | 8239 | CG | ASN A 589 | 6.417 | 68.384 | -2.570 | 1.00 17.40 | C |
| ATOM | 8240 | OD1 | ASN A 589 | 5.738 | 69.322 | -2.184 | 1.00 19.26 | O |
| ATOM | 8241 | ND2 | ASN A 589 | 7.779 | 68.447 | -2.627 | 1.00 15.79 | N |
| ATOM | 8244 | C | ASN A 589 | 4.316 | 66.301 | -1.067 | 1.00 16.21 | C |
| ATOM | 8245 | O | ASN A 589 | 4.906 | 65.245 | -0.794 | 1.00 16.66 | O |
| ATOM | 8247 | N | SER A 590 | 3.659 | 67.029 | -0.160 | 1.00 16.68 | N |
| ATOM | 8248 | CA | SER A 590 | 3.457 | 66.536 | 1.188 | 1.00 18.26 | C |
| ATOM | 8250 | CB | SER A 590 | 3.708 | 67.644 | 2.198 | 1.00 19.27 | C |
| ATOM | 8253 | OG | SER A 590 | 2.773 | 68.688 | 1.987 | 1.00 25.44 | O |
| ATOM | 8255 | C | SER A 590 | 2.065 | 65.964 | 1.401 | 1.00 16.62 | C |
| ATOM | 8256 | O | SER A 590 | 1.751 | 65.496 | 2.506 | 1.00 17.25 | O |
| ATOM | 8258 | N | TYR A 591 | 1.232 | 66.007 | 0.354 | 1.00 15.15 | N |
| ATOM | 8259 | CA | TYR A 591 | -0.121 | 65.433 | 0.428 | 1.00 15.35 | C |
| ATOM | 8261 | CB | TYR A 591 | -1.009 | 65.975 | -0.707 | 1.00 16.75 | C |
| ATOM | 8264 | CG | TYR A 591 | -1.539 | 67.380 | -0.544 | 1.00 17.89 | C |
| ATOM | 8265 | CD1 | TYR A 591 | -2.896 | 67.656 | -0.875 | 1.00 20.35 | C |
| ATOM | 8267 | CE1 | TYR A 591 | -3.437 | 68.910 | -0.730 | 1.00 21.08 | C |
| ATOM | 8269 | CZ | TYR A 591 | -2.627 | 69.949 | -0.278 | 1.00 21.40 | C |
| ATOM | 8270 | OH | TYR A 591 | -3.202 | 71.200 | -0.134 | 1.00 23.99 | O |
| ATOM | 8272 | CE2 | TYR A 591 | -1.283 | 69.736 | 0.040 | 1.00 18.20 | C |
| ATOM | 8274 | CD2 | TYR A 591 | -0.738 | 68.441 | -0.078 | 1.00 18.97 | C |
| ATOM | 8276 | C | TYR A 591 | -0.074 | 63.932 | 0.245 | 1.00 14.83 | C |
| ATOM | 8277 | O | TYR A 591 | 0.708 | 63.423 | -0.540 | 1.00 15.70 | O |
| ATOM | 8279 | N | ASP A 592 | -1.029 | 63.247 | 0.848 | 1.00 13.45 | N |
| ATOM | 8280 | CA | ASP A 592 | -1.250 | 61.827 | 0.568 | 1.00 13.10 | C |
| ATOM | 8282 | CB | ASP A 592 | -2.190 | 61.209 | 1.620 | 1.00 13.39 | C |
| ATOM | 8285 | CG | ASP A 592 | -1.494 | 60.964 | 2.972 | 1.00 16.35 | C |
| ATOM | 8286 | OD1 | ASP A 592 | -0.271 | 61.187 | 3.073 | 1.00 16.44 | O |
| ATOM | 8287 | OD2 | ASP A 592 | -2.187 | 60.555 | 3.945 | 1.00 16.92 | O |
| ATOM | 8288 | C | ASP A 592 | -1.842 | 61.669 | -0.834 | 1.00 12.57 | C |
| ATOM | 8289 | O | ASP A 592 | -2.425 | 62.595 | -1.397 | 1.00 13.64 | O |
| ATOM | 8291 | N | LEU A 593 | -1.686 | 60.477 | -1.383 | 1.00 13.79 | N |
| ATOM | 8292 | CA | LEU A 593 | -1.951 | 60.256 | -2.803 | 1.00 13.25 | C |
| ATOM | 8294 | CB | LEU A 593 | -1.717 | 58.791 | -3.126 | 1.00 13.59 | C |
| ATOM | 8297 | CG | LEU A 593 | -1.839 | 58.338 | -4.594 | 1.00 14.08 | C |
| ATOM | 8299 | CD1 | LEU A 593 | -0.763 | 59.067 | -5.421 | 1.00 14.52 | C |
| ATOM | 8303 | CD2 | LEU A 593 | -1.703 | 56.803 | -4.740 | 1.00 13.43 | C |
| ATOM | 8307 | C | LEU A 593 | -3.354 | 60.649 | -3.238 | 1.00 14.06 | C |
| ATOM | 8308 | O | LEU A 593 | -3.557 | 61.348 | -4.258 | 1.00 11.87 | O |
| ATOM | 8310 | N | VAL A 594 | -4.339 | 60.146 | -2.508 | 1.00 13.93 | N |
| ATOM | 8311 | CA | VAL A 594 | -5.714 | 60.332 | -2.905 | 1.00 13.66 | C |
| ATOM | 8313 | CB | VAL A 594 | -6.689 | 59.415 | -2.107 | 1.00 14.24 | C |
| ATOM | 8315 | CG1 | VAL A 594 | -8.122 | 59.823 | -2.393 | 1.00 14.44 | C |

| ATOM | 8319 | CG2 | VAL A 594 | -6.409 | 57.933 | -2.453 | 1.00 | 14.00 | C |
|------|------|-----|-----------|--------|--------|--------|------|-------|---|
| ATOM | 8323 | C | VAL A 594 | -6.112 | 61.839 | -2.878 | 1.00 | 13.92 | C |
| ATOM | 8324 | O | VAL A 594 | -6.531 | 62.378 | -3.915 | 1.00 | 13.01 | O |
| ATOM | 8326 | N | PRO A 595 | -5.951 | 62.533 | -1.739 | 1.00 | 13.66 | N |
| ATOM | 8327 | CA | PRO A 595 | -6.267 | 63.974 | -1.775 | 1.00 | 13.89 | C |
| ATOM | 8329 | CB | PRO A 595 | -6.112 | 64.404 | -0.311 | 1.00 | 15.51 | C |
| ATOM | 8332 | CG | PRO A 595 | -5.298 | 63.347 | 0.347 | 1.00 | 14.63 | C |
| ATOM | 8335 | CD | PRO A 595 | -5.579 | 62.093 | -0.379 | 1.00 | 14.74 | C |
| ATOM | 8338 | C | PRO A 595 | -5.364 | 64.800 | -2.702 | 1.00 | 13.98 | C |
| ATOM | 8339 | O | PRO A 595 | -5.835 | 65.787 | -3.309 | 1.00 | 13.26 | O |
| ATOM | 8340 | N | ARG A 596 | -4.116 | 64.367 | -2.881 | 1.00 | 13.23 | N |
| ATOM | 8341 | CA | ARG A 596 | -3.253 | 65.067 | -3.831 | 1.00 | 12.93 | C |
| ATOM | 8343 | CB | ARG A 596 | -1.887 | 64.392 | -3.905 | 1.00 | 11.82 | C |
| ATOM | 8346 | CG | ARG A 596 | -0.895 | 65.224 | -4.655 | 1.00 | 15.42 | C |
| ATOM | 8349 | CD | ARG A 596 | 0.459 | 64.605 | -4.661 | 1.00 | 16.19 | C |
| ATOM | 8352 | NE | ARG A 596 | 1.470 | 65.561 | -5.166 | 1.00 | 13.97 | N |
| ATOM | 8354 | CZ | ARG A 596 | 2.702 | 65.222 | -5.503 | 1.00 | 18.90 | C |
| ATOM | 8355 | NH1 | ARG A 596 | 3.069 | 63.974 | -5.417 | 1.00 | 23.05 | N |
| ATOM | 8358 | NH2 | ARG A 596 | 3.559 | 66.138 | -5.942 | 1.00 | 18.92 | N |
| ATOM | 8361 | C | ARG A 596 | -3.865 | 65.203 | -5.242 | 1.00 | 12.55 | C |
| ATOM | 8362 | O | ARG A 596 | -3.893 | 66.295 | -5.839 | 1.00 | 12.25 | O |
| ATOM | 8364 | N | TRP A 597 | -4.338 | 64.089 | -5.758 | 1.00 | 12.25 | N |
| ATOM | 8365 | CA | TRP A 597 | -4.846 | 64.017 | -7.115 | 1.00 | 12.01 | C |
| ATOM | 8367 | CB | TRP A 597 | -4.814 | 62.562 | -7.633 | 1.00 | 12.47 | C |
| ATOM | 8370 | CG | TRP A 597 | -3.453 | 62.222 | -8.034 | 1.00 | 12.81 | C |
| ATOM | 8371 | CD1 | TRP A 597 | -2.620 | 61.387 | -7.400 | 1.00 | 13.63 | C |
| ATOM | 8373 | NE1 | TRP A 597 | -1.376 | 61.362 | -8.048 | 1.00 | 16.01 | N |
| ATOM | 8375 | CE2 | TRP A 597 | -1.411 | 62.246 | -9.093 | 1.00 | 14.13 | C |
| ATOM | 8376 | CD2 | TRP A 597 | -2.705 | 62.803 | -9.125 | 1.00 | 12.13 | C |
| ATOM | 8377 | CE3 | TRP A 597 | -3.005 | 63.752 | -10.116 | 1.00 | 12.93 | C |
| ATOM | 8379 | CZ3 | TRP A 597 | -2.021 | 64.054 | -11.061 | 1.00 | 14.46 | C |
| ATOM | 8381 | CH2 | TRP A 597 | -0.734 | 63.487 | -10.994 | 1.00 | 14.28 | C |
| ATOM | 8383 | CZ2 | TRP A 597 | -0.421 | 62.568 | -10.038 | 1.00 | 16.79 | C |
| ATOM | 8385 | C | TRP A 597 | -6.198 | 64.718 | -7.254 | 1.00 | 12.15 | C |
| ATOM | 8386 | O | TRP A 597 | -6.476 | 65.421 | -8.269 | 1.00 | 12.14 | O |
| ATOM | 8388 | N | HIS A 598 | -7.042 | 64.605 | -6.230 | 1.00 | 12.01 | N |
| ATOM | 8389 | CA | HIS A 598 | -8.306 | 65.328 | -6.275 | 1.00 | 12.14 | C |
| ATOM | 8391 | CB | HIS A 598 | -9.235 | 64.842 | -5.176 | 1.00 | 13.18 | C |
| ATOM | 8394 | CG | HIS A 598 | -9.873 | 63.544 | -5.506 | 1.00 | 14.19 | C |
| ATOM | 8395 | ND1 | HIS A 598 | -10.929 | 63.444 | -6.389 | 1.00 | 14.66 | N |
| ATOM | 8397 | CE1 | HIS A 598 | -11.269 | 62.173 | -6.522 | 1.00 | 14.01 | C |
| ATOM | 8399 | NE2 | HIS A 598 | -10.431 | 61.441 | -5.801 | 1.00 | 15.19 | N |
| ATOM | 8401 | CD2 | HIS A 598 | -9.562 | 62.276 | -5.142 | 1.00 | 15.97 | C |
| ATOM | 8403 | C | HIS A 598 | -8.021 | 66.835 | -6.224 | 1.00 | 10.82 | C |
| ATOM | 8404 | O | HIS A 598 | -8.674 | 67.588 | -6.907 | 1.00 | 11.82 | O |
| ATOM | 8406 | N | ASP A 599 | -7.032 | 67.256 | -5.425 | 1.00 | 10.43 | N |
| ATOM | 8407 | CA | ASP A 599 | -6.657 | 68.677 | -5.387 | 1.00 | 11.02 | C |
| ATOM | 8409 | CB | ASP A 599 | -5.616 | 68.890 | -4.286 | 1.00 | 11.83 | C |
| ATOM | 8412 | CG | ASP A 599 | -4.935 | 70.234 | -4.382 | 1.00 | 10.48 | C |
| ATOM | 8413 | OD1 | ASP A 599 | -4.004 | 70.372 | -5.222 | 1.00 | 13.57 | O |
| ATOM | 8414 | OD2 | ASP A 599 | -5.346 | 71.127 | -3.547 | 1.00 | 15.71 | O |
| ATOM | 8415 | C | ASP A 599 | -6.153 | 69.162 | -6.772 | 1.00 | 11.24 | C |
| ATOM | 8416 | O | ASP A 599 | -6.568 | 70.227 | -7.268 | 1.00 | 10.72 | O |
| ATOM | 8418 | N | ALA A 600 | -5.265 | 68.375 | -7.377 | 1.00 | 12.20 | N |
| ATOM | 8419 | CA | ALA A 600 | -4.649 | 68.753 | -8.664 | 1.00 | 12.35 | C |
| ATOM | 8421 | CB | ALA A 600 | -3.580 | 67.722 | -9.104 | 1.00 | 12.24 | C |
| ATOM | 8425 | C | ALA A 600 | -5.730 | 68.914 | -9.733 | 1.00 | 11.47 | C |

| | | | | | | | | |
|---|---|---|---|---|---|---|---|---|
| ATOM | 8426 | O | ALA A 600 | -5.766 | 69.914 | -10.465 | 1.00 | 13.07 | O |
| ATOM | 8428 | N | PHE A 601 | -6.618 | 67.924 | -9.852 | 1.00 | 10.42 | N |
| ATOM | 8429 | CA | PHE A 601 | -7.697 | 67.999 | -10.850 | 1.00 | 11.26 | C |
| ATOM | 8431 | CB | PHE A 601 | -8.185 | 66.608 | -11.209 | 1.00 | 11.51 | C |
| ATOM | 8434 | CG | PHE A 601 | -7.292 | 65.938 | -12.200 | 1.00 | 12.38 | C |
| ATOM | 8435 | CD1 | PHE A 601 | -7.336 | 66.341 | -13.509 | 1.00 | 11.66 | C |
| ATOM | 8437 | CE1 | PHE A 601 | -6.514 | 65.742 | -14.463 | 1.00 | 13.74 | C |
| ATOM | 8439 | CZ | PHE A 601 | -5.588 | 64.830 | -14.083 | 1.00 | 11.03 | C |
| ATOM | 8441 | CE2 | PHE A 601 | -5.513 | 64.404 | -12.760 | 1.00 | 13.87 | C |
| ATOM | 8443 | CD2 | PHE A 601 | -6.351 | 64.989 | -11.802 | 1.00 | 11.43 | C |
| ATOM | 8445 | C | PHE A 601 | -8.846 | 68.956 | -10.513 | 1.00 | 12.10 | C |
| ATOM | 8446 | O | PHE A 601 | -9.514 | 69.435 | -11.417 | 1.00 | 10.86 | O |
| ATOM | 8448 | N | SER A 602 | -9.028 | 69.293 | -9.226 | 1.00 | 11.39 | N |
| ATOM | 8449 | CA | SER A 602 | -9.921 | 70.383 | -8.843 | 1.00 | 11.72 | C |
| ATOM | 8451 | CB | SER A 602 | -10.052 | 70.476 | -7.331 | 1.00 | 11.27 | C |
| ATOM | 8454 | OG | SER A 602 | -10.982 | 71.443 | -7.016 | 1.00 | 15.20 | O |
| ATOM | 8456 | C | SER A 602 | -9.383 | 71.697 | -9.419 | 1.00 | 10.76 | C |
| ATOM | 8457 | O | SER A 602 | -10.132 | 72.430 | -10.001 | 1.00 | 11.30 | O |
| ATOM | 8459 | N | PHE A 603 | -8.073 | 71.900 | -9.323 | 1.00 | 10.68 | N |
| ATOM | 8460 | CA | PHE A 603 | -7.449 | 73.090 | -9.906 | 1.00 | 11.12 | C |
| ATOM | 8462 | CB | PHE A 603 | -5.991 | 73.145 | -9.552 | 1.00 | 11.33 | C |
| ATOM | 8465 | CG | PHE A 603 | -5.402 | 74.561 | -9.526 | 1.00 | 11.29 | C |
| ATOM | 8466 | CD1 | PHE A 603 | -4.249 | 74.824 | -8.832 | 1.00 | 20.05 | C |
| ATOM | 8468 | CE1 | PHE A 603 | -3.693 | 76.108 | -8.825 | 1.00 | 18.96 | C |
| ATOM | 8470 | CZ | PHE A 603 | -4.301 | 77.145 | -9.524 | 1.00 | 15.25 | C |
| ATOM | 8472 | CE2 | PHE A 603 | -5.406 | 76.900 | -10.212 | 1.00 | 15.23 | C |
| ATOM | 8474 | CD2 | PHE A 603 | -5.972 | 75.615 | -10.221 | 1.00 | 12.73 | C |
| ATOM | 8476 | C | PHE A 603 | -7.593 | 73.054 | -11.422 | 1.00 | 10.95 | C |
| ATOM | 8477 | O | PHE A 603 | -8.021 | 74.027 | -12.048 | 1.00 | 12.79 | O |
| ATOM | 8479 | N | ALA A 604 | -7.350 | 71.889 | -12.014 | 1.00 | 11.32 | N |
| ATOM | 8480 | CA | ALA A 604 | -7.427 | 71.790 | -13.460 | 1.00 | 11.25 | C |
| ATOM | 8482 | CB | ALA A 604 | -6.853 | 70.448 | -13.926 | 1.00 | 11.47 | C |
| ATOM | 8486 | C | ALA A 604 | -8.879 | 72.010 | -13.966 | 1.00 | 10.57 | C |
| ATOM | 8487 | O | ALA A 604 | -9.103 | 72.507 | -15.055 | 1.00 | 12.05 | O |
| ATOM | 8489 | N | ALA A 605 | -9.869 | 71.655 | -13.153 | 1.00 | 9.18 | N |
| ATOM | 8490 | CA | ALA A 605 | -11.266 | 71.880 | -13.513 | 1.00 | 11.01 | C |
| ATOM | 8492 | CB | ALA A 605 | -12.199 | 71.302 | -12.433 | 1.00 | 9.59 | C |
| ATOM | 8496 | C | ALA A 605 | -11.523 | 73.375 | -13.718 | 1.00 | 10.07 | C |
| ATOM | 8497 | O | ALA A 605 | -12.314 | 73.798 | -14.562 | 1.00 | 10.17 | O |
| ATOM | 8499 | N | GLY A 606 | -10.822 | 74.208 | -12.936 | 1.00 | 10.21 | N |
| ATOM | 8500 | CA | GLY A 606 | -10.883 | 75.655 | -13.000 | 1.00 | 11.24 | C |
| ATOM | 8503 | C | GLY A 606 | -10.396 | 76.083 | -14.443 | 1.00 | 11.06 | C |
| ATOM | 8504 | O | GLY A 606 | -10.970 | 76.945 | -15.112 | 1.00 | 11.64 | O |
| ATOM | 8506 | N | THR A 607 | -9.299 | 75.473 | -14.858 | 1.00 | 11.38 | N |
| ATOM | 8507 | CA | THR A 607 | -8.775 | 75.672 | -16.198 | 1.00 | 10.68 | C |
| ATOM | 8509 | CB | THR A 607 | -7.447 | 74.938 | -16.359 | 1.00 | 11.35 | C |
| ATOM | 8511 | OG1 | THR A 607 | -6.509 | 75.475 | -15.434 | 1.00 | 12.56 | O |
| ATOM | 8513 | CG2 | THR A 607 | -6.927 | 75.045 | -17.791 | 1.00 | 12.57 | C |
| ATOM | 8517 | C | THR A 607 | -9.764 | 75.260 | -17.271 | 1.00 | 10.17 | C |
| ATOM | 8518 | O | THR A 607 | -9.953 | 75.965 | -18.239 | 1.00 | 10.56 | O |
| ATOM | 8520 | N | VAL A 608 | -10.444 | 74.129 | -17.090 | 1.00 | 9.74 | N |
| ATOM | 8521 | CA | VAL A 608 | -11.458 | 73.673 | -18.038 | 1.00 | 9.68 | C |
| ATOM | 8523 | CB | VAL A 608 | -12.048 | 72.281 | -17.671 | 1.00 | 10.59 | C |
| ATOM | 8525 | CG1 | VAL A 608 | -13.233 | 71.949 | -18.553 | 1.00 | 9.70 | C |
| ATOM | 8529 | CG2 | VAL A 608 | -10.909 | 71.191 | -17.668 | 1.00 | 10.39 | C |
| ATOM | 8533 | C | VAL A 608 | -12.592 | 74.715 | -18.181 | 1.00 | 9.37 | C |
| ATOM | 8534 | O | VAL A 608 | -13.076 | 74.969 | -19.260 | 1.00 | 9.44 | O |

| ATOM | 8536 | N | VAL A 609 | -13.006 | 75.287 | -17.043 | 1.00 | 9.63 | N |
|------|------|-----|-----------|---------|--------|---------|------|-------|---|
| ATOM | 8537 | CA | VAL A 609 | -14.092 | 76.267 | -17.025 | 1.00 | 10.01 | C |
| ATOM | 8539 | CB | VAL A 609 | -14.436 | 76.755 | -15.589 | 1.00 | 10.28 | C |
| ATOM | 8541 | CG1 | VAL A 609 | -15.265 | 78.037 | -15.643 | 1.00 | 12.56 | C |
| ATOM | 8545 | CG2 | VAL A 609 | -15.126 | 75.636 | -14.790 | 1.00 | 12.12 | C |
| ATOM | 8549 | C | VAL A 609 | -13.678 | 77.428 | -17.921 | 1.00 | 10.18 | C |
| ATOM | 8550 | O | VAL A 609 | -14.472 | 77.939 | -18.660 | 1.00 | 10.53 | O |
| ATOM | 8552 | N | GLU A 610 | -12.409 | 77.839 | -17.838 | 1.00 | 10.39 | N |
| ATOM | 8553 | CA | GLU A 610 | -11.949 | 78.957 | -18.648 | 1.00 | 12.21 | C |
| ATOM | 8555 | CB | GLU A 610 | -10.598 | 79.459 | -18.145 | 1.00 | 12.67 | C |
| ATOM | 8558 | CG | GLU A 610 | -10.017 | 80.639 | -18.921 | 1.00 | 14.62 | C |
| ATOM | 8561 | CD | GLU A 610 | -8.673 | 81.141 | -18.343 | 1.00 | 18.23 | C |
| ATOM | 8562 | OE1 | GLU A 610 | -8.301 | 80.776 | -17.184 | 1.00 | 23.82 | O |
| ATOM | 8563 | OE2 | GLU A 610 | -8.006 | 81.926 | -19.067 | 1.00 | 27.55 | O |
| ATOM | 8564 | C | GLU A 610 | -11.819 | 78.577 | -20.123 | 1.00 | 10.93 | C |
| ATOM | 8565 | O | GLU A 610 | -12.355 | 79.230 | -20.984 | 1.00 | 10.34 | O |
| ATOM | 8567 | N | VAL A 611 | -11.022 | 77.564 | -20.405 | 1.00 | 10.21 | N |
| ATOM | 8568 | CA | VAL A 611 | -10.723 | 77.222 | -21.793 | 1.00 | 9.76 | C |
| ATOM | 8570 | CB | VAL A 611 | -9.658 | 76.107 | -21.872 | 1.00 | 10.01 | C |
| ATOM | 8572 | CG1 | VAL A 611 | -9.405 | 75.736 | -23.334 | 1.00 | 11.41 | C |
| ATOM | 8576 | CG2 | VAL A 611 | -8.382 | 76.566 | -21.193 | 1.00 | 10.54 | C |
| ATOM | 8580 | C | VAL A 611 | -11.980 | 76.791 | -22.570 | 1.00 | 9.04 | C |
| ATOM | 8581 | O | VAL A 611 | -12.139 | 77.136 | -23.756 | 1.00 | 10.63 | O |
| ATOM | 8583 | N | LEU A 612 | -12.870 | 76.054 | -21.899 | 1.00 | 9.19 | N |
| ATOM | 8584 | CA | LEU A 612 | -14.069 | 75.554 | -22.517 | 1.00 | 9.63 | C |
| ATOM | 8586 | CB | LEU A 612 | -14.299 | 74.085 | -22.177 | 1.00 | 9.86 | C |
| ATOM | 8589 | CG | LEU A 612 | -13.181 | 73.091 | -22.584 | 1.00 | 9.87 | C |
| ATOM | 8591 | CD1 | LEU A 612 | -13.719 | 71.644 | -22.467 | 1.00 | 11.74 | C |
| ATOM | 8595 | CD2 | LEU A 612 | -12.728 | 73.371 | -24.000 | 1.00 | 10.11 | C |
| ATOM | 8599 | C | LEU A 612 | -15.302 | 76.389 | -22.145 | 1.00 | 10.01 | C |
| ATOM | 8600 | O | LEU A 612 | -16.433 | 75.928 | -22.259 | 1.00 | 8.79 | O |
| ATOM | 8602 | N | SER A 613 | -15.067 | 77.643 | -21.763 | 1.00 | 10.78 | N |
| ATOM | 8603 | CA | SER A 613 | -16.144 | 78.553 | -21.347 | 1.00 | 10.95 | C |
| ATOM | 8605 | CB | SER A 613 | -15.563 | 79.911 | -20.928 | 1.00 | 11.37 | C |
| ATOM | 8608 | OG | SER A 613 | -15.136 | 80.653 | -22.054 | 1.00 | 14.14 | O |
| ATOM | 8610 | C | SER A 613 | -17.256 | 78.737 | -22.376 | 1.00 | 10.97 | C |
| ATOM | 8611 | O | SER A 613 | -18.385 | 79.030 | -21.987 | 1.00 | 13.52 | O |
| ATOM | 8613 | N | SER A 614 | -16.975 | 78.539 | -23.672 | 1.00 | 10.86 | N |
| ATOM | 8614 | CA | SER A 614 | -17.963 | 78.733 | -24.724 | 1.00 | 11.09 | C |
| ATOM | 8616 | CB | SER A 614 | -17.302 | 79.251 | -26.014 | 1.00 | 12.80 | C |
| ATOM | 8619 | OG | SER A 614 | -16.537 | 78.210 | -26.597 | 1.00 | 17.47 | O |
| ATOM | 8621 | C | SER A 614 | -18.753 | 77.449 | -25.064 | 1.00 | 11.15 | C |
| ATOM | 8622 | O | SER A 614 | -19.618 | 77.488 | -25.922 | 1.00 | 10.86 | O |
| ATOM | 8624 | N | THR A 615 | -18.439 | 76.331 | -24.401 | 1.00 | 10.20 | N |
| ATOM | 8625 | CA | THR A 615 | -19.037 | 75.048 | -24.740 | 1.00 | 11.11 | C |
| ATOM | 8627 | CB | THR A 615 | -18.049 | 73.894 | -24.554 | 1.00 | 11.30 | C |
| ATOM | 8629 | OG1 | THR A 615 | -17.845 | 73.683 | -23.162 | 1.00 | 10.85 | O |
| ATOM | 8631 | CG2 | THR A 615 | -16.734 | 74.141 | -25.287 | 1.00 | 12.60 | C |
| ATOM | 8635 | C | THR A 615 | -20.308 | 74.797 | -23.928 | 1.00 | 10.59 | C |
| ATOM | 8636 | O | THR A 615 | -20.601 | 75.525 | -22.996 | 1.00 | 11.09 | O |
| ATOM | 8638 | N | SER A 616 | -20.982 | 73.701 | -24.244 | 1.00 | 10.33 | N |
| ATOM | 8639 | CA | SER A 616 | -22.263 | 73.337 | -23.685 | 1.00 | 11.98 | C |
| ATOM | 8641 | CB | SER A 616 | -23.094 | 72.617 | -24.786 | 1.00 | 13.10 | C |
| ATOM | 8644 | OG | SER A 616 | -22.441 | 71.399 | -25.144 | 1.00 | 15.06 | O |
| ATOM | 8646 | C | SER A 616 | -22.134 | 72.407 | -22.471 | 1.00 | 10.46 | C |
| ATOM | 8647 | O | SER A 616 | -23.155 | 71.951 | -21.974 | 1.00 | 10.86 | O |
| ATOM | 8649 | N | LEU A 617 | -20.923 | 72.147 | -21.980 | 1.00 | 10.64 | N |

| | | | | | | | | |
|---|---|---|---|---|---|---|---|---|
| ATOM | 8650 | CA  | LEU A 617 | -20.700 | 71.193 | -20.919 | 1.00 | 10.54 | C |
| ATOM | 8652 | CB  | LEU A 617 | -19.219 | 71.066 | -20.612 | 1.00 | 9.98  | C |
| ATOM | 8655 | CG  | LEU A 617 | -18.400 | 70.308 | -21.632 | 1.00 | 9.73  | C |
| ATOM | 8657 | CD1 | LEU A 617 | -16.947 | 70.615 | -21.475 | 1.00 | 10.73 | C |
| ATOM | 8661 | CD2 | LEU A 617 | -18.667 | 68.817 | -21.466 | 1.00 | 10.05 | C |
| ATOM | 8665 | C   | LEU A 617 | -21.416 | 71.606 | -19.637 | 1.00 | 10.68 | C |
| ATOM | 8666 | O   | LEU A 617 | -21.480 | 72.793 | -19.320 | 1.00 | 11.85 | O |
| ATOM | 8668 | N   | SER A 618 | -21.941 | 70.624 | -18.921 | 1.00 | 9.52  | N |
| ATOM | 8669 | CA  | SER A 618 | -22.531 | 70.883 | -17.610 | 1.00 | 9.62  | C |
| ATOM | 8671 | CB  | SER A 618 | -23.542 | 69.811 | -17.250 | 1.00 | 9.58  | C |
| ATOM | 8674 | OG  | SER A 618 | -22.887 | 68.545 | -17.123 | 1.00 | 10.06 | O |
| ATOM | 8676 | C   | SER A 618 | -21.446 | 70.880 | -16.569 | 1.00 | 10.84 | C |
| ATOM | 8677 | O   | SER A 618 | -20.357 | 70.340 | -16.765 | 1.00 | 10.35 | O |
| ATOM | 8679 | N   | LEU A 619 | -21.747 | 71.418 | -15.398 | 1.00 | 10.26 | N |
| ATOM | 8680 | CA  | LEU A 619 | -20.819 | 71.260 | -14.303 | 1.00 | 10.43 | C |
| ATOM | 8682 | CB  | LEU A 619 | -21.224 | 72.159 | -13.135 | 1.00 | 10.04 | C |
| ATOM | 8685 | CG  | LEU A 619 | -21.135 | 73.652 | -13.415 | 1.00 | 13.49 | C |
| ATOM | 8687 | CD1 | LEU A 619 | -21.435 | 74.401 | -12.114 | 1.00 | 14.26 | C |
| ATOM | 8691 | CD2 | LEU A 619 | -19.795 | 74.078 | -13.941 | 1.00 | 15.50 | C |
| ATOM | 8695 | C   | LEU A 619 | -20.669 | 69.780 | -13.840 | 1.00 | 9.63  | C |
| ATOM | 8696 | O   | LEU A 619 | -19.577 | 69.364 | -13.459 | 1.00 | 10.59 | O |
| ATOM | 8698 | N   | ALA A 620 | -21.729 | 68.982 | -13.950 | 1.00 | 10.82 | N |
| ATOM | 8699 | CA  | ALA A 620 | -21.654 | 67.544 | -13.636 | 1.00 | 10.70 | C |
| ATOM | 8701 | CB  | ALA A 620 | -22.983 | 66.897 | -13.785 | 1.00 | 11.15 | C |
| ATOM | 8705 | C   | ALA A 620 | -20.630 | 66.833 | -14.509 | 1.00 | 9.85  | C |
| ATOM | 8706 | O   | ALA A 620 | -19.833 | 66.027 | -14.014 | 1.00 | 9.72  | O |
| ATOM | 8708 | N   | ALA A 621 | -20.622 | 67.198 | -15.790 | 1.00 | 9.94  | N |
| ATOM | 8709 | CA  | ALA A 621 | -19.688 | 66.614 | -16.773 | 1.00 | 9.80  | C |
| ATOM | 8711 | CB  | ALA A 621 | -20.007 | 67.123 | -18.152 | 1.00 | 10.90 | C |
| ATOM | 8715 | C   | ALA A 621 | -18.221 | 66.956 | -16.423 | 1.00 | 9.74  | C |
| ATOM | 8716 | O   | ALA A 621 | -17.312 | 66.114 | -16.466 | 1.00 | 10.44 | O |
| ATOM | 8718 | N   | VAL A 622 | -17.977 | 68.206 | -16.063 | 1.00 | 9.71  | N |
| ATOM | 8719 | CA  | VAL A 622 | -16.612 | 68.599 | -15.758 | 1.00 | 10.12 | C |
| ATOM | 8721 | CB  | VAL A 622 | -16.436 | 70.144 | -15.721 | 1.00 | 9.41  | C |
| ATOM | 8723 | CG1 | VAL A 622 | -14.967 | 70.510 | -15.325 | 1.00 | 11.45 | C |
| ATOM | 8727 | CG2 | VAL A 622 | -16.839 | 70.789 | -17.035 | 1.00 | 9.87  | C |
| ATOM | 8731 | C   | VAL A 622 | -16.174 | 67.933 | -14.436 | 1.00 | 9.50  | C |
| ATOM | 8732 | O   | VAL A 622 | -15.056 | 67.426 | -14.314 | 1.00 | 9.09  | O |
| ATOM | 8734 | N   | ASN A 623 | -17.075 | 67.915 | -13.442 | 1.00 | 10.12 | N |
| ATOM | 8735 | CA  | ASN A 623 | -16.761 | 67.250 | -12.179 | 1.00 | 10.86 | C |
| ATOM | 8737 | CB  | ASN A 623 | -17.911 | 67.448 | -11.193 | 1.00 | 11.89 | C |
| ATOM | 8740 | CG  | ASN A 623 | -17.528 | 67.069 | -9.790  | 1.00 | 11.50 | C |
| ATOM | 8741 | OD1 | ASN A 623 | -16.494 | 67.476 | -9.279  | 1.00 | 16.14 | O |
| ATOM | 8742 | ND2 | ASN A 623 | -18.346 | 66.218 | -9.188  | 1.00 | 18.64 | N |
| ATOM | 8745 | C   | ASN A 623 | -16.488 | 65.746 | -12.383 | 1.00 | 10.15 | C |
| ATOM | 8746 | O   | ASN A 623 | -15.590 | 65.189 | -11.748 | 1.00 | 10.86 | O |
| ATOM | 8748 | N   | ALA A 624 | -17.248 | 65.135 | -13.284 | 1.00 | 10.04 | N |
| ATOM | 8749 | CA  | ALA A 624 | -17.098 | 63.722 | -13.562 | 1.00 | 9.77  | C |
| ATOM | 8751 | CB  | ALA A 624 | -18.173 | 63.220 | -14.474 | 1.00 | 9.72  | C |
| ATOM | 8755 | C   | ALA A 624 | -15.739 | 63.449 | -14.173 | 1.00 | 10.67 | C |
| ATOM | 8756 | O   | ALA A 624 | -15.094 | 62.473 | -13.827 | 1.00 | 11.00 | O |
| ATOM | 8758 | N   | TRP A 625 | -15.298 | 64.324 | -15.077 | 1.00 | 10.28 | N |
| ATOM | 8759 | CA  | TRP A 625 | -13.950 | 64.228 | -15.629 | 1.00 | 10.43 | C |
| ATOM | 8761 | CB  | TRP A 625 | -13.737 | 65.338 | -16.665 | 1.00 | 10.70 | C |
| ATOM | 8764 | CG  | TRP A 625 | -12.333 | 65.495 | -17.110 | 1.00 | 8.80  | C |
| ATOM | 8765 | CD1 | TRP A 625 | -11.656 | 64.744 | -18.056 | 1.00 | 11.73 | C |
| ATOM | 8767 | NE1 | TRP A 625 | -10.365 | 65.210 | -18.177 | 1.00 | 12.83 | N |

| | | | | | | | | | |
|---|---|---|---|---|---|---|---|---|---|
| ATOM | 8769 | CE2 | TRP A 625 | -10.170 | 66.261 | -17.329 | 1.00 | 11.84 | C |
| ATOM | 8770 | CD2 | TRP A 625 | -11.389 | 66.473 | -16.627 | 1.00 | 10.58 | C |
| ATOM | 8771 | CE3 | TRP A 625 | -11.470 | 67.516 | -15.716 | 1.00 | 10.89 | C |
| ATOM | 8773 | CZ3 | TRP A 625 | -10.358 | 68.274 | -15.492 | 1.00 | 10.78 | C |
| ATOM | 8775 | CH2 | TRP A 625 | -9.154 | 68.034 | -16.181 | 1.00 | 11.48 | C |
| ATOM | 8777 | CZ2 | TRP A 625 | -9.051 | 67.066 | -17.128 | 1.00 | 12.75 | C |
| ATOM | 8779 | C | TRP A 625 | -12.908 | 64.353 | -14.533 | 1.00 | 10.55 | C |
| ATOM | 8780 | O | TRP A 625 | -11.926 | 63.611 | -14.481 | 1.00 | 11.05 | O |
| ATOM | 8782 | N | LYS A 626 | -13.092 | 65.342 | -13.661 | 1.00 | 10.36 | N |
| ATOM | 8783 | CA | LYS A 626 | -12.159 | 65.593 | -12.561 | 1.00 | 11.72 | C |
| ATOM | 8785 | CB | LYS A 626 | -12.686 | 66.786 | -11.752 | 1.00 | 12.26 | C |
| ATOM | 8788 | CG | LYS A 626 | -11.948 | 67.132 | -10.470 | 1.00 | 13.70 | C |
| ATOM | 8791 | CD | LYS A 626 | -12.455 | 66.313 | -9.275 | 1.00 | 14.38 | C |
| ATOM | 8794 | CE | LYS A 626 | -11.979 | 66.906 | -7.960 | 1.00 | 14.91 | C |
| ATOM | 8797 | NZ | LYS A 626 | -12.425 | 66.066 | -6.818 | 1.00 | 15.52 | N |
| ATOM | 8801 | C | LYS A 626 | -11.993 | 64.329 | -11.686 | 1.00 | 11.19 | C |
| ATOM | 8802 | O | LYS A 626 | -10.879 | 63.930 | -11.332 | 1.00 | 11.21 | O |
| ATOM | 8804 | N | VAL A 627 | -13.113 | 63.708 | -11.355 | 1.00 | 11.23 | N |
| ATOM | 8805 | CA | VAL A 627 | -13.092 | 62.525 | -10.527 | 1.00 | 12.16 | C |
| ATOM | 8807 | CB | VAL A 627 | -14.509 | 62.147 | -10.059 | 1.00 | 12.86 | C |
| ATOM | 8809 | CG1 | VAL A 627 | -14.507 | 60.745 | -9.465 | 1.00 | 14.22 | C |
| ATOM | 8813 | CG2 | VAL A 627 | -15.080 | 63.150 | -9.081 | 1.00 | 11.64 | C |
| ATOM | 8817 | C | VAL A 627 | -12.405 | 61.348 | -11.261 | 1.00 | 12.19 | C |
| ATOM | 8818 | O | VAL A 627 | -11.546 | 60.679 | -10.675 | 1.00 | 11.68 | O |
| ATOM | 8820 | N | ALA A 628 | -12.766 | 61.112 | -12.521 | 1.00 | 11.83 | N |
| ATOM | 8821 | CA | ALA A 628 | -12.204 | 59.982 | -13.314 | 1.00 | 12.20 | C |
| ATOM | 8823 | CB | ALA A 628 | -12.881 | 59.882 | -14.690 | 1.00 | 12.14 | C |
| ATOM | 8827 | C | ALA A 628 | -10.716 | 60.210 | -13.488 | 1.00 | 12.35 | C |
| ATOM | 8828 | O | ALA A 628 | -9.883 | 59.275 | -13.421 | 1.00 | 13.91 | O |
| ATOM | 8830 | N | ALA A 629 | -10.347 | 61.457 | -13.724 | 1.00 | 11.81 | N |
| ATOM | 8831 | CA | ALA A 629 | -8.942 | 61.773 | -13.938 | 1.00 | 11.27 | C |
| ATOM | 8833 | CB | ALA A 629 | -8.760 | 63.150 | -14.529 | 1.00 | 11.23 | C |
| ATOM | 8837 | C | ALA A 629 | -8.131 | 61.595 | -12.678 | 1.00 | 11.16 | C |
| ATOM | 8838 | O | ALA A 629 | -7.073 | 60.999 | -12.717 | 1.00 | 11.40 | O |
| ATOM | 8840 | N | ALA A 630 | -8.629 | 62.098 | -11.540 | 1.00 | 11.10 | N |
| ATOM | 8841 | CA | ALA A 630 | -7.931 | 61.839 | -10.278 | 1.00 | 11.75 | C |
| ATOM | 8843 | CB | ALA A 630 | -8.662 | 62.497 | -9.121 | 1.00 | 12.01 | C |
| ATOM | 8847 | C | ALA A 630 | -7.781 | 60.337 | -10.018 | 1.00 | 11.86 | C |
| ATOM | 8848 | O | ALA A 630 | -6.696 | 59.833 | -9.653 | 1.00 | 12.39 | O |
| ATOM | 8850 | N | GLU A 631 | -8.868 | 59.602 | -10.209 | 1.00 | 12.10 | N |
| ATOM | 8851 | CA | GLU A 631 | -8.850 | 58.142 | -9.990 | 1.00 | 14.31 | C |
| ATOM | 8853 | CB | GLU A 631 | -10.222 | 57.524 | -10.210 | 1.00 | 14.81 | C |
| ATOM | 8856 | CG | GLU A 631 | -11.193 | 57.833 | -9.107 | 1.00 | 17.40 | C |
| ATOM | 8859 | CD | GLU A 631 | -12.614 | 57.355 | -9.406 | 1.00 | 20.07 | C |
| ATOM | 8860 | OE1 | GLU A 631 | -12.988 | 57.188 | -10.599 | 1.00 | 28.18 | O |
| ATOM | 8861 | OE2 | GLU A 631 | -13.366 | 57.169 | -8.425 | 1.00 | 29.95 | O |
| ATOM | 8862 | C | GLU A 631 | -7.832 | 57.470 | -10.885 | 1.00 | 14.42 | C |
| ATOM | 8863 | O | GLU A 631 | -7.119 | 56.550 | -10.461 | 1.00 | 15.65 | O |
| ATOM | 8865 | N | SER A 632 | -7.773 | 57.923 | -12.128 | 1.00 | 13.47 | N |
| ATOM | 8866 | CA | SER A 632 | -6.817 | 57.370 | -13.095 | 1.00 | 14.22 | C |
| ATOM | 8868 | CB | SER A 632 | -7.074 | 57.984 | -14.481 | 1.00 | 14.77 | C |
| ATOM | 8871 | OG | SER A 632 | -6.019 | 57.722 | -15.386 | 1.00 | 17.58 | O |
| ATOM | 8873 | C | SER A 632 | -5.383 | 57.627 | -12.634 | 1.00 | 13.75 | C |
| ATOM | 8874 | O | SER A 632 | -4.521 | 56.709 | -12.692 | 1.00 | 15.80 | O |
| ATOM | 8876 | N | ALA A 633 | -5.100 | 58.845 | -12.197 | 1.00 | 13.66 | N |
| ATOM | 8877 | CA | ALA A 633 | -3.754 | 59.180 | -11.726 | 1.00 | 13.42 | C |
| ATOM | 8879 | CB | ALA A 633 | -3.638 | 60.641 | -11.406 | 1.00 | 13.98 | C |

| | | | | | | | | | |
|---|---|---|---|---|---|---|---|---|---|
| ATOM | 8883 | C | ALA A 633 | | -3.367 | 58.377 | -10.499 | 1.00 | 13.55 | C |
| ATOM | 8884 | O | ALA A 633 | | -2.222 | 57.942 | -10.356 | 1.00 | 14.71 | O |
| ATOM | 8886 | N | ILE A 634 | | -4.328 | 58.222 | -9.598 | 1.00 | 13.88 | N |
| ATOM | 8887 | CA | ILE A 634 | | -4.106 | 57.461 | -8.346 | 1.00 | 13.53 | C |
| ATOM | 8889 | CB | ILE A 634 | | -5.366 | 57.508 | -7.470 | 1.00 | 12.71 | C |
| ATOM | 8891 | CG1 | ILE A 634 | | -5.517 | 58.902 | -6.892 | 1.00 | 12.78 | C |
| ATOM | 8894 | CD1 | ILE A 634 | | -6.901 | 59.209 | -6.399 | 1.00 | 13.89 | C |
| ATOM | 8898 | CG2 | ILE A 634 | | -5.367 | 56.450 | -6.327 | 1.00 | 14.97 | C |
| ATOM | 8902 | C | ILE A 634 | | -3.750 | 56.007 | -8.695 | 1.00 | 14.25 | C |
| ATOM | 8903 | O | ILE A 634 | | -2.708 | 55.498 | -8.278 | 1.00 | 13.76 | O |
| ATOM | 8905 | N | SER A 635 | | -4.603 | 55.350 | -9.485 | 1.00 | 14.49 | N |
| ATOM | 8906 | CA | SER A 635 | | -4.344 | 53.957 | -9.861 | 1.00 | 14.69 | C |
| ATOM | 8908 | CB | SER A 635 | | -5.522 | 53.355 | -10.623 | 1.00 | 16.73 | C |
| ATOM | 8911 | OG | SER A 635 | | -5.771 | 54.109 | -11.769 | 1.00 | 25.07 | O |
| ATOM | 8913 | C | SER A 635 | | -3.022 | 53.836 | -10.642 | 1.00 | 14.27 | C |
| ATOM | 8914 | O | SER A 635 | | -2.266 | 52.913 | -10.410 | 1.00 | 14.30 | O |
| ATOM | 8916 | N | LEU A 636 | | -2.721 | 54.777 | -11.541 | 1.00 | 13.76 | N |
| ATOM | 8917 | CA | LEU A 636 | | -1.461 | 54.719 | -12.304 | 1.00 | 14.49 | C |
| ATOM | 8919 | CB | LEU A 636 | | -1.445 | 55.815 | -13.366 | 1.00 | 14.21 | C |
| ATOM | 8922 | CG | LEU A 636 | | -0.174 | 55.919 | -14.210 | 1.00 | 14.92 | C |
| ATOM | 8924 | CD1 | LEU A 636 | | 0.077 | 54.598 | -14.945 | 1.00 | 16.43 | C |
| ATOM | 8928 | CD2 | LEU A 636 | | -0.317 | 57.064 | -15.176 | 1.00 | 16.71 | C |
| ATOM | 8932 | C | LEU A 636 | | -0.253 | 54.851 | -11.396 | 1.00 | 13.58 | C |
| ATOM | 8933 | O | LEU A 636 | | 0.740 | 54.150 | -11.533 | 1.00 | 14.31 | O |
| ATOM | 8935 | N | THR A 637 | | -0.335 | 55.754 | -10.431 | 1.00 | 11.92 | N |
| ATOM | 8936 | CA | THR A 637 | | 0.759 | 55.919 | -9.470 | 1.00 | 12.66 | C |
| ATOM | 8938 | CB | THR A 637 | | 0.467 | 57.009 | -8.432 | 1.00 | 13.06 | C |
| ATOM | 8940 | OG1 | THR A 637 | | 0.325 | 58.285 | -9.060 | 1.00 | 11.56 | O |
| ATOM | 8942 | CG2 | THR A 637 | | 1.621 | 57.084 | -7.452 | 1.00 | 14.97 | C |
| ATOM | 8946 | C | THR A 637 | | 1.007 | 54.596 | -8.729 | 1.00 | 12.54 | C |
| ATOM | 8947 | O | THR A 637 | | 2.133 | 54.169 | -8.570 | 1.00 | 12.76 | O |
| ATOM | 8949 | N | ARG A 638 | | -0.066 | 53.926 | -8.302 | 1.00 | 12.69 | N |
| ATOM | 8950 | CA | ARG A 638 | | 0.079 | 52.691 | -7.564 | 1.00 | 13.68 | C |
| ATOM | 8952 | CB | ARG A 638 | | -1.271 | 52.191 | -7.026 | 1.00 | 13.58 | C |
| ATOM | 8955 | CG | ARG A 638 | | -1.823 | 53.071 | -5.948 | 1.00 | 16.58 | C |
| ATOM | 8958 | CD | ARG A 638 | | -3.163 | 52.587 | -5.466 | 1.00 | 16.47 | C |
| ATOM | 8961 | NE | ARG A 638 | | -3.613 | 53.422 | -4.345 | 1.00 | 18.04 | N |
| ATOM | 8963 | CZ | ARG A 638 | | -4.885 | 53.754 | -4.109 | 1.00 | 18.34 | C |
| ATOM | 8964 | NH1 | ARG A 638 | | -5.848 | 53.369 | -4.907 | 1.00 | 20.09 | N |
| ATOM | 8967 | NH2 | ARG A 638 | | -5.181 | 54.508 | -3.088 | 1.00 | 17.58 | N |
| ATOM | 8970 | C | ARG A 638 | | 0.767 | 51.655 | -8.450 | 1.00 | 13.94 | C |
| ATOM | 8971 | O | ARG A 638 | | 1.632 | 50.924 | -7.978 | 1.00 | 14.48 | O |
| ATOM | 8973 | N | GLN A 639 | | 0.372 | 51.581 | -9.731 | 1.00 | 13.49 | N |
| ATOM | 8974 | CA | GLN A 639 | | 0.970 | 50.649 | -10.683 | 1.00 | 15.93 | C |
| ATOM | 8976 | CB | GLN A 639 | | 0.179 | 50.741 | -11.962 | 1.00 | 15.96 | C |
| ATOM | 8979 | CG | GLN A 639 | | 0.632 | 49.900 | -13.160 | 1.00 | 19.42 | C |
| ATOM | 8982 | CD | GLN A 639 | | -0.448 | 49.887 | -14.289 | 1.00 | 22.16 | C |
| ATOM | 8983 | OE1 | GLN A 639 | | -1.114 | 50.915 | -14.600 | 1.00 | 27.22 | O |
| ATOM | 8984 | NE2 | GLN A 639 | | -0.654 | 48.700 | -14.878 | 1.00 | 32.53 | N |
| ATOM | 8987 | C | GLN A 639 | | 2.462 | 50.925 | -10.954 | 1.00 | 15.49 | C |
| ATOM | 8988 | O | GLN A 639 | | 3.287 | 49.992 | -10.972 | 1.00 | 16.30 | O |
| ATOM | 8990 | N | VAL A 640 | | 2.795 | 52.195 | -11.175 | 1.00 | 14.97 | N |
| ATOM | 8991 | CA | VAL A 640 | | 4.177 | 52.566 | -11.437 | 1.00 | 14.82 | C |
| ATOM | 8993 | CB | VAL A 640 | | 4.301 | 54.046 | -11.876 | 1.00 | 14.95 | C |
| ATOM | 8995 | CG1 | VAL A 640 | | 5.743 | 54.502 | -11.885 | 1.00 | 17.15 | C |
| ATOM | 8999 | CG2 | VAL A 640 | | 3.688 | 54.213 | -13.231 | 1.00 | 14.84 | C |
| ATOM | 9003 | C | VAL A 640 | | 5.056 | 52.234 | -10.219 | 1.00 | 14.93 | C |

| ATOM | 9004 | O   | VAL A 640 | 6.192  | 51.739 | -10.356 | 1.00 | 14.97 | O |
|------|------|-----|-----------|--------|--------|---------|------|-------|---|
| ATOM | 9006 | N   | ARG A 641 | 4.518  | 52.460 | -9.035  | 1.00 | 14.22 | N |
| ATOM | 9007 | CA  | ARG A 641 | 5.228  | 52.092 | -7.804  | 1.00 | 15.04 | C |
| ATOM | 9009 | CB  | ARG A 641 | 4.443  | 52.536 | -6.587  | 1.00 | 15.53 | C |
| ATOM | 9012 | CG  | ARG A 641 | 4.441  | 54.006 | -6.437  | 1.00 | 14.90 | C |
| ATOM | 9015 | CD  | ARG A 641 | 3.531  | 54.430 | -5.283  | 1.00 | 16.01 | C |
| ATOM | 9018 | NE  | ARG A 641 | 3.733  | 55.826 | -4.903  | 1.00 | 15.65 | N |
| ATOM | 9020 | CZ  | ARG A 641 | 2.917  | 56.480 | -4.065  | 1.00 | 13.75 | C |
| ATOM | 9021 | NH1 | ARG A 641 | 1.852  | 55.878 | -3.540  | 1.00 | 14.02 | N |
| ATOM | 9024 | NH2 | ARG A 641 | 3.149  | 57.727 | -3.756  | 1.00 | 17.61 | N |
| ATOM | 9027 | C   | ARG A 641 | 5.450  | 50.592 | -7.716  | 1.00 | 15.30 | C |
| ATOM | 9028 | O   | ARG A 641 | 6.546  | 50.121 | -7.478  | 1.00 | 14.60 | O |
| ATOM | 9030 | N   | GLU A 642 | 4.394  | 49.831 | -7.913  | 1.00 | 14.84 | N |
| ATOM | 9031 | CA  | GLU A 642 | 4.505  | 48.367 | -7.873  | 1.00 | 15.36 | C |
| ATOM | 9033 | CB  | GLU A 642 | 3.128  | 47.749 | -8.094  | 1.00 | 15.69 | C |
| ATOM | 9036 | CG  | GLU A 642 | 2.320  | 47.724 | -6.858  | 1.00 | 19.57 | C |
| ATOM | 9039 | CD  | GLU A 642 | 3.050  | 46.973 | -5.746  | 1.00 | 25.78 | C |
| ATOM | 9040 | OE1 | GLU A 642 | 3.629  | 45.885 | -5.994  | 1.00 | 32.26 | O |
| ATOM | 9041 | OE2 | GLU A 642 | 3.035  | 47.459 | -4.618  | 1.00 | 25.34 | O |
| ATOM | 9042 | C   | GLU A 642 | 5.519  | 47.830 | -8.891  | 1.00 | 15.10 | C |
| ATOM | 9043 | O   | GLU A 642 | 6.304  | 46.938 | -8.600  | 1.00 | 15.75 | O |
| ATOM | 9045 | N   | THR A 643 | 5.517  | 48.402 | -10.081 | 1.00 | 15.41 | N |
| ATOM | 9046 | CA  | THR A 643 | 6.474  | 48.005 | -11.115 | 1.00 | 15.57 | C |
| ATOM | 9048 | CB  | THR A 643 | 6.161  | 48.745 | -12.413 | 1.00 | 16.22 | C |
| ATOM | 9050 | OG1 | THR A 643 | 4.874  | 48.310 | -12.902 | 1.00 | 14.88 | O |
| ATOM | 9052 | CG2 | THR A 643 | 7.177  | 48.431 | -13.489 | 1.00 | 16.00 | C |
| ATOM | 9056 | C   | THR A 643 | 7.920  | 48.215 | -10.633 | 1.00 | 15.44 | C |
| ATOM | 9057 | O   | THR A 643 | 8.776  | 47.355 | -10.791 | 1.00 | 14.65 | O |
| ATOM | 9059 | N   | PHE A 644 | 8.169  | 49.353 | -10.000 | 1.00 | 15.44 | N |
| ATOM | 9060 | CA  | PHE A 644 | 9.486  | 49.649 | -9.407  | 1.00 | 15.55 | C |
| ATOM | 9062 | CB  | PHE A 644 | 9.512  | 51.051 | -8.855  | 1.00 | 15.79 | C |
| ATOM | 9065 | CG  | PHE A 644 | 10.760 | 51.357 | -8.060  | 1.00 | 14.60 | C |
| ATOM | 9066 | CD1 | PHE A 644 | 11.902 | 51.784 | -8.693  | 1.00 | 18.28 | C |
| ATOM | 9068 | CE1 | PHE A 644 | 13.074 | 52.074 | -7.952  | 1.00 | 18.32 | C |
| ATOM | 9070 | CZ  | PHE A 644 | 13.062 | 51.912 | -6.585  | 1.00 | 19.52 | C |
| ATOM | 9072 | CE2 | PHE A 644 | 11.913 | 51.494 | -5.944  | 1.00 | 17.77 | C |
| ATOM | 9074 | CD2 | PHE A 644 | 10.773 | 51.220 | -6.676  | 1.00 | 16.17 | C |
| ATOM | 9076 | C   | PHE A 644 | 9.879  | 48.667 | -8.319  | 1.00 | 15.34 | C |
| ATOM | 9077 | O   | PHE A 644 | 10.994 | 48.126 | -8.333  | 1.00 | 14.91 | O |
| ATOM | 9079 | N   | TRP A 645 | 8.969  | 48.412 | -7.391  | 1.00 | 15.11 | N |
| ATOM | 9080 | CA  | TRP A 645 | 9.287  | 47.631 | -6.199  | 1.00 | 17.04 | C |
| ATOM | 9082 | CB  | TRP A 645 | 8.279  | 47.952 | -5.070  | 1.00 | 16.19 | C |
| ATOM | 9085 | CG  | TRP A 645 | 8.461  | 49.345 | -4.520  | 1.00 | 15.94 | C |
| ATOM | 9086 | CD1 | TRP A 645 | 7.650  | 50.409 | -4.701  | 1.00 | 14.28 | C |
| ATOM | 9088 | NE1 | TRP A 645 | 8.146  | 51.510 | -4.052  | 1.00 | 15.10 | N |
| ATOM | 9090 | CE2 | TRP A 645 | 9.347  | 51.183 | -3.474  | 1.00 | 15.40 | C |
| ATOM | 9091 | CD2 | TRP A 645 | 9.583  | 49.825 | -3.763  | 1.00 | 14.40 | C |
| ATOM | 9092 | CE3 | TRP A 645 | 10.747 | 49.219 | -3.269  | 1.00 | 18.52 | C |
| ATOM | 9094 | CZ3 | TRP A 645 | 11.647 | 49.983 | -2.514  | 1.00 | 15.85 | C |
| ATOM | 9096 | CH2 | TRP A 645 | 11.397 | 51.344 | -2.259  | 1.00 | 15.45 | C |
| ATOM | 9098 | CZ2 | TRP A 645 | 10.255 | 51.963 | -2.731  | 1.00 | 15.41 | C |
| ATOM | 9100 | C   | TRP A 645 | 9.346  | 46.132 | -6.474  | 1.00 | 18.25 | C |
| ATOM | 9101 | O   | TRP A 645 | 9.941  | 45.418 | -5.682  | 1.00 | 18.93 | O |
| ATOM | 9103 | N   | SER A 646 | 8.739  | 45.671 | -7.571  | 1.00 | 18.96 | N |
| ATOM | 9104 | CA  | SER A 646 | 8.666  | 44.253 | -7.951  | 1.00 | 20.62 | C |
| ATOM | 9106 | CB  | SER A 646 | 7.469  | 44.027 | -8.895  | 1.00 | 20.12 | C |
| ATOM | 9109 | OG  | SER A 646 | 6.312  | 44.060 | -8.135  | 1.00 | 24.98 | O |

| | | | | | | | | | |
|---|---|---|---|---|---|---|---|---|---|
| ATOM | 9111 | C   | SER A 646 |  9.884 | 43.768 |  -8.684 | 1.00 | 21.34 | C |
| ATOM | 9112 | O   | SER A 646 | 10.077 | 42.559 |  -8.844 | 1.00 | 24.21 | O |
| ATOM | 9114 | N   | ALA A 647 | 10.636 | 44.702 |  -9.227 | 1.00 | 22.04 | N |
| ATOM | 9115 | CA  | ALA A 647 | 11.783 | 44.374 | -10.051 | 1.00 | 21.34 | C |
| ATOM | 9117 | CB  | ALA A 647 | 11.869 | 45.321 | -11.202 | 1.00 | 22.24 | C |
| ATOM | 9121 | C   | ALA A 647 | 13.030 | 44.490 |  -9.221 | 1.00 | 21.10 | C |
| ATOM | 9122 | O   | ALA A 647 | 13.035 | 45.160 |  -8.189 | 1.00 | 20.69 | O |
| ATOM | 9124 | N   | ALA A 648 | 14.102 | 43.864 |  -9.691 | 1.00 | 21.10 | N |
| ATOM | 9125 | CA  | ALA A 648 | 15.398 | 43.980 |  -9.036 | 1.00 | 20.96 | C |
| ATOM | 9127 | CB  | ALA A 648 | 16.348 | 42.931 |  -9.600 | 1.00 | 21.50 | C |
| ATOM | 9131 | C   | ALA A 648 | 15.937 | 45.388 |  -9.287 | 1.00 | 20.54 | C |
| ATOM | 9132 | O   | ALA A 648 | 15.590 | 46.022 | -10.277 | 1.00 | 20.26 | O |
| ATOM | 9134 | N   | SER A 649 | 16.824 | 45.842 |  -8.411 | 1.00 | 19.87 | N |
| ATOM | 9135 | CA  | SER A 649 | 17.451 | 47.157 |  -8.529 | 1.00 | 19.14 | C |
| ATOM | 9137 | CB  | SER A 649 | 18.199 | 47.547 |  -7.237 | 1.00 | 19.27 | C |
| ATOM | 9140 | OG  | SER A 649 | 18.964 | 46.479 |  -6.735 | 1.00 | 18.26 | O |
| ATOM | 9142 | C   | SER A 649 | 18.367 | 47.231 |  -9.728 | 1.00 | 18.83 | C |
| ATOM | 9143 | O   | SER A 649 | 18.630 | 48.312 | -10.228 | 1.00 | 16.98 | O |
| ATOM | 9145 | N   | THR A 650 | 18.804 | 46.073 | -10.227 | 1.00 | 17.73 | N |
| ATOM | 9146 | CA  | THR A 650 | 19.602 | 46.005 | -11.453 | 1.00 | 18.17 | C |
| ATOM | 9148 | CB  | THR A 650 | 20.226 | 44.631 | -11.625 | 1.00 | 18.33 | C |
| ATOM | 9150 | OG1 | THR A 650 | 19.250 | 43.607 | -11.382 | 1.00 | 17.55 | O |
| ATOM | 9152 | CG2 | THR A 650 | 21.393 | 44.435 | -10.657 | 1.00 | 18.32 | C |
| ATOM | 9156 | C   | THR A 650 | 18.753 | 46.351 | -12.685 | 1.00 | 17.90 | C |
| ATOM | 9157 | O   | THR A 650 | 19.306 | 46.622 | -13.744 | 1.00 | 17.90 | O |
| ATOM | 9159 | N   | SER A 651 | 17.426 | 46.369 | -12.508 | 1.00 | 18.63 | N |
| ATOM | 9160 | CA  | SER A 651 | 16.475 | 46.888 | -13.493 | 1.00 | 18.23 | C |
| ATOM | 9162 | CB  | SER A 651 | 15.415 | 45.815 | -13.787 | 1.00 | 19.45 | C |
| ATOM | 9165 | OG  | SER A 651 | 16.010 | 44.765 | -14.511 | 1.00 | 20.60 | O |
| ATOM | 9167 | C   | SER A 651 | 15.783 | 48.180 | -13.044 | 1.00 | 17.99 | C |
| ATOM | 9168 | O   | SER A 651 | 14.717 | 48.529 | -13.565 | 1.00 | 18.15 | O |
| ATOM | 9170 | N   | SER A 652 | 16.396 | 48.919 | -12.112 | 1.00 | 16.12 | N |
| ATOM | 9171 | CA  | SER A 652 | 15.809 | 50.148 | -11.663 | 1.00 | 15.97 | C |
| ATOM | 9173 | CB  | SER A 652 | 16.691 | 50.836 | -10.614 | 1.00 | 16.24 | C |
| ATOM | 9176 | OG  | SER A 652 | 16.176 | 52.110 | -10.383 | 1.00 | 18.93 | O |
| ATOM | 9178 | C   | SER A 652 | 15.623 | 51.110 | -12.854 | 1.00 | 15.08 | C |
| ATOM | 9179 | O   | SER A 652 | 16.530 | 51.272 | -13.672 | 1.00 | 14.37 | O |
| ATOM | 9181 | N   | PRO A 653 | 14.485 | 51.812 | -12.900 | 1.00 | 15.66 | N |
| ATOM | 9182 | CA  | PRO A 653 | 14.280 | 52.802 | -13.946 | 1.00 | 15.59 | C |
| ATOM | 9184 | CB  | PRO A 653 | 12.840 | 53.227 | -13.765 | 1.00 | 15.67 | C |
| ATOM | 9187 | CG  | PRO A 653 | 12.563 | 52.997 | -12.313 | 1.00 | 16.68 | C |
| ATOM | 9190 | CD  | PRO A 653 | 13.365 | 51.769 | -11.950 | 1.00 | 16.28 | C |
| ATOM | 9193 | C   | PRO A 653 | 15.232 | 53.961 | -13.805 | 1.00 | 15.28 | C |
| ATOM | 9194 | O   | PRO A 653 | 15.476 | 54.645 | -14.795 | 1.00 | 17.21 | O |
| ATOM | 9195 | N   | ALA A 654 | 15.808 | 54.181 | -12.609 | 1.00 | 15.40 | N |
| ATOM | 9196 | CA  | ALA A 654 | 16.886 | 55.147 | -12.470 | 1.00 | 14.87 | C |
| ATOM | 9198 | CB  | ALA A 654 | 17.471 | 55.133 | -11.036 | 1.00 | 14.85 | C |
| ATOM | 9202 | C   | ALA A 654 | 17.999 | 54.956 | -13.511 | 1.00 | 15.59 | C |
| ATOM | 9203 | O   | ALA A 654 | 18.605 | 55.936 | -13.970 | 1.00 | 15.37 | O |
| ATOM | 9205 | N   | LEU A 655 | 18.270 | 53.704 | -13.868 | 1.00 | 15.14 | N |
| ATOM | 9206 | CA  | LEU A 655 | 19.331 | 53.388 | -14.817 | 1.00 | 16.53 | C |
| ATOM | 9208 | CB  | LEU A 655 | 19.681 | 51.905 | -14.788 | 1.00 | 16.59 | C |
| ATOM | 9211 | CG  | LEU A 655 | 20.139 | 51.339 | -13.435 | 1.00 | 16.83 | C |
| ATOM | 9213 | CD1 | LEU A 655 | 20.212 | 49.800 | -13.533 | 1.00 | 18.54 | C |
| ATOM | 9217 | CD2 | LEU A 655 | 21.460 | 51.963 | -13.013 | 1.00 | 19.36 | C |
| ATOM | 9221 | C   | LEU A 655 | 19.013 | 53.884 | -16.231 | 1.00 | 17.13 | C |
| ATOM | 9222 | O   | LEU A 655 | 19.912 | 53.952 | -17.072 | 1.00 | 18.65 | O |

| ATOM | 9224 | N | SER A 656 | 17.751 | 54.209 | -16.498 | 1.00 | 17.03 | N |
| --- | --- | --- | --- | --- | --- | --- | --- | --- | --- |
| ATOM | 9225 | CA | SER A 656 | 17.370 | 54.819 | -17.772 | 1.00 | 18.22 | C |
| ATOM | 9227 | CB | SER A 656 | 15.865 | 54.659 | -17.986 | 1.00 | 18.55 | C |
| ATOM | 9230 | OG | SER A 656 | 15.555 | 53.280 | -18.068 | 1.00 | 21.34 | O |
| ATOM | 9232 | C | SER A 656 | 17.745 | 56.321 | -17.894 | 1.00 | 17.95 | C |
| ATOM | 9233 | O | SER A 656 | 17.815 | 56.835 | -19.006 | 1.00 | 18.26 | O |
| ATOM | 9235 | N | TYR A 657 | 18.025 | 57.003 | -16.769 | 1.00 | 17.78 | N |
| ATOM | 9236 | CA | TYR A 657 | 18.174 | 58.464 | -16.770 | 1.00 | 17.40 | C |
| ATOM | 9238 | CB | TYR A 657 | 17.013 | 59.116 | -16.010 | 1.00 | 17.57 | C |
| ATOM | 9241 | CG | TYR A 657 | 15.642 | 58.661 | -16.468 | 1.00 | 18.66 | C |
| ATOM | 9242 | CD1 | TYR A 657 | 15.171 | 59.031 | -17.700 | 1.00 | 21.47 | C |
| ATOM | 9244 | CE1 | TYR A 657 | 13.931 | 58.592 | -18.162 | 1.00 | 21.89 | C |
| ATOM | 9246 | CZ | TYR A 657 | 13.140 | 57.791 | -17.358 | 1.00 | 19.53 | C |
| ATOM | 9247 | OH | TYR A 657 | 11.889 | 57.401 | -17.856 | 1.00 | 19.94 | O |
| ATOM | 9249 | CE2 | TYR A 657 | 13.585 | 57.401 | -16.105 | 1.00 | 19.65 | C |
| ATOM | 9251 | CD2 | TYR A 657 | 14.841 | 57.827 | -15.667 | 1.00 | 17.94 | C |
| ATOM | 9253 | C | TYR A 657 | 19.508 | 58.952 | -16.163 | 1.00 | 16.32 | C |
| ATOM | 9254 | O | TYR A 657 | 19.970 | 60.008 | -16.513 | 1.00 | 16.45 | O |
| ATOM | 9256 | N | LEU A 658 | 20.114 | 58.160 | -15.285 | 1.00 | 15.72 | N |
| ATOM | 9257 | CA | LEU A 658 | 21.384 | 58.530 | -14.674 | 1.00 | 15.43 | C |
| ATOM | 9259 | CB | LEU A 658 | 21.816 | 57.509 | -13.659 | 1.00 | 15.77 | C |
| ATOM | 9262 | CG | LEU A 658 | 21.221 | 57.490 | -12.265 | 1.00 | 18.96 | C |
| ATOM | 9264 | CD1 | LEU A 658 | 21.713 | 56.269 | -11.531 | 1.00 | 22.82 | C |
| ATOM | 9268 | CD2 | LEU A 658 | 21.651 | 58.688 | -11.516 | 1.00 | 19.47 | C |
| ATOM | 9272 | C | LEU A 658 | 22.457 | 58.599 | -15.734 | 1.00 | 14.43 | C |
| ATOM | 9273 | O | LEU A 658 | 22.485 | 57.795 | -16.649 | 1.00 | 14.01 | O |
| ATOM | 9275 | N | SER A 659 | 23.347 | 59.564 | -15.582 | 1.00 | 14.74 | N |
| ATOM | 9276 | CA | SER A 659 | 24.550 | 59.630 | -16.370 | 1.00 | 14.02 | C |
| ATOM | 9278 | CB | SER A 659 | 25.427 | 60.807 | -15.901 | 1.00 | 15.06 | C |
| ATOM | 9281 | OG | SER A 659 | 26.682 | 60.301 | -15.487 | 1.00 | 15.86 | O |
| ATOM | 9283 | C | SER A 659 | 25.308 | 58.294 | -16.219 | 1.00 | 14.00 | C |
| ATOM | 9284 | O | SER A 659 | 25.216 | 57.615 | -15.185 | 1.00 | 14.00 | O |
| ATOM | 9286 | N | PRO A 660 | 26.079 | 57.906 | -17.236 | 1.00 | 14.94 | N |
| ATOM | 9287 | CA | PRO A 660 | 26.769 | 56.598 | -17.148 | 1.00 | 14.13 | C |
| ATOM | 9289 | CB | PRO A 660 | 27.419 | 56.412 | -18.508 | 1.00 | 14.78 | C |
| ATOM | 9292 | CG | PRO A 660 | 27.364 | 57.736 | -19.170 | 1.00 | 16.22 | C |
| ATOM | 9295 | CD | PRO A 660 | 26.333 | 58.598 | -18.515 | 1.00 | 15.93 | C |
| ATOM | 9298 | C | PRO A 660 | 27.832 | 56.545 | -16.067 | 1.00 | 15.03 | C |
| ATOM | 9299 | O | PRO A 660 | 28.053 | 55.495 | -15.479 | 1.00 | 15.86 | O |
| ATOM | 9300 | N | ARG A 661 | 28.447 | 57.683 | -15.776 | 1.00 | 15.36 | N |
| ATOM | 9301 | CA | ARG A 661 | 29.402 | 57.784 | -14.653 | 1.00 | 15.27 | C |
| ATOM | 9303 | CB | ARG A 661 | 30.279 | 59.032 | -14.818 | 1.00 | 14.59 | C |
| ATOM | 9306 | CG | ARG A 661 | 31.197 | 58.905 | -16.008 | 1.00 | 15.21 | C |
| ATOM | 9309 | CD | ARG A 661 | 31.980 | 60.194 | -16.320 | 1.00 | 17.55 | C |
| ATOM | 9312 | NE | ARG A 661 | 32.816 | 60.032 | -17.520 | 1.00 | 17.73 | N |
| ATOM | 9314 | CZ | ARG A 661 | 34.032 | 59.495 | -17.538 | 1.00 | 21.34 | C |
| ATOM | 9315 | NH1 | ARG A 661 | 34.591 | 59.028 | -16.433 | 1.00 | 21.75 | N |
| ATOM | 9318 | NH2 | ARG A 661 | 34.690 | 59.396 | -18.691 | 1.00 | 22.82 | N |
| ATOM | 9321 | C | ARG A 661 | 28.708 | 57.774 | -13.288 | 1.00 | 15.42 | C |
| ATOM | 9322 | O | ARG A 661 | 29.181 | 57.151 | -12.359 | 1.00 | 16.25 | O |
| ATOM | 9324 | N | THR A 662 | 27.588 | 58.459 | -13.127 | 1.00 | 14.84 | N |
| ATOM | 9325 | CA | THR A 662 | 26.963 | 58.434 | -11.799 | 1.00 | 15.15 | C |
| ATOM | 9327 | CB | THR A 662 | 25.990 | 59.557 | -11.532 | 1.00 | 15.62 | C |
| ATOM | 9329 | OG1 | THR A 662 | 24.962 | 59.587 | -12.524 | 1.00 | 16.61 | O |
| ATOM | 9331 | CG2 | THR A 662 | 26.757 | 60.863 | -11.482 | 1.00 | 15.32 | C |
| ATOM | 9335 | C | THR A 662 | 26.274 | 57.115 | -11.538 | 1.00 | 15.21 | C |
| ATOM | 9336 | O | THR A 662 | 26.131 | 56.720 | -10.393 | 1.00 | 15.13 | O |

| ATOM | 9338 | N   | GLN | A | 663 | 25.869 | 56.422 | -12.607 | 1.00 | 16.05 | N |
|------|------|-----|-----|---|-----|--------|--------|---------|------|-------|---|
| ATOM | 9339 | CA  | GLN | A | 663 | 25.362 | 55.044 | -12.489 | 1.00 | 17.43 | C |
| ATOM | 9341 | CB  | GLN | A | 663 | 25.115 | 54.471 | -13.873 | 1.00 | 18.33 | C |
| ATOM | 9344 | CG  | GLN | A | 663 | 23.853 | 54.943 | -14.527 | 1.00 | 21.74 | C |
| ATOM | 9347 | CD  | GLN | A | 663 | 23.564 | 54.197 | -15.799 | 1.00 | 21.58 | C |
| ATOM | 9348 | OE1 | GLN | A | 663 | 23.853 | 52.985 | -15.914 | 1.00 | 29.33 | O |
| ATOM | 9349 | NE2 | GLN | A | 663 | 22.998 | 54.901 | -16.777 | 1.00 | 23.45 | N |
| ATOM | 9352 | C   | GLN | A | 663 | 26.358 | 54.115 | -11.745 | 1.00 | 17.09 | C |
| ATOM | 9353 | O   | GLN | A | 663 | 25.970 | 53.154 | -11.058 | 1.00 | 15.76 | O |
| ATOM | 9355 | N   | ILE | A | 664 | 27.649 | 54.404 | -11.877 | 1.00 | 15.70 | N |
| ATOM | 9356 | CA  | ILE | A | 664 | 28.677 | 53.620 | -11.238 | 1.00 | 16.11 | C |
| ATOM | 9358 | CB  | ILE | A | 664 | 30.083 | 54.143 | -11.679 | 1.00 | 15.75 | C |
| ATOM | 9360 | CG1 | ILE | A | 664 | 30.265 | 53.892 | -13.186 | 1.00 | 17.12 | C |
| ATOM | 9363 | CD1 | ILE | A | 664 | 31.494 | 54.549 | -13.743 | 1.00 | 17.56 | C |
| ATOM | 9367 | CG2 | ILE | A | 664 | 31.214 | 53.517 | -10.820 | 1.00 | 17.62 | C |
| ATOM | 9371 | C   | ILE | A | 664 | 28.519 | 53.661 | -9.689  | 1.00 | 16.05 | C |
| ATOM | 9372 | O   | ILE | A | 664 | 28.604 | 52.625 | -9.024  | 1.00 | 15.60 | O |
| ATOM | 9374 | N   | LEU | A | 665 | 28.331 | 54.846 | -9.127  | 1.00 | 14.93 | N |
| ATOM | 9375 | CA  | LEU | A | 665 | 28.168 | 54.964 | -7.691  | 1.00 | 14.25 | C |
| ATOM | 9377 | CB  | LEU | A | 665 | 28.342 | 56.435 | -7.267  | 1.00 | 14.43 | C |
| ATOM | 9380 | CG  | LEU | A | 665 | 28.400 | 56.692 | -5.765  | 1.00 | 14.45 | C |
| ATOM | 9382 | CD1 | LEU | A | 665 | 29.272 | 55.705 | -5.099  | 1.00 | 16.42 | C |
| ATOM | 9386 | CD2 | LEU | A | 665 | 28.827 | 58.107 | -5.472  | 1.00 | 16.30 | C |
| ATOM | 9390 | C   | LEU | A | 665 | 26.792 | 54.405 | -7.264  | 1.00 | 15.16 | C |
| ATOM | 9391 | O   | LEU | A | 665 | 26.643 | 53.781 | -6.217  | 1.00 | 14.37 | O |
| ATOM | 9393 | N   | TYR | A | 666 | 25.776 | 54.639 | -8.079  | 1.00 | 15.36 | N |
| ATOM | 9394 | CA  | TYR | A | 666 | 24.448 | 54.110 | -7.788  | 1.00 | 15.47 | C |
| ATOM | 9396 | CB  | TYR | A | 666 | 23.481 | 54.524 | -8.911  | 1.00 | 15.60 | C |
| ATOM | 9399 | CG  | TYR | A | 666 | 22.073 | 54.018 | -8.739  | 1.00 | 16.42 | C |
| ATOM | 9400 | CD1 | TYR | A | 666 | 21.088 | 54.826 | -8.171  | 1.00 | 15.89 | C |
| ATOM | 9402 | CE1 | TYR | A | 666 | 19.791 | 54.371 | -8.027  | 1.00 | 14.96 | C |
| ATOM | 9404 | CZ  | TYR | A | 666 | 19.470 | 53.077 | -8.462  | 1.00 | 15.27 | C |
| ATOM | 9405 | OH  | TYR | A | 666 | 18.164 | 52.598 | -8.298  | 1.00 | 16.95 | O |
| ATOM | 9407 | CE2 | TYR | A | 666 | 20.439 | 52.261 | -9.031  | 1.00 | 16.37 | C |
| ATOM | 9409 | CD2 | TYR | A | 666 | 21.733 | 52.747 | -9.169  | 1.00 | 17.89 | C |
| ATOM | 9411 | C   | TYR | A | 666 | 24.517 | 52.584 | -7.655  | 1.00 | 14.92 | C |
| ATOM | 9412 | O   | TYR | A | 666 | 24.023 | 52.028 | -6.689  | 1.00 | 15.54 | O |
| ATOM | 9414 | N   | ALA | A | 667 | 25.141 | 51.913 | -8.624  | 1.00 | 15.49 | N |
| ATOM | 9415 | CA  | ALA | A | 667 | 25.275 | 50.452 | -8.602  | 1.00 | 14.71 | C |
| ATOM | 9417 | CB  | ALA | A | 667 | 25.862 | 49.969 | -9.898  | 1.00 | 15.46 | C |
| ATOM | 9421 | C   | ALA | A | 667 | 26.153 | 49.970 | -7.416  | 1.00 | 14.22 | C |
| ATOM | 9422 | O   | ALA | A | 667 | 25.831 | 48.994 | -6.752  | 1.00 | 13.34 | O |
| ATOM | 9424 | N   | PHE | A | 668 | 27.205 | 50.717 | -7.097  | 1.00 | 13.84 | N |
| ATOM | 9425 | CA  | PHE | A | 668 | 28.055 | 50.327 | -5.971  | 1.00 | 13.01 | C |
| ATOM | 9427 | CB  | PHE | A | 668 | 29.205 | 51.308 | -5.804  | 1.00 | 13.13 | C |
| ATOM | 9430 | CG  | PHE | A | 668 | 30.049 | 51.044 | -4.592  | 1.00 | 14.16 | C |
| ATOM | 9431 | CD1 | PHE | A | 668 | 30.842 | 49.889 | -4.519  | 1.00 | 14.42 | C |
| ATOM | 9433 | CE1 | PHE | A | 668 | 31.595 | 49.654 | -3.393  | 1.00 | 13.94 | C |
| ATOM | 9435 | CZ  | PHE | A | 668 | 31.598 | 50.574 | -2.365  | 1.00 | 14.16 | C |
| ATOM | 9437 | CE2 | PHE | A | 668 | 30.833 | 51.732 | -2.440  | 1.00 | 14.08 | C |
| ATOM | 9439 | CD2 | PHE | A | 668 | 30.079 | 51.961 | -3.555  | 1.00 | 13.46 | C |
| ATOM | 9441 | C   | PHE | A | 668 | 27.228 | 50.232 | -4.690  | 1.00 | 12.86 | C |
| ATOM | 9442 | O   | PHE | A | 668 | 27.277 | 49.247 | -3.959  | 1.00 | 13.52 | O |
| ATOM | 9444 | N   | VAL | A | 669 | 26.434 | 51.244 | -4.415  | 1.00 | 12.19 | N |
| ATOM | 9445 | CA  | VAL | A | 669 | 25.652 | 51.240 | -3.181  | 1.00 | 13.07 | C |
| ATOM | 9447 | CB  | VAL | A | 669 | 25.166 | 52.646 | -2.838  | 1.00 | 13.49 | C |
| ATOM | 9449 | CG1 | VAL | A | 669 | 24.371 | 52.655 | -1.581  | 1.00 | 14.68 | C |

| ATOM | 9453 | CG2 | VAL A 669 | 26.362 | 53.600 | -2.692 | 1.00 | 13.98 | C |
| --- | --- | --- | --- | --- | --- | --- | --- | --- | --- |
| ATOM | 9457 | C | VAL A 669 | 24.477 | 50.285 | -3.233 | 1.00 | 13.39 | C |
| ATOM | 9458 | O | VAL A 669 | 24.278 | 49.513 | -2.303 | 1.00 | 13.31 | O |
| ATOM | 9460 | N | ARG A 670 | 23.694 | 50.344 | -4.315 | 1.00 | 13.75 | N |
| ATOM | 9461 | CA | ARG A 670 | 22.481 | 49.505 | -4.452 | 1.00 | 14.02 | C |
| ATOM | 9463 | CB | ARG A 670 | 21.621 | 49.964 | -5.649 | 1.00 | 14.67 | C |
| ATOM | 9466 | CG | ARG A 670 | 20.944 | 51.334 | -5.448 | 1.00 | 14.45 | C |
| ATOM | 9469 | CD | ARG A 670 | 19.601 | 51.181 | -4.750 | 1.00 | 14.73 | C |
| ATOM | 9472 | NE | ARG A 670 | 18.831 | 52.427 | -4.560 | 1.00 | 14.78 | N |
| ATOM | 9474 | CZ | ARG A 670 | 18.840 | 53.176 | -3.462 | 1.00 | 14.42 | C |
| ATOM | 9475 | NH1 | ARG A 670 | 19.639 | 52.853 | -2.446 | 1.00 | 16.45 | N |
| ATOM | 9478 | NH2 | ARG A 670 | 18.069 | 54.281 | -3.358 | 1.00 | 13.02 | N |
| ATOM | 9481 | C | ARG A 670 | 22.811 | 48.029 | -4.580 | 1.00 | 14.04 | C |
| ATOM | 9482 | O | ARG A 670 | 22.113 | 47.198 | -4.004 | 1.00 | 15.33 | O |
| ATOM | 9484 | N | GLU A 671 | 23.872 | 47.718 | -5.331 | 1.00 | 14.89 | N |
| ATOM | 9485 | CA | GLU A 671 | 24.238 | 46.341 | -5.585 | 1.00 | 14.40 | C |
| ATOM | 9487 | CB | GLU A 671 | 24.636 | 46.105 | -7.061 | 1.00 | 14.76 | C |
| ATOM | 9490 | CG | GLU A 671 | 23.619 | 46.612 | -8.074 | 1.00 | 16.25 | C |
| ATOM | 9493 | CD | GLU A 671 | 22.155 | 46.247 | -7.738 | 1.00 | 15.43 | C |
| ATOM | 9494 | OE1 | GLU A 671 | 21.886 | 45.143 | -7.232 | 1.00 | 20.87 | O |
| ATOM | 9495 | OE2 | GLU A 671 | 21.272 | 47.094 | -8.008 | 1.00 | 18.09 | O |
| ATOM | 9496 | C | GLU A 671 | 25.342 | 45.846 | -4.627 | 1.00 | 15.73 | C |
| ATOM | 9497 | O | GLU A 671 | 25.113 | 44.936 | -3.831 | 1.00 | 15.94 | O |
| ATOM | 9499 | N | GLU A 672 | 26.528 | 46.435 | -4.682 | 1.00 | 15.89 | N |
| ATOM | 9500 | CA | GLU A 672 | 27.631 | 45.889 | -3.891 | 1.00 | 16.54 | C |
| ATOM | 9502 | CB | GLU A 672 | 28.969 | 46.516 | -4.300 | 1.00 | 15.76 | C |
| ATOM | 9505 | CG | GLU A 672 | 29.449 | 46.037 | -5.637 | 1.00 | 19.61 | C |
| ATOM | 9508 | CD | GLU A 672 | 30.866 | 46.517 | -5.948 | 1.00 | 19.99 | C |
| ATOM | 9509 | OE1 | GLU A 672 | 31.818 | 46.025 | -5.287 | 1.00 | 21.36 | O |
| ATOM | 9510 | OE2 | GLU A 672 | 30.996 | 47.390 | -6.840 | 1.00 | 23.96 | O |
| ATOM | 9511 | C | GLU A 672 | 27.411 | 46.014 | -2.377 | 1.00 | 16.23 | C |
| ATOM | 9512 | O | GLU A 672 | 27.674 | 45.046 | -1.634 | 1.00 | 16.46 | O |
| ATOM | 9514 | N | LEU A 673 | 26.925 | 47.171 | -1.924 | 1.00 | 15.96 | N |
| ATOM | 9515 | CA | LEU A 673 | 26.623 | 47.367 | -0.495 | 1.00 | 15.89 | C |
| ATOM | 9517 | CB | LEU A 673 | 26.730 | 48.827 | -0.099 | 1.00 | 15.92 | C |
| ATOM | 9520 | CG | LEU A 673 | 28.062 | 49.509 | -0.371 | 1.00 | 15.11 | C |
| ATOM | 9522 | CD1 | LEU A 673 | 28.107 | 50.878 | 0.299 | 1.00 | 16.47 | C |
| ATOM | 9526 | CD2 | LEU A 673 | 29.268 | 48.630 | 0.038 | 1.00 | 15.46 | C |
| ATOM | 9530 | C | LEU A 673 | 25.242 | 46.829 | -0.105 | 1.00 | 15.79 | C |
| ATOM | 9531 | O | LEU A 673 | 24.958 | 46.660 | 1.096 | 1.00 | 16.11 | O |
| ATOM | 9533 | N | GLY A 674 | 24.379 | 46.605 | -1.092 | 1.00 | 14.39 | N |
| ATOM | 9534 | CA | GLY A 674 | 23.052 | 46.040 | -0.842 | 1.00 | 14.76 | C |
| ATOM | 9537 | C | GLY A 674 | 22.066 | 46.967 | -0.149 | 1.00 | 15.43 | C |
| ATOM | 9538 | O | GLY A 674 | 21.075 | 46.491 | 0.435 | 1.00 | 14.31 | O |
| ATOM | 9540 | N | VAL A 675 | 22.324 | 48.277 | -0.244 | 1.00 | 14.71 | N |
| ATOM | 9541 | CA | VAL A 675 | 21.486 | 49.321 | 0.358 | 1.00 | 13.67 | C |
| ATOM | 9543 | CB | VAL A 675 | 22.296 | 50.544 | 0.831 | 1.00 | 14.81 | C |
| ATOM | 9545 | CG1 | VAL A 675 | 21.356 | 51.626 | 1.261 | 1.00 | 14.07 | C |
| ATOM | 9549 | CG2 | VAL A 675 | 23.257 | 50.129 | 1.962 | 1.00 | 14.33 | C |
| ATOM | 9553 | C | VAL A 675 | 20.420 | 49.711 | -0.686 | 1.00 | 13.69 | C |
| ATOM | 9554 | O | VAL A 675 | 20.743 | 50.307 | -1.710 | 1.00 | 14.26 | O |
| ATOM | 9556 | N | LYS A 676 | 19.166 | 49.355 | -0.407 | 1.00 | 12.88 | N |
| ATOM | 9557 | CA | LYS A 676 | 18.106 | 49.501 | -1.376 | 1.00 | 13.09 | C |
| ATOM | 9559 | CB | LYS A 676 | 17.200 | 48.272 | -1.337 | 1.00 | 14.45 | C |
| ATOM | 9562 | CG | LYS A 676 | 17.932 | 46.954 | -1.474 | 1.00 | 13.39 | C |
| ATOM | 9565 | CD | LYS A 676 | 18.628 | 46.856 | -2.809 | 1.00 | 15.95 | C |
| ATOM | 9568 | CE | LYS A 676 | 19.241 | 45.490 | -3.038 | 1.00 | 15.49 | C |

| ATOM | 9571 | NZ | LYS A 676 | 19.885 | 45.409 | -4.384 | 1.00 | 13.67 | N |
|------|------|-----|-----------|--------|--------|--------|------|-------|---|
| ATOM | 9575 | C | LYS A 676 | 17.299 | 50.728 | -1.024 | 1.00 | 13.54 | C |
| ATOM | 9576 | O | LYS A 676 | 17.374 | 51.271 | 0.073 | 1.00 | 13.74 | O |
| ATOM | 9578 | N | ALA A 677 | 16.525 | 51.184 | -1.991 | 1.00 | 12.74 | N |
| ATOM | 9579 | CA | ALA A 677 | 15.497 | 52.177 | -1.699 | 1.00 | 12.90 | C |
| ATOM | 9581 | CB | ALA A 677 | 14.709 | 52.438 | -2.997 | 1.00 | 14.07 | C |
| ATOM | 9585 | C | ALA A 677 | 14.563 | 51.614 | -0.586 | 1.00 | 13.05 | C |
| ATOM | 9586 | O | ALA A 677 | 14.425 | 50.399 | -0.451 | 1.00 | 13.38 | O |
| ATOM | 9588 | N | ARG A 678 | 13.952 | 52.508 | 0.191 | 1.00 | 12.73 | N |
| ATOM | 9589 | CA | ARG A 678 | 13.144 | 52.156 | 1.357 | 1.00 | 12.82 | C |
| ATOM | 9591 | CB | ARG A 678 | 13.571 | 52.908 | 2.613 | 1.00 | 13.46 | C |
| ATOM | 9594 | CG | ARG A 678 | 13.047 | 52.298 | 3.877 | 1.00 | 12.87 | C |
| ATOM | 9597 | CD | ARG A 678 | 13.336 | 53.125 | 5.093 | 1.00 | 15.11 | C |
| ATOM | 9600 | NE | ARG A 678 | 12.944 | 52.389 | 6.287 | 1.00 | 13.62 | N |
| ATOM | 9602 | CZ | ARG A 678 | 13.700 | 51.494 | 6.921 | 1.00 | 14.06 | C |
| ATOM | 9603 | NH1 | ARG A 678 | 14.932 | 51.252 | 6.521 | 1.00 | 13.54 | N |
| ATOM | 9606 | NH2 | ARG A 678 | 13.179 | 50.847 | 7.956 | 1.00 | 14.98 | N |
| ATOM | 9609 | C | ARG A 678 | 11.714 | 52.508 | 1.062 | 1.00 | 12.97 | C |
| ATOM | 9610 | O | ARG A 678 | 11.402 | 53.661 | 0.761 | 1.00 | 12.45 | O |
| ATOM | 9612 | N | ARG A 679 | 10.826 | 51.527 | 1.157 | 1.00 | 13.41 | N |
| ATOM | 9613 | CA | ARG A 679 | 9.430 | 51.750 | 0.780 | 1.00 | 13.35 | C |
| ATOM | 9615 | CB | ARG A 679 | 8.759 | 50.455 | 0.295 | 1.00 | 13.60 | C |
| ATOM | 9618 | CG | ARG A 679 | 7.457 | 50.737 | -0.385 | 1.00 | 13.22 | C |
| ATOM | 9621 | CD | ARG A 679 | 6.912 | 49.563 | -1.209 | 1.00 | 13.59 | C |
| ATOM | 9624 | NE | ARG A 679 | 5.782 | 50.057 | -1.990 | 1.00 | 13.39 | N |
| ATOM | 9626 | CZ | ARG A 679 | 5.100 | 49.348 | -2.871 | 1.00 | 14.70 | C |
| ATOM | 9627 | NH1 | ARG A 679 | 5.391 | 48.065 | -3.061 | 1.00 | 13.34 | N |
| ATOM | 9630 | NH2 | ARG A 679 | 4.108 | 49.917 | -3.532 | 1.00 | 15.13 | N |
| ATOM | 9633 | C | ARG A 679 | 8.626 | 52.377 | 1.917 | 1.00 | 14.13 | C |
| ATOM | 9634 | O | ARG A 679 | 7.719 | 53.150 | 1.654 | 1.00 | 13.59 | O |
| ATOM | 9636 | N | GLY A 680 | 8.935 | 52.016 | 3.166 | 1.00 | 14.41 | N |
| ATOM | 9637 | CA | GLY A 680 | 8.216 | 52.566 | 4.326 | 1.00 | 13.75 | C |
| ATOM | 9640 | C | GLY A 680 | 7.685 | 51.495 | 5.276 | 1.00 | 13.53 | C |
| ATOM | 9641 | O | GLY A 680 | 6.882 | 50.630 | 4.869 | 1.00 | 14.03 | O |
| ATOM | 9643 | N | ASP A 681 | 8.096 | 51.562 | 6.537 | 1.00 | 13.21 | N |
| ATOM | 9644 | CA | ASP A 681 | 7.661 | 50.556 | 7.534 | 1.00 | 13.88 | C |
| ATOM | 9646 | CB | ASP A 681 | 8.208 | 50.877 | 8.919 | 1.00 | 12.92 | C |
| ATOM | 9649 | CG | ASP A 681 | 9.712 | 50.619 | 9.067 | 1.00 | 15.17 | C |
| ATOM | 9650 | OD1 | ASP A 681 | 10.400 | 50.192 | 8.112 | 1.00 | 14.74 | O |
| ATOM | 9651 | OD2 | ASP A 681 | 10.192 | 50.866 | 10.209 | 1.00 | 14.94 | O |
| ATOM | 9652 | C | ASP A 681 | 6.135 | 50.418 | 7.661 | 1.00 | 13.83 | C |
| ATOM | 9653 | O | ASP A 681 | 5.596 | 49.296 | 7.831 | 1.00 | 14.72 | O |
| ATOM | 9655 | N | VAL A 682 | 5.443 | 51.547 | 7.655 | 1.00 | 14.51 | N |
| ATOM | 9656 | CA | VAL A 682 | 3.978 | 51.544 | 7.815 | 1.00 | 14.92 | C |
| ATOM | 9658 | CB | VAL A 682 | 3.434 | 52.929 | 8.140 | 1.00 | 15.13 | C |
| ATOM | 9660 | CG1 | VAL A 682 | 1.939 | 52.925 | 8.106 | 1.00 | 15.37 | C |
| ATOM | 9664 | CG2 | VAL A 682 | 3.924 | 53.355 | 9.489 | 1.00 | 14.35 | C |
| ATOM | 9668 | C | VAL A 682 | 3.325 | 50.966 | 6.550 | 1.00 | 14.96 | C |
| ATOM | 9669 | O | VAL A 682 | 2.467 | 50.100 | 6.647 | 1.00 | 14.16 | O |
| ATOM | 9671 | N | PHE A 683 | 3.722 | 51.429 | 5.374 | 1.00 | 15.24 | N |
| ATOM | 9672 | CA | PHE A 683 | 3.171 | 50.824 | 4.149 | 1.00 | 14.90 | C |
| ATOM | 9674 | CB | PHE A 683 | 3.802 | 51.391 | 2.876 | 1.00 | 15.41 | C |
| ATOM | 9677 | CG | PHE A 683 | 3.284 | 50.723 | 1.625 | 1.00 | 15.06 | C |
| ATOM | 9678 | CD1 | PHE A 683 | 2.124 | 51.177 | 1.009 | 1.00 | 17.41 | C |
| ATOM | 9680 | CE1 | PHE A 683 | 1.627 | 50.531 | -0.139 | 1.00 | 15.73 | C |
| ATOM | 9682 | CZ | PHE A 683 | 2.313 | 49.454 | -0.662 | 1.00 | 15.81 | C |
| ATOM | 9684 | CE2 | PHE A 683 | 3.446 | 48.990 | -0.053 | 1.00 | 17.27 | C |

| ATOM | 9686 | CD2 | PHE A 683 | 3.943 | 49.638 | 1.081 | 1.00 | 17.45 | C |
| --- | --- | --- | --- | --- | --- | --- | --- | --- | --- |
| ATOM | 9688 | C | PHE A 683 | 3.338 | 49.298 | 4.103 | 1.00 | 15.41 | C |
| ATOM | 9689 | O | PHE A 683 | 2.416 | 48.563 | 3.778 | 1.00 | 15.02 | O |
| ATOM | 9691 | N | LEU A 684 | 4.544 | 48.841 | 4.422 | 1.00 | 15.64 | N |
| ATOM | 9692 | CA | LEU A 684 | 4.882 | 47.412 | 4.394 | 1.00 | 15.37 | C |
| ATOM | 9694 | CB | LEU A 684 | 6.394 | 47.267 | 4.455 | 1.00 | 14.93 | C |
| ATOM | 9697 | CG | LEU A 684 | 7.132 | 47.777 | 3.242 | 1.00 | 14.97 | C |
| ATOM | 9699 | CD1 | LEU A 684 | 8.647 | 47.675 | 3.494 | 1.00 | 18.07 | C |
| ATOM | 9703 | CD2 | LEU A 684 | 6.710 | 47.008 | 2.016 | 1.00 | 17.91 | C |
| ATOM | 9707 | C | LEU A 684 | 4.292 | 46.579 | 5.528 | 1.00 | 15.41 | C |
| ATOM | 9708 | O | LEU A 684 | 4.269 | 45.347 | 5.460 | 1.00 | 15.13 | O |
| ATOM | 9710 | N | GLY A 685 | 3.865 | 47.244 | 6.591 | 1.00 | 15.44 | N |
| ATOM | 9711 | CA | GLY A 685 | 3.377 | 46.572 | 7.780 | 1.00 | 15.54 | C |
| ATOM | 9714 | C | GLY A 685 | 4.513 | 45.867 | 8.480 | 1.00 | 16.66 | C |
| ATOM | 9715 | O | GLY A 685 | 4.302 | 44.846 | 9.152 | 1.00 | 16.17 | O |
| ATOM | 9717 | N | LYS A 686 | 5.725 | 46.392 | 8.342 | 1.00 | 16.77 | N |
| ATOM | 9718 | CA | LYS A 686 | 6.822 | 45.813 | 9.096 | 1.00 | 18.86 | C |
| ATOM | 9720 | CB | LYS A 686 | 7.341 | 44.551 | 8.442 | 1.00 | 19.95 | C |
| ATOM | 9723 | CG | LYS A 686 | 8.164 | 44.742 | 7.218 | 1.00 | 21.43 | C |
| ATOM | 9726 | CD | LYS A 686 | 8.919 | 43.451 | 6.837 | 1.00 | 23.18 | C |
| ATOM | 9729 | CE | LYS A 686 | 10.139 | 43.209 | 7.669 | 1.00 | 26.57 | C |
| ATOM | 9732 | NZ | LYS A 686 | 10.897 | 42.073 | 7.044 | 1.00 | 27.84 | N |
| ATOM | 9736 | C | LYS A 686 | 7.967 | 46.753 | 9.328 | 1.00 | 17.94 | C |
| ATOM | 9737 | O | LYS A 686 | 8.251 | 47.600 | 8.507 | 1.00 | 17.04 | O |
| ATOM | 9739 | N | GLN A 687 | 8.646 | 46.527 | 10.435 | 1.00 | 16.57 | N |
| ATOM | 9740 | CA | GLN A 687 | 9.745 | 47.375 | 10.868 | 1.00 | 16.92 | C |
| ATOM | 9742 | CB | GLN A 687 | 9.764 | 47.482 | 12.376 | 1.00 | 16.63 | C |
| ATOM | 9745 | CG | GLN A 687 | 8.555 | 48.287 | 12.862 | 1.00 | 17.77 | C |
| ATOM | 9748 | CD | GLN A 687 | 8.514 | 48.427 | 14.346 | 1.00 | 17.92 | C |
| ATOM | 9749 | OE1 | GLN A 687 | 8.238 | 47.464 | 15.064 | 1.00 | 22.71 | O |
| ATOM | 9750 | NE2 | GLN A 687 | 8.774 | 49.639 | 14.831 | 1.00 | 14.46 | N |
| ATOM | 9753 | C | GLN A 687 | 11.014 | 46.801 | 10.313 | 1.00 | 16.43 | C |
| ATOM | 9754 | O | GLN A 687 | 11.618 | 45.939 | 10.910 | 1.00 | 18.01 | O |
| ATOM | 9756 | N | GLU A 688 | 11.416 | 47.302 | 9.151 | 1.00 | 16.21 | N |
| ATOM | 9757 | CA | GLU A 688 | 12.600 | 46.782 | 8.471 | 1.00 | 15.33 | C |
| ATOM | 9759 | CB | GLU A 688 | 12.650 | 47.296 | 7.047 | 1.00 | 15.15 | C |
| ATOM | 9762 | CG | GLU A 688 | 11.440 | 46.863 | 6.166 | 1.00 | 15.36 | C |
| ATOM | 9765 | CD | GLU A 688 | 11.749 | 47.000 | 4.669 | 1.00 | 17.15 | C |
| ATOM | 9766 | OE1 | GLU A 688 | 11.908 | 48.150 | 4.166 | 1.00 | 16.11 | O |
| ATOM | 9767 | OE2 | GLU A 688 | 11.788 | 45.935 | 3.985 | 1.00 | 18.20 | O |
| ATOM | 9768 | C | GLU A 688 | 13.871 | 47.224 | 9.176 | 1.00 | 14.94 | C |
| ATOM | 9769 | O | GLU A 688 | 13.874 | 48.186 | 9.932 | 1.00 | 15.75 | O |
| ATOM | 9771 | N | VAL A 689 | 14.956 | 46.545 | 8.838 | 1.00 | 14.23 | N |
| ATOM | 9772 | CA | VAL A 689 | 16.308 | 46.961 | 9.219 | 1.00 | 14.04 | C |
| ATOM | 9774 | CB | VAL A 689 | 17.368 | 46.200 | 8.368 | 1.00 | 14.36 | C |
| ATOM | 9776 | CG1 | VAL A 689 | 18.721 | 46.879 | 8.432 | 1.00 | 14.74 | C |
| ATOM | 9780 | CG2 | VAL A 689 | 17.457 | 44.687 | 8.814 | 1.00 | 14.89 | C |
| ATOM | 9784 | C | VAL A 689 | 16.430 | 48.470 | 9.017 | 1.00 | 13.56 | C |
| ATOM | 9785 | O | VAL A 689 | 15.991 | 49.016 | 8.020 | 1.00 | 13.65 | O |
| ATOM | 9787 | N | THR A 690 | 16.966 | 49.129 | 10.017 | 1.00 | 12.57 | N |
| ATOM | 9788 | CA | THR A 690 | 16.827 | 50.575 | 10.099 | 1.00 | 12.61 | C |
| ATOM | 9790 | CB | THR A 690 | 17.269 | 51.083 | 11.480 | 1.00 | 13.60 | C |
| ATOM | 9792 | OG1 | THR A 690 | 18.670 | 50.796 | 11.643 | 1.00 | 14.08 | O |
| ATOM | 9794 | CG2 | THR A 690 | 16.468 | 50.455 | 12.644 | 1.00 | 13.72 | C |
| ATOM | 9798 | C | THR A 690 | 17.594 | 51.315 | 9.033 | 1.00 | 13.20 | C |
| ATOM | 9799 | O | THR A 690 | 18.602 | 50.859 | 8.483 | 1.00 | 12.04 | O |
| ATOM | 9801 | N | ILE A 691 | 17.143 | 52.551 | 8.835 | 1.00 | 13.05 | N |

| | | | | | | | | | |
|---|---|---|---|---|---|---|---|---|---|
| ATOM | 9802 | CA | ILE A 691 | 17.823 | 53.531 | 7.983 | 1.00 | 12.96 | C |
| ATOM | 9804 | CB | ILE A 691 | 17.115 | 54.855 | 8.135 | 1.00 | 13.53 | C |
| ATOM | 9806 | CG1 | ILE A 691 | 15.717 | 54.803 | 7.512 | 1.00 | 13.68 | C |
| ATOM | 9809 | CD1 | ILE A 691 | 14.810 | 55.930 | 7.917 | 1.00 | 13.22 | C |
| ATOM | 9813 | CG2 | ILE A 691 | 17.956 | 55.968 | 7.549 | 1.00 | 14.07 | C |
| ATOM | 9817 | C | ILE A 691 | 19.298 | 53.641 | 8.431 | 1.00 | 13.09 | C |
| ATOM | 9818 | O | ILE A 691 | 20.253 | 53.604 | 7.593 | 1.00 | 13.55 | O |
| ATOM | 9820 | N | GLY A 692 | 19.503 | 53.724 | 9.741 | 1.00 | 12.78 | N |
| ATOM | 9821 | CA | GLY A 692 | 20.856 | 53.863 | 10.312 | 1.00 | 14.13 | C |
| ATOM | 9824 | C | GLY A 692 | 21.771 | 52.697 | 9.974 | 1.00 | 13.43 | C |
| ATOM | 9825 | O | GLY A 692 | 22.941 | 52.885 | 9.621 | 1.00 | 13.60 | O |
| ATOM | 9827 | N | SER A 693 | 21.229 | 51.480 | 10.049 | 1.00 | 13.03 | N |
| ATOM | 9828 | CA | SER A 693 | 21.968 | 50.288 | 9.659 | 1.00 | 13.31 | C |
| ATOM | 9830 | CB | SER A 693 | 21.118 | 49.023 | 9.853 | 1.00 | 13.63 | C |
| ATOM | 9833 | OG | SER A 693 | 20.895 | 48.766 | 11.246 | 1.00 | 15.71 | O |
| ATOM | 9835 | C | SER A 693 | 22.470 | 50.391 | 8.210 | 1.00 | 13.72 | C |
| ATOM | 9836 | O | SER A 693 | 23.587 | 50.000 | 7.888 | 1.00 | 13.74 | O |
| ATOM | 9838 | N | ASN A 694 | 21.628 | 50.936 | 7.337 | 1.00 | 13.52 | N |
| ATOM | 9839 | CA | ASN A 694 | 21.974 | 51.072 | 5.941 | 1.00 | 13.33 | C |
| ATOM | 9841 | CB | ASN A 694 | 20.712 | 51.229 | 5.117 | 1.00 | 13.48 | C |
| ATOM | 9844 | CG | ASN A 694 | 19.903 | 49.940 | 5.081 | 1.00 | 15.97 | C |
| ATOM | 9845 | OD1 | ASN A 694 | 20.487 | 48.870 | 4.891 | 1.00 | 21.14 | O |
| ATOM | 9846 | ND2 | ASN A 694 | 18.588 | 50.015 | 5.269 | 1.00 | 17.15 | N |
| ATOM | 9849 | C | ASN A 694 | 22.984 | 52.198 | 5.712 | 1.00 | 11.86 | C |
| ATOM | 9850 | O | ASN A 694 | 23.951 | 52.024 | 4.996 | 1.00 | 12.06 | O |
| ATOM | 9852 | N | VAL A 695 | 22.763 | 53.370 | 6.290 | 1.00 | 12.68 | N |
| ATOM | 9853 | CA | VAL A 695 | 23.760 | 54.415 | 6.232 | 1.00 | 12.33 | C |
| ATOM | 9855 | CB | VAL A 695 | 23.282 | 55.670 | 7.027 | 1.00 | 12.76 | C |
| ATOM | 9857 | CG1 | VAL A 695 | 24.357 | 56.727 | 7.059 | 1.00 | 14.57 | C |
| ATOM | 9861 | CG2 | VAL A 695 | 22.054 | 56.243 | 6.406 | 1.00 | 12.66 | C |
| ATOM | 9865 | C | VAL A 695 | 25.118 | 53.903 | 6.773 | 1.00 | 12.19 | C |
| ATOM | 9866 | O | VAL A 695 | 26.153 | 54.232 | 6.233 | 1.00 | 13.63 | O |
| ATOM | 9868 | N | SER A 696 | 25.099 | 53.075 | 7.833 | 1.00 | 12.17 | N |
| ATOM | 9869 | CA | SER A 696 | 26.334 | 52.525 | 8.407 | 1.00 | 12.47 | C |
| ATOM | 9871 | CB | SER A 696 | 26.043 | 51.683 | 9.651 | 1.00 | 13.38 | C |
| ATOM | 9874 | OG | SER A 696 | 25.424 | 52.496 | 10.653 | 1.00 | 12.23 | O |
| ATOM | 9876 | C | SER A 696 | 27.122 | 51.693 | 7.392 | 1.00 | 13.60 | C |
| ATOM | 9877 | O | SER A 696 | 28.347 | 51.770 | 7.318 | 1.00 | 12.39 | O |
| ATOM | 9879 | N | LYS A 697 | 26.417 | 50.967 | 6.532 | 1.00 | 13.08 | N |
| ATOM | 9880 | CA | LYS A 697 | 27.120 | 50.212 | 5.495 | 1.00 | 14.09 | C |
| ATOM | 9882 | CB | LYS A 697 | 26.145 | 49.375 | 4.651 | 1.00 | 14.64 | C |
| ATOM | 9885 | CG | LYS A 697 | 25.526 | 48.209 | 5.374 | 1.00 | 16.62 | C |
| ATOM | 9891 | C | LYS A 697 | 27.879 | 51.111 | 4.539 | 1.00 | 13.41 | C |
| ATOM | 9892 | O | LYS A 697 | 28.996 | 50.790 | 4.111 | 1.00 | 13.95 | O |
| ATOM | 9894 | N | ILE A 698 | 27.234 | 52.217 | 4.181 | 1.00 | 12.34 | N |
| ATOM | 9895 | CA | ILE A 698 | 27.847 | 53.205 | 3.340 | 1.00 | 12.26 | C |
| ATOM | 9897 | CB | ILE A 698 | 26.821 | 54.289 | 2.859 | 1.00 | 12.02 | C |
| ATOM | 9899 | CG1 | ILE A 698 | 25.650 | 53.639 | 2.078 | 1.00 | 12.69 | C |
| ATOM | 9902 | CD1 | ILE A 698 | 24.557 | 54.694 | 1.714 | 1.00 | 12.85 | C |
| ATOM | 9906 | CG2 | ILE A 698 | 27.571 | 55.423 | 2.017 | 1.00 | 12.89 | C |
| ATOM | 9910 | C | ILE A 698 | 29.044 | 53.857 | 4.063 | 1.00 | 12.42 | C |
| ATOM | 9911 | O | ILE A 698 | 30.123 | 53.934 | 3.503 | 1.00 | 12.68 | O |
| ATOM | 9913 | N | TYR A 699 | 28.858 | 54.291 | 5.307 | 1.00 | 12.18 | N |
| ATOM | 9914 | CA | TYR A 699 | 29.955 | 54.847 | 6.116 | 1.00 | 12.27 | C |
| ATOM | 9916 | CB | TYR A 699 | 29.426 | 55.120 | 7.492 | 1.00 | 12.38 | C |
| ATOM | 9919 | CG | TYR A 699 | 30.434 | 55.399 | 8.544 | 1.00 | 12.81 | C |
| ATOM | 9920 | CD1 | TYR A 699 | 31.045 | 56.671 | 8.684 | 1.00 | 13.65 | C |

| ATOM | 9922 | CE1 | TYR A 699 | 31.972 | 56.915 | 9.725 | 1.00 | 15.10 | C |
|------|------|-----|-----------|--------|--------|-------|------|-------|---|
| ATOM | 9924 | CZ  | TYR A 699 | 32.271 | 55.871 | 10.578 | 1.00 | 12.57 | C |
| ATOM | 9925 | OH  | TYR A 699 | 33.160 | 56.110 | 11.617 | 1.00 | 15.23 | O |
| ATOM | 9927 | CE2 | TYR A 699 | 31.666 | 54.616 | 10.433 | 1.00 | 14.58 | C |
| ATOM | 9929 | CD2 | TYR A 699 | 30.755 | 54.410 | 9.423 | 1.00 | 12.37 | C |
| ATOM | 9931 | C   | TYR A 699 | 31.130 | 53.902 | 6.186 | 1.00 | 11.92 | C |
| ATOM | 9932 | O   | TYR A 699 | 32.264 | 54.314 | 6.004 | 1.00 | 12.54 | O |
| ATOM | 9934 | N   | GLU A 700 | 30.859 | 52.615 | 6.440 | 1.00 | 11.67 | N |
| ATOM | 9935 | CA  | GLU A 700 | 31.941 | 51.624 | 6.487 | 1.00 | 12.94 | C |
| ATOM | 9937 | CB  | GLU A 700 | 31.429 | 50.271 | 6.982 | 1.00 | 12.78 | C |
| ATOM | 9940 | CG  | GLU A 700 | 31.062 | 50.352 | 8.466 | 1.00 | 16.06 | C |
| ATOM | 9943 | CD  | GLU A 700 | 30.323 | 49.155 | 9.042 | 1.00 | 16.92 | C |
| ATOM | 9944 | OE1 | GLU A 700 | 29.769 | 48.311 | 8.306 | 1.00 | 21.08 | O |
| ATOM | 9945 | OE2 | GLU A 700 | 30.295 | 49.073 | 10.291 | 1.00 | 18.93 | O |
| ATOM | 9946 | C   | GLU A 700 | 32.752 | 51.514 | 5.202 | 1.00 | 12.69 | C |
| ATOM | 9947 | O   | GLU A 700 | 33.967 | 51.396 | 5.263 | 1.00 | 14.36 | O |
| ATOM | 9949 | N   | ALA A 701 | 32.076 | 51.572 | 4.054 | 1.00 | 12.93 | N |
| ATOM | 9950 | CA  | ALA A 701 | 32.702 | 51.577 | 2.732 | 1.00 | 12.30 | C |
| ATOM | 9952 | CB  | ALA A 701 | 31.630 | 51.491 | 1.652 | 1.00 | 12.68 | C |
| ATOM | 9956 | C   | ALA A 701 | 33.571 | 52.767 | 2.460 | 1.00 | 13.14 | C |
| ATOM | 9957 | O   | ALA A 701 | 34.500 | 52.667 | 1.684 | 1.00 | 12.84 | O |
| ATOM | 9959 | N   | ILE A 702 | 33.228 | 53.917 | 3.037 | 1.00 | 13.64 | N |
| ATOM | 9960 | CA  | ILE A 702 | 34.016 | 55.107 | 2.950 | 1.00 | 14.14 | C |
| ATOM | 9962 | CB  | ILE A 702 | 33.222 | 56.352 | 3.369 | 1.00 | 13.53 | C |
| ATOM | 9964 | CG1 | ILE A 702 | 32.039 | 56.578 | 2.393 | 1.00 | 15.02 | C |
| ATOM | 9967 | CD1 | ILE A 702 | 31.045 | 57.672 | 2.792 | 1.00 | 15.09 | C |
| ATOM | 9971 | CG2 | ILE A 702 | 34.121 | 57.592 | 3.372 | 1.00 | 14.70 | C |
| ATOM | 9975 | C   | ILE A 702 | 35.247 | 54.952 | 3.839 | 1.00 | 14.36 | C |
| ATOM | 9976 | O   | ILE A 702 | 36.380 | 55.141 | 3.393 | 1.00 | 13.83 | O |
| ATOM | 9978 | N   | LYS A 703 | 35.029 | 54.590 | 5.097 | 1.00 | 14.83 | N |
| ATOM | 9979 | CA  | LYS A 703 | 36.163 | 54.503 | 6.030 | 1.00 | 15.81 | C |
| ATOM | 9981 | CB  | LYS A 703 | 35.687 | 54.226 | 7.462 | 1.00 | 16.39 | C |
| ATOM | 9984 | CG  | LYS A 703 | 34.819 | 55.296 | 8.085 | 1.00 | 18.47 | C |
| ATOM | 9987 | CD  | LYS A 703 | 35.610 | 56.519 | 8.514 | 1.00 | 23.31 | C |
| ATOM | 9990 | CE  | LYS A 703 | 36.335 | 56.275 | 9.892 | 1.00 | 25.30 | C |
| ATOM | 9993 | NZ  | LYS A 703 | 37.355 | 57.286 | 9.973 | 1.00 | 34.34 | N |
| ATOM | 9997 | C   | LYS A 703 | 37.203 | 53.450 | 5.633 | 1.00 | 14.94 | C |
| ATOM | 9998 | O   | LYS A 703 | 38.405 | 53.657 | 5.840 | 1.00 | 14.81 | O |
| ATOM | 10000 | N  | SER A 704 | 36.755 | 52.327 | 5.079 | 1.00 | 13.98 | N |
| ATOM | 10001 | CA | SER A 704 | 37.649 | 51.224 | 4.682 | 1.00 | 15.37 | C |
| ATOM | 10003 | CB | SER A 704 | 36.833 | 49.957 | 4.459 | 1.00 | 15.63 | C |
| ATOM | 10006 | OG | SER A 704 | 36.015 | 50.093 | 3.303 | 1.00 | 15.43 | O |
| ATOM | 10008 | C  | SER A 704 | 38.392 | 51.551 | 3.393 | 1.00 | 16.05 | C |
| ATOM | 10009 | O  | SER A 704 | 39.360 | 50.897 | 3.022 | 1.00 | 16.59 | O |
| ATOM | 10011 | N  | GLY A 705 | 37.922 | 52.558 | 2.681 | 1.00 | 15.67 | N |
| ATOM | 10012 | CA | GLY A 705 | 38.483 | 52.874 | 1.359 | 1.00 | 14.94 | C |
| ATOM | 10015 | C  | GLY A 705 | 37.889 | 52.076 | 0.208 | 1.00 | 13.81 | C |
| ATOM | 10016 | O  | GLY A 705 | 38.308 | 52.215 | -0.945 | 1.00 | 13.07 | O |
| ATOM | 10018 | N  | ARG A 706 | 36.933 | 51.198 | 0.480 | 1.00 | 12.80 | N |
| ATOM | 10019 | CA | ARG A 706 | 36.340 | 50.395 | -0.583 | 1.00 | 14.02 | C |
| ATOM | 10021 | CB | ARG A 706 | 35.267 | 49.524 | 0.018 | 1.00 | 14.09 | C |
| ATOM | 10024 | CG | ARG A 706 | 34.718 | 48.506 | -0.999 | 1.00 | 14.55 | C |
| ATOM | 10027 | CD | ARG A 706 | 33.583 | 47.701 | -0.460 | 1.00 | 16.34 | C |
| ATOM | 10030 | NE | ARG A 706 | 33.056 | 46.792 | -1.462 | 1.00 | 16.72 | N |
| ATOM | 10032 | CZ | ARG A 706 | 32.109 | 45.910 | -1.200 | 1.00 | 16.48 | C |
| ATOM | 10033 | NH1| ARG A 706 | 31.620 | 45.836 | 0.032 | 1.00 | 15.66 | N |
| ATOM | 10036 | NH2| ARG A 706 | 31.634 | 45.120 | -2.159 | 1.00 | 18.49 | N |

| ATOM | 10039 | C | ARG A 706 | 35.739 | 51.339 | -1.674 | 1.00 | 13.32 | C |
|---|---|---|---|---|---|---|---|---|---|
| ATOM | 10040 | O | ARG A 706 | 35.749 | 51.027 | -2.874 | 1.00 | 14.36 | O |
| ATOM | 10042 | N | ILE A 707 | 35.199 | 52.485 | -1.268 | 1.00 | 13.59 | N |
| ATOM | 10043 | CA | ILE A 707 | 34.614 | 53.423 | -2.227 | 1.00 | 13.05 | C |
| ATOM | 10045 | CB | ILE A 707 | 33.787 | 54.491 | -1.468 | 1.00 | 13.54 | C |
| ATOM | 10047 | CG1 | ILE A 707 | 32.799 | 55.215 | -2.405 | 1.00 | 15.01 | C |
| ATOM | 10050 | CD1 | ILE A 707 | 31.786 | 56.023 | -1.653 | 1.00 | 14.22 | C |
| ATOM | 10054 | CG2 | ILE A 707 | 34.723 | 55.522 | -0.820 | 1.00 | 14.46 | C |
| ATOM | 10058 | C | ILE A 707 | 35.645 | 54.141 | -3.140 | 1.00 | 13.26 | C |
| ATOM | 10059 | O | ILE A 707 | 35.303 | 54.695 | -4.160 | 1.00 | 14.66 | O |
| ATOM | 10061 | N | ASN A 708 | 36.915 | 54.119 | -2.753 | 1.00 | 13.42 | N |
| ATOM | 10062 | CA | ASN A 708 | 37.929 | 54.933 | -3.403 | 1.00 | 14.51 | C |
| ATOM | 10064 | CB | ASN A 708 | 39.276 | 54.789 | -2.698 | 1.00 | 14.56 | C |
| ATOM | 10067 | CG | ASN A 708 | 39.253 | 55.343 | -1.266 | 1.00 | 15.75 | C |
| ATOM | 10068 | OD1 | ASN A 708 | 38.306 | 56.001 | -0.880 | 1.00 | 14.20 | O |
| ATOM | 10069 | ND2 | ASN A 708 | 40.290 | 55.020 | -0.466 | 1.00 | 15.67 | N |
| ATOM | 10072 | C | ASN A 708 | 38.086 | 54.591 | -4.871 | 1.00 | 13.43 | C |
| ATOM | 10073 | O | ASN A 708 | 38.151 | 55.477 | -5.711 | 1.00 | 13.63 | O |
| ATOM | 10075 | N | ASN A 709 | 38.187 | 53.299 | -5.200 | 1.00 | 14.05 | N |
| ATOM | 10076 | CA | ASN A 709 | 38.334 | 52.915 | -6.633 | 1.00 | 15.07 | C |
| ATOM | 10078 | CB | ASN A 709 | 38.728 | 51.449 | -6.734 | 1.00 | 15.48 | C |
| ATOM | 10081 | CG | ASN A 709 | 40.168 | 51.239 | -6.423 | 1.00 | 20.57 | C |
| ATOM | 10082 | OD1 | ASN A 709 | 40.984 | 52.198 | -6.383 | 1.00 | 22.19 | O |
| ATOM | 10083 | ND2 | ASN A 709 | 40.533 | 49.976 | -6.230 | 1.00 | 25.66 | N |
| ATOM | 10086 | C | ASN A 709 | 37.071 | 53.225 | -7.444 | 1.00 | 14.33 | C |
| ATOM | 10087 | O | ASN A 709 | 37.112 | 53.396 | -8.666 | 1.00 | 15.65 | O |
| ATOM | 10089 | N | VAL A 710 | 35.951 | 53.276 | -6.754 | 1.00 | 15.01 | N |
| ATOM | 10090 | CA | VAL A 710 | 34.684 | 53.640 | -7.388 | 1.00 | 14.57 | C |
| ATOM | 10092 | CB | VAL A 710 | 33.478 | 53.364 | -6.447 | 1.00 | 14.35 | C |
| ATOM | 10094 | CG1 | VAL A 710 | 32.144 | 53.614 | -7.169 | 1.00 | 16.06 | C |
| ATOM | 10098 | CG2 | VAL A 710 | 33.544 | 51.970 | -5.901 | 1.00 | 17.11 | C |
| ATOM | 10102 | C | VAL A 710 | 34.725 | 55.101 | -7.833 | 1.00 | 13.82 | C |
| ATOM | 10103 | O | VAL A 710 | 34.357 | 55.442 | -8.970 | 1.00 | 13.85 | O |
| ATOM | 10105 | N | LEU A 711 | 35.158 | 55.967 | -6.909 | 1.00 | 14.05 | N |
| ATOM | 10106 | CA | LEU A 711 | 35.315 | 57.387 | -7.201 | 1.00 | 14.33 | C |
| ATOM | 10108 | CB | LEU A 711 | 35.814 | 58.105 | -5.941 | 1.00 | 15.70 | C |
| ATOM | 10111 | CG | LEU A 711 | 34.843 | 58.102 | -4.753 | 1.00 | 17.70 | C |
| ATOM | 10113 | CD1 | LEU A 711 | 35.549 | 58.704 | -3.548 | 1.00 | 18.75 | C |
| ATOM | 10117 | CD2 | LEU A 711 | 33.584 | 58.872 | -5.060 | 1.00 | 19.17 | C |
| ATOM | 10121 | C | LEU A 711 | 36.305 | 57.572 | -8.351 | 1.00 | 15.59 | C |
| ATOM | 10122 | O | LEU A 711 | 36.094 | 58.375 | -9.262 | 1.00 | 14.63 | O |
| ATOM | 10124 | N | LEU A 712 | 37.389 | 56.801 | -8.311 | 1.00 | 16.65 | N |
| ATOM | 10125 | CA | LEU A 712 | 38.388 | 56.900 | -9.367 | 1.00 | 18.36 | C |
| ATOM | 10127 | CB | LEU A 712 | 39.621 | 56.087 | -8.989 | 1.00 | 17.91 | C |
| ATOM | 10130 | CG | LEU A 712 | 40.784 | 56.182 | -9.979 | 1.00 | 21.76 | C |
| ATOM | 10132 | CD1 | LEU A 712 | 41.290 | 57.610 | -10.052 | 1.00 | 24.79 | C |
| ATOM | 10136 | CD2 | LEU A 712 | 41.895 | 55.177 | -9.600 | 1.00 | 21.94 | C |
| ATOM | 10140 | C | LEU A 712 | 37.795 | 56.510 | -10.730 | 1.00 | 18.12 | C |
| ATOM | 10141 | O | LEU A 712 | 37.922 | 57.251 | -11.710 | 1.00 | 19.96 | O |
| ATOM | 10143 | N | LYS A 713 | 37.129 | 55.368 | -10.782 | 1.00 | 16.88 | N |
| ATOM | 10144 | CA | LYS A 713 | 36.458 | 54.907 | -12.001 | 1.00 | 17.89 | C |
| ATOM | 10146 | CB | LYS A 713 | 35.681 | 53.626 | -11.683 | 1.00 | 18.48 | C |
| ATOM | 10149 | CG | LYS A 713 | 35.168 | 52.942 | -12.884 | 1.00 | 23.13 | C |
| ATOM | 10152 | CD | LYS A 713 | 34.654 | 51.556 | -12.506 | 1.00 | 26.79 | C |
| ATOM | 10155 | CE | LYS A 713 | 33.762 | 50.972 | -13.584 | 1.00 | 31.02 | C |
| ATOM | 10158 | NZ | LYS A 713 | 33.164 | 49.697 | -13.058 | 1.00 | 33.57 | N |
| ATOM | 10162 | C | LYS A 713 | 35.499 | 55.935 | -12.608 | 1.00 | 18.70 | C |

```
ATOM  10163  O    LYS A 713      35.498  56.147 -13.818  1.00 17.50           O
ATOM  10165  N    MSE A 714      34.700  56.583 -11.766  1.00 19.48           N
ATOM  10166  CA   MSE A 714      33.715  57.563 -12.222  1.00 21.64           C
ATOM  10168  CB   MSE A 714      32.876  58.090 -11.078  1.00 21.08           C
ATOM  10171  CG   MSE A 714      32.044  57.126 -10.367  1.00 22.90           C
ATOM  10174  SE   MSE A 714      31.514  58.038  -8.643  1.00 29.52           SE
ATOM  10175  CE   MSE A 714      29.914  59.070  -9.432  1.00 21.35           C
ATOM  10179  C    MSE A 714      34.362  58.778 -12.845  1.00 21.99           C
ATOM  10180  O    MSE A 714      33.794  59.373 -13.733  1.00 21.28           O
ATOM  10182  N    LEU A 715      35.522  59.162 -12.326  1.00 23.56           N
ATOM  10183  CA   LEU A 715      36.208  60.400 -12.705  1.00 25.33           C
ATOM  10185  CB   LEU A 715      36.672  61.142 -11.453  1.00 25.90           C
ATOM  10188  CG   LEU A 715      35.565  61.712 -10.550  1.00 27.06           C
ATOM  10190  CD1  LEU A 715      36.056  62.012  -9.146  1.00 28.05           C
ATOM  10194  CD2  LEU A 715      34.967  62.963 -11.211  1.00 27.29           C
ATOM  10198  C    LEU A 715      37.388  60.099 -13.628  1.00 27.57           C
ATOM  10199  O    LEU A 715      37.997  61.042 -14.149  1.00 29.80           O
ATOM  10201  N    ALA B  26      48.268  88.710 -18.934  1.00 36.71           N
ATOM  10202  CA   ALA B  26      48.565  88.191 -17.548  1.00 36.58           C
ATOM  10204  CB   ALA B  26      47.553  87.100 -17.144  1.00 36.48           C
ATOM  10208  C    ALA B  26      50.024  87.682 -17.436  1.00 36.63           C
ATOM  10209  O    ALA B  26      50.493  86.892 -18.273  1.00 36.62           O
ATOM  10213  N    SER B  27      50.749  88.147 -16.419  1.00 36.40           N
ATOM  10214  CA   SER B  27      52.185  87.858 -16.308  1.00 36.52           C
ATOM  10216  CB   SER B  27      52.848  88.830 -15.325  1.00 36.77           C
ATOM  10219  OG   SER B  27      54.240  88.594 -15.189  1.00 36.07           O
ATOM  10221  C    SER B  27      52.487  86.408 -15.900  1.00 36.93           C
ATOM  10222  O    SER B  27      51.895  85.877 -14.965  1.00 36.92           O
ATOM  10224  N    THR B  28      53.439  85.793 -16.612  1.00 37.07           N
ATOM  10225  CA   THR B  28      53.973  84.461 -16.292  1.00 37.19           C
ATOM  10227  CB   THR B  28      54.435  83.776 -17.582  1.00 37.59           C
ATOM  10229  OG1  THR B  28      55.428  84.594 -18.217  1.00 37.80           O
ATOM  10231  CG2  THR B  28      53.242  83.597 -18.539  1.00 38.74           C
ATOM  10235  C    THR B  28      55.173  84.534 -15.323  1.00 36.92           C
ATOM  10236  O    THR B  28      55.699  83.504 -14.893  1.00 36.99           O
ATOM  10238  N    ASN B  29      55.618  85.753 -15.007  1.00 36.58           N
ATOM  10239  CA   ASN B  29      56.677  85.962 -14.028  1.00 35.74           C
ATOM  10241  CB   ASN B  29      57.156  87.418 -14.058  1.00 36.39           C
ATOM  10244  CG   ASN B  29      58.313  87.707 -13.069  1.00 37.74           C
ATOM  10245  OD1  ASN B  29      58.657  86.886 -12.189  1.00 40.34           O
ATOM  10246  ND2  ASN B  29      58.921  88.895 -13.227  1.00 39.49           N
ATOM  10249  C    ASN B  29      56.095  85.626 -12.671  1.00 35.07           C
ATOM  10250  O    ASN B  29      55.115  86.255 -12.236  1.00 34.69           O
ATOM  10252  N    LEU B  30      56.693  84.640 -12.002  1.00 33.62           N
ATOM  10253  CA   LEU B  30      56.165  84.186 -10.719  1.00 33.27           C
ATOM  10255  CB   LEU B  30      56.884  82.894 -10.248  1.00 33.66           C
ATOM  10258  CG   LEU B  30      56.568  81.521 -10.889  1.00 34.56           C
ATOM  10260  CD1  LEU B  30      56.999  80.377  -9.958  1.00 35.74           C
ATOM  10264  CD2  LEU B  30      55.097  81.348 -11.231  1.00 36.30           C
ATOM  10268  C    LEU B  30      56.250  85.293  -9.639  1.00 32.99           C
ATOM  10269  O    LEU B  30      55.447  85.282  -8.672  1.00 31.34           O
ATOM  10271  N    ALA B  31      57.209  86.229  -9.775  1.00 31.61           N
ATOM  10272  CA   ALA B  31      57.274  87.405  -8.854  1.00 31.66           C
ATOM  10274  CB   ALA B  31      58.515  88.231  -9.117  1.00 31.63           C
ATOM  10278  C    ALA B  31      56.020  88.286  -8.975  1.00 31.64           C
ATOM  10279  O    ALA B  31      55.652  89.011  -8.043  1.00 30.89           O
ATOM  10281  N    VAL B  32      55.352  88.246 -10.130  1.00 30.82           N
```

| ATOM | 10282 | CA | VAL | B | 32 | 54.032 | 88.901 | -10.254 | 1.00 | 31.74 | C |
|---|---|---|---|---|---|---|---|---|---|---|---|
| ATOM | 10284 | CB | VAL | B | 32 | 53.782 | 89.391 | -11.710 | 1.00 | 31.67 | C |
| ATOM | 10286 | CG1 | VAL | B | 32 | 52.295 | 89.775 | -11.910 | 1.00 | 32.13 | C |
| ATOM | 10290 | CG2 | VAL | B | 32 | 54.725 | 90.557 | -12.024 | 1.00 | 31.24 | C |
| ATOM | 10294 | C | VAL | B | 32 | 52.874 | 87.965 | -9.838 | 1.00 | 31.94 | C |
| ATOM | 10295 | O | VAL | B | 32 | 51.935 | 88.351 | -9.111 | 1.00 | 30.99 | O |
| ATOM | 10297 | N | ALA | B | 33 | 52.983 | 86.725 | -10.309 | 1.00 | 32.32 | N |
| ATOM | 10298 | CA | ALA | B | 33 | 51.891 | 85.753 | -10.280 | 1.00 | 32.41 | C |
| ATOM | 10300 | CB | ALA | B | 33 | 52.120 | 84.727 | -11.395 | 1.00 | 32.22 | C |
| ATOM | 10304 | C | ALA | B | 33 | 51.644 | 85.025 | -8.939 | 1.00 | 32.59 | C |
| ATOM | 10305 | O | ALA | B | 33 | 50.595 | 84.417 | -8.789 | 1.00 | 32.54 | O |
| ATOM | 10307 | N | GLY | B | 34 | 52.578 | 85.076 | -7.975 | 1.00 | 32.45 | N |
| ATOM | 10308 | CA | GLY | B | 34 | 52.538 | 84.166 | -6.795 | 1.00 | 32.29 | C |
| ATOM | 10311 | C | GLY | B | 34 | 52.763 | 82.729 | -7.253 | 1.00 | 33.02 | C |
| ATOM | 10312 | O | GLY | B | 34 | 52.986 | 82.478 | -8.480 | 1.00 | 32.16 | O |
| ATOM | 10314 | N | THR | B | 39 | 57.840 | 76.212 | -4.291 | 1.00 | 27.00 | N |
| ATOM | 10315 | CA | THR | B | 39 | 58.856 | 76.322 | -5.319 | 1.00 | 27.86 | C |
| ATOM | 10317 | CB | THR | B | 39 | 58.264 | 76.739 | -6.725 | 1.00 | 28.37 | C |
| ATOM | 10319 | OG1 | THR | B | 39 | 59.334 | 76.829 | -7.680 | 1.00 | 26.04 | O |
| ATOM | 10321 | CG2 | THR | B | 39 | 57.494 | 78.089 | -6.694 | 1.00 | 28.96 | C |
| ATOM | 10325 | C | THR | B | 39 | 59.977 | 77.275 | -4.969 | 1.00 | 28.93 | C |
| ATOM | 10326 | O | THR | B | 39 | 59.752 | 78.361 | -4.434 | 1.00 | 29.09 | O |
| ATOM | 10328 | N | THR | B | 40 | 61.190 | 76.861 | -5.301 | 1.00 | 29.97 | N |
| ATOM | 10329 | CA | THR | B | 40 | 62.373 | 77.670 | -5.069 | 1.00 | 31.34 | C |
| ATOM | 10331 | CB | THR | B | 40 | 63.637 | 76.780 | -5.123 | 1.00 | 31.30 | C |
| ATOM | 10333 | OG1 | THR | B | 40 | 63.609 | 76.002 | -6.337 | 1.00 | 32.64 | O |
| ATOM | 10335 | CG2 | THR | B | 40 | 63.751 | 75.864 | -3.829 | 1.00 | 31.62 | C |
| ATOM | 10339 | C | THR | B | 40 | 62.486 | 78.786 | -6.135 | 1.00 | 31.50 | C |
| ATOM | 10340 | O | THR | B | 40 | 63.347 | 79.669 | -6.036 | 1.00 | 32.06 | O |
| ATOM | 10342 | N | GLN | B | 41 | 61.625 | 78.748 | -7.151 | 1.00 | 31.66 | N |
| ATOM | 10343 | CA | GLN | B | 41 | 61.737 | 79.698 | -8.267 | 1.00 | 32.08 | C |
| ATOM | 10345 | CB | GLN | B | 41 | 61.261 | 79.071 | -9.587 | 1.00 | 33.03 | C |
| ATOM | 10348 | CG | GLN | B | 41 | 61.839 | 79.776 | -10.826 | 1.00 | 38.65 | C |
| ATOM | 10351 | CD | GLN | B | 41 | 63.353 | 80.031 | -10.714 | 1.00 | 43.61 | C |
| ATOM | 10352 | OE1 | GLN | B | 41 | 64.162 | 79.094 | -10.809 | 1.00 | 46.86 | O |
| ATOM | 10353 | NE2 | GLN | B | 41 | 63.737 | 81.306 | -10.494 | 1.00 | 46.24 | N |
| ATOM | 10356 | C | GLN | B | 41 | 61.016 | 81.038 | -8.019 | 1.00 | 30.56 | C |
| ATOM | 10357 | O | GLN | B | 41 | 61.038 | 81.911 | -8.885 | 1.00 | 30.42 | O |
| ATOM | 10359 | N | VAL | B | 42 | 60.390 | 81.223 | -6.859 | 1.00 | 27.72 | N |
| ATOM | 10360 | CA | VAL | B | 42 | 59.862 | 82.546 | -6.530 | 1.00 | 26.44 | C |
| ATOM | 10362 | CB | VAL | B | 42 | 58.435 | 82.740 | -7.000 | 1.00 | 26.11 | C |
| ATOM | 10364 | CG1 | VAL | B | 42 | 57.442 | 81.890 | -6.144 | 1.00 | 29.38 | C |
| ATOM | 10368 | CG2 | VAL | B | 42 | 58.069 | 84.248 | -7.011 | 1.00 | 27.02 | C |
| ATOM | 10372 | C | VAL | B | 42 | 59.905 | 82.702 | -5.039 | 1.00 | 24.98 | C |
| ATOM | 10373 | O | VAL | B | 42 | 59.773 | 81.709 | -4.311 | 1.00 | 26.69 | O |
| ATOM | 10375 | N | THR | B | 43 | 60.144 | 83.914 | -4.580 | 1.00 | 21.37 | N |
| ATOM | 10376 | CA | THR | B | 43 | 60.255 | 84.145 | -3.151 | 1.00 | 18.25 | C |
| ATOM | 10378 | CB | THR | B | 43 | 61.697 | 84.463 | -2.728 | 1.00 | 18.23 | C |
| ATOM | 10380 | OG1 | THR | B | 43 | 62.097 | 85.699 | -3.363 | 1.00 | 16.24 | O |
| ATOM | 10382 | CG2 | THR | B | 43 | 62.663 | 83.316 | -3.111 | 1.00 | 19.20 | C |
| ATOM | 10386 | C | THR | B | 43 | 59.384 | 85.312 | -2.767 | 1.00 | 17.03 | C |
| ATOM | 10387 | O | THR | B | 43 | 58.987 | 86.134 | -3.598 | 1.00 | 15.99 | O |
| ATOM | 10389 | N | GLN | B | 44 | 59.153 | 85.438 | -1.469 | 1.00 | 15.53 | N |
| ATOM | 10390 | CA | GLN | B | 44 | 58.373 | 86.539 | -0.949 | 1.00 | 15.03 | C |
| ATOM | 10392 | CB | GLN | B | 44 | 58.101 | 86.327 | 0.543 | 1.00 | 16.57 | C |
| ATOM | 10395 | CG | GLN | B | 44 | 57.262 | 87.409 | 1.174 | 1.00 | 16.29 | C |
| ATOM | 10398 | CD | GLN | B | 44 | 56.776 | 86.974 | 2.525 | 1.00 | 15.16 | C |

| | | | | | | | | | |
|---|---|---|---|---|---|---|---|---|---|
| ATOM | 10399 | OE1 | GLN | B | 44 | 57.617 | 86.597 | 3.357 | 1.00 16.75 | O |
| ATOM | 10400 | NE2 | GLN | B | 44 | 55.435 | 86.995 | 2.770 | 1.00 13.55 | N |
| ATOM | 10403 | C | GLN | B | 44 | 59.090 | 87.853 | -1.219 | 1.00 14.72 | C |
| ATOM | 10404 | O | GLN | B | 44 | 58.474 | 88.824 | -1.612 | 1.00 13.44 | O |
| ATOM | 10406 | N | VAL | B | 45 | 60.413 | 87.889 | -1.024 | 1.00 14.86 | N |
| ATOM | 10407 | CA | VAL | B | 45 | 61.139 | 89.098 | -1.368 | 1.00 15.32 | C |
| ATOM | 10409 | CB | VAL | B | 45 | 62.676 | 88.982 | -1.036 | 1.00 15.57 | C |
| ATOM | 10411 | CG1 | VAL | B | 45 | 63.415 | 90.261 | -1.523 | 1.00 19.35 | C |
| ATOM | 10415 | CG2 | VAL | B | 45 | 62.928 | 88.793 | 0.465 | 1.00 19.26 | C |
| ATOM | 10419 | C | VAL | B | 45 | 60.951 | 89.476 | -2.845 | 1.00 14.97 | C |
| ATOM | 10420 | O | VAL | B | 45 | 60.738 | 90.667 | -3.131 | 1.00 14.90 | O |
| ATOM | 10422 | N | ASP | B | 46 | 61.035 | 88.503 | -3.774 | 1.00 14.88 | N |
| ATOM | 10423 | CA | ASP | B | 46 | 60.761 | 88.772 | -5.216 | 1.00 15.19 | C |
| ATOM | 10425 | CB | ASP | B | 46 | 60.748 | 87.476 | -6.057 | 1.00 15.98 | C |
| ATOM | 10428 | CG | ASP | B | 46 | 62.111 | 86.816 | -6.199 | 1.00 19.15 | C |
| ATOM | 10429 | OD1 | ASP | B | 46 | 63.142 | 87.521 | -5.988 | 1.00 22.53 | O |
| ATOM | 10430 | OD2 | ASP | B | 46 | 62.124 | 85.584 | -6.540 | 1.00 22.48 | O |
| ATOM | 10431 | C | ASP | B | 46 | 59.372 | 89.430 | -5.412 | 1.00 15.14 | C |
| ATOM | 10432 | O | ASP | B | 46 | 59.224 | 90.402 | -6.161 | 1.00 14.92 | O |
| ATOM | 10434 | N | ILE | B | 47 | 58.367 | 88.862 | -4.743 | 1.00 14.32 | N |
| ATOM | 10435 | CA | ILE | B | 47 | 56.988 | 89.334 | -4.789 | 1.00 14.79 | C |
| ATOM | 10437 | CB | ILE | B | 47 | 56.059 | 88.379 | -4.005 | 1.00 14.79 | C |
| ATOM | 10439 | CG1 | ILE | B | 47 | 55.941 | 87.082 | -4.831 | 1.00 15.18 | C |
| ATOM | 10442 | CD1 | ILE | B | 47 | 55.231 | 85.890 | -4.156 | 1.00 16.64 | C |
| ATOM | 10446 | CG2 | ILE | B | 47 | 54.714 | 89.058 | -3.726 | 1.00 15.62 | C |
| ATOM | 10450 | C | ILE | B | 47 | 56.861 | 90.766 | -4.258 | 1.00 14.38 | C |
| ATOM | 10451 | O | ILE | B | 47 | 56.248 | 91.641 | -4.866 | 1.00 16.05 | O |
| ATOM | 10453 | N | VAL | B | 48 | 57.487 | 91.003 | -3.113 | 1.00 14.60 | N |
| ATOM | 10454 | CA | VAL | B | 48 | 57.483 | 92.331 | -2.524 | 1.00 14.02 | C |
| ATOM | 10456 | CB | VAL | B | 48 | 58.094 | 92.264 | -1.105 | 1.00 13.85 | C |
| ATOM | 10458 | CG1 | VAL | B | 48 | 58.462 | 93.646 | -0.571 | 1.00 14.62 | C |
| ATOM | 10462 | CG2 | VAL | B | 48 | 57.141 | 91.523 | -0.172 | 1.00 15.56 | C |
| ATOM | 10466 | C | VAL | B | 48 | 58.184 | 93.364 | -3.409 | 1.00 13.85 | C |
| ATOM | 10467 | O | VAL | B | 48 | 57.708 | 94.482 | -3.589 | 1.00 13.53 | O |
| ATOM | 10469 | N | GLU | B | 49 | 59.327 | 92.981 | -3.960 | 1.00 13.83 | N |
| ATOM | 10470 | CA | GLU | B | 49 | 60.087 | 93.907 | -4.770 | 1.00 16.22 | C |
| ATOM | 10472 | CB | GLU | B | 49 | 61.341 | 93.209 | -5.286 | 1.00 16.94 | C |
| ATOM | 10475 | CG | GLU | B | 49 | 62.184 | 94.065 | -6.186 | 1.00 20.81 | C |
| ATOM | 10478 | CD | GLU | B | 49 | 63.430 | 93.327 | -6.667 | 1.00 24.08 | C |
| ATOM | 10479 | OE1 | GLU | B | 49 | 63.337 | 92.100 | -7.003 | 1.00 34.03 | O |
| ATOM | 10480 | OE2 | GLU | B | 49 | 64.512 | 93.964 | -6.739 | 1.00 35.54 | O |
| ATOM | 10481 | C | GLU | B | 49 | 59.219 | 94.363 | -5.944 | 1.00 15.46 | C |
| ATOM | 10482 | O | GLU | B | 49 | 59.179 | 95.530 | -6.279 | 1.00 13.90 | O |
| ATOM | 10484 | N | LYS | B | 50 | 58.480 | 93.426 | -6.535 | 1.00 15.09 | N |
| ATOM | 10485 | CA | LYS | B | 50 | 57.661 | 93.782 | -7.679 | 1.00 16.23 | C |
| ATOM | 10487 | CB | LYS | B | 50 | 57.130 | 92.535 | -8.355 | 1.00 17.67 | C |
| ATOM | 10490 | CG | LYS | B | 50 | 58.232 | 91.672 | -8.970 | 1.00 23.29 | C |
| ATOM | 10493 | CD | LYS | B | 50 | 58.978 | 92.363 | -10.146 | 1.00 28.53 | C |
| ATOM | 10496 | CE | LYS | B | 50 | 60.510 | 92.051 | -10.160 | 1.00 29.13 | C |
| ATOM | 10499 | NZ | LYS | B | 50 | 60.840 | 90.599 | -10.535 | 1.00 34.70 | N |
| ATOM | 10503 | C | LYS | B | 50 | 56.511 | 94.676 | -7.250 | 1.00 17.03 | C |
| ATOM | 10504 | O | LYS | B | 50 | 56.154 | 95.634 | -7.935 | 1.00 16.52 | O |
| ATOM | 10506 | N | MSE | B | 51 | 55.928 | 94.368 | -6.110 | 1.00 17.43 | N |
| ATOM | 10507 | CA | MSE | B | 51 | 54.821 | 95.219 | -5.607 | 1.00 19.56 | C |
| ATOM | 10509 | CB | MSE | B | 51 | 54.235 | 94.640 | -4.303 | 1.00 19.78 | C |
| ATOM | 10512 | CG | MSE | B | 51 | 53.463 | 93.401 | -4.486 | 1.00 19.60 | C |
| ATOM | 10515 | SE | MSE | B | 51 | 52.251 | 93.196 | -2.892 | 1.00 30.85 | SE |

| | | | | | | | | | | |
|---|---|---|---|---|---|---|---|---|---|---|
| ATOM | 10516 | CE | MSE | B | 51 | 50.556 | 94.272 | -3.501 | 1.00 36.52 | C |
| ATOM | 10520 | C | MSE | B | 51 | 55.251 | 96.639 | -5.364 | 1.00 18.69 | C |
| ATOM | 10521 | O | MSE | B | 51 | 54.577 | 97.592 | -5.748 | 1.00 18.70 | O |
| ATOM | 10523 | N | LEU | B | 52 | 56.403 | 96.792 | -4.735 | 1.00 18.42 | N |
| ATOM | 10524 | CA | LEU | B | 52 | 56.900 | 98.095 | -4.339 | 1.00 19.13 | C |
| ATOM | 10526 | CB | LEU | B | 52 | 58.012 | 97.961 | -3.272 | 1.00 19.38 | C |
| ATOM | 10529 | CG | LEU | B | 52 | 57.567 | 97.404 | -1.908 | 1.00 20.07 | C |
| ATOM | 10531 | CD1 | LEU | B | 52 | 58.752 | 97.244 | -0.982 | 1.00 23.04 | C |
| ATOM | 10535 | CD2 | LEU | B | 52 | 56.510 | 98.252 | -1.218 | 1.00 22.45 | C |
| ATOM | 10539 | C | LEU | B | 52 | 57.382 | 98.880 | -5.534 | 1.00 19.01 | C |
| ATOM | 10540 | O | LEU | B | 52 | 57.508 | 100.093 | -5.452 | 1.00 19.68 | O |
| ATOM | 10542 | N | ALA | B | 53 | 57.655 | 98.190 | -6.637 | 1.00 19.26 | N |
| ATOM | 10543 | CA | ALA | B | 53 | 58.053 | 98.831 | -7.893 | 1.00 19.39 | C |
| ATOM | 10545 | CB | ALA | B | 53 | 58.884 | 97.852 | -8.731 | 1.00 19.64 | C |
| ATOM | 10549 | C | ALA | B | 53 | 56.855 | 99.346 | -8.716 | 1.00 19.78 | C |
| ATOM | 10550 | O | ALA | B | 53 | 57.051 | 100.001 | -9.739 | 1.00 19.41 | O |
| ATOM | 10552 | N | ALA | B | 54 | 55.619 | 99.050 | -8.315 | 1.00 19.50 | N |
| ATOM | 10553 | CA | ALA | B | 54 | 54.452 | 99.560 | -9.055 | 1.00 20.28 | C |
| ATOM | 10555 | CB | ALA | B | 54 | 53.185 | 99.183 | -8.359 | 1.00 20.37 | C |
| ATOM | 10559 | C | ALA | B | 54 | 54.543 | 101.090 | -9.171 | 1.00 20.48 | C |
| ATOM | 10560 | O | ALA | B | 54 | 54.764 | 101.766 | -8.158 | 1.00 20.84 | O |
| ATOM | 10562 | N | PRO | B | 55 | 54.426 | 101.640 | -10.400 | 1.00 20.96 | N |
| ATOM | 10563 | CA | PRO | B | 55 | 54.346 | 103.108 | -10.603 | 1.00 21.72 | C |
| ATOM | 10565 | CB | PRO | B | 55 | 53.998 | 103.252 | -12.096 | 1.00 21.70 | C |
| ATOM | 10568 | CG | PRO | B | 55 | 54.443 | 102.026 | -12.712 | 1.00 21.81 | C |
| ATOM | 10571 | CD | PRO | B | 55 | 54.403 | 100.913 | -11.678 | 1.00 21.29 | C |
| ATOM | 10574 | C | PRO | B | 55 | 53.250 | 103.748 | -9.769 | 1.00 22.79 | C |
| ATOM | 10575 | O | PRO | B | 55 | 52.215 | 103.117 | -9.534 | 1.00 22.55 | O |
| ATOM | 10576 | N | THR | B | 56 | 53.469 | 104.974 | -9.309 | 1.00 24.48 | N |
| ATOM | 10577 | CA | THR | B | 56 | 52.373 | 105.726 | -8.651 | 1.00 25.78 | C |
| ATOM | 10579 | CB | THR | B | 56 | 52.733 | 106.129 | -7.230 | 1.00 26.14 | C |
| ATOM | 10581 | OG1 | THR | B | 56 | 53.886 | 106.995 | -7.270 | 1.00 27.10 | O |
| ATOM | 10583 | CG2 | THR | B | 56 | 52.984 | 104.887 | -6.367 | 1.00 26.99 | C |
| ATOM | 10587 | C | THR | B | 56 | 51.932 | 106.970 | -9.438 | 1.00 26.21 | C |
| ATOM | 10588 | O | THR | B | 56 | 50.870 | 107.549 | -9.172 | 1.00 27.04 | O |
| ATOM | 10590 | N | ASP | B | 57 | 52.750 | 107.365 | -10.403 | 1.00 26.57 | N |
| ATOM | 10591 | CA | ASP | B | 57 | 52.538 | 108.605 | -11.156 | 1.00 26.57 | C |
| ATOM | 10593 | CB | ASP | B | 57 | 53.894 | 109.322 | -11.341 | 1.00 27.36 | C |
| ATOM | 10596 | CG | ASP | B | 57 | 54.981 | 108.396 | -11.952 | 1.00 31.12 | C |
| ATOM | 10597 | OD1 | ASP | B | 57 | 54.977 | 107.154 | -11.676 | 1.00 35.42 | O |
| ATOM | 10598 | OD2 | ASP | B | 57 | 55.845 | 108.898 | -12.721 | 1.00 38.20 | O |
| ATOM | 10599 | C | ASP | B | 57 | 51.893 | 108.320 | -12.509 | 1.00 25.45 | C |
| ATOM | 10600 | O | ASP | B | 57 | 50.982 | 109.047 | -12.950 | 1.00 25.14 | O |
| ATOM | 10602 | N | SER | B | 58 | 52.380 | 107.287 | -13.194 | 1.00 23.34 | N |
| ATOM | 10603 | CA | SER | B | 58 | 51.929 | 107.008 | -14.540 | 1.00 22.10 | C |
| ATOM | 10605 | CB | SER | B | 58 | 52.972 | 106.211 | -15.310 | 1.00 22.07 | C |
| ATOM | 10608 | OG | SER | B | 58 | 53.241 | 104.993 | -14.663 | 1.00 22.37 | O |
| ATOM | 10610 | C | SER | B | 58 | 50.624 | 106.241 | -14.488 | 1.00 20.78 | C |
| ATOM | 10611 | O | SER | B | 58 | 50.300 | 105.584 | -13.508 | 1.00 19.70 | O |
| ATOM | 10613 | N | THR | B | 59 | 49.860 | 106.353 | -15.557 | 1.00 19.57 | N |
| ATOM | 10614 | CA | THR | B | 59 | 48.512 | 105.855 | -15.504 | 1.00 18.49 | C |
| ATOM | 10616 | CB | THR | B | 59 | 47.700 | 106.428 | -16.672 | 1.00 19.04 | C |
| ATOM | 10618 | OG1 | THR | B | 59 | 47.697 | 107.860 | -16.567 | 1.00 20.47 | O |
| ATOM | 10620 | CG2 | THR | B | 59 | 46.246 | 105.897 | -16.654 | 1.00 19.61 | C |
| ATOM | 10624 | C | THR | B | 59 | 48.473 | 104.342 | -15.542 | 1.00 17.43 | C |
| ATOM | 10625 | O | THR | B | 59 | 49.131 | 103.688 | -16.376 | 1.00 17.62 | O |
| ATOM | 10627 | N | LEU | B | 60 | 47.639 | 103.800 | -14.668 | 1.00 15.45 | N |

| ATOM | 10628 | CA  | LEU | B | 60 | 47.354 | 102.375 | -14.659 | 1.00 | 15.12 | C |
|------|-------|-----|-----|---|----|--------|---------|---------|------|-------|---|
| ATOM | 10630 | CB  | LEU | B | 60 | 46.868 | 101.936 | -13.285 | 1.00 | 15.08 | C |
| ATOM | 10633 | CG  | LEU | B | 60 | 46.414 | 100.479 | -13.159 | 1.00 | 14.29 | C |
| ATOM | 10635 | CD1 | LEU | B | 60 | 47.527 | 99.473  | -13.559 | 1.00 | 14.92 | C |
| ATOM | 10639 | CD2 | LEU | B | 60 | 45.904 | 100.174 | -11.744 | 1.00 | 15.26 | C |
| ATOM | 10643 | C   | LEU | B | 60 | 46.299 | 102.121 | -15.706 | 1.00 | 14.81 | C |
| ATOM | 10644 | O   | LEU | B | 60 | 45.161 | 102.536 | -15.539 | 1.00 | 14.92 | O |
| ATOM | 10646 | N   | GLU | B | 61 | 46.694 | 101.438 | -16.769 | 1.00 | 14.65 | N |
| ATOM | 10647 | CA  | GLU | B | 61 | 45.819 | 101.071 | -17.867 | 1.00 | 16.41 | C |
| ATOM | 10649 | CB  | GLU | B | 61 | 46.593 | 101.089 | -19.186 | 1.00 | 16.45 | C |
| ATOM | 10652 | CG  | GLU | B | 61 | 46.786 | 102.497 | -19.722 | 1.00 | 20.93 | C |
| ATOM | 10655 | CD  | GLU | B | 61 | 47.167 | 102.528 | -21.210 | 1.00 | 21.91 | C |
| ATOM | 10656 | OE1 | GLU | B | 61 | 48.312 | 102.109 | -21.465 | 1.00 | 26.07 | O |
| ATOM | 10657 | OE2 | GLU | B | 61 | 46.355 | 102.959 | -22.097 | 1.00 | 28.70 | O |
| ATOM | 10658 | C   | GLU | B | 61 | 45.216 | 99.690  | -17.664 | 1.00 | 15.05 | C |
| ATOM | 10659 | O   | GLU | B | 61 | 45.934 | 98.695  | -17.587 | 1.00 | 17.59 | O |
| ATOM | 10661 | N   | LEU | B | 62 | 43.907 | 99.633  | -17.530 | 1.00 | 13.78 | N |
| ATOM | 10662 | CA  | LEU | B | 62 | 43.197 | 98.391  | -17.230 | 1.00 | 13.52 | C |
| ATOM | 10664 | CB  | LEU | B | 62 | 41.975 | 98.691  | -16.365 | 1.00 | 14.28 | C |
| ATOM | 10667 | CG  | LEU | B | 62 | 42.302 | 99.308  | -15.023 | 1.00 | 12.75 | C |
| ATOM | 10669 | CD1 | LEU | B | 62 | 41.028 | 99.631  | -14.261 | 1.00 | 13.47 | C |
| ATOM | 10673 | CD2 | LEU | B | 62 | 43.257 | 98.405  | -14.229 | 1.00 | 14.15 | C |
| ATOM | 10677 | C   | LEU | B | 62 | 42.745 | 97.695  | -18.520 | 1.00 | 14.82 | C |
| ATOM | 10678 | O   | LEU | B | 62 | 42.068 | 98.292  | -19.360 | 1.00 | 14.16 | O |
| ATOM | 10680 | N   | ASP | B | 63 | 43.168 | 96.443  | -18.681 | 1.00 | 13.34 | N |
| ATOM | 10681 | CA  | ASP | B | 63 | 42.853 | 95.692  | -19.875 | 1.00 | 13.38 | C |
| ATOM | 10683 | CB  | ASP | B | 63 | 44.114 | 95.457  | -20.739 | 1.00 | 13.76 | C |
| ATOM | 10686 | CG  | ASP | B | 63 | 45.181 | 94.639  | -20.022 | 1.00 | 16.41 | C |
| ATOM | 10687 | OD1 | ASP | B | 63 | 44.840 | 93.738  | -19.244 | 1.00 | 13.94 | O |
| ATOM | 10688 | OD2 | ASP | B | 63 | 46.384 | 94.878  | -20.236 | 1.00 | 18.61 | O |
| ATOM | 10689 | C   | ASP | B | 63 | 42.136 | 94.376  | -19.608 | 1.00 | 13.17 | C |
| ATOM | 10690 | O   | ASP | B | 63 | 41.905 | 93.623  | -20.534 | 1.00 | 12.94 | O |
| ATOM | 10692 | N   | GLY | B | 64 | 41.770 | 94.119  | -18.355 | 1.00 | 13.05 | N |
| ATOM | 10693 | CA  | GLY | B | 64 | 41.046 | 92.890  | -17.992 | 1.00 | 13.52 | C |
| ATOM | 10696 | C   | GLY | B | 64 | 41.936 | 91.704  | -17.597 | 1.00 | 14.02 | C |
| ATOM | 10697 | O   | GLY | B | 64 | 41.444 | 90.714  | -17.067 | 1.00 | 13.45 | O |
| ATOM | 10699 | N   | TYR | B | 65 | 43.244 | 91.794  | -17.809 | 1.00 | 13.53 | N |
| ATOM | 10700 | CA  | TYR | B | 65 | 44.162 | 90.621  | -17.651 | 1.00 | 13.56 | C |
| ATOM | 10702 | CB  | TYR | B | 65 | 44.456 | 89.975  | -19.027 | 1.00 | 14.19 | C |
| ATOM | 10705 | CG  | TYR | B | 65 | 43.253 | 89.359  | -19.668 | 1.00 | 17.16 | C |
| ATOM | 10706 | CD1 | TYR | B | 65 | 43.010 | 87.987  | -19.569 | 1.00 | 16.60 | C |
| ATOM | 10708 | CE1 | TYR | B | 65 | 41.868 | 87.418  | -20.152 | 1.00 | 17.76 | C |
| ATOM | 10710 | CZ  | TYR | B | 65 | 40.943 | 88.246  | -20.782 | 1.00 | 17.50 | C |
| ATOM | 10711 | OH  | TYR | B | 65 | 39.792 | 87.748  | -21.311 | 1.00 | 20.32 | O |
| ATOM | 10713 | CE2 | TYR | B | 65 | 41.183 | 89.604  | -20.894 | 1.00 | 15.97 | C |
| ATOM | 10715 | CD2 | TYR | B | 65 | 42.327 | 90.144  | -20.358 | 1.00 | 15.20 | C |
| ATOM | 10717 | C   | TYR | B | 65 | 45.500 | 90.914  | -16.951 | 1.00 | 13.39 | C |
| ATOM | 10718 | O   | TYR | B | 65 | 46.057 | 90.022  | -16.313 | 1.00 | 12.83 | O |
| ATOM | 10720 | N   | SER | B | 66 | 46.027 | 92.144  | -17.113 | 1.00 | 14.09 | N |
| ATOM | 10721 | CA  | SER | B | 66 | 47.363 | 92.547  | -16.674 | 1.00 | 14.24 | C |
| ATOM | 10723 | CB  | SER | B | 66 | 47.895 | 93.703  | -17.582 | 1.00 | 13.27 | C |
| ATOM | 10726 | OG  | SER | B | 66 | 47.996 | 93.294  | -18.917 | 1.00 | 17.95 | O |
| ATOM | 10728 | C   | SER | B | 66 | 47.453 | 93.036  | -15.263 | 1.00 | 13.48 | C |
| ATOM | 10729 | O   | SER | B | 66 | 48.547 | 93.162  | -14.714 | 1.00 | 14.28 | O |
| ATOM | 10731 | N   | LEU | B | 67 | 46.309 | 93.412  | -14.690 | 1.00 | 12.57 | N |
| ATOM | 10732 | CA  | LEU | B | 67 | 46.303 | 94.078  | -13.407 | 1.00 | 13.19 | C |
| ATOM | 10734 | CB  | LEU | B | 67 | 44.874 | 94.375  | -12.990 | 1.00 | 12.56 | C |

| | | | | | | | | | | |
|---|---|---|---|---|---|---|---|---|---|---|
| ATOM | 10737 | CG | LEU | B | 67 | 44.622 | 95.014 | -11.644 | 1.00 13.33 | C |
| ATOM | 10739 | CD1 | LEU | B | 67 | 45.300 | 96.357 | -11.617 | 1.00 13.82 | C |
| ATOM | 10743 | CD2 | LEU | B | 67 | 43.138 | 95.136 | -11.253 | 1.00 13.22 | C |
| ATOM | 10747 | C | LEU | B | 67 | 46.946 | 93.167 | -12.371 | 1.00 13.25 | C |
| ATOM | 10748 | O | LEU | B | 67 | 46.556 | 92.004 | -12.256 | 1.00 14.90 | O |
| ATOM | 10750 | N | ASN | B | 68 | 47.884 | 93.698 | -11.588 | 1.00 13.69 | N |
| ATOM | 10751 | CA | ASN | B | 68 | 48.514 | 92.912 | -10.509 | 1.00 13.34 | C |
| ATOM | 10753 | CB | ASN | B | 68 | 50.007 | 92.682 | -10.769 | 1.00 13.69 | C |
| ATOM | 10756 | CG | ASN | B | 68 | 50.806 | 93.982 | -10.829 | 1.00 10.87 | C |
| ATOM | 10757 | OD1 | ASN | B | 68 | 50.612 | 94.878 | -9.986 | 1.00 14.55 | O |
| ATOM | 10758 | ND2 | ASN | B | 68 | 51.695 | 94.089 | -11.794 | 1.00 15.28 | N |
| ATOM | 10761 | C | ASN | B | 68 | 48.291 | 93.559 | -9.158 | 1.00 13.43 | C |
| ATOM | 10762 | O | ASN | B | 68 | 47.690 | 94.637 | -9.057 | 1.00 13.82 | O |
| ATOM | 10764 | N | LEU | B | 69 | 48.720 | 92.905 | -8.096 | 1.00 13.67 | N |
| ATOM | 10765 | CA | LEU | B | 69 | 48.358 | 93.347 | -6.780 | 1.00 13.58 | C |
| ATOM | 10767 | CB | LEU | B | 69 | 48.544 | 92.217 | -5.758 | 1.00 13.58 | C |
| ATOM | 10770 | CG | LEU | B | 69 | 47.775 | 90.916 | -6.022 | 1.00 14.15 | C |
| ATOM | 10772 | CD1 | LEU | B | 69 | 47.878 | 90.015 | -4.828 | 1.00 16.22 | C |
| ATOM | 10776 | CD2 | LEU | B | 69 | 46.368 | 91.297 | -6.336 | 1.00 13.77 | C |
| ATOM | 10780 | C | LEU | B | 69 | 49.064 | 94.619 | -6.348 | 1.00 12.94 | C |
| ATOM | 10781 | O | LEU | B | 69 | 48.461 | 95.495 | -5.697 | 1.00 13.80 | O |
| ATOM | 10783 | N | GLY | B | 70 | 50.322 | 94.773 | -6.771 | 1.00 13.33 | N |
| ATOM | 10784 | CA | GLY | B | 70 | 51.014 | 96.043 | -6.560 | 1.00 13.34 | C |
| ATOM | 10787 | C | GLY | B | 70 | 50.286 | 97.207 | -7.222 | 1.00 13.41 | C |
| ATOM | 10788 | O | GLY | B | 70 | 50.189 | 98.286 | -6.631 | 1.00 14.18 | O |
| ATOM | 10790 | N | ASP | B | 71 | 49.751 | 96.977 | -8.429 | 1.00 14.03 | N |
| ATOM | 10791 | CA | ASP | B | 71 | 48.979 | 97.987 | -9.164 | 1.00 14.63 | C |
| ATOM | 10793 | CB | ASP | B | 71 | 48.451 | 97.415 | -10.461 | 1.00 15.42 | C |
| ATOM | 10796 | CG | ASP | B | 71 | 49.489 | 97.221 | -11.540 | 1.00 16.76 | C |
| ATOM | 10797 | OD1 | ASP | B | 71 | 50.491 | 97.995 | -11.615 | 1.00 18.02 | O |
| ATOM | 10798 | OD2 | ASP | B | 71 | 49.220 | 96.330 | -12.423 | 1.00 17.38 | O |
| ATOM | 10799 | C | ASP | B | 71 | 47.754 | 98.372 | -8.351 | 1.00 13.63 | C |
| ATOM | 10800 | O | ASP | B | 71 | 47.419 | 99.562 | -8.227 | 1.00 13.38 | O |
| ATOM | 10802 | N | VAL | B | 72 | 47.066 | 97.352 | -7.807 | 1.00 12.38 | N |
| ATOM | 10803 | CA | VAL | B | 72 | 45.841 | 97.606 | -7.018 | 1.00 13.07 | C |
| ATOM | 10805 | CB | VAL | B | 72 | 45.167 | 96.297 | -6.554 | 1.00 13.53 | C |
| ATOM | 10807 | CG1 | VAL | B | 72 | 44.111 | 96.587 | -5.493 | 1.00 13.18 | C |
| ATOM | 10811 | CG2 | VAL | B | 72 | 44.588 | 95.496 | -7.749 | 1.00 14.68 | C |
| ATOM | 10815 | C | VAL | B | 72 | 46.156 | 98.513 | -5.831 | 1.00 13.20 | C |
| ATOM | 10816 | O | VAL | B | 72 | 45.488 | 99.531 | -5.584 | 1.00 14.44 | O |
| ATOM | 10818 | N | VAL | B | 73 | 47.216 | 98.160 | -5.116 | 1.00 12.33 | N |
| ATOM | 10819 | CA | VAL | B | 73 | 47.617 | 98.967 | -3.951 | 1.00 12.68 | C |
| ATOM | 10821 | CB | VAL | B | 73 | 48.783 | 98.326 | -3.197 | 1.00 12.62 | C |
| ATOM | 10823 | CG1 | VAL | B | 73 | 49.255 | 99.266 | -2.038 | 1.00 12.78 | C |
| ATOM | 10827 | CG2 | VAL | B | 73 | 48.374 | 96.969 | -2.621 | 1.00 15.17 | C |
| ATOM | 10831 | C | VAL | B | 73 | 47.985 | 100.396 | -4.407 | 1.00 12.52 | C |
| ATOM | 10832 | O | VAL | B | 73 | 47.615 | 101.366 | -3.759 | 1.00 14.15 | O |
| ATOM | 10834 | N | SER | B | 74 | 48.688 | 100.543 | -5.526 | 1.00 13.16 | N |
| ATOM | 10835 | CA | SER | B | 74 | 49.040 | 101.904 | -6.003 | 1.00 14.53 | C |
| ATOM | 10837 | CB | SER | B | 74 | 49.939 | 101.874 | -7.221 | 1.00 14.32 | C |
| ATOM | 10840 | OG | SER | B | 74 | 49.340 | 101.268 | -8.370 | 1.00 16.05 | O |
| ATOM | 10842 | C | SER | B | 74 | 47.820 | 102.764 | -6.275 | 1.00 14.42 | C |
| ATOM | 10843 | O | SER | B | 74 | 47.788 | 103.957 | -5.948 | 1.00 16.72 | O |
| ATOM | 10845 | N | ALA | B | 75 | 46.786 | 102.163 | -6.864 | 1.00 13.70 | N |
| ATOM | 10846 | CA | ALA | B | 75 | 45.544 | 102.908 | -7.163 | 1.00 14.26 | C |
| ATOM | 10848 | CB | ALA | B | 75 | 44.700 | 102.102 | -8.108 | 1.00 15.54 | C |
| ATOM | 10852 | C | ALA | B | 75 | 44.764 | 103.178 | -5.866 | 1.00 15.33 | C |

| ATOM | 10853 | O   | ALA B | 75 | 44.250 | 104.269 | -5.672  | 1.00 | 17.20 | O |
|------|-------|-----|-------|----|--------|---------|---------|------|-------|---|
| ATOM | 10855 | N   | ALA B | 76 | 44.689 | 102.181 | -4.993  | 1.00 | 14.46 | N |
| ATOM | 10856 | CA  | ALA B | 76 | 43.910 | 102.313 | -3.749  | 1.00 | 13.94 | C |
| ATOM | 10858 | CB  | ALA B | 76 | 43.794 | 100.978 | -3.046  | 1.00 | 15.02 | C |
| ATOM | 10862 | C   | ALA B | 76 | 44.502 | 103.325 | -2.770  | 1.00 | 15.37 | C |
| ATOM | 10863 | O   | ALA B | 76 | 43.771 | 104.151 | -2.202  | 1.00 | 14.78 | O |
| ATOM | 10865 | N   | ARG B | 77 | 45.814 | 103.206 | -2.540  | 1.00 | 14.86 | N |
| ATOM | 10866 | CA  | ARG B | 77 | 46.535 | 103.998 | -1.520  | 1.00 | 16.21 | C |
| ATOM | 10868 | CB  | ARG B | 77 | 47.506 | 103.085 | -0.823  | 1.00 | 17.02 | C |
| ATOM | 10871 | CG  | ARG B | 77 | 46.838 | 102.185 | 0.109   | 1.00 | 17.60 | C |
| ATOM | 10874 | CD  | ARG B | 77 | 47.895 | 101.621 | 1.127   | 1.00 | 17.26 | C |
| ATOM | 10877 | NE  | ARG B | 77 | 47.168 | 100.774 | 2.051   | 1.00 | 18.26 | N |
| ATOM | 10879 | CZ  | ARG B | 77 | 47.645 | 99.695  | 2.653   | 1.00 | 16.55 | C |
| ATOM | 10880 | NH1 | ARG B | 77 | 48.875 | 99.249  | 2.430   | 1.00 | 18.13 | N |
| ATOM | 10883 | NH2 | ARG B | 77 | 46.858 | 99.038  | 3.476   | 1.00 | 15.40 | N |
| ATOM | 10886 | C   | ARG B | 77 | 47.370 | 105.160 | -1.980  | 1.00 | 17.00 | C |
| ATOM | 10887 | O   | ARG B | 77 | 47.647 | 106.093 | -1.190  | 1.00 | 18.40 | O |
| ATOM | 10889 | N   | LYS B | 78 | 47.862 | 105.116 | -3.211  | 1.00 | 17.86 | N |
| ATOM | 10890 | CA  | LYS B | 78 | 48.838 | 106.115 | -3.659  | 1.00 | 18.31 | C |
| ATOM | 10892 | CB  | LYS B | 78 | 50.120 | 105.449 | -4.191  | 1.00 | 19.66 | C |
| ATOM | 10895 | CG  | LYS B | 78 | 50.710 | 104.351 | -3.336  | 1.00 | 22.12 | C |
| ATOM | 10898 | CD  | LYS B | 78 | 51.400 | 104.912 | -2.150  | 1.00 | 28.92 | C |
| ATOM | 10901 | CE  | LYS B | 78 | 52.020 | 103.842 | -1.253  | 1.00 | 30.41 | C |
| ATOM | 10904 | NZ  | LYS B | 78 | 52.926 | 104.537 | -0.309  | 1.00 | 31.31 | N |
| ATOM | 10908 | C   | LYS B | 78 | 48.338 | 107.109 | -4.703  | 1.00 | 16.83 | C |
| ATOM | 10909 | O   | LYS B | 78 | 49.130 | 107.861 | -5.300  | 1.00 | 18.42 | O |
| ATOM | 10911 | N   | GLY B | 79 | 47.030 | 107.136 | -4.925  | 1.00 | 15.99 | N |
| ATOM | 10912 | CA  | GLY B | 79 | 46.446 | 108.095 | -5.855  | 1.00 | 15.89 | C |
| ATOM | 10915 | C   | GLY B | 79 | 46.828 | 107.952 | -7.310  | 1.00 | 15.90 | C |
| ATOM | 10916 | O   | GLY B | 79 | 46.671 | 108.896 | -8.098  | 1.00 | 16.98 | O |
| ATOM | 10918 | N   | ARG B | 80 | 47.272 | 106.772 | -7.710  | 1.00 | 15.43 | N |
| ATOM | 10919 | CA  | ARG B | 80 | 47.667 | 106.566 | -9.085  | 1.00 | 15.97 | C |
| ATOM | 10921 | CB  | ARG B | 80 | 48.188 | 105.167 | -9.275  | 1.00 | 16.36 | C |
| ATOM | 10924 | CG  | ARG B | 80 | 48.789 | 104.955 | -10.656 | 1.00 | 15.94 | C |
| ATOM | 10927 | CD  | ARG B | 80 | 49.362 | 103.604 | -10.656 | 1.00 | 15.46 | C |
| ATOM | 10930 | NE  | ARG B | 80 | 50.019 | 103.241 | -11.912 | 1.00 | 15.05 | N |
| ATOM | 10932 | CZ  | ARG B | 80 | 50.427 | 102.003 | -12.149 | 1.00 | 16.11 | C |
| ATOM | 10933 | NH1 | ARG B | 80 | 50.296 | 101.061 | -11.200 | 1.00 | 14.23 | N |
| ATOM | 10936 | NH2 | ARG B | 80 | 50.980 | 101.716 | -13.313 | 1.00 | 17.22 | N |
| ATOM | 10939 | C   | ARG B | 80 | 46.505 | 106.721 | -10.031 | 1.00 | 14.83 | C |
| ATOM | 10940 | O   | ARG B | 80 | 45.430 | 106.180 | -9.737  | 1.00 | 14.54 | O |
| ATOM | 10942 | N   | PRO B | 81 | 46.695 | 107.451 | -11.148 | 1.00 | 15.72 | N |
| ATOM | 10943 | CA  | PRO B | 81 | 45.597 | 107.593 | -12.111 | 1.00 | 15.09 | C |
| ATOM | 10945 | CB  | PRO B | 81 | 46.179 | 108.485 | -13.198 | 1.00 | 15.42 | C |
| ATOM | 10948 | CG  | PRO B | 81 | 47.310 | 109.166 | -12.576 | 1.00 | 16.68 | C |
| ATOM | 10951 | CD  | PRO B | 81 | 47.874 | 108.214 | -11.575 | 1.00 | 15.69 | C |
| ATOM | 10954 | C   | PRO B | 81 | 45.239 | 106.232 | -12.702 | 1.00 | 14.25 | C |
| ATOM | 10955 | O   | PRO B | 81 | 46.125 | 105.406 | -12.886 | 1.00 | 12.96 | O |
| ATOM | 10956 | N   | VAL B | 82 | 43.977 | 106.029 | -13.049 | 1.00 | 14.13 | N |
| ATOM | 10957 | CA  | VAL B | 82 | 43.497 | 104.746 | -13.561 | 1.00 | 13.64 | C |
| ATOM | 10959 | CB  | VAL B | 82 | 42.684 | 103.966 | -12.483 | 1.00 | 14.82 | C |
| ATOM | 10961 | CG1 | VAL B | 82 | 42.070 | 102.687 | -13.035 | 1.00 | 13.10 | C |
| ATOM | 10965 | CG2 | VAL B | 82 | 43.530 | 103.696 | -11.278 | 1.00 | 14.41 | C |
| ATOM | 10969 | C   | VAL B | 82 | 42.638 | 105.037 | -14.787 | 1.00 | 14.75 | C |
| ATOM | 10970 | O   | VAL B | 82 | 41.819 | 105.965 | -14.771 | 1.00 | 14.22 | O |
| ATOM | 10972 | N   | ARG B | 83 | 42.827 | 104.265 | -15.850 | 1.00 | 14.26 | N |
| ATOM | 10973 | CA  | ARG B | 83 | 41.927 | 104.327 | -16.998 | 1.00 | 16.80 | C |

| ATOM | 10975 | CB  | ARG | B | 83 | 42.443 | 105.363 | -18.032 | 1.00 | 17.76 | C |
|------|-------|-----|-----|---|----|--------|---------|---------|------|-------|---|
| ATOM | 10978 | CG  | ARG | B | 83 | 42.292 | 106.828 | -17.597 | 1.00 | 23.43 | C |
| ATOM | 10981 | CD  | ARG | B | 83 | 43.151 | 107.787 | -18.433 | 1.00 | 26.44 | C |
| ATOM | 10984 | NE  | ARG | B | 83 | 42.494 | 109.046 | -18.818 | 1.00 | 34.41 | N |
| ATOM | 10986 | CZ  | ARG | B | 83 | 41.546 | 109.146 | -19.762 | 1.00 | 38.40 | C |
| ATOM | 10987 | NH1 | ARG | B | 83 | 41.090 | 108.057 | -20.386 | 1.00 | 41.70 | N |
| ATOM | 10990 | NH2 | ARG | B | 83 | 41.014 | 110.335 | -20.071 | 1.00 | 38.98 | N |
| ATOM | 10993 | C   | ARG | B | 83 | 41.768 | 102.959 | -17.673 | 1.00 | 15.57 | C |
| ATOM | 10994 | O   | ARG | B | 83 | 42.642 | 102.104 | -17.606 | 1.00 | 13.95 | O |
| ATOM | 10996 | N   | VAL | B | 84 | 40.642 | 102.769 | -18.330 | 1.00 | 14.38 | N |
| ATOM | 10997 | CA  | VAL | B | 84 | 40.515 | 101.658 | -19.261 | 1.00 | 14.61 | C |
| ATOM | 10999 | CB  | VAL | B | 84 | 39.109 | 101.566 | -19.867 | 1.00 | 13.21 | C |
| ATOM | 11001 | CG1 | VAL | B | 84 | 39.052 | 100.473 | -20.908 | 1.00 | 14.05 | C |
| ATOM | 11005 | CG2 | VAL | B | 84 | 38.079 | 101.330 | -18.782 | 1.00 | 12.48 | C |
| ATOM | 11009 | C   | VAL | B | 84 | 41.537 | 101.855 | -20.362 | 1.00 | 14.46 | C |
| ATOM | 11010 | O   | VAL | B | 84 | 41.639 | 102.915 | -20.943 | 1.00 | 16.21 | O |
| ATOM | 11012 | N   | LYS | B | 85 | 42.256 | 100.795 | -20.699 | 1.00 | 15.05 | N |
| ATOM | 11013 | CA  | LYS | B | 85 | 43.265 | 100.885 | -21.735 | 1.00 | 16.73 | C |
| ATOM | 11015 | CB  | LYS | B | 85 | 43.812 | 99.503  | -22.073 | 1.00 | 17.04 | C |
| ATOM | 11018 | CG  | LYS | B | 85 | 44.904 | 99.575  | -23.094 | 1.00 | 18.45 | C |
| ATOM | 11021 | CD  | LYS | B | 85 | 45.774 | 98.366  | -23.090 | 1.00 | 22.04 | C |
| ATOM | 11024 | CE  | LYS | B | 85 | 46.857 | 98.458  | -24.166 | 1.00 | 22.89 | C |
| ATOM | 11027 | NZ  | LYS | B | 85 | 46.657 | 97.347  | -25.112 | 1.00 | 29.09 | N |
| ATOM | 11031 | C   | LYS | B | 85 | 42.708 | 101.546 | -22.998 | 1.00 | 17.95 | C |
| ATOM | 11032 | O   | LYS | B | 85 | 41.625 | 101.206 | -23.465 | 1.00 | 17.90 | O |
| ATOM | 11034 | N   | ASP | B | 86 | 43.491 | 102.487 | -23.533 | 1.00 | 20.11 | N |
| ATOM | 11035 | CA  | ASP | B | 86 | 43.160 | 103.231 | -24.733 | 1.00 | 22.62 | C |
| ATOM | 11037 | CB  | ASP | B | 86 | 44.005 | 104.518 | -24.741 | 1.00 | 23.18 | C |
| ATOM | 11040 | CG  | ASP | B | 86 | 43.621 | 105.485 | -25.847 | 1.00 | 25.44 | C |
| ATOM | 11041 | OD1 | ASP | B | 86 | 44.158 | 106.620 | -25.849 | 1.00 | 29.81 | O |
| ATOM | 11042 | OD2 | ASP | B | 86 | 42.814 | 105.120 | -26.720 | 1.00 | 25.55 | O |
| ATOM | 11043 | C   | ASP | B | 86 | 43.483 | 102.310 | -25.896 | 1.00 | 23.00 | C |
| ATOM | 11044 | O   | ASP | B | 86 | 44.589 | 102.349 | -26.455 | 1.00 | 24.89 | O |
| ATOM | 11046 | N   | SER | B | 87 | 42.526 | 101.461 | -26.243 | 1.00 | 23.26 | N |
| ATOM | 11047 | CA  | SER | B | 87 | 42.735 | 100.424 | -27.252 | 1.00 | 23.49 | C |
| ATOM | 11049 | CB  | SER | B | 87 | 43.246 | 99.163  | -26.573 | 1.00 | 24.20 | C |
| ATOM | 11052 | OG  | SER | B | 87 | 42.727 | 97.998  | -27.160 | 1.00 | 26.53 | O |
| ATOM | 11054 | C   | SER | B | 87 | 41.426 | 100.138 | -27.980 | 1.00 | 23.13 | C |
| ATOM | 11055 | O   | SER | B | 87 | 40.383 | 99.998  | -27.366 | 1.00 | 21.89 | O |
| ATOM | 11057 | N   | ASP | B | 88 | 41.484 | 100.089 | -29.302 | 1.00 | 23.24 | N |
| ATOM | 11058 | CA  | ASP | B | 88 | 40.303 | 99.769  | -30.095 | 1.00 | 23.66 | C |
| ATOM | 11060 | CB  | ASP | B | 88 | 40.618 | 99.898  | -31.607 | 1.00 | 24.35 | C |
| ATOM | 11063 | CG  | ASP | B | 88 | 40.724 | 101.335 | -32.073 | 1.00 | 26.50 | C |
| ATOM | 11064 | OD1 | ASP | B | 88 | 40.570 | 102.268 | -31.250 | 1.00 | 31.46 | O |
| ATOM | 11065 | OD2 | ASP | B | 88 | 40.954 | 101.540 | -33.289 | 1.00 | 28.84 | O |
| ATOM | 11066 | C   | ASP | B | 88 | 39.788 | 98.368  | -29.830 | 1.00 | 24.08 | C |
| ATOM | 11067 | O   | ASP | B | 88 | 38.588 | 98.140  | -29.858 | 1.00 | 23.37 | O |
| ATOM | 11069 | N   | GLU | B | 89 | 40.696 | 97.427  | -29.596 | 1.00 | 24.66 | N |
| ATOM | 11070 | CA  | GLU | B | 89 | 40.322 | 96.050  | -29.277 | 1.00 | 26.61 | C |
| ATOM | 11072 | CB  | GLU | B | 89 | 41.564 | 95.176  | -29.131 | 1.00 | 26.50 | C |
| ATOM | 11075 | CG  | GLU | B | 89 | 42.235 | 94.878  | -30.461 | 1.00 | 31.18 | C |
| ATOM | 11078 | CD  | GLU | B | 89 | 43.210 | 93.704  | -30.380 | 1.00 | 31.40 | C |
| ATOM | 11079 | OE1 | GLU | B | 89 | 43.693 | 93.410  | -29.242 | 1.00 | 37.53 | O |
| ATOM | 11080 | OE2 | GLU | B | 89 | 43.486 | 93.092  | -31.458 | 1.00 | 37.18 | O |
| ATOM | 11081 | C   | GLU | B | 89 | 39.517 | 95.950  | -27.975 | 1.00 | 25.16 | C |
| ATOM | 11082 | O   | GLU | B | 89 | 38.503 | 95.286  | -27.918 | 1.00 | 24.06 | O |
| ATOM | 11084 | N   | ILE | B | 90 | 40.000 | 96.609  | -26.934 | 1.00 | 25.76 | N |

| ATOM | 11085 | CA | ILE | B | 90 | 39.300 | 96.601 | -25.651 | 1.00 | 25.54 | C |
|------|-------|-----|-----|---|----|--------|--------|---------|------|-------|---|
| ATOM | 11087 | CB | ILE | B | 90 | 40.103 | 97.344 | -24.537 | 1.00 | 26.08 | C |
| ATOM | 11089 | CG1 | ILE | B | 90 | 41.489 | 96.714 | -24.331 | 1.00 | 27.77 | C |
| ATOM | 11092 | CD1 | ILE | B | 90 | 41.478 | 95.378 | -23.628 | 1.00 | 30.83 | C |
| ATOM | 11096 | CG2 | ILE | B | 90 | 39.296 | 97.398 | -23.232 | 1.00 | 26.80 | C |
| ATOM | 11100 | C | ILE | B | 90 | 37.935 | 97.249 | -25.829 | 1.00 | 25.00 | C |
| ATOM | 11101 | O | ILE | B | 90 | 36.911 | 96.654 | -25.500 | 1.00 | 24.57 | O |
| ATOM | 11103 | N | ARG | B | 91 | 37.913 | 98.469 | -26.355 | 1.00 | 25.08 | N |
| ATOM | 11104 | CA | ARG | B | 91 | 36.638 | 99.165 | -26.591 | 1.00 | 25.48 | C |
| ATOM | 11106 | CB | ARG | B | 91 | 36.837 | 100.440 | -27.388 | 1.00 | 25.86 | C |
| ATOM | 11109 | CG | ARG | B | 91 | 37.203 | 101.612 | -26.566 | 1.00 | 27.48 | C |
| ATOM | 11112 | CD | ARG | B | 91 | 37.401 | 102.842 | -27.459 | 1.00 | 29.70 | C |
| ATOM | 11115 | NE | ARG | B | 91 | 38.499 | 103.573 | -26.876 | 1.00 | 33.53 | N |
| ATOM | 11117 | CZ | ARG | B | 91 | 39.690 | 103.758 | -27.418 | 1.00 | 32.77 | C |
| ATOM | 11118 | NH1 | ARG | B | 91 | 39.986 | 103.374 | -28.665 | 1.00 | 33.87 | N |
| ATOM | 11121 | NH2 | ARG | B | 91 | 40.587 | 104.387 | -26.688 | 1.00 | 32.89 | N |
| ATOM | 11124 | C | ARG | B | 91 | 35.651 | 98.336 | -27.365 | 1.00 | 24.41 | C |
| ATOM | 11125 | O | ARG | B | 91 | 34.470 | 98.306 | -27.035 | 1.00 | 23.84 | O |
| ATOM | 11127 | N | SER | B | 92 | 36.116 | 97.723 | -28.447 | 1.00 | 23.77 | N |
| ATOM | 11128 | CA | SER | B | 92 | 35.267 | 96.915 | -29.283 | 1.00 | 23.74 | C |
| ATOM | 11130 | CB | SER | B | 92 | 36.034 | 96.454 | -30.529 | 1.00 | 24.30 | C |
| ATOM | 11133 | OG | SER | B | 92 | 35.223 | 95.599 | -31.316 | 1.00 | 27.40 | O |
| ATOM | 11135 | C | SER | B | 92 | 34.701 | 95.700 | -28.552 | 1.00 | 23.32 | C |
| ATOM | 11136 | O | SER | B | 92 | 33.556 | 95.348 | -28.723 | 1.00 | 22.81 | O |
| ATOM | 11138 | N | LYS | B | 93 | 35.514 | 95.059 | -27.736 | 1.00 | 23.53 | N |
| ATOM | 11139 | CA | LYS | B | 93 | 35.056 | 93.952 | -26.920 | 1.00 | 23.80 | C |
| ATOM | 11141 | CB | LYS | B | 93 | 36.255 | 93.426 | -26.150 | 1.00 | 24.79 | C |
| ATOM | 11144 | CG | LYS | B | 93 | 36.074 | 92.091 | -25.517 | 1.00 | 26.84 | C |
| ATOM | 11147 | CD | LYS | B | 93 | 37.131 | 91.895 | -24.434 | 1.00 | 28.91 | C |
| ATOM | 11150 | CE | LYS | B | 93 | 38.540 | 92.091 | -24.955 | 1.00 | 29.01 | C |
| ATOM | 11153 | NZ | LYS | B | 93 | 39.562 | 91.473 | -24.080 | 1.00 | 27.78 | N |
| ATOM | 11157 | C | LYS | B | 93 | 33.944 | 94.414 | -25.943 | 1.00 | 22.86 | C |
| ATOM | 11158 | O | LYS | B | 93 | 32.880 | 93.784 | -25.827 | 1.00 | 21.65 | O |
| ATOM | 11160 | N | ILE | B | 94 | 34.192 | 95.537 | -25.261 | 1.00 | 22.69 | N |
| ATOM | 11161 | CA | ILE | B | 94 | 33.177 | 96.092 | -24.360 | 1.00 | 22.15 | C |
| ATOM | 11163 | CB | ILE | B | 94 | 33.697 | 97.323 | -23.566 | 1.00 | 22.06 | C |
| ATOM | 11165 | CG1 | ILE | B | 94 | 34.777 | 96.866 | -22.585 | 1.00 | 21.76 | C |
| ATOM | 11168 | CD1 | ILE | B | 94 | 35.744 | 97.991 | -22.084 | 1.00 | 22.33 | C |
| ATOM | 11172 | CG2 | ILE | B | 94 | 32.566 | 98.008 | -22.802 | 1.00 | 22.70 | C |
| ATOM | 11176 | C | ILE | B | 94 | 31.929 | 96.415 | -25.135 | 1.00 | 22.16 | C |
| ATOM | 11177 | O | ILE | B | 94 | 30.830 | 95.950 | -24.791 | 1.00 | 22.25 | O |
| ATOM | 11179 | N | ASP | B | 95 | 32.085 | 97.195 | -26.211 | 1.00 | 22.09 | N |
| ATOM | 11180 | CA | ASP | B | 95 | 30.913 | 97.652 | -26.960 | 1.00 | 22.49 | C |
| ATOM | 11182 | CB | ASP | B | 95 | 31.285 | 98.655 | -28.067 | 1.00 | 22.73 | C |
| ATOM | 11185 | CG | ASP | B | 95 | 32.043 | 99.955 | -27.536 | 1.00 | 26.31 | C |
| ATOM | 11186 | OD1 | ASP | B | 95 | 32.247 | 100.193 | -26.286 | 1.00 | 25.81 | O |
| ATOM | 11187 | OD2 | ASP | B | 95 | 32.463 | 100.746 | -28.440 | 1.00 | 31.19 | O |
| ATOM | 11188 | C | ASP | B | 95 | 30.146 | 96.453 | -27.536 | 1.00 | 22.05 | C |
| ATOM | 11189 | O | ASP | B | 95 | 28.925 | 96.433 | -27.529 | 1.00 | 22.07 | O |
| ATOM | 11191 | N | LYS | B | 96 | 30.857 | 95.439 | -28.018 | 1.00 | 22.58 | N |
| ATOM | 11192 | CA | LYS | B | 96 | 30.186 | 94.302 | -28.654 | 1.00 | 22.93 | C |
| ATOM | 11194 | CB | LYS | B | 96 | 31.191 | 93.448 | -29.447 | 1.00 | 23.71 | C |
| ATOM | 11197 | CG | LYS | B | 96 | 31.520 | 94.088 | -30.812 | 1.00 | 25.72 | C |
| ATOM | 11200 | CD | LYS | B | 96 | 32.650 | 93.391 | -31.567 | 1.00 | 26.69 | C |
| ATOM | 11203 | CE | LYS | B | 96 | 32.815 | 94.041 | -32.947 | 1.00 | 28.29 | C |
| ATOM | 11206 | NZ | LYS | B | 96 | 31.588 | 93.954 | -33.818 | 1.00 | 31.53 | N |
| ATOM | 11210 | C | LYS | B | 96 | 29.332 | 93.449 | -27.705 | 1.00 | 22.30 | C |

| ATOM | 11211 | O | LYS B 96 | 28.353 | 92.841 | -28.143 | 1.00 | 21.04 | O |
|------|-------|-----|------------|---------|---------|---------|------|-------|---|
| ATOM | 11213 | N | SER B 97 | 29.682 | 93.391 | -26.421 | 1.00 | 21.17 | N |
| ATOM | 11214 | CA | SER B 97 | 28.841 | 92.635 | -25.466 | 1.00 | 21.44 | C |
| ATOM | 11216 | CB | SER B 97 | 29.564 | 92.291 | -24.124 | 1.00 | 22.26 | C |
| ATOM | 11219 | OG | SER B 97 | 29.979 | 93.444 | -23.449 | 1.00 | 26.19 | O |
| ATOM | 11221 | C | SER B 97 | 27.550 | 93.385 | -25.193 | 1.00 | 19.85 | C |
| ATOM | 11222 | O | SER B 97 | 26.481 | 92.781 | -25.060 | 1.00 | 18.98 | O |
| ATOM | 11224 | N | VAL B 98 | 27.652 | 94.714 | -25.109 | 1.00 | 18.99 | N |
| ATOM | 11225 | CA | VAL B 98 | 26.453 | 95.537 | -24.922 | 1.00 | 18.56 | C |
| ATOM | 11227 | CB | VAL B 98 | 26.816 | 97.017 | -24.775 | 1.00 | 18.27 | C |
| ATOM | 11229 | CG1 | VAL B 98 | 25.531 | 97.847 | -24.707 | 1.00 | 17.52 | C |
| ATOM | 11233 | CG2 | VAL B 98 | 27.703 | 97.215 | -23.561 | 1.00 | 18.75 | C |
| ATOM | 11237 | C | VAL B 98 | 25.526 | 95.392 | -26.120 | 1.00 | 18.83 | C |
| ATOM | 11238 | O | VAL B 98 | 24.307 | 95.233 | -25.973 | 1.00 | 17.81 | O |
| ATOM | 11240 | N | GLU B 99 | 26.131 | 95.458 | -27.301 | 1.00 | 20.30 | N |
| ATOM | 11241 | CA | GLU B 99 | 25.367 | 95.392 | -28.555 | 1.00 | 21.33 | C |
| ATOM | 11243 | CB | GLU B 99 | 26.280 | 95.660 | -29.754 | 1.00 | 21.30 | C |
| ATOM | 11246 | CG | GLU B 99 | 25.635 | 95.392 | -31.141 | 1.00 | 23.99 | C |
| ATOM | 11249 | CD | GLU B 99 | 24.362 | 96.196 | -31.388 | 1.00 | 28.39 | C |
| ATOM | 11250 | OE1 | GLU B 99 | 24.129 | 97.203 | -30.662 | 1.00 | 29.77 | O |
| ATOM | 11251 | OE2 | GLU B 99 | 23.613 | 95.831 | -32.336 | 1.00 | 30.94 | O |
| ATOM | 11252 | C | GLU B 99 | 24.698 | 94.035 | -28.691 | 1.00 | 21.48 | C |
| ATOM | 11253 | O | GLU B 99 | 23.557 | 93.933 | -29.130 | 1.00 | 21.45 | O |
| ATOM | 11255 | N | PHE B 100 | 25.410 | 92.985 | -28.286 | 1.00 | 21.52 | N |
| ATOM | 11256 | CA | PHE B 100 | 24.857 | 91.642 | -28.353 | 1.00 | 21.89 | C |
| ATOM | 11258 | CB | PHE B 100 | 25.823 | 90.591 | -27.813 | 1.00 | 22.11 | C |
| ATOM | 11261 | CG | PHE B 100 | 25.189 | 89.246 | -27.668 | 1.00 | 21.92 | C |
| ATOM | 11262 | CD1 | PHE B 100 | 24.930 | 88.485 | -28.800 | 1.00 | 22.50 | C |
| ATOM | 11264 | CE1 | PHE B 100 | 24.302 | 87.252 | -28.680 | 1.00 | 24.09 | C |
| ATOM | 11266 | CZ | PHE B 100 | 23.923 | 86.773 | -27.445 | 1.00 | 21.63 | C |
| ATOM | 11268 | CE2 | PHE B 100 | 24.144 | 87.538 | -26.310 | 1.00 | 23.25 | C |
| ATOM | 11270 | CD2 | PHE B 100 | 24.766 | 88.771 | -26.430 | 1.00 | 23.02 | C |
| ATOM | 11272 | C | PHE B 100 | 23.575 | 91.590 | -27.561 | 1.00 | 22.95 | C |
| ATOM | 11273 | O | PHE B 100 | 22.538 | 91.157 | -28.043 | 1.00 | 23.31 | O |
| ATOM | 11275 | N | LEU B 101 | 23.651 | 92.047 | -26.322 | 1.00 | 23.80 | N |
| ATOM | 11276 | CA | LEU B 101 | 22.498 | 92.012 | -25.463 | 1.00 | 25.07 | C |
| ATOM | 11278 | CB | LEU B 101 | 22.892 | 92.521 | -24.069 | 1.00 | 25.38 | C |
| ATOM | 11281 | CG | LEU B 101 | 21.978 | 92.056 | -22.970 | 1.00 | 27.93 | C |
| ATOM | 11283 | CD1 | LEU B 101 | 21.786 | 90.513 | -22.981 | 1.00 | 30.38 | C |
| ATOM | 11287 | CD2 | LEU B 101 | 22.538 | 92.514 | -21.661 | 1.00 | 27.59 | C |
| ATOM | 11291 | C | LEU B 101 | 21.353 | 92.834 | -26.050 | 1.00 | 26.09 | C |
| ATOM | 11292 | O | LEU B 101 | 20.225 | 92.379 | -26.110 | 1.00 | 25.96 | O |
| ATOM | 11294 | N | ARG B 102 | 21.666 | 94.035 | -26.513 | 1.00 | 27.59 | N |
| ATOM | 11295 | CA | ARG B 102 | 20.676 | 94.929 | -27.099 | 1.00 | 29.70 | C |
| ATOM | 11297 | CB | ARG B 102 | 21.391 | 96.197 | -27.545 | 1.00 | 29.89 | C |
| ATOM | 11300 | CG | ARG B 102 | 20.537 | 97.248 | -28.243 | 1.00 | 31.42 | C |
| ATOM | 11303 | CD | ARG B 102 | 21.466 | 98.343 | -28.737 | 1.00 | 34.13 | C |
| ATOM | 11306 | NE | ARG B 102 | 21.010 | 98.979 | -29.964 | 1.00 | 38.69 | N |
| ATOM | 11308 | CZ | ARG B 102 | 21.635 | 100.009 | -30.558 | 1.00 | 41.64 | C |
| ATOM | 11309 | NH1 | ARG B 102 | 22.753 | 100.533 | -30.035 | 1.00 | 42.85 | N |
| ATOM | 11312 | NH2 | ARG B 102 | 21.135 | 100.533 | -31.682 | 1.00 | 41.16 | N |
| ATOM | 11315 | C | ARG B 102 | 19.981 | 94.277 | -28.292 | 1.00 | 30.11 | C |
| ATOM | 11316 | O | ARG B 102 | 18.746 | 94.224 | -28.374 | 1.00 | 29.72 | O |
| ATOM | 11318 | N | SER B 103 | 20.796 | 93.787 | -29.219 | 1.00 | 31.09 | N |
| ATOM | 11319 | CA | SER B 103 | 20.273 | 93.182 | -30.438 | 1.00 | 32.03 | C |
| ATOM | 11321 | CB | SER B 103 | 21.393 | 92.879 | -31.428 | 1.00 | 32.26 | C |
| ATOM | 11324 | OG | SER B 103 | 21.991 | 91.654 | -31.078 | 1.00 | 34.05 | O |

| ATOM | 11326 | C | SER | B | 103 | 19.481 | 91.909 | -30.131 | 1.00 | 32.88 | C |
| ATOM | 11327 | O | SER | B | 103 | 18.414 | 91.708 | -30.703 | 1.00 | 31.91 | O |
| ATOM | 11329 | N | ASN | B | 104 | 19.985 | 91.045 | -29.252 | 1.00 | 33.90 | N |
| ATOM | 11330 | CA | ASN | B | 104 | 19.215 | 89.857 | -28.894 | 1.00 | 36.27 | C |
| ATOM | 11332 | CB | ASN | B | 104 | 20.030 | 88.808 | -28.080 | 1.00 | 36.76 | C |
| ATOM | 11335 | CG | ASN | B | 104 | 20.232 | 87.450 | -28.868 | 1.00 | 39.47 | C |
| ATOM | 11336 | OD1 | ASN | B | 104 | 19.958 | 86.367 | -28.336 | 1.00 | 42.07 | O |
| ATOM | 11337 | ND2 | ASN | B | 104 | 20.688 | 87.531 | -30.134 | 1.00 | 40.85 | N |
| ATOM | 11340 | C | ASN | B | 104 | 17.902 | 90.252 | -28.216 | 1.00 | 37.20 | C |
| ATOM | 11341 | O | ASN | B | 104 | 16.901 | 89.581 | -28.373 | 1.00 | 37.23 | O |
| ATOM | 11343 | N | LEU | B | 105 | 17.887 | 91.383 | -27.522 | 1.00 | 39.18 | N |
| ATOM | 11344 | CA | LEU | B | 105 | 16.641 | 91.892 | -26.939 | 1.00 | 40.64 | C |
| ATOM | 11346 | CB | LEU | B | 105 | 16.927 | 93.019 | -25.953 | 1.00 | 40.84 | C |
| ATOM | 11349 | CG | LEU | B | 105 | 15.718 | 93.302 | -25.058 | 1.00 | 42.70 | C |
| ATOM | 11351 | CD1 | LEU | B | 105 | 16.160 | 93.379 | -23.609 | 1.00 | 44.64 | C |
| ATOM | 11355 | CD2 | LEU | B | 105 | 14.948 | 94.563 | -25.494 | 1.00 | 44.02 | C |
| ATOM | 11359 | C | LEU | B | 105 | 15.648 | 92.393 | -27.988 | 1.00 | 41.89 | C |
| ATOM | 11360 | O | LEU | B | 105 | 14.447 | 92.128 | -27.893 | 1.00 | 41.43 | O |
| ATOM | 11362 | N | SER | B | 106 | 16.153 | 93.133 | -28.972 | 1.00 | 43.49 | N |
| ATOM | 11363 | CA | SER | B | 106 | 15.315 | 93.658 | -30.047 | 1.00 | 45.19 | C |
| ATOM | 11365 | CB | SER | B | 106 | 16.095 | 94.678 | -30.885 | 1.00 | 45.23 | C |
| ATOM | 11368 | OG | SER | B | 106 | 17.231 | 94.088 | -31.496 | 1.00 | 45.67 | O |
| ATOM | 11370 | C | SER | B | 106 | 14.779 | 92.545 | -30.953 | 1.00 | 46.94 | C |
| ATOM | 11371 | O | SER | B | 106 | 13.737 | 92.705 | -31.598 | 1.00 | 47.07 | O |
| ATOM | 11373 | N | MSE | B | 107 | 15.491 | 91.423 | -31.007 | 1.00 | 48.86 | N |
| ATOM | 11374 | CA | MSE | B | 107 | 15.067 | 90.293 | -31.827 | 1.00 | 51.36 | C |
| ATOM | 11376 | CB | MSE | B | 107 | 16.271 | 89.535 | -32.333 | 1.00 | 51.09 | C |
| ATOM | 11379 | CG | MSE | B | 107 | 17.022 | 90.237 | -33.413 | 1.00 | 54.06 | C |
| ATOM | 11382 | SE | MSE | B | 107 | 18.556 | 89.081 | -33.829 | 1.00 | 60.70 | SE |
| ATOM | 11383 | CE | MSE | B | 107 | 17.619 | 87.744 | -35.081 | 1.00 | 58.17 | C |
| ATOM | 11387 | C | MSE | B | 107 | 14.179 | 89.303 | -31.102 | 1.00 | 49.91 | C |
| ATOM | 11388 | O | MSE | B | 107 | 13.644 | 88.410 | -31.740 | 1.00 | 49.42 | O |
| ATOM | 11390 | N | SER | B | 108 | 14.033 | 89.425 | -29.785 | 1.00 | 49.43 | N |
| ATOM | 11391 | CA | SER | B | 108 | 13.259 | 88.436 | -29.050 | 1.00 | 49.23 | C |
| ATOM | 11393 | CB | SER | B | 108 | 13.537 | 88.488 | -27.542 | 1.00 | 49.35 | C |
| ATOM | 11396 | OG | SER | B | 108 | 12.692 | 89.415 | -26.890 | 1.00 | 49.53 | O |
| ATOM | 11398 | C | SER | B | 108 | 11.775 | 88.634 | -29.343 | 1.00 | 48.98 | C |
| ATOM | 11399 | O | SER | B | 108 | 11.094 | 87.682 | -29.697 | 1.00 | 48.89 | O |
| ATOM | 11401 | N | THR | B | 124 | 12.246 | 100.179 | -22.398 | 1.00 | 41.41 | N |
| ATOM | 11402 | CA | THR | B | 124 | 13.502 | 100.681 | -21.824 | 1.00 | 41.78 | C |
| ATOM | 11404 | CB | THR | B | 124 | 14.256 | 101.615 | -22.818 | 1.00 | 42.23 | C |
| ATOM | 11406 | OG1 | THR | B | 124 | 13.903 | 102.990 | -22.586 | 1.00 | 44.10 | O |
| ATOM | 11408 | CG2 | THR | B | 124 | 13.953 | 101.232 | -24.270 | 1.00 | 42.25 | C |
| ATOM | 11412 | C | THR | B | 124 | 13.292 | 101.412 | -20.473 | 1.00 | 41.03 | C |
| ATOM | 11413 | O | THR | B | 124 | 14.221 | 101.522 | -19.657 | 1.00 | 40.08 | O |
| ATOM | 11415 | N | GLU | B | 125 | 12.072 | 101.928 | -20.277 | 1.00 | 40.32 | N |
| ATOM | 11416 | CA | GLU | B | 125 | 11.598 | 102.421 | -18.981 | 1.00 | 40.08 | C |
| ATOM | 11418 | CB | GLU | B | 125 | 10.127 | 102.863 | -19.086 | 1.00 | 40.32 | C |
| ATOM | 11421 | CG | GLU | B | 125 | 9.853 | 104.025 | -20.057 | 1.00 | 42.73 | C |
| ATOM | 11424 | CD | GLU | B | 125 | 8.354 | 104.176 | -20.450 | 1.00 | 43.19 | C |
| ATOM | 11425 | OE1 | GLU | B | 125 | 7.583 | 103.173 | -20.416 | 1.00 | 46.61 | O |
| ATOM | 11426 | OE2 | GLU | B | 125 | 7.957 | 105.315 | -20.810 | 1.00 | 47.70 | O |
| ATOM | 11427 | C | GLU | B | 125 | 11.690 | 101.308 | -17.920 | 1.00 | 38.13 | C |
| ATOM | 11428 | O | GLU | B | 125 | 12.261 | 101.507 | -16.848 | 1.00 | 36.49 | O |
| ATOM | 11430 | N | ASP | B | 126 | 11.106 | 100.146 | -18.221 | 1.00 | 36.31 | N |
| ATOM | 11431 | CA | ASP | B | 126 | 11.048 | 99.055 | -17.241 | 1.00 | 35.28 | C |
| ATOM | 11433 | CB | ASP | B | 126 | 10.173 | 97.919 | -17.743 | 1.00 | 35.75 | C |

| ATOM | 11436 | CG  | ASP B 126 | 8.777  | 98.386  | -18.088 | 1.00 | 37.62 | C |
|------|-------|-----|-----------|--------|---------|---------|------|-------|---|
| ATOM | 11437 | OD1 | ASP B 126 | 8.300  | 99.331  | -17.412 | 1.00 | 40.94 | O |
| ATOM | 11438 | OD2 | ASP B 126 | 8.173  | 97.829  | -19.037 | 1.00 | 38.79 | O |
| ATOM | 11439 | C   | ASP B 126 | 12.441 | 98.520  | -16.908 | 1.00 | 33.16 | C |
| ATOM | 11440 | O   | ASP B 126 | 12.721 | 98.219  | -15.754 | 1.00 | 32.46 | O |
| ATOM | 11442 | N   | ALA B 127 | 13.304 | 98.390  | -17.921 | 1.00 | 30.91 | N |
| ATOM | 11443 | CA  | ALA B 127 | 14.719 | 98.048  | -17.670 | 1.00 | 28.60 | C |
| ATOM | 11445 | CB  | ALA B 127 | 15.511 | 97.947  | -18.998 | 1.00 | 28.79 | C |
| ATOM | 11449 | C   | ALA B 127 | 15.367 | 99.069  | -16.744 | 1.00 | 26.91 | C |
| ATOM | 11450 | O   | ALA B 127 | 16.144 | 98.701  | -15.857 | 1.00 | 25.75 | O |
| ATOM | 11452 | N   | ILE B 128 | 15.073 | 100.353 | -16.963 | 1.00 | 24.08 | N |
| ATOM | 11453 | CA  | ILE B 128 | 15.635 | 101.396 | -16.102 | 1.00 | 23.56 | C |
| ATOM | 11455 | CB  | ILE B 128 | 15.355 | 102.842 | -16.642 | 1.00 | 24.06 | C |
| ATOM | 11457 | CG1 | ILE B 128 | 16.290 | 103.133 | -17.833 | 1.00 | 24.27 | C |
| ATOM | 11460 | CD1 | ILE B 128 | 15.887 | 104.339 | -18.705 | 1.00 | 25.37 | C |
| ATOM | 11464 | CG2 | ILE B 128 | 15.619 | 103.898 | -15.568 | 1.00 | 24.37 | C |
| ATOM | 11468 | C   | ILE B 128 | 15.097 | 101.180 | -14.669 | 1.00 | 22.17 | C |
| ATOM | 11469 | O   | ILE B 128 | 15.867 | 101.242 | -13.707 | 1.00 | 20.11 | O |
| ATOM | 11471 | N   | SER B 129 | 13.786 | 100.939 | -14.564 | 1.00 | 21.62 | N |
| ATOM | 11472 | CA  | SER B 129 | 13.131 | 100.634 | -13.262 | 1.00 | 21.58 | C |
| ATOM | 11474 | CB  | SER B 129 | 11.610 | 100.468 | -13.440 | 1.00 | 21.39 | C |
| ATOM | 11477 | OG  | SER B 129 | 10.998 | 101.714 | -13.731 | 1.00 | 24.13 | O |
| ATOM | 11479 | C   | SER B 129 | 13.691 | 99.397  | -12.534 | 1.00 | 20.41 | C |
| ATOM | 11480 | O   | SER B 129 | 13.824 | 99.385  | -11.295 | 1.00 | 19.39 | O |
| ATOM | 11482 | N   | LEU B 130 | 14.014 | 98.351  | -13.293 | 1.00 | 19.82 | N |
| ATOM | 11483 | CA  | LEU B 130 | 14.565 | 97.126  | -12.710 | 1.00 | 19.56 | C |
| ATOM | 11485 | CB  | LEU B 130 | 14.748 | 96.041  | -13.785 | 1.00 | 19.58 | C |
| ATOM | 11488 | CG  | LEU B 130 | 15.382 | 94.723  | -13.320 | 1.00 | 21.54 | C |
| ATOM | 11490 | CD1 | LEU B 130 | 14.651 | 94.111  | -12.135 | 1.00 | 21.65 | C |
| ATOM | 11494 | CD2 | LEU B 130 | 15.429 | 93.734  | -14.498 | 1.00 | 21.40 | C |
| ATOM | 11498 | C   | LEU B 130 | 15.896 | 97.415  | -12.064 | 1.00 | 17.51 | C |
| ATOM | 11499 | O   | LEU B 130 | 16.188 | 96.895  | -10.988 | 1.00 | 18.28 | O |
| ATOM | 11501 | N   | GLN B 131 | 16.742 | 98.221  | -12.703 | 1.00 | 16.30 | N |
| ATOM | 11502 | CA  | GLN B 131 | 18.045 | 98.488  | -12.104 | 1.00 | 16.30 | C |
| ATOM | 11504 | CB  | GLN B 131 | 18.980 | 99.307  | -13.017 | 1.00 | 16.30 | C |
| ATOM | 11507 | CG  | GLN B 131 | 19.076 | 98.885  | -14.495 | 1.00 | 14.54 | C |
| ATOM | 11510 | CD  | GLN B 131 | 19.164 | 97.388  | -14.655 | 1.00 | 18.06 | C |
| ATOM | 11511 | OE1 | GLN B 131 | 20.077 | 96.742  | -14.100 | 1.00 | 18.68 | O |
| ATOM | 11512 | NE2 | GLN B 131 | 18.232 | 96.819  | -15.410 | 1.00 | 18.31 | N |
| ATOM | 11515 | C   | GLN B 131 | 17.812 | 99.244  | -10.790 | 1.00 | 14.35 | C |
| ATOM | 11516 | O   | GLN B 131 | 18.513 | 99.039  | -9.802  | 1.00 | 15.10 | O |
| ATOM | 11518 | N   | LYS B 132 | 16.850 | 100.161 | -10.810 | 1.00 | 15.54 | N |
| ATOM | 11519 | CA  | LYS B 132 | 16.486 | 100.932 | -9.602  | 1.00 | 14.54 | C |
| ATOM | 11521 | CB  | LYS B 132 | 15.459 | 102.013 | -9.941  | 1.00 | 14.49 | C |
| ATOM | 11524 | CG  | LYS B 132 | 16.127 | 103.196 | -10.731 | 1.00 | 15.44 | C |
| ATOM | 11527 | CD  | LYS B 132 | 15.157 | 104.258 | -11.161 | 1.00 | 16.19 | C |
| ATOM | 11530 | CE  | LYS B 132 | 15.838 | 105.369 | -11.956 | 1.00 | 17.10 | C |
| ATOM | 11533 | NZ  | LYS B 132 | 14.851 | 106.403 | -12.420 | 1.00 | 17.57 | N |
| ATOM | 11537 | C   | LYS B 132 | 15.967 | 100.020 | -8.473  | 1.00 | 13.37 | C |
| ATOM | 11538 | O   | LYS B 132 | 16.313 | 100.226 | -7.296  | 1.00 | 13.13 | O |
| ATOM | 11540 | N   | ALA B 133 | 15.177 | 99.021  | -8.814  | 1.00 | 13.17 | N |
| ATOM | 11541 | CA  | ALA B 133 | 14.738 | 98.039  | -7.764  | 1.00 | 13.37 | C |
| ATOM | 11543 | CB  | ALA B 133 | 13.672 | 97.088  | -8.275  | 1.00 | 13.50 | C |
| ATOM | 11547 | C   | ALA B 133 | 15.903 | 97.238  | -7.223  | 1.00 | 14.19 | C |
| ATOM | 11548 | O   | ALA B 133 | 15.918 | 96.876  | -6.054  | 1.00 | 12.94 | O |
| ATOM | 11550 | N   | LEU B 134 | 16.872 | 96.922  | -8.085  | 1.00 | 13.73 | N |
| ATOM | 11551 | CA  | LEU B 134 | 18.063 | 96.230  | -7.613  | 1.00 | 15.33 | C |

| ATOM | 11553 | CB | LEU | B | 134 | 18.976 | 95.859 | -8.781 | 1.00 | 16.07 | C |
|------|-------|-----|-----|---|-----|--------|--------|--------|------|-------|---|
| ATOM | 11556 | CG | LEU | B | 134 | 18.387 | 94.823 | -9.724 | 1.00 | 19.49 | C |
| ATOM | 11558 | CD1 | LEU | B | 134 | 19.375 | 94.580 | -10.927 | 1.00 | 24.46 | C |
| ATOM | 11562 | CD2 | LEU | B | 134 | 18.039 | 93.474 | -9.017 | 1.00 | 21.52 | C |
| ATOM | 11566 | C | LEU | B | 134 | 18.832 | 97.043 | -6.584 | 1.00 | 14.41 | C |
| ATOM | 11567 | O | LEU | B | 134 | 19.181 | 96.533 | -5.479 | 1.00 | 16.43 | O |
| ATOM | 11569 | N | LEU | B | 135 | 19.054 | 98.325 | -6.896 | 1.00 | 13.84 | N |
| ATOM | 11570 | CA | LEU | B | 135 | 19.822 | 99.187 | -5.971 | 1.00 | 14.55 | C |
| ATOM | 11572 | CB | LEU | B | 135 | 20.186 | 100.565 | -6.586 | 1.00 | 15.35 | C |
| ATOM | 11575 | CG | LEU | B | 135 | 21.160 | 100.586 | -7.764 | 1.00 | 18.35 | C |
| ATOM | 11577 | CD1 | LEU | B | 135 | 21.629 | 101.998 | -8.069 | 1.00 | 19.50 | C |
| ATOM | 11581 | CD2 | LEU | B | 135 | 22.302 | 99.652 | -7.550 | 1.00 | 21.25 | C |
| ATOM | 11585 | C | LEU | B | 135 | 19.000 | 99.438 | -4.732 | 1.00 | 14.04 | C |
| ATOM | 11586 | O | LEU | B | 135 | 19.520 | 99.485 | -3.640 | 1.00 | 13.63 | O |
| ATOM | 11588 | N | GLU | B | 136 | 17.709 | 99.697 | -4.916 | 1.00 | 12.88 | N |
| ATOM | 11589 | CA | GLU | B | 136 | 16.849 | 100.063 | -3.792 | 1.00 | 12.26 | C |
| ATOM | 11591 | CB | GLU | B | 136 | 15.372 | 100.024 | -4.165 | 1.00 | 12.09 | C |
| ATOM | 11594 | CG | GLU | B | 136 | 14.383 | 100.264 | -2.977 | 1.00 | 13.34 | C |
| ATOM | 11597 | CD | GLU | B | 136 | 12.924 | 100.093 | -3.368 | 1.00 | 13.26 | C |
| ATOM | 11598 | OE1 | GLU | B | 136 | 12.646 | 99.417 | -4.343 | 1.00 | 10.80 | O |
| ATOM | 11599 | OE2 | GLU | B | 136 | 12.021 | 100.652 | -2.707 | 1.00 | 13.89 | O |
| ATOM | 11600 | C | GLU | B | 136 | 17.072 | 99.118 | -2.598 | 1.00 | 11.58 | C |
| ATOM | 11601 | O | GLU | B | 136 | 17.343 | 99.562 | -1.481 | 1.00 | 11.54 | O |
| ATOM | 11603 | N | HIS | B | 137 | 16.898 | 97.814 | -2.827 | 1.00 | 11.75 | N |
| ATOM | 11604 | CA | HIS | B | 137 | 16.953 | 96.840 | -1.721 | 1.00 | 11.25 | C |
| ATOM | 11606 | CB | HIS | B | 137 | 16.270 | 95.519 | -2.101 | 1.00 | 11.20 | C |
| ATOM | 11609 | CG | HIS | B | 137 | 17.107 | 94.587 | -2.932 | 1.00 | 10.53 | C |
| ATOM | 11610 | ND1 | HIS | B | 137 | 17.195 | 94.689 | -4.313 | 1.00 | 15.70 | N |
| ATOM | 11612 | CE1 | HIS | B | 137 | 17.984 | 93.729 | -4.766 | 1.00 | 15.74 | C |
| ATOM | 11614 | NE2 | HIS | B | 137 | 18.379 | 92.989 | -3.750 | 1.00 | 13.80 | N |
| ATOM | 11616 | CD2 | HIS | B | 137 | 17.839 | 93.505 | -2.589 | 1.00 | 12.82 | C |
| ATOM | 11618 | C | HIS | B | 137 | 18.361 | 96.628 | -1.146 | 1.00 | 11.30 | C |
| ATOM | 11619 | O | HIS | B | 137 | 18.494 | 96.162 | -0.009 | 1.00 | 11.26 | O |
| ATOM | 11621 | N | GLN | B | 138 | 19.398 | 96.925 | -1.945 | 1.00 | 10.24 | N |
| ATOM | 11622 | CA | GLN | B | 138 | 20.759 | 96.732 | -1.538 | 1.00 | 11.50 | C |
| ATOM | 11624 | CB | GLN | B | 138 | 21.622 | 96.335 | -2.734 | 1.00 | 12.15 | C |
| ATOM | 11627 | CG | GLN | B | 138 | 21.338 | 94.909 | -3.241 | 1.00 | 14.14 | C |
| ATOM | 11630 | CD | GLN | B | 138 | 21.777 | 93.839 | -2.242 | 1.00 | 15.65 | C |
| ATOM | 11631 | OE1 | GLN | B | 138 | 22.607 | 94.091 | -1.371 | 1.00 | 17.97 | O |
| ATOM | 11632 | NE2 | GLN | B | 138 | 21.157 | 92.630 | -2.324 | 1.00 | 17.64 | N |
| ATOM | 11635 | C | GLN | B | 138 | 21.371 | 97.927 | -0.790 | 1.00 | 10.47 | C |
| ATOM | 11636 | O | GLN | B | 138 | 22.389 | 97.740 | -0.105 | 1.00 | 11.46 | O |
| ATOM | 11638 | N | LEU | B | 139 | 20.711 | 99.086 | -0.845 | 1.00 | 10.79 | N |
| ATOM | 11639 | CA | LEU | B | 139 | 21.162 | 100.271 | -0.112 | 1.00 | 10.34 | C |
| ATOM | 11641 | CB | LEU | B | 139 | 20.765 | 101.540 | -0.856 | 1.00 | 11.01 | C |
| ATOM | 11644 | CG | LEU | B | 139 | 21.347 | 101.701 | -2.263 | 1.00 | 11.05 | C |
| ATOM | 11646 | CD1 | LEU | B | 139 | 20.675 | 102.907 | -3.030 | 1.00 | 11.99 | C |
| ATOM | 11650 | CD2 | LEU | B | 139 | 22.885 | 101.871 | -2.164 | 1.00 | 13.00 | C |
| ATOM | 11654 | C | LEU | B | 139 | 20.544 | 100.196 | 1.288 | 1.00 | 10.28 | C |
| ATOM | 11655 | O | LEU | B | 139 | 19.749 | 101.026 | 1.693 | 1.00 | 10.82 | O |
| ATOM | 11657 | N | CYS | B | 140 | 20.980 | 99.180 | 2.028 | 1.00 | 11.31 | N |
| ATOM | 11658 | CA | CYS | B | 140 | 20.330 | 98.804 | 3.250 | 1.00 | 12.04 | C |
| ATOM | 11660 | CB | CYS | B | 140 | 19.717 | 97.427 | 3.054 | 1.00 | 12.38 | C |
| ATOM | 11663 | SG | CYS | B | 140 | 20.821 | 96.072 | 2.686 | 1.00 | 14.77 | S |
| ATOM | 11665 | C | CYS | B | 140 | 21.240 | 98.727 | 4.455 | 1.00 | 12.38 | C |
| ATOM | 11666 | O | CYS | B | 140 | 20.818 | 98.182 | 5.507 | 1.00 | 12.77 | O |
| ATOM | 11668 | N | GLY | B | 141 | 22.435 | 99.323 | 4.346 | 1.00 | 10.97 | N |

| ATOM | 11669 | CA | GLY B 141 | 23.439 | 99.257 | 5.419 | 1.00 | 11.00 | C |
|---|---|---|---|---|---|---|---|---|---|
| ATOM | 11672 | C | GLY B 141 | 23.381 | 100.492 | 6.274 | 1.00 | 11.50 | C |
| ATOM | 11673 | O | GLY B 141 | 22.749 | 101.491 | 5.910 | 1.00 | 12.63 | O |
| ATOM | 11675 | N | VAL B 142 | 24.118 | 100.426 | 7.386 | 1.00 | 10.68 | N |
| ATOM | 11676 | CA | VAL B 142 | 24.096 | 101.468 | 8.397 | 1.00 | 11.02 | C |
| ATOM | 11678 | CB | VAL B 142 | 23.974 | 100.830 | 9.807 | 1.00 | 12.71 | C |
| ATOM | 11680 | CG1 | VAL B 142 | 24.266 | 101.831 | 10.902 | 1.00 | 11.50 | C |
| ATOM | 11684 | CG2 | VAL B 142 | 22.673 | 100.124 | 9.942 | 1.00 | 12.29 | C |
| ATOM | 11688 | C | VAL B 142 | 25.320 | 102.380 | 8.283 | 1.00 | 12.48 | C |
| ATOM | 11689 | O | VAL B 142 | 26.466 | 101.947 | 8.193 | 1.00 | 11.67 | O |
| ATOM | 11691 | N | LEU B 143 | 25.009 | 103.673 | 8.288 | 1.00 | 11.35 | N |
| ATOM | 11692 | CA | LEU B 143 | 25.961 | 104.769 | 8.243 | 1.00 | 12.90 | C |
| ATOM | 11694 | CB | LEU B 143 | 26.027 | 105.293 | 6.812 | 1.00 | 13.63 | C |
| ATOM | 11697 | CG | LEU B 143 | 26.734 | 104.458 | 5.781 | 1.00 | 13.28 | C |
| ATOM | 11699 | CD1 | LEU B 143 | 26.414 | 105.007 | 4.391 | 1.00 | 13.45 | C |
| ATOM | 11703 | CB2 | LEU B 143 | 28.233 | 104.416 | 6.066 | 1.00 | 15.38 | C |
| ATOM | 11707 | C | LEU B 143 | 25.448 | 105.883 | 9.167 | 1.00 | 12.67 | C |
| ATOM | 11708 | O | LEU B 143 | 24.242 | 105.947 | 9.441 | 1.00 | 13.49 | O |
| ATOM | 11710 | N | PRO B 144 | 26.321 | 106.812 | 9.644 | 1.00 | 14.17 | N |
| ATOM | 11711 | CA | PRO B 144 | 25.851 | 107.891 | 10.480 | 1.00 | 14.69 | C |
| ATOM | 11713 | CB | PRO B 144 | 27.116 | 108.740 | 10.745 | 1.00 | 15.33 | C |
| ATOM | 11716 | CG | PRO B 144 | 28.206 | 108.093 | 10.091 | 1.00 | 15.12 | C |
| ATOM | 11719 | CD | PRO B 144 | 27.771 | 106.839 | 9.429 | 1.00 | 15.08 | C |
| ATOM | 11722 | C | PRO B 144 | 24.823 | 108.728 | 9.743 | 1.00 | 15.36 | C |
| ATOM | 11723 | O | PRO B 144 | 24.994 | 109.010 | 8.556 | 1.00 | 15.83 | O |
| ATOM | 11724 | N | SER B 145 | 23.775 | 109.121 | 10.437 | 1.00 | 15.81 | N |
| ATOM | 11725 | CA | SER B 145 | 22.694 | 109.878 | 9.804 | 1.00 | 16.40 | C |
| ATOM | 11727 | CB | SER B 145 | 21.371 | 109.796 | 10.626 | 1.00 | 16.02 | C |
| ATOM | 11730 | OG | SER B 145 | 21.554 | 110.332 | 11.912 | 1.00 | 17.19 | O |
| ATOM | 11732 | C | SER B 145 | 23.110 | 111.349 | 9.559 | 1.00 | 17.15 | C |
| ATOM | 11733 | O | SER B 145 | 22.545 | 112.009 | 8.692 | 1.00 | 17.61 | O |
| ATOM | 11735 | N | SER B 146 | 24.064 | 111.851 | 10.344 | 1.00 | 17.59 | N |
| ATOM | 11736 | CA | SER B 146 | 24.374 | 113.298 | 10.424 | 1.00 | 20.32 | C |
| ATOM | 11738 | CB | SER B 146 | 23.446 | 113.995 | 11.437 | 1.00 | 21.01 | C |
| ATOM | 11741 | OG | SER B 146 | 23.839 | 115.343 | 11.705 | 1.00 | 24.87 | O |
| ATOM | 11743 | C | SER B 146 | 25.780 | 113.500 | 10.918 | 1.00 | 21.45 | C |
| ATOM | 11744 | O | SER B 146 | 26.372 | 112.616 | 11.581 | 1.00 | 22.05 | O |
| ATOM | 11746 | N | PHE B 147 | 26.309 | 114.682 | 10.612 | 1.00 | 22.81 | N |
| ATOM | 11747 | CA | PHE B 147 | 27.591 | 115.081 | 11.154 | 1.00 | 22.62 | C |
| ATOM | 11749 | CB | PHE B 147 | 28.124 | 116.325 | 10.449 | 1.00 | 23.23 | C |
| ATOM | 11752 | CG | PHE B 147 | 28.776 | 116.023 | 9.160 | 1.00 | 24.74 | C |
| ATOM | 11753 | CD1 | PHE B 147 | 29.852 | 115.162 | 9.126 | 1.00 | 24.58 | C |
| ATOM | 11755 | CE1 | PHE B 147 | 30.494 | 114.852 | 7.936 | 1.00 | 29.38 | C |
| ATOM | 11757 | CZ | PHE B 147 | 30.066 | 115.431 | 6.743 | 1.00 | 29.08 | C |
| ATOM | 11759 | CE2 | PHE B 147 | 28.968 | 116.325 | 6.746 | 1.00 | 30.91 | C |
| ATOM | 11761 | CD2 | PHE B 147 | 28.324 | 116.613 | 7.974 | 1.00 | 29.98 | C |
| ATOM | 11763 | C | PHE B 147 | 27.491 | 115.348 | 12.645 | 1.00 | 23.15 | C |
| ATOM | 11764 | O | PHE B 147 | 28.529 | 115.415 | 13.315 | 1.00 | 23.43 | O |
| ATOM | 11766 | N | ASP B 148 | 26.264 | 115.494 | 13.162 | 1.00 | 23.56 | N |
| ATOM | 11767 | CA | ASP B 148 | 26.072 | 115.816 | 14.591 | 1.00 | 23.86 | C |
| ATOM | 11769 | CB | ASP B 148 | 24.577 | 115.923 | 14.945 | 1.00 | 24.51 | C |
| ATOM | 11772 | CG | ASP B 148 | 23.904 | 117.118 | 14.324 | 1.00 | 29.84 | C |
| ATOM | 11773 | OD1 | ASP B 148 | 24.594 | 118.008 | 13.737 | 1.00 | 34.58 | O |
| ATOM | 11774 | OD2 | ASP B 148 | 22.647 | 117.169 | 14.460 | 1.00 | 35.73 | O |
| ATOM | 11775 | C | ASP B 148 | 26.653 | 114.746 | 15.493 | 1.00 | 22.28 | C |
| ATOM | 11776 | O | ASP B 148 | 26.902 | 115.020 | 16.665 | 1.00 | 21.85 | O |
| ATOM | 11778 | N | SER B 149 | 26.813 | 113.510 | 14.999 | 1.00 | 20.78 | N |

| | | | | | | | | | |
|---|---|---|---|---|---|---|---|---|---|
| ATOM | 11779 | CA | SER | B | 149 | 27.353 | 112.422 | 15.820 | 1.00 21.23 | C |
| ATOM | 11781 | CB | SER | B | 149 | 26.806 | 111.065 | 15.348 | 1.00 21.48 | C |
| ATOM | 11784 | OG | SER | B | 149 | 27.154 | 110.831 | 13.984 | 1.00 20.37 | O |
| ATOM | 11786 | C | SER | B | 149 | 28.873 | 112.339 | 15.801 | 1.00 20.82 | C |
| ATOM | 11787 | O | SER | B | 149 | 29.454 | 111.585 | 16.593 | 1.00 20.30 | O |
| ATOM | 11789 | N | PHE | B | 150 | 29.509 | 113.074 | 14.877 | 1.00 20.42 | N |
| ATOM | 11790 | CA | PHE | B | 150 | 30.972 | 113.011 | 14.750 | 1.00 20.37 | C |
| ATOM | 11792 | CB | PHE | B | 150 | 31.481 | 113.644 | 13.477 | 1.00 19.90 | C |
| ATOM | 11795 | CG | PHE | B | 150 | 31.276 | 112.811 | 12.224 | 1.00 19.21 | C |
| ATOM | 11796 | CD1 | PHE | B | 150 | 30.102 | 112.096 | 11.975 | 1.00 18.07 | C |
| ATOM | 11798 | CE1 | PHE | B | 150 | 29.920 | 111.420 | 10.757 | 1.00 19.52 | C |
| ATOM | 11800 | CZ | PHE | B | 150 | 30.933 | 111.447 | 9.789 | 1.00 17.27 | C |
| ATOM | 11802 | CE2 | PHE | B | 150 | 32.091 | 112.134 | 10.058 | 1.00 17.12 | C |
| ATOM | 11804 | CD2 | PHE | B | 150 | 32.256 | 112.812 | 11.253 | 1.00 18.78 | C |
| ATOM | 11806 | C | PHE | B | 150 | 31.613 | 113.764 | 15.890 | 1.00 20.40 | C |
| ATOM | 11807 | O | PHE | B | 150 | 31.084 | 114.765 | 16.378 | 1.00 21.09 | O |
| ATOM | 11809 | N | ARG | B | 151 | 32.756 | 113.245 | 16.289 | 1.00 18.82 | N |
| ATOM | 11810 | CA | ARG | B | 151 | 33.549 | 113.752 | 17.421 | 1.00 17.34 | C |
| ATOM | 11812 | CB | ARG | B | 151 | 33.381 | 112.854 | 18.635 | 1.00 18.40 | C |
| ATOM | 11815 | CG | ARG | B | 151 | 31.950 | 112.810 | 19.160 | 1.00 21.14 | C |
| ATOM | 11818 | CD | ARG | B | 151 | 31.582 | 114.114 | 19.777 | 1.00 24.45 | C |
| ATOM | 11821 | NE | ARG | B | 151 | 30.266 | 114.043 | 20.393 | 1.00 25.13 | N |
| ATOM | 11823 | CZ | ARG | B | 151 | 29.126 | 114.321 | 19.768 | 1.00 28.07 | C |
| ATOM | 11824 | NH1 | ARG | B | 151 | 29.113 | 114.689 | 18.493 | 1.00 28.39 | N |
| ATOM | 11827 | NH2 | ARG | B | 151 | 27.987 | 114.223 | 20.438 | 1.00 29.10 | N |
| ATOM | 11830 | C | ARG | B | 151 | 34.982 | 113.760 | 16.949 | 1.00 16.47 | C |
| ATOM | 11831 | O | ARG | B | 151 | 35.311 | 113.186 | 15.923 | 1.00 17.21 | O |
| ATOM | 11833 | N | LEU | B | 152 | 35.851 | 114.436 | 17.685 | 1.00 16.25 | N |
| ATOM | 11834 | CA | LEU | B | 152 | 37.237 | 114.524 | 17.337 | 1.00 15.42 | C |
| ATOM | 11836 | CB | LEU | B | 152 | 37.968 | 115.378 | 18.397 | 1.00 16.05 | C |
| ATOM | 11839 | CG | LEU | B | 152 | 39.470 | 115.392 | 18.259 | 1.00 17.36 | C |
| ATOM | 11841 | CD1 | LEU | B | 152 | 39.965 | 116.068 | 17.020 | 1.00 19.39 | C |
| ATOM | 11845 | CD2 | LEU | B | 152 | 39.971 | 116.139 | 19.472 | 1.00 19.23 | C |
| ATOM | 11849 | C | LEU | B | 152 | 37.799 | 113.113 | 17.265 | 1.00 15.42 | C |
| ATOM | 11850 | O | LEU | B | 152 | 37.698 | 112.347 | 18.225 | 1.00 14.57 | O |
| ATOM | 11852 | N | GLY | B | 153 | 38.395 | 112.766 | 16.120 | 1.00 15.00 | N |
| ATOM | 11853 | CA | GLY | B | 153 | 39.021 | 111.467 | 15.916 | 1.00 15.25 | C |
| ATOM | 11856 | C | GLY | B | 153 | 38.069 | 110.312 | 15.767 | 1.00 14.51 | C |
| ATOM | 11857 | O | GLY | B | 153 | 38.486 | 109.123 | 15.755 | 1.00 14.62 | O |
| ATOM | 11859 | N | ARG | B | 154 | 36.777 | 110.629 | 15.612 | 1.00 13.81 | N |
| ATOM | 11860 | CA | ARG | B | 154 | 35.755 | 109.567 | 15.533 | 1.00 13.77 | C |
| ATOM | 11862 | CB | ARG | B | 154 | 35.023 | 109.398 | 16.878 | 1.00 16.27 | C |
| ATOM | 11865 | CG | ARG | B | 154 | 35.917 | 109.218 | 18.095 | 1.00 15.99 | C |
| ATOM | 11868 | CD | ARG | B | 154 | 36.489 | 107.846 | 18.186 | 1.00 16.83 | C |
| ATOM | 11871 | NE | ARG | B | 154 | 37.150 | 107.621 | 19.493 | 1.00 14.56 | N |
| ATOM | 11873 | CZ | ARG | B | 154 | 37.690 | 106.442 | 19.874 | 1.00 11.14 | C |
| ATOM | 11874 | NH1 | ARG | B | 154 | 37.695 | 105.344 | 19.115 | 1.00 16.56 | N |
| ATOM | 11877 | NH2 | ARG | B | 154 | 38.269 | 106.372 | 21.085 | 1.00 14.81 | N |
| ATOM | 11880 | C | ARG | B | 154 | 34.654 | 109.953 | 14.534 | 1.00 13.51 | C |
| ATOM | 11881 | O | ARG | B | 154 | 34.509 | 111.117 | 14.199 | 1.00 15.43 | O |
| ATOM | 11883 | N | GLY | B | 155 | 33.862 | 108.950 | 14.168 | 1.00 14.33 | N |
| ATOM | 11884 | CA | GLY | B | 155 | 32.603 | 109.149 | 13.453 | 1.00 13.74 | C |
| ATOM | 11887 | C | GLY | B | 155 | 32.298 | 108.328 | 12.213 | 1.00 13.78 | C |
| ATOM | 11888 | O | GLY | B | 155 | 31.115 | 108.162 | 11.870 | 1.00 12.87 | O |
| ATOM | 11890 | N | LEU | B | 156 | 33.321 | 107.825 | 11.536 | 1.00 13.75 | N |
| ATOM | 11891 | CA | LEU | B | 156 | 33.134 | 107.025 | 10.310 | 1.00 13.69 | C |
| ATOM | 11893 | CB | LEU | B | 156 | 33.940 | 107.653 | 9.154 | 1.00 14.25 | C |

| ATOM | 11896 | CG | LEU | B | 156 | 33.284 | 108.867 | 8.511 | 1.00 | 15.61 | C |
|------|-------|-----|-----|---|-----|--------|---------|-------|------|-------|---|
| ATOM | 11898 | CD1 | LEU | B | 156 | 34.203 | 109.433 | 7.484 | 1.00 | 15.81 | C |
| ATOM | 11902 | CD2 | LEU | B | 156 | 31.962 | 108.445 | 7.835 | 1.00 | 17.57 | C |
| ATOM | 11906 | C | LEU | B | 156 | 33.445 | 105.546 | 10.518 | 1.00 | 14.11 | C |
| ATOM | 11907 | O | LEU | B | 156 | 33.640 | 104.774 | 9.547 | 1.00 | 14.03 | O |
| ATOM | 11909 | N | GLU | B | 157 | 33.382 | 105.112 | 11.796 | 1.00 | 13.94 | N |
| ATOM | 11910 | CA | GLU | B | 157 | 33.673 | 103.701 | 12.124 | 1.00 | 15.70 | C |
| ATOM | 11912 | CB | GLU | B | 157 | 33.556 | 103.471 | 13.607 | 1.00 | 16.57 | C |
| ATOM | 11915 | CG | GLU | B | 157 | 34.564 | 104.226 | 14.448 | 1.00 | 21.46 | C |
| ATOM | 11918 | CD | GLU | B | 157 | 34.095 | 105.623 | 14.858 | 1.00 | 27.81 | C |
| ATOM | 11919 | OE1 | GLU | B | 157 | 33.038 | 106.100 | 14.372 | 1.00 | 18.56 | O |
| ATOM | 11920 | OE2 | GLU | B | 157 | 34.818 | 106.226 | 15.714 | 1.00 | 31.27 | O |
| ATOM | 11921 | C | GLU | B | 157 | 32.786 | 102.720 | 11.403 | 1.00 | 15.12 | C |
| ATOM | 11922 | O | GLU | B | 157 | 33.182 | 101.558 | 11.191 | 1.00 | 14.15 | O |
| ATOM | 11924 | N | ASN | B | 158 | 31.576 | 103.133 | 11.074 | 1.00 | 13.50 | N |
| ATOM | 11925 | CA | ASN | B | 158 | 30.644 | 102.241 | 10.348 | 1.00 | 13.00 | C |
| ATOM | 11927 | CB | ASN | B | 158 | 29.211 | 102.503 | 10.801 | 1.00 | 13.17 | C |
| ATOM | 11930 | CG | ASN | B | 158 | 28.916 | 101.869 | 12.135 | 1.00 | 14.45 | C |
| ATOM | 11931 | OD1 | ASN | B | 158 | 29.526 | 100.843 | 12.439 | 1.00 | 15.78 | O |
| ATOM | 11932 | ND2 | ASN | B | 158 | 27.976 | 102.424 | 12.904 | 1.00 | 16.36 | N |
| ATOM | 11935 | C | ASN | B | 158 | 30.715 | 102.311 | 8.821 | 1.00 | 12.81 | C |
| ATOM | 11936 | O | ASN | B | 158 | 29.800 | 101.837 | 8.156 | 1.00 | 12.84 | O |
| ATOM | 11938 | N | SER | B | 159 | 31.780 | 102.917 | 8.309 | 1.00 | 12.91 | N |
| ATOM | 11939 | CA | SER | B | 159 | 32.004 | 102.959 | 6.857 | 1.00 | 13.92 | C |
| ATOM | 11941 | CB | SER | B | 159 | 32.056 | 104.402 | 6.380 | 1.00 | 14.11 | C |
| ATOM | 11944 | OG | SER | B | 159 | 33.243 | 105.048 | 6.812 | 1.00 | 15.79 | O |
| ATOM | 11946 | C | SER | B | 159 | 33.282 | 102.288 | 6.461 | 1.00 | 13.79 | C |
| ATOM | 11947 | O | SER | B | 159 | 34.205 | 102.142 | 7.258 | 1.00 | 14.01 | O |
| ATOM | 11949 | N | LEU | B | 160 | 33.300 | 101.814 | 5.236 | 1.00 | 13.79 | N |
| ATOM | 11950 | CA | LEU | B | 160 | 34.465 | 101.124 | 4.710 | 1.00 | 14.84 | C |
| ATOM | 11952 | CB | LEU | B | 160 | 34.219 | 100.461 | 3.367 | 1.00 | 15.46 | C |
| ATOM | 11955 | CG | LEU | B | 160 | 33.560 | 99.107 | 3.279 | 1.00 | 18.51 | C |
| ATOM | 11957 | CD1 | LEU | B | 160 | 33.310 | 98.804 | 1.784 | 1.00 | 20.20 | C |
| ATOM | 11961 | CD2 | LEU | B | 160 | 34.401 | 98.034 | 3.964 | 1.00 | 18.34 | C |
| ATOM | 11965 | C | LEU | B | 160 | 35.588 | 102.153 | 4.529 | 1.00 | 13.44 | C |
| ATOM | 11966 | O | LEU | B | 160 | 35.374 | 103.302 | 4.091 | 1.00 | 13.97 | O |
| ATOM | 11968 | N | PRO | B | 161 | 36.834 | 101.740 | 4.836 | 1.00 | 14.39 | N |
| ATOM | 11969 | CA | PRO | B | 161 | 37.943 | 102.624 | 4.573 | 1.00 | 14.98 | C |
| ATOM | 11971 | CB | PRO | B | 161 | 39.163 | 101.748 | 4.852 | 1.00 | 15.32 | C |
| ATOM | 11974 | CG | PRO | B | 161 | 38.657 | 100.761 | 5.879 | 1.00 | 16.56 | C |
| ATOM | 11977 | CD | PRO | B | 161 | 37.272 | 100.486 | 5.469 | 1.00 | 15.96 | C |
| ATOM | 11980 | C | PRO | B | 161 | 37.991 | 103.115 | 3.121 | 1.00 | 13.35 | C |
| ATOM | 11981 | O | PRO | B | 161 | 37.724 | 102.341 | 2.186 | 1.00 | 14.75 | O |
| ATOM | 11982 | N | LEU | B | 162 | 38.402 | 104.358 | 2.957 | 1.00 | 13.75 | N |
| ATOM | 11983 | CA | LEU | B | 162 | 38.408 | 104.984 | 1.623 | 1.00 | 12.40 | C |
| ATOM | 11985 | CB | LEU | B | 162 | 38.867 | 106.453 | 1.671 | 1.00 | 13.09 | C |
| ATOM | 11988 | CG | LEU | B | 162 | 37.953 | 107.328 | 2.552 | 1.00 | 13.21 | C |
| ATOM | 11990 | CD1 | LEU | B | 162 | 38.576 | 108.723 | 2.558 | 1.00 | 17.59 | C |
| ATOM | 11994 | CD2 | LEU | B | 162 | 36.549 | 107.317 | 2.045 | 1.00 | 14.81 | C |
| ATOM | 11998 | C | LEU | B | 162 | 39.303 | 104.128 | 0.661 | 1.00 | 12.97 | C |
| ATOM | 11999 | O | LEU | B | 162 | 38.964 | 103.899 | -0.506 | 1.00 | 12.00 | O |
| ATOM | 12001 | N | GLU | B | 163 | 40.451 | 103.659 | 1.147 | 1.00 | 13.38 | N |
| ATOM | 12002 | CA | GLU | B | 163 | 41.364 | 102.892 | 0.288 | 1.00 | 14.14 | C |
| ATOM | 12004 | CB | GLU | B | 163 | 42.709 | 102.549 | 0.987 | 1.00 | 14.74 | C |
| ATOM | 12007 | CG | GLU | B | 163 | 42.603 | 101.714 | 2.228 | 1.00 | 14.50 | C |
| ATOM | 12010 | CD | GLU | B | 163 | 43.945 | 101.312 | 2.861 | 1.00 | 18.01 | C |
| ATOM | 12011 | OE1 | GLU | B | 163 | 44.887 | 102.104 | 2.782 | 1.00 | 23.36 | O |

| | | | | | | | | | |
|---|---|---|---|---|---|---|---|---|---|
| ATOM | 12012 | OE2 | GLU | B | 163 | 44.101 | 100.181 | 3.400 | 1.00 19.06 | O |
| ATOM | 12013 | C | GLU | B | 163 | 40.708 | 101.605 | -0.229 | 1.00 13.22 | C |
| ATOM | 12014 | O | GLU | B | 163 | 40.974 | 101.155 | -1.354 | 1.00 14.04 | O |
| ATOM | 12016 | N | VAL | B | 164 | 39.867 | 100.988 | 0.596 | 1.00 12.34 | N |
| ATOM | 12017 | CA | VAL | B | 164 | 39.242 | 99.757 | 0.196 | 1.00 12.49 | C |
| ATOM | 12019 | CB | VAL | B | 164 | 38.529 | 99.118 | 1.394 | 1.00 12.40 | C |
| ATOM | 12021 | CG1 | VAL | B | 164 | 37.584 | 98.014 | 0.946 | 1.00 12.95 | C |
| ATOM | 12025 | CG2 | VAL | B | 164 | 39.600 | 98.555 | 2.360 | 1.00 12.04 | C |
| ATOM | 12029 | C | VAL | B | 164 | 38.278 | 100.040 | -0.935 | 1.00 12.25 | C |
| ATOM | 12030 | O | VAL | B | 164 | 38.215 | 99.322 | -1.938 | 1.00 12.74 | O |
| ATOM | 12032 | N | VAL | B | 165 | 37.522 | 101.113 | -0.768 | 1.00 11.62 | N |
| ATOM | 12033 | CA | VAL | B | 165 | 36.583 | 101.561 | -1.815 | 1.00 12.03 | C |
| ATOM | 12035 | CB | VAL | B | 165 | 35.671 | 102.716 | -1.353 | 1.00 12.66 | C |
| ATOM | 12037 | CG1 | VAL | B | 165 | 34.729 | 103.130 | -2.499 | 1.00 14.22 | C |
| ATOM | 12041 | CG2 | VAL | B | 165 | 34.909 | 102.296 | -0.094 | 1.00 13.63 | C |
| ATOM | 12045 | C | VAL | B | 165 | 37.271 | 101.878 | -3.135 | 1.00 11.81 | C |
| ATOM | 12046 | O | VAL | B | 165 | 36.827 | 101.431 | -4.197 | 1.00 11.83 | O |
| ATOM | 12048 | N | ARG | B | 166 | 38.396 | 102.599 | -3.068 | 1.00 11.21 | N |
| ATOM | 12049 | CA | ARG | B | 166 | 39.167 | 102.878 | -4.280 | 1.00 11.67 | C |
| ATOM | 12051 | CB | ARG | B | 166 | 40.379 | 103.764 | -3.952 | 1.00 10.94 | C |
| ATOM | 12054 | CG | ARG | B | 166 | 39.967 | 105.261 | -3.734 | 1.00 11.92 | C |
| ATOM | 12057 | CD | ARG | B | 166 | 41.142 | 106.150 | -3.562 | 1.00 13.97 | C |
| ATOM | 12060 | NE | ARG | B | 166 | 42.127 | 106.037 | -4.648 | 1.00 14.62 | N |
| ATOM | 12062 | CZ | ARG | B | 166 | 42.100 | 106.763 | -5.764 | 1.00 13.98 | C |
| ATOM | 12063 | NH1 | ARG | B | 166 | 41.115 | 107.626 | -5.999 | 1.00 12.45 | N |
| ATOM | 12066 | NH2 | ARG | B | 166 | 43.024 | 106.611 | -6.708 | 1.00 15.07 | N |
| ATOM | 12069 | C | ARG | B | 166 | 39.677 | 101.590 | -4.938 | 1.00 12.27 | C |
| ATOM | 12070 | O | ARG | B | 166 | 39.581 | 101.434 | -6.154 | 1.00 12.51 | O |
| ATOM | 12072 | N | GLY | B | 167 | 40.221 | 100.665 | -4.137 | 1.00 12.25 | N |
| ATOM | 12073 | CA | GLY | B | 167 | 40.699 | 99.404 | -4.684 | 1.00 12.87 | C |
| ATOM | 12076 | C | GLY | B | 167 | 39.545 | 98.625 | -5.342 | 1.00 11.91 | C |
| ATOM | 12077 | O | GLY | B | 167 | 39.712 | 98.012 | -6.389 | 1.00 12.92 | O |
| ATOM | 12079 | N | ALA | B | 168 | 38.350 | 98.732 | -4.743 | 1.00 12.40 | N |
| ATOM | 12080 | CA | ALA | B | 168 | 37.170 | 98.049 | -5.245 | 1.00 12.70 | C |
| ATOM | 12082 | CB | ALA | B | 168 | 36.031 | 98.176 | -4.253 | 1.00 13.43 | C |
| ATOM | 12086 | C | ALA | B | 168 | 36.733 | 98.599 | -6.578 | 1.00 12.89 | C |
| ATOM | 12087 | O | ALA | B | 168 | 36.403 | 97.863 | -7.504 | 1.00 11.49 | O |
| ATOM | 12089 | N | MSE | B | 169 | 36.765 | 99.918 | -6.704 | 1.00 11.88 | N |
| ATOM | 12090 | CA | MSE | B | 169 | 36.396 | 100.545 | -7.980 | 1.00 13.73 | C |
| ATOM | 12092 | CB | MSE | B | 169 | 36.269 | 102.053 | -7.863 | 1.00 13.32 | C |
| ATOM | 12095 | CG | MSE | B | 169 | 35.163 | 102.406 | -6.922 | 1.00 13.77 | C |
| ATOM | 12098 | SE | MSE | B | 169 | 34.697 | 104.356 | -7.083 | 1.00 22.37 | SE |
| ATOM | 12099 | CE | MSE | B | 169 | 36.243 | 105.141 | -6.023 | 1.00 15.35 | C |
| ATOM | 12103 | C | MSE | B | 169 | 37.363 | 100.152 | -9.079 | 1.00 11.50 | C |
| ATOM | 12104 | O | MSE | B | 169 | 36.946 | 99.941 | -10.221 | 1.00 12.00 | O |
| ATOM | 12106 | N | THR | B | 170 | 38.644 | 100.038 | -8.744 | 1.00 10.05 | N |
| ATOM | 12107 | CA | THR | B | 170 | 39.677 | 99.710 | -9.709 | 1.00 10.67 | C |
| ATOM | 12109 | CB | THR | B | 170 | 41.076 | 99.816 | -9.060 | 1.00 11.07 | C |
| ATOM | 12111 | OG1 | THR | B | 170 | 41.288 | 101.149 | -8.574 | 1.00 12.19 | O |
| ATOM | 12113 | CG2 | THR | B | 170 | 42.142 | 99.484 | -10.018 | 1.00 12.04 | C |
| ATOM | 12117 | C | THR | B | 170 | 39.456 | 98.273 | -10.247 | 1.00 11.29 | C |
| ATOM | 12118 | O | THR | B | 170 | 39.490 | 97.979 | -11.453 | 1.00 11.58 | O |
| ATOM | 12120 | N | ILE | B | 171 | 39.291 | 97.338 | -9.296 | 1.00 11.14 | N |
| ATOM | 12121 | CA | ILE | B | 171 | 39.099 | 95.913 | -9.652 | 1.00 11.65 | C |
| ATOM | 12123 | CB | ILE | B | 171 | 39.140 | 95.003 | -8.395 | 1.00 11.80 | C |
| ATOM | 12125 | CG1 | ILE | B | 171 | 40.533 | 95.025 | -7.770 | 1.00 12.31 | C |
| ATOM | 12128 | CD1 | ILE | B | 171 | 40.565 | 94.419 | -6.360 | 1.00 14.34 | C |

| ATOM | 12132 | CG2 | ILE | B | 171 | 38.596 | 93.628 | -8.652 | 1.00 | 12.48 | C |
|---|---|---|---|---|---|---|---|---|---|---|---|
| ATOM | 12136 | C | ILE | B | 171 | 37.776 | 95.779 | -10.404 | 1.00 | 11.94 | C |
| ATOM | 12137 | O | ILE | B | 171 | 37.678 | 95.046 | -11.378 | 1.00 | 12.19 | O |
| ATOM | 12139 | N | ARG | B | 172 | 36.756 | 96.510 | -9.950 | 1.00 | 11.73 | N |
| ATOM | 12140 | CA | ARG | B | 172 | 35.447 | 96.437 | -10.612 | 1.00 | 13.01 | C |
| ATOM | 12142 | CB | ARG | B | 172 | 34.414 | 97.355 | -9.947 | 1.00 | 13.75 | C |
| ATOM | 12145 | CG | ARG | B | 172 | 33.090 | 97.394 | -10.681 | 1.00 | 14.82 | C |
| ATOM | 12148 | CD | ARG | B | 172 | 32.837 | 95.999 | -11.343 | 1.00 | 23.26 | C |
| ATOM | 12151 | NE | ARG | B | 172 | 31.899 | 95.311 | -10.608 | 1.00 | 25.39 | N |
| ATOM | 12153 | CZ | ARG | B | 172 | 31.596 | 94.024 | -10.641 | 1.00 | 20.08 | C |
| ATOM | 12154 | NH1 | ARG | B | 172 | 32.166 | 93.088 | -11.415 | 1.00 | 22.04 | N |
| ATOM | 12157 | NH2 | ARG | B | 172 | 30.657 | 93.695 | -9.828 | 1.00 | 21.32 | N |
| ATOM | 12160 | C | ARG | B | 172 | 35.592 | 96.818 | -12.085 | 1.00 | 12.18 | C |
| ATOM | 12161 | O | ARG | B | 172 | 35.096 | 96.105 | -12.965 | 1.00 | 13.24 | O |
| ATOM | 12163 | N | VAL | B | 173 | 36.292 | 97.908 | -12.377 | 1.00 | 11.97 | N |
| ATOM | 12164 | CA | VAL | B | 173 | 36.493 | 98.310 | -13.762 | 1.00 | 12.28 | C |
| ATOM | 12166 | CB | VAL | B | 173 | 37.241 | 99.659 | -13.888 | 1.00 | 13.24 | C |
| ATOM | 12168 | CG1 | VAL | B | 173 | 37.622 | 99.962 | -15.307 | 1.00 | 13.33 | C |
| ATOM | 12172 | CG2 | VAL | B | 173 | 36.370 | 100.808 | -13.309 | 1.00 | 14.19 | C |
| ATOM | 12176 | C | VAL | B | 173 | 37.233 | 97.225 | -14.549 | 1.00 | 12.16 | C |
| ATOM | 12177 | O | VAL | B | 173 | 36.837 | 96.854 | -15.656 | 1.00 | 12.61 | O |
| ATOM | 12179 | N | ASN | B | 174 | 38.344 | 96.767 | -13.989 | 1.00 | 12.39 | N |
| ATOM | 12180 | CA | ASN | B | 174 | 39.126 | 95.762 | -14.677 | 1.00 | 12.26 | C |
| ATOM | 12182 | CB | ASN | B | 174 | 40.308 | 95.335 | -13.833 | 1.00 | 12.67 | C |
| ATOM | 12185 | CG | ASN | B | 174 | 41.313 | 94.477 | -14.610 | 1.00 | 13.01 | C |
| ATOM | 12186 | OD1 | ASN | B | 174 | 42.001 | 94.971 | -15.492 | 1.00 | 13.02 | O |
| ATOM | 12187 | ND2 | ASN | B | 174 | 41.411 | 93.190 | -14.239 | 1.00 | 12.59 | N |
| ATOM | 12190 | C | ASN | B | 174 | 38.266 | 94.564 | -15.022 | 1.00 | 12.28 | C |
| ATOM | 12191 | O | ASN | B | 174 | 38.333 | 94.086 | -16.146 | 1.00 | 13.38 | O |
| ATOM | 12193 | N | SER | B | 175 | 37.470 | 94.093 | -14.064 | 1.00 | 12.94 | N |
| ATOM | 12194 | CA | SER | B | 175 | 36.652 | 92.873 | -14.250 | 1.00 | 14.67 | C |
| ATOM | 12196 | CB | SER | B | 175 | 36.004 | 92.406 | -12.945 | 1.00 | 15.40 | C |
| ATOM | 12199 | OG | SER | B | 175 | 35.032 | 93.329 | -12.491 | 1.00 | 19.64 | O |
| ATOM | 12201 | C | SER | B | 175 | 35.565 | 93.028 | -15.324 | 1.00 | 15.79 | C |
| ATOM | 12202 | O | SER | B | 175 | 35.083 | 92.024 | -15.916 | 1.00 | 17.40 | O |
| ATOM | 12204 | N | LEU | B | 176 | 35.184 | 94.271 | -15.595 | 1.00 | 15.07 | N |
| ATOM | 12205 | CA | LEU | B | 176 | 34.196 | 94.575 | -16.655 | 1.00 | 14.79 | C |
| ATOM | 12207 | CB | LEU | B | 176 | 33.289 | 95.725 | -16.204 | 1.00 | 15.09 | C |
| ATOM | 12210 | CG | LEU | B | 176 | 32.448 | 95.432 | -14.945 | 1.00 | 14.45 | C |
| ATOM | 12212 | CD1 | LEU | B | 176 | 31.757 | 96.681 | -14.482 | 1.00 | 17.46 | C |
| ATOM | 12216 | CD2 | LEU | B | 176 | 31.424 | 94.317 | -15.135 | 1.00 | 14.44 | C |
| ATOM | 12220 | C | LEU | B | 176 | 34.794 | 94.886 | -18.031 | 1.00 | 14.38 | C |
| ATOM | 12221 | O | LEU | B | 176 | 34.054 | 94.919 | -19.023 | 1.00 | 15.42 | O |
| ATOM | 12223 | N | THR | B | 177 | 36.124 | 95.104 | -18.105 | 1.00 | 14.39 | N |
| ATOM | 12224 | CA | THR | B | 177 | 36.768 | 95.379 | -19.377 | 1.00 | 15.57 | C |
| ATOM | 12226 | CB | THR | B | 177 | 38.157 | 96.006 | -19.270 | 1.00 | 17.12 | C |
| ATOM | 12228 | OG1 | THR | B | 177 | 39.059 | 95.060 | -18.690 | 1.00 | 20.51 | O |
| ATOM | 12230 | CG2 | THR | B | 177 | 38.109 | 97.266 | -18.449 | 1.00 | 15.10 | C |
| ATOM | 12234 | C | THR | B | 177 | 36.922 | 94.104 | -20.184 | 1.00 | 16.52 | C |
| ATOM | 12235 | O | THR | B | 177 | 37.301 | 94.143 | -21.350 | 1.00 | 15.41 | O |
| ATOM | 12237 | N | ARG | B | 178 | 36.662 | 92.976 | -19.529 | 1.00 | 16.94 | N |
| ATOM | 12238 | CA | ARG | B | 178 | 36.896 | 91.658 | -20.125 | 1.00 | 16.65 | C |
| ATOM | 12240 | CB | ARG | B | 178 | 37.050 | 90.601 | -19.003 | 1.00 | 15.85 | C |
| ATOM | 12243 | CG | ARG | B | 178 | 38.265 | 90.818 | -18.092 | 1.00 | 17.46 | C |
| ATOM | 12246 | CD | ARG | B | 178 | 38.222 | 90.071 | -16.755 | 1.00 | 16.92 | C |
| ATOM | 12249 | NE | ARG | B | 178 | 37.986 | 88.638 | -16.891 | 1.00 | 14.16 | N |
| ATOM | 12251 | CZ | ARG | B | 178 | 38.901 | 87.758 | -17.321 | 1.00 | 15.44 | C |

| | | | | | | | | | |
|---|---|---|---|---|---|---|---|---|---|
| ATOM | 12252 | NH1 | ARG | B | 178 | 40.125 | 88.174 | -17.634 | 1.00 15.81 | N |
| ATOM | 12255 | NH2 | ARG | B | 178 | 38.600 | 86.463 | -17.403 | 1.00 16.07 | N |
| ATOM | 12258 | C | ARG | B | 178 | 35.859 | 91.261 | -21.159 | 1.00 16.68 | C |
| ATOM | 12259 | O | ARG | B | 178 | 36.062 | 90.289 | -21.890 | 1.00 17.23 | O |
| ATOM | 12261 | N | GLY | B | 179 | 34.753 | 92.014 | -21.255 | 1.00 16.89 | N |
| ATOM | 12262 | CA | GLY | B | 179 | 33.787 | 91.824 | -22.328 | 1.00 16.22 | C |
| ATOM | 12265 | C | GLY | B | 179 | 32.735 | 90.742 | -22.124 | 1.00 15.86 | C |
| ATOM | 12266 | O | GLY | B | 179 | 32.067 | 90.319 | -23.079 | 1.00 15.82 | O |
| ATOM | 12268 | N | HIS | B | 180 | 32.558 | 90.320 | -20.878 | 1.00 14.43 | N |
| ATOM | 12269 | CA | HIS | B | 180 | 31.628 | 89.202 | -20.536 | 1.00 14.83 | C |
| ATOM | 12271 | CB | HIS | B | 180 | 32.342 | 88.252 | -19.563 | 1.00 14.33 | C |
| ATOM | 12274 | CG | HIS | B | 180 | 33.635 | 87.694 | -20.091 | 1.00 15.70 | C |
| ATOM | 12275 | ND1 | HIS | B | 180 | 34.745 | 87.531 | -19.291 | 1.00 13.97 | N |
| ATOM | 12277 | CE1 | HIS | B | 180 | 35.730 | 87.020 | -20.002 | 1.00 11.22 | C |
| ATOM | 12279 | NE2 | HIS | B | 180 | 35.306 | 86.840 | -21.239 | 1.00 14.92 | N |
| ATOM | 12281 | CD2 | HIS | B | 180 | 33.997 | 87.266 | -21.324 | 1.00 13.97 | C |
| ATOM | 12283 | C | HIS | B | 180 | 30.291 | 89.618 | -19.862 | 1.00 12.75 | C |
| ATOM | 12286 | N | SER | B | 181 | 30.249 | 90.952 | -19.675 | 1.00 13.43 | N |
| ATOM | 12287 | CA | SER | B | 181 | 29.319 | 91.544 | -18.765 | 1.00 12.97 | C |
| ATOM | 12289 | CB | SER | B | 181 | 30.107 | 92.260 | -17.682 | 1.00 13.16 | C |
| ATOM | 12292 | OG | SER | B | 181 | 31.060 | 91.411 | -17.065 | 1.00 15.44 | O |
| ATOM | 12294 | C | SER | B | 181 | 28.269 | 92.520 | -19.333 | 1.00 13.71 | C |
| ATOM | 12295 | O | SER | B | 181 | 27.257 | 92.735 | -18.675 | 1.00 13.41 | O |
| ATOM | 12297 | N | ALA | B | 182 | 28.506 | 93.097 | -20.524 | 1.00 13.83 | N |
| ATOM | 12298 | CA | ALA | B | 182 | 27.546 | 94.006 | -21.177 | 1.00 13.85 | C |
| ATOM | 12300 | CB | ALA | B | 182 | 26.249 | 93.286 | -21.511 | 1.00 14.12 | C |
| ATOM | 12304 | C | ALA | B | 182 | 27.292 | 95.274 | -20.383 | 1.00 14.67 | C |
| ATOM | 12305 | O | ALA | B | 182 | 26.200 | 95.818 | -20.363 | 1.00 15.97 | O |
| ATOM | 12307 | N | VAL | B | 183 | 28.359 | 95.788 | -19.774 | 1.00 14.81 | N |
| ATOM | 12308 | CA | VAL | B | 183 | 28.309 | 97.106 | -19.151 | 1.00 14.56 | C |
| ATOM | 12310 | CB | VAL | B | 183 | 28.979 | 97.071 | -17.770 | 1.00 14.36 | C |
| ATOM | 12312 | CG1 | VAL | B | 183 | 29.010 | 98.481 | -17.158 | 1.00 15.34 | C |
| ATOM | 12316 | CG2 | VAL | B | 183 | 28.237 | 96.083 | -16.796 | 1.00 14.66 | C |
| ATOM | 12320 | C | VAL | B | 183 | 29.023 | 98.099 | -20.076 | 1.00 14.74 | C |
| ATOM | 12321 | O | VAL | B | 183 | 30.150 | 97.830 | -20.538 | 1.00 14.86 | O |
| ATOM | 12323 | N | ARG | B | 184 | 28.396 | 99.243 | -20.349 | 1.00 14.78 | N |
| ATOM | 12324 | CA | ARG | B | 184 | 28.989 | 100.212 | -21.272 | 1.00 15.20 | C |
| ATOM | 12326 | CB | ARG | B | 184 | 28.049 | 101.357 | -21.578 | 1.00 15.77 | C |
| ATOM | 12329 | CG | ARG | B | 184 | 26.714 | 100.987 | -22.256 | 1.00 16.73 | C |
| ATOM | 12332 | CD | ARG | B | 184 | 25.766 | 102.184 | -22.188 | 1.00 17.28 | C |
| ATOM | 12335 | NE | ARG | B | 184 | 25.338 | 102.400 | -20.813 | 1.00 19.43 | N |
| ATOM | 12337 | CZ | ARG | B | 184 | 24.956 | 103.556 | -20.277 | 1.00 18.34 | C |
| ATOM | 12338 | NH1 | ARG | B | 184 | 24.883 | 104.663 | -20.999 | 1.00 20.96 | N |
| ATOM | 12341 | NH2 | ARG | B | 184 | 24.608 | 103.584 | -18.990 | 1.00 19.11 | N |
| ATOM | 12344 | C | ARG | B | 184 | 30.281 | 100.835 | -20.775 | 1.00 14.27 | C |
| ATOM | 12345 | O | ARG | B | 184 | 30.502 | 101.031 | -19.586 | 1.00 14.32 | O |
| ATOM | 12347 | N | LEU | B | 185 | 31.109 | 101.206 | -21.737 | 1.00 14.23 | N |
| ATOM | 12348 | CA | LEU | B | 185 | 32.343 | 101.894 | -21.451 | 1.00 14.42 | C |
| ATOM | 12350 | CB | LEU | B | 185 | 33.070 | 102.225 | -22.741 | 1.00 13.59 | C |
| ATOM | 12353 | CG | LEU | B | 185 | 34.422 | 102.892 | -22.596 | 1.00 15.32 | C |
| ATOM | 12355 | CD1 | LEU | B | 185 | 35.381 | 101.998 | -21.807 | 1.00 15.43 | C |
| ATOM | 12359 | CD2 | LEU | B | 185 | 34.980 | 103.239 | -23.972 | 1.00 16.09 | C |
| ATOM | 12363 | C | LEU | B | 185 | 32.112 | 103.183 | -20.663 | 1.00 13.42 | C |
| ATOM | 12364 | O | LEU | B | 185 | 32.878 | 103.478 | -19.749 | 1.00 12.67 | O |
| ATOM | 12366 | N | VAL | B | 186 | 31.052 | 103.912 | -20.969 | 1.00 13.55 | N |
| ATOM | 12367 | CA | VAL | B | 186 | 30.752 | 105.135 | -20.250 | 1.00 14.11 | C |
| ATOM | 12369 | CB | VAL | B | 186 | 29.548 | 105.851 | -20.874 | 1.00 14.37 | C |

| | | | | | | | | | | |
|---|---|---|---|---|---|---|---|---|---|---|
| ATOM | 12371 | CG1 | VAL | B | 186 | 28.306 | 105.083 | -20.702 | 1.00 15.81 | C |
| ATOM | 12375 | CG2 | VAL | B | 186 | 29.419 | 107.220 | -20.282 | 1.00 17.95 | C |
| ATOM | 12379 | C | VAL | B | 186 | 30.566 | 104.910 | -18.732 | 1.00 13.26 | C |
| ATOM | 12380 | O | VAL | B | 186 | 30.926 | 105.783 | -17.905 | 1.00 15.03 | O |
| ATOM | 12382 | N | VAL | B | 187 | 30.024 | 103.751 | -18.367 | 1.00 12.70 | N |
| ATOM | 12383 | CA | VAL | B | 187 | 29.861 | 103.366 | -16.967 | 1.00 13.21 | C |
| ATOM | 12385 | CB | VAL | B | 187 | 28.946 | 102.131 | -16.828 | 1.00 12.92 | C |
| ATOM | 12387 | CG1 | VAL | B | 187 | 28.925 | 101.585 | -15.404 | 1.00 16.79 | C |
| ATOM | 12391 | CG2 | VAL | B | 187 | 27.565 | 102.471 | -17.290 | 1.00 15.56 | C |
| ATOM | 12395 | C | VAL | B | 187 | 31.251 | 103.119 | -16.323 | 1.00 12.66 | C |
| ATOM | 12396 | O | VAL | B | 187 | 31.522 | 103.526 | -15.175 | 1.00 14.81 | O |
| ATOM | 12398 | N | LEU | B | 188 | 32.124 | 102.418 | -17.037 | 1.00 11.81 | N |
| ATOM | 12399 | CA | LEU | B | 188 | 33.451 | 102.151 | -16.514 | 1.00 12.03 | C |
| ATOM | 12401 | CB | LEU | B | 188 | 34.252 | 101.195 | -17.427 | 1.00 12.39 | C |
| ATOM | 12404 | CG | LEU | B | 188 | 33.523 | 99.888 | -17.770 | 1.00 15.14 | C |
| ATOM | 12406 | CD1 | LEU | B | 188 | 34.571 | 98.949 | -18.467 | 1.00 15.20 | C |
| ATOM | 12410 | CD2 | LEU | B | 188 | 32.873 | 99.256 | -16.610 | 1.00 20.67 | C |
| ATOM | 12414 | C | LEU | B | 188 | 34.206 | 103.454 | -16.347 | 1.00 12.17 | C |
| ATOM | 12415 | O | LEU | B | 188 | 34.875 | 103.665 | -15.314 | 1.00 12.44 | O |
| ATOM | 12417 | N | GLU | B | 189 | 34.063 | 104.343 | -17.334 | 1.00 13.33 | N |
| ATOM | 12418 | CA | GLU | B | 189 | 34.629 | 105.682 | -17.246 | 1.00 14.11 | C |
| ATOM | 12420 | CB | GLU | B | 189 | 34.452 | 106.442 | -18.578 | 1.00 14.62 | C |
| ATOM | 12423 | CG | GLU | B | 189 | 35.275 | 105.830 | -19.689 | 1.00 15.62 | C |
| ATOM | 12426 | CD | GLU | B | 189 | 35.061 | 106.546 | -21.042 | 1.00 17.72 | C |
| ATOM | 12427 | OE1 | GLU | B | 189 | 33.994 | 107.195 | -21.265 | 1.00 20.26 | O |
| ATOM | 12428 | OE2 | GLU | B | 189 | 35.930 | 106.397 | -21.927 | 1.00 20.23 | O |
| ATOM | 12429 | C | GLU | B | 189 | 34.083 | 106.504 | -16.083 | 1.00 13.34 | C |
| ATOM | 12430 | O | GLU | B | 189 | 34.786 | 107.333 | -15.530 | 1.00 13.30 | O |
| ATOM | 12432 | N | ALA | B | 190 | 32.844 | 106.266 | -15.689 | 1.00 13.66 | N |
| ATOM | 12433 | CA | ALA | B | 190 | 32.278 | 106.970 | -14.515 | 1.00 12.92 | C |
| ATOM | 12435 | CB | ALA | B | 190 | 30.844 | 106.622 | -14.338 | 1.00 13.26 | C |
| ATOM | 12439 | C | ALA | B | 190 | 33.065 | 106.597 | -13.262 | 1.00 12.60 | C |
| ATOM | 12440 | O | ALA | B | 190 | 33.408 | 107.441 | -12.441 | 1.00 12.63 | O |
| ATOM | 12442 | N | LEU | B | 191 | 33.408 | 105.326 | -13.159 | 1.00 11.98 | N |
| ATOM | 12443 | CA | LEU | B | 191 | 34.250 | 104.822 | -12.064 | 1.00 11.91 | C |
| ATOM | 12445 | CB | LEU | B | 191 | 34.244 | 103.277 | -12.037 | 1.00 13.41 | C |
| ATOM | 12448 | CG | LEU | B | 191 | 32.871 | 102.690 | -11.714 | 1.00 12.73 | C |
| ATOM | 12450 | CD1 | LEU | B | 191 | 32.859 | 101.194 | -12.089 | 1.00 15.69 | C |
| ATOM | 12454 | CD2 | LEU | B | 191 | 32.533 | 102.927 | -10.244 | 1.00 11.23 | C |
| ATOM | 12458 | C | LEU | B | 191 | 35.676 | 105.352 | -12.118 | 1.00 11.54 | C |
| ATOM | 12459 | O | LEU | B | 191 | 36.259 | 105.791 | -11.096 | 1.00 11.96 | O |
| ATOM | 12461 | N | THR | B | 192 | 36.270 | 105.304 | -13.308 | 1.00 11.37 | N |
| ATOM | 12462 | CA | THR | B | 192 | 37.648 | 105.799 | -13.396 | 1.00 11.19 | C |
| ATOM | 12464 | CB | THR | B | 192 | 38.378 | 105.332 | -14.712 | 1.00 12.74 | C |
| ATOM | 12466 | OG1 | THR | B | 192 | 37.712 | 105.902 | -15.850 | 1.00 11.23 | O |
| ATOM | 12468 | CG2 | THR | B | 192 | 38.402 | 103.804 | -14.816 | 1.00 11.95 | C |
| ATOM | 12472 | C | THR | B | 192 | 37.703 | 107.330 | -13.159 | 1.00 11.22 | C |
| ATOM | 12473 | O | THR | B | 192 | 38.651 | 107.830 | -12.554 | 1.00 11.08 | O |
| ATOM | 12475 | N | ASN | B | 193 | 36.660 | 108.039 | -13.552 | 1.00 10.88 | N |
| ATOM | 12476 | CA | ASN | B | 193 | 36.586 | 109.487 | -13.235 | 1.00 11.75 | C |
| ATOM | 12478 | CB | ASN | B | 193 | 35.476 | 110.158 | -13.994 | 1.00 11.49 | C |
| ATOM | 12481 | CG | ASN | B | 193 | 35.808 | 110.424 | -15.432 | 1.00 12.78 | C |
| ATOM | 12482 | OD1 | ASN | B | 193 | 36.979 | 110.584 | -15.800 | 1.00 13.44 | O |
| ATOM | 12483 | ND2 | ASN | B | 193 | 34.788 | 110.507 | -16.254 | 1.00 14.87 | N |
| ATOM | 12486 | C | ASN | B | 193 | 36.436 | 109.725 | -11.732 | 1.00 11.69 | C |
| ATOM | 12487 | O | ASN | B | 193 | 37.098 | 110.622 | -11.187 | 1.00 11.35 | O |
| ATOM | 12489 | N | PHE | B | 194 | 35.663 | 108.899 | -11.030 | 1.00 11.50 | N |

| ATOM | 12490 | CA | PHE | B | 194 | 35.644 | 108.979 | -9.567 | 1.00 | 11.45 | C |
|------|-------|-----|-----|---|-----|--------|---------|--------|------|-------|---|
| ATOM | 12492 | CB | PHE | B | 194 | 34.674 | 107.991 | -8.948 | 1.00 | 11.46 | C |
| ATOM | 12495 | CG | PHE | B | 194 | 33.272 | 108.508 | -8.814 | 1.00 | 11.77 | C |
| ATOM | 12496 | CD1 | PHE | B | 194 | 32.724 | 109.376 | -9.733 | 1.00 | 11.72 | C |
| ATOM | 12498 | CE1 | PHE | B | 194 | 31.409 | 109.817 | -9.556 | 1.00 | 13.56 | C |
| ATOM | 12500 | CZ | PHE | B | 194 | 30.680 | 109.375 | -8.475 | 1.00 | 11.62 | C |
| ATOM | 12502 | CE2 | PHE | B | 194 | 31.226 | 108.505 | -7.595 | 1.00 | 13.43 | C |
| ATOM | 12504 | CD2 | PHE | B | 194 | 32.507 | 108.088 | -7.763 | 1.00 | 12.42 | C |
| ATOM | 12506 | C | PHE | B | 194 | 37.027 | 108.766 | -9.005 | 1.00 | 12.45 | C |
| ATOM | 12507 | O | PHE | B | 194 | 37.500 | 109.532 | -8.155 | 1.00 | 12.70 | O |
| ATOM | 12509 | N | LEU | B | 195 | 37.710 | 107.715 | -9.460 | 1.00 | 12.34 | N |
| ATOM | 12510 | CA | LEU | B | 195 | 39.067 | 107.489 | -8.982 | 1.00 | 12.97 | C |
| ATOM | 12512 | CB | LEU | B | 195 | 39.694 | 106.222 | -9.631 | 1.00 | 12.22 | C |
| ATOM | 12515 | CG | LEU | B | 195 | 39.109 | 104.881 | -9.095 | 1.00 | 12.45 | C |
| ATOM | 12517 | CD1 | LEU | B | 195 | 39.385 | 103.756 | -10.079 | 1.00 | 14.62 | C |
| ATOM | 12521 | CD2 | LEU | B | 195 | 39.668 | 104.541 | -7.734 | 1.00 | 13.02 | C |
| ATOM | 12525 | C | LEU | B | 195 | 39.983 | 108.701 | -9.224 | 1.00 | 12.49 | C |
| ATOM | 12526 | O | LEU | B | 195 | 40.715 | 109.107 | -8.344 | 1.00 | 12.30 | O |
| ATOM | 12528 | N | ASN | B | 196 | 39.955 | 109.219 | -10.432 | 1.00 | 13.07 | N |
| ATOM | 12529 | CA | ASN | B | 196 | 40.961 | 110.188 | -10.868 | 1.00 | 13.15 | C |
| ATOM | 12531 | CB | ASN | B | 196 | 41.081 | 110.195 | -12.373 | 1.00 | 13.41 | C |
| ATOM | 12534 | CG | ASN | B | 196 | 41.555 | 108.860 | -12.912 | 1.00 | 14.07 | C |
| ATOM | 12535 | OD1 | ASN | B | 196 | 42.238 | 108.117 | -12.215 | 1.00 | 11.80 | O |
| ATOM | 12536 | ND2 | ASN | B | 196 | 41.207 | 108.562 | -14.159 | 1.00 | 13.61 | N |
| ATOM | 12539 | C | ASN | B | 196 | 40.690 | 111.559 | -10.305 | 1.00 | 13.95 | C |
| ATOM | 12540 | O | ASN | B | 196 | 41.587 | 112.381 | -10.268 | 1.00 | 15.14 | O |
| ATOM | 12542 | N | HIS | B | 197 | 39.449 | 111.788 | -9.889 | 1.00 | 13.19 | N |
| ATOM | 12543 | CA | HIS | B | 197 | 39.075 | 113.038 | -9.213 | 1.00 | 13.29 | C |
| ATOM | 12545 | CB | HIS | B | 197 | 37.759 | 113.567 | -9.779 | 1.00 | 13.79 | C |
| ATOM | 12548 | CG | HIS | B | 197 | 37.861 | 114.027 | -11.199 | 1.00 | 16.19 | C |
| ATOM | 12549 | ND1 | HIS | B | 197 | 38.635 | 115.102 | -11.566 | 1.00 | 19.67 | N |
| ATOM | 12551 | CE1 | HIS | B | 197 | 38.547 | 115.274 | -12.877 | 1.00 | 18.71 | C |
| ATOM | 12553 | NE2 | HIS | B | 197 | 37.773 | 114.330 | -13.375 | 1.00 | 19.34 | N |
| ATOM | 12555 | CD2 | HIS | B | 197 | 37.336 | 113.533 | -12.343 | 1.00 | 18.75 | C |
| ATOM | 12557 | C | HIS | B | 197 | 38.952 | 112.857 | -7.688 | 1.00 | 13.57 | C |
| ATOM | 12558 | O | HIS | B | 197 | 38.573 | 113.792 | -6.998 | 1.00 | 15.76 | O |
| ATOM | 12560 | N | GLY | B | 198 | 39.304 | 111.692 | -7.152 | 1.00 | 12.90 | N |
| ATOM | 12561 | CA | GLY | B | 198 | 39.314 | 111.492 | -5.734 | 1.00 | 12.83 | C |
| ATOM | 12564 | C | GLY | B | 198 | 37.947 | 111.588 | -5.092 | 1.00 | 12.91 | C |
| ATOM | 12565 | O | GLY | B | 198 | 37.805 | 112.095 | -3.944 | 1.00 | 13.51 | O |
| ATOM | 12567 | N | ILE | B | 199 | 36.946 | 111.084 | -5.804 | 1.00 | 12.84 | N |
| ATOM | 12568 | CA | ILE | B | 199 | 35.563 | 110.975 | -5.266 | 1.00 | 12.41 | C |
| ATOM | 12570 | CB | ILE | B | 199 | 34.527 | 111.281 | -6.337 | 1.00 | 13.12 | C |
| ATOM | 12572 | CG1 | ILE | B | 199 | 34.705 | 112.698 | -6.881 | 1.00 | 12.73 | C |
| ATOM | 12575 | CD1 | ILE | B | 199 | 33.895 | 112.950 | -8.107 | 1.00 | 13.95 | C |
| ATOM | 12579 | CG2 | ILE | B | 199 | 33.132 | 111.090 | -5.719 | 1.00 | 13.09 | C |
| ATOM | 12583 | C | ILE | B | 199 | 35.401 | 109.531 | -4.799 | 1.00 | 12.76 | C |
| ATOM | 12584 | O | ILE | B | 199 | 35.528 | 108.619 | -5.600 | 1.00 | 12.80 | O |
| ATOM | 12586 | N | THR | B | 200 | 35.159 | 109.317 | -3.510 | 1.00 | 11.81 | N |
| ATOM | 12587 | CA | THR | B | 200 | 35.127 | 107.971 | -2.936 | 1.00 | 11.54 | C |
| ATOM | 12589 | CB | THR | B | 200 | 36.283 | 107.684 | -1.947 | 1.00 | 12.25 | C |
| ATOM | 12591 | OG1 | THR | B | 200 | 37.549 | 108.031 | -2.505 | 1.00 | 13.11 | O |
| ATOM | 12593 | CG2 | THR | B | 200 | 36.306 | 106.218 | -1.608 | 1.00 | 13.06 | C |
| ATOM | 12597 | C | THR | B | 200 | 33.798 | 107.796 | -2.203 | 1.00 | 11.26 | C |
| ATOM | 12598 | O | THR | B | 200 | 33.492 | 108.534 | -1.249 | 1.00 | 12.21 | O |
| ATOM | 12600 | N | PRO | B | 201 | 32.959 | 106.885 | -2.733 | 1.00 | 12.19 | N |
| ATOM | 12601 | CA | PRO | B | 201 | 31.685 | 106.634 | -2.098 | 1.00 | 11.21 | C |

| | | | | | | | | | |
|---|---|---|---|---|---|---|---|---|---|
| ATOM | 12603 | CB | PRO | B | 201 | 31.109 | 105.493 | -2.919 | 1.00 | 11.29 | C |
| ATOM | 12606 | CG | PRO | B | 201 | 31.661 | 105.695 | -4.294 | 1.00 | 11.41 | C |
| ATOM | 12609 | CD | PRO | B | 201 | 33.082 | 106.161 | -4.018 | 1.00 | 13.24 | C |
| ATOM | 12612 | C | PRO | B | 201 | 31.801 | 106.262 | -0.636 | 1.00 | 11.64 | C |
| ATOM | 12613 | O | PRO | B | 201 | 32.704 | 105.534 | -0.253 | 1.00 | 12.33 | O |
| ATOM | 12614 | N | ILE | B | 202 | 30.854 | 106.746 | 0.145 | 1.00 | 11.99 | N |
| ATOM | 12615 | CA | ILE | B | 202 | 30.746 | 106.371 | 1.539 | 1.00 | 12.91 | C |
| ATOM | 12617 | CB | ILE | B | 202 | 30.074 | 107.498 | 2.368 | 1.00 | 13.37 | C |
| ATOM | 12619 | CG1 | ILE | B | 202 | 30.965 | 108.703 | 2.387 | 1.00 | 13.72 | C |
| ATOM | 12622 | CD1 | ILE | B | 202 | 32.323 | 108.503 | 2.973 | 1.00 | 16.59 | C |
| ATOM | 12626 | CG2 | ILE | B | 202 | 29.753 | 107.049 | 3.782 | 1.00 | 13.97 | C |
| ATOM | 12630 | C | ILE | B | 202 | 29.894 | 105.096 | 1.563 | 1.00 | 13.12 | C |
| ATOM | 12631 | O | ILE | B | 202 | 28.736 | 105.096 | 1.098 | 1.00 | 14.23 | O |
| ATOM | 12633 | N | VAL | B | 203 | 30.469 | 104.003 | 2.048 | 1.00 | 13.87 | N |
| ATOM | 12634 | CA | VAL | B | 203 | 29.832 | 102.709 | 1.944 | 1.00 | 12.69 | C |
| ATOM | 12636 | CB | VAL | B | 203 | 30.688 | 101.813 | 0.984 | 1.00 | 13.18 | C |
| ATOM | 12638 | CG1 | VAL | B | 203 | 30.121 | 100.398 | 0.842 | 1.00 | 16.21 | C |
| ATOM | 12642 | CG2 | VAL | B | 203 | 30.893 | 102.468 | -0.379 | 1.00 | 13.57 | C |
| ATOM | 12646 | C | VAL | B | 203 | 29.811 | 102.085 | 3.340 | 1.00 | 12.18 | C |
| ATOM | 12647 | O | VAL | B | 203 | 30.781 | 102.177 | 4.060 | 1.00 | 12.34 | O |
| ATOM | 12649 | N | PRO | B | 204 | 28.692 | 101.475 | 3.723 | 1.00 | 12.62 | N |
| ATOM | 12650 | CA | PRO | B | 204 | 28.661 | 100.808 | 5.040 | 1.00 | 11.59 | C |
| ATOM | 12652 | CB | PRO | B | 204 | 27.257 | 100.146 | 5.059 | 1.00 | 11.91 | C |
| ATOM | 12655 | CG | PRO | B | 204 | 26.451 | 100.984 | 4.108 | 1.00 | 11.74 | C |
| ATOM | 12658 | CD | PRO | B | 204 | 27.415 | 101.345 | 3.000 | 1.00 | 13.43 | C |
| ATOM | 12661 | C | PRO | B | 204 | 29.747 | 99.735 | 5.178 | 1.00 | 11.96 | C |
| ATOM | 12662 | O | PRO | B | 204 | 30.041 | 99.015 | 4.250 | 1.00 | 12.89 | O |
| ATOM | 12663 | N | LEU | B | 205 | 30.250 | 99.584 | 6.395 | 1.00 | 12.18 | N |
| ATOM | 12664 | CA | LEU | B | 205 | 31.298 | 98.606 | 6.713 | 1.00 | 12.27 | C |
| ATOM | 12666 | CB | LEU | B | 205 | 31.764 | 98.799 | 8.145 | 1.00 | 13.78 | C |
| ATOM | 12669 | CG | LEU | B | 205 | 32.855 | 97.862 | 8.663 | 1.00 | 13.69 | C |
| ATOM | 12671 | CD1 | LEU | B | 205 | 34.072 | 97.939 | 7.798 | 1.00 | 13.76 | C |
| ATOM | 12675 | CD2 | LEU | B | 205 | 33.211 | 98.226 | 10.054 | 1.00 | 12.53 | C |
| ATOM | 12679 | C | LEU | B | 205 | 30.731 | 97.210 | 6.608 | 1.00 | 11.83 | C |
| ATOM | 12680 | O | LEU | B | 205 | 31.381 | 96.258 | 6.147 | 1.00 | 11.80 | O |
| ATOM | 12682 | N | ARG | B | 206 | 29.504 | 97.079 | 7.110 | 1.00 | 12.43 | N |
| ATOM | 12683 | CA | ARG | B | 206 | 28.880 | 95.760 | 7.279 | 1.00 | 11.95 | C |
| ATOM | 12685 | CB | ARG | B | 206 | 28.566 | 95.506 | 8.760 | 1.00 | 11.42 | C |
| ATOM | 12688 | CG | ARG | B | 206 | 29.732 | 95.539 | 9.682 | 1.00 | 12.39 | C |
| ATOM | 12691 | CD | ARG | B | 206 | 29.323 | 95.096 | 11.104 | 1.00 | 13.86 | C |
| ATOM | 12694 | NE | ARG | B | 206 | 30.428 | 94.958 | 12.035 | 1.00 | 12.27 | N |
| ATOM | 12696 | CZ | ARG | B | 206 | 30.825 | 95.880 | 12.905 | 1.00 | 15.14 | C |
| ATOM | 12697 | NH1 | ARG | B | 206 | 30.244 | 97.079 | 12.973 | 1.00 | 17.10 | N |
| ATOM | 12700 | NH2 | ARG | B | 206 | 31.768 | 95.602 | 13.792 | 1.00 | 17.66 | N |
| ATOM | 12703 | C | ARG | B | 206 | 27.603 | 95.574 | 6.470 | 1.00 | 11.44 | C |
| ATOM | 12704 | O | ARG | B | 206 | 26.901 | 96.542 | 6.131 | 1.00 | 12.85 | O |
| ATOM | 12706 | N | GLY | B | 207 | 27.271 | 94.298 | 6.242 | 1.00 | 12.04 | N |
| ATOM | 12707 | CA | GLY | B | 207 | 26.040 | 93.941 | 5.609 | 1.00 | 12.16 | C |
| ATOM | 12710 | C | GLY | B | 207 | 26.159 | 92.940 | 4.488 | 1.00 | 13.35 | C |
| ATOM | 12711 | O | GLY | B | 207 | 25.147 | 92.378 | 4.106 | 1.00 | 15.23 | O |
| ATOM | 12713 | N | THR | B | 208 | 27.369 | 92.756 | 3.946 | 1.00 | 12.07 | N |
| ATOM | 12714 | CA | THR | B | 208 | 27.541 | 91.753 | 2.895 | 1.00 | 12.30 | C |
| ATOM | 12716 | CB | THR | B | 208 | 28.518 | 92.216 | 1.818 | 1.00 | 12.86 | C |
| ATOM | 12718 | OG1 | THR | B | 208 | 28.513 | 91.242 | 0.757 | 1.00 | 11.86 | O |
| ATOM | 12720 | CG2 | THR | B | 208 | 29.907 | 92.382 | 2.344 | 1.00 | 12.55 | C |
| ATOM | 12724 | C | THR | B | 208 | 27.998 | 90.414 | 3.480 | 1.00 | 12.14 | C |
| ATOM | 12725 | O | THR | B | 208 | 28.743 | 90.364 | 4.474 | 1.00 | 12.42 | O |

| ATOM | 12727 | N | ILE | B | 209 | 27.544 | 89.323 | 2.832 | 1.00 | 11.37 | N |
|------|-------|------|-----|---|-----|--------|--------|--------|------|-------|---|
| ATOM | 12728 | CA | ILE | B | 209 | 28.030 | 87.956 | 3.047 | 1.00 | 11.79 | C |
| ATOM | 12730 | CB | ILE | B | 209 | 26.878 | 86.943 | 3.208 | 1.00 | 12.53 | C |
| ATOM | 12732 | CG1 | ILE | B | 209 | 26.008 | 86.951 | 1.948 | 1.00 | 14.26 | C |
| ATOM | 12735 | CD1 | ILE | B | 209 | 24.806 | 86.039 | 2.079 | 1.00 | 12.23 | C |
| ATOM | 12739 | CG2 | ILE | B | 209 | 26.026 | 87.254 | 4.452 | 1.00 | 11.66 | C |
| ATOM | 12743 | C | ILE | B | 209 | 28.970 | 87.531 | 1.878 | 1.00 | 10.40 | C |
| ATOM | 12744 | O | ILE | B | 209 | 29.422 | 86.402 | 1.857 | 1.00 | 11.74 | O |
| ATOM | 12746 | N | SER | B | 210 | 29.310 | 88.475 | 0.972 | 1.00 | 11.39 | N |
| ATOM | 12747 | CA | SER | B | 210 | 30.267 | 88.234 | -0.078 | 1.00 | 11.11 | C |
| ATOM | 12749 | CB | SER | B | 210 | 31.659 | 88.190 | 0.483 | 1.00 | 10.90 | C |
| ATOM | 12752 | OG | SER | B | 210 | 31.969 | 89.336 | 1.247 | 1.00 | 12.29 | O |
| ATOM | 12754 | C | SER | B | 210 | 29.941 | 87.002 | -0.959 | 1.00 | 11.99 | C |
| ATOM | 12755 | O | SER | B | 210 | 30.796 | 86.207 | -1.300 | 1.00 | 13.07 | O |
| ATOM | 12757 | N | ALA | B | 211 | 28.658 | 86.897 | -1.351 | 1.00 | 11.96 | N |
| ATOM | 12758 | CA | ALA | B | 211 | 28.224 | 85.947 | -2.418 | 1.00 | 11.22 | C |
| ATOM | 12760 | CB | ALA | B | 211 | 27.464 | 84.797 | -1.875 | 1.00 | 10.96 | C |
| ATOM | 12764 | C | ALA | B | 211 | 27.425 | 86.845 | -3.392 | 1.00 | 13.05 | C |
| ATOM | 12767 | N | SER | B | 212 | 26.280 | 86.591 | -4.023 | 1.00 | 12.70 | N |
| ATOM | 12768 | CA | SER | B | 212 | 26.115 | 87.313 | -5.265 | 1.00 | 14.75 | C |
| ATOM | 12770 | CB | SER | B | 212 | 24.753 | 87.739 | -5.659 | 1.00 | 15.99 | C |
| ATOM | 12774 | C | SER | B | 212 | 27.199 | 88.326 | -5.135 | 1.00 | 13.62 | C |
| ATOM | 12775 | O | SER | B | 212 | 27.374 | 89.300 | -5.873 | 1.00 | 13.10 | O |
| ATOM | 12777 | N | GLY | B | 213 | 28.104 | 87.925 | -4.248 | 1.00 | 13.27 | N |
| ATOM | 12778 | CA | GLY | B | 213 | 29.264 | 88.667 | -3.889 | 1.00 | 12.62 | C |
| ATOM | 12781 | C | GLY | B | 213 | 28.936 | 89.787 | -2.967 | 1.00 | 13.66 | C |
| ATOM | 12782 | O | GLY | B | 213 | 28.047 | 89.686 | -2.057 | 1.00 | 12.53 | O |
| ATOM | 12784 | N | ASP | B | 214 | 29.720 | 90.830 | -3.150 | 1.00 | 12.59 | N |
| ATOM | 12785 | CA | ASP | B | 214 | 29.733 | 91.998 | -2.245 | 1.00 | 11.95 | C |
| ATOM | 12787 | CB | ASP | B | 214 | 31.114 | 92.668 | -2.359 | 1.00 | 12.29 | C |
| ATOM | 12790 | CG | ASP | B | 214 | 32.220 | 91.793 | -1.865 | 1.00 | 14.46 | C |
| ATOM | 12791 | OD1 | ASP | B | 214 | 32.015 | 91.134 | -0.832 | 1.00 | 16.13 | O |
| ATOM | 12792 | OD2 | ASP | B | 214 | 33.292 | 91.783 | -2.525 | 1.00 | 14.17 | O |
| ATOM | 12793 | C | ASP | B | 214 | 28.593 | 92.952 | -2.655 | 1.00 | 12.73 | C |
| ATOM | 12794 | O | ASP | B | 214 | 28.795 | 94.155 | -2.972 | 1.00 | 13.43 | O |
| ATOM | 12796 | N | LEU | B | 215 | 27.354 | 92.430 | -2.645 | 1.00 | 13.22 | N |
| ATOM | 12797 | CA | LEU | B | 215 | 26.227 | 93.142 | -3.247 | 1.00 | 11.78 | C |
| ATOM | 12799 | CB | LEU | B | 215 | 24.960 | 92.296 | -3.079 | 1.00 | 12.10 | C |
| ATOM | 12802 | CG | LEU | B | 215 | 24.909 | 90.978 | -3.832 | 1.00 | 14.21 | C |
| ATOM | 12804 | CD1 | LEU | B | 215 | 23.754 | 90.140 | -3.312 | 1.00 | 15.14 | C |
| ATOM | 12808 | CD2 | LEU | B | 215 | 24.815 | 91.235 | -5.346 | 1.00 | 16.94 | C |
| ATOM | 12812 | C | LEU | B | 215 | 25.970 | 94.538 | -2.660 | 1.00 | 12.09 | C |
| ATOM | 12813 | O | LEU | B | 215 | 25.878 | 95.512 | -3.380 | 1.00 | 12.97 | O |
| ATOM | 12815 | N | SER | B | 216 | 25.813 | 94.595 | -1.366 | 1.00 | 12.70 | N |
| ATOM | 12816 | CA | SER | B | 216 | 25.449 | 95.846 | -0.759 | 1.00 | 13.43 | C |
| ATOM | 12818 | CB | SER | B | 216 | 25.097 | 95.664 | 0.726 | 1.00 | 14.57 | C |
| ATOM | 12821 | OG | SER | B | 216 | 24.613 | 96.915 | 1.214 | 1.00 | 14.10 | O |
| ATOM | 12823 | C | SER | B | 216 | 26.511 | 96.928 | -0.998 | 1.00 | 12.55 | C |
| ATOM | 12824 | O | SER | B | 216 | 26.187 | 97.981 | -1.560 | 1.00 | 13.06 | O |
| ATOM | 12826 | N | PRO | B | 217 | 27.774 | 96.656 | -0.626 | 1.00 | 12.82 | N |
| ATOM | 12827 | CA | PRO | B | 217 | 28.757 | 97.739 | -0.861 | 1.00 | 12.66 | C |
| ATOM | 12829 | CB | PRO | B | 217 | 30.055 | 97.161 | -0.313 | 1.00 | 14.07 | C |
| ATOM | 12832 | CG | PRO | B | 217 | 29.863 | 95.708 | -0.214 | 1.00 | 13.24 | C |
| ATOM | 12835 | CD | PRO | B | 217 | 28.398 | 95.522 | 0.075 | 1.00 | 12.59 | C |
| ATOM | 12838 | C | PRO | B | 217 | 28.911 | 98.138 | -2.332 | 1.00 | 13.13 | C |
| ATOM | 12839 | O | PRO | B | 217 | 29.053 | 99.332 | -2.673 | 1.00 | 13.21 | O |
| ATOM | 12840 | N | LEU | B | 218 | 28.878 | 97.164 | -3.223 | 1.00 | 12.65 | N |

| | | | | | | | | | |
|---|---|---|---|---|---|---|---|---|---|
| ATOM | 12841 | CA | LEU | B | 218 | 28.961 | 97.483 | -4.645 | 1.00 12.14 | C |
| ATOM | 12843 | CB | LEU | B | 218 | 29.074 | 96.217 | -5.487 | 1.00 13.94 | C |
| ATOM | 12846 | CG | LEU | B | 218 | 30.468 | 95.548 | -5.396 | 1.00 14.52 | C |
| ATOM | 12848 | CD1 | LEU | B | 218 | 30.510 | 94.253 | -6.104 | 1.00 13.28 | C |
| ATOM | 12852 | CD2 | LEU | B | 218 | 31.556 | 96.395 | -6.002 | 1.00 12.46 | C |
| ATOM | 12856 | C | LEU | B | 218 | 27.722 | 98.291 | -5.087 | 1.00 13.03 | C |
| ATOM | 12857 | O | LEU | B | 218 | 27.814 | 99.123 | -5.994 | 1.00 12.43 | O |
| ATOM | 12859 | N | SER | B | 219 | 26.566 | 98.035 | -4.478 | 1.00 13.40 | N |
| ATOM | 12860 | CA | SER | B | 219 | 25.374 | 98.862 | -4.766 | 1.00 12.79 | C |
| ATOM | 12862 | CB | SER | B | 219 | 24.112 | 98.289 | -4.107 | 1.00 14.14 | C |
| ATOM | 12865 | OG | SER | B | 219 | 23.804 | 97.033 | -4.749 | 1.00 17.79 | O |
| ATOM | 12867 | C | SER | B | 219 | 25.571 | 100.313 | -4.372 | 1.00 12.38 | C |
| ATOM | 12868 | O | SER | B | 219 | 25.084 | 101.186 | -5.053 | 1.00 11.84 | O |
| ATOM | 12870 | N | TYR | B | 220 | 26.267 | 100.557 | -3.264 | 1.00 11.42 | N |
| ATOM | 12871 | CA | TYR | B | 220 | 26.577 | 101.936 | -2.883 | 1.00 11.60 | C |
| ATOM | 12873 | CB | TYR | B | 220 | 27.171 | 102.067 | -1.484 | 1.00 12.06 | C |
| ATOM | 12876 | CG | TYR | B | 220 | 26.137 | 101.933 | -0.401 | 1.00 9.96 | C |
| ATOM | 12877 | CD1 | TYR | B | 220 | 25.608 | 103.044 | 0.199 | 1.00 13.36 | C |
| ATOM | 12879 | CE1 | TYR | B | 220 | 24.612 | 102.930 | 1.134 | 1.00 14.37 | C |
| ATOM | 12881 | CZ | TYR | B | 220 | 24.176 | 101.695 | 1.538 | 1.00 11.62 | C |
| ATOM | 12882 | OH | TYR | B | 220 | 23.166 | 101.579 | 2.486 | 1.00 12.25 | O |
| ATOM | 12884 | CE2 | TYR | B | 220 | 24.694 | 100.569 | 0.981 | 1.00 11.33 | C |
| ATOM | 12886 | CD2 | TYR | B | 220 | 25.680 | 100.695 | 0.010 | 1.00 10.67 | C |
| ATOM | 12888 | C | TYR | B | 220 | 27.459 | 102.597 | -3.936 | 1.00 11.49 | C |
| ATOM | 12889 | O | TYR | B | 220 | 27.239 | 103.761 | -4.276 | 1.00 13.51 | O |
| ATOM | 12891 | N | ILE | B | 221 | 28.430 | 101.854 | -4.473 | 1.00 11.59 | N |
| ATOM | 12892 | CA | ILE | B | 221 | 29.252 | 102.413 | -5.544 | 1.00 12.34 | C |
| ATOM | 12894 | CB | ILE | B | 221 | 30.423 | 101.480 | -5.844 | 1.00 12.27 | C |
| ATOM | 12896 | CG1 | ILE | B | 221 | 31.390 | 101.525 | -4.678 | 1.00 10.87 | C |
| ATOM | 12899 | CD1 | ILE | B | 221 | 32.399 | 100.357 | -4.619 | 1.00 12.91 | C |
| ATOM | 12903 | CG2 | ILE | B | 221 | 31.121 | 101.827 | -7.126 | 1.00 13.31 | C |
| ATOM | 12907 | C | ILE | B | 221 | 28.422 | 102.742 | -6.794 | 1.00 12.12 | C |
| ATOM | 12908 | O | ILE | B | 221 | 28.520 | 103.846 | -7.348 | 1.00 10.50 | O |
| ATOM | 12910 | N | ALA | B | 222 | 27.555 | 101.834 | -7.198 | 1.00 11.55 | N |
| ATOM | 12911 | CA | ALA | B | 222 | 26.710 | 102.030 | -8.340 | 1.00 12.02 | C |
| ATOM | 12913 | CB | ALA | B | 222 | 25.933 | 100.764 | -8.621 | 1.00 11.59 | C |
| ATOM | 12917 | C | ALA | B | 222 | 25.739 | 103.189 | -8.157 | 1.00 11.34 | C |
| ATOM | 12918 | O | ALA | B | 222 | 25.501 | 103.980 | -9.060 | 1.00 12.42 | O |
| ATOM | 12920 | N | ALA | B | 223 | 25.172 | 103.293 | -6.958 | 1.00 10.97 | N |
| ATOM | 12921 | CA | ALA | B | 223 | 24.288 | 104.413 | -6.636 | 1.00 10.65 | C |
| ATOM | 12923 | CB | ALA | B | 223 | 23.697 | 104.212 | -5.263 | 1.00 11.47 | C |
| ATOM | 12927 | C | ALA | B | 223 | 24.991 | 105.798 | -6.736 | 1.00 10.90 | C |
| ATOM | 12928 | O | ALA | B | 223 | 24.396 | 106.767 | -7.160 | 1.00 11.69 | O |
| ATOM | 12930 | N | ALA | B | 224 | 26.253 | 105.844 | -6.300 | 1.00 11.05 | N |
| ATOM | 12931 | CA | ALA | B | 224 | 27.033 | 107.045 | -6.340 | 1.00 11.85 | C |
| ATOM | 12933 | CB | ALA | B | 224 | 28.314 | 106.897 | -5.591 | 1.00 12.34 | C |
| ATOM | 12937 | C | ALA | B | 224 | 27.262 | 107.496 | -7.799 | 1.00 11.15 | C |
| ATOM | 12938 | O | ALA | B | 224 | 26.957 | 108.664 | -8.115 | 1.00 11.96 | O |
| ATOM | 12940 | N | ILE | B | 225 | 27.788 | 106.631 | -8.667 | 1.00 11.67 | N |
| ATOM | 12941 | CA | ILE | B | 225 | 28.028 | 107.047 | -10.043 | 1.00 11.30 | C |
| ATOM | 12943 | CB | ILE | B | 225 | 28.898 | 106.036 | -10.852 | 1.00 10.38 | C |
| ATOM | 12945 | CG1 | ILE | B | 225 | 28.232 | 104.653 | -10.949 | 1.00 11.23 | C |
| ATOM | 12948 | CD1 | ILE | B | 225 | 28.873 | 103.763 | -12.021 | 1.00 12.85 | C |
| ATOM | 12952 | CG2 | ILE | B | 225 | 30.244 | 105.945 | -10.240 | 1.00 12.56 | C |
| ATOM | 12956 | C | ILE | B | 225 | 26.734 | 107.382 | -10.797 | 1.00 10.48 | C |
| ATOM | 12957 | O | ILE | B | 225 | 26.751 | 108.103 | -11.801 | 1.00 10.79 | O |
| ATOM | 12959 | N | SER | B | 226 | 25.625 | 106.798 | -10.350 | 1.00 10.59 | N |

| | | | | | | | | | |
|---|---|---|---|---|---|---|---|---|---|
| ATOM | 12960 | CA | SER | B | 226 | 24.342 | 107.068 | -10.962 | 1.00 10.88 | C |
| ATOM | 12962 | CB | SER | B | 226 | 23.516 | 105.769 | -11.025 | 1.00 13.31 | C |
| ATOM | 12965 | OG | SER | B | 226 | 23.176 | 105.368 | -9.769 | 1.00 18.15 | O |
| ATOM | 12967 | C | SER | B | 226 | 23.581 | 108.242 | -10.290 | 1.00 11.87 | C |
| ATOM | 12968 | O | SER | B | 226 | 22.490 | 108.605 | -10.718 | 1.00 11.78 | O |
| ATOM | 12970 | N | GLY | B | 227 | 24.164 | 108.855 | -9.268 | 1.00 11.25 | N |
| ATOM | 12971 | CA | GLY | B | 227 | 23.581 | 110.046 | -8.682 | 1.00 12.25 | C |
| ATOM | 12974 | C | GLY | B | 227 | 22.290 | 109.793 | -7.898 | 1.00 12.30 | C |
| ATOM | 12975 | O | GLY | B | 227 | 21.403 | 110.653 | -7.893 | 1.00 12.38 | O |
| ATOM | 12977 | N | HIS | B | 228 | 22.189 | 108.623 | -7.258 | 1.00 11.29 | N |
| ATOM | 12978 | CA | HIS | B | 228 | 21.057 | 108.352 | -6.344 | 1.00 11.26 | C |
| ATOM | 12980 | CB | HIS | B | 228 | 21.313 | 107.098 | -5.520 | 1.00 12.17 | C |
| ATOM | 12983 | CG | HIS | B | 228 | 20.110 | 106.606 | -4.776 | 1.00 13.15 | C |
| ATOM | 12984 | ND1 | HIS | B | 228 | 19.619 | 107.239 | -3.652 | 1.00 12.14 | N |
| ATOM | 12986 | CE1 | HIS | B | 228 | 18.586 | 106.553 | -3.189 | 1.00 13.63 | C |
| ATOM | 12988 | NE2 | HIS | B | 228 | 18.400 | 105.494 | -3.953 | 1.00 11.20 | N |
| ATOM | 12990 | CD2 | HIS | B | 228 | 19.353 | 105.493 | -4.947 | 1.00 10.29 | C |
| ATOM | 12992 | C | HIS | B | 228 | 20.918 | 109.548 | -5.394 | 1.00 11.80 | C |
| ATOM | 12993 | O | HIS | B | 228 | 21.901 | 110.059 | -4.905 | 1.00 12.65 | O |
| ATOM | 12995 | N | PRO | B | 229 | 19.691 | 110.017 | -5.150 | 1.00 12.06 | N |
| ATOM | 12996 | CA | PRO | B | 229 | 19.512 | 111.201 | -4.277 | 1.00 12.49 | C |
| ATOM | 12998 | CB | PRO | B | 229 | 17.999 | 111.396 | -4.238 | 1.00 12.52 | C |
| ATOM | 13001 | CG | PRO | B | 229 | 17.439 | 110.560 | -5.330 | 1.00 13.65 | C |
| ATOM | 13004 | CD | PRO | B | 229 | 18.424 | 109.504 | -5.692 | 1.00 12.24 | C |
| ATOM | 13007 | C | PRO | B | 229 | 20.004 | 111.111 | -2.836 | 1.00 13.78 | C |
| ATOM | 13008 | O | PRO | B | 229 | 20.189 | 112.151 | -2.178 | 1.00 13.06 | O |
| ATOM | 13009 | N | ASP | B | 230 | 20.175 | 109.896 | -2.344 | 1.00 13.12 | N |
| ATOM | 13010 | CA | ASP | B | 230 | 20.621 | 109.634 | -0.961 | 1.00 14.10 | C |
| ATOM | 13012 | CB | ASP | B | 230 | 19.609 | 108.695 | -0.257 | 1.00 14.35 | C |
| ATOM | 13015 | CG | ASP | B | 230 | 19.770 | 108.667 | 1.239 | 1.00 17.35 | C |
| ATOM | 13016 | OD1 | ASP | B | 230 | 20.263 | 109.659 | 1.818 | 1.00 16.00 | O |
| ATOM | 13017 | OD2 | ASP | B | 230 | 19.410 | 107.640 | 1.856 | 1.00 13.69 | O |
| ATOM | 13018 | C | ASP | B | 230 | 22.005 | 109.027 | -0.927 | 1.00 14.36 | C |
| ATOM | 13019 | O | ASP | B | 230 | 22.422 | 108.504 | 0.091 | 1.00 15.47 | O |
| ATOM | 13021 | N | SER | B | 231 | 22.747 | 109.113 | -2.019 | 1.00 14.12 | N |
| ATOM | 13022 | CA | SER | B | 231 | 24.124 | 108.635 | -2.054 | 1.00 14.74 | C |
| ATOM | 13024 | CB | SER | B | 231 | 24.442 | 108.104 | -3.462 | 1.00 14.25 | C |
| ATOM | 13027 | OG | SER | B | 231 | 25.834 | 108.044 | -3.657 | 1.00 16.85 | O |
| ATOM | 13029 | C | SER | B | 231 | 25.118 | 109.734 | -1.620 | 1.00 12.93 | C |
| ATOM | 13030 | O | SER | B | 231 | 25.039 | 110.869 | -2.084 | 1.00 13.10 | O |
| ATOM | 13032 | N | LYS | B | 232 | 26.025 | 109.376 | -0.701 | 1.00 14.46 | N |
| ATOM | 13033 | CA | LYS | B | 232 | 27.063 | 110.300 | -0.205 | 1.00 14.56 | C |
| ATOM | 13035 | CB | LYS | B | 232 | 27.036 | 110.413 | 1.328 | 1.00 16.72 | C |
| ATOM | 13038 | CG | LYS | B | 232 | 25.649 | 110.317 | 1.964 | 1.00 25.16 | C |
| ATOM | 13041 | CD | LYS | B | 232 | 24.847 | 111.541 | 2.024 | 1.00 29.10 | C |
| ATOM | 13044 | CE | LYS | B | 232 | 23.605 | 111.232 | 2.941 | 1.00 30.65 | C |
| ATOM | 13047 | NZ | LYS | B | 232 | 22.888 | 112.463 | 3.526 | 1.00 36.59 | N |
| ATOM | 13051 | C | LYS | B | 232 | 28.447 | 109.866 | -0.660 | 1.00 13.32 | C |
| ATOM | 13052 | O | LYS | B | 232 | 28.737 | 108.672 | -0.766 | 1.00 11.05 | O |
| ATOM | 13054 | N | VAL | B | 233 | 29.323 | 110.847 | -0.882 | 1.00 11.33 | N |
| ATOM | 13055 | CA | VAL | B | 233 | 30.683 | 110.577 | -1.316 | 1.00 12.03 | C |
| ATOM | 13057 | CB | VAL | B | 233 | 30.837 | 110.764 | -2.865 | 1.00 12.60 | C |
| ATOM | 13059 | CG1 | VAL | B | 233 | 29.864 | 109.844 | -3.597 | 1.00 12.67 | C |
| ATOM | 13063 | CG2 | VAL | B | 233 | 30.612 | 112.243 | -3.225 | 1.00 11.05 | C |
| ATOM | 13067 | C | VAL | B | 233 | 31.632 | 111.489 | -0.586 | 1.00 11.94 | C |
| ATOM | 13068 | O | VAL | B | 233 | 31.245 | 112.545 | -0.122 | 1.00 13.02 | O |
| ATOM | 13070 | N | HIS | B | 234 | 32.877 | 111.052 | -0.472 | 1.00 11.79 | N |

| | | | | | | | | | |
|---|---|---|---|---|---|---|---|---|---|
| ATOM | 13071 | CA | HIS | B | 234 | 33.934 | 111.794 | 0.187 | 1.00 12.32 | C |
| ATOM | 13073 | CB | HIS | B | 234 | 34.748 | 110.851 | 1.045 | 1.00 12.42 | C |
| ATOM | 13076 | CG | HIS | B | 234 | 36.004 | 111.443 | 1.589 | 1.00 11.49 | C |
| ATOM | 13077 | ND1 | HIS | B | 234 | 37.134 | 111.624 | 0.822 | 1.00 17.02 | N |
| ATOM | 13079 | CE1 | HIS | B | 234 | 38.093 | 112.142 | 1.579 | 1.00 17.34 | C |
| ATOM | 13081 | NE2 | HIS | B | 234 | 37.634 | 112.239 | 2.820 | 1.00 13.93 | N |
| ATOM | 13083 | CD2 | HIS | B | 234 | 36.334 | 111.795 | 2.845 | 1.00 14.08 | C |
| ATOM | 13085 | C | HIS | B | 234 | 34.815 | 112.413 | -0.928 | 1.00 13.35 | C |
| ATOM | 13086 | O | HIS | B | 234 | 35.135 | 111.747 | -1.911 | 1.00 14.30 | O |
| ATOM | 13088 | N | VAL | B | 235 | 35.142 | 113.684 | -0.783 | 1.00 12.98 | N |
| ATOM | 13089 | CA | VAL | B | 235 | 36.051 | 114.415 | -1.649 | 1.00 14.48 | C |
| ATOM | 13091 | CB | VAL | B | 235 | 35.304 | 115.272 | -2.692 | 1.00 14.42 | C |
| ATOM | 13093 | CG1 | VAL | B | 235 | 34.402 | 114.379 | -3.521 | 1.00 20.24 | C |
| ATOM | 13097 | CG2 | VAL | B | 235 | 34.484 | 116.426 | -2.030 | 1.00 16.53 | C |
| ATOM | 13101 | C | VAL | B | 235 | 36.895 | 115.341 | -0.797 | 1.00 15.16 | C |
| ATOM | 13102 | O | VAL | B | 235 | 36.472 | 115.780 | 0.275 | 1.00 16.76 | O |
| ATOM | 13104 | N | VAL | B | 236 | 38.070 | 115.688 | -1.307 | 1.00 14.99 | N |
| ATOM | 13105 | CA | VAL | B | 236 | 38.774 | 116.859 | -0.782 | 1.00 15.50 | C |
| ATOM | 13107 | CB | VAL | B | 236 | 40.296 | 116.591 | -0.687 | 1.00 15.04 | C |
| ATOM | 13109 | CG1 | VAL | B | 236 | 41.056 | 117.874 | -0.261 | 1.00 17.11 | C |
| ATOM | 13113 | CG2 | VAL | B | 236 | 40.577 | 115.427 | 0.241 | 1.00 16.71 | C |
| ATOM | 13117 | C | VAL | B | 236 | 38.505 | 118.058 | -1.693 | 1.00 15.46 | C |
| ATOM | 13118 | O | VAL | B | 236 | 38.689 | 117.993 | -2.903 | 1.00 15.92 | O |
| ATOM | 13120 | N | HIS | B | 237 | 37.992 | 119.140 | -1.116 | 1.00 14.27 | N |
| ATOM | 13121 | CA | HIS | B | 237 | 37.634 | 120.321 | -1.847 | 1.00 14.77 | C |
| ATOM | 13123 | CB | HIS | B | 237 | 36.136 | 120.305 | -2.072 | 1.00 15.37 | C |
| ATOM | 13126 | CG | HIS | B | 237 | 35.629 | 121.470 | -2.831 | 1.00 18.01 | C |
| ATOM | 13127 | ND1 | HIS | B | 237 | 34.849 | 122.450 | -2.259 | 1.00 19.49 | N |
| ATOM | 13129 | CE1 | HIS | B | 237 | 34.570 | 123.362 | -3.172 | 1.00 19.65 | C |
| ATOM | 13131 | NE2 | HIS | B | 237 | 35.149 | 123.012 | -4.305 | 1.00 20.66 | N |
| ATOM | 13133 | CD2 | HIS | B | 237 | 35.847 | 121.852 | -4.106 | 1.00 19.59 | C |
| ATOM | 13135 | C | HIS | B | 237 | 38.019 | 121.515 | -0.999 | 1.00 14.45 | C |
| ATOM | 13136 | O | HIS | B | 237 | 37.747 | 121.514 | 0.201 | 1.00 13.61 | O |
| ATOM | 13138 | N | GLU | B | 238 | 38.659 | 122.496 | -1.618 | 1.00 14.66 | N |
| ATOM | 13139 | CA | GLU | B | 238 | 39.094 | 123.717 | -0.918 | 1.00 14.59 | C |
| ATOM | 13141 | CB | GLU | B | 238 | 37.907 | 124.641 | -0.678 | 1.00 14.89 | C |
| ATOM | 13144 | CG | GLU | B | 238 | 37.515 | 125.291 | -1.942 | 1.00 16.15 | C |
| ATOM | 13147 | CD | GLU | B | 238 | 36.395 | 126.272 | -1.823 | 1.00 18.03 | C |
| ATOM | 13148 | OE1 | GLU | B | 238 | 35.717 | 126.343 | -0.777 | 1.00 23.15 | O |
| ATOM | 13149 | OE2 | GLU | B | 238 | 36.216 | 126.980 | -2.804 | 1.00 21.22 | O |
| ATOM | 13150 | C | GLU | B | 238 | 39.847 | 123.338 | 0.361 | 1.00 15.89 | C |
| ATOM | 13151 | O | GLU | B | 238 | 39.606 | 123.831 | 1.463 | 1.00 15.67 | O |
| ATOM | 13153 | N | GLY | B | 239 | 40.739 | 122.382 | 0.225 | 1.00 16.53 | N |
| ATOM | 13154 | CA | GLY | B | 239 | 41.644 | 122.038 | 1.297 | 1.00 17.79 | C |
| ATOM | 13157 | C | GLY | B | 239 | 41.060 | 121.238 | 2.427 | 1.00 19.20 | C |
| ATOM | 13158 | O | GLY | B | 239 | 41.775 | 120.974 | 3.420 | 1.00 20.92 | O |
| ATOM | 13160 | N | LYS | B | 240 | 39.790 | 120.819 | 2.295 | 1.00 18.57 | N |
| ATOM | 13161 | CA | LYS | B | 240 | 39.057 | 120.148 | 3.383 | 1.00 19.10 | C |
| ATOM | 13163 | CB | LYS | B | 240 | 37.877 | 120.999 | 3.870 | 1.00 18.18 | C |
| ATOM | 13166 | CG | LYS | B | 240 | 38.284 | 122.268 | 4.637 | 1.00 24.67 | C |
| ATOM | 13169 | CD | LYS | B | 240 | 37.111 | 123.227 | 4.846 | 1.00 23.61 | C |
| ATOM | 13172 | CE | LYS | B | 240 | 36.711 | 124.018 | 3.554 | 1.00 27.62 | C |
| ATOM | 13175 | NZ | LYS | B | 240 | 37.722 | 124.977 | 2.953 | 1.00 23.15 | N |
| ATOM | 13179 | C | LYS | B | 240 | 38.444 | 118.862 | 2.878 | 1.00 16.63 | C |
| ATOM | 13180 | O | LYS | B | 240 | 37.922 | 118.832 | 1.775 | 1.00 15.23 | O |
| ATOM | 13182 | N | GLU | B | 241 | 38.454 | 117.830 | 3.717 | 1.00 17.04 | N |
| ATOM | 13183 | CA | GLU | B | 241 | 37.654 | 116.664 | 3.452 | 1.00 15.01 | C |

| | | | | | | | | | |
|---|---|---|---|---|---|---|---|---|---|
| ATOM | 13185 | CB  | GLU | B | 241 | 37.963 | 115.527 |  4.429 | 1.00 16.17 | C |
| ATOM | 13188 | CG  | GLU | B | 241 | 39.330 | 114.882 |  4.254 | 1.00 16.42 | C |
| ATOM | 13191 | CD  | GLU | B | 241 | 39.536 | 113.784 |  5.233 | 1.00 16.64 | C |
| ATOM | 13192 | OE1 | GLU | B | 241 | 39.028 | 112.634 |  5.026 | 1.00 16.17 | O |
| ATOM | 13193 | OE2 | GLU | B | 241 | 40.114 | 114.098 |  6.309 | 1.00 19.08 | O |
| ATOM | 13194 | C   | GLU | B | 241 | 36.196 | 117.060 |  3.632 | 1.00 15.61 | C |
| ATOM | 13195 | O   | GLU | B | 241 | 35.811 | 117.618 |  4.671 | 1.00 15.10 | O |
| ATOM | 13197 | N   | LYS | B | 242 | 35.356 | 116.658 |  2.686 | 1.00 14.11 | N |
| ATOM | 13198 | CA  | LYS | B | 242 | 33.932 | 116.908 |  2.742 | 1.00 14.57 | C |
| ATOM | 13200 | CB  | LYS | B | 242 | 33.541 | 117.996 |  1.744 | 1.00 14.59 | C |
| ATOM | 13203 | CG  | LYS | B | 242 | 34.276 | 119.278 |  1.960 | 1.00 15.56 | C |
| ATOM | 13206 | CD  | LYS | B | 242 | 33.703 | 120.383 |  1.146 | 1.00 16.74 | C |
| ATOM | 13209 | CE  | LYS | B | 242 | 34.485 | 121.650 |  1.394 | 1.00 17.27 | C |
| ATOM | 13212 | NZ  | LYS | B | 242 | 33.926 | 122.797 |  0.605 | 1.00 17.29 | N |
| ATOM | 13216 | C   | LYS | B | 242 | 33.190 | 115.630 |  2.376 | 1.00 14.78 | C |
| ATOM | 13217 | O   | LYS | B | 242 | 33.705 | 114.821 |  1.593 | 1.00 13.86 | O |
| ATOM | 13219 | N   | ILE | B | 243 | 32.005 | 115.465 |  2.948 | 1.00 14.72 | N |
| ATOM | 13220 | CA  | ILE | B | 243 | 31.051 | 114.445 |  2.514 | 1.00 15.08 | C |
| ATOM | 13222 | CB  | ILE | B | 243 | 30.618 | 113.486 |  3.654 | 1.00 15.57 | C |
| ATOM | 13224 | CG1 | ILE | B | 243 | 31.831 | 112.666 |  4.149 | 1.00 16.82 | C |
| ATOM | 13227 | CD1 | ILE | B | 243 | 31.619 | 111.938 |  5.488 | 1.00 19.14 | C |
| ATOM | 13231 | CG2 | ILE | B | 243 | 29.563 | 112.459 |  3.153 | 1.00 14.64 | C |
| ATOM | 13235 | C   | ILE | B | 243 | 29.855 | 115.141 |  1.924 | 1.00 14.44 | C |
| ATOM | 13236 | O   | ILE | B | 243 | 29.190 | 115.923 |  2.584 | 1.00 15.89 | O |
| ATOM | 13238 | N   | LEU | B | 244 | 29.610 | 114.904 |  0.641 | 1.00 12.77 | N |
| ATOM | 13239 | CA  | LEU | B | 244 | 28.583 | 115.555 | -0.120 | 1.00 13.85 | C |
| ATOM | 13241 | CB  | LEU | B | 244 | 29.253 | 116.357 | -1.242 | 1.00 13.17 | C |
| ATOM | 13244 | CG  | LEU | B | 244 | 30.341 | 117.353 | -0.907 | 1.00 13.89 | C |
| ATOM | 13246 | CD1 | LEU | B | 244 | 30.942 | 117.932 | -2.160 | 1.00 15.39 | C |
| ATOM | 13250 | CD2 | LEU | B | 244 | 29.767 | 118.443 | -0.025 | 1.00 17.85 | C |
| ATOM | 13254 | C   | LEU | B | 244 | 27.656 | 114.525 | -0.782 | 1.00 11.93 | C |
| ATOM | 13255 | O   | LEU | B | 244 | 27.996 | 113.348 | -0.933 | 1.00 11.68 | O |
| ATOM | 13257 | N   | TYR | B | 245 | 26.485 | 114.961 | -1.177 | 1.00 13.26 | N |
| ATOM | 13258 | CA  | TYR | B | 245 | 25.679 | 114.121 | -2.031 | 1.00 13.80 | C |
| ATOM | 13260 | CB  | TYR | B | 245 | 24.303 | 114.719 | -2.283 | 1.00 14.78 | C |
| ATOM | 13263 | CG  | TYR | B | 245 | 23.451 | 114.581 | -1.068 | 1.00 16.10 | C |
| ATOM | 13264 | CD1 | TYR | B | 245 | 22.816 | 113.367 | -0.769 | 1.00 21.10 | C |
| ATOM | 13266 | CE1 | TYR | B | 245 | 22.060 | 113.223 |  0.440 | 1.00 22.75 | C |
| ATOM | 13268 | CZ  | TYR | B | 245 | 21.920 | 114.339 |  1.285 | 1.00 21.85 | C |
| ATOM | 13269 | OH  | TYR | B | 245 | 21.156 | 114.230 |  2.453 | 1.00 23.24 | O |
| ATOM | 13271 | CE2 | TYR | B | 245 | 22.560 | 115.525 |  0.998 | 1.00 22.71 | C |
| ATOM | 13273 | CD2 | TYR | B | 245 | 23.309 | 115.647 | -0.178 | 1.00 22.53 | C |
| ATOM | 13275 | C   | TYR | B | 245 | 26.433 | 113.866 | -3.326 | 1.00 13.97 | C |
| ATOM | 13276 | O   | TYR | B | 245 | 27.191 | 114.739 | -3.818 | 1.00 11.26 | O |
| ATOM | 13278 | N   | ALA | B | 246 | 26.220 | 112.672 | -3.892 | 1.00 11.57 | N |
| ATOM | 13279 | CA  | ALA | B | 246 | 26.954 | 112.275 | -5.100 | 1.00 12.55 | C |
| ATOM | 13281 | CB  | ALA | B | 246 | 26.544 | 110.924 | -5.584 | 1.00 13.17 | C |
| ATOM | 13285 | C   | ALA | B | 246 | 26.781 | 113.298 | -6.214 | 1.00 11.77 | C |
| ATOM | 13286 | O   | ALA | B | 246 | 27.760 | 113.651 | -6.860 | 1.00 12.42 | O |
| ATOM | 13288 | N   | ARG | B | 247 | 25.553 | 113.765 | -6.449 | 1.00 12.25 | N |
| ATOM | 13289 | CA  | ARG | B | 247 | 25.354 | 114.782 | -7.521 | 1.00 12.91 | C |
| ATOM | 13291 | CB  | ARG | B | 247 | 23.868 | 115.025 | -7.770 | 1.00 12.84 | C |
| ATOM | 13294 | CG  | ARG | B | 247 | 23.231 | 113.839 | -8.463 | 1.00 16.09 | C |
| ATOM | 13297 | CD  | ARG | B | 247 | 21.820 | 114.107 | -8.800 | 1.00 16.64 | C |
| ATOM | 13300 | NE  | ARG | B | 247 | 21.295 | 112.984 | -9.556 | 1.00 15.82 | N |
| ATOM | 13302 | CZ  | ARG | B | 247 | 21.129 | 112.946 | -10.872 | 1.00 17.37 | C |
| ATOM | 13303 | NH1 | ARG | B | 247 | 21.341 | 114.009 | -11.650 | 1.00 15.09 | N |

| | | | | | | | | | |
|---|---|---|---|---|---|---|---|---|---|
| ATOM | 13306 | NH2 | ARG | B | 247 | 20.664 | 111.836 | -11.419 | 1.00 17.53 | N |
| ATOM | 13309 | C | ARG | B | 247 | 26.081 | 116.100 | -7.288 | 1.00 13.66 | C |
| ATOM | 13310 | O | ARG | B | 247 | 26.614 | 116.677 | -8.204 | 1.00 12.77 | O |
| ATOM | 13312 | N | GLU | B | 248 | 26.143 | 116.556 | -6.040 | 1.00 14.33 | N |
| ATOM | 13313 | CA | GLU | B | 248 | 26.926 | 117.749 | -5.702 | 1.00 15.23 | C |
| ATOM | 13315 | CB | GLU | B | 248 | 26.787 | 118.093 | -4.225 | 1.00 15.80 | C |
| ATOM | 13318 | CG | GLU | B | 248 | 25.403 | 118.461 | -3.841 | 1.00 18.62 | C |
| ATOM | 13321 | CD | GLU | B | 248 | 25.202 | 118.591 | -2.325 | 1.00 19.00 | C |
| ATOM | 13322 | OE1 | GLU | B | 248 | 25.938 | 117.999 | -1.475 | 1.00 21.26 | O |
| ATOM | 13323 | OE2 | GLU | B | 248 | 24.204 | 119.261 | -1.979 | 1.00 24.00 | O |
| ATOM | 13324 | C | GLU | B | 248 | 28.409 | 117.538 | -6.034 | 1.00 13.64 | C |
| ATOM | 13325 | O | GLU | B | 248 | 29.052 | 118.421 | -6.652 | 1.00 14.68 | O |
| ATOM | 13327 | N | ALA | B | 249 | 28.955 | 116.402 | -5.638 | 1.00 15.05 | N |
| ATOM | 13328 | CA | ALA | B | 249 | 30.369 | 116.142 | -5.901 | 1.00 15.38 | C |
| ATOM | 13330 | CB | ALA | B | 249 | 30.834 | 114.844 | -5.223 | 1.00 15.57 | C |
| ATOM | 13334 | C | ALA | B | 249 | 30.620 | 116.086 | -7.401 | 1.00 15.76 | C |
| ATOM | 13335 | O | ALA | B | 249 | 31.584 | 116.664 | -7.910 | 1.00 13.87 | O |
| ATOM | 13337 | N | MSE | B | 250 | 29.745 | 115.409 | -8.132 | 1.00 14.09 | N |
| ATOM | 13338 | CA | MSE | B | 250 | 29.929 | 115.272 | -9.557 | 1.00 15.30 | C |
| ATOM | 13340 | CB | MSE | B | 250 | 28.896 | 114.343 | -10.136 | 1.00 13.56 | C |
| ATOM | 13343 | CG | MSE | B | 250 | 29.279 | 112.907 | -9.801 | 1.00 14.93 | C |
| ATOM | 13346 | SE | MSE | B | 250 | 28.200 | 111.574 | -10.737 | 1.00 24.60 | SE |
| ATOM | 13347 | CE | MSE | B | 250 | 26.566 | 111.742 | -9.494 | 1.00 18.80 | C |
| ATOM | 13351 | C | MSE | B | 250 | 29.893 | 116.620 | -10.250 | 1.00 14.36 | C |
| ATOM | 13352 | O | MSE | B | 250 | 30.642 | 116.862 | -11.206 | 1.00 16.11 | O |
| ATOM | 13354 | N | ALA | B | 251 | 29.046 | 117.519 | -9.756 | 1.00 15.12 | N |
| ATOM | 13355 | CA | ALA | B | 251 | 28.906 | 118.849 | -10.378 | 1.00 15.91 | C |
| ATOM | 13357 | CB | ALA | B | 251 | 27.732 | 119.582 | -9.806 | 1.00 16.65 | C |
| ATOM | 13361 | C | ALA | B | 251 | 30.180 | 119.680 | -10.191 | 1.00 16.16 | C |
| ATOM | 13362 | O | ALA | B | 251 | 30.548 | 120.444 | -11.079 | 1.00 15.10 | O |
| ATOM | 13364 | N | LEU | B | 252 | 30.835 | 119.558 | -9.027 | 1.00 17.04 | N |
| ATOM | 13365 | CA | LEU | B | 252 | 32.156 | 120.189 | -8.804 | 1.00 19.08 | C |
| ATOM | 13367 | CB | LEU | B | 252 | 32.747 | 119.806 | -7.434 | 1.00 19.84 | C |
| ATOM | 13370 | CG | LEU | B | 252 | 32.092 | 120.341 | -6.173 | 1.00 23.84 | C |
| ATOM | 13372 | CD1 | LEU | B | 252 | 32.804 | 119.726 | -4.937 | 1.00 26.22 | C |
| ATOM | 13376 | CD2 | LEU | B | 252 | 32.118 | 121.841 | -6.122 | 1.00 27.45 | C |
| ATOM | 13380 | C | LEU | B | 252 | 33.158 | 119.779 | -9.868 | 1.00 21.21 | C |
| ATOM | 13381 | O | LEU | B | 252 | 34.006 | 120.577 | -10.302 | 1.00 21.41 | O |
| ATOM | 13383 | N | PHE | B | 253 | 33.086 | 118.528 | -10.307 | 1.00 23.56 | N |
| ATOM | 13384 | CA | PHE | B | 253 | 34.058 | 118.012 | -11.266 | 1.00 24.32 | C |
| ATOM | 13386 | CB | PHE | B | 253 | 34.615 | 116.670 | -10.719 | 1.00 25.63 | C |
| ATOM | 13389 | CG | PHE | B | 253 | 35.360 | 116.842 | -9.423 | 1.00 25.62 | C |
| ATOM | 13390 | CD1 | PHE | B | 253 | 36.686 | 117.187 | -9.436 | 1.00 28.52 | C |
| ATOM | 13392 | CE1 | PHE | B | 253 | 37.358 | 117.425 | -8.296 | 1.00 27.17 | C |
| ATOM | 13394 | CZ | PHE | B | 253 | 36.718 | 117.341 | -7.079 | 1.00 29.24 | C |
| ATOM | 13396 | CE2 | PHE | B | 253 | 35.375 | 117.035 | -7.046 | 1.00 30.65 | C |
| ATOM | 13398 | CD2 | PHE | B | 253 | 34.704 | 116.806 | -8.224 | 1.00 28.15 | C |
| ATOM | 13400 | C | PHE | B | 253 | 33.525 | 117.946 | -12.684 | 1.00 24.77 | C |
| ATOM | 13401 | O | PHE | B | 253 | 34.202 | 117.422 | -13.540 | 1.00 26.98 | O |
| ATOM | 13403 | N | ASN | B | 254 | 32.363 | 118.563 | -12.964 | 1.00 24.18 | N |
| ATOM | 13404 | CA | ASN | B | 254 | 31.616 | 118.431 | -14.234 | 1.00 23.64 | C |
| ATOM | 13406 | CB | ASN | B | 254 | 32.100 | 119.395 | -15.362 | 1.00 25.04 | C |
| ATOM | 13409 | CG | ASN | B | 254 | 30.975 | 119.678 | -16.448 | 1.00 26.96 | C |
| ATOM | 13410 | OD1 | ASN | B | 254 | 29.760 | 119.602 | -16.159 | 1.00 34.40 | O |
| ATOM | 13411 | ND2 | ASN | B | 254 | 31.390 | 119.992 | -17.689 | 1.00 32.59 | N |
| ATOM | 13414 | C | ASN | B | 254 | 31.449 | 116.990 | -14.774 | 1.00 21.91 | C |
| ATOM | 13415 | O | ASN | B | 254 | 31.479 | 116.745 | -15.986 | 1.00 21.89 | O |

| ATOM | 13417 | N | LEU B 255 | 31.197 | 116.060 | -13.860 | 1.00 | 18.31 | N |
|------|-------|-----|-----------|--------|---------|---------|------|-------|---|
| ATOM | 13418 | CA | LEU B 255 | 30.965 | 114.674 | -14.219 | 1.00 | 17.32 | C |
| ATOM | 13420 | CB | LEU B 255 | 31.520 | 113.752 | -13.121 | 1.00 | 15.20 | C |
| ATOM | 13423 | CG | LEU B 255 | 33.001 | 113.894 | -12.796 | 1.00 | 14.33 | C |
| ATOM | 13425 | CD1 | LEU B 255 | 33.401 | 112.949 | -11.664 | 1.00 | 14.32 | C |
| ATOM | 13429 | CD2 | LEU B 255 | 33.849 | 113.641 | -14.046 | 1.00 | 16.28 | C |
| ATOM | 13433 | C | LEU B 255 | 29.465 | 114.450 | -14.346 | 1.00 | 17.19 | C |
| ATOM | 13434 | O | LEU B 255 | 28.685 | 114.985 | -13.559 | 1.00 | 18.72 | O |
| ATOM | 13436 | N | GLU B 256 | 29.071 | 113.646 | -15.316 | 1.00 | 16.09 | N |
| ATOM | 13437 | CA | GLU B 256 | 27.675 | 113.339 | -15.536 | 1.00 | 17.06 | C |
| ATOM | 13439 | CB | GLU B 256 | 27.417 | 113.211 | -17.021 | 1.00 | 17.55 | C |
| ATOM | 13442 | CG | GLU B 256 | 25.996 | 112.835 | -17.341 | 1.00 | 21.29 | C |
| ATOM | 13445 | CD | GLU B 256 | 25.626 | 113.100 | -18.768 | 1.00 | 24.13 | C |
| ATOM | 13446 | OE1 | GLU B 256 | 26.240 | 113.995 | -19.376 | 1.00 | 24.26 | O |
| ATOM | 13447 | OE2 | GLU B 256 | 24.712 | 112.418 | -19.270 | 1.00 | 30.57 | O |
| ATOM | 13448 | C | GLU B 256 | 27.269 | 112.018 | -14.899 | 1.00 | 16.22 | C |
| ATOM | 13449 | O | GLU B 256 | 27.899 | 111.014 | -15.149 | 1.00 | 15.41 | O |
| ATOM | 13451 | N | PRO B 257 | 26.175 | 112.015 | -14.103 | 1.00 | 16.85 | N |
| ATOM | 13452 | CA | PRO B 257 | 25.605 | 110.750 | -13.583 | 1.00 | 16.71 | C |
| ATOM | 13454 | CB | PRO B 257 | 24.318 | 111.187 | -12.883 | 1.00 | 17.76 | C |
| ATOM | 13457 | CG | PRO B 257 | 24.556 | 112.639 | -12.538 | 1.00 | 17.74 | C |
| ATOM | 13460 | CD | PRO B 257 | 25.447 | 113.196 | -13.619 | 1.00 | 17.22 | C |
| ATOM | 13463 | C | PRO B 257 | 25.258 | 109.823 | -14.725 | 1.00 | 16.00 | C |
| ATOM | 13464 | O | PRO B 257 | 24.765 | 110.293 | -15.764 | 1.00 | 16.19 | O |
| ATOM | 13465 | N | VAL B 258 | 25.537 | 108.544 | -14.550 | 1.00 | 15.10 | N |
| ATOM | 13466 | CA | VAL B 258 | 25.091 | 107.535 | -15.507 | 1.00 | 15.09 | C |
| ATOM | 13468 | CB | VAL B 258 | 26.027 | 106.299 | -15.557 | 1.00 | 16.29 | C |
| ATOM | 13470 | CG1 | VAL B 258 | 27.377 | 106.697 | -16.150 | 1.00 | 17.42 | C |
| ATOM | 13474 | CG2 | VAL B 258 | 26.190 | 105.689 | -14.244 | 1.00 | 16.52 | C |
| ATOM | 13478 | C | VAL B 258 | 23.691 | 107.065 | -15.169 | 1.00 | 15.75 | C |
| ATOM | 13479 | O | VAL B 258 | 23.277 | 107.116 | -14.002 | 1.00 | 15.04 | O |
| ATOM | 13481 | N | VAL B 259 | 22.962 | 106.645 | -16.202 | 1.00 | 15.98 | N |
| ATOM | 13482 | CA | VAL B 259 | 21.659 | 106.010 | -16.049 | 1.00 | 16.00 | C |
| ATOM | 13484 | CB | VAL B 259 | 20.613 | 106.674 | -16.982 | 1.00 | 16.06 | C |
| ATOM | 13486 | CG1 | VAL B 259 | 19.314 | 105.929 | -16.943 | 1.00 | 16.96 | C |
| ATOM | 13490 | CG2 | VAL B 259 | 20.455 | 108.144 | -16.605 | 1.00 | 16.12 | C |
| ATOM | 13494 | C | VAL B 259 | 21.845 | 104.543 | -16.407 | 1.00 | 16.77 | C |
| ATOM | 13495 | O | VAL B 259 | 22.238 | 104.246 | -17.555 | 1.00 | 17.51 | O |
| ATOM | 13497 | N | LEU B 260 | 21.581 | 103.647 | -15.450 | 1.00 | 17.63 | N |
| ATOM | 13498 | CA | LEU B 260 | 21.873 | 102.225 | -15.627 | 1.00 | 17.14 | C |
| ATOM | 13500 | CB | LEU B 260 | 21.936 | 101.488 | -14.286 | 1.00 | 17.81 | C |
| ATOM | 13503 | CG | LEU B 260 | 22.982 | 102.060 | -13.320 | 1.00 | 17.71 | C |
| ATOM | 13505 | CD1 | LEU B 260 | 23.097 | 101.202 | -12.084 | 1.00 | 20.82 | C |
| ATOM | 13509 | CD2 | LEU B 260 | 24.353 | 102.218 | -13.967 | 1.00 | 16.90 | C |
| ATOM | 13513 | C | LEU B 260 | 20.847 | 101.578 | -16.537 | 1.00 | 18.50 | C |
| ATOM | 13514 | O | LEU B 260 | 19.626 | 101.765 | -16.389 | 1.00 | 19.26 | O |
| ATOM | 13516 | N | GLY B 261 | 21.359 | 100.834 | -17.510 | 1.00 | 18.07 | N |
| ATOM | 13517 | CA | GLY B 261 | 20.524 | 100.122 | -18.453 | 1.00 | 17.83 | C |
| ATOM | 13520 | C | GLY B 261 | 20.477 | 98.641 | -18.179 | 1.00 | 17.26 | C |
| ATOM | 13521 | O | GLY B 261 | 20.894 | 98.172 | -17.099 | 1.00 | 16.84 | O |
| ATOM | 13523 | N | PRO B 262 | 19.960 | 97.871 | -19.159 | 1.00 | 16.56 | N |
| ATOM | 13524 | CA | PRO B 262 | 19.848 | 96.432 | -19.040 | 1.00 | 16.40 | C |
| ATOM | 13526 | CB | PRO B 262 | 19.394 | 95.978 | -20.439 | 1.00 | 17.26 | C |
| ATOM | 13529 | CG | PRO B 262 | 18.828 | 97.162 | -21.059 | 1.00 | 17.97 | C |
| ATOM | 13532 | CD | PRO B 262 | 19.483 | 98.368 | -20.460 | 1.00 | 17.16 | C |
| ATOM | 13535 | C | PRO B 262 | 21.175 | 95.789 | -18.662 | 1.00 | 15.94 | C |
| ATOM | 13536 | O | PRO B 262 | 22.214 | 96.109 | -19.231 | 1.00 | 15.69 | O |

| ATOM | 13537 | N | LYS | B | 263 | 21.096 | 94.937 | -17.655 | 1.00 | 15.76 | N |
|------|-------|-----|-----|---|-----|--------|--------|---------|------|-------|---|
| ATOM | 13538 | CA | LYS | B | 263 | 22.201 | 94.158 | -17.109 | 1.00 | 15.86 | C |
| ATOM | 13540 | CB | LYS | B | 263 | 22.813 | 93.276 | -18.214 | 1.00 | 16.60 | C |
| ATOM | 13543 | CG | LYS | B | 263 | 24.088 | 92.517 | -17.863 | 1.00 | 16.28 | C |
| ATOM | 13546 | CD | LYS | B | 263 | 23.864 | 91.364 | -16.869 | 1.00 | 17.69 | C |
| ATOM | 13549 | CE | LYS | B | 263 | 25.081 | 91.192 | -15.978 | 1.00 | 19.50 | C |
| ATOM | 13552 | NZ | LYS | B | 263 | 26.304 | 90.885 | -16.743 | 1.00 | 17.29 | N |
| ATOM | 13556 | C | LYS | B | 263 | 23.242 | 94.997 | -16.351 | 1.00 | 15.33 | C |
| ATOM | 13557 | O | LYS | B | 263 | 24.096 | 94.454 | -15.637 | 1.00 | 15.04 | O |
| ATOM | 13559 | N | GLU | B | 264 | 23.149 | 96.321 | -16.413 | 1.00 | 14.14 | N |
| ATOM | 13560 | CA | GLU | B | 264 | 24.172 | 97.124 | -15.722 | 1.00 | 14.37 | C |
| ATOM | 13562 | CB | GLU | B | 264 | 24.242 | 98.528 | -16.303 | 1.00 | 14.55 | C |
| ATOM | 13565 | CG | GLU | B | 264 | 24.565 | 98.498 | -17.751 | 1.00 | 16.09 | C |
| ATOM | 13568 | CD | GLU | B | 264 | 24.855 | 99.873 | -18.354 | 1.00 | 17.36 | C |
| ATOM | 13569 | OE1 | GLU | B | 264 | 24.247 | 100.891 | -17.922 | 1.00 | 19.62 | O |
| ATOM | 13570 | OE2 | GLU | B | 264 | 25.669 | 99.939 | -19.290 | 1.00 | 16.89 | O |
| ATOM | 13571 | C | GLU | B | 264 | 24.082 | 97.154 | -14.193 | 1.00 | 13.95 | C |
| ATOM | 13572 | O | GLU | B | 264 | 25.103 | 97.202 | -13.506 | 1.00 | 15.17 | O |
| ATOM | 13574 | N | GLY | B | 265 | 22.876 | 97.031 | -13.649 | 1.00 | 13.99 | N |
| ATOM | 13575 | CA | GLY | B | 265 | 22.720 | 96.818 | -12.236 | 1.00 | 14.14 | C |
| ATOM | 13578 | C | GLY | B | 265 | 23.466 | 95.580 | -11.760 | 1.00 | 14.14 | C |
| ATOM | 13579 | O | GLY | B | 265 | 24.323 | 95.667 | -10.896 | 1.00 | 15.41 | O |
| ATOM | 13581 | N | LEU | B | 266 | 23.156 | 94.421 | -12.341 | 1.00 | 14.84 | N |
| ATOM | 13582 | CA | LEU | B | 266 | 23.838 | 93.184 | -11.928 | 1.00 | 15.01 | C |
| ATOM | 13584 | CB | LEU | B | 266 | 23.236 | 91.934 | -12.565 | 1.00 | 16.21 | C |
| ATOM | 13587 | CG | LEU | B | 266 | 21.843 | 91.557 | -12.098 | 1.00 | 17.93 | C |
| ATOM | 13589 | CD1 | LEU | B | 266 | 21.415 | 90.325 | -12.847 | 1.00 | 20.12 | C |
| ATOM | 13593 | CD2 | LEU | B | 266 | 21.828 | 91.382 | -10.598 | 1.00 | 20.28 | C |
| ATOM | 13597 | C | LEU | B | 266 | 25.309 | 93.231 | -12.278 | 1.00 | 15.08 | C |
| ATOM | 13598 | O | LEU | B | 266 | 26.162 | 92.725 | -11.517 | 1.00 | 15.43 | O |
| ATOM | 13600 | N | GLY | B | 267 | 25.625 | 93.841 | -13.416 | 1.00 | 14.25 | N |
| ATOM | 13601 | CA | GLY | B | 267 | 27.030 | 93.999 | -13.863 | 1.00 | 15.52 | C |
| ATOM | 13604 | C | GLY | B | 267 | 27.887 | 94.764 | -12.864 | 1.00 | 15.41 | C |
| ATOM | 13605 | O | GLY | B | 267 | 29.071 | 94.456 | -12.665 | 1.00 | 15.50 | O |
| ATOM | 13607 | N | LEU | B | 268 | 27.286 | 95.736 | -12.180 | 1.00 | 14.32 | N |
| ATOM | 13608 | CA | LEU | B | 268 | 28.007 | 96.532 | -11.213 | 1.00 | 14.29 | C |
| ATOM | 13610 | CB | LEU | B | 268 | 27.423 | 97.915 | -11.145 | 1.00 | 14.47 | C |
| ATOM | 13613 | CG | LEU | B | 268 | 27.822 | 98.788 | -12.329 | 1.00 | 13.83 | C |
| ATOM | 13615 | CD1 | LEU | B | 268 | 26.932 | 100.035 | -12.338 | 1.00 | 14.72 | C |
| ATOM | 13619 | CD2 | LEU | B | 268 | 29.302 | 99.213 | -12.288 | 1.00 | 15.50 | C |
| ATOM | 13623 | C | LEU | B | 268 | 27.960 | 95.938 | -9.838 | 1.00 | 14.73 | C |
| ATOM | 13624 | O | LEU | B | 268 | 28.930 | 96.056 | -9.110 | 1.00 | 15.60 | O |
| ATOM | 13626 | N | VAL | B | 269 | 26.817 | 95.353 | -9.451 | 1.00 | 14.27 | N |
| ATOM | 13627 | CA | VAL | B | 269 | 26.640 | 94.912 | -8.059 | 1.00 | 15.82 | C |
| ATOM | 13629 | CB | VAL | B | 269 | 25.219 | 95.276 | -7.499 | 1.00 | 16.57 | C |
| ATOM | 13631 | CG1 | VAL | B | 269 | 24.909 | 96.739 | -7.854 | 1.00 | 16.79 | C |
| ATOM | 13635 | CG2 | VAL | B | 269 | 24.206 | 94.332 | -7.960 | 1.00 | 20.09 | C |
| ATOM | 13639 | C | VAL | B | 269 | 27.008 | 93.477 | -7.699 | 1.00 | 15.47 | C |
| ATOM | 13640 | O | VAL | B | 269 | 27.316 | 93.204 | -6.531 | 1.00 | 16.12 | O |
| ATOM | 13642 | N | ASN | B | 270 | 26.962 | 92.580 | -8.680 | 1.00 | 14.73 | N |
| ATOM | 13643 | CA | ASN | B | 270 | 27.382 | 91.173 | -8.517 | 1.00 | 14.20 | C |
| ATOM | 13645 | CB | ASN | B | 270 | 26.828 | 90.239 | -9.637 | 1.00 | 15.03 | C |
| ATOM | 13648 | CG | ASN | B | 270 | 25.439 | 89.753 | -9.392 | 1.00 | 20.71 | C |
| ATOM | 13649 | OD1 | ASN | B | 270 | 24.791 | 90.112 | -8.414 | 1.00 | 25.48 | O |
| ATOM | 13650 | ND2 | ASN | B | 270 | 24.968 | 88.889 | -10.283 | 1.00 | 22.62 | N |
| ATOM | 13653 | C | ASN | B | 270 | 28.873 | 91.126 | -8.678 | 1.00 | 13.94 | C |
| ATOM | 13654 | O | ASN | B | 270 | 29.404 | 91.600 | -9.689 | 1.00 | 15.23 | O |

| ATOM | 13656 | N | GLY B 271 | 29.564 | 90.489 | -7.741 | 1.00 | 14.53 | N |
|------|-------|------|-----------|--------|--------|--------|------|-------|------|
| ATOM | 13657 | CA | GLY B 271 | 31.008 | 90.362 | -7.871 | 1.00 | 14.26 | C |
| ATOM | 13660 | C | GLY B 271 | 31.739 | 90.471 | -6.576 | 1.00 | 13.01 | C |
| ATOM | 13661 | O | GLY B 271 | 31.163 | 90.640 | -5.503 | 1.00 | 13.61 | O |
| ATOM | 13663 | N | THR B 272 | 33.055 | 90.367 | -6.672 | 1.00 | 12.73 | N |
| ATOM | 13664 | CA | THR B 272 | 33.889 | 90.148 | -5.518 | 1.00 | 12.91 | C |
| ATOM | 13666 | CB | THR B 272 | 34.689 | 88.836 | -5.637 | 1.00 | 12.69 | C |
| ATOM | 13668 | OG1 | THR B 272 | 35.725 | 88.991 | -6.624 | 1.00 | 13.12 | O |
| ATOM | 13670 | CG2 | THR B 272 | 33.789 | 87.669 | -5.979 | 1.00 | 13.84 | C |
| ATOM | 13674 | C | THR B 272 | 34.867 | 91.322 | -5.291 | 1.00 | 11.78 | C |
| ATOM | 13675 | O | THR B 272 | 35.790 | 91.214 | -4.495 | 1.00 | 11.39 | O |
| ATOM | 13677 | N | ALA B 273 | 34.648 | 92.448 | -5.961 | 1.00 | 11.70 | N |
| ATOM | 13678 | CA | ALA B 273 | 35.663 | 93.512 | -5.950 | 1.00 | 13.04 | C |
| ATOM | 13680 | CB | ALA B 273 | 35.320 | 94.599 | -6.931 | 1.00 | 13.29 | C |
| ATOM | 13684 | C | ALA B 273 | 35.978 | 94.103 | -4.594 | 1.00 | 12.74 | C |
| ATOM | 13685 | O | ALA B 273 | 37.081 | 94.568 | -4.349 | 1.00 | 13.39 | O |
| ATOM | 13687 | N | VAL B 274 | 34.994 | 94.169 | -3.691 | 1.00 | 12.11 | N |
| ATOM | 13688 | CA | VAL B 274 | 35.233 | 94.835 | -2.419 | 1.00 | 11.22 | C |
| ATOM | 13690 | CB | VAL B 274 | 33.914 | 95.219 | -1.767 | 1.00 | 12.51 | C |
| ATOM | 13692 | CG1 | VAL B 274 | 34.175 | 95.863 | -0.412 | 1.00 | 11.78 | C |
| ATOM | 13696 | CG2 | VAL B 274 | 33.086 | 96.131 | -2.715 | 1.00 | 13.03 | C |
| ATOM | 13700 | C | VAL B 274 | 36.086 | 93.933 | -1.525 | 1.00 | 12.14 | C |
| ATOM | 13701 | O | VAL B 274 | 37.104 | 94.352 | -0.992 | 1.00 | 12.26 | O |
| ATOM | 13703 | N | ASER B 275 | 35.684 | 92.678 | -1.388 | 0.50 | 12.04 | N |
| ATOM | 13704 | N | BSER B 275 | 35.641 | 92.685 | -1.421 | 0.50 | 11.97 | N |
| ATOM | 13705 | CA | ASER B 275 | 36.503 | 91.732 | -0.620 | 0.50 | 12.04 | C |
| ATOM | 13706 | CA | BSER B 275 | 36.399 | 91.634 | -0.743 | 0.50 | 12.18 | C |
| ATOM | 13709 | CB | ASER B 275 | 35.783 | 90.398 | -0.465 | 0.50 | 12.02 | C |
| ATOM | 13710 | CB | BSER B 275 | 35.683 | 90.288 | -0.913 | 0.50 | 11.91 | C |
| ATOM | 13715 | OG | ASER B 275 | 35.389 | 89.931 | -1.730 | 0.50 | 11.80 | O |
| ATOM | 13716 | OG | BSER B 275 | 34.465 | 90.296 | -0.178 | 0.50 | 13.29 | O |
| ATOM | 13719 | C | ASER B 275 | 37.873 | 91.531 | -1.252 | 0.50 | 12.45 | C |
| ATOM | 13720 | C | BSER B 275 | 37.815 | 91.552 | -1.261 | 0.50 | 12.42 | C |
| ATOM | 13721 | O | ASER B 275 | 38.887 | 91.475 | -0.542 | 0.50 | 13.10 | O |
| ATOM | 13722 | O | BSER B 275 | 38.786 | 91.619 | -0.488 | 0.50 | 13.14 | O |
| ATOM | 13725 | N | ALA B 276 | 37.929 | 91.427 | -2.579 | 1.00 | 13.05 | N |
| ATOM | 13726 | CA | ALA B 276 | 39.247 | 91.318 | -3.253 | 1.00 | 12.19 | C |
| ATOM | 13728 | CB | ALA B 276 | 39.071 | 91.093 | -4.733 | 1.00 | 12.90 | C |
| ATOM | 13732 | C | ALA B 276 | 40.125 | 92.568 | -2.970 | 1.00 | 12.66 | C |
| ATOM | 13733 | O | ALA B 276 | 41.360 | 92.476 | -2.793 | 1.00 | 12.80 | O |
| ATOM | 13735 | N | SER B 277 | 39.509 | 93.740 | -3.004 | 1.00 | 12.70 | N |
| ATOM | 13736 | CA | SER B 277 | 40.249 | 94.953 | -2.701 | 1.00 | 12.38 | C |
| ATOM | 13738 | CB | SER B 277 | 39.343 | 96.159 | -2.770 | 1.00 | 12.78 | C |
| ATOM | 13741 | OG | SER B 277 | 40.108 | 97.275 | -2.356 | 1.00 | 12.08 | O |
| ATOM | 13743 | C | SER B 277 | 40.840 | 94.878 | -1.284 | 1.00 | 11.94 | C |
| ATOM | 13744 | O | SER B 277 | 42.047 | 95.024 | -1.051 | 1.00 | 12.98 | O |
| ATOM | 13746 | N | MSE B 278 | 39.974 | 94.682 | -0.303 | 1.00 | 12.68 | N |
| ATOM | 13747 | CA | MSE B 278 | 40.472 | 94.661 | 1.081 | 1.00 | 13.44 | C |
| ATOM | 13749 | CB | MSE B 278 | 39.338 | 94.554 | 2.090 | 1.00 | 14.23 | C |
| ATOM | 13752 | CG | MSE B 278 | 39.824 | 94.914 | 3.459 | 1.00 | 14.85 | C |
| ATOM | 13755 | SE | MSE B 278 | 38.313 | 95.298 | 4.655 | 1.00 | 23.49 | SE |
| ATOM | 13756 | CE | MSE B 278 | 39.275 | 96.464 | 6.020 | 1.00 | 15.11 | C |
| ATOM | 13760 | C | MSE B 278 | 41.491 | 93.547 | 1.346 | 1.00 | 12.87 | C |
| ATOM | 13761 | O | MSE B 278 | 42.484 | 93.740 | 2.095 | 1.00 | 13.05 | O |
| ATOM | 13763 | N | ALA B 279 | 41.229 | 92.392 | 0.740 | 1.00 | 12.49 | N |
| ATOM | 13764 | CA | ALA B 279 | 42.122 | 91.254 | 0.812 | 1.00 | 12.40 | C |
| ATOM | 13766 | CB | ALA B 279 | 41.465 | 90.015 | 0.193 | 1.00 | 11.94 | C |

| ATOM | 13770 | C | ALA | B | 279 | 43.498 | 91.566 | 0.200 | 1.00 | 13.06 | C |
|---|---|---|---|---|---|---|---|---|---|---|---|
| ATOM | 13771 | O | ALA | B | 279 | 44.530 | 91.135 | 0.723 | 1.00 | 13.09 | O |
| ATOM | 13773 | N | THR | B | 280 | 43.514 | 92.267 | -0.931 | 1.00 | 11.86 | N |
| ATOM | 13774 | CA | THR | B | 280 | 44.779 | 92.639 | -1.573 | 1.00 | 13.27 | C |
| ATOM | 13776 | CB | THR | B | 280 | 44.537 | 93.323 | -2.937 | 1.00 | 13.64 | C |
| ATOM | 13778 | OG1 | THR | B | 280 | 43.950 | 92.391 | -3.854 | 1.00 | 13.07 | O |
| ATOM | 13780 | CG2 | THR | B | 280 | 45.826 | 93.837 | -3.451 | 1.00 | 13.69 | C |
| ATOM | 13784 | C | THR | B | 280 | 45.591 | 93.551 | -0.676 | 1.00 | 12.43 | C |
| ATOM | 13785 | O | THR | B | 280 | 46.796 | 93.342 | -0.490 | 1.00 | 13.63 | O |
| ATOM | 13787 | N | LEU | B | 281 | 44.947 | 94.554 | -0.072 | 1.00 | 12.04 | N |
| ATOM | 13788 | CA | LEU | B | 281 | 45.625 | 95.455 | 0.852 | 1.00 | 12.68 | C |
| ATOM | 13790 | CB | LEU | B | 281 | 44.664 | 96.557 | 1.254 | 1.00 | 13.62 | C |
| ATOM | 13793 | CG | LEU | B | 281 | 44.304 | 97.458 | 0.052 | 1.00 | 13.90 | C |
| ATOM | 13795 | CD1 | LEU | B | 281 | 43.049 | 98.236 | 0.390 | 1.00 | 16.36 | C |
| ATOM | 13799 | CD2 | LEU | B | 281 | 45.439 | 98.418 | -0.323 | 1.00 | 17.86 | C |
| ATOM | 13803 | C | LEU | B | 281 | 46.168 | 94.685 | 2.047 | 1.00 | 12.81 | C |
| ATOM | 13804 | O | LEU | B | 281 | 47.304 | 94.939 | 2.502 | 1.00 | 13.32 | O |
| ATOM | 13806 | N | ALA | B | 282 | 45.364 | 93.762 | 2.565 | 1.00 | 13.05 | N |
| ATOM | 13807 | CA | ALA | B | 282 | 45.765 | 92.991 | 3.740 | 1.00 | 13.14 | C |
| ATOM | 13809 | CB | ALA | B | 282 | 44.594 | 92.270 | 4.309 | 1.00 | 13.95 | C |
| ATOM | 13813 | C | ALA | B | 282 | 46.932 | 92.042 | 3.439 | 1.00 | 12.43 | C |
| ATOM | 13814 | O | ALA | B | 282 | 47.875 | 91.893 | 4.236 | 1.00 | 13.06 | O |
| ATOM | 13816 | N | LEU | B | 283 | 46.911 | 91.441 | 2.258 | 1.00 | 11.04 | N |
| ATOM | 13817 | CA | LEU | B | 283 | 48.007 | 90.558 | 1.884 | 1.00 | 12.54 | C |
| ATOM | 13819 | CB | LEU | B | 283 | 47.670 | 89.789 | 0.619 | 1.00 | 11.12 | C |
| ATOM | 13822 | CG | LEU | B | 283 | 48.783 | 88.802 | 0.209 | 1.00 | 12.47 | C |
| ATOM | 13824 | CD1 | LEU | B | 283 | 49.108 | 87.811 | 1.305 | 1.00 | 15.43 | C |
| ATOM | 13828 | CD2 | LEU | B | 283 | 48.395 | 88.067 | -1.067 | 1.00 | 13.60 | C |
| ATOM | 13832 | C | LEU | B | 283 | 49.301 | 91.332 | 1.671 | 1.00 | 12.96 | C |
| ATOM | 13833 | O | LEU | B | 283 | 50.370 | 90.927 | 2.138 | 1.00 | 13.58 | O |
| ATOM | 13835 | N | HIS | B | 284 | 49.203 | 92.465 | 0.965 | 1.00 | 13.05 | N |
| ATOM | 13836 | CA | HIS | B | 284 | 50.343 | 93.376 | 0.853 | 1.00 | 13.07 | C |
| ATOM | 13838 | CB | HIS | B | 284 | 49.889 | 94.655 | 0.152 | 1.00 | 12.29 | C |
| ATOM | 13841 | CG | HIS | B | 284 | 50.877 | 95.777 | 0.160 | 1.00 | 13.14 | C |
| ATOM | 13842 | ND1 | HIS | B | 284 | 51.070 | 96.585 | 1.258 | 1.00 | 15.54 | N |
| ATOM | 13844 | CE1 | HIS | B | 284 | 51.957 | 97.528 | 0.938 | 1.00 | 14.57 | C |
| ATOM | 13846 | NE2 | HIS | B | 284 | 52.313 | 97.381 | -0.321 | 1.00 | 16.39 | N |
| ATOM | 13848 | CD2 | HIS | B | 284 | 51.639 | 96.300 | -0.840 | 1.00 | 16.72 | C |
| ATOM | 13850 | C | HIS | B | 284 | 50.974 | 93.671 | 2.217 | 1.00 | 12.58 | C |
| ATOM | 13851 | O | HIS | B | 284 | 52.200 | 93.512 | 2.401 | 1.00 | 13.89 | O |
| ATOM | 13853 | N | ASP | B | 285 | 50.140 | 94.009 | 3.184 | 1.00 | 12.89 | N |
| ATOM | 13854 | CA | ASP | B | 285 | 50.675 | 94.406 | 4.479 | 1.00 | 13.31 | C |
| ATOM | 13856 | CB | ASP | B | 285 | 49.567 | 95.102 | 5.277 | 1.00 | 13.27 | C |
| ATOM | 13859 | CG | ASP | B | 285 | 49.199 | 96.481 | 4.735 | 1.00 | 16.45 | C |
| ATOM | 13860 | OD1 | ASP | B | 285 | 49.914 | 97.056 | 3.896 | 1.00 | 14.40 | O |
| ATOM | 13861 | OD2 | ASP | B | 285 | 48.172 | 97.000 | 5.211 | 1.00 | 17.31 | O |
| ATOM | 13862 | C | ASP | B | 285 | 51.284 | 93.211 | 5.211 | 1.00 | 14.16 | C |
| ATOM | 13863 | O | ASP | B | 285 | 52.319 | 93.332 | 5.867 | 1.00 | 14.48 | O |
| ATOM | 13865 | N | ALA | B | 286 | 50.636 | 92.056 | 5.065 | 1.00 | 13.09 | N |
| ATOM | 13866 | CA | ALA | B | 286 | 51.102 | 90.811 | 5.693 | 1.00 | 13.30 | C |
| ATOM | 13868 | CB | ALA | B | 286 | 50.100 | 89.695 | 5.480 | 1.00 | 13.25 | C |
| ATOM | 13872 | C | ALA | B | 286 | 52.448 | 90.440 | 5.149 | 1.00 | 12.89 | C |
| ATOM | 13873 | O | ALA | B | 286 | 53.303 | 89.960 | 5.878 | 1.00 | 13.76 | O |
| ATOM | 13875 | N | HIS | B | 287 | 52.671 | 90.627 | 3.852 | 1.00 | 11.18 | N |
| ATOM | 13876 | CA | HIS | B | 287 | 54.004 | 90.277 | 3.290 | 1.00 | 11.71 | C |
| ATOM | 13878 | CB | HIS | B | 287 | 54.080 | 90.623 | 1.816 | 1.00 | 12.01 | C |
| ATOM | 13881 | CG | HIS | B | 287 | 53.391 | 89.652 | 0.886 | 1.00 | 12.11 | C |

| ATOM | 13882 | ND1 | HIS | B | 287 | 53.614 | 88.289 | 0.903 | 1.00 | 14.04 | N |
|------|-------|-----|-----|---|-----|--------|--------|-------|------|-------|---|
| ATOM | 13884 | CE1 | HIS | B | 287 | 52.919 | 87.732 | -0.081 | 1.00 | 15.02 | C |
| ATOM | 13886 | NE2 | HIS | B | 287 | 52.292 | 88.689 | -0.760 | 1.00 | 14.85 | N |
| ATOM | 13888 | CD2 | HIS | B | 287 | 52.576 | 89.892 | -0.176 | 1.00 | 13.66 | C |
| ATOM | 13890 | C | HIS | B | 287 | 55.102 | 91.076 | 3.981 | 1.00 | 11.79 | C |
| ATOM | 13891 | O | HIS | B | 287 | 56.189 | 90.580 | 4.288 | 1.00 | 12.35 | O |
| ATOM | 13893 | N | MSE | B | 288 | 54.808 | 92.364 | 4.200 | 1.00 | 12.47 | N |
| ATOM | 13894 | CA | MSE | B | 288 | 55.802 | 93.245 | 4.820 | 1.00 | 12.67 | C |
| ATOM | 13896 | CB | MSE | B | 288 | 55.354 | 94.706 | 4.836 | 1.00 | 13.89 | C |
| ATOM | 13899 | CG | MSE | B | 288 | 54.934 | 95.252 | 3.523 | 1.00 | 14.55 | C |
| ATOM | 13902 | SE | MSE | B | 288 | 56.283 | 94.983 | 2.106 | 1.00 | 24.66 | SE |
| ATOM | 13903 | CE | MSE | B | 288 | 54.987 | 95.434 | 0.623 | 1.00 | 22.10 | C |
| ATOM | 13907 | C | MSE | B | 288 | 56.102 | 92.819 | 6.250 | 1.00 | 13.13 | C |
| ATOM | 13908 | O | MSE | B | 288 | 57.234 | 92.833 | 6.707 | 1.00 | 13.25 | O |
| ATOM | 13910 | N | LEU | B | 289 | 55.053 | 92.414 | 6.964 | 1.00 | 11.73 | N |
| ATOM | 13911 | CA | LEU | B | 289 | 55.168 | 92.044 | 8.345 | 1.00 | 12.14 | C |
| ATOM | 13913 | CB | LEU | B | 289 | 53.795 | 91.961 | 8.987 | 1.00 | 11.92 | C |
| ATOM | 13916 | CG | LEU | B | 289 | 53.061 | 93.260 | 9.249 | 1.00 | 13.18 | C |
| ATOM | 13918 | CD1 | LEU | B | 289 | 51.623 | 92.992 | 9.662 | 1.00 | 15.28 | C |
| ATOM | 13922 | CD2 | LEU | B | 289 | 53.759 | 94.061 | 10.336 | 1.00 | 13.81 | C |
| ATOM | 13926 | C | LEU | B | 289 | 55.931 | 90.691 | 8.434 | 1.00 | 11.75 | C |
| ATOM | 13927 | O | LEU | B | 289 | 56.712 | 90.491 | 9.339 | 1.00 | 12.66 | O |
| ATOM | 13929 | N | SER | B | 290 | 55.778 | 89.823 | 7.447 | 1.00 | 13.26 | N |
| ATOM | 13930 | CA | SER | B | 290 | 56.512 | 88.573 | 7.387 | 1.00 | 12.45 | C |
| ATOM | 13932 | CB | SER | B | 290 | 56.046 | 87.781 | 6.152 | 1.00 | 13.35 | C |
| ATOM | 13935 | OG | SER | B | 290 | 56.827 | 86.633 | 5.955 | 1.00 | 16.81 | O |
| ATOM | 13937 | C | SER | B | 290 | 57.986 | 88.880 | 7.238 | 1.00 | 12.90 | C |
| ATOM | 13938 | O | SER | B | 290 | 58.827 | 88.305 | 7.919 | 1.00 | 12.85 | O |
| ATOM | 13940 | N | LEU | B | 291 | 58.319 | 89.833 | 6.355 | 1.00 | 11.44 | N |
| ATOM | 13941 | CA | LEU | B | 291 | 59.742 | 90.205 | 6.158 | 1.00 | 12.64 | C |
| ATOM | 13943 | CB | LEU | B | 291 | 59.931 | 91.074 | 4.921 | 1.00 | 13.78 | C |
| ATOM | 13946 | CG | LEU | B | 291 | 59.669 | 90.365 | 3.569 | 1.00 | 14.72 | C |
| ATOM | 13948 | CD1 | LEU | B | 291 | 59.993 | 91.321 | 2.391 | 1.00 | 15.79 | C |
| ATOM | 13952 | CD2 | LEU | B | 291 | 60.455 | 89.084 | 3.412 | 1.00 | 17.59 | C |
| ATOM | 13956 | C | LEU | B | 291 | 60.304 | 90.864 | 7.404 | 1.00 | 12.37 | C |
| ATOM | 13957 | O | LEU | B | 291 | 61.447 | 90.631 | 7.805 | 1.00 | 13.36 | O |
| ATOM | 13959 | N | LEU | B | 292 | 59.506 | 91.681 | 8.042 | 1.00 | 12.12 | N |
| ATOM | 13960 | CA | LEU | B | 292 | 59.934 | 92.345 | 9.296 | 1.00 | 12.51 | C |
| ATOM | 13962 | CB | LEU | B | 292 | 58.943 | 93.436 | 9.699 | 1.00 | 11.92 | C |
| ATOM | 13965 | CG | LEU | B | 292 | 59.152 | 94.170 | 11.028 | 1.00 | 13.10 | C |
| ATOM | 13967 | CD1 | LEU | B | 292 | 60.545 | 94.870 | 11.025 | 1.00 | 13.70 | C |
| ATOM | 13971 | CD2 | LEU | B | 292 | 58.041 | 95.150 | 11.353 | 1.00 | 13.88 | C |
| ATOM | 13975 | C | LEU | B | 292 | 60.186 | 91.324 | 10.423 | 1.00 | 12.50 | C |
| ATOM | 13976 | O | LEU | B | 292 | 61.117 | 91.452 | 11.222 | 1.00 | 12.39 | O |
| ATOM | 13978 | N | SER | B | 293 | 59.366 | 90.287 | 10.472 | 1.00 | 11.39 | N |
| ATOM | 13979 | CA | SER | B | 293 | 59.531 | 89.196 | 11.442 | 1.00 | 11.54 | C |
| ATOM | 13981 | CB | SER | B | 293 | 58.431 | 88.144 | 11.245 | 1.00 | 13.44 | C |
| ATOM | 13984 | OG | SER | B | 293 | 58.658 | 87.102 | 12.178 | 1.00 | 12.17 | O |
| ATOM | 13986 | C | SER | B | 293 | 60.906 | 88.528 | 11.279 | 1.00 | 12.88 | C |
| ATOM | 13987 | O | SER | B | 293 | 61.583 | 88.187 | 12.254 | 1.00 | 13.02 | O |
| ATOM | 13989 | N | GLN | B | 294 | 61.301 | 88.350 | 10.026 | 1.00 | 12.09 | N |
| ATOM | 13990 | CA | GLN | B | 294 | 62.599 | 87.748 | 9.691 | 1.00 | 12.83 | C |
| ATOM | 13992 | CB | GLN | B | 294 | 62.658 | 87.444 | 8.215 | 1.00 | 12.59 | C |
| ATOM | 13995 | CG | GLN | B | 294 | 61.748 | 86.276 | 7.912 | 1.00 | 11.97 | C |
| ATOM | 13998 | CD | GLN | B | 294 | 61.676 | 85.904 | 6.452 | 1.00 | 13.23 | C |
| ATOM | 13999 | OE1 | GLN | B | 294 | 62.712 | 85.725 | 5.823 | 1.00 | 14.40 | O |
| ATOM | 14000 | NE2 | GLN | B | 294 | 60.479 | 85.769 | 5.924 | 1.00 | 15.48 | N |

| ATOM | 14003 | C   | GLN B 294 | 63.756 | 88.675 | 10.103 | 1.00 | 12.48 | C  |
|------|-------|-----|-----------|--------|--------|--------|------|-------|----|
| ATOM | 14004 | O   | GLN B 294 | 64.768 | 88.252 | 10.670 | 1.00 | 12.19 | O  |
| ATOM | 14006 | N   | SER B 295 | 63.586 | 89.947 | 9.798  | 1.00 | 12.45 | N  |
| ATOM | 14007 | CA  | SER B 295 | 64.556 | 90.958 | 10.188 | 1.00 | 13.67 | C  |
| ATOM | 14009 | CB  | SER B 295 | 64.197 | 92.330 | 9.583  | 1.00 | 15.24 | C  |
| ATOM | 14012 | OG  | SER B 295 | 64.232 | 92.286 | 8.144  | 1.00 | 15.82 | O  |
| ATOM | 14014 | C   | SER B 295 | 64.735 | 91.037 | 11.705 | 1.00 | 12.09 | C  |
| ATOM | 14015 | O   | SER B 295 | 65.847 | 91.097 | 12.228 | 1.00 | 12.87 | O  |
| ATOM | 14017 | N   | LEU B 296 | 63.624 | 90.998 | 12.432 | 1.00 | 11.93 | N  |
| ATOM | 14018 | CA  | LEU B 296 | 63.645 | 91.010 | 13.875 | 1.00 | 12.08 | C  |
| ATOM | 14020 | CB  | LEU B 296 | 62.220 | 91.177 | 14.395 | 1.00 | 13.92 | C  |
| ATOM | 14023 | CG  | LEU B 296 | 61.671 | 92.584 | 14.259 | 1.00 | 13.28 | C  |
| ATOM | 14025 | CD1 | LEU B 296 | 60.210 | 92.582 | 14.554 | 1.00 | 14.00 | C  |
| ATOM | 14029 | CD2 | LEU B 296 | 62.382 | 93.488 | 15.230 | 1.00 | 14.70 | C  |
| ATOM | 14033 | C   | LEU B 296 | 64.263 | 89.743 | 14.448 | 1.00 | 12.60 | C  |
| ATOM | 14034 | O   | LEU B 296 | 64.994 | 89.821 | 15.432 | 1.00 | 12.82 | O  |
| ATOM | 14036 | N   | THR B 297 | 64.037 | 88.602 | 13.818 | 1.00 | 11.34 | N  |
| ATOM | 14037 | CA  | THR B 297 | 64.711 | 87.368 | 14.173 | 1.00 | 11.86 | C  |
| ATOM | 14039 | CB  | THR B 297 | 64.268 | 86.179 | 13.272 | 1.00 | 12.64 | C  |
| ATOM | 14041 | OG1 | THR B 297 | 62.873 | 85.938 | 13.454 | 1.00 | 12.79 | O  |
| ATOM | 14043 | CG2 | THR B 297 | 65.027 | 84.926 | 13.674 | 1.00 | 11.10 | C  |
| ATOM | 14047 | C   | THR B 297 | 66.252 | 87.547 | 14.132 | 1.00 | 12.23 | C  |
| ATOM | 14048 | O   | THR B 297 | 66.954 | 87.212 | 15.094 | 1.00 | 12.57 | O  |
| ATOM | 14050 | N   | ALA B 298 | 66.734 | 88.080 | 13.016 | 1.00 | 12.16 | N  |
| ATOM | 14051 | CA  | ALA B 298 | 68.181 | 88.305 | 12.816 | 1.00 | 11.43 | C  |
| ATOM | 14053 | CB  | ALA B 298 | 68.459 | 88.861 | 11.457 | 1.00 | 11.99 | C  |
| ATOM | 14057 | C   | ALA B 298 | 68.690 | 89.268 | 13.921 | 1.00 | 12.03 | C  |
| ATOM | 14058 | O   | ALA B 298 | 69.707 | 88.990 | 14.607 | 1.00 | 12.69 | O  |
| ATOM | 14060 | N   | MSE B 299 | 67.985 | 90.369 | 14.147 | 1.00 | 13.08 | N  |
| ATOM | 14061 | CA  | MSE B 299 | 68.484 | 91.366 | 15.127 | 1.00 | 14.65 | C  |
| ATOM | 14063 | CB  | MSE B 299 | 67.728 | 92.668 | 14.974 | 1.00 | 14.85 | C  |
| ATOM | 14066 | CG  | MSE B 299 | 67.985 | 93.222 | 13.646 | 1.00 | 19.58 | C  |
| ATOM | 14069 | SE  | MSE B 299 | 67.147 | 94.980 | 13.395 | 1.00 | 32.21 | SE |
| ATOM | 14070 | CE  | MSE B 299 | 68.538 | 96.049 | 14.090 | 1.00 | 31.10 | C  |
| ATOM | 14074 | C   | MSE B 299 | 68.470 | 90.839 | 16.543 | 1.00 | 12.67 | C  |
| ATOM | 14075 | O   | MSE B 299 | 69.280 | 91.208 | 17.405 | 1.00 | 12.64 | O  |
| ATOM | 14077 | N   | THR B 300 | 67.489 | 89.988 | 16.809 | 1.00 | 11.37 | N  |
| ATOM | 14078 | CA  | THR B 300 | 67.444 | 89.281 | 18.114 | 1.00 | 11.89 | C  |
| ATOM | 14080 | CB  | THR B 300 | 66.073 | 88.623 | 18.351 | 1.00 | 12.14 | C  |
| ATOM | 14082 | OG1 | THR B 300 | 65.015 | 89.602 | 18.203 | 1.00 | 12.66 | O  |
| ATOM | 14084 | CG2 | THR B 300 | 65.987 | 88.023 | 19.761 | 1.00 | 11.71 | C  |
| ATOM | 14088 | C   | THR B 300 | 68.608 | 88.304 | 18.279 | 1.00 | 11.87 | C  |
| ATOM | 14089 | O   | THR B 300 | 69.157 | 88.162 | 19.376 | 1.00 | 13.35 | O  |
| ATOM | 14091 | N   | VAL B 301 | 68.966 | 87.563 | 17.231 | 1.00 | 11.65 | N  |
| ATOM | 14092 | CA  | VAL B 301 | 70.115 | 86.667 | 17.338 | 1.00 | 12.32 | C  |
| ATOM | 14094 | CB  | VAL B 301 | 70.374 | 85.893 | 16.019 | 1.00 | 13.33 | C  |
| ATOM | 14096 | CG1 | VAL B 301 | 71.707 | 85.165 | 16.067 | 1.00 | 14.01 | C  |
| ATOM | 14100 | CG2 | VAL B 301 | 69.217 | 84.903 | 15.688 | 1.00 | 14.04 | C  |
| ATOM | 14104 | C   | VAL B 301 | 71.323 | 87.551 | 17.710 | 1.00 | 12.52 | C  |
| ATOM | 14105 | O   | VAL B 301 | 72.137 | 87.186 | 18.571 | 1.00 | 13.61 | O  |
| ATOM | 14107 | N   | GLU B 302 | 71.430 | 88.720 | 17.079 | 1.00 | 13.27 | N  |
| ATOM | 14108 | CA  | GLU B 302 | 72.548 | 89.625 | 17.391 | 1.00 | 13.07 | C  |
| ATOM | 14110 | CB  | GLU B 302 | 72.569 | 90.811 | 16.418 | 1.00 | 13.78 | C  |
| ATOM | 14113 | CG  | GLU B 302 | 72.893 | 90.395 | 14.997 | 1.00 | 12.93 | C  |
| ATOM | 14116 | CD  | GLU B 302 | 73.103 | 91.625 | 14.106 | 1.00 | 14.18 | C  |
| ATOM | 14117 | OE1 | GLU B 302 | 72.073 | 92.269 | 13.827 | 1.00 | 15.13 | O  |
| ATOM | 14118 | OE2 | GLU B 302 | 74.271 | 91.973 | 13.724 | 1.00 | 14.21 | O  |

| ATOM | 14119 | C   | GLU | B | 302 | 72.512 | 90.109 | 18.856 | 1.00 | 13.56 | C  |
|------|-------|-----|-----|---|-----|--------|--------|--------|------|-------|----|
| ATOM | 14120 | O   | GLU | B | 302 | 73.480 | 89.989 | 19.584 | 1.00 | 14.02 | O  |
| ATOM | 14122 | N   | ALA | B | 303 | 71.357 | 90.596 | 19.316 | 1.00 | 12.89 | N  |
| ATOM | 14123 | CA  | ALA | B | 303 | 71.239 | 91.096 | 20.692 | 1.00 | 13.05 | C  |
| ATOM | 14125 | CB  | ALA | B | 303 | 69.868 | 91.650 | 20.951 | 1.00 | 15.00 | C  |
| ATOM | 14129 | C   | ALA | B | 303 | 71.522 | 89.974 | 21.703 | 1.00 | 13.54 | C  |
| ATOM | 14130 | O   | ALA | B | 303 | 72.045 | 90.225 | 22.756 | 1.00 | 13.52 | O  |
| ATOM | 14132 | N   | MSE | B | 304 | 71.165 | 88.738 | 21.351 | 1.00 | 12.53 | N  |
| ATOM | 14133 | CA  | MSE | B | 304 | 71.318 | 87.573 | 22.259 | 1.00 | 13.25 | C  |
| ATOM | 14135 | CB  | MSE | B | 304 | 70.229 | 86.559 | 21.953 | 1.00 | 14.31 | C  |
| ATOM | 14138 | CG  | MSE | B | 304 | 68.833 | 87.045 | 22.251 | 1.00 | 13.82 | C  |
| ATOM | 14141 | SE  | MSE | B | 304 | 68.548 | 86.872 | 24.230 | 1.00 | 25.45 | SE |
| ATOM | 14142 | CE  | MSE | B | 304 | 68.413 | 84.876 | 24.400 | 1.00 | 20.24 | C  |
| ATOM | 14146 | C   | MSE | B | 304 | 72.680 | 86.913 | 22.121 | 1.00 | 13.48 | C  |
| ATOM | 14147 | O   | MSE | B | 304 | 72.935 | 85.924 | 22.762 | 1.00 | 14.36 | O  |
| ATOM | 14149 | N   | VAL | B | 305 | 73.566 | 87.504 | 21.316 | 1.00 | 13.71 | N  |
| ATOM | 14150 | CA  | VAL | B | 305 | 74.843 | 86.889 | 20.929 | 1.00 | 14.54 | C  |
| ATOM | 14152 | CB  | VAL | B | 305 | 75.992 | 87.196 | 21.923 | 1.00 | 14.52 | C  |
| ATOM | 14154 | CG1 | VAL | B | 305 | 77.303 | 86.645 | 21.447 | 1.00 | 20.00 | C  |
| ATOM | 14158 | CG2 | VAL | B | 305 | 76.193 | 88.689 | 21.965 | 1.00 | 16.97 | C  |
| ATOM | 14162 | C   | VAL | B | 305 | 74.632 | 85.391 | 20.630 | 1.00 | 14.43 | C  |
| ATOM | 14163 | O   | VAL | B | 305 | 75.367 | 84.498 | 21.085 | 1.00 | 15.33 | O  |
| ATOM | 14165 | N   | GLY | B | 306 | 73.597 | 85.137 | 19.837 | 1.00 | 14.08 | N  |
| ATOM | 14166 | CA  | GLY | B | 306 | 73.205 | 83.799 | 19.502 | 1.00 | 14.24 | C  |
| ATOM | 14169 | C   | GLY | B | 306 | 73.881 | 83.265 | 18.264 | 1.00 | 15.00 | C  |
| ATOM | 14170 | O   | GLY | B | 306 | 74.818 | 83.871 | 17.740 | 1.00 | 15.13 | O  |
| ATOM | 14172 | N   | HIS | B | 307 | 73.376 | 82.119 | 17.813 | 1.00 | 14.55 | N  |
| ATOM | 14173 | CA  | HIS | B | 307 | 74.070 | 81.360 | 16.764 | 1.00 | 15.15 | C  |
| ATOM | 14175 | CB  | HIS | B | 307 | 73.968 | 79.879 | 17.052 | 1.00 | 15.17 | C  |
| ATOM | 14178 | CG  | HIS | B | 307 | 74.709 | 79.457 | 18.275 | 1.00 | 18.30 | C  |
| ATOM | 14179 | ND1 | HIS | B | 307 | 74.098 | 79.273 | 19.496 | 1.00 | 24.84 | N  |
| ATOM | 14181 | CE1 | HIS | B | 307 | 75.002 | 78.881 | 20.380 | 1.00 | 24.68 | C  |
| ATOM | 14183 | NE2 | HIS | B | 307 | 76.175 | 78.793 | 19.770 | 1.00 | 22.15 | N  |
| ATOM | 14185 | CD2 | HIS | B | 307 | 76.010 | 79.127 | 18.448 | 1.00 | 20.81 | C  |
| ATOM | 14187 | C   | HIS | B | 307 | 73.504 | 81.622 | 15.374 | 1.00 | 14.34 | C  |
| ATOM | 14188 | O   | HIS | B | 307 | 72.355 | 81.268 | 15.041 | 1.00 | 14.43 | O  |
| ATOM | 14190 | N   | ALA | B | 308 | 74.350 | 82.147 | 14.504 | 1.00 | 12.80 | N  |
| ATOM | 14191 | CA  | ALA | B | 308 | 73.963 | 82.274 | 13.097 | 1.00 | 13.58 | C  |
| ATOM | 14193 | CB  | ALA | B | 308 | 74.942 | 83.131 | 12.398 | 1.00 | 15.25 | C  |
| ATOM | 14197 | C   | ALA | B | 308 | 73.886 | 80.867 | 12.450 | 1.00 | 13.25 | C  |
| ATOM | 14198 | O   | ALA | B | 308 | 73.301 | 80.709 | 11.373 | 1.00 | 13.45 | O  |
| ATOM | 14200 | N   | GLY | B | 309 | 74.508 | 79.875 | 13.080 | 1.00 | 11.83 | N  |
| ATOM | 14201 | CA  | GLY | B | 309 | 74.580 | 78.497 | 12.575 | 1.00 | 12.45 | C  |
| ATOM | 14204 | C   | GLY | B | 309 | 73.195 | 77.887 | 12.326 | 1.00 | 11.46 | C  |
| ATOM | 14205 | O   | GLY | B | 309 | 73.057 | 77.002 | 11.508 | 1.00 | 11.57 | O  |
| ATOM | 14207 | N   | SER | B | 310 | 72.185 | 78.340 | 13.064 | 1.00 | 11.44 | N  |
| ATOM | 14208 | CA  | SER | B | 310 | 70.797 | 77.821 | 12.880 | 1.00 | 11.64 | C  |
| ATOM | 14210 | CB  | SER | B | 310 | 69.793 | 78.527 | 13.789 | 1.00 | 11.33 | C  |
| ATOM | 14213 | OG  | SER | B | 310 | 70.098 | 78.325 | 15.120 | 1.00 | 12.23 | O  |
| ATOM | 14215 | C   | SER | B | 310 | 70.333 | 77.949 | 11.430 | 1.00 | 12.76 | C  |
| ATOM | 14216 | O   | SER | B | 310 | 69.420 | 77.239 | 11.016 | 1.00 | 13.11 | O  |
| ATOM | 14218 | N   | PHE | B | 311 | 70.934 | 78.879 | 10.677 | 1.00 | 11.46 | N  |
| ATOM | 14219 | CA  | PHE | B | 311 | 70.438 | 79.244 | 9.345  | 1.00 | 11.30 | C  |
| ATOM | 14221 | CB  | PHE | B | 311 | 70.267 | 80.756 | 9.292  | 1.00 | 12.43 | C  |
| ATOM | 14224 | CG  | PHE | B | 311 | 69.545 | 81.274 | 10.486 | 1.00 | 11.75 | C  |
| ATOM | 14225 | CD1 | PHE | B | 311 | 68.185 | 81.094 | 10.575 | 1.00 | 13.25 | C  |
| ATOM | 14227 | CE1 | PHE | B | 311 | 67.512 | 81.472 | 11.673 | 1.00 | 13.56 | C  |

| | | | | | | | | | |
|---|---|---|---|---|---|---|---|---|---|
| ATOM | 14229 | CZ | PHE | B | 311 | 68.177 | 82.032 | 12.752 | 1.00 12.57 | C |
| ATOM | 14231 | CE2 | PHE | B | 311 | 69.522 | 82.194 | 12.700 | 1.00 12.37 | C |
| ATOM | 14233 | CD2 | PHE | B | 311 | 70.204 | 81.857 | 11.547 | 1.00 12.18 | C |
| ATOM | 14235 | C | PHE | B | 311 | 71.337 | 78.742 | 8.226 | 1.00 11.42 | C |
| ATOM | 14236 | O | PHE | B | 311 | 71.189 | 79.142 | 7.112 | 1.00 12.67 | O |
| ATOM | 14238 | N | HIS | B | 312 | 72.292 | 77.876 | 8.563 | 1.00 11.85 | N |
| ATOM | 14239 | CA | HIS | B | 312 | 73.222 | 77.305 | 7.617 | 1.00 11.37 | C |
| ATOM | 14241 | CB | HIS | B | 312 | 74.202 | 76.412 | 8.377 | 1.00 11.33 | C |
| ATOM | 14244 | CG | HIS | B | 312 | 75.391 | 76.030 | 7.574 | 1.00 12.77 | C |
| ATOM | 14245 | ND1 | HIS | B | 312 | 75.364 | 75.025 | 6.623 | 1.00 11.07 | N |
| ATOM | 14247 | CE1 | HIS | B | 312 | 76.565 | 74.912 | 6.091 | 1.00 12.65 | C |
| ATOM | 14249 | NE2 | HIS | B | 312 | 77.371 | 75.796 | 6.668 | 1.00 12.81 | N |
| ATOM | 14251 | CD2 | HIS | B | 312 | 76.662 | 76.497 | 7.596 | 1.00 11.21 | C |
| ATOM | 14253 | C | HIS | B | 312 | 72.489 | 76.482 | 6.560 | 1.00 11.97 | C |
| ATOM | 14254 | O | HIS | B | 312 | 71.542 | 75.788 | 6.907 | 1.00 12.10 | O |
| ATOM | 14256 | N | PRO | B | 313 | 72.900 | 76.567 | 5.272 | 1.00 12.97 | N |
| ATOM | 14257 | CA | PRO | B | 313 | 72.216 | 75.758 | 4.238 | 1.00 11.80 | C |
| ATOM | 14259 | CB | PRO | B | 313 | 73.096 | 75.918 | 2.996 | 1.00 13.51 | C |
| ATOM | 14262 | CG | PRO | B | 313 | 73.945 | 77.113 | 3.250 | 1.00 13.48 | C |
| ATOM | 14265 | CD | PRO | B | 313 | 73.975 | 77.406 | 4.696 | 1.00 12.02 | C |
| ATOM | 14268 | C | PRO | B | 313 | 72.109 | 74.265 | 4.518 | 1.00 11.29 | C |
| ATOM | 14269 | O | PRO | B | 313 | 71.181 | 73.620 | 4.009 | 1.00 12.10 | O |
| ATOM | 14270 | N | PHE | B | 314 | 73.067 | 73.676 | 5.228 | 1.00 9.64 | N |
| ATOM | 14271 | CA | PHE | B | 314 | 72.989 | 72.248 | 5.462 | 1.00 9.92 | C |
| ATOM | 14273 | CB | PHE | B | 314 | 74.177 | 71.757 | 6.280 | 1.00 8.60 | C |
| ATOM | 14276 | CG | PHE | B | 314 | 74.186 | 70.300 | 6.447 | 1.00 10.02 | C |
| ATOM | 14277 | CD1 | PHE | B | 314 | 74.515 | 69.447 | 5.378 | 1.00 9.24 | C |
| ATOM | 14279 | CE1 | PHE | B | 314 | 74.515 | 68.033 | 5.543 | 1.00 10.22 | C |
| ATOM | 14281 | CZ | PHE | B | 314 | 74.078 | 67.522 | 6.793 | 1.00 9.16 | C |
| ATOM | 14283 | CE2 | PHE | B | 314 | 73.760 | 68.365 | 7.790 | 1.00 8.11 | C |
| ATOM | 14285 | CD2 | PHE | B | 314 | 73.786 | 69.759 | 7.626 | 1.00 9.48 | C |
| ATOM | 14287 | C | PHE | B | 314 | 71.685 | 71.890 | 6.195 | 1.00 8.68 | C |
| ATOM | 14288 | O | PHE | B | 314 | 71.081 | 70.846 | 5.946 | 1.00 9.71 | O |
| ATOM | 14290 | N | LEU | B | 315 | 71.259 | 72.773 | 7.068 | 1.00 9.50 | N |
| ATOM | 14291 | CA | LEU | B | 315 | 70.108 | 72.545 | 7.947 | 1.00 9.59 | C |
| ATOM | 14293 | CB | LEU | B | 315 | 70.191 | 73.408 | 9.201 | 1.00 11.14 | C |
| ATOM | 14296 | CG | LEU | B | 315 | 71.249 | 73.003 | 10.236 | 1.00 9.91 | C |
| ATOM | 14298 | CD1 | LEU | B | 315 | 71.355 | 74.070 | 11.336 | 1.00 11.00 | C |
| ATOM | 14302 | CD2 | LEU | B | 315 | 70.901 | 71.674 | 10.861 | 1.00 13.64 | C |
| ATOM | 14306 | C | LEU | B | 315 | 68.787 | 72.756 | 7.273 | 1.00 9.56 | C |
| ATOM | 14307 | O | LEU | B | 315 | 67.729 | 72.573 | 7.893 | 1.00 11.17 | O |
| ATOM | 14309 | N | HIS | B | 316 | 68.813 | 73.231 | 6.026 | 1.00 9.87 | N |
| ATOM | 14310 | CA | HIS | B | 316 | 67.574 | 73.520 | 5.305 | 1.00 10.23 | C |
| ATOM | 14312 | CB | HIS | B | 316 | 67.322 | 75.023 | 5.332 | 1.00 9.65 | C |
| ATOM | 14315 | CG | HIS | B | 316 | 67.404 | 75.593 | 6.697 | 1.00 11.20 | C |
| ATOM | 14316 | ND1 | HIS | B | 316 | 66.373 | 75.509 | 7.610 | 1.00 11.25 | N |
| ATOM | 14318 | CE1 | HIS | B | 316 | 66.762 | 76.050 | 8.758 | 1.00 14.23 | C |
| ATOM | 14320 | NE2 | HIS | B | 316 | 68.039 | 76.398 | 8.643 | 1.00 10.70 | N |
| ATOM | 14322 | CD2 | HIS | B | 316 | 68.455 | 76.121 | 7.363 | 1.00 13.24 | C |
| ATOM | 14324 | C | HIS | B | 316 | 67.629 | 72.954 | 3.880 | 1.00 10.98 | C |
| ATOM | 14325 | O | HIS | B | 316 | 67.038 | 71.883 | 3.591 | 1.00 12.49 | O |
| ATOM | 14327 | N | ASP | B | 317 | 68.439 | 73.595 | 3.038 | 1.00 12.19 | N |
| ATOM | 14328 | CA | ASP | B | 317 | 68.601 | 73.198 | 1.635 | 1.00 12.34 | C |
| ATOM | 14330 | CB | ASP | B | 317 | 69.734 | 74.002 | 0.993 | 1.00 12.71 | C |
| ATOM | 14333 | CG | ASP | B | 317 | 69.576 | 75.531 | 1.121 | 1.00 15.92 | C |
| ATOM | 14334 | OD1 | ASP | B | 317 | 69.721 | 76.195 | 0.073 | 1.00 18.54 | O |
| ATOM | 14335 | OD2 | ASP | B | 317 | 69.312 | 76.076 | 2.224 | 1.00 12.32 | O |

| ATOM | 14336 | C | ASP | B | 317 | 68.910 | 71.705 | 1.459 | 1.00 | 12.36 | C |
|---|---|---|---|---|---|---|---|---|---|---|---|
| ATOM | 14337 | O | ASP | B | 317 | 68.372 | 71.035 | 0.553 | 1.00 | 12.97 | O |
| ATOM | 14339 | N | VAL | B | 318 | 69.806 | 71.173 | 2.304 | 1.00 | 11.61 | N |
| ATOM | 14340 | CA | VAL | B | 318 | 70.243 | 69.807 | 2.161 | 1.00 | 11.36 | C |
| ATOM | 14342 | CB | VAL | B | 318 | 71.638 | 69.608 | 2.710 | 1.00 | 12.26 | C |
| ATOM | 14344 | CG1 | VAL | B | 318 | 72.029 | 68.132 | 2.631 | 1.00 | 11.62 | C |
| ATOM | 14348 | CG2 | VAL | B | 318 | 72.628 | 70.473 | 1.891 | 1.00 | 12.13 | C |
| ATOM | 14352 | C | VAL | B | 318 | 69.286 | 68.871 | 2.881 | 1.00 | 12.26 | C |
| ATOM | 14353 | O | VAL | B | 318 | 68.909 | 67.803 | 2.335 | 1.00 | 14.69 | O |
| ATOM | 14355 | N | THR | B | 319 | 69.005 | 69.195 | 4.124 | 1.00 | 11.95 | N |
| ATOM | 14356 | CA | THR | B | 319 | 68.364 | 68.224 | 5.014 | 1.00 | 11.57 | C |
| ATOM | 14358 | CB | THR | B | 319 | 68.895 | 68.367 | 6.470 | 1.00 | 10.93 | C |
| ATOM | 14360 | OG1 | THR | B | 319 | 68.814 | 69.739 | 6.895 | 1.00 | 9.86 | O |
| ATOM | 14362 | CG2 | THR | B | 319 | 70.292 | 67.865 | 6.560 | 1.00 | 12.29 | C |
| ATOM | 14366 | C | THR | B | 319 | 66.829 | 68.237 | 5.064 | 1.00 | 11.01 | C |
| ATOM | 14367 | O | THR | B | 319 | 66.219 | 67.172 | 5.309 | 1.00 | 10.43 | O |
| ATOM | 14369 | N | ARG | B | 320 | 66.206 | 69.392 | 4.836 | 1.00 | 10.80 | N |
| ATOM | 14370 | CA | ARG | B | 320 | 64.749 | 69.482 | 4.953 | 1.00 | 11.53 | C |
| ATOM | 14372 | CB | ARG | B | 320 | 64.301 | 69.766 | 6.403 | 1.00 | 11.07 | C |
| ATOM | 14375 | CG | ARG | B | 320 | 62.767 | 69.800 | 6.566 | 1.00 | 11.69 | C |
| ATOM | 14378 | CD | ARG | B | 320 | 62.443 | 69.748 | 8.030 | 1.00 | 12.62 | C |
| ATOM | 14381 | NE | ARG | B | 320 | 61.011 | 69.705 | 8.411 | 1.00 | 13.08 | N |
| ATOM | 14383 | CZ | ARG | B | 320 | 60.391 | 70.579 | 9.167 | 1.00 | 14.17 | C |
| ATOM | 14384 | NH1 | ARG | B | 320 | 60.956 | 71.745 | 9.499 | 1.00 | 14.11 | N |
| ATOM | 14387 | NH2 | ARG | B | 320 | 59.144 | 70.313 | 9.543 | 1.00 | 14.62 | N |
| ATOM | 14390 | C | ARG | B | 320 | 64.228 | 70.533 | 3.962 | 1.00 | 11.67 | C |
| ATOM | 14391 | O | ARG | B | 320 | 63.940 | 71.690 | 4.313 | 1.00 | 11.62 | O |
| ATOM | 14393 | N | PRO | B | 321 | 64.212 | 70.134 | 2.675 | 1.00 | 11.53 | N |
| ATOM | 14394 | CA | PRO | B | 321 | 64.135 | 71.110 | 1.593 | 1.00 | 12.03 | C |
| ATOM | 14396 | CB | PRO | B | 321 | 64.823 | 70.380 | 0.418 | 1.00 | 12.17 | C |
| ATOM | 14399 | CG | PRO | B | 321 | 64.510 | 68.954 | 0.637 | 1.00 | 12.88 | C |
| ATOM | 14402 | CD | PRO | B | 321 | 64.466 | 68.763 | 2.158 | 1.00 | 11.74 | C |
| ATOM | 14405 | C | PRO | B | 321 | 62.743 | 71.642 | 1.243 | 1.00 | 11.78 | C |
| ATOM | 14406 | O | PRO | B | 321 | 62.359 | 71.637 | 0.087 | 1.00 | 12.21 | O |
| ATOM | 14407 | N | HIS | B | 322 | 62.017 | 72.108 | 2.249 | 1.00 | 11.28 | N |
| ATOM | 14408 | CA | HIS | B | 322 | 60.799 | 72.827 | 2.021 | 1.00 | 11.35 | C |
| ATOM | 14410 | CB | HIS | B | 322 | 60.061 | 73.079 | 3.318 | 1.00 | 12.52 | C |
| ATOM | 14413 | CG | HIS | B | 322 | 59.425 | 71.874 | 3.900 | 1.00 | 14.09 | C |
| ATOM | 14414 | ND1 | HIS | B | 322 | 58.334 | 71.256 | 3.323 | 1.00 | 12.30 | N |
| ATOM | 14416 | CE1 | HIS | B | 322 | 57.982 | 70.230 | 4.071 | 1.00 | 13.05 | C |
| ATOM | 14418 | NE2 | HIS | B | 322 | 58.795 | 70.162 | 5.113 | 1.00 | 13.88 | N |
| ATOM | 14420 | CD2 | HIS | B | 322 | 59.696 | 71.194 | 5.034 | 1.00 | 14.71 | C |
| ATOM | 14422 | C | HIS | B | 322 | 61.204 | 74.166 | 1.440 | 1.00 | 11.54 | C |
| ATOM | 14423 | O | HIS | B | 322 | 61.979 | 74.919 | 2.059 | 1.00 | 11.31 | O |
| ATOM | 14425 | N | PRO | B | 323 | 60.715 | 74.477 | 0.232 | 1.00 | 12.40 | N |
| ATOM | 14426 | CA | PRO | B | 323 | 61.193 | 75.712 | -0.403 | 1.00 | 12.05 | C |
| ATOM | 14428 | CB | PRO | B | 323 | 60.318 | 75.821 | -1.656 | 1.00 | 12.48 | C |
| ATOM | 14431 | CG | PRO | B | 323 | 60.065 | 74.352 | -2.036 | 1.00 | 12.65 | C |
| ATOM | 14434 | CD | PRO | B | 323 | 59.890 | 73.647 | -0.684 | 1.00 | 13.19 | C |
| ATOM | 14437 | C | PRO | B | 323 | 61.148 | 76.977 | 0.424 | 1.00 | 11.54 | C |
| ATOM | 14438 | O | PRO | B | 323 | 62.100 | 77.766 | 0.401 | 1.00 | 12.67 | O |
| ATOM | 14439 | N | THR | B | 324 | 60.088 | 77.180 | 1.187 | 1.00 | 10.86 | N |
| ATOM | 14440 | CA | THR | B | 324 | 59.965 | 78.427 | 1.966 | 1.00 | 11.41 | C |
| ATOM | 14442 | CB | THR | B | 324 | 58.524 | 78.795 | 2.268 | 1.00 | 11.39 | C |
| ATOM | 14444 | OG1 | THR | B | 324 | 57.872 | 77.656 | 2.841 | 1.00 | 12.67 | O |
| ATOM | 14446 | CG2 | THR | B | 324 | 57.810 | 79.280 | 0.971 | 1.00 | 12.44 | C |
| ATOM | 14450 | C | THR | B | 324 | 60.759 | 78.347 | 3.253 | 1.00 | 10.40 | C |

| | | | | | | | | | |
|---|---|---|---|---|---|---|---|---|---|
| ATOM | 14451 | O | THR | B | 324 | 61.112 | 79.398 | 3.806 | 1.00 12.80 | O |
| ATOM | 14453 | N | GLN | B | 325 | 61.077 | 77.146 | 3.737 | 1.00 11.29 | N |
| ATOM | 14454 | CA | GLN | B | 325 | 62.014 | 77.049 | 4.846 | 1.00 10.48 | C |
| ATOM | 14456 | CB | GLN | B | 325 | 62.092 | 75.615 | 5.342 | 1.00 10.35 | C |
| ATOM | 14459 | CG | GLN | B | 325 | 62.920 | 75.488 | 6.618 | 1.00 10.79 | C |
| ATOM | 14462 | CD | GLN | B | 325 | 62.973 | 74.074 | 7.141 | 1.00 10.18 | C |
| ATOM | 14463 | OE1 | GLN | B | 325 | 61.950 | 73.390 | 7.207 | 1.00 12.44 | O |
| ATOM | 14464 | NE2 | GLN | B | 325 | 64.172 | 73.639 | 7.591 | 1.00 10.71 | N |
| ATOM | 14467 | C | GLN | B | 325 | 63.416 | 77.492 | 4.378 | 1.00 10.47 | C |
| ATOM | 14468 | O | GLN | B | 325 | 64.128 | 78.263 | 5.058 | 1.00 11.65 | O |
| ATOM | 14470 | N | ILE | B | 326 | 63.820 | 76.969 | 3.228 | 1.00 11.90 | N |
| ATOM | 14471 | CA | ILE | B | 326 | 65.068 | 77.374 | 2.581 | 1.00 10.37 | C |
| ATOM | 14473 | CB | ILE | B | 326 | 65.200 | 76.699 | 1.238 | 1.00 10.22 | C |
| ATOM | 14475 | CG1 | ILE | B | 326 | 65.385 | 75.182 | 1.411 | 1.00 11.70 | C |
| ATOM | 14478 | CD1 | ILE | B | 326 | 65.296 | 74.412 | 0.105 | 1.00 12.35 | C |
| ATOM | 14482 | CG2 | ILE | B | 326 | 66.322 | 77.315 | 0.425 | 1.00 11.74 | C |
| ATOM | 14486 | C | ILE | B | 326 | 65.096 | 78.892 | 2.419 | 1.00 11.43 | C |
| ATOM | 14487 | O | ILE | B | 326 | 66.084 | 79.533 | 2.712 | 1.00 11.56 | O |
| ATOM | 14489 | N | GLU | B | 327 | 63.979 | 79.443 | 1.944 | 1.00 12.50 | N |
| ATOM | 14490 | CA | GLU | B | 327 | 63.879 | 80.875 | 1.715 | 1.00 12.68 | C |
| ATOM | 14492 | CB | GLU | B | 327 | 62.525 | 81.190 | 1.105 | 1.00 14.40 | C |
| ATOM | 14495 | CG | GLU | B | 327 | 62.171 | 82.634 | 1.049 | 1.00 14.91 | C |
| ATOM | 14498 | CD | GLU | B | 327 | 60.774 | 82.880 | 0.410 | 1.00 16.14 | C |
| ATOM | 14499 | OE1 | GLU | B | 327 | 60.231 | 81.942 | -0.210 | 1.00 19.10 | O |
| ATOM | 14500 | OE2 | GLU | B | 327 | 60.271 | 83.994 | 0.542 | 1.00 21.43 | O |
| ATOM | 14501 | C | GLU | B | 327 | 64.115 | 81.693 | 2.973 | 1.00 12.82 | C |
| ATOM | 14502 | O | GLU | B | 327 | 64.879 | 82.653 | 2.981 | 1.00 13.33 | O |
| ATOM | 14504 | N | VAL | B | 328 | 63.398 | 81.339 | 4.030 | 1.00 10.86 | N |
| ATOM | 14505 | CA | VAL | B | 328 | 63.478 | 82.110 | 5.278 | 1.00 11.33 | C |
| ATOM | 14507 | CB | VAL | B | 328 | 62.403 | 81.638 | 6.274 | 1.00 11.98 | C |
| ATOM | 14509 | CG1 | VAL | B | 328 | 62.647 | 82.278 | 7.632 | 1.00 12.69 | C |
| ATOM | 14513 | CG2 | VAL | B | 328 | 60.981 | 81.925 | 5.722 | 1.00 12.37 | C |
| ATOM | 14517 | C | VAL | B | 328 | 64.916 | 82.000 | 5.897 | 1.00 11.57 | C |
| ATOM | 14518 | O | VAL | B | 328 | 65.527 | 82.996 | 6.317 | 1.00 12.30 | O |
| ATOM | 14520 | N | ALA | B | 329 | 65.445 | 80.800 | 5.967 | 1.00 11.82 | N |
| ATOM | 14521 | CA | ALA | B | 329 | 66.804 | 80.583 | 6.479 | 1.00 11.57 | C |
| ATOM | 14523 | CB | ALA | B | 329 | 67.156 | 79.139 | 6.448 | 1.00 12.22 | C |
| ATOM | 14527 | C | ALA | B | 329 | 67.804 | 81.408 | 5.682 | 1.00 11.46 | C |
| ATOM | 14528 | O | ALA | B | 329 | 68.709 | 82.026 | 6.225 | 1.00 12.90 | O |
| ATOM | 14530 | N | GLY | B | 330 | 67.611 | 81.440 | 4.375 | 1.00 12.04 | N |
| ATOM | 14531 | CA | GLY | B | 330 | 68.501 | 82.221 | 3.502 | 1.00 12.28 | C |
| ATOM | 14534 | C | GLY | B | 330 | 68.398 | 83.712 | 3.761 | 1.00 12.37 | C |
| ATOM | 14535 | O | GLY | B | 330 | 69.426 | 84.418 | 3.718 | 1.00 12.50 | O |
| ATOM | 14537 | N | ASN | B | 331 | 67.184 | 84.226 | 3.955 | 1.00 11.52 | N |
| ATOM | 14538 | CA | ASN | B | 331 | 67.019 | 85.656 | 4.290 | 1.00 12.10 | C |
| ATOM | 14540 | CB | ASN | B | 331 | 65.547 | 86.046 | 4.417 | 1.00 12.24 | C |
| ATOM | 14543 | CG | ASN | B | 331 | 64.801 | 86.054 | 3.084 | 1.00 13.01 | C |
| ATOM | 14544 | OD1 | ASN | B | 331 | 65.405 | 86.183 | 2.029 | 1.00 14.78 | O |
| ATOM | 14545 | ND2 | ASN | B | 331 | 63.433 | 86.002 | 3.164 | 1.00 13.38 | N |
| ATOM | 14548 | C | ASN | B | 331 | 67.728 | 85.979 | 5.594 | 1.00 11.14 | C |
| ATOM | 14549 | O | ASN | B | 331 | 68.499 | 86.924 | 5.654 | 1.00 13.10 | O |
| ATOM | 14551 | N | ILE | B | 332 | 67.515 | 85.161 | 6.617 | 1.00 12.12 | N |
| ATOM | 14552 | CA | ILE | B | 332 | 68.131 | 85.428 | 7.916 | 1.00 11.89 | C |
| ATOM | 14554 | CB | ILE | B | 332 | 67.479 | 84.599 | 9.041 | 1.00 12.73 | C |
| ATOM | 14556 | CG1 | ILE | B | 332 | 65.996 | 84.967 | 9.152 | 1.00 12.03 | C |
| ATOM | 14559 | CD1 | ILE | B | 332 | 65.242 | 83.979 | 10.000 | 1.00 12.91 | C |
| ATOM | 14563 | CG2 | ILE | B | 332 | 68.202 | 84.774 | 10.348 | 1.00 11.57 | C |

| | | | | | | | | | |
|---|---|---|---|---|---|---|---|---|---|
| ATOM | 14567 | C | ILE | B | 332 | 69.657 | 85.221 | 7.843 | 1.00 11.85 | C |
| ATOM | 14568 | O | ILE | B | 332 | 70.428 | 86.005 | 8.409 | 1.00 11.40 | O |
| ATOM | 14570 | N | ARG | B | 333 | 70.108 | 84.192 | 7.130 | 1.00 11.01 | N |
| ATOM | 14571 | CA | ARG | B | 333 | 71.522 | 83.990 | 6.898 | 1.00 11.82 | C |
| ATOM | 14573 | CB | ARG | B | 333 | 71.729 | 82.748 | 5.980 | 1.00 11.33 | C |
| ATOM | 14576 | CG | ARG | B | 333 | 73.198 | 82.399 | 5.722 | 1.00 12.57 | C |
| ATOM | 14579 | CD | ARG | B | 333 | 73.374 | 81.030 | 5.083 | 1.00 12.66 | C |
| ATOM | 14582 | NE | ARG | B | 333 | 72.773 | 80.932 | 3.729 | 1.00 12.65 | N |
| ATOM | 14584 | CZ | ARG | B | 333 | 71.651 | 80.260 | 3.416 | 1.00 12.77 | C |
| ATOM | 14585 | NH1 | ARG | B | 333 | 70.888 | 79.637 | 4.353 | 1.00 13.26 | N |
| ATOM | 14588 | NH2 | ARG | B | 333 | 71.251 | 80.223 | 2.153 | 1.00 12.50 | N |
| ATOM | 14591 | C | ARG | B | 333 | 72.170 | 85.252 | 6.263 | 1.00 12.37 | C |
| ATOM | 14592 | O | ARG | B | 333 | 73.213 | 85.720 | 6.726 | 1.00 12.46 | O |
| ATOM | 14594 | N | LYS | B | 334 | 71.518 | 85.775 | 5.234 | 1.00 13.01 | N |
| ATOM | 14595 | CA | LYS | B | 334 | 71.976 | 86.983 | 4.527 | 1.00 13.30 | C |
| ATOM | 14597 | CB | LYS | B | 334 | 71.025 | 87.325 | 3.383 | 1.00 14.74 | C |
| ATOM | 14600 | CG | LYS | B | 334 | 71.340 | 88.686 | 2.745 | 1.00 20.30 | C |
| ATOM | 14603 | CD | LYS | B | 334 | 71.330 | 88.681 | 1.227 | 1.00 28.40 | C |
| ATOM | 14606 | CE | LYS | B | 334 | 70.042 | 88.311 | 0.631 | 1.00 30.15 | C |
| ATOM | 14609 | NZ | LYS | B | 334 | 70.113 | 88.519 | -0.864 | 1.00 33.32 | N |
| ATOM | 14613 | C | LYS | B | 334 | 72.114 | 88.145 | 5.503 | 1.00 12.82 | C |
| ATOM | 14614 | O | LYS | B | 334 | 73.145 | 88.809 | 5.554 | 1.00 12.22 | O |
| ATOM | 14616 | N | LEU | B | 335 | 71.085 | 88.349 | 6.311 | 1.00 12.36 | N |
| ATOM | 14617 | CA | LEU | B | 335 | 71.077 | 89.455 | 7.268 | 1.00 12.92 | C |
| ATOM | 14619 | CB | LEU | B | 335 | 69.737 | 89.562 | 7.964 | 1.00 13.39 | C |
| ATOM | 14622 | CG | LEU | B | 335 | 68.530 | 89.910 | 7.070 | 1.00 15.00 | C |
| ATOM | 14624 | CD1 | LEU | B | 335 | 67.308 | 89.834 | 7.896 | 1.00 16.85 | C |
| ATOM | 14628 | CD2 | LEU | B | 335 | 68.695 | 91.310 | 6.435 | 1.00 14.08 | C |
| ATOM | 14632 | C | LEU | B | 335 | 72.171 | 89.330 | 8.304 | 1.00 13.60 | C |
| ATOM | 14633 | O | LEU | B | 335 | 72.673 | 90.359 | 8.744 | 1.00 15.61 | O |
| ATOM | 14635 | N | LEU | B | 336 | 72.501 | 88.105 | 8.741 | 1.00 12.70 | N |
| ATOM | 14636 | CA | LEU | B | 336 | 73.530 | 87.904 | 9.779 | 1.00 13.04 | C |
| ATOM | 14638 | CB | LEU | B | 336 | 73.279 | 86.610 | 10.596 | 1.00 12.08 | C |
| ATOM | 14641 | CG | LEU | B | 336 | 71.972 | 86.685 | 11.414 | 1.00 11.44 | C |
| ATOM | 14643 | CD1 | LEU | B | 336 | 71.625 | 85.314 | 12.005 | 1.00 12.03 | C |
| ATOM | 14647 | CD2 | LEU | B | 336 | 72.108 | 87.765 | 12.490 | 1.00 12.36 | C |
| ATOM | 14651 | C | LEU | B | 336 | 74.978 | 87.919 | 9.289 | 1.00 13.77 | C |
| ATOM | 14652 | O | LEU | B | 336 | 75.908 | 88.007 | 10.108 | 1.00 13.51 | O |
| ATOM | 14654 | N | GLU | B | 337 | 75.199 | 87.839 | 7.984 | 1.00 14.34 | N |
| ATOM | 14655 | CA | GLU | B | 337 | 76.561 | 87.907 | 7.462 | 1.00 15.94 | C |
| ATOM | 14657 | CB | GLU | B | 337 | 76.586 | 87.831 | 5.956 | 1.00 17.19 | C |
| ATOM | 14660 | CG | GLU | B | 337 | 76.155 | 86.494 | 5.520 | 1.00 22.91 | C |
| ATOM | 14663 | CD | GLU | B | 337 | 76.993 | 85.887 | 4.442 | 1.00 30.43 | C |
| ATOM | 14664 | OE1 | GLU | B | 337 | 78.028 | 86.484 | 4.013 | 1.00 34.40 | O |
| ATOM | 14665 | OE2 | GLU | B | 337 | 76.587 | 84.765 | 4.063 | 1.00 36.55 | O |
| ATOM | 14666 | C | GLU | B | 337 | 77.214 | 89.181 | 7.899 | 1.00 15.15 | C |
| ATOM | 14667 | O | GLU | B | 337 | 76.625 | 90.249 | 7.791 | 1.00 14.95 | O |
| ATOM | 14669 | N | GLY | B | 338 | 78.423 | 89.047 | 8.408 | 1.00 15.01 | N |
| ATOM | 14670 | CA | GLY | B | 338 | 79.172 | 90.225 | 8.808 | 1.00 15.10 | C |
| ATOM | 14673 | C | GLY | B | 338 | 78.869 | 90.736 | 10.201 | 1.00 14.40 | C |
| ATOM | 14674 | O | GLY | B | 338 | 79.537 | 91.687 | 10.667 | 1.00 15.67 | O |
| ATOM | 14676 | N | SER | B | 339 | 77.872 | 90.159 | 10.874 | 1.00 14.14 | N |
| ATOM | 14677 | CA | SER | B | 339 | 77.600 | 90.507 | 12.269 | 1.00 12.80 | C |
| ATOM | 14679 | CB | SER | B | 339 | 76.370 | 89.777 | 12.812 | 1.00 14.05 | C |
| ATOM | 14682 | OG | SER | B | 339 | 76.083 | 90.226 | 14.142 | 1.00 13.79 | O |
| ATOM | 14684 | C | SER | B | 339 | 78.799 | 90.164 | 13.157 | 1.00 13.42 | C |
| ATOM | 14685 | O | SER | B | 339 | 79.387 | 89.119 | 13.019 | 1.00 13.21 | O |

```
ATOM  14687  N    ARG B 340      79.163  91.064  14.061  1.00 13.75           N
ATOM  14688  CA   ARG B 340      80.136  90.745  15.091  1.00 15.17           C
ATOM  14690  CB   ARG B 340      81.179  91.868  15.205  1.00 14.44           C
ATOM  14693  CG   ARG B 340      82.047  92.004  13.955  1.00 18.72           C
ATOM  14696  CD   ARG B 340      83.004  93.192  14.009  1.00 22.64           C
ATOM  14699  NE   ARG B 340      83.891  93.140  15.167  1.00 28.94           N
ATOM  14701  CZ   ARG B 340      84.381  94.196  15.824  1.00 30.70           C
ATOM  14702  NH1  ARG B 340      84.100  95.462  15.464  1.00 30.42           N
ATOM  14705  NH2  ARG B 340      85.171  93.971  16.867  1.00 31.50           N
ATOM  14708  C    ARG B 340      79.441  90.504  16.417  1.00 14.07           C
ATOM  14709  O    ARG B 340      80.102  90.288  17.414  1.00 14.34           O
ATOM  14711  N    PHE B 341      78.115  90.473  16.423  1.00 13.16           N
ATOM  14712  CA   PHE B 341      77.336  90.089  17.611  1.00 12.81           C
ATOM  14714  CB   PHE B 341      76.017  90.843  17.686  1.00 12.66           C
ATOM  14717  CG   PHE B 341      76.092  92.286  18.149  1.00 12.74           C
ATOM  14718  CD1  PHE B 341      76.655  92.642  19.372  1.00 14.83           C
ATOM  14720  CE1  PHE B 341      76.639  93.951  19.822  1.00 17.55           C
ATOM  14722  CZ   PHE B 341      76.063  94.945  19.048  1.00 14.79           C
ATOM  14724  CE2  PHE B 341      75.513  94.630  17.833  1.00 17.70           C
ATOM  14726  CD2  PHE B 341      75.508  93.289  17.380  1.00 16.35           C
ATOM  14728  C    PHE B 341      76.975  88.572  17.547  1.00 13.53           C
ATOM  14729  O    PHE B 341      77.215  87.798  18.477  1.00 14.05           O
ATOM  14731  N    ALA B 342      76.390  88.164  16.432  1.00 13.96           N
ATOM  14732  CA   ALA B 342      76.037  86.745  16.226  1.00 14.50           C
ATOM  14734  CB   ALA B 342      75.192  86.576  14.994  1.00 14.91           C
ATOM  14738  C    ALA B 342      77.308  85.929  16.079  1.00 16.04           C
ATOM  14739  O    ALA B 342      78.307  86.403  15.494  1.00 16.16           O
ATOM  14741  N    VAL B 343      77.266  84.698  16.591  1.00 16.46           N
ATOM  14742  CA   VAL B 343      78.345  83.713  16.464  1.00 17.35           C
ATOM  14744  CB   VAL B 343      78.339  82.780  17.677  1.00 18.08           C
ATOM  14746  CG1  VAL B 343      79.461  81.745  17.596  1.00 19.84           C
ATOM  14750  CG2  VAL B 343      78.459  83.629  18.959  1.00 20.72           C
ATOM  14754  C    VAL B 343      78.206  82.919  15.158  1.00 17.17           C
ATOM  14755  O    VAL B 343      77.139  82.383  14.864  1.00 17.45           O
ATOM  14757  N    HIS B 344      79.290  82.871  14.377  1.00 18.35           N
ATOM  14758  CA   HIS B 344      79.269  82.247  13.047  1.00 19.13           C
ATOM  14760  CB   HIS B 344      80.065  83.121  12.076  1.00 19.51           C
ATOM  14763  CG   HIS B 344      79.441  84.464  11.898  1.00 19.70           C
ATOM  14764  ND1  HIS B 344      78.349  84.659  11.080  1.00 18.35           N
ATOM  14766  CE1  HIS B 344      77.960  85.918  11.175  1.00 19.84           C
ATOM  14768  NE2  HIS B 344      78.756  86.538  12.030  1.00 19.11           N
ATOM  14770  CD2  HIS B 344      79.672  85.645  12.515  1.00 19.87           C
ATOM  14772  C    HIS B 344      79.777  80.802  13.035  1.00 20.27           C
ATOM  14773  O    HIS B 344      80.772  80.513  13.672  1.00 19.20           O
ATOM  14775  N    HIS B 345      79.074  79.926  12.296  1.00 21.38           N
ATOM  14776  CA   HIS B 345      79.381  78.476  12.278  1.00 22.30           C
ATOM  14778  CB   HIS B 345      78.389  77.673  11.362  1.00 23.14           C
ATOM  14781  CG   HIS B 345      78.874  76.301  10.993  1.00 23.23           C
ATOM  14782  ND1  HIS B 345      78.725  75.201  11.814  1.00 26.85           N
ATOM  14784  CE1  HIS B 345      79.244  74.139  11.226  1.00 26.68           C
ATOM  14786  NE2  HIS B 345      79.766  74.516  10.068  1.00 26.45           N
ATOM  14788  CD2  HIS B 345      79.524  75.856   9.887  1.00 22.82           C
ATOM  14790  C    HIS B 345      80.825  78.275  11.836  1.00 23.05           C
ATOM  14791  O    HIS B 345      81.561  77.483  12.419  1.00 22.74           O
ATOM  14793  N    GLU B 346      81.213  79.003  10.800  1.00 24.60           N
ATOM  14794  CA   GLU B 346      82.548  78.829  10.210  1.00 26.32           C
ATOM  14796  CB   GLU B 346      82.679  79.556   8.867  1.00 26.62           C
```

| ATOM | 14799 | CG | GLU B 346 | 82.692 | 81.060 | 8.974 | 1.00 | 28.47 | C |
|------|-------|-----|-----------|--------|--------|--------|------|-------|---|
| ATOM | 14802 | CD | GLU B 346 | 81.313 | 81.690 | 8.906 | 1.00 | 29.80 | C |
| ATOM | 14803 | OE1 | GLU B 346 | 80.275 | 80.990 | 9.094 | 1.00 | 30.56 | O |
| ATOM | 14804 | OE2 | GLU B 346 | 81.284 | 82.914 | 8.683 | 1.00 | 31.54 | O |
| ATOM | 14805 | C | GLU B 346 | 83.678 | 79.259 | 11.153 | 1.00 | 27.54 | C |
| ATOM | 14806 | O | GLU B 346 | 84.831 | 78.863 | 10.943 | 1.00 | 27.03 | O |
| ATOM | 14808 | N | GLU B 347 | 83.359 | 80.071 | 12.164 | 1.00 | 28.59 | N |
| ATOM | 14809 | CA | GLU B 347 | 84.337 | 80.394 | 13.209 | 1.00 | 31.22 | C |
| ATOM | 14811 | CB | GLU B 347 | 84.095 | 81.801 | 13.774 | 1.00 | 31.38 | C |
| ATOM | 14814 | CG | GLU B 347 | 84.288 | 82.950 | 12.759 | 1.00 | 33.54 | C |
| ATOM | 14817 | CD | GLU B 347 | 83.562 | 84.267 | 13.166 | 1.00 | 36.10 | C |
| ATOM | 14818 | OE1 | GLU B 347 | 83.169 | 84.430 | 14.362 | 1.00 | 44.49 | O |
| ATOM | 14819 | OE2 | GLU B 347 | 83.359 | 85.139 | 12.271 | 1.00 | 42.96 | O |
| ATOM | 14820 | C | GLU B 347 | 84.257 | 79.365 | 14.339 | 1.00 | 31.14 | C |
| ATOM | 14821 | O | GLU B 347 | 85.278 | 78.964 | 14.896 | 1.00 | 30.12 | O |
| ATOM | 14823 | N | GLU B 348 | 83.035 | 78.939 | 14.674 | 1.00 | 31.52 | N |
| ATOM | 14824 | CA | GLU B 348 | 82.829 | 77.934 | 15.750 | 1.00 | 32.70 | C |
| ATOM | 14826 | CB | GLU B 348 | 81.352 | 77.580 | 15.915 | 1.00 | 32.60 | C |
| ATOM | 14829 | CG | GLU B 348 | 80.479 | 78.643 | 16.406 | 1.00 | 33.50 | C |
| ATOM | 14832 | CD | GLU B 348 | 79.053 | 78.145 | 16.486 | 1.00 | 34.09 | C |
| ATOM | 14833 | OE1 | GLU B 348 | 78.593 | 77.954 | 17.620 | 1.00 | 35.57 | O |
| ATOM | 14834 | OE2 | GLU B 348 | 78.423 | 77.880 | 15.427 | 1.00 | 33.61 | O |
| ATOM | 14835 | C | GLU B 348 | 83.533 | 76.607 | 15.474 | 1.00 | 33.52 | C |
| ATOM | 14836 | O | GLU B 348 | 84.064 | 75.974 | 16.392 | 1.00 | 34.00 | O |
| ATOM | 14838 | N | VAL B 349 | 83.493 | 76.185 | 14.213 | 1.00 | 34.36 | N |
| ATOM | 14839 | CA | VAL B 349 | 84.140 | 74.946 | 13.781 | 1.00 | 35.55 | C |
| ATOM | 14841 | CB | VAL B 349 | 83.900 | 74.621 | 12.261 | 1.00 | 35.72 | C |
| ATOM | 14843 | CG1 | VAL B 349 | 82.406 | 74.524 | 11.952 | 1.00 | 35.48 | C |
| ATOM | 14847 | CG2 | VAL B 349 | 84.605 | 75.629 | 11.330 | 1.00 | 35.15 | C |
| ATOM | 14851 | C | VAL B 349 | 85.649 | 74.975 | 14.040 | 1.00 | 36.62 | C |
| ATOM | 14852 | O | VAL B 349 | 86.299 | 73.930 | 13.994 | 1.00 | 36.51 | O |
| ATOM | 14854 | N | LYS B 350 | 86.210 | 76.165 | 14.265 | 1.00 | 37.36 | N |
| ATOM | 14855 | CA | LYS B 350 | 87.606 | 76.264 | 14.692 | 1.00 | 38.21 | C |
| ATOM | 14857 | CB | LYS B 350 | 88.269 | 77.537 | 14.145 | 1.00 | 38.45 | C |
| ATOM | 14860 | CG | LYS B 350 | 88.079 | 77.788 | 12.633 | 1.00 | 39.31 | C |
| ATOM | 14863 | CD | LYS B 350 | 88.373 | 79.262 | 12.299 | 1.00 | 39.34 | C |
| ATOM | 14866 | CE | LYS B 350 | 88.173 | 79.570 | 10.816 | 1.00 | 40.28 | C |
| ATOM | 14869 | NZ | LYS B 350 | 88.167 | 81.043 | 10.542 | 1.00 | 41.16 | N |
| ATOM | 14873 | C | LYS B 350 | 87.620 | 76.243 | 16.219 | 1.00 | 38.03 | C |
| ATOM | 14874 | O | LYS B 350 | 88.658 | 75.957 | 16.816 | 1.00 | 38.53 | O |
| ATOM | 14876 | N | ASP B 354 | 78.907 | 69.559 | 33.750 | 1.00 | 63.19 | N |
| ATOM | 14877 | CA | ASP B 354 | 78.202 | 69.025 | 34.923 | 1.00 | 62.99 | C |
| ATOM | 14879 | CB | ASP B 354 | 79.166 | 68.220 | 35.810 | 1.00 | 63.10 | C |
| ATOM | 14882 | CG | ASP B 354 | 80.545 | 68.887 | 35.972 | 1.00 | 64.07 | C |
| ATOM | 14883 | OD1 | ASP B 354 | 80.682 | 70.123 | 35.760 | 1.00 | 64.85 | O |
| ATOM | 14884 | OD2 | ASP B 354 | 81.501 | 68.153 | 36.326 | 1.00 | 64.48 | O |
| ATOM | 14885 | C | ASP B 354 | 77.504 | 70.153 | 35.698 | 1.00 | 62.84 | C |
| ATOM | 14886 | O | ASP B 354 | 77.500 | 70.175 | 36.942 | 1.00 | 61.81 | O |
| ATOM | 14888 | N | GLU B 355 | 76.922 | 71.075 | 34.915 | 1.00 | 62.74 | N |
| ATOM | 14889 | CA | GLU B 355 | 76.242 | 72.295 | 35.402 | 1.00 | 62.66 | C |
| ATOM | 14891 | CB | GLU B 355 | 77.120 | 73.531 | 35.163 | 1.00 | 62.72 | C |
| ATOM | 14894 | CG | GLU B 355 | 78.555 | 73.429 | 35.638 | 1.00 | 63.33 | C |
| ATOM | 14897 | CD | GLU B 355 | 79.359 | 74.677 | 35.276 | 1.00 | 64.15 | C |
| ATOM | 14898 | OE1 | GLU B 355 | 78.756 | 75.679 | 34.808 | 1.00 | 65.50 | O |
| ATOM | 14899 | OE2 | GLU B 355 | 80.597 | 74.658 | 35.465 | 1.00 | 66.28 | O |
| ATOM | 14900 | C | GLU B 355 | 74.895 | 72.569 | 34.714 | 1.00 | 62.03 | C |
| ATOM | 14901 | O | GLU B 355 | 74.227 | 73.551 | 35.045 | 1.00 | 61.80 | O |

| ATOM | 14903 | N    | GLY  | B | 356 | 74.513 | 71.721 | 33.756 | 1.00 | 61.60 | N |
|------|-------|------|------|---|-----|--------|--------|--------|------|-------|---|
| ATOM | 14904 | CA   | GLY  | B | 356 | 73.343 | 71.965 | 32.902 | 1.00 | 61.25 | C |
| ATOM | 14907 | C    | GLY  | B | 356 | 73.502 | 73.163 | 31.968 | 1.00 | 60.44 | C |
| ATOM | 14908 | O    | GLY  | B | 356 | 72.535 | 73.913 | 31.752 | 1.00 | 60.66 | O |
| ATOM | 14910 | N    | ILE  | B | 357 | 74.708 | 73.332 | 31.405 | 1.00 | 59.03 | N |
| ATOM | 14911 | CA   | ILE  | B | 357 | 75.041 | 74.527 | 30.601 | 1.00 | 57.87 | C |
| ATOM | 14913 | CB   | ILE  | B | 357 | 76.554 | 74.610 | 30.225 | 1.00 | 58.03 | C |
| ATOM | 14915 | CG1  | ILE  | B | 357 | 77.452 | 74.617 | 31.476 | 1.00 | 58.40 | C |
| ATOM | 14918 | CD1  | ILE  | B | 357 | 78.960 | 74.518 | 31.173 | 1.00 | 58.34 | C |
| ATOM | 14922 | CG2  | ILE  | B | 357 | 76.815 | 75.860 | 29.343 | 1.00 | 58.62 | C |
| ATOM | 14926 | C    | ILE  | B | 357 | 74.235 | 74.553 | 29.299 | 1.00 | 55.98 | C |
| ATOM | 14927 | O    | ILE  | B | 357 | 74.325 | 73.612 | 28.489 | 1.00 | 56.14 | O |
| ATOM | 14929 | N    | LEU  | B | 358 | 73.458 | 75.628 | 29.108 | 1.00 | 53.35 | N |
| ATOM | 14930 | CA   | LEU  | B | 358 | 72.661 | 75.811 | 27.878 | 1.00 | 51.13 | C |
| ATOM | 14932 | CB   | LEU  | B | 358 | 71.351 | 76.587 | 28.148 | 1.00 | 51.44 | C |
| ATOM | 14935 | CG   | LEU  | B | 358 | 70.350 | 76.663 | 26.967 | 1.00 | 52.79 | C |
| ATOM | 14937 | CD1  | LEU  | B | 358 | 68.927 | 76.233 | 27.362 | 1.00 | 52.72 | C |
| ATOM | 14941 | CD2  | LEU  | B | 358 | 70.325 | 78.063 | 26.328 | 1.00 | 53.06 | C |
| ATOM | 14945 | C    | LEU  | B | 358 | 73.514 | 76.503 | 26.802 | 1.00 | 47.88 | C |
| ATOM | 14946 | O    | LEU  | B | 358 | 73.692 | 77.733 | 26.813 | 1.00 | 48.82 | O |
| ATOM | 14948 | N    | ARG  | B | 359 | 74.017 | 75.686 | 25.874 | 1.00 | 43.13 | N |
| ATOM | 14949 | CA   | ARG  | B | 359 | 74.948 | 76.110 | 24.827 | 1.00 | 38.87 | C |
| ATOM | 14951 | CB   | ARG  | B | 359 | 75.976 | 74.989 | 24.599 | 1.00 | 39.38 | C |
| ATOM | 14954 | CG   | ARG  | B | 359 | 76.623 | 74.511 | 25.910 | 1.00 | 42.21 | C |
| ATOM | 14957 | CD   | ARG  | B | 359 | 77.396 | 73.216 | 25.797 | 1.00 | 43.21 | C |
| ATOM | 14960 | NE   | ARG  | B | 359 | 77.879 | 72.818 | 27.125 | 1.00 | 47.35 | N |
| ATOM | 14962 | CZ   | ARG  | B | 359 | 78.557 | 71.698 | 27.382 | 1.00 | 48.97 | C |
| ATOM | 14963 | NH1  | ARG  | B | 359 | 78.850 | 70.847 | 26.405 | 1.00 | 50.75 | N |
| ATOM | 14966 | NH2  | ARG  | B | 359 | 78.950 | 71.426 | 28.624 | 1.00 | 48.94 | N |
| ATOM | 14969 | C    | ARG  | B | 359 | 74.230 | 76.402 | 23.513 | 1.00 | 33.40 | C |
| ATOM | 14970 | O    | ARG  | B | 359 | 74.795 | 77.063 | 22.644 | 1.00 | 34.03 | O |
| ATOM | 14972 | N    | AGLN | B | 360 | 73.008 | 75.931 | 23.350 | 0.50 | 29.43 | N |
| ATOM | 14973 | N    | BGLN | B | 360 | 73.023 | 75.855 | 23.346 | 0.50 | 29.87 | N |
| ATOM | 14974 | CA   | AGLN | B | 360 | 72.346 | 76.196 | 22.102 | 0.50 | 26.05 | C |
| ATOM | 14975 | CA   | BGLN | B | 360 | 72.235 | 76.021 | 22.120 | 0.50 | 26.84 | C |
| ATOM | 14978 | CB   | AGLN | B | 360 | 72.000 | 74.901 | 21.380 | 0.50 | 26.41 | C |
| ATOM | 14979 | CB   | BGLN | B | 360 | 71.500 | 74.703 | 21.744 | 0.50 | 27.54 | C |
| ATOM | 14984 | CG   | AGLN | B | 360 | 71.861 | 75.053 | 19.867 | 0.50 | 26.14 | C |
| ATOM | 14985 | CG   | BGLN | B | 360 | 72.187 | 73.744 | 20.643 | 0.50 | 27.55 | C |
| ATOM | 14990 | CD   | AGLN | B | 360 | 72.812 | 76.078 | 19.275 | 0.50 | 23.16 | C |
| ATOM | 14991 | CD   | BGLN | B | 360 | 71.278 | 72.555 | 20.262 | 0.50 | 27.74 | C |
| ATOM | 14992 | OE1  | AGLN | B | 360 | 72.351 | 77.139 | 18.816 | 0.50 | 14.82 | O |
| ATOM | 14993 | OE1  | BGLN | B | 360 | 70.431 | 72.172 | 21.068 | 0.50 | 32.76 | O |
| ATOM | 14994 | NE2  | AGLN | B | 360 | 74.175 | 75.784 | 19.315 | 0.50 | 20.13 | N |
| ATOM | 14995 | NE2  | BGLN | B | 360 | 71.462 | 71.951 | 19.068 | 0.50 | 25.46 | N |
| ATOM | 15000 | C    | AGLN | B | 360 | 71.143 | 77.097 | 22.266 | 0.50 | 23.54 | C |
| ATOM | 15001 | C    | BGLN | B | 360 | 71.233 | 77.184 | 22.296 | 0.50 | 24.10 | C |
| ATOM | 15002 | O    | AGLN | B | 360 | 70.515 | 77.165 | 23.338 | 0.50 | 21.57 | O |
| ATOM | 15003 | O    | BGLN | B | 360 | 70.849 | 77.543 | 23.428 | 0.50 | 22.76 | O |
| ATOM | 15006 | N    | ASP  | B | 361 | 70.826 | 77.791 | 21.183 | 1.00 | 19.82 | N |
| ATOM | 15007 | CA   | ASP  | B | 361 | 69.723 | 78.755 | 21.200 | 1.00 | 16.94 | C |
| ATOM | 15009 | CB   | ASP  | B | 361 | 69.666 | 79.544 | 19.886 | 1.00 | 17.43 | C |
| ATOM | 15012 | CG   | ASP  | B | 361 | 70.796 | 80.530 | 19.743 | 1.00 | 17.39 | C |
| ATOM | 15013 | OD1  | ASP  | B | 361 | 71.555 | 80.744 | 20.731 | 1.00 | 19.98 | O |
| ATOM | 15014 | OD2  | ASP  | B | 361 | 70.915 | 81.107 | 18.649 | 1.00 | 17.83 | O |
| ATOM | 15015 | C    | ASP  | B | 361 | 68.418 | 78.049 | 21.437 | 1.00 | 15.51 | C |
| ATOM | 15016 | O    | ASP  | B | 361 | 68.238 | 76.928 | 21.035 | 1.00 | 13.38 | O |

| ATOM | 15018 | N | ARG B 362 | 67.465 | 78.745 | 22.043 | 1.00 | 13.76 | N |
|---|---|---|---|---|---|---|---|---|---|
| ATOM | 15019 | CA | ARG B 362 | 66.172 | 78.165 | 22.244 | 1.00 | 13.58 | C |
| ATOM | 15021 | CB | ARG B 362 | 65.474 | 78.879 | 23.406 | 1.00 | 12.73 | C |
| ATOM | 15024 | CG | ARG B 362 | 66.230 | 78.680 | 24.738 | 1.00 | 13.74 | C |
| ATOM | 15027 | CD | ARG B 362 | 65.533 | 79.479 | 25.806 | 1.00 | 16.53 | C |
| ATOM | 15030 | NE | ARG B 362 | 66.241 | 79.413 | 27.083 | 1.00 | 18.41 | N |
| ATOM | 15032 | CZ | ARG B 362 | 67.161 | 80.293 | 27.471 | 1.00 | 18.61 | C |
| ATOM | 15033 | NH1 | ARG B 362 | 67.518 | 81.304 | 26.692 | 1.00 | 20.96 | N |
| ATOM | 15036 | NH2 | ARG B 362 | 67.734 | 80.150 | 28.664 | 1.00 | 22.60 | N |
| ATOM | 15039 | C | ARG B 362 | 65.347 | 78.239 | 20.945 | 1.00 | 12.21 | C |
| ATOM | 15040 | O | ARG B 362 | 65.779 | 78.790 | 19.941 | 1.00 | 13.34 | O |
| ATOM | 15042 | N | TYR B 363 | 64.146 | 77.698 | 20.999 | 1.00 | 11.71 | N |
| ATOM | 15043 | CA | TYR B 363 | 63.422 | 77.449 | 19.760 | 1.00 | 12.25 | C |
| ATOM | 15045 | CB | TYR B 363 | 62.229 | 76.516 | 19.990 | 1.00 | 13.57 | C |
| ATOM | 15048 | CG | TYR B 363 | 62.527 | 75.059 | 20.219 | 1.00 | 12.30 | C |
| ATOM | 15049 | CD1 | TYR B 363 | 63.803 | 74.562 | 20.488 | 1.00 | 15.42 | C |
| ATOM | 15051 | CE1 | TYR B 363 | 63.999 | 73.158 | 20.746 | 1.00 | 15.54 | C |
| ATOM | 15053 | CZ | TYR B 363 | 62.864 | 72.364 | 20.774 | 1.00 | 15.62 | C |
| ATOM | 15054 | OH | TYR B 363 | 62.910 | 71.006 | 21.067 | 1.00 | 19.34 | O |
| ATOM | 15056 | CE2 | TYR B 363 | 61.617 | 72.886 | 20.570 | 1.00 | 15.84 | C |
| ATOM | 15058 | CD2 | TYR B 363 | 61.441 | 74.167 | 20.294 | 1.00 | 16.43 | C |
| ATOM | 15060 | C | TYR B 363 | 62.973 | 78.708 | 19.044 | 1.00 | 11.95 | C |
| ATOM | 15061 | O | TYR B 363 | 62.867 | 78.681 | 17.772 | 1.00 | 12.79 | O |
| ATOM | 15063 | N | PRO B 364 | 62.640 | 79.804 | 19.783 | 1.00 | 12.33 | N |
| ATOM | 15064 | CA | PRO B 364 | 62.231 | 81.009 | 19.052 | 1.00 | 12.98 | C |
| ATOM | 15066 | CB | PRO B 364 | 61.989 | 82.033 | 20.175 | 1.00 | 13.89 | C |
| ATOM | 15069 | CG | PRO B 364 | 61.459 | 81.095 | 21.294 | 1.00 | 12.57 | C |
| ATOM | 15072 | CD | PRO B 364 | 62.454 | 79.970 | 21.251 | 1.00 | 12.38 | C |
| ATOM | 15075 | C | PRO B 364 | 63.222 | 81.501 | 17.979 | 1.00 | 13.30 | C |
| ATOM | 15076 | O | PRO B 364 | 62.829 | 82.027 | 16.953 | 1.00 | 12.64 | O |
| ATOM | 15077 | N | LEU B 365 | 64.505 | 81.281 | 18.222 | 1.00 | 12.71 | N |
| ATOM | 15078 | CA | LEU B 365 | 65.543 | 81.611 | 17.255 | 1.00 | 13.54 | C |
| ATOM | 15080 | CB | LEU B 365 | 66.773 | 82.096 | 18.025 | 1.00 | 13.97 | C |
| ATOM | 15083 | CG | LEU B 365 | 66.564 | 83.438 | 18.730 | 1.00 | 15.08 | C |
| ATOM | 15085 | CD1 | LEU B 365 | 67.861 | 83.866 | 19.471 | 1.00 | 15.97 | C |
| ATOM | 15089 | CD2 | LEU B 365 | 66.033 | 84.577 | 17.786 | 1.00 | 15.60 | C |
| ATOM | 15093 | C | LEU B 365 | 65.914 | 80.390 | 16.390 | 1.00 | 13.56 | C |
| ATOM | 15094 | O | LEU B 365 | 65.927 | 80.470 | 15.158 | 1.00 | 13.60 | O |
| ATOM | 15096 | N | ARG B 366 | 66.206 | 79.261 | 17.027 | 1.00 | 13.78 | N |
| ATOM | 15097 | CA | ARG B 366 | 66.759 | 78.104 | 16.309 | 1.00 | 13.67 | C |
| ATOM | 15099 | CB | ARG B 366 | 67.349 | 77.111 | 17.286 | 1.00 | 12.82 | C |
| ATOM | 15102 | CG | ARG B 366 | 67.871 | 75.762 | 16.704 | 1.00 | 13.60 | C |
| ATOM | 15105 | CD | ARG B 366 | 68.902 | 75.136 | 17.611 | 1.00 | 15.09 | C |
| ATOM | 15108 | NE | ARG B 366 | 68.444 | 74.899 | 18.980 | 1.00 | 15.85 | N |
| ATOM | 15110 | CZ | ARG B 366 | 68.075 | 73.729 | 19.484 | 1.00 | 15.17 | C |
| ATOM | 15111 | NH1 | ARG B 366 | 68.005 | 72.640 | 18.725 | 1.00 | 15.79 | N |
| ATOM | 15114 | NH2 | ARG B 366 | 67.729 | 73.660 | 20.762 | 1.00 | 17.55 | N |
| ATOM | 15117 | C | ARG B 366 | 65.749 | 77.406 | 15.391 | 1.00 | 12.97 | C |
| ATOM | 15118 | O | ARG B 366 | 66.167 | 76.767 | 14.436 | 1.00 | 13.37 | O |
| ATOM | 15120 | N | THR B 367 | 64.456 | 77.514 | 15.694 | 1.00 | 11.74 | N |
| ATOM | 15121 | CA | THR B 367 | 63.436 | 76.902 | 14.823 | 1.00 | 11.98 | C |
| ATOM | 15123 | CB | THR B 367 | 62.398 | 76.024 | 15.623 | 1.00 | 12.22 | C |
| ATOM | 15125 | OG1 | THR B 367 | 61.485 | 76.856 | 16.347 | 1.00 | 10.95 | O |
| ATOM | 15127 | CG2 | THR B 367 | 63.091 | 75.000 | 16.503 | 1.00 | 11.90 | C |
| ATOM | 15131 | C | THR B 367 | 62.678 | 77.912 | 13.985 | 1.00 | 11.48 | C |
| ATOM | 15132 | O | THR B 367 | 61.621 | 77.586 | 13.385 | 1.00 | 11.61 | O |
| ATOM | 15134 | N | SER B 368 | 63.185 | 79.148 | 13.914 | 1.00 | 11.81 | N |

| ATOM | 15135 | CA | SER | B | 368 | 62.488 | 80.209 | 13.186 | 1.00 | 11.19 | C |
| --- | --- | --- | --- | --- | --- | --- | --- | --- | --- | --- | --- |
| ATOM | 15137 | CB | SER | B | 368 | 63.145 | 81.583 | 13.439 | 1.00 | 12.05 | C |
| ATOM | 15140 | OG | SER | B | 368 | 64.530 | 81.608 | 13.148 | 1.00 | 11.89 | O |
| ATOM | 15142 | C | SER | B | 368 | 62.203 | 79.889 | 11.712 | 1.00 | 11.72 | C |
| ATOM | 15143 | O | SER | B | 368 | 61.086 | 80.114 | 11.246 | 1.00 | 12.22 | O |
| ATOM | 15145 | N | PRO | B | 369 | 63.189 | 79.327 | 10.963 | 1.00 | 12.33 | N |
| ATOM | 15146 | CA | PRO | B | 369 | 62.830 | 79.026 | 9.522 | 1.00 | 11.59 | C |
| ATOM | 15148 | CB | PRO | B | 369 | 64.135 | 78.523 | 8.916 | 1.00 | 12.44 | C |
| ATOM | 15151 | CG | PRO | B | 369 | 65.226 | 79.063 | 9.875 | 1.00 | 12.31 | C |
| ATOM | 15154 | CD | PRO | B | 369 | 64.605 | 78.979 | 11.241 | 1.00 | 11.36 | C |
| ATOM | 15157 | C | PRO | B | 369 | 61.719 | 77.962 | 9.418 | 1.00 | 12.62 | C |
| ATOM | 15158 | O | PRO | B | 369 | 60.865 | 78.022 | 8.513 | 1.00 | 12.38 | O |
| ATOM | 15159 | N | GLN | B | 370 | 61.798 | 76.989 | 10.310 | 1.00 | 10.09 | N |
| ATOM | 15160 | CA | GLN | B | 370 | 60.848 | 75.902 | 10.340 | 1.00 | 10.31 | C |
| ATOM | 15162 | CB | GLN | B | 370 | 61.366 | 74.767 | 11.239 | 1.00 | 11.03 | C |
| ATOM | 15165 | CG | GLN | B | 370 | 62.634 | 74.094 | 10.776 | 1.00 | 10.09 | C |
| ATOM | 15168 | CD | GLN | B | 370 | 63.875 | 74.749 | 11.263 | 1.00 | 10.08 | C |
| ATOM | 15169 | OE1 | GLN | B | 370 | 63.816 | 75.804 | 11.851 | 1.00 | 11.90 | O |
| ATOM | 15170 | NE2 | GLN | B | 370 | 65.016 | 74.086 | 11.056 | 1.00 | 8.88 | N |
| ATOM | 15173 | C | GLN | B | 370 | 59.464 | 76.420 | 10.788 | 1.00 | 10.81 | C |
| ATOM | 15174 | O | GLN | B | 370 | 58.426 | 75.860 | 10.417 | 1.00 | 12.12 | O |
| ATOM | 15176 | N | TRP | B | 371 | 59.441 | 77.492 | 11.586 | 1.00 | 11.00 | N |
| ATOM | 15177 | CA | TRP | B | 371 | 58.193 | 78.056 | 12.070 | 1.00 | 11.82 | C |
| ATOM | 15179 | CB | TRP | B | 371 | 58.470 | 78.896 | 13.312 | 1.00 | 12.70 | C |
| ATOM | 15182 | CG | TRP | B | 371 | 57.196 | 79.307 | 14.041 | 1.00 | 12.13 | C |
| ATOM | 15183 | CD1 | TRP | B | 371 | 56.535 | 80.508 | 14.010 | 1.00 | 13.20 | C |
| ATOM | 15185 | NE1 | TRP | B | 371 | 55.431 | 80.469 | 14.848 | 1.00 | 13.47 | N |
| ATOM | 15187 | CE2 | TRP | B | 371 | 55.354 | 79.236 | 15.426 | 1.00 | 14.02 | C |
| ATOM | 15188 | CD2 | TRP | B | 371 | 56.442 | 78.473 | 14.939 | 1.00 | 14.08 | C |
| ATOM | 15189 | CE3 | TRP | B | 371 | 56.565 | 77.145 | 15.350 | 1.00 | 12.42 | C |
| ATOM | 15191 | CZ3 | TRP | B | 371 | 55.629 | 76.641 | 16.254 | 1.00 | 14.37 | C |
| ATOM | 15193 | CH2 | TRP | B | 371 | 54.578 | 77.416 | 16.715 | 1.00 | 13.76 | C |
| ATOM | 15195 | CZ2 | TRP | B | 371 | 54.414 | 78.705 | 16.336 | 1.00 | 13.53 | C |
| ATOM | 15197 | C | TRP | B | 371 | 57.588 | 78.999 | 11.008 | 1.00 | 12.30 | C |
| ATOM | 15198 | O | TRP | B | 371 | 56.365 | 78.993 | 10.757 | 1.00 | 14.50 | O |
| ATOM | 15200 | N | LEU | B | 372 | 58.427 | 79.834 | 10.416 | 1.00 | 11.73 | N |
| ATOM | 15201 | CA | LEU | B | 372 | 57.935 | 80.833 | 9.476 | 1.00 | 11.42 | C |
| ATOM | 15203 | CB | LEU | B | 372 | 58.928 | 81.979 | 9.426 | 1.00 | 11.81 | C |
| ATOM | 15206 | CG | LEU | B | 372 | 58.970 | 82.878 | 10.684 | 1.00 | 11.86 | C |
| ATOM | 15208 | CD1 | LEU | B | 372 | 60.132 | 83.878 | 10.571 | 1.00 | 16.20 | C |
| ATOM | 15212 | CD2 | LEU | B | 372 | 57.688 | 83.597 | 10.968 | 1.00 | 12.61 | C |
| ATOM | 15216 | C | LEU | B | 372 | 57.707 | 80.246 | 8.064 | 1.00 | 11.21 | C |
| ATOM | 15217 | O | LEU | B | 372 | 56.888 | 80.758 | 7.267 | 1.00 | 11.86 | O |
| ATOM | 15219 | N | GLY | B | 373 | 58.486 | 79.229 | 7.684 | 1.00 | 10.41 | N |
| ATOM | 15220 | CA | GLY | B | 373 | 58.432 | 78.697 | 6.322 | 1.00 | 11.51 | C |
| ATOM | 15223 | C | GLY | B | 373 | 57.009 | 78.340 | 5.879 | 1.00 | 11.74 | C |
| ATOM | 15224 | O | GLY | B | 373 | 56.531 | 78.782 | 4.804 | 1.00 | 11.22 | O |
| ATOM | 15226 | N | PRO | B | 374 | 56.309 | 77.557 | 6.705 | 1.00 | 11.86 | N |
| ATOM | 15227 | CA | PRO | B | 374 | 54.982 | 77.138 | 6.270 | 1.00 | 12.09 | C |
| ATOM | 15229 | CB | PRO | B | 374 | 54.521 | 76.223 | 7.402 | 1.00 | 13.67 | C |
| ATOM | 15232 | CG | PRO | B | 374 | 55.759 | 75.606 | 7.886 | 1.00 | 13.07 | C |
| ATOM | 15235 | CD | PRO | B | 374 | 56.717 | 76.826 | 7.908 | 1.00 | 13.54 | C |
| ATOM | 15238 | C | PRO | B | 374 | 54.018 | 78.261 | 5.994 | 1.00 | 12.83 | C |
| ATOM | 15239 | O | PRO | B | 374 | 53.288 | 78.249 | 4.989 | 1.00 | 14.06 | O |
| ATOM | 15240 | N | LEU | B | 375 | 54.011 | 79.252 | 6.870 | 1.00 | 12.86 | N |
| ATOM | 15241 | CA | LEU | B | 375 | 53.090 | 80.350 | 6.702 | 1.00 | 13.15 | C |
| ATOM | 15243 | CB | LEU | B | 375 | 52.905 | 81.148 | 7.961 | 1.00 | 14.82 | C |

| | | | | | | | | | | |
|---|---|---|---|---|---|---|---|---|---|---|
| ATOM | 15246 | CG | LEU | B | 375 | 54.056 | 81.963 | 8.508 | 1.00 15.28 | C |
| ATOM | 15248 | CD1 | LEU | B | 375 | 54.080 | 83.371 | 7.930 | 1.00 16.82 | C |
| ATOM | 15252 | CD2 | LEU | B | 375 | 53.979 | 81.937 | 10.077 | 1.00 16.77 | C |
| ATOM | 15256 | C | LEU | B | 375 | 53.508 | 81.256 | 5.507 | 1.00 13.05 | C |
| ATOM | 15257 | O | LEU | B | 375 | 52.661 | 81.881 | 4.848 | 1.00 14.07 | O |
| ATOM | 15259 | N | VAL | B | 376 | 54.801 | 81.302 | 5.211 | 1.00 12.68 | N |
| ATOM | 15260 | CA | VAL | B | 376 | 55.250 | 82.043 | 4.044 | 1.00 11.82 | C |
| ATOM | 15262 | CB | VAL | B | 376 | 56.781 | 82.242 | 4.072 | 1.00 12.03 | C |
| ATOM | 15264 | CG1 | VAL | B | 376 | 57.299 | 82.798 | 2.749 | 1.00 14.58 | C |
| ATOM | 15268 | CG2 | VAL | B | 376 | 57.116 | 83.177 | 5.225 | 1.00 13.11 | C |
| ATOM | 15272 | C | VAL | B | 376 | 54.754 | 81.395 | 2.789 | 1.00 12.72 | C |
| ATOM | 15273 | O | VAL | B | 376 | 54.370 | 82.086 | 1.846 | 1.00 12.87 | O |
| ATOM | 15275 | N | SER | B | 377 | 54.766 | 80.056 | 2.749 | 1.00 12.38 | N |
| ATOM | 15276 | CA | SER | B | 377 | 54.211 | 79.357 | 1.599 | 1.00 12.35 | C |
| ATOM | 15278 | CB | SER | B | 377 | 54.400 | 77.808 | 1.663 | 1.00 12.06 | C |
| ATOM | 15281 | OG | SER | B | 377 | 54.102 | 77.238 | 0.415 | 1.00 12.83 | O |
| ATOM | 15283 | C | SER | B | 377 | 52.748 | 79.725 | 1.402 | 1.00 12.03 | C |
| ATOM | 15284 | O | SER | B | 377 | 52.310 | 79.895 | 0.285 | 1.00 12.27 | O |
| ATOM | 15286 | N | ASP | B | 378 | 52.004 | 79.842 | 2.508 | 1.00 12.76 | N |
| ATOM | 15287 | CA | ASP | B | 378 | 50.604 | 80.222 | 2.461 | 1.00 13.03 | C |
| ATOM | 15289 | CB | ASP | B | 378 | 49.970 | 80.134 | 3.844 | 1.00 13.80 | C |
| ATOM | 15292 | CG | ASP | B | 378 | 49.679 | 78.738 | 4.250 | 1.00 16.07 | C |
| ATOM | 15293 | OD1 | ASP | B | 378 | 49.740 | 77.827 | 3.406 | 1.00 17.68 | O |
| ATOM | 15294 | OD2 | ASP | B | 378 | 49.295 | 78.572 | 5.457 | 1.00 18.23 | O |
| ATOM | 15295 | C | ASP | B | 378 | 50.459 | 81.631 | 1.913 | 1.00 13.01 | C |
| ATOM | 15296 | O | ASP | B | 378 | 49.575 | 81.871 | 1.083 | 1.00 12.75 | O |
| ATOM | 15298 | N | LEU | B | 379 | 51.330 | 82.554 | 2.315 | 1.00 11.72 | N |
| ATOM | 15299 | CA | LEU | B | 379 | 51.217 | 83.900 | 1.784 | 1.00 12.03 | C |
| ATOM | 15301 | CB | LEU | B | 379 | 52.169 | 84.809 | 2.529 | 1.00 12.22 | C |
| ATOM | 15304 | CG | LEU | B | 379 | 51.806 | 85.052 | 4.002 | 1.00 13.36 | C |
| ATOM | 15306 | CD1 | LEU | B | 379 | 52.917 | 85.744 | 4.765 | 1.00 14.29 | C |
| ATOM | 15310 | CD2 | LEU | B | 379 | 50.480 | 85.787 | 4.093 | 1.00 16.82 | C |
| ATOM | 15314 | C | LEU | B | 379 | 51.517 | 83.972 | 0.280 | 1.00 11.76 | C |
| ATOM | 15315 | O | LEU | B | 379 | 50.859 | 84.697 | -0.448 | 1.00 13.22 | O |
| ATOM | 15317 | N | ILE | B | 380 | 52.497 | 83.212 | -0.174 | 1.00 11.22 | N |
| ATOM | 15318 | CA | ILE | B | 380 | 52.766 | 83.125 | -1.622 | 1.00 12.02 | C |
| ATOM | 15320 | CB | ILE | B | 380 | 54.071 | 82.350 | -1.837 | 1.00 12.01 | C |
| ATOM | 15322 | CG1 | ILE | B | 380 | 55.235 | 83.125 | -1.197 | 1.00 12.23 | C |
| ATOM | 15325 | CD1 | ILE | B | 380 | 56.543 | 82.354 | -1.247 | 1.00 14.44 | C |
| ATOM | 15329 | CG2 | ILE | B | 380 | 54.338 | 82.013 | -3.322 | 1.00 13.65 | C |
| ATOM | 15333 | C | ILE | B | 380 | 51.604 | 82.480 | -2.428 | 1.00 12.36 | C |
| ATOM | 15334 | O | ILE | B | 380 | 51.254 | 82.895 | -3.550 | 1.00 11.53 | O |
| ATOM | 15336 | N | HIS | B | 381 | 51.009 | 81.450 | -1.828 | 1.00 11.63 | N |
| ATOM | 15337 | CA | HIS | B | 381 | 49.803 | 80.860 | -2.419 | 1.00 12.30 | C |
| ATOM | 15339 | CB | HIS | B | 381 | 49.364 | 79.662 | -1.565 | 1.00 12.52 | C |
| ATOM | 15342 | CG | HIS | B | 381 | 48.244 | 78.873 | -2.160 | 1.00 12.03 | C |
| ATOM | 15343 | ND1 | HIS | B | 381 | 46.922 | 79.239 | -2.014 | 1.00 18.15 | N |
| ATOM | 15345 | CE1 | HIS | B | 381 | 46.156 | 78.328 | -2.609 | 1.00 13.83 | C |
| ATOM | 15347 | NE2 | HIS | B | 381 | 46.922 | 77.396 | -3.112 | 1.00 13.49 | N |
| ATOM | 15349 | CD2 | HIS | B | 381 | 48.239 | 77.706 | -2.849 | 1.00 13.13 | C |
| ATOM | 15351 | C | HIS | B | 381 | 48.658 | 81.872 | -2.511 | 1.00 11.91 | C |
| ATOM | 15352 | O | HIS | B | 381 | 48.058 | 82.086 | -3.604 | 1.00 12.25 | O |
| ATOM | 15354 | N | ALA | B | 382 | 48.397 | 82.562 | -1.409 | 1.00 11.07 | N |
| ATOM | 15355 | CA | ALA | B | 382 | 47.375 | 83.590 | -1.408 | 1.00 10.90 | C |
| ATOM | 15357 | CB | ALA | B | 382 | 47.300 | 84.264 | -0.082 | 1.00 11.52 | C |
| ATOM | 15361 | C | ALA | B | 382 | 47.628 | 84.643 | -2.491 | 1.00 11.48 | C |
| ATOM | 15362 | O | ALA | B | 382 | 46.700 | 85.108 | -3.178 | 1.00 12.81 | O |

| ATOM | 15364 | N | HIS | B | 383 | 48.893 | 84.993 | -2.678 | 1.00 | 11.65 | N |
|------|-------|-----|-----|---|-----|--------|--------|--------|------|-------|---|
| ATOM | 15365 | CA | HIS | B | 383 | 49.246 | 85.978 | -3.694 | 1.00 | 10.12 | C |
| ATOM | 15367 | CB | HIS | B | 383 | 50.763 | 86.214 | -3.702 | 1.00 | 10.90 | C |
| ATOM | 15370 | CG | HIS | B | 383 | 51.123 | 87.519 | -4.285 | 1.00 | 12.81 | C |
| ATOM | 15371 | ND1 | HIS | B | 383 | 51.317 | 88.631 | -3.498 | 1.00 | 15.13 | N |
| ATOM | 15373 | CE1 | HIS | B | 383 | 51.614 | 89.656 | -4.277 | 1.00 | 16.71 | C |
| ATOM | 15375 | NE2 | HIS | B | 383 | 51.597 | 89.253 | -5.535 | 1.00 | 18.58 | N |
| ATOM | 15377 | CD2 | HIS | B | 383 | 51.288 | 87.917 | -5.565 | 1.00 | 14.53 | C |
| ATOM | 15379 | C | HIS | B | 383 | 48.818 | 85.434 | -5.083 | 1.00 | 11.16 | C |
| ATOM | 15380 | O | HIS | B | 383 | 48.282 | 86.164 | -5.939 | 1.00 | 12.31 | O |
| ATOM | 15382 | N | ALA | B | 384 | 49.091 | 84.160 | -5.351 | 1.00 | 12.03 | N |
| ATOM | 15383 | CA | ALA | B | 384 | 48.691 | 83.601 | -6.639 | 1.00 | 12.33 | C |
| ATOM | 15385 | CB | ALA | B | 384 | 49.181 | 82.206 | -6.756 | 1.00 | 12.20 | C |
| ATOM | 15389 | C | ALA | B | 384 | 47.171 | 83.648 | -6.810 | 1.00 | 12.36 | C |
| ATOM | 15390 | O | ALA | B | 384 | 46.668 | 84.009 | -7.877 | 1.00 | 11.88 | O |
| ATOM | 15392 | N | VAL | B | 385 | 46.445 | 83.318 | -5.743 | 1.00 | 11.80 | N |
| ATOM | 15393 | CA | VAL | B | 385 | 44.956 | 83.297 | -5.794 | 1.00 | 12.73 | C |
| ATOM | 15395 | CB | VAL | B | 385 | 44.379 | 82.665 | -4.509 | 1.00 | 12.52 | C |
| ATOM | 15397 | CG1 | VAL | B | 385 | 42.887 | 82.831 | -4.459 | 1.00 | 15.84 | C |
| ATOM | 15401 | CG2 | VAL | B | 385 | 44.826 | 81.236 | -4.386 | 1.00 | 14.00 | C |
| ATOM | 15405 | C | VAL | B | 385 | 44.403 | 84.709 | -6.056 | 1.00 | 12.56 | C |
| ATOM | 15406 | O | VAL | B | 385 | 43.546 | 84.951 | -6.953 | 1.00 | 11.45 | O |
| ATOM | 15408 | N | LEU | B | 386 | 44.831 | 85.668 | -5.244 | 1.00 | 11.89 | N |
| ATOM | 15409 | CA | LEU | B | 386 | 44.291 | 87.020 | -5.316 | 1.00 | 13.08 | C |
| ATOM | 15411 | CB | LEU | B | 386 | 44.750 | 87.858 | -4.123 | 1.00 | 13.24 | C |
| ATOM | 15414 | CG | LEU | B | 386 | 44.101 | 87.606 | -2.777 | 1.00 | 14.83 | C |
| ATOM | 15416 | CD1 | LEU | B | 386 | 44.536 | 88.620 | -1.730 | 1.00 | 15.40 | C |
| ATOM | 15420 | CD2 | LEU | B | 386 | 42.577 | 87.648 | -2.936 | 1.00 | 16.11 | C |
| ATOM | 15424 | C | LEU | B | 386 | 44.717 | 87.684 | -6.622 | 1.00 | 12.62 | C |
| ATOM | 15425 | O | LEU | B | 386 | 43.987 | 88.525 | -7.148 | 1.00 | 14.00 | O |
| ATOM | 15427 | N | THR | B | 387 | 45.860 | 87.309 | -7.181 | 1.00 | 13.21 | N |
| ATOM | 15428 | CA | THR | B | 387 | 46.257 | 87.890 | -8.454 | 1.00 | 12.63 | C |
| ATOM | 15430 | CB | THR | B | 387 | 47.673 | 87.459 | -8.864 | 1.00 | 12.69 | C |
| ATOM | 15432 | OG1 | THR | B | 387 | 48.616 | 87.986 | -7.918 | 1.00 | 12.64 | O |
| ATOM | 15434 | CG2 | THR | B | 387 | 48.031 | 88.017 | -10.247 | 1.00 | 14.03 | C |
| ATOM | 15438 | C | THR | B | 387 | 45.239 | 87.529 | -9.553 | 1.00 | 13.12 | C |
| ATOM | 15439 | O | THR | B | 387 | 44.804 | 88.375 | -10.357 | 1.00 | 13.68 | O |
| ATOM | 15441 | N | ILE | B | 388 | 44.846 | 86.264 | -9.592 | 1.00 | 12.38 | N |
| ATOM | 15442 | CA | ILE | B | 388 | 43.810 | 85.832 | -10.556 | 1.00 | 12.17 | C |
| ATOM | 15444 | CB | ILE | B | 388 | 43.661 | 84.315 | -10.564 | 1.00 | 11.93 | C |
| ATOM | 15446 | CG1 | ILE | B | 388 | 44.857 | 83.707 | -11.262 | 1.00 | 12.80 | C |
| ATOM | 15449 | CD1 | ILE | B | 388 | 44.908 | 82.223 | -11.236 | 1.00 | 18.28 | C |
| ATOM | 15453 | CG2 | ILE | B | 388 | 42.376 | 83.901 | -11.310 | 1.00 | 13.70 | C |
| ATOM | 15457 | C | ILE | B | 388 | 42.488 | 86.515 | -10.223 | 1.00 | 13.27 | C |
| ATOM | 15458 | O | ILE | B | 388 | 41.778 | 87.000 | -11.139 | 1.00 | 13.71 | O |
| ATOM | 15460 | N | GLU | B | 389 | 42.155 | 86.571 | -8.932 | 1.00 | 13.37 | N |
| ATOM | 15461 | CA | GLU | B | 389 | 40.838 | 87.092 | -8.538 | 1.00 | 13.23 | C |
| ATOM | 15463 | CB | GLU | B | 389 | 40.570 | 86.799 | -7.050 | 1.00 | 13.77 | C |
| ATOM | 15466 | CG | GLU | B | 389 | 39.176 | 87.158 | -6.582 | 1.00 | 15.29 | C |
| ATOM | 15469 | CD | GLU | B | 389 | 38.079 | 86.279 | -7.113 | 1.00 | 15.19 | C |
| ATOM | 15470 | OE1 | GLU | B | 389 | 38.386 | 85.373 | -7.879 | 1.00 | 14.47 | O |
| ATOM | 15471 | OE2 | GLU | B | 389 | 36.907 | 86.541 | -6.733 | 1.00 | 16.17 | O |
| ATOM | 15472 | C | GLU | B | 389 | 40.730 | 88.579 | -8.860 | 1.00 | 13.53 | C |
| ATOM | 15473 | O | GLU | B | 389 | 39.745 | 89.021 | -9.429 | 1.00 | 15.44 | O |
| ATOM | 15475 | N | ALA | B | 390 | 41.728 | 89.361 | -8.488 | 1.00 | 13.40 | N |
| ATOM | 15476 | CA | ALA | B | 390 | 41.692 | 90.818 | -8.630 | 1.00 | 13.85 | C |
| ATOM | 15478 | CB | ALA | B | 390 | 42.707 | 91.423 | -7.674 | 1.00 | 14.24 | C |

| ATOM | 15482 | C | ALA | B | 390 | 41.997 | 91.233 | -10.055 | 1.00 | 14.43 | C |
| ATOM | 15483 | O | ALA | B | 390 | 41.421 | 92.193 | -10.557 | 1.00 | 16.83 | O |
| ATOM | 15485 | N | GLY | B | 391 | 42.842 | 90.470 | -10.737 | 1.00 | 14.30 | N |
| ATOM | 15486 | CA | GLY | B | 391 | 43.370 | 90.881 | -12.042 | 1.00 | 14.30 | C |
| ATOM | 15489 | C | GLY | B | 391 | 42.895 | 90.259 | -13.318 | 1.00 | 14.55 | C |
| ATOM | 15490 | O | GLY | B | 391 | 43.079 | 90.834 | -14.398 | 1.00 | 14.99 | O |
| ATOM | 15492 | N | GLN | B | 392 | 42.320 | 89.056 | -13.209 | 1.00 | 13.60 | N |
| ATOM | 15493 | CA | GLN | B | 392 | 42.026 | 88.207 | -14.339 | 1.00 | 15.22 | C |
| ATOM | 15495 | CB | GLN | B | 392 | 43.093 | 87.117 | -14.448 | 1.00 | 15.82 | C |
| ATOM | 15498 | CG | GLN | B | 392 | 44.462 | 87.637 | -14.536 | 1.00 | 17.17 | C |
| ATOM | 15501 | CD | GLN | B | 392 | 45.509 | 86.583 | -14.219 | 1.00 | 17.76 | C |
| ATOM | 15502 | OE1 | GLN | B | 392 | 46.431 | 86.850 | -13.424 | 1.00 | 25.17 | O |
| ATOM | 15503 | NE2 | GLN | B | 392 | 45.397 | 85.438 | -14.831 | 1.00 | 17.74 | N |
| ATOM | 15506 | C | GLN | B | 392 | 40.693 | 87.503 | -14.239 | 1.00 | 14.90 | C |
| ATOM | 15507 | O | GLN | B | 392 | 40.516 | 86.463 | -14.856 | 1.00 | 14.92 | O |
| ATOM | 15509 | N | SER | B | 393 | 39.746 | 88.046 | -13.489 | 1.00 | 14.59 | N |
| ATOM | 15510 | CA | SER | B | 393 | 38.470 | 87.369 | -13.337 | 1.00 | 13.52 | C |
| ATOM | 15512 | CB | SER | B | 393 | 38.343 | 86.732 | -11.941 | 1.00 | 13.88 | C |
| ATOM | 15515 | OG | SER | B | 393 | 39.410 | 85.817 | -11.694 | 1.00 | 15.68 | O |
| ATOM | 15517 | C | SER | B | 393 | 37.291 | 88.285 | -13.598 | 1.00 | 14.69 | C |
| ATOM | 15518 | O | SER | B | 393 | 37.311 | 89.469 | -13.284 | 1.00 | 15.55 | O |
| ATOM | 15520 | N | THR | B | 394 | 36.271 | 87.677 | -14.187 | 1.00 | 12.48 | N |
| ATOM | 15521 | CA | THR | B | 394 | 34.937 | 88.244 | -14.303 | 1.00 | 13.16 | C |
| ATOM | 15523 | CB | THR | B | 394 | 34.319 | 87.931 | -15.665 | 1.00 | 13.81 | C |
| ATOM | 15525 | OG1 | THR | B | 394 | 35.196 | 88.374 | -16.718 | 1.00 | 14.01 | O |
| ATOM | 15527 | CG2 | THR | B | 394 | 32.987 | 88.608 | -15.780 | 1.00 | 15.52 | C |
| ATOM | 15531 | C | THR | B | 394 | 34.075 | 87.623 | -13.217 | 1.00 | 13.48 | C |
| ATOM | 15532 | O | THR | B | 394 | 33.946 | 86.387 | -13.150 | 1.00 | 13.64 | O |
| ATOM | 15534 | N | THR | B | 395 | 33.521 | 88.470 | -12.357 | 1.00 | 13.70 | N |
| ATOM | 15535 | CA | THR | B | 395 | 32.842 | 87.992 | -11.179 | 1.00 | 14.26 | C |
| ATOM | 15537 | CB | THR | B | 395 | 33.585 | 88.428 | -9.835 | 1.00 | 14.35 | C |
| ATOM | 15539 | OG1 | THR | B | 395 | 33.608 | 89.862 | -9.698 | 1.00 | 14.84 | O |
| ATOM | 15541 | CG2 | THR | B | 395 | 34.988 | 87.854 | -9.817 | 1.00 | 16.12 | C |
| ATOM | 15545 | C | THR | B | 395 | 31.380 | 88.383 | -11.091 | 1.00 | 14.27 | C |
| ATOM | 15546 | O | THR | B | 395 | 30.736 | 88.049 | -10.081 | 1.00 | 15.20 | O |
| ATOM | 15548 | N | ASP | B | 396 | 30.844 | 89.071 | -12.103 | 1.00 | 14.07 | N |
| ATOM | 15549 | CA | ASP | B | 396 | 29.404 | 89.280 | -12.148 | 1.00 | 14.28 | C |
| ATOM | 15551 | CB | ASP | B | 396 | 29.045 | 90.613 | -12.834 | 1.00 | 15.32 | C |
| ATOM | 15554 | CG | ASP | B | 396 | 29.393 | 90.657 | -14.312 | 1.00 | 16.95 | C |
| ATOM | 15555 | OD1 | ASP | B | 396 | 30.610 | 90.514 | -14.667 | 1.00 | 17.78 | O |
| ATOM | 15556 | OD2 | ASP | B | 396 | 28.448 | 90.904 | -15.117 | 1.00 | 18.45 | O |
| ATOM | 15557 | C | ASP | B | 396 | 28.669 | 88.055 | -12.725 | 1.00 | 14.02 | C |
| ATOM | 15558 | O | ASP | B | 396 | 29.267 | 86.989 | -12.916 | 1.00 | 13.71 | O |
| ATOM | 15560 | N | ASN | B | 397 | 27.384 | 88.224 | -13.023 | 1.00 | 13.69 | N |
| ATOM | 15561 | CA | ASN | B | 397 | 26.527 | 87.136 | -13.493 | 1.00 | 13.06 | C |
| ATOM | 15563 | CB | ASN | B | 397 | 26.247 | 86.158 | -12.332 | 1.00 | 13.13 | C |
| ATOM | 15566 | CG | ASN | B | 397 | 25.624 | 84.889 | -12.788 | 1.00 | 13.76 | C |
| ATOM | 15567 | OD1 | ASN | B | 397 | 26.271 | 84.105 | -13.454 | 1.00 | 14.49 | O |
| ATOM | 15568 | ND2 | ASN | B | 397 | 24.335 | 84.700 | -12.487 | 1.00 | 15.61 | N |
| ATOM | 15571 | C | ASN | B | 397 | 25.189 | 87.751 | -13.924 | 1.00 | 13.84 | C |
| ATOM | 15572 | O | ASN | B | 397 | 24.806 | 88.760 | -13.362 | 1.00 | 15.35 | O |
| ATOM | 15574 | N | PRO | B | 398 | 24.451 | 87.121 | -14.842 | 1.00 | 13.94 | N |
| ATOM | 15575 | CA | PRO | B | 398 | 24.963 | 86.155 | -15.828 | 1.00 | 14.15 | C |
| ATOM | 15577 | CB | PRO | B | 398 | 23.720 | 85.773 | -16.631 | 1.00 | 14.37 | C |
| ATOM | 15580 | CG | PRO | B | 398 | 22.706 | 86.836 | -16.364 | 1.00 | 16.43 | C |
| ATOM | 15583 | CD | PRO | B | 398 | 23.140 | 87.687 | -15.220 | 1.00 | 14.73 | C |
| ATOM | 15586 | C | PRO | B | 398 | 26.049 | 86.730 | -16.728 | 1.00 | 14.09 | C |

| ATOM | 15587 | O   | PRO | B | 398 | 26.140 | 87.952 | -16.838 | 1.00 | 14.42 | O |
|------|-------|-----|-----|---|-----|--------|--------|---------|------|-------|---|
| ATOM | 15588 | N   | LEU | B | 399 | 26.838 | 85.848 | -17.345 | 1.00 | 13.02 | N |
| ATOM | 15589 | CA  | LEU | B | 399 | 27.986 | 86.218 | -18.163 | 1.00 | 13.60 | C |
| ATOM | 15591 | CB  | LEU | B | 399 | 29.225 | 85.510 | -17.621 | 1.00 | 12.54 | C |
| ATOM | 15594 | CG  | LEU | B | 399 | 29.637 | 85.925 | -16.202 | 1.00 | 14.88 | C |
| ATOM | 15596 | CD1 | LEU | B | 399 | 30.911 | 85.316 | -15.729 | 1.00 | 15.06 | C |
| ATOM | 15600 | CD2 | LEU | B | 399 | 29.756 | 87.418 | -16.120 | 1.00 | 16.35 | C |
| ATOM | 15604 | C   | LEU | B | 399 | 27.720 | 85.882 | -19.627 | 1.00 | 14.23 | C |
| ATOM | 15605 | O   | LEU | B | 399 | 27.033 | 84.898 | -19.935 | 1.00 | 14.07 | O |
| ATOM | 15607 | N   | ILE | B | 400 | 28.200 | 86.731 | -20.525 | 1.00 | 14.18 | N |
| ATOM | 15608 | CA  | ILE | B | 400 | 27.760 | 86.696 | -21.923 | 1.00 | 16.26 | C |
| ATOM | 15610 | CB  | ILE | B | 400 | 27.266 | 88.112 | -22.369 | 1.00 | 17.04 | C |
| ATOM | 15612 | CG1 | ILE | B | 400 | 25.955 | 88.472 | -21.628 | 1.00 | 21.78 | C |
| ATOM | 15615 | CD1 | ILE | B | 400 | 26.120 | 89.376 | -20.578 | 1.00 | 24.44 | C |
| ATOM | 15619 | CG2 | ILE | B | 400 | 27.043 | 88.193 | -23.841 | 1.00 | 19.22 | C |
| ATOM | 15623 | C   | ILE | B | 400 | 28.904 | 86.223 | -22.800 | 1.00 | 16.66 | C |
| ATOM | 15624 | O   | ILE | B | 400 | 29.986 | 86.832 | -22.801 | 1.00 | 15.47 | O |
| ATOM | 15626 | N   | ASP | B | 401 | 28.654 | 85.140 | -23.542 | 1.00 | 17.09 | N |
| ATOM | 15627 | CA  | ASP | B | 401 | 29.592 | 84.600 | -24.510 | 1.00 | 18.19 | C |
| ATOM | 15629 | CB  | ASP | B | 401 | 29.664 | 83.063 | -24.444 | 1.00 | 18.87 | C |
| ATOM | 15632 | CG  | ASP | B | 401 | 30.622 | 82.469 | -25.479 | 1.00 | 20.63 | C |
| ATOM | 15633 | OD1 | ASP | B | 401 | 31.039 | 83.152 | -26.454 | 1.00 | 27.19 | O |
| ATOM | 15634 | OD2 | ASP | B | 401 | 30.969 | 81.283 | -25.348 | 1.00 | 30.45 | O |
| ATOM | 15635 | C   | ASP | B | 401 | 29.094 | 85.045 | -25.892 | 1.00 | 18.80 | C |
| ATOM | 15636 | O   | ASP | B | 401 | 28.182 | 84.442 | -26.459 | 1.00 | 18.25 | O |
| ATOM | 15638 | N   | VAL | B | 402 | 29.697 | 86.109 | -26.409 | 1.00 | 20.61 | N |
| ATOM | 15639 | CA  | VAL | B | 402 | 29.157 | 86.784 | -27.598 | 1.00 | 22.54 | C |
| ATOM | 15641 | CB  | VAL | B | 402 | 29.760 | 88.206 | -27.788 | 1.00 | 22.65 | C |
| ATOM | 15643 | CG1 | VAL | B | 402 | 29.269 | 88.848 | -29.096 | 1.00 | 24.34 | C |
| ATOM | 15647 | CG2 | VAL | B | 402 | 29.408 | 89.103 | -26.612 | 1.00 | 21.73 | C |
| ATOM | 15651 | C   | VAL | B | 402 | 29.409 | 85.908 | -28.819 | 1.00 | 24.09 | C |
| ATOM | 15652 | O   | VAL | B | 402 | 28.529 | 85.751 | -29.644 | 1.00 | 23.54 | O |
| ATOM | 15654 | N   | GLU | B | 403 | 30.600 | 85.314 | -28.878 | 1.00 | 26.54 | N |
| ATOM | 15655 | CA  | GLU | B | 403 | 31.020 | 84.441 | -29.997 | 1.00 | 28.16 | C |
| ATOM | 15657 | CB  | GLU | B | 403 | 32.402 | 83.851 | -29.684 | 1.00 | 28.53 | C |
| ATOM | 15660 | CG  | GLU | B | 403 | 33.015 | 82.981 | -30.777 | 1.00 | 29.52 | C |
| ATOM | 15663 | CD  | GLU | B | 403 | 34.433 | 82.455 | -30.427 | 1.00 | 32.19 | C |
| ATOM | 15664 | OE1 | GLU | B | 403 | 34.824 | 82.435 | -29.213 | 1.00 | 36.87 | O |
| ATOM | 15665 | OE2 | GLU | B | 403 | 35.149 | 82.052 | -31.393 | 1.00 | 37.36 | O |
| ATOM | 15666 | C   | GLU | B | 403 | 29.995 | 83.330 | -30.230 | 1.00 | 27.63 | C |
| ATOM | 15667 | O   | GLU | B | 403 | 29.556 | 83.090 | -31.366 | 1.00 | 27.75 | O |
| ATOM | 15669 | N   | ASN | B | 404 | 29.568 | 82.705 | -29.136 | 1.00 | 27.43 | N |
| ATOM | 15670 | CA  | ASN | B | 404 | 28.564 | 81.641 | -29.166 | 1.00 | 27.25 | C |
| ATOM | 15672 | CB  | ASN | B | 404 | 29.068 | 80.518 | -28.259 | 1.00 | 27.70 | C |
| ATOM | 15675 | CG  | ASN | B | 404 | 30.453 | 80.022 | -28.697 | 1.00 | 28.78 | C |
| ATOM | 15676 | OD1 | ASN | B | 404 | 30.629 | 79.607 | -29.844 | 1.00 | 30.25 | O |
| ATOM | 15677 | ND2 | ASN | B | 404 | 31.442 | 80.119 | -27.815 | 1.00 | 29.04 | N |
| ATOM | 15680 | C   | ASN | B | 404 | 27.142 | 82.087 | -28.815 | 1.00 | 26.67 | C |
| ATOM | 15681 | O   | ASN | B | 404 | 26.268 | 81.274 | -28.515 | 1.00 | 26.10 | O |
| ATOM | 15683 | N   | LYS | B | 405 | 26.920 | 83.397 | -28.838 | 1.00 | 26.52 | N |
| ATOM | 15684 | CA  | LYS | B | 405 | 25.611 | 83.978 | -28.613 | 1.00 | 27.01 | C |
| ATOM | 15686 | CB  | LYS | B | 405 | 24.774 | 83.867 | -29.887 | 1.00 | 27.53 | C |
| ATOM | 15689 | CG  | LYS | B | 405 | 25.386 | 84.528 | -31.105 | 1.00 | 29.82 | C |
| ATOM | 15692 | CD  | LYS | B | 405 | 24.452 | 84.415 | -32.327 | 1.00 | 29.71 | C |
| ATOM | 15695 | CE  | LYS | B | 405 | 23.962 | 82.969 | -32.533 | 1.00 | 32.39 | C |
| ATOM | 15698 | NZ  | LYS | B | 405 | 23.532 | 82.664 | -33.936 | 1.00 | 33.51 | N |
| ATOM | 15702 | C   | LYS | B | 405 | 24.854 | 83.360 | -27.460 | 1.00 | 25.85 | C |

| ATOM | 15703 | O   | LYS | B | 405 | 23.685 | 83.041 | -27.581 | 1.00 | 25.58 | O |
|------|-------|-----|-----|---|-----|--------|--------|---------|------|-------|---|
| ATOM | 15705 | N   | THR | B | 406 | 25.523 | 83.225 | -26.313 | 1.00 | 24.67 | N |
| ATOM | 15706 | CA  | THR | B | 406 | 24.936 | 82.559 | -25.177 | 1.00 | 24.60 | C |
| ATOM | 15708 | CB  | THR | B | 406 | 25.534 | 81.150 | -25.036 | 1.00 | 24.75 | C |
| ATOM | 15710 | OG1 | THR | B | 406 | 25.331 | 80.413 | -26.263 | 1.00 | 27.45 | O |
| ATOM | 15712 | CG2 | THR | B | 406 | 24.897 | 80.417 | -23.893 | 1.00 | 26.10 | C |
| ATOM | 15716 | C   | THR | B | 406 | 25.184 | 83.361 | -23.885 | 1.00 | 23.31 | C |
| ATOM | 15717 | O   | THR | B | 406 | 26.228 | 83.983 | -23.709 | 1.00 | 23.28 | O |
| ATOM | 15719 | N   | SER | B | 407 | 24.187 | 83.353 | -23.012 | 1.00 | 21.92 | N |
| ATOM | 15720 | CA  | SER | B | 407 | 24.295 | 83.939 | -21.689 | 1.00 | 21.14 | C |
| ATOM | 15722 | CB  | SER | B | 407 | 23.125 | 84.882 | -21.490 | 1.00 | 21.84 | C |
| ATOM | 15725 | OG  | SER | B | 407 | 22.977 | 85.235 | -20.143 | 1.00 | 24.78 | O |
| ATOM | 15727 | C   | SER | B | 407 | 24.299 | 82.788 | -20.666 | 1.00 | 20.66 | C |
| ATOM | 15728 | O   | SER | B | 407 | 23.432 | 81.917 | -20.700 | 1.00 | 22.64 | O |
| ATOM | 15730 | N   | HIS | B | 408 | 25.285 | 82.781 | -19.773 | 1.00 | 15.94 | N |
| ATOM | 15731 | CA  | HIS | B | 408 | 25.519 | 81.653 | -18.884 | 1.00 | 14.99 | C |
| ATOM | 15733 | CB  | HIS | B | 408 | 26.989 | 81.215 | -18.981 | 1.00 | 14.15 | C |
| ATOM | 15736 | CG  | HIS | B | 408 | 27.383 | 80.655 | -20.307 | 1.00 | 14.10 | C |
| ATOM | 15737 | ND1 | HIS | B | 408 | 27.305 | 79.309 | -20.591 | 1.00 | 13.43 | N |
| ATOM | 15739 | CE1 | HIS | B | 408 | 27.728 | 79.085 | -21.823 | 1.00 | 14.75 | C |
| ATOM | 15741 | NE2 | HIS | B | 408 | 28.086 | 80.244 | -22.355 | 1.00 | 14.59 | N |
| ATOM | 15743 | CD2 | HIS | B | 408 | 27.889 | 81.243 | -21.424 | 1.00 | 15.64 | C |
| ATOM | 15745 | C   | HIS | B | 408 | 25.232 | 82.048 | -17.445 | 1.00 | 13.33 | C |
| ATOM | 15746 | O   | HIS | B | 408 | 25.615 | 83.116 | -16.997 | 1.00 | 14.02 | O |
| ATOM | 15748 | N   | HIS | B | 409 | 24.587 | 81.140 | -16.713 | 1.00 | 13.63 | N |
| ATOM | 15749 | CA  | HIS | B | 409 | 24.207 | 81.388 | -15.330 | 1.00 | 13.86 | C |
| ATOM | 15751 | CB  | HIS | B | 409 | 22.740 | 81.040 | -15.130 | 1.00 | 14.89 | C |
| ATOM | 15754 | CG  | HIS | B | 409 | 21.853 | 81.869 | -15.990 | 1.00 | 17.88 | C |
| ATOM | 15755 | ND1 | HIS | B | 409 | 21.350 | 83.078 | -15.572 | 1.00 | 23.50 | N |
| ATOM | 15757 | CE1 | HIS | B | 409 | 20.645 | 83.621 | -16.547 | 1.00 | 22.78 | C |
| ATOM | 15759 | NE2 | HIS | B | 409 | 20.689 | 82.814 | -17.591 | 1.00 | 23.79 | N |
| ATOM | 15761 | CD2 | HIS | B | 409 | 21.443 | 81.709 | -17.270 | 1.00 | 22.75 | C |
| ATOM | 15763 | C   | HIS | B | 409 | 25.136 | 80.603 | -14.409 | 1.00 | 13.43 | C |
| ATOM | 15764 | O   | HIS | B | 409 | 25.086 | 79.400 | -14.388 | 1.00 | 12.39 | O |
| ATOM | 15766 | N   | GLY | B | 410 | 26.012 | 81.315 | -13.704 | 1.00 | 12.78 | N |
| ATOM | 15767 | CA  | GLY | B | 410 | -27.048 | 80.683 | -12.900 | 1.00 | 12.67 | C |
| ATOM | 15770 | C   | GLY | B | 410 | 27.156 | 81.289 | -11.518 | 1.00 | 12.73 | C |
| ATOM | 15771 | O   | GLY | B | 410 | 26.176 | 81.831 | -10.996 | 1.00 | 11.46 | O |
| ATOM | 15773 | N   | GLY | B | 411 | 28.359 | 81.198 | -10.953 | 1.00 | 12.54 | N |
| ATOM | 15774 | CA  | GLY | B | 411 | 28.581 | 81.478 | -9.551  | 1.00 | 12.22 | C |
| ATOM | 15777 | C   | GLY | B | 411 | 29.863 | 82.221 | -9.279  | 1.00 | 11.11 | C |
| ATOM | 15778 | O   | GLY | B | 411 | 30.409 | 82.139 | -8.162  | 1.00 | 11.76 | O |
| ATOM | 15780 | N   | ASN | B | 412 | 30.362 | 82.981 | -10.252 | 1.00 | 11.58 | N |
| ATOM | 15781 | CA  | ASN | B | 412 | 31.676 | 83.625 | -10.051 | 1.00 | 11.84 | C |
| ATOM | 15783 | CB  | ASN | B | 412 | 32.298 | 84.047 | -11.391 | 1.00 | 11.99 | C |
| ATOM | 15786 | CG  | ASN | B | 412 | 32.788 | 82.878 | -12.202 | 1.00 | 13.05 | C |
| ATOM | 15787 | OD1 | ASN | B | 412 | 33.163 | 81.821 | -11.661 | 1.00 | 11.36 | O |
| ATOM | 15788 | ND2 | ASN | B | 412 | 32.850 | 83.076 | -13.527 | 1.00 | 11.72 | N |
| ATOM | 15791 | C   | ASN | B | 412 | 31.741 | 84.784 | -9.036  | 1.00 | 11.78 | C |
| ATOM | 15792 | O   | ASN | B | 412 | 32.797 | 85.339 | -8.732  | 1.00 | 13.37 | O |
| ATOM | 15794 | N   | PHE | B | 413 | 30.593 | 85.163 | -8.521  | 1.00 | 9.77  | N |
| ATOM | 15795 | CA  | PHE | B | 413 | 30.521 | 86.114 | -7.440  | 1.00 | 11.08 | C |
| ATOM | 15797 | CB  | PHE | B | 413 | 29.145 | 86.770 | -7.481  | 1.00 | 10.81 | C |
| ATOM | 15800 | CG  | PHE | B | 413 | 28.020 | 85.756 | -7.621  | 1.00 | 10.75 | C |
| ATOM | 15801 | CD1 | PHE | B | 413 | 27.665 | 84.891 | -6.576  | 1.00 | 11.18 | C |
| ATOM | 15803 | CE1 | PHE | B | 413 | 26.675 | 83.962 | -6.704  | 1.00 | 12.94 | C |
| ATOM | 15805 | CZ  | PHE | B | 413 | 26.042 | 83.820 | -7.897  | 1.00 | 13.37 | C |

| ATOM | 15807 | CE2 | PHE B 413 | 26.395 | 84.633 | -8.949 | 1.00 | 15.16 | C |
|---|---|---|---|---|---|---|---|---|---|
| ATOM | 15809 | CD2 | PHE B 413 | 27.379 | 85.580 | -8.818 | 1.00 | 13.68 | C |
| ATOM | 15811 | C | PHE B 413 | 30.762 | 85.483 | -6.044 | 1.00 | 10.79 | C |
| ATOM | 15812 | O | PHE B 413 | 30.772 | 86.201 | -5.055 | 1.00 | 10.82 | O |
| ATOM | 15814 | N | GLN B 414 | 30.884 | 84.138 | -5.983 | 1.00 | 10.09 | N |
| ATOM | 15815 | CA | GLN B 414 | 31.066 | 83.452 | -4.712 | 1.00 | 11.03 | C |
| ATOM | 15817 | CB | GLN B 414 | 30.648 | 81.990 | -4.861 | 1.00 | 11.28 | C |
| ATOM | 15820 | CG | GLN B 414 | 30.759 | 81.132 | -3.637 | 1.00 | 9.91 | C |
| ATOM | 15823 | CD | GLN B 414 | 29.750 | 81.522 | -2.580 | 1.00 | 11.43 | C |
| ATOM | 15824 | OE1 | GLN B 414 | 30.004 | 82.407 | -1.780 | 1.00 | 13.12 | O |
| ATOM | 15825 | NE2 | GLN B 414 | 28.609 | 80.840 | -2.567 | 1.00 | 11.71 | N |
| ATOM | 15828 | C | GLN B 414 | 32.539 | 83.597 | -4.321 | 1.00 | 12.10 | C |
| ATOM | 15829 | O | GLN B 414 | 33.395 | 82.834 | -4.836 | 1.00 | 13.93 | O |
| ATOM | 15831 | N | ALA B 415 | 32.791 | 84.475 | -3.381 | 1.00 | 12.17 | N |
| ATOM | 15832 | CA | ALA B 415 | 34.180 | 84.950 | -3.136 | 1.00 | 11.73 | C |
| ATOM | 15834 | CB | ALA B 415 | 34.234 | 86.362 | -2.606 | 1.00 | 12.80 | C |
| ATOM | 15838 | C | ALA B 415 | 34.959 | 83.990 | -2.212 | 1.00 | 12.86 | C |
| ATOM | 15839 | O | ALA B 415 | 35.732 | 84.475 | -1.365 | 1.00 | 12.35 | O |
| ATOM | 15841 | N | ALA B 416 | 34.766 | 82.675 | -2.359 | 1.00 | 12.35 | N |
| ATOM | 15842 | CA | ALA B 416 | 35.448 | 81.684 | -1.510 | 1.00 | 12.02 | C |
| ATOM | 15844 | CB | ALA B 416 | 34.891 | 80.321 | -1.725 | 1.00 | 11.93 | C |
| ATOM | 15848 | C | ALA B 416 | 36.956 | 81.727 | -1.720 | 1.00 | 11.64 | C |
| ATOM | 15849 | O | ALA B 416 | 37.731 | 81.623 | -0.772 | 1.00 | 13.31 | O |
| ATOM | 15851 | N | ALA B 417 | 37.388 | 82.008 | -2.929 | 1.00 | 12.30 | N |
| ATOM | 15852 | CA | ALA B 417 | 38.850 | 82.091 | -3.187 | 1.00 | 12.25 | C |
| ATOM | 15854 | CB | ALA B 417 | 39.092 | 82.378 | -4.614 | 1.00 | 14.48 | C |
| ATOM | 15858 | C | ALA B 417 | 39.421 | 83.221 | -2.316 | 1.00 | 13.02 | C |
| ATOM | 15859 | O | ALA B 417 | 40.484 | 83.036 | -1.692 | 1.00 | 13.30 | O |
| ATOM | 15861 | N | VAL B 418 | 38.688 | 84.333 | -2.185 | 1.00 | 12.62 | N |
| ATOM | 15862 | CA | VAL B 418 | 39.173 | 85.495 | -1.405 | 1.00 | 12.98 | C |
| ATOM | 15864 | CB | VAL B 418 | 38.355 | 86.779 | -1.649 | 1.00 | 13.35 | C |
| ATOM | 15866 | CG1 | VAL B 418 | 38.881 | 87.901 | -0.786 | 1.00 | 12.92 | C |
| ATOM | 15870 | CG2 | VAL B 418 | 38.330 | 87.134 | -3.127 | 1.00 | 13.80 | C |
| ATOM | 15874 | C | VAL B 418 | 39.133 | 85.157 | 0.079 | 1.00 | 12.14 | C |
| ATOM | 15875 | O | VAL B 418 | 40.096 | 85.439 | 0.813 | 1.00 | 13.11 | O |
| ATOM | 15877 | N | ALA B 419 | 38.011 | 84.553 | 0.530 | 1.00 | 12.48 | N |
| ATOM | 15878 | CA | ALA B 419 | 37.851 | 84.257 | 1.946 | 1.00 | 13.31 | C |
| ATOM | 15880 | CB | ALA B 419 | 36.543 | 83.616 | 2.175 | 1.00 | 13.75 | C |
| ATOM | 15884 | C | ALA B 419 | 38.975 | 83.302 | 2.352 | 1.00 | 13.68 | C |
| ATOM | 15885 | O | ALA B 419 | 39.601 | 83.492 | 3.438 | 1.00 | 12.82 | O |
| ATOM | 15887 | N | ASN B 420 | 39.265 | 82.341 | 1.470 | 1.00 | 14.15 | N |
| ATOM | 15888 | CA | ASN B 420 | 40.348 | 81.366 | 1.701 | 1.00 | 14.48 | C |
| ATOM | 15890 | CB | ASN B 420 | 40.476 | 80.453 | 0.454 | 1.00 | 16.03 | C |
| ATOM | 15893 | CG | ASN B 420 | 41.684 | 79.450 | 0.500 | 1.00 | 18.07 | C |
| ATOM | 15894 | OD1 | ASN B 420 | 42.752 | 79.726 | -0.107 | 1.00 | 24.58 | O |
| ATOM | 15895 | ND2 | ASN B 420 | 41.480 | 78.274 | 1.113 | 1.00 | 20.41 | N |
| ATOM | 15898 | C | ASN B 420 | 41.665 | 82.041 | 2.010 | 1.00 | 13.00 | C |
| ATOM | 15899 | O | ASN B 420 | 42.346 | 81.699 | 2.989 | 1.00 | 14.45 | O |
| ATOM | 15901 | N | THR B 421 | 42.027 | 83.025 | 1.208 | 1.00 | 11.61 | N |
| ATOM | 15902 | CA | THR B 421 | 43.300 | 83.703 | 1.439 | 1.00 | 12.75 | C |
| ATOM | 15904 | CB | THR B 421 | 43.642 | 84.737 | 0.337 | 1.00 | 11.48 | C |
| ATOM | 15906 | OG1 | THR B 421 | 42.752 | 85.858 | 0.357 | 1.00 | 12.42 | O |
| ATOM | 15908 | CG2 | THR B 421 | 43.579 | 84.051 | -1.043 | 1.00 | 13.36 | C |
| ATOM | 15912 | C | THR B 421 | 43.327 | 84.395 | 2.790 | 1.00 | 13.39 | C |
| ATOM | 15913 | O | THR B 421 | 44.372 | 84.471 | 3.481 | 1.00 | 13.70 | O |
| ATOM | 15915 | N | MSE B 422 | 42.185 | 84.947 | 3.156 | 1.00 | 11.91 | N |
| ATOM | 15916 | CA | MSE B 422 | 42.116 | 85.744 | 4.412 | 1.00 | 12.60 | C |

| ATOM | 15918 | CB | MSE | B | 422 | 40.904 | 86.598 | 4.386 | 1.00 | 13.68 | C |
| ATOM | 15921 | CG | MSE | B | 422 | 41.013 | 87.711 | 3.361 | 1.00 | 14.51 | C |
| ATOM | 15924 | SE | MSE | B | 422 | 42.506 | 88.973 | 3.746 | 1.00 | 21.13 | SE |
| ATOM | 15925 | CE | MSE | B | 422 | 43.985 | 88.283 | 2.622 | 1.00 | 15.68 | C |
| ATOM | 15929 | C | MSE | B | 422 | 42.153 | 84.861 | 5.667 | 1.00 | 11.98 | C |
| ATOM | 15930 | O | MSE | B | 422 | 42.777 | 85.191 | 6.663 | 1.00 | 13.33 | O |
| ATOM | 15932 | N | GLU | B | 423 | 41.465 | 83.721 | 5.610 | 1.00 | 12.78 | N |
| ATOM | 15933 | CA | GLU | B | 423 | 41.445 | 82.775 | 6.763 | 1.00 | 12.11 | C |
| ATOM | 15935 | CB | GLU | B | 423 | 40.557 | 81.565 | 6.485 | 1.00 | 13.33 | C |
| ATOM | 15938 | CG | GLU | B | 423 | 39.090 | 81.867 | 6.225 | 1.00 | 14.55 | C |
| ATOM | 15941 | CD | GLU | B | 423 | 38.278 | 82.218 | 7.462 | 1.00 | 16.21 | C |
| ATOM | 15942 | OE1 | GLU | B | 423 | 37.619 | 81.306 | 7.961 | 1.00 | 17.47 | O |
| ATOM | 15943 | OE2 | GLU | B | 423 | 38.239 | 83.370 | 7.867 | 1.00 | 14.12 | O |
| ATOM | 15944 | C | GLU | B | 423 | 42.891 | 82.357 | 7.013 | 1.00 | 13.43 | C |
| ATOM | 15945 | O | GLU | B | 423 | 43.372 | 82.437 | 8.168 | 1.00 | 13.22 | O |
| ATOM | 15947 | N | LYS | B | 424 | 43.568 | 81.908 | 5.954 | 1.00 | 14.34 | N |
| ATOM | 15948 | CA | LYS | B | 424 | 44.957 | 81.406 | 6.074 | 1.00 | 16.78 | C |
| ATOM | 15950 | CB | LYS | B | 424 | 45.472 | 80.804 | 4.750 | 1.00 | 17.38 | C |
| ATOM | 15953 | CG | LYS | B | 424 | 44.644 | 79.672 | 4.180 | 1.00 | 22.50 | C |
| ATOM | 15956 | CD | LYS | B | 424 | 44.943 | 79.412 | 2.644 | 1.00 | 23.09 | C |
| ATOM | 15959 | CE | LYS | B | 424 | 46.383 | 79.736 | 2.280 | 1.00 | 25.32 | C |
| ATOM | 15962 | NZ | LYS | B | 424 | 46.823 | 81.185 | 2.062 | 1.00 | 26.31 | N |
| ATOM | 15966 | C | LYS | B | 424 | 45.926 | 82.489 | 6.512 | 1.00 | 14.45 | C |
| ATOM | 15967 | O | LYS | B | 424 | 46.825 | 82.284 | 7.348 | 1.00 | 14.49 | O |
| ATOM | 15969 | N | THR | B | 425 | 45.764 | 83.684 | 5.949 | 1.00 | 13.37 | N |
| ATOM | 15970 | CA | THR | B | 425 | 46.681 | 84.765 | 6.314 | 1.00 | 13.25 | C |
| ATOM | 15972 | CB | THR | B | 425 | 46.479 | 85.959 | 5.369 | 1.00 | 13.11 | C |
| ATOM | 15974 | OG1 | THR | B | 425 | 46.742 | 85.542 | 4.022 | 1.00 | 12.99 | O |
| ATOM | 15976 | CG2 | THR | B | 425 | 47.354 | 87.205 | 5.764 | 1.00 | 15.45 | C |
| ATOM | 15980 | C | THR | B | 425 | 46.484 | 85.129 | 7.787 | 1.00 | 13.56 | C |
| ATOM | 15981 | O | THR | B | 425 | 47.473 | 85.441 | 8.489 | 1.00 | 13.66 | O |
| ATOM | 15983 | N | ARG | B | 426 | 45.243 | 85.122 | 8.301 | 1.00 | 12.52 | N |
| ATOM | 15984 | CA | ARG | B | 426 | 45.047 | 85.591 | 9.677 | 1.00 | 12.85 | C |
| ATOM | 15986 | CB | ARG | B | 426 | 43.548 | 85.768 | 9.921 | 1.00 | 13.93 | C |
| ATOM | 15989 | CG | ARG | B | 426 | 43.262 | 86.587 | 11.151 | 1.00 | 12.35 | C |
| ATOM | 15992 | CD | ARG | B | 426 | 41.818 | 87.042 | 11.255 | 1.00 | 13.78 | C |
| ATOM | 15995 | NE | ARG | B | 426 | 40.832 | 85.965 | 11.196 | 1.00 | 12.27 | N |
| ATOM | 15997 | CZ | ARG | B | 426 | 40.130 | 85.566 | 10.116 | 1.00 | 11.70 | C |
| ATOM | 15998 | NH1 | ARG | B | 426 | 39.251 | 84.592 | 10.234 | 1.00 | 13.55 | N |
| ATOM | 16001 | NH2 | ARG | B | 426 | 40.268 | 86.104 | 8.914 | 1.00 | 12.56 | N |
| ATOM | 16004 | C | ARG | B | 426 | 45.666 | 84.598 | 10.677 | 1.00 | 13.15 | C |
| ATOM | 16005 | O | ARG | B | 426 | 46.210 | 84.978 | 11.730 | 1.00 | 13.51 | O |
| ATOM | 16007 | N | LEU | B | 427 | 45.628 | 83.350 | 10.320 | 1.00 | 13.44 | N |
| ATOM | 16008 | CA | LEU | B | 427 | 46.233 | 82.323 | 11.150 | 1.00 | 13.91 | C |
| ATOM | 16010 | CB | LEU | B | 427 | 45.787 | 80.908 | 10.725 | 1.00 | 14.83 | C |
| ATOM | 16013 | CG | LEU | B | 427 | 46.392 | 79.779 | 11.577 | 1.00 | 14.77 | C |
| ATOM | 16015 | CD1 | LEU | B | 427 | 46.163 | 79.908 | 13.054 | 1.00 | 13.26 | C |
| ATOM | 16019 | CD2 | LEU | B | 427 | 45.870 | 78.480 | 11.054 | 1.00 | 15.91 | C |
| ATOM | 16023 | C | LEU | B | 427 | 47.739 | 82.501 | 11.071 | 1.00 | 13.08 | C |
| ATOM | 16024 | O | LEU | B | 427 | 48.423 | 82.495 | 12.090 | 1.00 | 12.96 | O |
| ATOM | 16026 | N | GLY | B | 428 | 48.267 | 82.718 | 9.878 | 1.00 | 13.26 | N |
| ATOM | 16027 | CA | GLY | B | 428 | 49.700 | 83.051 | 9.762 | 1.00 | 13.62 | C |
| ATOM | 16030 | C | GLY | B | 428 | 50.197 | 84.229 | 10.574 | 1.00 | 14.10 | C |
| ATOM | 16031 | O | GLY | B | 428 | 51.253 | 84.172 | 11.193 | 1.00 | 13.35 | O |
| ATOM | 16033 | N | LEU | B | 429 | 49.391 | 85.293 | 10.606 | 1.00 | 12.88 | N |
| ATOM | 16034 | CA | LEU | B | 429 | 49.727 | 86.513 | 11.378 | 1.00 | 13.06 | C |
| ATOM | 16036 | CB | LEU | B | 429 | 48.716 | 87.628 | 11.140 | 1.00 | 12.63 | C |

| ATOM | 16039 | CG | LEU B 429 | 48.727 | 88.180 | 9.710 | 1.00 | 12.29 | C |
|---|---|---|---|---|---|---|---|---|---|
| ATOM | 16041 | CD1 | LEU B 429 | 47.496 | 89.029 | 9.464 | 1.00 | 13.75 | C |
| ATOM | 16045 | CD2 | LEU B 429 | 50.048 | 88.929 | 9.433 | 1.00 | 12.76 | C |
| ATOM | 16049 | C | LEU B 429 | 49.843 | 86.144 | 12.861 | 1.00 | 12.54 | C |
| ATOM | 16050 | O | LEU B 429 | 50.716 | 86.650 | 13.593 | 1.00 | 11.69 | O |
| ATOM | 16052 | N | ALA B 430 | 48.951 | 85.272 | 13.320 | 1.00 | 12.19 | N |
| ATOM | 16053 | CA | ALA B 430 | 48.986 | 84.863 | 14.714 | 1.00 | 13.17 | C |
| ATOM | 16055 | CB | ALA B 430 | 47.763 | 84.053 | 15.051 | 1.00 | 14.17 | C |
| ATOM | 16059 | C | ALA B 430 | 50.257 | 84.031 | 14.986 | 1.00 | 12.80 | C |
| ATOM | 16060 | O | ALA B 430 | 50.847 | 84.109 | 16.060 | 1.00 | 13.23 | O |
| ATOM | 16062 | N | GLN B 431 | 50.673 | 83.227 | 14.020 | 1.00 | 13.16 | N |
| ATOM | 16063 | CA | GLN B 431 | 51.875 | 82.411 | 14.161 | 1.00 | 13.28 | C |
| ATOM | 16065 | CB | GLN B 431 | 51.985 | 81.330 | 13.088 | 1.00 | 12.86 | C |
| ATOM | 16068 | CG | GLN B 431 | 50.831 | 80.320 | 13.152 | 1.00 | 14.76 | C |
| ATOM | 16071 | CD | GLN B 431 | 50.656 | 79.756 | 14.506 | 1.00 | 21.82 | C |
| ATOM | 16072 | OE1 | GLN B 431 | 51.413 | 78.865 | 14.913 | 1.00 | 26.94 | O |
| ATOM | 16073 | NE2 | GLN B 431 | 49.646 | 80.258 | 15.248 | 1.00 | 28.10 | N |
| ATOM | 16076 | C | GLN B 431 | 53.156 | 83.268 | 14.150 | 1.00 | 13.27 | C |
| ATOM | 16077 | O | GLN B 431 | 54.102 | 83.022 | 14.928 | 1.00 | 13.79 | O |
| ATOM | 16079 | N | ILE B 432 | 53.212 | 84.247 | 13.255 | 1.00 | 13.23 | N |
| ATOM | 16080 | CA | ILE B 432 | 54.307 | 85.224 | 13.270 | 1.00 | 12.68 | C |
| ATOM | 16082 | CB | ILE B 432 | 54.135 | 86.314 | 12.169 | 1.00 | 13.23 | C |
| ATOM | 16084 | CG1 | ILE B 432 | 54.186 | 85.693 | 10.765 | 1.00 | 13.09 | C |
| ATOM | 16087 | CD1 | ILE B 432 | 53.771 | 86.623 | 9.666 | 1.00 | 14.18 | C |
| ATOM | 16091 | CG2 | ILE B 432 | 55.212 | 87.400 | 12.340 | 1.00 | 12.50 | C |
| ATOM | 16095 | C | ILE B 432 | 54.331 | 85.911 | 14.634 | 1.00 | 12.95 | C |
| ATOM | 16096 | O | ILE B 432 | 55.364 | 85.992 | 15.304 | 1.00 | 13.31 | O |
| ATOM | 16098 | N | GLY B 433 | 53.173 | 86.419 | 15.074 | 1.00 | 12.49 | N |
| ATOM | 16099 | CA | GLY B 433 | 53.095 | 87.091 | 16.377 | 1.00 | 12.54 | C |
| ATOM | 16102 | C | GLY B 433 | 53.611 | 86.189 | 17.529 | 1.00 | 12.26 | C |
| ATOM | 16103 | O | GLY B 433 | 54.419 | 86.617 | 18.365 | 1.00 | 14.19 | O |
| ATOM | 16105 | N | LYS B 434 | 53.161 | 84.946 | 17.608 | 1.00 | 13.02 | N |
| ATOM | 16106 | CA | LYS B 434 | 53.643 | 84.056 | 18.654 | 1.00 | 13.17 | C |
| ATOM | 16108 | CB | LYS B 434 | 52.927 | 82.714 | 18.561 | 1.00 | 14.03 | C |
| ATOM | 16111 | CG | LYS B 434 | 53.379 | 81.750 | 19.621 | 1.00 | 13.96 | C |
| ATOM | 16114 | CD | LYS B 434 | 52.955 | 82.144 | 21.037 | 1.00 | 14.72 | C |
| ATOM | 16117 | CE | LYS B 434 | 53.344 | 81.044 | 22.020 | 1.00 | 18.53 | C |
| ATOM | 16120 | NZ | LYS B 434 | 52.832 | 81.171 | 23.456 | 1.00 | 19.73 | N |
| ATOM | 16124 | C | LYS B 434 | 55.166 | 83.917 | 18.587 | 1.00 | 12.93 | C |
| ATOM | 16125 | O | LYS B 434 | 55.831 | 84.015 | 19.606 | 1.00 | 14.99 | O |
| ATOM | 16127 | N | LEU B 435 | 55.737 | 83.757 | 17.400 | 1.00 | 13.38 | N |
| ATOM | 16128 | CA | LEU B 435 | 57.196 | 83.664 | 17.275 | 1.00 | 12.44 | C |
| ATOM | 16130 | CB | LEU B 435 | 57.580 | 83.496 | 15.804 | 1.00 | 12.94 | C |
| ATOM | 16133 | CG | LEU B 435 | 59.093 | 83.230 | 15.608 | 1.00 | 12.50 | C |
| ATOM | 16135 | CD1 | LEU B 435 | 59.512 | 81.865 | 16.325 | 1.00 | 14.36 | C |
| ATOM | 16139 | CD2 | LEU B 435 | 59.464 | 83.216 | 14.162 | 1.00 | 15.45 | C |
| ATOM | 16143 | C | LEU B 435 | 57.926 | 84.872 | 17.821 | 1.00 | 13.17 | C |
| ATOM | 16144 | O | LEU B 435 | 58.800 | 84.774 | 18.700 | 1.00 | 12.86 | O |
| ATOM | 16146 | N | ASN B 436 | 57.581 | 86.036 | 17.301 | 1.00 | 13.71 | N |
| ATOM | 16147 | CA | ASN B 436 | 58.297 | 87.229 | 17.719 | 1.00 | 13.87 | C |
| ATOM | 16149 | CB | ASN B 436 | 57.968 | 88.427 | 16.805 | 1.00 | 13.77 | C |
| ATOM | 16152 | CG | ASN B 436 | 58.481 | 88.190 | 15.381 | 1.00 | 15.51 | C |
| ATOM | 16153 | OD1 | ASN B 436 | 57.711 | 88.004 | 14.491 | 1.00 | 17.47 | O |
| ATOM | 16154 | ND2 | ASN B 436 | 59.812 | 88.142 | 15.197 | 1.00 | 18.74 | N |
| ATOM | 16157 | C | ASN B 436 | 58.004 | 87.526 | 19.198 | 1.00 | 13.93 | C |
| ATOM | 16158 | O | ASN B 436 | 58.873 | 88.010 | 19.912 | 1.00 | 13.40 | O |
| ATOM | 16160 | N | PHE B 437 | 56.798 | 87.261 | 19.680 | 1.00 | 12.37 | N |

| | | | | | | | | | |
|---|---|---|---|---|---|---|---|---|---|
| ATOM | 16161 | CA | PHE | B | 437 | 56.557 | 87.461 | 21.134 | 1.00 13.07 | C |
| ATOM | 16163 | CB | PHE | B | 437 | 55.160 | 87.004 | 21.493 | 1.00 13.61 | C |
| ATOM | 16166 | CG | PHE | B | 437 | 54.949 | 86.832 | 22.968 | 1.00 13.20 | C |
| ATOM | 16167 | CD1 | PHE | B | 437 | 54.964 | 87.905 | 23.829 | 1.00 15.94 | C |
| ATOM | 16169 | CE1 | PHE | B | 437 | 54.805 | 87.738 | 25.191 | 1.00 15.82 | C |
| ATOM | 16171 | CZ | PHE | B | 437 | 54.654 | 86.486 | 25.696 | 1.00 15.02 | C |
| ATOM | 16173 | CE2 | PHE | B | 437 | 54.647 | 85.393 | 24.853 | 1.00 16.67 | C |
| ATOM | 16175 | CD2 | PHE | B | 437 | 54.786 | 85.581 | 23.482 | 1.00 15.09 | C |
| ATOM | 16177 | C | PHE | B | 437 | 57.558 | 86.581 | 21.919 | 1.00 13.34 | C |
| ATOM | 16178 | O | PHE | B | 437 | 58.155 | 87.003 | 22.899 | 1.00 12.67 | O |
| ATOM | 16180 | N | THR | B | 438 | 57.672 | 85.314 | 21.543 | 1.00 12.20 | N |
| ATOM | 16181 | CA | THR | B | 438 | 58.535 | 84.388 | 22.305 | 1.00 13.79 | C |
| ATOM | 16183 | CB | THR | B | 438 | 58.436 | 82.896 | 21.905 | 1.00 14.34 | C |
| ATOM | 16185 | OG1 | THR | B | 438 | 58.856 | 82.673 | 20.541 | 1.00 14.23 | O |
| ATOM | 16187 | CG2 | THR | B | 438 | 57.006 | 82.401 | 22.074 | 1.00 13.10 | C |
| ATOM | 16191 | C | THR | B | 438 | 59.987 | 84.799 | 22.222 | 1.00 12.34 | C |
| ATOM | 16192 | O | THR | B | 438 | 60.750 | 84.697 | 23.221 | 1.00 13.08 | O |
| ATOM | 16194 | N | GLN | B | 439 | 60.379 | 85.330 | 21.071 | 1.00 12.76 | N |
| ATOM | 16195 | CA | GLN | B | 439 | 61.779 | 85.910 | 20.953 | 1.00 12.44 | C |
| ATOM | 16197 | CB | GLN | B | 439 | 62.077 | 86.374 | 19.524 | 1.00 12.47 | C |
| ATOM | 16200 | CG | GLN | B | 439 | 62.140 | 85.272 | 18.510 | 1.00 12.69 | C |
| ATOM | 16203 | CD | GLN | B | 439 | 62.196 | 85.786 | 17.089 | 1.00 12.01 | C |
| ATOM | 16204 | OE1 | GLN | B | 439 | 62.048 | 86.995 | 16.866 | 1.00 13.82 | O |
| ATOM | 16205 | NE2 | GLN | B | 439 | 62.392 | 84.876 | 16.106 | 1.00 12.81 | N |
| ATOM | 16208 | C | GLN | B | 439 | 61.974 | 87.092 | 21.891 | 1.00 14.03 | C |
| ATOM | 16209 | O | GLN | B | 439 | 63.007 | 87.179 | 22.601 | 1.00 13.78 | O |
| ATOM | 16211 | N | LEU | B | 440 | 61.020 | 88.016 | 21.864 | 1.00 13.07 | N |
| ATOM | 16212 | CA | LEU | B | 440 | 61.114 | 89.246 | 22.627 | 1.00 13.46 | C |
| ATOM | 16214 | CB | LEU | B | 440 | 59.960 | 90.158 | 22.276 | 1.00 13.96 | C |
| ATOM | 16217 | CG | LEU | B | 440 | 59.843 | 91.426 | 23.144 | 1.00 13.78 | C |
| ATOM | 16219 | CD1 | LEU | B | 440 | 61.068 | 92.270 | 23.001 | 1.00 13.66 | C |
| ATOM | 16223 | CD2 | LEU | B | 440 | 58.647 | 92.270 | 22.698 | 1.00 15.33 | C |
| ATOM | 16227 | C | LEU | B | 440 | 61.070 | 88.907 | 24.123 | 1.00 12.79 | C |
| ATOM | 16228 | O | LEU | B | 440 | 61.877 | 89.392 | 24.875 | 1.00 13.09 | O |
| ATOM | 16230 | N | THR | B | 441 | 60.154 | 88.039 | 24.554 | 1.00 13.28 | N |
| ATOM | 16231 | CA | THR | B | 441 | 59.975 | 87.838 | 25.996 | 1.00 14.00 | C |
| ATOM | 16233 | CB | THR | B | 441 | 58.605 | 87.247 | 26.297 | 1.00 15.46 | C |
| ATOM | 16235 | OG1 | THR | B | 441 | 58.294 | 87.505 | 27.696 | 1.00 15.25 | O |
| ATOM | 16237 | CG2 | THR | B | 441 | 58.559 | 85.798 | 25.968 | 1.00 15.84 | C |
| ATOM | 16241 | C | THR | B | 441 | 61.182 | 87.084 | 26.594 | 1.00 15.35 | C |
| ATOM | 16242 | O | THR | B | 441 | 61.555 | 87.277 | 27.758 | 1.00 16.10 | O |
| ATOM | 16244 | N | GLU | B | 442 | 61.858 | 86.275 | 25.784 | 1.00 15.53 | N |
| ATOM | 16245 | CA | GLU | B | 442 | 63.098 | 85.637 | 26.197 | 1.00 15.93 | C |
| ATOM | 16247 | CB | GLU | B | 442 | 63.527 | 84.613 | 25.154 | 1.00 16.32 | C |
| ATOM | 16250 | CG | GLU | B | 442 | 64.816 | 83.870 | 25.481 | 1.00 18.98 | C |
| ATOM | 16253 | CD | GLU | B | 442 | 65.213 | 82.881 | 24.401 | 1.00 21.36 | C |
| ATOM | 16254 | OE1 | GLU | B | 442 | 64.380 | 82.544 | 23.492 | 1.00 22.98 | O |
| ATOM | 16255 | OE2 | GLU | B | 442 | 66.398 | 82.445 | 24.451 | 1.00 21.33 | O |
| ATOM | 16256 | C | GLU | B | 442 | 64.172 | 86.697 | 26.406 | 1.00 14.78 | C |
| ATOM | 16257 | O | GLU | B | 442 | 64.879 | 86.692 | 27.412 | 1.00 15.71 | O |
| ATOM | 16259 | N | MSE | B | 443 | 64.266 | 87.605 | 25.450 | 1.00 14.07 | N |
| ATOM | 16260 | CA | MSE | B | 443 | 65.239 | 88.682 | 25.493 | 1.00 15.36 | C |
| ATOM | 16262 | CB | MSE | B | 443 | 65.216 | 89.516 | 24.189 | 1.00 15.41 | C |
| ATOM | 16265 | CG | MSE | B | 443 | 66.325 | 90.441 | 24.087 | 1.00 18.13 | C |
| ATOM | 16268 | SE | MSE | B | 443 | 66.369 | 91.307 | 22.306 | 1.00 23.79 | SE |
| ATOM | 16269 | CE | MSE | B | 443 | 64.560 | 92.102 | 22.365 | 1.00 24.89 | C |
| ATOM | 16273 | C | MSE | B | 443 | 65.040 | 89.620 | 26.694 | 1.00 15.18 | C |

| ATOM | 16274 | O | MSE | B | 443 | 66.011 | 90.174 | 27.187 | 1.00 | 14.49 | O |
|---|---|---|---|---|---|---|---|---|---|---|---|
| ATOM | 16276 | N | LEU | B | 444 | 63.782 | 89.799 | 27.113 | 1.00 | 15.08 | N |
| ATOM | 16277 | CA | LEU | B | 444 | 63.421 | 90.630 | 28.258 | 1.00 | 15.33 | C |
| ATOM | 16279 | CB | LEU | B | 444 | 62.040 | 91.234 | 28.023 | 1.00 | 15.46 | C |
| ATOM | 16282 | CG | LEU | B | 444 | 61.971 | 92.158 | 26.789 | 1.00 | 12.34 | C |
| ATOM | 16284 | CD1 | LEU | B | 444 | 60.539 | 92.774 | 26.726 | 1.00 | 16.93 | C |
| ATOM | 16288 | CD2 | LEU | B | 444 | 63.064 | 93.178 | 26.738 | 1.00 | 15.33 | C |
| ATOM | 16292 | C | LEU | B | 444 | 63.440 | 89.888 | 29.601 | 1.00 | 16.67 | C |
| ATOM | 16293 | O | LEU | B | 444 | 63.038 | 90.454 | 30.656 | 1.00 | 17.99 | O |
| ATOM | 16295 | N | ASN | B | 445 | 63.845 | 88.628 | 29.562 | 1.00 | 16.59 | N |
| ATOM | 16296 | CA | ASN | B | 445 | 63.974 | 87.789 | 30.761 | 1.00 | 15.78 | C |
| ATOM | 16298 | CB | ASN | B | 445 | 63.418 | 86.388 | 30.451 | 1.00 | 15.82 | C |
| ATOM | 16301 | CG | ASN | B | 445 | 63.293 | 85.519 | 31.697 | 1.00 | 18.60 | C |
| ATOM | 16302 | OD1 | ASN | B | 445 | 64.185 | 85.517 | 32.549 | 1.00 | 21.68 | O |
| ATOM | 16303 | ND2 | ASN | B | 445 | 62.193 | 84.803 | 31.829 | 1.00 | 16.74 | N |
| ATOM | 16306 | C | ASN | B | 445 | 65.416 | 87.709 | 31.209 | 1.00 | 15.80 | C |
| ATOM | 16307 | O | ASN | B | 445 | 66.251 | 87.103 | 30.541 | 1.00 | 14.93 | O |
| ATOM | 16309 | N | ALA | B | 446 | 65.691 | 88.322 | 32.360 | 1.00 | 16.90 | N |
| ATOM | 16310 | CA | ALA | B | 446 | 67.068 | 88.448 | 32.889 | 1.00 | 17.12 | C |
| ATOM | 16312 | CB | ALA | B | 446 | 67.027 | 89.219 | 34.246 | 1.00 | 18.18 | C |
| ATOM | 16316 | C | ALA | B | 446 | 67.713 | 87.095 | 33.103 | 1.00 | 17.42 | C |
| ATOM | 16317 | O | ALA | B | 446 | 68.920 | 86.944 | 32.994 | 1.00 | 16.98 | O |
| ATOM | 16319 | N | GLY | B | 447 | 66.891 | 86.112 | 33.433 | 1.00 | 17.21 | N |
| ATOM | 16320 | CA | GLY | B | 447 | 67.361 | 84.752 | 33.612 | 1.00 | 18.21 | C |
| ATOM | 16323 | C | GLY | B | 447 | 67.688 | 84.021 | 32.348 | 1.00 | 18.42 | C |
| ATOM | 16324 | O | GLY | B | 447 | 68.354 | 83.009 | 32.405 | 1.00 | 19.68 | O |
| ATOM | 16326 | N | MSE | B | 448 | 67.246 | 84.523 | 31.199 | 1.00 | 16.79 | N |
| ATOM | 16327 | CA | MSE | B | 448 | 67.451 | 83.821 | 29.927 | 1.00 | 18.74 | C |
| ATOM | 16329 | CB | MSE | B | 448 | 66.083 | 83.523 | 29.291 | 1.00 | 18.01 | C |
| ATOM | 16332 | CG | MSE | B | 448 | 65.173 | 82.805 | 30.182 | 1.00 | 20.54 | C |
| ATOM | 16335 | SE | MSE | B | 448 | 63.326 | 82.544 | 29.449 | 1.00 | 30.11 | SE |
| ATOM | 16336 | CE | MSE | B | 448 | 63.800 | 81.254 | 28.169 | 1.00 | 21.86 | C |
| ATOM | 16340 | C | MSE | B | 448 | 68.258 | 84.590 | 28.873 | 1.00 | 17.73 | C |
| ATOM | 16341 | O | MSE | B | 448 | 68.545 | 84.041 | 27.847 | 1.00 | 17.25 | O |
| ATOM | 16343 | N | ASN | B | 449 | 68.534 | 85.881 | 29.074 | 1.00 | 16.97 | N |
| ATOM | 16344 | CA | ASN | B | 449 | 68.994 | 86.779 | 28.009 | 1.00 | 17.86 | C |
| ATOM | 16346 | CB | ASN | B | 449 | 68.192 | 88.097 | 28.091 | 1.00 | 17.47 | C |
| ATOM | 16349 | CG | ASN | B | 449 | 68.478 | 88.883 | 29.349 | 1.00 | 19.74 | C |
| ATOM | 16350 | OD1 | ASN | B | 449 | 69.325 | 88.479 | 30.163 | 1.00 | 18.75 | O |
| ATOM | 16351 | ND2 | ASN | B | 449 | 67.783 | 90.013 | 29.535 | 1.00 | 15.69 | N |
| ATOM | 16354 | C | ASN | B | 449 | 70.487 | 86.994 | 27.930 | 1.00 | 17.59 | C |
| ATOM | 16355 | O | ASN | B | 449 | 70.993 | 87.990 | 27.426 | 1.00 | 17.52 | O |
| ATOM | 16357 | N | ARG | B | 450 | 71.234 | 86.000 | 28.410 | 1.00 | 17.31 | N |
| ATOM | 16358 | CA | ARG | B | 450 | 72.686 | 85.982 | 28.243 | 1.00 | 19.31 | C |
| ATOM | 16360 | CB | ARG | B | 450 | 73.019 | 85.622 | 26.773 | 1.00 | 20.04 | C |
| ATOM | 16363 | CG | ARG | B | 450 | 72.380 | 84.267 | 26.373 | 1.00 | 24.93 | C |
| ATOM | 16366 | CD | ARG | B | 450 | 72.364 | 83.925 | 24.865 | 1.00 | 25.07 | C |
| ATOM | 16373 | C | ARG | B | 450 | 73.312 | 87.271 | 28.778 | 1.00 | 17.64 | C |
| ATOM | 16374 | O | ARG | B | 450 | 74.230 | 87.839 | 28.197 | 1.00 | 19.35 | O |
| ATOM | 16376 | N | GLY | B | 451 | 72.804 | 87.727 | 29.924 | 1.00 | 15.85 | N |
| ATOM | 16377 | CA | GLY | B | 451 | 73.426 | 88.827 | 30.637 | 1.00 | 15.39 | C |
| ATOM | 16380 | C | GLY | B | 451 | 73.038 | 90.243 | 30.245 | 1.00 | 15.50 | C |
| ATOM | 16381 | O | GLY | B | 451 | 73.659 | 91.201 | 30.713 | 1.00 | 16.33 | O |
| ATOM | 16383 | N | LEU | B | 452 | 71.999 | 90.381 | 29.426 | 1.00 | 15.41 | N |
| ATOM | 16384 | CA | LEU | B | 452 | 71.515 | 91.730 | 29.134 | 1.00 | 14.98 | C |
| ATOM | 16386 | CB | LEU | B | 452 | 70.432 | 91.723 | 28.039 | 1.00 | 16.10 | C |
| ATOM | 16389 | CG | LEU | B | 452 | 70.918 | 91.482 | 26.608 | 1.00 | 16.70 | C |

| | | | | | | | | | |
|---|---|---|---|---|---|---|---|---|---|
| ATOM | 16391 | CD1 | LEU | B | 452 | 69.838 | 91.068 | 25.654 | 1.00 17.68 | C |
| ATOM | 16395 | CD2 | LEU | B | 452 | 71.642 | 92.775 | 26.132 | 1.00 18.08 | C |
| ATOM | 16399 | C | LEU | B | 452 | 70.930 | 92.296 | 30.431 | 1.00 15.14 | C |
| ATOM | 16400 | O | LEU | B | 452 | 70.379 | 91.558 | 31.238 | 1.00 15.00 | O |
| ATOM | 16402 | N | PRO | B | 453 | 71.000 | 93.616 | 30.612 | 1.00 15.13 | N |
| ATOM | 16403 | CA | PRO | B | 453 | 70.448 | 94.213 | 31.831 | 1.00 15.26 | C |
| ATOM | 16405 | CB | PRO | B | 453 | 70.634 | 95.716 | 31.589 | 1.00 16.34 | C |
| ATOM | 16408 | CG | PRO | B | 453 | 71.798 | 95.797 | 30.705 | 1.00 16.32 | C |
| ATOM | 16411 | CD | PRO | B | 453 | 71.632 | 94.632 | 29.747 | 1.00 16.39 | C |
| ATOM | 16414 | C | PRO | B | 453 | 68.981 | 93.886 | 32.022 | 1.00 15.19 | C |
| ATOM | 16415 | O | PRO | B | 453 | 68.254 | 93.854 | 31.048 | 1.00 13.69 | O |
| ATOM | 16416 | N | SER | B | 454 | 68.583 | 93.649 | 33.262 | 1.00 15.22 | N |
| ATOM | 16417 | CA | SER | B | 454 | 67.157 | 93.468 | 33.614 | 1.00 15.84 | C |
| ATOM | 16419 | CB | SER | B | 454 | 66.939 | 93.533 | 35.122 | 1.00 18.26 | C |
| ATOM | 16422 | OG | SER | B | 454 | 67.584 | 94.700 | 35.574 | 1.00 25.75 | O |
| ATOM | 16424 | C | SER | B | 454 | 66.284 | 94.555 | 32.968 | 1.00 14.98 | C |
| ATOM | 16425 | O | SER | B | 454 | 66.610 | 95.756 | 33.015 | 1.00 14.55 | O |
| ATOM | 16427 | N | CYS | B | 455 | 65.235 | 94.120 | 32.294 | 1.00 15.65 | N |
| ATOM | 16428 | CA | CYS | B | 455 | 64.258 | 95.002 | 31.648 | 1.00 15.44 | C |
| ATOM | 16430 | CB | CYS | B | 455 | 63.521 | 95.856 | 32.662 | 1.00 16.40 | C |
| ATOM | 16433 | SG | CYS | B | 455 | 62.604 | 94.836 | 33.858 | 1.00 21.61 | S |
| ATOM | 16435 | C | CYS | B | 455 | 64.863 | 95.907 | 30.572 | 1.00 13.42 | C |
| ATOM | 16436 | O | CYS | B | 455 | 64.203 | 96.799 | 30.091 | 1.00 15.08 | O |
| ATOM | 16438 | N | LEU | B | 456 | 66.086 | 95.599 | 30.136 | 1.00 12.96 | N |
| ATOM | 16439 | CA | LEU | B | 456 | 66.857 | 96.473 | 29.256 | 1.00 13.39 | C |
| ATOM | 16441 | CB | LEU | B | 456 | 66.330 | 96.464 | 27.814 | 1.00 13.01 | C |
| ATOM | 16444 | CG | LEU | B | 456 | 66.130 | 95.106 | 27.159 | 1.00 14.92 | C |
| ATOM | 16446 | CD1 | LEU | B | 456 | 65.705 | 95.251 | 25.695 | 1.00 14.45 | C |
| ATOM | 16450 | CD2 | LEU | B | 456 | 67.345 | 94.230 | 27.225 | 1.00 15.82 | C |
| ATOM | 16454 | C | LEU | B | 456 | 67.022 | 97.881 | 29.839 | 1.00 13.90 | C |
| ATOM | 16455 | O | LEU | B | 456 | 67.109 | 98.910 | 29.132 | 1.00 14.32 | O |
| ATOM | 16457 | N | ALA | B | 457 | 67.114 | 97.931 | 31.157 | 1.00 14.84 | N |
| ATOM | 16458 | CA | ALA | B | 457 | 67.366 | 99.195 | 31.831 | 1.00 13.83 | C |
| ATOM | 16460 | CB | ALA | B | 457 | 67.153 | 99.016 | 33.320 | 1.00 14.06 | C |
| ATOM | 16464 | C | ALA | B | 457 | 68.824 | 99.588 | 31.573 | 1.00 14.12 | C |
| ATOM | 16465 | O | ALA | B | 457 | 69.726 | 98.748 | 31.731 | 1.00 14.25 | O |
| ATOM | 16467 | N | ALA | B | 458 | 69.064 | 100.837 | 31.210 | 1.00 14.29 | N |
| ATOM | 16468 | CA | ALA | B | 458 | 70.440 | 101.307 | 30.957 | 1.00 13.66 | C |
| ATOM | 16470 | CB | ALA | B | 458 | 70.411 | 102.610 | 30.119 | 1.00 14.43 | C |
| ATOM | 16474 | C | ALA | B | 458 | 71.254 | 101.575 | 32.219 | 1.00 14.23 | C |
| ATOM | 16475 | O | ALA | B | 458 | 72.478 | 101.596 | 32.155 | 1.00 14.70 | O |
| ATOM | 16477 | N | GLU | B | 459 | 70.548 | 101.901 | 33.287 | 1.00 14.27 | N |
| ATOM | 16478 | CA | GLU | B | 459 | 71.164 | 102.285 | 34.550 | 1.00 15.50 | C |
| ATOM | 16480 | CB | GLU | B | 459 | 70.902 | 103.764 | 34.863 | 1.00 14.56 | C |
| ATOM | 16483 | CG | GLU | B | 459 | 71.540 | 104.727 | 33.799 | 1.00 14.69 | C |
| ATOM | 16486 | CD | GLU | B | 459 | 73.053 | 104.813 | 33.883 | 1.00 15.61 | C |
| ATOM | 16487 | OE1 | GLU | B | 459 | 73.654 | 104.529 | 34.962 | 1.00 14.46 | O |
| ATOM | 16488 | OE2 | GLU | B | 459 | 73.659 | 105.253 | 32.890 | 1.00 15.25 | O |
| ATOM | 16489 | C | GLU | B | 459 | 70.713 | 101.322 | 35.635 | 1.00 16.14 | C |
| ATOM | 16490 | O | GLU | B | 459 | 70.233 | 100.213 | 35.326 | 1.00 17.27 | O |
| ATOM | 16492 | N | ASP | B | 460 | 70.907 | 101.689 | 36.906 | 1.00 15.46 | N |
| ATOM | 16493 | CA | ASP | B | 460 | 70.577 | 100.730 | 38.002 | 1.00 15.52 | C |
| ATOM | 16495 | CB | ASP | B | 460 | 70.875 | 101.332 | 39.378 | 1.00 16.42 | C |
| ATOM | 16498 | CG | ASP | B | 460 | 72.333 | 101.162 | 39.813 | 1.00 15.21 | C |
| ATOM | 16499 | OD1 | ASP | B | 460 | 73.155 | 100.534 | 39.132 | 1.00 15.08 | O |
| ATOM | 16500 | OD2 | ASP | B | 460 | 72.641 | 101.665 | 40.904 | 1.00 16.96 | O |
| ATOM | 16501 | C | ASP | B | 460 | 69.127 | 100.248 | 37.925 | 1.00 15.50 | C |

| ATOM | 16502 | O   | ASP B 460 | 68.211 | 101.068 | 37.851 | 1.00 | 14.62 | O |
| --- | --- | --- | --- | --- | --- | --- | --- | --- | --- |
| ATOM | 16504 | N   | PRO B 461 | 68.928 | 98.917  | 37.885 | 1.00 | 16.13 | N |
| ATOM | 16505 | CA  | PRO B 461 | 67.603 | 98.342  | 37.728 | 1.00 | 16.94 | C |
| ATOM | 16507 | CB  | PRO B 461 | 67.884 | 96.843  | 37.506 | 1.00 | 18.98 | C |
| ATOM | 16510 | CG  | PRO B 461 | 69.270 | 96.678  | 37.315 | 1.00 | 19.40 | C |
| ATOM | 16513 | CD  | PRO B 461 | 69.989 | 97.893  | 37.768 | 1.00 | 16.74 | C |
| ATOM | 16516 | C   | PRO B 461 | 66.698 | 98.552  | 38.924 | 1.00 | 16.74 | C |
| ATOM | 16517 | O   | PRO B 461 | 65.479 | 98.385  | 38.796 | 1.00 | 16.48 | O |
| ATOM | 16518 | N   | SER B 462 | 67.252 | 98.875  | 40.083 | 1.00 | 16.06 | N |
| ATOM | 16519 | CA  | SER B 462 | 66.417 | 99.134  | 41.260 | 1.00 | 16.22 | C |
| ATOM | 16521 | CB  | SER B 462 | 67.229 | 99.373  | 42.518 | 1.00 | 15.34 | C |
| ATOM | 16524 | OG  | SER B 462 | 68.067 | 100.455 | 42.379 | 1.00 | 14.80 | O |
| ATOM | 16526 | C   | SER B 462 | 65.419 | 100.236 | 41.057 | 1.00 | 16.18 | C |
| ATOM | 16527 | O   | SER B 462 | 64.344 | 100.234 | 41.691 | 1.00 | 18.02 | O |
| ATOM | 16529 | N   | LEU B 463 | 65.709 | 101.132 | 40.130 | 1.00 | 15.67 | N |
| ATOM | 16530 | CA  | LEU B 463 | 64.823 | 102.290 | 39.863 | 1.00 | 16.77 | C |
| ATOM | 16532 | CB  | LEU B 463 | 65.346 | 103.565 | 40.521 | 1.00 | 18.97 | C |
| ATOM | 16535 | CG  | LEU B 463 | 65.200 | 103.593 | 42.054 | 1.00 | 20.40 | C |
| ATOM | 16537 | CD1 | LEU B 463 | 65.849 | 104.810 | 42.658 | 1.00 | 23.14 | C |
| ATOM | 16541 | CD2 | LEU B 463 | 63.733 | 103.577 | 42.468 | 1.00 | 22.18 | C |
| ATOM | 16545 | C   | LEU B 463 | 64.564 | 102.469 | 38.386 | 1.00 | 15.50 | C |
| ATOM | 16546 | O   | LEU B 463 | 64.238 | 103.541 | 37.925 | 1.00 | 15.17 | O |
| ATOM | 16548 | N   | SER B 464 | 64.659 | 101.374 | 37.661 | 1.00 | 15.12 | N |
| ATOM | 16549 | CA  | SER B 464 | 64.388 | 101.413 | 36.220 | 1.00 | 14.91 | C |
| ATOM | 16551 | CB  | SER B 464 | 65.635 | 101.848 | 35.459 | 1.00 | 14.97 | C |
| ATOM | 16554 | OG  | SER B 464 | 65.407 | 101.812 | 34.053 | 1.00 | 15.81 | O |
| ATOM | 16556 | C   | SER B 464 | 63.952 | 100.053 | 35.736 | 1.00 | 15.14 | C |
| ATOM | 16557 | O   | SER B 464 | 64.728 | 99.066  | 35.815 | 1.00 | 14.35 | O |
| ATOM | 16559 | N   | TYR B 465 | 62.715 | 100.018 | 35.227 | 1.00 | 14.33 | N |
| ATOM | 16560 | CA  | TYR B 465 | 62.069 | 98.797  | 34.722 | 1.00 | 16.15 | C |
| ATOM | 16562 | CB  | TYR B 465 | 60.775 | 98.521  | 35.496 | 1.00 | 17.60 | C |
| ATOM | 16565 | CG  | TYR B 465 | 60.908 | 98.811  | 36.958 | 1.00 | 21.33 | C |
| ATOM | 16566 | CD1 | TYR B 465 | 61.846 | 98.162  | 37.712 | 1.00 | 21.75 | C |
| ATOM | 16568 | CE1 | TYR B 465 | 62.029 | 98.512  | 39.114 | 1.00 | 22.68 | C |
| ATOM | 16570 | CZ  | TYR B 465 | 61.230 | 99.525  | 39.663 | 1.00 | 26.02 | C |
| ATOM | 16571 | OH  | TYR B 465 | 61.334 | 99.896  | 40.993 | 1.00 | 26.45 | O |
| ATOM | 16573 | CE2 | TYR B 465 | 60.290 | 100.175 | 38.881 | 1.00 | 26.30 | C |
| ATOM | 16575 | CD2 | TYR B 465 | 60.137 | 99.818  | 37.553 | 1.00 | 25.49 | C |
| ATOM | 16577 | C   | TYR B 465 | 61.763 | 98.907  | 33.215 | 1.00 | 15.05 | C |
| ATOM | 16578 | O   | TYR B 465 | 60.827 | 98.283  | 32.711 | 1.00 | 14.46 | O |
| ATOM | 16580 | N   | HIS B 466 | 62.592 | 99.671  | 32.519 | 1.00 | 14.09 | N |
| ATOM | 16581 | CA  | HIS B 466 | 62.417 | 100.092 | 31.151 | 1.00 | 13.16 | C |
| ATOM | 16583 | CB  | HIS B 466 | 63.781 | 100.104 | 30.453 | 1.00 | 11.95 | C |
| ATOM | 16586 | CG  | HIS B 466 | 63.758 | 100.679 | 29.052 | 1.00 | 14.45 | C |
| ATOM | 16587 | ND1 | HIS B 466 | 64.849 | 100.603 | 28.216 | 1.00 | 14.15 | N |
| ATOM | 16589 | CE1 | HIS B 466 | 64.545 | 101.130 | 27.044 | 1.00 | 15.84 | C |
| ATOM | 16591 | NE2 | HIS B 466 | 63.295 | 101.547 | 27.082 | 1.00 | 14.24 | N |
| ATOM | 16593 | CD2 | HIS B 466 | 62.766 | 101.257 | 28.323 | 1.00 | 14.35 | C |
| ATOM | 16595 | C   | HIS B 466 | 61.391 | 99.343  | 30.328 | 1.00 | 13.04 | C |
| ATOM | 16596 | O   | HIS B 466 | 60.279 | 99.843  | 30.164 | 1.00 | 12.76 | O |
| ATOM | 16598 | N   | CYS B 467 | 61.736 | 98.128  | 29.830 | 1.00 | 13.52 | N |
| ATOM | 16599 | CA  | CYS B 467 | 60.878 | 97.403  | 28.850 | 1.00 | 13.30 | C |
| ATOM | 16601 | CB  | CYS B 467 | 61.728 | 96.720  | 27.802 | 1.00 | 13.85 | C |
| ATOM | 16604 | SG  | CYS B 467 | 62.571 | 97.873  | 26.703 | 1.00 | 15.66 | S |
| ATOM | 16606 | C   | CYS B 467 | 59.847 | 96.409  | 29.475 | 1.00 | 13.08 | C |
| ATOM | 16607 | O   | CYS B 467 | 59.258 | 95.612  | 28.768 | 1.00 | 15.11 | O |
| ATOM | 16609 | N   | LYS B 468 | 59.679 | 96.435  | 30.798 | 1.00 | 13.00 | N |

| | | | | | | | | | |
|---|---|---|---|---|---|---|---|---|---|
| ATOM | 16610 | CA | LYS | B | 468 | 58.751 | 95.509 | 31.491 | 1.00 13.54 | C |
| ATOM | 16612 | CB | LYS | B | 468 | 58.830 | 95.711 | 33.000 | 1.00 13.43 | C |
| ATOM | 16615 | CG | LYS | B | 468 | 57.933 | 94.802 | 33.768 | 1.00 15.32 | C |
| ATOM | 16618 | CD | LYS | B | 468 | 57.950 | 95.100 | 35.233 | 1.00 18.20 | C |
| ATOM | 16621 | CE | LYS | B | 468 | 59.239 | 94.717 | 35.902 | 1.00 24.01 | C |
| ATOM | 16624 | NZ | LYS | B | 468 | 59.356 | 93.261 | 36.010 | 1.00 29.96 | N |
| ATOM | 16628 | C | LYS | B | 468 | 57.294 | 95.687 | 30.989 | 1.00 13.38 | C |
| ATOM | 16629 | O | LYS | B | 468 | 56.550 | 94.704 | 30.777 | 1.00 14.93 | O |
| ATOM | 16631 | N | GLY | B | 469 | 56.883 | 96.949 | 30.804 | 1.00 14.68 | N |
| ATOM | 16632 | CA | GLY | B | 469 | 55.558 | 97.227 | 30.318 | 1.00 12.73 | C |
| ATOM | 16635 | C | GLY | B | 469 | 55.393 | 96.696 | 28.927 | 1.00 13.55 | C |
| ATOM | 16636 | O | GLY | B | 469 | 54.351 | 96.172 | 28.547 | 1.00 14.94 | O |
| ATOM | 16638 | N | LEU | B | 470 | 56.427 | 96.841 | 28.126 | 1.00 14.90 | N |
| ATOM | 16639 | CA | LEU | B | 470 | 56.409 | 96.319 | 26.748 | 1.00 13.94 | C |
| ATOM | 16641 | CB | LEU | B | 470 | 57.526 | 96.908 | 25.902 | 1.00 13.52 | C |
| ATOM | 16644 | CG | LEU | B | 470 | 57.450 | 98.382 | 25.559 | 1.00 13.82 | C |
| ATOM | 16646 | CD1 | LEU | B | 470 | 58.734 | 98.819 | 24.788 | 1.00 17.30 | C |
| ATOM | 16650 | CD2 | LEU | B | 470 | 56.196 | 98.724 | 24.779 | 1.00 14.50 | C |
| ATOM | 16654 | C | LEU | B | 470 | 56.357 | 94.779 | 26.675 | 1.00 14.20 | C |
| ATOM | 16655 | O | LEU | B | 470 | 55.728 | 94.201 | 25.808 | 1.00 13.79 | O |
| ATOM | 16657 | N | ASP | B | 471 | 57.011 | 94.117 | 27.621 | 1.00 13.68 | N |
| ATOM | 16658 | CA | ASP | B | 471 | 56.909 | 92.655 | 27.736 | 1.00 14.10 | C |
| ATOM | 16660 | CB | ASP | B | 471 | 57.708 | 92.211 | 28.971 | 1.00 15.47 | C |
| ATOM | 16663 | CG | ASP | B | 471 | 58.088 | 90.742 | 28.945 | 1.00 19.06 | C |
| ATOM | 16664 | OD1 | ASP | B | 471 | 58.128 | 90.088 | 27.851 | 1.00 20.33 | O |
| ATOM | 16665 | OD2 | ASP | B | 471 | 58.445 | 90.227 | 30.052 | 1.00 21.42 | O |
| ATOM | 16666 | C | ASP | B | 471 | 55.433 | 92.286 | 27.899 | 1.00 14.40 | C |
| ATOM | 16667 | O | ASP | B | 471 | 54.909 | 91.409 | 27.237 | 1.00 14.35 | O |
| ATOM | 16669 | N | ILE | B | 472 | 54.770 | 92.997 | 28.799 | 1.00 13.35 | N |
| ATOM | 16670 | CA | ILE | B | 472 | 53.339 | 92.766 | 29.068 | 1.00 12.64 | C |
| ATOM | 16672 | CB | ILE | B | 472 | 52.902 | 93.591 | 30.300 | 1.00 14.41 | C |
| ATOM | 16674 | CG1 | ILE | B | 472 | 53.598 | 93.070 | 31.570 | 1.00 13.32 | C |
| ATOM | 16677 | CD1 | ILE | B | 472 | 53.639 | 94.105 | 32.740 | 1.00 12.29 | C |
| ATOM | 16681 | CG2 | ILE | B | 472 | 51.382 | 93.592 | 30.465 | 1.00 14.12 | C |
| ATOM | 16685 | C | ILE | B | 472 | 52.497 | 93.139 | 27.831 | 1.00 12.81 | C |
| ATOM | 16686 | O | ILE | B | 472 | 51.565 | 92.389 | 27.475 | 1.00 13.45 | O |
| ATOM | 16688 | N | ALA | B | 473 | 52.765 | 94.293 | 27.202 | 1.00 12.48 | N |
| ATOM | 16689 | CA | ALA | B | 473 | 52.064 | 94.651 | 25.974 | 1.00 12.64 | C |
| ATOM | 16691 | CB | ALA | B | 473 | 52.521 | 96.033 | 25.460 | 1.00 12.63 | C |
| ATOM | 16695 | C | ALA | B | 473 | 52.185 | 93.580 | 24.893 | 1.00 12.66 | C |
| ATOM | 16696 | O | ALA | B | 473 | 51.209 | 93.286 | 24.216 | 1.00 13.09 | O |
| ATOM | 16698 | N | ALA | B | 474 | 53.394 | 93.030 | 24.703 | 1.00 11.92 | N |
| ATOM | 16699 | CA | ALA | B | 474 | 53.639 | 92.058 | 23.686 | 1.00 13.33 | C |
| ATOM | 16701 | CB | ALA | B | 474 | 55.107 | 91.645 | 23.686 | 1.00 15.26 | C |
| ATOM | 16705 | C | ALA | B | 474 | 52.730 | 90.858 | 23.951 | 1.00 12.87 | C |
| ATOM | 16706 | O | ALA | B | 474 | 52.136 | 90.252 | 23.023 | 1.00 14.34 | O |
| ATOM | 16708 | N | ALA | B | 475 | 52.610 | 90.479 | 25.215 | 1.00 13.45 | N |
| ATOM | 16709 | CA | ALA | B | 475 | 51.735 | 89.345 | 25.583 | 1.00 12.83 | C |
| ATOM | 16711 | CB | ALA | B | 475 | 51.769 | 89.086 | 27.059 | 1.00 12.67 | C |
| ATOM | 16715 | C | ALA | B | 475 | 50.294 | 89.679 | 25.136 | 1.00 12.93 | C |
| ATOM | 16716 | O | ALA | B | 475 | 49.575 | 88.859 | 24.570 | 1.00 13.17 | O |
| ATOM | 16718 | N | ALA | B | 476 | 49.861 | 90.877 | 25.472 | 1.00 12.17 | N |
| ATOM | 16719 | CA | ALA | B | 476 | 48.476 | 91.289 | 25.194 | 1.00 13.41 | C |
| ATOM | 16721 | CB | ALA | B | 476 | 48.257 | 92.694 | 25.693 | 1.00 14.37 | C |
| ATOM | 16725 | C | ALA | B | 476 | 48.195 | 91.216 | 23.678 | 1.00 14.14 | C |
| ATOM | 16726 | O | ALA | B | 476 | 47.121 | 90.797 | 23.210 | 1.00 13.34 | O |
| ATOM | 16728 | N | TYR | B | 477 | 49.151 | 91.709 | 22.880 | 1.00 12.49 | N |

| ATOM | 16729 | CA | TYR B 477 | 48.938 | 91.734 | 21.422 | 1.00 | 12.59 | C |
|---|---|---|---|---|---|---|---|---|---|
| ATOM | 16731 | CB | TYR B 477 | 50.049 | 92.505 | 20.734 | 1.00 | 12.93 | C |
| ATOM | 16734 | CG | TYR B 477 | 50.264 | 93.912 | 21.191 | 1.00 | 10.91 | C |
| ATOM | 16735 | CD1 | TYR B 477 | 49.223 | 94.767 | 21.589 | 1.00 | 14.63 | C |
| ATOM | 16737 | CE1 | TYR B 477 | 49.491 | 96.115 | 21.989 | 1.00 | 14.83 | C |
| ATOM | 16739 | CZ | TYR B 477 | 50.801 | 96.615 | 22.039 | 1.00 | 12.63 | C |
| ATOM | 16740 | OH | TYR B 477 | 51.061 | 97.916 | 22.422 | 1.00 | 13.53 | O |
| ATOM | 16742 | CE2 | TYR B 477 | 51.855 | 95.801 | 21.633 | 1.00 | 12.66 | C |
| ATOM | 16744 | CD2 | TYR B 477 | 51.582 | 94.437 | 21.229 | 1.00 | 11.52 | C |
| ATOM | 16746 | C | TYR B 477 | 48.851 | 90.308 | 20.918 | 1.00 | 13.14 | C |
| ATOM | 16747 | O | TYR B 477 | 48.023 | 89.990 | 20.052 | 1.00 | 13.49 | O |
| ATOM | 16749 | N | THR B 478 | 49.717 | 89.446 | 21.450 | 1.00 | 11.92 | N |
| ATOM | 16750 | CA | THR B 478 | 49.770 | 88.074 | 21.022 | 1.00 | 12.74 | C |
| ATOM | 16752 | CB | THR B 478 | 50.995 | 87.370 | 21.635 | 1.00 | 13.83 | C |
| ATOM | 16754 | OG1 | THR B 478 | 52.154 | 88.089 | 21.230 | 1.00 | 13.19 | O |
| ATOM | 16756 | CG2 | THR B 478 | 51.117 | 85.967 | 21.207 | 1.00 | 14.78 | C |
| ATOM | 16760 | C | THR B 478 | 48.441 | 87.376 | 21.370 | 1.00 | 11.49 | C |
| ATOM | 16761 | O | THR B 478 | 47.866 | 86.639 | 20.547 | 1.00 | 12.35 | O |
| ATOM | 16763 | N | SER B 479 | 47.901 | 87.602 | 22.571 | 1.00 | 12.52 | N |
| ATOM | 16764 | CA | SER B 479 | 46.622 | 86.991 | 22.930 | 1.00 | 13.20 | C |
| ATOM | 16766 | CB | SER B 479 | 46.186 | 87.433 | 24.318 | 1.00 | 14.73 | C |
| ATOM | 16769 | OG | SER B 479 | 47.100 | 87.007 | 25.325 | 1.00 | 12.27 | O |
| ATOM | 16771 | C | SER B 479 | 45.535 | 87.433 | 21.961 | 1.00 | 12.78 | C |
| ATOM | 16772 | O | SER B 479 | 44.739 | 86.637 | 21.472 | 1.00 | 12.78 | O |
| ATOM | 16774 | N | GLU B 480 | 45.529 | 88.731 | 21.660 | 1.00 | 11.53 | N |
| ATOM | 16775 | CA | GLU B 480 | 44.512 | 89.287 | 20.750 | 1.00 | 11.27 | C |
| ATOM | 16777 | CB | GLU B 480 | 44.598 | 90.804 | 20.693 | 1.00 | 11.72 | C |
| ATOM | 16780 | CG | GLU B 480 | 43.476 | 91.374 | 19.878 | 1.00 | 13.85 | C |
| ATOM | 16783 | CD | GLU B 480 | 43.303 | 92.892 | 20.060 | 1.00 | 13.38 | C |
| ATOM | 16784 | OE1 | GLU B 480 | 43.836 | 93.451 | 21.078 | 1.00 | 13.18 | O |
| ATOM | 16785 | OE2 | GLU B 480 | 42.660 | 93.541 | 19.172 | 1.00 | 14.51 | O |
| ATOM | 16786 | C | GLU B 480 | 44.588 | 88.666 | 19.355 | 1.00 | 12.46 | C |
| ATOM | 16787 | O | GLU B 480 | 43.554 | 88.283 | 18.780 | 1.00 | 12.93 | O |
| ATOM | 16789 | N | LEU B 481 | 45.827 | 88.483 | 18.868 | 1.00 | 11.48 | N |
| ATOM | 16790 | CA | LEU B 481 | 46.020 | 87.751 | 17.612 | 1.00 | 12.70 | C |
| ATOM | 16792 | CB | LEU B 481 | 47.492 | 87.709 | 17.220 | 1.00 | 11.70 | C |
| ATOM | 16795 | CG | LEU B 481 | 48.061 | 89.044 | 16.740 | 1.00 | 12.23 | C |
| ATOM | 16797 | CD1 | LEU B 481 | 49.638 | 89.002 | 16.758 | 1.00 | 14.58 | C |
| ATOM | 16801 | CD2 | LEU B 481 | 47.523 | 89.416 | 15.360 | 1.00 | 13.05 | C |
| ATOM | 16805 | C | LEU B 481 | 45.438 | 86.350 | 17.631 | 1.00 | 11.57 | C |
| ATOM | 16806 | O | LEU B 481 | 44.883 | 85.876 | 16.622 | 1.00 | 11.54 | O |
| ATOM | 16808 | N | GLY B 482 | 45.590 | 85.634 | 18.757 | 1.00 | 11.63 | N |
| ATOM | 16809 | CA | GLY B 482 | 45.119 | 84.260 | 18.840 | 1.00 | 13.10 | C |
| ATOM | 16812 | C | GLY B 482 | 43.604 | 84.196 | 18.609 | 1.00 | 14.08 | C |
| ATOM | 16813 | O | GLY B 482 | 43.129 | 83.401 | 17.816 | 1.00 | 13.53 | O |
| ATOM | 16815 | N | HIS B 483 | 42.851 | 85.020 | 19.343 | 1.00 | 14.32 | N |
| ATOM | 16816 | CA | HIS B 483 | 41.389 | 85.005 | 19.182 | 1.00 | 13.13 | C |
| ATOM | 16818 | CB | HIS B 483 | 40.764 | 85.900 | 20.257 | 1.00 | 14.11 | C |
| ATOM | 16821 | CG | HIS B 483 | 39.329 | 86.178 | 20.057 | 1.00 | 15.25 | C |
| ATOM | 16822 | ND1 | HIS B 483 | 38.859 | 87.258 | 19.343 | 1.00 | 16.46 | N |
| ATOM | 16824 | CE1 | HIS B 483 | 37.533 | 87.237 | 19.361 | 1.00 | 15.34 | C |
| ATOM | 16826 | NE2 | HIS B 483 | 37.138 | 86.211 | 20.107 | 1.00 | 12.86 | N |
| ATOM | 16828 | CD2 | HIS B 483 | 38.241 | 85.520 | 20.525 | 1.00 | 16.14 | C |
| ATOM | 16830 | C | HIS B 483 | 40.988 | 85.435 | 17.781 | 1.00 | 12.84 | C |
| ATOM | 16831 | O | HIS B 483 | 40.058 | 84.881 | 17.201 | 1.00 | 13.11 | O |
| ATOM | 16833 | N | LEU B 484 | 41.674 | 86.435 | 17.234 | 1.00 | 12.03 | N |
| ATOM | 16834 | CA | LEU B 484 | 41.355 | 86.908 | 15.865 | 1.00 | 12.28 | C |

| ATOM | 16836 | CB | LEU | B | 484 | 42.294 | 88.043 | 15.431 | 1.00 | 13.32 | C |
|------|-------|-----|-----|---|-----|--------|--------|--------|------|-------|---|
| ATOM | 16839 | CG | LEU | B | 484 | 41.794 | 89.405 | 15.912 | 1.00 | 14.00 | C |
| ATOM | 16841 | CD1 | LEU | B | 484 | 42.884 | 90.469 | 15.855 | 1.00 | 14.35 | C |
| ATOM | 16845 | CD2 | LEU | B | 484 | 40.580 | 89.857 | 15.034 | 1.00 | 17.18 | C |
| ATOM | 16849 | C | LEU | B | 484 | 41.419 | 85.746 | 14.875 | 1.00 | 13.48 | C |
| ATOM | 16850 | O | LEU | B | 484 | 40.662 | 85.738 | 13.891 | 1.00 | 12.77 | O |
| ATOM | 16852 | N | ALA | B | 485 | 42.412 | 84.873 | 15.042 | 1.00 | 12.02 | N |
| ATOM | 16853 | CA | ALA | B | 485 | 42.780 | 83.757 | 14.103 | 1.00 | 12.41 | C |
| ATOM | 16855 | CB | ALA | B | 485 | 44.120 | 83.144 | 14.465 | 1.00 | 13.52 | C |
| ATOM | 16859 | C | ALA | B | 485 | 41.757 | 82.684 | 13.898 | 1.00 | 10.96 | C |
| ATOM | 16860 | O | ALA | B | 485 | 41.891 | 81.827 | 12.961 | 1.00 | 12.87 | O |
| ATOM | 16862 | N | ASN | B | 486 | 40.736 | 82.580 | 14.761 | 1.00 | 10.48 | N |
| ATOM | 16863 | CA | ASN | B | 486 | 39.648 | 81.624 | 14.525 | 1.00 | 11.80 | C |
| ATOM | 16865 | CB | ASN | B | 486 | 38.611 | 81.627 | 15.661 | 1.00 | 12.45 | C |
| ATOM | 16868 | CG | ASN | B | 486 | 39.216 | 81.148 | 16.967 | 1.00 | 13.51 | C |
| ATOM | 16869 | OD1 | ASN | B | 486 | 39.862 | 80.077 | 16.995 | 1.00 | 12.32 | O |
| ATOM | 16870 | ND2 | ASN | B | 486 | 39.094 | 81.980 | 18.015 | 1.00 | 14.05 | N |
| ATOM | 16873 | C | ASN | B | 486 | 38.970 | 81.930 | 13.213 | 1.00 | 11.78 | C |
| ATOM | 16874 | O | ASN | B | 486 | 38.913 | 83.089 | 12.798 | 1.00 | 11.29 | O |
| ATOM | 16876 | N | PRO | B | 487 | 38.489 | 80.887 | 12.534 | 1.00 | 12.68 | N |
| ATOM | 16877 | CA | PRO | B | 487 | 37.890 | 81.160 | 11.218 | 1.00 | 12.35 | C |
| ATOM | 16879 | CB | PRO | B | 487 | 37.690 | 79.773 | 10.622 | 1.00 | 12.30 | C |
| ATOM | 16882 | CG | PRO | B | 487 | 37.624 | 78.827 | 11.780 | 1.00 | 14.14 | C |
| ATOM | 16885 | CD | PRO | B | 487 | 38.554 | 79.436 | 12.826 | 1.00 | 13.25 | C |
| ATOM | 16888 | C | PRO | B | 487 | 36.550 | 81.876 | 11.286 | 1.00 | 11.88 | C |
| ATOM | 16889 | O | PRO | B | 487 | 35.756 | 81.660 | 12.199 | 1.00 | 13.54 | O |
| ATOM | 16890 | N | VAL | B | 488 | 36.318 | 82.743 | 10.295 | 1.00 | 12.65 | N |
| ATOM | 16891 | CA | VAL | B | 488 | 35.004 | 83.317 | 10.086 | 1.00 | 12.32 | C |
| ATOM | 16893 | CB | VAL | B | 488 | 35.173 | 84.698 | 9.378 | 1.00 | 12.60 | C |
| ATOM | 16895 | CG1 | VAL | B | 488 | 33.904 | 85.241 | 8.714 | 1.00 | 16.32 | C |
| ATOM | 16899 | CG2 | VAL | B | 488 | 35.794 | 85.718 | 10.344 | 1.00 | 13.48 | C |
| ATOM | 16903 | C | VAL | B | 488 | 34.132 | 82.427 | 9.216 | 1.00 | 10.41 | C |
| ATOM | 16904 | O | VAL | B | 488 | 32.914 | 82.366 | 9.407 | 1.00 | 12.34 | O |
| ATOM | 16906 | N | THR | B | 489 | 34.753 | 81.650 | 8.320 | 1.00 | 12.51 | N |
| ATOM | 16907 | CA | THR | B | 489 | 34.018 | 80.912 | 7.317 | 1.00 | 12.60 | C |
| ATOM | 16909 | CB | THR | B | 489 | 34.920 | 80.527 | 6.168 | 1.00 | 12.63 | C |
| ATOM | 16911 | OG1 | THR | B | 489 | 35.962 | 79.660 | 6.648 | 1.00 | 13.53 | O |
| ATOM | 16913 | CG2 | THR | B | 489 | 35.488 | 81.728 | 5.481 | 1.00 | 14.48 | C |
| ATOM | 16917 | C | THR | B | 489 | 33.219 | 79.694 | 7.788 | 1.00 | 13.07 | C |
| ATOM | 16918 | O | THR | B | 489 | 32.395 | 79.170 | 7.031 | 1.00 | 15.68 | O |
| ATOM | 16920 | N | THR | B | 490 | 33.374 | 79.308 | 9.041 | 1.00 | 12.12 | N |
| ATOM | 16921 | CA | THR | B | 490 | 32.536 | 78.278 | 9.661 | 1.00 | 13.59 | C |
| ATOM | 16923 | CB | THR | B | 490 | 33.304 | 77.638 | 10.830 | 1.00 | 13.82 | C |
| ATOM | 16925 | OG1 | THR | B | 490 | 33.779 | 78.664 | 11.707 | 1.00 | 14.96 | O |
| ATOM | 16927 | CG2 | THR | B | 490 | 34.462 | 76.796 | 10.312 | 1.00 | 16.86 | C |
| ATOM | 16931 | C | THR | B | 490 | 31.224 | 78.847 | 10.220 | 1.00 | 14.23 | C |
| ATOM | 16932 | O | THR | B | 490 | 30.458 | 78.102 | 10.877 | 1.00 | 17.85 | O |
| ATOM | 16934 | N | HIS | B | 491 | 30.978 | 80.130 | 10.004 | 1.00 | 13.40 | N |
| ATOM | 16935 | CA | HIS | B | 491 | 29.796 | 80.826 | 10.565 | 1.00 | 12.67 | C |
| ATOM | 16937 | CB | HIS | B | 491 | 30.224 | 82.026 | 11.417 | 1.00 | 13.85 | C |
| ATOM | 16940 | CG | HIS | B | 491 | 31.001 | 81.580 | 12.603 | 1.00 | 13.12 | C |
| ATOM | 16941 | ND1 | HIS | B | 491 | 30.367 | 81.021 | 13.684 | 1.00 | 15.36 | N |
| ATOM | 16943 | CE1 | HIS | B | 491 | 31.268 | 80.647 | 14.576 | 1.00 | 15.22 | C |
| ATOM | 16945 | NE2 | HIS | B | 491 | 32.470 | 80.874 | 14.079 | 1.00 | 13.86 | N |
| ATOM | 16947 | CD2 | HIS | B | 491 | 32.338 | 81.509 | 12.860 | 1.00 | 12.01 | C |
| ATOM | 16949 | C | HIS | B | 491 | 28.765 | 81.227 | 9.502 | 1.00 | 12.92 | C |
| ATOM | 16950 | O | HIS | B | 491 | 27.923 | 82.098 | 9.724 | 1.00 | 13.77 | O |

| ATOM | 16952 | N | VAL | B | 492 | 28.782 | 80.520 | 8.401 | 1.00 | 12.61 | N |
|------|-------|-----|-----|---|-----|--------|--------|-------|------|-------|----|
| ATOM | 16953 | CA | VAL | B | 492 | 27.844 | 80.742 | 7.281 | 1.00 | 12.02 | C |
| ATOM | 16955 | CB | VAL | B | 492 | 28.262 | 79.802 | 6.087 | 1.00 | 12.72 | C |
| ATOM | 16957 | CG1 | VAL | B | 492 | 27.228 | 79.833 | 4.952 | 1.00 | 14.31 | C |
| ATOM | 16961 | CG2 | VAL | B | 492 | 29.628 | 80.178 | 5.616 | 1.00 | 14.47 | C |
| ATOM | 16965 | C | VAL | B | 492 | 26.397 | 80.451 | 7.723 | 1.00 | 12.09 | C |
| ATOM | 16966 | O | VAL | B | 492 | 26.125 | 79.416 | 8.323 | 1.00 | 15.04 | O |
| ATOM | 16968 | N | GLN | B | 493 | 25.515 | 81.402 | 7.401 | 1.00 | 12.37 | N |
| ATOM | 16969 | CA | GLN | B | 493 | 24.092 | 81.362 | 7.679 | 1.00 | 12.47 | C |
| ATOM | 16971 | CB | GLN | B | 493 | 23.592 | 82.662 | 8.279 | 1.00 | 12.62 | C |
| ATOM | 16974 | CG | GLN | B | 493 | 24.321 | 83.046 | 9.558 | 1.00 | 13.97 | C |
| ATOM | 16977 | CD | GLN | B | 493 | 24.099 | 81.990 | 10.652 | 1.00 | 15.90 | C |
| ATOM | 16978 | OE1 | GLN | B | 493 | 22.951 | 81.547 | 10.886 | 1.00 | 15.69 | O |
| ATOM | 16979 | NE2 | GLN | B | 493 | 25.206 | 81.539 | 11.296 | 1.00 | 14.14 | N |
| ATOM | 16982 | C | GLN | B | 493 | 23.335 | 81.104 | 6.372 | 1.00 | 12.52 | C |
| ATOM | 16983 | O | GLN | B | 493 | 23.788 | 81.502 | 5.312 | 1.00 | 13.68 | O |
| ATOM | 16985 | N | PRO | B | 494 | 22.135 | 80.550 | 6.482 | 1.00 | 13.54 | N |
| ATOM | 16986 | CA | PRO | B | 494 | 21.250 | 80.276 | 5.315 | 1.00 | 15.26 | C |
| ATOM | 16988 | CB | PRO | B | 494 | 20.190 | 79.350 | 5.930 | 1.00 | 15.44 | C |
| ATOM | 16991 | CG | PRO | B | 494 | 20.106 | 79.794 | 7.297 | 1.00 | 14.59 | C |
| ATOM | 16994 | CD | PRO | B | 494 | 21.513 | 80.039 | 7.716 | 1.00 | 13.56 | C |
| ATOM | 16997 | C | PRO | B | 494 | 20.577 | 81.483 | 4.707 | 1.00 | 17.49 | C |
| ATOM | 16998 | O | PRO | B | 494 | 19.314 | 81.581 | 4.742 | 1.00 | 21.01 | O |
| ATOM | 16999 | N | ALA | B | 495 | 21.345 | 82.321 | 4.047 | 1.00 | 17.15 | N |
| ATOM | 17000 | CA | ALA | B | 495 | 20.872 | 83.591 | 3.615 | 1.00 | 17.33 | C |
| ATOM | 17002 | CB | ALA | B | 495 | 22.063 | 84.535 | 3.331 | 1.00 | 17.01 | C |
| ATOM | 17006 | C | ALA | B | 495 | 19.922 | 83.613 | 2.445 | 1.00 | 17.35 | C |
| ATOM | 17007 | O | ALA | B | 495 | 20.008 | 82.826 | 1.498 | 1.00 | 15.79 | O |
| ATOM | 17009 | N | GLU | B | 496 | 19.025 | 84.583 | 2.491 | 1.00 | 18.36 | N |
| ATOM | 17010 | CA | GLU | B | 496 | 18.147 | 84.892 | 1.367 | 1.00 | 19.70 | C |
| ATOM | 17012 | CB | GLU | B | 496 | 18.980 | 85.395 | 0.190 | 1.00 | 20.75 | C |
| ATOM | 17015 | CG | GLU | B | 496 | 18.198 | 86.279 | -0.754 | 1.00 | 23.35 | C |
| ATOM | 17018 | CD | GLU | B | 496 | 18.258 | 85.791 | -2.181 | 1.00 | 25.90 | C |
| ATOM | 17019 | OE1 | GLU | B | 496 | 19.346 | 85.735 | -2.820 | 1.00 | 21.81 | O |
| ATOM | 17020 | OE2 | GLU | B | 496 | 17.188 | 85.435 | -2.653 | 1.00 | 31.11 | O |
| ATOM | 17021 | C | GLU | B | 496 | 17.242 | 83.732 | 0.918 | 1.00 | 19.45 | C |
| ATOM | 17022 | O | GLU | B | 496 | 17.327 | 83.283 | -0.209 | 1.00 | 18.95 | O |
| ATOM | 17024 | N | MSE | B | 497 | 16.394 | 83.222 | 1.827 | 1.00 | 19.93 | N |
| ATOM | 17025 | CA | MSE | B | 497 | 15.512 | 82.086 | 1.553 | 1.00 | 21.20 | C |
| ATOM | 17027 | CB | MSE | B | 497 | 14.462 | 82.411 | 0.484 | 1.00 | 21.56 | C |
| ATOM | 17030 | CG | MSE | B | 497 | 13.678 | 83.627 | 0.871 | 1.00 | 23.03 | C |
| ATOM | 17033 | SE | MSE | B | 497 | 12.225 | 83.958 | -0.434 | 1.00 | 33.51 | SE |
| ATOM | 17034 | CE | MSE | B | 497 | 11.439 | 82.230 | -0.793 | 1.00 | 29.60 | C |
| ATOM | 17038 | C | MSE | B | 497 | 16.295 | 80.850 | 1.163 | 1.00 | 18.21 | C |
| ATOM | 17039 | O | MSE | B | 497 | 15.806 | 80.002 | 0.376 | 1.00 | 17.63 | O |
| ATOM | 17041 | N | ALA | B | 498 | 17.500 | 80.766 | 1.730 | 1.00 | 16.09 | N |
| ATOM | 17042 | CA | ALA | B | 498 | 18.441 | 79.714 | 1.429 | 1.00 | 15.50 | C |
| ATOM | 17044 | CB | ALA | B | 498 | 17.920 | 78.372 | 1.905 | 1.00 | 15.75 | C |
| ATOM | 17048 | C | ALA | B | 498 | 18.858 | 79.666 | -0.047 | 1.00 | 15.20 | C |
| ATOM | 17049 | O | ALA | B | 498 | 19.566 | 78.722 | -0.454 | 1.00 | 14.24 | O |
| ATOM | 17051 | N | ASN | B | 499 | 18.534 | 80.704 | -0.852 | 1.00 | 13.73 | N |
| ATOM | 17052 | CA | ASN | B | 499 | 19.146 | 80.809 | -2.188 | 1.00 | 14.26 | C |
| ATOM | 17054 | CB | ASN | B | 499 | 18.644 | 82.033 | -3.001 | 1.00 | 12.99 | C |
| ATOM | 17057 | CG | ASN | B | 499 | 19.276 | 82.121 | -4.404 | 1.00 | 15.15 | C |
| ATOM | 17058 | OD1 | ASN | B | 499 | 19.268 | 81.142 | -5.170 | 1.00 | 19.77 | O |
| ATOM | 17059 | ND2 | ASN | B | 499 | 19.759 | 83.311 | -4.778 | 1.00 | 22.63 | N |
| ATOM | 17062 | C | ASN | B | 499 | 20.650 | 80.920 | -1.990 | 1.00 | 13.72 | C |

| | | | | | | | | | |
|---|---|---|---|---|---|---|---|---|---|
| ATOM | 17063 | O | ASN | B | 499 | 21.416 | 80.315 | -2.723 | 1.00 14.58 | O |
| ATOM | 17065 | N | GLN | B | 500 | 21.067 | 81.686 | -0.981 | 1.00 12.17 | N |
| ATOM | 17066 | CA | GLN | B | 500 | 22.483 | 81.904 | -0.712 | 1.00 13.37 | C |
| ATOM | 17068 | CB | GLN | B | 500 | 22.796 | 83.386 | -0.494 | 1.00 12.85 | C |
| ATOM | 17071 | CG | GLN | B | 500 | 22.251 | 84.279 | -1.629 | 1.00 11.50 | C |
| ATOM | 17074 | CD | GLN | B | 500 | 22.856 | 85.644 | -1.694 | 1.00 15.27 | C |
| ATOM | 17075 | OE1 | GLN | B | 500 | 23.988 | 85.875 | -1.291 | 1.00 17.54 | O |
| ATOM | 17076 | NE2 | GLN | B | 500 | 22.090 | 86.573 | -2.255 | 1.00 14.66 | N |
| ATOM | 17079 | C | GLN | B | 500 | 22.901 | 81.060 | 0.502 | 1.00 12.25 | C |
| ATOM | 17080 | O | GLN | B | 500 | 23.620 | 81.530 | 1.397 | 1.00 13.81 | O |
| ATOM | 17082 | N | ALA | B | 501 | 22.550 | 79.776 | 0.481 | 1.00 12.72 | N |
| ATOM | 17083 | CA | ALA | B | 501 | 22.767 | 78.934 | 1.650 | 1.00 12.00 | C |
| ATOM | 17085 | CB | ALA | B | 501 | 22.054 | 77.630 | 1.512 | 1.00 12.17 | C |
| ATOM | 17089 | C | ALA | B | 501 | 24.260 | 78.704 | 1.961 | 1.00 12.66 | C |
| ATOM | 17090 | O | ALA | B | 501 | 24.620 | 78.369 | 3.071 | 1.00 13.07 | O |
| ATOM | 17092 | N | VAL | B | 502 | 25.088 | 78.770 | 0.924 | 1.00 11.41 | N |
| ATOM | 17093 | CA | VAL | B | 502 | 26.530 | 78.917 | 1.082 | 1.00 12.51 | C |
| ATOM | 17095 | CB | VAL | B | 502 | 27.352 | 77.832 | 0.372 | 1.00 12.71 | C |
| ATOM | 17097 | CG1 | VAL | B | 502 | 27.272 | 76.496 | 1.148 | 1.00 11.51 | C |
| ATOM | 17101 | CG2 | VAL | B | 502 | 26.939 | 77.650 | -1.061 | 1.00 14.42 | C |
| ATOM | 17105 | C | VAL | B | 502 | 26.886 | 80.335 | 0.629 | 1.00 12.37 | C |
| ATOM | 17106 | O | VAL | B | 502 | 26.473 | 80.794 | -0.441 | 1.00 11.77 | O |
| ATOM | 17108 | N | ASN | B | 503 | 27.694 | 81.012 | 1.442 | 1.00 11.83 | N |
| ATOM | 17109 | CA | ASN | B | 503 | 28.170 | 82.379 | 1.158 | 1.00 10.39 | C |
| ATOM | 17111 | CB | ASN | B | 503 | 27.228 | 83.442 | 1.670 | 1.00 11.24 | C |
| ATOM | 17114 | CG | ASN | B | 503 | 26.791 | 83.171 | 3.100 | 1.00 9.99 | C |
| ATOM | 17115 | OD1 | ASN | B | 503 | 27.452 | 83.596 | 4.038 | 1.00 11.50 | O |
| ATOM | 17116 | ND2 | ASN | B | 503 | 25.633 | 82.550 | 3.247 | 1.00 12.25 | N |
| ATOM | 17119 | C | ASN | B | 503 | 29.567 | 82.499 | 1.767 | 1.00 11.03 | C |
| ATOM | 17120 | O | ASN | B | 503 | 29.810 | 81.922 | 2.822 | 1.00 10.51 | O |
| ATOM | 17122 | N | SER | B | 504 | 30.474 | 83.196 | 1.071 | 1.00 11.15 | N |
| ATOM | 17123 | CA | SER | B | 504 | 31.905 | 83.137 | 1.387 | 1.00 10.95 | C |
| ATOM | 17125 | CB | SER | B | 504 | 32.791 | 83.660 | 0.252 | 1.00 11.63 | C |
| ATOM | 17128 | OG | SER | B | 504 | 32.764 | 85.066 | 0.199 | 1.00 12.46 | O |
| ATOM | 17130 | C | SER | B | 504 | 32.336 | 83.859 | 2.676 | 1.00 11.13 | C |
| ATOM | 17131 | O | SER | B | 504 | 33.423 | 83.511 | 3.249 | 1.00 12.68 | O |
| ATOM | 17133 | N | LEU | B | 505 | 31.622 | 84.930 | 3.029 | 1.00 10.03 | N |
| ATOM | 17134 | CA | LEU | B | 505 | 32.010 | 85.789 | 4.160 | 1.00 10.58 | C |
| ATOM | 17136 | CB | LEU | B | 505 | 31.903 | 85.044 | 5.495 | 1.00 11.32 | C |
| ATOM | 17139 | CG | LEU | B | 505 | 30.546 | 84.424 | 5.785 | 1.00 10.19 | C |
| ATOM | 17141 | CD1 | LEU | B | 505 | 30.701 | 83.618 | 7.077 | 1.00 13.29 | C |
| ATOM | 17145 | CD2 | LEU | B | 505 | 29.525 | 85.574 | 5.874 | 1.00 11.32 | C |
| ATOM | 17149 | C | LEU | B | 505 | 33.421 | 86.411 | 3.977 | 1.00 10.19 | C |
| ATOM | 17150 | O | LEU | B | 505 | 34.080 | 86.821 | 4.964 | 1.00 12.49 | O |
| ATOM | 17152 | N | ALA | B | 506 | 33.829 | 86.602 | 2.713 | 1.00 11.35 | N |
| ATOM | 17153 | CA | ALA | B | 506 | 35.191 | 87.067 | 2.436 | 1.00 10.81 | C |
| ATOM | 17155 | CB | ALA | B | 506 | 35.464 | 87.120 | 0.957 | 1.00 12.06 | C |
| ATOM | 17159 | C | ALA | B | 506 | 35.435 | 88.450 | 3.053 | 1.00 11.48 | C |
| ATOM | 17160 | O | ALA | B | 506 | 36.521 | 88.688 | 3.554 | 1.00 11.76 | O |
| ATOM | 17162 | N | LEU | B | 507 | 34.488 | 89.392 | 2.921 | 1.00 12.31 | N |
| ATOM | 17163 | CA | LEU | B | 507 | 34.762 | 90.755 | 3.386 | 1.00 12.49 | C |
| ATOM | 17165 | CB | LEU | B | 507 | 33.697 | 91.776 | 2.951 | 1.00 13.59 | C |
| ATOM | 17168 | CG | LEU | B | 507 | 34.108 | 93.199 | 3.358 | 1.00 13.92 | C |
| ATOM | 17170 | CD1 | LEU | B | 507 | 35.441 | 93.716 | 2.725 | 1.00 15.50 | C |
| ATOM | 17174 | CD2 | LEU | B | 507 | 32.977 | 94.105 | 2.996 | 1.00 17.73 | C |
| ATOM | 17178 | C | LEU | B | 507 | 34.956 | 90.784 | 4.915 | 1.00 12.10 | C |
| ATOM | 17179 | O | LEU | B | 507 | 35.793 | 91.513 | 5.457 | 1.00 13.20 | O |

| ATOM | 17181 | N   | ILE B 508 | 34.100 | 90.021 | 5.590  | 1.00 | 12.15 | N |
|------|-------|-----|-----------|--------|--------|--------|------|-------|---|
| ATOM | 17182 | CA  | ILE B 508 | 34.218 | 89.910 | 7.087  | 1.00 | 12.81 | C |
| ATOM | 17184 | CB  | ILE B 508 | 33.095 | 89.132 | 7.713  | 1.00 | 12.96 | C |
| ATOM | 17186 | CG1 | ILE B 508 | 31.725 | 89.770 | 7.438  | 1.00 | 13.42 | C |
| ATOM | 17189 | CD1 | ILE B 508 | 30.541 | 88.862 | 7.766  | 1.00 | 15.33 | C |
| ATOM | 17193 | CG2 | ILE B 508 | 33.291 | 89.016 | 9.242  | 1.00 | 14.25 | C |
| ATOM | 17197 | C   | ILE B 508 | 35.586 | 89.302 | 7.435  | 1.00 | 12.23 | C |
| ATOM | 17198 | O   | ILE B 508 | 36.326 | 89.775 | 8.308  | 1.00 | 12.92 | O |
| ATOM | 17200 | N   | SER B 509 | 35.907 | 88.220 | 6.735  | 1.00 | 12.72 | N |
| ATOM | 17201 | CA  | SER B 509 | 37.229 | 87.612 | 6.964  | 1.00 | 11.58 | C |
| ATOM | 17203 | CB  | SER B 509 | 37.410 | 86.350 | 6.119  | 1.00 | 12.71 | C |
| ATOM | 17206 | OG  | SER B 509 | 38.548 | 85.650 | 6.581  | 1.00 | 13.89 | O |
| ATOM | 17208 | C   | SER B 509 | 38.362 | 88.650 | 6.705  | 1.00 | 11.34 | C |
| ATOM | 17209 | O   | SER B 509 | 39.303 | 88.765 | 7.521  | 1.00 | 12.29 | O |
| ATOM | 17211 | N   | ALA B 510 | 38.281 | 89.396 | 5.583  | 1.00 | 10.75 | N |
| ATOM | 17212 | CA  | ALA B 510 | 39.287 | 90.421 | 5.229  | 1.00 | 11.40 | C |
| ATOM | 17214 | CB  | ALA B 510 | 38.984 | 91.004 | 3.916  | 1.00 | 12.40 | C |
| ATOM | 17218 | C   | ALA B 510 | 39.446 | 91.476 | 6.329  | 1.00 | 11.47 | C |
| ATOM | 17219 | O   | ALA B 510 | 40.550 | 91.941 | 6.660  | 1.00 | 11.84 | O |
| ATOM | 17221 | N   | ARG B 511 | 38.299 | 91.876 | 6.889  | 1.00 | 11.62 | N |
| ATOM | 17222 | CA  | ARG B 511 | 38.270 | 92.836 | 7.989  | 1.00 | 12.49 | C |
| ATOM | 17224 | CB  | ARG B 511 | 36.845 | 93.214 | 8.356  | 1.00 | 12.20 | C |
| ATOM | 17227 | CG  | ARG B 511 | 36.173 | 94.190 | 7.378  | 1.00 | 12.85 | C |
| ATOM | 17230 | CD  | ARG B 511 | 34.722 | 94.466 | 7.647  | 1.00 | 11.94 | C |
| ATOM | 17233 | NE  | ARG B 511 | 34.561 | 94.650 | 9.069  | 1.00 | 13.17 | N |
| ATOM | 17235 | CZ  | ARG B 511 | 33.669 | 94.046 | 9.844  | 1.00 | 14.09 | C |
| ATOM | 17236 | NH1 | ARG B 511 | 32.748 | 93.195 | 9.369  | 1.00 | 12.54 | N |
| ATOM | 17239 | NH2 | ARG B 511 | 33.767 | 94.274 | 11.141 | 1.00 | 14.23 | N |
| ATOM | 17242 | C   | ARG B 511 | 39.022 | 92.307 | 9.174  | 1.00 | 13.27 | C |
| ATOM | 17243 | O   | ARG B 511 | 39.833 | 93.053 | 9.786  | 1.00 | 13.18 | O |
| ATOM | 17245 | N   | ARG B 512 | 38.775 | 91.045 | 9.512  | 1.00 | 12.18 | N |
| ATOM | 17246 | CA  | ARG B 512 | 39.475 | 90.491 | 10.681 | 1.00 | 12.21 | C |
| ATOM | 17248 | CB  | ARG B 512 | 38.839 | 89.162 | 11.113 | 1.00 | 13.13 | C |
| ATOM | 17251 | CG  | ARG B 512 | 37.410 | 89.244 | 11.580 | 1.00 | 12.26 | C |
| ATOM | 17254 | CD  | ARG B 512 | 37.255 | 90.276 | 12.700 | 1.00 | 15.14 | C |
| ATOM | 17257 | NE  | ARG B 512 | 35.901 | 90.298 | 13.224 | 1.00 | 16.64 | N |
| ATOM | 17259 | CZ  | ARG B 512 | 35.263 | 91.338 | 13.696 | 1.00 | 12.65 | C |
| ATOM | 17260 | NH1 | ARG B 512 | 35.716 | 92.598 | 13.517 | 1.00 | 15.27 | N |
| ATOM | 17263 | NH2 | ARG B 512 | 34.040 | 91.113 | 14.199 | 1.00 | 13.47 | N |
| ATOM | 17266 | C   | ARG B 512 | 40.967 | 90.357 | 10.404 | 1.00 | 12.50 | C |
| ATOM | 17267 | O   | ARG B 512 | 41.802 | 90.680 | 11.279 | 1.00 | 13.87 | O |
| ATOM | 17269 | N   | THR B 513 | 41.344 | 89.962 | 9.193  | 1.00 | 12.47 | N |
| ATOM | 17270 | CA  | THR B 513 | 42.782 | 89.842 | 8.882  | 1.00 | 11.38 | C |
| ATOM | 17272 | CB  | THR B 513 | 42.954 | 89.138 | 7.526  | 1.00 | 10.73 | C |
| ATOM | 17274 | OG1 | THR B 513 | 42.268 | 87.884 | 7.617  | 1.00 | 11.03 | O |
| ATOM | 17276 | CG2 | THR B 513 | 44.445 | 88.996 | 7.169  | 1.00 | 11.54 | C |
| ATOM | 17280 | C   | THR B 513 | 43.440 | 91.245 | 8.890  | 1.00 | 11.89 | C |
| ATOM | 17281 | O   | THR B 513 | 44.584 | 91.353 | 9.281  | 1.00 | 12.28 | O |
| ATOM | 17283 | N   | THR B 514 | 42.732 | 92.322 | 8.459  | 1.00 | 11.15 | N |
| ATOM | 17284 | CA  | THR B 514 | 43.254 | 93.671 | 8.500  | 1.00 | 11.71 | C |
| ATOM | 17286 | CB  | THR B 514 | 42.252 | 94.612 | 7.813  | 1.00 | 12.13 | C |
| ATOM | 17288 | OG1 | THR B 514 | 42.117 | 94.247 | 6.425  | 1.00 | 10.84 | O |
| ATOM | 17290 | CG2 | THR B 514 | 42.692 | 96.015 | 7.932  | 1.00 | 13.89 | C |
| ATOM | 17294 | C   | THR B 514 | 43.510 | 94.060 | 9.937  | 1.00 | 12.64 | C |
| ATOM | 17295 | O   | THR B 514 | 44.525 | 94.716 | 10.223 | 1.00 | 12.68 | O |
| ATOM | 17297 | N   | GLU B 515 | 42.621 | 93.646 | 10.864 | 1.00 | 12.34 | N |
| ATOM | 17298 | CA  | GLU B 515 | 42.811 | 93.968 | 12.278 | 1.00 | 13.86 | C |

| ATOM | 17300 | CB | GLU | B | 515 | 41.580 | 93.637 | 13.087 | 1.00 | 14.08 | C |
| --- | --- | --- | --- | --- | --- | --- | --- | --- | --- | --- | --- |
| ATOM | 17303 | CG | GLU | B | 515 | 41.737 | 94.128 | 14.527 | 1.00 | 13.78 | C |
| ATOM | 17306 | CD | GLU | B | 515 | 40.497 | 94.060 | 15.416 | 1.00 | 18.14 | C |
| ATOM | 17307 | OE1 | GLU | B | 515 | 39.364 | 93.704 | 14.946 | 1.00 | 18.13 | O |
| ATOM | 17308 | OE2 | GLU | B | 515 | 40.651 | 94.378 | 16.635 | 1.00 | 17.24 | O |
| ATOM | 17309 | C | GLU | B | 515 | 44.030 | 93.192 | 12.798 | 1.00 | 13.09 | C |
| ATOM | 17310 | O | GLU | B | 515 | 44.842 | 93.741 | 13.559 | 1.00 | 13.69 | O |
| ATOM | 17312 | N | SER | B | 516 | 44.184 | 91.928 | 12.387 | 1.00 | 13.05 | N |
| ATOM | 17313 | CA | SER | B | 516 | 45.370 | 91.176 | 12.791 | 1.00 | 12.35 | C |
| ATOM | 17315 | CB | SER | B | 516 | 45.332 | 89.733 | 12.324 | 1.00 | 13.23 | C |
| ATOM | 17318 | OG | SER | B | 516 | 44.307 | 89.051 | 13.034 | 1.00 | 13.12 | O |
| ATOM | 17320 | C | SER | B | 516 | 46.648 | 91.837 | 12.264 | 1.00 | 12.32 | C |
| ATOM | 17321 | O | SER | B | 516 | 47.655 | 91.909 | 12.978 | 1.00 | 12.65 | O |
| ATOM | 17323 | N | ASN | B | 517 | 46.618 | 92.399 | 11.046 | 1.00 | 12.58 | N |
| ATOM | 17324 | CA | ASN | B | 517 | 47.781 | 93.164 | 10.566 | 1.00 | 12.09 | C |
| ATOM | 17326 | CB | ASN | B | 517 | 47.658 | 93.753 | 9.150 | 1.00 | 13.07 | C |
| ATOM | 17329 | CG | ASN | B | 517 | 47.816 | 92.735 | 8.060 | 1.00 | 14.56 | C |
| ATOM | 17330 | OD1 | ASN | B | 517 | 48.561 | 91.771 | 8.207 | 1.00 | 13.43 | O |
| ATOM | 17331 | ND2 | ASN | B | 517 | 47.181 | 93.001 | 6.892 | 1.00 | 11.57 | N |
| ATOM | 17334 | C | ASN | B | 517 | 48.112 | 94.279 | 11.518 | 1.00 | 12.02 | C |
| ATOM | 17335 | O | ASN | B | 517 | 49.284 | 94.519 | 11.822 | 1.00 | 13.33 | O |
| ATOM | 17337 | N | ASP | B | 518 | 47.092 | 94.966 | 12.011 | 1.00 | 12.71 | N |
| ATOM | 17338 | CA | ASP | B | 518 | 47.253 | 96.123 | 12.862 | 1.00 | 12.81 | C |
| ATOM | 17340 | CB | ASP | B | 518 | 45.889 | 96.757 | 13.122 | 1.00 | 14.71 | C |
| ATOM | 17343 | CG | ASP | B | 518 | 45.994 | 98.184 | 13.695 | 1.00 | 17.29 | C |
| ATOM | 17344 | OD1 | ASP | B | 518 | 47.010 | 98.919 | 13.422 | 1.00 | 19.26 | O |
| ATOM | 17345 | OD2 | ASP | B | 518 | 45.017 | 98.596 | 14.375 | 1.00 | 20.00 | O |
| ATOM | 17346 | C | ASP | B | 518 | 47.881 | 95.699 | 14.190 | 1.00 | 11.96 | C |
| ATOM | 17347 | O | ASP | B | 518 | 48.872 | 96.277 | 14.685 | 1.00 | 13.65 | O |
| ATOM | 17349 | N | VAL | B | 519 | 47.302 | 94.663 | 14.791 | 1.00 | 12.05 | N |
| ATOM | 17350 | CA | VAL | B | 519 | 47.833 | 94.162 | 16.075 | 1.00 | 12.20 | C |
| ATOM | 17352 | CB | VAL | B | 519 | 46.886 | 93.136 | 16.668 | 1.00 | 13.00 | C |
| ATOM | 17354 | CG1 | VAL | B | 519 | 47.436 | 92.553 | 17.963 | 1.00 | 12.45 | C |
| ATOM | 17358 | CG2 | VAL | B | 519 | 45.530 | 93.817 | 16.872 | 1.00 | 13.71 | C |
| ATOM | 17362 | C | VAL | B | 519 | 49.232 | 93.644 | 15.931 | 1.00 | 12.29 | C |
| ATOM | 17363 | O | VAL | B | 519 | 50.088 | 93.882 | 16.821 | 1.00 | 12.99 | O |
| ATOM | 17365 | N | LEU | B | 520 | 49.503 | 92.919 | 14.842 | 1.00 | 12.56 | N |
| ATOM | 17366 | CA | LEU | B | 520 | 50.875 | 92.411 | 14.626 | 1.00 | 12.29 | C |
| ATOM | 17368 | CB | LEU | B | 520 | 50.980 | 91.500 | 13.406 | 1.00 | 13.18 | C |
| ATOM | 17371 | CG | LEU | B | 520 | 52.344 | 90.823 | 13.198 | 1.00 | 13.72 | C |
| ATOM | 17373 | CD1 | LEU | B | 520 | 52.928 | 90.175 | 14.445 | 1.00 | 15.45 | C |
| ATOM | 17377 | CD2 | LEU | B | 520 | 52.312 | 89.742 | 12.114 | 1.00 | 13.56 | C |
| ATOM | 17381 | C | LEU | B | 520 | 51.810 | 93.604 | 14.460 | 1.00 | 12.47 | C |
| ATOM | 17382 | O | LEU | B | 520 | 52.965 | 93.524 | 14.894 | 1.00 | 12.63 | O |
| ATOM | 17384 | N | SER | B | 521 | 51.367 | 94.701 | 13.817 | 1.00 | 12.57 | N |
| ATOM | 17385 | CA | SER | B | 521 | 52.231 | 95.888 | 13.652 | 1.00 | 12.32 | C |
| ATOM | 17387 | CB | SER | B | 521 | 51.558 | 96.928 | 12.780 | 1.00 | 12.37 | C |
| ATOM | 17390 | OG | SER | B | 521 | 51.296 | 96.412 | 11.458 | 1.00 | 14.06 | O |
| ATOM | 17392 | C | SER | B | 521 | 52.578 | 96.483 | 15.001 | 1.00 | 11.37 | C |
| ATOM | 17393 | O | SER | B | 521 | 53.688 | 96.961 | 15.204 | 1.00 | 12.63 | O |
| ATOM | 17395 | N | LEU | B | 522 | 51.627 | 96.463 | 15.928 | 1.00 | 11.35 | N |
| ATOM | 17396 | CA | LEU | B | 522 | 51.916 | 96.975 | 17.285 | 1.00 | 12.23 | C |
| ATOM | 17398 | CB | LEU | B | 522 | 50.650 | 96.910 | 18.160 | 1.00 | 12.63 | C |
| ATOM | 17401 | CG | LEU | B | 522 | 49.518 | 97.884 | 17.808 | 1.00 | 12.98 | C |
| ATOM | 17403 | CD1 | LEU | B | 522 | 48.222 | 97.560 | 18.523 | 1.00 | 12.97 | C |
| ATOM | 17407 | CD2 | LEU | B | 522 | 49.940 | 99.304 | 18.113 | 1.00 | 15.44 | C |
| ATOM | 17411 | C | LEU | B | 522 | 52.982 | 96.093 | 17.943 | 1.00 | 13.34 | C |

| ATOM | 17412 | O | LEU | B | 522 | 53.919 | 96.591 | 18.584 | 1.00 | 12.60 | O |
|------|-------|-----|-----|---|-----|--------|--------|--------|------|-------|---|
| ATOM | 17414 | N | LEU | B | 523 | 52.818 | 94.785 | 17.809 | 1.00 | 12.40 | N |
| ATOM | 17415 | CA | LEU | B | 523 | 53.759 | 93.818 | 18.396 | 1.00 | 13.04 | C |
| ATOM | 17417 | CB | LEU | B | 523 | 53.215 | 92.407 | 18.224 | 1.00 | 13.45 | C |
| ATOM | 17420 | CG | LEU | B | 523 | 54.065 | 91.270 | 18.741 | 1.00 | 12.38 | C |
| ATOM | 17422 | CD1 | LEU | B | 523 | 54.500 | 91.416 | 20.136 | 1.00 | 12.41 | C |
| ATOM | 17426 | CD2 | LEU | B | 523 | 53.386 | 89.891 | 18.451 | 1.00 | 14.74 | C |
| ATOM | 17430 | C | LEU | B | 523 | 55.145 | 93.969 | 17.785 | 1.00 | 12.90 | C |
| ATOM | 17431 | O | LEU | B | 523 | 56.169 | 93.959 | 18.507 | 1.00 | 13.35 | O |
| ATOM | 17433 | N | LEU | B | 524 | 55.206 | 94.028 | 16.454 | 1.00 | 12.70 | N |
| ATOM | 17434 | CA | LEU | B | 524 | 56.518 | 94.065 | 15.816 | 1.00 | 12.59 | C |
| ATOM | 17436 | CB | LEU | B | 524 | 56.425 | 93.692 | 14.331 | 1.00 | 12.28 | C |
| ATOM | 17439 | CG | LEU | B | 524 | 55.965 | 92.248 | 14.114 | 1.00 | 14.33 | C |
| ATOM | 17441 | CD1 | LEU | B | 524 | 56.217 | 91.908 | 12.658 | 1.00 | 13.39 | C |
| ATOM | 17445 | CD2 | LEU | B | 524 | 56.643 | 91.215 | 15.012 | 1.00 | 15.34 | C |
| ATOM | 17449 | C | LEU | B | 524 | 57.199 | 95.443 | 16.042 | 1.00 | 13.41 | C |
| ATOM | 17450 | O | LEU | B | 524 | 58.438 | 95.524 | 16.154 | 1.00 | 13.67 | O |
| ATOM | 17452 | N | ALA | B | 525 | 56.402 | 96.514 | 16.140 | 1.00 | 12.67 | N |
| ATOM | 17453 | CA | ALA | B | 525 | 56.958 | 97.863 | 16.516 | 1.00 | 13.07 | C |
| ATOM | 17455 | CB | ALA | B | 525 | 55.933 | 98.925 | 16.468 | 1.00 | 14.20 | C |
| ATOM | 17459 | C | ALA | B | 525 | 57.592 | 97.769 | 17.925 | 1.00 | 12.68 | C |
| ATOM | 17460 | O | ALA | B | 525 | 58.644 | 98.303 | 18.176 | 1.00 | 12.94 | O |
| ATOM | 17462 | N | THR | B | 526 | 56.881 | 97.134 | 18.822 | 1.00 | 12.53 | N |
| ATOM | 17463 | CA | THR | B | 526 | 57.371 | 96.901 | 20.193 | 1.00 | 12.10 | C |
| ATOM | 17465 | CB | THR | B | 526 | 56.265 | 96.199 | 20.993 | 1.00 | 14.43 | C |
| ATOM | 17467 | OG1 | THR | B | 526 | 55.167 | 97.103 | 21.121 | 1.00 | 12.51 | O |
| ATOM | 17469 | CG2 | THR | B | 526 | 56.710 | 95.717 | 22.365 | 1.00 | 13.61 | C |
| ATOM | 17473 | C | THR | B | 526 | 58.695 | 96.108 | 20.217 | 1.00 | 12.61 | C |
| ATOM | 17474 | O | THR | B | 526 | 59.677 | 96.446 | 20.897 | 1.00 | 12.30 | O |
| ATOM | 17476 | N | HIS | B | 527 | 58.705 | 94.999 | 19.507 | 1.00 | 13.09 | N |
| ATOM | 17477 | CA | HIS | B | 527 | 59.900 | 94.162 | 19.419 | 1.00 | 12.62 | C |
| ATOM | 17479 | CB | HIS | B | 527 | 59.558 | 92.925 | 18.580 | 1.00 | 13.29 | C |
| ATOM | 17482 | CG | HIS | B | 527 | 60.634 | 91.857 | 18.537 | 1.00 | 11.06 | C |
| ATOM | 17483 | ND1 | HIS | B | 527 | 60.467 | 90.658 | 17.869 | 1.00 | 14.18 | N |
| ATOM | 17485 | CE1 | HIS | B | 527 | 61.571 | 89.935 | 18.010 | 1.00 | 14.99 | C |
| ATOM | 17487 | NE2 | HIS | B | 527 | 62.448 | 90.620 | 18.720 | 1.00 | 13.37 | N |
| ATOM | 17489 | CD2 | HIS | B | 527 | 61.884 | 91.822 | 19.069 | 1.00 | 13.34 | C |
| ATOM | 17491 | C | HIS | B | 527 | 61.062 | 94.990 | 18.850 | 1.00 | 11.93 | C |
| ATOM | 17492 | O | HIS | B | 527 | 62.213 | 94.905 | 19.318 | 1.00 | 13.84 | O |
| ATOM | 17494 | N | LEU | B | 528 | 60.834 | 95.692 | 17.755 | 1.00 | 11.79 | N |
| ATOM | 17495 | CA | LEU | B | 528 | 61.897 | 96.517 | 17.163 | 1.00 | 11.27 | C |
| ATOM | 17497 | CB | LEU | B | 528 | 61.382 | 97.194 | 15.890 | 1.00 | 11.50 | C |
| ATOM | 17500 | CG | LEU | B | 528 | 62.349 | 98.024 | 15.050 | 1.00 | 11.44 | C |
| ATOM | 17502 | CD1 | LEU | B | 528 | 63.667 | 97.273 | 14.803 | 1.00 | 12.22 | C |
| ATOM | 17506 | CD2 | LEU | B | 528 | 61.687 | 98.385 | 13.693 | 1.00 | 12.63 | C |
| ATOM | 17510 | C | LEU | B | 528 | 62.416 | 97.567 | 18.146 | 1.00 | 12.09 | C |
| ATOM | 17511 | O | LEU | B | 528 | 63.631 | 97.727 | 18.291 | 1.00 | 11.86 | O |
| ATOM | 17513 | N | TYR | B | 529 | 61.507 | 98.222 | 18.861 | 1.00 | 11.58 | N |
| ATOM | 17514 | CA | TYR | B | 529 | 61.926 | 99.172 | 19.907 | 1.00 | 11.95 | C |
| ATOM | 17516 | CB | TYR | B | 529 | 60.717 | 99.736 | 20.639 | 1.00 | 13.11 | C |
| ATOM | 17519 | CG | TYR | B | 529 | 61.119 | 100.615 | 21.796 | 1.00 | 12.68 | C |
| ATOM | 17520 | CD1 | TYR | B | 529 | 61.274 | 101.991 | 21.648 | 1.00 | 13.38 | C |
| ATOM | 17522 | CE1 | TYR | B | 529 | 61.672 | 102.770 | 22.714 | 1.00 | 12.92 | C |
| ATOM | 17524 | CZ | TYR | B | 529 | 61.914 | 102.188 | 23.943 | 1.00 | 12.85 | C |
| ATOM | 17525 | OH | TYR | B | 529 | 62.326 | 102.956 | 25.036 | 1.00 | 14.96 | O |
| ATOM | 17527 | CE2 | TYR | B | 529 | 61.754 | 100.857 | 24.102 | 1.00 | 12.19 | C |
| ATOM | 17529 | CD2 | TYR | B | 529 | 61.338 | 100.058 | 23.036 | 1.00 | 12.78 | C |

| ATOM | 17531 | C | TYR | B | 529 | 62.887 | 98.480 | 20.869 | 1.00 | 11.81 | C |
|------|-------|------|-----|---|-----|--------|--------|--------|------|-------|---|
| ATOM | 17532 | O | TYR | B | 529 | 63.969 | 98.998 | 21.179 | 1.00 | 12.44 | O |
| ATOM | 17534 | N | CYS | B | 530 | 62.473 | 97.308 | 21.349 | 1.00 | 11.68 | N |
| ATOM | 17535 | CA | CYS | B | 530 | 63.268 | 96.592 | 22.391 | 1.00 | 11.61 | C |
| ATOM | 17537 | CB | CYS | B | 530 | 62.496 | 95.502 | 23.023 | 1.00 | 12.28 | C |
| ATOM | 17540 | SG | CYS | B | 530 | 61.040 | 96.001 | 23.941 | 1.00 | 14.49 | S |
| ATOM | 17542 | C | CYS | B | 530 | 64.617 | 96.069 | 21.886 | 1.00 | 11.82 | C |
| ATOM | 17543 | O | CYS | B | 530 | 65.662 | 96.211 | 22.562 | 1.00 | 12.30 | O |
| ATOM | 17545 | N | VAL | B | 531 | 64.605 | 95.451 | 20.705 | 1.00 | 11.89 | N |
| ATOM | 17546 | CA | VAL | B | 531 | 65.837 | 94.844 | 20.192 | 1.00 | 12.34 | C |
| ATOM | 17548 | CB | VAL | B | 531 | 65.574 | 93.953 | 18.915 | 1.00 | 11.99 | C |
| ATOM | 17550 | CG1 | VAL | B | 531 | 65.448 | 94.832 | 17.661 | 1.00 | 13.33 | C |
| ATOM | 17554 | CG2 | VAL | B | 531 | 66.673 | 92.911 | 18.740 | 1.00 | 13.18 | C |
| ATOM | 17558 | C | VAL | B | 531 | 66.900 | 95.909 | 19.986 | 1.00 | 11.91 | C |
| ATOM | 17559 | O | VAL | B | 531 | 68.085 | 95.666 | 20.128 | 1.00 | 12.14 | O |
| ATOM | 17561 | N | LEU | B | 532 | 66.495 | 97.118 | 19.594 | 1.00 | 11.49 | N |
| ATOM | 17562 | CA | LEU | B | 532 | 67.488 | 98.178 | 19.355 | 1.00 | 12.01 | C |
| ATOM | 17564 | CB | LEU | B | 532 | 66.841 | 99.386 | 18.674 | 1.00 | 12.16 | C |
| ATOM | 17567 | CG | LEU | B | 532 | 66.276 | 99.053 | 17.306 | 1.00 | 12.67 | C |
| ATOM | 17569 | CD1 | LEU | B | 532 | 65.458 | 100.212 | 16.815 | 1.00 | 17.83 | C |
| ATOM | 17573 | CD2 | LEU | B | 532 | 67.365 | 98.618 | 16.276 | 1.00 | 16.41 | C |
| ATOM | 17577 | C | LEU | B | 532 | 68.118 | 98.618 | 20.689 | 1.00 | 11.46 | C |
| ATOM | 17578 | O | LEU | B | 532 | 69.329 | 98.825 | 20.754 | 1.00 | 13.92 | O |
| ATOM | 17580 | N | GLN | B | 533 | 67.285 | 98.726 | 21.728 | 1.00 | 13.23 | N |
| ATOM | 17581 | CA | GLN | B | 533 | 67.821 | 98.965 | 23.088 | 1.00 | 13.18 | C |
| ATOM | 17583 | CB | GLN | B | 533 | 66.729 | 99.074 | 24.126 | 1.00 | 13.64 | C |
| ATOM | 17586 | CG | GLN | B | 533 | 67.285 | 99.352 | 25.540 | 1.00 | 13.98 | C |
| ATOM | 17589 | CD | GLN | B | 533 | 67.555 | 100.817 | 25.873 | 1.00 | 14.42 | C |
| ATOM | 17590 | OE1 | GLN | B | 533 | 67.503 | 101.724 | 25.028 | 1.00 | 15.15 | O |
| ATOM | 17591 | NE2 | GLN | B | 533 | 67.882 | 101.048 | 27.156 | 1.00 | 12.32 | N |
| ATOM | 17594 | C | GLN | B | 533 | 68.782 | 97.883 | 23.482 | 1.00 | 12.69 | C |
| ATOM | 17595 | O | GLN | B | 533 | 69.898 | 98.184 | 23.961 | 1.00 | 13.49 | O |
| ATOM | 17597 | N | ALA | B | 534 | 68.390 | 96.621 | 23.278 | 1.00 | 11.63 | N |
| ATOM | 17598 | CA | ALA | B | 534 | 69.260 | 95.495 | 23.641 | 1.00 | 11.55 | C |
| ATOM | 17600 | CB | ALA | B | 534 | 68.546 | 94.189 | 23.359 | 1.00 | 12.28 | C |
| ATOM | 17604 | C | ALA | B | 534 | 70.579 | 95.554 | 22.877 | 1.00 | 12.03 | C |
| ATOM | 17605 | O | ALA | B | 534 | 71.656 | 95.322 | 23.427 | 1.00 | 11.74 | O |
| ATOM | 17607 | N | ILE | B | 535 | 70.499 | 95.901 | 21.584 | 1.00 | 12.33 | N |
| ATOM | 17608 | CA | ILE | B | 535 | 71.704 | 96.013 | 20.725 | 1.00 | 13.15 | C |
| ATOM | 17610 | CB | ILE | B | 535 | 71.322 | 96.332 | 19.282 | 1.00 | 12.20 | C |
| ATOM | 17612 | CG1 | ILE | B | 535 | 70.858 | 95.032 | 18.619 | 1.00 | 11.74 | C |
| ATOM | 17615 | CD1 | ILE | B | 535 | 70.083 | 95.203 | 17.321 | 1.00 | 14.72 | C |
| ATOM | 17619 | CG2 | ILE | B | 535 | 72.447 | 96.923 | 18.531 | 1.00 | 14.19 | C |
| ATOM | 17623 | C | ILE | B | 535 | 72.682 | 97.072 | 21.290 | 1.00 | 11.85 | C |
| ATOM | 17624 | O | ILE | B | 535 | 73.863 | 96.878 | 21.373 | 1.00 | 13.11 | O |
| ATOM | 17626 | N | ASP | B | 536 | 72.138 | 98.229 | 21.656 | 1.00 | 11.55 | N |
| ATOM | 17627 | CA | ASP | B | 536 | 72.956 | 99.272 | 22.238 | 1.00 | 12.07 | C |
| ATOM | 17629 | CB | ASP | B | 536 | 72.079 | 100.501 | 22.386 | 1.00 | 12.09 | C |
| ATOM | 17632 | CG | ASP | B | 536 | 71.931 | 101.261 | 21.102 | 1.00 | 14.51 | C |
| ATOM | 17633 | OD1 | ASP | B | 536 | 72.834 | 101.184 | 20.208 | 1.00 | 14.78 | O |
| ATOM | 17634 | OD2 | ASP | B | 536 | 70.919 | 102.025 | 20.967 | 1.00 | 14.51 | O |
| ATOM | 17635 | C | ASP | B | 536 | 73.564 | 98.831 | 23.581 | 1.00 | 12.06 | C |
| ATOM | 17636 | O | ASP | B | 536 | 74.712 | 99.136 | 23.858 | 1.00 | 13.35 | O |
| ATOM | 17638 | N | LEU | B | 537 | 72.804 | 98.128 | 24.413 | 1.00 | 11.02 | N |
| ATOM | 17639 | CA | LEU | B | 537 | 73.329 | 97.649 | 25.710 | 1.00 | 12.08 | C |
| ATOM | 17641 | CB | LEU | B | 537 | 72.208 | 97.130 | 26.604 | 1.00 | 12.17 | C |
| ATOM | 17644 | CG | LEU | B | 537 | 71.221 | 98.217 | 27.089 | 1.00 | 12.29 | C |

| | | | | | | | | | |
|---|---|---|---|---|---|---|---|---|---|
| ATOM | 17646 | CD1 | LEU | B | 537 | 70.023 | 97.570 | 27.846 | 1.00 16.80 | C |
| ATOM | 17650 | CD2 | LEU | B | 537 | 71.925 | 99.241 | 27.940 | 1.00 13.75 | C |
| ATOM | 17654 | C | LEU | B | 537 | 74.406 | 96.572 | 25.509 | 1.00 12.50 | C |
| ATOM | 17655 | O | LEU | B | 537 | 75.434 | 96.486 | 26.249 | 1.00 11.97 | O |
| ATOM | 17657 | N | ARG | B | 538 | 74.171 | 95.722 | 24.520 | 1.00 11.48 | N |
| ATOM | 17658 | CA | ARG | B | 538 | 75.191 | 94.749 | 24.188 | 1.00 12.74 | C |
| ATOM | 17660 | CB | ARG | B | 538 | 74.683 | 93.746 | 23.171 | 1.00 12.62 | C |
| ATOM | 17663 | CG | ARG | B | 538 | 75.601 | 92.520 | 23.056 | 1.00 11.86 | C |
| ATOM | 17666 | CD | ARG | B | 538 | 75.564 | 91.619 | 24.269 | 1.00 13.06 | C |
| ATOM | 17669 | NE | ARG | B | 538 | 74.375 | 90.758 | 24.306 | 1.00 12.07 | N |
| ATOM | 17671 | CZ | ARG | B | 538 | 74.055 | 89.940 | 25.311 | 1.00 11.60 | C |
| ATOM | 17672 | NH1 | ARG | B | 538 | 74.804 | 89.951 | 26.415 | 1.00 15.11 | N |
| ATOM | 17675 | NH2 | ARG | B | 538 | 73.026 | 89.142 | 25.210 | 1.00 13.62 | N |
| ATOM | 17678 | C | ARG | B | 538 | 76.483 | 95.399 | 23.698 | 1.00 12.62 | C |
| ATOM | 17679 | O | ARG | B | 538 | 77.608 | 94.981 | 24.007 | 1.00 12.76 | O |
| ATOM | 17681 | N | ALA | B | 539 | 76.328 | 96.452 | 22.906 | 1.00 11.45 | N |
| ATOM | 17682 | CA | ALA | B | 539 | 77.508 | 97.173 | 22.391 | 1.00 12.00 | C |
| ATOM | 17684 | CB | ALA | B | 539 | 77.084 | 98.197 | 21.394 | 1.00 12.55 | C |
| ATOM | 17688 | C | ALA | B | 539 | 78.298 | 97.810 | 23.538 | 1.00 11.96 | C |
| ATOM | 17689 | O | ALA | B | 539 | 79.547 | 97.774 | 23.487 | 1.00 11.79 | O |
| ATOM | 17691 | N | ILE | B | 540 | 77.589 | 98.379 | 24.530 | 1.00 12.53 | N |
| ATOM | 17692 | CA | ILE | B | 540 | 78.223 | 98.884 | 25.772 | 1.00 13.81 | C |
| ATOM | 17694 | CB | ILE | B | 540 | 77.172 | 99.527 | 26.730 | 1.00 14.11 | C |
| ATOM | 17696 | CG1 | ILE | B | 540 | 76.717 | 100.835 | 26.135 | 1.00 16.46 | C |
| ATOM | 17699 | CD1 | ILE | B | 540 | 75.417 | 101.404 | 26.782 | 1.00 16.69 | C |
| ATOM | 17703 | CG2 | ILE | B | 540 | 77.735 | 99.751 | 28.103 | 1.00 15.81 | C |
| ATOM | 17707 | C | ILE | B | 540 | 79.007 | 97.773 | 26.495 | 1.00 13.16 | C |
| ATOM | 17708 | O | ILE | B | 540 | 80.159 | 97.966 | 26.913 | 1.00 14.05 | O |
| ATOM | 17710 | N | GLU | B | 541 | 78.396 | 96.606 | 26.600 | 1.00 13.44 | N |
| ATOM | 17711 | CA | GLU | B | 541 | 79.072 | 95.452 | 27.180 | 1.00 14.44 | C |
| ATOM | 17713 | CB | GLU | B | 541 | 78.173 | 94.243 | 27.184 | 1.00 15.19 | C |
| ATOM | 17716 | CG | GLU | B | 541 | 78.833 | 92.959 | 27.605 | 1.00 16.39 | C |
| ATOM | 17719 | CD | GLU | B | 541 | 77.908 | 91.739 | 27.471 | 1.00 18.13 | C |
| ATOM | 17720 | OE1 | GLU | B | 541 | 76.671 | 91.882 | 27.429 | 1.00 17.17 | O |
| ATOM | 17721 | OE2 | GLU | B | 541 | 78.439 | 90.618 | 27.372 | 1.00 25.27 | O |
| ATOM | 17722 | C | GLU | B | 541 | 80.352 | 95.133 | 26.420 | 1.00 12.85 | C |
| ATOM | 17723 | O | GLU | B | 541 | 81.407 | 94.929 | 27.021 | 1.00 13.14 | O |
| ATOM | 17725 | N | PHE | B | 542 | 80.266 | 95.124 | 25.099 | 1.00 13.20 | N |
| ATOM | 17726 | CA | PHE | B | 542 | 81.454 | 94.870 | 24.270 | 1.00 13.39 | C |
| ATOM | 17728 | CB | PHE | B | 542 | 81.061 | 94.758 | 22.807 | 1.00 13.95 | C |
| ATOM | 17731 | CG | PHE | B | 542 | 80.473 | 93.421 | 22.424 | 1.00 15.16 | C |
| ATOM | 17732 | CD1 | PHE | B | 542 | 80.039 | 92.501 | 23.373 | 1.00 14.22 | C |
| ATOM | 17734 | CE1 | PHE | B | 542 | 79.465 | 91.258 | 22.984 | 1.00 16.99 | C |
| ATOM | 17736 | CZ | PHE | B | 542 | 79.363 | 90.967 | 21.633 | 1.00 17.19 | C |
| ATOM | 17738 | CE2 | PHE | B | 542 | 79.802 | 91.876 | 20.683 | 1.00 18.06 | C |
| ATOM | 17740 | CD2 | PHE | B | 542 | 80.357 | 93.094 | 21.078 | 1.00 17.43 | C |
| ATOM | 17742 | C | PHE | B | 542 | 82.546 | 95.929 | 24.429 | 1.00 13.87 | C |
| ATOM | 17743 | O | PHE | B | 542 | 83.732 | 95.585 | 24.544 | 1.00 13.45 | O |
| ATOM | 17745 | N | GLU | B | 543 | 82.157 | 97.212 | 24.465 | 1.00 13.43 | N |
| ATOM | 17746 | CA | GLU | B | 543 | 83.145 | 98.287 | 24.688 | 1.00 13.52 | C |
| ATOM | 17748 | CB | GLU | B | 543 | 82.524 | 99.679 | 24.577 | 1.00 13.87 | C |
| ATOM | 17751 | CG | GLU | B | 543 | 82.035 | 99.978 | 23.196 | 1.00 14.82 | C |
| ATOM | 17754 | CD | GLU | B | 543 | 83.154 | 100.033 | 22.200 | 1.00 18.05 | C |
| ATOM | 17755 | OE1 | GLU | B | 543 | 84.099 | 100.814 | 22.418 | 1.00 20.70 | O |
| ATOM | 17756 | OE2 | GLU | B | 543 | 83.131 | 99.274 | 21.215 | 1.00 19.22 | O |
| ATOM | 17757 | C | GLU | B | 543 | 83.821 | 98.167 | 26.043 | 1.00 13.25 | C |
| ATOM | 17758 | O | GLU | B | 543 | 85.049 | 98.334 | 26.152 | 1.00 13.28 | O |

| ATOM | 17760 | N | PHE | B | 544 | 83.017 | 97.831 | 27.057 | 1.00 | 13.59 | N |
|------|-------|-----|-----|---|-----|--------|--------|--------|------|-------|---|
| ATOM | 17761 | CA | PHE | B | 544 | 83.535 | 97.596 | 28.415 | 1.00 | 13.89 | C |
| ATOM | 17763 | CB | PHE | B | 544 | 82.376 | 97.244 | 29.340 | 1.00 | 14.02 | C |
| ATOM | 17766 | CG | PHE | B | 544 | 82.820 | 96.887 | 30.725 | 1.00 | 13.60 | C |
| ATOM | 17767 | CD1 | PHE | B | 544 | 83.029 | 97.847 | 31.669 | 1.00 | 13.55 | C |
| ATOM | 17769 | CE1 | PHE | B | 544 | 83.453 | 97.486 | 32.952 | 1.00 | 15.97 | C |
| ATOM | 17771 | CZ | PHE | B | 544 | 83.638 | 96.187 | 33.282 | 1.00 | 15.56 | C |
| ATOM | 17773 | CE2 | PHE | B | 544 | 83.428 | 95.209 | 32.359 | 1.00 | 15.74 | C |
| ATOM | 17775 | CD2 | PHE | B | 544 | 82.972 | 95.559 | 31.080 | 1.00 | 16.51 | C |
| ATOM | 17777 | C | PHE | B | 544 | 84.571 | 96.459 | 28.433 | 1.00 | 14.66 | C |
| ATOM | 17778 | O | PHE | B | 544 | 85.658 | 96.598 | 28.972 | 1.00 | 13.57 | O |
| ATOM | 17780 | N | LYS | B | 545 | 84.198 | 95.317 | 27.857 | 1.00 | 15.89 | N |
| ATOM | 17781 | CA | LYS | B | 545 | 85.062 | 94.141 | 27.826 | 1.00 | 18.77 | C |
| ATOM | 17783 | CB | LYS | B | 545 | 84.350 | 92.973 | 27.146 | 1.00 | 19.10 | C |
| ATOM | 17786 | CG | LYS | B | 545 | 83.292 | 92.349 | 28.003 | 1.00 | 21.85 | C |
| ATOM | 17789 | CD | LYS | B | 545 | 82.525 | 91.264 | 27.269 | 1.00 | 23.64 | C |
| ATOM | 17792 | CE | LYS | B | 545 | 81.489 | 90.617 | 28.217 | 1.00 | 25.72 | C |
| ATOM | 17795 | NZ | LYS | B | 545 | 80.832 | 89.399 | 27.609 | 1.00 | 29.32 | N |
| ATOM | 17799 | C | LYS | B | 545 | 86.411 | 94.441 | 27.127 | 1.00 | 17.92 | C |
| ATOM | 17800 | O | LYS | B | 545 | 87.454 | 93.920 | 27.539 | 1.00 | 18.13 | O |
| ATOM | 17802 | N | LYS | B | 546 | 86.412 | 95.292 | 26.099 | 1.00 | 18.53 | N |
| ATOM | 17803 | CA | LYS | B | 546 | 87.684 | 95.649 | 25.431 | 1.00 | 19.40 | C |
| ATOM | 17805 | CB | LYS | B | 546 | 87.495 | 96.734 | 24.367 | 1.00 | 20.60 | C |
| ATOM | 17808 | CG | LYS | B | 546 | 86.949 | 96.303 | 23.060 | 1.00 | 25.22 | C |
| ATOM | 17811 | CD | LYS | B | 546 | 86.765 | 97.554 | 22.183 | 1.00 | 22.94 | C |
| ATOM | 17814 | CE | LYS | B | 546 | 86.292 | 97.185 | 20.765 | 1.00 | 29.35 | C |
| ATOM | 17817 | NZ | LYS | B | 546 | 85.803 | 98.413 | 19.997 | 1.00 | 29.86 | N |
| ATOM | 17821 | C | LYS | B | 546 | 88.651 | 96.223 | 26.418 | 1.00 | 18.56 | C |
| ATOM | 17822 | O | LYS | B | 546 | 89.869 | 95.993 | 26.337 | 1.00 | 18.84 | O |
| ATOM | 17824 | N | GLN | B | 547 | 88.126 | 97.054 | 27.311 | 1.00 | 17.20 | N |
| ATOM | 17825 | CA | GLN | B | 547 | 88.980 | 97.713 | 28.297 | 1.00 | 17.74 | C |
| ATOM | 17827 | CB | GLN | B | 547 | 88.363 | 99.035 | 28.680 | 1.00 | 18.41 | C |
| ATOM | 17830 | CG | GLN | B | 547 | 88.596 | 100.086 | 27.616 | 1.00 | 20.65 | C |
| ATOM | 17833 | CD | GLN | B | 547 | 88.481 | 101.438 | 28.218 | 1.00 | 22.29 | C |
| ATOM | 17834 | OE1 | GLN | B | 547 | 89.366 | 101.898 | 29.006 | 1.00 | 27.36 | O |
| ATOM | 17835 | NE2 | GLN | B | 547 | 87.398 | 102.088 | 27.896 | 1.00 | 17.60 | N |
| ATOM | 17838 | C | GLN | B | 547 | 89.180 | 96.901 | 29.558 | 1.00 | 17.08 | C |
| ATOM | 17839 | O | GLN | B | 547 | 90.234 | 96.938 | 30.181 | 1.00 | 17.34 | O |
| ATOM | 17841 | N | PHE | B | 548 | 88.166 | 96.150 | 29.942 | 1.00 | 16.56 | N |
| ATOM | 17842 | CA | PHE | B | 548 | 88.267 | 95.457 | 31.198 | 1.00 | 16.94 | C |
| ATOM | 17844 | CB | PHE | B | 548 | 86.907 | 95.183 | 31.819 | 1.00 | 18.17 | C |
| ATOM | 17847 | CG | PHE | B | 548 | 86.997 | 95.000 | 33.309 | 1.00 | 18.76 | C |
| ATOM | 17848 | CD1 | PHE | B | 548 | 87.596 | 95.985 | 34.109 | 1.00 | 20.91 | C |
| ATOM | 17850 | CE1 | PHE | B | 548 | 87.727 | 95.816 | 35.475 | 1.00 | 22.28 | C |
| ATOM | 17852 | CZ | PHE | B | 548 | 87.254 | 94.640 | 36.053 | 1.00 | 19.56 | C |
| ATOM | 17854 | CE2 | PHE | B | 548 | 86.678 | 93.662 | 35.238 | 1.00 | 17.74 | C |
| ATOM | 17856 | CD2 | PHE | B | 548 | 86.559 | 93.859 | 33.879 | 1.00 | 19.07 | C |
| ATOM | 17858 | C | PHE | B | 548 | 89.128 | 94.194 | 31.186 | 1.00 | 17.18 | C |
| ATOM | 17859 | O | PHE | B | 548 | 89.818 | 93.903 | 32.188 | 1.00 | 17.93 | O |
| ATOM | 17861 | N | GLY | B | 549 | 89.114 | 93.455 | 30.070 | 1.00 | 16.61 | N |
| ATOM | 17862 | CA | GLY | B | 549 | 90.059 | 92.328 | 29.896 | 1.00 | 17.52 | C |
| ATOM | 17865 | C | GLY | B | 549 | 91.502 | 92.642 | 30.291 | 1.00 | 17.48 | C |
| ATOM | 17866 | O | GLY | B | 549 | 92.108 | 91.953 | 31.136 | 1.00 | 17.85 | O |
| ATOM | 17868 | N | PRO | B | 550 | 92.104 | 93.661 | 29.671 | 1.00 | 16.89 | N |
| ATOM | 17869 | CA | PRO | B | 550 | 93.426 | 94.122 | 30.055 | 1.00 | 17.42 | C |
| ATOM | 17871 | CB | PRO | B | 550 | 93.674 | 95.291 | 29.084 | 1.00 | 18.17 | C |
| ATOM | 17874 | CG | PRO | B | 550 | 92.888 | 94.919 | 27.895 | 1.00 | 17.40 | C |

| ATOM | 17877 | CD | PRO | B | 550 | 91.630 | 94.325 | 28.436 | 1.00 | 17.27 | C |
|------|-------|-----|-----|---|-----|--------|--------|--------|------|-------|---|
| ATOM | 17880 | C | PRO | B | 550 | 93.568 | 94.596 | 31.507 | 1.00 | 17.09 | C |
| ATOM | 17881 | O | PRO | B | 550 | 94.614 | 94.382 | 32.151 | 1.00 | 16.71 | O |
| ATOM | 17882 | N | ALA | B | 551 | 92.530 | 95.275 | 31.993 | 1.00 | 17.58 | N |
| ATOM | 17883 | CA | ALA | B | 551 | 92.494 | 95.792 | 33.370 | 1.00 | 18.14 | C |
| ATOM | 17885 | CB | ALA | B | 551 | 91.215 | 96.618 | 33.602 | 1.00 | 18.68 | C |
| ATOM | 17889 | C | ALA | B | 551 | 92.619 | 94.655 | 34.411 | 1.00 | 18.15 | C |
| ATOM | 17890 | O | ALA | B | 551 | 93.341 | 94.779 | 35.409 | 1.00 | 17.85 | O |
| ATOM | 17892 | N | ILE | B | 552 | 91.939 | 93.552 | 34.150 | 1.00 | 17.70 | N |
| ATOM | 17893 | CA | ILE | B | 552 | 92.011 | 92.343 | 35.000 | 1.00 | 17.56 | C |
| ATOM | 17895 | CB | ILE | B | 552 | 91.101 | 91.245 | 34.445 | 1.00 | 17.64 | C |
| ATOM | 17897 | CG1 | ILE | B | 552 | 89.652 | 91.599 | 34.723 | 1.00 | 20.06 | C |
| ATOM | 17900 | CD1 | ILE | B | 552 | 88.675 | 90.879 | 33.842 | 1.00 | 21.60 | C |
| ATOM | 17904 | CG2 | ILE | B | 552 | 91.420 | 89.829 | 35.061 | 1.00 | 18.38 | C |
| ATOM | 17908 | C | ILE | B | 552 | 93.435 | 91.828 | 35.085 | 1.00 | 17.53 | C |
| ATOM | 17909 | O | ILE | B | 552 | 93.982 | 91.618 | 36.172 | 1.00 | 17.29 | O |
| ATOM | 17911 | N | VAL | B | 553 | 94.032 | 91.636 | 33.918 | 1.00 | 17.46 | N |
| ATOM | 17912 | CA | VAL | B | 553 | 95.412 | 91.159 | 33.857 | 1.00 | 17.33 | C |
| ATOM | 17914 | CB | VAL | B | 553 | 95.870 | 91.036 | 32.391 | 1.00 | 16.64 | C |
| ATOM | 17916 | CG1 | VAL | B | 553 | 97.345 | 90.659 | 32.332 | 1.00 | 18.54 | C |
| ATOM | 17920 | CG2 | VAL | B | 553 | 95.000 | 90.022 | 31.644 | 1.00 | 16.22 | C |
| ATOM | 17924 | C | VAL | B | 553 | 96.324 | 92.089 | 34.654 | 1.00 | 16.62 | C |
| ATOM | 17925 | O | VAL | B | 553 | 97.191 | 91.656 | 35.427 | 1.00 | 16.94 | O |
| ATOM | 17927 | N | SER | B | 554 | 96.168 | 93.386 | 34.430 | 1.00 | 17.38 | N |
| ATOM | 17928 | CA | SER | B | 554 | 97.003 | 94.390 | 35.054 | 1.00 | 17.17 | C |
| ATOM | 17930 | CB | SER | B | 554 | 96.620 | 95.760 | 34.523 | 1.00 | 18.79 | C |
| ATOM | 17933 | OG | SER | B | 554 | 97.291 | 96.779 | 35.254 | 1.00 | 23.07 | O |
| ATOM | 17935 | C | SER | B | 554 | 96.898 | 94.394 | 36.570 | 1.00 | 16.87 | C |
| ATOM | 17936 | O | SER | B | 554 | 97.907 | 94.472 | 37.280 | 1.00 | 15.74 | O |
| ATOM | 17938 | N | LEU | B | 555 | 95.655 | 94.316 | 37.068 | 1.00 | 16.35 | N |
| ATOM | 17939 | CA | LEU | B | 555 | 95.429 | 94.308 | 38.520 | 1.00 | 17.37 | C |
| ATOM | 17941 | CB | LEU | B | 555 | 93.945 | 94.479 | 38.854 | 1.00 | 18.80 | C |
| ATOM | 17944 | CG | LEU | B | 555 | 93.442 | 95.928 | 38.795 | 1.00 | 22.52 | C |
| ATOM | 17946 | CD1 | LEU | B | 555 | 91.931 | 95.997 | 38.715 | 1.00 | 25.77 | C |
| ATOM | 17950 | CD2 | LEU | B | 555 | 93.985 | 96.755 | 39.967 | 1.00 | 25.77 | C |
| ATOM | 17954 | C | LEU | B | 555 | 95.973 | 93.033 | 39.145 | 1.00 | 15.97 | C |
| ATOM | 17955 | O | LEU | B | 555 | 96.533 | 93.066 | 40.229 | 1.00 | 15.74 | O |
| ATOM | 17957 | N | ILE | B | 556 | 95.790 | 91.910 | 38.458 | 1.00 | 16.43 | N |
| ATOM | 17958 | CA | ILE | B | 556 | 96.373 | 90.632 | 38.894 | 1.00 | 15.76 | C |
| ATOM | 17960 | CB | ILE | B | 556 | 95.938 | 89.483 | 37.957 | 1.00 | 15.89 | C |
| ATOM | 17962 | CG1 | ILE | B | 556 | 94.530 | 88.992 | 38.316 | 1.00 | 16.17 | C |
| ATOM | 17965 | CD1 | ILE | B | 556 | 93.998 | 87.927 | 37.361 | 1.00 | 16.16 | C |
| ATOM | 17969 | CG2 | ILE | B | 556 | 96.915 | 88.326 | 37.983 | 1.00 | 15.74 | C |
| ATOM | 17973 | C | ILE | B | 556 | 97.901 | 90.740 | 38.967 | 1.00 | 15.45 | C |
| ATOM | 17974 | O | ILE | B | 556 | 98.549 | 90.264 | 39.910 | 1.00 | 13.50 | O |
| ATOM | 17976 | N | ASP | B | 557 | 98.501 | 91.367 | 37.963 | 1.00 | 14.59 | N |
| ATOM | 17977 | CA | ASP | B | 557 | 99.962 | 91.530 | 37.996 | 1.00 | 15.55 | C |
| ATOM | 17979 | CB | ASP | B | 557 | 100.478 | 92.104 | 36.679 | 1.00 | 16.82 | C |
| ATOM | 17982 | CG | ASP | B | 557 | 100.492 | 91.089 | 35.583 | 1.00 | 20.06 | C |
| ATOM | 17983 | OD1 | ASP | B | 557 | 100.486 | 89.873 | 35.898 | 1.00 | 21.76 | O |
| ATOM | 17984 | OD2 | ASP | B | 557 | 100.546 | 91.508 | 34.407 | 1.00 | 22.20 | O |
| ATOM | 17985 | C | ASP | B | 557 | 100.408 | 92.426 | 39.128 | 1.00 | 15.09 | C |
| ATOM | 17986 | O | ASP | B | 557 | 101.373 | 92.118 | 39.858 | 1.00 | 15.31 | O |
| ATOM | 17988 | N | GLN | B | 558 | 99.718 | 93.545 | 39.272 | 1.00 | 14.47 | N |
| ATOM | 17989 | CA | GLN | B | 558 | 100.041 | 94.497 | 40.294 | 1.00 | 15.82 | C |
| ATOM | 17991 | CB | GLN | B | 558 | 99.145 | 95.709 | 40.181 | 1.00 | 15.71 | C |
| ATOM | 17994 | CG | GLN | B | 558 | 99.396 | 96.767 | 41.236 | 1.00 | 19.45 | C |

| ATOM | 17997 | CD | GLN | B | 558 | 98.411 | 97.940 | 41.166 | 1.00 | 20.94 | C |
| --- | --- | --- | --- | --- | --- | --- | --- | --- | --- | --- | --- |
| ATOM | 17998 | OE1 | GLN | B | 558 | 97.342 | 97.846 | 40.538 | 1.00 | 26.93 | O |
| ATOM | 17999 | NE2 | GLN | B | 558 | 98.769 | 99.050 | 41.826 | 1.00 | 26.80 | N |
| ATOM | 18002 | C | GLN | B | 558 | 99.930 | 93.882 | 41.689 | 1.00 | 14.44 | C |
| ATOM | 18003 | O | GLN | B | 558 | 100.819 | 94.090 | 42.532 | 1.00 | 15.27 | O |
| ATOM | 18005 | N | HIS | B | 559 | 98.870 | 93.114 | 41.927 | 1.00 | 14.23 | N |
| ATOM | 18006 | CA | HIS | B | 559 | 98.600 | 92.620 | 43.283 | 1.00 | 13.16 | C |
| ATOM | 18008 | CB | HIS | B | 559 | 97.074 | 92.492 | 43.526 | 1.00 | 12.60 | C |
| ATOM | 18011 | CG | HIS | B | 559 | 96.408 | 93.816 | 43.679 | 1.00 | 13.48 | C |
| ATOM | 18012 | ND1 | HIS | B | 559 | 96.188 | 94.399 | 44.904 | 1.00 | 14.75 | N |
| ATOM | 18014 | CE1 | HIS | B | 559 | 95.629 | 95.583 | 44.734 | 1.00 | 14.21 | C |
| ATOM | 18016 | NE2 | HIS | B | 559 | 95.525 | 95.811 | 43.440 | 1.00 | 15.97 | N |
| ATOM | 18018 | CD2 | HIS | B | 559 | 96.026 | 94.729 | 42.758 | 1.00 | 12.86 | C |
| ATOM | 18020 | C | HIS | B | 559 | 99.335 | 91.341 | 43.606 | 1.00 | 12.74 | C |
| ATOM | 18021 | O | HIS | B | 559 | 99.806 | 91.167 | 44.719 | 1.00 | 12.76 | O |
| ATOM | 18023 | N | PHE | B | 560 | 99.412 | 90.441 | 42.630 | 1.00 | 12.52 | N |
| ATOM | 18024 | CA | PHE | B | 560 | 99.867 | 89.090 | 42.856 | 1.00 | 12.64 | C |
| ATOM | 18026 | CB | PHE | B | 560 | 98.792 | 88.111 | 42.416 | 1.00 | 12.73 | C |
| ATOM | 18029 | CG | PHE | B | 560 | 97.423 | 88.359 | 43.031 | 1.00 | 12.44 | C |
| ATOM | 18030 | CD1 | PHE | B | 560 | 97.286 | 88.786 | 44.365 | 1.00 | 13.39 | C |
| ATOM | 18032 | CE1 | PHE | B | 560 | 96.014 | 88.989 | 44.918 | 1.00 | 10.87 | C |
| ATOM | 18034 | CZ | PHE | B | 560 | 94.915 | 88.747 | 44.154 | 1.00 | 12.41 | C |
| ATOM | 18036 | CE2 | PHE | B | 560 | 95.042 | 88.356 | 42.840 | 1.00 | 13.63 | C |
| ATOM | 18038 | CD2 | PHE | B | 560 | 96.281 | 88.155 | 42.284 | 1.00 | 14.51 | C |
| ATOM | 18040 | C | PHE | B | 560 | 101.135 | 88.723 | 42.119 | 1.00 | 13.00 | C |
| ATOM | 18041 | O | PHE | B | 560 | 101.695 | 87.664 | 42.379 | 1.00 | 13.56 | O |
| ATOM | 18043 | N | GLY | B | 561 | 101.622 | 89.587 | 41.230 | 1.00 | 14.37 | N |
| ATOM | 18044 | CA | GLY | B | 561 | 102.745 | 89.205 | 40.383 | 1.00 | 14.97 | C |
| ATOM | 18047 | C | GLY | B | 561 | 103.967 | 88.720 | 41.169 | 1.00 | 15.36 | C |
| ATOM | 18048 | O | GLY | B | 561 | 104.601 | 87.710 | 40.817 | 1.00 | 15.62 | O |
| ATOM | 18050 | N | SER | B | 562 | 104.305 | 89.407 | 42.251 | 1.00 | 15.44 | N |
| ATOM | 18051 | CA | SER | B | 562 | 105.511 | 89.012 | 42.981 | 1.00 | 16.70 | C |
| ATOM | 18053 | CB | SER | B | 562 | 106.012 | 90.111 | 43.923 | 1.00 | 17.64 | C |
| ATOM | 18056 | OG | SER | B | 562 | 104.965 | 90.673 | 44.664 | 1.00 | 22.07 | O |
| ATOM | 18058 | C | SER | B | 562 | 105.314 | 87.690 | 43.698 | 1.00 | 16.43 | C |
| ATOM | 18059 | O | SER | B | 562 | 106.202 | 86.868 | 43.720 | 1.00 | 15.58 | O |
| ATOM | 18061 | N | ALA | B | 563 | 104.126 | 87.465 | 44.249 | 1.00 | 16.43 | N |
| ATOM | 18062 | CA | ALA | B | 563 | 103.821 | 86.183 | 44.872 | 1.00 | 16.96 | C |
| ATOM | 18064 | CB | ALA | B | 563 | 102.508 | 86.267 | 45.618 | 1.00 | 16.87 | C |
| ATOM | 18068 | C | ALA | B | 563 | 103.821 | 85.020 | 43.858 | 1.00 | 17.34 | C |
| ATOM | 18069 | O | ALA | B | 563 | 104.000 | 83.871 | 44.253 | 1.00 | 16.83 | O |
| ATOM | 18071 | N | MSE | B | 564 | 103.639 | 85.306 | 42.557 | 1.00 | 16.86 | N |
| ATOM | 18072 | CA | MSE | B | 564 | 103.630 | 84.243 | 41.541 | 1.00 | 18.48 | C |
| ATOM | 18074 | CB | MSE | B | 564 | 102.536 | 84.498 | 40.501 | 1.00 | 17.84 | C |
| ATOM | 18077 | CG | MSE | B | 564 | 101.186 | 84.597 | 41.092 | 1.00 | 19.27 | C |
| ATOM | 18080 | SE | MSE | B | 564 | 99.788 | 84.812 | 39.687 | 1.00 | 26.34 | SE |
| ATOM | 18081 | CE | MSE | B | 564 | 100.378 | 86.622 | 38.906 | 1.00 | 21.27 | C |
| ATOM | 18085 | C | MSE | B | 564 | 104.965 | 84.096 | 40.810 | 1.00 | 18.02 | C |
| ATOM | 18086 | O | MSE | B | 564 | 105.111 | 83.265 | 39.926 | 1.00 | 16.74 | O |
| ATOM | 18088 | N | THR | B | 565 | 105.943 | 84.911 | 41.163 | 1.00 | 18.63 | N |
| ATOM | 18089 | CA | THR | B | 565 | 107.213 | 84.862 | 40.444 | 1.00 | 19.80 | C |
| ATOM | 18091 | CB | THR | B | 565 | 108.190 | 85.938 | 40.965 | 1.00 | 19.98 | C |
| ATOM | 18093 | OG1 | THR | B | 565 | 109.441 | 85.827 | 40.268 | 1.00 | 25.49 | O |
| ATOM | 18095 | CG2 | THR | B | 565 | 108.461 | 85.793 | 42.459 | 1.00 | 22.39 | C |
| ATOM | 18099 | C | THR | B | 565 | 107.830 | 83.454 | 40.566 | 1.00 | 19.10 | C |
| ATOM | 18100 | O | THR | B | 565 | 107.793 | 82.852 | 41.641 | 1.00 | 19.09 | O |
| ATOM | 18102 | N | GLY | B | 566 | 108.344 | 82.916 | 39.451 | 1.00 | 17.92 | N |

| | | | | | | | | | |
|---|---|---|---|---|---|---|---|---|---|
| ATOM | 18103 | CA | GLY | B | 566 | 108.989 | 81.610 | 39.453 | 1.00 16.99 | C |
| ATOM | 18106 | C | GLY | B | 566 | 108.007 | 80.468 | 39.400 | 1.00 16.43 | C |
| ATOM | 18107 | O | GLY | B | 566 | 108.401 | 79.310 | 39.434 | 1.00 17.19 | O |
| ATOM | 18109 | N | SER | B | 567 | 106.724 | 80.779 | 39.294 | 1.00 16.04 | N |
| ATOM | 18110 | CA | SER | B | 567 | 105.716 | 79.744 | 39.235 | 1.00 15.57 | C |
| ATOM | 18112 | CB | SER | B | 567 | 104.589 | 80.048 | 40.233 | 1.00 15.79 | C |
| ATOM | 18115 | OG | SER | B | 567 | 103.719 | 81.057 | 39.733 | 1.00 18.20 | O |
| ATOM | 18117 | C | SER | B | 567 | 105.114 | 79.649 | 37.840 | 1.00 15.12 | C |
| ATOM | 18118 | O | SER | B | 567 | 105.368 | 80.478 | 36.935 | 1.00 14.69 | O |
| ATOM | 18120 | N | ASN | B | 568 | 104.259 | 78.659 | 37.688 | 1.00 14.16 | N |
| ATOM | 18121 | CA | ASN | B | 568 | 103.464 | 78.541 | 36.493 | 1.00 13.89 | C |
| ATOM | 18123 | CB | ASN | B | 568 | 103.719 | 77.176 | 35.830 | 1.00 13.75 | C |
| ATOM | 18126 | CG | ASN | B | 568 | 103.060 | 77.062 | 34.487 | 1.00 14.75 | C |
| ATOM | 18127 | OD1 | ASN | B | 568 | 102.890 | 78.070 | 33.779 | 1.00 14.70 | O |
| ATOM | 18128 | ND2 | ASN | B | 568 | 102.615 | 75.848 | 34.142 | 1.00 17.21 | N |
| ATOM | 18131 | C | ASN | B | 568 | 101.999 | 78.746 | 36.855 | 1.00 13.48 | C |
| ATOM | 18132 | O | ASN | B | 568 | 101.111 | 78.071 | 36.316 | 1.00 13.31 | O |
| ATOM | 18134 | N | LEU | B | 569 | 101.751 | 79.774 | 37.685 | 1.00 13.46 | N |
| ATOM | 18135 | CA | LEU | B | 569 | 100.375 | 80.084 | 38.163 | 1.00 13.28 | C |
| ATOM | 18137 | CB | LEU | B | 569 | 100.393 | 80.471 | 39.640 | 1.00 13.21 | C |
| ATOM | 18140 | CG | LEU | B | 569 | 100.936 | 79.421 | 40.584 | 1.00 13.14 | C |
| ATOM | 18142 | CD1 | LEU | B | 569 | 101.124 | 80.024 | 41.954 | 1.00 15.25 | C |
| ATOM | 18146 | CD2 | LEU | B | 569 | 99.988 | 78.261 | 40.587 | 1.00 12.37 | C |
| ATOM | 18150 | C | LEU | B | 569 | 99.629 | 81.203 | 37.427 | 1.00 13.86 | C |
| ATOM | 18151 | O | LEU | B | 569 | 98.400 | 81.294 | 37.518 | 1.00 13.16 | O |
| ATOM | 18153 | N | ARG | B | 570 | 100.348 | 82.045 | 36.689 | 1.00 15.21 | N |
| ATOM | 18154 | CA | ARG | B | 570 | 99.719 | 83.241 | 36.081 | 1.00 17.14 | C |
| ATOM | 18156 | CB | ARG | B | 570 | 100.776 | 84.217 | 35.596 | 1.00 18.11 | C |
| ATOM | 18159 | CG | ARG | B | 570 | 100.187 | 85.477 | 34.979 | 1.00 19.20 | C |
| ATOM | 18162 | CD | ARG | B | 570 | 101.269 | 86.533 | 34.872 | 1.00 24.13 | C |
| ATOM | 18165 | NE | ARG | B | 570 | 100.857 | 87.771 | 34.186 | 1.00 24.33 | N |
| ATOM | 18167 | CZ | ARG | B | 570 | 100.854 | 87.950 | 32.858 | 1.00 28.62 | C |
| ATOM | 18168 | NH1 | ARG | B | 570 | 101.130 | 86.955 | 32.020 | 1.00 32.00 | N |
| ATOM | 18171 | NH2 | ARG | B | 570 | 100.506 | 89.125 | 32.362 | 1.00 28.34 | N |
| ATOM | 18174 | C | ARG | B | 570 | 98.698 | 82.942 | 34.976 | 1.00 17.66 | C |
| ATOM | 18175 | O | ARG | B | 570 | 97.565 | 83.447 | 35.011 | 1.00 16.50 | O |
| ATOM | 18177 | N | ASP | B | 571 | 99.089 | 82.151 | 33.976 | 1.00 18.71 | N |
| ATOM | 18178 | CA | ASP | B | 571 | 98.146 | 81.693 | 32.936 | 1.00 19.57 | C |
| ATOM | 18180 | CB | ASP | B | 571 | 98.771 | 80.581 | 32.088 | 1.00 21.16 | C |
| ATOM | 18183 | CG | ASP | B | 571 | 99.365 | 81.078 | 30.829 | 1.00 24.53 | C |
| ATOM | 18184 | OD1 | ASP | B | 571 | 99.679 | 82.299 | 30.785 | 1.00 31.42 | O |
| ATOM | 18185 | OD2 | ASP | B | 571 | 99.539 | 80.220 | 29.909 | 1.00 28.45 | O |
| ATOM | 18186 | C | ASP | B | 571 | 96.905 | 81.106 | 33.554 | 1.00 19.03 | C |
| ATOM | 18187 | O | ASP | B | 571 | 95.791 | 81.485 | 33.220 | 1.00 18.99 | O |
| ATOM | 18189 | N | GLU | B | 572 | 97.109 | 80.150 | 34.454 | 1.00 18.44 | N |
| ATOM | 18190 | CA | GLU | B | 572 | 95.984 | 79.395 | 35.087 | 1.00 17.64 | C |
| ATOM | 18192 | CB | GLU | B | 572 | 96.481 | 78.444 | 36.086 | 1.00 18.11 | C |
| ATOM | 18195 | CG | GLU | B | 572 | 95.383 | 77.589 | 36.645 | 1.00 19.27 | C |
| ATOM | 18198 | CD | GLU | B | 572 | 95.801 | 76.669 | 37.790 | 1.00 19.42 | C |
| ATOM | 18199 | OE1 | GLU | B | 572 | 97.001 | 76.613 | 38.178 | 1.00 21.78 | O |
| ATOM | 18200 | OE2 | GLU | B | 572 | 94.888 | 75.990 | 38.303 | 1.00 27.33 | O |
| ATOM | 18201 | C | GLU | B | 572 | 95.069 | 80.500 | 35.804 | 1.00 15.85 | C |
| ATOM | 18202 | O | GLU | B | 572 | 93.836 | 80.420 | 35.711 | 1.00 14.86 | O |
| ATOM | 18204 | N | LEU | B | 573 | 95.686 | 81.428 | 36.539 | 1.00 14.36 | N |
| ATOM | 18205 | CA | LEU | B | 573 | 94.887 | 82.360 | 37.335 | 1.00 14.61 | C |
| ATOM | 18207 | CB | LEU | B | 573 | 95.755 | 83.223 | 38.245 | 1.00 15.33 | C |
| ATOM | 18210 | CG | LEU | B | 573 | 94.937 | 84.137 | 39.192 | 1.00 14.90 | C |

| | | | | | | | | | |
|---|---|---|---|---|---|---|---|---|---|
| ATOM | 18212 | CD1 | LEU | B | 573 | 94.153 | 83.287 | 40.193 | 1.00 14.91 | C |
| ATOM | 18216 | CD2 | LEU | B | 573 | 95.766 | 85.155 | 39.920 | 1.00 14.84 | C |
| ATOM | 18220 | C | LEU | B | 573 | 94.048 | 83.271 | 36.452 | 1.00 14.30 | C |
| ATOM | 18221 | O | LEU | B | 573 | 92.857 | 83.496 | 36.706 | 1.00 12.96 | O |
| ATOM | 18223 | N | VAL | B | 574 | 94.702 | 83.861 | 35.445 | 1.00 14.51 | N |
| ATOM | 18224 | CA | VAL | B | 574 | 93.982 | 84.775 | 34.538 | 1.00 14.66 | C |
| ATOM | 18226 | CB | VAL | B | 574 | 94.895 | 85.360 | 33.453 | 1.00 13.84 | C |
| ATOM | 18228 | CG1 | VAL | B | 574 | 94.055 | 86.179 | 32.484 | 1.00 14.01 | C |
| ATOM | 18232 | CG2 | VAL | B | 574 | 95.958 | 86.225 | 34.069 | 1.00 12.90 | C |
| ATOM | 18236 | C | VAL | B | 574 | 92.821 | 84.040 | 33.871 | 1.00 15.46 | C |
| ATOM | 18237 | O | VAL | B | 574 | 91.694 | 84.558 | 33.795 | 1.00 16.16 | O |
| ATOM | 18239 | N | GLU | B | 575 | 93.103 | 82.836 | 33.390 | 1.00 16.80 | N |
| ATOM | 18240 | CA | GLU | B | 575 | 92.083 | 82.056 | 32.704 | 1.00 17.68 | C |
| ATOM | 18242 | CB | GLU | B | 575 | 92.623 | 80.701 | 32.223 | 1.00 17.78 | C |
| ATOM | 18245 | CG | GLU | B | 575 | 91.515 | 79.757 | 31.712 | 1.00 20.59 | C |
| ATOM | 18248 | CD | GLU | B | 575 | 91.983 | 78.296 | 31.550 | 1.00 25.24 | C |
| ATOM | 18249 | OE1 | GLU | B | 575 | 92.372 | 77.640 | 32.576 | 1.00 36.53 | O |
| ATOM | 18250 | OE2 | GLU | B | 575 | 91.928 | 77.803 | 30.386 | 1.00 37.23 | O |
| ATOM | 18251 | C | GLU | B | 575 | 90.904 | 81.810 | 33.640 | 1.00 16.23 | C |
| ATOM | 18252 | O | GLU | B | 575 | 89.778 | 81.985 | 33.246 | 1.00 15.75 | O |
| ATOM | 18254 | N | LYS | B | 576 | 91.187 | 81.352 | 34.863 | 1.00 15.49 | N |
| ATOM | 18255 | CA | LYS | B | 576 | 90.128 | 80.896 | 35.768 | 1.00 16.52 | C |
| ATOM | 18257 | CB | LYS | B | 576 | 90.706 | 79.968 | 36.829 | 1.00 16.76 | C |
| ATOM | 18260 | CG | LYS | B | 576 | 91.123 | 78.599 | 36.276 | 1.00 18.82 | C |
| ATOM | 18263 | CD | LYS | B | 576 | 91.500 | 77.646 | 37.418 | 1.00 20.21 | C |
| ATOM | 18266 | CE | LYS | B | 576 | 92.032 | 76.321 | 36.940 | 1.00 23.82 | C |
| ATOM | 18269 | NZ | LYS | B | 576 | 91.186 | 75.811 | 35.858 | 1.00 29.77 | N |
| ATOM | 18273 | C | LYS | B | 576 | 89.372 | 82.068 | 36.383 | 1.00 14.45 | C |
| ATOM | 18274 | O | LYS | B | 576 | 88.139 | 82.004 | 36.575 | 1.00 15.10 | O |
| ATOM | 18276 | N | VAL | B | 577 | 90.060 | 83.166 | 36.651 | 1.00 13.12 | N |
| ATOM | 18277 | CA | VAL | B | 577 | 89.389 | 84.394 | 37.133 | 1.00 13.39 | C |
| ATOM | 18279 | CB | VAL | B | 577 | 90.381 | 85.488 | 37.605 | 1.00 14.34 | C |
| ATOM | 18281 | CG1 | VAL | B | 577 | 89.738 | 86.868 | 37.682 | 1.00 12.98 | C |
| ATOM | 18285 | CG2 | VAL | B | 577 | 90.952 | 85.112 | 38.961 | 1.00 13.26 | C |
| ATOM | 18289 | C | VAL | B | 577 | 88.433 | 84.906 | 36.061 | 1.00 13.78 | C |
| ATOM | 18290 | O | VAL | B | 577 | 87.295 | 85.207 | 36.362 | 1.00 13.78 | O |
| ATOM | 18292 | N | ASN | B | 578 | 88.871 | 84.956 | 34.812 | 1.00 14.66 | N |
| ATOM | 18293 | CA | ASN | B | 578 | 87.989 | 85.356 | 33.715 | 1.00 16.26 | C |
| ATOM | 18295 | CB | ASN | B | 578 | 88.775 | 85.366 | 32.378 | 1.00 16.85 | C |
| ATOM | 18298 | CG | ASN | B | 578 | 89.747 | 86.556 | 32.224 | 1.00 19.00 | C |
| ATOM | 18299 | OD1 | ASN | B | 578 | 89.601 | 87.594 | 32.843 | 1.00 24.37 | O |
| ATOM | 18300 | ND2 | ASN | B | 578 | 90.735 | 86.388 | 31.361 | 1.00 22.16 | N |
| ATOM | 18303 | C | ASN | B | 578 | 86.774 | 84.454 | 33.600 | 1.00 15.69 | C |
| ATOM | 18304 | O | ASN | B | 578 | 85.644 | 84.925 | 33.400 | 1.00 15.87 | O |
| ATOM | 18306 | N | LYS | B | 579 | 86.953 | 83.152 | 33.777 | 1.00 15.71 | N |
| ATOM | 18307 | CA | LYS | B | 579 | 85.844 | 82.258 | 33.616 | 1.00 17.44 | C |
| ATOM | 18309 | CB | LYS | B | 579 | 86.287 | 80.819 | 33.574 | 1.00 17.40 | C |
| ATOM | 18312 | CG | LYS | B | 579 | 87.057 | 80.437 | 32.322 | 1.00 21.45 | C |
| ATOM | 18315 | CD | LYS | B | 579 | 87.298 | 78.922 | 32.107 | 1.00 22.94 | C |
| ATOM | 18318 | CE | LYS | B | 579 | 86.946 | 78.036 | 33.289 | 1.00 28.96 | C |
| ATOM | 18321 | NZ | LYS | B | 579 | 85.469 | 77.706 | 33.354 | 1.00 33.21 | N |
| ATOM | 18325 | C | LYS | B | 579 | 84.858 | 82.444 | 34.766 | 1.00 16.55 | C |
| ATOM | 18326 | O | LYS | B | 579 | 83.650 | 82.401 | 34.563 | 1.00 18.38 | O |
| ATOM | 18328 | N | THR | B | 580 | 85.390 | 82.650 | 35.962 | 1.00 15.50 | N |
| ATOM | 18329 | CA | THR | B | 580 | 84.498 | 82.819 | 37.111 | 1.00 15.46 | C |
| ATOM | 18331 | CB | THR | B | 580 | 85.312 | 82.839 | 38.391 | 1.00 15.47 | C |
| ATOM | 18333 | OG1 | THR | B | 580 | 85.924 | 81.553 | 38.595 | 1.00 14.32 | O |

| | | | | | | | | | |
|---|---|---|---|---|---|---|---|---|---|
| ATOM | 18335 | CG2 | THR B 580 | 84.449 | 83.269 | 39.626 | 1.00 | 15.94 | C |
| ATOM | 18339 | C | THR B 580 | 83.699 | 84.121 | 36.972 | 1.00 | 14.90 | C |
| ATOM | 18340 | O | THR B 580 | 82.471 | 84.160 | 37.228 | 1.00 | 15.45 | O |
| ATOM | 18342 | N | LEU B 581 | 84.376 | 85.194 | 36.589 | 1.00 | 14.81 | N |
| ATOM | 18343 | CA | LEU B 581 | 83.693 | 86.472 | 36.396 | 1.00 | 15.55 | C |
| ATOM | 18345 | CB | LEU B 581 | 84.680 | 87.553 | 36.046 | 1.00 | 15.31 | C |
| ATOM | 18348 | CG | LEU B 581 | 85.669 | 87.991 | 37.125 | 1.00 | 15.14 | C |
| ATOM | 18350 | CD1 | LEU B 581 | 86.771 | 88.806 | 36.454 | 1.00 | 15.59 | C |
| ATOM | 18354 | CD2 | LEU B 581 | 84.951 | 88.787 | 38.238 | 1.00 | 14.95 | C |
| ATOM | 18358 | C | LEU B 581 | 82.607 | 86.374 | 35.308 | 1.00 | 17.10 | C |
| ATOM | 18359 | O | LEU B 581 | 81.467 | 86.822 | 35.481 | 1.00 | 18.06 | O |
| ATOM | 18361 | N | ALA B 582 | 82.935 | 85.753 | 34.183 | 1.00 | 18.81 | N |
| ATOM | 18362 | CA | ALA B 582 | 81.975 | 85.672 | 33.072 | 1.00 | 21.54 | C |
| ATOM | 18364 | CB | ALA B 582 | 82.597 | 84.956 | 31.859 | 1.00 | 21.95 | C |
| ATOM | 18368 | C | ALA B 582 | 80.736 | 84.940 | 33.511 | 1.00 | 22.59 | C |
| ATOM | 18369 | O | ALA B 582 | 79.605 | 85.408 | 33.310 | 1.00 | 24.52 | O |
| ATOM | 18371 | N | LYS B 583 | 80.932 | 83.773 | 34.100 | 1.00 | 22.91 | N |
| ATOM | 18372 | CA | LYS B 583 | 79.791 | 82.944 | 34.456 | 1.00 | 24.30 | C |
| ATOM | 18374 | CB | LYS B 583 | 80.239 | 81.582 | 34.945 | 1.00 | 24.10 | C |
| ATOM | 18377 | CG | LYS B 583 | 79.068 | 80.680 | 35.341 | 1.00 | 28.09 | C |
| ATOM | 18380 | CD | LYS B 583 | 79.301 | 79.159 | 35.095 | 1.00 | 30.23 | C |
| ATOM | 18383 | CE | LYS B 583 | 78.491 | 78.601 | 33.870 | 1.00 | 34.80 | C |
| ATOM | 18386 | NZ | LYS B 583 | 79.361 | 77.706 | 33.015 | 1.00 | 36.74 | N |
| ATOM | 18390 | C | LYS B 583 | 78.920 | 83.658 | 35.512 | 1.00 | 22.39 | C |
| ATOM | 18391 | O | LYS B 583 | 77.680 | 83.684 | 35.413 | 1.00 | 22.46 | O |
| ATOM | 18393 | N | ARG B 584 | 79.559 | 84.302 | 36.481 | 1.00 | 19.79 | N |
| ATOM | 18394 | CA | ARG B 584 | 78.798 | 84.969 | 37.542 | 1.00 | 18.19 | C |
| ATOM | 18396 | CB | ARG B 584 | 79.722 | 85.375 | 38.702 | 1.00 | 18.33 | C |
| ATOM | 18399 | CG | ARG B 584 | 79.021 | 86.016 | 39.886 | 1.00 | 17.13 | C |
| ATOM | 18402 | CD | ARG B 584 | 77.831 | 85.172 | 40.381 | 1.00 | 17.40 | C |
| ATOM | 18405 | NE | ARG B 584 | 77.217 | 85.771 | 41.571 | 1.00 | 16.12 | N |
| ATOM | 18407 | CZ | ARG B 584 | 76.135 | 85.313 | 42.166 | 1.00 | 19.38 | C |
| ATOM | 18408 | NH1 | ARG B 584 | 75.488 | 84.273 | 41.655 | 1.00 | 21.09 | N |
| ATOM | 18411 | NH2 | ARG B 584 | 75.650 | 85.932 | 43.226 | 1.00 | 17.74 | N |
| ATOM | 18414 | C | ARG B 584 | 78.045 | 86.202 | 37.019 | 1.00 | 18.30 | C |
| ATOM | 18415 | O | ARG B 584 | 76.887 | 86.406 | 37.343 | 1.00 | 17.45 | O |
| ATOM | 18417 | N | LEU B 585 | 78.708 | 87.023 | 36.238 | 1.00 | 18.17 | N |
| ATOM | 18418 | CA | LEU B 585 | 78.067 | 88.252 | 35.759 | 1.00 | 18.71 | C |
| ATOM | 18420 | CB | LEU B 585 | 79.059 | 89.101 | 34.990 | 1.00 | 18.77 | C |
| ATOM | 18423 | CG | LEU B 585 | 80.142 | 89.739 | 35.847 | 1.00 | 16.80 | C |
| ATOM | 18425 | CD1 | LEU B 585 | 81.295 | 90.142 | 34.933 | 1.00 | 18.30 | C |
| ATOM | 18429 | CD2 | LEU B 585 | 79.604 | 90.938 | 36.622 | 1.00 | 18.24 | C |
| ATOM | 18433 | C | LEU B 585 | 76.820 | 87.978 | 34.921 | 1.00 | 19.52 | C |
| ATOM | 18434 | O | LEU B 585 | 75.872 | 88.769 | 34.971 | 1.00 | 19.01 | O |
| ATOM | 18436 | N | GLU B 586 | 76.803 | 86.874 | 34.174 | 1.00 | 20.01 | N |
| ATOM | 18437 | CA | GLU B 586 | 75.614 | 86.527 | 33.354 | 1.00 | 21.35 | C |
| ATOM | 18439 | CB | GLU B 586 | 75.841 | 85.219 | 32.599 | 1.00 | 21.82 | C |
| ATOM | 18442 | CG | GLU B 586 | 74.597 | 84.695 | 31.883 | 1.00 | 24.07 | C |
| ATOM | 18445 | CD | GLU B 586 | 74.884 | 83.786 | 30.667 | 1.00 | 26.87 | C |
| ATOM | 18446 | OE1 | GLU B 586 | 76.031 | 83.794 | 30.135 | 1.00 | 32.92 | O |
| ATOM | 18447 | OE2 | GLU B 586 | 73.926 | 83.098 | 30.232 | 1.00 | 25.77 | O |
| ATOM | 18448 | C | GLU B 586 | 74.370 | 86.422 | 34.222 | 1.00 | 21.39 | C |
| ATOM | 18449 | O | GLU B 586 | 73.246 | 86.619 | 33.760 | 1.00 | 20.80 | O |
| ATOM | 18451 | N | GLN B 587 | 74.554 | 86.126 | 35.497 | 1.00 | 19.74 | N |
| ATOM | 18452 | CA | GLN B 587 | 73.442 | 85.867 | 36.360 | 1.00 | 21.28 | C |
| ATOM | 18454 | CB | GLN B 587 | 73.598 | 84.485 | 37.008 | 1.00 | 23.33 | C |
| ATOM | 18457 | CG | GLN B 587 | 74.568 | 84.382 | 38.055 | 1.00 | 25.60 | C |

| ATOM | 18460 | CD | GLN | B | 587 | 75.025 | 82.929 | 38.385 | 1.00 | 25.64 | C |
| --- | --- | --- | --- | --- | --- | --- | --- | --- | --- | --- | --- |
| ATOM | 18461 | OE1 | GLN | B | 587 | 76.068 | 82.772 | 38.939 | 1.00 | 31.13 | O |
| ATOM | 18462 | NE2 | GLN | B | 587 | 74.209 | 81.909 | 38.087 | 1.00 | 29.75 | N |
| ATOM | 18465 | C | GLN | B | 587 | 73.135 | 86.980 | 37.366 | 1.00 | 19.51 | C |
| ATOM | 18466 | O | GLN | B | 587 | 72.139 | 86.906 | 38.067 | 1.00 | 20.77 | O |
| ATOM | 18468 | N | THR | B | 588 | 73.953 | 88.018 | 37.409 | 1.00 | 16.13 | N |
| ATOM | 18469 | CA | THR | B | 588 | 73.723 | 89.147 | 38.293 | 1.00 | 14.95 | C |
| ATOM | 18471 | CB | THR | B | 588 | 74.954 | 89.437 | 39.140 | 1.00 | 15.04 | C |
| ATOM | 18473 | OG1 | THR | B | 588 | 76.078 | 89.690 | 38.297 | 1.00 | 13.46 | O |
| ATOM | 18475 | CG2 | THR | B | 588 | 75.254 | 88.201 | 40.010 | 1.00 | 15.17 | C |
| ATOM | 18479 | C | THR | B | 588 | 73.320 | 90.397 | 37.519 | 1.00 | 14.47 | C |
| ATOM | 18480 | O | THR | B | 588 | 73.493 | 91.516 | 37.996 | 1.00 | 14.39 | O |
| ATOM | 18482 | N | ASN | B | 589 | 72.651 | 90.181 | 36.392 | 1.00 | 14.97 | N |
| ATOM | 18483 | CA | ASN | B | 589 | 72.231 | 91.258 | 35.531 | 1.00 | 15.52 | C |
| ATOM | 18485 | CB | ASN | B | 589 | 72.017 | 90.756 | 34.090 | 1.00 | 14.99 | C |
| ATOM | 18488 | CG | ASN | B | 589 | 71.095 | 89.505 | 34.003 | 1.00 | 15.25 | C |
| ATOM | 18489 | OD1 | ASN | B | 589 | 70.993 | 88.697 | 34.958 | 1.00 | 16.76 | O |
| ATOM | 18490 | ND2 | ASN | B | 589 | 70.415 | 89.342 | 32.840 | 1.00 | 14.42 | N |
| ATOM | 18493 | C | ASN | B | 589 | 71.015 | 92.067 | 36.068 | 1.00 | 15.98 | C |
| ATOM | 18494 | O | ASN | B | 589 | 70.628 | 93.076 | 35.456 | 1.00 | 17.51 | O |
| ATOM | 18496 | N | SER | B | 590 | 70.469 | 91.650 | 37.230 | 1.00 | 15.97 | N |
| ATOM | 18497 | CA | SER | B | 590 | 69.447 | 92.437 | 37.946 | 1.00 | 16.10 | C |
| ATOM | 18499 | CB | SER | B | 590 | 68.283 | 91.569 | 38.417 | 1.00 | 17.85 | C |
| ATOM | 18502 | OG | SER | B | 590 | 67.742 | 90.861 | 37.300 | 1.00 | 19.81 | O |
| ATOM | 18504 | C | SER | B | 590 | 69.992 | 93.182 | 39.145 | 1.00 | 16.57 | C |
| ATOM | 18505 | O | SER | B | 590 | 69.210 | 93.791 | 39.841 | 1.00 | 16.81 | O |
| ATOM | 18507 | N | TYR | B | 591 | 71.304 | 93.076 | 39.432 | 1.00 | 14.30 | N |
| ATOM | 18508 | CA | TYR | B | 591 | 71.935 | 93.778 | 40.529 | 1.00 | 14.33 | C |
| ATOM | 18510 | CB | TYR | B | 591 | 73.262 | 93.104 | 40.925 | 1.00 | 15.14 | C |
| ATOM | 18513 | CG | TYR | B | 591 | 73.224 | 91.820 | 41.731 | 1.00 | 15.69 | C |
| ATOM | 18514 | CD1 | TYR | B | 591 | 74.151 | 91.628 | 42.750 | 1.00 | 17.56 | C |
| ATOM | 18516 | CE1 | TYR | B | 591 | 74.177 | 90.483 | 43.492 | 1.00 | 16.71 | C |
| ATOM | 18518 | CZ | TYR | B | 591 | 73.299 | 89.486 | 43.218 | 1.00 | 18.51 | C |
| ATOM | 18519 | OH | TYR | B | 591 | 73.398 | 88.382 | 44.015 | 1.00 | 20.01 | O |
| ATOM | 18521 | CE2 | TYR | B | 591 | 72.377 | 89.607 | 42.211 | 1.00 | 19.48 | C |
| ATOM | 18523 | CD2 | TYR | B | 591 | 72.338 | 90.788 | 41.454 | 1.00 | 17.17 | C |
| ATOM | 18525 | C | TYR | B | 591 | 72.297 | 95.175 | 40.113 | 1.00 | 14.32 | C |
| ATOM | 18526 | O | TYR | B | 591 | 72.698 | 95.407 | 38.959 | 1.00 | 14.51 | O |
| ATOM | 18528 | N | ASP | B | 592 | 72.219 | 96.088 | 41.077 | 1.00 | 13.99 | N |
| ATOM | 18529 | CA | ASP | B | 592 | 72.728 | 97.417 | 40.915 | 1.00 | 13.96 | C |
| ATOM | 18531 | CB | ASP | B | 592 | 72.304 | 98.259 | 42.079 | 1.00 | 13.85 | C |
| ATOM | 18534 | CG | ASP | B | 592 | 70.853 | 98.773 | 41.955 | 1.00 | 15.65 | C |
| ATOM | 18535 | OD1 | ASP | B | 592 | 70.133 | 98.423 | 41.008 | 1.00 | 15.50 | O |
| ATOM | 18536 | OD2 | ASP | B | 592 | 70.437 | 99.527 | 42.861 | 1.00 | 16.73 | O |
| ATOM | 18537 | C | ASP | B | 592 | 74.270 | 97.356 | 40.763 | 1.00 | 13.68 | C |
| ATOM | 18538 | O | ASP | B | 592 | 74.922 | 96.362 | 41.153 | 1.00 | 13.61 | O |
| ATOM | 18540 | N | LEU | B | 593 | 74.826 | 98.404 | 40.157 | 1.00 | 14.50 | N |
| ATOM | 18541 | CA | LEU | B | 593 | 76.199 | 98.369 | 39.676 | 1.00 | 14.73 | C |
| ATOM | 18543 | CB | LEU | B | 593 | 76.526 | 99.669 | 38.954 | 1.00 | 14.81 | C |
| ATOM | 18546 | CG | LEU | B | 593 | 77.939 | 99.778 | 38.404 | 1.00 | 15.80 | C |
| ATOM | 18548 | CD1 | LEU | B | 593 | 78.129 | 98.796 | 37.285 | 1.00 | 15.18 | C |
| ATOM | 18552 | CD2 | LEU | B | 593 | 78.263 | 101.205 | 37.932 | 1.00 | 16.45 | C |
| ATOM | 18556 | C | LEU | B | 593 | 77.217 | 98.073 | 40.768 | 1.00 | 15.24 | C |
| ATOM | 18557 | O | LEU | B | 593 | 78.053 | 97.183 | 40.639 | 1.00 | 13.80 | O |
| ATOM | 18559 | N | VAL | B | 594 | 77.114 | 98.800 | 41.868 | 1.00 | 15.11 | N |
| ATOM | 18560 | CA | VAL | B | 594 | 78.098 | 98.662 | 42.923 | 1.00 | 15.12 | C |
| ATOM | 18562 | CB | VAL | B | 594 | 77.951 | 99.767 | 43.957 | 1.00 | 15.81 | C |

| | | | | | | | | | |
|---|---|---|---|---|---|---|---|---|---|
| ATOM | 18564 | CG1 | VAL | B | 594 | 78.860 | 99.506 | 45.191 | 1.00 15.69 | C |
| ATOM | 18568 | CG2 | VAL | B | 594 | 78.317 | 101.102 | 43.284 | 1.00 15.16 | C |
| ATOM | 18572 | C | VAL | B | 594 | 78.063 | 97.251 | 43.551 | 1.00 14.20 | C |
| ATOM | 18573 | O | VAL | B | 594 | 79.084 | 96.570 | 43.574 | 1.00 14.08 | O |
| ATOM | 18575 | N | PRO | B | 595 | 76.894 | 96.818 | 44.063 | 1.00 14.55 | N |
| ATOM | 18576 | CA | PRO | B | 595 | 76.932 | 95.434 | 44.603 | 1.00 14.45 | C |
| ATOM | 18578 | CB | PRO | B | 595 | 75.538 | 95.240 | 45.224 | 1.00 14.36 | C |
| ATOM | 18581 | CG | PRO | B | 595 | 74.650 | 96.216 | 44.489 | 1.00 13.96 | C |
| ATOM | 18584 | CD | PRO | B | 595 | 75.582 | 97.441 | 44.280 | 1.00 14.33 | C |
| ATOM | 18587 | C | PRO | B | 595 | 77.242 | 94.350 | 43.566 | 1.00 12.69 | C |
| ATOM | 18588 | O | PRO | B | 595 | 77.790 | 93.317 | 43.954 | 1.00 13.14 | O |
| ATOM | 18589 | N | ARG | B | 596 | 76.875 | 94.556 | 42.310 | 1.00 12.20 | N |
| ATOM | 18590 | CA | ARG | B | 596 | 77.182 | 93.619 | 41.254 | 1.00 13.56 | C |
| ATOM | 18592 | CB | ARG | B | 596 | 76.732 | 94.149 | 39.907 | 1.00 14.46 | C |
| ATOM | 18595 | CG | ARG | B | 596 | 76.776 | 93.041 | 38.869 | 1.00 14.37 | C |
| ATOM | 18598 | CD | ARG | B | 596 | 76.235 | 93.462 | 37.538 | 1.00 14.24 | C |
| ATOM | 18601 | NE | ARG | B | 596 | 76.107 | 92.333 | 36.621 | 1.00 15.08 | N |
| ATOM | 18603 | CZ | ARG | B | 596 | 75.734 | 92.485 | 35.365 | 1.00 18.27 | C |
| ATOM | 18604 | NH1 | ARG | B | 596 | 75.440 | 93.699 | 34.920 | 1.00 21.55 | N |
| ATOM | 18607 | NH2 | ARG | B | 596 | 75.628 | 91.449 | 34.573 | 1.00 20.56 | N |
| ATOM | 18610 | C | ARG | B | 596 | 78.661 | 93.331 | 41.192 | 1.00 12.63 | C |
| ATOM | 18611 | O | ARG | B | 596 | 79.089 | 92.189 | 41.117 | 1.00 12.08 | O |
| ATOM | 18613 | N | TRP | B | 597 | 79.454 | 94.393 | 41.154 | 1.00 12.66 | N |
| ATOM | 18614 | CA | TRP | B | 597 | 80.905 | 94.215 | 40.981 | 1.00 13.40 | C |
| ATOM | 18616 | CB | TRP | B | 597 | 81.546 | 95.502 | 40.463 | 1.00 14.26 | C |
| ATOM | 18619 | CG | TRP | B | 597 | 81.258 | 95.593 | 38.980 | 1.00 13.87 | C |
| ATOM | 18620 | CD1 | TRP | B | 597 | 80.404 | 96.439 | 38.348 | 1.00 16.08 | C |
| ATOM | 18622 | NE1 | TRP | B | 597 | 80.385 | 96.171 | 37.010 | 1.00 16.07 | N |
| ATOM | 18624 | CE2 | TRP | B | 597 | 81.232 | 95.125 | 36.754 | 1.00 15.40 | C |
| ATOM | 18625 | CD2 | TRP | B | 597 | 81.781 | 94.721 | 37.989 | 1.00 15.14 | C |
| ATOM | 18626 | CE3 | TRP | B | 597 | 82.670 | 93.628 | 38.017 | 1.00 15.66 | C |
| ATOM | 18628 | CZ3 | TRP | B | 597 | 82.993 | 92.991 | 36.819 | 1.00 16.62 | C |
| ATOM | 18630 | CH2 | TRP | B | 597 | 82.422 | 93.425 | 35.601 | 1.00 15.28 | C |
| ATOM | 18632 | CZ2 | TRP | B | 597 | 81.543 | 94.469 | 35.554 | 1.00 16.19 | C |
| ATOM | 18634 | C | TRP | B | 597 | 81.589 | 93.674 | 42.231 | 1.00 13.38 | C |
| ATOM | 18635 | O | TRP | B | 597 | 82.536 | 92.919 | 42.128 | 1.00 13.81 | O |
| ATOM | 18637 | N | HIS | B | 598 | 81.123 | 94.063 | 43.414 | 1.00 13.05 | N |
| ATOM | 18638 | CA | HIS | B | 598 | 81.639 | 93.480 | 44.626 | 1.00 13.14 | C |
| ATOM | 18640 | CB | HIS | B | 598 | 81.218 | 94.299 | 45.848 | 1.00 12.96 | C |
| ATOM | 18643 | CG | HIS | B | 598 | 81.968 | 95.585 | 45.949 | 1.00 16.04 | C |
| ATOM | 18644 | ND1 | HIS | B | 598 | 83.264 | 95.662 | 46.417 | 1.00 17.90 | N |
| ATOM | 18646 | CE1 | HIS | B | 598 | 83.691 | 96.905 | 46.334 | 1.00 19.02 | C |
| ATOM | 18648 | NE2 | HIS | B | 598 | 82.715 | 97.645 | 45.844 | 1.00 18.38 | N |
| ATOM | 18650 | CD2 | HIS | B | 598 | 81.628 | 96.841 | 45.582 | 1.00 17.77 | C |
| ATOM | 18652 | C | HIS | B | 598 | 81.282 | 91.998 | 44.720 | 1.00 12.35 | C |
| ATOM | 18653 | O | HIS | B | 598 | 82.109 | 91.205 | 45.140 | 1.00 12.24 | O |
| ATOM | 18655 | N | ASP | B | 599 | 80.081 | 91.644 | 44.293 | 1.00 11.35 | N |
| ATOM | 18656 | CA | ASP | B | 599 | 79.703 | 90.228 | 44.228 | 1.00 11.47 | C |
| ATOM | 18658 | CB | ASP | B | 599 | 78.220 | 90.131 | 43.846 | 1.00 10.84 | C |
| ATOM | 18661 | CG | ASP | B | 599 | 77.812 | 88.704 | 43.492 | 1.00 12.98 | C |
| ATOM | 18662 | OD1 | ASP | B | 599 | 77.284 | 88.005 | 44.406 | 1.00 15.04 | O |
| ATOM | 18663 | OD2 | ASP | B | 599 | 78.105 | 88.266 | 42.356 | 1.00 12.25 | O |
| ATOM | 18664 | C | ASP | B | 599 | 80.607 | 89.393 | 43.274 | 1.00 11.17 | C |
| ATOM | 18665 | O | ASP | B | 599 | 81.156 | 88.329 | 43.630 | 1.00 10.85 | O |
| ATOM | 18667 | N | ALA | B | 600 | 80.808 | 89.918 | 42.085 | 1.00 12.15 | N |
| ATOM | 18668 | CA | ALA | B | 600 | 81.622 | 89.216 | 41.077 | 1.00 12.32 | C |
| ATOM | 18670 | CB | ALA | B | 600 | 81.657 | 90.010 | 39.798 | 1.00 12.08 | C |

| ATOM | 18674 | C   | ALA B 600 | 83.051 | 88.957 | 41.560 | 1.00 | 12.02 | C |
| ATOM | 18675 | O   | ALA B 600 | 83.596 | 87.838 | 41.453 | 1.00 | 11.41 | O |
| ATOM | 18677 | N   | PHE B 601 | 83.691 | 89.987 | 42.087 | 1.00 | 10.71 | N |
| ATOM | 18678 | CA  | PHE B 601 | 85.047 | 89.827 | 42.581 | 1.00 | 10.88 | C |
| ATOM | 18680 | CB  | PHE B 601 | 85.811 | 91.165 | 42.575 | 1.00 | 10.80 | C |
| ATOM | 18683 | CG  | PHE B 601 | 86.292 | 91.523 | 41.205 | 1.00 | 10.81 | C |
| ATOM | 18684 | CD1 | PHE B 601 | 87.433 | 90.890 | 40.710 | 1.00 | 13.85 | C |
| ATOM | 18686 | CE1 | PHE B 601 | 87.890 | 91.119 | 39.447 | 1.00 | 14.24 | C |
| ATOM | 18688 | CZ  | PHE B 601 | 87.220 | 91.998 | 38.627 | 1.00 | 12.99 | C |
| ATOM | 18690 | CE2 | PHE B 601 | 86.053 | 92.645 | 39.103 | 1.00 | 12.94 | C |
| ATOM | 18692 | CD2 | PHE B 601 | 85.585 | 92.394 | 40.369 | 1.00 | 13.20 | C |
| ATOM | 18694 | C   | PHE B 601 | 85.156 | 89.062 | 43.890 | 1.00 | 10.14 | C |
| ATOM | 18695 | O   | PHE B 601 | 86.230 | 88.516 | 44.177 | 1.00 | 11.13 | O |
| ATOM | 18697 | N   | SER B 602 | 84.089 | 89.022 | 44.676 | 1.00 | 10.07 | N |
| ATOM | 18698 | CA  | SER B 602 | 84.040 | 88.161 | 45.851 | 1.00 | 10.60 | C |
| ATOM | 18700 | CB  | SER B 602 | 82.770 | 88.368 | 46.659 | 1.00 | 11.10 | C |
| ATOM | 18703 | OG  | SER B 602 | 82.775 | 87.503 | 47.780 | 1.00 | 14.31 | O |
| ATOM | 18705 | C   | SER B 602 | 84.150 | 86.705 | 45.397 | 1.00 | 11.55 | C |
| ATOM | 18706 | O   | SER B 602 | 84.970 | 85.943 | 45.903 | 1.00 | 12.06 | O |
| ATOM | 18708 | N   | PHE B 603 | 83.338 | 86.373 | 44.396 | 1.00 | 11.14 | N |
| ATOM | 18709 | CA  | PHE B 603 | 83.388 | 85.040 | 43.811 | 1.00 | 12.57 | C |
| ATOM | 18711 | CB  | PHE B 603 | 82.315 | 84.894 | 42.750 | 1.00 | 13.54 | C |
| ATOM | 18714 | CG  | PHE B 603 | 81.866 | 83.478 | 42.493 | 1.00 | 15.54 | C |
| ATOM | 18715 | CD1 | PHE B 603 | 82.599 | 82.376 | 42.886 | 1.00 | 14.79 | C |
| ATOM | 18717 | CE1 | PHE B 603 | 82.128 | 81.061 | 42.630 | 1.00 | 15.10 | C |
| ATOM | 18719 | CZ  | PHE B 603 | 80.976 | 80.888 | 41.962 | 1.00 | 18.22 | C |
| ATOM | 18721 | CE2 | PHE B 603 | 80.248 | 81.964 | 41.580 | 1.00 | 22.11 | C |
| ATOM | 18723 | CD2 | PHE B 603 | 80.685 | 83.259 | 41.847 | 1.00 | 20.22 | C |
| ATOM | 18725 | C   | PHE B 603 | 84.790 | 84.797 | 43.239 | 1.00 | 11.34 | C |
| ATOM | 18726 | O   | PHE B 603 | 85.430 | 83.765 | 43.535 | 1.00 | 12.78 | O |
| ATOM | 18728 | N   | ALA B 604 | 85.318 | 85.770 | 42.478 | 1.00 |  9.86 | N |
| ATOM | 18729 | CA  | ALA B 604 | 86.681 | 85.614 | 41.928 | 1.00 | 10.45 | C |
| ATOM | 18731 | CB  | ALA B 604 | 87.068 | 86.778 | 41.007 | 1.00 | 10.94 | C |
| ATOM | 18735 | C   | ALA B 604 | 87.771 | 85.396 | 43.006 | 1.00 |  9.73 | C |
| ATOM | 18736 | O   | ALA B 604 | 88.768 | 84.651 | 42.825 | 1.00 |  9.13 | O |
| ATOM | 18738 | N   | ALA B 605 | 87.581 | 86.006 | 44.168 | 1.00 | 10.45 | N |
| ATOM | 18739 | CA  | ALA B 605 | 88.533 | 85.861 | 45.265 | 1.00 |  9.99 | C |
| ATOM | 18741 | CB  | ALA B 605 | 88.133 | 86.771 | 46.437 | 1.00 | 10.82 | C |
| ATOM | 18745 | C   | ALA B 605 | 88.627 | 84.399 | 45.728 | 1.00 |  9.08 | C |
| ATOM | 18746 | O   | ALA B 605 | 89.674 | 83.959 | 46.134 | 1.00 |  9.89 | O |
| ATOM | 18748 | N   | GLY B 606 | 87.476 | 83.675 | 45.712 | 1.00 |  9.32 | N |
| ATOM | 18749 | CA  | GLY B 606 | 87.481 | 82.223 | 45.958 | 1.00 | 10.12 | C |
| ATOM | 18752 | C   | GLY B 606 | 88.362 | 81.477 | 44.965 | 1.00 |  9.33 | C |
| ATOM | 18753 | O   | GLY B 606 | 89.104 | 80.592 | 45.356 | 1.00 | 11.17 | O |
| ATOM | 18755 | N   | THR B 607 | 88.330 | 81.912 | 43.703 | 1.00 | 10.52 | N |
| ATOM | 18756 | CA  | THR B 607 | 89.174 | 81.293 | 42.662 | 1.00 | 10.25 | C |
| ATOM | 18758 | CB  | THR B 607 | 88.742 | 81.793 | 41.268 | 1.00 | 10.90 | C |
| ATOM | 18760 | OG1 | THR B 607 | 87.380 | 81.376 | 40.993 | 1.00 | 13.25 | O |
| ATOM | 18762 | CG2 | THR B 607 | 89.710 | 81.260 | 40.209 | 1.00 | 12.63 | C |
| ATOM | 18766 | C   | THR B 607 | 90.639 | 81.605 | 42.974 | 1.00 | 10.22 | C |
| ATOM | 18767 | O   | THR B 607 | 91.540 | 80.738 | 42.883 | 1.00 |  9.53 | O |
| ATOM | 18769 | N   | VAL B 608 | 90.913 | 82.832 | 43.406 | 1.00 | 10.15 | N |
| ATOM | 18770 | CA  | VAL B 608 | 92.276 | 83.176 | 43.804 | 1.00 |  9.83 | C |
| ATOM | 18772 | CB  | VAL B 608 | 92.438 | 84.665 | 44.185 | 1.00 | 10.33 | C |
| ATOM | 18774 | CG1 | VAL B 608 | 93.851 | 84.992 | 44.711 | 1.00 | 12.32 | C |
| ATOM | 18778 | CG2 | VAL B 608 | 92.039 | 85.562 | 42.989 | 1.00 | 11.04 | C |
| ATOM | 18782 | C   | VAL B 608 | 92.808 | 82.286 | 44.939 | 1.00 |  9.96 | C |

| ATOM | 18783 | O   | VAL B 608 | 93.933  | 81.801 | 44.902 | 1.00 | 9.29  | O |
|------|-------|-----|-----------|---------|--------|--------|------|-------|---|
| ATOM | 18785 | N   | VAL B 609 | 91.958  | 82.065 | 45.964 | 1.00 | 9.60  | N |
| ATOM | 18786 | CA  | VAL B 609 | 92.308  | 81.222 | 47.089 | 1.00 | 9.97  | C |
| ATOM | 18788 | CB  | VAL B 609 | 91.134  | 81.089 | 48.095 | 1.00 | 10.61 | C |
| ATOM | 18790 | CG1 | VAL B 609 | 91.395  | 79.979 | 49.099 | 1.00 | 10.99 | C |
| ATOM | 18794 | CG2 | VAL B 609 | 90.899  | 82.427 | 48.833 | 1.00 | 11.52 | C |
| ATOM | 18798 | C   | VAL B 609 | 92.780  | 79.817 | 46.616 | 1.00 | 9.83  | C |
| ATOM | 18799 | O   | VAL B 609 | 93.765  | 79.284 | 47.131 | 1.00 | 10.94 | O |
| ATOM | 18801 | N   | GLU B 610 | 92.032  | 79.225 | 45.667 | 1.00 | 10.66 | N |
| ATOM | 18802 | CA  | GLU B 610 | 92.371  | 77.931 | 45.115 | 1.00 | 11.85 | C |
| ATOM | 18804 | CB  | GLU B 610 | 91.248  | 77.391 | 44.245 | 1.00 | 12.12 | C |
| ATOM | 18807 | CG  | GLU B 610 | 91.526  | 76.043 | 43.649 | 1.00 | 15.69 | C |
| ATOM | 18810 | CD  | GLU B 610 | 90.292  | 75.398 | 43.020 | 1.00 | 17.95 | C |
| ATOM | 18811 | OE1 | GLU B 610 | 89.149  | 75.896 | 43.215 | 1.00 | 25.01 | O |
| ATOM | 18812 | OE2 | GLU B 610 | 90.470  | 74.354 | 42.350 | 1.00 | 27.66 | O |
| ATOM | 18813 | C   | GLU B 610 | 93.657  | 77.995 | 44.278 | 1.00 | 10.21 | C |
| ATOM | 18814 | O   | GLU B 610 | 94.616  | 77.274 | 44.531 | 1.00 | 10.11 | O |
| ATOM | 18816 | N   | VAL B 611 | 93.644  | 78.865 | 43.276 | 1.00 | 10.05 | N |
| ATOM | 18817 | CA  | VAL B 611 | 94.731  | 78.868 | 42.278 | 1.00 | 9.21  | C |
| ATOM | 18819 | CB  | VAL B 611 | 94.383  | 79.762 | 41.077 | 1.00 | 9.16  | C |
| ATOM | 18821 | CG1 | VAL B 611 | 95.580  | 79.869 | 40.159 | 1.00 | 10.31 | C |
| ATOM | 18825 | CG2 | VAL B 611 | 93.187  | 79.188 | 40.345 | 1.00 | 10.63 | C |
| ATOM | 18829 | C   | VAL B 611 | 96.076  | 79.260 | 42.912 | 1.00 | 8.66  | C |
| ATOM | 18830 | O   | VAL B 611 | 97.140  | 78.698 | 42.592 | 1.00 | 9.56  | O |
| ATOM | 18832 | N   | LEU B 612 | 96.017  | 80.194 | 43.848 | 1.00 | 8.01  | N |
| ATOM | 18833 | CA  | LEU B 612 | 97.203  | 80.689 | 44.521 | 1.00 | 8.78  | C |
| ATOM | 18835 | CB  | LEU B 612 | 97.184  | 82.217 | 44.575 | 1.00 | 8.49  | C |
| ATOM | 18838 | CG  | LEU B 612 | 97.188  | 82.981 | 43.237 | 1.00 | 9.31  | C |
| ATOM | 18840 | CD1 | LEU B 612 | 97.499  | 84.433 | 43.477 | 1.00 | 10.21 | C |
| ATOM | 18844 | CD2 | LEU B 612 | 98.138  | 82.384 | 42.193 | 1.00 | 11.75 | C |
| ATOM | 18848 | C   | LEU B 612 | 97.339  | 80.129 | 45.947 | 1.00 | 9.88  | C |
| ATOM | 18849 | O   | LEU B 612 | 98.062  | 80.688 | 46.793 | 1.00 | 8.55  | O |
| ATOM | 18851 | N   | SER B 613 | 96.696  | 79.000 | 46.213 | 1.00 | 10.33 | N |
| ATOM | 18852 | CA  | SER B 613 | 96.760  | 78.446 | 47.569 | 1.00 | 11.68 | C |
| ATOM | 18854 | CB  | SER B 613 | 95.912  | 77.181 | 47.676 | 1.00 | 13.01 | C |
| ATOM | 18857 | OG  | SER B 613 | 96.535  | 76.171 | 46.920 | 1.00 | 15.22 | O |
| ATOM | 18859 | C   | SER B 613 | 98.196  | 78.093 | 48.028 | 1.00 | 11.47 | C |
| ATOM | 18860 | O   | SER B 613 | 98.453  | 77.937 | 49.246 | 1.00 | 12.85 | O |
| ATOM | 18862 | N   | SER B 614 | 99.131  | 77.887 | 47.092 | 1.00 | 11.88 | N |
| ATOM | 18863 | CA  | SER B 614 | 100.544 | 77.625 | 47.462 | 1.00 | 12.69 | C |
| ATOM | 18865 | CB  | SER B 614 | 101.265 | 76.907 | 46.320 | 1.00 | 13.59 | C |
| ATOM | 18868 | OG  | SER B 614 | 101.441 | 77.805 | 45.239 | 1.00 | 14.91 | O |
| ATOM | 18870 | C   | SER B 614 | 101.385 | 78.867 | 47.866 | 1.00 | 12.20 | C |
| ATOM | 18871 | O   | SER B 614 | 102.534 | 78.729 | 48.355 | 1.00 | 13.72 | O |
| ATOM | 18873 | N   | THR B 615 | 100.834 | 80.064 | 47.635 | 1.00 | 12.39 | N |
| ATOM | 18874 | CA  | THR B 615 | 101.570 | 81.324 | 47.803 | 1.00 | 12.32 | C |
| ATOM | 18876 | CB  | THR B 615 | 101.071 | 82.387 | 46.821 | 1.00 | 12.00 | C |
| ATOM | 18878 | OG1 | THR B 615 | 99.746  | 82.829 | 47.200 | 1.00 | 11.95 | O |
| ATOM | 18880 | CG2 | THR B 615 | 101.072 | 81.834 | 45.387 | 1.00 | 13.94 | C |
| ATOM | 18884 | C   | THR B 615 | 101.501 | 81.936 | 49.201 | 1.00 | 12.73 | C |
| ATOM | 18885 | O   | THR B 615 | 100.704 | 81.534 | 50.047 | 1.00 | 11.93 | O |
| ATOM | 18887 | N   | SER B 616 | 102.299 | 82.975 | 49.398 | 1.00 | 12.45 | N |
| ATOM | 18888 | CA  | SER B 616 | 102.426 | 83.624 | 50.682 | 1.00 | 12.16 | C |
| ATOM | 18890 | CB  | SER B 616 | 103.873 | 84.113 | 50.835 | 1.00 | 14.00 | C |
| ATOM | 18893 | OG  | SER B 616 | 104.100 | 85.040 | 49.803 | 1.00 | 17.39 | O |
| ATOM | 18895 | C   | SER B 616 | 101.447 | 84.806 | 50.879 | 1.00 | 11.47 | C |
| ATOM | 18896 | O   | SER B 616 | 101.547 | 85.522 | 51.883 | 1.00 | 11.02 | O |

| | | | | | | | | | |
|---|---|---|---|---|---|---|---|---|---|
| ATOM | 18898 | N | LEU | B | 617 | 100.525 | 85.005 | 49.943 | 1.00 11.82 | N |
| ATOM | 18899 | CA | LEU | B | 617 | 99.587 | 86.127 | 49.980 | 1.00 11.42 | C |
| ATOM | 18901 | CB | LEU | B | 617 | 98.665 | 86.114 | 48.772 | 1.00 11.29 | C |
| ATOM | 18904 | CG | LEU | B | 617 | 99.398 | 86.576 | 47.494 | 1.00 9.94 | C |
| ATOM | 18906 | CD1 | LEU | B | 617 | 98.671 | 86.175 | 46.217 | 1.00 13.39 | C |
| ATOM | 18910 | CD2 | LEU | B | 617 | 99.692 | 88.097 | 47.551 | 1.00 12.60 | C |
| ATOM | 18914 | C | LEU | B | 617 | 98.741 | 86.123 | 51.236 | 1.00 12.28 | C |
| ATOM | 18915 | O | LEU | B | 617 | 98.201 | 85.103 | 51.608 | 1.00 12.76 | O |
| ATOM | 18917 | N | SER | B | 618 | 98.595 | 87.281 | 51.849 | 1.00 12.14 | N |
| ATOM | 18918 | CA | SER | B | 618 | 97.660 | 87.398 | 52.958 | 1.00 11.56 | C |
| ATOM | 18920 | CB | SER | B | 618 | 98.038 | 88.605 | 53.786 | 1.00 11.61 | C |
| ATOM | 18923 | OG | SER | B | 618 | 97.721 | 89.780 | 53.083 | 1.00 10.66 | O |
| ATOM | 18925 | C | SER | B | 618 | 96.217 | 87.537 | 52.501 | 1.00 11.30 | C |
| ATOM | 18926 | O | SER | B | 618 | 95.914 | 87.990 | 51.373 | 1.00 10.73 | O |
| ATOM | 18928 | N | LEU | B | 619 | 95.275 | 87.225 | 53.395 | 1.00 10.30 | N |
| ATOM | 18929 | CA | LEU | B | 619 | 93.883 | 87.473 | 53.085 | 1.00 10.06 | C |
| ATOM | 18931 | CB | LEU | B | 619 | 92.942 | 86.961 | 54.167 | 1.00 10.28 | C |
| ATOM | 18934 | CG | LEU | B | 619 | 93.006 | 85.441 | 54.385 | 1.00 11.05 | C |
| ATOM | 18936 | CD1 | LEU | B | 619 | 91.896 | 84.991 | 55.369 | 1.00 12.40 | C |
| ATOM | 18940 | CD2 | LEU | B | 619 | 92.774 | 84.788 | 53.083 | 1.00 13.76 | C |
| ATOM | 18944 | C | LEU | B | 619 | 93.663 | 88.956 | 52.845 | 1.00 9.60 | C |
| ATOM | 18945 | O | LEU | B | 619 | 92.907 | 89.318 | 51.945 | 1.00 10.59 | O |
| ATOM | 18947 | N | ALA | B | 620 | 94.381 | 89.803 | 53.584 | 1.00 10.14 | N |
| ATOM | 18948 | CA | ALA | B | 620 | 94.237 | 91.255 | 53.393 | 1.00 11.25 | C |
| ATOM | 18950 | CB | ALA | B | 620 | 95.091 | 92.016 | 54.386 | 1.00 10.57 | C |
| ATOM | 18954 | C | ALA | B | 620 | 94.593 | 91.660 | 51.948 | 1.00 10.98 | C |
| ATOM | 18955 | O | ALA | B | 620 | 93.958 | 92.519 | 51.343 | 1.00 11.99 | O |
| ATOM | 18957 | N | ALA | B | 621 | 95.642 | 91.033 | 51.416 | 1.00 12.07 | N |
| ATOM | 18958 | CA | ALA | B | 621 | 96.143 | 91.317 | 50.060 | 1.00 11.77 | C |
| ATOM | 18960 | CB | ALA | B | 621 | 97.462 | 90.668 | 49.863 | 1.00 10.63 | C |
| ATOM | 18964 | C | ALA | B | 621 | 95.177 | 90.861 | 48.994 | 1.00 11.19 | C |
| ATOM | 18965 | O | ALA | B | 621 | 94.926 | 91.565 | 48.013 | 1.00 11.43 | O |
| ATOM | 18967 | N | VAL | B | 622 | 94.593 | 89.675 | 49.190 | 1.00 10.87 | N |
| ATOM | 18968 | CA | VAL | B | 622 | 93.571 | 89.185 | 48.274 | 1.00 10.72 | C |
| ATOM | 18970 | CB | VAL | B | 622 | 93.232 | 87.690 | 48.489 | 1.00 10.69 | C |
| ATOM | 18972 | CG1 | VAL | B | 622 | 92.195 | 87.283 | 47.517 | 1.00 10.79 | C |
| ATOM | 18976 | CG2 | VAL | B | 622 | 94.480 | 86.868 | 48.267 | 1.00 11.69 | C |
| ATOM | 18980 | C | VAL | B | 622 | 92.331 | 90.065 | 48.370 | 1.00 10.68 | C |
| ATOM | 18981 | O | VAL | B | 622 | 91.748 | 90.426 | 47.345 | 1.00 10.92 | O |
| ATOM | 18983 | N | ASN | B | 623 | 91.937 | 90.451 | 49.577 | 1.00 9.80 | N |
| ATOM | 18984 | CA | ASN | B | 623 | 90.740 | 91.297 | 49.700 | 1.00 11.47 | C |
| ATOM | 18986 | CB | ASN | B | 623 | 90.352 | 91.456 | 51.164 | 1.00 11.29 | C |
| ATOM | 18989 | CG | ASN | B | 623 | 88.962 | 92.084 | 51.355 | 1.00 11.52 | C |
| ATOM | 18990 | OD1 | ASN | B | 623 | 87.983 | 91.655 | 50.772 | 1.00 14.03 | O |
| ATOM | 18991 | ND2 | ASN | B | 623 | 88.892 | 93.077 | 52.241 | 1.00 17.35 | N |
| ATOM | 18994 | C | ASN | B | 623 | 90.966 | 92.665 | 49.041 | 1.00 11.53 | C |
| ATOM | 18995 | O | ASN | B | 623 | 90.064 | 93.256 | 48.444 | 1.00 11.60 | O |
| ATOM | 18997 | N | ALA | B | 624 | 92.189 | 93.169 | 49.179 | 1.00 12.23 | N |
| ATOM | 18998 | CA | ALA | B | 624 | 92.581 | 94.462 | 48.560 | 1.00 12.66 | C |
| ATOM | 19000 | CB | ALA | B | 624 | 93.968 | 94.837 | 48.962 | 1.00 12.68 | C |
| ATOM | 19004 | C | ALA | B | 624 | 92.466 | 94.427 | 47.054 | 1.00 11.83 | C |
| ATOM | 19005 | O | ALA | B | 624 | 91.980 | 95.367 | 46.441 | 1.00 13.09 | O |
| ATOM | 19007 | N | TRP | B | 625 | 92.948 | 93.344 | 46.449 | 1.00 11.56 | N |
| ATOM | 19008 | CA | TRP | B | 625 | 92.773 | 93.124 | 45.020 | 1.00 11.08 | C |
| ATOM | 19010 | CB | TRP | B | 625 | 93.411 | 91.796 | 44.636 | 1.00 11.03 | C |
| ATOM | 19013 | CG | TRP | B | 625 | 93.072 | 91.389 | 43.275 | 1.00 11.67 | C |
| ATOM | 19014 | CD1 | TRP | B | 625 | 93.603 | 91.871 | 42.112 | 1.00 13.40 | C |

| | | | | | | | | | |
|---|---|---|---|---|---|---|---|---|---|
| ATOM | 19016 | NE1 | TRP | B | 625 | 93.025 | 91.261 | 41.033 | 1.00 14.09 | N |
| ATOM | 19018 | CE2 | TRP | B | 625 | 92.081 | 90.372 | 41.480 | 1.00 13.10 | C |
| ATOM | 19019 | CD2 | TRP | B | 625 | 92.086 | 90.424 | 42.889 | 1.00 12.04 | C |
| ATOM | 19020 | CE3 | TRP | B | 625 | 91.171 | 89.621 | 43.594 | 1.00 13.31 | C |
| ATOM | 19022 | CZ3 | TRP | B | 625 | 90.365 | 88.770 | 42.881 | 1.00 13.49 | C |
| ATOM | 19024 | CH2 | TRP | B | 625 | 90.402 | 88.729 | 41.497 | 1.00 13.37 | C |
| ATOM | 19026 | CZ2 | TRP | B | 625 | 91.250 | 89.527 | 40.774 | 1.00 14.78 | C |
| ATOM | 19028 | C | TRP | B | 625 | 91.290 | 93.134 | 44.641 | 1.00 11.85 | C |
| ATOM | 19029 | O | TRP | B | 625 | 90.852 | 93.841 | 43.718 | 1.00 12.43 | O |
| ATOM | 19031 | N | LYS | B | 626 | 90.504 | 92.360 | 45.385 | 1.00 12.58 | N |
| ATOM | 19032 | CA | LYS | B | 626 | 89.061 | 92.272 | 45.175 | 1.00 12.44 | C |
| ATOM | 19034 | CB | LYS | B | 626 | 88.455 | 91.373 | 46.271 | 1.00 13.55 | C |
| ATOM | 19037 | CG | LYS | B | 626 | 86.932 | 91.261 | 46.232 | 1.00 16.34 | C |
| ATOM | 19040 | CD | LYS | B | 626 | 86.219 | 92.372 | 46.999 | 1.00 18.39 | C |
| ATOM | 19043 | CE | LYS | B | 626 | 84.736 | 92.042 | 47.194 | 1.00 17.91 | C |
| ATOM | 19046 | NZ | LYS | B | 626 | 84.048 | 92.989 | 48.142 | 1.00 18.40 | N |
| ATOM | 19050 | C | LYS | B | 626 | 88.389 | 93.662 | 45.165 | 1.00 13.32 | C |
| ATOM | 19051 | O | LYS | B | 626 | 87.580 | 93.994 | 44.304 | 1.00 13.63 | O |
| ATOM | 19053 | N | VAL | B | 627 | 88.723 | 94.466 | 46.165 | 1.00 13.46 | N |
| ATOM | 19054 | CA | VAL | B | 627 | 88.133 | 95.795 | 46.289 | 1.00 14.17 | C |
| ATOM | 19056 | CB | VAL | B | 627 | 88.409 | 96.399 | 47.669 | 1.00 14.44 | C |
| ATOM | 19058 | CG1 | VAL | B | 627 | 88.001 | 97.852 | 47.692 | 1.00 15.32 | C |
| ATOM | 19062 | CG2 | VAL | B | 627 | 87.628 | 95.622 | 48.753 | 1.00 14.86 | C |
| ATOM | 19066 | C | VAL | B | 627 | 88.606 | 96.697 | 45.130 | 1.00 14.11 | C |
| ATOM | 19067 | O | VAL | B | 627 | 87.791 | 97.386 | 44.465 | 1.00 15.17 | O |
| ATOM | 19069 | N | ALA | B | 628 | 89.910 | 96.694 | 44.862 | 1.00 13.92 | N |
| ATOM | 19070 | CA | ALA | B | 628 | 90.442 | 97.529 | 43.763 | 1.00 13.64 | C |
| ATOM | 19072 | CB | ALA | B | 628 | 91.934 | 97.441 | 43.701 | 1.00 14.40 | C |
| ATOM | 19076 | C | ALA | B | 628 | 89.834 | 97.106 | 42.435 | 1.00 13.19 | C |
| ATOM | 19077 | O | ALA | B | 628 | 89.482 | 97.928 | 41.596 | 1.00 12.30 | O |
| ATOM | 19079 | N | ALA | B | 629 | 89.678 | 95.802 | 42.224 | 1.00 12.25 | N |
| ATOM | 19080 | CA | ALA | B | 629 | 89.162 | 95.349 | 40.964 | 1.00 12.44 | C |
| ATOM | 19082 | CB | ALA | B | 629 | 89.345 | 93.874 | 40.835 | 1.00 12.66 | C |
| ATOM | 19086 | C | ALA | B | 629 | 87.705 | 95.751 | 40.797 | 1.00 13.00 | C |
| ATOM | 19087 | O | ALA | B | 629 | 87.292 | 96.161 | 39.709 | 1.00 13.25 | O |
| ATOM | 19089 | N | ALA | B | 630 | 86.909 | 95.583 | 41.857 | 1.00 12.40 | N |
| ATOM | 19090 | CA | ALA | B | 630 | 85.507 | 96.003 | 41.795 | 1.00 13.49 | C |
| ATOM | 19092 | CB | ALA | B | 630 | 84.786 | 95.646 | 43.051 | 1.00 13.65 | C |
| ATOM | 19096 | C | ALA | B | 630 | 85.392 | 97.517 | 41.510 | 1.00 14.03 | C |
| ATOM | 19097 | O | ALA | B | 630 | 84.580 | 97.947 | 40.681 | 1.00 13.48 | O |
| ATOM | 19099 | N | GLU | B | 631 | 86.186 | 98.327 | 42.216 | 1.00 14.22 | N |
| ATOM | 19100 | CA | GLU | B | 631 | 86.156 | 99.797 | 42.027 | 1.00 15.62 | C |
| ATOM | 19102 | CB | GLU | B | 631 | 87.063 | 100.515 | 43.029 | 1.00 15.67 | C |
| ATOM | 19105 | CG | GLU | B | 631 | 86.497 | 100.497 | 44.422 | 1.00 17.08 | C |
| ATOM | 19108 | CD | GLU | B | 631 | 87.486 | 101.005 | 45.442 | 1.00 21.91 | C |
| ATOM | 19109 | OE1 | GLU | B | 631 | 88.687 | 101.188 | 45.080 | 1.00 26.95 | O |
| ATOM | 19110 | OE2 | GLU | B | 631 | 87.087 | 101.184 | 46.629 | 1.00 29.01 | O |
| ATOM | 19111 | C | GLU | B | 631 | 86.513 | 100.151 | 40.599 | 1.00 15.05 | C |
| ATOM | 19112 | O | GLU | B | 631 | 85.889 | 101.025 | 39.976 | 1.00 15.16 | O |
| ATOM | 19114 | N | SER | B | 632 | 87.504 | 99.447 | 40.076 | 1.00 14.97 | N |
| ATOM | 19115 | CA | SER | B | 632 | 87.935 | 99.644 | 38.704 | 1.00 15.35 | C |
| ATOM | 19117 | CB | SER | B | 632 | 89.182 | 98.791 | 38.421 | 1.00 15.90 | C |
| ATOM | 19120 | OG | SER | B | 632 | 89.548 | 98.836 | 37.046 | 1.00 19.74 | O |
| ATOM | 19122 | C | SER | B | 632 | 86.798 | 99.332 | 37.732 | 1.00 15.05 | C |
| ATOM | 19123 | O | SER | B | 632 | 86.536 | 100.073 | 36.776 | 1.00 14.40 | O |
| ATOM | 19125 | N | ALA | B | 633 | 86.106 | 98.208 | 37.937 | 1.00 14.25 | N |
| ATOM | 19126 | CA | ALA | B | 633 | 84.993 | 97.825 | 37.068 | 1.00 14.24 | C |

| ATOM | 19128 | CB  | ALA B 633 | 84.545 | 96.438  | 37.367 | 1.00 | 15.19 | C |
|------|-------|-----|-----------|--------|---------|--------|------|-------|---|
| ATOM | 19132 | C   | ALA B 633 | 83.814 | 98.813  | 37.146 | 1.00 | 12.92 | C |
| ATOM | 19133 | O   | ALA B 633 | 83.191 | 99.150  | 36.131 | 1.00 | 14.67 | O |
| ATOM | 19135 | N   | ILE B 634 | 83.539 | 99.286  | 38.352 | 1.00 | 12.73 | N |
| ATOM | 19136 | CA  | ILE B 634 | 82.487 | 100.258 | 38.567 | 1.00 | 13.48 | C |
| ATOM | 19138 | CB  | ILE B 634 | 82.298 | 100.506 | 40.071 | 1.00 | 12.33 | C |
| ATOM | 19140 | CG1 | ILE B 634 | 81.727 | 99.216  | 40.739 | 1.00 | 14.32 | C |
| ATOM | 19143 | CD1 | ILE B 634 | 81.861 | 99.120  | 42.217 | 1.00 | 14.22 | C |
| ATOM | 19147 | CG2 | ILE B 634 | 81.344 | 101.704 | 40.307 | 1.00 | 14.63 | C |
| ATOM | 19151 | C   | ILE B 634 | 82.810 | 101.580 | 37.810 | 1.00 | 14.06 | C |
| ATOM | 19152 | O   | ILE B 634 | 81.978 | 102.112 | 37.048 | 1.00 | 13.27 | O |
| ATOM | 19154 | N   | SER B 635 | 84.023 | 102.092 | 37.990 | 1.00 | 14.21 | N |
| ATOM | 19155 | CA  | SER B 635 | 84.447 | 103.293 | 37.258 | 1.00 | 15.55 | C |
| ATOM | 19157 | CB  | SER B 635 | 85.850 | 103.753 | 37.658 | 1.00 | 16.78 | C |
| ATOM | 19160 | OG  | SER B 635 | 85.885 | 103.830 | 39.061 | 1.00 | 21.79 | O |
| ATOM | 19162 | C   | SER B 635 | 84.443 | 103.088 | 35.789 | 1.00 | 15.34 | C |
| ATOM | 19163 | O   | SER B 635 | 83.979 | 103.954 | 35.053 | 1.00 | 15.97 | O |
| ATOM | 19165 | N   | LEU B 636 | 84.986 | 101.978 | 35.322 | 1.00 | 14.69 | N |
| ATOM | 19166 | CA  | LEU B 636 | 85.029 | 101.759 | 33.890 | 1.00 | 15.74 | C |
| ATOM | 19168 | CB  | LEU B 636 | 85.788 | 100.485 | 33.588 | 1.00 | 15.85 | C |
| ATOM | 19171 | CG  | LEU B 636 | 85.972 | 100.080 | 32.120 | 1.00 | 17.73 | C |
| ATOM | 19173 | CD1 | LEU B 636 | 86.577 | 101.224 | 31.278 | 1.00 | 19.51 | C |
| ATOM | 19177 | CD2 | LEU B 636 | 86.894 | 98.875  | 32.045 | 1.00 | 18.24 | C |
| ATOM | 19181 | C   | LEU B 636 | 83.606 | 101.695 | 33.274 | 1.00 | 14.74 | C |
| ATOM | 19182 | O   | LEU B 636 | 83.341 | 102.233 | 32.203 | 1.00 | 16.13 | O |
| ATOM | 19184 | N   | THR B 637 | 82.687 | 101.026 | 33.964 | 1.00 | 13.81 | N |
| ATOM | 19185 | CA  | THR B 637 | 81.310 | 100.946 | 33.505 | 1.00 | 13.54 | C |
| ATOM | 19187 | CB  | THR B 637 | 80.452 | 100.126 | 34.499 | 1.00 | 13.85 | C |
| ATOM | 19189 | OG1 | THR B 637 | 80.941 | 98.794  | 34.547 | 1.00 | 13.50 | O |
| ATOM | 19191 | CG2 | THR B 637 | 79.012 | 100.101 | 34.060 | 1.00 | 15.02 | C |
| ATOM | 19195 | C   | THR B 637 | 80.734 | 102.356 | 33.355 | 1.00 | 13.45 | C |
| ATOM | 19196 | O   | THR B 637 | 80.132 | 102.681 | 32.335 | 1.00 | 12.90 | O |
| ATOM | 19198 | N   | ARG B 638 | 80.933 | 103.189 | 34.365 | 1.00 | 12.97 | N |
| ATOM | 19199 | CA  | ARG B 638 | 80.366 | 104.534 | 34.314 | 1.00 | 14.39 | C |
| ATOM | 19201 | CB  | ARG B 638 | 80.611 | 105.262 | 35.632 | 1.00 | 14.83 | C |
| ATOM | 19204 | CG  | ARG B 638 | 79.799 | 104.670 | 36.752 | 1.00 | 14.51 | C |
| ATOM | 19207 | CD  | ARG B 638 | 79.806 | 105.526 | 37.987 | 1.00 | 18.83 | C |
| ATOM | 19210 | NE  | ARG B 638 | 79.051 | 104.933 | 39.109 | 1.00 | 18.41 | N |
| ATOM | 19212 | CZ  | ARG B 638 | 79.533 | 104.720 | 40.326 | 1.00 | 20.92 | C |
| ATOM | 19213 | NH1 | ARG B 638 | 80.781 | 105.063 | 40.642 | 1.00 | 21.35 | N |
| ATOM | 19216 | NH2 | ARG B 638 | 78.734 | 104.197 | 41.249 | 1.00 | 20.91 | N |
| ATOM | 19219 | C   | ARG B 638 | 80.961 | 105.303 | 33.126 | 1.00 | 14.46 | C |
| ATOM | 19220 | O   | ARG B 638 | 80.248 | 106.031 | 32.419 | 1.00 | 14.12 | O |
| ATOM | 19222 | N   | GLN B 639 | 82.261 | 105.123 | 32.882 | 1.00 | 14.26 | N |
| ATOM | 19223 | CA  | GLN B 639 | 82.917 | 105.879 | 31.797 | 1.00 | 17.03 | C |
| ATOM | 19225 | CB  | GLN B 639 | 84.432 | 105.974 | 31.934 | 1.00 | 18.96 | C |
| ATOM | 19228 | CG  | GLN B 639 | 85.278 | 104.787 | 31.740 | 1.00 | 23.03 | C |
| ATOM | 19231 | CD  | GLN B 639 | 86.807 | 105.109 | 32.045 | 1.00 | 23.14 | C |
| ATOM | 19232 | OE1 | GLN B 639 | 87.140 | 105.790 | 33.034 | 1.00 | 32.96 | O |
| ATOM | 19233 | NE2 | GLN B 639 | 87.705 | 104.624 | 31.192 | 1.00 | 29.79 | N |
| ATOM | 19236 | C   | GLN B 639 | 82.467 | 105.414 | 30.420 | 1.00 | 15.82 | C |
| ATOM | 19237 | O   | GLN B 639 | 82.168 | 106.236 | 29.546 | 1.00 | 16.43 | O |
| ATOM | 19239 | N   | VAL B 640 | 82.293 | 104.112 | 30.263 | 1.00 | 15.15 | N |
| ATOM | 19240 | CA  | VAL B 640 | 81.810 | 103.566 | 28.989 | 1.00 | 14.47 | C |
| ATOM | 19242 | CB  | VAL B 640 | 81.927 | 102.034 | 28.955 | 1.00 | 15.96 | C |
| ATOM | 19244 | CG1 | VAL B 640 | 81.312 | 101.462 | 27.725 | 1.00 | 17.06 | C |
| ATOM | 19248 | CG2 | VAL B 640 | 83.408 | 101.631 | 29.058 | 1.00 | 16.01 | C |

| ATOM | 19252 | C | VAL | B | 640 | 80.361 | 104.002 | 28.711 | 1.00 | 13.09 | C |
|---|---|---|---|---|---|---|---|---|---|---|---|
| ATOM | 19253 | O | VAL | B | 640 | 80.013 | 104.381 | 27.587 | 1.00 | 12.85 | O |
| ATOM | 19255 | N | ARG | B | 641 | 79.535 | 103.984 | 29.746 | 1.00 | 12.64 | N |
| ATOM | 19256 | CA | ARG | B | 641 | 78.201 | 104.525 | 29.611 | 1.00 | 13.23 | C |
| ATOM | 19258 | CB | ARG | B | 641 | 77.454 | 104.405 | 30.902 | 1.00 | 14.02 | C |
| ATOM | 19261 | CG | ARG | B | 641 | 77.050 | 102.989 | 31.142 | 1.00 | 13.24 | C |
| ATOM | 19264 | CD | ARG | B | 641 | 76.589 | 102.830 | 32.602 | 1.00 | 15.56 | C |
| ATOM | 19267 | NE | ARG | B | 641 | 75.975 | 101.541 | 32.901 | 1.00 | 17.11 | N |
| ATOM | 19269 | CZ | ARG | B | 641 | 75.550 | 101.221 | 34.123 | 1.00 | 15.04 | C |
| ATOM | 19270 | NH1 | ARG | B | 641 | 75.672 | 102.071 | 35.117 | 1.00 | 16.77 | N |
| ATOM | 19273 | NH2 | ARG | B | 641 | 74.945 | 100.074 | 34.325 | 1.00 | 18.80 | N |
| ATOM | 19276 | C | ARG | B | 641 | 78.222 | 106.005 | 29.223 | 1.00 | 13.78 | C |
| ATOM | 19277 | O | ARG | B | 641 | 77.523 | 106.414 | 28.299 | 1.00 | 13.49 | O |
| ATOM | 19279 | N | GLU | B | 642 | 79.041 | 106.807 | 29.899 | 1.00 | 14.92 | N |
| ATOM | 19280 | CA | GLU | B | 642 | 79.074 | 108.238 | 29.580 | 1.00 | 15.30 | C |
| ATOM | 19282 | CB | GLU | B | 642 | 79.943 | 109.021 | 30.555 | 1.00 | 16.44 | C |
| ATOM | 19285 | CG | GLU | B | 642 | 79.219 | 109.510 | 31.716 | 1.00 | 20.40 | C |
| ATOM | 19288 | CD | GLU | B | 642 | 77.968 | 110.297 | 31.342 | 1.00 | 24.59 | C |
| ATOM | 19289 | OE1 | GLU | B | 642 | 78.035 | 111.231 | 30.513 | 1.00 | 27.48 | O |
| ATOM | 19290 | OE2 | GLU | B | 642 | 76.916 | 109.972 | 31.902 | 1.00 | 24.36 | O |
| ATOM | 19291 | C | GLU | B | 642 | 79.536 | 108.470 | 28.157 | 1.00 | 15.87 | C |
| ATOM | 19292 | O | GLU | B | 642 | 78.979 | 109.342 | 27.469 | 1.00 | 16.19 | O |
| ATOM | 19294 | N | THR | B | 643 | 80.507 | 107.678 | 27.701 | 1.00 | 13.82 | N |
| ATOM | 19295 | CA | THR | B | 643 | 80.998 | 107.800 | 26.335 | 1.00 | 14.87 | C |
| ATOM | 19297 | CB | THR | B | 643 | 82.136 | 106.853 | 26.082 | 1.00 | 14.69 | C |
| ATOM | 19299 | OG1 | THR | B | 643 | 83.243 | 107.247 | 26.884 | 1.00 | 15.48 | O |
| ATOM | 19301 | CG2 | THR | B | 643 | 82.525 | 106.845 | 24.615 | 1.00 | 15.31 | C |
| ATOM | 19305 | C | THR | B | 643 | 79.844 | 107.561 | 25.353 | 1.00 | 14.68 | C |
| ATOM | 19306 | O | THR | B | 643 | 79.677 | 108.345 | 24.407 | 1.00 | 14.83 | O |
| ATOM | 19308 | N | PHE | B | 644 | 79.034 | 106.514 | 25.577 | 1.00 | 14.13 | N |
| ATOM | 19309 | CA | PHE | B | 644 | 77.839 | 106.280 | 24.772 | 1.00 | 14.74 | C |
| ATOM | 19311 | CB | PHE | B | 644 | 77.128 | 105.020 | 25.287 | 1.00 | 16.26 | C |
| ATOM | 19314 | CG | PHE | B | 644 | 75.860 | 104.677 | 24.561 | 1.00 | 16.33 | C |
| ATOM | 19315 | CD1 | PHE | B | 644 | 75.892 | 103.948 | 23.393 | 1.00 | 23.06 | C |
| ATOM | 19317 | CE1 | PHE | B | 644 | 74.716 | 103.604 | 22.725 | 1.00 | 22.67 | C |
| ATOM | 19319 | CZ | PHE | B | 644 | 73.471 | 103.998 | 23.250 | 1.00 | 20.00 | C |
| ATOM | 19321 | CE2 | PHE | B | 644 | 73.428 | 104.692 | 24.440 | 1.00 | 17.34 | C |
| ATOM | 19323 | CD2 | PHE | B | 644 | 74.620 | 105.016 | 25.094 | 1.00 | 15.84 | C |
| ATOM | 19325 | C | PHE | B | 644 | 76.852 | 107.439 | 24.821 | 1.00 | 14.98 | C |
| ATOM | 19326 | O | PHE | B | 644 | 76.393 | 107.910 | 23.787 | 1.00 | 14.20 | O |
| ATOM | 19328 | N | TRP | B | 645 | 76.449 | 107.831 | 26.022 | 1.00 | 13.48 | N |
| ATOM | 19329 | CA | TRP | B | 645 | 75.306 | 108.757 | 26.124 | 1.00 | 14.42 | C |
| ATOM | 19331 | CB | TRP | B | 645 | 74.702 | 108.718 | 27.512 | 1.00 | 14.04 | C |
| ATOM | 19334 | CG | TRP | B | 645 | 73.993 | 107.438 | 27.785 | 1.00 | 14.25 | C |
| ATOM | 19335 | CD1 | TRP | B | 645 | 74.409 | 106.433 | 28.611 | 1.00 | 14.95 | C |
| ATOM | 19337 | NE1 | TRP | B | 645 | 73.509 | 105.424 | 28.592 | 1.00 | 14.58 | N |
| ATOM | 19339 | CE2 | TRP | B | 645 | 72.467 | 105.742 | 27.754 | 1.00 | 13.53 | C |
| ATOM | 19340 | CD2 | TRP | B | 645 | 72.742 | 106.997 | 27.215 | 1.00 | 13.49 | C |
| ATOM | 19341 | CE3 | TRP | B | 645 | 71.820 | 107.561 | 26.311 | 1.00 | 13.70 | C |
| ATOM | 19343 | CZ3 | TRP | B | 645 | 70.685 | 106.816 | 25.971 | 1.00 | 13.93 | C |
| ATOM | 19345 | CH2 | TRP | B | 645 | 70.431 | 105.597 | 26.560 | 1.00 | 14.07 | C |
| ATOM | 19347 | CZ2 | TRP | B | 645 | 71.333 | 105.018 | 27.421 | 1.00 | 15.06 | C |
| ATOM | 19349 | C | TRP | B | 645 | 75.649 | 110.201 | 25.784 | 1.00 | 15.59 | C |
| ATOM | 19350 | O | TRP | B | 645 | 74.745 | 111.000 | 25.493 | 1.00 | 17.58 | O |
| ATOM | 19352 | N | SER | B | 646 | 76.911 | 110.567 | 25.856 | 1.00 | 15.63 | N |
| ATOM | 19353 | CA | SER | B | 646 | 77.274 | 111.961 | 25.676 | 1.00 | 15.82 | C |
| ATOM | 19355 | CB | SER | B | 646 | 78.511 | 112.294 | 26.526 | 1.00 | 16.46 | C |

| | | | | | | | | | |
|---|---|---|---|---|---|---|---|---|---|
| ATOM | 19358 | OG | SER | B | 646 | 79.630 | 111.610 | 26.013 | 1.00 18.19 | O |
| ATOM | 19360 | C | SER | B | 646 | 77.480 | 112.309 | 24.182 | 1.00 16.45 | C |
| ATOM | 19361 | O | SER | B | 646 | 77.659 | 113.496 | 23.796 | 1.00 18.15 | O |
| ATOM | 19363 | N | ALA | B | 647 | 77.485 | 111.270 | 23.354 | 1.00 16.01 | N |
| ATOM | 19364 | CA | ALA | B | 647 | 77.674 | 111.420 | 21.927 | 1.00 16.75 | C |
| ATOM | 19366 | CB | ALA | B | 647 | 78.730 | 110.455 | 21.432 | 1.00 17.43 | C |
| ATOM | 19370 | C | ALA | B | 647 | 76.362 | 111.161 | 21.218 | 1.00 16.44 | C |
| ATOM | 19371 | O | ALA | B | 647 | 75.516 | 110.459 | 21.705 | 1.00 16.05 | O |
| ATOM | 19373 | N | ALA | B | 648 | 76.246 | 111.690 | 20.000 | 1.00 15.89 | N |
| ATOM | 19374 | CA | ALA | B | 648 | 75.069 | 111.402 | 19.167 | 1.00 16.67 | C |
| ATOM | 19376 | CB | ALA | B | 648 | 75.161 | 112.190 | 17.864 | 1.00 17.11 | C |
| ATOM | 19380 | C | ALA | B | 648 | 74.896 | 109.908 | 18.839 | 1.00 16.19 | C |
| ATOM | 19381 | O | ALA | B | 648 | 75.873 | 109.161 | 18.823 | 1.00 16.03 | O |
| ATOM | 19383 | N | SER | B | 649 | 73.664 | 109.497 | 18.532 | 1.00 15.62 | N |
| ATOM | 19384 | CA | SER | B | 649 | 73.379 | 108.116 | 18.129 | 1.00 15.23 | C |
| ATOM | 19386 | CB | SER | B | 649 | 71.873 | 107.867 | 17.943 | 1.00 15.62 | C |
| ATOM | 19389 | OG | SER | B | 649 | 71.349 | 108.858 | 17.068 | 1.00 16.49 | O |
| ATOM | 19391 | C | SER | B | 649 | 74.123 | 107.704 | 16.844 | 1.00 15.69 | C |
| ATOM | 19392 | O | SER | B | 649 | 74.348 | 106.513 | 16.602 | 1.00 15.83 | O |
| ATOM | 19394 | N | THR | B | 650 | 74.480 | 108.681 | 16.010 | 1.00 14.74 | N |
| ATOM | 19395 | CA | THR | B | 650 | 75.287 | 108.415 | 14.825 | 1.00 13.89 | C |
| ATOM | 19397 | CB | THR | B | 650 | 75.391 | 109.681 | 13.924 | 1.00 14.14 | C |
| ATOM | 19399 | OG1 | THR | B | 650 | 75.592 | 110.820 | 14.753 | 1.00 13.38 | O |
| ATOM | 19401 | CG2 | THR | B | 650 | 74.109 | 109.874 | 13.151 | 1.00 14.52 | C |
| ATOM | 19405 | C | THR | B | 650 | 76.689 | 107.917 | 15.177 | 1.00 14.64 | C |
| ATOM | 19406 | O | THR | B | 650 | 77.431 | 107.510 | 14.266 | 1.00 14.04 | O |
| ATOM | 19408 | N | SER | B | 651 | 77.095 | 108.032 | 16.461 | 1.00 15.18 | N |
| ATOM | 19409 | CA | SER | B | 651 | 78.400 | 107.517 | 16.921 | 1.00 14.22 | C |
| ATOM | 19411 | CB | SER | B | 651 | 79.152 | 108.558 | 17.753 | 1.00 15.07 | C |
| ATOM | 19414 | OG | SER | B | 651 | 79.519 | 109.667 | 16.950 | 1.00 16.75 | O |
| ATOM | 19416 | C | SER | B | 651 | 78.237 | 106.247 | 17.757 | 1.00 13.26 | C |
| ATOM | 19417 | O | SER | B | 651 | 79.199 | 105.816 | 18.437 | 1.00 12.61 | O |
| ATOM | 19419 | N | SER | B | 652 | 77.046 | 105.672 | 17.746 | 1.00 13.78 | N |
| ATOM | 19420 | CA | SER | B | 652 | 76.783 | 104.509 | 18.609 | 1.00 14.33 | C |
| ATOM | 19422 | CB | SER | B | 652 | 75.418 | 103.896 | 18.366 | 1.00 15.53 | C |
| ATOM | 19425 | OG | SER | B | 652 | 75.290 | 102.708 | 19.142 | 1.00 19.31 | O |
| ATOM | 19427 | C | SER | B | 652 | 77.789 | 103.379 | 18.367 | 1.00 14.84 | C |
| ATOM | 19428 | O | SER | B | 652 | 78.015 | 103.000 | 17.219 | 1.00 14.34 | O |
| ATOM | 19430 | N | PRO | B | 653 | 78.327 | 102.769 | 19.445 | 1.00 15.24 | N |
| ATOM | 19431 | CA | PRO | B | 653 | 79.229 | 101.642 | 19.276 | 1.00 14.75 | C |
| ATOM | 19433 | CB | PRO | B | 653 | 79.714 | 101.334 | 20.699 | 1.00 14.51 | C |
| ATOM | 19436 | CG | PRO | B | 653 | 78.678 | 101.853 | 21.574 | 1.00 15.98 | C |
| ATOM | 19439 | CD | PRO | B | 653 | 78.160 | 103.101 | 20.863 | 1.00 16.65 | C |
| ATOM | 19442 | C | PRO | B | 653 | 78.558 | 100.427 | 18.612 | 1.00 14.65 | C |
| ATOM | 19443 | O | PRO | B | 653 | 79.265 | 99.612 | 18.036 | 1.00 16.43 | O |
| ATOM | 19444 | N | ALA | B | 654 | 77.235 | 100.352 | 18.617 | 1.00 13.97 | N |
| ATOM | 19445 | CA | ALA | B | 654 | 76.512 | 99.294 | 17.912 | 1.00 13.69 | C |
| ATOM | 19447 | CB | ALA | B | 654 | 75.023 | 99.517 | 18.024 | 1.00 15.10 | C |
| ATOM | 19451 | C | ALA | B | 654 | 76.918 | 99.255 | 16.432 | 1.00 15.47 | C |
| ATOM | 19452 | O | ALA | B | 654 | 76.943 | 98.183 | 15.824 | 1.00 14.62 | O |
| ATOM | 19454 | N | LEU | B | 655 | 77.206 | 100.425 | 15.857 | 1.00 14.85 | N |
| ATOM | 19455 | CA | LEU | B | 655 | 77.592 | 100.467 | 14.441 | 1.00 16.41 | C |
| ATOM | 19457 | CB | LEU | B | 655 | 77.739 | 101.917 | 13.988 | 1.00 16.26 | C |
| ATOM | 19460 | CG | LEU | B | 655 | 76.467 | 102.732 | 14.164 | 1.00 18.04 | C |
| ATOM | 19462 | CD1 | LEU | B | 655 | 76.736 | 104.198 | 13.846 | 1.00 19.07 | C |
| ATOM | 19466 | CD2 | LEU | B | 655 | 75.298 | 102.250 | 13.346 | 1.00 19.31 | C |
| ATOM | 19470 | C | LEU | B | 655 | 78.883 | 99.694 | 14.191 | 1.00 16.68 | C |

| ATOM | 19471 | O | LEU B 655 | 79.178 | 99.349 | 13.043 | 1.00 | 18.57 | O |
|---|---|---|---|---|---|---|---|---|---|
| ATOM | 19473 | N | SER B 656 | 79.662 | 99.463 | 15.241 | 1.00 | 16.24 | N |
| ATOM | 19474 | CA | SER B 656 | 80.922 | 98.677 | 15.154 | 1.00 | 16.78 | C |
| ATOM | 19476 | CB | SER B 656 | 81.805 | 98.931 | 16.375 | 1.00 | 17.39 | C |
| ATOM | 19479 | OG | SER B 656 | 82.292 | 100.259 | 16.398 | 1.00 | 21.55 | O |
| ATOM | 19481 | C | SER B 656 | 80.708 | 97.154 | 15.039 | 1.00 | 15.93 | C |
| ATOM | 19482 | O | SER B 656 | 81.638 | 96.420 | 14.638 | 1.00 | 16.08 | O |
| ATOM | 19484 | N | TYR B 657 | 79.520 | 96.669 | 15.404 | 1.00 | 13.59 | N |
| ATOM | 19485 | CA | TYR B 657 | 79.298 | 95.257 | 15.536 | 1.00 | 13.49 | C |
| ATOM | 19487 | CB | TYR B 657 | 79.033 | 94.925 | 17.005 | 1.00 | 13.62 | C |
| ATOM | 19490 | CG | TYR B 657 | 80.140 | 95.384 | 17.930 | 1.00 | 14.35 | C |
| ATOM | 19491 | CD1 | TYR B 657 | 81.383 | 94.761 | 17.932 | 1.00 | 19.38 | C |
| ATOM | 19493 | CE1 | TYR B 657 | 82.410 | 95.192 | 18.792 | 1.00 | 18.33 | C |
| ATOM | 19495 | CZ | TYR B 657 | 82.170 | 96.281 | 19.626 | 1.00 | 17.17 | C |
| ATOM | 19496 | OH | TYR B 657 | 83.162 | 96.736 | 20.470 | 1.00 | 17.36 | O |
| ATOM | 19498 | CE2 | TYR B 657 | 80.956 | 96.905 | 19.626 | 1.00 | 14.40 | C |
| ATOM | 19500 | CD2 | TYR B 657 | 79.940 | 96.443 | 18.796 | 1.00 | 15.52 | C |
| ATOM | 19502 | C | TYR B 657 | 78.154 | 94.733 | 14.713 | 1.00 | 14.40 | C |
| ATOM | 19503 | O | TYR B 657 | 78.110 | 93.545 | 14.428 | 1.00 | 13.55 | O |
| ATOM | 19505 | N | LEU B 658 | 77.181 | 95.597 | 14.389 | 1.00 | 13.69 | N |
| ATOM | 19506 | CA | LEU B 658 | 76.016 | 95.135 | 13.642 | 1.00 | 14.42 | C |
| ATOM | 19508 | CB | LEU B 658 | 75.035 | 96.275 | 13.420 | 1.00 | 14.62 | C |
| ATOM | 19511 | CG | LEU B 658 | 74.210 | 96.616 | 14.637 | 1.00 | 17.10 | C |
| ATOM | 19513 | CD1 | LEU B 658 | 73.648 | 97.985 | 14.479 | 1.00 | 19.05 | C |
| ATOM | 19517 | CD2 | LEU B 658 | 73.147 | 95.664 | 14.813 | 1.00 | 18.06 | C |
| ATOM | 19521 | C | LEU B 658 | 76.440 | 94.623 | 12.278 | 1.00 | 13.91 | C |
| ATOM | 19522 | O | LEU B 658 | 77.401 | 95.136 | 11.693 | 1.00 | 13.44 | O |
| ATOM | 19524 | N | SER B 659 | 75.667 | 93.674 | 11.747 | 1.00 | 14.64 | N |
| ATOM | 19525 | CA | SER B 659 | 75.738 | 93.335 | 10.323 | 1.00 | 15.83 | C |
| ATOM | 19527 | CB | SER B 659 | 74.590 | 92.425 | 9.878 | 1.00 | 17.24 | C |
| ATOM | 19530 | OG | SER B 659 | 75.000 | 91.147 | 10.223 | 1.00 | 27.55 | O |
| ATOM | 19532 | C | SER B 659 | 75.554 | 94.559 | 9.525 | 1.00 | 15.21 | C |
| ATOM | 19533 | O | SER B 659 | 74.753 | 95.378 | 9.913 | 1.00 | 14.97 | O |
| ATOM | 19535 | N | PRO B 660 | 76.200 | 94.638 | 8.347 | 1.00 | 14.63 | N |
| ATOM | 19536 | CA | PRO B 660 | 75.896 | 95.773 | 7.491 | 1.00 | 14.64 | C |
| ATOM | 19538 | CB | PRO B 660 | 76.764 | 95.531 | 6.249 | 1.00 | 15.40 | C |
| ATOM | 19541 | CG | PRO B 660 | 77.158 | 94.132 | 6.299 | 1.00 | 15.76 | C |
| ATOM | 19544 | CD | PRO B 660 | 77.251 | 93.793 | 7.764 | 1.00 | 16.06 | C |
| ATOM | 19547 | C | PRO B 660 | 74.434 | 95.896 | 7.094 | 1.00 | 15.14 | C |
| ATOM | 19548 | O | PRO B 660 | 73.972 | 97.007 | 6.832 | 1.00 | 15.70 | O |
| ATOM | 19549 | N | ARG B 661 | 73.740 | 94.758 | 7.009 | 1.00 | 13.00 | N |
| ATOM | 19550 | CA | ARG B 661 | 72.346 | 94.739 | 6.583 | 1.00 | 14.88 | C |
| ATOM | 19552 | CB | ARG B 661 | 71.954 | 93.402 | 5.922 | 1.00 | 15.12 | C |
| ATOM | 19555 | CG | ARG B 661 | 72.600 | 93.207 | 4.566 | 1.00 | 16.07 | C |
| ATOM | 19558 | CD | ARG B 661 | 72.268 | 91.889 | 3.925 | 1.00 | 18.18 | C |
| ATOM | 19561 | NE | ARG B 661 | 72.947 | 91.733 | 2.640 | 1.00 | 20.30 | N |
| ATOM | 19563 | CZ | ARG B 661 | 72.495 | 92.180 | 1.463 | 1.00 | 22.06 | C |
| ATOM | 19564 | NH1 | ARG B 661 | 71.322 | 92.797 | 1.352 | 1.00 | 21.76 | N |
| ATOM | 19567 | NH2 | ARG B 661 | 73.211 | 91.967 | 0.366 | 1.00 | 22.75 | N |
| ATOM | 19570 | C | ARG B 661 | 71.439 | 95.086 | 7.726 | 1.00 | 14.66 | C |
| ATOM | 19571 | O | ARG B 661 | 70.409 | 95.725 | 7.537 | 1.00 | 14.89 | O |
| ATOM | 19573 | N | THR B 662 | 71.755 | 94.631 | 8.931 | 1.00 | 12.89 | N |
| ATOM | 19574 | CA | THR B 662 | 70.855 | 94.971 | 10.051 | 1.00 | 14.21 | C |
| ATOM | 19576 | CB | THR B 662 | 70.965 | 94.029 | 11.252 | 1.00 | 14.17 | C |
| ATOM | 19578 | OG1 | THR B 662 | 72.297 | 93.984 | 11.737 | 1.00 | 13.35 | O |
| ATOM | 19580 | CG2 | THR B 662 | 70.515 | 92.579 | 10.912 | 1.00 | 15.62 | C |
| ATOM | 19584 | C | THR B 662 | 71.079 | 96.419 | 10.506 | 1.00 | 14.12 | C |

| | | | | | | | | | |
|---|---|---|---|---|---|---|---|---|---|
| ATOM | 19585 | O | THR | B | 662 | 70.187 | 97.030 | 11.084 | 1.00 13.71 | O |
| ATOM | 19587 | N | GLN | B | 663 | 72.282 | 96.955 | 10.231 | 1.00 14.00 | N |
| ATOM | 19588 | CA | GLN | B | 663 | 72.556 | 98.359 | 10.516 | 1.00 15.65 | C |
| ATOM | 19590 | CB | GLN | B | 663 | 73.998 | 98.690 | 10.158 | 1.00 16.28 | C |
| ATOM | 19593 | CG | GLN | B | 663 | 74.456 | 100.121 | 10.546 | 1.00 18.23 | C |
| ATOM | 19596 | CD | GLN | B | 663 | 75.906 | 100.373 | 10.105 | 1.00 20.93 | C |
| ATOM | 19597 | OE1 | GLN | B | 663 | 76.760 | 99.517 | 10.314 | 1.00 29.50 | O |
| ATOM | 19598 | NE2 | GLN | B | 663 | 76.155 | 101.508 | 9.434 | 1.00 27.93 | N |
| ATOM | 19601 | C | GLN | B | 663 | 71.562 | 99.284 | 9.750 | 1.00 13.60 | C |
| ATOM | 19602 | O | GLN | B | 663 | 71.245 | 100.392 | 10.207 | 1.00 15.55 | O |
| ATOM | 19604 | N | ILE | B | 664 | 71.089 | 98.845 | 8.584 | 1.00 13.11 | N |
| ATOM | 19605 | CA | ILE | B | 664 | 70.125 | 99.621 | 7.798 | 1.00 13.45 | C |
| ATOM | 19607 | CB | ILE | B | 664 | 69.787 | 98.910 | 6.469 | 1.00 12.68 | C |
| ATOM | 19609 | CG1 | ILE | B | 664 | 71.040 | 98.849 | 5.607 | 1.00 12.28 | C |
| ATOM | 19612 | CD1 | ILE | B | 664 | 70.956 | 97.884 | 4.360 | 1.00 14.77 | C |
| ATOM | 19616 | CG2 | ILE | B | 664 | 68.684 | 99.673 | 5.716 | 1.00 15.03 | C |
| ATOM | 19620 | C | ILE | B | 664 | 68.884 | 99.945 | 8.605 | 1.00 13.48 | C |
| ATOM | 19621 | O | ILE | B | 664 | 68.385 | 101.110 | 8.620 | 1.00 13.84 | O |
| ATOM | 19623 | N | LEU | B | 665 | 68.346 | 98.909 | 9.254 | 1.00 13.38 | N |
| ATOM | 19624 | CA | LEU | B | 665 | 67.117 | 99.061 | 10.037 | 1.00 12.91 | C |
| ATOM | 19626 | CB | LEU | B | 665 | 66.504 | 97.709 | 10.374 | 1.00 13.67 | C |
| ATOM | 19629 | CG | LEU | B | 665 | 65.073 | 97.729 | 10.967 | 1.00 14.12 | C |
| ATOM | 19631 | CD1 | LEU | B | 665 | 64.164 | 98.700 | 10.276 | 1.00 14.00 | C |
| ATOM | 19635 | CD2 | LEU | B | 665 | 64.458 | 96.366 | 11.054 | 1.00 13.94 | C |
| ATOM | 19639 | C | LEU | B | 665 | 67.427 | 99.857 | 11.311 | 1.00 13.40 | C |
| ATOM | 19640 | O | LEU | B | 665 | 66.651 | 100.703 | 11.753 | 1.00 14.82 | O |
| ATOM | 19642 | N | TYR | B | 666 | 68.566 | 99.572 | 11.927 | 1.00 13.36 | N |
| ATOM | 19643 | CA | TYR | B | 666 | 68.985 | 100.305 | 13.122 | 1.00 13.40 | C |
| ATOM | 19645 | CB | TYR | B | 666 | 70.368 | 99.833 | 13.555 | 1.00 13.89 | C |
| ATOM | 19648 | CG | TYR | B | 666 | 70.962 | 100.522 | 14.765 | 1.00 13.24 | C |
| ATOM | 19649 | CD1 | TYR | B | 666 | 70.822 | 99.982 | 16.042 | 1.00 12.04 | C |
| ATOM | 19651 | CE1 | TYR | B | 666 | 71.363 | 100.614 | 17.176 | 1.00 11.65 | C |
| ATOM | 19653 | CZ | TYR | B | 666 | 72.085 | 101.784 | 17.010 | 1.00 14.76 | C |
| ATOM | 19654 | OH | TYR | B | 666 | 72.623 | 102.382 | 18.126 | 1.00 15.48 | O |
| ATOM | 19656 | CE2 | TYR | B | 666 | 72.238 | 102.336 | 15.759 | 1.00 15.14 | C |
| ATOM | 19658 | CD2 | TYR | B | 666 | 71.690 | 101.689 | 14.632 | 1.00 15.34 | C |
| ATOM | 19660 | C | TYR | B | 666 | 69.032 | 101.827 | 12.852 | 1.00 13.48 | C |
| ATOM | 19661 | O | TYR | B | 666 | 68.428 | 102.619 | 13.555 | 1.00 12.71 | O |
| ATOM | 19663 | N | ALA | B | 667 | 69.744 | 102.200 | 11.790 | 1.00 13.06 | N |
| ATOM | 19664 | CA | ALA | B | 667 | 69.859 | 103.602 | 11.364 | 1.00 13.58 | C |
| ATOM | 19666 | CB | ALA | B | 667 | 70.810 | 103.745 | 10.168 | 1.00 13.86 | C |
| ATOM | 19670 | C | ALA | B | 667 | 68.493 | 104.178 | 11.033 | 1.00 13.97 | C |
| ATOM | 19671 | O | ALA | B | 667 | 68.196 | 105.299 | 11.386 | 1.00 14.77 | O |
| ATOM | 19673 | N | PHE | B | 668 | 67.638 | 103.394 | 10.383 | 1.00 13.66 | N |
| ATOM | 19674 | CA | PHE | B | 668 | 66.306 | 103.913 | 10.038 | 1.00 13.39 | C |
| ATOM | 19676 | CB | PHE | B | 668 | 65.507 | 102.842 | 9.305 | 1.00 13.87 | C |
| ATOM | 19679 | CG | PHE | B | 668 | 64.099 | 103.248 | 8.983 | 1.00 13.13 | C |
| ATOM | 19680 | CD1 | PHE | B | 668 | 63.858 | 104.285 | 8.063 | 1.00 16.73 | C |
| ATOM | 19682 | CE1 | PHE | B | 668 | 62.539 | 104.685 | 7.751 | 1.00 16.11 | C |
| ATOM | 19684 | CZ | PHE | B | 668 | 61.482 | 104.017 | 8.353 | 1.00 15.71 | C |
| ATOM | 19686 | CE2 | PHE | B | 668 | 61.728 | 102.988 | 9.290 | 1.00 15.50 | C |
| ATOM | 19688 | CD2 | PHE | B | 668 | 63.014 | 102.604 | 9.596 | 1.00 14.30 | C |
| ATOM | 19690 | C | PHE | B | 668 | 65.541 | 104.358 | 11.259 | 1.00 13.59 | C |
| ATOM | 19691 | O | PHE | B | 668 | 64.962 | 105.437 | 11.301 | 1.00 12.79 | O |
| ATOM | 19693 | N | VAL | B | 669 | 65.541 | 103.513 | 12.291 | 1.00 12.01 | N |
| ATOM | 19694 | CA | VAL | B | 669 | 64.745 | 103.805 | 13.474 | 1.00 12.03 | C |
| ATOM | 19696 | CB | VAL | B | 669 | 64.485 | 102.548 | 14.299 | 1.00 12.78 | C |

| | | | | | | | | | | |
|---|---|---|---|---|---|---|---|---|---|---|
| ATOM | 19698 | CG1 | VAL | B | 669 | 63.757 | 102.930 | 15.553 | 1.00 | 13.78 | C |
| ATOM | 19702 | CG2 | VAL | B | 669 | 63.646 | 101.601 | 13.513 | 1.00 | 13.41 | C |
| ATOM | 19706 | C | VAL | B | 669 | 65.433 | 104.894 | 14.327 | 1.00 | 11.95 | C |
| ATOM | 19707 | O | VAL | B | 669 | 64.793 | 105.867 | 14.767 | 1.00 | 12.32 | O |
| ATOM | 19709 | N | ARG | B | 670 | 66.724 | 104.757 | 14.565 | 1.00 | 11.74 | N |
| ATOM | 19710 | CA | ARG | B | 670 | 67.433 | 105.642 | 15.441 | 1.00 | 12.57 | C |
| ATOM | 19712 | CB | ARG | B | 670 | 68.815 | 105.022 | 15.759 | 1.00 | 12.22 | C |
| ATOM | 19715 | CG | ARG | B | 670 | 68.789 | 103.889 | 16.786 | 1.00 | 12.86 | C |
| ATOM | 19718 | CD | ARG | B | 670 | 68.908 | 104.460 | 18.199 | 1.00 | 13.28 | C |
| ATOM | 19721 | NE | ARG | B | 670 | 68.970 | 103.395 | 19.211 | 1.00 | 13.25 | N |
| ATOM | 19723 | CZ | ARG | B | 670 | 67.931 | 102.816 | 19.764 | 1.00 | 12.74 | C |
| ATOM | 19724 | NH1 | ARG | B | 670 | 66.698 | 103.156 | 19.424 | 1.00 | 12.92 | N |
| ATOM | 19727 | NH2 | ARG | B | 670 | 68.111 | 101.895 | 20.698 | 1.00 | 12.25 | N |
| ATOM | 19730 | C | ARG | B | 670 | 67.570 | 107.055 | 14.843 | 1.00 | 13.85 | C |
| ATOM | 19731 | O | ARG | B | 670 | 67.492 | 108.067 | 15.566 | 1.00 | 15.18 | O |
| ATOM | 19733 | N | GLU | B | 671 | 67.832 | 107.132 | 13.540 | 1.00 | 12.35 | N |
| ATOM | 19734 | CA | GLU | B | 671 | 68.067 | 108.403 | 12.868 | 1.00 | 12.83 | C |
| ATOM | 19736 | CB | GLU | B | 671 | 69.206 | 108.294 | 11.883 | 1.00 | 12.48 | C |
| ATOM | 19739 | CG | GLU | B | 671 | 70.495 | 107.824 | 12.490 | 1.00 | 14.23 | C |
| ATOM | 19742 | CD | GLU | B | 671 | 70.853 | 108.462 | 13.824 | 1.00 | 18.92 | C |
| ATOM | 19743 | OE1 | GLU | B | 671 | 70.680 | 109.683 | 14.003 | 1.00 | 20.58 | O |
| ATOM | 19744 | OE2 | GLU | B | 671 | 71.376 | 107.730 | 14.703 | 1.00 | 20.37 | O |
| ATOM | 19745 | C | GLU | B | 671 | 66.840 | 108.905 | 12.161 | 1.00 | 14.32 | C |
| ATOM | 19746 | O | GLU | B | 671 | 66.351 | 109.994 | 12.487 | 1.00 | 16.45 | O |
| ATOM | 19748 | N | GLU | B | 672 | 66.298 | 108.171 | 11.188 | 1.00 | 13.59 | N |
| ATOM | 19749 | CA | GLU | B | 672 | 65.179 | 108.736 | 10.430 | 1.00 | 15.47 | C |
| ATOM | 19751 | CB | GLU | B | 672 | 64.835 | 107.917 | 9.188 | 1.00 | 15.99 | C |
| ATOM | 19754 | CG | GLU | B | 672 | 65.860 | 108.012 | 8.087 | 1.00 | 18.14 | C |
| ATOM | 19757 | CD | GLU | B | 672 | 65.404 | 107.356 | 6.779 | 1.00 | 20.08 | C |
| ATOM | 19758 | OE1 | GLU | B | 672 | 64.400 | 107.819 | 6.169 | 1.00 | 25.33 | O |
| ATOM | 19759 | OE2 | GLU | B | 672 | 66.070 | 106.402 | 6.323 | 1.00 | 22.95 | O |
| ATOM | 19760 | C | GLU | B | 672 | 63.923 | 108.904 | 11.250 | 1.00 | 15.17 | C |
| ATOM | 19761 | O | GLU | B | 672 | 63.227 | 109.928 | 11.127 | 1.00 | 15.10 | O |
| ATOM | 19763 | N | LEU | B | 673 | 63.637 | 107.928 | 12.122 | 1.00 | 14.19 | N |
| ATOM | 19764 | CA | LEU | B | 673 | 62.463 | 107.999 | 12.991 | 1.00 | 14.83 | C |
| ATOM | 19766 | CB | LEU | B | 673 | 61.910 | 106.615 | 13.302 | 1.00 | 15.07 | C |
| ATOM | 19769 | CG | LEU | B | 673 | 61.484 | 105.745 | 12.133 | 1.00 | 14.64 | C |
| ATOM | 19771 | CD1 | LEU | B | 673 | 60.711 | 104.518 | 12.642 | 1.00 | 14.56 | C |
| ATOM | 19775 | CD2 | LEU | B | 673 | 60.724 | 106.551 | 11.087 | 1.00 | 15.09 | C |
| ATOM | 19779 | C | LEU | B | 673 | 62.736 | 108.748 | 14.295 | 1.00 | 14.85 | C |
| ATOM | 19780 | O | LEU | B | 673 | 61.789 | 109.111 | 15.005 | 1.00 | 16.54 | O |
| ATOM | 19782 | N | GLY | B | 674 | 64.001 | 108.974 | 14.627 | 1.00 | 14.39 | N |
| ATOM | 19783 | CA | GLY | B | 674 | 64.360 | 109.712 | 15.826 | 1.00 | 14.49 | C |
| ATOM | 19786 | C | GLY | B | 674 | 64.158 | 108.994 | 17.145 | 1.00 | 15.34 | C |
| ATOM | 19787 | O | GLY | B | 674 | 64.133 | 109.657 | 18.191 | 1.00 | 15.90 | O |
| ATOM | 19789 | N | VAL | B | 675 | 64.021 | 107.667 | 17.108 | 1.00 | 14.11 | N |
| ATOM | 19790 | CA | VAL | B | 675 | 63.755 | 106.847 | 18.290 | 1.00 | 13.69 | C |
| ATOM | 19792 | CB | VAL | B | 675 | 62.904 | 105.598 | 17.950 | 1.00 | 14.51 | C |
| ATOM | 19794 | CG1 | VAL | B | 675 | 62.756 | 104.760 | 19.152 | 1.00 | 12.87 | C |
| ATOM | 19798 | CG2 | VAL | B | 675 | 61.519 | 106.027 | 17.413 | 1.00 | 15.81 | C |
| ATOM | 19802 | C | VAL | B | 675 | 65.090 | 106.411 | 18.886 | 1.00 | 14.35 | C |
| ATOM | 19803 | O | VAL | B | 675 | 65.763 | 105.572 | 18.295 | 1.00 | 13.38 | O |
| ATOM | 19805 | N | LYS | B | 676 | 65.435 | 106.980 | 20.047 | 1.00 | 14.21 | N |
| ATOM | 19806 | CA | LYS | B | 676 | 66.744 | 106.866 | 20.672 | 1.00 | 12.93 | C |
| ATOM | 19808 | CB | LYS | B | 676 | 67.184 | 108.195 | 21.299 | 1.00 | 14.45 | C |
| ATOM | 19811 | CG | LYS | B | 676 | 67.280 | 109.372 | 20.304 | 1.00 | 14.79 | C |
| ATOM | 19814 | CD | LYS | B | 676 | 68.072 | 109.015 | 18.981 | 1.00 | 15.12 | C |

| | | | | | | | | | |
|---|---|---|---|---|---|---|---|---|---|
| ATOM | 19817 | CE | LYS | B | 676 | 68.392 | 110.138 | 17.973 | 1.00 20.50 | C |
| ATOM | 19820 | NZ | LYS | B | 676 | 67.172 | 110.737 | 17.559 | 1.00 29.39 | N |
| ATOM | 19824 | C | LYS | B | 676 | 66.694 | 105.757 | 21.746 | 1.00 12.85 | C |
| ATOM | 19825 | O | LYS | B | 676 | 65.642 | 105.418 | 22.312 | 1.00 12.91 | O |
| ATOM | 19827 | N | ALA | B | 677 | 67.863 | 105.230 | 22.067 | 1.00 12.56 | N |
| ATOM | 19828 | CA | ALA | B | 677 | 68.022 | 104.469 | 23.313 | 1.00 13.37 | C |
| ATOM | 19830 | CB | ALA | B | 677 | 69.444 | 104.112 | 23.516 | 1.00 13.04 | C |
| ATOM | 19834 | C | ALA | B | 677 | 67.530 | 105.337 | 24.487 | 1.00 13.70 | C |
| ATOM | 19835 | O | ALA | B | 677 | 67.595 | 106.567 | 24.433 | 1.00 13.53 | O |
| ATOM | 19837 | N | ARG | B | 678 | 67.073 | 104.682 | 25.546 | 1.00 13.39 | N |
| ATOM | 19838 | CA | ARG | B | 678 | 66.487 | 105.342 | 26.695 | 1.00 12.67 | C |
| ATOM | 19840 | CB | ARG | B | 678 | 65.078 | 104.827 | 26.964 | 1.00 11.38 | C |
| ATOM | 19843 | CG | ARG | B | 678 | 64.326 | 105.685 | 27.978 | 1.00 11.85 | C |
| ATOM | 19846 | CD | ARG | B | 678 | 62.989 | 105.085 | 28.375 | 1.00 13.34 | C |
| ATOM | 19849 | NE | ARG | B | 678 | 62.194 | 106.085 | 29.123 | 1.00 12.06 | N |
| ATOM | 19851 | CZ | ARG | B | 678 | 61.423 | 107.012 | 28.558 | 1.00 13.92 | C |
| ATOM | 19852 | NH1 | ARG | B | 678 | 61.224 | 107.057 | 27.253 | 1.00 13.61 | N |
| ATOM | 19855 | NH2 | ARG | B | 678 | 60.818 | 107.893 | 29.328 | 1.00 13.65 | N |
| ATOM | 19858 | C | ARG | B | 678 | 67.315 | 105.090 | 27.929 | 1.00 13.23 | C |
| ATOM | 19859 | O | ARG | B | 678 | 67.537 | 103.928 | 28.336 | 1.00 12.58 | O |
| ATOM | 19861 | N | ARG | B | 679 | 67.785 | 106.156 | 28.529 | 1.00 14.31 | N |
| ATOM | 19862 | CA | ARG | B | 679 | 68.686 | 106.017 | 29.678 | 1.00 13.39 | C |
| ATOM | 19864 | CB | ARG | B | 679 | 69.591 | 107.226 | 29.823 | 1.00 13.69 | C |
| ATOM | 19867 | CG | ARG | B | 679 | 70.740 | 106.987 | 30.758 | 1.00 12.60 | C |
| ATOM | 19870 | CD | ARG | B | 679 | 71.890 | 107.945 | 30.617 | 1.00 13.04 | C |
| ATOM | 19873 | NE | ARG | B | 679 | 73.086 | 107.501 | 31.336 | 1.00 12.66 | N |
| ATOM | 19875 | CZ | ARG | B | 679 | 74.203 | 108.208 | 31.474 | 1.00 14.38 | C |
| ATOM | 19876 | NH1 | ARG | B | 679 | 74.360 | 109.421 | 30.901 | 1.00 13.47 | N |
| ATOM | 19879 | NH2 | ARG | B | 679 | 75.216 | 107.667 | 32.157 | 1.00 16.73 | N |
| ATOM | 19882 | C | ARG | B | 679 | 67.996 | 105.812 | 30.996 | 1.00 13.02 | C |
| ATOM | 19883 | O | ARG | B | 679 | 68.522 | 105.122 | 31.830 | 1.00 13.73 | O |
| ATOM | 19885 | N | GLY | B | 680 | 66.791 | 106.384 | 31.169 | 1.00 13.20 | N |
| ATOM | 19886 | CA | GLY | B | 680 | 65.996 | 106.137 | 32.361 | 1.00 13.94 | C |
| ATOM | 19889 | C | GLY | B | 680 | 65.581 | 107.417 | 33.066 | 1.00 13.65 | C |
| ATOM | 19890 | O | GLY | B | 680 | 66.418 | 108.268 | 33.369 | 1.00 14.42 | O |
| ATOM | 19892 | N | ASP | B | 681 | 64.266 | 107.555 | 33.310 | 1.00 14.54 | N |
| ATOM | 19893 | CA | ASP | B | 681 | 63.743 | 108.781 | 33.930 | 1.00 13.79 | C |
| ATOM | 19895 | CB | ASP | B | 681 | 62.244 | 108.701 | 34.124 | 1.00 13.65 | C |
| ATOM | 19898 | CG | ASP | B | 681 | 61.468 | 108.749 | 32.814 | 1.00 15.97 | C |
| ATOM | 19899 | OD1 | ASP | B | 681 | 62.081 | 108.857 | 31.733 | 1.00 15.58 | O |
| ATOM | 19900 | OD2 | ASP | B | 681 | 60.213 | 108.671 | 32.894 | 1.00 15.07 | O |
| ATOM | 19901 | C | ASP | B | 681 | 64.375 | 109.092 | 35.299 | 1.00 13.55 | C |
| ATOM | 19902 | O | ASP | B | 681 | 64.578 | 110.243 | 35.641 | 1.00 14.21 | O |
| ATOM | 19904 | N | VAL | B | 682 | 64.597 | 108.070 | 36.107 | 1.00 12.75 | N |
| ATOM | 19905 | CA | VAL | B | 682 | 65.123 | 108.315 | 37.452 | 1.00 13.48 | C |
| ATOM | 19907 | CB | VAL | B | 682 | 64.915 | 107.108 | 38.372 | 1.00 13.62 | C |
| ATOM | 19909 | CG1 | VAL | B | 682 | 65.594 | 107.305 | 39.693 | 1.00 12.50 | C |
| ATOM | 19913 | CG2 | VAL | B | 682 | 63.437 | 106.848 | 38.586 | 1.00 15.86 | C |
| ATOM | 19917 | C | VAL | B | 682 | 66.600 | 108.732 | 37.375 | 1.00 13.69 | C |
| ATOM | 19918 | O | VAL | B | 682 | 66.982 | 109.721 | 37.987 | 1.00 15.90 | O |
| ATOM | 19920 | N | PHE | B | 683 | 67.404 | 108.005 | 36.615 | 1.00 13.18 | N |
| ATOM | 19921 | CA | PHE | B | 683 | 68.801 | 108.374 | 36.443 | 1.00 14.49 | C |
| ATOM | 19923 | CB | PHE | B | 683 | 69.526 | 107.472 | 35.438 | 1.00 14.09 | C |
| ATOM | 19926 | CG | PHE | B | 683 | 70.961 | 107.888 | 35.243 | 1.00 14.03 | C |
| ATOM | 19927 | CD1 | PHE | B | 683 | 71.959 | 107.433 | 36.129 | 1.00 16.43 | C |
| ATOM | 19929 | CE1 | PHE | B | 683 | 73.283 | 107.848 | 36.009 | 1.00 17.12 | C |
| ATOM | 19931 | CZ | PHE | B | 683 | 73.601 | 108.717 | 35.031 | 1.00 16.12 | C |

| ATOM | 19933 | CE2 | PHE | B | 683 | 72.640 | 109.203 | 34.171 | 1.00 | 15.86 | C |
|------|-------|-----|-----|---|-----|--------|---------|--------|------|-------|---|
| ATOM | 19935 | CD2 | PHE | B | 683 | 71.307 | 108.794 | 34.285 | 1.00 | 15.35 | C |
| ATOM | 19937 | C | PHE | B | 683 | 68.907 | 109.824 | 35.966 | 1.00 | 14.30 | C |
| ATOM | 19938 | O | PHE | B | 683 | 69.766 | 110.629 | 36.417 | 1.00 | 13.42 | O |
| ATOM | 19940 | N | LEU | B | 684 | 68.065 | 110.179 | 34.983 | 1.00 | 13.37 | N |
| ATOM | 19941 | CA | LEU | B | 684 | 68.104 | 111.510 | 34.368 | 1.00 | 12.92 | C |
| ATOM | 19943 | CB | LEU | B | 684 | 67.441 | 111.506 | 32.976 | 1.00 | 14.34 | C |
| ATOM | 19946 | CG | LEU | B | 684 | 68.151 | 110.681 | 31.906 | 1.00 | 15.38 | C |
| ATOM | 19948 | CD1 | LEU | B | 684 | 67.295 | 110.663 | 30.639 | 1.00 | 16.17 | C |
| ATOM | 19952 | CD2 | LEU | B | 684 | 69.518 | 111.225 | 31.552 | 1.00 | 16.65 | C |
| ATOM | 19956 | C | LEU | B | 684 | 67.462 | 112.609 | 35.221 | 1.00 | 13.72 | C |
| ATOM | 19957 | O | LEU | B | 684 | 67.680 | 113.802 | 34.981 | 1.00 | 15.12 | O |
| ATOM | 19959 | N | GLY | B | 685 | 66.679 | 112.243 | 36.210 | 1.00 | 13.49 | N |
| ATOM | 19960 | CA | GLY | B | 685 | 65.888 | 113.219 | 36.967 | 1.00 | 15.65 | C |
| ATOM | 19963 | C | GLY | B | 685 | 64.931 | 113.977 | 36.068 | 1.00 | 16.20 | C |
| ATOM | 19964 | O | GLY | B | 685 | 64.654 | 115.165 | 36.299 | 1.00 | 16.76 | O |
| ATOM | 19966 | N | LYS | B | 686 | 64.436 | 113.308 | 35.042 | 1.00 | 16.22 | N |
| ATOM | 19967 | CA | LYS | B | 686 | 63.549 | 113.914 | 34.056 | 1.00 | 18.31 | C |
| ATOM | 19969 | CB | LYS | B | 686 | 64.374 | 114.465 | 32.884 | 1.00 | 19.68 | C |
| ATOM | 19972 | CG | LYS | B | 686 | 63.582 | 115.331 | 31.912 | 1.00 | 21.38 | C |
| ATOM | 19975 | CD | LYS | B | 686 | 64.288 | 115.424 | 30.579 | 1.00 | 22.07 | C |
| ATOM | 19978 | CE | LYS | B | 686 | 63.431 | 116.185 | 29.546 | 1.00 | 25.53 | C |
| ATOM | 19981 | NZ | LYS | B | 686 | 64.307 | 116.773 | 28.522 | 1.00 | 25.40 | N |
| ATOM | 19985 | C | LYS | B | 686 | 62.607 | 112.838 | 33.552 | 1.00 | 17.33 | C |
| ATOM | 19986 | O | LYS | B | 686 | 63.042 | 111.709 | 33.253 | 1.00 | 17.46 | O |
| ATOM | 19988 | N | GLN | B | 687 | 61.319 | 113.169 | 33.494 | 1.00 | 15.15 | N |
| ATOM | 19989 | CA | GLN | B | 687 | 60.325 | 112.265 | 32.918 | 1.00 | 15.16 | C |
| ATOM | 19991 | CB | GLN | B | 687 | 58.993 | 112.505 | 33.621 | 1.00 | 14.86 | C |
| ATOM | 19994 | CG | GLN | B | 687 | 59.004 | 111.997 | 35.064 | 1.00 | 17.39 | C |
| ATOM | 19997 | CD | GLN | B | 687 | 57.660 | 112.157 | 35.712 | 1.00 | 18.37 | C |
| ATOM | 19998 | OE1 | GLN | B | 687 | 57.266 | 113.278 | 36.091 | 1.00 | 21.89 | O |
| ATOM | 19999 | NE2 | GLN | B | 687 | 56.934 | 111.065 | 35.834 | 1.00 | 17.57 | N |
| ATOM | 20002 | C | GLN | B | 687 | 60.247 | 112.526 | 31.425 | 1.00 | 15.32 | C |
| ATOM | 20003 | O | GLN | B | 687 | 59.550 | 113.446 | 30.977 | 1.00 | 15.88 | O |
| ATOM | 20005 | N | GLU | B | 688 | 61.005 | 111.743 | 30.645 | 1.00 | 15.55 | N |
| ATOM | 20006 | CA | GLU | B | 688 | 61.144 | 112.007 | 29.228 | 1.00 | 15.85 | C |
| ATOM | 20008 | CB | GLU | B | 688 | 62.331 | 111.245 | 28.643 | 1.00 | 16.14 | C |
| ATOM | 20011 | CG | GLU | B | 688 | 63.661 | 111.553 | 29.241 | 1.00 | 17.75 | C |
| ATOM | 20014 | CD | GLU | B | 688 | 64.822 | 111.113 | 28.352 | 1.00 | 15.95 | C |
| ATOM | 20015 | OE1 | GLU | B | 688 | 65.046 | 109.878 | 28.188 | 1.00 | 15.56 | O |
| ATOM | 20016 | OE2 | GLU | B | 688 | 65.539 | 112.045 | 27.828 | 1.00 | 18.62 | O |
| ATOM | 20017 | C | GLU | B | 688 | 59.893 | 111.557 | 28.482 | 1.00 | 15.45 | C |
| ATOM | 20018 | O | GLU | B | 688 | 59.095 | 110.788 | 28.988 | 1.00 | 15.47 | O |
| ATOM | 20020 | N | VAL | B | 689 | 59.761 | 112.060 | 27.254 | 1.00 | 15.06 | N |
| ATOM | 20021 | CA | VAL | B | 689 | 58.732 | 111.594 | 26.326 | 1.00 | 15.07 | C |
| ATOM | 20023 | CB | VAL | B | 689 | 59.065 | 112.072 | 24.891 | 1.00 | 14.72 | C |
| ATOM | 20025 | CG1 | VAL | B | 689 | 58.258 | 111.335 | 23.871 | 1.00 | 15.70 | C |
| ATOM | 20029 | CG2 | VAL | B | 689 | 58.801 | 113.587 | 24.784 | 1.00 | 14.63 | C |
| ATOM | 20033 | C | VAL | B | 689 | 58.662 | 110.083 | 26.405 | 1.00 | 14.29 | C |
| ATOM | 20034 | O | VAL | B | 689 | 59.708 | 109.429 | 26.484 | 1.00 | 13.95 | O |
| ATOM | 20036 | N | THR | B | 690 | 57.466 | 109.516 | 26.473 | 1.00 | 13.37 | N |
| ATOM | 20037 | CA | THR | B | 690 | 57.284 | 108.176 | 26.951 | 1.00 | 12.74 | C |
| ATOM | 20039 | CB | THR | B | 690 | 55.781 | 107.868 | 27.217 | 1.00 | 13.57 | C |
| ATOM | 20041 | OG1 | THR | B | 690 | 55.061 | 108.073 | 25.989 | 1.00 | 14.56 | O |
| ATOM | 20043 | CG2 | THR | B | 690 | 55.241 | 108.765 | 28.345 | 1.00 | 12.56 | C |
| ATOM | 20047 | C | THR | B | 690 | 57.759 | 107.135 | 25.981 | 1.00 | 12.90 | C |
| ATOM | 20048 | O | THR | B | 690 | 57.857 | 107.341 | 24.760 | 1.00 | 12.47 | O |

| | | | | | | | | | |
|---|---|---|---|---|---|---|---|---|---|
| ATOM | 20050 | N | ILE | B | 691 | 57.955 | 105.955 | 26.539 | 1.00 12.00 | N |
| ATOM | 20051 | CA | ILE | B | 691 | 58.248 | 104.782 | 25.718 | 1.00 12.79 | C |
| ATOM | 20053 | CB | ILE | B | 691 | 58.319 | 103.563 | 26.648 | 1.00 12.65 | C |
| ATOM | 20055 | CG1 | ILE | B | 691 | 59.538 | 103.723 | 27.557 | 1.00 13.62 | C |
| ATOM | 20058 | CD1 | ILE | B | 691 | 59.454 | 102.846 | 28.793 | 1.00 15.33 | C |
| ATOM | 20062 | CG2 | ILE | B | 691 | 58.344 | 102.202 | 25.846 | 1.00 13.55 | C |
| ATOM | 20066 | C | ILE | B | 691 | 57.176 | 104.582 | 24.645 | 1.00 12.41 | C |
| ATOM | 20067 | O | ILE | B | 691 | 57.515 | 104.330 | 23.444 | 1.00 13.94 | O |
| ATOM | 20069 | N | GLY | B | 692 | 55.920 | 104.730 | 25.044 | 1.00 12.06 | N |
| ATOM | 20070 | CA | GLY | B | 692 | 54.800 | 104.570 | 24.102 | 1.00 12.66 | C |
| ATOM | 20073 | C | GLY | B | 692 | 54.852 | 105.520 | 22.931 | 1.00 13.31 | C |
| ATOM | 20074 | O | GLY | B | 692 | 54.584 | 105.123 | 21.793 | 1.00 14.11 | O |
| ATOM | 20076 | N | SER | B | 693 | 55.210 | 106.781 | 23.212 | 1.00 11.87 | N |
| ATOM | 20077 | CA | SER | B | 693 | 55.338 | 107.800 | 22.166 | 1.00 13.75 | C |
| ATOM | 20079 | CB | SER | B | 693 | 55.686 | 109.159 | 22.744 | 1.00 13.87 | C |
| ATOM | 20082 | OG | SER | B | 693 | 54.571 | 109.711 | 23.449 | 1.00 15.95 | O |
| ATOM | 20084 | C | SER | B | 693 | 56.373 | 107.379 | 21.144 | 1.00 13.84 | C |
| ATOM | 20085 | O | SER | B | 693 | 56.189 | 107.563 | 19.954 | 1.00 14.54 | O |
| ATOM | 20087 | N | ASN | B | 694 | 57.449 | 106.746 | 21.622 | 1.00 13.63 | N |
| ATOM | 20088 | CA | ASN | B | 694 | 58.525 | 106.258 | 20.718 | 1.00 14.35 | C |
| ATOM | 20090 | CB | ASN | B | 694 | 59.855 | 106.087 | 21.479 | 1.00 14.91 | C |
| ATOM | 20093 | CG | ASN | B | 694 | 60.373 | 107.425 | 21.986 | 1.00 15.38 | C |
| ATOM | 20094 | OD1 | ASN | B | 694 | 60.674 | 107.630 | 23.173 | 1.00 17.82 | O |
| ATOM | 20095 | ND2 | ASN | B | 694 | 60.445 | 108.378 | 21.088 | 1.00 17.80 | N |
| ATOM | 20098 | C | ASN | B | 694 | 58.092 | 105.012 | 19.931 | 1.00 13.28 | C |
| ATOM | 20099 | O | ASN | B | 694 | 58.305 | 104.930 | 18.699 | 1.00 14.19 | O |
| ATOM | 20101 | N | VAL | B | 695 | 57.526 | 104.025 | 20.605 | 1.00 13.40 | N |
| ATOM | 20102 | CA | VAL | B | 695 | 56.999 | 102.855 | 19.909 | 1.00 12.26 | C |
| ATOM | 20104 | CB | VAL | B | 695 | 56.377 | 101.814 | 20.886 | 1.00 12.71 | C |
| ATOM | 20106 | CG1 | VAL | B | 695 | 55.759 | 100.655 | 20.113 | 1.00 12.00 | C |
| ATOM | 20110 | CG2 | VAL | B | 695 | 57.429 | 101.334 | 21.869 | 1.00 12.11 | C |
| ATOM | 20114 | C | VAL | B | 695 | 55.976 | 103.303 | 18.821 | 1.00 12.61 | C |
| ATOM | 20115 | O | VAL | B | 695 | 55.954 | 102.784 | 17.678 | 1.00 13.05 | O |
| ATOM | 20117 | N | SER | B | 696 | 55.138 | 104.273 | 19.165 | 1.00 12.60 | N |
| ATOM | 20118 | CA | SER | B | 696 | 54.169 | 104.816 | 18.213 | 1.00 13.35 | C |
| ATOM | 20120 | CB | SER | B | 696 | 53.346 | 105.905 | 18.863 | 1.00 15.16 | C |
| ATOM | 20123 | OG | SER | B | 696 | 52.614 | 105.363 | 19.975 | 1.00 14.38 | O |
| ATOM | 20125 | C | SER | B | 696 | 54.793 | 105.266 | 16.905 | 1.00 13.34 | C |
| ATOM | 20126 | O | SER | B | 696 | 54.212 | 105.056 | 15.832 | 1.00 14.65 | O |
| ATOM | 20128 | N | LYS | B | 697 | 55.932 | 105.926 | 16.978 | 1.00 13.35 | N |
| ATOM | 20129 | CA | LYS | B | 697 | 56.626 | 106.373 | 15.778 | 1.00 14.30 | C |
| ATOM | 20131 | CB | LYS | B | 697 | 57.842 | 107.207 | 16.165 | 1.00 15.42 | C |
| ATOM | 20134 | CG | LYS | B | 697 | 57.444 | 108.556 | 16.688 | 1.00 18.26 | C |
| ATOM | 20137 | CD | LYS | B | 697 | 58.611 | 109.441 | 17.056 | 1.00 20.88 | C |
| ATOM | 20140 | CE | LYS | B | 697 | 58.113 | 110.901 | 17.363 | 1.00 27.60 | C |
| ATOM | 20143 | NZ | LYS | B | 697 | 56.929 | 111.296 | 16.535 | 1.00 32.30 | N |
| ATOM | 20147 | C | LYS | B | 697 | 57.052 | 105.203 | 14.907 | 1.00 13.97 | C |
| ATOM | 20148 | O | LYS | B | 697 | 56.980 | 105.298 | 13.675 | 1.00 12.88 | O |
| ATOM | 20150 | N | ILE | B | 698 | 57.441 | 104.083 | 15.522 | 1.00 12.37 | N |
| ATOM | 20151 | CA | ILE | B | 698 | 57.812 | 102.876 | 14.767 | 1.00 12.71 | C |
| ATOM | 20153 | CB | ILE | B | 698 | 58.544 | 101.859 | 15.638 | 1.00 11.84 | C |
| ATOM | 20155 | CG1 | ILE | B | 698 | 59.798 | 102.513 | 16.270 | 1.00 13.95 | C |
| ATOM | 20158 | CD1 | ILE | B | 698 | 60.640 | 101.624 | 17.151 | 1.00 14.72 | C |
| ATOM | 20162 | CG2 | ILE | B | 698 | 58.917 | 100.646 | 14.816 | 1.00 13.71 | C |
| ATOM | 20166 | C | ILE | B | 698 | 56.565 | 102.286 | 14.092 | 1.00 12.06 | C |
| ATOM | 20167 | O | ILE | B | 698 | 56.557 | 101.952 | 12.900 | 1.00 13.43 | O |
| ATOM | 20169 | N | TYR | B | 699 | 55.549 | 102.069 | 14.915 | 1.00 13.12 | N |

| ATOM | 20170 | CA | TYR B 699 | 54.215 | 101.596 | 14.442 | 1.00 | 13.26 | C |
|------|-------|-----|-----------|--------|---------|--------|------|-------|---|
| ATOM | 20172 | CB | TYR B 699 | 53.208 | 101.668 | 15.560 | 1.00 | 14.22 | C |
| ATOM | 20175 | CG | TYR B 699 | 51.745 | 101.476 | 15.173 | 1.00 | 12.36 | C |
| ATOM | 20176 | CD1 | TYR B 699 | 51.176 | 100.214 | 14.999 | 1.00 | 16.06 | C |
| ATOM | 20178 | CE1 | TYR B 699 | 49.812 | 100.072 | 14.709 | 1.00 | 12.83 | C |
| ATOM | 20180 | CZ | TYR B 699 | 49.043 | 101.207 | 14.529 | 1.00 | 16.17 | C |
| ATOM | 20181 | OH | TYR B 699 | 47.688 | 101.154 | 14.240 | 1.00 | 17.42 | O |
| ATOM | 20183 | CE2 | TYR B 699 | 49.604 | 102.429 | 14.702 | 1.00 | 12.30 | C |
| ATOM | 20185 | CD2 | TYR B 699 | 50.934 | 102.585 | 15.020 | 1.00 | 15.17 | C |
| ATOM | 20187 | C | TYR B 699 | 53.749 | 102.446 | 13.236 | 1.00 | 13.29 | C |
| ATOM | 20188 | O | TYR B 699 | 53.307 | 101.916 | 12.240 | 1.00 | 13.06 | O |
| ATOM | 20190 | N | GLU B 700 | 53.846 | 103.764 | 13.344 | 1.00 | 13.54 | N |
| ATOM | 20191 | CA | GLU B 700 | 53.346 | 104.638 | 12.267 | 1.00 | 14.57 | C |
| ATOM | 20193 | CB | GLU B 700 | 53.336 | 106.096 | 12.707 | 1.00 | 14.98 | C |
| ATOM | 20196 | CG | GLU B 700 | 52.244 | 106.363 | 13.752 | 1.00 | 15.18 | C |
| ATOM | 20199 | CD | GLU B 700 | 52.200 | 107.772 | 14.328 | 1.00 | 17.77 | C |
| ATOM | 20200 | OE1 | GLU B 700 | 53.219 | 108.488 | 14.250 | 1.00 | 19.83 | O |
| ATOM | 20201 | OE2 | GLU B 700 | 51.113 | 108.168 | 14.850 | 1.00 | 16.42 | O |
| ATOM | 20202 | C | GLU B 700 | 54.129 | 104.421 | 10.978 | 1.00 | 14.00 | C |
| ATOM | 20203 | O | GLU B 700 | 53.552 | 104.413 | 9.885 | 1.00 | 14.25 | O |
| ATOM | 20205 | N | ALA B 701 | 55.439 | 104.205 | 11.106 | 1.00 | 12.87 | N |
| ATOM | 20206 | CA | ALA B 701 | 56.286 | 103.868 | 9.964 | 1.00 | 13.33 | C |
| ATOM | 20208 | CB | ALA B 701 | 57.757 | 103.987 | 10.352 | 1.00 | 14.40 | C |
| ATOM | 20212 | C | ALA B 701 | 56.004 | 102.507 | 9.333 | 1.00 | 11.91 | C |
| ATOM | 20213 | O | ALA B 701 | 56.229 | 102.317 | 8.139 | 1.00 | 12.98 | O |
| ATOM | 20215 | N | ILE B 702 | 55.500 | 101.568 | 10.120 | 1.00 | 13.17 | N |
| ATOM | 20216 | CA | ILE B 702 | 55.033 | 100.284 | 9.607 | 1.00 | 13.11 | C |
| ATOM | 20218 | CB | ILE B 702 | 54.877 | 99.218 | 10.727 | 1.00 | 14.19 | C |
| ATOM | 20220 | CG1 | ILE B 702 | 56.266 | 98.902 | 11.319 | 1.00 | 14.43 | C |
| ATOM | 20223 | CD1 | ILE B 702 | 56.203 | 98.118 | 12.605 | 1.00 | 13.60 | C |
| ATOM | 20227 | CG2 | ILE B 702 | 54.230 | 97.973 | 10.183 | 1.00 | 15.39 | C |
| ATOM | 20231 | C | ILE B 702 | 53.716 | 100.519 | 8.853 | 1.00 | 12.87 | C |
| ATOM | 20232 | O | ILE B 702 | 53.562 | 100.164 | 7.700 | 1.00 | 13.92 | O |
| ATOM | 20234 | N | LYS B 703 | 52.767 | 101.152 | 9.513 | 1.00 | 14.13 | N |
| ATOM | 20235 | CA | LYS B 703 | 51.419 | 101.283 | 8.932 | 1.00 | 14.25 | C |
| ATOM | 20237 | CB | LYS B 703 | 50.444 | 101.863 | 9.959 | 1.00 | 14.03 | C |
| ATOM | 20240 | CG | LYS B 703 | 50.169 | 101.042 | 11.172 | 1.00 | 16.27 | C |
| ATOM | 20243 | CD | LYS B 703 | 49.573 | 99.635 | 10.902 | 1.00 | 18.64 | C |
| ATOM | 20246 | CE | LYS B 703 | 48.198 | 99.628 | 10.233 | 1.00 | 21.14 | C |
| ATOM | 20249 | NZ | LYS B 703 | 47.162 | 100.305 | 11.020 | 1.00 | 22.87 | N |
| ATOM | 20253 | C | LYS B 703 | 51.400 | 102.096 | 7.639 | 1.00 | 13.72 | C |
| ATOM | 20254 | O | LYS B 703 | 50.645 | 101.772 | 6.697 | 1.00 | 16.36 | O |
| ATOM | 20256 | N | SER B 704 | 52.248 | 103.105 | 7.578 | 1.00 | 14.76 | N |
| ATOM | 20257 | CA | SER B 704 | 52.356 | 103.981 | 6.414 | 1.00 | 15.46 | C |
| ATOM | 20259 | CB | SER B 704 | 53.112 | 105.273 | 6.741 | 1.00 | 15.46 | C |
| ATOM | 20262 | OG | SER B 704 | 54.505 | 104.992 | 6.940 | 1.00 | 15.78 | O |
| ATOM | 20264 | C | SER B 704 | 53.101 | 103.296 | 5.269 | 1.00 | 14.62 | C |
| ATOM | 20265 | O | SER B 704 | 53.068 | 103.801 | 4.153 | 1.00 | 15.96 | O |
| ATOM | 20267 | N | GLY B 705 | 53.810 | 102.208 | 5.551 | 1.00 | 14.45 | N |
| ATOM | 20268 | CA | GLY B 705 | 54.667 | 101.529 | 4.572 | 1.00 | 14.37 | C |
| ATOM | 20271 | C | GLY B 705 | 56.027 | 102.209 | 4.391 | 1.00 | 13.55 | C |
| ATOM | 20272 | O | GLY B 705 | 56.839 | 101.765 | 3.542 | 1.00 | 13.93 | O |
| ATOM | 20274 | N | ARG B 706 | 56.333 | 103.251 | 5.178 | 1.00 | 14.09 | N |
| ATOM | 20275 | CA | ARG B 706 | 57.655 | 103.849 | 5.147 | 1.00 | 13.47 | C |
| ATOM | 20277 | CB | ARG B 706 | 57.785 | 104.975 | 6.170 | 1.00 | 13.77 | C |
| ATOM | 20280 | CG | ARG B 706 | 59.017 | 105.779 | 6.004 | 1.00 | 15.98 | C |
| ATOM | 20283 | CD | ARG B 706 | 59.090 | 106.915 | 6.989 | 1.00 | 15.95 | C |

| ATOM | 20286 | NE | ARG | B | 706 | 60.326 | 107.660 | 6.838 | 1.00 | 17.73 | N |
|------|-------|-----|-----|---|-----|--------|---------|-------|------|-------|---|
| ATOM | 20288 | CZ | ARG | B | 706 | 60.677 | 108.691 | 7.602 | 1.00 | 18.04 | C |
| ATOM | 20289 | NH1 | ARG | B | 706 | 59.907 | 109.090 | 8.598 | 1.00 | 18.96 | N |
| ATOM | 20292 | NH2 | ARG | B | 706 | 61.792 | 109.326 | 7.369 | 1.00 | 19.48 | N |
| ATOM | 20295 | C | ARG | B | 706 | 58.791 | 102.850 | 5.351 | 1.00 | 13.24 | C |
| ATOM | 20296 | O | ARG | B | 706 | 59.847 | 102.923 | 4.670 | 1.00 | 13.52 | O |
| ATOM | 20298 | N | ILE | B | 707 | 58.549 | 101.854 | 6.201 | 1.00 | 12.51 | N |
| ATOM | 20299 | CA | ILE | B | 707 | 59.557 | 100.828 | 6.527 | 1.00 | 13.16 | C |
| ATOM | 20301 | CB | ILE | B | 707 | 59.143 | 100.041 | 7.770 | 1.00 | 13.00 | C |
| ATOM | 20303 | CG1 | ILE | B | 707 | 60.362 | 99.390 | 8.388 | 1.00 | 13.27 | C |
| ATOM | 20306 | CD1 | ILE | B | 707 | 60.102 | 98.893 | 9.729 | 1.00 | 16.26 | C |
| ATOM | 20310 | CG2 | ILE | B | 707 | 57.968 | 99.069 | 7.460 | 1.00 | 14.79 | C |
| ATOM | 20314 | C | ILE | B | 707 | 59.786 | 99.853 | 5.350 | 1.00 | 12.67 | C |
| ATOM | 20315 | O | ILE | B | 707 | 60.782 | 99.131 | 5.273 | 1.00 | 14.00 | O |
| ATOM | 20317 | N | ASN | B | 708 | 58.833 | 99.825 | 4.413 | 1.00 | 13.91 | N |
| ATOM | 20318 | CA | ASN | B | 708 | 58.861 | 98.803 | 3.368 | 1.00 | 14.08 | C |
| ATOM | 20320 | CB | ASN | B | 708 | 57.637 | 98.852 | 2.470 | 1.00 | 14.82 | C |
| ATOM | 20323 | CG | ASN | B | 708 | 56.328 | 98.575 | 3.241 | 1.00 | 14.32 | C |
| ATOM | 20324 | OD1 | ASN | B | 708 | 56.348 | 98.093 | 4.389 | 1.00 | 14.43 | O |
| ATOM | 20325 | ND2 | ASN | B | 708 | 55.167 | 98.918 | 2.601 | 1.00 | 14.11 | N |
| ATOM | 20328 | C | ASN | B | 708 | 60.085 | 98.815 | 2.506 | 1.00 | 13.96 | C |
| ATOM | 20329 | O | ASN | B | 708 | 60.696 | 97.759 | 2.314 | 1.00 | 13.61 | O |
| ATOM | 20331 | N | ASN | B | 709 | 60.497 | 99.986 | 2.033 | 1.00 | 13.35 | N |
| ATOM | 20332 | CA | ASN | B | 709 | 61.730 | 100.052 | 1.216 | 1.00 | 14.58 | C |
| ATOM | 20334 | CB | ASN | B | 709 | 61.839 | 101.391 | 0.499 | 1.00 | 15.32 | C |
| ATOM | 20337 | CG | ASN | B | 709 | 60.892 | 101.490 | -0.734 | 1.00 | 20.80 | C |
| ATOM | 20338 | OD1 | ASN | B | 709 | 60.459 | 100.469 | -1.327 | 1.00 | 25.40 | O |
| ATOM | 20339 | ND2 | ASN | B | 709 | 60.596 | 102.731 | -1.143 | 1.00 | 27.12 | N |
| ATOM | 20342 | C | ASN | B | 709 | 62.995 | 99.753 | 2.014 | 1.00 | 14.32 | C |
| ATOM | 20343 | O | ASN | B | 709 | 63.993 | 99.355 | 1.456 | 1.00 | 15.61 | O |
| ATOM | 20345 | N | VAL | B | 710 | 62.934 | 99.972 | 3.312 | 1.00 | 13.76 | N |
| ATOM | 20346 | CA | VAL | B | 710 | 64.025 | 99.585 | 4.238 | 1.00 | 14.08 | C |
| ATOM | 20348 | CB | VAL | B | 710 | 63.805 | 100.174 | 5.637 | 1.00 | 15.23 | C |
| ATOM | 20350 | CG1 | VAL | B | 710 | 65.000 | 99.922 | 6.511 | 1.00 | 14.65 | C |
| ATOM | 20354 | CG2 | VAL | B | 710 | 63.558 | 101.643 | 5.536 | 1.00 | 17.05 | C |
| ATOM | 20358 | C | VAL | B | 710 | 64.217 | 98.075 | 4.304 | 1.00 | 14.06 | C |
| ATOM | 20359 | O | VAL | B | 710 | 65.328 | 97.611 | 4.172 | 1.00 | 13.97 | O |
| ATOM | 20361 | N | LEU | B | 711 | 63.125 | 97.337 | 4.449 | 1.00 | 14.52 | N |
| ATOM | 20362 | CA | LEU | B | 711 | 63.135 | 95.867 | 4.448 | 1.00 | 14.55 | C |
| ATOM | 20364 | CB | LEU | B | 711 | 61.713 | 95.350 | 4.702 | 1.00 | 14.77 | C |
| ATOM | 20367 | CG | LEU | B | 711 | 61.173 | 95.725 | 6.087 | 1.00 | 17.27 | C |
| ATOM | 20369 | CD1 | LEU | B | 711 | 59.688 | 95.377 | 6.183 | 1.00 | 17.75 | C |
| ATOM | 20373 | CD2 | LEU | B | 711 | 61.950 | 94.939 | 7.117 | 1.00 | 17.96 | C |
| ATOM | 20377 | C | LEU | B | 711 | 63.664 | 95.378 | 3.130 | 1.00 | 14.99 | C |
| ATOM | 20378 | O | LEU | B | 711 | 64.473 | 94.435 | 3.094 | 1.00 | 15.18 | O |
| ATOM | 20380 | N | LEU | B | 712 | 63.249 | 96.036 | 2.048 | 1.00 | 15.79 | N |
| ATOM | 20381 | CA | LEU | B | 712 | 63.706 | 95.607 | 0.715 | 1.00 | 16.23 | C |
| ATOM | 20383 | CB | LEU | B | 712 | 62.946 | 96.345 | -0.389 | 1.00 | 16.65 | C |
| ATOM | 20386 | CG | LEU | B | 712 | 63.206 | 95.861 | -1.817 | 1.00 | 19.32 | C |
| ATOM | 20388 | CD1 | LEU | B | 712 | 62.805 | 94.418 | -2.021 | 1.00 | 22.93 | C |
| ATOM | 20392 | CD2 | LEU | B | 712 | 62.494 | 96.783 | -2.840 | 1.00 | 20.75 | C |
| ATOM | 20396 | C | LEU | B | 712 | 65.193 | 95.812 | 0.581 | 1.00 | 16.00 | C |
| ATOM | 20397 | O | LEU | B | 712 | 65.911 | 94.926 | 0.147 | 1.00 | 15.93 | O |
| ATOM | 20399 | N | LYS | B | 713 | 65.677 | 96.978 | 0.981 | 1.00 | 16.84 | N |
| ATOM | 20400 | CA | LYS | B | 713 | 67.107 | 97.269 | 0.878 | 1.00 | 18.11 | C |
| ATOM | 20402 | CB | LYS | B | 713 | 67.364 | 98.672 | 1.411 | 1.00 | 20.02 | C |
| ATOM | 20405 | CG | LYS | B | 713 | 68.573 | 99.325 | 0.881 | 1.00 | 25.54 | C |

| | | | | | | | | | | |
|---|---|---|---|---|---|---|---|---|---|---|
| ATOM | 20408 | CD | LYS | B | 713 | 69.135 | 100.403 | 1.802 | 1.00 | 25.38 | C |
| ATOM | 20411 | CE | LYS | B | 713 | 68.334 | 101.714 | 1.794 | 1.00 | 30.22 | C |
| ATOM | 20414 | NZ | LYS | B | 713 | 69.218 | 102.833 | 2.376 | 1.00 | 31.56 | N |
| ATOM | 20418 | C | LYS | B | 713 | 67.961 | 96.265 | 1.685 | 1.00 | 17.59 | C |
| ATOM | 20419 | O | LYS | B | 713 | 69.022 | 95.859 | 1.244 | 1.00 | 15.50 | O |
| ATOM | 20421 | N | MSE | B | 714 | 67.502 | 95.910 | 2.877 | 1.00 | 17.87 | N |
| ATOM | 20422 | CA | MSE | B | 714 | 68.217 | 94.970 | 3.727 | 1.00 | 19.89 | C |
| ATOM | 20424 | CB | MSE | B | 714 | 67.572 | 94.820 | 5.122 | 1.00 | 20.10 | C |
| ATOM | 20427 | CG | MSE | B | 714 | 67.474 | 96.019 | 5.976 | 1.00 | 22.32 | C |
| ATOM | 20430 | SE | MSE | B | 714 | 66.030 | 95.519 | 7.322 | 1.00 | 27.47 | SE |
| ATOM | 20431 | CE | MSE | B | 714 | 67.120 | 94.329 | 8.456 | 1.00 | 21.63 | C |
| ATOM | 20435 | C | MSE | B | 714 | 68.282 | 93.585 | 3.123 | 1.00 | 20.52 | C |
| ATOM | 20436 | O | MSE | B | 714 | 69.258 | 92.887 | 3.325 | 1.00 | 18.58 | O |
| ATOM | 20438 | N | LEU | B | 715 | 67.218 | 93.166 | 2.432 | 1.00 | 22.66 | N |
| ATOM | 20439 | CA | LEU | B | 715 | 67.101 | 91.801 | 1.919 | 1.00 | 26.35 | C |
| ATOM | 20441 | CB | LEU | B | 715 | 65.678 | 91.262 | 2.143 | 1.00 | 26.20 | C |
| ATOM | 20444 | CG | LEU | B | 715 | 65.332 | 90.998 | 3.607 | 1.00 | 27.88 | C |
| ATOM | 20446 | CD1 | LEU | B | 715 | 63.831 | 90.953 | 3.896 | 1.00 | 30.46 | C |
| ATOM | 20450 | CD2 | LEU | B | 715 | 65.995 | 89.696 | 4.093 | 1.00 | 30.03 | C |
| ATOM | 20454 | C | LEU | B | 715 | 67.497 | 91.692 | 0.475 | 1.00 | 28.93 | C |
| ATOM | 20455 | O | LEU | B | 715 | 67.317 | 90.636 | -0.134 | 1.00 | 31.69 | O |
| ATOM | 20457 | N | ALA | B | 716 | 68.093 | 92.758 | -0.057 | 1.00 | 30.92 | N |
| ATOM | 20458 | CA | ALA | B | 716 | 68.494 | 92.829 | -1.467 | 1.00 | 32.15 | C |
| ATOM | 20460 | CB | ALA | B | 716 | 69.065 | 94.201 | -1.775 | 1.00 | 32.24 | C |
| ATOM | 20464 | C | ALA | B | 716 | 69.517 | 91.760 | -1.801 | 1.00 | 32.97 | C |
| ATOM | 20465 | O | ALA | B | 716 | 69.602 | 91.337 | -2.959 | 1.00 | 34.78 | O |
| ATOM | 20467 | N | ALA | C | 26 | 11.046 | 68.910 | 45.566 | 1.00 | 29.99 | N |
| ATOM | 20468 | CA | ALA | C | 26 | 12.385 | 69.508 | 45.169 | 1.00 | 29.51 | C |
| ATOM | 20470 | CB | ALA | C | 26 | 12.203 | 70.576 | 44.129 | 1.00 | 29.90 | C |
| ATOM | 20474 | C | ALA | C | 26 | 13.092 | 70.092 | 46.389 | 1.00 | 29.32 | C |
| ATOM | 20475 | O | ALA | C | 26 | 12.489 | 70.864 | 47.148 | 1.00 | 28.92 | O |
| ATOM | 20479 | N | SER | C | 27 | 14.360 | 69.736 | 46.589 | 1.00 | 28.34 | N |
| ATOM | 20480 | CA | SER | C | 27 | 15.077 | 70.177 | 47.804 | 1.00 | 28.39 | C |
| ATOM | 20482 | CB | SER | C | 27 | 16.444 | 69.481 | 47.951 | 1.00 | 29.10 | C |
| ATOM | 20485 | OG | SER | C | 27 | 17.135 | 69.902 | 49.132 | 1.00 | 27.25 | O |
| ATOM | 20487 | C | SER | C | 27 | 15.300 | 71.694 | 47.825 | 1.00 | 28.24 | C |
| ATOM | 20488 | O | SER | C | 27 | 15.685 | 72.292 | 46.807 | 1.00 | 27.15 | O |
| ATOM | 20490 | N | THR | C | 28 | 15.098 | 72.294 | 49.002 | 1.00 | 28.28 | N |
| ATOM | 20491 | CA | THR | C | 28 | 15.477 | 73.700 | 49.207 | 1.00 | 27.82 | C |
| ATOM | 20493 | CB | THR | C | 28 | 14.461 | 74.466 | 50.106 | 1.00 | 28.02 | C |
| ATOM | 20495 | OG1 | THR | C | 28 | 14.411 | 73.862 | 51.407 | 1.00 | 29.37 | O |
| ATOM | 20497 | CG2 | THR | C | 28 | 13.060 | 74.499 | 49.458 | 1.00 | 28.35 | C |
| ATOM | 20501 | C | THR | C | 28 | 16.862 | 73.804 | 49.835 | 1.00 | 27.74 | C |
| ATOM | 20502 | O | THR | C | 28 | 17.288 | 74.904 | 50.195 | 1.00 | 28.05 | O |
| ATOM | 20504 | N | ASN | C | 29 | 17.562 | 72.680 | 49.976 | 1.00 | 25.91 | N |
| ATOM | 20505 | CA | ASN | C | 29 | 18.920 | 72.719 | 50.514 | 1.00 | 25.58 | C |
| ATOM | 20507 | CB | ASN | C | 29 | 19.299 | 71.355 | 51.061 | 1.00 | 25.78 | C |
| ATOM | 20510 | CG | ASN | C | 29 | 20.577 | 71.376 | 51.821 | 1.00 | 26.44 | C |
| ATOM | 20511 | OD1 | ASN | C | 29 | 21.497 | 72.145 | 51.520 | 1.00 | 24.58 | O |
| ATOM | 20512 | ND2 | ASN | C | 29 | 20.660 | 70.514 | 52.829 | 1.00 | 27.13 | N |
| ATOM | 20515 | C | ASN | C | 29 | 19.837 | 73.135 | 49.363 | 1.00 | 24.90 | C |
| ATOM | 20516 | O | ASN | C | 29 | 19.866 | 72.448 | 48.339 | 1.00 | 24.38 | O |
| ATOM | 20518 | N | LEU | C | 30 | 20.519 | 74.275 | 49.498 | 1.00 | 24.74 | N |
| ATOM | 20519 | CA | LEU | C | 30 | 21.410 | 74.755 | 48.436 | 1.00 | 24.56 | C |
| ATOM | 20521 | CB | LEU | C | 30 | 22.039 | 76.125 | 48.770 | 1.00 | 25.28 | C |
| ATOM | 20524 | CG | LEU | C | 30 | 21.111 | 77.334 | 48.772 | 1.00 | 27.31 | C |
| ATOM | 20526 | CD1 | LEU | C | 30 | 21.821 | 78.593 | 49.292 | 1.00 | 30.70 | C |

| ATOM | 20530 | CD2 | LEU | C | 30 | 20.555 | 77.588 | 47.384 | 1.00 | 27.87 | C |
| ATOM | 20534 | C | LEU | C | 30 | 22.512 | 73.741 | 48.114 | 1.00 | 24.07 | C |
| ATOM | 20535 | O | LEU | C | 30 | 22.986 | 73.705 | 46.953 | 1.00 | 24.32 | O |
| ATOM | 20537 | N | ALA | C | 31 | 22.935 | 72.935 | 49.108 | 1.00 | 22.90 | N |
| ATOM | 20538 | CA | ALA | C | 31 | 23.929 | 71.882 | 48.837 | 1.00 | 23.46 | C |
| ATOM | 20540 | CB | ALA | C | 31 | 24.329 | 71.146 | 50.111 | 1.00 | 22.38 | C |
| ATOM | 20544 | C | ALA | C | 31 | 23.419 | 70.874 | 47.807 | 1.00 | 23.17 | C |
| ATOM | 20545 | O | ALA | C | 31 | 24.210 | 70.253 | 47.093 | 1.00 | 24.03 | O |
| ATOM | 20547 | N | VAL | C | 32 | 22.102 | 70.692 | 47.745 | 1.00 | 23.30 | N |
| ATOM | 20548 | CA | VAL | C | 32 | 21.475 | 69.862 | 46.686 | 1.00 | 23.73 | C |
| ATOM | 20550 | CB | VAL | C | 32 | 20.143 | 69.240 | 47.173 | 1.00 | 23.20 | C |
| ATOM | 20552 | CG1 | VAL | C | 32 | 19.512 | 68.354 | 46.086 | 1.00 | 25.21 | C |
| ATOM | 20556 | CG2 | VAL | C | 32 | 20.371 | 68.440 | 48.479 | 1.00 | 24.61 | C |
| ATOM | 20560 | C | VAL | C | 32 | 21.194 | 70.677 | 45.424 | 1.00 | 23.68 | C |
| ATOM | 20561 | O | VAL | C | 32 | 21.520 | 70.267 | 44.288 | 1.00 | 24.64 | O |
| ATOM | 20563 | N | ALA | C | 33 | 20.597 | 71.834 | 45.632 | 1.00 | 24.09 | N |
| ATOM | 20564 | CA | ALA | C | 33 | 20.051 | 72.641 | 44.544 | 1.00 | 23.50 | C |
| ATOM | 20566 | CB | ALA | C | 33 | 19.026 | 73.618 | 45.101 | 1.00 | 23.77 | C |
| ATOM | 20570 | C | ALA | C | 33 | 21.100 | 73.419 | 43.751 | 1.00 | 23.58 | C |
| ATOM | 20571 | O | ALA | C | 33 | 20.794 | 73.879 | 42.665 | 1.00 | 23.90 | O |
| ATOM | 20573 | N | GLY | C | 34 | 22.310 | 73.615 | 44.283 | 1.00 | 22.40 | N |
| ATOM | 20574 | CA | GLY | C | 34 | 23.209 | 74.670 | 43.712 | 1.00 | 22.84 | C |
| ATOM | 20577 | C | GLY | C | 34 | 22.604 | 76.076 | 43.824 | 1.00 | 22.84 | C |
| ATOM | 20578 | O | GLY | C | 34 | 21.581 | 76.281 | 44.496 | 1.00 | 22.34 | O |
| ATOM | 20580 | N | SER | C | 35 | 23.228 | 77.053 | 43.145 | 1.00 | 22.06 | N |
| ATOM | 20581 | CA | SER | C | 35 | 22.725 | 78.429 | 43.165 | 1.00 | 22.54 | C |
| ATOM | 20583 | CB | SER | C | 35 | 23.389 | 79.224 | 44.280 | 1.00 | 22.60 | C |
| ATOM | 20586 | OG | SER | C | 35 | 22.859 | 80.537 | 44.325 | 1.00 | 19.91 | O |
| ATOM | 20588 | C | SER | C | 35 | 22.960 | 79.177 | 41.885 | 1.00 | 21.34 | C |
| ATOM | 20589 | O | SER | C | 35 | 24.066 | 79.142 | 41.382 | 1.00 | 23.03 | O |
| ATOM | 20591 | N | HIS | C | 36 | 21.908 | 79.844 | 41.386 | 1.00 | 22.76 | N |
| ATOM | 20592 | CA | HIS | C | 36 | 21.994 | 80.677 | 40.141 | 1.00 | 22.16 | C |
| ATOM | 20594 | CB | HIS | C | 36 | 20.594 | 80.945 | 39.546 | 1.00 | 20.59 | C |
| ATOM | 20597 | CG | HIS | C | 36 | 19.918 | 79.733 | 38.990 | 1.00 | 23.02 | C |
| ATOM | 20598 | ND1 | HIS | C | 36 | 18.974 | 79.011 | 39.703 | 1.00 | 21.74 | N |
| ATOM | 20600 | CE1 | HIS | C | 36 | 18.519 | 78.021 | 38.945 | 1.00 | 23.27 | C |
| ATOM | 20602 | NE2 | HIS | C | 36 | 19.117 | 78.091 | 37.768 | 1.00 | 22.68 | N |
| ATOM | 20604 | CD2 | HIS | C | 36 | 19.995 | 79.147 | 37.774 | 1.00 | 19.31 | C |
| ATOM | 20606 | C | HIS | C | 36 | 22.703 | 82.018 | 40.322 | 1.00 | 22.48 | C |
| ATOM | 20607 | O | HIS | C | 36 | 23.108 | 82.677 | 39.326 | 1.00 | 22.65 | O |
| ATOM | 20609 | N | LEU | C | 37 | 22.818 | 82.426 | 41.570 | 1.00 | 20.61 | N |
| ATOM | 20610 | CA | LEU | C | 37 | 23.637 | 83.558 | 42.006 | 1.00 | 23.05 | C |
| ATOM | 20612 | CB | LEU | C | 37 | 22.733 | 84.527 | 42.799 | 1.00 | 22.56 | C |
| ATOM | 20615 | CG | LEU | C | 37 | 21.952 | 84.030 | 44.074 | 1.00 | 27.13 | C |
| ATOM | 20617 | CD1 | LEU | C | 37 | 22.787 | 83.961 | 45.391 | 1.00 | 29.31 | C |
| ATOM | 20621 | CD2 | LEU | C | 37 | 20.654 | 84.844 | 44.395 | 1.00 | 26.95 | C |
| ATOM | 20625 | C | LEU | C | 37 | 24.854 | 83.212 | 42.928 | 1.00 | 21.32 | C |
| ATOM | 20626 | O | LEU | C | 37 | 24.822 | 82.253 | 43.736 | 1.00 | 21.96 | O |
| ATOM | 20628 | N | PRO | C | 38 | 25.903 | 84.031 | 42.866 | 1.00 | 19.37 | N |
| ATOM | 20629 | CA | PRO | C | 38 | 26.934 | 83.842 | 43.935 | 1.00 | 19.82 | C |
| ATOM | 20631 | CB | PRO | C | 38 | 27.991 | 84.881 | 43.576 | 1.00 | 20.78 | C |
| ATOM | 20634 | CG | PRO | C | 38 | 27.733 | 85.243 | 42.069 | 1.00 | 17.53 | C |
| ATOM | 20637 | CD | PRO | C | 38 | 26.256 | 85.092 | 41.923 | 1.00 | 18.09 | C |
| ATOM | 20640 | C | PRO | C | 38 | 26.387 | 84.103 | 45.356 | 1.00 | 20.33 | C |
| ATOM | 20641 | O | PRO | C | 38 | 25.633 | 85.058 | 45.574 | 1.00 | 20.60 | O |
| ATOM | 20642 | N | THR | C | 39 | 26.785 | 83.254 | 46.308 | 1.00 | 20.02 | N |
| ATOM | 20643 | CA | THR | C | 39 | 26.337 | 83.356 | 47.662 | 1.00 | 21.19 | C |

| | | | | | | | | | |
|---|---|---|---|---|---|---|---|---|---|
| ATOM | 20645 | CB | THR | C | 39 | 24.849 | 82.840 | 47.843 | 1.00 22.25 | C |
| ATOM | 20647 | OG1 | THR | C | 39 | 24.541 | 82.717 | 49.225 | 1.00 22.90 | O |
| ATOM | 20649 | CG2 | THR | C | 39 | 24.635 | 81.481 | 47.242 | 1.00 23.77 | C |
| ATOM | 20653 | C | THR | C | 39 | 27.231 | 82.578 | 48.613 | 1.00 21.64 | C |
| ATOM | 20654 | O | THR | C | 39 | 27.700 | 81.496 | 48.321 | 1.00 21.66 | O |
| ATOM | 20656 | N | THR | C | 40 | 27.478 | 83.149 | 49.769 | 1.00 20.64 | N |
| ATOM | 20657 | CA | THR | C | 40 | 28.258 | 82.451 | 50.769 | 1.00 23.55 | C |
| ATOM | 20659 | CB | THR | C | 40 | 28.745 | 83.434 | 51.860 | 1.00 22.72 | C |
| ATOM | 20661 | OG1 | THR | C | 40 | 27.610 | 84.044 | 52.488 | 1.00 24.67 | O |
| ATOM | 20663 | CG2 | THR | C | 40 | 29.682 | 84.517 | 51.237 | 1.00 24.68 | C |
| ATOM | 20667 | C | THR | C | 40 | 27.423 | 81.358 | 51.459 | 1.00 23.56 | C |
| ATOM | 20668 | O | THR | C | 40 | 27.946 | 80.643 | 52.328 | 1.00 24.74 | O |
| ATOM | 20670 | N | GLN | C | 41 | 26.139 | 81.233 | 51.102 | 1.00 23.47 | N |
| ATOM | 20671 | CA | GLN | C | 41 | 25.283 | 80.220 | 51.743 | 1.00 24.11 | C |
| ATOM | 20673 | CB | AGLN | C | 41 | 23.793 | 80.572 | 51.583 | 0.50 24.48 | C |
| ATOM | 20674 | CB | BGLN | C | 41 | 23.800 | 80.612 | 51.612 | 0.50 24.42 | C |
| ATOM | 20679 | CG | AGLN | C | 41 | 23.372 | 81.881 | 52.228 | 0.50 25.61 | C |
| ATOM | 20680 | CG | BGLN | C | 41 | 23.463 | 81.955 | 52.255 | 0.50 25.39 | C |
| ATOM | 20685 | CD | AGLN | C | 41 | 21.898 | 82.189 | 52.048 | 0.50 26.16 | C |
| ATOM | 20686 | CD | BGLN | C | 41 | 23.960 | 82.038 | 53.685 | 0.50 25.93 | C |
| ATOM | 20687 | OE1 | AGLN | C | 41 | 21.125 | 81.380 | 51.509 | 0.50 29.17 | O |
| ATOM | 20688 | OE1 | BGLN | C | 41 | 23.585 | 81.224 | 54.518 | 0.50 25.88 | O |
| ATOM | 20689 | NE2 | AGLN | C | 41 | 21.494 | 83.361 | 52.503 | 0.50 27.52 | N |
| ATOM | 20690 | NE2 | BGLN | C | 41 | 24.832 | 83.004 | 53.963 | 0.50 26.92 | N |
| ATOM | 20695 | C | GLN | C | 41 | 25.529 | 78.777 | 51.212 | 1.00 23.91 | C |
| ATOM | 20696 | O | GLN | C | 41 | 24.985 | 77.809 | 51.777 | 1.00 24.69 | O |
| ATOM | 20698 | N | VAL | C | 42 | 26.318 | 78.620 | 50.152 | 1.00 22.75 | N |
| ATOM | 20699 | CA | VAL | C | 42 | 26.622 | 77.273 | 49.620 | 1.00 22.57 | C |
| ATOM | 20701 | CB | VAL | C | 42 | 25.597 | 76.777 | 48.632 | 1.00 22.63 | C |
| ATOM | 20703 | CG1 | VAL | C | 42 | 25.689 | 77.547 | 47.295 | 1.00 23.84 | C |
| ATOM | 20707 | CG2 | VAL | C | 42 | 25.731 | 75.271 | 48.418 | 1.00 24.08 | C |
| ATOM | 20711 | C | VAL | C | 42 | 27.991 | 77.262 | 48.966 | 1.00 22.50 | C |
| ATOM | 20712 | O | VAL | C | 42 | 28.447 | 78.297 | 48.447 | 1.00 23.69 | O |
| ATOM | 20714 | N | THR | C | 43 | 28.676 | 76.126 | 49.076 | 1.00 19.98 | N |
| ATOM | 20715 | CA | THR | C | 43 | 29.996 | 75.964 | 48.492 | 1.00 17.75 | C |
| ATOM | 20717 | CB | THR | C | 43 | 31.053 | 75.803 | 49.601 | 1.00 18.65 | C |
| ATOM | 20719 | OG1 | THR | C | 43 | 30.793 | 74.581 | 50.326 | 1.00 16.90 | O |
| ATOM | 20721 | CG2 | THR | C | 43 | 31.020 | 76.995 | 50.586 | 1.00 18.14 | C |
| ATOM | 20725 | C | THR | C | 43 | 30.036 | 74.721 | 47.628 | 1.00 15.80 | C |
| ATOM | 20726 | O | THR | C | 43 | 29.211 | 73.793 | 47.737 | 1.00 13.89 | O |
| ATOM | 20728 | N | GLN | C | 44 | 31.037 | 74.680 | 46.769 | 1.00 15.01 | N |
| ATOM | 20729 | CA | GLN | C | 44 | 31.274 | 73.490 | 45.953 | 1.00 14.90 | C |
| ATOM | 20731 | CB | GLN | C | 44 | 32.412 | 73.757 | 45.003 | 1.00 15.92 | C |
| ATOM | 20734 | CG | GLN | C | 44 | 32.630 | 72.708 | 43.987 | 1.00 15.62 | C |
| ATOM | 20737 | CD | GLN | C | 44 | 33.577 | 73.179 | 42.905 | 1.00 16.08 | C |
| ATOM | 20738 | OE1 | GLN | C | 44 | 34.673 | 73.671 | 43.212 | 1.00 15.91 | O |
| ATOM | 20739 | NE2 | GLN | C | 44 | 33.203 | 72.984 | 41.637 | 1.00 15.05 | N |
| ATOM | 20742 | C | GLN | C | 44 | 31.567 | 72.255 | 46.809 | 1.00 15.33 | C |
| ATOM | 20743 | O | GLN | C | 44 | 31.128 | 71.153 | 46.485 | 1.00 14.12 | O |
| ATOM | 20745 | N | VAL | C | 45 | 32.313 | 72.419 | 47.912 | 1.00 14.67 | N |
| ATOM | 20746 | CA | VAL | C | 45 | 32.515 | 71.285 | 48.793 | 1.00 15.58 | C |
| ATOM | 20748 | CB | VAL | C | 45 | 33.455 | 71.651 | 49.952 | 1.00 15.29 | C |
| ATOM | 20750 | CG1 | VAL | C | 45 | 33.442 | 70.593 | 51.066 | 1.00 18.15 | C |
| ATOM | 20754 | CG2 | VAL | C | 45 | 34.834 | 71.891 | 49.398 | 1.00 16.92 | C |
| ATOM | 20758 | C | VAL | C | 45 | 31.168 | 70.744 | 49.316 | 1.00 15.25 | C |
| ATOM | 20759 | O | VAL | C | 45 | 30.962 | 69.533 | 49.382 | 1.00 16.21 | O |
| ATOM | 20761 | N | ASP | C | 46 | 30.269 | 71.644 | 49.708 | 1.00 15.89 | N |

| ATOM | 20762 | CA | ASP | C | 46 | 28.923 | 71.239 | 50.200 | 1.00 | 16.16 | C |
|------|-------|-----|-----|---|----|--------|--------|--------|------|-------|---|
| ATOM | 20764 | CB | ASP | C | 46 | 27.983 | 72.415 | 50.507 | 1.00 | 15.99 | C |
| ATOM | 20767 | CG | ASP | C | 46 | 28.437 | 73.322 | 51.656 | 1.00 | 20.19 | C |
| ATOM | 20768 | OD1 | ASP | C | 46 | 29.110 | 72.845 | 52.578 | 1.00 | 19.38 | O |
| ATOM | 20769 | OD2 | ASP | C | 46 | 28.045 | 74.534 | 51.648 | 1.00 | 20.01 | O |
| ATOM | 20770 | C | ASP | C | 46 | 28.217 | 70.423 | 49.151 | 1.00 | 15.16 | C |
| ATOM | 20771 | O | ASP | C | 46 | 27.596 | 69.404 | 49.458 | 1.00 | 15.29 | O |
| ATOM | 20773 | N | ILE | C | 47 | 28.280 | 70.910 | 47.916 | 1.00 | 13.87 | N |
| ATOM | 20774 | CA | ILE | C | 47 | 27.646 | 70.226 | 46.803 | 1.00 | 14.37 | C |
| ATOM | 20776 | CB | ILE | C | 47 | 27.654 | 71.124 | 45.505 | 1.00 | 14.29 | C |
| ATOM | 20778 | CG1 | ILE | C | 47 | 26.703 | 72.307 | 45.759 | 1.00 | 14.68 | C |
| ATOM | 20781 | CD1 | ILE | C | 47 | 26.879 | 73.487 | 44.825 | 1.00 | 16.24 | C |
| ATOM | 20785 | CG2 | ILE | C | 47 | 27.302 | 70.310 | 44.284 | 1.00 | 15.30 | C |
| ATOM | 20789 | C | ILE | C | 47 | 28.227 | 68.848 | 46.550 | 1.00 | 13.83 | C |
| ATOM | 20790 | O | ILE | C | 47 | 27.478 | 67.901 | 46.320 | 1.00 | 14.81 | O |
| ATOM | 20792 | N | VAL | C | 48 | 29.548 | 68.733 | 46.593 | 1.00 | 13.52 | N |
| ATOM | 20793 | CA | VAL | C | 48 | 30.210 | 67.466 | 46.321 | 1.00 | 14.45 | C |
| ATOM | 20795 | CB | VAL | C | 48 | 31.737 | 67.682 | 46.201 | 1.00 | 14.91 | C |
| ATOM | 20797 | CG1 | VAL | C | 48 | 32.506 | 66.390 | 46.328 | 1.00 | 17.34 | C |
| ATOM | 20801 | CG2 | VAL | C | 48 | 32.038 | 68.397 | 44.865 | 1.00 | 17.06 | C |
| ATOM | 20805 | C | VAL | C | 48 | 29.911 | 66.513 | 47.452 | 1.00 | 14.48 | C |
| ATOM | 20806 | O | VAL | C | 48 | 29.671 | 65.320 | 47.221 | 1.00 | 14.66 | O |
| ATOM | 20808 | N | GLU | C | 49 | 29.905 | 67.025 | 48.683 | 1.00 | 13.66 | N |
| ATOM | 20809 | CA | GLU | C | 49 | 29.594 | 66.171 | 49.826 | 1.00 | 14.47 | C |
| ATOM | 20811 | CB | GLU | C | 49 | 29.628 | 66.991 | 51.114 | 1.00 | 14.83 | C |
| ATOM | 20814 | CG | GLU | C | 49 | 29.326 | 66.130 | 52.311 | 1.00 | 17.72 | C |
| ATOM | 20817 | CD | GLU | C | 49 | 29.376 | 66.915 | 53.578 | 1.00 | 28.73 | C |
| ATOM | 20818 | OE1 | GLU | C | 49 | 29.004 | 68.113 | 53.538 | 1.00 | 36.20 | O |
| ATOM | 20819 | OE2 | GLU | C | 49 | 29.772 | 66.324 | 54.612 | 1.00 | 34.05 | O |
| ATOM | 20820 | C | GLU | C | 49 | 28.228 | 65.518 | 49.642 | 1.00 | 14.45 | C |
| ATOM | 20821 | O | GLU | C | 49 | 28.047 | 64.300 | 49.811 | 1.00 | 15.07 | O |
| ATOM | 20823 | N | LYS | C | 50 | 27.240 | 66.322 | 49.252 | 1.00 | 14.73 | N |
| ATOM | 20824 | CA | LYS | C | 50 | 25.897 | 65.783 | 49.013 | 1.00 | 16.90 | C |
| ATOM | 20826 | CB | LYS | C | 50 | 24.911 | 66.894 | 48.743 | 1.00 | 18.53 | C |
| ATOM | 20829 | CG | LYS | C | 50 | 24.626 | 67.773 | 49.963 | 1.00 | 24.85 | C |
| ATOM | 20832 | CD | LYS | C | 50 | 23.754 | 67.076 | 51.013 | 1.00 | 31.31 | C |
| ATOM | 20835 | CE | LYS | C | 50 | 24.605 | 66.535 | 52.207 | 1.00 | 34.79 | C |
| ATOM | 20838 | NZ | LYS | C | 50 | 25.063 | 67.610 | 53.141 | 1.00 | 36.96 | N |
| ATOM | 20842 | C | LYS | C | 50 | 25.867 | 64.786 | 47.858 | 1.00 | 16.75 | C |
| ATOM | 20843 | O | LYS | C | 50 | 25.200 | 63.766 | 47.964 | 1.00 | 16.21 | O |
| ATOM | 20845 | N | MSE | C | 51 | 26.573 | 65.057 | 46.762 | 1.00 | 17.13 | N |
| ATOM | 20846 | CA | MSE | C | 51 | 26.579 | 64.095 | 45.641 | 1.00 | 19.45 | C |
| ATOM | 20848 | CB | MSE | C | 51 | 27.361 | 64.627 | 44.437 | 1.00 | 18.61 | C |
| ATOM | 20851 | CG | MSE | C | 51 | 26.726 | 65.768 | 43.805 | 1.00 | 19.72 | C |
| ATOM | 20854 | SE | MSE | C | 51 | 27.555 | 66.040 | 41.978 | 1.00 | 30.05 | SE |
| ATOM | 20855 | CE | MSE | C | 51 | 26.457 | 64.620 | 40.952 | 1.00 | 32.91 | C |
| ATOM | 20859 | C | MSE | C | 51 | 27.208 | 62.779 | 46.055 | 1.00 | 18.27 | C |
| ATOM | 20860 | O | MSE | C | 51 | 26.717 | 61.693 | 45.751 | 1.00 | 18.49 | O |
| ATOM | 20862 | N | LEU | C | 52 | 28.335 | 62.851 | 46.759 | 1.00 | 17.12 | N |
| ATOM | 20863 | CA | LEU | C | 52 | 29.010 | 61.623 | 47.135 | 1.00 | 17.97 | C |
| ATOM | 20865 | CB | LEU | C | 52 | 30.445 | 61.882 | 47.580 | 1.00 | 18.39 | C |
| ATOM | 20868 | CG | LEU | C | 52 | 31.354 | 62.561 | 46.562 | 1.00 | 20.12 | C |
| ATOM | 20870 | CD1 | LEU | C | 52 | 32.676 | 62.924 | 47.169 | 1.00 | 22.19 | C |
| ATOM | 20874 | CD2 | LEU | C | 52 | 31.610 | 61.728 | 45.342 | 1.00 | 21.00 | C |
| ATOM | 20878 | C | LEU | C | 52 | 28.265 | 60.810 | 48.194 | 1.00 | 18.13 | C |
| ATOM | 20879 | O | LEU | C | 52 | 28.555 | 59.638 | 48.377 | 1.00 | 19.56 | O |
| ATOM | 20881 | N | ALA | C | 53 | 27.341 | 61.453 | 48.894 | 1.00 | 18.01 | N |

| ATOM | 20882 | CA | ALA | C | 53 | 26.508 | 60.772 | 49.869 | 1.00 | 18.62 | C |
|------|-------|-----|-----|---|----|--------|--------|--------|------|-------|---|
| ATOM | 20884 | CB | ALA | C | 53 | 25.982 | 61.775 | 50.893 | 1.00 | 18.84 | C |
| ATOM | 20888 | C | ALA | C | 53 | 25.324 | 60.022 | 49.253 | 1.00 | 18.18 | C |
| ATOM | 20889 | O | ALA | C | 53 | 24.612 | 59.343 | 49.989 | 1.00 | 17.34 | O |
| ATOM | 20891 | N | ALA | C | 54 | 25.079 | 60.148 | 47.947 | 1.00 | 18.88 | N |
| ATOM | 20892 | CA | ALA | C | 54 | 23.931 | 59.455 | 47.318 | 1.00 | 19.49 | C |
| ATOM | 20894 | CB | ALA | C | 54 | 23.879 | 59.731 | 45.838 | 1.00 | 19.63 | C |
| ATOM | 20898 | C | ALA | C | 54 | 24.048 | 57.948 | 47.571 | 1.00 | 19.89 | C |
| ATOM | 20899 | O | ALA | C | 54 | 25.111 | 57.377 | 47.327 | 1.00 | 20.62 | O |
| ATOM | 20901 | N | PRO | C | 55 | 22.961 | 57.311 | 48.052 | 1.00 | 20.66 | N |
| ATOM | 20902 | CA | PRO | C | 55 | 22.945 | 55.857 | 48.190 | 1.00 | 21.32 | C |
| ATOM | 20904 | CB | PRO | C | 55 | 21.498 | 55.554 | 48.621 | 1.00 | 21.21 | C |
| ATOM | 20907 | CG | PRO | C | 55 | 20.973 | 56.798 | 49.199 | 1.00 | 20.93 | C |
| ATOM | 20910 | CD | PRO | C | 55 | 21.687 | 57.918 | 48.487 | 1.00 | 20.26 | C |
| ATOM | 20913 | C | PRO | C | 55 | 23.225 | 55.163 | 46.867 | 1.00 | 22.53 | C |
| ATOM | 20914 | O | PRO | C | 55 | 22.873 | 55.678 | 45.795 | 1.00 | 22.79 | O |
| ATOM | 20915 | N | THR | C | 56 | 23.874 | 54.010 | 46.932 | 1.00 | 23.39 | N |
| ATOM | 20916 | CA | THR | C | 56 | 24.074 | 53.186 | 45.731 | 1.00 | 24.90 | C |
| ATOM | 20918 | CB | THR | C | 56 | 25.559 | 52.921 | 45.463 | 1.00 | 25.66 | C |
| ATOM | 20920 | OG1 | THR | C | 56 | 26.168 | 52.313 | 46.615 | 1.00 | 24.85 | O |
| ATOM | 20922 | CG2 | THR | C | 56 | 26.259 | 54.212 | 45.163 | 1.00 | 27.51 | C |
| ATOM | 20926 | C | THR | C | 56 | 23.331 | 51.866 | 45.792 | 1.00 | 25.30 | C |
| ATOM | 20927 | O | THR | C | 56 | 23.151 | 51.222 | 44.752 | 1.00 | 25.08 | O |
| ATOM | 20929 | N | ASP | C | 57 | 22.884 | 51.491 | 47.000 | 1.00 | 25.35 | N |
| ATOM | 20930 | CA | ASP | C | 57 | 22.272 | 50.191 | 47.256 | 1.00 | 25.72 | C |
| ATOM | 20932 | CB | ASP | C | 57 | 22.808 | 49.621 | 48.580 | 1.00 | 26.24 | C |
| ATOM | 20935 | CG | ASP | C | 57 | 22.614 | 50.590 | 49.774 | 1.00 | 29.92 | C |
| ATOM | 20936 | OD1 | ASP | C | 57 | 22.694 | 51.848 | 49.593 | 1.00 | 32.10 | O |
| ATOM | 20937 | OD2 | ASP | C | 57 | 22.367 | 50.076 | 50.901 | 1.00 | 37.40 | O |
| ATOM | 20938 | C | ASP | C | 57 | 20.751 | 50.221 | 47.315 | 1.00 | 24.55 | C |
| ATOM | 20939 | O | ASP | C | 57 | 20.083 | 49.365 | 46.743 | 1.00 | 24.64 | O |
| ATOM | 20941 | N | SER | C | 58 | 20.213 | 51.204 | 48.030 | 1.00 | 23.44 | N |
| ATOM | 20942 | CA | SER | C | 58 | 18.778 | 51.357 | 48.171 | 1.00 | 22.33 | C |
| ATOM | 20944 | CB | SER | C | 58 | 18.476 | 52.258 | 49.364 | 1.00 | 22.70 | C |
| ATOM | 20947 | OG | SER | C | 58 | 19.186 | 53.476 | 49.300 | 1.00 | 24.81 | O |
| ATOM | 20949 | C | SER | C | 58 | 18.185 | 51.947 | 46.902 | 1.00 | 19.98 | C |
| ATOM | 20950 | O | SER | C | 58 | 18.875 | 52.561 | 46.105 | 1.00 | 19.67 | O |
| ATOM | 20952 | N | THR | C | 59 | 16.892 | 51.745 | 46.739 | 1.00 | 18.73 | N |
| ATOM | 20953 | CA | THR | C | 59 | 16.222 | 52.051 | 45.511 | 1.00 | 17.11 | C |
| ATOM | 20955 | CB | THR | C | 59 | 14.893 | 51.306 | 45.414 | 1.00 | 18.03 | C |
| ATOM | 20957 | OG1 | THR | C | 59 | 15.161 | 49.897 | 45.440 | 1.00 | 17.85 | O |
| ATOM | 20959 | CG2 | THR | C | 59 | 14.126 | 51.671 | 44.132 | 1.00 | 16.90 | C |
| ATOM | 20963 | C | THR | C | 59 | 15.984 | 53.538 | 45.390 | 1.00 | 17.14 | C |
| ATOM | 20964 | O | THR | C | 59 | 15.506 | 54.200 | 46.321 | 1.00 | 17.17 | O |
| ATOM | 20966 | N | LEU | C | 60 | 16.330 | 54.054 | 44.222 | 1.00 | 16.13 | N |
| ATOM | 20967 | CA | LEU | C | 60 | 15.993 | 55.418 | 43.856 | 1.00 | 15.75 | C |
| ATOM | 20969 | CB | LEU | C | 60 | 16.907 | 55.861 | 42.743 | 1.00 | 16.02 | C |
| ATOM | 20972 | CG | LEU | C | 60 | 16.652 | 57.237 | 42.130 | 1.00 | 15.02 | C |
| ATOM | 20974 | CD1 | LEU | C | 60 | 16.652 | 58.321 | 43.173 | 1.00 | 15.93 | C |
| ATOM | 20978 | CD2 | LEU | C | 60 | 17.640 | 57.535 | 41.034 | 1.00 | 15.16 | C |
| ATOM | 20982 | C | LEU | C | 60 | 14.535 | 55.438 | 43.375 | 1.00 | 16.48 | C |
| ATOM | 20983 | O | LEU | C | 60 | 14.206 | 54.839 | 42.360 | 1.00 | 15.26 | O |
| ATOM | 20985 | N | GLU | C | 61 | 13.679 | 56.116 | 44.140 | 1.00 | 15.93 | N |
| ATOM | 20986 | CA | GLU | C | 61 | 12.293 | 56.232 | 43.843 | 1.00 | 17.25 | C |
| ATOM | 20988 | CB | GLU | C | 61 | 11.493 | 56.185 | 45.145 | 1.00 | 17.24 | C |
| ATOM | 20991 | CG | GLU | C | 61 | 11.260 | 54.761 | 45.696 | 1.00 | 20.61 | C |
| ATOM | 20994 | CD | GLU | C | 61 | 10.010 | 54.723 | 46.580 | 1.00 | 22.40 | C |

| ATOM | 20995 | OE1 | GLU | C | 61 | 10.089 | 55.424 | 47.613 | 1.00 | 26.27 | O |
|------|-------|-----|-----|---|----|--------|--------|--------|------|-------|---|
| ATOM | 20996 | OE2 | GLU | C | 61 | 8.966 | 54.035 | 46.272 | 1.00 | 28.47 | O |
| ATOM | 20997 | C | GLU | C | 61 | 12.075 | 57.561 | 43.136 | 1.00 | 16.46 | C |
| ATOM | 20998 | O | GLU | C | 61 | 12.376 | 58.616 | 43.677 | 1.00 | 16.45 | O |
| ATOM | 21000 | N | LEU | C | 62 | 11.589 | 57.502 | 41.908 | 1.00 | 14.88 | N |
| ATOM | 21001 | CA | LEU | C | 62 | 11.404 | 58.687 | 41.080 | 1.00 | 14.36 | C |
| ATOM | 21003 | CB | LEU | C | 62 | 11.602 | 58.310 | 39.615 | 1.00 | 14.10 | C |
| ATOM | 21006 | CG | LEU | C | 62 | 12.984 | 57.787 | 39.241 | 1.00 | 15.92 | C |
| ATOM | 21008 | CD1 | LEU | C | 62 | 13.094 | 57.470 | 37.755 | 1.00 | 16.97 | C |
| ATOM | 21012 | CD2 | LEU | C | 62 | 14.042 | 58.819 | 39.668 | 1.00 | 16.34 | C |
| ATOM | 21016 | C | LEU | C | 62 | 9.977 | 59.215 | 41.253 | 1.00 | 13.17 | C |
| ATOM | 21017 | O | LEU | C | 62 | 9.034 | 58.463 | 41.082 | 1.00 | 14.78 | O |
| ATOM | 21019 | N | ASP | C | 63 | 9.827 | 60.493 | 41.605 | 1.00 | 13.64 | N |
| ATOM | 21020 | CA | ASP | C | 63 | 8.527 | 61.104 | 41.834 | 1.00 | 13.23 | C |
| ATOM | 21022 | CB | ASP | C | 63 | 8.325 | 61.435 | 43.327 | 1.00 | 13.66 | C |
| ATOM | 21025 | CG | ASP | C | 63 | 9.386 | 62.393 | 43.873 | 1.00 | 18.01 | C |
| ATOM | 21026 | OD1 | ASP | C | 63 | 9.803 | 63.284 | 43.133 | 1.00 | 16.40 | O |
| ATOM | 21027 | OD2 | ASP | C | 63 | 9.817 | 62.262 | 45.053 | 1.00 | 18.84 | O |
| ATOM | 21028 | C | ASP | C | 63 | 8.286 | 62.356 | 40.982 | 1.00 | 13.09 | C |
| ATOM | 21029 | O | ASP | C | 63 | 7.267 | 63.016 | 41.113 | 1.00 | 13.90 | O |
| ATOM | 21031 | N | GLY | C | 64 | 9.242 | 62.697 | 40.124 | 1.00 | 12.52 | N |
| ATOM | 21032 | CA | GLY | C | 64 | 9.065 | 63.824 | 39.217 | 1.00 | 11.62 | C |
| ATOM | 21035 | C | GLY | C | 64 | 9.665 | 65.137 | 39.708 | 1.00 | 12.40 | C |
| ATOM | 21036 | O | GLY | C | 64 | 9.737 | 66.079 | 38.948 | 1.00 | 11.90 | O |
| ATOM | 21038 | N | TYR | C | 65 | 10.132 | 65.197 | 40.949 | 1.00 | 12.35 | N |
| ATOM | 21039 | CA | TYR | C | 65 | 10.506 | 66.439 | 41.629 | 1.00 | 12.64 | C |
| ATOM | 21041 | CB | TYR | C | 65 | 9.330 | 66.938 | 42.494 | 1.00 | 13.39 | C |
| ATOM | 21044 | CG | TYR | C | 65 | 8.142 | 67.366 | 41.693 | 1.00 | 14.36 | C |
| ATOM | 21045 | CD1 | TYR | C | 65 | 8.008 | 68.673 | 41.292 | 1.00 | 17.37 | C |
| ATOM | 21047 | CE1 | TYR | C | 65 | 6.941 | 69.067 | 40.517 | 1.00 | 17.44 | C |
| ATOM | 21049 | CZ | TYR | C | 65 | 6.013 | 68.142 | 40.119 | 1.00 | 17.64 | C |
| ATOM | 21050 | OH | TYR | C | 65 | 4.957 | 68.542 | 39.321 | 1.00 | 17.67 | O |
| ATOM | 21052 | CE2 | TYR | C | 65 | 6.127 | 66.828 | 40.487 | 1.00 | 15.23 | C |
| ATOM | 21054 | CD2 | TYR | C | 65 | 7.169 | 66.438 | 41.279 | 1.00 | 14.48 | C |
| ATOM | 21056 | C | TYR | C | 65 | 11.758 | 66.308 | 42.494 | 1.00 | 12.87 | C |
| ATOM | 21057 | O | TYR | C | 65 | 12.521 | 67.270 | 42.602 | 1.00 | 12.86 | O |
| ATOM | 21059 | N | SER | C | 66 | 11.967 | 65.132 | 43.113 | 1.00 | 12.32 | N |
| ATOM | 21060 | CA | SER | C | 66 | 13.051 | 64.914 | 44.118 | 1.00 | 13.70 | C |
| ATOM | 21062 | CB | SER | C | 66 | 12.651 | 63.799 | 45.089 | 1.00 | 13.20 | C |
| ATOM | 21065 | OG | SER | C | 66 | 11.443 | 64.105 | 45.694 | 1.00 | 19.10 | O |
| ATOM | 21067 | C | SER | C | 66 | 14.426 | 64.561 | 43.571 | 1.00 | 13.57 | C |
| ATOM | 21068 | O | SER | C | 66 | 15.413 | 64.638 | 44.300 | 1.00 | 14.52 | O |
| ATOM | 21070 | N | LEU | C | 67 | 14.488 | 64.106 | 42.326 | 1.00 | 13.05 | N |
| ATOM | 21071 | CA | LEU | C | 67 | 15.715 | 63.567 | 41.764 | 1.00 | 13.46 | C |
| ATOM | 21073 | CB | LEU | C | 67 | 15.457 | 63.099 | 40.358 | 1.00 | 13.40 | C |
| ATOM | 21076 | CG | LEU | C | 67 | 16.593 | 62.532 | 39.552 | 1.00 | 14.35 | C |
| ATOM | 21078 | CD1 | LEU | C | 67 | 17.119 | 61.213 | 40.232 | 1.00 | 15.58 | C |
| ATOM | 21082 | CD2 | LEU | C | 67 | 16.144 | 62.266 | 38.156 | 1.00 | 14.63 | C |
| ATOM | 21086 | C | LEU | C | 67 | 16.771 | 64.643 | 41.753 | 1.00 | 12.85 | C |
| ATOM | 21087 | O | LEU | C | 67 | 16.537 | 65.697 | 41.247 | 1.00 | 14.48 | O |
| ATOM | 21089 | N | ASN | C | 68 | 17.933 | 64.340 | 42.301 | 1.00 | 12.28 | N |
| ATOM | 21090 | CA | ASN | C | 68 | 19.051 | 65.269 | 42.257 | 1.00 | 12.45 | C |
| ATOM | 21092 | CB | ASN | C | 68 | 19.442 | 65.623 | 43.691 | 1.00 | 12.52 | C |
| ATOM | 21095 | CG | ASN | C | 68 | 19.932 | 64.431 | 44.487 | 1.00 | 14.21 | C |
| ATOM | 21096 | OD1 | ASN | C | 68 | 20.724 | 63.605 | 44.014 | 1.00 | 13.44 | O |
| ATOM | 21097 | ND2 | ASN | C | 68 | 19.476 | 64.350 | 45.730 | 1.00 | 17.93 | N |
| ATOM | 21100 | C | ASN | C | 68 | 20.218 | 64.723 | 41.442 | 1.00 | 12.14 | C |

| ATOM | 21101 | O | ASN | C | 68 | 20.168 | 63.624 | 40.906 | 1.00 | 13.53 | O |
|------|-------|-----|-----|---|----|--------|--------|--------|------|-------|---|
| ATOM | 21103 | N | LEU | C | 69 | 21.278 | 65.503 | 41.310 | 1.00 | 11.91 | N |
| ATOM | 21104 | CA | LEU | C | 69 | 22.359 | 65.075 | 40.422 | 1.00 | 12.48 | C |
| ATOM | 21106 | CB | LEU | C | 69 | 23.254 | 66.264 | 40.050 | 1.00 | 13.15 | C |
| ATOM | 21109 | CG | LEU | C | 69 | 22.488 | 67.422 | 39.373 | 1.00 | 14.71 | C |
| ATOM | 21111 | CD1 | LEU | C | 69 | 23.503 | 68.456 | 38.930 | 1.00 | 17.02 | C |
| ATOM | 21115 | CD2 | LEU | C | 69 | 21.630 | 66.943 | 38.188 | 1.00 | 14.26 | C |
| ATOM | 21119 | C | LEU | C | 69 | 23.158 | 63.898 | 40.992 | 1.00 | 12.98 | C |
| ATOM | 21120 | O | LEU | C | 69 | 23.590 | 62.989 | 40.248 | 1.00 | 12.12 | O |
| ATOM | 21122 | N | GLY | C | 70 | 23.377 | 63.883 | 42.292 | 1.00 | 12.39 | N |
| ATOM | 21123 | CA | GLY | C | 70 | 24.104 | 62.700 | 42.876 | 1.00 | 13.02 | C |
| ATOM | 21126 | C | GLY | C | 70 | 23.306 | 61.430 | 42.598 | 1.00 | 12.88 | C |
| ATOM | 21127 | O | GLY | C | 70 | 23.856 | 60.359 | 42.325 | 1.00 | 13.33 | O |
| ATOM | 21129 | N | ASP | C | 71 | 21.977 | 61.536 | 42.674 | 1.00 | 13.22 | N |
| ATOM | 21130 | CA | ASP | C | 71 | 21.122 | 60.376 | 42.382 | 1.00 | 13.19 | C |
| ATOM | 21132 | CB | ASP | C | 71 | 19.656 | 60.716 | 42.496 | 1.00 | 12.76 | C |
| ATOM | 21135 | CG | ASP | C | 71 | 19.162 | 60.917 | 43.901 | 1.00 | 16.18 | C |
| ATOM | 21136 | OD1 | ASP | C | 71 | 19.627 | 60.269 | 44.866 | 1.00 | 15.96 | O |
| ATOM | 21137 | OD2 | ASP | C | 71 | 18.218 | 61.739 | 44.023 | 1.00 | 16.83 | O |
| ATOM | 21138 | C | ASP | C | 71 | 21.346 | 59.906 | 40.955 | 1.00 | 12.99 | C |
| ATOM | 21139 | O | ASP | C | 71 | 21.436 | 58.688 | 40.706 | 1.00 | 14.51 | O |
| ATOM | 21141 | N | VAL | C | 72 | 21.334 | 60.856 | 40.022 | 1.00 | 14.16 | N |
| ATOM | 21142 | CA | VAL | C | 72 | 21.513 | 60.506 | 38.609 | 1.00 | 12.93 | C |
| ATOM | 21144 | CB | VAL | C | 72 | 21.472 | 61.734 | 37.673 | 1.00 | 13.00 | C |
| ATOM | 21146 | CG1 | VAL | C | 72 | 21.912 | 61.363 | 36.276 | 1.00 | 15.28 | C |
| ATOM | 21150 | CG2 | VAL | C | 72 | 20.086 | 62.357 | 37.673 | 1.00 | 13.50 | C |
| ATOM | 21154 | C | VAL | C | 72 | 22.817 | 59.729 | 38.432 | 1.00 | 12.97 | C |
| ATOM | 21155 | O | VAL | C | 72 | 22.843 | 58.715 | 37.765 | 1.00 | 11.58 | O |
| ATOM | 21157 | N | VAL | C | 73 | 23.895 | 60.225 | 39.031 | 1.00 | 12.73 | N |
| ATOM | 21158 | CA | VAL | C | 73 | 25.199 | 59.585 | 38.911 | 1.00 | 13.20 | C |
| ATOM | 21160 | CB | VAL | C | 73 | 26.335 | 60.478 | 39.514 | 1.00 | 13.60 | C |
| ATOM | 21162 | CG1 | VAL | C | 73 | 27.711 | 59.742 | 39.471 | 1.00 | 14.33 | C |
| ATOM | 21166 | CG2 | VAL | C | 73 | 26.401 | 61.813 | 38.764 | 1.00 | 13.90 | C |
| ATOM | 21170 | C | VAL | C | 73 | 25.153 | 58.182 | 39.524 | 1.00 | 12.95 | C |
| ATOM | 21171 | O | VAL | C | 73 | 25.731 | 57.211 | 39.013 | 1.00 | 14.09 | O |
| ATOM | 21173 | N | SER | C | 74 | 24.434 | 58.050 | 40.630 | 1.00 | 12.82 | N |
| ATOM | 21174 | CA | SER | C | 74 | 24.422 | 56.729 | 41.308 | 1.00 | 14.21 | C |
| ATOM | 21176 | CB | SER | C | 74 | 23.779 | 56.804 | 42.688 | 1.00 | 14.39 | C |
| ATOM | 21179 | OG | SER | C | 74 | 22.408 | 57.134 | 42.649 | 1.00 | 16.59 | O |
| ATOM | 21181 | C | SER | C | 74 | 23.714 | 55.684 | 40.443 | 1.00 | 14.60 | C |
| ATOM | 21182 | O | SER | C | 74 | 24.116 | 54.516 | 40.421 | 1.00 | 14.84 | O |
| ATOM | 21184 | N | ALA | C | 75 | 22.649 | 56.109 | 39.748 | 1.00 | 14.27 | N |
| ATOM | 21185 | CA | ALA | C | 75 | 21.925 | 55.244 | 38.833 | 1.00 | 14.15 | C |
| ATOM | 21187 | CB | ALA | C | 75 | 20.608 | 55.898 | 38.458 | 1.00 | 14.76 | C |
| ATOM | 21191 | C | ALA | C | 75 | 22.752 | 54.935 | 37.574 | 1.00 | 15.26 | C |
| ATOM | 21192 | O | ALA | C | 75 | 22.733 | 53.821 | 37.058 | 1.00 | 15.06 | O |
| ATOM | 21194 | N | ALA | C | 76 | 23.398 | 55.952 | 37.009 | 1.00 | 15.10 | N |
| ATOM | 21195 | CA | ALA | C | 76 | 24.150 | 55.794 | 35.754 | 1.00 | 15.23 | C |
| ATOM | 21197 | CB | ALA | C | 76 | 24.477 | 57.174 | 35.160 | 1.00 | 15.61 | C |
| ATOM | 21201 | C | ALA | C | 76 | 25.413 | 54.947 | 35.901 | 1.00 | 16.24 | C |
| ATOM | 21202 | O | ALA | C | 76 | 25.672 | 54.040 | 35.085 | 1.00 | 15.70 | O |
| ATOM | 21204 | N | ARG | C | 77 | 26.184 | 55.220 | 36.960 | 1.00 | 17.56 | N |
| ATOM | 21205 | CA | ARG | C | 77 | 27.502 | 54.624 | 37.143 | 1.00 | 18.10 | C |
| ATOM | 21207 | CB | ARG | C | 77 | 28.503 | 55.680 | 37.566 | 1.00 | 18.24 | C |
| ATOM | 21210 | CG | ARG | C | 77 | 28.835 | 56.579 | 36.510 | 1.00 | 17.03 | C |
| ATOM | 21213 | CD | ARG | C | 77 | 30.030 | 57.444 | 36.907 | 1.00 | 18.33 | C |
| ATOM | 21216 | NE | ARG | C | 77 | 30.423 | 58.259 | 35.772 | 1.00 | 17.42 | N |

| | | | | | | | | | |
|---|---|---|---|---|---|---|---|---|---|
| ATOM | 21218 | CZ | ARG | C | 77 | 31.086 | 59.407 | 35.858 | 1.00 16.16 | C |
| ATOM | 21219 | NH1 | ARG | C | 77 | 31.435 | 59.871 | 37.049 | 1.00 16.32 | N |
| ATOM | 21222 | NH2 | ARG | C | 77 | 31.417 | 60.066 | 34.762 | 1.00 16.05 | N |
| ATOM | 21225 | C | ARG | C | 77 | 27.582 | 53.521 | 38.174 | 1.00 18.92 | C |
| ATOM | 21226 | O | ARG | C | 77 | 28.430 | 52.661 | 38.065 | 1.00 20.07 | O |
| ATOM | 21228 | N | LYS | C | 78 | 26.720 | 53.564 | 39.187 | 1.00 18.43 | N |
| ATOM | 21229 | CA | LYS | C | 78 | 26.900 | 52.723 | 40.350 | 1.00 18.81 | C |
| ATOM | 21231 | CB | LYS | C | 78 | 26.875 | 53.566 | 41.631 | 1.00 18.52 | C |
| ATOM | 21234 | CG | LYS | C | 78 | 27.819 | 54.744 | 41.642 | 1.00 21.33 | C |
| ATOM | 21237 | CD | LYS | C | 78 | 29.241 | 54.287 | 41.537 | 1.00 26.69 | C |
| ATOM | 21240 | CE | LYS | C | 78 | 30.196 | 55.445 | 41.804 | 1.00 30.22 | C |
| ATOM | 21243 | NZ | LYS | C | 78 | 31.478 | 54.890 | 42.313 | 1.00 32.79 | N |
| ATOM | 21247 | C | LYS | C | 78 | 25.865 | 51.640 | 40.457 | 1.00 18.00 | C |
| ATOM | 21248 | O | LYS | C | 78 | 25.795 | 50.963 | 41.496 | 1.00 19.21 | O |
| ATOM | 21250 | N | GLY | C | 79 | 25.030 | 51.491 | 39.418 | 1.00 17.05 | N |
| ATOM | 21251 | CA | GLY | C | 79 | 24.097 | 50.374 | 39.342 | 1.00 16.73 | C |
| ATOM | 21254 | C | GLY | C | 79 | 22.934 | 50.460 | 40.319 | 1.00 17.15 | C |
| ATOM | 21255 | O | GLY | C | 79 | 22.273 | 49.450 | 40.593 | 1.00 17.48 | O |
| ATOM | 21257 | N | ARG | C | 80 | 22.638 | 51.661 | 40.818 | 1.00 15.74 | N |
| ATOM | 21258 | CA | ARG | C | 80 | 21.616 | 51.802 | 41.843 | 1.00 15.84 | C |
| ATOM | 21260 | CB | ARG | C | 80 | 21.540 | 53.218 | 42.326 | 1.00 15.80 | C |
| ATOM | 21263 | CG | ARG | C | 80 | 20.612 | 53.394 | 43.492 | 1.00 16.27 | C |
| ATOM | 21266 | CD | ARG | C | 80 | 20.665 | 54.815 | 43.916 | 1.00 16.27 | C |
| ATOM | 21269 | NE | ARG | C | 80 | 19.758 | 55.142 | 45.005 | 1.00 17.45 | N |
| ATOM | 21271 | CZ | ARG | C | 80 | 19.528 | 56.406 | 45.373 | 1.00 17.39 | C |
| ATOM | 21272 | NH1 | ARG | C | 80 | 20.161 | 57.405 | 44.792 | 1.00 16.95 | N |
| ATOM | 21275 | NH2 | ARG | C | 80 | 18.694 | 56.656 | 46.359 | 1.00 17.58 | N |
| ATOM | 21278 | C | ARG | C | 80 | 20.265 | 51.406 | 41.261 | 1.00 15.00 | C |
| ATOM | 21279 | O | ARG | C | 80 | 19.970 | 51.813 | 40.145 | 1.00 13.62 | O |
| ATOM | 21281 | N | PRO | C | 81 | 19.483 | 50.559 | 41.967 | 1.00 14.30 | N |
| ATOM | 21282 | CA | PRO | C | 81 | 18.131 | 50.260 | 41.487 | 1.00 14.30 | C |
| ATOM | 21284 | CB | PRO | C | 81 | 17.565 | 49.343 | 42.575 | 1.00 13.98 | C |
| ATOM | 21287 | CG | PRO | C | 81 | 18.766 | 48.697 | 43.135 | 1.00 15.59 | C |
| ATOM | 21290 | CD | PRO | C | 81 | 19.775 | 49.780 | 43.187 | 1.00 14.85 | C |
| ATOM | 21293 | C | PRO | C | 81 | 17.274 | 51.520 | 41.397 | 1.00 14.43 | C |
| ATOM | 21294 | O | PRO | C | 81 | 17.428 | 52.463 | 42.217 | 1.00 14.56 | O |
| ATOM | 21295 | N | VAL | C | 82 | 16.355 | 51.503 | 40.432 | 1.00 14.71 | N |
| ATOM | 21296 | CA | VAL | C | 82 | 15.512 | 52.656 | 40.116 | 1.00 14.80 | C |
| ATOM | 21298 | CB | VAL | C | 82 | 15.972 | 53.386 | 38.815 | 1.00 14.52 | C |
| ATOM | 21300 | CG1 | VAL | C | 82 | 15.086 | 54.586 | 38.516 | 1.00 14.61 | C |
| ATOM | 21304 | CG2 | VAL | C | 82 | 17.430 | 53.875 | 38.955 | 1.00 13.99 | C |
| ATOM | 21308 | C | VAL | C | 82 | 14.081 | 52.191 | 39.894 | 1.00 15.61 | C |
| ATOM | 21309 | O | VAL | C | 82 | 13.872 | 51.218 | 39.170 | 1.00 16.13 | O |
| ATOM | 21311 | N | ARG | C | 83 | 13.111 | 52.899 | 40.490 | 1.00 15.73 | N |
| ATOM | 21312 | CA | ARG | C | 83 | 11.695 | 52.625 | 40.276 | 1.00 16.52 | C |
| ATOM | 21314 | CB | ARG | C | 83 | 11.154 | 51.655 | 41.343 | 1.00 18.07 | C |
| ATOM | 21317 | CG | ARG | C | 83 | 11.622 | 50.217 | 41.095 | 1.00 24.32 | C |
| ATOM | 21320 | CD | ARG | C | 83 | 12.229 | 49.570 | 42.352 | 1.00 32.34 | C |
| ATOM | 21323 | NE | ARG | C | 83 | 12.668 | 48.178 | 42.190 | 1.00 32.86 | N |
| ATOM | 21325 | CZ | ARG | C | 83 | 11.862 | 47.136 | 42.007 | 1.00 38.59 | C |
| ATOM | 21326 | NH1 | ARG | C | 83 | 10.534 | 47.289 | 41.940 | 1.00 40.57 | N |
| ATOM | 21329 | NH2 | ARG | C | 83 | 12.389 | 45.918 | 41.885 | 1.00 39.39 | N |
| ATOM | 21332 | C | ARG | C | 83 | 10.895 | 53.918 | 40.330 | 1.00 15.86 | C |
| ATOM | 21333 | O | ARG | C | 83 | 11.312 | 54.900 | 40.964 | 1.00 15.45 | O |
| ATOM | 21335 | N | VAL | C | 84 | 9.766 | 53.927 | 39.640 | 1.00 15.00 | N |
| ATOM | 21336 | CA | VAL | C | 84 | 8.767 | 54.939 | 39.861 | 1.00 14.96 | C |
| ATOM | 21338 | CB | VAL | C | 84 | 7.581 | 54.826 | 38.885 | 1.00 15.42 | C |

| | | | | | | | | | |
|---|---|---|---|---|---|---|---|---|---|
| ATOM | 21340 | CG1 | VAL C | 84 | 6.469 | 55.809 | 39.282 | 1.00 15.18 | C |
| ATOM | 21344 | CG2 | VAL C | 84 | 8.058 | 55.079 | 37.477 | 1.00 17.10 | C |
| ATOM | 21348 | C | VAL C | 84 | 8.284 | 54.776 | 41.300 | 1.00 15.03 | C |
| ATOM | 21349 | O | VAL C | 84 | 7.975 | 53.664 | 41.728 | 1.00 15.56 | O |
| ATOM | 21351 | N | LYS C | 85 | 8.197 | 55.891 | 42.023 | 1.00 15.99 | N |
| ATOM | 21352 | CA | LYS C | 85 | 7.766 | 55.913 | 43.409 | 1.00 17.26 | C |
| ATOM | 21354 | CB | LYS C | 85 | 7.552 | 57.349 | 43.888 | 1.00 17.28 | C |
| ATOM | 21357 | CG | LYS C | 85 | 7.041 | 57.509 | 45.338 | 1.00 18.54 | C |
| ATOM | 21360 | CD | LYS C | 85 | 7.960 | 58.203 | 46.266 | 1.00 23.79 | C |
| ATOM | 21363 | CE | LYS C | 85 | 7.441 | 58.185 | 47.718 | 1.00 23.84 | C |
| ATOM | 21366 | NZ | LYS C | 85 | 6.178 | 58.965 | 47.763 | 1.00 28.65 | N |
| ATOM | 21370 | C | LYS C | 85 | 6.469 | 55.137 | 43.552 | 1.00 18.81 | C |
| ATOM | 21371 | O | LYS C | 85 | 5.496 | 55.390 | 42.843 | 1.00 17.51 | O |
| ATOM | 21373 | N | ASP C | 86 | 6.469 | 54.235 | 44.528 | 1.00 20.57 | N |
| ATOM | 21374 | CA | ASP C | 86 | 5.333 | 53.389 | 44.833 | 1.00 22.97 | C |
| ATOM | 21376 | CB | ASP C | 86 | 5.849 | 52.243 | 45.717 | 1.00 23.53 | C |
| ATOM | 21379 | CG | ASP C | 86 | 4.833 | 51.157 | 45.949 | 1.00 27.00 | C |
| ATOM | 21380 | OD1 | ASP C | 86 | 5.259 | 50.089 | 46.468 | 1.00 30.57 | O |
| ATOM | 21381 | OD2 | ASP C | 86 | 3.640 | 51.370 | 45.643 | 1.00 30.09 | O |
| ATOM | 21382 | C | ASP C | 86 | 4.284 | 54.231 | 45.556 | 1.00 23.15 | C |
| ATOM | 21383 | O | ASP C | 86 | 4.309 | 54.337 | 46.778 | 1.00 23.84 | O |
| ATOM | 21385 | N | SER C | 87 | 3.374 | 54.816 | 44.785 | 1.00 23.74 | N |
| ATOM | 21386 | CA | SER C | 87 | 2.500 | 55.887 | 45.246 | 1.00 24.44 | C |
| ATOM | 21388 | CB | SER C | 87 | 3.237 | 57.233 | 45.098 | 1.00 24.85 | C |
| ATOM | 21391 | OG | SER C | 87 | 2.360 | 58.349 | 45.074 | 1.00 24.88 | O |
| ATOM | 21393 | C | SER C | 87 | 1.181 | 55.902 | 44.454 | 1.00 24.84 | C |
| ATOM | 21394 | O | SER C | 87 | 1.187 | 55.852 | 43.226 | 1.00 24.24 | O |
| ATOM | 21396 | N | ASP C | 88 | 0.052 | 55.979 | 45.159 | 1.00 24.95 | N |
| ATOM | 21397 | CA | ASP C | 88 | -1.246 | 56.153 | 44.515 | 1.00 25.49 | C |
| ATOM | 21399 | CB | ASP C | 88 | -2.387 | 56.017 | 45.523 | 1.00 26.26 | C |
| ATOM | 21402 | CG | ASP C | 88 | -2.772 | 54.581 | 45.781 | 1.00 27.93 | C |
| ATOM | 21403 | OD1 | ASP C | 88 | -2.116 | 53.647 | 45.253 | 1.00 30.53 | O |
| ATOM | 21404 | OD2 | ASP C | 88 | -3.756 | 54.386 | 46.522 | 1.00 32.92 | O |
| ATOM | 21405 | C | ASP C | 88 | -1.386 | 57.506 | 43.846 | 1.00 25.82 | C |
| ATOM | 21406 | O | ASP C | 88 | -1.959 | 57.603 | 42.763 | 1.00 24.96 | O |
| ATOM | 21408 | N | GLU C | 89 | -0.886 | 58.569 | 44.467 | 1.00 26.54 | N |
| ATOM | 21409 | CA | GLU C | 89 | -1.082 | 59.872 | 43.840 | 1.00 27.92 | C |
| ATOM | 21411 | CB | GLU C | 89 | -0.805 | 61.027 | 44.808 | 1.00 28.45 | C |
| ATOM | 21414 | CG | GLU C | 89 | 0.614 | 61.492 | 44.870 | 1.00 32.55 | C |
| ATOM | 21417 | CD | GLU C | 89 | 0.738 | 62.929 | 45.391 | 1.00 33.04 | C |
| ATOM | 21418 | OE1 | GLU C | 89 | 1.438 | 63.729 | 44.717 | 1.00 37.24 | O |
| ATOM | 21419 | OE2 | GLU C | 89 | 0.120 | 63.235 | 46.454 | 1.00 40.07 | O |
| ATOM | 21420 | C | GLU C | 89 | -0.272 | 59.995 | 42.530 | 1.00 26.67 | C |
| ATOM | 21421 | O | GLU C | 89 | -0.746 | 60.593 | 41.562 | 1.00 26.48 | O |
| ATOM | 21423 | N | ILE C | 90 | 0.915 | 59.396 | 42.501 | 1.00 26.19 | N |
| ATOM | 21424 | CA | ILE C | 90 | 1.740 | 59.372 | 41.283 | 1.00 26.49 | C |
| ATOM | 21426 | CB | ILE C | 90 | 3.143 | 58.798 | 41.551 | 1.00 26.38 | C |
| ATOM | 21428 | CG1 | ILE C | 90 | 3.915 | 59.683 | 42.544 | 1.00 27.86 | C |
| ATOM | 21431 | CD1 | ILE C | 90 | 4.570 | 60.880 | 41.933 | 1.00 30.65 | C |
| ATOM | 21435 | CG2 | ILE C | 90 | 3.907 | 58.600 | 40.225 | 1.00 26.52 | C |
| ATOM | 21439 | C | ILE C | 90 | 1.065 | 58.521 | 40.215 | 1.00 25.91 | C |
| ATOM | 21440 | O | ILE C | 90 | 0.880 | 58.952 | 39.084 | 1.00 23.88 | O |
| ATOM | 21442 | N | ARG C | 91 | 0.680 | 57.307 | 40.587 | 1.00 26.09 | N |
| ATOM | 21443 | CA | ARG C | 91 | -0.003 | 56.436 | 39.632 | 1.00 27.09 | C |
| ATOM | 21445 | CB | ARG C | 91 | -0.430 | 55.124 | 40.264 | 1.00 27.68 | C |
| ATOM | 21448 | CG | ARG C | 91 | 0.682 | 54.151 | 40.399 | 1.00 28.98 | C |
| ATOM | 21451 | CD | ARG C | 91 | 0.169 | 52.783 | 40.870 | 1.00 30.74 | C |

| ATOM | 21454 | NE | ARG | C | 91 | 1.251 | 52.239 | 41.648 | 1.00 | 34.07 | N |
|------|-------|-----|-----|---|----|-------|--------|--------|------|-------|---|
| ATOM | 21456 | CZ | ARG | C | 91 | 1.390 | 52.370 | 42.962 | 1.00 | 35.63 | C |
| ATOM | 21457 | NH1 | ARG | C | 91 | 0.442 | 52.933 | 43.716 | 1.00 | 37.22 | N |
| ATOM | 21460 | NH2 | ARG | C | 91 | 2.481 | 51.882 | 43.530 | 1.00 | 36.06 | N |
| ATOM | 21463 | C | ARG | C | 91 | -1.228 | 57.085 | 39.069 | 1.00 | 26.32 | C |
| ATOM | 21464 | O | ARG | C | 91 | -1.486 | 56.976 | 37.875 | 1.00 | 24.69 | O |
| ATOM | 21466 | N | SER | C | 92 | -2.012 | 57.725 | 39.932 | 1.00 | 26.30 | N |
| ATOM | 21467 | CA | SER | C | 92 | -3.249 | 58.344 | 39.471 | 1.00 | 27.08 | C |
| ATOM | 21469 | CB | SER | C | 92 | -4.087 | 58.867 | 40.641 | 1.00 | 27.34 | C |
| ATOM | 21472 | OG | SER | C | 92 | -5.163 | 59.651 | 40.144 | 1.00 | 29.47 | O |
| ATOM | 21474 | C | SER | C | 92 | -2.964 | 59.485 | 38.494 | 1.00 | 27.04 | C |
| ATOM | 21475 | O | SER | C | 92 | -3.604 | 59.559 | 37.440 | 1.00 | 26.89 | O |
| ATOM | 21477 | N | LYS | C | 93 | -2.011 | 60.354 | 38.851 | 1.00 | 26.66 | N |
| ATOM | 21478 | CA | LYS | C | 93 | -1.601 | 61.460 | 37.963 | 1.00 | 27.11 | C |
| ATOM | 21480 | CB | LYS | C | 93 | -0.396 | 62.246 | 38.508 | 1.00 | 27.48 | C |
| ATOM | 21483 | CG | LYS | C | 93 | -0.751 | 63.419 | 39.414 | 1.00 | 30.18 | C |
| ATOM | 21486 | CD | LYS | C | 93 | 0.366 | 64.491 | 39.464 | 1.00 | 29.59 | C |
| ATOM | 21489 | CE | LYS | C | 93 | 1.609 | 64.102 | 40.279 | 1.00 | 31.37 | C |
| ATOM | 21492 | NZ | LYS | C | 93 | 2.377 | 63.071 | 39.584 | 1.00 | 32.72 | N |
| ATOM | 21496 | C | LYS | C | 93 | -1.237 | 60.968 | 36.561 | 1.00 | 24.99 | C |
| ATOM | 21497 | O | LYS | C | 93 | -1.686 | 61.540 | 35.568 | 1.00 | 24.48 | O |
| ATOM | 21499 | N | ILE | C | 94 | -0.429 | 59.907 | 36.517 | 1.00 | 24.04 | N |
| ATOM | 21500 | CA | ILE | C | 94 | 0.002 | 59.289 | 35.253 | 1.00 | 23.49 | C |
| ATOM | 21502 | CB | ILE | C | 94 | 1.069 | 58.161 | 35.482 | 1.00 | 22.95 | C |
| ATOM | 21504 | CG1 | ILE | C | 94 | 2.380 | 58.740 | 36.018 | 1.00 | 23.01 | C |
| ATOM | 21507 | CD1 | ILE | C | 94 | 3.328 | 57.673 | 36.513 | 1.00 | 22.93 | C |
| ATOM | 21511 | CG2 | ILE | C | 94 | 1.364 | 57.414 | 34.184 | 1.00 | 23.25 | C |
| ATOM | 21515 | C | ILE | C | 94 | -1.214 | 58.720 | 34.522 | 1.00 | 23.55 | C |
| ATOM | 21516 | O | ILE | C | 94 | -1.405 | 58.978 | 33.334 | 1.00 | 23.31 | O |
| ATOM | 21518 | N | ASP | C | 95 | -2.049 | 57.976 | 35.249 | 1.00 | 23.06 | N |
| ATOM | 21519 | CA | ASP | C | 95 | -3.171 | 57.274 | 34.626 | 1.00 | 23.57 | C |
| ATOM | 21521 | CB | ASP | C | 95 | -3.831 | 56.252 | 35.602 | 1.00 | 23.90 | C |
| ATOM | 21524 | CG | ASP | C | 95 | -2.861 | 55.093 | 36.063 | 1.00 | 27.71 | C |
| ATOM | 21525 | OD1 | ASP | C | 95 | -1.634 | 55.058 | 35.735 | 1.00 | 32.72 | O |
| ATOM | 21526 | OD2 | ASP | C | 95 | -3.341 | 54.195 | 36.816 | 1.00 | 33.13 | O |
| ATOM | 21527 | C | ASP | C | 95 | -4.184 | 58.285 | 34.093 | 1.00 | 22.95 | C |
| ATOM | 21528 | O | ASP | C | 95 | -4.711 | 58.112 | 33.015 | 1.00 | 22.70 | O |
| ATOM | 21530 | N | LYS | C | 96 | -4.412 | 59.371 | 34.823 | 1.00 | 23.52 | N |
| ATOM | 21531 | CA | LYS | C | 96 | -5.331 | 60.425 | 34.393 | 1.00 | 24.04 | C |
| ATOM | 21533 | CB | LYS | C | 96 | -5.543 | 61.453 | 35.507 | 1.00 | 25.27 | C |
| ATOM | 21536 | CG | LYS | C | 96 | -6.440 | 61.001 | 36.633 | 1.00 | 27.18 | C |
| ATOM | 21539 | CD | LYS | C | 96 | -6.731 | 62.163 | 37.619 | 1.00 | 27.80 | C |
| ATOM | 21542 | CE | LYS | C | 96 | -7.897 | 61.822 | 38.582 | 1.00 | 30.05 | C |
| ATOM | 21545 | NZ | LYS | C | 96 | -8.577 | 63.034 | 39.228 | 1.00 | 31.76 | N |
| ATOM | 21549 | C | LYS | C | 96 | -4.883 | 61.159 | 33.144 | 1.00 | 22.67 | C |
| ATOM | 21550 | O | LYS | C | 96 | -5.694 | 61.488 | 32.297 | 1.00 | 22.23 | O |
| ATOM | 21552 | N | SER | C | 97 | -3.588 | 61.468 | 33.024 | 1.00 | 22.27 | N |
| ATOM | 21553 | CA | SER | C | 97 | -3.122 | 62.125 | 31.801 | 1.00 | 21.15 | C |
| ATOM | 21555 | CB | SER | C | 97 | -1.649 | 62.558 | 31.849 | 1.00 | 21.62 | C |
| ATOM | 21558 | OG | SER | C | 97 | -0.873 | 61.448 | 32.186 | 1.00 | 22.43 | O |
| ATOM | 21560 | C | SER | C | 97 | -3.368 | 61.219 | 30.602 | 1.00 | 20.31 | C |
| ATOM | 21561 | O | SER | C | 97 | -3.743 | 61.701 | 29.557 | 1.00 | 20.36 | O |
| ATOM | 21563 | N | VAL | C | 98 | -3.177 | 59.912 | 30.751 | 1.00 | 20.56 | N |
| ATOM | 21564 | CA | VAL | C | 98 | -3.442 | 58.980 | 29.644 | 1.00 | 21.28 | C |
| ATOM | 21566 | CB | VAL | C | 98 | -2.972 | 57.536 | 29.996 | 1.00 | 20.97 | C |
| ATOM | 21568 | CG1 | VAL | C | 98 | -3.373 | 56.543 | 28.887 | 1.00 | 20.92 | C |
| ATOM | 21572 | CG2 | VAL | C | 98 | -1.467 | 57.474 | 30.242 | 1.00 | 20.40 | C |

| ATOM | 21576 | C | VAL | C | 98 | -4.938 | 58.964 | 29.246 | 1.00 | 22.63 | C |
|---|---|---|---|---|---|---|---|---|---|---|---|
| ATOM | 21577 | O | VAL | C | 98 | -5.302 | 59.066 | 28.070 | 1.00 | 22.16 | O |
| ATOM | 21579 | N | GLU | C | 99 | -5.797 | 58.840 | 30.246 | 1.00 | 24.62 | N |
| ATOM | 21580 | CA | GLU | C | 99 | -7.236 | 58.856 | 30.048 | 1.00 | 25.33 | C |
| ATOM | 21582 | CB | GLU | C | 99 | -7.925 | 58.499 | 31.369 | 1.00 | 25.87 | C |
| ATOM | 21585 | CG | GLU | C | 99 | -9.480 | 58.560 | 31.365 | 1.00 | 28.07 | C |
| ATOM | 21588 | CD | GLU | C | 99 | -10.201 | 57.640 | 30.329 | 1.00 | 34.60 | C |
| ATOM | 21589 | OE1 | GLU | C | 99 | -9.573 | 57.184 | 29.327 | 1.00 | 37.00 | O |
| ATOM | 21590 | OE2 | GLU | C | 99 | -11.431 | 57.383 | 30.529 | 1.00 | 37.21 | O |
| ATOM | 21591 | C | GLU | C | 99 | -7.756 | 60.187 | 29.466 | 1.00 | 26.30 | C |
| ATOM | 21592 | O | GLU | C | 99 | -8.596 | 60.198 | 28.565 | 1.00 | 25.74 | O |
| ATOM | 21594 | N | PHE | C | 100 | -7.250 | 61.316 | 29.939 | 1.00 | 27.54 | N |
| ATOM | 21595 | CA | PHE | C | 100 | -7.642 | 62.581 | 29.338 | 1.00 | 28.88 | C |
| ATOM | 21597 | CB | PHE | C | 100 | -6.964 | 63.785 | 30.018 | 1.00 | 29.36 | C |
| ATOM | 21600 | CG | PHE | C | 100 | -7.262 | 65.068 | 29.323 | 1.00 | 29.92 | C |
| ATOM | 21601 | CD1 | PHE | C | 100 | -8.503 | 65.686 | 29.502 | 1.00 | 30.98 | C |
| ATOM | 21603 | CE1 | PHE | C | 100 | -8.812 | 66.848 | 28.821 | 1.00 | 31.13 | C |
| ATOM | 21605 | CZ | PHE | C | 100 | -7.913 | 67.377 | 27.914 | 1.00 | 29.57 | C |
| ATOM | 21607 | CE2 | PHE | C | 100 | -6.695 | 66.755 | 27.697 | 1.00 | 30.96 | C |
| ATOM | 21609 | CD2 | PHE | C | 100 | -6.378 | 65.598 | 28.394 | 1.00 | 30.59 | C |
| ATOM | 21611 | C | PHE | C | 100 | -7.284 | 62.613 | 27.847 | 1.00 | 30.22 | C |
| ATOM | 21612 | O | PHE | C | 100 | -8.101 | 62.956 | 27.003 | 1.00 | 30.15 | O |
| ATOM | 21614 | N | LEU | C | 101 | -6.038 | 62.285 | 27.533 | 1.00 | 31.66 | N |
| ATOM | 21615 | CA | LEU | C | 101 | -5.583 | 62.277 | 26.145 | 1.00 | 33.26 | C |
| ATOM | 21617 | CB | LEU | C | 101 | -4.105 | 61.890 | 26.075 | 1.00 | 33.68 | C |
| ATOM | 21620 | CG | LEU | C | 101 | -3.522 | 61.921 | 24.660 | 1.00 | 34.27 | C |
| ATOM | 21622 | CD1 | LEU | C | 101 | -2.640 | 63.117 | 24.497 | 1.00 | 34.41 | C |
| ATOM | 21626 | CD2 | LEU | C | 101 | -2.753 | 60.653 | 24.381 | 1.00 | 35.44 | C |
| ATOM | 21630 | C | LEU | C | 101 | -6.412 | 61.297 | 25.315 | 1.00 | 34.44 | C |
| ATOM | 21631 | O | LEU | C | 101 | -6.755 | 61.576 | 24.179 | 1.00 | 33.97 | O |
| ATOM | 21633 | N | ARG | C | 102 | -6.705 | 60.144 | 25.901 | 1.00 | 36.08 | N |
| ATOM | 21634 | CA | ARG | C | 102 | -7.557 | 59.134 | 25.279 | 1.00 | 38.10 | C |
| ATOM | 21636 | CB | ARG | C | 102 | -7.676 | 57.925 | 26.201 | 1.00 | 38.08 | C |
| ATOM | 21639 | CG | ARG | C | 102 | -8.676 | 56.890 | 25.750 | 1.00 | 40.18 | C |
| ATOM | 21642 | CD | ARG | C | 102 | -8.574 | 55.617 | 26.595 | 1.00 | 41.68 | C |
| ATOM | 21645 | NE | ARG | C | 102 | -8.599 | 54.427 | 25.743 | 1.00 | 45.56 | N |
| ATOM | 21647 | CZ | ARG | C | 102 | -8.476 | 53.174 | 26.183 | 1.00 | 47.98 | C |
| ATOM | 21648 | NH1 | ARG | C | 102 | -8.342 | 52.913 | 27.487 | 1.00 | 50.34 | N |
| ATOM | 21651 | NH2 | ARG | C | 102 | -8.504 | 52.170 | 25.308 | 1.00 | 47.75 | N |
| ATOM | 21654 | C | ARG | C | 102 | -8.950 | 59.671 | 24.939 | 1.00 | 38.04 | C |
| ATOM | 21655 | O | ARG | C | 102 | -9.440 | 59.433 | 23.841 | 1.00 | 37.81 | O |
| ATOM | 21657 | N | SER | C | 103 | -9.578 | 60.381 | 25.879 | 1.00 | 38.68 | N |
| ATOM | 21658 | CA | SER | C | 103 | -10.894 | 61.004 | 25.654 | 1.00 | 38.88 | C |
| ATOM | 21662 | C | SER | C | 103 | -10.819 | 62.275 | 24.795 | 1.00 | 39.62 | C |
| ATOM | 21663 | O | SER | C | 103 | -10.249 | 63.298 | 25.203 | 1.00 | 39.77 | O |
| ATOM | 21665 | N | GLU | C | 125 | -4.905 | 50.946 | 15.676 | 1.00 | 34.72 | N |
| ATOM | 21666 | CA | GLU | C | 125 | -3.852 | 50.476 | 14.763 | 1.00 | 34.27 | C |
| ATOM | 21668 | CB | GLU | C | 125 | -4.397 | 49.393 | 13.816 | 1.00 | 35.11 | C |
| ATOM | 21671 | CG | GLU | C | 125 | -4.741 | 48.046 | 14.519 | 1.00 | 37.68 | C |
| ATOM | 21674 | CD | GLU | C | 125 | -3.586 | 47.477 | 15.396 | 1.00 | 40.05 | C |
| ATOM | 21675 | OE1 | GLU | C | 125 | -2.394 | 47.622 | 15.019 | 1.00 | 39.73 | O |
| ATOM | 21676 | OE2 | GLU | C | 125 | -3.883 | 46.862 | 16.454 | 1.00 | 41.28 | O |
| ATOM | 21677 | C | GLU | C | 125 | -3.200 | 51.612 | 13.962 | 1.00 | 32.91 | C |
| ATOM | 21678 | O | GLU | C | 125 | -2.010 | 51.551 | 13.623 | 1.00 | 31.68 | O |
| ATOM | 21680 | N | ASP | C | 126 | -3.962 | 52.659 | 13.670 | 1.00 | 31.21 | N |
| ATOM | 21681 | CA | ASP | C | 126 | -3.371 | 53.806 | 13.008 | 1.00 | 30.15 | C |
| ATOM | 21683 | CB | ASP | C | 126 | -4.443 | 54.726 | 12.444 | 1.00 | 30.86 | C |

| ATOM | 21686 | CG | ASP | C | 126 | -5.301 | 54.034 | 11.385 | 1.00 | 33.40 | C |
|---|---|---|---|---|---|---|---|---|---|---|---|
| ATOM | 21687 | OD1 | ASP | C | 126 | -4.735 | 53.237 | 10.590 | 1.00 | 36.75 | O |
| ATOM | 21688 | OD2 | ASP | C | 126 | -6.531 | 54.282 | 11.359 | 1.00 | 37.07 | O |
| ATOM | 21689 | C | ASP | C | 126 | -2.475 | 54.547 | 13.983 | 1.00 | 28.05 | C |
| ATOM | 21690 | O | ASP | C | 126 | -1.416 | 55.037 | 13.587 | 1.00 | 28.28 | O |
| ATOM | 21692 | N | ALA | C | 127 | -2.894 | 54.649 | 15.247 | 1.00 | 25.75 | N |
| ATOM | 21693 | CA | ALA | C | 127 | -2.031 | 55.263 | 16.282 | 1.00 | 24.33 | C |
| ATOM | 21695 | CB | ALA | C | 127 | -2.786 | 55.438 | 17.617 | 1.00 | 24.45 | C |
| ATOM | 21699 | C | ALA | C | 127 | -0.767 | 54.432 | 16.503 | 1.00 | 22.84 | C |
| ATOM | 21700 | O | ALA | C | 127 | 0.320 | 54.995 | 16.718 | 1.00 | 22.50 | O |
| ATOM | 21702 | N | ILE | C | 128 | -0.917 | 53.101 | 16.452 | 1.00 | 20.89 | N |
| ATOM | 21703 | CA | ILE | C | 128 | 0.238 | 52.211 | 16.571 | 1.00 | 19.97 | C |
| ATOM | 21705 | CB | ILE | C | 128 | -0.192 | 50.735 | 16.622 | 1.00 | 19.62 | C |
| ATOM | 21707 | CG1 | ILE | C | 128 | -0.769 | 50.426 | 18.012 | 1.00 | 21.05 | C |
| ATOM | 21710 | CD1 | ILE | C | 128 | -1.627 | 49.172 | 18.102 | 1.00 | 21.42 | C |
| ATOM | 21714 | CG2 | ILE | C | 128 | 0.979 | 49.813 | 16.292 | 1.00 | 19.21 | C |
| ATOM | 21718 | C | ILE | C | 128 | 1.199 | 52.464 | 15.409 | 1.00 | 18.30 | C |
| ATOM | 21719 | O | ILE | C | 128 | 2.406 | 52.614 | 15.631 | 1.00 | 18.24 | O |
| ATOM | 21721 | N | SER | C | 129 | 0.656 | 52.547 | 14.185 | 1.00 | 17.59 | N |
| ATOM | 21722 | CA | SER | C | 129 | 1.475 | 52.794 | 12.985 | 1.00 | 17.61 | C |
| ATOM | 21724 | CB | SER | C | 129 | 0.592 | 52.786 | 11.714 | 1.00 | 18.08 | C |
| ATOM | 21727 | OG | SER | C | 129 | 0.099 | 51.483 | 11.464 | 1.00 | 17.33 | O |
| ATOM | 21729 | C | SER | C | 129 | 2.215 | 54.135 | 13.082 | 1.00 | 17.40 | C |
| ATOM | 21730 | O | SER | C | 129 | 3.404 | 54.252 | 12.719 | 1.00 | 16.44 | O |
| ATOM | 21732 | N | LEU | C | 130 | 1.511 | 55.161 | 13.571 | 1.00 | 17.44 | N |
| ATOM | 21733 | CA | LEU | C | 130 | 2.117 | 56.475 | 13.683 | 1.00 | 17.78 | C |
| ATOM | 21735 | CB | LEU | C | 130 | 1.096 | 57.472 | 14.178 | 1.00 | 18.17 | C |
| ATOM | 21738 | CG | LEU | C | 130 | 1.630 | 58.868 | 14.394 | 1.00 | 20.48 | C |
| ATOM | 21740 | CD1 | LEU | C | 130 | 2.138 | 59.448 | 13.086 | 1.00 | 21.62 | C |
| ATOM | 21744 | CD2 | LEU | C | 130 | 0.546 | 59.754 | 15.001 | 1.00 | 20.87 | C |
| ATOM | 21748 | C | LEU | C | 130 | 3.344 | 56.481 | 14.614 | 1.00 | 16.31 | C |
| ATOM | 21749 | O | LEU | C | 130 | 4.362 | 57.078 | 14.294 | 1.00 | 15.19 | O |
| ATOM | 21751 | N | GLN | C | 131 | 3.266 | 55.812 | 15.755 | 1.00 | 15.25 | N |
| ATOM | 21752 | CA | GLN | C | 131 | 4.449 | 55.712 | 16.605 | 1.00 | 15.27 | C |
| ATOM | 21754 | CB | GLN | C | 131 | 4.165 | 55.013 | 17.946 | 1.00 | 15.84 | C |
| ATOM | 21757 | CG | GLN | C | 131 | 2.846 | 55.349 | 18.621 | 1.00 | 15.56 | C |
| ATOM | 21760 | CD | GLN | C | 131 | 2.566 | 56.834 | 18.647 | 1.00 | 17.73 | C |
| ATOM | 21761 | OE1 | GLN | C | 131 | 3.378 | 57.647 | 19.120 | 1.00 | 16.86 | O |
| ATOM | 21762 | NE2 | GLN | C | 131 | 1.415 | 57.203 | 18.119 | 1.00 | 15.35 | N |
| ATOM | 21765 | C | GLN | C | 131 | 5.606 | 55.002 | 15.877 | 1.00 | 14.60 | C |
| ATOM | 21766 | O | GLN | C | 131 | 6.754 | 55.339 | 16.078 | 1.00 | 14.34 | O |
| ATOM | 21768 | N | LYS | C | 132 | 5.309 | 53.991 | 15.074 | 1.00 | 14.51 | N |
| ATOM | 21769 | CA | LYS | C | 132 | 6.347 | 53.262 | 14.311 | 1.00 | 14.14 | C |
| ATOM | 21771 | CB | LYS | C | 132 | 5.753 | 51.980 | 13.698 | 1.00 | 14.08 | C |
| ATOM | 21774 | CG | LYS | C | 132 | 5.375 | 50.927 | 14.732 | 1.00 | 14.63 | C |
| ATOM | 21777 | CD | LYS | C | 132 | 4.755 | 49.709 | 14.109 | 1.00 | 14.55 | C |
| ATOM | 21780 | CE | LYS | C | 132 | 4.567 | 48.592 | 15.159 | 1.00 | 14.45 | C |
| ATOM | 21783 | NZ | LYS | C | 132 | 3.804 | 47.439 | 14.621 | 1.00 | 13.73 | N |
| ATOM | 21787 | C | LYS | C | 132 | 6.993 | 54.127 | 13.223 | 1.00 | 13.68 | C |
| ATOM | 21788 | O | LYS | C | 132 | 8.215 | 54.011 | 12.985 | 1.00 | 14.42 | O |
| ATOM | 21790 | N | ALA | C | 133 | 6.200 | 54.997 | 12.585 | 1.00 | 13.23 | N |
| ATOM | 21791 | CA | ALA | C | 133 | 6.744 | 56.011 | 11.621 | 1.00 | 12.33 | C |
| ATOM | 21793 | CB | ALA | C | 133 | 5.643 | 56.744 | 10.942 | 1.00 | 13.42 | C |
| ATOM | 21797 | C | ALA | C | 133 | 7.641 | 57.007 | 12.353 | 1.00 | 12.12 | C |
| ATOM | 21798 | O | ALA | C | 133 | 8.635 | 57.489 | 11.816 | 1.00 | 11.06 | O |
| ATOM | 21800 | N | LEU | C | 134 | 7.301 | 57.317 | 13.593 | 1.00 | 13.06 | N |
| ATOM | 21801 | CA | LEU | C | 134 | 8.104 | 58.251 | 14.367 | 1.00 | 14.98 | C |

| ATOM | 21803 | CB  | LEU | C | 134 | 7.403  | 58.680 | 15.668 | 1.00 | 16.51 | C |
|------|-------|-----|-----|---|-----|--------|--------|--------|------|-------|---|
| ATOM | 21806 | CG  | LEU | C | 134 | 6.186  | 59.596 | 15.446 | 1.00 | 20.34 | C |
| ATOM | 21808 | CD1 | LEU | C | 134 | 5.354  | 59.756 | 16.740 | 1.00 | 24.31 | C |
| ATOM | 21812 | CD2 | LEU | C | 134 | 6.581  | 61.032 | 14.850 | 1.00 | 24.23 | C |
| ATOM | 21816 | C   | LEU | C | 134 | 9.439  | 57.635 | 14.647 | 1.00 | 13.57 | C |
| ATOM | 21817 | O   | LEU | C | 134 | 10.471 | 58.296 | 14.506 | 1.00 | 14.23 | O |
| ATOM | 21819 | N   | LEU | C | 135 | 9.457  | 56.351 | 15.051 | 1.00 | 13.77 | N |
| ATOM | 21820 | CA  | LEU | C | 135 | 10.730 | 55.734 | 15.347 | 1.00 | 13.59 | C |
| ATOM | 21822 | CB  | LEU | C | 135 | 10.571 | 54.428 | 16.110 | 1.00 | 14.20 | C |
| ATOM | 21825 | CG  | LEU | C | 135 | 9.854  | 54.528 | 17.446 | 1.00 | 17.91 | C |
| ATOM | 21827 | CD1 | LEU | C | 135 | 9.894  | 53.131 | 18.100 | 1.00 | 20.65 | C |
| ATOM | 21831 | CD2 | LEU | C | 135 | 10.386 | 55.572 | 18.340 | 1.00 | 19.58 | C |
| ATOM | 21835 | C   | LEU | C | 135 | 11.516 | 55.484 | 14.087 | 1.00 | 12.92 | C |
| ATOM | 21836 | O   | LEU | C | 135 | 12.718 | 55.729 | 14.075 | 1.00 | 12.53 | O |
| ATOM | 21838 | N   | GLU | C | 136 | 10.819 | 55.039 | 13.043 | 1.00 | 12.56 | N |
| ATOM | 21839 | CA  | GLU | C | 136 | 11.437 | 54.629 | 11.791 | 1.00 | 12.97 | C |
| ATOM | 21841 | CB  | GLU | C | 136 | 10.379 | 54.453 | 10.690 | 1.00 | 12.25 | C |
| ATOM | 21844 | CG  | GLU | C | 136 | 10.966 | 54.029 | 9.352  | 1.00 | 14.60 | C |
| ATOM | 21847 | CD  | GLU | C | 136 | 10.005 | 54.111 | 8.188  | 1.00 | 13.19 | C |
| ATOM | 21848 | OE1 | GLU | C | 136 | 8.931  | 54.775 | 8.292  | 1.00 | 12.35 | O |
| ATOM | 21849 | OE2 | GLU | C | 136 | 10.304 | 53.475 | 7.125  | 1.00 | 13.14 | O |
| ATOM | 21850 | C   | GLU | C | 136 | 12.461 | 55.665 | 11.355 | 1.00 | 12.28 | C |
| ATOM | 21851 | O   | GLU | C | 136 | 13.623 | 55.339 | 11.144 | 1.00 | 12.62 | O |
| ATOM | 21853 | N   | HIS | C | 137 | 12.019 | 56.912 | 11.231 | 1.00 | 13.10 | N |
| ATOM | 21854 | CA  | HIS | C | 137 | 12.893 | 57.956 | 10.688 | 1.00 | 12.29 | C |
| ATOM | 21856 | CB  | HIS | C | 137 | 12.093 | 59.132 | 10.126 | 1.00 | 11.98 | C |
| ATOM | 21859 | CG  | HIS | C | 137 | 11.636 | 60.147 | 11.147 | 1.00 | 13.23 | C |
| ATOM | 21860 | ND1 | HIS | C | 137 | 10.484 | 59.983 | 11.894 | 1.00 | 15.79 | N |
| ATOM | 21862 | CE1 | HIS | C | 137 | 10.325 | 61.040 | 12.673 | 1.00 | 17.31 | C |
| ATOM | 21864 | NE2 | HIS | C | 137 | 11.302 | 61.893 | 12.440 | 1.00 | 15.36 | N |
| ATOM | 21866 | CD2 | HIS | C | 137 | 12.127 | 61.369 | 11.477 | 1.00 | 15.03 | C |
| ATOM | 21868 | C   | HIS | C | 137 | 14.017 | 58.407 | 11.617 | 1.00 | 12.04 | C |
| ATOM | 21869 | O   | HIS | C | 137 | 15.055 | 58.940 | 11.145 | 1.00 | 12.18 | O |
| ATOM | 21871 | N   | GLN | C | 138 | 13.839 | 58.165 | 12.916 | 1.00 | 11.90 | N |
| ATOM | 21872 | CA  | GLN | C | 138 | 14.809 | 58.583 | 13.916 | 1.00 | 11.85 | C |
| ATOM | 21874 | CB  | GLN | C | 138 | 14.060 | 58.979 | 15.200 | 1.00 | 12.88 | C |
| ATOM | 21877 | CG  | GLN | C | 138 | 13.305 | 60.323 | 15.046 | 1.00 | 14.23 | C |
| ATOM | 21880 | CD  | GLN | C | 138 | 14.187 | 61.541 | 14.887 | 1.00 | 15.60 | C |
| ATOM | 21881 | OE1 | GLN | C | 138 | 15.362 | 61.532 | 15.246 | 1.00 | 18.72 | O |
| ATOM | 21882 | NE2 | GLN | C | 138 | 13.627 | 62.591 | 14.330 | 1.00 | 18.40 | N |
| ATOM | 21885 | C   | GLN | C | 138 | 15.920 | 57.570 | 14.208 | 1.00 | 10.76 | C |
| ATOM | 21886 | O   | GLN | C | 138 | 16.938 | 57.911 | 14.845 | 1.00 | 11.82 | O |
| ATOM | 21888 | N   | LEU | C | 139 | 15.716 | 56.332 | 13.746 | 1.00 | 11.51 | N |
| ATOM | 21889 | CA  | LEU | C | 139 | 16.694 | 55.255 | 13.851 | 1.00 | 11.51 | C |
| ATOM | 21891 | CB  | LEU | C | 139 | 15.954 | 53.912 | 13.905 | 1.00 | 10.92 | C |
| ATOM | 21894 | CG  | LEU | C | 139 | 15.074 | 53.748 | 15.148 | 1.00 | 11.34 | C |
| ATOM | 21896 | CD1 | LEU | C | 139 | 14.217 | 52.546 | 15.041 | 1.00 | 12.88 | C |
| ATOM | 21900 | CD2 | LEU | C | 139 | 15.866 | 53.740 | 16.475 | 1.00 | 11.35 | C |
| ATOM | 21904 | C   | LEU | C | 139 | 17.642 | 55.362 | 12.682 | 1.00 | 11.05 | C |
| ATOM | 21905 | O   | LEU | C | 139 | 17.712 | 54.469 | 11.844 | 1.00 | 12.71 | O |
| ATOM | 21907 | N   | CYS | C | 140 | 18.359 | 56.494 | 12.644 | 1.00 | 11.51 | N |
| ATOM | 21908 | CA  | CYS | C | 140 | 19.091 | 56.871 | 11.450 | 1.00 | 11.75 | C |
| ATOM | 21910 | CB  | CYS | C | 140 | 18.494 | 58.145 | 10.873 | 1.00 | 11.66 | C |
| ATOM | 21913 | SG  | CYS | C | 140 | 18.455 | 59.561 | 11.939 | 1.00 | 16.22 | S |
| ATOM | 21915 | C   | CYS | C | 140 | 20.572 | 57.115 | 11.678 | 1.00 | 12.40 | C |
| ATOM | 21916 | O   | CYS | C | 140 | 21.210 | 57.743 | 10.850 | 1.00 | 13.22 | O |
| ATOM | 21918 | N   | GLY | C | 141 | 21.093 | 56.660 | 12.810 | 1.00 | 12.04 | N |

| ATOM | 21919 | CA  | GLY | C | 141 | 22.443 | 56.943 | 13.222 | 1.00 | 11.49 | C |
|------|-------|-----|-----|---|-----|--------|--------|--------|------|-------|---|
| ATOM | 21922 | C   | GLY | C | 141 | 23.364 | 55.798 | 12.917 | 1.00 | 11.71 | C |
| ATOM | 21923 | O   | GLY | C | 141 | 22.897 | 54.669 | 12.605 | 1.00 | 12.37 | O |
| ATOM | 21925 | N   | VAL | C | 142 | 24.670 | 56.103 | 12.975 | 1.00 | 11.38 | N |
| ATOM | 21926 | CA  | VAL | C | 142 | 25.708 | 55.138 | 12.593 | 1.00 | 11.13 | C |
| ATOM | 21928 | CB  | VAL | C | 142 | 26.835 | 55.804 | 11.760 | 1.00 | 11.54 | C |
| ATOM | 21930 | CG1 | VAL | C | 142 | 27.971 | 54.859 | 11.530 | 1.00 | 12.56 | C |
| ATOM | 21934 | CG2 | VAL | C | 142 | 26.272 | 56.199 | 10.414 | 1.00 | 12.33 | C |
| ATOM | 21938 | C   | VAL | C | 142 | 26.244 | 54.362 | 13.789 | 1.00 | 11.95 | C |
| ATOM | 21939 | O   | VAL | C | 142 | 26.648 | 54.938 | 14.807 | 1.00 | 11.14 | O |
| ATOM | 21941 | N   | LEU | C | 143 | 26.249 | 53.037 | 13.601 | 1.00 | 11.86 | N |
| ATOM | 21942 | CA  | LEU | C | 143 | 26.800 | 52.062 | 14.528 | 1.00 | 12.24 | C |
| ATOM | 21944 | CB  | LEU | C | 143 | 25.663 | 51.437 | 15.317 | 1.00 | 12.55 | C |
| ATOM | 21947 | CG  | LEU | C | 143 | 24.966 | 52.234 | 16.410 | 1.00 | 10.92 | C |
| ATOM | 21949 | CD1 | LEU | C | 143 | 23.604 | 51.638 | 16.828 | 1.00 | 13.43 | C |
| ATOM | 21953 | CD2 | LEU | C | 143 | 25.908 | 52.508 | 17.588 | 1.00 | 13.60 | C |
| ATOM | 21957 | C   | LEU | C | 143 | 27.518 | 50.979 | 13.709 | 1.00 | 13.03 | C |
| ATOM | 21958 | O   | LEU | C | 143 | 27.229 | 50.812 | 12.513 | 1.00 | 13.55 | O |
| ATOM | 21960 | N   | PRO | C | 144 | 28.444 | 50.211 | 14.331 | 1.00 | 13.91 | N |
| ATOM | 21961 | CA  | PRO | C | 144 | 29.103 | 49.131 | 13.599 | 1.00 | 13.81 | C |
| ATOM | 21963 | CB  | PRO | C | 144 | 30.005 | 48.441 | 14.648 | 1.00 | 14.66 | C |
| ATOM | 21966 | CG  | PRO | C | 144 | 29.848 | 49.175 | 15.885 | 1.00 | 14.40 | C |
| ATOM | 21969 | CD  | PRO | C | 144 | 28.943 | 50.347 | 15.706 | 1.00 | 14.80 | C |
| ATOM | 21972 | C   | PRO | C | 144 | 28.083 | 48.131 | 13.092 | 1.00 | 14.01 | C |
| ATOM | 21973 | O   | PRO | C | 144 | 27.143 | 47.787 | 13.818 | 1.00 | 15.01 | O |
| ATOM | 21974 | N   | SER | C | 145 | 28.266 | 47.658 | 11.868 | 1.00 | 15.40 | N |
| ATOM | 21975 | CA  | SER | C | 145 | 27.305 | 46.747 | 11.289 | 1.00 | 17.06 | C |
| ATOM | 21977 | CB  | SER | C | 145 | 27.417 | 46.802 | 9.763  | 1.00 | 16.11 | C |
| ATOM | 21980 | OG  | SER | C | 145 | 28.661 | 46.257 | 9.359  | 1.00 | 17.98 | O |
| ATOM | 21982 | C   | SER | C | 145 | 27.449 | 45.317 | 11.866 | 1.00 | 17.83 | C |
| ATOM | 21983 | O   | SER | C | 145 | 26.477 | 44.561 | 11.892 | 1.00 | 18.65 | O |
| ATOM | 21985 | N   | SER | C | 146 | 28.666 | 44.970 | 12.311 | 1.00 | 18.83 | N |
| ATOM | 21986 | CA  | SER | C | 146 | 29.014 | 43.616 | 12.793 | 1.00 | 21.14 | C |
| ATOM | 21988 | CB  | SER | C | 146 | 29.671 | 42.782 | 11.679 | 1.00 | 21.35 | C |
| ATOM | 21991 | OG  | SER | C | 146 | 28.868 | 42.734 | 10.546 | 1.00 | 28.86 | O |
| ATOM | 21993 | C   | SER | C | 146 | 30.069 | 43.643 | 13.854 | 1.00 | 22.61 | C |
| ATOM | 21994 | O   | SER | C | 146 | 30.847 | 44.574 | 13.933 | 1.00 | 22.58 | O |
| ATOM | 21996 | N   | PHE | C | 147 | 30.172 | 42.544 | 14.589 | 1.00 | 23.99 | N |
| ATOM | 21997 | CA  | PHE | C | 147 | 31.353 | 42.317 | 15.429 | 1.00 | 25.22 | C |
| ATOM | 21999 | CB  | PHE | C | 147 | 31.162 | 41.100 | 16.327 | 1.00 | 25.66 | C |
| ATOM | 22002 | CG  | PHE | C | 147 | 30.334 | 41.359 | 17.528 | 1.00 | 27.40 | C |
| ATOM | 22003 | CD1 | PHE | C | 147 | 30.530 | 42.495 | 18.296 | 1.00 | 28.74 | C |
| ATOM | 22005 | CE1 | PHE | C | 147 | 29.770 | 42.736 | 19.425 | 1.00 | 29.82 | C |
| ATOM | 22007 | CZ  | PHE | C | 147 | 28.806 | 41.817 | 19.828 | 1.00 | 30.55 | C |
| ATOM | 22009 | CE2 | PHE | C | 147 | 28.594 | 40.673 | 19.082 | 1.00 | 31.08 | C |
| ATOM | 22011 | CD2 | PHE | C | 147 | 29.360 | 40.443 | 17.922 | 1.00 | 30.40 | C |
| ATOM | 22013 | C   | PHE | C | 147 | 32.644 | 42.107 | 14.635 | 1.00 | 25.30 | C |
| ATOM | 22014 | O   | PHE | C | 147 | 33.715 | 42.130 | 15.225 | 1.00 | 24.70 | O |
| ATOM | 22016 | N   | ASP | C | 148 | 32.543 | 41.877 | 13.322 | 1.00 | 25.26 | N |
| ATOM | 22017 | CA  | ASP | C | 148 | 33.732 | 41.650 | 12.493 | 1.00 | 25.69 | C |
| ATOM | 22019 | CB  | ASP | C | 148 | 33.357 | 41.353 | 11.038 | 1.00 | 26.29 | C |
| ATOM | 22022 | CG  | ASP | C | 148 | 32.550 | 40.079 | 10.896 | 1.00 | 28.97 | C |
| ATOM | 22023 | OD1 | ASP | C | 148 | 32.574 | 39.242 | 11.831 | 1.00 | 34.02 | O |
| ATOM | 22024 | OD2 | ASP | C | 148 | 31.885 | 39.906 | 9.847  | 1.00 | 33.16 | O |
| ATOM | 22025 | C   | ASP | C | 148 | 34.668 | 42.837 | 12.510 | 1.00 | 24.74 | C |
| ATOM | 22026 | O   | ASP | C | 148 | 35.844 | 42.666 | 12.246 | 1.00 | 25.00 | O |
| ATOM | 22028 | N   | SER | C | 149 | 34.158 | 44.030 | 12.845 | 1.00 | 24.04 | N |

| ATOM | 22029 | CA | SER | C | 149 | 34.976 | 45.244 | 12.859 | 1.00 | 22.91 | C |
|------|-------|-----|-----|---|-----|--------|--------|--------|------|-------|---|
| ATOM | 22031 | CB | SER | C | 149 | 34.115 | 46.474 | 12.467 | 1.00 | 22.87 | C |
| ATOM | 22034 | OG | SER | C | 149 | 32.973 | 46.601 | 13.308 | 1.00 | 21.91 | O |
| ATOM | 22036 | C | SER | C | 149 | 35.671 | 45.509 | 14.208 | 1.00 | 22.13 | C |
| ATOM | 22037 | O | SER | C | 149 | 36.612 | 46.327 | 14.282 | 1.00 | 21.32 | O |
| ATOM | 22039 | N | PHE | C | 150 | 35.225 | 44.808 | 15.256 | 1.00 | 21.85 | N |
| ATOM | 22040 | CA | PHE | C | 150 | 35.782 | 44.987 | 16.607 | 1.00 | 21.21 | C |
| ATOM | 22042 | CB | PHE | C | 150 | 34.958 | 44.303 | 17.699 | 1.00 | 20.25 | C |
| ATOM | 22045 | CG | PHE | C | 150 | 33.662 | 45.002 | 18.050 | 1.00 | 19.79 | C |
| ATOM | 22046 | CD1 | PHE | C | 150 | 32.786 | 45.442 | 17.072 | 1.00 | 21.91 | C |
| ATOM | 22048 | CE1 | PHE | C | 150 | 31.583 | 46.023 | 17.398 | 1.00 | 18.43 | C |
| ATOM | 22050 | CZ | PHE | C | 150 | 31.245 | 46.202 | 18.708 | 1.00 | 18.60 | C |
| ATOM | 22052 | CE2 | PHE | C | 150 | 32.117 | 45.762 | 19.694 | 1.00 | 16.60 | C |
| ATOM | 22054 | CD2 | PHE | C | 150 | 33.304 | 45.166 | 19.360 | 1.00 | 18.00 | C |
| ATOM | 22056 | C | PHE | C | 150 | 37.196 | 44.455 | 16.670 | 1.00 | 21.05 | C |
| ATOM | 22057 | O | PHE | C | 150 | 37.507 | 43.403 | 16.131 | 1.00 | 22.15 | O |
| ATOM | 22059 | N | ARG | C | 151 | 38.057 | 45.209 | 17.325 | 1.00 | 19.77 | N |
| ATOM | 22060 | CA | ARG | C | 151 | 39.409 | 44.758 | 17.569 | 1.00 | 18.99 | C |
| ATOM | 22062 | CB | ARG | C | 151 | 40.387 | 45.609 | 16.760 | 1.00 | 19.10 | C |
| ATOM | 22065 | CG | ARG | C | 151 | 40.223 | 45.512 | 15.269 | 1.00 | 20.65 | C |
| ATOM | 22068 | CD | ARG | C | 151 | 40.745 | 44.220 | 14.695 | 1.00 | 24.39 | C |
| ATOM | 22071 | NE | ARG | C | 151 | 40.647 | 44.206 | 13.222 | 1.00 | 24.02 | N |
| ATOM | 22073 | CZ | ARG | C | 151 | 39.543 | 43.920 | 12.531 | 1.00 | 26.73 | C |
| ATOM | 22074 | NH1 | ARG | C | 151 | 38.405 | 43.574 | 13.142 | 1.00 | 24.67 | N |
| ATOM | 22077 | NH2 | ARG | C | 151 | 39.584 | 43.949 | 11.203 | 1.00 | 28.46 | N |
| ATOM | 22080 | C | ARG | C | 151 | 39.690 | 44.903 | 19.065 | 1.00 | 17.75 | C |
| ATOM | 22081 | O | ARG | C | 151 | 38.890 | 45.464 | 19.831 | 1.00 | 16.62 | O |
| ATOM | 22083 | N | LEU | C | 152 | 40.851 | 44.455 | 19.489 | 1.00 | 16.37 | N |
| ATOM | 22084 | CA | LEU | C | 152 | 41.183 | 44.554 | 20.872 | 1.00 | 16.29 | C |
| ATOM | 22086 | CB | LEU | C | 152 | 42.540 | 43.905 | 21.090 | 1.00 | 15.70 | C |
| ATOM | 22089 | CG | LEU | C | 152 | 43.140 | 44.020 | 22.491 | 1.00 | 16.89 | C |
| ATOM | 22091 | CD1 | LEU | C | 152 | 42.313 | 43.221 | 23.483 | 1.00 | 16.22 | C |
| ATOM | 22095 | CD2 | LEU | C | 152 | 44.524 | 43.463 | 22.456 | 1.00 | 17.81 | C |
| ATOM | 22099 | C | LEU | C | 152 | 41.162 | 46.041 | 21.277 | 1.00 | 15.51 | C |
| ATOM | 22100 | O | LEU | C | 152 | 41.805 | 46.858 | 20.641 | 1.00 | 15.63 | O |
| ATOM | 22102 | N | GLY | C | 153 | 40.388 | 46.398 | 22.305 | 1.00 | 15.44 | N |
| ATOM | 22103 | CA | GLY | C | 153 | 40.400 | 47.730 | 22.849 | 1.00 | 15.02 | C |
| ATOM | 22106 | C | GLY | C | 153 | 39.665 | 48.750 | 22.003 | 1.00 | 13.65 | C |
| ATOM | 22107 | O | GLY | C | 153 | 39.724 | 49.937 | 22.314 | 1.00 | 13.14 | O |
| ATOM | 22109 | N | ARG | C | 154 | 38.960 | 48.285 | 20.966 | 1.00 | 13.68 | N |
| ATOM | 22110 | CA | ARG | C | 154 | 38.276 | 49.143 | 20.016 | 1.00 | 14.07 | C |
| ATOM | 22112 | CB | ARG | C | 154 | 39.132 | 49.352 | 18.755 | 1.00 | 14.70 | C |
| ATOM | 22115 | CG | ARG | C | 154 | 40.583 | 49.732 | 18.941 | 1.00 | 17.22 | C |
| ATOM | 22118 | CD | ARG | C | 154 | 40.754 | 51.138 | 19.249 | 1.00 | 17.15 | C |
| ATOM | 22121 | NE | ARG | C | 154 | 42.169 | 51.492 | 19.241 | 1.00 | 15.95 | N |
| ATOM | 22123 | CZ | ARG | C | 154 | 42.634 | 52.718 | 19.462 | 1.00 | 16.64 | C |
| ATOM | 22124 | NH1 | ARG | C | 154 | 41.813 | 53.722 | 19.682 | 1.00 | 16.30 | N |
| ATOM | 22127 | NH2 | ARG | C | 154 | 43.945 | 52.936 | 19.428 | 1.00 | 14.34 | N |
| ATOM | 22130 | C | ARG | C | 154 | 36.943 | 48.520 | 19.565 | 1.00 | 14.17 | C |
| ATOM | 22131 | O | ARG | C | 154 | 36.723 | 47.340 | 19.753 | 1.00 | 13.05 | O |
| ATOM | 22133 | N | GLY | C | 155 | 36.058 | 49.361 | 19.004 | 1.00 | 13.37 | N |
| ATOM | 22134 | CA | GLY | C | 155 | 34.918 | 48.877 | 18.219 | 1.00 | 13.03 | C |
| ATOM | 22137 | C | GLY | C | 155 | 33.602 | 49.580 | 18.480 | 1.00 | 13.71 | C |
| ATOM | 22138 | O | GLY | C | 155 | 32.701 | 49.544 | 17.596 | 1.00 | 14.42 | O |
| ATOM | 22140 | N | LEU | C | 156 | 33.437 | 50.144 | 19.679 | 1.00 | 13.13 | N |
| ATOM | 22141 | CA | LEU | C | 156 | 32.187 | 50.878 | 20.035 | 1.00 | 13.73 | C |
| ATOM | 22143 | CB | LEU | C | 156 | 31.599 | 50.280 | 21.325 | 1.00 | 13.70 | C |

| ATOM | 22146 | CG | LEU | C | 156 | 30.834 | 48.964 | 21.208 | 1.00 | 14.99 | C |
|------|-------|-----|-----|---|-----|--------|--------|--------|------|-------|---|
| ATOM | 22148 | CD1 | LEU | C | 156 | 30.371 | 48.464 | 22.586 | 1.00 | 16.15 | C |
| ATOM | 22152 | CD2 | LEU | C | 156 | 29.641 | 49.089 | 20.292 | 1.00 | 17.95 | C |
| ATOM | 22156 | C   | LEU | C | 156 | 32.312 | 52.409 | 20.144 | 1.00 | 13.47 | C |
| ATOM | 22157 | O   | LEU | C | 156 | 31.468 | 53.090 | 20.759 | 1.00 | 13.53 | O |
| ATOM | 22159 | N   | GLU | C | 157 | 33.334 | 52.929 | 19.486 | 1.00 | 14.14 | N |
| ATOM | 22160 | CA  | GLU | C | 157 | 33.566 | 54.362 | 19.425 | 1.00 | 16.35 | C |
| ATOM | 22162 | CB  | GLU | C | 157 | 34.758 | 54.670 | 18.529 | 1.00 | 16.59 | C |
| ATOM | 22165 | CG  | GLU | C | 157 | 36.034 | 54.141 | 19.118 | 1.00 | 20.65 | C |
| ATOM | 22168 | CD  | GLU | C | 157 | 36.400 | 52.724 | 18.619 | 1.00 | 25.00 | C |
| ATOM | 22169 | OE1 | GLU | C | 157 | 35.531 | 52.053 | 18.032 | 1.00 | 18.29 | O |
| ATOM | 22170 | OE2 | GLU | C | 157 | 37.569 | 52.301 | 18.867 | 1.00 | 28.12 | O |
| ATOM | 22171 | C   | GLU | C | 157 | 32.382 | 55.137 | 18.903 | 1.00 | 14.89 | C |
| ATOM | 22172 | O   | GLU | C | 157 | 32.178 | 56.271 | 19.303 | 1.00 | 15.80 | O |
| ATOM | 22174 | N   | ASN | C | 158 | 31.630 | 54.572 | 17.958 | 1.00 | 13.72 | N |
| ATOM | 22175 | CA  | ASN | C | 158 | 30.466 | 55.286 | 17.420 | 1.00 | 13.99 | C |
| ATOM | 22177 | CB  | ASN | C | 158 | 30.260 | 54.889 | 15.962 | 1.00 | 15.17 | C |
| ATOM | 22180 | CG  | ASN | C | 158 | 31.255 | 55.539 | 15.051 | 1.00 | 15.34 | C |
| ATOM | 22181 | OD1 | ASN | C | 158 | 31.705 | 56.663 | 15.321 | 1.00 | 17.67 | O |
| ATOM | 22182 | ND2 | ASN | C | 158 | 31.576 | 54.859 | 13.934 | 1.00 | 16.32 | N |
| ATOM | 22185 | C   | ASN | C | 158 | 29.168 | 55.119 | 18.229 | 1.00 | 13.76 | C |
| ATOM | 22186 | O   | ASN | C | 158 | 28.089 | 55.529 | 17.762 | 1.00 | 13.65 | O |
| ATOM | 22188 | N   | SER | C | 159 | 29.276 | 54.560 | 19.451 | 1.00 | 12.83 | N |
| ATOM | 22189 | CA  | SER | C | 159 | 28.113 | 54.464 | 20.383 | 1.00 | 13.35 | C |
| ATOM | 22191 | CB  | SER | C | 159 | 27.832 | 53.024 | 20.797 | 1.00 | 13.84 | C |
| ATOM | 22194 | OG  | SER | C | 159 | 28.872 | 52.468 | 21.613 | 1.00 | 15.20 | O |
| ATOM | 22196 | C   | SER | C | 159 | 28.264 | 55.311 | 21.645 | 1.00 | 12.47 | C |
| ATOM | 22197 | O   | SER | C | 159 | 29.368 | 55.560 | 22.111 | 1.00 | 13.76 | O |
| ATOM | 22199 | N   | LEU | C | 160 | 27.122 | 55.720 | 22.185 | 1.00 | 13.71 | N |
| ATOM | 22200 | CA  | LEU | C | 160 | 27.117 | 56.462 | 23.424 | 1.00 | 14.56 | C |
| ATOM | 22202 | CB  | LEU | C | 160 | 25.712 | 56.952 | 23.769 | 1.00 | 15.68 | C |
| ATOM | 22205 | CG  | LEU | C | 160 | 25.182 | 58.233 | 23.123 | 1.00 | 19.08 | C |
| ATOM | 22207 | CD1 | LEU | C | 160 | 23.702 | 58.409 | 23.536 | 1.00 | 19.28 | C |
| ATOM | 22211 | CD2 | LEU | C | 160 | 26.022 | 59.419 | 23.461 | 1.00 | 19.12 | C |
| ATOM | 22215 | C   | LEU | C | 160 | 27.618 | 55.587 | 24.567 | 1.00 | 13.99 | C |
| ATOM | 22216 | O   | LEU | C | 160 | 27.234 | 54.459 | 24.673 | 1.00 | 12.64 | O |
| ATOM | 22218 | N   | PRO | C | 161 | 28.389 | 56.157 | 25.492 | 1.00 | 12.65 | N |
| ATOM | 22219 | CA  | PRO | C | 161 | 28.797 | 55.389 | 26.683 | 1.00 | 13.73 | C |
| ATOM | 22221 | CB  | PRO | C | 161 | 29.511 | 56.449 | 27.521 | 1.00 | 13.93 | C |
| ATOM | 22224 | CG  | PRO | C | 161 | 30.087 | 57.363 | 26.483 | 1.00 | 14.90 | C |
| ATOM | 22227 | CD  | PRO | C | 161 | 28.975 | 57.508 | 25.480 | 1.00 | 14.82 | C |
| ATOM | 22230 | C   | PRO | C | 161 | 27.590 | 54.830 | 27.411 | 1.00 | 13.19 | C |
| ATOM | 22231 | O   | PRO | C | 161 | 26.552 | 55.485 | 27.475 | 1.00 | 11.91 | O |
| ATOM | 22232 | N   | LEU | C | 162 | 27.726 | 53.613 | 27.924 | 1.00 | 14.18 | N |
| ATOM | 22233 | CA  | LEU | C | 162 | 26.615 | 52.908 | 28.591 | 1.00 | 13.14 | C |
| ATOM | 22235 | CB  | LEU | C | 162 | 27.071 | 51.518 | 29.034 | 1.00 | 15.22 | C |
| ATOM | 22238 | CG  | LEU | C | 162 | 27.533 | 50.578 | 27.911 | 1.00 | 13.28 | C |
| ATOM | 22240 | CD1 | LEU | C | 162 | 28.055 | 49.312 | 28.498 | 1.00 | 17.82 | C |
| ATOM | 22244 | CD2 | LEU | C | 162 | 26.442 | 50.287 | 26.857 | 1.00 | 18.43 | C |
| ATOM | 22248 | C   | LEU | C | 162 | 26.073 | 53.739 | 29.791 | 1.00 | 13.85 | C |
| ATOM | 22249 | O   | LEU | C | 162 | 24.869 | 53.764 | 30.068 | 1.00 | 13.03 | O |
| ATOM | 22251 | N   | GLU | C | 163 | 26.980 | 54.385 | 30.515 | 1.00 | 13.72 | N |
| ATOM | 22252 | CA  | GLU | C | 163 | 26.578 | 55.210 | 31.646 | 1.00 | 15.06 | C |
| ATOM | 22254 | CB  | GLU | C | 163 | 27.782 | 55.766 | 32.433 | 1.00 | 14.93 | C |
| ATOM | 22257 | CG  | GLU | C | 163 | 28.710 | 56.741 | 31.730 | 1.00 | 16.23 | C |
| ATOM | 22260 | CD  | GLU | C | 163 | 29.779 | 57.280 | 32.665 | 1.00 | 19.16 | C |
| ATOM | 22261 | OE1 | GLU | C | 163 | 30.157 | 56.524 | 33.594 | 1.00 | 23.60 | O |

| | | | | | | | | | |
|---|---|---|---|---|---|---|---|---|---|
| ATOM | 22262 | OE2 | GLU | C | 163 | 30.243 | 58.440 | 32.476 | 1.00 21.48 | O |
| ATOM | 22263 | C | GLU | C | 163 | 25.646 | 56.334 | 31.203 | 1.00 13.42 | C |
| ATOM | 22264 | O | GLU | C | 163 | 24.723 | 56.683 | 31.938 | 1.00 12.83 | O |
| ATOM | 22266 | N | VAL | C | 164 | 25.896 | 56.939 | 30.034 | 1.00 12.80 | N |
| ATOM | 22267 | CA | VAL | C | 164 | 25.071 | 58.046 | 29.559 | 1.00 13.11 | C |
| ATOM | 22269 | CB | VAL | C | 164 | 25.704 | 58.731 | 28.314 | 1.00 12.33 | C |
| ATOM | 22271 | CG1 | VAL | C | 164 | 24.728 | 59.732 | 27.671 | 1.00 14.08 | C |
| ATOM | 22275 | CG2 | VAL | C | 164 | 27.001 | 59.390 | 28.716 | 1.00 14.48 | C |
| ATOM | 22279 | C | VAL | C | 164 | 23.667 | 57.554 | 29.294 | 1.00 13.62 | C |
| ATOM | 22280 | O | VAL | C | 164 | 22.645 | 58.223 | 29.618 | 1.00 12.65 | O |
| ATOM | 22282 | N | VAL | C | 165 | 23.609 | 56.366 | 28.695 | 1.00 12.31 | N |
| ATOM | 22283 | CA | VAL | C | 165 | 22.319 | 55.787 | 28.321 | 1.00 12.90 | C |
| ATOM | 22285 | CB | VAL | C | 165 | 22.476 | 54.563 | 27.407 | 1.00 13.73 | C |
| ATOM | 22287 | CG1 | VAL | C | 165 | 21.129 | 53.934 | 27.145 | 1.00 12.40 | C |
| ATOM | 22291 | CG2 | VAL | C | 165 | 23.203 | 54.962 | 26.096 | 1.00 13.63 | C |
| ATOM | 22295 | C | VAL | C | 165 | 21.523 | 55.461 | 29.614 | 1.00 12.88 | C |
| ATOM | 22296 | O | VAL | C | 165 | 20.309 | 55.699 | 29.699 | 1.00 12.53 | O |
| ATOM | 22298 | N | ARG | C | 166 | 22.223 | 54.978 | 30.631 | 1.00 12.65 | N |
| ATOM | 22299 | CA | ARG | C | 166 | 21.539 | 54.652 | 31.894 | 1.00 12.53 | C |
| ATOM | 22301 | CB | ARG | C | 166 | 22.454 | 53.864 | 32.827 | 1.00 12.59 | C |
| ATOM | 22304 | CG | ARG | C | 166 | 22.650 | 52.386 | 32.465 | 1.00 13.61 | C |
| ATOM | 22307 | CD | ARG | C | 166 | 23.499 | 51.730 | 33.503 | 1.00 14.32 | C |
| ATOM | 22310 | NE | ARG | C | 166 | 22.930 | 51.816 | 34.848 | 1.00 14.39 | N |
| ATOM | 22312 | CZ | ARG | C | 166 | 22.005 | 51.009 | 35.364 | 1.00 13.03 | C |
| ATOM | 22313 | NH1 | ARG | C | 166 | 21.446 | 50.029 | 34.641 | 1.00 12.00 | N |
| ATOM | 22316 | NH2 | ARG | C | 166 | 21.562 | 51.226 | 36.599 | 1.00 13.29 | N |
| ATOM | 22319 | C | ARG | C | 166 | 21.022 | 55.913 | 32.595 | 1.00 12.79 | C |
| ATOM | 22320 | O | ARG | C | 166 | 19.906 | 55.981 | 33.090 | 1.00 12.98 | O |
| ATOM | 22322 | N | GLY | C | 167 | 21.853 | 56.946 | 32.619 | 1.00 11.82 | N |
| ATOM | 22323 | CA | GLY | C | 167 | 21.411 | 58.236 | 33.153 | 1.00 12.67 | C |
| ATOM | 22326 | C | GLY | C | 167 | 20.227 | 58.784 | 32.379 | 1.00 12.43 | C |
| ATOM | 22327 | O | GLY | C | 167 | 19.304 | 59.367 | 32.964 | 1.00 12.04 | O |
| ATOM | 22329 | N | ALA | C | 168 | 20.232 | 58.569 | 31.063 | 1.00 11.45 | N |
| ATOM | 22330 | CA | ALA | C | 168 | 19.164 | 59.094 | 30.204 | 1.00 11.60 | C |
| ATOM | 22332 | CB | ALA | C | 168 | 19.545 | 59.002 | 28.739 | 1.00 12.61 | C |
| ATOM | 22336 | C | ALA | C | 168 | 17.820 | 58.397 | 30.481 | 1.00 11.97 | C |
| ATOM | 22337 | O | ALA | C | 168 | 16.768 | 59.069 | 30.586 | 1.00 12.50 | O |
| ATOM | 22339 | N | MSE | C | 169 | 17.873 | 57.077 | 30.667 | 1.00 12.63 | N |
| ATOM | 22340 | CA | MSE | C | 169 | 16.647 | 56.317 | 30.965 | 1.00 13.96 | C |
| ATOM | 22342 | CB | MSE | C | 169 | 16.910 | 54.811 | 30.892 | 1.00 13.44 | C |
| ATOM | 22345 | CG | MSE | C | 169 | 17.256 | 54.350 | 29.478 | 1.00 15.41 | C |
| ATOM | 22348 | SE | MSE | C | 169 | 17.144 | 52.410 | 29.345 | 1.00 22.99 | SE |
| ATOM | 22349 | CE | MSE | C | 169 | 18.874 | 52.037 | 30.332 | 1.00 15.53 | C |
| ATOM | 22353 | C | MSE | C | 169 | 16.066 | 56.779 | 32.339 | 1.00 12.26 | C |
| ATOM | 22354 | O | MSE | C | 169 | 14.844 | 56.950 | 32.537 | 1.00 11.59 | O |
| ATOM | 22356 | N | THR | C | 170 | 16.964 | 57.026 | 33.283 | 1.00 11.41 | N |
| ATOM | 22357 | CA | THR | C | 170 | 16.547 | 57.463 | 34.614 | 1.00 12.04 | C |
| ATOM | 22359 | CB | THR | C | 170 | 17.776 | 57.580 | 35.534 | 1.00 13.11 | C |
| ATOM | 22361 | OG1 | THR | C | 170 | 18.432 | 56.306 | 35.636 | 1.00 13.77 | O |
| ATOM | 22363 | CG2 | THR | C | 170 | 17.378 | 58.004 | 36.881 | 1.00 11.86 | C |
| ATOM | 22367 | C | THR | C | 170 | 15.842 | 58.842 | 34.545 | 1.00 11.36 | C |
| ATOM | 22368 | O | THR | C | 170 | 14.711 | 59.030 | 35.061 | 1.00 11.08 | O |
| ATOM | 22370 | N | ILE | C | 171 | 16.491 | 59.787 | 33.859 | 1.00 11.83 | N |
| ATOM | 22371 | CA | ILE | C | 171 | 15.906 | 61.145 | 33.739 | 1.00 12.75 | C |
| ATOM | 22373 | CB | ILE | C | 171 | 16.924 | 62.140 | 33.161 | 1.00 12.55 | C |
| ATOM | 22375 | CG1 | ILE | C | 171 | 18.055 | 62.347 | 34.173 | 1.00 12.72 | C |
| ATOM | 22378 | CD1 | ILE | C | 171 | 19.344 | 63.020 | 33.578 | 1.00 13.43 | C |

| ATOM | 22382 | CG2 | ILE | C | 171 | 16.256 | 63.416 | 32.720 | 1.00 | 11.51 | C |
| ATOM | 22386 | C | ILE | C | 171 | 14.581 | 61.123 | 32.934 | 1.00 | 13.25 | C |
| ATOM | 22387 | O | ILE | C | 171 | 13.602 | 61.831 | 33.263 | 1.00 | 13.12 | O |
| ATOM | 22389 | N | ARG | C | 172 | 14.589 | 60.367 | 31.846 | 1.00 | 12.62 | N |
| ATOM | 22390 | CA | ARG | C | 172 | 13.404 | 60.188 | 30.991 | 1.00 | 13.22 | C |
| ATOM | 22392 | CB | ARG | C | 172 | 13.724 | 59.189 | 29.871 | 1.00 | 13.20 | C |
| ATOM | 22395 | CG | ARG | C | 172 | 12.555 | 58.771 | 29.046 | 1.00 | 13.91 | C |
| ATOM | 22398 | CD | ARG | C | 172 | 12.150 | 59.735 | 27.996 | 1.00 | 15.54 | C |
| ATOM | 22401 | NE | ARG | C | 172 | 11.595 | 60.957 | 28.533 | 1.00 | 15.99 | N |
| ATOM | 22403 | CZ | ARG | C | 172 | 11.325 | 62.030 | 27.775 | 1.00 | 16.18 | C |
| ATOM | 22404 | NH1 | ARG | C | 172 | 11.557 | 61.996 | 26.468 | 1.00 | 17.72 | N |
| ATOM | 22407 | NH2 | ARG | C | 172 | 10.814 | 63.135 | 28.323 | 1.00 | 18.61 | N |
| ATOM | 22410 | C | ARG | C | 172 | 12.232 | 59.689 | 31.847 | 1.00 | 13.00 | C |
| ATOM | 22411 | O | ARG | C | 172 | 11.107 | 60.187 | 31.739 | 1.00 | 14.85 | O |
| ATOM | 22413 | N | VAL | C | 173 | 12.456 | 58.655 | 32.676 | 1.00 | 12.55 | N |
| ATOM | 22414 | CA | VAL | C | 173 | 11.371 | 58.153 | 33.521 | 1.00 | 12.58 | C |
| ATOM | 22416 | CB | VAL | C | 173 | 11.764 | 56.878 | 34.302 | 1.00 | 13.18 | C |
| ATOM | 22418 | CG1 | VAL | C | 173 | 10.686 | 56.533 | 35.304 | 1.00 | 14.94 | C |
| ATOM | 22422 | CG2 | VAL | C | 173 | 11.975 | 55.699 | 33.358 | 1.00 | 14.93 | C |
| ATOM | 22426 | C | VAL | C | 173 | 10.906 | 59.233 | 34.475 | 1.00 | 12.23 | C |
| ATOM | 22427 | O | VAL | C | 173 | 9.703 | 59.490 | 34.624 | 1.00 | 11.92 | O |
| ATOM | 22429 | N | ASN | C | 174 | 11.862 | 59.874 | 35.130 | 1.00 | 12.31 | N |
| ATOM | 22430 | CA | ASN | C | 174 | 11.508 | 60.911 | 36.096 | 1.00 | 12.79 | C |
| ATOM | 22432 | CB | ASN | C | 174 | 12.738 | 61.607 | 36.675 | 1.00 | 13.79 | C |
| ATOM | 22435 | CG | ASN | C | 174 | 12.380 | 62.436 | 37.881 | 1.00 | 13.09 | C |
| ATOM | 22436 | OD1 | ASN | C | 174 | 11.904 | 61.893 | 38.901 | 1.00 | 14.35 | O |
| ATOM | 22437 | ND2 | ASN | C | 174 | 12.550 | 63.776 | 37.761 | 1.00 | 13.14 | N |
| ATOM | 22440 | C | ASN | C | 174 | 10.631 | 61.971 | 35.444 | 1.00 | 13.19 | C |
| ATOM | 22441 | O | ASN | C | 174 | 9.624 | 62.364 | 36.027 | 1.00 | 14.28 | O |
| ATOM | 22443 | N | SER | C | 175 | 11.037 | 62.414 | 34.248 | 1.00 | 14.16 | N |
| ATOM | 22444 | CA | SER | C | 175 | 10.372 | 63.490 | 33.525 | 1.00 | 14.54 | C |
| ATOM | 22446 | CB | SER | C | 175 | 11.166 | 63.900 | 32.277 | 1.00 | 16.28 | C |
| ATOM | 22449 | OG | SER | C | 175 | 11.120 | 62.906 | 31.264 | 1.00 | 17.72 | O |
| ATOM | 22451 | C | SER | C | 175 | 8.932 | 63.149 | 33.137 | 1.00 | 16.26 | C |
| ATOM | 22452 | O | SER | C | 175 | 8.117 | 64.048 | 32.925 | 1.00 | 17.94 | O |
| ATOM | 22454 | N | LEU | C | 176 | 8.640 | 61.860 | 33.020 | 1.00 | 15.03 | N |
| ATOM | 22455 | CA | LEU | C | 176 | 7.320 | 61.358 | 32.638 | 1.00 | 14.83 | C |
| ATOM | 22457 | CB | LEU | C | 176 | 7.470 | 60.171 | 31.664 | 1.00 | 14.15 | C |
| ATOM | 22460 | CG | LEU | C | 176 | 8.113 | 60.471 | 30.299 | 1.00 | 15.61 | C |
| ATOM | 22462 | CD1 | LEU | C | 176 | 8.436 | 59.235 | 29.514 | 1.00 | 17.45 | C |
| ATOM | 22466 | CD2 | LEU | C | 176 | 7.242 | 61.377 | 29.467 | 1.00 | 14.24 | C |
| ATOM | 22470 | C | LEU | C | 176 | 6.424 | 60.977 | 33.824 | 1.00 | 14.43 | C |
| ATOM | 22471 | O | LEU | C | 176 | 5.232 | 60.767 | 33.646 | 1.00 | 15.43 | O |
| ATOM | 22473 | N | THR | C | 177 | 6.970 | 60.921 | 35.033 | 1.00 | 13.27 | N |
| ATOM | 22474 | CA | THR | C | 177 | 6.153 | 60.655 | 36.213 | 1.00 | 14.22 | C |
| ATOM | 22476 | CB | THR | C | 177 | 6.982 | 60.239 | 37.411 | 1.00 | 15.13 | C |
| ATOM | 22478 | OG1 | THR | C | 177 | 7.755 | 61.383 | 37.830 | 1.00 | 17.01 | O |
| ATOM | 22480 | CG2 | THR | C | 177 | 7.892 | 59.049 | 37.051 | 1.00 | 13.88 | C |
| ATOM | 22484 | C | THR | C | 177 | 5.377 | 61.889 | 36.648 | 1.00 | 15.19 | C |
| ATOM | 22485 | O | THR | C | 177 | 4.539 | 61.810 | 37.529 | 1.00 | 13.85 | O |
| ATOM | 22487 | N | ARG | C | 178 | 5.628 | 63.030 | 35.998 | 1.00 | 15.64 | N |
| ATOM | 22488 | CA | ARG | C | 178 | 5.065 | 64.318 | 36.416 | 1.00 | 15.68 | C |
| ATOM | 22490 | CB | ARG | C | 178 | 6.001 | 65.441 | 35.942 | 1.00 | 15.51 | C |
| ATOM | 22493 | CG | ARG | C | 178 | 7.371 | 65.399 | 36.639 | 1.00 | 16.78 | C |
| ATOM | 22496 | CD | ARG | C | 178 | 8.458 | 66.192 | 35.878 | 1.00 | 15.45 | C |
| ATOM | 22499 | NE | ARG | C | 178 | 8.052 | 67.574 | 35.594 | 1.00 | 14.69 | N |
| ATOM | 22501 | CZ | ARG | C | 178 | 7.996 | 68.549 | 36.514 | 1.00 | 17.35 | C |

```
ATOM  22502  NH1  ARG  C  178    8.347  68.325  37.783  1.00  17.17           N
ATOM  22505  NH2  ARG  C  178    7.599  69.778  36.158  1.00  16.47           N
ATOM  22508  C    ARG  C  178    3.618  64.526  35.982  1.00  15.69           C
ATOM  22509  O    ARG  C  178    2.937  65.474  36.398  1.00  16.14           O
ATOM  22511  N    GLY  C  179    3.129  63.670  35.104  1.00  15.28           N
ATOM  22512  CA   GLY  C  179    1.730  63.686  34.806  1.00  15.05           C
ATOM  22515  C    GLY  C  179    1.312  64.625  33.697  1.00  14.74           C
ATOM  22516  O    GLY  C  179    0.104  64.841  33.490  1.00  15.70           O
ATOM  22518  N    HIS  C  180    2.286  65.129  32.941  1.00  14.00           N
ATOM  22519  CA   HIS  C  180    2.041  66.104  31.879  1.00  13.55           C
ATOM  22521  CB   HIS  C  180    3.098  67.209  31.987  1.00  13.73           C
ATOM  22524  CG   HIS  C  180    3.167  67.853  33.335  1.00  13.19           C
ATOM  22525  ND1  HIS  C  180    4.361  68.181  33.937  1.00  12.93           N
ATOM  22527  CE1  HIS  C  180    4.120  68.763  35.095  1.00  13.52           C
ATOM  22529  NE2  HIS  C  180    2.809  68.828  35.270  1.00  14.27           N
ATOM  22531  CD2  HIS  C  180    2.190  68.284  34.168  1.00  14.36           C
ATOM  22533  C    HIS  C  180    2.110  65.493  30.470  1.00  13.24           C
ATOM  22534  O    HIS  C  180    1.988  66.203  29.470  1.00  14.91           O
ATOM  22536  N    SER  C  181    2.364  64.197  30.379  1.00  13.23           N
ATOM  22537  CA   SER  C  181    2.841  63.608  29.113  1.00  12.81           C
ATOM  22539  CB   SER  C  181    4.255  63.092  29.301  1.00  13.77           C
ATOM  22542  OG   SER  C  181    5.072  64.166  29.792  1.00  12.20           O
ATOM  22544  C    SER  C  181    1.994  62.525  28.484  1.00  13.33           C
ATOM  22545  O    SER  C  181    2.146  62.225  27.316  1.00  13.61           O
ATOM  22547  N    ALA  C  182    1.112  61.922  29.272  1.00  13.92           N
ATOM  22548  CA   ALA  C  182    0.258  60.832  28.818  1.00  14.86           C
ATOM  22550  CB   ALA  C  182   -0.736  61.301  27.799  1.00  14.71           C
ATOM  22554  C    ALA  C  182    1.007  59.604  28.319  1.00  14.41           C
ATOM  22555  O    ALA  C  182    0.547  58.918  27.393  1.00  15.33           O
ATOM  22557  N    VAL  C  183    2.112  59.284  28.971  1.00  14.85           N
ATOM  22558  CA   VAL  C  183    2.804  58.034  28.732  1.00  14.99           C
ATOM  22560  CB   VAL  C  183    4.327  58.208  28.656  1.00  14.67           C
ATOM  22562  CG1  VAL  C  183    4.986  56.864  28.465  1.00  13.64           C
ATOM  22566  CG2  VAL  C  183    4.683  59.147  27.517  1.00  15.04           C
ATOM  22570  C    VAL  C  183    2.437  57.027  29.863  1.00  14.80           C
ATOM  22571  O    VAL  C  183    2.526  57.355  31.040  1.00  14.34           O
ATOM  22573  N    ARG  C  184    1.980  55.831  29.503  1.00  14.77           N
ATOM  22574  CA   ARG  C  184    1.551  54.863  30.523  1.00  14.41           C
ATOM  22576  CB   ARG  C  184    1.023  53.586  29.857  1.00  14.18           C
ATOM  22579  CG   ARG  C  184   -0.246  53.773  29.085  1.00  14.73           C
ATOM  22582  CD   ARG  C  184   -0.560  52.532  28.288  1.00  15.62           C
ATOM  22585  NE   ARG  C  184    0.460  52.353  27.252  1.00  17.41           N
ATOM  22587  CZ   ARG  C  184    0.822  51.193  26.701  1.00  19.76           C
ATOM  22588  NH1  ARG  C  184    0.210  50.055  27.018  1.00  19.12           N
ATOM  22591  NH2  ARG  C  184    1.770  51.187  25.771  1.00  17.82           N
ATOM  22594  C    ARG  C  184    2.654  54.464  31.489  1.00  14.47           C
ATOM  22595  O    ARG  C  184    3.811  54.382  31.123  1.00  14.02           O
ATOM  22597  N    LEU  C  185    2.254  54.155  32.717  1.00  14.54           N
ATOM  22598  CA   LEU  C  185    3.150  53.571  33.719  1.00  14.69           C
ATOM  22600  CB   LEU  C  185    2.365  53.209  34.997  1.00  15.62           C
ATOM  22603  CG   LEU  C  185    3.211  52.634  36.156  1.00  14.96           C
ATOM  22605  CD1  LEU  C  185    4.343  53.582  36.572  1.00  17.44           C
ATOM  22609  CD2  LEU  C  185    2.286  52.329  37.329  1.00  15.97           C
ATOM  22613  C    LEU  C  185    3.888  52.328  33.223  1.00  13.64           C
ATOM  22614  O    LEU  C  185    5.075  52.141  33.481  1.00  13.96           O
ATOM  22616  N    VAL  C  186    3.179  51.475  32.496  1.00  13.85           N
ATOM  22617  CA   VAL  C  186    3.791  50.234  32.003  1.00  14.15           C
```

| | | | | | | | | | |
|---|---|---|---|---|---|---|---|---|---|
| ATOM | 22619 | CB | VAL | C | 186 | 2.749 | 49.301 | 31.301 | 1.00 15.15 | C |
| ATOM | 22621 | CG1 | VAL | C | 186 | 2.223 | 49.918 | 30.027 | 1.00 13.42 | C |
| ATOM | 22625 | CG2 | VAL | C | 186 | 3.350 | 47.942 | 31.029 | 1.00 16.27 | C |
| ATOM | 22629 | C | VAL | C | 186 | 5.004 | 50.563 | 31.100 | 1.00 14.11 | C |
| ATOM | 22630 | O | VAL | C | 186 | 6.007 | 49.836 | 31.088 | 1.00 15.21 | O |
| ATOM | 22632 | N | VAL | C | 187 | 4.924 | 51.674 | 30.368 | 1.00 13.74 | N |
| ATOM | 22633 | CA | VAL | C | 187 | 6.059 | 52.120 | 29.536 | 1.00 13.08 | C |
| ATOM | 22635 | CB | VAL | C | 187 | 5.611 | 53.190 | 28.467 | 1.00 12.84 | C |
| ATOM | 22637 | CG1 | VAL | C | 187 | 6.815 | 53.798 | 27.719 | 1.00 13.64 | C |
| ATOM | 22641 | CG2 | VAL | C | 187 | 4.628 | 52.558 | 27.527 | 1.00 14.77 | C |
| ATOM | 22645 | C | VAL | C | 187 | 7.239 | 52.574 | 30.420 | 1.00 12.67 | C |
| ATOM | 22646 | O | VAL | C | 187 | 8.388 | 52.188 | 30.193 | 1.00 13.21 | O |
| ATOM | 22648 | N | LEU | C | 188 | 6.951 | 53.355 | 31.456 | 1.00 13.20 | N |
| ATOM | 22649 | CA | LEU | C | 188 | 7.976 | 53.791 | 32.399 | 1.00 13.94 | C |
| ATOM | 22651 | CB | LEU | C | 188 | 7.408 | 54.802 | 33.427 | 1.00 14.69 | C |
| ATOM | 22654 | CG | LEU | C | 188 | 6.690 | 56.061 | 32.903 | 1.00 17.78 | C |
| ATOM | 22656 | CD1 | LEU | C | 188 | 6.400 | 57.008 | 34.056 | 1.00 19.35 | C |
| ATOM | 22660 | CD2 | LEU | C | 188 | 7.438 | 56.760 | 31.802 | 1.00 20.66 | C |
| ATOM | 22664 | C | LEU | C | 188 | 8.608 | 52.620 | 33.103 | 1.00 13.81 | C |
| ATOM | 22665 | O | LEU | C | 188 | 9.824 | 52.584 | 33.275 | 1.00 13.50 | O |
| ATOM | 22667 | N | GLU | C | 189 | 7.796 | 51.617 | 33.433 | 1.00 13.63 | N |
| ATOM | 22668 | CA | GLU | C | 189 | 8.300 | 50.396 | 34.076 | 1.00 13.39 | C |
| ATOM | 22670 | CB | GLU | C | 189 | 7.134 | 49.553 | 34.564 | 1.00 13.79 | C |
| ATOM | 22673 | CG | GLU | C | 189 | 6.448 | 50.188 | 35.721 | 1.00 14.73 | C |
| ATOM | 22676 | CD | GLU | C | 189 | 5.173 | 49.441 | 36.139 | 1.00 16.39 | C |
| ATOM | 22677 | OE1 | GLU | C | 189 | 4.537 | 48.734 | 35.296 | 1.00 19.95 | O |
| ATOM | 22678 | OE2 | GLU | C | 189 | 4.803 | 49.568 | 37.315 | 1.00 21.77 | O |
| ATOM | 22679 | C | GLU | C | 189 | 9.176 | 49.587 | 33.129 | 1.00 13.27 | C |
| ATOM | 22680 | O | GLU | C | 189 | 10.063 | 48.851 | 33.572 | 1.00 14.34 | O |
| ATOM | 22682 | N | ALA | C | 190 | 8.923 | 49.700 | 31.826 | 1.00 13.07 | N |
| ATOM | 22683 | CA | ALA | C | 190 | 9.778 | 48.990 | 30.867 | 1.00 12.95 | C |
| ATOM | 22685 | CB | ALA | C | 190 | 9.180 | 49.003 | 29.441 | 1.00 12.54 | C |
| ATOM | 22689 | C | ALA | C | 190 | 11.190 | 49.553 | 30.916 | 1.00 12.83 | C |
| ATOM | 22690 | O | ALA | C | 190 | 12.163 | 48.795 | 30.836 | 1.00 13.17 | O |
| ATOM | 22692 | N | LEU | C | 191 | 11.310 | 50.876 | 31.094 | 1.00 12.98 | N |
| ATOM | 22693 | CA | LEU | C | 191 | 12.620 | 51.543 | 31.224 | 1.00 11.78 | C |
| ATOM | 22695 | CB | LEU | C | 191 | 12.474 | 53.060 | 31.053 | 1.00 12.73 | C |
| ATOM | 22698 | CG | LEU | C | 191 | 12.015 | 53.525 | 29.660 | 1.00 12.36 | C |
| ATOM | 22700 | CD1 | LEU | C | 191 | 11.489 | 54.963 | 29.813 | 1.00 13.59 | C |
| ATOM | 22704 | CD2 | LEU | C | 191 | 13.179 | 53.488 | 28.683 | 1.00 14.29 | C |
| ATOM | 22708 | C | LEU | C | 191 | 13.273 | 51.212 | 32.565 | 1.00 12.55 | C |
| ATOM | 22709 | O | LEU | C | 191 | 14.473 | 50.930 | 32.623 | 1.00 13.72 | O |
| ATOM | 22711 | N | THR | C | 192 | 12.505 | 51.240 | 33.661 | 1.00 11.84 | N |
| ATOM | 22712 | CA | THR | C | 192 | 13.094 | 50.877 | 34.968 | 1.00 11.69 | C |
| ATOM | 22714 | CB | THR | C | 192 | 12.172 | 51.268 | 36.179 | 1.00 11.71 | C |
| ATOM | 22716 | OG1 | THR | C | 192 | 10.952 | 50.535 | 36.163 | 1.00 11.81 | O |
| ATOM | 22718 | CG2 | THR | C | 192 | 11.876 | 52.788 | 36.199 | 1.00 11.89 | C |
| ATOM | 22722 | C | THR | C | 192 | 13.513 | 49.390 | 35.013 | 1.00 10.91 | C |
| ATOM | 22723 | O | THR | C | 192 | 14.521 | 49.054 | 35.632 | 1.00 10.87 | O |
| ATOM | 22725 | N | ASN | C | 193 | 12.761 | 48.516 | 34.345 | 1.00 11.02 | N |
| ATOM | 22726 | CA | ASN | C | 193 | 13.178 | 47.107 | 34.200 | 1.00 11.03 | C |
| ATOM | 22728 | CB | ASN | C | 193 | 12.059 | 46.261 | 33.611 | 1.00 11.30 | C |
| ATOM | 22731 | CG | ASN | C | 193 | 10.940 | 45.995 | 34.642 | 1.00 11.35 | C |
| ATOM | 22732 | OD1 | ASN | C | 193 | 11.194 | 46.095 | 35.851 | 1.00 14.88 | O |
| ATOM | 22733 | ND2 | ASN | C | 193 | 9.733 | 45.714 | 34.190 | 1.00 12.27 | N |
| ATOM | 22736 | C | ASN | C | 193 | 14.479 | 46.973 | 33.415 | 1.00 12.03 | C |
| ATOM | 22737 | O | ASN | C | 193 | 15.341 | 46.149 | 33.770 | 1.00 13.49 | O |

| ATOM | 22739 | N   | PHE C 194 | 14.664 | 47.817 | 32.397 | 1.00 | 12.70 | N |
|------|-------|-----|-----------|--------|--------|--------|------|-------|---|
| ATOM | 22740 | CA  | PHE C 194 | 15.923 | 47.801 | 31.659 | 1.00 | 13.20 | C |
| ATOM | 22742 | CB  | PHE C 194 | 15.887 | 48.712 | 30.445 | 1.00 | 13.86 | C |
| ATOM | 22745 | CG  | PHE C 194 | 15.465 | 48.018 | 29.185 | 1.00 | 13.45 | C |
| ATOM | 22746 | CD1 | PHE C 194 | 14.553 | 46.965 | 29.208 | 1.00 | 14.63 | C |
| ATOM | 22748 | CE1 | PHE C 194 | 14.141 | 46.320 | 28.040 | 1.00 | 16.10 | C |
| ATOM | 22750 | CZ  | PHE C 194 | 14.664 | 46.709 | 26.827 | 1.00 | 15.21 | C |
| ATOM | 22752 | CE2 | PHE C 194 | 15.595 | 47.738 | 26.781 | 1.00 | 13.37 | C |
| ATOM | 22754 | CD2 | PHE C 194 | 15.993 | 48.405 | 27.970 | 1.00 | 12.00 | C |
| ATOM | 22756 | C   | PHE C 194 | 17.064 | 48.195 | 32.594 | 1.00 | 13.49 | C |
| ATOM | 22757 | O   | PHE C 194 | 18.107 | 47.535 | 32.648 | 1.00 | 14.34 | O |
| ATOM | 22759 | N   | LEU C 195 | 16.830 | 49.237 | 33.372 | 1.00 | 13.48 | N |
| ATOM | 22760 | CA  | LEU C 195 | 17.837 | 49.741 | 34.287 | 1.00 | 13.36 | C |
| ATOM | 22762 | CB  | LEU C 195 | 17.333 | 50.994 | 35.001 | 1.00 | 12.94 | C |
| ATOM | 22765 | CG  | LEU C 195 | 17.406 | 52.290 | 34.145 | 1.00 | 10.91 | C |
| ATOM | 22767 | CD1 | LEU C 195 | 16.440 | 53.439 | 34.684 | 1.00 | 13.58 | C |
| ATOM | 22771 | CD2 | LEU C 195 | 18.876 | 52.802 | 33.992 | 1.00 | 12.45 | C |
| ATOM | 22775 | C   | LEU C 195 | 18.189 | 48.665 | 35.298 | 1.00 | 13.70 | C |
| ATOM | 22776 | O   | LEU C 195 | 19.343 | 48.377 | 35.538 | 1.00 | 13.62 | O |
| ATOM | 22778 | N   | ASN C 196 | 17.162 | 48.066 | 35.884 | 1.00 | 13.53 | N |
| ATOM | 22779 | CA  | ASN C 196 | 17.371 | 47.158 | 37.017 | 1.00 | 13.70 | C |
| ATOM | 22781 | CB  | ASN C 196 | 16.098 | 47.035 | 37.837 | 1.00 | 13.64 | C |
| ATOM | 22784 | CG  | ASN C 196 | 15.693 | 48.340 | 38.472 | 1.00 | 12.97 | C |
| ATOM | 22785 | OD1 | ASN C 196 | 16.528 | 49.209 | 38.695 | 1.00 | 15.48 | O |
| ATOM | 22786 | ND2 | ASN C 196 | 14.394 | 48.499 | 38.738 | 1.00 | 12.09 | N |
| ATOM | 22789 | C   | ASN C 196 | 17.912 | 45.802 | 36.611 | 1.00 | 14.55 | C |
| ATOM | 22790 | O   | ASN C 196 | 18.514 | 45.090 | 37.450 | 1.00 | 15.39 | O |
| ATOM | 22792 | N   | HIS C 197 | 17.702 | 45.439 | 35.349 | 1.00 | 14.07 | N |
| ATOM | 22793 | CA  | HIS C 197 | 18.296 | 44.229 | 34.790 | 1.00 | 15.55 | C |
| ATOM | 22795 | CB  | HIS C 197 | 17.285 | 43.492 | 33.933 | 1.00 | 14.45 | C |
| ATOM | 22798 | CG  | HIS C 197 | 16.172 | 42.913 | 34.728 | 1.00 | 15.82 | C |
| ATOM | 22799 | ND1 | HIS C 197 | 16.400 | 41.973 | 35.710 | 1.00 | 16.93 | N |
| ATOM | 22801 | CE1 | HIS C 197 | 15.253 | 41.652 | 36.276 | 1.00 | 17.41 | C |
| ATOM | 22803 | NE2 | HIS C 197 | 14.289 | 42.325 | 35.681 | 1.00 | 15.72 | N |
| ATOM | 22805 | CD2 | HIS C 197 | 14.848 | 43.162 | 34.738 | 1.00 | 17.51 | C |
| ATOM | 22807 | C   | HIS C 197 | 19.593 | 44.481 | 34.029 | 1.00 | 15.06 | C |
| ATOM | 22808 | O   | HIS C 197 | 20.198 | 43.539 | 33.492 | 1.00 | 17.37 | O |
| ATOM | 22810 | N   | GLY C 198 | 20.068 | 45.713 | 34.019 | 1.00 | 15.62 | N |
| ATOM | 22811 | CA  | GLY C 198 | 21.351 | 45.986 | 33.392 | 1.00 | 15.25 | C |
| ATOM | 22814 | C   | GLY C 198 | 21.320 | 45.833 | 31.883 | 1.00 | 14.63 | C |
| ATOM | 22815 | O   | GLY C 198 | 22.299 | 45.411 | 31.284 | 1.00 | 14.91 | O |
| ATOM | 22817 | N   | ILE C 199 | 20.183 | 46.179 | 31.296 | 1.00 | 12.67 | N |
| ATOM | 22818 | CA  | ILE C 199 | 19.991 | 46.168 | 29.841 | 1.00 | 13.14 | C |
| ATOM | 22820 | CB  | ILE C 199 | 18.582 | 45.656 | 29.459 | 1.00 | 13.75 | C |
| ATOM | 22822 | CG1 | ILE C 199 | 18.366 | 44.247 | 29.980 | 1.00 | 13.87 | C |
| ATOM | 22825 | CD1 | ILE C 199 | 16.938 | 43.748 | 29.807 | 1.00 | 15.16 | C |
| ATOM | 22829 | CG2 | ILE C 199 | 18.403 | 45.685 | 27.944 | 1.00 | 13.74 | C |
| ATOM | 22833 | C   | ILE C 199 | 20.142 | 47.595 | 29.350 | 1.00 | 13.55 | C |
| ATOM | 22834 | O   | ILE C 199 | 19.313 | 48.452 | 29.693 | 1.00 | 13.33 | O |
| ATOM | 22836 | N   | THR C 200 | 21.175 | 47.841 | 28.546 | 1.00 | 13.26 | N |
| ATOM | 22837 | CA  | THR C 200 | 21.464 | 49.189 | 28.092 | 1.00 | 12.64 | C |
| ATOM | 22839 | CB  | THR C 200 | 22.854 | 49.684 | 28.620 | 1.00 | 13.61 | C |
| ATOM | 22841 | OG1 | THR C 200 | 22.915 | 49.526 | 30.038 | 1.00 | 14.56 | O |
| ATOM | 22843 | CG2 | THR C 200 | 23.061 | 51.142 | 28.327 | 1.00 | 12.87 | C |
| ATOM | 22847 | C   | THR C 200 | 21.451 | 49.299 | 26.576 | 1.00 | 12.91 | C |
| ATOM | 22848 | O   | THR C 200 | 22.326 | 48.745 | 25.911 | 1.00 | 13.39 | O |
| ATOM | 22850 | N   | PRO C 201 | 20.463 | 50.009 | 26.010 | 1.00 | 11.54 | N |

| ATOM | 22851 | CA | PRO | C | 201 | 20.439 | 50.141 | 24.561 | 1.00 | 12.09 | C |
| ATOM | 22853 | CB | PRO | C | 201 | 19.356 | 51.212 | 24.342 | 1.00 | 11.81 | C |
| ATOM | 22856 | CG | PRO | C | 201 | 18.377 | 50.956 | 25.497 | 1.00 | 12.36 | C |
| ATOM | 22859 | CD | PRO | C | 201 | 19.277 | 50.627 | 26.650 | 1.00 | 12.08 | C |
| ATOM | 22862 | C | PRO | C | 201 | 21.750 | 50.623 | 23.978 | 1.00 | 11.50 | C |
| ATOM | 22863 | O | PRO | C | 201 | 22.408 | 51.495 | 24.546 | 1.00 | 11.82 | O |
| ATOM | 22864 | N | ILE | C | 202 | 22.127 | 50.037 | 22.853 | 1.00 | 12.52 | N |
| ATOM | 22865 | CA | ILE | C | 202 | 23.206 | 50.533 | 22.022 | 1.00 | 13.24 | C |
| ATOM | 22867 | CB | ILE | C | 202 | 23.776 | 49.447 | 21.111 | 1.00 | 14.21 | C |
| ATOM | 22869 | CG1 | ILE | C | 202 | 24.383 | 48.292 | 21.954 | 1.00 | 16.30 | C |
| ATOM | 22872 | CD1 | ILE | C | 202 | 25.520 | 48.642 | 22.868 | 1.00 | 18.15 | C |
| ATOM | 22876 | CG2 | ILE | C | 202 | 24.827 | 50.031 | 20.162 | 1.00 | 13.97 | C |
| ATOM | 22880 | C | ILE | C | 202 | 22.674 | 51.682 | 21.162 | 1.00 | 13.26 | C |
| ATOM | 22881 | O | ILE | C | 202 | 21.779 | 51.473 | 20.324 | 1.00 | 14.14 | O |
| ATOM | 22883 | N | VAL | C | 203 | 23.303 | 52.837 | 21.333 | 1.00 | 12.34 | N |
| ATOM | 22884 | CA | VAL | C | 203 | 22.778 | 54.092 | 20.765 | 1.00 | 13.36 | C |
| ATOM | 22886 | CB | VAL | C | 203 | 22.211 | 55.017 | 21.875 | 1.00 | 14.61 | C |
| ATOM | 22888 | CG1 | VAL | C | 203 | 21.626 | 56.314 | 21.272 | 1.00 | 15.70 | C |
| ATOM | 22892 | CG2 | VAL | C | 203 | 21.187 | 54.289 | 22.716 | 1.00 | 14.74 | C |
| ATOM | 22896 | C | VAL | C | 203 | 23.908 | 54.791 | 20.028 | 1.00 | 13.56 | C |
| ATOM | 22897 | O | VAL | C | 203 | 25.004 | 54.908 | 20.552 | 1.00 | 13.16 | O |
| ATOM | 22899 | N | PRO | C | 204 | 23.650 | 55.279 | 18.829 | 1.00 | 13.05 | N |
| ATOM | 22900 | CA | PRO | C | 204 | 24.692 | 56.040 | 18.148 | 1.00 | 12.67 | C |
| ATOM | 22902 | CB | PRO | C | 204 | 23.991 | 56.455 | 16.823 | 1.00 | 13.32 | C |
| ATOM | 22905 | CG | PRO | C | 204 | 22.947 | 55.478 | 16.636 | 1.00 | 13.16 | C |
| ATOM | 22908 | CD | PRO | C | 204 | 22.439 | 55.233 | 18.009 | 1.00 | 13.30 | C |
| ATOM | 22911 | C | PRO | C | 204 | 25.176 | 57.243 | 18.914 | 1.00 | 12.22 | C |
| ATOM | 22912 | O | PRO | C | 204 | 24.405 | 57.932 | 19.573 | 1.00 | 12.85 | O |
| ATOM | 22913 | N | LEU | C | 205 | 26.465 | 57.518 | 18.785 | 1.00 | 13.20 | N |
| ATOM | 22914 | CA | LEU | C | 205 | 27.078 | 58.668 | 19.466 | 1.00 | 12.36 | C |
| ATOM | 22916 | CB | LEU | C | 205 | 28.586 | 58.618 | 19.292 | 1.00 | 13.50 | C |
| ATOM | 22919 | CG | LEU | C | 205 | 29.395 | 59.739 | 19.909 | 1.00 | 13.87 | C |
| ATOM | 22921 | CD1 | LEU | C | 205 | 29.268 | 59.690 | 21.385 | 1.00 | 15.09 | C |
| ATOM | 22925 | CD2 | LEU | C | 205 | 30.829 | 59.604 | 19.473 | 1.00 | 13.86 | C |
| ATOM | 22929 | C | LEU | C | 205 | 26.565 | 60.034 | 18.930 | 1.00 | 12.19 | C |
| ATOM | 22930 | O | LEU | C | 205 | 26.339 | 60.982 | 19.678 | 1.00 | 12.94 | O |
| ATOM | 22932 | N | ARG | C | 206 | 26.412 | 60.081 | 17.617 | 1.00 | 12.75 | N |
| ATOM | 22933 | CA | ARG | C | 206 | 26.127 | 61.270 | 16.873 | 1.00 | 12.09 | C |
| ATOM | 22935 | CB | ARG | C | 206 | 27.266 | 61.560 | 15.879 | 1.00 | 12.97 | C |
| ATOM | 22938 | CG | ARG | C | 206 | 28.664 | 61.674 | 16.488 | 1.00 | 12.91 | C |
| ATOM | 22941 | CD | ARG | C | 206 | 29.663 | 62.201 | 15.458 | 1.00 | 14.59 | C |
| ATOM | 22944 | NE | ARG | C | 206 | 30.999 | 62.551 | 15.947 | 1.00 | 12.58 | N |
| ATOM | 22946 | CZ | ARG | C | 206 | 32.069 | 61.781 | 15.938 | 1.00 | 15.81 | C |
| ATOM | 22947 | NH1 | ARG | C | 206 | 31.993 | 60.533 | 15.530 | 1.00 | 17.45 | N |
| ATOM | 22950 | NH2 | ARG | C | 206 | 33.218 | 62.270 | 16.336 | 1.00 | 16.67 | N |
| ATOM | 22953 | C | ARG | C | 206 | 24.820 | 61.198 | 16.112 | 1.00 | 11.59 | C |
| ATOM | 22954 | O | ARG | C | 206 | 24.287 | 60.115 | 15.769 | 1.00 | 11.66 | O |
| ATOM | 22956 | N | GLY | C | 207 | 24.310 | 62.402 | 15.820 | 1.00 | 11.77 | N |
| ATOM | 22957 | CA | GLY | C | 207 | 23.159 | 62.583 | 14.970 | 1.00 | 12.17 | C |
| ATOM | 22960 | C | GLY | C | 207 | 22.112 | 63.504 | 15.545 | 1.00 | 13.73 | C |
| ATOM | 22961 | O | GLY | C | 207 | 21.221 | 63.919 | 14.797 | 1.00 | 15.36 | O |
| ATOM | 22963 | N | THR | C | 208 | 22.139 | 63.743 | 16.853 | 1.00 | 13.19 | N |
| ATOM | 22964 | CA | THR | C | 208 | 21.164 | 64.692 | 17.441 | 1.00 | 12.40 | C |
| ATOM | 22966 | CB | THR | C | 208 | 20.668 | 64.290 | 18.857 | 1.00 | 13.96 | C |
| ATOM | 22968 | OG1 | THR | C | 208 | 19.594 | 65.135 | 19.249 | 1.00 | 15.15 | O |
| ATOM | 22970 | CG2 | THR | C | 208 | 21.758 | 64.341 | 19.890 | 1.00 | 15.05 | C |
| ATOM | 22974 | C | THR | C | 208 | 21.703 | 66.137 | 17.494 | 1.00 | 12.76 | C |

| ATOM | 22975 | O | THR | C | 208 | 22.889 | 66.400 | 17.728 | 1.00 | 12.47 | O |
| ATOM | 22977 | N | ILE | C | 209 | 20.800 | 67.064 | 17.255 | 1.00 | 11.79 | N |
| ATOM | 22978 | CA | ILE | C | 209 | 21.004 | 68.470 | 17.509 | 1.00 | 11.67 | C |
| ATOM | 22980 | CB | ILE | C | 209 | 20.502 | 69.310 | 16.325 | 1.00 | 12.46 | C |
| ATOM | 22982 | CG1 | ILE | C | 209 | 18.986 | 69.194 | 16.170 | 1.00 | 10.90 | C |
| ATOM | 22985 | CD1 | ILE | C | 209 | 18.485 | 69.913 | 14.899 | 1.00 | 11.31 | C |
| ATOM | 22989 | CG2 | ILE | C | 209 | 21.265 | 68.963 | 15.071 | 1.00 | 12.60 | C |
| ATOM | 22993 | C | ILE | C | 209 | 20.372 | 68.969 | 18.835 | 1.00 | 11.64 | C |
| ATOM | 22994 | O | ILE | C | 209 | 20.409 | 70.150 | 19.136 | 1.00 | 12.03 | O |
| ATOM | 22996 | N | SER | C | 210 | 19.781 | 68.041 | 19.604 | 1.00 | 11.97 | N |
| ATOM | 22997 | CA | SER | C | 210 | 19.291 | 68.316 | 20.930 | 1.00 | 12.35 | C |
| ATOM | 22999 | CB | SER | C | 210 | 20.446 | 68.615 | 21.918 | 1.00 | 12.92 | C |
| ATOM | 23002 | OG | SER | C | 210 | 21.438 | 67.595 | 21.889 | 1.00 | 12.29 | O |
| ATOM | 23004 | C | SER | C | 210 | 18.223 | 69.421 | 20.966 | 1.00 | 12.72 | C |
| ATOM | 23005 | O | SER | C | 210 | 18.274 | 70.348 | 21.803 | 1.00 | 13.33 | O |
| ATOM | 23007 | N | ALA | C | 211 | 17.268 | 69.332 | 20.026 | 1.00 | 11.80 | N |
| ATOM | 23008 | CA | ALA | C | 211 | 16.055 | 70.154 | 20.028 | 1.00 | 13.63 | C |
| ATOM | 23010 | CB | ALA | C | 211 | 16.044 | 71.095 | 18.932 | 1.00 | 13.85 | C |
| ATOM | 23014 | C | ALA | C | 211 | 14.891 | 69.192 | 19.951 | 1.00 | 13.67 | C |
| ATOM | 23017 | N | SER | C | 212 | 13.822 | 69.197 | 19.138 | 1.00 | 14.65 | N |
| ATOM | 23018 | CA | SER | C | 212 | 12.747 | 68.399 | 19.686 | 1.00 | 15.47 | C |
| ATOM | 23020 | CB | SER | C | 212 | 11.760 | 67.755 | 18.750 | 1.00 | 15.83 | C |
| ATOM | 23024 | C | SER | C | 212 | 13.527 | 67.523 | 20.641 | 1.00 | 14.98 | C |
| ATOM | 23025 | O | SER | C | 212 | 13.081 | 66.532 | 21.176 | 1.00 | 13.58 | O |
| ATOM | 23027 | N | GLY | C | 213 | 14.653 | 68.108 | 21.029 | 1.00 | 14.24 | N |
| ATOM | 23028 | CA | GLY | C | 213 | 15.619 | 67.512 | 21.900 | 1.00 | 13.90 | C |
| ATOM | 23031 | C | GLY | C | 213 | 16.423 | 66.412 | 21.280 | 1.00 | 13.35 | C |
| ATOM | 23032 | O | GLY | C | 213 | 16.758 | 66.433 | 20.097 | 1.00 | 12.77 | O |
| ATOM | 23034 | N | ASP | C | 214 | 16.726 | 65.405 | 22.095 | 1.00 | 12.59 | N |
| ATOM | 23035 | CA | ASP | C | 214 | 17.656 | 64.377 | 21.758 | 1.00 | 12.23 | C |
| ATOM | 23037 | CB | ASP | C | 214 | 18.275 | 63.854 | 23.057 | 1.00 | 13.12 | C |
| ATOM | 23040 | CG | ASP | C | 214 | 19.084 | 64.927 | 23.790 | 1.00 | 13.16 | C |
| ATOM | 23041 | OD1 | ASP | C | 214 | 19.819 | 65.662 | 23.139 | 1.00 | 16.03 | O |
| ATOM | 23042 | OD2 | ASP | C | 214 | 19.007 | 64.999 | 25.040 | 1.00 | 15.70 | O |
| ATOM | 23043 | C | ASP | C | 214 | 16.900 | 63.277 | 21.010 | 1.00 | 12.77 | C |
| ATOM | 23044 | O | ASP | C | 214 | 16.845 | 62.117 | 21.438 | 1.00 | 11.95 | O |
| ATOM | 23046 | N | LEU | C | 215 | 16.280 | 63.668 | 19.888 | 1.00 | 13.25 | N |
| ATOM | 23047 | CA | LEU | C | 215 | 15.332 | 62.798 | 19.207 | 1.00 | 12.84 | C |
| ATOM | 23049 | CB | LEU | C | 215 | 14.773 | 63.480 | 17.963 | 1.00 | 12.78 | C |
| ATOM | 23052 | CG | LEU | C | 215 | 13.892 | 64.707 | 18.193 | 1.00 | 13.01 | C |
| ATOM | 23054 | CD1 | LEU | C | 215 | 13.716 | 65.398 | 16.875 | 1.00 | 13.77 | C |
| ATOM | 23058 | CD2 | LEU | C | 215 | 12.581 | 64.321 | 18.748 | 1.00 | 15.81 | C |
| ATOM | 23062 | C | LEU | C | 215 | 15.891 | 61.435 | 18.805 | 1.00 | 12.79 | C |
| ATOM | 23063 | O | LEU | C | 215 | 15.308 | 60.422 | 19.170 | 1.00 | 11.45 | O |
| ATOM | 23065 | N | SER | C | 216 | 16.988 | 61.413 | 18.067 | 1.00 | 12.11 | N |
| ATOM | 23066 | CA | SER | C | 216 | 17.547 | 60.131 | 17.619 | 1.00 | 12.77 | C |
| ATOM | 23068 | CB | SER | C | 216 | 18.671 | 60.309 | 16.604 | 1.00 | 14.05 | C |
| ATOM | 23071 | OG | SER | C | 216 | 18.955 | 59.052 | 16.019 | 1.00 | 15.57 | O |
| ATOM | 23073 | C | SER | C | 216 | 17.922 | 59.182 | 18.761 | 1.00 | 12.52 | C |
| ATOM | 23074 | O | SER | C | 216 | 17.388 | 58.067 | 18.811 | 1.00 | 13.55 | O |
| ATOM | 23076 | N | PRO | C | 217 | 18.795 | 59.612 | 19.681 | 1.00 | 12.40 | N |
| ATOM | 23077 | CA | PRO | C | 217 | 19.166 | 58.676 | 20.736 | 1.00 | 12.01 | C |
| ATOM | 23079 | CB | PRO | C | 217 | 20.166 | 59.460 | 21.602 | 1.00 | 12.78 | C |
| ATOM | 23082 | CG | PRO | C | 217 | 20.088 | 60.810 | 21.179 | 1.00 | 13.04 | C |
| ATOM | 23085 | CD | PRO | C | 217 | 19.525 | 60.877 | 19.789 | 1.00 | 11.92 | C |
| ATOM | 23088 | C | PRO | C | 217 | 17.964 | 58.209 | 21.569 | 1.00 | 11.52 | C |
| ATOM | 23089 | O | PRO | C | 217 | 17.868 | 57.058 | 21.918 | 1.00 | 12.96 | O |

| ATOM | 23090 | N | LEU | C | 218 | 17.033 | 59.111 | 21.897 | 1.00 | 11.96 | N |
|------|-------|-----|-----|---|-----|--------|--------|--------|------|-------|---|
| ATOM | 23091 | CA | LEU | C | 218 | 15.841 | 58.704 | 22.644 | 1.00 | 12.50 | C |
| ATOM | 23093 | CB | LEU | C | 218 | 15.029 | 59.937 | 23.068 | 1.00 | 13.88 | C |
| ATOM | 23096 | CG | LEU | C | 218 | 15.678 | 60.737 | 24.191 | 1.00 | 13.84 | C |
| ATOM | 23098 | CD1 | LEU | C | 218 | 14.919 | 62.019 | 24.436 | 1.00 | 15.11 | C |
| ATOM | 23102 | CD2 | LEU | C | 218 | 15.770 | 59.871 | 25.458 | 1.00 | 12.15 | C |
| ATOM | 23106 | C | LEU | C | 218 | 14.987 | 57.699 | 21.836 | 1.00 | 13.17 | C |
| ATOM | 23107 | O | LEU | C | 218 | 14.297 | 56.817 | 22.397 | 1.00 | 12.50 | O |
| ATOM | 23109 | N | SER | C | 219 | 15.035 | 57.814 | 20.510 | 1.00 | 12.59 | N |
| ATOM | 23110 | CA | SER | C | 219 | 14.333 | 56.864 | 19.629 | 1.00 | 13.09 | C |
| ATOM | 23112 | CB | SER | C | 219 | 14.296 | 57.349 | 18.179 | 1.00 | 13.51 | C |
| ATOM | 23115 | OG | SER | C | 219 | 13.377 | 58.459 | 18.136 | 1.00 | 18.98 | O |
| ATOM | 23117 | C | SER | C | 219 | 14.906 | 55.451 | 19.736 | 1.00 | 11.38 | C |
| ATOM | 23118 | O | SER | C | 219 | 14.158 | 54.464 | 19.716 | 1.00 | 11.71 | O |
| ATOM | 23120 | N | TYR | C | 220 | 16.225 | 55.346 | 19.846 | 1.00 | 10.93 | N |
| ATOM | 23121 | CA | TYR | C | 220 | 16.844 | 54.050 | 20.053 | 1.00 | 11.20 | C |
| ATOM | 23123 | CB | TYR | C | 220 | 18.368 | 54.155 | 20.001 | 1.00 | 11.54 | C |
| ATOM | 23126 | CG | TYR | C | 220 | 18.846 | 54.231 | 18.567 | 1.00 | 11.40 | C |
| ATOM | 23127 | CD1 | TYR | C | 220 | 18.896 | 55.432 | 17.872 | 1.00 | 10.53 | C |
| ATOM | 23129 | CE1 | TYR | C | 220 | 19.274 | 55.477 | 16.526 | 1.00 | 11.36 | C |
| ATOM | 23131 | CZ | TYR | C | 220 | 19.675 | 54.320 | 15.885 | 1.00 | 12.46 | C |
| ATOM | 23132 | OH | TYR | C | 220 | 20.047 | 54.307 | 14.565 | 1.00 | 11.65 | O |
| ATOM | 23134 | CE2 | TYR | C | 220 | 19.640 | 53.122 | 16.574 | 1.00 | 11.54 | C |
| ATOM | 23136 | CD2 | TYR | C | 220 | 19.236 | 53.089 | 17.903 | 1.00 | 10.80 | C |
| ATOM | 23138 | C | TYR | C | 220 | 16.395 | 53.413 | 21.349 | 1.00 | 11.86 | C |
| ATOM | 23139 | O | TYR | C | 220 | 16.156 | 52.204 | 21.394 | 1.00 | 12.75 | O |
| ATOM | 23141 | N | ILE | C | 221 | 16.223 | 54.230 | 22.365 | 1.00 | 12.07 | N |
| ATOM | 23142 | CA | ILE | C | 221 | 15.799 | 53.728 | 23.664 | 1.00 | 11.83 | C |
| ATOM | 23144 | CB | ILE | C | 221 | 16.016 | 54.810 | 24.777 | 1.00 | 12.03 | C |
| ATOM | 23146 | CG1 | ILE | C | 221 | 17.536 | 55.002 | 25.025 | 1.00 | 9.93 | C |
| ATOM | 23149 | CD1 | ILE | C | 221 | 17.876 | 56.223 | 25.905 | 1.00 | 12.72 | C |
| ATOM | 23153 | CG2 | ILE | C | 221 | 15.268 | 54.485 | 26.079 | 1.00 | 12.48 | C |
| ATOM | 23157 | C | ILE | C | 221 | 14.341 | 53.209 | 23.568 | 1.00 | 11.74 | C |
| ATOM | 23158 | O | ILE | C | 221 | 14.017 | 52.065 | 23.981 | 1.00 | 10.76 | O |
| ATOM | 23160 | N | ALA | C | 222 | 13.500 | 54.032 | 22.938 | 1.00 | 10.91 | N |
| ATOM | 23161 | CA | ALA | C | 222 | 12.092 | 53.707 | 22.703 | 1.00 | 11.63 | C |
| ATOM | 23163 | CB | ALA | C | 222 | 11.369 | 54.872 | 22.044 | 1.00 | 11.63 | C |
| ATOM | 23167 | C | ALA | C | 222 | 11.973 | 52.436 | 21.861 | 1.00 | 11.71 | C |
| ATOM | 23168 | O | ALA | C | 222 | 11.149 | 51.568 | 22.142 | 1.00 | 12.85 | O |
| ATOM | 23170 | N | ALA | C | 223 | 12.811 | 52.309 | 20.833 | 1.00 | 12.04 | N |
| ATOM | 23171 | CA | ALA | C | 223 | 12.768 | 51.121 | 19.984 | 1.00 | 12.01 | C |
| ATOM | 23173 | CB | ALA | C | 223 | 13.667 | 51.305 | 18.795 | 1.00 | 12.61 | C |
| ATOM | 23177 | C | ALA | C | 223 | 13.167 | 49.858 | 20.746 | 1.00 | 11.90 | C |
| ATOM | 23178 | O | ALA | C | 223 | 12.623 | 48.782 | 20.477 | 1.00 | 11.29 | O |
| ATOM | 23180 | N | ALA | C | 224 | 14.140 | 49.990 | 21.648 | 1.00 | 12.35 | N |
| ATOM | 23181 | CA | ALA | C | 224 | 14.621 | 48.879 | 22.474 | 1.00 | 12.21 | C |
| ATOM | 23183 | CB | ALA | C | 224 | 15.854 | 49.240 | 23.269 | 1.00 | 13.77 | C |
| ATOM | 23187 | C | ALA | C | 224 | 13.510 | 48.343 | 23.376 | 1.00 | 13.51 | C |
| ATOM | 23188 | O | ALA | C | 224 | 13.258 | 47.127 | 23.389 | 1.00 | 13.13 | O |
| ATOM | 23190 | N | ILE | C | 225 | 12.819 | 49.219 | 24.113 | 1.00 | 13.14 | N |
| ATOM | 23191 | CA | ILE | C | 225 | 11.772 | 48.713 | 25.055 | 1.00 | 13.51 | C |
| ATOM | 23193 | CB | ILE | C | 225 | 11.324 | 49.758 | 26.145 | 1.00 | 12.63 | C |
| ATOM | 23195 | CG1 | ILE | C | 225 | 10.814 | 51.061 | 25.494 | 1.00 | 13.75 | C |
| ATOM | 23198 | CD1 | ILE | C | 225 | 10.040 | 51.909 | 26.455 | 1.00 | 14.62 | C |
| ATOM | 23202 | CG2 | ILE | C | 225 | 12.461 | 50.036 | 27.101 | 1.00 | 13.01 | C |
| ATOM | 23206 | C | ILE | C | 225 | 10.531 | 48.205 | 24.324 | 1.00 | 14.06 | C |
| ATOM | 23207 | O | ILE | C | 225 | 9.704 | 47.482 | 24.916 | 1.00 | 14.49 | O |

| ATOM | 23209 | N   | SER | C | 226 | 10.386 | 48.599 | 23.054 | 1.00 | 14.37 | N |
|------|-------|-----|-----|---|-----|--------|--------|--------|------|-------|---|
| ATOM | 23210 | CA  | SER | C | 226 | 9.313  | 48.051 | 22.232 | 1.00 | 14.72 | C |
| ATOM | 23212 | CB  | SER | C | 226 | 8.530  | 49.146 | 21.501 | 1.00 | 15.35 | C |
| ATOM | 23215 | OG  | SER | C | 226 | 9.316  | 50.010 | 20.837 | 1.00 | 17.29 | O |
| ATOM | 23217 | C   | SER | C | 226 | 9.747  | 46.893 | 21.296 | 1.00 | 14.22 | C |
| ATOM | 23218 | O   | SER | C | 226 | 8.973  | 46.437 | 20.483 | 1.00 | 14.52 | O |
| ATOM | 23220 | N   | GLY | C | 227 | 10.976 | 46.432 | 21.429 | 1.00 | 14.14 | N |
| ATOM | 23221 | CA  | GLY | C | 227 | 11.377 | 45.200 | 20.762 | 1.00 | 13.93 | C |
| ATOM | 23224 | C   | GLY | C | 227 | 11.472 | 45.344 | 19.266 | 1.00 | 13.61 | C |
| ATOM | 23225 | O   | GLY | C | 227 | 11.161 | 44.412 | 18.524 | 1.00 | 14.84 | O |
| ATOM | 23227 | N   | HIS | C | 228 | 11.895 | 46.522 | 18.811 | 1.00 | 13.65 | N |
| ATOM | 23228 | CA  | HIS | C | 228 | 12.094 | 46.714 | 17.380 | 1.00 | 13.91 | C |
| ATOM | 23230 | CB  | HIS | C | 228 | 12.667 | 48.120 | 17.110 | 1.00 | 13.14 | C |
| ATOM | 23233 | CG  | HIS | C | 228 | 12.818 | 48.465 | 15.662 | 1.00 | 13.19 | C |
| ATOM | 23234 | ND1 | HIS | C | 228 | 13.683 | 47.800 | 14.811 | 1.00 | 13.32 | N |
| ATOM | 23236 | CE1 | HIS | C | 228 | 13.604 | 48.350 | 13.613 | 1.00 | 13.01 | C |
| ATOM | 23238 | NE2 | HIS | C | 228 | 12.745 | 49.350 | 13.662 | 1.00 | 11.89 | N |
| ATOM | 23240 | CD2 | HIS | C | 228 | 12.257 | 49.456 | 14.931 | 1.00 | 12.24 | C |
| ATOM | 23242 | C   | HIS | C | 228 | 13.045 | 45.595 | 16.903 | 1.00 | 13.74 | C |
| ATOM | 23243 | O   | HIS | C | 228 | 14.036 | 45.312 | 17.571 | 1.00 | 13.17 | O |
| ATOM | 23245 | N   | PRO | C | 229 | 12.747 | 44.961 | 15.747 | 1.00 | 13.92 | N |
| ATOM | 23246 | CA  | PRO | C | 229 | 13.619 | 43.854 | 15.272 | 1.00 | 14.84 | C |
| ATOM | 23248 | CB  | PRO | C | 229 | 12.983 | 43.447 | 13.928 | 1.00 | 14.96 | C |
| ATOM | 23251 | CG  | PRO | C | 229 | 11.644 | 44.054 | 13.893 | 1.00 | 14.95 | C |
| ATOM | 23254 | CD  | PRO | C | 229 | 11.620 | 45.223 | 14.828 | 1.00 | 13.83 | C |
| ATOM | 23257 | C   | PRO | C | 229 | 15.112 | 44.150 | 15.032 | 1.00 | 14.54 | C |
| ATOM | 23258 | O   | PRO | C | 229 | 15.902 | 43.213 | 14.945 | 1.00 | 15.56 | O |
| ATOM | 23259 | N   | ASP | C | 230 | 15.479 | 45.414 | 14.852 | 1.00 | 14.98 | N |
| ATOM | 23260 | CA  | ASP | C | 230 | 16.864 | 45.803 | 14.535 | 1.00 | 15.23 | C |
| ATOM | 23262 | CB  | ASP | C | 230 | 16.884 | 46.647 | 13.247 | 1.00 | 16.26 | C |
| ATOM | 23265 | CG  | ASP | C | 230 | 18.294 | 46.794 | 12.641 | 1.00 | 18.66 | C |
| ATOM | 23266 | OD1 | ASP | C | 230 | 19.139 | 45.895 | 12.886 | 1.00 | 22.04 | O |
| ATOM | 23267 | OD2 | ASP | C | 230 | 18.548 | 47.797 | 11.913 | 1.00 | 14.20 | O |
| ATOM | 23268 | C   | ASP | C | 230 | 17.478 | 46.601 | 15.695 | 1.00 | 15.52 | C |
| ATOM | 23269 | O   | ASP | C | 230 | 18.433 | 47.352 | 15.495 | 1.00 | 17.19 | O |
| ATOM | 23271 | N   | SER | C | 231 | 16.868 | 46.494 | 16.878 | 1.00 | 14.42 | N |
| ATOM | 23272 | CA  | SER | C | 231 | 17.359 | 47.162 | 18.070 | 1.00 | 13.84 | C |
| ATOM | 23274 | CB  | SER | C | 231 | 16.176 | 47.560 | 18.983 | 1.00 | 14.14 | C |
| ATOM | 23277 | OG  | SER | C | 231 | 16.667 | 47.975 | 20.263 | 1.00 | 17.10 | O |
| ATOM | 23279 | C   | SER | C | 231 | 18.371 | 46.241 | 18.803 | 1.00 | 12.80 | C |
| ATOM | 23280 | O   | SER | C | 231 | 18.095 | 45.043 | 19.037 | 1.00 | 13.10 | O |
| ATOM | 23282 | N   | LYS | C | 232 | 19.531 | 46.801 | 19.149 | 1.00 | 14.29 | N |
| ATOM | 23283 | CA  | LYS | C | 232 | 20.527 | 46.071 | 19.898 | 1.00 | 14.18 | C |
| ATOM | 23285 | CB  | LYS | C | 232 | 21.855 | 45.964 | 19.121 | 1.00 | 15.39 | C |
| ATOM | 23288 | CG  | LYS | C | 232 | 21.780 | 45.081 | 17.818 | 1.00 | 20.87 | C |
| ATOM | 23291 | CD  | LYS | C | 232 | 21.714 | 46.087 | 16.668 | 1.00 | 26.12 | C |
| ATOM | 23294 | CE  | LYS | C | 232 | 21.417 | 45.506 | 15.320 | 1.00 | 27.36 | C |
| ATOM | 23297 | NZ  | LYS | C | 232 | 21.299 | 46.652 | 14.405 | 1.00 | 30.10 | N |
| ATOM | 23301 | C   | LYS | C | 232 | 20.704 | 46.676 | 21.295 | 1.00 | 12.99 | C |
| ATOM | 23302 | O   | LYS | C | 232 | 20.543 | 47.890 | 21.514 | 1.00 | 13.31 | O |
| ATOM | 23304 | N   | VAL | C | 233 | 20.981 | 45.791 | 22.244 | 1.00 | 13.35 | N |
| ATOM | 23305 | CA  | VAL | C | 233 | 21.198 | 46.167 | 23.644 | 1.00 | 12.88 | C |
| ATOM | 23307 | CB  | VAL | C | 233 | 19.927 | 45.874 | 24.524 | 1.00 | 13.14 | C |
| ATOM | 23309 | CG1 | VAL | C | 233 | 18.706 | 46.524 | 23.900 | 1.00 | 13.03 | C |
| ATOM | 23313 | CG2 | VAL | C | 233 | 19.697 | 44.370 | 24.703 | 1.00 | 13.02 | C |
| ATOM | 23317 | C   | VAL | C | 233 | 22.390 | 45.436 | 24.202 | 1.00 | 13.55 | C |
| ATOM | 23318 | O   | VAL | C | 233 | 22.737 | 44.324 | 23.752 | 1.00 | 12.45 | O |

| | | | | | | | | | |
|---|---|---|---|---|---|---|---|---|---|
| ATOM | 23320 | N | HIS | C | 234 | 23.000 | 46.055 | 25.199 | 1.00 14.34 | N |
| ATOM | 23321 | CA | HIS | C | 234 | 24.133 | 45.505 | 25.937 | 1.00 14.75 | C |
| ATOM | 23323 | CB | HIS | C | 234 | 25.153 | 46.631 | 26.175 | 1.00 15.56 | C |
| ATOM | 23326 | CG | HIS | C | 234 | 26.300 | 46.253 | 27.060 | 1.00 16.39 | C |
| ATOM | 23327 | ND1 | HIS | C | 234 | 26.199 | 46.208 | 28.435 | 1.00 20.12 | N |
| ATOM | 23329 | CE1 | HIS | C | 234 | 27.366 | 45.860 | 28.948 | 1.00 20.18 | C |
| ATOM | 23331 | NE2 | HIS | C | 234 | 28.234 | 45.725 | 27.958 | 1.00 19.38 | N |
| ATOM | 23333 | CD2 | HIS | C | 234 | 27.596 | 45.979 | 26.770 | 1.00 17.84 | C |
| ATOM | 23335 | C | HIS | C | 234 | 23.628 | 44.956 | 27.273 | 1.00 16.46 | C |
| ATOM | 23336 | O | HIS | C | 234 | 22.825 | 45.609 | 27.975 | 1.00 16.44 | O |
| ATOM | 23338 | N | VAL | C | 235 | 24.089 | 43.751 | 27.615 | 1.00 16.76 | N |
| ATOM | 23339 | CA | VAL | C | 235 | 23.815 | 43.154 | 28.925 | 1.00 18.87 | C |
| ATOM | 23341 | CB | VAL | C | 235 | 22.670 | 42.114 | 28.899 | 1.00 19.72 | C |
| ATOM | 23343 | CG1 | VAL | C | 235 | 21.438 | 42.736 | 28.380 | 1.00 23.04 | C |
| ATOM | 23347 | CG2 | VAL | C | 235 | 23.061 | 40.884 | 28.047 | 1.00 20.84 | C |
| ATOM | 23351 | C | VAL | C | 235 | 25.051 | 42.400 | 29.367 | 1.00 19.94 | C |
| ATOM | 23352 | O | VAL | C | 235 | 25.840 | 41.948 | 28.537 | 1.00 21.43 | O |
| ATOM | 23354 | N | VAL | C | 236 | 25.191 | 42.200 | 30.664 | 1.00 20.99 | N |
| ATOM | 23355 | CA | VAL | C | 236 | 26.177 | 41.244 | 31.135 | 1.00 22.17 | C |
| ATOM | 23357 | CB | VAL | C | 236 | 26.950 | 41.774 | 32.341 | 1.00 21.94 | C |
| ATOM | 23359 | CG1 | VAL | C | 236 | 27.860 | 40.658 | 32.938 | 1.00 22.03 | C |
| ATOM | 23363 | CG2 | VAL | C | 236 | 27.774 | 42.972 | 31.933 | 1.00 21.58 | C |
| ATOM | 23367 | C | VAL | C | 236 | 25.424 | 39.963 | 31.457 | 1.00 23.22 | C |
| ATOM | 23368 | O | VAL | C | 236 | 24.506 | 39.990 | 32.261 | 1.00 24.02 | O |
| ATOM | 23370 | N | HIS | C | 237 | 25.765 | 38.872 | 30.772 | 1.00 23.63 | N |
| ATOM | 23371 | CA | HIS | C | 237 | 25.053 | 37.611 | 30.911 | 1.00 26.00 | C |
| ATOM | 23373 | CB | HIS | C | 237 | 24.227 | 37.356 | 29.649 | 1.00 25.46 | C |
| ATOM | 23376 | CG | HIS | C | 237 | 23.393 | 36.106 | 29.692 | 1.00 27.05 | C |
| ATOM | 23377 | ND1 | HIS | C | 237 | 23.659 | 35.004 | 28.905 | 1.00 25.58 | N |
| ATOM | 23379 | CE1 | HIS | C | 237 | 22.759 | 34.065 | 29.153 | 1.00 27.48 | C |
| ATOM | 23381 | NE2 | HIS | C | 237 | 21.928 | 34.513 | 30.081 | 1.00 26.97 | N |
| ATOM | 23383 | CD2 | HIS | C | 237 | 22.306 | 35.787 | 30.437 | 1.00 26.59 | C |
| ATOM | 23385 | C | HIS | C | 237 | 26.087 | 36.513 | 31.106 | 1.00 26.58 | C |
| ATOM | 23386 | O | HIS | C | 237 | 27.043 | 36.420 | 30.337 | 1.00 26.88 | O |
| ATOM | 23388 | N | GLU | C | 238 | 25.884 | 35.672 | 32.123 | 1.00 28.47 | N |
| ATOM | 23389 | CA | GLU | C | 238 | 26.812 | 34.590 | 32.416 | 1.00 29.65 | C |
| ATOM | 23391 | CB | GLU | C | 238 | 26.661 | 33.487 | 31.373 | 1.00 29.48 | C |
| ATOM | 23394 | CG | GLU | C | 238 | 25.258 | 32.871 | 31.395 | 1.00 31.22 | C |
| ATOM | 23397 | CD | GLU | C | 238 | 25.039 | 31.777 | 30.352 | 1.00 32.61 | C |
| ATOM | 23398 | OE1 | GLU | C | 238 | 25.753 | 31.781 | 29.321 | 1.00 39.42 | O |
| ATOM | 23399 | OE2 | GLU | C | 238 | 24.129 | 30.931 | 30.550 | 1.00 37.05 | O |
| ATOM | 23400 | C | GLU | C | 238 | 28.237 | 35.144 | 32.468 | 1.00 29.06 | C |
| ATOM | 23401 | O | GLU | C | 238 | 29.139 | 34.622 | 31.832 | 1.00 29.75 | O |
| ATOM | 23403 | N | GLY | C | 239 | 28.411 | 36.234 | 33.208 | 1.00 28.94 | N |
| ATOM | 23404 | CA | GLY | C | 239 | 29.717 | 36.817 | 33.406 | 1.00 28.54 | C |
| ATOM | 23407 | C | GLY | C | 239 | 30.382 | 37.454 | 32.202 | 1.00 28.30 | C |
| ATOM | 23408 | O | GLY | C | 239 | 31.528 | 37.889 | 32.299 | 1.00 28.64 | O |
| ATOM | 23410 | N | LYS | C | 240 | 29.693 | 37.592 | 31.072 | 1.00 27.03 | N |
| ATOM | 23411 | CA | LYS | C | 240 | 30.337 | 38.310 | 29.991 | 1.00 26.10 | C |
| ATOM | 23413 | CB | LYS | C | 240 | 30.890 | 37.345 | 28.944 | 1.00 27.02 | C |
| ATOM | 23416 | CG | LYS | C | 240 | 29.854 | 36.625 | 28.129 | 1.00 30.67 | C |
| ATOM | 23419 | CD | LYS | C | 240 | 30.385 | 35.269 | 27.673 | 1.00 34.77 | C |
| ATOM | 23422 | CE | LYS | C | 240 | 30.591 | 34.316 | 28.858 | 1.00 36.37 | C |
| ATOM | 23425 | NZ | LYS | C | 240 | 30.592 | 32.873 | 28.450 | 1.00 36.09 | N |
| ATOM | 23429 | C | LYS | C | 240 | 29.428 | 39.357 | 29.371 | 1.00 23.48 | C |
| ATOM | 23430 | O | LYS | C | 240 | 28.210 | 39.183 | 29.362 | 1.00 22.06 | O |
| ATOM | 23432 | N | GLU | C | 241 | 30.036 | 40.440 | 28.883 | 1.00 21.61 | N |

```
ATOM  23433  CA   GLU C 241      29.295  41.481  28.150  1.00 19.78           C
ATOM  23435  CB   GLU C 241      30.162  42.690  27.831  1.00 19.33           C
ATOM  23438  CG   GLU C 241      30.530  43.511  29.012  1.00 18.28           C
ATOM  23441  CD   GLU C 241      31.368  44.662  28.586  1.00 18.17           C
ATOM  23442  OE1  GLU C 241      30.794  45.701  28.179  1.00 17.45           O
ATOM  23443  OE2  GLU C 241      32.616  44.508  28.633  1.00 19.30           O
ATOM  23444  C    GLU C 241      28.844  40.909  26.829  1.00 19.34           C
ATOM  23445  O    GLU C 241      29.636  40.301  26.120  1.00 20.13           O
ATOM  23447  N    LYS C 242      27.583  41.116  26.487  1.00 18.07           N
ATOM  23448  CA   LYS C 242      27.037  40.622  25.227  1.00 17.85           C
ATOM  23450  CB   LYS C 242      26.105  39.456  25.484  1.00 18.09           C
ATOM  23453  CG   LYS C 242      26.794  38.209  25.989  1.00 18.59           C
ATOM  23456  CD   LYS C 242      25.825  37.040  26.006  1.00 20.21           C
ATOM  23459  CE   LYS C 242      26.414  35.872  26.758  1.00 22.08           C
ATOM  23462  NZ   LYS C 242      25.520  34.705  26.612  1.00 24.23           N
ATOM  23466  C    LYS C 242      26.239  41.745  24.575  1.00 17.21           C
ATOM  23467  O    LYS C 242      25.667  42.591  25.270  1.00 14.93           O
ATOM  23469  N    ILE C 243      26.202  41.756  23.246  1.00 16.14           N
ATOM  23470  CA   ILE C 243      25.259  42.623  22.547  1.00 15.70           C
ATOM  23472  CB   ILE C 243      25.958  43.582  21.589  1.00 15.59           C
ATOM  23474  CG1  ILE C 243      26.914  44.480  22.394  1.00 17.02           C
ATOM  23477  CD1  ILE C 243      27.688  45.388  21.561  1.00 19.89           C
ATOM  23481  CG2  ILE C 243      24.902  44.403  20.787  1.00 16.50           C
ATOM  23485  C    ILE C 243      24.299  41.700  21.842  1.00 15.54           C
ATOM  23486  O    ILE C 243      24.713  40.812  21.092  1.00 15.80           O
ATOM  23488  N    LEU C 244      23.016  41.898  22.147  1.00 15.11           N
ATOM  23489  CA   LEU C 244      21.906  41.100  21.688  1.00 14.90           C
ATOM  23491  CB   LEU C 244      21.277  40.450  22.918  1.00 15.37           C
ATOM  23494  CG   LEU C 244      22.202  39.627  23.828  1.00 16.24           C
ATOM  23496  CD1  LEU C 244      21.442  38.984  24.979  1.00 15.09           C
ATOM  23500  CD2  LEU C 244      22.842  38.591  23.005  1.00 15.44           C
ATOM  23504  C    LEU C 244      20.832  41.972  21.053  1.00 13.64           C
ATOM  23505  O    LEU C 244      20.776  43.161  21.301  1.00 13.03           O
ATOM  23507  N    TYR C 245      19.912  41.353  20.313  1.00 13.17           N
ATOM  23508  CA   TYR C 245      18.675  42.023  19.959  1.00 14.91           C
ATOM  23510  CB   TYR C 245      17.918  41.245  18.897  1.00 16.52           C
ATOM  23513  CG   TYR C 245      18.627  41.314  17.570  1.00 18.47           C
ATOM  23514  CD1  TYR C 245      18.482  42.422  16.743  1.00 19.30           C
ATOM  23516  CE1  TYR C 245      19.146  42.498  15.540  1.00 19.72           C
ATOM  23518  CZ   TYR C 245      19.979  41.460  15.148  1.00 23.20           C
ATOM  23519  OH   TYR C 245      20.660  41.521  13.940  1.00 22.40           O
ATOM  23521  CE2  TYR C 245      20.166  40.366  15.978  1.00 21.15           C
ATOM  23523  CD2  TYR C 245      19.494  40.301  17.171  1.00 20.86           C
ATOM  23525  C    TYR C 245      17.826  42.273  21.213  1.00 14.83           C
ATOM  23526  O    TYR C 245      17.886  41.497  22.176  1.00 14.39           O
ATOM  23528  N    ALA C 246      17.137  43.413  21.231  1.00 14.34           N
ATOM  23529  CA   ALA C 246      16.271  43.786  22.335  1.00 13.50           C
ATOM  23531  CB   ALA C 246      15.429  44.968  21.950  1.00 14.68           C
ATOM  23535  C    ALA C 246      15.364  42.622  22.809  1.00 14.13           C
ATOM  23536  O    ALA C 246      15.284  42.368  24.010  1.00 12.52           O
ATOM  23538  N    ARG C 247      14.703  41.936  21.874  1.00 15.20           N
ATOM  23539  CA   ARG C 247      13.775  40.877  22.238  1.00 16.27           C
ATOM  23541  CB   ARG C 247      12.958  40.459  21.030  1.00 16.65           C
ATOM  23544  CG   ARG C 247      11.812  41.386  20.768  1.00 17.27           C
ATOM  23547  CD   ARG C 247      11.082  40.968  19.540  1.00 21.53           C
ATOM  23550  NE   ARG C 247      10.020  41.917  19.267  1.00 22.70           N
ATOM  23552  CZ   ARG C 247       8.772  41.843  19.729  1.00 21.94           C
```

| | | | | | | | | | |
|---|---|---|---|---|---|---|---|---|---|
| ATOM | 23553 | NH1 | ARG | C | 247 | 8.352 | 40.847 | 20.508 | 1.00 19.69 | N |
| ATOM | 23556 | NH2 | ARG | C | 247 | 7.931 | 42.819 | 19.404 | 1.00 23.69 | N |
| ATOM | 23559 | C | ARG | C | 247 | 14.477 | 39.667 | 22.887 | 1.00 16.49 | C |
| ATOM | 23560 | O | ARG | C | 247 | 13.942 | 39.089 | 23.833 | 1.00 16.49 | O |
| ATOM | 23562 | N | GLU | C | 248 | 15.676 | 39.335 | 22.401 | 1.00 17.20 | N |
| ATOM | 23563 | CA | GLU | C | 248 | 16.549 | 38.325 | 23.036 | 1.00 18.30 | C |
| ATOM | 23565 | CB | GLU | C | 248 | 17.855 | 38.156 | 22.243 | 1.00 18.83 | C |
| ATOM | 23568 | CG | GLU | C | 248 | 17.646 | 37.603 | 20.847 | 1.00 20.95 | C |
| ATOM | 23571 | CD | GLU | C | 248 | 18.938 | 37.473 | 20.031 | 1.00 21.83 | C |
| ATOM | 23572 | OE1 | GLU | C | 248 | 19.907 | 38.276 | 20.220 | 1.00 21.09 | O |
| ATOM | 23573 | OE2 | GLU | C | 248 | 18.935 | 36.560 | 19.152 | 1.00 26.50 | O |
| ATOM | 23574 | C | GLU | C | 248 | 16.903 | 38.660 | 24.470 | 1.00 17.41 | C |
| ATOM | 23575 | O | GLU | C | 248 | 16.855 | 37.780 | 25.356 | 1.00 16.69 | O |
| ATOM | 23577 | N | ALA | C | 249 | 17.314 | 39.909 | 24.719 | 1.00 15.63 | N |
| ATOM | 23578 | CA | ALA | C | 249 | 17.654 | 40.283 | 26.072 | 1.00 16.63 | C |
| ATOM | 23580 | CB | ALA | C | 249 | 18.346 | 41.664 | 26.127 | 1.00 16.91 | C |
| ATOM | 23584 | C | ALA | C | 249 | 16.392 | 40.243 | 26.935 | 1.00 17.14 | C |
| ATOM | 23585 | O | ALA | C | 249 | 16.452 | 39.807 | 28.075 | 1.00 16.84 | O |
| ATOM | 23587 | N | MSE | C | 250 | 15.252 | 40.667 | 26.389 | 1.00 17.20 | N |
| ATOM | 23588 | CA | MSE | C | 250 | 14.025 | 40.721 | 27.183 | 1.00 19.25 | C |
| ATOM | 23590 | CB | MSE | C | 250 | 12.870 | 41.356 | 26.419 | 1.00 19.36 | C |
| ATOM | 23593 | CG | AMSE | C | 250 | 13.056 | 42.906 | 26.522 | 0.50 17.67 | C |
| ATOM | 23594 | CG | BMSE | C | 250 | 12.765 | 42.822 | 26.243 | 0.50 19.27 | C |
| ATOM | 23599 | SE | AMSE | C | 250 | 11.738 | 44.196 | 25.869 | 0.50 21.18 | SE |
| ATOM | 23600 | SE | BMSE | C | 250 | 11.259 | 42.928 | 24.911 | 0.50 24.73 | SE |
| ATOM | 23601 | CE | AMSE | C | 250 | 12.126 | 44.116 | 23.990 | 0.50 17.58 | C |
| ATOM | 23602 | CE | BMSE | C | 250 | 11.711 | 44.644 | 24.197 | 0.50 21.29 | C |
| ATOM | 23609 | C | MSE | C | 250 | 13.625 | 39.323 | 27.606 | 1.00 18.86 | C |
| ATOM | 23610 | O | MSE | C | 250 | 13.215 | 39.117 | 28.748 | 1.00 19.74 | O |
| ATOM | 23612 | N | ALA | C | 251 | 13.756 | 38.372 | 26.680 | 1.00 19.11 | N |
| ATOM | 23613 | CA | ALA | C | 251 | 13.449 | 36.982 | 26.972 | 1.00 19.43 | C |
| ATOM | 23615 | CB | ALA | C | 251 | 13.565 | 36.093 | 25.698 | 1.00 19.08 | C |
| ATOM | 23619 | C | ALA | C | 251 | 14.320 | 36.437 | 28.078 | 1.00 19.78 | C |
| ATOM | 23620 | O | ALA | C | 251 | 13.849 | 35.577 | 28.837 | 1.00 20.44 | O |
| ATOM | 23622 | N | LEU | C | 252 | 15.574 | 36.875 | 28.174 | 1.00 20.57 | N |
| ATOM | 23623 | CA | LEU | C | 252 | 16.420 | 36.484 | 29.303 | 1.00 22.50 | C |
| ATOM | 23625 | CB | LEU | C | 252 | 17.837 | 37.037 | 29.229 | 1.00 22.96 | C |
| ATOM | 23628 | CG | LEU | C | 252 | 18.762 | 36.517 | 28.137 | 1.00 25.32 | C |
| ATOM | 23630 | CD1 | LEU | C | 252 | 20.060 | 37.323 | 28.240 | 1.00 26.38 | C |
| ATOM | 23634 | CD2 | LEU | C | 252 | 19.010 | 35.026 | 28.220 | 1.00 28.29 | C |
| ATOM | 23638 | C | LEU | C | 252 | 15.857 | 36.797 | 30.679 | 1.00 22.80 | C |
| ATOM | 23639 | O | LEU | C | 252 | 16.173 | 36.073 | 31.621 | 1.00 23.04 | O |
| ATOM | 23641 | N | PHE | C | 253 | 15.016 | 37.827 | 30.791 | 1.00 23.55 | N |
| ATOM | 23642 | CA | PHE | C | 253 | 14.459 | 38.283 | 32.078 | 1.00 23.54 | C |
| ATOM | 23644 | CB | PHE | C | 253 | 14.981 | 39.701 | 32.386 | 1.00 25.07 | C |
| ATOM | 23647 | CG | PHE | C | 253 | 16.465 | 39.795 | 32.388 | 1.00 25.03 | C |
| ATOM | 23648 | CD1 | PHE | C | 253 | 17.209 | 39.359 | 33.488 | 1.00 27.42 | C |
| ATOM | 23650 | CE1 | PHE | C | 253 | 18.588 | 39.438 | 33.473 | 1.00 25.70 | C |
| ATOM | 23652 | CZ | PHE | C | 253 | 19.237 | 39.919 | 32.374 | 1.00 26.55 | C |
| ATOM | 23654 | CE2 | PHE | C | 253 | 18.512 | 40.332 | 31.275 | 1.00 25.57 | C |
| ATOM | 23656 | CD2 | PHE | C | 253 | 17.135 | 40.271 | 31.293 | 1.00 24.95 | C |
| ATOM | 23658 | C | PHE | C | 253 | 12.930 | 38.249 | 32.114 | 1.00 24.43 | C |
| ATOM | 23659 | O | PHE | C | 253 | 12.301 | 38.870 | 32.990 | 1.00 25.54 | O |
| ATOM | 23661 | N | ASN | C | 254 | 12.329 | 37.515 | 31.189 | 1.00 23.05 | N |
| ATOM | 23662 | CA | ASN | C | 254 | 10.876 | 37.467 | 31.063 | 1.00 23.86 | C |
| ATOM | 23664 | CB | ASN | C | 254 | 10.259 | 36.601 | 32.175 | 1.00 25.08 | C |
| ATOM | 23667 | CG | ASN | C | 254 | 10.583 | 35.124 | 32.002 | 1.00 28.32 | C |

| | | | | | | | | | |
|---|---|---|---|---|---|---|---|---|---|
| ATOM | 23668 | OD1 | ASN | C | 254 | 11.729 | 34.758 | 31.713 | 1.00 33.79 | O |
| ATOM | 23669 | ND2 | ASN | C | 254 | 9.584 | 34.270 | 32.187 | 1.00 34.95 | N |
| ATOM | 23672 | C | ASN | C | 254 | 10.216 | 38.846 | 31.002 | 1.00 22.77 | C |
| ATOM | 23673 | O | ASN | C | 254 | 9.102 | 39.056 | 31.519 | 1.00 23.30 | O |
| ATOM | 23675 | N | LEU | C | 255 | 10.877 | 39.762 | 30.304 | 1.00 20.06 | N |
| ATOM | 23676 | CA | LEU | C | 255 | 10.304 | 41.065 | 30.063 | 1.00 19.31 | C |
| ATOM | 23678 | CB | LEU | C | 255 | 11.421 | 42.098 | 29.949 | 1.00 18.53 | C |
| ATOM | 23681 | CG | LEU | C | 255 | 12.268 | 42.232 | 31.207 | 1.00 19.87 | C |
| ATOM | 23683 | CD1 | LEU | C | 255 | 13.368 | 43.231 | 30.896 | 1.00 17.61 | C |
| ATOM | 23687 | CD2 | LEU | C | 255 | 11.439 | 42.685 | 32.396 | 1.00 18.52 | C |
| ATOM | 23691 | C | LEU | C | 255 | 9.480 | 41.056 | 28.785 | 1.00 18.89 | C |
| ATOM | 23692 | O | LEU | C | 255 | 9.806 | 40.333 | 27.843 | 1.00 18.44 | O |
| ATOM | 23694 | N | GLU | C | 256 | 8.398 | 41.826 | 28.784 | 1.00 18.52 | N |
| ATOM | 23695 | CA | GLU | C | 256 | 7.514 | 41.938 | 27.614 | 1.00 19.43 | C |
| ATOM | 23697 | CB | GLU | C | 256 | 6.028 | 41.868 | 28.008 | 1.00 19.76 | C |
| ATOM | 23700 | CG | GLU | C | 256 | 5.526 | 40.486 | 28.428 | 1.00 23.93 | C |
| ATOM | 23703 | CD | GLU | C | 256 | 5.618 | 39.471 | 27.299 | 1.00 27.61 | C |
| ATOM | 23704 | OE1 | GLU | C | 256 | 5.398 | 39.850 | 26.119 | 1.00 31.95 | O |
| ATOM | 23705 | OE2 | GLU | C | 256 | 5.902 | 38.283 | 27.595 | 1.00 33.49 | O |
| ATOM | 23706 | C | GLU | C | 256 | 7.744 | 43.247 | 26.893 | 1.00 17.95 | C |
| ATOM | 23707 | O | GLU | C | 256 | 7.900 | 44.287 | 27.544 | 1.00 16.44 | O |
| ATOM | 23709 | N | PRO | C | 257 | 7.803 | 43.214 | 25.552 | 1.00 17.42 | N |
| ATOM | 23710 | CA | PRO | C | 257 | 7.907 | 44.530 | 24.896 | 1.00 17.16 | C |
| ATOM | 23712 | CB | PRO | C | 257 | 8.041 | 44.211 | 23.400 | 1.00 17.09 | C |
| ATOM | 23715 | CG | PRO | C | 257 | 8.104 | 42.773 | 23.284 | 1.00 19.49 | C |
| ATOM | 23718 | CD | PRO | C | 257 | 7.908 | 42.106 | 24.596 | 1.00 18.70 | C |
| ATOM | 23721 | C | PRO | C | 257 | 6.653 | 45.330 | 25.132 | 1.00 16.78 | C |
| ATOM | 23722 | O | PRO | C | 257 | 5.583 | 44.747 | 25.355 | 1.00 15.87 | O |
| ATOM | 23723 | N | VAL | C | 258 | 6.783 | 46.640 | 25.074 | 1.00 16.14 | N |
| ATOM | 23724 | CA | VAL | C | 258 | 5.612 | 47.505 | 25.033 | 1.00 16.36 | C |
| ATOM | 23726 | CB | VAL | C | 258 | 5.809 | 48.818 | 25.844 | 1.00 16.07 | C |
| ATOM | 23728 | CG1 | VAL | C | 258 | 6.000 | 48.502 | 27.345 | 1.00 18.32 | C |
| ATOM | 23732 | CG2 | VAL | C | 258 | 6.942 | 49.655 | 25.297 | 1.00 15.94 | C |
| ATOM | 23736 | C | VAL | C | 258 | 5.235 | 47.839 | 23.590 | 1.00 15.49 | C |
| ATOM | 23737 | O | VAL | C | 258 | 6.075 | 47.859 | 22.703 | 1.00 16.90 | O |
| ATOM | 23739 | N | VAL | C | 259 | 3.950 | 48.104 | 23.369 | 1.00 15.80 | N |
| ATOM | 23740 | CA | VAL | C | 259 | 3.459 | 48.572 | 22.094 | 1.00 14.78 | C |
| ATOM | 23742 | CB | VAL | C | 259 | 2.238 | 47.793 | 21.582 | 1.00 15.32 | C |
| ATOM | 23744 | CG1 | VAL | C | 259 | 1.846 | 48.286 | 20.186 | 1.00 15.22 | C |
| ATOM | 23748 | CG2 | VAL | C | 259 | 2.528 | 46.327 | 21.539 | 1.00 15.27 | C |
| ATOM | 23752 | C | VAL | C | 259 | 3.045 | 50.018 | 22.330 | 1.00 14.88 | C |
| ATOM | 23753 | O | VAL | C | 259 | 2.136 | 50.294 | 23.132 | 1.00 14.29 | O |
| ATOM | 23755 | N | LEU | C | 260 | 3.711 | 50.932 | 21.624 | 1.00 14.94 | N |
| ATOM | 23756 | CA | LEU | C | 260 | 3.507 | 52.338 | 21.854 | 1.00 14.73 | C |
| ATOM | 23758 | CB | LEU | C | 260 | 4.651 | 53.140 | 21.236 | 1.00 14.61 | C |
| ATOM | 23761 | CG | LEU | C | 260 | 6.034 | 52.841 | 21.812 | 1.00 15.34 | C |
| ATOM | 23763 | CD1 | LEU | C | 260 | 7.073 | 53.764 | 21.180 | 1.00 14.62 | C |
| ATOM | 23767 | CD2 | LEU | C | 260 | 6.028 | 52.965 | 23.322 | 1.00 14.81 | C |
| ATOM | 23771 | C | LEU | C | 260 | 2.146 | 52.801 | 21.300 | 1.00 14.85 | C |
| ATOM | 23772 | O | LEU | C | 260 | 1.740 | 52.463 | 20.168 | 1.00 15.52 | O |
| ATOM | 23774 | N | GLY | C | 261 | 1.426 | 53.543 | 22.134 | 1.00 14.63 | N |
| ATOM | 23775 | CA | GLY | C | 261 | 0.101 | 54.045 | 21.812 | 1.00 15.07 | C |
| ATOM | 23778 | C | GLY | C | 261 | 0.112 | 55.532 | 21.537 | 1.00 14.53 | C |
| ATOM | 23779 | O | GLY | C | 261 | 1.181 | 56.127 | 21.381 | 1.00 13.95 | O |
| ATOM | 23781 | N | PRO | C | 262 | -1.073 | 56.157 | 21.451 | 1.00 15.07 | N |
| ATOM | 23782 | CA | PRO | C | 262 | -1.158 | 57.606 | 21.156 | 1.00 15.17 | C |
| ATOM | 23784 | CB | PRO | C | 262 | -2.644 | 57.953 | 21.417 | 1.00 15.84 | C |

| | | | | | | | | | |
|---|---|---|---|---|---|---|---|---|---|
| ATOM | 23787 | CG | PRO | C | 262 | -3.345 | 56.705 | 21.380 | 1.00 16.85 | C |
| ATOM | 23790 | CD | PRO | C | 262 | -2.396 | 55.541 | 21.600 | 1.00 15.29 | C |
| ATOM | 23793 | C | PRO | C | 262 | -0.278 | 58.430 | 22.073 | 1.00 14.34 | C |
| ATOM | 23794 | O | PRO | C | 262 | -0.236 | 58.161 | 23.273 | 1.00 15.36 | O |
| ATOM | 23795 | N | LYS | C | 263 | 0.402 | 59.411 | 21.498 | 1.00 14.23 | N |
| ATOM | 23796 | CA | LYS | C | 263 | 1.337 | 60.298 | 22.225 | 1.00 14.10 | C |
| ATOM | 23798 | CB | LYS | C | 263 | 0.616 | 61.067 | 23.346 | 1.00 14.05 | C |
| ATOM | 23801 | CG | LYS | C | 263 | 1.417 | 62.083 | 24.139 | 1.00 14.37 | C |
| ATOM | 23804 | CD | LYS | C | 263 | 2.133 | 63.129 | 23.327 | 1.00 15.72 | C |
| ATOM | 23807 | CE | LYS | C | 263 | 3.425 | 63.615 | 24.018 | 1.00 15.37 | C |
| ATOM | 23810 | NZ | LYS | C | 263 | 3.245 | 64.108 | 25.420 | 1.00 13.05 | N |
| ATOM | 23814 | C | LYS | C | 263 | 2.612 | 59.659 | 22.778 | 1.00 14.97 | C |
| ATOM | 23815 | O | LYS | C | 263 | 3.519 | 60.376 | 23.172 | 1.00 15.55 | O |
| ATOM | 23817 | N | GLU | C | 264 | 2.713 | 58.336 | 22.801 | 1.00 15.02 | N |
| ATOM | 23818 | CA | GLU | C | 264 | 3.821 | 57.688 | 23.520 | 1.00 15.47 | C |
| ATOM | 23820 | CB | GLU | C | 264 | 3.468 | 56.249 | 23.896 | 1.00 16.70 | C |
| ATOM | 23823 | CG | GLU | C | 264 | 2.384 | 56.201 | 24.951 | 1.00 16.21 | C |
| ATOM | 23826 | CD | GLU | C | 264 | 2.161 | 54.840 | 25.551 | 1.00 17.38 | C |
| ATOM | 23827 | OE1 | GLU | C | 264 | 2.288 | 53.830 | 24.806 | 1.00 16.16 | O |
| ATOM | 23828 | OE2 | GLU | C | 264 | 1.803 | 54.799 | 26.758 | 1.00 15.14 | O |
| ATOM | 23829 | C | GLU | C | 264 | 5.151 | 57.774 | 22.773 | 1.00 16.39 | C |
| ATOM | 23830 | O | GLU | C | 264 | 6.216 | 57.787 | 23.393 | 1.00 16.03 | O |
| ATOM | 23832 | N | GLY | C | 265 | 5.075 | 57.883 | 21.443 | 1.00 15.77 | N |
| ATOM | 23833 | CA | GLY | C | 265 | 6.270 | 58.063 | 20.611 | 1.00 16.14 | C |
| ATOM | 23836 | C | GLY | C | 265 | 6.918 | 59.386 | 20.956 | 1.00 16.03 | C |
| ATOM | 23837 | O | GLY | C | 265 | 8.085 | 59.424 | 21.389 | 1.00 15.88 | O |
| ATOM | 23839 | N | LEU | C | 266 | 6.163 | 60.464 | 20.768 | 1.00 15.52 | N |
| ATOM | 23840 | CA | LEU | C | 266 | 6.645 | 61.821 | 21.156 | 1.00 16.26 | C |
| ATOM | 23842 | CB | LEU | C | 266 | 5.604 | 62.887 | 20.824 | 1.00 17.26 | C |
| ATOM | 23845 | CG | LEU | C | 266 | 5.351 | 63.104 | 19.341 | 1.00 19.84 | C |
| ATOM | 23847 | CD1 | LEU | C | 266 | 4.360 | 64.255 | 19.153 | 1.00 22.24 | C |
| ATOM | 23851 | CD2 | LEU | C | 266 | 6.664 | 63.374 | 18.620 | 1.00 21.49 | C |
| ATOM | 23855 | C | LEU | C | 266 | 6.981 | 61.917 | 22.622 | 1.00 15.89 | C |
| ATOM | 23856 | O | LEU | C | 266 | 7.963 | 62.536 | 22.972 | 1.00 16.47 | O |
| ATOM | 23858 | N | GLY | C | 267 | 6.175 | 61.306 | 23.494 | 1.00 14.87 | N |
| ATOM | 23859 | CA | GLY | C | 267 | 6.454 | 61.322 | 24.923 | 1.00 14.92 | C |
| ATOM | 23862 | C | GLY | C | 267 | 7.819 | 60.736 | 25.275 | 1.00 15.01 | C |
| ATOM | 23863 | O | GLY | C | 267 | 8.523 | 61.263 | 26.179 | 1.00 15.96 | O |
| ATOM | 23865 | N | LEU | C | 268 | 8.237 | 59.691 | 24.555 | 1.00 14.92 | N |
| ATOM | 23866 | CA | LEU | C | 268 | 9.546 | 59.067 | 24.781 | 1.00 14.90 | C |
| ATOM | 23868 | CB | LEU | C | 268 | 9.547 | 57.616 | 24.364 | 1.00 14.57 | C |
| ATOM | 23871 | CG | LEU | C | 268 | 8.713 | 56.717 | 25.253 | 1.00 12.40 | C |
| ATOM | 23873 | CD1 | LEU | C | 268 | 8.519 | 55.376 | 24.576 | 1.00 13.09 | C |
| ATOM | 23877 | CD2 | LEU | C | 268 | 9.331 | 56.573 | 26.657 | 1.00 12.09 | C |
| ATOM | 23881 | C | LEU | C | 268 | 10.701 | 59.712 | 24.050 | 1.00 15.48 | C |
| ATOM | 23882 | O | LEU | C | 268 | 11.837 | 59.691 | 24.544 | 1.00 14.93 | O |
| ATOM | 23884 | N | VAL | C | 269 | 10.441 | 60.171 | 22.839 | 1.00 15.23 | N |
| ATOM | 23885 | CA | VAL | C | 269 | 11.522 | 60.708 | 21.987 | 1.00 15.62 | C |
| ATOM | 23887 | CB | VAL | C | 269 | 11.408 | 60.279 | 20.485 | 1.00 16.79 | C |
| ATOM | 23889 | CG1 | VAL | C | 269 | 11.103 | 58.794 | 20.364 | 1.00 17.58 | C |
| ATOM | 23893 | CG2 | VAL | C | 269 | 10.379 | 61.104 | 19.748 | 1.00 20.31 | C |
| ATOM | 23897 | C | VAL | C | 269 | 11.769 | 62.214 | 22.068 | 1.00 14.60 | C |
| ATOM | 23898 | O | VAL | C | 269 | 12.904 | 62.649 | 21.761 | 1.00 13.41 | O |
| ATOM | 23900 | N | ASN | C | 270 | 10.749 | 63.013 | 22.423 | 1.00 14.08 | N |
| ATOM | 23901 | CA | ASN | C | 270 | 10.931 | 64.476 | 22.539 | 1.00 14.44 | C |
| ATOM | 23903 | CB | ASN | C | 270 | 9.615 | 65.228 | 22.468 | 1.00 15.57 | C |
| ATOM | 23906 | CG | ASN | C | 270 | 9.104 | 65.469 | 21.076 | 1.00 19.82 | C |

| ATOM | 23907 | OD1 | ASN C 270 | 9.776 | 65.174 | 20.073 | 1.00 | 23.79 | O |
|------|-------|-----|-----------|-------|--------|--------|------|-------|---|
| ATOM | 23908 | ND2 | ASN C 270 | 7.877 | 66.021 | 21.002 | 1.00 | 19.46 | N |
| ATOM | 23911 | C | ASN C 270 | 11.458 | 64.767 | 23.931 | 1.00 | 13.37 | C |
| ATOM | 23912 | O | ASN C 270 | 10.851 | 64.406 | 24.920 | 1.00 | 14.30 | O |
| ATOM | 23914 | N | GLY C 271 | 12.582 | 65.436 | 24.033 | 1.00 | 13.64 | N |
| ATOM | 23915 | CA | GLY C 271 | 13.075 | 65.787 | 25.375 | 1.00 | 13.64 | C |
| ATOM | 23918 | C | GLY C 271 | 14.578 | 65.838 | 25.460 | 1.00 | 13.77 | C |
| ATOM | 23919 | O | GLY C 271 | 15.275 | 65.636 | 24.475 | 1.00 | 14.01 | O |
| ATOM | 23921 | N | THR C 272 | 15.056 | 66.091 | 26.670 | 1.00 | 12.77 | N |
| ATOM | 23922 | CA | THR C 272 | 16.468 | 66.478 | 26.844 | 1.00 | 12.72 | C |
| ATOM | 23924 | CB | THR C 272 | 16.577 | 67.882 | 27.481 | 1.00 | 12.97 | C |
| ATOM | 23926 | OG1 | THR C 272 | 16.206 | 67.807 | 28.864 | 1.00 | 11.88 | O |
| ATOM | 23928 | CG2 | THR C 272 | 15.710 | 68.888 | 26.768 | 1.00 | 12.87 | C |
| ATOM | 23932 | C | THR C 272 | 17.268 | 65.490 | 27.690 | 1.00 | 12.76 | C |
| ATOM | 23933 | O | THR C 272 | 18.391 | 65.762 | 28.102 | 1.00 | 12.29 | O |
| ATOM | 23935 | N | ALA C 273 | 16.727 | 64.314 | 27.921 | 1.00 | 12.75 | N |
| ATOM | 23936 | CA | ALA C 273 | 17.312 | 63.418 | 28.919 | 1.00 | 12.21 | C |
| ATOM | 23938 | CB | ALA C 273 | 16.365 | 62.241 | 29.166 | 1.00 | 14.09 | C |
| ATOM | 23942 | C | ALA C 273 | 18.720 | 62.918 | 28.569 | 1.00 | 11.66 | C |
| ATOM | 23943 | O | ALA C 273 | 19.527 | 62.620 | 29.462 | 1.00 | 12.40 | O |
| ATOM | 23945 | N | VAL C 274 | 19.056 | 62.811 | 27.283 | 1.00 | 12.79 | N |
| ATOM | 23946 | CA | VAL C 274 | 20.357 | 62.225 | 26.916 | 1.00 | 11.77 | C |
| ATOM | 23948 | CB | VAL C 274 | 20.402 | 61.714 | 25.463 | 1.00 | 12.00 | C |
| ATOM | 23950 | CG1 | VAL C 274 | 21.821 | 61.149 | 25.138 | 1.00 | 14.16 | C |
| ATOM | 23954 | CG2 | VAL C 274 | 19.372 | 60.648 | 25.294 | 1.00 | 13.42 | C |
| ATOM | 23958 | C | VAL C 274 | 21.449 | 63.255 | 27.114 | 1.00 | 12.60 | C |
| ATOM | 23959 | O | VAL C 274 | 22.459 | 63.010 | 27.791 | 1.00 | 12.93 | O |
| ATOM | 23961 | N | SER C 275 | 21.190 | 64.469 | 26.661 | 1.00 | 12.44 | N |
| ATOM | 23962 | CA | SER C 275 | 22.151 | 65.572 | 26.903 | 1.00 | 14.02 | C |
| ATOM | 23964 | CB | SER C 275 | 21.841 | 66.758 | 25.979 | 1.00 | 16.50 | C |
| ATOM | 23967 | OG | SER C 275 | 20.599 | 67.292 | 26.245 | 1.00 | 19.93 | O |
| ATOM | 23969 | C | SER C 275 | 22.210 | 65.904 | 28.415 | 1.00 | 13.85 | C |
| ATOM | 23970 | O | SER C 275 | 23.304 | 66.124 | 28.966 | 1.00 | 12.69 | O |
| ATOM | 23972 | N | ALA C 276 | 21.054 | 65.852 | 29.093 | 1.00 | 12.47 | N |
| ATOM | 23973 | CA | ALA C 276 | 21.019 | 66.100 | 30.539 | 1.00 | 12.64 | C |
| ATOM | 23975 | CB | ALA C 276 | 19.612 | 66.174 | 31.064 | 1.00 | 12.84 | C |
| ATOM | 23979 | C | ALA C 276 | 21.834 | 65.075 | 31.327 | 1.00 | 12.45 | C |
| ATOM | 23980 | O | ALA C 276 | 22.590 | 65.428 | 32.251 | 1.00 | 13.26 | O |
| ATOM | 23982 | N | SER C 277 | 21.786 | 63.825 | 30.887 | 1.00 | 12.59 | N |
| ATOM | 23983 | CA | SER C 277 | 22.549 | 62.753 | 31.553 | 1.00 | 12.17 | C |
| ATOM | 23985 | CB | SER C 277 | 22.138 | 61.422 | 30.971 | 1.00 | 13.46 | C |
| ATOM | 23988 | OG | SER C 277 | 22.992 | 60.361 | 31.320 | 1.00 | 12.09 | O |
| ATOM | 23990 | C | SER C 277 | 24.036 | 62.966 | 31.368 | 1.00 | 11.54 | C |
| ATOM | 23991 | O | SER C 277 | 24.816 | 62.987 | 32.333 | 1.00 | 13.01 | O |
| ATOM | 23993 | N | MSE C 278 | 24.454 | 63.080 | 30.107 | 1.00 | 12.92 | N |
| ATOM | 23994 | CA | MSE C 278 | 25.899 | 63.266 | 29.872 | 1.00 | 13.31 | C |
| ATOM | 23996 | CB | MSE C 278 | 26.255 | 63.299 | 28.392 | 1.00 | 14.01 | C |
| ATOM | 23999 | CG | MSE C 278 | 27.716 | 63.077 | 28.219 | 1.00 | 15.38 | C |
| ATOM | 24002 | SE | MSE C 278 | 28.086 | 62.700 | 26.338 | 1.00 | 24.24 | SE |
| ATOM | 24003 | CE | MSE C 278 | 29.824 | 61.689 | 26.599 | 1.00 | 17.16 | C |
| ATOM | 24007 | C | MSE C 278 | 26.401 | 64.550 | 30.564 | 1.00 | 12.77 | C |
| ATOM | 24008 | O | MSE C 278 | 27.508 | 64.576 | 31.154 | 1.00 | 11.72 | O |
| ATOM | 24010 | N | ALA C 279 | 25.606 | 65.609 | 30.531 | 1.00 | 12.61 | N |
| ATOM | 24011 | CA | ALA C 279 | 25.993 | 66.827 | 31.214 | 1.00 | 12.27 | C |
| ATOM | 24013 | CB | ALA C 279 | 25.026 | 67.972 | 30.871 | 1.00 | 12.17 | C |
| ATOM | 24017 | C | ALA C 279 | 26.135 | 66.684 | 32.717 | 1.00 | 12.09 | C |
| ATOM | 24018 | O | ALA C 279 | 27.003 | 67.284 | 33.355 | 1.00 | 13.24 | O |

| | | | | | | | | | |
|---|---|---|---|---|---|---|---|---|---|
| ATOM | 24020 | N | THR | C | 280 | 25.184 | 65.993 | 33.307 | 1.00 11.20 | N |
| ATOM | 24021 | CA | THR | C | 280 | 25.238 | 65.658 | 34.746 | 1.00 11.99 | C |
| ATOM | 24023 | CB | THR | C | 280 | 23.987 | 64.870 | 35.159 | 1.00 12.81 | C |
| ATOM | 24025 | OG1 | THR | C | 280 | 22.833 | 65.709 | 35.037 | 1.00 12.67 | O |
| ATOM | 24027 | CG2 | THR | C | 280 | 24.090 | 64.425 | 36.569 | 1.00 13.90 | C |
| ATOM | 24031 | C | THR | C | 280 | 26.518 | 64.924 | 35.127 | 1.00 11.80 | C |
| ATOM | 24032 | O | THR | C | 280 | 27.204 | 65.315 | 36.093 | 1.00 13.37 | O |
| ATOM | 24034 | N | LEU | C | 281 | 26.840 | 63.881 | 34.388 | 1.00 12.14 | N |
| ATOM | 24035 | CA | LEU | C | 281 | 28.076 | 63.129 | 34.592 | 1.00 12.36 | C |
| ATOM | 24037 | CB | LEU | C | 281 | 28.175 | 61.952 | 33.617 | 1.00 13.15 | C |
| ATOM | 24040 | CG | LEU | C | 281 | 27.040 | 60.945 | 33.905 | 1.00 14.04 | C |
| ATOM | 24042 | CD1 | LEU | C | 281 | 26.771 | 59.991 | 32.729 | 1.00 16.85 | C |
| ATOM | 24046 | CD2 | LEU | C | 281 | 27.405 | 60.182 | 35.179 | 1.00 17.67 | C |
| ATOM | 24050 | C | LEU | C | 281 | 29.280 | 64.080 | 34.455 | 1.00 12.30 | C |
| ATOM | 24051 | O | LEU | C | 281 | 30.241 | 64.037 | 35.261 | 1.00 12.39 | O |
| ATOM | 24053 | N | ALA | C | 282 | 29.270 | 64.912 | 33.396 | 1.00 11.13 | N |
| ATOM | 24054 | CA | ALA | C | 282 | 30.403 | 65.810 | 33.134 | 1.00 12.25 | C |
| ATOM | 24056 | CB | ALA | C | 282 | 30.210 | 66.508 | 31.822 | 1.00 12.17 | C |
| ATOM | 24060 | C | ALA | C | 282 | 30.554 | 66.836 | 34.287 | 1.00 11.45 | C |
| ATOM | 24061 | O | ALA | C | 282 | 31.670 | 67.161 | 34.726 | 1.00 12.78 | O |
| ATOM | 24063 | N | LEU | C | 283 | 29.448 | 67.414 | 34.734 | 1.00 11.85 | N |
| ATOM | 24064 | CA | LEU | C | 283 | 29.498 | 68.416 | 35.818 | 1.00 12.55 | C |
| ATOM | 24066 | CB | LEU | C | 283 | 28.115 | 69.009 | 36.051 | 1.00 11.62 | C |
| ATOM | 24069 | CG | LEU | C | 283 | 28.100 | 70.081 | 37.155 | 1.00 13.17 | C |
| ATOM | 24071 | CD1 | LEU | C | 283 | 29.024 | 71.179 | 36.790 | 1.00 14.97 | C |
| ATOM | 24075 | CD2 | LEU | C | 283 | 26.770 | 70.614 | 37.335 | 1.00 12.34 | C |
| ATOM | 24079 | C | LEU | C | 283 | 30.034 | 67.764 | 37.109 | 1.00 11.52 | C |
| ATOM | 24080 | O | LEU | C | 283 | 30.898 | 68.302 | 37.796 | 1.00 12.47 | O |
| ATOM | 24082 | N | HIS | C | 284 | 29.497 | 66.595 | 37.436 | 1.00 11.30 | N |
| ATOM | 24083 | CA | HIS | C | 284 | 29.975 | 65.821 | 38.579 | 1.00 12.22 | C |
| ATOM | 24085 | CB | HIS | C | 284 | 29.326 | 64.420 | 38.557 | 1.00 12.78 | C |
| ATOM | 24088 | CG | HIS | C | 284 | 29.913 | 63.432 | 39.531 | 1.00 15.45 | C |
| ATOM | 24089 | ND1 | HIS | C | 284 | 31.077 | 62.727 | 39.278 | 1.00 15.78 | N |
| ATOM | 24091 | CE1 | HIS | C | 284 | 31.314 | 61.897 | 40.279 | 1.00 17.39 | C |
| ATOM | 24093 | NE2 | HIS | C | 284 | 30.353 | 62.025 | 41.171 | 1.00 15.40 | N |
| ATOM | 24095 | CD2 | HIS | C | 284 | 29.456 | 62.971 | 40.719 | 1.00 16.07 | C |
| ATOM | 24097 | C | HIS | C | 284 | 31.491 | 65.734 | 38.526 | 1.00 12.28 | C |
| ATOM | 24098 | O | HIS | C | 284 | 32.165 | 66.003 | 39.511 | 1.00 12.52 | O |
| ATOM | 24100 | N | ASP | C | 285 | 32.018 | 65.287 | 37.389 | 1.00 11.59 | N |
| ATOM | 24101 | CA | ASP | C | 285 | 33.459 | 65.133 | 37.245 | 1.00 11.99 | C |
| ATOM | 24103 | CB | ASP | C | 285 | 33.773 | 64.378 | 35.957 | 1.00 12.25 | C |
| ATOM | 24106 | CG | ASP | C | 285 | 33.286 | 62.905 | 35.988 | 1.00 15.01 | C |
| ATOM | 24107 | OD1 | ASP | C | 285 | 32.862 | 62.424 | 37.058 | 1.00 17.29 | O |
| ATOM | 24108 | OD2 | ASP | C | 285 | 33.402 | 62.210 | 34.959 | 1.00 16.92 | O |
| ATOM | 24109 | C | ASP | C | 285 | 34.238 | 66.454 | 37.307 | 1.00 11.99 | C |
| ATOM | 24110 | O | ASP | C | 285 | 35.377 | 66.516 | 37.888 | 1.00 13.08 | O |
| ATOM | 24112 | N | ALA | C | 286 | 33.667 | 67.493 | 36.707 | 1.00 11.19 | N |
| ATOM | 24113 | CA | ALA | C | 286 | 34.243 | 68.814 | 36.755 | 1.00 11.39 | C |
| ATOM | 24115 | CB | ALA | C | 286 | 33.481 | 69.825 | 35.831 | 1.00 11.34 | C |
| ATOM | 24119 | C | ALA | C | 286 | 34.348 | 69.376 | 38.193 | 1.00 11.51 | C |
| ATOM | 24120 | O | ALA | C | 286 | 35.360 | 70.024 | 38.544 | 1.00 13.47 | O |
| ATOM | 24122 | N | HIS | C | 287 | 33.314 | 69.132 | 39.030 | 1.00 12.17 | N |
| ATOM | 24123 | CA | HIS | C | 287 | 33.401 | 69.564 | 40.441 | 1.00 12.65 | C |
| ATOM | 24125 | CB | HIS | C | 287 | 32.197 | 69.132 | 41.258 | 1.00 12.87 | C |
| ATOM | 24128 | CG | HIS | C | 287 | 30.932 | 69.908 | 40.985 | 1.00 13.76 | C |
| ATOM | 24129 | ND1 | HIS | C | 287 | 30.862 | 71.288 | 40.996 | 1.00 13.81 | N |
| ATOM | 24131 | CE1 | HIS | C | 287 | 29.607 | 71.669 | 40.784 | 1.00 14.97 | C |

| ATOM | 24133 | NE2 | HIS | C | 287 | 28.855 | 70.584 | 40.660 | 1.00 | 14.38 | N |
|------|-------|-----|-----|---|-----|--------|--------|--------|------|-------|---|
| ATOM | 24135 | CD2 | HIS | C | 287 | 29.665 | 69.473 | 40.762 | 1.00 | 11.34 | C |
| ATOM | 24137 | C | HIS | C | 287 | 34.624 | 68.952 | 41.104 | 1.00 | 12.91 | C |
| ATOM | 24138 | O | HIS | C | 287 | 35.359 | 69.581 | 41.842 | 1.00 | 12.83 | O |
| ATOM | 24140 | N | MSE | C | 288 | 34.831 | 67.663 | 40.849 | 1.00 | 12.79 | N |
| ATOM | 24141 | CA | MSE | C | 288 | 35.977 | 66.964 | 41.479 | 1.00 | 12.17 | C |
| ATOM | 24143 | CB | MSE | C | 288 | 35.954 | 65.460 | 41.184 | 1.00 | 13.59 | C |
| ATOM | 24146 | CG | MSE | C | 288 | 34.673 | 64.744 | 41.534 | 1.00 | 12.50 | C |
| ATOM | 24149 | SE | MSE | C | 288 | 34.051 | 65.123 | 43.331 | 1.00 | 23.59 | SE |
| ATOM | 24150 | CE | MSE | C | 288 | 32.228 | 64.362 | 43.004 | 1.00 | 20.45 | C |
| ATOM | 24154 | C | MSE | C | 288 | 37.323 | 67.542 | 40.991 | 1.00 | 12.90 | C |
| ATOM | 24155 | O | MSE | C | 288 | 38.251 | 67.827 | 41.774 | 1.00 | 13.59 | O |
| ATOM | 24157 | N | LEU | C | 289 | 37.425 | 67.803 | 39.695 | 1.00 | 12.40 | N |
| ATOM | 24158 | CA | LEU | C | 289 | 38.665 | 68.412 | 39.155 | 1.00 | 12.23 | C |
| ATOM | 24160 | CB | LEU | C | 289 | 38.639 | 68.465 | 37.655 | 1.00 | 12.58 | C |
| ATOM | 24163 | CG | LEU | C | 289 | 38.592 | 67.065 | 36.995 | 1.00 | 14.14 | C |
| ATOM | 24165 | CD1 | LEU | C | 289 | 38.310 | 67.088 | 35.537 | 1.00 | 15.86 | C |
| ATOM | 24169 | CD2 | LEU | C | 289 | 39.938 | 66.333 | 37.239 | 1.00 | 16.24 | C |
| ATOM | 24173 | C | LEU | C | 289 | 38.929 | 69.818 | 39.725 | 1.00 | 11.64 | C |
| ATOM | 24174 | O | LEU | C | 289 | 40.078 | 70.237 | 39.925 | 1.00 | 13.51 | O |
| ATOM | 24176 | N | SER | C | 290 | 37.849 | 70.573 | 39.932 | 1.00 | 13.16 | N |
| ATOM | 24177 | CA | SER | C | 290 | 37.945 | 71.898 | 40.587 | 1.00 | 13.82 | C |
| ATOM | 24179 | CB | SER | C | 290 | 36.568 | 72.553 | 40.672 | 1.00 | 14.94 | C |
| ATOM | 24182 | OG | SER | C | 290 | 36.622 | 73.788 | 41.369 | 1.00 | 16.22 | O |
| ATOM | 24184 | C | SER | C | 290 | 38.567 | 71.757 | 41.983 | 1.00 | 13.62 | C |
| ATOM | 24185 | O | SER | C | 290 | 39.488 | 72.520 | 42.370 | 1.00 | 12.98 | O |
| ATOM | 24187 | N | LEU | C | 291 | 38.059 | 70.811 | 42.767 | 1.00 | 12.71 | N |
| ATOM | 24188 | CA | LEU | C | 291 | 38.594 | 70.583 | 44.123 | 1.00 | 12.35 | C |
| ATOM | 24190 | CB | LEU | C | 291 | 37.713 | 69.668 | 44.948 | 1.00 | 13.26 | C |
| ATOM | 24193 | CG | LEU | C | 291 | 36.297 | 70.157 | 45.226 | 1.00 | 12.53 | C |
| ATOM | 24195 | CD1 | LEU | C | 291 | 35.587 | 69.177 | 46.135 | 1.00 | 17.45 | C |
| ATOM | 24199 | CD2 | LEU | C | 291 | 36.346 | 71.547 | 45.851 | 1.00 | 13.88 | C |
| ATOM | 24203 | C | LEU | C | 291 | 40.044 | 70.094 | 44.036 | 1.00 | 12.36 | C |
| ATOM | 24204 | O | LEU | C | 291 | 40.919 | 70.537 | 44.803 | 1.00 | 12.41 | O |
| ATOM | 24206 | N | LEU | C | 292 | 40.326 | 69.176 | 43.096 | 1.00 | 11.87 | N |
| ATOM | 24207 | CA | LEU | C | 292 | 41.714 | 68.674 | 42.936 | 1.00 | 12.47 | C |
| ATOM | 24209 | CB | LEU | C | 292 | 41.802 | 67.592 | 41.857 | 1.00 | 12.50 | C |
| ATOM | 24212 | CG | LEU | C | 292 | 43.189 | 66.940 | 41.572 | 1.00 | 11.25 | C |
| ATOM | 24214 | CD1 | LEU | C | 292 | 43.921 | 66.439 | 42.789 | 1.00 | 13.35 | C |
| ATOM | 24218 | CD2 | LEU | C | 292 | 43.030 | 65.799 | 40.536 | 1.00 | 13.57 | C |
| ATOM | 24222 | C | LEU | C | 292 | 42.687 | 69.852 | 42.576 | 1.00 | 11.94 | C |
| ATOM | 24223 | O | LEU | C | 292 | 43.843 | 69.931 | 43.048 | 1.00 | 12.33 | O |
| ATOM | 24225 | N | SER | C | 293 | 42.258 | 70.756 | 41.702 | 1.00 | 11.58 | N |
| ATOM | 24226 | CA | SER | C | 293 | 43.077 | 71.918 | 41.347 | 1.00 | 11.64 | C |
| ATOM | 24228 | CB | SER | C | 293 | 42.290 | 72.795 | 40.348 | 1.00 | 14.06 | C |
| ATOM | 24231 | OG | SER | C | 293 | 42.989 | 73.990 | 40.018 | 1.00 | 13.76 | O |
| ATOM | 24233 | C | SER | C | 293 | 43.493 | 72.759 | 42.566 | 1.00 | 12.25 | C |
| ATOM | 24234 | O | SER | C | 293 | 44.594 | 73.239 | 42.625 | 1.00 | 12.69 | O |
| ATOM | 24236 | N | GLN | C | 294 | 42.532 | 72.976 | 43.477 | 1.00 | 11.76 | N |
| ATOM | 24237 | CA | GLN | C | 294 | 42.761 | 73.679 | 44.720 | 1.00 | 11.87 | C |
| ATOM | 24239 | CB | GLN | C | 294 | 41.452 | 73.918 | 45.423 | 1.00 | 12.87 | C |
| ATOM | 24242 | CG | GLN | C | 294 | 40.586 | 74.870 | 44.625 | 1.00 | 13.98 | C |
| ATOM | 24245 | CD | GLN | C | 294 | 39.216 | 75.099 | 45.236 | 1.00 | 14.94 | C |
| ATOM | 24246 | OE1 | GLN | C | 294 | 39.100 | 75.439 | 46.397 | 1.00 | 15.24 | O |
| ATOM | 24247 | NE2 | GLN | C | 294 | 38.152 | 74.933 | 44.410 | 1.00 | 15.30 | N |
| ATOM | 24250 | C | GLN | C | 294 | 43.733 | 72.944 | 45.643 | 1.00 | 13.41 | C |
| ATOM | 24251 | O | GLN | C | 294 | 44.660 | 73.531 | 46.229 | 1.00 | 14.46 | O |

| ATOM | 24253 | N | SER | C | 295 | 43.508 | 71.634 | 45.780 | 1.00 | 13.34 | N |
|------|-------|------|-----|---|-----|--------|--------|--------|------|-------|----|
| ATOM | 24254 | CA | SER | C | 295 | 44.479 | 70.769 | 46.504 | 1.00 | 14.31 | C |
| ATOM | 24256 | CB | SER | C | 295 | 44.013 | 69.360 | 46.511 | 1.00 | 15.41 | C |
| ATOM | 24259 | OG | SER | C | 295 | 42.750 | 69.307 | 47.169 | 1.00 | 16.26 | O |
| ATOM | 24261 | C | SER | C | 295 | 45.890 | 70.862 | 45.936 | 1.00 | 14.13 | C |
| ATOM | 24262 | O | SER | C | 295 | 46.879 | 70.979 | 46.682 | 1.00 | 14.75 | O |
| ATOM | 24264 | N | LEU | C | 296 | 46.009 | 70.803 | 44.609 | 1.00 | 12.55 | N |
| ATOM | 24265 | CA | LEU | C | 296 | 47.298 | 70.941 | 43.942 | 1.00 | 13.21 | C |
| ATOM | 24267 | CB | LEU | C | 296 | 47.140 | 70.610 | 42.462 | 1.00 | 13.01 | C |
| ATOM | 24270 | CG | LEU | C | 296 | 46.917 | 69.111 | 42.149 | 1.00 | 15.52 | C |
| ATOM | 24272 | CD1 | LEU | C | 296 | 46.473 | 68.927 | 40.736 | 1.00 | 15.73 | C |
| ATOM | 24276 | CD2 | LEU | C | 296 | 48.185 | 68.362 | 42.402 | 1.00 | 14.98 | C |
| ATOM | 24280 | C | LEU | C | 296 | 47.904 | 72.307 | 44.159 | 1.00 | 13.56 | C |
| ATOM | 24281 | O | LEU | C | 296 | 49.122 | 72.400 | 44.272 | 1.00 | 12.96 | O |
| ATOM | 24283 | N | THR | C | 297 | 47.073 | 73.348 | 44.156 | 1.00 | 12.12 | N |
| ATOM | 24284 | CA | THR | C | 297 | 47.527 | 74.675 | 44.445 | 1.00 | 12.49 | C |
| ATOM | 24286 | CB | THR | C | 297 | 46.383 | 75.732 | 44.361 | 1.00 | 12.19 | C |
| ATOM | 24288 | OG1 | THR | C | 297 | 45.870 | 75.762 | 43.049 | 1.00 | 10.93 | O |
| ATOM | 24290 | CG2 | THR | C | 297 | 46.902 | 77.102 | 44.691 | 1.00 | 13.33 | C |
| ATOM | 24294 | C | THR | C | 297 | 48.221 | 74.729 | 45.814 | 1.00 | 11.59 | C |
| ATOM | 24295 | O | THR | C | 297 | 49.379 | 75.157 | 45.957 | 1.00 | 11.59 | O |
| ATOM | 24297 | N | ALA | C | 298 | 47.543 | 74.150 | 46.809 | 1.00 | 10.76 | N |
| ATOM | 24298 | CA | ALA | C | 298 | 48.067 | 74.099 | 48.181 | 1.00 | 11.87 | C |
| ATOM | 24300 | CB | ALA | C | 298 | 47.068 | 73.479 | 49.099 | 1.00 | 11.70 | C |
| ATOM | 24304 | C | ALA | C | 298 | 49.413 | 73.346 | 48.195 | 1.00 | 12.13 | C |
| ATOM | 24305 | O | ALA | C | 298 | 50.400 | 73.811 | 48.776 | 1.00 | 13.34 | O |
| ATOM | 24307 | N | MSE | C | 299 | 49.451 | 72.186 | 47.567 | 1.00 | 12.94 | N |
| ATOM | 24308 | CA | MSE | C | 299 | 50.643 | 71.329 | 47.624 | 1.00 | 15.89 | C |
| ATOM | 24310 | CB | MSE | C | 299 | 50.345 | 69.911 | 47.135 | 1.00 | 16.02 | C |
| ATOM | 24313 | CG | MSE | C | 299 | 49.372 | 69.257 | 48.014 | 1.00 | 19.19 | C |
| ATOM | 24316 | SE | MSE | C | 299 | 48.993 | 67.382 | 47.555 | 1.00 | 34.38 | SE |
| ATOM | 24317 | CE | MSE | C | 299 | 50.470 | 66.519 | 48.496 | 1.00 | 30.99 | C |
| ATOM | 24321 | C | MSE | C | 299 | 51.787 | 71.962 | 46.877 | 1.00 | 13.81 | C |
| ATOM | 24322 | O | MSE | C | 299 | 52.959 | 71.751 | 47.229 | 1.00 | 14.22 | O |
| ATOM | 24324 | N | THR | C | 300 | 51.473 | 72.734 | 45.828 | 1.00 | 12.66 | N |
| ATOM | 24325 | CA | THR | C | 300 | 52.521 | 73.441 | 45.093 | 1.00 | 12.60 | C |
| ATOM | 24327 | CB | THR | C | 300 | 52.007 | 73.926 | 43.690 | 1.00 | 12.62 | C |
| ATOM | 24329 | OG1 | THR | C | 300 | 51.511 | 72.769 | 42.993 | 1.00 | 15.16 | O |
| ATOM | 24331 | CG2 | THR | C | 300 | 53.108 | 74.535 | 42.939 | 1.00 | 15.17 | C |
| ATOM | 24335 | C | THR | C | 300 | 53.081 | 74.585 | 45.932 | 1.00 | 12.02 | C |
| ATOM | 24336 | O | THR | C | 300 | 54.302 | 74.813 | 45.925 | 1.00 | 11.82 | O |
| ATOM | 24338 | N | VAL | C | 301 | 52.223 | 75.259 | 46.713 | 1.00 | 10.96 | N |
| ATOM | 24339 | CA | VAL | C | 301 | 52.725 | 76.278 | 47.611 | 1.00 | 12.34 | C |
| ATOM | 24341 | CB | VAL | C | 301 | 51.607 | 76.906 | 48.426 | 1.00 | 11.48 | C |
| ATOM | 24343 | CG1 | VAL | C | 301 | 52.187 | 77.808 | 49.484 | 1.00 | 13.56 | C |
| ATOM | 24347 | CG2 | VAL | C | 301 | 50.667 | 77.696 | 47.503 | 1.00 | 12.36 | C |
| ATOM | 24351 | C | VAL | C | 301 | 53.730 | 75.622 | 48.570 | 1.00 | 11.69 | C |
| ATOM | 24352 | O | VAL | C | 301 | 54.814 | 76.144 | 48.802 | 1.00 | 13.64 | O |
| ATOM | 24354 | N | GLU | C | 302 | 53.390 | 74.447 | 49.103 | 1.00 | 11.71 | N |
| ATOM | 24355 | CA | GLU | C | 302 | 54.299 | 73.731 | 50.029 | 1.00 | 11.58 | C |
| ATOM | 24357 | CB | GLU | C | 302 | 53.616 | 72.473 | 50.564 | 1.00 | 11.02 | C |
| ATOM | 24360 | CG | GLU | C | 302 | 52.448 | 72.791 | 51.495 | 1.00 | 13.11 | C |
| ATOM | 24363 | CD | GLU | C | 302 | 51.914 | 71.522 | 52.186 | 1.00 | 13.24 | C |
| ATOM | 24364 | OE1 | GLU | C | 302 | 51.315 | 70.684 | 51.478 | 1.00 | 14.35 | O |
| ATOM | 24365 | OE2 | GLU | C | 302 | 52.113 | 71.361 | 53.440 | 1.00 | 14.38 | O |
| ATOM | 24366 | C | GLU | C | 302 | 55.598 | 73.384 | 49.295 | 1.00 | 12.52 | C |
| ATOM | 24367 | O | GLU | C | 302 | 56.700 | 73.715 | 49.775 | 1.00 | 12.13 | O |

```
ATOM  24369  N    ALA C 303      55.495  72.768  48.103  1.00 11.45           N
ATOM  24370  CA   ALA C 303      56.723  72.370  47.362  1.00 12.99           C
ATOM  24372  CB   ALA C 303      56.376  71.695  46.080  1.00 13.28           C
ATOM  24376  C    ALA C 303      57.608  73.577  47.044  1.00 12.79           C
ATOM  24377  O    ALA C 303      58.846  73.480  47.037  1.00 13.20           O
ATOM  24379  N    MSE C 304      56.981  74.735  46.775  1.00 12.15           N
ATOM  24380  CA   MSE C 304      57.699  75.933  46.418  1.00 12.83           C
ATOM  24382  CB   MSE C 304      56.812  76.790  45.508  1.00 14.31           C
ATOM  24385  CG   MSE C 304      56.476  76.136  44.194  1.00 14.85           C
ATOM  24388  SE   MSE C 304      58.074  76.411  43.034  1.00 25.82          SE
ATOM  24389  CE   MSE C 304      57.986  78.414  42.825  1.00 20.09           C
ATOM  24393  C    MSE C 304      58.162  76.782  47.620  1.00 14.13           C
ATOM  24394  O    MSE C 304      58.693  77.905  47.419  1.00 12.52           O
ATOM  24396  N    VAL C 305      57.903  76.264  48.834  1.00 13.59           N
ATOM  24397  CA   VAL C 305      58.104  77.011  50.062  1.00 14.77           C
ATOM  24399  CB   VAL C 305      59.550  76.878  50.585  1.00 15.83           C
ATOM  24401  CG1  VAL C 305      59.758  75.418  51.026  1.00 18.88           C
ATOM  24405  CG2  VAL C 305      60.562  77.251  49.629  1.00 17.63           C
ATOM  24409  C    VAL C 305      57.546  78.433  49.875  1.00 13.23           C
ATOM  24410  O    VAL C 305      58.166  79.464  50.219  1.00 13.95           O
ATOM  24412  N    GLY C 306      56.342  78.461  49.330  1.00 12.70           N
ATOM  24413  CA   GLY C 306      55.640  79.696  49.030  1.00 12.59           C
ATOM  24416  C    GLY C 306      54.805  80.197  50.206  1.00 12.82           C
ATOM  24417  O    GLY C 306      54.924  79.698  51.341  1.00 12.54           O
ATOM  24419  N    HIS C 307      53.991  81.234  49.945  1.00 12.98           N
ATOM  24420  CA   HIS C 307      53.354  81.974  51.019  1.00 14.05           C
ATOM  24422  CB   HIS C 307      53.425  83.457  50.736  1.00 15.54           C
ATOM  24425  CG   HIS C 307      54.801  83.997  50.850  1.00 19.57           C
ATOM  24426  ND1  HIS C 307      55.697  83.949  49.806  1.00 25.19           N
ATOM  24428  CE1  HIS C 307      56.835  84.496  50.192  1.00 27.30           C
ATOM  24430  NE2  HIS C 307      56.714  84.856  51.460  1.00 26.48           N
ATOM  24432  CD2  HIS C 307      55.450  84.545  51.898  1.00 23.79           C
ATOM  24434  C    HIS C 307      51.895  81.620  51.248  1.00 14.98           C
ATOM  24435  O    HIS C 307      51.016  81.750  50.351  1.00 14.48           O
ATOM  24437  N    ALA C 308      51.628  81.167  52.448  1.00 14.55           N
ATOM  24438  CA   ALA C 308      50.252  80.944  52.851  1.00 13.66           C
ATOM  24440  CB   ALA C 308      50.234  80.261  54.195  1.00 15.11           C
ATOM  24444  C    ALA C 308      49.451  82.259  52.916  1.00 13.31           C
ATOM  24445  O    ALA C 308      48.207  82.223  52.927  1.00 13.28           O
ATOM  24447  N    GLY C 309      50.162  83.397  53.000  1.00 12.86           N
ATOM  24448  CA   GLY C 309      49.570  84.704  53.214  1.00 13.37           C
ATOM  24451  C    GLY C 309      48.619  85.081  52.090  1.00 12.19           C
ATOM  24452  O    GLY C 309      47.678  85.876  52.314  1.00 11.52           O
ATOM  24454  N    SER C 310      48.847  84.517  50.897  1.00 11.98           N
ATOM  24455  CA   SER C 310      48.019  84.831  49.751  1.00 11.06           C
ATOM  24457  CB   SER C 310      48.469  84.044  48.489  1.00 11.95           C
ATOM  24460  OG   SER C 310      49.814  84.327  48.146  1.00 11.31           O
ATOM  24462  C    SER C 310      46.525  84.523  50.003  1.00 11.22           C
ATOM  24463  O    SER C 310      45.640  85.074  49.345  1.00 11.90           O
ATOM  24465  N    PHE C 311      46.270  83.665  50.972  1.00 11.39           N
ATOM  24466  CA   PHE C 311      44.950  83.129  51.249  1.00 11.58           C
ATOM  24468  CB   PHE C 311      45.029  81.593  51.234  1.00 11.08           C
ATOM  24471  CG   PHE C 311      45.794  81.057  50.060  1.00 11.32           C
ATOM  24472  CD1  PHE C 311      45.255  81.119  48.805  1.00 12.12           C
ATOM  24474  CE1  PHE C 311      46.001  80.691  47.700  1.00 14.31           C
ATOM  24476  CZ   PHE C 311      47.294  80.276  47.842  1.00 14.58           C
ATOM  24478  CE2  PHE C 311      47.842  80.210  49.087  1.00 12.18           C
```

| | | | | | | | | | |
|---|---|---|---|---|---|---|---|---|---|
| ATOM | 24480 | CD2 | PHE | C | 311 | 47.105 | 80.642 | 50.193 | 1.00 12.27 | C |
| ATOM | 24482 | C | PHE | C | 311 | 44.324 | 83.660 | 52.528 | 1.00 11.64 | C |
| ATOM | 24483 | O | PHE | C | 311 | 43.262 | 83.199 | 52.932 | 1.00 12.24 | O |
| ATOM | 24485 | N | HIS | C | 312 | 44.961 | 84.673 | 53.136 | 1.00 11.80 | N |
| ATOM | 24486 | CA | HIS | C | 312 | 44.475 | 85.275 | 54.364 | 1.00 12.02 | C |
| ATOM | 24488 | CB | HIS | C | 312 | 45.516 | 86.269 | 54.863 | 1.00 11.32 | C |
| ATOM | 24491 | CG | HIS | C | 312 | 45.190 | 86.862 | 56.189 | 1.00 12.94 | C |
| ATOM | 24492 | ND1 | HIS | C | 312 | 44.125 | 87.712 | 56.384 | 1.00 12.55 | N |
| ATOM | 24494 | CE1 | HIS | C | 312 | 44.074 | 88.061 | 57.660 | 1.00 15.37 | C |
| ATOM | 24496 | NE2 | HIS | C | 312 | 45.068 | 87.466 | 58.300 | 1.00 12.86 | N |
| ATOM | 24498 | CD2 | HIS | C | 312 | 45.772 | 86.706 | 57.402 | 1.00 12.88 | C |
| ATOM | 24500 | C | HIS | C | 312 | 43.133 | 85.928 | 54.105 | 1.00 11.47 | C |
| ATOM | 24501 | O | HIS | C | 312 | 42.936 | 86.512 | 53.020 | 1.00 11.59 | O |
| ATOM | 24503 | N | PRO | C | 313 | 42.159 | 85.791 | 55.028 | 1.00 10.92 | N |
| ATOM | 24504 | CA | PRO | C | 313 | 40.822 | 86.320 | 54.710 | 1.00 11.80 | C |
| ATOM | 24506 | CB | PRO | C | 313 | 39.972 | 85.875 | 55.917 | 1.00 12.18 | C |
| ATOM | 24509 | CG | PRO | C | 313 | 40.890 | 85.524 | 56.977 | 1.00 12.45 | C |
| ATOM | 24512 | CD | PRO | C | 313 | 42.196 | 85.135 | 56.346 | 1.00 12.23 | C |
| ATOM | 24515 | C | PRO | C | 313 | 40.711 | 87.826 | 54.453 | 1.00 11.48 | C |
| ATOM | 24516 | O | PRO | C | 313 | 39.768 | 88.277 | 53.785 | 1.00 10.79 | O |
| ATOM | 24517 | N | PHE | C | 314 | 41.662 | 88.610 | 54.944 | 1.00 10.89 | N |
| ATOM | 24518 | CA | PHE | C | 314 | 41.668 | 90.054 | 54.669 | 1.00 10.66 | C |
| ATOM | 24520 | CB | PHE | C | 314 | 42.848 | 90.767 | 55.300 | 1.00 10.67 | C |
| ATOM | 24523 | CG | PHE | C | 314 | 42.844 | 92.230 | 55.027 | 1.00 10.84 | C |
| ATOM | 24524 | CD1 | PHE | C | 314 | 41.955 | 93.054 | 55.674 | 1.00 12.66 | C |
| ATOM | 24526 | CE1 | PHE | C | 314 | 41.930 | 94.410 | 55.431 | 1.00 14.71 | C |
| ATOM | 24528 | CZ | PHE | C | 314 | 42.782 | 94.938 | 54.475 | 1.00 15.24 | C |
| ATOM | 24530 | CE2 | PHE | C | 314 | 43.649 | 94.147 | 53.813 | 1.00 12.12 | C |
| ATOM | 24532 | CD2 | PHE | C | 314 | 43.709 | 92.773 | 54.089 | 1.00 11.35 | C |
| ATOM | 24534 | C | PHE | C | 314 | 41.720 | 90.280 | 53.142 | 1.00 10.68 | C |
| ATOM | 24535 | O | PHE | C | 314 | 41.132 | 91.211 | 52.627 | 1.00 10.78 | O |
| ATOM | 24537 | N | LEU | C | 315 | 42.454 | 89.407 | 52.450 | 1.00 10.54 | N |
| ATOM | 24538 | CA | LEU | C | 315 | 42.648 | 89.548 | 51.010 | 1.00 10.68 | C |
| ATOM | 24540 | CB | LEU | C | 315 | 43.897 | 88.773 | 50.582 | 1.00 10.76 | C |
| ATOM | 24543 | CG | LEU | C | 315 | 45.191 | 89.391 | 51.066 | 1.00 10.85 | C |
| ATOM | 24545 | CD1 | LEU | C | 315 | 46.366 | 88.468 | 50.852 | 1.00 14.12 | C |
| ATOM | 24549 | CD2 | LEU | C | 315 | 45.458 | 90.779 | 50.370 | 1.00 11.83 | C |
| ATOM | 24553 | C | LEU | C | 315 | 41.448 | 89.102 | 50.149 | 1.00 11.91 | C |
| ATOM | 24554 | O | LEU | C | 315 | 41.529 | 89.157 | 48.905 | 1.00 13.45 | O |
| ATOM | 24556 | N | HIS | C | 316 | 40.379 | 88.592 | 50.773 | 1.00 9.66 | N |
| ATOM | 24557 | CA | HIS | C | 316 | 39.260 | 88.025 | 50.052 | 1.00 10.90 | C |
| ATOM | 24559 | CB | HIS | C | 316 | 39.380 | 86.466 | 50.010 | 1.00 11.36 | C |
| ATOM | 24562 | CG | HIS | C | 316 | 40.707 | 86.026 | 49.480 | 1.00 11.64 | C |
| ATOM | 24563 | ND1 | HIS | C | 316 | 40.997 | 86.019 | 48.134 | 1.00 12.13 | N |
| ATOM | 24565 | CE1 | HIS | C | 316 | 42.254 | 85.651 | 47.954 | 1.00 14.09 | C |
| ATOM | 24567 | NE2 | HIS | C | 316 | 42.816 | 85.470 | 49.145 | 1.00 12.10 | N |
| ATOM | 24569 | CD2 | HIS | C | 316 | 41.859 | 85.683 | 50.115 | 1.00 10.47 | C |
| ATOM | 24571 | C | HIS | C | 316 | 37.989 | 88.527 | 50.713 | 1.00 10.14 | C |
| ATOM | 24572 | O | HIS | C | 316 | 37.325 | 89.451 | 50.223 | 1.00 11.17 | O |
| ATOM | 24574 | N | ASP | C | 317 | 37.662 | 87.932 | 51.859 | 1.00 9.83 | N |
| ATOM | 24575 | CA | ASP | C | 317 | 36.492 | 88.267 | 52.607 | 1.00 11.36 | C |
| ATOM | 24577 | CB | ASP | C | 317 | 36.536 | 87.569 | 53.974 | 1.00 10.99 | C |
| ATOM | 24580 | CG | ASP | C | 317 | 36.706 | 86.072 | 53.890 | 1.00 12.82 | C |
| ATOM | 24581 | OD1 | ASP | C | 317 | 36.018 | 85.379 | 54.688 | 1.00 18.41 | O |
| ATOM | 24582 | OD2 | ASP | C | 317 | 37.570 | 85.589 | 53.149 | 1.00 13.24 | O |
| ATOM | 24583 | C | ASP | C | 317 | 36.312 | 89.777 | 52.863 | 1.00 11.13 | C |
| ATOM | 24584 | O | ASP | C | 317 | 35.206 | 90.295 | 52.748 | 1.00 11.41 | O |

| ATOM | 24586 | N | VAL | C | 318 | 37.372 | 90.461 | 53.266 | 1.00 | 12.00 | N |
|------|-------|-----|-----|---|-----|--------|--------|--------|------|-------|---|
| ATOM | 24587 | CA | VAL | C | 318 | 37.288 | 91.847 | 53.605 | 1.00 | 12.33 | C |
| ATOM | 24589 | CB | VAL | C | 318 | 38.370 | 92.260 | 54.616 | 1.00 | 12.95 | C |
| ATOM | 24591 | CG1 | VAL | C | 318 | 38.319 | 93.726 | 54.900 | 1.00 | 12.19 | C |
| ATOM | 24595 | CG2 | VAL | C | 318 | 38.205 | 91.499 | 55.932 | 1.00 | 12.95 | C |
| ATOM | 24599 | C | VAL | C | 318 | 37.395 | 92.734 | 52.339 | 1.00 | 12.97 | C |
| ATOM | 24600 | O | VAL | C | 318 | 36.634 | 93.669 | 52.176 | 1.00 | 14.72 | O |
| ATOM | 24602 | N | THR | C | 319 | 38.380 | 92.466 | 51.522 | 1.00 | 11.21 | N |
| ATOM | 24603 | CA | THR | C | 319 | 38.757 | 93.400 | 50.454 | 1.00 | 11.65 | C |
| ATOM | 24605 | CB | THR | C | 319 | 40.308 | 93.408 | 50.238 | 1.00 | 11.02 | C |
| ATOM | 24607 | OG1 | THR | C | 319 | 40.766 | 92.074 | 50.014 | 1.00 | 11.94 | O |
| ATOM | 24609 | CG2 | THR | C | 319 | 40.989 | 94.051 | 51.417 | 1.00 | 11.99 | C |
| ATOM | 24613 | C | THR | C | 319 | 38.056 | 93.213 | 49.122 | 1.00 | 11.28 | C |
| ATOM | 24614 | O | THR | C | 319 | 37.815 | 94.216 | 48.441 | 1.00 | 11.82 | O |
| ATOM | 24616 | N | ARG | C | 320 | 37.740 | 91.968 | 48.744 | 1.00 | 10.63 | N |
| ATOM | 24617 | CA | ARG | C | 320 | 37.152 | 91.691 | 47.438 | 1.00 | 10.55 | C |
| ATOM | 24619 | CB | ARG | C | 320 | 38.247 | 91.448 | 46.384 | 1.00 | 11.41 | C |
| ATOM | 24622 | CG | ARG | C | 320 | 37.653 | 91.266 | 44.993 | 1.00 | 14.30 | C |
| ATOM | 24625 | CD | ARG | C | 320 | 38.773 | 91.356 | 43.991 | 1.00 | 12.83 | C |
| ATOM | 24628 | NE | ARG | C | 320 | 38.483 | 91.263 | 42.555 | 1.00 | 12.24 | N |
| ATOM | 24630 | CZ | ARG | C | 320 | 39.021 | 90.371 | 41.723 | 1.00 | 14.13 | C |
| ATOM | 24631 | NH1 | ARG | C | 320 | 39.699 | 89.297 | 42.106 | 1.00 | 13.37 | N |
| ATOM | 24634 | NH2 | ARG | C | 320 | 38.800 | 90.534 | 40.431 | 1.00 | 14.20 | N |
| ATOM | 24637 | C | ARG | C | 320 | 36.205 | 90.496 | 47.520 | 1.00 | 9.27 | C |
| ATOM | 24638 | O | ARG | C | 320 | 36.535 | 89.404 | 47.120 | 1.00 | 12.03 | O |
| ATOM | 24640 | N | PRO | C | 321 | 35.037 | 90.760 | 48.144 | 1.00 | 11.15 | N |
| ATOM | 24641 | CA | PRO | C | 321 | 34.209 | 89.683 | 48.637 | 1.00 | 11.75 | C |
| ATOM | 24643 | CB | PRO | C | 321 | 33.412 | 90.383 | 49.727 | 1.00 | 12.00 | C |
| ATOM | 24646 | CG | PRO | C | 321 | 33.153 | 91.782 | 49.183 | 1.00 | 12.21 | C |
| ATOM | 24649 | CD | PRO | C | 321 | 34.485 | 92.103 | 48.470 | 1.00 | 11.26 | C |
| ATOM | 24652 | C | PRO | C | 321 | 33.303 | 88.934 | 47.642 | 1.00 | 11.77 | C |
| ATOM | 24653 | O | PRO | C | 321 | 32.067 | 88.758 | 47.890 | 1.00 | 11.45 | O |
| ATOM | 24654 | N | HIS | C | 322 | 33.867 | 88.548 | 46.504 | 1.00 | 12.04 | N |
| ATOM | 24655 | CA | HIS | C | 322 | 33.176 | 87.610 | 45.625 | 1.00 | 11.95 | C |
| ATOM | 24657 | CB | HIS | C | 322 | 33.972 | 87.336 | 44.368 | 1.00 | 12.85 | C |
| ATOM | 24660 | CG | HIS | C | 322 | 34.084 | 88.527 | 43.456 | 1.00 | 12.44 | C |
| ATOM | 24661 | ND1 | HIS | C | 322 | 33.002 | 88.988 | 42.730 | 1.00 | 12.80 | N |
| ATOM | 24663 | CE1 | HIS | C | 322 | 33.389 | 90.036 | 42.007 | 1.00 | 12.47 | C |
| ATOM | 24665 | NE2 | HIS | C | 322 | 34.675 | 90.258 | 42.227 | 1.00 | 11.35 | N |
| ATOM | 24667 | CD2 | HIS | C | 322 | 35.123 | 89.337 | 43.148 | 1.00 | 13.53 | C |
| ATOM | 24669 | C | HIS | C | 322 | 33.016 | 86.289 | 46.405 | 1.00 | 12.02 | C |
| ATOM | 24670 | O | HIS | C | 322 | 34.034 | 85.725 | 46.852 | 1.00 | 11.30 | O |
| ATOM | 24672 | N | PRO | C | 323 | 31.774 | 85.807 | 46.565 | 1.00 | 11.79 | N |
| ATOM | 24673 | CA | PRO | C | 323 | 31.541 | 84.619 | 47.411 | 1.00 | 11.01 | C |
| ATOM | 24675 | CB | PRO | C | 323 | 30.057 | 84.320 | 47.176 | 1.00 | 12.71 | C |
| ATOM | 24678 | CG | PRO | C | 323 | 29.455 | 85.637 | 47.008 | 1.00 | 13.78 | C |
| ATOM | 24681 | CD | PRO | C | 323 | 30.484 | 86.426 | 46.179 | 1.00 | 11.90 | C |
| ATOM | 24684 | C | PRO | C | 323 | 32.455 | 83.431 | 47.077 | 1.00 | 11.26 | C |
| ATOM | 24685 | O | PRO | C | 323 | 32.986 | 82.753 | 47.966 | 1.00 | 12.74 | O |
| ATOM | 24686 | N | THR | C | 324 | 32.667 | 83.192 | 45.790 | 1.00 | 11.45 | N |
| ATOM | 24687 | CA | THR | C | 324 | 33.463 | 82.026 | 45.431 | 1.00 | 11.87 | C |
| ATOM | 24689 | CB | THR | C | 324 | 33.110 | 81.408 | 44.084 | 1.00 | 13.67 | C |
| ATOM | 24691 | OG1 | THR | C | 324 | 33.242 | 82.407 | 43.058 | 1.00 | 11.97 | O |
| ATOM | 24693 | CG2 | THR | C | 324 | 31.717 | 80.887 | 44.113 | 1.00 | 14.49 | C |
| ATOM | 24697 | C | THR | C | 324 | 34.969 | 82.280 | 45.505 | 1.00 | 11.83 | C |
| ATOM | 24698 | O | THR | C | 324 | 35.753 | 81.324 | 45.601 | 1.00 | 11.64 | O |
| ATOM | 24700 | N | GLN | C | 325 | 35.377 | 83.533 | 45.435 | 1.00 | 11.72 | N |

| | | | | | | | | | |
|---|---|---|---|---|---|---|---|---|---|
| ATOM | 24701 | CA | GLN | C | 325 | 36.780 | 83.844 | 45.754 | 1.00 11.19 | C |
| ATOM | 24703 | CB | GLN | C | 325 | 37.096 | 85.310 | 45.470 | 1.00 10.25 | C |
| ATOM | 24706 | CG | GLN | C | 325 | 38.589 | 85.599 | 45.533 | 1.00 12.81 | C |
| ATOM | 24709 | CD | GLN | C | 325 | 38.917 | 87.063 | 45.240 | 1.00 11.91 | C |
| ATOM | 24710 | OE1 | GLN | C | 325 | 38.417 | 87.640 | 44.228 | 1.00 12.03 | O |
| ATOM | 24711 | NE2 | GLN | C | 325 | 39.740 | 87.691 | 46.104 | 1.00 12.53 | N |
| ATOM | 24714 | C | GLN | C | 325 | 37.073 | 83.533 | 47.211 | 1.00 11.29 | C |
| ATOM | 24715 | O | GLN | C | 325 | 38.106 | 82.952 | 47.559 | 1.00 11.84 | O |
| ATOM | 24717 | N | ILE | C | 326 | 36.176 | 83.992 | 48.085 | 1.00 11.64 | N |
| ATOM | 24718 | CA | ILE | C | 326 | 36.227 | 83.666 | 49.522 | 1.00 11.90 | C |
| ATOM | 24720 | CB | ILE | C | 326 | 34.949 | 84.237 | 50.205 | 1.00 12.33 | C |
| ATOM | 24722 | CG1 | ILE | C | 326 | 35.027 | 85.771 | 50.196 | 1.00 12.06 | C |
| ATOM | 24725 | CD1 | ILE | C | 326 | 33.757 | 86.486 | 50.677 | 1.00 13.41 | C |
| ATOM | 24729 | CG2 | ILE | C | 326 | 34.858 | 83.740 | 51.602 | 1.00 12.73 | C |
| ATOM | 24733 | C | ILE | C | 326 | 36.341 | 82.154 | 49.736 | 1.00 11.85 | C |
| ATOM | 24734 | O | ILE | C | 326 | 37.145 | 81.667 | 50.546 | 1.00 11.93 | O |
| ATOM | 24736 | N | GLU | C | 327 | 35.468 | 81.430 | 49.050 | 1.00 11.57 | N |
| ATOM | 24737 | CA | GLU | C | 327 | 35.371 | 79.980 | 49.169 | 1.00 12.81 | C |
| ATOM | 24739 | CB | GLU | C | 327 | 34.236 | 79.453 | 48.281 | 1.00 13.32 | C |
| ATOM | 24742 | CG | GLU | C | 327 | 34.277 | 77.976 | 48.085 | 1.00 16.84 | C |
| ATOM | 24745 | CD | GLU | C | 327 | 33.164 | 77.491 | 47.130 | 1.00 16.42 | C |
| ATOM | 24746 | OE1 | GLU | C | 327 | 32.231 | 78.280 | 46.820 | 1.00 19.16 | O |
| ATOM | 24747 | OE2 | GLU | C | 327 | 33.250 | 76.322 | 46.717 | 1.00 18.47 | O |
| ATOM | 24748 | C | GLU | C | 327 | 36.705 | 79.332 | 48.808 | 1.00 11.37 | C |
| ATOM | 24749 | O | GLU | C | 327 | 37.257 | 78.540 | 49.571 | 1.00 13.12 | O |
| ATOM | 24751 | N | VAL | C | 328 | 37.252 | 79.658 | 47.632 | 1.00 12.05 | N |
| ATOM | 24752 | CA | VAL | C | 328 | 38.517 | 79.031 | 47.191 | 1.00 10.83 | C |
| ATOM | 24754 | CB | VAL | C | 328 | 38.888 | 79.416 | 45.730 | 1.00 11.54 | C |
| ATOM | 24756 | CG1 | VAL | C | 328 | 40.277 | 78.985 | 45.385 | 1.00 11.37 | C |
| ATOM | 24760 | CG2 | VAL | C | 328 | 37.856 | 78.885 | 44.730 | 1.00 12.01 | C |
| ATOM | 24764 | C | VAL | C | 328 | 39.687 | 79.406 | 48.140 | 1.00 11.90 | C |
| ATOM | 24765 | O | VAL | C | 328 | 40.521 | 78.547 | 48.501 | 1.00 12.45 | O |
| ATOM | 24767 | N | ALA | C | 329 | 39.765 | 80.685 | 48.488 | 1.00 10.70 | N |
| ATOM | 24768 | CA | ALA | C | 329 | 40.843 | 81.166 | 49.421 | 1.00 10.99 | C |
| ATOM | 24770 | CB | ALA | C | 329 | 40.744 | 82.616 | 49.647 | 1.00 11.87 | C |
| ATOM | 24774 | C | ALA | C | 329 | 40.701 | 80.362 | 50.740 | 1.00 11.62 | C |
| ATOM | 24775 | O | ALA | C | 329 | 41.689 | 79.894 | 51.302 | 1.00 11.47 | O |
| ATOM | 24777 | N | GLY | C | 330 | 39.473 | 80.168 | 51.208 | 1.00 12.66 | N |
| ATOM | 24778 | CA | GLY | C | 330 | 39.258 | 79.425 | 52.441 | 1.00 12.31 | C |
| ATOM | 24781 | C | GLY | C | 330 | 39.675 | 77.965 | 52.329 | 1.00 11.77 | C |
| ATOM | 24782 | O | GLY | C | 330 | 40.237 | 77.414 | 53.267 | 1.00 12.27 | O |
| ATOM | 24784 | N | ASN | C | 331 | 39.398 | 77.323 | 51.188 | 1.00 11.92 | N |
| ATOM | 24785 | CA | ASN | C | 331 | 39.758 | 75.916 | 51.003 | 1.00 12.06 | C |
| ATOM | 24787 | CB | ASN | C | 331 | 39.251 | 75.394 | 49.662 | 1.00 11.87 | C |
| ATOM | 24790 | CG | ASN | C | 331 | 37.728 | 75.150 | 49.633 | 1.00 12.95 | C |
| ATOM | 24791 | OD1 | ASN | C | 331 | 37.081 | 74.965 | 50.701 | 1.00 15.22 | O |
| ATOM | 24792 | ND2 | ASN | C | 331 | 37.144 | 75.106 | 48.413 | 1.00 15.16 | N |
| ATOM | 24795 | C | ASN | C | 331 | 41.249 | 75.825 | 51.053 | 1.00 11.84 | C |
| ATOM | 24796 | O | ASN | C | 331 | 41.814 | 74.944 | 51.733 | 1.00 12.62 | O |
| ATOM | 24798 | N | ILE | C | 332 | 41.943 | 76.720 | 50.324 | 1.00 11.81 | N |
| ATOM | 24799 | CA | ILE | C | 332 | 43.405 | 76.619 | 50.266 | 1.00 11.04 | C |
| ATOM | 24801 | CB | ILE | C | 332 | 43.975 | 77.433 | 49.069 | 1.00 11.37 | C |
| ATOM | 24803 | CG1 | ILE | C | 332 | 43.420 | 76.864 | 47.762 | 1.00 12.95 | C |
| ATOM | 24806 | CD1 | ILE | C | 332 | 43.722 | 77.817 | 46.577 | 1.00 13.80 | C |
| ATOM | 24810 | CG2 | ILE | C | 332 | 45.544 | 77.476 | 49.082 | 1.00 12.15 | C |
| ATOM | 24814 | C | ILE | C | 332 | 44.035 | 76.949 | 51.625 | 1.00 11.53 | C |
| ATOM | 24815 | O | ILE | C | 332 | 44.972 | 76.276 | 52.065 | 1.00 12.22 | O |

| | | | | | | | | | |
|---|---|---|---|---|---|---|---|---|---|
| ATOM | 24817 | N | ARG | C | 333 | 43.508 | 77.988 | 52.293 | 1.00 11.20 | N |
| ATOM | 24818 | CA | ARG | C | 333 | 43.938 | 78.342 | 53.645 | 1.00 11.69 | C |
| ATOM | 24820 | CB | ARG | C | 333 | 43.118 | 79.513 | 54.138 | 1.00 12.35 | C |
| ATOM | 24823 | CG | ARG | C | 333 | 43.450 | 79.963 | 55.532 | 1.00 14.10 | C |
| ATOM | 24826 | CD | ARG | C | 333 | 42.748 | 81.299 | 55.795 | 1.00 12.88 | C |
| ATOM | 24829 | NE | ARG | C | 333 | 41.294 | 81.221 | 55.927 | 1.00 12.60 | N |
| ATOM | 24831 | CZ | ARG | C | 333 | 40.405 | 81.774 | 55.106 | 1.00 14.35 | C |
| ATOM | 24832 | NH1 | ARG | C | 333 | 40.795 | 82.448 | 54.032 | 1.00 11.93 | N |
| ATOM | 24835 | NH2 | ARG | C | 333 | 39.115 | 81.656 | 55.348 | 1.00 14.22 | N |
| ATOM | 24838 | C | ARG | C | 333 | 43.789 | 77.140 | 54.602 | 1.00 12.17 | C |
| ATOM | 24839 | O | ARG | C | 333 | 44.714 | 76.828 | 55.350 | 1.00 12.86 | O |
| ATOM | 24841 | N | LYS | C | 334 | 42.647 | 76.458 | 54.543 | 1.00 11.65 | N |
| ATOM | 24842 | CA | LYS | C | 334 | 42.408 | 75.270 | 55.378 | 1.00 14.22 | C |
| ATOM | 24844 | CB | LYS | C | 334 | 40.993 | 74.744 | 55.143 | 1.00 14.47 | C |
| ATOM | 24847 | CG | LYS | C | 334 | 40.614 | 73.539 | 55.980 | 1.00 17.90 | C |
| ATOM | 24850 | CD | LYS | C | 334 | 39.231 | 73.019 | 55.570 | 1.00 20.82 | C |
| ATOM | 24853 | CE | LYS | C | 334 | 38.113 | 73.795 | 56.216 | 1.00 26.06 | C |
| ATOM | 24856 | NZ | LYS | C | 334 | 37.851 | 73.322 | 57.593 | 1.00 30.68 | N |
| ATOM | 24860 | C | LYS | C | 334 | 43.492 | 74.220 | 55.101 | 1.00 13.26 | C |
| ATOM | 24861 | O | LYS | C | 334 | 44.068 | 73.666 | 56.030 | 1.00 13.28 | O |
| ATOM | 24863 | N | LEU | C | 335 | 43.740 | 73.963 | 53.821 | 1.00 12.87 | N |
| ATOM | 24864 | CA | LEU | C | 335 | 44.718 | 72.941 | 53.418 | 1.00 13.63 | C |
| ATOM | 24866 | CB | LEU | C | 335 | 44.727 | 72.735 | 51.903 | 1.00 14.14 | C |
| ATOM | 24869 | CG | LEU | C | 335 | 43.486 | 72.129 | 51.266 | 1.00 14.64 | C |
| ATOM | 24871 | CD1 | LEU | C | 335 | 43.712 | 72.031 | 49.764 | 1.00 15.98 | C |
| ATOM | 24875 | CD2 | LEU | C | 335 | 43.165 | 70.730 | 51.902 | 1.00 17.36 | C |
| ATOM | 24879 | C | LEU | C | 335 | 46.133 | 73.225 | 53.910 | 1.00 13.96 | C |
| ATOM | 24880 | O | LEU | C | 335 | 46.896 | 72.282 | 54.209 | 1.00 14.71 | O |
| ATOM | 24882 | N | LEU | C | 336 | 46.494 | 74.505 | 53.970 | 1.00 13.45 | N |
| ATOM | 24883 | CA | LEU | C | 336 | 47.845 | 74.929 | 54.371 | 1.00 13.52 | C |
| ATOM | 24885 | CB | LEU | C | 336 | 48.227 | 76.197 | 53.632 | 1.00 13.85 | C |
| ATOM | 24888 | CG | LEU | C | 336 | 48.385 | 76.044 | 52.120 | 1.00 12.82 | C |
| ATOM | 24890 | CD1 | LEU | C | 336 | 48.675 | 77.374 | 51.522 | 1.00 14.99 | C |
| ATOM | 24894 | CD2 | LEU | C | 336 | 49.533 | 75.016 | 51.836 | 1.00 13.97 | C |
| ATOM | 24898 | C | LEU | C | 336 | 48.052 | 75.092 | 55.877 | 1.00 14.42 | C |
| ATOM | 24899 | O | LEU | C | 336 | 49.183 | 75.209 | 56.341 | 1.00 13.90 | O |
| ATOM | 24901 | N | GLU | C | 337 | 46.976 | 75.118 | 56.629 | 1.00 14.29 | N |
| ATOM | 24902 | CA | GLU | C | 337 | 47.081 | 75.172 | 58.077 | 1.00 16.24 | C |
| ATOM | 24904 | CB | GLU | C | 337 | 45.676 | 75.017 | 58.649 | 1.00 16.70 | C |
| ATOM | 24907 | CG | GLU | C | 337 | 45.552 | 75.224 | 60.084 | 1.00 22.29 | C |
| ATOM | 24910 | CD | GLU | C | 337 | 44.121 | 74.883 | 60.605 | 1.00 22.91 | C |
| ATOM | 24911 | OE1 | GLU | C | 337 | 43.172 | 74.764 | 59.765 | 1.00 32.82 | O |
| ATOM | 24912 | OE2 | GLU | C | 337 | 43.998 | 74.714 | 61.849 | 1.00 34.15 | O |
| ATOM | 24913 | C | GLU | C | 337 | 48.012 | 74.067 | 58.582 | 1.00 15.43 | C |
| ATOM | 24914 | O | GLU | C | 337 | 47.862 | 72.911 | 58.234 | 1.00 14.92 | O |
| ATOM | 24916 | N | GLY | C | 338 | 48.979 | 74.441 | 59.402 | 1.00 15.51 | N |
| ATOM | 24917 | CA | GLY | C | 338 | 49.920 | 73.471 | 59.947 | 1.00 15.30 | C |
| ATOM | 24920 | C | GLY | C | 338 | 51.071 | 73.015 | 59.065 | 1.00 15.14 | C |
| ATOM | 24921 | O | GLY | C | 338 | 51.899 | 72.235 | 59.499 | 1.00 14.92 | O |
| ATOM | 24923 | N | SER | C | 339 | 51.107 | 73.447 | 57.816 | 1.00 13.66 | N |
| ATOM | 24924 | CA | SER | C | 339 | 52.253 | 73.167 | 56.975 | 1.00 14.72 | C |
| ATOM | 24926 | CB | SER | C | 339 | 52.059 | 73.802 | 55.609 | 1.00 14.14 | C |
| ATOM | 24929 | OG | SER | C | 339 | 53.111 | 73.353 | 54.780 | 1.00 13.37 | O |
| ATOM | 24931 | C | SER | C | 339 | 53.540 | 73.738 | 57.556 | 1.00 13.90 | C |
| ATOM | 24932 | O | SER | C | 339 | 53.537 | 74.869 | 58.015 | 1.00 16.42 | O |
| ATOM | 24934 | N | ARG | C | 340 | 54.643 | 72.996 | 57.522 | 1.00 14.09 | N |
| ATOM | 24935 | CA | ARG | C | 340 | 55.966 | 73.551 | 57.829 | 1.00 14.15 | C |

| | | | | | | | | | |
|---|---|---|---|---|---|---|---|---|---|
| ATOM | 24937 | CB | ARG | C | 340 | 56.751 | 72.612 | 58.757 | 1.00 15.21 | C |
| ATOM | 24940 | CG | ARG | C | 340 | 56.047 | 72.340 | 60.025 | 1.00 19.73 | C |
| ATOM | 24943 | CD | ARG | C | 340 | 56.329 | 73.336 | 61.085 | 1.00 30.44 | C |
| ATOM | 24946 | NE | ARG | C | 340 | 55.677 | 72.869 | 62.321 | 1.00 35.15 | N |
| ATOM | 24948 | CZ | ARG | C | 340 | 54.696 | 73.509 | 62.967 | 1.00 35.62 | C |
| ATOM | 24949 | NH1 | ARG | C | 340 | 54.235 | 74.699 | 62.546 | 1.00 34.63 | N |
| ATOM | 24952 | NH2 | ARG | C | 340 | 54.196 | 72.950 | 64.063 | 1.00 35.66 | N |
| ATOM | 24955 | C | ARG | C | 340 | 56.765 | 73.757 | 56.569 | 1.00 14.32 | C |
| ATOM | 24956 | O | ARG | C | 340 | 57.944 | 74.169 | 56.636 | 1.00 15.10 | O |
| ATOM | 24958 | N | PHE | C | 341 | 56.127 | 73.525 | 55.420 | 1.00 14.48 | N |
| ATOM | 24959 | CA | PHE | C | 341 | 56.732 | 73.881 | 54.144 | 1.00 13.60 | C |
| ATOM | 24961 | CB | PHE | C | 341 | 56.241 | 72.979 | 53.020 | 1.00 13.48 | C |
| ATOM | 24964 | CG | PHE | C | 341 | 56.902 | 71.618 | 52.932 | 1.00 13.42 | C |
| ATOM | 24965 | CD1 | PHE | C | 341 | 58.276 | 71.489 | 52.799 | 1.00 16.92 | C |
| ATOM | 24967 | CE1 | PHE | C | 341 | 58.858 | 70.236 | 52.636 | 1.00 15.19 | C |
| ATOM | 24969 | CZ | PHE | C | 341 | 58.034 | 69.101 | 52.639 | 1.00 14.51 | C |
| ATOM | 24971 | CE2 | PHE | C | 341 | 56.668 | 69.245 | 52.759 | 1.00 16.10 | C |
| ATOM | 24973 | CD2 | PHE | C | 341 | 56.119 | 70.485 | 52.940 | 1.00 15.40 | C |
| ATOM | 24975 | C | PHE | C | 341 | 56.306 | 75.329 | 53.718 | 1.00 14.26 | C |
| ATOM | 24976 | O | PHE | C | 341 | 57.125 | 76.164 | 53.343 | 1.00 14.93 | O |
| ATOM | 24978 | N | ALA | C | 342 | 55.006 | 75.590 | 53.733 | 1.00 14.85 | N |
| ATOM | 24979 | CA | ALA | C | 342 | 54.499 | 76.923 | 53.367 | 1.00 14.86 | C |
| ATOM | 24981 | CB | ALA | C | 342 | 53.010 | 76.880 | 53.231 | 1.00 15.99 | C |
| ATOM | 24985 | C | ALA | C | 342 | 54.906 | 77.890 | 54.471 | 1.00 15.68 | C |
| ATOM | 24986 | O | ALA | C | 342 | 54.956 | 77.500 | 55.649 | 1.00 16.25 | O |
| ATOM | 24988 | N | VAL | C | 343 | 55.119 | 79.144 | 54.113 | 1.00 14.97 | N |
| ATOM | 24989 | CA | VAL | C | 343 | 55.483 | 80.184 | 55.049 | 1.00 15.42 | C |
| ATOM | 24991 | CB | VAL | C | 343 | 56.411 | 81.209 | 54.368 | 1.00 16.12 | C |
| ATOM | 24993 | CG1 | VAL | C | 343 | 56.745 | 82.377 | 55.276 | 1.00 19.07 | C |
| ATOM | 24997 | CG2 | VAL | C | 343 | 57.704 | 80.524 | 53.873 | 1.00 19.77 | C |
| ATOM | 25001 | C | VAL | C | 343 | 54.249 | 80.908 | 55.524 | 1.00 16.89 | C |
| ATOM | 25002 | O | VAL | C | 343 | 53.404 | 81.286 | 54.707 | 1.00 14.89 | O |
| ATOM | 25004 | N | HIS | C | 344 | 54.158 | 81.135 | 56.833 | 1.00 17.77 | N |
| ATOM | 25005 | CA | HIS | C | 344 | 52.955 | 81.705 | 57.444 | 1.00 20.21 | C |
| ATOM | 25007 | CB | HIS | C | 344 | 52.477 | 80.826 | 58.612 | 1.00 19.09 | C |
| ATOM | 25010 | CG | HIS | C | 344 | 52.151 | 79.429 | 58.197 | 1.00 20.04 | C |
| ATOM | 25011 | ND1 | HIS | C | 344 | 50.970 | 79.096 | 57.571 | 1.00 20.62 | N |
| ATOM | 25013 | CE1 | HIS | C | 344 | 50.990 | 77.815 | 57.266 | 1.00 18.70 | C |
| ATOM | 25015 | NE2 | HIS | C | 344 | 52.141 | 77.307 | 57.672 | 1.00 21.31 | N |
| ATOM | 25017 | CD2 | HIS | C | 344 | 52.898 | 78.305 | 58.222 | 1.00 19.71 | C |
| ATOM | 25019 | C | HIS | C | 344 | 53.137 | 83.128 | 57.909 | 1.00 24.72 | C |
| ATOM | 25020 | O | HIS | C | 344 | 52.221 | 83.908 | 57.809 | 1.00 27.35 | O |
| ATOM | 25022 | N | HIS | C | 345 | 54.272 | 83.465 | 58.479 | 1.00 28.78 | N |
| ATOM | 25023 | CA | HIS | C | 345 | 54.486 | 84.813 | 58.996 | 1.00 31.50 | C |
| ATOM | 25025 | CB | HIS | C | 345 | 55.210 | 84.784 | 60.339 | 1.00 31.55 | C |
| ATOM | 25028 | CG | HIS | C | 345 | 54.367 | 84.274 | 61.460 | 1.00 32.74 | C |
| ATOM | 25029 | ND1 | HIS | C | 345 | 54.291 | 82.935 | 61.787 | 1.00 34.03 | N |
| ATOM | 25031 | CE1 | HIS | C | 345 | 53.452 | 82.779 | 62.794 | 1.00 34.25 | C |
| ATOM | 25033 | NE2 | HIS | C | 345 | 52.991 | 83.969 | 63.141 | 1.00 33.82 | N |
| ATOM | 25035 | CD2 | HIS | C | 345 | 53.552 | 84.922 | 62.326 | 1.00 32.76 | C |
| ATOM | 25037 | C | HIS | C | 345 | 55.352 | 85.483 | 57.979 | 1.00 33.79 | C |
| ATOM | 25038 | O | HIS | C | 345 | 56.463 | 85.032 | 57.763 | 1.00 34.56 | O |
| ATOM | 25040 | N | GLU | C | 346 | 54.844 | 86.542 | 57.355 | 1.00 37.03 | N |
| ATOM | 25041 | CA | GLU | C | 346 | 55.628 | 87.340 | 56.412 | 1.00 39.31 | C |
| ATOM | 25043 | CB | GLU | C | 346 | 54.922 | 88.642 | 56.100 | 1.00 40.09 | C |
| ATOM | 25046 | CG | GLU | C | 346 | 53.690 | 88.420 | 55.255 | 1.00 42.61 | C |
| ATOM | 25049 | CD | GLU | C | 346 | 53.342 | 89.606 | 54.461 | 1.00 43.14 | C |

| | | | | | | | | | |
|---|---|---|---|---|---|---|---|---|---|
| ATOM | 25050 | OE1 | GLU | C | 346 | 54.206 | 89.995 | 53.635 | 1.00 43.67 | O |
| ATOM | 25051 | OE2 | GLU | C | 346 | 52.219 | 90.126 | 54.665 | 1.00 42.05 | O |
| ATOM | 25052 | C | GLU | C | 346 | 57.010 | 87.685 | 56.936 | 1.00 40.55 | C |
| ATOM | 25053 | O | GLU | C | 346 | 57.191 | 87.923 | 58.137 | 1.00 40.17 | O |
| ATOM | 25055 | N | GLU | C | 347 | 57.950 | 87.766 | 56.002 | 1.00 42.26 | N |
| ATOM | 25056 | CA | GLU | C | 347 | 59.377 | 87.770 | 56.297 | 1.00 44.23 | C |
| ATOM | 25058 | CB | GLU | C | 347 | 60.102 | 86.940 | 55.225 | 1.00 44.38 | C |
| ATOM | 25061 | CG | GLU | C | 347 | 61.367 | 86.253 | 55.735 | 1.00 47.31 | C |
| ATOM | 25064 | CD | GLU | C | 347 | 62.050 | 85.393 | 54.683 | 1.00 47.83 | C |
| ATOM | 25065 | OE1 | GLU | C | 347 | 61.325 | 84.762 | 53.863 | 1.00 53.29 | O |
| ATOM | 25066 | OE2 | GLU | C | 347 | 63.308 | 85.330 | 54.700 | 1.00 52.14 | O |
| ATOM | 25067 | C | GLU | C | 347 | 59.980 | 89.178 | 56.381 | 1.00 43.69 | C |
| ATOM | 25068 | O | GLU | C | 347 | 59.251 | 90.164 | 56.445 | 1.00 43.24 | O |
| ATOM | 25070 | N | ASP | C | 354 | 68.357 | 95.960 | 46.031 | 1.00 28.24 | N |
| ATOM | 25071 | CA | ASP | C | 354 | 69.378 | 96.287 | 44.991 | 1.00 27.91 | C |
| ATOM | 25073 | CB | ASP | C | 354 | 70.556 | 97.049 | 45.624 | 1.00 27.79 | C |
| ATOM | 25076 | CG | ASP | C | 354 | 71.311 | 96.229 | 46.668 | 1.00 27.91 | C |
| ATOM | 25077 | OD1 | ASP | C | 354 | 70.929 | 95.088 | 46.984 | 1.00 29.93 | O |
| ATOM | 25078 | OD2 | ASP | C | 354 | 72.326 | 96.690 | 47.175 | 1.00 32.52 | O |
| ATOM | 25079 | C | ASP | C | 354 | 69.891 | 95.056 | 44.205 | 1.00 27.71 | C |
| ATOM | 25080 | O | ASP | C | 354 | 70.978 | 95.089 | 43.583 | 1.00 25.69 | O |
| ATOM | 25082 | N | GLU | C | 355 | 69.130 | 93.965 | 44.246 | 1.00 28.00 | N |
| ATOM | 25083 | CA | GLU | C | 355 | 69.519 | 92.726 | 43.550 | 1.00 29.06 | C |
| ATOM | 25085 | CB | GLU | C | 355 | 70.038 | 91.714 | 44.567 | 1.00 28.98 | C |
| ATOM | 25088 | CG | GLU | C | 355 | 71.294 | 92.188 | 45.264 | 1.00 30.12 | C |
| ATOM | 25091 | CD | GLU | C | 355 | 71.870 | 91.149 | 46.220 | 1.00 31.89 | C |
| ATOM | 25092 | OE1 | GLU | C | 355 | 71.385 | 89.986 | 46.209 | 1.00 38.73 | O |
| ATOM | 25093 | OE2 | GLU | C | 355 | 72.828 | 91.498 | 46.960 | 1.00 38.00 | O |
| ATOM | 25094 | C | GLU | C | 355 | 68.416 | 92.133 | 42.688 | 1.00 29.36 | C |
| ATOM | 25095 | O | GLU | C | 355 | 68.613 | 91.099 | 42.058 | 1.00 29.07 | O |
| ATOM | 25097 | N | GLY | C | 356 | 67.259 | 92.797 | 42.665 | 1.00 29.78 | N |
| ATOM | 25098 | CA | GLY | C | 356 | 66.126 | 92.364 | 41.878 | 1.00 31.50 | C |
| ATOM | 25101 | C | GLY | C | 356 | 65.526 | 91.068 | 42.391 | 1.00 32.20 | C |
| ATOM | 25102 | O | GLY | C | 356 | 64.988 | 90.281 | 41.621 | 1.00 33.00 | O |
| ATOM | 25104 | N | ILE | C | 357 | 65.613 | 90.845 | 43.693 | 1.00 33.16 | N |
| ATOM | 25105 | CA | ILE | C | 357 | 65.095 | 89.604 | 44.268 | 1.00 34.42 | C |
| ATOM | 25107 | CB | ILE | C | 357 | 65.638 | 89.344 | 45.690 | 1.00 34.39 | C |
| ATOM | 25109 | CG1 | ILE | C | 357 | 67.130 | 89.005 | 45.609 | 1.00 35.62 | C |
| ATOM | 25112 | CD1 | ILE | C | 357 | 67.810 | 88.946 | 46.952 | 1.00 35.03 | C |
| ATOM | 25116 | CG2 | ILE | C | 357 | 64.875 | 88.193 | 46.371 | 1.00 34.24 | C |
| ATOM | 25120 | C | ILE | C | 357 | 63.583 | 89.683 | 44.253 | 1.00 34.78 | C |
| ATOM | 25121 | O | ILE | C | 357 | 62.981 | 90.729 | 44.496 | 1.00 35.10 | O |
| ATOM | 25123 | N | LEU | C | 358 | 62.974 | 88.569 | 43.883 | 1.00 35.26 | N |
| ATOM | 25124 | CA | LEU | C | 358 | 61.536 | 88.455 | 43.860 | 1.00 35.11 | C |
| ATOM | 25126 | CB | LEU | C | 358 | 61.144 | 87.483 | 42.749 | 1.00 36.36 | C |
| ATOM | 25129 | CG | LEU | C | 358 | 59.697 | 87.011 | 42.730 | 1.00 38.00 | C |
| ATOM | 25131 | CD1 | LEU | C | 358 | 59.184 | 86.982 | 41.302 | 1.00 38.14 | C |
| ATOM | 25135 | CD2 | LEU | C | 358 | 59.585 | 85.643 | 43.427 | 1.00 40.13 | C |
| ATOM | 25139 | C | LEU | C | 358 | 61.135 | 87.962 | 45.245 | 1.00 33.28 | C |
| ATOM | 25140 | O | LEU | C | 358 | 61.533 | 86.883 | 45.661 | 1.00 34.47 | O |
| ATOM | 25142 | N | ARG | C | 359 | 60.406 | 88.790 | 45.985 | 1.00 31.45 | N |
| ATOM | 25143 | CA | ARG | C | 359 | 60.038 | 88.470 | 47.376 | 1.00 30.51 | C |
| ATOM | 25145 | CB | ARG | C | 359 | 60.140 | 89.725 | 48.238 | 1.00 30.62 | C |
| ATOM | 25148 | CG | ARG | C | 359 | 61.571 | 90.129 | 48.692 | 1.00 34.58 | C |
| ATOM | 25151 | CD | ARG | C | 359 | 61.463 | 91.404 | 49.532 | 1.00 37.10 | C |
| ATOM | 25154 | NE | ARG | C | 359 | 60.401 | 92.257 | 48.972 | 1.00 44.08 | N |
| ATOM | 25156 | CZ | ARG | C | 359 | 59.207 | 92.531 | 49.529 | 1.00 47.25 | C |

```
ATOM  25157  NH1 ARG  C 359      58.865  92.094  50.751  1.00 49.03           N
ATOM  25160  NH2 ARG  C 359      58.336  93.286  48.848  1.00 47.38           N
ATOM  25163  C   ARG  C 359      58.620  87.866  47.509  1.00 25.54           C
ATOM  25166  N   AGLN C 360      57.841  87.997  46.442  0.50 22.88           N
ATOM  25167  N   BGLN C 360      57.795  88.052  46.476  0.50 22.48           N
ATOM  25168  CA  AGLN C 360      56.487  87.507  46.480  0.50 20.60           C
ATOM  25169  CA  BGLN C 360      56.402  87.606  46.510  0.50 19.85           C
ATOM  25172  CB  AGLN C 360      55.491  88.633  46.221  0.50 21.86           C
ATOM  25173  CB  BGLN C 360      55.455  88.807  46.280  0.50 20.90           C
ATOM  25178  CG  AGLN C 360      54.093  88.231  46.665  0.50 22.03           C
ATOM  25179  CG  BGLN C 360      55.495  89.951  47.330  0.50 19.39           C
ATOM  25184  CD  AGLN C 360      54.110  87.538  48.033  0.50 20.83           C
ATOM  25185  CD  BGLN C 360      55.728  89.493  48.788  0.50 19.26           C
ATOM  25186  OE1 AGLN C 360      53.827  86.342  48.135  0.50  8.72           O
ATOM  25187  OE1 BGLN C 360      55.288  88.430  49.213  0.50 18.09           O
ATOM  25188  NE2 AGLN C 360      54.523  88.300  49.090  0.50 22.06           N
ATOM  25189  NE2 BGLN C 360      56.414  90.311  49.546  0.50 15.92           N
ATOM  25194  C   AGLN C 360      56.272  86.386  45.496  0.50 18.61           C
ATOM  25195  C   BGLN C 360      56.159  86.517  45.462  0.50 18.13           C
ATOM  25196  O   AGLN C 360      56.983  86.255  44.505  0.50 17.47           O
ATOM  25197  O   BGLN C 360      56.738  86.561  44.372  0.50 16.68           O
ATOM  25200  N   ASP  C 361      55.285  85.550  45.792  1.00 15.75           N
ATOM  25201  CA  ASP  C 361      54.943  84.445  44.906  1.00 15.20           C
ATOM  25203  CB  ASP  C 361      53.842  83.586  45.531  1.00 14.58           C
ATOM  25206  CG  ASP  C 361      54.329  82.773  46.744  1.00 18.85           C
ATOM  25207  OD1 ASP  C 361      55.572  82.714  46.989  1.00 19.41           O
ATOM  25208  OD2 ASP  C 361      53.489  82.142  47.402  1.00 18.46           O
ATOM  25209  C   ASP  C 361      54.443  84.992  43.577  1.00 13.17           C
ATOM  25210  O   ASP  C 361      53.831  86.033  43.524  1.00 13.42           O
ATOM  25212  N   ARG  C 362      54.719  84.270  42.506  1.00 12.11           N
ATOM  25213  CA  ARG  C 362      54.175  84.606  41.180  1.00 13.13           C
ATOM  25215  CB  ARG  C 362      54.959  83.836  40.122  1.00 13.33           C
ATOM  25218  CG  ARG  C 362      56.414  84.277  40.095  1.00 13.70           C
ATOM  25221  CD  ARG  C 362      57.205  83.447  39.082  1.00 15.00           C
ATOM  25224  NE  ARG  C 362      58.636  83.695  39.091  1.00 19.34           N
ATOM  25226  CZ  ARG  C 362      59.495  82.975  39.804  1.00 19.21           C
ATOM  25227  NH1 ARG  C 362      59.077  81.996  40.588  1.00 17.74           N
ATOM  25230  NH2 ARG  C 362      60.793  83.261  39.731  1.00 21.60           N
ATOM  25233  C   ARG  C 362      52.671  84.310  41.106  1.00 11.00           C
ATOM  25234  O   ARG  C 362      52.062  83.790  42.042  1.00 12.37           O
ATOM  25236  N   TYR  C 363      52.037  84.730  40.031  1.00 12.22           N
ATOM  25237  CA  TYR  C 363      50.603  84.705  40.018  1.00 11.73           C
ATOM  25239  CB  TYR  C 363      50.121  85.489  38.796  1.00 13.75           C
ATOM  25242  CG  TYR  C 363      50.295  86.975  38.771  1.00 14.13           C
ATOM  25243  CD1 TYR  C 363      51.061  87.686  39.713  1.00 13.51           C
ATOM  25245  CE1 TYR  C 363      51.214  89.107  39.609  1.00 14.33           C
ATOM  25247  CZ  TYR  C 363      50.591  89.723  38.550  1.00 16.96           C
ATOM  25248  OH  TYR  C 363      50.758  91.080  38.407  1.00 21.86           O
ATOM  25250  CE2 TYR  C 363      49.869  89.029  37.633  1.00 17.46           C
ATOM  25252  CD2 TYR  C 363      49.716  87.693  37.732  1.00 17.91           C
ATOM  25254  C   TYR  C 363      49.910  83.365  40.040  1.00 12.14           C
ATOM  25255  O   TYR  C 363      48.772  83.252  40.514  1.00 12.26           O
ATOM  25257  N   PRO  C 364      50.515  82.350  39.428  1.00 12.35           N
ATOM  25258  CA  PRO  C 364      49.834  81.048  39.516  1.00 12.40           C
ATOM  25260  CB  PRO  C 364      50.803  80.089  38.837  1.00 12.58           C
ATOM  25263  CG  PRO  C 364      51.516  80.949  37.833  1.00 12.51           C
ATOM  25266  CD  PRO  C 364      51.706  82.284  38.537  1.00 12.30           C
```

| | | | | | | | | | |
|---|---|---|---|---|---|---|---|---|---|
| ATOM | 25269 | C | PRO | C | 364 | 49.456 | 80.617 | 40.932 | 1.00 12.68 | C |
| ATOM | 25270 | O | PRO | C | 364 | 48.460 | 79.923 | 41.126 | 1.00 13.58 | O |
| ATOM | 25271 | N | LEU | C | 365 | 50.280 | 80.986 | 41.917 | 1.00 11.31 | N |
| ATOM | 25272 | CA | LEU | C | 365 | 49.935 | 80.723 | 43.312 | 1.00 11.67 | C |
| ATOM | 25274 | CB | LEU | C | 365 | 51.214 | 80.423 | 44.117 | 1.00 12.49 | C |
| ATOM | 25277 | CG | LEU | C | 365 | 51.897 | 79.125 | 43.643 | 1.00 13.06 | C |
| ATOM | 25279 | CD1 | LEU | C | 365 | 53.184 | 78.967 | 44.461 | 1.00 15.67 | C |
| ATOM | 25283 | CD2 | LEU | C | 365 | 51.033 | 77.929 | 43.696 | 1.00 14.71 | C |
| ATOM | 25287 | C | LEU | C | 365 | 49.176 | 81.884 | 43.941 | 1.00 11.89 | C |
| ATOM | 25288 | O | LEU | C | 365 | 48.129 | 81.694 | 44.569 | 1.00 12.42 | O |
| ATOM | 25290 | N | ARG | C | 366 | 49.738 | 83.088 | 43.798 | 1.00 11.98 | N |
| ATOM | 25291 | CA | ARG | C | 366 | 49.245 | 84.262 | 44.546 | 1.00 12.21 | C |
| ATOM | 25293 | CB | ARG | C | 366 | 50.261 | 85.368 | 44.509 | 1.00 12.58 | C |
| ATOM | 25296 | CG | ARG | C | 366 | 49.814 | 86.613 | 45.206 | 1.00 10.94 | C |
| ATOM | 25299 | CD | ARG | C | 366 | 50.952 | 87.526 | 45.638 | 1.00 12.06 | C |
| ATOM | 25302 | NE | ARG | C | 366 | 51.874 | 87.793 | 44.569 | 1.00 12.60 | N |
| ATOM | 25304 | CZ | ARG | C | 366 | 51.982 | 88.945 | 43.897 | 1.00 15.50 | C |
| ATOM | 25305 | NH1 | ARG | C | 366 | 51.118 | 89.971 | 44.097 | 1.00 15.37 | N |
| ATOM | 25308 | NH2 | ARG | C | 366 | 52.950 | 89.048 | 42.976 | 1.00 17.34 | N |
| ATOM | 25311 | C | ARG | C | 366 | 47.876 | 84.741 | 44.035 | 1.00 12.09 | C |
| ATOM | 25312 | O | ARG | C | 366 | 47.085 | 85.298 | 44.834 | 1.00 12.95 | O |
| ATOM | 25314 | N | THR | C | 367 | 47.546 | 84.479 | 42.761 | 1.00 11.21 | N |
| ATOM | 25315 | CA | THR | C | 367 | 46.213 | 84.900 | 42.267 | 1.00 11.31 | C |
| ATOM | 25317 | CB | THR | C | 367 | 46.314 | 85.708 | 40.930 | 1.00 10.99 | C |
| ATOM | 25319 | OG1 | THR | C | 367 | 46.625 | 84.848 | 39.807 | 1.00 11.70 | O |
| ATOM | 25321 | CG2 | THR | C | 367 | 47.309 | 86.853 | 41.094 | 1.00 12.93 | C |
| ATOM | 25325 | C | THR | C | 367 | 45.262 | 83.742 | 42.064 | 1.00 11.67 | C |
| ATOM | 25326 | O | THR | C | 367 | 44.250 | 83.891 | 41.432 | 1.00 10.43 | O |
| ATOM | 25328 | N | SER | C | 368 | 45.574 | 82.590 | 42.668 | 1.00 10.95 | N |
| ATOM | 25329 | CA | SER | C | 368 | 44.788 | 81.400 | 42.428 | 1.00 11.69 | C |
| ATOM | 25331 | CB | SER | C | 368 | 45.462 | 80.134 | 42.958 | 1.00 12.23 | C |
| ATOM | 25334 | OG | SER | C | 368 | 45.778 | 80.231 | 44.359 | 1.00 12.65 | O |
| ATOM | 25336 | C | SER | C | 368 | 43.310 | 81.537 | 42.862 | 1.00 11.21 | C |
| ATOM | 25337 | O | SER | C | 368 | 42.428 | 81.035 | 42.147 | 1.00 11.93 | O |
| ATOM | 25339 | N | PRO | C | 369 | 43.003 | 82.191 | 44.014 | 1.00 11.05 | N |
| ATOM | 25340 | CA | PRO | C | 369 | 41.574 | 82.293 | 44.365 | 1.00 10.99 | C |
| ATOM | 25342 | CB | PRO | C | 369 | 41.612 | 82.870 | 45.782 | 1.00 11.74 | C |
| ATOM | 25345 | CG | PRO | C | 369 | 42.962 | 82.477 | 46.282 | 1.00 9.96 | C |
| ATOM | 25348 | CD | PRO | C | 369 | 43.842 | 82.678 | 45.137 | 1.00 10.91 | C |
| ATOM | 25351 | C | PRO | C | 369 | 40.789 | 83.191 | 43.400 | 1.00 11.34 | C |
| ATOM | 25352 | O | PRO | C | 369 | 39.592 | 82.977 | 43.094 | 1.00 11.46 | O |
| ATOM | 25353 | N | GLN | C | 370 | 41.469 | 84.240 | 42.955 | 1.00 10.77 | N |
| ATOM | 25354 | CA | GLN | C | 370 | 40.932 | 85.163 | 41.957 | 1.00 10.69 | C |
| ATOM | 25356 | CB | GLN | C | 370 | 41.819 | 86.395 | 41.863 | 1.00 10.21 | C |
| ATOM | 25359 | CG | GLN | C | 370 | 41.922 | 87.298 | 43.141 | 1.00 10.78 | C |
| ATOM | 25362 | CD | GLN | C | 370 | 42.990 | 86.797 | 44.150 | 1.00 10.29 | C |
| ATOM | 25363 | OE1 | GLN | C | 370 | 43.630 | 85.730 | 43.908 | 1.00 11.71 | O |
| ATOM | 25364 | NE2 | GLN | C | 370 | 43.205 | 87.547 | 45.239 | 1.00 12.45 | N |
| ATOM | 25367 | C | GLN | C | 370 | 40.780 | 84.552 | 40.585 | 1.00 11.16 | C |
| ATOM | 25368 | O | GLN | C | 370 | 39.892 | 84.912 | 39.791 | 1.00 12.18 | O |
| ATOM | 25370 | N | TRP | C | 371 | 41.630 | 83.596 | 40.293 | 1.00 10.61 | N |
| ATOM | 25371 | CA | TRP | C | 371 | 41.516 | 82.876 | 39.039 | 1.00 10.94 | C |
| ATOM | 25373 | CB | TRP | C | 371 | 42.841 | 82.272 | 38.725 | 1.00 11.34 | C |
| ATOM | 25376 | CG | TRP | C | 371 | 42.949 | 81.758 | 37.326 | 1.00 11.62 | C |
| ATOM | 25377 | CD1 | TRP | C | 371 | 42.777 | 80.461 | 36.900 | 1.00 11.62 | C |
| ATOM | 25379 | NE1 | TRP | C | 371 | 42.989 | 80.357 | 35.565 | 1.00 12.57 | N |
| ATOM | 25381 | CE2 | TRP | C | 371 | 43.327 | 81.592 | 35.081 | 1.00 11.37 | C |

| ATOM | 25382 | CD2 | TRP | C | 371 | 43.326 | 82.496 | 36.167 | 1.00 | 10.61 | C |
|---|---|---|---|---|---|---|---|---|---|---|---|
| ATOM | 25383 | CE3 | TRP | C | 371 | 43.537 | 83.852 | 35.920 | 1.00 | 12.97 | C |
| ATOM | 25385 | CZ3 | TRP | C | 371 | 43.806 | 84.256 | 34.626 | 1.00 | 13.73 | C |
| ATOM | 25387 | CH2 | TRP | C | 371 | 43.860 | 83.321 | 33.596 | 1.00 | 12.83 | C |
| ATOM | 25389 | CZ2 | TRP | C | 371 | 43.570 | 81.996 | 33.793 | 1.00 | 12.78 | C |
| ATOM | 25391 | C | TRP | C | 371 | 40.433 | 81.830 | 39.051 | 1.00 | 12.73 | C |
| ATOM | 25392 | O | TRP | C | 371 | 39.663 | 81.706 | 38.116 | 1.00 | 14.47 | O |
| ATOM | 25394 | N | LEU | C | 372 | 40.396 | 81.034 | 40.110 | 1.00 | 12.87 | N |
| ATOM | 25395 | CA | LEU | C | 372 | 39.467 | 79.879 | 40.200 | 1.00 | 11.22 | C |
| ATOM | 25397 | CB | LEU | C | 372 | 39.999 | 78.838 | 41.175 | 1.00 | 11.99 | C |
| ATOM | 25400 | CG | LEU | C | 372 | 41.238 | 78.084 | 40.707 | 1.00 | 10.66 | C |
| ATOM | 25402 | CD1 | LEU | C | 372 | 41.801 | 77.172 | 41.814 | 1.00 | 14.48 | C |
| ATOM | 25406 | CD2 | LEU | C | 372 | 40.991 | 77.373 | 39.428 | 1.00 | 14.46 | C |
| ATOM | 25410 | C | LEU | C | 372 | 38.056 | 80.353 | 40.650 | 1.00 | 11.85 | C |
| ATOM | 25411 | O | LEU | C | 372 | 37.030 | 79.708 | 40.307 | 1.00 | 12.03 | O |
| ATOM | 25413 | N | GLY | C | 373 | 37.967 | 81.387 | 41.460 | 1.00 | 11.33 | N |
| ATOM | 25414 | CA | GLY | C | 373 | 36.672 | 81.769 | 41.967 | 1.00 | 11.81 | C |
| ATOM | 25417 | C | GLY | C | 373 | 35.597 | 81.904 | 40.897 | 1.00 | 11.65 | C |
| ATOM | 25418 | O | GLY | C | 373 | 34.502 | 81.366 | 41.038 | 1.00 | 12.05 | O |
| ATOM | 25420 | N | PRO | C | 374 | 35.873 | 82.692 | 39.849 | 1.00 | 13.22 | N |
| ATOM | 25421 | CA | PRO | C | 374 | 34.834 | 82.928 | 38.866 | 1.00 | 14.43 | C |
| ATOM | 25423 | CB | PRO | C | 374 | 35.548 | 83.839 | 37.878 | 1.00 | 14.10 | C |
| ATOM | 25426 | CG | PRO | C | 374 | 36.445 | 84.662 | 38.787 | 1.00 | 14.24 | C |
| ATOM | 25429 | CD | PRO | C | 374 | 37.021 | 83.577 | 39.629 | 1.00 | 13.31 | C |
| ATOM | 25432 | C | PRO | C | 374 | 34.307 | 81.659 | 38.208 | 1.00 | 13.97 | C |
| ATOM | 25433 | O | PRO | C | 374 | 33.107 | 81.489 | 38.078 | 1.00 | 15.17 | O |
| ATOM | 25434 | N | LEU | C | 375 | 35.184 | 80.743 | 37.838 | 1.00 | 13.17 | N |
| ATOM | 25435 | CA | LEU | C | 375 | 34.743 | 79.517 | 37.215 | 1.00 | 13.97 | C |
| ATOM | 25437 | CB | LEU | C | 375 | 35.894 | 78.842 | 36.514 | 1.00 | 14.70 | C |
| ATOM | 25440 | CG | LEU | C | 375 | 36.999 | 78.223 | 37.321 | 1.00 | 12.87 | C |
| ATOM | 25442 | CD1 | LEU | C | 375 | 36.604 | 76.771 | 37.716 | 1.00 | 17.13 | C |
| ATOM | 25446 | CD2 | LEU | C | 375 | 38.345 | 78.253 | 36.506 | 1.00 | 15.30 | C |
| ATOM | 25450 | C | LEU | C | 375 | 34.040 | 78.592 | 38.226 | 1.00 | 12.90 | C |
| ATOM | 25451 | O | LEU | C | 375 | 33.153 | 77.826 | 37.852 | 1.00 | 13.75 | O |
| ATOM | 25453 | N | VAL | C | 376 | 34.417 | 78.678 | 39.502 | 1.00 | 12.36 | N |
| ATOM | 25454 | CA | VAL | C | 376 | 33.679 | 77.922 | 40.528 | 1.00 | 12.58 | C |
| ATOM | 25456 | CB | VAL | C | 376 | 34.391 | 77.968 | 41.881 | 1.00 | 12.57 | C |
| ATOM | 25458 | CG1 | VAL | C | 376 | 33.482 | 77.435 | 42.966 | 1.00 | 14.42 | C |
| ATOM | 25462 | CG2 | VAL | C | 376 | 35.660 | 77.154 | 41.779 | 1.00 | 14.10 | C |
| ATOM | 25466 | C | VAL | C | 376 | 32.227 | 78.416 | 40.601 | 1.00 | 12.69 | C |
| ATOM | 25467 | O | VAL | C | 376 | 31.262 | 77.625 | 40.713 | 1.00 | 11.94 | O |
| ATOM | 25469 | N | SER | C | 377 | 32.024 | 79.726 | 40.532 | 1.00 | 12.18 | N |
| ATOM | 25470 | CA | SER | C | 377 | 30.647 | 80.245 | 40.588 | 1.00 | 12.79 | C |
| ATOM | 25472 | CB | SER | C | 377 | 30.625 | 81.759 | 40.525 | 1.00 | 13.90 | C |
| ATOM | 25475 | OG | SER | C | 377 | 29.331 | 82.255 | 40.855 | 1.00 | 14.72 | O |
| ATOM | 25477 | C | SER | C | 377 | 29.839 | 79.673 | 39.400 | 1.00 | 12.50 | C |
| ATOM | 25478 | O | SER | C | 377 | 28.650 | 79.355 | 39.491 | 1.00 | 13.63 | O |
| ATOM | 25480 | N | ASP | C | 378 | 30.511 | 79.590 | 38.250 | 1.00 | 12.68 | N |
| ATOM | 25481 | CA | ASP | C | 378 | 29.901 | 79.013 | 37.040 | 1.00 | 13.24 | C |
| ATOM | 25483 | CB | ASP | C | 378 | 30.838 | 79.095 | 35.830 | 1.00 | 13.82 | C |
| ATOM | 25486 | CG | ASP | C | 378 | 30.865 | 80.471 | 35.220 | 1.00 | 17.83 | C |
| ATOM | 25487 | OD1 | ASP | C | 378 | 30.106 | 81.400 | 35.645 | 1.00 | 18.82 | O |
| ATOM | 25488 | OD2 | ASP | C | 378 | 31.664 | 80.688 | 34.257 | 1.00 | 18.13 | O |
| ATOM | 25489 | C | ASP | C | 378 | 29.471 | 77.568 | 37.273 | 1.00 | 13.14 | C |
| ATOM | 25490 | O | ASP | C | 378 | 28.412 | 77.135 | 36.813 | 1.00 | 13.56 | O |
| ATOM | 25492 | N | LEU | C | 379 | 30.347 | 76.804 | 37.923 | 1.00 | 13.34 | N |
| ATOM | 25493 | CA | LEU | C | 379 | 30.067 | 75.406 | 38.207 | 1.00 | 12.57 | C |

| ATOM | 25495 | CB | LEU C 379 | 31.301 | 74.687 | 38.749 | 1.00 | 14.39 | C |
| ATOM | 25498 | CG | LEU C 379 | 32.411 | 74.483 | 37.706 | 1.00 | 14.53 | C |
| ATOM | 25500 | CD1 | LEU C 379 | 33.687 | 73.990 | 38.413 | 1.00 | 12.10 | C |
| ATOM | 25504 | CD2 | LEU C 379 | 32.047 | 73.524 | 36.595 | 1.00 | 15.95 | C |
| ATOM | 25508 | C | LEU C 379 | 28.891 | 75.258 | 39.169 | 1.00 | 13.14 | C |
| ATOM | 25509 | O | LEU C 379 | 28.043 | 74.405 | 39.000 | 1.00 | 13.13 | O |
| ATOM | 25511 | N | ILE C 380 | 28.801 | 76.150 | 40.138 | 1.00 | 11.98 | N |
| ATOM | 25512 | CA | ILE C 380 | 27.664 | 76.154 | 41.044 | 1.00 | 12.11 | C |
| ATOM | 25514 | CB | ILE C 380 | 27.962 | 77.045 | 42.283 | 1.00 | 12.45 | C |
| ATOM | 25516 | CG1 | ILE C 380 | 29.162 | 76.414 | 43.034 | 1.00 | 13.08 | C |
| ATOM | 25519 | CD1 | ILE C 380 | 29.679 | 77.245 | 44.181 | 1.00 | 13.05 | C |
| ATOM | 25523 | CG2 | ILE C 380 | 26.742 | 77.266 | 43.163 | 1.00 | 11.89 | C |
| ATOM | 25527 | C | ILE C 380 | 26.366 | 76.542 | 40.347 | 1.00 | 12.83 | C |
| ATOM | 25528 | O | ILE C 380 | 25.309 | 75.967 | 40.607 | 1.00 | 12.80 | O |
| ATOM | 25530 | N | HIS C 381 | 26.439 | 77.494 | 39.417 | 1.00 | 12.59 | N |
| ATOM | 25531 | CA | HIS C 381 | 25.268 | 77.861 | 38.643 | 1.00 | 12.69 | C |
| ATOM | 25533 | CB | HIS C 381 | 25.673 | 79.107 | 37.817 | 1.00 | 12.31 | C |
| ATOM | 25536 | CG | HIS C 381 | 24.590 | 79.643 | 36.926 | 1.00 | 12.62 | C |
| ATOM | 25537 | ND1 | HIS C 381 | 24.290 | 79.074 | 35.699 | 1.00 | 13.94 | N |
| ATOM | 25539 | CE1 | HIS C 381 | 23.315 | 79.765 | 35.136 | 1.00 | 14.66 | C |
| ATOM | 25541 | NE2 | HIS C 381 | 22.941 | 80.717 | 35.968 | 1.00 | 13.85 | N |
| ATOM | 25543 | CD2 | HIS C 381 | 23.748 | 80.686 | 37.077 | 1.00 | 14.43 | C |
| ATOM | 25545 | C | HIS C 381 | 24.808 | 76.692 | 37.751 | 1.00 | 11.02 | C |
| ATOM | 25546 | O | HIS C 381 | 23.618 | 76.359 | 37.676 | 1.00 | 12.77 | O |
| ATOM | 25548 | N | ALA C 382 | 25.756 | 76.062 | 37.050 | 1.00 | 11.42 | N |
| ATOM | 25549 | CA | ALA C 382 | 25.461 | 74.881 | 36.244 | 1.00 | 11.06 | C |
| ATOM | 25551 | CB | ALA C 382 | 26.720 | 74.332 | 35.650 | 1.00 | 11.12 | C |
| ATOM | 25555 | C | ALA C 382 | 24.757 | 73.824 | 37.075 | 1.00 | 10.48 | C |
| ATOM | 25556 | O | ALA C 382 | 23.819 | 73.137 | 36.603 | 1.00 | 13.61 | O |
| ATOM | 25558 | N | HIS C 383 | 25.193 | 73.695 | 38.333 | 1.00 | 11.19 | N |
| ATOM | 25559 | CA | HIS C 383 | 24.584 | 72.711 | 39.222 | 1.00 | 12.46 | C |
| ATOM | 25561 | CB | HIS C 383 | 25.281 | 72.670 | 40.582 | 1.00 | 12.71 | C |
| ATOM | 25564 | CG | HIS C 383 | 25.067 | 71.385 | 41.283 | 1.00 | 13.14 | C |
| ATOM | 25565 | ND1 | HIS C 383 | 25.922 | 70.311 | 41.134 | 1.00 | 12.31 | N |
| ATOM | 25567 | CE1 | HIS C 383 | 25.444 | 69.296 | 41.842 | 1.00 | 15.69 | C |
| ATOM | 25569 | NE2 | HIS C 383 | 24.316 | 69.671 | 42.423 | 1.00 | 14.93 | N |
| ATOM | 25571 | CD2 | HIS C 383 | 24.051 | 70.963 | 42.073 | 1.00 | 15.76 | C |
| ATOM | 25573 | C | HIS C 383 | 23.117 | 73.031 | 39.410 | 1.00 | 11.78 | C |
| ATOM | 25574 | O | HIS C 383 | 22.233 | 72.131 | 39.375 | 1.00 | 12.02 | O |
| ATOM | 25576 | N | ALA C 384 | 22.835 | 74.323 | 39.644 | 1.00 | 11.90 | N |
| ATOM | 25577 | CA | ALA C 384 | 21.436 | 74.725 | 39.848 | 1.00 | 12.35 | C |
| ATOM | 25579 | CB | ALA C 384 | 21.331 | 76.198 | 40.274 | 1.00 | 13.04 | C |
| ATOM | 25583 | C | ALA C 384 | 20.598 | 74.483 | 38.589 | 1.00 | 12.47 | C |
| ATOM | 25584 | O | ALA C 384 | 19.464 | 74.048 | 38.674 | 1.00 | 12.41 | O |
| ATOM | 25586 | N | VAL C 385 | 21.163 | 74.782 | 37.427 | 1.00 | 12.56 | N |
| ATOM | 25587 | CA | VAL C 385 | 20.438 | 74.605 | 36.144 | 1.00 | 13.36 | C |
| ATOM | 25589 | CB | VAL C 385 | 21.208 | 75.205 | 34.950 | 1.00 | 12.52 | C |
| ATOM | 25591 | CG1 | VAL C 385 | 20.515 | 74.819 | 33.663 | 1.00 | 13.41 | C |
| ATOM | 25595 | CG2 | VAL C 385 | 21.322 | 76.720 | 35.123 | 1.00 | 13.57 | C |
| ATOM | 25599 | C | VAL C 385 | 20.157 | 73.132 | 35.878 | 1.00 | 12.98 | C |
| ATOM | 25600 | O | VAL C 385 | 19.032 | 72.728 | 35.590 | 1.00 | 12.60 | O |
| ATOM | 25602 | N | LEU C 386 | 21.202 | 72.294 | 35.944 | 1.00 | 11.53 | N |
| ATOM | 25603 | CA | LEU C 386 | 21.008 | 70.854 | 35.689 | 1.00 | 12.32 | C |
| ATOM | 25605 | CB | LEU C 386 | 22.352 | 70.155 | 35.596 | 1.00 | 13.19 | C |
| ATOM | 25608 | CG | LEU C 386 | 23.197 | 70.486 | 34.403 | 1.00 | 13.28 | C |
| ATOM | 25610 | CD1 | LEU C 386 | 24.434 | 69.620 | 34.387 | 1.00 | 14.17 | C |
| ATOM | 25614 | CD2 | LEU C 386 | 22.424 | 70.298 | 33.106 | 1.00 | 14.63 | C |

| | | | | | | | | | |
|---|---|---|---|---|---|---|---|---|---|
| ATOM | 25618 | C | LEU | C | 386 | 20.099 | 70.191 | 36.700 | 1.00 12.04 | C |
| ATOM | 25619 | O | LEU | C | 386 | 19.387 | 69.224 | 36.360 | 1.00 13.82 | O |
| ATOM | 25621 | N | THR | C | 387 | 20.141 | 70.626 | 37.967 | 1.00 12.04 | N |
| ATOM | 25622 | CA | THR | C | 387 | 19.253 | 69.996 | 38.951 | 1.00 13.22 | C |
| ATOM | 25624 | CB | THR | C | 387 | 19.481 | 70.551 | 40.354 | 1.00 13.29 | C |
| ATOM | 25626 | OG1 | THR | C | 387 | 20.827 | 70.273 | 40.730 | 1.00 13.25 | O |
| ATOM | 25628 | CG2 | THR | C | 387 | 18.530 | 69.918 | 41.322 | 1.00 13.30 | C |
| ATOM | 25632 | C | THR | C | 387 | 17.780 | 70.168 | 38.536 | 1.00 12.98 | C |
| ATOM | 25633 | O | THR | C | 387 | 16.992 | 69.231 | 38.587 | 1.00 12.29 | O |
| ATOM | 25635 | N | ILE | C | 388 | 17.414 | 71.366 | 38.112 | 1.00 13.19 | N |
| ATOM | 25636 | CA | ILE | C | 388 | 16.059 | 71.554 | 37.586 | 1.00 14.19 | C |
| ATOM | 25638 | CB | ILE | C | 388 | 15.762 | 73.014 | 37.358 | 1.00 13.64 | C |
| ATOM | 25640 | CG1 | ILE | C | 388 | 15.657 | 73.732 | 38.700 | 1.00 15.76 | C |
| ATOM | 25643 | CD1 | ILE | C | 388 | 15.747 | 75.266 | 38.558 | 1.00 17.77 | C |
| ATOM | 25647 | CG2 | ILE | C | 388 | 14.455 | 73.205 | 36.527 | 1.00 12.71 | C |
| ATOM | 25651 | C | ILE | C | 388 | 15.836 | 70.766 | 36.310 | 1.00 13.59 | C |
| ATOM | 25652 | O | ILE | C | 388 | 14.796 | 70.115 | 36.174 | 1.00 13.28 | O |
| ATOM | 25654 | N | GLU | C | 389 | 16.764 | 70.853 | 35.354 | 1.00 13.05 | N |
| ATOM | 25655 | CA | GLU | C | 389 | 16.563 | 70.127 | 34.082 | 1.00 14.69 | C |
| ATOM | 25657 | CB | GLU | C | 389 | 17.711 | 70.395 | 33.116 | 1.00 15.42 | C |
| ATOM | 25660 | CG | GLU | C | 389 | 17.512 | 69.848 | 31.748 | 1.00 14.31 | C |
| ATOM | 25663 | CD | GLU | C | 389 | 16.478 | 70.611 | 30.916 | 1.00 16.40 | C |
| ATOM | 25664 | OE1 | GLU | C | 389 | 15.812 | 71.542 | 31.468 | 1.00 14.95 | O |
| ATOM | 25665 | OE2 | GLU | C | 389 | 16.313 | 70.258 | 29.705 | 1.00 16.91 | O |
| ATOM | 25666 | C | GLU | C | 389 | 16.421 | 68.620 | 34.270 | 1.00 15.15 | C |
| ATOM | 25667 | O | GLU | C | 389 | 15.553 | 68.000 | 33.659 | 1.00 14.69 | O |
| ATOM | 25669 | N | ALA | C | 390 | 17.288 | 68.010 | 35.094 | 1.00 13.88 | N |
| ATOM | 25670 | CA | ALA | C | 390 | 17.316 | 66.548 | 35.239 | 1.00 15.55 | C |
| ATOM | 25672 | CB | ALA | C | 390 | 18.650 | 66.091 | 35.771 | 1.00 15.17 | C |
| ATOM | 25676 | C | ALA | C | 390 | 16.241 | 66.035 | 36.172 | 1.00 14.98 | C |
| ATOM | 25677 | O | ALA | C | 390 | 15.674 | 64.941 | 35.955 | 1.00 17.56 | O |
| ATOM | 25679 | N | GLY | C | 391 | 15.934 | 66.811 | 37.205 | 1.00 14.40 | N |
| ATOM | 25680 | CA | GLY | C | 391 | 15.071 | 66.359 | 38.275 | 1.00 13.54 | C |
| ATOM | 25683 | C | GLY | C | 391 | 13.665 | 66.927 | 38.426 | 1.00 14.58 | C |
| ATOM | 25684 | O | GLY | C | 391 | 12.851 | 66.395 | 39.191 | 1.00 15.27 | O |
| ATOM | 25686 | N | GLN | C | 392 | 13.382 | 68.045 | 37.748 | 1.00 13.50 | N |
| ATOM | 25687 | CA | GLN | C | 392 | 12.148 | 68.777 | 37.997 | 1.00 13.79 | C |
| ATOM | 25689 | CB | GLN | C | 392 | 12.415 | 69.974 | 38.917 | 1.00 13.35 | C |
| ATOM | 25692 | CG | GLN | C | 392 | 13.041 | 69.647 | 40.208 | 1.00 16.14 | C |
| ATOM | 25695 | CD | GLN | C | 392 | 13.602 | 70.875 | 40.909 | 1.00 16.95 | C |
| ATOM | 25696 | OE1 | GLN | C | 392 | 14.751 | 70.837 | 41.398 | 1.00 19.11 | O |
| ATOM | 25697 | NE2 | GLN | C | 392 | 12.841 | 71.986 | 40.895 | 1.00 15.78 | N |
| ATOM | 25700 | C | GLN | C | 392 | 11.535 | 69.331 | 36.696 | 1.00 13.47 | C |
| ATOM | 25701 | O | GLN | C | 392 | 10.738 | 70.286 | 36.745 | 1.00 15.14 | O |
| ATOM | 25703 | N | SER | C | 393 | 11.792 | 68.689 | 35.569 | 1.00 13.36 | N |
| ATOM | 25704 | CA | SER | C | 393 | 11.293 | 69.250 | 34.301 | 1.00 13.55 | C |
| ATOM | 25706 | CB | SER | C | 393 | 12.445 | 69.883 | 33.524 | 1.00 13.25 | C |
| ATOM | 25709 | OG | SER | C | 393 | 12.970 | 70.994 | 34.229 | 1.00 15.40 | O |
| ATOM | 25711 | C | SER | C | 393 | 10.635 | 68.206 | 33.425 | 1.00 13.19 | C |
| ATOM | 25712 | O | SER | C | 393 | 11.117 | 67.068 | 33.324 | 1.00 14.20 | O |
| ATOM | 25714 | N | THR | C | 394 | 9.568 | 68.625 | 32.755 | 1.00 11.49 | N |
| ATOM | 25715 | CA | THR | C | 394 | 8.942 | 67.872 | 31.718 | 1.00 11.54 | C |
| ATOM | 25717 | CB | THR | C | 394 | 7.412 | 68.028 | 31.815 | 1.00 11.60 | C |
| ATOM | 25719 | OG1 | THR | C | 394 | 6.921 | 67.609 | 33.117 | 1.00 12.44 | O |
| ATOM | 25721 | CG2 | THR | C | 394 | 6.690 | 67.244 | 30.680 | 1.00 12.64 | C |
| ATOM | 25725 | C | THR | C | 394 | 9.427 | 68.457 | 30.395 | 1.00 13.19 | C |
| ATOM | 25726 | O | THR | C | 394 | 9.249 | 69.650 | 30.130 | 1.00 13.06 | O |

| ATOM | 25728 | N   | THR | C | 395 | 10.027 | 67.614 | 29.563 | 1.00 | 13.02 | N |
|------|-------|-----|-----|---|-----|--------|--------|--------|------|-------|---|
| ATOM | 25729 | CA  | THR | C | 395 | 10.724 | 68.116 | 28.381 | 1.00 | 13.74 | C |
| ATOM | 25731 | CB  | THR | C | 395 | 12.235 | 67.880 | 28.473 | 1.00 | 13.85 | C |
| ATOM | 25733 | OG1 | THR | C | 395 | 12.543 | 66.483 | 28.519 | 1.00 | 14.41 | O |
| ATOM | 25735 | CG2 | THR | C | 395 | 12.811 | 68.571 | 29.689 | 1.00 | 14.74 | C |
| ATOM | 25739 | C   | THR | C | 395 | 10.158 | 67.567 | 27.096 | 1.00 | 14.03 | C |
| ATOM | 25740 | O   | THR | C | 395 | 10.686 | 67.909 | 26.044 | 1.00 | 14.37 | O |
| ATOM | 25742 | N   | ASP | C | 396 | 9.083  | 66.762 | 27.138 | 1.00 | 13.54 | N |
| ATOM | 25743 | CA  | ASP | C | 396 | 8.450  | 66.321 | 25.912 | 1.00 | 13.37 | C |
| ATOM | 25745 | CB  | ASP | C | 396 | 7.869  | 64.891 | 26.039 | 1.00 | 12.95 | C |
| ATOM | 25748 | CG  | ASP | C | 396 | 6.717  | 64.768 | 27.048 | 1.00 | 14.68 | C |
| ATOM | 25749 | OD1 | ASP | C | 396 | 6.943  | 65.021 | 28.279 | 1.00 | 15.92 | O |
| ATOM | 25750 | OD2 | ASP | C | 396 | 5.584  | 64.336 | 26.633 | 1.00 | 16.91 | O |
| ATOM | 25751 | C   | ASP | C | 396 | 7.412  | 67.372 | 25.476 | 1.00 | 13.71 | C |
| ATOM | 25752 | O   | ASP | C | 396 | 7.381  | 68.493 | 25.999 | 1.00 | 13.88 | O |
| ATOM | 25754 | N   | ASN | C | 397 | 6.573  | 67.017 | 24.503 | 1.00 | 12.86 | N |
| ATOM | 25755 | CA  | ASN | C | 397 | 5.657  | 67.964 | 23.895 | 1.00 | 13.11 | C |
| ATOM | 25757 | CB  | ASN | C | 397 | 6.453  | 68.987 | 23.080 | 1.00 | 12.18 | C |
| ATOM | 25760 | CG  | ASN | C | 397 | 5.583  | 70.124 | 22.577 | 1.00 | 12.49 | C |
| ATOM | 25761 | OD1 | ASN | C | 397 | 5.124  | 70.943 | 23.384 | 1.00 | 15.48 | O |
| ATOM | 25762 | ND2 | ASN | C | 397 | 5.286  | 70.131 | 21.282 | 1.00 | 12.98 | N |
| ATOM | 25765 | C   | ASN | C | 397 | 4.762  | 67.165 | 22.956 | 1.00 | 13.70 | C |
| ATOM | 25766 | O   | ASN | C | 397 | 5.213  | 66.167 | 22.438 | 1.00 | 14.06 | O |
| ATOM | 25768 | N   | PRO | C | 398 | 3.529  | 67.591 | 22.683 | 1.00 | 13.79 | N |
| ATOM | 25769 | CA  | PRO | C | 398 | 2.734  | 68.526 | 23.470 | 1.00 | 14.29 | C |
| ATOM | 25771 | CB  | PRO | C | 398 | 1.368  | 68.500 | 22.773 | 1.00 | 14.36 | C |
| ATOM | 25774 | CG  | PRO | C | 398 | 1.552  | 67.764 | 21.541 | 1.00 | 17.12 | C |
| ATOM | 25777 | CD  | PRO | C | 398 | 2.739  | 66.903 | 21.652 | 1.00 | 15.76 | C |
| ATOM | 25780 | C   | PRO | C | 398 | 2.517  | 68.096 | 24.902 | 1.00 | 13.94 | C |
| ATOM | 25781 | O   | PRO | C | 398 | 2.606  | 66.912 | 25.179 | 1.00 | 14.98 | O |
| ATOM | 25782 | N   | LEU | C | 399 | 2.161  | 69.038 | 25.779 | 1.00 | 14.61 | N |
| ATOM | 25783 | CA  | LEU | C | 399 | 1.978  | 68.734 | 27.209 | 1.00 | 13.99 | C |
| ATOM | 25785 | CB  | LEU | C | 399 | 2.907  | 69.603 | 28.053 | 1.00 | 15.73 | C |
| ATOM | 25788 | CG  | LEU | C | 399 | 4.396  | 69.339 | 27.740 | 1.00 | 15.11 | C |
| ATOM | 25790 | CD1 | LEU | C | 399 | 5.328  | 70.183 | 28.636 | 1.00 | 16.42 | C |
| ATOM | 25794 | CD2 | LEU | C | 399 | 4.817  | 67.828 | 27.853 | 1.00 | 16.73 | C |
| ATOM | 25798 | C   | LEU | C | 399 | 0.527  | 68.880 | 27.598 | 1.00 | 14.89 | C |
| ATOM | 25799 | O   | LEU | C | 399 | -0.172 | 69.725 | 27.051 | 1.00 | 14.15 | O |
| ATOM | 25801 | N   | ILE | C | 400 | 0.093  | 68.051 | 28.550 | 1.00 | 14.30 | N |
| ATOM | 25802 | CA  | ILE | C | 400 | -1.317 | 67.897 | 28.895 | 1.00 | 15.19 | C |
| ATOM | 25804 | CB  | ILE | C | 400 | -1.669 | 66.378 | 28.975 | 1.00 | 16.46 | C |
| ATOM | 25806 | CG1 | ILE | C | 400 | -1.250 | 65.659 | 27.683 | 1.00 | 19.23 | C |
| ATOM | 25809 | CD1 | ILE | C | 400 | -1.739 | 66.294 | 26.477 | 1.00 | 21.04 | C |
| ATOM | 25813 | CG2 | ILE | C | 400 | -3.126 | 66.150 | 29.351 | 1.00 | 16.89 | C |
| ATOM | 25817 | C   | ILE | C | 400 | -1.548 | 68.482 | 30.281 | 1.00 | 15.28 | C |
| ATOM | 25818 | O   | ILE | C | 400 | -0.835 | 68.087 | 31.217 | 1.00 | 13.92 | O |
| ATOM | 25820 | N   | ASP | C | 401 | -2.495 | 69.427 | 30.385 | 1.00 | 16.92 | N |
| ATOM | 25821 | CA  | ASP | C | 401 | -2.942 | 69.977 | 31.657 | 1.00 | 18.10 | C |
| ATOM | 25823 | CB  | ASP | C | 401 | -3.172 | 71.497 | 31.600 | 1.00 | 18.88 | C |
| ATOM | 25826 | CG  | ASP | C | 401 | -3.515 | 72.092 | 32.990 | 1.00 | 19.40 | C |
| ATOM | 25827 | OD1 | ASP | C | 401 | -3.551 | 71.352 | 34.041 | 1.00 | 26.96 | O |
| ATOM | 25828 | OD2 | ASP | C | 401 | -3.694 | 73.310 | 33.062 | 1.00 | 22.56 | O |
| ATOM | 25829 | C   | ASP | C | 401 | -4.239 | 69.301 | 32.037 | 1.00 | 18.78 | C |
| ATOM | 25830 | O   | ASP | C | 401 | -5.289 | 69.719 | 31.599 | 1.00 | 17.81 | O |
| ATOM | 25832 | N   | VAL | C | 402 | -4.149 | 68.258 | 32.837 | 1.00 | 20.96 | N |
| ATOM | 25833 | CA  | VAL | C | 402 | -5.345 | 67.469 | 33.150 | 1.00 | 22.70 | C |
| ATOM | 25835 | CB  | VAL | C | 402 | -4.972 | 66.187 | 33.911 | 1.00 | 22.96 | C |

| ATOM | 25837 | CG1 | VAL | C | 402 | -6.210 | 65.463 | 34.387 | 1.00 | 25.35 | C |
| --- | --- | --- | --- | --- | --- | --- | --- | --- | --- | --- | --- |
| ATOM | 25841 | CG2 | VAL | C | 402 | -4.137 | 65.283 | 33.015 | 1.00 | 23.97 | C |
| ATOM | 25845 | C | VAL | C | 402 | -6.348 | 68.316 | 33.936 | 1.00 | 24.21 | C |
| ATOM | 25846 | O | VAL | C | 402 | -7.550 | 68.301 | 33.639 | 1.00 | 24.63 | O |
| ATOM | 25848 | N | GLU | C | 403 | -5.857 | 69.081 | 34.910 | 1.00 | 26.00 | N |
| ATOM | 25849 | CA | GLU | C | 403 | -6.737 | 69.902 | 35.757 | 1.00 | 27.71 | C |
| ATOM | 25851 | CB | GLU | C | 403 | -5.937 | 70.776 | 36.730 | 1.00 | 28.50 | C |
| ATOM | 25854 | CG | GLU | C | 403 | -5.366 | 70.048 | 37.939 | 1.00 | 32.48 | C |
| ATOM | 25857 | CD | GLU | C | 403 | -6.126 | 68.774 | 38.283 | 1.00 | 36.57 | C |
| ATOM | 25858 | OE1 | GLU | C | 403 | -7.374 | 68.838 | 38.488 | 1.00 | 40.48 | O |
| ATOM | 25859 | OE2 | GLU | C | 403 | -5.471 | 67.705 | 38.336 | 1.00 | 40.29 | O |
| ATOM | 25860 | C | GLU | C | 403 | -7.639 | 70.789 | 34.938 | 1.00 | 27.06 | C |
| ATOM | 25861 | O | GLU | C | 403 | -8.823 | 70.910 | 35.236 | 1.00 | 28.11 | O |
| ATOM | 25863 | N | ASN | C | 404 | -7.078 | 71.404 | 33.907 | 1.00 | 25.88 | N |
| ATOM | 25864 | CA | ASN | C | 404 | -7.802 | 72.364 | 33.088 | 1.00 | 24.92 | C |
| ATOM | 25866 | CB | ASN | C | 404 | -6.973 | 73.627 | 32.902 | 1.00 | 25.45 | C |
| ATOM | 25869 | CG | ASN | C | 404 | -6.801 | 74.376 | 34.205 | 1.00 | 26.55 | C |
| ATOM | 25870 | OD1 | ASN | C | 404 | -7.786 | 74.855 | 34.776 | 1.00 | 31.23 | O |
| ATOM | 25871 | ND2 | ASN | C | 404 | -5.573 | 74.430 | 34.723 | 1.00 | 23.20 | N |
| ATOM | 25874 | C | ASN | C | 404 | -8.221 | 71.794 | 31.753 | 1.00 | 24.13 | C |
| ATOM | 25875 | O | ASN | C | 404 | -8.631 | 72.539 | 30.860 | 1.00 | 24.04 | O |
| ATOM | 25877 | N | LYS | C | 405 | -8.131 | 70.466 | 31.631 | 1.00 | 22.75 | N |
| ATOM | 25878 | CA | LYS | C | 405 | -8.584 | 69.748 | 30.463 | 1.00 | 22.19 | C |
| ATOM | 25880 | CB | LYS | C | 405 | -10.116 | 69.585 | 30.518 | 1.00 | 21.77 | C |
| ATOM | 25883 | CG | LYS | C | 405 | -10.517 | 68.663 | 31.637 | 1.00 | 24.02 | C |
| ATOM | 25886 | CD | LYS | C | 405 | -12.025 | 68.501 | 31.709 | 1.00 | 25.31 | C |
| ATOM | 25889 | CE | LYS | C | 405 | -12.718 | 69.831 | 32.049 | 1.00 | 30.95 | C |
| ATOM | 25892 | NZ | LYS | C | 405 | -12.107 | 70.518 | 33.249 | 1.00 | 34.66 | N |
| ATOM | 25896 | C | LYS | C | 405 | -8.138 | 70.401 | 29.177 | 1.00 | 21.39 | C |
| ATOM | 25897 | O | LYS | C | 405 | -8.932 | 70.739 | 28.297 | 1.00 | 19.87 | O |
| ATOM | 25899 | N | THR | C | 406 | -6.826 | 70.581 | 29.060 | 1.00 | 20.33 | N |
| ATOM | 25900 | CA | THR | C | 406 | -6.305 | 71.198 | 27.887 | 1.00 | 21.12 | C |
| ATOM | 25902 | CB | THR | C | 406 | -6.362 | 72.751 | 28.037 | 1.00 | 21.30 | C |
| ATOM | 25904 | OG1 | THR | C | 406 | -6.091 | 73.374 | 26.778 | 1.00 | 25.21 | O |
| ATOM | 25906 | CG2 | THR | C | 406 | -5.385 | 73.244 | 29.114 | 1.00 | 22.75 | C |
| ATOM | 25910 | C | THR | C | 406 | -4.907 | 70.648 | 27.609 | 1.00 | 20.20 | C |
| ATOM | 25911 | O | THR | C | 406 | -4.336 | 69.911 | 28.427 | 1.00 | 19.48 | O |
| ATOM | 25913 | N | SER | C | 407 | -4.426 | 70.928 | 26.411 | 1.00 | 18.97 | N |
| ATOM | 25914 | CA | SER | C | 407 | -3.070 | 70.589 | 26.023 | 1.00 | 18.84 | C |
| ATOM | 25916 | CB | SER | C | 407 | -3.013 | 69.501 | 24.974 | 1.00 | 19.52 | C |
| ATOM | 25919 | OG | SER | C | 407 | -4.052 | 69.695 | 24.078 | 1.00 | 23.03 | O |
| ATOM | 25921 | C | SER | C | 407 | -2.412 | 71.835 | 25.478 | 1.00 | 17.33 | C |
| ATOM | 25922 | O | SER | C | 407 | -3.081 | 72.774 | 25.063 | 1.00 | 16.46 | O |
| ATOM | 25924 | N | HIS | C | 408 | -1.089 | 71.811 | 25.493 | 1.00 | 15.16 | N |
| ATOM | 25925 | CA | HIS | C | 408 | -0.308 | 72.995 | 25.218 | 1.00 | 14.44 | C |
| ATOM | 25927 | CB | HIS | C | 408 | 0.259 | 73.556 | 26.523 | 1.00 | 14.23 | C |
| ATOM | 25930 | CG | HIS | C | 408 | -0.770 | 74.137 | 27.430 | 1.00 | 14.09 | C |
| ATOM | 25931 | ND1 | HIS | C | 408 | -1.196 | 75.446 | 27.331 | 1.00 | 14.89 | N |
| ATOM | 25933 | CE1 | HIS | C | 408 | -2.104 | 75.682 | 28.266 | 1.00 | 14.96 | C |
| ATOM | 25935 | NE2 | HIS | C | 408 | -2.280 | 74.575 | 28.967 | 1.00 | 14.56 | N |
| ATOM | 25937 | CD2 | HIS | C | 408 | -1.463 | 73.591 | 28.462 | 1.00 | 15.63 | C |
| ATOM | 25939 | C | HIS | C | 408 | 0.825 | 72.620 | 24.307 | 1.00 | 14.36 | C |
| ATOM | 25940 | O | HIS | C | 408 | 1.472 | 71.581 | 24.502 | 1.00 | 12.87 | O |
| ATOM | 25942 | N | HIS | C | 409 | 1.081 | 73.502 | 23.331 | 1.00 | 13.37 | N |
| ATOM | 25943 | CA | HIS | C | 409 | 2.119 | 73.298 | 22.335 | 1.00 | 13.45 | C |
| ATOM | 25945 | CB | HIS | C | 409 | 1.544 | 73.529 | 20.939 | 1.00 | 13.29 | C |
| ATOM | 25948 | CG | HIS | C | 409 | 0.545 | 72.487 | 20.578 | 1.00 | 17.07 | C |

| ATOM | 25949 | ND1 | HIS | C | 409 | 0.912 | 71.265 | 20.057 | 1.00 | 19.40 | N |
|------|-------|-----|-----|---|-----|-------|--------|--------|------|-------|---|
| ATOM | 25951 | CE1 | HIS | C | 409 | -0.176 | 70.528 | 19.873 | 1.00 | 20.92 | C |
| ATOM | 25953 | NE2 | HIS | C | 409 | -1.224 | 71.210 | 20.310 | 1.00 | 22.22 | N |
| ATOM | 25955 | CD2 | HIS | C | 409 | -0.796 | 72.435 | 20.766 | 1.00 | 21.07 | C |
| ATOM | 25957 | C | HIS | C | 409 | 3.302 | 74.215 | 22.609 | 1.00 | 12.57 | C |
| ATOM | 25958 | O | HIS | C | 409 | 3.237 | 75.390 | 22.398 | 1.00 | 12.82 | O |
| ATOM | 25960 | N | GLY | C | 410 | 4.369 | 73.632 | 23.124 | 1.00 | 12.17 | N |
| ATOM | 25961 | CA | GLY | C | 410 | 5.540 | 74.410 | 23.541 | 1.00 | 11.58 | C |
| ATOM | 25964 | C | GLY | C | 410 | 6.884 | 73.927 | 23.040 | 1.00 | 12.42 | C |
| ATOM | 25965 | O | GLY | C | 410 | 6.999 | 73.313 | 21.994 | 1.00 | 11.72 | O |
| ATOM | 25967 | N | GLY | C | 411 | 7.914 | 74.213 | 23.824 | 1.00 | 13.00 | N |
| ATOM | 25968 | CA | GLY | C | 411 | 9.277 | 74.010 | 23.390 | 1.00 | 12.76 | C |
| ATOM | 25971 | C | GLY | C | 411 | 10.233 | 73.521 | 24.446 | 1.00 | 11.77 | C |
| ATOM | 25972 | O | GLY | C | 411 | 11.425 | 73.803 | 24.373 | 1.00 | 11.35 | O |
| ATOM | 25974 | N | ASN | C | 412 | 9.745 | 72.746 | 25.401 | 1.00 | 12.42 | N |
| ATOM | 25975 | CA | ASN | C | 412 | 10.601 | 72.278 | 26.525 | 1.00 | 12.56 | C |
| ATOM | 25977 | CB | ASN | C | 412 | 9.771 | 71.846 | 27.743 | 1.00 | 11.22 | C |
| ATOM | 25980 | CG | ASN | C | 412 | 9.148 | 73.017 | 28.461 | 1.00 | 13.63 | C |
| ATOM | 25981 | OD1 | ASN | C | 412 | 9.649 | 74.129 | 28.341 | 1.00 | 12.19 | O |
| ATOM | 25982 | ND2 | ASN | C | 412 | 8.038 | 72.789 | 29.188 | 1.00 | 14.01 | N |
| ATOM | 25985 | C | ASN | C | 412 | 11.659 | 71.245 | 26.183 | 1.00 | 12.30 | C |
| ATOM | 25986 | O | ASN | C | 412 | 12.493 | 70.887 | 27.039 | 1.00 | 13.43 | O |
| ATOM | 25988 | N | PHE | C | 413 | 11.661 | 70.791 | 24.919 | 1.00 | 11.86 | N |
| ATOM | 25989 | CA | PHE | C | 413 | 12.681 | 69.865 | 24.410 | 1.00 | 10.75 | C |
| ATOM | 25991 | CB | PHE | C | 413 | 12.058 | 69.050 | 23.259 | 1.00 | 11.32 | C |
| ATOM | 25994 | CG | PHE | C | 413 | 11.331 | 69.896 | 22.272 | 1.00 | 9.65 | C |
| ATOM | 25995 | CD1 | PHE | C | 413 | 12.040 | 70.769 | 21.465 | 1.00 | 13.04 | C |
| ATOM | 25997 | CE1 | PHE | C | 413 | 11.439 | 71.589 | 20.590 | 1.00 | 11.79 | C |
| ATOM | 25999 | CZ | PHE | C | 413 | 10.056 | 71.583 | 20.481 | 1.00 | 11.88 | C |
| ATOM | 26001 | CE2 | PHE | C | 413 | 9.324 | 70.692 | 21.280 | 1.00 | 14.91 | C |
| ATOM | 26003 | CD2 | PHE | C | 413 | 9.968 | 69.887 | 22.190 | 1.00 | 12.40 | C |
| ATOM | 26005 | C | PHE | C | 413 | 13.955 | 70.622 | 23.927 | 1.00 | 10.75 | C |
| ATOM | 26006 | O | PHE | C | 413 | 14.949 | 70.018 | 23.540 | 1.00 | 11.32 | O |
| ATOM | 26008 | N | GLN | C | 414 | 13.879 | 71.937 | 23.934 | 1.00 | 11.20 | N |
| ATOM | 26009 | CA | GLN | C | 414 | 14.973 | 72.769 | 23.454 | 1.00 | 11.13 | C |
| ATOM | 26011 | CB | GLN | C | 414 | 14.477 | 74.182 | 23.107 | 1.00 | 11.56 | C |
| ATOM | 26014 | CG | GLN | C | 414 | 15.537 | 75.112 | 22.582 | 1.00 | 10.97 | C |
| ATOM | 26017 | CD | GLN | C | 414 | 16.049 | 74.699 | 21.207 | 1.00 | 13.67 | C |
| ATOM | 26018 | OE1 | GLN | C | 414 | 16.978 | 73.845 | 21.099 | 1.00 | 13.82 | O |
| ATOM | 26019 | NE2 | GLN | C | 414 | 15.415 | 75.231 | 20.140 | 1.00 | 13.49 | N |
| ATOM | 26022 | C | GLN | C | 414 | 16.038 | 72.811 | 24.556 | 1.00 | 11.52 | C |
| ATOM | 26023 | O | GLN | C | 414 | 15.875 | 73.579 | 25.498 | 1.00 | 13.05 | O |
| ATOM | 26025 | N | ALA | C | 415 | 17.097 | 71.994 | 24.444 | 1.00 | 12.84 | N |
| ATOM | 26026 | CA | ALA | C | 415 | 18.049 | 71.780 | 25.580 | 1.00 | 11.85 | C |
| ATOM | 26028 | CB | ALA | C | 415 | 18.733 | 70.449 | 25.440 | 1.00 | 11.41 | C |
| ATOM | 26032 | C | ALA | C | 415 | 19.088 | 72.914 | 25.730 | 1.00 | 12.58 | C |
| ATOM | 26033 | O | ALA | C | 415 | 20.223 | 72.644 | 26.112 | 1.00 | 13.28 | O |
| ATOM | 26035 | N | ALA | C | 416 | 18.723 | 74.168 | 25.502 | 1.00 | 11.96 | N |
| ATOM | 26036 | CA | ALA | C | 416 | 19.689 | 75.260 | 25.616 | 1.00 | 12.58 | C |
| ATOM | 26038 | CB | ALA | C | 416 | 19.124 | 76.518 | 25.071 | 1.00 | 12.78 | C |
| ATOM | 26042 | C | ALA | C | 416 | 20.181 | 75.431 | 27.064 | 1.00 | 12.11 | C |
| ATOM | 26043 | O | ALA | C | 416 | 21.347 | 75.715 | 27.291 | 1.00 | 13.24 | O |
| ATOM | 26045 | N | ALA | C | 417 | 19.335 | 75.143 | 28.030 | 1.00 | 12.09 | N |
| ATOM | 26046 | CA | ALA | C | 417 | 19.776 | 75.196 | 29.450 | 1.00 | 12.58 | C |
| ATOM | 26048 | CB | ALA | C | 417 | 18.650 | 74.864 | 30.349 | 1.00 | 14.03 | C |
| ATOM | 26052 | C | ALA | C | 417 | 20.934 | 74.220 | 29.662 | 1.00 | 13.84 | C |
| ATOM | 26053 | O | ALA | C | 417 | 21.909 | 74.527 | 30.321 | 1.00 | 13.44 | O |

| ATOM | 26055 | N | VAL | C | 418 | 20.843 | 73.044 | 29.068 | 1.00 | 12.09 | N |
|------|-------|------|-----|---|-----|--------|--------|--------|------|-------|----|
| ATOM | 26056 | CA | VAL | C | 418 | 21.906 | 72.038 | 29.202 | 1.00 | 12.83 | C |
| ATOM | 26058 | CB | VAL | C | 418 | 21.492 | 70.653 | 28.697 | 1.00 | 12.63 | C |
| ATOM | 26060 | CG1 | VAL | C | 418 | 22.633 | 69.580 | 28.855 | 1.00 | 14.16 | C |
| ATOM | 26064 | CG2 | VAL | C | 418 | 20.279 | 70.177 | 29.451 | 1.00 | 13.75 | C |
| ATOM | 26068 | C | VAL | C | 418 | 23.158 | 72.486 | 28.475 | 1.00 | 12.11 | C |
| ATOM | 26069 | O | VAL | C | 418 | 24.250 | 72.398 | 29.002 | 1.00 | 12.62 | O |
| ATOM | 26071 | N | ALA | C | 419 | 22.964 | 72.948 | 27.231 | 1.00 | 12.24 | N |
| ATOM | 26072 | CA | ALA | C | 419 | 24.102 | 73.350 | 26.406 | 1.00 | 12.28 | C |
| ATOM | 26074 | CB | ALA | C | 419 | 23.694 | 73.802 | 25.066 | 1.00 | 13.31 | C |
| ATOM | 26078 | C | ALA | C | 419 | 24.865 | 74.471 | 27.126 | 1.00 | 13.44 | C |
| ATOM | 26079 | O | ALA | C | 419 | 26.096 | 74.455 | 27.177 | 1.00 | 12.63 | O |
| ATOM | 26081 | N | ASN | C | 420 | 24.123 | 75.385 | 27.726 | 1.00 | 13.87 | N |
| ATOM | 26082 | CA | ASN | C | 420 | 24.699 | 76.532 | 28.417 | 1.00 | 15.34 | C |
| ATOM | 26084 | CB | ASN | C | 420 | 23.537 | 77.359 | 29.012 | 1.00 | 16.71 | C |
| ATOM | 26087 | CG | ASN | C | 420 | 23.979 | 78.465 | 29.940 | 1.00 | 21.42 | C |
| ATOM | 26088 | OD1 | ASN | C | 420 | 24.103 | 78.261 | 31.169 | 1.00 | 23.33 | O |
| ATOM | 26089 | ND2 | ASN | C | 420 | 24.158 | 79.654 | 29.375 | 1.00 | 23.33 | N |
| ATOM | 26092 | C | ASN | C | 420 | 25.655 | 76.054 | 29.498 | 1.00 | 13.19 | C |
| ATOM | 26093 | O | ASN | C | 420 | 26.789 | 76.546 | 29.612 | 1.00 | 15.10 | O |
| ATOM | 26095 | N | THR | C | 421 | 25.223 | 75.079 | 30.294 | 1.00 | 12.12 | N |
| ATOM | 26096 | CA | THR | C | 421 | 26.076 | 74.558 | 31.378 | 1.00 | 12.57 | C |
| ATOM | 26098 | CB | THR | C | 421 | 25.371 | 73.492 | 32.262 | 1.00 | 12.04 | C |
| ATOM | 26100 | OG1 | THR | C | 421 | 25.213 | 72.265 | 31.536 | 1.00 | 12.91 | O |
| ATOM | 26102 | CG2 | THR | C | 421 | 24.042 | 73.999 | 32.784 | 1.00 | 13.94 | C |
| ATOM | 26106 | C | THR | C | 421 | 27.343 | 73.946 | 30.801 | 1.00 | 12.41 | C |
| ATOM | 26107 | O | THR | C | 421 | 28.429 | 74.059 | 31.387 | 1.00 | 13.35 | O |
| ATOM | 26109 | N | MSE | C | 422 | 27.247 | 73.302 | 29.638 | 1.00 | 10.53 | N |
| ATOM | 26110 | CA | MSE | C | 422 | 28.395 | 72.598 | 29.053 | 1.00 | 12.20 | C |
| ATOM | 26112 | CB | MSE | C | 422 | 27.986 | 71.524 | 28.060 | 1.00 | 12.28 | C |
| ATOM | 26115 | CG | MSE | C | 422 | 27.195 | 70.376 | 28.723 | 1.00 | 12.38 | C |
| ATOM | 26118 | SE | MSE | C | 422 | 28.410 | 69.385 | 29.960 | 1.00 | 21.28 | SE |
| ATOM | 26119 | CE | MSE | C | 422 | 28.075 | 70.292 | 31.628 | 1.00 | 16.26 | C |
| ATOM | 26123 | C | MSE | C | 422 | 29.389 | 73.526 | 28.418 | 1.00 | 13.24 | C |
| ATOM | 26124 | O | MSE | C | 422 | 30.597 | 73.318 | 28.538 | 1.00 | 13.23 | O |
| ATOM | 26126 | N | GLU | C | 423 | 28.881 | 74.563 | 27.761 | 1.00 | 13.20 | N |
| ATOM | 26127 | CA | GLU | C | 423 | 29.773 | 75.589 | 27.150 | 1.00 | 13.26 | C |
| ATOM | 26129 | CB | GLU | C | 423 | 28.967 | 76.647 | 26.416 | 1.00 | 14.73 | C |
| ATOM | 26132 | CG | GLU | C | 423 | 28.123 | 76.101 | 25.284 | 1.00 | 13.48 | C |
| ATOM | 26135 | CD | GLU | C | 423 | 28.899 | 75.785 | 24.044 | 1.00 | 12.54 | C |
| ATOM | 26136 | OE1 | GLU | C | 423 | 28.954 | 76.696 | 23.144 | 1.00 | 17.03 | O |
| ATOM | 26137 | OE2 | GLU | C | 423 | 29.384 | 74.666 | 23.898 | 1.00 | 15.83 | O |
| ATOM | 26138 | C | GLU | C | 423 | 30.644 | 76.262 | 28.240 | 1.00 | 14.57 | C |
| ATOM | 26139 | O | GLU | C | 423 | 31.876 | 76.329 | 28.116 | 1.00 | 14.85 | O |
| ATOM | 26141 | N | LYS | C | 424 | 29.996 | 76.717 | 29.321 | 1.00 | 14.86 | N |
| ATOM | 26142 | CA | LYS | C | 424 | 30.725 | 77.442 | 30.385 | 1.00 | 15.98 | C |
| ATOM | 26144 | CB | LYS | C | 424 | 29.816 | 78.172 | 31.367 | 1.00 | 17.90 | C |
| ATOM | 26147 | CG | LYS | C | 424 | 28.831 | 77.386 | 32.065 | 1.00 | 23.24 | C |
| ATOM | 26150 | CD | LYS | C | 424 | 28.119 | 78.226 | 33.210 | 1.00 | 23.38 | C |
| ATOM | 26153 | CE | LYS | C | 424 | 27.353 | 79.390 | 32.566 | 1.00 | 26.98 | C |
| ATOM | 26156 | NZ | LYS | C | 424 | 26.348 | 79.891 | 33.513 | 1.00 | 27.16 | N |
| ATOM | 26160 | C | LYS | C | 424 | 31.636 | 76.467 | 31.127 | 1.00 | 14.03 | C |
| ATOM | 26161 | O | LYS | C | 424 | 32.728 | 76.861 | 31.539 | 1.00 | 14.85 | O |
| ATOM | 26163 | N | THR | C | 425 | 31.168 | 75.256 | 31.414 | 1.00 | 13.15 | N |
| ATOM | 26164 | CA | THR | C | 425 | 32.024 | 74.312 | 32.111 | 1.00 | 12.41 | C |
| ATOM | 26166 | CB | THR | C | 425 | 31.288 | 73.007 | 32.404 | 1.00 | 12.36 | C |
| ATOM | 26168 | OG1 | THR | C | 425 | 30.173 | 73.305 | 33.254 | 1.00 | 13.06 | O |

| | | | | | | | | | |
|---|---|---|---|---|---|---|---|---|---|
| ATOM | 26170 | CG2 | THR | C | 425 | 32.171 | 71.966 | 33.109 | 1.00 14.33 | C |
| ATOM | 26174 | C | THR | C | 425 | 33.281 | 74.026 | 31.293 | 1.00 12.51 | C |
| ATOM | 26175 | O | THR | C | 425 | 34.398 | 73.919 | 31.826 | 1.00 13.01 | O |
| ATOM | 26177 | N | ARG | C | 426 | 33.128 | 73.923 | 29.972 | 1.00 11.53 | N |
| ATOM | 26178 | CA | ARG | C | 426 | 34.291 | 73.575 | 29.156 | 1.00 12.99 | C |
| ATOM | 26180 | CB | ARG | C | 426 | 33.901 | 73.214 | 27.718 | 1.00 13.49 | C |
| ATOM | 26183 | CG | ARG | C | 426 | 34.974 | 72.451 | 26.969 | 1.00 13.53 | C |
| ATOM | 26186 | CD | ARG | C | 426 | 34.408 | 71.785 | 25.699 | 1.00 12.92 | C |
| ATOM | 26189 | NE | ARG | C | 426 | 33.821 | 72.736 | 24.749 | 1.00 12.43 | N |
| ATOM | 26191 | CZ | ARG | C | 426 | 32.516 | 72.957 | 24.603 | 1.00 13.17 | C |
| ATOM | 26192 | NH1 | ARG | C | 426 | 31.617 | 72.320 | 25.352 | 1.00 14.12 | N |
| ATOM | 26195 | NH2 | ARG | C | 426 | 32.060 | 73.828 | 23.721 | 1.00 12.94 | N |
| ATOM | 26198 | C | ARG | C | 426 | 35.326 | 74.673 | 29.167 | 1.00 13.28 | C |
| ATOM | 26199 | O | ARG | C | 426 | 36.536 | 74.391 | 29.164 | 1.00 13.66 | O |
| ATOM | 26201 | N | LEU | C | 427 | 34.872 | 75.928 | 29.115 | 1.00 12.23 | N |
| ATOM | 26202 | CA | LEU | C | 427 | 35.791 | 77.057 | 29.236 | 1.00 13.63 | C |
| ATOM | 26204 | CB | LEU | C | 427 | 35.055 | 78.380 | 28.988 | 1.00 13.24 | C |
| ATOM | 26207 | CG | LEU | C | 427 | 35.898 | 79.632 | 29.026 | 1.00 15.38 | C |
| ATOM | 26209 | CD1 | LEU | C | 427 | 37.123 | 79.559 | 28.140 | 1.00 16.37 | C |
| ATOM | 26213 | CD2 | LEU | C | 427 | 35.012 | 80.802 | 28.637 | 1.00 16.72 | C |
| ATOM | 26217 | C | LEU | C | 427 | 36.454 | 77.059 | 30.620 | 1.00 12.67 | C |
| ATOM | 26218 | O | LEU | C | 427 | 37.669 | 77.257 | 30.754 | 1.00 15.07 | O |
| ATOM | 26220 | N | GLY | C | 428 | 35.662 | 76.763 | 31.648 | 1.00 13.45 | N |
| ATOM | 26221 | CA | GLY | C | 428 | 36.198 | 76.671 | 33.016 | 1.00 12.99 | C |
| ATOM | 26224 | C | GLY | C | 428 | 37.300 | 75.644 | 33.146 | 1.00 13.53 | C |
| ATOM | 26225 | O | GLY | C | 428 | 38.317 | 75.861 | 33.788 | 1.00 13.30 | O |
| ATOM | 26227 | N | LEU | C | 429 | 37.114 | 74.516 | 32.495 | 1.00 12.20 | N |
| ATOM | 26228 | CA | LEU | C | 429 | 38.106 | 73.403 | 32.547 | 1.00 12.33 | C |
| ATOM | 26230 | CB | LEU | C | 429 | 37.574 | 72.115 | 31.892 | 1.00 13.52 | C |
| ATOM | 26233 | CG | LEU | C | 429 | 36.388 | 71.431 | 32.606 | 1.00 10.95 | C |
| ATOM | 26235 | CD1 | LEU | C | 429 | 35.773 | 70.423 | 31.624 | 1.00 10.86 | C |
| ATOM | 26239 | CD2 | LEU | C | 429 | 36.879 | 70.793 | 33.852 | 1.00 13.41 | C |
| ATOM | 26243 | C | LEU | C | 429 | 39.397 | 73.863 | 31.906 | 1.00 12.37 | C |
| ATOM | 26244 | O | LEU | C | 429 | 40.489 | 73.535 | 32.381 | 1.00 12.33 | O |
| ATOM | 26246 | N | ALA | C | 430 | 39.309 | 74.645 | 30.833 | 1.00 12.37 | N |
| ATOM | 26247 | CA | ALA | C | 430 | 40.535 | 75.126 | 30.188 | 1.00 12.47 | C |
| ATOM | 26249 | CB | ALA | C | 430 | 40.206 | 75.756 | 28.821 | 1.00 14.51 | C |
| ATOM | 26253 | C | ALA | C | 430 | 41.216 | 76.153 | 31.132 | 1.00 13.08 | C |
| ATOM | 26254 | O | ALA | C | 430 | 42.434 | 76.236 | 31.172 | 1.00 13.04 | O |
| ATOM | 26256 | N | GLN | C | 431 | 40.431 | 76.950 | 31.861 | 1.00 12.74 | N |
| ATOM | 26257 | CA | GLN | C | 431 | 40.996 | 77.932 | 32.799 | 1.00 13.64 | C |
| ATOM | 26259 | CB | GLN | C | 431 | 39.912 | 78.878 | 33.282 | 1.00 14.63 | C |
| ATOM | 26262 | CG | GLN | C | 431 | 39.319 | 79.747 | 32.194 | 1.00 19.10 | C |
| ATOM | 26265 | CD | GLN | C | 431 | 40.356 | 80.370 | 31.309 | 1.00 25.69 | C |
| ATOM | 26266 | OE1 | GLN | C | 431 | 40.574 | 79.919 | 30.159 | 1.00 33.16 | O |
| ATOM | 26267 | NE2 | GLN | C | 431 | 40.980 | 81.437 | 31.794 | 1.00 25.44 | N |
| ATOM | 26270 | C | GLN | C | 431 | 41.727 | 77.231 | 33.989 | 1.00 12.87 | C |
| ATOM | 26271 | O | GLN | C | 431 | 42.798 | 77.663 | 34.411 | 1.00 12.72 | O |
| ATOM | 26273 | N | ILE | C | 432 | 41.063 | 76.237 | 34.577 | 1.00 13.13 | N |
| ATOM | 26274 | CA | ILE | C | 432 | 41.704 | 75.353 | 35.561 | 1.00 13.21 | C |
| ATOM | 26276 | CB | ILE | C | 432 | 40.814 | 74.196 | 36.007 | 1.00 12.36 | C |
| ATOM | 26278 | CG1 | ILE | C | 432 | 39.586 | 74.728 | 36.758 | 1.00 14.35 | C |
| ATOM | 26281 | CD1 | ILE | C | 432 | 38.468 | 73.689 | 36.971 | 1.00 15.08 | C |
| ATOM | 26285 | CG2 | ILE | C | 432 | 41.608 | 73.241 | 36.880 | 1.00 11.65 | C |
| ATOM | 26289 | C | ILE | C | 432 | 42.997 | 74.806 | 35.003 | 1.00 11.78 | C |
| ATOM | 26290 | O | ILE | C | 432 | 44.078 | 74.934 | 35.644 | 1.00 13.46 | O |
| ATOM | 26292 | N | GLY | C | 433 | 42.931 | 74.163 | 33.834 | 1.00 11.41 | N |

| | | | | | | | | | |
|---|---|---|---|---|---|---|---|---|---|
| ATOM | 26293 | CA | GLY C 433 | 44.124 | 73.586 | 33.187 | 1.00 | 12.42 | C |
| ATOM | 26296 | C | GLY C 433 | 45.252 | 74.612 | 33.050 | 1.00 | 12.29 | C |
| ATOM | 26297 | O | GLY C 433 | 46.383 | 74.337 | 33.420 | 1.00 | 12.66 | O |
| ATOM | 26299 | N | LYS C 434 | 44.969 | 75.790 | 32.512 | 1.00 | 12.08 | N |
| ATOM | 26300 | CA | LYS C 434 | 45.983 | 76.837 | 32.397 | 1.00 | 13.94 | C |
| ATOM | 26302 | CB | LYS C 434 | 45.398 | 78.065 | 31.758 | 1.00 | 14.19 | C |
| ATOM | 26305 | CG | LYS C 434 | 46.399 | 79.170 | 31.537 | 1.00 | 12.74 | C |
| ATOM | 26308 | CD | LYS C 434 | 47.494 | 78.805 | 30.544 | 1.00 | 14.72 | C |
| ATOM | 26311 | CE | LYS C 434 | 48.383 | 79.965 | 30.253 | 1.00 | 15.05 | C |
| ATOM | 26314 | NZ | LYS C 434 | 49.466 | 79.888 | 29.162 | 1.00 | 16.23 | N |
| ATOM | 26318 | C | LYS C 434 | 46.616 | 77.129 | 33.770 | 1.00 | 12.87 | C |
| ATOM | 26319 | O | LYS C 434 | 47.842 | 77.265 | 33.875 | 1.00 | 12.41 | O |
| ATOM | 26321 | N | LEU C 435 | 45.805 | 77.191 | 34.806 | 1.00 | 12.70 | N |
| ATOM | 26322 | CA | LEU C 435 | 46.342 | 77.561 | 36.112 | 1.00 | 13.26 | C |
| ATOM | 26324 | CB | LEU C 435 | 45.221 | 77.728 | 37.151 | 1.00 | 13.30 | C |
| ATOM | 26327 | CG | LEU C 435 | 45.785 | 78.113 | 38.528 | 1.00 | 13.33 | C |
| ATOM | 26329 | CD1 | LEU C 435 | 46.372 | 79.526 | 38.503 | 1.00 | 14.15 | C |
| ATOM | 26333 | CD2 | LEU C 435 | 44.724 | 77.952 | 39.587 | 1.00 | 13.37 | C |
| ATOM | 26337 | C | LEU C 435 | 47.321 | 76.491 | 36.567 | 1.00 | 11.83 | C |
| ATOM | 26338 | O | LEU C 435 | 48.459 | 76.730 | 36.943 | 1.00 | 12.17 | O |
| ATOM | 26340 | N | ASN C 436 | 46.845 | 75.263 | 36.623 | 1.00 | 11.73 | N |
| ATOM | 26341 | CA | ASN C 436 | 47.736 | 74.213 | 37.143 | 1.00 | 13.84 | C |
| ATOM | 26343 | CB | ASN C 436 | 46.951 | 72.933 | 37.365 | 1.00 | 14.65 | C |
| ATOM | 26346 | CG | ASN C 436 | 45.931 | 73.077 | 38.479 | 1.00 | 17.73 | C |
| ATOM | 26347 | OD1 | ASN C 436 | 44.755 | 73.170 | 38.239 | 1.00 | 18.62 | O |
| ATOM | 26348 | ND2 | ASN C 436 | 46.400 | 73.065 | 39.723 | 1.00 | 21.52 | N |
| ATOM | 26351 | C | ASN C 436 | 48.954 | 74.014 | 36.246 | 1.00 | 13.66 | C |
| ATOM | 26352 | O | ASN C 436 | 50.070 | 73.744 | 36.719 | 1.00 | 13.16 | O |
| ATOM | 26354 | N | PHE C 437 | 48.789 | 74.159 | 34.927 | 1.00 | 13.05 | N |
| ATOM | 26355 | CA | PHE C 437 | 49.931 | 74.084 | 34.027 | 1.00 | 14.08 | C |
| ATOM | 26357 | CB | PHE C 437 | 49.540 | 74.278 | 32.576 | 1.00 | 15.14 | C |
| ATOM | 26360 | CG | PHE C 437 | 50.707 | 74.572 | 31.688 | 1.00 | 13.26 | C |
| ATOM | 26361 | CD1 | PHE C 437 | 51.609 | 73.560 | 31.385 | 1.00 | 17.00 | C |
| ATOM | 26363 | CE1 | PHE C 437 | 52.764 | 73.838 | 30.608 | 1.00 | 15.79 | C |
| ATOM | 26365 | CZ | PHE C 437 | 52.986 | 75.139 | 30.158 | 1.00 | 16.63 | C |
| ATOM | 26367 | CE2 | PHE C 437 | 52.092 | 76.169 | 30.490 | 1.00 | 16.49 | C |
| ATOM | 26369 | CD2 | PHE C 437 | 50.972 | 75.880 | 31.278 | 1.00 | 15.86 | C |
| ATOM | 26371 | C | PHE C 437 | 50.966 | 75.136 | 34.457 | 1.00 | 13.20 | C |
| ATOM | 26372 | O | PHE C 437 | 52.161 | 74.833 | 34.600 | 1.00 | 12.94 | O |
| ATOM | 26374 | N | THR C 438 | 50.548 | 76.402 | 34.636 | 1.00 | 12.12 | N |
| ATOM | 26375 | CA | THR C 438 | 51.515 | 77.459 | 35.014 | 1.00 | 12.64 | C |
| ATOM | 26377 | CB | THR C 438 | 50.912 | 78.880 | 34.968 | 1.00 | 14.33 | C |
| ATOM | 26379 | OG1 | THR C 438 | 49.889 | 79.000 | 35.933 | 1.00 | 13.20 | O |
| ATOM | 26381 | CG2 | THR C 438 | 50.385 | 79.209 | 33.549 | 1.00 | 13.77 | C |
| ATOM | 26385 | C | THR C 438 | 52.189 | 77.146 | 36.360 | 1.00 | 12.45 | C |
| ATOM | 26386 | O | THR C 438 | 53.373 | 77.425 | 36.513 | 1.00 | 12.85 | O |
| ATOM | 26388 | N | GLN C 439 | 51.445 | 76.612 | 37.321 | 1.00 | 12.09 | N |
| ATOM | 26389 | CA | GLN C 439 | 52.010 | 76.234 | 38.627 | 1.00 | 12.90 | C |
| ATOM | 26391 | CB | GLN C 439 | 50.924 | 75.689 | 39.542 | 1.00 | 13.50 | C |
| ATOM | 26394 | CG | GLN C 439 | 49.889 | 76.702 | 39.988 | 1.00 | 15.80 | C |
| ATOM | 26397 | CD | GLN C 439 | 48.747 | 76.126 | 40.780 | 1.00 | 13.40 | C |
| ATOM | 26398 | OE1 | GLN C 439 | 48.613 | 74.926 | 40.864 | 1.00 | 15.10 | O |
| ATOM | 26399 | NE2 | GLN C 439 | 47.897 | 76.996 | 41.368 | 1.00 | 12.05 | N |
| ATOM | 26402 | C | GLN C 439 | 53.069 | 75.159 | 38.440 | 1.00 | 12.31 | C |
| ATOM | 26403 | O | GLN C 439 | 54.177 | 75.229 | 38.942 | 1.00 | 12.99 | O |
| ATOM | 26405 | N | LEU C 440 | 52.701 | 74.140 | 37.703 | 1.00 | 13.19 | N |
| ATOM | 26406 | CA | LEU C 440 | 53.583 | 73.010 | 37.491 | 1.00 | 13.61 | C |

| ATOM | 26408 | CB | LEU | C | 440 | 52.845 | 71.922 | 36.673 | 1.00 | 13.22 | C |
| ATOM | 26411 | CG | LEU | C | 440 | 53.679 | 70.731 | 36.200 | 1.00 | 13.65 | C |
| ATOM | 26413 | CD1 | LEU | C | 440 | 54.251 | 69.981 | 37.389 | 1.00 | 13.55 | C |
| ATOM | 26417 | CD2 | LEU | C | 440 | 52.823 | 69.772 | 35.392 | 1.00 | 14.70 | C |
| ATOM | 26421 | C | LEU | C | 440 | 54.846 | 73.414 | 36.736 | 1.00 | 12.80 | C |
| ATOM | 26422 | O | LEU | C | 440 | 55.962 | 73.022 | 37.084 | 1.00 | 13.01 | O |
| ATOM | 26424 | N | THR | C | 441 | 54.695 | 74.144 | 35.634 | 1.00 | 12.73 | N |
| ATOM | 26425 | CA | THR | C | 441 | 55.859 | 74.460 | 34.806 | 1.00 | 13.53 | C |
| ATOM | 26427 | CB | THR | C | 441 | 55.441 | 74.956 | 33.399 | 1.00 | 14.53 | C |
| ATOM | 26429 | OG1 | THR | C | 441 | 56.559 | 74.770 | 32.496 | 1.00 | 15.26 | O |
| ATOM | 26431 | CG2 | THR | C | 441 | 54.967 | 76.408 | 33.428 | 1.00 | 16.41 | C |
| ATOM | 26435 | C | THR | C | 441 | 56.832 | 75.432 | 35.518 | 1.00 | 13.59 | C |
| ATOM | 26436 | O | THR | C | 441 | 58.049 | 75.380 | 35.322 | 1.00 | 16.06 | O |
| ATOM | 26438 | N | GLU | C | 442 | 56.308 | 76.268 | 36.386 | 1.00 | 13.56 | N |
| ATOM | 26439 | CA | GLU | C | 442 | 57.139 | 77.081 | 37.254 | 1.00 | 15.41 | C |
| ATOM | 26441 | CB | GLU | C | 442 | 56.286 | 78.083 | 38.013 | 1.00 | 15.68 | C |
| ATOM | 26444 | CG | GLU | C | 442 | 57.038 | 78.832 | 39.103 | 1.00 | 17.64 | C |
| ATOM | 26447 | CD | GLU | C | 442 | 56.184 | 79.874 | 39.812 | 1.00 | 20.05 | C |
| ATOM | 26448 | OE1 | GLU | C | 442 | 55.049 | 80.157 | 39.341 | 1.00 | 20.82 | O |
| ATOM | 26449 | OE2 | GLU | C | 442 | 56.707 | 80.500 | 40.765 | 1.00 | 20.30 | O |
| ATOM | 26450 | C | GLU | C | 442 | 57.944 | 76.178 | 38.206 | 1.00 | 15.62 | C |
| ATOM | 26451 | O | GLU | C | 442 | 59.173 | 76.303 | 38.344 | 1.00 | 15.66 | O |
| ATOM | 26453 | N | MSE | C | 443 | 57.264 | 75.216 | 38.818 | 1.00 | 15.24 | N |
| ATOM | 26454 | CA | MSE | C | 443 | 57.933 | 74.299 | 39.761 | 1.00 | 16.08 | C |
| ATOM | 26456 | CB | MSE | C | 443 | 56.886 | 73.412 | 40.443 | 1.00 | 15.88 | C |
| ATOM | 26459 | CG | MSE | C | 443 | 57.471 | 72.482 | 41.436 | 1.00 | 17.89 | C |
| ATOM | 26462 | SE | MSE | C | 443 | 55.985 | 71.574 | 42.380 | 1.00 | 25.06 | SE |
| ATOM | 26463 | CE | MSE | C | 443 | 55.288 | 70.560 | 40.871 | 1.00 | 21.81 | C |
| ATOM | 26467 | C | MSE | C | 443 | 58.998 | 73.435 | 39.071 | 1.00 | 15.94 | C |
| ATOM | 26468 | O | MSE | C | 443 | 59.979 | 73.010 | 39.715 | 1.00 | 16.44 | O |
| ATOM | 26470 | N | LEU | C | 444 | 58.802 | 73.152 | 37.773 | 1.00 | 14.92 | N |
| ATOM | 26471 | CA | LEU | C | 444 | 59.780 | 72.389 | 37.018 | 1.00 | 15.42 | C |
| ATOM | 26473 | CB | LEU | C | 444 | 59.093 | 71.520 | 35.959 | 1.00 | 15.66 | C |
| ATOM | 26476 | CG | LEU | C | 444 | 58.059 | 70.523 | 36.504 | 1.00 | 14.46 | C |
| ATOM | 26478 | CD1 | LEU | C | 444 | 57.345 | 69.786 | 35.350 | 1.00 | 14.16 | C |
| ATOM | 26482 | CD2 | LEU | C | 444 | 58.624 | 69.490 | 37.512 | 1.00 | 15.03 | C |
| ATOM | 26486 | C | LEU | C | 444 | 60.894 | 73.181 | 36.379 | 1.00 | 17.51 | C |
| ATOM | 26487 | O | LEU | C | 444 | 61.706 | 72.583 | 35.612 | 1.00 | 19.76 | O |
| ATOM | 26489 | N | ASN | C | 445 | 60.902 | 74.490 | 36.610 | 1.00 | 16.68 | N |
| ATOM | 26490 | CA | ASN | C | 445 | 61.894 | 75.396 | 36.028 | 1.00 | 16.84 | C |
| ATOM | 26492 | CB | ASN | C | 445 | 61.206 | 76.629 | 35.487 | 1.00 | 17.38 | C |
| ATOM | 26495 | CG | ASN | C | 445 | 62.151 | 77.557 | 34.760 | 1.00 | 17.71 | C |
| ATOM | 26496 | OD1 | ASN | C | 445 | 63.290 | 77.734 | 35.183 | 1.00 | 18.79 | O |
| ATOM | 26497 | ND2 | ASN | C | 445 | 61.677 | 78.207 | 33.704 | 1.00 | 14.77 | N |
| ATOM | 26500 | C | ASN | C | 445 | 62.944 | 75.718 | 37.098 | 1.00 | 15.85 | C |
| ATOM | 26501 | O | ASN | C | 445 | 62.652 | 76.409 | 38.089 | 1.00 | 15.41 | O |
| ATOM | 26503 | N | ALA | C | 446 | 64.152 | 75.154 | 36.908 | 1.00 | 16.22 | N |
| ATOM | 26504 | CA | ALA | C | 446 | 65.237 | 75.275 | 37.860 | 1.00 | 15.40 | C |
| ATOM | 26506 | CB | ALA | C | 446 | 66.550 | 74.548 | 37.318 | 1.00 | 16.93 | C |
| ATOM | 26510 | C | ALA | C | 446 | 65.562 | 76.741 | 38.210 | 1.00 | 15.47 | C |
| ATOM | 26511 | O | ALA | C | 446 | 66.038 | 77.001 | 39.299 | 1.00 | 15.48 | O |
| ATOM | 26513 | N | GLY | C | 447 | 65.310 | 77.673 | 37.293 | 1.00 | 15.26 | N |
| ATOM | 26514 | CA | GLY | C | 447 | 65.551 | 79.084 | 37.540 | 1.00 | 17.29 | C |
| ATOM | 26517 | C | GLY | C | 447 | 64.509 | 79.747 | 38.393 | 1.00 | 18.02 | C |
| ATOM | 26518 | O | GLY | C | 447 | 64.756 | 80.838 | 38.947 | 1.00 | 20.51 | O |
| ATOM | 26520 | N | MSE | C | 448 | 63.341 | 79.111 | 38.528 | 1.00 | 17.13 | N |
| ATOM | 26521 | CA | MSE | C | 448 | 62.201 | 79.721 | 39.184 | 1.00 | 18.55 | C |

| ATOM | 26523 | CB | MSE | C | 448 | 61.016 | 79.763 | 38.183 | 1.00 | 17.95 | C |
|------|-------|-----|-----|---|-----|--------|--------|--------|------|-------|---|
| ATOM | 26526 | CG | MSE | C | 448 | 61.333 | 80.523 | 36.931 | 1.00 | 20.27 | C |
| ATOM | 26529 | SE | MSE | C | 448 | 59.749 | 80.345 | 35.715 | 1.00 | 28.57 | SE |
| ATOM | 26530 | CE | MSE | C | 448 | 58.540 | 81.636 | 36.649 | 1.00 | 17.76 | C |
| ATOM | 26534 | C | MSE | C | 448 | 61.742 | 79.013 | 40.448 | 1.00 | 16.82 | C |
| ATOM | 26535 | O | MSE | C | 448 | 60.919 | 79.552 | 41.194 | 1.00 | 16.72 | O |
| ATOM | 26537 | N | ASN | C | 449 | 62.292 | 77.828 | 40.717 | 1.00 | 16.54 | N |
| ATOM | 26538 | CA | ASN | C | 449 | 61.665 | 76.896 | 41.684 | 1.00 | 15.53 | C |
| ATOM | 26540 | CB | ASN | C | 449 | 61.499 | 75.519 | 41.049 | 1.00 | 15.51 | C |
| ATOM | 26543 | CG | ASN | C | 449 | 62.819 | 74.840 | 40.815 | 1.00 | 14.21 | C |
| ATOM | 26544 | OD1 | ASN | C | 449 | 63.851 | 75.428 | 41.165 | 1.00 | 15.09 | O |
| ATOM | 26545 | ND2 | ASN | C | 449 | 62.828 | 73.655 | 40.161 | 1.00 | 13.62 | N |
| ATOM | 26548 | C | ASN | C | 449 | 62.297 | 76.846 | 43.087 | 1.00 | 16.35 | C |
| ATOM | 26549 | O | ASN | C | 449 | 62.139 | 75.886 | 43.848 | 1.00 | 15.00 | O |
| ATOM | 26551 | N | ARG | C | 450 | 63.032 | 77.892 | 43.429 | 1.00 | 16.75 | N |
| ATOM | 26552 | CA | ARG | C | 450 | 63.589 | 78.070 | 44.771 | 1.00 | 18.26 | C |
| ATOM | 26554 | CB | ARG | C | 450 | 62.463 | 78.213 | 45.805 | 1.00 | 19.86 | C |
| ATOM | 26557 | CG | ARG | C | 450 | 61.706 | 79.505 | 45.713 | 1.00 | 27.39 | C |
| ATOM | 26560 | CD | ARG | C | 450 | 62.091 | 80.396 | 46.919 | 1.00 | 38.38 | C |
| ATOM | 26563 | NE | ARG | C | 450 | 60.942 | 80.608 | 47.818 | 1.00 | 42.98 | N |
| ATOM | 26565 | CZ | ARG | C | 450 | 60.007 | 81.546 | 47.632 | 1.00 | 44.49 | C |
| ATOM | 26566 | NH1 | ARG | C | 450 | 60.074 | 82.382 | 46.605 | 1.00 | 46.75 | N |
| ATOM | 26569 | NH2 | ARG | C | 450 | 59.007 | 81.681 | 48.489 | 1.00 | 45.51 | N |
| ATOM | 26572 | C | ARG | C | 450 | 64.464 | 76.910 | 45.171 | 1.00 | 16.57 | C |
| ATOM | 26573 | O | ARG | C | 450 | 64.432 | 76.477 | 46.309 | 1.00 | 18.16 | O |
| ATOM | 26575 | N | GLY | C | 451 | 65.230 | 76.421 | 44.221 | 1.00 | 15.35 | N |
| ATOM | 26576 | CA | GLY | C | 451 | 66.343 | 75.542 | 44.527 | 1.00 | 15.96 | C |
| ATOM | 26579 | C | GLY | C | 451 | 65.990 | 74.071 | 44.481 | 1.00 | 15.29 | C |
| ATOM | 26580 | O | GLY | C | 451 | 66.789 | 73.255 | 44.944 | 1.00 | 17.08 | O |
| ATOM | 26582 | N | LEU | C | 452 | 64.795 | 73.735 | 43.982 | 1.00 | 16.10 | N |
| ATOM | 26583 | CA | LEU | C | 452 | 64.469 | 72.311 | 43.706 | 1.00 | 14.14 | C |
| ATOM | 26585 | CB | LEU | C | 452 | 63.012 | 72.114 | 43.313 | 1.00 | 15.68 | C |
| ATOM | 26588 | CG | LEU | C | 452 | 61.971 | 72.263 | 44.412 | 1.00 | 15.14 | C |
| ATOM | 26590 | CD1 | LEU | C | 452 | 60.546 | 72.437 | 43.910 | 1.00 | 19.00 | C |
| ATOM | 26594 | CD2 | LEU | C | 452 | 62.032 | 71.063 | 45.327 | 1.00 | 17.12 | C |
| ATOM | 26598 | C | LEU | C | 452 | 65.386 | 71.739 | 42.609 | 1.00 | 15.59 | C |
| ATOM | 26599 | O | LEU | C | 452 | 65.759 | 72.448 | 41.659 | 1.00 | 14.91 | O |
| ATOM | 26601 | N | PRO | C | 453 | 65.762 | 70.448 | 42.746 | 1.00 | 15.69 | N |
| ATOM | 26602 | CA | PRO | C | 453 | 66.614 | 69.904 | 41.709 | 1.00 | 15.73 | C |
| ATOM | 26604 | CB | PRO | C | 453 | 66.719 | 68.414 | 42.070 | 1.00 | 16.40 | C |
| ATOM | 26607 | CG | PRO | C | 453 | 66.510 | 68.354 | 43.530 | 1.00 | 17.04 | C |
| ATOM | 26610 | CD | PRO | C | 453 | 65.482 | 69.435 | 43.789 | 1.00 | 16.50 | C |
| ATOM | 26613 | C | PRO | C | 453 | 66.043 | 70.054 | 40.302 | 1.00 | 15.85 | C |
| ATOM | 26614 | O | PRO | C | 453 | 64.833 | 69.938 | 40.102 | 1.00 | 14.87 | O |
| ATOM | 26615 | N | SER | C | 454 | 66.943 | 70.241 | 39.345 | 1.00 | 16.07 | N |
| ATOM | 26616 | CA | SER | C | 454 | 66.651 | 70.269 | 37.921 | 1.00 | 15.93 | C |
| ATOM | 26618 | CB | SER | C | 454 | 67.984 | 70.190 | 37.174 | 1.00 | 16.34 | C |
| ATOM | 26621 | OG | SER | C | 454 | 67.785 | 70.059 | 35.795 | 1.00 | 21.12 | O |
| ATOM | 26623 | C | SER | C | 454 | 65.775 | 69.104 | 37.543 | 1.00 | 15.65 | C |
| ATOM | 26624 | O | SER | C | 454 | 66.095 | 67.985 | 37.904 | 1.00 | 13.57 | O |
| ATOM | 26626 | N | CYS | C | 455 | 64.638 | 69.390 | 36.921 | 1.00 | 15.10 | N |
| ATOM | 26627 | CA | CYS | C | 455 | 63.705 | 68.362 | 36.425 | 1.00 | 15.07 | C |
| ATOM | 26629 | CB | CYS | C | 455 | 64.323 | 67.484 | 35.381 | 1.00 | 14.41 | C |
| ATOM | 26632 | SG | CYS | C | 455 | 64.926 | 68.377 | 33.956 | 1.00 | 21.53 | S |
| ATOM | 26634 | C | CYS | C | 455 | 63.147 | 67.491 | 37.534 | 1.00 | 13.19 | C |
| ATOM | 26635 | O | CYS | C | 455 | 62.595 | 66.422 | 37.268 | 1.00 | 14.84 | O |
| ATOM | 26637 | N | LEU | C | 456 | 63.298 | 67.920 | 38.797 | 1.00 | 13.01 | N |

| | | | | | | | | | |
|---|---|---|---|---|---|---|---|---|---|
| ATOM | 26638 | CA | LEU | C | 456 | 62.968 | 67.058 | 39.948 | 1.00 13.69 | C |
| ATOM | 26640 | CB | LEU | C | 456 | 61.448 | 66.918 | 40.129 | 1.00 13.43 | C |
| ATOM | 26643 | CG | LEU | C | 456 | 60.631 | 68.216 | 40.151 | 1.00 12.52 | C |
| ATOM | 26645 | CD1 | LEU | C | 456 | 59.146 | 67.880 | 40.418 | 1.00 16.87 | C |
| ATOM | 26649 | CD2 | LEU | C | 456 | 61.203 | 69.103 | 41.191 | 1.00 13.11 | C |
| ATOM | 26653 | C | LEU | C | 456 | 63.732 | 65.710 | 39.922 | 1.00 14.31 | C |
| ATOM | 26654 | O | LEU | C | 456 | 63.235 | 64.676 | 40.454 | 1.00 14.00 | O |
| ATOM | 26656 | N | ALA | C | 457 | 64.955 | 65.745 | 39.391 | 1.00 14.55 | N |
| ATOM | 26657 | CA | ALA | C | 457 | 65.878 | 64.601 | 39.474 | 1.00 14.89 | C |
| ATOM | 26659 | CB | ALA | C | 457 | 67.123 | 64.835 | 38.609 | 1.00 15.10 | C |
| ATOM | 26663 | C | ALA | C | 457 | 66.308 | 64.403 | 40.916 | 1.00 14.85 | C |
| ATOM | 26664 | O | ALA | C | 457 | 66.679 | 65.361 | 41.598 | 1.00 14.76 | O |
| ATOM | 26666 | N | ALA | C | 458 | 66.292 | 63.155 | 41.370 | 1.00 14.13 | N |
| ATOM | 26667 | CA | ALA | C | 458 | 66.714 | 62.862 | 42.726 | 1.00 12.95 | C |
| ATOM | 26669 | CB | ALA | C | 458 | 66.113 | 61.583 | 43.170 | 1.00 13.53 | C |
| ATOM | 26673 | C | ALA | C | 458 | 68.216 | 62.782 | 42.869 | 1.00 13.82 | C |
| ATOM | 26674 | O | ALA | C | 458 | 68.721 | 62.904 | 43.991 | 1.00 15.66 | O |
| ATOM | 26676 | N | GLU | C | 459 | 68.897 | 62.435 | 41.780 | 1.00 13.39 | N |
| ATOM | 26677 | CA | GLU | C | 459 | 70.334 | 62.244 | 41.780 | 1.00 14.09 | C |
| ATOM | 26679 | CB | GLU | C | 459 | 70.646 | 60.751 | 41.559 | 1.00 14.04 | C |
| ATOM | 26682 | CG | GLU | C | 459 | 70.145 | 59.878 | 42.697 | 1.00 15.28 | C |
| ATOM | 26685 | CD | GLU | C | 459 | 70.995 | 59.916 | 43.933 | 1.00 16.95 | C |
| ATOM | 26686 | OE1 | GLU | C | 459 | 72.185 | 60.320 | 43.851 | 1.00 14.77 | O |
| ATOM | 26687 | OE2 | GLU | C | 459 | 70.453 | 59.528 | 44.996 | 1.00 15.06 | O |
| ATOM | 26688 | C | GLU | C | 459 | 70.962 | 63.194 | 40.764 | 1.00 15.56 | C |
| ATOM | 26689 | O | GLU | C | 459 | 70.312 | 64.188 | 40.386 | 1.00 16.05 | O |
| ATOM | 26691 | N | ASP | C | 460 | 72.208 | 62.969 | 40.336 | 1.00 14.58 | N |
| ATOM | 26692 | CA | ASP | C | 460 | 72.862 | 63.946 | 39.463 | 1.00 15.10 | C |
| ATOM | 26694 | CB | ASP | C | 460 | 74.253 | 63.451 | 39.075 | 1.00 14.90 | C |
| ATOM | 26697 | CG | ASP | C | 460 | 75.351 | 63.852 | 40.079 | 1.00 17.46 | C |
| ATOM | 26698 | OD1 | ASP | C | 460 | 75.087 | 64.608 | 41.049 | 1.00 14.82 | O |
| ATOM | 26699 | OD2 | ASP | C | 460 | 76.514 | 63.411 | 39.851 | 1.00 15.72 | O |
| ATOM | 26700 | C | ASP | C | 460 | 72.068 | 64.265 | 38.199 | 1.00 14.71 | C |
| ATOM | 26701 | O | ASP | C | 460 | 71.682 | 63.375 | 37.464 | 1.00 12.85 | O |
| ATOM | 26703 | N | PRO | C | 461 | 71.753 | 65.552 | 37.982 | 1.00 14.39 | N |
| ATOM | 26704 | CA | PRO | C | 461 | 70.938 | 65.972 | 36.823 | 1.00 15.21 | C |
| ATOM | 26706 | CB | PRO | C | 461 | 70.745 | 67.459 | 37.063 | 1.00 15.11 | C |
| ATOM | 26709 | CG | PRO | C | 461 | 71.273 | 67.731 | 38.382 | 1.00 16.38 | C |
| ATOM | 26712 | CD | PRO | C | 461 | 72.051 | 66.668 | 38.891 | 1.00 14.47 | C |
| ATOM | 26715 | C | PRO | C | 461 | 71.596 | 65.754 | 35.452 | 1.00 14.98 | C |
| ATOM | 26716 | O | PRO | C | 461 | 70.893 | 65.659 | 34.448 | 1.00 16.92 | O |
| ATOM | 26717 | N | SER | C | 462 | 72.917 | 65.658 | 35.397 | 1.00 16.11 | N |
| ATOM | 26718 | CA | SER | C | 462 | 73.566 | 65.381 | 34.127 | 1.00 16.08 | C |
| ATOM | 26720 | CB | SER | C | 462 | 75.094 | 65.309 | 34.283 | 1.00 16.44 | C |
| ATOM | 26723 | OG | SER | C | 462 | 75.488 | 64.186 | 34.981 | 1.00 18.17 | O |
| ATOM | 26725 | C | SER | C | 462 | 73.026 | 64.107 | 33.446 | 1.00 15.99 | C |
| ATOM | 26726 | O | SER | C | 462 | 73.067 | 64.021 | 32.227 | 1.00 17.68 | O |
| ATOM | 26728 | N | LEU | C | 463 | 72.539 | 63.115 | 34.204 | 1.00 15.31 | N |
| ATOM | 26729 | CA | LEU | C | 463 | 72.064 | 61.864 | 33.623 | 1.00 16.17 | C |
| ATOM | 26731 | CB | LEU | C | 463 | 73.055 | 60.735 | 33.927 | 1.00 17.13 | C |
| ATOM | 26734 | CG | LEU | C | 463 | 74.389 | 60.788 | 33.116 | 1.00 18.61 | C |
| ATOM | 26736 | CD1 | LEU | C | 463 | 75.362 | 59.746 | 33.570 | 1.00 21.12 | C |
| ATOM | 26740 | CD2 | LEU | C | 463 | 74.146 | 60.612 | 31.632 | 1.00 20.33 | C |
| ATOM | 26744 | C | LEU | C | 463 | 70.651 | 61.528 | 34.107 | 1.00 13.91 | C |
| ATOM | 26745 | O | LEU | C | 463 | 70.256 | 60.364 | 34.154 | 1.00 13.77 | O |
| ATOM | 26747 | N | SER | C | 464 | 69.892 | 62.552 | 34.503 | 1.00 14.39 | N |
| ATOM | 26748 | CA | SER | C | 464 | 68.528 | 62.332 | 34.988 | 1.00 15.15 | C |

| ATOM | 26750 | CB | SER | C | 464 | 68.493 | 62.134 | 36.497 | 1.00 | 15.78 | C |
|------|-------|-----|-----|---|-----|--------|--------|--------|------|-------|---|
| ATOM | 26753 | OG | SER | C | 464 | 67.169 | 61.902 | 36.926 | 1.00 | 14.91 | O |
| ATOM | 26755 | C | SER | C | 464 | 67.703 | 63.581 | 34.678 | 1.00 | 15.36 | C |
| ATOM | 26756 | O | SER | C | 464 | 68.006 | 64.655 | 35.180 | 1.00 | 14.39 | O |
| ATOM | 26758 | N | TYR | C | 465 | 66.697 | 63.437 | 33.807 | 1.00 | 14.93 | N |
| ATOM | 26759 | CA | TYR | C | 465 | 65.842 | 64.557 | 33.366 | 1.00 | 16.67 | C |
| ATOM | 26761 | CB | TYR | C | 465 | 65.910 | 64.748 | 31.831 | 1.00 | 17.60 | C |
| ATOM | 26764 | CG | TYR | C | 465 | 67.307 | 64.561 | 31.336 | 1.00 | 21.02 | C |
| ATOM | 26765 | CD1 | TYR | C | 465 | 68.338 | 65.379 | 31.781 | 1.00 | 26.43 | C |
| ATOM | 26767 | CE1 | TYR | C | 465 | 69.671 | 65.121 | 31.398 | 1.00 | 23.63 | C |
| ATOM | 26769 | CZ | TYR | C | 465 | 69.935 | 64.064 | 30.569 | 1.00 | 23.48 | C |
| ATOM | 26770 | OH | TYR | C | 465 | 71.240 | 63.750 | 30.158 | 1.00 | 26.21 | O |
| ATOM | 26772 | CE2 | TYR | C | 465 | 68.912 | 63.243 | 30.117 | 1.00 | 25.37 | C |
| ATOM | 26774 | CD2 | TYR | C | 465 | 67.619 | 63.482 | 30.516 | 1.00 | 24.43 | C |
| ATOM | 26776 | C | TYR | C | 465 | 64.420 | 64.283 | 33.811 | 1.00 | 15.17 | C |
| ATOM | 26777 | O | TYR | C | 465 | 63.472 | 64.776 | 33.202 | 1.00 | 15.40 | O |
| ATOM | 26779 | N | HIS | C | 466 | 64.298 | 63.556 | 34.922 | 1.00 | 15.21 | N |
| ATOM | 26780 | CA | HIS | C | 466 | 63.043 | 63.031 | 35.475 | 1.00 | 14.09 | C |
| ATOM | 26782 | CB | HIS | C | 466 | 63.074 | 63.117 | 37.011 | 1.00 | 14.26 | C |
| ATOM | 26785 | CG | HIS | C | 466 | 61.927 | 62.419 | 37.678 | 1.00 | 12.96 | C |
| ATOM | 26786 | ND1 | HIS | C | 466 | 61.652 | 62.543 | 39.022 | 1.00 | 13.72 | N |
| ATOM | 26788 | CE1 | HIS | C | 466 | 60.538 | 61.868 | 39.301 | 1.00 | 13.07 | C |
| ATOM | 26790 | NE2 | HIS | C | 466 | 60.110 | 61.272 | 38.199 | 1.00 | 11.92 | N |
| ATOM | 26792 | CD2 | HIS | C | 466 | 60.949 | 61.622 | 37.160 | 1.00 | 12.22 | C |
| ATOM | 26794 | C | HIS | C | 466 | 61.761 | 63.599 | 34.862 | 1.00 | 15.31 | C |
| ATOM | 26795 | O | HIS | C | 466 | 61.146 | 62.906 | 34.065 | 1.00 | 14.58 | O |
| ATOM | 26797 | N | CYS | C | 467 | 61.348 | 64.781 | 35.308 | 1.00 | 13.96 | N |
| ATOM | 26798 | CA | CYS | C | 467 | 60.028 | 65.369 | 34.986 | 1.00 | 14.66 | C |
| ATOM | 26800 | CB | CYS | C | 467 | 59.424 | 66.096 | 36.222 | 1.00 | 14.94 | C |
| ATOM | 26803 | SG | CYS | C | 467 | 58.943 | 64.952 | 37.557 | 1.00 | 16.15 | S |
| ATOM | 26805 | C | CYS | C | 467 | 59.977 | 66.260 | 33.713 | 1.00 | 15.10 | C |
| ATOM | 26806 | O | CYS | C | 467 | 58.951 | 66.866 | 33.432 | 1.00 | 15.18 | O |
| ATOM | 26808 | N | LYS | C | 468 | 61.028 | 66.255 | 32.915 | 1.00 | 14.91 | N |
| ATOM | 26809 | CA | LYS | C | 468 | 61.087 | 67.147 | 31.739 | 1.00 | 14.65 | C |
| ATOM | 26811 | CB | LYS | C | 468 | 62.475 | 67.093 | 31.083 | 1.00 | 15.57 | C |
| ATOM | 26814 | CG | LYS | C | 468 | 62.622 | 67.896 | 29.815 | 1.00 | 17.91 | C |
| ATOM | 26817 | CD | LYS | C | 468 | 64.028 | 67.800 | 29.239 | 1.00 | 19.46 | C |
| ATOM | 26820 | CE | LYS | C | 468 | 65.058 | 68.537 | 30.061 | 1.00 | 24.05 | C |
| ATOM | 26823 | NZ | LYS | C | 468 | 64.741 | 70.017 | 30.214 | 1.00 | 28.09 | N |
| ATOM | 26827 | C | LYS | C | 468 | 60.026 | 66.715 | 30.708 | 1.00 | 13.65 | C |
| ATOM | 26828 | O | LYS | C | 468 | 59.327 | 67.575 | 30.123 | 1.00 | 13.38 | O |
| ATOM | 26830 | N | GLY | C | 469 | 59.861 | 65.415 | 30.510 | 1.00 | 12.88 | N |
| ATOM | 26831 | CA | GLY | C | 469 | 58.798 | 64.894 | 29.627 | 1.00 | 13.46 | C |
| ATOM | 26834 | C | GLY | C | 469 | 57.401 | 65.326 | 30.072 | 1.00 | 13.26 | C |
| ATOM | 26835 | O | GLY | C | 469 | 56.505 | 65.665 | 29.279 | 1.00 | 11.74 | O |
| ATOM | 26837 | N | LEU | C | 470 | 57.173 | 65.256 | 31.385 | 1.00 | 13.47 | N |
| ATOM | 26838 | CA | LEU | C | 470 | 55.877 | 65.668 | 31.931 | 1.00 | 13.94 | C |
| ATOM | 26840 | CB | LEU | C | 470 | 55.770 | 65.245 | 33.415 | 1.00 | 13.18 | C |
| ATOM | 26843 | CG | LEU | C | 470 | 55.649 | 63.721 | 33.661 | 1.00 | 12.83 | C |
| ATOM | 26845 | CD1 | LEU | C | 470 | 55.581 | 63.442 | 35.134 | 1.00 | 13.87 | C |
| ATOM | 26849 | CD2 | LEU | C | 470 | 54.424 | 63.098 | 32.925 | 1.00 | 14.60 | C |
| ATOM | 26853 | C | LEU | C | 470 | 55.626 | 67.152 | 31.796 | 1.00 | 13.84 | C |
| ATOM | 26854 | O | LEU | C | 470 | 54.471 | 67.577 | 31.634 | 1.00 | 13.17 | O |
| ATOM | 26856 | N | ASP | C | 471 | 56.673 | 67.960 | 31.893 | 1.00 | 15.08 | N |
| ATOM | 26857 | CA | ASP | C | 471 | 56.533 | 69.399 | 31.633 | 1.00 | 14.87 | C |
| ATOM | 26859 | CB | ASP | C | 471 | 57.909 | 70.062 | 31.751 | 1.00 | 15.83 | C |
| ATOM | 26862 | CG | ASP | C | 471 | 57.841 | 71.566 | 31.973 | 1.00 | 19.50 | C |

| ATOM | 26863 | OD1 | ASP | C | 471 | 56.781 | 72.094 | 32.402 | 1.00 | 19.25 | O |
|------|-------|-----|-----|---|-----|--------|--------|--------|------|-------|---|
| ATOM | 26864 | OD2 | ASP | C | 471 | 58.929 | 72.239 | 31.779 | 1.00 | 20.13 | O |
| ATOM | 26865 | C | ASP | C | 471 | 55.940 | 69.603 | 30.233 | 1.00 | 14.76 | C |
| ATOM | 26866 | O | ASP | C | 471 | 55.048 | 70.418 | 30.034 | 1.00 | 15.38 | O |
| ATOM | 26868 | N | ILE | C | 472 | 56.518 | 68.892 | 29.280 | 1.00 | 13.95 | N |
| ATOM | 26869 | CA | ILE | C | 472 | 56.120 | 68.949 | 27.873 | 1.00 | 12.42 | C |
| ATOM | 26871 | CB | ILE | C | 472 | 57.143 | 68.175 | 26.989 | 1.00 | 14.12 | C |
| ATOM | 26873 | CG1 | ILE | C | 472 | 58.468 | 68.929 | 26.974 | 1.00 | 12.94 | C |
| ATOM | 26876 | CD1 | ILE | C | 472 | 59.636 | 68.130 | 26.512 | 1.00 | 14.18 | C |
| ATOM | 26880 | CG2 | ILE | C | 472 | 56.594 | 67.949 | 25.574 | 1.00 | 14.17 | C |
| ATOM | 26884 | C | ILE | C | 472 | 54.688 | 68.439 | 27.731 | 1.00 | 12.38 | C |
| ATOM | 26885 | O | ILE | C | 472 | 53.855 | 69.065 | 27.072 | 1.00 | 13.44 | O |
| ATOM | 26887 | N | ALA | C | 473 | 54.400 | 67.288 | 28.340 | 1.00 | 13.10 | N |
| ATOM | 26888 | CA | ALA | C | 473 | 53.060 | 66.683 | 28.319 | 1.00 | 13.71 | C |
| ATOM | 26890 | CB | ALA | C | 473 | 53.042 | 65.390 | 29.150 | 1.00 | 15.06 | C |
| ATOM | 26894 | C | ALA | C | 473 | 52.028 | 67.637 | 28.853 | 1.00 | 13.92 | C |
| ATOM | 26895 | O | ALA | C | 473 | 50.923 | 67.752 | 28.289 | 1.00 | 14.64 | O |
| ATOM | 26897 | N | ALA | C | 474 | 52.381 | 68.331 | 29.952 | 1.00 | 14.39 | N |
| ATOM | 26898 | CA | ALA | C | 474 | 51.458 | 69.266 | 30.596 | 1.00 | 14.30 | C |
| ATOM | 26900 | CB | ALA | C | 474 | 52.070 | 69.864 | 31.876 | 1.00 | 15.66 | C |
| ATOM | 26904 | C | ALA | C | 474 | 51.111 | 70.391 | 29.607 | 1.00 | 14.19 | C |
| ATOM | 26905 | O | ALA | C | 474 | 49.974 | 70.798 | 29.516 | 1.00 | 13.03 | O |
| ATOM | 26907 | N | ALA | C | 475 | 52.098 | 70.880 | 28.867 | 1.00 | 12.45 | N |
| ATOM | 26908 | CA | ALA | C | 475 | 51.841 | 71.854 | 27.811 | 1.00 | 12.52 | C |
| ATOM | 26910 | CB | ALA | C | 475 | 53.126 | 72.272 | 27.172 | 1.00 | 12.69 | C |
| ATOM | 26914 | C | ALA | C | 475 | 50.859 | 71.318 | 26.761 | 1.00 | 11.23 | C |
| ATOM | 26915 | O | ALA | C | 475 | 49.906 | 72.013 | 26.357 | 1.00 | 12.71 | O |
| ATOM | 26917 | N | ALA | C | 476 | 51.116 | 70.104 | 26.282 | 1.00 | 12.86 | N |
| ATOM | 26918 | CA | ALA | C | 476 | 50.248 | 69.476 | 25.286 | 1.00 | 12.78 | C |
| ATOM | 26920 | CB | ALA | C | 476 | 50.789 | 68.124 | 24.913 | 1.00 | 13.58 | C |
| ATOM | 26924 | C | ALA | C | 476 | 48.792 | 69.362 | 25.774 | 1.00 | 12.92 | C |
| ATOM | 26925 | O | ALA | C | 476 | 47.846 | 69.664 | 25.037 | 1.00 | 14.28 | O |
| ATOM | 26927 | N | TYR | C | 477 | 48.624 | 68.961 | 27.019 | 1.00 | 11.96 | N |
| ATOM | 26928 | CA | TYR | C | 477 | 47.260 | 68.790 | 27.583 | 1.00 | 11.81 | C |
| ATOM | 26930 | CB | TYR | C | 477 | 47.281 | 68.127 | 28.943 | 1.00 | 12.11 | C |
| ATOM | 26933 | CG | TYR | C | 477 | 47.974 | 66.808 | 29.024 | 1.00 | 12.48 | C |
| ATOM | 26934 | CD1 | TYR | C | 477 | 47.923 | 65.862 | 27.985 | 1.00 | 12.56 | C |
| ATOM | 26936 | CE1 | TYR | C | 477 | 48.602 | 64.617 | 28.108 | 1.00 | 13.54 | C |
| ATOM | 26938 | CZ | TYR | C | 477 | 49.263 | 64.304 | 29.284 | 1.00 | 13.46 | C |
| ATOM | 26939 | OH | TYR | C | 477 | 49.873 | 63.099 | 29.355 | 1.00 | 14.44 | O |
| ATOM | 26941 | CE2 | TYR | C | 477 | 49.306 | 65.241 | 30.318 | 1.00 | 14.06 | C |
| ATOM | 26943 | CD2 | TYR | C | 477 | 48.649 | 66.446 | 30.187 | 1.00 | 12.26 | C |
| ATOM | 26945 | C | TYR | C | 477 | 46.589 | 70.141 | 27.606 | 1.00 | 11.86 | C |
| ATOM | 26946 | O | TYR | C | 477 | 45.430 | 70.268 | 27.211 | 1.00 | 13.95 | O |
| ATOM | 26948 | N | THR | C | 478 | 47.328 | 71.156 | 28.036 | 1.00 | 10.91 | N |
| ATOM | 26949 | CA | THR | C | 478 | 46.821 | 72.524 | 28.144 | 1.00 | 11.86 | C |
| ATOM | 26951 | CB | THR | C | 478 | 47.881 | 73.400 | 28.863 | 1.00 | 11.09 | C |
| ATOM | 26953 | OG1 | THR | C | 478 | 48.115 | 72.820 | 30.150 | 1.00 | 13.03 | O |
| ATOM | 26955 | CG2 | THR | C | 478 | 47.354 | 74.769 | 29.024 | 1.00 | 13.38 | C |
| ATOM | 26959 | C | THR | C | 478 | 46.405 | 73.082 | 26.775 | 1.00 | 12.29 | C |
| ATOM | 26960 | O | THR | C | 478 | 45.364 | 73.716 | 26.629 | 1.00 | 13.20 | O |
| ATOM | 26962 | N | SER | C | 479 | 47.253 | 72.882 | 25.770 | 1.00 | 13.64 | N |
| ATOM | 26963 | CA | SER | C | 479 | 46.940 | 73.331 | 24.422 | 1.00 | 12.54 | C |
| ATOM | 26965 | CB | SER | C | 479 | 48.053 | 72.937 | 23.483 | 1.00 | 13.78 | C |
| ATOM | 26968 | OG | SER | C | 479 | 49.236 | 73.636 | 23.785 | 1.00 | 12.58 | O |
| ATOM | 26970 | C | SER | C | 479 | 45.627 | 72.704 | 23.950 | 1.00 | 12.95 | C |
| ATOM | 26971 | O | SER | C | 479 | 44.762 | 73.345 | 23.370 | 1.00 | 12.21 | O |

| ATOM | 26973 | N   | GLU | C | 480 | 45.533 | 71.396 | 24.189 | 1.00 | 12.42 | N |
|------|-------|-----|-----|---|-----|--------|--------|--------|------|-------|---|
| ATOM | 26974 | CA  | GLU | C | 480 | 44.331 | 70.625 | 23.758 | 1.00 | 13.67 | C |
| ATOM | 26976 | CB  | GLU | C | 480 | 44.518 | 69.148 | 23.986 | 1.00 | 13.81 | C |
| ATOM | 26979 | CG  | GLU | C | 480 | 43.363 | 68.345 | 23.425 | 1.00 | 14.05 | C |
| ATOM | 26982 | CD  | GLU | C | 480 | 43.631 | 66.829 | 23.298 | 1.00 | 13.77 | C |
| ATOM | 26983 | OE1 | GLU | C | 480 | 44.822 | 66.378 | 23.320 | 1.00 | 14.50 | O |
| ATOM | 26984 | OE2 | GLU | C | 480 | 42.636 | 66.103 | 23.182 | 1.00 | 14.08 | O |
| ATOM | 26985 | C   | GLU | C | 480 | 43.065 | 71.154 | 24.425 | 1.00 | 13.41 | C |
| ATOM | 26986 | O   | GLU | C | 480 | 42.033 | 71.365 | 23.768 | 1.00 | 13.93 | O |
| ATOM | 26988 | N   | LEU | C | 481 | 43.136 | 71.451 | 25.730 | 1.00 | 12.89 | N |
| ATOM | 26989 | CA  | LEU | C | 481 | 42.016 | 72.081 | 26.436 | 1.00 | 13.34 | C |
| ATOM | 26991 | CB  | LEU | C | 481 | 42.344 | 72.317 | 27.894 | 1.00 | 13.67 | C |
| ATOM | 26994 | CG  | LEU | C | 481 | 42.361 | 71.073 | 28.751 | 1.00 | 13.87 | C |
| ATOM | 26996 | CD1 | LEU | C | 481 | 43.063 | 71.357 | 30.081 | 1.00 | 14.17 | C |
| ATOM | 27000 | CD2 | LEU | C | 481 | 41.003 | 70.428 | 28.912 | 1.00 | 14.26 | C |
| ATOM | 27004 | C   | LEU | C | 481 | 41.564 | 73.439 | 25.817 | 1.00 | 13.01 | C |
| ATOM | 27005 | O   | LEU | C | 481 | 40.367 | 73.781 | 25.820 | 1.00 | 12.65 | O |
| ATOM | 27007 | N   | GLY | C | 482 | 42.528 | 74.268 | 25.389 | 1.00 | 12.07 | N |
| ATOM | 27008 | CA  | GLY | C | 482 | 42.261 | 75.592 | 24.791 | 1.00 | 13.24 | C |
| ATOM | 27011 | C   | GLY | C | 482 | 41.383 | 75.417 | 23.583 | 1.00 | 13.79 | C |
| ATOM | 27012 | O   | GLY | C | 482 | 40.344 | 76.053 | 23.478 | 1.00 | 13.44 | O |
| ATOM | 27014 | N   | HIS | C | 483 | 41.787 | 74.543 | 22.657 | 1.00 | 13.03 | N |
| ATOM | 27015 | CA  | HIS | C | 483 | 41.005 | 74.372 | 21.459 | 1.00 | 12.25 | C |
| ATOM | 27017 | CB  | HIS | C | 483 | 41.779 | 73.499 | 20.455 | 1.00 | 13.64 | C |
| ATOM | 27020 | CG  | HIS | C | 483 | 40.970 | 73.065 | 19.289 | 1.00 | 14.90 | C |
| ATOM | 27021 | ND1 | HIS | C | 483 | 40.248 | 71.897 | 19.299 | 1.00 | 15.02 | N |
| ATOM | 27023 | CE1 | HIS | C | 483 | 39.628 | 71.757 | 18.143 | 1.00 | 15.77 | C |
| ATOM | 27025 | NE2 | HIS | C | 483 | 39.944 | 72.775 | 17.371 | 1.00 | 14.30 | N |
| ATOM | 27027 | CD2 | HIS | C | 483 | 40.776 | 73.622 | 18.063 | 1.00 | 14.61 | C |
| ATOM | 27029 | C   | HIS | C | 483 | 39.634 | 73.794 | 21.762 | 1.00 | 12.90 | C |
| ATOM | 27030 | O   | HIS | C | 483 | 38.628 | 74.176 | 21.174 | 1.00 | 12.82 | O |
| ATOM | 27032 | N   | LEU | C | 484 | 39.569 | 72.861 | 22.702 | 1.00 | 11.18 | N |
| ATOM | 27033 | CA  | LEU | C | 484 | 38.271 | 72.264 | 23.058 | 1.00 | 12.11 | C |
| ATOM | 27035 | CB  | LEU | C | 484 | 38.412 | 71.209 | 24.154 | 1.00 | 12.95 | C |
| ATOM | 27038 | CG  | LEU | C | 484 | 38.870 | 69.839 | 23.675 | 1.00 | 13.30 | C |
| ATOM | 27040 | CD1 | LEU | C | 484 | 39.527 | 68.993 | 24.747 | 1.00 | 13.58 | C |
| ATOM | 27044 | CD2 | LEU | C | 484 | 37.661 | 69.064 | 23.029 | 1.00 | 17.97 | C |
| ATOM | 27048 | C   | LEU | C | 484 | 37.284 | 73.301 | 23.534 | 1.00 | 10.76 | C |
| ATOM | 27049 | O   | LEU | C | 484 | 36.080 | 73.208 | 23.295 | 1.00 | 11.76 | O |
| ATOM | 27051 | N   | ALA | C | 485 | 37.804 | 74.337 | 24.198 | 1.00 | 11.45 | N |
| ATOM | 27052 | CA  | ALA | C | 485 | 36.969 | 75.315 | 24.932 | 1.00 | 11.68 | C |
| ATOM | 27054 | CB  | ALA | C | 485 | 37.821 | 76.112 | 25.909 | 1.00 | 13.79 | C |
| ATOM | 27058 | C   | ALA | C | 485 | 36.215 | 76.314 | 24.036 | 1.00 | 12.98 | C |
| ATOM | 27059 | O   | ALA | C | 485 | 35.342 | 77.040 | 24.503 | 1.00 | 14.78 | O |
| ATOM | 27061 | N   | ASN | C | 486 | 36.530 | 76.351 | 22.740 | 1.00 | 12.48 | N |
| ATOM | 27062 | CA  | ASN | C | 486 | 35.702 | 77.124 | 21.849 | 1.00 | 11.91 | C |
| ATOM | 27064 | CB  | ASN | C | 486 | 36.212 | 77.074 | 20.409 | 1.00 | 12.99 | C |
| ATOM | 27067 | CG  | ASN | C | 486 | 37.558 | 77.710 | 20.256 | 1.00 | 11.33 | C |
| ATOM | 27068 | OD1 | ASN | C | 486 | 37.751 | 78.864 | 20.712 | 1.00 | 13.19 | O |
| ATOM | 27069 | ND2 | ASN | C | 486 | 38.502 | 77.007 | 19.637 | 1.00 | 12.11 | N |
| ATOM | 27072 | C   | ASN | C | 486 | 34.237 | 76.602 | 21.899 | 1.00 | 12.08 | C |
| ATOM | 27073 | O   | ASN | C | 486 | 33.988 | 75.419 | 22.144 | 1.00 | 12.55 | O |
| ATOM | 27075 | N   | PRO | C | 487 | 33.263 | 77.528 | 21.700 | 1.00 | 12.59 | N |
| ATOM | 27076 | CA  | PRO | C | 487 | 31.863 | 77.127 | 21.809 | 1.00 | 13.43 | C |
| ATOM | 27078 | CB  | PRO | C | 487 | 31.100 | 78.439 | 21.776 | 1.00 | 13.11 | C |
| ATOM | 27081 | CG  | PRO | C | 487 | 32.027 | 79.388 | 21.044 | 1.00 | 13.35 | C |
| ATOM | 27084 | CD  | PRO | C | 487 | 33.406 | 78.972 | 21.521 | 1.00 | 13.31 | C |

| ATOM | 27087 | C | PRO | C | 487 | 31.412 | 76.235 | 20.656 | 1.00 | 13.20 | C |
| ATOM | 27088 | O | PRO | C | 487 | 31.802 | 76.464 | 19.507 | 1.00 | 13.54 | O |
| ATOM | 27089 | N | VAL | C | 488 | 30.547 | 75.283 | 20.973 | 1.00 | 12.91 | N |
| ATOM | 27090 | CA | VAL | C | 488 | 29.814 | 74.507 | 19.969 | 1.00 | 13.60 | C |
| ATOM | 27092 | CB | VAL | C | 488 | 29.454 | 73.105 | 20.608 | 1.00 | 13.98 | C |
| ATOM | 27094 | CG1 | VAL | C | 488 | 28.406 | 72.404 | 19.855 | 1.00 | 15.55 | C |
| ATOM | 27098 | CG2 | VAL | C | 488 | 30.740 | 72.227 | 20.731 | 1.00 | 13.13 | C |
| ATOM | 27102 | C | VAL | C | 488 | 28.555 | 75.247 | 19.506 | 1.00 | 13.21 | C |
| ATOM | 27103 | O | VAL | C | 488 | 28.086 | 75.111 | 18.353 | 1.00 | 12.16 | O |
| ATOM | 27105 | N | THR | C | 489 | 27.973 | 76.021 | 20.425 | 1.00 | 12.89 | N |
| ATOM | 27106 | CA | THR | C | 489 | 26.654 | 76.553 | 20.213 | 1.00 | 13.63 | C |
| ATOM | 27108 | CB | THR | C | 489 | 26.004 | 77.033 | 21.531 | 1.00 | 14.20 | C |
| ATOM | 27110 | OG1 | THR | C | 489 | 26.875 | 77.962 | 22.151 | 1.00 | 15.37 | O |
| ATOM | 27112 | CG2 | THR | C | 489 | 25.659 | 75.873 | 22.440 | 1.00 | 14.80 | C |
| ATOM | 27116 | C | THR | C | 489 | 26.551 | 77.668 | 19.177 | 1.00 | 12.52 | C |
| ATOM | 27117 | O | THR | C | 489 | 25.439 | 78.083 | 18.792 | 1.00 | 15.20 | O |
| ATOM | 27119 | N | THR | C | 490 | 27.699 | 78.180 | 18.696 | 1.00 | 12.29 | N |
| ATOM | 27120 | CA | THR | C | 490 | 27.707 | 79.108 | 17.578 | 1.00 | 14.04 | C |
| ATOM | 27122 | CB | THR | C | 490 | 28.929 | 79.955 | 17.660 | 1.00 | 14.28 | C |
| ATOM | 27124 | OG1 | THR | C | 490 | 30.058 | 79.092 | 17.754 | 1.00 | 14.39 | O |
| ATOM | 27126 | CG2 | THR | C | 490 | 28.813 | 80.865 | 18.900 | 1.00 | 16.34 | C |
| ATOM | 27130 | C | THR | C | 490 | 27.686 | 78.430 | 16.208 | 1.00 | 14.76 | C |
| ATOM | 27131 | O | THR | C | 490 | 27.751 | 79.118 | 15.178 | 1.00 | 16.97 | O |
| ATOM | 27133 | N | HIS | C | 491 | 27.517 | 77.121 | 16.197 | 1.00 | 12.34 | N |
| ATOM | 27134 | CA | HIS | C | 491 | 27.576 | 76.328 | 14.966 | 1.00 | 12.11 | C |
| ATOM | 27136 | CB | HIS | C | 491 | 28.691 | 75.253 | 15.043 | 1.00 | 13.46 | C |
| ATOM | 27139 | CG | HIS | C | 491 | 30.025 | 75.875 | 15.118 | 1.00 | 13.58 | C |
| ATOM | 27140 | ND1 | HIS | C | 491 | 30.603 | 76.467 | 14.016 | 1.00 | 15.85 | N |
| ATOM | 27142 | CE1 | HIS | C | 491 | 31.726 | 77.061 | 14.389 | 1.00 | 14.01 | C |
| ATOM | 27144 | NE2 | HIS | C | 491 | 31.846 | 76.956 | 15.695 | 1.00 | 14.23 | N |
| ATOM | 27146 | CD2 | HIS | C | 491 | 30.794 | 76.218 | 16.186 | 1.00 | 14.86 | C |
| ATOM | 27148 | C | HIS | C | 491 | 26.214 | 75.774 | 14.575 | 1.00 | 13.01 | C |
| ATOM | 27149 | O | HIS | C | 491 | 26.120 | 74.847 | 13.776 | 1.00 | 12.97 | O |
| ATOM | 27151 | N | VAL | C | 492 | 25.165 | 76.427 | 15.068 | 1.00 | 12.32 | N |
| ATOM | 27152 | CA | VAL | C | 492 | 23.798 | 76.011 | 14.785 | 1.00 | 13.41 | C |
| ATOM | 27154 | CB | VAL | C | 492 | 22.801 | 76.914 | 15.554 | 1.00 | 13.45 | C |
| ATOM | 27156 | CG1 | VAL | C | 492 | 21.340 | 76.519 | 15.231 | 1.00 | 16.11 | C |
| ATOM | 27160 | CG2 | VAL | C | 492 | 23.030 | 76.826 | 17.047 | -1.00 | 15.90 | C |
| ATOM | 27164 | C | VAL | C | 492 | 23.475 | 76.109 | 13.298 | 1.00 | 13.07 | C |
| ATOM | 27165 | O | VAL | C | 492 | 23.668 | 77.163 | 12.689 | 1.00 | 13.89 | O |
| ATOM | 27167 | N | GLN | C | 493 | 22.905 | 75.027 | 12.746 | 1.00 | 13.83 | N |
| ATOM | 27168 | CA | GLN | C | 493 | 22.481 | 74.953 | 11.347 | 1.00 | 13.59 | C |
| ATOM | 27170 | CB | GLN | C | 493 | 23.004 | 73.697 | 10.670 | 1.00 | 13.49 | C |
| ATOM | 27173 | CG | GLN | C | 493 | 24.511 | 73.465 | 10.739 | 1.00 | 13.76 | C |
| ATOM | 27176 | CD | GLN | C | 493 | 25.244 | 74.559 | 10.007 | 1.00 | 15.10 | C |
| ATOM | 27177 | OE1 | GLN | C | 493 | 24.860 | 74.864 | 8.881 | 1.00 | 14.68 | O |
| ATOM | 27178 | NE2 | GLN | C | 493 | 26.262 | 75.189 | 10.642 | 1.00 | 15.48 | N |
| ATOM | 27181 | C | GLN | C | 493 | 20.930 | 74.945 | 11.260 | 1.00 | 13.83 | C |
| ATOM | 27182 | O | GLN | C | 493 | 20.253 | 74.578 | 12.236 | 1.00 | 13.80 | O |
| ATOM | 27184 | N | PRO | C | 494 | 20.362 | 75.379 | 10.100 | 1.00 | 14.92 | N |
| ATOM | 27185 | CA | PRO | C | 494 | 18.901 | 75.484 | 9.876 | 1.00 | 15.48 | C |
| ATOM | 27187 | CB | PRO | C | 494 | 18.820 | 76.358 | 8.642 | 1.00 | 16.76 | C |
| ATOM | 27190 | CG | PRO | C | 494 | 20.043 | 76.054 | 7.882 | 1.00 | 17.08 | C |
| ATOM | 27193 | CD | PRO | C | 494 | 21.111 | 75.935 | 8.955 | 1.00 | 14.71 | C |
| ATOM | 27196 | C | PRO | C | 494 | 18.203 | 74.157 | 9.625 | 1.00 | 17.73 | C |
| ATOM | 27197 | O | PRO | C | 494 | 17.590 | 73.917 | 8.571 | 1.00 | 18.96 | O |
| ATOM | 27198 | N | ALA | C | 495 | 18.189 | 73.355 | 10.656 | 1.00 | 16.59 | N |

| ATOM | 27199 | CA | ALA | C | 495 | 17.773 | 71.971 | 10.574 | 1.00 | 16.41 | C |
|---|---|---|---|---|---|---|---|---|---|---|---|
| ATOM | 27201 | CB | ALA | C | 495 | 18.210 | 71.238 | 11.866 | 1.00 | 16.51 | C |
| ATOM | 27205 | C | ALA | C | 495 | 16.282 | 71.768 | 10.301 | 1.00 | 15.92 | C |
| ATOM | 27206 | O | ALA | C | 495 | 15.387 | 72.574 | 10.723 | 1.00 | 15.20 | O |
| ATOM | 27208 | N | GLU | C | 496 | 16.010 | 70.714 | 9.545 | 1.00 | 16.59 | N |
| ATOM | 27209 | CA | GLU | C | 496 | 14.653 | 70.220 | 9.316 | 1.00 | 18.48 | C |
| ATOM | 27211 | CB | GLU | C | 496 | 14.051 | 69.704 | 10.635 | 1.00 | 19.66 | C |
| ATOM | 27214 | CG | GLU | C | 496 | 12.931 | 68.658 | 10.398 | 1.00 | 23.17 | C |
| ATOM | 27217 | CD | GLU | C | 496 | 11.628 | 69.001 | 11.094 | 1.00 | 27.09 | C |
| ATOM | 27218 | OE1 | GLU | C | 496 | 11.616 | 69.360 | 12.317 | 1.00 | 26.30 | O |
| ATOM | 27219 | OE2 | GLU | C | 496 | 10.604 | 68.903 | 10.413 | 1.00 | 29.16 | O |
| ATOM | 27220 | C | GLU | C | 496 | 13.701 | 71.239 | 8.665 | 1.00 | 18.09 | C |
| ATOM | 27221 | O | GLU | C | 496 | 12.723 | 71.665 | 9.276 | 1.00 | 17.56 | O |
| ATOM | 27223 | N | MSE | C | 497 | 13.989 | 71.626 | 7.412 | 1.00 | 19.13 | N |
| ATOM | 27224 | CA | MSE | C | 497 | 13.212 | 72.620 | 6.689 | 1.00 | 20.80 | C |
| ATOM | 27226 | CB | MSE | C | 497 | 11.830 | 72.068 | 6.362 | 1.00 | 21.14 | C |
| ATOM | 27229 | CG | MSE | C | 497 | 11.949 | 70.841 | 5.588 | 1.00 | 22.56 | C |
| ATOM | 27232 | SE | MSE | C | 497 | 10.218 | 70.339 | 4.876 | 1.00 | 34.35 | SE |
| ATOM | 27233 | CE | MSE | C | 497 | 9.471 | 72.010 | 4.107 | 1.00 | 30.87 | C |
| ATOM | 27237 | C | MSE | C | 497 | 13.100 | 73.911 | 7.471 | 1.00 | 18.87 | C |
| ATOM | 27238 | O | MSE | C | 497 | 12.096 | 74.656 | 7.354 | 1.00 | 18.93 | O |
| ATOM | 27240 | N | ALA | C | 498 | 14.162 | 74.185 | 8.241 | 1.00 | 18.51 | N |
| ATOM | 27241 | CA | ALA | C | 498 | 14.212 | 75.344 | 9.132 | 1.00 | 17.96 | C |
| ATOM | 27243 | CB | ALA | C | 498 | 14.229 | 76.704 | 8.345 | 1.00 | 18.46 | C |
| ATOM | 27247 | C | ALA | C | 498 | 13.115 | 75.338 | 10.196 | 1.00 | 17.05 | C |
| ATOM | 27248 | O | ALA | C | 498 | 12.970 | 76.316 | 10.945 | 1.00 | 16.45 | O |
| ATOM | 27250 | N | ASN | C | 499 | 12.415 | 74.203 | 10.386 | 1.00 | 15.82 | N |
| ATOM | 27251 | CA | ASN | C | 499 | 11.537 | 74.086 | 11.545 | 1.00 | 15.80 | C |
| ATOM | 27253 | CB | ASN | C | 499 | 10.764 | 72.765 | 11.577 | 1.00 | 15.81 | C |
| ATOM | 27256 | CG | ASN | C | 499 | 9.834 | 72.678 | 12.792 | 1.00 | 19.04 | C |
| ATOM | 27257 | OD1 | ASN | C | 499 | 9.069 | 73.636 | 13.089 | 1.00 | 24.75 | O |
| ATOM | 27258 | ND2 | ASN | C | 499 | 9.869 | 71.515 | 13.518 | 1.00 | 23.76 | N |
| ATOM | 27261 | C | ASN | C | 499 | 12.379 | 74.194 | 12.808 | 1.00 | 14.47 | C |
| ATOM | 27262 | O | ASN | C | 499 | 12.002 | 74.886 | 13.757 | 1.00 | 15.83 | O |
| ATOM | 27264 | N | GLN | C | 500 | 13.547 | 73.528 | 12.770 | 1.00 | 13.34 | N |
| ATOM | 27265 | CA | GLN | C | 500 | 14.431 | 73.488 | 13.909 | 1.00 | 13.60 | C |
| ATOM | 27267 | CB | GLN | C | 500 | 14.924 | 72.072 | 14.206 | 1.00 | 13.39 | C |
| ATOM | 27270 | CG | GLN | C | 500 | 13.824 | 71.067 | 14.292 | 1.00 | 13.23 | C |
| ATOM | 27273 | CD | GLN | C | 500 | 14.191 | 69.741 | 14.958 | 1.00 | 15.37 | C |
| ATOM | 27274 | OE1 | GLN | C | 500 | 15.095 | 69.669 | 15.790 | 1.00 | 16.14 | O |
| ATOM | 27275 | NE2 | GLN | C | 500 | 13.402 | 68.705 | 14.655 | 1.00 | 18.67 | N |
| ATOM | 27278 | C | GLN | C | 500 | 15.601 | 74.458 | 13.682 | 1.00 | 14.37 | C |
| ATOM | 27279 | O | GLN | C | 500 | 16.756 | 74.115 | 13.916 | 1.00 | 14.83 | O |
| ATOM | 27281 | N | ALA | C | 501 | 15.273 | 75.680 | 13.253 | 1.00 | 13.83 | N |
| ATOM | 27282 | CA | ALA | C | 501 | 16.289 | 76.697 | 12.849 | 1.00 | 13.39 | C |
| ATOM | 27284 | CB | ALA | C | 501 | 15.609 | 77.904 | 12.222 | 1.00 | 16.26 | C |
| ATOM | 27288 | C | ALA | C | 501 | 17.188 | 77.127 | 13.996 | 1.00 | 14.25 | C |
| ATOM | 27289 | O | ALA | C | 501 | 18.310 | 77.601 | 13.747 | 1.00 | 14.39 | O |
| ATOM | 27291 | N | VAL | C | 502 | 16.668 | 77.053 | 15.230 | 1.00 | 11.99 | N |
| ATOM | 27292 | CA | VAL | C | 502 | 17.500 | 77.135 | 16.441 | 1.00 | 11.85 | C |
| ATOM | 27294 | CB | VAL | C | 502 | 17.113 | 78.277 | 17.414 | 1.00 | 12.26 | C |
| ATOM | 27296 | CG1 | VAL | C | 502 | 17.506 | 79.614 | 16.912 | 1.00 | 13.90 | C |
| ATOM | 27300 | CG2 | VAL | C | 502 | 15.632 | 78.284 | 17.701 | 1.00 | 12.54 | C |
| ATOM | 27304 | C | VAL | C | 502 | 17.451 | 75.760 | 17.108 | 1.00 | 11.73 | C |
| ATOM | 27305 | O | VAL | C | 502 | 16.371 | 75.172 | 17.236 | 1.00 | 11.74 | O |
| ATOM | 27307 | N | ASN | C | 503 | 18.623 | 75.231 | 17.448 | 1.00 | 11.34 | N |
| ATOM | 27308 | CA | ASN | C | 503 | 18.774 | 73.940 | 18.099 | 1.00 | 11.16 | C |

| ATOM | 27310 | CB | ASN | C | 503 | 18.876 | 72.790 | 17.078 | 1.00 | 11.80 | C |
|---|---|---|---|---|---|---|---|---|---|---|---|
| ATOM | 27313 | CG | ASN | C | 503 | 19.931 | 73.046 | 15.984 | 1.00 | 11.07 | C |
| ATOM | 27314 | OD1 | ASN | C | 503 | 21.110 | 72.776 | 16.211 | 1.00 | 12.73 | O |
| ATOM | 27315 | ND2 | ASN | C | 503 | 19.507 | 73.551 | 14.813 | 1.00 | 11.35 | N |
| ATOM | 27318 | C | ASN | C | 503 | 19.975 | 74.049 | 19.037 | 1.00 | 12.18 | C |
| ATOM | 27319 | O | ASN | C | 503 | 20.981 | 74.703 | 18.688 | 1.00 | 12.73 | O |
| ATOM | 27321 | N | SER | C | 504 | 19.892 | 73.393 | 20.181 | 1.00 | 12.34 | N |
| ATOM | 27322 | CA | SER | C | 504 | 20.778 | 73.707 | 21.286 | 1.00 | 12.16 | C |
| ATOM | 27324 | CB | SER | C | 504 | 20.173 | 73.189 | 22.615 | 1.00 | 13.25 | C |
| ATOM | 27327 | OG | SER | C | 504 | 20.302 | 71.801 | 22.718 | 1.00 | 11.50 | O |
| ATOM | 27329 | C | SER | C | 504 | 22.164 | 73.109 | 21.140 | 1.00 | 11.53 | C |
| ATOM | 27330 | O | SER | C | 504 | 23.096 | 73.628 | 21.747 | 1.00 | 14.23 | O |
| ATOM | 27332 | N | LEU | C | 505 | 22.289 | 71.992 | 20.418 | 1.00 | 11.49 | N |
| ATOM | 27333 | CA | LEU | C | 505 | 23.572 | 71.253 | 20.309 | 1.00 | 11.81 | C |
| ATOM | 27335 | CB | LEU | C | 505 | 24.645 | 72.022 | 19.491 | 1.00 | 11.79 | C |
| ATOM | 27338 | CG | LEU | C | 505 | 24.136 | 72.531 | 18.129 | 1.00 | 11.80 | C |
| ATOM | 27340 | CD1 | LEU | C | 505 | 25.168 | 73.472 | 17.535 | 1.00 | 13.78 | C |
| ATOM | 27344 | CD2 | LEU | C | 505 | 23.829 | 71.397 | 17.227 | 1.00 | 15.98 | C |
| ATOM | 27348 | C | LEU | C | 505 | 24.115 | 70.788 | 21.670 | 1.00 | 12.08 | C |
| ATOM | 27349 | O | LEU | C | 505 | 25.317 | 70.532 | 21.845 | 1.00 | 12.70 | O |
| ATOM | 27351 | N | ALA | C | 506 | 23.221 | 70.607 | 22.632 | 1.00 | 11.80 | N |
| ATOM | 27352 | CA | ALA | C | 506 | 23.653 | 70.251 | 23.995 | 1.00 | 12.21 | C |
| ATOM | 27354 | CB | ALA | C | 506 | 22.433 | 70.115 | 24.911 | 1.00 | 13.52 | C |
| ATOM | 27358 | C | ALA | C | 506 | 24.465 | 68.946 | 24.042 | 1.00 | 12.18 | C |
| ATOM | 27359 | O | ALA | C | 506 | 25.446 | 68.853 | 24.770 | 1.00 | 12.57 | O |
| ATOM | 27361 | N | LEU | C | 507 | 24.062 | 67.887 | 23.325 | 1.00 | 12.56 | N |
| ATOM | 27362 | CA | LEU | C | 507 | 24.798 | 66.645 | 23.490 | 1.00 | 12.70 | C |
| ATOM | 27364 | CB | LEU | C | 507 | 24.062 | 65.502 | 22.822 | 1.00 | 12.73 | C |
| ATOM | 27367 | CG | LEU | C | 507 | 24.711 | 64.120 | 23.056 | 1.00 | 12.68 | C |
| ATOM | 27369 | CD1 | LEU | C | 507 | 24.961 | 63.839 | 24.551 | 1.00 | 12.12 | C |
| ATOM | 27373 | CD2 | LEU | C | 507 | 23.955 | 63.041 | 22.385 | 1.00 | 14.56 | C |
| ATOM | 27377 | C | LEU | C | 507 | 26.215 | 66.780 | 22.926 | 1.00 | 12.22 | C |
| ATOM | 27378 | O | LEU | C | 507 | 27.178 | 66.279 | 23.507 | 1.00 | 12.10 | O |
| ATOM | 27380 | N | ILE | C | 508 | 26.330 | 67.454 | 21.786 | 1.00 | 11.80 | N |
| ATOM | 27381 | CA | ILE | C | 508 | 27.675 | 67.640 | 21.191 | 1.00 | 11.57 | C |
| ATOM | 27383 | CB | ILE | C | 508 | 27.624 | 68.363 | 19.843 | 1.00 | 12.53 | C |
| ATOM | 27385 | CG1 | ILE | C | 508 | 26.835 | 67.525 | 18.817 | 1.00 | 12.27 | C |
| ATOM | 27388 | CD1 | ILE | C | 508 | 26.391 | 68.288 | 17.579 | 1.00 | 14.25 | C |
| ATOM | 27392 | CG2 | ILE | C | 508 | 29.043 | 68.699 | 19.346 | 1.00 | 12.62 | C |
| ATOM | 27396 | C | ILE | C | 508 | 28.519 | 68.450 | 22.182 | 1.00 | 11.24 | C |
| ATOM | 27397 | O | ILE | C | 508 | 29.669 | 68.140 | 22.462 | 1.00 | 11.56 | O |
| ATOM | 27399 | N | SER | C | 509 | 27.919 | 69.482 | 22.741 | 1.00 | 11.98 | N |
| ATOM | 27400 | CA | SER | C | 509 | 28.663 | 70.279 | 23.734 | 1.00 | 12.28 | C |
| ATOM | 27402 | CB | SER | C | 509 | 27.865 | 71.459 | 24.177 | 1.00 | 12.53 | C |
| ATOM | 27405 | OG | SER | C | 509 | 28.667 | 72.361 | 24.925 | 1.00 | 13.09 | O |
| ATOM | 27407 | C | SER | C | 509 | 29.093 | 69.428 | 24.939 | 1.00 | 12.31 | C |
| ATOM | 27408 | O | SER | C | 509 | 30.241 | 69.471 | 25.404 | 1.00 | 12.46 | O |
| ATOM | 27410 | N | ALA | C | 510 | 28.145 | 68.658 | 25.443 | 1.00 | 10.90 | N |
| ATOM | 27411 | CA | ALA | C | 510 | 28.423 | 67.697 | 26.522 | 1.00 | 11.36 | C |
| ATOM | 27413 | CB | ALA | C | 510 | 27.189 | 66.987 | 26.924 | 1.00 | 11.13 | C |
| ATOM | 27417 | C | ALA | C | 510 | 29.547 | 66.711 | 26.210 | 1.00 | 10.97 | C |
| ATOM | 27418 | O | ALA | C | 510 | 30.386 | 66.381 | 27.080 | 1.00 | 14.07 | O |
| ATOM | 27420 | N | ARG | C | 511 | 29.584 | 66.213 | 24.971 | 1.00 | 11.56 | N |
| ATOM | 27421 | CA | ARG | C | 511 | 30.656 | 65.353 | 24.541 | 1.00 | 12.87 | C |
| ATOM | 27423 | CB | ARG | C | 511 | 30.422 | 64.793 | 23.149 | 1.00 | 12.05 | C |
| ATOM | 27426 | CG | ARG | C | 511 | 29.345 | 63.685 | 23.105 | 1.00 | 12.04 | C |
| ATOM | 27429 | CD | ARG | C | 511 | 28.939 | 63.322 | 21.690 | 1.00 | 11.85 | C |

| ATOM | 27432 | NE  | ARG | C | 511 | 30.180 | 63.210 | 20.892 | 1.00 | 12.86 | N |
|------|-------|-----|-----|---|-----|--------|--------|--------|------|-------|---|
| ATOM | 27434 | CZ  | ARG | C | 511 | 30.366 | 63.758 | 19.708 | 1.00 | 13.39 | C |
| ATOM | 27435 | NH1 | ARG | C | 511 | 29.386 | 64.404 | 19.097 | 1.00 | 14.47 | N |
| ATOM | 27438 | NH2 | ARG | C | 511 | 31.570 | 63.687 | 19.158 | 1.00 | 14.95 | N |
| ATOM | 27441 | C   | ARG | C | 511 | 31.980 | 66.065 | 24.603 | 1.00 | 12.11 | C |
| ATOM | 27442 | O   | ARG | C | 511 | 32.970 | 65.466 | 25.122 | 1.00 | 13.33 | O |
| ATOM | 27444 | N   | ARG | C | 512 | 32.019 | 67.303 | 24.140 | 1.00 | 12.33 | N |
| ATOM | 27445 | CA  | ARG | C | 512 | 33.308 | 67.995 | 24.174 | 1.00 | 11.60 | C |
| ATOM | 27447 | CB  | ARG | C | 512 | 33.247 | 69.247 | 23.351 | 1.00 | 12.95 | C |
| ATOM | 27450 | CG  | ARG | C | 512 | 32.964 | 69.030 | 21.893 | 1.00 | 13.18 | C |
| ATOM | 27453 | CD  | ARG | C | 512 | 33.945 | 68.037 | 21.292 | 1.00 | 15.61 | C |
| ATOM | 27456 | NE  | ARG | C | 512 | 33.898 | 67.962 | 19.833 | 1.00 | 17.37 | N |
| ATOM | 27458 | CZ  | ARG | C | 512 | 34.097 | 66.861 | 19.124 | 1.00 | 16.65 | C |
| ATOM | 27459 | NH1 | ARG | C | 512 | 34.305 | 65.684 | 19.696 | 1.00 | 18.31 | N |
| ATOM | 27462 | NH2 | ARG | C | 512 | 34.106 | 66.960 | 17.798 | 1.00 | 16.06 | N |
| ATOM | 27465 | C   | ARG | C | 512 | 33.757 | 68.295 | 25.618 | 1.00 | 10.57 | C |
| ATOM | 27466 | O   | ARG | C | 512 | 34.922 | 68.230 | 25.916 | 1.00 | 12.80 | O |
| ATOM | 27468 | N   | THR | C | 513 | 32.819 | 68.660 | 26.478 | 1.00 | 10.96 | N |
| ATOM | 27469 | CA  | THR | C | 513 | 33.140 | 68.929 | 27.907 | 1.00 | 11.96 | C |
| ATOM | 27471 | CB  | THR | C | 513 | 31.965 | 69.504 | 28.623 | 1.00 | 12.55 | C |
| ATOM | 27473 | OG1 | THR | C | 513 | 31.603 | 70.698 | 27.922 | 1.00 | 12.07 | O |
| ATOM | 27475 | CG2 | THR | C | 513 | 32.270 | 69.904 | 30.061 | 1.00 | 13.55 | C |
| ATOM | 27479 | C   | THR | C | 513 | 33.649 | 67.651 | 28.573 | 1.00 | 12.01 | C |
| ATOM | 27480 | O   | THR | C | 513 | 34.576 | 67.676 | 29.359 | 1.00 | 12.73 | O |
| ATOM | 27482 | N   | THR | C | 514 | 33.050 | 66.503 | 28.215 | 1.00 | 11.07 | N |
| ATOM | 27483 | CA  | THR | C | 514 | 33.525 | 65.235 | 28.741 | 1.00 | 11.68 | C |
| ATOM | 27485 | CB  | THR | C | 514 | 32.597 | 64.133 | 28.249 | 1.00 | 11.62 | C |
| ATOM | 27487 | OG1 | THR | C | 514 | 31.287 | 64.380 | 28.758 | 1.00 | 11.43 | O |
| ATOM | 27489 | CG2 | THR | C | 514 | 33.044 | 62.765 | 28.761 | 1.00 | 13.04 | C |
| ATOM | 27493 | C   | THR | C | 514 | 34.988 | 64.935 | 28.319 | 1.00 | 12.30 | C |
| ATOM | 27494 | O   | THR | C | 514 | 35.808 | 64.470 | 29.128 | 1.00 | 13.03 | O |
| ATOM | 27496 | N   | GLU | C | 515 | 35.315 | 65.255 | 27.076 | 1.00 | 12.72 | N |
| ATOM | 27497 | CA  | GLU | C | 515 | 36.697 | 65.113 | 26.588 | 1.00 | 13.52 | C |
| ATOM | 27499 | CB  | GLU | C | 515 | 36.802 | 65.444 | 25.101 | 1.00 | 12.88 | C |
| ATOM | 27502 | CG  | GLU | C | 515 | 38.195 | 65.101 | 24.607 | 1.00 | 14.27 | C |
| ATOM | 27505 | CD  | GLU | C | 515 | 38.395 | 65.087 | 23.081 | 1.00 | 17.62 | C |
| ATOM | 27506 | OE1 | GLU | C | 515 | 37.421 | 65.269 | 22.294 | 1.00 | 18.15 | O |
| ATOM | 27507 | OE2 | GLU | C | 515 | 39.571 | 64.894 | 22.658 | 1.00 | 18.66 | O |
| ATOM | 27508 | C   | GLU | C | 515 | 37.640 | 66.038 | 27.371 | 1.00 | 13.76 | C |
| ATOM | 27509 | O   | GLU | C | 515 | 38.742 | 65.654 | 27.769 | 1.00 | 12.36 | O |
| ATOM | 27511 | N   | SER | C | 516 | 37.187 | 67.269 | 27.634 | 1.00 | 13.33 | N |
| ATOM | 27512 | CA  | SER | C | 516 | 37.978 | 68.267 | 28.414 | 1.00 | 13.43 | C |
| ATOM | 27514 | CB  | SER | C | 516 | 37.336 | 69.641 | 28.441 | 1.00 | 13.62 | C |
| ATOM | 27517 | OG  | SER | C | 516 | 37.426 | 70.351 | 27.183 | 1.00 | 11.44 | O |
| ATOM | 27519 | C   | SER | C | 516 | 38.186 | 67.748 | 29.853 | 1.00 | 12.42 | C |
| ATOM | 27520 | O   | SER | C | 516 | 39.261 | 67.858 | 30.414 | 1.00 | 11.85 | O |
| ATOM | 27522 | N   | ASN | C | 517 | 37.169 | 67.126 | 30.449 | 1.00 | 11.53 | N |
| ATOM | 27523 | CA  | ASN | C | 517 | 37.386 | 66.442 | 31.767 | 1.00 | 12.53 | C |
| ATOM | 27525 | CB  | ASN | C | 517 | 36.129 | 65.751 | 32.271 | 1.00 | 13.11 | C |
| ATOM | 27528 | CG  | ASN | C | 517 | 35.128 | 66.728 | 32.929 | 1.00 | 12.25 | C |
| ATOM | 27529 | OD1 | ASN | C | 517 | 35.501 | 67.800 | 33.457 | 1.00 | 14.79 | O |
| ATOM | 27530 | ND2 | ASN | C | 517 | 33.826 | 66.331 | 32.918 | 1.00 | 12.60 | N |
| ATOM | 27533 | C   | ASN | C | 517 | 38.504 | 65.422 | 31.701 | 1.00 | 13.03 | C |
| ATOM | 27534 | O   | ASN | C | 517 | 39.327 | 65.332 | 32.601 | 1.00 | 13.42 | O |
| ATOM | 27536 | N   | ASP | C | 518 | 38.518 | 64.660 | 30.619 | 1.00 | 12.72 | N |
| ATOM | 27537 | CA  | ASP | C | 518 | 39.504 | 63.607 | 30.447 | 1.00 | 13.95 | C |
| ATOM | 27539 | CB  | ASP | C | 518 | 39.155 | 62.773 | 29.212 | 1.00 | 12.79 | C |

| ATOM | 27542 | CG | ASP | C | 518 | 39.972 | 61.516 | 29.102 | 1.00 | 17.89 | C |
|------|-------|-----|-----|---|-----|--------|--------|--------|------|-------|---|
| ATOM | 27543 | OD1 | ASP | C | 518 | 40.327 | 60.939 | 30.156 | 1.00 | 20.39 | O |
| ATOM | 27544 | OD2 | ASP | C | 518 | 40.169 | 61.043 | 27.947 | 1.00 | 23.27 | O |
| ATOM | 27545 | C | ASP | C | 518 | 40.891 | 64.218 | 30.313 | 1.00 | 12.94 | C |
| ATOM | 27546 | O | ASP | C | 518 | 41.878 | 63.818 | 30.954 | 1.00 | 12.98 | O |
| ATOM | 27548 | N | VAL | C | 519 | 41.010 | 65.224 | 29.470 | 1.00 | 11.93 | N |
| ATOM | 27549 | CA | VAL | C | 519 | 42.314 | 65.811 | 29.243 | 1.00 | 11.97 | C |
| ATOM | 27551 | CB | VAL | C | 519 | 42.292 | 66.759 | 28.033 | 1.00 | 11.63 | C |
| ATOM | 27553 | CG1 | VAL | C | 519 | 43.608 | 67.511 | 27.892 | 1.00 | 11.65 | C |
| ATOM | 27557 | CG2 | VAL | C | 519 | 41.932 | 66.039 | 26.766 | 1.00 | 12.26 | C |
| ATOM | 27561 | C | VAL | C | 519 | 42.807 | 66.554 | 30.524 | 1.00 | 11.54 | C |
| ATOM | 27562 | O | VAL | C | 519 | 44.012 | 66.505 | 30.915 | 1.00 | 12.74 | O |
| ATOM | 27564 | N | LEU | C | 520 | 41.892 | 67.244 | 31.191 | 1.00 | 12.09 | N |
| ATOM | 27565 | CA | LEU | C | 520 | 42.268 | 67.877 | 32.445 | 1.00 | 12.24 | C |
| ATOM | 27567 | CB | LEU | C | 520 | 41.155 | 68.768 | 33.002 | 1.00 | 12.30 | C |
| ATOM | 27570 | CG | LEU | C | 520 | 41.518 | 69.493 | 34.289 | 1.00 | 11.29 | C |
| ATOM | 27572 | CD1 | LEU | C | 520 | 42.788 | 70.363 | 34.134 | 1.00 | 12.45 | C |
| ATOM | 27576 | CD2 | LEU | C | 520 | 40.336 | 70.259 | 34.744 | 1.00 | 12.02 | C |
| ATOM | 27580 | C | LEU | C | 520 | 42.690 | 66.796 | 33.483 | 1.00 | 12.45 | C |
| ATOM | 27581 | O | LEU | C | 520 | 43.583 | 67.022 | 34.285 | 1.00 | 13.08 | O |
| ATOM | 27583 | N | SER | C | 521 | 42.039 | 65.642 | 33.477 | 1.00 | 11.97 | N |
| ATOM | 27584 | CA | SER | C | 521 | 42.453 | 64.544 | 34.373 | 1.00 | 12.93 | C |
| ATOM | 27586 | CB | SER | C | 521 | 41.493 | 63.372 | 34.227 | 1.00 | 12.73 | C |
| ATOM | 27589 | OG | SER | C | 521 | 40.167 | 63.771 | 34.610 | 1.00 | 13.50 | O |
| ATOM | 27591 | C | SER | C | 521 | 43.890 | 64.142 | 34.087 | 1.00 | 12.75 | C |
| ATOM | 27592 | O | SER | C | 521 | 44.667 | 63.850 | 35.007 | 1.00 | 12.89 | O |
| ATOM | 27594 | N | LEU | C | 522 | 44.253 | 64.054 | 32.807 | 1.00 | 14.10 | N |
| ATOM | 27595 | CA | LEU | C | 522 | 45.661 | 63.744 | 32.448 | 1.00 | 12.79 | C |
| ATOM | 27597 | CB | LEU | C | 522 | 45.838 | 63.671 | 30.945 | 1.00 | 12.26 | C |
| ATOM | 27600 | CG | LEU | C | 522 | 45.182 | 62.516 | 30.196 | 1.00 | 12.81 | C |
| ATOM | 27602 | CD1 | LEU | C | 522 | 45.162 | 62.749 | 28.702 | 1.00 | 13.30 | C |
| ATOM | 27606 | CD2 | LEU | C | 522 | 45.873 | 61.278 | 30.456 | 1.00 | 13.78 | C |
| ATOM | 27610 | C | LEU | C | 522 | 46.611 | 64.799 | 33.028 | 1.00 | 13.29 | C |
| ATOM | 27611 | O | LEU | C | 522 | 47.670 | 64.492 | 33.584 | 1.00 | 14.59 | O |
| ATOM | 27613 | N | LEU | C | 523 | 46.214 | 66.063 | 32.891 | 1.00 | 13.66 | N |
| ATOM | 27614 | CA | LEU | C | 523 | 47.054 | 67.197 | 33.345 | 1.00 | 12.65 | C |
| ATOM | 27616 | CB | LEU | C | 523 | 46.437 | 68.504 | 32.841 | 1.00 | 12.66 | C |
| ATOM | 27619 | CG | LEU | C | 523 | 47.148 | 69.777 | 33.314 | 1.00 | 13.89 | C |
| ATOM | 27621 | CD1 | LEU | C | 523 | 48.639 | 69.802 | 33.018 | 1.00 | 14.84 | C |
| ATOM | 27625 | CD2 | LEU | C | 523 | 46.459 | 70.965 | 32.643 | 1.00 | 13.45 | C |
| ATOM | 27629 | C | LEU | C | 523 | 47.202 | 67.237 | 34.872 | 1.00 | 11.72 | C |
| ATOM | 27630 | O | LEU | C | 523 | 48.306 | 67.379 | 35.428 | 1.00 | 13.44 | O |
| ATOM | 27632 | N | LEU | C | 524 | 46.090 | 67.117 | 35.569 | 1.00 | 11.68 | N |
| ATOM | 27633 | CA | LEU | C | 524 | 46.114 | 67.051 | 37.022 | 1.00 | 12.05 | C |
| ATOM | 27635 | CB | LEU | C | 524 | 44.711 | 67.302 | 37.605 | 1.00 | 12.52 | C |
| ATOM | 27638 | CG | LEU | C | 524 | 44.110 | 68.647 | 37.218 | 1.00 | 12.82 | C |
| ATOM | 27640 | CD1 | LEU | C | 524 | 42.925 | 68.931 | 38.072 | 1.00 | 13.91 | C |
| ATOM | 27644 | CD2 | LEU | C | 524 | 45.073 | 69.868 | 37.243 | 1.00 | 13.24 | C |
| ATOM | 27648 | C | LEU | C | 524 | 46.813 | 65.833 | 37.620 | 1.00 | 13.34 | C |
| ATOM | 27649 | O | LEU | C | 524 | 47.475 | 65.924 | 38.685 | 1.00 | 14.15 | O |
| ATOM | 27651 | N | ALA | C | 525 | 46.667 | 64.664 | 36.955 | 1.00 | 11.80 | N |
| ATOM | 27652 | CA | ALA | C | 525 | 47.394 | 63.447 | 37.381 | 1.00 | 12.56 | C |
| ATOM | 27654 | CB | ALA | C | 525 | 46.996 | 62.314 | 36.567 | 1.00 | 13.21 | C |
| ATOM | 27658 | C | ALA | C | 525 | 48.896 | 63.718 | 37.221 | 1.00 | 12.27 | C |
| ATOM | 27659 | O | ALA | C | 525 | 49.703 | 63.319 | 38.062 | 1.00 | 12.88 | O |
| ATOM | 27661 | N | THR | C | 526 | 49.259 | 64.397 | 36.130 | 1.00 | 11.55 | N |
| ATOM | 27662 | CA | THR | C | 526 | 50.668 | 64.763 | 35.860 | 1.00 | 12.72 | C |

| ATOM | 27664 | CB | THR | C | 526 | 50.807 | 65.316 | 34.450 | 1.00 | 11.81 | C |
| --- | --- | --- | --- | --- | --- | --- | --- | --- | --- | --- | --- |
| ATOM | 27666 | OG1 | THR | C | 526 | 50.538 | 64.268 | 33.508 | 1.00 | 14.11 | O |
| ATOM | 27668 | CG2 | THR | C | 526 | 52.175 | 65.898 | 34.212 | 1.00 | 13.46 | C |
| ATOM | 27672 | C | THR | C | 526 | 51.208 | 65.741 | 36.916 | 1.00 | 12.41 | C |
| ATOM | 27673 | O | THR | C | 526 | 52.292 | 65.537 | 37.478 | 1.00 | 13.42 | O |
| ATOM | 27675 | N | HIS | C | 527 | 50.408 | 66.743 | 37.257 | 1.00 | 12.44 | N |
| ATOM | 27676 | CA | HIS | C | 527 | 50.801 | 67.757 | 38.288 | 1.00 | 12.94 | C |
| ATOM | 27678 | CB | HIS | C | 527 | 49.737 | 68.876 | 38.318 | 1.00 | 13.70 | C |
| ATOM | 27681 | CG | HIS | C | 527 | 50.096 | 70.043 | 39.161 | 1.00 | 13.65 | C |
| ATOM | 27682 | ND1 | HIS | C | 527 | 49.315 | 71.177 | 39.234 | 1.00 | 14.25 | N |
| ATOM | 27684 | CE1 | HIS | C | 527 | 49.878 | 72.039 | 40.075 | 1.00 | 13.06 | C |
| ATOM | 27686 | NE2 | HIS | C | 527 | 50.977 | 71.497 | 40.564 | 1.00 | 13.72 | N |
| ATOM | 27688 | CD2 | HIS | C | 527 | 51.131 | 70.240 | 40.013 | 1.00 | 13.97 | C |
| ATOM | 27690 | C | HIS | C | 527 | 50.950 | 67.057 | 39.661 | 1.00 | 13.13 | C |
| ATOM | 27691 | O | HIS | C | 527 | 51.920 | 67.279 | 40.407 | 1.00 | 13.54 | O |
| ATOM | 27693 | N | LEU | C | 528 | 50.004 | 66.169 | 39.994 | 1.00 | 11.88 | N |
| ATOM | 27694 | CA | LEU | C | 528 | 50.017 | 65.505 | 41.294 | 1.00 | 12.75 | C |
| ATOM | 27696 | CB | LEU | C | 528 | 48.706 | 64.705 | 41.473 | 1.00 | 11.21 | C |
| ATOM | 27699 | CG | LEU | C | 528 | 48.594 | 63.948 | 42.795 | 1.00 | 14.01 | C |
| ATOM | 27701 | CD1 | LEU | C | 528 | 48.927 | 64.751 | 44.028 | 1.00 | 16.82 | C |
| ATOM | 27705 | CD2 | LEU | C | 528 | 47.218 | 63.327 | 42.889 | 1.00 | 13.89 | C |
| ATOM | 27709 | C | LEU | C | 528 | 51.287 | 64.610 | 41.388 | 1.00 | 12.21 | C |
| ATOM | 27710 | O | LEU | C | 528 | 51.995 | 64.594 | 42.395 | 1.00 | 11.79 | O |
| ATOM | 27712 | N | TYR | C | 529 | 51.617 | 63.883 | 40.304 | 1.00 | 11.33 | N |
| ATOM | 27713 | CA | TYR | C | 529 | 52.832 | 63.080 | 40.270 | 1.00 | 13.20 | C |
| ATOM | 27715 | CB | TYR | C | 529 | 52.976 | 62.397 | 38.891 | 1.00 | 12.24 | C |
| ATOM | 27718 | CG | TYR | C | 529 | 54.281 | 61.671 | 38.751 | 1.00 | 11.67 | C |
| ATOM | 27719 | CD1 | TYR | C | 529 | 54.406 | 60.301 | 39.051 | 1.00 | 14.01 | C |
| ATOM | 27721 | CE1 | TYR | C | 529 | 55.649 | 59.669 | 38.942 | 1.00 | 12.36 | C |
| ATOM | 27723 | CZ | TYR | C | 529 | 56.785 | 60.383 | 38.521 | 1.00 | 14.06 | C |
| ATOM | 27724 | OH | TYR | C | 529 | 57.985 | 59.696 | 38.447 | 1.00 | 13.00 | O |
| ATOM | 27726 | CE2 | TYR | C | 529 | 56.671 | 61.702 | 38.177 | 1.00 | 12.56 | C |
| ATOM | 27728 | CD2 | TYR | C | 529 | 55.418 | 62.346 | 38.316 | 1.00 | 14.87 | C |
| ATOM | 27730 | C | TYR | C | 529 | 54.060 | 63.981 | 40.586 | 1.00 | 11.90 | C |
| ATOM | 27731 | O | TYR | C | 529 | 54.929 | 63.654 | 41.420 | 1.00 | 11.93 | O |
| ATOM | 27733 | N | CYS | C | 530 | 54.132 | 65.117 | 39.892 | 1.00 | 12.34 | N |
| ATOM | 27734 | CA | CYS | C | 530 | 55.319 | 65.956 | 40.019 | 1.00 | 13.22 | C |
| ATOM | 27736 | CB | CYS | C | 530 | 55.376 | 67.012 | 38.951 | 1.00 | 13.08 | C |
| ATOM | 27739 | SG | CYS | C | 530 | 55.582 | 66.355 | 37.323 | 1.00 | 15.35 | S |
| ATOM | 27741 | C | CYS | C | 530 | 55.398 | 66.611 | 41.396 | 1.00 | 12.65 | C |
| ATOM | 27742 | O | CYS | C | 530 | 56.472 | 66.702 | 41.981 | 1.00 | 13.06 | O |
| ATOM | 27744 | N | VAL | C | 531 | 54.291 | 67.111 | 41.902 | 1.00 | 11.55 | N |
| ATOM | 27745 | CA | VAL | C | 531 | 54.349 | 67.843 | 43.169 | 1.00 | 11.86 | C |
| ATOM | 27747 | CB | VAL | C | 531 | 53.034 | 68.574 | 43.490 | 1.00 | 11.98 | C |
| ATOM | 27749 | CG1 | VAL | C | 531 | 51.936 | 67.670 | 43.995 | 1.00 | 13.23 | C |
| ATOM | 27753 | CG2 | VAL | C | 531 | 53.271 | 69.734 | 44.431 | 1.00 | 11.58 | C |
| ATOM | 27757 | C | VAL | C | 531 | 54.765 | 66.896 | 44.314 | 1.00 | 11.58 | C |
| ATOM | 27758 | O | VAL | C | 531 | 55.459 | 67.279 | 45.260 | 1.00 | 12.57 | O |
| ATOM | 27760 | N | LEU | C | 532 | 54.390 | 65.627 | 44.188 | 1.00 | 11.10 | N |
| ATOM | 27761 | CA | LEU | C | 532 | 54.787 | 64.700 | 45.276 | 1.00 | 12.23 | C |
| ATOM | 27763 | CB | LEU | C | 532 | 54.099 | 63.339 | 45.160 | 1.00 | 13.49 | C |
| ATOM | 27766 | CG | LEU | C | 532 | 52.596 | 63.497 | 45.242 | 1.00 | 14.94 | C |
| ATOM | 27768 | CD1 | LEU | C | 532 | 51.898 | 62.199 | 44.843 | 1.00 | 17.01 | C |
| ATOM | 27772 | CD2 | LEU | C | 532 | 52.249 | 63.923 | 46.645 | 1.00 | 16.52 | C |
| ATOM | 27776 | C | LEU | C | 532 | 56.308 | 64.477 | 45.272 | 1.00 | 11.53 | C |
| ATOM | 27777 | O | LEU | C | 532 | 56.951 | 64.405 | 46.334 | 1.00 | 12.54 | O |
| ATOM | 27779 | N | GLN | C | 533 | 56.872 | 64.278 | 44.069 | 1.00 | 11.53 | N |

| ATOM | 27780 | CA | GLN | C | 533 | 58.334 | 64.206 | 43.924 | 1.00 | 11.62 | C |
| ATOM | 27782 | CB | GLN | C | 533 | 58.734 | 63.981 | 42.456 | 1.00 | 11.83 | C |
| ATOM | 27785 | CG | GLN | C | 533 | 60.235 | 63.887 | 42.187 | 1.00 | 10.99 | C |
| ATOM | 27788 | CD | GLN | C | 533 | 60.893 | 62.544 | 42.496 | 1.00 | 12.46 | C |
| ATOM | 27789 | OE1 | GLN | C | 533 | 60.251 | 61.594 | 42.937 | 1.00 | 13.84 | O |
| ATOM | 27790 | NE2 | GLN | C | 533 | 62.214 | 62.467 | 42.224 | 1.00 | 12.68 | N |
| ATOM | 27793 | C | GLN | C | 533 | 59.007 | 65.487 | 44.478 | 1.00 | 12.22 | C |
| ATOM | 27794 | O | GLN | C | 533 | 59.978 | 65.426 | 45.231 | 1.00 | 11.85 | O |
| ATOM | 27796 | N | ALA | C | 534 | 58.473 | 66.653 | 44.128 | 1.00 | 11.56 | N |
| ATOM | 27797 | CA | ALA | C | 534 | 59.023 | 67.925 | 44.614 | 1.00 | 12.53 | C |
| ATOM | 27799 | CB | ALA | C | 534 | 58.277 | 69.058 | 44.034 | 1.00 | 13.11 | C |
| ATOM | 27803 | C | ALA | C | 534 | 58.991 | 68.002 | 46.141 | 1.00 | 12.43 | C |
| ATOM | 27804 | O | ALA | C | 534 | 59.926 | 68.452 | 46.785 | 1.00 | 12.59 | O |
| ATOM | 27806 | N | ILE | C | 535 | 57.878 | 67.610 | 46.728 | 1.00 | 12.27 | N |
| ATOM | 27807 | CA | ILE | C | 535 | 57.715 | 67.570 | 48.206 | 1.00 | 12.67 | C |
| ATOM | 27809 | CB | ILE | C | 535 | 56.303 | 67.087 | 48.577 | 1.00 | 12.76 | C |
| ATOM | 27811 | CG1 | ILE | C | 535 | 55.337 | 68.272 | 48.331 | 1.00 | 13.66 | C |
| ATOM | 27814 | CD1 | ILE | C | 535 | 53.844 | 67.924 | 48.284 | 1.00 | 16.35 | C |
| ATOM | 27818 | CG2 | ILE | C | 535 | 56.220 | 66.593 | 50.017 | 1.00 | 15.55 | C |
| ATOM | 27822 | C | ILE | C | 535 | 58.774 | 66.694 | 48.874 | 1.00 | 12.72 | C |
| ATOM | 27823 | O | ILE | C | 535 | 59.404 | 67.084 | 49.849 | 1.00 | 11.90 | O |
| ATOM | 27825 | N | ASP | C | 536 | 58.958 | 65.517 | 48.306 | 1.00 | 11.78 | N |
| ATOM | 27826 | CA | ASP | C | 536 | 60.000 | 64.612 | 48.811 | 1.00 | 12.85 | C |
| ATOM | 27828 | CB | ASP | C | 536 | 59.928 | 63.263 | 48.096 | 1.00 | 14.52 | C |
| ATOM | 27831 | CG | ASP | C | 536 | 58.824 | 62.382 | 48.615 | 1.00 | 14.39 | C |
| ATOM | 27832 | OD1 | ASP | C | 536 | 58.451 | 62.470 | 49.801 | 1.00 | 15.60 | O |
| ATOM | 27833 | OD2 | ASP | C | 536 | 58.346 | 61.529 | 47.834 | 1.00 | 13.94 | O |
| ATOM | 27834 | C | ASP | C | 536 | 61.403 | 65.231 | 48.693 | 1.00 | 12.83 | C |
| ATOM | 27835 | O | ASP | C | 536 | 62.210 | 65.160 | 49.651 | 1.00 | 13.30 | O |
| ATOM | 27837 | N | LEU | C | 537 | 61.700 | 65.865 | 47.568 | 1.00 | 13.18 | N |
| ATOM | 27838 | CA | LEU | C | 537 | 63.022 | 66.487 | 47.381 | 1.00 | 12.50 | C |
| ATOM | 27840 | CB | LEU | C | 537 | 63.210 | 66.905 | 45.926 | 1.00 | 13.64 | C |
| ATOM | 27843 | CG | LEU | C | 537 | 63.276 | 65.748 | 44.907 | 1.00 | 13.70 | C |
| ATOM | 27845 | CD1 | LEU | C | 537 | 63.329 | 66.233 | 43.467 | 1.00 | 16.74 | C |
| ATOM | 27849 | CD2 | LEU | C | 537 | 64.471 | 64.848 | 45.214 | 1.00 | 15.64 | C |
| ATOM | 27853 | C | LEU | C | 537 | 63.197 | 67.702 | 48.355 | 1.00 | 12.91 | C |
| ATOM | 27854 | O | LEU | C | 537 | 64.277 | 67.961 | 48.905 | 1.00 | 11.08 | O |
| ATOM | 27856 | N | ARG | C | 538 | 62.119 | 68.437 | 48.565 | 1.00 | 11.14 | N |
| ATOM | 27857 | CA | ARG | C | 538 | 62.192 | 69.529 | 49.535 | 1.00 | 11.84 | C |
| ATOM | 27859 | CB | ARG | C | 538 | 60.938 | 70.378 | 49.427 | 1.00 | 13.21 | C |
| ATOM | 27862 | CG | ARG | C | 538 | 60.995 | 71.708 | 50.206 | 1.00 | 12.68 | C |
| ATOM | 27865 | CD | ARG | C | 538 | 62.008 | 72.680 | 49.562 | 1.00 | 14.24 | C |
| ATOM | 27868 | NE | ARG | C | 538 | 61.410 | 73.307 | 48.422 | 1.00 | 12.66 | N |
| ATOM | 27870 | CZ | ARG | C | 538 | 62.028 | 74.146 | 47.595 | 1.00 | 12.59 | C |
| ATOM | 27871 | NH1 | ARG | C | 538 | 63.332 | 74.393 | 47.775 | 1.00 | 12.97 | N |
| ATOM | 27874 | NH2 | ARG | C | 538 | 61.355 | 74.704 | 46.600 | 1.00 | 14.82 | N |
| ATOM | 27877 | C | ARG | C | 538 | 62.421 | 69.039 | 50.967 | 1.00 | 12.10 | C |
| ATOM | 27878 | O | ARG | C | 538 | 63.194 | 69.617 | 51.765 | 1.00 | 11.95 | O |
| ATOM | 27880 | N | ALA | C | 539 | 61.778 | 67.925 | 51.295 | 1.00 | 11.74 | N |
| ATOM | 27881 | CA | ALA | C | 539 | 61.934 | 67.280 | 52.608 | 1.00 | 11.94 | C |
| ATOM | 27883 | CB | ALA | C | 539 | 60.975 | 66.108 | 52.725 | 1.00 | 13.72 | C |
| ATOM | 27887 | C | ALA | C | 539 | 63.394 | 66.843 | 52.797 | 1.00 | 11.33 | C |
| ATOM | 27888 | O | ALA | C | 539 | 64.000 | 67.104 | 53.832 | 1.00 | 11.27 | O |
| ATOM | 27890 | N | ILE | C | 540 | 63.963 | 66.250 | 51.757 | 1.00 | 11.68 | N |
| ATOM | 27891 | CA | ILE | C | 540 | 65.394 | 65.864 | 51.779 | 1.00 | 12.43 | C |
| ATOM | 27893 | CB | ILE | C | 540 | 65.842 | 65.135 | 50.495 | 1.00 | 12.04 | C |
| ATOM | 27895 | CG1 | ILE | C | 540 | 65.203 | 63.753 | 50.435 | 1.00 | 14.28 | C |

| | | | | | | | | | |
|---|---|---|---|---|---|---|---|---|---|
| ATOM | 27898 | CD1 | ILE | C | 540 | 65.454 | 63.092 | 49.103 | 1.00 15.82 | C |
| ATOM | 27902 | CG2 | ILE | C | 540 | 67.354 | 65.049 | 50.385 | 1.00 14.83 | C |
| ATOM | 27906 | C | ILE | C | 540 | 66.238 | 67.121 | 52.015 | 1.00 11.16 | C |
| ATOM | 27907 | O | ILE | C | 540 | 67.185 | 67.085 | 52.804 | 1.00 13.33 | O |
| ATOM | 27909 | N | GLU | C | 541 | 65.930 | 68.224 | 51.335 | 1.00 11.20 | N |
| ATOM | 27910 | CA | GLU | C | 541 | 66.640 | 69.497 | 51.581 | 1.00 12.46 | C |
| ATOM | 27912 | CB | GLU | C | 541 | 66.103 | 70.569 | 50.647 | 1.00 11.75 | C |
| ATOM | 27915 | CG | GLU | C | 541 | 66.638 | 71.959 | 50.876 | 1.00 14.48 | C |
| ATOM | 27918 | CD | GLU | C | 541 | 65.890 | 73.014 | 50.056 | 1.00 16.76 | C |
| ATOM | 27919 | OE1 | GLU | C | 541 | 65.176 | 72.675 | 49.071 | 1.00 17.29 | O |
| ATOM | 27920 | OE2 | GLU | C | 541 | 66.015 | 74.210 | 50.414 | 1.00 23.71 | O |
| ATOM | 27921 | C | GLU | C | 541 | 66.568 | 69.973 | 53.025 | 1.00 11.32 | C |
| ATOM | 27922 | O | GLU | C | 541 | 67.577 | 70.283 | 53.632 | 1.00 12.48 | O |
| ATOM | 27924 | N | PHE | C | 542 | 65.371 | 69.969 | 53.600 | 1.00 12.12 | N |
| ATOM | 27925 | CA | PHE | C | 542 | 65.194 | 70.339 | 54.991 | 1.00 12.37 | C |
| ATOM | 27927 | CB | PHE | C | 542 | 63.720 | 70.289 | 55.343 | 1.00 14.61 | C |
| ATOM | 27930 | CG | PHE | C | 542 | 62.929 | 71.466 | 54.831 | 1.00 15.06 | C |
| ATOM | 27931 | CD1 | PHE | C | 542 | 63.430 | 72.346 | 53.879 | 1.00 17.24 | C |
| ATOM | 27933 | CE1 | PHE | C | 542 | 62.652 | 73.436 | 53.408 | 1.00 17.95 | C |
| ATOM | 27935 | CZ | PHE | C | 542 | 61.390 | 73.630 | 53.936 | 1.00 16.33 | C |
| ATOM | 27937 | CE2 | PHE | C | 542 | 60.889 | 72.742 | 54.866 | 1.00 19.99 | C |
| ATOM | 27939 | CD2 | PHE | C | 542 | 61.648 | 71.674 | 55.317 | 1.00 18.34 | C |
| ATOM | 27941 | C | PHE | C | 542 | 65.949 | 69.420 | 55.936 | 1.00 12.90 | C |
| ATOM | 27942 | O | PHE | C | 542 | 66.530 | 69.857 | 56.902 | 1.00 13.54 | O |
| ATOM | 27944 | N | GLU | C | 543 | 65.918 | 68.128 | 55.668 | 1.00 12.33 | N |
| ATOM | 27945 | CA | GLU | C | 543 | 66.650 | 67.178 | 56.522 | 1.00 13.44 | C |
| ATOM | 27947 | CB | GLU | C | 543 | 66.336 | 65.743 | 56.118 | 1.00 14.22 | C |
| ATOM | 27950 | CG | GLU | C | 543 | 64.879 | 65.339 | 56.375 | 1.00 15.83 | C |
| ATOM | 27953 | CD | GLU | C | 543 | 64.561 | 65.242 | 57.844 | 1.00 17.79 | C |
| ATOM | 27954 | OE1 | GLU | C | 543 | 65.284 | 64.473 | 58.547 | 1.00 19.53 | O |
| ATOM | 27955 | OE2 | GLU | C | 543 | 63.635 | 65.933 | 58.329 | 1.00 20.39 | O |
| ATOM | 27956 | C | GLU | C | 543 | 68.151 | 67.473 | 56.433 | 1.00 13.40 | C |
| ATOM | 27957 | O | GLU | C | 543 | 68.849 | 67.510 | 57.446 | 1.00 14.66 | O |
| ATOM | 27959 | N | PHE | C | 544 | 68.639 | 67.742 | 55.230 | 1.00 12.05 | N |
| ATOM | 27960 | CA | PHE | C | 544 | 70.040 | 68.039 | 55.043 | 1.00 12.87 | C |
| ATOM | 27962 | CB | PHE | C | 544 | 70.312 | 68.275 | 53.549 | 1.00 13.58 | C |
| ATOM | 27965 | CG | PHE | C | 544 | 71.692 | 68.823 | 53.251 | 1.00 12.13 | C |
| ATOM | 27966 | CD1 | PHE | C | 544 | 72.760 | 67.965 | 53.080 | 1.00 13.32 | C |
| ATOM | 27968 | CE1 | PHE | C | 544 | 74.074 | 68.480 | 52.816 | 1.00 12.77 | C |
| ATOM | 27970 | CZ | PHE | C | 544 | 74.243 | 69.836 | 52.676 | 1.00 14.36 | C |
| ATOM | 27972 | CE2 | PHE | C | 544 | 73.176 | 70.672 | 52.823 | 1.00 12.96 | C |
| ATOM | 27974 | CD2 | PHE | C | 544 | 71.916 | 70.167 | 53.090 | 1.00 13.00 | C |
| ATOM | 27976 | C | PHE | C | 544 | 70.454 | 69.256 | 55.861 | 1.00 13.20 | C |
| ATOM | 27977 | O | PHE | C | 544 | 71.485 | 69.269 | 56.538 | 1.00 12.68 | O |
| ATOM | 27979 | N | LYS | C | 545 | 69.640 | 70.302 | 55.753 | 1.00 13.73 | N |
| ATOM | 27980 | CA | LYS | C | 545 | 69.924 | 71.600 | 56.436 | 1.00 15.61 | C |
| ATOM | 27982 | CB | LYS | C | 545 | 68.864 | 72.600 | 56.057 | 1.00 15.67 | C |
| ATOM | 27985 | CG | LYS | C | 545 | 69.063 | 73.134 | 54.698 | 1.00 18.14 | C |
| ATOM | 27988 | CD | LYS | C | 545 | 68.060 | 74.234 | 54.421 | 1.00 22.52 | C |
| ATOM | 27991 | CE | LYS | C | 545 | 68.314 | 74.860 | 53.084 | 1.00 24.25 | C |
| ATOM | 27994 | NZ | LYS | C | 545 | 67.107 | 75.624 | 52.670 | 1.00 26.20 | N |
| ATOM | 27998 | C | LYS | C | 545 | 70.048 | 71.472 | 57.960 | 1.00 15.45 | C |
| ATOM | 27999 | O | LYS | C | 545 | 70.904 | 72.135 | 58.588 | 1.00 16.16 | O |
| ATOM | 28001 | N | LYS | C | 546 | 69.236 | 70.590 | 58.569 | 1.00 15.95 | N |
| ATOM | 28002 | CA | LYS | C | 546 | 69.324 | 70.303 | 60.008 | 1.00 17.10 | C |
| ATOM | 28004 | CB | LYS | C | 546 | 68.460 | 69.086 | 60.428 | 1.00 18.42 | C |
| ATOM | 28007 | CG | LYS | C | 546 | 66.990 | 69.166 | 60.226 | 1.00 21.02 | C |

| | | | | | | | | | |
|---|---|---|---|---|---|---|---|---|---|
|ATOM|28010|CD|LYS|C|546|66.290|67.961|60.830|1.00 21.30|C|
|ATOM|28013|CE|LYS|C|546|64.778|68.174|60.821|1.00 26.73|C|
|ATOM|28016|NZ|LYS|C|546|64.022|66.914|61.124|1.00 26.83|N|
|ATOM|28020|C|LYS|C|546|70.722|69.882|60.413|1.00 15.82|C|
|ATOM|28021|O|LYS|C|546|71.169|70.161|61.539|1.00 14.62|O|
|ATOM|28023|N|GLN|C|547|71.347|69.055|59.578|1.00 15.54|N|
|ATOM|28024|CA|GLN|C|547|72.689|68.578|59.844|1.00 16.28|C|
|ATOM|28026|CB|GLN|C|547|72.830|67.130|59.358|1.00 16.85|C|
|ATOM|28029|CG|GLN|C|547|71.794|66.211|60.099|1.00 20.34|C|
|ATOM|28032|CD|GLN|C|547|71.406|64.957|59.296|1.00 21.16|C|
|ATOM|28033|OE1|GLN|C|547|72.276|64.082|59.116|1.00 21.53|O|
|ATOM|28034|NE2|GLN|C|547|70.091|64.862|58.816|1.00 23.22|N|
|ATOM|28037|C|GLN|C|547|73.799|69.457|59.282|1.00 15.49|C|
|ATOM|28038|O|GLN|C|547|74.919|69.541|59.845|1.00 14.96|O|
|ATOM|28040|N|PHE|C|548|73.492|70.130|58.189|1.00 14.50|N|
|ATOM|28041|CA|PHE|C|548|74.490|70.992|57.515|1.00 14.84|C|
|ATOM|28043|CB|PHE|C|548|73.951|71.377|56.136|1.00 15.70|C|
|ATOM|28046|CG|PHE|C|548|74.906|72.174|55.257|1.00 17.75|C|
|ATOM|28047|CD1|PHE|C|548|76.225|71.839|55.141|1.00 15.73|C|
|ATOM|28049|CE1|PHE|C|548|77.084|72.576|54.293|1.00 15.11|C|
|ATOM|28051|CZ|PHE|C|548|76.592|73.629|53.539|1.00 19.56|C|
|ATOM|28053|CE2|PHE|C|548|75.249|73.988|53.639|1.00 17.26|C|
|ATOM|28055|CD2|PHE|C|548|74.410|73.249|54.489|1.00 19.03|C|
|ATOM|28057|C|PHE|C|548|74.857|72.225|58.347|1.00 14.99|C|
|ATOM|28058|O|PHE|C|548|76.024|72.597|58.419|1.00 14.82|O|
|ATOM|28060|N|GLY|C|549|73.875|72.851|58.993|1.00 13.97|N|
|ATOM|28061|CA|GLY|C|549|74.157|74.063|59.744|1.00 13.35|C|
|ATOM|28064|C|GLY|C|549|75.244|73.852|60.788|1.00 12.86|C|
|ATOM|28065|O|GLY|C|549|76.261|74.541|60.821|1.00 13.27|O|
|ATOM|28067|N|PRO|C|550|75.058|72.875|61.678|1.00 12.50|N|
|ATOM|28068|CA|PRO|C|550|76.118|72.566|62.616|1.00 13.14|C|
|ATOM|28070|CB|PRO|C|550|75.524|71.406|63.435|1.00 13.70|C|
|ATOM|28073|CG|PRO|C|550|74.068|71.501|63.261|1.00 12.14|C|
|ATOM|28076|CD|PRO|C|550|73.821|72.100|61.921|1.00 12.93|C|
|ATOM|28079|C|PRO|C|550|77.473|72.183|61.960|1.00 12.69|C|
|ATOM|28080|O|PRO|C|550|78.514|72.452|62.530|1.00 12.95|O|
|ATOM|28081|N|ALA|C|551|77.442|71.533|60.805|1.00 12.84|N|
|ATOM|28082|CA|ALA|C|551|78.703|71.101|60.138|1.00 14.32|C|
|ATOM|28084|CB|ALA|C|551|78.387|70.164|58.982|1.00 13.95|C|
|ATOM|28088|C|ALA|C|551|79.486|72.318|59.658|1.00 14.23|C|
|ATOM|28089|O|ALA|C|551|80.729|72.404|59.810|1.00 16.29|O|
|ATOM|28091|N|ILE|C|552|78.768|73.302|59.181|1.00 13.83|N|
|ATOM|28092|CA|ILE|C|552|79.383|74.574|58.722|1.00 14.82|C|
|ATOM|28094|CB|ILE|C|552|78.312|75.516|58.203|1.00 14.94|C|
|ATOM|28096|CG1|ILE|C|552|77.744|75.054|56.856|1.00 12.60|C|
|ATOM|28099|CD1|ILE|C|552|76.427|75.740|56.400|1.00 15.94|C|
|ATOM|28103|CG2|ILE|C|552|78.896|76.899|57.998|1.00 15.70|C|
|ATOM|28107|C|ILE|C|552|80.115|75.220|59.909|1.00 13.43|C|
|ATOM|28108|O|ILE|C|552|81.310|75.647|59.832|1.00 13.89|O|
|ATOM|28110|N|VAL|C|553|79.423|75.268|61.052|1.00 12.65|N|
|ATOM|28111|CA|VAL|C|553|79.965|75.925|62.229|1.00 12.81|C|
|ATOM|28113|CB|VAL|C|553|78.886|75.994|63.365|1.00 12.91|C|
|ATOM|28115|CG1|VAL|C|553|79.528|76.501|64.673|1.00 14.44|C|
|ATOM|28119|CG2|VAL|C|553|77.733|76.869|62.915|1.00 14.44|C|
|ATOM|28123|C|VAL|C|553|81.163|75.156|62.733|1.00 11.60|C|
|ATOM|28124|O|VAL|C|553|82.175|75.737|63.078|1.00 11.59|O|
|ATOM|28126|N|SER|C|554|81.046|73.827|62.756|1.00 13.39|N|

| ATOM | 28127 | CA | SER | C | 554 | 82.105 | 73.015 | 63.276 | 1.00 | 14.28 | C |
| ATOM | 28129 | CB | SER | C | 554 | 81.657 | 71.550 | 63.349 | 1.00 | 15.60 | C |
| ATOM | 28132 | OG | SER | C | 554 | 82.749 | 70.717 | 63.663 | 1.00 | 20.60 | O |
| ATOM | 28134 | C | SER | C | 554 | 83.395 | 73.168 | 62.457 | 1.00 | 13.50 | C |
| ATOM | 28135 | O | SER | C | 554 | 84.479 | 73.310 | 63.029 | 1.00 | 13.26 | O |
| ATOM | 28137 | N | LEU | C | 555 | 83.271 | 73.171 | 61.139 | 1.00 | 13.38 | N |
| ATOM | 28138 | CA | LEU | C | 555 | 84.468 | 73.324 | 60.272 | 1.00 | 14.29 | C |
| ATOM | 28140 | CB | LEU | C | 555 | 84.177 | 72.880 | 58.844 | 1.00 | 15.07 | C |
| ATOM | 28143 | CG | LEU | C | 555 | 84.087 | 71.366 | 58.641 | 1.00 | 19.84 | C |
| ATOM | 28145 | CD1 | LEU | C | 555 | 83.775 | 71.096 | 57.191 | 1.00 | 23.29 | C |
| ATOM | 28149 | CD2 | LEU | C | 555 | 85.302 | 70.611 | 59.019 | 1.00 | 23.88 | C |
| ATOM | 28153 | C | LEU | C | 555 | 85.043 | 74.735 | 60.326 | 1.00 | 14.12 | C |
| ATOM | 28154 | O | LEU | C | 555 | 86.254 | 74.915 | 60.309 | 1.00 | 12.59 | O |
| ATOM | 28156 | N | ILE | C | 556 | 84.192 | 75.751 | 60.420 | 1.00 | 13.53 | N |
| ATOM | 28157 | CA | ILE | C | 556 | 84.688 | 77.104 | 60.649 | 1.00 | 13.12 | C |
| ATOM | 28159 | CB | ILE | C | 556 | 83.542 | 78.094 | 60.663 | 1.00 | 13.10 | C |
| ATOM | 28161 | CG1 | ILE | C | 556 | 83.115 | 78.437 | 59.238 | 1.00 | 13.20 | C |
| ATOM | 28164 | CD1 | ILE | C | 556 | 81.805 | 79.251 | 59.156 | 1.00 | 12.58 | C |
| ATOM | 28168 | CG2 | ILE | C | 556 | 83.928 | 79.372 | 61.436 | 1.00 | 13.56 | C |
| ATOM | 28172 | C | ILE | C | 556 | 85.495 | 77.192 | 61.947 | 1.00 | 13.04 | C |
| ATOM | 28173 | O | ILE | C | 556 | 86.594 | 77.777 | 61.992 | 1.00 | 12.31 | O |
| ATOM | 28175 | N | ASP | C | 557 | 84.984 | 76.583 | 63.017 | 1.00 | 11.76 | N |
| ATOM | 28176 | CA | ASP | C | 557 | 85.692 | 76.625 | 64.302 | 1.00 | 13.07 | C |
| ATOM | 28178 | CB | ASP | C | 557 | 84.771 | 76.098 | 65.423 | 1.00 | 13.97 | C |
| ATOM | 28181 | CG | ASP | C | 557 | 83.714 | 77.134 | 65.864 | 1.00 | 17.58 | C |
| ATOM | 28182 | OD1 | ASP | C | 557 | 83.902 | 78.356 | 65.629 | 1.00 | 19.74 | O |
| ATOM | 28183 | OD2 | ASP | C | 557 | 82.685 | 76.699 | 66.470 | 1.00 | 20.17 | O |
| ATOM | 28184 | C | ASP | C | 557 | 87.020 | 75.867 | 64.284 | 1.00 | 12.58 | C |
| ATOM | 28185 | O | ASP | C | 557 | 88.033 | 76.312 | 64.821 | 1.00 | 13.09 | O |
| ATOM | 28187 | N | GLN | C | 558 | 87.000 | 74.709 | 63.651 | 1.00 | 13.81 | N |
| ATOM | 28188 | CA | GLN | C | 558 | 88.166 | 73.855 | 63.566 | 1.00 | 15.01 | C |
| ATOM | 28190 | CB | GLN | C | 558 | 87.774 | 72.548 | 62.919 | 1.00 | 14.86 | C |
| ATOM | 28193 | CG | GLN | C | 558 | 88.903 | 71.612 | 62.658 | 1.00 | 19.63 | C |
| ATOM | 28196 | CD | GLN | C | 558 | 88.450 | 70.305 | 61.983 | 1.00 | 21.37 | C |
| ATOM | 28197 | OE1 | GLN | C | 558 | 87.492 | 70.277 | 61.212 | 1.00 | 28.15 | O |
| ATOM | 28198 | NE2 | GLN | C | 558 | 89.182 | 69.214 | 62.275 | 1.00 | 28.50 | N |
| ATOM | 28201 | C | GLN | C | 558 | 89.266 | 74.500 | 62.757 | 1.00 | 13.80 | C |
| ATOM | 28202 | O | GLN | C | 558 | 90.437 | 74.504 | 63.163 | 1.00 | 14.24 | O |
| ATOM | 28204 | N | HIS | C | 559 | 88.871 | 75.060 | 61.609 | 1.00 | 13.57 | N |
| ATOM | 28205 | CA | HIS | C | 559 | 89.859 | 75.598 | 60.678 | 1.00 | 12.36 | C |
| ATOM | 28207 | CB | HIS | C | 559 | 89.357 | 75.582 | 59.238 | 1.00 | 12.42 | C |
| ATOM | 28210 | CG | HIS | C | 559 | 89.317 | 74.219 | 58.633 | 1.00 | 12.45 | C |
| ATOM | 28211 | ND1 | HIS | C | 559 | 90.334 | 73.727 | 57.838 | 1.00 | 12.83 | N |
| ATOM | 28213 | CE1 | HIS | C | 559 | 90.039 | 72.489 | 57.475 | 1.00 | 14.28 | C |
| ATOM | 28215 | NE2 | HIS | C | 559 | 88.890 | 72.144 | 58.041 | 1.00 | 14.24 | N |
| ATOM | 28217 | CD2 | HIS | C | 559 | 88.419 | 73.205 | 58.768 | 1.00 | 13.02 | C |
| ATOM | 28219 | C | HIS | C | 559 | 90.300 | 76.994 | 61.052 | 1.00 | 12.26 | C |
| ATOM | 28220 | O | HIS | C | 559 | 91.457 | 77.328 | 60.864 | 1.00 | 12.21 | O |
| ATOM | 28222 | N | PHE | C | 560 | 89.371 | 77.818 | 61.511 | 1.00 | 11.55 | N |
| ATOM | 28223 | CA | PHE | C | 560 | 89.622 | 79.249 | 61.650 | 1.00 | 12.18 | C |
| ATOM | 28225 | CB | PHE | C | 560 | 88.610 | 80.077 | 60.826 | 1.00 | 11.49 | C |
| ATOM | 28228 | CG | PHE | C | 560 | 88.559 | 79.719 | 59.359 | 1.00 | 9.37 | C |
| ATOM | 28229 | CD1 | PHE | C | 560 | 89.717 | 79.358 | 58.650 | 1.00 | 10.45 | C |
| ATOM | 28231 | CE1 | PHE | C | 560 | 89.671 | 79.070 | 57.274 | 1.00 | 10.24 | C |
| ATOM | 28233 | CZ | PHE | C | 560 | 88.462 | 79.104 | 56.608 | 1.00 | 11.06 | C |
| ATOM | 28235 | CE2 | PHE | C | 560 | 87.296 | 79.486 | 57.300 | 1.00 | 9.72 | C |
| ATOM | 28237 | CD2 | PHE | C | 560 | 87.358 | 79.773 | 58.668 | 1.00 | 10.62 | C |

| | | | | | | | | | |
|---|---|---|---|---|---|---|---|---|---|
| ATOM | 28239 | C | PHE | C | 560 | 89.617 | 79.734 | 63.095 | 1.00 13.16 | C |
| ATOM | 28240 | O | PHE | C | 560 | 89.996 | 80.878 | 63.348 | 1.00 14.52 | O |
| ATOM | 28242 | N | GLY | C | 561 | 89.156 | 78.890 | 64.027 | 1.00 13.79 | N |
| ATOM | 28243 | CA | GLY | C | 561 | 88.992 | 79.290 | 65.418 | 1.00 14.54 | C |
| ATOM | 28246 | C | GLY | C | 561 | 90.239 | 79.910 | 66.005 | 1.00 15.06 | C |
| ATOM | 28247 | O | GLY | C | 561 | 90.175 | 80.950 | 66.632 | 1.00 16.01 | O |
| ATOM | 28249 | N | SER | C | 562 | 91.381 | 79.293 | 65.798 | 1.00 16.15 | N |
| ATOM | 28250 | CA | SER | C | 562 | 92.607 | 79.871 | 66.358 | 1.00 18.44 | C |
| ATOM | 28252 | CB | SER | C | 562 | 93.780 | 78.974 | 66.049 | 1.00 18.82 | C |
| ATOM | 28255 | OG | SER | C | 562 | 93.670 | 77.793 | 66.805 | 1.00 25.46 | O |
| ATOM | 28257 | C | SER | C | 562 | 92.862 | 81.296 | 65.797 | 1.00 18.52 | C |
| ATOM | 28258 | O | SER | C | 562 | 93.219 | 82.216 | 66.526 | 1.00 18.98 | O |
| ATOM | 28260 | N | ALA | C | 563 | 92.681 | 81.475 | 64.494 | 1.00 19.06 | N |
| ATOM | 28261 | CA | ALA | C | 563 | 92.946 | 82.782 | 63.878 | 1.00 19.00 | C |
| ATOM | 28263 | CB | ALA | C | 563 | 92.950 | 82.682 | 62.346 | 1.00 18.96 | C |
| ATOM | 28267 | C | ALA | C | 563 | 91.959 | 83.857 | 64.325 | 1.00 19.44 | C |
| ATOM | 28268 | O | ALA | C | 563 | 92.243 | 85.032 | 64.218 | 1.00 19.29 | O |
| ATOM | 28270 | N | MSE | C | 564 | 90.793 | 83.457 | 64.815 | 1.00 19.32 | N |
| ATOM | 28271 | CA | MSE | C | 564 | 89.776 | 84.423 | 65.202 | 1.00 21.00 | C |
| ATOM | 28273 | CB | MSE | C | 564 | 88.400 | 83.919 | 64.773 | 1.00 20.15 | C |
| ATOM | 28276 | CG | MSE | C | 564 | 88.308 | 83.680 | 63.262 | 1.00 19.29 | C |
| ATOM | 28279 | SE | MSE | C | 564 | 86.493 | 83.121 | 62.717 | 1.00 26.08 | SE |
| ATOM | 28280 | CE | MSE | C | 564 | 86.236 | 81.433 | 63.827 | 1.00 23.59 | C |
| ATOM | 28284 | C | MSE | C | 564 | 89.749 | 84.728 | 66.699 | 1.00 21.42 | C |
| ATOM | 28285 | O | MSE | C | 564 | 89.000 | 85.597 | 67.127 | 1.00 20.29 | O |
| ATOM | 28287 | N | THR | C | 565 | 90.563 | 84.016 | 67.472 | 1.00 22.96 | N |
| ATOM | 28288 | CA | THR | C | 565 | 90.633 | 84.208 | 68.932 | 1.00 24.00 | C |
| ATOM | 28290 | CB | THR | C | 565 | 91.826 | 83.495 | 69.557 | 1.00 24.33 | C |
| ATOM | 28292 | OG1 | THR | C | 565 | 92.022 | 82.208 | 68.955 | 1.00 26.37 | O |
| ATOM | 28294 | CG2 | THR | C | 565 | 91.582 | 83.303 | 71.059 | 1.00 24.75 | C |
| ATOM | 28298 | C | THR | C | 565 | 90.782 | 85.674 | 69.279 | 1.00 24.29 | C |
| ATOM | 28299 | O | THR | C | 565 | 91.645 | 86.348 | 68.732 | 1.00 24.44 | O |
| ATOM | 28301 | N | GLY | C | 566 | 89.911 | 86.166 | 70.150 | 1.00 25.72 | N |
| ATOM | 28302 | CA | GLY | C | 566 | 90.014 | 87.535 | 70.662 | 1.00 26.71 | C |
| ATOM | 28305 | C | GLY | C | 566 | 89.371 | 88.563 | 69.760 | 1.00 27.36 | C |
| ATOM | 28306 | O | GLY | C | 566 | 89.291 | 89.736 | 70.097 | 1.00 28.77 | O |
| ATOM | 28308 | N | SER | C | 567 | 88.877 | 88.116 | 68.619 | 1.00 27.45 | N |
| ATOM | 28309 | CA | SER | C | 567 | 88.188 | 88.991 | 67.699 | 1.00 27.37 | C |
| ATOM | 28311 | CB | SER | C | 567 | 88.608 | 88.658 | 66.279 | 1.00 27.54 | C |
| ATOM | 28314 | OG | SER | C | 567 | 87.831 | 87.574 | 65.785 | 1.00 25.70 | O |
| ATOM | 28316 | C | SER | C | 567 | 86.703 | 88.730 | 67.860 | 1.00 27.66 | C |
| ATOM | 28317 | O | SER | C | 567 | 86.285 | 87.813 | 68.580 | 1.00 28.59 | O |
| ATOM | 28319 | N | ASN | C | 568 | 85.893 | 89.521 | 67.192 | 1.00 27.51 | N |
| ATOM | 28320 | CA | ASN | C | 568 | 84.485 | 89.243 | 67.179 | 1.00 27.34 | C |
| ATOM | 28322 | CB | ASN | C | 568 | 83.705 | 90.471 | 67.619 | 1.00 28.68 | C |
| ATOM | 28325 | CG | ASN | C | 568 | 82.561 | 90.107 | 68.541 | 1.00 32.41 | C |
| ATOM | 28326 | OD1 | ASN | C | 568 | 81.510 | 89.645 | 68.091 | 1.00 37.26 | O |
| ATOM | 28327 | ND2 | ASN | C | 568 | 82.778 | 90.275 | 69.848 | 1.00 36.57 | N |
| ATOM | 28330 | C | ASN | C | 568 | 84.049 | 88.772 | 65.798 | 1.00 25.04 | C |
| ATOM | 28331 | O | ASN | C | 568 | 82.896 | 88.926 | 65.390 | 1.00 26.04 | O |
| ATOM | 28333 | N | LEU | C | 569 | 84.983 | 88.139 | 65.101 | 1.00 22.03 | N |
| ATOM | 28334 | CA | LEU | C | 569 | 84.784 | 87.772 | 63.700 | 1.00 19.74 | C |
| ATOM | 28336 | CB | LEU | C | 569 | 86.147 | 87.583 | 63.046 | 1.00 19.48 | C |
| ATOM | 28339 | CG | LEU | C | 569 | 86.958 | 88.864 | 62.899 | 1.00 19.74 | C |
| ATOM | 28341 | CD1 | LEU | C | 569 | 88.311 | 88.583 | 62.305 | 1.00 21.54 | C |
| ATOM | 28345 | CD2 | LEU | C | 569 | 86.197 | 89.878 | 62.044 | 1.00 20.27 | C |
| ATOM | 28349 | C | LEU | C | 569 | 83.954 | 86.506 | 63.519 | 1.00 18.14 | C |

| ATOM | 28350 | O   | LEU | C | 569 | 83.275 | 86.315 | 62.496 | 1.00 | 15.66 | O |
|------|-------|-----|-----|---|-----|--------|--------|--------|------|-------|---|
| ATOM | 28352 | N   | ARG | C | 570 | 83.981 | 85.617 | 64.505 | 1.00 | 17.47 | N |
| ATOM | 28353 | CA  | ARG | C | 570 | 83.350 | 84.316 | 64.345 | 1.00 | 17.63 | C |
| ATOM | 28355 | CB  | ARG | C | 570 | 83.655 | 83.438 | 65.581 | 1.00 | 18.12 | C |
| ATOM | 28358 | CG  | ARG | C | 570 | 83.292 | 81.977 | 65.421 | 1.00 | 20.64 | C |
| ATOM | 28361 | CD  | ARG | C | 570 | 81.924 | 81.696 | 65.906 | 1.00 | 24.13 | C |
| ATOM | 28364 | NE  | ARG | C | 570 | 81.727 | 80.288 | 66.217 | 1.00 | 24.58 | N |
| ATOM | 28366 | CZ  | ARG | C | 570 | 80.634 | 79.821 | 66.816 | 1.00 | 23.65 | C |
| ATOM | 28367 | NH1 | ARG | C | 570 | 79.663 | 80.639 | 67.162 | 1.00 | 24.72 | N |
| ATOM | 28370 | NH2 | ARG | C | 570 | 80.499 | 78.538 | 67.048 | 1.00 | 21.00 | N |
| ATOM | 28373 | C   | ARG | C | 570 | 81.846 | 84.367 | 64.025 | 1.00 | 17.83 | C |
| ATOM | 28374 | O   | ARG | C | 570 | 81.382 | 83.740 | 63.070 | 1.00 | 17.89 | O |
| ATOM | 28376 | N   | ASP | C | 571 | 81.063 | 85.120 | 64.784 | 1.00 | 17.70 | N |
| ATOM | 28377 | CA  | ASP | C | 571 | 79.623 | 85.112 | 64.555 | 1.00 | 18.15 | C |
| ATOM | 28379 | CB  | ASP | C | 571 | 78.862 | 85.816 | 65.690 | 1.00 | 19.21 | C |
| ATOM | 28382 | CG  | ASP | C | 571 | 78.733 | 84.950 | 66.941 | 1.00 | 24.53 | C |
| ATOM | 28383 | OD1 | ASP | C | 571 | 78.995 | 83.726 | 66.858 | 1.00 | 29.85 | O |
| ATOM | 28384 | OD2 | ASP | C | 571 | 78.359 | 85.492 | 67.999 | 1.00 | 29.10 | O |
| ATOM | 28385 | C   | ASP | C | 571 | 79.331 | 85.776 | 63.204 | 1.00 | 17.09 | C |
| ATOM | 28386 | O   | ASP | C | 571 | 78.455 | 85.349 | 62.481 | 1.00 | 16.98 | O |
| ATOM | 28388 | N   | GLU | C | 572 | 80.091 | 86.826 | 62.871 | 1.00 | 16.06 | N |
| ATOM | 28389 | CA  | GLU | C | 572 | 79.955 | 87.515 | 61.571 | 1.00 | 16.57 | C |
| ATOM | 28391 | CB  | GLU | C | 572 | 80.948 | 88.665 | 61.435 | 1.00 | 16.52 | C |
| ATOM | 28394 | CG  | GLU | C | 572 | 80.725 | 89.490 | 60.180 | 1.00 | 19.04 | C |
| ATOM | 28397 | CD  | GLU | C | 572 | 81.784 | 90.572 | 59.883 | 1.00 | 19.67 | C |
| ATOM | 28398 | OE1 | GLU | C | 572 | 82.659 | 90.850 | 60.722 | 1.00 | 22.85 | O |
| ATOM | 28399 | OE2 | GLU | C | 572 | 81.715 | 91.149 | 58.768 | 1.00 | 26.17 | O |
| ATOM | 28400 | C   | GLU | C | 572 | 80.204 | 86.516 | 60.441 | 1.00 | 13.85 | C |
| ATOM | 28401 | O   | GLU | C | 572 | 79.458 | 86.460 | 59.474 | 1.00 | 14.65 | O |
| ATOM | 28403 | N   | LEU | C | 573 | 81.262 | 85.721 | 60.577 | 1.00 | 12.89 | N |
| ATOM | 28404 | CA  | LEU | C | 573 | 81.644 | 84.783 | 59.509 | 1.00 | 12.57 | C |
| ATOM | 28406 | CB  | LEU | C | 573 | 83.022 | 84.172 | 59.789 | 1.00 | 12.48 | C |
| ATOM | 28409 | CG  | LEU | C | 573 | 83.487 | 83.212 | 58.697 | 1.00 | 11.41 | C |
| ATOM | 28411 | CD1 | LEU | C | 573 | 83.706 | 83.977 | 57.370 | 1.00 | 13.42 | C |
| ATOM | 28415 | CD2 | LEU | C | 573 | 84.718 | 82.479 | 59.083 | 1.00 | 12.11 | C |
| ATOM | 28419 | C   | LEU | C | 573 | 80.586 | 83.689 | 59.336 | 1.00 | 13.02 | C |
| ATOM | 28420 | O   | LEU | C | 573 | 80.172 | 83.349 | 58.227 | 1.00 | 11.41 | O |
| ATOM | 28422 | N   | VAL | C | 574 | 80.117 | 83.138 | 60.452 | 1.00 | 12.80 | N |
| ATOM | 28423 | CA  | VAL | C | 574 | 79.048 | 82.139 | 60.354 | 1.00 | 14.04 | C |
| ATOM | 28425 | CB  | VAL | C | 574 | 78.639 | 81.613 | 61.741 | 1.00 | 14.50 | C |
| ATOM | 28427 | CG1 | VAL | C | 574 | 77.462 | 80.660 | 61.621 | 1.00 | 14.10 | C |
| ATOM | 28431 | CG2 | VAL | C | 574 | 79.810 | 80.918 | 62.418 | 1.00 | 15.20 | C |
| ATOM | 28435 | C   | VAL | C | 574 | 77.831 | 82.695 | 59.631 | 1.00 | 13.65 | C |
| ATOM | 28436 | O   | VAL | C | 574 | 77.305 | 82.068 | 58.728 | 1.00 | 14.17 | O |
| ATOM | 28438 | N   | GLU | C | 575 | 77.363 | 83.889 | 59.991 | 1.00 | 13.92 | N |
| ATOM | 28439 | CA  | GLU | C | 575 | 76.207 | 84.457 | 59.289 | 1.00 | 15.15 | C |
| ATOM | 28441 | CB  | GLU | C | 575 | 75.830 | 85.791 | 59.919 | 1.00 | 15.55 | C |
| ATOM | 28444 | CG  | GLU | C | 575 | 74.709 | 86.470 | 59.160 | 1.00 | 19.38 | C |
| ATOM | 28447 | CD  | GLU | C | 575 | 74.034 | 87.609 | 59.910 | 1.00 | 20.12 | C |
| ATOM | 28448 | OE1 | GLU | C | 575 | 74.593 | 88.146 | 60.912 | 1.00 | 28.16 | O |
| ATOM | 28449 | OE2 | GLU | C | 575 | 72.899 | 87.920 | 59.492 | 1.00 | 31.58 | O |
| ATOM | 28450 | C   | GLU | C | 575 | 76.434 | 84.679 | 57.799 | 1.00 | 14.39 | C |
| ATOM | 28451 | O   | GLU | C | 575 | 75.582 | 84.383 | 56.963 | 1.00 | 12.62 | O |
| ATOM | 28453 | N   | LYS | C | 576 | 77.569 | 85.287 | 57.466 | 1.00 | 14.09 | N |
| ATOM | 28454 | CA  | LYS | C | 576 | 77.811 | 85.685 | 56.073 | 1.00 | 14.75 | C |
| ATOM | 28456 | CB  | LYS | C | 576 | 78.939 | 86.690 | 56.001 | 1.00 | 15.66 | C |
| ATOM | 28459 | CG  | LYS | C | 576 | 78.598 | 87.987 | 56.701 | 1.00 | 15.62 | C |

| | | | | | | | | | |
|---|---|---|---|---|---|---|---|---|---|
| ATOM | 28462 | CD | LYS | C | 576 | 79.520 | 89.168 | 56.361 | 1.00 19.05 | C |
| ATOM | 28465 | CE | LYS | C | 576 | 79.065 | 90.475 | 57.024 | 1.00 22.67 | C |
| ATOM | 28468 | NZ | LYS | C | 576 | 77.599 | 90.498 | 57.167 | 1.00 27.68 | N |
| ATOM | 28472 | C | LYS | C | 576 | 78.103 | 84.456 | 55.229 | 1.00 14.02 | C |
| ATOM | 28473 | O | LYS | C | 576 | 77.710 | 84.376 | 54.047 | 1.00 14.18 | O |
| ATOM | 28475 | N | VAL | C | 577 | 78.730 | 83.454 | 55.846 | 1.00 12.89 | N |
| ATOM | 28476 | CA | VAL | C | 577 | 78.971 | 82.227 | 55.113 | 1.00 13.50 | C |
| ATOM | 28478 | CB | VAL | C | 577 | 80.030 | 81.286 | 55.781 | 1.00 14.41 | C |
| ATOM | 28480 | CG1 | VAL | C | 577 | 79.949 | 79.859 | 55.212 | 1.00 14.92 | C |
| ATOM | 28484 | CG2 | VAL | C | 577 | 81.426 | 81.862 | 55.611 | 1.00 13.83 | C |
| ATOM | 28488 | C | VAL | C | 577 | 77.616 | 81.508 | 54.870 | 1.00 14.89 | C |
| ATOM | 28489 | O | VAL | C | 577 | 77.352 | 81.018 | 53.792 | 1.00 16.39 | O |
| ATOM | 28491 | N | ASN | C | 578 | 76.769 | 81.465 | 55.892 | 1.00 15.54 | N |
| ATOM | 28492 | CA | ASN | C | 578 | 75.459 | 80.852 | 55.744 | 1.00 16.40 | C |
| ATOM | 28494 | CB | ASN | C | 578 | 74.649 | 80.905 | 57.063 | 1.00 16.30 | C |
| ATOM | 28497 | CG | ASN | C | 578 | 75.070 | 79.854 | 58.102 | 1.00 16.06 | C |
| ATOM | 28498 | OD1 | ASN | C | 578 | 75.703 | 78.870 | 57.772 | 1.00 20.14 | O |
| ATOM | 28499 | ND2 | ASN | C | 578 | 74.715 | 80.104 | 59.395 | 1.00 17.71 | N |
| ATOM | 28502 | C | ASN | C | 578 | 74.653 | 81.556 | 54.629 | 1.00 16.78 | C |
| ATOM | 28503 | O | ASN | C | 578 | 74.019 | 80.882 | 53.783 | 1.00 17.62 | O |
| ATOM | 28505 | N | LYS | C | 579 | 74.678 | 82.904 | 54.617 | 1.00 17.33 | N |
| ATOM | 28506 | CA | LYS | C | 579 | 74.006 | 83.710 | 53.579 | 1.00 18.25 | C |
| ATOM | 28508 | CB | LYS | C | 579 | 74.080 | 85.203 | 53.902 | 1.00 19.33 | C |
| ATOM | 28511 | CG | LYS | C | 579 | 73.385 | 85.551 | 55.195 | 1.00 23.44 | C |
| ATOM | 28514 | CD | LYS | C | 579 | 72.862 | 86.994 | 55.195 | 1.00 29.39 | C |
| ATOM | 28517 | CE | LYS | C | 579 | 72.680 | 87.527 | 56.610 | 1.00 31.19 | C |
| ATOM | 28520 | NZ | LYS | C | 579 | 71.940 | 86.600 | 57.532 | 1.00 33.09 | N |
| ATOM | 28524 | C | LYS | C | 579 | 74.550 | 83.451 | 52.185 | 1.00 17.96 | C |
| ATOM | 28525 | O | LYS | C | 579 | 73.792 | 83.300 | 51.228 | 1.00 19.63 | O |
| ATOM | 28527 | N | THR | C | 580 | 75.872 | 83.394 | 52.059 | 1.00 17.13 | N |
| ATOM | 28528 | CA | THR | C | 580 | 76.488 | 83.177 | 50.783 | 1.00 17.60 | C |
| ATOM | 28530 | CB | THR | C | 580 | 78.012 | 83.322 | 50.863 | 1.00 17.12 | C |
| ATOM | 28532 | OG1 | THR | C | 580 | 78.319 | 84.696 | 51.132 | 1.00 19.92 | O |
| ATOM | 28534 | CG2 | THR | C | 580 | 78.693 | 82.915 | 49.539 | 1.00 17.87 | C |
| ATOM | 28538 | C | THR | C | 580 | 76.084 | 81.824 | 50.240 | 1.00 16.53 | C |
| ATOM | 28539 | O | THR | C | 580 | 75.753 | 81.686 | 49.078 | 1.00 16.09 | O |
| ATOM | 28541 | N | LEU | C | 581 | 76.115 | 80.811 | 51.093 | 1.00 16.49 | N |
| ATOM | 28542 | CA | LEU | C | 581 | 75.831 | 79.500 | 50.621 | 1.00 17.19 | C |
| ATOM | 28544 | CB | LEU | C | 581 | 76.110 | 78.499 | 51.729 | 1.00 16.43 | C |
| ATOM | 28547 | CG | LEU | C | 581 | 77.577 | 78.220 | 52.082 | 1.00 14.18 | C |
| ATOM | 28549 | CD1 | LEU | C | 581 | 77.694 | 77.389 | 53.346 | 1.00 17.08 | C |
| ATOM | 28553 | CD2 | LEU | C | 581 | 78.259 | 77.528 | 50.911 | 1.00 14.88 | C |
| ATOM | 28557 | C | LEU | C | 581 | 74.354 | 79.370 | 50.208 | 1.00 18.67 | C |
| ATOM | 28558 | O | LEU | C | 581 | 74.042 | 78.785 | 49.167 | 1.00 19.98 | O |
| ATOM | 28560 | N | ALA | C | 582 | 73.481 | 79.836 | 51.092 | 1.00 21.01 | N |
| ATOM | 28561 | CA | ALA | C | 582 | 72.029 | 79.831 | 50.859 | 1.00 22.00 | C |
| ATOM | 28563 | CB | ALA | C | 582 | 71.291 | 80.586 | 51.974 | 1.00 22.01 | C |
| ATOM | 28567 | C | ALA | C | 582 | 71.688 | 80.408 | 49.531 | 1.00 23.51 | C |
| ATOM | 28568 | O | ALA | C | 582 | 70.905 | 79.791 | 48.762 | 1.00 24.02 | O |
| ATOM | 28570 | N | LYS | C | 583 | 72.233 | 81.584 | 49.222 | 1.00 23.74 | N |
| ATOM | 28571 | CA | LYS | C | 583 | 71.818 | 82.243 | 48.017 | 1.00 25.25 | C |
| ATOM | 28573 | CB | LYS | C | 583 | 72.176 | 83.740 | 48.004 | 1.00 26.39 | C |
| ATOM | 28576 | CG | LYS | C | 583 | 73.569 | 84.111 | 47.481 | 1.00 29.59 | C |
| ATOM | 28579 | CD | LYS | C | 583 | 73.726 | 85.640 | 47.247 | 1.00 30.01 | C |
| ATOM | 28582 | CE | LYS | C | 583 | 75.222 | 86.040 | 47.053 | 1.00 32.62 | C |
| ATOM | 28585 | NZ | LYS | C | 583 | 76.166 | 86.049 | 48.272 | 1.00 32.21 | N |
| ATOM | 28589 | C | LYS | C | 583 | 72.386 | 81.518 | 46.824 | 1.00 23.86 | C |

| | | | | | | | | | |
|---|---|---|---|---|---|---|---|---|---|
| ATOM | 28590 | O | LYS | C | 583 | 71.726 | 81.415 | 45.823 | 1.00 22.92 | O |
| ATOM | 28592 | N | ARG | C | 584 | 73.603 | 80.975 | 46.950 | 1.00 21.04 | N |
| ATOM | 28593 | CA | ARG | C | 584 | 74.288 | 80.409 | 45.798 | 1.00 20.32 | C |
| ATOM | 28595 | CB | ARG | C | 584 | 75.790 | 80.223 | 46.083 | 1.00 20.18 | C |
| ATOM | 28598 | CG | ARG | C | 584 | 76.599 | 79.599 | 44.957 | 1.00 19.80 | C |
| ATOM | 28601 | CD | ARG | C | 584 | 76.414 | 80.297 | 43.650 | 1.00 18.95 | C |
| ATOM | 28604 | NE | ARG | C | 584 | 77.222 | 79.762 | 42.575 | 1.00 18.44 | N |
| ATOM | 28606 | CZ | ARG | C | 584 | 77.067 | 80.086 | 41.294 | 1.00 22.01 | C |
| ATOM | 28607 | NH1 | ARG | C | 584 | 76.183 | 81.010 | 40.938 | 1.00 22.69 | N |
| ATOM | 28610 | NH2 | ARG | C | 584 | 77.817 | 79.540 | 40.367 | 1.00 20.25 | N |
| ATOM | 28613 | C | ARG | C | 584 | 73.664 | 79.072 | 45.415 | 1.00 19.25 | C |
| ATOM | 28614 | O | ARG | C | 584 | 73.445 | 78.780 | 44.233 | 1.00 18.04 | O |
| ATOM | 28616 | N | LEU | C | 585 | 73.349 | 78.300 | 46.444 | 1.00 19.16 | N |
| ATOM | 28617 | CA | LEU | C | 585 | 72.797 | 76.940 | 46.257 | 1.00 19.98 | C |
| ATOM | 28619 | CB | LEU | C | 585 | 72.674 | 76.214 | 47.581 | 1.00 21.23 | C |
| ATOM | 28622 | CG | LEU | C | 585 | 74.049 | 75.782 | 48.124 | 1.00 19.26 | C |
| ATOM | 28624 | CD1 | LEU | C | 585 | 73.954 | 75.420 | 49.586 | 1.00 20.04 | C |
| ATOM | 28628 | CD2 | LEU | C | 585 | 74.693 | 74.670 | 47.299 | 1.00 19.85 | C |
| ATOM | 28632 | C | LEU | C | 585 | 71.466 | 77.013 | 45.534 | 1.00 21.79 | C |
| ATOM | 28633 | O | LEU | C | 585 | 71.164 | 76.185 | 44.691 | 1.00 20.66 | O |
| ATOM | 28635 | N | GLU | C | 586 | 70.704 | 78.065 | 45.790 | 1.00 23.18 | N |
| ATOM | 28636 | CA | GLU | C | 586 | 69.419 | 78.206 | 45.086 | 1.00 25.43 | C |
| ATOM | 28638 | CB | GLU | C | 586 | 68.662 | 79.442 | 45.591 | 1.00 25.73 | C |
| ATOM | 28641 | CG | GLU | C | 586 | 68.903 | 80.642 | 44.693 | 1.00 30.60 | C |
| ATOM | 28644 | CD | GLU | C | 586 | 68.513 | 81.998 | 45.310 | 1.00 31.86 | C |
| ATOM | 28645 | OE1 | GLU | C | 586 | 67.305 | 82.133 | 45.700 | 1.00 36.89 | O |
| ATOM | 28646 | OE2 | GLU | C | 586 | 69.414 | 82.916 | 45.339 | 1.00 34.76 | O |
| ATOM | 28647 | C | GLU | C | 586 | 69.604 | 78.284 | 43.546 | 1.00 24.43 | C |
| ATOM | 28648 | O | GLU | C | 586 | 68.659 | 78.052 | 42.800 | 1.00 25.99 | O |
| ATOM | 28650 | N | GLN | C | 587 | 70.784 | 78.653 | 43.040 | 1.00 23.05 | N |
| ATOM | 28651 | CA | GLN | C | 587 | 70.951 | 78.829 | 41.634 | 1.00 23.07 | C |
| ATOM | 28653 | CB | GLN | C | 587 | 71.414 | 80.264 | 41.308 | 1.00 25.47 | C |
| ATOM | 28656 | CG | GLN | C | 587 | 72.796 | 80.610 | 41.658 | 1.00 28.04 | C |
| ATOM | 28659 | CD | GLN | C | 587 | 73.003 | 82.126 | 41.983 | 1.00 27.91 | C |
| ATOM | 28660 | OE1 | GLN | C | 587 | 73.784 | 82.452 | 42.857 | 1.00 29.99 | O |
| ATOM | 28661 | NE2 | GLN | C | 587 | 72.316 | 83.023 | 41.257 | 1.00 33.39 | N |
| ATOM | 28664 | C | GLN | C | 587 | 71.838 | 77.762 | 40.990 | 1.00 19.97 | C |
| ATOM | 28665 | O | GLN | C | 587 | 72.132 | 77.843 | 39.811 | 1.00 20.06 | O |
| ATOM | 28667 | N | THR | C | 588 | 72.335 | 76.814 | 41.778 | 1.00 16.72 | N |
| ATOM | 28668 | CA | THR | C | 588 | 73.194 | 75.747 | 41.204 | 1.00 16.16 | C |
| ATOM | 28670 | CB | THR | C | 588 | 74.548 | 75.762 | 41.912 | 1.00 15.10 | C |
| ATOM | 28672 | OG1 | THR | C | 588 | 74.338 | 75.467 | 43.300 | 1.00 16.48 | O |
| ATOM | 28674 | CG2 | THR | C | 588 | 75.251 | 77.144 | 41.683 | 1.00 17.94 | C |
| ATOM | 28678 | C | THR | C | 588 | 72.498 | 74.381 | 41.297 | 1.00 15.04 | C |
| ATOM | 28679 | O | THR | C | 588 | 73.147 | 73.301 | 41.306 | 1.00 14.33 | O |
| ATOM | 28681 | N | ASN | C | 589 | 71.150 | 74.432 | 41.270 | 1.00 15.24 | N |
| ATOM | 28682 | CA | ASN | C | 589 | 70.307 | 73.260 | 41.345 | 1.00 15.23 | C |
| ATOM | 28684 | CB | ASN | C | 589 | 68.867 | 73.627 | 41.755 | 1.00 15.43 | C |
| ATOM | 28687 | CG | ASN | C | 589 | 68.264 | 74.755 | 40.924 | 1.00 17.40 | C |
| ATOM | 28688 | OD1 | ASN | C | 589 | 68.978 | 75.613 | 40.379 | 1.00 20.78 | O |
| ATOM | 28689 | ND2 | ASN | C | 589 | 66.918 | 74.802 | 40.882 | 1.00 15.44 | N |
| ATOM | 28692 | C | ASN | C | 589 | 70.322 | 72.387 | 40.092 | 1.00 15.67 | C |
| ATOM | 28693 | O | ASN | C | 589 | 69.753 | 71.266 | 40.140 | 1.00 16.90 | O |
| ATOM | 28695 | N | SER | C | 590 | 71.010 | 72.826 | 39.024 | 1.00 16.15 | N |
| ATOM | 28696 | CA | SER | C | 590 | 71.257 | 71.991 | 37.852 | 1.00 17.17 | C |
| ATOM | 28698 | CB | SER | C | 590 | 71.011 | 72.803 | 36.587 | 1.00 18.79 | C |
| ATOM | 28701 | OG | SER | C | 590 | 69.676 | 73.246 | 36.577 | 1.00 24.07 | O |

| ATOM | 28703 | C | SER | C | 590 | 72.658 | 71.410 | 37.774 | 1.00 | 16.16 | C |
|------|-------|-----|-----|---|-----|--------|--------|--------|------|-------|---|
| ATOM | 28704 | O | SER | C | 590 | 72.974 | 70.688 | 36.837 | 1.00 | 18.20 | O |
| ATOM | 28706 | N | TYR | C | 591 | 73.501 | 71.726 | 38.772 | 1.00 | 15.33 | N |
| ATOM | 28707 | CA | TYR | C | 591 | 74.838 | 71.148 | 38.894 | 1.00 | 15.14 | C |
| ATOM | 28709 | CB | TYR | C | 591 | 75.694 | 72.005 | 39.822 | 1.00 | 16.50 | C |
| ATOM | 28712 | CG | TYR | C | 591 | 76.229 | 73.307 | 39.274 | 1.00 | 17.67 | C |
| ATOM | 28713 | CD1 | TYR | C | 591 | 75.413 | 74.220 | 38.629 | 1.00 | 19.55 | C |
| ATOM | 28715 | CE1 | TYR | C | 591 | 75.922 | 75.423 | 38.173 | 1.00 | 20.12 | C |
| ATOM | 28717 | CZ | TYR | C | 591 | 77.279 | 75.710 | 38.359 | 1.00 | 22.16 | C |
| ATOM | 28718 | OH | TYR | C | 591 | 77.821 | 76.909 | 37.889 | 1.00 | 24.21 | O |
| ATOM | 28720 | CE2 | TYR | C | 591 | 78.097 | 74.822 | 39.005 | 1.00 | 21.56 | C |
| ATOM | 28722 | CD2 | TYR | C | 591 | 77.573 | 73.646 | 39.456 | 1.00 | 17.57 | C |
| ATOM | 28724 | C | TYR | C | 591 | 74.800 | 69.735 | 39.488 | 1.00 | 14.17 | C |
| ATOM | 28725 | O | TYR | C | 591 | 73.997 | 69.459 | 40.395 | 1.00 | 13.89 | O |
| ATOM | 28727 | N | ASP | C | 592 | 75.721 | 68.887 | 39.031 | 1.00 | 13.40 | N |
| ATOM | 28728 | CA | ASP | C | 592 | 75.987 | 67.613 | 39.709 | 1.00 | 12.64 | C |
| ATOM | 28730 | CB | ASP | C | 592 | 76.893 | 66.725 | 38.870 | 1.00 | 13.30 | C |
| ATOM | 28733 | CG | ASP | C | 592 | 76.192 | 66.146 | 37.642 | 1.00 | 14.37 | C |
| ATOM | 28734 | OD1 | ASP | C | 592 | 74.975 | 66.366 | 37.416 | 1.00 | 16.40 | O |
| ATOM | 28735 | OD2 | ASP | C | 592 | 76.913 | 65.466 | 36.885 | 1.00 | 20.26 | O |
| ATOM | 28736 | C | ASP | C | 592 | 76.607 | 67.885 | 41.063 | 1.00 | 13.01 | C |
| ATOM | 28737 | O | ASP | C | 592 | 77.212 | 68.959 | 41.321 | 1.00 | 12.34 | O |
| ATOM | 28739 | N | LEU | C | 593 | 76.489 | 66.876 | 41.912 | 1.00 | 12.89 | N |
| ATOM | 28740 | CA | LEU | C | 593 | 76.708 | 67.051 | 43.345 | 1.00 | 13.17 | C |
| ATOM | 28742 | CB | LEU | C | 593 | 76.493 | 65.732 | 44.078 | 1.00 | 13.74 | C |
| ATOM | 28745 | CG | LEU | C | 593 | 76.618 | 65.725 | 45.593 | 1.00 | 13.29 | C |
| ATOM | 28747 | CD1 | LEU | C | 593 | 75.500 | 66.587 | 46.214 | 1.00 | 14.26 | C |
| ATOM | 28751 | CD2 | LEU | C | 593 | 76.530 | 64.273 | 46.111 | 1.00 | 14.93 | C |
| ATOM | 28755 | C | LEU | C | 593 | 78.096 | 67.558 | 43.675 | 1.00 | 12.47 | C |
| ATOM | 28756 | O | LEU | C | 593 | 78.262 | 68.482 | 44.456 | 1.00 | 13.50 | O |
| ATOM | 28758 | N | VAL | C | 594 | 79.109 | 66.870 | 43.137 | 1.00 | 13.08 | N |
| ATOM | 28759 | CA | VAL | C | 594 | 80.492 | 67.183 | 43.496 | 1.00 | 13.75 | C |
| ATOM | 28761 | CB | VAL | C | 594 | 81.469 | 66.126 | 42.985 | 1.00 | 14.40 | C |
| ATOM | 28763 | CG1 | VAL | C | 594 | 82.884 | 66.599 | 43.143 | 1.00 | 13.94 | C |
| ATOM | 28767 | CG2 | VAL | C | 594 | 81.279 | 64.774 | 43.751 | 1.00 | 15.22 | C |
| ATOM | 28771 | C | VAL | C | 594 | 80.876 | 68.637 | 43.033 | 1.00 | 13.14 | C |
| ATOM | 28772 | O | VAL | C | 594 | 81.319 | 69.466 | 43.842 | 1.00 | 13.58 | O |
| ATOM | 28774 | N | PRO | C | 595 | 80.696 | 68.960 | 41.745 | 1.00 | 14.04 | N |
| ATOM | 28775 | CA | PRO | C | 595 | 80.997 | 70.341 | 41.328 | 1.00 | 13.57 | C |
| ATOM | 28777 | CB | PRO | C | 595 | 80.697 | 70.342 | 39.828 | 1.00 | 14.98 | C |
| ATOM | 28780 | CG | PRO | C | 595 | 79.897 | 69.117 | 39.607 | 1.00 | 15.34 | C |
| ATOM | 28783 | CD | PRO | C | 595 | 80.265 | 68.139 | 40.621 | 1.00 | 14.29 | C |
| ATOM | 28786 | C | PRO | C | 595 | 80.127 | 71.369 | 42.037 | 1.00 | 13.52 | C |
| ATOM | 28787 | O | PRO | C | 595 | 80.592 | 72.484 | 42.276 | 1.00 | 13.57 | O |
| ATOM | 28788 | N | ARG | C | 596 | 78.884 | 71.003 | 42.342 | 1.00 | 13.12 | N |
| ATOM | 28789 | CA | ARG | C | 596 | 77.989 | 71.910 | 43.025 | 1.00 | 13.40 | C |
| ATOM | 28791 | CB | ARG | C | 596 | 76.653 | 71.300 | 43.291 | 1.00 | 13.02 | C |
| ATOM | 28794 | CG | ARG | C | 596 | 75.661 | 72.296 | 43.871 | 1.00 | 16.30 | C |
| ATOM | 28797 | CD | ARG | C | 596 | 74.309 | 71.661 | 44.041 | 1.00 | 18.10 | C |
| ATOM | 28800 | NE | ARG | C | 596 | 73.298 | 72.692 | 44.290 | 1.00 | 18.92 | N |
| ATOM | 28802 | CZ | ARG | C | 596 | 72.032 | 72.422 | 44.615 | 1.00 | 21.33 | C |
| ATOM | 28803 | NH1 | ARG | C | 596 | 71.619 | 71.174 | 44.756 | 1.00 | 20.85 | N |
| ATOM | 28806 | NH2 | ARG | C | 596 | 71.166 | 73.407 | 44.757 | 1.00 | 21.01 | N |
| ATOM | 28809 | C | ARG | C | 596 | 78.585 | 72.388 | 44.352 | 1.00 | 13.18 | C |
| ATOM | 28810 | O | ARG | C | 596 | 78.571 | 73.561 | 44.677 | 1.00 | 12.54 | O |
| ATOM | 28812 | N | TRP | C | 597 | 79.105 | 71.463 | 45.130 | 1.00 | 12.70 | N |
| ATOM | 28813 | CA | TRP | C | 597 | 79.576 | 71.834 | 46.446 | 1.00 | 13.29 | C |

| ATOM | 28815 | CB | TRP | C | 597 | 79.569 | 70.625 | 47.397 | 1.00 | 13.56 | C |
| ATOM | 28818 | CG | TRP | C | 597 | 78.187 | 70.392 | 47.877 | 1.00 | 14.20 | C |
| ATOM | 28819 | CD1 | TRP | C | 597 | 77.358 | 69.348 | 47.539 | 1.00 | 17.14 | C |
| ATOM | 28821 | NE1 | TRP | C | 597 | 76.122 | 69.515 | 48.139 | 1.00 | 16.60 | N |
| ATOM | 28823 | CE2 | TRP | C | 597 | 76.140 | 70.672 | 48.889 | 1.00 | 15.78 | C |
| ATOM | 28824 | CD2 | TRP | C | 597 | 77.414 | 71.265 | 48.726 | 1.00 | 13.36 | C |
| ATOM | 28825 | CE3 | TRP | C | 597 | 77.709 | 72.454 | 49.419 | 1.00 | 15.73 | C |
| ATOM | 28827 | CZ3 | TRP | C | 597 | 76.709 | 73.033 | 50.229 | 1.00 | 16.27 | C |
| ATOM | 28829 | CH2 | TRP | C | 597 | 75.436 | 72.412 | 50.351 | 1.00 | 17.50 | C |
| ATOM | 28831 | CZ2 | TRP | C | 597 | 75.142 | 71.232 | 49.707 | 1.00 | 15.14 | C |
| ATOM | 28833 | C | TRP | C | 597 | 80.919 | 72.507 | 46.422 | 1.00 | 12.28 | C |
| ATOM | 28834 | O | TRP | C | 597 | 81.182 | 73.367 | 47.266 | 1.00 | 11.69 | O |
| ATOM | 28836 | N | HIS | C | 598 | 81.787 | 72.129 | 45.483 | 1.00 | 11.92 | N |
| ATOM | 28837 | CA | HIS | C | 598 | 83.003 | 72.905 | 45.302 | 1.00 | 11.77 | C |
| ATOM | 28839 | CB | HIS | C | 598 | 84.002 | 72.212 | 44.405 | 1.00 | 12.98 | C |
| ATOM | 28842 | CG | HIS | C | 598 | 84.648 | 71.061 | 45.078 | 1.00 | 14.54 | C |
| ATOM | 28843 | ND1 | HIS | C | 598 | 85.696 | 71.199 | 45.959 | 1.00 | 12.71 | N |
| ATOM | 28845 | CE1 | HIS | C | 598 | 86.014 | 70.010 | 46.439 | 1.00 | 16.55 | C |
| ATOM | 28847 | NE2 | HIS | C | 598 | 85.175 | 69.123 | 45.943 | 1.00 | 15.19 | N |
| ATOM | 28849 | CD2 | HIS | C | 598 | 84.299 | 69.755 | 45.110 | 1.00 | 16.15 | C |
| ATOM | 28851 | C | HIS | C | 598 | 82.737 | 74.329 | 44.859 | 1.00 | 12.18 | C |
| ATOM | 28852 | O | HIS | C | 598 | 83.388 | 75.266 | 45.330 | 1.00 | 12.76 | O |
| ATOM | 28854 | N | ASP | C | 599 | 81.730 | 74.494 | 44.018 | 1.00 | 12.70 | N |
| ATOM | 28855 | CA | ASP | C | 599 | 81.303 | 75.839 | 43.606 | 1.00 | 13.34 | C |
| ATOM | 28857 | CB | ASP | C | 599 | 80.229 | 75.732 | 42.534 | 1.00 | 13.96 | C |
| ATOM | 28860 | CG | ASP | C | 599 | 79.593 | 77.052 | 42.203 | 1.00 | 14.28 | C |
| ATOM | 28861 | OD1 | ASP | C | 599 | 80.022 | 77.708 | 41.217 | 1.00 | 18.78 | O |
| ATOM | 28862 | OD2 | ASP | C | 599 | 78.643 | 77.417 | 42.909 | 1.00 | 16.04 | O |
| ATOM | 28863 | C | ASP | C | 599 | 80.801 | 76.665 | 44.806 | 1.00 | 12.92 | C |
| ATOM | 28864 | O | ASP | C | 599 | 81.184 | 77.821 | 44.989 | 1.00 | 11.64 | O |
| ATOM | 28866 | N | ALA | C | 600 | 79.940 | 76.076 | 45.619 | 1.00 | 12.89 | N |
| ATOM | 28867 | CA | ALA | C | 600 | 79.330 | 76.826 | 46.710 | 1.00 | 12.94 | C |
| ATOM | 28869 | CB | ALA | C | 600 | 78.318 | 75.974 | 47.411 | 1.00 | 12.80 | C |
| ATOM | 28873 | C | ALA | C | 600 | 80.399 | 77.314 | 47.672 | 1.00 | 11.70 | C |
| ATOM | 28874 | O | ALA | C | 600 | 80.419 | 78.494 | 48.124 | 1.00 | 11.09 | O |
| ATOM | 28876 | N | PHE | C | 601 | 81.329 | 76.425 | 48.010 | 1.00 | 10.44 | N |
| ATOM | 28877 | CA | PHE | C | 601 | 82.371 | 76.739 | 48.992 | 1.00 | 10.73 | C |
| ATOM | 28879 | CB | PHE | C | 601 | 82.839 | 75.441 | 49.744 | 1.00 | 10.52 | C |
| ATOM | 28882 | CG | PHE | C | 601 | 81.952 | 75.087 | 50.885 | 1.00 | 10.77 | C |
| ATOM | 28883 | CD1 | PHE | C | 601 | 81.973 | 75.854 | 52.040 | 1.00 | 12.73 | C |
| ATOM | 28885 | CE1 | PHE | C | 601 | 81.089 | 75.621 | 53.086 | 1.00 | 12.85 | C |
| ATOM | 28887 | CZ | PHE | C | 601 | 80.161 | 74.617 | 52.963 | 1.00 | 12.75 | C |
| ATOM | 28889 | CE2 | PHE | C | 601 | 80.108 | 73.863 | 51.806 | 1.00 | 10.56 | C |
| ATOM | 28891 | CD2 | PHE | C | 601 | 80.968 | 74.145 | 50.734 | 1.00 | 12.55 | C |
| ATOM | 28893 | C | PHE | C | 601 | 83.520 | 77.587 | 48.404 | 1.00 | 10.95 | C |
| ATOM | 28894 | O | PHE | C | 601 | 84.224 | 78.281 | 49.143 | 1.00 | 11.50 | O |
| ATOM | 28896 | N | SER | C | 602 | 83.696 | 77.546 | 47.087 | 1.00 | 12.29 | N |
| ATOM | 28897 | CA | SER | C | 602 | 84.594 | 78.486 | 46.401 | 1.00 | 13.24 | C |
| ATOM | 28899 | CB | SER | C | 602 | 84.730 | 78.140 | 44.911 | 1.00 | 13.53 | C |
| ATOM | 28902 | OG | SER | C | 602 | 85.594 | 79.041 | 44.270 | 1.00 | 15.50 | O |
| ATOM | 28904 | C | SER | C | 602 | 84.024 | 79.923 | 46.590 | 1.00 | 12.01 | C |
| ATOM | 28905 | O | SER | C | 602 | 84.723 | 80.854 | 47.005 | 1.00 | 11.61 | O |
| ATOM | 28907 | N | PHE | C | 603 | 82.715 | 80.058 | 46.393 | 1.00 | 12.12 | N |
| ATOM | 28908 | CA | PHE | C | 603 | 82.088 | 81.362 | 46.591 | 1.00 | 12.63 | C |
| ATOM | 28910 | CB | PHE | C | 603 | 80.639 | 81.303 | 46.162 | 1.00 | 13.52 | C |
| ATOM | 28913 | CG | PHE | C | 603 | 80.045 | 82.633 | 45.794 | 1.00 | 14.44 | C |
| ATOM | 28914 | CD1 | PHE | C | 603 | 80.615 | 83.849 | 46.184 | 1.00 | 16.84 | C |

| ATOM | 28916 | CE1 | PHE | C | 603 | 80.018 | 85.061 | 45.809 | 1.00 | 16.58 | C |
| --- | --- | --- | --- | --- | --- | --- | --- | --- | --- | --- | --- |
| ATOM | 28918 | CZ | PHE | C | 603 | 78.876 | 85.041 | 45.065 | 1.00 | 17.81 | C |
| ATOM | 28920 | CE2 | PHE | C | 603 | 78.343 | 83.862 | 44.653 | 1.00 | 22.19 | C |
| ATOM | 28922 | CD2 | PHE | C | 603 | 78.930 | 82.667 | 45.008 | 1.00 | 19.70 | C |
| ATOM | 28924 | C | PHE | C | 603 | 82.215 | 81.758 | 48.069 | 1.00 | 12.15 | C |
| ATOM | 28925 | O | PHE | C | 603 | 82.660 | 82.843 | 48.402 | 1.00 | 12.09 | O |
| ATOM | 28927 | N | ALA | C | 604 | 81.935 | 80.832 | 48.976 | 1.00 | 11.97 | N |
| ATOM | 28928 | CA | ALA | C | 604 | 82.067 | 81.152 | 50.406 | 1.00 | 11.80 | C |
| ATOM | 28930 | CB | ALA | C | 604 | 81.564 | 79.989 | 51.241 | 1.00 | 11.57 | C |
| ATOM | 28934 | C | ALA | C | 604 | 83.504 | 81.523 | 50.807 | 1.00 | 11.37 | C |
| ATOM | 28935 | O | ALA | C | 604 | 83.720 | 82.350 | 51.717 | 1.00 | 12.14 | O |
| ATOM | 28937 | N | ALA | C | 605 | 84.511 | 80.927 | 50.142 | 1.00 | 10.79 | N |
| ATOM | 28938 | CA | ALA | C | 605 | 85.893 | 81.309 | 50.390 | 1.00 | 10.43 | C |
| ATOM | 28940 | CB | ALA | C | 605 | 86.857 | 80.490 | 49.555 | 1.00 | 10.17 | C |
| ATOM | 28944 | C | ALA | C | 605 | 86.146 | 82.814 | 50.145 | 1.00 | 11.31 | C |
| ATOM | 28945 | O | ALA | C | 605 | 86.979 | 83.449 | 50.780 | 1.00 | 11.07 | O |
| ATOM | 28947 | N | GLY | C | 606 | 85.463 | 83.349 | 49.151 | 1.00 | 11.32 | N |
| ATOM | 28948 | CA | GLY | C | 606 | 85.560 | 84.794 | 48.870 | 1.00 | 12.07 | C |
| ATOM | 28951 | C | GLY | C | 606 | 85.009 | 85.588 | 50.047 | 1.00 | 12.54 | C |
| ATOM | 28952 | O | GLY | C | 606 | 85.566 | 86.617 | 50.431 | 1.00 | 12.39 | O |
| ATOM | 28954 | N | THR | C | 607 | 83.937 | 85.048 | 50.655 | 1.00 | 12.61 | N |
| ATOM | 28955 | CA | THR | C | 607 | 83.394 | 85.648 | 51.883 | 1.00 | 13.08 | C |
| ATOM | 28957 | CB | THR | C | 607 | 82.037 | 85.024 | 52.280 | 1.00 | 14.55 | C |
| ATOM | 28959 | OG1 | THR | C | 607 | 81.091 | 85.280 | 51.234 | 1.00 | 14.93 | O |
| ATOM | 28961 | CG2 | THR | C | 607 | 81.524 | 85.680 | 53.555 | 1.00 | 15.17 | C |
| ATOM | 28965 | C | THR | C | 607 | 84.406 | 85.584 | 53.018 | 1.00 | 12.48 | C |
| ATOM | 28966 | O | THR | C | 607 | 84.599 | 86.560 | 53.776 | 1.00 | 11.42 | O |
| ATOM | 28968 | N | VAL | C | 608 | 85.115 | 84.458 | 53.130 | 1.00 | 10.90 | N |
| ATOM | 28969 | CA | VAL | C | 608 | 86.139 | 84.320 | 54.162 | 1.00 | 10.86 | C |
| ATOM | 28971 | CB | VAL | C | 608 | 86.708 | 82.885 | 54.201 | 1.00 | 12.56 | C |
| ATOM | 28973 | CG1 | VAL | C | 608 | 87.942 | 82.781 | 55.106 | 1.00 | 13.64 | C |
| ATOM | 28977 | CG2 | VAL | C | 608 | 85.577 | 81.920 | 54.629 | 1.00 | 12.04 | C |
| ATOM | 28981 | C | VAL | C | 608 | 87.255 | 85.361 | 53.991 | 1.00 | 10.06 | C |
| ATOM | 28982 | O | VAL | C | 608 | 87.750 | 85.986 | 54.950 | 1.00 | 10.34 | O |
| ATOM | 28984 | N | VAL | C | 609 | 87.663 | 85.539 | 52.736 | 1.00 | 10.17 | N |
| ATOM | 28985 | CA | VAL | C | 609 | 88.717 | 86.520 | 52.411 | 1.00 | 10.89 | C |
| ATOM | 28987 | CB | VAL | C | 609 | 89.015 | 86.542 | 50.909 | 1.00 | 10.48 | C |
| ATOM | 28989 | CG1 | VAL | C | 609 | 89.803 | 87.789 | 50.528 | 1.00 | 12.07 | C |
| ATOM | 28993 | CG2 | VAL | C | 609 | 89.770 | 85.281 | 50.462 | 1.00 | 11.46 | C |
| ATOM | 28997 | C | VAL | C | 609 | 88.346 | 87.901 | 52.942 | 1.00 | 11.08 | C |
| ATOM | 28998 | O | VAL | C | 609 | 89.212 | 88.603 | 53.500 | 1.00 | 12.77 | O |
| ATOM | 29000 | N | GLU | C | 610 | 87.075 | 88.289 | 52.756 | 1.00 | 11.32 | N |
| ATOM | 29001 | CA | GLU | C | 610 | 86.611 | 89.615 | 53.192 | 1.00 | 13.07 | C |
| ATOM | 29003 | CB | GLU | C | 610 | 85.263 | 89.956 | 52.548 | 1.00 | 13.24 | C |
| ATOM | 29006 | CG | GLU | C | 610 | 84.711 | 91.302 | 52.961 | 1.00 | 15.71 | C |
| ATOM | 29009 | CD | GLU | C | 610 | 83.387 | 91.591 | 52.306 | 1.00 | 19.38 | C |
| ATOM | 29010 | OE1 | GLU | C | 610 | 83.041 | 90.879 | 51.311 | 1.00 | 24.65 | O |
| ATOM | 29011 | OE2 | GLU | C | 610 | 82.673 | 92.529 | 52.784 | 1.00 | 26.62 | O |
| ATOM | 29012 | C | GLU | C | 610 | 86.487 | 89.634 | 54.709 | 1.00 | 11.98 | C |
| ATOM | 29013 | O | GLU | C | 610 | 87.091 | 90.484 | 55.363 | 1.00 | 11.16 | O |
| ATOM | 29015 | N | VAL | C | 611 | 85.727 | 88.693 | 55.267 | 1.00 | 12.08 | N |
| ATOM | 29016 | CA | VAL | C | 611 | 85.454 | 88.738 | 56.722 | 1.00 | 12.26 | C |
| ATOM | 29018 | CB | VAL | C | 611 | 84.338 | 87.723 | 57.120 | 1.00 | 11.97 | C |
| ATOM | 29020 | CG1 | VAL | C | 611 | 84.161 | 87.688 | 58.621 | 1.00 | 12.91 | C |
| ATOM | 29024 | CG2 | VAL | C | 611 | 83.077 | 88.122 | 56.432 | 1.00 | 11.82 | C |
| ATOM | 29028 | C | VAL | C | 611 | 86.708 | 88.561 | 57.595 | 1.00 | 11.70 | C |
| ATOM | 29029 | O | VAL | C | 611 | 86.897 | 89.256 | 58.639 | 1.00 | 12.13 | O |

```
ATOM  29031  N    LEU C 612      87.591  87.659  57.169  1.00 11.50           N
ATOM  29032  CA   LEU C 612      88.800  87.346  57.903  1.00 11.80           C
ATOM  29034  CB   LEU C 612      89.007  85.818  57.955  1.00 12.25           C
ATOM  29037  CG   LEU C 612      87.877  85.040  58.656  1.00 13.21           C
ATOM  29039  CD1  LEU C 612      88.335  83.654  58.949  1.00 12.51           C
ATOM  29043  CD2  LEU C 612      87.366  85.702  59.916  1.00 13.82           C
ATOM  29047  C    LEU C 612      90.026  88.069  57.301  1.00 12.22           C
ATOM  29048  O    LEU C 612      91.165  87.645  57.508  1.00 10.90           O
ATOM  29050  N    SER C 613      89.790  89.183  56.598  1.00 12.44           N
ATOM  29051  CA   SER C 613      90.895  89.870  55.915  1.00 13.53           C
ATOM  29053  CB   SER C 613      90.355  91.051  55.100  1.00 14.49           C
ATOM  29056  OG   SER C 613      89.921  92.090  55.955  1.00 16.42           O
ATOM  29058  C    SER C 613      92.005  90.364  56.864  1.00 14.59           C
ATOM  29059  O    SER C 613      93.148  90.569  56.423  1.00 15.25           O
ATOM  29061  N    SER C 614      91.699  90.579  58.142  1.00 13.90           N
ATOM  29062  CA   SER C 614      92.717  91.054  59.108  1.00 14.08           C
ATOM  29064  CB   SER C 614      92.037  91.790  60.241  1.00 14.25           C
ATOM  29067  OG   SER C 614      91.222  90.897  60.984  1.00 16.10           O
ATOM  29069  C    SER C 614      93.530  89.926  59.728  1.00 13.93           C
ATOM  29070  O    SER C 614      94.446  90.192  60.471  1.00 14.60           O
ATOM  29072  N    THR C 615      93.156  88.675  59.471  1.00 13.78           N
ATOM  29073  CA   THR C 615      93.796  87.534  60.129  1.00 13.90           C
ATOM  29075  CB   THR C 615      92.843  86.324  60.290  1.00 13.39           C
ATOM  29077  OG1  THR C 615      92.645  85.685  59.036  1.00 14.49           O
ATOM  29079  CG2  THR C 615      91.521  86.733  60.879  1.00 14.47           C
ATOM  29083  C    THR C 615      95.062  87.054  59.398  1.00 14.28           C
ATOM  29084  O    THR C 615      95.335  87.418  58.258  1.00 13.83           O
ATOM  29086  N    SER C 616      95.766  86.162  60.068  1.00 13.08           N
ATOM  29087  CA   SER C 616      97.028  85.592  59.637  1.00 14.05           C
ATOM  29089  CB   SER C 616      97.867  85.262  60.881  1.00 14.97           C
ATOM  29092  OG   SER C 616      97.182  84.235  61.618  1.00 19.12           O
ATOM  29094  C    SER C 616      96.866  84.315  58.785  1.00 13.22           C
ATOM  29095  O    SER C 616      97.852  83.668  58.436  1.00 13.71           O
ATOM  29097  N    LEU C 617      95.633  83.953  58.441  1.00 12.73           N
ATOM  29098  CA   LEU C 617      95.370  82.707  57.738  1.00 12.73           C
ATOM  29100  CB   LEU C 617      93.880  82.497  57.571  1.00 13.58           C
ATOM  29103  CG   LEU C 617      93.175  82.041  58.845  1.00 13.69           C
ATOM  29105  CD1  LEU C 617      91.676  82.331  58.710  1.00 13.82           C
ATOM  29109  CD2  LEU C 617      93.409  80.536  59.042  1.00 15.26           C
ATOM  29113  C    LEU C 617      96.011  82.681  56.362  1.00 12.97           C
ATOM  29114  O    LEU C 617      95.927  83.662  55.626  1.00 13.15           O
ATOM  29116  N    SER C 618      96.660  81.571  56.035  1.00 12.72           N
ATOM  29117  CA   SER C 618      97.214  81.407  54.685  1.00 12.68           C
ATOM  29119  CB   SER C 618      98.263  80.289  54.677  1.00 12.86           C
ATOM  29122  OG   SER C 618      97.669  79.017  54.850  1.00 13.37           O
ATOM  29124  C    SER C 618      96.128  81.080  53.660  1.00 12.13           C
ATOM  29125  O    SER C 618      95.012  80.625  53.989  1.00 11.64           O
ATOM  29127  N    LEU C 619      96.443  81.250  52.374  1.00 12.28           N
ATOM  29128  CA   LEU C 619      95.479  80.871  51.357  1.00 11.33           C
ATOM  29130  CB   LEU C 619      95.888  81.368  49.971  1.00 10.65           C
ATOM  29133  CG   LEU C 619      95.984  82.871  49.761  1.00 12.23           C
ATOM  29135  CD1  LEU C 619      96.101  83.084  48.258  1.00 13.10           C
ATOM  29139  CD2  LEU C 619      94.770  83.624  50.280  1.00 13.09           C
ATOM  29143  C    LEU C 619      95.336  79.378  51.349  1.00 10.87           C
ATOM  29144  O    LEU C 619      94.249  78.865  51.070  1.00 11.27           O
ATOM  29146  N    ALA C 620      96.421  78.669  51.642  1.00 11.41           N
ATOM  29147  CA   ALA C 620      96.349  77.230  51.766  1.00 11.13           C
```

| | | | | | | | | | |
|---|---|---|---|---|---|---|---|---|---|
| ATOM | 29149 | CB | ALA | C | 620 | 97.661 | 76.659 | 52.074 | 1.00 11.77 | C |
| ATOM | 29153 | C | ALA | C | 620 | 95.353 | 76.810 | 52.835 | 1.00 10.76 | C |
| ATOM | 29154 | O | ALA | C | 620 | 94.590 | 75.854 | 52.624 | 1.00 11.24 | O |
| ATOM | 29156 | N | ALA | C | 621 | 95.346 | 77.524 | 53.960 | 1.00 10.23 | N |
| ATOM | 29157 | CA | ALA | C | 621 | 94.435 | 77.206 | 55.069 | 1.00 10.73 | C |
| ATOM | 29159 | CB | ALA | C | 621 | 94.733 | 78.060 | 56.208 | 1.00 10.63 | C |
| ATOM | 29163 | C | ALA | C | 621 | 92.986 | 77.408 | 54.653 | 1.00 11.39 | C |
| ATOM | 29164 | O | ALA | C | 621 | 92.080 | 76.600 | 54.973 | 1.00 12.31 | O |
| ATOM | 29166 | N | VAL | C | 622 | 92.740 | 78.511 | 53.948 | 1.00 11.08 | N |
| ATOM | 29167 | CA | VAL | C | 622 | 91.384 | 78.791 | 53.504 | 1.00 10.11 | C |
| ATOM | 29169 | CB | VAL | C | 622 | 91.204 | 80.257 | 53.020 | 1.00 11.12 | C |
| ATOM | 29171 | CG1 | VAL | C | 622 | 89.799 | 80.436 | 52.495 | 1.00 9.98 | C |
| ATOM | 29175 | CG2 | VAL | C | 622 | 91.517 | 81.243 | 54.150 | 1.00 11.65 | C |
| ATOM | 29179 | C | VAL | C | 622 | 90.933 | 77.744 | 52.446 | 1.00 10.45 | C |
| ATOM | 29180 | O | VAL | C | 622 | 89.830 | 77.179 | 52.496 | 1.00 8.98 | O |
| ATOM | 29182 | N | ASN | C | 623 | 91.814 | 77.470 | 51.491 | 1.00 10.02 | N |
| ATOM | 29183 | CA | ASN | C | 623 | 91.520 | 76.442 | 50.504 | 1.00 10.95 | C |
| ATOM | 29185 | CB | ASN | C | 623 | 92.655 | 76.303 | 49.489 | 1.00 11.68 | C |
| ATOM | 29188 | CG | ASN | C | 623 | 92.243 | 75.493 | 48.265 | 1.00 14.19 | C |
| ATOM | 29189 | OD1 | ASN | C | 623 | 91.233 | 75.784 | 47.617 | 1.00 16.41 | O |
| ATOM | 29190 | ND2 | ASN | C | 623 | 93.026 | 74.481 | 47.941 | 1.00 17.56 | N |
| ATOM | 29193 | C | ASN | C | 623 | 91.241 | 75.079 | 51.132 | 1.00 11.19 | C |
| ATOM | 29194 | O | ASN | C | 623 | 90.351 | 74.329 | 50.685 | 1.00 11.53 | O |
| ATOM | 29196 | N | ALA | C | 624 | 92.013 | 74.739 | 52.173 | 1.00 11.24 | N |
| ATOM | 29197 | CA | ALA | C | 624 | 91.793 | 73.445 | 52.838 | 1.00 10.72 | C |
| ATOM | 29199 | CB | ALA | C | 624 | 92.877 | 73.144 | 53.819 | 1.00 10.92 | C |
| ATOM | 29203 | C | ALA | C | 624 | 90.436 | 73.385 | 53.511 | 1.00 10.88 | C |
| ATOM | 29204 | O | ALA | C | 624 | 89.775 | 72.369 | 53.474 | 1.00 11.76 | O |
| ATOM | 29206 | N | TRP | C | 625 | 90.017 | 74.498 | 54.099 | 1.00 9.33 | N |
| ATOM | 29207 | CA | TRP | C | 625 | 88.676 | 74.575 | 54.673 | 1.00 10.17 | C |
| ATOM | 29209 | CB | TRP | C | 625 | 88.477 | 75.920 | 55.360 | 1.00 10.67 | C |
| ATOM | 29212 | CG | TRP | C | 625 | 87.055 | 76.212 | 55.694 | 1.00 10.23 | C |
| ATOM | 29213 | CD1 | TRP | C | 625 | 86.339 | 75.724 | 56.767 | 1.00 12.51 | C |
| ATOM | 29215 | NE1 | TRP | C | 625 | 85.043 | 76.194 | 56.709 | 1.00 13.03 | N |
| ATOM | 29217 | CE2 | TRP | C | 625 | 84.903 | 76.992 | 55.598 | 1.00 13.08 | C |
| ATOM | 29218 | CD2 | TRP | C | 625 | 86.150 | 77.016 | 54.929 | 1.00 10.88 | C |
| ATOM | 29219 | CE3 | TRP | C | 625 | 86.283 | 77.782 | 53.752 | 1.00 11.54 | C |
| ATOM | 29221 | CZ3 | TRP | C | 625 | 85.171 | 78.468 | 53.273 | 1.00 12.70 | C |
| ATOM | 29223 | CH2 | TRP | C | 625 | 83.951 | 78.416 | 53.953 | 1.00 12.40 | C |
| ATOM | 29225 | CZ2 | TRP | C | 625 | 83.797 | 77.709 | 55.133 | 1.00 13.55 | C |
| ATOM | 29227 | C | TRP | C | 625 | 87.639 | 74.345 | 53.577 | 1.00 10.15 | C |
| ATOM | 29228 | O | TRP | C | 625 | 86.662 | 73.558 | 53.738 | 1.00 11.12 | O |
| ATOM | 29230 | N | LYS | C | 626 | 87.798 | 75.066 | 52.470 | 1.00 10.34 | N |
| ATOM | 29231 | CA | LYS | C | 626 | 86.865 | 75.016 | 51.355 | 1.00 11.62 | C |
| ATOM | 29233 | CB | LYS | C | 626 | 87.344 | 75.942 | 50.222 | 1.00 11.27 | C |
| ATOM | 29236 | CG | LYS | C | 626 | 86.599 | 75.867 | 48.943 | 1.00 13.02 | C |
| ATOM | 29239 | CD | LYS | C | 626 | 87.020 | 74.675 | 48.087 | 1.00 13.12 | C |
| ATOM | 29242 | CE | LYS | C | 626 | 86.585 | 74.830 | 46.644 | 1.00 13.37 | C |
| ATOM | 29245 | NZ | LYS | C | 626 | 87.177 | 73.838 | 45.713 | 1.00 14.88 | N |
| ATOM | 29249 | C | LYS | C | 626 | 86.698 | 73.556 | 50.870 | 1.00 11.47 | C |
| ATOM | 29250 | O | LYS | C | 626 | 85.565 | 73.060 | 50.679 | 1.00 11.82 | O |
| ATOM | 29252 | N | VAL | C | 627 | 87.828 | 72.878 | 50.660 | 1.00 11.35 | N |
| ATOM | 29253 | CA | VAL | C | 627 | 87.818 | 71.466 | 50.250 | 1.00 12.38 | C |
| ATOM | 29255 | CB | VAL | C | 627 | 89.232 | 70.990 | 49.896 | 1.00 12.39 | C |
| ATOM | 29257 | CG1 | VAL | C | 627 | 89.282 | 69.478 | 49.658 | 1.00 14.52 | C |
| ATOM | 29261 | CG2 | VAL | C | 627 | 89.779 | 71.797 | 48.679 | 1.00 13.74 | C |
| ATOM | 29265 | C | VAL | C | 627 | 87.157 | 70.555 | 51.308 | 1.00 12.06 | C |

```
ATOM  29266  O    VAL C 627      86.277  69.734  50.970  1.00 12.95           O
ATOM  29268  N    ALA C 628      87.535  70.700  52.561  1.00 11.94           N
ATOM  29269  CA   ALA C 628      86.936  69.851  53.635  1.00 12.22           C
ATOM  29271  CB   ALA C 628      87.596  70.132  54.968  1.00 13.12           C
ATOM  29275  C    ALA C 628      85.418  70.080  53.743  1.00 12.47           C
ATOM  29276  O    ALA C 628      84.604  69.123  53.913  1.00 12.24           O
ATOM  29278  N    ALA C 629      85.026  71.348  53.630  1.00 11.13           N
ATOM  29279  CA   ALA C 629      83.603  71.733  53.731  1.00 10.60           C
ATOM  29281  CB   ALA C 629      83.463  73.207  53.798  1.00 10.64           C
ATOM  29285  C    ALA C 629      82.799  71.193  52.574  1.00 11.09           C
ATOM  29286  O    ALA C 629      81.722  70.638  52.763  1.00 12.64           O
ATOM  29288  N    ALA C 630      83.331  71.308  51.359  1.00 10.36           N
ATOM  29289  CA   ALA C 630      82.709  70.665  50.200  1.00 11.52           C
ATOM  29291  CB   ALA C 630      83.447  71.040  48.891  1.00 11.04           C
ATOM  29295  C    ALA C 630      82.588  69.147  50.355  1.00 11.94           C
ATOM  29296  O    ALA C 630      81.495  68.605  50.114  1.00 11.51           O
ATOM  29298  N    GLU C 631      83.671  68.463  50.726  1.00 12.50           N
ATOM  29299  CA   GLU C 631      83.619  67.009  50.936  1.00 14.49           C
ATOM  29301  CB   GLU C 631      84.990  66.478  51.309  1.00 14.91           C
ATOM  29304  CG   GLU C 631      86.029  66.617  50.187  1.00 16.98           C
ATOM  29307  CD   GLU C 631      87.432  66.229  50.614  1.00 19.22           C
ATOM  29308  OE1  GLU C 631      87.705  66.172  51.835  1.00 26.56           O
ATOM  29309  OE2  GLU C 631      88.264  66.013  49.706  1.00 24.76           O
ATOM  29310  C    GLU C 631      82.602  66.653  52.002  1.00 13.98           C
ATOM  29311  O    GLU C 631      81.858  65.695  51.863  1.00 14.93           O
ATOM  29313  N    SER C 632      82.546  67.437  53.055  1.00 14.55           N
ATOM  29314  CA   SER C 632      81.576  67.186  54.119  1.00 15.25           C
ATOM  29316  CB   SER C 632      81.722  68.233  55.204  1.00 16.15           C
ATOM  29319  OG   SER C 632      80.674  68.128  56.158  1.00 19.96           O
ATOM  29321  C    SER C 632      80.142  67.278  53.579  1.00 13.91           C
ATOM  29322  O    SER C 632      79.283  66.436  53.893  1.00 13.94           O
ATOM  29324  N    ALA C 633      79.868  68.306  52.780  1.00 12.04           N
ATOM  29325  CA   ALA C 633      78.526  68.523  52.222  1.00 12.61           C
ATOM  29327  CB   ALA C 633      78.400  69.870  51.542  1.00 12.65           C
ATOM  29331  C    ALA C 633      78.145  67.422  51.249  1.00 12.97           C
ATOM  29332  O    ALA C 633      76.993  66.986  51.200  1.00 12.83           O
ATOM  29334  N    ILE C 634      79.120  67.002  50.464  1.00 12.61           N
ATOM  29335  CA   ILE C 634      78.878  65.948  49.478  1.00 13.33           C
ATOM  29337  CB   ILE C 634      80.124  65.724  48.605  1.00 14.13           C
ATOM  29339  CG1  ILE C 634      80.338  66.922  47.668  1.00 12.03           C
ATOM  29342  CD1  ILE C 634      81.729  67.019  47.089  1.00 14.69           C
ATOM  29346  CG2  ILE C 634      80.016  64.402  47.791  1.00 16.38           C
ATOM  29350  C    ILE C 634      78.502  64.665  50.241  1.00 13.66           C
ATOM  29351  O    ILE C 634      77.510  63.969  49.907  1.00 13.82           O
ATOM  29353  N    SER C 635      79.305  64.331  51.234  1.00 13.07           N
ATOM  29354  CA   SER C 635      79.081  63.100  52.053  1.00 14.52           C
ATOM  29356  CB   SER C 635      80.220  62.936  53.042  1.00 15.66           C
ATOM  29359  OG   SER C 635      81.380  62.594  52.275  1.00 19.57           O
ATOM  29361  C    SER C 635      77.723  63.116  52.786  1.00 14.40           C
ATOM  29362  O    SER C 635      76.960  62.142  52.753  1.00 14.41           O
ATOM  29364  N    LEU C 636      77.407  64.248  53.401  1.00 15.17           N
ATOM  29365  CA   LEU C 636      76.131  64.419  54.104  1.00 15.45           C
ATOM  29367  CB   LEU C 636      76.115  65.780  54.778  1.00 16.02           C
ATOM  29370  CG   LEU C 636      74.850  66.129  55.573  1.00 17.06           C
ATOM  29372  CD1  LEU C 636      74.678  65.068  56.694  1.00 18.80           C
ATOM  29376  CD2  LEU C 636      74.870  67.558  56.146  1.00 18.83           C
ATOM  29380  C    LEU C 636      74.937  64.300  53.148  1.00 14.36           C
```

| | | | | | | | | | |
|---|---|---|---|---|---|---|---|---|---|
| ATOM | 29381 | O | LEU | C | 636 | 73.919 | 63.665 | 53.469 | 1.00 14.27 | O |
| ATOM | 29383 | N | THR | C | 637 | 75.072 | 64.885 | 51.956 | 1.00 13.59 | N |
| ATOM | 29384 | CA | THR | C | 637 | 74.007 | 64.792 | 50.969 | 1.00 13.00 | C |
| ATOM | 29386 | CB | THR | C | 637 | 74.312 | 65.551 | 49.662 | 1.00 12.71 | C |
| ATOM | 29388 | OG1 | THR | C | 637 | 74.455 | 66.946 | 49.938 | 1.00 11.10 | O |
| ATOM | 29390 | CG2 | THR | C | 637 | 73.197 | 65.348 | 48.642 | 1.00 13.69 | C |
| ATOM | 29394 | C | THR | C | 637 | 73.784 | 63.328 | 50.636 | 1.00 12.43 | C |
| ATOM | 29395 | O | THR | C | 637 | 72.646 | 62.884 | 50.631 | 1.00 13.11 | O |
| ATOM | 29397 | N | ARG | C | 638 | 74.858 | 62.575 | 50.406 | 1.00 11.94 | N |
| ATOM | 29398 | CA | ARG | C | 638 | 74.691 | 61.170 | 50.083 | 1.00 12.35 | C |
| ATOM | 29400 | CB | ARG | C | 638 | 76.049 | 60.542 | 49.729 | 1.00 11.74 | C |
| ATOM | 29403 | CG | ARG | C | 638 | 76.574 | 61.020 | 48.415 | 1.00 13.98 | C |
| ATOM | 29406 | CD | ARG | C | 638 | 77.883 | 60.427 | 48.116 | 1.00 18.10 | C |
| ATOM | 29409 | NE | ARG | C | 638 | 78.356 | 60.893 | 46.804 | 1.00 17.82 | N |
| ATOM | 29411 | CZ | ARG | C | 638 | 79.625 | 61.134 | 46.521 | 1.00 17.55 | C |
| ATOM | 29412 | NH1 | ARG | C | 638 | 80.571 | 60.930 | 47.416 | 1.00 20.91 | N |
| ATOM | 29415 | NH2 | ARG | C | 638 | 79.931 | 61.567 | 45.310 | 1.00 17.52 | N |
| ATOM | 29418 | C | ARG | C | 638 | 74.005 | 60.428 | 51.232 | 1.00 12.62 | C |
| ATOM | 29419 | O | ARG | C | 638 | 73.173 | 59.581 | 50.989 | 1.00 13.67 | O |
| ATOM | 29421 | N | GLN | C | 639 | 74.378 | 60.744 | 52.467 | 1.00 13.97 | N |
| ATOM | 29422 | CA | GLN | C | 639 | 73.826 | 60.062 | 53.656 | 1.00 15.17 | C |
| ATOM | 29424 | CB | GLN | C | 639 | 74.624 | 60.465 | 54.885 | 1.00 15.14 | C |
| ATOM | 29427 | CG | GLN | C | 639 | 74.310 | 59.803 | 56.206 | 1.00 16.88 | C |
| ATOM | 29430 | CD | GLN | C | 639 | 75.357 | 60.222 | 57.326 | 1.00 22.81 | C |
| ATOM | 29431 | OE1 | GLN | C | 639 | 75.688 | 61.434 | 57.517 | 1.00 29.65 | O |
| ATOM | 29432 | NE2 | GLN | C | 639 | 75.903 | 59.209 | 58.034 | 1.00 32.67 | N |
| ATOM | 29435 | C | GLN | C | 639 | 72.358 | 60.398 | 53.814 | 1.00 13.83 | C |
| ATOM | 29436 | O | GLN | C | 639 | 71.526 | 59.509 | 54.052 | 1.00 13.56 | O |
| ATOM | 29438 | N | VAL | C | 640 | 72.010 | 61.672 | 53.621 | 1.00 12.67 | N |
| ATOM | 29439 | CA | VAL | C | 640 | 70.619 | 62.065 | 53.796 | 1.00 12.19 | C |
| ATOM | 29441 | CB | VAL | C | 640 | 70.485 | 63.582 | 53.824 | 1.00 13.93 | C |
| ATOM | 29443 | CG1 | VAL | C | 640 | 69.047 | 63.980 | 53.774 | 1.00 15.73 | C |
| ATOM | 29447 | CG2 | VAL | C | 640 | 71.168 | 64.110 | 55.092 | 1.00 13.72 | C |
| ATOM | 29451 | C | VAL | C | 640 | 69.732 | 61.383 | 52.727 | 1.00 11.76 | C |
| ATOM | 29452 | O | VAL | C | 640 | 68.584 | 60.923 | 52.984 | 1.00 12.39 | O |
| ATOM | 29454 | N | ARG | C | 641 | 70.240 | 61.325 | 51.499 | 1.00 12.66 | N |
| ATOM | 29455 | CA | ARG | C | 641 | 69.526 | 60.632 | 50.424 | 1.00 12.82 | C |
| ATOM | 29457 | CB | ARG | C | 641 | 70.284 | 60.797 | 49.098 | 1.00 12.34 | C |
| ATOM | 29460 | CG | ARG | C | 641 | 70.224 | 62.218 | 48.542 | 1.00 12.93 | C |
| ATOM | 29463 | CD | ARG | C | 641 | 71.088 | 62.304 | 47.340 | 1.00 13.37 | C |
| ATOM | 29466 | NE | ARG | C | 641 | 70.938 | 63.513 | 46.552 | 1.00 14.25 | N |
| ATOM | 29468 | CZ | ARG | C | 641 | 71.804 | 63.861 | 45.591 | 1.00 14.97 | C |
| ATOM | 29469 | NH1 | ARG | C | 641 | 72.874 | 63.133 | 45.343 | 1.00 16.81 | N |
| ATOM | 29472 | NH2 | ARG | C | 641 | 71.551 | 64.943 | 44.889 | 1.00 18.56 | N |
| ATOM | 29475 | C | ARG | C | 641 | 69.339 | 59.118 | 50.737 | 1.00 12.81 | C |
| ATOM | 29476 | O | ARG | C | 641 | 68.236 | 58.568 | 50.607 | 1.00 13.90 | O |
| ATOM | 29478 | N | GLU | C | 642 | 70.414 | 58.476 | 51.158 | 1.00 12.67 | N |
| ATOM | 29479 | CA | GLU | C | 642 | 70.330 | 57.067 | 51.542 | 1.00 13.41 | C |
| ATOM | 29481 | CB | GLU | C | 642 | 71.683 | 56.583 | 51.968 | 1.00 14.68 | C |
| ATOM | 29484 | CG | GLU | C | 642 | 72.537 | 56.375 | 50.801 | 1.00 16.36 | C |
| ATOM | 29487 | CD | GLU | C | 642 | 72.028 | 55.223 | 49.974 | 1.00 25.67 | C |
| ATOM | 29488 | OE1 | GLU | C | 642 | 71.917 | 54.127 | 50.533 | 1.00 29.03 | O |
| ATOM | 29489 | OE2 | GLU | C | 642 | 71.726 | 55.403 | 48.793 | 1.00 23.03 | O |
| ATOM | 29490 | C | GLU | C | 642 | 69.292 | 56.843 | 52.626 | 1.00 13.49 | C |
| ATOM | 29491 | O | GLU | C | 642 | 68.518 | 55.868 | 52.568 | 1.00 13.84 | O |
| ATOM | 29493 | N | THR | C | 643 | 69.273 | 57.727 | 53.615 | 1.00 13.32 | N |
| ATOM | 29494 | CA | THR | C | 643 | 68.316 | 57.604 | 54.700 | 1.00 12.74 | C |

| | | | | | | | | | |
|---|---|---|---|---|---|---|---|---|---|
| ATOM | 29496 | CB | THR | C | 643 | 68.584 | 58.683 | 55.761 | 1.00 12.64 | C |
| ATOM | 29498 | OG1 | THR | C | 643 | 69.854 | 58.454 | 56.347 | 1.00 12.29 | O |
| ATOM | 29500 | CG2 | THR | C | 643 | 67.508 | 58.717 | 56.816 | 1.00 14.11 | C |
| ATOM | 29504 | C | THR | C | 643 | 66.913 | 57.651 | 54.131 | 1.00 13.47 | C |
| ATOM | 29505 | O | THR | C | 643 | 66.040 | 56.886 | 54.520 | 1.00 14.23 | O |
| ATOM | 29507 | N | PHE | C | 644 | 66.674 | 58.544 | 53.186 | 1.00 12.38 | N |
| ATOM | 29508 | CA | PHE | C | 644 | 65.361 | 58.669 | 52.560 | 1.00 13.13 | C |
| ATOM | 29510 | CB | PHE | C | 644 | 65.376 | 59.848 | 51.569 | 1.00 13.71 | C |
| ATOM | 29513 | CG | PHE | C | 644 | 64.115 | 59.967 | 50.786 | 1.00 12.28 | C |
| ATOM | 29514 | CD1 | PHE | C | 644 | 63.048 | 60.655 | 51.309 | 1.00 16.39 | C |
| ATOM | 29516 | CE1 | PHE | C | 644 | 61.858 | 60.767 | 50.620 | 1.00 17.21 | C |
| ATOM | 29518 | CZ | PHE | C | 644 | 61.709 | 60.130 | 49.346 | 1.00 15.32 | C |
| ATOM | 29520 | CE2 | PHE | C | 644 | 62.778 | 59.471 | 48.822 | 1.00 14.03 | C |
| ATOM | 29522 | CD2 | PHE | C | 644 | 63.968 | 59.378 | 49.537 | 1.00 14.66 | C |
| ATOM | 29524 | C | PHE | C | 644 | 64.958 | 57.413 | 51.820 | 1.00 13.90 | C |
| ATOM | 29525 | O | PHE | C | 644 | 63.846 | 56.878 | 51.984 | 1.00 14.01 | O |
| ATOM | 29527 | N | TRP | C | 645 | 65.877 | 56.911 | 51.001 | 1.00 14.52 | N |
| ATOM | 29528 | CA | TRP | C | 645 | 65.586 | 55.786 | 50.118 | 1.00 14.73 | C |
| ATOM | 29530 | CB | TRP | C | 645 | 66.560 | 55.784 | 48.964 | 1.00 14.90 | C |
| ATOM | 29533 | CG | TRP | C | 645 | 66.324 | 56.914 | 48.019 | 1.00 13.71 | C |
| ATOM | 29534 | CD1 | TRP | C | 645 | 67.088 | 58.043 | 47.865 | 1.00 14.51 | C |
| ATOM | 29536 | NE1 | TRP | C | 645 | 66.548 | 58.861 | 46.924 | 1.00 15.21 | N |
| ATOM | 29538 | CE2 | TRP | C | 645 | 65.381 | 58.301 | 46.461 | 1.00 14.10 | C |
| ATOM | 29539 | CD2 | TRP | C | 645 | 65.182 | 57.109 | 47.171 | 1.00 15.03 | C |
| ATOM | 29540 | CE3 | TRP | C | 645 | 64.048 | 56.339 | 46.883 | 1.00 12.60 | C |
| ATOM | 29542 | CZ3 | TRP | C | 645 | 63.151 | 56.792 | 45.947 | 1.00 13.59 | C |
| ATOM | 29544 | CH2 | TRP | C | 645 | 63.344 | 58.010 | 45.264 | 1.00 12.16 | C |
| ATOM | 29546 | CZ2 | TRP | C | 645 | 64.441 | 58.795 | 45.517 | 1.00 14.65 | C |
| ATOM | 29548 | C | TRP | C | 645 | 65.593 | 54.405 | 50.791 | 1.00 15.42 | C |
| ATOM | 29549 | O | TRP | C | 645 | 65.035 | 53.420 | 50.252 | 1.00 17.87 | O |
| ATOM | 29551 | N | SER | C | 646 | 66.183 | 54.333 | 51.971 | 1.00 15.52 | N |
| ATOM | 29552 | CA | SER | C | 646 | 66.385 | 53.062 | 52.643 | 1.00 16.19 | C |
| ATOM | 29554 | CB | SER | C | 646 | 67.660 | 53.126 | 53.470 | 1.00 16.97 | C |
| ATOM | 29557 | OG | SER | C | 646 | 67.456 | 53.961 | 54.605 | 1.00 22.12 | O |
| ATOM | 29559 | C | SER | C | 646 | 65.201 | 52.717 | 53.532 | 1.00 15.33 | C |
| ATOM | 29560 | O | SER | C | 646 | 65.191 | 51.626 | 54.097 | 1.00 17.14 | O |
| ATOM | 29562 | N | ALA | C | 647 | 64.212 | 53.604 | 53.627 | 1.00 14.82 | N |
| ATOM | 29563 | CA | ALA | C | 647 | 62.974 | 53.324 | 54.324 | 1.00 14.48 | C |
| ATOM | 29565 | CB | ALA | C | 647 | 62.893 | 54.099 | 55.597 | 1.00 15.25 | C |
| ATOM | 29569 | C | ALA | C | 647 | 61.774 | 53.645 | 53.445 | 1.00 13.76 | C |
| ATOM | 29570 | O | ALA | C | 647 | 61.877 | 54.426 | 52.471 | 1.00 14.06 | O |
| ATOM | 29572 | N | ALA | C | 648 | 60.643 | 53.015 | 53.779 | 1.00 13.14 | N |
| ATOM | 29573 | CA | ALA | C | 648 | 59.425 | 53.202 | 52.996 | 1.00 13.63 | C |
| ATOM | 29575 | CB | ALA | C | 648 | 58.377 | 52.184 | 53.444 | 1.00 14.30 | C |
| ATOM | 29579 | C | ALA | C | 648 | 58.862 | 54.624 | 53.057 | 1.00 14.38 | C |
| ATOM | 29580 | O | ALA | C | 648 | 59.252 | 55.400 | 53.917 | 1.00 14.12 | O |
| ATOM | 29582 | N | SER | C | 649 | 57.927 | 54.938 | 52.165 | 1.00 13.50 | N |
| ATOM | 29583 | CA | SER | C | 649 | 57.306 | 56.262 | 52.132 | 1.00 14.29 | C |
| ATOM | 29585 | CB | SER | C | 649 | 56.516 | 56.457 | 50.821 | 1.00 13.87 | C |
| ATOM | 29588 | OG | SER | C | 649 | 55.645 | 55.375 | 50.596 | 1.00 16.51 | O |
| ATOM | 29590 | C | SER | C | 649 | 56.463 | 56.525 | 53.373 | 1.00 14.64 | C |
| ATOM | 29591 | O | SER | C | 649 | 56.191 | 57.675 | 53.697 | 1.00 16.18 | O |
| ATOM | 29593 | N | THR | C | 650 | 56.059 | 55.477 | 54.098 | 1.00 14.79 | N |
| ATOM | 29594 | CA | THR | C | 650 | 55.381 | 55.677 | 55.396 | 1.00 15.83 | C |
| ATOM | 29596 | CB | THR | C | 650 | 54.763 | 54.370 | 55.962 | 1.00 15.05 | C |
| ATOM | 29598 | OG1 | THR | C | 650 | 55.713 | 53.284 | 55.883 | 1.00 14.54 | O |
| ATOM | 29600 | CG2 | THR | C | 650 | 53.440 | 54.018 | 55.210 | 1.00 16.98 | C |

| ATOM | 29604 | C | THR C 650 | 56.306 | 56.319 | 56.449 | 1.00 | 16.57 | C |
| ATOM | 29605 | O | THR C 650 | 55.835 | 56.786 | 57.482 | 1.00 | 18.36 | O |
| ATOM | 29607 | N | SER C 651 | 57.615 | 56.280 | 56.198 | 1.00 | 16.32 | N |
| ATOM | 29608 | CA | SER C 651 | 58.636 | 56.948 | 57.020 | 1.00 | 16.58 | C |
| ATOM | 29610 | CB | SER C 651 | 59.762 | 55.949 | 57.357 | 1.00 | 15.99 | C |
| ATOM | 29613 | OG | SER C 651 | 59.267 | 54.932 | 58.212 | 1.00 | 18.17 | O |
| ATOM | 29615 | C | SER C 651 | 59.214 | 58.192 | 56.325 | 1.00 | 15.61 | C |
| ATOM | 29616 | O | SER C 651 | 60.274 | 58.726 | 56.704 | 1.00 | 16.23 | O |
| ATOM | 29618 | N | SER C 652 | 58.556 | 58.688 | 55.269 | 1.00 | 16.24 | N |
| ATOM | 29619 | CA | SER C 652 | 59.158 | 59.787 | 54.502 | 1.00 | 15.86 | C |
| ATOM | 29621 | CB | SER C 652 | 58.271 | 60.208 | 53.320 | 1.00 | 16.12 | C |
| ATOM | 29624 | OG | SER C 652 | 58.847 | 61.299 | 52.676 | 1.00 | 16.48 | O |
| ATOM | 29626 | C | SER C 652 | 59.301 | 61.005 | 55.379 | 1.00 | 14.47 | C |
| ATOM | 29627 | O | SER C 652 | 58.390 | 61.318 | 56.152 | 1.00 | 14.03 | O |
| ATOM | 29629 | N | PRO C 653 | 60.417 | 61.708 | 55.250 | 1.00 | 14.43 | N |
| ATOM | 29630 | CA | PRO C 653 | 60.563 | 62.942 | 56.043 | 1.00 | 14.42 | C |
| ATOM | 29632 | CB | PRO C 653 | 62.024 | 63.360 | 55.777 | 1.00 | 14.53 | C |
| ATOM | 29635 | CG | PRO C 653 | 62.362 | 62.784 | 54.462 | 1.00 | 16.03 | C |
| ATOM | 29638 | CD | PRO C 653 | 61.589 | 61.472 | 54.384 | 1.00 | 13.54 | C |
| ATOM | 29641 | C | PRO C 653 | 59.548 | 64.008 | 55.584 | 1.00 | 13.91 | C |
| ATOM | 29642 | O | PRO C 653 | 59.299 | 64.964 | 56.305 | 1.00 | 14.42 | O |
| ATOM | 29643 | N | ALA C 654 | 58.929 | 63.805 | 54.431 | 1.00 | 13.56 | N |
| ATOM | 29644 | CA | ALA C 654 | 57.890 | 64.727 | 53.930 | 1.00 | 12.99 | C |
| ATOM | 29646 | CB | ALA C 654 | 57.342 | 64.234 | 52.612 | 1.00 | 13.25 | C |
| ATOM | 29650 | C | ALA C 654 | 56.763 | 64.816 | 54.983 | 1.00 | 13.64 | C |
| ATOM | 29651 | O | ALA C 654 | 56.141 | 65.861 | 55.209 | 1.00 | 14.87 | O |
| ATOM | 29653 | N | LEU C 655 | 56.518 | 63.695 | 55.648 | 1.00 | 13.48 | N |
| ATOM | 29654 | CA | LEU C 655 | 55.467 | 63.633 | 56.665 | 1.00 | 15.21 | C |
| ATOM | 29656 | CB | LEU C 655 | 55.274 | 62.194 | 57.087 | 1.00 | 15.22 | C |
| ATOM | 29659 | CG | LEU C 655 | 54.924 | 61.205 | 55.972 | 1.00 | 15.09 | C |
| ATOM | 29661 | CD1 | LEU C 655 | 54.832 | 59.832 | 56.597 | 1.00 | 17.37 | C |
| ATOM | 29665 | CD2 | LEU C 655 | 53.636 | 61.570 | 55.317 | 1.00 | 18.83 | C |
| ATOM | 29669 | C | LEU C 655 | 55.726 | 64.509 | 57.899 | 1.00 | 15.46 | C |
| ATOM | 29670 | O | LEU C 655 | 54.797 | 64.817 | 58.650 | 1.00 | 17.94 | O |
| ATOM | 29672 | N | SER C 656 | 56.970 | 64.913 | 58.121 | 1.00 | 15.05 | N |
| ATOM | 29673 | CA | SER C 656 | 57.321 | 65.857 | 59.184 | 1.00 | 15.88 | C |
| ATOM | 29675 | CB | SER C 656 | 58.821 | 65.821 | 59.468 | 1.00 | 16.12 | C |
| ATOM | 29678 | OG | SER C 656 | 59.289 | 64.547 | 59.813 | 1.00 | 19.29 | O |
| ATOM | 29680 | C | SER C 656 | 56.986 | 67.312 | 58.864 | 1.00 | 15.40 | C |
| ATOM | 29681 | O | SER C 656 | 57.031 | 68.151 | 59.764 | 1.00 | 17.35 | O |
| ATOM | 29683 | N | TYR C 657 | 56.708 | 67.601 | 57.589 | 1.00 | 14.53 | N |
| ATOM | 29684 | CA | TYR C 657 | 56.548 | 68.986 | 57.120 | 1.00 | 13.98 | C |
| ATOM | 29686 | CB | TYR C 657 | 57.687 | 69.419 | 56.190 | 1.00 | 15.36 | C |
| ATOM | 29689 | CG | TYR C 657 | 59.081 | 69.123 | 56.760 | 1.00 | 14.03 | C |
| ATOM | 29690 | CD1 | TYR C 657 | 59.598 | 69.889 | 57.760 | 1.00 | 19.93 | C |
| ATOM | 29692 | CE1 | TYR C 657 | 60.868 | 69.609 | 58.301 | 1.00 | 19.00 | C |
| ATOM | 29694 | CZ | TYR C 657 | 61.631 | 68.586 | 57.759 | 1.00 | 17.01 | C |
| ATOM | 29695 | OH | TYR C 657 | 62.906 | 68.345 | 58.293 | 1.00 | 17.33 | O |
| ATOM | 29697 | CE2 | TYR C 657 | 61.115 | 67.798 | 56.766 | 1.00 | 17.57 | C |
| ATOM | 29699 | CD2 | TYR C 657 | 59.852 | 68.084 | 56.252 | 1.00 | 17.38 | C |
| ATOM | 29701 | C | TYR C 657 | 55.217 | 69.256 | 56.429 | 1.00 | 14.48 | C |
| ATOM | 29702 | O | TYR C 657 | 54.753 | 70.390 | 56.429 | 1.00 | 14.54 | O |
| ATOM | 29704 | N | LEU C 658 | 54.633 | 68.253 | 55.780 | 1.00 | 13.50 | N |
| ATOM | 29705 | CA | LEU C 658 | 53.355 | 68.481 | 55.115 | 1.00 | 13.91 | C |
| ATOM | 29707 | CB | LEU C 658 | 52.871 | 67.172 | 54.467 | 1.00 | 14.69 | C |
| ATOM | 29710 | CG | LEU C 658 | 53.529 | 66.781 | 53.144 | 1.00 | 18.87 | C |
| ATOM | 29712 | CD1 | LEU C 658 | 53.148 | 65.360 | 52.727 | 1.00 | 21.30 | C |

| ATOM | 29716 | CD2 | LEU | C | 658 | 53.141 | 67.714 | 52.071 | 1.00 | 20.11 | C |
| --- | --- | --- | --- | --- | --- | --- | --- | --- | --- | --- | --- |
| ATOM | 29720 | C | LEU | C | 658 | 52.282 | 68.891 | 56.141 | 1.00 | 13.73 | C |
| ATOM | 29721 | O | LEU | C | 658 | 52.240 | 68.420 | 57.269 | 1.00 | 13.28 | O |
| ATOM | 29723 | N | SER | C | 659 | 51.320 | 69.682 | 55.682 | 1.00 | 13.53 | N |
| ATOM | 29724 | CA | SER | C | 659 | 50.147 | 69.958 | 56.480 | 1.00 | 13.74 | C |
| ATOM | 29726 | CB | SER | C | 659 | 49.214 | 70.970 | 55.789 | 1.00 | 14.64 | C |
| ATOM | 29729 | OG | SER | C | 659 | 48.002 | 70.426 | 55.399 | 1.00 | 14.67 | O |
| ATOM | 29731 | C | SER | C | 659 | 49.396 | 68.624 | 56.720 | 1.00 | 13.18 | C |
| ATOM | 29732 | O | SER | C | 659 | 49.458 | 67.702 | 55.904 | 1.00 | 12.75 | O |
| ATOM | 29734 | N | PRO | C | 660 | 48.668 | 68.532 | 57.813 | 1.00 | 13.23 | N |
| ATOM | 29735 | CA | PRO | C | 660 | 47.880 | 67.308 | 58.087 | 1.00 | 13.47 | C |
| ATOM | 29737 | CB | PRO | C | 660 | 47.180 | 67.623 | 59.404 | 1.00 | 14.56 | C |
| ATOM | 29740 | CG | PRO | C | 660 | 47.437 | 69.000 | 59.711 | 1.00 | 16.16 | C |
| ATOM | 29743 | CD | PRO | C | 660 | 48.526 | 69.515 | 58.902 | 1.00 | 15.12 | C |
| ATOM | 29746 | C | PRO | C | 660 | 46.888 | 66.977 | 56.991 | 1.00 | 15.10 | C |
| ATOM | 29747 | O | PRO | C | 660 | 46.603 | 65.804 | 56.755 | 1.00 | 14.34 | O |
| ATOM | 29748 | N | ARG | C | 661 | 46.340 | 67.990 | 56.327 | 1.00 | 13.94 | N |
| ATOM | 29749 | CA | ARG | C | 661 | 45.379 | 67.775 | 55.267 | 1.00 | 15.21 | C |
| ATOM | 29751 | CB | ARG | C | 661 | 44.461 | 68.998 | 55.096 | 1.00 | 15.12 | C |
| ATOM | 29754 | CG | ARG | C | 661 | 43.454 | 69.145 | 56.236 | 1.00 | 15.01 | C |
| ATOM | 29757 | CD | ARG | C | 661 | 42.652 | 70.423 | 56.209 | 1.00 | 17.22 | C |
| ATOM | 29760 | NE | ARG | C | 661 | 41.827 | 70.532 | 57.406 | 1.00 | 19.20 | N |
| ATOM | 29762 | CZ | ARG | C | 661 | 40.648 | 69.953 | 57.586 | 1.00 | 26.61 | C |
| ATOM | 29763 | NH1 | ARG | C | 661 | 40.044 | 69.233 | 56.626 | 1.00 | 30.16 | N |
| ATOM | 29766 | NH2 | ARG | C | 661 | 40.049 | 70.110 | 58.757 | 1.00 | 26.10 | N |
| ATOM | 29769 | C | ARG | C | 661 | 46.074 | 67.394 | 53.972 | 1.00 | 14.64 | C |
| ATOM | 29770 | O | ARG | C | 661 | 45.604 | 66.494 | 53.294 | 1.00 | 14.99 | O |
| ATOM | 29772 | N | THR | C | 662 | 47.164 | 68.075 | 53.561 | 1.00 | 13.77 | N |
| ATOM | 29773 | CA | THR | C | 662 | 47.817 | 67.639 | 52.324 | 1.00 | 14.17 | C |
| ATOM | 29775 | CB | THR | C | 662 | 48.799 | 68.668 | 51.803 | 1.00 | 14.02 | C |
| ATOM | 29777 | OG1 | THR | C | 662 | 49.784 | 68.900 | 52.807 | 1.00 | 14.11 | O |
| ATOM | 29779 | CG2 | THR | C | 662 | 48.034 | 69.975 | 51.410 | 1.00 | 13.88 | C |
| ATOM | 29783 | C | THR | C | 662 | 48.506 | 66.260 | 52.451 | 1.00 | 14.66 | C |
| ATOM | 29784 | O | THR | C | 662 | 48.655 | 65.537 | 51.460 | 1.00 | 15.31 | O |
| ATOM | 29786 | N | GLN | C | 663 | 48.904 | 65.894 | 53.668 | 1.00 | 15.02 | N |
| ATOM | 29787 | CA | GLN | C | 663 | 49.386 | 64.536 | 53.948 | 1.00 | 16.56 | C |
| ATOM | 29789 | CB | GLN | C | 663 | 49.645 | 64.424 | 55.458 | 1.00 | 17.26 | C |
| ATOM | 29792 | CG | GLN | C | 663 | 50.533 | 63.358 | 55.849 | 1.00 | 23.39 | C |
| ATOM | 29795 | CD | GLN | C | 663 | 51.057 | 63.582 | 57.278 | 1.00 | 23.51 | C |
| ATOM | 29796 | OE1 | GLN | C | 663 | 51.557 | 64.685 | 57.619 | 1.00 | 36.14 | O |
| ATOM | 29797 | NE2 | GLN | C | 663 | 50.954 | 62.548 | 58.101 | 1.00 | 33.29 | N |
| ATOM | 29800 | C | GLN | C | 663 | 48.403 | 63.454 | 53.487 | 1.00 | 15.15 | C |
| ATOM | 29801 | O | GLN | C | 663 | 48.801 | 62.379 | 53.101 | 1.00 | 14.14 | O |
| ATOM | 29803 | N | ILE | C | 664 | 47.113 | 63.744 | 53.555 | 1.00 | 15.20 | N |
| ATOM | 29804 | CA | ILE | C | 664 | 46.094 | 62.788 | 53.167 | 1.00 | 15.06 | C |
| ATOM | 29806 | CB | ILE | C | 664 | 44.703 | 63.365 | 53.426 | 1.00 | 15.20 | C |
| ATOM | 29808 | CG1 | ILE | C | 664 | 44.530 | 63.541 | 54.953 | 1.00 | 16.46 | C |
| ATOM | 29811 | CD1 | ILE | C | 664 | 43.311 | 64.282 | 55.333 | 1.00 | 18.11 | C |
| ATOM | 29815 | CG2 | ILE | C | 664 | 43.607 | 62.433 | 52.863 | 1.00 | 15.38 | C |
| ATOM | 29819 | C | ILE | C | 664 | 46.249 | 62.389 | 51.700 | 1.00 | 14.91 | C |
| ATOM | 29820 | O | ILE | C | 664 | 46.174 | 61.209 | 51.349 | 1.00 | 14.51 | O |
| ATOM | 29822 | N | LEU | C | 665 | 46.484 | 63.389 | 50.852 | 1.00 | 13.84 | N |
| ATOM | 29823 | CA | LEU | C | 665 | 46.615 | 63.128 | 49.435 | 1.00 | 14.72 | C |
| ATOM | 29825 | CB | LEU | C | 665 | 46.408 | 64.410 | 48.626 | 1.00 | 14.94 | C |
| ATOM | 29828 | CG | LEU | C | 665 | 46.313 | 64.255 | 47.105 | 1.00 | 15.67 | C |
| ATOM | 29830 | CD1 | LEU | C | 665 | 45.377 | 63.168 | 46.625 | 1.00 | 18.39 | C |
| ATOM | 29834 | CD2 | LEU | C | 665 | 45.962 | 65.623 | 46.464 | 1.00 | 16.27 | C |

```
ATOM  29838  C   LEU C 665      47.975  62.498  49.136  1.00 14.03           C
ATOM  29839  O   LEU C 665      48.086  61.574  48.338  1.00 13.80           O
ATOM  29841  N   TYR C 666      49.040  62.967  49.784  1.00 14.03           N
ATOM  29842  CA  TYR C 666      50.354  62.288  49.686  1.00 13.00           C
ATOM  29844  CB  TYR C 666      51.301  62.921  50.687  1.00 14.17           C
ATOM  29847  CG  TYR C 666      52.701  62.424  50.674  1.00 14.25           C
ATOM  29848  CD1 TYR C 666      53.693  63.077  49.927  1.00 12.90           C
ATOM  29850  CE1 TYR C 666      55.004  62.610  49.920  1.00 11.77           C
ATOM  29852  CZ  TYR C 666      55.345  61.512  50.736  1.00 12.90           C
ATOM  29853  OH  TYR C 666      56.670  61.068  50.748  1.00 16.60           O
ATOM  29855  CE2 TYR C 666      54.376  60.855  51.471  1.00 15.25           C
ATOM  29857  CD2 TYR C 666      53.060  61.348  51.462  1.00 15.23           C
ATOM  29859  C   TYR C 666      50.276  60.786  49.939  1.00 13.19           C
ATOM  29860  O   TYR C 666      50.713  59.985  49.124  1.00 13.98           O
ATOM  29862  N   ALA C 667      49.699  60.417  51.079  1.00 13.41           N
ATOM  29863  CA  ALA C 667      49.554  59.014  51.491  1.00 13.90           C
ATOM  29865  CB  ALA C 667      49.016  58.951  52.889  1.00 14.81           C
ATOM  29869  C   ALA C 667      48.648  58.218  50.524  1.00 11.86           C
ATOM  29870  O   ALA C 667      48.933  57.071  50.239  1.00 13.34           O
ATOM  29872  N   PHE C 668      47.582  58.827  50.025  1.00 13.52           N
ATOM  29873  CA  PHE C 668      46.735  58.168  49.033  1.00 12.61           C
ATOM  29875  CB  PHE C 668      45.570  59.064  48.649  1.00 14.45           C
ATOM  29878  CG  PHE C 668      44.719  58.505  47.553  1.00 11.56           C
ATOM  29879  CD1 PHE C 668      43.894  57.439  47.818  1.00 13.62           C
ATOM  29881  CE1 PHE C 668      43.105  56.878  46.811  1.00 13.16           C
ATOM  29883  CZ  PHE C 668      43.123  57.414  45.533  1.00 14.04           C
ATOM  29885  CE2 PHE C 668      43.970  58.475  45.245  1.00 14.04           C
ATOM  29887  CD2 PHE C 668      44.737  59.041  46.253  1.00 12.97           C
ATOM  29889  C   PHE C 668      47.521  57.731  47.844  1.00 12.25           C
ATOM  29890  O   PHE C 668      47.442  56.591  47.406  1.00 13.20           O
ATOM  29892  N   VAL C 669      48.313  58.638  47.297  1.00 12.33           N
ATOM  29893  CA  VAL C 669      49.102  58.309  46.112  1.00 11.92           C
ATOM  29895  CB  VAL C 669      49.588  59.571  45.407  1.00 13.02           C
ATOM  29897  CG1 VAL C 669      50.398  59.202  44.212  1.00 11.96           C
ATOM  29901  CG2 VAL C 669      48.396  60.462  44.977  1.00 11.17           C
ATOM  29905  C   VAL C 669      50.291  57.385  46.427  1.00 12.27           C
ATOM  29906  O   VAL C 669      50.492  56.369  45.768  1.00 12.78           O
ATOM  29908  N   ARG C 670      51.075  57.761  47.414  1.00 12.00           N
ATOM  29909  CA  ARG C 670      52.315  57.009  47.760  1.00 12.54           C
ATOM  29911  CB  ARG C 670      53.157  57.844  48.770  1.00 11.89           C
ATOM  29914  CG  ARG C 670      53.866  59.032  48.130  1.00 13.42           C
ATOM  29917  CD  ARG C 670      55.235  58.663  47.635  1.00 12.05           C
ATOM  29920  NE  ARG C 670      56.009  59.788  47.124  1.00 12.75           N
ATOM  29922  CZ  ARG C 670      55.977  60.263  45.866  1.00 12.55           C
ATOM  29923  NH1 ARG C 670      55.137  59.777  44.967  1.00 11.58           N
ATOM  29926  NH2 ARG C 670      56.766  61.313  45.526  1.00 11.37           N
ATOM  29929  C   ARG C 670      52.003  55.600  48.271  1.00 13.03           C
ATOM  29930  O   ARG C 670      52.713  54.634  47.942  1.00 14.41           O
ATOM  29932  N   GLU C 671      50.975  55.481  49.101  1.00 13.51           N
ATOM  29933  CA  GLU C 671      50.600  54.198  49.738  1.00 14.16           C
ATOM  29935  CB  GLU C 671      50.187  54.416  51.171  1.00 14.14           C
ATOM  29938  CG  GLU C 671      51.191  55.284  51.979  1.00 15.80           C
ATOM  29941  CD  GLU C 671      52.671  54.893  51.778  1.00 18.23           C
ATOM  29942  OE1 GLU C 671      52.968  53.696  51.617  1.00 19.80           O
ATOM  29943  OE2 GLU C 671      53.542  55.799  51.815  1.00 19.92           O
ATOM  29944  C   GLU C 671      49.487  53.513  48.981  1.00 15.06           C
ATOM  29945  O   GLU C 671      49.714  52.435  48.434  1.00 16.76           O
```

| | | | | | | | | | |
|---|---|---|---|---|---|---|---|---|---|
| ATOM | 29947 | N | GLU | C | 672 | 48.296 | 54.125 | 48.884 | 1.00 14.75 | N |
| ATOM | 29948 | CA | GLU | C | 672 | 47.198 | 53.393 | 48.257 | 1.00 14.50 | C |
| ATOM | 29950 | CB | GLU | C | 672 | 45.853 | 54.085 | 48.451 | 1.00 13.99 | C |
| ATOM | 29953 | CG | GLU | C | 672 | 45.394 | 53.991 | 49.852 | 1.00 19.14 | C |
| ATOM | 29956 | CD | GLU | C | 672 | 43.961 | 54.434 | 49.982 | 1.00 24.65 | C |
| ATOM | 29957 | OE1 | GLU | C | 672 | 43.092 | 53.821 | 49.310 | 1.00 22.49 | O |
| ATOM | 29958 | OE2 | GLU | C | 672 | 43.735 | 55.390 | 50.755 | 1.00 23.88 | O |
| ATOM | 29959 | C | GLU | C | 672 | 47.402 | 53.112 | 46.784 | 1.00 14.34 | C |
| ATOM | 29960 | O | GLU | C | 672 | 47.112 | 52.018 | 46.357 | 1.00 16.10 | O |
| ATOM | 29962 | N | LEU | C | 673 | 47.899 | 54.069 | 46.017 | 1.00 13.85 | N |
| ATOM | 29963 | CA | LEU | C | 673 | 48.181 | 53.834 | 44.586 | 1.00 14.05 | C |
| ATOM | 29965 | CB | LEU | C | 673 | 48.051 | 55.123 | 43.777 | 1.00 13.45 | C |
| ATOM | 29968 | CG | LEU | C | 673 | 46.711 | 55.839 | 43.968 | 1.00 12.45 | C |
| ATOM | 29970 | CD1 | LEU | C | 673 | 46.654 | 56.952 | 42.952 | 1.00 13.17 | C |
| ATOM | 29974 | CD2 | LEU | C | 673 | 45.529 | 54.927 | 43.804 | 1.00 14.06 | C |
| ATOM | 29978 | C | LEU | C | 673 | 49.558 | 53.253 | 44.358 | 1.00 13.88 | C |
| ATOM | 29979 | O | LEU | C | 673 | 49.857 | 52.763 | 43.255 | 1.00 14.50 | O |
| ATOM | 29981 | N | GLY | C | 674 | 50.404 | 53.302 | 45.383 | 1.00 14.24 | N |
| ATOM | 29982 | CA | GLY | C | 674 | 51.762 | 52.767 | 45.268 | 1.00 14.25 | C |
| ATOM | 29985 | C | GLY | C | 674 | 52.696 | 53.492 | 44.347 | 1.00 14.11 | C |
| ATOM | 29986 | O | GLY | C | 674 | 53.696 | 52.929 | 43.852 | 1.00 14.00 | O |
| ATOM | 29988 | N | VAL | C | 675 | 52.404 | 54.755 | 44.087 | 1.00 13.38 | N |
| ATOM | 29989 | CA | VAL | C | 675 | 53.273 | 55.557 | 43.266 | 1.00 13.40 | C |
| ATOM | 29991 | CB | VAL | C | 675 | 52.456 | 56.586 | 42.465 | 1.00 12.49 | C |
| ATOM | 29993 | CG1 | VAL | C | 675 | 53.351 | 57.493 | 41.709 | 1.00 15.16 | C |
| ATOM | 29997 | CG2 | VAL | C | 675 | 51.497 | 55.879 | 41.487 | 1.00 14.06 | C |
| ATOM | 30001 | C | VAL | C | 675 | 54.322 | 56.247 | 44.122 | 1.00 13.87 | C |
| ATOM | 30002 | O | VAL | C | 675 | 53.994 | 57.123 | 44.918 | 1.00 13.96 | O |
| ATOM | 30004 | N | LYS | C | 676 | 55.580 | 55.828 | 43.945 | 1.00 14.79 | N |
| ATOM | 30005 | CA | LYS | C | 676 | 56.677 | 56.263 | 44.805 | 1.00 13.54 | C |
| ATOM | 30007 | CB | LYS | C | 676 | 57.613 | 55.091 | 45.077 | 1.00 14.00 | C |
| ATOM | 30010 | CG | LYS | C | 676 | 56.936 | 53.835 | 45.607 | 1.00 12.53 | C |
| ATOM | 30013 | CD | LYS | C | 676 | 56.194 | 54.163 | 46.836 | 1.00 11.81 | C |
| ATOM | 30016 | CE | LYS | C | 676 | 55.582 | 52.918 | 47.501 | 1.00 15.40 | C |
| ATOM | 30019 | NZ | LYS | C | 676 | 54.983 | 53.235 | 48.870 | 1.00 13.21 | N |
| ATOM | 30023 | C | LYS | C | 676 | 57.508 | 57.362 | 44.138 | 1.00 13.24 | C |
| ATOM | 30024 | O | LYS | C | 676 | 57.480 | 57.528 | 42.920 | 1.00 12.40 | O |
| ATOM | 30026 | N | ALA | C | 677 | 58.301 | 58.067 | 44.952 | 1.00 12.47 | N |
| ATOM | 30027 | CA | ALA | C | 677 | 59.351 | 58.913 | 44.435 | 1.00 13.30 | C |
| ATOM | 30029 | CB | ALA | C | 677 | 60.191 | 59.515 | 45.600 | 1.00 13.00 | C |
| ATOM | 30033 | C | ALA | C | 677 | 60.246 | 58.050 | 43.530 | 1.00 12.69 | C |
| ATOM | 30034 | O | ALA | C | 677 | 60.389 | 56.834 | 43.744 | 1.00 14.48 | O |
| ATOM | 30036 | N | ARG | C | 678 | 60.857 | 58.691 | 42.534 | 1.00 11.84 | N |
| ATOM | 30037 | CA | ARG | C | 678 | 61.653 | 58.005 | 41.538 | 1.00 12.75 | C |
| ATOM | 30039 | CB | ARG | C | 678 | 61.226 | 58.366 | 40.130 | 1.00 13.18 | C |
| ATOM | 30042 | CG | ARG | C | 678 | 61.791 | 57.431 | 39.052 | 1.00 11.05 | C |
| ATOM | 30045 | CD | ARG | C | 678 | 61.533 | 57.953 | 37.620 | 1.00 12.78 | C |
| ATOM | 30048 | NE | ARG | C | 678 | 61.937 | 56.919 | 36.671 | 1.00 15.98 | N |
| ATOM | 30050 | CZ | ARG | C | 678 | 61.217 | 55.838 | 36.349 | 1.00 16.98 | C |
| ATOM | 30051 | NH1 | ARG | C | 678 | 59.993 | 55.665 | 36.821 | 1.00 15.52 | N |
| ATOM | 30054 | NH2 | ARG | C | 678 | 61.751 | 54.902 | 35.546 | 1.00 16.94 | N |
| ATOM | 30057 | C | ARG | C | 678 | 63.101 | 58.412 | 41.701 | 1.00 13.35 | C |
| ATOM | 30058 | O | ARG | C | 678 | 63.400 | 59.595 | 41.585 | 1.00 13.55 | O |
| ATOM | 30060 | N | ARG | C | 679 | 64.006 | 57.439 | 41.908 | 1.00 13.47 | N |
| ATOM | 30061 | CA | ARG | C | 679 | 65.397 | 57.780 | 42.165 | 1.00 12.84 | C |
| ATOM | 30063 | CB | ARG | C | 679 | 66.095 | 56.743 | 43.038 | 1.00 12.30 | C |
| ATOM | 30066 | CG | ARG | C | 679 | 67.401 | 57.301 | 43.599 | 1.00 11.99 | C |

| ATOM | 30069 | CD | ARG | C | 679 | 67.918 | 56.460 | 44.729 | 1.00 | 11.91 | C |
| --- | --- | --- | --- | --- | --- | --- | --- | --- | --- | --- | --- |
| ATOM | 30072 | NE | ARG | C | 679 | 69.072 | 57.100 | 45.380 | 1.00 | 12.44 | N |
| ATOM | 30074 | CZ | ARG | C | 679 | 69.780 | 56.587 | 46.380 | 1.00 | 11.27 | C |
| ATOM | 30075 | NH1 | ARG | C | 679 | 69.523 | 55.383 | 46.879 | 1.00 | 13.42 | N |
| ATOM | 30078 | NH2 | ARG | C | 679 | 70.800 | 57.269 | 46.906 | 1.00 | 12.59 | N |
| ATOM | 30081 | C | ARG | C | 679 | 66.214 | 58.057 | 40.899 | 1.00 | 12.31 | C |
| ATOM | 30082 | O | ARG | C | 679 | 67.100 | 58.865 | 40.954 | 1.00 | 14.19 | O |
| ATOM | 30084 | N | GLY | C | 680 | 65.914 | 57.358 | 39.785 | 1.00 | 13.78 | N |
| ATOM | 30085 | CA | GLY | C | 680 | 66.556 | 57.601 | 38.495 | 1.00 | 13.14 | C |
| ATOM | 30088 | C | GLY | C | 680 | 67.146 | 56.349 | 37.878 | 1.00 | 13.38 | C |
| ATOM | 30089 | O | GLY | C | 680 | 67.943 | 55.642 | 38.519 | 1.00 | 13.84 | O |
| ATOM | 30091 | N | ASP | C | 681 | 66.741 | 56.070 | 36.627 | 1.00 | 13.85 | N |
| ATOM | 30092 | CA | ASP | C | 681 | 67.214 | 54.840 | 35.968 | 1.00 | 13.81 | C |
| ATOM | 30094 | CB | ASP | C | 681 | 66.648 | 54.728 | 34.541 | 1.00 | 13.64 | C |
| ATOM | 30097 | CG | ASP | C | 681 | 65.153 | 54.422 | 34.494 | 1.00 | 17.79 | C |
| ATOM | 30098 | OD1 | ASP | C | 681 | 64.492 | 54.190 | 35.535 | 1.00 | 16.22 | O |
| ATOM | 30099 | OD2 | ASP | C | 681 | 64.662 | 54.351 | 33.342 | 1.00 | 17.71 | O |
| ATOM | 30100 | C | ASP | C | 681 | 68.741 | 54.728 | 35.911 | 1.00 | 12.99 | C |
| ATOM | 30101 | O | ASP | C | 681 | 69.269 | 53.625 | 36.042 | 1.00 | 13.59 | O |
| ATOM | 30103 | N | VAL | C | 682 | 69.443 | 55.824 | 35.635 | 1.00 | 13.65 | N |
| ATOM | 30104 | CA | VAL | C | 682 | 70.903 | 55.748 | 35.481 | 1.00 | 13.58 | C |
| ATOM | 30106 | CB | VAL | C | 682 | 71.458 | 57.010 | 34.839 | 1.00 | 11.99 | C |
| ATOM | 30108 | CG1 | VAL | C | 682 | 73.002 | 56.990 | 34.846 | 1.00 | 14.54 | C |
| ATOM | 30112 | CG2 | VAL | C | 682 | 70.943 | 57.119 | 33.429 | 1.00 | 13.61 | C |
| ATOM | 30116 | C | VAL | C | 682 | 71.533 | 55.482 | 36.836 | 1.00 | 13.28 | C |
| ATOM | 30117 | O | VAL | C | 682 | 72.399 | 54.580 | 36.972 | 1.00 | 12.45 | O |
| ATOM | 30119 | N | PHE | C | 683 | 71.093 | 56.234 | 37.847 | 1.00 | 13.53 | N |
| ATOM | 30120 | CA | PHE | C | 683 | 71.660 | 56.034 | 39.177 | 1.00 | 14.38 | C |
| ATOM | 30122 | CB | PHE | C | 683 | 71.060 | 56.984 | 40.229 | 1.00 | 15.17 | C |
| ATOM | 30125 | CG | PHE | C | 683 | 71.594 | 56.748 | 41.594 | 1.00 | 15.92 | C |
| ATOM | 30126 | CD1 | PHE | C | 683 | 72.749 | 57.399 | 42.004 | 1.00 | 16.90 | C |
| ATOM | 30128 | CE1 | PHE | C | 683 | 73.291 | 57.154 | 43.254 | 1.00 | 19.33 | C |
| ATOM | 30130 | CZ | PHE | C | 683 | 72.694 | 56.239 | 44.111 | 1.00 | 15.14 | C |
| ATOM | 30132 | CE2 | PHE | C | 683 | 71.548 | 55.575 | 43.723 | 1.00 | 16.35 | C |
| ATOM | 30134 | CD2 | PHE | C | 683 | 70.999 | 55.821 | 42.458 | 1.00 | 16.32 | C |
| ATOM | 30136 | C | PHE | C | 683 | 71.474 | 54.588 | 39.656 | 1.00 | 13.84 | C |
| ATOM | 30137 | O | PHE | C | 683 | 72.380 | 53.981 | 40.214 | 1.00 | 13.58 | O |
| ATOM | 30139 | N | LEU | C | 684 | 70.291 | 54.047 | 39.448 | 1.00 | 13.61 | N |
| ATOM | 30140 | CA | LEU | C | 684 | 69.978 | 52.684 | 39.891 | 1.00 | 14.26 | C |
| ATOM | 30142 | CB | LEU | C | 684 | 68.453 | 52.499 | 39.943 | 1.00 | 14.74 | C |
| ATOM | 30145 | CG | LEU | C | 684 | 67.690 | 53.363 | 40.949 | 1.00 | 15.13 | C |
| ATOM | 30147 | CD1 | LEU | C | 684 | 66.181 | 53.293 | 40.725 | 1.00 | 15.16 | C |
| ATOM | 30151 | CD2 | LEU | C | 684 | 68.103 | 53.020 | 42.371 | 1.00 | 14.82 | C |
| ATOM | 30155 | C | LEU | C | 684 | 70.590 | 51.569 | 38.988 | 1.00 | 14.72 | C |
| ATOM | 30156 | O | LEU | C | 684 | 70.640 | 50.397 | 39.368 | 1.00 | 15.74 | O |
| ATOM | 30158 | N | GLY | C | 685 | 71.005 | 51.954 | 37.793 | 1.00 | 15.61 | N |
| ATOM | 30159 | CA | GLY | C | 685 | 71.423 | 50.999 | 36.752 | 1.00 | 15.14 | C |
| ATOM | 30162 | C | GLY | C | 685 | 70.310 | 50.066 | 36.348 | 1.00 | 16.86 | C |
| ATOM | 30163 | O | GLY | C | 685 | 70.567 | 48.908 | 36.021 | 1.00 | 16.67 | O |
| ATOM | 30165 | N | LYS | C | 686 | 69.073 | 50.553 | 36.391 | 1.00 | 17.32 | N |
| ATOM | 30166 | CA | LYS | C | 686 | 67.903 | 49.744 | 36.076 | 1.00 | 19.87 | C |
| ATOM | 30168 | CB | LYS | C | 686 | 67.321 | 49.209 | 37.362 | 1.00 | 20.57 | C |
| ATOM | 30171 | CG | LYS | C | 686 | 66.148 | 48.273 | 37.184 | 1.00 | 23.81 | C |
| ATOM | 30174 | CD | LYS | C | 686 | 65.437 | 48.057 | 38.510 | 1.00 | 24.30 | C |
| ATOM | 30177 | CE | LYS | C | 686 | 64.186 | 47.184 | 38.315 | 1.00 | 26.53 | C |
| ATOM | 30180 | NZ | LYS | C | 686 | 63.733 | 46.591 | 39.628 | 1.00 | 31.48 | N |
| ATOM | 30184 | C | LYS | C | 686 | 66.863 | 50.635 | 35.407 | 1.00 | 18.95 | C |

| ATOM | 30185 | O | LYS | C | 686 | 66.622 | -51.765 | 35.884 | 1.00 | 19.07 | O |
|---|---|---|---|---|---|---|---|---|---|---|---|
| ATOM | 30187 | N | GLN | C | 687 | 66.230 | 50.133 | 34.333 | 1.00 | 17.51 | N |
| ATOM | 30188 | CA | GLN | C | 687 | 65.157 | 50.872 | 33.693 | 1.00 | 17.76 | C |
| ATOM | 30190 | CB | GLN | C | 687 | 65.099 | 50.558 | 32.212 | 1.00 | 17.90 | C |
| ATOM | 30193 | CG | GLN | C | 687 | 66.318 | 51.096 | 31.513 | 1.00 | 18.27 | C |
| ATOM | 30196 | CD | GLN | C | 687 | 66.281 | 50.830 | 30.042 | 1.00 | 20.19 | C |
| ATOM | 30197 | OE1 | GLN | C | 687 | 66.411 | 49.686 | 29.618 | 1.00 | 21.69 | O |
| ATOM | 30198 | NE2 | GLN | C | 687 | 66.065 | 51.889 | 29.246 | 1.00 | 19.62 | N |
| ATOM | 30201 | C | GLN | C | 687 | 63.883 | 50.473 | 34.383 | -1.00 | 16.89 | C |
| ATOM | 30202 | O | GLN | C | 687 | 63.309 | 49.426 | 34.066 | 1.00 | 17.67 | O |
| ATOM | 30204 | N | GLU | C | 688 | 63.477 | 51.272 | 35.369 | 1.00 | 16.26 | N |
| ATOM | 30205 | CA | GLU | C | 688 | 62.337 | 50.927 | 36.185 | 1.00 | 15.95 | C |
| ATOM | 30207 | CB | GLU | C | 688 | 62.293 | 51.795 | 37.432 | 1.00 | 16.90 | C |
| ATOM | 30210 | CG | GLU | C | 688 | 63.447 | 51.634 | 38.400 | 1.00 | 17.85 | C |
| ATOM | 30213 | CD | GLU | C | 688 | 63.092 | 52.209 | 39.778 | 1.00 | 18.20 | C |
| ATOM | 30214 | OE1 | GLU | C | 688 | 62.869 | 53.443 | 39.871 | 1.00 | 14.50 | O |
| ATOM | 30215 | OE2 | GLU | C | 688 | 63.025 | 51.420 | 40.749 | 1.00 | 22.01 | O |
| ATOM | 30216 | C | GLU | C | 688 | 61.042 | 51.136 | 35.412 | 1.00 | 15.46 | C |
| ATOM | 30217 | O | GLU | C | 688 | 60.994 | 51.832 | 34.384 | 1.00 | 15.05 | O |
| ATOM | 30219 | N | VAL | C | 689 | 59.984 | 50.537 | 35.925 | 1.00 | 15.14 | N |
| ATOM | 30220 | CA | VAL | C | 689 | 58.613 | 50.805 | 35.433 | 1.00 | 14.75 | C |
| ATOM | 30222 | CB | VAL | C | 689 | 57.549 | 50.306 | 36.439 | 1.00 | 15.28 | C |
| ATOM | 30224 | CG1 | VAL | C | 689 | 56.180 | 50.903 | 36.201 | 1.00 | 16.52 | C |
| ATOM | 30228 | CG2 | VAL | C | 689 | 57.515 | 48.755 | 36.426 | 1.00 | 16.47 | C |
| ATOM | 30232 | C | VAL | C | 689 | 58.475 | 52.309 | 35.196 | 1.00 | 13.73 | C |
| ATOM | 30233 | O | VAL | C | 689 | 58.960 | 53.126 | 36.006 | 1.00 | 13.89 | O |
| ATOM | 30235 | N | THR | C | 690 | 57.885 | 52.657 | 34.070 | 1.00 | 12.48 | N |
| ATOM | 30236 | CA | THR | C | 690 | 57.994 | 54.010 | 33.553 | 1.00 | 12.91 | C |
| ATOM | 30238 | CB | THR | C | 690 | 57.548 | 54.122 | 32.099 | 1.00 | 12.59 | C |
| ATOM | 30240 | OG1 | THR | C | 690 | 56.141 | 53.800 | 31.986 | 1.00 | 14.92 | O |
| ATOM | 30242 | CG2 | THR | C | 690 | 58.385 | 53.222 | 31.145 | 1.00 | 12.33 | C |
| ATOM | 30246 | C | THR | C | 690 | 57.221 | 55.067 | 34.343 | 1.00 | 12.04 | C |
| ATOM | 30247 | O | THR | C | 690 | 56.232 | 54.787 | 35.031 | 1.00 | 11.89 | O |
| ATOM | 30249 | N | ILE | C | 691 | 57.674 | 56.301 | 34.195 | 1.00 | 12.96 | N |
| ATOM | 30250 | CA | ILE | C | 691 | 56.957 | 57.446 | 34.732 | 1.00 | 13.08 | C |
| ATOM | 30252 | CB | ILE | C | 691 | 57.632 | 58.758 | 34.261 | 1.00 | 12.95 | C |
| ATOM | 30254 | CG1 | ILE | C | 691 | 59.018 | 58.864 | 34.874 | 1.00 | 13.64 | C |
| ATOM | 30257 | CD1 | ILE | C | 691 | 59.949 | 59.839 | 34.110 | 1.00 | 13.52 | C |
| ATOM | 30261 | CG2 | ILE | C | 691 | 56.766 | 59.962 | 34.582 | 1.00 | 14.00 | C |
| ATOM | 30265 | C | ILE | C | 691 | 55.487 | 57.419 | 34.301 | 1.00 | 13.33 | C |
| ATOM | 30266 | O | ILE | C | 691 | 54.576 | 57.645 | 35.103 | 1.00 | 12.72 | O |
| ATOM | 30268 | N | GLY | C | 692 | 55.284 | 57.084 | 33.021 | 1.00 | 12.85 | N |
| ATOM | 30269 | CA | GLY | C | 692 | 53.953 | 57.055 | 32.421 | 1.00 | 13.07 | C |
| ATOM | 30272 | C | GLY | C | 692 | 53.065 | 56.032 | 33.081 | 1.00 | 12.50 | C |
| ATOM | 30273 | O | GLY | C | 692 | 51.871 | 56.292 | 33.344 | 1.00 | 13.24 | O |
| ATOM | 30275 | N | SER | C | 693 | 53.620 | 54.848 | 33.354 | 1.00 | 13.58 | N |
| ATOM | 30276 | CA | SER | C | 693 | 52.866 | 53.809 | 34.076 | 1.00 | 14.29 | C |
| ATOM | 30278 | CB | SER | C | 693 | 53.721 | 52.558 | 34.221 | 1.00 | 15.20 | C |
| ATOM | 30281 | OG | SER | C | 693 | 53.901 | 51.964 | 32.933 | 1.00 | 17.11 | O |
| ATOM | 30283 | C | SER | C | 693 | 52.375 | 54.332 | 35.434 | 1.00 | 14.26 | C |
| ATOM | 30284 | O | SER | C | 693 | 51.245 | 54.087 | 35.866 | 1.00 | 14.76 | O |
| ATOM | 30286 | N | ASN | C | 694 | 53.230 | 55.084 | 36.109 | 1.00 | 14.18 | N |
| ATOM | 30287 | CA | ASN | C | 694 | 52.883 | 55.633 | 37.392 | 1.00 | 14.71 | C |
| ATOM | 30289 | CB | ASN | C | 694 | 54.187 | 56.048 | 38.068 | 1.00 | 15.01 | C |
| ATOM | 30292 | CG | ASN | C | 694 | 54.946 | 54.845 | 38.567 | 1.00 | 17.58 | C |
| ATOM | 30293 | OD1 | ASN | C | 694 | 54.330 | 53.941 | 39.113 | 1.00 | 21.41 | O |
| ATOM | 30294 | ND2 | ASN | C | 694 | 56.244 | 54.779 | 38.351 | 1.00 | 15.94 | N |

| ATOM | 30297 | C | ASN | C | 694 | 51.869 | 56.778 | 37.292 | 1.00 | 13.98 | C |
|------|-------|---|-----|---|-----|--------|--------|--------|------|-------|---|
| ATOM | 30298 | O | ASN | C | 694 | 50.902 | 56.848 | 38.066 | 1.00 | 15.24 | O |
| ATOM | 30300 | N | VAL | C | 695 | 52.072 | 57.697 | 36.370 | 1.00 | 11.91 | N |
| ATOM | 30301 | CA | VAL | C | 695 | 51.047 | 58.734 | 36.166 | 1.00 | 12.50 | C |
| ATOM | 30303 | CB | VAL | C | 695 | 51.480 | 59.740 | 35.063 | 1.00 | 12.91 | C |
| ATOM | 30305 | CG1 | VAL | C | 695 | 50.377 | 60.712 | 34.738 | 1.00 | 13.55 | C |
| ATOM | 30309 | CG2 | VAL | C | 695 | 52.708 | 60.455 | 35.503 | 1.00 | 14.04 | C |
| ATOM | 30313 | C | VAL | C | 695 | 49.714 | 58.090 | 35.826 | 1.00 | 12.56 | C |
| ATOM | 30314 | O | VAL | C | 695 | 48.675 | 58.593 | 36.204 | 1.00 | 13.98 | O |
| ATOM | 30316 | N | SER | C | 696 | 49.744 | 57.020 | 35.022 | 1.00 | 12.22 | N |
| ATOM | 30317 | CA | SER | C | 696 | 48.498 | 56.351 | 34.615 | 1.00 | 13.54 | C |
| ATOM | 30319 | CB | SER | C | 696 | 48.792 | 55.198 | 33.642 | 1.00 | 13.20 | C |
| ATOM | 30322 | OG | SER | C | 696 | 49.445 | 55.716 | 32.478 | 1.00 | 13.48 | O |
| ATOM | 30324 | C | SER | C | 696 | 47.681 | 55.860 | 35.837 | 1.00 | 14.15 | C |
| ATOM | 30325 | O | SER | C | 696 | 46.457 | 55.909 | 35.820 | 1.00 | 13.96 | O |
| ATOM | 30327 | N | LYS | C | 697 | 48.360 | 55.403 | 36.889 | 1.00 | 13.98 | N |
| ATOM | 30328 | CA | LYS | C | 697 | 47.694 | 54.891 | 38.080 | 1.00 | 14.19 | C |
| ATOM | 30330 | CB | LYS | C | 697 | 48.707 | 54.326 | 39.081 | 1.00 | 14.66 | C |
| ATOM | 30333 | CG | LYS | C | 697 | 49.241 | 53.018 | 38.593 | 1.00 | 15.20 | C |
| ATOM | 30336 | CD | LYS | C | 697 | 50.132 | 52.286 | 39.603 | 1.00 | 19.23 | C |
| ATOM | 30339 | CE | LYS | C | 697 | 50.325 | 50.830 | 39.170 | 1.00 | 25.80 | C |
| ATOM | 30342 | NZ | LYS | C | 697 | 49.141 | 49.950 | 39.435 | 1.00 | 32.45 | N |
| ATOM | 30346 | C | LYS | C | 697 | 46.925 | 56.055 | 38.741 | 1.00 | 13.69 | C |
| ATOM | 30347 | O | LYS | C | 697 | 45.808 | 55.851 | 39.269 | 1.00 | 13.73 | O |
| ATOM | 30349 | N | ILE | C | 698 | 47.512 | 57.260 | 38.733 | 1.00 | 13.29 | N |
| ATOM | 30350 | CA | ILE | C | 698 | 46.878 | 58.404 | 39.344 | 1.00 | 13.37 | C |
| ATOM | 30352 | CB | ILE | C | 698 | 47.861 | 59.594 | 39.460 | 1.00 | 10.66 | C |
| ATOM | 30354 | CG1 | ILE | C | 698 | 49.035 | 59.226 | 40.377 | 1.00 | 13.05 | C |
| ATOM | 30357 | CD1 | ILE | C | 698 | 50.127 | 60.280 | 40.397 | 1.00 | 12.88 | C |
| ATOM | 30361 | CG2 | ILE | C | 698 | 47.195 | 60.846 | 40.027 | 1.00 | 13.90 | C |
| ATOM | 30365 | C | ILE | C | 698 | 45.675 | 58.823 | 38.484 | 1.00 | 13.65 | C |
| ATOM | 30366 | O | ILE | C | 698 | 44.565 | 59.081 | 38.985 | 1.00 | 13.40 | O |
| ATOM | 30368 | N | TYR | C | 699 | 45.888 | 58.914 | 37.165 | 1.00 | 14.14 | N |
| ATOM | 30369 | CA | TYR | C | 699 | 44.782 | 59.214 | 36.225 | 1.00 | 12.83 | C |
| ATOM | 30371 | CB | TYR | C | 699 | 45.320 | 59.147 | 34.795 | 1.00 | 13.16 | C |
| ATOM | 30374 | CG | TYR | C | 699 | 44.293 | 59.103 | 33.703 | 1.00 | 11.54 | C |
| ATOM | 30375 | CD1 | TYR | C | 699 | 43.657 | 60.249 | 33.231 | 1.00 | 13.47 | C |
| ATOM | 30377 | CE1 | TYR | C | 699 | 42.756 | 60.169 | 32.162 | 1.00 | 12.40 | C |
| ATOM | 30379 | CZ | TYR | C | 699 | 42.470 | 58.927 | 31.601 | 1.00 | 12.73 | C |
| ATOM | 30380 | OH | TYR | C | 699 | 41.607 | 58.802 | 30.528 | 1.00 | 14.41 | O |
| ATOM | 30382 | CE2 | TYR | C | 699 | 43.092 | 57.803 | 32.055 | 1.00 | 12.58 | C |
| ATOM | 30384 | CD2 | TYR | C | 699 | 43.988 | 57.899 | 33.110 | 1.00 | 9.63 | C |
| ATOM | 30386 | C | TYR | C | 699 | 43.596 | 58.244 | 36.417 | 1.00 | 13.30 | C |
| ATOM | 30387 | O | TYR | C | 699 | 42.445 | 58.656 | 36.440 | 1.00 | 13.56 | O |
| ATOM | 30389 | N | GLU | C | 700 | 43.874 | 56.968 | 36.534 | 1.00 | 12.54 | N |
| ATOM | 30390 | CA | GLU | C | 700 | 42.813 | 55.985 | 36.701 | 1.00 | 13.37 | C |
| ATOM | 30392 | CB | GLU | C | 700 | 43.381 | 54.581 | 36.552 | 1.00 | 13.54 | C |
| ATOM | 30395 | CG | GLU | C | 700 | 43.769 | 54.281 | 35.159 | 1.00 | 13.43 | C |
| ATOM | 30398 | CD | GLU | C | 700 | 44.465 | 52.916 | 34.970 | 1.00 | 16.01 | C |
| ATOM | 30399 | OE1 | GLU | C | 700 | 44.969 | 52.326 | 35.977 | 1.00 | 20.36 | O |
| ATOM | 30400 | OE2 | GLU | C | 700 | 44.469 | 52.444 | 33.798 | 1.00 | 17.11 | O |
| ATOM | 30401 | C | GLU | C | 700 | 42.041 | 56.196 | 37.996 | 1.00 | 13.86 | C |
| ATOM | 30402 | O | GLU | C | 700 | 40.825 | 56.027 | 38.012 | 1.00 | 15.54 | O |
| ATOM | 30404 | N | ALA | C | 701 | 42.738 | 56.586 | 39.061 | 1.00 | 14.32 | N |
| ATOM | 30405 | CA | ALA | C | 701 | 42.096 | 56.931 | 40.338 | 1.00 | 13.77 | C |
| ATOM | 30407 | CB | ALA | C | 701 | 43.136 | 57.121 | 41.434 | 1.00 | 14.25 | C |
| ATOM | 30411 | C | ALA | C | 701 | 41.234 | 58.191 | 40.251 | 1.00 | 14.04 | C |

| | | | | | | | | | |
|---|---|---|---|---|---|---|---|---|---|
| ATOM | 30412 | O | ALA | C | 701 | 40.275 | 58.352 | 41.000 | 1.00 15.87 | O |
| ATOM | 30414 | N | ILE | C | 702 | 41.593 | 59.111 | 39.369 | 1.00 14.36 | N |
| ATOM | 30415 | CA | ILE | C | 702 | 40.758 | 60.296 | 39.127 | 1.00 13.74 | C |
| ATOM | 30417 | CB | ILE | C | 702 | 41.513 | 61.396 | 38.382 | 1.00 15.23 | C |
| ATOM | 30419 | CG1 | ILE | C | 702 | 42.656 | 61.915 | 39.261 | 1.00 15.10 | C |
| ATOM | 30422 | CD1 | ILE | C | 702 | 43.692 | 62.809 | 38.569 | 1.00 16.37 | C |
| ATOM | 30426 | CG2 | ILE | C | 702 | 40.538 | 62.555 | 38.032 | 1.00 14.05 | C |
| ATOM | 30430 | C | ILE | C | 702 | 39.526 | 59.862 | 38.350 | 1.00 14.36 | C |
| ATOM | 30431 | O | ILE | C | 702 | 38.415 | 60.220 | 38.703 | 1.00 15.19 | O |
| ATOM | 30433 | N | LYS | C | 703 | 39.745 | 59.137 | 37.257 | 1.00 13.70 | N |
| ATOM | 30434 | CA | LYS | C | 703 | 38.634 | 58.793 | 36.373 | 1.00 14.42 | C |
| ATOM | 30436 | CB | LYS | C | 703 | 39.183 | 58.138 | 35.101 | 1.00 14.20 | C |
| ATOM | 30439 | CG | LYS | C | 703 | 39.992 | 59.082 | 34.160 | 1.00 15.46 | C |
| ATOM | 30442 | CD | LYS | C | 703 | 39.223 | 60.325 | 33.572 | 1.00 17.74 | C |
| ATOM | 30445 | CE | LYS | C | 703 | 38.066 | 59.956 | 32.632 | 1.00 21.51 | C |
| ATOM | 30448 | NZ | LYS | C | 703 | 38.443 | 59.134 | 31.483 | 1.00 20.35 | N |
| ATOM | 30452 | C | LYS | C | 703 | 37.602 | 57.883 | 37.024 | 1.00 16.05 | C |
| ATOM | 30453 | O | LYS | C | 703 | 36.394 | 57.996 | 36.777 | 1.00 16.88 | O |
| ATOM | 30455 | N | SER | C | 704 | 38.065 | 56.954 | 37.864 | 1.00 14.10 | N |
| ATOM | 30456 | CA | SER | C | 704 | 37.171 | 56.016 | 38.562 | 1.00 14.79 | C |
| ATOM | 30458 | CB | SER | C | 704 | 37.981 | 54.879 | 39.161 | 1.00 15.56 | C |
| ATOM | 30461 | OG | SER | C | 704 | 38.776 | 55.351 | 40.232 | 1.00 14.66 | O |
| ATOM | 30463 | C | SER | C | 704 | 36.418 | 56.710 | 39.705 | 1.00 14.82 | C |
| ATOM | 30464 | O | SER | C | 704 | 35.512 | 56.112 | 40.298 | 1.00 16.44 | O |
| ATOM | 30466 | N | GLY | C | 705 | 36.893 | 57.887 | 40.107 | 1.00 13.73 | N |
| ATOM | 30467 | CA | GLY | C | 705 | 36.356 | 58.559 | 41.276 | 1.00 14.06 | C |
| ATOM | 30470 | C | GLY | C | 705 | 36.913 | 58.138 | 42.615 | 1.00 14.95 | C |
| ATOM | 30471 | O | GLY | C | 705 | 36.494 | 58.637 | 43.657 | 1.00 14.11 | O |
| ATOM | 30473 | N | ARG | C | 706 | 37.862 | 57.221 | 42.610 | 1.00 13.98 | N |
| ATOM | 30474 | CA | ARG | C | 706 | 38.449 | 56.752 | 43.877 | 1.00 14.05 | C |
| ATOM | 30476 | CB | ARG | C | 706 | 39.518 | 55.712 | 43.578 | 1.00 14.10 | C |
| ATOM | 30479 | CG | ARG | C | 706 | 40.111 | 55.133 | 44.831 | 1.00 13.73 | C |
| ATOM | 30482 | CD | ARG | C | 706 | 41.139 | 54.066 | 44.514 | 1.00 15.87 | C |
| ATOM | 30485 | NE | ARG | C | 706 | 41.682 | 53.471 | 45.741 | 1.00 19.67 | N |
| ATOM | 30487 | CZ | ARG | C | 706 | 42.672 | 52.607 | 45.739 | 1.00 17.41 | C |
| ATOM | 30488 | NH1 | ARG | C | 706 | 43.226 | 52.244 | 44.589 | 1.00 18.18 | N |
| ATOM | 30491 | NH2 | ARG | C | 706 | 43.096 | 52.090 | 46.885 | 1.00 20.78 | N |
| ATOM | 30494 | C | ARG | C | 706 | 39.032 | 57.970 | 44.683 | 1.00 14.17 | C |
| ATOM | 30495 | O | ARG | C | 706 | 38.992 | 57.993 | 45.915 | 1.00 14.64 | O |
| ATOM | 30497 | N | ILE | C | 707 | 39.583 | 58.965 | 43.980 | 1.00 12.62 | N |
| ATOM | 30498 | CA | ILE | C | 707 | 40.158 | 60.132 | 44.640 | 1.00 13.35 | C |
| ATOM | 30500 | CB | ILE | C | 707 | 40.997 | 60.913 | 43.611 | 1.00 13.45 | C |
| ATOM | 30502 | CG1 | ILE | C | 707 | 42.144 | 61.671 | 44.305 | 1.00 15.22 | C |
| ATOM | 30505 | CD1 | ILE | C | 707 | 43.050 | 62.352 | 43.371 | 1.00 16.77 | C |
| ATOM | 30509 | CG2 | ILE | C | 707 | 40.079 | 61.736 | 42.727 | 1.00 13.29 | C |
| ATOM | 30513 | C | ILE | C | 707 | 39.107 | 61.040 | 45.296 | 1.00 13.90 | C |
| ATOM | 30514 | O | ILE | C | 707 | 39.424 | 61.918 | 46.126 | 1.00 13.35 | O |
| ATOM | 30516 | N | ASN | C | 708 | 37.847 | 60.872 | 44.923 | 1.00 13.13 | N |
| ATOM | 30517 | CA | ASN | C | 708 | 36.810 | 61.833 | 45.293 | 1.00 13.70 | C |
| ATOM | 30519 | CB | ASN | C | 708 | 35.482 | 61.502 | 44.620 | 1.00 14.13 | C |
| ATOM | 30522 | CG | ASN | C | 708 | 35.537 | 61.673 | 43.106 | 1.00 14.59 | C |
| ATOM | 30523 | OD1 | ASN | C | 708 | 36.464 | 62.298 | 42.558 | 1.00 15.42 | O |
| ATOM | 30524 | ND2 | ASN | C | 708 | 34.515 | 61.094 | 42.405 | 1.00 15.24 | N |
| ATOM | 30527 | C | ASN | C | 708 | 36.630 | 61.932 | 46.815 | 1.00 14.28 | C |
| ATOM | 30528 | O | ASN | C | 708 | 36.556 | 63.023 | 47.381 | 1.00 13.75 | O |
| ATOM | 30530 | N | ASN | C | 709 | 36.538 | 60.789 | 47.499 | 1.00 14.09 | N |
| ATOM | 30531 | CA | ASN | C | 709 | 36.393 | 60.825 | 48.949 | 1.00 14.76 | C |

```
ATOM  30533  CB   ASN C 709      36.045  59.439  49.463  1.00 15.79           C
ATOM  30536  CG   ASN C 709      34.574  59.091  49.263  1.00 19.33           C
ATOM  30537  OD1  ASN C 709      33.727  59.967  49.047  1.00 23.23           O
ATOM  30538  ND2  ASN C 709      34.248  57.827  49.430  1.00 23.77           N
ATOM  30541  C    ASN C 709      37.649  61.354  49.640  1.00 13.99           C
ATOM  30542  O    ASN C 709      37.588  61.860  50.758  1.00 13.92           O
ATOM  30544  N    VAL C 710      38.786  61.176  48.996  1.00 13.14           N
ATOM  30545  CA   VAL C 710      40.050  61.695  49.532  1.00 13.62           C
ATOM  30547  CB   VAL C 710      41.261  61.237  48.708  1.00 12.70           C
ATOM  30549  CG1  VAL C 710      42.550  61.810  49.266  1.00 15.82           C
ATOM  30553  CG2  VAL C 710      41.269  59.708  48.646  1.00 17.29           C
ATOM  30557  C    VAL C 710      39.975  63.236  49.511  1.00 14.26           C
ATOM  30558  O    VAL C 710      40.276  63.871  50.514  1.00 15.07           O
ATOM  30560  N    LEU C 711      39.524  63.826  48.398  1.00 15.06           N
ATOM  30561  CA   LEU C 711      39.402  65.281  48.304  1.00 14.75           C
ATOM  30563  CB   LEU C 711      38.951  65.724  46.891  1.00 15.23           C
ATOM  30566  CG   LEU C 711      39.917  65.369  45.740  1.00 16.25           C
ATOM  30568  CD1  LEU C 711      39.244  65.474  44.378  1.00 16.20           C
ATOM  30572  CD2  LEU C 711      41.201  66.175  45.807  1.00 17.16           C
ATOM  30576  C    LEU C 711      38.413  65.813  49.350  1.00 15.47           C
ATOM  30577  O    LEU C 711      38.625  66.829  49.986  1.00 14.78           O
ATOM  30579  N    LEU C 712      37.288  65.126  49.478  1.00 15.38           N
ATOM  30580  CA   LEU C 712      36.300  65.468  50.476  1.00 16.53           C
ATOM  30582  CB   LEU C 712      35.139  64.467  50.413  1.00 17.24           C
ATOM  30585  CG   LEU C 712      33.928  64.808  51.291  1.00 19.44           C
ATOM  30587  CD1  LEU C 712      33.332  66.225  50.997  1.00 22.48           C
ATOM  30591  CD2  LEU C 712      32.855  63.723  51.115  1.00 20.48           C
ATOM  30595  C    LEU C 712      36.896  65.439  51.877  1.00 16.55           C
ATOM  30596  O    LEU C 712      36.671  66.341  52.664  1.00 17.93           O
ATOM  30598  N    LYS C 713      37.633  64.390  52.197  1.00 15.87           N
ATOM  30599  CA   LYS C 713      38.220  64.283  53.522  1.00 16.36           C
ATOM  30601  CB   LYS C 713      38.990  62.948  53.674  1.00 16.41           C
ATOM  30604  CG   LYS C 713      39.519  62.742  55.075  1.00 18.24           C
ATOM  30607  CD   LYS C 713      40.192  61.370  55.175  1.00 20.64           C
ATOM  30610  CE   LYS C 713      40.974  61.151  56.501  1.00 22.53           C
ATOM  30613  NZ   LYS C 713      41.532  59.754  56.559  1.00 26.23           N
ATOM  30617  C    LYS C 713      39.123  65.467  53.846  1.00 16.86           C
ATOM  30618  O    LYS C 713      39.127  65.998  54.949  1.00 15.59           O
ATOM  30620  N    MSE C 714      39.932  65.842  52.873  1.00 18.39           N
ATOM  30621  CA   MSE C 714      40.886  66.927  53.060  1.00 20.99           C
ATOM  30623  CB   MSE C 714      41.708  67.058  51.807  1.00 21.42           C
ATOM  30626  CG   MSE C 714      42.635  65.979  51.509  1.00 22.91           C
ATOM  30629  SE   MSE C 714      43.207  66.205  49.558  1.00 32.14           SE
ATOM  30630  CE   MSE C 714      42.189  67.723  48.966  1.00 35.26           C
ATOM  30634  C    MSE C 714      40.197  68.269  53.247  1.00 20.97           C
ATOM  30635  O    MSE C 714      40.710  69.146  53.945  1.00 20.91           O
ATOM  30637  N    LEU C 715      39.072  68.451  52.561  1.00 20.86           N
ATOM  30638  CA   LEU C 715      38.444  69.759  52.456  1.00 22.15           C
ATOM  30640  CB   LEU C 715      38.056  70.058  51.003  1.00 22.02           C
ATOM  30643  CG   LEU C 715      39.216  70.413  50.113  1.00 19.61           C
ATOM  30645  CD1  LEU C 715      38.751  70.332  48.679  1.00 21.94           C
ATOM  30649  CD2  LEU C 715      39.733  71.783  50.466  1.00 22.45           C
ATOM  30653  C    LEU C 715      37.229  69.948  53.313  1.00 24.97           C
ATOM  30654  O    LEU C 715      36.737  71.069  53.415  1.00 26.26           O
ATOM  30656  N    ALA C 716      36.703  68.878  53.893  1.00 26.99           N
ATOM  30657  CA   ALA C 716      35.454  68.980  54.636  1.00 29.26           C
ATOM  30659  CB   ALA C 716      34.862  67.610  54.885  1.00 29.94           C
```

| ATOM | 30663 | C   | ALA | C | 716 | 35.714 | 69.707 | 55.953 | 1.00 | 30.37 | C |
|------|-------|-----|-----|---|-----|--------|--------|--------|------|-------|---|
| ATOM | 30664 | O   | ALA | C | 716 | 34.789 | 70.349 | 56.472 | 1.00 | 33.19 | O |
| ATOM | 30666 | OXT | ALA | C | 716 | 36.820 | 69.701 | 56.521 | 1.00 | 31.15 | O |
| ATOM | 30667 | N   | ALA | D | 26  | 26.238 | 98.589 | 50.819 | 1.00 | 39.11 | N |
| ATOM | 30668 | CA  | ALA | D | 26  | 25.956 | 97.766 | 49.591 | 1.00 | 39.11 | C |
| ATOM | 30670 | CB  | ALA | D | 26  | 26.917 | 96.596 | 49.501 | 1.00 | 39.30 | C |
| ATOM | 30674 | C   | ALA | D | 26  | 24.512 | 97.257 | 49.629 | 1.00 | 39.17 | C |
| ATOM | 30675 | O   | ALA | D | 26  | 24.059 | 96.759 | 50.672 | 1.00 | 39.27 | O |
| ATOM | 30679 | N   | SER | D | 27  | 23.788 | 97.371 | 48.513 | 1.00 | 38.87 | N |
| ATOM | 30680 | CA  | SER | D | 27  | 22.359 | 96.998 | 48.495 | 1.00 | 38.65 | C |
| ATOM | 30682 | CB  | SER | D | 27  | 21.669 | 97.557 | 47.247 | 1.00 | 38.64 | C |
| ATOM | 30685 | OG  | SER | D | 27  | 20.264 | 97.405 | 47.334 | 1.00 | 37.01 | O |
| ATOM | 30687 | C   | SER | D | 27  | 22.107 | 95.477 | 48.576 | 1.00 | 39.13 | C |
| ATOM | 30688 | O   | SER | D | 27  | 22.786 | 94.679 | 47.923 | 1.00 | 38.68 | O |
| ATOM | 30690 | N   | THR | D | 28  | 21.115 | 95.093 | 49.386 | 1.00 | 39.27 | N |
| ATOM | 30691 | CA  | THR | D | 28  | 20.660 | 93.705 | 49.484 | 1.00 | 39.73 | C |
| ATOM | 30693 | CB  | THR | D | 28  | 20.324 | 93.331 | 50.953 | 1.00 | 39.90 | C |
| ATOM | 30695 | OG1 | THR | D | 28  | 19.078 | 93.932 | 51.334 | 1.00 | 40.20 | O |
| ATOM | 30697 | CG2 | THR | D | 28  | 21.416 | 93.831 | 51.903 | 1.00 | 40.56 | C |
| ATOM | 30701 | C   | THR | D | 28  | 19.417 | 93.499 | 48.592 | 1.00 | 39.92 | C |
| ATOM | 30702 | O   | THR | D | 28  | 18.865 | 92.400 | 48.529 | 1.00 | 40.72 | O |
| ATOM | 30704 | N   | ASN | D | 29  | 18.969 | 94.567 | 47.929 | 1.00 | 39.98 | N |
| ATOM | 30705 | CA  | ASN | D | 29  | 17.915 | 94.488 | 46.912 | 1.00 | 39.19 | C |
| ATOM | 30707 | CB  | ASN | D | 29  | 17.343 | 95.885 | 46.636 | 1.00 | 39.38 | C |
| ATOM | 30710 | CG  | ASN | D | 29  | 16.368 | 95.924 | 45.450 | 1.00 | 41.07 | C |
| ATOM | 30711 | OD1 | ASN | D | 29  | 15.984 | 94.886 | 44.877 | 1.00 | 43.46 | O |
| ATOM | 30712 | ND2 | ASN | D | 29  | 15.949 | 97.144 | 45.089 | 1.00 | 44.42 | N |
| ATOM | 30715 | C   | ASN | D | 29  | 18.486 | 93.853 | 45.634 | 1.00 | 38.51 | C |
| ATOM | 30716 | O   | ASN | D | 29  | 19.435 | 94.374 | 45.021 | 1.00 | 37.34 | O |
| ATOM | 30718 | N   | LEU | D | 30  | 17.902 | 92.721 | 45.243 | 1.00 | 37.60 | N |
| ATOM | 30719 | CA  | LEU | D | 30  | 18.431 | 91.951 | 44.109 | 1.00 | 37.11 | C |
| ATOM | 30721 | CB  | LEU | D | 30  | 17.751 | 90.557 | 44.016 | 1.00 | 37.58 | C |
| ATOM | 30724 | CG  | LEU | D | 30  | 18.103 | 89.474 | 45.071 | 1.00 | 38.89 | C |
| ATOM | 30726 | CD1 | LEU | D | 30  | 17.434 | 88.135 | 44.773 | 1.00 | 38.46 | C |
| ATOM | 30730 | CD2 | LEU | D | 30  | 19.610 | 89.244 | 45.155 | 1.00 | 39.90 | C |
| ATOM | 30734 | C   | LEU | D | 30  | 18.310 | 92.708 | 42.779 | 1.00 | 36.27 | C |
| ATOM | 30735 | O   | LEU | D | 30  | 19.084 | 92.433 | 41.860 | 1.00 | 36.17 | O |
| ATOM | 30737 | N   | ALA | D | 31  | 17.346 | 93.629 | 42.665 | 1.00 | 35.50 | N |
| ATOM | 30738 | CA  | ALA | D | 31  | 17.281 | 94.535 | 41.479 | 1.00 | 35.54 | C |
| ATOM | 30740 | CB  | ALA | D | 31  | 16.039 | 95.414 | 41.520 | 1.00 | 34.88 | C |
| ATOM | 30744 | C   | ALA | D | 31  | 18.563 | 95.387 | 41.344 | 1.00 | 35.56 | C |
| ATOM | 30745 | O   | ALA | D | 31  | 19.013 | 95.684 | 40.221 | 1.00 | 34.60 | O |
| ATOM | 30747 | N   | VAL | D | 32  | 19.176 | 95.733 | 42.477 | 1.00 | 35.43 | N |
| ATOM | 30748 | CA  | VAL | D | 32  | 20.575 | 96.227 | 42.485 | 1.00 | 36.61 | C |
| ATOM | 30750 | CB  | VAL | D | 32  | 20.986 | 96.892 | 43.835 | 1.00 | 37.24 | C |
| ATOM | 30752 | CG1 | VAL | D | 32  | 22.392 | 97.617 | 43.716 | 1.00 | 38.08 | C |
| ATOM | 30756 | CG2 | VAL | D | 32  | 19.867 | 97.779 | 44.402 | 1.00 | 38.75 | C |
| ATOM | 30760 | C   | VAL | D | 32  | 21.575 | 95.092 | 42.233 | 1.00 | 36.21 | C |
| ATOM | 30761 | O   | VAL | D | 32  | 22.544 | 95.288 | 41.489 | 1.00 | 36.22 | O |
| ATOM | 30763 | N   | THR | D | 39  | 16.765 | 82.512 | 40.210 | 1.00 | 29.00 | N |
| ATOM | 30764 | CA  | THR | D | 39  | 15.775 | 82.869 | 41.206 | 1.00 | 29.34 | C |
| ATOM | 30766 | CB  | THR | D | 39  | 16.370 | 83.668 | 42.430 | 1.00 | 30.11 | C |
| ATOM | 30768 | OG1 | THR | D | 39  | 15.300 | 84.101 | 43.295 | 1.00 | 28.37 | O |
| ATOM | 30770 | CG2 | THR | D | 39  | 17.187 | 84.909 | 41.971 | 1.00 | 31.35 | C |
| ATOM | 30774 | C   | THR | D | 39  | 14.642 | 83.695 | 40.631 | 1.00 | 30.56 | C |
| ATOM | 30775 | O   | THR | D | 39  | 14.865 | 84.603 | 39.825 | 1.00 | 30.89 | O |
| ATOM | 30777 | N   | THR | D | 40  | 13.424 | 83.385 | 41.067 | 1.00 | 30.60 | N |

| ATOM | 30778 | CA | THR | D | 40 | 12.242 | 84.128 | 40.640 | 1.00 | 31.81 | C |
|------|-------|-----|-----|---|----|--------|--------|--------|------|-------|---|
| ATOM | 30780 | CB | THR | D | 40 | 10.937 | 83.301 | 40.871 | 1.00 | 31.66 | C |
| ATOM | 30782 | OG1 | THR | D | 40 | 10.933 | 82.791 | 42.210 | 1.00 | 32.32 | O |
| ATOM | 30784 | CG2 | THR | D | 40 | 10.797 | 82.115 | 39.838 | 1.00 | 31.44 | C |
| ATOM | 30788 | C | THR | D | 40 | 12.137 | 85.467 | 41.392 | 1.00 | 32.25 | C |
| ATOM | 30789 | O | THR | D | 40 | 11.228 | 86.268 | 41.131 | 1.00 | 32.33 | O |
| ATOM | 30791 | N | GLN | D | 41 | 13.068 | 85.713 | 42.321 | 1.00 | 32.24 | N |
| ATOM | 30792 | CA | GLN | D | 41 | 13.027 | 86.919 | 43.131 | 1.00 | 32.59 | C |
| ATOM | 30794 | CB | GLN | D | 41 | 13.749 | 86.692 | 44.458 | 1.00 | 32.98 | C |
| ATOM | 30797 | CG | GLN | D | 41 | 13.108 | 85.660 | 45.342 | 1.00 | 35.35 | C |
| ATOM | 30800 | CD | GLN | D | 41 | 13.483 | 85.864 | 46.801 | 1.00 | 36.90 | C |
| ATOM | 30801 | OE1 | GLN | D | 41 | 14.407 | 86.635 | 47.121 | 1.00 | 42.77 | O |
| ATOM | 30802 | NE2 | GLN | D | 41 | 12.759 | 85.187 | 47.701 | 1.00 | 42.10 | N |
| ATOM | 30805 | C | GLN | D | 41 | 13.650 | 88.147 | 42.461 | 1.00 | 30.77 | C |
| ATOM | 30806 | O | GLN | D | 41 | 13.627 | 89.242 | 43.049 | 1.00 | 31.67 | O |
| ATOM | 30808 | N | VAL | D | 42 | 14.256 | 88.006 | 41.289 | 1.00 | 26.91 | N |
| ATOM | 30809 | CA | VAL | D | 42 | 14.754 | 89.219 | 40.645 | 1.00 | 25.65 | C |
| ATOM | 30811 | CB | VAL | D | 42 | 16.023 | 89.678 | 41.226 | 1.00 | 25.97 | C |
| ATOM | 30813 | CG1 | VAL | D | 42 | 17.161 | 88.718 | 40.818 | 1.00 | 27.51 | C |
| ATOM | 30817 | CG2 | VAL | D | 42 | 16.309 | 91.137 | 40.826 | 1.00 | 26.28 | C |
| ATOM | 30821 | C | VAL | D | 42 | 15.065 | 89.085 | 39.195 | 1.00 | 23.93 | C |
| ATOM | 30822 | O | VAL | D | 42 | 15.974 | 88.335 | 38.812 | 1.00 | 24.88 | O |
| ATOM | 30824 | N | THR | D | 43 | 14.430 | 89.932 | 38.407 | 1.00 | 19.73 | N |
| ATOM | 30825 | CA | THR | D | 43 | 14.411 | 89.757 | 36.991 | 1.00 | 18.03 | C |
| ATOM | 30827 | CB | THR | D | 43 | 12.983 | 89.965 | 36.472 | 1.00 | 17.15 | C |
| ATOM | 30829 | OG1 | THR | D | 43 | 12.583 | 91.325 | 36.715 | 1.00 | 17.58 | O |
| ATOM | 30831 | CG2 | THR | D | 43 | 12.004 | 88.993 | 37.158 | 1.00 | 17.53 | C |
| ATOM | 30835 | C | THR | D | 43 | 15.263 | 90.788 | 36.287 | 1.00 | 16.17 | C |
| ATOM | 30836 | O | THR | D | 43 | 15.655 | 91.818 | 36.863 | 1.00 | 14.79 | O |
| ATOM | 30838 | N | GLN | D | 44 | 15.550 | 90.517 | 35.022 | 1.00 | 15.59 | N |
| ATOM | 30839 | CA | GLN | D | 44 | 16.250 | 91.500 | 34.200 | 1.00 | 15.17 | C |
| ATOM | 30841 | CB | GLN | D | 44 | 16.507 | 90.941 | 32.798 | 1.00 | 15.31 | C |
| ATOM | 30844 | CG | GLN | D | 44 | 17.456 | 91.724 | 31.973 | 1.00 | 15.81 | C |
| ATOM | 30847 | CD | GLN | D | 44 | 17.900 | 90.887 | 30.796 | 1.00 | 16.66 | C |
| ATOM | 30848 | OE1 | GLN | D | 44 | 17.053 | 90.336 | 30.103 | 1.00 | 14.73 | O |
| ATOM | 30849 | NE2 | GLN | D | 44 | 19.203 | 90.851 | 30.517 | 1.00 | 15.26 | N |
| ATOM | 30852 | C | GLN | D | 44 | 15.482 | 92.805 | 34.086 | 1.00 | 15.04 | C |
| ATOM | 30853 | O | GLN | D | 44 | 16.076 | 93.877 | 34.105 | 1.00 | 15.32 | O |
| ATOM | 30855 | N | VAL | D | 45 | 14.180 | 92.747 | 33.946 | 1.00 | 14.55 | N |
| ATOM | 30856 | CA | VAL | D | 45 | 13.425 | 94.008 | 33.929 | 1.00 | 15.60 | C |
| ATOM | 30858 | CB | VAL | D | 45 | 11.945 | 93.755 | 33.714 | 1.00 | 17.30 | C |
| ATOM | 30860 | CG1 | VAL | D | 45 | 11.115 | 94.999 | 34.031 | 1.00 | 18.99 | C |
| ATOM | 30864 | CG2 | VAL | D | 45 | 11.715 | 93.362 | 32.283 | 1.00 | 19.16 | C |
| ATOM | 30868 | C | VAL | D | 45 | 13.679 | 94.805 | 35.222 | 1.00 | 14.52 | C |
| ATOM | 30869 | O | VAL | D | 45 | 13.891 | 96.009 | 35.169 | 1.00 | 15.08 | O |
| ATOM | 30871 | N | ASP | D | 46 | 13.642 | 94.144 | 36.377 | 1.00 | 14.59 | N |
| ATOM | 30872 | CA | ASP | D | 46 | 13.882 | 94.807 | 37.657 | 1.00 | 15.50 | C |
| ATOM | 30874 | CB | ASP | D | 46 | 13.911 | 93.794 | 38.810 | 1.00 | 16.29 | C |
| ATOM | 30877 | CG | ASP | D | 46 | 12.579 | 93.172 | 39.120 | 1.00 | 21.59 | C |
| ATOM | 30878 | OD1 | ASP | D | 46 | 11.539 | 93.785 | 38.769 | 1.00 | 20.70 | O |
| ATOM | 30879 | OD2 | ASP | D | 46 | 12.598 | 92.062 | 39.772 | 1.00 | 22.35 | O |
| ATOM | 30880 | C | ASP | D | 46 | 15.236 | 95.484 | 37.652 | 1.00 | 15.33 | C |
| ATOM | 30881 | O | ASP | D | 46 | 15.398 | 96.620 | 38.124 | 1.00 | 15.35 | O |
| ATOM | 30883 | N | ILE | D | 47 | 16.233 | 94.739 | 37.193 | 1.00 | 14.16 | N |
| ATOM | 30884 | CA | ILE | D | 47 | 17.605 | 95.271 | 37.113 | 1.00 | 15.23 | C |
| ATOM | 30886 | CB | ILE | D | 47 | 18.550 | 94.127 | 36.661 | 1.00 | 15.14 | C |
| ATOM | 30888 | CG1 | ILE | D | 47 | 18.647 | 93.082 | 37.774 | 1.00 | 16.78 | C |

| ATOM | 30891 | CD1 | ILE | D | 47 | 19.474 | 91.875 | 37.386 | 1.00 | 19.05 | C |
|---|---|---|---|---|---|---|---|---|---|---|---|
| ATOM | 30895 | CG2 | ILE | D | 47 | 19.923 | 94.623 | 36.284 | 1.00 | 17.05 | C |
| ATOM | 30899 | C | ILE | D | 47 | 17.739 | 96.483 | 36.194 | 1.00 | 15.18 | C |
| ATOM | 30900 | O | ILE | D | 47 | 18.341 | 97.517 | 36.520 | 1.00 | 14.99 | O |
| ATOM | 30902 | N | VAL | D | 48 | 17.135 | 96.374 | 35.034 | 1.00 | 13.73 | N |
| ATOM | 30903 | CA | VAL | D | 48 | 17.102 | 97.445 | 34.069 | 1.00 | 13.44 | C |
| ATOM | 30905 | CB | VAL | D | 48 | 16.439 | 96.982 | 32.777 | 1.00 | 12.69 | C |
| ATOM | 30907 | CG1 | VAL | D | 48 | 16.139 | 98.145 | 31.914 | 1.00 | 15.36 | C |
| ATOM | 30911 | CG2 | VAL | D | 48 | 17.377 | 96.049 | 32.048 | 1.00 | 13.35 | C |
| ATOM | 30915 | C | VAL | D | 48 | 16.370 | 98.700 | 34.605 | 1.00 | 14.25 | C |
| ATOM | 30916 | O | VAL | D | 48 | 16.858 | 99.807 | 34.465 | 1.00 | 14.38 | O |
| ATOM | 30918 | N | GLU | D | 49 | 15.208 | 98.491 | 35.232 | 1.00 | 14.62 | N |
| ATOM | 30919 | CA | GLU | D | 49 | 14.461 | 99.581 | 35.842 | 1.00 | 15.83 | C |
| ATOM | 30921 | CB | GLU | D | 49 | 13.260 | 99.030 | 36.586 | 1.00 | 15.68 | C |
| ATOM | 30924 | CG | GLU | D | 49 | 12.393 | 100.115 | 37.193 | 1.00 | 19.60 | C |
| ATOM | 30927 | CD | GLU | D | 49 | 11.065 | 99.565 | 37.711 | 1.00 | 23.85 | C |
| ATOM | 30928 | OE1 | GLU | D | 49 | 10.866 | 98.325 | 37.733 | 1.00 | 34.09 | O |
| ATOM | 30929 | OE2 | GLU | D | 49 | 10.194 | 100.389 | 38.092 | 1.00 | 35.47 | O |
| ATOM | 30930 | C | GLU | D | 49 | 15.357 | 100.339 | 36.826 | 1.00 | 14.47 | C |
| ATOM | 30931 | O | GLU | D | 49 | 15.430 | 101.562 | 36.792 | 1.00 | 14.31 | O |
| ATOM | 30933 | N | LYS | D | 50 | 16.060 | 99.607 | 37.677 | 1.00 | 14.78 | N |
| ATOM | 30934 | CA | LYS | D | 50 | 16.926 | 100.240 | 38.669 | 1.00 | 15.86 | C |
| ATOM | 30936 | CB | LYS | D | 50 | 17.492 | 99.199 | 39.613 | 1.00 | 17.14 | C |
| ATOM | 30939 | CG | LYS | D | 50 | 18.404 | 99.823 | 40.634 | 1.00 | 22.17 | C |
| ATOM | 30942 | CD | LYS | D | 50 | 19.284 | 98.818 | 41.260 | 1.00 | 30.06 | C |
| ATOM | 30945 | CE | LYS | D | 50 | 20.517 | 99.497 | 41.896 | 1.00 | 34.85 | C |
| ATOM | 30948 | NZ | LYS | D | 50 | 20.148 | 100.126 | 43.184 | 1.00 | 37.85 | N |
| ATOM | 30952 | C | LYS | D | 50 | 18.079 | 100.984 | 37.983 | 1.00 | 16.26 | C |
| ATOM | 30953 | O | LYS | D | 50 | 18.431 | 102.084 | 38.369 | 1.00 | 15.47 | O |
| ATOM | 30955 | N | MSE | D | 51 | 18.698 | 100.367 | 36.985 | 1.00 | 17.61 | N |
| ATOM | 30956 | CA | MSE | D | 51 | 19.785 | 101.066 | 36.235 | 1.00 | 18.99 | C |
| ATOM | 30958 | CB | MSE | D | 51 | 20.393 | 100.163 | 35.132 | 1.00 | 19.55 | C |
| ATOM | 30961 | CG | MSE | D | 51 | 21.208 | 99.076 | 35.651 | 1.00 | 21.16 | C |
| ATOM | 30964 | SE | MSE | D | 51 | 22.367 | 98.444 | 34.191 | 1.00 | 31.45 | SE |
| ATOM | 30965 | CE | MSE | D | 51 | 24.005 | 99.551 | 34.581 | 1.00 | 33.72 | C |
| ATOM | 30969 | C | MSE | D | 51 | 19.336 | 102.366 | 35.605 | 1.00 | 18.83 | C |
| ATOM | 30970 | O | MSE | D | 51 | 20.009 | 103.387 | 35.710 | 1.00 | 18.25 | O |
| ATOM | 30972 | N | LEU | D | 52 | 18.200 | 102.325 | 34.916 | 1.00 | 17.69 | N |
| ATOM | 30973 | CA | LEU | D | 52 | 17.702 | 103.503 | 34.227 | 1.00 | 18.38 | C |
| ATOM | 30975 | CB | LEU | D | 52 | 16.578 | 103.101 | 33.253 | 1.00 | 18.76 | C |
| ATOM | 30978 | CG | LEU | D | 52 | 16.995 | 102.156 | 32.103 | 1.00 | 21.06 | C |
| ATOM | 30980 | CD1 | LEU | D | 52 | 15.846 | 101.730 | 31.233 | 1.00 | 20.93 | C |
| ATOM | 30984 | CD2 | LEU | D | 52 | 18.059 | 102.738 | 31.219 | 1.00 | 22.99 | C |
| ATOM | 30988 | C | LEU | D | 52 | 17.256 | 104.598 | 35.204 | 1.00 | 18.43 | C |
| ATOM | 30989 | O | LEU | D | 52 | 17.193 | 105.755 | 34.837 | 1.00 | 20.31 | O |
| ATOM | 30991 | N | ALA | D | 53 | 16.910 | 104.231 | 36.443 | 1.00 | 17.58 | N |
| ATOM | 30992 | CA | ALA | D | 53 | 16.555 | 105.223 | 37.441 | 1.00 | 17.07 | C |
| ATOM | 30994 | CB | ALA | D | 53 | 15.695 | 104.585 | 38.526 | 1.00 | 17.34 | C |
| ATOM | 30998 | C | ALA | D | 53 | 17.753 | 105.919 | 38.081 | 1.00 | 17.28 | C |
| ATOM | 30999 | O | ALA | D | 53 | 17.561 | 106.757 | 38.969 | 1.00 | 17.71 | O |
| ATOM | 31001 | N | ALA | D | 54 | 18.986 | 105.561 | 37.721 | 1.00 | 17.83 | N |
| ATOM | 31002 | CA | ALA | D | 54 | 20.138 | 106.246 | 38.314 | 1.00 | 18.07 | C |
| ATOM | 31004 | CB | ALA | D | 54 | 21.482 | 105.671 | 37.810 | 1.00 | 18.65 | C |
| ATOM | 31008 | C | ALA | D | 54 | 20.062 | 107.739 | 38.032 | 1.00 | 19.50 | C |
| ATOM | 31009 | O | ALA | D | 54 | 19.874 | 108.156 | 36.874 | 1.00 | 18.51 | O |
| ATOM | 31011 | N | PRO | D | 55 | 20.223 | 108.556 | 39.082 | 1.00 | 20.08 | N |
| ATOM | 31012 | CA | PRO | D | 55 | 20.218 | 110.005 | 38.831 | 1.00 | 21.14 | C |

| | | | | | | | | | | |
|---|---|---|---|---|---|---|---|---|---|---|
| ATOM | 31014 | CB | PRO | D | 55 | 20.471 | 110.614 | 40.222 | 1.00 20.84 | C |
| ATOM | 31017 | CG | PRO | D | 55 | 20.190 | 109.528 | 41.187 | 1.00 19.74 | C |
| ATOM | 31020 | CD | PRO | D | 55 | 20.345 | 108.220 | 40.512 | 1.00 20.83 | C |
| ATOM | 31023 | C | PRO | D | 55 | 21.332 | 110.379 | 37.855 | 1.00 22.04 | C |
| ATOM | 31024 | O | PRO | D | 55 | 22.351 | 109.674 | 37.783 | 1.00 21.65 | O |
| ATOM | 31025 | N | THR | D | 56 | 21.136 | 111.467 | 37.109 | 1.00 23.51 | N |
| ATOM | 31026 | CA | THR | D | 56 | 22.209 | 112.057 | 36.312 | 1.00 24.64 | C |
| ATOM | 31028 | CB | THR | D | 56 | 21.823 | 112.162 | 34.830 | 1.00 25.91 | C |
| ATOM | 31030 | OG1 | THR | D | 56 | 20.640 | 112.952 | 34.710 | 1.00 26.64 | O |
| ATOM | 31032 | CG2 | THR | D | 56 | 21.569 | 110.794 | 34.256 | 1.00 27.65 | C |
| ATOM | 31036 | C | THR | D | 56 | 22.656 | 113.443 | 36.761 | 1.00 24.87 | C |
| ATOM | 31037 | O | THR | D | 56 | 23.735 | 113.871 | 36.387 | 1.00 24.64 | O |
| ATOM | 31039 | N | ASP | D | 57 | 21.830 | 114.142 | 37.535 | 1.00 23.93 | N |
| ATOM | 31040 | CA | ASP | D | 57 | 22.115 | 115.519 | 37.920 | 1.00 25.23 | C |
| ATOM | 31042 | CB | ASP | D | 57 | 20.825 | 116.368 | 37.924 | 1.00 25.38 | C |
| ATOM | 31045 | CG | ASP | D | 57 | 19.613 | 115.662 | 38.628 | 1.00 30.16 | C |
| ATOM | 31046 | OD1 | ASP | D | 57 | 19.595 | 114.407 | 38.805 | 1.00 34.40 | O |
| ATOM | 31047 | OD2 | ASP | D | 57 | 18.661 | 116.388 | 39.016 | 1.00 35.74 | O |
| ATOM | 31048 | C | ASP | D | 57 | 22.790 | 115.587 | 39.287 | 1.00 23.33 | C |
| ATOM | 31049 | O | ASP | D | 57 | 23.791 | 116.310 | 39.473 | 1.00 24.53 | O |
| ATOM | 31051 | N | SER | D | 58 | 22.247 | 114.831 | 40.243 | 1.00 21.04 | N |
| ATOM | 31052 | CA | SER | D | 58 | 22.727 | 114.887 | 41.610 | 1.00 19.56 | C |
| ATOM | 31054 | CB | SER | D | 58 | 21.702 | 114.296 | 42.561 | 1.00 19.72 | C |
| ATOM | 31057 | OG | SER | D | 58 | 21.303 | 113.033 | 42.092 | 1.00 21.92 | O |
| ATOM | 31059 | C | SER | D | 58 | 24.064 | 114.158 | 41.751 | 1.00 17.52 | C |
| ATOM | 31060 | O | SER | D | 58 | 24.366 | 113.203 | 41.033 | 1.00 16.47 | O |
| ATOM | 31062 | N | THR | D | 59 | 24.876 | 114.675 | 42.654 | 1.00 15.86 | N |
| ATOM | 31063 | CA | THR | D | 59 | 26.209 | 114.130 | 42.855 | 1.00 15.34 | C |
| ATOM | 31065 | CB | THR | D | 59 | 26.993 | 115.005 | 43.820 | 1.00 15.87 | C |
| ATOM | 31067 | OG1 | THR | D | 59 | 26.974 | 116.345 | 43.313 | 1.00 18.93 | O |
| ATOM | 31069 | CG2 | THR | D | 59 | 28.415 | 114.541 | 43.956 | 1.00 16.35 | C |
| ATOM | 31073 | C | THR | D | 59 | 26.167 | 112.657 | 43.298 | 1.00 15.54 | C |
| ATOM | 31074 | O | THR | D | 59 | 25.444 | 112.295 | 44.240 | 1.00 15.16 | O |
| ATOM | 31076 | N | LEU | D | 60 | 26.951 | 111.850 | 42.601 | 1.00 15.07 | N |
| ATOM | 31077 | CA | LEU | D | 60 | 27.248 | 110.489 | 43.009 | 1.00 14.97 | C |
| ATOM | 31079 | CB | LEU | D | 60 | 27.741 | 109.683 | 41.807 | 1.00 15.46 | C |
| ATOM | 31082 | CG | LEU | D | 60 | 28.206 | 108.265 | 42.104 | 1.00 13.51 | C |
| ATOM | 31084 | CD1 | LEU | D | 60 | 27.077 | 107.474 | 42.765 | 1.00 14.89 | C |
| ATOM | 31088 | CD2 | LEU | D | 60 | 28.685 | 107.587 | 40.835 | 1.00 15.75 | C |
| ATOM | 31092 | C | LEU | D | 60 | 28.320 | 110.564 | 44.117 | 1.00 15.39 | C |
| ATOM | 31093 | O | LEU | D | 60 | 29.462 | 110.997 | 43.878 | 1.00 14.34 | O |
| ATOM | 31095 | N | GLU | D | 61 | 27.944 | 110.144 | 45.323 | 1.00 14.98 | N |
| ATOM | 31096 | CA | GLU | D | 61 | 28.863 | 110.166 | 46.439 | 1.00 16.12 | C |
| ATOM | 31098 | CB | GLU | D | 61 | 28.176 | 110.611 | 47.732 | 1.00 15.81 | C |
| ATOM | 31101 | CG | GLU | D | 61 | 27.927 | 112.115 | 47.874 | 1.00 19.72 | C |
| ATOM | 31104 | CD | GLU | D | 61 | 27.669 | 112.512 | 49.356 | 1.00 21.52 | C |
| ATOM | 31105 | OE1 | GLU | D | 61 | 26.643 | 112.005 | 49.875 | 1.00 26.40 | O |
| ATOM | 31106 | OE2 | GLU | D | 61 | 28.457 | 113.295 | 49.996 | 1.00 28.35 | O |
| ATOM | 31107 | C | GLU | D | 61 | 29.433 | 108.753 | 46.600 | 1.00 15.48 | C |
| ATOM | 31108 | O | GLU | D | 61 | 28.686 | 107.792 | 46.834 | 1.00 15.81 | O |
| ATOM | 31110 | N | LEU | D | 62 | 30.755 | 108.653 | 46.482 | 1.00 14.29 | N |
| ATOM | 31111 | CA | LEU | D | 62 | 31.453 | 107.373 | 46.566 | 1.00 13.43 | C |
| ATOM | 31113 | CB | LEU | D | 62 | 32.675 | 107.418 | 45.679 | 1.00 13.95 | C |
| ATOM | 31116 | CG | LEU | D | 62 | 32.358 | 107.695 | 44.194 | 1.00 14.11 | C |
| ATOM | 31118 | CD1 | LEU | D | 62 | 33.639 | 107.824 | 43.362 | 1.00 14.86 | C |
| ATOM | 31122 | CD2 | LEU | D | 62 | 31.431 | 106.665 | 43.589 | 1.00 14.71 | C |
| ATOM | 31126 | C | LEU | D | 62 | 31.894 | 107.066 | 47.983 | 1.00 14.32 | C |

| ATOM | 31127 | O   | LEU | D | 62 | 32.573 | 107.879 | 48.610 | 1.00 | 13.22 | O |
|------|-------|-----|-----|---|----|--------|---------|--------|------|-------|---|
| ATOM | 31129 | N   | ASP | D | 63 | 31.466 | 105.917 | 48.493 | 1.00 | 13.40 | N |
| ATOM | 31130 | CA  | ASP | D | 63 | 31.751 | 105.523 | 49.880 | 1.00 | 14.01 | C |
| ATOM | 31132 | CB  | ASP | D | 63 | 30.468 | 105.529 | 50.727 | 1.00 | 14.13 | C |
| ATOM | 31135 | CG  | ASP | D | 63 | 29.435 | 104.514 | 50.268 | 1.00 | 15.28 | C |
| ATOM | 31136 | OD1 | ASP | D | 63 | 29.779 | 103.430 | 49.741 | 1.00 | 14.40 | O |
| ATOM | 31137 | OD2 | ASP | D | 63 | 28.235 | 104.827 | 50.467 | 1.00 | 15.87 | O |
| ATOM | 31138 | C   | ASP | D | 63 | 32.472 | 104.170 | 49.978 | 1.00 | 13.88 | C |
| ATOM | 31139 | O   | ASP | D | 63 | 32.728 | 103.682 | 51.102 | 1.00 | 15.33 | O |
| ATOM | 31141 | N   | GLY | D | 64 | 32.781 | 103.546 | 48.825 | 1.00 | 13.95 | N |
| ATOM | 31142 | CA  | GLY | D | 64 | 33.494 | 102.254 | 48.754 | 1.00 | 13.03 | C |
| ATOM | 31145 | C   | GLY | D | 64 | 32.618 | 100.990 | 48.797 | 1.00 | 13.14 | C |
| ATOM | 31146 | O   | GLY | D | 64 | 33.129 |  99.874 | 48.610 | 1.00 | 12.82 | O |
| ATOM | 31148 | N   | TYR | D | 65 | 31.299 | 101.162 | 48.956 | 1.00 | 11.84 | N |
| ATOM | 31149 | CA  | TYR | D | 65 | 30.374 | 100.046 | 49.119 | 1.00 | 12.66 | C |
| ATOM | 31151 | CB  | TYR | D | 65 | 30.055 |  99.872 | 50.604 | 1.00 | 13.25 | C |
| ATOM | 31154 | CG  | TYR | D | 65 | 31.251 |  99.464 | 51.389 | 1.00 | 14.04 | C |
| ATOM | 31155 | CD1 | TYR | D | 65 | 31.509 |  98.114 | 51.637 | 1.00 | 16.23 | C |
| ATOM | 31157 | CE1 | TYR | D | 65 | 32.632 |  97.720 | 52.312 | 1.00 | 16.33 | C |
| ATOM | 31159 | CZ  | TYR | D | 65 | 33.533 |  98.665 | 52.736 | 1.00 | 15.58 | C |
| ATOM | 31160 | OH  | TYR | D | 65 | 34.672 |  98.255 | 53.394 | 1.00 | 18.10 | O |
| ATOM | 31162 | CE2 | TYR | D | 65 | 33.326 |  99.996 | 52.487 | 1.00 | 15.69 | C |
| ATOM | 31164 | CD2 | TYR | D | 65 | 32.185 | 100.398 | 51.835 | 1.00 | 14.86 | C |
| ATOM | 31166 | C   | TYR | D | 65 | 29.065 | 100.167 | 48.315 | 1.00 | 13.85 | C |
| ATOM | 31167 | O   | TYR | D | 65 | 28.496 |  99.157 | 47.924 | 1.00 | 13.88 | O |
| ATOM | 31169 | N   | SER | D | 66 | 28.558 | 101.403 | 48.180 | 1.00 | 13.05 | N |
| ATOM | 31170 | CA  | SER | D | 66 | 27.217 | 101.672 | 47.680 | 1.00 | 14.34 | C |
| ATOM | 31172 | CB  | SER | D | 66 | 26.701 | 103.023 | 48.264 | 1.00 | 14.43 | C |
| ATOM | 31175 | OG  | SER | D | 66 | 26.640 | 102.942 | 49.659 | 1.00 | 19.31 | O |
| ATOM | 31177 | C   | SER | D | 66 | 27.107 | 101.734 | 46.155 | 1.00 | 13.69 | C |
| ATOM | 31178 | O   | SER | D | 66 | 26.008 | 101.671 | 45.605 | 1.00 | 14.30 | O |
| ATOM | 31180 | N   | LEU | D | 67 | 28.242 | 101.905 | 45.481 | 1.00 | 13.64 | N |
| ATOM | 31181 | CA  | LEU | D | 67 | 28.295 | 102.173 | 44.059 | 1.00 | 13.41 | C |
| ATOM | 31183 | CB  | LEU | D | 67 | 29.737 | 102.343 | 43.616 | 1.00 | 13.16 | C |
| ATOM | 31186 | CG  | LEU | D | 67 | 29.974 | 102.578 | 42.142 | 1.00 | 12.61 | C |
| ATOM | 31188 | CD1 | LEU | D | 67 | 29.337 | 103.879 | 41.704 | 1.00 | 11.96 | C |
| ATOM | 31192 | CD2 | LEU | D | 67 | 31.412 | 102.636 | 41.821 | 1.00 | 13.98 | C |
| ATOM | 31196 | C   | LEU | D | 67 | 27.664 | 101.025 | 43.297 | 1.00 | 14.15 | C |
| ATOM | 31197 | O   | LEU | D | 67 | 28.005 |  99.882 | 43.524 | 1.00 | 14.63 | O |
| ATOM | 31199 | N   | ASN | D | 68 | 26.709 | 101.337 | 42.420 | 1.00 | 13.32 | N |
| ATOM | 31200 | CA  | ASN | D | 68 | 26.085 | 100.308 | 41.624 | 1.00 | 12.83 | C |
| ATOM | 31202 | CB  | ASN | D | 68 | 24.598 | 100.129 | 41.979 | 1.00 | 13.05 | C |
| ATOM | 31205 | CG  | ASN | D | 68 | 23.761 | 101.368 | 41.665 | 1.00 | 14.06 | C |
| ATOM | 31206 | OD1 | ASN | D | 68 | 23.955 | 101.957 | 40.616 | 1.00 | 15.24 | O |
| ATOM | 31207 | ND2 | ASN | D | 68 | 22.852 | 101.766 | 42.565 | 1.00 | 18.31 | N |
| ATOM | 31210 | C   | ASN | D | 68 | 26.319 | 100.533 | 40.132 | 1.00 | 12.50 | C |
| ATOM | 31211 | O   | ASN | D | 68 | 26.946 | 101.525 | 39.710 | 1.00 | 12.91 | O |
| ATOM | 31213 | N   | LEU | D | 69 | 25.948 |  99.543 | 39.321 | 1.00 | 13.11 | N |
| ATOM | 31214 | CA  | LEU | D | 69 | 26.244 |  99.652 | 37.880 | 1.00 | 12.18 | C |
| ATOM | 31216 | CB  | LEU | D | 69 | 26.026 |  98.317 | 37.149 | 1.00 | 12.17 | C |
| ATOM | 31219 | CG  | LEU | D | 69 | 26.758 |  97.124 | 37.807 | 1.00 | 13.66 | C |
| ATOM | 31221 | CD1 | LEU | D | 69 | 26.642 |  95.972 | 36.882 | 1.00 | 16.43 | C |
| ATOM | 31225 | CD2 | LEU | D | 69 | 28.273 |  97.462 | 38.061 | 1.00 | 16.10 | C |
| ATOM | 31229 | C   | LEU | D | 69 | 25.547 | 100.841 | 37.177 | 1.00 | 11.62 | C |
| ATOM | 31230 | O   | LEU | D | 69 | 26.136 | 101.493 | 36.309 | 1.00 | 12.14 | O |
| ATOM | 31232 | N   | GLY | D | 70 | 24.285 | 101.079 | 37.513 | 1.00 | 12.42 | N |
| ATOM | 31233 | CA  | GLY | D | 70 | 23.586 | 102.215 | 36.950 | 1.00 | 13.02 | C |

| | | | | | | | | | |
|---|---|---|---|---|---|---|---|---|---|
| ATOM | 31236 | C | GLY | D | 70 | 24.335 | 103.515 | 37.247 | 1.00 13.46 | C |
| ATOM | 31237 | O | GLY | D | 70 | 24.471 | 104.370 | 36.387 | 1.00 12.19 | O |
| ATOM | 31239 | N | ASP | D | 71 | 24.833 | 103.625 | 38.469 | 1.00 13.74 | N |
| ATOM | 31240 | CA | ASP | D | 71 | 25.653 | 104.759 | 38.900 | 1.00 13.19 | C |
| ATOM | 31242 | CB | ASP | D | 71 | 26.148 | 104.548 | 40.326 | 1.00 14.75 | C |
| ATOM | 31245 | CG | ASP | D | 71 | 25.077 | 104.749 | 41.405 | 1.00 16.71 | C |
| ATOM | 31246 | OD1 | ASP | D | 71 | 24.061 | 105.484 | 41.190 | 1.00 15.92 | O |
| ATOM | 31247 | OD2 | ASP | D | 71 | 25.294 | 104.140 | 42.505 | 1.00 18.76 | O |
| ATOM | 31248 | C | ASP | D | 71 | 26.883 | 104.899 | 38.030 | 1.00 12.36 | C |
| ATOM | 31249 | O | ASP | D | 71 | 27.191 | 105.963 | 37.511 | 1.00 12.26 | O |
| ATOM | 31251 | N | VAL | D | 72 | 27.594 | 103.796 | 37.864 | 1.00 11.38 | N |
| ATOM | 31252 | CA | VAL | D | 72 | 28.772 | 103.818 | 36.981 | 1.00 12.21 | C |
| ATOM | 31254 | CB | VAL | D | 72 | 29.422 | 102.421 | 36.887 | 1.00 13.20 | C |
| ATOM | 31256 | CG1 | VAL | D | 72 | 30.533 | 102.425 | 35.835 | 1.00 14.18 | C |
| ATOM | 31260 | CG2 | VAL | D | 72 | 29.911 | 101.955 | 38.251 | 1.00 14.21 | C |
| ATOM | 31264 | C | VAL | D | 72 | 28.427 | 104.328 | 35.596 | 1.00 12.73 | C |
| ATOM | 31265 | O | VAL | D | 72 | 29.119 | 105.175 | 35.046 | 1.00 12.92 | O |
| ATOM | 31267 | N | VAL | D | 73 | 27.366 | 103.795 | 34.997 | 1.00 11.42 | N |
| ATOM | 31268 | CA | VAL | D | 73 | 26.984 | 104.277 | 33.668 | 1.00 13.23 | C |
| ATOM | 31270 | CB | VAL | D | 73 | 25.829 | 103.427 | 33.126 | 1.00 12.84 | C |
| ATOM | 31272 | CG1 | VAL | D | 73 | 25.329 | 103.970 | 31.794 | 1.00 15.21 | C |
| ATOM | 31276 | CG2 | VAL | D | 73 | 26.297 | 101.972 | 33.008 | 1.00 13.40 | C |
| ATOM | 31280 | C | VAL | D | 73 | 26.619 | 105.791 | 33.651 | 1.00 13.11 | C |
| ATOM | 31281 | O | VAL | D | 73 | 26.924 | 106.556 | 32.700 | 1.00 13.82 | O |
| ATOM | 31283 | N | SER | D | 74 | 25.924 | 106.246 | 34.694 | 1.00 12.38 | N |
| ATOM | 31284 | CA | SER | D | 74 | 25.517 | 107.674 | 34.786 | 1.00 13.60 | C |
| ATOM | 31286 | CB | SER | D | 74 | 24.614 | 107.876 | 35.978 | 1.00 13.85 | C |
| ATOM | 31289 | OG | SER | D | 74 | 25.335 | 107.725 | 37.195 | 1.00 14.93 | O |
| ATOM | 31291 | C | SER | D | 74 | 26.758 | 108.606 | 34.814 | 1.00 13.54 | C |
| ATOM | 31292 | O | SER | D | 74 | 26.755 | 109.697 | 34.219 | 1.00 15.97 | O |
| ATOM | 31294 | N | ALA | D | 75 | 27.792 | 108.181 | 35.537 | 1.00 12.95 | N |
| ATOM | 31295 | CA | ALA | D | 75 | 29.027 | 108.930 | 35.616 | 1.00 13.22 | C |
| ATOM | 31297 | CB | ALA | D | 75 | 29.917 | 108.377 | 36.780 | 1.00 13.28 | C |
| ATOM | 31301 | C | ALA | D | 75 | 29.800 | 108.820 | 34.298 | 1.00 13.73 | C |
| ATOM | 31302 | O | ALA | D | 75 | 30.363 | 109.814 | 33.828 | 1.00 14.88 | O |
| ATOM | 31304 | N | ALA | D | 76 | 29.856 | 107.632 | 33.710 | 1.00 13.06 | N |
| ATOM | 31305 | CA | ALA | D | 76 | 30.671 | 107.410 | 32.537 | 1.00 14.04 | C |
| ATOM | 31307 | CB | ALA | D | 76 | 30.834 | 105.889 | 32.245 | 1.00 14.76 | C |
| ATOM | 31311 | C | ALA | D | 76 | 30.104 | 108.133 | 31.319 | 1.00 15.64 | C |
| ATOM | 31312 | O | ALA | D | 76 | 30.850 | 108.802 | 30.598 | 1.00 16.08 | O |
| ATOM | 31314 | N | ARG | D | 77 | 28.777 | 108.045 | 31.147 | 1.00 15.58 | N |
| ATOM | 31315 | CA | ARG | D | 77 | 28.079 | 108.478 | 29.922 | 1.00 16.52 | C |
| ATOM | 31317 | CB | ARG | D | 77 | 27.110 | 107.396 | 29.410 | 1.00 17.35 | C |
| ATOM | 31320 | CG | ARG | D | 77 | 27.751 | 106.208 | 28.877 | 1.00 19.26 | C |
| ATOM | 31323 | CD | ARG | D | 77 | 26.739 | 105.383 | 28.106 | 1.00 18.52 | C |
| ATOM | 31326 | NE | ARG | D | 77 | 27.441 | 104.326 | 27.427 | 1.00 18.48 | N |
| ATOM | 31328 | CZ | ARG | D | 77 | 26.932 | 103.130 | 27.125 | 1.00 18.04 | C |
| ATOM | 31329 | NH1 | ARG | D | 77 | 25.681 | 102.772 | 27.470 | 1.00 18.63 | N |
| ATOM | 31332 | NH2 | ARG | D | 77 | 27.705 | 102.273 | 26.514 | 1.00 19.30 | N |
| ATOM | 31335 | C | ARG | D | 77 | 27.240 | 109.692 | 30.025 | 1.00 18.14 | C |
| ATOM | 31336 | O | ARG | D | 77 | 26.978 | 110.307 | 28.985 | 1.00 18.59 | O |
| ATOM | 31338 | N | LYS | D | 78 | 26.733 | 110.013 | 31.217 | 1.00 17.56 | N |
| ATOM | 31339 | CA | LYS | D | 78 | 25.739 | 111.079 | 31.348 | 1.00 18.74 | C |
| ATOM | 31341 | CB | LYS | D | 78 | 24.467 | 110.553 | 32.017 | 1.00 19.38 | C |
| ATOM | 31344 | CG | LYS | D | 78 | 23.959 | 109.225 | 31.436 | 1.00 23.96 | C |
| ATOM | 31347 | CD | LYS | D | 78 | 23.536 | 109.383 | 30.002 | 1.00 29.86 | C |
| ATOM | 31350 | CE | LYS | D | 78 | 22.311 | 108.512 | 29.686 | 1.00 32.64 | C |

| ATOM | 31353 | NZ | LYS | D | 78 | 21.786 | 108.841 | 28.338 | 1.00 | 34.45 | N |
|------|-------|-----|-----|---|----|--------|---------|--------|------|-------|---|
| ATOM | 31357 | C | LYS | D | 78 | 26.272 | 112.277 | 32.087 | 1.00 | 17.79 | C |
| ATOM | 31358 | O | LYS | D | 78 | 25.512 | 113.188 | 32.403 | 1.00 | 17.68 | O |
| ATOM | 31360 | N | GLY | D | 79 | 27.577 | 112.283 | 32.368 | 1.00 | 16.48 | N |
| ATOM | 31361 | CA | GLY | D | 79 | 28.213 | 113.472 | 32.928 | 1.00 | 15.34 | C |
| ATOM | 31364 | C | GLY | D | 79 | 27.868 | 113.755 | 34.384 | 1.00 | 14.36 | C |
| ATOM | 31365 | O | GLY | D | 79 | 28.060 | 114.871 | 34.888 | 1.00 | 15.10 | O |
| ATOM | 31367 | N | ARG | D | 80 | 27.398 | 112.741 | 35.103 | 1.00 | 14.70 | N |
| ATOM | 31368 | CA | ARG | D | 80 | 27.002 | 112.934 | 36.495 | 1.00 | 14.33 | C |
| ATOM | 31370 | CB | ARG | D | 80 | 26.414 | 111.659 | 37.056 | 1.00 | 15.09 | C |
| ATOM | 31373 | CG | ARG | D | 80 | 25.811 | 111.819 | 38.415 | 1.00 | 15.64 | C |
| ATOM | 31376 | CD | ARG | D | 80 | 25.272 | 110.495 | 38.838 | 1.00 | 16.40 | C |
| ATOM | 31379 | NE | ARG | D | 80 | 24.672 | 110.498 | 40.170 | 1.00 | 16.96 | N |
| ATOM | 31381 | CZ | ARG | D | 80 | 24.213 | 109.379 | 40.725 | 1.00 | 16.09 | C |
| ATOM | 31382 | NH1 | ARG | D | 80 | 24.300 | 108.245 | 40.073 | 1.00 | 14.84 | N |
| ATOM | 31385 | NH2 | ARG | D | 80 | 23.706 | 109.401 | 41.944 | 1.00 | 16.79 | N |
| ATOM | 31388 | C | ARG | D | 80 | 28.187 | 113.383 | 37.353 | 1.00 | 13.78 | C |
| ATOM | 31389 | O | ARG | D | 80 | 29.256 | 112.785 | 37.234 | 1.00 | 13.89 | O |
| ATOM | 31391 | N | PRO | D | 81 | 28.014 | 114.408 | 38.209 | 1.00 | 13.87 | N |
| ATOM | 31392 | CA | PRO | D | 81 | 29.077 | 114.807 | 39.152 | 1.00 | 14.29 | C |
| ATOM | 31394 | CB | PRO | D | 81 | 28.462 | 115.970 | 39.936 | 1.00 | 14.89 | C |
| ATOM | 31397 | CG | PRO | D | 81 | 27.415 | 116.477 | 39.059 | 1.00 | 14.97 | C |
| ATOM | 31400 | CD | PRO | D | 81 | 26.852 | 115.308 | 38.319 | 1.00 | 14.68 | C |
| ATOM | 31403 | C | PRO | D | 81 | 29.409 | 113.667 | 40.098 | 1.00 | 14.18 | C |
| ATOM | 31404 | O | PRO | D | 81 | 28.501 | 112.938 | 40.479 | 1.00 | 15.08 | O |
| ATOM | 31405 | N | VAL | D | 82 | 30.678 | 113.564 | 40.490 | 1.00 | 13.68 | N |
| ATOM | 31406 | CA | VAL | D | 82 | 31.162 | 112.475 | 41.327 | 1.00 | 13.58 | C |
| ATOM | 31408 | CB | VAL | D | 82 | 32.013 | 111.454 | 40.494 | 1.00 | 14.93 | C |
| ATOM | 31410 | CG1 | VAL | D | 82 | 32.582 | 110.361 | 41.399 | 1.00 | 14.34 | C |
| ATOM | 31414 | CG2 | VAL | D | 82 | 31.185 | 110.908 | 39.389 | 1.00 | 14.12 | C |
| ATOM | 31418 | C | VAL | D | 82 | 32.032 | 113.043 | 42.426 | 1.00 | 14.84 | C |
| ATOM | 31419 | O | VAL | D | 82 | 32.879 | 113.892 | 42.157 | 1.00 | 13.87 | O |
| ATOM | 31421 | N | ARG | D | 83 | 31.881 | 112.552 | 43.645 | 1.00 | 15.51 | N |
| ATOM | 31422 | CA | ARG | D | 83 | 32.758 | 113.002 | 44.751 | 1.00 | 17.28 | C |
| ATOM | 31424 | CB | ARG | D | 83 | 32.123 | 114.181 | 45.508 | 1.00 | 18.28 | C |
| ATOM | 31427 | CG | ARG | D | 83 | 32.260 | 115.499 | 44.777 | 1.00 | 22.87 | C |
| ATOM | 31430 | CD | ARG | D | 83 | 31.554 | 116.674 | 45.481 | 1.00 | 26.51 | C |
| ATOM | 31433 | NE | ARG | D | 83 | 31.820 | 117.953 | 44.772 | 1.00 | 31.35 | N |
| ATOM | 31435 | CZ | ARG | D | 83 | 31.432 | 118.230 | 43.521 | 1.00 | 35.35 | C |
| ATOM | 31436 | NH1 | ARG | D | 83 | 30.727 | 117.355 | 42.795 | 1.00 | 37.62 | N |
| ATOM | 31439 | NH2 | ARG | D | 83 | 31.751 | 119.403 | 42.976 | 1.00 | 37.74 | N |
| ATOM | 31442 | C | ARG | D | 83 | 32.950 | 111.856 | 45.716 | 1.00 | 14.37 | C |
| ATOM | 31443 | O | ARG | D | 83 | 32.080 | 111.023 | 45.850 | 1.00 | 14.63 | O |
| ATOM | 31445 | N | VAL | D | 84 | 34.062 | 111.865 | 46.436 | 1.00 | 13.40 | N |
| ATOM | 31446 | CA | VAL | D | 84 | 34.186 | 111.027 | 47.623 | 1.00 | 13.72 | C |
| ATOM | 31448 | CB | VAL | D | 84 | 35.601 | 111.126 | 48.213 | 1.00 | 13.70 | C |
| ATOM | 31450 | CG1 | VAL | D | 84 | 35.686 | 110.422 | 49.535 | 1.00 | 14.32 | C |
| ATOM | 31454 | CG2 | VAL | D | 84 | 36.619 | 110.606 | 47.248 | 1.00 | 14.31 | C |
| ATOM | 31458 | C | VAL | D | 84 | 33.128 | 111.538 | 48.627 | 1.00 | 14.50 | C |
| ATOM | 31459 | O | VAL | D | 84 | 33.003 | 112.743 | 48.859 | 1.00 | 16.48 | O |
| ATOM | 31461 | N | LYS | D | 85 | 32.401 | 110.613 | 49.237 | 1.00 | 15.10 | N |
| ATOM | 31462 | CA | LYS | D | 85 | 31.364 | 110.972 | 50.171 | 1.00 | 16.29 | C |
| ATOM | 31464 | CB | LYS | D | 85 | 30.792 | 109.715 | 50.813 | 1.00 | 15.85 | C |
| ATOM | 31467 | CG | LYS | D | 85 | 29.699 | 110.056 | 51.820 | 1.00 | 18.01 | C |
| ATOM | 31470 | CD | LYS | D | 85 | 28.976 | 108.841 | 52.259 | 1.00 | 21.20 | C |
| ATOM | 31473 | CE | LYS | D | 85 | 28.002 | 109.163 | 53.352 | 1.00 | 23.02 | C |
| ATOM | 31476 | NZ | LYS | D | 85 | 27.002 | 110.150 | 52.862 | 1.00 | 29.12 | N |

| ATOM | 31480 | C | LYS | D | 85 | 31.907 | 111.896 | 51.244 | 1.00 | 16.62 | C |
|------|-------|-----|-----|---|----|--------|---------|--------|------|-------|---|
| ATOM | 31481 | O | LYS | D | 85 | 32.972 | 111.655 | 51.756 | 1.00 | 15.54 | O |
| ATOM | 31483 | N | ASP | D | 86 | 31.152 | 112.946 | 51.573 | 1.00 | 18.94 | N |
| ATOM | 31484 | CA | ASP | D | 86 | 31.553 | 113.960 | 52.526 | 1.00 | 21.92 | C |
| ATOM | 31486 | CB | ASP | D | 86 | 30.698 | 115.214 | 52.268 | 1.00 | 22.51 | C |
| ATOM | 31489 | CG | ASP | D | 86 | 31.077 | 116.394 | 53.130 | 1.00 | 26.13 | C |
| ATOM | 31490 | OD1 | ASP | D | 86 | 32.008 | 116.288 | 53.952 | 1.00 | 27.42 | O |
| ATOM | 31491 | OD2 | ASP | D | 86 | 30.409 | 117.438 | 52.961 | 1.00 | 31.64 | O |
| ATOM | 31492 | C | ASP | D | 86 | 31.256 | 113.354 | 53.895 | 1.00 | 22.50 | C |
| ATOM | 31493 | O | ASP | D | 86 | 30.116 | 113.396 | 54.348 | 1.00 | 24.25 | O |
| ATOM | 31495 | N | SER | D | 87 | 32.243 | 112.720 | 54.497 | 1.00 | 23.15 | N |
| ATOM | 31496 | CA | SER | D | 87 | 32.074 | 112.171 | 55.830 | 1.00 | 24.30 | C |
| ATOM | 31498 | CB | SER | D | 87 | 31.261 | 110.858 | 55.775 | 1.00 | 24.73 | C |
| ATOM | 31501 | OG | SER | D | 87 | 32.051 | 109.705 | 55.957 | 1.00 | 25.72 | O |
| ATOM | 31503 | C | SER | D | 87 | 33.404 | 111.996 | 56.549 | 1.00 | 24.64 | C |
| ATOM | 31504 | O | SER | D | 87 | 34.403 | 111.565 | 55.978 | 1.00 | 24.28 | O |
| ATOM | 31506 | N | ASP | D | 88 | 33.418 | 112.344 | 57.825 | 1.00 | 24.40 | N |
| ATOM | 31507 | CA | ASP | D | 88 | 34.599 | 112.169 | 58.642 | 1.00 | 25.14 | C |
| ATOM | 31509 | CB | ASP | D | 88 | 34.371 | 112.721 | 60.056 | 1.00 | 26.01 | C |
| ATOM | 31512 | CG | ASP | D | 88 | 34.170 | 114.249 | 60.077 | 1.00 | 29.87 | C |
| ATOM | 31513 | OD1 | ASP | D | 88 | 34.474 | 114.946 | 59.073 | 1.00 | 32.23 | O |
| ATOM | 31514 | OD2 | ASP | D | 88 | 33.715 | 114.768 | 61.126 | 1.00 | 34.66 | O |
| ATOM | 31515 | C | ASP | D | 88 | 35.030 | 110.705 | 58.717 | 1.00 | 24.66 | C |
| ATOM | 31516 | O | ASP | D | 88 | 36.235 | 110.410 | 58.729 | 1.00 | 23.37 | O |
| ATOM | 31518 | N | GLU | D | 89 | 34.059 | 109.798 | 58.765 | 1.00 | 24.86 | N |
| ATOM | 31519 | CA | GLU | D | 89 | 34.338 | 108.361 | 58.834 | 1.00 | 25.93 | C |
| ATOM | 31521 | CB | GLU | D | 89 | 33.033 | 107.557 | 58.975 | 1.00 | 26.71 | C |
| ATOM | 31524 | CG | GLU | D | 89 | 32.519 | 107.515 | 60.440 | 1.00 | 30.77 | C |
| ATOM | 31527 | CD | GLU | D | 89 | 31.003 | 107.204 | 60.590 | 1.00 | 31.96 | C |
| ATOM | 31528 | OE1 | GLU | D | 89 | 30.378 | 106.725 | 59.595 | 1.00 | 40.21 | O |
| ATOM | 31529 | OE2 | GLU | D | 89 | 30.451 | 107.449 | 61.710 | 1.00 | 38.38 | O |
| ATOM | 31530 | C | GLU | D | 89 | 35.140 | 107.908 | 57.611 | 1.00 | 23.75 | C |
| ATOM | 31531 | O | GLU | D | 89 | 36.175 | 107.272 | 57.744 | 1.00 | 22.08 | O |
| ATOM | 31533 | N | ILE | D | 90 | 34.689 | 108.288 | 56.424 | 1.00 | 23.50 | N |
| ATOM | 31534 | CA | ILE | D | 90 | 35.468 | 107.989 | 55.183 | 1.00 | 23.88 | C |
| ATOM | 31536 | CB | ILE | D | 90 | 34.729 | 108.423 | 53.892 | 1.00 | 24.53 | C |
| ATOM | 31538 | CG1 | ILE | D | 90 | 33.350 | 107.753 | 53.759 | 1.00 | 27.31 | C |
| ATOM | 31541 | CD1 | ILE | D | 90 | 33.369 | 106.317 | 54.010 | 1.00 | 30.43 | C |
| ATOM | 31545 | CG2 | ILE | D | 90 | 35.590 | 108.133 | 52.647 | 1.00 | 24.61 | C |
| ATOM | 31549 | C | ILE | D | 90 | 36.838 | 108.662 | 55.191 | 1.00 | 23.09 | C |
| ATOM | 31550 | O | ILE | D | 90 | 37.841 | 108.026 | 54.935 | 1.00 | 21.60 | O |
| ATOM | 31552 | N | ARG | D | 91 | 36.901 | 109.965 | 55.445 | 1.00 | 23.59 | N |
| ATOM | 31553 | CA | ARG | D | 91 | 38.225 | 110.624 | 55.500 | 1.00 | 24.62 | C |
| ATOM | 31555 | CB | ARG | D | 91 | 38.095 | 112.086 | 55.852 | 1.00 | 25.07 | C |
| ATOM | 31558 | CG | ARG | D | 91 | 37.449 | 112.909 | 54.823 | 1.00 | 27.14 | C |
| ATOM | 31561 | CD | ARG | D | 91 | 37.303 | 114.363 | 55.323 | 1.00 | 29.39 | C |
| ATOM | 31564 | NE | ARG | D | 91 | 36.248 | 114.915 | 54.521 | 1.00 | 32.95 | N |
| ATOM | 31566 | CZ | ARG | D | 91 | 35.037 | 115.237 | 54.934 | 1.00 | 31.87 | C |
| ATOM | 31567 | NH1 | ARG | D | 91 | 34.696 | 115.209 | 56.219 | 1.00 | 34.70 | N |
| ATOM | 31570 | NH2 | ARG | D | 91 | 34.171 | 115.646 | 54.027 | 1.00 | 33.68 | N |
| ATOM | 31573 | C | ARG | D | 91 | 39.187 | 110.003 | 56.489 | 1.00 | 23.87 | C |
| ATOM | 31574 | O | ARG | D | 91 | 40.397 | 109.905 | 56.231 | 1.00 | 22.98 | O |
| ATOM | 31576 | N | SER | D | 92 | 38.679 | 109.649 | 57.671 | 1.00 | 23.89 | N |
| ATOM | 31577 | CA | SER | D | 92 | 39.537 | 109.067 | 58.694 | 1.00 | 24.07 | C |
| ATOM | 31579 | CB | SER | D | 92 | 38.798 | 108.898 | 60.035 | 1.00 | 24.89 | C |
| ATOM | 31582 | OG | SER | D | 92 | 39.630 | 108.221 | 60.971 | 1.00 | 27.30 | O |
| ATOM | 31584 | C | SER | D | 92 | 40.097 | 107.731 | 58.233 | 1.00 | 23.70 | C |

| ATOM | 31585 | O   | SER | D | 92 | 41.263 | 107.449 | 58.438 | 1.00 | 23.23 | O |
|------|-------|-----|-----|---|----|--------|---------|--------|------|-------|---|
| ATOM | 31587 | N   | LYS | D | 93 | 39.246 | 106.922 | 57.619 | 1.00 | 23.97 | N |
| ATOM | 31588 | CA  | LYS | D | 93 | 39.611 | 105.621 | 57.106 | 1.00 | 24.63 | C |
| ATOM | 31590 | CB  | LYS | D | 93 | 38.368 | 105.031 | 56.450 | 1.00 | 25.77 | C |
| ATOM | 31593 | CG  | LYS | D | 93 | 38.464 | 103.631 | 56.007 | 1.00 | 29.75 | C |
| ATOM | 31596 | CD  | LYS | D | 93 | 37.113 | 102.904 | 56.206 | 1.00 | 31.75 | C |
| ATOM | 31599 | CE  | LYS | D | 93 | 36.005 | 103.520 | 55.394 | 1.00 | 30.60 | C |
| ATOM | 31602 | NZ  | LYS | D | 93 | 34.816 | 102.600 | 55.238 | 1.00 | 30.67 | N |
| ATOM | 31606 | C   | LYS | D | 93 | 40.746 | 105.791 | 56.095 | 1.00 | 23.32 | C |
| ATOM | 31607 | O   | LYS | D | 93 | 41.797 | 105.177 | 56.228 | 1.00 | 23.84 | O |
| ATOM | 31609 | N   | ILE | D | 94 | 40.554 | 106.708 | 55.158 | 1.00 | 22.05 | N |
| ATOM | 31610 | CA  | ILE | D | 94 | 41.591 | 107.006 | 54.159 | 1.00 | 21.84 | C |
| ATOM | 31612 | CB  | ILE | D | 94 | 41.068 | 108.006 | 53.098 | 1.00 | 21.46 | C |
| ATOM | 31614 | CG1 | ILE | D | 94 | 39.989 | 107.369 | 52.217 | 1.00 | 21.23 | C |
| ATOM | 31617 | CD1 | ILE | D | 94 | 39.147 | 108.383 | 51.470 | 1.00 | 21.74 | C |
| ATOM | 31621 | CG2 | ILE | D | 94 | 42.227 | 108.470 | 52.172 | 1.00 | 21.63 | C |
| ATOM | 31625 | C   | ILE | D | 94 | 42.888 | 107.524 | 54.787 | 1.00 | 21.93 | C |
| ATOM | 31626 | O   | ILE | D | 94 | 43.975 | 106.985 | 54.562 | 1.00 | 21.32 | O |
| ATOM | 31628 | N   | ASP | D | 95 | 42.770 | 108.547 | 55.632 | 1.00 | 21.82 | N |
| ATOM | 31629 | CA  | ASP | D | 95 | 43.933 | 109.159 | 56.271 | 1.00 | 23.09 | C |
| ATOM | 31631 | CB  | ASP | D | 95 | 43.547 | 110.425 | 57.092 | 1.00 | 23.63 | C |
| ATOM | 31634 | CG  | ASP | D | 95 | 42.733 | 111.509 | 56.283 | 1.00 | 27.63 | C |
| ATOM | 31635 | OD1 | ASP | D | 95 | 42.634 | 111.514 | 54.998 | 1.00 | 31.18 | O |
| ATOM | 31636 | OD2 | ASP | D | 95 | 42.153 | 112.414 | 56.970 | 1.00 | 33.39 | O |
| ATOM | 31637 | C   | ASP | D | 95 | 44.700 | 108.167 | 57.176 | 1.00 | 22.24 | C |
| ATOM | 31638 | O   | ASP | D | 95 | 45.926 | 108.170 | 57.188 | 1.00 | 22.97 | O |
| ATOM | 31640 | N   | LYS | D | 96 | 43.986 | 107.321 | 57.938 | 1.00 | 23.02 | N |
| ATOM | 31641 | CA  | LYS | D | 96 | 44.638 | 106.287 | 58.774 | 1.00 | 23.02 | C |
| ATOM | 31643 | CB  | LYS | D | 96 | 43.635 | 105.553 | 59.675 | 1.00 | 24.46 | C |
| ATOM | 31646 | CG  | LYS | D | 96 | 43.572 | 106.047 | 61.128 | 1.00 | 28.69 | C |
| ATOM | 31649 | CD  | LYS | D | 96 | 42.519 | 107.075 | 61.273 | 1.00 | 32.06 | C |
| ATOM | 31652 | CE  | LYS | D | 96 | 42.489 | 107.739 | 62.660 | 1.00 | 32.27 | C |
| ATOM | 31655 | NZ  | LYS | D | 96 | 41.709 | 109.045 | 62.490 | 1.00 | 36.08 | N |
| ATOM | 31659 | C   | LYS | D | 96 | 45.439 | 105.239 | 57.996 | 1.00 | 21.48 | C |
| ATOM | 31660 | O   | LYS | D | 96 | 46.456 | 104.788 | 58.473 | 1.00 | 20.85 | O |
| ATOM | 31662 | N   | SER | D | 97 | 45.018 | 104.877 | 56.783 | 1.00 | 20.54 | N |
| ATOM | 31663 | CA  | SER | D | 97 | 45.796 | 103.916 | 55.994 | 1.00 | 19.80 | C |
| ATOM | 31665 | CB  | SER | D | 97 | 45.013 | 103.339 | 54.792 | 1.00 | 21.48 | C |
| ATOM | 31668 | OG  | SER | D | 97 | 44.534 | 104.386 | 53.989 | 1.00 | 22.81 | O |
| ATOM | 31670 | C   | SER | D | 97 | 47.093 | 104.556 | 55.547 | 1.00 | 18.62 | C |
| ATOM | 31671 | O   | SER | D | 97 | 48.120 | 103.917 | 55.552 | 1.00 | 18.20 | O |
| ATOM | 31673 | N   | VAL | D | 98 | 47.033 | 105.818 | 55.118 | 1.00 | 18.16 | N |
| ATOM | 31674 | CA  | VAL | D | 98 | 48.237 | 106.555 | 54.729 | 1.00 | 17.06 | C |
| ATOM | 31676 | CB  | VAL | D | 98 | 47.875 | 107.962 | 54.213 | 1.00 | 17.32 | C |
| ATOM | 31678 | CG1 | VAL | D | 98 | 49.155 | 108.827 | 53.997 | 1.00 | 16.37 | C |
| ATOM | 31682 | CG2 | VAL | D | 98 | 47.032 | 107.875 | 52.945 | 1.00 | 17.71 | C |
| ATOM | 31686 | C   | VAL | D | 98 | 49.189 | 106.670 | 55.920 | 1.00 | 18.44 | C |
| ATOM | 31687 | O   | VAL | D | 98 | 50.387 | 106.427 | 55.798 | 1.00 | 18.06 | O |
| ATOM | 31689 | N   | GLU | D | 99 | 48.621 | 107.011 | 57.063 | 1.00 | 19.52 | N |
| ATOM | 31690 | CA  | GLU | D | 99 | 49.429 | 107.220 | 58.254 | 1.00 | 22.28 | C |
| ATOM | 31692 | CB  | GLU | D | 99 | 48.594 | 107.902 | 59.332 | 1.00 | 22.85 | C |
| ATOM | 31695 | CG  | GLU | D | 99 | 49.303 | 108.103 | 60.667 | 1.00 | 27.15 | C |
| ATOM | 31698 | CD  | GLU | D | 99 | 50.607 | 108.921 | 60.557 | 1.00 | 32.33 | C |
| ATOM | 31699 | OE1 | GLU | D | 99 | 50.736 | 109.790 | 59.646 | 1.00 | 35.63 | O |
| ATOM | 31700 | OE2 | GLU | D | 99 | 51.497 | 108.700 | 61.413 | 1.00 | 38.47 | O |
| ATOM | 31701 | C   | GLU | D | 99 | 50.038 | 105.917 | 58.746 | 1.00 | 22.48 | C |
| ATOM | 31702 | O   | GLU | D | 99 | 51.177 | 105.890 | 59.171 | 1.00 | 22.39 | O |

| ATOM | 31704 | N | PHE | D | 100 | 49.284 | 104.828 | 58.664 | 1.00 | 23.57 | N |
|------|-------|-----|-----|---|-----|--------|---------|--------|------|-------|---|
| ATOM | 31705 | CA | PHE | D | 100 | 49.806 | 103.516 | 59.064 | 1.00 | 24.58 | C |
| ATOM | 31707 | CB | PHE | D | 100 | 48.825 | 102.352 | 58.819 | 1.00 | 25.77 | C |
| ATOM | 31710 | CG | PHE | D | 100 | 49.468 | 100.979 | 58.999 | 1.00 | 25.25 | C |
| ATOM | 31711 | CD1 | PHE | D | 100 | 49.704 | 100.476 | 60.285 | 1.00 | 28.35 | C |
| ATOM | 31713 | CE1 | PHE | D | 100 | 50.319 | 99.231 | 60.465 | 1.00 | 28.79 | C |
| ATOM | 31715 | CZ | PHE | D | 100 | 50.739 | 98.493 | 59.378 | 1.00 | 28.50 | C |
| ATOM | 31717 | CE2 | PHE | D | 100 | 50.529 | 98.987 | 58.096 | 1.00 | 29.10 | C |
| ATOM | 31719 | CD2 | PHE | D | 100 | 49.903 | 100.237 | 57.916 | 1.00 | 27.45 | C |
| ATOM | 31721 | C | PHE | D | 100 | 51.053 | 103.251 | 58.279 | 1.00 | 25.14 | C |
| ATOM | 31722 | O | PHE | D | 100 | 52.075 | 102.856 | 58.821 | 1.00 | 25.38 | O |
| ATOM | 31724 | N | LEU | D | 101 | 50.969 | 103.475 | 56.975 | 1.00 | 26.63 | N |
| ATOM | 31725 | CA | LEU | D | 101 | 52.071 | 103.167 | 56.120 | 1.00 | 28.07 | C |
| ATOM | 31727 | CB | LEU | D | 101 | 51.645 | 103.273 | 54.648 | 1.00 | 28.08 | C |
| ATOM | 31730 | CG | LEU | D | 101 | 52.557 | 102.533 | 53.695 | 1.00 | 29.79 | C |
| ATOM | 31732 | CD1 | LEU | D | 101 | 52.549 | 101.041 | 53.978 | 1.00 | 31.17 | C |
| ATOM | 31736 | CD2 | LEU | D | 101 | 52.102 | 102.807 | 52.284 | 1.00 | 28.56 | C |
| ATOM | 31740 | C | LEU | D | 101 | 53.264 | 104.038 | 56.442 | 1.00 | 28.96 | C |
| ATOM | 31741 | O | LEU | D | 101 | 54.367 | 103.533 | 56.494 | 1.00 | 30.31 | O |
| ATOM | 31743 | N | ARG | D | 102 | 53.028 | 105.320 | 56.727 | 1.00 | 30.35 | N |
| ATOM | 31744 | CA | ARG | D | 102 | 54.092 | 106.273 | 57.102 | 1.00 | 31.74 | C |
| ATOM | 31746 | CB | ARG | D | 102 | 53.572 | 107.726 | 57.084 | 1.00 | 31.59 | C |
| ATOM | 31755 | C | ARG | D | 102 | 54.690 | 105.925 | 58.467 | 1.00 | 32.17 | C |
| ATOM | 31756 | O | ARG | D | 102 | 55.901 | 105.950 | 58.628 | 1.00 | 33.08 | O |
| ATOM | 31758 | N | SER | D | 103 | 53.825 | 105.600 | 59.433 | 1.00 | 33.30 | N |
| ATOM | 31759 | CA | SER | D | 103 | 54.215 | 105.191 | 60.788 | 1.00 | 33.78 | C |
| ATOM | 31763 | C | SER | D | 103 | 54.582 | 103.713 | 60.796 | 1.00 | 34.73 | C |
| ATOM | 31764 | O | SER | D | 103 | 55.406 | 103.266 | 59.997 | 1.00 | 35.49 | O |
| ATOM | 31766 | N | THR | D | 124 | 62.343 | 110.027 | 51.233 | 1.00 | 37.97 | N |
| ATOM | 31767 | CA | THR | D | 124 | 61.229 | 110.714 | 50.565 | 1.00 | 38.22 | C |
| ATOM | 31769 | CB | THR | D | 124 | 60.939 | 112.113 | 51.199 | 1.00 | 38.94 | C |
| ATOM | 31771 | OG1 | THR | D | 124 | 62.152 | 112.658 | 51.743 | 1.00 | 41.96 | O |
| ATOM | 31773 | CG2 | THR | D | 124 | 59.906 | 112.003 | 52.321 | 1.00 | 39.96 | C |
| ATOM | 31777 | C | THR | D | 124 | 61.436 | 110.908 | 49.045 | 1.00 | 37.60 | C |
| ATOM | 31778 | O | THR | D | 124 | 60.496 | 110.710 | 48.262 | 1.00 | 36.74 | O |
| ATOM | 31780 | N | GLU | D | 125 | 62.642 | 111.326 | 48.639 | 1.00 | 36.16 | N |
| ATOM | 31781 | CA | GLU | D | 125 | 62.919 | 111.574 | 47.219 | 1.00 | 36.23 | C |
| ATOM | 31783 | CB | GLU | D | 125 | 64.297 | 112.222 | 47.000 | 1.00 | 36.35 | C |
| ATOM | 31786 | CG | GLU | D | 125 | 64.591 | 113.485 | 47.791 | 1.00 | 39.29 | C |
| ATOM | 31789 | CD | GLU | D | 125 | 65.998 | 114.038 | 47.498 | 1.00 | 40.53 | C |
| ATOM | 31790 | OE1 | GLU | D | 125 | 66.623 | 113.598 | 46.482 | 1.00 | 46.47 | O |
| ATOM | 31791 | OE2 | GLU | D | 125 | 66.474 | 114.908 | 48.282 | 1.00 | 46.14 | O |
| ATOM | 31792 | C | GLU | D | 125 | 62.902 | 110.261 | 46.469 | 1.00 | 32.70 | C |
| ATOM | 31793 | O | GLU | D | 125 | 62.397 | 110.181 | 45.363 | 1.00 | 31.14 | O |
| ATOM | 31795 | N | ASP | D | 126 | 63.481 | 109.237 | 47.087 | 1.00 | 30.08 | N |
| ATOM | 31796 | CA | ASP | D | 126 | 63.565 | 107.904 | 46.499 | 1.00 | 28.94 | C |
| ATOM | 31798 | CB | ASP | D | 126 | 64.406 | 106.999 | 47.391 | 1.00 | 30.39 | C |
| ATOM | 31801 | CG | ASP | D | 126 | 65.753 | 107.608 | 47.698 | 1.00 | 33.22 | C |
| ATOM | 31802 | OD1 | ASP | D | 126 | 66.407 | 108.034 | 46.709 | 1.00 | 36.98 | O |
| ATOM | 31803 | OD2 | ASP | D | 126 | 66.111 | 107.689 | 48.906 | 1.00 | 37.77 | O |
| ATOM | 31804 | C | ASP | D | 126 | 62.189 | 107.259 | 46.311 | 1.00 | 26.22 | C |
| ATOM | 31805 | O | ASP | D | 126 | 61.989 | 106.496 | 45.366 | 1.00 | 24.58 | O |
| ATOM | 31807 | N | ALA | D | 127 | 61.273 | 107.542 | 47.240 | 1.00 | 24.24 | N |
| ATOM | 31808 | CA | ALA | D | 127 | 59.879 | 107.082 | 47.122 | 1.00 | 22.14 | C |
| ATOM | 31810 | CB | ALA | D | 127 | 59.064 | 107.368 | 48.399 | 1.00 | 22.17 | C |
| ATOM | 31814 | C | ALA | D | 127 | 59.208 | 107.763 | 45.953 | 1.00 | 20.82 | C |
| ATOM | 31815 | O | ALA | D | 127 | 58.484 | 107.118 | 45.197 | 1.00 | 20.41 | O |

| | | | | | | | | | |
|---|---|---|---|---|---|---|---|---|---|
| ATOM | 31817 | N | ILE | D | 128 | 59.458 | 109.059 | 45.807 | 1.00 19.64 | N |
| ATOM | 31818 | CA | ILE | D | 128 | 58.937 | 109.830 | 44.684 | 1.00 19.70 | C |
| ATOM | 31820 | CB | ILE | D | 128 | 59.259 | 111.343 | 44.801 | 1.00 19.82 | C |
| ATOM | 31822 | CG1 | ILE | D | 128 | 58.392 | 111.967 | 45.920 | 1.00 21.49 | C |
| ATOM | 31825 | CD1 | ILE | D | 128 | 58.744 | 113.445 | 46.231 | 1.00 22.02 | C |
| ATOM | 31829 | CG2 | ILE | D | 128 | 59.003 | 112.041 | 43.472 | 1.00 20.86 | C |
| ATOM | 31833 | C | ILE | D | 128 | 59.495 | 109.245 | 43.395 | 1.00 18.70 | C |
| ATOM | 31834 | O | ILE | D | 128 | 58.755 | 109.007 | 42.451 | 1.00 19.07 | O |
| ATOM | 31836 | N | SER | D | 129 | 60.801 | 108.963 | 43.379 | 1.00 18.18 | N |
| ATOM | 31837 | CA | SER | D | 129 | 61.421 | 108.377 | 42.184 | 1.00 18.05 | C |
| ATOM | 31839 | CB | SER | D | 129 | 62.920 | 108.192 | 42.382 | 1.00 18.76 | C |
| ATOM | 31842 | OG | SER | D | 129 | 63.523 | 109.458 | 42.353 | 1.00 20.59 | O |
| ATOM | 31844 | C | SER | D | 129 | 60.820 | 107.027 | 41.831 | 1.00 17.40 | C |
| ATOM | 31845 | O | SER | D | 129 | 60.646 | 106.705 | 40.661 | 1.00 15.32 | O |
| ATOM | 31847 | N | LEU | D | 130 | 60.584 | 106.191 | 42.840 | 1.00 17.09 | N |
| ATOM | 31848 | CA | LEU | D | 130 | 60.060 | 104.879 | 42.582 | 1.00 17.47 | C |
| ATOM | 31850 | CB | LEU | D | 130 | 59.928 | 104.125 | 43.900 | 1.00 18.51 | C |
| ATOM | 31853 | CG | LEU | D | 130 | 59.261 | 102.771 | 43.834 | 1.00 22.44 | C |
| ATOM | 31855 | CD1 | LEU | D | 130 | 59.955 | 101.875 | 42.842 | 1.00 22.73 | C |
| ATOM | 31859 | CD2 | LEU | D | 130 | 59.309 | 102.161 | 45.237 | 1.00 21.73 | C |
| ATOM | 31863 | C | LEU | D | 130 | 58.690 | 104.963 | 41.886 | 1.00 15.97 | C |
| ATOM | 31864 | O | LEU | D | 130 | 58.399 | 104.182 | 40.967 | 1.00 16.30 | O |
| ATOM | 31866 | N | GLN | D | 131 | 57.853 | 105.922 | 42.277 | 1.00 15.35 | N |
| ATOM | 31867 | CA | GLN | D | 131 | 56.525 | 106.004 | 41.623 | 1.00 15.65 | C |
| ATOM | 31869 | CB | GLN | D | 131 | 55.532 | 106.949 | 42.290 | 1.00 14.98 | C |
| ATOM | 31872 | CG | GLN | D | 131 | 55.480 | 106.948 | 43.824 | 1.00 14.49 | C |
| ATOM | 31875 | CD | GLN | D | 131 | 55.470 | 105.574 | 44.414 | 1.00 15.04 | C |
| ATOM | 31876 | OE1 | GLN | D | 131 | 54.608 | 104.748 | 44.069 | 1.00 14.59 | O |
| ATOM | 31877 | NE2 | GLN | D | 131 | 56.448 | 105.299 | 45.300 | 1.00 15.84 | N |
| ATOM | 31880 | C | GLN | D | 131 | 56.750 | 106.401 | 40.165 | 1.00 14.46 | C |
| ATOM | 31881 | O | GLN | D | 131 | 56.049 | 105.929 | 39.276 | 1.00 15.24 | O |
| ATOM | 31883 | N | LYS | D | 132 | 57.728 | 107.272 | 39.935 | 1.00 14.72 | N |
| ATOM | 31884 | CA | LYS | D | 132 | 58.024 | 107.691 | 38.573 | 1.00 13.69 | C |
| ATOM | 31886 | CB | LYS | D | 132 | 58.998 | 108.821 | 38.569 | 1.00 13.81 | C |
| ATOM | 31889 | CG | LYS | D | 132 | 58.329 | 110.120 | 39.117 | 1.00 13.33 | C |
| ATOM | 31892 | CD | LYS | D | 132 | 59.318 | 111.289 | 39.153 | 1.00 14.81 | C |
| ATOM | 31895 | CE | LYS | D | 132 | 58.682 | 112.538 | 39.716 | 1.00 18.06 | C |
| ATOM | 31898 | NZ | LYS | D | 132 | 59.650 | 113.686 | 39.819 | 1.00 17.13 | N |
| ATOM | 31902 | C | LYS | D | 132 | 58.567 | 106.521 | 37.731 | 1.00 13.11 | C |
| ATOM | 31903 | O | LYS | D | 132 | 58.227 | 106.431 | 36.549 | 1.00 13.18 | O |
| ATOM | 31905 | N | ALA | D | 133 | 59.360 | 105.632 | 38.320 | 1.00 13.92 | N |
| ATOM | 31906 | CA | ALA | D | 133 | 59.827 | 104.440 | 37.589 | 1.00 13.77 | C |
| ATOM | 31908 | CB | ALA | D | 133 | 60.896 | 103.653 | 38.372 | 1.00 14.14 | C |
| ATOM | 31912 | C | ALA | D | 133 | 58.666 | 103.493 | 37.257 | 1.00 14.60 | C |
| ATOM | 31913 | O | ALA | D | 133 | 58.655 | 102.836 | 36.215 | 1.00 14.97 | O |
| ATOM | 31915 | N | LEU | D | 134 | 57.703 | 103.415 | 38.170 | 1.00 15.10 | N |
| ATOM | 31916 | CA | LEU | D | 134 | 56.497 | 102.592 | 37.931 | 1.00 16.14 | C |
| ATOM | 31918 | CB | LEU | D | 134 | 55.609 | 102.568 | 39.178 | 1.00 15.99 | C |
| ATOM | 31921 | CG | LEU | D | 134 | 56.249 | 101.720 | 40.287 | 1.00 19.27 | C |
| ATOM | 31923 | CD1 | LEU | D | 134 | 55.503 | 101.885 | 41.661 | 1.00 22.06 | C |
| ATOM | 31927 | CD2 | LEU | D | 134 | 56.360 | 100.245 | 39.894 | 1.00 22.03 | C |
| ATOM | 31931 | C | LEU | D | 134 | 55.742 | 103.152 | 36.753 | 1.00 15.82 | C |
| ATOM | 31932 | O | LEU | D | 134 | 55.376 | 102.440 | 35.811 | 1.00 16.58 | O |
| ATOM | 31934 | N | LEU | D | 135 | 55.499 | 104.453 | 36.745 | 1.00 15.87 | N |
| ATOM | 31935 | CA | LEU | D | 135 | 54.805 | 104.998 | 35.571 | 1.00 15.14 | C |
| ATOM | 31937 | CB | LEU | D | 135 | 54.368 | 106.449 | 35.768 | 1.00 15.61 | C |
| ATOM | 31940 | CG | LEU | D | 135 | 53.507 | 106.717 | 36.994 | 1.00 19.07 | C |

| | | | | | | | | | |
|---|---|---|---|---|---|---|---|---|---|
| ATOM | 31942 | CD1 | LEU | D | 135 | 52.904 | 108.098 | 36.892 | 1.00 19.58 | C |
| ATOM | 31946 | CD2 | LEU | D | 135 | 52.431 | 105.755 | 37.208 | 1.00 20.42 | C |
| ATOM | 31950 | C | LEU | D | 135 | 55.607 | 104.900 | 34.288 | 1.00 14.97 | C |
| ATOM | 31951 | O | LEU | D | 135 | 55.044 | 104.607 | 33.225 | 1.00 14.58 | O |
| ATOM | 31953 | N | GLU | D | 136 | 56.919 | 105.150 | 34.366 | 1.00 13.05 | N |
| ATOM | 31954 | CA | GLU | D | 136 | 57.702 | 105.271 | 33.147 | 1.00 12.70 | C |
| ATOM | 31956 | CB | GLU | D | 136 | 59.183 | 105.412 | 33.494 | 1.00 12.80 | C |
| ATOM | 31959 | CG | GLU | D | 136 | 60.182 | 105.276 | 32.331 | 1.00 13.33 | C |
| ATOM | 31962 | CD | GLU | D | 136 | 61.652 | 105.185 | 32.787 | 1.00 14.45 | C |
| ATOM | 31963 | OE1 | GLU | D | 136 | 61.973 | 104.697 | 33.925 | 1.00 14.55 | O |
| ATOM | 31964 | OE2 | GLU | D | 136 | 62.569 | 105.603 | 32.006 | 1.00 15.82 | O |
| ATOM | 31965 | C | GLU | D | 136 | 57.532 | 104.040 | 32.284 | 1.00 12.20 | C |
| ATOM | 31966 | O | GLU | D | 136 | 57.263 | 104.142 | 31.107 | 1.00 13.01 | O |
| ATOM | 31968 | N | HIS | D | 137 | 57.680 | 102.837 | 32.871 | 1.00 11.52 | N |
| ATOM | 31969 | CA | HIS | D | 137 | 57.646 | 101.610 | 32.058 | 1.00 11.70 | C |
| ATOM | 31971 | CB | HIS | D | 137 | 58.364 | 100.454 | 32.785 | 1.00 12.63 | C |
| ATOM | 31974 | CG | HIS | D | 137 | 57.536 | 99.770 | 33.832 | 1.00 13.43 | C |
| ATOM | 31975 | ND1 | HIS | D | 137 | 57.440 | 100.246 | 35.122 | 1.00 17.27 | N |
| ATOM | 31977 | CE1 | HIS | D | 137 | 56.696 | 99.413 | 35.841 | 1.00 17.20 | C |
| ATOM | 31979 | NE2 | HIS | D | 137 | 56.296 | 98.428 | 35.062 | 1.00 15.41 | N |
| ATOM | 31981 | CD2 | HIS | D | 137 | 56.819 | 98.618 | 33.802 | 1.00 15.71 | C |
| ATOM | 31983 | C | HIS | D | 137 | 56.227 | 101.221 | 31.586 | 1.00 11.21 | C |
| ATOM | 31984 | O | HIS | D | 137 | 56.080 | 100.509 | 30.613 | 1.00 12.79 | O |
| ATOM | 31986 | N | GLN | D | 138 | 55.186 | 101.692 | 32.279 | 1.00 11.28 | N |
| ATOM | 31987 | CA | GLN | D | 138 | 53.840 | 101.366 | 31.913 | 1.00 11.20 | C |
| ATOM | 31989 | CB | GLN | D | 138 | 52.969 | 101.332 | 33.149 | 1.00 11.57 | C |
| ATOM | 31992 | CG | GLN | D | 138 | 53.264 | 100.138 | 34.039 | 1.00 13.94 | C |
| ATOM | 31995 | CD | GLN | D | 138 | 52.859 | 98.824 | 33.431 | 1.00 15.93 | C |
| ATOM | 31996 | OE1 | GLN | D | 138 | 51.986 | 98.765 | 32.582 | 1.00 18.83 | O |
| ATOM | 31997 | NE2 | GLN | D | 138 | 53.516 | 97.720 | 33.851 | 1.00 16.45 | N |
| ATOM | 32000 | C | GLN | D | 138 | 53.232 | 102.323 | 30.883 | 1.00 11.65 | C |
| ATOM | 32001 | O | GLN | D | 138 | 52.202 | 101.976 | 30.296 | 1.00 12.72 | O |
| ATOM | 32003 | N | LEU | D | 139 | 53.877 | 103.478 | 30.643 | 1.00 11.25 | N |
| ATOM | 32004 | CA | LEU | D | 139 | 53.444 | 104.425 | 29.613 | 1.00 11.04 | C |
| ATOM | 32006 | CB | LEU | D | 139 | 53.837 | 105.851 | 30.015 | 1.00 10.94 | C |
| ATOM | 32009 | CG | LEU | D | 139 | 53.191 | 106.335 | 31.292 | 1.00 11.31 | C |
| ATOM | 32011 | CD1 | LEU | D | 139 | 53.848 | 107.632 | 31.809 | 1.00 14.25 | C |
| ATOM | 32015 | CD2 | LEU | D | 139 | 51.705 | 106.550 | 31.105 | 1.00 14.16 | C |
| ATOM | 32019 | C | LEU | D | 139 | 54.006 | 103.968 | 28.274 | 1.00 10.27 | C |
| ATOM | 32020 | O | LEU | D | 139 | 54.827 | 104.681 | 27.646 | 1.00 12.06 | O |
| ATOM | 32022 | N | CYS | D | 140 | 53.543 | 102.794 | 27.813 | 1.00 12.07 | N |
| ATOM | 32023 | CA | CYS | D | 140 | 54.229 | 102.072 | 26.737 | 1.00 11.73 | C |
| ATOM | 32025 | CB | CYS | D | 140 | 54.923 | 100.861 | 27.338 | 1.00 11.82 | C |
| ATOM | 32028 | SG | CYS | D | 140 | 53.810 | 99.666 | 28.025 | 1.00 15.77 | S |
| ATOM | 32030 | C | CYS | D | 140 | 53.335 | 101.651 | 25.602 | 1.00 12.49 | C |
| ATOM | 32031 | O | CYS | D | 140 | 53.762 | 100.882 | 24.735 | 1.00 12.68 | O |
| ATOM | 32033 | N | GLY | D | 141 | 52.120 | 102.217 | 25.566 | 1.00 12.89 | N |
| ATOM | 32034 | CA | GLY | D | 141 | 51.165 | 101.887 | 24.559 | 1.00 13.45 | C |
| ATOM | 32037 | C | GLY | D | 141 | 51.201 | 102.864 | 23.389 | 1.00 12.69 | C |
| ATOM | 32038 | O | GLY | D | 141 | 51.844 | 103.963 | 23.437 | 1.00 13.15 | O |
| ATOM | 32040 | N | VAL | D | 142 | 50.460 | 102.490 | 22.337 | 1.00 11.93 | N |
| ATOM | 32041 | CA | VAL | D | 142 | 50.506 | 103.250 | 21.089 | 1.00 11.13 | C |
| ATOM | 32043 | CB | VAL | D | 142 | 50.575 | 102.281 | 19.887 | 1.00 11.43 | C |
| ATOM | 32045 | CG1 | VAL | D | 142 | 50.312 | 102.919 | 18.560 | 1.00 12.73 | C |
| ATOM | 32049 | CG2 | VAL | D | 142 | 51.930 | 101.572 | 19.883 | 1.00 12.55 | C |
| ATOM | 32053 | C | VAL | D | 142 | 49.290 | 104.195 | 20.931 | 1.00 12.34 | C |
| ATOM | 32054 | O | VAL | D | 142 | 48.136 | 103.806 | 21.123 | 1.00 12.46 | O |

```
ATOM  32056  N    LEU D 143      49.592 105.425  20.593  1.00 12.47           N
ATOM  32057  CA   LEU D 143      48.613 106.467  20.321  1.00 11.98           C
ATOM  32059  CB   LEU D 143      48.502 107.442  21.508  1.00 13.81           C
ATOM  32062  CG   LEU D 143      47.804 106.930  22.752  1.00 13.36           C
ATOM  32064  CD1  LEU D 143      48.140 107.800  23.954  1.00 13.34           C
ATOM  32068  CD2  LEU D 143      46.345 106.834  22.510  1.00 14.85           C
ATOM  32072  C    LEU D 143      49.123 107.252  19.103  1.00 12.28           C
ATOM  32073  O    LEU D 143      50.367 107.289  18.853  1.00 11.41           O
ATOM  32075  N    PRO D 144      48.210 107.963  18.405  1.00 13.10           N
ATOM  32076  CA   PRO D 144      48.690 108.835  17.346  1.00 13.70           C
ATOM  32078  CB   PRO D 144      47.421 109.550  16.847  1.00 14.99           C
ATOM  32081  CG   PRO D 144      46.353 109.257  17.772  1.00 15.80           C
ATOM  32084  CD   PRO D 144      46.743 108.067  18.600  1.00 13.12           C
ATOM  32087  C    PRO D 144      49.715 109.863  17.803  1.00 13.52           C
ATOM  32088  O    PRO D 144      49.511 110.515  18.824  1.00 14.17           O
ATOM  32089  N    SER D 145      50.801 110.036  17.071  1.00 13.67           N
ATOM  32090  CA   SER D 145      51.853 110.951  17.498  1.00 16.13           C
ATOM  32092  CB   SER D 145      53.172 110.663  16.769  1.00 16.45           C
ATOM  32095  OG   SER D 145      53.000 110.969  15.404  1.00 18.55           O
ATOM  32097  C    SER D 145      51.485 112.398  17.266  1.00 16.65           C
ATOM  32098  O    SER D 145      52.038 113.240  17.935  1.00 17.27           O
ATOM  32100  N    SER D 146      50.613 112.676  16.299  1.00 17.67           N
ATOM  32101  CA   SER D 146      50.264 114.057  15.928  1.00 19.82           C
ATOM  32103  CB   SER D 146      51.220 114.528  14.819  1.00 20.30           C
ATOM  32106  OG   SER D 146      50.731 115.634  14.134  1.00 25.52           O
ATOM  32108  C    SER D 146      48.841 114.129  15.379  1.00 21.14           C
ATOM  32109  O    SER D 146      48.286 113.144  14.908  1.00 19.35           O
ATOM  32111  N    PHE D 147      48.268 115.327  15.401  1.00 22.85           N
ATOM  32112  CA   PHE D 147      47.002 115.556  14.715  1.00 23.75           C
ATOM  32114  CB   PHE D 147      46.456 116.932  15.060  1.00 24.79           C
ATOM  32117  CG   PHE D 147      45.753 116.974  16.374  1.00 26.90           C
ATOM  32118  CD1  PHE D 147      44.617 116.200  16.576  1.00 25.68           C
ATOM  32120  CE1  PHE D 147      43.941 116.245  17.784  1.00 27.56           C
ATOM  32122  CZ   PHE D 147      44.378 117.074  18.796  1.00 27.25           C
ATOM  32124  CE2  PHE D 147      45.517 117.862  18.618  1.00 30.16           C
ATOM  32126  CD2  PHE D 147      46.201 117.807  17.392  1.00 29.08           C
ATOM  32128  C    PHE D 147      47.097 115.417  13.195  1.00 23.89           C
ATOM  32129  O    PHE D 147      46.076 115.366  12.522  1.00 22.80           O
ATOM  32131  N    ASP D 148      48.321 115.387  12.659  1.00 23.38           N
ATOM  32132  CA   ASP D 148      48.499 115.287  11.205  1.00 23.38           C
ATOM  32134  CB   ASP D 148      49.995 115.269  10.848  1.00 24.33           C
ATOM  32137  CG   ASP D 148      50.705 116.544  11.213  1.00 30.41           C
ATOM  32138  OD1  ASP D 148      50.044 117.607  11.416  1.00 33.89           O
ATOM  32139  OD2  ASP D 148      51.961 116.469  11.280  1.00 34.80           O
ATOM  32140  C    ASP D 148      47.883 114.035  10.607  1.00 22.43           C
ATOM  32141  O    ASP D 148      47.608 113.999   9.410  1.00 21.33           O
ATOM  32143  N    SER D 149      47.718 113.004  11.438  1.00 20.67           N
ATOM  32144  CA   SER D 149      47.204 111.697  11.005  1.00 20.12           C
ATOM  32146  CB   SER D 149      47.782 110.533  11.856  1.00 20.46           C
ATOM  32149  OG   SER D 149      47.518 110.723  13.252  1.00 18.36           O
ATOM  32151  C    SER D 149      45.694 111.642  11.042  1.00 20.16           C
ATOM  32152  O    SER D 149      45.089 110.687  10.495  1.00 20.05           O
ATOM  32154  N    PHE D 150      45.076 112.594  11.758  1.00 19.32           N
ATOM  32155  CA   PHE D 150      43.609 112.564  11.882  1.00 18.56           C
ATOM  32157  CB   PHE D 150      43.079 113.577  12.899  1.00 17.74           C
ATOM  32160  CG   PHE D 150      43.296 113.178  14.348  1.00 17.02           C
ATOM  32161  CD1  PHE D 150      44.506 112.670  14.800  1.00 18.75           C
```

| | | | | | | | | | |
|---|---|---|---|---|---|---|---|---|---|
| ATOM | 32163 | CE1 | PHE | D | 150 | 44.688 | 112.353 | 16.151 | 1.00 16.98 | C |
| ATOM | 32165 | CZ | PHE | D | 150 | 43.668 | 112.527 | 17.048 | 1.00 16.01 | C |
| ATOM | 32167 | CE2 | PHE | D | 150 | 42.488 | 113.014 | 16.625 | 1.00 17.60 | C |
| ATOM | 32169 | CD2 | PHE | D | 150 | 42.295 | 113.353 | 15.266 | 1.00 16.69 | C |
| ATOM | 32171 | C | PHE | D | 150 | 43.016 | 112.910 | 10.548 | 1.00 18.63 | C |
| ATOM | 32172 | O | PHE | D | 150 | 43.597 | 113.639 | 9.759 | 1.00 19.39 | O |
| ATOM | 32174 | N | ARG | D | 151 | 41.820 | 112.422 | 10.338 | 1.00 17.56 | N |
| ATOM | 32175 | CA | ARG | D | 151 | 41.058 | 112.644 | 9.118 | 1.00 17.46 | C |
| ATOM | 32177 | CB | ARG | D | 151 | 41.250 | 111.513 | 8.167 | 1.00 18.49 | C |
| ATOM | 32180 | CG | ARG | D | 151 | 42.632 | 111.304 | 7.639 | 1.00 20.36 | C |
| ATOM | 32183 | CD | ARG | D | 151 | 43.029 | 112.350 | 6.706 | 1.00 21.17 | C |
| ATOM | 32186 | NE | ARG | D | 151 | 44.340 | 112.086 | 6.149 | 1.00 21.54 | N |
| ATOM | 32188 | CZ | ARG | D | 151 | 45.490 | 112.497 | 6.693 | 1.00 23.77 | C |
| ATOM | 32189 | NH1 | ARG | D | 151 | 45.516 | 113.203 | 7.816 | 1.00 20.74 | N |
| ATOM | 32192 | NH2 | ARG | D | 151 | 46.637 | 112.201 | 6.104 | 1.00 23.72 | N |
| ATOM | 32195 | C | ARG | D | 151 | 39.612 | 112.695 | 9.517 | 1.00 16.66 | C |
| ATOM | 32196 | O | ARG | D | 151 | 39.251 | 112.357 | 10.659 | 1.00 17.76 | O |
| ATOM | 32198 | N | LEU | D | 152 | 38.756 | 113.138 | 8.594 | 1.00 16.10 | N |
| ATOM | 32199 | CA | LEU | D | 152 | 37.348 | 113.276 | 8.890 | 1.00 15.40 | C |
| ATOM | 32201 | CB | LEU | D | 152 | 36.576 | 113.761 | 7.662 | 1.00 14.71 | C |
| ATOM | 32204 | CG | LEU | D | 152 | 35.083 | 113.948 | 7.840 | 1.00 16.95 | C |
| ATOM | 32206 | CD1 | LEU | D | 152 | 34.785 | 115.046 | 8.838 | 1.00 17.02 | C |
| ATOM | 32210 | CD2 | LEU | D | 152 | 34.534 | 114.325 | 6.489 | 1.00 16.93 | C |
| ATOM | 32214 | C | LEU | D | 152 | 36.789 | 111.942 | 9.376 | 1.00 15.19 | C |
| ATOM | 32215 | O | LEU | D | 152 | 36.914 | 110.901 | 8.717 | 1.00 14.94 | O |
| ATOM | 32217 | N | GLY | D | 153 | 36.171 | 111.961 | 10.551 | 1.00 14.61 | N |
| ATOM | 32218 | CA | GLY | D | 153 | 35.623 | 110.725 | 11.061 | 1.00 13.72 | C |
| ATOM | 32221 | C | GLY | D | 153 | 36.560 | 109.631 | 11.610 | 1.00 15.19 | C |
| ATOM | 32222 | O | GLY | D | 153 | 36.136 | 108.541 | 11.926 | 1.00 13.60 | O |
| ATOM | 32224 | N | ARG | D | 154 | 37.838 | 109.964 | 11.729 | 1.00 14.82 | N |
| ATOM | 32225 | CA | ARG | D | 154 | 38.870 | 109.014 | 12.053 | 1.00 14.75 | C |
| ATOM | 32227 | CB | ARG | D | 154 | 39.590 | 108.528 | 10.779 | 1.00 15.34 | C |
| ATOM | 32230 | CG | ARG | D | 154 | 38.720 | 108.023 | 9.658 | 1.00 16.37 | C |
| ATOM | 32233 | CD | ARG | D | 154 | 38.137 | 106.633 | 9.917 | 1.00 18.12 | C |
| ATOM | 32236 | NE | ARG | D | 154 | 37.440 | 106.091 | 8.745 | 1.00 17.37 | N |
| ATOM | 32238 | CZ | ARG | D | 154 | 36.901 | 104.883 | 8.653 | 1.00 16.92 | C |
| ATOM | 32239 | NH1 | ARG | D | 154 | 36.984 | 103.995 | 9.674 | 1.00 14.46 | N |
| ATOM | 32242 | NH2 | ARG | D | 154 | 36.336 | 104.541 | 7.503 | 1.00 16.81 | N |
| ATOM | 32245 | C | ARG | D | 154 | 39.930 | 109.672 | 12.928 | 1.00 14.39 | C |
| ATOM | 32246 | O | ARG | D | 154 | 40.044 | 110.897 | 12.956 | 1.00 14.88 | O |
| ATOM | 32248 | N | GLY | D | 155 | 40.748 | 108.828 | 13.558 | 1.00 14.19 | N |
| ATOM | 32249 | CA | GLY | D | 155 | 41.957 | 109.347 | 14.191 | 1.00 13.36 | C |
| ATOM | 32252 | C | GLY | D | 155 | 42.269 | 108.789 | 15.573 | 1.00 14.22 | C |
| ATOM | 32253 | O | GLY | D | 155 | 43.471 | 108.688 | 15.922 | 1.00 14.66 | O |
| ATOM | 32255 | N | LEU | D | 156 | 41.222 | 108.466 | 16.338 | 1.00 14.08 | N |
| ATOM | 32256 | CA | LEU | D | 156 | 41.353 | 108.072 | 17.738 | 1.00 14.41 | C |
| ATOM | 32258 | CB | LEU | D | 156 | 40.543 | 109.033 | 18.641 | 1.00 14.26 | C |
| ATOM | 32261 | CG | LEU | D | 156 | 41.255 | 110.328 | 19.045 | 1.00 12.74 | C |
| ATOM | 32263 | CD1 | LEU | D | 156 | 40.384 | 111.135 | 19.958 | 1.00 13.90 | C |
| ATOM | 32267 | CD2 | LEU | D | 156 | 42.618 | 109.989 | 19.711 | 1.00 14.52 | C |
| ATOM | 32271 | C | LEU | D | 156 | 41.089 | 106.584 | 17.971 | 1.00 13.61 | C |
| ATOM | 32272 | O | LEU | D | 156 | 40.890 | 106.113 | 19.102 | 1.00 13.98 | O |
| ATOM | 32274 | N | GLU | D | 157 | 41.124 | 105.818 | 16.874 | 1.00 13.71 | N |
| ATOM | 32275 | CA | GLU | D | 157 | 40.896 | 104.360 | 16.948 | 1.00 14.28 | C |
| ATOM | 32277 | CB | GLU | D | 157 | 40.954 | 103.695 | 15.563 | 1.00 15.82 | C |
| ATOM | 32280 | CG | GLU | D | 157 | 42.192 | 103.882 | 14.823 | 1.00 21.24 | C |
| ATOM | 32283 | CD | GLU | D | 157 | 42.191 | 105.124 | 13.888 | 1.00 24.97 | C |

| ATOM | 32284 | OE1 | GLU | D | 157 | 41.390 | 106.076 | 14.092 | 1.00 | 19.57 | O |
| --- | --- | --- | --- | --- | --- | --- | --- | --- | --- | --- | --- |
| ATOM | 32285 | OE2 | GLU | D | 157 | 43.000 | 105.121 | 12.918 | 1.00 | 30.68 | O |
| ATOM | 32286 | C | GLU | D | 157 | 41.847 | 103.618 | 17.878 | 1.00 | 14.82 | C |
| ATOM | 32287 | O | GLU | D | 157 | 41.467 | 102.599 | 18.405 | 1.00 | 14.52 | O |
| ATOM | 32289 | N | ASN | D | 158 | 43.058 | 104.121 | 18.046 | 1.00 | 12.66 | N |
| ATOM | 32290 | CA | ASN | D | 158 | 43.998 | 103.515 | 18.986 | 1.00 | 13.29 | C |
| ATOM | 32292 | CB | ASN | D | 158 | 45.412 | 103.592 | 18.478 | 1.00 | 15.20 | C |
| ATOM | 32295 | CG | ASN | D | 158 | 45.687 | 102.599 | 17.342 | 1.00 | 14.22 | C |
| ATOM | 32296 | OD1 | ASN | D | 158 | 45.048 | 101.524 | 17.233 | 1.00 | 15.04 | O |
| ATOM | 32297 | ND2 | ASN | D | 158 | 46.571 | 103.028 | 16.414 | 1.00 | 13.72 | N |
| ATOM | 32300 | C | ASN | D | 158 | 43.907 | 103.990 | 20.424 | 1.00 | 13.31 | C |
| ATOM | 32301 | O | ASN | D | 158 | 44.788 | 103.656 | 21.233 | 1.00 | 12.89 | O |
| ATOM | 32303 | N | SER | D | 159 | 42.830 | 104.709 | 20.756 | 1.00 | 12.29 | N |
| ATOM | 32304 | CA | SER | D | 159 | 42.609 | 105.120 | 22.150 | 1.00 | 12.79 | C |
| ATOM | 32306 | CB | SER | D | 159 | 42.585 | 106.614 | 22.242 | 1.00 | 12.51 | C |
| ATOM | 32309 | OG | SER | D | 159 | 41.412 | 107.152 | 21.610 | 1.00 | 14.69 | O |
| ATOM | 32311 | C | SER | D | 159 | 41.319 | 104.536 | 22.716 | 1.00 | 13.18 | C |
| ATOM | 32312 | O | SER | D | 159 | 40.385 | 104.238 | 21.966 | 1.00 | 13.77 | O |
| ATOM | 32314 | N | LEU | D | 160 | 41.258 | 104.408 | 24.045 | 1.00 | 12.88 | N |
| ATOM | 32315 | CA | LEU | D | 160 | 40.079 | 103.892 | 24.704 | 1.00 | 13.48 | C |
| ATOM | 32317 | CB | LEU | D | 160 | 40.333 | 103.709 | 26.195 | 1.00 | 15.32 | C |
| ATOM | 32320 | CG | LEU | D | 160 | 41.045 | 102.466 | 26.611 | 1.00 | 17.74 | C |
| ATOM | 32322 | CD1 | LEU | D | 160 | 41.249 | 102.564 | 28.136 | 1.00 | 18.30 | C |
| ATOM | 32326 | CD2 | LEU | D | 160 | 40.222 | 101.245 | 26.319 | 1.00 | 18.56 | C |
| ATOM | 32330 | C | LEU | D | 160 | 38.963 | 104.896 | 24.581 | 1.00 | 14.00 | C |
| ATOM | 32331 | O | LEU | D | 160 | 39.188 | 106.124 | 24.719 | 1.00 | 12.59 | O |
| ATOM | 32333 | N | PRO | D | 161 | 37.732 | 104.410 | 24.362 | 1.00 | 14.47 | N |
| ATOM | 32334 | CA | PRO | D | 161 | 36.627 | 105.381 | 24.429 | 1.00 | 13.98 | C |
| ATOM | 32336 | CB | PRO | D | 161 | 35.398 | 104.499 | 24.361 | 1.00 | 13.90 | C |
| ATOM | 32339 | CG | PRO | D | 161 | 35.877 | 103.237 | 23.628 | 1.00 | 14.72 | C |
| ATOM | 32342 | CD | PRO | D | 161 | 37.291 | 103.048 | 24.076 | 1.00 | 15.22 | C |
| ATOM | 32345 | C | PRO | D | 161 | 36.606 | 106.229 | 25.735 | 1.00 | 13.98 | C |
| ATOM | 32346 | O | PRO | D | 161 | 36.918 | 105.770 | 26.833 | 1.00 | 13.01 | O |
| ATOM | 32347 | N | LEU | D | 162 | 36.247 | 107.490 | 25.575 | 1.00 | 12.75 | N |
| ATOM | 32348 | CA | LEU | D | 162 | 36.162 | 108.447 | 26.669 | 1.00 | 13.02 | C |
| ATOM | 32350 | CB | LEU | D | 162 | 35.701 | 109.811 | 26.214 | 1.00 | 13.56 | C |
| ATOM | 32353 | CG | LEU | D | 162 | 36.623 | 110.491 | 25.161 | 1.00 | 13.54 | C |
| ATOM | 32355 | CD1 | LEU | D | 162 | 36.049 | 111.791 | 24.740 | 1.00 | 14.44 | C |
| ATOM | 32359 | CD2 | LEU | D | 162 | 38.023 | 110.636 | 25.636 | 1.00 | 14.35 | C |
| ATOM | 32363 | C | LEU | D | 162 | 35.256 | 107.957 | 27.779 | 1.00 | 12.93 | C |
| ATOM | 32364 | O | LEU | D | 162 | 35.627 | 108.070 | 28.962 | 1.00 | 13.05 | O |
| ATOM | 32366 | N | GLU | D | 163 | 34.124 | 107.356 | 27.427 | 1.00 | 12.92 | N |
| ATOM | 32367 | CA | GLU | D | 163 | 33.226 | 106.858 | 28.486 | 1.00 | 13.64 | C |
| ATOM | 32369 | CB | GLU | D | 163 | 31.893 | 106.344 | 27.914 | 1.00 | 14.77 | C |
| ATOM | 32372 | CG | GLU | D | 163 | 32.016 | 105.169 | 26.965 | 1.00 | 15.56 | C |
| ATOM | 32375 | CD | GLU | D | 163 | 30.657 | 104.637 | 26.482 | 1.00 | 19.41 | C |
| ATOM | 32376 | OE1 | GLU | D | 163 | 29.763 | 105.489 | 26.307 | 1.00 | 24.04 | O |
| ATOM | 32377 | OE2 | GLU | D | 163 | 30.490 | 103.416 | 26.255 | 1.00 | 20.23 | O |
| ATOM | 32378 | C | GLU | D | 163 | 33.889 | 105.767 | 29.323 | 1.00 | 12.90 | C |
| ATOM | 32379 | O | GLU | D | 163 | 33.645 | 105.669 | 30.511 | 1.00 | 12.85 | O |
| ATOM | 32381 | N | VAL | D | 164 | 34.693 | 104.914 | 28.683 | 1.00 | 12.71 | N |
| ATOM | 32382 | CA | VAL | D | 164 | 35.390 | 103.860 | 29.438 | 1.00 | 13.25 | C |
| ATOM | 32384 | CB | VAL | D | 164 | 36.144 | 102.935 | 28.518 | 1.00 | 13.36 | C |
| ATOM | 32386 | CG1 | VAL | D | 164 | 37.013 | 101.934 | 29.312 | 1.00 | 11.87 | C |
| ATOM | 32390 | CG2 | VAL | D | 164 | 35.120 | 102.261 | 27.623 | 1.00 | 14.22 | C |
| ATOM | 32394 | C | VAL | D | 164 | 36.314 | 104.483 | 30.458 | 1.00 | 12.99 | C |
| ATOM | 32395 | O | VAL | D | 164 | 36.428 | 104.013 | 31.587 | 1.00 | 12.55 | O |

```
ATOM  32397  N    VAL D 165      37.069 105.473 30.022  1.00 12.56           N
ATOM  32398  CA   VAL D 165      38.048 106.132 30.877  1.00 13.45           C
ATOM  32400  CB   VAL D 165      38.967 107.092 30.093  1.00 13.08           C
ATOM  32402  CG1  VAL D 165      39.927 107.858 31.037  1.00 13.01           C
ATOM  32406  CG2  VAL D 165      39.734 106.324 29.063  1.00 14.37           C
ATOM  32410  C    VAL D 165      37.352 106.840 32.046  1.00 12.32           C
ATOM  32411  O    VAL D 165      37.762 106.692 33.198  1.00 12.96           O
ATOM  32413  N    ARG D 166      36.239 107.519 31.797  1.00 11.88           N
ATOM  32414  CA   ARG D 166      35.444 108.114 32.899  1.00 11.97           C
ATOM  32416  CB   ARG D 166      34.254 108.838 32.304  1.00 12.32           C
ATOM  32419  CG   ARG D 166      34.636 110.161 31.657  1.00 11.29           C
ATOM  32422  CD   ARG D 166      33.433 111.081 31.251  1.00 12.80           C
ATOM  32425  NE   ARG D 166      32.484 111.282 32.339  1.00 12.94           N
ATOM  32427  CZ   ARG D 166      32.570 112.251 33.251  1.00 13.47           C
ATOM  32428  NH1  ARG D 166      33.574 113.121 33.252  1.00 12.59           N
ATOM  32431  NH2  ARG D 166      31.655 112.358 34.225  1.00 13.24           N
ATOM  32434  C    ARG D 166      34.942 107.064 33.894  1.00 12.66           C
ATOM  32435  O    ARG D 166      35.029 107.254 35.095  1.00 11.56           O
ATOM  32437  N    GLY D 167      34.393 105.975 33.385  1.00 12.76           N
ATOM  32438  CA   GLY D 167      33.912 104.882 34.236  1.00 13.44           C
ATOM  32441  C    GLY D 167      35.062 104.345 35.076  1.00 13.13           C
ATOM  32442  O    GLY D 167      34.892 104.002 36.246  1.00 13.75           O
ATOM  32444  N    ALA D 168      36.240 104.261 34.471  1.00 11.60           N
ATOM  32445  CA   ALA D 168      37.426 103.735 35.171  1.00 12.81           C
ATOM  32447  CB   ALA D 168      38.524 103.610 34.209  1.00 13.21           C
ATOM  32451  C    ALA D 168      37.854 104.627 36.312  1.00 12.82           C
ATOM  32452  O    ALA D 168      38.190 104.142 37.426  1.00 11.92           O
ATOM  32454  N    MSE D 169      37.848 105.920 36.049  1.00 13.23           N
ATOM  32455  CA   MSE D 169      38.200 106.905 37.091  1.00 14.51           C
ATOM  32457  CB   MSE D 169      38.322 108.325 36.539  1.00 14.15           C
ATOM  32460  CG   MSE D 169      39.492 108.445 35.620  1.00 13.61           C
ATOM  32463  SE   MSE D 169      39.945 110.278 35.152  1.00 22.78           SE
ATOM  32464  CE   MSE D 169      38.336 110.645 34.045  1.00 15.36           C
ATOM  32468  C    MSE D 169      37.224 106.817 38.268  1.00 12.87           C
ATOM  32469  O    MSE D 169      37.641 106.875 39.420  1.00 13.15           O
ATOM  32471  N    THR D 170      35.944 106.633 37.958  1.00 12.42           N
ATOM  32472  CA   THR D 170      34.902 106.559 38.955  1.00 11.60           C
ATOM  32474  CB   THR D 170      33.523 106.530 38.293  1.00 12.65           C
ATOM  32476  OG1  THR D 170      33.351 107.698 37.472  1.00 13.99           O
ATOM  32478  CG2  THR D 170      32.454 106.471 39.344  1.00 13.03           C
ATOM  32482  C    THR D 170      35.121 105.306 39.841  1.00 12.71           C
ATOM  32483  O    THR D 170      35.139 105.386 41.079  1.00 11.99           O
ATOM  32485  N    ILE D 171      35.322 104.153 39.186  1.00 11.99           N
ATOM  32486  CA   ILE D 171      35.562 102.899 39.906  1.00 11.53           C
ATOM  32488  CB   ILE D 171      35.507 101.697 38.958  1.00 11.30           C
ATOM  32490  CG1  ILE D 171      34.088 101.516 38.431  1.00 11.60           C
ATOM  32493  CD1  ILE D 171      33.979 100.518 37.279  1.00 13.15           C
ATOM  32497  CG2  ILE D 171      36.062 100.453 39.630  1.00 11.91           C
ATOM  32501  C    ILE D 171      36.852 102.968 40.701  1.00 11.29           C
ATOM  32502  O    ILE D 171      36.885 102.578 41.881  1.00 13.61           O
ATOM  32504  N    ARG D 172      37.882 103.529 40.095  1.00 11.30           N
ATOM  32505  CA   ARG D 172      39.187 103.627 40.761  1.00 12.45           C
ATOM  32507  CB   ARG D 172      40.213 104.292 39.850  1.00 13.80           C
ATOM  32510  CG   ARG D 172      41.562 104.646 40.523  1.00 12.97           C
ATOM  32513  CD   ARG D 172      42.557 103.521 40.521  1.00 16.18           C
ATOM  32516  NE   ARG D 172      42.169 102.490 41.445  1.00 16.73           N
ATOM  32518  CZ   ARG D 172      42.852 101.365 41.605  1.00 17.94           C
```

```
ATOM  32519  NH1 ARG D 172      43.915 101.118 40.848  1.00 18.65           N
ATOM  32522  NH2 ARG D 172      42.450 100.473 42.491  1.00 20.39           N
ATOM  32525  C   ARG D 172      39.040 104.392 42.086  1.00 12.31           C
ATOM  32526  O   ARG D 172      39.549 103.965 43.131  1.00 13.69           O
ATOM  32528  N   VAL D 173      38.353 105.522 42.069  1.00 11.68           N
ATOM  32529  CA  VAL D 173      38.184 106.314 43.262  1.00 11.68           C
ATOM  32531  CB  VAL D 173      37.507 107.661 42.994  1.00 13.05           C
ATOM  32533  CG1 VAL D 173      37.094 108.331 44.308  1.00 11.39           C
ATOM  32537  CG2 VAL D 173      38.436 108.567 42.156  1.00 12.51           C
ATOM  32541  C   VAL D 173      37.403 105.532 44.303  1.00 11.86           C
ATOM  32542  O   VAL D 173      37.826 105.452 45.452  1.00 12.31           O
ATOM  32544  N   ASN D 174      36.306 104.913 43.883  1.00 10.53           N
ATOM  32545  CA  ASN D 174      35.527 104.100 44.804  1.00 11.23           C
ATOM  32547  CB  ASN D 174      34.331 103.460 44.110  1.00 11.05           C
ATOM  32550  CG  ASN D 174      33.341 102.905 45.110  1.00 12.49           C
ATOM  32551  OD1 ASN D 174      32.644 103.680 45.817  1.00 14.31           O
ATOM  32552  ND2 ASN D 174      33.282 101.564 45.192  1.00 13.99           N
ATOM  32555  C   ASN D 174      36.347 103.052 45.526  1.00 12.05           C
ATOM  32556  O   ASN D 174      36.255 102.924 46.750  1.00 12.99           O
ATOM  32558  N   SER D 175      37.162 102.338 44.753  1.00 12.92           N
ATOM  32559  CA  SER D 175      37.955 101.218 45.247  1.00 14.42           C
ATOM  32561  CB  SER D 175      38.576 100.462 44.078  1.00 14.67           C
ATOM  32564  OG  SER D 175      39.568 101.253 43.413  1.00 17.26           O
ATOM  32566  C   SER D 175      39.023 101.705 46.239  1.00 14.48           C
ATOM  32567  O   SER D 175      39.550 100.891 47.041  1.00 17.30           O
ATOM  32569  N   LEU D 176      39.377 102.988 46.181  1.00 13.75           N
ATOM  32570  CA  LEU D 176      40.415 103.549 47.050  1.00 13.07           C
ATOM  32572  CB  LEU D 176      41.311 104.520 46.254  1.00 12.83           C
ATOM  32575  CG  LEU D 176      42.144 103.860 45.171  1.00 13.85           C
ATOM  32577  CD1 LEU D 176      42.900 104.835 44.315  1.00 15.20           C
ATOM  32581  CD2 LEU D 176      43.143 102.830 45.772  1.00 14.88           C
ATOM  32585  C   LEU D 176      39.822 104.239 48.283  1.00 13.83           C
ATOM  32586  O   LEU D 176      40.571 104.540 49.216  1.00 14.02           O
ATOM  32588  N   THR D 177      38.505 104.463 48.313  1.00 13.66           N
ATOM  32589  CA  THR D 177      37.865 105.062 49.480  1.00 15.48           C
ATOM  32591  CB  THR D 177      36.473 105.649 49.182  1.00 16.81           C
ATOM  32593  OG1 THR D 177      35.571 104.577 48.937  1.00 18.79           O
ATOM  32595  CG2 THR D 177      36.508 106.632 47.992  1.00 15.96           C
ATOM  32599  C   THR D 177      37.689 104.052 50.612  1.00 15.13           C
ATOM  32600  O   THR D 177      37.258 104.419 51.721  1.00 14.72           O
ATOM  32602  N   ARG D 178      37.984 102.787 50.305  1.00 15.00           N
ATOM  32603  CA  ARG D 178      37.747 101.700 51.244  1.00 15.14           C
ATOM  32605  CB  ARG D 178      37.612 100.367 50.475  1.00 14.91           C
ATOM  32608  CG  ARG D 178      36.420 100.340 49.534  1.00 15.49           C
ATOM  32611  CD  ARG D 178      36.449  99.296 48.468  1.00 15.33           C
ATOM  32614  NE  ARG D 178      36.655  97.954 48.994  1.00 15.27           N
ATOM  32616  CZ  ARG D 178      35.724  97.224 49.591  1.00 13.53           C
ATOM  32617  NH1 ARG D 178      34.464  97.697 49.755  1.00 14.07           N
ATOM  32620  NH2 ARG D 178      36.056  96.015 50.041  1.00 16.17           N
ATOM  32623  C   ARG D 178      38.761 101.610 52.379  1.00 14.87           C
ATOM  32624  O   ARG D 178      38.546 100.865 53.357  1.00 16.10           O
ATOM  32626  N   GLY D 179      39.838 102.402 52.304  1.00 15.71           N
ATOM  32627  CA  GLY D 179      40.806 102.505 53.369  1.00 15.56           C
ATOM  32630  C   GLY D 179      41.828 101.374 53.457  1.00 15.55           C
ATOM  32631  O   GLY D 179      42.477 101.184 54.475  1.00 17.29           O
ATOM  32633  N   HIS D 180      41.964 100.620 52.377  1.00 13.81           N
ATOM  32634  CA  HIS D 180      42.857  99.469 52.323  1.00 13.49           C
```

| | | | | | | | | | |
|---|---|---|---|---|---|---|---|---|---|
| ATOM | 32636 | CB | HIS | D | 180 | 42.152 | 98.280 | 51.657 | 1.00 12.65 | C |
| ATOM | 32639 | CG | HIS | D | 180 | 40.865 | 97.883 | 52.294 | 1.00 13.00 | C |
| ATOM | 32640 | ND1 | HIS | D | 180 | 39.750 | 97.541 | 51.557 | 1.00 12.77 | N |
| ATOM | 32642 | CE1 | HIS | D | 180 | 38.778 | 97.217 | 52.384 | 1.00 11.57 | C |
| ATOM | 32644 | NE2 | HIS | D | 180 | 39.204 | 97.371 | 53.626 | 1.00 12.18 | N |
| ATOM | 32646 | CD2 | HIS | D | 180 | 40.510 | 97.785 | 53.593 | 1.00 12.52 | C |
| ATOM | 32648 | C | HIS | D | 180 | 44.130 | 99.714 | 51.525 | 1.00 13.81 | C |
| ATOM | 32649 | O | HIS | D | 180 | 44.957 | 98.790 | 51.374 | 1.00 14.06 | O |
| ATOM | 32651 | N | SER | D | 181 | 44.283 | 100.930 | 50.994 | 1.00 13.62 | N |
| ATOM | 32652 | CA | SER | D | 181 | 45.240 | 101.199 | 49.922 | 1.00 13.88 | C |
| ATOM | 32654 | CB | SER | D | 181 | 44.481 | 101.556 | 48.641 | 1.00 15.83 | C |
| ATOM | 32657 | OG | SER | D | 181 | 43.494 | 100.605 | 48.336 | 1.00 15.07 | O |
| ATOM | 32659 | C | SER | D | 181 | 46.302 | 102.271 | 50.171 | 1.00 12.82 | C |
| ATOM | 32660 | O | SER | D | 181 | 47.308 | 102.334 | 49.420 | 1.00 14.79 | O |
| ATOM | 32662 | N | ALA | D | 182 | 46.104 | 103.120 | 51.187 | 1.00 12.98 | N |
| ATOM | 32663 | CA | ALA | D | 182 | 47.089 | 104.167 | 51.542 | 1.00 13.24 | C |
| ATOM | 32665 | CB | ALA | D | 182 | 48.414 | 103.572 | 52.003 | 1.00 14.45 | C |
| ATOM | 32669 | C | ALA | D | 182 | 47.336 | 105.164 | 50.424 | 1.00 13.30 | C |
| ATOM | 32670 | O | ALA | D | 182 | 48.460 | 105.661 | 50.266 | 1.00 15.14 | O |
| ATOM | 32672 | N | VAL | D | 183 | 46.288 | 105.483 | 49.667 | 1.00 13.57 | N |
| ATOM | 32673 | CA | VAL | D | 183 | 46.321 | 106.575 | 48.718 | 1.00 13.46 | C |
| ATOM | 32675 | CB | VAL | D | 183 | 45.683 | 106.177 | 47.404 | 1.00 14.57 | C |
| ATOM | 32677 | CG1 | VAL | D | 183 | 45.606 | 107.367 | 46.459 | 1.00 15.20 | C |
| ATOM | 32681 | CG2 | VAL | D | 183 | 46.463 | 105.046 | 46.764 | 1.00 16.12 | C |
| ATOM | 32685 | C | VAL | D | 183 | 45.592 | 107.794 | 49.324 | 1.00 13.65 | C |
| ATOM | 32686 | O | VAL | D | 183 | 44.460 | 107.684 | 49.837 | 1.00 11.60 | O |
| ATOM | 32688 | N | ARG | D | 184 | 46.250 | 108.937 | 49.287 | 1.00 12.54 | N |
| ATOM | 32689 | CA | ARG | D | 184 | 45.697 | 110.118 | 49.955 | 1.00 13.67 | C |
| ATOM | 32691 | CB | ARG | D | 184 | 46.693 | 111.281 | 49.945 | 1.00 13.49 | C |
| ATOM | 32694 | CG | ARG | D | 184 | 47.999 | 111.127 | 50.725 | 1.00 14.32 | C |
| ATOM | 32697 | CD | ARG | D | 184 | 48.956 | 112.249 | 50.343 | 1.00 15.65 | C |
| ATOM | 32700 | NE | ARG | D | 184 | 49.450 | 112.051 | 49.003 | 1.00 17.33 | N |
| ATOM | 32702 | CZ | ARG | D | 184 | 49.884 | 112.995 | 48.163 | 1.00 19.59 | C |
| ATOM | 32703 | NH1 | ARG | D | 184 | 49.965 | 114.273 | 48.519 | 1.00 21.93 | N |
| ATOM | 32706 | NH2 | ARG | D | 184 | 50.290 | 112.635 | 46.959 | 1.00 19.01 | N |
| ATOM | 32709 | C | ARG | D | 184 | 44.399 | 110.645 | 49.321 | 1.00 13.62 | C |
| ATOM | 32710 | O | ARG | D | 184 | 44.186 | 110.553 | 48.116 | 1.00 13.83 | O |
| ATOM | 32712 | N | LEU | D | 185 | 43.566 | 111.234 | 50.151 | 1.00 13.35 | N |
| ATOM | 32713 | CA | LEU | D | 185 | 42.351 | 111.848 | 49.688 | 1.00 14.83 | C |
| ATOM | 32715 | CB | LEU | D | 185 | 41.645 | 112.509 | 50.870 | 1.00 15.03 | C |
| ATOM | 32718 | CG | LEU | D | 185 | 40.315 | 113.187 | 50.532 | 1.00 17.62 | C |
| ATOM | 32720 | CD1 | LEU | D | 185 | 39.326 | 112.240 | 49.847 | 1.00 19.82 | C |
| ATOM | 32724 | CD2 | LEU | D | 185 | 39.728 | 113.757 | 51.781 | 1.00 16.89 | C |
| ATOM | 32728 | C | LEU | D | 185 | 42.619 | 112.867 | 48.569 | 1.00 14.83 | C |
| ATOM | 32729 | O | LEU | D | 185 | 41.872 | 112.950 | 47.573 | 1.00 14.86 | O |
| ATOM | 32731 | N | VAL | D | 186 | 43.684 | 113.632 | 48.693 | 1.00 14.27 | N |
| ATOM | 32732 | CA | VAL | D | 186 | 43.966 | 114.635 | 47.643 | 1.00 14.04 | C |
| ATOM | 32734 | CB | VAL | D | 186 | 45.160 | 115.575 | 48.004 | 1.00 14.31 | C |
| ATOM | 32736 | CG1 | VAL | D | 186 | 46.477 | 114.809 | 48.158 | 1.00 13.87 | C |
| ATOM | 32740 | CG2 | VAL | D | 186 | 45.303 | 116.673 | 46.962 | 1.00 17.25 | C |
| ATOM | 32744 | C | VAL | D | 186 | 44.149 | 113.999 | 46.245 | 1.00 13.05 | C |
| ATOM | 32745 | O | VAL | D | 186 | 43.770 | 114.615 | 45.209 | 1.00 13.36 | O |
| ATOM | 32747 | N | VAL | D | 187 | 44.650 | 112.762 | 46.217 | 1.00 13.08 | N |
| ATOM | 32748 | CA | VAL | D | 187 | 44.826 | 112.033 | 44.956 | 1.00 12.14 | C |
| ATOM | 32750 | CB | VAL | D | 187 | 45.831 | 110.861 | 45.155 | 1.00 11.77 | C |
| ATOM | 32752 | CG1 | VAL | D | 187 | 45.846 | 109.970 | 43.957 | 1.00 14.53 | C |
| ATOM | 32756 | CG2 | VAL | D | 187 | 47.223 | 111.428 | 45.477 | 1.00 13.46 | C |

| | | | | | | | | | |
|---|---|---|---|---|---|---|---|---|---|
| ATOM | 32760 | C | VAL | D | 187 | 43.481 | 111.571 | 44.414 | 1.00 13.06 | C |
| ATOM | 32761 | O | VAL | D | 187 | 43.215 | 111.674 | 43.210 | 1.00 12.63 | O |
| ATOM | 32763 | N | LEU | D | 188 | 42.620 | 111.073 | 45.302 | 1.00 12.70 | N |
| ATOM | 32764 | CA | LEU | D | 188 | 41.267 | 110.707 | 44.890 | 1.00 13.37 | C |
| ATOM | 32766 | CB | LEU | D | 188 | 40.477 | 110.096 | 46.036 | 1.00 14.55 | C |
| ATOM | 32769 | CG | LEU | D | 188 | 41.098 | 108.859 | 46.676 | 1.00 15.08 | C |
| ATOM | 32771 | CD1 | LEU | D | 188 | 40.087 | 108.365 | 47.650 | 1.00 15.24 | C |
| ATOM | 32775 | CD2 | LEU | D | 188 | 41.512 | 107.862 | 45.665 | 1.00 19.70 | C |
| ATOM | 32779 | C | LEU | D | 188 | 40.517 | 111.939 | 44.367 | 1.00 13.13 | C |
| ATOM | 32780 | O | LEU | D | 188 | 39.808 | 111.872 | 43.351 | 1.00 12.46 | O |
| ATOM | 32782 | N | GLU | D | 189 | 40.692 | 113.077 | 45.029 | 1.00 13.18 | N |
| ATOM | 32783 | CA | GLU | D | 189 | 40.064 | 114.329 | 44.582 | 1.00 14.92 | C |
| ATOM | 32785 | CB | GLU | D | 189 | 40.219 | 115.383 | 45.661 | 1.00 15.42 | C |
| ATOM | 32788 | CG | GLU | D | 189 | 39.527 | 115.031 | 46.974 | 1.00 18.19 | C |
| ATOM | 32791 | CD | GLU | D | 189 | 39.775 | 116.087 | 48.043 | 1.00 18.23 | C |
| ATOM | 32792 | OE1 | GLU | D | 189 | 40.858 | 116.769 | 48.033 | 1.00 22.50 | O |
| ATOM | 32793 | OE2 | GLU | D | 189 | 38.904 | 116.214 | 48.943 | 1.00 22.42 | O |
| ATOM | 32794 | C | GLU | D | 189 | 40.627 | 114.840 | 43.262 | 1.00 14.20 | C |
| ATOM | 32795 | O | GLU | D | 189 | 39.940 | 115.477 | 42.482 | 1.00 14.33 | O |
| ATOM | 32797 | N | ALA | D | 190 | 41.873 | 114.514 | 42.969 | 1.00 13.65 | N |
| ATOM | 32798 | CA | ALA | D | 190 | 42.404 | 114.833 | 41.634 | 1.00 14.04 | C |
| ATOM | 32800 | CB | ALA | D | 190 | 43.911 | 114.523 | 41.546 | 1.00 13.85 | C |
| ATOM | 32804 | C | ALA | D | 190 | 41.619 | 114.118 | 40.521 | 1.00 12.19 | C |
| ATOM | 32805 | O | ALA | D | 190 | 41.306 | 114.689 | 39.445 | 1.00 12.33 | O |
| ATOM | 32807 | N | LEU | D | 191 | 41.240 | 112.860 | 40.776 | 1.00 12.15 | N |
| ATOM | 32808 | CA | LEU | D | 191 | 40.437 | 112.079 | 39.830 | 1.00 11.70 | C |
| ATOM | 32810 | CB | LEU | D | 191 | 40.429 | 110.607 | 40.229 | 1.00 12.17 | C |
| ATOM | 32813 | CG | LEU | D | 191 | 41.797 | 109.914 | 40.126 | 1.00 13.54 | C |
| ATOM | 32815 | CD1 | LEU | D | 191 | 41.775 | 108.563 | 40.865 | 1.00 14.77 | C |
| ATOM | 32819 | CD2 | LEU | D | 191 | 42.178 | 109.742 | 38.681 | 1.00 16.12 | C |
| ATOM | 32823 | C | LEU | D | 191 | 38.990 | 112.622 | 39.753 | 1.00 12.06 | C |
| ATOM | 32824 | O | LEU | D | 191 | 38.422 | 112.736 | 38.649 | 1.00 12.26 | O |
| ATOM | 32826 | N | THR | D | 192 | 38.357 | 112.890 | 40.905 | 1.00 12.54 | N |
| ATOM | 32827 | CA | THR | D | 192 | 36.987 | 113.410 | 40.852 | 1.00 11.83 | C |
| ATOM | 32829 | CB | THR | D | 192 | 36.271 | 113.419 | 42.246 | 1.00 12.79 | C |
| ATOM | 32831 | OG1 | THR | D | 192 | 36.979 | 114.241 | 43.196 | 1.00 13.35 | O |
| ATOM | 32833 | CG2 | THR | D | 192 | 36.168 | 111.991 | 42.733 | 1.00 13.41 | C |
| ATOM | 32837 | C | THR | D | 192 | 36.973 | 114.784 | 40.182 | 1.00 12.79 | C |
| ATOM | 32838 | O | THR | D | 192 | 36.040 | 115.108 | 39.442 | 1.00 12.90 | O |
| ATOM | 32840 | N | ASN | D | 193 | 38.014 | 115.580 | 40.417 | 1.00 12.50 | N |
| ATOM | 32841 | CA | ASN | D | 193 | 38.126 | 116.874 | 39.743 | 1.00 12.76 | C |
| ATOM | 32843 | CB | ASN | D | 193 | 39.277 | 117.682 | 40.283 | 1.00 11.93 | C |
| ATOM | 32846 | CG | ASN | D | 193 | 38.936 | 118.393 | 41.590 | 1.00 13.09 | C |
| ATOM | 32847 | OD1 | ASN | D | 193 | 37.741 | 118.633 | 41.888 | 1.00 12.45 | O |
| ATOM | 32848 | ND2 | ASN | D | 193 | 39.962 | 118.702 | 42.392 | 1.00 14.05 | N |
| ATOM | 32851 | C | ASN | D | 193 | 38.241 | 116.692 | 38.222 | 1.00 12.20 | C |
| ATOM | 32852 | O | ASN | D | 193 | 37.605 | 117.423 | 37.462 | 1.00 11.89 | O |
| ATOM | 32854 | N | PHE | D | 194 | 39.005 | 115.691 | 37.756 | 1.00 11.40 | N |
| ATOM | 32855 | CA | PHE | D | 194 | 39.042 | 115.432 | 36.294 | 1.00 12.10 | C |
| ATOM | 32857 | CB | PHE | D | 194 | 40.003 | 114.318 | 35.942 | 1.00 12.80 | C |
| ATOM | 32860 | CG | PHE | D | 194 | 41.407 | 114.770 | 35.690 | 1.00 12.58 | C |
| ATOM | 32861 | CD1 | PHE | D | 194 | 41.966 | 115.841 | 36.337 | 1.00 12.78 | C |
| ATOM | 32863 | CE1 | PHE | D | 194 | 43.257 | 116.206 | 36.081 | 1.00 11.92 | C |
| ATOM | 32865 | CZ | PHE | D | 194 | 44.053 | 115.486 | 35.206 | 1.00 12.77 | C |
| ATOM | 32867 | CE2 | PHE | D | 194 | 43.525 | 114.459 | 34.567 | 1.00 13.38 | C |
| ATOM | 32869 | CD2 | PHE | D | 194 | 42.205 | 114.047 | 34.837 | 1.00 15.57 | C |
| ATOM | 32871 | C | PHE | D | 194 | 37.653 | 115.042 | 35.747 | 1.00 12.52 | C |

| ATOM | 32872 | O | PHE | D | 194 | 37.174 | 115.565 | 34.730 | 1.00 | 12.65 | O |
|---|---|---|---|---|---|---|---|---|---|---|---|
| ATOM | 32874 | N | LEU | D | 195 | 36.956 | 114.195 | 36.492 | 1.00 | 12.24 | N |
| ATOM | 32875 | CA | LEU | D | 195 | 35.606 | 113.786 | 36.131 | 1.00 | 12.11 | C |
| ATOM | 32877 | CB | LEU | D | 195 | 35.074 | 112.795 | 37.151 | 1.00 | 11.71 | C |
| ATOM | 32880 | CG | LEU | D | 195 | 35.616 | 111.347 | 37.029 | 1.00 | 12.92 | C |
| ATOM | 32882 | CD1 | LEU | D | 195 | 35.315 | 110.474 | 38.269 | 1.00 | 12.80 | C |
| ATOM | 32886 | CD2 | LEU | D | 195 | 34.989 | 110.697 | 35.793 | 1.00 | 14.30 | C |
| ATOM | 32890 | C | LEU | D | 195 | 34.695 | 114.996 | 36.045 | 1.00 | 10.98 | C |
| ATOM | 32891 | O | LEU | D | 195 | 33.960 | 115.179 | 35.072 | 1.00 | 12.39 | O |
| ATOM | 32893 | N | ASN | D | 196 | 34.767 | 115.825 | 37.077 | 1.00 | 11.28 | N |
| ATOM | 32894 | CA | ASN | D | 196 | 33.785 | 116.909 | 37.218 | 1.00 | 10.59 | C |
| ATOM | 32896 | CB | ASN | D | 196 | 33.691 | 117.317 | 38.657 | 1.00 | 11.02 | C |
| ATOM | 32899 | CG | ASN | D | 196 | 33.080 | 116.246 | 39.527 | 1.00 | 10.14 | C |
| ATOM | 32900 | OD1 | ASN | D | 196 | 32.309 | 115.387 | 39.049 | 1.00 | 12.75 | O |
| ATOM | 32901 | ND2 | ASN | D | 196 | 33.367 | 116.346 | 40.839 | 1.00 | 12.97 | N |
| ATOM | 32904 | C | ASN | D | 196 | 34.076 | 118.097 | 36.295 | 1.00 | 12.03 | C |
| ATOM | 32905 | O | ASN | D | 196 | 33.195 | 118.899 | 36.035 | 1.00 | 13.92 | O |
| ATOM | 32907 | N | HIS | D | 197 | 35.281 | 118.178 | 35.772 | 1.00 | 10.66 | N |
| ATOM | 32908 | CA | HIS | D | 197 | 35.616 | 119.159 | 34.740 | 1.00 | 12.52 | C |
| ATOM | 32910 | CB | HIS | D | 197 | 36.943 | 119.826 | 35.083 | 1.00 | 12.63 | C |
| ATOM | 32913 | CG | HIS | D | 197 | 36.862 | 120.682 | 36.311 | 1.00 | 13.91 | C |
| ATOM | 32914 | ND1 | HIS | D | 197 | 36.090 | 121.824 | 36.361 | 1.00 | 18.02 | N |
| ATOM | 32916 | CE1 | HIS | D | 197 | 36.212 | 122.381 | 37.556 | 1.00 | 16.70 | C |
| ATOM | 32918 | NE2 | HIS | D | 197 | 36.991 | 121.612 | 38.295 | 1.00 | 17.96 | N |
| ATOM | 32920 | CD2 | HIS | D | 197 | 37.390 | 120.532 | 37.544 | 1.00 | 16.81 | C |
| ATOM | 32922 | C | HIS | D | 197 | 35.674 | 118.599 | 33.321 | 1.00 | 12.75 | C |
| ATOM | 32923 | O | HIS | D | 197 | 36.094 | 119.319 | 32.402 | 1.00 | 14.26 | O |
| ATOM | 32925 | N | GLY | D | 198 | 35.286 | 117.327 | 33.163 | 1.00 | 12.91 | N |
| ATOM | 32926 | CA | GLY | D | 198 | 35.260 | 116.672 | 31.879 | 1.00 | 13.76 | C |
| ATOM | 32929 | C | GLY | D | 198 | 36.636 | 116.565 | 31.230 | 1.00 | 14.16 | C |
| ATOM | 32930 | O | GLY | D | 198 | 36.755 | 116.710 | 30.004 | 1.00 | 15.16 | O |
| ATOM | 32932 | N | ILE | D | 199 | 37.660 | 116.406 | 32.075 | 1.00 | 12.97 | N |
| ATOM | 32933 | CA | ILE | D | 199 | 39.032 | 116.121 | 31.644 | 1.00 | 12.96 | C |
| ATOM | 32935 | CB | ILE | D | 199 | 40.102 | 116.732 | 32.603 | 1.00 | 13.85 | C |
| ATOM | 32937 | CG1 | ILE | D | 199 | 39.879 | 118.222 | 32.744 | 1.00 | 13.47 | C |
| ATOM | 32940 | CD1 | ILE | D | 199 | 40.783 | 118.831 | 33.701 | 1.00 | 15.95 | C |
| ATOM | 32944 | CG2 | ILE | D | 199 | 41.497 | 116.412 | 32.078 | 1.00 | 15.52 | C |
| ATOM | 32948 | C | ILE | D | 199 | 39.211 | 114.607 | 31.587 | 1.00 | 13.68 | C |
| ATOM | 32949 | O | ILE | D | 199 | 39.144 | 113.916 | 32.601 | 1.00 | 13.50 | O |
| ATOM | 32951 | N | THR | D | 200 | 39.413 | 114.063 | 30.404 | 1.00 | 12.59 | N |
| ATOM | 32952 | CA | THR | D | 200 | 39.480 | 112.589 | 30.226 | 1.00 | 12.06 | C |
| ATOM | 32954 | CB | THR | D | 200 | 38.353 | 112.047 | 29.312 | 1.00 | 13.30 | C |
| ATOM | 32956 | OG1 | THR | D | 200 | 37.079 | 112.542 | 29.772 | 1.00 | 14.28 | O |
| ATOM | 32958 | CG2 | THR | D | 200 | 38.327 | 110.568 | 29.309 | 1.00 | 13.60 | C |
| ATOM | 32962 | C | THR | D | 200 | 40.830 | 112.207 | 29.626 | 1.00 | 12.14 | C |
| ATOM | 32963 | O | THR | D | 200 | 41.109 | 112.582 | 28.470 | 1.00 | 12.77 | O |
| ATOM | 32965 | N | PRO | D | 201 | 41.658 | 111.482 | 30.386 | 1.00 | 12.82 | N |
| ATOM | 32966 | CA | PRO | D | 201 | 42.920 | 111.021 | 29.792 | 1.00 | 11.39 | C |
| ATOM | 32968 | CB | PRO | D | 201 | 43.541 | 110.182 | 30.898 | 1.00 | 11.32 | C |
| ATOM | 32971 | CG | PRO | D | 201 | 42.948 | 110.795 | 32.186 | 1.00 | 12.93 | C |
| ATOM | 32974 | CD | PRO | D | 201 | 41.561 | 111.130 | 31.810 | 1.00 | 11.46 | C |
| ATOM | 32977 | C | PRO | D | 201 | 42.795 | 110.268 | 28.474 | 1.00 | 11.45 | C |
| ATOM | 32978 | O | PRO | D | 201 | 41.838 | 109.532 | 28.272 | 1.00 | 13.02 | O |
| ATOM | 32979 | N | ILE | D | 202 | 43.736 | 110.556 | 27.569 | 1.00 | 12.20 | N |
| ATOM | 32980 | CA | ILE | D | 202 | 43.874 | 109.816 | 26.315 | 1.00 | 12.99 | C |
| ATOM | 32982 | CB | ILE | D | 202 | 44.479 | 110.659 | 25.211 | 1.00 | 12.73 | C |
| ATOM | 32984 | CG1 | ILE | D | 202 | 43.514 | 111.786 | 24.771 | 1.00 | 12.71 | C |

| | | | | | | | | | |
|---|---|---|---|---|---|---|---|---|---|
| ATOM | 32987 | CD1 | ILE | D | 202 | 42.204 | 111.388 | 24.288 | 1.00 17.28 | C |
| ATOM | 32991 | CG2 | ILE | D | 202 | 44.837 | 109.837 | 24.009 | 1.00 10.88 | C |
| ATOM | 32995 | C | ILE | D | 202 | 44.739 | 108.600 | 26.660 | 1.00 13.13 | C |
| ATOM | 32996 | O | ILE | D | 202 | 45.895 | 108.754 | 27.055 | 1.00 13.04 | O |
| ATOM | 32998 | N | VAL | D | 203 | 44.181 | 107.413 | 26.470 | 1.00 14.15 | N |
| ATOM | 32999 | CA | VAL | D | 203 | 44.762 | 106.170 | 26.966 | 1.00 13.50 | C |
| ATOM | 33001 | CB | VAL | D | 203 | 43.905 | 105.572 | 28.108 | 1.00 13.78 | C |
| ATOM | 33003 | CG1 | VAL | D | 203 | 44.470 | 104.246 | 28.661 | 1.00 16.87 | C |
| ATOM | 33007 | CG2 | VAL | D | 203 | 43.728 | 106.644 | 29.245 | 1.00 14.17 | C |
| ATOM | 33011 | C | VAL | D | 203 | 44.807 | 105.203 | 25.805 | 1.00 13.51 | C |
| ATOM | 33012 | O | VAL | D | 203 | 43.833 | 105.079 | 25.043 | 1.00 12.37 | O |
| ATOM | 33014 | N | PRO | D | 204 | 45.939 | 104.552 | 25.606 | 1.00 12.30 | N |
| ATOM | 33015 | CA | PRO | D | 204 | 45.944 | 103.578 | 24.494 | 1.00 12.43 | C |
| ATOM | 33017 | CB | PRO | D | 204 | 47.332 | 102.947 | 24.596 | 1.00 12.41 | C |
| ATOM | 33020 | CG | PRO | D | 204 | 48.161 | 104.005 | 25.275 | 1.00 12.08 | C |
| ATOM | 33023 | CD | PRO | D | 204 | 47.224 | 104.570 | 26.315 | 1.00 13.69 | C |
| ATOM | 33026 | C | PRO | D | 204 | 44.839 | 102.501 | 24.649 | 1.00 11.51 | C |
| ATOM | 33027 | O | PRO | D | 204 | 44.566 | 102.016 | 25.747 | 1.00 12.46 | O |
| ATOM | 33028 | N | LEU | D | 205 | 44.301 | 102.051 | 23.520 | 1.00 11.68 | N |
| ATOM | 33029 | CA | LEU | D | 205 | 43.313 | 100.958 | 23.467 | 1.00 11.95 | C |
| ATOM | 33031 | CB | LEU | D | 205 | 42.843 | 100.830 | 22.023 | 1.00 12.66 | C |
| ATOM | 33034 | CG | LEU | D | 205 | 41.778 | 99.768 | 21.812 | 1.00 13.39 | C |
| ATOM | 33036 | CD1 | LEU | D | 205 | 40.478 | 100.092 | 22.582 | 1.00 15.01 | C |
| ATOM | 33040 | CD2 | LEU | D | 205 | 41.514 | 99.632 | 20.342 | 1.00 12.76 | C |
| ATOM | 33044 | C | LEU | D | 205 | 43.862 | 99.591 | 23.942 | 1.00 10.67 | C |
| ATOM | 33045 | O | LEU | D | 205 | 43.199 | 98.845 | 24.652 | 1.00 12.04 | O |
| ATOM | 33047 | N | ARG | D | 206 | 45.090 | 99.317 | 23.526 | 1.00 12.22 | N |
| ATOM | 33048 | CA | ARG | D | 206 | 45.734 | 98.051 | 23.726 | 1.00 12.34 | C |
| ATOM | 33050 | CB | ARG | D | 206 | 46.057 | 97.417 | 22.354 | 1.00 12.76 | C |
| ATOM | 33053 | CG | ARG | D | 206 | 44.823 | 97.148 | 21.475 | 1.00 13.81 | C |
| ATOM | 33056 | CD | ARG | D | 206 | 45.216 | 96.366 | 20.180 | 1.00 14.59 | C |
| ATOM | 33059 | NE | ARG | D | 206 | 44.094 | 95.986 | 19.318 | 1.00 13.36 | N |
| ATOM | 33061 | CZ | ARG | D | 206 | 43.726 | 96.619 | 18.223 | 1.00 18.10 | C |
| ATOM | 33062 | NH1 | ARG | D | 206 | 44.299 | 97.779 | 17.865 | 1.00 19.83 | N |
| ATOM | 33065 | NH2 | ARG | D | 206 | 42.779 | 96.087 | 17.451 | 1.00 16.75 | N |
| ATOM | 33068 | C | ARG | D | 206 | 47.032 | 98.123 | 24.528 | 1.00 11.77 | C |
| ATOM | 33069 | O | ARG | D | 206 | 47.695 | 99.158 | 24.602 | 1.00 12.92 | O |
| ATOM | 33071 | N | GLY | D | 207 | 47.361 | 96.979 | 25.142 | 1.00 12.47 | N |
| ATOM | 33072 | CA | GLY | D | 207 | 48.618 | 96.849 | 25.891 | 1.00 12.74 | C |
| ATOM | 33075 | C | GLY | D | 207 | 48.455 | 96.131 | 27.197 | 1.00 13.11 | C |
| ATOM | 33076 | O | GLY | D | 207 | 49.423 | 95.574 | 27.688 | 1.00 16.28 | O |
| ATOM | 33078 | N | THR | D | 208 | 47.241 | 96.117 | 27.727 | 1.00 12.73 | N |
| ATOM | 33079 | CA | THR | D | 208 | 47.033 | 95.428 | 29.027 | 1.00 11.42 | C |
| ATOM | 33081 | CB | THR | D | 208 | 46.076 | 96.212 | 29.982 | 1.00 12.45 | C |
| ATOM | 33083 | OG1 | THR | D | 208 | 46.107 | 95.603 | 31.281 | 1.00 13.56 | O |
| ATOM | 33085 | CG2 | THR | D | 208 | 44.660 | 96.237 | 29.442 | 1.00 14.13 | C |
| ATOM | 33089 | C | THR | D | 208 | 46.571 | 93.995 | 28.840 | 1.00 11.65 | C |
| ATOM | 33090 | O | THR | D | 208 | 45.830 | 93.669 | 27.891 | 1.00 12.37 | O |
| ATOM | 33092 | N | ILE | D | 209 | 47.042 | 93.189 | 29.777 | 1.00 10.68 | N |
| ATOM | 33093 | CA | ILE | D | 209 | 46.586 | 91.816 | 29.972 | 1.00 11.58 | C |
| ATOM | 33095 | CB | ILE | D | 209 | 47.768 | 90.809 | 30.111 | 1.00 13.11 | C |
| ATOM | 33097 | CG1 | ILE | D | 209 | 48.642 | 91.122 | 31.318 | 1.00 13.29 | C |
| ATOM | 33100 | CD1 | ILE | D | 209 | 49.848 | 90.202 | 31.419 | 1.00 12.62 | C |
| ATOM | 33104 | CG2 | ILE | D | 209 | 48.578 | 90.774 | 28.854 | 1.00 13.99 | C |
| ATOM | 33108 | C | ILE | D | 209 | 45.599 | 91.713 | 31.174 | 1.00 11.44 | C |
| ATOM | 33109 | O | ILE | D | 209 | 45.167 | 90.604 | 31.479 | 1.00 13.20 | O |
| ATOM | 33111 | N | SER | D | 210 | 45.336 | 92.831 | 31.874 | 1.00 11.42 | N |

| | | | | | | | | | |
|---|---|---|---|---|---|---|---|---|---|
| ATOM | 33112 | CA | SER | D | 210 | 44.327 | 92.862 | 32.908 | 1.00 12.17 | C |
| ATOM | 33114 | CB | SER | D | 210 | 42.937 | 92.623 | 32.326 | 1.00 12.35 | C |
| ATOM | 33117 | OG | SER | D | 210 | 42.630 | 93.566 | 31.292 | 1.00 11.65 | O |
| ATOM | 33119 | C | SER | D | 210 | 44.673 | 91.961 | 34.068 | 1.00 11.12 | C |
| ATOM | 33120 | O | SER | D | 210 | 43.806 | 91.277 | 34.621 | 1.00 12.19 | O |
| ATOM | 33122 | N | ALA | D | 211 | 45.944 | 91.965 | 34.456 | 1.00 10.13 | N |
| ATOM | 33123 | CA | ALA | D | 211 | 46.400 | 91.347 | 35.725 | 1.00 11.09 | C |
| ATOM | 33125 | CB | ALA | D | 211 | 47.190 | 90.092 | 35.542 | 1.00 11.67 | C |
| ATOM | 33129 | C | ALA | D | 211 | 47.148 | 92.365 | 36.550 | 1.00 12.11 | C |
| ATOM | 33132 | N | SER | D | 212 | 48.340 | 92.302 | 37.121 | 1.00 13.68 | N |
| ATOM | 33133 | CA | SER | D | 212 | 48.442 | 93.382 | 38.095 | 1.00 15.71 | C |
| ATOM | 33135 | CB | SER | D | 212 | 49.799 | 93.861 | 38.530 | 1.00 15.70 | C |
| ATOM | 33139 | C | SER | D | 212 | 47.346 | 94.346 | 37.706 | 1.00 14.20 | C |
| ATOM | 33140 | O | SER | D | 212 | 47.152 | 95.492 | 38.164 | 1.00 14.76 | O |
| ATOM | 33142 | N | GLY | D | 213 | 46.470 | 93.751 | 36.902 | 1.00 12.73 | N |
| ATOM | 33143 | CA | GLY | D | 213 | 45.270 | 94.331 | 36.404 | 1.00 12.27 | C |
| ATOM | 33146 | C | GLY | D | 213 | 45.603 | 95.177 | 35.205 | 1.00 12.59 | C |
| ATOM | 33147 | O | GLY | D | 213 | 46.517 | 94.874 | 34.413 | 1.00 12.48 | O |
| ATOM | 33149 | N | ASP | D | 214 | 44.832 | 96.214 | 35.069 | 1.00 12.35 | N |
| ATOM | 33150 | CA | ASP | D | 214 | 44.854 | 97.106 | 33.909 | 1.00 11.82 | C |
| ATOM | 33152 | CB | ASP | D | 214 | 43.451 | 97.768 | 33.831 | 1.00 13.15 | C |
| ATOM | 33155 | CG | ASP | D | 214 | 42.323 | 96.752 | 33.632 | 1.00 12.93 | C |
| ATOM | 33156 | OD1 | ASP | D | 214 | 42.487 | 95.823 | 32.814 | 1.00 12.90 | O |
| ATOM | 33157 | OD2 | ASP | D | 214 | 41.280 | 96.929 | 34.266 | 1.00 16.36 | O |
| ATOM | 33158 | C | ASP | D | 214 | 45.999 | 98.149 | 34.031 | 1.00 13.01 | C |
| ATOM | 33159 | O | ASP | D | 214 | 45.792 | 99.381 | 33.944 | 1.00 13.45 | O |
| ATOM | 33161 | N | LEU | D | 215 | 47.218 | 97.641 | 34.209 | 1.00 12.98 | N |
| ATOM | 33162 | CA | LEU | D | 215 | 48.385 | 98.450 | 34.568 | 1.00 13.40 | C |
| ATOM | 33164 | CB | LEU | D | 215 | 49.647 | 97.562 | 34.572 | 1.00 14.65 | C |
| ATOM | 33167 | CG | LEU | D | 215 | 49.710 | 96.555 | 35.718 | 1.00 13.96 | C |
| ATOM | 33169 | CD1 | LEU | D | 215 | 50.865 | 95.546 | 35.582 | 1.00 14.26 | C |
| ATOM | 33173 | CD2 | LEU | D | 215 | 49.861 | 97.205 | 37.050 | 1.00 14.25 | C |
| ATOM | 33177 | C | LEU | D | 215 | 48.607 | 99.584 | 33.644 | 1.00 13.18 | C |
| ATOM | 33178 | O | LEU | D | 215 | 48.674 | 100.748 | 34.068 | 1.00 11.79 | O |
| ATOM | 33180 | N | SER | D | 216 | 48.737 | 99.271 | 32.367 | 1.00 13.13 | N |
| ATOM | 33181 | CA | SER | D | 216 | 49.123 | 100.323 | 31.428 | 1.00 12.06 | C |
| ATOM | 33183 | CB | SER | D | 216 | 49.460 | 99.780 | 30.048 | 1.00 12.63 | C |
| ATOM | 33186 | OG | SER | D | 216 | 50.020 | 100.826 | 29.237 | 1.00 15.98 | O |
| ATOM | 33188 | C | SER | D | 216 | 48.084 | 101.437 | 31.376 | 1.00 12.67 | C |
| ATOM | 33189 | O | SER | D | 216 | 48.407 | 102.573 | 31.623 | 1.00 12.64 | O |
| ATOM | 33191 | N | PRO | D | 217 | 46.821 | 101.094 | 31.098 | 1.00 13.02 | N |
| ATOM | 33192 | CA | PRO | D | 217 | 45.865 | 102.203 | 31.004 | 1.00 12.59 | C |
| ATOM | 33194 | CB | PRO | D | 217 | 44.563 | 101.514 | 30.554 | 1.00 13.79 | C |
| ATOM | 33197 | CG | PRO | D | 217 | 44.751 | 100.076 | 30.883 | 1.00 14.58 | C |
| ATOM | 33200 | CD | PRO | D | 217 | 46.213 | 99.798 | 30.761 | 1.00 12.68 | C |
| ATOM | 33203 | C | PRO | D | 217 | 45.684 | 102.982 | 32.328 | 1.00 12.39 | C |
| ATOM | 33204 | O | PRO | D | 217 | 45.529 | 104.208 | 32.299 | 1.00 14.27 | O |
| ATOM | 33205 | N | LEU | D | 218 | 45.747 | 102.294 | 33.471 | 1.00 12.91 | N |
| ATOM | 33206 | CA | LEU | D | 218 | 45.696 | 102.989 | 34.759 | 1.00 12.69 | C |
| ATOM | 33208 | CB | LEU | D | 218 | 45.538 | 101.986 | 35.881 | 1.00 12.87 | C |
| ATOM | 33211 | CG | LEU | D | 218 | 44.132 | 101.340 | 35.981 | 1.00 12.34 | C |
| ATOM | 33213 | CD1 | LEU | D | 218 | 44.155 | 100.242 | 37.002 | 1.00 14.68 | C |
| ATOM | 33217 | CD2 | LEU | D | 218 | 43.065 | 102.384 | 36.356 | 1.00 14.70 | C |
| ATOM | 33221 | C | LEU | D | 218 | 46.891 | 103.907 | 34.957 | 1.00 11.77 | C |
| ATOM | 33222 | O | LEU | D | 218 | 46.785 | 104.948 | 35.589 | 1.00 13.54 | O |
| ATOM | 33224 | N | SER | D | 219 | 48.051 | 103.532 | 34.414 | 1.00 12.85 | N |
| ATOM | 33225 | CA | SER | D | 219 | 49.246 | 104.349 | 34.522 | 1.00 13.33 | C |

| ATOM | 33227 | CB  | SER | D | 219 | 50.480 | 103.593 | 34.039 | 1.00 | 14.04 | C |
| ATOM | 33230 | OG  | SER | D | 219 | 50.788 | 102.525 | 34.916 | 1.00 | 19.34 | O |
| ATOM | 33232 | C   | SER | D | 219 | 49.090 | 105.651 | 33.714 | 1.00 | 12.48 | C |
| ATOM | 33233 | O   | SER | D | 219 | 49.615 | 106.712 | 34.078 | 1.00 | 12.64 | O |
| ATOM | 33235 | N   | TYR | D | 220 | 48.389 | 105.580 | 32.586 | 1.00 | 12.85 | N |
| ATOM | 33236 | CA  | TYR | D | 220 | 48.040 | 106.816 | 31.837 | 1.00 | 11.67 | C |
| ATOM | 33238 | CB  | TYR | D | 220 | 47.370 | 106.507 | 30.482 | 1.00 | 12.51 | C |
| ATOM | 33241 | CG  | TYR | D | 220 | 48.395 | 106.060 | 29.425 | 1.00 | 12.32 | C |
| ATOM | 33242 | CD1 | TYR | D | 220 | 48.891 | 104.780 | 29.381 | 1.00 | 12.03 | C |
| ATOM | 33244 | CE1 | TYR | D | 220 | 49.878 | 104.419 | 28.481 | 1.00 | 11.93 | C |
| ATOM | 33246 | CZ  | TYR | D | 220 | 50.415 | 105.334 | 27.596 | 1.00 | 12.54 | C |
| ATOM | 33247 | OH  | TYR | D | 220 | 51.408 | 104.980 | 26.710 | 1.00 | 13.15 | O |
| ATOM | 33249 | CE2 | TYR | D | 220 | 49.948 | 106.650 | 27.615 | 1.00 | 12.72 | C |
| ATOM | 33251 | CD2 | TYR | D | 220 | 48.963 | 106.996 | 28.548 | 1.00 | 12.97 | C |
| ATOM | 33253 | C   | TYR | D | 220 | 47.185 | 107.770 | 32.655 | 1.00 | 12.43 | C |
| ATOM | 33254 | O   | TYR | D | 220 | 47.416 | 108.959 | 32.629 | 1.00 | 13.05 | O |
| ATOM | 33256 | N   | ILE | D | 221 | 46.225 | 107.229 | 33.374 | 1.00 | 12.57 | N |
| ATOM | 33257 | CA  | ILE | D | 221 | 45.362 | 108.013 | 34.247 | 1.00 | 11.78 | C |
| ATOM | 33259 | CB  | ILE | D | 221 | 44.178 | 107.179 | 34.792 | 1.00 | 12.03 | C |
| ATOM | 33261 | CG1 | ILE | D | 221 | 43.217 | 106.835 | 33.614 | 1.00 | 12.47 | C |
| ATOM | 33264 | CD1 | ILE | D | 221 | 42.193 | 105.731 | 33.877 | 1.00 | 12.92 | C |
| ATOM | 33268 | CG2 | ILE | D | 221 | 43.465 | 107.912 | 35.896 | 1.00 | 13.08 | C |
| ATOM | 33272 | C   | ILE | D | 221 | 46.200 | 108.641 | 35.357 | 1.00 | 12.34 | C |
| ATOM | 33273 | O   | ILE | D | 221 | 46.131 | 109.828 | 35.623 | 1.00 | 12.53 | O |
| ATOM | 33275 | N   | ALA | D | 222 | 47.035 | 107.827 | 35.995 | 1.00 | 12.97 | N |
| ATOM | 33276 | CA  | ALA | D | 222 | 47.954 | 108.328 | 37.031 | 1.00 | 12.17 | C |
| ATOM | 33278 | CB  | ALA | D | 222 | 48.715 | 107.140 | 37.631 | 1.00 | 11.51 | C |
| ATOM | 33282 | C   | ALA | D | 222 | 48.939 | 109.399 | 36.547 | 1.00 | 11.30 | C |
| ATOM | 33283 | O   | ALA | D | 222 | 49.178 | 110.455 | 37.227 | 1.00 | 12.19 | O |
| ATOM | 33285 | N   | ALA | D | 223 | 49.464 | 109.217 | 35.347 | 1.00 | 11.19 | N |
| ATOM | 33286 | CA  | ALA | D | 223 | 50.401 | 110.150 | 34.770 | 1.00 | 10.60 | C |
| ATOM | 33288 | CB  | ALA | D | 223 | 50.955 | 109.592 | 33.518 | 1.00 | 12.99 | C |
| ATOM | 33292 | C   | ALA | D | 223 | 49.710 | 111.470 | 34.483 | 1.00 | 10.75 | C |
| ATOM | 33293 | O   | ALA | D | 223 | 50.310 | 112.533 | 34.626 | 1.00 | 11.73 | O |
| ATOM | 33295 | N   | ALA | D | 224 | 48.441 | 111.378 | 34.101 | 1.00 | 11.29 | N |
| ATOM | 33296 | CA  | ALA | D | 224 | 47.673 | 112.594 | 33.783 | 1.00 | 11.96 | C |
| ATOM | 33298 | CB  | ALA | D | 224 | 46.375 | 112.308 | 33.087 | 1.00 | 11.77 | C |
| ATOM | 33302 | C   | ALA | D | 224 | 47.442 | 113.429 | 35.021 | 1.00 | 12.93 | C |
| ATOM | 33303 | O   | ALA | D | 224 | 47.750 | 114.613 | 35.022 | 1.00 | 12.85 | O |
| ATOM | 33305 | N   | ILE | D | 225 | 46.958 | 112.808 | 36.098 | 1.00 | 11.49 | N |
| ATOM | 33306 | CA  | ILE | D | 225 | 46.689 | 113.657 | 37.306 | 1.00 | 12.03 | C |
| ATOM | 33308 | CB  | ILE | D | 225 | 45.803 | 112.925 | 38.345 | 1.00 | 12.59 | C |
| ATOM | 33310 | CG1 | ILE | D | 225 | 46.453 | 111.656 | 38.861 | 1.00 | 11.38 | C |
| ATOM | 33313 | CD1 | ILE | D | 225 | 45.766 | 111.089 | 40.034 | 1.00 | 11.68 | C |
| ATOM | 33317 | CG2 | ILE | D | 225 | 44.428 | 112.706 | 37.787 | 1.00 | 14.12 | C |
| ATOM | 33321 | C   | ILE | D | 225 | 47.959 | 114.148 | 37.980 | 1.00 | 12.41 | C |
| ATOM | 33322 | O   | ILE | D | 225 | 47.939 | 115.101 | 38.799 | 1.00 | 13.19 | O |
| ATOM | 33324 | N   | SER | D | 226 | 49.084 | 113.479 | 37.656 | 1.00 | 13.31 | N |
| ATOM | 33325 | CA  | SER | D | 226 | 50.404 | 113.899 | 38.149 | 1.00 | 13.83 | C |
| ATOM | 33327 | CB  | SER | D | 226 | 51.217 | 112.674 | 38.610 | 1.00 | 15.48 | C |
| ATOM | 33330 | OG  | SER | D | 226 | 51.610 | 111.897 | 37.536 | 1.00 | 20.01 | O |
| ATOM | 33332 | C   | SER | D | 226 | 51.178 | 114.845 | 37.178 | 1.00 | 13.44 | C |
| ATOM | 33333 | O   | SER | D | 226 | 52.317 | 115.277 | 37.446 | 1.00 | 13.06 | O |
| ATOM | 33335 | N   | GLY | D | 227 | 50.547 | 115.212 | 36.086 | 1.00 | 12.93 | N |
| ATOM | 33336 | CA  | GLY | D | 227 | 51.096 | 116.172 | 35.165 | 1.00 | 13.47 | C |
| ATOM | 33339 | C   | GLY | D | 227 | 52.367 | 115.702 | 34.505 | 1.00 | 13.74 | C |
| ATOM | 33340 | O   | GLY | D | 227 | 53.304 | 116.503 | 34.294 | 1.00 | 14.98 | O |

| ATOM | 33342 | N | HIS | D | 228 | 52.398 | 114.431 | 34.143 | 1.00 | 14.00 | N |
|------|-------|------|-----|---|-----|--------|---------|--------|------|-------|---|
| ATOM | 33343 | CA | HIS | D | 228 | 53.543 | 113.933 | 33.397 | 1.00 | 13.09 | C |
| ATOM | 33345 | CB | HIS | D | 228 | 53.301 | 112.506 | 33.038 | 1.00 | 13.38 | C |
| ATOM | 33348 | CG | HIS | D | 228 | 54.447 | 111.855 | 32.374 | 1.00 | 12.12 | C |
| ATOM | 33349 | ND1 | HIS | D | 228 | 54.896 | 112.224 | 31.114 | 1.00 | 12.10 | N |
| ATOM | 33351 | CE1 | HIS | D | 228 | 55.897 | 111.420 | 30.783 | 1.00 | 13.20 | C |
| ATOM | 33353 | NE2 | HIS | D | 228 | 56.136 | 110.603 | 31.792 | 1.00 | 12.95 | N |
| ATOM | 33355 | CD2 | HIS | D | 228 | 55.238 | 110.849 | 32.792 | 1.00 | 12.57 | C |
| ATOM | 33357 | C | HIS | D | 228 | 53.674 | 114.792 | 32.142 | 1.00 | 13.28 | C |
| ATOM | 33358 | O | HIS | D | 228 | 52.641 | 115.125 | 31.523 | 1.00 | 13.33 | O |
| ATOM | 33360 | N | PRO | D | 229 | 54.911 | 115.167 | 31.762 | 1.00 | 12.87 | N |
| ATOM | 33361 | CA | PRO | D | 229 | 55.061 | 116.072 | 30.596 | 1.00 | 14.29 | C |
| ATOM | 33363 | CB | PRO | D | 229 | 56.549 | 116.339 | 30.542 | 1.00 | 14.62 | C |
| ATOM | 33366 | CG | PRO | D | 229 | 57.124 | 115.807 | 31.762 | 1.00 | 15.36 | C |
| ATOM | 33369 | CD | PRO | D | 229 | 56.210 | 114.838 | 32.389 | 1.00 | 12.99 | C |
| ATOM | 33372 | C | PRO | D | 229 | 54.611 | 115.525 | 29.230 | 1.00 | 14.27 | C |
| ATOM | 33373 | O | PRO | D | 229 | 54.490 | 116.305 | 28.272 | 1.00 | 13.99 | O |
| ATOM | 33374 | N | ASP | D | 230 | 54.406 | 114.218 | 29.129 | 1.00 | 13.51 | N |
| ATOM | 33375 | CA | ASP | D | 230 | 53.938 | 113.620 | 27.868 | 1.00 | 14.27 | C |
| ATOM | 33377 | CB | ASP | D | 230 | 54.981 | 112.604 | 27.413 | 1.00 | 14.20 | C |
| ATOM | 33380 | CG | ASP | D | 230 | 54.848 | 112.198 | 25.963 | 1.00 | 17.03 | C |
| ATOM | 33381 | OD1 | ASP | D | 230 | 54.374 | 112.992 | 25.143 | 1.00 | 17.48 | O |
| ATOM | 33382 | OD2 | ASP | D | 230 | 55.210 | 111.041 | 25.632 | 1.00 | 14.60 | O |
| ATOM | 33383 | C | ASP | D | 230 | 52.568 | 112.988 | 28.025 | 1.00 | 15.44 | C |
| ATOM | 33384 | O | ASP | D | 230 | 52.161 | 112.165 | 27.204 | 1.00 | 17.12 | O |
| ATOM | 33386 | N | SER | D | 231 | 51.827 | 113.398 | 29.057 | 1.00 | 13.85 | N |
| ATOM | 33387 | CA | SER | D | 231 | 50.452 | 112.979 | 29.216 | 1.00 | 14.08 | C |
| ATOM | 33389 | CB | SER | D | 231 | 50.078 | 113.027 | 30.690 | 1.00 | 14.64 | C |
| ATOM | 33392 | OG | SER | D | 231 | 48.705 | 112.789 | 30.847 | 1.00 | 17.99 | O |
| ATOM | 33394 | C | SER | D | 231 | 49.515 | 113.896 | 28.435 | 1.00 | 12.82 | C |
| ATOM | 33395 | O | SER | D | 231 | 49.597 | 115.122 | 28.566 | 1.00 | 12.43 | O |
| ATOM | 33397 | N | LYS | D | 232 | 48.630 | 113.293 | 27.633 | 1.00 | 13.19 | N |
| ATOM | 33398 | CA | LYS | D | 232 | 47.572 | 114.051 | 26.946 | 1.00 | 13.36 | C |
| ATOM | 33400 | CB | LYS | D | 232 | 47.561 | 113.721 | 25.452 | 1.00 | 15.06 | C |
| ATOM | 33403 | CG | LYS | D | 232 | 48.503 | 114.534 | 24.630 | 1.00 | 20.77 | C |
| ATOM | 33406 | CD | LYS | D | 232 | 49.911 | 114.142 | 24.794 | 1.00 | 23.79 | C |
| ATOM | 33409 | CE | LYS | D | 232 | 50.217 | 112.804 | 24.177 | 1.00 | 27.04 | C |
| ATOM | 33412 | NZ | LYS | D | 232 | 51.720 | 112.604 | 24.073 | 1.00 | 26.36 | N |
| ATOM | 33416 | C | LYS | D | 232 | 46.198 | 113.713 | 27.503 | 1.00 | 13.66 | C |
| ATOM | 33417 | O | LYS | D | 232 | 45.924 | 112.580 | 27.926 | 1.00 | 12.96 | O |
| ATOM | 33419 | N | VAL | D | 233 | 45.323 | 114.723 | 27.460 | 1.00 | 12.24 | N |
| ATOM | 33420 | CA | VAL | D | 233 | 43.969 | 114.584 | 27.916 | 1.00 | 12.86 | C |
| ATOM | 33422 | CB | VAL | D | 233 | 43.792 | 115.211 | 29.338 | 1.00 | 13.14 | C |
| ATOM | 33424 | CG1 | VAL | D | 233 | 44.721 | 114.524 | 30.343 | 1.00 | 14.59 | C |
| ATOM | 33428 | CG2 | VAL | D | 233 | 43.991 | 116.736 | 29.333 | 1.00 | 14.06 | C |
| ATOM | 33432 | C | VAL | D | 233 | 43.035 | 115.300 | 26.919 | 1.00 | 12.06 | C |
| ATOM | 33433 | O | VAL | D | 233 | 43.452 | 116.190 | 26.180 | 1.00 | 13.95 | O |
| ATOM | 33435 | N | HIS | D | 234 | 41.806 | 114.814 | 26.878 | 1.00 | 12.24 | N |
| ATOM | 33436 | CA | HIS | D | 234 | 40.709 | 115.378 | 26.123 | 1.00 | 11.93 | C |
| ATOM | 33438 | CB | HIS | D | 234 | 39.841 | 114.233 | 25.608 | 1.00 | 13.27 | C |
| ATOM | 33441 | CG | HIS | D | 234 | 38.605 | 114.692 | 24.915 | 1.00 | 14.43 | C |
| ATOM | 33442 | ND1 | HIS | D | 234 | 37.468 | 115.046 | 25.603 | 1.00 | 13.05 | N |
| ATOM | 33444 | CE1 | HIS | D | 234 | 36.510 | 115.351 | 24.740 | 1.00 | 14.99 | C |
| ATOM | 33446 | NE2 | HIS | D | 234 | 36.977 | 115.176 | 23.516 | 1.00 | 16.34 | N |
| ATOM | 33448 | CD2 | HIS | D | 234 | 38.281 | 114.730 | 23.601 | 1.00 | 15.21 | C |
| ATOM | 33450 | C | HIS | D | 234 | 39.845 | 116.258 | 27.043 | 1.00 | 14.00 | C |
| ATOM | 33451 | O | HIS | D | 234 | 39.538 | 115.889 | 28.177 | 1.00 | 12.41 | O |

| ATOM | 33453 | N | VAL | D | 235 | 39.426 | 117.399 | 26.528 | 1.00 | 14.05 | N |
|------|-------|-----|-----|---|-----|--------|---------|--------|------|-------|---|
| ATOM | 33454 | CA | VAL | D | 235 | 38.537 | 118.249 | 27.294 | 1.00 | 15.61 | C |
| ATOM | 33456 | CB | VAL | D | 235 | 39.348 | 119.258 | 28.161 | 1.00 | 16.27 | C |
| ATOM | 33458 | CG1 | VAL | D | 235 | 40.053 | 120.274 | 27.283 | 1.00 | 18.61 | C |
| ATOM | 33462 | CG2 | VAL | D | 235 | 38.427 | 119.945 | 29.170 | 1.00 | 20.55 | C |
| ATOM | 33466 | C | VAL | D | 235 | 37.665 | 118.981 | 26.287 | 1.00 | 17.14 | C |
| ATOM | 33467 | O | VAL | D | 235 | 38.020 | 119.083 | 25.112 | 1.00 | 16.11 | O |
| ATOM | 33469 | N | VAL | D | 236 | 36.525 | 119.487 | 26.760 | 1.00 | 18.42 | N |
| ATOM | 33470 | CA | VAL | D | 236 | 35.752 | 120.398 | 25.985 | 1.00 | 20.39 | C |
| ATOM | 33472 | CB | VAL | D | 236 | 34.247 | 120.045 | 25.962 | 1.00 | 21.15 | C |
| ATOM | 33474 | CG1 | VAL | D | 236 | 33.416 | 121.213 | 25.388 | 1.00 | 22.62 | C |
| ATOM | 33478 | CG2 | VAL | D | 236 | 34.015 | 118.749 | 25.200 | 1.00 | 21.02 | C |
| ATOM | 33482 | C | VAL | D | 236 | 35.983 | 121.750 | 26.644 | 1.00 | 21.39 | C |
| ATOM | 33483 | O | VAL | D | 236 | 35.816 | 121.908 | 27.868 | 1.00 | 20.37 | O |
| ATOM | 33485 | N | HIS | D | 237 | 36.402 | 122.706 | 25.833 | 1.00 | 22.60 | N |
| ATOM | 33486 | CA | HIS | D | 237 | 36.758 | 124.003 | 26.324 | 1.00 | 23.61 | C |
| ATOM | 33488 | CB | HIS | D | 237 | 38.232 | 123.989 | 26.684 | 1.00 | 23.93 | C |
| ATOM | 33491 | CG | HIS | D | 237 | 38.762 | 125.292 | 27.186 | 1.00 | 24.24 | C |
| ATOM | 33492 | ND1 | HIS | D | 237 | 39.512 | 126.134 | 26.393 | 1.00 | 25.16 | N |
| ATOM | 33494 | CE1 | HIS | D | 237 | 39.867 | 127.202 | 27.095 | 1.00 | 26.64 | C |
| ATOM | 33496 | NE2 | HIS | D | 237 | 39.380 | 127.076 | 28.322 | 1.00 | 28.56 | N |
| ATOM | 33498 | CD2 | HIS | D | 237 | 38.676 | 125.890 | 28.401 | 1.00 | 27.19 | C |
| ATOM | 33500 | C | HIS | D | 237 | 36.450 | 125.027 | 25.230 | 1.00 | 24.60 | C |
| ATOM | 33501 | O | HIS | D | 237 | 36.758 | 124.819 | 24.057 | 1.00 | 23.11 | O |
| ATOM | 33503 | N | GLU | D | 238 | 35.836 | 126.146 | 25.620 | 1.00 | 26.22 | N |
| ATOM | 33504 | CA | GLU | D | 238 | 35.427 | 127.174 | 24.631 | 1.00 | 27.23 | C |
| ATOM | 33506 | CB | GLU | D | 238 | 36.647 | 127.826 | 23.989 | 1.00 | 27.29 | C |
| ATOM | 33509 | CG | GLU | D | 238 | 37.500 | 128.580 | 24.954 | 1.00 | 30.88 | C |
| ATOM | 33512 | CD | GLU | D | 238 | 38.671 | 129.269 | 24.282 | 1.00 | 30.88 | C |
| ATOM | 33513 | OE1 | GLU | D | 238 | 39.333 | 128.639 | 23.410 | 1.00 | 39.00 | O |
| ATOM | 33514 | OE2 | GLU | D | 238 | 38.924 | 130.435 | 24.636 | 1.00 | 38.12 | O |
| ATOM | 33515 | C | GLU | D | 238 | 34.593 | 126.542 | 23.545 | 1.00 | 26.26 | C |
| ATOM | 33516 | O | GLU | D | 238 | 34.753 | 126.836 | 22.350 | 1.00 | 28.03 | O |
| ATOM | 33518 | N | GLY | D | 239 | 33.718 | 125.641 | 23.944 | 1.00 | 24.77 | N |
| ATOM | 33519 | CA | GLY | D | 239 | 32.806 | 125.030 | 23.020 | 1.00 | 24.37 | C |
| ATOM | 33522 | C | GLY | D | 239 | 33.367 | 124.028 | 22.029 | 1.00 | 24.43 | C |
| ATOM | 33523 | O | GLY | D | 239 | 32.672 | 123.645 | 21.113 | 1.00 | 24.63 | O |
| ATOM | 33525 | N | LYS | D | 240 | 34.611 | 123.575 | 22.179 | 1.00 | 23.27 | N |
| ATOM | 33526 | CA | LYS | D | 240 | 35.075 | 122.531 | 21.279 | 1.00 | 22.63 | C |
| ATOM | 33528 | CB | LYS | D | 240 | 35.762 | 123.121 | 20.066 | 1.00 | 24.06 | C |
| ATOM | 33531 | CG | LYS | D | 240 | 37.059 | 123.786 | 20.378 | 1.00 | 28.04 | C |
| ATOM | 33534 | CD | LYS | D | 240 | 37.385 | 124.918 | 19.378 | 1.00 | 33.16 | C |
| ATOM | 33537 | CE | LYS | D | 240 | 36.801 | 126.272 | 19.837 | 1.00 | 35.34 | C |
| ATOM | 33540 | NZ | LYS | D | 240 | 37.224 | 127.447 | 18.984 | 1.00 | 35.99 | N |
| ATOM | 33544 | C | LYS | D | 240 | 35.994 | 121.529 | 21.959 | 1.00 | 19.55 | C |
| ATOM | 33545 | O | LYS | D | 240 | 36.646 | 121.832 | 22.952 | 1.00 | 18.78 | O |
| ATOM | 33547 | N | GLU | D | 241 | 36.031 | 120.350 | 21.375 | 1.00 | 18.53 | N |
| ATOM | 33548 | CA | GLU | D | 241 | 36.885 | 119.292 | 21.862 | 1.00 | 17.14 | C |
| ATOM | 33550 | CB | GLU | D | 241 | 36.543 | 118.026 | 21.115 | 1.00 | 16.10 | C |
| ATOM | 33553 | CG | GLU | D | 241 | 35.192 | 117.424 | 21.430 | 1.00 | 16.61 | C |
| ATOM | 33556 | CD | GLU | D | 241 | 35.040 | 116.062 | 20.740 | 1.00 | 18.16 | C |
| ATOM | 33557 | OE1 | GLU | D | 241 | 35.539 | 115.008 | 21.267 | 1.00 | 17.60 | O |
| ATOM | 33558 | OE2 | GLU | D | 241 | 34.543 | 116.065 | 19.589 | 1.00 | 20.58 | O |
| ATOM | 33559 | C | GLU | D | 241 | 38.353 | 119.615 | 21.598 | 1.00 | 17.13 | C |
| ATOM | 33560 | O | GLU | D | 241 | 38.697 | 120.020 | 20.474 | 1.00 | 19.52 | O |
| ATOM | 33562 | N | LYS | D | 242 | 39.215 | 119.458 | 22.603 | 1.00 | 15.64 | N |
| ATOM | 33563 | CA | LYS | D | 242 | 40.641 | 119.683 | 22.420 | 1.00 | 15.32 | C |

| ATOM | 33565 | CB  | LYS | D | 242 | 41.122 | 120.954 | 23.110 | 1.00 | 15.46 | C |
|------|-------|-----|-----|---|-----|--------|---------|--------|------|-------|---|
| ATOM | 33568 | CG  | LYS | D | 242 | 40.351 | 122.187 | 22.723 | 1.00 | 17.28 | C |
| ATOM | 33571 | CD  | LYS | D | 242 | 40.769 | 123.378 | 23.551 | 1.00 | 17.16 | C |
| ATOM | 33574 | CE  | LYS | D | 242 | 40.132 | 124.671 | 23.007 | 1.00 | 19.29 | C |
| ATOM | 33577 | NZ  | LYS | D | 242 | 40.544 | 125.895 | 23.756 | 1.00 | 20.59 | N |
| ATOM | 33581 | C   | LYS | D | 242 | 41.355 | 118.527 | 23.068 | 1.00 | 15.00 | C |
| ATOM | 33582 | O   | LYS | D | 242 | 40.848 | 117.946 | 24.008 | 1.00 | 14.91 | O |
| ATOM | 33584 | N   | ILE | D | 243 | 42.530 | 118.210 | 22.551 | 1.00 | 14.88 | N |
| ATOM | 33585 | CA  | ILE | D | 243 | 43.454 | 117.313 | 23.225 | 1.00 | 14.50 | C |
| ATOM | 33587 | CB  | ILE | D | 243 | 43.817 | 116.084 | 22.357 | 1.00 | 15.01 | C |
| ATOM | 33589 | CG1 | ILE | D | 243 | 42.565 | 115.244 | 22.129 | 1.00 | 16.50 | C |
| ATOM | 33592 | CD1 | ILE | D | 243 | 42.774 | 114.134 | 21.178 | 1.00 | 19.41 | C |
| ATOM | 33596 | CG2 | ILE | D | 243 | 44.910 | 115.309 | 23.001 | 1.00 | 14.07 | C |
| ATOM | 33600 | C   | ILE | D | 243 | 44.680 | 118.160 | 23.547 | 1.00 | 14.01 | C |
| ATOM | 33601 | O   | ILE | D | 243 | 45.280 | 118.784 | 22.637 | 1.00 | 13.40 | O |
| ATOM | 33603 | N   | LEU | D | 244 | 45.015 | 118.198 | 24.830 | 1.00 | 14.70 | N |
| ATOM | 33604 | CA  | LEU | D | 244 | 46.064 | 119.049 | 25.368 | 1.00 | 14.03 | C |
| ATOM | 33606 | CB  | LEU | D | 244 | 45.427 | 120.156 | 26.236 | 1.00 | 15.11 | C |
| ATOM | 33609 | CG  | LEU | D | 244 | 44.337 | 121.006 | 25.595 | 1.00 | 17.68 | C |
| ATOM | 33611 | CD1 | LEU | D | 244 | 43.657 | 121.851 | 26.694 | 1.00 | 20.99 | C |
| ATOM | 33615 | CD2 | LEU | D | 244 | 44.912 | 121.906 | 24.504 | 1.00 | 18.26 | C |
| ATOM | 33619 | C   | LEU | D | 244 | 46.966 | 118.234 | 26.245 | 1.00 | 13.82 | C |
| ATOM | 33620 | O   | LEU | D | 244 | 46.615 | 117.137 | 26.690 | 1.00 | 12.95 | O |
| ATOM | 33622 | N   | TYR | D | 245 | 48.128 | 118.771 | 26.544 | 1.00 | 12.98 | N |
| ATOM | 33623 | CA  | TYR | D | 245 | 48.938 | 118.148 | 27.590 | 1.00 | 13.58 | C |
| ATOM | 33625 | CB  | TYR | D | 245 | 50.339 | 118.757 | 27.626 | 1.00 | 15.03 | C |
| ATOM | 33628 | CG  | TYR | D | 245 | 51.155 | 118.290 | 26.442 | 1.00 | 17.96 | C |
| ATOM | 33629 | CD1 | TYR | D | 245 | 51.760 | 117.051 | 26.453 | 1.00 | 19.37 | C |
| ATOM | 33631 | CE1 | TYR | D | 245 | 52.499 | 116.592 | 25.361 | 1.00 | 21.02 | C |
| ATOM | 33633 | CZ  | TYR | D | 245 | 52.679 | 117.431 | 24.263 | 1.00 | 21.88 | C |
| ATOM | 33634 | OH  | TYR | D | 245 | 53.415 | 116.946 | 23.200 | 1.00 | 22.09 | O |
| ATOM | 33636 | CE2 | TYR | D | 245 | 52.104 | 118.687 | 24.236 | 1.00 | 20.68 | C |
| ATOM | 33638 | CD2 | TYR | D | 245 | 51.356 | 119.122 | 25.325 | 1.00 | 20.13 | C |
| ATOM | 33640 | C   | TYR | D | 245 | 48.213 | 118.291 | 28.920 | 1.00 | 12.84 | C |
| ATOM | 33641 | O   | TYR | D | 245 | 47.468 | 119.251 | 29.136 | 1.00 | 13.78 | O |
| ATOM | 33643 | N   | ALA | D | 246 | 48.446 | 117.356 | 29.838 | 1.00 | 12.22 | N |
| ATOM | 33644 | CA  | ALA | D | 246 | 47.707 | 117.352 | 31.108 | 1.00 | 12.19 | C |
| ATOM | 33646 | CB  | ALA | D | 246 | 48.137 | 116.176 | 31.976 | 1.00 | 13.04 | C |
| ATOM | 33650 | C   | ALA | D | 246 | 47.898 | 118.668 | 31.859 | 1.00 | 12.53 | C |
| ATOM | 33651 | O   | ALA | D | 246 | 46.927 | 119.213 | 32.344 | 1.00 | 13.43 | O |
| ATOM | 33653 | N   | ARG | D | 247 | 49.131 | 119.164 | 31.960 | 1.00 | 13.57 | N |
| ATOM | 33654 | CA  | ARG | D | 247 | 49.343 | 120.411 | 32.720 | 1.00 | 15.61 | C |
| ATOM | 33656 | CB  | ARG | D | 247 | 50.819 | 120.680 | 32.954 | 1.00 | 16.39 | C |
| ATOM | 33659 | CG  | ARG | D | 247 | 51.409 | 119.811 | 34.040 | 1.00 | 19.52 | C |
| ATOM | 33662 | CD  | ARG | D | 247 | 52.884 | 120.014 | 34.150 | 1.00 | 21.16 | C |
| ATOM | 33665 | NE  | ARG | D | 247 | 53.500 | 119.155 | 35.169 | 1.00 | 21.01 | N |
| ATOM | 33667 | CZ  | ARG | D | 247 | 53.774 | 119.533 | 36.422 | 1.00 | 22.06 | C |
| ATOM | 33668 | NH1 | ARG | D | 247 | 53.488 | 120.754 | 36.873 | 1.00 | 21.76 | N |
| ATOM | 33671 | NH2 | ARG | D | 247 | 54.333 | 118.661 | 37.249 | 1.00 | 23.54 | N |
| ATOM | 33674 | C   | ARG | D | 247 | 48.617 | 121.597 | 32.064 | 1.00 | 16.25 | C |
| ATOM | 33675 | O   | ARG | D | 247 | 48.108 | 122.473 | 32.772 | 1.00 | 14.92 | O |
| ATOM | 33677 | N   | GLU | D | 248 | 48.568 | 121.622 | 30.728 | 1.00 | 16.70 | N |
| ATOM | 33678 | CA  | GLU | D | 248 | 47.806 | 122.689 | 30.003 | 1.00 | 17.63 | C |
| ATOM | 33680 | CB  | GLU | D | 248 | 47.919 | 122.469 | 28.494 | 1.00 | 18.40 | C |
| ATOM | 33683 | CG  | GLU | D | 248 | 49.227 | 122.963 | 27.934 | 1.00 | 20.57 | C |
| ATOM | 33686 | CD  | GLU | D | 248 | 49.646 | 122.345 | 26.565 | 1.00 | 24.33 | C |
| ATOM | 33687 | OE1 | GLU | D | 248 | 48.889 | 121.563 | 25.860 | 1.00 | 24.12 | O |

| ATOM | 33688 | OE2 | GLU | D | 248 | 50.824 | 122.659 | 26.232 | 1.00 | 29.62 | O |
|------|-------|-----|-----|---|-----|--------|---------|--------|------|-------|---|
| ATOM | 33689 | C | GLU | D | 248 | 46.343 | 122.676 | 30.368 | 1.00 | 16.60 | C |
| ATOM | 33690 | O | GLU | D | 248 | 45.731 | 123.692 | 30.676 | 1.00 | 15.69 | O |
| ATOM | 33692 | N | ALA | D | 249 | 45.785 | 121.488 | 30.331 | 1.00 | 15.66 | N |
| ATOM | 33693 | CA | ALA | D | 249 | 44.397 | 121.270 | 30.653 | 1.00 | 16.73 | C |
| ATOM | 33695 | CB | ALA | D | 249 | 44.036 | 119.829 | 30.410 | 1.00 | 17.32 | C |
| ATOM | 33699 | C | ALA | D | 249 | 44.124 | 121.661 | 32.115 | 1.00 | 17.22 | C |
| ATOM | 33700 | O | ALA | D | 249 | 43.164 | 122.348 | 32.395 | 1.00 | 16.18 | O |
| ATOM | 33702 | N | MSE | D | 250 | 44.971 | 121.222 | 33.030 | 1.00 | 17.03 | N |
| ATOM | 33703 | CA | MSE | D | 250 | 44.763 | 121.504 | 34.443 | 1.00 | 19.09 | C |
| ATOM | 33705 | CB | MSE | D | 250 | 45.831 | 120.817 | 35.299 | 1.00 | 18.55 | C |
| ATOM | 33708 | CG | AMSE | D | 250 | 45.482 | 119.268 | 35.443 | 0.50 | 17.51 | C |
| ATOM | 33709 | CG | BMSE | D | 250 | 45.743 | 119.366 | 35.495 | 0.50 | 19.81 | C |
| ATOM | 33714 | SE | AMSE | D | 250 | 46.464 | 118.146 | 36.771 | 0.50 | 19.54 | SE |
| ATOM | 33715 | SE | BMSE | D | 250 | 47.336 | 119.124 | 36.595 | 0.50 | 28.08 | SE |
| ATOM | 33716 | CE | AMSE | D | 250 | 48.318 | 119.047 | 36.250 | 0.50 | 18.12 | C |
| ATOM | 33717 | CE | BMSE | D | 250 | 48.091 | 117.625 | 35.658 | 0.50 | 19.17 | C |
| ATOM | 33724 | C | MSE | D | 250 | 44.776 | 123.012 | 34.655 | 1.00 | 18.02 | C |
| ATOM | 33725 | O | MSE | D | 250 | 43.972 | 123.537 | 35.445 | 1.00 | 17.63 | O |
| ATOM | 33727 | N | ALA | D | 251 | 45.650 | 123.744 | 33.947 | 1.00 | 17.66 | N |
| ATOM | 33728 | CA | ALA | D | 251 | 45.702 | 125.196 | 34.078 | 1.00 | 18.34 | C |
| ATOM | 33730 | CB | ALA | D | 251 | 46.838 | 125.784 | 33.262 | 1.00 | 17.39 | C |
| ATOM | 33734 | C | ALA | D | 251 | 44.406 | 125.841 | 33.641 | 1.00 | 17.95 | C |
| ATOM | 33735 | O | ALA | D | 251 | 44.023 | 126.897 | 34.172 | 1.00 | 18.03 | O |
| ATOM | 33737 | N | LEU | D | 252 | 43.761 | 125.252 | 32.640 | 1.00 | 19.08 | N |
| ATOM | 33738 | CA | LEU | D | 252 | 42.491 | 125.777 | 32.151 | 1.00 | 18.49 | C |
| ATOM | 33740 | CB | LEU | D | 252 | 42.026 | 125.062 | 30.855 | 1.00 | 19.84 | C |
| ATOM | 33743 | CG | LEU | D | 252 | 42.854 | 125.273 | 29.601 | 1.00 | 23.14 | C |
| ATOM | 33745 | CD1 | LEU | D | 252 | 42.115 | 124.516 | 28.432 | 1.00 | 26.16 | C |
| ATOM | 33749 | CD2 | LEU | D | 252 | 43.078 | 126.735 | 29.297 | 1.00 | 27.98 | C |
| ATOM | 33753 | C | LEU | D | 252 | 41.374 | 125.660 | 33.165 | 1.00 | 16.67 | C |
| ATOM | 33754 | O | LEU | D | 252 | 40.398 | 126.403 | 33.053 | 1.00 | 17.40 | O |
| ATOM | 33756 | N | PHE | D | 253 | 41.478 | 124.721 | 34.111 | 1.00 | 15.19 | N |
| ATOM | 33757 | CA | PHE | D | 253 | 40.472 | 124.559 | 35.129 | 1.00 | 15.13 | C |
| ATOM | 33759 | CB | PHE | D | 253 | 39.864 | 123.167 | 35.026 | 1.00 | 16.16 | C |
| ATOM | 33762 | CG | PHE | D | 253 | 39.189 | 122.943 | 33.729 | 1.00 | 17.52 | C |
| ATOM | 33763 | CD1 | PHE | D | 253 | 37.879 | 123.388 | 33.551 | 1.00 | 18.74 | C |
| ATOM | 33765 | CE1 | PHE | D | 253 | 37.245 | 123.205 | 32.344 | 1.00 | 17.29 | C |
| ATOM | 33767 | CZ | PHE | D | 253 | 37.921 | 122.670 | 31.277 | 1.00 | 17.98 | C |
| ATOM | 33769 | CE2 | PHE | D | 253 | 39.228 | 122.246 | 31.421 | 1.00 | 20.14 | C |
| ATOM | 33771 | CD2 | PHE | D | 253 | 39.869 | 122.410 | 32.663 | 1.00 | 18.80 | C |
| ATOM | 33773 | C | PHE | D | 253 | 40.959 | 124.818 | 36.540 | 1.00 | 14.27 | C |
| ATOM | 33774 | O | PHE | D | 253 | 40.236 | 124.595 | 37.493 | 1.00 | 14.73 | O |
| ATOM | 33776 | N | ASN | D | 254 | 42.154 | 125.374 | 36.659 | 1.00 | 12.15 | N |
| ATOM | 33777 | CA | ASN | D | 254 | 42.745 | 125.713 | 37.962 | 1.00 | 11.50 | C |
| ATOM | 33779 | CB | ASN | D | 254 | 41.995 | 126.866 | 38.666 | 1.00 | 11.81 | C |
| ATOM | 33782 | CG | ASN | D | 254 | 42.852 | 127.520 | 39.740 | 1.00 | 11.38 | C |
| ATOM | 33783 | OD1 | ASN | D | 254 | 44.050 | 127.227 | 39.822 | 1.00 | 12.50 | O |
| ATOM | 33784 | ND2 | ASN | D | 254 | 42.275 | 128.432 | 40.527 | 1.00 | 13.12 | N |
| ATOM | 33787 | C | ASN | D | 254 | 42.907 | 124.501 | 38.861 | 1.00 | 12.66 | C |
| ATOM | 33788 | O | ASN | D | 254 | 42.606 | 124.543 | 40.070 | 1.00 | 13.09 | O |
| ATOM | 33790 | N | LEU | D | 255 | 43.432 | 123.417 | 38.275 | 1.00 | 11.61 | N |
| ATOM | 33791 | CA | LEU | D | 255 | 43.768 | 122.229 | 39.052 | 1.00 | 11.97 | C |
| ATOM | 33793 | CB | LEU | D | 255 | 43.243 | 121.009 | 38.346 | 1.00 | 12.52 | C |
| ATOM | 33796 | CG | LEU | D | 255 | 41.734 | 121.004 | 38.068 | 1.00 | 13.47 | C |
| ATOM | 33798 | CD1 | LEU | D | 255 | 41.351 | 119.777 | 37.236 | 1.00 | 14.10 | C |
| ATOM | 33802 | CD2 | LEU | D | 255 | 40.928 | 121.157 | 39.389 | 1.00 | 13.71 | C |

| ATOM | 33806 | C | LEU | D | 255 | 45.281 | 122.119 | 39.170 | 1.00 | 12.70 | C |
| --- | --- | --- | --- | --- | --- | --- | --- | --- | --- | --- | --- |
| ATOM | 33807 | O | LEU | D | 255 | 46.018 | 122.558 | 38.258 | 1.00 | 12.99 | O |
| ATOM | 33809 | N | GLU | D | 256 | 45.737 | 121.526 | 40.271 | 1.00 | 12.73 | N |
| ATOM | 33810 | CA | GLU | D | 256 | 47.152 | 121.291 | 40.510 | 1.00 | 13.50 | C |
| ATOM | 33812 | CB | GLU | D | 256 | 47.518 | 121.740 | 41.939 | 1.00 | 14.77 | C |
| ATOM | 33815 | CG | GLU | D | 256 | 47.569 | 123.237 | 42.129 | 1.00 | 17.24 | C |
| ATOM | 33818 | CD | GLU | D | 256 | 48.643 | 123.926 | 41.242 | 1.00 | 22.29 | C |
| ATOM | 33819 | OE1 | GLU | D | 256 | 49.743 | 123.389 | 41.073 | 1.00 | 26.02 | O |
| ATOM | 33820 | OE2 | GLU | D | 256 | 48.397 | 125.011 | 40.691 | 1.00 | 23.78 | O |
| ATOM | 33821 | C | GLU | D | 256 | 47.492 | 119.841 | 40.390 | 1.00 | 13.68 | C |
| ATOM | 33822 | O | GLU | D | 256 | 46.711 | 118.985 | 40.801 | 1.00 | 12.57 | O |
| ATOM | 33824 | N | PRO | D | 257 | 48.664 | 119.556 | 39.830 | 1.00 | 14.34 | N |
| ATOM | 33825 | CA | PRO | D | 257 | 49.048 | 118.156 | 39.798 | 1.00 | 14.49 | C |
| ATOM | 33827 | CB | PRO | D | 257 | 50.313 | 118.115 | 38.941 | 1.00 | 14.89 | C |
| ATOM | 33830 | CG | PRO | D | 257 | 50.868 | 119.444 | 38.993 | 1.00 | 16.82 | C |
| ATOM | 33833 | CD | PRO | D | 257 | 49.691 | 120.425 | 39.226 | 1.00 | 15.47 | C |
| ATOM | 33836 | C | PRO | D | 257 | 49.382 | 117.651 | 41.172 | 1.00 | 15.09 | C |
| ATOM | 33837 | O | PRO | D | 257 | 49.852 | 118.401 | 42.000 | 1.00 | 13.31 | O |
| ATOM | 33838 | N | VAL | D | 258 | 49.112 | 116.372 | 41.380 | 1.00 | 13.84 | N |
| ATOM | 33839 | CA | VAL | D | 258 | 49.611 | 115.654 | 42.543 | 1.00 | 15.00 | C |
| ATOM | 33841 | CB | VAL | D | 258 | 48.650 | 114.512 | 42.990 | 1.00 | 15.11 | C |
| ATOM | 33843 | CG1 | VAL | D | 258 | 47.298 | 115.090 | 43.460 | 1.00 | 17.44 | C |
| ATOM | 33847 | CG2 | VAL | D | 258 | 48.407 | 113.528 | 41.910 | 1.00 | 16.02 | C |
| ATOM | 33851 | C | VAL | D | 258 | 51.000 | 115.090 | 42.288 | 1.00 | 15.23 | C |
| ATOM | 33852 | O | VAL | D | 258 | 51.361 | 114.780 | 41.175 | 1.00 | 15.14 | O |
| ATOM | 33854 | N | VAL | D | 259 | 51.787 | 115.000 | 43.357 | 1.00 | 15.69 | N |
| ATOM | 33855 | CA | VAL | D | 259 | 53.062 | 114.270 | 43.335 | 1.00 | 15.68 | C |
| ATOM | 33857 | CB | VAL | D | 259 | 54.212 | 115.071 | 44.002 | 1.00 | 14.74 | C |
| ATOM | 33859 | CG1 | VAL | D | 259 | 55.499 | 114.249 | 43.984 | 1.00 | 15.27 | C |
| ATOM | 33863 | CG2 | VAL | D | 259 | 54.393 | 116.439 | 43.307 | 1.00 | 16.93 | C |
| ATOM | 33867 | C | VAL | D | 259 | 52.838 | 112.960 | 44.091 | 1.00 | 15.74 | C |
| ATOM | 33868 | O | VAL | D | 259 | 52.490 | 112.999 | 45.275 | 1.00 | 15.17 | O |
| ATOM | 33870 | N | LEU | D | 260 | 53.065 | 111.824 | 43.413 | 1.00 | 15.90 | N |
| ATOM | 33871 | CA | LEU | D | 260 | 52.788 | 110.502 | 43.984 | 1.00 | 15.81 | C |
| ATOM | 33873 | CB | LEU | D | 260 | 52.714 | 109.460 | 42.893 | 1.00 | 15.19 | C |
| ATOM | 33876 | CG | LEU | D | 260 | 51.659 | 109.730 | 41.802 | 1.00 | 15.06 | C |
| ATOM | 33878 | CD1 | LEU | D | 260 | 51.602 | 108.530 | 40.856 | 1.00 | 16.93 | C |
| ATOM | 33882 | CD2 | LEU | D | 260 | 50.245 | 110.003 | 42.312 | 1.00 | 18.26 | C |
| ATOM | 33886 | C | LEU | D | 260 | 53.821 | 110.124 | 45.050 | 1.00 | 16.25 | C |
| ATOM | 33887 | O | LEU | D | 260 | 55.055 | 110.250 | 44.859 | 1.00 | 16.51 | O |
| ATOM | 33889 | N | GLY | D | 261 | 53.290 | 109.696 | 46.192 | 1.00 | 16.45 | N |
| ATOM | 33890 | CA | GLY | D | 261 | 54.129 | 109.279 | 47.319 | 1.00 | 16.13 | C |
| ATOM | 33893 | C | GLY | D | 261 | 54.113 | 107.776 | 47.480 | 1.00 | 15.07 | C |
| ATOM | 33894 | O | GLY | D | 261 | 53.622 | 107.025 | 46.616 | 1.00 | 13.80 | O |
| ATOM | 33896 | N | PRO | D | 262 | 54.647 | 107.317 | 48.614 | 1.00 | 15.63 | N |
| ATOM | 33897 | CA | PRO | D | 262 | 54.803 | 105.895 | 48.783 | 1.00 | 16.01 | C |
| ATOM | 33899 | CB | PRO | D | 262 | 55.275 | 105.750 | 50.220 | 1.00 | 16.64 | C |
| ATOM | 33902 | CG | PRO | D | 262 | 55.702 | 107.060 | 50.633 | 1.00 | 17.61 | C |
| ATOM | 33905 | CD | PRO | D | 262 | 55.138 | 108.096 | 49.749 | 1.00 | 16.14 | C |
| ATOM | 33908 | C | PRO | D | 262 | 53.473 | 105.158 | 48.605 | 1.00 | 15.18 | C |
| ATOM | 33909 | O | PRO | D | 262 | 52.408 | 105.630 | 49.082 | 1.00 | 15.64 | O |
| ATOM | 33910 | N | LYS | D | 263 | 53.550 | 104.038 | 47.891 | 1.00 | 14.64 | N |
| ATOM | 33911 | CA | LYS | D | 263 | 52.382 | 103.182 | 47.615 | 1.00 | 14.52 | C |
| ATOM | 33913 | CB | LYS | D | 263 | 51.710 | 102.734 | 48.930 | 1.00 | 14.76 | C |
| ATOM | 33916 | CG | LYS | D | 263 | 50.482 | 101.829 | 48.838 | 1.00 | 14.98 | C |
| ATOM | 33919 | CD | LYS | D | 263 | 50.724 | 100.517 | 48.075 | 1.00 | 15.49 | C |
| ATOM | 33922 | CE | LYS | D | 263 | 49.543 | 100.112 | 47.268 | 1.00 | 15.73 | C |

```
ATOM  33925  NZ   LYS D 263      48.314  99.905  48.110  1.00 15.83           N
ATOM  33929  C    LYS D 263      51.377 103.803  46.640  1.00 13.89           C
ATOM  33930  O    LYS D 263      50.514 103.080  46.167  1.00 16.54           O
ATOM  33932  N    GLU D 264      51.478 105.090  46.292  1.00 14.94           N
ATOM  33933  CA   GLU D 264      50.449 105.686  45.454  1.00 14.39           C
ATOM  33935  CB   GLU D 264      50.393 107.189  45.642  1.00 13.39           C
ATOM  33938  CG   GLU D 264      49.981 107.569  47.081  1.00 13.41           C
ATOM  33941  CD   GLU D 264      49.754 109.039  47.291  1.00 17.37           C
ATOM  33942  OE1  GLU D 264      50.422 109.876  46.593  1.00 15.30           O
ATOM  33943  OE2  GLU D 264      48.926 109.324  48.172  1.00 15.15           O
ATOM  33944  C    GLU D 264      50.562 105.320  43.984  1.00 14.76           C
ATOM  33945  O    GLU D 264      49.556 105.269  43.279  1.00 16.17           O
ATOM  33947  N    GLY D 265      51.773 104.992  43.530  1.00 12.48           N
ATOM  33948  CA   GLY D 265      51.895 104.459  42.168  1.00 15.41           C
ATOM  33951  C    GLY D 265      51.136 103.124  42.050  1.00 14.84           C
ATOM  33952  O    GLY D 265      50.250 103.003  41.202  1.00 16.05           O
ATOM  33954  N    LEU D 266      51.450 102.135  42.909  1.00 14.77           N
ATOM  33955  CA   LEU D 266      50.721 100.853  42.866  1.00 15.10           C
ATOM  33957  CB   LEU D 266      51.373  99.830  43.819  1.00 16.05           C
ATOM  33960  CG   LEU D 266      52.789  99.336  43.472  1.00 17.80           C
ATOM  33962  CD1  LEU D 266      53.215  98.362  44.547  1.00 20.71           C
ATOM  33966  CD2  LEU D 266      52.787  98.709  42.109  1.00 20.54           C
ATOM  33970  C    LEU D 266      49.244 101.017  43.237  1.00 15.71           C
ATOM  33971  O    LEU D 266      48.366 100.352  42.678  1.00 16.29           O
ATOM  33973  N    GLY D 267      48.964 101.923  44.169  1.00 15.44           N
ATOM  33974  CA   GLY D 267      47.577 102.159  44.560  1.00 15.63           C
ATOM  33977  C    GLY D 267      46.722 102.650  43.404  1.00 15.70           C
ATOM  33978  O    GLY D 267      45.517 102.321  43.321  1.00 17.35           O
ATOM  33980  N    LEU D 268      47.336 103.405  42.500  1.00 13.61           N
ATOM  33981  CA   LEU D 268      46.636 103.923  41.336  1.00 14.73           C
ATOM  33983  CB   LEU D 268      47.231 105.234  40.869  1.00 14.22           C
ATOM  33986  CG   LEU D 268      46.869 106.439  41.705  1.00 14.04           C
ATOM  33988  CD1  LEU D 268      47.646 107.690  41.213  1.00 14.49           C
ATOM  33992  CD2  LEU D 268      45.364 106.700  41.644  1.00 14.24           C
ATOM  33996  C    LEU D 268      46.632 102.964  40.145  1.00 15.61           C
ATOM  33997  O    LEU D 268      45.657 102.950  39.394  1.00 17.12           O
ATOM  33999  N    VAL D 269      47.741 102.251  39.932  1.00 14.87           N
ATOM  34000  CA   VAL D 269      47.925 101.539  38.680  1.00 14.57           C
ATOM  34002  CB   VAL D 269      49.315 101.735  38.019  1.00 15.47           C
ATOM  34004  CG1  VAL D 269      49.670 103.259  37.977  1.00 16.63           C
ATOM  34008  CG2  VAL D 269      50.330 100.949  38.675  1.00 19.70           C
ATOM  34012  C    VAL D 269      47.581 100.046  38.757  1.00 13.59           C
ATOM  34013  O    VAL D 269      47.304  99.450  37.740  1.00 14.72           O
ATOM  34015  N    ASN D 270      47.645  99.467  39.952  1.00 14.65           N
ATOM  34016  CA   ASN D 270      47.258  98.059  40.171  1.00 14.23           C
ATOM  34018  CB   ASN D 270      47.809  97.438  41.462  1.00 14.47           C
ATOM  34021  CG   ASN D 270      49.191  96.938  41.361  1.00 20.94           C
ATOM  34022  OD1  ASN D 270      49.857  97.069  40.329  1.00 28.06           O
ATOM  34023  ND2  ASN D 270      49.664  96.341  42.453  1.00 22.10           N
ATOM  34026  C    ASN D 270      45.751  98.024  40.341  1.00 13.71           C
ATOM  34027  O    ASN D 270      45.209  98.657  41.249  1.00 14.51           O
ATOM  34029  N    GLY D 271      45.082  97.184  39.575  1.00 13.30           N
ATOM  34030  CA   GLY D 271      43.648  97.023  39.781  1.00 13.55           C
ATOM  34033  C    GLY D 271      42.876  96.791  38.523  1.00 12.18           C
ATOM  34034  O    GLY D 271      43.467  96.621  37.429  1.00 11.54           O
ATOM  34036  N    THR D 272      41.544  96.740  38.669  1.00 11.13           N
ATOM  34037  CA   THR D 272      40.692  96.258  37.572  1.00 11.69           C
```

| ATOM | 34039 | CB | THR | D | 272 | 39.918 | 94.970 | 37.984 | 1.00 | 11.24 | C |
| ATOM | 34041 | OG1 | THR | D | 272 | 38.911 | 95.312 | 38.954 | 1.00 | 13.09 | O |
| ATOM | 34043 | CG2 | THR | D | 272 | 40.808 | 93.925 | 38.608 | 1.00 | 13.44 | C |
| ATOM | 34047 | C | THR | D | 272 | 39.681 | 97.277 | 37.038 | 1.00 | 12.00 | C |
| ATOM | 34048 | O | THR | D | 272 | 38.756 | 96.910 | 36.283 | 1.00 | 12.24 | O |
| ATOM | 34050 | N | ALA | D | 273 | 39.896 | 98.567 | 37.362 | 1.00 | 12.65 | N |
| ATOM | 34051 | CA | ALA | D | 273 | 38.894 | 99.588 | 37.065 | 1.00 | 12.03 | C |
| ATOM | 34053 | CB | ALA | D | 273 | 39.289 | 100.884 | 37.714 | 1.00 | 13.69 | C |
| ATOM | 34057 | C | ALA | D | 273 | 38.587 | 99.784 | 35.600 | 1.00 | 12.45 | C |
| ATOM | 34058 | O | ALA | D | 273 | 37.478 | 100.129 | 35.232 | 1.00 | 12.94 | O |
| ATOM | 34060 | N | VAL | D | 274 | 39.574 | 99.580 | 34.721 | 1.00 | 11.62 | N |
| ATOM | 34061 | CA | VAL | D | 274 | 39.367 | 99.887 | 33.293 | 1.00 | 12.83 | C |
| ATOM | 34063 | CB | VAL | D | 274 | 40.682 | 100.020 | 32.549 | 1.00 | 12.90 | C |
| ATOM | 34065 | CG1 | VAL | D | 274 | 40.420 | 100.362 | 31.115 | 1.00 | 14.62 | C |
| ATOM | 34069 | CG2 | VAL | D | 274 | 41.518 | 101.145 | 33.201 | 1.00 | 12.42 | C |
| ATOM | 34073 | C | VAL | D | 274 | 38.526 | 98.812 | 32.662 | 1.00 | 13.80 | C |
| ATOM | 34074 | O | VAL | D | 274 | 37.510 | 99.079 | 32.025 | 1.00 | 13.31 | O |
| ATOM | 34076 | N | SER | D | 275 | 38.913 | 97.572 | 32.892 | 1.00 | 12.55 | N |
| ATOM | 34077 | CA | SER | D | 275 | 38.145 | 96.409 | 32.425 | 1.00 | 14.00 | C |
| ATOM | 34079 | CB | SER | D | 275 | 38.988 | 95.125 | 32.627 | 1.00 | 15.51 | C |
| ATOM | 34082 | OG | SER | D | 275 | 39.224 | 94.894 | 33.960 | 1.00 | 20.37 | O |
| ATOM | 34084 | C | SER | D | 275 | 36.750 | 96.404 | 33.095 | 1.00 | 12.72 | C |
| ATOM | 34085 | O | SER | D | 275 | 35.742 | 96.189 | 32.435 | 1.00 | 12.94 | O |
| ATOM | 34087 | N | ALA | D | 276 | 36.673 | 96.706 | 34.383 | 1.00 | 11.45 | N |
| ATOM | 34088 | CA | ALA | D | 276 | 35.363 | 96.714 | 35.052 | 1.00 | 12.16 | C |
| ATOM | 34090 | CB | ALA | D | 276 | 35.505 | 96.937 | 36.524 | 1.00 | 13.07 | C |
| ATOM | 34094 | C | ALA | D | 276 | 34.450 | 97.797 | 34.477 | 1.00 | 12.75 | C |
| ATOM | 34095 | O | ALA | D | 276 | 33.259 | 97.607 | 34.315 | 1.00 | 13.50 | O |
| ATOM | 34097 | N | SER | D | 277 | 35.028 | 98.922 | 34.070 | 1.00 | 12.05 | N |
| ATOM | 34098 | CA | SER | D | 277 | 34.244 | 99.999 | 33.498 | 1.00 | 11.89 | C |
| ATOM | 34100 | CB | SER | D | 277 | 35.143 | 101.241 | 33.329 | 1.00 | 11.48 | C |
| ATOM | 34103 | OG | SER | D | 277 | 34.522 | 102.234 | 32.529 | 1.00 | 13.23 | O |
| ATOM | 34105 | C | SER | D | 277 | 33.665 | 99.590 | 32.154 | 1.00 | 11.60 | C |
| ATOM | 34106 | O | SER | D | 277 | 32.475 | 99.705 | 31.860 | 1.00 | 13.14 | O |
| ATOM | 34108 | N | MSE | D | 278 | 34.541 | 99.138 | 31.295 | 1.00 | 12.96 | N |
| ATOM | 34109 | CA | MSE | D | 278 | 34.116 | 98.697 | 29.984 | 1.00 | 13.76 | C |
| ATOM | 34111 | CB | MSE | D | 278 | 35.282 | 98.308 | 29.104 | 1.00 | 14.15 | C |
| ATOM | 34114 | CG | MSE | D | 278 | 34.807 | 98.233 | 27.673 | 1.00 | 16.30 | C |
| ATOM | 34117 | SE | MSE | D | 278 | 36.307 | 98.374 | 26.376 | 1.00 | 23.90 | SE |
| ATOM | 34118 | CE | MSE | D | 278 | 37.337 | 99.855 | 26.834 | 1.00 | 31.22 | C |
| ATOM | 34122 | C | MSE | D | 278 | 33.113 | 97.573 | 30.036 | 1.00 | 13.29 | C |
| ATOM | 34123 | O | MSE | D | 278 | 32.112 | 97.564 | 29.292 | 1.00 | 13.49 | O |
| ATOM | 34125 | N | ALA | D | 279 | 33.367 | 96.617 | 30.927 | 1.00 | 11.59 | N |
| ATOM | 34126 | CA | ALA | D | 279 | 32.429 | 95.543 | 31.125 | 1.00 | 12.38 | C |
| ATOM | 34128 | CB | ALA | D | 279 | 33.050 | 94.509 | 32.052 | 1.00 | 11.73 | C |
| ATOM | 34132 | C | ALA | D | 279 | 31.078 | 96.018 | 31.655 | 1.00 | 12.09 | C |
| ATOM | 34133 | O | ALA | D | 279 | 30.023 | 95.478 | 31.296 | 1.00 | 13.26 | O |
| ATOM | 34135 | N | THR | D | 280 | 31.084 | 97.009 | 32.548 | 1.00 | 11.52 | N |
| ATOM | 34136 | CA | THR | D | 280 | 29.810 | 97.486 | 33.084 | 1.00 | 11.68 | C |
| ATOM | 34138 | CB | THR | D | 280 | 30.060 | 98.515 | 34.227 | 1.00 | 12.41 | C |
| ATOM | 34140 | OG1 | THR | D | 280 | 30.668 | 97.809 | 35.323 | 1.00 | 12.60 | O |
| ATOM | 34142 | CG2 | THR | D | 280 | 28.790 | 99.184 | 34.657 | 1.00 | 12.95 | C |
| ATOM | 34146 | C | THR | D | 280 | 28.938 | 98.106 | 31.951 | 1.00 | 11.22 | C |
| ATOM | 34147 | O | THR | D | 280 | 27.715 | 97.856 | 31.840 | 1.00 | 12.29 | O |
| ATOM | 34149 | N | LEU | D | 281 | 29.591 | 98.898 | 31.118 | 1.00 | 12.05 | N |
| ATOM | 34150 | CA | LEU | D | 281 | 28.939 | 99.556 | 29.991 | 1.00 | 12.46 | C |
| ATOM | 34152 | CB | LEU | D | 281 | 29.896 | 100.536 | 29.319 | 1.00 | 13.38 | C |

| | | | | | | | | | |
|---|---|---|---|---|---|---|---|---|---|
| ATOM | 34155 | CG | LEU | D | 281 | 30.285 | 101.714 | 30.219 | 1.00 14.76 | C |
| ATOM | 34157 | CD1 | LEU | D | 281 | 31.534 | 102.429 | 29.750 | 1.00 18.52 | C |
| ATOM | 34161 | CD2 | LEU | D | 281 | 29.153 | 102.745 | 30.261 | 1.00 17.90 | C |
| ATOM | 34165 | C | LEU | D | 281 | 28.419 | 98.491 | 29.047 | 1.00 13.01 | C |
| ATOM | 34166 | O | LEU | D | 281 | 27.316 | 98.600 | 28.546 | 1.00 13.33 | O |
| ATOM | 34168 | N | ALA | D | 282 | 29.234 | 97.480 | 28.775 | 1.00 12.88 | N |
| ATOM | 34169 | CA | ALA | D | 282 | 28.846 | 96.381 | 27.863 | 1.00 13.29 | C |
| ATOM | 34171 | CB | ALA | D | 282 | 29.999 | 95.464 | 27.628 | 1.00 14.17 | C |
| ATOM | 34175 | C | ALA | D | 282 | 27.659 | 95.609 | 28.448 | 1.00 13.41 | C |
| ATOM | 34176 | O | ALA | D | 282 | 26.728 | 95.249 | 27.714 | 1.00 13.47 | O |
| ATOM | 34178 | N | LEU | D | 283 | 27.673 | 95.335 | 29.757 | 1.00 11.08 | N |
| ATOM | 34179 | CA | LEU | D | 283 | 26.583 | 94.580 | 30.361 | 1.00 12.70 | C |
| ATOM | 34181 | CB | LEU | D | 283 | 26.934 | 94.132 | 31.766 | 1.00 11.84 | C |
| ATOM | 34184 | CG | LEU | D | 283 | 25.841 | 93.308 | 32.437 | 1.00 15.05 | C |
| ATOM | 34186 | CD1 | LEU | D | 283 | 25.551 | 92.013 | 31.641 | 1.00 16.84 | C |
| ATOM | 34190 | CD2 | LEU | D | 283 | 26.192 | 92.953 | 33.884 | 1.00 14.68 | C |
| ATOM | 34194 | C | LEU | D | 283 | 25.292 | 95.396 | 30.330 | 1.00 11.60 | C |
| ATOM | 34195 | O | LEU | D | 283 | 24.231 | 94.869 | 29.983 | 1.00 12.48 | O |
| ATOM | 34197 | N | HIS | D | 284 | 25.370 | 96.682 | 30.698 | 1.00 12.58 | N |
| ATOM | 34198 | CA | HIS | D | 284 | 24.249 | 97.594 | 30.593 | 1.00 13.18 | C |
| ATOM | 34200 | CB | HIS | D | 284 | 24.747 | 99.005 | 30.893 | 1.00 13.70 | C |
| ATOM | 34203 | CG | HIS | D | 284 | 23.766 | 100.094 | 30.593 | 1.00 14.12 | C |
| ATOM | 34204 | ND1 | HIS | D | 284 | 23.535 | 100.549 | 29.317 | 1.00 14.62 | N |
| ATOM | 34206 | CE1 | HIS | D | 284 | 22.643 | 101.524 | 29.347 | 1.00 17.27 | C |
| ATOM | 34208 | NE2 | HIS | D | 284 | 22.287 | 101.734 | 30.599 | 1.00 17.04 | N |
| ATOM | 34210 | CD2 | HIS | D | 284 | 22.983 | 100.862 | 31.405 | 1.00 16.61 | C |
| ATOM | 34212 | C | HIS | D | 284 | 23.620 | 97.490 | 29.205 | 1.00 13.76 | C |
| ATOM | 34213 | O | HIS | D | 284 | 22.425 | 97.339 | 29.062 | 1.00 14.73 | O |
| ATOM | 34215 | N | ASP | D | 285 | 24.419 | 97.588 | 28.173 | 1.00 13.46 | N |
| ATOM | 34216 | CA | ASP | D | 285 | 23.887 | 97.581 | 26.800 | 1.00 14.01 | C |
| ATOM | 34218 | CB | ASP | D | 285 | 24.961 | 97.988 | 25.801 | 1.00 13.29 | C |
| ATOM | 34221 | CG | ASP | D | 285 | 25.397 | 99.443 | 25.956 | 1.00 14.18 | C |
| ATOM | 34222 | OD1 | ASP | D | 285 | 24.732 | 100.219 | 26.682 | 1.00 15.66 | O |
| ATOM | 34223 | OD2 | ASP | D | 285 | 26.411 | 99.839 | 25.314 | 1.00 15.14 | O |
| ATOM | 34224 | C | ASP | D | 285 | 23.328 | 96.191 | 26.445 | 1.00 12.68 | C |
| ATOM | 34225 | O | ASP | D | 285 | 22.310 | 96.087 | 25.707 | 1.00 13.77 | O |
| ATOM | 34227 | N | ALA | D | 286 | 23.983 | 95.132 | 26.925 | 1.00 12.43 | N |
| ATOM | 34228 | CA | ALA | D | 286 | 23.544 | 93.739 | 26.648 | 1.00 12.16 | C |
| ATOM | 34230 | CB | ALA | D | 286 | 24.593 | 92.735 | 27.116 | 1.00 12.41 | C |
| ATOM | 34234 | C | ALA | D | 286 | 22.166 | 93.498 | 27.295 | 1.00 12.58 | C |
| ATOM | 34235 | O | ALA | D | 286 | 21.283 | 92.838 | 26.703 | 1.00 12.30 | O |
| ATOM | 34237 | N | HIS | D | 287 | 21.948 | 94.078 | 28.476 | 1.00 12.03 | N |
| ATOM | 34238 | CA | HIS | D | 287 | 20.621 | 93.925 | 29.088 | 1.00 12.86 | C |
| ATOM | 34240 | CB | HIS | D | 287 | 20.500 | 94.654 | 30.415 | 1.00 13.43 | C |
| ATOM | 34243 | CG | HIS | D | 287 | 21.199 | 94.000 | 31.571 | 1.00 12.32 | C |
| ATOM | 34244 | ND1 | HIS | D | 287 | 21.007 | 92.678 | 31.913 | 1.00 12.76 | N |
| ATOM | 34246 | CE1 | HIS | D | 287 | 21.699 | 92.420 | 33.016 | 1.00 12.21 | C |
| ATOM | 34248 | NE2 | HIS | D | 287 | 22.295 | 93.537 | 33.422 | 1.00 13.97 | N |
| ATOM | 34250 | CD2 | HIS | D | 287 | 21.986 | 94.539 | 32.536 | 1.00 13.23 | C |
| ATOM | 34252 | C | HIS | D | 287 | 19.511 | 94.491 | 28.165 | 1.00 12.59 | C |
| ATOM | 34253 | O | HIS | D | 287 | 18.420 | 93.954 | 28.021 | 1.00 12.91 | O |
| ATOM | 34255 | N | MSE | D | 288 | 19.794 | 95.666 | 27.585 | 1.00 13.24 | N |
| ATOM | 34256 | CA | MSE | D | 288 | 18.764 | 96.331 | 26.737 | 1.00 12.03 | C |
| ATOM | 34258 | CB | MSE | D | 288 | 19.259 | 97.730 | 26.351 | 1.00 14.08 | C |
| ATOM | 34261 | CG | MSE | D | 288 | 19.671 | 98.565 | 27.502 | 1.00 15.42 | C |
| ATOM | 34264 | SE | MSE | D | 288 | 18.326 | 98.737 | 28.928 | 1.00 24.48 | SE |
| ATOM | 34265 | CE | MSE | D | 288 | 19.691 | 99.385 | 30.314 | 1.00 22.24 | C |

| ATOM | 34269 | C   | MSE | D | 288 | 18.490 | 95.466 | 25.504 | 1.00 | 12.82 | C |
|------|-------|-----|-----|---|-----|--------|--------|--------|------|-------|---|
| ATOM | 34270 | O   | MSE | D | 288 | 17.336 | 95.304 | 25.063 | 1.00 | 13.71 | O |
| ATOM | 34272 | N   | LEU | D | 289 | 19.567 | 94.970 | 24.904 | 1.00 | 11.28 | N |
| ATOM | 34273 | CA  | LEU | D | 289 | 19.437 | 94.106 | 23.697 | 1.00 | 11.97 | C |
| ATOM | 34275 | CB  | LEU | D | 289 | 20.809 | 93.823 | 23.097 | 1.00 | 12.56 | C |
| ATOM | 34278 | CG  | LEU | D | 289 | 21.490 | 95.093 | 22.571 | 1.00 | 11.91 | C |
| ATOM | 34280 | CD1 | LEU | D | 289 | 22.956 | 94.874 | 22.202 | 1.00 | 14.03 | C |
| ATOM | 34284 | CD2 | LEU | D | 289 | 20.750 | 95.617 | 21.323 | 1.00 | 12.81 | C |
| ATOM | 34288 | C   | LEU | D | 289 | 18.673 | 92.822 | 24.012 | 1.00 | 13.53 | C |
| ATOM | 34289 | O   | LEU | D | 289 | 17.860 | 92.319 | 23.194 | 1.00 | 13.64 | O |
| ATOM | 34291 | N   | SER | D | 290 | 18.880 | 92.285 | 25.199 | 1.00 | 14.29 | N |
| ATOM | 34292 | CA  | SER | D | 290 | 18.136 | 91.125 | 25.652 | 1.00 | 13.00 | C |
| ATOM | 34294 | CB  | SER | D | 290 | 18.578 | 90.723 | 27.070 | 1.00 | 13.73 | C |
| ATOM | 34297 | OG  | SER | D | 290 | 17.786 | 89.627 | 27.516 | 1.00 | 16.25 | O |
| ATOM | 34299 | C   | SER | D | 290 | 16.622 | 91.464 | 25.659 | 1.00 | 12.90 | C |
| ATOM | 34300 | O   | SER | D | 290 | 15.805 | 90.686 | 25.150 | 1.00 | 14.29 | O |
| ATOM | 34302 | N   | LEU | D | 291 | 16.242 | 92.568 | 26.271 | 1.00 | 12.34 | N |
| ATOM | 34303 | CA  | LEU | D | 291 | 14.833 | 92.962 | 26.315 | 1.00 | 12.39 | C |
| ATOM | 34305 | CB  | LEU | D | 291 | 14.675 | 94.119 | 27.245 | 1.00 | 13.61 | C |
| ATOM | 34308 | CG  | LEU | D | 291 | 15.007 | 93.842 | 28.706 | 1.00 | 14.29 | C |
| ATOM | 34310 | CD1 | LEU | D | 291 | 14.673 | 95.104 | 29.514 | 1.00 | 17.60 | C |
| ATOM | 34314 | CD2 | LEU | D | 291 | 14.249 | 92.654 | 29.271 | 1.00 | 15.85 | C |
| ATOM | 34318 | C   | LEU | D | 291 | 14.278 | 93.292 | 24.920 | 1.00 | 11.53 | C |
| ATOM | 34319 | O   | LEU | D | 291 | 13.109 | 92.967 | 24.588 | 1.00 | 12.19 | O |
| ATOM | 34321 | N   | LEU | D | 292 | 15.113 | 93.924 | 24.098 | 1.00 | 12.42 | N |
| ATOM | 34322 | CA  | LEU | D | 292 | 14.658 | 94.228 | 22.737 | 1.00 | 11.31 | C |
| ATOM | 34324 | CB  | LEU | D | 292 | 15.646 | 95.102 | 22.042 | 1.00 | 12.06 | C |
| ATOM | 34327 | CG  | LEU | D | 292 | 15.397 | 95.409 | 20.556 | 1.00 | 12.31 | C |
| ATOM | 34329 | CD1 | LEU | D | 292 | 14.030 | 95.992 | 20.350 | 1.00 | 14.29 | C |
| ATOM | 34333 | CD2 | LEU | D | 292 | 16.475 | 96.341 | 20.042 | 1.00 | 12.81 | C |
| ATOM | 34337 | C   | LEU | D | 292 | 14.423 | 92.917 | 21.953 | 1.00 | 12.99 | C |
| ATOM | 34338 | O   | LEU | D | 292 | 13.476 | 92.789 | 21.207 | 1.00 | 13.56 | O |
| ATOM | 34340 | N   | SER | D | 293 | 15.276 | 91.919 | 22.146 | 1.00 | 11.93 | N |
| ATOM | 34341 | CA  | SER | D | 293 | 15.049 | 90.612 | 21.537 | 1.00 | 13.29 | C |
| ATOM | 34343 | CB  | SER | D | 293 | 16.135 | 89.617 | 21.993 | 1.00 | 13.20 | C |
| ATOM | 34346 | OG  | SER | D | 293 | 15.920 | 88.309 | 21.442 | 1.00 | 13.57 | O |
| ATOM | 34348 | C   | SER | D | 293 | 13.685 | 90.012 | 21.857 | 1.00 | 11.49 | C |
| ATOM | 34349 | O   | SER | D | 293 | 13.024 | 89.458 | 21.012 | 1.00 | 13.73 | O |
| ATOM | 34351 | N   | GLN | D | 294 | 13.311 | 90.088 | 23.117 | 1.00 | 12.54 | N |
| ATOM | 34352 | CA  | GLN | D | 294 | 12.009 | 89.628 | 23.598 | 1.00 | 11.76 | C |
| ATOM | 34354 | CB  | GLN | D | 294 | 11.935 | 89.666 | 25.110 | 1.00 | 12.44 | C |
| ATOM | 34357 | CG  | GLN | D | 294 | 12.965 | 88.706 | 25.737 | 1.00 | 13.31 | C |
| ATOM | 34360 | CD  | GLN | D | 294 | 13.013 | 88.753 | 27.237 | 1.00 | 12.94 | C |
| ATOM | 34361 | OE1 | GLN | D | 294 | 11.981 | 88.725 | 27.913 | 1.00 | 14.56 | O |
| ATOM | 34362 | NE2 | GLN | D | 294 | 14.224 | 88.815 | 27.781 | 1.00 | 16.51 | N |
| ATOM | 34365 | C   | GLN | D | 294 | 10.859 | 90.403 | 22.964 | 1.00 | 12.03 | C |
| ATOM | 34366 | O   | GLN | D | 294 | 9.855  | 89.804 | 22.563 | 1.00 | 12.81 | O |
| ATOM | 34368 | N   | SER | D | 295 | 10.989 | 91.723 | 22.898 | 1.00 | 12.87 | N |
| ATOM | 34369 | CA  | SER | D | 295 | 9.995  | 92.597 | 22.236 | 1.00 | 13.13 | C |
| ATOM | 34371 | CB  | SER | D | 295 | 10.380 | 94.062 | 22.417 | 1.00 | 13.50 | C |
| ATOM | 34374 | OG  | SER | D | 295 | 10.391 | 94.391 | 23.823 | 1.00 | 15.06 | O |
| ATOM | 34376 | C   | SER | D | 295 | 9.858  | 92.233 | 20.756 | 1.00 | 12.56 | C |
| ATOM | 34377 | O   | SER | D | 295 | 8.744  | 92.108 | 20.247 | 1.00 | 12.79 | O |
| ATOM | 34379 | N   | LEU | D | 296 | 10.990 | 91.989 | 20.085 | 1.00 | 12.23 | N |
| ATOM | 34380 | CA  | LEU | D | 296 | 10.991 | 91.586 | 18.677 | 1.00 | 12.76 | C |
| ATOM | 34382 | CB  | LEU | D | 296 | 12.389 | 91.582 | 18.121 | 1.00 | 13.28 | C |
| ATOM | 34385 | CG  | LEU | D | 296 | 12.913 | 92.994 | 17.832 | 1.00 | 13.93 | C |

```
ATOM  34387  CD1  LEU D 296      14.386  92.920  17.509  1.00 15.53           C
ATOM  34391  CD2  LEU D 296      12.156  93.668  16.731  1.00 14.34           C
ATOM  34395  C    LEU D 296      10.343  90.208  18.527  1.00 12.90           C
ATOM  34396  O    LEU D 296       9.643  89.938  17.558  1.00 12.41           O
ATOM  34398  N    THR D 297      10.586  89.313  19.486  1.00 11.33           N
ATOM  34399  CA   THR D 297       9.934  88.031  19.433  1.00 12.04           C
ATOM  34401  CB   THR D 297      10.382  87.134  20.602  1.00 12.60           C
ATOM  34403  OG1  THR D 297      11.810  86.864  20.510  1.00 12.74           O
ATOM  34405  CG2  THR D 297       9.611  85.805  20.516  1.00 12.58           C
ATOM  34409  C    THR D 297       8.411  88.222  19.438  1.00 12.21           C
ATOM  34410  O    THR D 297       7.693  87.623  18.601  1.00 11.50           O
ATOM  34412  N    ALA D 298       7.927  89.012  20.395  1.00 12.18           N
ATOM  34413  CA   ALA D 298       6.470  89.224  20.486  1.00 11.89           C
ATOM  34415  CB   ALA D 298       6.176  90.124  21.614  1.00 12.05           C
ATOM  34419  C    ALA D 298       5.904  89.826  19.182  1.00 12.13           C
ATOM  34420  O    ALA D 298       4.904  89.354  18.632  1.00 12.83           O
ATOM  34422  N    MSE D 299       6.584  90.861  18.669  1.00 12.79           N
ATOM  34423  CA   MSE D 299       6.122  91.534  17.426  1.00 15.09           C
ATOM  34425  CB   MSE D 299       6.872  92.830  17.197  1.00 15.65           C
ATOM  34428  CG   MSE D 299       6.533  93.773  18.328  1.00 19.45           C
ATOM  34431  SE   MSE D 299       7.370  95.523  18.080  1.00 34.58          SE
ATOM  34432  CE   MSE D 299       5.877  96.527  17.151  1.00 34.19           C
ATOM  34436  C    MSE D 299       6.175  90.613  16.224  1.00 13.52           C
ATOM  34437  O    MSE D 299       5.368  90.727  15.295  1.00 12.64           O
ATOM  34439  N    THR D 300       7.126  89.682  16.227  1.00 11.20           N
ATOM  34440  CA   THR D 300       7.226  88.716  15.112  1.00 11.97           C
ATOM  34442  CB   THR D 300       8.580  88.047  15.114  1.00 13.39           C
ATOM  34444  OG1  THR D 300       9.598  89.056  15.038  1.00 13.13           O
ATOM  34446  CG2  THR D 300       8.707  87.141  13.954  1.00 14.71           C
ATOM  34450  C    THR D 300       6.067  87.708  15.217  1.00 12.48           C
ATOM  34451  O    THR D 300       5.479  87.322  14.224  1.00 13.07           O
ATOM  34453  N    VAL D 301       5.718  87.269  16.429  1.00 11.34           N
ATOM  34454  CA   VAL D 301       4.530  86.445  16.605  1.00 12.39           C
ATOM  34456  CB   VAL D 301       4.255  86.125  18.089  1.00 11.78           C
ATOM  34458  CG1  VAL D 301       2.989  85.270  18.189  1.00 13.32           C
ATOM  34462  CG2  VAL D 301       5.406  85.343  18.723  1.00 12.51           C
ATOM  34466  C    VAL D 301       3.311  87.184  16.029  1.00 11.14           C
ATOM  34467  O    VAL D 301       2.465  86.619  15.318  1.00 11.78           O
ATOM  34469  N    GLU D 302       3.217  88.479  16.306  1.00 12.24           N
ATOM  34470  CA   GLU D 302       2.108  89.235  15.762  1.00 11.77           C
ATOM  34472  CB   GLU D 302       2.073  90.643  16.348  1.00 12.44           C
ATOM  34475  CG   GLU D 302       1.764  90.677  17.838  1.00 10.85           C
ATOM  34478  CD   GLU D 302       1.595  92.128  18.350  1.00 12.98           C
ATOM  34479  OE1  GLU D 302       2.599  92.881  18.496  1.00 13.54           O
ATOM  34480  OE2  GLU D 302       0.404  92.496  18.595  1.00 12.87           O
ATOM  34481  C    GLU D 302       2.111  89.298  14.217  1.00 11.74           C
ATOM  34482  O    GLU D 302       1.130  88.994  13.577  1.00 12.22           O
ATOM  34484  N    ALA D 303       3.250  89.630  13.628  1.00 12.88           N
ATOM  34485  CA   ALA D 303       3.376  89.685  12.165  1.00 12.77           C
ATOM  34487  CB   ALA D 303       4.775  90.127  11.794  1.00 14.23           C
ATOM  34491  C    ALA D 303       3.072  88.372  11.480  1.00 13.74           C
ATOM  34492  O    ALA D 303       2.527  88.340  10.372  1.00 13.21           O
ATOM  34494  N    MSE D 304       3.453  87.284  12.129  1.00 13.52           N
ATOM  34495  CA   MSE D 304       3.288  85.941  11.577  1.00 14.86           C
ATOM  34497  CB   MSE D 304       4.369  85.056  12.181  1.00 15.35           C
ATOM  34500  CG   MSE D 304       5.739  85.464  11.768  1.00 17.51           C
ATOM  34503  SE   MSE D 304       6.114  84.782   9.931  1.00 26.42          SE
```

| | | | | | | | | | |
|---|---|---|---|---|---|---|---|---|---|
| ATOM | 34504 | CE | MSE | D | 304 | 6.321 | 82.852 | 10.323 | 1.00 22.51 | C |
| ATOM | 34508 | C | MSE | D | 304 | 1.945 | 85.350 | 11.944 | 1.00 14.31 | C |
| ATOM | 34509 | O | MSE | D | 304 | 1.686 | 84.211 | 11.603 | 1.00 14.14 | O |
| ATOM | 34511 | N | VAL | D | 305 | 1.075 | 86.134 | 12.605 | 1.00 14.64 | N |
| ATOM | 34512 | CA | VAL | D | 305 | -0.216 | 85.670 | 13.147 | 1.00 14.79 | C |
| ATOM | 34514 | CB | VAL | D | 305 | -1.342 | 85.735 | 12.101 | 1.00 15.16 | C |
| ATOM | 34516 | CG1 | VAL | D | 305 | -1.592 | 87.170 | 11.738 | 1.00 17.48 | C |
| ATOM | 34520 | CG2 | VAL | D | 305 | -1.028 | 84.980 | 10.876 | 1.00 18.53 | C |
| ATOM | 34524 | C | VAL | D | 305 | -0.011 | 84.279 | 13.801 | 1.00 14.98 | C |
| ATOM | 34525 | O | VAL | D | 305 | -0.727 | 83.306 | 13.543 | 1.00 16.00 | O |
| ATOM | 34527 | N | GLY | D | 306 | 1.028 | 84.245 | 14.637 | 1.00 13.83 | N |
| ATOM | 34528 | CA | GLY | D | 306 | 1.440 | 83.069 | 15.333 | 1.00 14.26 | C |
| ATOM | 34531 | C | GLY | D | 306 | 0.746 | 82.930 | 16.660 | 1.00 14.64 | C |
| ATOM | 34532 | O | GLY | D | 306 | -0.218 | 83.645 | 16.995 | 1.00 14.78 | O |
| ATOM | 34534 | N | HIS | D | 307 | 1.271 | 81.994 | 17.450 | 1.00 15.30 | N |
| ATOM | 34535 | CA | HIS | D | 307 | 0.587 | 81.509 | 18.633 | 1.00 15.87 | C |
| ATOM | 34537 | CB | HIS | D | 307 | 0.735 | 80.010 | 18.748 | 1.00 16.60 | C |
| ATOM | 34540 | CG | HIS | D | 307 | -0.030 | 79.247 | 17.723 | 1.00 18.53 | C |
| ATOM | 34541 | ND1 | HIS | D | 307 | -1.393 | 79.064 | 17.793 | 1.00 20.26 | N |
| ATOM | 34543 | CE1 | HIS | D | 307 | -1.784 | 78.347 | 16.751 | 1.00 20.07 | C |
| ATOM | 34545 | NE2 | HIS | D | 307 | -0.728 | 78.072 | 16.008 | 1.00 24.29 | N |
| ATOM | 34547 | CD2 | HIS | D | 307 | 0.384 | 78.636 | 16.590 | 1.00 23.14 | C |
| ATOM | 34549 | C | HIS | D | 307 | 1.133 | 82.118 | 19.906 | 1.00 15.41 | C |
| ATOM | 34550 | O | HIS | D | 307 | 2.249 | 81.858 | 20.322 | 1.00 15.19 | O |
| ATOM | 34552 | N | ALA | D | 308 | 0.281 | 82.858 | 20.580 | 1.00 14.68 | N |
| ATOM | 34553 | CA | ALA | D | 308 | 0.635 | 83.346 | 21.903 | 1.00 13.93 | C |
| ATOM | 34555 | CB | ALA | D | 308 | -0.407 | 84.355 | 22.378 | 1.00 14.19 | C |
| ATOM | 34559 | C | ALA | D | 308 | 0.770 | 82.178 | 22.908 | 1.00 13.69 | C |
| ATOM | 34560 | O | ALA | D | 308 | 1.351 | 82.343 | 23.971 | 1.00 13.55 | O |
| ATOM | 34562 | N | GLY | D | 309 | 0.154 | 81.040 | 22.592 | 1.00 12.85 | N |
| ATOM | 34563 | CA | GLY | D | 309 | 0.124 | 79.877 | 23.471 | 1.00 12.92 | C |
| ATOM | 34566 | C | GLY | D | 309 | 1.479 | 79.334 | 23.843 | 1.00 12.06 | C |
| ATOM | 34567 | O | GLY | D | 309 | 1.627 | 78.689 | 24.920 | 1.00 12.58 | O |
| ATOM | 34569 | N | SER | D | 310 | 2.484 | 79.625 | 23.002 | 1.00 12.18 | N |
| ATOM | 34570 | CA | SER | D | 310 | 3.878 | 79.226 | 23.320 | 1.00 11.63 | C |
| ATOM | 34572 | CB | SER | D | 310 | 4.854 | 79.675 | 22.249 | 1.00 13.06 | C |
| ATOM | 34575 | OG | SER | D | 310 | 4.517 | 79.133 | 21.012 | 1.00 12.89 | O |
| ATOM | 34577 | C | SER | D | 310 | 4.345 | 79.745 | 24.658 | 1.00 11.24 | C |
| ATOM | 34578 | O | SER | D | 310 | 5.278 | 79.173 | 25.223 | 1.00 11.87 | O |
| ATOM | 34580 | N | PHE | D | 311 | 3.717 | 80.822 | 25.156 | 1.00 11.46 | N |
| ATOM | 34581 | CA | PHE | D | 311 | 4.190 | 81.553 | 26.327 | 1.00 11.45 | C |
| ATOM | 34583 | CB | PHE | D | 311 | 4.362 | 83.034 | 25.962 | 1.00 11.86 | C |
| ATOM | 34586 | CG | PHE | D | 311 | 5.090 | 83.217 | 24.671 | 1.00 12.68 | C |
| ATOM | 34587 | CD1 | PHE | D | 311 | 6.464 | 82.986 | 24.610 | 1.00 12.71 | C |
| ATOM | 34589 | CE1 | PHE | D | 311 | 7.142 | 83.079 | 23.393 | 1.00 15.18 | C |
| ATOM | 34591 | CZ | PHE | D | 311 | 6.410 | 83.330 | 22.205 | 1.00 13.35 | C |
| ATOM | 34593 | CE2 | PHE | D | 311 | 5.064 | 83.573 | 22.278 | 1.00 13.22 | C |
| ATOM | 34595 | CD2 | PHE | D | 311 | 4.411 | 83.491 | 23.490 | 1.00 12.95 | C |
| ATOM | 34597 | C | PHE | D | 311 | 3.274 | 81.352 | 27.536 | 1.00 11.33 | C |
| ATOM | 34598 | O | PHE | D | 311 | 3.411 | 82.045 | 28.542 | 1.00 11.34 | O |
| ATOM | 34600 | N | HIS | D | 312 | 2.399 | 80.340 | 27.472 | 1.00 12.23 | N |
| ATOM | 34601 | CA | HIS | D | 312 | 1.430 | 80.077 | 28.512 | 1.00 11.98 | C |
| ATOM | 34603 | CB | HIS | D | 312 | 0.418 | 79.053 | 28.011 | 1.00 12.87 | C |
| ATOM | 34606 | CG | HIS | D | 312 | -0.741 | 78.889 | 28.923 | 1.00 12.20 | C |
| ATOM | 34607 | ND1 | HIS | D | 312 | -0.634 | 78.257 | 30.141 | 1.00 12.21 | N |
| ATOM | 34609 | CE1 | HIS | D | 312 | -1.808 | 78.276 | 30.738 | 1.00 14.29 | C |
| ATOM | 34611 | NE2 | HIS | D | 312 | -2.684 | 78.877 | 29.947 | 1.00 13.47 | N |

| | | | | | | | | | |
|---|---|---|---|---|---|---|---|---|---|
| ATOM | 34613 | CD2 | HIS | D | 312 | -2.039 | 79.276 | 28.809 | 1.00 13.97 | C |
| ATOM | 34615 | C | HIS | D | 312 | 2.150 | 79.533 | 29.755 | 1.00 12.44 | C |
| ATOM | 34616 | O | HIS | D | 312 | 3.130 | 78.780 | 29.609 | 1.00 12.60 | O |
| ATOM | 34618 | N | PRO | D | 313 | 1.736 | 79.958 | 30.976 | 1.00 13.02 | N |
| ATOM | 34619 | CA | PRO | D | 313 | 2.484 | 79.525 | 32.181 | 1.00 12.52 | C |
| ATOM | 34621 | CB | PRO | D | 313 | 1.754 | 80.185 | 33.361 | 1.00 13.70 | C |
| ATOM | 34624 | CG | PRO | D | 313 | 0.673 | 80.956 | 32.797 | 1.00 14.72 | C |
| ATOM | 34627 | CD | PRO | D | 313 | 0.687 | 80.924 | 31.314 | 1.00 13.62 | C |
| ATOM | 34630 | C | PRO | D | 313 | 2.573 | 78.037 | 32.370 | 1.00 12.38 | C |
| ATOM | 34631 | O | PRO | D | 313 | 3.521 | 77.577 | 32.996 | 1.00 11.44 | O |
| ATOM | 34632 | N | PHE | D | 314 | 1.622 | 77.281 | 31.846 | 1.00 10.95 | N |
| ATOM | 34633 | CA | PHE | D | 314 | 1.676 | 75.839 | 32.004 | 1.00 11.40 | C |
| ATOM | 34635 | CB | PHE | D | 314 | 0.491 | 75.135 | 31.375 | 1.00 11.81 | C |
| ATOM | 34638 | CG | PHE | D | 314 | 0.484 | 73.646 | 31.631 | 1.00 10.78 | C |
| ATOM | 34639 | CD1 | PHE | D | 314 | 0.160 | 73.140 | 32.873 | 1.00 11.56 | C |
| ATOM | 34641 | CE1 | PHE | D | 314 | 0.188 | 71.755 | 33.139 | 1.00 11.29 | C |
| ATOM | 34643 | CZ | PHE | D | 314 | 0.566 | 70.874 | 32.130 | 1.00 10.78 | C |
| ATOM | 34645 | CE2 | PHE | D | 314 | 0.905 | 71.346 | 30.890 | 1.00 13.23 | C |
| ATOM | 34647 | CD2 | PHE | D | 314 | 0.895 | 72.755 | 30.631 | 1.00 11.78 | C |
| ATOM | 34649 | C | PHE | D | 314 | 3.003 | 75.348 | 31.400 | 1.00 11.14 | C |
| ATOM | 34650 | O | PHE | D | 314 | 3.616 | 74.438 | 31.920 | 1.00 11.65 | O |
| ATOM | 34652 | N | LEU | D | 315 | 3.413 | 75.977 | 30.311 | 1.00 10.09 | N |
| ATOM | 34653 | CA | LEU | D | 315 | 4.609 | 75.557 | 29.540 | 1.00 10.12 | C |
| ATOM | 34655 | CB | LEU | D | 315 | 4.541 | 76.033 | 28.083 | 1.00 10.80 | C |
| ATOM | 34658 | CG | LEU | D | 315 | 3.466 | 75.373 | 27.257 | 1.00 11.55 | C |
| ATOM | 34660 | CD1 | LEU | D | 315 | 3.276 | 76.089 | 25.898 | 1.00 13.23 | C |
| ATOM | 34664 | CD2 | LEU | D | 315 | 3.739 | 73.881 | 27.071 | 1.00 12.16 | C |
| ATOM | 34668 | C | LEU | D | 315 | 5.951 | 75.886 | 30.122 | 1.00 10.83 | C |
| ATOM | 34669 | O | LEU | D | 315 | 6.981 | 75.491 | 29.550 | 1.00 12.06 | O |
| ATOM | 34671 | N | HIS | D | 316 | 5.928 | 76.677 | 31.191 | 1.00 10.32 | N |
| ATOM | 34672 | CA | HIS | D | 316 | 7.128 | 77.212 | 31.825 | 1.00 11.06 | C |
| ATOM | 34674 | CB | HIS | D | 316 | 7.330 | 78.679 | 31.392 | 1.00 10.86 | C |
| ATOM | 34677 | CG | HIS | D | 316 | 7.246 | 78.831 | 29.900 | 1.00 10.50 | C |
| ATOM | 34678 | ND1 | HIS | D | 316 | 8.293 | 78.506 | 29.061 | 1.00 11.52 | N |
| ATOM | 34680 | CE1 | HIS | D | 316 | 7.902 | 78.652 | 27.802 | 1.00 12.82 | C |
| ATOM | 34682 | NE2 | HIS | D | 316 | 6.615 | 78.989 | 27.794 | 1.00 10.76 | N |
| ATOM | 34684 | CD2 | HIS | D | 316 | 6.193 | 79.133 | 29.088 | 1.00 11.02 | C |
| ATOM | 34686 | C | HIS | D | 316 | 7.058 | 77.060 | 33.327 | 1.00 10.95 | C |
| ATOM | 34687 | O | HIS | D | 316 | 7.665 | 76.144 | 33.903 | 1.00 12.95 | O |
| ATOM | 34689 | N | ASP | D | 317 | 6.273 | 77.912 | 33.985 | 1.00 10.91 | N |
| ATOM | 34690 | CA | ASP | D | 317 | 6.096 | 77.871 | 35.445 | 1.00 12.75 | C |
| ATOM | 34692 | CB | ASP | D | 317 | 4.940 | 78.798 | 35.801 | 1.00 14.74 | C |
| ATOM | 34695 | CG | ASP | D | 317 | 5.381 | 80.213 | 36.107 | 1.00 22.18 | C |
| ATOM | 34696 | OD1 | ASP | D | 317 | 6.361 | 80.379 | 36.880 | 1.00 36.88 | O |
| ATOM | 34697 | OD2 | ASP | D | 317 | 4.740 | 81.174 | 35.717 | 1.00 23.93 | O |
| ATOM | 34698 | C | ASP | D | 317 | 5.778 | 76.455 | 35.982 | 1.00 12.71 | C |
| ATOM | 34699 | O | ASP | D | 317 | 6.307 | 76.029 | 37.008 | 1.00 12.57 | O |
| ATOM | 34701 | N | VAL | D | 318 | 4.856 | 75.753 | 35.336 | 1.00 13.16 | N |
| ATOM | 34702 | CA | VAL | D | 318 | 4.446 | 74.455 | 35.814 | 1.00 12.62 | C |
| ATOM | 34704 | CB | VAL | D | 318 | 2.995 | 74.120 | 35.410 | 1.00 14.03 | C |
| ATOM | 34706 | CG1 | VAL | D | 318 | 2.577 | 72.781 | 35.938 | 1.00 13.84 | C |
| ATOM | 34710 | CG2 | VAL | D | 318 | 2.021 | 75.189 | 35.945 | 1.00 12.13 | C |
| ATOM | 34714 | C | VAL | D | 318 | 5.407 | 73.341 | 35.369 | 1.00 13.62 | C |
| ATOM | 34715 | O | VAL | D | 318 | 5.839 | 72.544 | 36.195 | 1.00 15.28 | O |
| ATOM | 34717 | N | THR | D | 319 | 5.725 | 73.280 | 34.080 | 1.00 13.43 | N |
| ATOM | 34718 | CA | THR | D | 319 | 6.325 | 72.078 | 33.523 | 1.00 12.31 | C |
| ATOM | 34720 | CB | THR | D | 319 | 5.814 | 71.814 | 32.106 | 1.00 12.29 | C |

| ATOM | 34722 | OG1 | THR | D | 319 | 5.917 | 73.017 | 31.327 | 1.00 | 11.58 | O |
|---|---|---|---|---|---|---|---|---|---|---|---|
| ATOM | 34724 | CG2 | THR | D | 319 | 4.390 | 71.305 | 32.144 | 1.00 | 13.06 | C |
| ATOM | 34728 | C | THR | D | 319 | 7.866 | 72.083 | 33.490 | 1.00 | 11.73 | C |
| ATOM | 34729 | O | THR | D | 319 | 8.461 | 71.020 | 33.595 | 1.00 | 12.29 | O |
| ATOM | 34731 | N | ARG | D | 320 | 8.484 | 73.249 | 33.368 | 1.00 | 11.41 | N |
| ATOM | 34732 | CA | ARG | D | 320 | 9.942 | 73.362 | 33.297 | 1.00 | 11.03 | C |
| ATOM | 34734 | CB | ARG | D | 320 | 10.395 | 73.248 | 31.859 | 1.00 | 12.22 | C |
| ATOM | 34737 | CG | ARG | D | 320 | 11.930 | 73.195 | 31.711 | 1.00 | 13.05 | C |
| ATOM | 34740 | CD | ARG | D | 320 | 12.244 | 72.905 | 30.284 | 1.00 | 14.85 | C |
| ATOM | 34743 | NE | ARG | D | 320 | 13.645 | 72.655 | 29.922 | 1.00 | 13.62 | N |
| ATOM | 34745 | CZ | ARG | D | 320 | 14.295 | 73.236 | 28.915 | 1.00 | 13.83 | C |
| ATOM | 34746 | NH1 | ARG | D | 320 | 13.827 | 74.326 | 28.296 | 1.00 | 13.16 | N |
| ATOM | 34749 | NH2 | ARG | D | 320 | 15.519 | 72.785 | 28.610 | 1.00 | 15.80 | N |
| ATOM | 34752 | C | ARG | D | 320 | 10.435 | 74.653 | 33.940 | 1.00 | 10.93 | C |
| ATOM | 34753 | O | ARG | D | 320 | 10.775 | 75.599 | 33.253 | 1.00 | 10.87 | O |
| ATOM | 34755 | N | PRO | D | 321 | 10.455 | 74.667 | 35.286 | 1.00 | 11.34 | N |
| ATOM | 34756 | CA | PRO | D | 321 | 10.542 | 75.928 | 36.015 | 1.00 | 11.83 | C |
| ATOM | 34758 | CB | PRO | D | 321 | 9.875 | 75.571 | 37.339 | 1.00 | 11.54 | C |
| ATOM | 34761 | CG | PRO | D | 321 | 10.261 | 74.115 | 37.549 | 1.00 | 13.21 | C |
| ATOM | 34764 | CD | PRO | D | 321 | 10.193 | 73.510 | 36.169 | 1.00 | 12.60 | C |
| ATOM | 34767 | C | PRO | D | 321 | 11.939 | 76.510 | 36.198 | 1.00 | 12.20 | C |
| ATOM | 34768 | O | PRO | D | 321 | 12.328 | 76.904 | 37.301 | 1.00 | 14.81 | O |
| ATOM | 34769 | N | HIS | D | 322 | 12.661 | 76.639 | 35.110 | 1.00 | 11.61 | N |
| ATOM | 34770 | CA | HIS | D | 322 | 13.886 | 77.406 | 35.138 | 1.00 | 11.77 | C |
| ATOM | 34772 | CB | HIS | D | 322 | 14.664 | 77.263 | 33.825 | 1.00 | 12.50 | C |
| ATOM | 34775 | CG | HIS | D | 322 | 15.267 | 75.913 | 33.620 | 1.00 | 12.24 | C |
| ATOM | 34776 | ND1 | HIS | D | 322 | 16.375 | 75.470 | 34.324 | 1.00 | 11.80 | N |
| ATOM | 34778 | CE1 | HIS | D | 322 | 16.710 | 74.270 | 33.888 | 1.00 | 14.64 | C |
| ATOM | 34780 | NE2 | HIS | D | 322 | 15.872 | 73.924 | 32.928 | 1.00 | 13.33 | N |
| ATOM | 34782 | CD2 | HIS | D | 322 | 14.977 | 74.943 | 32.725 | 1.00 | 13.98 | C |
| ATOM | 34784 | C | HIS | D | 322 | 13.483 | 78.885 | 35.351 | 1.00 | 12.58 | C |
| ATOM | 34785 | O | HIS | D | 322 | 12.710 | 79.437 | 34.555 | 1.00 | 10.70 | O |
| ATOM | 34787 | N | PRO | D | 323 | 13.994 | 79.505 | 36.424 | 1.00 | 12.51 | N |
| ATOM | 34788 | CA | PRO | D | 323 | 13.464 | 80.836 | 36.723 | 1.00 | 13.03 | C |
| ATOM | 34790 | CB | PRO | D | 323 | 14.343 | 81.330 | 37.868 | 1.00 | 13.48 | C |
| ATOM | 34793 | CG | PRO | D | 323 | 14.750 | 80.028 | 38.601 | 1.00 | 13.71 | C |
| ATOM | 34796 | CD | PRO | D | 323 | 14.877 | 79.001 | 37.495 | 1.00 | 13.70 | C |
| ATOM | 34799 | C | PRO | D | 323 | 13.484 | 81.803 | 35.543 | 1.00 | 12.30 | C |
| ATOM | 34800 | O | PRO | D | 323 | 12.510 | 82.561 | 35.354 | 1.00 | 13.38 | O |
| ATOM | 34801 | N | THR | D | 324 | 14.574 | 81.856 | 34.784 | 1.00 | 11.35 | N |
| ATOM | 34802 | CA | THR | D | 324 | 14.659 | 82.821 | 33.663 | 1.00 | 11.25 | C |
| ATOM | 34804 | CB | THR | D | 324 | 16.084 | 83.180 | 33.278 | 1.00 | 12.94 | C |
| ATOM | 34806 | OG1 | THR | D | 324 | 16.792 | 81.972 | 32.969 | 1.00 | 12.30 | O |
| ATOM | 34808 | CG2 | THR | D | 324 | 16.742 | 83.966 | 34.452 | 1.00 | 13.82 | C |
| ATOM | 34812 | C | THR | D | 324 | 13.855 | 82.416 | 32.450 | 1.00 | 11.77 | C |
| ATOM | 34813 | O | THR | D | 324 | 13.501 | 83.270 | 31.632 | 1.00 | 11.80 | O |
| ATOM | 34815 | N | GLN | D | 325 | 13.567 | 81.116 | 32.313 | 1.00 | 10.64 | N |
| ATOM | 34816 | CA | GLN | D | 325 | 12.634 | 80.677 | 31.258 | 1.00 | 12.07 | C |
| ATOM | 34818 | CB | GLN | D | 325 | 12.578 | 79.168 | 31.168 | 1.00 | 11.20 | C |
| ATOM | 34821 | CG | GLN | D | 325 | 11.817 | 78.696 | 29.958 | 1.00 | 12.69 | C |
| ATOM | 34824 | CD | GLN | D | 325 | 11.721 | 77.180 | 29.856 | 1.00 | 12.90 | C |
| ATOM | 34825 | OE1 | GLN | D | 325 | 12.756 | 76.501 | 29.955 | 1.00 | 13.27 | O |
| ATOM | 34826 | NE2 | GLN | D | 325 | 10.499 | 76.641 | 29.639 | 1.00 | 11.85 | N |
| ATOM | 34829 | C | GLN | D | 325 | 11.243 | 81.236 | 31.573 | 1.00 | 11.11 | C |
| ATOM | 34830 | O | GLN | D | 325 | 10.562 | 81.826 | 30.703 | 1.00 | 11.48 | O |
| ATOM | 34832 | N | ILE | D | 326 | 10.816 | 81.028 | 32.812 | 1.00 | 11.08 | N |
| ATOM | 34833 | CA | ILE | D | 326 | 9.579 | 81.616 | 33.317 | 1.00 | 10.93 | C |

| | | | | | | | | | |
|---|---|---|---|---|---|---|---|---|---|
| ATOM | 34835 | CB | ILE | D | 326 | 9.464 | 81.342 | 34.798 | 1.00 11.04 | C |
| ATOM | 34837 | CG1 | ILE | D | 326 | 9.260 | 79.854 | 35.078 | 1.00 9.81 | C |
| ATOM | 34840 | CD1 | ILE | D | 326 | 9.382 | 79.458 | 36.517 | 1.00 11.64 | C |
| ATOM | 34844 | CG2 | ILE | D | 326 | 8.393 | 82.228 | 35.469 | 1.00 13.60 | C |
| ATOM | 34848 | C | ILE | D | 326 | 9.556 | 83.151 | 33.084 | 1.00 11.99 | C |
| ATOM | 34849 | O | ILE | D | 326 | 8.543 | 83.709 | 32.630 | 1.00 13.14 | O |
| ATOM | 34851 | N | GLU | D | 327 | 10.664 | 83.820 | 33.369 | 1.00 12.99 | N |
| ATOM | 34852 | CA | GLU | D | 327 | 10.780 | 85.261 | 33.193 | 1.00 13.55 | C |
| ATOM | 34854 | CB | GLU | D | 327 | 12.158 | 85.759 | 33.677 | 1.00 14.56 | C |
| ATOM | 34857 | CG | GLU | D | 327 | 12.450 | 87.204 | 33.475 | 1.00 17.01 | C |
| ATOM | 34860 | CD | GLU | D | 327 | 13.874 | 87.605 | 33.892 | 1.00 15.69 | C |
| ATOM | 34861 | OE1 | GLU | D | 327 | 14.457 | 86.934 | 34.727 | 1.00 16.92 | O |
| ATOM | 34862 | OE2 | GLU | D | 327 | 14.392 | 88.619 | 33.398 | 1.00 18.41 | O |
| ATOM | 34863 | C | GLU | D | 327 | 10.534 | 85.670 | 31.755 | 1.00 12.81 | C |
| ATOM | 34864 | O | GLU | D | 327 | 9.758 | 86.598 | 31.472 | 1.00 13.13 | O |
| ATOM | 34866 | N | VAL | D | 328 | 11.238 | 85.011 | 30.844 | 1.00 11.76 | N |
| ATOM | 34867 | CA | VAL | D | 328 | 11.193 | 85.384 | 29.430 | 1.00 11.79 | C |
| ATOM | 34869 | CB | VAL | D | 328 | 12.233 | 84.670 | 28.612 | 1.00 11.07 | C |
| ATOM | 34871 | CG1 | VAL | D | 328 | 11.967 | 84.974 | 27.133 | 1.00 12.00 | C |
| ATOM | 34875 | CG2 | VAL | D | 328 | 13.649 | 85.160 | 28.999 | 1.00 13.49 | C |
| ATOM | 34879 | C | VAL | D | 328 | 9.781 | 85.091 | 28.908 | 1.00 10.86 | C |
| ATOM | 34880 | O | VAL | D | 328 | 9.165 | 85.949 | 28.214 | 1.00 13.07 | O |
| ATOM | 34882 | N | ALA | D | 329 | 9.262 | 83.909 | 29.217 | 1.00 12.11 | N |
| ATOM | 34883 | CA | ALA | D | 329 | 7.908 | 83.569 | 28.776 | 1.00 11.59 | C |
| ATOM | 34885 | CB | ALA | D | 329 | 7.523 | 82.175 | 29.274 | 1.00 11.59 | C |
| ATOM | 34889 | C | ALA | D | 329 | 6.916 | 84.625 | 29.297 | 1.00 12.26 | C |
| ATOM | 34890 | O | ALA | D | 329 | 5.992 | 85.035 | 28.588 | 1.00 13.81 | O |
| ATOM | 34892 | N | GLY | D | 330 | 7.097 | 85.048 | 30.537 | 1.00 11.62 | N |
| ATOM | 34893 | CA | GLY | D | 330 | 6.200 | 86.005 | 31.156 | 1.00 12.84 | C |
| ATOM | 34896 | C | GLY | D | 330 | 6.247 | 87.370 | 30.490 | 1.00 11.73 | C |
| ATOM | 34897 | O | GLY | D | 330 | 5.196 | 88.018 | 30.302 | 1.00 13.93 | O |
| ATOM | 34899 | N | ASN | D | 331 | 7.449 | 87.835 | 30.145 | 1.00 11.28 | N |
| ATOM | 34900 | CA | ASN | D | 331 | 7.616 | 89.099 | 29.417 | 1.00 12.32 | C |
| ATOM | 34902 | CB | ASN | D | 331 | 9.087 | 89.356 | 29.167 | 1.00 12.74 | C |
| ATOM | 34905 | CG | ASN | D | 331 | 9.830 | 89.820 | 30.423 | 1.00 14.47 | C |
| ATOM | 34906 | OD1 | ASN | D | 331 | 9.217 | 90.151 | 31.441 | 1.00 14.72 | O |
| ATOM | 34907 | ND2 | ASN | D | 331 | 11.171 | 89.799 | 30.361 | 1.00 13.22 | N |
| ATOM | 34910 | C | ASN | D | 331 | 6.873 | 89.057 | 28.078 | 1.00 12.48 | C |
| ATOM | 34911 | O | ASN | D | 331 | 6.127 | 89.943 | 27.732 | 1.00 13.03 | O |
| ATOM | 34913 | N | ILE | D | 332 | 7.088 | 87.984 | 27.332 | 1.00 12.01 | N |
| ATOM | 34914 | CA | ILE | D | 332 | 6.479 | 87.867 | 26.030 | 1.00 11.76 | C |
| ATOM | 34916 | CB | ILE | D | 332 | 7.157 | 86.769 | 25.175 | 1.00 11.11 | C |
| ATOM | 34918 | CG1 | ILE | D | 332 | 8.628 | 87.114 | 24.915 | 1.00 12.09 | C |
| ATOM | 34921 | CD1 | ILE | D | 332 | 9.485 | 85.947 | 24.507 | 1.00 12.69 | C |
| ATOM | 34925 | CG2 | ILE | D | 332 | 6.441 | 86.664 | 23.834 | 1.00 9.77 | C |
| ATOM | 34929 | C | ILE | D | 332 | 4.960 | 87.744 | 26.122 | 1.00 11.95 | C |
| ATOM | 34930 | O | ILE | D | 332 | 4.230 | 88.369 | 25.372 | 1.00 12.41 | O |
| ATOM | 34932 | N | ARG | D | 333 | 4.501 | 86.918 | 27.049 | 1.00 12.36 | N |
| ATOM | 34933 | CA | ARG | D | 333 | 3.076 | 86.764 | 27.329 | 1.00 12.24 | C |
| ATOM | 34935 | CB | ARG | D | 333 | 2.894 | 85.768 | 28.503 | 1.00 11.72 | C |
| ATOM | 34938 | CG | ARG | D | 333 | 1.464 | 85.579 | 28.903 | 1.00 13.42 | C |
| ATOM | 34941 | CD | ARG | D | 333 | 1.330 | 84.433 | 29.842 | 1.00 13.73 | C |
| ATOM | 34944 | NE | ARG | D | 333 | 1.840 | 84.675 | 31.187 | 1.00 13.43 | N |
| ATOM | 34946 | CZ | ARG | D | 333 | 2.971 | 84.169 | 31.696 | 1.00 13.57 | C |
| ATOM | 34947 | NH1 | ARG | D | 333 | 3.794 | 83.404 | 30.980 | 1.00 14.23 | N |
| ATOM | 34950 | NH2 | ARG | D | 333 | 3.266 | 84.460 | 32.935 | 1.00 13.75 | N |
| ATOM | 34953 | C | ARG | D | 333 | 2.452 | 88.143 | 27.621 | 1.00 12.85 | C |

| ATOM | 34954 | O   | ARG | D | 333 | 1.383   | 88.472 | 27.090 | 1.00 | 13.01 | O |
|------|-------|-----|-----|---|-----|---------|--------|--------|------|-------|---|
| ATOM | 34956 | N   | LYS | D | 334 | 3.132   | 88.939 | 28.429 | 1.00 | 13.60 | N |
| ATOM | 34957 | CA  | LYS | D | 334 | 2.630   | 90.268 | 28.823 | 1.00 | 15.22 | C |
| ATOM | 34959 | CB  | LYS | D | 334 | 3.534   | 90.907 | 29.872 | 1.00 | 16.11 | C |
| ATOM | 34962 | CG  | LYS | D | 334 | 3.026   | 92.238 | 30.348 | 1.00 | 19.18 | C |
| ATOM | 34965 | CD  | LYS | D | 334 | 3.870   | 92.739 | 31.525 | 1.00 | 20.84 | C |
| ATOM | 34968 | CE  | LYS | D | 334 | 5.346   | 92.798 | 31.175 | 1.00 | 28.32 | C |
| ATOM | 34971 | NZ  | LYS | D | 334 | 5.696   | 93.096 | 29.729 | 1.00 | 33.47 | N |
| ATOM | 34975 | C   | LYS | D | 334 | 2.541   | 91.120 | 27.563 | 1.00 | 13.76 | C |
| ATOM | 34976 | O   | LYS | D | 334 | 1.538   | 91.798 | 27.349 | 1.00 | 12.29 | O |
| ATOM | 34978 | N   | LEU | D | 335 | 3.575   | 91.076 | 26.735 | 1.00 | 13.21 | N |
| ATOM | 34979 | CA  | LEU | D | 335 | 3.565   | 91.890 | 25.514 | 1.00 | 11.87 | C |
| ATOM | 34981 | CB  | LEU | D | 335 | 4.918   | 91.862 | 24.826 | 1.00 | 12.74 | C |
| ATOM | 34984 | CG  | LEU | D | 335 | 6.092   | 92.414 | 25.587 | 1.00 | 13.42 | C |
| ATOM | 34986 | CD1 | LEU | D | 335 | 7.317   | 92.200 | 24.764 | 1.00 | 13.97 | C |
| ATOM | 34990 | CD2 | LEU | D | 335 | 5.884   | 93.890 | 25.733 | 1.00 | 14.48 | C |
| ATOM | 34994 | C   | LEU | D | 335 | 2.464   | 91.498 | 24.543 | 1.00 | 12.30 | C |
| ATOM | 34995 | O   | LEU | D | 335 | 1.924   | 92.371 | 23.820 | 1.00 | 13.00 | O |
| ATOM | 34997 | N   | LEU | D | 336 | 2.108   | 90.210 | 24.458 | 1.00 | 11.74 | N |
| ATOM | 34998 | CA  | LEU | D | 336 | 1.089   | 89.738 | 23.507 | 1.00 | 11.90 | C |
| ATOM | 35000 | CB  | LEU | D | 336 | 1.337   | 88.269 | 23.143 | 1.00 | 11.09 | C |
| ATOM | 35003 | CG  | LEU | D | 336 | 2.636   | 88.087 | 22.352 | 1.00 | 11.43 | C |
| ATOM | 35005 | CD1 | LEU | D | 336 | 2.887   | 86.635 | 22.101 | 1.00 | 13.92 | C |
| ATOM | 35009 | CD2 | LEU | D | 336 | 2.493   | 88.769 | 20.986 | 1.00 | 14.27 | C |
| ATOM | 35013 | C   | LEU | D | 336 | -0.340  | 89.908 | 23.990 | 1.00 | 14.06 | C |
| ATOM | 35014 | O   | LEU | D | 336 | -1.257  | 89.793 | 23.198 | 1.00 | 13.25 | O |
| ATOM | 35016 | N   | GLU | D | 337 | -0.527  | 90.171 | 25.258 | 1.00 | 13.76 | N |
| ATOM | 35017 | CA  | GLU | D | 337 | -1.902  | 90.327 | 25.808 | 1.00 | 16.46 | C |
| ATOM | 35019 | CB  | GLU | D | 337 | -1.869  | 90.680 | 27.273 | 1.00 | 17.69 | C |
| ATOM | 35022 | CG  | GLU | D | 337 | -1.337  | 89.528 | 28.045 | 1.00 | 24.55 | C |
| ATOM | 35025 | CD  | GLU | D | 337 | -2.175  | 89.133 | 29.224 | 1.00 | 32.55 | C |
| ATOM | 35026 | OE1 | GLU | D | 337 | -3.245  | 89.778 | 29.443 | 1.00 | 36.13 | O |
| ATOM | 35027 | OE2 | GLU | D | 337 | -1.725  | 88.168 | 29.911 | 1.00 | 38.74 | O |
| ATOM | 35028 | C   | GLU | D | 337 | -2.596  | 91.410 | 25.029 | 1.00 | 15.96 | C |
| ATOM | 35029 | O   | GLU | D | 337 | -2.027  | 92.465 | 24.815 | 1.00 | 15.85 | O |
| ATOM | 35031 | N   | GLY | D | 338 | -3.823  | 91.140 | 24.600 | 1.00 | 15.74 | N |
| ATOM | 35032 | CA  | GLY | D | 338 | -4.568  | 92.134 | 23.866 | 1.00 | 16.06 | C |
| ATOM | 35035 | C   | GLY | D | 338 | -4.250  | 92.254 | 22.400 | 1.00 | 15.96 | C |
| ATOM | 35036 | O   | GLY | D | 338 | -4.900  | 93.020 | 21.710 | 1.00 | 15.42 | O |
| ATOM | 35038 | N   | SER | D | 339 | -3.299  | 91.469 | 21.884 | 1.00 | 14.72 | N |
| ATOM | 35039 | CA  | SER | D | 339 | -3.030  | 91.517 | 20.455 | 1.00 | 15.13 | C |
| ATOM | 35041 | CB  | SER | D | 339 | -1.743  | 90.776 | 20.104 | 1.00 | 15.20 | C |
| ATOM | 35044 | OG  | SER | D | 339 | -1.511  | 90.694 | 18.729 | 1.00 | 14.84 | O |
| ATOM | 35046 | C   | SER | D | 339 | -4.187  | 90.883 | 19.709 | 1.00 | 14.97 | C |
| ATOM | 35047 | O   | SER | D | 339 | -4.725  | 89.858 | 20.152 | 1.00 | 14.67 | O |
| ATOM | 35049 | N   | ARG | D | 340 | -4.583  | 91.487 | 18.594 | 1.00 | 14.51 | N |
| ATOM | 35050 | CA  | ARG | D | 340 | -5.512  | 90.854 | 17.673 | 1.00 | 16.06 | C |
| ATOM | 35052 | CB  | ARG | D | 340 | -6.610  | 91.848 | 17.264 | 1.00 | 16.70 | C |
| ATOM | 35055 | CG  | ARG | D | 340 | -7.480  | 92.290 | 18.431 | 1.00 | 20.07 | C |
| ATOM | 35058 | CD  | ARG | D | 340 | -8.368  | 93.455 | 18.033 | 1.00 | 22.93 | C |
| ATOM | 35061 | NE  | ARG | D | 340 | -9.237  | 93.097 | 16.928 | 1.00 | 28.89 | N |
| ATOM | 35063 | CZ  | ARG | D | 340 | -9.799  | 93.953 | 16.065 | 1.00 | 31.04 | C |
| ATOM | 35064 | NH1 | ARG | D | 340 | -9.605  | 95.279 | 16.144 | 1.00 | 29.51 | N |
| ATOM | 35067 | NH2 | ARG | D | 340 | -10.580 | 93.462 | 15.110 | 1.00 | 31.69 | N |
| ATOM | 35070 | C   | ARG | D | 340 | -4.808  | 90.279 | 16.456 | 1.00 | 15.54 | C |
| ATOM | 35071 | O   | ARG | D | 340 | -5.451  | 89.847 | 15.548 | 1.00 | 15.69 | O |
| ATOM | 35073 | N   | PHE | D | 341 | -3.473  | 90.346 | 16.412 | 1.00 | 14.14 | N |

```
ATOM  35074 CA  PHE D 341     -2.689  89.648  15.422  1.00 14.11           C
ATOM  35076 CB  PHE D 341     -1.380  90.356  15.194  1.00 13.99           C
ATOM  35079 CG  PHE D 341     -1.449  91.562  14.324  1.00 13.26           C
ATOM  35080 CD1 PHE D 341     -2.010  91.518  13.064  1.00 15.31           C
ATOM  35082 CE1 PHE D 341     -2.016  92.633  12.258  1.00 15.29           C
ATOM  35084 CZ  PHE D 341     -1.456  93.803  12.703  1.00 14.81           C
ATOM  35086 CE2 PHE D 341     -0.928  93.885  13.953  1.00 14.71           C
ATOM  35088 CD2 PHE D 341     -0.886  92.755  14.757  1.00 17.15           C
ATOM  35090 C   PHE D 341     -2.338  88.237  15.923  1.00 15.33           C
ATOM  35091 O   PHE D 341     -2.533  87.233  15.217  1.00 14.58           O
ATOM  35093 N   ALA D 342     -1.758  88.154  17.119  1.00 16.09           N
ATOM  35094 CA  ALA D 342     -1.442  86.830  17.692  1.00 16.12           C
ATOM  35096 CB  ALA D 342     -0.607  86.983  18.920  1.00 16.07           C
ATOM  35100 C   ALA D 342     -2.698  86.048  18.051  1.00 17.71           C
ATOM  35101 O   ALA D 342     -3.711  86.631  18.412  1.00 17.86           O
ATOM  35103 N   VAL D 343     -2.640  84.724  17.905  1.00 17.50           N
ATOM  35104 CA  VAL D 343     -3.747  83.844  18.299  1.00 18.13           C
ATOM  35106 CB  VAL D 343     -3.809  82.598  17.370  1.00 18.27           C
ATOM  35108 CG1 VAL D 343     -4.944  81.680  17.783  1.00 19.19           C
ATOM  35112 CG2 VAL D 343     -3.950  83.049  15.914  1.00 20.38           C
ATOM  35116 C   VAL D 343     -3.591  83.427  19.759  1.00 18.41           C
ATOM  35117 O   VAL D 343     -2.519  82.974  20.185  1.00 17.88           O
ATOM  35119 N   HIS D 344     -4.653  83.560  20.527  1.00 19.03           N
ATOM  35120 CA  HIS D 344     -4.581  83.281  21.967  1.00 20.35           C
ATOM  35122 CB  HIS D 344     -5.336  84.384  22.725  1.00 19.86           C
ATOM  35125 CG  HIS D 344     -4.758  85.738  22.496  1.00 20.08           C
ATOM  35126 ND1 HIS D 344     -3.716  86.238  23.245  1.00 21.82           N
ATOM  35128 CE1 HIS D 344     -3.375  87.427  22.777  1.00 22.55           C
ATOM  35130 NE2 HIS D 344     -4.154  87.713  21.748  1.00 19.73           N
ATOM  35132 CD2 HIS D 344     -5.030  86.672  21.551  1.00 23.91           C
ATOM  35134 C   HIS D 344     -5.055  81.869  22.366  1.00 22.01           C
ATOM  35135 O   HIS D 344     -6.096  81.395  21.880  1.00 21.29           O
ATOM  35137 N   HIS D 345     -4.271  81.206  23.235  1.00 22.39           N
ATOM  35138 CA  HIS D 345     -4.603  79.843  23.679  1.00 22.83           C
ATOM  35140 CB  HIS D 345     -3.639  79.325  24.798  1.00 22.72           C
ATOM  35143 CG  HIS D 345     -4.142  78.091  25.481  1.00 23.36           C
ATOM  35144 ND1 HIS D 345     -4.055  76.836  24.911  1.00 26.04           N
ATOM  35146 CE1 HIS D 345     -4.614  75.952  25.719  1.00 25.17           C
ATOM  35148 NE2 HIS D 345     -5.104  76.592  26.770  1.00 24.85           N
ATOM  35150 CD2 HIS D 345     -4.830  77.931  26.642  1.00 24.62           C
ATOM  35152 C   HIS D 345     -6.078  79.780  24.156  1.00 24.05           C
ATOM  35153 O   HIS D 345     -6.821  78.855  23.809  1.00 24.89           O
ATOM  35155 N   GLU D 346     -6.487  80.760  24.957  1.00 25.21           N
ATOM  35156 CA  GLU D 346     -7.817  80.708  25.584  1.00 27.08           C
ATOM  35158 CB  GLU D 346     -7.922  81.667  26.789  1.00 27.88           C
ATOM  35161 CG  GLU D 346     -7.974  83.165  26.463  1.00 30.21           C
ATOM  35164 CD  GLU D 346     -6.594  83.815  26.285  1.00 33.23           C
ATOM  35165 OE1 GLU D 346     -5.566  83.094  26.140  1.00 29.39           O
ATOM  35166 OE2 GLU D 346     -6.558  85.070  26.273  1.00 37.08           O
ATOM  35167 C   GLU D 346     -8.942  80.956  24.574  1.00 27.79           C
ATOM  35168 O   GLU D 346    -10.103  80.679  24.853  1.00 26.34           O
ATOM  35170 N   GLU D 347     -8.596  81.421  23.383  1.00 28.83           N
ATOM  35171 CA  GLU D 347     -9.567  81.475  22.292  1.00 30.45           C
ATOM  35173 CB  GLU D 347     -9.347  82.747  21.470  1.00 31.34           C
ATOM  35176 CG  GLU D 347     -9.773  83.981  22.259  1.00 34.42           C
ATOM  35179 CD  GLU D 347     -8.949  85.192  21.938  1.00 40.24           C
ATOM  35180 OE1 GLU D 347     -8.791  85.490  20.724  1.00 42.53           O
```

| | | | | | | | | | |
|---|---|---|---|---|---|---|---|---|---|
| ATOM | 35181 | OE2 | GLU | D | 347 | -8.460 | 85.839 | 22.909 | 1.00 44.05 | O |
| ATOM | 35182 | C | GLU | D | 347 | -9.509 | 80.235 | 21.409 | 1.00 30.65 | C |
| ATOM | 35183 | O | GLU | D | 347 | -10.550 | 79.746 | 20.974 | 1.00 29.51 | O |
| ATOM | 35185 | N | GLU | D | 348 | -8.300 | 79.727 | 21.150 | 1.00 31.04 | N |
| ATOM | 35186 | CA | GLU | D | 348 | -8.121 | 78.538 | 20.307 | 1.00 32.26 | C |
| ATOM | 35188 | CB | GLU | D | 348 | -6.672 | 78.086 | 20.309 | 1.00 32.66 | C |
| ATOM | 35191 | CG | GLU | D | 348 | -5.791 | 78.914 | 19.536 | 1.00 34.44 | C |
| ATOM | 35194 | CD | GLU | D | 348 | -4.371 | 78.452 | 19.685 | 1.00 37.50 | C |
| ATOM | 35195 | OE1 | GLU | D | 348 | -3.791 | 78.104 | 18.648 | 1.00 40.34 | O |
| ATOM | 35196 | OE2 | GLU | D | 348 | -3.853 | 78.402 | 20.832 | 1.00 38.21 | O |
| ATOM | 35197 | C | GLU | D | 348 | -8.889 | 77.340 | 20.802 | 1.00 33.20 | C |
| ATOM | 35198 | O | GLU | D | 348 | -9.474 | 76.587 | 20.016 | 1.00 33.75 | O |
| ATOM | 35200 | N | VAL | D | 349 | -8.820 | 77.127 | 22.107 | 1.00 33.81 | N |
| ATOM | 35201 | CA | VAL | D | 349 | -9.492 | 75.993 | 22.719 | 1.00 34.86 | C |
| ATOM | 35203 | CB | VAL | D | 349 | -9.062 | 75.786 | 24.199 | 1.00 34.87 | C |
| ATOM | 35205 | CG1 | VAL | D | 349 | -7.572 | 75.462 | 24.264 | 1.00 35.52 | C |
| ATOM | 35209 | CG2 | VAL | D | 349 | -9.415 | 77.016 | 25.089 | 1.00 35.25 | C |
| ATOM | 35213 | C | VAL | D | 349 | -11.007 | 76.155 | 22.612 | 1.00 34.87 | C |
| ATOM | 35214 | O | VAL | D | 349 | -11.738 | 75.550 | 23.397 | 1.00 36.70 | O |
| ATOM | 35216 | N | ASP | D | 354 | -3.270 | 64.467 | 6.006 | 1.00 60.10 | N |
| ATOM | 35217 | CA | ASP | D | 354 | -2.982 | 63.987 | 4.654 | 1.00 60.02 | C |
| ATOM | 35219 | CB | ASP | D | 354 | -4.142 | 63.110 | 4.138 | 1.00 60.11 | C |
| ATOM | 35222 | CG | ASP | D | 354 | -5.469 | 63.854 | 4.057 | 1.00 61.14 | C |
| ATOM | 35223 | OD1 | ASP | D | 354 | -5.474 | 65.107 | 4.005 | 1.00 62.88 | O |
| ATOM | 35224 | OD2 | ASP | D | 354 | -6.522 | 63.172 | 4.030 | 1.00 61.80 | O |
| ATOM | 35225 | C | ASP | D | 354 | -2.642 | 65.132 | 3.668 | 1.00 59.75 | C |
| ATOM | 35226 | O | ASP | D | 354 | -2.871 | 65.009 | 2.455 | 1.00 58.40 | O |
| ATOM | 35228 | N | GLU | D | 355 | -2.117 | 66.242 | 4.219 | 1.00 59.87 | N |
| ATOM | 35229 | CA | GLU | D | 355 | -1.584 | 67.392 | 3.433 | 1.00 59.89 | C |
| ATOM | 35231 | CB | GLU | D | 355 | -2.641 | 68.486 | 3.300 | 1.00 60.02 | C |
| ATOM | 35234 | CG | GLU | D | 355 | -3.964 | 68.011 | 2.736 | 1.00 60.46 | C |
| ATOM | 35237 | CD | GLU | D | 355 | -5.058 | 69.032 | 2.917 | 1.00 60.90 | C |
| ATOM | 35238 | OE1 | GLU | D | 355 | -4.732 | 70.226 | 3.142 | 1.00 62.56 | O |
| ATOM | 35239 | OE2 | GLU | D | 355 | -6.242 | 68.630 | 2.839 | 1.00 61.67 | O |
| ATOM | 35240 | C | GLU | D | 355 | -0.289 | 68.032 | 3.997 | 1.00 59.54 | C |
| ATOM | 35241 | O | GLU | D | 355 | 0.211 | 69.014 | 3.441 | 1.00 59.26 | O |
| ATOM | 35243 | N | GLY | D | 356 | 0.240 | 67.486 | 5.095 | 1.00 59.34 | N |
| ATOM | 35244 | CA | GLY | D | 356 | 1.528 | 67.923 | 5.655 | 1.00 59.00 | C |
| ATOM | 35247 | C | GLY | D | 356 | 1.634 | 69.399 | 6.025 | 1.00 58.76 | C |
| ATOM | 35248 | O | GLY | D | 356 | 2.726 | 69.977 | 5.955 | 1.00 59.01 | O |
| ATOM | 35250 | N | ILE | D | 357 | 0.509 | 70.002 | 6.425 | 1.00 57.92 | N |
| ATOM | 35251 | CA | ILE | D | 357 | 0.459 | 71.431 | 6.805 | 1.00 57.25 | C |
| ATOM | 35253 | CB | ILE | D | 357 | -1.034 | 71.939 | 6.944 | 1.00 57.44 | C |
| ATOM | 35255 | CG1 | ILE | D | 357 | -1.706 | 72.018 | 5.558 | 1.00 58.14 | C |
| ATOM | 35258 | CD1 | ILE | D | 357 | -3.194 | 71.627 | 5.556 | 1.00 58.14 | C |
| ATOM | 35262 | CG2 | ILE | D | 357 | -1.110 | 73.311 | 7.672 | 1.00 57.70 | C |
| ATOM | 35266 | C | ILE | D | 357 | 1.245 | 71.706 | 8.108 | 1.00 54.75 | C |
| ATOM | 35267 | O | ILE | D | 357 | 1.337 | 70.831 | 8.985 | 1.00 55.07 | O |
| ATOM | 35269 | N | LEU | D | 358 | 1.814 | 72.916 | 8.198 | 1.00 51.60 | N |
| ATOM | 35270 | CA | LEU | D | 358 | 2.391 | 73.440 | 9.437 | 1.00 48.56 | C |
| ATOM | 35272 | CB | LEU | D | 358 | 3.612 | 74.341 | 9.151 | 1.00 49.42 | C |
| ATOM | 35275 | CG | LEU | D | 358 | 4.632 | 74.576 | 10.294 | 1.00 50.70 | C |
| ATOM | 35277 | CD1 | LEU | D | 358 | 5.922 | 73.755 | 10.114 | 1.00 50.74 | C |
| ATOM | 35281 | CD2 | LEU | D | 358 | 5.018 | 76.067 | 10.464 | 1.00 49.83 | C |
| ATOM | 35285 | C | LEU | D | 358 | 1.267 | 74.211 | 10.170 | 1.00 46.91 | C |
| ATOM | 35286 | O | LEU | D | 358 | 0.687 | 75.178 | 9.641 | 1.00 47.93 | O |
| ATOM | 35288 | N | ARG | D | 359 | 0.930 | 73.726 | 11.359 | 1.00 43.28 | N |

```
ATOM  35289  CA   ARG D 359     -0.077  74.343  12.244  1.00 40.57           C
ATOM  35291  CB   ARG D 359     -1.060  73.267  12.706  1.00 40.08           C
ATOM  35294  CG   ARG D 359     -1.438  72.357  11.537  1.00 42.99           C
ATOM  35297  CD   ARG D 359     -2.622  71.446  11.787  1.00 44.05           C
ATOM  35300  NE   ARG D 359     -3.380  71.231  10.548  1.00 48.11           N
ATOM  35302  CZ   ARG D 359     -4.222  70.215  10.320  1.00 49.75           C
ATOM  35303  NH1  ARG D 359     -4.419  69.268  11.242  1.00 50.60           N
ATOM  35306  NH2  ARG D 359     -4.875  70.142   9.151  1.00 49.79           N
ATOM  35309  C    ARG D 359      0.610  74.985  13.448  1.00 34.21           C
ATOM  35310  O    ARG D 359      0.149  76.003  13.966  1.00 34.83           O
ATOM  35312  N   AGLN D 360      1.730  74.429  13.867  0.50 31.05           N
ATOM  35313  N   BGLN D 360      1.686  74.344  13.914  0.50 30.74           N
ATOM  35314  CA  AGLN D 360      2.409  74.999  14.993  0.50 27.70           C
ATOM  35315  CA  BGLN D 360      2.510  74.853  15.011  0.50 26.73           C
ATOM  35318  CB  AGLN D 360      2.861  73.883  15.938  0.50 27.81           C
ATOM  35319  CB  BGLN D 360      3.301  73.694  15.700  0.50 27.72           C
ATOM  35324  CG  AGLN D 360      2.971  74.290  17.398  0.50 26.24           C
ATOM  35325  CG  BGLN D 360      2.528  72.731  16.729  0.50 26.91           C
ATOM  35330  CD  AGLN D 360      2.050  75.448  17.765  0.50 24.07           C
ATOM  35331  CD  BGLN D 360      3.260  72.596  18.100  0.50 27.38           C
ATOM  35332  OE1 AGLN D 360      2.514  76.587  17.842  0.50 13.97           O
ATOM  35333  OE1 BGLN D 360      3.348  71.518  18.750  0.50 27.67           O
ATOM  35334  NE2 AGLN D 360      0.718  75.162  17.946  0.50 21.58           N
ATOM  35335  NE2 BGLN D 360      3.753  73.711  18.555  0.50 31.22           N
ATOM  35340  C   AGLN D 360      3.554  75.906  14.528  0.50 25.35           C
ATOM  35341  C   BGLN D 360      3.481  75.963  14.493  0.50 25.07           C
ATOM  35342  O   AGLN D 360      4.101  75.768  13.420  0.50 24.09           O
ATOM  35343  O   BGLN D 360      3.836  76.020  13.304  0.50 23.91           O
ATOM  35346  N    ASP D 361      3.904  76.859  15.379  1.00 22.12           N
ATOM  35347  CA   ASP D 361      4.971  77.810  15.046  1.00 20.19           C
ATOM  35349  CB   ASP D 361      5.056  78.949  16.063  1.00 19.24           C
ATOM  35352  CG   ASP D 361      3.872  79.913  15.969  1.00 19.01           C
ATOM  35353  OD1  ASP D 361      3.114  79.868  14.972  1.00 20.05           O
ATOM  35354  OD2  ASP D 361      3.750  80.746  16.866  1.00 19.12           O
ATOM  35355  C    ASP D 361      6.274  77.053  15.023  1.00 17.69           C
ATOM  35356  O    ASP D 361      6.413  76.020  15.685  1.00 15.90           O
ATOM  35358  N    ARG D 362      7.230  77.542  14.251  1.00 14.66           N
ATOM  35359  CA   ARG D 362      8.546  76.900  14.216  1.00 14.42           C
ATOM  35361  CB   ARG D 362      9.294  77.236  12.920  1.00 14.28           C
ATOM  35364  CG   ARG D 362      8.500  76.807  11.713  1.00 15.47           C
ATOM  35367  CD   ARG D 362      9.159  77.280  10.413  1.00 17.39           C
ATOM  35370  NE   ARG D 362      8.447  76.780   9.211  1.00 18.26           N
ATOM  35372  CZ   ARG D 362      7.496  77.465   8.573  1.00 19.40           C
ATOM  35373  NH1  ARG D 362      7.170  78.681   8.973  1.00 18.04           N
ATOM  35376  NH2  ARG D 362      6.904  76.952   7.484  1.00 21.64           N
ATOM  35379  C    ARG D 362      9.341  77.321  15.447  1.00 13.94           C
ATOM  35380  O    ARG D 362      8.876  78.113  16.267  1.00 14.17           O
ATOM  35382  N    TYR D 363     10.525  76.747  15.598  1.00 13.86           N
ATOM  35383  CA   TYR D 363     11.261  76.975  16.846  1.00 14.12           C
ATOM  35385  CB   TYR D 363     12.492  76.049  16.915  1.00 15.42           C
ATOM  35388  CG   TYR D 363     12.197  74.553  17.044  1.00 13.40           C
ATOM  35389  CD1  TYR D 363     10.906  74.004  16.937  1.00 13.96           C
ATOM  35391  CE1  TYR D 363     10.730  72.610  17.048  1.00 14.43           C
ATOM  35393  CZ   TYR D 363     11.861  71.806  17.222  1.00 16.43           C
ATOM  35394  OH   TYR D 363     11.810  70.430  17.340  1.00 20.91           O
ATOM  35396  CE2  TYR D 363     13.081  72.355  17.334  1.00 16.75           C
ATOM  35398  CD2  TYR D 363     13.273  73.663  17.247  1.00 15.34           C
```

| | | | | | | | | | |
|---|---|---|---|---|---|---|---|---|---|
| ATOM | 35400 | C | TYR | D | 363 | 11.682 | 78.393 | 17.196 | 1.00 14.15 | C |
| ATOM | 35401 | O | TYR | D | 363 | 11.764 | 78.719 | 18.379 | 1.00 14.70 | O |
| ATOM | 35403 | N | PRO | D | 364 | 12.044 | 79.201 | 16.203 | 1.00 13.29 | N |
| ATOM | 35404 | CA | PRO | D | 364 | 12.488 | 80.598 | 16.537 | 1.00 13.81 | C |
| ATOM | 35406 | CB | PRO | D | 364 | 12.664 | 81.235 | 15.157 | 1.00 13.53 | C |
| ATOM | 35409 | CG | PRO | D | 364 | 13.112 | 79.967 | 14.296 | 1.00 12.87 | C |
| ATOM | 35412 | CD | PRO | D | 364 | 12.197 | 78.907 | 14.765 | 1.00 14.43 | C |
| ATOM | 35415 | C | PRO | D | 364 | 11.463 | 81.282 | 17.409 | 1.00 13.21 | C |
| ATOM | 35416 | O | PRO | D | 364 | 11.848 | 82.090 | 18.238 | 1.00 13.80 | O |
| ATOM | 35417 | N | LEU | D | 365 | 10.169 | 80.991 | 17.222 | 1.00 13.12 | N |
| ATOM | 35418 | CA | LEU | D | 365 | 9.110 | 81.559 | 18.081 | 1.00 13.53 | C |
| ATOM | 35420 | CB | LEU | D | 365 | 7.860 | 81.888 | 17.274 | 1.00 14.15 | C |
| ATOM | 35423 | CG | LEU | D | 365 | 8.136 | 82.900 | 16.166 | 1.00 14.04 | C |
| ATOM | 35425 | CD1 | LEU | D | 365 | 6.844 | 83.051 | 15.344 | 1.00 14.91 | C |
| ATOM | 35429 | CD2 | LEU | D | 365 | 8.632 | 84.275 | 16.690 | 1.00 14.32 | C |
| ATOM | 35433 | C | LEU | D | 365 | 8.768 | 80.624 | 19.237 | 1.00 12.50 | C |
| ATOM | 35434 | O | LEU | D | 365 | 8.767 | 81.013 | 20.412 | 1.00 13.41 | O |
| ATOM | 35436 | N | ARG | D | 366 | 8.473 | 79.368 | 18.910 | 1.00 12.30 | N |
| ATOM | 35437 | CA | ARG | D | 366 | 7.899 | 78.459 | 19.898 | 1.00 12.52 | C |
| ATOM | 35439 | CB | ARG | D | 366 | 7.390 | 77.194 | 19.220 | 1.00 13.41 | C |
| ATOM | 35442 | CG | ARG | D | 366 | 6.716 | 76.256 | 20.175 | 1.00 13.76 | C |
| ATOM | 35445 | CD | ARG | D | 366 | 5.774 | 75.276 | 19.486 | 1.00 13.47 | C |
| ATOM | 35448 | NE | ARG | D | 366 | 6.292 | 74.656 | 18.269 | 1.00 15.62 | N |
| ATOM | 35450 | CZ | ARG | D | 366 | 6.643 | 73.377 | 18.150 | 1.00 18.63 | C |
| ATOM | 35451 | NH1 | ARG | D | 366 | 6.641 | 72.569 | 19.212 | 1.00 17.45 | N |
| ATOM | 35454 | NH2 | ARG | D | 366 | 7.022 | 72.905 | 16.962 | 1.00 17.94 | N |
| ATOM | 35457 | C | ARG | D | 366 | 8.904 | 78.083 | 21.008 | 1.00 12.90 | C |
| ATOM | 35458 | O | ARG | D | 366 | 8.488 | 77.735 | 22.120 | 1.00 12.96 | O |
| ATOM | 35460 | N | THR | D | 367 | 10.204 | 78.126 | 20.697 | 1.00 12.84 | N |
| ATOM | 35461 | CA | THR | D | 367 | 11.208 | 77.762 | 21.695 | 1.00 12.61 | C |
| ATOM | 35463 | CB | THR | D | 367 | 12.241 | 76.713 | 21.178 | 1.00 13.03 | C |
| ATOM | 35465 | OG1 | THR | D | 367 | 13.159 | 77.307 | 20.234 | 1.00 14.59 | O |
| ATOM | 35467 | CG2 | THR | D | 367 | 11.543 | 75.382 | 20.655 | 1.00 11.58 | C |
| ATOM | 35471 | C | THR | D | 367 | 11.985 | 78.982 | 22.233 | 1.00 12.25 | C |
| ATOM | 35472 | O | THR | D | 367 | 13.042 | 78.819 | 22.844 | 1.00 12.95 | O |
| ATOM | 35474 | N | SER | D | 368 | 11.494 | 80.190 | 21.956 | 1.00 11.79 | N |
| ATOM | 35475 | CA | SER | D | 368 | 12.186 | 81.405 | 22.334 | 1.00 12.01 | C |
| ATOM | 35477 | CB | SER | D | 368 | 11.525 | 82.680 | 21.756 | 1.00 12.18 | C |
| ATOM | 35480 | OG | SER | D | 368 | 10.153 | 82.724 | 22.032 | 1.00 12.04 | O |
| ATOM | 35482 | C | SER | D | 368 | 12.442 | 81.524 | 23.847 | 1.00 12.28 | C |
| ATOM | 35483 | O | SER | D | 368 | 13.538 | 81.936 | 24.224 | 1.00 12.15 | O |
| ATOM | 35485 | N | PRO | D | 369 | 11.483 | 81.159 | 24.715 | 1.00 11.59 | N |
| ATOM | 35486 | CA | PRO | D | 369 | 11.818 | 81.262 | 26.150 | 1.00 11.54 | C |
| ATOM | 35488 | CB | PRO | D | 369 | 10.507 | 80.947 | 26.849 | 1.00 12.36 | C |
| ATOM | 35491 | CG | PRO | D | 369 | 9.441 | 81.310 | 25.846 | 1.00 11.43 | C |
| ATOM | 35494 | CD | PRO | D | 369 | 10.062 | 80.790 | 24.555 | 1.00 11.17 | C |
| ATOM | 35497 | C | PRO | D | 369 | 12.903 | 80.278 | 26.616 | 1.00 11.64 | C |
| ATOM | 35498 | O | PRO | D | 369 | 13.726 | 80.604 | 27.488 | 1.00 11.64 | O |
| ATOM | 35499 | N | GLN | D | 370 | 12.896 | 79.090 | 25.991 | 1.00 10.61 | N |
| ATOM | 35500 | CA | GLN | D | 370 | 13.862 | 78.036 | 26.269 | 1.00 10.72 | C |
| ATOM | 35502 | CB | GLN | D | 370 | 13.376 | 76.714 | 25.681 | 1.00 11.22 | C |
| ATOM | 35505 | CG | GLN | D | 370 | 12.127 | 76.149 | 26.282 | 1.00 10.48 | C |
| ATOM | 35508 | CD | GLN | D | 370 | 10.827 | 76.703 | 25.702 | 1.00 10.79 | C |
| ATOM | 35509 | OE1 | GLN | D | 370 | 10.853 | 77.598 | 24.868 | 1.00 13.82 | O |
| ATOM | 35510 | NE2 | GLN | D | 370 | 9.686 | 76.202 | 26.190 | 1.00 12.05 | N |
| ATOM | 35513 | C | GLN | D | 370 | 15.255 | 78.419 | 25.708 | 1.00 11.16 | C |
| ATOM | 35514 | O | GLN | D | 370 | 16.291 | 78.019 | 26.222 | 1.00 12.64 | O |

| ATOM | 35516 | N | TRP | D | 371 | 15.240 | 79.238 | 24.668 | 1.00 | 11.56 | N |
|---|---|---|---|---|---|---|---|---|---|---|---|
| ATOM | 35517 | CA | TRP | D | 371 | 16.491 | 79.697 | 24.047 | 1.00 | 11.86 | C |
| ATOM | 35519 | CB | TRP | D | 371 | 16.245 | 80.083 | 22.616 | 1.00 | 12.44 | C |
| ATOM | 35522 | CG | TRP | D | 371 | 17.477 | 80.265 | 21.830 | 1.00 | 12.22 | C |
| ATOM | 35523 | CD1 | TRP | D | 371 | 18.114 | 81.447 | 21.508 | 1.00 | 13.31 | C |
| ATOM | 35525 | NE1 | TRP | D | 371 | 19.203 | 81.200 | 20.700 | 1.00 | 13.37 | N |
| ATOM | 35527 | CE2 | TRP | D | 371 | 19.291 | 79.850 | 20.494 | 1.00 | 11.73 | C |
| ATOM | 35528 | CD2 | TRP | D | 371 | 18.232 | 79.231 | 21.189 | 1.00 | 11.66 | C |
| ATOM | 35529 | CE3 | TRP | D | 371 | 18.124 | 77.842 | 21.133 | 1.00 | 11.87 | C |
| ATOM | 35531 | CZ3 | TRP | D | 371 | 19.032 | 77.126 | 20.419 | 1.00 | 13.78 | C |
| ATOM | 35533 | CH2 | TRP | D | 371 | 20.099 | 77.749 | 19.777 | 1.00 | 12.47 | C |
| ATOM | 35535 | CZ2 | TRP | D | 371 | 20.225 | 79.120 | 19.767 | 1.00 | 10.97 | C |
| ATOM | 35537 | C | TRP | D | 371 | 17.098 | 80.895 | 24.800 | 1.00 | 12.38 | C |
| ATOM | 35538 | O | TRP | D | 371 | 18.310 | 80.974 | 25.053 | 1.00 | 13.23 | O |
| ATOM | 35540 | N | LEU | D | 372 | 16.260 | 81.879 | 25.128 | 1.00 | 12.64 | N |
| ATOM | 35541 | CA | LEU | D | 372 | 16.742 | 83.079 | 25.761 | 1.00 | 12.57 | C |
| ATOM | 35543 | CB | LEU | D | 372 | 15.780 | 84.228 | 25.486 | 1.00 | 12.47 | C |
| ATOM | 35546 | CG | LEU | D | 372 | 15.674 | 84.693 | 24.026 | 1.00 | 12.27 | C |
| ATOM | 35548 | CD1 | LEU | D | 372 | 14.532 | 85.701 | 23.903 | 1.00 | 15.75 | C |
| ATOM | 35552 | CD2 | LEU | D | 372 | 16.990 | 85.252 | 23.511 | 1.00 | 14.42 | C |
| ATOM | 35556 | C | LEU | D | 372 | 16.939 | 82.880 | 27.296 | 1.00 | 12.15 | C |
| ATOM | 35557 | O | LEU | D | 372 | 17.807 | 83.571 | 27.915 | 1.00 | 12.87 | O |
| ATOM | 35559 | N | GLY | D | 373 | 16.124 | 82.058 | 27.928 | 1.00 | 11.87 | N |
| ATOM | 35560 | CA | GLY | D | 373 | 16.197 | 81.886 | 29.348 | 1.00 | 11.63 | C |
| ATOM | 35563 | C | GLY | D | 373 | 17.630 | 81.673 | 29.846 | 1.00 | 11.98 | C |
| ATOM | 35564 | O | GLY | D | 373 | 18.114 | 82.400 | 30.767 | 1.00 | 12.90 | O |
| ATOM | 35566 | N | PRO | D | 374 | 18.338 | 80.701 | 29.264 | 1.00 | 12.87 | N |
| ATOM | 35567 | CA | PRO | D | 374 | 19.684 | 80.437 | 29.823 | 1.00 | 12.48 | C |
| ATOM | 35569 | CB | PRO | D | 374 | 20.137 | 79.218 | 29.034 | 1.00 | 13.36 | C |
| ATOM | 35572 | CG | PRO | D | 374 | 18.793 | 78.456 | 28.737 | 1.00 | 12.28 | C |
| ATOM | 35575 | CD | PRO | D | 374 | 17.931 | 79.645 | 28.303 | 1.00 | 12.30 | C |
| ATOM | 35578 | C | PRO | D | 374 | 20.654 | 81.593 | 29.784 | 1.00 | 13.53 | C |
| ATOM | 35579 | O | PRO | D | 374 | 21.374 | 81.864 | 30.776 | 1.00 | 13.43 | O |
| ATOM | 35580 | N | LEU | D | 375 | 20.667 | 82.295 | 28.671 | 1.00 | 12.37 | N |
| ATOM | 35581 | CA | LEU | D | 375 | 21.550 | 83.497 | 28.560 | 1.00 | 11.85 | C |
| ATOM | 35583 | CB | LEU | D | 375 | 21.797 | 83.915 | 27.135 | 1.00 | 14.67 | C |
| ATOM | 35586 | CG | LEU | D | 375 | 20.612 | 84.404 | 26.357 | 1.00 | 13.88 | C |
| ATOM | 35588 | CD1 | LEU | D | 375 | 20.551 | 85.943 | 26.423 | 1.00 | 16.57 | C |
| ATOM | 35592 | CD2 | LEU | D | 375 | 20.727 | 83.986 | 24.906 | 1.00 | 14.80 | C |
| ATOM | 35596 | C | LEU | D | 375 | 21.126 | 84.662 | 29.433 | 1.00 | 13.39 | C |
| ATOM | 35597 | O | LEU | D | 375 | 21.973 | 85.415 | 29.922 | 1.00 | 13.71 | O |
| ATOM | 35599 | N | VAL | D | 376 | 19.819 | 84.762 | 29.691 | 1.00 | 12.76 | N |
| ATOM | 35600 | CA | VAL | D | 376 | 19.354 | 85.782 | 30.602 | 1.00 | 11.91 | C |
| ATOM | 35602 | CB | VAL | D | 376 | 17.826 | 85.941 | 30.545 | 1.00 | 13.00 | C |
| ATOM | 35604 | CG1 | VAL | D | 376 | 17.311 | 86.843 | 31.696 | 1.00 | 13.04 | C |
| ATOM | 35608 | CG2 | VAL | D | 376 | 17.484 | 86.554 | 29.187 | 1.00 | 13.10 | C |
| ATOM | 35612 | C | VAL | D | 376 | 19.881 | 85.455 | 32.005 | 1.00 | 11.80 | C |
| ATOM | 35613 | O | VAL | D | 376 | 20.336 | 86.379 | 32.713 | 1.00 | 11.70 | O |
| ATOM | 35615 | N | SER | D | 377 | 19.835 | 84.185 | 32.423 | 1.00 | 11.55 | N |
| ATOM | 35616 | CA | SER | D | 377 | 20.441 | 83.823 | 33.728 | 1.00 | 11.59 | C |
| ATOM | 35618 | CB | SER | D | 377 | 20.264 | 82.345 | 34.059 | 1.00 | 12.48 | C |
| ATOM | 35621 | OG | SER | D | 377 | 20.576 | 82.109 | 35.412 | 1.00 | 12.21 | O |
| ATOM | 35623 | C | SER | D | 377 | 21.921 | 84.212 | 33.813 | 1.00 | 12.23 | C |
| ATOM | 35624 | O | SER | D | 377 | 22.385 | 84.731 | 34.856 | 1.00 | 12.86 | O |
| ATOM | 35626 | N | ASP | D | 378 | 22.659 | 84.020 | 32.717 | 1.00 | 12.70 | N |
| ATOM | 35627 | CA | ASP | D | 378 | 24.067 | 84.445 | 32.655 | 1.00 | 13.33 | C |
| ATOM | 35629 | CB | ASP | D | 378 | 24.684 | 83.984 | 31.335 | 1.00 | 12.71 | C |

| | | | | | | | | | |
|---|---|---|---|---|---|---|---|---|---|
| ATOM | 35632 | CG | ASP | D | 378 | 24.977 | 82.498 | 31.301 | 1.00 16.01 | C |
| ATOM | 35633 | OD1 | ASP | D | 378 | 24.880 | 81.809 | 32.350 | 1.00 19.56 | O |
| ATOM | 35634 | OD2 | ASP | D | 378 | 25.352 | 81.988 | 30.197 | 1.00 18.65 | O |
| ATOM | 35635 | C | ASP | D | 378 | 24.233 | 85.951 | 32.837 | 1.00 13.54 | C |
| ATOM | 35636 | O | ASP | D | 378 | 25.141 | 86.411 | 33.540 | 1.00 13.05 | O |
| ATOM | 35638 | N | LEU | D | 379 | 23.370 | 86.734 | 32.177 | 1.00 12.71 | N |
| ATOM | 35639 | CA | LEU | D | 379 | 23.410 | 88.187 | 32.293 | 1.00 12.45 | C |
| ATOM | 35641 | CB | LEU | D | 379 | 22.461 | 88.852 | 31.277 | 1.00 12.90 | C |
| ATOM | 35644 | CG | LEU | D | 379 | 22.806 | 88.645 | 29.807 | 1.00 12.94 | C |
| ATOM | 35646 | CD1 | LEU | D | 379 | 21.668 | 89.148 | 28.869 | 1.00 12.66 | C |
| ATOM | 35650 | CD2 | LEU | D | 379 | 24.109 | 89.358 | 29.452 | 1.00 17.59 | C |
| ATOM | 35654 | C | LEU | D | 379 | 23.100 | 88.644 | 33.713 | 1.00 11.90 | C |
| ATOM | 35655 | O | LEU | D | 379 | 23.714 | 89.603 | 34.221 | 1.00 13.38 | O |
| ATOM | 35657 | N | ILE | D | 380 | 22.139 | 87.992 | 34.362 | 1.00 11.43 | N |
| ATOM | 35658 | CA | ILE | D | 380 | 21.805 | 88.316 | 35.743 | 1.00 12.12 | C |
| ATOM | 35660 | CB | ILE | D | 380 | 20.517 | 87.642 | 36.167 | 1.00 13.44 | C |
| ATOM | 35662 | CG1 | ILE | D | 380 | 19.366 | 88.268 | 35.351 | 1.00 12.73 | C |
| ATOM | 35665 | CD1 | ILE | D | 380 | 18.024 | 87.600 | 35.564 | 1.00 13.16 | C |
| ATOM | 35669 | CG2 | ILE | D | 380 | 20.289 | 87.773 | 37.634 | 1.00 13.50 | C |
| ATOM | 35673 | C | ILE | D | 380 | 22.998 | 87.970 | 36.687 | 1.00 12.15 | C |
| ATOM | 35674 | O | ILE | D | 380 | 23.342 | 88.727 | 37.625 | 1.00 12.04 | O |
| ATOM | 35676 | N | HIS | D | 381 | 23.641 | 86.836 | 36.417 | 1.00 12.09 | N |
| ATOM | 35677 | CA | HIS | D | 381 | 24.833 | 86.436 | 37.159 | 1.00 12.42 | C |
| ATOM | 35679 | CB | HIS | D | 381 | 25.238 | 84.997 | 36.749 | 1.00 14.32 | C |
| ATOM | 35682 | CG | HIS | D | 381 | 26.373 | 84.425 | 37.522 | 1.00 12.96 | C |
| ATOM | 35683 | ND1 | HIS | D | 381 | 27.688 | 84.783 | 37.297 | 1.00 16.54 | N |
| ATOM | 35685 | CE1 | HIS | D | 381 | 28.461 | 84.091 | 38.133 | 1.00 16.16 | C |
| ATOM | 35687 | NE2 | HIS | D | 381 | 27.706 | 83.289 | 38.850 | 1.00 15.75 | N |
| ATOM | 35689 | CD2 | HIS | D | 381 | 26.389 | 83.486 | 38.502 | 1.00 16.04 | C |
| ATOM | 35691 | C | HIS | D | 381 | 25.983 | 87.455 | 36.980 | 1.00 12.25 | C |
| ATOM | 35692 | O | HIS | D | 381 | 26.568 | 87.908 | 37.980 | 1.00 12.43 | O |
| ATOM | 35694 | N | ALA | D | 382 | 26.228 | 87.846 | 35.741 | 1.00 11.95 | N |
| ATOM | 35695 | CA | ALA | D | 382 | 27.235 | 88.823 | 35.408 | 1.00 12.59 | C |
| ATOM | 35697 | CB | ALA | D | 382 | 27.262 | 89.050 | 33.951 | 1.00 12.04 | C |
| ATOM | 35701 | C | ALA | D | 382 | 26.946 | 90.113 | 36.178 | 1.00 11.94 | C |
| ATOM | 35702 | O | ALA | D | 382 | 27.873 | 90.791 | 36.692 | 1.00 13.53 | O |
| ATOM | 35704 | N | HIS | D | 383 | 25.663 | 90.488 | 36.281 | 1.00 10.96 | N |
| ATOM | 35705 | CA | HIS | D | 383 | 25.332 | 91.694 | 37.001 | 1.00 11.03 | C |
| ATOM | 35707 | CB | HIS | D | 383 | 23.847 | 91.952 | 36.926 | 1.00 11.85 | C |
| ATOM | 35710 | CG | HIS | D | 383 | 23.502 | 93.379 | 37.132 | 1.00 12.36 | C |
| ATOM | 35711 | ND1 | HIS | D | 383 | 23.328 | 94.266 | 36.083 | 1.00 14.94 | N |
| ATOM | 35713 | CE1 | HIS | D | 383 | 23.035 | 95.455 | 36.582 | 1.00 16.93 | C |
| ATOM | 35715 | NE2 | HIS | D | 383 | 23.058 | 95.384 | 37.905 | 1.00 15.06 | N |
| ATOM | 35717 | CD2 | HIS | D | 383 | 23.326 | 94.087 | 38.271 | 1.00 15.35 | C |
| ATOM | 35719 | C | HIS | D | 383 | 25.778 | 91.616 | 38.465 | 1.00 11.08 | C |
| ATOM | 35720 | O | HIS | D | 383 | 26.320 | 92.589 | 39.038 | 1.00 12.09 | O |
| ATOM | 35722 | N | ALA | D | 384 | 25.518 | 90.463 | 39.094 | 1.00 10.93 | N |
| ATOM | 35723 | CA | ALA | D | 384 | 25.916 | 90.256 | 40.495 | 1.00 10.01 | C |
| ATOM | 35725 | CB | ALA | D | 384 | 25.441 | 88.923 | 41.005 | 1.00 11.50 | C |
| ATOM | 35729 | C | ALA | D | 384 | 27.460 | 90.364 | 40.636 | 1.00 10.64 | C |
| ATOM | 35730 | O | ALA | D | 384 | 27.989 | 90.999 | 41.574 | 1.00 11.60 | O |
| ATOM | 35732 | N | VAL | D | 385 | 28.185 | 89.745 | 39.711 | 1.00 12.28 | N |
| ATOM | 35733 | CA | VAL | D | 385 | 29.628 | 89.728 | 39.777 | 1.00 11.93 | C |
| ATOM | 35735 | CB | VAL | D | 385 | 30.231 | 88.787 | 38.714 | 1.00 13.58 | C |
| ATOM | 35737 | CG1 | VAL | D | 385 | 31.719 | 88.933 | 38.644 | 1.00 13.80 | C |
| ATOM | 35741 | CG2 | VAL | D | 385 | 29.828 | 87.389 | 38.989 | 1.00 13.00 | C |
| ATOM | 35745 | C | VAL | D | 385 | 30.202 | 91.149 | 39.585 | 1.00 12.23 | C |

| ATOM | 35746 | O   | VAL | D | 385 | 31.060 | 91.599 | 40.346 | 1.00 | 12.38 | O |
| ATOM | 35748 | N   | LEU | D | 386 | 29.719 | 91.836 | 38.554 | 1.00 | 11.08 | N |
| ATOM | 35749 | CA  | LEU | D | 386 | 30.217 | 93.174 | 38.281 | 1.00 | 12.19 | C |
| ATOM | 35751 | CB  | LEU | D | 386 | 29.830 | 93.676 | 36.924 | 1.00 | 11.98 | C |
| ATOM | 35754 | CG  | LEU | D | 386 | 30.406 | 93.013 | 35.713 | 1.00 | 13.69 | C |
| ATOM | 35756 | CD1 | LEU | D | 386 | 30.048 | 93.796 | 34.432 | 1.00 | 14.01 | C |
| ATOM | 35760 | CD2 | LEU | D | 386 | 31.919 | 92.887 | 35.885 | 1.00 | 15.65 | C |
| ATOM | 35764 | C   | LEU | D | 386 | 29.822 | 94.132 | 39.378 | 1.00 | 12.65 | C |
| ATOM | 35765 | O   | LEU | D | 386 | 30.590 | 95.043 | 39.657 | 1.00 | 12.02 | O |
| ATOM | 35767 | N   | THR | D | 387 | 28.656 | 93.955 | 40.012 | 1.00 | 12.10 | N |
| ATOM | 35768 | CA  | THR | D | 387 | 28.296 | 94.847 | 41.092 | 1.00 | 12.85 | C |
| ATOM | 35770 | CB  | THR | D | 387 | 26.856 | 94.581 | 41.562 | 1.00 | 13.82 | C |
| ATOM | 35772 | OG1 | THR | D | 387 | 25.946 | 94.871 | 40.481 | 1.00 | 14.39 | O |
| ATOM | 35774 | CG2 | THR | D | 387 | 26.524 | 95.400 | 42.787 | 1.00 | 13.77 | C |
| ATOM | 35778 | C   | THR | D | 387 | 29.328 | 94.799 | 42.224 | 1.00 | 12.54 | C |
| ATOM | 35779 | O   | THR | D | 387 | 29.776 | 95.846 | 42.669 | 1.00 | 13.09 | O |
| ATOM | 35781 | N   | ILE | D | 388 | 29.767 | 93.592 | 42.591 | 1.00 | 12.28 | N |
| ATOM | 35782 | CA  | ILE | D | 388 | 30.798 | 93.457 | 43.603 | 1.00 | 13.57 | C |
| ATOM | 35784 | CB  | ILE | D | 388 | 30.973 | 91.991 | 44.072 | 1.00 | 14.29 | C |
| ATOM | 35786 | CG1 | ILE | D | 388 | 29.700 | 91.521 | 44.796 | 1.00 | 12.92 | C |
| ATOM | 35789 | CD1 | ILE | D | 388 | 29.844 | 90.093 | 45.401 | 1.00 | 17.27 | C |
| ATOM | 35793 | CG2 | ILE | D | 388 | 32.222 | 91.924 | 44.927 | 1.00 | 13.66 | C |
| ATOM | 35797 | C   | ILE | D | 388 | 32.128 | 94.044 | 43.093 | 1.00 | 12.54 | C |
| ATOM | 35798 | O   | ILE | D | 388 | 32.819 | 94.719 | 43.810 | 1.00 | 13.83 | O |
| ATOM | 35800 | N   | GLU | D | 389 | 32.494 | 93.713 | 41.859 | 1.00 | 12.72 | N |
| ATOM | 35801 | CA  | GLU | D | 389 | 33.790 | 94.156 | 41.328 | 1.00 | 13.39 | C |
| ATOM | 35803 | CB  | GLU | D | 389 | 34.063 | 93.536 | 39.965 | 1.00 | 13.56 | C |
| ATOM | 35806 | CG  | GLU | D | 389 | 35.430 | 93.801 | 39.444 | 1.00 | 13.07 | C |
| ATOM | 35809 | CD  | GLU | D | 389 | 36.520 | 93.018 | 40.150 | 1.00 | 13.82 | C |
| ATOM | 35810 | OE1 | GLU | D | 389 | 36.218 | 92.293 | 41.141 | 1.00 | 14.87 | O |
| ATOM | 35811 | OE2 | GLU | D | 389 | 37.688 | 93.129 | 39.702 | 1.00 | 17.50 | O |
| ATOM | 35812 | C   | GLU | D | 389 | 33.924 | 95.658 | 41.193 | 1.00 | 14.95 | C |
| ATOM | 35813 | O   | GLU | D | 389 | 34.948 | 96.266 | 41.551 | 1.00 | 15.27 | O |
| ATOM | 35815 | N   | ALA | D | 390 | 32.882 | 96.270 | 40.660 | 1.00 | 14.98 | N |
| ATOM | 35816 | CA  | ALA | D | 390 | 32.885 | 97.675 | 40.379 | 1.00 | 14.86 | C |
| ATOM | 35818 | CB  | ALA | D | 390 | 31.907 | 97.996 | 39.286 | 1.00 | 15.63 | C |
| ATOM | 35822 | C   | ALA | D | 390 | 32.581 | 98.500 | 41.630 | 1.00 | 16.03 | C |
| ATOM | 35823 | O   | ALA | D | 390 | 33.178 | 99.531 | 41.830 | 1.00 | 18.73 | O |
| ATOM | 35825 | N   | GLY | D | 391 | 31.726 | 97.990 | 42.502 | 1.00 | 14.40 | N |
| ATOM | 35826 | CA  | GLY | D | 391 | 31.196 | 98.790 | 43.620 | 1.00 | 14.69 | C |
| ATOM | 35829 | C   | GLY | D | 391 | 31.667 | 98.485 | 45.020 | 1.00 | 15.12 | C |
| ATOM | 35830 | O   | GLY | D | 391 | 31.451 | 99.277 | 45.953 | 1.00 | 14.31 | O |
| ATOM | 35832 | N   | GLN | D | 392 | 32.300 | 97.328 | 45.221 | 1.00 | 14.52 | N |
| ATOM | 35833 | CA  | GLN | D | 392 | 32.534 | 96.825 | 46.582 | 1.00 | 15.67 | C |
| ATOM | 35835 | CB  | GLN | D | 392 | 31.437 | 95.817 | 46.999 | 1.00 | 14.82 | C |
| ATOM | 35838 | CG  | GLN | D | 392 | 30.043 | 96.344 | 46.933 | 1.00 | 18.47 | C |
| ATOM | 35841 | CD  | GLN | D | 392 | 29.007 | 95.242 | 46.984 | 1.00 | 19.69 | C |
| ATOM | 35842 | OE1 | GLN | D | 392 | 28.041 | 95.268 | 46.224 | 1.00 | 25.22 | O |
| ATOM | 35843 | NE2 | GLN | D | 392 | 29.216 | 94.272 | 47.835 | 1.00 | 19.59 | N |
| ATOM | 35846 | C   | GLN | D | 392 | 33.883 | 96.120 | 46.742 | 1.00 | 14.69 | C |
| ATOM | 35847 | O   | GLN | D | 392 | 34.039 | 95.270 | 47.622 | 1.00 | 15.12 | O |
| ATOM | 35849 | N   | SER | D | 393 | 34.832 | 96.477 | 45.888 | 1.00 | 13.80 | N |
| ATOM | 35850 | CA  | SER | D | 393 | 36.082 | 95.753 | 45.853 | 1.00 | 13.42 | C |
| ATOM | 35852 | CB  | SER | D | 393 | 36.175 | 94.851 | 44.609 | 1.00 | 14.96 | C |
| ATOM | 35855 | OG  | SER | D | 393 | 35.257 | 93.775 | 44.738 | 1.00 | 15.04 | O |
| ATOM | 35857 | C   | SER | D | 393 | 37.293 | 96.681 | 45.883 | 1.00 | 14.06 | C |
| ATOM | 35858 | O   | SER | D | 393 | 37.351 | 97.699 | 45.219 | 1.00 | 14.60 | O |

| | | | | | | | | | |
|---|---|---|---|---|---|---|---|---|---|
| ATOM | 35860 | N | THR | D | 394 | 38.301 | 96.202 | 46.575 | 1.00 12.12 | N |
| ATOM | 35861 | CA | THR | D | 394 | 39.620 | 96.818 | 46.545 | 1.00 12.64 | C |
| ATOM | 35863 | CB | THR | D | 394 | 40.247 | 96.896 | 47.949 | 1.00 13.60 | C |
| ATOM | 35865 | OG1 | THR | D | 394 | 39.393 | 97.647 | 48.827 | 1.00 13.41 | O |
| ATOM | 35867 | CG2 | THR | D | 394 | 41.619 | 97.565 | 47.858 | 1.00 14.22 | C |
| ATOM | 35871 | C | THR | D | 394 | 40.502 | 95.949 | 45.671 | 1.00 12.53 | C |
| ATOM | 35872 | O | THR | D | 394 | 40.654 | 94.763 | 45.979 | 1.00 12.80 | O |
| ATOM | 35874 | N | THR | D | 395 | 41.070 | 96.523 | 44.610 | 1.00 11.89 | N |
| ATOM | 35875 | CA | THR | D | 395 | 41.751 | 95.700 | 43.619 | 1.00 12.27 | C |
| ATOM | 35877 | CB | THR | D | 395 | 40.991 | 95.773 | 42.236 | 1.00 13.34 | C |
| ATOM | 35879 | OG1 | THR | D | 395 | 40.948 | 97.106 | 41.693 | 1.00 14.64 | O |
| ATOM | 35881 | CG2 | THR | D | 395 | 39.564 | 95.284 | 42.399 | 1.00 14.80 | C |
| ATOM | 35885 | C | THR | D | 395 | 43.222 | 96.044 | 43.438 | 1.00 12.69 | C |
| ATOM | 35886 | O | THR | D | 395 | 43.868 | 95.473 | 42.548 | 1.00 14.37 | O |
| ATOM | 35888 | N | ASP | D | 396 | 43.767 | 96.981 | 44.234 | 1.00 12.86 | N |
| ATOM | 35889 | CA | ASP | D | 396 | 45.171 | 97.221 | 44.190 | 1.00 13.44 | C |
| ATOM | 35891 | CB | ASP | D | 396 | 45.546 | 98.679 | 44.454 | 1.00 13.82 | C |
| ATOM | 35894 | CG | ASP | D | 396 | 45.158 | 99.205 | 45.825 | 1.00 16.81 | C |
| ATOM | 35895 | OD1 | ASP | D | 396 | 43.962 | 99.136 | 46.225 | 1.00 16.43 | O |
| ATOM | 35896 | OD2 | ASP | D | 396 | 46.064 | 99.719 | 46.569 | 1.00 16.77 | O |
| ATOM | 35897 | C | ASP | D | 396 | 45.889 | 96.239 | 45.124 | 1.00 12.91 | C |
| ATOM | 35898 | O | ASP | D | 396 | 45.282 | 95.254 | 45.562 | 1.00 12.85 | O |
| ATOM | 35900 | N | ASN | D | 397 | 47.179 | 96.481 | 45.369 | 1.00 13.31 | N |
| ATOM | 35901 | CA | ASN | D | 397 | 48.045 | 95.560 | 46.083 | 1.00 13.11 | C |
| ATOM | 35903 | CB | ASN | D | 397 | 48.353 | 94.350 | 45.226 | 1.00 13.08 | C |
| ATOM | 35906 | CG | ASN | D | 397 | 48.968 | 93.242 | 46.036 | 1.00 14.21 | C |
| ATOM | 35907 | OD1 | ASN | D | 397 | 48.315 | 92.688 | 46.932 | 1.00 15.63 | O |
| ATOM | 35908 | ND2 | ASN | D | 397 | 50.229 | 92.909 | 45.739 | 1.00 15.54 | N |
| ATOM | 35911 | C | ASN | D | 397 | 49.358 | 96.261 | 46.319 | 1.00 12.90 | C |
| ATOM | 35912 | O | ASN | D | 397 | 49.738 | 97.032 | 45.457 | 1.00 14.72 | O |
| ATOM | 35914 | N | PRO | D | 398 | 50.091 | 95.921 | 47.382 | 1.00 13.37 | N |
| ATOM | 35915 | CA | PRO | D | 398 | 49.593 | 95.274 | 48.603 | 1.00 13.77 | C |
| ATOM | 35917 | CB | PRO | D | 398 | 50.860 | 95.116 | 49.511 | 1.00 14.04 | C |
| ATOM | 35920 | CG | PRO | D | 398 | 51.808 | 96.106 | 48.998 | 1.00 16.64 | C |
| ATOM | 35923 | CD | PRO | D | 398 | 51.450 | 96.487 | 47.568 | 1.00 14.16 | C |
| ATOM | 35926 | C | PRO | D | 398 | 48.547 | 96.084 | 49.334 | 1.00 14.20 | C |
| ATOM | 35927 | O | PRO | D | 398 | 48.421 | 97.276 | 49.105 | 1.00 14.42 | O |
| ATOM | 35928 | N | LEU | D | 399 | 47.801 | 95.406 | 50.195 | 1.00 14.69 | N |
| ATOM | 35929 | CA | LEU | D | 399 | 46.670 | 96.003 | 50.883 | 1.00 13.95 | C |
| ATOM | 35931 | CB | LEU | D | 399 | 45.412 | 95.219 | 50.543 | 1.00 14.13 | C |
| ATOM | 35934 | CG | LEU | D | 399 | 45.050 | 95.205 | 49.046 | 1.00 15.45 | C |
| ATOM | 35936 | CD1 | LEU | D | 399 | 43.739 | 94.502 | 48.866 | 1.00 16.51 | C |
| ATOM | 35940 | CD2 | LEU | D | 399 | 44.955 | 96.590 | 48.510 | 1.00 16.40 | C |
| ATOM | 35944 | C | LEU | D | 399 | 46.931 | 96.080 | 52.373 | 1.00 14.97 | C |
| ATOM | 35945 | O | LEU | D | 399 | 47.623 | 95.226 | 52.931 | 1.00 14.68 | O |
| ATOM | 35947 | N | ILE | D | 400 | 46.388 | 97.116 | 52.998 | 1.00 15.39 | N |
| ATOM | 35948 | CA | ILE | D | 400 | 46.713 | 97.486 | 54.375 | 1.00 16.24 | C |
| ATOM | 35950 | CB | ILE | D | 400 | 47.144 | 98.985 | 54.421 | 1.00 17.63 | C |
| ATOM | 35952 | CG1 | ILE | D | 400 | 48.546 | 99.150 | 53.791 | 1.00 23.35 | C |
| ATOM | 35955 | CD1 | ILE | D | 400 | 48.545 | 99.553 | 52.384 | 1.00 27.66 | C |
| ATOM | 35959 | CG2 | ILE | D | 400 | 47.207 | 99.493 | 55.834 | 1.00 19.67 | C |
| ATOM | 35963 | C | ILE | D | 400 | 45.511 | 97.224 | 55.261 | 1.00 16.18 | C |
| ATOM | 35964 | O | ILE | D | 400 | 44.431 | 97.768 | 54.981 | 1.00 14.06 | O |
| ATOM | 35966 | N | ASP | D | 401 | 45.689 | 96.386 | 56.294 | 1.00 16.70 | N |
| ATOM | 35967 | CA | ASP | D | 401 | 44.694 | 96.148 | 57.328 | 1.00 17.68 | C |
| ATOM | 35969 | CB | ASP | D | 401 | 44.622 | 94.681 | 57.814 | 1.00 19.26 | C |
| ATOM | 35972 | CG | ASP | D | 401 | 43.477 | 94.474 | 58.799 | 1.00 18.73 | C |

| ATOM | 35973 | OD1 | ASP | D | 401 | 42.888 | 95.475 | 59.311 | 1.00 | 24.54 | O |
|---|---|---|---|---|---|---|---|---|---|---|---|
| ATOM | 35974 | OD2 | ASP | D | 401 | 43.082 | 93.335 | 59.106 | 1.00 | 24.21 | O |
| ATOM | 35975 | C | ASP | D | 401 | 45.111 | 97.026 | 58.509 | 1.00 | 18.25 | C |
| ATOM | 35976 | O | ASP | D | 401 | 46.020 | 96.660 | 59.258 | 1.00 | 18.18 | O |
| ATOM | 35978 | N | VAL | D | 402 | 44.490 | 98.192 | 58.598 | 1.00 | 19.94 | N |
| ATOM | 35979 | CA | VAL | D | 402 | 44.889 | 99.193 | 59.608 | 1.00 | 22.07 | C |
| ATOM | 35981 | CB | VAL | D | 402 | 44.246 | 100.557 | 59.338 | 1.00 | 22.65 | C |
| ATOM | 35983 | CG1 | VAL | D | 402 | 44.534 | 101.551 | 60.492 | 1.00 | 23.92 | C |
| ATOM | 35987 | CG2 | VAL | D | 402 | 44.747 | 101.114 | 58.025 | 1.00 | 22.29 | C |
| ATOM | 35991 | C | VAL | D | 402 | 44.519 | 98.728 | 60.995 | 1.00 | 23.95 | C |
| ATOM | 35992 | O | VAL | D | 402 | 45.334 | 98.890 | 61.922 | 1.00 | 23.12 | O |
| ATOM | 35994 | N | GLU | D | 403 | 43.322 | 98.138 | 61.134 | 1.00 | 25.31 | N |
| ATOM | 35995 | CA | GLU | D | 403 | 42.851 | 97.696 | 62.441 | 1.00 | 27.89 | C |
| ATOM | 35997 | CB | GLU | D | 403 | 41.428 | 97.131 | 62.384 | 1.00 | 28.99 | C |
| ATOM | 36000 | CG | GLU | D | 403 | 40.703 | 97.173 | 63.757 | 1.00 | 34.67 | C |
| ATOM | 36003 | CD | GLU | D | 403 | 40.624 | 98.600 | 64.352 | 1.00 | 41.61 | C |
| ATOM | 36004 | OE1 | GLU | D | 403 | 40.780 | 99.591 | 63.576 | 1.00 | 46.87 | O |
| ATOM | 36005 | OE2 | GLU | D | 403 | 40.406 | 98.734 | 65.591 | 1.00 | 44.91 | O |
| ATOM | 36006 | C | GLU | D | 403 | 43.801 | 96.666 | 63.040 | 1.00 | 27.72 | C |
| ATOM | 36007 | O | GLU | D | 403 | 44.102 | 96.722 | 64.241 | 1.00 | 29.26 | O |
| ATOM | 36009 | N | ASN | D | 404 | 44.288 | 95.752 | 62.221 | 1.00 | 26.42 | N |
| ATOM | 36010 | CA | ASN | D | 404 | 45.236 | 94.737 | 62.677 | 1.00 | 26.39 | C |
| ATOM | 36012 | CB | ASN | D | 404 | 44.863 | 93.388 | 62.068 | 1.00 | 26.42 | C |
| ATOM | 36015 | CG | ASN | D | 404 | 43.536 | 92.852 | 62.621 | 1.00 | 30.07 | C |
| ATOM | 36016 | OD1 | ASN | D | 404 | 43.464 | 92.428 | 63.779 | 1.00 | 34.18 | O |
| ATOM | 36017 | ND2 | ASN | D | 404 | 42.484 | 92.883 | 61.802 | 1.00 | 33.15 | N |
| ATOM | 36020 | C | ASN | D | 404 | 46.714 | 95.063 | 62.401 | 1.00 | 25.06 | C |
| ATOM | 36021 | O | ASN | D | 404 | 47.575 | 94.223 | 62.573 | 1.00 | 24.49 | O |
| ATOM | 36023 | N | LYS | D | 405 | 46.994 | 96.277 | 61.933 | 1.00 | 23.27 | N |
| ATOM | 36024 | CA | LYS | D | 405 | 48.361 | 96.737 | 61.702 | 1.00 | 23.52 | C |
| ATOM | 36026 | CB | LYS | D | 405 | 49.048 | 97.030 | 63.049 | 1.00 | 24.13 | C |
| ATOM | 36029 | CG | LYS | D | 405 | 48.365 | 98.114 | 63.823 | 1.00 | 25.55 | C |
| ATOM | 36032 | CD | LYS | D | 405 | 49.252 | 98.573 | 64.969 | 1.00 | 25.84 | C |
| ATOM | 36035 | CE | LYS | D | 405 | 48.742 | 99.870 | 65.535 | 1.00 | 29.42 | C |
| ATOM | 36038 | NZ | LYS | D | 405 | 47.367 | 99.662 | 66.067 | 1.00 | 32.24 | N |
| ATOM | 36042 | C | LYS | D | 405 | 49.241 | 95.813 | 60.853 | 1.00 | 22.60 | C |
| ATOM | 36043 | O | LYS | D | 405 | 50.402 | 95.496 | 61.201 | 1.00 | 21.56 | O |
| ATOM | 36045 | N | THR | D | 406 | 48.700 | 95.399 | 59.706 | 1.00 | 21.43 | N |
| ATOM | 36046 | CA | THR | D | 406 | 49.408 | 94.456 | 58.851 | 1.00 | 22.45 | C |
| ATOM | 36048 | CB | THR | D | 406 | 48.952 | 92.992 | 59.099 | 1.00 | 22.51 | C |
| ATOM | 36050 | OG1 | THR | D | 406 | 47.535 | 92.889 | 59.003 | 1.00 | 27.67 | O |
| ATOM | 36052 | CG2 | THR | D | 406 | 49.367 | 92.531 | 60.490 | 1.00 | 24.80 | C |
| ATOM | 36056 | C | THR | D | 406 | 49.165 | 94.825 | 57.388 | 1.00 | 20.95 | C |
| ATOM | 36057 | O | THR | D | 406 | 48.089 | 95.298 | 57.029 | 1.00 | 21.29 | O |
| ATOM | 36059 | N | SER | D | 407 | 50.184 | 94.617 | 56.576 | 1.00 | 19.17 | N |
| ATOM | 36060 | CA | SER | D | 407 | 50.086 | 94.663 | 55.113 | 1.00 | 19.65 | C |
| ATOM | 36062 | CB | SER | D | 407 | 51.325 | 95.301 | 54.518 | 1.00 | 20.59 | C |
| ATOM | 36065 | OG | SER | D | 407 | 51.337 | 96.694 | 54.778 | 1.00 | 26.72 | O |
| ATOM | 36067 | C | SER | D | 407 | 49.972 | 93.229 | 54.585 | 1.00 | 17.43 | C |
| ATOM | 36068 | O | SER | D | 407 | 50.467 | 92.293 | 55.214 | 1.00 | 18.49 | O |
| ATOM | 36070 | N | HIS | D | 408 | 49.318 | 93.068 | 53.453 | 1.00 | 14.95 | N |
| ATOM | 36071 | CA | HIS | D | 408 | 49.037 | 91.768 | 52.871 | 1.00 | 13.38 | C |
| ATOM | 36073 | CB | HIS | D | 408 | 47.572 | 91.390 | 53.080 | 1.00 | 13.21 | C |
| ATOM | 36076 | CG | HIS | D | 408 | 47.183 | 91.241 | 54.514 | 1.00 | 13.87 | C |
| ATOM | 36077 | ND1 | HIS | D | 408 | 47.219 | 90.032 | 55.169 | 1.00 | 14.93 | N |
| ATOM | 36079 | CE1 | HIS | D | 408 | 46.791 | 90.186 | 56.412 | 1.00 | 16.53 | C |
| ATOM | 36081 | NE2 | HIS | D | 408 | 46.413 | 91.436 | 56.567 | 1.00 | 18.28 | N |

| | | | | | | | | | |
|---|---|---|---|---|---|---|---|---|---|
| ATOM | 36083 | CD2 | HIS | D | 408 | 46.667 | 92.127 | 55.402 | 1.00 17.32 | C |
| ATOM | 36085 | C | HIS | D | 408 | 49.336 | 91.773 | 51.383 | 1.00 13.40 | C |
| ATOM | 36086 | O | HIS | D | 408 | 48.965 | 92.720 | 50.659 | 1.00 13.63 | O |
| ATOM | 36088 | N | HIS | D | 409 | 50.011 | 90.720 | 50.918 | 1.00 13.45 | N |
| ATOM | 36089 | CA | HIS | D | 409 | 50.381 | 90.596 | 49.527 | 1.00 13.43 | C |
| ATOM | 36091 | CB | HIS | D | 409 | 51.848 | 90.183 | 49.424 | 1.00 15.50 | C |
| ATOM | 36094 | CG | HIS | D | 409 | 52.781 | 91.290 | 49.835 | 1.00 19.57 | C |
| ATOM | 36095 | ND1 | HIS | D | 409 | 53.220 | 91.457 | 51.134 | 1.00 27.19 | N |
| ATOM | 36097 | CE1 | HIS | D | 409 | 53.992 | 92.531 | 51.194 | 1.00 24.74 | C |
| ATOM | 36099 | NE2 | HIS | D | 409 | 54.052 | 93.066 | 49.985 | 1.00 25.79 | N |
| ATOM | 36101 | CD2 | HIS | D | 409 | 53.306 | 92.309 | 49.120 | 1.00 23.48 | C |
| ATOM | 36103 | C | HIS | D | 409 | 49.465 | 89.585 | 48.849 | 1.00 12.71 | C |
| ATOM | 36104 | O | HIS | D | 409 | 49.481 | 88.428 | 49.140 | 1.00 11.50 | O |
| ATOM | 36106 | N | GLY | D | 410 | 48.630 | 90.078 | 47.962 | 1.00 12.73 | N |
| ATOM | 36107 | CA | GLY | D | 410 | 47.555 | 89.303 | 47.383 | 1.00 12.53 | C |
| ATOM | 36110 | C | GLY | D | 410 | 47.445 | 89.478 | 45.879 | 1.00 12.52 | C |
| ATOM | 36111 | O | GLY | D | 410 | 48.424 | 89.747 | 45.190 | 1.00 12.18 | O |
| ATOM | 36113 | N | GLY | D | 411 | 46.247 | 89.267 | 45.352 | 1.00 13.47 | N |
| ATOM | 36114 | CA | GLY | D | 411 | 46.056 | 89.216 | 43.909 | 1.00 13.25 | C |
| ATOM | 36117 | C | GLY | D | 411 | 44.739 | 89.752 | 43.396 | 1.00 10.75 | C |
| ATOM | 36118 | O | GLY | D | 411 | 44.232 | 89.248 | 42.366 | 1.00 11.31 | O |
| ATOM | 36120 | N | ASN | D | 412 | 44.210 | 90.760 | 44.094 | 1.00 11.52 | N |
| ATOM | 36121 | CA | ASN | D | 412 | 42.908 | 91.280 | 43.764 | 1.00 11.26 | C |
| ATOM | 36123 | CB | ASN | D | 412 | 42.324 | 92.064 | 44.929 | 1.00 10.29 | C |
| ATOM | 36126 | CG | ASN | D | 412 | 41.791 | 91.140 | 46.041 | 1.00 13.76 | C |
| ATOM | 36127 | OD1 | ASN | D | 412 | 41.460 | 89.955 | 45.795 | 1.00 14.01 | O |
| ATOM | 36128 | ND2 | ASN | D | 412 | 41.678 | 91.685 | 47.256 | 1.00 13.14 | N |
| ATOM | 36131 | C | ASN | D | 412 | 42.831 | 92.079 | 42.485 | 1.00 11.70 | C |
| ATOM | 36132 | O | ASN | D | 412 | 41.736 | 92.477 | 42.071 | 1.00 12.23 | O |
| ATOM | 36134 | N | PHE | D | 413 | 43.985 | 92.284 | 41.851 | 1.00 10.46 | N |
| ATOM | 36135 | CA | PHE | D | 413 | 44.104 | 92.914 | 40.541 | 1.00 10.95 | C |
| ATOM | 36137 | CB | PHE | D | 413 | 45.484 | 93.543 | 40.405 | 1.00 11.25 | C |
| ATOM | 36140 | CG | PHE | D | 413 | 46.597 | 92.610 | 40.777 | 1.00 10.62 | C |
| ATOM | 36141 | CD1 | PHE | D | 413 | 46.914 | 91.477 | 40.020 | 1.00 12.39 | C |
| ATOM | 36143 | CE1 | PHE | D | 413 | 47.886 | 90.607 | 40.445 | 1.00 10.40 | C |
| ATOM | 36145 | CZ | PHE | D | 413 | 48.541 | 90.805 | 41.641 | 1.00 12.18 | C |
| ATOM | 36147 | CE2 | PHE | D | 413 | 48.260 | 91.942 | 42.396 | 1.00 13.06 | C |
| ATOM | 36149 | CD2 | PHE | D | 413 | 47.290 | 92.812 | 41.972 | 1.00 12.42 | C |
| ATOM | 36151 | C | PHE | D | 413 | 43.867 | 91.906 | 39.383 | 1.00 10.45 | C |
| ATOM | 36152 | O | PHE | D | 413 | 43.849 | 92.325 | 38.219 | 1.00 11.77 | O |
| ATOM | 36154 | N | GLN | D | 414 | 43.732 | 90.590 | 39.717 | 1.00 11.72 | N |
| ATOM | 36155 | CA | GLN | D | 414 | 43.519 | 89.618 | 38.662 | 1.00 10.89 | C |
| ATOM | 36157 | CB | GLN | D | 414 | 43.935 | 88.297 | 39.193 | 1.00 11.58 | C |
| ATOM | 36160 | CG | GLN | D | 414 | 43.813 | 87.141 | 38.242 | 1.00 12.62 | C |
| ATOM | 36163 | CD | GLN | D | 414 | 44.835 | 87.184 | 37.129 | 1.00 11.53 | C |
| ATOM | 36164 | OE1 | GLN | D | 414 | 44.589 | 87.821 | 36.114 | 1.00 12.59 | O |
| ATOM | 36165 | NE2 | GLN | D | 414 | 45.998 | 86.521 | 37.329 | 1.00 11.94 | N |
| ATOM | 36168 | C | GLN | D | 414 | 42.044 | 89.609 | 38.230 | 1.00 11.78 | C |
| ATOM | 36169 | O | GLN | D | 414 | 41.180 | 89.087 | 38.947 | 1.00 12.59 | O |
| ATOM | 36171 | N | ALA | D | 415 | 41.761 | 90.273 | 37.112 | 1.00 12.77 | N |
| ATOM | 36172 | CA | ALA | D | 415 | 40.395 | 90.674 | 36.733 | 1.00 12.95 | C |
| ATOM | 36174 | CB | ALA | D | 415 | 40.459 | 91.879 | 35.818 | 1.00 13.84 | C |
| ATOM | 36178 | C | ALA | D | 415 | 39.648 | 89.476 | 36.075 | 1.00 13.22 | C |
| ATOM | 36179 | O | ALA | D | 415 | 38.853 | 89.634 | 35.144 | 1.00 12.00 | O |
| ATOM | 36181 | N | ALA | D | 416 | 39.897 | 88.262 | 36.544 | 1.00 13.03 | N |
| ATOM | 36182 | CA | ALA | D | 416 | 39.184 | 87.076 | 35.999 | 1.00 12.63 | C |
| ATOM | 36184 | CB | ALA | D | 416 | 39.727 | 85.818 | 36.530 | 1.00 12.69 | C |

| ATOM | 36188 | C | ALA | D | 416 | 37.670 | 87.180 | 36.242 | 1.00 | 12.75 | C |
|---|---|---|---|---|---|---|---|---|---|---|---|
| ATOM | 36189 | O | ALA | D | 416 | 36.868 | 86.770 | 35.387 | 1.00 | 13.38 | O |
| ATOM | 36191 | N | ALA | D | 417 | 37.254 | 87.807 | 37.354 | 1.00 | 12.57 | N |
| ATOM | 36192 | CA | ALA | D | 417 | 35.801 | 87.928 | 37.560 | 1.00 | 13.76 | C |
| ATOM | 36194 | CB | ALA | D | 417 | 35.486 | 88.590 | 38.834 | 1.00 | 13.85 | C |
| ATOM | 36198 | C | ALA | D | 417 | 35.183 | 88.735 | 36.423 | 1.00 | 13.51 | C |
| ATOM | 36199 | O | ALA | D | 417 | 34.115 | 88.393 | 35.908 | 1.00 | 13.87 | O |
| ATOM | 36201 | N | VAL | D | 418 | 35.881 | 89.797 | 36.002 | 1.00 | 12.52 | N |
| ATOM | 36202 | CA | VAL | D | 418 | 35.417 | 90.645 | 34.872 | 1.00 | 13.15 | C |
| ATOM | 36204 | CB | VAL | D | 418 | 36.247 | 91.897 | 34.715 | 1.00 | 12.75 | C |
| ATOM | 36206 | CG1 | VAL | D | 418 | 35.716 | 92.715 | 33.536 | 1.00 | 13.83 | C |
| ATOM | 36210 | CG2 | VAL | D | 418 | 36.254 | 92.769 | 36.006 | 1.00 | 14.33 | C |
| ATOM | 36214 | C | VAL | D | 418 | 35.453 | 89.908 | 33.550 | 1.00 | 12.20 | C |
| ATOM | 36215 | O | VAL | D | 418 | 34.482 | 89.905 | 32.820 | 1.00 | 12.90 | O |
| ATOM | 36217 | N | ALA | D | 419 | 36.584 | 89.278 | 33.248 | 1.00 | 13.36 | N |
| ATOM | 36218 | CA | ALA | D | 419 | 36.705 | 88.507 | 32.003 | 1.00 | 11.79 | C |
| ATOM | 36220 | CB | ALA | D | 419 | 38.038 | 87.839 | 31.931 | 1.00 | 13.85 | C |
| ATOM | 36224 | C | ALA | D | 419 | 35.584 | 87.495 | 31.916 | 1.00 | 13.17 | C |
| ATOM | 36225 | O | ALA | D | 419 | 34.960 | 87.306 | 30.850 | 1.00 | 13.24 | O |
| ATOM | 36227 | N | ASN | D | 420 | 35.328 | 86.784 | 33.014 | 1.00 | 13.44 | N |
| ATOM | 36228 | CA | ASN | D | 420 | 34.285 | 85.754 | 33.077 | 1.00 | 15.45 | C |
| ATOM | 36230 | CB | ASN | D | 420 | 34.189 | 85.229 | 34.493 | 1.00 | 16.19 | C |
| ATOM | 36233 | CG | ASN | D | 420 | 33.039 | 84.245 | 34.716 | 1.00 | 19.55 | C |
| ATOM | 36234 | OD1 | ASN | D | 420 | 31.963 | 84.659 | 35.136 | 1.00 | 24.62 | O |
| ATOM | 36235 | ND2 | ASN | D | 420 | 33.322 | 82.965 | 34.627 | 1.00 | 19.58 | N |
| ATOM | 36238 | C | ASN | D | 420 | 32.948 | 86.310 | 32.594 | 1.00 | 13.96 | C |
| ATOM | 36239 | O | ASN | D | 420 | 32.263 | 85.691 | 31.779 | 1.00 | 16.52 | O |
| ATOM | 36241 | N | THR | D | 421 | 32.583 | 87.477 | 33.100 | 1.00 | 13.62 | N |
| ATOM | 36242 | CA | THR | D | 421 | 31.315 | 88.129 | 32.665 | 1.00 | 13.23 | C |
| ATOM | 36244 | CB | THR | D | 421 | 30.989 | 89.414 | 33.436 | 1.00 | 14.25 | C |
| ATOM | 36246 | OG1 | THR | D | 421 | 31.877 | 90.481 | 33.049 | 1.00 | 11.30 | O |
| ATOM | 36248 | CG2 | THR | D | 421 | 30.962 | 89.118 | 34.949 | 1.00 | 15.04 | C |
| ATOM | 36252 | C | THR | D | 421 | 31.286 | 88.383 | 31.170 | 1.00 | 13.51 | C |
| ATOM | 36253 | O | THR | D | 421 | 30.230 | 88.293 | 30.489 | 1.00 | 14.20 | O |
| ATOM | 36255 | N | MSE | D | 422 | 32.432 | 88.813 | 30.659 | 1.00 | 12.55 | N |
| ATOM | 36256 | CA | MSE | D | 422 | 32.493 | 89.265 | 29.271 | 1.00 | 12.03 | C |
| ATOM | 36258 | CB | MSE | D | 422 | 33.695 | 90.129 | 29.082 | 1.00 | 12.68 | C |
| ATOM | 36261 | CG | MSE | D | 422 | 33.579 | 91.444 | 29.827 | 1.00 | 11.84 | C |
| ATOM | 36264 | SE | MSE | D | 422 | 32.118 | 92.556 | 28.990 | 1.00 | 21.43 | SE |
| ATOM | 36265 | CE | MSE | D | 422 | 30.659 | 92.171 | 30.287 | 1.00 | 16.12 | C |
| ATOM | 36269 | C | MSE | D | 422 | 32.505 | 88.080 | 28.300 | 1.00 | 12.41 | C |
| ATOM | 36270 | O | MSE | D | 422 | 31.882 | 88.158 | 27.225 | 1.00 | 13.67 | O |
| ATOM | 36272 | N | GLU | D | 423 | 33.144 | 86.981 | 28.685 | 1.00 | 12.74 | N |
| ATOM | 36273 | CA | GLU | D | 423 | 33.154 | 85.810 | 27.811 | 1.00 | 13.54 | C |
| ATOM | 36275 | CB | GLU | D | 423 | 34.031 | 84.694 | 28.380 | 1.00 | 13.52 | C |
| ATOM | 36278 | CG | GLU | D | 423 | 35.519 | 85.115 | 28.532 | 1.00 | 13.09 | C |
| ATOM | 36281 | CD | GLU | D | 423 | 36.322 | 85.075 | 27.260 | 1.00 | 16.37 | C |
| ATOM | 36282 | OE1 | GLU | D | 423 | 36.993 | 84.041 | 27.031 | 1.00 | 17.10 | O |
| ATOM | 36283 | OE2 | GLU | D | 423 | 36.327 | 86.050 | 26.537 | 1.00 | 14.05 | O |
| ATOM | 36284 | C | GLU | D | 423 | 31.736 | 85.237 | 27.688 | 1.00 | 14.25 | C |
| ATOM | 36285 | O | GLU | D | 423 | 31.265 | 84.990 | 26.577 | 1.00 | 14.31 | O |
| ATOM | 36287 | N | LYS | D | 424 | 31.059 | 85.072 | 28.828 | 1.00 | 14.83 | N |
| ATOM | 36288 | CA | LYS | D | 424 | 29.675 | 84.540 | 28.840 | 1.00 | 15.41 | C |
| ATOM | 36290 | CB | LYS | D | 424 | 29.177 | 84.224 | 30.268 | 1.00 | 16.95 | C |
| ATOM | 36293 | CG | LYS | D | 424 | 28.893 | 85.381 | 31.230 | 1.00 | 23.31 | C |
| ATOM | 36296 | CD | LYS | D | 424 | 28.268 | 84.905 | 32.598 | 1.00 | 22.40 | C |
| ATOM | 36299 | CE | LYS | D | 424 | 29.056 | 83.677 | 33.145 | 1.00 | 26.11 | C |

| | | | | | | | | | | |
|---|---|---|---|---|---|---|---|---|---|---|
| ATOM | 36302 | NZ | LYS | D | 424 | 28.663 | 83.359 | 34.548 | 1.00 28.18 | N |
| ATOM | 36306 | C | LYS | D | 424 | 28.705 | 85.499 | 28.092 | 1.00 14.00 | C |
| ATOM | 36307 | O | LYS | D | 424 | 27.819 | 85.063 | 27.305 | 1.00 13.99 | O |
| ATOM | 36309 | N | THR | D | 425 | 28.817 | 86.789 | 28.357 | 1.00 13.37 | N |
| ATOM | 36310 | CA | THR | D | 425 | 27.942 | 87.748 | 27.690 | 1.00 12.42 | C |
| ATOM | 36312 | CB | THR | D | 425 | 28.213 | 89.193 | 28.238 | 1.00 12.39 | C |
| ATOM | 36314 | OG1 | THR | D | 425 | 27.917 | 89.226 | 29.648 | 1.00 11.55 | O |
| ATOM | 36316 | CG2 | THR | D | 425 | 27.352 | 90.252 | 27.571 | 1.00 15.35 | C |
| ATOM | 36320 | C | THR | D | 425 | 28.113 | 87.681 | 26.179 | 1.00 13.22 | C |
| ATOM | 36321 | O | THR | D | 425 | 27.126 | 87.780 | 25.406 | 1.00 14.01 | O |
| ATOM | 36323 | N | ARG | D | 426 | 29.348 | 87.602 | 25.697 | 1.00 12.03 | N |
| ATOM | 36324 | CA | ARG | D | 426 | 29.570 | 87.615 | 24.252 | 1.00 12.32 | C |
| ATOM | 36326 | CB | ARG | D | 426 | 31.067 | 87.807 | 23.960 | 1.00 12.69 | C |
| ATOM | 36329 | CG | ARG | D | 426 | 31.352 | 88.101 | 22.529 | 1.00 13.73 | C |
| ATOM | 36332 | CD | ARG | D | 426 | 32.792 | 88.638 | 22.308 | 1.00 13.25 | C |
| ATOM | 36335 | NE | ARG | D | 426 | 33.787 | 87.621 | 22.653 | 1.00 12.57 | N |
| ATOM | 36337 | CZ | ARG | D | 426 | 34.489 | 87.506 | 23.797 | 1.00 12.08 | C |
| ATOM | 36338 | NH1 | ARG | D | 426 | 34.331 | 88.336 | 24.816 | 1.00 14.00 | N |
| ATOM | 36341 | NH2 | ARG | D | 426 | 35.401 | 86.559 | 23.921 | 1.00 13.64 | N |
| ATOM | 36344 | C | ARG | D | 426 | 29.002 | 86.392 | 23.577 | 1.00 11.47 | C |
| ATOM | 36345 | O | ARG | D | 426 | 28.470 | 86.489 | 22.480 | 1.00 12.16 | O |
| ATOM | 36347 | N | LEU | D | 427 | 29.117 | 85.235 | 24.229 | 1.00 11.89 | N |
| ATOM | 36348 | CA | LEU | D | 427 | 28.445 | 84.008 | 23.720 | 1.00 12.77 | C |
| ATOM | 36350 | CB | LEU | D | 427 | 28.834 | 82.816 | 24.518 | 1.00 13.88 | C |
| ATOM | 36353 | CG | LEU | D | 427 | 28.245 | 81.502 | 24.019 | 1.00 15.30 | C |
| ATOM | 36355 | CD1 | LEU | D | 427 | 28.549 | 81.272 | 22.550 | 1.00 15.92 | C |
| ATOM | 36359 | CD2 | LEU | D | 427 | 28.779 | 80.365 | 24.862 | 1.00 18.56 | C |
| ATOM | 36363 | C | LEU | D | 427 | 26.915 | 84.239 | 23.738 | 1.00 13.13 | C |
| ATOM | 36364 | O | LEU | D | 427 | 26.219 | 83.896 | 22.777 | 1.00 12.32 | O |
| ATOM | 36366 | N | GLY | D | 428 | 26.409 | 84.872 | 24.811 | 1.00 13.15 | N |
| ATOM | 36367 | CA | GLY | D | 428 | 24.964 | 85.146 | 24.897 | 1.00 12.95 | C |
| ATOM | 36370 | C | GLY | D | 428 | 24.489 | 86.085 | 23.799 | 1.00 11.85 | C |
| ATOM | 36371 | O | GLY | D | 428 | 23.438 | 85.868 | 23.203 | 1.00 12.29 | O |
| ATOM | 36373 | N | LEU | D | 429 | 25.285 | 87.074 | 23.411 | 1.00 11.49 | N |
| ATOM | 36374 | CA | LEU | D | 429 | 24.867 | 88.013 | 22.353 | 1.00 12.12 | C |
| ATOM | 36376 | CB | LEU | D | 429 | 25.841 | 89.172 | 22.264 | 1.00 11.56 | C |
| ATOM | 36379 | CG | LEU | D | 429 | 25.904 | 90.034 | 23.540 | 1.00 11.85 | C |
| ATOM | 36381 | CD1 | LEU | D | 429 | 27.162 | 90.926 | 23.542 | 1.00 12.60 | C |
| ATOM | 36385 | CD2 | LEU | D | 429 | 24.600 | 90.883 | 23.599 | 1.00 12.41 | C |
| ATOM | 36389 | C | LEU | D | 429 | 24.776 | 87.256 | 20.997 | 1.00 13.24 | C |
| ATOM | 36390 | O | LEU | D | 429 | 23.892 | 87.504 | 20.170 | 1.00 12.77 | O |
| ATOM | 36392 | N | ALA | D | 430 | 25.699 | 86.323 | 20.787 | 1.00 12.52 | N |
| ATOM | 36393 | CA | ALA | D | 430 | 25.652 | 85.487 | 19.585 | 1.00 11.80 | C |
| ATOM | 36395 | CB | ALA | D | 430 | 26.899 | 84.606 | 19.489 | 1.00 12.79 | C |
| ATOM | 36399 | C | ALA | D | 430 | 24.383 | 84.646 | 19.589 | 1.00 12.20 | C |
| ATOM | 36400 | O | ALA | D | 430 | 23.783 | 84.427 | 18.552 | 1.00 13.82 | O |
| ATOM | 36402 | N | GLN | D | 431 | 24.000 | 84.133 | 20.751 | 1.00 12.15 | N |
| ATOM | 36403 | CA | GLN | D | 431 | 22.799 | 83.292 | 20.854 | 1.00 12.87 | C |
| ATOM | 36405 | CB | GLN | D | 431 | 22.747 | 82.561 | 22.181 | 1.00 14.72 | C |
| ATOM | 36408 | CG | GLN | D | 431 | 23.896 | 81.560 | 22.365 | 1.00 17.29 | C |
| ATOM | 36411 | CD | GLN | D | 431 | 24.015 | 80.565 | 21.277 | 1.00 25.70 | C |
| ATOM | 36412 | OE1 | GLN | D | 431 | 23.205 | 79.627 | 21.164 | 1.00 29.95 | O |
| ATOM | 36413 | NE2 | GLN | D | 431 | 25.067 | 80.723 | 20.469 | 1.00 31.20 | N |
| ATOM | 36416 | C | GLN | D | 431 | 21.514 | 84.129 | 20.630 | 1.00 13.02 | C |
| ATOM | 36417 | O | GLN | D | 431 | 20.585 | 83.679 | 19.965 | 1.00 12.94 | O |
| ATOM | 36419 | N | ILE | D | 432 | 21.454 | 85.339 | 21.175 | 1.00 12.62 | N |
| ATOM | 36420 | CA | ILE | D | 432 | 20.337 | 86.241 | 20.876 | 1.00 12.69 | C |

| | | | | | | | | | | |
|---|---|---|---|---|---|---|---|---|---|---|
| ATOM | 36422 | CB | ILE | D | 432 | 20.504 | 87.600 | 21.617 | 1.00 12.88 | C |
| ATOM | 36424 | CG1 | ILE | D | 432 | 20.433 | 87.356 | 23.131 | 1.00 12.96 | C |
| ATOM | 36427 | CD1 | ILE | D | 432 | 20.866 | 88.505 | 23.935 | 1.00 13.34 | C |
| ATOM | 36431 | CG2 | ILE | D | 432 | 19.486 | 88.562 | 21.138 | 1.00 12.90 | C |
| ATOM | 36435 | C | ILE | D | 432 | 20.313 | 86.496 | 19.393 | 1.00 13.28 | C |
| ATOM | 36436 | O | ILE | D | 432 | 19.280 | 86.422 | 18.761 | 1.00 13.75 | O |
| ATOM | 36438 | N | GLY | D | 433 | 21.466 | 86.831 | 18.822 | 1.00 12.82 | N |
| ATOM | 36439 | CA | GLY | D | 433 | 21.536 | 87.184 | 17.417 | 1.00 13.96 | C |
| ATOM | 36442 | C | GLY | D | 433 | 21.051 | 86.030 | 16.537 | 1.00 13.59 | C |
| ATOM | 36443 | O | GLY | D | 433 | 20.248 | 86.240 | 15.598 | 1.00 12.66 | O |
| ATOM | 36445 | N | LYS | D | 434 | 21.493 | 84.793 | 16.816 | 1.00 12.84 | N |
| ATOM | 36446 | CA | LYS | D | 434 | 21.039 | 83.639 | 16.056 | 1.00 14.15 | C |
| ATOM | 36448 | CB | LYS | D | 434 | 21.747 | 82.392 | 16.523 | 1.00 15.21 | C |
| ATOM | 36451 | CG | LYS | D | 434 | 21.312 | 81.123 | 15.789 | 1.00 13.65 | C |
| ATOM | 36454 | CD | LYS | D | 434 | 21.717 | 81.093 | 14.298 | 1.00 16.42 | C |
| ATOM | 36457 | CE | LYS | D | 434 | 21.220 | 79.856 | 13.620 | 1.00 18.26 | C |
| ATOM | 36460 | NZ | LYS | D | 434 | 21.837 | 79.537 | 12.252 | 1.00 18.64 | N |
| ATOM | 36464 | C | LYS | D | 434 | 19.486 | 83.526 | 16.161 | 1.00 13.24 | C |
| ATOM | 36465 | O | LYS | D | 434 | 18.797 | 83.294 | 15.170 | 1.00 13.36 | O |
| ATOM | 36467 | N | LEU | D | 435 | 18.925 | 83.750 | 17.347 | 1.00 12.79 | N |
| ATOM | 36468 | CA | LEU | D | 435 | 17.466 | 83.663 | 17.490 | 1.00 13.14 | C |
| ATOM | 36470 | CB | LEU | D | 435 | 17.064 | 83.967 | 18.924 | 1.00 13.22 | C |
| ATOM | 36473 | CG | LEU | D | 435 | 15.574 | 83.645 | 19.189 | 1.00 13.00 | C |
| ATOM | 36475 | CD1 | LEU | D | 435 | 15.234 | 82.187 | 19.000 | 1.00 14.70 | C |
| ATOM | 36479 | CD2 | LEU | D | 435 | 15.117 | 84.099 | 20.559 | 1.00 14.30 | C |
| ATOM | 36483 | C | LEU | D | 435 | 16.752 | 84.660 | 16.624 | 1.00 12.25 | C |
| ATOM | 36484 | O | LEU | D | 435 | 15.863 | 84.321 | 15.838 | 1.00 12.63 | O |
| ATOM | 36486 | N | ASN | D | 436 | 17.087 | 85.920 | 16.795 | 1.00 11.91 | N |
| ATOM | 36487 | CA | ASN | D | 436 | 16.370 | 86.947 | 16.060 | 1.00 13.85 | C |
| ATOM | 36489 | CB | ASN | D | 436 | 16.645 | 88.324 | 16.609 | 1.00 13.86 | C |
| ATOM | 36492 | CG | ASN | D | 436 | 16.105 | 88.494 | 18.014 | 1.00 17.26 | C |
| ATOM | 36493 | OD1 | ASN | D | 436 | 16.834 | 88.550 | 18.935 | 1.00 16.48 | O |
| ATOM | 36494 | ND2 | ASN | D | 436 | 14.788 | 88.492 | 18.168 | 1.00 19.94 | N |
| ATOM | 36497 | C | ASN | D | 436 | 16.646 | 86.800 | 14.546 | 1.00 12.60 | C |
| ATOM | 36498 | O | ASN | D | 436 | 15.732 | 87.061 | 13.724 | 1.00 15.08 | O |
| ATOM | 36500 | N | PHE | D | 437 | 17.860 | 86.421 | 14.139 | 1.00 11.22 | N |
| ATOM | 36501 | CA | PHE | D | 437 | 18.090 | 86.215 | 12.725 | 1.00 12.79 | C |
| ATOM | 36503 | CB | PHE | D | 437 | 19.510 | 85.718 | 12.496 | 1.00 13.64 | C |
| ATOM | 36506 | CG | PHE | D | 437 | 19.700 | 85.118 | 11.139 | 1.00 11.87 | C |
| ATOM | 36507 | CD1 | PHE | D | 437 | 19.702 | 85.918 | 10.018 | 1.00 15.65 | C |
| ATOM | 36509 | CE1 | PHE | D | 437 | 19.815 | 85.374 | 8.743 | 1.00 15.81 | C |
| ATOM | 36511 | CZ | PHE | D | 437 | 19.959 | 84.013 | 8.594 | 1.00 13.54 | C |
| ATOM | 36513 | CE2 | PHE | D | 437 | 19.951 | 83.166 | 9.711 | 1.00 16.99 | C |
| ATOM | 36515 | CD2 | PHE | D | 437 | 19.821 | 83.746 | 10.993 | 1.00 13.93 | C |
| ATOM | 36517 | C | PHE | D | 437 | 17.116 | 85.108 | 12.198 | 1.00 13.11 | C |
| ATOM | 36518 | O | PHE | D | 437 | 16.469 | 85.247 | 11.130 | 1.00 13.24 | O |
| ATOM | 36520 | N | THR | D | 438 | 16.981 | 84.000 | 12.928 | 1.00 12.91 | N |
| ATOM | 36521 | CA | THR | D | 438 | 16.127 | 82.910 | 12.457 | 1.00 13.10 | C |
| ATOM | 36523 | CB | THR | D | 438 | 16.268 | 81.584 | 13.270 | 1.00 14.11 | C |
| ATOM | 36525 | OG1 | THR | D | 438 | 15.835 | 81.756 | 14.626 | 1.00 13.95 | O |
| ATOM | 36527 | CG2 | THR | D | 438 | 17.694 | 81.108 | 13.206 | 1.00 12.93 | C |
| ATOM | 36531 | C | THR | D | 438 | 14.668 | 83.361 | 12.370 | 1.00 12.71 | C |
| ATOM | 36532 | O | THR | D | 438 | 13.935 | 82.965 | 11.444 | 1.00 13.94 | O |
| ATOM | 36534 | N | GLN | D | 439 | 14.241 | 84.180 | 13.316 | 1.00 11.52 | N |
| ATOM | 36535 | CA | GLN | D | 439 | 12.855 | 84.688 | 13.318 | 1.00 11.81 | C |
| ATOM | 36537 | CB | GLN | D | 439 | 12.613 | 85.510 | 14.551 | 1.00 12.80 | C |
| ATOM | 36540 | CG | GLN | D | 439 | 12.492 | 84.768 | 15.869 | 1.00 12.50 | C |

```
ATOM   36543  CD  GLN D 439      12.500  85.657  17.089  1.00 12.53           C
ATOM   36544  OE1 GLN D 439      12.645  86.866  16.981  1.00 14.79           O
ATOM   36545  NE2 GLN D 439      12.312  85.051  18.288  1.00 12.14           N
ATOM   36548  C   GLN D 439      12.656  85.578  12.106  1.00 13.55           C
ATOM   36549  O   GLN D 439      11.699  85.412  11.352  1.00 13.34           O
ATOM   36551  N   LEU D 440      13.612  86.488  11.890  1.00 13.71           N
ATOM   36552  CA  LEU D 440      13.539  87.438  10.783  1.00 12.82           C
ATOM   36554  CB  LEU D 440      14.687  88.454  10.911  1.00 13.56           C
ATOM   36557  CG  LEU D 440      14.834  89.487   9.778  1.00 14.22           C
ATOM   36559  CD1 LEU D 440      13.589  90.335   9.527  1.00 13.21           C
ATOM   36563  CD2 LEU D 440      16.064  90.372   9.988  1.00 13.71           C
ATOM   36567  C   LEU D 440      13.567  86.744   9.442  1.00 13.87           C
ATOM   36568  O   LEU D 440      12.760  87.031   8.559  1.00 13.17           O
ATOM   36570  N   THR D 441      14.499  85.844   9.266  1.00 14.09           N
ATOM   36571  CA  THR D 441      14.684  85.306   7.923  1.00 14.13           C
ATOM   36573  CB  THR D 441      16.043  84.605   7.763  1.00 15.49           C
ATOM   36575  OG1 THR D 441      16.347  84.442   6.372  1.00 16.97           O
ATOM   36577  CG2 THR D 441      16.055  83.319   8.453  1.00 14.81           C
ATOM   36581  C   THR D 441      13.473  84.394   7.585  1.00 15.16           C
ATOM   36582  O   THR D 441      13.082  84.275   6.391  1.00 15.45           O
ATOM   36584  N   GLU D 442      12.867  83.788   8.610  1.00 14.77           N
ATOM   36585  CA  GLU D 442      11.606  83.072   8.403  1.00 16.45           C
ATOM   36587  CB  GLU D 442      11.167  82.399   9.704  1.00 16.32           C
ATOM   36590  CG  GLU D 442       9.870  81.600   9.581  1.00 18.29           C
ATOM   36593  CD  GLU D 442       9.487  80.827  10.844  1.00 19.88           C
ATOM   36594  OE1 GLU D 442      10.365  80.597  11.726  1.00 24.67           O
ATOM   36595  OE2 GLU D 442       8.290  80.390  10.932  1.00 20.91           O
ATOM   36596  C   GLU D 442      10.513  84.030   7.913  1.00 15.85           C
ATOM   36597  O   GLU D 442       9.783  83.752   6.949  1.00 16.42           O
ATOM   36599  N   MSE D 443      10.422  85.174   8.560  1.00 14.68           N
ATOM   36600  CA  MSE D 443       9.429  86.160   8.226  1.00 15.13           C
ATOM   36602  CB  MSE D 443       9.419  87.258   9.296  1.00 14.51           C
ATOM   36605  CG  MSE D 443       8.360  88.269   9.068  1.00 15.95           C
ATOM   36608  SE  MSE D 443       8.246  89.567  10.521  1.00 24.34          SE
ATOM   36609  CE  MSE D 443      10.093  90.224  10.505  1.00 22.44           C
ATOM   36613  C   MSE D 443       9.616  86.756   6.810  1.00 14.57           C
ATOM   36614  O   MSE D 443       8.640  87.127   6.126  1.00 16.59           O
ATOM   36616  N   LEU D 444      10.862  86.793   6.364  1.00 14.68           N
ATOM   36617  CA  LEU D 444      11.185  87.298   5.013  1.00 16.67           C
ATOM   36619  CB  LEU D 444      12.547  87.954   5.042  1.00 15.43           C
ATOM   36622  CG  LEU D 444      12.739  89.139   6.001  1.00 14.69           C
ATOM   36624  CD1 LEU D 444      14.133  89.678   5.898  1.00 16.46           C
ATOM   36628  CD2 LEU D 444      11.668  90.162   5.703  1.00 12.85           C
ATOM   36632  C   LEU D 444      11.167  86.208   3.940  1.00 17.92           C
ATOM   36633  O   LEU D 444      11.494  86.485   2.771  1.00 20.64           O
ATOM   36635  N   ASN D 445      10.833  84.980   4.320  1.00 17.67           N
ATOM   36636  CA  ASN D 445      10.750  83.887   3.362  1.00 16.91           C
ATOM   36638  CB  ASN D 445      11.362  82.619   3.977  1.00 17.90           C
ATOM   36641  CG  ASN D 445      11.413  81.426   3.021  1.00 20.84           C
ATOM   36642  OD1 ASN D 445      10.458  81.139   2.279  1.00 20.93           O
ATOM   36643  ND2 ASN D 445      12.499  80.683   3.094  1.00 15.79           N
ATOM   36646  C   ASN D 445       9.294  83.671   2.930  1.00 16.06           C
ATOM   36647  O   ASN D 445       8.454  83.238   3.724  1.00 15.43           O
ATOM   36649  N   ALA D 446       8.980  83.970   1.658  1.00 17.52           N
ATOM   36650  CA  ALA D 446       7.582  83.888   1.196  1.00 17.22           C
ATOM   36652  CB  ALA D 446       7.494  84.294  -0.268  1.00 17.61           C
ATOM   36656  C   ALA D 446       6.957  82.490   1.359  1.00 17.63           C
```

| ATOM | 36657 | O | ALA | D | 446 | 5.738 | 82.367 | 1.503 | 1.00 | 17.60 | O |
|---|---|---|---|---|---|---|---|---|---|---|---|
| ATOM | 36659 | N | GLY | D | 447 | 7.800 | 81.456 | 1.343 | 1.00 | 17.00 | N |
| ATOM | 36660 | CA | GLY | D | 447 | 7.341 | 80.124 | 1.501 | 1.00 | 18.27 | C |
| ATOM | 36663 | C | GLY | D | 447 | 6.952 | 79.775 | 2.912 | 1.00 | 18.99 | C |
| ATOM | 36664 | O | GLY | D | 447 | 6.254 | 78.789 | 3.110 | 1.00 | 19.39 | O |
| ATOM | 36666 | N | MSE | D | 448 | 7.391 | 80.569 | 3.894 | 1.00 | 17.43 | N |
| ATOM | 36667 | CA | MSE | D | 448 | 7.236 | 80.253 | 5.317 | 1.00 | 18.86 | C |
| ATOM | 36669 | CB | MSE | D | 448 | 8.648 | 80.176 | 5.945 | 1.00 | 18.24 | C |
| ATOM | 36672 | CG | MSE | D | 448 | 9.509 | 79.190 | 5.274 | 1.00 | 20.05 | C |
| ATOM | 36675 | SE | MSE | D | 448 | 11.348 | 79.208 | 6.094 | 1.00 | 30.44 | SE |
| ATOM | 36676 | CE | MSE | D | 448 | 10.868 | 78.355 | 7.683 | 1.00 | 22.93 | C |
| ATOM | 36680 | C | MSE | D | 448 | 6.432 | 81.257 | 6.154 | 1.00 | 18.43 | C |
| ATOM | 36681 | O | MSE | D | 448 | 6.090 | 80.994 | 7.327 | 1.00 | 17.99 | O |
| ATOM | 36683 | N | ASN | D | 449 | 6.101 | 82.392 | 5.549 | 1.00 | 18.06 | N |
| ATOM | 36684 | CA | ASN | D | 449 | 5.675 | 83.557 | 6.327 | 1.00 | 17.66 | C |
| ATOM | 36686 | CB | ASN | D | 449 | 6.471 | 84.778 | 5.884 | 1.00 | 17.88 | C |
| ATOM | 36689 | CG | ASN | D | 449 | 6.118 | 85.230 | 4.497 | 1.00 | 18.00 | C |
| ATOM | 36690 | OD1 | ASN | D | 449 | 5.222 | 84.659 | 3.869 | 1.00 | 19.90 | O |
| ATOM | 36691 | ND2 | ASN | D | 449 | 6.844 | 86.245 | 3.979 | 1.00 | 15.78 | N |
| ATOM | 36694 | C | ASN | D | 449 | 4.173 | 83.810 | 6.345 | 1.00 | 18.53 | C |
| ATOM | 36695 | O | ASN | D | 449 | 3.711 | 84.939 | 6.558 | 1.00 | 18.17 | O |
| ATOM | 36697 | N | ARG | D | 450 | 3.404 | 82.745 | 6.153 | 1.00 | 19.22 | N |
| ATOM | 36698 | CA | ARG | D | 450 | 1.954 | 82.782 | 6.292 | 1.00 | 20.70 | C |
| ATOM | 36700 | CB | ARG | D | 450 | 1.558 | 82.944 | 7.765 | 1.00 | 24.15 | C |
| ATOM | 36703 | CG | ARG | D | 450 | 2.010 | 81.775 | 8.630 | 1.00 | 31.19 | C |
| ATOM | 36706 | CD | ARG | D | 450 | 1.216 | 80.514 | 8.294 | 1.00 | 42.11 | C |
| ATOM | 36709 | NE | ARG | D | 450 | 1.907 | 79.274 | 8.713 | 1.00 | 48.05 | N |
| ATOM | 36711 | CZ | ARG | D | 450 | 1.551 | 78.501 | 9.747 | 1.00 | 50.71 | C |
| ATOM | 36712 | NH1 | ARG | D | 450 | 0.490 | 78.798 | 10.520 | 1.00 | 53.66 | N |
| ATOM | 36715 | NH2 | ARG | D | 450 | 2.262 | 77.412 | 10.004 | 1.00 | 50.11 | N |
| ATOM | 36718 | C | ARG | D | 450 | 1.360 | 83.872 | 5.415 | 1.00 | 19.74 | C |
| ATOM | 36719 | O | ARG | D | 450 | 0.403 | 84.561 | 5.758 | 1.00 | 18.81 | O |
| ATOM | 36721 | N | GLY | D | 451 | 1.882 | 83.984 | 4.214 | 1.00 | 17.37 | N |
| ATOM | 36722 | CA | GLY | D | 451 | 1.230 | 84.829 | 3.229 | 1.00 | 17.29 | C |
| ATOM | 36725 | C | GLY | D | 451 | 1.592 | 86.294 | 3.230 | 1.00 | 17.16 | C |
| ATOM | 36726 | O | GLY | D | 451 | 0.987 | 87.066 | 2.508 | 1.00 | 17.97 | O |
| ATOM | 36728 | N | LEU | D | 452 | 2.622 | 86.683 | 3.975 | 1.00 | 15.53 | N |
| ATOM | 36729 | CA | LEU | D | 452 | 3.119 | 88.063 | 3.860 | 1.00 | 16.04 | C |
| ATOM | 36731 | CB | LEU | D | 452 | 4.200 | 88.383 | 4.906 | 1.00 | 16.23 | C |
| ATOM | 36734 | CG | LEU | D | 452 | 3.673 | 88.527 | 6.332 | 1.00 | 16.98 | C |
| ATOM | 36736 | CD1 | LEU | D | 452 | 4.796 | 88.389 | 7.333 | 1.00 | 19.56 | C |
| ATOM | 36740 | CD2 | LEU | D | 452 | 2.947 | 89.806 | 6.511 | 1.00 | 17.77 | C |
| ATOM | 36744 | C | LEU | D | 452 | 3.696 | 88.274 | 2.449 | 1.00 | 14.93 | C |
| ATOM | 36745 | O | LEU | D | 452 | 4.255 | 87.361 | 1.896 | 1.00 | 15.40 | O |
| ATOM | 36747 | N | PRO | D | 453 | 3.548 | 89.495 | 1.882 | 1.00 | 15.62 | N |
| ATOM | 36748 | CA | PRO | D | 453 | 4.142 | 89.723 | 0.577 | 1.00 | 15.20 | C |
| ATOM | 36750 | CB | PRO | D | 453 | 3.971 | 91.244 | 0.369 | 1.00 | 15.92 | C |
| ATOM | 36753 | CG | PRO | D | 453 | 2.842 | 91.606 | 1.186 | 1.00 | 16.35 | C |
| ATOM | 36756 | CD | PRO | D | 453 | 2.889 | 90.703 | 2.413 | 1.00 | 16.55 | C |
| ATOM | 36759 | C | PRO | D | 453 | 5.597 | 89.362 | 0.484 | 1.00 | 15.15 | C |
| ATOM | 36760 | O | PRO | D | 453 | 6.371 | 89.571 | 1.410 | 1.00 | 14.75 | O |
| ATOM | 36761 | N | SER | D | 454 | 6.010 | 88.861 | -0.666 | 1.00 | 15.57 | N |
| ATOM | 36762 | CA | SER | D | 454 | 7.429 | 88.545 | -0.830 | 1.00 | 16.77 | C |
| ATOM | 36764 | CB | SER | D | 454 | 7.688 | 88.012 | -2.234 | 1.00 | 18.82 | C |
| ATOM | 36767 | OG | SER | D | 454 | 7.109 | 88.923 | -3.108 | 1.00 | 23.73 | O |
| ATOM | 36769 | C | SER | D | 454 | 8.307 | 89.776 | -0.598 | 1.00 | 15.48 | C |
| ATOM | 36770 | O | SER | D | 454 | 7.986 | 90.890 | -1.076 | 1.00 | 16.04 | O |

| ATOM | 36772 | N   | CYS | D | 455 | 9.359  | 89.545  | 0.178   | 1.00 | 16.82 | N |
|------|-------|-----|-----|---|-----|--------|---------|---------|------|-------|---|
| ATOM | 36773 | CA  | CYS | D | 455 | 10.328 | 90.560  | 0.565   | 1.00 | 16.25 | C |
| ATOM | 36775 | CB  | CYS | D | 455 | 11.025 | 91.137  | -0.650  | 1.00 | 17.57 | C |
| ATOM | 36778 | SG  | CYS | D | 455 | 11.971 | 89.907  | -1.605  | 1.00 | 21.79 | S |
| ATOM | 36780 | C   | CYS | D | 455 | 9.726  | 91.721  | 1.341   | 1.00 | 13.96 | C |
| ATOM | 36781 | O   | CYS | D | 455 | 10.356 | 92.752  | 1.474   | 1.00 | 14.24 | O |
| ATOM | 36783 | N   | LEU | D | 456 | 8.507  | 91.533  | 1.836   | 1.00 | 13.00 | N |
| ATOM | 36784 | CA  | LEU | D | 456 | 7.722  | 92.593  | 2.449   | 1.00 | 13.97 | C |
| ATOM | 36786 | CB  | LEU | D | 456 | 8.256  | 92.970  | 3.826   | 1.00 | 14.29 | C |
| ATOM | 36789 | CG  | LEU | D | 456 | 8.507  | 91.808  | 4.798   | 1.00 | 14.25 | C |
| ATOM | 36791 | CD1 | LEU | D | 456 | 8.987  | 92.396  | 6.166   | 1.00 | 13.33 | C |
| ATOM | 36795 | CD2 | LEU | D | 456 | 7.229  | 90.977  | 4.970   | 1.00 | 15.81 | C |
| ATOM | 36799 | C   | LEU | D | 456 | 7.547  | 93.813  | 1.529   | 1.00 | 14.20 | C |
| ATOM | 36800 | O   | LEU | D | 456 | 7.455  | 94.980  | 1.983   | 1.00 | 14.54 | O |
| ATOM | 36802 | N   | ALA | D | 457 | 7.472  | 93.544  | 0.222   | 1.00 | 14.31 | N |
| ATOM | 36803 | CA  | ALA | D | 457 | 7.166  | 94.579  | -0.777  | 1.00 | 14.48 | C |
| ATOM | 36805 | CB  | ALA | D | 457 | 7.354  | 94.038  | -2.153  | 1.00 | 14.71 | C |
| ATOM | 36809 | C   | ALA | D | 457 | 5.716  | 95.009  | -0.586  | 1.00 | 14.80 | C |
| ATOM | 36810 | O   | ALA | D | 457 | 4.831  | 94.147  | -0.432  | 1.00 | 16.28 | O |
| ATOM | 36812 | N   | ALA | D | 458 | 5.468  | 96.327  | -0.629  | 1.00 | 14.62 | N |
| ATOM | 36813 | CA  | ALA | D | 458 | 4.098  | 96.861  | -0.468  | 1.00 | 14.19 | C |
| ATOM | 36815 | CB  | ALA | D | 458 | 4.114  | 98.260  | -0.001  | 1.00 | 14.59 | C |
| ATOM | 36819 | C   | ALA | D | 458 | 3.245  | 96.750  | -1.743  | 1.00 | 14.52 | C |
| ATOM | 36820 | O   | ALA | D | 458 | 2.031  | 96.703  | -1.653  | 1.00 | 16.31 | O |
| ATOM | 36822 | N   | GLU | D | 459 | 3.917  | 96.723  | -2.897  | 1.00 | 14.41 | N |
| ATOM | 36823 | CA  | GLU | D | 459 | 3.291  | 96.758  | -4.191  | 1.00 | 14.42 | C |
| ATOM | 36825 | CB  | GLU | D | 459 | 3.557  | 98.124  | -4.845  | 1.00 | 15.22 | C |
| ATOM | 36828 | CG  | GLU | D | 459 | 2.953  | 99.310  | -4.093  | 1.00 | 15.00 | C |
| ATOM | 36831 | CD  | GLU | D | 459 | 1.420  | 99.403  | -4.241  | 1.00 | 17.23 | C |
| ATOM | 36832 | OE1 | GLU | D | 459 | 0.855  | 98.865  | -5.235  | 1.00 | 15.11 | O |
| ATOM | 36833 | OE2 | GLU | D | 459 | 0.746  | 100.070 | -3.408  | 1.00 | 15.69 | O |
| ATOM | 36834 | C   | GLU | D | 459 | 3.822  | 95.523  | -4.980  | 1.00 | 15.32 | C |
| ATOM | 36835 | O   | GLU | D | 459 | 4.385  | 94.605  | -4.361  | 1.00 | 17.41 | O |
| ATOM | 36837 | N   | ASP | D | 460 | 3.663  | 95.476  | -6.312  | 1.00 | 14.58 | N |
| ATOM | 36838 | CA  | ASP | D | 460 | 3.936  | 94.252  | -7.058  | 1.00 | 15.43 | C |
| ATOM | 36840 | CB  | ASP | D | 460 | 3.678  | 94.445  | -8.537  | 1.00 | 15.22 | C |
| ATOM | 36843 | CG  | ASP | D | 460 | 2.250  | 94.127  | -8.934  | 1.00 | 14.80 | C |
| ATOM | 36844 | OD1 | ASP | D | 460 | 1.449  | 93.649  | -8.100  | 1.00 | 16.44 | O |
| ATOM | 36845 | OD2 | ASP | D | 460 | 1.917  | 94.368  | -10.115 | 1.00 | 16.23 | O |
| ATOM | 36846 | C   | ASP | D | 460 | 5.363  | 93.811  | -6.844  | 1.00 | 16.08 | C |
| ATOM | 36847 | O   | ASP | D | 460 | 6.291  | 94.629  | -6.997  | 1.00 | 15.58 | O |
| ATOM | 36849 | N   | PRO | D | 461 | 5.538  | 92.564  | -6.390  | 1.00 | 16.65 | N |
| ATOM | 36850 | CA  | PRO | D | 461 | 6.902  | 92.141  | -6.106  | 1.00 | 17.15 | C |
| ATOM | 36852 | CB  | PRO | D | 461 | 6.733  | 90.770  | -5.451  | 1.00 | 17.01 | C |
| ATOM | 36855 | CG  | PRO | D | 461 | 5.363  | 90.484  | -5.290  | 1.00 | 19.86 | C |
| ATOM | 36858 | CD  | PRO | D | 461 | 4.531  | 91.557  | -5.989  | 1.00 | 17.21 | C |
| ATOM | 36861 | C   | PRO | D | 461 | 7.836  | 91.988  | -7.300  | 1.00 | 16.77 | C |
| ATOM | 36862 | O   | PRO | D | 461 | 9.052  | 91.941  | -7.107  | 1.00 | 16.58 | O |
| ATOM | 36863 | N   | SER | D | 462 | 7.302  | 91.900  | -8.518  | 1.00 | 17.30 | N |
| ATOM | 36864 | CA  | SER | D | 462 | 8.163  | 91.794  | -9.671  | 1.00 | 17.82 | C |
| ATOM | 36866 | CB  | SER | D | 462 | 7.355  | 91.619  | -10.975 | 1.00 | 18.17 | C |
| ATOM | 36869 | OG  | SER | D | 462 | 6.559  | 92.739  | -11.224 | 1.00 | 16.82 | O |
| ATOM | 36871 | C   | SER | D | 462 | 9.147  | 92.973  | -9.796  | 1.00 | 19.03 | C |
| ATOM | 36872 | O   | SER | D | 462 | 10.225 | 92.818  | -10.367 | 1.00 | 21.50 | O |
| ATOM | 36874 | N   | LEU | D | 463 | 8.798  | 94.122  | -9.232  | 1.00 | 18.74 | N |
| ATOM | 36875 | CA  | LEU | D | 463 | 9.664  | 95.286  | -9.289  | 1.00 | 19.28 | C |
| ATOM | 36877 | CB  | LEU | D | 463 | 9.067  | 96.325  | -10.219 | 1.00 | 20.55 | C |

```
ATOM  36880  CG   LEU D 463       9.171  95.905 -11.706  1.00 23.79           C
ATOM  36882  CD1  LEU D 463       8.428  96.912 -12.571  1.00 25.63           C
ATOM  36886  CD2  LEU D 463      10.613  95.762 -12.177  1.00 25.61           C
ATOM  36890  C    LEU D 463       9.976  95.892  -7.918  1.00 17.05           C
ATOM  36891  O    LEU D 463      10.366  97.057  -7.816  1.00 16.18           O
ATOM  36893  N    SER D 464       9.878  95.071  -6.887  1.00 15.96           N
ATOM  36894  CA   SER D 464      10.157  95.517  -5.544  1.00 15.10           C
ATOM  36896  CB   SER D 464       8.906  96.114  -4.940  1.00 16.15           C
ATOM  36899  OG   SER D 464       9.177  96.558  -3.629  1.00 16.09           O
ATOM  36901  C    SER D 464      10.652  94.344  -4.694  1.00 15.30           C
ATOM  36902  O    SER D 464       9.922  93.362  -4.468  1.00 16.07           O
ATOM  36904  N    TYR D 465      11.884  94.430  -4.218  1.00 15.18           N
ATOM  36905  CA   TYR D 465      12.507  93.366  -3.435  1.00 15.96           C
ATOM  36907  CB   TYR D 465      13.781  92.892  -4.128  1.00 18.30           C
ATOM  36910  CG   TYR D 465      13.627  92.805  -5.624  1.00 20.06           C
ATOM  36911  CD1  TYR D 465      12.666  92.007  -6.191  1.00 25.07           C
ATOM  36913  CE1  TYR D 465      12.473  91.967  -7.590  1.00 23.66           C
ATOM  36915  CZ   TYR D 465      13.276  92.750  -8.390  1.00 26.55           C
ATOM  36916  OH   TYR D 465      13.136  92.756  -9.795  1.00 28.81           O
ATOM  36918  CE2  TYR D 465      14.239  93.563  -7.830  1.00 24.40           C
ATOM  36920  CD2  TYR D 465      14.392  93.606  -6.452  1.00 22.94           C
ATOM  36922  C    TYR D 465      12.835  93.898  -2.035  1.00 15.83           C
ATOM  36923  O    TYR D 465      13.771  93.428  -1.389  1.00 15.83           O
ATOM  36925  N    HIS D 466      12.002  94.836  -1.596  1.00 14.47           N
ATOM  36926  CA   HIS D 466      12.155  95.607  -0.362  1.00 13.45           C
ATOM  36928  CB   HIS D 466      10.790  95.814   0.301  1.00 13.23           C
ATOM  36931  CG   HIS D 466      10.823  96.753   1.466  1.00 14.81           C
ATOM  36932  ND1  HIS D 466       9.752  96.924   2.320  1.00 14.22           N
ATOM  36934  CE1  HIS D 466      10.084  97.796   3.262  1.00 14.13           C
ATOM  36936  NE2  HIS D 466      11.331  98.191   3.039  1.00 14.05           N
ATOM  36938  CD2  HIS D 466      11.809  97.553   1.925  1.00 16.90           C
ATOM  36940  C    HIS D 466      13.202  95.106   0.636  1.00 13.14           C
ATOM  36941  O    HIS D 466      14.274  95.655   0.685  1.00 14.14           O
ATOM  36943  N    CYS D 467      12.859  94.107   1.448  1.00 15.07           N
ATOM  36944  CA   CYS D 467      13.735  93.647   2.538  1.00 14.13           C
ATOM  36946  CB   CYS D 467      12.875  93.283   3.754  1.00 15.44           C
ATOM  36949  SG   CYS D 467      12.001  94.699   4.500  1.00 16.12           S
ATOM  36951  C    CYS D 467      14.731  92.515   2.204  1.00 15.07           C
ATOM  36952  O    CYS D 467      15.327  91.932   3.134  1.00 15.50           O
ATOM  36954  N    LYS D 468      14.900  92.207   0.918  1.00 14.73           N
ATOM  36955  CA   LYS D 468      15.844  91.171   0.514  1.00 15.07           C
ATOM  36957  CB   LYS D 468      15.768  90.981  -0.985  1.00 14.03           C
ATOM  36960  CG   LYS D 468      16.644  89.841  -1.461  1.00 18.90           C
ATOM  36963  CD   LYS D 468      16.554  89.762  -2.984  1.00 23.30           C
ATOM  36966  CE   LYS D 468      15.234  89.227  -3.445  1.00 26.06           C
ATOM  36969  NZ   LYS D 468      15.042  87.916  -2.808  1.00 30.53           N
ATOM  36973  C    LYS D 468      17.285  91.489   0.926  1.00 15.35           C
ATOM  36974  O    LYS D 468      18.021  90.613   1.404  1.00 16.22           O
ATOM  36976  N    GLY D 469      17.727  92.735   0.760  1.00 14.10           N
ATOM  36977  CA   GLY D 469      19.065  93.106   1.214  1.00 14.13           C
ATOM  36980  C    GLY D 469      19.225  92.981   2.717  1.00 14.04           C
ATOM  36981  O    GLY D 469      20.286  92.642   3.215  1.00 13.12           O
ATOM  36983  N    LEU D 470      18.174  93.337   3.461  1.00 13.72           N
ATOM  36984  CA   LEU D 470      18.236  93.245   4.922  1.00 13.43           C
ATOM  36986  CB   LEU D 470      17.046  93.979   5.539  1.00 14.02           C
ATOM  36989  CG   LEU D 470      17.083  95.500   5.457  1.00 14.69           C
ATOM  36991  CD1  LEU D 470      15.794  96.066   6.102  1.00 15.11           C
```

| | | | | | | | | | |
|---|---|---|---|---|---|---|---|---|---|
| ATOM | 36995 | CD2 | LEU | D | 470 | 18.371 | 96.060 | 6.117 | 1.00 14.59 | C |
| ATOM | 36999 | C | LEU | D | 470 | 18.274 | 91.780 | 5.368 | 1.00 14.17 | C |
| ATOM | 37000 | O | LEU | D | 470 | 18.858 | 91.464 | 6.391 | 1.00 14.01 | O |
| ATOM | 37002 | N | ASP | D | 471 | 17.633 | 90.887 | 4.630 | 1.00 14.19 | N |
| ATOM | 37003 | CA | ASP | D | 471 | 17.710 | 89.440 | 4.940 | 1.00 15.00 | C |
| ATOM | 37005 | CB | ASP | D | 471 | 16.853 | 88.683 | 3.905 | 1.00 16.42 | C |
| ATOM | 37008 | CG | ASP | D | 471 | 16.531 | 87.241 | 4.293 | 1.00 20.64 | C |
| ATOM | 37009 | OD1 | ASP | D | 471 | 16.603 | 86.840 | 5.481 | 1.00 20.55 | O |
| ATOM | 37010 | OD2 | ASP | D | 471 | 16.143 | 86.504 | 3.339 | 1.00 19.36 | O |
| ATOM | 37011 | C | ASP | D | 471 | 19.196 | 89.026 | 4.888 | 1.00 15.16 | C |
| ATOM | 37012 | O | ASP | D | 471 | 19.767 | 88.362 | 5.767 | 1.00 14.76 | O |
| ATOM | 37014 | N | ILE | D | 472 | 19.856 | 89.460 | 3.832 | 1.00 14.29 | N |
| ATOM | 37015 | CA | ILE | D | 472 | 21.297 | 89.209 | 3.622 | 1.00 13.91 | C |
| ATOM | 37017 | CB | ILE | D | 472 | 21.741 | 89.699 | 2.212 | 1.00 13.96 | C |
| ATOM | 37019 | CG1 | ILE | D | 472 | 21.044 | 88.816 | 1.174 | 1.00 16.97 | C |
| ATOM | 37022 | CD1 | ILE | D | 472 | 21.121 | 89.392 | -0.237 | 1.00 17.81 | C |
| ATOM | 37026 | CG2 | ILE | D | 472 | 23.224 | 89.563 | 2.006 | 1.00 15.00 | C |
| ATOM | 37030 | C | ILE | D | 472 | 22.145 | 89.852 | 4.731 | 1.00 13.50 | C |
| ATOM | 37031 | O | ILE | D | 472 | 23.073 | 89.229 | 5.305 | 1.00 14.94 | O |
| ATOM | 37033 | N | ALA | D | 473 | 21.864 | 91.133 | 5.008 | 1.00 14.32 | N |
| ATOM | 37034 | CA | ALA | D | 473 | 22.606 | 91.870 | 6.065 | 1.00 13.78 | C |
| ATOM | 37036 | CB | ALA | D | 473 | 22.121 | 93.298 | 6.206 | 1.00 14.74 | C |
| ATOM | 37040 | C | ALA | D | 473 | 22.491 | 91.150 | 7.394 | 1.00 13.61 | C |
| ATOM | 37041 | O | ALA | D | 473 | 23.459 | 91.019 | 8.194 | 1.00 13.48 | O |
| ATOM | 37043 | N | ALA | D | 474 | 21.270 | 90.674 | 7.666 | 1.00 12.83 | N |
| ATOM | 37044 | CA | ALA | D | 474 | 21.010 | 89.996 | 8.940 | 1.00 13.74 | C |
| ATOM | 37046 | CB | ALA | D | 474 | 19.539 | 89.698 | 9.115 | 1.00 14.96 | C |
| ATOM | 37050 | C | ALA | D | 474 | 21.888 | 88.760 | 9.046 | 1.00 12.47 | C |
| ATOM | 37051 | O | ALA | D | 474 | 22.453 | 88.459 | 10.127 | 1.00 14.20 | O |
| ATOM | 37053 | N | ALA | D | 475 | 22.053 | 88.018 | 7.936 | 1.00 12.10 | N |
| ATOM | 37054 | CA | ALA | D | 475 | 22.957 | 86.878 | 7.916 | 1.00 11.04 | C |
| ATOM | 37056 | CB | ALA | D | 475 | 22.900 | 86.210 | 6.595 | 1.00 10.83 | C |
| ATOM | 37060 | C | ALA | D | 475 | 24.387 | 87.287 | 8.227 | 1.00 12.62 | C |
| ATOM | 37061 | O | ALA | D | 475 | 25.101 | 86.686 | 9.034 | 1.00 13.41 | O |
| ATOM | 37063 | N | ALA | D | 476 | 24.814 | 88.341 | 7.561 | 1.00 12.03 | N |
| ATOM | 37064 | CA | ALA | D | 476 | 26.170 | 88.832 | 7.709 | 1.00 12.43 | C |
| ATOM | 37066 | CB | ALA | D | 476 | 26.348 | 90.069 | 6.915 | 1.00 13.56 | C |
| ATOM | 37070 | C | ALA | D | 476 | 26.452 | 89.216 | 9.189 | 1.00 12.31 | C |
| ATOM | 37071 | O | ALA | D | 476 | 27.529 | 88.904 | 9.744 | 1.00 13.53 | O |
| ATOM | 37073 | N | TYR | D | 477 | 25.508 | 89.908 | 9.821 | 1.00 12.00 | N |
| ATOM | 37074 | CA | TYR | D | 477 | 25.677 | 90.331 | 11.223 | 1.00 12.80 | C |
| ATOM | 37076 | CB | TYR | D | 477 | 24.485 | 91.165 | 11.712 | 1.00 12.11 | C |
| ATOM | 37079 | CG | TYR | D | 477 | 24.256 | 92.435 | 10.881 | 1.00 12.17 | C |
| ATOM | 37080 | CD1 | TYR | D | 477 | 25.319 | 93.145 | 10.326 | 1.00 12.87 | C |
| ATOM | 37082 | CE1 | TYR | D | 477 | 25.116 | 94.323 | 9.590 | 1.00 13.78 | C |
| ATOM | 37084 | CZ | TYR | D | 477 | 23.839 | 94.773 | 9.376 | 1.00 10.88 | C |
| ATOM | 37085 | OH | TYR | D | 477 | 23.572 | 95.900 | 8.615 | 1.00 14.45 | O |
| ATOM | 37087 | CE2 | TYR | D | 477 | 22.759 | 94.055 | 9.919 | 1.00 12.79 | C |
| ATOM | 37089 | CD2 | TYR | D | 477 | 22.973 | 92.917 | 10.641 | 1.00 12.21 | C |
| ATOM | 37091 | C | TYR | D | 477 | 25.786 | 89.090 | 12.103 | 1.00 13.19 | C |
| ATOM | 37092 | O | TYR | D | 477 | 26.610 | 88.990 | 13.035 | 1.00 12.77 | O |
| ATOM | 37094 | N | THR | D | 478 | 24.916 | 88.102 | 11.861 | 1.00 11.95 | N |
| ATOM | 37095 | CA | THR | D | 478 | 24.906 | 86.880 | 12.648 | 1.00 12.31 | C |
| ATOM | 37097 | CB | THR | D | 478 | 23.691 | 86.043 | 12.241 | 1.00 13.14 | C |
| ATOM | 37099 | OG1 | THR | D | 478 | 22.512 | 86.863 | 12.429 | 1.00 12.26 | O |
| ATOM | 37101 | CG2 | THR | D | 478 | 23.582 | 84.829 | 13.053 | 1.00 16.17 | C |
| ATOM | 37105 | C | THR | D | 478 | 26.222 | 86.120 | 12.509 | 1.00 12.04 | C |

| | | | | | | | | | |
|---|---|---|---|---|---|---|---|---|---|
| ATOM | 37106 | O | THR | D | 478 | 26.778 | 85.648 | 13.463 | 1.00 13.19 | O |
| ATOM | 37108 | N | SER | D | 479 | 26.719 | 85.985 | 11.282 | 1.00 12.40 | N |
| ATOM | 37109 | CA | SER | D | 479 | 28.003 | 85.330 | 11.097 | 1.00 13.01 | C |
| ATOM | 37111 | CB | SER | D | 479 | 28.389 | 85.344 | 9.632 | 1.00 12.94 | C |
| ATOM | 37114 | OG | SER | D | 479 | 27.509 | 84.544 | 8.850 | 1.00 13.66 | O |
| ATOM | 37116 | C | SER | D | 479 | 29.110 | 86.016 | 11.912 | 1.00 12.33 | C |
| ATOM | 37117 | O | SER | D | 479 | 29.925 | 85.350 | 12.549 | 1.00 13.02 | O |
| ATOM | 37119 | N | GLU | D | 480 | 29.147 | 87.327 | 11.798 | 1.00 13.80 | N |
| ATOM | 37120 | CA | GLU | D | 480 | 30.137 | 88.148 | 12.541 | 1.00 13.04 | C |
| ATOM | 37122 | CB | GLU | D | 480 | 29.991 | 89.628 | 12.238 | 1.00 14.88 | C |
| ATOM | 37125 | CG | GLU | D | 480 | 31.167 | 90.403 | 12.824 | 1.00 12.87 | C |
| ATOM | 37128 | CD | GLU | D | 480 | 31.340 | 91.807 | 12.223 | 1.00 14.24 | C |
| ATOM | 37129 | OE1 | GLU | D | 480 | 30.784 | 92.053 | 11.095 | 1.00 13.83 | O |
| ATOM | 37130 | OE2 | GLU | D | 480 | 32.002 | 92.669 | 12.861 | 1.00 14.56 | O |
| ATOM | 37131 | C | GLU | D | 480 | 30.054 | 87.887 | 14.068 | 1.00 11.90 | C |
| ATOM | 37132 | O | GLU | D | 480 | 31.072 | 87.711 | 14.746 | 1.00 13.67 | O |
| ATOM | 37134 | N | LEU | D | 481 | 28.843 | 87.828 | 14.614 | 1.00 12.15 | N |
| ATOM | 37135 | CA | LEU | D | 481 | 28.652 | 87.510 | 16.037 | 1.00 12.22 | C |
| ATOM | 37137 | CB | LEU | D | 481 | 27.174 | 87.577 | 16.436 | 1.00 12.47 | C |
| ATOM | 37140 | CG | LEU | D | 481 | 26.585 | 88.963 | 16.478 | 1.00 14.69 | C |
| ATOM | 37142 | CD1 | LEU | D | 481 | 25.019 | 88.847 | 16.493 | 1.00 14.70 | C |
| ATOM | 37146 | CD2 | LEU | D | 481 | 27.089 | 89.813 | 17.627 | 1.00 14.22 | C |
| ATOM | 37150 | C | LEU | D | 481 | 29.219 | 86.162 | 16.404 | 1.00 11.33 | C |
| ATOM | 37151 | O | LEU | D | 481 | 29.701 | 85.957 | 17.494 | 1.00 12.49 | O |
| ATOM | 37153 | N | GLY | D | 482 | 29.045 | 85.177 | 15.530 | 1.00 11.65 | N |
| ATOM | 37154 | CA | GLY | D | 482 | 29.518 | 83.794 | 15.816 | 1.00 13.45 | C |
| ATOM | 37157 | C | GLY | D | 482 | 31.027 | 83.752 | 16.007 | 1.00 13.56 | C |
| ATOM | 37158 | O | GLY | D | 482 | 31.530 | 83.232 | 16.996 | 1.00 13.87 | O |
| ATOM | 37160 | N | HIS | D | 483 | 31.746 | 84.389 | 15.087 | 1.00 13.80 | N |
| ATOM | 37161 | CA | HIS | D | 483 | 33.202 | 84.429 | 15.204 | 1.00 13.22 | C |
| ATOM | 37163 | CB | HIS | D | 483 | 33.813 | 85.004 | 13.931 | 1.00 12.80 | C |
| ATOM | 37166 | CG | HIS | D | 483 | 35.269 | 85.292 | 14.039 | 1.00 14.09 | C |
| ATOM | 37167 | ND1 | HIS | D | 483 | 35.759 | 86.505 | 14.467 | 1.00 16.45 | N |
| ATOM | 37169 | CE1 | HIS | D | 483 | 37.087 | 86.467 | 14.459 | 1.00 14.94 | C |
| ATOM | 37171 | NE2 | HIS | D | 483 | 37.465 | 85.276 | 14.016 | 1.00 14.00 | N |
| ATOM | 37173 | CD2 | HIS | D | 483 | 36.351 | 84.518 | 13.764 | 1.00 15.16 | C |
| ATOM | 37175 | C | HIS | D | 483 | 33.611 | 85.226 | 16.448 | 1.00 13.50 | C |
| ATOM | 37176 | O | HIS | D | 483 | 34.547 | 84.823 | 17.153 | 1.00 13.18 | O |
| ATOM | 37178 | N | LEU | D | 484 | 32.924 | 86.367 | 16.710 | 1.00 12.32 | N |
| ATOM | 37179 | CA | LEU | D | 484 | 33.291 | 87.200 | 17.891 | 1.00 12.02 | C |
| ATOM | 37181 | CB | LEU | D | 484 | 32.396 | 88.415 | 18.039 | 1.00 12.66 | C |
| ATOM | 37184 | CG | LEU | D | 484 | 32.841 | 89.605 | 17.212 | 1.00 13.61 | C |
| ATOM | 37186 | CD1 | LEU | D | 484 | 31.679 | 90.514 | 16.925 | 1.00 12.18 | C |
| ATOM | 37190 | CD2 | LEU | D | 484 | 33.969 | 90.333 | 17.949 | 1.00 16.09 | C |
| ATOM | 37194 | C | LEU | D | 484 | 33.195 | 86.359 | 19.192 | 1.00 11.71 | C |
| ATOM | 37195 | O | LEU | D | 484 | 33.969 | 86.608 | 20.136 | 1.00 12.82 | O |
| ATOM | 37197 | N | ALA | D | 485 | 32.241 | 85.398 | 19.258 | 1.00 11.11 | N |
| ATOM | 37198 | CA | ALA | D | 485 | 31.904 | 84.678 | 20.486 | 1.00 11.90 | C |
| ATOM | 37200 | CB | ALA | D | 485 | 30.565 | 84.054 | 20.343 | 1.00 13.09 | C |
| ATOM | 37204 | C | ALA | D | 485 | 32.907 | 83.638 | 20.973 | 1.00 12.47 | C |
| ATOM | 37205 | O | ALA | D | 485 | 32.747 | 83.064 | 22.070 | 1.00 14.96 | O |
| ATOM | 37207 | N | ASN | D | 486 | 33.943 | 83.360 | 20.177 | 1.00 12.08 | N |
| ATOM | 37208 | CA | ASN | D | 486 | 35.019 | 82.459 | 20.672 | 1.00 12.66 | C |
| ATOM | 37210 | CB | ASN | D | 486 | 36.054 | 82.167 | 19.577 | 1.00 14.01 | C |
| ATOM | 37213 | CG | ASN | D | 486 | 35.450 | 81.350 | 18.437 | 1.00 13.00 | C |
| ATOM | 37214 | OD1 | ASN | D | 486 | 34.782 | 80.374 | 18.721 | 1.00 12.24 | O |
| ATOM | 37215 | ND2 | ASN | D | 486 | 35.634 | 81.777 | 17.192 | 1.00 13.85 | N |

| ATOM | 37218 | C | ASN | D | 486 | 35.679 | 83.158 | 21.848 | 1.00 | 12.49 | C |
|---|---|---|---|---|---|---|---|---|---|---|---|
| ATOM | 37219 | O | ASN | D | 486 | 35.686 | 84.367 | 21.922 | 1.00 | 11.93 | O |
| ATOM | 37221 | N | PRO | D | 487 | 36.143 | 82.379 | 22.834 | 1.00 | 13.54 | N |
| ATOM | 37222 | CA | PRO | D | 487 | 36.769 | 82.944 | 24.034 | 1.00 | 12.96 | C |
| ATOM | 37224 | CB | PRO | D | 487 | 36.949 | 81.714 | 24.936 | 1.00 | 13.05 | C |
| ATOM | 37227 | CG | PRO | D | 487 | 37.017 | 80.581 | 23.982 | 1.00 | 12.52 | C |
| ATOM | 37230 | CD | PRO | D | 487 | 36.043 | 80.923 | 22.927 | 1.00 | 13.12 | C |
| ATOM | 37233 | C | PRO | D | 487 | 38.103 | 83.649 | 23.749 | 1.00 | 13.82 | C |
| ATOM | 37234 | O | PRO | D | 487 | 38.905 | 83.188 | 22.939 | 1.00 | 13.66 | O |
| ATOM | 37235 | N | VAL | D | 488 | 38.323 | 84.746 | 24.438 | 1.00 | 13.58 | N |
| ATOM | 37236 | CA | VAL | D | 488 | 39.628 | 85.418 | 24.473 | 1.00 | 12.69 | C |
| ATOM | 37238 | CB | VAL | D | 488 | 39.458 | 86.961 | 24.763 | 1.00 | 13.26 | C |
| ATOM | 37240 | CG1 | VAL | D | 488 | 40.728 | 87.629 | 25.296 | 1.00 | 17.04 | C |
| ATOM | 37244 | CG2 | VAL | D | 488 | 38.877 | 87.632 | 23.538 | 1.00 | 12.05 | C |
| ATOM | 37248 | C | VAL | D | 488 | 40.531 | 84.738 | 25.545 | 1.00 | 11.99 | C |
| ATOM | 37249 | O | VAL | D | 488 | 41.752 | 84.658 | 25.430 | 1.00 | 11.79 | O |
| ATOM | 37251 | N | THR | D | 489 | 39.891 | 84.260 | 26.589 | 1.00 | 13.01 | N |
| ATOM | 37252 | CA | THR | D | 489 | 40.583 | 83.844 | 27.816 | 1.00 | 12.78 | C |
| ATOM | 37254 | CB | THR | D | 489 | 39.666 | 83.706 | 29.003 | 1.00 | 13.95 | C |
| ATOM | 37256 | OG1 | THR | D | 489 | 38.608 | 82.778 | 28.745 | 1.00 | 13.36 | O |
| ATOM | 37258 | CG2 | THR | D | 489 | 39.099 | 85.062 | 29.351 | 1.00 | 14.86 | C |
| ATOM | 37262 | C | THR | D | 489 | 41.424 | 82.585 | 27.675 | 1.00 | 13.32 | C |
| ATOM | 37263 | O | THR | D | 489 | 42.153 | 82.236 | 28.568 | 1.00 | 15.30 | O |
| ATOM | 37265 | N | THR | D | 490 | 41.274 | 81.893 | 26.568 | 1.00 | 12.91 | N |
| ATOM | 37266 | CA | THR | D | 490 | 42.106 | 80.784 | 26.282 | 1.00 | 13.37 | C |
| ATOM | 37268 | CB | THR | D | 490 | 41.363 | 79.787 | 25.402 | 1.00 | 13.65 | C |
| ATOM | 37270 | OG1 | THR | D | 490 | 40.818 | 80.437 | 24.253 | 1.00 | 13.51 | O |
| ATOM | 37272 | CG2 | THR | D | 490 | 40.238 | 79.046 | 26.186 | 1.00 | 15.11 | C |
| ATOM | 37276 | C | THR | D | 490 | 43.429 | 81.135 | 25.557 | 1.00 | 13.50 | C |
| ATOM | 37277 | O | THR | D | 490 | 44.200 | 80.197 | 25.167 | 1.00 | 16.42 | O |
| ATOM | 37279 | N | HIS | D | 491 | 43.698 | 82.412 | 25.422 | 1.00 | 12.56 | N |
| ATOM | 37280 | CA | HIS | D | 491 | 44.875 | 82.862 | 24.680 | 1.00 | 12.44 | C |
| ATOM | 37282 | CB | HIS | D | 491 | 44.411 | 83.759 | 23.553 | 1.00 | 13.91 | C |
| ATOM | 37285 | CG | HIS | D | 491 | 43.686 | 82.972 | 22.551 | 1.00 | 11.69 | C |
| ATOM | 37286 | ND1 | HIS | D | 491 | 44.317 | 82.159 | 21.645 | 1.00 | 14.64 | N |
| ATOM | 37288 | CE1 | HIS | D | 491 | 43.394 | 81.531 | 20.933 | 1.00 | 14.96 | C |
| ATOM | 37290 | NE2 | HIS | D | 491 | 42.194 | 81.913 | 21.359 | 1.00 | 14.59 | N |
| ATOM | 37292 | CD2 | HIS | D | 491 | 42.353 | 82.810 | 22.372 | 1.00 | 14.99 | C |
| ATOM | 37294 | C | HIS | D | 491 | 45.902 | 83.507 | 25.608 | 1.00 | 13.93 | C |
| ATOM | 37295 | O | HIS | D | 491 | 46.718 | 84.294 | 25.177 | 1.00 | 12.63 | O |
| ATOM | 37297 | N | VAL | D | 492 | 45.870 | 83.091 | 26.870 | 1.00 | 13.37 | N |
| ATOM | 37298 | CA | VAL | D | 492 | 46.787 | 83.622 | 27.881 | 1.00 | 13.14 | C |
| ATOM | 37300 | CB | VAL | D | 492 | 46.397 | 83.126 | 29.276 | 1.00 | 12.14 | C |
| ATOM | 37302 | CG1 | VAL | D | 492 | 47.435 | 83.569 | 30.330 | 1.00 | 16.16 | C |
| ATOM | 37306 | CG2 | VAL | D | 492 | 45.028 | 83.632 | 29.629 | 1.00 | 13.44 | C |
| ATOM | 37310 | C | VAL | D | 492 | 48.238 | 83.252 | 27.558 | 1.00 | 13.06 | C |
| ATOM | 37311 | O | VAL | D | 492 | 48.530 | 82.109 | 27.322 | 1.00 | 12.31 | O |
| ATOM | 37313 | N | GLN | D | 493 | 49.112 | 84.257 | 27.594 | 1.00 | 12.62 | N |
| ATOM | 37314 | CA | GLN | D | 493 | 50.528 | 84.142 | 27.384 | 1.00 | 13.12 | C |
| ATOM | 37316 | CB | GLN | D | 493 | 50.981 | 85.216 | 26.415 | 1.00 | 13.43 | C |
| ATOM | 37319 | CG | GLN | D | 493 | 50.273 | 85.207 | 25.083 | 1.00 | 13.61 | C |
| ATOM | 37322 | CD | GLN | D | 493 | 50.507 | 83.911 | 24.293 | 1.00 | 16.45 | C |
| ATOM | 37323 | OE1 | GLN | D | 493 | 51.629 | 83.444 | 24.181 | 1.00 | 17.46 | O |
| ATOM | 37324 | NE2 | GLN | D | 493 | 49.410 | 83.276 | 23.813 | 1.00 | 14.59 | N |
| ATOM | 37327 | C | GLN | D | 493 | 51.324 | 84.312 | 28.677 | 1.00 | 13.42 | C |
| ATOM | 37328 | O | GLN | D | 493 | 50.850 | 84.939 | 29.611 | 1.00 | 13.92 | O |
| ATOM | 37330 | N | PRO | D | 494 | 52.531 | 83.735 | 28.747 | 1.00 | 14.44 | N |

| | | | | | | | | | |
|---|---|---|---|---|---|---|---|---|---|
| ATOM | 37331 | CA | PRO | D | 494 | 53.368 | 83.821 | 29.968 | 1.00 15.37 | C |
| ATOM | 37333 | CB | PRO | D | 494 | 54.423 | 82.768 | 29.711 | 1.00 15.18 | C |
| ATOM | 37336 | CG | PRO | D | 494 | 54.577 | 82.788 | 28.235 | 1.00 14.78 | C |
| ATOM | 37339 | CD | PRO | D | 494 | 53.166 | 82.892 | 27.729 | 1.00 13.94 | C |
| ATOM | 37342 | C | PRO | D | 494 | 54.031 | 85.144 | 30.206 | 1.00 18.17 | C |
| ATOM | 37343 | O | PRO | D | 494 | 55.278 | 85.251 | 30.159 | 1.00 21.42 | O |
| ATOM | 37344 | N | ALA | D | 495 | 53.244 | 86.121 | 30.575 | 1.00 17.72 | N |
| ATOM | 37345 | CA | ALA | D | 495 | 53.730 | 87.472 | 30.601 | 1.00 17.98 | C |
| ATOM | 37347 | CB | ALA | D | 495 | 52.527 | 88.460 | 30.520 | 1.00 18.00 | C |
| ATOM | 37351 | C | ALA | D | 495 | 54.696 | 87.816 | 31.747 | 1.00 17.85 | C |
| ATOM | 37352 | O | ALA | D | 495 | 54.569 | 87.331 | 32.879 | 1.00 17.32 | O |
| ATOM | 37354 | N | GLU | D | 496 | 55.629 | 88.724 | 31.451 | 1.00 18.95 | N |
| ATOM | 37355 | CA | GLU | D | 496 | 56.482 | 89.340 | 32.440 | 1.00 18.99 | C |
| ATOM | 37357 | CB | GLU | D | 496 | 55.654 | 90.204 | 33.432 | 1.00 21.05 | C |
| ATOM | 37360 | CG | GLU | D | 496 | 56.510 | 91.197 | 34.195 | 1.00 22.24 | C |
| ATOM | 37363 | CD | GLU | D | 496 | 56.336 | 91.164 | 35.702 | 1.00 25.59 | C |
| ATOM | 37364 | OE1 | GLU | D | 496 | 55.199 | 91.121 | 36.270 | 1.00 24.16 | O |
| ATOM | 37365 | OE2 | GLU | D | 496 | 57.391 | 91.221 | 36.341 | 1.00 29.67 | O |
| ATOM | 37366 | C | GLU | D | 496 | 57.349 | 88.342 | 33.187 | 1.00 18.95 | C |
| ATOM | 37367 | O | GLU | D | 496 | 57.259 | 88.166 | 34.396 | 1.00 18.48 | O |
| ATOM | 37369 | N | MSE | D | 497 | 58.208 | 87.656 | 32.432 | 1.00 19.74 | N |
| ATOM | 37370 | CA | MSE | D | 497 | 59.091 | 86.645 | 33.007 | 1.00 20.25 | C |
| ATOM | 37372 | CB | MSE | D | 497 | 60.143 | 87.247 | 33.933 | 1.00 21.78 | C |
| ATOM | 37375 | CG | MSE | D | 497 | 61.050 | 88.169 | 33.176 | 1.00 22.02 | C |
| ATOM | 37378 | SE | MSE | D | 497 | 62.437 | 88.911 | 34.407 | 1.00 34.33 | SE |
| ATOM | 37379 | CE | MSE | D | 497 | 63.196 | 87.328 | 35.151 | 1.00 29.96 | C |
| ATOM | 37383 | C | MSE | D | 497 | 58.317 | 85.531 | 33.716 | 1.00 17.47 | C |
| ATOM | 37384 | O | MSE | D | 497 | 58.826 | 84.901 | 34.662 | 1.00 17.69 | O |
| ATOM | 37386 | N | ALA | D | 498 | 57.108 | 85.281 | 33.203 | 1.00 15.99 | N |
| ATOM | 37387 | CA | ALA | D | 498 | 56.176 | 84.340 | 33.824 | 1.00 14.60 | C |
| ATOM | 37389 | CB | ALA | D | 498 | 56.678 | 82.914 | 33.794 | 1.00 16.56 | C |
| ATOM | 37393 | C | ALA | D | 498 | 55.754 | 84.718 | 35.241 | 1.00 14.98 | C |
| ATOM | 37394 | O | ALA | D | 498 | 55.044 | 83.932 | 35.902 | 1.00 13.32 | O |
| ATOM | 37396 | N | ASN | D | 499 | 56.064 | 85.930 | 35.728 | 1.00 14.54 | N |
| ATOM | 37397 | CA | ASN | D | 499 | 55.452 | 86.365 | 36.985 | 1.00 13.55 | C |
| ATOM | 37399 | CB | ASN | D | 499 | 56.017 | 87.680 | 37.499 | 1.00 14.41 | C |
| ATOM | 37402 | CG | ASN | D | 499 | 55.316 | 88.144 | 38.816 | 1.00 16.99 | C |
| ATOM | 37403 | OD1 | ASN | D | 499 | 55.276 | 87.412 | 39.812 | 1.00 22.66 | O |
| ATOM | 37404 | ND2 | ASN | D | 499 | 54.804 | 89.411 | 38.820 | 1.00 22.26 | N |
| ATOM | 37407 | C | ASN | D | 499 | 53.924 | 86.466 | 36.812 | 1.00 12.32 | C |
| ATOM | 37408 | O | ASN | D | 499 | 53.123 | 86.085 | 37.703 | 1.00 13.61 | O |
| ATOM | 37410 | N | GLN | D | 500 | 53.528 | 86.912 | 35.610 | 1.00 11.60 | N |
| ATOM | 37411 | CA | GLN | D | 500 | 52.149 | 87.047 | 35.249 | 1.00 12.12 | C |
| ATOM | 37413 | CB | GLN | D | 500 | 51.836 | 88.421 | 34.672 | 1.00 13.02 | C |
| ATOM | 37416 | CG | GLN | D | 500 | 52.388 | 89.602 | 35.483 | 1.00 14.44 | C |
| ATOM | 37419 | CD | GLN | D | 500 | 51.774 | 90.941 | 35.186 | 1.00 13.11 | C |
| ATOM | 37420 | OE1 | GLN | D | 500 | 50.643 | 91.042 | 34.688 | 1.00 14.61 | O |
| ATOM | 37421 | NE2 | GLN | D | 500 | 52.512 | 92.015 | 35.519 | 1.00 16.64 | N |
| ATOM | 37424 | C | GLN | D | 500 | 51.715 | 85.902 | 34.334 | 1.00 13.12 | C |
| ATOM | 37425 | O | GLN | D | 500 | 51.059 | 86.101 | 33.308 | 1.00 13.93 | O |
| ATOM | 37427 | N | ALA | D | 501 | 52.101 | 84.680 | 34.704 | 1.00 11.57 | N |
| ATOM | 37428 | CA | ALA | D | 501 | 51.869 | 83.524 | 33.822 | 1.00 11.73 | C |
| ATOM | 37430 | CB | ALA | D | 501 | 52.575 | 82.327 | 34.348 | 1.00 13.16 | C |
| ATOM | 37434 | C | ALA | D | 501 | 50.367 | 83.189 | 33.564 | 1.00 11.29 | C |
| ATOM | 37435 | O | ALA | D | 501 | 50.019 | 82.540 | 32.565 | 1.00 12.55 | O |
| ATOM | 37437 | N | VAL | D | 502 | 49.523 | 83.590 | 34.522 | 1.00 10.98 | N |
| ATOM | 37438 | CA | VAL | D | 502 | 48.080 | 83.660 | 34.338 | 1.00 11.82 | C |

| ATOM | 37440 | CB | VAL | D | 502 | 47.252 | 82.893 | 35.370 | 1.00 | 11.61 | C |
|------|-------|-----|-----|---|-----|--------|--------|--------|------|-------|---|
| ATOM | 37442 | CG1 | VAL | D | 502 | 47.276 | 81.402 | 35.052 | 1.00 | 9.39 | C |
| ATOM | 37446 | CG2 | VAL | D | 502 | 47.690 | 83.143 | 36.761 | 1.00 | 12.00 | C |
| ATOM | 37450 | C | VAL | D | 502 | 47.690 | 85.147 | 34.402 | 1.00 | 11.14 | C |
| ATOM | 37451 | O | VAL | D | 502 | 48.146 | 85.896 | 35.270 | 1.00 | 11.76 | O |
| ATOM | 37453 | N | ASN | D | 503 | 46.880 | 85.560 | 33.439 | 1.00 | 11.53 | N |
| ATOM | 37454 | CA | ASN | D | 503 | 46.427 | 86.923 | 33.290 | 1.00 | 10.95 | C |
| ATOM | 37456 | CB | ASN | D | 503 | 47.449 | 87.786 | 32.550 | 1.00 | 10.98 | C |
| ATOM | 37459 | CG | ASN | D | 503 | 47.903 | 87.180 | 31.227 | 1.00 | 10.06 | C |
| ATOM | 37460 | OD1 | ASN | D | 503 | 47.204 | 87.297 | 30.219 | 1.00 | 13.06 | O |
| ATOM | 37461 | ND2 | ASN | D | 503 | 49.088 | 86.593 | 31.217 | 1.00 | 12.46 | N |
| ATOM | 37464 | C | ASN | D | 503 | 45.033 | 86.860 | 32.642 | 1.00 | 12.03 | C |
| ATOM | 37465 | O | ASN | D | 503 | 44.755 | 85.968 | 31.828 | 1.00 | 11.31 | O |
| ATOM | 37467 | N | SER | D | 504 | 44.145 | 87.764 | 33.057 | 1.00 | 12.47 | N |
| ATOM | 37468 | CA | SER | D | 504 | 42.735 | 87.539 | 32.825 | 1.00 | 12.45 | C |
| ATOM | 37470 | CB | SER | D | 504 | 41.882 | 88.355 | 33.796 | 1.00 | 13.07 | C |
| ATOM | 37473 | OG | SER | D | 504 | 41.855 | 89.719 | 33.475 | 1.00 | 12.34 | O |
| ATOM | 37475 | C | SER | D | 504 | 42.289 | 87.888 | 31.425 | 1.00 | 11.69 | C |
| ATOM | 37476 | O | SER | D | 504 | 41.236 | 87.414 | 30.977 | 1.00 | 11.84 | O |
| ATOM | 37478 | N | LEU | D | 505 | 43.003 | 88.815 | 30.797 | 1.00 | 11.25 | N |
| ATOM | 37479 | CA | LEU | D | 505 | 42.629 | 89.365 | 29.481 | 1.00 | 12.55 | C |
| ATOM | 37481 | CB | LEU | D | 505 | 42.731 | 88.212 | 28.463 | 1.00 | 11.28 | C |
| ATOM | 37484 | CG | LEU | D | 505 | 44.122 | 87.662 | 28.284 | 1.00 | 11.78 | C |
| ATOM | 37486 | CD1 | LEU | D | 505 | 44.042 | 86.564 | 27.218 | 1.00 | 14.10 | C |
| ATOM | 37490 | CD2 | LEU | D | 505 | 45.124 | 88.685 | 27.918 | 1.00 | 14.28 | C |
| ATOM | 37494 | C | LEU | D | 505 | 41.224 | 90.004 | 29.493 | 1.00 | 11.74 | C |
| ATOM | 37495 | O | LEU | D | 505 | 40.552 | 90.132 | 28.447 | 1.00 | 12.60 | O |
| ATOM | 37497 | N | ALA | D | 506 | 40.809 | 90.507 | 30.658 | 1.00 | 12.41 | N |
| ATOM | 37498 | CA | ALA | D | 506 | 39.479 | 91.069 | 30.802 | 1.00 | 12.17 | C |
| ATOM | 37500 | CB | ALA | D | 506 | 39.248 | 91.514 | 32.243 | 1.00 | 11.83 | C |
| ATOM | 37504 | C | ALA | D | 506 | 39.192 | 92.240 | 29.861 | 1.00 | 12.70 | C |
| ATOM | 37505 | O | ALA | D | 506 | 38.096 | 92.333 | 29.284 | 1.00 | 13.40 | O |
| ATOM | 37507 | N | LEU | D | 507 | 40.134 | 93.168 | 29.689 | 1.00 | 11.59 | N |
| ATOM | 37508 | CA | LEU | D | 507 | 39.841 | 94.333 | 28.826 | 1.00 | 12.22 | C |
| ATOM | 37510 | CB | LEU | D | 507 | 40.901 | 95.419 | 28.945 | 1.00 | 13.12 | C |
| ATOM | 37513 | CG | LEU | D | 507 | 40.501 | 96.700 | 28.209 | 1.00 | 12.61 | C |
| ATOM | 37515 | CD1 | LEU | D | 507 | 39.231 | 97.370 | 28.720 | 1.00 | 13.59 | C |
| ATOM | 37519 | CD2 | LEU | D | 507 | 41.670 | 97.667 | 28.328 | 1.00 | 15.09 | C |
| ATOM | 37523 | C | LEU | D | 507 | 39.676 | 93.922 | 27.369 | 1.00 | 11.60 | C |
| ATOM | 37524 | O | LEU | D | 507 | 38.791 | 94.434 | 26.668 | 1.00 | 13.60 | O |
| ATOM | 37526 | N | ILE | D | 508 | 40.543 | 93.018 | 26.892 | 1.00 | 11.98 | N |
| ATOM | 37527 | CA | ILE | D | 508 | 40.413 | 92.519 | 25.509 | 1.00 | 12.13 | C |
| ATOM | 37529 | CB | ILE | D | 508 | 41.556 | 91.603 | 25.084 | 1.00 | 12.37 | C |
| ATOM | 37531 | CG1 | ILE | D | 508 | 42.910 | 92.300 | 25.242 | 1.00 | 12.75 | C |
| ATOM | 37534 | CD1 | ILE | D | 508 | 44.065 | 91.374 | 25.216 | 1.00 | 15.94 | C |
| ATOM | 37538 | CG2 | ILE | D | 508 | 41.309 | 91.048 | 23.679 | 1.00 | 12.36 | C |
| ATOM | 37542 | C | ILE | D | 508 | 39.041 | 91.839 | 25.352 | 1.00 | 11.39 | C |
| ATOM | 37543 | O | ILE | D | 508 | 38.302 | 92.106 | 24.383 | 1.00 | 13.00 | O |
| ATOM | 37545 | N | SER | D | 509 | 38.662 | 91.027 | 26.307 | 1.00 | 11.68 | N |
| ATOM | 37546 | CA | SER | D | 509 | 37.361 | 90.384 | 26.255 | 1.00 | 11.99 | C |
| ATOM | 37548 | CB | SER | D | 509 | 37.149 | 89.450 | 27.420 | 1.00 | 14.16 | C |
| ATOM | 37551 | OG | SER | D | 509 | 36.012 | 88.636 | 27.260 | 1.00 | 13.79 | O |
| ATOM | 37553 | C | SER | D | 509 | 36.223 | 91.423 | 26.199 | 1.00 | 11.79 | C |
| ATOM | 37554 | O | SER | D | 509 | 35.250 | 91.301 | 25.426 | 1.00 | 12.20 | O |
| ATOM | 37556 | N | ALA | D | 510 | 36.312 | 92.390 | 27.100 | 1.00 | 10.94 | N |
| ATOM | 37557 | CA | ALA | D | 510 | 35.352 | 93.476 | 27.149 | 1.00 | 11.43 | C |
| ATOM | 37559 | CB | ALA | D | 510 | 35.662 | 94.417 | 28.272 | 1.00 | 11.78 | C |

| | | | | | | | | | |
|---|---|---|---|---|---|---|---|---|---|
| ATOM | 37563 | C   | ALA | D | 510 | 35.199 | 94.245 | 25.841 | 1.00 11.87 | C |
| ATOM | 37564 | O   | ALA | D | 510 | 34.106 | 94.586 | 25.413 | 1.00 12.81 | O |
| ATOM | 37566 | N   | ARG | D | 511 | 36.335 | 94.523 | 25.201 | 1.00 12.31 | N |
| ATOM | 37567 | CA  | ARG | D | 511 | 36.316 | 95.137 | 23.854 | 1.00 13.40 | C |
| ATOM | 37569 | CB  | ARG | D | 511 | 37.724 | 95.409 | 23.355 | 1.00 12.58 | C |
| ATOM | 37572 | CG  | ARG | D | 511 | 38.401 | 96.572 | 24.057 | 1.00 12.23 | C |
| ATOM | 37575 | CD  | ARG | D | 511 | 39.870 | 96.665 | 23.720 | 1.00 13.56 | C |
| ATOM | 37578 | NE  | ARG | D | 511 | 40.045 | 96.503 | 22.284 | 1.00 13.05 | N |
| ATOM | 37580 | CZ  | ARG | D | 511 | 40.921 | 95.686 | 21.710 | 1.00 13.88 | C |
| ATOM | 37581 | NH1 | ARG | D | 511 | 41.835 | 95.039 | 22.421 | 1.00 12.93 | N |
| ATOM | 37584 | NH2 | ARG | D | 511 | 40.874 | 95.585 | 20.393 | 1.00 14.29 | N |
| ATOM | 37587 | C   | ARG | D | 511 | 35.573 | 94.277 | 22.853 | 1.00 12.92 | C |
| ATOM | 37588 | O   | ARG | D | 511 | 34.757 | 94.778 | 22.102 | 1.00 12.28 | O |
| ATOM | 37590 | N   | ARG | D | 512 | 35.806 | 92.973 | 22.877 | 1.00 11.84 | N |
| ATOM | 37591 | CA  | ARG | D | 512 | 35.116 | 92.091 | 21.951 | 1.00 12.15 | C |
| ATOM | 37593 | CB  | ARG | D | 512 | 35.718 | 90.700 | 21.953 | 1.00 13.10 | C |
| ATOM | 37596 | CG  | ARG | D | 512 | 37.156 | 90.621 | 21.421 | 1.00 12.63 | C |
| ATOM | 37599 | CD  | ARG | D | 512 | 37.332 | 91.345 | 20.068 | 1.00 16.50 | C |
| ATOM | 37602 | NE  | ARG | D | 512 | 38.679 | 91.118 | 19.498 | 1.00 16.22 | N |
| ATOM | 37604 | CZ  | ARG | D | 512 | 39.380 | 92.039 | 18.825 | 1.00 16.07 | C |
| ATOM | 37605 | NH1 | ARG | D | 512 | 38.925 | 93.268 | 18.609 | 1.00 20.86 | N |
| ATOM | 37608 | NH2 | ARG | D | 512 | 40.565 | 91.704 | 18.307 | 1.00 15.58 | N |
| ATOM | 37611 | C   | ARG | D | 512 | 33.630 | 92.096 | 22.210 | 1.00 11.50 | C |
| ATOM | 37612 | O   | ARG | D | 512 | 32.799 | 92.138 | 21.248 | 1.00 12.94 | O |
| ATOM | 37614 | N   | THR | D | 513 | 33.240 | 92.079 | 23.497 | 1.00 11.44 | N |
| ATOM | 37615 | CA  | THR | D | 513 | 31.829 | 92.023 | 23.828 | 1.00 11.53 | C |
| ATOM | 37617 | CB  | THR | D | 513 | 31.673 | 91.740 | 25.299 | 1.00 11.43 | C |
| ATOM | 37619 | OG1 | THR | D | 513 | 32.333 | 90.480 | 25.567 | 1.00 11.33 | O |
| ATOM | 37621 | CG2 | THR | D | 513 | 30.200 | 91.691 | 25.684 | 1.00 13.40 | C |
| ATOM | 37625 | C   | THR | D | 513 | 31.150 | 93.345 | 23.423 | 1.00 11.56 | C |
| ATOM | 37626 | O   | THR | D | 513 | 29.989 | 93.353 | 22.995 | 1.00 12.08 | O |
| ATOM | 37628 | N   | THR | D | 514 | 31.890 | 94.419 | 23.565 | 1.00 12.11 | N |
| ATOM | 37629 | CA  | THR | D | 514 | 31.397 | 95.726 | 23.149 | 1.00 12.50 | C |
| ATOM | 37631 | CB  | THR | D | 514 | 32.341 | 96.845 | 23.554 | 1.00 13.05 | C |
| ATOM | 37633 | OG1 | THR | D | 514 | 32.502 | 96.817 | 24.977 | 1.00 12.79 | O |
| ATOM | 37635 | CG2 | THR | D | 514 | 31.824 | 98.157 | 23.087 | 1.00 14.46 | C |
| ATOM | 37639 | C   | THR | D | 514 | 31.104 | 95.722 | 21.631 | 1.00 13.73 | C |
| ATOM | 37640 | O   | THR | D | 514 | 30.080 | 96.258 | 21.168 | 1.00 12.62 | O |
| ATOM | 37642 | N   | GLU | D | 515 | 32.016 | 95.144 | 20.855 | 1.00 12.85 | N |
| ATOM | 37643 | CA  | GLU | D | 515 | 31.799 | 94.991 | 19.403 | 1.00 13.59 | C |
| ATOM | 37645 | CB  | GLU | D | 515 | 33.036 | 94.451 | 18.716 | 1.00 14.38 | C |
| ATOM | 37648 | CG  | GLU | D | 515 | 32.843 | 94.335 | 17.211 | 1.00 16.66 | C |
| ATOM | 37651 | CD  | GLU | D | 515 | 34.152 | 94.186 | 16.380 | 1.00 18.37 | C |
| ATOM | 37652 | OE1 | GLU | D | 515 | 35.263 | 94.073 | 16.964 | 1.00 20.54 | O |
| ATOM | 37653 | OE2 | GLU | D | 515 | 34.044 | 94.173 | 15.108 | 1.00 17.25 | O |
| ATOM | 37654 | C   | GLU | D | 515 | 30.568 | 94.089 | 19.095 | 1.00 11.87 | C |
| ATOM | 37655 | O   | GLU | D | 515 | 29.736 | 94.397 | 18.222 | 1.00 12.51 | O |
| ATOM | 37657 | N   | SER | D | 516 | 30.406 | 92.995 | 19.844 | 1.00 12.20 | N |
| ATOM | 37658 | CA  | SER | D | 516 | 29.206 | 92.174 | 19.719 | 1.00 12.33 | C |
| ATOM | 37660 | CB  | SER | D | 516 | 29.335 | 90.910 | 20.562 | 1.00 12.54 | C |
| ATOM | 37663 | OG  | SER | D | 516 | 30.343 | 90.024 | 20.071 | 1.00 12.54 | O |
| ATOM | 37665 | C   | SER | D | 516 | 27.934 | 92.940 | 20.029 | 1.00 12.62 | C |
| ATOM | 37666 | O   | SER | D | 516 | 26.918 | 92.813 | 19.308 | 1.00 12.12 | O |
| ATOM | 37668 | N   | ASN | D | 517 | 27.956 | 93.804 | 21.043 | 1.00 11.51 | N |
| ATOM | 37669 | CA  | ASN | D | 517 | 26.784 | 94.643 | 21.301 | 1.00 11.53 | C |
| ATOM | 37671 | CB  | ASN | D | 517 | 26.996 | 95.601 | 22.502 | 1.00 12.51 | C |
| ATOM | 37674 | CG  | ASN | D | 517 | 26.756 | 94.920 | 23.858 | 1.00 13.57 | C |

```
ATOM  37675  OD1  ASN  D  517    25.978  93.949  23.957  1.00  14.28    O
ATOM  37676  ND2  ASN  D  517    27.429  95.447  24.908  1.00  12.51    N
ATOM  37679  C    ASN  D  517    26.469  95.475  20.047  1.00  11.73    C
ATOM  37680  O    ASN  D  517    25.328  95.674  19.677  1.00  12.37    O
ATOM  37682  N    ASP  D  518    27.495  96.047  19.446  1.00  11.56    N
ATOM  37683  CA   ASP  D  518    27.334  96.889  18.286  1.00  13.34    C
ATOM  37685  CB   ASP  D  518    28.673  97.520  17.928  1.00  14.22    C
ATOM  37688  CG   ASP  D  518    28.540  98.632  16.899  1.00  17.45    C
ATOM  37689  OD1  ASP  D  518    27.507  99.365  16.888  1.00  20.36    O
ATOM  37690  OD2  ASP  D  518    29.532  98.830  16.161  1.00  22.43    O
ATOM  37691  C    ASP  D  518    26.760  96.112  17.115  1.00  12.72    C
ATOM  37692  O    ASP  D  518    25.765  96.549  16.479  1.00  13.32    O
ATOM  37694  N    VAL  D  519    27.334  94.947  16.823  1.00  12.16    N
ATOM  37695  CA   VAL  D  519    26.837  94.123  15.709  1.00  12.52    C
ATOM  37697  CB   VAL  D  519    27.798  92.967  15.429  1.00  13.60    C
ATOM  37699  CG1  VAL  D  519    27.233  92.071  14.361  1.00  13.79    C
ATOM  37703  CG2  VAL  D  519    29.118  93.506  15.017  1.00  13.33    C
ATOM  37707  C    VAL  D  519    25.371  93.668  15.993  1.00  12.35    C
ATOM  37708  O    VAL  D  519    24.493  93.699  15.112  1.00  12.68    O
ATOM  37710  N    LEU  D  520    25.089  93.250  17.225  1.00  12.22    N
ATOM  37711  CA   LEU  D  520    23.710  92.849  17.532  1.00  12.92    C
ATOM  37713  CB   LEU  D  520    23.654  92.221  18.926  1.00  14.35    C
ATOM  37716  CG   LEU  D  520    22.300  91.665  19.376  1.00  13.71    C
ATOM  37718  CD1  LEU  D  520    21.738  90.669  18.418  1.00  14.97    C
ATOM  37722  CD2  LEU  D  520    22.373  91.078  20.773  1.00  13.80    C
ATOM  37726  C    LEU  D  520    22.732  93.998  17.428  1.00  13.23    C
ATOM  37727  O    LEU  D  520    21.598  93.803  17.009  1.00  12.76    O
ATOM  37729  N    SER  D  521    23.206  95.194  17.762  1.00  13.32    N
ATOM  37730  CA   SER  D  521    22.419  96.402  17.572  1.00  12.16    C
ATOM  37732  CB   SER  D  521    23.139  97.627  18.149  1.00  13.68    C
ATOM  37735  OG   SER  D  521    23.321  97.502  19.559  1.00  13.33    O
ATOM  37737  C    SER  D  521    22.042  96.609  16.091  1.00  12.35    C
ATOM  37738  O    SER  D  521    20.894  96.960  15.775  1.00  12.19    O
ATOM  37740  N    LEU  D  522    22.991  96.356  15.203  1.00  12.76    N
ATOM  37741  CA   LEU  D  522    22.704  96.456  13.784  1.00  12.14    C
ATOM  37743  CB   LEU  D  522    23.961  96.191  12.958  1.00  13.04    C
ATOM  37746  CG   LEU  D  522    25.086  97.224  13.019  1.00  12.38    C
ATOM  37748  CD1  LEU  D  522    26.362  96.667  12.403  1.00  13.81    C
ATOM  37752  CD2  LEU  D  522    24.719  98.514  12.343  1.00  14.18    C
ATOM  37756  C    LEU  D  522    21.634  95.422  13.383  1.00  11.90    C
ATOM  37757  O    LEU  D  522    20.703  95.717  12.646  1.00  12.42    O
ATOM  37759  N    LEU  D  523    21.782  94.230  13.906  1.00  12.28    N
ATOM  37760  CA   LEU  D  523    20.862  93.130  13.617  1.00  12.85    C
ATOM  37762  CB   LEU  D  523    21.406  91.796  14.130  1.00  13.21    C
ATOM  37765  CG   LEU  D  523    20.516  90.549  14.019  1.00  12.58    C
ATOM  37767  CD1  LEU  D  523    20.122  90.254  12.607  1.00  15.58    C
ATOM  37771  CD2  LEU  D  523    21.249  89.358  14.650  1.00  14.87    C
ATOM  37775  C    LEU  D  523    19.454  93.392  14.164  1.00  11.65    C
ATOM  37776  O    LEU  D  523    18.427  93.202  13.455  1.00  13.05    O
ATOM  37778  N    LEU  D  524    19.371  93.811  15.427  1.00  11.93    N
ATOM  37779  CA   LEU  D  524    18.065  94.125  16.014  1.00  12.23    C
ATOM  37781  CB   LEU  D  524    18.139  94.164  17.546  1.00  11.95    C
ATOM  37784  CG   LEU  D  524    18.573  92.805  18.150  1.00  12.38    C
ATOM  37786  CD1  LEU  D  524    18.360  92.846  19.666  1.00  14.34    C
ATOM  37790  CD2  LEU  D  524    17.902  91.501  17.567  1.00  13.93    C
ATOM  37794  C    LEU  D  524    17.393  95.346  15.400  1.00  13.04    C
ATOM  37795  O    LEU  D  524    16.168  95.399  15.243  1.00  12.64    O
```

| ATOM | 37797 | N | ALA | D | 525 | 18.178 | 96.320 | 14.976 | 1.00 | 12.78 | N |
| ATOM | 37798 | CA | ALA | D | 525 | 17.615 | 97.491 | 14.258 | 1.00 | 12.68 | C |
| ATOM | 37800 | CB | ALA | D | 525 | 18.685 | 98.546 | 13.948 | 1.00 | 14.52 | C |
| ATOM | 37804 | C | ALA | D | 525 | 16.960 | 97.007 | 12.952 | 1.00 | 12.24 | C |
| ATOM | 37805 | O | ALA | D | 525 | 15.865 | 97.437 | 12.567 | 1.00 | 14.19 | O |
| ATOM | 37807 | N | THR | D | 526 | 17.678 | 96.118 | 12.283 | 1.00 | 12.18 | N |
| ATOM | 37808 | CA | THR | D | 526 | 17.226 | 95.522 | 11.046 | 1.00 | 12.27 | C |
| ATOM | 37810 | CB | THR | D | 526 | 18.365 | 94.661 | 10.423 | 1.00 | 13.02 | C |
| ATOM | 37812 | OG1 | THR | D | 526 | 19.435 | 95.553 | 10.048 | 1.00 | 12.65 | O |
| ATOM | 37814 | CG2 | THR | D | 526 | 17.876 | 93.904 | 9.230 | 1.00 | 12.84 | C |
| ATOM | 37818 | C | THR | D | 526 | 15.933 | 94.737 | 11.225 | 1.00 | 12.42 | C |
| ATOM | 37819 | O | THR | D | 526 | 14.939 | 94.899 | 10.491 | 1.00 | 12.76 | O |
| ATOM | 37821 | N | HIS | D | 527 | 15.921 | 93.920 | 12.245 | 1.00 | 11.87 | N |
| ATOM | 37822 | CA | HIS | D | 527 | 14.742 | 93.110 | 12.559 | 1.00 | 12.90 | C |
| ATOM | 37824 | CB | HIS | D | 527 | 15.081 | 92.142 | 13.691 | 1.00 | 13.98 | C |
| ATOM | 37827 | CG | HIS | D | 527 | 14.013 | 91.130 | 14.014 | 1.00 | 14.11 | C |
| ATOM | 37828 | ND1 | HIS | D | 527 | 14.181 | 90.105 | 14.937 | 1.00 | 15.44 | N |
| ATOM | 37830 | CE1 | HIS | D | 527 | 13.071 | 89.385 | 15.003 | 1.00 | 15.18 | C |
| ATOM | 37832 | NE2 | HIS | D | 527 | 12.188 | 89.888 | 14.139 | 1.00 | 13.13 | N |
| ATOM | 37834 | CD2 | HIS | D | 527 | 12.757 | 90.980 | 13.519 | 1.00 | 14.04 | C |
| ATOM | 37836 | C | HIS | D | 527 | 13.565 | 94.048 | 12.896 | 1.00 | 12.10 | C |
| ATOM | 37837 | O | HIS | D | 527 | 12.432 | 93.868 | 12.376 | 1.00 | 11.40 | O |
| ATOM | 37839 | N | LEU | D | 528 | 13.803 | 95.078 | 13.689 | 1.00 | 12.66 | N |
| ATOM | 37840 | CA | LEU | D | 528 | 12.711 | 95.986 | 14.057 | 1.00 | 12.21 | C |
| ATOM | 37842 | CB | LEU | D | 528 | 13.214 | 96.986 | 15.086 | 1.00 | 13.34 | C |
| ATOM | 37845 | CG | LEU | D | 528 | 12.243 | 98.018 | 15.623 | 1.00 | 12.75 | C |
| ATOM | 37847 | CD1 | LEU | D | 528 | 10.931 | 97.408 | 16.029 | 1.00 | 12.07 | C |
| ATOM | 37851 | CD2 | LEU | D | 528 | 12.897 | 98.806 | 16.749 | 1.00 | 15.32 | C |
| ATOM | 37855 | C | LEU | D | 528 | 12.182 | 96.679 | 12.810 | 1.00 | 12.50 | C |
| ATOM | 37856 | O | LEU | D | 528 | 10.975 | 96.783 | 12.589 | 1.00 | 12.86 | O |
| ATOM | 37858 | N | TYR | D | 529 | 13.090 | 97.167 | 11.964 | 1.00 | 11.43 | N |
| ATOM | 37859 | CA | TYR | D | 529 | 12.636 | 97.779 | 10.709 | 1.00 | 12.10 | C |
| ATOM | 37861 | CB | TYR | D | 529 | 13.847 | 98.105 | 9.826 | 1.00 | 13.38 | C |
| ATOM | 37864 | CG | TYR | D | 529 | 13.455 | 98.638 | 8.473 | 1.00 | 11.36 | C |
| ATOM | 37865 | CD1 | TYR | D | 529 | 13.296 | 99.984 | 8.233 | 1.00 | 12.31 | C |
| ATOM | 37867 | CE1 | TYR | D | 529 | 12.851 | 100.457 | 6.969 | 1.00 | 11.68 | C |
| ATOM | 37869 | CZ | TYR | D | 529 | 12.616 | 99.589 | 5.942 | 1.00 | 12.52 | C |
| ATOM | 37870 | OH | TYR | D | 529 | 12.199 | 100.048 | 4.686 | 1.00 | 13.00 | O |
| ATOM | 37872 | CE2 | TYR | D | 529 | 12.821 | 98.240 | 6.163 | 1.00 | 10.52 | C |
| ATOM | 37874 | CD2 | TYR | D | 529 | 13.212 | 97.774 | 7.433 | 1.00 | 11.56 | C |
| ATOM | 37876 | C | TYR | D | 529 | 11.653 | 96.858 | 9.939 | 1.00 | 11.68 | C |
| ATOM | 37877 | O | TYR | D | 529 | 10.569 | 97.310 | 9.492 | 1.00 | 12.02 | O |
| ATOM | 37879 | N | CYS | D | 530 | 12.090 | 95.606 | 9.756 | 1.00 | 12.41 | N |
| ATOM | 37880 | CA | CYS | D | 530 | 11.326 | 94.637 | 8.967 | 1.00 | 12.54 | C |
| ATOM | 37882 | CB | CYS | D | 530 | 12.129 | 93.388 | 8.698 | 1.00 | 12.55 | C |
| ATOM | 37885 | SG | CYS | D | 530 | 13.544 | 93.656 | 7.643 | 1.00 | 15.01 | S |
| ATOM | 37887 | C | CYS | D | 530 | 9.998 | 94.267 | 9.628 | 1.00 | 12.74 | C |
| ATOM | 37888 | O | CYS | D | 530 | 8.955 | 94.234 | 8.962 | 1.00 | 12.58 | O |
| ATOM | 37890 | N | VAL | D | 531 | 10.024 | 94.064 | 10.943 | 1.00 | 12.97 | N |
| ATOM | 37891 | CA | VAL | D | 531 | 8.811 | 93.596 | 11.600 | 1.00 | 12.51 | C |
| ATOM | 37893 | CB | VAL | D | 531 | 9.040 | 93.127 | 13.053 | 1.00 | 13.15 | C |
| ATOM | 37895 | CG1 | VAL | D | 531 | 9.197 | 94.251 | 14.052 | 1.00 | 13.93 | C |
| ATOM | 37899 | CG2 | VAL | D | 531 | 7.940 | 92.171 | 13.435 | 1.00 | 15.57 | C |
| ATOM | 37903 | C | VAL | D | 531 | 7.730 | 94.658 | 11.510 | 1.00 | 11.80 | C |
| ATOM | 37904 | O | VAL | D | 531 | 6.505 | 94.332 | 11.419 | 1.00 | 12.23 | O |
| ATOM | 37906 | N | LEU | D | 532 | 8.134 | 95.934 | 11.557 | 1.00 | 12.21 | N |
| ATOM | 37907 | CA | LEU | D | 532 | 7.129 | 97.008 | 11.488 | 1.00 | 11.83 | C |

| ATOM | 37909 | CB | LEU | D | 532 | 7.735 | 98.375 | 11.772 | 1.00 | 13.64 | C |
|------|-------|-----|-----|---|-----|-------|--------|--------|------|-------|---|
| ATOM | 37912 | CG | LEU | D | 532 | 8.278 | 98.434 | 13.208 | 1.00 | 14.18 | C |
| ATOM | 37914 | CD1 | LEU | D | 532 | 9.109 | 99.696 | 13.390 | 1.00 | 15.85 | C |
| ATOM | 37918 | CD2 | LEU | D | 532 | 7.127 | 98.397 | 14.182 | 1.00 | 15.34 | C |
| ATOM | 37922 | C | LEU | D | 532 | 6.477 | 97.054 | 10.087 | 1.00 | 12.83 | C |
| ATOM | 37923 | O | LEU | D | 532 | 5.272 | 97.193 | 9.978 | 1.00 | 13.20 | O |
| ATOM | 37925 | N | GLN | D | 533 | 7.287 | 96.907 | 9.032 | 1.00 | 12.41 | N |
| ATOM | 37926 | CA | GLN | D | 533 | 6.745 | 96.774 | 7.662 | 1.00 | 13.41 | C |
| ATOM | 37928 | CB | GLN | D | 533 | 7.840 | 96.622 | 6.626 | 1.00 | 13.33 | C |
| ATOM | 37931 | CG | GLN | D | 533 | 7.363 | 96.444 | 5.158 | 1.00 | 14.44 | C |
| ATOM | 37934 | CD | GLN | D | 533 | 7.019 | 97.732 | 4.468 | 1.00 | 14.69 | C |
| ATOM | 37935 | OE1 | GLN | D | 533 | 7.157 | 98.846 | 5.043 | 1.00 | 13.31 | O |
| ATOM | 37936 | NE2 | GLN | D | 533 | 6.659 | 97.616 | 3.172 | 1.00 | 14.33 | N |
| ATOM | 37939 | C | GLN | D | 533 | 5.783 | 95.584 | 7.594 | 1.00 | 12.75 | C |
| ATOM | 37940 | O | GLN | D | 533 | 4.658 | 95.709 | 7.109 | 1.00 | 13.98 | O |
| ATOM | 37942 | N | ALA | D | 534 | 6.192 | 94.425 | 8.126 | 1.00 | 12.61 | N |
| ATOM | 37943 | CA | ALA | D | 534 | 5.326 | 93.217 | 8.108 | 1.00 | 11.68 | C |
| ATOM | 37945 | CB | ALA | D | 534 | 6.002 | 92.039 | 8.738 | 1.00 | 11.47 | C |
| ATOM | 37949 | C | ALA | D | 534 | 4.012 | 93.467 | 8.831 | 1.00 | 12.34 | C |
| ATOM | 37950 | O | ALA | D | 534 | 2.925 | 93.035 | 8.395 | 1.00 | 11.94 | O |
| ATOM | 37952 | N | ILE | D | 535 | 4.078 | 94.200 | 9.949 | 1.00 | 11.23 | N |
| ATOM | 37953 | CA | ILE | D | 535 | 2.878 | 94.460 | 10.756 | 1.00 | 12.37 | C |
| ATOM | 37955 | CB | ILE | D | 535 | 3.234 | 95.152 | 12.080 | 1.00 | 12.96 | C |
| ATOM | 37957 | CG1 | ILE | D | 535 | 3.719 | 94.075 | 13.067 | 1.00 | 13.62 | C |
| ATOM | 37960 | CD1 | ILE | D | 535 | 4.530 | 94.508 | 14.233 | 1.00 | 16.53 | C |
| ATOM | 37964 | CG2 | ILE | D | 535 | 2.078 | 95.965 | 12.662 | 1.00 | 12.36 | C |
| ATOM | 37968 | C | ILE | D | 535 | 1.922 | 95.295 | 9.929 | 1.00 | 12.07 | C |
| ATOM | 37969 | O | ILE | D | 535 | 0.732 | 95.001 | 9.886 | 1.00 | 12.42 | O |
| ATOM | 37971 | N | ASP | D | 536 | 2.461 | 96.300 | 9.232 | 1.00 | 11.07 | N |
| ATOM | 37972 | CA | ASP | D | 536 | 1.616 | 97.149 | 8.366 | 1.00 | 12.72 | C |
| ATOM | 37974 | CB | ASP | D | 536 | 2.400 | 98.335 | 7.824 | 1.00 | 11.78 | C |
| ATOM | 37977 | CG | ASP | D | 536 | 2.612 | 99.401 | 8.892 | 1.00 | 13.45 | C |
| ATOM | 37978 | OD1 | ASP | D | 536 | 1.735 | 99.563 | 9.770 | 1.00 | 13.72 | O |
| ATOM | 37979 | OD2 | ASP | D | 536 | 3.680 | 100.049 | 8.854 | 1.00 | 14.35 | O |
| ATOM | 37980 | C | ASP | D | 536 | 0.989 | 96.357 | 7.233 | 1.00 | 11.66 | C |
| ATOM | 37981 | O | ASP | D | 536 | -0.158 | 96.564 | 6.896 | 1.00 | 12.59 | O |
| ATOM | 37983 | N | LEU | D | 537 | 1.745 | 95.455 | 6.641 | 1.00 | 11.40 | N |
| ATOM | 37984 | CA | LEU | D | 537 | 1.221 | 94.672 | 5.537 | 1.00 | 11.01 | C |
| ATOM | 37986 | CB | LEU | D | 537 | 2.351 | 93.931 | 4.833 | 1.00 | 12.22 | C |
| ATOM | 37989 | CG | LEU | D | 537 | 3.362 | 94.824 | 4.105 | 1.00 | 12.83 | C |
| ATOM | 37991 | CD1 | LEU | D | 537 | 4.478 | 93.932 | 3.566 | 1.00 | 14.62 | C |
| ATOM | 37995 | CD2 | LEU | D | 537 | 2.712 | 95.603 | 3.004 | 1.00 | 16.40 | C |
| ATOM | 37999 | C | LEU | D | 537 | 0.178 | 93.718 | 6.037 | 1.00 | 10.93 | C |
| ATOM | 38000 | O | LEU | D | 537 | -0.828 | 93.458 | 5.347 | 1.00 | 12.30 | O |
| ATOM | 38002 | N | ARG | D | 538 | 0.397 | 93.169 | 7.231 | 1.00 | 10.20 | N |
| ATOM | 38003 | CA | ARG | D | 538 | -0.634 | 92.289 | 7.814 | 1.00 | 10.18 | C |
| ATOM | 38005 | CB | ARG | D | 538 | -0.110 | 91.590 | 9.069 | 1.00 | 11.11 | C |
| ATOM | 38008 | CG | ARG | D | 538 | -1.012 | 90.489 | 9.597 | 1.00 | 11.68 | C |
| ATOM | 38011 | CD | ARG | D | 538 | -0.993 | 89.281 | 8.644 | 1.00 | 13.69 | C |
| ATOM | 38014 | NE | ARG | D | 538 | 0.202 | 88.459 | 8.794 | 1.00 | 14.64 | N |
| ATOM | 38016 | CZ | ARG | D | 538 | 0.508 | 87.413 | 8.026 | 1.00 | 12.80 | C |
| ATOM | 38017 | NH1 | ARG | D | 538 | -0.260 | 87.086 | 6.974 | 1.00 | 16.18 | N |
| ATOM | 38020 | NH2 | ARG | D | 538 | 1.590 | 86.697 | 8.285 | 1.00 | 15.11 | N |
| ATOM | 38023 | C | ARG | D | 538 | -1.923 | 93.057 | 8.132 | 1.00 | 11.81 | C |
| ATOM | 38024 | O | ARG | D | 538 | -3.028 | 92.532 | 7.993 | 1.00 | 12.15 | O |
| ATOM | 38026 | N | ALA | D | 539 | -1.784 | 94.292 | 8.606 | 1.00 | 11.56 | N |
| ATOM | 38027 | CA | ALA | D | 539 | -2.959 | 95.131 | 8.912 | 1.00 | 13.07 | C |

| ATOM | 38029 | CB  | ALA | D | 539 | -2.523  | 96.426 | 9.559  | 1.00 | 12.88 | C |
|------|-------|-----|-----|---|-----|---------|--------|--------|------|-------|---|
| ATOM | 38033 | C   | ALA | D | 539 | -3.730  | 95.409 | 7.615  | 1.00 | 12.12 | C |
| ATOM | 38034 | O   | ALA | D | 539 | -4.958  | 95.427 | 7.599  | 1.00 | 12.76 | O |
| ATOM | 38036 | N   | ILE | D | 540 | -2.995  | 95.667 | 6.518  | 1.00 | 13.81 | N |
| ATOM | 38037 | CA  | ILE | D | 540 | -3.632  | 95.883 | 5.206  | 1.00 | 14.01 | C |
| ATOM | 38039 | CB  | ILE | D | 540 | -2.585  | 96.249 | 4.142  | 1.00 | 14.30 | C |
| ATOM | 38041 | CG1 | ILE | D | 540 | -2.122  | 97.693 | 4.382  | 1.00 | 14.35 | C |
| ATOM | 38044 | CD1 | ILE | D | 540 | -0.819  | 98.043 | 3.613  | 1.00 | 14.89 | C |
| ATOM | 38048 | CG2 | ILE | D | 540 | -3.148  | 96.075 | 2.684  | 1.00 | 14.62 | C |
| ATOM | 38052 | C   | ILE | D | 540 | -4.397  | 94.630 | 4.799  | 1.00 | 13.19 | C |
| ATOM | 38053 | O   | ILE | D | 540 | -5.546  | 94.703 | 4.378  | 1.00 | 13.55 | O |
| ATOM | 38055 | N   | GLU | D | 541 | -3.784  | 93.475 | 5.037  | 1.00 | 12.93 | N |
| ATOM | 38056 | CA  | GLU | D | 541 | -4.460  | 92.198 | 4.783  | 1.00 | 13.54 | C |
| ATOM | 38058 | CB  | GLU | D | 541 | -3.582  | 91.046 | 5.157  | 1.00 | 14.55 | C |
| ATOM | 38061 | CG  | GLU | D | 541 | -4.137  | 89.706 | 4.854  | 1.00 | 15.95 | C |
| ATOM | 38064 | CD  | GLU | D | 541 | -3.318  | 88.625 | 5.516  | 1.00 | 20.16 | C |
| ATOM | 38065 | OE1 | GLU | D | 541 | -2.054  | 88.699 | 5.498  | 1.00 | 17.99 | O |
| ATOM | 38066 | OE2 | GLU | D | 541 | -3.939  | 87.708 | 6.082  | 1.00 | 27.08 | O |
| ATOM | 38067 | C   | GLU | D | 541 | -5.733  | 92.101 | 5.597  | 1.00 | 13.12 | C |
| ATOM | 38068 | O   | GLU | D | 541 | -6.778  | 91.709 | 5.056  | 1.00 | 13.52 | O |
| ATOM | 38070 | N   | PHE | D | 542 | -5.687  | 92.491 | 6.877  | 1.00 | 12.35 | N |
| ATOM | 38071 | CA  | PHE | D | 542 | -6.858  | 92.363 | 7.699  | 1.00 | 12.54 | C |
| ATOM | 38073 | CB  | PHE | D | 542 | -6.540  | 92.592 | 9.178  | 1.00 | 13.70 | C |
| ATOM | 38076 | CG  | PHE | D | 542 | -5.882  | 91.421 | 9.888  | 1.00 | 14.85 | C |
| ATOM | 38077 | CD1 | PHE | D | 542 | -5.470  | 90.279 | 9.220  | 1.00 | 14.11 | C |
| ATOM | 38079 | CE1 | PHE | D | 542 | -4.843  | 89.217 | 9.907  | 1.00 | 17.07 | C |
| ATOM | 38081 | CZ  | PHE | D | 542 | -4.639  | 89.318 | 11.283 | 1.00 | 17.74 | C |
| ATOM | 38083 | CE2 | PHE | D | 542 | -5.028  | 90.460 | 11.954 | 1.00 | 18.56 | C |
| ATOM | 38085 | CD2 | PHE | D | 542 | -5.642  | 91.515 | 11.255 | 1.00 | 19.62 | C |
| ATOM | 38087 | C   | PHE | D | 542 | -7.978  | 93.329 | 7.247  | 1.00 | 11.67 | C |
| ATOM | 38088 | O   | PHE | D | 542 | -9.155  | 92.976 | 7.223  | 1.00 | 12.70 | O |
| ATOM | 38090 | N   | GLU | D | 543 | -7.590  | 94.547 | 6.847  | 1.00 | 10.62 | N |
| ATOM | 38091 | CA  | GLU | D | 543 | -8.590  | 95.544 | 6.370  | 1.00 | 11.73 | C |
| ATOM | 38093 | CB  | GLU | D | 543 | -7.923  | 96.874 | 6.097  | 1.00 | 12.59 | C |
| ATOM | 38096 | CG  | GLU | D | 543 | -7.410  | 97.576 | 7.387  | 1.00 | 12.73 | C |
| ATOM | 38099 | CD  | GLU | D | 543 | -8.530  | 97.856 | 8.359  | 1.00 | 16.57 | C |
| ATOM | 38100 | OE1 | GLU | D | 543 | -9.500  | 98.543 | 7.997  | 1.00 | 18.85 | O |
| ATOM | 38101 | OE2 | GLU | D | 543 | -8.479  | 97.378 | 9.498  | 1.00 | 17.33 | O |
| ATOM | 38102 | C   | GLU | D | 543 | -9.234  | 95.008 | 5.084  | 1.00 | 12.25 | C |
| ATOM | 38103 | O   | GLU | D | 543 | -10.441 | 95.109 | 4.895  | 1.00 | 12.07 | O |
| ATOM | 38105 | N   | PHE | D | 544 | -8.412  | 94.451 | 4.196  | 1.00 | 12.25 | N |
| ATOM | 38106 | CA  | PHE | D | 544 | -8.955  | 93.801 | 2.994  | 1.00 | 13.48 | C |
| ATOM | 38108 | CB  | PHE | D | 544 | -7.805  | 93.177 | 2.198  | 1.00 | 13.63 | C |
| ATOM | 38111 | CG  | PHE | D | 544 | -8.236  | 92.419 | 0.971  | 1.00 | 14.43 | C |
| ATOM | 38112 | CD1 | PHE | D | 544 | -8.442  | 93.058 | -0.228 | 1.00 | 13.14 | C |
| ATOM | 38114 | CE1 | PHE | D | 544 | -8.841  | 92.316 | -1.364 | 1.00 | 15.08 | C |
| ATOM | 38116 | CZ  | PHE | D | 544 | -9.014  | 90.931 | -1.281 | 1.00 | 14.05 | C |
| ATOM | 38118 | CE2 | PHE | D | 544 | -8.782  | 90.282 | -0.096 | 1.00 | 15.41 | C |
| ATOM | 38120 | CD2 | PHE | D | 544 | -8.389  | 91.033 | 1.036  | 1.00 | 13.73 | C |
| ATOM | 38122 | C   | PHE | D | 544 | -9.993  | 92.728 | 3.341  | 1.00 | 13.54 | C |
| ATOM | 38123 | O   | PHE | D | 544 | -11.071 | 92.652 | 2.753  | 1.00 | 12.90 | O |
| ATOM | 38125 | N   | LYS | D | 545 | -9.622  | 91.852 | 4.252  | 1.00 | 14.95 | N |
| ATOM | 38126 | CA  | LYS | D | 545 | -10.486 | 90.731 | 4.609  | 1.00 | 17.27 | C |
| ATOM | 38128 | CB  | LYS | D | 545 | -9.812  | 89.796 | 5.611  | 1.00 | 18.58 | C |
| ATOM | 38131 | CG  | LYS | D | 545 | -8.731  | 88.961 | 4.952  | 1.00 | 19.89 | C |
| ATOM | 38134 | CD  | LYS | D | 545 | -7.922  | 88.175 | 5.978  | 1.00 | 22.11 | C |
| ATOM | 38137 | CE  | LYS | D | 545 | -6.879  | 87.270 | 5.301  | 1.00 | 26.07 | C |

| ATOM | 38140 | NZ | LYS | D | 545 | -6.115 | 86.420 | 6.275 | 1.00 | 27.29 | N |
|------|-------|-----|-----|---|-----|--------|--------|-------|------|-------|---|
| ATOM | 38144 | C | LYS | D | 545 | -11.833 | 91.228 | 5.088 | 1.00 | 16.85 | C |
| ATOM | 38145 | O | LYS | D | 545 | -12.863 | 90.599 | 4.784 | 1.00 | 16.23 | O |
| ATOM | 38147 | N | LYS | D | 546 | -11.849 | 92.356 | 5.805 | 1.00 | 17.37 | N |
| ATOM | 38148 | CA | LYS | D | 546 | -13.111 | 92.928 | 6.306 | 1.00 | 19.50 | C |
| ATOM | 38150 | CB | LYS | D | 546 | -12.855 | 94.232 | 7.089 | 1.00 | 19.69 | C |
| ATOM | 38153 | CG | LYS | D | 546 | -12.572 | 93.984 | 8.539 | 1.00 | 23.14 | C |
| ATOM | 38156 | CD | LYS | D | 546 | -11.848 | 95.133 | 9.227 | 1.00 | 24.98 | C |
| ATOM | 38159 | CE | LYS | D | 546 | -12.544 | 96.447 | 9.091 | 1.00 | 30.77 | C |
| ATOM | 38162 | NZ | LYS | D | 546 | -12.006 | 97.409 | 10.161 | 1.00 | 34.59 | N |
| ATOM | 38166 | C | LYS | D | 546 | -14.113 | 93.182 | 5.224 | 1.00 | 18.85 | C |
| ATOM | 38167 | O | LYS | D | 546 | -15.317 | 92.957 | 5.397 | 1.00 | 19.65 | O |
| ATOM | 38169 | N | GLN | D | 547 | -13.621 | 93.688 | 4.101 | 1.00 | 17.11 | N |
| ATOM | 38170 | CA | GLN | D | 547 | -14.471 | 93.980 | 2.974 | 1.00 | 17.79 | C |
| ATOM | 38172 | CB | GLN | D | 547 | -13.903 | 95.136 | 2.232 | 1.00 | 17.48 | C |
| ATOM | 38175 | CG | GLN | D | 547 | -13.989 | 96.442 | 2.983 | 1.00 | 20.80 | C |
| ATOM | 38178 | CD | GLN | D | 547 | -13.823 | 97.585 | 2.037 | 1.00 | 20.00 | C |
| ATOM | 38179 | OE1 | GLN | D | 547 | -14.641 | 97.747 | 1.110 | 1.00 | 29.28 | O |
| ATOM | 38180 | NE2 | GLN | D | 547 | -12.775 | 98.368 | 2.223 | 1.00 | 16.37 | N |
| ATOM | 38183 | C | GLN | D | 547 | -14.616 | 92.785 | 2.044 | 1.00 | 17.54 | C |
| ATOM | 38184 | O | GLN | D | 547 | -15.648 | 92.639 | 1.382 | 1.00 | 17.57 | O |
| ATOM | 38186 | N | PHE | D | 548 | -13.590 | 91.946 | 1.947 | 1.00 | 17.50 | N |
| ATOM | 38187 | CA | PHE | D | 548 | -13.671 | 90.880 | 0.983 | 1.00 | 18.26 | C |
| ATOM | 38189 | CB | PHE | D | 548 | -12.295 | 90.486 | 0.475 | 1.00 | 18.94 | C |
| ATOM | 38192 | CG | PHE | D | 548 | -12.351 | 89.873 | -0.894 | 1.00 | 21.32 | C |
| ATOM | 38193 | CD1 | PHE | D | 548 | -12.906 | 90.571 | -1.950 | 1.00 | 22.08 | C |
| ATOM | 38195 | CE1 | PHE | D | 548 | -12.987 | 89.987 | -3.220 | 1.00 | 23.11 | C |
| ATOM | 38197 | CZ | PHE | D | 548 | -12.502 | 88.689 | -3.380 | 1.00 | 21.80 | C |
| ATOM | 38199 | CE2 | PHE | D | 548 | -11.972 | 88.015 | -2.313 | 1.00 | 21.34 | C |
| ATOM | 38201 | CD2 | PHE | D | 548 | -11.918 | 88.608 | -1.086 | 1.00 | 23.42 | C |
| ATOM | 38203 | C | PHE | D | 548 | -14.554 | 89.682 | 1.358 | 1.00 | 17.99 | C |
| ATOM | 38204 | O | PHE | D | 548 | -15.221 | 89.121 | 0.481 | 1.00 | 17.57 | O |
| ATOM | 38206 | N | GLY | D | 549 | -14.654 | 89.335 | 2.635 | 1.00 | 18.40 | N |
| ATOM | 38207 | CA | GLY | D | 549 | -15.603 | 88.275 | 3.032 | 1.00 | 18.96 | C |
| ATOM | 38210 | C | GLY | D | 549 | -17.018 | 88.535 | 2.523 | 1.00 | 19.43 | C |
| ATOM | 38211 | O | GLY | D | 549 | -17.645 | 87.686 | 1.853 | 1.00 | 19.58 | O |
| ATOM | 38213 | N | PRO | D | 550 | -17.564 | 89.716 | 2.826 | 1.00 | 19.84 | N |
| ATOM | 38214 | CA | PRO | D | 550 | -18.890 | 90.046 | 2.274 | 1.00 | 19.93 | C |
| ATOM | 38216 | CB | PRO | D | 550 | -19.240 | 91.403 | 2.947 | 1.00 | 20.66 | C |
| ATOM | 38219 | CG | PRO | D | 550 | -18.304 | 91.513 | 4.095 | 1.00 | 19.13 | C |
| ATOM | 38222 | CD | PRO | D | 550 | -17.071 | 90.751 | 3.759 | 1.00 | 19.95 | C |
| ATOM | 38225 | C | PRO | D | 550 | -18.945 | 90.137 | 0.723 | 1.00 | 20.17 | C |
| ATOM | 38226 | O | PRO | D | 550 | -19.980 | 89.852 | 0.129 | 1.00 | 20.84 | O |
| ATOM | 38227 | N | ALA | D | 551 | -17.849 | 90.529 | 0.076 | 1.00 | 19.75 | N |
| ATOM | 38228 | CA | ALA | D | 551 | -17.816 | 90.592 | -1.404 | 1.00 | 19.35 | C |
| ATOM | 38230 | CB | ALA | D | 551 | -16.547 | 91.290 | -1.898 | 1.00 | 19.36 | C |
| ATOM | 38234 | C | ALA | D | 551 | -17.927 | 89.203 | -2.028 | 1.00 | 18.55 | C |
| ATOM | 38235 | O | ALA | D | 551 | -18.639 | 89.007 | -3.048 | 1.00 | 20.17 | O |
| ATOM | 38237 | N | ILE | D | 552 | -17.253 | 88.235 | -1.407 | 1.00 | 18.38 | N |
| ATOM | 38238 | CA | ILE | D | 552 | -17.310 | 86.837 | -1.870 | 1.00 | 17.99 | C |
| ATOM | 38240 | CB | ILE | D | 552 | -16.466 | 85.919 | -0.976 | 1.00 | 17.91 | C |
| ATOM | 38242 | CG1 | ILE | D | 552 | -14.988 | 86.227 | -1.165 | 1.00 | 20.64 | C |
| ATOM | 38245 | CD1 | ILE | D | 552 | -14.137 | 85.559 | -0.173 | 1.00 | 21.53 | C |
| ATOM | 38249 | CG2 | ILE | D | 552 | -16.754 | 84.418 | -1.268 | 1.00 | 19.25 | C |
| ATOM | 38253 | C | ILE | D | 552 | -18.772 | 86.374 | -1.846 | 1.00 | 17.24 | C |
| ATOM | 38254 | O | ILE | D | 552 | -19.307 | 85.812 | -2.828 | 1.00 | 16.24 | O |
| ATOM | 38256 | N | VAL | D | 553 | -19.435 | 86.660 | -0.732 | 1.00 | 16.39 | N |

| | | | | | | | | | |
|---|---|---|---|---|---|---|---|---|---|
| ATOM | 38257 | CA | VAL | D 553 | -20.815 | 86.227 | -0.575 | 1.00 16.63 | C |
| ATOM | 38259 | CB | VAL | D 553 | -21.328 | 86.503 | 0.835 | 1.00 16.41 | C |
| ATOM | 38261 | CG1 | VAL | D 553 | -22.811 | 86.174 | 0.921 | 1.00 19.37 | C |
| ATOM | 38265 | CG2 | VAL | D 553 | -20.558 | 85.683 | 1.820 | 1.00 18.52 | C |
| ATOM | 38269 | C | VAL | D 553 | -21.688 | 86.931 | -1.613 | 1.00 16.27 | C |
| ATOM | 38270 | O | VAL | D 553 | -22.515 | 86.288 | -2.255 | 1.00 14.80 | O |
| ATOM | 38272 | N | SER | D 554 | -21.506 | 88.238 | -1.805 | 1.00 15.64 | N |
| ATOM | 38273 | CA | SER | D 554 | -22.389 | 88.973 | -2.702 | 1.00 17.89 | C |
| ATOM | 38275 | CB | SER | D 554 | -22.099 | 90.463 | -2.675 | 1.00 18.71 | C |
| ATOM | 38278 | OG | SER | D 554 | -22.142 | 90.948 | -1.343 | 1.00 25.05 | O |
| ATOM | 38280 | C | SER | D 554 | -22.252 | 88.517 | -4.135 | 1.00 16.68 | C |
| ATOM | 38281 | O | SER | D 554 | -23.242 | 88.452 | -4.872 | 1.00 15.77 | O |
| ATOM | 38283 | N | LEU | D 555 | -21.011 | 88.233 | -4.533 | 1.00 15.81 | N |
| ATOM | 38284 | CA | LEU | D 555 | -20.778 | 87.782 | -5.919 | 1.00 16.11 | C |
| ATOM | 38286 | CB | LEU | D 555 | -19.300 | 87.923 | -6.344 | 1.00 16.72 | C |
| ATOM | 38289 | CG | LEU | D 555 | -19.146 | 89.260 | -7.077 | 1.00 20.35 | C |
| ATOM | 38291 | CD1 | LEU | D 555 | -19.250 | 90.366 | -6.058 | 1.00 24.37 | C |
| ATOM | 38295 | CD2 | LEU | D 555 | -17.881 | 89.400 | -7.827 | 1.00 23.99 | C |
| ATOM | 38299 | C | LEU | D 555 | -21.336 | 86.380 | -6.148 | 1.00 14.48 | C |
| ATOM | 38300 | O | LEU | D 555 | -21.884 | 86.123 | -7.192 | 1.00 14.05 | O |
| ATOM | 38302 | N | ILE | D 556 | -21.203 | 85.510 | -5.147 | 1.00 14.34 | N |
| ATOM | 38303 | CA | ILE | D 556 | -21.773 | 84.179 | -5.199 | 1.00 13.62 | C |
| ATOM | 38305 | CB | ILE | D 556 | -21.346 | 83.344 | -3.981 | 1.00 13.60 | C |
| ATOM | 38307 | CG1 | ILE | D 556 | -19.939 | 82.811 | -4.197 | 1.00 12.52 | C |
| ATOM | 38310 | CD1 | ILE | D 556 | -19.320 | 82.079 | -3.006 | 1.00 13.29 | C |
| ATOM | 38314 | CG2 | ILE | D 556 | -22.306 | 82.175 | -3.731 | 1.00 13.97 | C |
| ATOM | 38318 | C | ILE | D 556 | -23.298 | 84.269 | -5.360 | 1.00 14.37 | C |
| ATOM | 38319 | O | ILE | D 556 | -23.913 | 83.573 | -6.165 | 1.00 13.95 | O |
| ATOM | 38321 | N | ASP | D 557 | -23.906 | 85.163 | -4.591 | 1.00 14.58 | N |
| ATOM | 38322 | CA | ASP | D 557 | -25.352 | 85.342 | -4.673 | 1.00 14.64 | C |
| ATOM | 38324 | CB | ASP | D 557 | -25.843 | 86.242 | -3.524 | 1.00 14.92 | C |
| ATOM | 38327 | CG | ASP | D 557 | -25.842 | 85.533 | -2.188 | 1.00 17.78 | C |
| ATOM | 38328 | OD1 | ASP | D 557 | -25.855 | 84.284 | -2.160 | 1.00 20.35 | O |
| ATOM | 38329 | OD2 | ASP | D 557 | -25.862 | 86.230 | -1.140 | 1.00 22.21 | O |
| ATOM | 38330 | C | ASP | D 557 | -25.780 | 85.912 | -5.996 | 1.00 15.30 | C |
| ATOM | 38331 | O | ASP | D 557 | -26.788 | 85.475 | -6.564 | 1.00 14.86 | O |
| ATOM | 38333 | N | GLN | D 558 | -25.045 | 86.908 | -6.478 | 1.00 15.52 | N |
| ATOM | 38334 | CA | GLN | D 558 | -25.386 | 87.563 | -7.733 | 1.00 16.44 | C |
| ATOM | 38336 | CB | GLN | D 558 | -24.469 | 88.773 | -7.957 | 1.00 17.31 | C |
| ATOM | 38339 | CG | GLN | D 558 | -24.732 | 89.564 | -9.242 | 1.00 18.86 | C |
| ATOM | 38342 | CD | GLN | D 558 | -23.584 | 90.531 | -9.639 | 1.00 21.61 | C |
| ATOM | 38343 | OE1 | GLN | D 558 | -22.475 | 90.492 | -9.100 | 1.00 25.37 | O |
| ATOM | 38344 | NE2 | GLN | D 558 | -23.863 | 91.377 | -10.632 | 1.00 27.79 | N |
| ATOM | 38347 | C | GLN | D 558 | -25.288 | 86.593 | -8.913 | 1.00 15.33 | C |
| ATOM | 38348 | O | GLN | D 558 | -26.185 | 86.521 | -9.750 | 1.00 14.46 | O |
| ATOM | 38350 | N | HIS | D 559 | -24.205 | 85.829 | -8.978 | 1.00 14.49 | N |
| ATOM | 38351 | CA | HIS | D 559 | -23.955 | 84.945 | -10.149 | 1.00 13.64 | C |
| ATOM | 38353 | CB | HIS | D 559 | -22.466 | 84.740 | -10.403 | 1.00 13.00 | C |
| ATOM | 38356 | CG | HIS | D 559 | -21.758 | 85.972 | -10.869 | 1.00 12.59 | C |
| ATOM | 38357 | ND1 | HIS | D 559 | -21.491 | 86.226 | -12.194 | 1.00 13.28 | N |
| ATOM | 38359 | CE1 | HIS | D 559 | -20.883 | 87.393 | -12.304 | 1.00 15.79 | C |
| ATOM | 38361 | NE2 | HIS | D 559 | -20.777 | 87.919 | -11.097 | 1.00 14.43 | N |
| ATOM | 38363 | CD2 | HIS | D 559 | -21.303 | 87.046 | -10.181 | 1.00 11.57 | C |
| ATOM | 38365 | C | HIS | D 559 | -24.624 | 83.583 | -10.047 | 1.00 12.87 | C |
| ATOM | 38366 | O | HIS | D 559 | -25.042 | 83.012 | -11.075 | 1.00 13.16 | O |
| ATOM | 38368 | N | PHE | D 560 | -24.674 | 83.045 | -8.823 | 1.00 12.90 | N |
| ATOM | 38369 | CA | PHE | D 560 | -25.143 | 81.689 | -8.603 | 1.00 12.50 | C |

| ATOM | 38371 | CB | PHE | D | 560 | -24.074 | 80.871 | -7.905 | 1.00 | 11.42 | C |
|---|---|---|---|---|---|---|---|---|---|---|---|
| ATOM | 38374 | CG | PHE | D | 560 | -22.720 | 80.923 | -8.577 | 1.00 | 10.54 | C |
| ATOM | 38375 | CD1 | PHE | D | 560 | -22.591 | 80.968 | -9.978 | 1.00 | 12.63 | C |
| ATOM | 38377 | CE1 | PHE | D | 560 | -21.280 | 81.004 | -10.572 | 1.00 | 12.12 | C |
| ATOM | 38379 | CZ | PHE | D | 560 | -20.151 | 80.975 | -9.774 | 1.00 | 12.71 | C |
| ATOM | 38381 | CE2 | PHE | D | 560 | -20.282 | 80.910 | -8.408 | 1.00 | 12.34 | C |
| ATOM | 38383 | CD2 | PHE | D | 560 | -21.583 | 80.890 | -7.816 | 1.00 | 9.45 | C |
| ATOM | 38385 | C | PHE | D | 560 | -26.452 | 81.526 | -7.805 | 1.00 | 13.35 | C |
| ATOM | 38386 | O | PHE | D | 560 | -26.970 | 80.401 | -7.710 | 1.00 | 14.07 | O |
| ATOM | 38388 | N | GLY | D | 561 | -26.964 | 82.616 | -7.234 | 1.00 | 13.95 | N |
| ATOM | 38389 | CA | GLY | D | 561 | -28.166 | 82.526 | -6.373 | 1.00 | 14.00 | C |
| ATOM | 38392 | C | GLY | D | 561 | -29.335 | 81.785 | -6.997 | 1.00 | 14.25 | C |
| ATOM | 38393 | O | GLY | D | 561 | -29.901 | 80.864 | -6.427 | 1.00 | 13.55 | O |
| ATOM | 38395 | N | SER | D | 562 | -29.695 | 82.187 | -8.193 | 1.00 | 14.67 | N |
| ATOM | 38396 | CA | SER | D | 562 | -30.818 | 81.573 | -8.891 | 1.00 | 16.21 | C |
| ATOM | 38398 | CB | SER | D | 562 | -30.987 | 82.276 | -10.233 | 1.00 | 16.71 | C |
| ATOM | 38401 | OG | SER | D | 562 | -31.852 | 81.534 | -11.068 | 1.00 | 22.07 | O |
| ATOM | 38403 | C | SER | D | 562 | -30.629 | 80.064 | -9.105 | 1.00 | 15.99 | C |
| ATOM | 38404 | O | SER | D | 562 | -31.553 | 79.275 | -8.935 | 1.00 | 16.31 | O |
| ATOM | 38406 | N | ALA | D | 563 | -29.422 | 79.671 | -9.507 | 1.00 | 15.40 | N |
| ATOM | 38407 | CA | ALA | D | 563 | -29.103 | 78.267 | -9.749 | 1.00 | 15.35 | C |
| ATOM | 38409 | CB | ALA | D | 563 | -27.737 | 78.165 | -10.388 | 1.00 | 14.78 | C |
| ATOM | 38413 | C | ALA | D | 563 | -29.133 | 77.430 | -8.463 | 1.00 | 16.08 | C |
| ATOM | 38414 | O | ALA | D | 563 | -29.370 | 76.223 | -8.524 | 1.00 | 15.76 | O |
| ATOM | 38416 | N | MSE | D | 564 | -28.963 | 78.070 | -7.305 | 1.00 | 16.37 | N |
| ATOM | 38417 | CA | MSE | D | 564 | -28.928 | 77.358 | -6.030 | 1.00 | 17.84 | C |
| ATOM | 38419 | CB | MSE | D | 564 | -27.889 | 77.960 | -5.101 | 1.00 | 18.55 | C |
| ATOM | 38422 | CG | MSE | D | 564 | -26.495 | 77.871 | -5.645 | 1.00 | 18.34 | C |
| ATOM | 38425 | SE | MSE | D | 564 | -25.144 | 78.537 | -4.399 | 1.00 | 24.83 | SE |
| ATOM | 38426 | CE | MSE | D | 564 | -24.636 | 77.053 | -3.712 | 1.00 | 28.10 | C |
| ATOM | 38430 | C | MSE | D | 564 | -30.272 | 77.387 | -5.321 | 1.00 | 17.40 | C |
| ATOM | 38431 | O | MSE | D | 564 | -30.414 | 76.743 | -4.326 | 1.00 | 16.35 | O |
| ATOM | 38433 | N | THR | D | 565 | -31.244 | 78.127 | -5.832 | 1.00 | 18.09 | N |
| ATOM | 38434 | CA | THR | D | 565 | -32.529 | 78.259 | -5.123 | 1.00 | 19.10 | C |
| ATOM | 38436 | CB | THR | D | 565 | -33.520 | 79.178 | -5.880 | 1.00 | 19.77 | C |
| ATOM | 38438 | OG1 | THR | D | 565 | -33.753 | 78.681 | -7.184 | 1.00 | 22.88 | O |
| ATOM | 38440 | CG2 | THR | D | 565 | -32.968 | 80.578 | -6.010 | 1.00 | 22.14 | C |
| ATOM | 38444 | C | THR | D | 565 | -33.173 | 76.898 | -4.848 | 1.00 | 18.65 | C |
| ATOM | 38445 | O | THR | D | 565 | -33.156 | 76.009 | -5.686 | 1.00 | 19.44 | O |
| ATOM | 38447 | N | GLY | D | 566 | -33.718 | 76.733 | -3.640 | 1.00 | 17.96 | N |
| ATOM | 38448 | CA | GLY | D | 566 | -34.332 | 75.474 | -3.232 | 1.00 | 17.03 | C |
| ATOM | 38451 | C | GLY | D | 566 | -33.367 | 74.384 | -2.801 | 1.00 | 16.22 | C |
| ATOM | 38452 | O | GLY | D | 566 | -33.799 | 73.297 | -2.391 | 1.00 | 16.10 | O |
| ATOM | 38454 | N | SER | D | 567 | -32.076 | 74.669 | -2.882 | 1.00 | 16.01 | N |
| ATOM | 38455 | CA | SER | D | 567 | -31.053 | 73.722 | -2.513 | 1.00 | 15.04 | C |
| ATOM | 38457 | CB | SER | D | 567 | -29.923 | 73.718 | -3.564 | 1.00 | 15.80 | C |
| ATOM | 38460 | OG | SER | D | 567 | -28.967 | 74.739 | -3.269 | 1.00 | 14.66 | O |
| ATOM | 38462 | C | SER | D | 567 | -30.445 | 74.109 | -1.178 | 1.00 | 14.56 | C |
| ATOM | 38463 | O | SER | D | 567 | -30.712 | 75.173 | -0.600 | 1.00 | 14.26 | O |
| ATOM | 38465 | N | ASN | D | 568 | -29.599 | 73.225 | -0.707 | 1.00 | 13.08 | N |
| ATOM | 38466 | CA | ASN | D | 568 | -28.836 | 73.460 | 0.475 | 1.00 | 12.76 | C |
| ATOM | 38468 | CB | ASN | D | 568 | -28.987 | 72.272 | 1.426 | 1.00 | 12.85 | C |
| ATOM | 38471 | CG | ASN | D | 568 | -28.395 | 72.539 | 2.766 | 1.00 | 14.45 | C |
| ATOM | 38472 | OD1 | ASN | D | 568 | -28.252 | 73.693 | 3.166 | 1.00 | 14.87 | O |
| ATOM | 38473 | ND2 | ASN | D | 568 | -27.967 | 71.487 | 3.444 | 1.00 | 15.36 | N |
| ATOM | 38476 | C | ASN | D | 568 | -27.382 | 73.647 | 0.066 | 1.00 | 11.85 | C |
| ATOM | 38477 | O | ASN | D | 568 | -26.499 | 73.235 | 0.775 | 1.00 | 12.14 | O |

| ATOM | 38479 | N   | LEU | D | 569 | -27.130 | 74.320 | -1.056 | 1.00 | 11.88 | N |
|------|-------|-----|-----|---|-----|---------|--------|--------|------|-------|---|
| ATOM | 38480 | CA  | LEU | D | 569 | -25.730 | 74.422 | -1.569 | 1.00 | 12.06 | C |
| ATOM | 38482 | CB  | LEU | D | 569 | -25.727 | 74.302 | -3.095 | 1.00 | 11.74 | C |
| ATOM | 38485 | CG  | LEU | D | 569 | -26.174 | 72.955 | -3.668 | 1.00 | 12.73 | C |
| ATOM | 38487 | CD1 | LEU | D | 569 | -26.332 | 73.083 | -5.179 | 1.00 | 14.53 | C |
| ATOM | 38491 | CD2 | LEU | D | 569 | -25.203 | 71.842 | -3.260 | 1.00 | 12.71 | C |
| ATOM | 38495 | C   | LEU | D | 569 | -24.957 | 75.680 | -1.169 | 1.00 | 13.14 | C |
| ATOM | 38496 | O   | LEU | D | 569 | -23.738 | 75.693 | -1.226 | 1.00 | 12.92 | O |
| ATOM | 38498 | N   | ARG | D | 570 | -25.670 | 76.742 | -0.780 | 1.00 | 14.89 | N |
| ATOM | 38499 | CA  | ARG | D | 570 | -25.051 | 78.067 | -0.609 | 1.00 | 16.31 | C |
| ATOM | 38501 | CB  | ARG | D | 570 | -26.127 | 79.150 | -0.445 | 1.00 | 16.49 | C |
| ATOM | 38504 | CG  | ARG | D | 570 | -25.564 | 80.514 | -0.056 | 1.00 | 16.68 | C |
| ATOM | 38507 | CD  | ARG | D | 570 | -26.642 | 81.552 | -0.120 | 1.00 | 19.62 | C |
| ATOM | 38510 | NE  | ARG | D | 570 | -26.164 | 82.913 | 0.128  | 1.00 | 22.02 | N |
| ATOM | 38512 | CZ  | ARG | D | 570 | -26.351 | 83.598 | 1.253  | 1.00 | 26.51 | C |
| ATOM | 38513 | NH1 | ARG | D | 570 | -26.998 | 83.068 | 2.296  | 1.00 | 29.58 | N |
| ATOM | 38516 | NH2 | ARG | D | 570 | -25.922 | 84.839 | 1.323  | 1.00 | 23.55 | N |
| ATOM | 38519 | C   | ARG | D | 570 | -24.058 | 78.110 | 0.545  | 1.00 | 15.91 | C |
| ATOM | 38520 | O   | ARG | D | 570 | -22.934 | 78.586 | 0.401  | 1.00 | 14.77 | O |
| ATOM | 38522 | N   | ASP | D | 571 | -24.469 | 77.651 | 1.724  | 1.00 | 16.78 | N |
| ATOM | 38523 | CA  | ASP | D | 571 | -23.516 | 77.580 | 2.842  | 1.00 | 18.49 | C |
| ATOM | 38525 | CB  | ASP | D | 571 | -24.181 | 76.976 | 4.082  | 1.00 | 20.41 | C |
| ATOM | 38528 | CG  | ASP | D | 571 | -24.824 | 78.020 | 4.957  | 1.00 | 25.82 | C |
| ATOM | 38529 | OD1 | ASP | D | 571 | -25.287 | 79.054 | 4.397  | 1.00 | 30.51 | O |
| ATOM | 38530 | OD2 | ASP | D | 571 | -24.869 | 77.785 | 6.205  | 1.00 | 31.43 | O |
| ATOM | 38531 | C   | ASP | D | 571 | -22.271 | 76.763 | 2.508  | 1.00 | 17.39 | C |
| ATOM | 38532 | O   | ASP | D | 571 | -21.135 | 77.162 | 2.796  | 1.00 | 17.06 | O |
| ATOM | 38534 | N   | GLU | D | 572 | -22.508 | 75.592 | 1.918  | 1.00 | 16.04 | N |
| ATOM | 38535 | CA  | GLU | D | 572 | -21.408 | 74.747 | 1.522  | 1.00 | 15.10 | C |
| ATOM | 38537 | CB  | GLU | D | 572 | -21.909 | 73.485 | 0.817  | 1.00 | 14.68 | C |
| ATOM | 38540 | CG  | GLU | D | 572 | -20.751 | 72.517 | 0.527  | 1.00 | 15.51 | C |
| ATOM | 38543 | CD  | GLU | D | 572 | -21.193 | 71.213 | -0.119 | 1.00 | 17.47 | C |
| ATOM | 38544 | OE1 | GLU | D | 572 | -20.335 | 70.309 | -0.226 | 1.00 | 23.36 | O |
| ATOM | 38545 | OE2 | GLU | D | 572 | -22.350 | 71.102 | -0.548 | 1.00 | 17.95 | O |
| ATOM | 38546 | C   | GLU | D | 572 | -20.458 | 75.487 | 0.586  | 1.00 | 13.78 | C |
| ATOM | 38547 | O   | GLU | D | 572 | -19.235 | 75.431 | 0.775  | 1.00 | 12.93 | O |
| ATOM | 38549 | N   | LEU | D | 573 | -21.020 | 76.151 | -0.423 | 1.00 | 12.88 | N |
| ATOM | 38550 | CA  | LEU | D | 573 | -20.188 | 76.823 | -1.454 | 1.00 | 12.71 | C |
| ATOM | 38552 | CB  | LEU | D | 573 | -21.038 | 77.358 | -2.606 | 1.00 | 13.41 | C |
| ATOM | 38555 | CG  | LEU | D | 573 | -20.212 | 78.014 | -3.719 | 1.00 | 12.28 | C |
| ATOM | 38557 | CD1 | LEU | D | 573 | -19.373 | 76.945 | -4.473 | 1.00 | 12.17 | C |
| ATOM | 38561 | CD2 | LEU | D | 573 | -21.076 | 78.803 | -4.650 | 1.00 | 12.30 | C |
| ATOM | 38565 | C   | LEU | D | 573 | -19.376 | 77.968 | -0.828 | 1.00 | 12.97 | C |
| ATOM | 38566 | O   | LEU | D | 573 | -18.197 | 78.112 | -1.095 | 1.00 | 11.94 | O |
| ATOM | 38568 | N   | VAL | D | 574 | -20.028 | 78.791 | -0.001 | 1.00 | 14.20 | N |
| ATOM | 38569 | CA  | VAL | D | 574 | -19.310 | 79.890 | 0.656  | 1.00 | 15.05 | C |
| ATOM | 38571 | CB  | VAL | D | 574 | -20.247 | 80.772 | 1.510  | 1.00 | 14.83 | C |
| ATOM | 38573 | CG1 | VAL | D | 574 | -19.408 | 81.750 | 2.351  | 1.00 | 14.68 | C |
| ATOM | 38577 | CG2 | VAL | D | 574 | -21.227 | 81.518 | 0.613  | 1.00 | 14.18 | C |
| ATOM | 38581 | C   | VAL | D | 574 | -18.148 | 79.341 | 1.496  | 1.00 | 15.15 | C |
| ATOM | 38582 | O   | VAL | D | 574 | -16.997 | 79.791 | 1.367  | 1.00 | 17.48 | O |
| ATOM | 38584 | N   | GLU | D | 575 | -18.426 | 78.332 | 2.313  | 1.00 | 16.28 | N |
| ATOM | 38585 | CA  | GLU | D | 575 | -17.398 | 77.760 | 3.166  | 1.00 | 18.21 | C |
| ATOM | 38587 | CB  | GLU | D | 575 | -17.957 | 76.575 | 3.970  | 1.00 | 19.35 | C |
| ATOM | 38590 | CG  | GLU | D | 575 | -16.995 | 76.142 | 5.072  | 1.00 | 25.63 | C |
| ATOM | 38593 | CD  | GLU | D | 575 | -16.740 | 74.616 | 5.171  | 1.00 | 33.32 | C |
| ATOM | 38594 | OE1 | GLU | D | 575 | -16.241 | 73.978 | 4.189  | 1.00 | 36.71 | O |

| | | | | | | | | | |
|---|---|---|---|---|---|---|---|---|---|
| ATOM | 38595 | OE2 | GLU | D | 575 | -16.985 | 74.076 | 6.282 | 1.00 38.65 | O |
| ATOM | 38596 | C | GLU | D | 575 | -16.219 | 77.266 | 2.328 | 1.00 17.19 | C |
| ATOM | 38597 | O | GLU | D | 575 | -15.032 | 77.600 | 2.601 | 1.00 16.81 | O |
| ATOM | 38599 | N | LYS | D | 576 | -16.548 | 76.468 | 1.310 | 1.00 15.46 | N |
| ATOM | 38600 | CA | LYS | D | 576 | -15.528 | 75.775 | 0.558 | 1.00 16.20 | C |
| ATOM | 38602 | CB | LYS | D | 576 | -16.087 | 74.604 | -0.213 | 1.00 16.90 | C |
| ATOM | 38605 | CG | LYS | D | 576 | -16.433 | 73.453 | 0.723 | 1.00 17.43 | C |
| ATOM | 38608 | CD | LYS | D | 576 | -17.030 | 72.262 | 0.047 | 1.00 18.77 | C |
| ATOM | 38611 | CE | LYS | D | 576 | -17.350 | 71.203 | 1.125 | 1.00 20.46 | C |
| ATOM | 38614 | NZ | LYS | D | 576 | -17.816 | 69.948 | 0.508 | 1.00 18.44 | N |
| ATOM | 38618 | C | LYS | D | 576 | -14.737 | 76.714 | -0.344 | 1.00 14.69 | C |
| ATOM | 38619 | O | LYS | D | 576 | -13.554 | 76.515 | -0.515 | 1.00 14.79 | O |
| ATOM | 38621 | N | VAL | D | 577 | -15.395 | 77.711 | -0.932 | 1.00 13.44 | N |
| ATOM | 38622 | CA | VAL | D | 577 | -14.689 | 78.724 | -1.724 | 1.00 14.03 | C |
| ATOM | 38624 | CB | VAL | D | 577 | -15.686 | 79.640 | -2.480 | 1.00 14.56 | C |
| ATOM | 38626 | CG1 | VAL | D | 577 | -15.032 | 80.937 | -2.963 | 1.00 13.57 | C |
| ATOM | 38630 | CG2 | VAL | D | 577 | -16.302 | 78.894 | -3.668 | 1.00 13.10 | C |
| ATOM | 38634 | C | VAL | D | 577 | -13.753 | 79.552 | -0.836 | 1.00 15.84 | C |
| ATOM | 38635 | O | VAL | D | 577 | -12.620 | 79.855 | -1.220 | 1.00 13.82 | O |
| ATOM | 38637 | N | ASN | D | 578 | -14.221 | 79.922 | 0.359 | 1.00 15.59 | N |
| ATOM | 38638 | CA | ASN | D | 578 | -13.336 | 80.606 | 1.308 | 1.00 17.33 | C |
| ATOM | 38640 | CB | ASN | D | 578 | -14.119 | 80.962 | 2.581 | 1.00 17.57 | C |
| ATOM | 38643 | CG | ASN | D | 578 | -15.032 | 82.157 | 2.398 | 1.00 20.52 | C |
| ATOM | 38644 | OD1 | ASN | D | 578 | -14.747 | 83.077 | 1.645 | 1.00 30.46 | O |
| ATOM | 38645 | ND2 | ASN | D | 578 | -16.100 | 82.171 | 3.141 | 1.00 26.90 | N |
| ATOM | 38648 | C | ASN | D | 578 | -12.089 | 79.781 | 1.659 | 1.00 16.71 | C |
| ATOM | 38649 | O | ASN | D | 578 | -10.962 | 80.292 | 1.626 | 1.00 16.52 | O |
| ATOM | 38651 | N | LYS | D | 579 | -12.281 | 78.501 | 1.967 | 1.00 17.27 | N |
| ATOM | 38652 | CA | LYS | D | 579 | -11.140 | 77.629 | 2.261 | 1.00 18.00 | C |
| ATOM | 38654 | CB | LYS | D | 579 | -11.555 | 76.219 | 2.667 | 1.00 18.28 | C |
| ATOM | 38657 | CG | LYS | D | 579 | -12.152 | 76.144 | 4.065 | 1.00 21.63 | C |
| ATOM | 38660 | CD | LYS | D | 579 | -12.728 | 74.763 | 4.373 | 1.00 23.89 | C |
| ATOM | 38663 | CE | LYS | D | 579 | -12.082 | 74.104 | 5.583 | 1.00 30.49 | C |
| ATOM | 38666 | NZ | LYS | D | 579 | -13.054 | 73.130 | 6.190 | 1.00 34.12 | N |
| ATOM | 38670 | C | LYS | D | 579 | -10.150 | 77.517 | 1.091 | 1.00 17.02 | C |
| ATOM | 38671 | O | LYS | D | 579 | -8.932 | 77.538 | 1.284 | 1.00 17.56 | O |
| ATOM | 38673 | N | THR | D | 580 | -10.688 | 77.394 | -0.116 | 1.00 15.19 | N |
| ATOM | 38674 | CA | THR | D | 580 | -9.855 | 77.222 | -1.300 | 1.00 14.68 | C |
| ATOM | 38676 | CB | THR | D | 580 | -10.695 | 76.895 | -2.558 | 1.00 14.26 | C |
| ATOM | 38678 | OG1 | THR | D | 580 | -11.288 | 75.607 | -2.371 | 1.00 14.89 | O |
| ATOM | 38680 | CG2 | THR | D | 580 | -9.814 | 76.919 | -3.833 | 1.00 13.93 | C |
| ATOM | 38684 | C | THR | D | 580 | -9.020 | 78.485 | -1.511 | 1.00 14.96 | C |
| ATOM | 38685 | O | THR | D | 580 | -7.807 | 78.388 | -1.780 | 1.00 14.96 | O |
| ATOM | 38687 | N | LEU | D | 581 | -9.670 | 79.644 | -1.420 | 1.00 15.41 | N |
| ATOM | 38688 | CA | LEU | D | 581 | -9.025 | 80.942 | -1.613 | 1.00 16.20 | C |
| ATOM | 38690 | CB | LEU | D | 581 | -10.028 | 82.088 | -1.524 | 1.00 16.57 | C |
| ATOM | 38693 | CG | LEU | D | 581 | -10.996 | 82.200 | -2.699 | 1.00 15.62 | C |
| ATOM | 38695 | CD1 | LEU | D | 581 | -12.108 | 83.174 | -2.391 | 1.00 17.07 | C |
| ATOM | 38699 | CD2 | LEU | D | 581 | -10.278 | 82.655 | -3.945 | 1.00 17.47 | C |
| ATOM | 38703 | C | LEU | D | 581 | -7.925 | 81.115 | -0.579 | 1.00 17.86 | C |
| ATOM | 38704 | O | LEU | D | 581 | -6.776 | 81.404 | -0.924 | 1.00 16.64 | O |
| ATOM | 38706 | N | ALA | D | 582 | -8.263 | 80.896 | 0.680 | 1.00 19.48 | N |
| ATOM | 38707 | CA | ALA | D | 582 | -7.259 | 81.062 | 1.775 | 1.00 20.26 | C |
| ATOM | 38709 | CB | ALA | D | 582 | -7.919 | 80.871 | 3.143 | 1.00 20.48 | C |
| ATOM | 38713 | C | ALA | D | 582 | -6.057 | 80.148 | 1.642 | 1.00 21.54 | C |
| ATOM | 38714 | O | ALA | D | 582 | -4.929 | 80.622 | 1.829 | 1.00 23.03 | O |
| ATOM | 38716 | N | LYS | D | 583 | -6.267 | 78.869 | 1.316 | 1.00 21.60 | N |

```
ATOM  38717  CA   LYS D 583      -5.174  77.921   1.141  1.00 22.54           C
ATOM  38719  CB   LYS D 583      -5.671  76.489   0.927  1.00 24.11           C
ATOM  38722  CG   LYS D 583      -6.557  75.900   2.089  1.00 31.56           C
ATOM  38725  CD   LYS D 583      -5.833  75.735   3.481  1.00 36.60           C
ATOM  38728  CE   LYS D 583      -5.022  74.412   3.594  1.00 40.25           C
ATOM  38731  NZ   LYS D 583      -3.732  74.627   4.352  1.00 40.13           N
ATOM  38735  C    LYS D 583      -4.281  78.363  -0.039  1.00 20.91           C
ATOM  38736  O    LYS D 583      -3.028  78.282   0.039  1.00 20.73           O
ATOM  38738  N    ARG D 584      -4.901  78.842  -1.124  1.00 18.81           N
ATOM  38739  CA   ARG D 584      -4.127  79.149  -2.332  1.00 18.18           C
ATOM  38741  CB   ARG D 584      -5.029  79.228  -3.580  1.00 18.12           C
ATOM  38744  CG   ARG D 584      -4.281  79.476  -4.873  1.00 17.94           C
ATOM  38747  CD   ARG D 584      -3.192  78.487  -5.164  1.00 18.88           C
ATOM  38750  NE   ARG D 584      -2.546  78.740  -6.452  1.00 17.95           N
ATOM  38752  CZ   ARG D 584      -1.409  78.178  -6.801  1.00 18.90           C
ATOM  38753  NH1  ARG D 584      -0.833  77.300  -5.988  1.00 21.43           N
ATOM  38756  NH2  ARG D 584      -0.847  78.479  -7.957  1.00 19.86           N
ATOM  38759  C    ARG D 584      -3.316  80.419  -2.170  1.00 17.43           C
ATOM  38760  O    ARG D 584      -2.121  80.470  -2.503  1.00 16.51           O
ATOM  38762  N    LEU D 585      -3.973  81.443  -1.662  1.00 17.62           N
ATOM  38763  CA   LEU D 585      -3.357  82.770  -1.515  1.00 18.44           C
ATOM  38765  CB   LEU D 585      -4.378  83.746  -0.958  1.00 18.09           C
ATOM  38768  CG   LEU D 585      -5.490  84.097  -1.965  1.00 18.64           C
ATOM  38770  CD1  LEU D 585      -6.678  84.745  -1.302  1.00 17.71           C
ATOM  38774  CD2  LEU D 585      -4.930  85.015  -3.058  1.00 18.73           C
ATOM  38778  C    LEU D 585      -2.106  82.751  -0.629  1.00 18.90           C
ATOM  38779  O    LEU D 585      -1.183  83.538  -0.836  1.00 19.17           O
ATOM  38781  N    GLU D 586      -2.098  81.859   0.353  1.00 20.17           N
ATOM  38782  CA   GLU D 586      -0.933  81.755   1.264  1.00 20.95           C
ATOM  38784  CB   GLU D 586      -1.144  80.673   2.349  1.00 20.32           C
ATOM  38787  CG   GLU D 586       0.054  80.540   3.296  1.00 22.62           C
ATOM  38790  CD   GLU D 586      -0.206  79.641   4.499  1.00 25.50           C
ATOM  38791  OE1  GLU D 586      -1.362  79.193   4.643  1.00 33.78           O
ATOM  38792  OE2  GLU D 586       0.740  79.407   5.292  1.00 25.19           O
ATOM  38793  C    GLU D 586       0.307  81.420   0.463  1.00 20.16           C
ATOM  38794  O    GLU D 586       1.435  81.725   0.883  1.00 19.30           O
ATOM  38796  N    GLN D 587       0.109  80.750  -0.681  1.00 18.97           N
ATOM  38797  CA   GLN D 587       1.182  80.256  -1.515  1.00 20.57           C
ATOM  38799  CB   GLN D 587       0.767  78.934  -2.163  1.00 21.17           C
ATOM  38802  CG   GLN D 587       0.309  77.837  -1.221  1.00 24.75           C
ATOM  38805  CD   GLN D 587      -0.171  76.641  -2.000  1.00 25.42           C
ATOM  38806  OE1  GLN D 587      -0.939  76.790  -2.955  1.00 27.15           O
ATOM  38807  NE2  GLN D 587       0.307  75.452  -1.637  1.00 29.32           N
ATOM  38810  C    GLN D 587       1.579  81.176  -2.661  1.00 19.32           C
ATOM  38811  O    GLN D 587       2.598  80.962  -3.279  1.00 20.05           O
ATOM  38813  N    THR D 588       0.750  82.155  -3.001  1.00 16.49           N
ATOM  38814  CA   THR D 588       1.012  82.958  -4.174  1.00 15.66           C
ATOM  38816  CB   THR D 588      -0.227  82.908  -5.100  1.00 15.62           C
ATOM  38818  OG1  THR D 588      -1.354  83.421  -4.415  1.00 13.35           O
ATOM  38820  CG2  THR D 588      -0.575  81.493  -5.501  1.00 16.07           C
ATOM  38824  C    THR D 588       1.346  84.391  -3.782  1.00 15.53           C
ATOM  38825  O    THR D 588       1.088  85.335  -4.536  1.00 15.21           O
ATOM  38827  N    ASN D 589       1.994  84.533  -2.629  1.00 14.41           N
ATOM  38828  CA   ASN D 589       2.390  85.839  -2.111  1.00 15.16           C
ATOM  38830  CB   ASN D 589       2.648  85.754  -0.588  1.00 15.14           C
ATOM  38833  CG   ASN D 589       3.526  84.599  -0.175  1.00 17.32           C
ATOM  38834  OD1  ASN D 589       3.640  83.592  -0.890  1.00 18.13           O
```

| | | | | | | | | | |
|---|---|---|---|---|---|---|---|---|---|
| ATOM | 38835 | ND2 | ASN | D | 589 | 4.145 | 84.703 | 1.042 | 1.00 15.67 | N |
| ATOM | 38838 | C | ASN | D | 589 | 3.584 | 86.455 | -2.882 | 1.00 16.15 | C |
| ATOM | 38839 | O | ASN | D | 589 | 3.981 | 87.614 | -2.601 | 1.00 15.87 | O |
| ATOM | 38841 | N | SER | D | 590 | 4.167 | 85.682 | -3.821 | 1.00 15.46 | N |
| ATOM | 38842 | CA | SER | D | 590 | 5.202 | 86.207 | -4.748 | 1.00 16.21 | C |
| ATOM | 38844 | CB | SER | D | 590 | 6.332 | 85.202 | -4.925 | 1.00 17.84 | C |
| ATOM | 38847 | OG | SER | D | 590 | 7.056 | 85.005 | -3.702 | 1.00 19.81 | O |
| ATOM | 38849 | C | SER | D | 590 | 4.660 | 86.633 | -6.110 | 1.00 16.40 | C |
| ATOM | 38850 | O | SER | D | 590 | 5.394 | 87.182 | -6.958 | 1.00 15.58 | O |
| ATOM | 38852 | N | TYR | D | 591 | 3.386 | 86.375 | -6.358 | 1.00 15.47 | N |
| ATOM | 38853 | CA | TYR | D | 591 | 2.764 | 86.823 | -7.603 | 1.00 15.59 | C |
| ATOM | 38855 | CB | TYR | D | 591 | 1.429 | 86.117 | -7.861 | 1.00 15.76 | C |
| ATOM | 38858 | CG | TYR | D | 591 | 1.427 | 84.659 | -8.280 | 1.00 15.98 | C |
| ATOM | 38859 | CD1 | TYR | D | 591 | 2.324 | 83.724 | -7.727 | 1.00 15.35 | C |
| ATOM | 38861 | CE1 | TYR | D | 591 | 2.289 | 82.395 | -8.124 | 1.00 19.04 | C |
| ATOM | 38863 | CZ | TYR | D | 591 | 1.325 | 81.994 | -9.055 | 1.00 20.64 | C |
| ATOM | 38864 | OH | TYR | D | 591 | 1.246 | 80.699 | -9.474 | 1.00 21.26 | O |
| ATOM | 38866 | CE2 | TYR | D | 591 | 0.440 | 82.883 | -9.603 | 1.00 17.56 | C |
| ATOM | 38868 | CD2 | TYR | D | 591 | 0.492 | 84.208 | -9.231 | 1.00 15.18 | C |
| ATOM | 38870 | C | TYR | D | 591 | 2.423 | 88.303 | -7.594 | 1.00 15.00 | C |
| ATOM | 38871 | O | TYR | D | 591 | 1.988 | 88.864 | -6.583 | 1.00 13.67 | O |
| ATOM | 38873 | N | ASP | D | 592 | 2.471 | 88.888 | -8.792 | 1.00 15.07 | N |
| ATOM | 38874 | CA | ASP | D | 592 | 1.900 | 90.210 | -9.000 | 1.00 13.92 | C |
| ATOM | 38876 | CB | ASP | D | 592 | 2.329 | 90.746 | -10.352 | 1.00 13.75 | C |
| ATOM | 38879 | CG | ASP | D | 592 | 3.754 | 91.266 | -10.364 | 1.00 17.27 | C |
| ATOM | 38880 | OD1 | ASP | D | 592 | 4.486 | 91.151 | -9.342 | 1.00 17.28 | O |
| ATOM | 38881 | OD2 | ASP | D | 592 | 4.129 | 91.808 | -11.448 | 1.00 19.23 | O |
| ATOM | 38882 | C | ASP | D | 592 | 0.362 | 90.193 | -8.832 | 1.00 13.87 | C |
| ATOM | 38883 | O | ASP | D | 592 | -0.290 | 89.177 | -8.968 | 1.00 13.13 | O |
| ATOM | 38885 | N | LEU | D | 593 | -0.204 | 91.336 | -8.484 | 1.00 13.74 | N |
| ATOM | 38886 | CA | LEU | D | 593 | -1.581 | 91.392 | -8.050 | 1.00 14.98 | C |
| ATOM | 38888 | CB | LEU | D | 593 | -1.964 | 92.842 | -7.727 | 1.00 15.17 | C |
| ATOM | 38891 | CG | LEU | D | 593 | -3.392 | 93.025 | -7.219 | 1.00 14.64 | C |
| ATOM | 38893 | CD1 | LEU | D | 593 | -3.539 | 92.462 | -5.852 | 1.00 16.65 | C |
| ATOM | 38897 | CD2 | LEU | D | 593 | -3.755 | 94.497 | -7.241 | 1.00 16.80 | C |
| ATOM | 38901 | C | LEU | D | 593 | -2.578 | 90.798 | -9.026 | 1.00 14.62 | C |
| ATOM | 38902 | O | LEU | D | 593 | -3.433 | 89.990 | -8.641 | 1.00 13.11 | O |
| ATOM | 38904 | N | VAL | D | 594 | -2.497 | 91.213 | -10.289 | 1.00 14.05 | N |
| ATOM | 38905 | CA | VAL | D | 594 | -3.484 | 90.780 | -11.277 | 1.00 15.28 | C |
| ATOM | 38907 | CB | VAL | D | 594 | -3.334 | 91.605 | -12.578 | 1.00 15.58 | C |
| ATOM | 38909 | CG1 | VAL | D | 594 | -4.281 | 91.116 | -13.674 | 1.00 16.84 | C |
| ATOM | 38913 | CG2 | VAL | D | 594 | -3.631 | 93.063 | -12.276 | 1.00 16.75 | C |
| ATOM | 38917 | C | VAL | D | 594 | -3.440 | 89.253 | -11.488 | 1.00 14.86 | C |
| ATOM | 38918 | O | VAL | D | 594 | -4.465 | 88.566 | -11.332 | 1.00 13.30 | O |
| ATOM | 38920 | N | PRO | D | 595 | -2.276 | 88.693 | -11.860 | 1.00 14.32 | N |
| ATOM | 38921 | CA | PRO | D | 595 | -2.262 | 87.213 | -12.012 | 1.00 14.48 | C |
| ATOM | 38923 | CB | PRO | D | 595 | -0.855 | 86.903 | -12.530 | 1.00 14.31 | C |
| ATOM | 38926 | CG | PRO | D | 595 | -0.035 | 88.116 | -12.159 | 1.00 15.35 | C |
| ATOM | 38929 | CD | PRO | D | 595 | -0.975 | 89.290 | -12.209 | 1.00 14.74 | C |
| ATOM | 38932 | C | PRO | D | 595 | -2.570 | 86.459 | -10.725 | 1.00 14.04 | C |
| ATOM | 38933 | O | PRO | D | 595 | -3.118 | 85.356 | -10.771 | 1.00 14.43 | O |
| ATOM | 38934 | N | ARG | D | 596 | -2.227 | 87.035 | -9.569 | 1.00 13.26 | N |
| ATOM | 38935 | CA | ARG | D | 596 | -2.520 | 86.393 | -8.319 | 1.00 13.52 | C |
| ATOM | 38937 | CB | ARG | D | 596 | -2.040 | 87.226 | -7.162 | 1.00 12.07 | C |
| ATOM | 38940 | CG | ARG | D | 596 | -2.165 | 86.486 | -5.835 | 1.00 14.82 | C |
| ATOM | 38943 | CD | ARG | D | 596 | -1.548 | 87.281 | -4.694 | 1.00 17.60 | C |
| ATOM | 38946 | NE | ARG | D | 596 | -1.443 | 86.477 | -3.493 | 1.00 18.06 | N |

| ATOM | 38948 | CZ | ARG | D | 596 | -1.107 | 86.962 | -2.302 | 1.00 | 21.59 | C |
|------|-------|-----|-----|---|-----|--------|--------|--------|------|-------|---|
| ATOM | 38949 | NH1 | ARG | D | 596 | -0.853 | 88.243 | -2.166 | 1.00 | 22.87 | N |
| ATOM | 38952 | NH2 | ARG | D | 596 | -1.012 | 86.156 | -1.258 | 1.00 | 23.35 | N |
| ATOM | 38955 | C | ARG | D | 596 | -4.010 | 86.130 | -8.137 | 1.00 | 12.60 | C |
| ATOM | 38956 | O | ARG | D | 596 | -4.436 | 85.055 | -7.768 | 1.00 | 13.01 | O |
| ATOM | 38958 | N | TRP | D | 597 | -4.823 | 87.131 | -8.410 | 1.00 | 12.28 | N |
| ATOM | 38959 | CA | TRP | D | 597 | -6.245 | 87.003 | -8.150 | 1.00 | 12.13 | C |
| ATOM | 38961 | CB | TRP | D | 597 | -6.938 | 88.366 | -7.966 | 1.00 | 14.06 | C |
| ATOM | 38964 | CG | TRP | D | 597 | -6.699 | 88.869 | -6.587 | 1.00 | 14.29 | C |
| ATOM | 38965 | CD1 | TRP | D | 597 | -5.854 | 89.883 | -6.217 | 1.00 | 16.04 | C |
| ATOM | 38967 | NE1 | TRP | D | 597 | -5.828 | 90.002 | -4.848 | 1.00 | 17.38 | N |
| ATOM | 38969 | CE2 | TRP | D | 597 | -6.641 | 89.032 | -4.313 | 1.00 | 17.57 | C |
| ATOM | 38970 | CD2 | TRP | D | 597 | -7.181 | 88.289 | -5.389 | 1.00 | 15.12 | C |
| ATOM | 38971 | CE3 | TRP | D | 597 | -8.034 | 87.217 | -5.112 | 1.00 | 15.20 | C |
| ATOM | 38973 | CZ3 | TRP | D | 597 | -8.338 | 86.924 | -3.792 | 1.00 | 16.25 | C |
| ATOM | 38975 | CH2 | TRP | D | 597 | -7.795 | 87.680 | -2.753 | 1.00 | 17.03 | C |
| ATOM | 38977 | CZ2 | TRP | D | 597 | -6.933 | 88.728 | -2.991 | 1.00 | 17.72 | C |
| ATOM | 38979 | C | TRP | D | 597 | -6.913 | 86.117 | -9.206 | 1.00 | 11.72 | C |
| ATOM | 38980 | O | TRP | D | 597 | -7.812 | 85.372 | -8.906 | 1.00 | 12.76 | O |
| ATOM | 38982 | N | HIS | D | 598 | -6.470 | 86.181 | -10.452 | 1.00 | 11.66 | N |
| ATOM | 38983 | CA | HIS | D | 598 | -7.018 | 85.257 | -11.424 | 1.00 | 11.25 | C |
| ATOM | 38985 | CB | HIS | D | 598 | -6.583 | 85.625 | -12.836 | 1.00 | 12.73 | C |
| ATOM | 38988 | CG | HIS | D | 598 | -7.348 | 86.796 | -13.365 | 1.00 | 13.95 | C |
| ATOM | 38989 | ND1 | HIS | D | 598 | -8.633 | 86.693 | -13.870 | 1.00 | 13.52 | N |
| ATOM | 38991 | CE1 | HIS | D | 598 | -9.075 | 87.896 | -14.184 | 1.00 | 16.01 | C |
| ATOM | 38993 | NE2 | HIS | D | 598 | -8.124 | 88.776 | -13.912 | 1.00 | 15.63 | N |
| ATOM | 38995 | CD2 | HIS | D | 598 | -7.050 | 88.120 | -13.363 | 1.00 | 14.83 | C |
| ATOM | 38997 | C | HIS | D | 598 | -6.670 | 83.807 | -11.100 | 1.00 | 11.42 | C |
| ATOM | 38998 | O | HIS | D | 598 | -7.477 | 82.904 | -11.351 | 1.00 | 11.31 | O |
| ATOM | 39000 | N | ASP | D | 599 | -5.460 | 83.614 | -10.596 | 1.00 | 11.51 | N |
| ATOM | 39001 | CA | ASP | D | 599 | -5.015 | 82.291 | -10.138 | 1.00 | 11.80 | C |
| ATOM | 39003 | CB | ASP | D | 599 | -3.553 | 82.316 | -9.703 | 1.00 | 11.56 | C |
| ATOM | 39006 | CG | ASP | D | 599 | -3.119 | 81.020 | -9.025 | 1.00 | 15.03 | C |
| ATOM | 39007 | OD1 | ASP | D | 599 | -2.541 | 80.147 | -9.720 | 1.00 | 13.61 | O |
| ATOM | 39008 | OD2 | ASP | D | 599 | -3.348 | 80.856 | -7.816 | 1.00 | 13.25 | O |
| ATOM | 39009 | C | ASP | D | 599 | -5.908 | 81.769 | -9.019 | 1.00 | 11.29 | C |
| ATOM | 39010 | O | ASP | D | 599 | -6.421 | 80.645 | -9.108 | 1.00 | 11.73 | O |
| ATOM | 39012 | N | ALA | D | 600 | -6.119 | 82.596 | -7.994 | 1.00 | 10.43 | N |
| ATOM | 39013 | CA | ALA | D | 600 | -6.925 | 82.175 | -6.825 | 1.00 | 11.51 | C |
| ATOM | 39015 | CB | ALA | D | 600 | -6.956 | 83.223 | -5.793 | 1.00 | 11.58 | C |
| ATOM | 39019 | C | ALA | D | 600 | -8.343 | 81.813 | -7.237 | 1.00 | 11.32 | C |
| ATOM | 39020 | O | ALA | D | 600 | -8.878 | 80.765 | -6.859 | 1.00 | 11.02 | O |
| ATOM | 39022 | N | PHE | D | 601 | -8.984 | 82.666 | -8.038 | 1.00 | 10.93 | N |
| ATOM | 39023 | CA | PHE | D | 601 | -10.339 | 82.356 | -8.474 | 1.00 | 11.22 | C |
| ATOM | 39025 | CB | PHE | D | 601 | -11.077 | 83.622 | -8.845 | 1.00 | 11.51 | C |
| ATOM | 39028 | CG | PHE | D | 601 | -11.595 | 84.338 | -7.635 | 1.00 | 11.65 | C |
| ATOM | 39029 | CD1 | PHE | D | 601 | -12.737 | 83.881 | -7.010 | 1.00 | 11.12 | C |
| ATOM | 39031 | CE1 | PHE | D | 601 | -13.184 | 84.494 | -5.872 | 1.00 | 14.41 | C |
| ATOM | 39033 | CZ | PHE | D | 601 | -12.504 | 85.554 | -5.354 | 1.00 | 13.08 | C |
| ATOM | 39035 | CE2 | PHE | D | 601 | -11.368 | 86.025 | -5.946 | 1.00 | 13.13 | C |
| ATOM | 39037 | CD2 | PHE | D | 601 | -10.886 | 85.388 | -7.085 | 1.00 | 10.50 | C |
| ATOM | 39039 | C | PHE | D | 601 | -10.484 | 81.256 | -9.553 | 1.00 | 10.77 | C |
| ATOM | 39040 | O | PHE | D | 601 | -11.515 | 80.593 | -9.660 | 1.00 | 11.27 | O |
| ATOM | 39042 | N | SER | D | 602 | -9.401 | 80.990 | -10.270 | 1.00 | 10.65 | N |
| ATOM | 39043 | CA | SER | D | 602 | -9.388 | 79.859 | -11.154 | 1.00 | 11.51 | C |
| ATOM | 39045 | CB | SER | D | 602 | -8.150 | 79.911 | -12.021 | 1.00 | 12.64 | C |
| ATOM | 39048 | OG | SER | D | 602 | -8.139 | 78.824 | -12.925 | 1.00 | 15.53 | O |

| | | | | | | | | | |
|---|---|---|---|---|---|---|---|---|---|
| ATOM | 39050 | C | SER | D | 602 | -9.461 | 78.585 | -10.299 | 1.00 11.39 | C |
| ATOM | 39051 | O | SER | D | 602 | -10.207 | 77.680 | -10.604 | 1.00 10.81 | O |
| ATOM | 39053 | N | PHE | D | 603 | -8.683 | 78.553 | -9.218 | 1.00 12.12 | N |
| ATOM | 39054 | CA | PHE | D | 603 | -8.717 | 77.409 | -8.323 | 1.00 12.49 | C |
| ATOM | 39056 | CB | PHE | D | 603 | -7.666 | 77.561 | -7.214 | 1.00 13.18 | C |
| ATOM | 39059 | CG | PHE | D | 603 | -7.208 | 76.252 | -6.556 | 1.00 16.08 | C |
| ATOM | 39060 | CD1 | PHE | D | 603 | -7.903 | 75.056 | -6.627 | 1.00 14.61 | C |
| ATOM | 39062 | CE1 | PHE | D | 603 | -7.430 | 73.874 | -6.023 | 1.00 15.36 | C |
| ATOM | 39064 | CZ | PHE | D | 603 | -6.303 | 73.875 | -5.344 | 1.00 15.70 | C |
| ATOM | 39066 | CE2 | PHE | D | 603 | -5.565 | 75.064 | -5.269 | 1.00 19.57 | C |
| ATOM | 39068 | CD2 | PHE | D | 603 | -6.038 | 76.242 | -5.865 | 1.00 17.93 | C |
| ATOM | 39070 | C | PHE | D | 603 | -10.120 | 77.333 | -7.708 | 1.00 11.99 | C |
| ATOM | 39071 | O | PHE | D | 603 | -10.737 | 76.269 | -7.666 | 1.00 13.13 | O |
| ATOM | 39073 | N | ALA | D | 604 | -10.653 | 78.461 | -7.250 | 1.00 11.47 | N |
| ATOM | 39074 | CA | ALA | D | 604 | -11.995 | 78.460 | -6.659 | 1.00 10.83 | C |
| ATOM | 39076 | CB | ALA | D | 604 | -12.342 | 79.859 | -6.117 | 1.00 10.85 | C |
| ATOM | 39080 | C | ALA | D | 604 | -13.084 | 77.995 | -7.647 | 1.00 10.39 | C |
| ATOM | 39081 | O | ALA | D | 604 | -14.070 | 77.374 | -7.258 | 1.00 12.49 | O |
| ATOM | 39083 | N | ALA | D | 605 | -12.910 | 78.298 | -8.935 | 1.00 9.67 | N |
| ATOM | 39084 | CA | ALA | D | 605 | -13.864 | 77.825 | -9.956 | 1.00 9.99 | C |
| ATOM | 39086 | CB | ALA | D | 605 | -13.467 | 78.343 | -11.348 | 1.00 10.93 | C |
| ATOM | 39090 | C | ALA | D | 605 | -13.950 | 76.291 | -9.969 | 1.00 8.12 | C |
| ATOM | 39091 | O | ALA | D | 605 | -14.976 | 75.713 | -10.270 | 1.00 9.63 | O |
| ATOM | 39093 | N | GLY | D | 606 | -12.816 | 75.633 | -9.682 | 1.00 7.81 | N |
| ATOM | 39094 | CA | GLY | D | 606 | -12.810 | 74.162 | -9.530 | 1.00 7.98 | C |
| ATOM | 39097 | C | GLY | D | 606 | -13.721 | 73.712 | -8.383 | 1.00 8.13 | C |
| ATOM | 39098 | O | GLY | D | 606 | -14.438 | 72.737 | -8.462 | 1.00 10.73 | O |
| ATOM | 39100 | N | THR | D | 607 | -13.638 | 74.441 | -7.271 | 1.00 9.66 | N |
| ATOM | 39101 | CA | THR | D | 607 | -14.535 | 74.185 | -6.152 | 1.00 9.90 | C |
| ATOM | 39103 | CB | THR | D | 607 | -14.115 | 75.061 | -4.949 | 1.00 10.00 | C |
| ATOM | 39105 | OG1 | THR | D | 607 | -12.749 | 74.772 | -4.599 | 1.00 12.65 | O |
| ATOM | 39107 | CG2 | THR | D | 607 | -15.077 | 74.863 | -3.748 | 1.00 11.26 | C |
| ATOM | 39111 | C | THR | D | 607 | -15.990 | 74.400 | -6.530 | 1.00 10.32 | C |
| ATOM | 39112 | O | THR | D | 607 | -16.871 | 73.632 | -6.143 | 1.00 9.83 | O |
| ATOM | 39114 | N | VAL | D | 608 | -16.286 | 75.440 | -7.315 | 1.00 10.23 | N |
| ATOM | 39115 | CA | VAL | D | 608 | -17.658 | 75.679 | -7.743 | 1.00 9.56 | C |
| ATOM | 39117 | CB | VAL | D | 608 | -17.762 | 77.018 | -8.555 | 1.00 9.47 | C |
| ATOM | 39119 | CG1 | VAL | D | 608 | -19.140 | 77.163 | -9.238 | 1.00 10.52 | C |
| ATOM | 39123 | CG2 | VAL | D | 608 | -17.337 | 78.281 | -7.684 | 1.00 11.22 | C |
| ATOM | 39127 | C | VAL | D | 608 | -18.132 | 74.476 | -8.574 | 1.00 9.58 | C |
| ATOM | 39128 | O | VAL | D | 608 | -19.248 | 73.953 | -8.409 | 1.00 9.45 | O |
| ATOM | 39130 | N | VAL | D | 609 | -17.287 | 74.011 | -9.494 | 1.00 9.05 | N |
| ATOM | 39131 | CA | VAL | D | 609 | -17.633 | 72.838 | -10.298 | 1.00 9.35 | C |
| ATOM | 39133 | CB | VAL | D | 609 | -16.441 | 72.384 | -11.207 | 1.00 10.18 | C |
| ATOM | 39135 | CG1 | VAL | D | 609 | -16.685 | 71.018 | -11.810 | 1.00 9.78 | C |
| ATOM | 39139 | CG2 | VAL | D | 609 | -16.225 | 73.417 | -12.290 | 1.00 11.71 | C |
| ATOM | 39143 | C | VAL | D | 609 | -18.072 | 71.664 | -9.437 | 1.00 9.19 | C |
| ATOM | 39144 | O | VAL | D | 609 | -19.046 | 71.005 | -9.780 | 1.00 10.43 | O |
| ATOM | 39146 | N | GLU | D | 610 | -17.343 | 71.389 | -8.353 | 1.00 9.75 | N |
| ATOM | 39147 | CA | GLU | D | 610 | -17.677 | 70.262 | -7.498 | 1.00 11.27 | C |
| ATOM | 39149 | CB | GLU | D | 610 | -16.540 | 69.937 | -6.544 | 1.00 11.35 | C |
| ATOM | 39152 | CG | GLU | D | 610 | -16.863 | 68.818 | -5.559 | 1.00 14.68 | C |
| ATOM | 39155 | CD | GLU | D | 610 | -15.673 | 68.421 | -4.690 | 1.00 18.07 | C |
| ATOM | 39156 | OE1 | GLU | D | 610 | -14.519 | 68.902 | -4.892 | 1.00 21.45 | O |
| ATOM | 39157 | OE2 | GLU | D | 610 | -15.902 | 67.620 | -3.761 | 1.00 26.62 | O |
| ATOM | 39158 | C | GLU | D | 610 | -18.969 | 70.550 | -6.700 | 1.00 10.32 | C |
| ATOM | 39159 | O | GLU | D | 610 | -19.940 | 69.796 | -6.732 | 1.00 10.74 | O |

```
ATOM  39161  N    VAL D 611     -18.975  71.679  -6.009  1.00 11.13      N
ATOM  39162  CA   VAL D 611     -20.081  71.941  -5.072  1.00 11.29      C
ATOM  39164  CB   VAL D 611     -19.770  73.134  -4.151  1.00 11.77      C
ATOM  39166  CG1  VAL D 611     -20.981  73.479  -3.315  1.00 12.55      C
ATOM  39170  CG2  VAL D 611     -18.542  72.864  -3.243  1.00 11.64      C
ATOM  39174  C    VAL D 611     -21.402  72.153  -5.815  1.00 11.37      C
ATOM  39175  O    VAL D 611     -22.462  71.721  -5.347  1.00  9.53      O
ATOM  39177  N    LEU D 612     -21.331  72.786  -6.995  1.00 10.06      N
ATOM  39178  CA   LEU D 612     -22.518  73.086  -7.799  1.00  9.90      C
ATOM  39180  CB   LEU D 612     -22.470  74.542  -8.265  1.00  9.55      C
ATOM  39183  CG   LEU D 612     -22.406  75.616  -7.189  1.00 10.62      C
ATOM  39185  CD1  LEU D 612     -22.695  77.002  -7.700  1.00 12.11      C
ATOM  39189  CD2  LEU D 612     -23.384  75.274  -6.073  1.00 11.33      C
ATOM  39193  C    LEU D 612     -22.667  72.143  -9.006  1.00  9.99      C
ATOM  39194  O    LEU D 612     -23.334  72.464  -9.998  1.00 10.49      O
ATOM  39196  N    SER D 613     -22.105  70.944  -8.880  1.00 10.43      N
ATOM  39197  CA   SER D 613     -22.163  69.970  -9.959  1.00 10.59      C
ATOM  39199  CB   SER D 613     -21.369  68.706  -9.581  1.00 11.09      C
ATOM  39202  OG   SER D 613     -21.961  68.033  -8.481  1.00 14.97      O
ATOM  39204  C    SER D 613     -23.580  69.596 -10.364  1.00 11.59      C
ATOM  39205  O    SER D 613     -23.809  69.203 -11.509  1.00 12.04      O
ATOM  39207  N    SER D 614     -24.545  69.707  -9.440  1.00 11.37      N
ATOM  39208  CA   SER D 614     -25.932  69.377  -9.724  1.00 11.84      C
ATOM  39210  CB   SER D 614     -26.649  69.022  -8.427  1.00 11.98      C
ATOM  39213  OG   SER D 614     -26.659  70.126  -7.515  1.00 14.82      O
ATOM  39215  C    SER D 614     -26.718  70.472 -10.446  1.00 11.09      C
ATOM  39216  O    SER D 614     -27.821  70.240 -10.918  1.00 13.50      O
ATOM  39218  N    THR D 615     -26.141  71.659 -10.555  1.00 10.99      N
ATOM  39219  CA   THR D 615     -26.869  72.820 -11.061  1.00 11.57      C
ATOM  39221  CB   THR D 615     -26.387  74.155 -10.432  1.00 11.58      C
ATOM  39223  OG1  THR D 615     -25.120  74.535 -10.975  1.00 11.53      O
ATOM  39225  CG2  THR D 615     -26.249  74.027  -8.923  1.00 11.77      C
ATOM  39229  C    THR D 615     -26.799  72.937 -12.589  1.00 11.70      C
ATOM  39230  O    THR D 615     -25.981  72.285 -13.248  1.00 12.40      O
ATOM  39232  N    SER D 616     -27.579  73.883 -13.092  1.00 10.99      N
ATOM  39233  CA   SER D 616     -27.729  74.144 -14.523  1.00 11.57      C
ATOM  39235  CB   SER D 616     -29.131  74.719 -14.750  1.00 12.64      C
ATOM  39238  OG   SER D 616     -29.319  75.809 -13.847  1.00 16.83      O
ATOM  39240  C    SER D 616     -26.727  75.153 -15.075  1.00 11.07      C
ATOM  39241  O    SER D 616     -26.839  75.554 -16.252  1.00 10.59      O
ATOM  39243  N    LEU D 617     -25.788  75.586 -14.240  1.00 11.28      N
ATOM  39244  CA   LEU D 617     -24.883  76.689 -14.604  1.00 10.81      C
ATOM  39246  CB   LEU D 617     -23.944  77.048 -13.450  1.00 11.65      C
ATOM  39249  CG   LEU D 617     -24.664  77.773 -12.312  1.00 10.62      C
ATOM  39251  CD1  LEU D 617     -23.847  77.717 -11.078  1.00 11.94      C
ATOM  39255  CD2  LEU D 617     -24.990  79.223 -12.693  1.00 12.32      C
ATOM  39259  C    LEU D 617     -24.045  76.326 -15.819  1.00 11.88      C
ATOM  39260  O    LEU D 617     -23.541  75.217 -15.895  1.00 12.15      O
ATOM  39262  N    SER D 618     -23.936  77.245 -16.774  1.00 11.18      N
ATOM  39263  CA   SER D 618     -22.969  77.064 -17.872  1.00 10.10      C
ATOM  39265  CB   SER D 618     -23.332  78.008 -19.020  1.00 10.56      C
ATOM  39268  OG   SER D 618     -23.020  79.362 -18.642  1.00  9.68      O
ATOM  39270  C    SER D 618     -21.515  77.312 -17.414  1.00  9.90      C
ATOM  39271  O    SER D 618     -21.231  77.991 -16.396  1.00  8.77      O
ATOM  39273  N    LEU D 619     -20.561  76.811 -18.199  1.00  9.36      N
ATOM  39274  CA   LEU D 619     -19.162  77.120 -17.940  1.00  9.29      C
ATOM  39276  CB   LEU D 619     -18.188  76.293 -18.815  1.00  9.09      C
```

```
ATOM  39279  CG   LEU D 619    -18.265  74.747 -18.658  1.00 11.52           C
ATOM  39281  CD1  LEU D 619    -17.079  74.080 -19.349  1.00 10.65           C
ATOM  39285  CD2  LEU D 619    -18.257  74.347 -17.174  1.00 13.69           C
ATOM  39289  C    LEU D 619    -18.915  78.632 -18.106  1.00  8.28           C
ATOM  39290  O    LEU D 619    -18.108  79.216 -17.359  1.00  9.98           O
ATOM  39292  N    ALA D 620    -19.630  79.258 -19.055  1.00  9.76           N
ATOM  39293  CA   ALA D 620    -19.495  80.699 -19.277  1.00  9.04           C
ATOM  39295  CB   ALA D 620    -20.366  81.157 -20.399  1.00  9.03           C
ATOM  39299  C    ALA D 620    -19.883  81.446 -17.995  1.00  8.24           C
ATOM  39300  O    ALA D 620    -19.188  82.371 -17.622  1.00  9.96           O
ATOM  39302  N    ALA D 621    -20.985  81.027 -17.364  1.00  8.99           N
ATOM  39303  CA   ALA D 621    -21.462  81.651 -16.100  1.00  9.47           C
ATOM  39305  CB   ALA D 621    -22.808  81.030 -15.670  1.00  9.48           C
ATOM  39309  C    ALA D 621    -20.434  81.516 -15.004  1.00  9.85           C
ATOM  39310  O    ALA D 621    -20.152  82.480 -14.273  1.00 10.51           O
ATOM  39312  N    VAL D 622    -19.864  80.323 -14.831  1.00  9.52           N
ATOM  39313  CA   VAL D 622    -18.839  80.140 -13.797  1.00  8.89           C
ATOM  39315  CB   VAL D 622    -18.480  78.650 -13.528  1.00  8.85           C
ATOM  39317  CG1  VAL D 622    -17.491  78.543 -12.480  1.00  9.37           C
ATOM  39321  CG2  VAL D 622    -19.735  77.859 -13.187  1.00  9.14           C
ATOM  39325  C    VAL D 622    -17.575  80.938 -14.130  1.00  9.53           C
ATOM  39326  O    VAL D 622    -17.003  81.597 -13.253  1.00  9.92           O
ATOM  39328  N    ASN D 623    -17.135  80.898 -15.390  1.00  9.38           N
ATOM  39329  CA   ASN D 623    -16.007  81.750 -15.787  1.00 10.69           C
ATOM  39331  CB   ASN D 623    -15.635  81.509 -17.266  1.00 10.59           C
ATOM  39334  CG   ASN D 623    -14.274  82.081 -17.610  1.00 12.79           C
ATOM  39335  OD1  ASN D 623    -13.292  81.763 -16.986  1.00 14.12           O
ATOM  39336  ND2  ASN D 623    -14.231  82.928 -18.617  1.00 17.20           N
ATOM  39339  C    ASN D 623    -16.267  83.238 -15.560  1.00 10.72           C
ATOM  39340  O    ASN D 623    -15.377  83.937 -15.128  1.00 10.32           O
ATOM  39342  N    ALA D 624    -17.484  83.693 -15.832  1.00 10.03           N
ATOM  39343  CA   ALA D 624    -17.839  85.108 -15.659  1.00 11.41           C
ATOM  39345  CB   ALA D 624    -19.178  85.388 -16.177  1.00 11.96           C
ATOM  39349  C    ALA D 624    -17.753  85.493 -14.196  1.00 11.55           C
ATOM  39350  O    ALA D 624    -17.275  86.564 -13.863  1.00 12.27           O
ATOM  39352  N    TRP D 625    -18.200  84.611 -13.315  1.00 10.72           N
ATOM  39353  CA   TRP D 625    -18.054  84.852 -11.864  1.00 11.57           C
ATOM  39355  CB   TRP D 625    -18.727  83.729 -11.089  1.00 11.65           C
ATOM  39358  CG   TRP D 625    -18.376  83.690  -9.643  1.00 10.91           C
ATOM  39359  CD1  TRP D 625    -18.957  84.440  -8.633  1.00 11.91           C
ATOM  39361  NE1  TRP D 625    -18.386  84.119  -7.426  1.00 12.42           N
ATOM  39363  CE2  TRP D 625    -17.407  83.175  -7.615  1.00 11.34           C
ATOM  39364  CD2  TRP D 625    -17.357  82.885  -9.007  1.00 10.22           C
ATOM  39365  CE3  TRP D 625    -16.429  81.936  -9.462  1.00 10.54           C
ATOM  39367  CZ3  TRP D 625    -15.583  81.327  -8.529  1.00 11.15           C
ATOM  39369  CH2  TRP D 625    -15.660  81.631  -7.174  1.00 11.76           C
ATOM  39371  CZ2  TRP D 625    -16.575  82.561  -6.696  1.00 11.79           C
ATOM  39373  C    TRP D 625    -16.583  84.953 -11.506  1.00 11.53           C
ATOM  39374  O    TRP D 625    -16.145  85.847 -10.777  1.00 11.63           O
ATOM  39376  N    LYS D 626    -15.807  84.003 -12.002  1.00 10.67           N
ATOM  39377  CA   LYS D 626    -14.363  83.952 -11.714  1.00 11.40           C
ATOM  39379  CB   LYS D 626    -13.746  82.737 -12.449  1.00 11.02           C
ATOM  39382  CG   LYS D 626    -12.273  82.594 -12.409  1.00 12.90           C
ATOM  39385  CD   LYS D 626    -11.557  83.406 -13.504  1.00 15.11           C
ATOM  39388  CE   LYS D 626    -10.038  83.139 -13.592  1.00 15.90           C
ATOM  39391  NZ   LYS D 626     -9.422  83.835 -14.805  1.00 12.21           N
ATOM  39395  C    LYS D 626    -13.689  85.284 -12.113  1.00 11.49           C
```

```
ATOM  39396  O    LYS D 626     -12.934  85.869 -11.353  1.00 12.18           O
ATOM  39398  N    VAL D 627     -14.026  85.780 -13.304  1.00 12.12           N
ATOM  39399  CA   VAL D 627     -13.454  87.027 -13.777  1.00 13.01           C
ATOM  39401  CB   VAL D 627     -13.750  87.249 -15.259  1.00 13.53           C
ATOM  39403  CG1  VAL D 627     -13.407  88.646 -15.663  1.00 15.32           C
ATOM  39407  CG2  VAL D 627     -12.949  86.227 -16.061  1.00 14.54           C
ATOM  39411  C    VAL D 627     -13.918  88.212 -12.915  1.00 12.72           C
ATOM  39412  O    VAL D 627     -13.104  89.027 -12.485  1.00 12.59           O
ATOM  39414  N    ALA D 628     -15.211  88.272 -12.670  1.00 12.76           N
ATOM  39415  CA   ALA D 628     -15.777  89.344 -11.857  1.00 13.29           C
ATOM  39417  CB   ALA D 628     -17.263  89.173 -11.752  1.00 13.36           C
ATOM  39421  C    ALA D 628     -15.156  89.352 -10.456  1.00 13.34           C
ATOM  39422  O    ALA D 628     -14.798  90.423  -9.878  1.00 13.71           O
ATOM  39424  N    ALA D 629     -15.031  88.168  -9.864  1.00 12.69           N
ATOM  39425  CA   ALA D 629     -14.542  88.087  -8.497  1.00 13.31           C
ATOM  39427  CB   ALA D 629     -14.774  86.730  -7.937  1.00 13.75           C
ATOM  39431  C    ALA D 629     -13.050  88.470  -8.394  1.00 13.06           C
ATOM  39432  O    ALA D 629     -12.611  89.177  -7.442  1.00 13.19           O
ATOM  39434  N    ALA D 630     -12.244  88.023  -9.369  1.00 12.45           N
ATOM  39435  CA   ALA D 630     -10.862  88.452  -9.443  1.00 13.68           C
ATOM  39437  CB   ALA D 630     -10.139  87.709 -10.563  1.00 13.24           C
ATOM  39441  C    ALA D 630     -10.739  89.973  -9.635  1.00 13.72           C
ATOM  39442  O    ALA D 630      -9.952  90.595  -8.950  1.00 14.31           O
ATOM  39444  N    GLU D 631     -11.515  90.566 -10.533  1.00 14.70           N
ATOM  39445  CA   GLU D 631     -11.476  92.022 -10.741  1.00 16.52           C
ATOM  39447  CB   GLU D 631     -12.356  92.425 -11.920  1.00 16.25           C
ATOM  39450  CG   GLU D 631     -11.847  91.907 -13.257  1.00 18.96           C
ATOM  39453  CD   GLU D 631     -12.828  92.156 -14.377  1.00 21.85           C
ATOM  39454  OE1  GLU D 631     -14.025  92.392 -14.086  1.00 28.98           O
ATOM  39455  OE2  GLU D 631     -12.407  92.083 -15.551  1.00 24.89           O
ATOM  39456  C    GLU D 631     -11.912  92.771  -9.452  1.00 15.85           C
ATOM  39457  O    GLU D 631     -11.275  93.765  -9.072  1.00 16.01           O
ATOM  39459  N    SER D 632     -12.933  92.259  -8.764  1.00 15.91           N
ATOM  39460  CA   SER D 632     -13.360  92.803  -7.432  1.00 16.16           C
ATOM  39462  CB   SER D 632     -14.556  92.008  -6.882  1.00 16.18           C
ATOM  39465  OG   SER D 632     -14.882  92.325  -5.529  1.00 18.58           O
ATOM  39467  C    SER D 632     -12.224  92.830  -6.411  1.00 16.00           C
ATOM  39468  O    SER D 632     -11.998  93.833  -5.701  1.00 15.87           O
ATOM  39470  N    ALA D 633     -11.494  91.719  -6.334  1.00 13.97           N
ATOM  39471  CA   ALA D 633     -10.414  91.564  -5.374  1.00 13.86           C
ATOM  39473  CB   ALA D 633      -9.996  90.113  -5.284  1.00 14.09           C
ATOM  39477  C    ALA D 633      -9.241  92.464  -5.726  1.00 14.00           C
ATOM  39478  O    ALA D 633      -8.611  93.074  -4.837  1.00 13.70           O
ATOM  39480  N    ILE D 634      -8.956  92.555  -7.017  1.00 14.55           N
ATOM  39481  CA   ILE D 634      -7.890  93.440  -7.495  1.00 13.74           C
ATOM  39483  CB   ILE D 634      -7.664  93.268  -9.000  1.00 14.51           C
ATOM  39485  CG1  ILE D 634      -7.026  91.914  -9.289  1.00 14.81           C
ATOM  39488  CD1  ILE D 634      -7.296  91.368 -10.697  1.00 14.39           C
ATOM  39492  CG2  ILE D 634      -6.807  94.339  -9.533  1.00 14.44           C
ATOM  39496  C    ILE D 634      -8.219  94.898  -7.119  1.00 14.93           C
ATOM  39497  O    ILE D 634      -7.406  95.610  -6.525  1.00 14.38           O
ATOM  39499  N    SER D 635      -9.433  95.334  -7.465  1.00 15.04           N
ATOM  39500  CA   SER D 635      -9.883  96.692  -7.100  1.00 16.63           C
ATOM  39502  CB   SER D 635     -11.253  96.943  -7.694  1.00 16.82           C
ATOM  39505  OG   SER D 635     -11.068  97.101  -9.104  1.00 22.02           O
ATOM  39507  C    SER D 635      -9.909  96.947  -5.582  1.00 16.29           C
ATOM  39508  O    SER D 635      -9.502  98.023  -5.109  1.00 17.82           O
```

```
ATOM  39510 N   LEU D 636     -10.395  95.982  -4.807  1.00 15.17           N
ATOM  39511 CA  LEU D 636     -10.454  96.157  -3.377  1.00 15.84           C
ATOM  39513 CB  LEU D 636     -11.217  95.021  -2.748  1.00 16.21           C
ATOM  39516 CG  LEU D 636     -11.371  95.085  -1.248  1.00 19.63           C
ATOM  39518 CD1 LEU D 636     -12.003  96.400  -0.822  1.00 22.86           C
ATOM  39522 CD2 LEU D 636     -12.202  93.894  -0.807  1.00 19.55           C
ATOM  39526 C   LEU D 636      -9.033  96.236  -2.780  1.00 15.25           C
ATOM  39527 O   LEU D 636      -8.747  97.058  -1.868  1.00 14.41           O
ATOM  39529 N   THR D 637      -8.124  95.410  -3.285  1.00 13.45           N
ATOM  39530 CA  THR D 637      -6.745  95.498  -2.831  1.00 13.17           C
ATOM  39532 CB  THR D 637      -5.836  94.428  -3.512  1.00 12.83           C
ATOM  39534 OG1 THR D 637      -6.275  93.116  -3.141  1.00 12.48           O
ATOM  39536 CG2 THR D 637      -4.434  94.591  -3.075  1.00 15.42           C
ATOM  39540 C   THR D 637      -6.163  96.892  -3.094  1.00 13.31           C
ATOM  39541 O   THR D 637      -5.556  97.500  -2.202  1.00 13.44           O
ATOM  39543 N   ARG D 638      -6.381  97.420  -4.300  1.00 14.82           N
ATOM  39544 CA  ARG D 638      -5.881  98.763  -4.647  1.00 15.62           C
ATOM  39546 CB  ARG D 638      -6.184  99.086  -6.092  1.00 16.56           C
ATOM  39549 CG  ARG D 638      -5.254  98.382  -6.998  1.00 17.46           C
ATOM  39552 CD  ARG D 638      -5.699  98.493  -8.428  1.00 20.91           C
ATOM  39555 NE  ARG D 638      -4.782  97.751  -9.297  1.00 19.84           N
ATOM  39557 CZ  ARG D 638      -5.116  97.277 -10.484  1.00 18.29           C
ATOM  39558 NH1 ARG D 638      -6.339  97.478 -10.958  1.00 17.99           N
ATOM  39561 NH2 ARG D 638      -4.218  96.606 -11.188  1.00 20.12           N
ATOM  39564 C   ARG D 638      -6.471  99.828  -3.731  1.00 15.66           C
ATOM  39565 O   ARG D 638      -5.770 100.749  -3.315  1.00 16.48           O
ATOM  39567 N   GLN D 639      -7.747  99.670  -3.403  1.00 15.76           N
ATOM  39568 CA  GLN D 639      -8.481 100.589  -2.494  1.00 15.76           C
ATOM  39570 CB  GLN D 639      -9.946 100.178  -2.410  1.00 16.05           C
ATOM  39573 CG  GLN D 639     -10.707 100.945  -1.310  1.00 16.73           C
ATOM  39576 CD  GLN D 639     -11.984 100.261  -0.860  1.00 17.83           C
ATOM  39577 OE1 GLN D 639     -12.155 100.067   0.342  1.00 22.89           O
ATOM  39578 NE2 GLN D 639     -12.948  99.963  -1.825  1.00 22.28           N
ATOM  39581 C   GLN D 639      -7.896 100.596  -1.097  1.00 15.43           C
ATOM  39582 O   GLN D 639      -7.580 101.657  -0.536  1.00 15.12           O
ATOM  39584 N   VAL D 640      -7.706  99.402  -0.540  1.00 15.00           N
ATOM  39585 CA  VAL D 640      -7.248  99.284   0.832  1.00 14.72           C
ATOM  39587 CB  VAL D 640      -7.349  97.853   1.334  1.00 15.84           C
ATOM  39589 CG1 VAL D 640      -6.692  97.709   2.641  1.00 18.87           C
ATOM  39593 CG2 VAL D 640      -8.837  97.439   1.448  1.00 17.76           C
ATOM  39597 C   VAL D 640      -5.837  99.856   0.924  1.00 14.79           C
ATOM  39598 O   VAL D 640      -5.480 100.488   1.898  1.00 14.61           O
ATOM  39600 N   ARG D 641      -5.026  99.604  -0.087  1.00 14.37           N
ATOM  39601 CA  ARG D 641      -3.685 100.182  -0.134  1.00 15.83           C
ATOM  39603 CB  ARG D 641      -2.929  99.652  -1.347  1.00 16.26           C
ATOM  39606 CG  ARG D 641      -2.493  98.229  -1.186  1.00 16.77           C
ATOM  39609 CD  ARG D 641      -1.901  97.786  -2.511  1.00 17.15           C
ATOM  39612 NE  ARG D 641      -1.315  96.467  -2.457  1.00 16.84           N
ATOM  39614 CZ  ARG D 641      -0.932  95.789  -3.547  1.00 17.98           C
ATOM  39615 NH1 ARG D 641      -1.107  96.280  -4.745  1.00 17.39           N
ATOM  39618 NH2 ARG D 641      -0.376  94.612  -3.404  1.00 17.76           N
ATOM  39621 C   ARG D 641      -3.747 101.721  -0.159  1.00 16.08           C
ATOM  39622 O   ARG D 641      -3.042 102.387   0.590  1.00 14.45           O
ATOM  39624 N   GLU D 642      -4.586 102.272  -1.014  1.00 16.71           N
ATOM  39625 CA  GLU D 642      -4.734 103.714  -1.041  1.00 18.54           C
ATOM  39627 CB  GLU D 642      -5.712 104.106  -2.151  1.00 20.48           C
ATOM  39630 CG  GLU D 642      -5.024 104.050  -3.508  1.00 26.43           C
```

| | | | | | | | | | |
|---|---|---|---|---|---|---|---|---|---|
| ATOM | 39633 | CD | GLU | D | 642 | -3.837 | 105.015 | -3.598 | 1.00 31.54 | C |
| ATOM | 39634 | OE1 | GLU | D | 642 | -4.027 | 106.185 | -3.158 | 1.00 33.93 | O |
| ATOM | 39635 | OE2 | GLU | D | 642 | -2.741 | 104.586 | -4.079 | 1.00 29.79 | O |
| ATOM | 39636 | C | GLU | D | 642 | -5.154 | 104.267 | 0.295 | 1.00 17.39 | C |
| ATOM | 39637 | O | GLU | D | 642 | -4.621 | 105.277 | 0.723 | 1.00 18.01 | O |
| ATOM | 39639 | N | THR | D | 643 | -6.111 | 103.627 | 0.952 | 1.00 15.57 | N |
| ATOM | 39640 | CA | THR | D | 643 | -6.587 | 104.119 | 2.226 | 1.00 15.03 | C |
| ATOM | 39642 | CB | THR | D | 643 | -7.759 | 103.286 | 2.730 | 1.00 15.84 | C |
| ATOM | 39644 | OG1 | THR | D | 643 | -8.879 | 103.491 | 1.868 | 1.00 15.45 | O |
| ATOM | 39646 | CG2 | THR | D | 643 | -8.154 | 103.647 | 4.150 | 1.00 15.10 | C |
| ATOM | 39650 | C | THR | D | 643 | -5.415 | 104.132 | 3.242 | 1.00 14.71 | C |
| ATOM | 39651 | O | THR | D | 643 | -5.305 | 105.049 | 4.028 | 1.00 15.71 | O |
| ATOM | 39653 | N | PHE | D | 644 | -4.568 | 103.109 | 3.195 | 1.00 13.85 | N |
| ATOM | 39654 | CA | PHE | D | 644 | -3.392 | 103.032 | 4.076 | 1.00 14.40 | C |
| ATOM | 39656 | CB | PHE | D | 644 | -2.680 | 101.698 | 3.930 | 1.00 14.44 | C |
| ATOM | 39659 | CG | PHE | D | 644 | -1.416 | 101.596 | 4.753 | 1.00 13.64 | C |
| ATOM | 39660 | CD1 | PHE | D | 644 | -1.463 | 101.126 | 6.062 | 1.00 15.33 | C |
| ATOM | 39662 | CE1 | PHE | D | 644 | -0.311 | 101.021 | 6.805 | 1.00 16.78 | C |
| ATOM | 39664 | CZ | PHE | D | 644 | 0.904 | 101.445 | 6.259 | 1.00 16.47 | C |
| ATOM | 39666 | CE2 | PHE | D | 644 | 0.965 | 101.911 | 4.990 | 1.00 14.09 | C |
| ATOM | 39668 | CD2 | PHE | D | 644 | -0.197 | 101.996 | 4.235 | 1.00 11.93 | C |
| ATOM | 39670 | C | PHE | D | 644 | -2.406 | 104.175 | 3.818 | 1.00 14.31 | C |
| ATOM | 39671 | O | PHE | D | 644 | -1.991 | 104.866 | 4.761 | 1.00 15.96 | O |
| ATOM | 39673 | N | TRP | D | 645 | -2.039 | 104.360 | 2.555 | 1.00 15.12 | N |
| ATOM | 39674 | CA | TRP | D | 645 | -1.017 | 105.332 | 2.181 | 1.00 15.64 | C |
| ATOM | 39676 | CB | TRP | D | 645 | -0.384 | 104.996 | 0.831 | 1.00 15.20 | C |
| ATOM | 39679 | CG | TRP | D | 645 | 0.378 | 103.698 | 0.885 | 1.00 13.67 | C |
| ATOM | 39680 | CD1 | TRP | D | 645 | 0.007 | 102.497 | 0.381 | 1.00 14.98 | C |
| ATOM | 39682 | NE1 | TRP | D | 645 | 0.960 | 101.539 | 0.647 | 1.00 13.77 | N |
| ATOM | 39684 | CE2 | TRP | D | 645 | 1.980 | 102.112 | 1.360 | 1.00 16.10 | C |
| ATOM | 39685 | CD2 | TRP | D | 645 | 1.651 | 103.473 | 1.533 | 1.00 13.35 | C |
| ATOM | 39686 | CE3 | TRP | D | 645 | 2.528 | 104.295 | 2.245 | 1.00 15.91 | C |
| ATOM | 39688 | CZ3 | TRP | D | 645 | 3.728 | 103.730 | 2.722 | 1.00 14.62 | C |
| ATOM | 39690 | CH2 | TRP | D | 645 | 4.020 | 102.376 | 2.554 | 1.00 15.59 | C |
| ATOM | 39692 | CZ2 | TRP | D | 645 | 3.165 | 101.541 | 1.864 | 1.00 15.32 | C |
| ATOM | 39694 | C | TRP | D | 645 | -1.437 | 106.794 | 2.239 | 1.00 17.46 | C |
| ATOM | 39695 | O | TRP | D | 645 | -0.557 | 107.632 | 2.365 | 1.00 21.27 | O |
| ATOM | 39697 | N | SER | D | 646 | -2.732 | 107.072 | 2.261 | 1.00 18.50 | N |
| ATOM | 39698 | CA | SER | D | 646 | -3.274 | 108.427 | 2.191 | 1.00 19.96 | C |
| ATOM | 39700 | CB | SER | D | 646 | -4.519 | 108.414 | 1.288 | 1.00 20.19 | C |
| ATOM | 39703 | OG | SER | D | 646 | -5.571 | 107.746 | 1.952 | 1.00 22.41 | O |
| ATOM | 39705 | C | SER | D | 646 | -3.611 | 108.994 | 3.592 | 1.00 20.37 | C |
| ATOM | 39706 | O | SER | D | 646 | -4.237 | 110.056 | 3.727 | 1.00 21.99 | O |
| ATOM | 39708 | N | ALA | D | 647 | -3.224 | 108.277 | 4.630 | 1.00 19.94 | N |
| ATOM | 39709 | CA | ALA | D | 647 | -3.400 | 108.758 | 5.988 | 1.00 19.60 | C |
| ATOM | 39711 | CB | ALA | D | 647 | -4.405 | 107.937 | 6.730 | 1.00 20.62 | C |
| ATOM | 39715 | C | ALA | D | 647 | -2.077 | 108.670 | 6.678 | 1.00 19.55 | C |
| ATOM | 39716 | O | ALA | D | 647 | -1.212 | 107.880 | 6.301 | 1.00 18.34 | O |
| ATOM | 39718 | N | ALA | D | 648 | -1.945 | 109.470 | 7.721 | 1.00 19.69 | N |
| ATOM | 39719 | CA | ALA | D | 648 | -0.730 | 109.432 | 8.504 | 1.00 19.34 | C |
| ATOM | 39721 | CB | ALA | D | 648 | -0.686 | 110.646 | 9.414 | 1.00 19.88 | C |
| ATOM | 39725 | C | ALA | D | 648 | -0.638 | 108.145 | 9.322 | 1.00 19.22 | C |
| ATOM | 39726 | O | ALA | D | 648 | -1.661 | 107.525 | 9.646 | 1.00 18.87 | O |
| ATOM | 39728 | N | SER | D | 649 | 0.580 | 107.820 | 9.728 | 1.00 17.90 | N |
| ATOM | 39729 | CA | SER | D | 649 | 0.840 | 106.595 | 10.471 | 1.00 17.99 | C |
| ATOM | 39731 | CB | SER | D | 649 | 2.344 | 106.333 | 10.581 | 1.00 18.07 | C |
| ATOM | 39734 | OG | SER | D | 649 | 3.012 | 107.498 | 11.030 | 1.00 20.47 | O |

| | | | | | | | | | |
|---|---|---|---|---|---|---|---|---|---|
| ATOM | 39736 | C | SER | D | 649 | 0.198 | 106.617 | 11.841 | 1.00 17.03 | C |
| ATOM | 39737 | O | SER | D | 649 | -0.019 | 105.582 | 12.439 | 1.00 16.71 | O |
| ATOM | 39739 | N | THR | D | 650 | -0.144 | 107.788 | 12.353 | 1.00 18.47 | N |
| ATOM | 39740 | CA | THR | D | 650 | -0.912 | 107.891 | 13.589 | 1.00 17.61 | C |
| ATOM | 39742 | CB | THR | D | 650 | -0.983 | 109.358 | 14.073 | 1.00 18.28 | C |
| ATOM | 39744 | OG1 | THR | D | 650 | -1.272 | 110.222 | 12.968 | 1.00 17.25 | O |
| ATOM | 39746 | CG2 | THR | D | 650 | 0.328 | 109.775 | 14.720 | 1.00 17.67 | C |
| ATOM | 39750 | C | THR | D | 650 | -2.344 | 107.313 | 13.473 | 1.00 18.47 | C |
| ATOM | 39751 | O | THR | D | 650 | -3.024 | 107.082 | 14.503 | 1.00 18.87 | O |
| ATOM | 39753 | N | SER | D | 651 | -2.790 | 107.134 | 12.230 | 1.00 18.87 | N |
| ATOM | 39754 | CA | SER | D | 651 | -4.059 | 106.453 | 11.894 | 1.00 18.41 | C |
| ATOM | 39756 | CB | SER | D | 651 | -4.908 | 107.365 | 10.980 | 1.00 19.09 | C |
| ATOM | 39759 | OG | SER | D | 651 | -5.283 | 108.538 | 11.689 | 1.00 20.25 | O |
| ATOM | 39761 | C | SER | D | 651 | -3.833 | 105.066 | 11.247 | 1.00 17.68 | C |
| ATOM | 39762 | O | SER | D | 651 | -4.736 | 104.477 | 10.627 | 1.00 16.70 | O |
| ATOM | 39764 | N | SER | D | 652 | -2.629 | 104.511 | 11.391 | 1.00 16.06 | N |
| ATOM | 39765 | CA | SER | D | 652 | -2.337 | 103.256 | 10.752 | 1.00 15.53 | C |
| ATOM | 39767 | CB | SER | D | 652 | -0.906 | 102.799 | 11.063 | 1.00 16.54 | C |
| ATOM | 39770 | OG | SER | D | 652 | -0.783 | 101.454 | 10.682 | 1.00 18.16 | O |
| ATOM | 39772 | C | SER | D | 652 | -3.323 | 102.198 | 11.235 | 1.00 15.27 | C |
| ATOM | 39773 | O | SER | D | 652 | -3.599 | 102.114 | 12.441 | 1.00 14.72 | O |
| ATOM | 39775 | N | PRO | D | 653 | -3.815 | 101.347 | 10.314 | 1.00 15.40 | N |
| ATOM | 39776 | CA | PRO | D | 653 | -4.686 | 100.273 | 10.768 | 1.00 15.06 | C |
| ATOM | 39778 | CB | PRO | D | 653 | -5.228 | 99.676 | 9.466 | 1.00 15.78 | C |
| ATOM | 39781 | CG | PRO | D | 653 | -4.184 | 99.936 | 8.451 | 1.00 16.52 | C |
| ATOM | 39784 | CD | PRO | D | 653 | -3.611 | 101.305 | 8.856 | 1.00 16.04 | C |
| ATOM | 39787 | C | PRO | D | 653 | -3.953 | 99.251 | 11.646 | 1.00 15.06 | C |
| ATOM | 39788 | O | PRO | D | 653 | -4.588 | 98.469 | 12.346 | 1.00 14.98 | O |
| ATOM | 39789 | N | ALA | D | 654 | -2.619 | 99.315 | 11.669 | 1.00 13.32 | N |
| ATOM | 39790 | CA | ALA | D | 654 | -1.844 | 98.453 | 12.589 | 1.00 14.67 | C |
| ATOM | 39792 | CB | ALA | D | 654 | -0.355 | 98.740 | 12.457 | 1.00 14.20 | C |
| ATOM | 39796 | C | ALA | D | 654 | -2.305 | 98.691 | 14.053 | 1.00 14.58 | C |
| ATOM | 39797 | O | ALA | D | 654 | -2.308 | 97.746 | 14.884 | 1.00 15.44 | O |
| ATOM | 39799 | N | LEU | D | 655 | -2.679 | 99.936 | 14.349 | 1.00 14.43 | N |
| ATOM | 39800 | CA | LEU | D | 655 | -3.073 | 100.323 | 15.702 | 1.00 14.70 | C |
| ATOM | 39802 | CB | LEU | D | 655 | -3.210 | 101.855 | 15.772 | 1.00 15.14 | C |
| ATOM | 39805 | CG | LEU | D | 655 | -1.939 | 102.643 | 15.428 | 1.00 15.60 | C |
| ATOM | 39807 | CD1 | LEU | D | 655 | -2.289 | 104.165 | 15.490 | 1.00 19.51 | C |
| ATOM | 39811 | CD2 | LEU | D | 655 | -0.814 | 102.331 | 16.352 | 1.00 18.25 | C |
| ATOM | 39815 | C | LEU | D | 655 | -4.359 | 99.640 | 16.147 | 1.00 15.36 | C |
| ATOM | 39816 | O | LEU | D | 655 | -4.620 | 99.550 | 17.356 | 1.00 16.56 | O |
| ATOM | 39818 | N | SER | D | 656 | -5.161 | 99.184 | 15.192 | 1.00 14.11 | N |
| ATOM | 39819 | CA | SER | D | 656 | -6.372 | 98.420 | 15.479 | 1.00 15.95 | C |
| ATOM | 39821 | CB | SER | D | 656 | -7.245 | 98.300 | 14.243 | 1.00 15.25 | C |
| ATOM | 39824 | OG | SER | D | 656 | -7.720 | 99.536 | 13.797 | 1.00 19.98 | O |
| ATOM | 39826 | C | SER | D | 656 | -6.115 | 96.987 | 15.950 | 1.00 15.32 | C |
| ATOM | 39827 | O | SER | D | 656 | -7.015 | 96.345 | 16.541 | 1.00 16.27 | O |
| ATOM | 39829 | N | TYR | D | 657 | -4.927 | 96.463 | 15.669 | 1.00 14.76 | N |
| ATOM | 39830 | CA | TYR | D | 657 | -4.648 | 95.043 | 15.914 | 1.00 15.15 | C |
| ATOM | 39832 | CB | TYR | D | 657 | -4.416 | 94.315 | 14.594 | 1.00 14.93 | C |
| ATOM | 39835 | CG | TYR | D | 657 | -5.516 | 94.533 | 13.595 | 1.00 15.48 | C |
| ATOM | 39836 | CD1 | TYR | D | 657 | -6.774 | 93.975 | 13.791 | 1.00 16.77 | C |
| ATOM | 39838 | CE1 | TYR | D | 657 | -7.812 | 94.187 | 12.876 | 1.00 17.16 | C |
| ATOM | 39840 | CZ | TYR | D | 657 | -7.571 | 94.984 | 11.761 | 1.00 16.94 | C |
| ATOM | 39841 | OH | TYR | D | 657 | -8.590 | 95.205 | 10.850 | 1.00 18.45 | O |
| ATOM | 39843 | CE2 | TYR | D | 657 | -6.348 | 95.584 | 11.574 | 1.00 14.12 | C |
| ATOM | 39845 | CD2 | TYR | D | 657 | -5.312 | 95.337 | 12.488 | 1.00 13.68 | C |

| ATOM | 39847 | C   | TYR | D | 657 | -3.460 | 94.774  | 16.847 | 1.00 | 15.21 | C |
|------|-------|-----|-----|---|-----|--------|---------|--------|------|-------|---|
| ATOM | 39848 | O   | TYR | D | 657 | -3.426 | 93.752  | 17.507 | 1.00 | 15.47 | O |
| ATOM | 39850 | N   | LEU | D | 658 | -2.484 | 95.664  | 16.879 | 1.00 | 14.73 | N |
| ATOM | 39851 | CA  | LEU | D | 658 | -1.340 | 95.497  | 17.795 | 1.00 | 14.68 | C |
| ATOM | 39853 | CB  | LEU | D | 658 | -0.400 | 96.675  | 17.668 | 1.00 | 15.66 | C |
| ATOM | 39856 | CG  | LEU | D | 658 | 0.526  | 96.680  | 16.453 | 1.00 | 17.96 | C |
| ATOM | 39858 | CD1 | LEU | D | 658 | 1.218  | 98.033  | 16.339 | 1.00 | 20.71 | C |
| ATOM | 39862 | CD2 | LEU | D | 658 | 1.503  | 95.531  | 16.518 | 1.00 | 18.93 | C |
| ATOM | 39866 | C   | LEU | D | 658 | -1.800 | 95.427  | 19.238 | 1.00 | 13.66 | C |
| ATOM | 39867 | O   | LEU | D | 658 | -2.683 | 96.160  | 19.663 | 1.00 | 12.99 | O |
| ATOM | 39869 | N   | SER | D | 659 | -1.093 | 94.608  | 20.026 | 1.00 | 14.97 | N |
| ATOM | 39870 | CA  | SER | D | 659 | -1.211 | 94.677  | 21.474 | 1.00 | 14.41 | C |
| ATOM | 39872 | CB  | SER | D | 659 | -0.184 | 93.689  | 22.093 | 1.00 | 15.35 | C |
| ATOM | 39875 | OG  | SER | D | 659 | 0.640  | 94.327  | 23.041 | 1.00 | 18.60 | O |
| ATOM | 39877 | C   | SER | D | 659 | -0.954 | 96.118  | 21.936 | 1.00 | 13.59 | C |
| ATOM | 39878 | O   | SER | D | 659 | -0.134 | 96.825  | 21.338 | 1.00 | 13.78 | O |
| ATOM | 39880 | N   | PRO | D | 660 | -1.568 | 96.540  | 23.039 | 1.00 | 14.29 | N |
| ATOM | 39881 | CA  | PRO | D | 660 | -1.292 | 97.883  | 23.558 | 1.00 | 14.93 | C |
| ATOM | 39883 | CB  | PRO | D | 660 | -2.236 | 98.009  | 24.765 | 1.00 | 16.28 | C |
| ATOM | 39886 | CG  | PRO | D | 660 | -2.541 | 96.607  | 25.158 | 1.00 | 16.09 | C |
| ATOM | 39889 | CD  | PRO | D | 660 | -2.535 | 95.803  | 23.860 | 1.00 | 14.81 | C |
| ATOM | 39892 | C   | PRO | D | 660 | 0.173  | 98.097  | 23.958 | 1.00 | 15.42 | C |
| ATOM | 39893 | O   | PRO | D | 660 | 0.659  | 99.213  | 23.891 | 1.00 | 15.40 | O |
| ATOM | 39894 | N   | ARG | D | 661 | 0.867  | 97.044  | 24.364 | 1.00 | 14.33 | N |
| ATOM | 39895 | CA  | ARG | D | 661 | 2.284  | 97.206  | 24.711 | 1.00 | 14.63 | C |
| ATOM | 39897 | CB  | ARG | D | 661 | 2.748  | 96.129  | 25.705 | 1.00 | 14.55 | C |
| ATOM | 39900 | CG  | ARG | D | 661 | 2.072  | 96.298  | 27.070 | 1.00 | 16.75 | C |
| ATOM | 39903 | CD  | ARG | D | 661 | 2.350  | 95.112  | 27.958 | 1.00 | 18.40 | C |
| ATOM | 39906 | NE  | ARG | D | 661 | 1.675  | 95.203  | 29.257 | 1.00 | 19.55 | N |
| ATOM | 39908 | CZ  | ARG | D | 661 | 2.124  | 95.894  | 30.314 | 1.00 | 22.83 | C |
| ATOM | 39909 | NH1 | ARG | D | 661 | 3.251  | 96.613  | 30.258 | 1.00 | 23.94 | N |
| ATOM | 39912 | NH2 | ARG | D | 661 | 1.410  | 95.893  | 31.446 | 1.00 | 25.87 | N |
| ATOM | 39915 | C   | ARG | D | 661 | 3.200  | 97.252  | 23.497 | 1.00 | 14.44 | C |
| ATOM | 39916 | O   | ARG | D | 661 | 4.155  | 98.040  | 23.483 | 1.00 | 14.65 | O |
| ATOM | 39918 | N   | THR | D | 662 | 2.949  | 96.432  | 22.479 | 1.00 | 15.16 | N |
| ATOM | 39919 | CA  | THR | D | 662 | 3.804  | 96.489  | 21.293 | 1.00 | 14.37 | C |
| ATOM | 39921 | CB  | THR | D | 662 | 3.709  | 95.238  | 20.411 | 1.00 | 15.57 | C |
| ATOM | 39923 | OG1 | THR | D | 662 | 2.356  | 95.040  | 20.035 | 1.00 | 15.86 | O |
| ATOM | 39925 | CG2 | THR | D | 662 | 4.177  | 94.015  | 21.171 | 1.00 | 15.21 | C |
| ATOM | 39929 | C   | THR | D | 662 | 3.541  | 97.760  | 20.483 | 1.00 | 14.77 | C |
| ATOM | 39930 | O   | THR | D | 662 | 4.429  | 98.234  | 19.753 | 1.00 | 13.94 | O |
| ATOM | 39932 | N   | GLN | D | 663 | 2.311  | 98.284  | 20.575 | 1.00 | 14.51 | N |
| ATOM | 39933 | CA  | GLN | D | 663 | 1.949  | 99.558  | 19.974 | 1.00 | 16.25 | C |
| ATOM | 39935 | CB  | GLN | D | 663 | 0.521  | 99.978  | 20.381 | 1.00 | 17.77 | C |
| ATOM | 39938 | CG  | GLN | D | 663 | -0.546 | 99.353  | 19.552 | 1.00 | 22.42 | C |
| ATOM | 39941 | CD  | GLN | D | 663 | -1.905 | 99.982  | 19.788 | 1.00 | 22.24 | C |
| ATOM | 39942 | OE1 | GLN | D | 663 | -2.022 | 101.230 | 19.925 | 1.00 | 26.88 | O |
| ATOM | 39943 | NE2 | GLN | D | 663 | -2.942 | 99.133  | 19.848 | 1.00 | 27.39 | N |
| ATOM | 39946 | C   | GLN | D | 663 | 2.954  | 100.656 | 20.389 | 1.00 | 14.17 | C |
| ATOM | 39947 | O   | GLN | D | 663 | 3.276  | 101.543 | 19.618 | 1.00 | 14.39 | O |
| ATOM | 39949 | N   | ILE | D | 664 | 3.442  | 100.580 | 21.622 | 1.00 | 13.34 | N |
| ATOM | 39950 | CA  | ILE | D | 664 | 4.385  | 101.578 | 22.126 | 1.00 | 12.97 | C |
| ATOM | 39952 | CB  | ILE | D | 664 | 4.754  | 101.241 | 23.604 | 1.00 | 13.52 | C |
| ATOM | 39954 | CG1 | ILE | D | 664 | 3.507  | 101.459 | 24.473 | 1.00 | 14.79 | C |
| ATOM | 39957 | CD1 | ILE | D | 664 | 3.662  | 100.910 | 25.834 | 1.00 | 15.73 | C |
| ATOM | 39961 | CG2 | ILE | D | 664 | 5.942  | 102.042 | 24.077 | 1.00 | 12.53 | C |
| ATOM | 39965 | C   | ILE | D | 664 | 5.651  | 101.627 | 21.252 | 1.00 | 13.91 | C |

| ATOM | 39966 | O   | ILE | D | 664 | 6.184  | 102.703 | 20.900 | 1.00 | 14.05 | O |
|------|-------|-----|-----|---|-----|--------|---------|--------|------|-------|---|
| ATOM | 39968 | N   | LEU | D | 665 | 6.149  | 100.454 | 20.892 | 1.00 | 12.71 | N |
| ATOM | 39969 | CA  | LEU | D | 665 | 7.383  | 100.412 | 20.065 | 1.00 | 14.05 | C |
| ATOM | 39971 | CB  | LEU | D | 665 | 8.071  | 99.069  | 20.140 | 1.00 | 13.32 | C |
| ATOM | 39974 | CG  | LEU | D | 665 | 9.505  | 98.918  | 19.592 | 1.00 | 14.14 | C |
| ATOM | 39976 | CD1 | LEU | D | 665 | 10.411 | 99.980  | 20.076 | 1.00 | 15.56 | C |
| ATOM | 39980 | CD2 | LEU | D | 665 | 10.102 | 97.560  | 19.970 | 1.00 | 16.30 | C |
| ATOM | 39984 | C   | LEU | D | 665 | 7.125  | 100.814 | 18.641 | 1.00 | 13.15 | C |
| ATOM | 39985 | O   | LEU | D | 665 | 7.943  | 101.482 | 18.000 | 1.00 | 14.50 | O |
| ATOM | 39987 | N   | TYR | D | 666 | 5.973  | 100.413 | 18.126 | 1.00 | 13.86 | N |
| ATOM | 39988 | CA  | TYR | D | 666 | 5.549  | 100.804 | 16.783 | 1.00 | 13.85 | C |
| ATOM | 39990 | CB  | TYR | D | 666 | 4.158  | 100.231 | 16.491 | 1.00 | 14.46 | C |
| ATOM | 39993 | CG  | TYR | D | 666 | 3.600  | 100.539 | 15.121 | 1.00 | 14.53 | C |
| ATOM | 39994 | CD1 | TYR | D | 666 | 3.727  | 99.636  | 14.072 | 1.00 | 13.99 | C |
| ATOM | 39996 | CE1 | TYR | D | 666 | 3.194  | 99.913  | 12.811 | 1.00 | 15.18 | C |
| ATOM | 39998 | CZ  | TYR | D | 666 | 2.523  | 101.103 | 12.618 | 1.00 | 13.50 | C |
| ATOM | 39999 | OH  | TYR | D | 666 | 1.976  | 101.438 | 11.380 | 1.00 | 16.43 | O |
| ATOM | 40001 | CE2 | TYR | D | 666 | 2.413  | 102.014 | 13.645 | 1.00 | 16.43 | C |
| ATOM | 40003 | CD2 | TYR | D | 666 | 2.924  | 101.724 | 14.874 | 1.00 | 14.84 | C |
| ATOM | 40005 | C   | TYR | D | 666 | 5.523  | 102.326 | 16.666 | 1.00 | 13.21 | C |
| ATOM | 40006 | O   | TYR | D | 666 | 6.096  | 102.882 | 15.737 | 1.00 | 14.29 | O |
| ATOM | 40008 | N   | ALA | D | 667 | 4.878  | 102.978 | 17.616 | 1.00 | 13.17 | N |
| ATOM | 40009 | CA  | ALA | D | 667 | 4.752  | 104.431 | 17.617 | 1.00 | 13.20 | C |
| ATOM | 40011 | CB  | ALA | D | 667 | 3.751  | 104.881 | 18.738 | 1.00 | 13.73 | C |
| ATOM | 40015 | C   | ALA | D | 667 | 6.116  | 105.077 | 17.791 | 1.00 | 13.62 | C |
| ATOM | 40016 | O   | ALA | D | 667 | 6.435  | 106.067 | 17.136 | 1.00 | 12.90 | O |
| ATOM | 40018 | N   | PHE | D | 668 | 6.961  | 104.498 | 18.640 | 1.00 | 12.81 | N |
| ATOM | 40019 | CA  | PHE | D | 668 | 8.300  | 105.067 | 18.828 | 1.00 | 12.92 | C |
| ATOM | 40021 | CB  | PHE | D | 668 | 9.105  | 104.252 | 19.835 | 1.00 | 12.82 | C |
| ATOM | 40024 | CG  | PHE | D | 668 | 10.535 | 104.713 | 19.966 | 1.00 | 12.67 | C |
| ATOM | 40025 | CD1 | PHE | D | 668 | 10.823 | 105.968 | 20.534 | 1.00 | 14.19 | C |
| ATOM | 40027 | CE1 | PHE | D | 668 | 12.136 | 106.416 | 20.700 | 1.00 | 15.70 | C |
| ATOM | 40029 | CZ  | PHE | D | 668 | 13.160 | 105.655 | 20.281 | 1.00 | 15.98 | C |
| ATOM | 40031 | CE2 | PHE | D | 668 | 12.899 | 104.368 | 19.705 | 1.00 | 15.17 | C |
| ATOM | 40033 | CD2 | PHE | D | 668 | 11.574 | 103.920 | 19.547 | 1.00 | 13.33 | C |
| ATOM | 40035 | C   | PHE | D | 668 | 9.058  | 105.160 | 17.492 | 1.00 | 12.87 | C |
| ATOM | 40036 | O   | PHE | D | 668 | 9.615  | 106.196 | 17.134 | 1.00 | 12.81 | O |
| ATOM | 40038 | N   | VAL | D | 669 | 9.061  | 104.078 | 16.738 | 1.00 | 12.93 | N |
| ATOM | 40039 | CA  | VAL | D | 669 | 9.779  | 104.083 | 15.446 | 1.00 | 12.57 | C |
| ATOM | 40041 | CB  | VAL | D | 669 | 10.065 | 102.655 | 14.949 | 1.00 | 12.17 | C |
| ATOM | 40043 | CG1 | VAL | D | 669 | 10.735 | 102.684 | 13.628 | 1.00 | 12.72 | C |
| ATOM | 40047 | CG2 | VAL | D | 669 | 10.883 | 101.901 | 16.007 | 1.00 | 14.26 | C |
| ATOM | 40051 | C   | VAL | D | 669 | 9.050  | 104.900 | 14.384 | 1.00 | 12.60 | C |
| ATOM | 40052 | O   | VAL | D | 669 | 9.663  | 105.709 | 13.674 | 1.00 | 12.86 | O |
| ATOM | 40054 | N   | ARG | D | 670 | 7.738  | 104.680 | 14.229 | 1.00 | 13.09 | N |
| ATOM | 40055 | CA  | ARG | D | 670 | 6.976  | 105.294 | 13.151 | 1.00 | 12.72 | C |
| ATOM | 40057 | CB  | ARG | D | 670 | 5.615  | 104.613 | 12.990 | 1.00 | 13.21 | C |
| ATOM | 40060 | CG  | ARG | D | 670 | 5.709  | 103.232 | 12.380 | 1.00 | 13.20 | C |
| ATOM | 40063 | CD  | ARG | D | 670 | 5.539  | 103.276 | 10.899 | 1.00 | 13.61 | C |
| ATOM | 40066 | NE  | ARG | D | 670 | 5.497  | 101.953 | 10.210 | 1.00 | 13.61 | N |
| ATOM | 40068 | CZ  | ARG | D | 670 | 6.571  | 101.289 | 9.786  | 1.00 | 13.22 | C |
| ATOM | 40069 | NH1 | ARG | D | 670 | 7.794  | 101.783 | 10.015 | 1.00 | 13.64 | N |
| ATOM | 40072 | NH2 | ARG | D | 670 | 6.451  | 100.126 | 9.135  | 1.00 | 15.52 | N |
| ATOM | 40075 | C   | ARG | D | 670 | 6.831  | 106.790 | 13.366 | 1.00 | 13.71 | C |
| ATOM | 40076 | O   | ARG | D | 670 | 6.871  | 107.550 | 12.418 | 1.00 | 14.55 | O |
| ATOM | 40078 | N   | GLU | D | 671 | 6.613  | 107.210 | 14.610 | 1.00 | 13.55 | N |
| ATOM | 40079 | CA  | GLU | D | 671 | 6.371  | 108.627 | 14.918 | 1.00 | 14.19 | C |

| ATOM | 40081 | CB | GLU | D | 671 | 5.246 | 108.801 | 15.932 | 1.00 | 15.41 | C |
| --- | --- | --- | --- | --- | --- | --- | --- | --- | --- | --- | --- |
| ATOM | 40084 | CG | GLU | D | 671 | 3.963 | 108.068 | 15.582 | 1.00 | 15.29 | C |
| ATOM | 40087 | CD | GLU | D | 671 | 3.505 | 108.274 | 14.164 | 1.00 | 18.02 | C |
| ATOM | 40088 | OE1 | GLU | D | 671 | 3.644 | 109.432 | 13.673 | 1.00 | 16.14 | O |
| ATOM | 40089 | OE2 | GLU | D | 671 | 3.014 | 107.272 | 13.546 | 1.00 | 19.44 | O |
| ATOM | 40090 | C | GLU | D | 671 | 7.648 | 109.323 | 15.424 | 1.00 | 15.49 | C |
| ATOM | 40091 | O | GLU | D | 671 | 8.140 | 110.247 | 14.787 | 1.00 | 16.00 | O |
| ATOM | 40093 | N | GLU | D | 672 | 8.234 | 108.891 | 16.540 | 1.00 | 14.94 | N |
| ATOM | 40094 | CA | GLU | D | 672 | 9.380 | 109.649 | 17.075 | 1.00 | 15.56 | C |
| ATOM | 40096 | CB | GLU | D | 672 | 9.747 | 109.181 | 18.486 | 1.00 | 14.51 | C |
| ATOM | 40099 | CG | GLU | D | 672 | 8.761 | 109.628 | 19.514 | 1.00 | 17.77 | C |
| ATOM | 40102 | CD | GLU | D | 672 | 9.248 | 109.386 | 20.938 | 1.00 | 19.62 | C |
| ATOM | 40103 | OE1 | GLU | D | 672 | 10.296 | 109.950 | 21.365 | 1.00 | 21.87 | O |
| ATOM | 40104 | OE2 | GLU | D | 672 | 8.586 | 108.600 | 21.630 | 1.00 | 22.74 | O |
| ATOM | 40105 | C | GLU | D | 672 | 10.613 | 109.591 | 16.180 | 1.00 | 14.66 | C |
| ATOM | 40106 | O | GLU | D | 672 | 11.290 | 110.566 | 16.007 | 1.00 | 15.90 | O |
| ATOM | 40108 | N | LEU | D | 673 | 10.932 | 108.426 | 15.648 | 1.00 | 14.02 | N |
| ATOM | 40109 | CA | LEU | D | 673 | 12.070 | 108.303 | 14.747 | 1.00 | 14.69 | C |
| ATOM | 40111 | CB | LEU | D | 673 | 12.648 | 106.911 | 14.802 | 1.00 | 15.81 | C |
| ATOM | 40114 | CG | LEU | D | 673 | 13.081 | 106.442 | 16.211 | 1.00 | 14.24 | C |
| ATOM | 40116 | CD1 | LEU | D | 673 | 13.877 | 105.127 | 16.103 | 1.00 | 15.74 | C |
| ATOM | 40120 | CD2 | LEU | D | 673 | 13.932 | 107.459 | 16.944 | 1.00 | 15.84 | C |
| ATOM | 40124 | C | LEU | D | 673 | 11.728 | 108.620 | 13.306 | 1.00 | 14.96 | C |
| ATOM | 40125 | O | LEU | D | 673 | 12.656 | 108.746 | 12.498 | 1.00 | 15.91 | O |
| ATOM | 40127 | N | GLY | D | 674 | 10.444 | 108.674 | 12.979 | 1.00 | 14.77 | N |
| ATOM | 40128 | CA | GLY | D | 674 | 9.981 | 109.070 | 11.643 | 1.00 | 14.03 | C |
| ATOM | 40131 | C | GLY | D | 674 | 10.223 | 108.019 | 10.560 | 1.00 | 15.44 | C |
| ATOM | 40132 | O | GLY | D | 674 | 10.181 | 108.333 | 9.346 | 1.00 | 15.56 | O |
| ATOM | 40134 | N | VAL | D | 675 | 10.473 | 106.783 | 10.982 | 1.00 | 13.46 | N |
| ATOM | 40135 | CA | VAL | D | 675 | 10.713 | 105.713 | 10.016 | 1.00 | 14.04 | C |
| ATOM | 40137 | CB | VAL | D | 675 | 11.635 | 104.615 | 10.545 | 1.00 | 14.24 | C |
| ATOM | 40139 | CG1 | VAL | D | 675 | 11.735 | 103.498 | 9.499 | 1.00 | 16.82 | C |
| ATOM | 40143 | CG2 | VAL | D | 675 | 13.012 | 105.228 | 10.886 | 1.00 | 15.89 | C |
| ATOM | 40147 | C | VAL | D | 675 | 9.363 | 105.135 | 9.598 | 1.00 | 14.43 | C |
| ATOM | 40148 | O | VAL | D | 675 | 8.696 | 104.469 | 10.398 | 1.00 | 13.13 | O |
| ATOM | 40150 | N | LYS | D | 676 | 8.981 | 105.374 | 8.345 | 1.00 | 15.07 | N |
| ATOM | 40151 | CA | LYS | D | 676 | 7.665 | 104.959 | 7.837 | 1.00 | 14.24 | C |
| ATOM | 40153 | CB | LYS | D | 676 | 7.132 | 106.037 | 6.915 | 1.00 | 15.04 | C |
| ATOM | 40156 | CG | LYS | D | 676 | 7.093 | 107.447 | 7.573 | 1.00 | 15.14 | C |
| ATOM | 40159 | CD | LYS | D | 676 | 6.194 | 107.508 | 8.806 | 1.00 | 15.74 | C |
| ATOM | 40162 | CE | LYS | D | 676 | 6.207 | 108.873 | 9.438 | 1.00 | 16.21 | C |
| ATOM | 40165 | NZ | LYS | D | 676 | 5.265 | 108.995 | 10.594 | 1.00 | 12.38 | N |
| ATOM | 40169 | C | LYS | D | 676 | 7.725 | 103.620 | 7.090 | 1.00 | 13.38 | C |
| ATOM | 40170 | O | LYS | D | 676 | 8.787 | 103.198 | 6.652 | 1.00 | 12.64 | O |
| ATOM | 40172 | N | ALA | D | 677 | 6.556 | 103.001 | 6.890 | 1.00 | 12.55 | N |
| ATOM | 40173 | CA | ALA | D | 677 | 6.458 | 101.947 | 5.906 | 1.00 | 12.56 | C |
| ATOM | 40175 | CB | ALA | D | 677 | 5.062 | 101.466 | 5.773 | 1.00 | 12.06 | C |
| ATOM | 40179 | C | ALA | D | 677 | 6.961 | 102.479 | 4.560 | 1.00 | 12.15 | C |
| ATOM | 40180 | O | ALA | D | 677 | 6.878 | 103.694 | 4.321 | 1.00 | 13.98 | O |
| ATOM | 40182 | N | ARG | D | 678 | 7.511 | 101.563 | 3.756 | 1.00 | 13.33 | N |
| ATOM | 40183 | CA | ARG | D | 678 | 8.089 | 101.901 | 2.464 | 1.00 | 13.34 | C |
| ATOM | 40185 | CB | ARG | D | 678 | 9.475 | 101.350 | 2.352 | 1.00 | 13.69 | C |
| ATOM | 40188 | CG | ARG | D | 678 | 10.238 | 101.928 | 1.177 | 1.00 | 13.20 | C |
| ATOM | 40191 | CD | ARG | D | 678 | 11.573 | 101.225 | 0.942 | 1.00 | 13.03 | C |
| ATOM | 40194 | NE | ARG | D | 678 | 12.357 | 101.978 | −0.044 | 1.00 | 12.85 | N |
| ATOM | 40196 | CZ | ARG | D | 678 | 13.144 | 103.030 | 0.233 | 1.00 | 16.08 | C |
| ATOM | 40197 | NH1 | ARG | D | 678 | 13.357 | 103.441 | 1.453 | 1.00 | 15.10 | N |

| ATOM | 40200 | NH2 | ARG | D | 678 | 13.733 | 103.692 | -0.757 | 1.00 | 16.07 | N |
|------|-------|-----|-----|---|-----|--------|---------|--------|------|-------|---|
| ATOM | 40203 | C | ARG | D | 678 | 7.202 | 101.308 | 1.372 | 1.00 | 13.80 | C |
| ATOM | 40204 | O | ARG | D | 678 | 6.973 | 100.104 | 1.341 | 1.00 | 12.26 | O |
| ATOM | 40206 | N | ARG | D | 679 | 6.719 | 102.163 | 0.493 | 1.00 | 13.22 | N |
| ATOM | 40207 | CA | ARG | D | 679 | 5.818 | 101.731 | -0.554 | 1.00 | 13.09 | C |
| ATOM | 40209 | CB | ARG | D | 679 | 4.947 | 102.881 | -1.034 | 1.00 | 13.31 | C |
| ATOM | 40212 | CG | ARG | D | 679 | 3.793 | 102.359 | -1.835 | 1.00 | 12.00 | C |
| ATOM | 40215 | CD | ARG | D | 679 | 2.709 | 103.359 | -2.087 | 1.00 | 13.32 | C |
| ATOM | 40218 | NE | ARG | D | 679 | 1.501 | 102.722 | -2.626 | 1.00 | 13.30 | N |
| ATOM | 40220 | CZ | ARG | D | 679 | 0.336 | 103.327 | -2.840 | 1.00 | 13.95 | C |
| ATOM | 40221 | NH1 | ARG | D | 679 | 0.180 | 104.613 | -2.547 | 1.00 | 13.67 | N |
| ATOM | 40224 | NH2 | ARG | D | 679 | -0.699 | 102.649 | -3.318 | 1.00 | 14.64 | N |
| ATOM | 40227 | C | ARG | D | 679 | 6.531 | 101.125 | -1.755 | 1.00 | 13.51 | C |
| ATOM | 40228 | O | ARG | D | 679 | 5.982 | 100.227 | -2.374 | 1.00 | 14.94 | O |
| ATOM | 40230 | N | GLY | D | 680 | 7.715 | 101.643 | -2.118 | 1.00 | 13.40 | N |
| ATOM | 40231 | CA | GLY | D | 680 | 8.538 | 101.057 | -3.165 | 1.00 | 13.43 | C |
| ATOM | 40234 | C | GLY | D | 680 | 8.933 | 102.085 | -4.237 | 1.00 | 13.33 | C |
| ATOM | 40235 | O | GLY | D | 680 | 8.085 | 102.808 | -4.790 | 1.00 | 13.96 | O |
| ATOM | 40237 | N | ASP | D | 681 | 10.239 | 102.173 | -4.517 | 1.00 | 13.27 | N |
| ATOM | 40238 | CA | ASP | D | 681 | 10.775 | 103.194 | -5.434 | 1.00 | 13.85 | C |
| ATOM | 40240 | CB | ASP | D | 681 | 12.297 | 103.077 | -5.595 | 1.00 | 13.02 | C |
| ATOM | 40243 | CG | ASP | D | 681 | 13.084 | 103.485 | -4.374 | 1.00 | 17.28 | C |
| ATOM | 40244 | OD1 | ASP | D | 681 | 12.488 | 103.918 | -3.363 | 1.00 | 17.29 | O |
| ATOM | 40245 | OD2 | ASP | D | 681 | 14.341 | 103.367 | -4.477 | 1.00 | 14.87 | O |
| ATOM | 40246 | C | ASP | D | 681 | 10.153 | 103.121 | -6.842 | 1.00 | 13.13 | C |
| ATOM | 40247 | O | ASP | D | 681 | 9.876 | 104.131 | -7.476 | 1.00 | 13.31 | O |
| ATOM | 40249 | N | VAL | D | 682 | 9.968 | 101.905 | -7.357 | 1.00 | 12.96 | N |
| ATOM | 40250 | CA | VAL | D | 682 | 9.437 | 101.769 | -8.712 | 1.00 | 13.19 | C |
| ATOM | 40252 | CB | VAL | D | 682 | 9.660 | 100.339 | -9.294 | 1.00 | 13.79 | C |
| ATOM | 40254 | CG1 | VAL | D | 682 | 8.960 | 100.221 | -10.650 | 1.00 | 14.82 | C |
| ATOM | 40258 | CG2 | VAL | D | 682 | 11.172 | 100.005 | -9.397 | 1.00 | 13.76 | C |
| ATOM | 40262 | C | VAL | D | 682 | 7.966 | 102.183 | -8.761 | 1.00 | 13.26 | C |
| ATOM | 40263 | O | VAL | D | 682 | 7.561 | 102.958 | -9.647 | 1.00 | 13.60 | O |
| ATOM | 40265 | N | PHE | D | 683 | 7.167 | 101.694 | -7.798 | 1.00 | 13.44 | N |
| ATOM | 40266 | CA | PHE | D | 683 | 5.766 | 102.116 | -7.711 | 1.00 | 14.01 | C |
| ATOM | 40268 | CB | PHE | D | 683 | 5.051 | 101.563 | -6.488 | 1.00 | 14.84 | C |
| ATOM | 40271 | CG | PHE | D | 683 | 3.621 | 101.988 | -6.428 | 1.00 | 14.25 | C |
| ATOM | 40272 | CD1 | PHE | D | 683 | 2.650 | 101.269 | -7.122 | 1.00 | 16.48 | C |
| ATOM | 40274 | CE1 | PHE | D | 683 | 1.337 | 101.686 | -7.113 | 1.00 | 15.35 | C |
| ATOM | 40276 | CZ | PHE | D | 683 | 0.984 | 102.815 | -6.428 | 1.00 | 17.54 | C |
| ATOM | 40278 | CE2 | PHE | D | 683 | 1.922 | 103.532 | -5.750 | 1.00 | 17.40 | C |
| ATOM | 40280 | CD2 | PHE | D | 683 | 3.240 | 103.128 | -5.745 | 1.00 | 16.86 | C |
| ATOM | 40282 | C | PHE | D | 683 | 5.642 | 103.616 | -7.683 | 1.00 | 13.06 | C |
| ATOM | 40283 | O | PHE | D | 683 | 4.779 | 104.225 | -8.369 | 1.00 | 13.58 | O |
| ATOM | 40285 | N | LEU | D | 684 | 6.483 | 104.222 | -6.832 | 1.00 | 13.03 | N |
| ATOM | 40286 | CA | LEU | D | 684 | 6.435 | 105.681 | -6.622 | 1.00 | 12.73 | C |
| ATOM | 40288 | CB | LEU | D | 684 | 7.135 | 106.028 | -5.315 | 1.00 | 14.40 | C |
| ATOM | 40291 | CG | LEU | D | 684 | 6.429 | 105.562 | -4.034 | 1.00 | 14.04 | C |
| ATOM | 40293 | CD1 | LEU | D | 684 | 7.368 | 105.766 | -2.841 | 1.00 | 14.18 | C |
| ATOM | 40297 | CD2 | LEU | D | 684 | 5.128 | 106.312 | -3.843 | 1.00 | 13.32 | C |
| ATOM | 40301 | C | LEU | D | 684 | 7.063 | 106.526 | -7.740 | 1.00 | 14.72 | C |
| ATOM | 40302 | O | LEU | D | 684 | 6.867 | 107.748 | -7.785 | 1.00 | 15.17 | O |
| ATOM | 40304 | N | GLY | D | 685 | 7.826 | 105.902 | -8.620 | 1.00 | 14.47 | N |
| ATOM | 40305 | CA | GLY | D | 685 | 8.618 | 106.644 | -9.587 | 1.00 | 16.13 | C |
| ATOM | 40308 | C | GLY | D | 685 | 9.616 | 107.591 | -8.930 | 1.00 | 17.03 | C |
| ATOM | 40309 | O | GLY | D | 685 | 9.978 | 108.608 | -9.514 | 1.00 | 17.50 | O |
| ATOM | 40311 | N | LYS | D | 686 | 10.099 | 107.220 | -7.747 | 1.00 | 16.91 | N |

| ATOM | 40312 | CA | LYS | D | 686 | 10.987 | 108.066 | -6.958 | 1.00 | 17.78 | C |
|---|---|---|---|---|---|---|---|---|---|---|---|
| ATOM | 40314 | CB | LYS | D | 686 | 10.166 | 108.870 | -5.942 | 1.00 | 18.44 | C |
| ATOM | 40317 | CG | LYS | D | 686 | 10.973 | 109.684 | -4.968 | 1.00 | 21.85 | C |
| ATOM | 40320 | CD | LYS | D | 686 | 10.115 | 110.499 | -3.982 | 1.00 | 21.63 | C |
| ATOM | 40323 | CE | LYS | D | 686 | 11.025 | 111.373 | -3.072 | 1.00 | 24.70 | C |
| ATOM | 40326 | NZ | LYS | D | 686 | 10.147 | 112.387 | -2.323 | 1.00 | 26.34 | N |
| ATOM | 40330 | C | LYS | D | 686 | 11.975 | 107.163 | -6.216 | 1.00 | 17.47 | C |
| ATOM | 40331 | O | LYS | D | 686 | 11.588 | 106.154 | -5.627 | 1.00 | 17.04 | O |
| ATOM | 40333 | N | GLN | D | 687 | 13.247 | 107.546 | -6.219 | 1.00 | 16.09 | N |
| ATOM | 40334 | CA | GLN | D | 687 | 14.216 | 106.853 | -5.399 | 1.00 | 15.87 | C |
| ATOM | 40336 | CB | GLN | D | 687 | 15.563 | 106.870 | -6.080 | 1.00 | 15.51 | C |
| ATOM | 40339 | CG | GLN | D | 687 | 15.526 | 106.116 | -7.371 | 1.00 | 16.03 | C |
| ATOM | 40342 | CD | GLN | D | 687 | 16.897 | 106.096 | -8.021 | 1.00 | 19.87 | C |
| ATOM | 40343 | OE1 | GLN | D | 687 | 17.322 | 107.090 | -8.603 | 1.00 | 22.45 | O |
| ATOM | 40344 | NE2 | GLN | D | 687 | 17.599 | 104.998 | -7.876 | 1.00 | 16.86 | N |
| ATOM | 40347 | C | GLN | D | 687 | 14.272 | 107.508 | -4.020 | 1.00 | 16.27 | C |
| ATOM | 40348 | O | GLN | D | 687 | 14.956 | 108.495 | -3.808 | 1.00 | 14.98 | O |
| ATOM | 40350 | N | GLU | D | 688 | 13.514 | 106.955 | -3.083 | 1.00 | 14.69 | N |
| ATOM | 40351 | CA | GLU | D | 688 | 13.389 | 107.616 | -1.788 | 1.00 | 14.91 | C |
| ATOM | 40353 | CB | GLU | D | 688 | 12.204 | 107.021 | -1.020 | 1.00 | 15.25 | C |
| ATOM | 40356 | CG | GLU | D | 688 | 10.854 | 107.192 | -1.713 | 1.00 | 16.50 | C |
| ATOM | 40359 | CD | GLU | D | 688 | 9.696 | 106.969 | -0.727 | 1.00 | 17.73 | C |
| ATOM | 40360 | OE1 | GLU | D | 688 | 9.468 | 105.804 | -0.265 | 1.00 | 17.22 | O |
| ATOM | 40361 | OE2 | GLU | D | 688 | 9.051 | 108.010 | -0.371 | 1.00 | 17.93 | O |
| ATOM | 40362 | C | GLU | D | 688 | 14.640 | 107.434 | -0.954 | 1.00 | 14.09 | C |
| ATOM | 40363 | O | GLU | D | 688 | 15.458 | 106.532 | -1.221 | 1.00 | 13.83 | O |
| ATOM | 40365 | N | VAL | D | 689 | 14.759 | 108.256 | 0.082 | 1.00 | 14.13 | N |
| ATOM | 40366 | CA | VAL | D | 689 | 15.789 | 108.023 | 1.134 | 1.00 | 13.88 | C |
| ATOM | 40368 | CB | VAL | D | 689 | 15.489 | 108.884 | 2.408 | 1.00 | 14.57 | C |
| ATOM | 40370 | CG1 | VAL | D | 689 | 16.270 | 108.400 | 3.593 | 1.00 | 15.70 | C |
| ATOM | 40374 | CG2 | VAL | D | 689 | 15.718 | 110.353 | 2.142 | 1.00 | 15.27 | C |
| ATOM | 40378 | C | VAL | D | 689 | 15.853 | 106.533 | 1.401 | 1.00 | 13.80 | C |
| ATOM | 40379 | O | VAL | D | 689 | 14.818 | 105.861 | 1.502 | 1.00 | 13.41 | O |
| ATOM | 40381 | N | THR | D | 690 | 17.060 | 106.026 | 1.470 | 1.00 | 12.36 | N |
| ATOM | 40382 | CA | THR | D | 690 | 17.284 | 104.587 | 1.419 | 1.00 | 12.36 | C |
| ATOM | 40384 | CB | THR | D | 690 | 18.755 | 104.247 | 1.221 | 1.00 | 13.55 | C |
| ATOM | 40386 | OG1 | THR | D | 690 | 19.486 | 104.699 | 2.371 | 1.00 | 14.99 | O |
| ATOM | 40388 | CG2 | THR | D | 690 | 19.273 | 104.839 | -0.095 | 1.00 | 15.32 | C |
| ATOM | 40392 | C | THR | D | 690 | 16.786 | 103.841 | 2.656 | 1.00 | 12.70 | C |
| ATOM | 40393 | O | THR | D | 690 | 16.649 | 104.374 | 3.775 | 1.00 | 12.37 | O |
| ATOM | 40395 | N | ILE | D | 691 | 16.558 | 102.554 | 2.450 | 1.00 | 13.28 | N |
| ATOM | 40396 | CA | ILE | D | 691 | 16.286 | 101.626 | 3.541 | 1.00 | 12.99 | C |
| ATOM | 40398 | CB | ILE | D | 691 | 16.258 | 100.202 | 2.995 | 1.00 | 13.45 | C |
| ATOM | 40400 | CG1 | ILE | D | 691 | 15.021 | 100.011 | 2.129 | 1.00 | 13.85 | C |
| ATOM | 40403 | CD1 | ILE | D | 691 | 15.143 | 98.867 | 1.170 | 1.00 | 14.54 | C |
| ATOM | 40407 | CG2 | ILE | D | 691 | 16.282 | 99.141 | 4.091 | 1.00 | 14.04 | C |
| ATOM | 40411 | C | ILE | D | 691 | 17.354 | 101.777 | 4.627 | 1.00 | 13.02 | C |
| ATOM | 40412 | O | ILE | D | 691 | 17.045 | 101.875 | 5.826 | 1.00 | 12.43 | O |
| ATOM | 40414 | N | GLY | D | 692 | 18.607 | 101.783 | 4.214 | 1.00 | 11.35 | N |
| ATOM | 40415 | CA | GLY | D | 692 | 19.716 | 101.812 | 5.170 | 1.00 | 11.12 | C |
| ATOM | 40418 | C | GLY | D | 692 | 19.715 | 103.065 | 6.023 | 1.00 | 11.56 | C |
| ATOM | 40419 | O | GLY | D | 692 | 20.041 | 103.008 | 7.230 | 1.00 | 13.04 | O |
| ATOM | 40421 | N | SER | D | 693 | 19.386 | 104.213 | 5.398 | 1.00 | 11.92 | N |
| ATOM | 40422 | CA | SER | D | 693 | 19.203 | 105.489 | 6.125 | 1.00 | 12.69 | C |
| ATOM | 40424 | CB | SER | D | 693 | 18.851 | 106.649 | 5.182 | 1.00 | 13.26 | C |
| ATOM | 40427 | OG | SER | D | 693 | 20.019 | 107.028 | 4.440 | 1.00 | 14.23 | O |
| ATOM | 40429 | C | SER | D | 693 | 18.168 | 105.348 | 7.272 | 1.00 | 12.20 | C |

| | | | | | | | | | |
|---|---|---|---|---|---|---|---|---|---|
| ATOM | 40430 | O | SER | D | 693 | 18.368 | 105.852 | 8.385 | 1.00 14.05 | O |
| ATOM | 40432 | N | ASN | D | 694 | 17.091 | 104.637 | 6.984 | 1.00 12.33 | N |
| ATOM | 40433 | CA | ASN | D | 694 | 16.024 | 104.434 | 7.983 | 1.00 13.04 | C |
| ATOM | 40435 | CB | ASN | D | 694 | 14.715 | 104.100 | 7.263 | 1.00 14.24 | C |
| ATOM | 40438 | CG | ASN | D | 694 | 14.223 | 105.269 | 6.439 | 1.00 16.25 | C |
| ATOM | 40439 | OD1 | ASN | D | 694 | 14.283 | 106.422 | 6.929 | 1.00 19.82 | O |
| ATOM | 40440 | ND2 | ASN | D | 694 | 13.781 | 105.033 | 5.189 | 1.00 16.02 | N |
| ATOM | 40443 | C | ASN | D | 694 | 16.432 | 103.418 | 9.046 | 1.00 12.80 | C |
| ATOM | 40444 | O | ASN | D | 694 | 16.246 | 103.656 | 10.239 | 1.00 13.31 | O |
| ATOM | 40446 | N | VAL | D | 695 | 17.068 | 102.315 | 8.654 | 1.00 12.79 | N |
| ATOM | 40447 | CA | VAL | D | 695 | 17.625 | 101.382 | 9.646 | 1.00 13.66 | C |
| ATOM | 40449 | CB | VAL | D | 695 | 18.261 | 100.126 | 8.985 | 1.00 12.60 | C |
| ATOM | 40451 | CG1 | VAL | D | 695 | 18.860 | 99.192 | 10.007 | 1.00 15.42 | C |
| ATOM | 40455 | CG2 | VAL | D | 695 | 17.170 | 99.376 | 8.166 | 1.00 13.91 | C |
| ATOM | 40459 | C | VAL | D | 695 | 18.614 | 102.093 | 10.552 | 1.00 13.58 | C |
| ATOM | 40460 | O | VAL | D | 695 | 18.647 | 101.826 | 11.760 | 1.00 13.60 | O |
| ATOM | 40462 | N | SER | D | 696 | 19.430 | 102.980 | 9.965 | 1.00 12.50 | N |
| ATOM | 40463 | CA | SER | D | 696 | 20.452 | 103.694 | 10.733 | 1.00 12.60 | C |
| ATOM | 40465 | CB | SER | D | 696 | 21.300 | 104.589 | 9.842 | 1.00 12.55 | C |
| ATOM | 40468 | OG | SER | D | 696 | 22.009 | 103.858 | 8.839 | 1.00 12.39 | O |
| ATOM | 40470 | C | SER | D | 696 | 19.804 | 104.547 | 11.850 | 1.00 13.05 | C |
| ATOM | 40471 | O | SER | D | 696 | 20.382 | 104.672 | 12.930 | 1.00 13.61 | O |
| ATOM | 40473 | N | LYS | D | 697 | 18.657 | 105.175 | 11.576 | 1.00 12.98 | N |
| ATOM | 40474 | CA | LYS | D | 697 | 17.927 | 105.948 | 12.616 | 1.00 13.59 | C |
| ATOM | 40476 | CB | LYS | D | 697 | 16.693 | 106.604 | 12.060 | 1.00 15.08 | C |
| ATOM | 40479 | CG | LYS | D | 697 | 16.997 | 107.755 | 11.095 | 1.00 17.08 | C |
| ATOM | 40482 | CD | LYS | D | 697 | 15.645 | 108.166 | 10.385 | 1.00 21.58 | C |
| ATOM | 40485 | CE | LYS | D | 697 | 15.423 | 109.648 | 10.000 | 1.00 26.93 | C |
| ATOM | 40488 | NZ | LYS | D | 697 | 13.850 | 109.892 | 9.782 | 1.00 26.21 | N |
| ATOM | 40492 | C | LYS | D | 697 | 17.564 | 105.022 | 13.798 | 1.00 13.07 | C |
| ATOM | 40493 | O | LYS | D | 697 | 17.648 | 105.397 | 14.974 | 1.00 14.25 | O |
| ATOM | 40495 | N | ILE | D | 698 | 17.148 | 103.808 | 13.475 | 1.00 12.46 | N |
| ATOM | 40496 | CA | ILE | D | 698 | 16.779 | 102.872 | 14.535 | 1.00 13.36 | C |
| ATOM | 40498 | CB | ILE | D | 698 | 16.036 | 101.663 | 13.958 | 1.00 12.50 | C |
| ATOM | 40500 | CG1 | ILE | D | 698 | 14.748 | 102.132 | 13.224 | 1.00 14.19 | C |
| ATOM | 40503 | CD1 | ILE | D | 698 | 14.084 | 101.007 | 12.452 | 1.00 14.66 | C |
| ATOM | 40507 | CG2 | ILE | D | 698 | 15.740 | 100.651 | 15.059 | 1.00 14.59 | C |
| ATOM | 40511 | C | ILE | D | 698 | 18.023 | 102.444 | 15.329 | 1.00 13.19 | C |
| ATOM | 40512 | O | ILE | D | 698 | 18.021 | 102.457 | 16.574 | 1.00 14.53 | O |
| ATOM | 40514 | N | TYR | D | 699 | 19.065 | 102.031 | 14.619 | 1.00 13.35 | N |
| ATOM | 40515 | CA | TYR | D | 699 | 20.353 | 101.692 | 15.230 | 1.00 12.76 | C |
| ATOM | 40517 | CB | TYR | D | 699 | 21.372 | 101.397 | 14.124 | 1.00 14.44 | C |
| ATOM | 40520 | CG | TYR | D | 699 | 22.805 | 101.381 | 14.542 | 1.00 13.01 | C |
| ATOM | 40521 | CD1 | TYR | D | 699 | 23.391 | 100.202 | 15.099 | 1.00 13.53 | C |
| ATOM | 40523 | CE1 | TYR | D | 699 | 24.749 | 100.184 | 15.449 | 1.00 12.64 | C |
| ATOM | 40525 | CZ | TYR | D | 699 | 25.543 | 101.321 | 15.225 | 1.00 13.45 | C |
| ATOM | 40526 | OH | TYR | D | 699 | 26.878 | 101.285 | 15.549 | 1.00 15.83 | O |
| ATOM | 40528 | CE2 | TYR | D | 699 | 24.987 | 102.503 | 14.695 | 1.00 12.73 | C |
| ATOM | 40530 | CD2 | TYR | D | 699 | 23.615 | 102.506 | 14.318 | 1.00 13.10 | C |
| ATOM | 40532 | C | TYR | D | 699 | 20.819 | 102.821 | 16.164 | 1.00 13.58 | C |
| ATOM | 40533 | O | TYR | D | 699 | 21.223 | 102.586 | 17.282 | 1.00 12.69 | O |
| ATOM | 40535 | N | GLU | D | 700 | 20.763 | 104.063 | 15.694 | 1.00 13.11 | N |
| ATOM | 40536 | CA | GLU | D | 700 | 21.208 | 105.210 | 16.522 | 1.00 14.72 | C |
| ATOM | 40538 | CB | GLU | D | 700 | 21.190 | 106.485 | 15.676 | 1.00 14.27 | C |
| ATOM | 40541 | CG | GLU | D | 700 | 22.316 | 106.481 | 14.661 | 1.00 14.12 | C |
| ATOM | 40544 | CD | GLU | D | 700 | 22.428 | 107.720 | 13.773 | 1.00 18.43 | C |
| ATOM | 40545 | OE1 | GLU | D | 700 | 21.409 | 108.432 | 13.604 | 1.00 20.70 | O |

```
ATOM  40546  OE2 GLU D 700     23.520 107.883  13.163  1.00 19.36      O
ATOM  40547  C   GLU D 700     20.427 105.329  17.815  1.00 14.18      C
ATOM  40548  O   GLU D 700     20.991 105.648  18.872  1.00 15.39      O
ATOM  40550  N   ALA D 701     19.129 105.036  17.755  1.00 13.34      N
ATOM  40551  CA  ALA D 701     18.283 105.099  18.959  1.00 13.28      C
ATOM  40553  CB  ALA D 701     16.859 105.023  18.581  1.00 13.90      C
ATOM  40557  C   ALA D 701     18.588 103.966  19.929  1.00 14.03      C
ATOM  40558  O   ALA D 701     18.323 104.085  21.145  1.00 13.66      O
ATOM  40560  N   ILE D 702     19.069 102.860  19.383  1.00 13.30      N
ATOM  40561  CA  ILE D 702     19.518 101.763  20.224  1.00 13.82      C
ATOM  40563  CB  ILE D 702     19.645 100.412  19.448  1.00 13.64      C
ATOM  40565  CG1 ILE D 702     18.255  99.933  18.956  1.00 14.41      C
ATOM  40568  CD1 ILE D 702     18.319  98.789  17.968  1.00 15.11      C
ATOM  40572  CG2 ILE D 702     20.315  99.379  20.330  1.00 15.84      C
ATOM  40576  C   ILE D 702     20.839 102.117  20.888  1.00 14.22      C
ATOM  40577  O   ILE D 702     20.968 102.036  22.123  1.00 14.48      O
ATOM  40579  N   LYS D 703     21.820 102.556  20.097  1.00 14.53      N
ATOM  40580  CA  LYS D 703     23.153 102.889  20.630  1.00 15.61      C
ATOM  40582  CB  LYS D 703     24.122 103.218  19.505  1.00 15.34      C
ATOM  40585  CG  LYS D 703     24.443 102.055  18.554  1.00 16.79      C
ATOM  40588  CD  LYS D 703     25.041 100.808  19.198  1.00 19.13      C
ATOM  40591  CE  LYS D 703     26.413 101.044  19.862  1.00 23.31      C
ATOM  40594  NZ  LYS D 703     27.433 101.597  18.970  1.00 21.06      N
ATOM  40598  C   LYS D 703     23.159 104.025  21.649  1.00 14.46      C
ATOM  40599  O   LYS D 703     23.939 103.987  22.606  1.00 15.42      O
ATOM  40601  N   SER D 704     22.285 105.014  21.451  1.00 14.02      N
ATOM  40602  CA  SER D 704     22.176 106.185  22.328  1.00 15.98      C
ATOM  40604  CB  SER D 704     21.438 107.326  21.655  1.00 15.56      C
ATOM  40607  OG  SER D 704     20.069 107.005  21.471  1.00 15.01      O
ATOM  40609  C   SER D 704     21.419 105.858  23.594  1.00 14.88      C
ATOM  40610  O   SER D 704     21.427 106.650  24.510  1.00 16.35      O
ATOM  40612  N   GLY D 705     20.708 104.735  23.608  1.00 15.82      N
ATOM  40613  CA  GLY D 705     19.880 104.398  24.758  1.00 15.81      C
ATOM  40616  C   GLY D 705     18.515 105.057  24.730  1.00 14.55      C
ATOM  40617  O   GLY D 705     17.687 104.819  25.648  1.00 14.33      O
ATOM  40619  N   ARG D 706     18.198 105.811  23.673  1.00 14.37      N
ATOM  40620  CA  ARG D 706     16.877 106.409  23.565  1.00 13.77      C
ATOM  40622  CB  ARG D 706     16.781 107.213  22.288  1.00 14.32      C
ATOM  40625  CG  ARG D 706     15.532 108.026  22.192  1.00 14.37      C
ATOM  40628  CD  ARG D 706     15.464 108.828  20.916  1.00 16.59      C
ATOM  40631  NE  ARG D 706     14.216 109.568  20.841  1.00 17.33      N
ATOM  40633  CZ  ARG D 706     13.878 110.335  19.818  1.00 17.44      C
ATOM  40634  NH1 ARG D 706     14.709 110.469  18.789  1.00 17.30      N
ATOM  40637  NH2 ARG D 706     12.735 111.008  19.851  1.00 17.94      N
ATOM  40640  C   ARG D 706     15.766 105.366  23.633  1.00 12.98      C
ATOM  40641  O   ARG D 706     14.712 105.588  24.203  1.00 14.54      O
ATOM  40643  N   ILE D 707     16.018 104.204  23.057  1.00 12.40      N
ATOM  40644  CA  ILE D 707     15.020 103.116  23.080  1.00 13.13      C
ATOM  40646  CB  ILE D 707     15.447 101.989  22.089  1.00 13.69      C
ATOM  40648  CG1 ILE D 707     14.229 101.118  21.690  1.00 14.02      C
ATOM  40651  CD1 ILE D 707     14.491 100.160  20.495  1.00 14.91      C
ATOM  40655  CG2 ILE D 707     16.623 101.210  22.719  1.00 12.68      C
ATOM  40659  C   ILE D 707     14.765 102.521  24.478  1.00 13.63      C
ATOM  40660  O   ILE D 707     13.768 101.808  24.691  1.00 13.51      O
ATOM  40662  N   ASN D 708     15.683 102.770  25.421  1.00 12.97      N
ATOM  40663  CA  ASN D 708     15.685 102.040  26.682  1.00 12.50      C
ATOM  40665  CB  ASN D 708     16.948 102.365  27.508  1.00 13.15      C
```

| | | | | | | | | | |
|---|---|---|---|---|---|---|---|---|---|
| ATOM | 40668 | CG | ASN | D | 708 | 18.226 | 101.918 | 26.838 | 1.00 13.22 | C |
| ATOM | 40669 | OD1 | ASN | D | 708 | 18.214 | 101.105 | 25.878 | 1.00 15.25 | O |
| ATOM | 40670 | ND2 | ASN | D | 708 | 19.384 | 102.385 | 27.389 | 1.00 14.40 | N |
| ATOM | 40673 | C | ASN | D | 708 | 14.407 | 102.250 | 27.500 | 1.00 12.99 | C |
| ATOM | 40674 | O | ASN | D | 708 | 13.802 | 101.282 | 28.008 | 1.00 14.10 | O |
| ATOM | 40676 | N | ASN | D | 709 | 14.001 | 103.493 | 27.643 | 1.00 13.66 | N |
| ATOM | 40677 | CA | ASN | D | 709 | 12.772 | 103.806 | 28.365 | 1.00 15.89 | C |
| ATOM | 40679 | CB | ASN | D | 709 | 12.693 | 105.282 | 28.684 | 1.00 17.52 | C |
| ATOM | 40682 | CG | ASN | D | 709 | 13.659 | 105.680 | 29.821 | 1.00 23.04 | C |
| ATOM | 40683 | OD1 | ASN | D | 709 | 14.059 | 104.852 | 30.677 | 1.00 25.70 | O |
| ATOM | 40684 | ND2 | ASN | D | 709 | 14.015 | 106.948 | 29.853 | 1.00 29.51 | N |
| ATOM | 40687 | C | ASN | D | 709 | 11.529 | 103.292 | 27.636 | 1.00 15.44 | C |
| ATOM | 40688 | O | ASN | D | 709 | 10.507 | 103.039 | 28.270 | 1.00 16.51 | O |
| ATOM | 40690 | N | VAL | D | 710 | 11.636 | 103.096 | 26.321 | 1.00 14.38 | N |
| ATOM | 40691 | CA | VAL | D | 710 | 10.515 | 102.556 | 25.542 | 1.00 14.48 | C |
| ATOM | 40693 | CB | VAL | D | 710 | 10.799 | 102.701 | 24.047 | 1.00 14.91 | C |
| ATOM | 40695 | CG1 | VAL | D | 710 | 9.647 | 102.115 | 23.264 | 1.00 15.46 | C |
| ATOM | 40699 | CG2 | VAL | D | 710 | 10.966 | 104.199 | 23.717 | 1.00 16.89 | C |
| ATOM | 40703 | C | VAL | D | 710 | 10.356 | 101.094 | 25.951 | 1.00 14.06 | C |
| ATOM | 40704 | O | VAL | D | 710 | 9.273 | 100.623 | 26.223 | 1.00 15.47 | O |
| ATOM | 40706 | N | LEU | D | 711 | 11.490 | 100.394 | 26.002 | 1.00 15.00 | N |
| ATOM | 40707 | CA | LEU | D | 711 | 11.496 | 98.998 | 26.398 | 1.00 14.51 | C |
| ATOM | 40709 | CB | LEU | D | 711 | 12.898 | 98.381 | 26.288 | 1.00 15.77 | C |
| ATOM | 40712 | CG | LEU | D | 711 | 13.458 | 98.389 | 24.849 | 1.00 16.06 | C |
| ATOM | 40714 | CD1 | LEU | D | 711 | 14.924 | 98.015 | 24.775 | 1.00 19.27 | C |
| ATOM | 40718 | CD2 | LEU | D | 711 | 12.640 | 97.494 | 23.937 | 1.00 17.89 | C |
| ATOM | 40722 | C | LEU | D | 711 | 10.948 | 98.820 | 27.798 | 1.00 16.40 | C |
| ATOM | 40723 | O | LEU | D | 711 | 10.165 | 97.897 | 28.061 | 1.00 14.97 | O |
| ATOM | 40725 | N | LEU | D | 712 | 11.369 | 99.709 | 28.700 | 1.00 16.67 | N |
| ATOM | 40726 | CA | LEU | D | 712 | 10.889 | 99.669 | 30.087 | 1.00 18.13 | C |
| ATOM | 40728 | CB | LEU | D | 712 | 11.640 | 100.705 | 30.917 | 1.00 17.94 | C |
| ATOM | 40731 | CG | LEU | D | 712 | 11.300 | 100.661 | 32.390 | 1.00 21.79 | C |
| ATOM | 40733 | CD1 | LEU | D | 712 | 11.762 | 99.314 | 32.989 | 1.00 25.30 | C |
| ATOM | 40737 | CD2 | LEU | D | 712 | 12.003 | 101.875 | 33.045 | 1.00 22.04 | C |
| ATOM | 40741 | C | LEU | D | 712 | 9.393 | 99.904 | 30.174 | 1.00 17.75 | C |
| ATOM | 40742 | O | LEU | D | 712 | 8.673 | 99.175 | 30.862 | 1.00 18.03 | O |
| ATOM | 40744 | N | LYS | D | 713 | 8.906 | 100.904 | 29.454 | 1.00 17.85 | N |
| ATOM | 40745 | CA | LYS | D | 713 | 7.468 | 101.176 | 29.407 | 1.00 20.07 | C |
| ATOM | 40747 | CB | LYS | D | 713 | 7.157 | 102.311 | 28.454 | 1.00 20.15 | C |
| ATOM | 40750 | CG | LYS | D | 713 | 7.389 | 103.683 | 29.009 | 1.00 24.81 | C |
| ATOM | 40753 | CD | LYS | D | 713 | 6.990 | 104.759 | 27.955 | 1.00 25.98 | C |
| ATOM | 40756 | CE | LYS | D | 713 | 5.510 | 104.736 | 27.597 | 1.00 31.04 | C |
| ATOM | 40759 | NZ | LYS | D | 713 | 5.120 | 105.829 | 26.636 | 1.00 32.92 | N |
| ATOM | 40763 | C | LYS | D | 713 | 6.676 | 99.962 | 28.951 | 1.00 19.69 | C |
| ATOM | 40764 | O | LYS | D | 713 | 5.667 | 99.625 | 29.550 | 1.00 17.45 | O |
| ATOM | 40766 | N | MSE | D | 714 | 7.135 | 99.309 | 27.904 | 1.00 19.40 | N |
| ATOM | 40767 | CA | MSE | D | 714 | 6.415 | 98.152 | 27.362 | 1.00 21.48 | C |
| ATOM | 40769 | CB | MSE | D | 714 | 7.104 | 97.618 | 26.102 | 1.00 21.58 | C |
| ATOM | 40772 | CG | MSE | D | 714 | 7.190 | 98.556 | 24.984 | 1.00 21.90 | C |
| ATOM | 40775 | SE | MSE | D | 714 | 8.540 | 97.817 | 23.710 | 1.00 27.80 | SE |
| ATOM | 40776 | CE | MSE | D | 714 | 7.439 | 96.304 | 22.941 | 1.00 20.39 | C |
| ATOM | 40780 | C | MSE | D | 714 | 6.344 | 97.003 | 28.344 | 1.00 22.37 | C |
| ATOM | 40781 | O | MSE | D | 714 | 5.380 | 96.239 | 28.326 | 1.00 19.02 | O |
| ATOM | 40783 | N | LEU | D | 715 | 7.377 | 96.878 | 29.185 | 1.00 23.71 | N |
| ATOM | 40784 | CA | LEU | D | 715 | 7.554 | 95.688 | 30.032 | 1.00 26.59 | C |
| ATOM | 40786 | CB | LEU | D | 715 | 8.963 | 95.112 | 29.868 | 1.00 26.20 | C |
| ATOM | 40789 | CG | LEU | D | 715 | 9.189 | 94.392 | 28.556 | 1.00 26.41 | C |

```
ATOM  40791  CD1  LEU D 715      10.697  94.218  28.322  1.00 27.31           C
ATOM  40795  CD2  LEU D 715       8.479  93.053  28.530  1.00 28.25           C
ATOM  40799  C    LEU D 715       7.196  95.861  31.505  1.00 29.62           C
ATOM  40800  O    LEU D 715       7.374  94.934  32.294  1.00 30.18           O
ATOM  40802  N    ALA D 716       6.664  97.023  31.876  1.00 31.90           N
ATOM  40803  CA   ALA D 716       5.959  97.150  33.151  1.00 34.21           C
ATOM  40805  CB   ALA D 716       6.943  97.450  34.251  1.00 34.85           C
ATOM  40809  C    ALA D 716       4.931  98.252  33.063  1.00 35.35           C
ATOM  40810  O    ALA D 716       5.313  99.407  32.850  1.00 37.80           O
ATOM  40812  O    HOH X   1      55.994  61.293  42.601  1.00 10.16           O
ATOM  40815  O    HOH X   2      51.126  67.749  19.171  1.00  9.29           O
ATOM  40818  O    HOH X   3      37.336  84.319  17.281  1.00  6.14           O
ATOM  40821  O    HOH X   4      29.129  87.583  19.821  1.00  8.70           O
ATOM  40824  O    HOH X   5      39.348  81.326  20.853  1.00  6.87           O
ATOM  40827  O    HOH X   7      27.317  65.653  15.549  1.00 10.27           O
ATOM  40830  O    HOH X   8      38.656  87.405  39.871  1.00 10.25           O
ATOM  40833  O    HOH X   9      29.255  98.669  10.871  1.00  8.61           O
ATOM  40836  O    HOH X  10      22.648  72.532  13.977  1.00  8.73           O
ATOM  40839  O    HOH X  13      52.087  73.910  23.788  1.00  8.74           O
ATOM  40842  O    HOH X  14      29.235  92.264   6.623  1.00  9.26           O
ATOM  40845  O    HOH X  16      34.877  84.858  42.097  1.00  9.15           O
ATOM  40848  O    HOH X  17      43.215  92.579  28.699  1.00  9.20           O
ATOM  40851  O    HOH X  18      24.403  97.143  40.294  1.00 14.59           O
ATOM  40854  O    HOH X  19      45.399  94.917  25.285  1.00  8.99           O
ATOM  40857  O    HOH X  20      46.896 101.058  21.437  1.00  9.25           O
ATOM  40860  O    HOH X  21      49.191  99.915  22.455  1.00  9.06           O
ATOM  40863  O    HOH X  22      37.348  74.371  18.706  1.00  8.24           O
ATOM  40866  O    HOH X  23      33.296 104.332   2.545  1.00 10.25           O
ATOM  40869  O    HOH X  24      72.039  76.678  16.170  1.00 12.37           O
ATOM  40872  O    HOH X  25       4.298 104.475   7.847  1.00 12.70           O
ATOM  40875  O    HOH X  26      50.801  97.134   8.817  1.00 10.33           O
ATOM  40878  O    HOH X  27      10.010 103.592  -1.824  1.00 12.48           O
ATOM  40881  O    HOH X  28      66.633 102.393  30.404  1.00 12.37           O
ATOM  40884  O    HOH X  29      27.678  99.289   8.633  1.00  8.44           O
ATOM  40887  O    HOH X  30      31.459  89.132   4.015  1.00  9.23           O
ATOM  40890  O    HOH X  31      42.386  80.781  17.938  1.00 11.59           O
ATOM  40893  O    HOH X  32      38.455  72.705  27.689  1.00  8.67           O
ATOM  40896  O    HOH X  33      38.453  83.100  52.708  1.00 10.53           O
ATOM  40899  O    HOH X  34      49.385  60.851  27.901  1.00  8.41           O
ATOM  40902  O    HOH X  35      64.880 103.009  23.630  1.00 10.00           O
ATOM  40905  O    HOH X  36      60.092  82.801  25.159  1.00 11.11           O
ATOM  40908  O    HOH X  37      23.562  67.888  20.081  1.00 11.21           O
ATOM  40911  O    HOH X  38      41.328 107.613  25.935  1.00 10.21           O
ATOM  40914  O    HOH X  39      76.826  75.743  44.280  1.00 15.51           O
ATOM  40917  O    HOH X  40      43.179  77.252  -8.068  1.00 10.52           O
ATOM  40920  O    HOH X  41      14.528  52.809  10.336  1.00 11.72           O
ATOM  40923  O    HOH X  42      28.809  91.490   9.320  1.00  7.82           O
ATOM  40926  O    HOH X  43      35.756  58.181  46.288  1.00 15.12           O
ATOM  40929  O    HOH X  44      42.799  96.070  24.940  1.00  8.18           O
ATOM  40932  O    HOH X  45      70.136 106.458  20.834  1.00 11.50           O
ATOM  40935  O    HOH X  47      43.209  95.632   4.366  1.00 12.38           O
ATOM  40938  O    HOH X  48      23.081  77.414   5.212  1.00 11.08           O
ATOM  40941  O    HOH X  49      64.359  55.323  38.371  1.00 14.78           O
ATOM  40944  O    HOH X  50      31.827  93.493   6.638  1.00  9.12           O
ATOM  40947  O    HOH X  51      45.796  93.393  22.940  1.00  6.56           O
ATOM  40950  O    HOH X  52      41.538  70.216  21.176  1.00  8.45           O
ATOM  40953  O    HOH X  53      52.827  84.030  53.845  1.00 13.80           O
```

```
ATOM  40956  O   HOH X  54     31.465  98.691  26.583  1.00 10.00           O
ATOM  40959  O   HOH X  55     35.921  81.064  -5.279  1.00 12.08           O
ATOM  40962  O   HOH X  56     39.831  78.614  22.548  1.00 11.66           O
ATOM  40965  O   HOH X  57     47.503  59.312  26.387  1.00 11.08           O
ATOM  40968  O   HOH X  59     64.002 105.213  35.624  1.00 10.87           O
ATOM  40971  O   HOH X  60     16.673 102.109  -0.452  1.00 10.74           O
ATOM  40974  O   HOH X  61     66.823 105.334  35.571  1.00 14.51           O
ATOM  40977  O   HOH X  62     26.148  83.953   6.371  1.00  7.62           O
ATOM  40980  O   HOH X  63     67.530 108.915  27.525  1.00 13.89           O
ATOM  40983  O   HOH X  64     41.041 100.890  49.473  1.00 13.27           O
ATOM  40986  O   HOH X  65     57.967  99.153  29.084  1.00  9.62           O
ATOM  40989  O   HOH X  66     31.441  84.577  43.531  1.00 10.92           O
ATOM  40992  O   HOH X  67     58.814 102.345   1.709  1.00 14.49           O
ATOM  40995  O   HOH X  68     49.724  52.408  19.901  1.00 14.09           O
ATOM  40998  O   HOH X  69     33.634  77.709  17.862  1.00  9.17           O
ATOM  41001  O   HOH X  70     16.663  95.258   1.809  1.00 10.21           O
ATOM  41004  O   HOH X  71     58.141  73.186   9.504  1.00 11.03           O
ATOM  41007  O   HOH X  72     61.015 102.300  34.797  1.00 11.32           O
ATOM  41010  O   HOH X  73      9.589 100.517   6.099  1.00 11.13           O
ATOM  41013  O   HOH X  74     25.388  97.876   7.964  1.00  8.76           O
ATOM  41016  O   HOH X  75     33.664  88.383  13.833  1.00  9.69           O
ATOM  41019  O   HOH X  76      9.321  99.569   8.653  1.00 10.60           O
ATOM  41022  O   HOH X  78     51.867 106.679  23.007  1.00 12.18           O
ATOM  41025  O   HOH X  79     78.695  64.359  41.385  1.00 13.68           O
ATOM  41028  O   HOH X  80     49.535  65.498  22.744  1.00 10.29           O
ATOM  41031  O   HOH X  81     48.619  94.780  31.934  1.00  9.15           O
ATOM  41034  O   HOH X  82     38.100 110.703  -1.563  1.00 11.73           O
ATOM  41037  O   HOH X  83     52.455 107.276  25.600  1.00 11.73           O
ATOM  41040  O   HOH X  84     45.542  86.830  13.915  1.00  7.10           O
ATOM  41043  O   HOH X  85     25.523  58.718  13.629  1.00 10.91           O
ATOM  41046  O   HOH X  86     48.798 110.082  30.558  1.00 13.96           O
ATOM  41049  O   HOH X  87     53.477  98.777  22.806  1.00 11.04           O
ATOM  41052  O   HOH X  88     17.849  77.506  35.520  1.00 11.55           O
ATOM  41055  O   HOH X  89     35.295  80.441  14.656  1.00  8.92           O
ATOM  41058  O   HOH X  90     51.297  86.323  49.100  1.00 12.57           O
ATOM  41061  O   HOH X  91     36.629  63.979  37.922  1.00 11.16           O
ATOM  41064  O   HOH X  92     25.989  90.251   0.341  1.00 10.19           O
ATOM  41067  O   HOH X  93     10.484 104.286   4.730  1.00 14.91           O
ATOM  41070  O   HOH X  94     18.376  74.107  41.276  1.00 14.03           O
ATOM  41073  O   HOH X  95     44.484  95.060 -16.479  1.00 15.82           O
ATOM  41076  O   HOH X  96     30.009 104.010  46.768  1.00 11.11           O
ATOM  41079  O   HOH X  97     12.658 102.658   4.154  1.00  9.90           O
ATOM  41082  O   HOH X  98     75.068 101.108  42.046  1.00 15.14           O
ATOM  41085  O   HOH X  99     65.240 101.476  21.414  1.00  9.18           O
ATOM  41088  O   HOH X 100     45.509  86.617  46.863  1.00 10.05           O
ATOM  41091  O   HOH X 101     26.478  80.623  41.152  1.00 11.82           O
ATOM  41094  O   HOH X 102     67.388  75.539  12.188  1.00  9.80           O
ATOM  41097  O   HOH X 103     57.860 106.254  29.447  1.00  8.92           O
ATOM  41100  O   HOH X 104     18.007  65.759  17.174  1.00 10.16           O
ATOM  41103  O   HOH X 105      5.151  54.023   4.793  1.00 16.63           O
ATOM  41106  O   HOH X 106     26.599  63.831  19.550  1.00  8.90           O
ATOM  41109  O   HOH X 107     45.447  92.480  46.284  1.00 10.85           O
ATOM  41112  O   HOH X 108     64.615 108.126  30.375  1.00 11.39           O
ATOM  41115  O   HOH X 109     22.551 106.591   7.327  1.00  9.79           O
ATOM  41118  O   HOH X 110     43.565  79.933  -7.632  1.00 12.92           O
ATOM  41121  O   HOH X 111     56.870  72.908   1.647  1.00 13.26           O
ATOM  41124  O   HOH X 112     38.012  59.015   3.193  1.00 12.35           O
```

| | | | | | | | | | | |
|---|---|---|---|---|---|---|---|---|---|---|
| ATOM | 41127 | O | HOH | X | 113 | 4.735 | 81.070 | 19.321 | 1.00 14.72 | O |
| ATOM | 41130 | O | HOH | X | 114 | 58.527 | 68.523 | 21.690 | 1.00 13.63 | O |
| ATOM | 41133 | O | HOH | X | 115 | 42.483 | 98.790 | 56.514 | 1.00 16.73 | O |
| ATOM | 41136 | O | HOH | X | 116 | 36.312 | 70.304 | 10.521 | 1.00 9.98 | O |
| ATOM | 41139 | O | HOH | X | 117 | 53.226 | 61.787 | -2.585 | 1.00 15.87 | O |
| ATOM | 41142 | O | HOH | X | 118 | 28.476 | 97.432 | 2.686 | 1.00 11.30 | O |
| ATOM | 41145 | O | HOH | X | 119 | 73.674 | 99.299 | 36.728 | 1.00 14.35 | O |
| ATOM | 41148 | O | HOH | X | 120 | 29.076 | 78.193 | -11.749 | 1.00 13.32 | O |
| ATOM | 41151 | O | HOH | X | 121 | 20.186 | 107.957 | 8.357 | 1.00 16.63 | O |
| ATOM | 41154 | O | HOH | X | 122 | 51.592 | 81.072 | 30.807 | 1.00 10.93 | O |
| ATOM | 41157 | O | HOH | X | 123 | 41.064 | 77.865 | 18.513 | 1.00 8.41 | O |
| ATOM | 41160 | O | HOH | X | 124 | 36.319 | 113.209 | 32.312 | 1.00 12.77 | O |
| ATOM | 41163 | O | HOH | X | 125 | 48.441 | 86.999 | 27.827 | 1.00 6.98 | O |
| ATOM | 41166 | O | HOH | X | 126 | -3.491 | 83.102 | -6.032 | 1.00 12.31 | O |
| ATOM | 41169 | O | HOH | X | 127 | 21.745 | 84.173 | 37.730 | 1.00 14.33 | O |
| ATOM | 41172 | O | HOH | X | 128 | 55.302 | 80.347 | 24.591 | 1.00 12.59 | O |
| ATOM | 41175 | O | HOH | X | 129 | 44.964 | 60.192 | 25.918 | 1.00 11.72 | O |
| ATOM | 41178 | O | HOH | X | 130 | 23.723 | 99.007 | 21.843 | 1.00 11.17 | O |
| ATOM | 41181 | O | HOH | X | 131 | 50.207 | 52.558 | 31.916 | 1.00 15.92 | O |
| ATOM | 41184 | O | HOH | X | 132 | 6.480 | 54.364 | 7.313 | 1.00 14.10 | O |
| ATOM | 41187 | O | HOH | X | 133 | 22.097 | 98.390 | 23.981 | 1.00 10.81 | O |
| ATOM | 41190 | O | HOH | X | 134 | 16.529 | 75.718 | 27.773 | 1.00 10.26 | O |
| ATOM | 41193 | O | HOH | X | 135 | 29.405 | 95.178 | 4.055 | 1.00 13.93 | O |
| ATOM | 41196 | O | HOH | X | 136 | 57.758 | 75.472 | 1.255 | 1.00 13.03 | O |
| ATOM | 41199 | O | HOH | X | 137 | 14.594 | 80.545 | 10.148 | 1.00 12.50 | O |
| ATOM | 41202 | O | HOH | X | 138 | 13.594 | 96.647 | -4.480 | 1.00 12.07 | O |
| ATOM | 41205 | O | HOH | X | 139 | 53.278 | 58.023 | 53.359 | 1.00 15.39 | O |
| ATOM | 41208 | O | HOH | X | 140 | 61.856 | 105.573 | 24.905 | 1.00 10.31 | O |
| ATOM | 41211 | O | HOH | X | 141 | 45.174 | 98.363 | 27.000 | 1.00 10.40 | O |
| ATOM | 41214 | O | HOH | X | 142 | 3.474 | 60.260 | 19.753 | 1.00 17.92 | O |
| ATOM | 41217 | O | HOH | X | 143 | 20.124 | 100.365 | 24.137 | 1.00 14.28 | O |
| ATOM | 41220 | O | HOH | X | 144 | 10.567 | 99.201 | -6.092 | 1.00 12.53 | O |
| ATOM | 41223 | O | HOH | X | 145 | 53.057 | 75.525 | 4.061 | 1.00 14.08 | O |
| ATOM | 41226 | O | HOH | X | 146 | 64.042 | 106.961 | 23.872 | 1.00 12.58 | O |
| ATOM | 41229 | O | HOH | X | 147 | 31.649 | 113.816 | 36.761 | 1.00 14.33 | O |
| ATOM | 41232 | O | HOH | X | 148 | 22.155 | 99.664 | 39.122 | 1.00 15.14 | O |
| ATOM | 41235 | O | HOH | X | 149 | 31.066 | 86.975 | 42.377 | 1.00 11.53 | O |
| ATOM | 41238 | O | HOH | X | 150 | 39.329 | 108.521 | 22.922 | 1.00 12.76 | O |
| ATOM | 41241 | O | HOH | X | 151 | -2.204 | 68.490 | -5.969 | 1.00 12.16 | O |
| ATOM | 41244 | O | HOH | X | 152 | 32.284 | 80.735 | 17.598 | 1.00 13.31 | O |
| ATOM | 41247 | O | HOH | X | 153 | 21.375 | 68.201 | 42.551 | 1.00 14.57 | O |
| ATOM | 41250 | O | HOH | X | 154 | 54.521 | 79.502 | 34.945 | 1.00 9.80 | O |
| ATOM | 41253 | O | HOH | X | 155 | 15.797 | 105.749 | 27.244 | 1.00 12.19 | O |
| ATOM | 41256 | O | HOH | X | 156 | 29.819 | 58.620 | 15.768 | 1.00 11.94 | O |
| ATOM | 41259 | O | HOH | X | 157 | 58.035 | 57.085 | 38.423 | 1.00 12.88 | O |
| ATOM | 41262 | O | HOH | X | 158 | 47.394 | 66.832 | 24.173 | 1.00 8.11 | O |
| ATOM | 41265 | O | HOH | X | 159 | -24.289 | 72.668 | -15.401 | 1.00 14.53 | O |
| ATOM | 41268 | O | HOH | X | 160 | 71.362 | 86.073 | 31.870 | 1.00 13.79 | O |
| ATOM | 41271 | O | HOH | X | 161 | 33.174 | 69.696 | 17.441 | 1.00 10.81 | O |
| ATOM | 41274 | O | HOH | X | 162 | 52.962 | 78.533 | -2.267 | 1.00 13.44 | O |
| ATOM | 41277 | O | HOH | X | 163 | 37.206 | 62.319 | 39.987 | 1.00 16.33 | O |
| ATOM | 41280 | O | HOH | X | 164 | 75.345 | 75.321 | 11.545 | 1.00 14.67 | O |
| ATOM | 41283 | O | HOH | X | 165 | 45.694 | 116.657 | 39.610 | 1.00 14.68 | O |
| ATOM | 41286 | O | HOH | X | 166 | 18.871 | 55.065 | -0.651 | 1.00 13.47 | O |
| ATOM | 41289 | O | HOH | X | 167 | -0.680 | 77.154 | 25.299 | 1.00 15.12 | O |
| ATOM | 41292 | O | HOH | X | 168 | 34.849 | 77.342 | 13.769 | 1.00 11.96 | O |
| ATOM | 41295 | O | HOH | X | 169 | 56.774 | 66.662 | 22.491 | 1.00 11.46 | O |

```
ATOM  41298  O   HOH X 170       3.464  80.079   5.064  1.00 17.15           O
ATOM  41301  O   HOH X 171      38.681 104.874 -18.282  1.00 17.46           O
ATOM  41304  O   HOH X 172      48.183  74.172  -4.637  1.00 14.95           O
ATOM  41307  O   HOH X 173      45.343  99.881  19.462  1.00  9.77           O
ATOM  41310  O   HOH X 174      37.151  86.511  42.017  1.00 10.01           O
ATOM  41313  O   HOH X 175      42.755 118.347  41.838  1.00 13.92           O
ATOM  41316  O   HOH X 176       7.810  99.432  -6.090  1.00 13.31           O
ATOM  41319  O   HOH X 177      25.234  64.727  17.201  1.00  9.13           O
ATOM  41322  O   HOH X 178      75.602  77.194  60.085  1.00 15.49           O
ATOM  41325  O   HOH X 179      73.638  60.375  46.066  1.00 16.26           O
ATOM  41328  O   HOH X 180      41.659 104.599   3.552  1.00 18.34           O
ATOM  41331  O   HOH X 181      69.900  80.853  16.197  1.00 13.23           O
ATOM  41334  O   HOH X 182      36.533 114.745  28.122  1.00 11.17           O
ATOM  41337  O   HOH X 183      45.292  80.981  -0.579  1.00 14.88           O
ATOM  41340  O   HOH X 184      40.992  89.142  19.498  1.00  9.08           O
ATOM  41343  O   HOH X 185      58.013  59.879  41.392  1.00 11.13           O
ATOM  41346  O   HOH X 186      36.207  73.382 -16.407  1.00 14.78           O
ATOM  41349  O   HOH X 187      60.020  85.279   3.166  1.00 13.80           O
ATOM  41352  O   HOH X 188      38.527 102.847  20.471  1.00 15.04           O
ATOM  41355  O   HOH X 189      58.079  75.522   4.975  1.00 12.31           O
ATOM  41358  O   HOH X 190      60.252  56.208  32.694  1.00 11.77           O
ATOM  41361  O   HOH X 191      99.012  77.443  44.267  1.00 19.42           O
ATOM  41364  O   HOH X 192      31.694 110.061  16.779  1.00 16.77           O
ATOM  41367  O   HOH X 193      25.754  97.584   3.568  1.00 11.18           O
ATOM  41370  O   HOH X 194      71.238  83.764  30.264  1.00 15.91           O
ATOM  41373  O   HOH X 195      91.037  69.877  53.282  1.00 16.68           O
ATOM  41376  O   HOH X 196       0.713  99.108  -0.777  1.00 17.39           O
ATOM  41379  O   HOH X 197      58.265  57.208  47.666  1.00 12.82           O
ATOM  41382  O   HOH X 198      46.195 100.936  27.665  1.00 11.63           O
ATOM  41385  O   HOH X 199      32.263  61.645  22.510  1.00 12.20           O
ATOM  41388  O   HOH X 200      33.021 107.643  24.790  1.00 14.05           O
ATOM  41391  O   HOH X 201      36.446  94.612  19.273  1.00 13.02           O
ATOM  41394  O   HOH X 202      62.097  53.767  32.675  1.00 16.10           O
ATOM  41397  O   HOH X 203      39.227  67.969  -7.246  1.00 15.97           O
ATOM  41400  O   HOH X 204      19.432  78.475  11.361  1.00 11.97           O
ATOM  41403  O   HOH X 205      24.715  68.004  45.255  1.00 15.57           O
ATOM  41406  O   HOH X 206      19.019 108.996  19.832  1.00 17.52           O
ATOM  41409  O   HOH X 207      23.467  61.698  18.761  1.00 14.07           O
ATOM  41412  O   HOH X 208      20.485  97.512  38.547  1.00 16.07           O
ATOM  41415  O   HOH X 209      28.724  98.740  21.386  1.00 13.74           O
ATOM  41418  O   HOH X 210     -17.995  63.888 -18.024  1.00 13.88           O
ATOM  41421  O   HOH X 211      57.966 108.636  34.753  1.00 16.73           O
ATOM  41424  O   HOH X 212      21.645  79.500  32.357  1.00 13.77           O
ATOM  41427  O   HOH X 213      38.177  93.600  12.523  1.00 12.93           O
ATOM  41430  O   HOH X 214      48.358  84.058 -10.118  1.00 16.30           O
ATOM  41433  O   HOH X 215      15.464  77.268  29.898  1.00 11.04           O
ATOM  41436  O   HOH X 216       8.919  57.421   9.026  1.00 15.48           O
ATOM  41439  O   HOH X 217       6.720  97.913  -3.443  1.00 16.39           O
ATOM  41442  O   HOH X 218      38.994  96.535  18.406  1.00 17.51           O
ATOM  41445  O   HOH X 219      17.339 108.070  15.641  1.00 14.72           O
ATOM  41448  O   HOH X 220      49.025  93.082  34.000  1.00 11.09           O
ATOM  41451  O   HOH X 221      14.543  42.798  18.985  1.00 17.95           O
ATOM  41454  O   HOH X 222      44.456 106.220  16.638  1.00 13.62           O
ATOM  41457  O   HOH X 223      76.280 104.921  35.272  1.00 14.61           O
ATOM  41460  O   HOH X 224      99.486  79.344  51.295  1.00 17.58           O
ATOM  41463  O   HOH X 225       7.075  71.343  25.615  1.00 13.49           O
ATOM  41466  O   HOH X 226      64.342  72.149  35.960  1.00 16.14           O
```

```
ATOM  41469  O   HOH X 227    48.858 100.848  26.764  1.00 10.55           O
ATOM  41472  O   HOH X 228    22.728 104.306   5.584  1.00 10.87           O
ATOM  41475  O   HOH X 229    35.231 108.117  22.797  1.00 12.32           O
ATOM  41478  O   HOH X 230    40.163  66.344 -12.652  1.00 17.94           O
ATOM  41481  O   HOH X 231    54.314 109.457  19.365  1.00 15.71           O
ATOM  41484  O   HOH X 232    75.296  74.593  14.137  1.00 15.47           O
ATOM  41487  O   HOH X 233     2.679  77.167  20.504  1.00 14.49           O
ATOM  41490  O   HOH X 234    22.030 104.049   2.959  1.00 14.17           O
ATOM  41493  O   HOH X 235    24.631  49.735  12.016  1.00 16.04           O
ATOM  41496  O   HOH X 237    45.811  95.576   6.055  1.00 14.24           O
ATOM  41499  O   HOH X 238    41.427  85.509 -17.397  1.00 15.81           O
ATOM  41502  O   HOH X 239    73.021  65.578  42.630  1.00 18.16           O
ATOM  41505  O   HOH X 240    68.261  60.921  45.969  1.00 18.32           O
ATOM  41508  O   HOH X 241    47.019  89.778 -13.714  1.00 15.11           O
ATOM  41511  O   HOH X 242    48.566  87.826  54.081  1.00 13.76           O
ATOM  41514  O   HOH X 243    30.270 101.071  15.106  1.00 14.87           O
ATOM  41517  O   HOH X 244    59.564  74.450  33.024  1.00 17.06           O
ATOM  41520  O   HOH X 245    21.554 114.412 -14.562  1.00 16.17           O
ATOM  41523  O   HOH X 246    53.619 102.339  44.715  1.00 15.84           O
ATOM  41526  O   HOH X 247     3.368  81.796   2.876  1.00 13.50           O
ATOM  41529  O   HOH X 248    16.180  67.883  17.445  1.00 13.11           O
ATOM  41532  O   HOH X 249    67.712 103.068  33.482  1.00 14.87           O
ATOM  41535  O   HOH X 250    33.489  78.959  33.296  1.00 15.09           O
ATOM  41538  O   HOH X 251    39.742  77.880  -6.738  1.00 10.08           O
ATOM  41541  O   HOH X 252    60.143  88.364  30.058  1.00 18.74           O
ATOM  41544  O   HOH X 253    43.176  77.922  28.750  1.00 11.82           O
ATOM  41547  O   HOH X 254    34.697  64.894  22.437  1.00 13.79           O
ATOM  41550  O   HOH X 255    72.490 111.120  29.415  1.00 17.80           O
ATOM  41553  O   HOH X 256    21.734  58.767  16.010  1.00 13.67           O
ATOM  41556  O   HOH X 257    58.350 108.803  30.987  1.00  9.73           O
ATOM  41559  O   HOH X 258    29.046  84.067 -12.761  1.00 15.14           O
ATOM  41562  O   HOH X 259    44.694  60.139  10.236  1.00 12.72           O
ATOM  41565  O   HOH X 260    17.082 108.945  18.210  1.00 20.92           O
ATOM  41568  O   HOH X 261    63.340  54.664  42.405  1.00 13.88           O
ATOM  41571  O   HOH X 262    50.776  88.685  52.840  1.00 17.06           O
ATOM  41574  O   HOH X 263    16.597  79.246  31.550  1.00 13.25           O
ATOM  41577  O   HOH X 264    69.542  61.089   8.094  1.00 14.64           O
ATOM  41580  O   HOH X 265    45.034  53.450  40.276  1.00 14.46           O
ATOM  41583  O   HOH X 266    78.451  72.919  65.294  1.00 18.63           O
ATOM  41586  O   HOH X 267    29.000 109.167 -13.297  1.00 12.62           O
ATOM  41589  O   HOH X 268    25.985  77.471 -19.009  1.00 15.09           O
ATOM  41592  O   HOH X 269    36.012 116.702  43.007  1.00 19.54           O
ATOM  41595  O   HOH X 270    31.071 108.490 -17.586  1.00 14.30           O
ATOM  41598  O   HOH X 271    16.920  80.194  35.147  1.00 12.41           O
ATOM  41601  O   HOH X 272    10.149  55.732   2.252  1.00 15.42           O
ATOM  41604  O   HOH X 273    54.816  81.396  36.918  1.00 13.67           O
ATOM  41607  O   HOH X 274    12.462  79.113  11.069  1.00 13.45           O
ATOM  41610  O   HOH X 275    15.776  59.736   8.651  1.00 13.46           O
ATOM  41613  O   HOH X 276   -22.153  76.324 -26.031  1.00 14.72           O
ATOM  41616  O   HOH X 277     7.301  77.249  24.697  1.00 11.09           O
ATOM  41619  O   HOH X 278    23.329  59.406   9.750  1.00 12.75           O
ATOM  41622  O   HOH X 279    50.696  80.570  25.985  1.00 13.90           O
ATOM  41625  O   HOH X 281    47.053  82.350  21.801  1.00 19.03           O
ATOM  41628  O   HOH X 282    37.079  58.543   5.692  1.00 12.04           O
ATOM  41631  O   HOH X 283    21.119  96.604   7.959  1.00 11.48           O
ATOM  41634  O   HOH X 284    16.689  50.299   2.476  1.00 16.45           O
ATOM  41637  O   HOH X 285    52.435  96.009   6.868  1.00 12.10           O
```

```
ATOM  41640  O   HOH X 286     42.309  98.243   4.350  1.00 16.37           O
ATOM  41643  O   HOH X 287     16.414  49.644  -4.430  1.00 15.74           O
ATOM  41646  O   HOH X 288     60.503 115.939  34.155  1.00 17.20           O
ATOM  41649  O   HOH X 289     22.140  59.164  18.760  1.00 14.94           O
ATOM  41652  O   HOH X 290     63.631  44.406  15.778  1.00 19.36           O
ATOM  41655  O   HOH X 291     43.372  46.933  18.477  1.00 19.90           O
ATOM  41658  O   HOH X 292     57.160 107.670  12.330  1.00 12.76           O
ATOM  41661  O   HOH X 293     35.533  95.726  12.983  1.00 16.28           O
ATOM  41664  O   HOH X 294     18.916  62.571  13.779  1.00 17.43           O
ATOM  41667  O   HOH X 295     24.059  92.342   0.261  1.00 15.83           O
ATOM  41670  O   HOH X 296     64.072 103.089  31.922  1.00 14.14           O
ATOM  41673  O   HOH X 297      5.229  64.371  32.536  1.00 17.73           O
ATOM  41676  O   HOH X 298     -0.630  75.617  22.978  1.00 14.61           O
ATOM  41679  O   HOH X 299     68.354  58.556  35.153  1.00 12.86           O
ATOM  41682  O   HOH X 300     52.058 108.490  20.735  1.00 12.40           O
ATOM  41685  O   HOH X 301     92.868  79.083  62.748  1.00 19.20           O
ATOM  41688  O   HOH X 302     25.709  83.254  27.910  1.00 17.17           O
ATOM  41691  O   HOH X 303     12.676 106.741   3.049  1.00 14.38           O
ATOM  41694  O   HOH X 304     10.011  86.805   0.501  1.00 15.63           O
ATOM  41697  O   HOH X 305     78.174  89.812  40.051  1.00 12.94           O
ATOM  41700  O   HOH X 306     15.115  67.909  42.144  1.00 14.93           O
ATOM  41703  O   HOH X 308     12.592 110.243   0.570  1.00 18.03           O
ATOM  41706  O   HOH X 309      6.671 106.148   3.282  1.00 12.12           O
ATOM  41709  O   HOH X 310     28.161 105.283  45.663  1.00 16.11           O
ATOM  41712  O   HOH X 311     24.418  47.127  30.262  1.00 17.30           O
ATOM  41715  O   HOH X 312     62.182  81.033  24.670  1.00 14.72           O
ATOM  41718  O   HOH X 313     92.608  74.994  57.116  1.00 15.33           O
ATOM  41721  O   HOH X 314     17.209  50.599  19.537  1.00 16.70           O
ATOM  41724  O   HOH X 315     53.845  46.837  12.982  1.00 16.93           O
ATOM  41727  O   HOH X 316     39.220  95.570  10.448  1.00 15.30           O
ATOM  41730  O   HOH X 318     65.707  62.191  10.514  1.00 15.16           O
ATOM  41733  O   HOH X 319     29.205  75.998  11.727  1.00 15.93           O
ATOM  41736  O   HOH X 320     50.859  82.052  47.633  1.00 11.06           O
ATOM  41739  O   HOH X 321     71.381  60.816  21.527  1.00 17.40           O
ATOM  41742  O   HOH X 322     56.249 110.347  42.410  1.00 15.60           O
ATOM  41745  O   HOH X 323     15.031  85.918  37.283  1.00 24.30           O
ATOM  41748  O   HOH X 324    -14.423  78.081 -24.996  1.00 18.02           O
ATOM  41751  O   HOH X 325     93.501  76.423  59.336  1.00 17.91           O
ATOM  41754  O   HOH X 326      1.754  59.083  -1.743  1.00 15.55           O
ATOM  41757  O   HOH X 327     29.723  48.257   3.778  1.00 19.30           O
ATOM  41760  O   HOH X 328     44.934 105.203  37.922  1.00 18.26           O
ATOM  41763  O   HOH X 329     68.189  44.953  14.087  1.00 18.34           O
ATOM  41766  O   HOH X 330      0.081  77.417  21.032  1.00 21.38           O
ATOM  41769  O   HOH X 331     68.982 102.927   6.877  1.00 17.66           O
ATOM  41772  O   HOH X 333     42.813  53.560  26.913  1.00 15.23           O
ATOM  41775  O   HOH X 334     48.933  80.383   7.433  1.00 16.37           O
ATOM  41778  O   HOH X 335     53.425 115.979  39.779  1.00 17.84           O
ATOM  41781  O   HOH X 336     24.571  85.875  28.492  1.00 15.47           O
ATOM  41784  O   HOH X 337     45.551  77.883  25.002  1.00 16.61           O
ATOM  41787  O   HOH X 338     38.725 113.616  13.440  1.00 18.30           O
ATOM  41790  O   HOH X 339    -18.233  66.086 -24.432  1.00 17.43           O
ATOM  41793  O   HOH X 340     33.138  95.107  50.267  1.00 14.26           O
ATOM  41796  O   HOH X 341     20.206  74.671   1.654  1.00 11.28           O
ATOM  41799  O   HOH X 342     16.773  52.108   4.565  1.00 14.63           O
ATOM  41802  O   HOH X 343     37.733  62.760  35.538  1.00 12.73           O
ATOM  41805  O   HOH X 344     35.190 106.012   5.117  1.00 15.63           O
ATOM  41808  O   HOH X 345     35.427  75.341  45.326  1.00 12.10           O
```

```
ATOM  41811  O    HOH X 346      43.605 117.205  44.216  1.00 13.58           O
ATOM  41814  O    HOH X 347      27.586  81.153  13.320  1.00 16.51           O
ATOM  41817  O    HOH X 348      33.522  91.387 -18.140  1.00 16.64           O
ATOM  41820  O    HOH X 349      58.431  52.893  38.733  1.00 14.08           O
ATOM  41823  O    HOH X 350      59.237  74.088   7.117  1.00 12.19           O
ATOM  41826  O    HOH X 351       5.891  88.847  -9.065  1.00 19.80           O
ATOM  41829  O    HOH X 352      32.779  59.124  43.469  1.00 15.90           O
ATOM  41832  O    HOH X 353      16.464 102.913  -6.279  1.00 14.52           O
ATOM  41835  O    HOH X 354      50.507  96.786  31.406  1.00 11.69           O
ATOM  41838  O    HOH X 355      74.503  68.700  35.842  1.00 20.09           O
ATOM  41841  O    HOH X 356      73.876 103.411  30.650  1.00 17.65           O
ATOM  41844  O    HOH X 357      45.674  71.638  57.260  1.00 16.16           O
ATOM  41847  O    HOH X 358      37.356 109.733  21.472  1.00 12.57           O
ATOM  41850  O    HOH X 359      31.850  52.096  16.603  1.00 15.57           O
ATOM  41853  O    HOH X 360      16.219 104.221  -2.539  1.00 12.29           O
ATOM  41856  O    HOH X 361      48.113  63.948  20.774  1.00 10.32           O
ATOM  41859  O    HOH X 362      96.787  93.464  47.417  1.00 16.94           O
ATOM  41862  O    HOH X 363      56.272  67.855  -2.853  1.00 16.53           O
ATOM  41865  O    HOH X 365      38.409 107.996  -5.133  1.00 10.99           O
ATOM  41868  O    HOH X 366      42.826  78.385  -2.685  1.00 15.48           O
ATOM  41871  O    HOH X 367      68.078  60.930  39.236  1.00 14.57           O
ATOM  41874  O    HOH X 368      36.116 101.290   9.061  1.00 16.03           O
ATOM  41877  O    HOH X 369      20.172  51.915  13.597  1.00 15.94           O
ATOM  41880  O    HOH X 370      45.284 109.328  13.845  1.00 17.32           O
ATOM  41883  O    HOH X 371      26.192  91.500  43.643  1.00 12.64           O
ATOM  41886  O    HOH X 372      33.193  76.742  35.119  1.00 16.90           O
ATOM  41889  O    HOH X 373      43.064 107.374  -9.601  1.00 13.45           O
ATOM  41892  O    HOH X 374      89.987  74.129  45.901  1.00 21.07           O
ATOM  41895  O    HOH X 375      46.328  51.224  19.640  1.00 16.72           O
ATOM  41898  O    HOH X 376      24.564  48.205   9.725  1.00 16.93           O
ATOM  41901  O    HOH X 377      96.456  86.236  55.929  1.00 17.10           O
ATOM  41904  O    HOH X 378       7.949  98.035  -0.380  1.00 13.87           O
ATOM  41907  O    HOH X 379      23.639 106.859  18.543  1.00 15.25           O
ATOM  41910  O    HOH X 380      29.675  98.816  -8.323  1.00 15.34           O
ATOM  41913  O    HOH X 381      14.576  84.528   3.881  1.00 17.74           O
ATOM  41916  O    HOH X 382      43.078 117.088  39.265  1.00 13.59           O
ATOM  41919  O    HOH X 383      46.530  80.928  54.613  1.00 16.68           O
ATOM  41922  O    HOH X 384      51.519 117.811  31.076  1.00 14.60           O
ATOM  41925  O    HOH X 385      46.496  96.708 -15.754  1.00 18.70           O
ATOM  41928  O    HOH X 386      -0.439  93.375 -11.114  1.00 15.71           O
ATOM  41931  O    HOH X 387      39.342 105.565   5.507  1.00 12.19           O
ATOM  41934  O    HOH X 388      68.732  78.428   2.947  1.00 15.48           O
ATOM  41937  O    HOH X 389      69.651  58.736  37.697  1.00 12.62           O
ATOM  41940  O    HOH X 390      34.544  80.999   1.969  1.00 19.86           O
ATOM  41943  O    HOH X 391      26.423  60.224  43.328  1.00 19.09           O
ATOM  41946  O    HOH X 392      -8.356  55.015  -8.401  1.00 26.18           O
ATOM  41949  O    HOH X 393      10.438  98.262  -1.903  1.00 13.93           O
ATOM  41952  O    HOH X 394      23.328  77.386 -13.957  1.00 16.76           O
ATOM  41955  O    HOH X 395      67.650  69.709  12.879  1.00 12.84           O
ATOM  41958  O    HOH X 396      62.426 111.338  37.246  1.00 21.60           O
ATOM  41961  O    HOH X 397       9.060  64.683  29.970  1.00 18.10           O
ATOM  41964  O    HOH X 398       1.601 105.379  14.883  1.00 16.70           O
ATOM  41967  O    HOH X 399      56.051  72.959  29.780  1.00 16.36           O
ATOM  41970  O    HOH X 400      65.936  60.912  32.669  1.00 14.10           O
ATOM  41973  O    HOH X 401      51.936  54.443  30.485  1.00 13.03           O
ATOM  41976  O    HOH X 402      50.429  45.045  15.194  1.00 20.58           O
ATOM  41979  O    HOH X 403      34.548 105.862  21.173  1.00 17.15           O
```

| | | | | | | | | | |
|---|---|---|---|---|---|---|---|---|---|
| ATOM | 41982 | O | HOH X 404 | 14.539 | 89.013 | 30.689 | 1.00 | 13.67 | O |
| ATOM | 41985 | O | HOH X 405 | 41.217 | 74.792 | 3.366 | 1.00 | 14.50 | O |
| ATOM | 41988 | O | HOH X 406 | 64.700 | 61.184 | 39.660 | 1.00 | 15.85 | O |
| ATOM | 41991 | O | HOH X 407 | 23.795 | 78.709 | -18.001 | 1.00 | 15.76 | O |
| ATOM | 41994 | O | HOH X 408 | 64.546 | 85.456 | -0.351 | 1.00 | 18.24 | O |
| ATOM | 41997 | O | HOH X 409 | 57.156 | 79.488 | 33.895 | 1.00 | 17.85 | O |
| ATOM | 42000 | O | HOH X 410 | 99.006 | 82.616 | 52.077 | 1.00 | 15.49 | O |
| ATOM | 42003 | O | HOH X 411 | 72.047 | 104.624 | 19.889 | 1.00 | 17.48 | O |
| ATOM | 42006 | O | HOH X 412 | 40.140 | 103.976 | 7.580 | 1.00 | 15.41 | O |
| ATOM | 42009 | O | HOH X 413 | 61.727 | 56.225 | 17.322 | 1.00 | 18.31 | O |
| ATOM | 42012 | O | HOH X 414 | 23.051 | 93.211 | 2.503 | 1.00 | 17.05 | O |
| ATOM | 42015 | O | HOH X 415 | 27.510 | 98.169 | 45.555 | 1.00 | 15.43 | O |
| ATOM | 42018 | O | HOH X 416 | 57.363 | 107.884 | 9.659 | 1.00 | 23.04 | O |
| ATOM | 42021 | O | HOH X 417 | 29.728 | 53.789 | 30.601 | 1.00 | 18.61 | O |
| ATOM | 42024 | O | HOH X 418 | 31.979 | 110.343 | -15.620 | 1.00 | 16.24 | O |
| ATOM | 42027 | O | HOH X 419 | 39.044 | 56.504 | 48.116 | 1.00 | 17.55 | O |
| ATOM | 42030 | O | HOH X 420 | 54.061 | 91.066 | -6.748 | 1.00 | 16.74 | O |
| ATOM | 42033 | O | HOH X 421 | 76.867 | 107.391 | 21.007 | 1.00 | 15.12 | O |
| ATOM | 42036 | O | HOH X 422 | 19.108 | 50.275 | 38.038 | 1.00 | 16.48 | O |
| ATOM | 42039 | O | HOH X 423 | 74.980 | 84.256 | 8.413 | 1.00 | 16.23 | O |
| ATOM | 42042 | O | HOH X 424 | 54.416 | 97.878 | 6.271 | 1.00 | 13.92 | O |
| ATOM | 42045 | O | HOH X 425 | 66.081 | 78.143 | 41.960 | 1.00 | 13.92 | O |
| ATOM | 42048 | O | HOH X 426 | 45.781 | 56.659 | 52.019 | 1.00 | 19.98 | O |
| ATOM | 42051 | O | HOH X 427 | 49.226 | 82.324 | 18.032 | 1.00 | 12.33 | O |
| ATOM | 42054 | O | HOH X 428 | 34.141 | 62.440 | 20.031 | 1.00 | 19.11 | O |
| ATOM | 42057 | O | HOH X 429 | -0.332 | 86.685 | 25.842 | 1.00 | 17.33 | O |
| ATOM | 42060 | O | HOH X 430 | 39.696 | 118.370 | 6.330 | 1.00 | 22.96 | O |
| ATOM | 42063 | O | HOH X 431 | 43.759 | 120.811 | 42.285 | 1.00 | 15.48 | O |
| ATOM | 42066 | O | HOH X 432 | 23.142 | 112.605 | -5.247 | 1.00 | 12.99 | O |
| ATOM | 42069 | O | HOH X 433 | -1.930 | 80.291 | 20.702 | 1.00 | 17.61 | O |
| ATOM | 42072 | O | HOH X 434 | 62.204 | 107.049 | 4.802 | 1.00 | 20.52 | O |
| ATOM | 42075 | O | HOH X 435 | 30.084 | 73.990 | 10.181 | 1.00 | 17.46 | O |
| ATOM | 42078 | O | HOH X 436 | 65.328 | 54.217 | 30.586 | 1.00 | 19.20 | O |
| ATOM | 42081 | O | HOH X 437 | 61.886 | 113.876 | 26.376 | 1.00 | 19.13 | O |
| ATOM | 42084 | O | HOH X 438 | 6.487 | 53.699 | -3.659 | 1.00 | 17.42 | O |
| ATOM | 42087 | O | HOH X 439 | 50.051 | 60.976 | -5.094 | 1.00 | 16.82 | O |
| ATOM | 42090 | O | HOH X 440 | 53.446 | 95.520 | -8.876 | 1.00 | 18.33 | O |
| ATOM | 42093 | O | HOH X 441 | 58.326 | 66.327 | -3.777 | 1.00 | 21.20 | O |
| ATOM | 42096 | O | HOH X 442 | 34.470 | 75.405 | 51.100 | 1.00 | 16.94 | O |
| ATOM | 42099 | O | HOH X 443 | 30.108 | 62.920 | 30.772 | 1.00 | 12.87 | O |
| ATOM | 42102 | O | HOH X 444 | 54.560 | 54.296 | 29.854 | 1.00 | 17.11 | O |
| ATOM | 42105 | O | HOH X 445 | 61.868 | 109.852 | 24.791 | 1.00 | 12.38 | O |
| ATOM | 42108 | O | HOH X 446 | 69.451 | 51.079 | 24.961 | 1.00 | 18.05 | O |
| ATOM | 42111 | O | HOH X 447 | 37.526 | 79.645 | -7.069 | 1.00 | 12.93 | O |
| ATOM | 42114 | O | HOH X 448 | 73.838 | 108.411 | 22.129 | 1.00 | 19.24 | O |
| ATOM | 42117 | O | HOH X 449 | 6.853 | 55.535 | 2.663 | 1.00 | 19.38 | O |
| ATOM | 42120 | O | HOH X 450 | -0.565 | 54.388 | 33.351 | 1.00 | 20.48 | O |
| ATOM | 42123 | O | HOH X 451 | 16.377 | 47.949 | 5.444 | 1.00 | 17.40 | O |
| ATOM | 42126 | O | HOH X 452 | 69.707 | 52.407 | 33.508 | 1.00 | 21.82 | O |
| ATOM | 42129 | O | HOH X 453 | 27.749 | 68.021 | -18.360 | 1.00 | 18.80 | O |
| ATOM | 42132 | O | HOH X 454 | 92.048 | 97.936 | 47.421 | 1.00 | 21.40 | O |
| ATOM | 42135 | O | HOH X 455 | 49.625 | 80.614 | 22.415 | 1.00 | 18.68 | O |
| ATOM | 42138 | O | HOH X 456 | 41.558 | 99.392 | 45.068 | 1.00 | 16.23 | O |
| ATOM | 42141 | O | HOH X 457 | 68.409 | 68.544 | 20.349 | 1.00 | 21.92 | O |
| ATOM | 42144 | O | HOH X 458 | 76.555 | 79.630 | 15.039 | 1.00 | 15.44 | O |
| ATOM | 42147 | O | HOH X 459 | 0.895 | 93.173 | -5.389 | 1.00 | 17.27 | O |
| ATOM | 42150 | O | HOH X 460 | 37.237 | 107.497 | 6.313 | 1.00 | 14.97 | O |

| | | | | | | | | | |
|---|---|---|---|---|---|---|---|---|---|
| ATOM | 42153 | O | HOH | X | 461 | 42.562 | 61.106 | 18.539 | 1.00 12.51 | O |
| ATOM | 42156 | O | HOH | X | 462 | 71.357 | 52.962 | 25.526 | 1.00 18.81 | O |
| ATOM | 42159 | O | HOH | X | 463 | 74.592 | 60.653 | 22.730 | 1.00 20.04 | O |
| ATOM | 42162 | O | HOH | X | 464 | 18.733 | 69.923 | 8.371 | 1.00 17.38 | O |
| ATOM | 42165 | O | HOH | X | 466 | 25.017 | 52.854 | 23.636 | 1.00 13.61 | O |
| ATOM | 42168 | O | HOH | X | 467 | 22.410 | 104.428 | 34.581 | 1.00 16.24 | O |
| ATOM | 42171 | O | HOH | X | 468 | 31.786 | 84.128 | 38.084 | 1.00 14.86 | O |
| ATOM | 42174 | O | HOH | X | 469 | 55.773 | 45.926 | 6.784 | 1.00 17.78 | O |
| ATOM | 42177 | O | HOH | X | 470 | 13.116 | 57.266 | 25.006 | 1.00 20.40 | O |
| ATOM | 42180 | O | HOH | X | 471 | -25.889 | 79.437 | -16.501 | 1.00 17.32 | O |
| ATOM | 42183 | O | HOH | X | 472 | 67.883 | 81.418 | 22.598 | 1.00 15.25 | O |
| ATOM | 42186 | O | HOH | X | 473 | 17.332 | 63.402 | 15.679 | 1.00 21.25 | O |
| ATOM | 42189 | O | HOH | X | 474 | 35.838 | 113.495 | 12.927 | 1.00 15.43 | O |
| ATOM | 42192 | O | HOH | X | 475 | -16.337 | 60.286 | -12.930 | 1.00 16.71 | O |
| ATOM | 42195 | O | HOH | X | 476 | 3.405 | 51.725 | 18.027 | 1.00 19.41 | O |
| ATOM | 42198 | O | HOH | X | 477 | 24.987 | 79.377 | 13.365 | 1.00 19.62 | O |
| ATOM | 42201 | O | HOH | X | 478 | 29.746 | 103.615 | -23.673 | 1.00 20.51 | O |
| ATOM | 42204 | O | HOH | X | 479 | 32.846 | 63.457 | 32.408 | 1.00 17.29 | O |
| ATOM | 42207 | O | HOH | X | 480 | 63.699 | 108.648 | 21.536 | 1.00 15.54 | O |
| ATOM | 42210 | O | HOH | X | 481 | 27.390 | 107.235 | 49.271 | 1.00 22.11 | O |
| ATOM | 42213 | O | HOH | X | 482 | 5.656 | 105.122 | 22.170 | 1.00 17.95 | O |
| ATOM | 42216 | O | HOH | X | 483 | 30.105 | 105.496 | 11.847 | 1.00 13.46 | O |
| ATOM | 42219 | O | HOH | X | 484 | 77.599 | 92.585 | 46.553 | 1.00 18.49 | O |
| ATOM | 42222 | O | HOH | X | 485 | 50.159 | 110.666 | 14.005 | 1.00 17.96 | O |
| ATOM | 42225 | O | HOH | X | 486 | 31.706 | 109.874 | -12.927 | 1.00 14.47 | O |
| ATOM | 42228 | O | HOH | X | 487 | 21.717 | 73.720 | -17.844 | 1.00 18.26 | O |
| ATOM | 42231 | O | HOH | X | 488 | -0.251 | 95.836 | -7.582 | 1.00 17.61 | O |
| ATOM | 42234 | O | HOH | X | 489 | 62.466 | 56.283 | -0.077 | 1.00 17.43 | O |
| ATOM | 42237 | O | HOH | X | 490 | 24.199 | 105.273 | 12.155 | 1.00 20.62 | O |
| ATOM | 42240 | O | HOH | X | 491 | 102.345 | 89.725 | 45.042 | 1.00 21.34 | O |
| ATOM | 42243 | O | HOH | X | 492 | 30.609 | 52.663 | 27.653 | 1.00 14.81 | O |
| ATOM | 42246 | O | HOH | X | 493 | 64.892 | 60.377 | 36.751 | 1.00 13.18 | O |
| ATOM | 42249 | O | HOH | X | 494 | 21.059 | 49.403 | 31.892 | 1.00 16.99 | O |
| ATOM | 42252 | O | HOH | X | 495 | 28.501 | 109.753 | -17.414 | 1.00 18.21 | O |
| ATOM | 42255 | O | HOH | X | 496 | 85.755 | 93.104 | 50.420 | 1.00 19.01 | O |
| ATOM | 42258 | O | HOH | X | 497 | 36.031 | 113.911 | 45.823 | 1.00 16.30 | O |
| ATOM | 42261 | O | HOH | X | 498 | -10.408 | 71.043 | -30.969 | 1.00 20.88 | O |
| ATOM | 42264 | O | HOH | X | 499 | 22.595 | 76.807 | -16.451 | 1.00 15.00 | O |
| ATOM | 42267 | O | HOH | X | 500 | 8.063 | 44.129 | 11.968 | 1.00 21.70 | O |
| ATOM | 42270 | O | HOH | X | 501 | 25.670 | 88.089 | -1.245 | 1.00 14.28 | O |
| ATOM | 42273 | O | HOH | X | 502 | 50.160 | 51.773 | 34.728 | 1.00 17.56 | O |
| ATOM | 42276 | O | HOH | X | 503 | 50.843 | 106.495 | 51.089 | 1.00 18.76 | O |
| ATOM | 42279 | O | HOH | X | 504 | 38.903 | 59.352 | 10.259 | 1.00 19.29 | O |
| ATOM | 42282 | O | HOH | X | 505 | 61.622 | 55.885 | 50.235 | 1.00 15.90 | O |
| ATOM | 42285 | O | HOH | X | 506 | 64.240 | 80.378 | 42.304 | 1.00 16.69 | O |
| ATOM | 42288 | O | HOH | X | 507 | 73.290 | 58.670 | 48.196 | 1.00 16.92 | O |
| ATOM | 42291 | O | HOH | X | 508 | -0.110 | 93.799 | 26.116 | 1.00 16.35 | O |
| ATOM | 42294 | O | HOH | X | 509 | 21.494 | 48.883 | -9.897 | 1.00 20.89 | O |
| ATOM | 42297 | O | HOH | X | 510 | 24.051 | 78.209 | 9.902 | 1.00 15.64 | O |
| ATOM | 42300 | O | HOH | X | 511 | 54.611 | 112.019 | 40.851 | 1.00 15.78 | O |
| ATOM | 42303 | O | HOH | X | 512 | 51.275 | 62.157 | 22.118 | 1.00 14.44 | O |
| ATOM | 42306 | O | HOH | X | 513 | 55.475 | 107.267 | 7.984 | 1.00 20.88 | O |
| ATOM | 42309 | O | HOH | X | 514 | 25.856 | 105.461 | -2.556 | 1.00 11.86 | O |
| ATOM | 42312 | O | HOH | X | 515 | 34.434 | 61.368 | 39.369 | 1.00 16.85 | O |
| ATOM | 42315 | O | HOH | X | 516 | -22.139 | 84.392 | -14.160 | 1.00 18.57 | O |
| ATOM | 42318 | O | HOH | X | 517 | 30.444 | 75.914 | 34.650 | 1.00 19.10 | O |
| ATOM | 42321 | O | HOH | X | 518 | 25.788 | 101.999 | 23.468 | 1.00 21.33 | O |

| | | | | | | | | | |
|---|---|---|---|---|---|---|---|---|---|
| ATOM | 42324 | O | HOH | X | 519 | 55.480 | 50.706 | 23.301 | 1.00 24.69 | O |
| ATOM | 42327 | O | HOH | X | 520 | 10.715 | 106.528 | 6.363 | 1.00 13.98 | O |
| ATOM | 42330 | O | HOH | X | 521 | 50.948 | 105.642 | 9.793 | 1.00 13.65 | O |
| ATOM | 42333 | O | HOH | X | 522 | 51.580 | 56.263 | -4.654 | 1.00 21.00 | O |
| ATOM | 42336 | O | HOH | X | 523 | 43.216 | 120.154 | 20.450 | 1.00 21.43 | O |
| ATOM | 42339 | O | HOH | X | 524 | 13.609 | 97.644 | 39.902 | 1.00 18.90 | O |
| ATOM | 42342 | O | HOH | X | 525 | 32.997 | 91.236 | -13.580 | 1.00 17.72 | O |
| ATOM | 42345 | O | HOH | X | 526 | 10.443 | 50.410 | 5.142 | 1.00 15.69 | O |
| ATOM | 42348 | O | HOH | X | 527 | 45.098 | 59.135 | 52.723 | 1.00 18.53 | O |
| ATOM | 42351 | O | HOH | X | 528 | 74.683 | 91.255 | 6.281 | 1.00 18.96 | O |
| ATOM | 42354 | O | HOH | X | 529 | 100.690 | 89.286 | 50.991 | 1.00 19.17 | O |
| ATOM | 42357 | O | HOH | X | 530 | -17.417 | 88.707 | -15.662 | 1.00 18.63 | O |
| ATOM | 42360 | O | HOH | X | 531 | 38.319 | 45.427 | 24.036 | 1.00 20.02 | O |
| ATOM | 42363 | O | HOH | X | 532 | 20.836 | 49.317 | 17.985 | 1.00 24.21 | O |
| ATOM | 42366 | O | HOH | X | 533 | 79.973 | 71.081 | 0.541 | 1.00 22.72 | O |
| ATOM | 42369 | O | HOH | X | 534 | 13.649 | 103.323 | 35.698 | 1.00 21.35 | O |
| ATOM | 42372 | O | HOH | X | 535 | 82.674 | 73.461 | 40.783 | 1.00 19.47 | O |
| ATOM | 42375 | O | HOH | X | 536 | 50.288 | 90.291 | -8.364 | 1.00 14.65 | O |
| ATOM | 42378 | O | HOH | X | 537 | 28.675 | 98.272 | 24.948 | 1.00 14.92 | O |
| ATOM | 42381 | O | HOH | X | 538 | 22.039 | 101.560 | 26.080 | 1.00 17.80 | O |
| ATOM | 42384 | O | HOH | X | 539 | 18.476 | 48.211 | 2.094 | 1.00 20.53 | O |
| ATOM | 42387 | O | HOH | X | 540 | 21.006 | 102.339 | 39.353 | 1.00 17.24 | O |
| ATOM | 42390 | O | HOH | X | 541 | 48.362 | 54.031 | -1.098 | 1.00 18.54 | O |
| ATOM | 42393 | O | HOH | X | 542 | 36.391 | 112.391 | 20.684 | 1.00 15.43 | O |
| ATOM | 42396 | O | HOH | X | 545 | 31.271 | 117.813 | 4.545 | 1.00 23.59 | O |
| ATOM | 42399 | O | HOH | X | 546 | -2.493 | 76.650 | -17.396 | 1.00 21.20 | O |
| ATOM | 42402 | O | HOH | X | 547 | 74.738 | 102.493 | 38.038 | 1.00 17.63 | O |
| ATOM | 42405 | O | HOH | X | 548 | 11.114 | 46.236 | 29.891 | 1.00 21.49 | O |
| ATOM | 42408 | O | HOH | X | 549 | 91.916 | 70.045 | 56.068 | 1.00 19.31 | O |
| ATOM | 42411 | O | HOH | X | 550 | 38.178 | 110.247 | 6.336 | 1.00 16.88 | O |
| ATOM | 42414 | O | HOH | X | 551 | 61.054 | 54.314 | 44.041 | 1.00 14.85 | O |
| ATOM | 42417 | O | HOH | X | 552 | -22.473 | 68.127 | -20.536 | 1.00 15.85 | O |
| ATOM | 42420 | O | HOH | X | 553 | 14.586 | 48.641 | 3.447 | 1.00 19.41 | O |
| ATOM | 42423 | O | HOH | X | 554 | 42.912 | 109.240 | 10.672 | 1.00 18.01 | O |
| ATOM | 42426 | O | HOH | X | 555 | 48.220 | 97.008 | 8.079 | 1.00 14.88 | O |
| ATOM | 42429 | O | HOH | X | 556 | 89.717 | 67.525 | 53.094 | 1.00 24.06 | O |
| ATOM | 42432 | O | HOH | X | 557 | 23.492 | 106.478 | 1.748 | 1.00 16.00 | O |
| ATOM | 42435 | O | HOH | X | 558 | 80.826 | 103.436 | 24.981 | 1.00 21.46 | O |
| ATOM | 42438 | O | HOH | X | 559 | -1.331 | 57.833 | 25.841 | 1.00 20.43 | O |
| ATOM | 42441 | O | HOH | X | 560 | 31.682 | 56.849 | 22.698 | 1.00 20.28 | O |
| ATOM | 42444 | O | HOH | X | 562 | 59.581 | 61.655 | -2.139 | 1.00 16.16 | O |
| ATOM | 42447 | O | HOH | X | 563 | 16.870 | 53.902 | 0.941 | 1.00 13.86 | O |
| ATOM | 42450 | O | HOH | X | 564 | 9.711 | 46.438 | 27.478 | 1.00 20.99 | O |
| ATOM | 42453 | O | HOH | X | 565 | 25.704 | 116.256 | -10.764 | 1.00 18.95 | O |
| ATOM | 42456 | O | HOH | X | 566 | 29.734 | 50.231 | -9.847 | 1.00 21.02 | O |
| ATOM | 42459 | O | HOH | X | 567 | 21.678 | 104.158 | 41.329 | 1.00 18.72 | O |
| ATOM | 42462 | O | HOH | X | 568 | 6.866 | 105.118 | 0.736 | 1.00 14.09 | O |
| ATOM | 42465 | O | HOH | X | 569 | -20.126 | 89.073 | -15.093 | 1.00 19.20 | O |
| ATOM | 42468 | O | HOH | X | 570 | 20.849 | 94.226 | -14.175 | 1.00 21.07 | O |
| ATOM | 42471 | O | HOH | X | 571 | 102.834 | 74.147 | 44.426 | 1.00 61.37 | O |
| ATOM | 42474 | O | HOH | X | 572 | 51.433 | 62.499 | 31.365 | 1.00 12.01 | O |
| ATOM | 42477 | O | HOH | X | 573 | 98.447 | 74.888 | 44.296 | 1.00 47.73 | O |
| ATOM | 42480 | O | HOH | X | 574 | 45.630 | 50.824 | 44.051 | 1.00 19.63 | O |
| ATOM | 42483 | O | HOH | X | 575 | 32.608 | 85.318 | 40.569 | 1.00 13.64 | O |
| ATOM | 42486 | O | HOH | X | 576 | 18.910 | 78.606 | 32.992 | 1.00 12.22 | O |
| ATOM | 42489 | O | HOH | X | 577 | 95.416 | 74.730 | 44.626 | 1.00 39.57 | O |
| ATOM | 42492 | O | HOH | X | 578 | 55.578 | 114.328 | 40.050 | 1.00 16.24 | O |

| | | | | | | | | | |
|---|---|---|---|---|---|---|---|---|---|
| ATOM | 42495 | O | HOH X | 579 | 29.210 | 109.086 | 13.718 | 1.00 18.76 | O |
| ATOM | 42498 | O | HOH X | 580 | 65.109 | 53.293 | 44.337 | 1.00 19.97 | O |
| ATOM | 42501 | O | HOH X | 581 | 59.037 | 63.198 | 32.450 | 1.00 10.87 | O |
| ATOM | 42504 | O | HOH X | 582 | 64.388 | 109.192 | 25.665 | 1.00 16.61 | O |
| ATOM | 42507 | O | HOH X | 584 | 31.470 | 74.884 | 8.013 | 1.00 15.12 | O |
| ATOM | 42510 | O | HOH X | 585 | 54.816 | 51.570 | 28.676 | 1.00 23.42 | O |
| ATOM | 42513 | O | HOH X | 586 | 44.530 | 76.385 | 26.970 | 1.00 13.21 | O |
| ATOM | 42516 | O | HOH X | 587 | 28.060 | 103.120 | 22.698 | 1.00 21.30 | O |
| ATOM | 42519 | O | HOH X | 588 | 29.275 | 86.196 | 35.391 | 1.00 17.11 | O |
| ATOM | 42522 | O | HOH X | 589 | 36.722 | 96.512 | 10.006 | 1.00 9.81 | O |
| ATOM | 42525 | O | HOH X | 590 | 71.124 | 108.931 | 21.747 | 1.00 17.79 | O |
| ATOM | 42528 | O | HOH X | 591 | 33.839 | 57.548 | 21.054 | 1.00 20.93 | O |
| ATOM | 42531 | O | HOH X | 592 | 44.760 | 57.467 | 11.530 | 1.00 17.88 | O |
| ATOM | 42534 | O | HOH X | 593 | 65.114 | 45.198 | 17.965 | 1.00 20.02 | O |
| ATOM | 42537 | O | HOH X | 594 | 44.366 | 101.060 | 14.730 | 1.00 15.70 | O |
| ATOM | 42540 | O | HOH X | 595 | 55.717 | 74.655 | 3.740 | 1.00 13.16 | O |
| ATOM | 42543 | O | HOH X | 596 | 69.263 | 66.022 | 42.198 | 1.00 23.15 | O |
| ATOM | 42546 | O | HOH X | 597 | 20.909 | 75.709 | 4.300 | 1.00 13.47 | O |
| ATOM | 42549 | O | HOH X | 598 | 43.285 | 58.584 | 17.654 | 1.00 17.70 | O |
| ATOM | 42552 | O | HOH X | 599 | 10.428 | 67.203 | 2.794 | 1.00 17.72 | O |
| ATOM | 42555 | O | HOH X | 600 | 10.197 | 105.752 | 2.439 | 1.00 15.99 | O |
| ATOM | 42558 | O | HOH X | 601 | 53.734 | 79.821 | 32.119 | 1.00 13.35 | O |
| ATOM | 42561 | O | HOH X | 602 | 68.049 | 103.751 | 37.400 | 1.00 19.23 | O |
| ATOM | 42564 | O | HOH X | 603 | 37.911 | 98.036 | 20.854 | 1.00 11.53 | O |
| ATOM | 42567 | O | HOH X | 604 | 58.866 | 77.472 | 33.098 | 1.00 22.44 | O |
| ATOM | 42570 | O | HOH X | 605 | 60.202 | 85.143 | 29.675 | 1.00 16.46 | O |
| ATOM | 42573 | O | HOH X | 606 | 51.077 | 109.869 | 26.065 | 1.00 19.43 | O |
| ATOM | 42576 | O | HOH X | 607 | 16.843 | 84.170 | 38.074 | 1.00 20.22 | O |
| ATOM | 42579 | O | HOH X | 608 | 30.597 | 50.551 | 25.525 | 1.00 16.93 | O |
| ATOM | 42582 | O | HOH X | 609 | 31.401 | 47.980 | 26.562 | 1.00 20.37 | O |
| ATOM | 42585 | O | HOH X | 610 | 65.802 | 43.304 | 14.593 | 1.00 20.56 | O |
| ATOM | 42588 | O | HOH X | 611 | 16.343 | 72.697 | 42.465 | 1.00 18.65 | O |
| ATOM | 42591 | O | HOH X | 612 | 22.922 | 51.899 | 12.900 | 1.00 14.44 | O |
| ATOM | 42594 | O | HOH X | 613 | 23.015 | 111.630 | 43.647 | 1.00 23.16 | O |
| ATOM | 42597 | O | HOH X | 614 | 10.018 | 55.650 | 5.311 | 1.00 17.53 | O |
| ATOM | 42600 | O | HOH X | 615 | 37.118 | 100.677 | 21.747 | 1.00 17.24 | O |
| ATOM | 42603 | O | HOH X | 616 | 30.585 | 52.350 | 13.392 | 1.00 23.74 | O |
| ATOM | 42606 | O | HOH X | 617 | 70.072 | 67.560 | 44.141 | 1.00 33.84 | O |
| ATOM | 42609 | O | HOH X | 618 | 22.996 | 106.953 | 43.205 | 1.00 25.66 | O |
| ATOM | 42612 | O | HOH X | 619 | 38.734 | 82.359 | 35.716 | 1.00 22.97 | O |
| ATOM | 42615 | O | HOH X | 620 | 78.123 | 111.062 | 15.113 | 1.00 15.96 | O |
| ATOM | 42618 | O | HOH X | 621 | 64.516 | 112.164 | 18.804 | 1.00 20.90 | O |
| ATOM | 42621 | O | HOH X | 622 | 76.347 | 107.058 | 11.703 | 1.00 15.24 | O |
| ATOM | 42624 | O | HOH X | 623 | 55.671 | 81.688 | 42.967 | 1.00 18.05 | O |
| ATOM | 42627 | O | HOH X | 624 | 1.867 | 61.908 | 18.027 | 1.00 24.28 | O |
| ATOM | 42630 | O | HOH X | 625 | 6.733 | 79.908 | 12.879 | 1.00 17.50 | O |
| ATOM | 42633 | O | HOH X | 626 | 35.050 | 54.124 | 13.768 | 1.00 27.55 | O |
| ATOM | 42636 | O | HOH X | 627 | 54.084 | 50.611 | 26.203 | 1.00 19.72 | O |
| ATOM | 42639 | O | HOH X | 628 | 35.348 | 97.105 | 20.836 | 1.00 16.87 | O |
| ATOM | 42642 | O | HOH X | 629 | 56.347 | 53.960 | 41.808 | 1.00 13.75 | O |
| ATOM | 42645 | O | HOH X | 630 | 7.714 | 43.155 | 31.260 | 1.00 21.37 | O |
| ATOM | 42648 | O | HOH X | 631 | 31.976 | 47.523 | 2.338 | 1.00 23.86 | O |
| ATOM | 42651 | O | HOH X | 632 | 40.977 | 128.497 | 43.300 | 1.00 31.88 | O |
| ATOM | 42654 | O | HOH X | 633 | 69.585 | 48.621 | 26.277 | 1.00 20.10 | O |
| ATOM | 42657 | O | HOH X | 634 | 40.100 | 85.354 | 32.776 | 1.00 15.61 | O |
| ATOM | 42660 | O | HOH X | 635 | 64.640 | 91.369 | 32.755 | 1.00 13.73 | O |
| ATOM | 42663 | O | HOH X | 636 | 54.275 | 103.458 | 1.574 | 1.00 22.79 | O |

```
ATOM  42666  O    HOH X 637    35.241  53.455  27.641  1.00 33.09           O
ATOM  42669  O    HOH X 638    32.121  50.065  28.663  1.00 22.32           O
ATOM  42672  O    HOH X 639     3.115 106.503   6.319  1.00 17.88           O
ATOM  42675  O    HOH X 640    44.567  99.159   7.963  1.00 19.71           O
ATOM  42678  O    HOH X 641    42.705  53.193  41.815  1.00 24.48           O
ATOM  42681  O    HOH X 642    35.816  62.562  33.623  1.00 19.10           O
ATOM  42684  O    HOH X 643    55.005 100.837   0.494  1.00 17.95           O
ATOM  42687  O    HOH X 644    52.454  74.889  13.890  1.00 17.06           O
ATOM  42690  O    HOH X 645    40.351  56.323   2.443  1.00 19.49           O
ATOM  42693  O    HOH X 646    51.580  96.991  28.990  1.00 13.70           O
ATOM  42696  O    HOH X 647    41.292  61.670  16.148  1.00 18.34           O
ATOM  42699  O    HOH X 648    69.679  49.819  32.768  1.00 25.53           O
ATOM  42702  O    HOH X 649    62.664 112.469  43.718  1.00 26.80           O
ATOM  42705  O    HOH X 650    57.651  51.417  24.482  1.00 19.09           O
ATOM  42708  O    HOH X 651    42.736  48.431  16.136  1.00 22.39           O
ATOM  42711  O    HOH X 652    53.160  60.160  25.650  1.00 11.18           O
ATOM  42714  O    HOH X 653    42.181  52.918  16.009  1.00 22.01           O
ATOM  42717  O    HOH X 654     0.386 105.814   6.005  1.00 18.01           O
ATOM  42720  O    HOH X 655    54.310  77.209  41.136  1.00 17.39           O
ATOM  42723  O    HOH X 657    40.410  53.273  40.757  1.00 18.71           O
ATOM  42726  O    HOH X 658    77.988  74.875  14.338  1.00 32.66           O
ATOM  42729  O    HOH X 659    58.294  55.921  40.806  1.00 13.91           O
ATOM  42732  O    HOH X 660    30.027  60.139  30.321  1.00 17.94           O
ATOM  42735  O    HOH X 661     9.019  84.772  43.028  1.00 70.17           O
ATOM  42738  O    HOH X 662    54.157 111.515  36.834  1.00 23.67           O
ATOM  42741  O    HOH X 663    38.619  52.265  28.563  1.00 39.96           O
ATOM  42744  O    HOH X 664    65.644  47.119   6.342  1.00 19.62           O
ATOM  42747  O    HOH X 665    77.732 106.780  33.743  1.00 16.61           O
ATOM  42750  O    HOH X 666     8.125  67.328   6.952  1.00 25.54           O
ATOM  42753  O    HOH X 667    13.762  47.864  -0.139  1.00 16.96           O
ATOM  42756  O    HOH X 668    69.329  43.533  11.830  1.00 23.16           O
ATOM  42759  O    HOH X 669    64.498 111.193  22.049  1.00 19.53           O
ATOM  42762  O    HOH X 671    57.352  82.073  25.801  1.00 13.04           O
ATOM  42765  O    HOH X 672    65.501 115.268  44.111  1.00 53.70           O
ATOM  42768  O    HOH X 673    53.372 108.260   9.400  1.00 27.59           O
ATOM  42771  O    HOH X 674     6.671  47.074  31.300  1.00 19.76           O
ATOM  42774  O    HOH X 675    41.902  38.776  18.638  1.00 24.21           O
ATOM  42777  O    HOH X 676     8.755  71.147  38.678  1.00 16.49           O
ATOM  42780  O    HOH X 677     9.473  51.600  12.823  1.00 21.65           O
ATOM  42783  O    HOH X 678    72.998  68.316  42.515  1.00 19.63           O
ATOM  42786  O    HOH X 679    60.511  83.026  27.944  1.00 17.83           O
ATOM  42789  O    HOH X 680    27.660  77.405   9.228  1.00 18.40           O
ATOM  42792  O    HOH X 681    51.058  75.496  11.529  1.00 18.97           O
ATOM  42795  O    HOH X 682    65.190  85.463  21.876  1.00 20.48           O
ATOM  42798  O    HOH X 683    79.548 106.992  21.467  1.00 20.20           O
ATOM  42801  O    HOH X 685    32.368 101.434  25.821  1.00 16.23           O
ATOM  42804  O    HOH X 686    61.711 104.463   3.549  1.00 17.99           O
ATOM  42807  O    HOH X 687    36.174  98.137  12.145  1.00 26.57           O
ATOM  42810  O    HOH X 688    67.985 109.158  24.656  1.00 17.74           O
ATOM  42813  O    HOH X 689    68.149 105.523   7.548  1.00 18.95           O
ATOM  42816  O    HOH X 690    33.587  48.439  15.194  1.00 22.64           O
ATOM  42819  O    HOH X 691    17.625  76.398  42.124  1.00 25.91           O
ATOM  42822  O    HOH X 692    81.966  74.015  33.660  1.00 48.10           O
ATOM  42825  O    HOH X 693    74.690  76.777  15.564  1.00 17.28           O
ATOM  42828  O    HOH X 694    65.906 111.237  39.986  1.00 28.16           O
ATOM  42831  O    HOH X 695    42.093 107.737   8.239  1.00 19.31           O
ATOM  42834  O    HOH X 696    26.191 106.712   0.671  1.00 21.14           O
```

| | | | | | | | | | |
|---|---|---|---|---|---|---|---|---|---|
| ATOM | 42837 | O | HOH X | 697 | 86.561 | 74.761 | 43.044 | 1.00 19.97 | O |
| ATOM | 42840 | O | AHOH X | 698 | 52.158 | 92.392 | 42.486 | 0.50 11.53 | O |
| ATOM | 42843 | O | HOH X | 699 | 26.642 | 104.903 | 12.261 | 1.00 21.35 | O |
| ATOM | 42846 | O | HOH X | 700 | 48.767 | 99.868 | 6.521 | 1.00 24.76 | O |
| ATOM | 42849 | O | HOH X | 701 | 12.786 | 107.485 | 24.831 | 1.00 17.87 | O |
| ATOM | 42852 | O | HOH X | 703 | 71.251 | 103.275 | 42.399 | 1.00 37.09 | O |
| ATOM | 42855 | O | HOH X | 704 | 63.819 | 39.229 | 23.686 | 1.00 37.53 | O |
| ATOM | 42858 | O | HOH X | 706 | 73.859 | 60.871 | 41.922 | 1.00 22.15 | O |
| ATOM | 42861 | O | HOH X | 707 | 68.363 | 73.793 | 34.245 | 1.00 22.60 | O |
| ATOM | 42864 | O | HOH X | 708 | 50.091 | 82.754 | 6.102 | 1.00 18.89 | O |
| ATOM | 42867 | O | HOH X | 709 | 49.220 | 104.928 | 11.941 | 1.00 16.88 | O |
| ATOM | 42870 | O | HOH X | 710 | 30.047 | 101.134 | 19.576 | 1.00 39.59 | O |
| ATOM | 42873 | O | HOH X | 711 | 74.521 | 106.125 | 20.964 | 1.00 37.10 | O |
| ATOM | 42876 | O | HOH X | 712 | 35.008 | 61.388 | 25.891 | 1.00 27.07 | O |
| ATOM | 42879 | O | HOH X | 713 | 25.374 | 82.207 | 17.193 | 1.00 16.05 | O |
| ATOM | 42882 | O | HOH X | 714 | 21.467 | 78.621 | 22.716 | 1.00 30.32 | O |
| ATOM | 42885 | O | HOH X | 715 | 12.685 | 90.302 | 32.952 | 1.00 15.04 | O |
| ATOM | 42888 | O | HOH X | 716 | 5.322 | 50.099 | 19.146 | 1.00 20.96 | O |
| ATOM | 42891 | O | HOH X | 717 | 25.774 | 106.927 | 14.314 | 1.00 33.17 | O |
| ATOM | 42894 | O | HOH X | 718 | 70.151 | 110.564 | 27.854 | 1.00 19.66 | O |
| ATOM | 42897 | O | HOH X | 719 | 28.366 | 110.700 | 18.742 | 1.00 28.34 | O |
| ATOM | 42900 | O | HOH X | 720 | 26.428 | 83.189 | 14.967 | 1.00 13.97 | O |
| ATOM | 42903 | O | HOH X | 721 | 61.253 | 71.284 | 32.422 | 1.00 26.11 | O |
| ATOM | 42906 | O | HOH X | 722 | 37.413 | 84.281 | 32.828 | 1.00 16.76 | O |
| ATOM | 42909 | O | HOH X | 723 | 12.737 | 50.524 | 11.130 | 1.00 17.07 | O |
| ATOM | 42912 | O | HOH X | 724 | 66.370 | 116.964 | 37.655 | 1.00 40.07 | O |
| ATOM | 42915 | O | HOH X | 725 | 10.247 | 71.905 | 40.874 | 1.00 23.47 | O |
| ATOM | 42918 | O | HOH X | 726 | 76.142 | 91.037 | 31.771 | 1.00 21.67 | O |
| ATOM | 42921 | O | HOH X | 727 | 40.607 | 57.082 | 11.068 | 1.00 27.84 | O |
| ATOM | 42924 | O | HOH X | 728 | 22.220 | 106.110 | 32.711 | 1.00 30.61 | O |
| ATOM | 42927 | O | HOH X | 729 | 28.345 | 80.762 | 43.030 | 1.00 17.62 | O |
| ATOM | 42930 | O | HOH X | 730 | 65.606 | 105.237 | 3.992 | 1.00 37.04 | O |
| ATOM | 42933 | O | HOH X | 731 | 65.867 | 65.903 | 0.313 | 1.00 17.15 | O |
| ATOM | 42936 | O | HOH X | 733 | 55.489 | 88.899 | 28.370 | 1.00 18.64 | O |
| ATOM | 42939 | O | HOH X | 734 | -0.048 | 104.187 | 8.173 | 1.00 23.90 | O |
| ATOM | 42942 | O | HOH X | 735 | 28.480 | 51.825 | 24.260 | 1.00 17.74 | O |
| ATOM | 42945 | O | HOH X | 736 | 22.201 | 76.079 | 23.137 | 1.00 13.53 | O |
| ATOM | 42948 | O | HOH X | 737 | 42.086 | 99.574 | 6.774 | 1.00 17.81 | O |
| ATOM | 42951 | O | HOH X | 738 | 69.133 | 43.988 | 16.641 | 1.00 25.53 | O |
| ATOM | 42954 | O | HOH X | 739 | 32.386 | 104.471 | 22.411 | 1.00 23.09 | O |
| ATOM | 42957 | O | HOH X | 740 | 39.977 | 64.224 | 17.803 | 1.00 13.58 | O |
| ATOM | 42960 | O | HOH X | 741 | 71.725 | 103.185 | 6.339 | 1.00 20.79 | O |
| ATOM | 42963 | O | HOH X | 742 | 66.094 | 78.304 | 30.442 | 1.00 52.27 | O |
| ATOM | 42966 | O | HOH X | 743 | 9.281 | 80.370 | 14.318 | 1.00 20.43 | O |
| ATOM | 42969 | O | HOH X | 744 | 55.680 | 88.171 | 42.368 | 1.00 15.89 | O |
| ATOM | 42972 | O | HOH X | 745 | 37.623 | 56.838 | 1.642 | 1.00 19.49 | O |
| ATOM | 42975 | O | HOH X | 746 | 46.351 | 109.203 | 8.741 | 1.00 22.93 | O |
| ATOM | 42978 | O | HOH X | 747 | 68.736 | 71.149 | 44.501 | 1.00 20.21 | O |
| ATOM | 42981 | O | HOH X | 748 | 40.482 | 108.431 | 6.258 | 1.00 16.79 | O |
| ATOM | 42984 | O | HOH X | 749 | 5.106 | 48.795 | 10.571 | 1.00 23.65 | O |
| ATOM | 42987 | O | HOH X | 750 | 41.531 | 72.060 | 2.295 | 1.00 18.51 | O |
| ATOM | 42990 | O | HOH X | 751 | 35.331 | 60.329 | 15.741 | 1.00 24.55 | O |
| ATOM | 42993 | O | HOH X | 752 | 13.704 | 66.151 | 32.952 | 1.00 24.73 | O |
| ATOM | 42996 | O | HOH X | 753 | 37.360 | 63.426 | 20.279 | 1.00 29.24 | O |
| ATOM | 42999 | O | HOH X | 754 | 7.951 | 44.775 | 14.449 | 1.00 26.66 | O |
| ATOM | 43002 | O | HOH X | 755 | 20.970 | 109.669 | 18.041 | 1.00 26.00 | O |
| ATOM | 43005 | O | HOH X | 756 | 52.580 | 43.296 | 9.005 | 1.00 34.13 | O |

| | | | | | | | | | |
|---|---|---|---|---|---|---|---|---|---|
| ATOM | 43008 | O | HOH | X | 757 | 43.863 | 129.182 | 43.355 | 1.00 15.98 | O |
| ATOM | 43011 | O | HOH | X | 758 | 2.221 | 49.655 | 10.857 | 1.00 29.07 | O |
| ATOM | 43014 | O | HOH | X | 759 | 52.523 | 98.426 | 4.006 | 1.00 18.32 | O |
| ATOM | 43017 | O | HOH | X | 760 | 53.505 | 48.494 | 30.237 | 1.00 32.42 | O |
| ATOM | 43020 | O | HOH | X | 762 | 37.914 | 104.378 | 12.370 | 1.00 20.52 | O |
| ATOM | 43023 | O | HOH | X | 763 | 34.681 | 120.297 | 18.727 | 1.00 24.42 | O |
| ATOM | 43026 | O | HOH | X | 764 | 53.266 | 81.091 | 41.432 | 1.00 17.22 | O |
| ATOM | 43029 | O | HOH | X | 765 | 75.245 | 50.513 | 21.572 | 1.00 34.46 | O |
| ATOM | 43032 | O | HOH | X | 766 | 32.916 | 56.727 | 33.865 | 1.00 33.82 | O |
| ATOM | 43035 | O | HOH | X | 767 | 25.319 | 105.599 | 16.815 | 1.00 22.75 | O |
| ATOM | 43038 | O | HOH | X | 768 | 32.768 | 76.832 | 25.398 | 1.00 22.11 | O |
| ATOM | 43041 | O | HOH | X | 769 | -0.677 | 84.901 | 32.998 | 1.00 34.81 | O |
| ATOM | 43044 | O | HOH | X | 770 | 80.881 | 86.995 | 15.439 | 1.00 24.43 | O |
| ATOM | 43047 | O | HOH | X | 771 | 76.826 | 83.262 | 6.737 | 1.00 27.17 | O |
| ATOM | 43050 | O | HOH | X | 772 | 3.139 | 46.462 | 17.236 | 1.00 24.97 | O |
| ATOM | 43053 | O | HOH | X | 773 | 35.024 | 50.438 | 7.731 | 1.00 21.57 | O |
| ATOM | 43056 | O | HOH | X | 774 | 39.734 | 101.692 | 9.418 | 1.00 32.89 | O |
| ATOM | 43059 | O | HOH | X | 775 | 55.125 | 31.089 | 17.954 | 1.00 42.73 | O |
| ATOM | 43062 | O | HOH | X | 776 | 74.484 | 101.267 | 44.711 | 1.00 26.74 | O |
| ATOM | 43065 | O | HOH | X | 777 | 32.398 | 109.492 | 19.486 | 1.00 17.47 | O |
| ATOM | 43068 | O | HOH | X | 778 | 33.469 | 62.924 | 24.483 | 1.00 20.27 | O |
| ATOM | 43071 | O | HOH | X | 779 | 76.104 | 56.649 | 16.479 | 1.00 21.72 | O |
| ATOM | 43074 | O | HOH | X | 780 | 37.387 | 78.445 | 4.633 | 1.00 28.82 | O |
| ATOM | 43077 | O | HOH | X | 781 | 41.301 | 116.227 | 7.073 | 1.00 26.56 | O |
| ATOM | 43080 | O | HOH | X | 782 | 9.943 | 108.765 | 5.104 | 1.00 23.29 | O |
| ATOM | 43083 | O | HOH | X | 783 | 12.266 | 62.159 | 41.719 | 1.00 15.37 | O |
| ATOM | 43086 | O | HOH | X | 784 | 57.400 | 64.786 | 24.525 | 1.00 14.02 | O |
| ATOM | 43089 | O | HOH | X | 785 | 10.020 | 87.630 | 39.551 | 1.00 46.47 | O |
| ATOM | 43092 | O | HOH | X | 786 | 80.204 | 107.845 | 13.751 | 1.00 20.07 | O |
| ATOM | 43095 | O | HOH | X | 787 | 28.189 | 50.412 | 42.945 | 1.00 62.89 | O |
| ATOM | 43098 | O | HOH | X | 788 | 74.626 | 81.505 | 1.332 | 1.00 36.76 | O |
| ATOM | 43101 | O | HOH | X | 789 | 23.643 | 116.377 | 44.515 | 1.00 28.38 | O |
| ATOM | 43104 | O | HOH | X | 790 | 92.071 | 91.863 | 38.580 | 1.00 31.40 | O |
| ATOM | 43107 | O | HOH | X | 791 | 45.416 | 54.764 | 32.345 | 1.00 20.26 | O |
| ATOM | 43110 | O | HOH | X | 792 | 22.280 | 111.045 | 5.714 | 1.00 47.24 | O |
| ATOM | 43113 | O | HOH | X | 793 | 102.491 | 82.651 | 31.696 | 1.00 28.24 | O |
| ATOM | 43116 | O | HOH | X | 794 | 38.385 | 56.381 | 12.678 | 1.00 33.12 | O |
| ATOM | 43119 | O | HOH | X | 795 | 58.249 | 115.922 | 35.552 | 1.00 24.01 | O |
| ATOM | 43122 | O | HOH | X | 796 | 4.947 | 63.460 | 39.758 | 1.00 20.77 | O |
| ATOM | 43125 | O | HOH | X | 797 | 21.564 | 104.532 | 30.469 | 1.00 23.63 | O |
| ATOM | 43128 | O | HOH | X | 798 | 41.028 | 57.650 | 21.070 | 1.00 18.97 | O |
| ATOM | 43131 | O | HOH | X | 799 | 38.956 | 98.476 | 40.915 | 1.00 32.27 | O |
| ATOM | 43134 | O | HOH | X | 800 | 5.117 | 83.722 | 35.820 | 1.00 31.27 | O |
| ATOM | 43137 | O | HOH | X | 801 | 18.679 | 110.689 | 21.769 | 1.00 31.86 | O |
| ATOM | 43140 | O | HOH | X | 802 | 46.965 | 79.950 | 26.802 | 1.00 19.31 | O |
| ATOM | 43143 | O | HOH | X | 803 | 40.580 | 62.570 | 20.606 | 1.00 17.75 | O |
| ATOM | 43146 | O | HOH | X | 804 | 84.286 | 75.505 | 41.825 | 1.00 19.20 | O |
| ATOM | 43149 | O | HOH | X | 805 | 39.063 | 101.405 | 18.110 | 1.00 16.88 | O |
| ATOM | 43152 | O | HOH | X | 806 | 4.501 | 78.039 | 6.361 | 1.00 26.78 | O |
| ATOM | 43155 | O | HOH | X | 807 | 31.992 | 97.704 | 15.880 | 1.00 23.75 | O |
| ATOM | 43158 | O | HOH | X | 808 | 10.089 | 90.160 | 33.946 | 1.00 18.96 | O |
| ATOM | 43161 | O | HOH | X | 809 | 17.351 | 79.830 | 9.750 | 1.00 15.42 | O |
| ATOM | 43164 | O | HOH | X | 810 | 19.070 | 85.627 | 5.296 | 1.00 20.48 | O |
| ATOM | 43167 | O | HOH | X | 811 | 0.562 | 106.147 | 17.207 | 1.00 22.32 | O |
| ATOM | 43170 | O | HOH | X | 812 | 62.637 | 47.261 | 35.306 | 1.00 28.03 | O |
| ATOM | 43173 | O | HOH | X | 813 | 29.841 | 116.861 | 15.377 | 1.00 36.53 | O |
| ATOM | 43176 | O | HOH | X | 814 | 61.902 | 112.828 | 41.363 | 1.00 24.32 | O |

| | | | | | | | | | | |
|---|---|---|---|---|---|---|---|---|---|---|
| ATOM | 43179 | O | HOH | X | 815 | 37.246 | 79.977 | 2.449 | 1.00 20.91 | O |
| ATOM | 43182 | O | HOH | X | 816 | 16.916 | 82.004 | 5.222 | 1.00 28.70 | O |
| ATOM | 43185 | O | HOH | X | 818 | 62.758 | 82.498 | 41.534 | 1.00 21.43 | O |
| ATOM | 43188 | O | HOH | X | 819 | 105.086 | 75.706 | 44.524 | 1.00 66.70 | O |
| ATOM | 43191 | O | HOH | X | 820 | 104.689 | 77.743 | 46.879 | 1.00 59.85 | O |
| ATOM | 43194 | O | HOH | X | 821 | 32.294 | 59.209 | 28.977 | 1.00 17.58 | O |
| ATOM | 43197 | O | HOH | X | 822 | 23.735 | 73.658 | -11.211 | 1.00 13.29 | O |
| ATOM | 43200 | O | HOH | X | 823 | 41.992 | 78.817 | -5.379 | 1.00 14.93 | O |
| ATOM | 43203 | O | HOH | X | 824 | -13.332 | 58.191 | -17.737 | 1.00 18.21 | O |
| ATOM | 43206 | O | HOH | X | 826 | 10.395 | 73.370 | -5.567 | 1.00 18.33 | O |
| ATOM | 43209 | O | HOH | X | 828 | 34.149 | 74.756 | 48.360 | 1.00 16.17 | O |
| ATOM | 43212 | O | HOH | X | 829 | 14.862 | 47.214 | -4.479 | 1.00 20.72 | O |
| ATOM | 43215 | O | HOH | X | 830 | 32.445 | 101.781 | 22.986 | 1.00 16.31 | O |
| ATOM | 43218 | O | HOH | X | 831 | 5.923 | 82.575 | 32.686 | 1.00 13.57 | O |
| ATOM | 43221 | O | HOH | X | 832 | 62.011 | 85.902 | 0.528 | 1.00 17.45 | O |
| ATOM | 43224 | O | HOH | X | 833 | 26.410 | 80.502 | 44.336 | 1.00 33.86 | O |
| ATOM | 43227 | O | HOH | X | 834 | 17.541 | 74.925 | 2.637 | 1.00 17.83 | O |
| ATOM | 43230 | O | HOH | X | 835 | 25.065 | 77.243 | 33.773 | 1.00 16.35 | O |
| ATOM | 43233 | O | HOH | X | 836 | 58.239 | 58.953 | 49.667 | 1.00 17.28 | O |
| ATOM | 43236 | O | HOH | X | 837 | 24.536 | 79.648 | 16.337 | 1.00 21.18 | O |
| ATOM | 43239 | O | HOH | X | 838 | 77.354 | 105.233 | 9.999 | 1.00 20.74 | O |
| ATOM | 43242 | O | HOH | X | 839 | 73.821 | 105.799 | 11.734 | 1.00 15.50 | O |
| ATOM | 43245 | O | HOH | X | 840 | -10.437 | 79.068 | -24.890 | 1.00 21.84 | O |
| ATOM | 43248 | O | HOH | X | 842 | 70.481 | 89.087 | 38.620 | 1.00 18.54 | O |
| ATOM | 43251 | O | HOH | X | 843 | -7.010 | 82.599 | -15.238 | 1.00 17.23 | O |
| ATOM | 43254 | O | HOH | X | 844 | 14.624 | 74.642 | 46.042 | 1.00 51.88 | O |
| ATOM | 43257 | O | HOH | X | 845 | 31.205 | 112.466 | -17.039 | 1.00 16.48 | O |
| ATOM | 43260 | O | HOH | X | 846 | 61.360 | 60.675 | 5.407 | 1.00 28.29 | O |
| ATOM | 43263 | O | HOH | X | 847 | 88.144 | 69.417 | 58.450 | 1.00 20.03 | O |
| ATOM | 43266 | O | HOH | X | 848 | 38.585 | 56.513 | 20.497 | 1.00 22.19 | O |
| ATOM | 43269 | O | HOH | X | 849 | 75.067 | 62.763 | 43.276 | 1.00 17.69 | O |
| ATOM | 43272 | O | HOH | X | 850 | 67.485 | 53.386 | 46.030 | 1.00 17.05 | O |
| ATOM | 43275 | O | HOH | X | 851 | 40.624 | 66.419 | -10.035 | 1.00 19.68 | O |
| ATOM | 43278 | O | HOH | X | 852 | 95.625 | 89.339 | 56.418 | 1.00 20.44 | O |
| ATOM | 43281 | O | HOH | X | 853 | 4.247 | 82.848 | -4.552 | 1.00 22.06 | O |
| ATOM | 43284 | O | HOH | X | 854 | -24.752 | -69.732 | -13.743 | 1.00 16.90 | O |
| ATOM | 43287 | O | HOH | X | 855 | -18.899 | 64.452 | -20.628 | 1.00 15.63 | O |
| ATOM | 43290 | O | HOH | X | 856 | 28.134 | 70.849 | -17.616 | 1.00 22.15 | O |
| ATOM | 43293 | O | HOH | X | 857 | 66.624 | 61.799 | 54.843 | 1.00 20.52 | O |
| ATOM | 43296 | O | HOH | X | 858 | 81.660 | 91.957 | 48.937 | 1.00 17.91 | O |
| ATOM | 43299 | O | HOH | X | 859 | 97.226 | 79.647 | 58.258 | 1.00 16.56 | O |
| ATOM | 43302 | O | HOH | X | 860 | 8.647 | 71.433 | -4.551 | 1.00 16.25 | O |
| ATOM | 43305 | O | HOH | X | 861 | 63.569 | 57.806 | 55.661 | 1.00 18.91 | O |
| ATOM | 43308 | O | HOH | X | 862 | 19.078 | 74.517 | -6.563 | 1.00 18.05 | O |
| ATOM | 43311 | O | HOH | X | 863 | -21.688 | 75.163 | -20.425 | 1.00 15.69 | O |
| ATOM | 43314 | O | HOH | X | 864 | 0.740 | 90.416 | -4.956 | 1.00 19.64 | O |
| ATOM | 43317 | O | HOH | X | 865 | -1.771 | 99.066 | -5.769 | 1.00 16.60 | O |
| ATOM | 43320 | O | HOH | X | 866 | 46.853 | 78.660 | 55.958 | 1.00 13.61 | O |
| ATOM | 43323 | O | HOH | X | 867 | 1.101 | 52.918 | -3.547 | 1.00 16.15 | O |
| ATOM | 43326 | O | HOH | X | 868 | 18.315 | 102.482 | -14.029 | 1.00 20.61 | O |
| ATOM | 43329 | O | HOH | X | 869 | 52.074 | 86.096 | 55.521 | 1.00 24.68 | O |
| ATOM | 43332 | O | HOH | X | 870 | 39.013 | 51.266 | -3.362 | 1.00 16.74 | O |
| ATOM | 43335 | O | HOH | X | 871 | 24.148 | 106.905 | -18.918 | 1.00 23.16 | O |
| ATOM | 43338 | O | HOH | X | 872 | 41.979 | 60.140 | 8.514 | 1.00 17.05 | O |
| ATOM | 43341 | O | HOH | X | 873 | -1.993 | 107.287 | 16.947 | 1.00 20.74 | O |
| ATOM | 43344 | O | HOH | X | 875 | 37.329 | 92.001 | 16.197 | 1.00 18.35 | O |
| ATOM | 43347 | O | HOH | X | 876 | 52.398 | 93.075 | -8.038 | 1.00 16.97 | O |

| | | | | | | | | | |
|---|---|---|---|---|---|---|---|---|---|
| ATOM | 43350 | O | HOH | X | 877 | 5.816 | 45.423 | 29.400 | 1.00 28.16 | O |
| ATOM | 43353 | O | HOH | X | 878 | 52.189 | 98.648 | -4.832 | 1.00 18.01 | O |
| ATOM | 43356 | O | HOH | X | 879 | 21.307 | 108.590 | -13.120 | 1.00 17.89 | O |
| ATOM | 43359 | O | HOH | X | 880 | -8.045 | 66.911 | -2.101 | 1.00 17.54 | O |
| ATOM | 43362 | O | HOH | X | 881 | 4.629 | 106.600 | -0.161 | 1.00 17.65 | O |
| ATOM | 43365 | O | HOH | X | 882 | -28.684 | 77.007 | 0.066 | 1.00 18.24 | O |
| ATOM | 43368 | O | HOH | X | 883 | 94.856 | 73.545 | 56.878 | 1.00 18.33 | O |
| ATOM | 43371 | O | HOH | X | 884 | 37.335 | 66.819 | 19.756 | 1.00 20.96 | O |
| ATOM | 43374 | O | HOH | X | 885 | 61.747 | 57.304 | 53.654 | 1.00 16.60 | O |
| ATOM | 43377 | O | HOH | X | 886 | 23.125 | 63.475 | 46.049 | 1.00 22.12 | O |
| ATOM | 43380 | O | HOH | X | 887 | 26.238 | 86.932 | 30.482 | 1.00 19.87 | O |
| ATOM | 43383 | O | HOH | X | 888 | 48.273 | 83.145 | 3.802 | 1.00 17.13 | O |
| ATOM | 43386 | O | HOH | X | 889 | 3.132 | 55.664 | 4.338 | 1.00 18.57 | O |
| ATOM | 43389 | O | HOH | X | 890 | 101.982 | 80.948 | 33.793 | 1.00 20.29 | O |
| ATOM | 43392 | O | HOH | X | 891 | 41.661 | 57.866 | 15.407 | 1.00 20.79 | O |
| ATOM | 43395 | O | HOH | X | 892 | 4.555 | 107.483 | 4.208 | 1.00 21.33 | O |
| ATOM | 43398 | O | HOH | X | 893 | 72.831 | 104.037 | 37.503 | 1.00 20.67 | O |
| ATOM | 43401 | O | HOH | X | 894 | 26.315 | 98.995 | 22.631 | 1.00 16.95 | O |
| ATOM | 43404 | O | HOH | X | 895 | 87.767 | 77.793 | 44.570 | 1.00 23.54 | O |
| ATOM | 43407 | O | HOH | X | 896 | 44.889 | 106.893 | -3.085 | 1.00 22.71 | O |
| ATOM | 43410 | O | HOH | X | 897 | 81.877 | 86.039 | 67.372 | 1.00 24.79 | O |
| ATOM | 43413 | O | HOH | X | 898 | -10.753 | 56.866 | -14.051 | 1.00 19.44 | O |
| ATOM | 43416 | O | HOH | X | 899 | 25.275 | 109.367 | 45.753 | 1.00 23.75 | O |
| ATOM | 43419 | O | HOH | X | 900 | 44.330 | 111.458 | 52.966 | 1.00 18.88 | O |
| ATOM | 43422 | O | HOH | X | 901 | 51.796 | 119.969 | 43.089 | 1.00 25.09 | O |
| ATOM | 43425 | O | HOH | X | 902 | 24.577 | 110.710 | 13.167 | 1.00 15.48 | O |
| ATOM | 43428 | O | HOH | X | 904 | -27.245 | 76.393 | 2.430 | 1.00 20.78 | O |
| ATOM | 43431 | O | HOH | X | 905 | 2.904 | 66.733 | 38.647 | 1.00 21.30 | O |
| ATOM | 43434 | O | HOH | X | 906 | 65.330 | 81.623 | 21.167 | 1.00 20.92 | O |
| ATOM | 43437 | O | HOH | X | 907 | 34.352 | 47.957 | 3.391 | 1.00 21.11 | O |
| ATOM | 43440 | O | HOH | X | 908 | 55.931 | 37.267 | 10.869 | 1.00 29.79 | O |
| ATOM | 43443 | O | HOH | X | 909 | 33.701 | 98.716 | 19.694 | 1.00 23.05 | O |
| ATOM | 43446 | O | HOH | X | 910 | 102.324 | 73.556 | 46.931 | 1.00 80.79 | O |
| ATOM | 43449 | O | HOH | X | 911 | 31.117 | 46.458 | 11.353 | 1.00 22.26 | O |
| ATOM | 43452 | O | HOH | X | 912 | 100.633 | 82.748 | 54.231 | 1.00 27.53 | O |
| ATOM | 43455 | O | HOH | X | 913 | -29.594 | 74.919 | -11.097 | 1.00 22.86 | O |
| ATOM | 43458 | O | HOH | X | 914 | 44.548 | 80.277 | 28.503 | 1.00 20.07 | O |
| ATOM | 43461 | O | HOH | X | 916 | 14.548 | 44.252 | 6.983 | 1.00 20.85 | O |
| ATOM | 43464 | O | HOH | X | 917 | 10.357 | 86.135 | -2.121 | 1.00 26.70 | O |
| ATOM | 43467 | O | HOH | X | 918 | 90.750 | 100.472 | 41.590 | 1.00 25.03 | O |
| ATOM | 43470 | O | HOH | X | 920 | 32.532 | 54.604 | 27.316 | 1.00 20.55 | O |
| ATOM | 43473 | O | HOH | X | 921 | 11.129 | 103.490 | -11.752 | 1.00 24.86 | O |
| ATOM | 43476 | O | HOH | X | 922 | 31.870 | 93.544 | -20.193 | 1.00 26.33 | O |
| ATOM | 43479 | O | HOH | X | 923 | 39.763 | 54.514 | 35.843 | 1.00 16.92 | O |
| ATOM | 43482 | O | HOH | X | 924 | 30.070 | 77.399 | 7.488 | 1.00 19.48 | O |
| ATOM | 43485 | O | HOH | X | 925 | 74.652 | 48.739 | 11.488 | 1.00 20.30 | O |
| ATOM | 43488 | O | HOH | X | 926 | 81.487 | 110.360 | 23.635 | 1.00 23.04 | O |
| ATOM | 43491 | O | HOH | X | 927 | 33.683 | 56.537 | 42.377 | 1.00 23.93 | O |
| ATOM | 43494 | O | HOH | X | 928 | 59.834 | 91.630 | 31.780 | 1.00 26.91 | O |
| ATOM | 43497 | O | HOH | X | 929 | 40.254 | 99.123 | 8.860 | 1.00 19.82 | O |
| ATOM | 43500 | O | HOH | X | 930 | 19.748 | 75.929 | -0.730 | 1.00 15.66 | O |
| ATOM | 43503 | O | HOH | X | 931 | 21.346 | 74.437 | -4.910 | 1.00 20.39 | O |
| ATOM | 43506 | O | HOH | X | 932 | 73.650 | 81.965 | 9.031 | 1.00 17.46 | O |
| ATOM | 43509 | O | HOH | X | 933 | 14.519 | 87.077 | 1.695 | 1.00 26.70 | O |
| ATOM | 43512 | O | HOH | X | 934 | 1.611 | 61.786 | -2.298 | 1.00 21.38 | O |
| ATOM | 43515 | O | HOH | X | 935 | 106.054 | 93.320 | 43.563 | 1.00 107.79 | O |
| ATOM | 43518 | O | HOH | X | 936 | -17.017 | 63.362 | -25.690 | 1.00 24.38 | O |

| | | | | | | | | | |
|---|---|---|---|---|---|---|---|---|---|
| ATOM | 43521 | O | HOH X 937 | 45.124 | 54.146 | -9.394 | 1.00 | 25.94 | O |
| ATOM | 43524 | O | HOH X 938 | 50.838 | 115.812 | 45.958 | 1.00 | 20.45 | O |
| ATOM | 43527 | O | HOH X 939 | 22.572 | 96.145 | -23.866 | 1.00 | 22.61 | O |
| ATOM | 43530 | O | HOH X 940 | 33.038 | 58.287 | 46.121 | 1.00 | 21.96 | O |
| ATOM | 43533 | O | HOH X 941 | -20.983 | 67.691 | -6.037 | 1.00 | 30.65 | O |
| ATOM | 43536 | O | HOH X 943 | 55.522 | 70.275 | -6.735 | 1.00 | 20.01 | O |
| ATOM | 43539 | O | HOH X 944 | 69.887 | 107.417 | 8.600 | 1.00 | 21.78 | O |
| ATOM | 43542 | O | HOH X 945 | 60.729 | 54.650 | -0.956 | 1.00 | 19.93 | O |
| ATOM | 43545 | O | HOH X 946 | 28.920 | 61.036 | -17.619 | 1.00 | 20.69 | O |
| ATOM | 43548 | O | HOH X 947 | 51.603 | 57.910 | 55.545 | 1.00 | 19.69 | O |
| ATOM | 43551 | O | HOH X 948 | 34.157 | 110.615 | 21.223 | 1.00 | 20.55 | O |
| ATOM | 43554 | O | HOH X 949 | -17.307 | 59.447 | -15.547 | 1.00 | 24.03 | O |
| ATOM | 43557 | O | HOH X 950 | 19.434 | 104.818 | 28.884 | 1.00 | 16.44 | O |
| ATOM | 43560 | O | HOH X 951 | 6.196 | 46.100 | 20.739 | 1.00 | 19.00 | O |
| ATOM | 43563 | O | HOH X 952 | 60.964 | 97.604 | -5.687 | 1.00 | 25.21 | O |
| ATOM | 43566 | O | HOH X 953 | -26.207 | 81.983 | -15.279 | 1.00 | 19.07 | O |
| ATOM | 43569 | O | HOH X 954 | -24.400 | 70.059 | -6.571 | 1.00 | 22.98 | O |
| ATOM | 43572 | O | HOH X 955 | 55.007 | 109.271 | 12.666 | 1.00 | 22.43 | O |
| ATOM | 43575 | O | HOH X 956 | 14.121 | 80.053 | 7.431 | 1.00 | 16.66 | O |
| ATOM | 43578 | O | HOH X 957 | 57.311 | 101.950 | -0.711 | 1.00 | 20.10 | O |
| ATOM | 43581 | O | HOH X 958 | 17.068 | 45.410 | 5.012 | 1.00 | 24.37 | O |
| ATOM | 43584 | O | HOH X 960 | 24.987 | 105.192 | 24.850 | 1.00 | 28.64 | O |
| ATOM | 43587 | O | HOH X 961 | 25.705 | 51.635 | 36.647 | 1.00 | 25.55 | O |
| ATOM | 43590 | O | HOH X 963 | 51.525 | 111.744 | 11.927 | 1.00 | 27.39 | O |
| ATOM | 43593 | O | HOH X 965 | 105.522 | 81.799 | 43.096 | 1.00 | 71.93 | O |
| ATOM | 43596 | O | HOH X 966 | 20.413 | 110.987 | -14.231 | 1.00 | 20.83 | O |
| ATOM | 43599 | O | HOH X 967 | 14.320 | 111.131 | -3.097 | 1.00 | 20.66 | O |
| ATOM | 43602 | O | HOH X 968 | 12.880 | 96.184 | 45.077 | 1.00 | 55.39 | O |
| ATOM | 43605 | O | HOH X 969 | -15.331 | 66.324 | -7.120 | 1.00 | 20.15 | O |
| ATOM | 43608 | O | HOH X 970 | -1.558 | 67.677 | 33.828 | 1.00 | 23.44 | O |
| ATOM | 43611 | O | HOH X 971 | 15.091 | 70.103 | 4.887 | 1.00 | 21.54 | O |
| ATOM | 43614 | O | HOH X 972 | 71.888 | 75.417 | 38.131 | 1.00 | 22.06 | O |
| ATOM | 43617 | O | HOH X 973 | 30.549 | 118.287 | 36.727 | 1.00 | 29.04 | O |
| ATOM | 43620 | O | HOH X 974 | 10.038 | 110.425 | -0.276 | 1.00 | 25.53 | O |
| ATOM | 43623 | O | HOH X 975 | -20.255 | 62.631 | -17.329 | 1.00 | 23.77 | O |
| ATOM | 43626 | O | HOH X 976 | 37.397 | 101.919 | -13.385 | 1.00 | 15.92 | O |
| ATOM | 43629 | O | HOH X 977 | 8.318 | 87.850 | 33.467 | 1.00 | 27.83 | O |
| ATOM | 43632 | O | HOH X 978 | 99.385 | 92.335 | 47.154 | 1.00 | 21.00 | O |
| ATOM | 43635 | O | HOH X 979 | 67.558 | 72.105 | 10.892 | 1.00 | 21.14 | O |
| ATOM | 43638 | O | HOH X 980 | 54.594 | 118.354 | 39.979 | 1.00 | 23.09 | O |
| ATOM | 43641 | O | HOH X 981 | 37.412 | 73.737 | 52.987 | 1.00 | 27.11 | O |
| ATOM | 43644 | O | HOH X 982 | 10.877 | 59.716 | 45.781 | 1.00 | 29.12 | O |
| ATOM | 43647 | O | HOH X 983 | 26.750 | 68.961 | 51.996 | 1.00 | 17.51 | O |
| ATOM | 43650 | O | HOH X 984 | 59.222 | 109.529 | 13.322 | 1.00 | 19.42 | O |
| ATOM | 43653 | O | HOH X 985 | 44.295 | 71.433 | 2.919 | 1.00 | 21.53 | O |
| ATOM | 43656 | O | HOH X 986 | 95.958 | 77.619 | 59.640 | 1.00 | 18.01 | O |
| ATOM | 43659 | O | HOH X 987 | 41.899 | 74.808 | 11.443 | 1.00 | 20.05 | O |
| ATOM | 43662 | O | HOH X 988 | 37.238 | 50.029 | 28.619 | 1.00 | 20.93 | O |
| ATOM | 43665 | O | HOH X 989 | 9.786 | 90.682 | -4.038 | 1.00 | 28.35 | O |
| ATOM | 43668 | O | HOH X 990 | 5.260 | 47.377 | 18.523 | 1.00 | 24.28 | O |
| ATOM | 43671 | O | HOH X 991 | -0.087 | 95.490 | 0.061 | 1.00 | 21.95 | O |
| ATOM | 43674 | O | HOH X 992 | 48.434 | 85.100 | -12.562 | 1.00 | 18.07 | O |
| ATOM | 43677 | O | HOH X 993 | 0.126 | 63.976 | 4.057 | 1.00 | 22.33 | O |
| ATOM | 43680 | O | HOH X 994 | 99.064 | 86.189 | 56.153 | 1.00 | 25.62 | O |
| ATOM | 43683 | O | HOH X 995 | 48.107 | 59.963 | -11.793 | 1.00 | 21.37 | O |
| ATOM | 43686 | O | HOH X 996 | 2.110 | 106.692 | -1.557 | 1.00 | 17.73 | O |
| ATOM | 43689 | O | HOH X 997 | 44.057 | 89.821 | 47.345 | 1.00 | 18.02 | O |

| | | | | | | | | | |
|---|---|---|---|---|---|---|---|---|---|
| ATOM | 43692 | O | HOH | X 998 | 36.575 | 98.133 | 42.403 | 1.00 24.15 | O |
| ATOM | 43695 | O | HOH | X 999 | 64.668 | 66.213 | -2.002 | 1.00 26.82 | O |
| ATOM | 43698 | O | HOH | X1000 | 35.765 | 49.101 | -4.718 | 1.00 23.27 | O |
| ATOM | 43701 | O | HOH | X1001 | 27.414 | 57.764 | 46.134 | 1.00 43.94 | O |
| ATOM | 43704 | O | HOH | X1002 | -15.061 | 57.978 | -11.922 | 1.00 24.38 | O |
| ATOM | 43707 | O | HOH | X1003 | 8.651 | 104.044 | -11.808 | 1.00 28.78 | O |
| ATOM | 43710 | O | HOH | X1004 | 1.683 | 72.417 | -21.177 | 1.00 24.00 | O |
| ATOM | 43713 | O | HOH | X1005 | -20.389 | 90.790 | -11.093 | 1.00 25.92 | O |
| ATOM | 43716 | O | HOH | X1006 | 12.338 | 109.508 | 23.072 | 1.00 21.47 | O |
| ATOM | 43719 | O | HOH | X1007 | 29.540 | 62.605 | 51.337 | 1.00 20.29 | O |
| ATOM | 43722 | O | HOH | X1008 | 23.784 | 96.481 | -21.364 | 1.00 17.75 | O |
| ATOM | 43725 | O | HOH | X1009 | 71.742 | 60.654 | 37.657 | 1.00 23.04 | O |
| ATOM | 43728 | O | HOH | X1010 | 82.305 | 108.199 | 34.232 | 1.00 26.83 | O |
| ATOM | 43731 | O | HOH | X1011 | 44.898 | 114.082 | 51.420 | 1.00 16.50 | O |
| ATOM | 43734 | O | HOH | X1012 | 37.059 | 102.349 | 16.152 | 1.00 17.83 | O |
| ATOM | 43737 | O | HOH | X1013 | 28.286 | 121.179 | -6.593 | 1.00 21.48 | O |
| ATOM | 43740 | O | HOH | X1014 | 72.776 | 105.496 | 14.135 | 1.00 17.46 | O |
| ATOM | 43743 | O | HOH | X1015 | 7.509 | 46.226 | -1.716 | 1.00 20.93 | O |
| ATOM | 43746 | O | HOH | X1016 | 46.478 | 100.969 | 6.883 | 1.00 21.33 | O |
| ATOM | 43749 | O | HOH | X1017 | 64.103 | 52.991 | -3.270 | 1.00 27.36 | O |
| ATOM | 43752 | O | HOH | X1018 | 33.154 | 84.199 | 24.544 | 1.00 20.74 | O |
| ATOM | 43755 | O | HOH | X1019 | -22.777 | 85.513 | -16.559 | 1.00 22.17 | O |
| ATOM | 43758 | O | HOH | X1020 | 70.792 | 60.842 | 57.225 | 1.00 22.16 | O |
| ATOM | 43761 | O | HOH | X1021 | 20.875 | 61.846 | 46.846 | 1.00 20.49 | O |
| ATOM | 43764 | O | HOH | X1022 | 16.940 | 79.560 | 7.054 | 1.00 20.88 | O |
| ATOM | 43767 | O | HOH | X1023 | -17.549 | 83.682 | -19.504 | 1.00 23.19 | O |
| ATOM | 43770 | O | HOH | X1024 | 36.182 | 56.618 | 21.925 | 1.00 19.16 | O |
| ATOM | 43773 | O | HOH | X1025 | 44.969 | 51.414 | 13.172 | 1.00 19.43 | O |
| ATOM | 43776 | O | HOH | X1026 | 73.818 | 96.623 | 36.965 | 1.00 22.00 | O |
| ATOM | 43779 | O | HOH | X1027 | 0.162 | 59.862 | 18.701 | 1.00 23.53 | O |
| ATOM | 43782 | O | HOH | X1028 | 59.115 | 85.901 | 37.380 | 1.00 22.36 | O |
| ATOM | 43785 | O | HOH | X1029 | -6.311 | 100.297 | 4.605 | 1.00 22.20 | O |
| ATOM | 43788 | O | HOH | X1030 | 1.682 | 97.585 | -7.663 | 1.00 18.25 | O |
| ATOM | 43791 | O | HOH | X1031 | 3.052 | 106.284 | -8.097 | 1.00 31.12 | O |
| ATOM | 43794 | O | HOH | X1032 | 44.165 | 107.187 | 12.059 | 1.00 29.80 | O |
| ATOM | 43797 | O | HOH | X1033 | 58.577 | 61.688 | -4.595 | 1.00 21.87 | O |
| ATOM | 43800 | O | HOH | X1034 | 14.770 | 108.431 | 26.692 | 1.00 28.46 | O |
| ATOM | 43803 | O | HOH | X1035 | 15.580 | 80.359 | -2.687 | 1.00 26.58 | O |
| ATOM | 43806 | O | HOH | X1036 | 46.233 | 73.422 | -9.112 | 1.00 21.79 | O |
| ATOM | 43809 | O | HOH | X1037 | 34.888 | 103.284 | 52.592 | 1.00 17.14 | O |
| ATOM | 43812 | O | HOH | X1038 | 28.673 | 72.300 | -19.878 | 1.00 21.06 | O |
| ATOM | 43815 | O | HOH | X1039 | 60.323 | 44.230 | 27.075 | 1.00 17.46 | O |
| ATOM | 43818 | O | HOH | X1040 | 68.094 | 74.959 | 23.425 | 1.00 28.27 | O |
| ATOM | 43821 | O | HOH | X1041 | 48.521 | 110.362 | 26.820 | 1.00 18.82 | O |
| ATOM | 43824 | O | HOH | X1042 | 37.715 | 126.655 | -5.279 | 1.00 20.50 | O |
| ATOM | 43827 | O | HOH | X1043 | 19.945 | 49.618 | 15.647 | 1.00 23.21 | O |
| ATOM | 43830 | O | HOH | X1044 | 36.340 | 60.646 | 23.016 | 1.00 38.12 | O |
| ATOM | 43833 | O | HOH | X1045 | 62.211 | 112.083 | 23.269 | 1.00 21.14 | O |
| ATOM | 43836 | O | HOH | X1046 | 57.246 | 53.297 | 57.881 | 1.00 26.44 | O |
| ATOM | 43839 | O | HOH | X1047 | -20.532 | 64.733 | -11.574 | 1.00 22.97 | O |
| ATOM | 43842 | O | HOH | X1048 | 16.296 | 109.451 | -8.804 | 1.00 23.41 | O |
| ATOM | 43845 | O | HOH | X1049 | 73.096 | 65.159 | 1.707 | 1.00 25.57 | O |
| ATOM | 43848 | O | HOH | X1050 | 36.317 | 100.025 | 54.570 | 1.00 20.29 | O |
| ATOM | 43851 | O | HOH | X1051 | 37.471 | 64.274 | -14.249 | 1.00 27.23 | O |
| ATOM | 43854 | O | HOH | X1052 | 43.086 | 56.444 | 19.702 | 1.00 20.95 | O |
| ATOM | 43857 | O | HOH | X1053 | 21.869 | 112.109 | -16.072 | 1.00 27.81 | O |
| ATOM | 43860 | O | HOH | X1054 | 69.778 | 58.017 | 1.358 | 1.00 23.20 | O |

| | | | | | | | | | |
|---|---|---|---|---|---|---|---|---|---|
| ATOM | 43863 | O | HOH | X1055 | 11.240 | 48.316 | 37.343 | 1.00 26.95 | O |
| ATOM | 43866 | O | HOH | X1056 | 24.314 | 87.073 | 44.339 | 1.00 32.78 | O |
| ATOM | 43869 | O | HOH | X1057 | 73.770 | 53.164 | 35.247 | 1.00 29.71 | O |
| ATOM | 43872 | O | HOH | X1059 | -8.417 | 99.515 | 11.300 | 1.00 31.58 | O |
| ATOM | 43875 | O | HOH | X1060 | 40.415 | 58.484 | 27.396 | 1.00 17.51 | O |
| ATOM | 43878 | O | HOH | X1061 | 13.124 | 107.167 | -9.921 | 1.00 24.71 | O |
| ATOM | 43881 | O | HOH | X1062 | 52.923 | 96.831 | -11.359 | 1.00 19.62 | O |
| ATOM | 43884 | O | HOH | X1063 | 6.326 | 108.672 | -0.724 | 1.00 23.55 | O |
| ATOM | 43887 | O | HOH | X1064 | 35.888 | 77.182 | 0.294 | 1.00 25.36 | O |
| ATOM | 43890 | O | HOH | X1065 | 84.654 | 102.907 | 41.769 | 1.00 23.37 | O |
| ATOM | 43893 | O | HOH | X1066 | 84.735 | 109.260 | 25.756 | 1.00 34.15 | O |
| ATOM | 43896 | O | HOH | X1067 | 52.655 | 59.799 | 22.878 | 1.00 13.94 | O |
| ATOM | 43899 | O | HOH | X1068 | -24.616 | 83.493 | -13.640 | 1.00 24.26 | O |
| ATOM | 43902 | O | HOH | X1069 | 44.216 | 54.780 | 30.018 | 1.00 25.24 | O |
| ATOM | 43905 | O | HOH | X1070 | -10.957 | 83.140 | -16.985 | 1.00 19.16 | O |
| ATOM | 43908 | O | HOH | X1071 | 9.048 | 45.538 | 31.282 | 1.00 19.90 | O |
| ATOM | 43911 | O | HOH | X1072 | -3.127 | 55.571 | -1.373 | 1.00 24.40 | O |
| ATOM | 43914 | O | HOH | X1073 | 52.067 | 106.703 | 53.503 | 1.00 20.20 | O |
| ATOM | 43917 | O | HOH | X1074 | 39.462 | 78.079 | 55.822 | 1.00 24.30 | O |
| ATOM | 43920 | O | HOH | X1075 | 42.099 | 54.308 | 13.510 | 1.00 23.75 | O |
| ATOM | 43923 | O | HOH | X1076 | 1.708 | 50.805 | -5.169 | 1.00 21.49 | O |
| ATOM | 43926 | O | HOH | X1077 | 24.120 | 95.308 | 45.678 | 1.00 31.11 | O |
| ATOM | 43929 | O | HOH | X1078 | 19.608 | 109.509 | 15.156 | 1.00 20.96 | O |
| ATOM | 43932 | O | HOH | X1079 | 11.478 | 112.744 | 17.893 | 1.00 25.10 | O |
| ATOM | 43935 | O | HOH | X1080 | 33.555 | 92.944 | -8.618 | 1.00 33.08 | O |
| ATOM | 43938 | O | HOH | X1081 | 39.393 | 61.730 | 25.480 | 1.00 26.43 | O |
| ATOM | 43941 | O | HOH | X1082 | 31.550 | 59.397 | 24.193 | 1.00 18.90 | O |
| ATOM | 43944 | O | HOH | X1083 | 86.103 | 101.074 | 25.861 | 1.00 25.65 | O |
| ATOM | 43947 | O | HOH | X1084 | 29.366 | 51.707 | 11.068 | 1.00 22.52 | O |
| ATOM | 43950 | O | HOH | X1085 | 30.493 | 81.281 | -13.049 | 1.00 20.42 | O |
| ATOM | 43953 | O | HOH | X1086 | 9.398 | 84.133 | 12.646 | 1.00 20.02 | O |
| ATOM | 43956 | O | HOH | X1087 | -27.527 | 81.593 | -10.995 | 1.00 21.70 | O |
| ATOM | 43959 | O | HOH | X1088 | 13.992 | 60.850 | 43.140 | 1.00 19.08 | O |
| ATOM | 43962 | O | HOH | X1089 | 51.590 | 59.103 | -3.798 | 1.00 19.12 | O |
| ATOM | 43965 | O | HOH | X1090 | 12.025 | 104.912 | -9.163 | 1.00 19.45 | O |
| ATOM | 43968 | O | HOH | X1091 | 41.781 | 125.944 | 44.562 | 1.00 46.82 | O |
| ATOM | 43971 | O | HOH | X1092 | 13.381 | 67.482 | 6.674 | 1.00 29.07 | O |
| ATOM | 43974 | O | HOH | X1094 | 28.474 | 88.320 | 43.015 | 1.00 19.93 | O |
| ATOM | 43977 | O | HOH | X1095 | 36.836 | 105.012 | 16.441 | 1.00 21.69 | O |
| ATOM | 43980 | O | HOH | X1096 | 38.310 | 77.729 | 1.174 | 1.00 19.61 | O |
| ATOM | 43983 | O | HOH | X1097 | -20.297 | 72.354 | -26.795 | 1.00 20.01 | O |
| ATOM | 43986 | O | HOH | X1098 | 34.894 | 118.982 | 41.230 | 1.00 25.52 | O |
| ATOM | 43989 | O | HOH | X1099 | 35.507 | 100.573 | 11.719 | 1.00 19.28 | O |
| ATOM | 43992 | O | HOH | X1100 | 39.184 | 114.316 | -3.490 | 1.00 24.59 | O |
| ATOM | 43995 | O | HOH | X1101 | 76.195 | 64.100 | 5.919 | 1.00 20.68 | O |
| ATOM | 43998 | O | HOH | X1102 | 35.783 | 54.280 | 22.897 | 1.00 22.65 | O |
| ATOM | 44001 | O | HOH | X1103 | 56.188 | 102.814 | 47.158 | 1.00 17.75 | O |
| ATOM | 44004 | O | HOH | X1104 | 34.382 | 56.738 | 14.809 | 1.00 20.75 | O |
| ATOM | 44007 | O | HOH | X1106 | 38.400 | 52.323 | 22.374 | 1.00 35.68 | O |
| ATOM | 44010 | O | HOH | X1107 | 70.358 | 69.063 | 41.886 | 1.00 24.16 | O |
| ATOM | 44013 | O | HOH | X1108 | 51.971 | 86.562 | 51.767 | 1.00 15.53 | O |
| ATOM | 44016 | O | HOH | X1109 | 25.563 | 110.898 | 18.622 | 1.00 28.38 | O |
| ATOM | 44019 | O | HOH | X1110 | 84.158 | 106.644 | 35.806 | 1.00 22.77 | O |
| ATOM | 44022 | O | HOH | X1111 | 21.965 | 90.078 | 39.899 | 1.00 24.05 | O |
| ATOM | 44025 | O | HOH | X1112 | 61.895 | 64.154 | 59.628 | 1.00 25.22 | O |
| ATOM | 44028 | O | HOH | X1113 | 46.584 | 110.350 | 29.036 | 1.00 30.12 | O |
| ATOM | 44031 | O | HOH | X1114 | 75.411 | 51.221 | 10.221 | 1.00 22.08 | O |

| | | | | | | | | | |
|---|---|---|---|---|---|---|---|---|---|
| ATOM | 44034 | O | HOH | X1115 | 48.288 | 119.118 | 44.543 | 1.00 27.15 | O |
| ATOM | 44037 | O | HOH | X1116 | 30.477 | 115.881 | 35.437 | 1.00 22.51 | O |
| ATOM | 44040 | O | HOH | X1117 | 37.639 | 48.248 | 15.829 | 1.00 23.11 | O |
| ATOM | 44043 | O | HOH | X1118 | 49.709 | 89.370 | -13.881 | 1.00 21.62 | O |
| ATOM | 44046 | O | HOH | X1119 | 68.326 | 75.837 | 48.091 | 1.00 39.02 | O |
| ATOM | 44049 | O | HOH | X1120 | -2.976 | 83.909 | -13.133 | 1.00 18.00 | O |
| ATOM | 44052 | O | HOH | X1121 | 49.309 | 122.420 | 35.270 | 1.00 28.98 | O |
| ATOM | 44055 | O | HOH | X1122 | 14.434 | 81.680 | 5.219 | 1.00 21.91 | O |
| ATOM | 44058 | O | HOH | X1123 | 54.048 | 94.737 | 44.869 | 1.00 36.11 | O |
| ATOM | 44061 | O | HOH | X1124 | 60.133 | 115.663 | 29.457 | 1.00 20.82 | O |
| ATOM | 44064 | O | HOH | X1125 | -3.815 | 58.197 | -0.142 | 1.00 16.39 | O |
| ATOM | 44067 | O | HOH | X1126 | 30.505 | 94.463 | 50.380 | 1.00 22.21 | O |
| ATOM | 44070 | O | HOH | X1127 | 18.194 | 59.516 | 47.027 | 1.00 27.39 | O |
| ATOM | 44073 | O | HOH | X1128 | 12.143 | 43.412 | 10.239 | 1.00 27.15 | O |
| ATOM | 44076 | O | HOH | X1129 | 20.009 | 105.815 | 43.062 | 1.00 33.17 | O |
| ATOM | 44079 | O | HOH | X1130 | 85.303 | 66.233 | 46.210 | 1.00 22.16 | O |
| ATOM | 44082 | O | HOH | X1131 | 68.080 | 95.923 | 49.122 | 1.00 36.58 | O |
| ATOM | 44085 | O | HOH | X1132 | 68.838 | 73.746 | 46.558 | 1.00 21.13 | O |
| ATOM | 44088 | O | HOH | X1133 | 68.645 | 96.116 | 41.372 | 1.00 18.04 | O |
| ATOM | 44091 | O | HOH | X1134 | 68.311 | 64.723 | 46.370 | 1.00 20.51 | O |
| ATOM | 44094 | O | HOH | X1135 | 77.913 | 59.575 | 52.835 | 1.00 21.92 | O |
| ATOM | 44097 | O | HOH | X1137 | 36.082 | 82.688 | 55.189 | 1.00 24.97 | O |
| ATOM | 44100 | O | HOH | X1138 | 17.116 | 106.108 | 29.630 | 1.00 23.72 | O |
| ATOM | 44103 | O | HOH | X1139 | 23.416 | 118.194 | -10.101 | 1.00 16.92 | O |
| ATOM | 44106 | O | HOH | X1140 | 45.845 | 118.700 | 43.731 | 1.00 21.57 | O |
| ATOM | 44109 | O | HOH | X1141 | 69.825 | 77.459 | 49.445 | 1.00 29.74 | O |
| ATOM | 44112 | O | HOH | X1142 | 11.489 | 48.706 | 1.418 | 1.00 21.54 | O |
| ATOM | 44115 | O | HOH | X1143 | 50.473 | 105.797 | 16.392 | 1.00 22.22 | O |
| ATOM | 44118 | O | HOH | X1144 | 9.118 | 51.525 | 38.092 | 1.00 22.47 | O |
| ATOM | 44121 | O | HOH | X1145 | 88.710 | 101.890 | 35.822 | 1.00 27.55 | O |
| ATOM | 44124 | O | HOH | X1146 | 61.516 | 113.844 | 37.435 | 1.00 21.61 | O |
| ATOM | 44127 | O | HOH | X1147 | 37.333 | 69.508 | 19.256 | 1.00 25.45 | O |
| ATOM | 44130 | O | HOH | X1148 | 7.384 | 65.680 | 45.311 | 1.00 41.78 | O |
| ATOM | 44133 | O | HOH | X1149 | 95.574 | 82.337 | 30.611 | 1.00 24.90 | O |
| ATOM | 44136 | O | HOH | X1150 | 72.139 | 44.625 | 6.216 | 1.00 40.69 | O |
| ATOM | 44139 | O | HOH | X1151 | 85.511 | 67.039 | 55.311 | 1.00 22.13 | O |
| ATOM | 44142 | O | HOH | X1152 | 2.558 | 90.026 | -2.768 | 1.00 26.18 | O |
| ATOM | 44145 | O | HOH | X1153 | 62.212 | 114.252 | 45.347 | 1.00 36.83 | O |
| ATOM | 44148 | O | HOH | X1154 | 76.464 | 105.732 | 37.949 | 1.00 22.41 | O |
| ATOM | 44151 | O | HOH | X1155 | 15.132 | 66.732 | -16.590 | 1.00 26.39 | O |
| ATOM | 44154 | O | HOH | X1156 | 36.559 | 44.989 | 21.656 | 1.00 20.05 | O |
| ATOM | 44157 | O | HOH | X1157 | 47.451 | 55.342 | 53.441 | 1.00 28.53 | O |
| ATOM | 44160 | O | HOH | X1158 | 87.101 | 79.295 | 36.861 | 1.00 25.44 | O |
| ATOM | 44163 | O | HOH | X1159 | 30.314 | 79.949 | 47.500 | 1.00 20.93 | O |
| ATOM | 44166 | O | HOH | X1160 | 51.460 | 98.843 | -13.868 | 1.00 28.37 | O |
| ATOM | 44169 | O | HOH | X1162 | 23.265 | 48.193 | -11.815 | 1.00 23.71 | O |
| ATOM | 44172 | O | HOH | X1163 | 62.165 | 48.961 | 40.139 | 1.00 31.21 | O |
| ATOM | 44175 | O | HOH | X1165 | 43.116 | 125.869 | 24.892 | 1.00 43.56 | O |
| ATOM | 44178 | O | HOH | X1166 | 39.775 | 92.813 | -21.993 | 1.00 21.36 | O |
| ATOM | 44181 | O | HOH | X1167 | 67.292 | 87.680 | 0.875 | 1.00 27.72 | O |
| ATOM | 44184 | O | HOH | X1168 | 18.817 | 80.906 | -7.841 | 1.00 19.11 | O |
| ATOM | 44187 | O | HOH | X1170 | 6.458 | 107.234 | 20.536 | 1.00 21.76 | O |
| ATOM | 44190 | O | HOH | X1171 | 97.445 | 95.095 | 49.408 | 1.00 27.78 | O |
| ATOM | 44193 | O | HOH | X1172 | 19.994 | 104.344 | -13.020 | 1.00 18.26 | O |
| ATOM | 44196 | O | HOH | X1173 | 34.626 | 51.144 | 29.007 | 1.00 23.38 | O |
| ATOM | 44199 | O | HOH | X1174 | 37.837 | 96.980 | 56.018 | 1.00 25.25 | O |
| ATOM | 44202 | O | HOH | X1175 | 84.438 | 63.033 | 42.326 | 1.00 48.82 | O |

```
ATOM  44205  O   HOH X1176     3.299  74.524 -15.290  1.00 29.10           O
ATOM  44208  O   HOH X1177    42.615  97.714  14.996  1.00 18.96           O
ATOM  44211  O   HOH X1178    57.950 -53.329  49.853  1.00 15.66           O
ATOM  44214  O   HOH X1179    57.378  50.706  40.004  1.00 26.00           O
ATOM  44217  O   HOH X1180    22.843  87.012 -10.988  1.00 30.11           O
ATOM  44220  O   HOH X1181    70.163  87.935  44.436  1.00 42.86           O
ATOM  44223  O   HOH X1183    39.593  51.974  15.880  1.00 32.21           O
ATOM  44226  O   HOH X1184    55.699  64.557  26.783  1.00 18.01           O
ATOM  44229  O   HOH X1186    12.850  53.095 -17.685  1.00 33.15           O
ATOM  44232  O   HOH X1187     7.142  74.319  26.738  1.00 17.66           O
ATOM  44235  O   HOH X1188    58.294  59.110  -5.409  1.00 25.73           O
ATOM  44238  O   HOH X1189    24.734  81.715  25.756  1.00 21.54           O
ATOM  44241  O   HOH X1190    29.029  48.119  -8.352  1.00 26.75           O
ATOM  44244  O   HOH X1191    42.352 102.284   6.752  1.00 19.79           O
ATOM  44247  O   HOH X1192    37.981  90.546 -10.613  1.00 20.10           O
ATOM  44250  O   HOH X1193     3.477  59.890  31.684  1.00 24.05           O
ATOM  44253  O   HOH X1194    60.285  48.929  38.294  1.00 23.04           O
ATOM  44256  O   HOH X1195    49.928  79.310   9.667  1.00 23.91           O
ATOM  44259  O   HOH X1196    12.566  43.636   5.185  1.00 25.11           O
ATOM  44262  O   HOH X1197    85.421  81.010  42.578  1.00 24.29           O
ATOM  44265  O   HOH X1198    79.523  64.842  56.287  1.00 27.42           O
ATOM  44268  O   HOH X1199   103.836  79.114  44.721  1.00 33.07           O
ATOM  44271  O   HOH X1200    43.635  49.710  33.434  1.00 20.23           O
ATOM  44274  O   HOH X1201    61.213  83.003  43.795  1.00 32.78           O
ATOM  44277  O   HOH X1202    46.932 109.058  -2.122  1.00 35.98           O
ATOM  44280  O   HOH X1203    14.049 111.306  16.114  1.00 23.60           O
ATOM  44283  O   HOH X1205    20.388 106.915  27.194  1.00 24.95           O
ATOM  44286  O   HOH X1206    39.769  59.877  15.412  1.00 24.22           O
ATOM  44289  O   HOH X1207    47.000  63.745  58.295  1.00 22.85           O
ATOM  44292  O   HOH X1208     0.963  84.217  25.973  1.00 20.64           O
ATOM  44295  O   HOH X1210    37.248  82.113  31.134  1.00 20.43           O
ATOM  44298  O   HOH X1211    82.406  91.305  63.267  1.00 32.22           O
ATOM  44301  O   HOH X1212    20.746  48.166  38.864  1.00 28.63           O
ATOM  44304  O   HOH X1213    35.058 103.531  20.009  1.00 29.25           O
ATOM  44307  O   HOH X1214    60.945  62.673   7.346  1.00 21.63           O
ATOM  44310  O   HOH X1215    66.463  54.940  56.431  1.00 24.49           O
ATOM  44313  O   HOH X1216    -7.558  64.441 -18.618  1.00 25.39           O
ATOM  44316  O   HOH X1217    10.438 107.245  26.111  1.00 28.28           O
ATOM  44319  O   HOH X1218    14.208  60.745  46.143  1.00 52.53           O
ATOM  44322  O   HOH X1219    24.922  97.795  45.791  1.00 21.36           O
ATOM  44325  O   HOH X1220    65.212  89.864  37.121  1.00 27.09           O
ATOM  44328  O   HOH X1221    35.945  80.265  32.911  1.00 21.28           O
ATOM  44331  O   HOH X1222    29.642  89.524  49.058  1.00 23.94           O
ATOM  44334  O   HOH X1223    51.670 122.837  35.867  1.00 29.96           O
ATOM  44337  O   HOH X1224    35.369  95.674  53.868  1.00 28.41           O
ATOM  44340  O   HOH X1225    80.465  95.070  12.092  1.00 28.34           O
ATOM  44343  O   HOH X1226    68.683  46.884  24.588  1.00 24.01           O
ATOM  44346  O   HOH X1227    39.308  56.571  31.704  1.00 24.46           O
ATOM  44349  O   HOH X1228    56.425 115.766  26.294  1.00 22.46           O
ATOM  44352  O   HOH X1229    29.936 101.052  22.194  1.00 26.87           O
ATOM  44355  O   HOH X1230    91.545  89.425  31.248  1.00 31.48           O
ATOM  44358  O   HOH X1231   -25.085  67.947 -20.169  1.00 24.86           O
ATOM  44361  O   HOH X1232    15.081  83.369 -11.090  1.00 37.97           O
ATOM  44364  O   HOH X1233    -0.320  56.194  -1.500  1.00 18.40           O
ATOM  44367  O   HOH X1234    44.563 109.783   4.453  1.00 42.03           O
ATOM  44370  O   HOH X1235     2.051  47.725  25.533  1.00 28.70           O
ATOM  44373  O   HOH X1236    55.078 114.383  36.991  1.00 25.31           O
```

| | | | | | | | | | |
|---|---|---|---|---|---|---|---|---|---|
| ATOM | 44376 | O | HOH | X1237 | 11.637 | 114.277 | -1.290 | 1.00 33.57 | O |
| ATOM | 44379 | O | HOH | X1238 | 61.436 | 85.374 | 37.978 | 1.00 33.59 | O |
| ATOM | 44382 | O | HOH | X1239 | 91.710 | 98.088 | 50.173 | 1.00 24.95 | O |
| ATOM | 44385 | O | HOH | X1240 | 85.182 | 91.490 | 59.196 | 1.00 27.95 | O |
| ATOM | 44388 | O | HOH | X1242 | 54.183 | 43.681 | 6.654 | 1.00 27.80 | O |
| ATOM | 44391 | O | HOH | X1243 | 22.869 | 104.294 | 26.501 | 1.00 32.41 | O |
| ATOM | 44394 | O | HOH | X1244 | 41.026 | 97.479 | 10.856 | 1.00 22.79 | O |
| ATOM | 44397 | O | HOH | X1245 | 57.451 | 51.764 | 42.430 | 1.00 21.48 | O |
| ATOM | 44400 | O | HOH | X1246 | 66.835 | 92.746 | 45.774 | 1.00 29.48 | O |
| ATOM | 44403 | O | HOH | X1247 | 24.145 | 118.918 | -7.469 | 1.00 26.16 | O |
| ATOM | 44406 | O | HOH | X1248 | -12.482 | 74.024 | -0.009 | 1.00 21.81 | O |
| ATOM | 44409 | O | HOH | X1249 | 32.109 | 110.131 | 25.137 | 1.00 30.80 | O |
| ATOM | 44412 | O | HOH | X1250 | 53.519 | 118.686 | 10.701 | 1.00 41.27 | O |
| ATOM | 44415 | O | HOH | X1251 | 3.075 | 108.704 | 8.147 | 1.00 27.89 | O |
| ATOM | 44418 | O | HOH | X1252 | 91.555 | 72.836 | 65.011 | 1.00 30.79 | O |
| ATOM | 44421 | O | HOH | X1253 | 64.112 | 103.981 | 2.441 | 1.00 24.57 | O |
| ATOM | 44424 | O | HOH | X1254 | 29.227 | 103.838 | 15.968 | 1.00 25.57 | O |
| ATOM | 44427 | O | HOH | X1255 | 104.253 | 83.181 | 47.115 | 1.00 20.82 | O |
| ATOM | 44430 | O | HOH | X1256 | 5.662 | 71.801 | -1.059 | 1.00 24.55 | O |
| ATOM | 44433 | O | HOH | X1257 | 73.361 | 101.363 | 7.498 | 1.00 31.61 | O |
| ATOM | 44436 | O | HOH | X1258 | 23.670 | 91.962 | 42.300 | 1.00 28.06 | O |
| ATOM | 44439 | O | HOH | X1259 | 38.865 | 76.271 | 3.374 | 1.00 25.60 | O |
| ATOM | 44442 | O | HOH | X1260 | -17.377 | 82.581 | -22.246 | 1.00 27.27 | O |
| ATOM | 44445 | O | HOH | X1261 | 42.446 | 56.831 | 13.086 | 1.00 20.49 | O |
| ATOM | 44448 | O | HOH | X1262 | 74.911 | 99.317 | 6.120 | 1.00 25.79 | O |
| ATOM | 44451 | O | HOH | X1263 | -3.177 | 50.307 | -9.716 | 1.00 23.64 | O |
| ATOM | 44454 | O | HOH | X1264 | 69.846 | 86.562 | 35.926 | 1.00 26.81 | O |
| ATOM | 44457 | O | HOH | X1265 | 2.018 | 46.237 | 2.125 | 1.00 31.25 | O |
| ATOM | 44460 | O | HOH | X1266 | 1.018 | 54.775 | 0.310 | 1.00 26.65 | O |
| ATOM | 44463 | O | HOH | X1267 | 67.141 | 41.086 | 15.304 | 1.00 20.34 | O |
| ATOM | 44466 | O | HOH | X1268 | 96.833 | 94.027 | 30.356 | 1.00 28.19 | O |
| ATOM | 44469 | O | HOH | X1270 | 17.097 | 73.157 | 6.233 | 1.00 23.18 | O |
| ATOM | 44472 | O | HOH | X1271 | 54.501 | 76.595 | -4.940 | 1.00 27.27 | O |
| ATOM | 44475 | O | HOH | X1272 | 33.369 | 122.431 | 17.894 | 1.00 34.19 | O |
| ATOM | 44478 | O | HOH | X1273 | 102.681 | 83.090 | 29.151 | 1.00 26.00 | O |
| ATOM | 44481 | O | HOH | X1274 | 25.098 | 106.840 | 20.780 | 1.00 26.04 | O |
| ATOM | 44484 | O | HOH | X1275 | 19.292 | 50.207 | 20.812 | 1.00 25.99 | O |
| ATOM | 44487 | O | HOH | X1277 | 39.563 | 92.058 | -12.504 | 1.00 26.09 | O |
| ATOM | 44490 | O | HOH | X1278 | -27.998 | 80.018 | 6.269 | 1.00 24.64 | O |
| ATOM | 44493 | O | HOH | X1279 | 38.186 | 89.133 | -22.931 | 1.00 22.53 | O |
| ATOM | 44496 | O | HOH | X1280 | 11.933 | 75.621 | -5.597 | 1.00 22.05 | O |
| ATOM | 44499 | O | HOH | X1281 | 49.636 | 72.904 | 3.320 | 1.00 18.87 | O |
| ATOM | 44502 | O | HOH | X1282 | 73.301 | 51.145 | 31.290 | 1.00 26.62 | O |
| ATOM | 44505 | O | HOH | X1283 | -10.748 | 73.966 | -6.063 | 1.00 25.62 | O |
| ATOM | 44508 | O | HOH | X1284 | 44.729 | 108.275 | 6.593 | 1.00 31.96 | O |
| ATOM | 44511 | O | HOH | X1285 | 44.883 | 93.764 | 66.207 | 1.00 37.26 | O |
| ATOM | 44514 | O | HOH | X1286 | -3.358 | 86.219 | 8.142 | 1.00 32.39 | O |
| ATOM | 44517 | O | HOH | X1287 | 95.098 | 98.561 | 42.421 | 1.00 25.77 | O |
| ATOM | 44520 | O | HOH | X1288 | 85.892 | 79.532 | 67.033 | 1.00 31.02 | O |
| ATOM | 44523 | O | HOH | X1289 | 14.667 | 57.223 | 46.670 | 1.00 27.81 | O |
| ATOM | 44526 | O | HOH | X1290 | 97.043 | 76.360 | 40.876 | 1.00 23.29 | O |
| ATOM | 44529 | O | HOH | X1291 | 72.659 | 68.482 | 45.100 | 1.00 27.72 | O |
| ATOM | 44532 | O | HOH | X1292 | 104.239 | 80.281 | 50.447 | 1.00 42.99 | O |
| ATOM | 44535 | O | HOH | X1293 | 43.147 | 72.657 | -13.218 | 1.00 26.58 | O |
| ATOM | 44538 | O | HOH | X1294 | -0.315 | 89.646 | 3.882 | 1.00 25.46 | O |
| ATOM | 44541 | O | HOH | X1295 | 72.728 | 47.087 | 19.392 | 1.00 23.63 | O |
| ATOM | 44544 | O | HOH | X1296 | 9.873 | 104.051 | 31.003 | 1.00 27.93 | O |

| ATOM | 44547 | O | HOH X1297 | 72.521 | 53.030 | 32.915 | 1.00 | 23.14 | O |
| ATOM | 44550 | O | HOH X1298 | 1.110 | 108.410 | 0.529 | 1.00 | 30.03 | O |
| ATOM | 44553 | O | HOH X1299 | 67.016 | 47.410 | 30.885 | 1.00 | 27.27 | O |
| ATOM | 44556 | O | HOH X1300 | 15.819 | 46.468 | 1.540 | 1.00 | 37.94 | O |
| ATOM | 44559 | O | HOH X1301 | 79.564 | 87.507 | 19.899 | 1.00 | 28.15 | O |
| ATOM | 44562 | O | HOH X1302 | 9.877 | 78.845 | -8.313 | 1.00 | 40.33 | O |
| ATOM | 44565 | O | HOH X1303 | 19.146 | 46.244 | 40.047 | 1.00 | 29.96 | O |
| ATOM | 44568 | O | HOH X1304 | 38.474 | 70.654 | -16.744 | 1.00 | 27.83 | O |
| ATOM | 44571 | O | HOH X1305 | 83.718 | 89.055 | 49.582 | 1.00 | 28.78 | O |
| ATOM | 44574 | O | HOH X1306 | 103.415 | 81.976 | 35.940 | 1.00 | 23.68 | O |
| ATOM | 44577 | O | HOH X1307 | 83.883 | 62.758 | 19.738 | 1.00 | 45.63 | O |
| ATOM | 44580 | O | HOH X1308 | 63.046 | 111.563 | 8.934 | 1.00 | 27.09 | O |
| ATOM | 44583 | O | HOH X1309 | 30.303 | 100.599 | -24.455 | 1.00 | 19.89 | O |
| ATOM | 44586 | O | HOH X1310 | -32.360 | 77.047 | -0.686 | 1.00 | 30.30 | O |
| ATOM | 44589 | O | HOH X1311 | 7.169 | 45.117 | 35.668 | 1.00 | 26.42 | O |
| ATOM | 44592 | O | HOH X1312 | 39.754 | 111.110 | -15.233 | 1.00 | 31.64 | O |
| ATOM | 44595 | O | HOH X1313 | -11.567 | 68.671 | -31.041 | 1.00 | 37.39 | O |
| ATOM | 44598 | O | HOH X1314 | 64.520 | 82.532 | 45.277 | 1.00 | 66.59 | O |
| ATOM | 44601 | O | HOH X1315 | -5.358 | 104.531 | 7.431 | 1.00 | 27.55 | O |
| ATOM | 44604 | O | HOH X1316 | 33.077 | 59.528 | 26.363 | 1.00 | 19.26 | O |
| ATOM | 44607 | O | HOH X1317 | -28.327 | 83.376 | -3.032 | 1.00 | 34.99 | O |
| ATOM | 44610 | O | HOH X1318 | 42.002 | 118.439 | 46.145 | 1.00 | 21.81 | O |
| ATOM | 44613 | O | HOH X1319 | -13.093 | 77.052 | -32.781 | 1.00 | 27.81 | O |
| ATOM | 44616 | O | HOH X1320 | 69.644 | 78.603 | -0.264 | 1.00 | 33.19 | O |
| ATOM | 44619 | O | HOH X1321 | 38.974 | 53.814 | 20.213 | 1.00 | 22.55 | O |
| ATOM | 44622 | O | HOH X1322 | 43.045 | 103.564 | 51.693 | 1.00 | 26.33 | O |
| ATOM | 44625 | O | HOH X1323 | 32.782 | 40.279 | 28.823 | 1.00 | 33.18 | O |
| ATOM | 44628 | O | HOH X1324 | -12.869 | 98.362 | -4.678 | 1.00 | 30.76 | O |
| ATOM | 44631 | O | HOH X1325 | 16.198 | 62.017 | 45.319 | 1.00 | 37.10 | O |
| ATOM | 44634 | O | HOH X1326 | 65.506 | 50.963 | 26.409 | 1.00 | 30.51 | O |
| ATOM | 44637 | O | HOH X1327 | 6.503 | 97.265 | -7.501 | 1.00 | 25.39 | O |
| ATOM | 44640 | O | HOH X1328 | 3.109 | 103.312 | -10.225 | 1.00 | 32.66 | O |
| ATOM | 44643 | O | HOH X1329 | 23.497 | 43.419 | 32.514 | 1.00 | 40.17 | O |
| ATOM | 44646 | O | HOH X1330 | 91.942 | 72.554 | 45.842 | 1.00 | 34.67 | O |
| ATOM | 44649 | O | HOH X1331 | -6.100 | 87.213 | 18.242 | 1.00 | 24.88 | O |
| ATOM | 44652 | O | HOH X1332 | 26.258 | 108.901 | -18.967 | 1.00 | 28.91 | O |
| ATOM | 44655 | O | HOH X1333 | -6.141 | 53.244 | 44.236 | 1.00 | 64.58 | O |
| ATOM | 44658 | O | HOH X1334 | 37.311 | 95.350 | 15.761 | 1.00 | 26.05 | O |
| ATOM | 44661 | O | HOH X1335 | 95.579 | 79.345 | 62.280 | 1.00 | 24.95 | O |
| ATOM | 44664 | O | HOH X1336 | 46.288 | 73.746 | -6.526 | 1.00 | 22.74 | O |
| ATOM | 44667 | O | HOH X1337 | -0.360 | 101.703 | 23.667 | 1.00 | 24.47 | O |
| ATOM | 44670 | O | HOH X1338 | 48.806 | 107.066 | 13.699 | 1.00 | 32.96 | O |
| ATOM | 44673 | O | HOH X1339 | 6.743 | 62.815 | 5.119 | 1.00 | 27.34 | O |
| ATOM | 44676 | O | HOH X1340 | 107.098 | 82.307 | 36.406 | 1.00 | 28.49 | O |
| ATOM | 44679 | O | HOH X1341 | 78.069 | 62.158 | 43.142 | 1.00 | 26.26 | O |
| ATOM | 44682 | O | HOH X1342 | 47.463 | 39.837 | 25.280 | 1.00 | 30.94 | O |
| ATOM | 44685 | O | HOH X1343 | 75.044 | 89.643 | 57.055 | 1.00 | 37.69 | O |
| ATOM | 44688 | O | HOH X1344 | 41.960 | 52.703 | -0.812 | 1.00 | 17.55 | O |
| ATOM | 44691 | O | HOH X1345 | 37.501 | 42.823 | 9.306 | 1.00 | 45.91 | O |
| ATOM | 44694 | O | HOH X1346 | 45.224 | 103.241 | 13.056 | 1.00 | 20.29 | O |
| ATOM | 44697 | O | HOH X1347 | -22.015 | 63.948 | -15.795 | 1.00 | 25.01 | O |
| ATOM | 44700 | O | HOH X1348 | 50.140 | 104.551 | -18.761 | 1.00 | 30.32 | O |
| ATOM | 44703 | O | HOH X1350 | 90.933 | 100.078 | 46.351 | 1.00 | 28.10 | O |
| ATOM | 44706 | O | HOH X1351 | 13.581 | 46.401 | -2.434 | 1.00 | 24.85 | O |
| ATOM | 44709 | O | HOH X1352 | 53.822 | 54.604 | -4.916 | 1.00 | 25.08 | O |
| ATOM | 44712 | O | HOH X1353 | 22.024 | 46.804 | -14.000 | 1.00 | 25.61 | O |
| ATOM | 44715 | O | HOH X1354 | 31.467 | 60.382 | 50.635 | 1.00 | 26.84 | O |

| ATOM | 44718 | O | HOH X1355 | 32.653 | 109.013 | -19.895 | 1.00 | 20.85 | O |
|---|---|---|---|---|---|---|---|---|---|
| ATOM | 44721 | O | HOH X1356 | 40.224 | 49.123 | 15.328 | 1.00 | 24.84 | O |
| ATOM | 44724 | O | HOH X1357 | 5.644 | 109.378 | -5.955 | 1.00 | 24.39 | O |
| ATOM | 44727 | O | HOH X1358 | 24.541 | 115.186 | 34.229 | 1.00 | 29.71 | O |
| ATOM | 44730 | O | HOH X1359 | 67.927 | 112.921 | 44.212 | 1.00 | 62.81 | O |
| ATOM | 44733 | O | HOH X1360 | 100.976 | 77.938 | 52.901 | 1.00 | 33.69 | O |
| ATOM | 44736 | O | HOH X1361 | 76.118 | 103.274 | 40.655 | 1.00 | 25.09 | O |
| ATOM | 44739 | O | HOH X1362 | 100.972 | 91.407 | 49.234 | 1.00 | 20.18 | O |
| ATOM | 44742 | O | HOH X1363 | 27.286 | 104.040 | 17.664 | 1.00 | 23.77 | O |
| ATOM | 44745 | O | HOH X1364 | -11.518 | 97.643 | 4.940 | 1.00 | 23.91 | O |
| ATOM | 44748 | O | HOH X1365 | 87.934 | 67.167 | 47.295 | 1.00 | 32.70 | O |
| ATOM | 44751 | O | HOH X1366 | 51.629 | 103.100 | -15.678 | 1.00 | 27.63 | O |
| ATOM | 44754 | O | HOH X1367 | -1.618 | 86.364 | 1.597 | 1.00 | 27.96 | O |
| ATOM | 44757 | O | HOH X1368 | 0.295 | 51.403 | 32.610 | 1.00 | 21.24 | O |
| ATOM | 44760 | O | HOH X1369 | -17.503 | 85.328 | -4.958 | 1.00 | 23.14 | O |
| ATOM | 44763 | O | HOH X1370 | 22.744 | 79.656 | 26.510 | 1.00 | 21.92 | O |
| ATOM | 44766 | O | HOH X1371 | 60.248 | 54.144 | 40.435 | 1.00 | 18.61 | O |
| ATOM | 44769 | O | HOH X1372 | 41.271 | 50.654 | 29.180 | 1.00 | 21.92 | O |
| ATOM | 44772 | O | HOH X1373 | 17.664 | 43.087 | -13.448 | 1.00 | 28.03 | O |
| ATOM | 44775 | O | HOH X1375 | 78.816 | 96.645 | 34.531 | 1.00 | 25.31 | O |
| ATOM | 44778 | O | HOH X1376 | 23.613 | 77.465 | 25.237 | 1.00 | 20.44 | O |
| ATOM | 44781 | O | HOH X1377 | 57.885 | 64.156 | -5.392 | 1.00 | 22.06 | O |
| ATOM | 44784 | O | HOH X1378 | 77.177 | 86.919 | 52.940 | 1.00 | 26.90 | O |
| ATOM | 44787 | O | HOH X1379 | 94.527 | 70.644 | 56.062 | 1.00 | 25.51 | O |
| ATOM | 44790 | O | HOH X1380 | 60.521 | 110.700 | 10.990 | 1.00 | 32.50 | O |
| ATOM | 44793 | O | HOH X1381 | 53.024 | 51.318 | 38.294 | 1.00 | 43.72 | O |
| ATOM | 44796 | O | HOH X1382 | 49.278 | 105.041 | 7.549 | 1.00 | 28.34 | O |
| ATOM | 44799 | O | HOH X1383 | 2.389 | 103.106 | 9.257 | 1.00 | 22.58 | O |
| ATOM | 44802 | O | HOH X1384 | 55.249 | 72.986 | -5.806 | 1.00 | 28.71 | O |
| ATOM | 44805 | O | HOH X1385 | 0.048 | 92.882 | -13.638 | 1.00 | 26.22 | O |
| ATOM | 44808 | O | HOH X1386 | 36.350 | 82.437 | 34.575 | 1.00 | 18.43 | O |
| ATOM | 44811 | O | HOH X1387 | -21.592 | 88.014 | -17.201 | 1.00 | 28.10 | O |
| ATOM | 44814 | O | HOH X1388 | 34.919 | 99.594 | 43.950 | 1.00 | 26.22 | O |
| ATOM | 44817 | O | HOH X1389 | 60.297 | 52.140 | 42.639 | 1.00 | 26.66 | O |
| ATOM | 44820 | O | HOH X1390 | 61.520 | 73.819 | -5.828 | 1.00 | 39.48 | O |
| ATOM | 44823 | O | HOH X1391 | 11.250 | 39.156 | 23.946 | 1.00 | 33.27 | O |
| ATOM | 44826 | O | HOH X1392 | 60.442 | 117.596 | 31.728 | 1.00 | 25.23 | O |
| ATOM | 44829 | O | HOH X1393 | 10.891 | 45.719 | -2.817 | 1.00 | 31.32 | O |
| ATOM | 44832 | O | HOH X1394 | 56.289 | 79.597 | 31.295 | 1.00 | 19.76 | O |
| ATOM | 44835 | O | HOH X1396 | 94.837 | 85.809 | 62.865 | 1.00 | 23.26 | O |
| ATOM | 44838 | O | HOH X1397 | -4.963 | 55.373 | 32.871 | 1.00 | 46.08 | O |
| ATOM | 44841 | O | HOH X1398 | -11.346 | 61.052 | 27.957 | 1.00 | 54.83 | O |
| ATOM | 44844 | O | HOH X1399 | 104.033 | 76.710 | 48.965 | 1.00 | 42.81 | O |
| ATOM | 44847 | O | HOH X1400 | 84.426 | 92.424 | 56.867 | 1.00 | 39.50 | O |
| ATOM | 44850 | O | HOH X1401 | 17.376 | 100.218 | -18.558 | 1.00 | 72.82 | O |
| ATOM | 44853 | O | HOH X1402 | 49.315 | 100.381 | -17.009 | 1.00 | 28.30 | O |
| ATOM | 44856 | O | HOH X1403 | 9.599 | 69.427 | 16.293 | 1.00 | 37.84 | O |
| ATOM | 44859 | O | HOH X1404 | 66.016 | 109.001 | 43.591 | 1.00 | 35.93 | O |
| ATOM | 44862 | O | HOH X1405 | -6.813 | 72.033 | -31.134 | 1.00 | 24.53 | O |
| ATOM | 44865 | O | HOH X1406 | -24.546 | 66.532 | -17.744 | 1.00 | 33.72 | O |
| ATOM | 44868 | O | HOH X1407 | -9.090 | 98.185 | -9.968 | 1.00 | 36.23 | O |
| ATOM | 44871 | O | HOH X1408 | -6.825 | 56.565 | -17.546 | 1.00 | 30.17 | O |
| ATOM | 44874 | O | HOH X1409 | 2.102 | 110.276 | 11.597 | 1.00 | 27.10 | O |
| ATOM | 44877 | O | HOH X1411 | 2.515 | 47.145 | -11.647 | 1.00 | 30.55 | O |
| ATOM | 44880 | O | HOH X1412 | -6.910 | 76.516 | -12.978 | 1.00 | 21.67 | O |
| ATOM | 44883 | O | HOH X1413 | 35.299 | 118.716 | 29.074 | 1.00 | 36.81 | O |
| ATOM | 44886 | O | HOH X1414 | -9.344 | 56.367 | -6.177 | 1.00 | 34.09 | O |

| ATOM | 44889 | O | HOH | X1415 | 71.134 | 42.041 | 12.831 | 1.00 | 31.96 | O |
|------|-------|---|-----|-------|--------|--------|--------|------|-------|---|
| ATOM | 44892 | O | HOH | X1416 | 20.344 | 70.840 | -3.712 | 1.00 | 21.14 | O |
| ATOM | 44895 | O | HOH | X1417 | 14.035 | 53.462 | 48.544 | 1.00 | 35.37 | O |
| ATOM | 44898 | O | HOH | X1418 | 63.530 | 42.166 | 4.357 | 1.00 | 38.58 | O |
| ATOM | 44901 | O | HOH | X1419 | 15.767 | 45.972 | 41.759 | 1.00 | 53.91 | O |
| ATOM | 44904 | O | HOH | X1420 | 62.654 | 70.765 | -2.347 | 1.00 | 26.08 | O |
| ATOM | 44907 | O | HOH | X1421 | 7.885 | 84.369 | -12.433 | 1.00 | 30.38 | O |
| ATOM | 44910 | O | HOH | X1422 | 8.064 | 52.105 | -12.589 | 1.00 | 24.19 | O |
| ATOM | 44913 | O | HOH | X1424 | 58.944 | 69.464 | 61.261 | 1.00 | 29.75 | O |
| ATOM | 44916 | O | HOH | X1425 | 46.966 | 124.550 | 37.088 | 1.00 | 31.88 | O |
| ATOM | 44919 | O | HOH | X1426 | -17.017 | 84.995 | 2.748 | 1.00 | 25.46 | O |
| ATOM | 44922 | O | HOH | X1427 | 46.440 | 105.699 | 14.834 | 1.00 | 26.30 | O |
| ATOM | 44925 | O | HOH | X1428 | 76.487 | 115.151 | 21.688 | 1.00 | 35.65 | O |
| ATOM | 44928 | O | HOH | X1429 | 6.149 | 63.884 | -5.183 | 1.00 | 24.14 | O |
| ATOM | 44931 | O | HOH | X1430 | -0.220 | 78.095 | -21.591 | 1.00 | 42.91 | O |
| ATOM | 44934 | O | HOH | X1431 | 40.527 | 54.177 | 48.189 | 1.00 | 20.56 | O |
| ATOM | 44937 | O | HOH | X1432 | -0.943 | 65.244 | -21.726 | 1.00 | 23.08 | O |
| ATOM | 44940 | O | HOH | X1433 | 37.515 | 98.802 | 8.412 | 1.00 | 18.43 | O |
| ATOM | 44943 | O | HOH | X1434 | -0.524 | 50.360 | 22.927 | 1.00 | 29.88 | O |
| ATOM | 44946 | O | HOH | X1435 | 17.288 | 55.052 | 48.221 | 1.00 | 27.27 | O |
| ATOM | 44949 | O | HOH | X1436 | 31.925 | 81.129 | 31.389 | 1.00 | 47.65 | O |
| ATOM | 44952 | O | HOH | X1437 | 83.265 | 108.942 | 29.635 | 1.00 | 22.57 | O |
| ATOM | 44955 | O | HOH | X1438 | 20.180 | 96.849 | -31.595 | 1.00 | 47.14 | O |
| ATOM | 44958 | O | HOH | X1439 | 64.177 | 83.510 | -6.602 | 1.00 | 36.77 | O |
| ATOM | 44961 | O | HOH | X1440 | 59.806 | 104.964 | 1.506 | 1.00 | 31.48 | O |
| ATOM | 44964 | O | HOH | X1441 | 34.108 | 46.787 | -3.882 | 1.00 | 26.43 | O |
| ATOM | 44967 | O | HOH | X1442 | 6.563 | 68.329 | 18.328 | 1.00 | 22.61 | O |
| ATOM | 44970 | O | HOH | X1443 | 59.821 | 54.990 | 48.387 | 1.00 | 15.31 | O |
| ATOM | 44973 | O | HOH | X1444 | 73.685 | 76.976 | 61.848 | 1.00 | 15.84 | O |
| ATOM | 44976 | O | HOH | X1445 | 76.290 | 74.457 | 65.962 | 1.00 | 18.93 | O |
| ATOM | 44979 | O | HOH | X1446 | 20.828 | 117.769 | -9.493 | 1.00 | 20.44 | O |
| ATOM | 44982 | O | HOH | X1447 | 72.367 | 107.084 | 9.572 | 1.00 | 16.42 | O |
| ATOM | 44985 | O | HOH | X1448 | 79.629 | 104.027 | 10.777 | 1.00 | 24.06 | O |
| ATOM | 44988 | O | HOH | X1449 | 67.800 | 72.018 | -1.810 | 1.00 | 26.73 | O |
| ATOM | 44991 | O | HOH | X1450 | 19.246 | 77.445 | 44.260 | 1.00 | 23.97 | O |
| ATOM | 44994 | O | HOH | X1451 | 79.505 | 110.375 | 12.879 | 1.00 | 18.73 | O |
| ATOM | 44997 | O | HOH | X1452 | 86.192 | 65.393 | 43.907 | 1.00 | 39.46 | O |
| ATOM | 45000 | O | HOH | X1453 | -10.163 | 105.938 | 1.981 | 1.00 | 21.94 | O |
| ATOM | 45003 | O | HOH | X1454 | 25.463 | 46.449 | -11.218 | 1.00 | 28.78 | O |
| ATOM | 45006 | O | HOH | X1455 | 55.140 | 96.570 | 47.212 | 1.00 | 31.16 | O |
| ATOM | 45009 | O | HOH | X1456 | 104.273 | 82.018 | 26.949 | 1.00 | 22.90 | O |
| ATOM | 45012 | O | HOH | X1457 | 77.040 | 82.344 | 65.326 | 1.00 | 28.66 | O |
| ATOM | 45015 | O | HOH | X1458 | 19.036 | 106.782 | -12.918 | 1.00 | 27.08 | O |
| ATOM | 45018 | O | HOH | X1459 | -6.178 | 101.945 | 6.716 | 1.00 | 24.07 | O |
| ATOM | 45021 | O | HOH | X1460 | 16.445 | 66.349 | 46.057 | 1.00 | 28.76 | O |
| ATOM | 45024 | O | HOH | X1461 | 10.211 | 50.647 | -13.020 | 1.00 | 26.47 | O |
| ATOM | 45027 | O | HOH | X1462 | -6.074 | 58.558 | 1.546 | 1.00 | 24.69 | O |
| ATOM | 45030 | O | HOH | X1463 | 15.767 | 112.574 | -1.346 | 1.00 | 21.77 | O |
| ATOM | 45033 | O | HOH | X1464 | -29.526 | 79.677 | 8.579 | 1.00 | 24.95 | O |
| ATOM | 45036 | O | HOH | X1465 | 99.352 | 76.329 | 37.128 | 1.00 | 28.45 | O |
| ATOM | 45039 | O | HOH | X1466 | 40.513 | 69.641 | -15.133 | 1.00 | 30.28 | O |
| ATOM | 45042 | O | HOH | X1467 | -4.817 | 81.962 | -13.699 | 1.00 | 21.55 | O |
| ATOM | 45045 | O | HOH | X1468 | 64.531 | 60.530 | 55.856 | 1.00 | 20.66 | O |
| ATOM | 45048 | O | HOH | X1469 | 6.226 | 74.062 | -2.751 | 1.00 | 34.29 | O |
| ATOM | 45051 | O | HOH | X1470 | -9.283 | 99.805 | 4.521 | 1.00 | 25.05 | O |
| ATOM | 45054 | O | HOH | X1471 | -5.776 | 68.564 | -31.516 | 1.00 | 27.88 | O |
| ATOM | 45057 | O | HOH | X1472 | -9.496 | 64.592 | -31.518 | 1.00 | 33.78 | O |

```
ATOM  45060  O  HOH X1473    57.368  50.122  44.829  1.00 22.42           O
ATOM  45063  O  HOH X1474    69.488  72.020  48.751  1.00 37.05           O
ATOM  45066  O  HOH X1475    13.988 112.087  -5.818  1.00 24.79           O
ATOM  45069  O  HOH X1476     9.857  46.857  -0.244  1.00 22.45           O
ATOM  45072  O  HOH X1477   -24.166  75.779 -21.836  1.00 18.03           O
ATOM  45075  O  HOH X1478    66.888  39.098  13.527  1.00 37.73           O
ATOM  45078  O  HOH X1479    32.684  56.563  29.306  1.00 27.90           O
ATOM  45081  O  HOH X1480    45.944  96.966   9.216  1.00 15.39           O
ATOM  45084  O  HOH X1481    35.875  62.224  30.899  1.00 15.29           O
ATOM  45087  O  HOH X1482    18.423  81.903  36.924  1.00 17.41           O
ATOM  45090  O  HOH X1483    22.818  86.003  40.463  1.00 24.39           O
ATOM  45093  O  HOH X1484     5.215  46.690  12.221  1.00 23.99           O
ATOM  45096  O  HOH X1485    23.095  65.851  44.581  1.00 18.90           O
ATOM  45099  O  HOH X1486    34.280 100.707  21.382  1.00 20.41           O
ATOM  45102  O  HOH X1487    57.776  82.614  28.414  1.00 20.03           O
ATOM  45105  O  HOH X1488    48.159  83.857  19.913  1.00 15.90           O
ATOM  45108  O  HOH X1489    63.368 110.907  39.920  1.00 22.16           O
ATOM  45111  O  HOH X1490    34.960  59.739  35.093  1.00 21.78           O
ATOM  45114  O  HOH X1491    37.660 125.217  37.152  1.00 28.50           O
ATOM  45117  O  HOH X1492    16.858  71.164  44.580  1.00 21.83           O
ATOM  45120  O  HOH X1493    66.829  47.354  33.537  1.00 21.06           O
ATOM  45123  O  HOH X1494    15.827  73.272   4.081  1.00 23.53           O
ATOM  45126  O  HOH X1495    29.748 111.621  30.755  1.00 22.73           O
ATOM  45129  O  HOH X1496    73.945  93.253  32.423  1.00 23.23           O
ATOM  45132  O  HOH X1497    71.775  61.601   1.549  1.00 26.10           O
ATOM  45135  O  HOH X1498    41.457  81.994  10.273  1.00 20.82           O
ATOM  45138  O  HOH X1499    19.145  84.921  39.226  1.00 17.17           O
ATOM  45141  O  HOH X1500    75.899  51.701  30.595  1.00 26.34           O
ATOM  45144  O  HOH X1501    47.327 103.030  11.327  1.00 23.29           O
ATOM  45147  O  HOH X1502    60.381  62.703   9.923  1.00 27.24           O
ATOM  45150  O  HOH X1503    74.646  99.992  30.830  1.00 20.34           O
ATOM  45153  O  HOH X1504    77.749 106.272   7.327  1.00 20.23           O
ATOM  45156  O  HOH X1505   101.301  75.114  31.567  1.00 25.55           O
ATOM  45159  O  HOH X1506    53.974  77.999  11.032  1.00 23.42           O
ATOM  45162  O  HOH X1507    64.811  96.471  35.686  1.00 24.55           O
ATOM  45165  O  HOH X1508    16.058  68.645  44.573  1.00 19.43           O
ATOM  45168  O  HOH X1509     1.839 108.177  18.664  1.00 25.24           O
ATOM  45171  O  HOH X1510    50.153  80.132  19.481  1.00 21.72           O
ATOM  45174  O  HOH X1511    15.615 109.686  14.266  1.00 27.19           O
ATOM  45177  O  HOH X1512    37.335  89.151  16.623  1.00 22.14           O
ATOM  45180  O  HOH X1513    76.178  81.932  33.920  1.00 28.27           O
ATOM  45183  O  HOH X1514     6.584  73.412  14.115  1.00 25.80           O
ATOM  45186  O  HOH X1515    39.654  55.966   7.047  1.00 25.18           O
ATOM  45189  O  HOH X1516    49.275  47.589   7.790  1.00 24.10           O
ATOM  45192  O  HOH X1517    25.545  79.269  24.298  1.00 22.95           O
ATOM  45195  O  HOH X1518    81.444 104.436   8.422  1.00 26.30           O
ATOM  45198  O  HOH X1519    72.935  62.751  22.685  1.00 27.07           O
ATOM  45201  O  HOH X1520    12.104 109.283   3.529  1.00 22.73           O
ATOM  45204  O  HOH X1521    30.314  46.994   6.144  1.00 24.42           O
ATOM  45207  O  HOH X1522    74.741 103.912   9.819  1.00 21.48           O
ATOM  45210  O  HOH X1523     1.683  48.204  13.057  1.00 24.24           O
ATOM  45213  O  HOH X1524    54.678  50.462  44.666  1.00 23.05           O
ATOM  45216  O  HOH X1525    34.397  58.418  33.036  1.00 25.50           O
ATOM  45219  O  HOH X1526     3.500 111.798  14.828  1.00 21.25           O
ATOM  45222  O  HOH X1527    58.197  85.400   7.944  1.00 27.13           O
ATOM  45225  O  HOH X1528    40.735  55.282  33.351  1.00 26.78           O
ATOM  45228  O  HOH X1529    29.003  44.555   0.820  1.00 27.07           O
```

| | | | | | | | | | |
|---|---|---|---|---|---|---|---|---|---|
| ATOM | 45231 | O | HOH | X1530 | 70.255 | 81.421 | 29.507 | 1.00 24.41 | O |
| ATOM | 45234 | O | HOH | X1531 | 1.531 | 69.834 | 37.567 | 1.00 23.85 | O |
| ATOM | 45237 | O | HOH | X1532 | 82.910 | 107.000 | 38.539 | 1.00 32.65 | O |
| ATOM | 45240 | O | HOH | X1533 | 20.230 | 44.177 | 0.660 | 1.00 26.73 | O |
| ATOM | 45243 | O | HOH | X1534 | 5.475 | 46.440 | 33.727 | 1.00 26.64 | O |
| ATOM | 45246 | O | HOH | X1535 | 57.965 | 47.504 | 44.287 | 1.00 26.84 | O |
| ATOM | 45249 | O | HOH | X1536 | 71.776 | 111.631 | 15.606 | 1.00 24.75 | O |
| ATOM | 45252 | O | HOH | X1537 | 21.564 | 89.661 | 42.565 | 1.00 26.62 | O |
| ATOM | 45255 | O | HOH | X1538 | 103.213 | 91.975 | 42.666 | 1.00 25.19 | O |
| ATOM | 45258 | O | HOH | X1539 | 67.933 | 67.329 | 34.937 | 1.00 33.91 | O |
| ATOM | 45261 | O | HOH | X1540 | 64.371 | 91.507 | 35.345 | 1.00 29.08 | O |
| ATOM | 45264 | O | HOH | X1541 | 1.415 | 103.451 | 21.885 | 1.00 24.17 | O |
| ATOM | 45267 | O | HOH | X1542 | 57.592 | 85.465 | 29.332 | 1.00 32.11 | O |
| ATOM | 45270 | O | HOH | X1543 | 14.394 | 40.679 | 17.369 | 1.00 32.43 | O |
| ATOM | 45273 | O | HOH | X1544 | 23.244 | 45.850 | 3.075 | 1.00 33.67 | O |
| ATOM | 45276 | O | HOH | X1545 | 38.829 | 58.884 | 7.659 | 1.00 21.53 | O |
| ATOM | 45279 | O | HOH | X1546 | 18.154 | 112.138 | -0.072 | 1.00 30.03 | O |
| ATOM | 45282 | O | HOH | X1547 | 4.477 | 108.662 | 19.539 | 1.00 25.97 | O |
| ATOM | 45285 | O | HOH | X1548 | 10.069 | 42.074 | 11.335 | 1.00 30.44 | O |
| ATOM | 45288 | O | HOH | X1549 | 38.782 | 75.222 | 41.437 | 1.00 21.42 | O |
| ATOM | 45291 | O | HOH | X1550 | 12.890 | 65.320 | 35.360 | 1.00 27.50 | O |
| ATOM | 45294 | O | HOH | X1551 | 57.805 | 76.669 | 30.889 | 1.00 26.16 | O |
| ATOM | 45297 | O | HOH | X1552 | 41.102 | 50.613 | 0.878 | 1.00 25.95 | O |
| ATOM | 45300 | O | HOH | X1553 | 60.867 | 110.728 | 17.155 | 1.00 27.81 | O |
| ATOM | 45303 | O | HOH | X1554 | 83.369 | 109.559 | 32.212 | 1.00 28.16 | O |
| ATOM | 45306 | O | HOH | X1555 | 31.640 | 58.505 | 39.764 | 1.00 30.92 | O |
| ATOM | 45309 | O | HOH | X1556 | 8.199 | 102.711 | 32.670 | 1.00 25.76 | O |
| ATOM | 45312 | O | HOH | X1557 | 34.298 | 122.900 | 34.373 | 1.00 29.76 | O |
| ATOM | 45315 | O | HOH | X1558 | 48.532 | 77.550 | 0.895 | 1.00 27.12 | O |
| ATOM | 45318 | O | HOH | X1559 | 37.700 | 47.599 | 11.987 | 1.00 28.04 | O |
| ATOM | 45321 | O | HOH | X1560 | 36.323 | 46.717 | 9.955 | 1.00 30.80 | O |
| ATOM | 45324 | O | HOH | X1561 | 51.849 | 77.412 | 9.642 | 1.00 18.03 | O |
| ATOM | 45327 | O | HOH | X1562 | 12.554 | 108.226 | 7.695 | 1.00 26.41 | O |
| ATOM | 45330 | O | HOH | X1563 | 77.636 | 84.156 | 22.690 | 1.00 24.80 | O |
| ATOM | 45333 | O | HOH | X1564 | 72.550 | 58.794 | 9.020 | 1.00 27.23 | O |
| ATOM | 45336 | O | HOH | X1565 | 69.992 | 110.150 | 23.711 | 1.00 26.32 | O |
| ATOM | 45339 | O | HOH | X1566 | 36.321 | 106.362 | 13.561 | 1.00 30.28 | O |
| ATOM | 45342 | O | HOH | X1567 | 19.311 | 79.704 | 42.615 | 1.00 22.06 | O |
| ATOM | 45345 | O | HOH | X1568 | 57.866 | 115.420 | 41.371 | 1.00 23.62 | O |
| ATOM | 45348 | O | HOH | X1569 | 18.420 | 75.747 | 5.029 | 1.00 23.96 | O |
| ATOM | 45351 | O | HOH | X1570 | 69.011 | 77.705 | 38.623 | 1.00 27.91 | O |
| ATOM | 45354 | O | HOH | X1571 | 39.709 | 56.444 | 28.906 | 1.00 26.56 | O |
| ATOM | 45357 | O | HOH | X1572 | 71.701 | 48.043 | 27.826 | 1.00 26.89 | O |
| ATOM | 45360 | O | HOH | X1573 | 11.672 | 84.087 | 37.293 | 1.00 28.56 | O |
| ATOM | 45363 | O | HOH | X1574 | 32.563 | 49.925 | 11.482 | 1.00 33.69 | O |
| ATOM | 45366 | O | HOH | X1575 | 9.665 | 110.681 | 8.282 | 1.00 23.47 | O |
| ATOM | 45369 | O | HOH | X1576 | 10.382 | 44.920 | 1.820 | 1.00 31.73 | O |
| ATOM | 45372 | O | HOH | X1577 | 72.170 | 86.230 | 42.914 | 1.00 25.69 | O |
| ATOM | 45375 | O | HOH | X1578 | 9.119 | 65.745 | 17.373 | 1.00 27.85 | O |
| ATOM | 45378 | O | HOH | X1579 | 33.984 | 51.910 | 9.937 | 1.00 26.58 | O |
| ATOM | 45381 | O | HOH | X1580 | 0.564 | 88.733 | 0.323 | 1.00 24.72 | O |
| ATOM | 45384 | O | HOH | X1581 | 66.526 | 95.741 | 42.935 | 1.00 27.85 | O |
| ATOM | 45387 | O | HOH | X1582 | 38.595 | 127.988 | 41.652 | 1.00 34.34 | O |
| ATOM | 45390 | O | HOH | X1583 | 9.450 | 74.171 | 8.887 | 1.00 29.68 | O |
| ATOM | 45393 | O | HOH | X1584 | 43.535 | 53.364 | 2.869 | 1.00 27.19 | O |
| ATOM | 45396 | O | HOH | X1585 | 34.071 | 78.356 | 1.727 | 1.00 30.51 | O |
| ATOM | 45399 | O | HOH | X1586 | 83.115 | 102.455 | 43.545 | 1.00 33.32 | O |

```
ATOM  45402  O  HOH X1587   38.518 106.495  14.500  1.00 31.22           O
ATOM  45405  O  HOH X1588   71.608 112.426  35.485  1.00 32.76           O
ATOM  45408  O  HOH X1589   33.301 117.756  18.215  1.00 31.20           O
ATOM  45411  O  HOH X1590   80.031  86.658   8.363  1.00 32.21           O
ATOM  45414  O  HOH X1591   66.339  83.204   0.638  1.00 29.01           O
ATOM  45417  O  HOH X1592   45.609 126.747  43.290  1.00 25.91           O
ATOM  45420  O  HOH X1593   44.485  51.743  38.397  1.00 29.07           O
ATOM  45423  O  HOH X1594   49.218 121.732  45.019  1.00 31.70           O
ATOM  45426  O  HOH X1595   33.819  56.882  37.084  1.00 25.63           O
ATOM  45429  O  HOH X1596   84.577  71.366  40.402  1.00 28.18           O
ATOM  45432  O  HOH X1597   41.301 120.535   6.332  1.00 28.63           O
ATOM  45435  O  HOH X1598   37.495 120.015  17.940  1.00 29.18           O
ATOM  45438  O  HOH X1599   40.352  55.190   9.282  1.00 31.10           O
ATOM  45441  O  HOH X1600   72.064  95.554  35.018  1.00 23.32           O
ATOM  45444  O  HOH X1601   74.928  93.058  28.775  1.00 28.70           O
ATOM  45447  O  HOH X1602   77.871 109.016  35.215  1.00 32.26           O
ATOM  45450  O  HOH X1603    3.154  88.020  32.170  1.00 29.06           O
ATOM  45453  O  HOH X1604   68.540 110.253   8.708  1.00 28.19           O
ATOM  45456  O  HOH X1605   30.607 107.746  16.122  1.00 31.14           O
ATOM  45459  O  HOH X1606   14.280  65.446  30.306  1.00 28.67           O
ATOM  45462  O  HOH X1607   71.394  57.055  10.199  1.00 27.25           O
ATOM  45465  O  HOH X1608   36.322  46.321   2.096  1.00 31.33           O
ATOM  45468  O  HOH X1609   75.991  60.118  44.963  1.00 25.75           O
ATOM  45471  O  HOH X1610   65.611  66.557  22.534  1.00 31.83           O
ATOM  45474  O  HOH X1611    2.986 105.202  22.855  1.00 28.14           O
ATOM  45477  O  HOH X1612   40.241 128.325  31.126  1.00 28.79           O
ATOM  45480  O  HOH X1614   55.448  46.140  33.817  1.00 34.06           O
ATOM  45483  O  HOH X1615   58.671 116.482  27.338  1.00 28.08           O
ATOM  45486  O  HOH X1616  102.603  82.393  24.677  1.00 24.23           O
ATOM  45489  O  HOH X1617   20.779  79.988  24.986  1.00 28.54           O
ATOM  45492  O  HOH X1618   62.935 118.199  26.760  1.00 31.17           O
ATOM  45495  O  HOH X1619   64.721  50.867  43.058  1.00 30.70           O
ATOM  45498  O  HOH X1620   69.730  47.229   3.086  1.00 30.61           O
ATOM  45501  O  HOH X1621    4.801  52.662  40.962  1.00 33.78           O
ATOM  45504  O  HOH X1622   60.708 112.615  21.021  1.00 27.38           O
ATOM  45507  O  HOH X1623   71.141  98.262  33.932  1.00 31.07           O
ATOM  45510  O  HOH X1624   84.773 105.194  27.693  1.00 25.61           O
ATOM  45513  O  HOH X1625   50.135 111.966   9.184  1.00 32.88           O
ATOM  45516  O  HOH X1626   47.097  52.055  41.768  1.00 26.16           O
ATOM  45519  O  HOH X1627   64.513 114.322  27.023  1.00 28.11           O
ATOM  45522  O  HOH X1628   79.484  65.492  37.070  1.00 29.49           O
ATOM  45525  O  HOH X1629   30.366  59.469  42.339  1.00 26.10           O
ATOM  45528  O  HOH X1630   33.121 106.753  18.777  1.00 31.39           O
ATOM  45531  O  HOH X1631   46.303 106.745  10.261  1.00 28.29           O
ATOM  45534  O  HOH X1632   13.282  78.376   1.995  1.00 30.17           O
ATOM  45537  O  HOH X1633   68.693 115.054  32.854  1.00 33.42           O
ATOM  45540  O  HOH X1634   27.920  58.212  43.365  1.00 31.70           O
ATOM  45543  O  HOH X1635   53.405 119.590  30.161  1.00 25.41           O
ATOM  45546  O  HOH X1636   68.307 112.620  27.613  1.00 24.59           O
ATOM  45549  O  HOH X1637   83.972 103.216  25.364  1.00 34.55           O
ATOM  45552  O  HOH X1638   37.850  50.892   8.273  1.00 28.75           O
ATOM  45555  O  HOH X1639   35.333 125.109   1.366  1.00 31.99           O
ATOM  45558  O  HOH X1640   30.007 110.118  20.926  1.00 29.12           O
ATOM  45561  O  HOH X1641   16.449  87.913  26.048  1.00 22.73           O
ATOM  45564  O  HOH X1642   24.829 116.271   8.812  1.00 27.33           O
ATOM  45567  O  HOH X1643   25.970  82.269  34.756  1.00 24.18           O
ATOM  45570  O  HOH X1644   76.129  96.352  35.303  1.00 25.53           O
```

| | | | | | | | | | |
|---|---|---|---|---|---|---|---|---|---|
| ATOM | 45573 | O | HOH | X1645 | 35.569 | 98.886 | 17.554 | 1.00 34.51 | O |
| ATOM | 45576 | O | HOH | X1646 | 66.160 | 110.834 | 24.203 | 1.00 27.55 | O |
| ATOM | 45579 | O | HOH | X1647 | 58.944 | 88.695 | 37.325 | 1.00 33.65 | O |
| ATOM | 45582 | O | HOH | X1648 | 40.528 | 82.908 | 33.966 | 1.00 32.99 | O |
| ATOM | 45585 | O | HOH | X1649 | 50.660 | 50.262 | 30.519 | 1.00 30.35 | O |
| ATOM | 45588 | O | HOH | X1650 | 18.592 | 108.665 | 25.846 | 1.00 35.21 | O |
| ATOM | 45591 | O | HOH | X1651 | 28.332 | 107.890 | 17.946 | 1.00 27.06 | O |
| ATOM | 45594 | O | HOH | X1652 | 78.577 | 81.406 | 38.376 | 1.00 30.55 | O |
| ATOM | 45597 | O | HOH | X1653 | 74.673 | 46.689 | 9.698 | 1.00 34.50 | O |
| ATOM | 45600 | O | HOH | X1654 | 95.213 | 99.826 | 44.603 | 1.00 32.41 | O |
| ATOM | 45603 | O | HOH | X1655 | 87.263 | 80.656 | 15.407 | 1.00 33.68 | O |
| ATOM | 45606 | O | HOH | X1656 | 54.114 | 121.734 | 39.545 | 1.00 32.10 | O |
| ATOM | 45609 | O | HOH | X1657 | 8.337 | 46.872 | 17.558 | 1.00 29.27 | O |
| ATOM | 45612 | O | HOH | X1658 | 88.980 | 82.528 | 30.565 | 1.00 27.60 | O |
| ATOM | 45615 | O | HOH | X1659 | 22.092 | 38.150 | 19.029 | 1.00 32.47 | O |
| ATOM | 45618 | O | HOH | X1660 | 71.484 | 110.386 | 38.331 | 1.00 27.16 | O |
| ATOM | 45621 | O | HOH | X1661 | 40.641 | 40.920 | 17.126 | 1.00 34.42 | O |
| ATOM | 45624 | O | HOH | X1662 | 53.208 | 77.662 | 13.633 | 1.00 26.31 | O |
| ATOM | 45627 | O | HOH | X1663 | 66.981 | 111.750 | 14.558 | 1.00 30.35 | O |
| ATOM | 45630 | O | HOH | X1664 | 8.303 | 108.037 | 2.812 | 1.00 31.71 | O |
| ATOM | 45633 | O | HOH | X1665 | 93.514 | 100.103 | 40.880 | 1.00 30.90 | O |
| ATOM | 45636 | O | HOH | X1666 | 72.814 | 52.273 | 42.421 | 1.00 28.44 | O |
| ATOM | 45639 | O | HOH | X1667 | 41.142 | 53.692 | 3.487 | 1.00 38.54 | O |
| ATOM | 45642 | O | HOH | X1668 | 55.055 | 49.644 | 39.620 | 1.00 27.27 | O |
| ATOM | 45645 | O | HOH | X1669 | 3.323 | 78.666 | 1.286 | 1.00 36.29 | O |
| ATOM | 45648 | O | HOH | X1670 | 66.663 | 48.566 | 27.217 | 1.00 28.79 | O |
| ATOM | 45651 | O | HOH | X1672 | 82.811 | 81.016 | 32.290 | 1.00 30.81 | O |
| ATOM | 45654 | O | HOH | X1673 | 73.245 | 105.279 | 7.473 | 1.00 24.98 | O |
| ATOM | 45657 | O | HOH | X1674 | 19.730 | 89.370 | 40.917 | 1.00 28.79 | O |
| ATOM | 45660 | O | HOH | X1675 | 34.468 | 60.043 | 30.613 | 1.00 29.79 | O |
| ATOM | 45663 | O | HOH | X1676 | 80.494 | 104.039 | 43.661 | 1.00 32.00 | O |
| ATOM | 45666 | O | HOH | X1677 | 16.992 | 43.160 | 12.215 | 1.00 33.51 | O |
| ATOM | 45669 | O | HOH | X1678 | 89.782 | 76.289 | 33.417 | 1.00 38.13 | O |
| ATOM | 45672 | O | HOH | X1679 | 8.391 | 110.651 | 5.967 | 1.00 29.77 | O |
| ATOM | 45675 | O | HOH | X1680 | 32.820 | 124.623 | 26.192 | 1.00 40.36 | O |
| ATOM | 45678 | O | HOH | X1681 | 18.438 | 112.612 | 37.058 | 1.00 32.41 | O |
| ATOM | 45681 | O | HOH | X1682 | 99.387 | 78.416 | 34.218 | 1.00 29.74 | O |
| ATOM | 45684 | O | HOH | X1683 | 77.672 | 60.048 | 26.393 | 1.00 29.78 | O |
| ATOM | 45687 | O | HOH | X1684 | 19.379 | 43.052 | 11.994 | 1.00 31.00 | O |
| ATOM | 45690 | O | HOH | X1685 | 76.148 | 53.790 | 17.589 | 1.00 36.13 | O |
| ATOM | 45693 | O | HOH | X1686 | 78.864 | 57.123 | 16.420 | 1.00 30.56 | O |
| ATOM | 45696 | O | HOH | X1687 | 37.061 | 117.918 | 7.248 | 1.00 28.97 | O |
| ATOM | 45699 | O | HOH | X1688 | 34.184 | 60.153 | 21.220 | 1.00 26.59 | O |
| ATOM | 45702 | O | HOH | X1689 | 27.910 | 40.449 | 14.256 | 1.00 32.59 | O |
| ATOM | 45705 | O | HOH | X1690 | 18.653 | 112.783 | 42.426 | 1.00 35.54 | O |
| ATOM | 45708 | O | HOH | X1691 | 32.079 | 44.500 | 9.603 | 1.00 39.15 | O |
| ATOM | 45711 | O | HOH | X1692 | 50.534 | 126.590 | 40.242 | 1.00 29.51 | O |
| ATOM | 45714 | O | HOH | X1693 | 16.871 | 35.211 | 24.909 | 1.00 32.88 | O |
| ATOM | 45717 | O | HOH | X1694 | 80.431 | 109.526 | 35.690 | 1.00 32.51 | O |
| ATOM | 45720 | O | HOH | X1695 | 84.650 | 93.349 | 23.257 | 1.00 34.34 | O |
| ATOM | 45723 | O | HOH | X1696 | 38.555 | 59.868 | 18.394 | 1.00 31.42 | O |
| ATOM | 45726 | O | HOH | X1697 | 79.418 | 101.124 | 10.591 | 1.00 23.24 | O |
| ATOM | 45729 | O | HOH | X1698 | 83.320 | 100.727 | 18.907 | 1.00 30.97 | O |
| ATOM | 45732 | O | HOH | X1699 | 15.300 | 41.967 | 8.050 | 1.00 29.75 | O |
| ATOM | 45735 | O | HOH | X1700 | 40.893 | 55.182 | 16.742 | 1.00 36.50 | O |
| ATOM | 45738 | O | HOH | X1701 | 49.799 | 117.350 | 16.765 | 1.00 29.56 | O |
| ATOM | 45741 | O | HOH | X1702 | -0.086 | 49.343 | 3.287 | 1.00 36.23 | O |

| | | | | | | | | | |
|---|---|---|---|---|---|---|---|---|---|
| ATOM | 45744 | O | HOH | X1703 | 9.067 | 49.645 | 17.646 | 1.00 29.61 | O |
| ATOM | 45747 | O | HOH | X1704 | 59.347 | 40.376 | 28.269 | 1.00 37.82 | O |
| ATOM | 45750 | O | HOH | X1705 | 12.967 | 45.979 | 38.062 | 1.00 34.83 | O |
| ATOM | 45753 | O | HOH | X1706 | 42.506 | 107.181 | 2.553 | 1.00 27.26 | O |
| ATOM | 45756 | O | HOH | X1707 | 77.781 | 59.504 | 5.209 | 1.00 29.87 | O |
| ATOM | 45759 | O | HOH | X1708 | 38.824 | 98.317 | 13.000 | 1.00 30.18 | O |
| ATOM | 45762 | O | HOH | X1709 | 80.052 | 52.191 | 9.680 | 1.00 45.57 | O |
| ATOM | 45765 | O | HOH | X1710 | 76.172 | 91.429 | 4.025 | 1.00 26.26 | O |
| ATOM | 45768 | O | HOH | X1711 | 76.884 | 80.652 | 10.583 | 1.00 26.29 | O |
| ATOM | 45771 | O | HOH | X1712 | 5.555 | 43.261 | 11.046 | 1.00 35.64 | O |
| ATOM | 45774 | O | HOH | X1713 | 24.546 | 118.226 | 37.723 | 1.00 34.75 | O |
| ATOM | 45777 | O | HOH | X1714 | 72.586 | 102.610 | 3.719 | 1.00 28.19 | O |
| ATOM | 45780 | O | HOH | X1715 | 103.019 | 88.913 | 36.826 | 1.00 34.79 | O |
| ATOM | 45783 | O | HOH | X1716 | 60.674 | 42.722 | 29.422 | 1.00 27.71 | O |
| ATOM | 45786 | O | HOH | X1717 | 26.432 | 88.976 | 44.988 | 1.00 33.53 | O |
| ATOM | 45789 | O | HOH | X1718 | 34.356 | 42.617 | 28.947 | 1.00 36.89 | O |
| ATOM | 45792 | O | HOH | X1719 | 55.698 | 116.590 | 35.887 | 1.00 30.20 | O |
| ATOM | 45795 | O | HOH | X1720 | 71.459 | 43.135 | 21.734 | 1.00 38.43 | O |
| ATOM | 45798 | O | HOH | X1721 | 55.608 | 108.435 | 5.742 | 1.00 33.40 | O |
| ATOM | 45801 | O | HOH | X1722 | 71.442 | 83.757 | 1.998 | 1.00 29.19 | O |
| ATOM | 45804 | O | HOH | X1723 | 84.399 | 79.527 | 40.487 | 1.00 31.61 | O |
| ATOM | 45807 | O | HOH | X1724 | 37.052 | 54.854 | 35.230 | 1.00 30.08 | O |
| ATOM | 45810 | O | HOH | X1725 | 77.714 | 51.749 | 11.476 | 1.00 36.82 | O |
| ATOM | 45813 | O | HOH | X1726 | 55.754 | 41.567 | 6.146 | 1.00 30.33 | O |
| ATOM | 45816 | O | HOH | X1727 | 77.616 | 63.116 | 33.699 | 1.00 37.03 | O |
| ATOM | 45819 | O | HOH | X1728 | 25.879 | 118.357 | 0.995 | 1.00 33.12 | O |
| ATOM | 45822 | O | HOH | X1729 | 76.378 | 76.057 | 17.446 | 1.00 30.55 | O |
| ATOM | 45825 | O | HOH | X1730 | 39.893 | 115.789 | 12.573 | 1.00 34.73 | O |
| ATOM | 45828 | O | HOH | X1731 | 8.993 | 113.467 | 18.723 | 1.00 32.66 | O |
| ATOM | 45831 | O | HOH | X1732 | 12.987 | 65.441 | 5.062 | 1.00 40.15 | O |
| ATOM | 45834 | O | HOH | X1733 | 20.684 | 46.768 | 3.392 | 1.00 30.70 | O |
| ATOM | 45837 | O | HOH | X1734 | 37.521 | 127.279 | 33.603 | 1.00 35.23 | O |
| ATOM | 45840 | O | HOH | X1735 | 61.781 | 92.501 | 36.600 | 1.00 28.76 | O |
| ATOM | 45843 | O | HOH | X1736 | 69.857 | 44.439 | 25.412 | 1.00 30.52 | O |
| ATOM | 45846 | O | HOH | X1737 | 68.696 | 112.577 | 15.887 | 1.00 28.20 | O |
| ATOM | 45849 | O | HOH | X1738 | 18.755 | 40.952 | 36.405 | 1.00 36.33 | O |
| ATOM | 45852 | O | HOH | X1739 | 50.945 | 122.588 | 43.157 | 1.00 27.76 | O |
| ATOM | 45855 | O | HOH | X1740 | 70.671 | 82.571 | 22.213 | 1.00 39.40 | O |
| ATOM | 45858 | O | HOH | X1741 | 78.841 | 79.094 | 7.826 | 1.00 26.77 | O |
| ATOM | 45861 | O | HOH | X1742 | 5.975 | 72.270 | 1.611 | 1.00 34.58 | O |
| ATOM | 45864 | O | HOH | X1743 | 13.563 | 112.639 | 0.284 | 1.00 29.70 | O |
| ATOM | 45867 | O | HOH | X1744 | 53.925 | 120.158 | 41.730 | 1.00 33.50 | O |
| ATOM | 45870 | O | HOH | X1745 | 7.340 | 105.479 | 24.369 | 1.00 31.10 | O |
| ATOM | 45873 | O | HOH | X1746 | 7.245 | 77.406 | 39.131 | 1.00 33.84 | O |
| ATOM | 45876 | O | HOH | X1747 | 42.058 | 99.929 | 16.841 | 1.00 36.08 | O |
| ATOM | 45879 | O | HOH | X1748 | 40.929 | 52.665 | 5.784 | 1.00 31.98 | O |
| ATOM | 45882 | O | HOH | X1749 | 21.932 | 46.820 | 6.360 | 1.00 37.62 | O |
| ATOM | 45885 | O | HOH | X1750 | 40.619 | 60.158 | 20.175 | 1.00 31.23 | O |
| ATOM | 45888 | O | HOH | X1751 | 6.602 | 50.819 | 39.074 | 1.00 30.19 | O |
| ATOM | 45891 | O | HOH | X1752 | 3.333 | 108.060 | 1.902 | 1.00 33.20 | O |
| ATOM | 45894 | O | HOH | X1753 | 51.565 | 100.838 | 2.997 | 1.00 30.67 | O |
| ATOM | 45897 | O | HOH | X1754 | 81.057 | 112.927 | 22.800 | 1.00 31.69 | O |
| ATOM | 45900 | O | HOH | X1755 | 4.459 | 70.896 | 38.298 | 1.00 31.82 | O |
| ATOM | 45903 | O | HOH | X1756 | 12.464 | 76.840 | -40.059 | 1.00 33.33 | O |
| ATOM | 45906 | O | HOH | X1757 | 14.709 | 42.351 | 10.633 | 1.00 27.43 | O |
| ATOM | 45909 | O | HOH | X1758 | 61.906 | 41.779 | 8.184 | 1.00 31.31 | O |
| ATOM | 45912 | O | HOH | X1759 | 102.908 | 95.764 | 42.056 | 1.00 32.91 | O |

| | | | | | | | | | |
|---|---|---|---|---|---|---|---|---|---|
| ATOM | 45915 | O | HOH | X1760 | 11.410 | 34.484 | 28.618 | 1.00 40.32 | O |
| ATOM | 45918 | O | HOH | X1761 | 74.107 | 53.202 | 44.399 | 1.00 34.17 | O |
| ATOM | 45921 | O | HOH | X1762 | 27.696 | 39.656 | 22.016 | 1.00 30.68 | O |
| ATOM | 45924 | O | HOH | X1763 | 36.423 | 56.475 | 33.071 | 1.00 31.73 | O |
| ATOM | 45927 | O | HOH | X1764 | 35.527 | 53.628 | 11.314 | 1.00 23.74 | O |
| ATOM | 45930 | O | HOH | X1765 | 81.206 | 81.971 | 38.199 | 1.00 33.96 | O |
| ATOM | 45933 | O | HOH | X1766 | 77.887 | 82.652 | 9.321 | 1.00 39.44 | O |
| ATOM | 45936 | O | HOH | X1767 | 54.217 | 113.087 | 14.444 | 1.00 38.16 | O |
| ATOM | 45939 | O | HOH | X1768 | 41.676 | 105.249 | 9.699 | 1.00 28.11 | O |
| ATOM | 45942 | O | HOH | X1769 | 34.401 | 58.442 | 17.284 | 1.00 40.40 | O |
| ATOM | 45945 | O | HOH | X1770 | 78.687 | 96.802 | 31.221 | 1.00 37.34 | O |
| ATOM | 45948 | O | HOH | X1771 | 83.491 | 68.220 | 38.123 | 1.00 46.80 | O |
| ATOM | 45951 | O | HOH | X1772 | 49.185 | 77.593 | 11.985 | 1.00 28.04 | O |
| ATOM | 45954 | O | HOH | X1773 | 58.254 | 119.626 | 31.122 | 1.00 28.32 | O |
| ATOM | 45957 | O | HOH | X1774 | 70.111 | 65.757 | 0.678 | 1.00 29.79 | O |
| ATOM | 45960 | O | HOH | X1775 | 16.185 | 108.750 | 7.172 | 1.00 30.26 | O |
| ATOM | 45963 | O | HOH | X1776 | 31.863 | 116.019 | 32.688 | 1.00 37.53 | O |
| ATOM | 45966 | O | HOH | X1777 | 45.404 | 48.455 | 12.257 | 1.00 33.03 | O |
| ATOM | 45969 | O | HOH | X1778 | 80.579 | 104.658 | 22.683 | 1.00 25.39 | O |
| ATOM | 45972 | O | HOH | X1779 | 29.295 | 51.670 | 32.347 | 1.00 37.22 | O |
| ATOM | 45975 | O | HOH | X1780 | 33.933 | 56.460 | 25.775 | 1.00 34.97 | O |
| ATOM | 45978 | O | HOH | X1781 | 47.943 | 34.657 | 13.767 | 1.00 40.65 | O |
| ATOM | 45981 | O | HOH | X1782 | 9.548 | 85.634 | 37.357 | 1.00 34.69 | O |
| ATOM | 45984 | O | HOH | X1783 | 42.552 | 48.483 | 35.663 | 1.00 31.91 | O |
| ATOM | 45987 | O | HOH | X1784 | 61.103 | 84.205 | 35.552 | 1.00 33.91 | O |
| ATOM | 45990 | O | HOH | X1785 | 7.873 | 100.215 | 33.152 | 1.00 85.48 | O |
| ATOM | 45993 | O | HOH | X1786 | 28.049 | 46.262 | 2.784 | 1.00 27.24 | O |
| ATOM | 45996 | O | HOH | X1787 | 80.988 | 77.286 | 38.766 | 1.00 30.84 | O |
| ATOM | 45999 | O | HOH | X1788 | 9.751 | 112.565 | 21.515 | 1.00 37.94 | O |
| ATOM | 46002 | O | HOH | X1789 | 41.571 | 111.152 | 3.671 | 1.00 35.97 | O |
| ATOM | 46005 | O | HOH | X1790 | 74.950 | 96.368 | 28.816 | 1.00 39.45 | O |
| ATOM | 46008 | O | HOH | X1791 | 5.434 | 111.459 | 10.979 | 1.00 34.35 | O |
| ATOM | 46011 | O | HOH | X1792 | 79.414 | 56.789 | 1.349 | 1.00 34.54 | O |
| ATOM | 46014 | O | HOH | X1793 | 51.723 | 51.429 | 41.716 | 1.00 35.90 | O |
| ATOM | 46017 | O | HOH | X1794 | 103.402 | 76.432 | 39.419 | 1.00 35.90 | O |
| ATOM | 46020 | O | HOH | X1795 | 0.653 | 54.277 | 4.138 | 1.00 33.48 | O |
| ATOM | 46023 | O | HOH | X1796 | 61.592 | 110.056 | 19.613 | 1.00 31.63 | O |
| ATOM | 46026 | O | HOH | X1797 | 69.296 | 46.555 | 34.741 | 1.00 40.15 | O |
| ATOM | 46029 | O | HOH | X1798 | 80.646 | 64.474 | 39.551 | 1.00 30.48 | O |
| ATOM | 46032 | O | HOH | X1799 | 77.166 | 88.631 | 30.696 | 1.00 33.15 | O |
| ATOM | 46035 | O | HOH | X1800 | 65.857 | 45.778 | 1.083 | 1.00 41.45 | O |
| ATOM | 46038 | O | HOH | X1801 | 27.390 | 52.280 | 34.139 | 1.00 33.52 | O |
| ATOM | 46041 | O | HOH | X1802 | 68.776 | 103.042 | 41.996 | 1.00 38.96 | O |
| ATOM | 46044 | O | HOH | X1803 | 36.594 | 59.326 | 29.392 | 1.00 35.65 | O |
| ATOM | 46047 | O | HOH | X1804 | 51.468 | 123.605 | 38.841 | 1.00 36.41 | O |
| ATOM | 46050 | O | HOH | X1805 | 5.538 | 43.811 | 3.587 | 1.00 34.10 | O |
| ATOM | 46053 | O | HOH | X1806 | 78.021 | 88.736 | 25.482 | 1.00 33.40 | O |
| ATOM | 46056 | O | HOH | X1807 | 35.220 | 44.224 | 9.328 | 1.00 35.29 | O |
| ATOM | 46059 | O | HOH | X1808 | 41.964 | 34.161 | 13.942 | 1.00 43.80 | O |
| ATOM | 46062 | O | HOH | X1809 | 13.701 | 105.128 | 33.501 | 1.00 31.84 | O |
| ATOM | 46065 | O | HOH | X1810 | 76.641 | 69.002 | 2.096 | 1.00 36.35 | O |
| ATOM | 46068 | O | HOH | X1811 | 102.490 | 86.098 | 27.877 | 1.00 28.04 | O |
| ATOM | 46071 | O | HOH | X1812 | 5.927 | 64.059 | 43.796 | 1.00 33.94 | O |
| ATOM | 46074 | O | HOH | X1813 | 69.477 | 49.421 | 41.507 | 1.00 28.22 | O |
| ATOM | 46077 | O | HOH | X1814 | 23.263 | 112.326 | 14.826 | 1.00 32.83 | O |
| ATOM | 46080 | O | HOH | X1815 | 102.791 | 73.649 | 36.116 | 1.00 29.18 | O |
| ATOM | 46083 | O | HOH | X1816 | 36.790 | 58.328 | 24.143 | 1.00 34.76 | O |

| | | | | | | | | | |
|---|---|---|---|---|---|---|---|---|---|
| ATOM | 46086 | O | HOH | X1817 | 47.009 | 80.144 | 23.915 | 1.00 37.74 | O |
| ATOM | 46089 | O | HOH | X1818 | 24.206 | 47.872 | 14.032 | 1.00 30.34 | O |
| ATOM | 46092 | O | HOH | X1819 | 66.604 | 70.543 | 32.052 | 1.00 37.04 | O |
| ATOM | 46095 | O | HOH | X1820 | 9.260 | 49.007 | 39.768 | 1.00 45.64 | O |
| ATOM | 46098 | O | HOH | X1821 | 71.803 | 111.965 | 18.444 | 1.00 35.91 | O |
| ATOM | 46101 | O | HOH | X1822 | 60.020 | 46.420 | 37.957 | 1.00 36.18 | O |
| ATOM | 46104 | O | HOH | X1823 | 6.921 | 85.427 | 34.653 | 1.00 41.84 | O |
| ATOM | 46107 | O | HOH | X1824 | 81.844 | 73.893 | 38.319 | 1.00 33.98 | O |
| ATOM | 46110 | O | HOH | X1825 | 44.818 | 116.196 | 10.404 | 1.00 40.45 | O |
| ATOM | 46113 | O | HOH | X1826 | 76.235 | 47.529 | 15.888 | 1.00 31.99 | O |
| ATOM | 46116 | O | HOH | X1827 | 41.011 | 79.019 | 4.171 | 1.00 35.93 | O |
| ATOM | 46119 | O | HOH | X1828 | 75.005 | 54.944 | 40.535 | 1.00 34.48 | O |
| ATOM | 46122 | O | HOH | X1829 | 72.595 | 112.848 | 31.465 | 1.00 35.18 | O |
| ATOM | 46125 | O | HOH | X1830 | 32.677 | 99.483 | 13.552 | 1.00 36.42 | O |
| ATOM | 46128 | O | HOH | X1831 | 62.429 | 116.759 | 35.917 | 1.00 34.48 | O |
| ATOM | 46131 | O | HOH | X1832 | 65.124 | 110.329 | 5.427 | 1.00 43.42 | O |
| ATOM | 46134 | O | HOH | X1833 | 41.812 | 107.323 | -0.059 | 1.00 35.48 | O |
| ATOM | 46137 | O | HOH | X1834 | 49.051 | 109.654 | 8.689 | 1.00 29.92 | O |
| ATOM | 46140 | O | HOH | X1835 | 65.917 | 93.975 | 38.415 | 1.00 32.91 | O |
| ATOM | 46143 | O | HOH | X1836 | 87.934 | 103.979 | 40.673 | 1.00 47.04 | O |
| ATOM | 46146 | O | HOH | X1837 | 78.126 | 76.658 | 21.858 | 1.00 52.19 | O |
| ATOM | 46149 | O | HOH | X1838 | 104.115 | 86.528 | 37.867 | 1.00 36.16 | O |
| ATOM | 46152 | O | HOH | X1839 | 92.168 | 99.038 | 36.604 | 1.00 35.62 | O |
| ATOM | 46155 | O | HOH | X1840 | 41.486 | 111.964 | 0.955 | 1.00 32.39 | O |
| ATOM | 46158 | O | HOH | X1841 | 58.386 | 110.685 | 20.335 | 1.00 37.23 | O |
| ATOM | 46161 | O | HOH | X1842 | 80.366 | 103.537 | 15.849 | 1.00 33.84 | O |
| ATOM | 46164 | O | HOH | X1843 | 63.455 | 33.371 | 19.865 | 1.00 39.13 | O |
| ATOM | 46167 | O | HOH | X1844 | 23.991 | 108.536 | 6.022 | 1.00 27.95 | O |
| ATOM | 46170 | O | HOH | X1845 | 3.054 | 46.791 | 27.931 | 1.00 44.72 | O |
| ATOM | 46173 | O | HOH | X1846 | 80.091 | 115.233 | 24.292 | 1.00 47.64 | O |
| ATOM | 46176 | O | HOH | X1847 | 85.366 | 97.144 | 17.726 | 1.00 43.60 | O |
| ATOM | 46179 | O | HOH | X1848 | 82.435 | 61.337 | 43.653 | 1.00 41.41 | O |
| ATOM | 46182 | O | HOH | X1849 | 43.289 | 123.828 | 4.120 | 1.00 40.72 | O |
| ATOM | 46185 | O | HOH | X1850 | 6.597 | 89.977 | 32.914 | 1.00 35.13 | O |
| ATOM | 46188 | O | HOH | X1851 | 68.222 | 46.356 | 5.603 | 1.00 41.30 | O |
| ATOM | 46191 | O | HOH | X1852 | 65.338 | 112.717 | 43.506 | 1.00 37.29 | O |
| ATOM | 46194 | O | HOH | X1853 | 40.762 | 59.484 | 24.166 | 1.00 38.12 | O |
| ATOM | 46197 | O | HOH | X1854 | 8.731 | 111.794 | 1.759 | 1.00 43.24 | O |
| ATOM | 46200 | O | HOH | X1855 | 77.636 | 99.554 | 6.704 | 1.00 34.91 | O |
| ATOM | 46203 | O | HOH | X1856 | 50.738 | 110.779 | 21.714 | 1.00 32.01 | O |
| ATOM | 46206 | O | HOH | X1857 | 19.566 | 44.695 | 5.350 | 1.00 34.63 | O |
| ATOM | 46209 | O | HOH | X1858 | 26.822 | 79.122 | 27.335 | 1.00 35.06 | O |
| ATOM | 46212 | O | HOH | X1859 | 51.546 | 75.805 | 16.613 | 1.00 37.16 | O |
| ATOM | 46215 | O | HOH | X1860 | 89.636 | 102.438 | 40.178 | 1.00 37.25 | O |
| ATOM | 46218 | O | HOH | X1862 | 74.458 | 59.781 | 37.406 | 1.00 35.67 | O |
| ATOM | 46221 | O | HOH | X1863 | 73.556 | 80.665 | 22.642 | 1.00 46.17 | O |
| ATOM | 46224 | O | HOH | X1864 | 49.292 | 113.436 | 6.956 | 1.00 32.08 | O |
| ATOM | 46227 | O | HOH | X1865 | 94.536 | 97.826 | 31.812 | 1.00 38.86 | O |
| ATOM | 46230 | O | HOH | X1866 | 57.887 | 46.171 | 33.440 | 1.00 32.56 | O |
| ATOM | 46233 | O | HOH | X1867 | 77.182 | 61.618 | 38.019 | 1.00 39.79 | O |
| ATOM | 46236 | O | HOH | X1868 | 93.460 | 83.493 | 29.229 | 1.00 28.25 | O |
| ATOM | 46239 | O | HOH | X1869 | 79.165 | 75.963 | 24.795 | 1.00 41.66 | O |
| ATOM | 46242 | O | HOH | X1870 | 30.125 | 119.125 | 39.266 | 1.00 35.05 | O |
| ATOM | 46245 | O | HOH | X1872 | 22.513 | 109.245 | 24.617 | 1.00 28.24 | O |
| ATOM | 46248 | O | HOH | X1873 | 82.854 | 87.936 | 14.007 | 1.00 46.77 | O |
| ATOM | 46251 | O | HOH | X1874 | 13.047 | 74.379 | 41.814 | 1.00 34.28 | O |
| ATOM | 46254 | O | HOH | X1875 | 72.153 | 69.477 | 34.133 | 1.00 40.33 | O |

| ATOM | 46257 | O | HOH X1876 | 45.989 | 47.908 | 37.170 | 1.00 | 34.93 | O |
|------|-------|---|-----------|--------|--------|--------|------|-------|---|
| ATOM | 46260 | O | HOH X1877 | -0.225 | 84.833 | 36.039 | 1.00 | 36.22 | O |
| ATOM | 46263 | O | HOH X1878 | 75.240 | 111.867 | 28.611 | 1.00 | 46.22 | O |
| ATOM | 46266 | O | HOH X1879 | 81.137 | 92.990 | 9.033 | 1.00 | 31.74 | O |
| ATOM | 46269 | O | HOH X1880 | 71.560 | 80.990 | 27.050 | 1.00 | 47.16 | O |
| ATOM | 46272 | O | HOH X1881 | 81.510 | 104.757 | 17.782 | 1.00 | 43.41 | O |
| ATOM | 46275 | O | HOH X1882 | 3.757 | 43.062 | 24.358 | 1.00 | 37.98 | O |
| ATOM | 46278 | O | HOH X1883 | 53.492 | 40.834 | 0.526 | 1.00 | 37.39 | O |
| ATOM | 46281 | O | HOH X1884 | 54.886 | 118.997 | 27.950 | 1.00 | 27.59 | O |
| ATOM | 46284 | O | HOH X1885 | 73.305 | 82.077 | 33.600 | 1.00 | 51.88 | O |
| ATOM | 46287 | O | HOH X1886 | 3.884 | 65.635 | 4.892 | 1.00 | 35.98 | O |
| ATOM | 46290 | O | HOH X1887 | 63.288 | 115.351 | 39.595 | 1.00 | 46.63 | O |
| ATOM | 46293 | O | HOH X1888 | 19.214 | 110.449 | 4.108 | 1.00 | 32.54 | O |
| ATOM | 46296 | O | HOH X1889 | 25.201 | 117.675 | 41.486 | 1.00 | 35.67 | O |
| ATOM | 46299 | O | HOH X1890 | 38.285 | 52.543 | 31.843 | 1.00 | 40.45 | O |
| ATOM | 46302 | O | HOH X1891 | 84.578 | 89.897 | 16.141 | 1.00 | 48.44 | O |
| ATOM | 46305 | O | HOH X1892 | 39.783 | 100.771 | 13.207 | 1.00 | 41.09 | O |
| ATOM | 46308 | O | HOH X1893 | 78.406 | 49.706 | 1.685 | 1.00 | 42.40 | O |
| ATOM | 46311 | O | HOH X1894 | 50.946 | 32.891 | 15.121 | 1.00 | 51.63 | O |
| ATOM | 46314 | O | HOH X1895 | 100.192 | 95.533 | 35.712 | 1.00 | 46.83 | O |
| ATOM | 46317 | O | HOH X1896 | 7.687 | 51.397 | 19.107 | 1.00 | 38.49 | O |
| ATOM | 46320 | O | HOH X1897 | 77.453 | 65.613 | 3.621 | 1.00 | 43.96 | O |
| ATOM | 46323 | O | HOH X1898 | 55.503 | 115.412 | 23.892 | 1.00 | 27.06 | O |
| ATOM | 46326 | O | HOH X1900 | 76.037 | 117.799 | 22.316 | 1.00 | 39.75 | O |
| ATOM | 46329 | O | HOH X1901 | 45.375 | 120.941 | 44.686 | 1.00 | 37.55 | O |
| ATOM | 46332 | O | HOH X1902 | 46.996 | 103.228 | 8.505 | 1.00 | 29.34 | O |
| ATOM | 46335 | O | HOH X1904 | 90.756 | 93.650 | 37.399 | 1.00 | 36.08 | O |
| ATOM | 46338 | O | HOH X1905 | 23.771 | 35.541 | 33.959 | 1.00 | 39.98 | O |
| ATOM | 46341 | O | HOH X1906 | 12.848 | 95.816 | 42.025 | 1.00 | 53.58 | O |
| ATOM | 46344 | O | HOH X1907 | 5.463 | 110.070 | 5.163 | 1.00 | 34.95 | O |
| ATOM | 46347 | O | HOH X1908 | 84.426 | 79.309 | 36.419 | 1.00 | 39.73 | O |
| ATOM | 46350 | O | HOH X1909 | 43.701 | 124.865 | 42.419 | 1.00 | 31.01 | O |
| ATOM | 46353 | O | HOH X1910 | 2.028 | 48.924 | 35.385 | 1.00 | 46.06 | O |
| ATOM | 46356 | O | HOH X1911 | 77.585 | 56.605 | -0.367 | 1.00 | 39.94 | O |
| ATOM | 46359 | O | HOH X1912 | 59.898 | 81.417 | 31.701 | 1.00 | 43.03 | O |
| ATOM | 46362 | O | HOH X1913 | 9.281 | 71.289 | 9.320 | 1.00 | 45.24 | O |
| ATOM | 46365 | O | HOH X1914 | 55.074 | 27.716 | 17.375 | 1.00 | 50.30 | O |
| ATOM | 46368 | O | HOH X1915 | 64.761 | 45.674 | 34.801 | 1.00 | 39.04 | O |
| ATOM | 46371 | O | HOH X1916 | 27.690 | 104.907 | 20.522 | 1.00 | 32.53 | O |
| ATOM | 46374 | O | HOH X1917 | 42.509 | 39.220 | 21.258 | 1.00 | 44.95 | O |
| ATOM | 46377 | O | HOH X1918 | 1.040 | 64.894 | 6.609 | 1.00 | 48.19 | O |
| ATOM | 46380 | O | HOH X1919 | 34.832 | 101.335 | 16.762 | 1.00 | 36.30 | O |
| ATOM | 46383 | O | HOH X1920 | 15.418 | 77.877 | 41.228 | 1.00 | 45.55 | O |
| ATOM | 46386 | O | HOH X1921 | 63.023 | 118.960 | 31.397 | 1.00 | 55.92 | O |
| ATOM | 46389 | O | HOH X1922 | 100.482 | 81.722 | 27.932 | 1.00 | 30.18 | O |
| ATOM | 46392 | O | HOH X1923 | 49.594 | 102.385 | 4.212 | 1.00 | 30.63 | O |
| ATOM | 46395 | O | HOH X1924 | 89.149 | 71.043 | 44.914 | 1.00 | 44.74 | O |
| ATOM | 46398 | O | HOH X1925 | 23.708 | 109.393 | 17.347 | 1.00 | 35.40 | O |
| ATOM | 46401 | O | HOH X1926 | 62.349 | 80.300 | 31.914 | 1.00 | 37.29 | O |
| ATOM | 46404 | O | HOH X1927 | 86.958 | 104.242 | 43.009 | 1.00 | 49.31 | O |
| ATOM | 46407 | O | HOH X1928 | 4.799 | 43.249 | 31.060 | 1.00 | 32.60 | O |
| ATOM | 46410 | O | HOH X1929 | 16.287 | 106.558 | 32.056 | 1.00 | 39.65 | O |
| ATOM | 46413 | O | HOH X1930 | 35.183 | 54.899 | 43.968 | 1.00 | 36.88 | O |
| ATOM | 46416 | O | HOH X1931 | 34.163 | 48.038 | 9.142 | 1.00 | 37.03 | O |
| ATOM | 46419 | O | HOH X1932 | 64.891 | 37.912 | 21.681 | 1.00 | 37.37 | O |
| ATOM | 46422 | O | HOH X1933 | 61.040 | 61.617 | 12.210 | 1.00 | 43.22 | O |
| ATOM | 46425 | O | HOH X1934 | 50.993 | 41.043 | 13.891 | 1.00 | 36.46 | O |

| ATOM | 46428 | O | HOH X1935 | 75.087 | 67.013 | 1.183 | 1.00 | 35.30 | O |
|------|-------|---|-----------|--------|--------|-------|------|-------|---|
| ATOM | 46431 | O | HOH X1936 | 64.195 | 80.886 | 34.384 | 1.00 | 51.96 | O |
| ATOM | 46434 | O | HOH X1937 | 83.660 | 54.434 | 16.213 | 1.00 | 46.60 | O |
| ATOM | 46437 | O | HOH X1938 | 21.089 | 45.495 | 11.246 | 1.00 | 40.10 | O |
| ATOM | 46440 | O | HOH X1939 | 74.270 | 111.795 | 36.117 | 1.00 | 33.61 | O |
| ATOM | 46443 | O | HOH X1940 | 42.860 | 49.744 | 41.604 | 1.00 | 44.51 | O |
| ATOM | 46446 | O | HOH X1941 | 79.749 | 55.965 | 32.100 | 1.00 | 53.38 | O |
| ATOM | 46449 | O | HOH X1942 | 39.922 | 47.685 | 36.121 | 1.00 | 43.84 | O |
| ATOM | 46452 | O | HOH X1943 | 13.916 | 63.577 | 28.005 | 1.00 | 36.51 | O |
| ATOM | 46455 | O | HOH X1944 | 36.655 | 117.412 | 16.099 | 1.00 | 45.93 | O |
| ATOM | 46458 | O | HOH X1945 | 92.332 | 98.454 | 30.202 | 1.00 | 35.32 | O |
| ATOM | 46461 | O | HOH X1946 | 23.703 | 45.552 | 12.576 | 1.00 | 43.32 | O |
| ATOM | 46464 | O | HOH X1947 | 48.828 | 121.453 | 23.140 | 1.00 | 36.78 | O |
| ATOM | 46467 | O | HOH X1948 | 76.380 | 86.690 | 26.900 | 1.00 | 37.51 | O |
| ATOM | 46470 | O | HOH X1949 | 12.795 | 111.510 | 24.379 | 1.00 | 40.04 | O |
| ATOM | 46473 | O | HOH X1950 | 39.983 | 124.203 | 40.574 | 1.00 | 37.72 | O |
| ATOM | 46476 | O | HOH X1951 | 28.792 | 66.239 | 29.337 | 1.00 | 59.28 | O |
| ATOM | 46479 | O | HOH X1952 | 29.630 | 108.227 | 25.942 | 1.00 | 43.98 | O |
| ATOM | 46482 | O | HOH X1953 | 57.893 | 35.170 | 23.592 | 1.00 | 33.15 | O |
| ATOM | 46485 | O | HOH X1954 | 0.319 | 89.370 | 31.193 | 1.00 | 52.19 | O |
| ATOM | 46488 | O | HOH X1955 | 76.575 | 47.713 | 13.485 | 1.00 | 39.32 | O |
| ATOM | 46491 | O | HOH X1957 | 32.687 | 110.878 | 27.651 | 1.00 | 41.55 | O |
| ATOM | 46494 | O | HOH X1958 | 44.933 | 39.094 | 24.361 | 1.00 | 50.91 | O |
| ATOM | 46497 | O | HOH X1959 | 59.103 | 42.996 | 31.499 | 1.00 | 40.49 | O |
| ATOM | 46500 | O | HOH X1960 | 76.032 | 81.956 | 20.524 | 1.00 | 37.60 | O |
| ATOM | 46503 | O | HOH X1961 | 9.594 | 113.071 | 14.392 | 1.00 | 43.34 | O |
| ATOM | 46506 | O | HOH X1962 | 12.203 | 111.757 | 7.593 | 1.00 | 39.95 | O |
| ATOM | 46509 | O | HOH X1963 | 74.032 | 97.160 | 33.365 | 1.00 | 40.52 | O |
| ATOM | 46512 | O | HOH X1964 | 76.318 | 48.481 | 22.974 | 1.00 | 39.14 | O |
| ATOM | 46515 | O | HOH X1966 | 28.300 | 119.436 | 35.786 | 1.00 | 43.65 | O |
| ATOM | 46518 | O | HOH X1967 | 87.097 | 74.645 | 18.793 | 1.00 | 45.21 | O |
| ATOM | 46521 | O | HOH X1968 | 94.599 | 74.954 | 41.582 | 1.00 | 50.64 | O |
| ATOM | 46524 | O | HOH X1969 | 4.183 | 67.697 | 17.683 | 1.00 | 43.24 | O |
| ATOM | 46527 | O | HOH X1970 | 33.741 | 118.881 | 5.883 | 1.00 | 46.62 | O |
| ATOM | 46530 | O | HOH X1971 | 62.037 | 109.281 | 3.105 | 1.00 | 48.71 | O |
| ATOM | 46533 | O | HOH X1972 | 42.320 | 84.271 | 30.540 | 1.00 | 45.02 | O |
| ATOM | 46536 | O | HOH X1973 | 23.190 | 76.233 | 20.175 | 1.00 | 39.97 | O |
| ATOM | 46539 | O | HOH X1974 | 77.023 | 47.380 | 5.859 | 1.00 | 60.83 | O |
| ATOM | 46542 | O | HOH X1975 | 10.106 | 91.881 | 36.853 | 1.00 | 43.37 | O |
| ATOM | 46545 | O | HOH X1976 | 77.564 | 115.873 | 25.187 | 1.00 | 41.33 | O |
| ATOM | 46548 | O | HOH X1977 | 30.960 | 106.486 | 23.596 | 1.00 | 42.54 | O |
| ATOM | 46551 | O | HOH X1978 | 44.234 | 50.924 | 16.083 | 1.00 | 16.51 | O |
| ATOM | 46554 | O | HOH X1979 | 44.280 | 49.543 | 18.662 | 1.00 | 19.19 | O |

We claim:

1. A phenylalanine ammonia lyase (PAL) comprising a mutant *Rhodosporidium toruloides* PAL, wherein said PAL has a mutation selected from the group consisting of: R91K, H137K and combinations thereof.

2. The PAL of claim 1, wherein the amino acid residue is replaced by site-directed mutagenesis, random mutagenesis, or by point mutagenesis.

3. The PAL of claim 1, further comprising pegylation.

4. The PAL of claim 3, wherein the PAL has a phenylalanine-converting activity greater than the wild-type PAL.

5. The PAL of claim 4, wherein the PAL has the phenylalanine-converting activity at least 20% greater than the wild-type PAL.

6. A composition comprising the PAL of claim 1 or 3.

7. A method for treating an amino acid metabolism disease by administering the composition of claim 6 to a patient in need thereof, wherein said amino acid metabolism disease is selected from the group consisting of phenylketonuria, hyperphenylalanemia, tyrosineamia and histidinemia.

* * * * *